US011845723B2

(12) United States Patent
Sawa et al.

(10) Patent No.: US 11,845,723 B2
(45) Date of Patent: Dec. 19, 2023

(54) DIACYLGLYCEROL KINASE MODULATING COMPOUNDS

(71) Applicants: GILEAD SCIENCES, INC., Foster City, CA (US); CARNA BIOSCIENCES, INC., Kobe (JP)

(72) Inventors: Masaaki Sawa, Kobe (JP); Mai Arai, Kobe (JP); Ryoko Nakai, Kobe (JP); Hirokazu Matsumoto, Kobe (JP); Catherine Pugh, Foster City, CA (US); Eric Hu, Foster City, CA (US); Juan Guerrero, Foster City, CA (US); Jesse Jacobsen, Foster City, CA (US); Jonathan William Medley, Foster City, CA (US); Jie Xu, Foster City, CA (US); Latesh Lad, Foster City, CA (US); Leena Patel, Foster City, CA (US); Michael Graupe, Foster City, CA (US); Qingming Zhu, Foster City, CA (US); Stephen Holmbo, Foster City, CA (US); Tetsuya Kobayashi, Foster City, CA (US); Will Watkins, Foster City, CA (US); Yasamin Moazami, Foster City, CA (US); Suet C. Yeung, Foster City, CA (US); Julian A. Codelli, Foster City, CA (US); Heath A. Weaver, Foster City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 244 days.

(21) Appl. No.: 17/127,297

(22) Filed: Dec. 18, 2020

(65) Prior Publication Data
US 2022/0324866 A1 Oct. 13, 2022

(30) Foreign Application Priority Data

Dec. 24, 2019 (JP) .................................. 2019-232938
Aug. 11, 2020 (JP) .................................. 2020-135810

(51) Int. Cl.
| | | |
|---|---|---|
| *C07D 487/04* | (2006.01) | |
| *A61K 31/519* | (2006.01) | |
| *A61K 31/5377* | (2006.01) | |
| *A61K 31/538* | (2006.01) | |
| *A61K 31/55* | (2006.01) | |
| *A61K 31/553* | (2006.01) | |
| *A61K 31/704* | (2006.01) | |
| *A61K 31/7068* | (2006.01) | |
| *C07D 519/00* | (2006.01) | |
| *A61K 31/554* | (2006.01) | |
| *A61K 31/695* | (2006.01) | |
| *A61K 31/395* | (2006.01) | |
| *A61K 35/15* | (2015.01) | |
| *A61K 35/17* | (2015.01) | |
| *A61K 39/395* | (2006.01) | |
| *A61K 45/06* | (2006.01) | |
| *C07F 7/18* | (2006.01) | |

(52) U.S. Cl.
CPC .......... *C07D 487/04* (2013.01); *A61K 31/519* (2013.01); *A61K 31/538* (2013.01); *A61K 31/5377* (2013.01); *A61K 31/55* (2013.01); *A61K 31/553* (2013.01); *A61K 31/5545* (2017.08); *A61K 31/695* (2013.01); *A61K 31/704* (2013.01); *A61K 31/7068* (2013.01); *A61K 35/15* (2013.01); *A61K 35/17* (2013.01); *A61K 39/3955* (2013.01); *A61K 45/06* (2013.01); *C07D 519/00* (2013.01); *C07F 7/1804* (2013.01)

(58) Field of Classification Search
CPC .. C07D 487/04; C07D 519/00; A61K 31/519; A61K 31/5377; A61K 31/538; A61K 31/55; A61K 31/553; A61K 31/5545; A61K 31/695; A61K 31/704; A61K 31/7068

See application file for complete search history.

(56) References Cited

U.S. PATENT DOCUMENTS

| | | |
|---|---|---|
| 2021/0188845 A1 | 6/2021 | Gentles et al. |
| 2022/0315603 A1 | 10/2022 | Watanabe et al. |
| 2023/0046340 A1 | 2/2023 | Codelli et al. |
| 2023/0060004 A1 | 2/2023 | Graupe et al. |

(Continued)

FOREIGN PATENT DOCUMENTS

| | | |
|---|---|---|
| WO | WO-2007114239 A1 | 10/2007 |
| WO | 2019005883 A1 | 1/2019 |
| WO | 2020006016 A1 | 1/2020 |

(Continued)

OTHER PUBLICATIONS

Deng, X., C. Xiao, C. Wei and Z. Quan, "Synthesis and anticonvulsant activity of 5-substituted-[1,24]-triazolo[4,3-a]quinazolines", Chinese Journal of Organic Chemistry (2011), 31 (12), pp. 2082-2087. (Year: 2011).*
English translation of Deng, X., C. Xiao, C. Wei and Z. Quan, "Synthesis and anticonvulsant activity of 5-substituted-[1,24]-triazolo[4,3-a]quinazolines", Chinese Journal of Organic Chemistry (2011), 31 (12), pp. 2082-2087. (Year: 2023).*
International Preliminary Report on Patentability and Written Opinion of the International Searching Authority, dated Jul. 7, 2022 for Intl. Appl. No. PCT/IB2020/062229.

(Continued)

*Primary Examiner* — Joseph R Kosack
*Assistant Examiner* — Sagar Patel

(57) ABSTRACT

The present disclosure provides diacylglycerol kinase modulating compounds, and pharmaceutical compositions thereof, for treating cancer, including solid tumors, and viral infections, such as HIV or hepatitis B virus infection. The compounds can be used alone or in combination with other agents.

41 Claims, No Drawings

(56) References Cited

U.S. PATENT DOCUMENTS

| | | |
|---|---|---|
| 2023/0060354 A1 | 3/2023 | Codelli et al. |
| 2023/0116253 A1 | 4/2023 | Codelli et al. |

FOREIGN PATENT DOCUMENTS

| | | |
|---|---|---|
| WO | 2020006018 A1 | 1/2020 |
| WO | 2021041588 A1 | 3/2021 |
| WO | 2021105115 A1 | 6/2021 |
| WO | 2021105116 A1 | 6/2021 |
| WO | 2021105117 A1 | 6/2021 |
| WO | 2021127554 A1 | 6/2021 |
| WO | 2021132422 A1 | 7/2021 |
| WO | 2021133748 A1 | 7/2021 |
| WO | 2021133749 A1 | 7/2021 |
| WO | 2021133750 A1 | 7/2021 |
| WO | 2021133751 A1 | 7/2021 |
| WO | 2021133752 A1 | 7/2021 |
| WO | WO-2021214019 A1 | 10/2021 |
| WO | WO-2021214020 A1 | 10/2021 |
| WO | WO-2021258010 A1 | 12/2021 |
| WO | WO-2022133083 A1 | 6/2022 |
| WO | WO-2022271650 A1 | 12/2022 |
| WO | WO-2022271659 A1 | 12/2022 |
| WO | WO-2022271677 A1 | 12/2022 |
| WO | WO-2022271684 A1 | 12/2022 |

OTHER PUBLICATIONS

Avila-Florez et al., "Predominant contribution of DGK? over DGKa in the control of PKC/PDK-1-regulated functions in T cells", Immunol, Cell. Biol., 2017, 95, 549-563.

Carrasco et al., "Diacylglycerol, when simplicity becomes complex", Trends Biochem. Sci. 2007, 32, 27-36.

Dominguez et al., "Diacylglycerol kinase a is a critical signaling node and novel therapeutic target in glioblastoma and other cancers", Cancer Discov., 2013, 782-797.

Examination and Search Report dated Oct. 19, 2021 for Gulf Co-Operation Council Application No. 2020-41329.

Joshi et al., "Diacylglycerol kinases: regulated controllers of T cell activation, function, and development", Int. J. Mol. Sci., 2013, 14, 6649-6673.

Jung et al., "CRISPR/Cas9-Mediated Knockout of DGK Improves Antitumor Activities of Human T Cells", Cancer Res., 2018, 78, 4692-4703.

Merida et al., "Diacylglycerol kinases in cancer", Adv. Biol. Regul., 2017, 63, 22-31.

Office Action and Search Report dated Nov. 17, 2021 for Taiwan (ROC) Application 109145843.

Riese et al., "Enhanced effector responses in activated CD8+ T cells deficient in diacylglycerol kinases", Cancer Res., 2013, 73, 3566-3577.

Sakane et al., "Diacylglycerol Kinases as Emerging Potential Drug Targets for a Variety of Diseases: An Update", Front. Cell Dev. Biol., 2016, 4, 82.

Spranger et al., "Impact of oncogenic pathways on evasion of antitumour immune responses", Nat. Rev. Cancer., 2018, 18, 139-147.

Torres-Ayuso et al., "Diacylglycerol kinase a promotes 3D cancer cell growth and limits drug sensitivity through functional interaction with Src", Oncotarget, 2014, 5, 9710-9726.

Zha et al., "T cell anergy is reversed by active Ras and is regulated by diacylglycerol kinase-alpha", Nat.Immunol., 2006, 7, 1166-1173.

International Search Report and Written Opinion received for PCT Application No. PCT/IB2020/062229, dated Feb. 19, 2021, 12 pages.

Hayashi et al. "Screening of Subtype-Specific Activators and Inhibitors for Diacylglycerol Kinase", Journal of Biochemistry, Jun. 1, 2019, 165(6):517-522.

Velnati et al. "Identification of a Novel DGKα Inhibitor for XLP-1 Therapy by Virtual Screening", European Journal of Medicinal Chemistry, Feb. 15, 2019, 164:378-390 (27 pages).

Deng et al. "Synthesis and Anticonvulsant Activity of 5-Substituted-[1,2,4]triazolo[4,3-a]quinazolines", Chinese Journal of Organic Chemistry, 2011, 31(12):2082-2087.

* cited by examiner

DIACYLGLYCEROL KINASE MODULATING COMPOUNDS

CROSS-REFERENCES TO RELATED APPLICATIONS

This application claims the benefit of priority to Japan Application Nos. 2019-232938, filed Dec. 24, 2019, and 2020-135810, filed Aug. 11, 2020, each of which is incorporated herein in its entirety.

BACKGROUND

Diacylglycerol (DAG) is known as a second messenger of signaling molecule and takes an important role in cellular proliferation, differentiation and/or metabolism (Carrasco, S., Merida, I. Trends Biochem. Sci. 2007, 32, 27-36.) Intracellular concentration and localization of DAG is strictly controlled, and diacylglycerol kinase (DGK) is one of enzymes controlling them. DGK is an enzyme that synthesizes a phosphatidic acid (PA) by transferring a phosphoryl group to DAG. Ten human isozymes (α, β, γ, δ, ε, ζ, η, θ, ι, κ) are known (Joshi, R. P., Koretzky, G. A. Int. J. Mol. Sci., 2013, 14, 6649-6673.) Each isozyme is believed to localize and associate with different proteins and/or with different cell types. DGK is reported to be involved in pathogenesis of multiple diseases including cancers, immune diseases, neurodegenerative diseases, and diabetes (Sakane, F., et al. Front. Cell Dev. Biol., 2016, 4, 82.)

DGKα has been a target of research, including research into possible cancer treatment. For example, an inhibitory activity on proliferation of glioblastoma cells was reported as a result of knockdown caused by RNA-interference targeting DGKα (Dominguez, C. L., et al. Cancer Discov., 2013, 782-797.) An inhibitory effect was also reported on a human colon carcinoma cell line in three-dimensional cell culture, and the knockdown of DGKα was further reported to inhibit tumor proliferation in a mouse model (Torres-Ayuso, P., et al. Oncotarget, 2014, 5, 9710-9726.) Inhibition of DGKα has been disclosed in WO 2007/114239. Accordingly, a compound with an inhibitory activity on DGKα may be useful for therapeutics, such as treating a cancer in which DGKα is involved in its proliferation.

In recent years, cancer immunotherapy has attracted attention as a potential cancer treatment. An immune checkpoint inhibitor such as anti-CTLA-4 (Cytotoxic T lymphocyte antigen 4) antibody, anti-PD-1 (Programmed death receptor 1) antibody, anti-PD-L1 (Programmed death ligand 1) antibody etc. could be administered and an antitumor immune response can be potentiated in a patient. Some immune checkpoint inhibitors have been already approved as a medicine for antitumor therapy. However, the antitumor effects are often limited to a few patients. Further, some patients become resistant to the inhibitors (Spranger, S., Gajewski, T. F., Nat. Rev. Cancer., 2018, 18, 139-147.)

DGKα is expressed in a T-cell, mediating a signaling of T-cell receptor (TCR,) and is believed to play a role in T-cell activation (Joshi et al. as above and Merida, I. et al., Adv. Biol. Regul., 2017, 63, 22-31.) When a T-cell is under a condition of immunological unresponsiveness such as anergy, expression of DGKα can be increased, and an overexpression of DGKα has been reported to induce a condition of anergy (Zha, Y. et al., Nat. Immunol., 2006, 7, 1166-1173.) Further, activation of a T-cell has been reported as a result of knockdown of DGKα in the T-cell by means of RNA-interference (Avila-Flores, A., et al. Immunol. Cell. Biol., 2017, 95, 549-563.) Accordingly, a compound with an activity to control DGKα may be useful for preventing and/or treating diseases related to a T-cell, such as immunologic or inflammatory diseases.

Recently CAR (Chimeric Antigen Receptor) T cell therapy has also attracted attention as a promising immune cancer therapy. It has been reported that DGKα-deficient CAR T cells have high effector function and anti-tumor effect on a solid cancer (Riese, M. J. et al. Cancer Res., 2013, 73, 3566-3577; Jung, I. Y., et al. Cancer Res., 2018, 78, 4692-4703.) Hence, use of a compound having inhibitory effect on DGKα may be complementary with CAR T cell therapy.

However, there remains a need for DGKα inhibitors, for example, with desirable pharmaceutical and therapeutic properties.

BRIEF SUMMARY

In one embodiment, the present disclosure provides a compound of Formula (I-1):

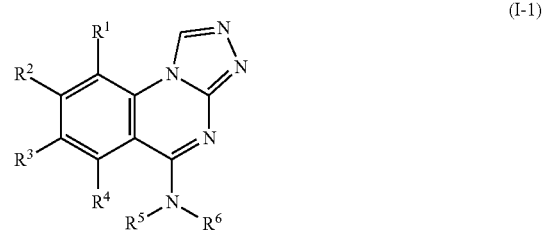

or a pharmaceutically acceptable salt thereof, wherein
$R^1$, $R^2$, $R^3$ and $R^4$ are independently a hydrogen atom, a halogen atom, a hydroxy group, a carboxy group, a formyl group, a cyano group, an amino group, a nitro group, a nitroso group, a alkoxycarbonyl group, an optionally substituted alkyl group, an optionally substituted alkenyl group, an optionally substituted alkynyl group, an optionally substituted cycloalkyl group, an optionally substituted alkoxy group, an optionally substituted alkylamino group, an optionally substituted aryl group, an optionally substituted heteroaryl group, an optionally substituted acyl group, an optionally substituted carbamoyl group, an optionally substituted acylamino group, an optionally substituted saturated heterocyclo group or an optionally substituted alkylsulfonylamino group;
$R^5$ is a hydrogen atom, an optionally substituted alkyl group, an optionally substituted alkynyl group, or an optionally substituted aryl group; and
$R^6$ is an optionally substituted alkyl group, an optionally substituted aryl group, an optionally substituted heteroaryl group, or $R^5$ and $R^6$ together with a nitrogen atom which they bound, may form a nitrogen-containing saturated heterocyclo ring to which an aryl ring is fused, and the fused ring may be substituted;
provided that the compound is not

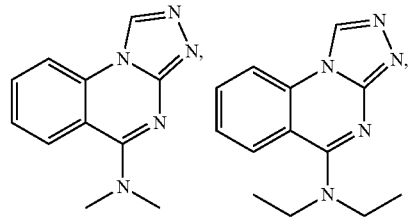

-continued

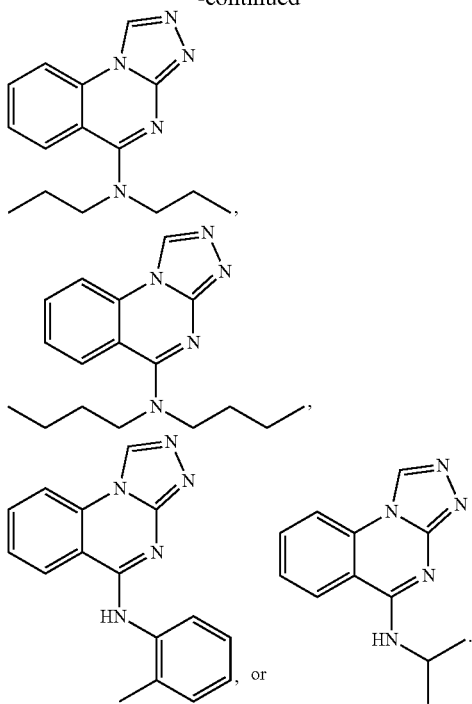

In another embodiment, the present disclosure provides a compound of Formula (I):

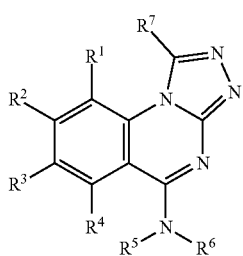

(I)

or a pharmaceutically acceptable salt thereof, wherein
$R^1$ is hydrogen, $C_{1-6}$ alkyl, $C_{2-6}$ alkenyl, $C_{2-6}$ alkynyl, $C_{1-6}$ alkoxy, halogen, $C_{1-6}$ haloalkyl, $C_{1-6}$ haloalkoxy, or —CN;

$R^2$ is hydrogen, $C_{1-6}$ alkyl, $C_{2-6}$ alkenyl, $C_{2-6}$ alkynyl, $C_{1-6}$ hydroxyalkyl, $C_{1-6}$ aminoalkyl, $C_{1-6}$ alkoxy, $C_{2-6}$ alkoxyalkyl, halogen, $C_{1-6}$ haloalkyl, $C_{1-6}$ haloalkoxy, —CN, —NO, —NO$_2$, —C(O)R$^{2a}$, —C(O)OR$^{2a}$, —OC(O)R$^{2a}$, —C(O)N(R$^{2a}$)(R$^{2b}$), —N(R$^{2a}$)C(O)R$^{2b}$, —OC(O)N(R$^{2a}$)(R$^{2b}$), —N(R$^{2a}$)C(O)OR$^{2b}$, —C(=NR$^{2a}$)N(R$^{2b}$)(R$^{2c}$), —N(R$^{2a}$)(R$^{2b}$), —N(R$^{2a}$)N(R$^{2b}$)(R$^{2c}$), —N(R$^{2a}$)N=C(R$^{2b}$)(OR$^{2c}$), —OR$^{2a}$, —SR$^{2a}$, —S(O)R$^{2a}$, —S(O)(NR$^{2a}$)(R$^{2b}$), —S(NR$^{2a}$)(NR$^{2b}$)(R$^{2c}$), —S(O)$_2$R$^{2a}$, —S(O)$_2$N(R$^{2a}$)(R$^{2b}$), —N(R$^{2a}$)S(O)$_2$(R$^{2b}$), —P(R$^{2a}$)(R$^{2b}$), —P(O)(R$^{2a}$)(R$^{2b}$), —P(O)(OR$^{2a}$)(R$^{2b}$), —P(O)(OR$^{2a}$)(OR$^{2b}$), $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, $C_{1-6}$ alkyl-(heterocycloalkyl), heteroaryl, or $C_{1-6}$ alkyl-(heteroaryl), wherein each alkyl, alkenyl or alkynyl is independently optionally substituted with 1 to 3 R$^{2d}$ groups, each cycloalkyl is optionally substituted with 1 to 3 R$^{2e}$ groups, each aryl is optionally substituted with 1 to 3 R$^{2f}$ groups, each heterocycloalkyl is optionally substituted with 1 to 3 R$^{2g}$ groups, and each heteroaryl is optionally substituted with 1 to 3 R$^{2h}$ groups;

each $R^{2a}$, $R^{2b}$, and $R^{2c}$ is independently hydrogen, $C_{1-6}$ alkyl, $C_{2-6}$ alkenyl, $C_{2-6}$ alkynyl, $C_{1-6}$ hydroxyalkyl, $C_{1-6}$ aminoalkyl, $C_{2-6}$ alkoxyalkyl, $C_{1-6}$ haloalkyl, $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, $C_{1-6}$ alkyl-(heterocycloalkyl), heteroaryl, or $C_{1-6}$ alkyl-(heteroaryl), wherein the aryl or heteroaryl is optionally substituted with 1 to 3 R$^{2j}$;

alternatively, $R^{2a}$, $R^{2b}$, and $R^{2c}$ when attached to the same atom can be combined with the atom to which they are attached to form a heterocycloalkyl;

each $R^{2d}$ is independently —CN, —C(O)R$^{2d1}$, —C(O)OR$^{2d1}$, —OC(O)R$^{2d1}$, —C(O)N(R$^{2d1}$)(R$^{2d2}$), —N(R$^{2d1}$)C(O)R$^{2d2}$, —OC(O)N(R$^{2d1}$)(R$^{2d2}$), —N(R$^{2d1}$)C(O)OR$^{2d2}$, —N(R$^{2d}$)(R$^{2d2}$), =O, —OR$^{2d1}$, —SR$^{2d1}$, —S(O)R$^{2d1}$, —S(O)(NR$^{2d1}$)(R$^{2d2}$), —S(O)$_2$R$^{2d1}$, —S(O)N(R$^{2d1}$)(R$^{2d2}$), —N(R$^{2d1}$)S(O)$_2$R$^{2d2}$, $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, $C_{1-6}$ alkyl-(heterocycloalkyl), heteroaryl, or $C_{1-6}$ alkyl-(heteroaryl);

each $R^{2d1}$ and $R^{2d2}$ is independently hydrogen, $C_{1-6}$ alkyl, $C_{1-6}$ hydroxyalkyl, $C_{1-6}$ aminoalkyl, $C_{2-6}$ alkoxyalkyl, or $C_{1-6}$ haloalkyl;

each $R^{2e}$, $R^{2f}$, $R^{2g}$, and $R^{2h}$ is independently hydrogen, $C_{1-6}$ alkyl, $C_{1-6}$ hydroxyalkyl, $C_{1-6}$ aminoalkyl, $C_{1-6}$ alkoxy, $C_{2-6}$ alkoxyalkyl, halogen, $C_{1-6}$ haloalkyl, $C_{1-6}$ haloalkoxy, —CN, or —OH;

each $R^{2j}$ is independently $C_{1-6}$ alkyl, $C_{1-6}$ hydroxyalkyl, $C_{1-6}$ aminoalkyl, $C_{1-6}$ alkoxy, $C_{2-6}$ alkoxyalkyl, halogen, $C_{1-6}$ haloalkyl, or $C_{1-6}$ haloalkoxy;

$R^3$ is hydrogen, $C_{1-6}$ alkyl, $C_{2-6}$ alkenyl, $C_{2-6}$ alkynyl, $C_{1-6}$ hydroxyalkyl, $C_{1-6}$ aminoalkyl, $C_{1-6}$ alkoxy, $C_{2-6}$ alkoxyalkyl, halogen, $C_{1-6}$ haloalkyl, $C_{1-6}$ haloalkoxy, —CN, —NO, —NO$_2$, —C(O)R$^{3a}$, —C(O)OR$^{3a}$, —OC(O)R$^{3a}$, —C(O)N(R$^{3a}$)(R$^{3b}$), —N(R$^{3a}$)C(O)R$^{3b}$, —OC(O)N(R$^{3a}$)(R$^{3b}$), —N(R$^{3a}$)C(O)OR$^{3b}$, —C(=NR$^{3a}$)N(R$^{3b}$)(R$^{3c}$), —N(R$^{3a}$)(R$^{3b}$), —N(R$^{3a}$)N(R$^{3b}$)(R$^{3c}$), —N(R$^{3a}$)N=C(R$^{3b}$)(OR$^{3c}$), —OR$^{3a}$, —SR$^{3a}$, —S(O)R$^{3a}$, —S(O)(NR$^{3a}$)(R$^{3b}$), —S(NR$^{3a}$)(NR$^{3b}$)(R$^{3c}$), —S(O)$_2$R$^{3a}$, —S(O)$_2$N(R$^{3a}$)(R$^{3b}$), —N(R$^{3a}$)S(O)$_2$(R$^{3b}$), —P(R$^{3a}$)(R$^{3b}$), —P(O)(R$^{3a}$)(R$^{3b}$), —P(O)(OR$^{3a}$)(R$^{3b}$), —P(O)(OR$^{3a}$)(OR$^{3b}$), $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, $C_{1-6}$ alkyl-(heterocycloalkyl), heteroaryl, or $C_{1-6}$ alkyl-(heteroaryl), wherein each alkenyl or alkynyl is independently optionally substituted with 1 to 3 R$^{3d}$ groups, each cycloalkyl is optionally substituted with 1 to 3 R$^{3e}$ groups, each aryl is optionally substituted with 1 to 3 R$^{3f}$ groups, each heterocycloalkyl is optionally substituted with 1 to 3 R$^{3g}$ groups, and each heteroaryl is optionally substituted with 1 to 3 R$^{3h}$ groups;

each $R^{3a}$, $R^{3b}$, and $R^{3c}$ is independently hydrogen, $C_{1-6}$ alkyl, $C_{1-6}$ hydroxyalkyl, $C_{2-6}$ alkoxyalkyl, $C_{1-6}$ haloalkyl, $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, or heteroaryl;

alternatively, $R^{3a}$, $R^{3b}$, and $R^{3c}$ when attached to the same atom can be combined with the atom to which they are attached to form a heterocycloalkyl;

each $R^{3d}$ is independently —N($R^{3d1}$)($R^{3d2}$), —O$R^{3d1}$, $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, or heteroaryl;

each $R^{3d1}$ and $R^{3d2}$ is independently hydrogen, $C_{1-6}$ alkyl, or —C(O)O—($C_{1-6}$ alkyl);

each $R^{3e}$, $R^{3f}$, $R^{3g}$, and $R^{3h}$ is independently hydrogen, $C_{1-6}$ alkyl, $C_{1-6}$ alkoxy, halogen, $C_{1-6}$ haloalkyl or $C_{1-6}$ haloalkoxy;

$R^4$ is hydrogen, $C_{1-6}$ alkyl, $C_{2-6}$ alkenyl, $C_{2-6}$ alkynyl, $C_{1-6}$ alkoxy, halogen, $C_{1-6}$ haloalkyl, $C_{1-6}$ haloalkoxy, or —CN;

$R^5$ is hydrogen, $C_{1-6}$ alkyl, $C_{2-6}$ alkenyl, $C_{2-6}$ alkynyl, $C_{1-6}$ hydroxyalkyl, $C_{2-6}$ alkoxyalkyl, $C_{1-6}$ haloalkyl, $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, $C_{1-6}$ alkyl-(heterocycloalkyl), heteroaryl, or $C_{1-6}$ alkyl-(heteroaryl), wherein the alkyl is optionally substituted with $R^{5a}$;

$R^{5a}$ is —OSi($R^{5a1}$)($R^{5a2}$)($R^{5a3}$);

$R^{5a1}$, $R^{5a2}$, and $R^{5a3}$ are each independently $C_{1-6}$ alkyl; and $R^6$ is $C_{1-6}$ alkyl, $C_{2-6}$ alkenyl, $C_{2-6}$ alkynyl, $C_{1-6}$ haloalkyl, $C_{6-12}$ aryl, or heteroaryl, wherein the aryl or heteroaryl are each optionally substituted with 1 to 3 $R^{6a}$;

each $R^{6a}$ is independently $C_{1-6}$ alkyl, $C_{2-6}$ alkenyl, $C_{2-6}$ alkynyl, $C_{1-6}$ hydroxyalkyl, $C_{1-6}$ aminoalkyl, $C_{1-6}$ alkoxy, $C_{2-6}$ alkoxyalkyl, halogen, $C_{1-6}$ haloalkyl, $C_{1-6}$ haloalkoxy, —CN, —NO$_2$, —C(O)$R^{6b}$, —C(O)O$R^{6b}$, —OC(O)$R^{6b}$, —C(O)N($R^{6b}$)($R^{6c}$), —N($R^{6b}$)C(O)$R^{6c}$, —C(=N$R^{6b}$)N($R^{6c}$)($R^{6d}$), —N($R^{6b}$)($R^{6c}$), —O$R^{6b}$, —S$R^{6b}$, —S(O)$R^{6b}$, —S(O)$_2R^{6b}$, —S(N$R^{6b}$)(N$R^{6c}$)$R^{6d}$, —S(O)(N$R^{6b}$)($R^{6c}$), —S(O)$_2$N($R^{6b}$)($R^{6c}$), —N($R^{6b}$)S(O)$_2$($R^{6c}$), —P($R^{6b}$)($R^{6c}$), —P(O)($R^{6b}$)($R^{6c}$), —P(O)(O$R^{6b}$)($R^{6c}$), —P(O)(O$R^{6b}$)(O$R^{6c}$), $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, $C_{1-6}$ alkyl-(heterocycloalkyl), heteroaryl, or $C_{1-6}$ alkyl-(heteroaryl), wherein the cycloalkyl, aryl, heterocycloalkyl, or heteroaryl is each optionally substituted with 1 to 3 $R^6$, the alkyl is optionally substituted with $R^{6f}$, and the alkynyl is optionally substituted with 1 to 4 $R^{6j}$;

each $R^{6b}$, $R^{6c}$ and $R^{6d}$ is independently hydrogen, $C_{1-6}$ alkyl, $C_{1-6}$ hydroxyalkyl, $C_{1-6}$ aminoalkyl, $C_{2-6}$ alkoxyalkyl, $C_{1-6}$ haloalkyl, $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, $C_{1-6}$ alkyl-(heterocycloalkyl), heteroaryl, or $C_{1-6}$ alkyl-(heteroaryl), wherein the cycloalkyl, aryl, heterocycloalkyl, or heteroaryl is optionally substituted by 1 to 3 $R^{6k}$;

each $R^{6k}$ is independently $C_{1-6}$ alkyl, $C_{1-6}$ hydroxyalkyl, $C_{1-6}$ aminoalkyl, $C_{1-6}$ alkoxy, $C_{2-6}$ alkoxyalkyl, $C_{1-6}$ haloalkyl, $C_{1-6}$ haloalkoxy, $C_{3-10}$ cycloalkyl, $C_{1-6}$ alkyl-$C_{3-10}$ cycloalkyl, heterocycloalkyl, or $C_{1-6}$ alkyl-(heterocycloalkyl);

each $R^{6e}$ is independently $C_{1-6}$ alkyl, $C_{2-6}$ alkenyl, $C_{2-6}$ alkynyl, $C_{1-6}$ hydroxyalkyl, $C_{1-6}$ aminoalkyl, $C_{1-6}$ alkoxy, $C_{2-6}$ alkoxyalkyl, halogen, $C_{1-6}$ haloalkyl, $C_{1-6}$ haloalkoxy, —CN, —NO$_2$, —C(O)$R^{6e1}$, —C(O)O$R^{6e1}$, —OC(O)$R^{6e1}$, —C(O)N($R^{6e1}$)($R^{6e2}$), —N($R^{6e1}$)C(O)$R^{6e2}$, —OC(O)N($R^{6e1}$)($R^{6e2}$), —N($R^{6e1}$)C(O)O$R^{6e2}$, —C(=N$R^{6e1}$)N($R^{6e2}$)($R^{6e3}$), —N($R^{6e1}$)($R^{6e2}$), =O, —O$R^{6e1}$, —S$R^{6e1}$, —S(O)$R^{6e1}$, —S(N$R^{6e1}$)(N$R^{6e2}$), —S(O)(N$R^{6e1}$)($R^{6e2}$), —S(O)$_2R^{6e1}$, —S(O)$_2$N($R^{6e1}$)($R^{6e2}$), —SF$_5$, —N($R^{6e1}$)S(O)$_2$($R^{6e2}$), —P($R^{6e1}$)($R^{6e2}$), —P(O)($R^{6e1}$)($R^{6e2}$), —P(O)(O$R^{6e1}$)($R^{6e2}$), —P(O)(O$R^{6e1}$)(O$R^{6e2}$), —Si($R^{6e1}$)($R^{6e2}$)($R^{6e3}$), $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, $C_{1-6}$ alkyl-heterocycloalkyl, heteroaryl, or $C_{1-6}$ alkyl-heteroaryl, wherein the cycloalkyl, aryl, heterocycloalkyl, or heteroaryl is each optionally substituted with 1 to 3 $R^{6h}$, and the alkyl is optionally substituted with 1 to 3 $R^{6m}$;

each $R^{6e1}$, $R^{6e2}$, and $R^{6e3}$ is independently hydrogen, $C_{1-6}$ alkyl, $C_{1-6}$ hydroxyalkyl, $C_{1-6}$ aminoalkyl, $C_{1-6}$ alkoxyalkyl, $C_{1-6}$ haloalkyl, $C_{3-10}$ cycloalkyl, $C_{1-6}$ alkyl-$C_{3-10}$ cycloalkyl, $C_{6-10}$ aryl, $C_{1-6}$ alkyl-$C_{6-10}$ aryl, heterocycloalkyl, $C_{1-6}$ alkyl-(heterocycloalkyl), heteroaryl, or $C_{1-6}$ alkyl-(heteroaryl), wherein the cycloalkyl, aryl, heterocycloalkyl, or heteroaryl is optionally substituted with 1 to 3 $R^{6n}$;

each $R^{6n}$ is $C_{1-6}$ alkyl, $C_{2-6}$ alkenyl, $C_{2-6}$ alkynyl, $C_{1-6}$ hydroxyalkyl, $C_{1-6}$ aminoalkyl, $C_{1-6}$ alkoxy, $C_{2-6}$ alkoxyalkyl, halogen, $C_{1-6}$ haloalkyl, $C_{1-6}$ haloalkoxy, —CN, —C(O)$R^{6n1}$, —C(O)O$R^{6n1}$, —OC(O)$R^{6n1}$, —C(O)N($R^{6n1}$)($R^{6n2}$), —N($R^{6n1}$)C(O)$R^{6n2}$, —OC(O)N($R^{6n1}$)($R^{6n2}$), —N($R^{6n1}$)C(O)O$R^{6n2}$, —C(=N$R^{6n1}$)N($R^{6n2}$)($R^{6n3}$), —N($R^{6n1}$)($R^{6n2}$), =O, —OH, —S$R^{6n1}$, —S(O)$R^{6n1}$, —S(N$R^{6n1}$)(N$R^{6n2}$)$R^{6n3}$, —S(O)(N$R^{6n1}$)($R^{6n2}$), —S(O)$_2R^{6n1}$, —S(O)$_2$N($R^{6n1}$)($R^{6n2}$), or —N($R^{6n1}$)S(O)$_2$($R^{6n2}$);

each $R^{6n1}$, $R^{6n2}$ and $R^{6n3}$ is independently hydrogen, $C_{1-6}$ alkyl, $C_{1-6}$ hydroxyalkyl, $C_{1-6}$ aminoalkyl, $C_{2-6}$ alkoxyalkyl, $C_{1-6}$ haloalkyl, $C_{3-10}$ cycloalkyl, $C_{1-6}$ alkyl-$C_{3-10}$ cycloalkyl, $C_{6-10}$ aryl, $C_{1-6}$ alkyl-$C_{6-10}$ aryl, heterocycloalkyl, $C_{1-6}$ alkyl-(heterocycloalkyl), heteroaryl, or $C_{1-6}$ alkyl-(heteroaryl);

each $R^{6h}$ is independently $C_{1-6}$ alkyl, $C_{2-6}$ alkenyl, $C_{2-6}$ alkynyl, $C_{1-6}$ hydroxyalkyl, $C_{1-6}$ aminoalkyl, $C_{1-6}$ alkoxy, $C_{2-6}$ alkoxyalkyl, halogen, $C_{1-6}$ haloalkyl, $C_{1-6}$ haloalkoxy, —CN, —C(O)$R^{6h1}$, —C(O)O$R^{6h1}$, —OC(O)$R^{6h1}$, —C(O)N($R^{6h1}$)($R^{6h2}$), —N($R^{6h1}$)C(O)$R^{6h2}$, —OC(O)N($R^{6h1}$)($R^{6h2}$), —N($R^{6h1}$)C(O)O$R^{6h2}$, —C(=N$R^{6h1}$)N($R^{6h2}$)($R^{6h3}$), —N($R^{6h1}$)($R^{6h2}$), =O, —OH, —S$R^{6h1}$, —S(O)$R^{6h1}$, —S(N$R^{6h1}$)(N$R^{6h2}$)$R^{6h3}$, —S(O)(N$R^{6h1}$)($R^{6h2}$), —S(O)$_2R^{6h1}$, —S(O)$_2$N($R^{6h1}$)($R^{6h2}$), —N($R^{6h1}$)S(O)$_2$($R^{6h2}$), $C_{3-10}$ cycloalkyl, $C_{1-6}$ alkyl-$C_{3-10}$ cycloalkyl, heterocycloalkyl, or $C_{1-6}$ alkyl-(heterocycloalkyl);

each $R^{6h1}$, $R^{6h2}$, and $R^{6h3}$ is independently hydrogen, $C_{1-6}$ alkyl, $C_{1-6}$ hydroxyalkyl, $C_{1-6}$ aminoalkyl, $C_{2-6}$ alkoxyalkyl, $C_{1-6}$ haloalkyl, $C_{3-10}$ cycloalkyl, $C_{1-6}$ alkyl-$C_{3-10}$ cycloalkyl, $C_{6-10}$ aryl, $C_{1-6}$ alkyl-$C_{6-10}$ aryl, heterocycloalkyl, $C_{1-6}$ alkyl-(heterocycloalkyl), heteroaryl, or $C_{1-6}$ alkyl-(heteroaryl);

each $R^{6m}$ is independently halogen, $C_{1-6}$ haloalkyl, $C_{1-6}$ haloalkoxy, —CN, —C(O)$R^{6m1}$, —C(O)O$R^{6m1}$, —OC(O)$R^{6m1}$, —C(O)N($R^{6m1}$)($R^{6m2}$), —N($R^{6m3}$)C(O)$R^{6m2}$, —OC(O)N($R^{6m1}$)($R^{6m2}$), —N($R^{6m1}$)C(O)O$R^{6m2}$, —C(=N$R^{6m3}$)N($R^{6m1}$)($R^{6m2}$), —N($R^{6m1}$)($R^{6m2}$), =O, —OH, —S$R^{6m1}$, —S(O)$R^{6m1}$, —S(N$R^{6m1}$)(N$R^{6m2}$)$R^{6m3}$, —S(O)(N$R^{6m1}$)($R^{6m2}$), —S(O)$_2R^{6m1}$, —S(O)$_2$N($R^{6m1}$)($R^{6m2}$), or —N($R^{6m3}$)S(O)$_2$($R^{6m2}$);

each $R^{6m1}$, $R^{6m2}$, and $R^{6m3}$ is independently hydrogen, $C_{1-6}$ alkyl, $C_{1-6}$ hydroxyalkyl, $C_{1-6}$ aminoalkyl, $C_{2-6}$ alkoxyalkyl, $C_{1-6}$ haloalkyl, $C_{3-10}$ cycloalkyl, $C_{1-6}$ alkyl-$C_{3-10}$ cycloalkyl, $C_{6-10}$ aryl, $C_{1-6}$ alkyl-$C_{6-10}$ aryl, heterocycloalkyl, $C_{1-6}$ alkyl-(heterocycloalkyl), heteroaryl, or $C_{1-6}$ alkyl-(heteroaryl);

$R^{6f}$ is —OSi($R^{6f1}$)($R^{6f2}$)($R^{6f3}$);

$R^{6f1}$, $R^{6f2}$, and $R^{6f3}$ are each independently $C_{1-6}$ alkyl;

each $R^{6j}$ is independently $C_{2-6}$ alkoxyalkyl, halogen, $C_{1-6}$ haloalkyl, $C_{1-6}$ haloalkoxy, —CN, —C(O)$R^{6j1}$, —C(O)O$R^{6j1}$, —OC(O)$R^{6j1}$, —C(O)N($R^{6j1}$)($R^{6j2}$), —N($R^{6j3}$)

C(O)R$^{6j2}$, —OC(O)N(R$^{6j1}$)(R$^{6j2}$), —N(R$^{6j1}$)C(O)OR$^{6j2}$, —C(=NR$^{6j3}$)N(R$^{6j1}$)(R$^{6j2}$), —N(R$^{6j1}$)(R$^{6j2}$), =O, —OR$^{6j}$, —SR$^{6j1}$, —S(O)R$^{6j1}$, —S(NR$^{6j1}$)(NR$^{6j2}$), —S(NR$^{6j1}$)(NR$^{6j2}$)R$^{6j3}$, —S(O)(NR$^{6j1}$)(R$^{6j2}$), —S(O)$_2$R$^{6j1}$, —S(O)$_2$N(R$^{6j1}$)(R$^{6j2}$), —N(R$^{6j1}$)S(O)$_2$(R$^{6j2}$), —Si(R$^{6j1}$)(R$^{6j2}$)(R$^{6j3}$), C$_{3-10}$ cycloalkyl, C$_{6-12}$ aryl, heterocycloalkyl, or heteroaryl, wherein the cycloalkyl, aryl, heterocycloalkyl, or heteroaryl is optionally substituted with 1 to 3 R$^{6p}$;

each R$^{6j1}$, R$^{6j2}$, and R$^{6j3}$ is independently hydrogen, C$_{1-6}$ alkyl, C$_{1-6}$ hydroxyalkyl, C$_{1-6}$ aminoalkyl, C$_{2-6}$ alkoxyalkyl, C$_{1-6}$ haloalkyl, C$_{3-10}$ cycloalkyl, C$_{1-6}$ alkyl-C$_{3-10}$ cycloalkyl, C$_{6-10}$ aryl, C$_{1-6}$ alkyl-C$_{6-10}$ aryl, heterocycloalkyl, C$_{1-6}$ alkyl-(heterocycloalkyl), heteroaryl, or C$_{1-6}$ alkyl-(heteroaryl);

each R$^{6p}$ is independently C$_{1-6}$ alkyl, C$_{1-6}$ hydroxyalkyl, C$_{1-6}$ aminoalkyl, C$_{1-6}$ alkoxy, C$_{2-6}$ alkoxyalkyl, halogen, C$_{1-6}$ haloalkyl, C$_{1-6}$ haloalkoxy, —CN, —C(O)R$^{6p1}$, —C(O)OR$^{6p1}$, —OC(O)R$^{6p1}$, —C(O)N(R$^{6p1}$)(R$^{6p2}$), —N(R$^{6p1}$)C(O)R$^{6p2}$, —OC(O)N(R$^{6p1}$)(R$^{6p2}$), —N(R$^{6p1}$)C(O)OR$^{6p2}$, —C(=NR$^{6p3}$)N(R$^{6p1}$)(R$^{6p2}$), —N(R$^{6p1}$)(R$^{6p2}$), =O, —OH, —SR$^{6p1}$, —S(O)R$^{6p1}$, —S(NR$^{6p1}$)(NR$^{6p2}$)R$^{6p3}$, —S(O)(NR$^{6p1}$)(R$^{6p2}$), —S(O)$_2$R$^{6p1}$, —S(O)$_2$N(R$^{6p1}$)(R$^{6p2}$), or —N(R$^{6p1}$)S(O)$_2$(R$^{6p2}$);

each R$^{6p1}$, R$^{6p2}$, and R$^{6p3}$ is independently hydrogen, C$_{1-6}$ alkyl, C$_{1-6}$ hydroxyalkyl, C$_{1-6}$ aminoalkyl, C$_{2-6}$ alkoxyalkyl, C$_{1-6}$ haloalkyl, C$_{3-10}$ cycloalkyl, C$_{1-6}$ alkyl-C$_{3-10}$ cycloalkyl, C$_{6-10}$ aryl, C$_{1-6}$ alkyl-C$_{6-10}$ aryl, heterocycloalkyl, C$_{1-6}$ alkyl-(heterocycloalkyl), heteroaryl, or C$_{1-6}$ alkyl-(heteroaryl);

or R$^5$ and one R$^{6a}$ together with the atoms to which they are attached form a heterocycloalkyl, optionally substituted with 1 to 3 R$^{6g}$;

each R$^{6g}$ is independently C$_{1-6}$ alkyl, C$_{2-6}$ alkenyl, C$_{2-6}$ alkynyl, C$_{1-6}$ hydroxyalkyl, C$_{1-6}$ aminoalkyl, C$_{2-6}$ alkoxyalkyl, halogen, C$_{1-6}$ haloalkyl, C$_{1-6}$ haloalkoxy, or —CN;

R$^7$ is hydrogen, C$_{1-6}$ alkyl, C$_{1-6}$ hydroxyalkyl, C$_{1-6}$ aminoalkyl, C$_{1-6}$ alkoxy, C$_{2-6}$ alkoxyalkyl, C$_{1-6}$ alkylthio, halogen, C$_{1-6}$ haloalkyl, —CN, —OH, —NH$_2$, C$_{3-10}$ cycloalkyl, C$_{1-6}$ alkyl-C$_{3-10}$ cycloalkyl, heterocycloalkyl, or C$_{1-6}$ alkyl-(heterocycloalkyl);

each heterocycloalkyl is a 3 to 20 membered ring having 1 to 4 heteroatoms each independently N, O or S; and each heteroaryl is a 5 to 18 membered ring having 1 to 4 heteroatoms each independently N, O or S;

provided that R$^5$ and R$^6$ are not both C$_{1-4}$ alkyl; and when R$^5$ is hydrogen, R$^6$ is not isopropyl or phenyl substituted with 2-Me.

In another embodiment, the present disclosure provides a pharmaceutical composition comprises a pharmaceutically effective amount of a compound of the present disclosure, or a pharmaceutically acceptable salt thereof, and a pharmaceutically acceptable carrier or excipient.

In another embodiment, the present disclosure provides a method of inhibiting DGKα in a subject in need thereof comprises administering to the subject a therapeutically effective amount of a compound of the present disclosure, or a pharmaceutically acceptable salt thereof, or a pharmaceutical composition of the present disclosure.

In another embodiment, the present disclosure provides a method of inhibiting DGKα in a subject in need thereof comprises administering to the subject a therapeutically effective amount of a compound of Formula (I):

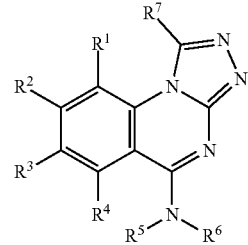

(I)

or a pharmaceutically acceptable salt thereof, wherein

R$^1$ is hydrogen, C$_{1-6}$ alkyl, C$_{2-6}$ alkenyl, C$_{2-6}$ alkynyl, C$_{1-6}$ alkoxy, halogen, C$_{1-6}$ haloalkyl, C$_{1-6}$ haloalkoxy, or —CN;

R$^2$ is hydrogen, C$_{1-6}$ alkyl, C$_{2-6}$ alkenyl, C$_{2-6}$ alkynyl, C$_{1-6}$ hydroxyalkyl, C$_{1-6}$ aminoalkyl, C$_{1-6}$ alkoxy, C$_{2-6}$ alkoxyalkyl, halogen, C$_{1-6}$ haloalkyl, C$_{1-6}$ haloalkoxy, —CN, —NO, —NO$_2$, —C(O)R$^{2a}$, —C(O)OR$^{2a}$, —OC(O)R$^{2a}$, —C(O)N(R$^{2a}$)(R$^{2b}$), —N(R$^{2a}$)C(O)R$^{2b}$, —OC(O)N(R$^{2a}$)(R$^{2b}$), —N(R$^{2a}$)C(O)OR$^{2b}$, —C(=NR$^{2a}$)N(R$^{2b}$)(R$^{2c}$), —N(R$^{2a}$)(R$^{2b}$), —N(R$^{2a}$)N(R$^{2b}$)(R$^{2c}$), —N(R$^{2a}$)N=C(R$^{2b}$)(OR$^{2c}$), —OR$^{2a}$, —SR$^{2a}$, —S(O)R$^{2a}$, —S(O)(NR$^{2a}$)(R$^{2b}$), —S(NR$^{2a}$)(NR$^{2b}$)(R$^{2c}$), —S(O)$_2$R$^{2a}$, —S(O)$_2$N(R$^{2a}$)(R$^{2b}$), —N(R$^{2a}$)S(O)$_2$(R$^{2b}$), —P(R$^{2a}$)(R$^{2b}$), —P(O)(R$^{2a}$)(R$^{2b}$), —P(O)(OR$^{2a}$)(R$^{2b}$), —P(O)(OR$^{2a}$)(OR$^{2b}$), C$_{3-10}$ cycloalkyl, C$_{1-6}$ alkyl-C$_{3-10}$ cycloalkyl, C$_{6-12}$ aryl, C$_{1-6}$ alkyl-C$_{6-12}$ aryl, heterocycloalkyl, C$_{1-6}$ alkyl-(heterocycloalkyl), heteroaryl, or C$_{1-6}$ alkyl-(heteroaryl), wherein each alkyl, alkenyl or alkynyl is independently optionally substituted with 1 to 3 R$^{2d}$ groups, each cycloalkyl is optionally substituted with 1 to 3 R$^{2e}$ groups, each aryl is optionally substituted with 1 to 3 R$^{2f}$ groups, each heterocycloalkyl is optionally substituted with 1 to 3 R$^{2g}$ groups, and each heteroaryl is optionally substituted with 1 to 3 R$^{2h}$ groups;

each R$^{2a}$, R$^{2b}$, and R$^{2c}$ is independently hydrogen, C$_{1-6}$ alkyl, C$_{2-6}$ alkenyl, C$_{2-6}$ alkynyl, C$_{1-6}$ hydroxyalkyl, C$_{1-6}$ aminoalkyl, C$_{2-6}$ alkoxyalkyl, C$_{1-6}$ haloalkyl, C$_{3-10}$ cycloalkyl, C$_{1-6}$ alkyl-C$_{3-10}$ cycloalkyl, C$_{6-12}$ aryl, C$_{1-6}$ alkyl-C$_{6-12}$ aryl, heterocycloalkyl, C$_{1-6}$ alkyl-(heterocycloalkyl), heteroaryl, or C$_{1-6}$ alkyl-(heteroaryl), wherein the aryl or heteroaryl is optionally substituted with 1 to 3 R$^{2j}$;

alternatively, R$^{2a}$, R$^{2b}$, and R$^{2c}$ when attached to the same atom can be combined with the atom to which they are attached to form a heterocycloalkyl;

each R$^{2d}$ is independently —CN, —C(O)R$^{2d1}$, —C(O)OR$^{2d1}$, —OC(O)R$^{2d1}$, —C(O)N(R$^{2d1}$)(R$^{2d2}$), —N(R$^{2d1}$)C(O)R$^{2d2}$, —OC(O)N(R$^{2d1}$)(R$^{2d2}$), —N(R$^{2d1}$)C(O)OR$^{2d2}$, —N(R$^{2d1}$)(R$^{2d2}$), =O, —OR$^{2d1}$, —SR$^{2d}$, —S(O)R$^{2d1}$, —S(O)(NR$^{2d1}$)(R$^{2d2}$), —S(O)$_2$R$^{2d1}$, —S(O)N(R$^{2d1}$)(R$^{2d2}$), —N(R$^{2d1}$)S(O)$_2$R$^{2d2}$, C$_{3-10}$ cycloalkyl, C$_{1-6}$ alkyl-C$_{3-10}$ cycloalkyl, C$_{6-12}$ aryl, C$_{1-6}$ alkyl-C$_{6-12}$ aryl, heterocycloalkyl, C$_{1-6}$ alkyl-(heterocycloalkyl), heteroaryl, or C$_{1-6}$ alkyl-(heteroaryl);

each R$^{2d1}$ and R$^{2d2}$ is independently hydrogen, C$_{1-6}$ alkyl, C$_{1-6}$ hydroxyalkyl, C$_{1-6}$ aminoalkyl, C$_{2-6}$ alkoxyalkyl, or C$_{1-6}$ haloalkyl;

each R$^{2e}$, R$^{2f}$, R$^{2g}$, and R$^{2h}$ is independently hydrogen, C$_{1-6}$ alkyl, C$_{1-6}$ hydroxyalkyl, C$_{1-6}$ aminoalkyl, C$_{1-6}$ alkoxy, C$_{2-6}$ alkoxyalkyl, halogen, C$_{1-6}$ haloalkyl, C$_{1-6}$ haloalkoxy, —CN, or —OH;

each $R^{2j}$ is independently $C_{1-6}$ alkyl, $C_{1-6}$ hydroxyalkyl, $C_{1-6}$ aminoalkyl, $C_{1-6}$ alkoxy, $C_{2-6}$ alkoxyalkyl, halogen, $C_{1-6}$ haloalkyl, or $C_{1-6}$ haloalkoxy;

$R^3$ is hydrogen, $C_{1-6}$ alkyl, $C_{2-6}$ alkenyl, $C_{2-6}$ alkynyl, $C_{1-6}$ hydroxyalkyl, $C_{1-6}$ aminoalkyl, $C_{1-6}$ alkoxy, $C_{2-6}$ alkoxyalkyl, halogen, $C_{1-6}$ haloalkyl, $C_{1-6}$ haloalkoxy, —CN, —NO, —NO$_2$, —C(O)R$^{3a}$, —C(O)OR$^{3a}$, —OC(O)R$^{3a}$, —C(O)N(R$^{3a}$)(R$^{3b}$), —N(R$^{3a}$)C(O)R$^{3b}$, —OC(O)N(R$^{3a}$)(R$^{3b}$), —N(R$^{3a}$)C(O)OR$^{3b}$, —C(=NR$^{3a}$)N(R$^{3b}$)(R$^{3c}$), —N(R$^{3a}$)(R$^{3b}$), —N(R$^{3a}$)N(R$^{3b}$)(R$^{3c}$), —N(R$^{3a}$)N=C(R$^{3b}$)(OR$^{3c}$), —OR$^{3a}$, —SR$^{3a}$, —S(O)R$^{3a}$, —S(O)(NR$^{3a}$)(R$^{3b}$), —S(NR$^{3a}$)(NR$^{3b}$)(R$^{3c}$), —S(O)$_2$R$^{3a}$, —S(O)$_2$N(R$^{3a}$)(R$^{3b}$), —N(R$^{3a}$)S(O)$_2$(R$^{3b}$), —P(R$^{3a}$)(R$^{3b}$), —P(O)(R$^{3a}$)(R$^{3b}$), —P(O)(OR$^{3a}$)(R$^{3b}$), —P(O)(OR$^{3a}$)(OR$^{3b}$), $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, $C_{1-6}$ alkyl-(heterocycloalkyl), heteroaryl, or $C_{1-6}$ alkyl-(heteroaryl), wherein each alkenyl or alkynyl is independently optionally substituted with 1 to 3 R$^{3d}$ groups, each cycloalkyl is optionally substituted with 1 to 3 R$^{3e}$ groups, each aryl is optionally substituted with 1 to 3 R$^{3f}$ groups, each heterocycloalkyl is optionally substituted with 1 to 3 R$^{3g}$ groups, and each heteroaryl is optionally substituted with 1 to 3 R$^{3h}$ groups;

each R$^{3a}$, R$^{3b}$, and R$^{3c}$ is independently hydrogen, $C_{1-6}$ alkyl, $C_{1-6}$ hydroxyalkyl, $C_{2-6}$ alkoxyalkyl, $C_{1-6}$ haloalkyl, $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, or heteroaryl;

alternatively, R$^{3a}$, R$^{3b}$, and R$^{3c}$ when attached to the same atom can be combined with the atom to which they are attached to form a heterocycloalkyl;

each R$^{3d}$ is independently —N(R$^{3d1}$)(R$^{3d2}$), —OR$^{3d1}$, $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, or heteroaryl;

each R$^{3d1}$ and R$^{3d2}$ is independently hydrogen, $C_{1-6}$ alkyl, or —C(O)O—($C_{1-6}$ alkyl);

each R$^{3e}$, R$^{3f}$, R$^{3g}$, and R$^{3h}$ is independently hydrogen, $C_{1-6}$ alkyl, $C_{1-6}$ alkoxy, halogen, $C_{1-6}$ haloalkyl or $C_{1-6}$ haloalkoxy;

R$^4$ is hydrogen, $C_{1-6}$ alkyl, $C_{2-6}$ alkenyl, $C_{2-6}$ alkynyl, $C_{1-6}$ alkoxy, halogen, $C_{1-6}$ haloalkyl, $C_{1-6}$ haloalkoxy, or —CN;

R$^5$ is hydrogen, $C_{1-6}$ alkyl, $C_{2-6}$ alkenyl, $C_{2-6}$ alkynyl, $C_{1-6}$ hydroxyalkyl, $C_{2-6}$ alkoxyalkyl, $C_{1-6}$ haloalkyl, $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, $C_{1-6}$ alkyl-(heterocycloalkyl), heteroaryl, or $C_{1-6}$ alkyl-(heteroaryl), wherein the alkyl is optionally substituted with R$^{5a}$;

R$^{5a}$ is —OSi(R$^{5a1}$)(R$^{5a2}$)(R$^{5a3}$);

R$^{5a1}$, R$^{5a2}$, and R$^{5a3}$ are each independently $C_{1-6}$ alkyl; and

R$^6$ is $C_{1-6}$ alkyl, $C_{2-6}$ alkenyl, $C_{2-6}$ alkynyl, $C_{1-6}$ haloalkyl, $C_{6-12}$ aryl, or heteroaryl, wherein the aryl or heteroaryl are each optionally substituted with 1 to 3 R$^{6a}$;

each R$^{6a}$ is independently $C_{1-6}$ alkyl, $C_{2-6}$ alkenyl, $C_{2-6}$ alkynyl, $C_{1-6}$ hydroxyalkyl, $C_{1-6}$ aminoalkyl, $C_{1-6}$ alkoxy, $C_{2-6}$ alkoxyalkyl, halogen, $C_{1-6}$ haloalkyl, $C_{1-6}$ haloalkoxy, —CN, —NO$_2$, —C(O)R$^{6b}$, —C(O)OR$^{6b}$, —OC(O)R$^{6b}$, —C(O)N(R$^{6b}$)(R$^{6c}$), —N(R$^{6b}$)C(O)R$^{6c}$, —C(=NR$^{6b}$)N(R$^{6c}$)(R$^{6d}$), —N(R$^{6b}$)(R$^{6c}$), —OR$^{6b}$, —SR$^{6b}$, —S(O)R$^{6b}$, —S(O)$_2$R$^{6b}$, —S(NR$^{6b}$)(NR$^{6c}$)R$^{6d}$, —S(O)(NR$^{6b}$)(R$^{6c}$), —S(O)$_2$N(R$^{6b}$)(R$^{6c}$), —N(R$^{6b}$)S(O)$_2$(R$^{6c}$), —P(R$^{6b}$)(R$^{6c}$), —P(O)(R$^{6b}$)(R$^{6c}$), —P(O)(OR$^{6b}$)(R$^{6c}$), —P(O)(OR$^{6b}$)(OR$^{6c}$), $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, $C_{1-6}$ alkyl-(heterocycloalkyl), heteroaryl, or $C_{1-6}$ alkyl-(heteroaryl), wherein the cycloalkyl, aryl, heterocycloalkyl, or heteroaryl is each optionally substituted with 1 to 3 R$^{6e}$, the alkyl is optionally substituted with R$^{6f}$, and the alkynyl is optionally substituted with 1 to 4 R$^{6j}$;

each R$^{6b}$, R$^{6c}$ and R$^{6d}$ is independently hydrogen, $C_{1-6}$ alkyl, $C_{1-6}$ hydroxyalkyl, $C_{1-6}$ aminoalkyl, $C_{2-6}$ alkoxyalkyl, $C_{1-6}$ haloalkyl, $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, $C_{1-6}$ alkyl-(heterocycloalkyl), heteroaryl, or $C_{1-6}$ alkyl-(heteroaryl), wherein the cycloalkyl, aryl, heterocycloalkyl, or heteroaryl is optionally substituted by 1 to 3 R$^{6k}$;

each R$^{6k}$ is independently $C_{1-6}$ alkyl, $C_{1-6}$ hydroxyalkyl, $C_{1-6}$ aminoalkyl, $C_{1-6}$ alkoxy, $C_{2-6}$ alkoxyalkyl, $C_{1-6}$ haloalkyl, $C_{1-6}$ haloalkoxy, $C_{3-10}$ cycloalkyl, $C_{1-6}$ alkyl-$C_{3-10}$ cycloalkyl, heterocycloalkyl, or $C_{1-6}$ alkyl-(heterocycloalkyl);

each R$^{6e}$ is independently $C_{1-6}$ alkyl, $C_{2-6}$ alkenyl, $C_{2-6}$ alkynyl, $C_{1-6}$ hydroxyalkyl, $C_{1-6}$ aminoalkyl, $C_{1-6}$ alkoxy, $C_{2-6}$ alkoxyalkyl, halogen, $C_{1-6}$ haloalkyl, $C_{1-6}$ haloalkoxy, —CN, —NO$_2$, —C(O)R$^{6e1}$, —C(O)OR$^{6e1}$, —OC(O)R$^{6e1}$, —C(O)N(R$^{6e1}$)(R$^{6e2}$), —N(R$^{6e1}$)C(O)R$^{6e2}$, —OC(O)N(R$^{6e1}$)(R$^{6e2}$), —N(R$^{6e1}$)C(O)OR$^{6e2}$, —C(=NR$^{6e1}$)N(R$^{6e2}$)(R$^{6e3}$), —N(R$^{6e1}$)(R$^{6e2}$), =O, —OR$^{6e1}$, —SR$^{6e1}$, —S(O)R$^{6e1}$, —S(NR$^{6e1}$)(NR$^{6e2}$), —S(O)(NR$^{6e1}$)(R$^{6e2}$), —S(O)$_2$R$^{6e1}$, —S(O)$_2$N(R$^{6e1}$)(R$^{6e2}$), —SF$_5$, —N(R$^{6e1}$)S(O)$_2$(R$^{6e2}$), —P(R$^{6e1}$)(R$^{6e2}$), —P(O)(R$^{6e1}$)(R$^{6e2}$), —P(O)(OR$^{6e1}$)(R$^{6e2}$), —P(O)(OR$^{6e1}$)(OR$^{6e2}$), —Si(R$^{6e1}$)(R$^{6e2}$)(R$^{6e3}$), $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, $C_{1-6}$ alkyl-heterocycloalkyl, heteroaryl, or $C_{1-6}$ alkyl-heteroaryl, wherein the cycloalkyl, aryl, heterocycloalkyl, or heteroaryl is each optionally substituted with 1 to 3 R$^{6h}$, and the alkyl is optionally substituted with 1 to 3 R$^{6m}$;

each R$^{6e1}$, R$^{6e2}$, and R$^{6e3}$ is independently hydrogen, $C_{1-6}$ alkyl, $C_{1-6}$ hydroxyalkyl, $C_{1-6}$ aminoalkyl, $C_{1-6}$ alkoxyalkyl, $C_{1-6}$ haloalkyl, $C_{3-10}$ cycloalkyl, $C_{1-6}$ alkyl-$C_{3-10}$ cycloalkyl, $C_{6-10}$ aryl, $C_{1-6}$ alkyl-$C_{6-10}$ aryl, heterocycloalkyl, $C_{1-6}$ alkyl-(heterocycloalkyl), heteroaryl, or $C_{1-6}$ alkyl-(heteroaryl), wherein the cycloalkyl, aryl, heterocycloalkyl, or heteroaryl is optionally substituted with 1 to 3 R$^{6n}$;

each R$^{6n}$ is $C_{1-6}$ alkyl, $C_{2-6}$ alkenyl, $C_{2-6}$ alkynyl, $C_{1-6}$ hydroxyalkyl, $C_{1-6}$ aminoalkyl, $C_{1-6}$ alkoxy, $C_{2-6}$ alkoxyalkyl, halogen, $C_{1-6}$ haloalkyl, $C_{1-6}$ haloalkoxy, —CN, —C(O)R$^{6n1}$, —C(O)OR$^{6n1}$, —OC(O)R$^{6n1}$, —C(O)N(R$^{6n1}$)(R$^{6n2}$), —N(R$^{6n1}$)C(O)R$^{6n2}$, —OC(O)N(R$^{6n1}$)(R$^{6n2}$), —N(R$^{6n1}$)C(O)OR$^{6n2}$, —C(=NR$^{6n1}$)N(R$^{6n2}$)(R$^{6n3}$), —N(R$^{6n1}$)(R$^{6n2}$), =O, —OH, —SR$^{6n1}$, —S(O)R$^{6n1}$, —S(NR$^{6n1}$)(NR$^{6n2}$)R$^{6n3}$, —S(O)(NR$^{6n1}$)(R$^{6n2}$), —S(O)$_2$R$^{6n1}$, —S(O)$_2$N(R$^{6n1}$)(R$^{6n2}$), or —N(R$^{6n1}$)S(O)$_2$(R$^{6n2}$);

each R$^{6n1}$, R$^{6n2}$ and R$^{6n3}$ is independently hydrogen, $C_{1-6}$ alkyl, $C_{1-6}$ hydroxyalkyl, $C_{1-6}$ aminoalkyl, $C_{2-6}$ alkoxyalkyl, $C_{1-6}$ haloalkyl, $C_{3-10}$ cycloalkyl, $C_{1-6}$ alkyl-$C_{3-10}$ cycloalkyl, $C_{6-10}$ aryl, $C_{1-6}$ alkyl-$C_{6-10}$ aryl, heterocycloalkyl, $C_{1-6}$ alkyl-(heterocycloalkyl), heteroaryl, or $C_{1-6}$ alkyl-(heteroaryl);

each R$^{6h}$ is independently $C_{1-6}$ alkyl, $C_{2-6}$ alkenyl, $C_{2-6}$ alkynyl, $C_{1-6}$ hydroxyalkyl, $C_{1-6}$ aminoalkyl, $C_{1-6}$ alkoxy, $C_{2-6}$ alkoxyalkyl, halogen, $C_{1-6}$ haloalkyl, $C_{1-6}$ haloalkoxy, —CN, —C(O)R$^{6h1}$, —C(O)OR$^{6h1}$, —OC(O)R$^{6h1}$, —C(O)N(R$^{6h1}$)(R$^{6h2}$), —N(R$^{6h1}$)C(O)R$^{6h2}$, —OC(O)N($R^{6h1}$)($R^{6h2}$), —N($R^{6h1}$)C(O)O$R^{6h2}$, —C(=N$R^{6h1}$)N($R^{6h2}$)($R^{6h3}$), —N($R^{6h1}$)($R^{6h2}$), =O, —OH, —S$R^{6h1}$, —S(O)$R^{6h1}$, —S(N$R^{6h1}$)(N$R^{6h2}$)$R^{6h3}$, —S(O)(N$R^{6h1}$)($R^{6h2}$), —S(O)$_2$$R^{6h1}$, —S(O)$_2$N($R^{6h1}$)($R^6$), —N($R^{6h1}$)S(O)$_2$($R^{6h1}$), $C_{3-10}$ cycloalkyl, $C_{1-6}$ alkyl-$C_{3-10}$ cycloalkyl, heterocycloalkyl, or $C_{1-6}$ alkyl-(heterocycloalkyl);

each $R^{6h1}$, $R^{6h2}$, and $R^{6h3}$ is independently hydrogen, $C_{1-6}$ alkyl, $C_{1-6}$ hydroxyalkyl, $C_{1-6}$ aminoalkyl, $C_{2-6}$ alkoxyalkyl, $C_{1-6}$ haloalkyl, $C_{3-10}$ cycloalkyl, $C_{1-6}$ alkyl-$C_{3-10}$ cycloalkyl, $C_{6-10}$ aryl, $C_{1-6}$ alkyl-$C_{6-10}$ aryl, heterocycloalkyl, $C_{1-6}$ alkyl-(heterocycloalkyl), heteroaryl, or $C_{1-6}$ alkyl-(heteroaryl);

each $R^{6m}$ is independently halogen, $C_{1-6}$ haloalkyl, $C_{1-6}$ haloalkoxy, —CN, —C(O)$R^{6m1}$, —C(O)O$R^{6m1}$, —OC(O)$R^{6m1}$, —C(O)N($R^{6m1}$)($R^{6m2}$), —N($R^{6m3}$)C(O)$R^{6m2}$, —OC(O)N($R^{6m1}$)($R^{6m2}$), —N($R^{6m1}$)C(O)O$R^{6m2}$, —C(=N$R^{6m3}$)N($R^{6m1}$)($R^{6m2}$), —N($R^{6m1}$)($R^{6m2}$), =O, —OH, —S$R^{6m1}$, —S(O)$R^{6m1}$, —S(N$R^{6m1}$)(N$R^{6m2}$)$R^{6m3}$, —S(O)(N$R^{6m1}$)($R^{6m2}$), —S(O)$_2$$R^{6m1}$, —S(O)$_2$N($R^{6m1}$)($R^{6m2}$), or —N($R^{6m3}$)S(O)$_2$($R^{6m2}$);

each $R^{6m1}$, $R^{6m2}$, and $R^{6m3}$ is independently hydrogen, $C_{1-6}$ alkyl, $C_{1-6}$ hydroxyalkyl, $C_{1-6}$ aminoalkyl, $C_{2-6}$ alkoxyalkyl, $C_{1-6}$ haloalkyl, $C_{3-10}$ cycloalkyl, $C_{1-6}$ alkyl-$C_{3-10}$ cycloalkyl, $C_{6-10}$ aryl, $C_{1-6}$ alkyl-$C_{6-10}$ aryl, heterocycloalkyl, $C_{1-6}$ alkyl-(heterocycloalkyl), heteroaryl, or $C_{1-6}$ alkyl-(heteroaryl);

$R^{6f}$ is —OSi($R^{6f1}$)($R^{6f2}$)($R^{6f3}$);

$R^{6f1}$, $R^{6f2}$, and $R^{6f3}$ are each independently $C_{1-6}$ alkyl;

each $R^{6j}$ is independently $C_{2-6}$ alkoxyalkyl, halogen, $C_{1-6}$ haloalkyl, $C_{1-6}$ haloalkoxy, —CN, —C(O)$R^{6j1}$, —C(O)O$R^{6j1}$, —OC(O)$R^{6j1}$, —C(O)N($R^{6j1}$)($R^{6j2}$), —N($R^{6j3}$)C(O)$R^{6j2}$, —OC(O)N($R^{6j1}$)($R^{6j2}$), —N($R^{6j1}$)C(O)O$R^{6j2}$, —C(=N$R^{6j3}$)N($R^{6j1}$)($R^{6j2}$), —N($R^{6j1}$)($R^{6j2}$), =O, —O$R^{6j1}$, —S$R^{6j1}$, —S(O)$R^{6j1}$, —S(N$R^{6j1}$)(N$R^{6j2}$), —S(N$R^{6j1}$)(N$R^{6j2}$)$R^{6j3}$, —S(O)(N$R^{6j1}$)($R^{6j2}$), —S(O)$_2$$R^{6j1}$, —S(O)$_2$N($R^{6j1}$)($R^{6j2}$), —N($R^{6j1}$)S(O)$_2$($R^{6j2}$), —Si($R^{6j1}$)($R^{6j2}$)($R^{6j3}$), $C_{3-10}$ cycloalkyl, $C_{6-12}$ aryl, heterocycloalkyl, or heteroaryl, wherein the cycloalkyl, aryl, heterocycloalkyl, or heteroaryl is optionally substituted with 1 to 3 $R^{6p}$;

each $R^{6j1}$, $R^{6j2}$, and $R^{6j3}$ is independently hydrogen, $C_{1-6}$ alkyl, $C_{1-6}$ hydroxyalkyl, $C_{1-6}$ aminoalkyl, $C_{2-6}$ alkoxyalkyl, $C_{1-6}$ haloalkyl, $C_{3-10}$ cycloalkyl, $C_{1-6}$ alkyl-$C_{3-10}$ cycloalkyl, $C_{6-10}$ aryl, $C_{1-6}$ alkyl-$C_{6-10}$ aryl, heterocycloalkyl, $C_{1-6}$ alkyl-(heterocycloalkyl), heteroaryl, or $C_{1-6}$ alkyl-(heteroaryl);

each $R^{6p}$ is independently $C_{1-6}$ alkyl, $C_{1-6}$ hydroxyalkyl, $C_{1-6}$ aminoalkyl, $C_{1-6}$ alkoxy, $C_{2-6}$ alkoxyalkyl, halogen, $C_{1-6}$ haloalkyl, $C_{1-6}$ haloalkoxy, —CN, —C(O)$R^{6p1}$, —C(O)O$R^{6p1}$, —OC(O)$R^{6p1}$, —C(O)N($R^{6p1}$)($R^{6p2}$), —N($R^{6p1}$)C(O)$R^{6p2}$, —OC(O)N($R^{6p1}$)($R^{6p2}$), —N($R^{6p1}$)C(O)O$R^{6p2}$, —C(=N$R^{6p3}$)N($R^{6p1}$)($R^{6p2}$), —N($R^{6p1}$)($R^{6p2}$), =O, —OH, —S$R^{6p1}$, —S(O)$R^{6p1}$, —S(N$R^{6p1}$)(N$R^{6p2}$)$R^{6p3}$, —S(O)(N$R^{6p1}$)($R^{6p2}$), —S(O)$_2$$R^{6p1}$, —S(O)$_2$N($R^{6p1}$)($R^{6p2}$), or —N($R^{6p1}$)S(O)$_2$($R^{6p2}$);

each $R^{6p1}$, $R^{6p2}$, and $R^{6p3}$ is independently hydrogen, $C_{1-6}$ alkyl, $C_{1-6}$ hydroxyalkyl, $C_{1-6}$ aminoalkyl, $C_{2-6}$ alkoxyalkyl, $C_{1-6}$ haloalkyl, $C_{3-10}$ cycloalkyl, $C_{1-6}$ alkyl-$C_{3-10}$ cycloalkyl, $C_{6-10}$ aryl, $C_{1-6}$ alkyl-$C_{6-10}$ aryl, heterocycloalkyl, $C_{1-6}$ alkyl-(heterocycloalkyl), heteroaryl, or $C_{1-6}$ alkyl-(heteroaryl);

or $R^5$ and one $R^{6a}$ together with the atoms to which they are attached form a heterocycloalkyl, optionally substituted with 1 to 3 $R^{6g}$;

each $R^{6g}$ is independently $C_{1-6}$ alkyl, $C_{2-6}$ alkenyl, $C_{2-6}$ alkynyl, $C_{1-6}$ hydroxyalkyl, $C_{1-6}$ aminoalkyl, $C_{2-6}$ alkoxyalkyl, halogen, $C_{1-6}$ haloalkyl, $C_{1-6}$ haloalkoxy, or —CN;

$R^7$ is hydrogen, $C_{1-6}$ alkyl, $C_{1-6}$ hydroxyalkyl, $C_{1-6}$ aminoalkyl, $C_{1-6}$ alkoxy, $C_{2-6}$ alkoxyalkyl, $C_{1-6}$ alkylthio, halogen, $C_{1-6}$ haloalkyl, —CN, —OH, —NH$_2$, $C_{3-10}$ cycloalkyl, $C_{1-6}$ alkyl-$C_{3-10}$ cycloalkyl, heterocycloalkyl, or $C_{1-6}$ alkyl-(heterocycloalkyl);

each heterocycloalkyl is a 3 to 20 membered ring having 1 to 4 heteroatoms each independently N, O or S; and each heteroaryl is a 5 to 18 membered ring having 1 to 4 heteroatoms each independently N, O or S.

In another embodiment, the present disclosure provides a method of treating cancer in a subject in need thereof comprises administering to the subject a therapeutically effective amount of a compound of the present disclosure, or a pharmaceutically acceptable salt thereof, or a pharmaceutical composition of the present disclosure.

In another embodiment, the present disclosure provides a method of treating an HIV or a hepatitis B virus infection in a subject in need thereof comprises administering to the subject a therapeutically effective amount of a compound of the present disclosure, or a pharmaceutically acceptable salt thereof, or a pharmaceutical composition of the present disclosure.

DETAILED DESCRIPTION

I. Definitions

"Alkyl" is a linear or branched saturated monovalent hydrocarbon. For example, an alkyl group can have 1 to 18 carbon atoms (i.e., $C_{1-18}$ alkyl) or 1 to 8 carbon atoms (i.e., $C_{1-8}$ alkyl) or 1 to 6 carbon atoms (i.e., $C_{1-6}$ alkyl) or 1 to 4 carbon atoms (i.e., $C_4$ alkyl). Examples of alkyl groups include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), and 3,3-dimethyl-2-butyl (—CH(CH$_3$)C(CH$_3$)$_3$. Other alkyl groups include heptyl, octyl, nonyl, decyl, undecyl, dodecyl, pentadcyl, hexadecyl, heptadecyl and octadecyl.

"Alkylene" refers to a straight or branched, saturated, aliphatic radical having the number of carbon atoms indicated, and linking at least two other groups, i.e., a divalent hydrocarbon radical. The two moieties linked to the alkylene can be linked to the same atom or different atoms of the alkylene group. For instance, a straight chain alkylene can be the bivalent radical of —(CH$_2$)$_n$—, where n is 1, 2, 3, 4, 5 or 6. Representative alkylene groups include, but are not limited to, methylene, ethylene, propylene, isopropylene, butylene, isobutylene, sec-butylene, pentylene and hexylene. Alkylene groups can be substituted or unsubstituted.

"Alkenyl" refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$.

Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can be substituted or unsubstituted.

"Alkynyl" refers to either a straight chain or branched hydrocarbon having at least 2 carbon atoms and at least one triple bond. Alkynyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$.

Examples of alkynyl groups include, but are not limited to, acetylenyl, propynyl, 1-butynyl, 2-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can be substituted or unsubstituted.

"Alkoxy" refers to an alkyl group having an oxygen atom that connects the alkyl group to the point of attachment: alkyl-O—. As for alkyl group, alkoxy groups can have any suitable number of carbon atoms, such as $C_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. Alkoxy groups can be substituted or unsubstituted.

"Alkoxyalkyl" refers an alkoxy group linked to an alkyl group which is linked to the remainder of the compound such that the alkyl group is divalent. Alkoxyalkyl can have any suitable number of carbon, such as from 2 to 6 ($C_{2-6}$ alkoxyalkyl), 2 to 5 ($C_{2-5}$ alkoxyalkyl), 2 to 4 ($C_{2-4}$ alkoxyalkyl), or 2 to 3 ($C_{2-3}$ alkoxyalkyl). The number of carbons refers to the total number of carbons in the alkoxy and the alkyl group. For example, $C_6$ alkoxyalkyl refers to ethoxy ($C_2$ alkoxy) linked to a butyl ($C_4$ alkyl), and n-propoxy ($C_3$ alkoxy) linked to a isopropyl ($C_3$ alkyl). Alkoxy and alkyl are as defined above where the alkyl is divalent, and can include, but is not limited to, methoxymethyl ($CH_3OCH_2$—), methoxyethyl ($CH_3OCH_2CH_2$—) and others.

"Aminoalkyl" refers to an amino group linked to an alkyl group which is linked to the remainder of the compound such that the alkyl group is divalent. The amino group may be unsubstituted amino (—$NH_2$) or substituted with an alkyl group, e.g., monosubstituted amino (e.g., —$NHCH_3$), or disubstituted amino (e.g., —$N(CH_3)_2$). Aminoalkyl can have any suitable number of carbons, such as from 1 to 8 ($C_{1-8}$ aminoalkyl), 1 to 6 ($C_{1-6}$ aminoalkyl), 2 to 6 ($C_{2-6}$ aminoalkyl), 2 to 4 ($C_{2-4}$ aminoalkyl), or 2 to 3 ($C_{2-3}$ aminoalkyl). The number of carbons refers to the total number of carbons in the amino and the alkyl group. For example, $C_6$ aminoalkyl refers to —$N(CH_3)_2$ ($C_2$ amino) linked to a butyl ($C_4$ alkyl), and —$NHCH_2CH_2CH_3$ ($C_3$ amino) linked to a isopropyl ($C_3$ alkyl). Alkyl is as defined above where the alkyl is divalent. Aminoalkyl can include, but is not limited to, aminomethyl ($H_2NCH_2$—), methylaminomethyl ($CH_3NHCH_2$—), dimethylaminomethyl (($CH_3)_2NCH_2$—), dimethylaminoethyl (($CH_3)_2NCH_2CH_2$—), and others.

"Alkoxy-alkoxy" refers an alkoxy group linked to a second alkoxy group which is linked to the remainder of the compound. Alkoxy is as defined above, and can include, but is not limited to, methoxy-methoxy ($CH_3OCH_2O$—), methoxy-ethoxy ($CH_3OCH_2CH_2O$—) and others.

"Halo" or "halogen" as used herein refers to fluoro (—F), chloro (—Cl), bromo (—Br) and iodo (—I).

"Haloalkyl" as used herein refers to an alkyl as defined herein, wherein one or more hydrogen atoms of the alkyl are independently replaced by a halo substituent, which may be the same or different. For example, $C_{1-4}$ haloalkyl is a $C_{1-4}$ alkyl wherein one or more of the hydrogen atoms of the $C_{1-4}$ alkyl have been replaced by a halo substituent. Examples of haloalkyl groups include but are not limited to fluoromethyl, fluorochloromethyl, difluoromethyl, difluorochloromethyl, trifluoromethyl, 1,1,1-trifluoroethyl and pentafluoroethyl.

"Haloalkoxy" refers to an alkoxy group where some or all of the hydrogen atoms are substituted with halogen atoms. As for an alkyl group, haloalkoxy groups can have any suitable number of carbon atoms, such as $C_{1-6}$. The alkoxy groups can be substituted with 1, 2, 3, or more halogens. When all the hydrogens are replaced with a halogen, for example by fluorine, the compounds are per-substituted, for example, perfluorinated. Haloalkoxy includes, but is not limited to, trifluoromethoxy, 2,2,2,-trifluoroethoxy, perfluoroethoxy, etc.

"Cycloalkyl" refers to a single saturated or partially unsaturated all carbon ring having 3 to 20 annular carbon atoms (i.e., $C_{3-20}$ cycloalkyl), for example from 3 to 12 annular atoms, for example from 3 to 10 annular atoms, or 3 to 8 annular atoms, or 3 to 6 annular atoms, or 3 to 5 annular atoms, or 3 to 4 annular atoms. The term "cycloalkyl" also includes multiple condensed, saturated and partially unsaturated all carbon ring systems (e.g., ring systems comprising 2, 3 or 4 carbocyclic rings). Accordingly, cycloalkyl includes multicyclic carbocyles such as a bicyclic carbocycles (e.g., bicyclic carbocycles having 6 to 12 annular carbon atoms such as bicyclo[3.1.0]hexane and bicyclo[2.1.1]hexane), and polycyclic carbocycles (e.g., tricyclic and tetracyclic carbocycles with up to 20 annular carbon atoms). The rings of a multiple condensed ring system can be connected to each other via fused, spiro and bridged bonds when allowed by valency requirements. Non-limiting examples of monocyclic cycloalkyl include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl and 1-cyclohex-3-enyl.

"Alkyl-cycloalkyl" refers to a radical having an alkyl component and a cycloalkyl component, where the alkyl component links the cycloalkyl component to the point of attachment. The alkyl component is as defined above, except that the alkyl component is at least divalent, an alkylene, to link to the cycloalkyl component and to the point of attachment. In some instances, the alkyl component can be absent. The alkyl component can include any number of carbons, such as $C_{1-6}$, $C_{1-2}$, $C_{1-3}$, $C_{1-4}$, $C_{1-5}$, $C_{2-3}$, $C_{2-5}$, $C_{2-6}$, $C_{3-4}$, $C_{3-5}$, $C_{3-6}$, $C_{4-5}$, $C_{4-6}$ and $C_{5-6}$. The cycloalkyl component is as defined within. Exemplary alkyl-cycloalkyl groups include, but are not limited to, methyl-cyclopropyl, methyl-cyclobutyl, methyl-cyclopentyl and methyl-cyclohexyl.

"Heterocyclyl" or "heterocycle" or "heterocycloalkyl" as used herein refers to a single saturated or partially unsaturated non-aromatic ring or a multiple ring system having at least one heteroatom in the ring (i.e., at least one annular heteroatom selected from oxygen, nitrogen, and sulfur)

wherein the multiple ring system includes at least non-aromatic ring containing at least one heteroatom. The multiple ring system can also include other aromatic rings and non-aromatic rings. Unless otherwise specified, a heterocyclyl group has from 3 to 20 annular atoms, for example from 3 to 12 annular atoms, for example from 3 to 10 annular atoms, or 3 to 8 annular atoms, or 3 to 6 annular atoms, or 3 to 5 annular atoms, or 4 to 6 annular atoms, or 4 to 5 annular atoms. Thus, the term includes single saturated or partially unsaturated rings (e.g., 3, 4, 5, 6 or 7-membered rings) having from 1 to 6 annular carbon atoms and from 1 to 3 annular heteroatoms selected from the group consisting of oxygen, nitrogen and sulfur in the ring. The heteroatoms can optionally be oxidized to form —N(—OH)—, =N(—O⁻)—, —S(=O)— or —S(=O)₂—. The rings of the multiple condensed ring (e.g. bicyclic heterocyclyl) system can be connected to each other via fused, spiro and bridged bonds when allowed by valency requirements. Heterocycles include, but are not limited to, azetidine, aziridine, imidazolidine, morpholine, oxirane (epoxide), oxetane, thietane, piperazine, piperidine, pyrazolidine, piperidine, pyrrolidine, pyrrolidinone, tetrahydrofuran, tetrahydrothiophene, dihydropyridine, tetrahydropyridine, quinuclidine, 2-oxa-6-azaspiro[3.3]heptan-6-yl, 6-oxa-1-azaspiro[3.3]heptan-1-yl, 2-thia-6-azaspiro[3.3]heptan-6-yl, 2,6-diazaspiro[3.3]heptan-2-yl, 2-azabicyclo[3.1.0]hexan-2-yl, 3-azabicyclo[3.1.0]hexanyl, 2-azabicyclo[2.1.1]hexanyl, 2-azabicyclo[2.2.1]heptan-2-yl, 4-azaspiro[2.4]heptanyl, 5-azaspiro[2.4]heptanyl, and the like.

Heterocycloalkyl rings also include 9 to 15 membered fused ring heterocycloalkyls having 2, 3, or more rings wherein at least one ring is an aryl ring and at least one ring is a non-aromatic ring containing at least one heteroatom. Representative fused bicyclic heterocycloalkyls include, but are not limited to, indoline (dihydroindole), isoindoline (dihydroisoindole), indazoline (dihydroindazole), benzo[d]imidazole, dihydroquinoline, dihydroisoquinoline, dihydrobenzofuran, dihydroisobenzofuran, benzo[d][1,3]dioxol, dihydrobenzo[b]dioxine, dihydrobenzo[d]oxazole, dihydrobenzo[b]thiophene, dihydroisobenzo[c]thiophene, dihydrobenzo[d]thiazole, dihydrobenzo[c]isothiazole, and benzo[b][1,4]thiazine, as shown in the structures below:

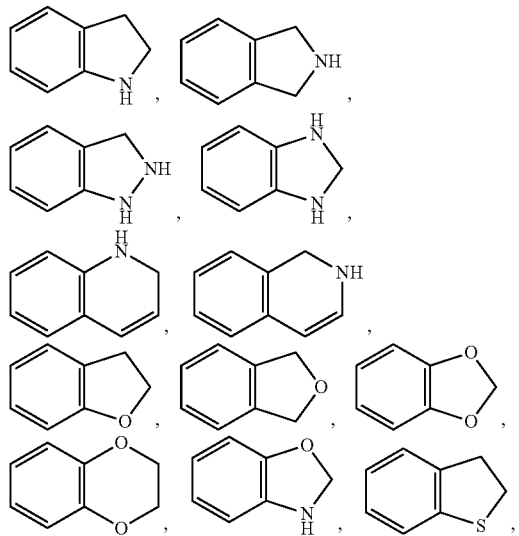

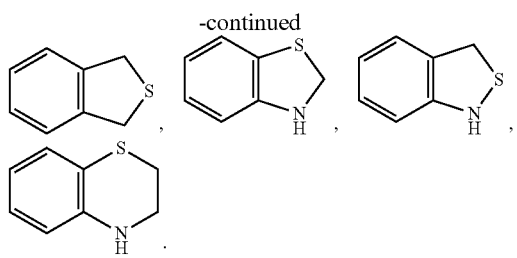

Fused bicyclic heterocycloalkyls can also be represented by the following structure:

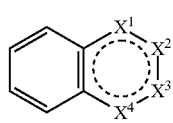

wherein $X^1$, $X^2$, $X^3$ and $X^4$ are each independently absent, —CH₂—, —NH—, —O— or —S—, at least one of $X^1$, $X^2$, $X^3$ and $X^4$ is —NH—, —O— or —S—, and the dashed circle represents a saturated or partially unsaturated non-aromatic ring. The fused bicyclic heterocycloalkyls are optionally substituted.

"Alkyl-heterocycloalkyl" refers to a radical having an alkyl component and a heterocycloalkyl component, where the alkyl component links the heterocycloalkyl component to the point of attachment. The alkyl component is as defined above, except that the alkyl component is at least divalent, an alkylene, to link to the heterocycloalkyl component and to the point of attachment. The alkyl component can include any number of carbons, such as $C_{0-6}$, $C_{1-2}$, $C_{1-3}$, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. In some instances, the alkyl component can be absent. The heterocycloalkyl component is as defined above. Alkyl-heterocycloalkyl groups can be substituted or unsubstituted.

"Aryl" as used herein refers to a single all carbon aromatic ring or a multiple condensed all carbon ring system wherein at least one of the rings is aromatic. For example, in some embodiments, an aryl group has 6 to 20 carbon atoms, 6 to 14 carbon atoms, or 6 to 12 carbon atoms. Aryl includes a phenyl radical. Aryl also includes multiple condensed ring systems (e.g., ring systems comprising 2, 3 or 4 rings) having 9 to 20 carbon atoms, e.g., 9 to 16 carbon atoms, in which at least one ring is aromatic and wherein the other rings may be aromatic or not aromatic (i.e., carbocycle). Such multiple condensed ring systems are optionally substituted with one or more (e.g., 1, 2 or 3) oxo groups on any carbocycle portion of the multiple condensed ring system. The rings of the multiple condensed ring system can be connected to each other via fused, spiro and bridged bonds when allowed by valency requirements. It is also to be understood that when reference is made to a certain atom-range membered aryl (e.g., 6-10 membered aryl), the atom range is for the total ring atoms of the aryl. For example, a 6-membered aryl would include phenyl and a 10-membered aryl would include naphthyl and 1,2,3,4-tetrahydronaphthyl. Non-limiting examples of aryl groups include, but are not limited to, phenyl, indenyl, naphthyl, 1,2,3,4-tetrahydronaphthyl, anthracenyl, and the like.

"Alkyl-aryl" refers to a radical having an alkyl component and an aryl component, where the alkyl component links the aryl component to the point of attachment. The alkyl component is as defined above, except that the alkyl component is at least divalent, an alkylene, to link to the aryl component and to the point of attachment. The alkyl component can include any number of carbons, such as $C_{0-6}$, $C_{1-2}$, $C_{1-3}$, $C_{1-4}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. In some instances, the alkyl component can be absent. The aryl component is as defined above. Examples of alkyl-aryl groups include, but are not limited to, benzyl and ethyl-benzene. Alkyl-aryl groups can be substituted or unsubstituted.

"Heteroaryl" as used herein refers to a single aromatic ring that has at least one atom other than carbon in the ring, wherein the atom is selected from the group consisting of oxygen, nitrogen and sulfur; "heteroaryl" also includes multiple condensed ring systems that have at least one such aromatic ring, which multiple condensed ring systems are further described below. Thus, "heteroaryl" includes single aromatic rings of from 1 to 6 carbon atoms and 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2, 3 or 4 rings) wherein a heteroaryl group, as defined above, is condensed with one or more rings selected from heteroaryls (to form for example 1,8-naphthyridinyl), heterocycles, (to form for example 1,2,3,4-tetrahydro-1,8-naphthyridinyl), carbocycles (to form for example 5,6,7,8-tetrahydroquinolyl) and aryls (to form for example indazolyl) to form the multiple condensed ring system. Thus, a heteroaryl (a single aromatic ring or multiple condensed ring system) has 1-20 carbon atoms and 1-6 heteroatoms within the heteroaryl ring. Such multiple condensed ring systems may be optionally substituted with one or more (e.g., 1, 2, 3 or 4) oxo groups on the carbocycle or heterocycle portions of the condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). It also to be understood that when a reference is made to a certain atom-range membered heteroaryl (e.g., a 5 to 10 membered heteroaryl), the atom range is for the total ring atoms of the heteroaryl and includes carbon atoms and heteroatoms. For example, a 5-membered heteroaryl would include a thiazolyl and a 10-membered heteroaryl would include a quinolinyl. Exemplary heteroaryls include but are not limited to pyridyl, pyrrolyl, pyrazinyl, pyrimidinyl, pyridazinyl, pyrazolyl, thienyl, indolyl, imidazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl, thianaphthenyl, pyrrolo[2,3-b]pyridinyl, quinazolinyl-4(3H)-one, and triazolyl.

"Alkyl-heteroaryl" refers to a radical having an alkyl component and a heteroaryl component, where the alkyl component links the heteroaryl component to the point of attachment. The alkyl component is as defined above, except that the alkyl component is at least divalent, an alkylene, to link to the heteroaryl component and to the point of attachment. The alkyl component can include any number of carbons, such as $C_{0-6}$, $C_{1-2}$, $C_{1-3}$, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. In some instances, the alkyl component can be absent. The heteroaryl component is as defined within. Alkyl-heteroaryl groups can be substituted or unsubstituted.

A "compound of the present disclosure" includes compounds disclosed herein, for example a compound of the present disclosure includes compounds of Formula (I), (I-1), (Ia), (Ia-1), (Ib), (Ic), (IIa), (IIa-1), (IIc), (IIc-1), (IIc-2), (IIc-3), (IIc-4), (IIc-5), (IIc-6), (IIc-7), and (IIc-8), including the compounds of the Examples.

"Composition" as used herein is intended to encompass a product comprising the specified ingredients in the specified amounts, as well as any product, which results, directly or indirectly, from combination of the specified ingredients in the specified amounts. By "pharmaceutically acceptable" it is meant the carrier, diluent or excipient must be compatible with the other ingredients of the formulation and deleterious to the recipient thereof.

"Pharmaceutically effective amount" refers to an amount of a compound of the present disclosure in a formulation or combination thereof, that provides the desired therapeutic or pharmaceutical result.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Treatment" or "treat" or "treating" as used herein refers to an approach for obtaining beneficial or desired results. For purposes of the present disclosure, beneficial or desired results include, but are not limited to, alleviation of a symptom and/or diminishment of the extent of a symptom and/or preventing a worsening of a symptom associated with a disease or condition. In some embodiments, "treatment" or "treating" includes one or more of the following: a) inhibiting the disease or condition (e.g., decreasing one or more symptoms resulting from the disease or condition, and/or diminishing the extent of the disease or condition); b) slowing or arresting the development of one or more symptoms associated with the disease or condition (e.g., stabilizing the disease or condition, delaying the worsening or progression of the disease or condition); and c) relieving the disease or condition, e.g., causing the regression of clinical symptoms, ameliorating the disease state, delaying the progression of the disease, increasing the quality of life, and/or prolonging survival.

"Therapeutically effective amount" or "effective amount" as used herein refers to an amount that is effective to elicit the desired biological or medical response, including the amount of a compound that, when administered to a subject for treating a disease, is sufficient to effect such treatment for the disease. The effective amount can vary depending on the compound, the disease, and its severity and the age, weight, etc., of the subject to be treated. The effective amount can include a range of amounts. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any co-administered compounds may optionally be lowered due to the combined action (e.g., additive or synergistic effects) of the compounds.

"Administering" refers to oral administration, administration as a suppository, topical contact, parenteral, intravenous, intraperitoneal, intramuscular, intralesional, intranasal or subcutaneous administration, intrathecal administration, or the implantation of a slow-release device e.g., a mini-osmotic pump, to the subject. The administration can be carried out according to a schedule specifying frequency of administration, dose for administration, and other factors.

"Co-administration" as used herein refers to administration of unit dosages of the compounds disclosed herein before or after administration of unit dosages of one or more additional therapeutic agents, for example, administration of the compound disclosed herein within seconds, minutes, or hours of the administration of one or more additional therapeutic agents. For example, in some embodiments, a unit dose of a compound of the present disclosure is administered first, followed within seconds or minutes by administration of a unit dose of one or more additional therapeutic agents. Alternatively, in other embodiments, a unit dose of one or more additional therapeutic agents is administered first, followed by administration of a unit dose of a compound of the present disclosure within seconds or minutes. In some embodiments, a unit dose of a compound of the present disclosure is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound of the present disclosure. Co-administration of a compound disclosed herein with one or more additional therapeutic agents generally refers to simultaneous or sequential administration of a compound disclosed herein and one or more additional therapeutic agents, such that therapeutically effective amounts of each agent are present in the body of the patient.

"Subject" refers to animals such as mammals, including, but not limited to, primates (e.g., humans), cows, sheep, goats, horses, dogs, cats, rabbits, rats, mice and the like. In some embodiments, the subject is a human.

"Disease" or "condition" refer to a state of being or health status of a patient or subject capable of being treated with a compound, pharmaceutical composition, or method provided herein. The disease may be an autoimmune, inflammatory, cancer, infectious (e.g., a viral infection), metabolic, developmental, cardiovascular, liver, intestinal, endocrine, neurological, or other disease. In some embodiments, the disease is cancer (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma).

"Cancer" refers to all types of cancer, neoplasm or malignant tumors found in mammals, including leukemias, lymphomas, melanomas, neuroendocrine tumors, carcinomas and sarcomas. Exemplary cancers that may be treated with a compound, pharmaceutical composition, or method provided herein include lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. triple negative, ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g. hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, melanoma, prostate cancer, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma.

Additional examples include, cancer of the thyroid, endocrine system, brain, breast, cervix, colon, head & neck, esophagus, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

"Leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound, pharmaceutical composition, or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocyte leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

"Sarcoma" generally refers to a tumor which is made up of a substance like the embryonic connective tissue and is generally composed of closely packed cells embedded in a fibrillar or homogeneous substance. Sarcomas that may be treated with a compound, pharmaceutical composition, or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

"Melanoma" is taken to mean a tumor arising from the melanocytic system of the skin and other organs. Melanomas that may be treated with a compound, pharmaceutical composition, or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

"Carcinoma" refers to a malignant new growth made up of epithelial cells tending to infiltrate the surrounding tissues and give rise to metastases. Exemplary carcinomas that may be treated with a compound, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basal oid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatinifori carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, or carcinoma villosum.

"Metastasis," "metastatic," and "metastatic cancer" can be used interchangeably and refer to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

"Associated" or "associated with" in the context of a substance or substance activity or function associated with a disease (e.g., diabetes, cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma)) means that the disease (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma) is caused by (in whole or in part), or a symptom of the disease is caused by (in whole or in part) the substance or substance activity or function.

Provided are also pharmaceutically acceptable salts, hydrates, solvates, tautomeric forms, polymorphs, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The compounds of the present disclosure as described herein may be prepared and/or formulated as pharmaceutically acceptable salts or when appropriate as a free base. Pharmaceutically acceptable salts are non-toxic salts of a free base form of a compound that possesses the desired pharmacological activity of the free base. These salts may be derived from inorganic or organic acids or bases. Examples of a pharmaceutically acceptable salt of the compound of Formula (I) of the present disclosure include an inorganic acid salt such as hydrochloride, sulfate, carbonate, and phosphate etc., and an organic acid salt such as fumarate, maleate, methanesulfonate, and p-toluenesulfonate etc. Further salts with an alkaline metal such as sodium, potassium etc., with an alkaline earth metal such as magnesium or calcium etc., with an organic amine such as a lower alkyl amine, or a lower alcoholamine, with a basic amino acid such as lysine, arginine, ornithine, or an ammonium salt is also included. For example, a compound that contains a basic nitrogen may be prepared as a pharmaceutically acceptable salt by contacting the compound with an inorganic or organic acid. Non-limiting examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington: The Science and Practice of Pharmacy, 21$^{st}$ Edition, Lippincott Williams and Wilkins, Philadelphia, Pa., 2006.

Examples of "pharmaceutically acceptable salts" of the compounds disclosed herein also include salts derived from an appropriate base, such as an alkali metal (for example, sodium, potassium), an alkaline earth metal (for example, magnesium), ammonium and $NX_4^+$ (wherein X is $C_1$-$C_4$ alkyl). Also included are base addition salts, such as sodium or potassium salts.

Provided are also compounds described herein or pharmaceutically acceptable salts, isomers, or a mixture thereof, in which from 1 to n hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such compounds may increase resistance to metabolism, and thus may be useful for increasing the half-life of the compounds described herein or pharmaceutically acceptable salts, isomer, or a mixture thereof when administered to a mammal. See, e.g., Foster, "Deuterium Isotope Effects in Studies of Drug Metabolism", Trends Pharmacol. Sci., 5(12):524-527 (1984). Such compounds are synthesized by means well known in the art, for example by employing starting materials in which one or more hydrogen atoms have been replaced by deuterium.

Examples of isotopes that can be incorporated into the disclosed compounds also include isotopes of hydrogen, carbon, nitrogen, oxygen, phosphorous, fluorine, chlorine, and iodine, such as $^{2}H$, $^{3}H$, $^{11}C$, $^{13}C$, C, $^{13}N$, $^{15}N$, $^{15}O$, $^{17}O$, $^{18}O$, $^{31}P$, $^{32}P$, $^{35}S$, $^{18}F$, $^{36}C$, $^{123}I$, and $^{125}I$, respectively. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of Formula (I), (I-1), (Ia), (Ia-1), (Ib), (Ic), (IIa), (IIa-1), (IIc), (IIc-1), (IIc-2), (IIc-3), (IIc-4), (IIc-5), (IIc-6), (IIc-7), or (IIc-8) can generally be prepared by conventional techniques known to those skilled in the art or by processes analogous to those described in the Examples as set out below using an appropriate isotopically-labeled reagent in place of the non-labeled reagent previously employed.

The compounds of the embodiments disclosed herein, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included. Where compounds are represented in their chiral form, it is understood that the embodiment encompasses, but is not limited to, the specific diastereomerically or enantiomerically enriched form. Where chirality is not specified but is present, it is understood that the embodiment is directed to either the specific diastereomerically or enantiomerically enriched form; or a racemic or scalemic mixture of such compound(s). As used herein, "scalemic mixture" is a mixture of stereoisomers at a ratio other than 1:1.

"Racemates" refers to a mixture of enantiomers. The mixture can comprise equal or unequal amounts of each enantiomer.

"Stereoisomer" and "stereoisomers" refer to compounds that differ in the chirality of one or more stereocenters. Stereoisomers include enantiomers and diastereomers. The compounds may exist in stereoisomeric form if they possess one or more asymmetric centers or a double bond with asymmetric substitution and, therefore, can be produced as individual stereoisomers or as mixtures. Unless otherwise indicated, the description is intended to include individual stereoisomers as well as mixtures. The methods for the determination of stereochemistry and the separation of stereoisomers are well-known in the art (see, e.g., Chapter 4 of Advanced Organic Chemistry, 4th ed., J. March, John Wiley and Sons, New York, 1992).

"Tautomer" refers to alternate forms of a compound that differ in the position of a proton, such as enol-keto and imine-enamine tautomers, or the tautomeric forms of heteroaryl groups containing a ring atom attached to both a ring —NH— and a ring =N— such as pyrazoles, imidazoles, benzimidazoles, triazoles, and tetrazoles.

Unless defined otherwise, all technical and scientific terms used herein have the same meaning as commonly understood by one of ordinary skill in the art. A dash at the front or end of a chemical group is a matter of convenience;

chemical groups may be depicted with or without one or more dashes without losing their ordinary meaning. A wavy line drawn through a line in a structure indicates a point of attachment of a group. A dashed line indicates an optional bond. Unless chemically or structurally required, no directionality is indicated or implied by the order in which a chemical group is written or the point at which it is attached to the remainder of the molecule. For instance, the group "—SO$_2$CH$_2$—" is equivalent to "—CH$_2$SO$_2$—" and both may be connected in either direction. Similarly, an "arylalkyl" group, for example, may be attached to the remainder of the molecule at either an aryl or an alkyl portion of the group. A prefix such as "C$_{u-v}$" or (C$_u$-C$_v$) indicates that the following group has from u to v carbon atoms. For example, "C$_{1-6}$alkyl" and "C$_1$-C$_6$ alkyl" both indicate that the alkyl group has from 1 to 6 carbon atoms.

"Solvate" as used herein refers to the result of the interaction of a solvent and a compound. Solvates of salts of the compounds described herein are also provided. Hydrates of the compounds described herein are also provided.

"Prodrug" as used herein refers to a derivative of a drug that upon administration to the human body is converted to the parent drug according to some chemical or enzymatic pathway.

II. Compounds

The present disclosure provides compounds of Formula (I), (I-1), (Ia), (Ia-1), (Ib), (Ic), (IIa), (IIa-1), (IIc), (IIc-1), (IIc-2), (IIc-3), (IIc-4), (IIc-5), (IIc-6), (IIc-7), and (IIc-8), and pharmaceutically acceptable salts thereof.

In some embodiments, the compound has the structure of Formula (I-1):

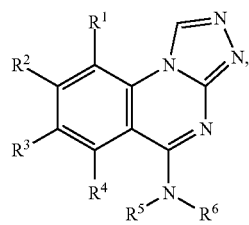

(I-1)

or a pharmaceutically acceptable salt thereof.

In some embodiments, the compound of Formula (I-1), or a pharmaceutically acceptable salt thereof, is the compound wherein R$^1$, R$^2$, R$^3$ and R$^4$ are independently a hydrogen atom, a halogen atom, a hydroxy group, a carboxy group, a formyl group, a cyano group, an amino group, a nitro group, a nitroso group, a alkoxycarbonyl group, an optionally substituted alkyl group, an optionally substituted alkenyl group, an optionally substituted alkynyl group, an optionally substituted cycloalkyl group, an optionally substituted alkoxy group, an optionally substituted alkylamino group, an optionally substituted aryl group, an optionally substituted heteroaryl group, an optionally substituted acyl group, an optionally substituted carbamoyl group, an optionally substituted acylamino group, an optionally substituted saturated heterocyclo group or an optionally substituted alkylsulfonylamino group;

R$^5$ is a hydrogen atom, an optionally substituted alkyl group, an optionally substituted alkynyl group, or an optionally substituted aryl group; and R$^6$ is an optionally substituted alkyl group, an optionally substituted aryl group, an optionally substituted heteroaryl group, or R$^5$ and R$^6$ together with a nitrogen atom which they bound, may form a nitrogen-containing saturated heterocyclo ring to which an aryl ring is fused, and the fused ring may be substituted;

provided that the compound is not

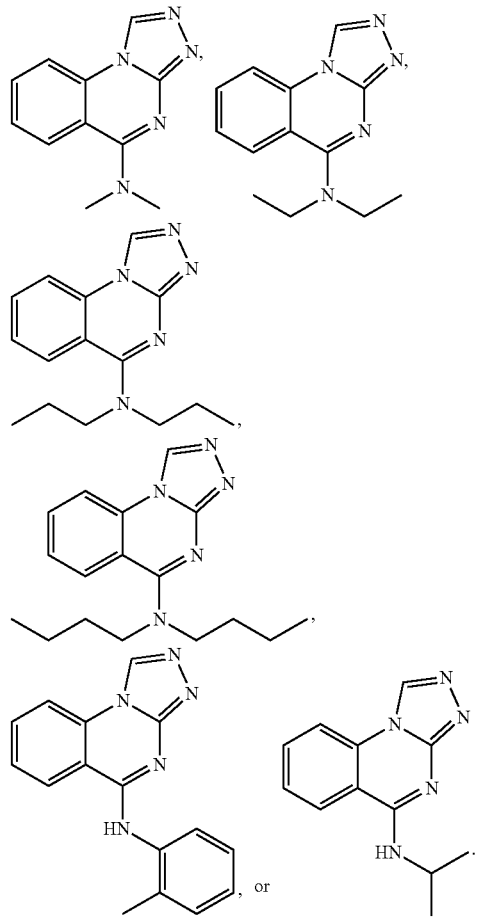

Examples of a substituent for R$^1$ to R$^4$ in a compound of Formula (I-1) include a halogen atom such as a fluorine atom, a chlorine atom, a bromine atom or an iodine atom; a hydroxy group; a carboxy group; a formyl group; a cyano group; an amino group; a nitro group; a nitroso group; an optionally substituted alkyl group (e.g., an optionally substituted C$_{1-6}$ alkyl group, or an optionally substituted aralkyl group is exemplified. In addition, a substituent of the substituted alkyl includes a hydroxy group, a methoxy group, a dimethylamino group, a morpholino group, a 4-methylpiperazin-1-yl group, and a piperidin-1-yl group.); an optionally substituted alkenyl(e.g., an optionally substituted C$_{2-6}$ alkenyl such as a vinyl group, an allyl group, an isopropenyl group, a butenyl group, an isobutenyl group etc.), an optionally substituted alkynyl group (e.g., an optionally substituted C$_{2-6}$ alkynyl group such as an ethynyl group, a 1-propynyl group, and a propargyl group was exemplified, and an amino group, a cyclopropyl group, a hydroxy group, a phenyl group and the like are included in a substituent of the substituted alkynyl group. In addition, the amino group may be protected by an amino-protecting group, an optionally substituted cycloalkyl group (e.g., an optionally substituted $C_{3-7}$ cycloalkyl group is exemplified), an optionally substituted alkoxy group (e.g., an optionally substituted $C_{1-6}$ alkoxy group), an optionally substituted alkylamino group (e.g., mono-$C_{1-6}$ alkylamino group, di-$C_{1-6}$ alkylamino group are exemplified, and a hydroxy group, a methoxy group and the like are included in a substituent of the substituted alkylamino group), an optionally substituted acylamino group (e.g., an optionally substituted $C_{1-4}$ aliphatic acylamino group or an arylacylamino group is exemplified and an acetylamino group, a benzoylamino group or a pyridylcarbonylamino group is included), an alkoxycarbonyl group (e.g., an optionally substituted $C_{1-4}$ alkoxycarbonyl group), an optionally substituted acyl group (an alkyl- or aryl-substituted carbonyl group is exemplified and e.g., an acetyl group or a benzoyl group is included), an optionally substituted carbamoyl group (e.g., an optionally substituted $C_{1-4}$ alkylcarbamoyl group), an optionally substituted ureido group (e.g., an optionally substituted $C_{1-4}$ alkylureido group), an optionally substituted aryl group (e.g., an optionally substituted phenyl group), an optionally substituted saturated heterocyclo group (e.g., an optionally substituted morpholinyl group, a 4-methylpiperazin-1-yl group, a piperidin-1-yl group, or a pyrrolidinyl group), an optionally substituted heteroaryl group (e.g., an optionally substituted pyridyl group, thienyl group or furanyl group), an optionally substituted thioalkyl group (e.g., an optionally substituted $C_{1-4}$ thioalkyl group), an optionally substituted alkylsulfonyl group (e.g., an optionally substituted $C_{1-4}$ alkylsulfonyl group), an optionally substituted alkylsulfonylamino group (e.g., an optionally substituted $C_{1-4}$ alkylsulfonylamino group) and the like.

Examples of $R^5$ in a compound of Formula (I-1) include a hydrogen atom, an optionally substituted alkyl group (e.g., an optionally substituted $C_{1-6}$ alkyl group is exemplified, and a $C_{3-6}$ cycloalkyl group, a hydroxy group, a methoxy group, a phenyl group and the like are included as a substituent of the substituted alkyl group. In addition, the hydroxy group may be protected by a OH-protecting group explained later), an optionally substituted alkynyl group (e.g., an optionally substituted $C_{2-6}$ alkynyl group is exemplified), an optionally substituted aryl group (an optionally substituted phenyl group is exemplified) and the like.

Examples of $R^6$ in a compound of Formula (I-1) include an optionally substituted alkyl group (e.g., an optionally substituted $C_{1-6}$ alkyl group is exemplified, and a $C_{3-6}$ cycloalkyl group, a hydroxy group, a methoxy group and the like are included as a substituent of the substituted alkyl group. In addition, the hydroxy group may be protected by a OH-protecting group explained later), an optionally substituted alkynyl group, an optionally substituted aryl group (e.g., a phenyl group and biphenyl group etc. are exemplified, and a halogen atom, a hydroxy group, a methoxy group, a cyano group, a nitro group, a $C_{1-4}$ alkyl group, a carboxy group, a carbamoyl group, an amino group, a methoxycarbonyl group, a cyclopropyl group, a formyl group, a fluoromethyl group, a trifluoromethyl group, a hydroxymethyl group, a methoxymethyl group, an acetylamino group, a phenyl group, 5- or 6-membered saturated or unsaturated heterocyclo group etc. are included as a substituent of these groups. In addition, the hydroxy group may be protected by a OH-protecting group explained later), and an optionally substituted heteroaryl group (e.g., a pyridyl group or a thienyl group is included) and the like.

Examples in a compound of Formula (Ic), (IIc), or (IIc-1) of a nitrogen-containing, 5- to 8-membered saturated heterocyclo ring which is formed by $R^5$ and $R^{6a}$ together with a nitrogen atom and an aryl ring (e.g., a phenyl group) is fused include e.g., 1,2,3,4-tetrahydroquinoline, 3,4-dihydro-2H-1,4-benzooxazine, tetrahydrobenzoazepine and hexahydrobenzoazocine etc.

In some embodiments, the present disclosure provides a compound of Formula (I):

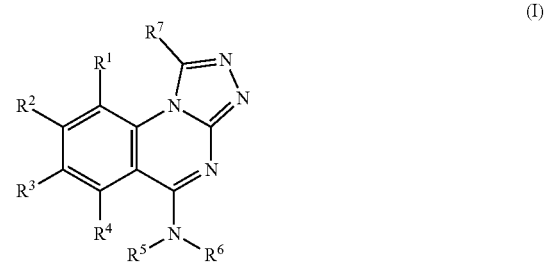

or a pharmaceutically acceptable salt thereof, wherein
$R^1$ is hydrogen, $C_{1-6}$ alkyl, $C_{2-6}$ alkenyl, $C_{2-6}$ alkynyl, $C_{1-6}$ alkoxy, halogen, $C_{1-6}$ haloalkyl, $C_{1-6}$ haloalkoxy, or —CN;
$R^2$ is hydrogen, $C_{1-6}$ alkyl, $C_{2-6}$ alkenyl, $C_{2-6}$ alkynyl, $C_{1-6}$ hydroxyalkyl, $C_{1-6}$ aminoalkyl, $C_{1-6}$ alkoxy, $C_{2-6}$ alkoxyalkyl, halogen, $C_{1-6}$ haloalkyl, $C_{1-6}$ haloalkoxy, —CN, —NO, —NO$_2$, —C(O)R$^{2a}$, —C(O)OR$^{2a}$, —OC(O)R$^{2a}$, —C(O)N(R$^{2a}$)(R$^{2b}$), —N(R$^{2a}$)C(O)R$^{2b}$, —OC(O)N(R$^{2a}$)(R$^{2b}$), —N(R$^{2a}$)C(O)OR$^{2b}$, —C(=NR$^{2a}$)N(R$^{2b}$)(R$^{2c}$), —N(R$^{2a}$)(R$^{2b}$), —N(R$^{2a}$)N(R$^{2b}$)(R$^{2c}$), —N(R$^{2a}$)N=C(R$^{2b}$)(OR$^{2c}$), —OR$^{2a}$, —SR$^{2a}$, —S(O)R$^{2a}$, —S(O)(NR$^{2a}$)(R$^{2b}$), —S(NR$^{2a}$)(NR$^{2b}$)(R$^{2c}$), —S(O)$_2$R$^{2a}$, —S(O)$_2$N(R$^{2a}$)(R$^{2b}$), —N(R$^{2a}$)S(O)$_2$(R$^{2b}$), —P(R$^{2a}$)(R$^{2b}$), —P(O)(R$^{2a}$)(R$^{2b}$), —P(O)(OR$^{2a}$)(R$^{2b}$), —P(O)(OR$^{2a}$)(OR$^{2b}$), $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, $C_{1-6}$ alkyl-(heterocycloalkyl), heteroaryl, or $C_{1-6}$ alkyl-(heteroaryl), wherein each alkyl, alkenyl or alkynyl is independently optionally substituted with 1 to 3 R$^{2d}$ groups, each cycloalkyl is optionally substituted with 1 to 3 R$^{2e}$ groups, each aryl is optionally substituted with 1 to 3 R$^{2f}$ groups, each heterocycloalkyl is optionally substituted with 1 to 3 R$^{2g}$ groups, and each heteroaryl is optionally substituted with 1 to 3 R$^{2h}$ groups;
each R$^{2a}$, R$^{2b}$, and R$^{2c}$ is independently hydrogen, $C_{1-6}$ alkyl, $C_{2-6}$ alkenyl, $C_{2-6}$ alkynyl, $C_{1-6}$ hydroxyalkyl, $C_{1-6}$ aminoalkyl, $C_{2-6}$ alkoxyalkyl, $C_{1-6}$ haloalkyl, $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, $C_{1-6}$ alkyl-(heterocycloalkyl), heteroaryl, or $C_{1-6}$ alkyl-(heteroaryl), wherein the aryl or heteroaryl is optionally substituted with 1 to 3 R$^{2j}$;
alternatively, R$^{2a}$, R$^{2b}$, and R$^{2c}$ when attached to the same atom can be combined with the atom to which they are attached to form a heterocycloalkyl;
each R$^{2d}$ is independently —CN, —C(O)R$^{2d1}$, —C(O)OR$^{2d1}$, —OC(O)R$^{2d1}$, —C(O)N(R$^{2d1}$)(R$^{2d2}$), —N(R$^{2d1}$)C(O)R$^{2d2}$, —OC(O)N(R$^{2d1}$)(R$^{2d2}$), —N(R$^{2d1}$)C(O)OR$^{2d2}$, —N(R$^{2d1}$)(R$^{2d2}$), =O, —OR$^{2d1}$, —SR$^{2d1}$, —S(O)R$^{2d1}$, —S(O)(NR$^{2d1}$)(R$^{2d2}$), —S(O)$_2$R$^{2d1}$, —S(O)N(R$^{2d1}$)(R$^{2d2}$), —N(R$^{2d1}$)S(O)$_2$R$^{2d2}$, $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, $C_{1-6}$ alkyl-(heterocycloalkyl), heteroaryl, or $C_{1-6}$ alkyl-(heteroaryl);

each $R^{2d1}$ and $R^{2d2}$ is independently hydrogen, $C_{1-6}$ alkyl, $C_{1-6}$ hydroxyalkyl, $C_{1-6}$ aminoalkyl, $C_{2-6}$ alkoxyalkyl, or $C_{1-6}$ haloalkyl;

each $R^{2e}$, $R^{2f}$, $R^{2g}$, and $R^{2h}$ is independently hydrogen, $C_{1-6}$ alkyl, $C_{1-6}$ hydroxyalkyl, $C_{1-6}$ aminoalkyl, $C_{1-6}$ alkoxy, $C_{2-6}$ alkoxyalkyl, halogen, $C_{1-6}$ haloalkyl, $C_{1-6}$ haloalkoxy, —CN, or —OH;

each $R^{2j}$ is independently $C_{1-6}$ alkyl, $C_{1-6}$ hydroxyalkyl, $C_{1-6}$ aminoalkyl, $C_{1-6}$ alkoxy, $C_{2-6}$ alkoxyalkyl, halogen, $C_{1-6}$ haloalkyl, or $C_{1-6}$ haloalkoxy;

$R^3$ is hydrogen, $C_{1-6}$ alkyl, $C_{2-6}$ alkenyl, $C_{2-6}$ alkynyl, $C_{1-6}$ hydroxyalkyl, $C_{1-6}$ aminoalkyl, $C_{1-6}$ alkoxy, $C_{2-6}$ alkoxyalkyl, halogen, $C_{1-6}$ haloalkyl, $C_{1-6}$ haloalkoxy, —CN, —NO, —NO$_2$, —C(O)R$^{3a}$, —C(O)OR$^{3a}$, —OC(O)R$^{3a}$, —C(O)N(R$^{3a}$)(R$^{3b}$), —N(R$^{3a}$)C(O)R$^{3b}$, —OC(O)N(R$^{3a}$)(R$^{3b}$), —N(R$^{3a}$)C(O)OR$^{3b}$, —C(=NR$^{3a}$)N(R$^{3b}$)(R$^{3c}$), —N(R$^{3a}$)(R$^{3b}$), —N(R$^{3a}$)N(R$^{3b}$)(R$^{3c}$), —N(R$^{3a}$)N=C(R$^{3b}$)(OR$^{3c}$), —OR$^{3a}$, —SR$^{3a}$, —S(O)R$^{3a}$, —S(O)(NR$^{3a}$)(R$^{3b}$), —S(NR$^{3a}$)(NR$^{3b}$)(R$^{3c}$), —S(O)$_2$R$^{3a}$, —S(O)$_2$N(R$^{3a}$)(R$^{3b}$), —N(R$^{3a}$)S(O)$_2$(R$^{3b}$), —P(R$^{3a}$)(R$^{3b}$), —P(O)(R$^{3a}$)(R$^{3b}$), —P(O)(OR$^{3a}$)(R$^{3b}$), —P(O)(OR$^{3a}$)(OR$^{3b}$), $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, $C_{1-6}$ alkyl-(heterocycloalkyl), heteroaryl, or $C_{1-6}$ alkyl-(heteroaryl), wherein each alkenyl or alkynyl is independently optionally substituted with 1 to 3 R$^{3d}$ groups, each cycloalkyl is optionally substituted with 1 to 3 R$^{3e}$ groups, each aryl is optionally substituted with 1 to 3 R$^{3f}$ groups, each heterocycloalkyl is optionally substituted with 1 to 3 R$^{3g}$ groups, and each heteroaryl is optionally substituted with 1 to 3 R$^{3h}$ groups;

each $R^{3a}$, $R^{3b}$, and $R^{3c}$ is independently hydrogen, $C_{1-6}$ alkyl, $C_{1-6}$ hydroxyalkyl, $C_{2-6}$ alkoxyalkyl, $C_{1-6}$ haloalkyl, $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, or heteroaryl;

alternatively, $R^{3a}$, $R^{3b}$, and $R^{3c}$ when attached to the same atom can be combined with the atom to which they are attached to form a heterocycloalkyl;

each $R^{3d}$ is independently —N(R$^{3d1}$)(R$^{3d2}$), —OR$^{3d1}$, $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, or heteroaryl;

each $R^{3d1}$ and $R^{3d2}$ is independently hydrogen, $C_{1-6}$ alkyl, or —C(O)O—(C$_{1-6}$ alkyl);

each $R^{3e}$, $R^{3f}$, $R^{3g}$, and $R^{3h}$ is independently hydrogen, $C_{1-6}$ alkyl, $C_{1-6}$ alkoxy, halogen, $C_{1-6}$ haloalkyl or $C_{1-6}$ haloalkoxy;

$R^4$ is hydrogen, $C_{1-6}$ alkyl, $C_{2-6}$ alkenyl, $C_{2-6}$ alkynyl, $C_{1-6}$ alkoxy, halogen, $C_{1-6}$ haloalkyl, $C_{1-6}$ haloalkoxy, or —CN;

$R^5$ is hydrogen, $C_{1-6}$ alkyl, $C_{2-6}$ alkenyl, $C_{2-6}$ alkynyl, $C_{1-6}$ hydroxyalkyl, $C_{2-6}$ alkoxyalkyl, $C_{1-6}$ haloalkyl, $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, $C_{1-6}$ alkyl-(heterocycloalkyl), heteroaryl, or $C_{1-6}$ alkyl-(heteroaryl), wherein the alkyl is optionally substituted with R$^{5a}$;

$R^{5a}$ is —OSi(R$^{5a1}$)(R$^{5a2}$)(R$^{5a3}$)

$R^{5a1}$, $R^{5a2}$, and $R^{5a3}$ are each independently $C_{1-6}$ alkyl; and $R^{6a}$ is $C_{1-6}$ alkyl, $C_{2-6}$ alkenyl, $C_{2-6}$ alkynyl, $C_{1-6}$ haloalkyl, $C_{6-12}$ aryl, or heteroaryl, wherein the aryl or heteroaryl are each optionally substituted with 1 to 3 R$^{6a}$;

each $R^{6a}$ is independently $C_{1-6}$ alkyl, $C_{2-6}$ alkenyl, $C_{2-6}$ alkynyl, $C_{1-6}$ hydroxyalkyl, $C_{1-6}$ aminoalkyl, $C_{1-6}$ alkoxy, $C_{2-6}$ alkoxyalkyl, halogen, $C_{1-6}$ haloalkyl, $C_{1-6}$ haloalkoxy, —CN, —NO$_2$, —C(O)R$^{6b}$, —C(O)OR$^{6b}$, —OC(O)R$^{6b}$, —C(O)N(R$^{6b}$)(R$^{6c}$), —N(R$^{6b}$)C(O)R$^{6c}$, —C(=NR$^{6b}$)N(R$^{6c}$)(R$^{6d}$), —N(R$^{6b}$)(R$^{6c}$), —OR$^{6b}$, —SR$^{6b}$, —S(O)R$^{6b}$, —S(O)$_2$R$^{6b}$, —S(NR$^{6b}$)(NR$^{6c}$)R$^{6d}$, —S(O)(NR$^{6b}$)(R$^{6c}$), —S(O)$_2$N(R$^{6b}$)(R$^{6c}$), —N(R$^{6b}$)S(O)$_2$(R$^{6c}$), —P(R$^{6b}$)(R$^{6c}$), —P(O)(R$^{6b}$)(R$^{6c}$), —P(O)(OR$^{6b}$)(R$^{6c}$), —P(O)(OR$^{6b}$)(OR$^{6c}$), $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, $C_{1-6}$ alkyl-(heterocycloalkyl), heteroaryl, or $C_{1-6}$ alkyl-(heteroaryl), wherein the cycloalkyl, aryl, heterocycloalkyl, or heteroaryl is each optionally substituted with 1 to 3 R$^{6e}$, the alkyl is optionally substituted with R$^{6f}$, and the alkynyl is optionally substituted with 1 to 4 R$^{6j}$;

each $R^{6b}$, $R^{6c}$ and $R^{6d}$ is independently hydrogen, $C_{1-6}$ alkyl, $C_{1-6}$ hydroxyalkyl, $C_{1-6}$ aminoalkyl, $C_{2-6}$ alkoxyalkyl, $C_{1-6}$ haloalkyl, $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, $C_{1-6}$ alkyl-(heterocycloalkyl), heteroaryl, or $C_{1-6}$ alkyl-(heteroaryl), wherein the cycloalkyl, aryl, heterocycloalkyl, or heteroaryl is optionally substituted by 1 to 3 R$^{6k}$;

each $R^{6k}$ is independently $C_{1-6}$ alkyl, $C_{1-6}$ hydroxyalkyl, $C_{1-6}$ aminoalkyl, $C_{1-6}$ alkoxy, $C_{2-6}$ alkoxyalkyl, $C_{1-6}$ haloalkyl, $C_{1-6}$ haloalkoxy, $C_{3-10}$ cycloalkyl, $C_{1-6}$ alkyl-$C_{3-10}$ cycloalkyl, heterocycloalkyl, or $C_{1-6}$ alkyl-(heterocycloalkyl);

each $R^{6e}$ is independently $C_{1-6}$ alkyl, $C_{2-6}$ alkenyl, $C_{2-6}$ alkynyl, $C_{1-6}$ hydroxyalkyl, $C_{1-6}$ aminoalkyl, $C_{1-6}$ alkoxy, $C_{2-6}$ alkoxyalkyl, halogen, $C_{1-6}$ haloalkyl, $C_{1-6}$ haloalkoxy, —CN, —NO$_2$, —C(O)R$^{6e1}$, —C(O)OR$^{6e1}$, —OC(O)R$^{6e1}$, —C(O)N(R$^{6e1}$)(R$^{6e2}$), —N(R$^{6e1}$)C(O)R$^{6e2}$, —OC(O)N(R$^{6e1}$)(R$^{6e2}$), —N(R$^{6e1}$)C(O)OR$^{6e2}$, —C(=NR$^{6e1}$)N(R$^{6e2}$)(R$^{6e3}$), —N(R$^{6e1}$)(R$^{6e2}$), =O, —OR$^{6e}$, —SR$^{6e1}$, —S(O)R$^{6e1}$, —S(NR$^{6e1}$)(NR$^{6e2}$), —S(O)(NR$^{6e1}$)(R$^{6e2}$), —S(O)$_2$R$^{6e1}$, —S(O)$_2$N(R$^{6e1}$)(R$^{6e2}$), —SF$_5$, —N(R$^{6e1}$)S(O)$_2$(R$^{6e2}$), —P(R$^{6e1}$)(R$^{6e2}$), —P(O)(R$^{6e1}$)(R$^{6e2}$), —P(O)(OR$^{6e1}$)(R$^{6e2}$), —P(O)(OR$^{6e1}$)(OR$^{6e2}$), —Si(R$^{6e1}$)(R$^{6e2}$)(R$^{6e3}$), $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, $C_{1-6}$ alkyl-heterocycloalkyl, heteroaryl, or $C_{1-6}$ alkyl-heteroaryl, wherein the cycloalkyl, aryl, heterocycloalkyl, or heteroaryl is each optionally substituted with 1 to 3 R$^{6h}$, and the alkyl is optionally substituted with 1 to 3 R$^{6m}$;

each $R^{6e1}$, $R^{6e2}$, and $R^{6e3}$ is independently hydrogen, $C_{1-6}$ alkyl, $C_{1-6}$ hydroxyalkyl, $C_{1-6}$ aminoalkyl, $C_{1-6}$ alkoxyalkyl, $C_{1-6}$ haloalkyl, $C_{3-10}$ cycloalkyl, $C_{1-6}$ alkyl-$C_{3-10}$ cycloalkyl, $C_{6-10}$ aryl, $C_{1-6}$ alkyl-$C_{6-10}$ aryl, heterocycloalkyl, $C_{1-6}$ alkyl-(heterocycloalkyl), heteroaryl, or $C_{1-6}$ alkyl-(heteroaryl), wherein the cycloalkyl, aryl, heterocycloalkyl, or heteroaryl is optionally substituted with 1 to 3 R$^{6n}$;

each $R^{6n}$ is $C_{1-6}$ alkyl, $C_{2-6}$ alkenyl, $C_{2-6}$ alkynyl, $C_{1-6}$ hydroxyalkyl, $C_{1-6}$ aminoalkyl, $C_{1-6}$ alkoxy, $C_{2-6}$ alkoxyalkyl, halogen, $C_{1-6}$ haloalkyl, $C_{1-6}$ haloalkoxy, —CN, —C(O)R$^{6n1}$, —C(O)OR$^{6n1}$, —OC(O)R$^{6n1}$, —C(O)N(R$^{6n1}$)(R$^{6n2}$), —N(R$^{6n1}$)C(O)R$^{6n2}$, —OC(O)N(R$^{6n1}$)(R$^{6n2}$), —N(R$^{6n1}$)C(O)OR$^{6n2}$, —C(=NR$^{6n1}$)N(R$^{6n2}$)(R$^{6n3}$), —N(R$^{6n1}$)(R$^{6n2}$), =O, —OH, —SR$^{6n1}$, —S(O)R$^{6n1}$, —S(NR$^{6n1}$)(NR$^{6n2}$)R$^{6n3}$, —S(O)(NR$^{6n1}$)(R$^{6n2}$), —S(O)$_2$R$^{6n}$, —S(O)$_2$N(R$^{6n1}$)(R$^{6n2}$), or —N(R$^{6n1}$)S(O)$_2$(R$^{6n2}$);

each $R^{6n1}$, $R^{6n2}$ and $R^{6n3}$ is independently hydrogen, $C_{1-6}$ alkyl, $C_{1-6}$ hydroxyalkyl, $C_{1-6}$ aminoalkyl, $C_{2-6}$ alkoxyalkyl, $C_{1-6}$ haloalkyl, $C_{3-10}$ cycloalkyl, $C_{1-6}$ alkyl-$C_{3-10}$ cycloalkyl, C$_{6-10}$ aryl, C$_{1-6}$ alkyl-C$_{6-10}$ aryl, heterocycloalkyl, C$_{1-6}$ alkyl-(heterocycloalkyl), heteroaryl, or C$_{1-6}$ alkyl-(heteroaryl);

each R$^{6h}$ is independently C$_{1-6}$ alkyl, C$_{2-6}$ alkenyl, C$_{2-6}$ alkynyl, C$_{1-6}$ hydroxyalkyl, C$_{1-6}$ aminoalkyl, C$_{1-6}$ alkoxy, C$_{2-6}$ alkoxyalkyl, halogen, C$_{1-6}$ haloalkyl, C$_{1-6}$ haloalkoxy, —CN, —C(O)R$^{6h1}$, —C(O)OR$^{6h1}$, —OC(O)R$^{6h1}$, —C(O)N(R$^{6h1}$)(R$^{6h2}$), —N(R$^{6h1}$)C(O)R$^{6h2}$, —OC(O)N(R$^{6h1}$)(R$^{6h2}$), —N(R$^{6h1}$)C(O)OR$^{6h2}$, —C(=NR$^{6h1}$)N(R$^{6h2}$)(R$^{6h3}$), —N(R$^{6h1}$)(R$^{6h2}$), =O, —OH, —SR$^{6h1}$, —S(O)R$^{6h1}$, —S(NR$^{6h1}$)(NR$^{6h2}$)R$^{6h3}$, —S(O)(NR$^{6h1}$)(R$^{6h2}$), —S(O)$_2$R$^{6h1}$, —S(O)$_2$N(R$^{6h1}$)(R$^{6}$), —N(R$^{6h1}$)S(O)$_2$(R$^{6h1}$), C$_{3-10}$ cycloalkyl, C$_{1-6}$ alkyl-C$_{3-10}$ cycloalkyl, heterocycloalkyl, or C$_{1-6}$ alkyl-(heterocycloalkyl);

each R$^{6h1}$, R$^{6h2}$, and R$^{6h3}$ is independently hydrogen, C$_{1-6}$ alkyl, C$_{1-6}$ hydroxyalkyl, C$_{1-6}$ aminoalkyl, C$_{2-6}$ alkoxyalkyl, C$_{1-6}$ haloalkyl, C$_{3-10}$ cycloalkyl, C$_{1-6}$ alkyl-C$_{3-10}$ cycloalkyl, C$_{6-10}$ aryl, C$_{1-6}$ alkyl-C$_{6-10}$ aryl, heterocycloalkyl, C$_{1-6}$ alkyl-(heterocycloalkyl), heteroaryl, or C$_{1-6}$ alkyl-(heteroaryl);

each R$^{6m}$ is independently halogen, C$_{1-6}$ haloalkyl, C$_{1-6}$ haloalkoxy, —CN, —C(O)R$^{6m1}$, —C(O)OR$^{6m1}$, —OC(O)R$^{6m1}$, —C(O)N(R$^{6m1}$)(R$^{6m2}$), —N(R$^{6m3}$)C(O)R$^{6m2}$, —OC(O)N(R$^{6m1}$)(R$^{6m2}$), —N(R$^{6m1}$)C(O)OR$^{6m2}$, —C(=NR$^{6m3}$)N(R$^{6m1}$)(R$^{6m2}$), —N(R$^{6m1}$)(R$^{6m2}$), =O, —OH, —SR$^{6m1}$, —S(O)R$^{6m1}$, —S(NR$^{6m1}$)(NR$^{6m2}$)R$^{6m3}$, —S(O)(NR$^{6m1}$)(R$^{6m2}$), —S(O)$_2$R$^{6m1}$, —S(O)$_2$N(R$^{6m1}$)(R$^{6m2}$), or —N(R$^{6m3}$)S(O)$_2$(R$^{6m2}$);

each R$^{6m1}$, R$^{6m2}$, and R$^{6m3}$ is independently hydrogen, C$_{1-6}$ alkyl, C$_{1-6}$ hydroxyalkyl, C$_{1-6}$ aminoalkyl, C$_{2-6}$ alkoxyalkyl, C$_{1-6}$ haloalkyl, C$_{3-10}$ cycloalkyl, C$_{1-6}$ alkyl-C$_{3-10}$ cycloalkyl, C$_{6-10}$ aryl, C$_{1-6}$ alkyl-C$_{6-10}$ aryl, heterocycloalkyl, C$_{1-6}$ alkyl-(heterocycloalkyl), heteroaryl, or C$_{1-6}$ alkyl-(heteroaryl);

R$^{6f}$ is —OSi(R$^{6f1}$)(R$^{6f2}$)(R$^{6f1}$);

R$^{6f}$, R$^{6f2}$, and R$^{6f1}$ are each independently C$_{1-6}$ alkyl;

each R$^{6j}$ is independently C$_{2-6}$ alkoxyalkyl, halogen, C$_{1-6}$ haloalkyl, C$_{1-6}$ haloalkoxy, —CN, —C(O)R$^{6j1}$, —C(O)OR$^{6j1}$, —OC(O)R$^{6j1}$, —C(O)N(R$^{6j1}$)(R$^{6j2}$), —N(R$^{6j3}$)C(O)R$^{6j2}$, —OC(O)N(R$^{6j1}$)(R$^{6j2}$), —N(R$^{6j1}$)C(O)OR$^{6j2}$, —C(=NR$^{6j3}$)N(R$^{6j1}$)(R$^{6j2}$), —N(R$^{6j1}$)(R$^{6j2}$), =O, —OR$^{6j}$, —SR$^{6j1}$, —S(O)R$^{6j1}$, —S(NR$^{6j1}$)(NR$^{6j2}$), —S(NR$^{6j1}$)(NR$^{6j2}$)R$^{6j3}$, —S(O)(NR$^{6j1}$)(R$^{6j2}$), —S(O)$_2$R$^{6j1}$, —S(O)$_2$N(R$^{6j1}$)(R$^{6j2}$), —N(R$^{6j1}$)S(O)$_2$(R$^{6j2}$), —Si(R$^{6j1}$)(R$^{6j2}$)(R$^{6j3}$), C$_{3-10}$ cycloalkyl, C$_{6-12}$ aryl, heterocycloalkyl, or heteroaryl, wherein the cycloalkyl, aryl, heterocycloalkyl, or heteroaryl is optionally substituted with 1 to 3 R$^{6p}$;

each R$^{6j1}$, R$^{6j2}$, and R$^{6j3}$ is independently hydrogen, C$_{1-6}$ alkyl, C$_{1-6}$ hydroxyalkyl, C$_{1-6}$ aminoalkyl, C$_{2-6}$ alkoxyalkyl, C$_{1-6}$ haloalkyl, C$_{3-10}$ cycloalkyl, C$_{1-6}$ alkyl-C$_{3-10}$ cycloalkyl, C$_{6-10}$ aryl, C$_{1-6}$ alkyl-C$_{6-10}$ aryl, heterocycloalkyl, C$_{1-6}$ alkyl-(heterocycloalkyl), heteroaryl, or C$_{1-6}$ alkyl-(heteroaryl);

each R$^{6p}$ is independently C$_{1-6}$ alkyl, C$_{1-6}$ hydroxyalkyl, C$_{1-6}$ aminoalkyl, C$_{1-6}$ alkoxy, C$_{2-6}$ alkoxyalkyl, halogen, C$_{1-6}$ haloalkyl, C$_{1-6}$ haloalkoxy, —CN, —C(O)R$^{6p1}$, —C(O)OR$^{6p1}$, —OC(O)R$^{6p1}$, —C(O)N(R$^{6p1}$)(R$^{6p2}$), —N(R$^{6p1}$)C(O)R$^{6p2}$, —OC(O)N(R$^{6p1}$)(R$^{6p2}$), —N(R$^{6p1}$)C(O)OR$^{6p2}$, —C(=NR$^{6p3}$)N(R$^{6p1}$)(R$^{6p2}$), —N(R$^{6p1}$)(R$^{6p2}$), =O, —OH, —SR$^{6p1}$, —S(O)R$^{6p1}$, —S(NR$^{6p1}$)(NR$^{6p2}$)R$^{6p3}$, —S(O)(NR$^{6p1}$)(R$^{6p2}$), —S(O)$_2$R$^{6p1}$, —S(O)$_2$N(R$^{6p1}$)(R$^{6p2}$), or —N(R$^{6p1}$)S(O)$_2$(R$^{6p2}$);

each R$^{6p1}$, R$^{6p2}$, and R$^{6p3}$ is independently hydrogen, C$_{1-6}$ alkyl, C$_{1-6}$ hydroxyalkyl, C$_{1-6}$ aminoalkyl, C$_{2-6}$ alkoxyalkyl, C$_{1-6}$ haloalkyl, C$_{3-10}$ cycloalkyl, C$_{1-6}$ alkyl-C$_{3-10}$ cycloalkyl, C$_{6-10}$ aryl, C$_{1-6}$ alkyl-C$_{6-10}$ aryl, heterocycloalkyl, C$_{1-6}$ alkyl-(heterocycloalkyl), heteroaryl, or C$_{1-6}$ alkyl-(heteroaryl);

or R$^5$ and one R$^{6a}$ together with the atoms to which they are attached form a heterocycloalkyl, optionally substituted with 1 to 3 R$^{6g}$;

each R$^{6g}$ is independently C$_{1-6}$ alkyl, C$_{2-6}$ alkenyl, C$_{2-6}$ alkynyl, C$_{1-6}$ hydroxyalkyl, C$_{1-6}$ aminoalkyl, C$_{2-6}$ alkoxyalkyl, halogen, C$_{1-6}$ haloalkyl, C$_{1-6}$ haloalkoxy, or —CN;

R$^7$ is hydrogen, C$_{1-6}$ alkyl, C$_{1-6}$ hydroxyalkyl, C$_{1-6}$ aminoalkyl, C$_{1-6}$ alkoxy, C$_{2-6}$ alkoxyalkyl, C$_{1-6}$ alkylthio, halogen, C$_{1-6}$ haloalkyl, —CN, —OH, —NH$_2$, C$_{3-10}$ cycloalkyl, C$_{1-6}$ alkyl-C$_{3-10}$ cycloalkyl, heterocycloalkyl, or C$_{1-6}$ alkyl-(heterocycloalkyl);

each heterocycloalkyl is a 3 to 20 membered ring having 1 to 4 heteroatoms each independently N, O or S; and each heteroaryl is a 5 to 18 membered ring having 1 to 4 heteroatoms each independently N, O or S;

provided that R$^5$ and R$^6$ are not both C$_{1a}$ alkyl; and when R$^5$ is hydrogen, R$^6$ is not isopropyl or phenyl substituted with 2-Me.

In some embodiments, the present disclosure provides a compound of Formula (I):

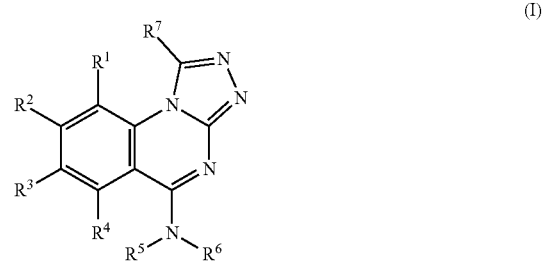

(I)

or a pharmaceutically acceptable salt thereof, wherein

R$^1$ is hydrogen, C$_{1-6}$ alkyl, C$_{2-6}$ alkenyl, C$_{2-6}$ alkynyl, C$_{1-6}$ alkoxy, halogen, C$_{1-6}$ haloalkyl, C$_{1-6}$ haloalkoxy, or —CN;

R$^2$ is hydrogen, C$_{1-6}$ alkyl, C$_{2-6}$ alkenyl, C$_{2-6}$ alkynyl, C$_{1-6}$ hydroxyalkyl, C$_{1-6}$ alkoxy, C$_{2-6}$ alkoxyalkyl, halogen, C$_{1-6}$ haloalkyl, C$_{1-6}$ haloalkoxy, —CN, —NO, —NO$_2$, —C(O)R$^{2a}$, —C(O)OR$^{2a}$, —OC(O)R$^{2a}$, —C(O)N(R$^{2a}$)(R$^{2b}$), —N(R$^{2a}$)C(O)R$^{2b}$, —OC(O)N(R$^{2a}$)(R$^{2b}$), —N(R$^{2a}$)C(O)OR$^{2b}$, —C(=NR$^{2a}$)N(R$^{2b}$)(R$^{2c}$), —N(R$^{2a}$)(R$^{2b}$), —OR$^{2a}$, —SR$^{2a}$, —S(O)R$^{2a}$, —S(O)$_2$R$^{2a}$, —S(O)$_2$N(R$^{2a}$)(R$^{2b}$), —N(R$^{2a}$)S(O)$_2$(R$^{2b}$), —P(O)(R$^{2a}$)(R$^{2b}$), —P(O)(OR$^{2a}$)(R$^{2b}$), —P(O)(OR$^{2a}$)(OR$^{2b}$), C$_{3-10}$ cycloalkyl, C$_{1-6}$ alkyl-C$_{3-10}$ cycloalkyl, C$_{6-12}$ aryl, C$_{1-6}$ alkyl-C$_{6-12}$ aryl, heterocycloalkyl, or heteroaryl, wherein each alkenyl or alkynyl is independently optionally substituted with 1 to 3 R$^{2a}$ groups, each cycloalkyl is optionally substituted with 1 to 3 R$^{2e}$ groups, each aryl is optionally substituted with 1 to 3 R$^{2f}$ groups, each heterocycloalkyl is optionally substituted with 1 to 3 R$^{2g}$ groups, and each heteroaryl is optionally substituted with 1 to 3 R$^{2h}$ groups;

each R$^{2a}$, R$^{2b}$, and R$^{2c}$ is independently hydrogen, C$_{1-6}$ alkyl, C$_{1-6}$ hydroxyalkyl, C$_{2-6}$ alkoxyalkyl, C$_{1-6}$ haloalkyl, $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, or heteroaryl;

alternatively, $R^{2a}$, $R^{2b}$, and $R^{2c}$ when attached to the same atom can be combined with the atom to which they are attached to form a heterocycloalkyl;

each $R^{2d}$ is independently —N($R^{2d1}$)($R^{2d2}$), —O$R^{2d1}$, $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, or heteroaryl;

each $R^{2d1}$ and $R^{2d2}$ is independently hydrogen, $C_{1-6}$ alkyl, or —C(O)O—($C_{1-6}$ alkyl);

each $R^{2e}$, $R^{2f}$, $R^{2g}$, and $R^{2h}$ is independently hydrogen, $C_{1-6}$ alkyl, $C_{1-6}$ alkoxy, halogen, $C_{1-6}$ haloalkyl or $C_{1-6}$ haloalkoxy;

$R^3$ is hydrogen, $C_{1-6}$ alkyl, $C_{2-6}$ alkenyl, $C_{2-6}$ alkynyl, $C_{1-6}$ hydroxyalkyl, $C_{1-6}$ alkoxy, $C_{2-6}$ alkoxyalkyl, halogen, $C_{1-6}$ haloalkyl, $C_{1-6}$ haloalkoxy, —CN, —NO, —NO$_2$, —C(O)$R^{3a}$, —C(O)O$R^{3a}$, —OC(O)$R^{3a}$, —C(O)N($R^{3a}$)($R^{3b}$), —N($R^{3a}$)C(O)$R^{3b}$, —OC(O)N($R^{3a}$)($R^{3b}$), —N($R^{3a}$)C(O)O$R^{3b}$, —C(=N$R^{3a}$)N($R^{3b}$)($R^{3c}$), —N($R^{3a}$)($R^{3b}$), —O$R^{3a}$, —S$R^{3a}$, —S(O)$R^{3a}$, —S(O)$_2$$R^{3a}$, —S(O)$_2$N($R^{3a}$)($R^{3b}$), —N($R^{3a}$)S(O)$_2$($R^{3b}$), —P(O)($R^{3a}$)($R^{3b}$), —P(O)(O$R^{3a}$)($R^{3b}$), —P(O)(O$R^{3a}$)(O$R^{3b}$), $C_{3-10}$ cycloalkyl, $C_{1-6}$alkyl-$C_{3-10}$ cycloalkyl, $C_{6-12}$ aryl, $C_{1-6}$ alkyl-$C_{6-12}$ aryl, heterocycloalkyl, or heteroaryl, wherein each alkenyl or alkynyl is independently optionally substituted with 1 to 3 $R^{3d}$ groups, each cycloalkyl is optionally substituted with 1 to 3 $R^{3e}$ groups, each aryl is optionally substituted with 1 to 3 $R^{3f}$ groups, each heterocycloalkyl is optionally substituted with 1 to 3 $R^{3g}$ groups, and each heteroaryl is optionally substituted with 1 to 3 $R^{3h}$ groups;

each $R^{3a}$, $R^{3b}$, and $R^{3c}$ is independently hydrogen, $C_{1-6}$ alkyl, $C_{1-6}$ hydroxyalkyl, $C_{2-6}$ alkoxyalkyl, $C_{1-6}$ haloalkyl, $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, or heteroaryl;

alternatively, $R^{3a}$, $R^{3b}$, and $R^{3c}$ when attached to the same atom can be combined with the atom to which they are attached to form a heterocycloalkyl;

each $R^{3d}$ is independently —N($R^{3d1}$)($R^{3d2}$), —O$R^{3d1}$, $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, or heteroaryl;

each $R^{3d1}$ and $R^{3d2}$ is independently hydrogen, $C_{1-6}$ alkyl, or —C(O)O—($C_{1-6}$ alkyl);

each $R^{3e}$, $R^{3f}$, $R^{3g}$, and $R^{3h}$ is independently hydrogen, $C_{1-6}$ alkyl, $C_{1-6}$ alkoxy, halogen, $C_{1-6}$ haloalkyl or $C_{1-6}$ haloalkoxy;

$R^4$ is hydrogen, $C_{1-6}$ alkyl, $C_{2-6}$ alkenyl, $C_{2-6}$ alkynyl, $C_{1-6}$ alkoxy, halogen, $C_{1-6}$ haloalkyl, $C_{1-6}$ haloalkoxy, or —CN;

$R^5$ is hydrogen, $C_{1-6}$ alkyl, $C_{2-6}$ alkenyl, $C_{2-6}$ alkynyl, $C_{1-6}$ hydroxyalkyl, $C_{2-6}$ alkoxyalkyl, $C_{1-6}$ haloalkyl, $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, $C_{1-6}$ alkyl-(heterocycloalkyl), heteroaryl, or $C_{1-6}$ alkyl-(heteroaryl), wherein the alkyl is optionally substituted with $R^{5a}$;

$R^{5a}$ is —OSi($R^{5a1}$)($R^{5a2}$)($R^{5a3}$);

$R^{5a1}$, $R^{5a2}$, and $R^{5a3}$ are each independently $C_{1-6}$ alkyl; and $R^6$ is $C_{1-6}$ alkyl, $C_{2-6}$ alkenyl, $C_{2-6}$ alkynyl, $C_{1-6}$ haloalkyl, $C_{6-12}$ aryl, or heteroaryl, wherein the aryl or heteroaryl are each optionally substituted with 1 to 3 $R^{6a}$;

each $R^{6a}$ is independently $C_{1-6}$ alkyl, $C_{2-6}$ alkenyl, $C_{2-6}$ alkynyl, $C_{1-6}$ hydroxyalkyl, $C_{1-6}$ alkoxy, $C_{2-6}$ alkoxyalkyl, halogen, $C_{1-6}$ haloalkyl, $C_{1-6}$ haloalkoxy, —CN, —NO$_2$, —C(O)$R^{6b}$, —C(O)O$R^{6b}$, —OC(O)$R^{6b}$, —C(O)N($R^{6b}$)($R^{6c}$), —N($R^{6b}$)C(O)$R^{6c}$, —C(=N$R^{6b}$)N($R^{6c}$)($R^{6d}$), —N($R^{6b}$)($R^{6c}$), —O$R^{6b}$, —S$R^{6b}$, —S(O)$R^{6b}$, —S(O)$_2$$R^{6b}$, —S(O)$_2$N($R^{6b}$)($R^{6c}$), —N($R^{6b}$)S(O)$_2$($R^{6c}$), $C_{3-10}$ cycloalkyl, $C_{6-12}$ aryl, heterocycloalkyl, or heteroaryl, wherein the cycloalkyl, aryl, heterocycloalkyl, or heteroaryl is each optionally substituted with 1 to 3 $R^{6e}$, and the alkyl is optionally substituted with $R^{6f}$;

or $R^5$ and one $R^{6a}$ together with the atoms to which they are attached form a heterocycloalkyl, optionally substituted with 1 to 3 $R^{6g}$;

each $R^{6b}$, $R^{6c}$ and $R^{6d}$ is independently hydrogen, $C_{1-6}$ alkyl, $C_{1-6}$ hydroxyalkyl, $C_{2-6}$ alkoxyalkyl, $C_{1-6}$ haloalkyl, $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, or heteroaryl;

each $R^{6e}$ is independently $C_{1-6}$ alkyl, $C_{2-6}$ alkenyl, $C_{2-6}$ alkynyl, $C_{1-6}$ hydroxyalkyl, $C_{1-6}$ alkoxy, $C_{2-6}$ alkoxyalkyl, halogen, $C_{1-6}$ haloalkyl, $C_{1-6}$ haloalkoxy, —CN, —NO$_2$, —C(O)$R^{6e1}$, —C(O)O$R^{6e1}$, —OC(O)$R^{6e1}$, —C(O)N($R^{6e1}$)($R^{6e2}$), —N($R^{6e1}$)C(O)$R^{6e2}$, —C(=N$R^{6e1}$)N($R^{6e2}$)($R^{6e3}$), —N($R^{6e1}$)($R^{6e2}$), —O$R^{6e1}$, —S$R^{6e1}$, —S(O)$R^{6e1}$, —S(O)$_2$$R^{6e1}$, —S(O)$_2$N($R^{6e1}$)($R^{6e2}$), —N($R^{6e1}$)S(O)$_2$($R^{6e2}$), $C_{3-10}$ cycloalkyl, $C_{6-12}$ aryl, heterocycloalkyl, or heteroaryl, wherein the cycloalkyl, aryl, heterocycloalkyl, or heteroaryl is each optionally substituted with 1 to 3 $R^{6h}$;

each $R^{6e1}$, $R^{6e2}$, and $R^{6e3}$ is independently hydrogen or $C_{1-6}$ alkyl;

$R^{6f}$ is —OSi($R^{6f1}$)($R^{6f2}$)($R^{6f3}$);

$R^{6f1}$, $R^{6f2}$, and $R^{6f3}$ are each independently $C_{1-6}$ alkyl;

each $R^{6g}$ is independently $C_{1-6}$ alkyl, $C_{2-6}$ alkenyl, $C_{2-6}$ alkynyl, halogen, $C_{1-6}$ haloalkyl, $C_{1-6}$ haloalkoxy, or —CN;

each $R^{6h}$ is independently $C_{1-6}$ alkyl, $C_{2-6}$ alkenyl, $C_{2-6}$ alkynyl, $C_{1-6}$ alkoxy, halogen, $C_{1-6}$ haloalkyl, $C_{1-6}$ haloalkoxy, —C(O)$R^{6h1}$, —C(O)O$R^{6h1}$, —OC(O)$R^{6h1}$, —C(O)N($R^{6h1}$)($R^{6h2}$), —N($R^{6h1}$)C(O)$R^{6h2}$, —C(=N$R^{6h1}$)N($R^{6h2}$)($R^{6h3}$), —N($R^{6h1}$)($R^{6h2}$), —OH, —S$R^{6h1}$, —S(O)$R^{6h1}$, —S(O)$_2$$R^{6h1}$, —S(O)$_2$N($R^{6h1}$)($R^{6h2}$), or —N($R^{6h1}$)S(O)$_2$($R^{6h2}$);

each $R^{6h1}$, $R^{6h2}$, and $R^{6h3}$ is independently hydrogen or $C_{1-6}$ alkyl;

$R^7$ is hydrogen, $C_{1-6}$ alkyl, halogen, $C_{1-6}$ haloalkyl, —CN, or —OH;

each heterocycloalkyl is a 3 to 10 membered ring having 1 to 4 heteroatoms each independently N, O or S; and each heteroaryl is a 5 to 10 membered ring having 1 to 4 heteroatoms each independently N, O or S, provided that $R^5$ and $R^6$ are not both C$_{1a}$ alkyl; and when $R^5$ is hydrogen, $R^6$ is not isopropyl or phenyl substituted with 2-Me.

In some embodiments, the compound of Formula (I) or (I-1), or a pharmaceutically acceptable salt thereof, is the compound wherein $R^5$ is $C_{1-6}$ alkyl, $C_{2-6}$ alkenyl, $C_{2-6}$ alkynyl, $C_{1-6}$ hydroxyalkyl, $C_{2-6}$ alkoxyalkyl, $C_{1-6}$ haloalkyl, $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, $C_{1-6}$ alkyl-(heterocycloalkyl), heteroaryl, or $C_{1-6}$ alkyl-(heteroaryl), wherein the alkyl is optionally substituted with $R^{5a}$; and $R^6$ is $C_{6-12}$ aryl or heteroaryl, wherein the aryl or heteroaryl are each optionally substituted with 1 to 3 $R^{6a}$; or $R^5$ and $R^{6a}$ together with the atoms to which they are attached form a heterocycloalkyl, optionally substituted with 1 to 3 $R^{6g}$.

In some embodiments, the compound of Formula (I), (I-1), (Ia), (Ib), (Ic), (IIa), (IIc), (IIc-3), (IIc-4), (IIc-5), (IIc-6), (IIc-7), or (IIc-8), or a pharmaceutically acceptable salt thereof, is the compound wherein $R^1$ is hydrogen, $C_{1-6}$ alkyl, $C_{1-6}$ alkoxy, halogen, $C_{1-6}$ haloalkyl, or —CN. In some embodiments, the compound of Formula (I), (I-1), (Ia), (Ib), (Ic), (IIa), (IIc), (IIc-3), (IIc-4), (IIc-5), (IIc-6), (IIc-7), or (IIc-8), or a pharmaceutically acceptable salt thereof, is the compound wherein $R^1$ is hydrogen, $C_{1-3}$ alkyl, $C_{1-3}$ alkoxy, or halogen. In some embodiments, the compound of Formula (I), (I-1), (Ia), (Ib), (Ic), (IIa), (IIc), (IIc-3), (IIc-4), (IIc-5), (IIc-6), (IIc-7), or (IIc-8), or a pharmaceutically acceptable salt thereof, is the compound wherein $R^1$ is hydrogen, Me, —OMe, F, or Cl. In some embodiments, the compound of Formula (I), (I-1), (Ia), (Ib), (Ic), (IIa), (IIc), (IIc-3), (IIc-4), (IIc-5), (IIc-6), (IIc-7), or (IIc-8), or a pharmaceutically acceptable salt thereof, is the compound wherein $R^1$ is hydrogen or F. In some embodiments, the compound of Formula (I), (I-1), (Ia), (Ib), (Ic), (IIa), (IIc), (IIc-3), (IIc-4), (IIc-5), (IIc-6), (IIc-7), or (IIc-8), or a pharmaceutically acceptable salt thereof, is the compound wherein $R^1$ is hydrogen. In some embodiments, the compound of Formula (I), (I-1), (Ia), (Ib), (Ic), (IIa), (IIc), (IIc-3), (IIc-4), (IIc-5), (IIc-6), (IIc-7), or (IIc-8), or a pharmaceutically acceptable salt thereof, is the compound wherein $R^1$ is F.

In some embodiments, the compound of Formula (I), (I-1), (Ia), (Ia-1), (Ib), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein $R^2$ is hydrogen, $C_{1-6}$ alkyl, $C_{2-6}$ alkenyl, $C_{2-6}$ alkynyl, $C_{1-6}$ hydroxyalkyl, $C_{1-6}$ alkoxy, $C_{2-6}$ alkoxyalkyl, halogen, $C_{1-6}$ haloalkyl, $C_{1-6}$ haloalkoxy, —CN, —NO, —NO$_2$, —C(O)R$^{2a}$, —C(O)OR$^{2a}$, —OC(O)R$^{2a}$, —C(O)N(R$^{2a}$)(R$^{2b}$), —N(R$^{2a}$)C(O)R$^{2b}$, —OC(O)N(R$^{2a}$)(R$^{2b}$), —N(R$^{2a}$)C(O)OR$^{2b}$, —N(R$^{2a}$)(R$^{2b}$), —OR$^{2a}$, —S(O)$_2$N(R$^{2a}$)(R$^{2b}$), —N(R$^{2a}$)S(O)$_2$(R$^{2b}$), $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, or heteroaryl, wherein each alkenyl or alkynyl is independently optionally substituted with 1 to 3 R$^{2d}$ groups, and each aryl is optionally substituted with 1 to 3 R$^{2f}$ groups. In some embodiments, the compound of Formula (I), (I-1), (Ia), (Ia-1), (Ib), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein $R^2$ is hydrogen, $C_{1-6}$ alkyl, $C_{2-6}$ alkenyl, $C_{2-6}$ alkynyl, $C_{1-6}$ hydroxyalkyl, $C_{1-6}$ alkoxy, $C_{2-6}$ alkoxyalkyl, halogen, $C_{1-6}$ haloalkyl, —CN, —NO, —NO$_2$, —C(O)R$^{2a}$, —C(O)OR$^{2a}$, —N(R$^{2a}$)C(O)R$^{2b}$, —N(R$^{2a}$)(R$^{2b}$), —OR$^{2a}$, —N(R$^{2a}$)S(O)$_2$(R$^{2b}$), $C_{3-10}$ cycloalkyl, $C_{6-10}$ aryl, heterocycloalkyl, or heteroaryl, wherein each alkenyl or alkynyl is independently optionally substituted with 1 to 3 R$^{2d}$ groups, and each aryl is optionally substituted with 1 to 3 R$^{2f}$ groups. In some embodiments, the compound of Formula (I), (I-1), (Ia), (Ia-1), (Ib), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein $R^2$ is hydrogen, $C_{1-3}$ alkyl, $C_{2-3}$ alkenyl, $C_{2-6}$ alkynyl, $C_{1-3}$ hydroxyalkyl, $C_{1-3}$ alkoxy, $C_{2-3}$ alkoxyalkyl, halogen, $C_{1-3}$ haloalkyl, —CN, —NO, —NO$_2$, —C(O)R$^{2a}$, —C(O)OR$^{2a}$, —N(R$^{2a}$)C(O)R$^{2b}$, —N(R$^{2a}$)(R$^{2b}$), —N(R$^{2a}$)S(O)$_2$(R$^{2b}$), $C_{3-6}$ cycloalkyl, phenyl, heterocycloalkyl, or heteroaryl, wherein each alkenyl or alkynyl is independently optionally substituted with 1 R$^{2d}$ group, and each phenyl is optionally substituted with 1 R$^{2f}$ group. In some embodiments, the compound of Formula (I), (I-1), (Ia), (Ia-1), (Ib), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein $R^2$ is hydrogen, $C_{1-3}$ alkyl, $C_{2-3}$ alkenyl, $C_{2-6}$ alkynyl, $C_{1-3}$ hydroxyalkyl, $C_{2-3}$ alkoxyalkyl, halogen, —CN, —NO, —NO$_2$, —C(O)R$^{2a}$, —N(R$^{2a}$)C(O)R$^{2b}$, —N(R$^{2a}$)(R$^{2b}$), —OR$^{2a}$, or heteroaryl; and the heteroaryl is a 5 to 6 membered ring having 1 to 3 heteroatoms each independently N, O, or S.

In some embodiments, the compound of Formula (I), (I-1), (Ia), (Ia-1), (Ib), (Ic), (IIa), (IIa-1), (IIc), (Ic-1), (IIc-2), (IIc-3), (IIc-4), (IIc-5), (IIc-6), (IIc-7), or (IIc-8), or a pharmaceutically acceptable salt thereof, is the compound wherein each R$^{2a}$ and R$^{2b}$ is independently hydrogen, $C_{1-6}$ alkyl, $C_{1-6}$ hydroxyalkyl, or $C_{2-6}$ alkoxyalkyl. In some embodiments, the compound of Formula (I), (I-1), (Ia), (Ia-1), (Ib), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein each R$^{2a}$ and R$^{2b}$ is independently hydrogen, $C_{1-3}$ alkyl, $C_{1-3}$ hydroxyalkyl, or $C_{2-3}$ alkoxyalkyl. In some embodiments, the compound of Formula (I), (I-1), (Ia), (Ia-1), (Ib), (Ic), (IIa), (IIa-1), (Ic), (Ic-1), (IIc-2), (IIc-3), (IIc-4), (IIc-5), (IIc-6), (IIc-7), or (IIc-8), or a pharmaceutically acceptable salt thereof, is the compound wherein each R$^{2a}$ and R$^{2b}$ is independently hydrogen or $C_{1-3}$ alkyl. In some embodiments, the compound of Formula (I), (I-1), (Ia), (Ia-1), (Ib), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein each R$^{2a}$ and R$^{2b}$ is independently hydrogen or Me.

In some embodiments, the compound of Formula (I), (I-1), (Ia), (Ia-1), (Ib), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein each R$^{2d}$ is independently —N(R$^{2d1}$)(R$^{2d2}$), —OR$^{2d1}$, $C_{3-10}$ cycloalkyl, or $C_{6-12}$ aryl. In some embodiments, the compound of Formula (I), (I-1), (Ia), (Ia-1), (Ib), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein each R$^{2d}$ is independently —N(R$^{2d1}$)(R$^{2d2}$), —OR$^{2d1}$, $C_{3-8}$ cycloalkyl, or phenyl.

In some embodiments, the compound of Formula (I), (I-1), (Ia), (Ia-1), (Ib), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein each R$^{2d1}$ and R$^{2d2}$ is independently hydrogen, $C_{1-4}$ alkyl, or —C(O)O(C$_{1-4}$ alkyl). In some embodiments, the compound of Formula (I), (I-1), (Ia), (Ia-1), (Ib), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein each R$^{2d1}$ and R$^{2d2}$ is independently hydrogen or —C(O)O(C$_{1-4}$ alkyl). In some embodiments, the compound of Formula (I), (I-1), (Ia), (Ia-1), (Ib), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein each R$^{2d1}$ and R$^{2d2}$ is independently hydrogen or —C(O)OtBu. In some embodiments, the compound of Formula (I), (I-1), (Ia), (Ia-1), (Ib) or (Ic), or a pharmaceutically acceptable salt thereof, is the compound wherein each R$^{2d1}$ and R$^{2d2}$ is hydrogen.

In some embodiments, the compound of Formula (I), (I-1), (Ia), (Ia-1), (Ib), (Ic), (IIa), (IIa-1), (Ic), (IIc-1), (IIc-2), (IIc-3), (IIc-4), (IIc-5), (IIc-6), (IIc-7), or (IIc-8), or a pharmaceutically acceptable salt thereof, is the compound wherein each R$^{2f}$ is independently $C_{1-6}$ alkoxy or halogen. In some embodiments, the compound of Formula (I), (I-1), (Ia), (Ia-1), (Ib), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein each R²¹ is independently $C_{1-3}$ alkoxy or halogen. In some embodiments, the compound of Formula (I), (I-1), (Ia), (Ia-1), (Ib), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein each R²¹ is independently —OMe or F.

In some embodiments, the compound of Formula (I), (I-1), (Ia), (Ia-1), (Ib), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein $R^2$ is hydrogen, $C_{1-6}$ alkyl, $C_{2-6}$ alkenyl, $C_{2-6}$ alkynyl, $C_{1-6}$ hydroxyalkyl, $C_{1-6}$ alkoxy, $C_{2-6}$ alkoxyalkyl, halogen, $C_{1-6}$ haloalkyl, $C_{1-6}$ haloalkoxy, —CN, —NO, —NO₂, —C(O)R²ᵃ, —C(O)OR²ᵃ, —OC(O)R²ᵃ, —C(O)N(R²ᵃ)(R²ᵇ), —N(R²ᵃ)C(O)R²ᵇ, —OC(O)N(R²ᵃ)(R²ᵇ), —N(R²ᵃ)C(O)OR²ᵇ, —N(R²ᵃ)(R²ᵇ), —OR²ᵃ, —S(O)₂N(R²ᵃ)(R²ᵇ), —N(R²ᵃ)S(O)₂(R²ᵇ), $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, a 3 to 8 membered heterocycloalkyl ring having 1 to 3 heteroatoms each independently N, O, or S, or a 5 to 10 membered heteroaryl ring having 1 to 3 heteroatoms each independently N, O, or S, wherein each alkenyl or alkynyl is independently optionally substituted with 1 to 3 R²ᵈ groups, and each aryl is optionally substituted with 1 to 3 R²ᶠ groups; each R²ᵃ and R²ᵇ is independently hydrogen, $C_{1-6}$ alkyl, $C_{1-6}$ hydroxyalkyl, $C_{2-6}$ alkoxyalkyl, or $C_{1-6}$ haloalkyl; each R²ᵈ is independently —N(R²ᵈ¹)(R²ᵈ²), —OR²ᵈ¹, $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl; each R²ᵈ¹ and R²ᵈ² is independently hydrogen, $C_{1-6}$ alkyl, or —C(O)O—($C_{1-6}$ alkyl); and each R²ᶠ is independently hydrogen, $C_{1-6}$ alkyl, $C_{1-6}$ alkoxy, or halogen.

In some embodiments, the compound of Formula (I), (I-1), (Ia), (Ia-1), (Ib), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein $R^2$ is hydrogen, $C_{1-6}$ alkyl, $C_{2-6}$ alkenyl, $C_{2-6}$ alkynyl, $C_{1-6}$ hydroxyalkyl, $C_{1-6}$ alkoxy, $C_{2-6}$ alkoxyalkyl, halogen, $C_{1-6}$ haloalkyl, —CN, —NO, —NO₂, —C(O)R²ᵃ, —C(O)OR²ᵃ, —N(R²ᵃ)C(O)R²ᵇ, —N(R²ᵃ)(R²ᵇ), —OR²ᵃ, —N(R²ᵃ)S(O)₂(R²ᵇ), $C_{3-10}$ cycloalkyl, $C_{6-10}$ aryl, a 5 to 8 membered heterocycloalkyl ring having 1 to 2 heteroatoms each independently N, O, or S, or a 5 to 6 membered heteroaryl ring having 1 to 3 heteroatoms each independently N, O, or S, wherein each alkenyl or alkynyl is independently optionally substituted with 1 to 3 R²ᵈ groups, and each aryl is optionally substituted with 1 to 3 R²ᶠ groups; each R²ᵃ and R²ᵇ is independently hydrogen, $C_{1-6}$ alkyl, $C_{1-6}$ hydroxyalkyl, or $C_{2-6}$ alkoxyalkyl; each R²ᵈ is independently —N(R²ᵈ¹)(R²ᵈ²), —OR²ᵈ¹, $C_{3-10}$ cycloalkyl, or $C_{6-12}$ aryl; each R²ᵈ¹ and R²ᵈ² is independently hydrogen, $C_{1-4}$ alkyl, or —C(O)O—($C_{1-4}$ alkyl); and each R²ᶠ is independently $C_{1-6}$ alkoxy or halogen.

In some embodiments, the compound of Formula (I), (I-1), (Ia), (Ia-1), (Ib), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein $R^2$ is hydrogen, $C_{1-3}$ alkyl, $C_{2-3}$ alkenyl, $C_{2-6}$ alkynyl, $C_{1-3}$ hydroxyalkyl, $C_{1-3}$ alkoxy, $C_{2-3}$ alkoxyalkyl, halogen, $C_{1-3}$ haloalkyl, —CN, —NO, —NO₂, —C(O)R²ᵃ, —C(O)OR²ᵃ, —N(R²ᵃ)C(O)R²ᵇ, —N(R²ᵃ)(R²ᵇ), —N(R²ᵃ)S(O)₂(R²ᵇ), $C_{3-6}$ cycloalkyl, phenyl, 5 to 6 membered heterocycloalkyl ring having 1 to 2 heteroatoms each independently N or O, or a 5 to 6 membered heteroaryl ring having 1 to 2 heteroatoms each independently N, O, or S, wherein each alkenyl or alkynyl is independently optionally substituted with 1 R²ᵈ group, and each phenyl is optionally substituted with 1 R²¹ group; each R²ᵃ and R²ᵇ is independently hydrogen, $C_{1-3}$ alkyl, $C_{1-3}$ hydroxyalkyl, or $C_{2-3}$ alkoxyalkyl; each R²ᵈ is independently —N(R²ᵈ¹)(R²ᵈ²), —OR²ᵈ¹, $C_{3-8}$ cycloalkyl, or phenyl; each R²ᵈ¹ and R²ᵈ² is independently hydrogen or —C(O)O—($C_{1-4}$ alkyl); and each R²¹ is independently $C_{1-3}$ alkoxy or halogen.

In some embodiments, the compound of Formula (I), (I-1), (Ia), (Ia-1), (Ib), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein $R^2$ is hydrogen, Me, Et, iPr, —CH=CH₂, —CH=CHMe, —C(Me)=CH₂, —CMe=CHMe, —CH=C(Me)₂, —CH=CHEt, —C≡CH, —C≡C-Me, —C≡C-Et, —C≡C-tBu, —C≡C—CH₂OH, —C≡C—CMe₂(OH), —C≡C—CH₂NH₂, —C≡C—CH₂NHC(O)OtBu, —C≡C—CMe₂(SO₂Me), —CH₂OH, —CH₂CH₂CH₂OH, —CH(OH)CH₂CH₃, —OMe, —OEt, —OCH₂CH=CH₂, —CH₂OMe, —CH₂NHMe, —CH₂NMe₂, —CH₂CH₂COOEt, F, Cl, Br, I, —CF₃, —CN, —NO, —NO₂, —C(O)H, —COOH, —COOMe, —NHCOMe, —NH₂, —NHMe, —NMe₂, —NHCH₂CH₂OH, —NHCH₂CH₂OMe, —NHSO₂Me, —OH, —NH—N=CH—OEt, —NH₂—NH₂, SMe, SO₂Me, cyclopropyl,

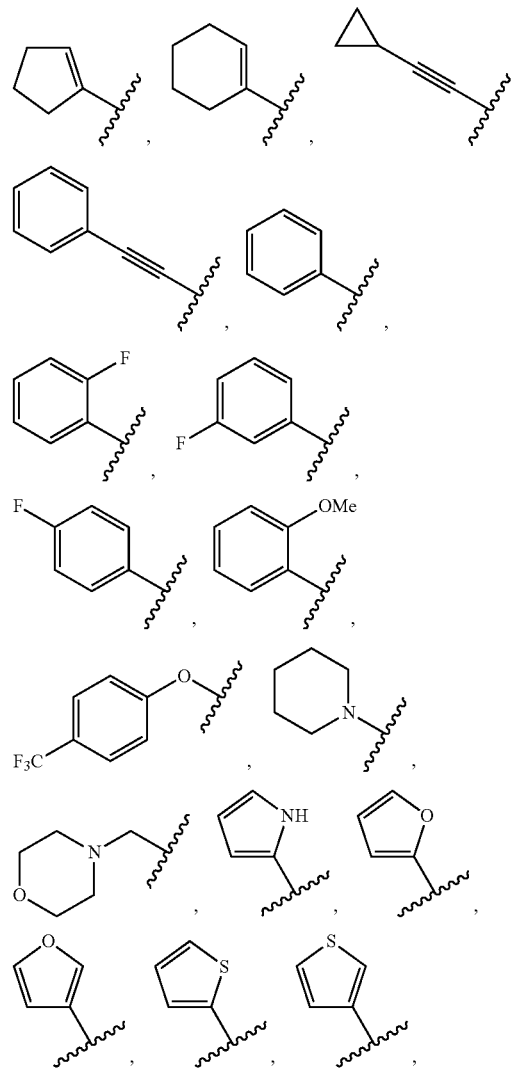

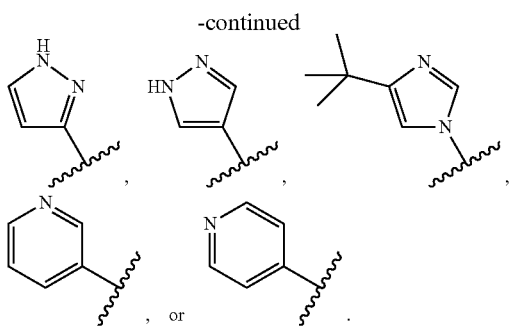

In some embodiments, the compound of Formula (I), (I-1), (Ia), (Ia-1), (Ib), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein $R^2$ is hydrogen, Me, Et, iPr, —CH=CH$_2$, —C(Me)=CH$_2$, —C≡C-Me, —C≡C-tBu, —C≡C—CH$_2$OH, —C≡C—CH$_2$NH$_2$, —C≡C—CH$_2$NHC(O)OtBu, —CH$_2$H, —OMe, —CH$_2$OMe, F, Cl, Br, I, —CF$_3$, —CN, —NO, —NO$_2$, —C(O)H, —COOH, —COOMe, —NHCOMe, —NH$_2$, —NHMe, —NMe$_2$, —NHCH$_2$CH$_2$OH, —NHCH$_2$CH$_2$OMe, —NHSO$_2$Me, —OH, cyclopropyl,

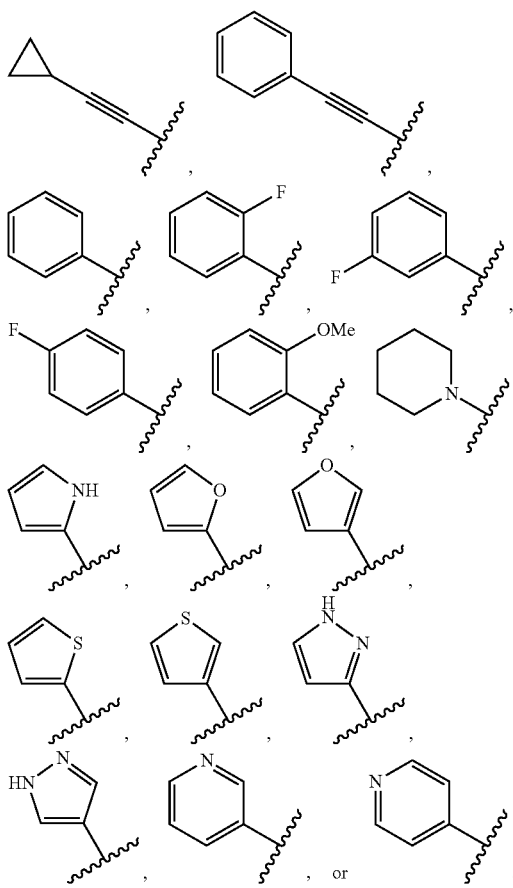

In some embodiments, the compound of Formula (I), (I-1), (Ia), (Ia-1), (Ib), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein $R^3$ is hydrogen, $C_{1-6}$ alkyl, $C_{2-6}$ alkenyl, $C_{2-6}$ alkynyl, $C_{1-6}$ hydroxyalkyl, $C_{1-6}$ alkoxy, $C_{2-6}$ alkoxyalkyl, halogen, $C_{1-6}$ haloalkyl, $C_{1-6}$ haloalkoxy, —CN, —NO, —NO$_2$, —C(O)R$^{3a}$, —C(O)OR$^{3a}$, —OC(O)R$^{3a}$, —C(O)N(R$^{3a}$)(R$^{3b}$), —N(R$^{3a}$)C(O)R$^{3b}$, —OC(O)N(R$^{3a}$)(R$^{3b}$), —N(R$^{3a}$)C(O)OR$^{3b}$, —N(R$^{3a}$)(R$^{3b}$), —OR$^{3a}$, —S(O)$_2$N(R$^{3a}$)(R$^{3b}$), —N(R$^{3a}$)S(O)$_2$(R$^{3b}$), $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, or heteroaryl, wherein each alkenyl or alkynyl is independently optionally substituted with 1 to 3 $R^{3d}$ groups, and each aryl is optionally substituted with 1 to 3 $R^{3f}$ groups.

In some embodiments, the compound of Formula (I), (I-1), (Ia), (Ia-1), (Ib), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein $R^3$ is hydrogen, $C_{1-6}$ alkyl, $C_{2-6}$ alkenyl, $C_{2-6}$ alkynyl, $C_{1-6}$ hydroxyalkyl, $C_{1-6}$ alkoxy, $C_{2-6}$ alkoxyalkyl, halogen, $C_{1-6}$ haloalkyl, $C_{1-6}$ haloalkoxy, —CN, —NO, —NO$_2$, —C(O)R$^{3a}$, —C(O)OR$^{3a}$, —OC(O)R$^{3a}$, —C(O)N(R$^{3a}$)(R$^{3b}$), —N(R$^{3a}$)C(O)R$^{3b}$, —OC(O)N(R$^{3a}$)(R$^{3b}$), —N(R$^{3a}$)C(O)OR$^{3b}$, —N(R$^{3a}$)(R$^{3b}$), —OR$^{3a}$, —S(O)$_2$N(R$^{3a}$)(R$^{3b}$), —N(R$^{3a}$)S(O)$_2$(R$^{3b}$), $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, a 3 to 8 membered heterocycloalkyl ring having 1 to 3 heteroatoms each independently N, O, or S, or a 5 to 10 membered heteroaryl ring having 1 to 3 heteroatoms each independently N, O, or S, wherein each alkenyl or alkynyl is independently optionally substituted with 1 to 3 $R^{3d}$ groups, and each aryl is optionally substituted with 1 to 3 $R^{3f}$ groups; each $R^{3a}$ and $R^{3b}$ is independently hydrogen, $C_{1-6}$ alkyl, $C_{1-6}$ hydroxyalkyl, or $C_{2-6}$ alkoxyalkyl; each $R^{3d}$ is independently —N(R$^{3d1}$)(R$^{3d2}$), —OR$^{3d1}$, $C_{3-10}$ cycloalkyl, or $C_{6-12}$ aryl; each $R^{3d1}$ and $R^{3d2}$ is independently hydrogen, $C_{1-4}$ alkyl, or —C(O)O—($C_{1-4}$ alkyl); and each $R^{3f}$ is independently $C_{1-6}$ alkoxy or halogen.

In some embodiments, the compound of Formula (I), (I-1), (Ia), (Ia-1), (Ib), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein $R^3$ is hydrogen, $C_{1-6}$ alkyl, $C_{1-6}$ hydroxyalkyl, $C_{1-6}$ alkoxy, $C_{2-6}$ alkoxyalkyl, halogen, $C_{1-6}$ haloalkyl, —CN, —NO$_2$, —C(O)OR$^{3a}$, —C(O)N(R$^{3a}$)(R$^{3b}$), —N(R$^{3a}$)(R$^{3b}$), —N(R$^{3a}$)S(O)$_2$(R$^{3b}$), or a 5 to 6 membered heteroaryl ring having 1 to 3 heteroatoms each independently N, O, or S; and each $R^{3a}$ and $R^{3b}$ is independently hydrogen or $C_{1-6}$ alkyl. In some embodiments, the compound of Formula (I), (I-1), (Ia), (Ia-1), (Ib), (Ic), (IIa), (IIa-1), (Ic), (IIc-1), (IIc-2), (IIc-3), (IIc-4), (IIc-5), (IIc-6), (IIc-7), or (IIc-8), or a pharmaceutically acceptable salt thereof, is the compound wherein $R^3$ is hydrogen, $C_{1-3}$ alkyl, $C_{1-3}$ hydroxyalkyl, $C_{1-3}$ alkoxy, $C_{2-3}$ alkoxyalkyl, halogen, $C_{1-3}$ haloalkyl, —CN, —NO$_2$, —C(O)OR$^{3a}$, —C(O)N(R$^{3a}$)(R$^{3b}$), —N(R$^{3a}$)(R$^{3b}$), —N(R$^{3a}$)S(O)$_2$(R$^{3b}$), or a 5 to 6 membered heteroaryl ring having 1 or 2 heteroatoms each N; and each $R^{3a}$ and $R^{3b}$ is independently hydrogen or $C_{1-3}$ alkyl. In some embodiments, the compound of Formula (I), (I-1), (Ia), (Ia-1), (Ib), (Ic), (IIa), (IIa-1), (Ic), (IIc-1), (IIc-2), (IIc-3), (IIc-4), (IIc-5), (IIc-6), (IIc-7), or (IIc-8), or a pharmaceutically acceptable salt thereof, is the compound wherein $R^3$ is hydrogen, Me, Et, —CH$_2$OH, —OMe, —CH$_2$OMe, F, Cl, Br, —CF$_3$, —CN, —NO$_2$, —COOMe, —CONH$_2$, —NH$_2$, —NHSO$_2$Me, or

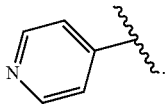

In some embodiments, the compound of Formula (I), (I-1), (Ia), (Ia-1), (Ib), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein $R^3$ is hydrogen, $C_{1-6}$ alkyl, $C_{1-6}$ hydroxyalkyl, $C_{1-6}$ alkoxy, $C_{2-6}$ alkoxyalkyl, halogen, —CN, —NO$_2$, —C(O)OR$^{3a}$, —C(O)N(R$^{3a}$)(R$^{3b}$), —N(R$^{3a}$)(R$^{3b}$), —N(R$^{3a}$)S(O)$_2$(R$^{3b}$), or a 5 to 6 membered heteroaryl ring having 1 to 3 heteroatoms each independently N, O, or S; and each $R^{3a}$ and $R^{3b}$ is independently hydrogen or $C_{1-6}$ alkyl. In some embodiments, the compound of Formula (I), (I-1), (Ia), (Ia-1), (Ib), (Ic), (IIa), (IIa-1), (Ic), (IIc-1), (IIc-2), (IIc-3), (IIc-4), (IIc-5), (IIc-6), (IIc-7), or (IIc-8), or a pharmaceutically acceptable salt thereof, is the compound wherein $R^3$ is hydrogen, $C_{1-3}$ alkyl, $C_{1-3}$ hydroxyalkyl, $C_{1-3}$ alkoxy, $C_{2-3}$ alkoxyalkyl, halogen, —CN, —NO$_2$, —C(O)OR$^{3a}$, —C(O)N(R$^{3a}$)(R$^{3b}$), —N(R$^{3a}$)(R$^{3b}$), —N(R$^{3a}$)S(O)$_2$(R$^{3b}$), or heteroaryl. In some embodiments, the compound of Formula (I), (I-1), (Ia), (Ia-1), (Ib), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein $R^3$ is hydrogen, $C_{1-3}$ alkyl, $C_{1-3}$ hydroxyalkyl, $C_{1-3}$ alkoxy, $C_{2-3}$ alkoxyalkyl, halogen, —CN, —NO$_2$, —C(O)OR$^{3a}$, —C(O)N(R$^{3a}$)(R$^{3b}$), —N(R$^{3a}$)(R$^{3b}$), —N(R$^{3a}$)S(O)$_2$(R$^{3b}$), or a 5 to 6 membered heteroaryl ring having 1 or 2 heteroatoms each N; and each $R^{3a}$ and $R^{3b}$ is independently hydrogen or $C_{1-3}$ alkyl.

In some embodiments, the compound of Formula (I), (I-1), (Ia), (Ia-1), (Ib), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein $R^3$ is hydrogen, $C_{1-3}$ alkyl, halogen, —CN or —NO$_2$. In some embodiments, the compound of Formula (I), (I-1), (Ia), (Ia-1), (Ib), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein $R^3$ is hydrogen, Me, Et, —CH$_2$OH, —OMe, —CH$_2$OMe, F, Cl, Br, —CN, —NO$_2$, —COOMe, —CONH$_2$, —NH$_2$, —NHSO$_2$Me, or

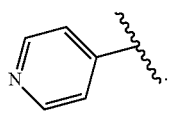

In some embodiments, the compound of Formula (I), (I-1), (Ia), (Ia-1), (Ib), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein $R^2$ is hydrogen, $C_{1-6}$ alkyl, $C_{2-6}$ alkenyl, $C_{2-6}$ alkynyl, $C_{1-6}$ hydroxyalkyl, $C_{1-6}$ alkoxy, $C_{2-6}$ alkoxyalkyl, halogen, $C_{1-6}$ haloalkyl, —CN, —NO, —NO$_2$, —C(O)R$^{2a}$, —C(O)OR$^{2a}$, —N(R$^{2a}$)C(O)R$^{2b}$, —N(R$^{2a}$)(R$^{2b}$), —OR$^{2a}$, —N(R$^{2a}$)S(O)$_2$(R$^{2b}$), $C_{3-10}$ cycloalkyl, $C_{6-10}$ aryl, heterocycloalkyl, or heteroaryl, wherein each alkenyl or alkynyl is independently optionally substituted with 1 to 3 $R^{2d}$ groups, and each aryl is optionally substituted with 1 to 3 $R^{2f}$ groups; each $R^{2a}$ and $R^{2b}$ is independently hydrogen, $C_{1-6}$ alkyl, $C_{1-6}$ hydroxyalkyl, or $C_{2-6}$ alkoxyalkyl; each $R^{2d}$ is independently —N(R$^{2d1}$)(R$^{2d2}$), —OR$^{2d1}$, $C_{3-10}$ cycloalkyl, or $C_{6-12}$ aryl; each $R^{2f}$ is independently $C_{1-6}$ alkoxy or halogen; the heterocycloalkyl is a 5 to 8 membered ring having 1 to 2 heteroatoms each independently N, O, or S; $R^3$ is hydrogen, $C_{1-6}$ alkyl, $C_{2-6}$ alkenyl, $C_{2-6}$ alkynyl, $C_{1-6}$ hydroxyalkyl, $C_{1-6}$ alkoxy, $C_{2-6}$ alkoxyalkyl, halogen, $C_{1-6}$ haloalkyl, $C_{1-6}$ haloalkoxy, —CN, —NO, —NO$_2$, —C(O)R$^{3a}$, —C(O)OR$^{3a}$, —OC(O)R$^{3a}$, —C(O)N(R$^{3a}$)(R$^{3b}$), —N(R$^{3a}$)C(O)R$^{3b}$, —OC(O)N(R$^{3a}$)(R$^{3b}$), —N(R$^{3a}$)C(O)OR$^{3b}$, —N(R$^{3a}$)(R$^{3b}$), —OR$^{3a}$, —S(O)$_2$N(R$^{3a}$)(R$^{3b}$), —N(R$^{3a}$)S(O)$_2$(R$^{3b}$), $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, or heteroaryl, wherein each alkenyl or alkynyl is independently optionally substituted with 1 to 3 $R^{3d}$ groups, and each aryl is optionally substituted with 1 to 3 $R^{3f}$ groups; and the heteroaryl is a 5 to 6 membered ring having 1 to 3 heteroatoms each independently N, O, or S.

In some embodiments, the compound of Formula (I), (I-1), (Ia), (Ia-1), (Ib), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein $R^2$ is hydrogen, $C_{1-3}$ alkyl, $C_{2-3}$ alkenyl, $C_{2-6}$ alkynyl, $C_{1-3}$ hydroxyalkyl, $C_{1-3}$ alkoxy, $C_{2-3}$ alkoxyalkyl, halogen, $C_{1-3}$ haloalkyl, —CN, —NO, —NO$_2$, —C(O)R$^{2a}$, —C(O)OR$^{2a}$, —N(R$^{2a}$)C(O)R$^{2b}$, —N(R$^{2a}$)(R$^{2b}$), —N(R$^{2a}$)S(O)$_2$(R$^{2b}$), $C_{3-6}$ cycloalkyl, phenyl, heterocycloalkyl, or heteroaryl, wherein each alkenyl or alkynyl is independently optionally substituted with 1 $R^{2d}$ group, and each phenyl is optionally substituted with 1 $R^{21}$ group; each $R^{2a}$ and $R^{2b}$ is independently hydrogen, $C_{1-3}$ alkyl, $C_{1-3}$ hydroxyalkyl, or $C_{2-3}$ alkoxyalkyl; each $R^{2d}$ is independently —N(R$^{2d1}$)(R$^{2d2}$), —OR$^{2d1}$, $C_{3-8}$ cycloalkyl, or phenyl; each $R^{2f}$ is independently $C_{1-3}$ alkoxy or halogen; $R^3$ is hydrogen, $C_{1-3}$ alkyl, $C_{1-3}$ hydroxyalkyl, $C_{1-3}$ alkoxy, $C_{2-3}$ alkoxyalkyl, halogen, —CN, —NO$_2$, —C(O)OR$^{3a}$, —C(O)N(R$^{3a}$)(R$^{3b}$), —N(R$^{3a}$)(R$^{3b}$), —N(R$^{3a}$)S(O)$_2$(R$^{3b}$), or heteroaryl; each $R^{3a}$ and $R^{3b}$ is independently hydrogen or $C_{1-3}$ alkyl; the heterocycloalkyl is a 5 to 6 membered ring having 1 to 2 heteroatoms each independently N or O; and the heteroaryl is a 5 to 6 membered ring having 1 to 2 heteroatoms each independently N, O, or S.

In some embodiments, the compound of Formula (I), (I-1), (Ia), (Ib), (Ic), (IIa), (IIc), (IIc-3), (IIc-4), (IIc-5), (IIc-6), (IIc-7), or (IIc-8), or a pharmaceutically acceptable salt thereof, is the compound wherein $R^2$ is hydrogen, F or Cl. In some embodiments, the compound of Formula (I), (I-1), (Ia), (Ib), (Ic), (IIa), (IIc), (IIc-3), (IIc-4), (IIc-5), (IIc-6), (IIc-7), or (IIc-8), or a pharmaceutically acceptable salt thereof, is the compound wherein $R^2$ is hydrogen. In some embodiments, the compound of Formula (I), (I-1), (Ia), (Ib), (Ic), (IIa), (IIc), (IIc-3), (IIc-4), (IIc-5), (IIc-6), (IIc-7), or (IIc-8), or a pharmaceutically acceptable salt thereof, is the compound wherein $R^2$ is F. In some embodiments, the compound of Formula (I), (I-1), (Ia), (Ib), (Ic), (IIa), (IIc), (IIc-3), (IIc-4), (IIc-5), (IIc-6), (IIc-7), or (IIc-8), or a pharmaceutically acceptable salt thereof, is the compound wherein $R^2$ is Cl.

In some embodiments, the compound of Formula (I), (I-1), (Ia), (Ia-1), (Ib), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein $R^2$ is hydrogen, Me, Et, iPr, —CH═CH$_2$, —C(Me)═CH$_2$, —C≡C-Me, —C≡C-tBu, —C≡C—CH$_2$OH, —C≡C—CH$_2$NH$_2$, —C≡C—CH$_2$NHC(O)OtBu, —CH$_2$OH, —OMe, —CH$_2$OMe, F, Cl, Br, I, —CF$_3$, —CN, —NO, —NO$_2$, —C(O)H, —COOH, —COOMe, —NHCOMe, —NH$_2$, —NHMe, —NMe$_2$, —NHCH$_2$CH$_2$OH, —NHCH$_2$CH$_2$OMe, —NHSO$_2$Me, —OH, cyclopropyl, and R³ is hydrogen, Me, Et, —CH₂OH, —OMe, —CH₂OMe, F, Cl, Br, —CN, —NO₂, —COOMe, —CONH₂, —NH₂, —NHSO₂Me, or

[pyridin-4-yl structure].

In some embodiments, the compound of Formula (I), (I-1), (Ia), (Ib), (Ic), (IIa), (IIc), (IIc-3), (IIc-4), (IIc-5), (IIc-6), (IIc-7), or (IIc-8), or a pharmaceutically acceptable salt thereof, is the compound wherein R³ is hydrogen, F or Cl. In some embodiments, the compound of Formula (I), (I-1), (Ia), (Ib), (Ic), (IIa), (IIc), (IIc-3), (IIc-4), (IIc-5), (IIc-6), (IIc-7), or (IIc-8), or a pharmaceutically acceptable salt thereof, is the compound wherein R³ is hydrogen. In some embodiments, the compound of Formula (I), (I-1), (Ia), (Ib), (Ic), (IIa), (IIc), (IIc-3), (IIc-4), (IIc-5), (IIc-6), (IIc-7), or (IIc-8), or a pharmaceutically acceptable salt thereof, is the compound wherein R³ is F.

In some embodiments, the compound of Formula (I), (I-1), (Ia), (Ib), (Ic), (IIa), (IIc), (IIc-3), (IIc-4), (IIc-5), (IIc-6), (IIc-7), or (IIc-8), or a pharmaceutically acceptable salt thereof, is the compound wherein R⁴ is hydrogen, C₁₋₆ alkyl, C₁₋₆ alkoxy, halogen, C₁₋₆ haloalkyl, or —CN. In some embodiments, the compound of Formula (I), (I-1), (Ia), (Ib), (Ic), (IIa), (IIc), (IIc-3), (IIc-4), (IIc-5), (IIc-6), (IIc-7), or (IIc-8), or a pharmaceutically acceptable salt thereof, is the compound wherein R⁴ is hydrogen, $C_{1-6}$ alkyl, or halogen. In some embodiments, the compound of Formula (I), (I-1), (Ia), (Ib), (Ic), (IIa), (IIc), (IIc-3), (IIc-4), (IIc-5), (IIc-6), (IIc-7), or (IIc-8), or a pharmaceutically acceptable salt thereof, is the compound wherein $R^4$ is hydrogen, $C_{1-3}$ alkyl, or halogen. In some embodiments, the compound of Formula (I), (I-1), (Ia), (Ib), (Ic), (IIa), (IIc), (IIc-3), (IIc-4), (IIc-5), (IIc-6), (IIc-7), or (IIc-8), or a pharmaceutically acceptable salt thereof, is the compound wherein $R^4$ is hydrogen, Me, F, Cl, or Br. In some embodiments, the compound of Formula (I), (I-1), (Ia), (Ib), (Ic), (IIa), (IIc), (IIc-3), (IIc-4), (IIc-5), (IIc-6), (IIc-7), or (IIc-8), or a pharmaceutically acceptable salt thereof, is the compound wherein $R^4$ is hydrogen, F, or Cl. In some embodiments, the compound of Formula (I), (I-1), (Ia), (Ib), (Ic), (IIa), (IIc), (IIc-3), (IIc-4), (IIc-5), (IIc-6), (IIc-7), or (IIc-8), or a pharmaceutically acceptable salt thereof, is the compound wherein $R^4$ is hydrogen. In some embodiments, the compound of Formula (I), (I-1), (Ia), (Ib), (Ic), (IIa), (IIc), (IIc-3), (IIc-4), (IIc-5), (IIc-6), (IIc-7), or (IIc-8), or a pharmaceutically acceptable salt thereof, is the compound wherein $R^4$ is F.

In some embodiments, the compound of Formula (I), (Ic), (IIa), (IIc), (IIc-3), (IIc-4), (IIc-5), (IIc-6), (IIc-7), or (IIc-8), or a pharmaceutically acceptable salt thereof, is the compound wherein $R^1$ and $R^2$ are each hydrogen. In some embodiments, the compound of Formula (I), (Ic), (IIa), (IIc), (IIc-3), (IIc-4), (IIc-5), (IIc-6), (IIc-7), or (IIc-8), or a pharmaceutically acceptable salt thereof, is the compound wherein $R^1$ and $R^3$ are each hydrogen. In some embodiments, the compound of Formula (I), (Ic), (IIa), (IIc), (IIc-3), (IIc-4), (IIc-5), (IIc-6), (IIc-7), or (IIc-8), or a pharmaceutically acceptable salt thereof, is the compound wherein $R^1$ and $R^4$ are each hydrogen. In some embodiments, the compound of Formula (I), (Ic), (IIa), (IIc), (IIc-3), (IIc-4), (IIc-5), (IIc-6), (IIc-7), or (IIc-8), or a pharmaceutically acceptable salt thereof, is the compound wherein $R^2$ and $R^3$ are each hydrogen. In some embodiments, the compound of Formula (I), (Ic), (IIa), (IIc), (IIc-3), (IIc-4), (IIc-5), (IIc-6), (IIc-7), or (IIc-8), or a pharmaceutically acceptable salt thereof, is the compound wherein $R^2$ and $R^4$ are each hydrogen. In some embodiments, the compound of Formula (I), (Ic), (IIa), (IIc), (IIc-3), (IIc-4), (IIc-5), (IIc-6), (IIc-7), or (IIc-8), or a pharmaceutically acceptable salt thereof, is the compound wherein $R^3$ and $R^4$ are each hydrogen.

In some embodiments, the compound of Formula (I), (Ic), (IIa), (IIc), (IIc-3), (IIc-4), (IIc-5), (IIc-6), (IIc-7), or (IIc-8), or a pharmaceutically acceptable salt thereof, is the compound wherein $R^1$, $R^2$, and $R^3$ are each hydrogen. In some embodiments, the compound of Formula (I), (Ic), (IIa), (IIc), (IIc-3), (IIc-4), (IIc-5), (IIc-6), (IIc-7), or (IIc-8), or a pharmaceutically acceptable salt thereof, is the compound wherein $R^1$, $R^2$, and $R^4$ are each hydrogen. In some embodiments, the compound of Formula (I), (Ic), (IIa), (IIc), (IIc-3), (IIc-4), (IIc-5), (IIc-6), (IIc-7), or (IIc-8), or a pharmaceutically acceptable salt thereof, is the compound wherein $R^1$, $R^3$, and $R^4$ are each hydrogen. In some embodiments, the compound of Formula (I), (Ic), (IIa), (IIc), (IIc-3), (IIc-4), (IIc-5), (IIc-6), (IIc-7), or (IIc-8), or a pharmaceutically acceptable salt thereof, is the compound wherein $R^2$, $R^3$, and $R^4$ are each hydrogen.

In some embodiments, the compound of Formula (I), (Ic), (IIa), (IIc), (IIc-3), (IIc-4), (IIc-5), (IIc-6), (IIc-7), or (IIc-8), or a pharmaceutically acceptable salt thereof, is the compound wherein $R^1$ is hydrogen; $R^2$ is hydrogen, $C_{1-3}$ alkyl, $C_{2-3}$ alkenyl, $C_{2-6}$ alkynyl, $C_{1-3}$ hydroxyalkyl, $C_{2-3}$ alkoxyalkyl, halogen, —CN, —NO, —NO$_2$, —C(O)R$^{2a}$, —N(R$^{2a}$)C(O)R$^{2b}$, —N(R$^{2a}$)(R$^{2b}$), —OR$^{2a}$, or a 5 to 6 membered heteroaryl ring having 1 to 2 heteroatoms each independently N, O, or S; $R^{2a}$ and $R^{2b}$ are each independently hydrogen or $C_{1-3}$ alkyl; $R^3$ is hydrogen, $C_{1-3}$ alkyl, halogen, —CN or —NO$_2$; $R^4$ is hydrogen or halogen; and $R^7$ is hydrogen or $C_{1-3}$ alkyl.

In some embodiments, the compound of Formula (I), (Ic), (IIa), (IIc), (IIc-3), (IIc-4), (IIc-5), (IIc-6), (IIc-7), or (IIc-8), or a pharmaceutically acceptable salt thereof, is the compound wherein $R^1$ is hydrogen; $R^2$ is hydrogen, $C_{1-3}$ alkyl, $C_{2-3}$ alkenyl, $C_{2-6}$ alkynyl, $C_{1-3}$ hydroxyalkyl, $C_{2-3}$ alkoxyalkyl, halogen, —CN, —NO, —NO$_2$, —C(O)R$^{2a}$, —N(R$^{2a}$)C(O)R$^{2b}$, —N(R$^{2a}$)(R$^{2b}$), —OR$^{2a}$, or a 5 to 6 membered heteroaryl ring having 1 to 2 heteroatoms each independently N, O, or S; $R^{2a}$ and $R^{2b}$ are each independently hydrogen or $C_{1-3}$ alkyl; $R^3$ is hydrogen, $C_{1-3}$ alkyl, halogen, —CN or —NO$_2$; $R^4$ is hydrogen; and $R^7$ is hydrogen.

In some embodiments, the compound of Formula (I), (I-1), (Ia), (Ib), (Ic), (IIa), (IIc), (IIc-3), (IIc-4), (IIc-5), (IIc-6), (IIc-7), or (IIc-8), or a pharmaceutically acceptable salt thereof, is the compound wherein $R^1$ is hydrogen; $R^2$ is hydrogen, $C_{1-6}$ alkyl, $C_{2-6}$ alkenyl, $C_{2-6}$ alkynyl, $C_{1-6}$ hydroxyalkyl, $C_{1-6}$ alkoxy, $C_{2-6}$ alkoxyalkyl, halogen, $C_{1-6}$ haloalkyl, —CN, —NO, —NO$_2$, —C(O)R$^{2a}$, —C(O)OR$^{2a}$, —N(R$^{2a}$)C(O)R$^{2b}$, —N(R$^{2a}$)(R$^{2b}$), —OR$^{2a}$, —N(R$^{2a}$)S(O)$_2$(R$^{2b}$), $C_{3-10}$ cycloalkyl, $C_{6-10}$ aryl, heterocycloalkyl, or heteroaryl, wherein each alkenyl or alkynyl is independently optionally substituted with 1 to 3 $R^{2d}$ groups, and each aryl is optionally substituted with 1 to 3 $R^{2f}$ groups; each $R^{2a}$ and $R^{2b}$ is independently hydrogen, $C_{1-6}$ alkyl, $C_{1-6}$ hydroxyalkyl, or $C_{2-6}$ alkoxyalkyl; each $R^{2d}$ is independently —N(R$^{2d1}$)(R$^{2d2}$), —OR$^{2d1}$, $C_{3-10}$ cycloalkyl, or $C_{6-12}$ aryl; each $R^{2f}$ is independently $C_{1-6}$ alkoxy or halogen; the heterocycloalkyl is a 5 to 8 membered ring having 1 to 2 heteroatoms each independently N, O, or S; $R^3$ is hydrogen, $C_{1-6}$ alkyl, $C_{2-6}$ alkenyl, $C_{2-6}$ alkynyl, $C_{1-6}$ hydroxyalkyl, $C_{1-6}$ alkoxy, $C_{2-6}$ alkoxyalkyl, halogen, $C_{1-6}$ haloalkyl, $C_{1-6}$ haloalkoxy, —CN, —NO, —NO$_2$, —C(O)R$^{3a}$, —C(O)OR$^{3a}$, —OC(O)R$^{3a}$, —C(O)N(R$^{3a}$)(R$^{3b}$), —N(R$^{3a}$)C(O)R$^{3b}$, —OC(O)N(R$^{3a}$)(R$^{3b}$), —N(R$^{3a}$)C(O)OR$^{3b}$, —N(R$^{3a}$)(R$^{3b}$), —OR$^{3a}$, —S(O)$_2$N(R$^{3a}$)(R$^{3b}$), —N(R$^{3a}$)S(O)$_2$(R$^{3b}$), $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, or heteroaryl, wherein each alkenyl or alkynyl is independently optionally substituted with 1 to 3 $R^{3d}$ groups, and each aryl is optionally substituted with 1 to 3 $R^{3f}$ groups; and the heteroaryl is a 5 to 6 membered ring having 1 to 3 heteroatoms each independently N, O, or S; and $R^4$ is hydrogen.

In some embodiments, the compound of Formula (I), (I-1), (Ia), (Ib), (Ic), (IIa), (IIc), (IIc-3), (IIc-4), (IIc-5), (IIc-6), (IIc-7), or (IIc-8), or a pharmaceutically acceptable salt thereof, is the compound wherein $R^1$ is hydrogen or F; $R^2$ is hydrogen, $C_{1-6}$ alkyl, $C_{2-6}$ alkenyl, $C_{2-6}$ alkynyl, $C_{1-6}$ hydroxyalkyl, $C_{2-6}$ alkoxyalkyl, halogen, —CN, —NO, —NO$_2$, —C(O)R$^{2a}$, —N(R$^{2a}$)C(O)R$^{2b}$, —N(R$^{2a}$)(R$^{2b}$), —OR$^{2a}$, or a 5 to 6 membered heteroaryl ring having 1 to 2 heteroatoms each independently N, O, or S; $R^{2a}$ and $R^{2b}$ are each independently hydrogen or $C_{1-6}$ alkyl; $R^3$ is hydrogen, $C_{1-6}$ alkyl, halogen, —CN or —NO$_2$; and $R^4$ is hydrogen, F, or Cl.

In some embodiments, the compound of Formula (I), (I-1), (Ia), (Ib), (Ic), (IIa), (IIc), (IIc-3), (IIc-4), (IIc-5), (IIc-6), (IIc-7), or (IIc-8), or a pharmaceutically acceptable salt thereof, is the compound wherein $R^1$ is hydrogen; $R^2$ is hydrogen, $C_{1-6}$ alkyl, $C_{2-6}$ alkenyl, $C_{2-6}$ alkynyl, $C_{1-6}$ hydroxyalkyl, $C_{2-6}$ alkoxyalkyl, halogen, —CN, —NO, —NO$_2$, —C(O)R$^{2a}$, —N(R$^{2a}$)C(O)R$^{2b}$, —N(R$^{2a}$)(R$^{2b}$), —OR$^{2a}$, or a 5 to 6 membered heteroaryl ring having 1 to 2 heteroatoms each independently N, O, or S; $R^{2a}$ and $R^{2b}$ are each independently hydrogen or $C_{1-6}$ alkyl; $R^3$ is hydrogen, $C_{1-6}$ alkyl, halogen, —CN or —NO$_2$; and $R^4$ is hydrogen.

In some embodiments, the compound of Formula (I), (I-1), (Ia), (Ib), (Ic), (IIa), (IIc), (IIc-3), (IIc-4), (IIc-5), (IIc-6), (IIc-7), or (IIc-8), or a pharmaceutically acceptable salt thereof, is the compound wherein $R^1$ is hydrogen; $R^2$ is hydrogen, $C_{1-3}$ alkyl, $C_{2-3}$ alkenyl, $C_{2-6}$ alkynyl, $C_{1-3}$ hydroxyalkyl, $C_{2-3}$ alkoxyalkyl, halogen, —CN, —NO, —NO$_2$, —C(O)R$^{2a}$, —N(R$^{2a}$)C(O)R$^{2b}$, —N(R$^{2a}$)(R$^{2b}$), —OR$^{2a}$, or a 5 to 6 membered heteroaryl ring having 1 to 2 heteroatoms each independently N, O, or S; $R^{2a}$ and $R^{2b}$ are each independently hydrogen or $C_{1-3}$ alkyl; $R^3$ is hydrogen, $C_{1-3}$ alkyl, halogen, —CN or —NO$_2$; and $R^4$ is hydrogen.

In some embodiments, the compound of Formula (I), (I-1), (Ia), (Ib), (Ic), (IIa), (IIc), (IIc-3), (IIc-4), (IIc-5), (IIc-6), (IIc-7), or (IIc-8), or a pharmaceutically acceptable salt thereof, is the compound wherein $R^1$ is hydrogen; $R^2$ is hydrogen, $C_{1-3}$ alkyl, $C_{2-3}$ alkenyl, $C_{2-6}$ alkynyl, $C_{1-3}$ hydroxyalkyl, $C_{2-3}$ alkoxyalkyl, halogen, —CN, —NO, —NO$_2$, —C(O)R$^{2a}$, —N(R$^{2a}$)C(O)R$^{2b}$, —N(R$^{2a}$)(R$^{2b}$), —OR$^{2a}$, or heteroaryl; $R^{2a}$ and $R^{2b}$ are each independently hydrogen or $C_{1-3}$ alkyl; $R^3$ is hydrogen; $R^4$ is hydrogen; and the heteroaryl is a 5 to 6 membered ring having 1 to 2 heteroatoms each independently N, O, or S.

In some embodiments, the compound of Formula (I), (I-1), (Ia), (Ia-1), (Ib), (IIa), or (IIa-1), or a pharmaceutically acceptable salt thereof, is the compound wherein $R^5$ is $C_{1-6}$ alkyl, $C_{2-6}$ alkenyl, $C_{2-6}$ alkynyl, $C_{1-6}$ hydroxyalkyl, $C_{2-6}$ alkoxyalkyl, $C_{1-6}$ haloalkyl, $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, $C_{1-6}$ alkyl-(heterocycloalkyl), or $C_{1-6}$ alkyl-(heteroaryl), wherein the alkyl is optionally substituted with $R^{5a}$; $R^{5a}$ is —OSi(R$^{5a1}$)(R$^{5a2}$)(R$^{5a3}$); $R^{5a1}$, $R^{5a2}$, and $R^{5a3}$ are each independently $C_{1-4}$ alkyl; and the heterocycloalkyl is a 5 to 8 membered ring having 1 to 2 heteroatoms each independently N, O, or S; and the heteroaryl is a 5 to 6 membered ring having 1 to 2 heteroatoms each independently N, O, or S. In some embodiments, the compound of Formula (I), (I-1), (Ia), (Ia-1), (Ib), (IIa), or (IIa-1), or a pharmaceutically acceptable salt thereof, is the compound wherein R is $C_{1-6}$ alkyl, $C_{2-6}$ alkynyl, $C_{2-6}$ alkoxyalkyl, $C_{1-6}$ haloalkyl, $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, or $C_{1-6}$ alkyl-(heterocycloalkyl), wherein the alkyl is optionally substituted with $R^{5a}$; $R^{5a}$ is —OSi(R$^{5a1}$)(R$^{5a2}$)(R$^{5a3}$); $R^{5a1}$, $R^{5a2}$, and $R^{5a3}$ are each independently $C_{1-4}$ alkyl, wherein $R^{5a1}$ and $R^{5a2}$ are different; and the heterocycloalkyl is a 5 to 6 membered ring having 1 to 2 heteroatoms each independently N or O. In some embodiments, the compound of Formula (I), (I-1), (Ia), (Ia-1), (Ib), (IIa), or (IIa-1), or a pharmaceutically acceptable salt thereof, is the compound wherein $R^5$ is $C_{1-6}$ alkyl, $C_{2-6}$ alkynyl, $C_{2-3}$ alkoxyalkyl, $C_{1-3}$ haloalkyl, $C_{3-8}$ cycloalkyl, $C_{1-3}$ alkyl-$C_{3-8}$ cycloalkyl, phenyl, $C_{1-3}$ alkyl-phenyl, or $C_{1-3}$ alkyl-(heterocycloalkyl), wherein the alkyl is optionally substituted with $R^{5a}$; $R^{5a}$ is —OSi(R$^{5a1}$)(R$^{5a2}$)(R$^{5a3}$); $R^{5a1}$, $R^{5a2}$, and $R^{5a3}$ are each independently Me or tBu, wherein $R^{5a1}$ and $R^{5a2}$ are different; and the heterocycloalkyl is a 6 membered ring having 1 heteroatom N or O. In some embodiments, the compound of Formula (I), (I-1), (Ia), (Ia-1), (Ib), (IIa), or (IIa-1), or a pharmaceutically acceptable salt thereof, is the compound wherein R⁵ is Me, Et, nPr, nBu, —CH₂CMe₃, —CH₂C≡CMe, —CH₂CH₂C—CH, —CH₂CH₂OMe, —CH₂CH₂OSi(Me)₂(tBu), CF₃, —CH₂CF₂H, —CH₂CF₃,

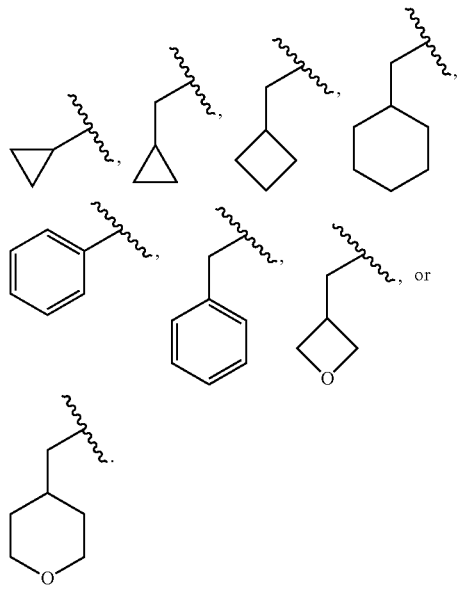

In some embodiments, the compound of Formula (I), (I-1), (Ia), (Ia-1), (Ib), (Ia), or (IIa-1), or a pharmaceutically acceptable salt thereof, is the compound wherein R⁵ is $C_{1-6}$ alkyl, $C_{2-6}$ alkenyl, $C_{2-6}$ alkynyl, $C_{1-6}$ hydroxyalkyl, $C_{2-6}$ alkoxyalkyl, $C_{1-6}$ haloalkyl, $C_{1-6}$ alkyl-$C_{3-10}$ cycloalkyl, $C_{6-12}$ aryl, $C_{1-6}$ alkyl-$C_{6-12}$ aryl, $C_{1-6}$ alkyl-(heterocycloalkyl), or $C_{1-6}$ alkyl-(heteroaryl), wherein the alkyl is optionally substituted with $R^{5a}$; $R^{5a}$ is —OSi($R^{5a1}$)($R^{5a2}$)($R^{5a3}$); $R^{5a1}$, $R^{5a2}$, and $R^{5a3}$ are each independently $C_{1-4}$ alkyl; the heterocycloalkyl is a 5 to 8 membered ring having 1 to 2 heteroatoms each independently N, O, or S; and the heteroaryl is a 5 to 6 membered ring having 1 to 2 heteroatoms each independently N, O, or S. In some embodiments, the compound of Formula (I), (I-1), (Ia), (Ia-1), (Ib), (IIa), or (IIa-1), or a pharmaceutically acceptable salt thereof, is the compound wherein R⁵ is $C_{1-6}$ alkyl, $C_{2-6}$ alkynyl, $C_{2-6}$ alkoxyalkyl, $C_{1-6}$ alkyl-$C_{3-10}$ cycloalkyl, $C_{6-12}$ aryl, $C_{1-6}$ alkyl-$C_{6-12}$ aryl, or $C_{1-6}$ alkyl-(heterocycloalkyl), wherein the alkyl is optionally substituted with $R^{5a}$; $R^{5a}$ is —OSi($R^{5a}$)($R^{5a2}$)($R^{5a3}$); $R^{5a1}$, $R^{5a2}$, and $R^{5a3}$ are each independently $C_{1-4}$ alkyl, wherein $R^{5a1}$ and $R^{5a2}$ are different; and the heterocycloalkyl is a 5 to 6 membered ring having 1 to 2 heteroatoms each independently N or O. In some embodiments, the compound of Formula (I), (I-1), (Ia), (Ia-1), (Ib), (IIa), or (IIa-1), or a pharmaceutically acceptable salt thereof, is the compound wherein R is $C_{1-6}$ alkyl, $C_{2-6}$ alkynyl, $C_{2-3}$ alkoxyalkyl, $C_{1-3}$ alkyl-$C_{3-8}$ cycloalkyl, phenyl, $C_{1-3}$ alkyl-phenyl, or $C_{1-3}$ alkyl-(heterocycloalkyl), wherein the alkyl is optionally substituted with $R^{5a}$; $R^{5a}$ is —OSi($R^{5a1}$)($R^{5a2}$)($R^{5a3}$); $R^{5a1}$, $R^{5a2}$, and $R^{5a3}$ are each independently Me or tBu, wherein $R^{5a1}$ and $R^{5a2}$ are different; and the heterocycloalkyl is a 6 membered ring having 1 heteroatom N or O.

In some embodiments, the compound of Formula (I), (I-1), (Ia), (Ia-1), (Ib), (IIa), or (IIa-1), or a pharmaceutically acceptable salt thereof, is the compound wherein R⁵ is Me, Et, nPr, nBu, —CH₂CMe₃, —CH₂C≡CMe, —CH₂CH₂C—CH, —CH₂CH₂OMe, —CH₂CH₂OSi(Me)₂(tBu),

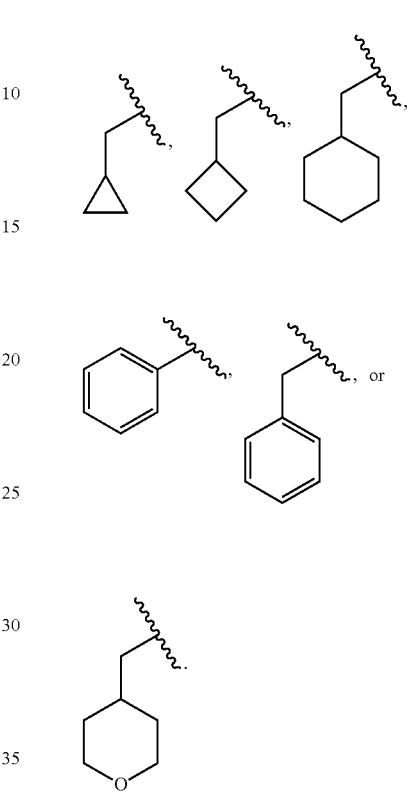

In some embodiments, the compound of Formula (I), (I-1), (Ia), (Ia-1), (Ib), (IIa), or (IIa-1), or a pharmaceutically acceptable salt thereof, is the compound wherein $R^{5a}$, $R^{5a2}$, and $R^{5a3}$ are each independently $C_{1-4}$ alkyl. In some embodiments, the compound of Formula (I), (I-1), (Ia), (Ia-1), or (Ib), or a pharmaceutically acceptable salt thereof, is the compound wherein $R^{5a1}$ and $R^{5a2}$ are each Me or tBu. In some embodiments, the compound of Formula (I), (I-1), (Ia), (Ia-1), (Ib), (IIa), or (IIa-1), or a pharmaceutically acceptable salt thereof, is the compound wherein $R^{5a1}$ and $R^{5a2}$ are different.

In some embodiments, the compound of Formula (I) or (I-1), or a pharmaceutically acceptable salt thereof, is the compound wherein R⁶ is phenyl, naphthyl, thienyl, thiazolyl, pyridyl, pyrazinyl, pyrimidinyl, or dibenzofuryl, which are each optionally substituted with 1 or 2 $R^{6a}$.

In some embodiments, the compound of Formula (I) or (I-1), or a pharmaceutically acceptable salt thereof, is the compound wherein R⁶ is phenyl or a 5 to 6 membered heteroaryl ring having 1 to 3 heteroatoms each independently N, O, or S, which are each optionally substituted with 1 or 2 $R^{6a}$. In some embodiments, the compound of Formula (I) or (I-1), or a pharmaceutically acceptable salt thereof, is the compound wherein R⁶ is phenyl, thienyl, thiazolyl, isothiazolyl, oxazolyl, isoxazolyl, pyrrolyl, pyrazolyl, pyridyl, or pyrimidinyl, which are each optionally substituted with 1 or 2 $R^{6a}$. In some embodiments, the compound of Formula (I) or (I-1), or a pharmaceutically acceptable salt thereof, is the compound wherein R⁶ is phenyl, thienyl, or pyridyl, optionally substituted with 1 or 2 $R^{6a}$. In some embodiments, the compound of Formula (I) or (I-1), or a pharmaceutically acceptable salt thereof, is the compound wherein $R^6$ is

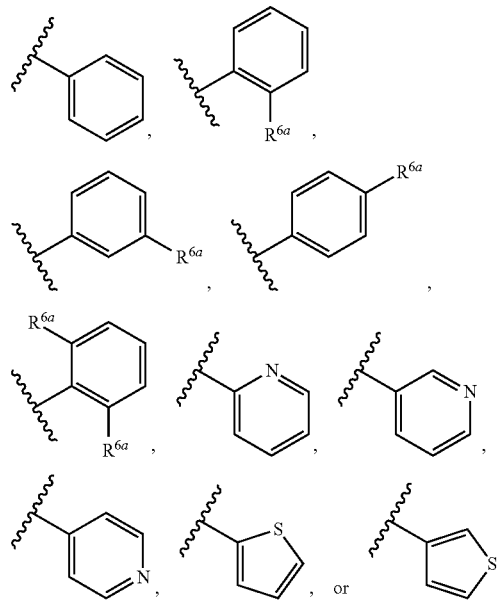

In some embodiments, the compound of Formula (I) or (I-1), or a pharmaceutically acceptable salt thereof, is the compound wherein $R^6$ is

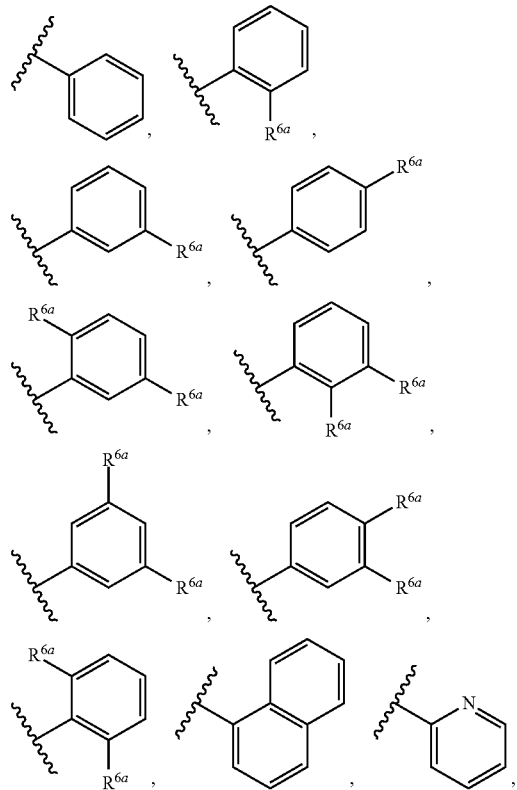

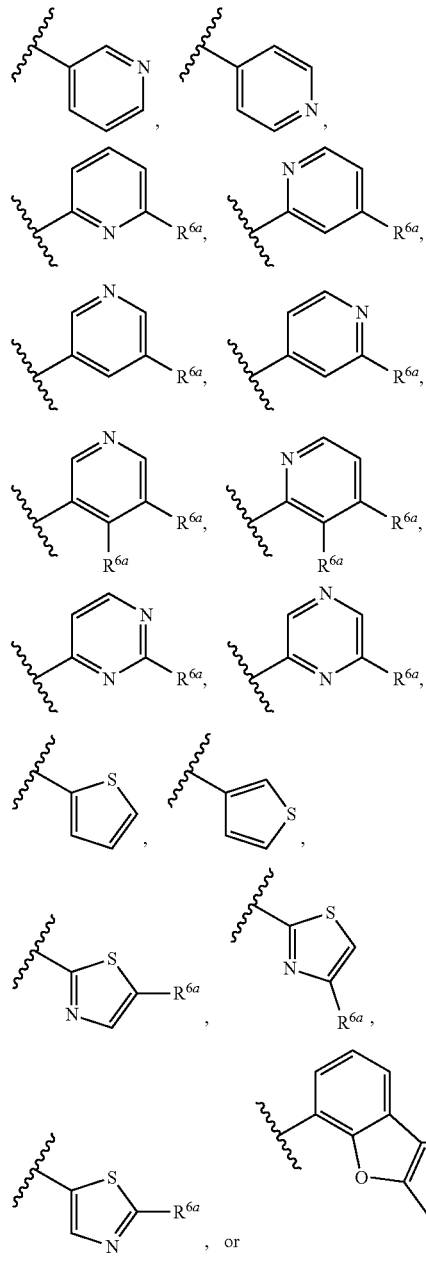

In some embodiments, the compound of Formula (I) or (I-1), or a pharmaceutically acceptable salt thereof, is the compound wherein $R^6$ is

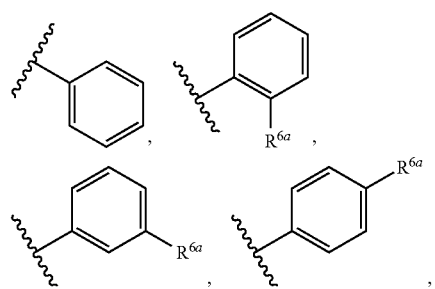

-continued

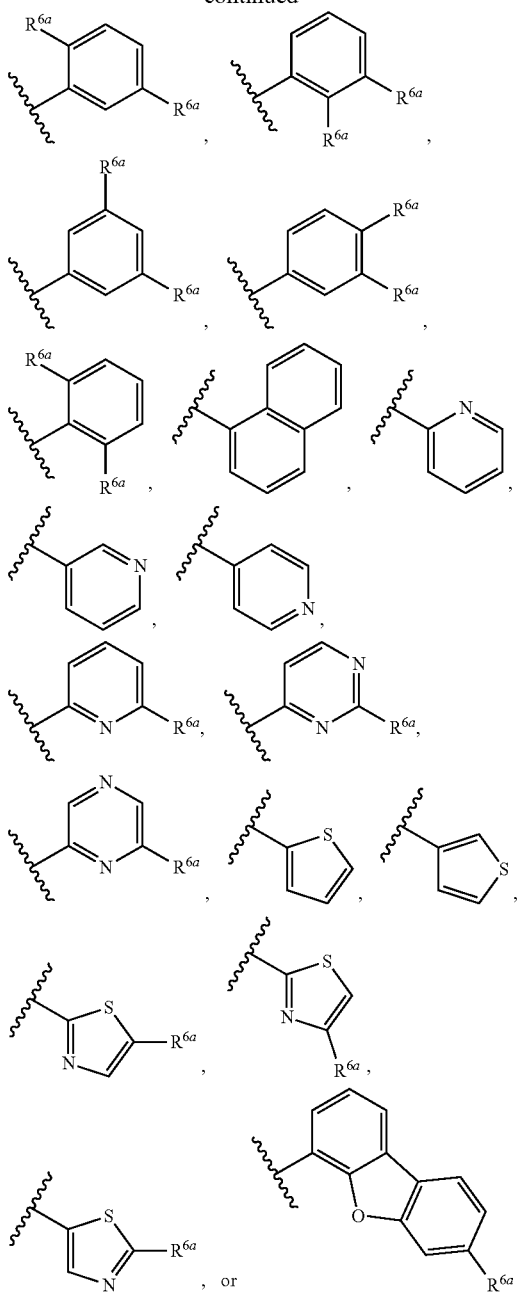

In some embodiments, the compound of Formula (I), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein $R^7$ is hydrogen, Me, Et, OMe, —CH₂OH, —CH₂OMe, —CH₂NMe₂, Cl, CHF₂, OH, NH₂, SMe, or

In some embodiments, the compound of Formula (I), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein $R^7$ is hydrogen, Me, —CH₂OMe, CHF₂, or NH₂.

In some embodiments, the compound of Formula (I), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein $R^7$ is hydrogen, Me, Et, OMe, —CH₂NMe₂, Cl, OH, NH₂, SMe, or

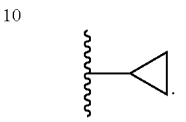

In some embodiments, the compound of Formula (I), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein $R^7$ is hydrogen or Me. In some embodiments, the compound of Formula (I), (IIa), (IIa-1), (IIc), (IIc-1), or (IIc-2), or a pharmaceutically acceptable salt thereof, is the compound wherein $R^7$ is hydrogen. In some embodiments, the compound of Formula (I), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein $R^7$ is Me.

In some embodiments, the compound of Formula (I) or a pharmaceutically acceptable salt thereof, is a compound that has the structure of Formula (I-1):

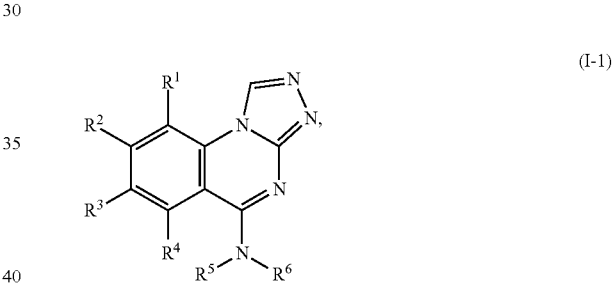

(I-1)

or a pharmaceutically acceptable salt thereof.

In some embodiments, the compound of Formula (I) or a pharmaceutically acceptable salt thereof, is a compound that has the structure of Formula (IIa):

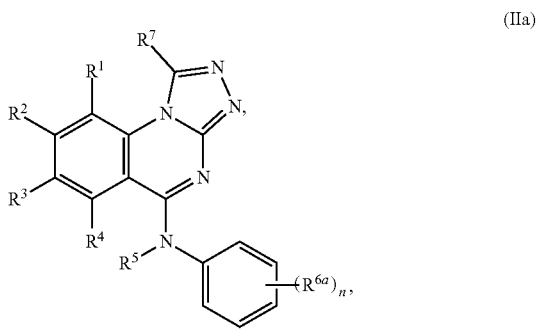

(IIa)

wherein n is 0, 1, 2, or 3. In some embodiments, the compound of Formula (IIa) or a pharmaceutically acceptable salt thereof, is a compound wherein n is 0. In some embodiments, the compound of Formula (IIa), or a pharmaceutically acceptable salt thereof, is a compound wherein n is 1. In some embodiments, the compound of Formula (IIa), or a pharmaceutically acceptable salt thereof, is a compound wherein n is 2. In some embodiments, the compound of Formula (IIa), or a pharmaceutically acceptable salt thereof, is a compound wherein n is 3.

In some embodiments, the compound of Formula (I) or (I-1), or a pharmaceutically acceptable salt thereof, is a compound that has the structure of Formula (Ia):

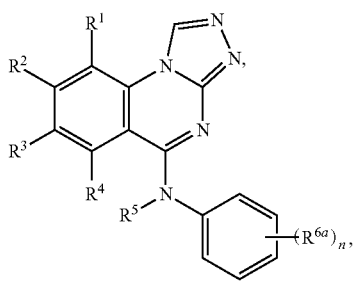

wherein n is 0, 1, 2, or 3. In some embodiments, the compound of Formula (Ia), or a pharmaceutically acceptable salt thereof, is a compound wherein n is 0. In some embodiments, the compound of Formula (Ia), or a pharmaceutically acceptable salt thereof, is a compound wherein n is 1. In some embodiments, the compound of Formula (Ia), or a pharmaceutically acceptable salt thereof, is a compound wherein n is 2. In some embodiments, the compound of Formula (Ia), or a pharmaceutically acceptable salt thereof, is a compound wherein n is 3.

In some embodiments, the compound of Formula (I), or a pharmaceutically acceptable salt thereof, is a compound that has the structure of Formula (IIa-1):

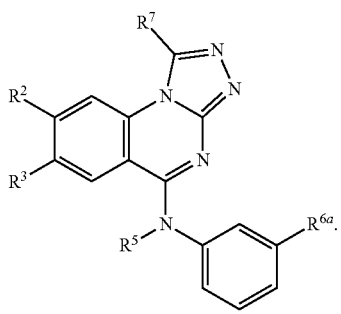

In some embodiments, the compound of Formula (I), (I-1), or (Ia), or a pharmaceutically acceptable salt thereof, is a compound that has the structure of Formula (Ia-1):

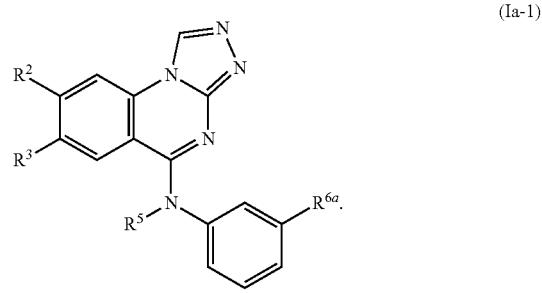

In some embodiments, the compound of Formula (I), (I-1), (Ia), (Ia-1), or (Ic), or a pharmaceutically acceptable salt thereof, is the compound wherein each $R^{6a}$ is independently a hydrogen atom, an optionally substituted $C_1$-$C_6$ alkyl group (a methyl group and an ethyl group, for example), an optionally substituted $C_2$-$C_6$ alkenyl group, an optionally substituted $C_2$-$C_6$ alkynyl group (a 1-propynyl group for example; a halogen atom, a hydroxy group and a methoxy group etc. are exemplified as the substituent of these alkyl, alkenyl and alkynyl groups), an optionally substituted $C_1$-$C_6$ alkoxy group (a halogen atom is exemplified as the substituent), $C_3$-$C_6$ cycloalkyl group (a cyclopropyl group and a cyclohexyl group for example), a hydroxy group, a halogen atom, a nitro group, a cyano group, an amino group, an acetylamino group, a methoxycarbonyl group, a carboxy group, a carbamoyl group, a formyl group, a 5- or 6-membered saturated cyclic amino group (a morpholino group, a pyrrolidyl group, a piperidyl group are exemplified), a 5- or 6-membered heteroaryl group (a furanyl group, a thienyl group, an imidazolyl group, a pyrrolyl group, a pyrazolyl group, a methylpyrazolyl group, a pyridyl group, a pyrimidyl group etc. are exemplified), a phenyl group, a substituted phenyl group (examples of the substituent include $C_1$-$C_6$ alkyl group, $C_3$-$C_6$ cycloalkyl group, a halogen atom, a methoxy group, a trifluoromethyl group, an acetylamino group etc.) and the like.

In some embodiments, the compound of Formula (I), (I-1), (Ia), (Ia-1), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein each $R^{6a}$ is independently $C_{1-6}$ alkyl, $C_{2-6}$ alkynyl, $C_{1-6}$ hydroxyalkyl, $C_{1-6}$ alkoxy, $C_{2-6}$ alkoxyalkyl, halogen, $C_{1-6}$ haloalkyl, $C_{1-6}$ haloalkoxy, —CN, —NO$_2$, —C(O)$R^{6b}$, —C(O)O$R^{6b}$, —C(O)N($R^{6b}$)($R^{6c}$), —N($R^{6b}$)($R^{6c}$), —O$R^{6b}$, $C_{3-10}$ cycloalkyl, $C_{6-12}$ aryl, heterocycloalkyl, or heteroaryl, wherein the cycloalkyl, aryl, heterocycloalkyl, or heteroaryl is each optionally substituted with 1 to 3 $R^{6e}$, and the alkyl is optionally substituted with $R^6$.

In some embodiments, the compound of Formula (I), (I-1), (Ia), (Ia-1), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein each $R^{6a}$ is independently $C_{1-6}$ alkyl, $C_{2-6}$ alkynyl, $C_{1-6}$ hydroxyalkyl, $C_{1-6}$ alkoxy, $C_{2-6}$ alkoxyalkyl, halogen, $C_{1-6}$ haloalkyl, $C_{1-6}$ haloalkoxy, —CN, —NO$_2$, —C(O)$R^{6b}$, —C(O)O$R^{6b}$, —C(O)N($R^{6b}$)($R^{6c}$), —N($R^{6b}$)($R^{6c}$), —O$R^{6b}$, $C_{3-10}$ cycloalkyl, $C_{6-12}$ aryl, heterocycloalkyl, or heteroaryl, wherein the cycloalkyl, aryl, heterocycloalkyl, or heteroaryl is each optionally substituted with 1 to 3 $R^{6e}$, and the alkyl is optionally substituted with $R^{61}$; each $R^{6b}$ and $R^{6c}$ is independently hydrogen or $C_{1-6}$ alkyl; each $R^{6e}$ is independently $C_{1-6}$ alkyl, $C_{2-6}$ alkenyl, $C_{2-6}$ alkynyl, $C_{1-6}$ hydroxyalkyl, $C_{1-6}$ alkoxy, $C_{2-6}$ alkoxyalkyl, halogen, $C_{1-6}$ haloalkyl, —C(O)OR$^{6e1}$, —OC(O)R$^{6e1}$, —C(O)N(R$^{6e1}$)(R$^{6e2}$), —N(R$^{6e1}$)C(O)R$^{6e2}$, —OR$^{6e1}$, —S(O)$_2$N(R$^{6e1}$)(R$^{6e2}$), —N(R$^{6e1}$)S(O)$_2$(R$^{6e2}$); each R$^{6e1}$ and R$^{6e2}$ is independently hydrogen or C$_{1-6}$ alkyl; R$^1$ is —OSi(R$^{6f1}$)(R$^{6f2}$)(R$^{6f3}$); and R$^{6f1}$, R$^{6f}$, and R$^{6f3}$ are each independently C$_{1-6}$ alkyl. In some embodiments, the compound of Formula (I), (I-1), (Ia), (Ia-1), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein each R$^{6a}$ is independently C$_{1-3}$ alkyl, C$_{2-3}$ alkynyl, C$_{1-3}$ hydroxyalkyl, C$_{1-3}$ alkoxy, C$_{2-3}$ alkoxyalkyl, halogen, C$_{1-3}$ haloalkyl, C$_{1-3}$ haloalkoxy, —CN, —NO$_2$, —C(O)R$^{6b}$, —C(O)OR$^{6b}$, —C(O)N(R$^{6b}$)(R$^{6c}$), —N(R$^{6b}$)(R$^{6c}$), —OR$^{6b}$, C$_{3-8}$ cycloalkyl, phenyl, a 5 to 6 membered heterocycloalkyl ring having 1 to 2 heteroatoms each independently N or O, or a 5 to 6 membered heteroaryl ring having 1 to 2 heteroatoms each independently N, O, or S, wherein the cycloalkyl, phenyl, heterocycloalkyl, or heteroaryl is each optionally substituted with 1 to 2 R$^{6e}$, and the alkyl is optionally substituted with R$^{6f}$; each R$^{6b}$ and R$^{6c}$ is independently hydrogen or C$_{1-3}$ alkyl; each R$^{6e}$ is independently C$_{1-6}$ alkyl, C$_{1-6}$ hydroxyalkyl, C$_{1-6}$ alkoxy, C$_{2-6}$ alkoxyalkyl, halogen, C$_{1-6}$ haloalkyl, —C(O)OR$^{6e1}$, —OC(O)R$^{6e1}$, —N(R$^{6e1}$)C(O)R$^{6e2}$, —OR$^{6e1}$; each R$^6$ and R$^{6e2}$ is independently hydrogen or C$_{1-6}$ alkyl; R$^{6f}$ is —OSi(R$^{6f1}$)(R$^{6f2}$)(R$^{6f1}$); and R$^{6f1}$, R$^{6f2}$, and R$^{6f3}$ are each independently Me or tBu.

In some embodiments, the compound of Formula (I), (I-1), (Ia), (Ia-1), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein each R$^{6b}$ and R$^{6c}$ is independently hydrogen, C$_{1-6}$ alkyl, C$_{1-6}$ hydroxyalkyl, C$_{2-6}$ alkoxyalkyl, C$_{1-6}$ haloalkyl, or C$_{3-10}$ cycloalkyl. In some embodiments, the compound of Formula (I), (I-1), (Ia), (Ia-1), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein each R$^{6b}$ and R$^{6c}$ is independently hydrogen, C$_{1-6}$ alkyl, or C$_{1-6}$ haloalkyl. In some embodiments, the compound of Formula (I), (I-1), (Ia), (Ia-1), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein each R$^{6b}$ and R$^{6c}$ is independently hydrogen or C$_{1-6}$ alkyl. In some embodiments, the compound of Formula (I), (I-1), (Ia), (Ia-1), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein each R$^{6b}$ and R$^{6c}$ is independently hydrogen or C$_{1-3}$ alkyl. In some embodiments, the compound of Formula (I), (I-1), (Ia), (Ia-1), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein each R$^{6b}$ and R$^{6c}$ is independently hydrogen or Me.

In some embodiments, the compound of Formula (I), (I-1), (Ia), (Ia-1), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein each R$^{6b}$, R$^{6c}$ and R$^{6d}$ is independently hydrogen, C$_{1-6}$ alkyl, C$_{1-6}$ hydroxyalkyl, C$_{2-6}$ alkoxyalkyl, C$_{1-6}$ haloalkyl, or C$_{3-10}$ cycloalkyl. In some embodiments, the compound of Formula (I), (I-1), (Ia), (Ia-1), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein each R$^{6b}$, R$^{6c}$ and R$^{6d}$ is independently hydrogen, C$_{1-6}$ alkyl, or C$_{1-6}$ haloalkyl. In some embodiments, the compound of Formula (I), (I-1), (Ia), (Ia-1), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein each R$^{6b}$, R$^{6c}$ and R$^{6d}$ is independently hydrogen or C$_{1-6}$ alkyl. In some embodiments, the compound of Formula (I), (I-1), (Ia), (Ia-1), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein each R$^{6b}$, R$^{6c}$ and R$^{6d}$ is independently hydrogen or C$_{1-3}$ alkyl. In some embodiments, the compound of Formula (I), (I-1), (Ia), (Ia-1), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein each R$^{6b}$, R$^{6c}$ and R$^{6d}$ is independently hydrogen or Me.

In some embodiments, the compound of Formula (I), (I-1), (Ia), (Ia-1), (Ib), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein each R$^{6e}$ is independently a hydrogen atom, a C$_1$-C$_6$ alkyl group (a methyl group, an ethyl group, and a tert-butyl group are exemplified), a C$_2$-C$_6$ alkenyl group, a C$_2$-C$_6$ alkynyl group, a C$_1$-C$_6$ alkoxy group (a methoxy group, for example), a C$_3$-C$_6$ cycloalkyl group, a hydroxy group, a halogen atom, a nitro group, a cyano group, a carbamoyl group, a formyl group, an acetylamino group and the like.

In some embodiments, the compound of Formula (I), (I-1), (Ia), (Ia-1), (Ib), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein each R$^{6e}$ is independently C$_{1-6}$ alkyl, C$_{2-6}$ alkenyl, C$_{2-6}$ alkynyl, C$_{1-6}$ hydroxyalkyl, C$_{1-6}$ alkoxy, C$_{2-6}$ alkoxyalkyl, halogen, C$_{1-6}$ haloalkyl, —C(O)OR$^{6e1}$, —OC(O)R$^{6e1}$, —C(O)N(R$^{6e1}$)(R$^{6e2}$), —N(R$^{6e1}$)C(O)R$^{6e2}$, —OR$^{6e1}$, —S(O)$_2$N(R$^{6e1}$)(R$^{6e2}$), —N(R$^{6e1}$)S(O)$_2$(R$^{6e2}$); and each R$^{6e1}$ and R$^{6e2}$ is independently hydrogen or C$_{1-6}$ alkyl. In some embodiments, the compound of Formula (I), (I-1), (Ia), (Ia-1), (Ib), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein each R$^{6e}$ is independently C$_{1-6}$ alkyl, C$_{1-6}$ hydroxyalkyl, C$_{1-6}$ alkoxy, C$_{2-6}$ alkoxyalkyl, halogen, C$_{1-6}$ haloalkyl, —C(O)OR$^{6e1}$, —OC(O)R$^{6e1}$, —N(R$^{6e1}$)C(O)R$^{6e2}$, —OR$^{6e1}$; and each R$^{6e1}$ and R$^{6e2}$ is independently hydrogen or C$_{1-6}$ alkyl. In some embodiments, the compound of Formula (I), (I-1), (Ia), (Ia-1), (Ib), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein each R$^{6e}$ is independently C$_{1-6}$ alkyl, C$_{1-3}$ alkoxy, halogen, C$_{1-6}$ haloalkyl, —N(R$^{6e1}$)C(O)R$^{6e2}$, or —OR$^{6e1}$; and each R$^{6e1}$ and R$^{6e2}$ is independently hydrogen or C$_{1-3}$ alkyl.

In some embodiments, the compound of Formula (I), (I-1), (Ia), (Ia-1), (Ib), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein each R$^{6n}$ is C$_{1-6}$ alkyl, C$_{1-6}$ hydroxyalkyl, —C(O) OR$^{6n1}$, —OC(O)R$^{6n1}$, —C(O)N(R$^{6n1}$)(R$^{6n2}$), —N(R$^{6n1}$)C(O)R$^6$, —OC(O)N(R$^{6n1}$)(R$^{6n2}$), —N(R$^{6n1}$)C(O)OR$^{6n2}$, =O, or —OH; wherein each R$^{6n1}$ and R$^{6n2}$ is independently hydrogen, C$_{1-6}$ alkyl, or C$_{1-6}$ hydroxyalkyl. In some embodiments, the compound of Formula (I), (I-1), (Ia), (Ia-1), (Ib), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein each R$^{6n}$ is C$_{1-6}$ alkyl, —C(O)OR$^{6n1}$, or —OC(O)R$^{6n1}$, —C(O)N(R$^{6n1}$) (R$^{6n2}$), —N(R$^{6n1}$)C(O)R$^{6n2}$, —OC(O)N(R$^{6n1}$)(R$^{6n2}$), —N(R$^{6n1}$)C(O)OR$^{6n2}$, =O, or —OH; wherein each R$^{6n1}$ and R$^{6n2}$ is independently hydrogen or C$_{1-6}$ alkyl. In some embodiments, the compound of Formula (I), (I-1), (Ia), (Ia-1), (Ib), (Ic), (IIa), (IIa-1), (IIc), (Ic-1), (IIc-2), (IIc-3), (IIc-4), (IIc-5), (IIc-6), (IIc-7), or (IIc-8), or a pharmaceutically acceptable salt thereof, is the compound wherein each $R^{6n}$ is independently Me or $CO_2tBu$.

In some embodiments, the compound of Formula (I), (I-1), (Ia), (Ia-1), (Ib), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein each $R^{6h}$ is independently $C_{1-6}$ alkyl, $C_{1-6}$ hydroxyalkyl, $C_{1-6}$ aminoalkyl, $C_{1-6}$ alkoxy, $C_{2-6}$ alkoxyalkyl, halogen, $C_{1-6}$ haloalkyl, —CN, —C(O)$R^{6h1}$, —C(O)O$R^{6h1}$, —OC(O)$R^{6h1}$, —C(O)N($R^{6h1}$)($R^{6h2}$), —N($R^{6h1}$)C(O)$R^{6h2}$, —OC(O)N($R^{6h1}$)($R^{6h2}$), —N($R^{6h1}$)C(O)O$R^{6h2}$, —N($R^{6h1}$)($R^{6h2}$), =O, —OH, —S$R^{6h1}$, —S(O)$R^{6h1}$, —S(O)$_2R^{6h1}$, —S(O)$_2$N($R^{6h1}$)($R^{6h2}$), —N($R^{6h1}$)S(O)$_2$($R^{6h1}$), $C_{3-10}$ cycloalkyl, $C_{1-6}$ alkyl-$C_{3-10}$ cycloalkyl, heterocycloalkyl, or $C_{1-6}$alkyl-(heterocycloalkyl); wherein each $R^{6h1}$ and $R^{6h2}$ is independently hydrogen, $C_{1-6}$ alkyl, $C_{1-6}$ hydroxyalkyl, $C_{1-6}$ aminoalkyl, $C_{2-6}$ alkoxyalkyl, $C_{1-6}$ haloalkyl, $C_{3-10}$ cycloalkyl, or $C_{1-6}$ alkyl-$C_{3-10}$ cycloalkyl. In some embodiments, the compound of Formula (I), (I-1), (Ia), (Ia-1), (Ib), (Ic), (Ia), (IIa-1), (Ic), (Ic-1), (IIc-2), (IIc-3), (IIc-4), (IIc-5), (IIc-6), (IIc-7), or (IIc-8), or a pharmaceutically acceptable salt thereof, is the compound wherein each $R^{6h}$ is independently $C_{1-6}$ alkyl, $C_{1-6}$ hydroxyalkyl, $C_{1-6}$ aminoalkyl, $C_{1-6}$ alkoxy, $C_{1-6}$ haloalkyl, —C(O)$R^{6h1}$, —C(O)O$R^{6h1}$, —N($R^{6h1}$)($R^{6h2}$), =O, or heterocycloalkyl; wherein each $R^{6h1}$ and $R^{6h2}$ is independently hydrogen, $C_{1-6}$ alkyl, or $C_{1-6}$ hydroxyalkyl. In some embodiments, the compound of Formula (I), (I-1), (Ia), (Ia-1), (Ib), (Ic), (Ia), (IIa-1), (IIc), (Ic-1), (IIc-2), (IIc-3), (IIc-4), (IIc-5), (IIc-6), (IIc-7), or (IIc-8), or a pharmaceutically acceptable salt thereof, is the compound wherein each $R^{6h}$ is independently Me, —CH$_2$OH, —CH$_2$NHMe, OMe, NH$_2$, CF$_3$, CN, —(CO)Me, —(CO)tBu, —(CO)—CH$_2$OH, CO$_2$Me, CO$_2$tBu, =O, or

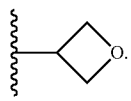

In some embodiments, the compound of Formula (I), (I-1), (Ia), (Ia-1), (Ib), (Ic), (Ia), (IIa-1), (IIc), (Ic-1), (IIc-2), (IIc-3), (IIc-4), (IIc-5), (IIc-6), (IIc-7), or (IIc-8), or a pharmaceutically acceptable salt thereof, is the compound wherein each $R^{6m}$ is independently halogen, $C_{1-6}$ haloalkyl, —CN, —C(O)$R^{6m1}$, —C(O)O$R^{6m1}$, —OC(O)$R^{6m1}$, —C(O)N($R^{6m1}$)($R^{6m2}$), —N($R^{6m3}$)C(O)$R^{6m2}$, —OC(O)N($R^{6m1}$)($R^{6m2}$), —N($R^{6m1}$)C(O)O$R^{6m2}$, —C(=N$R^{6m3}$)N($R^{6m1}$)($R^{6m2}$), —N($R^{6m1}$)($R^{6m2}$), =O, —OH, —S$R^{6m1}$, —S(O)$R^{6m1}$, —S(O)(N$R^{6m1}$)($R^{6m2}$), —S(O)$_2R^{6m1}$, or —S(O)$_2$N($R^{6m1}$)($R^{6m}$); wherein each $R^{6m1}$ and $R^{6m2}$ is independently hydrogen, $C_{1-6}$ alkyl, $C_{1-6}$ hydroxyalkyl, $C_{1-6}$ haloalkyl, $C_{3-10}$ cycloalkyl, or heterocycloalkyl. In some embodiments, the compound of Formula (I), (I-1), (Ia), (Ia-1), (Ib), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein each $R^{6m}$ is independently $C_{1-6}$ haloalkyl, —CN, —C(O)$R^{6m1}$, —C(O)O$R^{6m1}$, —C(O)N($R^{6m1}$)($R^{6m2}$), —N($R^{6m1}$)($R^{6m2}$), =O, —OH, or —S(O)$_2R^{6m1}$; wherein each $R^{6m1}$ and $R^{6m2}$ is independently hydrogen, $C_{1-6}$ alkyl, or heterocycloalkyl. In some embodiments, the compound of Formula (I), (I-1), (Ia), (Ia-1), (Ib), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein each $R^{6m}$ is independently OH, CF$_3$, CN, CO$_2$H, CONH$_2$, NMe$_2$, SO$_2$Me, or

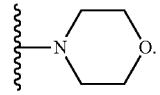

In some embodiments, the compound of Formula (I), (I-1), (Ia), (Ia-1), (Ib), (Ic), (IIa), (IIa-1), (IIc), (Ic-1), (IIc-2), (IIc-3), (IIc-4), (IIc-5), (IIc-6), (IIc-7), or (IIc-8), or a pharmaceutically acceptable salt thereof, is the compound wherein each $R^{6e}$ is independently Me, Et, iPr, tBu, —CH$_2$OH, —C(OH)Me$_2$, —OMe, —OEt, —OCH$_2$CH$_2$CH$_3$, —CH$_2$OMe, —OCH$_2$CH$_2$NMe$_2$, F, Cl, Br, CHF$_2$, —CF$_3$, —CH$_2$CHF$_2$, —CH$_2$CF$_3$, —CF$_2$CH$_3$, —C(CH$_3$)$_2$CF$_3$, OCF$_3$, —OCH$_2$CF$_3$, —OCH(CH$_3$)CF$_3$, CN, —C(O)Me, —C(O)tBu, CO$_2$H, CO$_2$Me, CO$_2$tBu, C(O)NH$_2$, =O, OH, NH$_2$, NMe$_2$, —NMeCH$_2$CH$_2$OMe, —NHC(O)Me, —NHC(O)tBu, —NHCO$_2$tBu, SO$_2$Me, SO$_2$Et, SO$_2$(iPr), SO$_2$(iBu), SO$_2$CF$_3$, —CH$_2$SO$_2$Me, SO(N=H)Me, SO$_2$NH$_2$, SO$_2$NHMe, SO$_2$NMe$_2$, —SO$_2$NHCH$_2$CH$_2$OH, —NHSO$_2$Me, SF$_5$, —POMe$_2$,

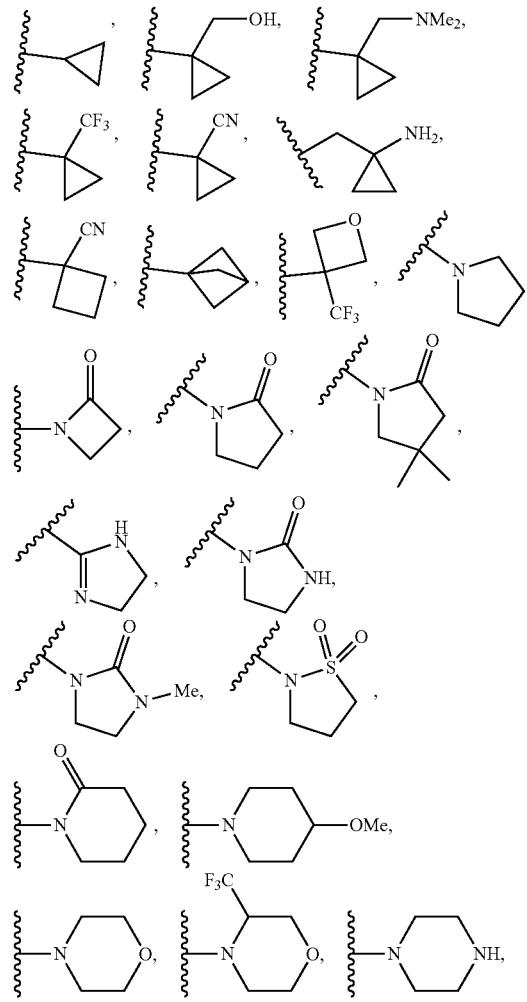

-continued

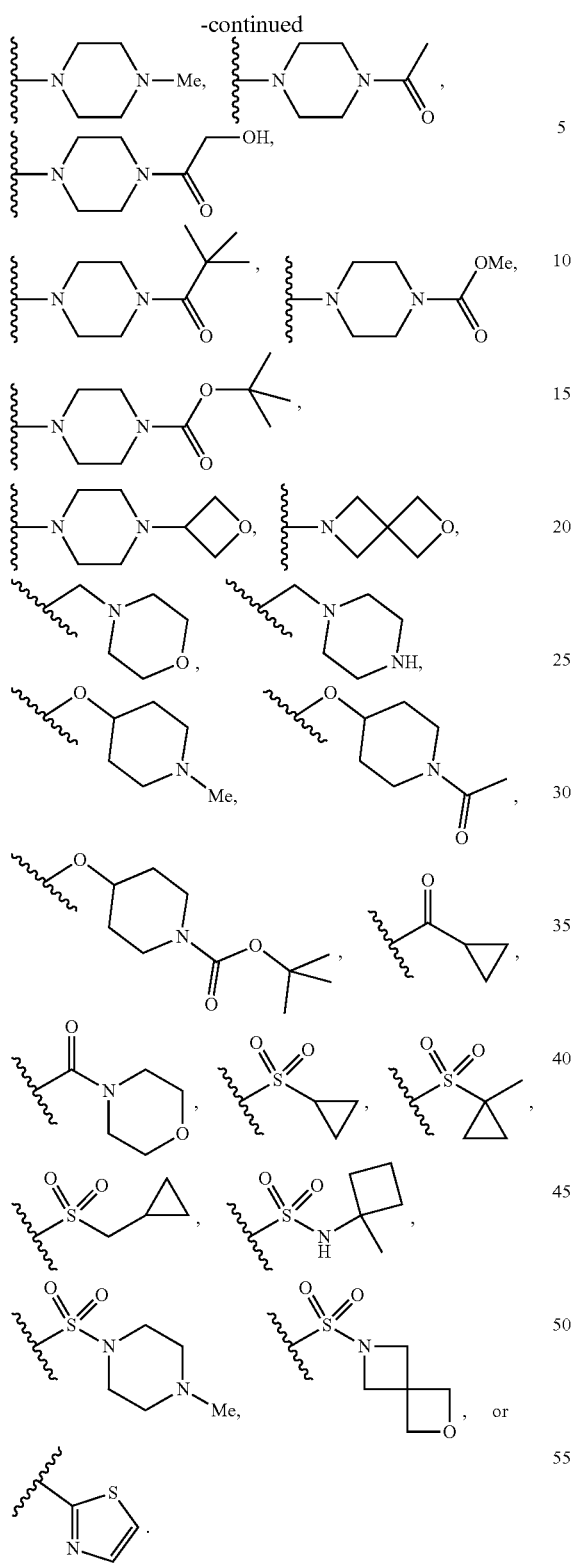

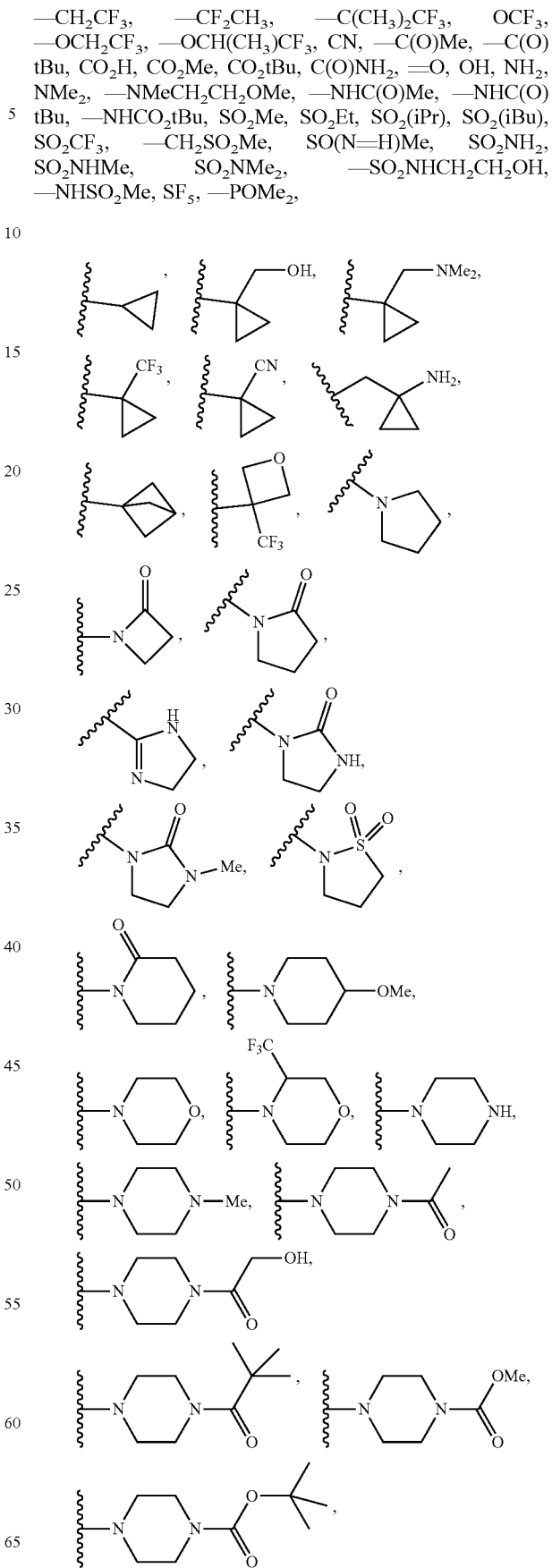

—CH$_2$CF$_3$, —CF$_2$CH$_3$, —C(CH$_3$)$_2$CF$_3$, OCF$_3$, —OCH$_2$CF$_3$, —OCH(CH$_3$)CF$_3$, CN, —C(O)Me, —C(O)tBu, CO$_2$H, CO$_2$Me, CO$_2$tBu, C(O)NH$_2$, =O, OH, NH$_2$, NMe$_2$, —NMeCH$_2$CH$_2$OMe, —NHC(O)Me, —NHC(O)tBu, —NHCO$_2$tBu, SO$_2$Me, SO$_2$Et, SO$_2$(iPr), SO$_2$(iBu), SO$_2$CF$_3$, —CH$_2$SO$_2$Me, SO(N=H)Me, SO$_2$NH$_2$, SO$_2$NHMe, SO$_2$NMe$_2$, —SO$_2$NHCH$_2$CH$_2$OH, —NHSO$_2$Me, SF$_5$, —POMe$_2$,

In some embodiments, the compound of Formula (I), (I-1), (Ia), (Ia-1), (Ib), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein each R$^6$, is Me, Et, iPr, tBu, —CH$_2$OH, —C(OH)Me$_2$, —OMe, —OEt, —OCH$_2$CH$_2$CH$_3$, —CH$_2$OMe, —OCH$_2$CH$_2$NMe$_2$, F, Cl, Br, CHF$_2$, —CF$_3$, —CH$_2$CHF$_2$,

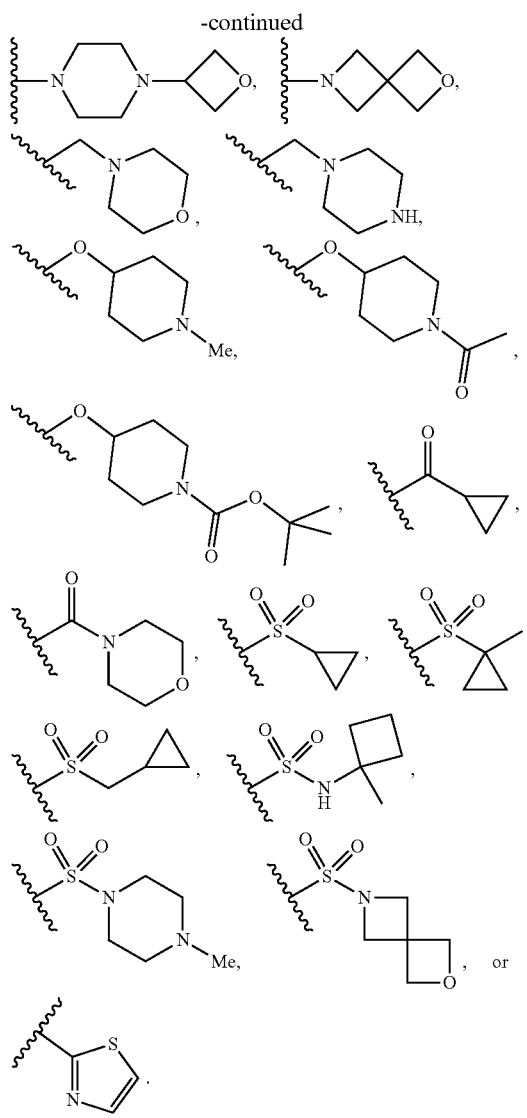

C$_{3-10}$ cycloalkyl, or heterocycloalkyl, wherein the cycloalkyl or heterocycloalkyl is optionally substituted with 1 to 3 R$^6$.

In some embodiments, the compound of Formula (I), (I-1), (Ia), (Ia-1), (Ib), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein each R$^{6j}$ is independently halogen, C$_{1-6}$ haloalkyl, —C(O)R$^{6j1}$, —C(O)OR$^{6j1}$, —OC(O)R$^{6j1}$, —C(O)N(R$^{6j1}$)(R$^{6j2}$), —N(R$^{6j3}$)C(O)R$^{6j2}$, —OC(O)N(R$^{6j1}$)(R$^{6j2}$), —N(R$^{6j1}$)C(O)OR$^{6j2}$, —N(R$^{6j1}$)(R$^{6j2}$), =O, —OR$^{6j}$, —S(O)$_2$R$^{6j1}$, —Si(R$^{6j1}$)(R$^{6j2}$)(R$^{6j3}$), C$_{3-10}$ cycloalkyl, C$_{6-12}$ aryl, heterocycloalkyl, or heteroaryl, wherein the cycloalkyl, aryl, heterocycloalkyl, or heteroaryl is optionally substituted with 1 to 3 R$^{6p}$; wherein each R$^{6j1}$, R$^{6j2}$, and R$^{6j3}$ is independently hydrogen or C$_{1-6}$ alkyl.

In some embodiments, the compound of Formula (I), (I-1), (Ia), (Ia-1), (Ib), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein each R$^6$ is independently OH, OMe, CH$_2$OMe, F, CHF$_2$, CF$_3$, CN, NH$_2$, NH(CO)CF$_3$, NH(CO)OtBu, SO$_2$Me, Si(iPr)$_3$,

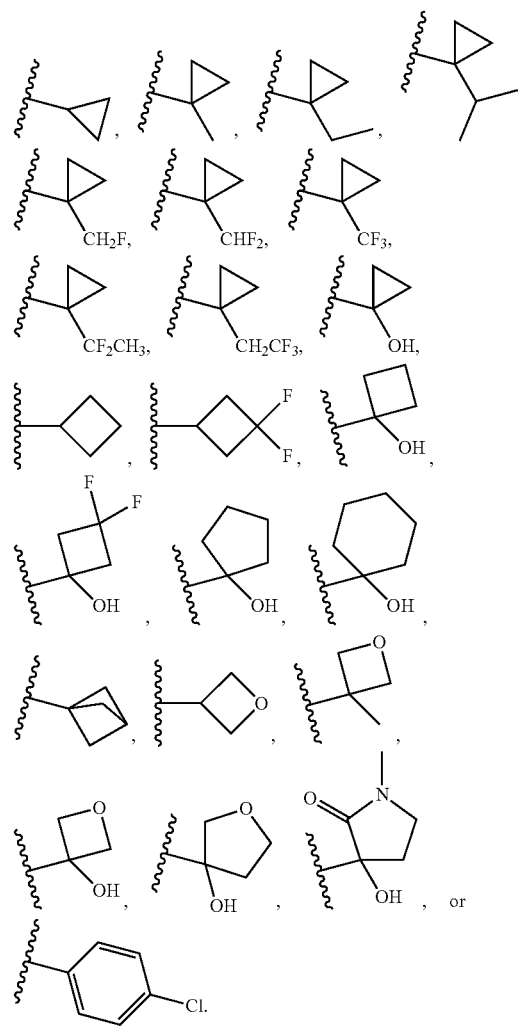

In some embodiments, the compound of Formula (I), (I-1), (Ia), (Ia-1), (Ib), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein each R$^{6e}$ is independently Me, Et, tBu, —OMe, F, Cl, —CF$_3$, —NHC(O)Me, or —OH.

In some embodiments, the compound of Formula (I), (I-1), (Ia), (Ia-1), (Ib), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein each R$^{6e1}$, R$^{6e2}$, and R$^{6e3}$ is independently hydrogen, C$_{1-6}$ alkyl, C$_{1-6}$ hydroxyalkyl, C$_{1-6}$ aminoalkyl, C$_{1-6}$ alkoxyalkyl, C$_{1-6}$ haloalkyl, C$_{3-10}$ cycloalkyl, C$_{1-6}$ alkyl-C$_{3-10}$ cycloalkyl, heterocycloalkyl, or C$_{1-6}$ alkyl-(heterocycloalkyl), wherein the cycloalkyl or heterocycloalkyl is optionally substituted with 1 to 3 R$^{6n}$. In some embodiments, the compound of Formula (I), (I-1), (Ia), (Ia-1), (Ib), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein each R$^{6e1}$, R$^{6e2}$, and R$^{6e3}$ is independently hydrogen, C$_{1-6}$ alkyl, C$_{1-6}$ hydroxyalkyl, C$_{1-6}$ alkoxyalkyl, C$_{3-10}$ cycloalkyl, C$_{1-6}$ alkyl- In some embodiments, the compound of Formula (I), (I-1), (Ia), (Ia-1), (Ib), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein each $R^6$ is independently OH, OMe, F, $CHF_2$, $CF_3$, $NH_2$, NH(CO)OtBu, $SO_2Me$, $Si(iPr)_3$,

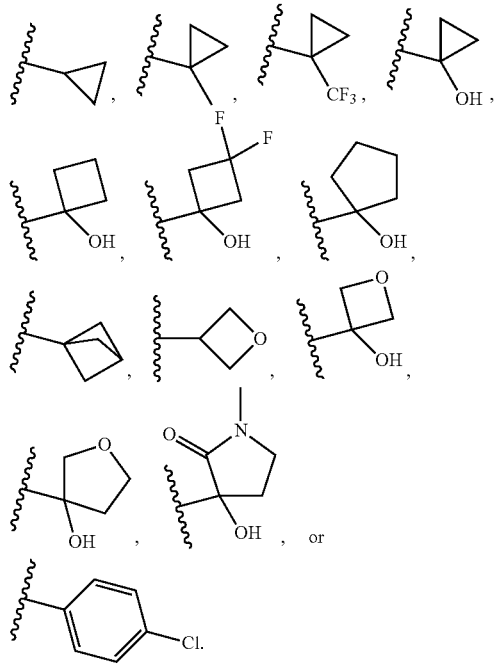

In some embodiments, the compound of Formula (I), (I-1), (Ia), (Ia-1), (Ib), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein each $R^6$ is independently $C_{1-6}$ alkyl, $C_{1-6}$ hydroxyalkyl, $C_{1-6}$ aminoalkyl, $C_{1-6}$ alkoxy, $C_{2-6}$ alkoxyalkyl, halogen, $C_{1-6}$ haloalkyl, $C_{1-6}$ haloalkoxy, —CN, —C(O)$R^{6p1}$, —C(O)O$R^{6p1}$, —OC(O)$R^{6p1}$, —C(O)N($R^{6p1}$)($R^{6p2}$), —N($R^{6p1}$)C(O)$R^{6p2}$, —OC(O)N($R^{6p1}$)($R^{6p2}$), —N($R^{6p1}$)C(O)O$R^{6p2}$, —C(=N$R^{6p3}$)N($R^{6p1}$)($R^{6p2}$), —N($R^{6p1}$)($R^{6p2}$), =O, —OH, —S$R^{6p1}$, —S(O)$R^{6p1}$, —S(N$R^{61}$)(N$R^{6p2}$)$R^{6p3}$, —S(O)(N$R^{6p1}$)($R^{6p2}$), —S(O)$_2R^{6p1}$, —S(O)$_2$N($R^{6p1}$)($R^{6p2}$), or —N($R^{6p1}$)S(O)$_2$($R^{6p2}$); wherein each $R^{6p1}$, $R^{6p2}$, and $R^{6p3}$ is independently hydrogen, $C_{1-6}$ alkyl, $C_{1-6}$ hydroxyalkyl, $C_{1-6}$ aminoalkyl, $C_{2-6}$ alkoxyalkyl, $C_{1-6}$ haloalkyl, $C_{3-10}$ cycloalkyl, $C_{1-6}$ alkyl-$C_{3-10}$ cycloalkyl, $C_{6-10}$ aryl, $C_{1-6}$ alkyl-$C_{6-10}$ aryl, heterocycloalkyl, $C_{1-6}$ alkyl-(heterocycloalkyl), heteroaryl, or $C_{1-6}$ alkyl-(heteroaryl). In some embodiments, the compound of Formula (I), (I-1), (Ia), (Ia-1), (Ib), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein each RP is independently $C_{1-6}$ alkyl, $C_{1-6}$ hydroxyalkyl, $C_{1-6}$ alkoxy, $C_{2-6}$ alkoxyalkyl, halogen, $C_{1-6}$ haloalkyl, —CN, —C(O)$R^{6p1}$, —C(O)O$R^{6p1}$, —OC(O)$R^{6p1}$, —C(O)N($R^{6p1}$)($R^{6p2}$), —N($R^{6p1}$)C(O)$R^{6p2}$, —OC(O)N($R^{6p1}$)($R^{6p2}$), —N($R^{6p1}$)C(O)O$R^{6p2}$, —N($R^{6p1}$)($R^{6p2}$), =O, —OH, —S$R^{6p1}$, —S(O)$R^{6p1}$, —S(O)$_2R^{6p1}$, —S(O)$_2$N($R^{6p1}$)($R^{6p2}$), or —N($R^{6p1}$)S(O)$_2$($R^{6p2}$); wherein each $R^{6p1}$ and $R^{6p2}$ is independently hydrogen or $C_{1-6}$ alkyl.

In some embodiments, the compound of Formula (I), (I-1), (Ia), (Ia-1), (Ib), (Ic), (IIa), (IIa-1), (IIc), (Ic-1), (IIc-2), (IIc-3), (IIc-4), (IIc-5), (IIc-6), (IIc-7), or (IIc-8), or a pharmaceutically acceptable salt thereof, is the compound wherein each $R^6$ is independently Me, Et, iPr, F, Cl, $CH_2F$, $CHF_2$, $CF_3$, $CF_2CH_3$, $CH_2CF_3$, =O, or OH.

In some embodiments, the compound of Formula (I), (I-1), (Ia), (Ia-1), (Ib), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein each $R^{6p}$ is independently Me, Cl, $CF_3$, =O, or OH.

In some embodiments, the compound of Formula (I), (I-1), (Ia), (Ia-1), (Ib), (Ic), (IIa), (IIa-1), (IIc), (Ic-1), (IIc-2), (IIc-3), (IIc-4), (IIc-5), (IIc-6), (IIc-7), or (IIc-8), or a pharmaceutically acceptable salt thereof, is the compound wherein each $R^{6a}$ is independently

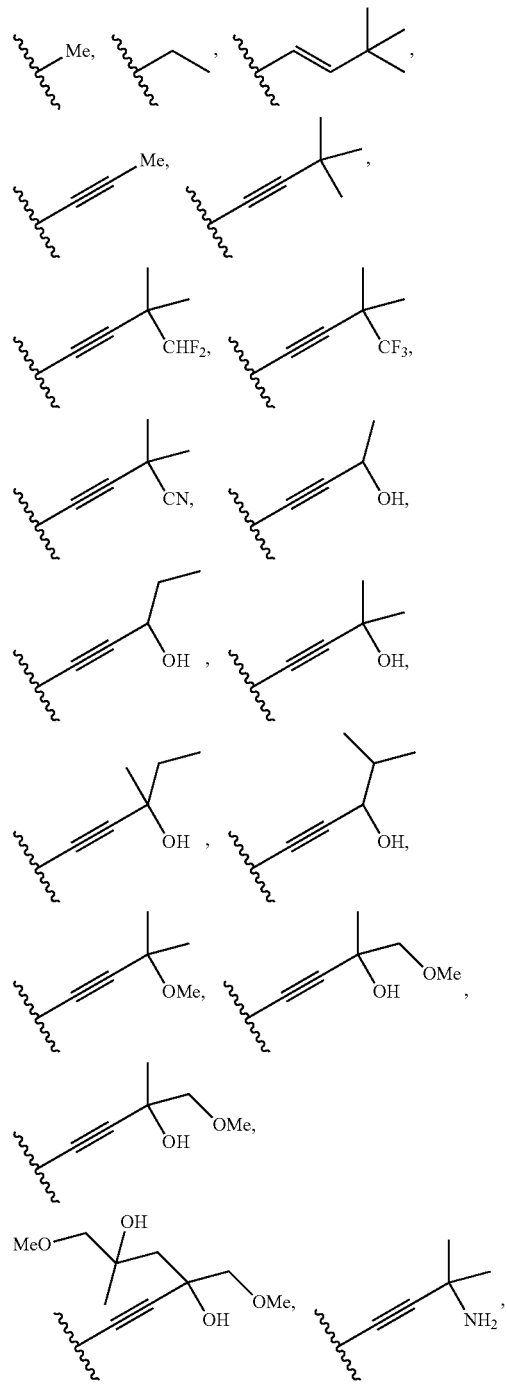

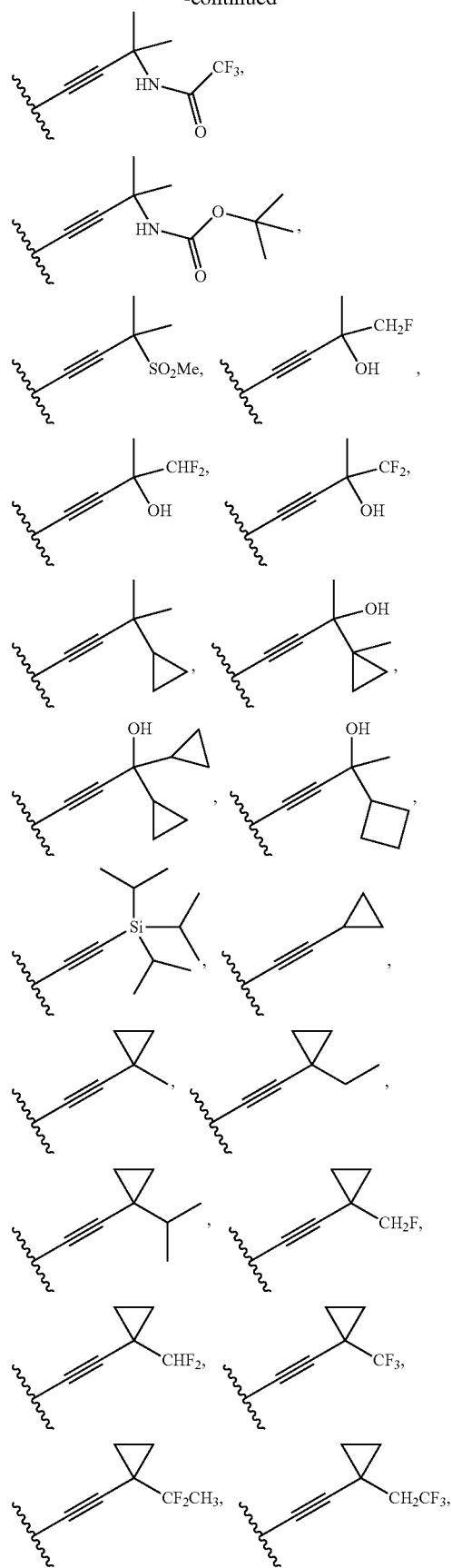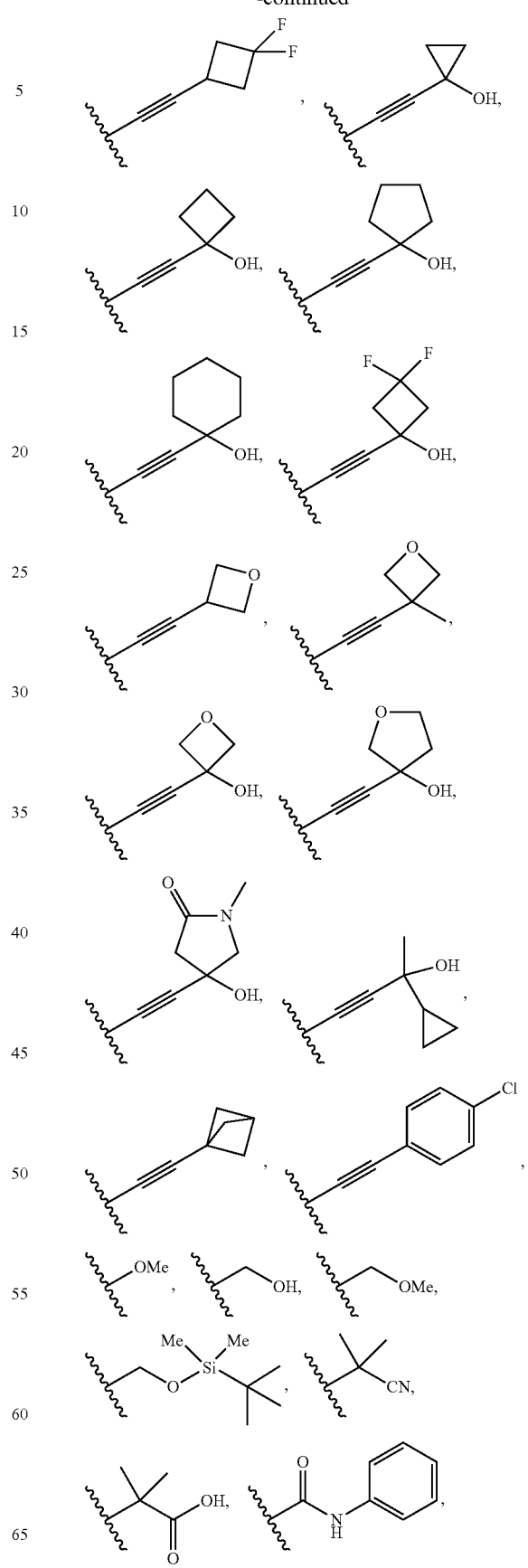

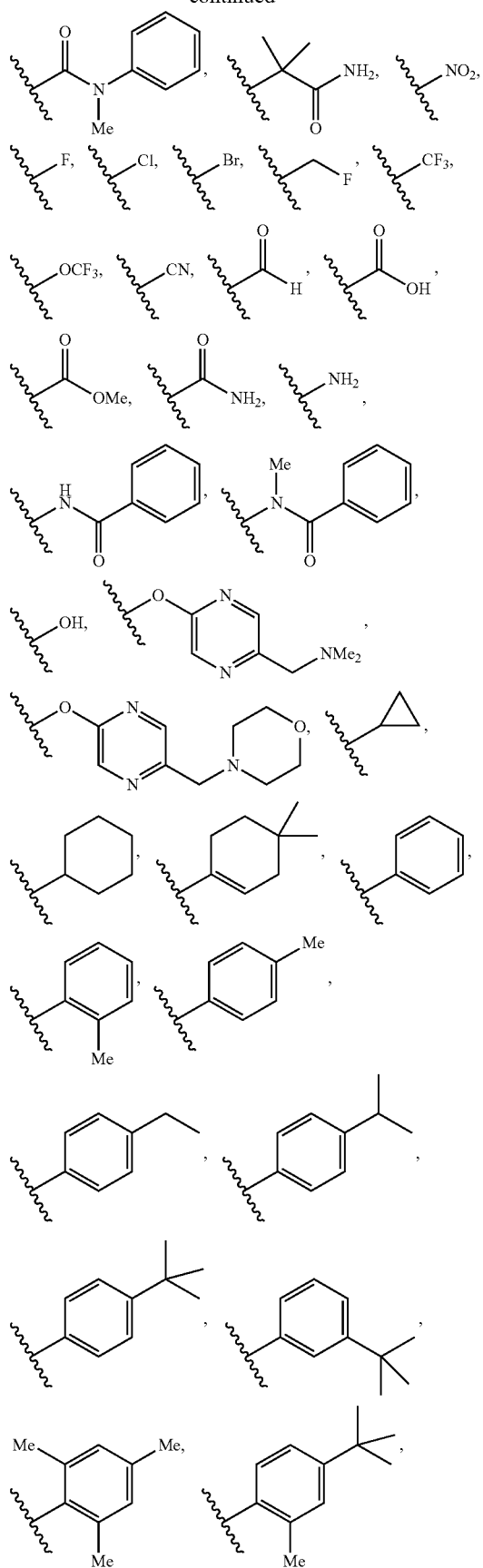
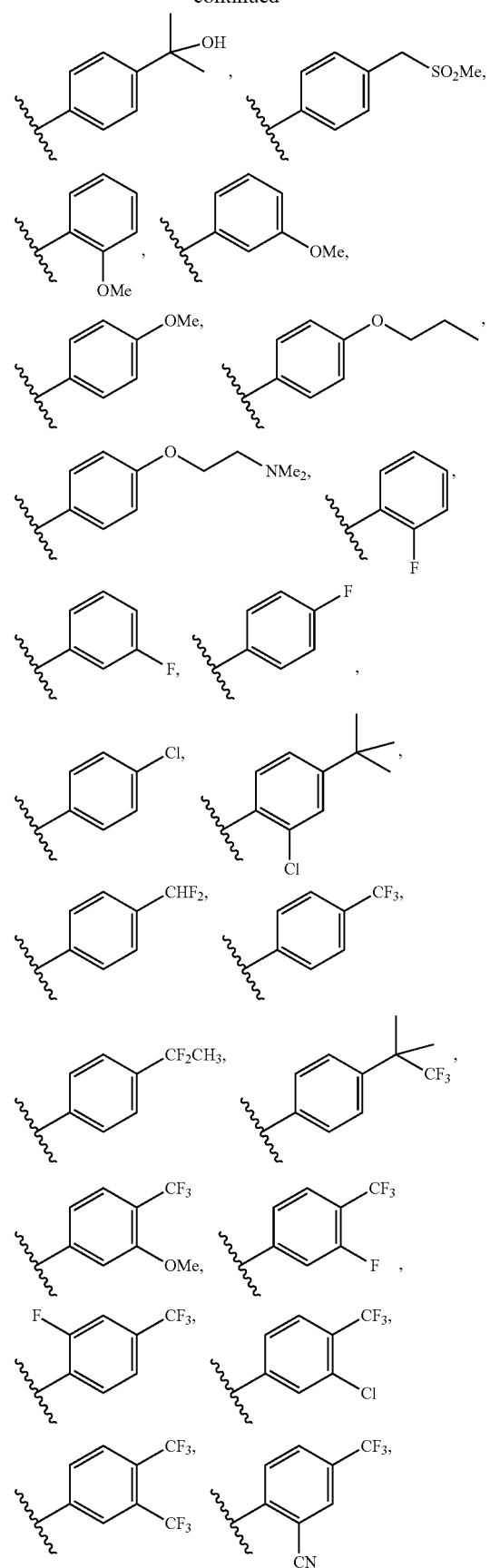

-continued
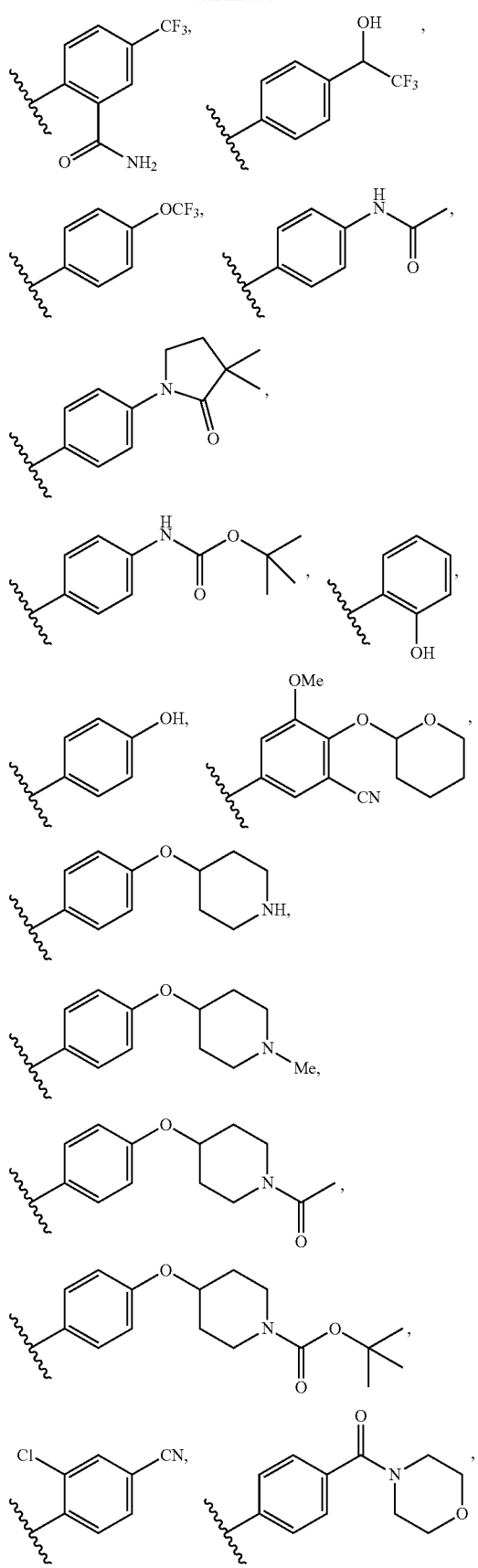
-continued
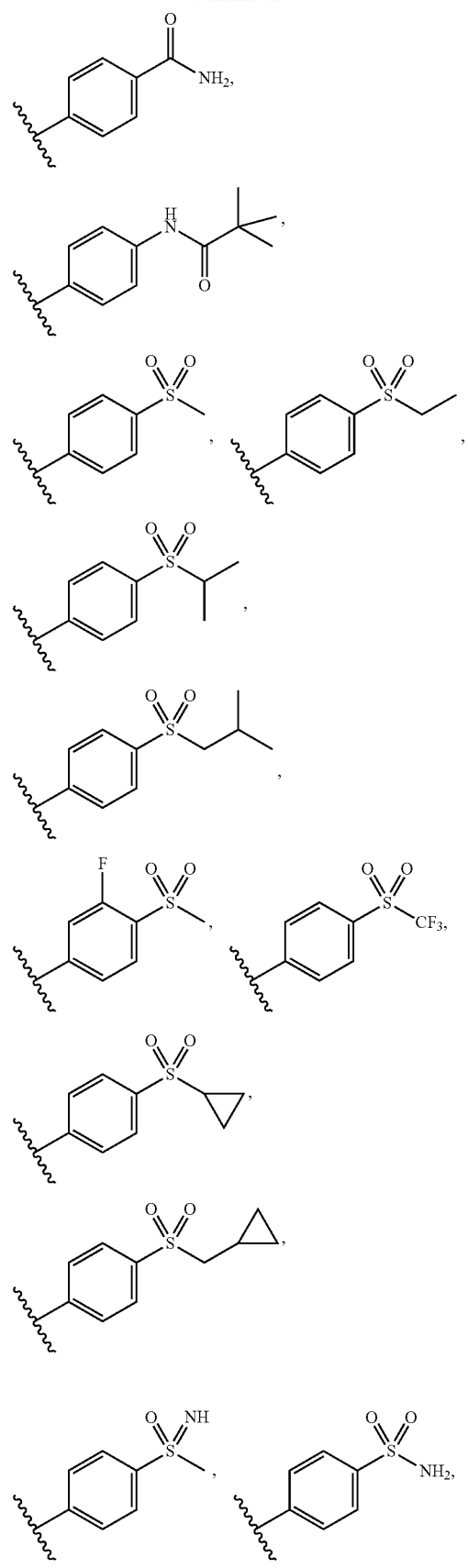

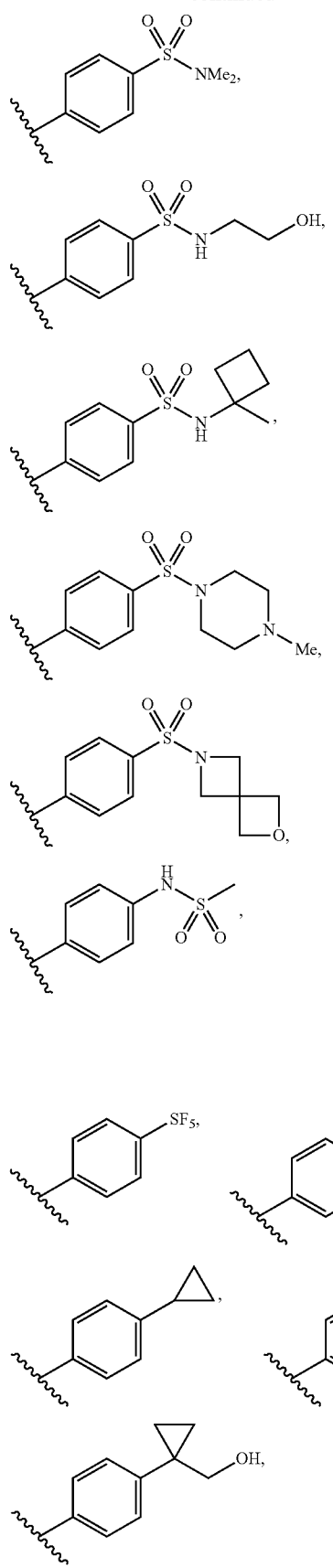
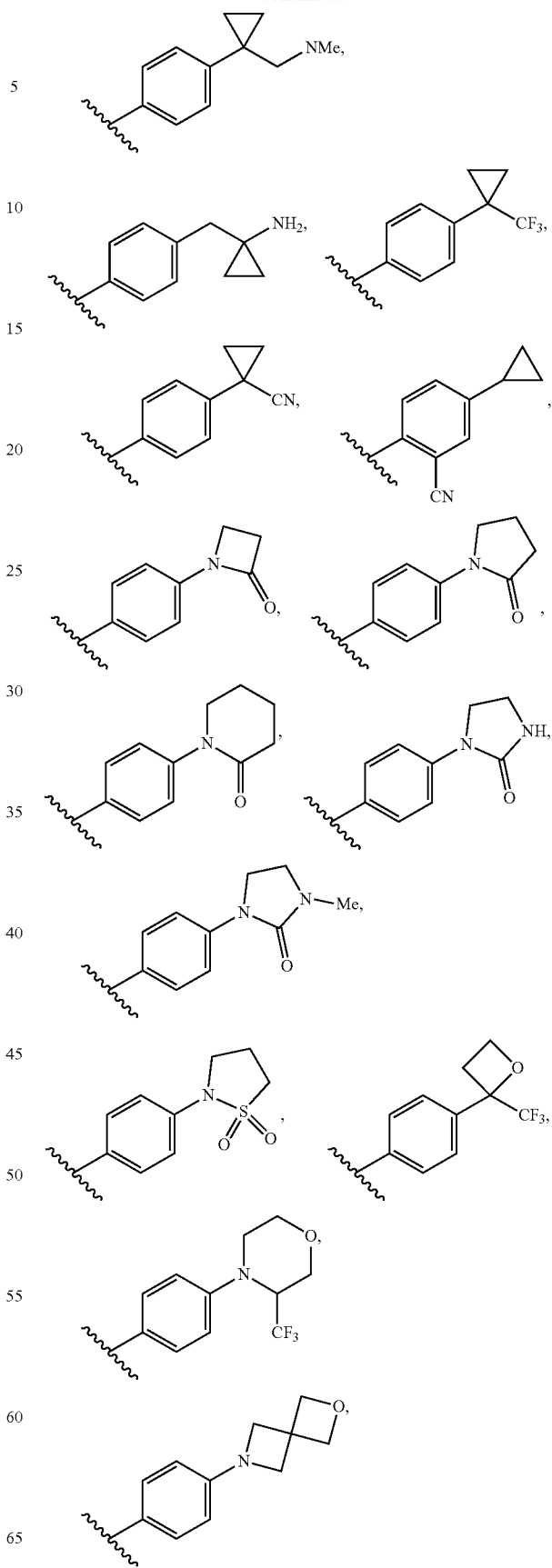

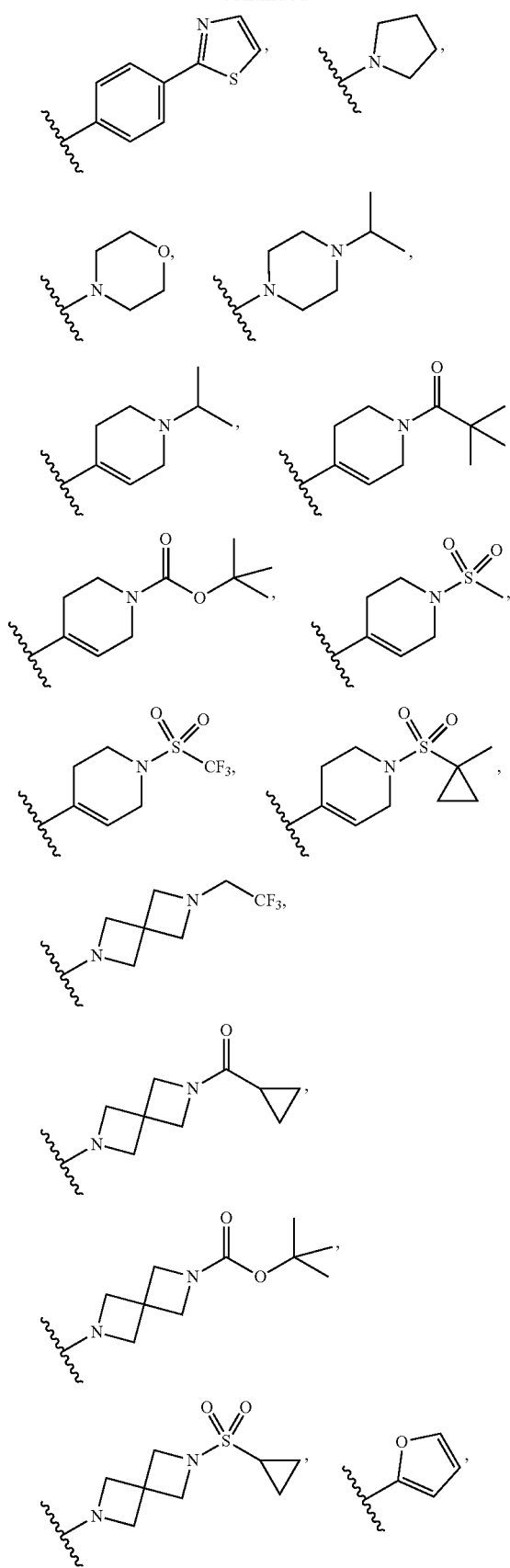
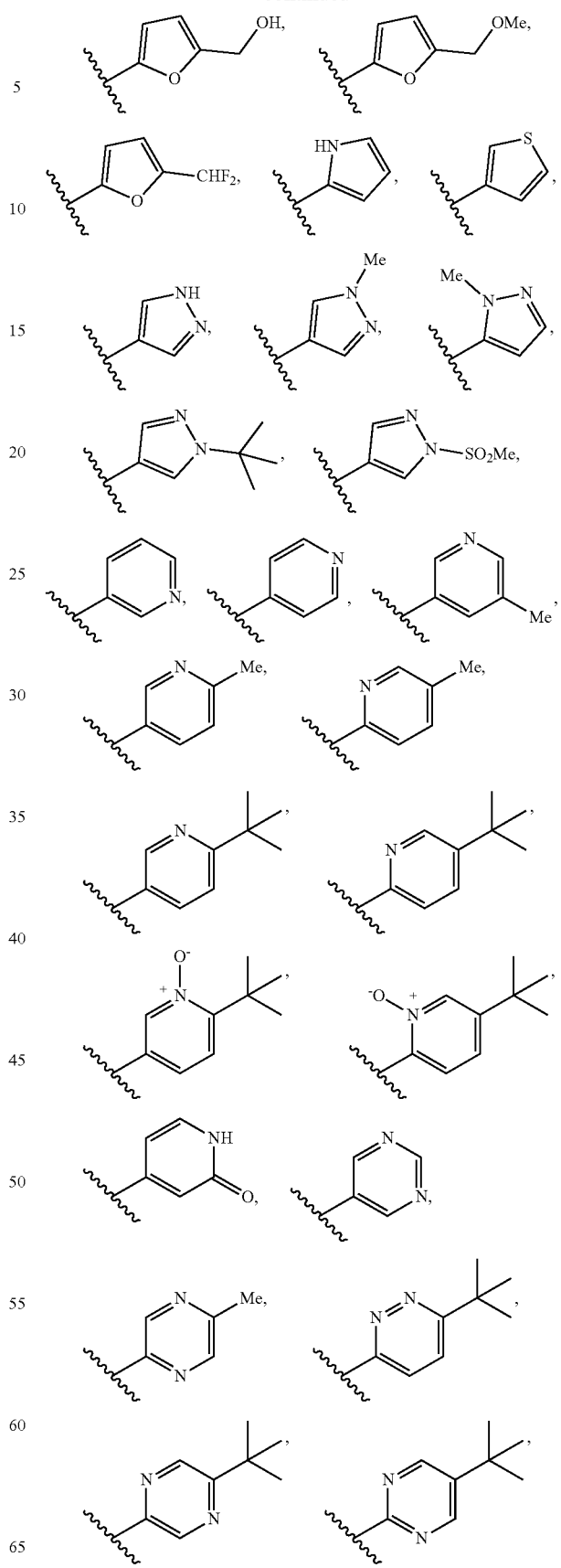

-continued
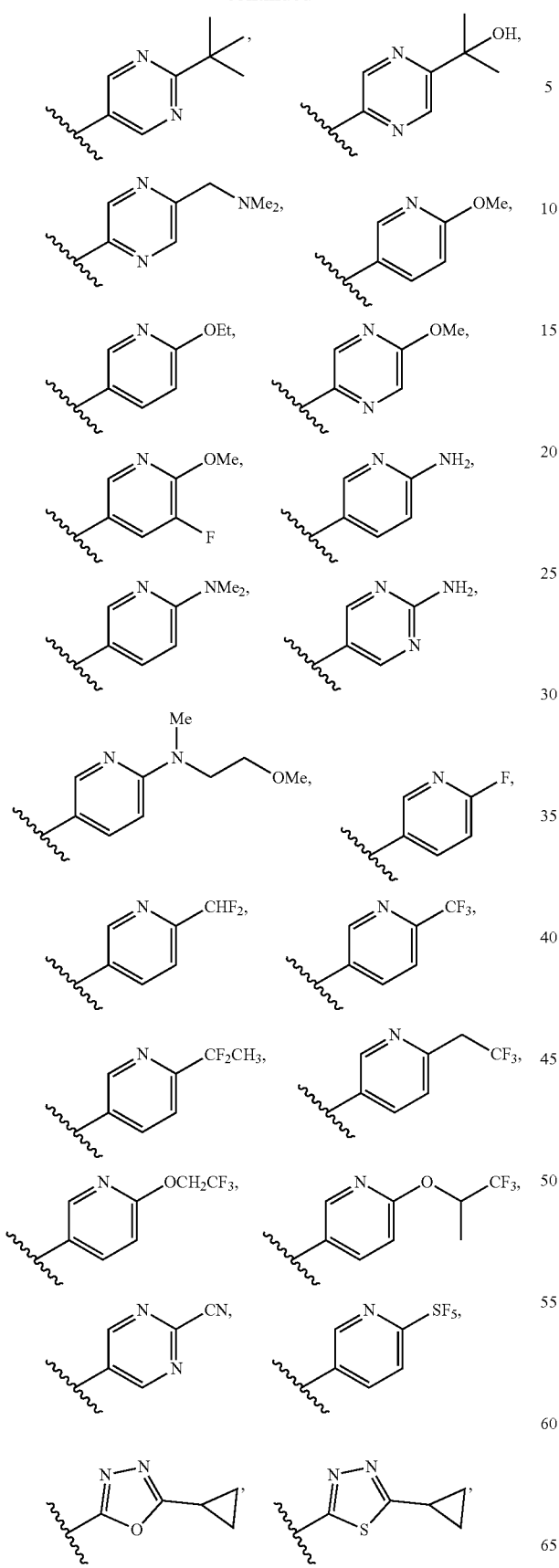
-continued
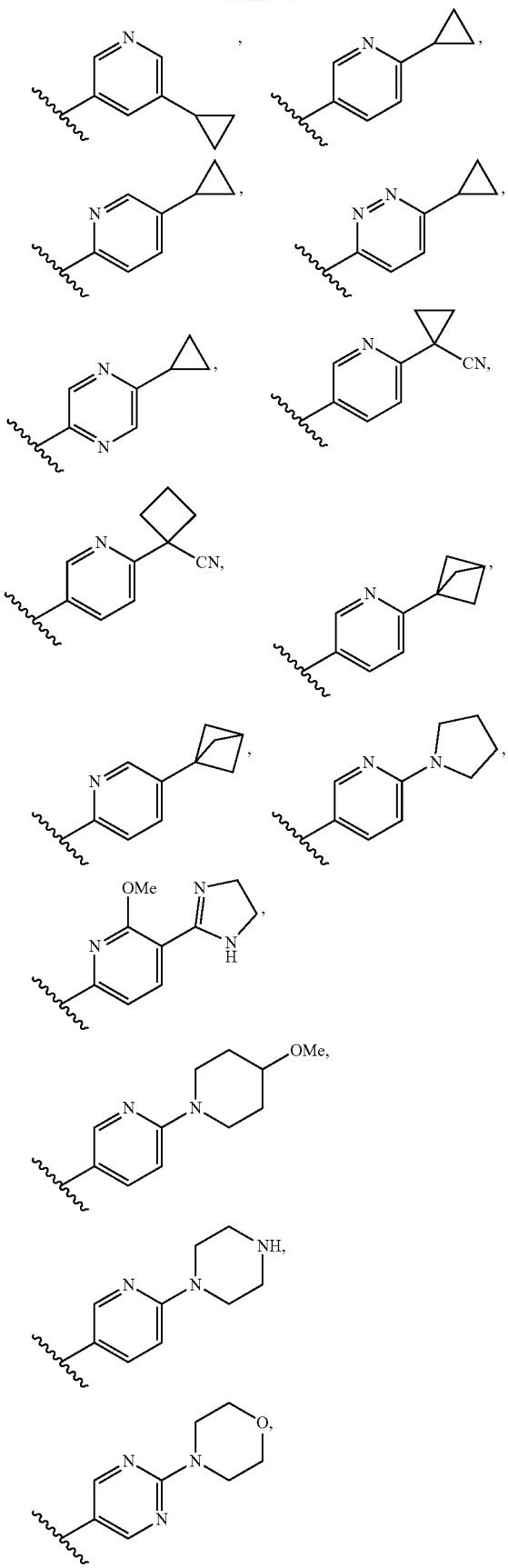

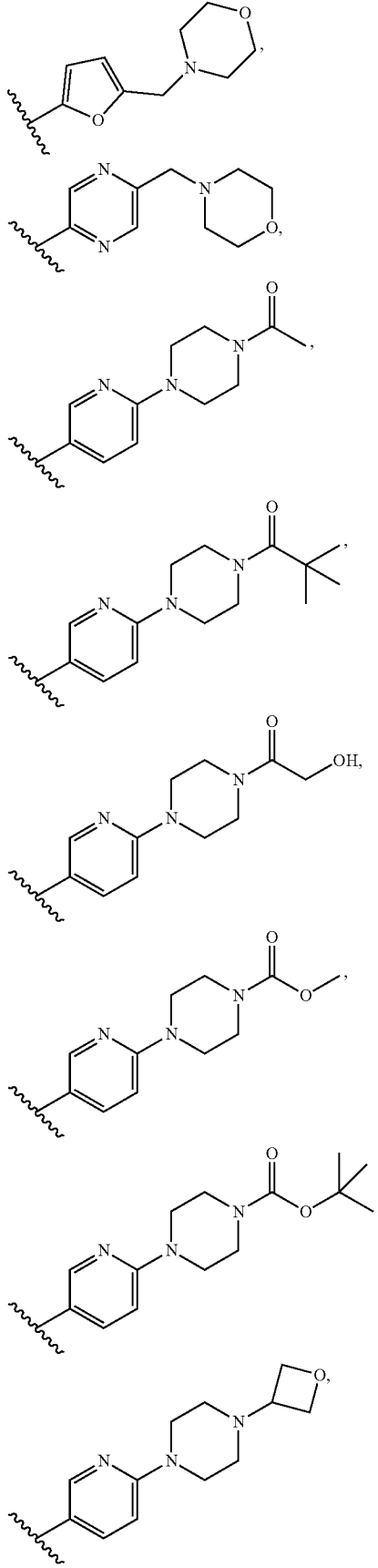
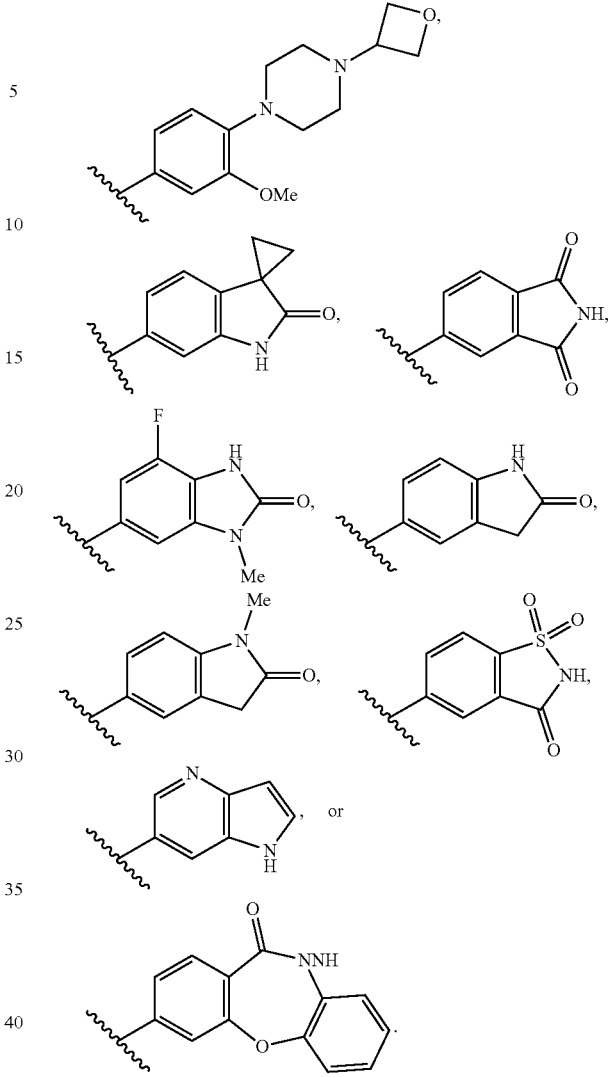
In some embodiments, the compound of Formula (I), (I-1), (Ia), (Ia-1), (Ic), (Ia), (Ia-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein each $R^{6a}$ is independently
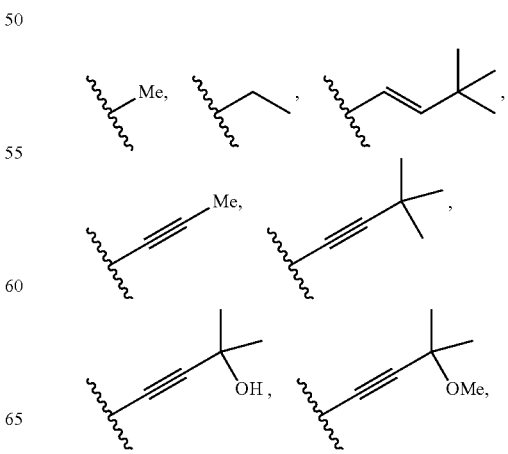

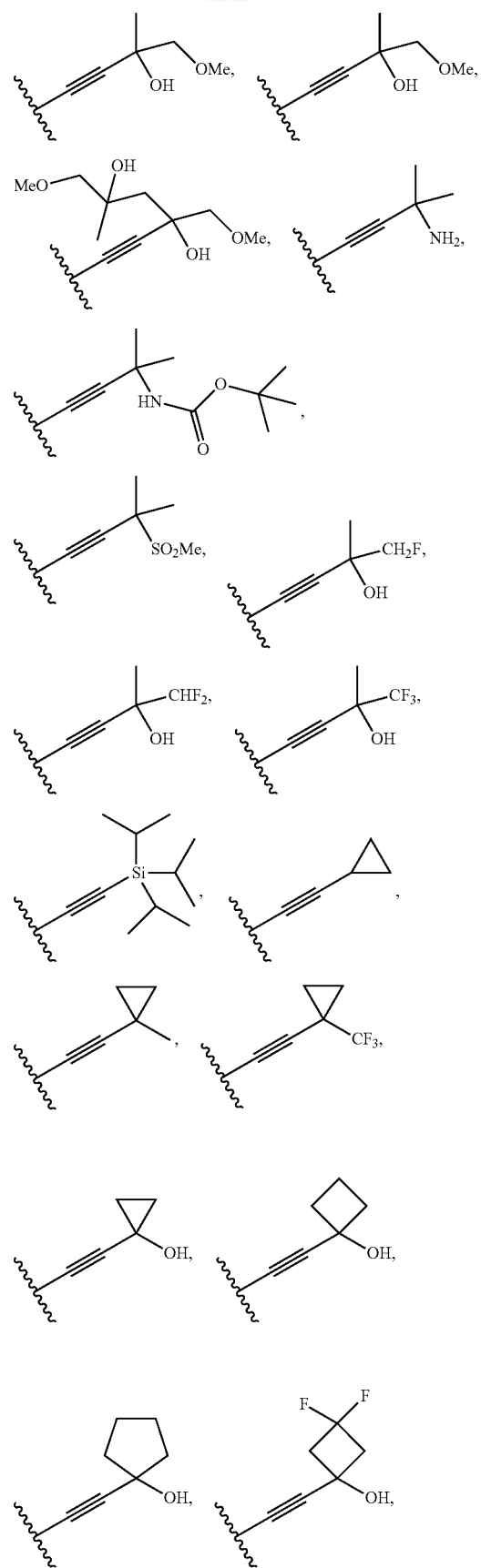
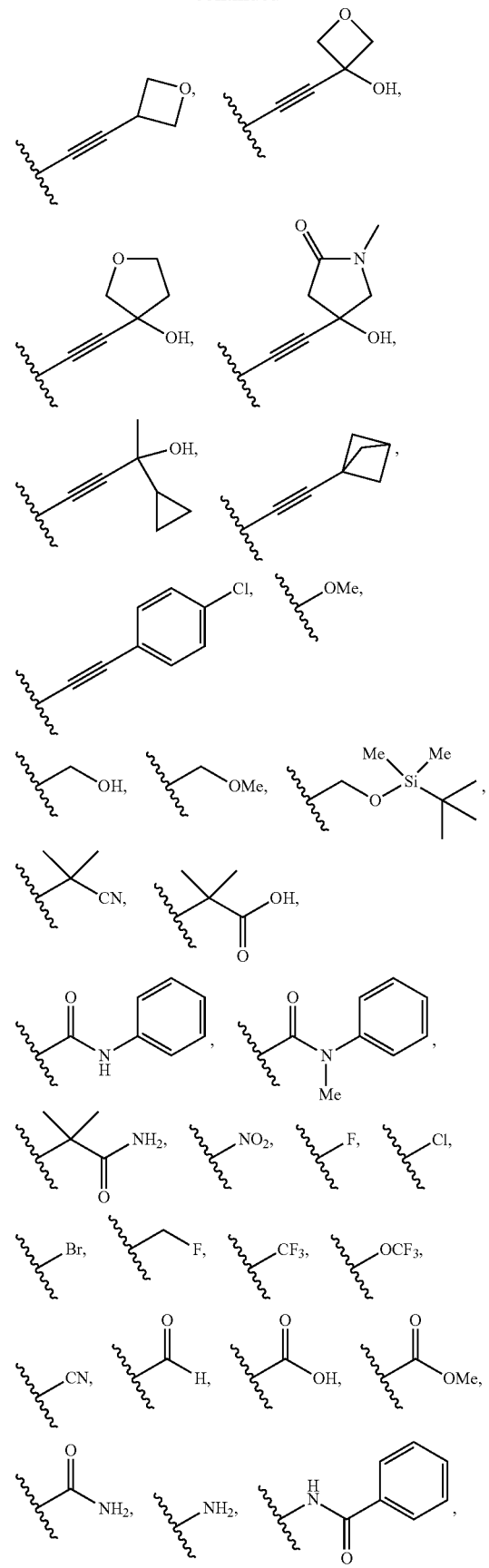

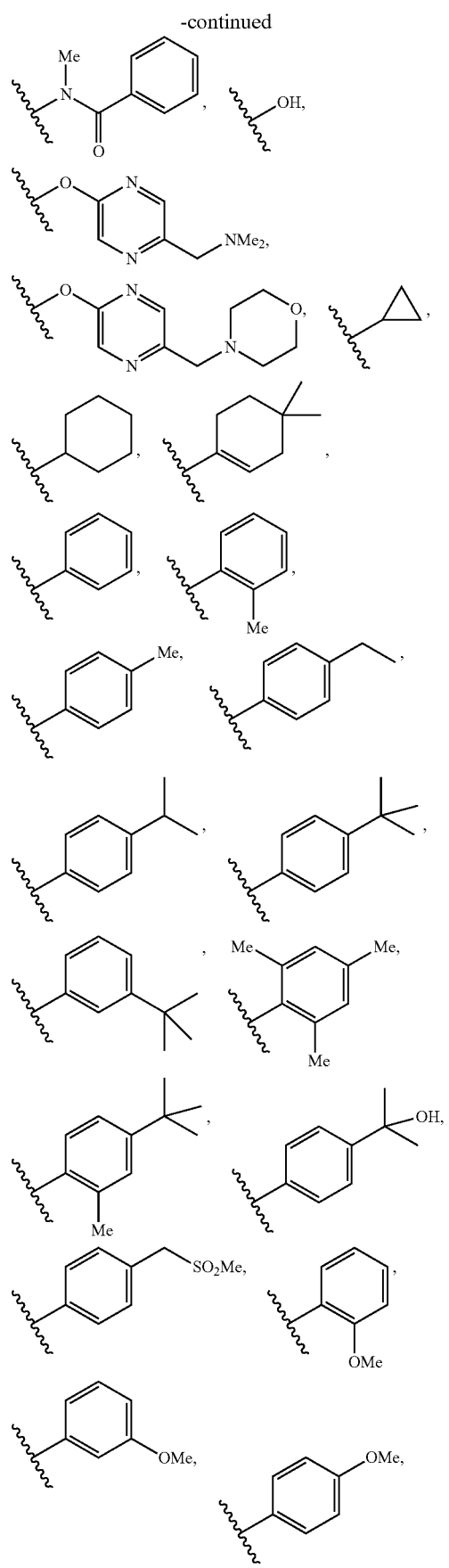
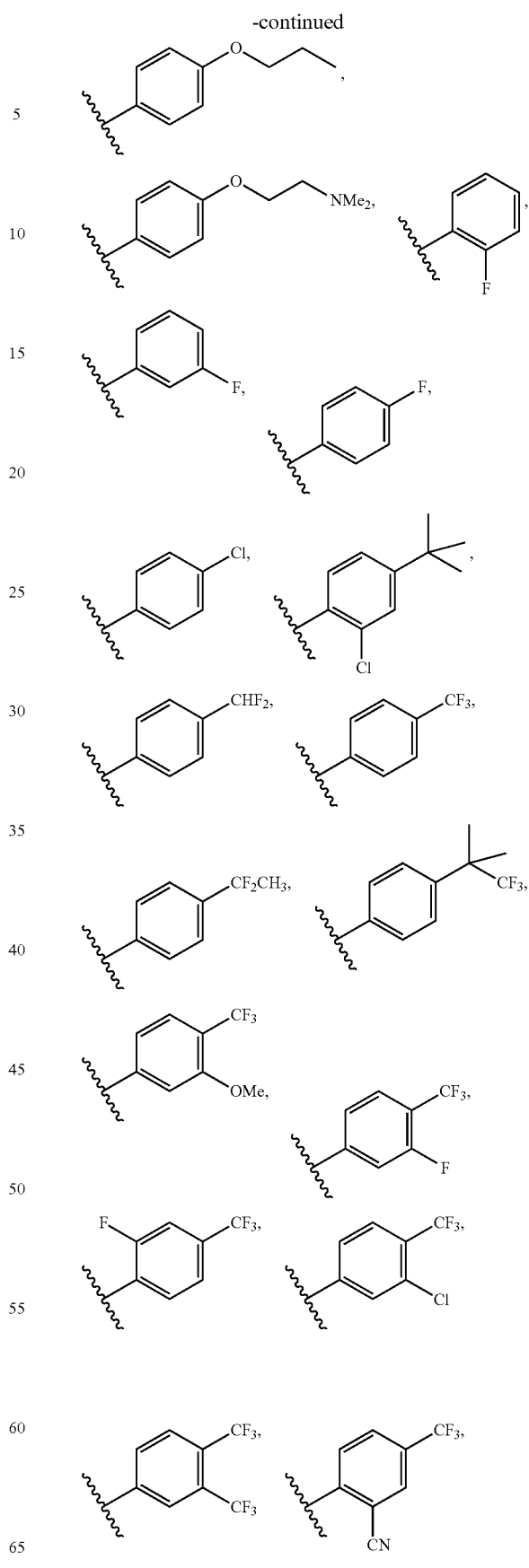

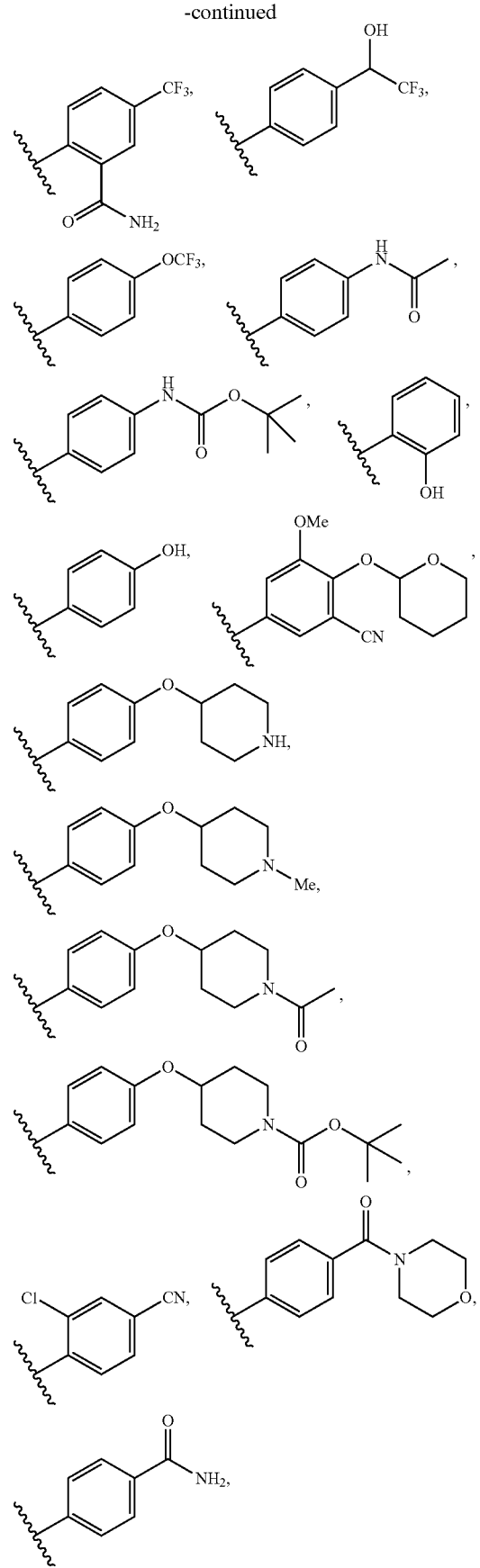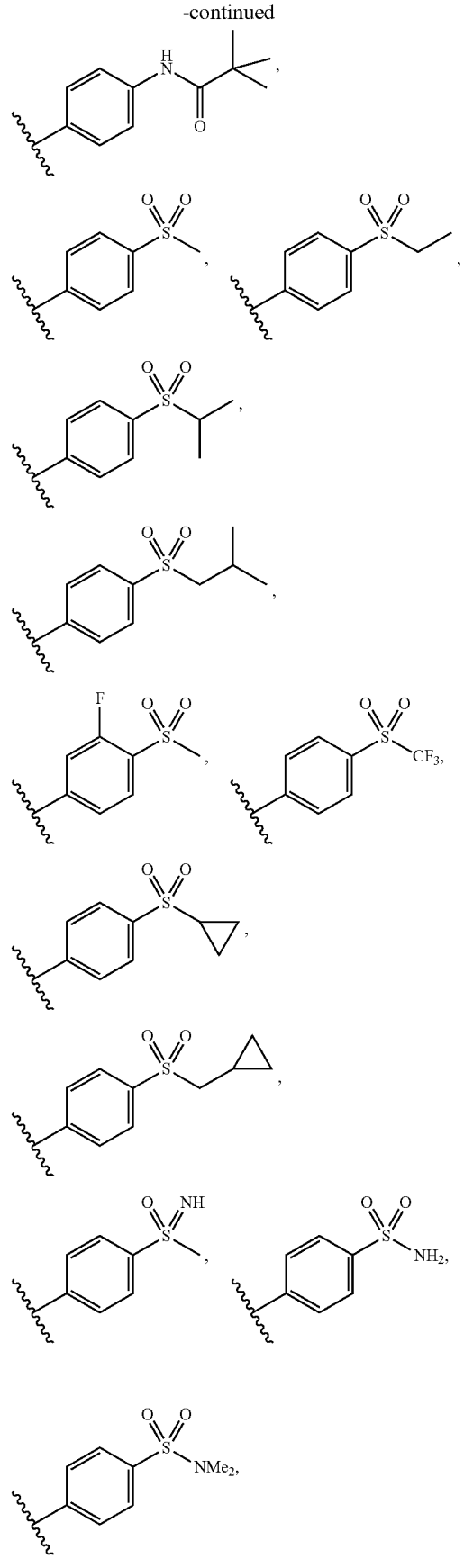

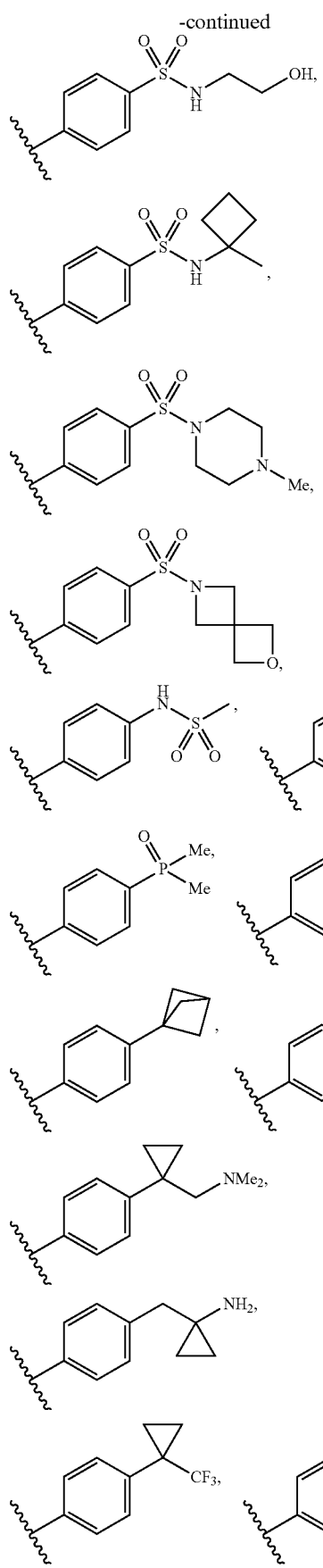
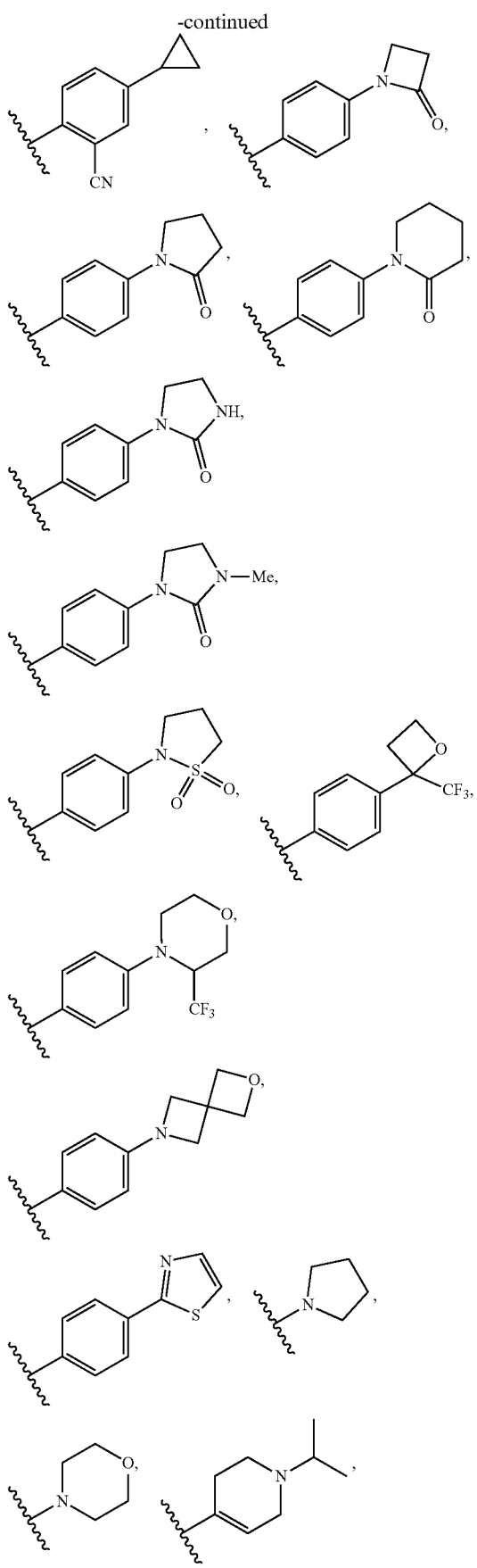

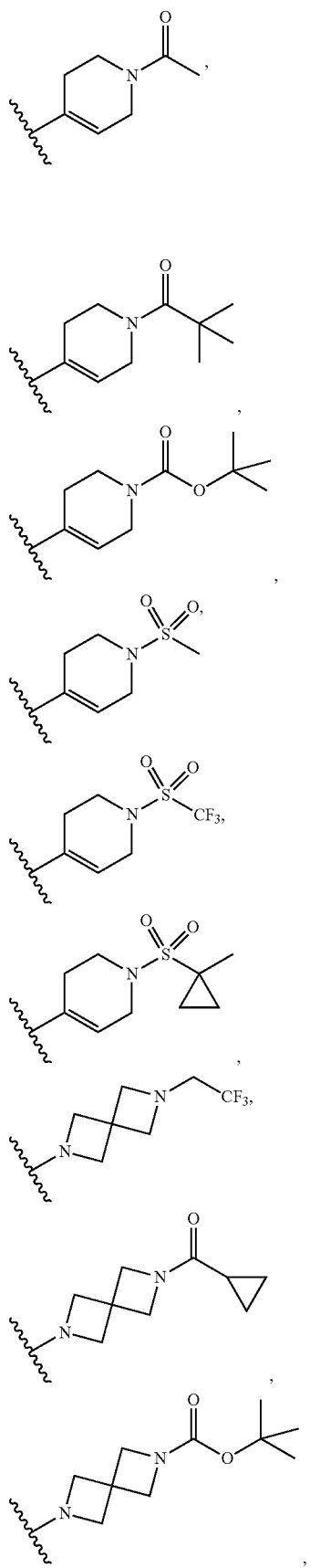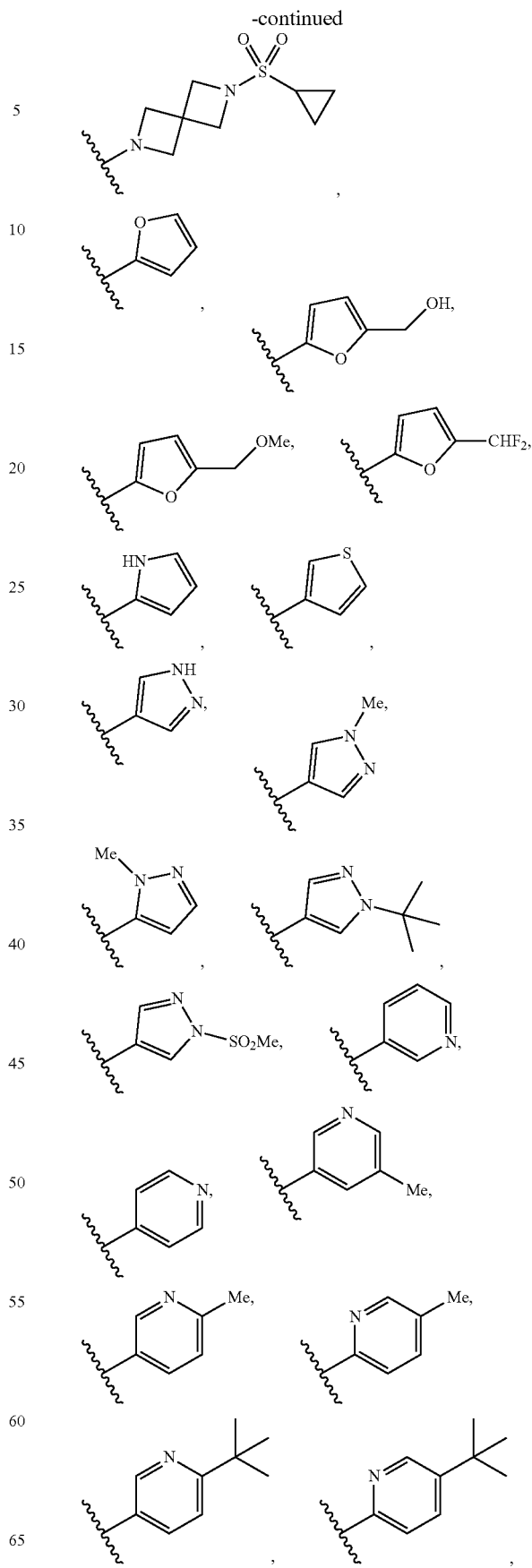

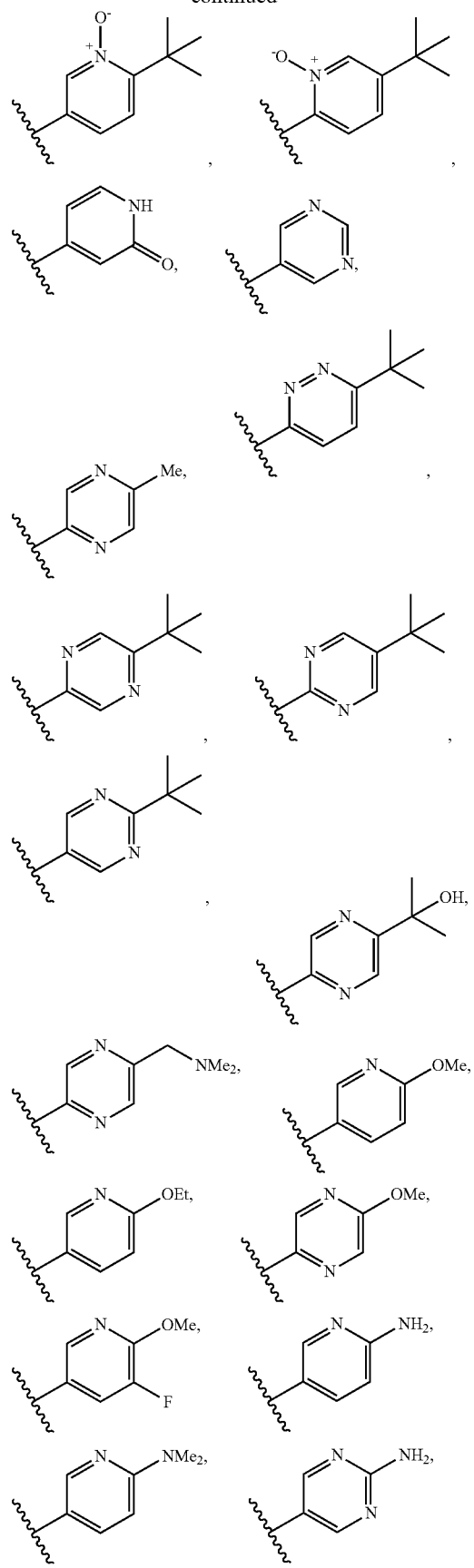
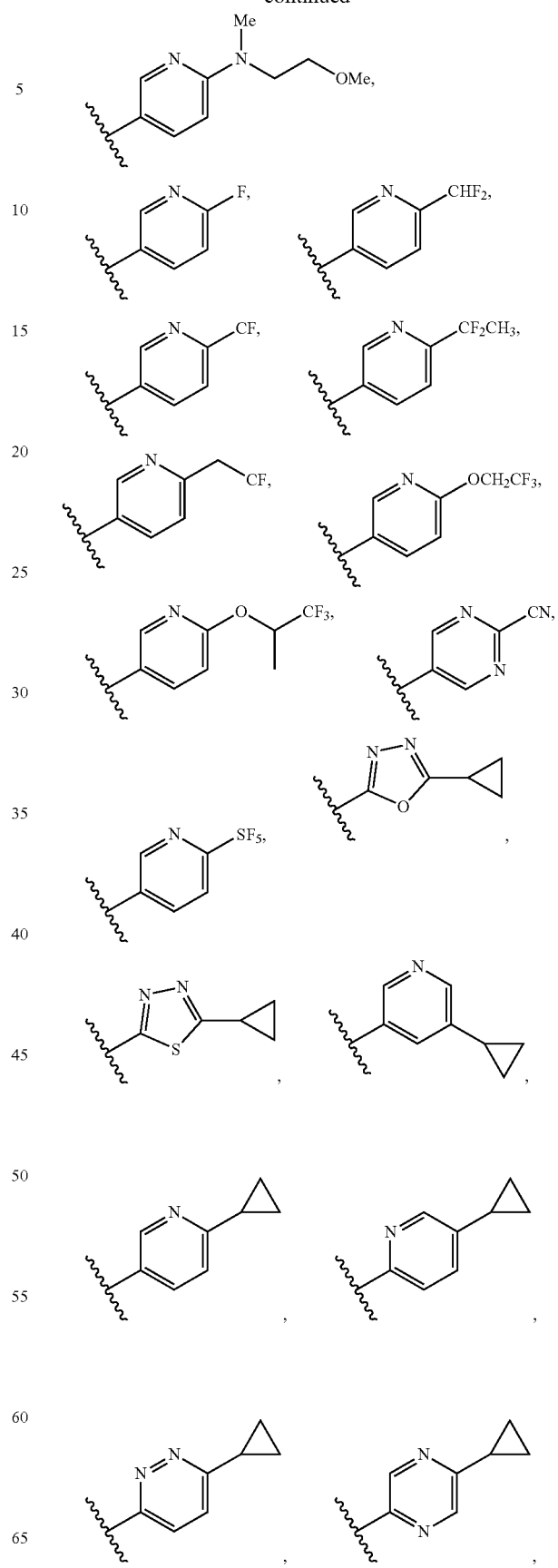

-continued
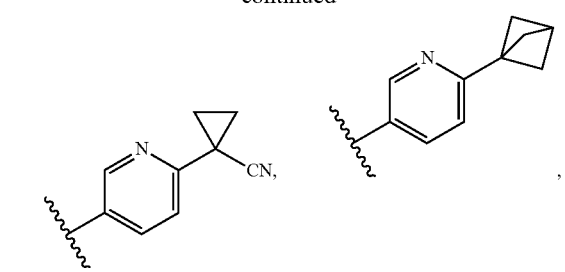
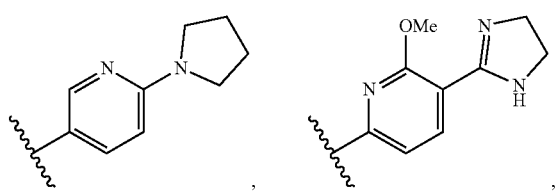
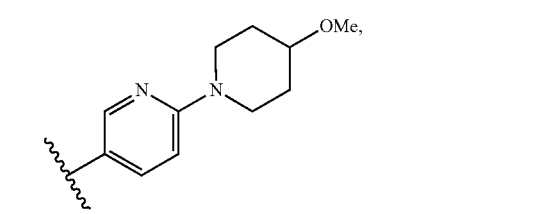
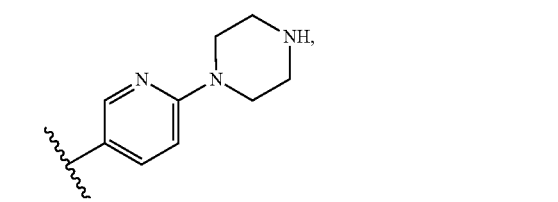
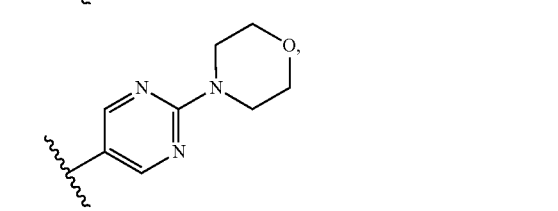
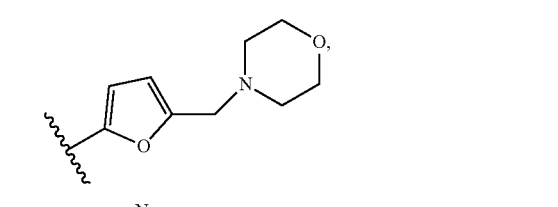
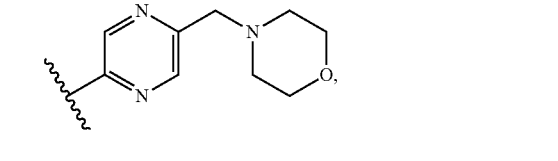
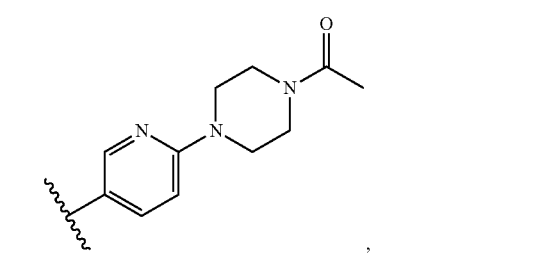
-continued
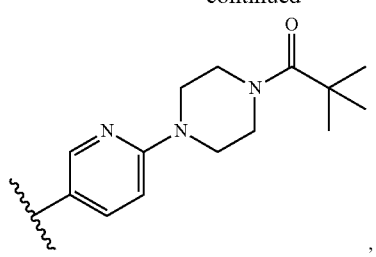
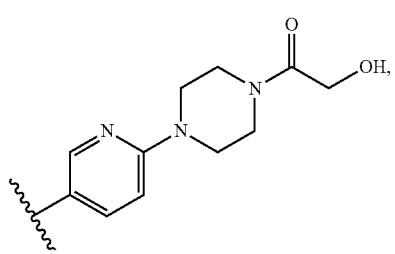
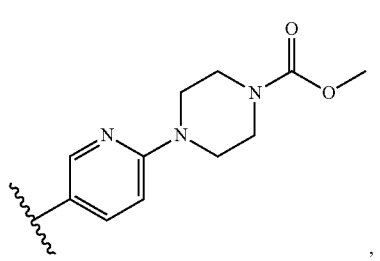
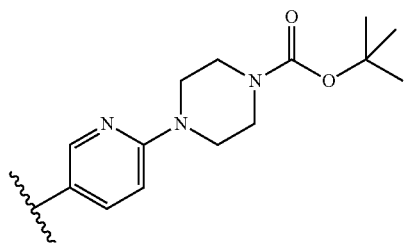
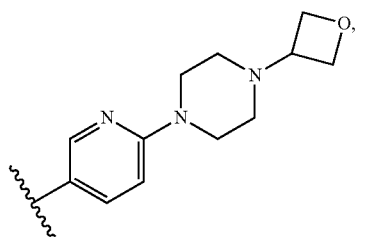
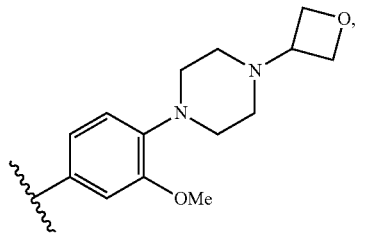
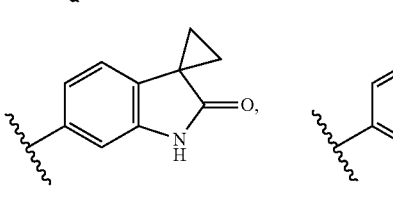

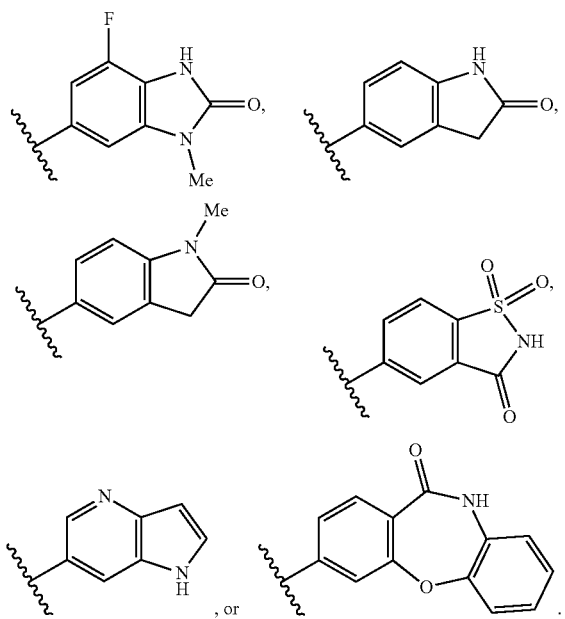

In some embodiments, the compound of Formula (I), (I-1), (Ia), (Ia-1), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein each $R^{6a}$ is independently Me, Et, —C≡CMe, —OMe, —CH$_2$OH, —CH$_2$OMe, —CH$_2$OSi(Me)$_2$(tBu), F, Cl, Br, I, —CH$_2$F, —CF$_3$, —OCF$_3$, —CN, —NO$_2$, —C(O)H, —COOH, —COOMe, —CONH$_2$, —NH$_2$, —OH, cyclopropyl, cyclohexyl, phenyl, In some embodiments, the compound of Formula (I), (I-1), (Ia), (Ia-1), (Ib), (IIa), or (IIa-1), or a pharmaceutically acceptable salt thereof, is the compound wherein $R^5$ is $C_{1-6}$ alkyl, $C_{2-6}$ alkynyl, $C_{2-6}$ alkoxyalkyl, $C_{1-6}$ alkyl-$C_{3-8}$ cycloalkyl, phenyl, $C_{1-6}$ alkyl-phenyl, or $C_{1-6}$ alkyl-(heterocycloalkyl); $R^6$ is phenyl, optionally substituted with 1 or 2 $R^{6a}$; each $R^{6a}$ is independently $C_{1-6}$ alkyl, $C_{2-6}$ alkynyl, $C_{1-6}$ hydroxyalkyl, $C_{1-6}$ alkoxy, $C_{2-6}$ alkoxyalkyl, halogen, $C_{1-6}$ haloalkyl, $C_{1-6}$ haloalkoxy, —CN, —NO$_2$, —C(O)$R^{6b}$, —C(O)$OR^{6b}$, —C(O)N($R^{6b}$)($R^{6c}$), —N($R^{6b}$)($R^{6c}$, —O$R^{6b}$, or phenyl, wherein the phenyl is optionally substituted with 1 or 2 $R^{6e}$; $R^{6b}$ and $R^{6c}$ are each independently hydrogen or $C_{1-6}$ alkyl; each $R^{6e}$ is independently $C_{1-6}$ alkyl, halogen, $C_{1-6}$ haloalkyl, —N($R^{6e1}$)C(O)$R^{6e2}$, or —O$R^{6e1}$; each $R^{6e1}$ and $R^{6e2}$ is independently hydrogen or $C_{1-8}$ alkyl; and the heterocycloalkyl is a 5 or 6 membered ring having 1 heteroatom N or O. In some embodiments, the compound of Formula (I), (I-1), (Ia), (Ia-1), (Ib), (IIa), or (IIa-1), or a pharmaceutically acceptable salt thereof, is the compound wherein $R^5$ is $C_{1-6}$ alkyl, $C_{2-6}$ alkynyl, $C_{2-3}$ alkoxyalkyl, $C_{1-3}$ alkyl-$C_{3-8}$ cycloalkyl, phenyl, $C_{1-3}$ alkyl-phenyl, or $C_{1-3}$ alkyl-(heterocycloalkyl); $R^6$ is phenyl, optionally substituted with $R^{6a}$; $R^{6a}$ is independently $C_{1-3}$ alkyl, $C_{2-3}$ alkynyl, $C_{1-3}$ hydroxyalkyl, $C_{1-3}$ alkoxy, $C_{2-3}$ alkoxyalkyl, halogen, $C_{1-3}$ haloalkyl, $C_{1-3}$ haloalkoxy, —CN, —NO$_2$, —C(O)$R^{6b}$, —C(O)$OR^{6b}$, —C(O)N($R^{6b}$)($R^{6c}$),) N($R^{6b}$)($R^{6c}$), —OH, or phenyl, wherein the phenyl is optionally substituted with $R^{6e}$; $R^{6b}$ and $R^{6c}$ are each independently hydrogen or $C_{1-3}$ alkyl; $R^{6e}$ is $C_{1-6}$ alkyl, halogen, $C_{1-3}$ haloalkyl, —N($R^{6e1}$)C(O)$R^{6e2}$, or —O$R^{6e1}$; $R^{6e1}$ and $R^{6e2}$ is independently hydrogen or $C_{1-3}$ alkyl; and the heterocycloalkyl is a 6 membered ring having 1 heteroatom N or O.

In some embodiments, the compound of Formula (I), (I-1), or (Ia), or a pharmaceutically acceptable salt thereof, is a compound that has the structure of Formula (Ib):

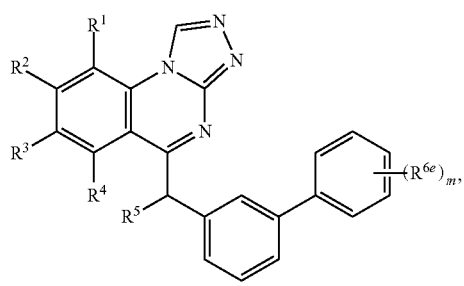

(Ib)

wherein m is 0, 1, 2, or 3. In some embodiments, the compound of Formula (I), (I-1), or (Ia), or a pharmaceutically acceptable salt thereof, is a compound wherein m is 0. In some embodiments, the compound of Formula (I), (I-1), or (Ia), or a pharmaceutically acceptable salt thereof, is a compound wherein m is 1. In some embodiments, the compound of Formula (I), (I-1), or (Ia), or a pharmaceutically acceptable salt thereof, is a compound wherein m is 2. In some embodiments, the compound of Formula (I), (I-1), or (Ia), or a pharmaceutically acceptable salt thereof, is a compound wherein m is 3.

In some embodiments, the compound of Formula (I) or (I-1), or a pharmaceutically acceptable salt thereof, is the compound wherein $R^6$ is

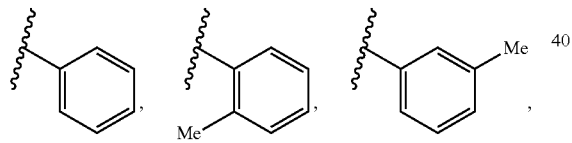

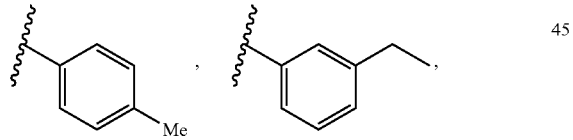

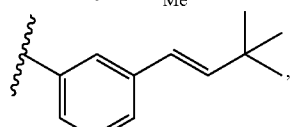

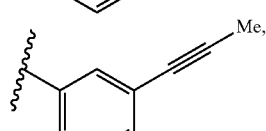

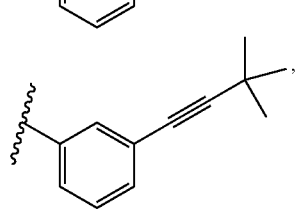

-continued

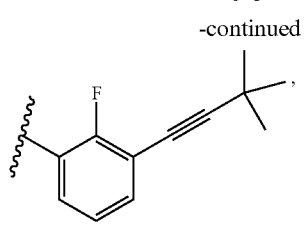

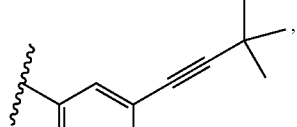

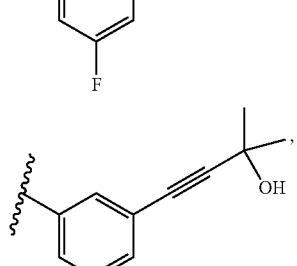

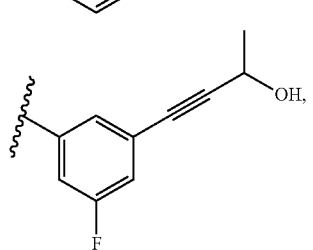

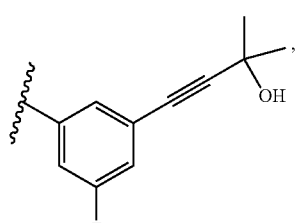

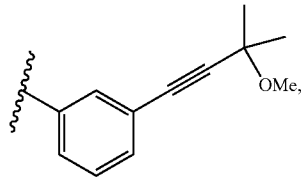

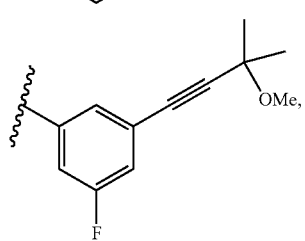

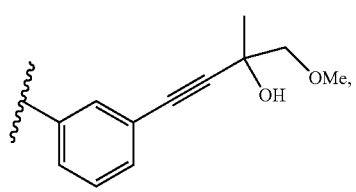

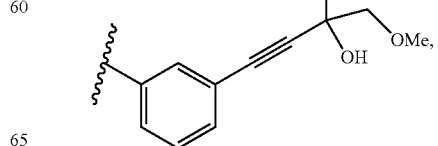

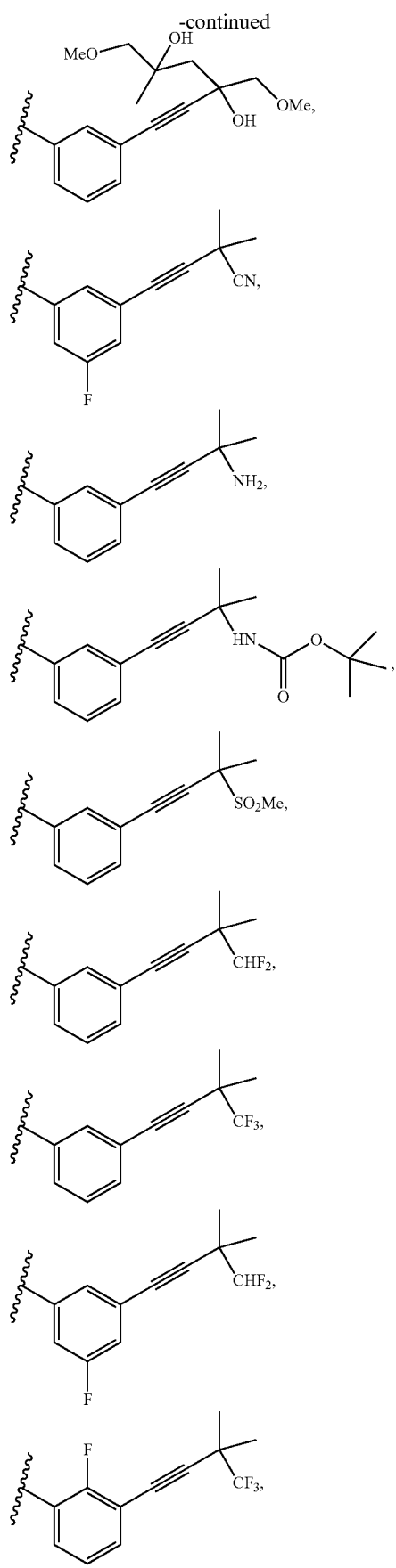
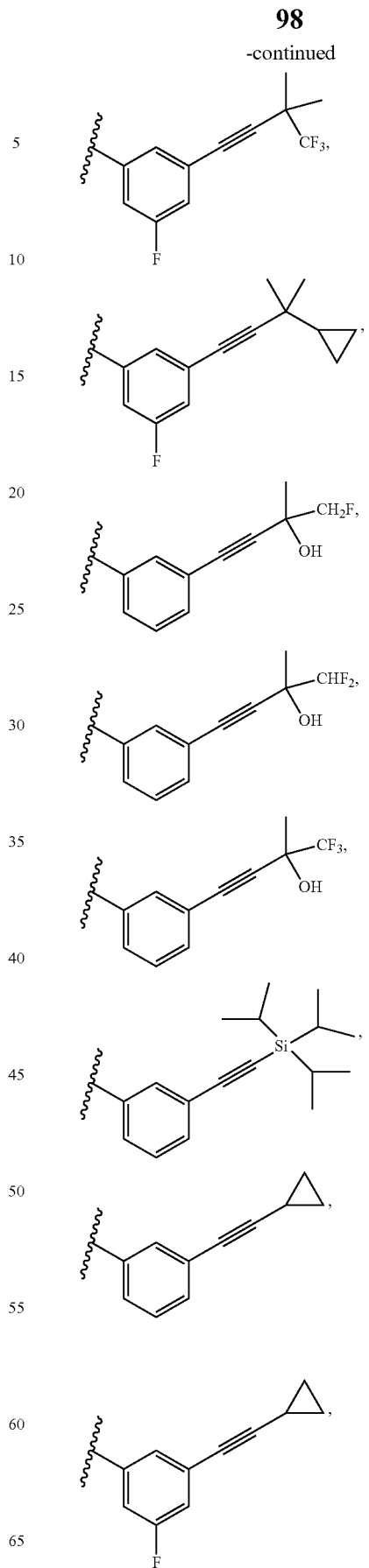

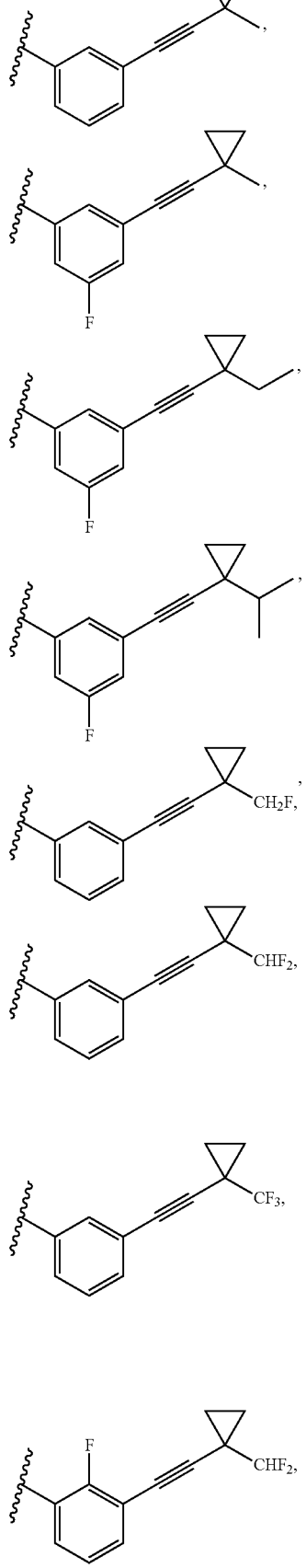
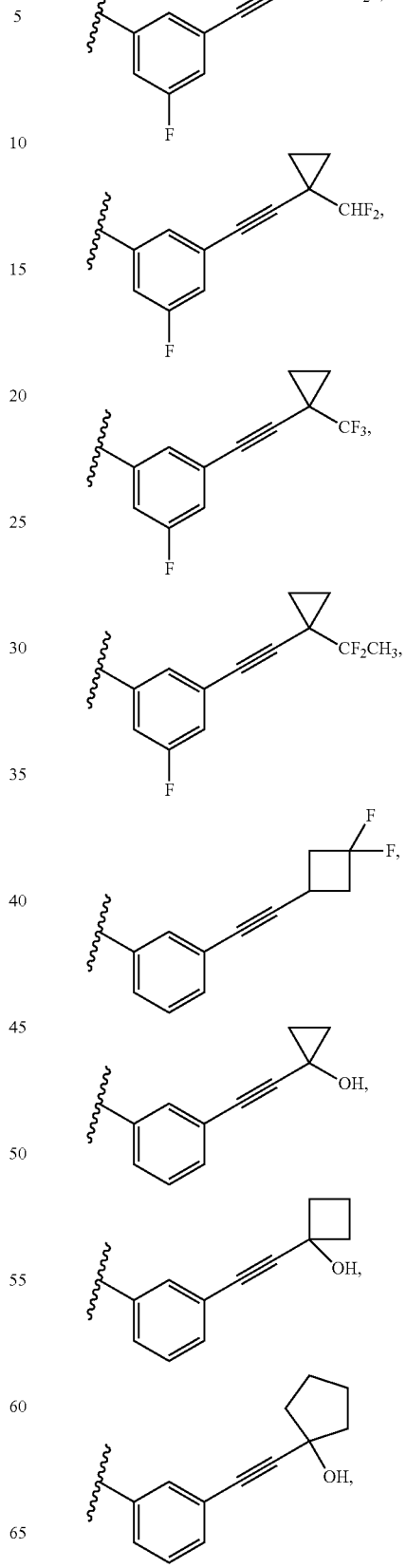

101
-continued
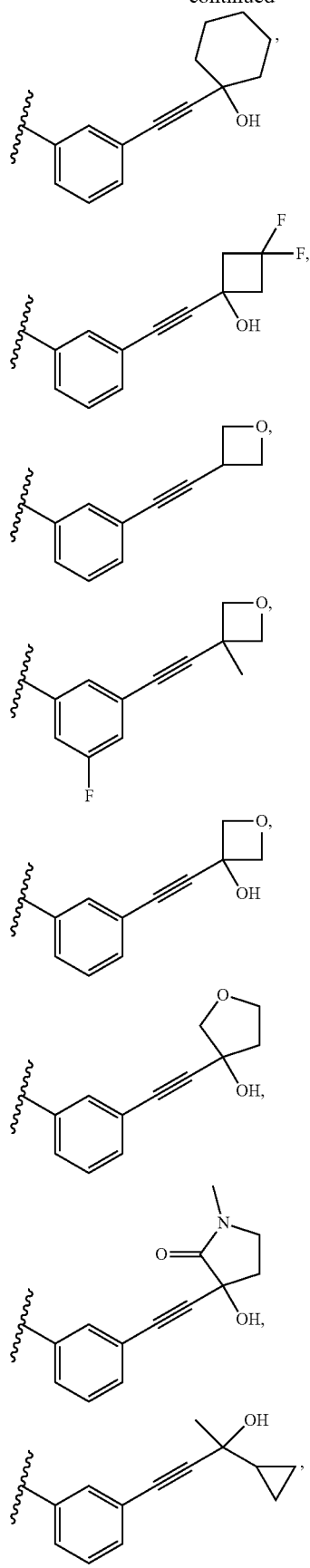
102
-continued
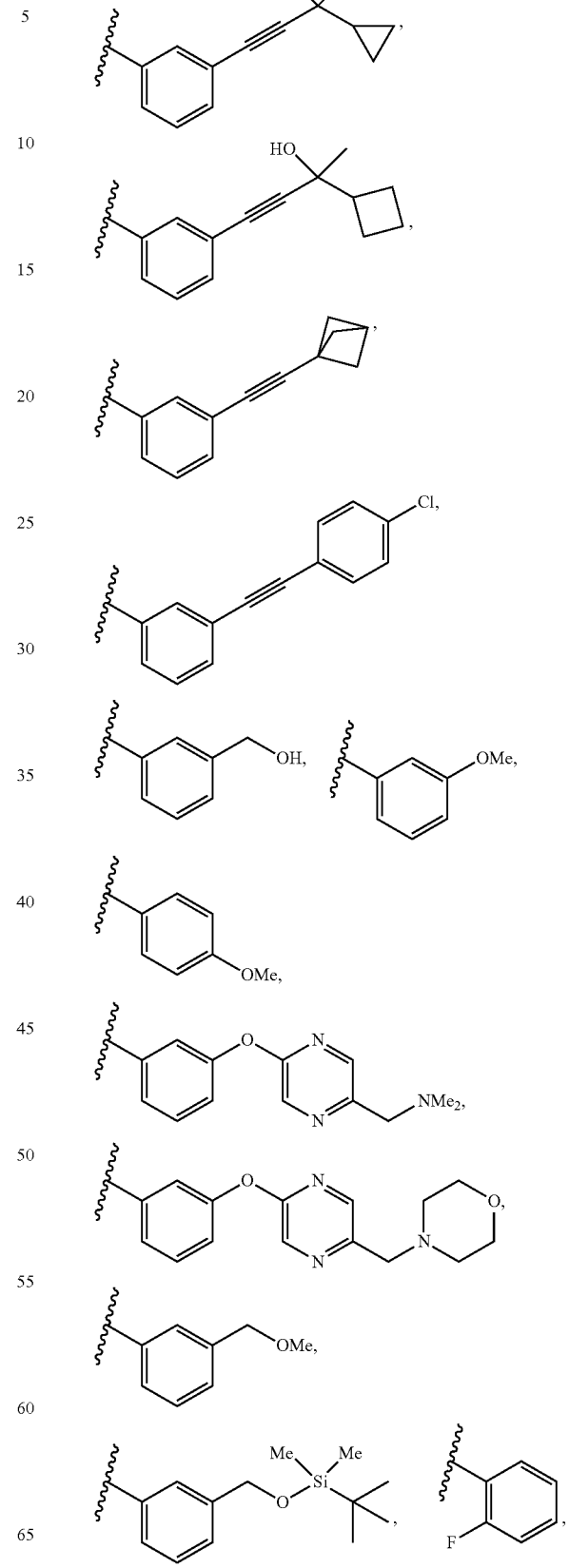

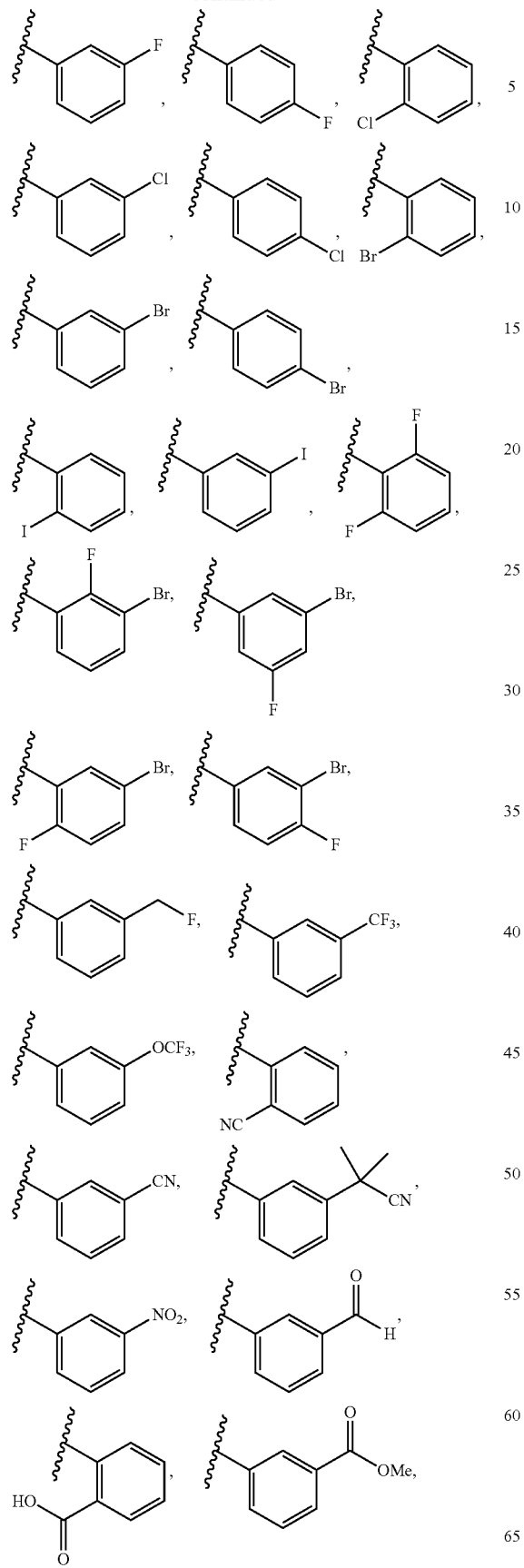
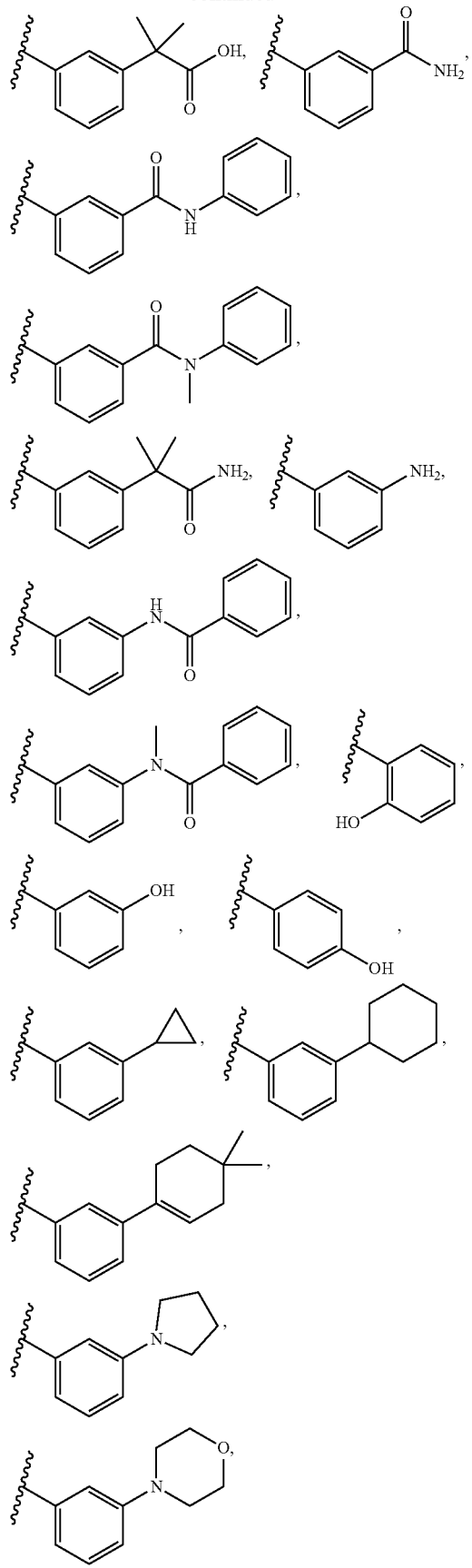

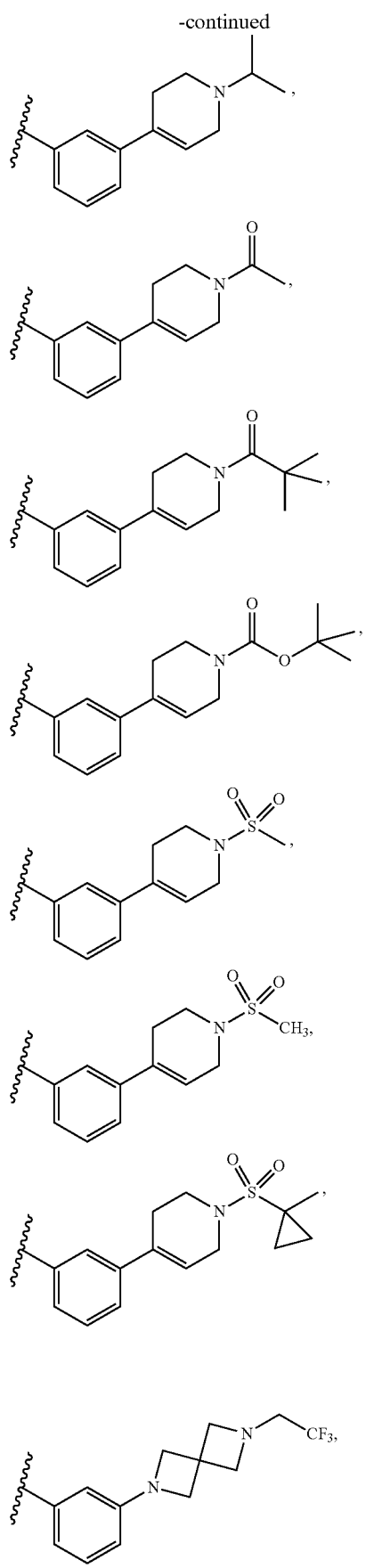
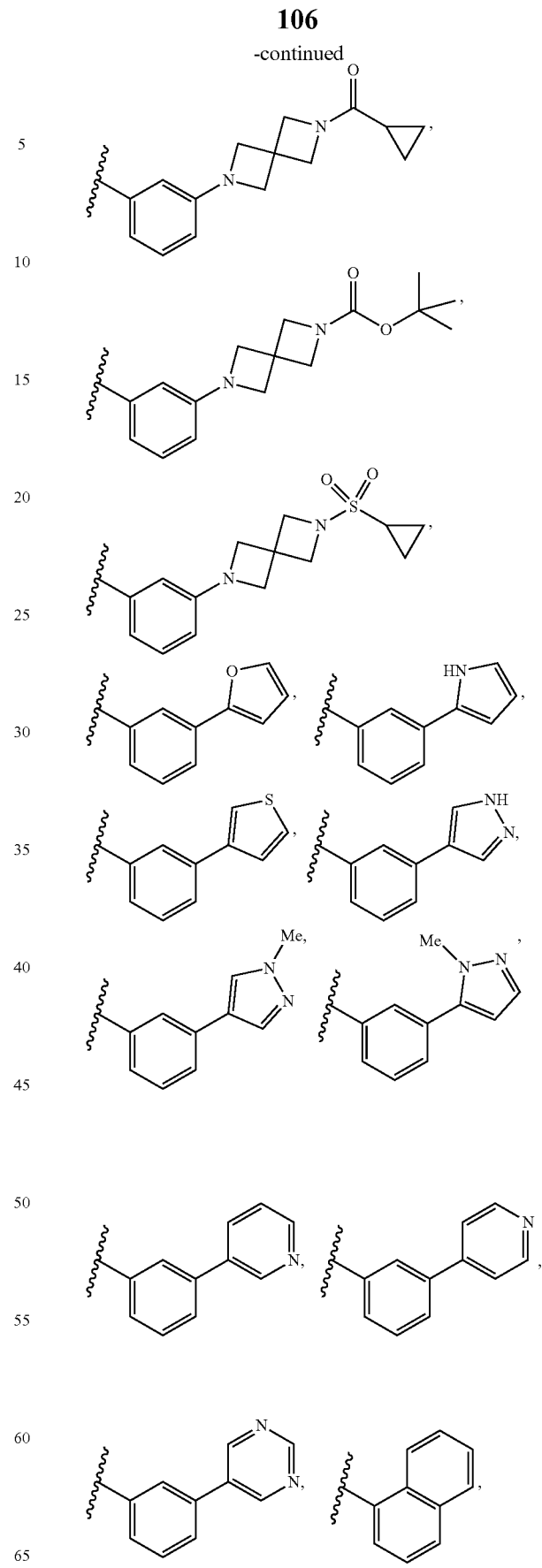

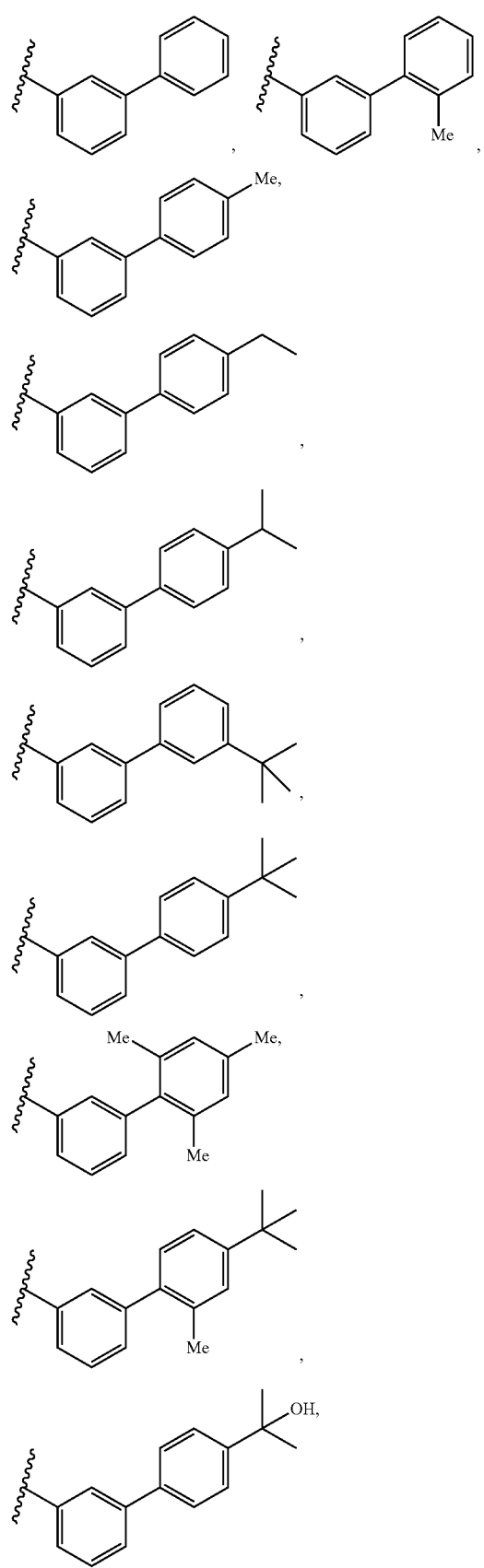
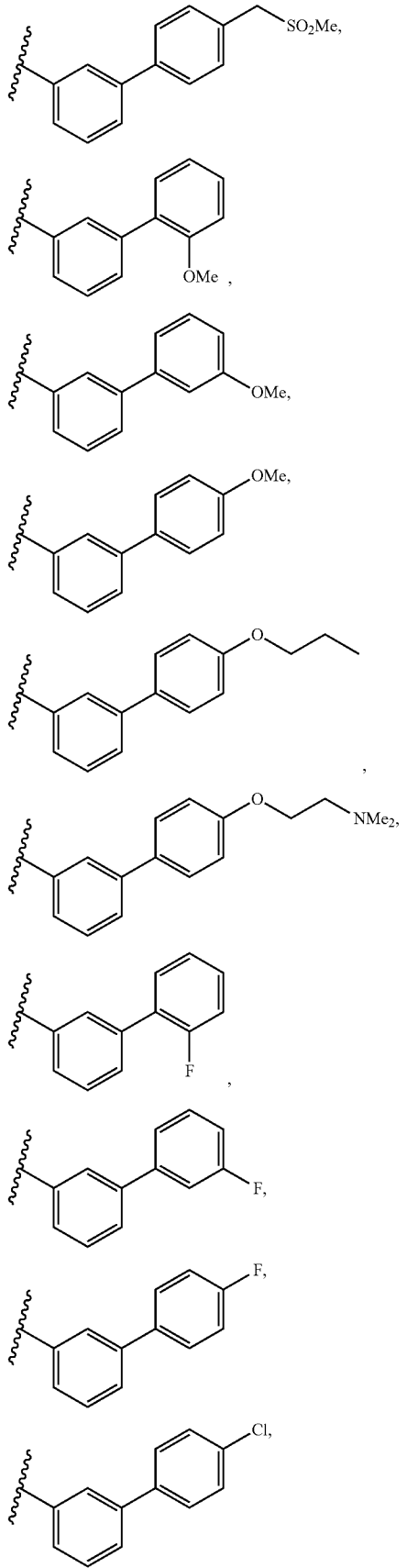

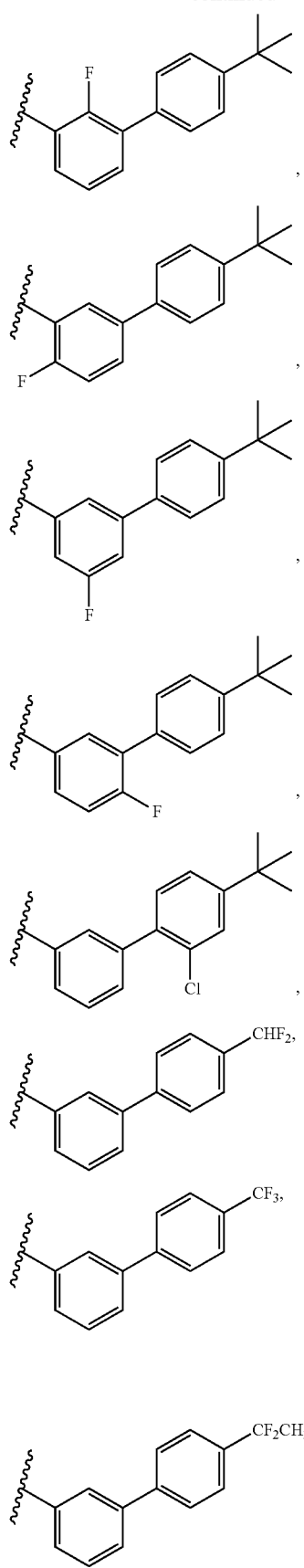
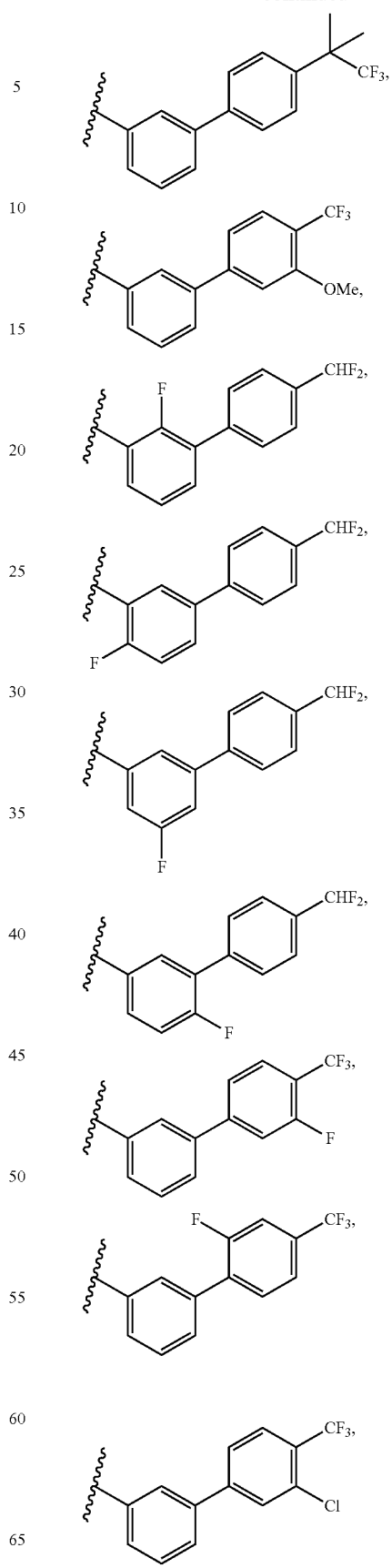

-continued
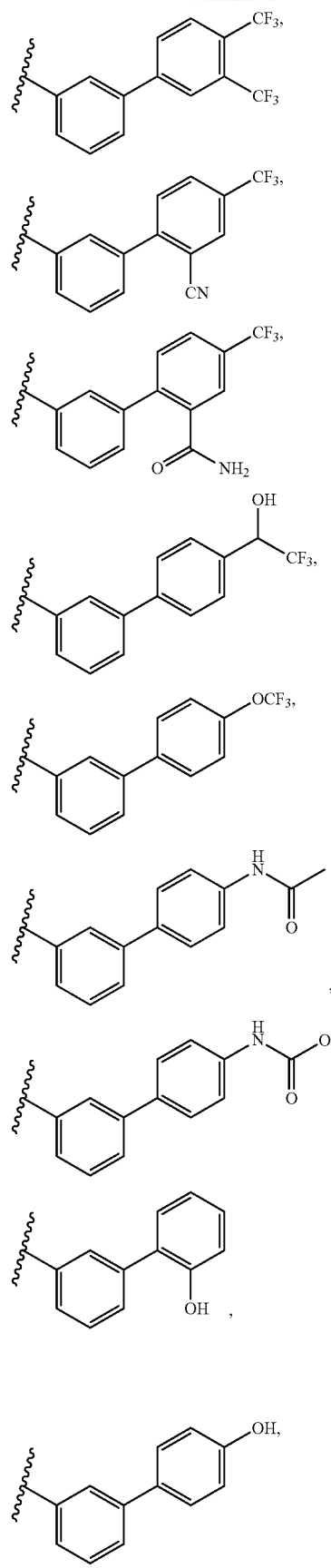
-continued
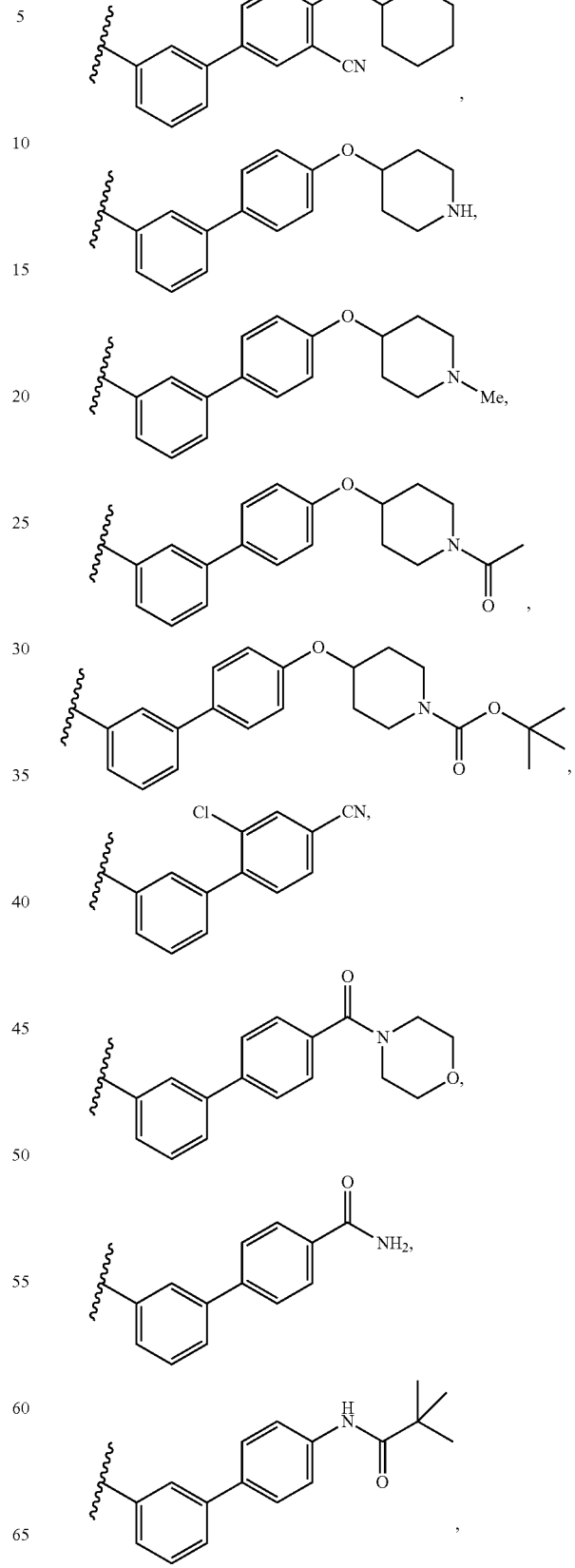

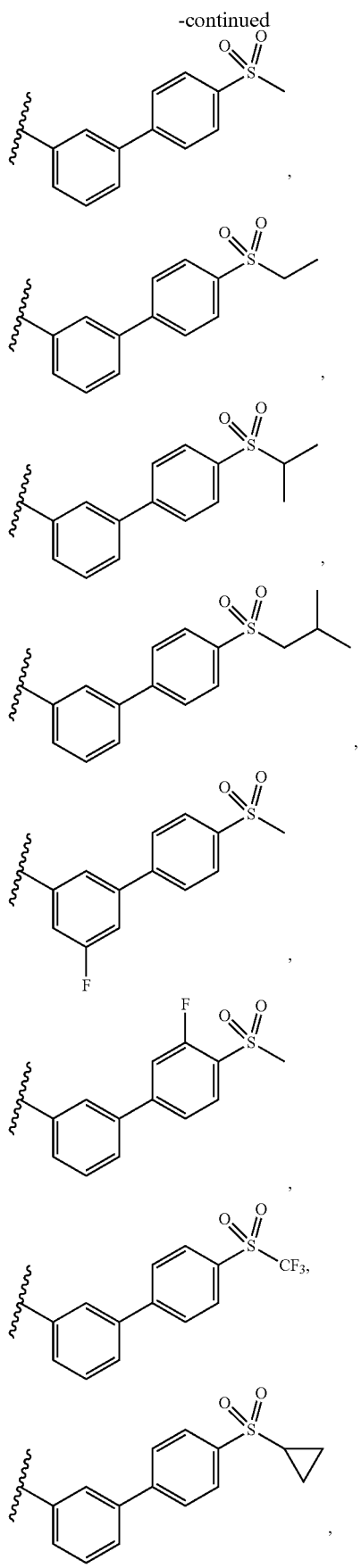
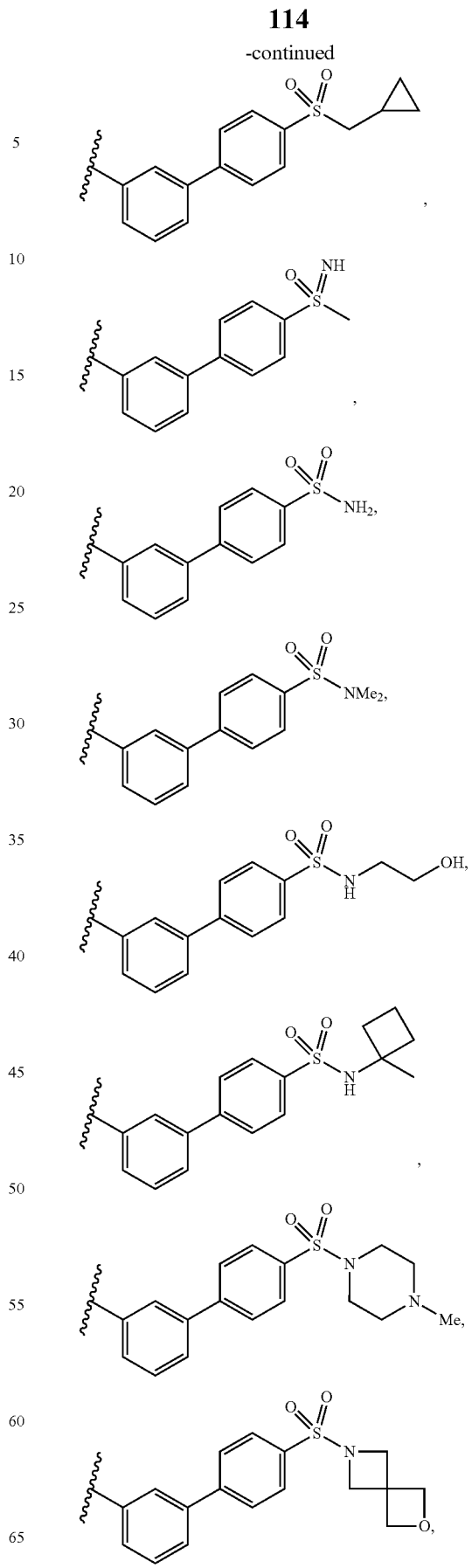

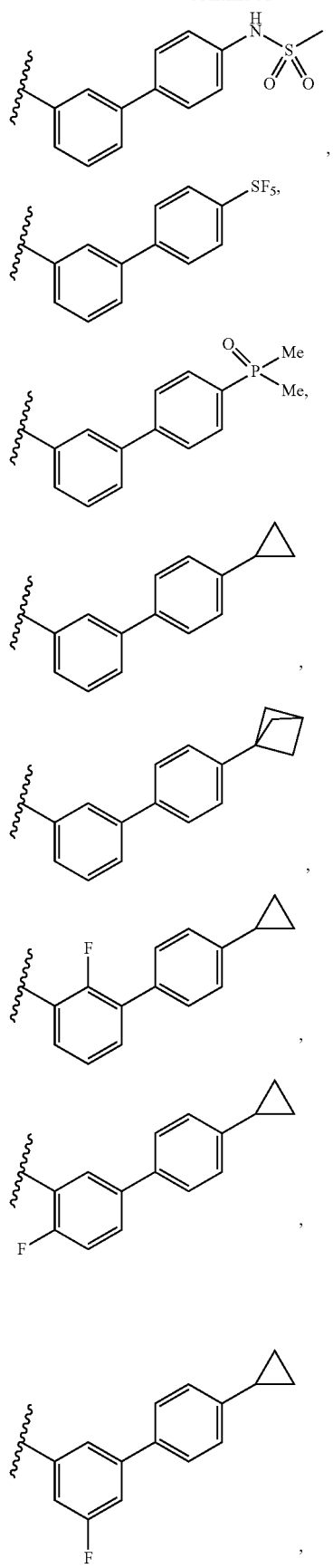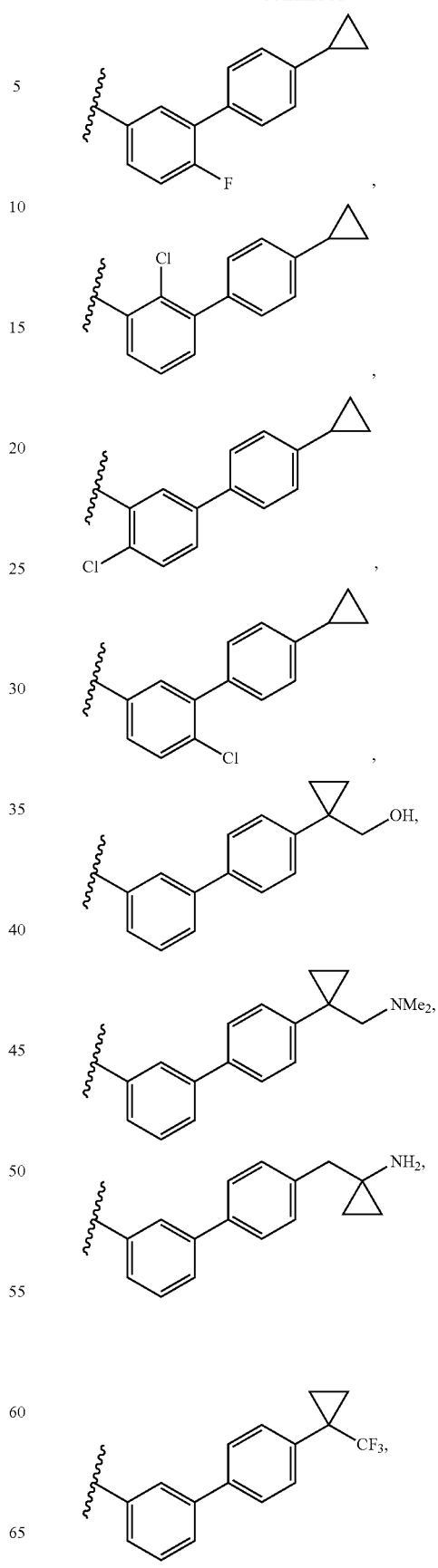

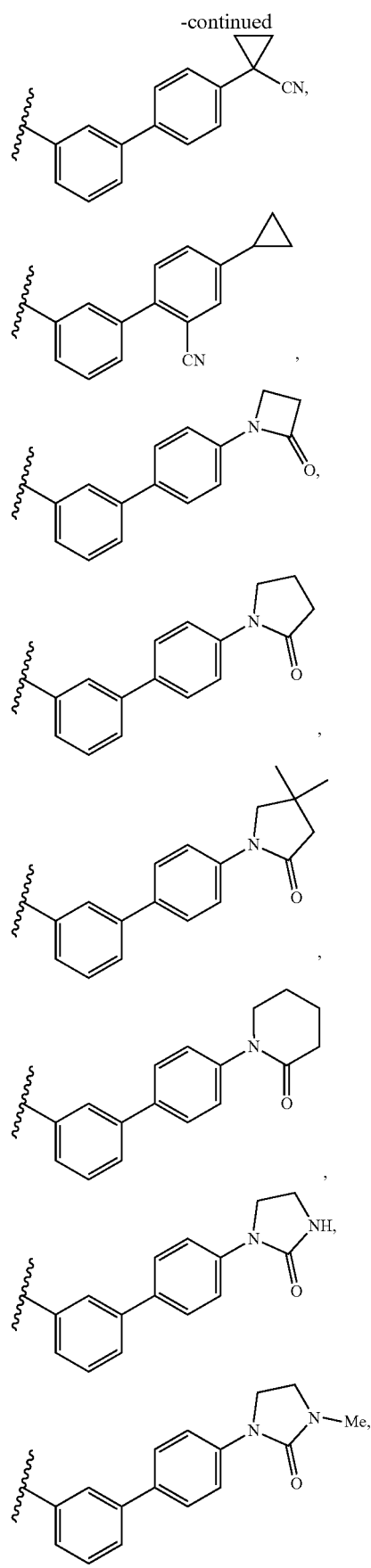
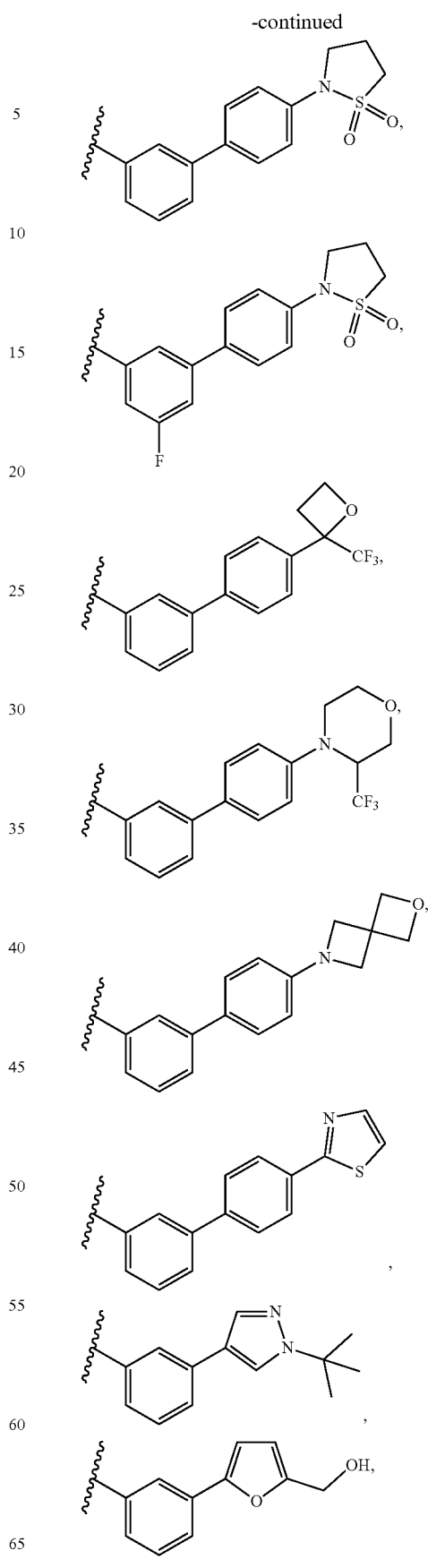

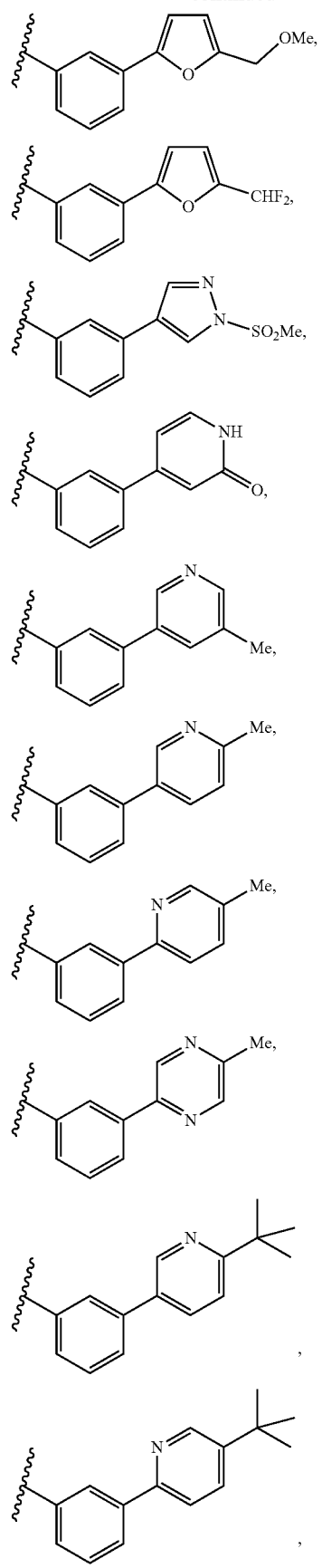
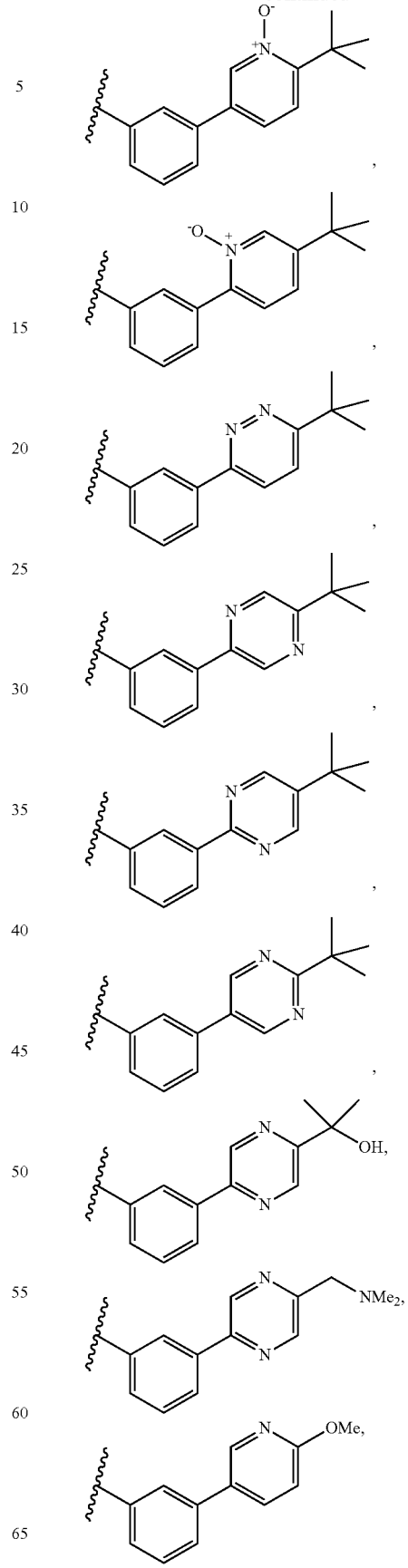

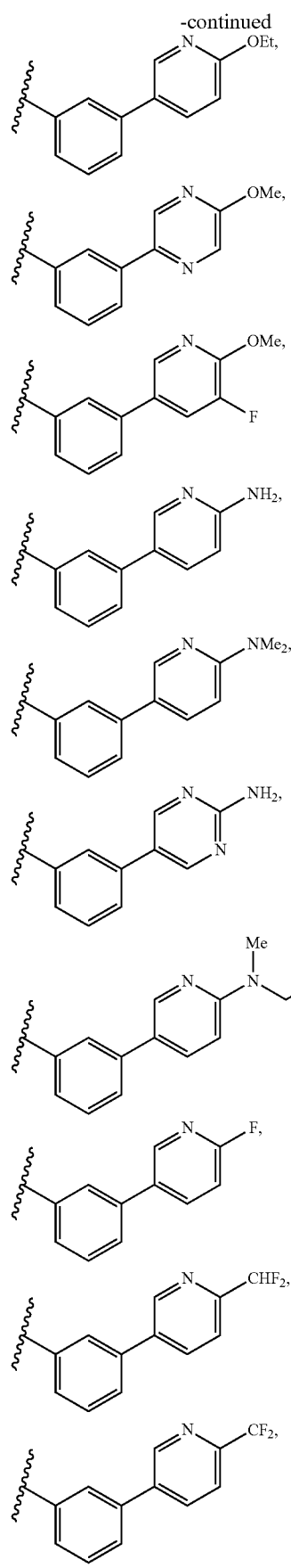
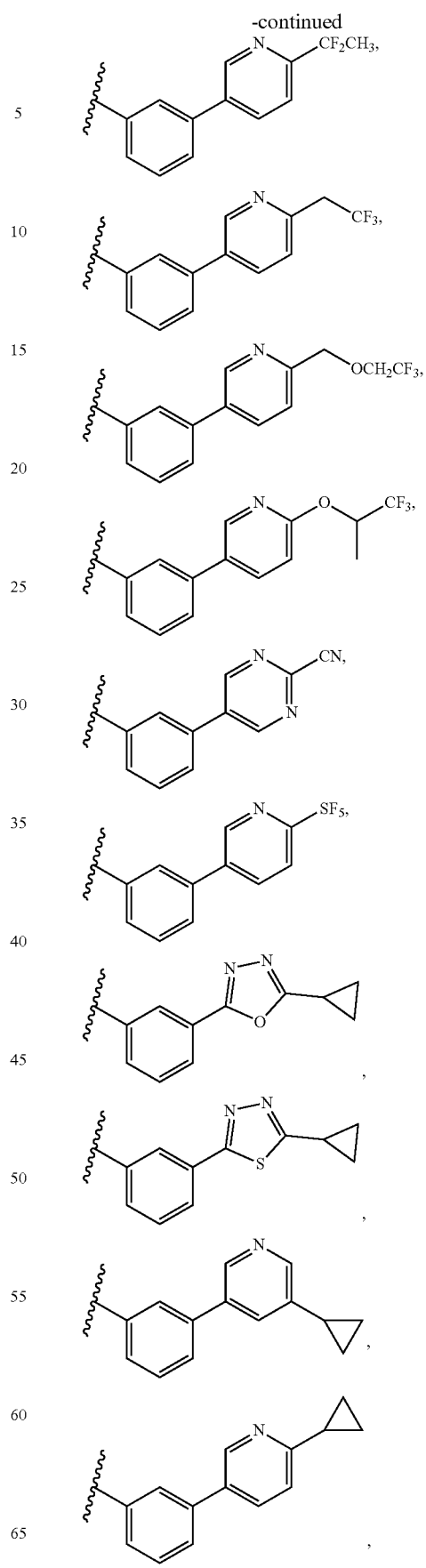

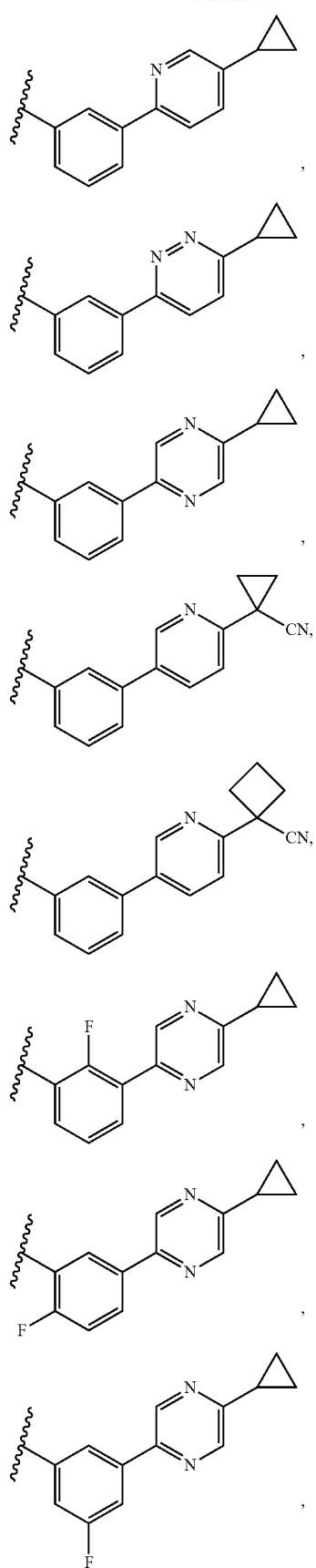
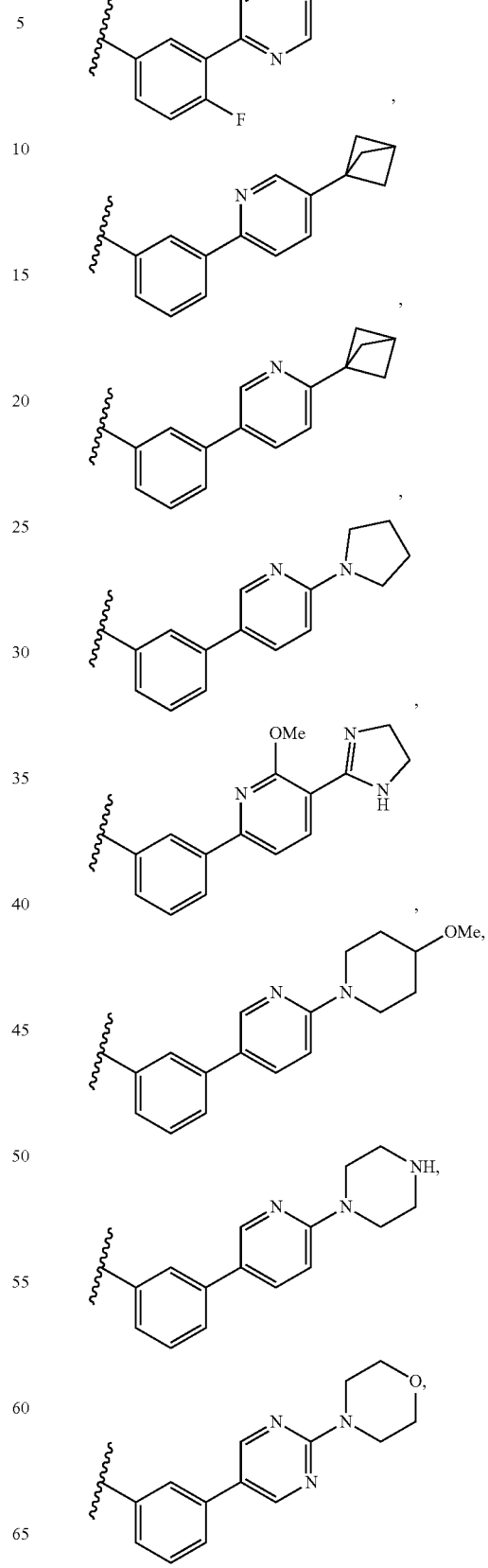

125
-continued
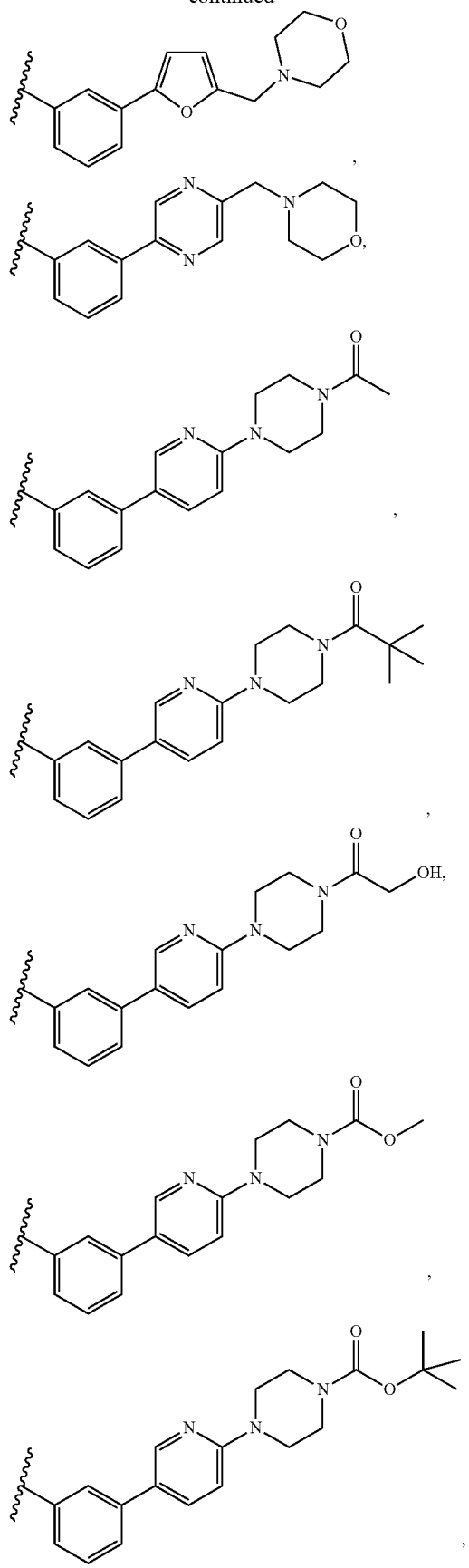
126
-continued
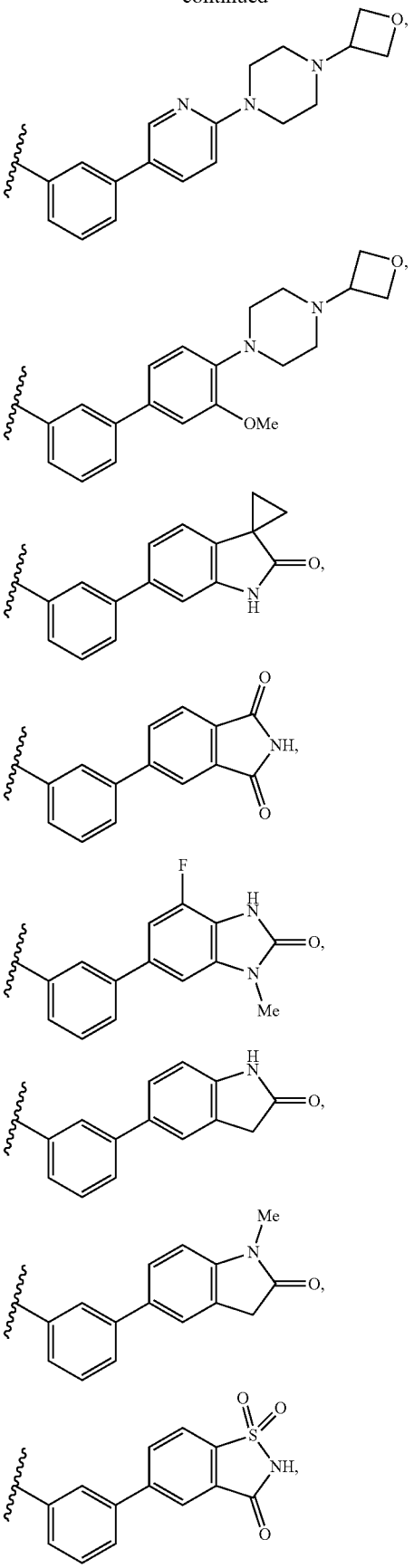

127
-continued
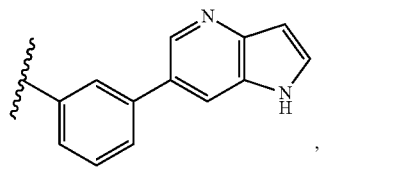
,
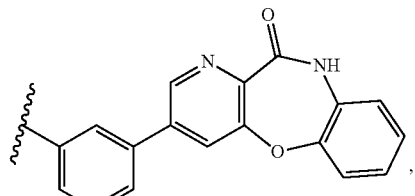
,
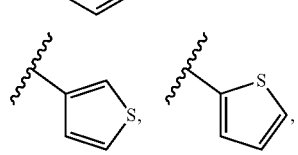
,
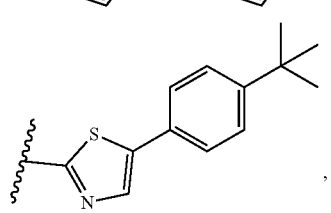
,
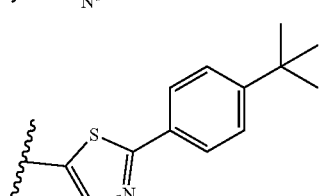
,
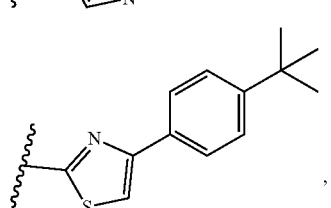
,
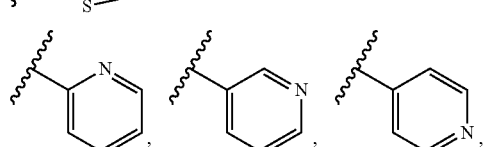
,
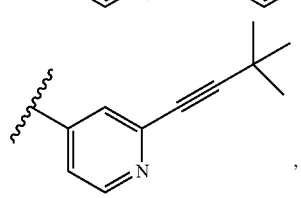
,
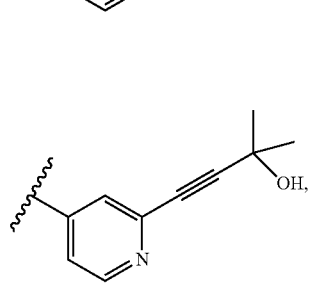
,
128
-continued
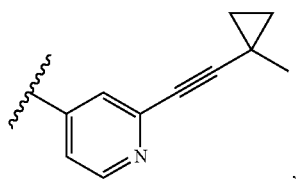
,
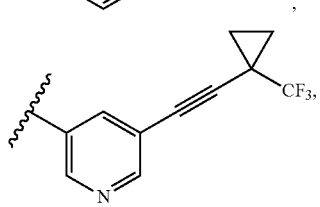
,
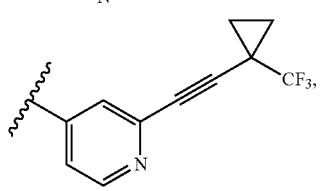
,
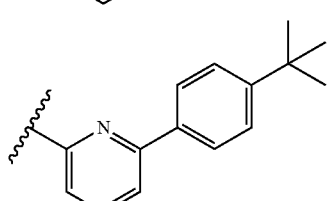
,
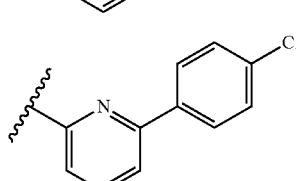
,
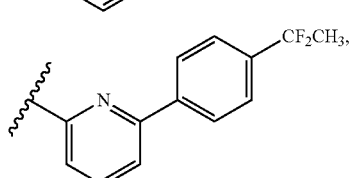
,
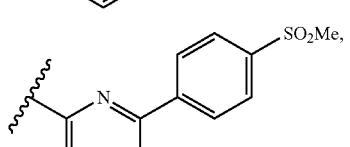
,
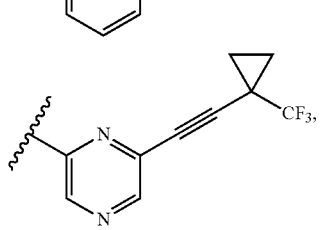
,
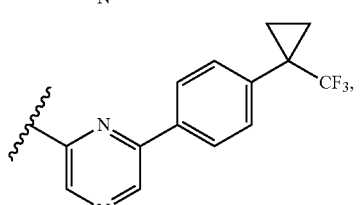
,

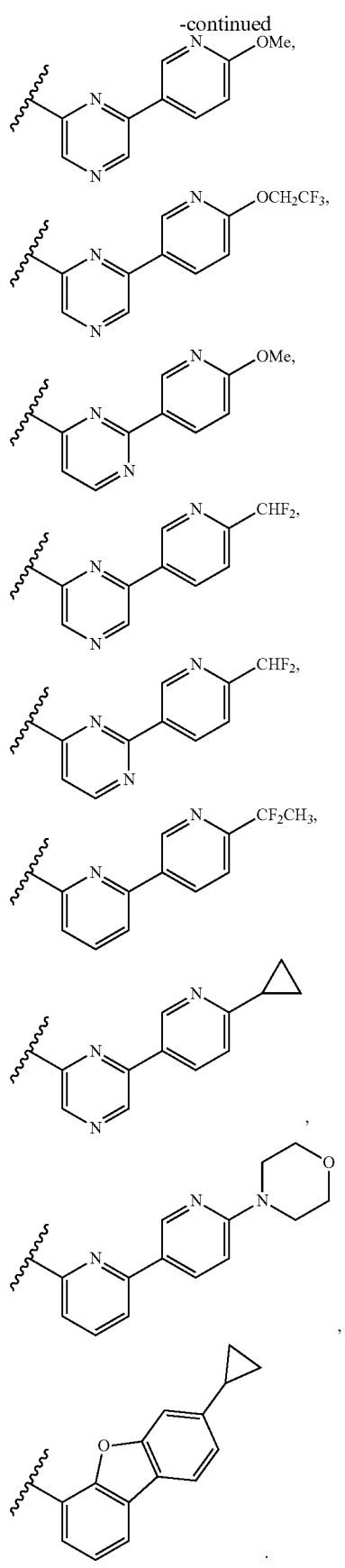
In some embodiments, the compound of Formula (I) or (I-1), or a pharmaceutically acceptable salt thereof, is the compound wherein $R^6$ is
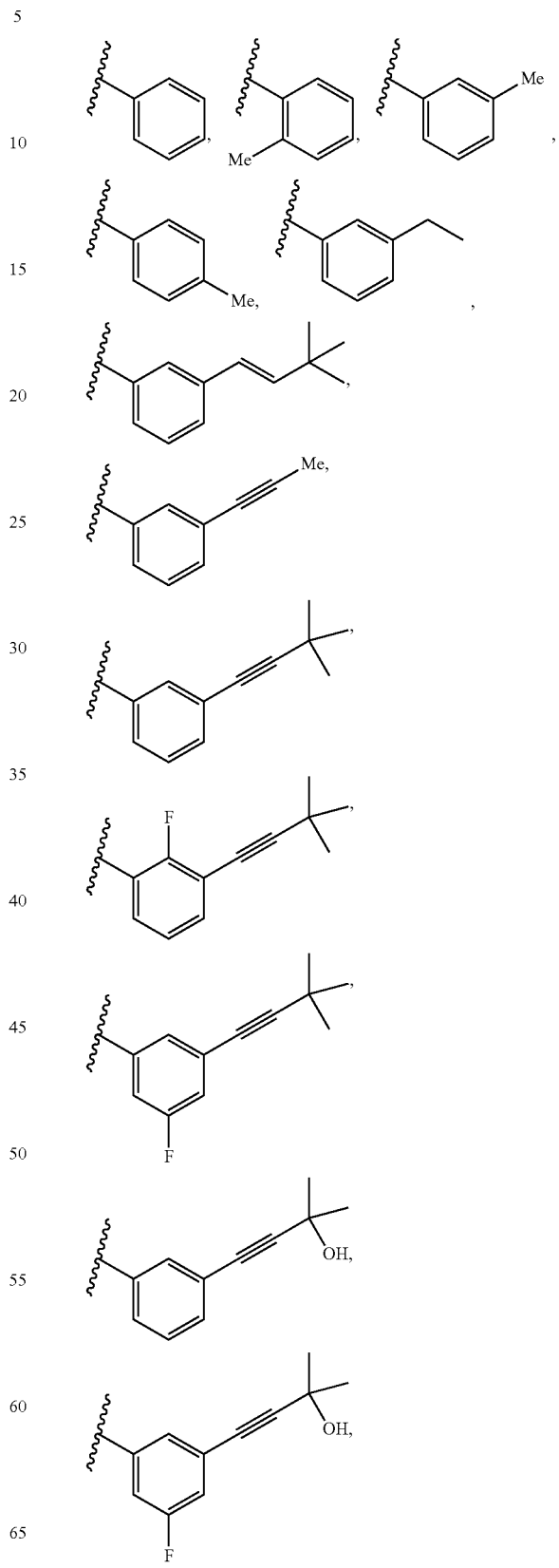

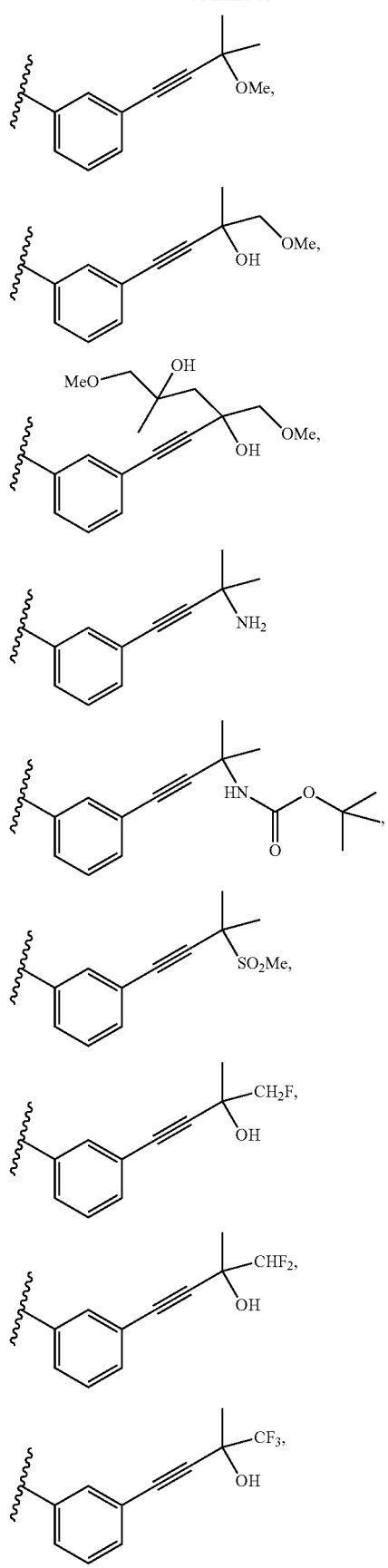
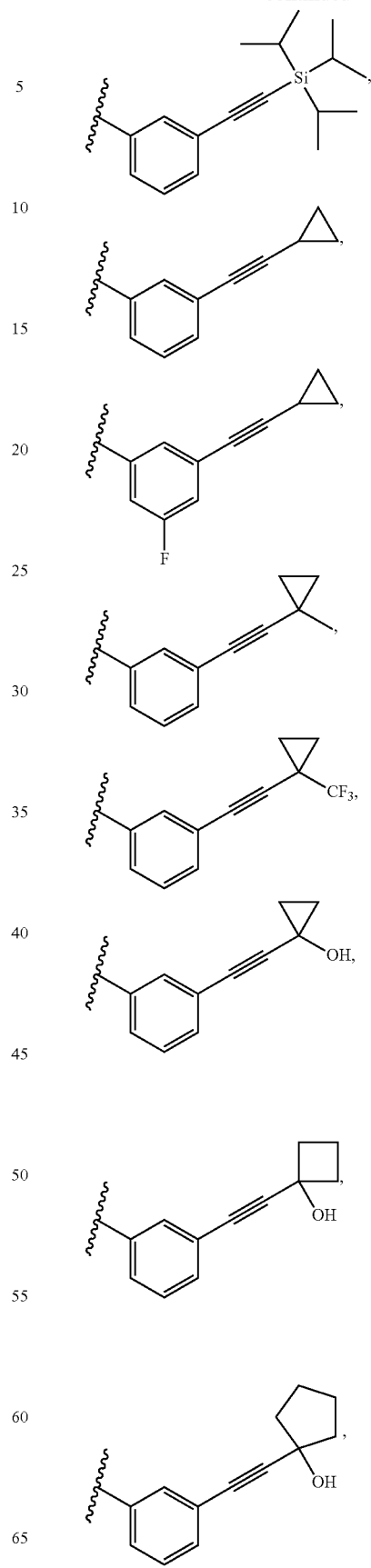

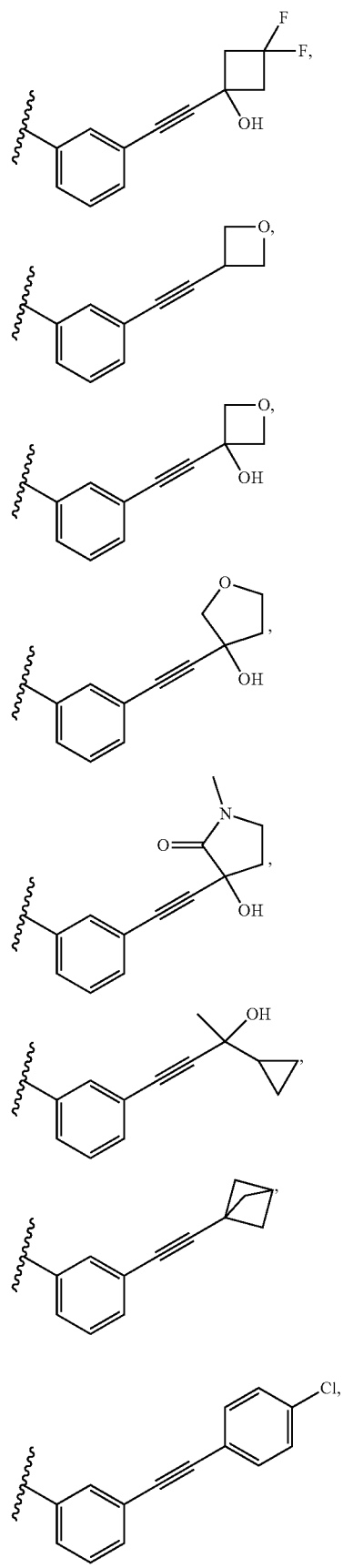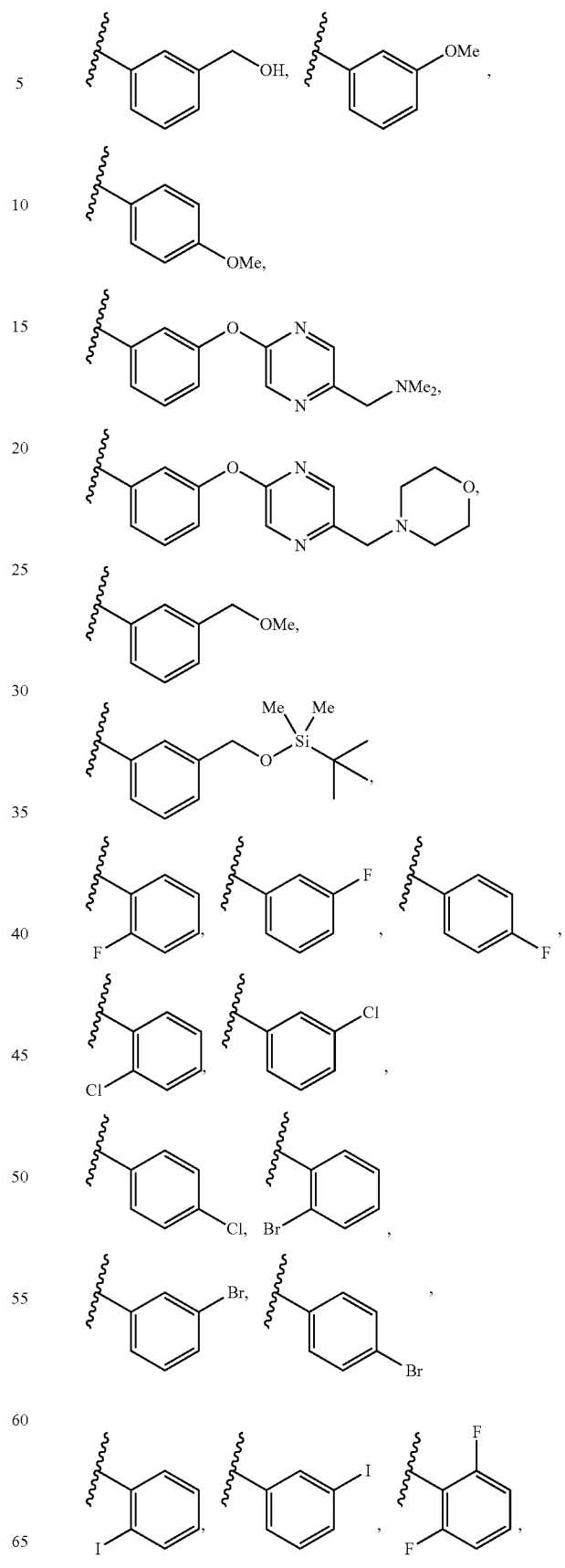

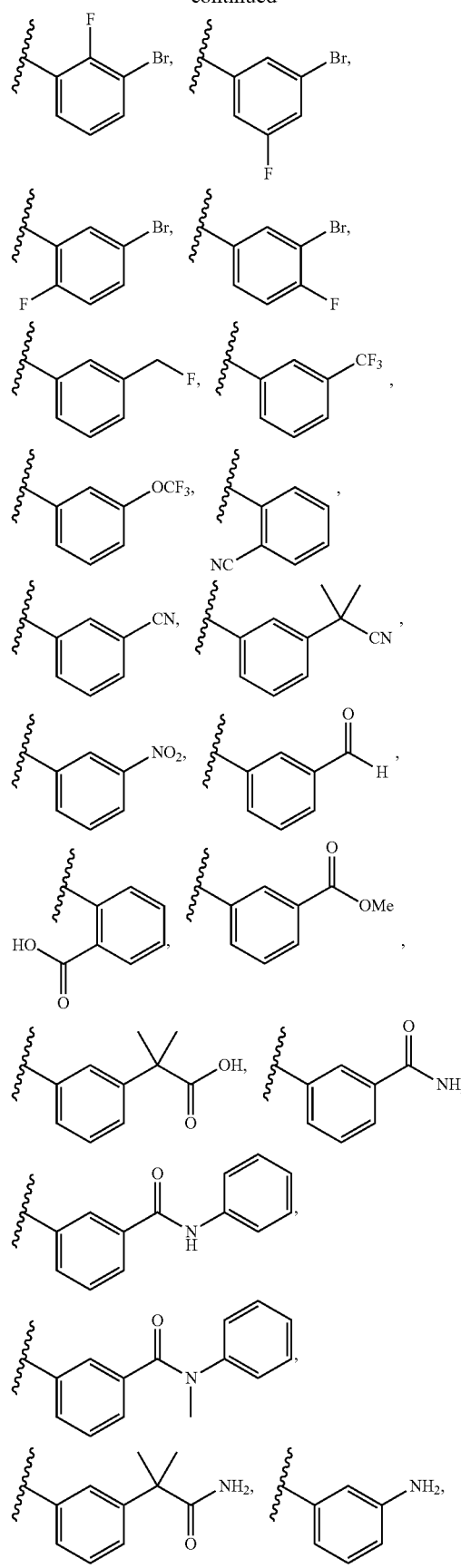
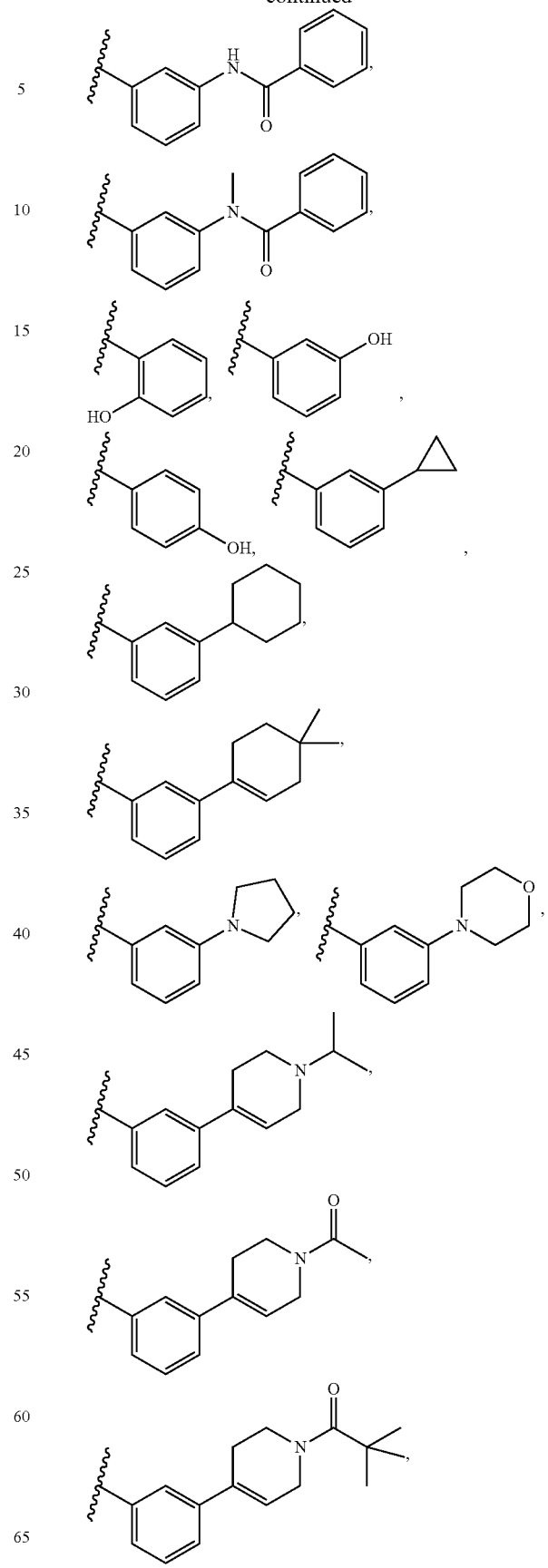

137
-continued
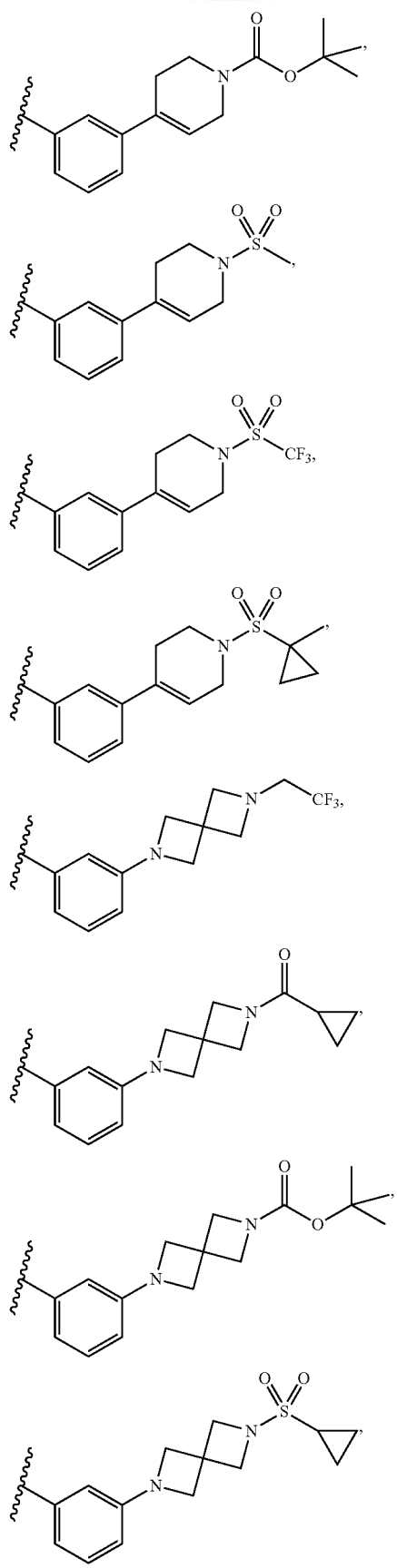
138
-continued
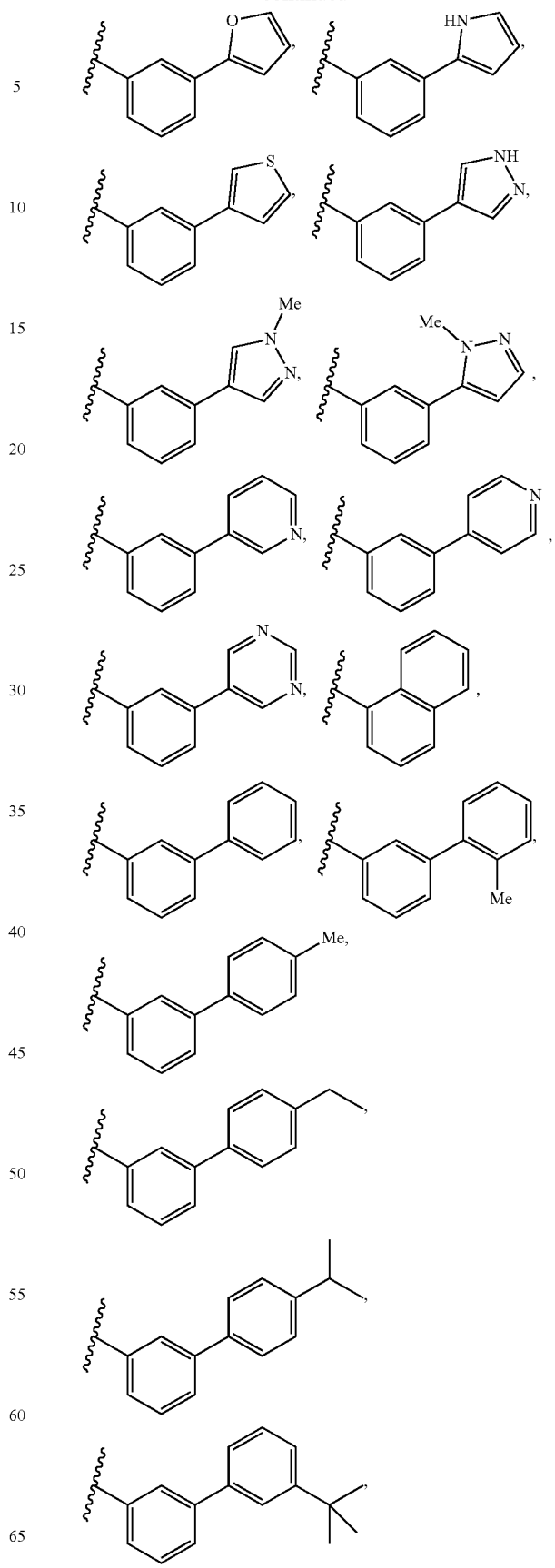

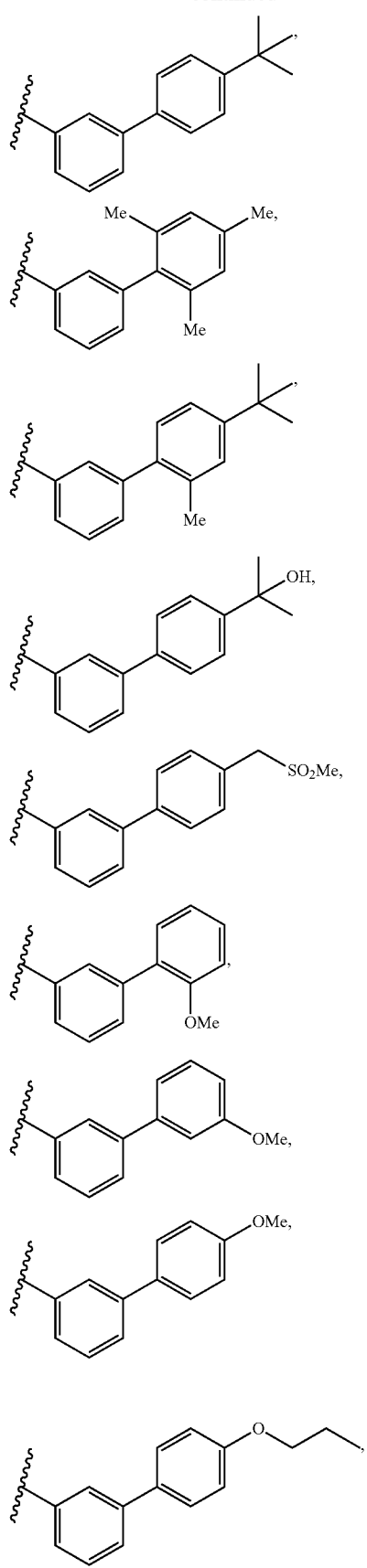
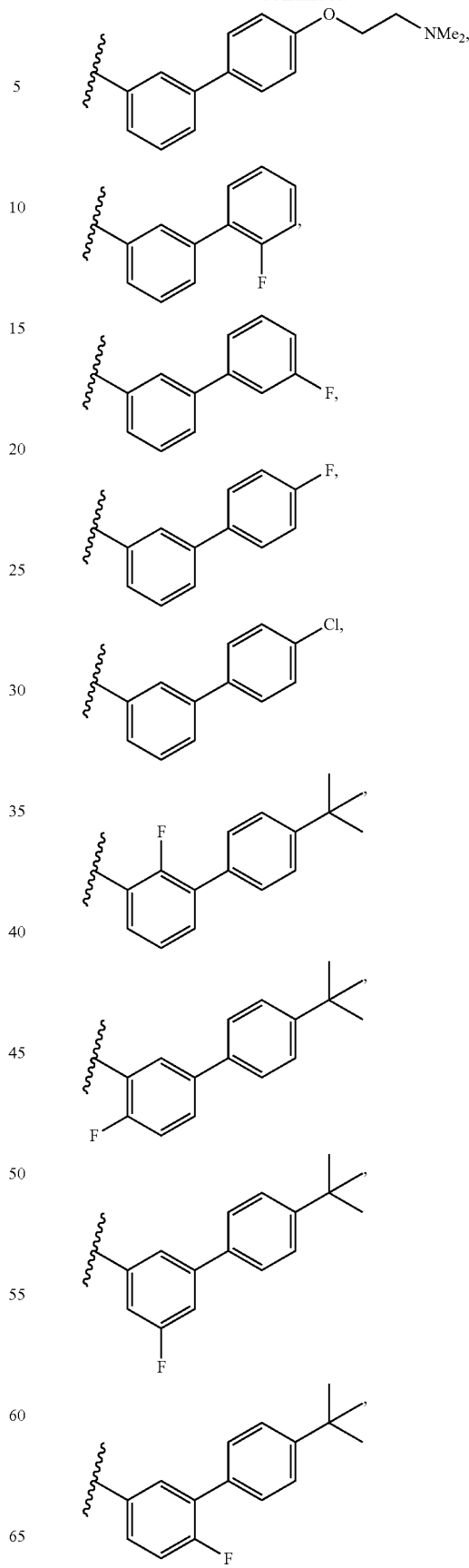

-continued
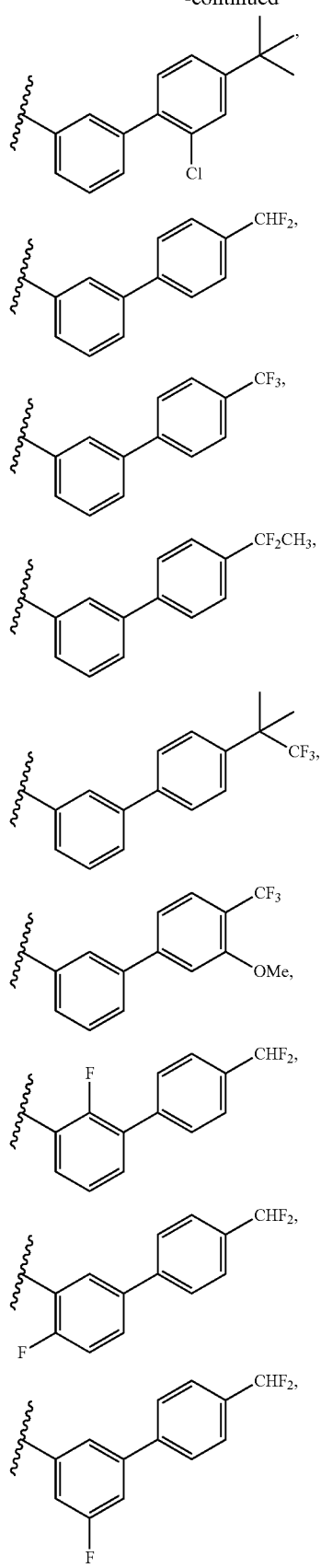
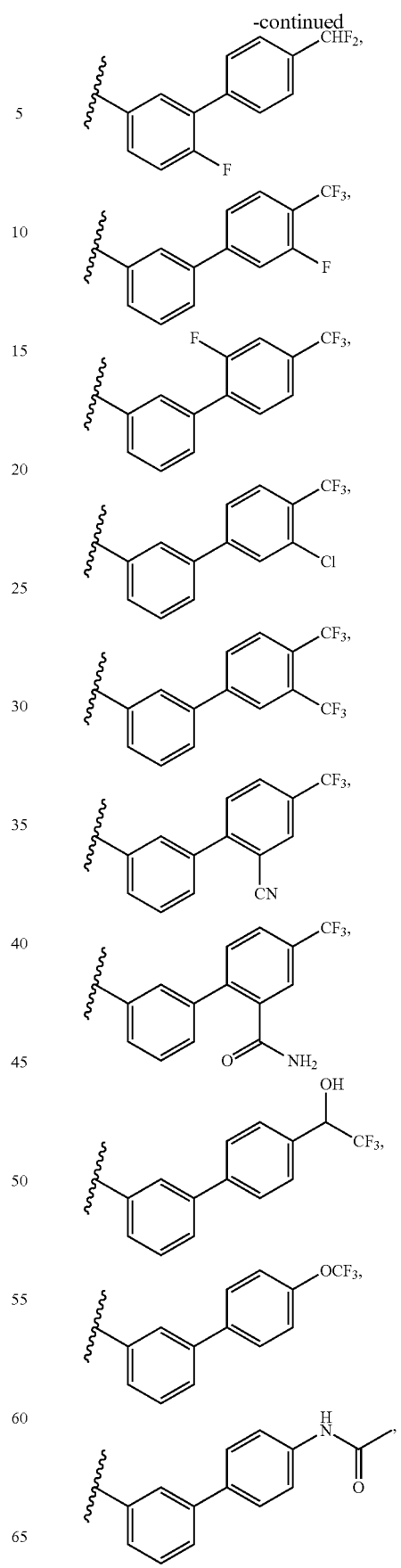

143
-continued
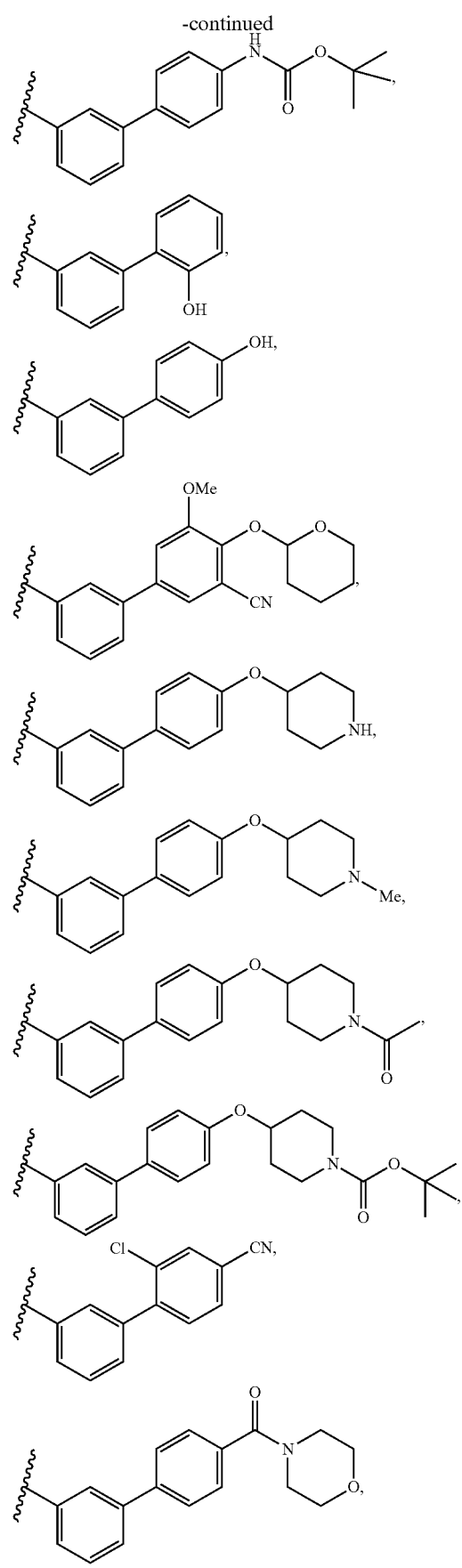
144
-continued
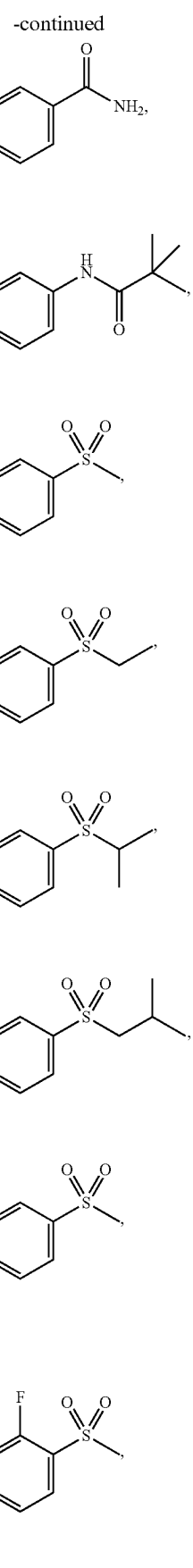

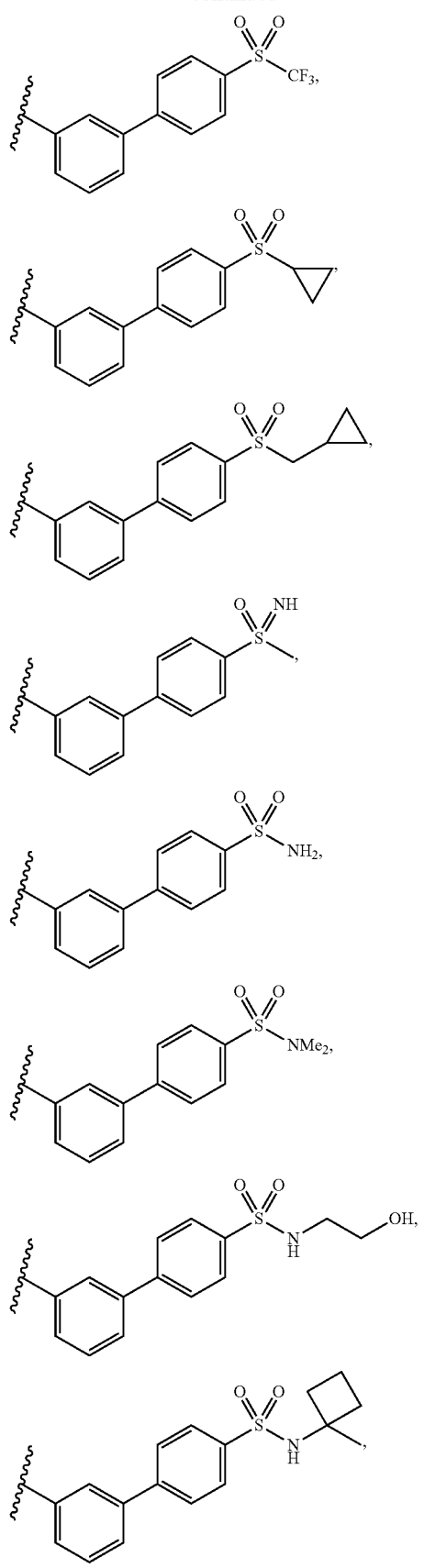
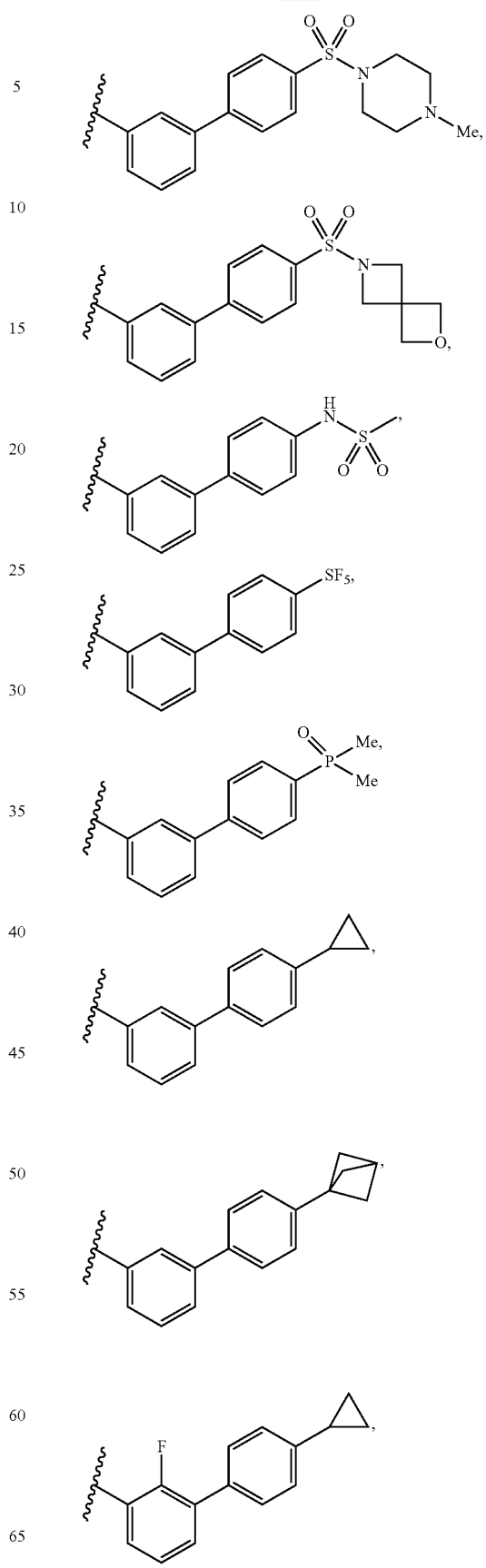

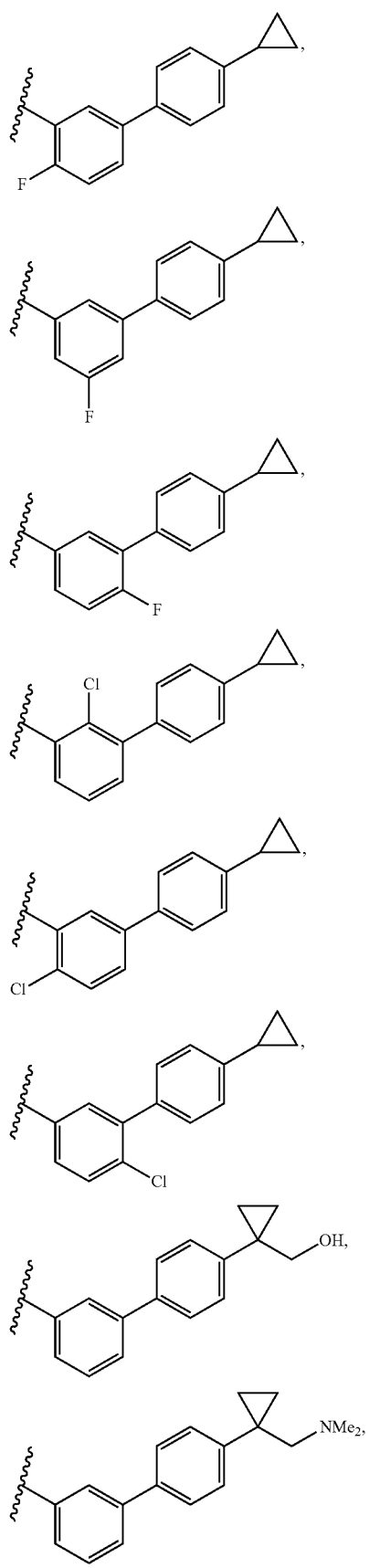
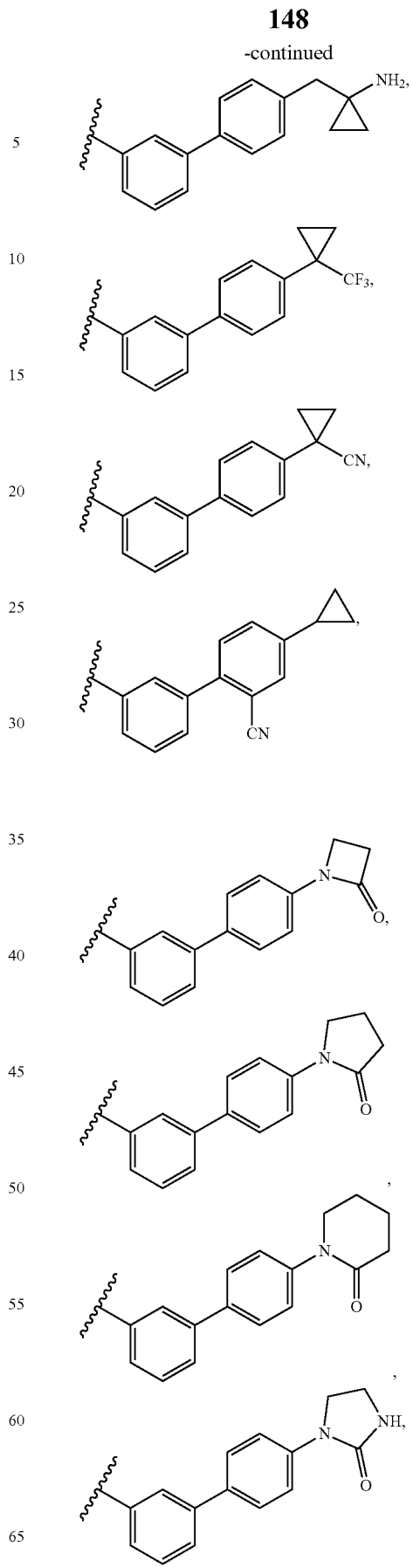

-continued
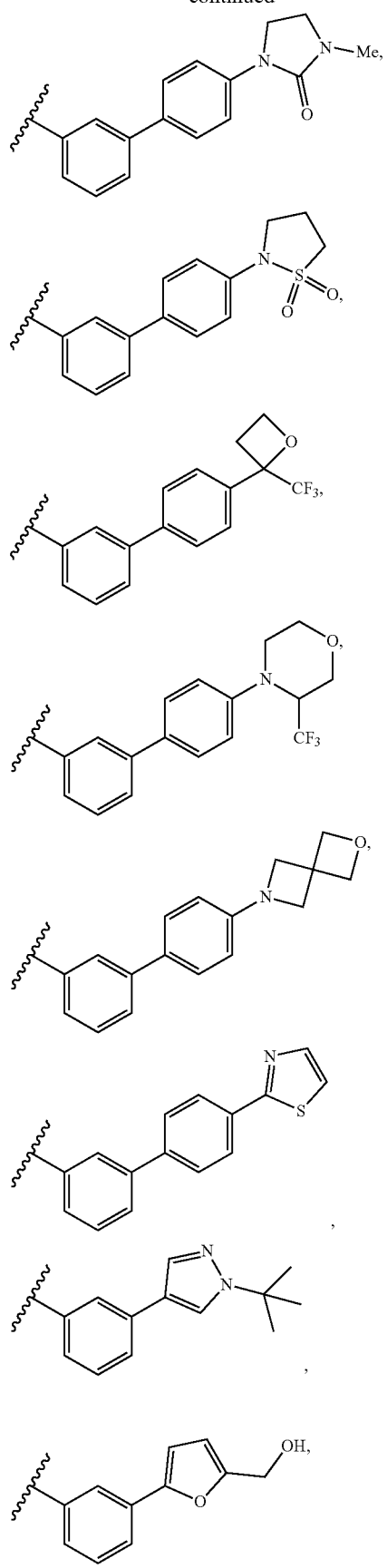
-continued
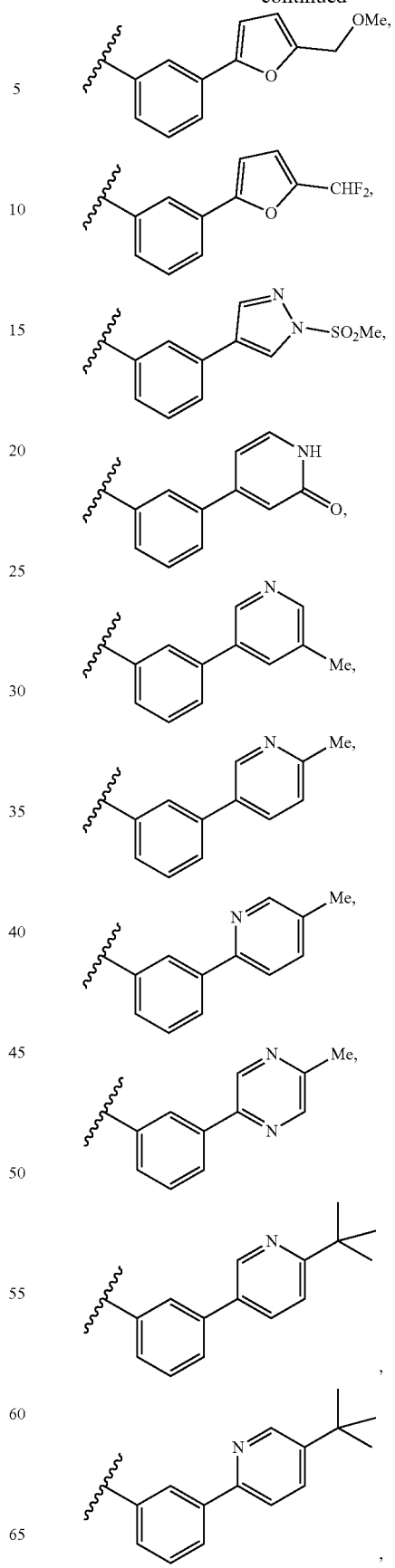

151
-continued
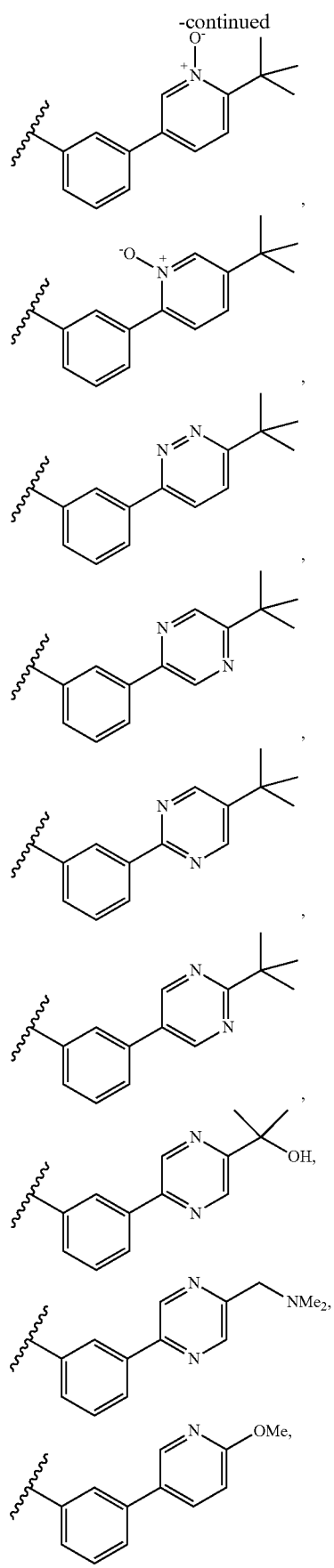
152
-continued
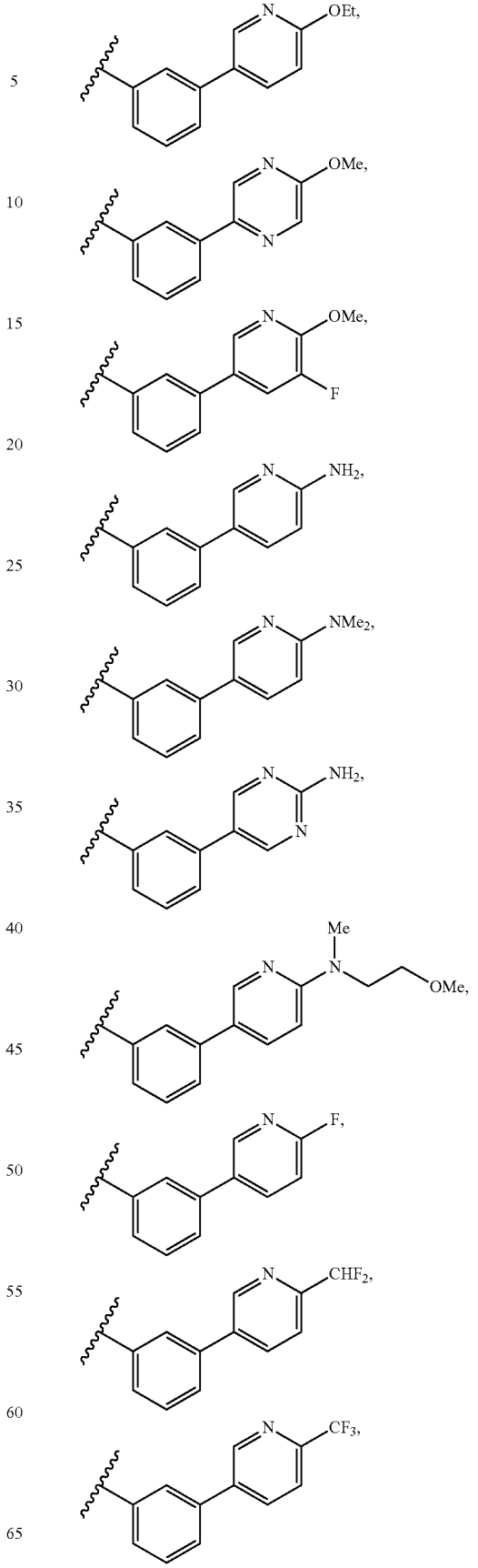

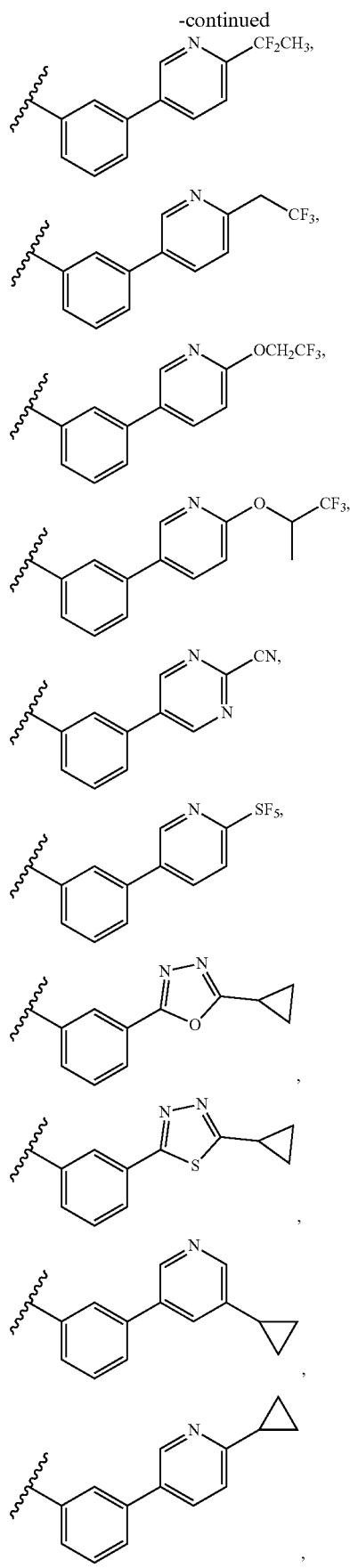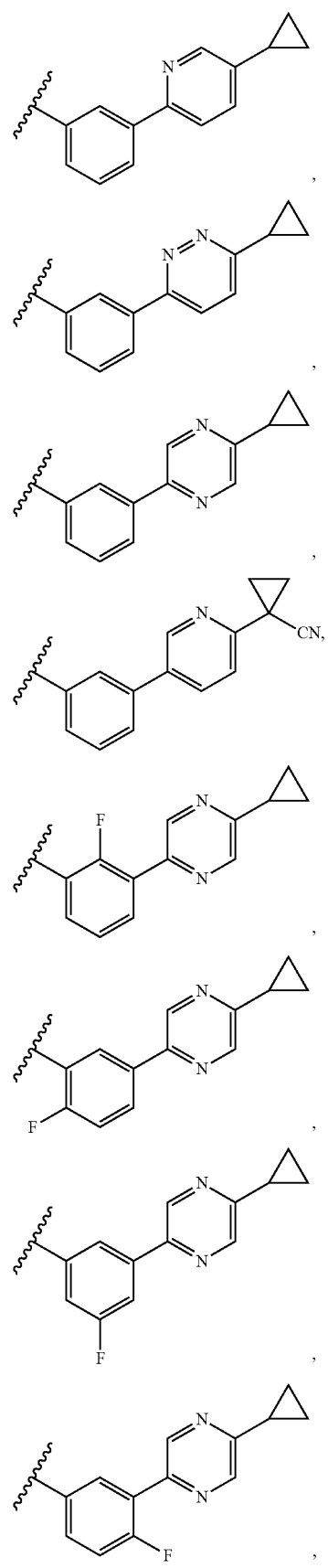

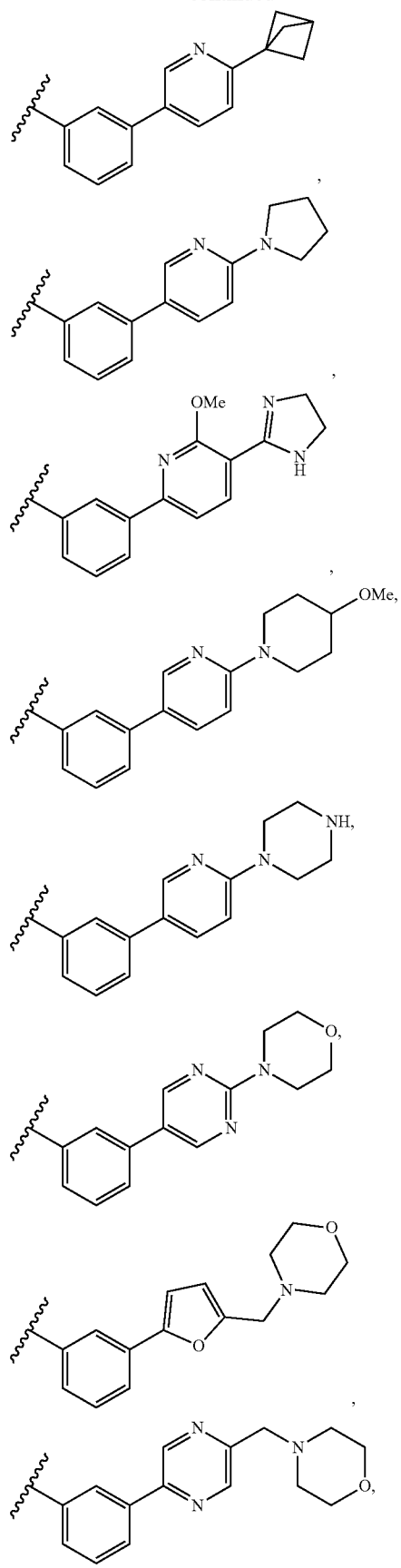
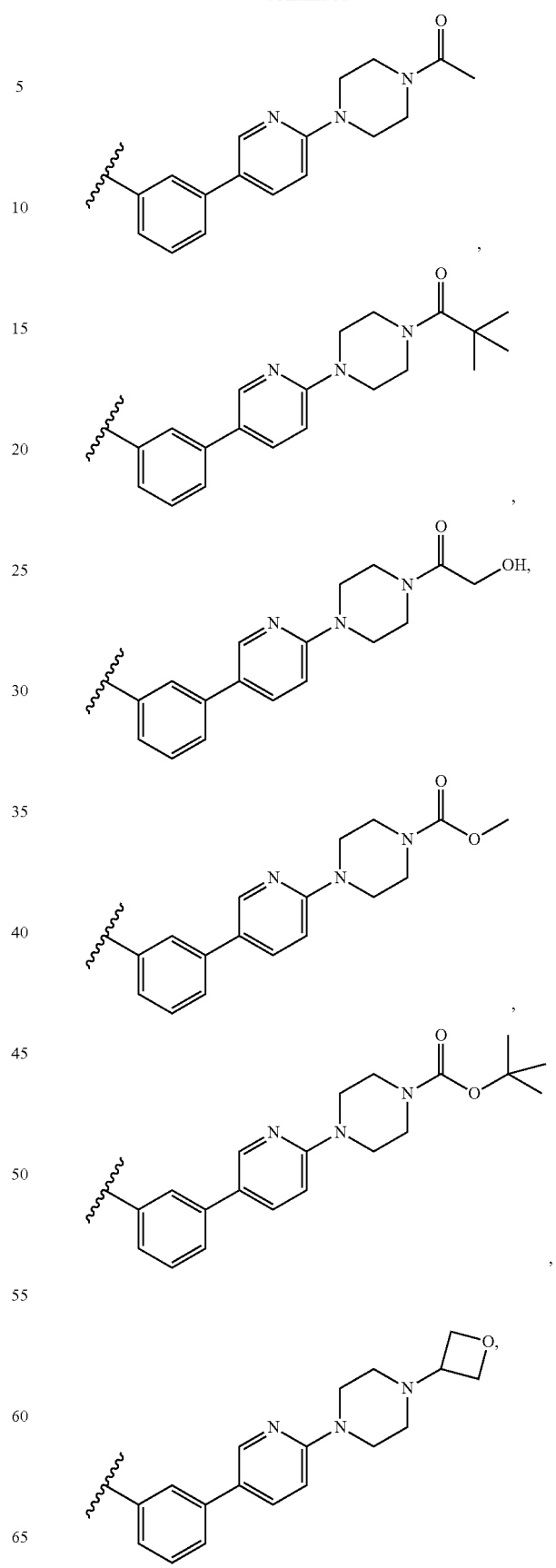

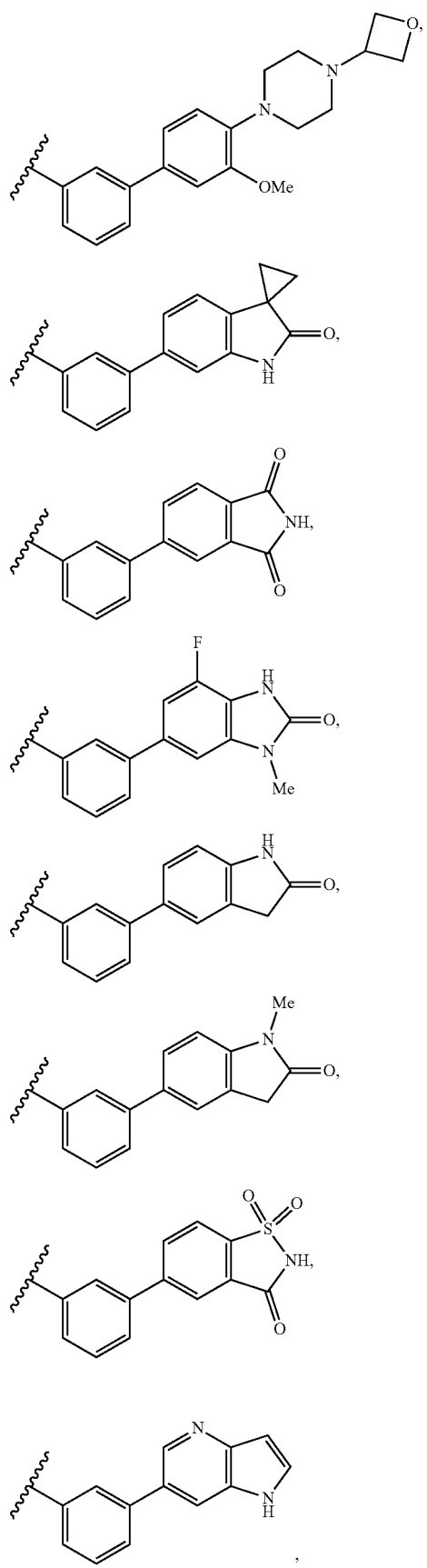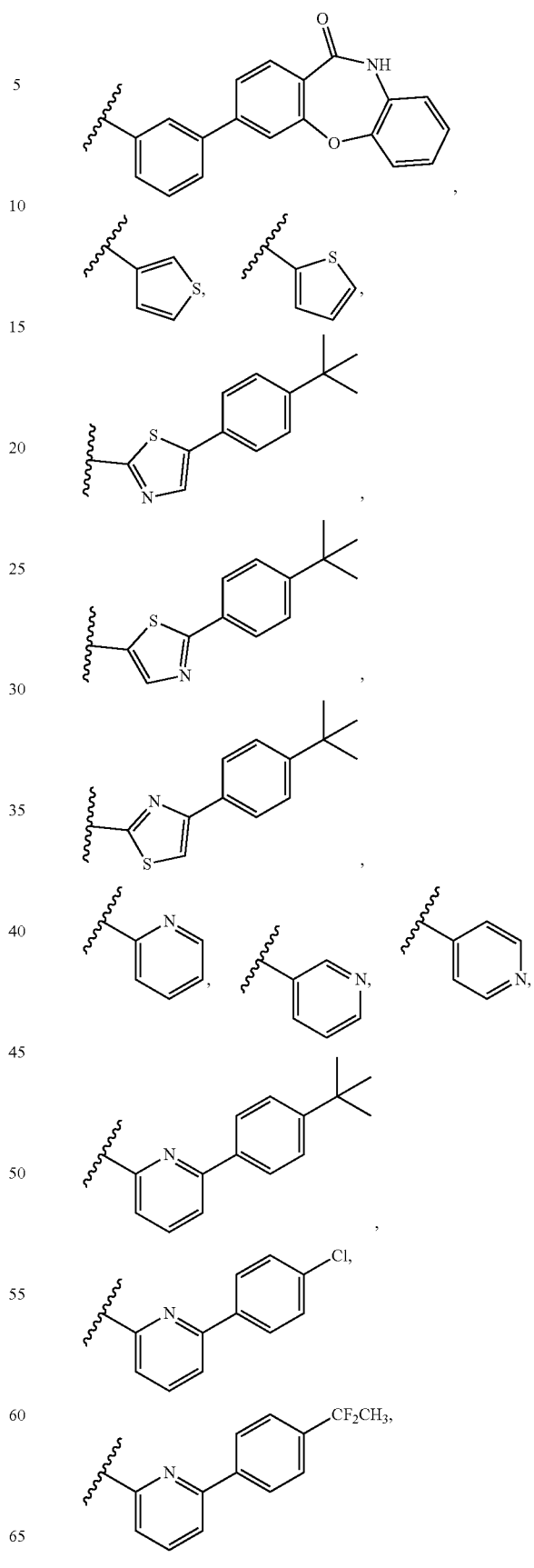

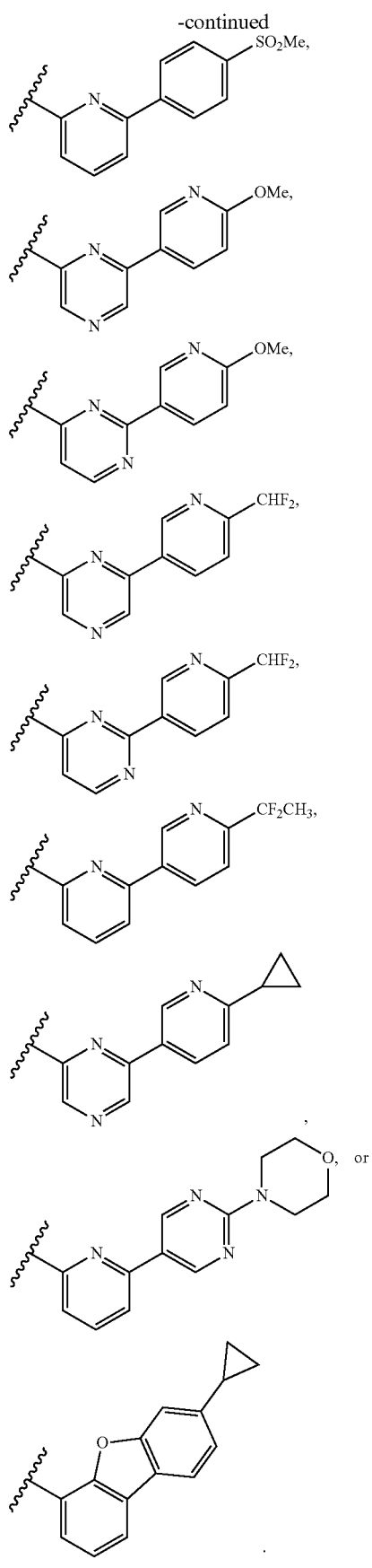
In some embodiments, the compound of Formula (I) or (I-1), or a pharmaceutically acceptable salt thereof, is the compound wherein $R^6$ is
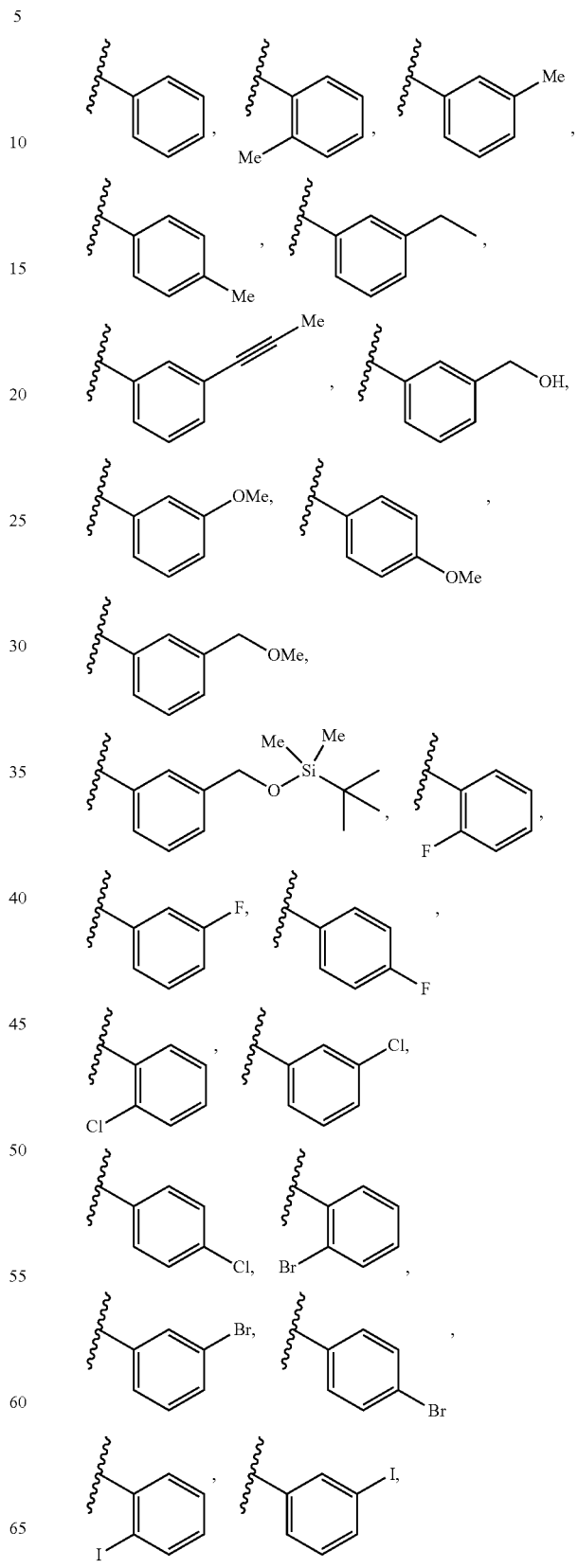

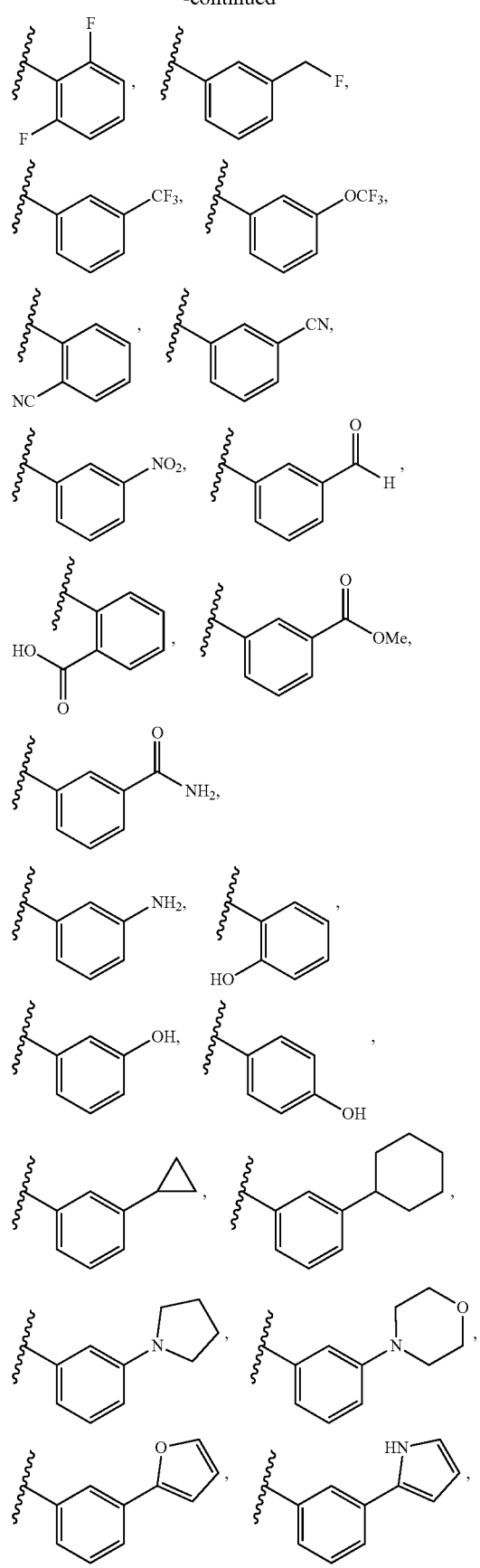
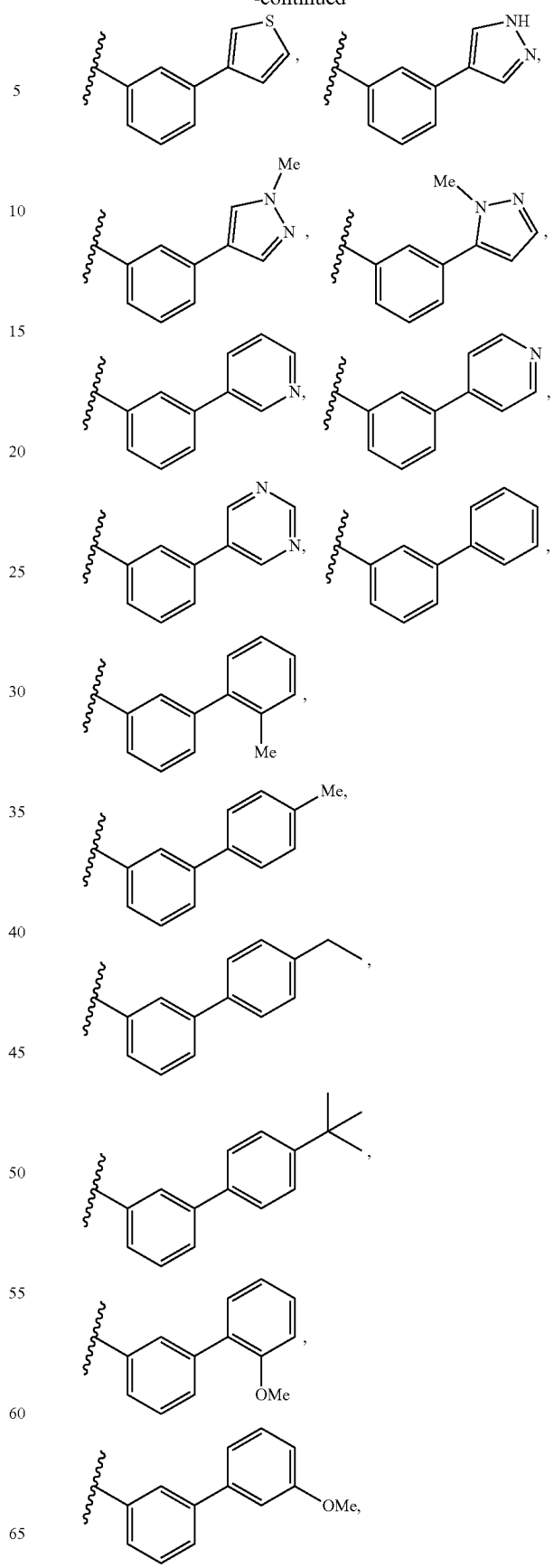

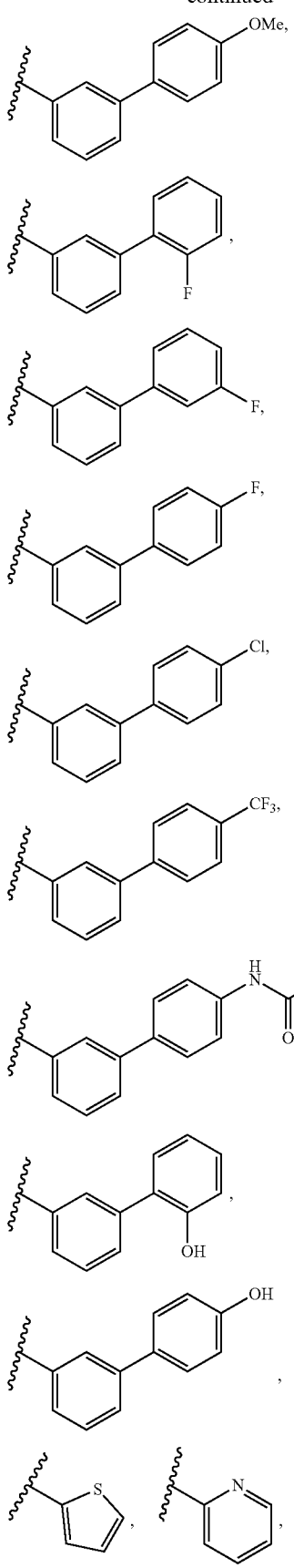
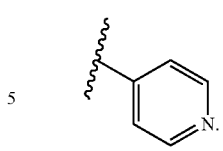
In some embodiments, the compound of Formula (I) or (I-1), or a pharmaceutically acceptable salt thereof, is a compound wherein $R^5$ and $R^6$, together with the nitrogen to which they are bound, have a structure:
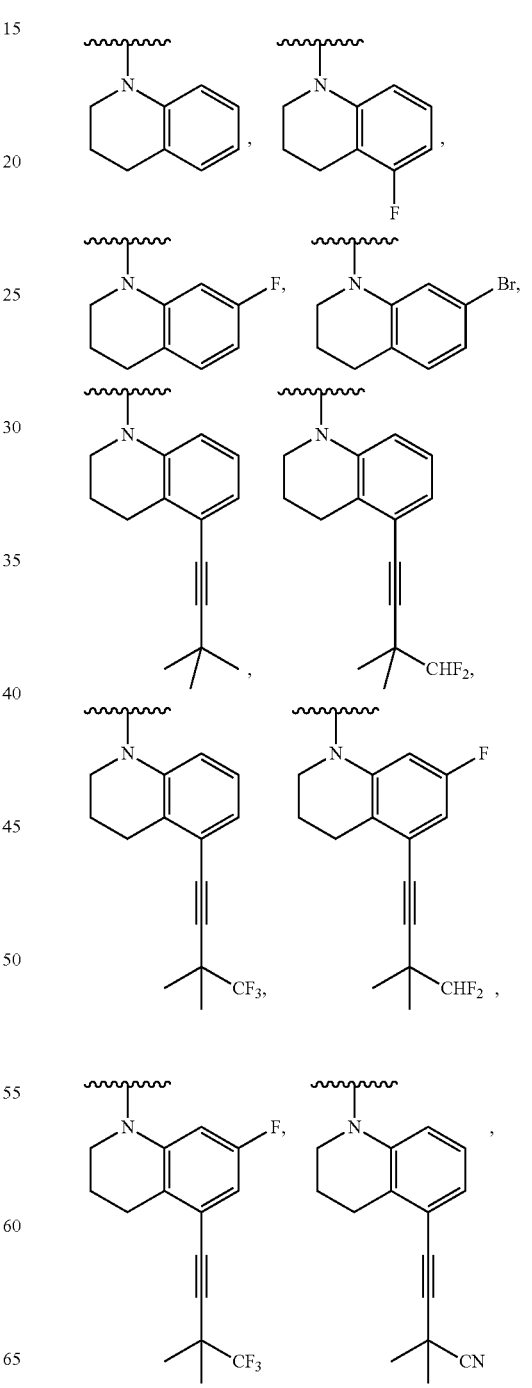

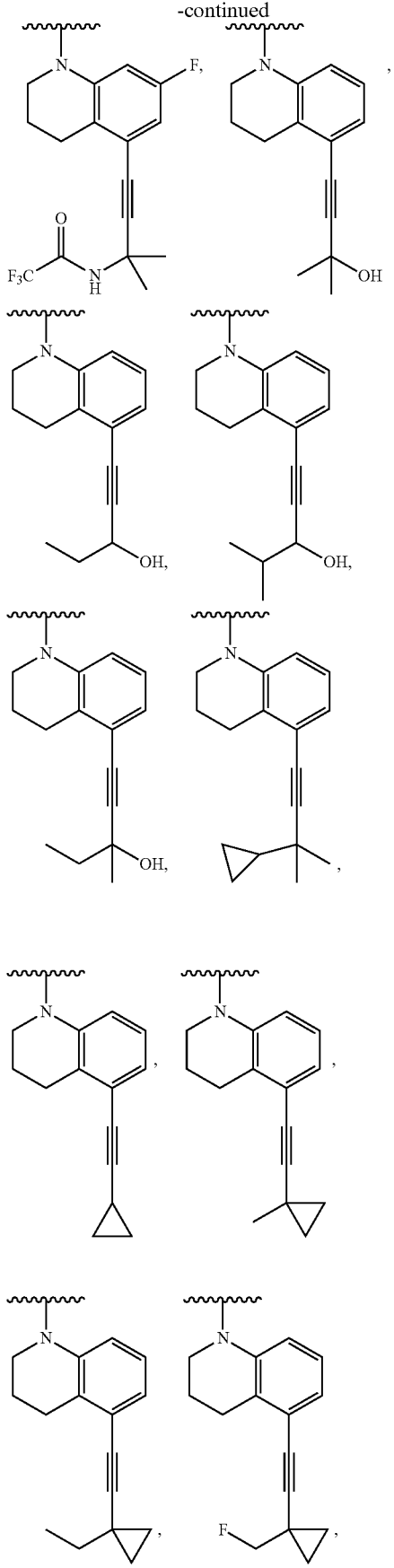
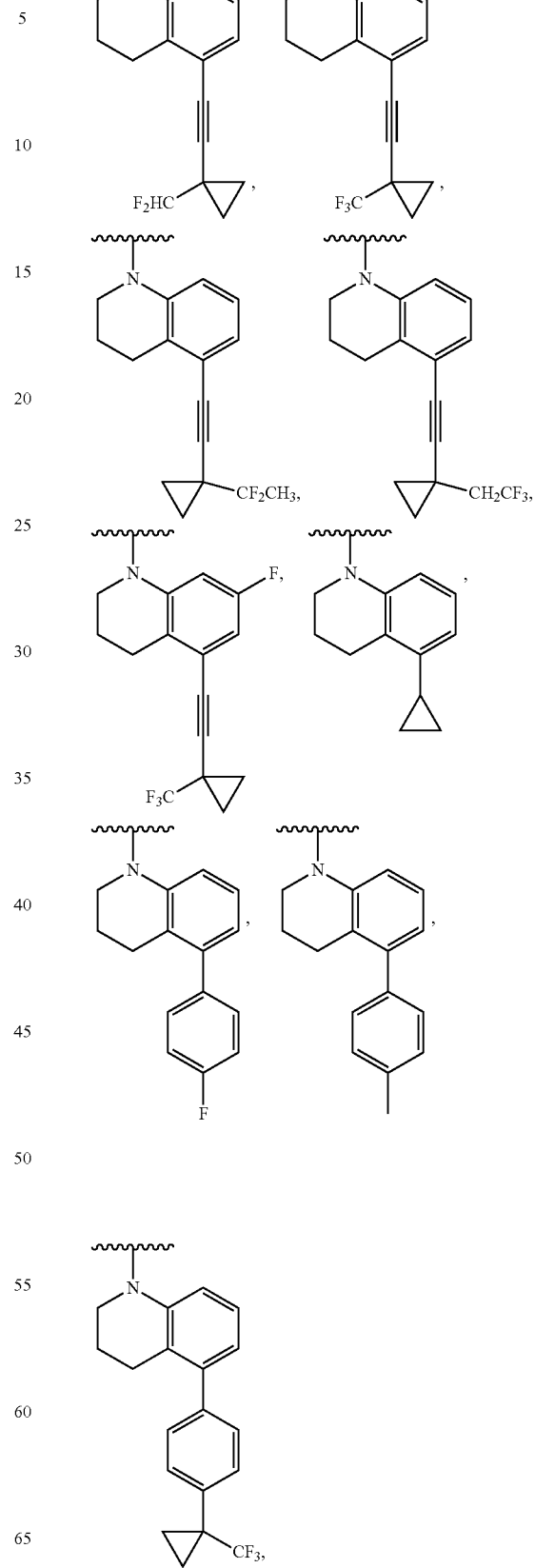

167
-continued
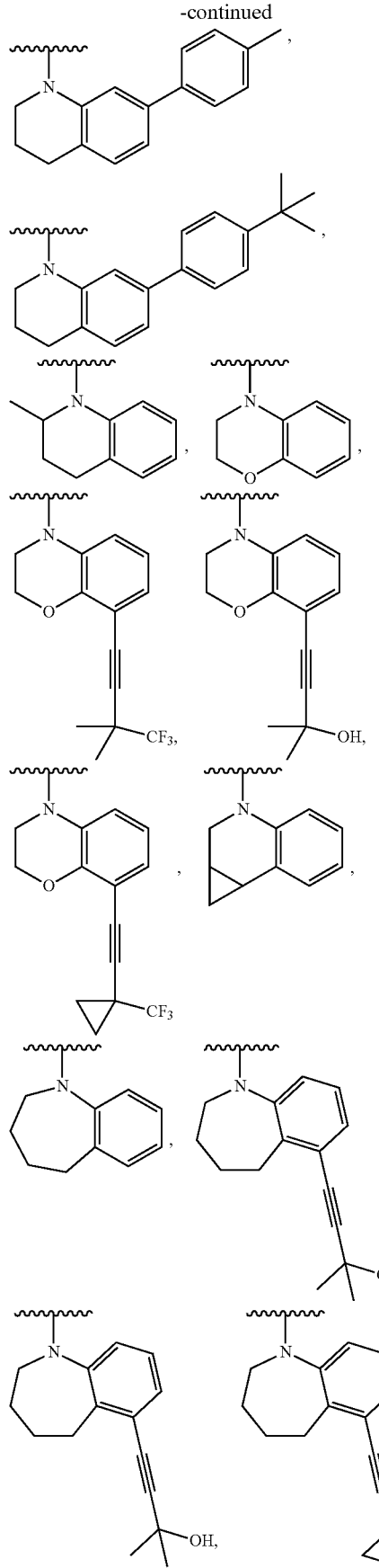
168
-continued
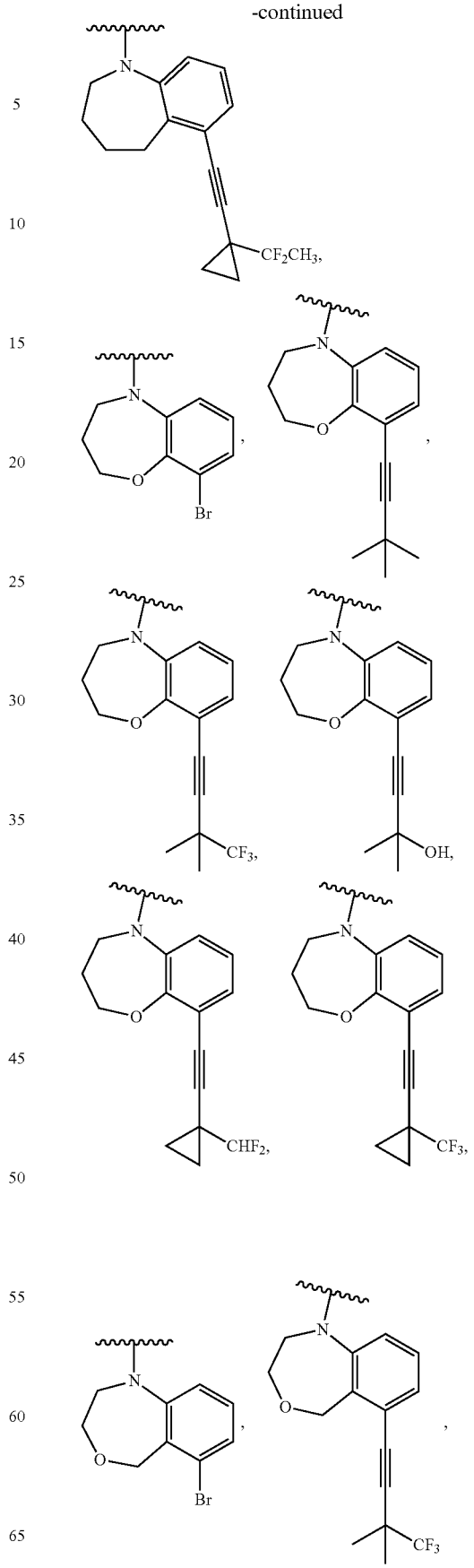

-continued

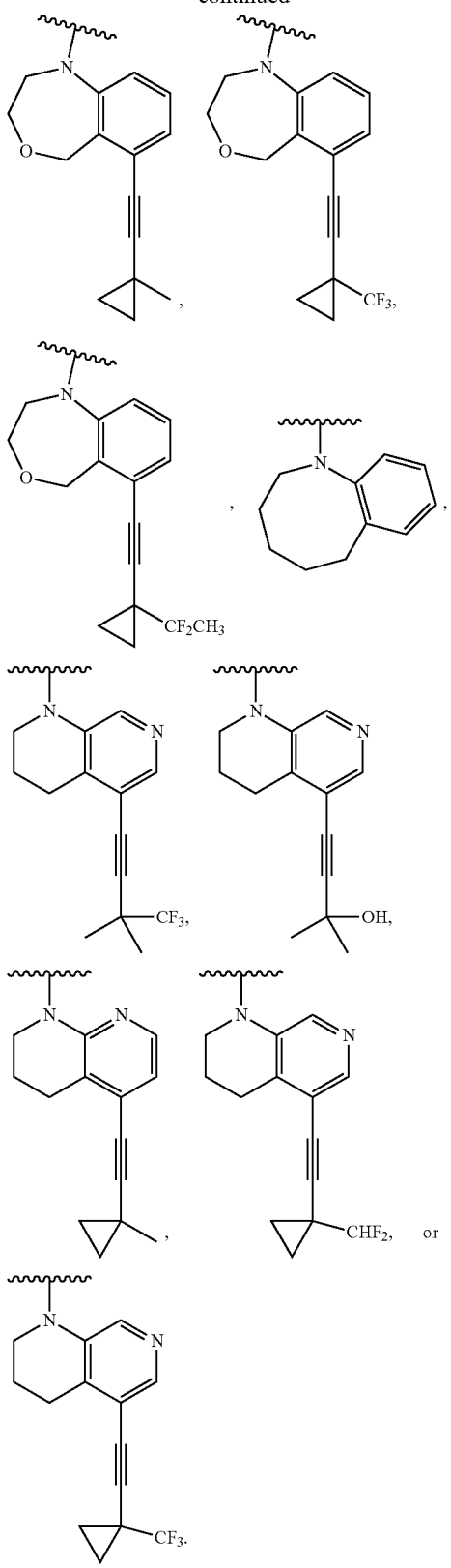

In some embodiments, the compound of Formula (I) or (I-1), or a pharmaceutically acceptable salt thereof, is a compound that has the structure of Formula (Ic):

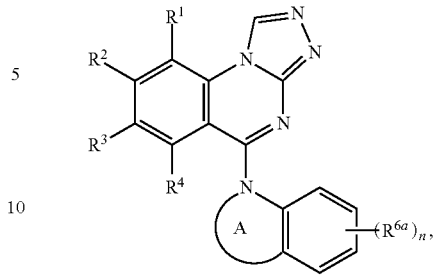

(Ic)

wherein Ring A is a 5 to 8 membered heterocycloalkyl optionally having 1 to 2 additional heteroatoms each independently N, O, or S, and optionally wherein Ring A is substituted with 1 or 2 $R^{6g}$; and n is 0, 1, or 2. In some embodiments, the compound of Formula (Ic), or a pharmaceutically acceptable salt thereof, is a compound wherein Ring A is a 5 to 8 membered heterocycloalkyl optionally having 1 to 2 additional heteroatoms each independently N, O, or S; and n is 0, 1, or 2. In some embodiments, the compound of Formula (Ic), or a pharmaceutically acceptable salt thereof, is a compound wherein n is 0. In some embodiments, the compound of Formula (Ic), or a pharmaceutically acceptable salt thereof, is a compound wherein n is 1. In some embodiments, the compound of Formula (Ic), or a pharmaceutically acceptable salt thereof, is a compound wherein n is 2. In some embodiments, the compound of Formula (Ic), or a pharmaceutically acceptable salt thereof, is a compound wherein Ring A is a 5 to 8 membered heterocycloalkyl. In some embodiments, the compound of Formula (Ic), or a pharmaceutically acceptable salt thereof, is a compound wherein Ring A is a 6 membered heterocycloalkyl having one additional heteroatom O.

In some embodiments, the compound of Formula (I), or a pharmaceutically acceptable salt thereof, is a compound that has the structure of Formula (IIc):

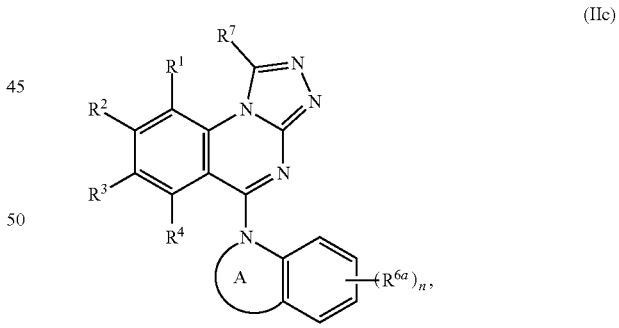

(IIc)

wherein Ring A is a 5 to 8 membered heterocycloalkyl optionally having 1 to 2 additional heteroatoms each independently N, O, or S, and optionally wherein Ring A is substituted with 1 or 2 $R^{6g}$; and n is 0, 1, or 2. In some embodiments, the compound of Formula (IIc), or a pharmaceutically acceptable salt thereof, is a compound wherein Ring A is a 5 to 8 membered heterocycloalkyl optionally having 1 to 2 additional heteroatoms each independently N, O, or S; and n is 0, 1, or 2. In some embodiments, the compound of Formula (IIc), or a pharmaceutically acceptable salt thereof, is a compound wherein n is 0. In some embodiments, the compound of Formula (IIc), or a pharmaceutically acceptable salt thereof, is a compound wherein n is 1. In some embodiments, the compound of Formula (IIc), or a pharmaceutically acceptable salt thereof, is a compound wherein n is 2. In some embodiments, the compound of Formula (IIc), or a pharmaceutically acceptable salt thereof, is a compound wherein Ring A is a 5 to 8 membered heterocycloalkyl. In some embodiments, the compound of Formula (IIc), or a pharmaceutically acceptable salt thereof, is a compound wherein Ring A is a 6 membered heterocycloalkyl having one additional heteroatom O.

In some embodiments, the compound of Formula (Ic) (IIc), (IIc-3), (IIc-4), (IIc-5), (IIc-6), (IIc-7), or (IIc-8), or a pharmaceutically acceptable salt thereof, is the compound wherein $R^1$ is hydrogen or halogen. In some embodiments, the compound of Formula (Ic) (IIc), (IIc-3), (IIc-4), (IIc-5), (IIc-6), (IIc-7), or (IIc-8), or a pharmaceutically acceptable salt thereof, is the compound wherein $R^1$ is hydrogen or F.

In some embodiments, the compound of Formula (Ic) (IIc), (IIc-3), (IIc-4), (IIc-5), (IIc-6), (IIc-7), or (IIc-8), or a pharmaceutically acceptable salt thereof, is the compound wherein $R^4$ is hydrogen, $C_{1-3}$ alkyl, or halogen. In some embodiments, the compound of Formula (Ic) (IIc), (IIc-3), (IIc-4), (IIc-5), (IIc-6), (IIc-7), or (IIc-8), or a pharmaceutically acceptable salt thereof, is the compound wherein $R^4$ is hydrogen, Me, or F.

In some embodiments, the compound of Formula (I), or a pharmaceutically acceptable salt thereof, is a compound that has the structure of Formula (IIc-1):

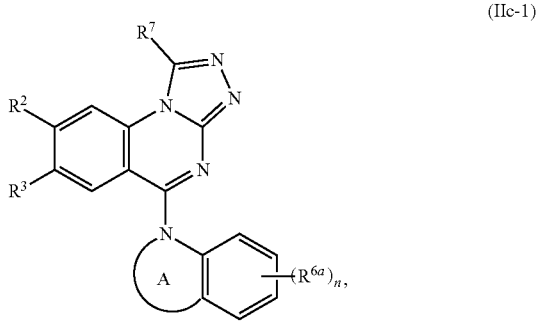

(IIc-1)

wherein Ring A is a 5 to 8 membered heterocycloalkyl optionally having 1 to 2 additional heteroatoms each independently N, O, or S, and optionally wherein Ring A is substituted with 1 or 2 $R^{6g}$; and n is 0, 1, or 2. In some embodiments, the compound of Formula (IIc-1), or a pharmaceutically acceptable salt thereof, is a compound wherein Ring A is a 5 to 8 membered heterocycloalkyl optionally having 1 to 2 additional heteroatoms each independently N, O, or S; and n is 0, 1, or 2. In some embodiments, the compound of Formula (IIc-1), or a pharmaceutically acceptable salt thereof, is a compound wherein n is 0. In some embodiments, the compound of Formula (IIc-1), or a pharmaceutically acceptable salt thereof, is a compound wherein n is 1. In some embodiments, the compound of Formula (IIc-1), or a pharmaceutically acceptable salt thereof, is a compound wherein n is 2. In some embodiments, the compound of Formula (IIc-1), or a pharmaceutically acceptable salt thereof, is a compound wherein Ring A is a 5 to 8 membered heterocycloalkyl. In some embodiments, the compound of Formula (IIc-1), or a pharmaceutically acceptable salt thereof, is a compound wherein Ring A is a 6 membered heterocycloalkyl having one additional heteroatom O.

In some embodiments, the compound of Formula (Ic), (IIc), or (IIc-1), or a pharmaceutically acceptable salt thereof, is a compound wherein

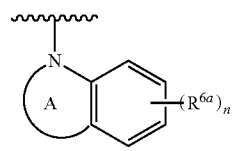

n has the structure

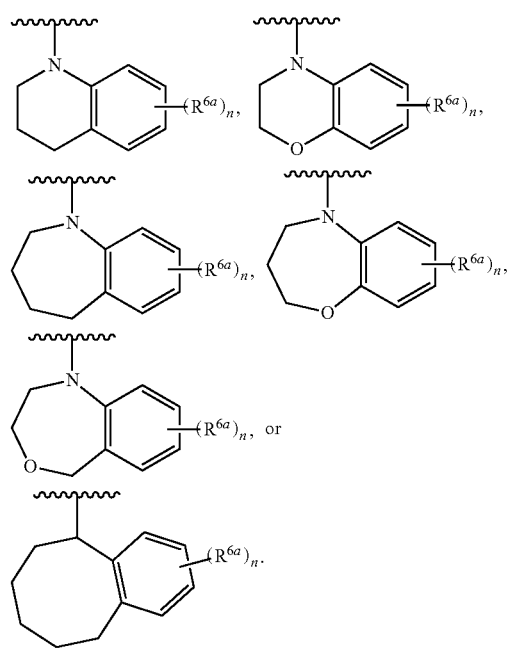

In some embodiments, the compound of Formula (I) or (Ic), or a pharmaceutically acceptable salt thereof, is a compound wherein each $R^{6g}$ is independently $C_{1-6}$ alkyl, halogen, $C_{1-6}$ haloalkyl, or —CN. In some embodiments, the compound of Formula (I) or (Ic), or a pharmaceutically acceptable salt thereof, is a compound wherein each $R^{6g}$ is independently $C_{1-6}$ alkyl or halogen. In some embodiments, the compound of Formula (I) or (Ic), or a pharmaceutically acceptable salt thereof, is a compound wherein each $R^{6g}$ is independently methyl.

In some embodiments, the compound of Formula (Ic), (IIc), or (IIc-1), or a pharmaceutically acceptable salt thereof, is a compound wherein

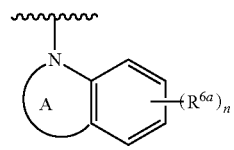

has the structure
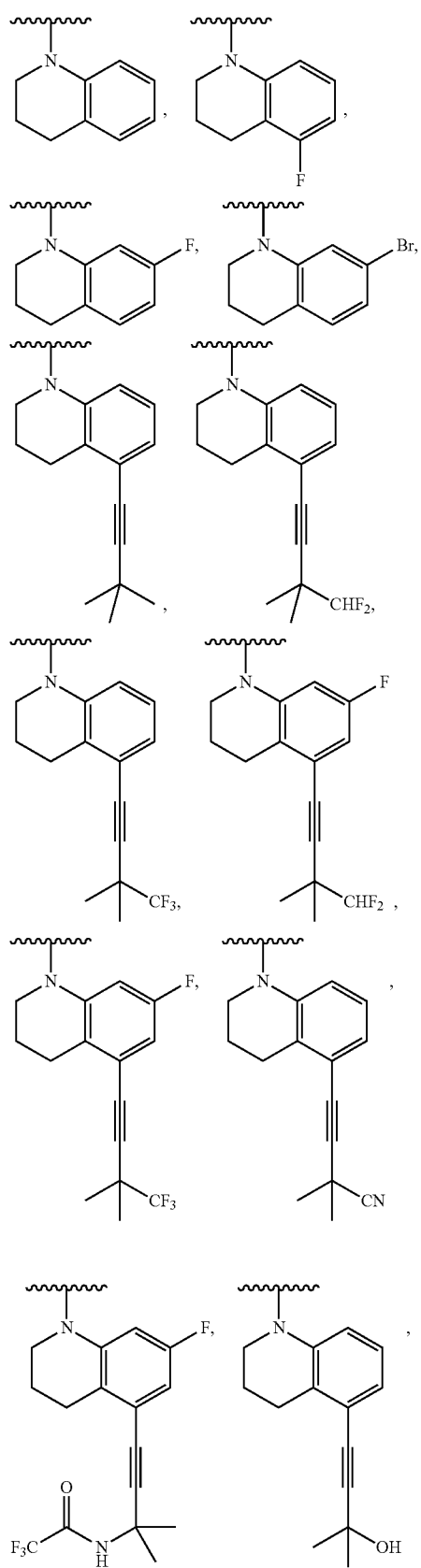
-continued
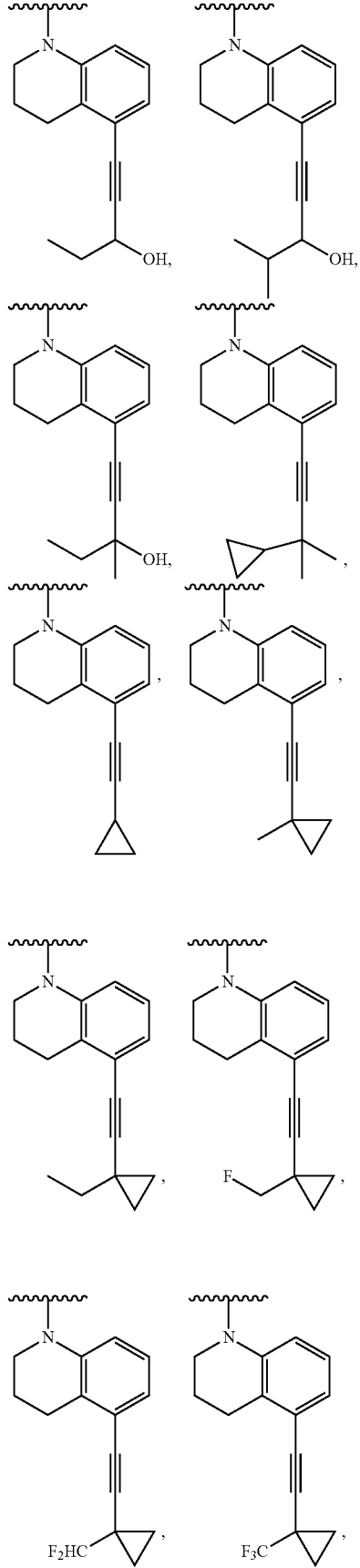

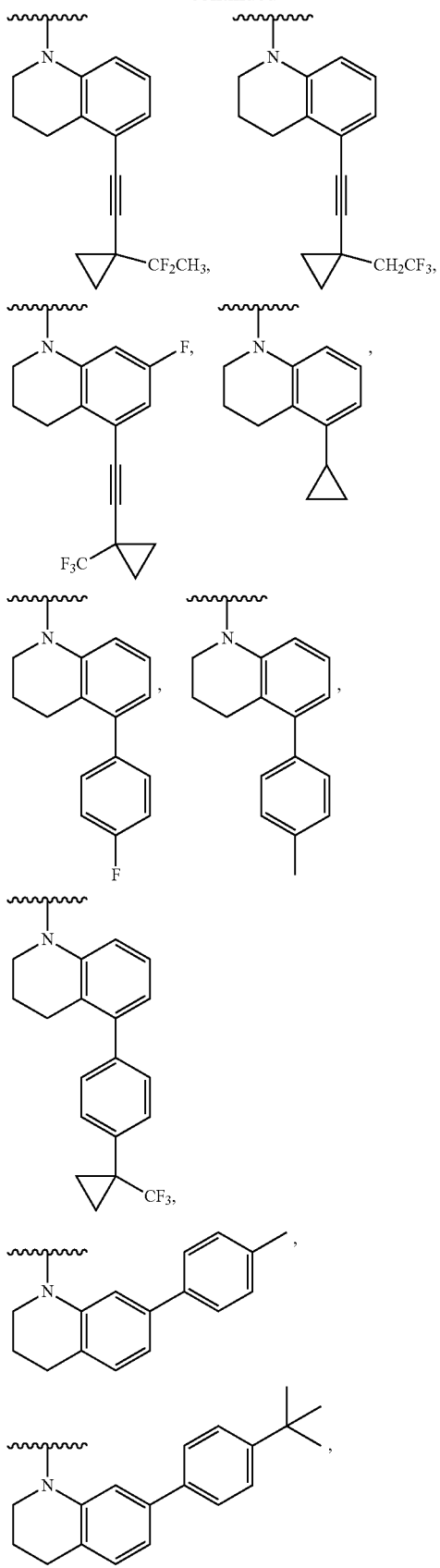
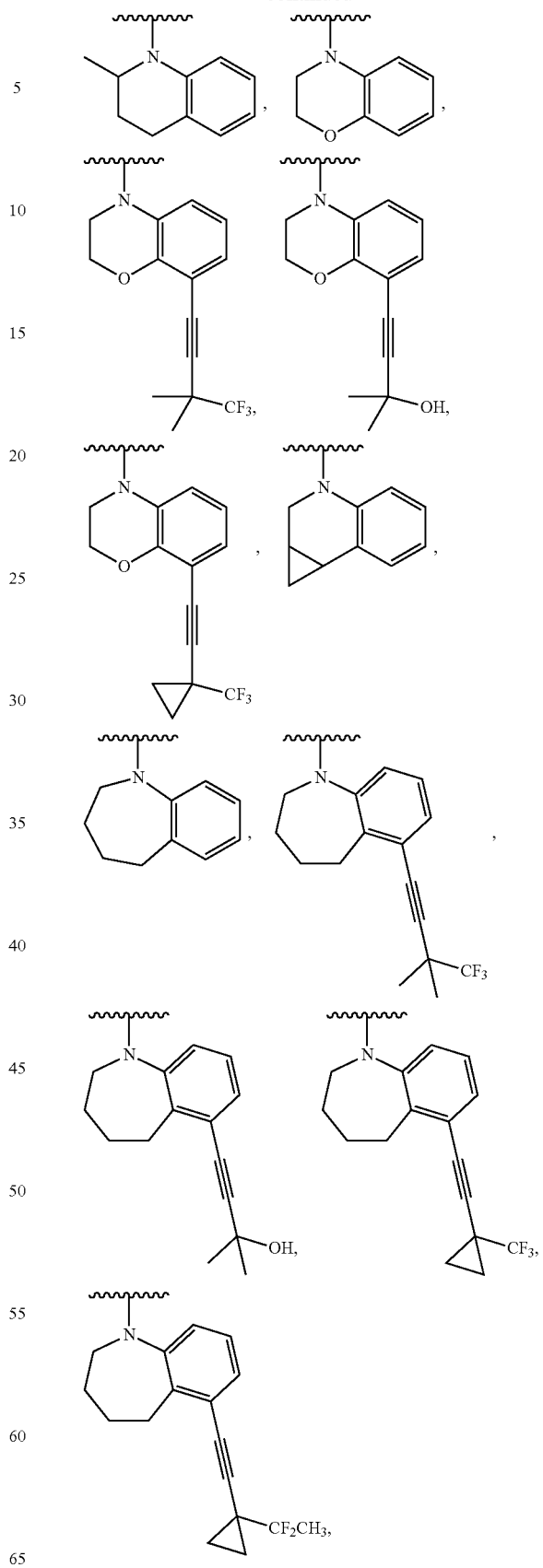

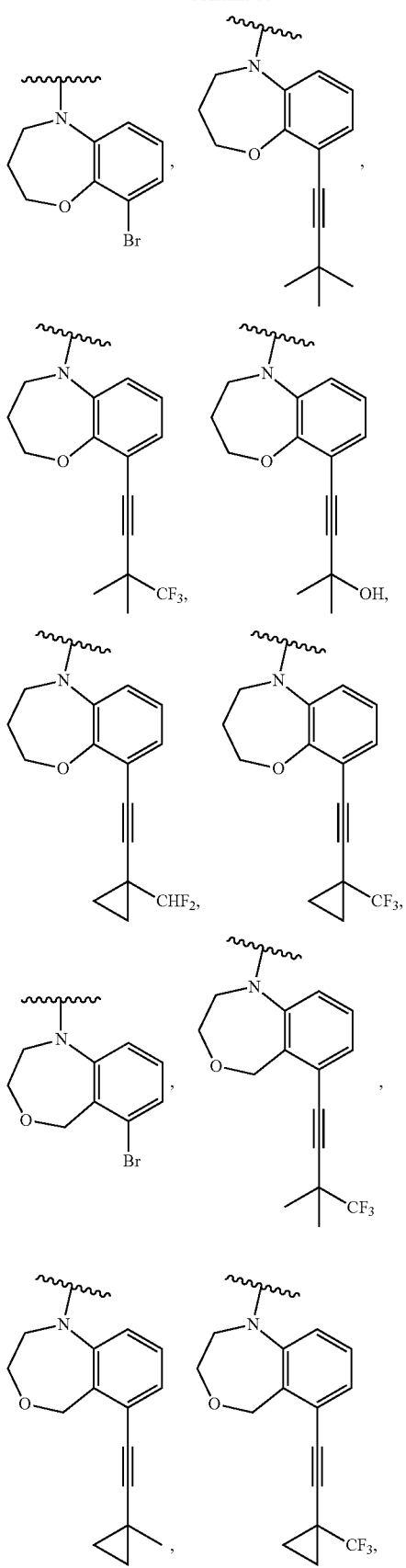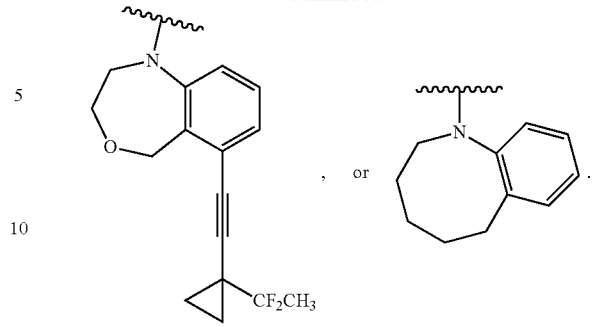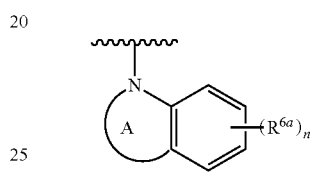
In some embodiments, the compound of Formula (Ic), (IIc), or (IIc-1), or a pharmaceutically acceptable salt thereof, is a compound wherein
has the structure
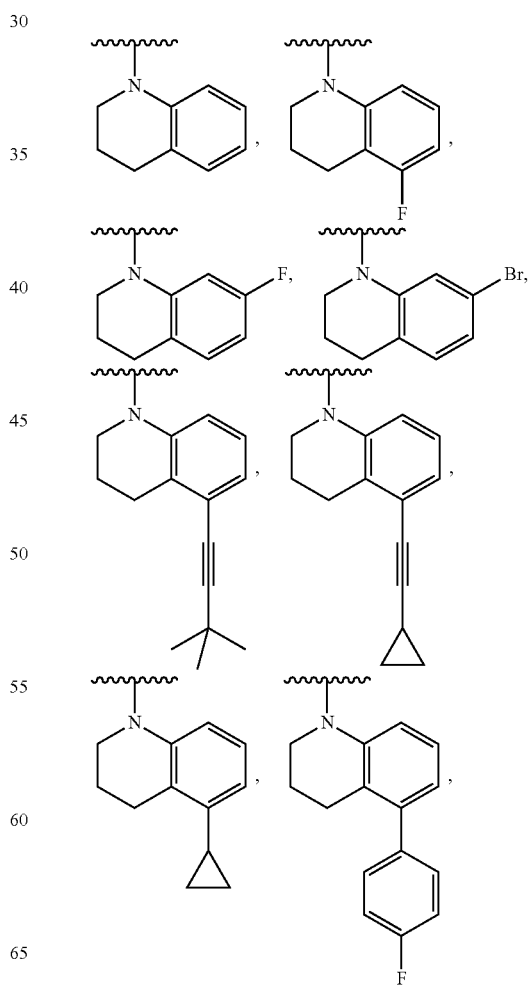

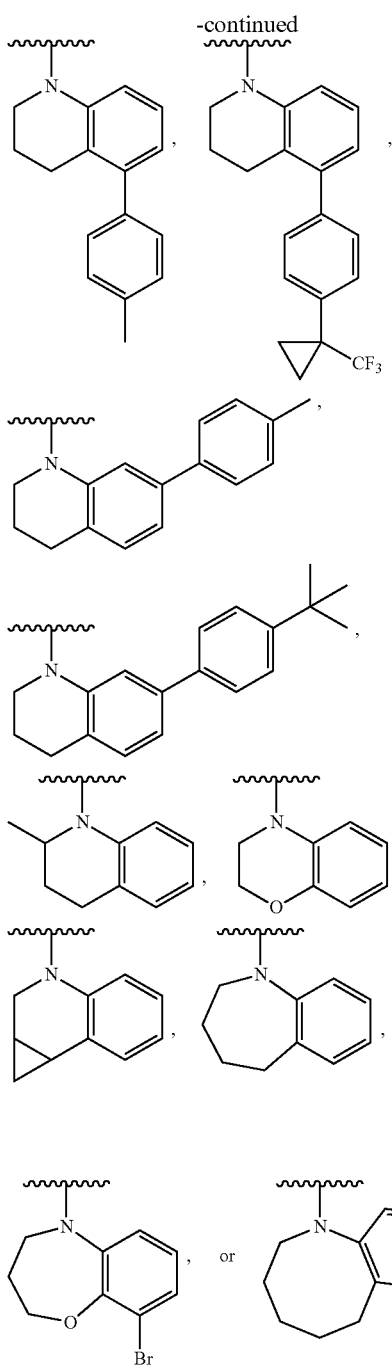

In some embodiments, the compound of Formula (Ic), or a pharmaceutically acceptable salt thereof, is a compound in which

has the structure

[structures shown]

In some embodiments, the compound of Formula (Ic), (IIc), or (IIc-1), or a pharmaceutically acceptable salt thereof, is a compound wherein

[structure with A and (R^{6a})_n]

has the structure

[structure with (R^{6a})_n]

In some embodiments, the compound of Formula (Ic), (Ic), or (IIc-1), or a pharmaceutically acceptable salt thereof, is a compound wherein

[structure with A and (R^{6a})_n]

has the structure

[structure with (R^{6a})_n]

In some embodiments, the compound of Formula (Ic), (IIc), or (IIc-1), or a pharmaceutically acceptable salt thereof, is a compound wherein

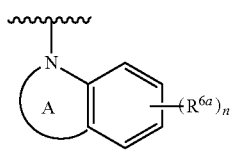

has the structure

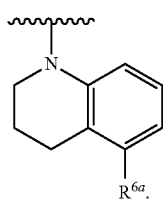

In some embodiments, the compound of Formula (I), or a pharmaceutically acceptable salt thereof, is a compound that has the structure of Formula (IIc-2):

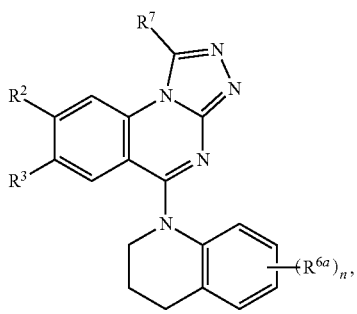

wherein n is 0, 1, or 2.

In some embodiments, the compound of Formula (Ic), (IIc), or (IIc-1), or a pharmaceutically acceptable salt thereof, is a compound wherein

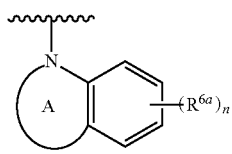

has the structure

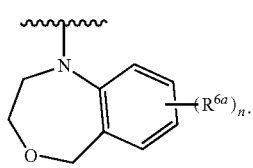

In some embodiments, the compound of Formula (I), (IIa), or (Ic), or a pharmaceutically acceptable salt thereof, is a compound that has the structure:

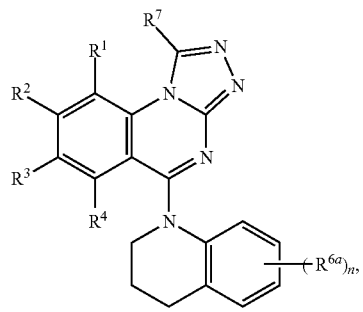

(IIc-3)

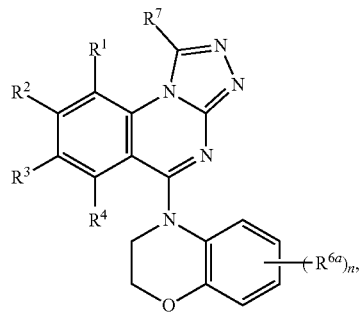

(IIc-4)

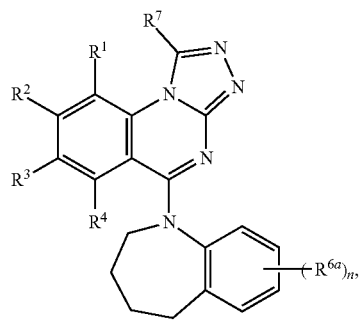

(IIc-5)

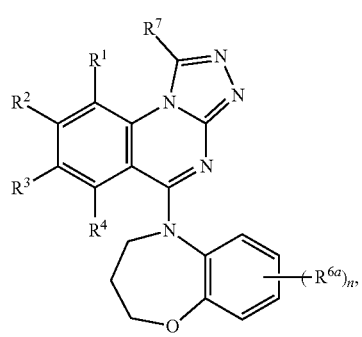

(IIc-6)

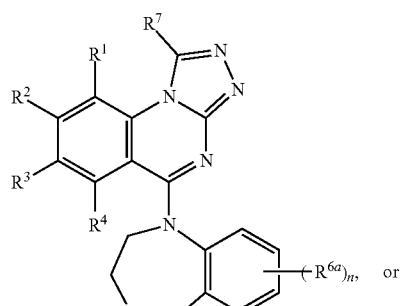

(IIc-7) or

183

-continued (IIc-8)

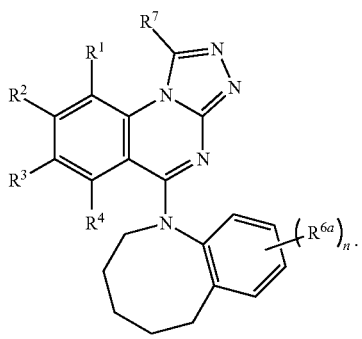

In some embodiments, the compound of Formula (IIc) is the compound of Formula (IIc-3), or a pharmaceutically acceptable salt thereof. In some embodiments, the compound of Formula (IIc) is the compound of Formula (IIc-4), or a pharmaceutically acceptable salt thereof. In some embodiments, the compound of Formula (IIc) is the compound of Formula (IIc-5), or a pharmaceutically acceptable salt thereof. In some embodiments, the compound of Formula (IIc) is the compound of Formula (IIc-6), or a pharmaceutically acceptable salt thereof. In some embodiments, the compound of Formula (IIc) is the compound of Formula (IIc-7), or a pharmaceutically acceptable salt thereof. In some embodiments, the compound of Formula (IIc) is the compound of Formula (IIc-8), or a pharmaceutically acceptable salt thereof.

In some embodiments, the compound of Formula (I), (IIa), (IIa-1), (IIc), (IIc-3), (IIc-4), (IIc-5), (IIc-6), (IIc-7), or (IIc-8), or a pharmaceutically acceptable salt thereof, is a compound wherein $R^1$ is hydrogen, $C_{1-3}$ alkyl, or halogen; $R^2$ is hydrogen, $C_{1-3}$ alkyl, $C_{1-3}$ hydroxyalkyl, $C_{2-3}$ alkoxyalkyl, halogen, or —CN; $R^3$ is hydrogen, $C_{1-3}$ alkyl, or halogen; $R^4$ is hydrogen, $C_{1-3}$ alkyl, or halogen; each $R^{6a}$ is independently $C_{1-3}$ alkyl, $C_{2-3}$ alkenyl, or $C_{2-3}$ alkynyl, wherein the alkynyl is optionally substituted with 1 to 3 $R^{6j}$; each $R^{6j}$ is independently $C_{2-3}$ alkoxyalkyl, halogen, $C_{1-3}$ haloalkyl, $C_{1-3}$ haloalkoxy, —CN, $C_{3-8}$ cycloalkyl, or heterocycloalkyl, wherein the cycloalkyl or heterocycloalkyl is optionally substituted with 1 to 3 $R^{6p}$; each $R^{6p}$ is independently $C_{1-3}$ alkyl, $C_{1-3}$ hydroxyalkyl, $C_{2-3}$ alkoxyalkyl, halogen, $C_{1-3}$ haloalkyl, $C_{1-3}$ haloalkoxy, or —CN; and $R^7$ is hydrogen, $C_{1-3}$ alkyl, $C_{2-3}$ alkoxyalkyl, $C_{1-3}$ haloalkyl, or —NH_2.

In some embodiments, the compound of Formula (I), (IIa), (IIa-1), (IIc), (IIc-3), (IIc-4), (IIc-5), (IIc-6), (IIc-7), or (IIc-8), or a pharmaceutically acceptable salt thereof, is a compound wherein $R^1$ is hydrogen, $C_{1-3}$ alkyl, or halogen; $R^2$ is hydrogen, $C_{1-3}$ alkyl, $C_{1-3}$ hydroxyalkyl, $C_{2-3}$ alkoxyalkyl, halogen, or —CN; $R^3$ is hydrogen, $C_{1-3}$ alkyl, or halogen; $R^4$ is hydrogen, $C_{1-3}$ alkyl, or halogen; each $R^{6a}$ is independently $C_{1-3}$ alkyl, $C_{2-3}$ alkenyl, or $C_{2-3}$ alkynyl, wherein the alkynyl is optionally substituted with 1 to 3 $R^{6j}$; each $R^{6j}$ is independently $C_{2-3}$ alkoxyalkyl, halogen, $C_{1-3}$ haloalkyl, $C_{1-3}$ haloalkoxy, —CN, $C_{3-8}$ cycloalkyl, or heterocycloalkyl, wherein the cycloalkyl or heterocycloalkyl is optionally substituted with 1 to 3 $R^{6p}$; each $R^{6p}$ is independently $C_{1-3}$ alkyl, $C_{1-3}$ hydroxyalkyl, $C_{2-3}$ alkoxyalkyl, halogen, $C_{1-3}$ haloalkyl, $C_{1-3}$ haloalkoxy, or —CN; and $R^7$ is hydrogen or $C_{1-3}$ alkyl.

184

In some embodiments, the compound of Formula (I), (IIa), (IIa-1), (IIc), (IIc-3), (IIc-4), (IIc-5), (IIc-6), (IIc-7), or (IIc-8), or a pharmaceutically acceptable salt thereof, is a compound wherein $R^1$ is hydrogen or F; $R^2$ is hydrogen, F or Cl; $R^3$ is hydrogen or F; $R^4$ is hydrogen or F; each $R^{6a}$ is independently $C_{1-3}$ alkyl, $C_{2-3}$ alkenyl, or $C_{2-3}$ alkynyl, wherein the alkynyl is optionally substituted with 1 to 3 $R^{6j}$; each $R^{6j}$ is independently $C_{2-3}$ alkoxyalkyl, halogen, $C_{1-3}$ haloalkyl, $C_{1-3}$ haloalkoxy, —CN, $C_{3-8}$ cycloalkyl, or heterocycloalkyl, wherein the cycloalkyl or heterocycloalkyl is optionally substituted with 1 to 3 $R^{6p}$; each $R^{6p}$ is independently $C_{1-3}$ alkyl, $C_{1-3}$ hydroxyalkyl, $C_{2-3}$ alkoxyalkyl, halogen, $C_{1-3}$ haloalkyl, $C_{1-3}$ haloalkoxy, or —CN; and $R^7$ is hydrogen or Me.

In some embodiments, the compound of Formula (Ic), (IIc), or (IIc-1), or a pharmaceutically acceptable salt thereof, is a compound wherein $R^2$ is hydrogen, $C_{1-3}$ alkyl, $C_{1-3}$ hydroxyalkyl, $C_{2-3}$ alkoxyalkyl, halogen, or —CN; $R^3$ is hydrogen, $C_{1-3}$ alkyl, or halogen; each $R^{6a}$ is independently $C_{1-3}$ alkyl, $C_{2-3}$ alkenyl, or $C_{2-3}$ alkynyl, wherein the alkynyl is optionally substituted with 1 to 3 $R^{6j}$; each $R^{6j}$ is independently $C_{2-3}$ alkoxyalkyl, halogen, $C_{1-3}$ haloalkyl, $C_{1-3}$ haloalkoxy, —CN, $C_{3-8}$ cycloalkyl, or heterocycloalkyl, wherein the cycloalkyl or heterocycloalkyl is optionally substituted with 1 to 3 $R^{6p}$; each $R^{6p}$ is independently $C_{1-3}$ alkyl, $C_{1-3}$ hydroxyalkyl, $C_{2-3}$ alkoxyalkyl, halogen, $C_{1-3}$ haloalkyl, $C_{1-3}$ haloalkoxy, or —CN; $R^7$ is hydrogen or $C_{1-3}$ alkyl; and

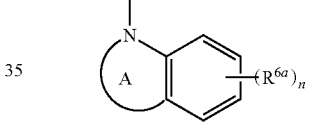

has the structure

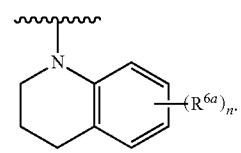

In some embodiments, the compound of Formula (Ic), (IIc), (IIc-1), (IIc-2), (IIc-3), (IIc-4), (IIc-5), (IIc-6), (IIc-7), or (IIc-8), or a pharmaceutically acceptable salt thereof, is a compound wherein $R^2$ is hydrogen, halogen, or —CN. In some embodiments, the compound of Formula (Ic), (IIc), (IIc-1), (IIc-2), (IIc-3), (IIc-4), (IIc-5), (IIc-6), (IIc-7), or (IIc-8), or a pharmaceutically acceptable salt thereof, is a compound wherein $R^2$ is hydrogen, F, or Cl.

In some embodiments, the compound of Formula (Ic), (IIc), (IIc-1), (IIc-2), (IIc-3), (IIc-4), (IIc-5), (IIc-6), (IIc-7), or (IIc-8), or a pharmaceutically acceptable salt thereof, is a compound wherein $R^3$ is hydrogen, F, or Cl.

In some embodiments, the compound of Formula (Ic), (IIc), (IIc-1), (IIc-2), (IIc-3), (IIc-4), (IIc-5), (IIc-6), (IIc-7), or (IIc-8), or a pharmaceutically acceptable salt thereof, is a compound wherein each $R^{6a}$ is independently $C_{2-3}$ alkynyl or halogen, wherein the alkynyl is optionally substituted with 1 to 3 $R^{6j}$. In some embodiments, the compound of Formula (Ic), (IIc), (IIc-1), (IIc-2), (IIc-3), (IIc-4), (IIc-5), (IIc-6), (IIc-7), or (IIc-8), or a pharmaceutically acceptable salt thereof, is a compound wherein each $R^{6a}$ is

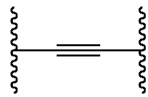

substituted with 1 $R^{6j}$.

In some embodiments, the compound of Formula (Ic), (IIc), (IIc-1), (IIc-2), (IIc-3), (IIc-4), (IIc-5), (IIc-6), (IIc-7), or (IIc-8), or a pharmaceutically acceptable salt thereof, is a compound wherein each $R^{6j}$ is independently $C_{2-3}$ alkoxyalkyl, halogen, $C_{1-3}$ haloalkyl, —CN, $C_{3-6}$ cycloalkyl, or heterocycloalkyl, wherein the cycloalkyl or heterocycloalkyl is optionally substituted with 1 to 3 $R^{6p}$, and each heterocycloalkyl is a 3 to 6 membered ring having 1 to 2 heteroatoms each independently N, O or S. In some embodiments, the compound of Formula (Ic), (IIc), (IIc-1), (IIc-2), (IIc-3), (IIc-4), (IIc-5), (IIc-6), (IIc-7), or (IIc-8), or a pharmaceutically acceptable salt thereof, is a compound wherein each $R^6$ is independently halogen, $C_{1-3}$ haloalkyl, $C_{3-6}$ cycloalkyl, or heterocycloalkyl, wherein the cycloalkyl or heterocycloalkyl is optionally substituted with 1 to 2 $R^{6p}$, and each heterocycloalkyl is a 3 to 6 membered ring having 1 to 2 heteroatoms each independently N, O or S. In some embodiments, the compound of Formula (Ic), (IIc), (IIc-1), (IIc-2), (IIc-3), (IIc-4), (IIc-5), (IIc-6), (IIc-7), or (IIc-8), or a pharmaceutically acceptable salt thereof, is a compound wherein each $R^{6j}$ is independently halogen, $C_{1-3}$ haloalkyl, or $C_{3-6}$ cycloalkyl, wherein the cycloalkyl is optionally substituted with one $R^{6p}$. In some embodiments, the compound of Formula (Ic), (IIc), (IIc-1), (IIc-2), (IIc-3), (IIc-4), (IIc-5), (IIc-6), (IIc-7), or (IIc-8), or a pharmaceutically acceptable salt thereof, is a compound wherein each $R^{6j}$ is independently F, $CH_2F$, $CHF_2$, $CF_3$, $CH_2CF_3$, $CF_2CH_3$, or cyclopropyl, wherein the cyclopropyl is optionally substituted with one $R^{6p}$.

In some embodiments, the compound of Formula (Ic), (IIc), (IIc-1), (IIc-2), (IIc-3), (IIc-4), (IIc-5), (IIc-6), (IIc-7), or (IIc-8), or a pharmaceutically acceptable salt thereof, is a compound wherein each $R^{6p}$ is independently $C_{1-3}$ alkyl, $C_{1-3}$ hydroxyalkyl, halogen, $C_{1-3}$ haloalkyl, or —CN. In some embodiments, the compound of Formula (Ic), (IIc), (IIc-1), (IIc-2), (IIc-3), (IIc-4), (IIc-5), (IIc-6), (IIc-7), or (IIc-8), or a pharmaceutically acceptable salt thereof, is a compound wherein each $R^{6p}$ is independently Me, Et, $CH_2OH$, F, $CH_2F$, $CHF_2$, $CF_3$, $CH_2CF_3$, $CF_2CH_3$, or —CN.

In some embodiments, the compound of Formula (Ic), (IIc), or (IIc-1), or a pharmaceutically acceptable salt thereof, is a compound wherein

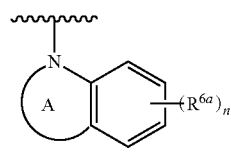

has the structure

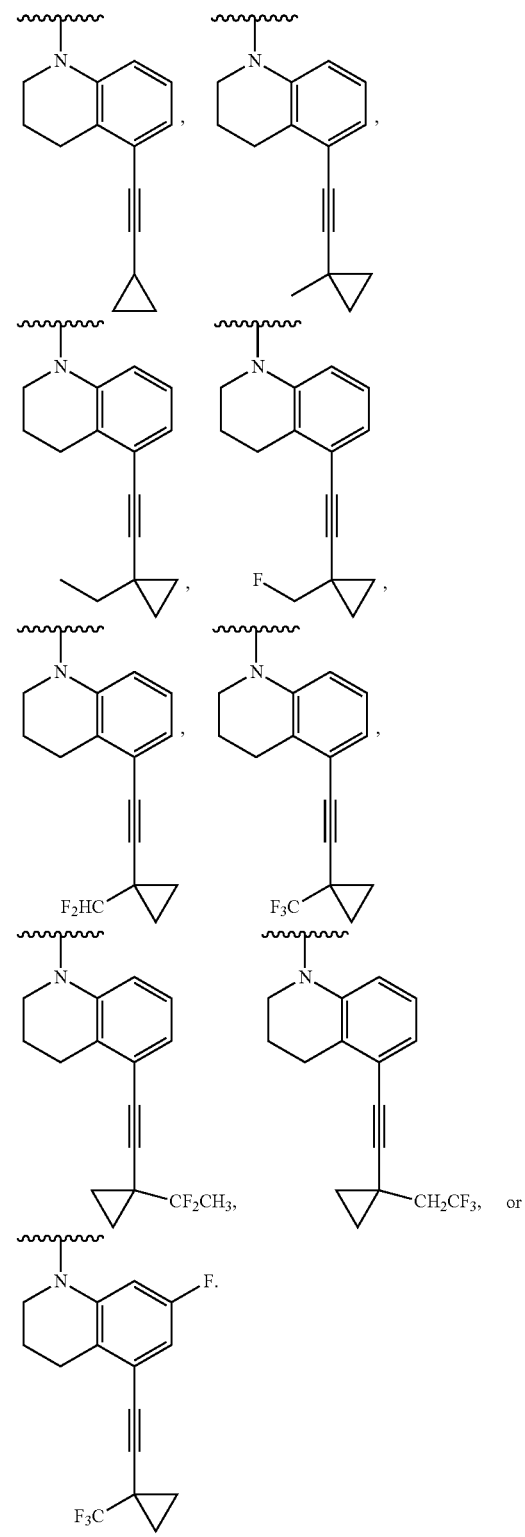

In some embodiments, the compound of Formula (I), (I-1), (Ia), (Ia-1), (Ib), (Ic), (IIa), (IIa-1), (Ic), (IIc-1)(IIc-2), (IIc-2), (IIc-3), (IIc-4), (IIc-5), (IIc-6), (IIc-7), or (IIc-8), or a pharmaceutically acceptable salt thereof, is the compound wherein the heterocycloalkyl is a 5 to 8 membered ring having 1 to 2 heteroatoms each independently N, O, or S. In some embodiments, the compound of Formula (I), (I-1), (Ia), (Ia-1), (Ib), (Ic), (IIa), (IIa-1), (IIc), (IIc-1)(IIc-2), (IIc-2), (IIc-3), (IIc-4), (IIc-5), (IIc-6), (IIc-7), or (IIc-8), or a pharmaceutically acceptable salt thereof, is the compound wherein the heterocycloalkyl is a 5 to 6 membered ring having 1 to 2 heteroatoms each independently N or O. In some embodiments, the compound of Formula (I), (I-1), (Ia), (Ia-1), (Ib), (Ic), (IIa), (IIa-1), (IIc), (IIc-1)(IIc-2), (IIc-2), (IIc-3), (IIc-4), (IIc-5), (IIc-6), (IIc-7), or (IIc-8), or a pharmaceutically acceptable salt thereof, is the compound wherein the heterocycloalkyl is a 6 membered ring having 1 heteratom N or O.

In some embodiments, the compound of Formula (I), (I-1), (Ia), (Ia-1), (Ib), (Ic), (IIa), (IIa-1), (IIc), (IIc-1)(IIc-2), (IIc-2), (IIc-3), (IIc-4), (IIc-5), (IIc-6), (IIc-7), or (IIc-8), or a pharmaceutically acceptable salt thereof, is the compound wherein the heteroaryl is a 5 to 6 membered ring having 1 to 2 heteroatoms each independently N, O, or S. In some embodiments, the compound of Formula (I), (I-1), (Ia), (Ia-1), (Ib), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound wherein the heteroaryl is a 6 membered ring having 1 to 2 heteroatoms each N.

In some embodiments, the compound of Formula (I), (I-1), (Ia), (Ia-1), (Ib), (Ic), (IIa), (IIa-1), (IIc), (IIc-1)(IIc-2), (IIc-2), (IIc-3), (IIc-4), (IIc-5), (IIc-6), (IIc-7), or (IIc-8), or a pharmaceutically acceptable salt thereof, is the compound wherein the heterocycloalkyl is a 5 to 6 membered ring having 1 to 2 heteroatoms each independently N or O; and the heteroaryl is a 5 to 6 membered ring having 1 to 2 heteroatoms each independently N, O, or S.

In some embodiments, the compound of Formula (I), (I-1), (Ia), (Ia-1), (Ib), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound having the structure of a compound in Table 1A, Table 1B, Table 1C, Table 1D, Table 1E, Table 1F, Table 1G, Table 1H, Table 1I, Table 1J, Table 2A, Table 2B, Table 2C, Table 2D, Table 2E, Table 2F, Table 2G, Table 2H, Table 2I, Table 2J, Table 2K, Table 2L, Table 3A, Table 3B, Table 3C, Table 3D, Table 3E, Table 3F, Table 3G, Table 3H, Table 3I, Table 3J, or Table 3K. In some embodiments, the compound of Formula (I), (I-1), (Ia), (Ia-1), (Ib), (Ic), (IIa), (IIa-1), (IIc), (IIc-1), (IIc-2), (IIc-3), (IIc-4), (IIc-5), (IIc-6), (IIc-7), or (IIc-8), or a pharmaceutically acceptable salt thereof, is the compound having the structure of a compound in Table 3F, Table 3H, Table 3I, Table 3J, or Table 3K.

TABLE 1A

| Compounds | |
|---|---|
| Ex. | Chemical Structure |
| 1 | [structure] |
| 2 | [structure] |
| 4 | [structure] |
| 5 | [structure] |
| 6 | [structure] |
| 8 | [structure] |

TABLE 1A-continued
Compounds
| Ex. | Chemical Structure |
|---|---|
| 9 | 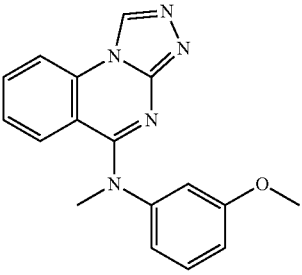 |
| 10 | 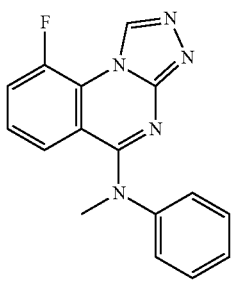 |
| 11 | 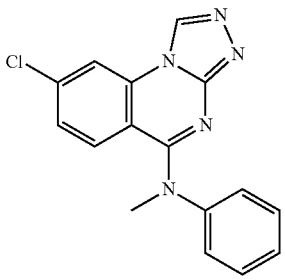 |
| 12 | 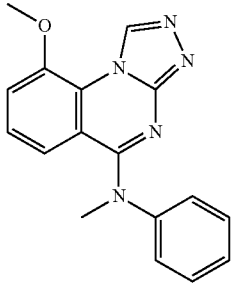 |
| 13 | 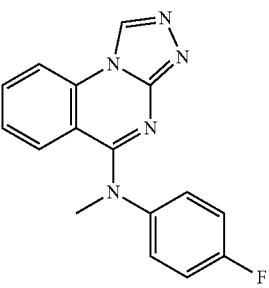 [SMILES: CN(c1ccc(F)cc1)c1nc2nncn2c2ccccc12] |
| 14 | 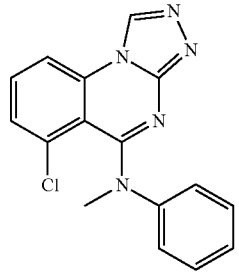 |
| 15 | 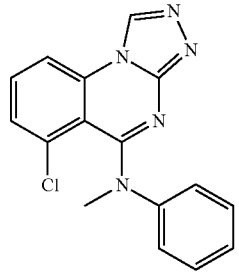 |
| 16 | 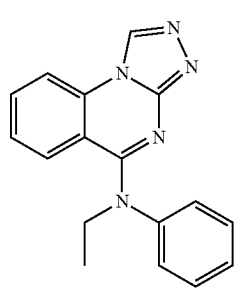 |
| 17 | 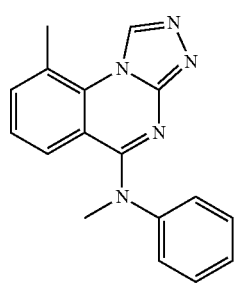 |
| 18 | 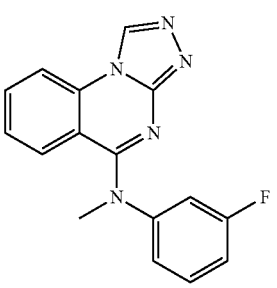 [SMILES: CN(c1cccc(F)c1)c1nc2nncn2c2ccccc12] |

TABLE 1A-continued

Compounds

| Ex. | Chemical Structure |
|---|---|
| 19 | 8-phenyl-N-methyl-N-phenyl-[1,2,4]triazolo[4,3-a]quinazolin-5-amine |
| 20 | 8-methoxy-N-methyl-N-phenyl-[1,2,4]triazolo[4,3-a]quinazolin-5-amine |
| 21 | 8-fluoro-N-methyl-N-phenyl-[1,2,4]triazolo[4,3-a]quinazolin-5-amine |
| 22 | N-methyl-N-(pyridin-2-yl)-[1,2,4]triazolo[4,3-a]quinazolin-5-amine |

TABLE 1B

Compounds

| Ex. | Chemical Structure |
|---|---|
| 23 | N-methyl-N-(pyridin-3-yl)-[1,2,4]triazolo[4,3-a]quinazolin-5-amine |
| 24 | N-methyl-N-(pyridin-4-yl)-[1,2,4]triazolo[4,3-a]quinazolin-5-amine |
| 25 | N-(2-chlorophenyl)-N-methyl-[1,2,4]triazolo[4,3-a]quinazolin-5-amine |
| 26 | 2-(methyl([1,2,4]triazolo[4,3-a]quinazolin-5-yl)amino)benzonitrile |
| 27 | N-(2-bromophenyl)-N-methyl-[1,2,4]triazolo[4,3-a]quinazolin-5-amine |

TABLE 1B-continued

Compounds

| Ex. | Chemical Structure |
|---|---|
| 28 | 8-bromo-N-methyl-N-phenyl-[1,2,4]triazolo[4,3-a]quinazolin-5-amine |
| 29 | 8-methyl-N-methyl-N-phenyl-[1,2,4]triazolo[4,3-a]quinazolin-5-amine |
| 30 | 8-cyclopropyl-N-methyl-N-phenyl-[1,2,4]triazolo[4,3-a]quinazolin-5-amine |
| 31 | N-methyl-N-phenyl-8-(pyridin-4-yl)-[1,2,4]triazolo[4,3-a]quinazolin-5-amine |
| 32 | N-(2-iodophenyl)-N-methyl-[1,2,4]triazolo[4,3-a]quinazolin-5-amine |

TABLE 1B-continued

Compounds

| Ex. | Chemical Structure |
|---|---|
| 33 | N-methyl-N-(2-methylphenyl)-[1,2,4]triazolo[4,3-a]quinazolin-5-amine |
| 34 | N-methyl-N-(3-methylphenyl)-[1,2,4]triazolo[4,3-a]quinazolin-5-amine |
| 35 | 8-chloro-N-methyl-N-phenyl-[1,2,4]triazolo[4,3-a]quinazolin-5-amine |
| 36 | 9-methyl-N-methyl-N-phenyl-[1,2,4]triazolo[4,3-a]quinazolin-5-amine |
| 37 | 8-ethynyl-N-methyl-N-phenyl-[1,2,4]triazolo[4,3-a]quinazolin-5-amine |

TABLE 1B-continued
| Ex. | Chemical Structure |
|---|---|
| 38 | 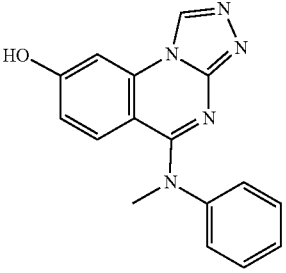 |
| 39 | 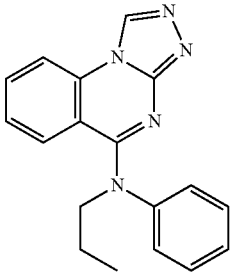 [SMILES: CCCN(c1ccccc1)c1nc2nncn2c2ccccc12] |
| 40 | 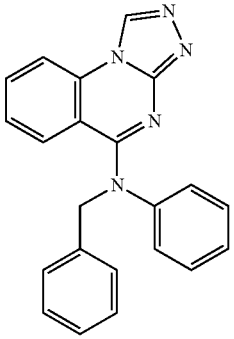 [SMILES: c1ccc(CN(c2ccccc2)c2nc3nncn3c3ccccc23)cc1] |
| 41 | 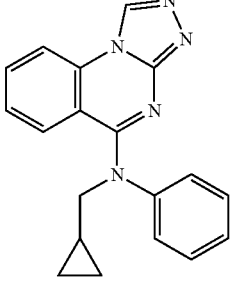 |
| 42 | 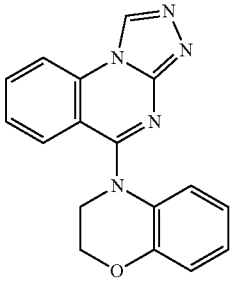 [SMILES: c1ccc2c(c1)OCCN2c1nc2nncn2c2ccccc12] |
| 43 | 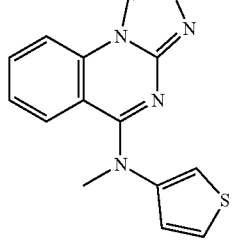 |
| 44 | 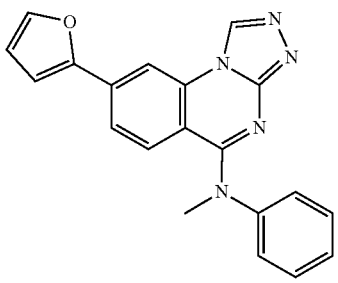 |
| 45 | 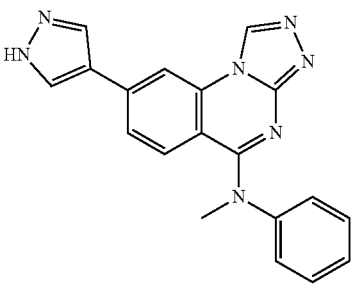 [SMILES: CN(c1ccccc1)c1nc2nncn2c2cc(-c3cn[nH]c3)ccc12] |
| 46 | 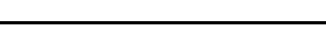 |
| 47 |  |

TABLE 1C

| Ex. | Chemical Structure |
|---|---|
| 48 | [triazoloquinazoline]-N(Me)-(4-hydroxyphenyl) |
| 49 | [triazoloquinazoline]-N(Me)-(2-hydroxyphenyl) |
| 50 | [triazoloquinazoline]-N(Me)-(3-hydroxyphenyl) |
| 51 | [triazoloquinazoline]-N(n-butyl)(phenyl) |
| 52 | [triazoloquinazoline]-N(2-methoxyethyl)(phenyl) |

TABLE 1C-continued

| Ex. | Chemical Structure |
|---|---|
| 53 | [triazoloquinazoline]-N(cyclohexylmethyl)(phenyl) |
| 54 | [triazoloquinazoline]-N(neopentyl)(phenyl) |
| 55 | [triazoloquinazoline]-N(propargyl)(phenyl) |
| 56 | [triazoloquinazoline]-N(but-3-yn-1-yl)(phenyl) |
| 57 | [triazoloquinazoline]-N(Me)(2-thienyl) |

TABLE 1C-continued
Compounds
| Ex. | Chemical Structure |
|---|---|
| 58 | 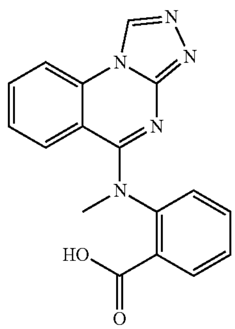 |
| 59 | 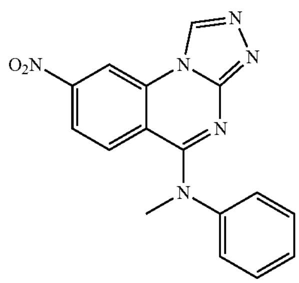 |
| 60 | 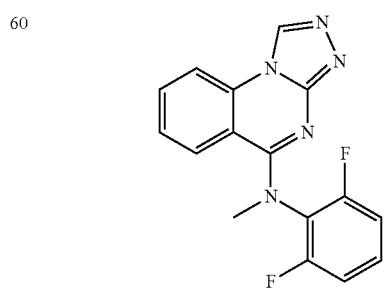 |
| 61 | 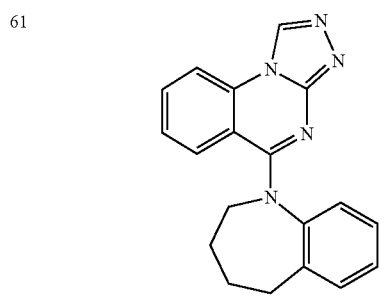 |
| 62 | 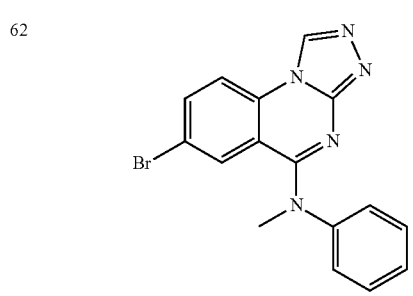 |
TABLE 1C-continued
Compounds
| Ex. | Chemical Structure |
|---|---|
| 63 | 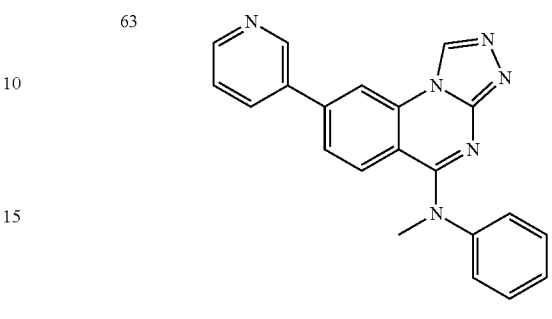 |
| 64 | 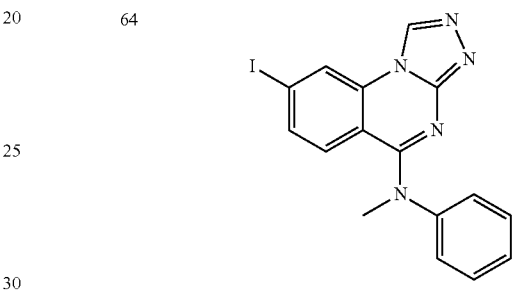 |
| 65 | 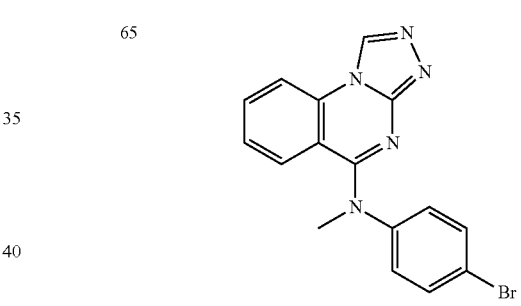 |
| 66 | 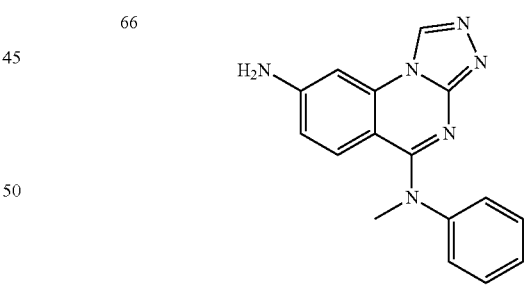 |
| 67 | 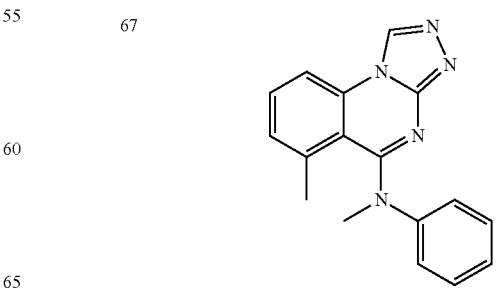 |

TABLE 1C-continued

Compounds

| Ex. | Chemical Structure |
|---|---|
| 68 | [structure] |
| 69 | [structure] |
| 70 | [structure] |
| 71 | [structure] |

TABLE 1D

Compounds

| Ex. | Chemical Structure |
|---|---|
| 72 | [structure] |
| 73 | [structure] |
| 74 | [structure] |
| 75 | [structure] |
| 76 | [structure] |

TABLE 1D-continued

Compounds

| Ex. | Chemical Structure |
|---|---|
| 77 | |
| 78 | |
| 79 | |
| 80 | |
| 81 | 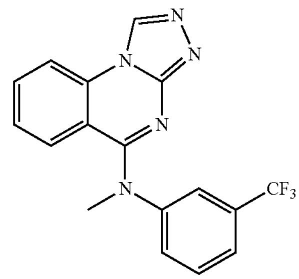 |
| 82 | 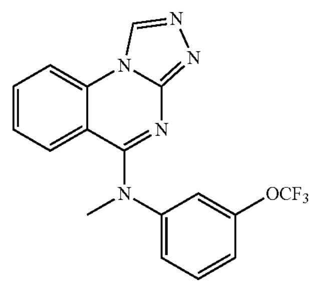 [SMILES: CN(c1cccc(OC(F)(F)F)c1)c1nc2nncn2c2ccccc12] |
| 83 | 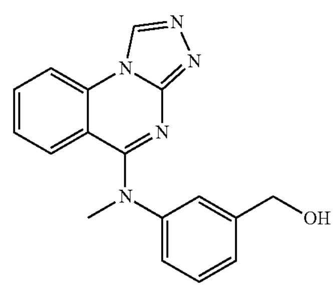 [SMILES: CN(c1cccc(CO)c1)c1nc2nncn2c2ccccc12] |
| 84 | 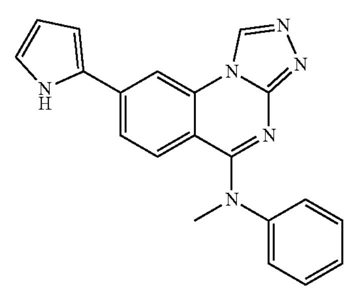 [SMILES: CN(c1ccccc1)c1nc2nncn2c2cc(-c3ccc[nH]3)ccc12] |
| 85 | 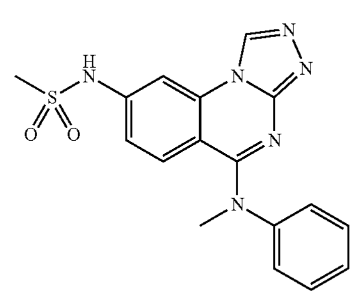 [SMILES: CN(c1ccccc1)c1nc2nncn2c2cc(NS(C)(=O)=O)ccc12] |

TABLE 1D-continued
Compounds
| Ex. | Chemical Structure |
|---|---|
| 86 | 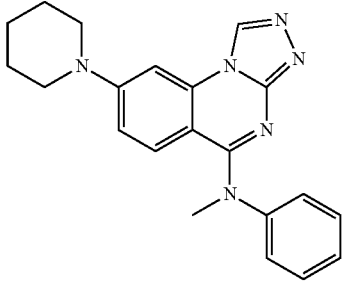 [SMILES: CN(c1ccccc1)c1nc2nncn2c2cc(N3CCCCC3)ccc12] |
| 87 | 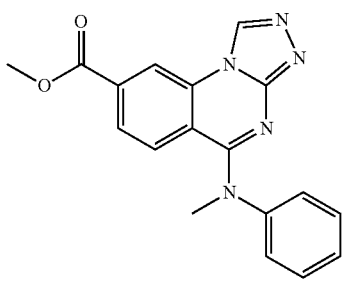 |
| 88 | 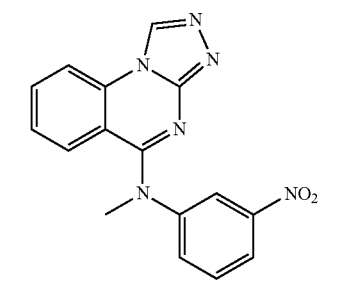 |
| 89 | 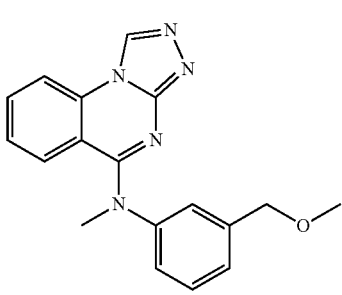 |
TABLE 1E
Compounds
| Ex. | Chemical Structure |
|---|---|
| 90 | 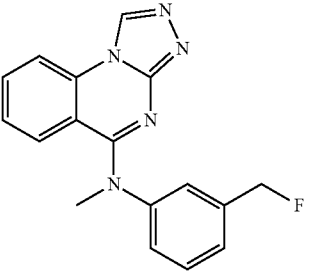 |
| 91 | 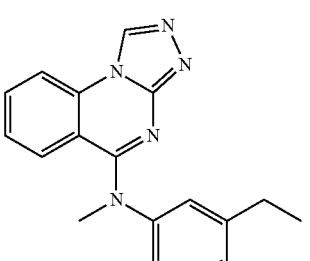 |
| 92 | 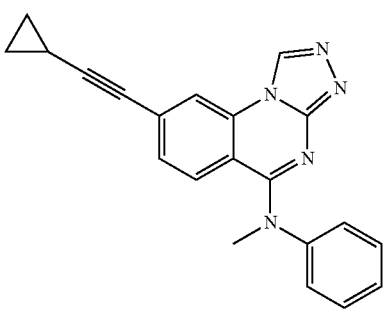 |
| 93 | 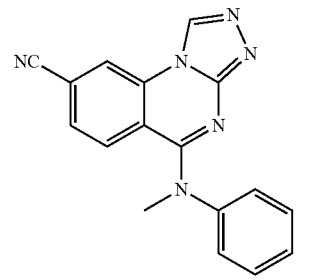 |
| 94 | 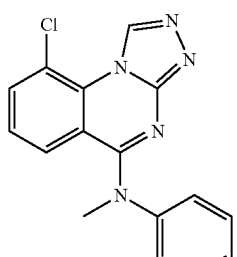 |

TABLE 1E-continued
Compounds
| Ex. | Chemical Structure |
|---|---|
| 95 | 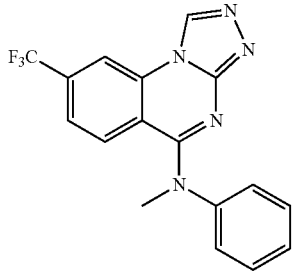 |
| 96 | 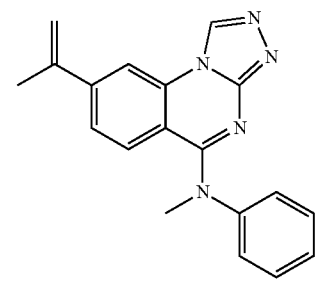 [SMILES: C=C(C)c1ccc2c(N(C)c3ccccc3)nc3nncn3c2c1] |
| 97 | 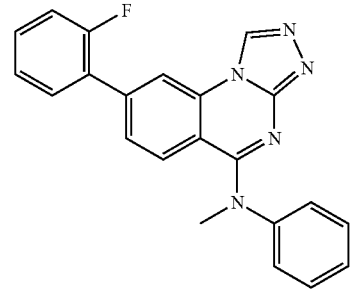 |
| 98 | 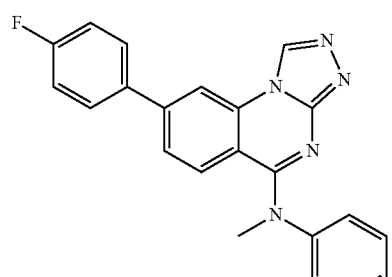 |
| 99 | 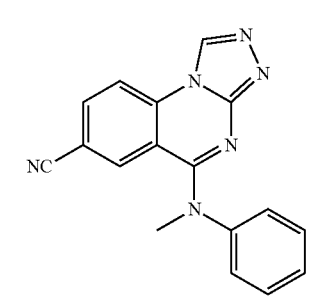 [SMILES: CN(c1ccccc1)c1nc2nncn2c2ccc(C#N)cc12] |
TABLE 1E-continued
Compounds
| Ex. | Chemical Structure |
|---|---|
| 100 | 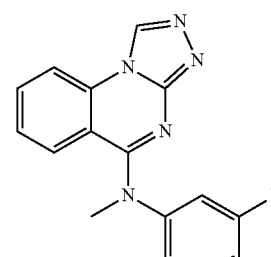 |
| 101 | 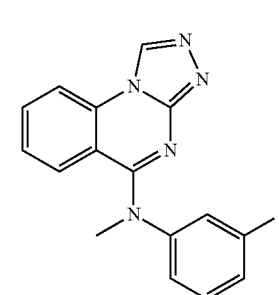 |
| 102 | 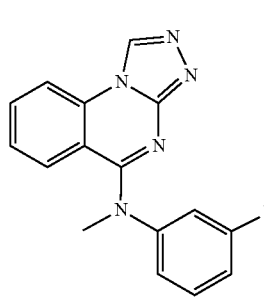 |
| 103 | 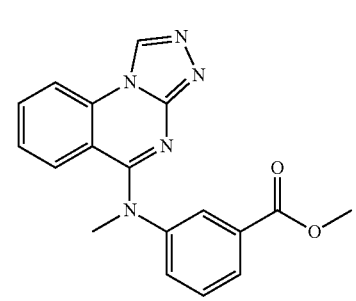 |
| 104 | 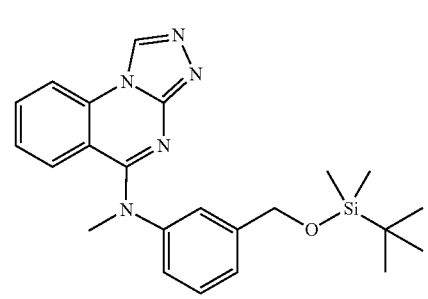 [SMILES: CN(c1cccc(CO[Si](C)(C)C(C)(C)C)c1)c1nc2nncn2c2ccccc12] |

TABLE 1E-continued

Compounds

| Ex. | Chemical Structure |
|---|---|
| 105 | 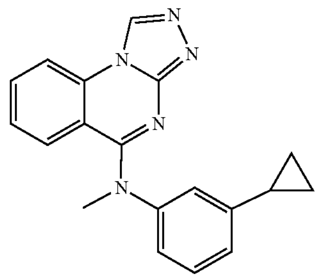 |
| 106 | 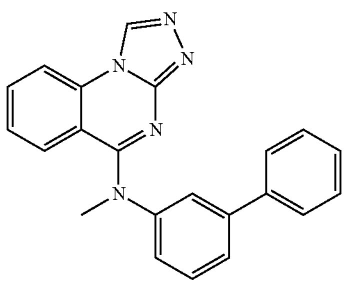 [SMILES: CN(c1cccc(-c2ccccc2)c1)c1nc2nncn2c2ccccc12] |
| 107 | 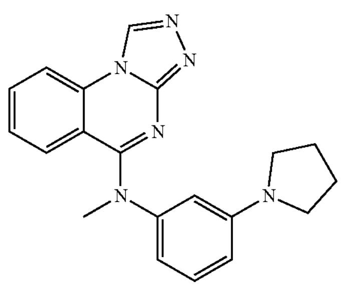 [SMILES: CN(c1cccc(N2CCCC2)c1)c1nc2nncn2c2ccccc12] |
| 108 | 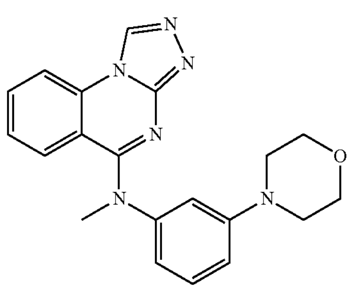 |
| 109 | 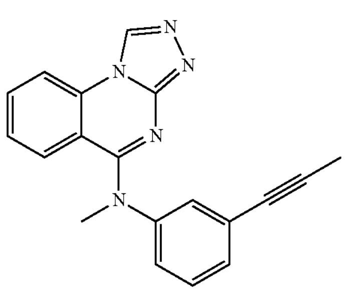 |
| 110 | |
| 111 | |
| 112 | |
| 113 | |

TABLE 1F

| Ex. | Chemical Structure |
|---|---|
| 114 | 2-methoxyphenyl-substituted [1,2,4]triazolo[4,3-a]quinazoline with N-methyl-N-phenylamine |
| 115 | 3-hydroxypropynyl-substituted [1,2,4]triazolo[4,3-a]quinazoline with N-methyl-N-phenylamine |
| 116 | 3-fluorophenyl-substituted [1,2,4]triazolo[4,3-a]quinazoline with N-methyl-N-phenylamine |
| 117 | formyl-substituted [1,2,4]triazolo[4,3-a]quinazoline with N-methyl-N-phenylamine |
| 118 | carboxy-substituted [1,2,4]triazolo[4,3-a]quinazoline with N-methyl-N-phenylamine |
| 119 | nitro-substituted [1,2,4]triazolo[4,3-a]quinazoline with N-methyl-N-(3-phenylphenyl)amine |
| 120 | [1,2,4]triazolo[4,3-a]quinazoline with N-methyl-N-(4'-fluorobiphenyl-3-yl)amine |
| 121 | [1,2,4]triazolo[4,3-a]quinazoline with N-methyl-N-(3-(furan-2-yl)phenyl)amine |
| 122 | [1,2,4]triazolo[4,3-a]quinazoline with N-methyl-N-(3-formylphenyl)amine |
| 123 | ethyl-substituted [1,2,4]triazolo[4,3-a]quinazoline with N-methyl-N-phenylamine |

TABLE 1F-continued

Compounds

| Ex. | Chemical Structure |
|---|---|
| 124 | 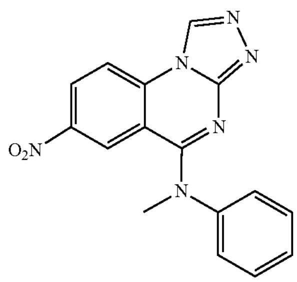 |
| 125 | 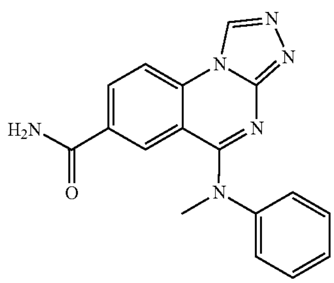 |
| 126 | 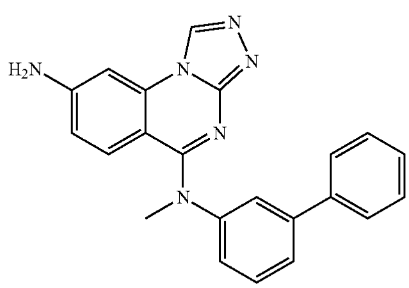 |
| 127 | 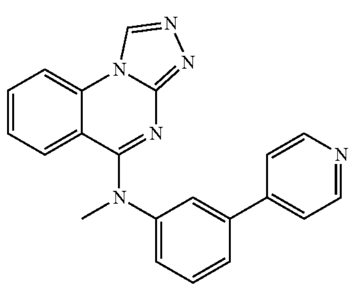 |
| 128 | 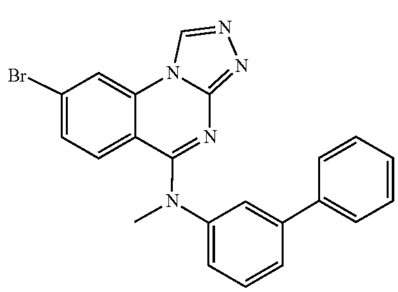 |
| 129 | |
| 130 | |
| 131 | |
| 132 | |
| 133 | |

TABLE 1F-continued

Compounds

| Ex. | Chemical Structure |
|---|---|
| 134 | 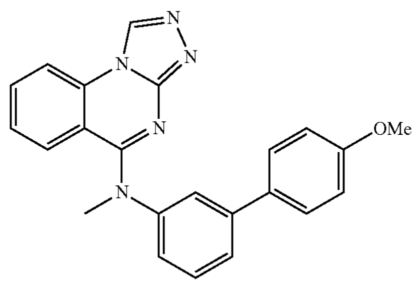 [SMILES: COc1ccc(-c2cccc(N(C)c3nc4nncn4c4ccccc34)c2)cc1] |
| 135 | 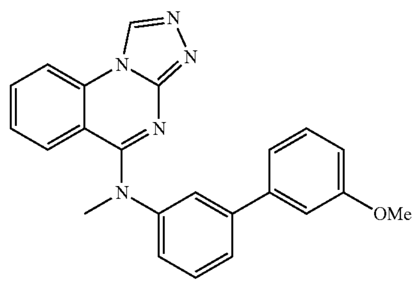 [SMILES: COc1cccc(-c2cccc(N(C)c3nc4nncn4c4ccccc34)c2)c1] |
| 136 | 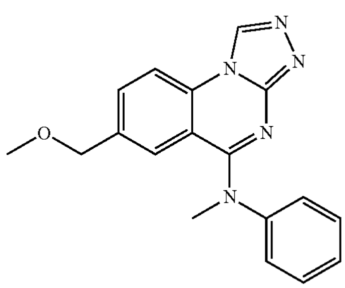 [SMILES: COCc1ccc2c(c1)c(N(C)c1ccccc1)nc1nncn12] |
| 137 | 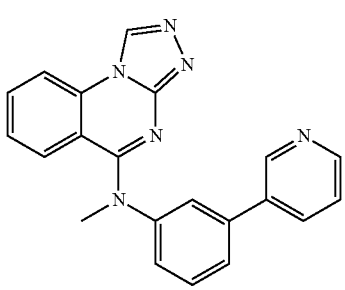 |

TABLE 1G

Compounds

| Ex. | Chemical Structure |
|---|---|
| 138 | 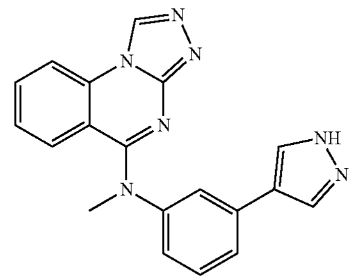 |
| 139 | 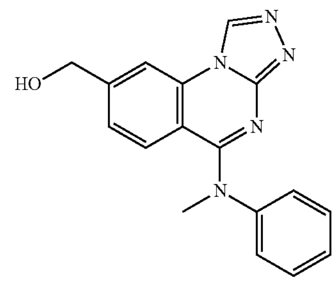 |
| 140 | 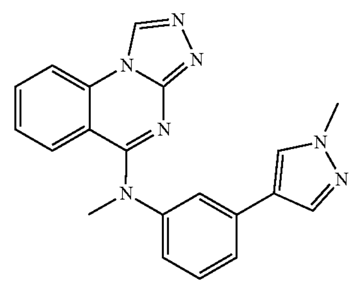 |
| 141 | 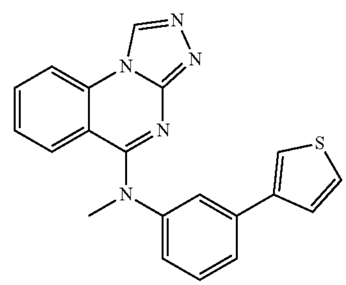 [SMILES: CN(c1cccc(-c2ccsc2)c1)c1nc2nncn2c2ccccc12] |
| 142 | 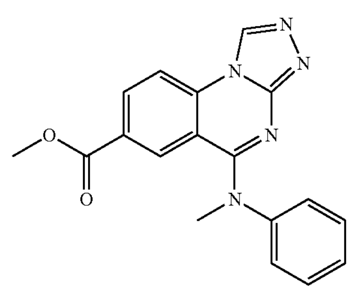 |

TABLE 1G-continued

Compounds

| Ex. | Chemical Structure |
|-----|-------------------|
| 143 | 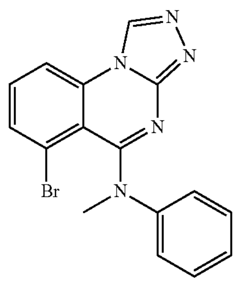 |
| 144 | 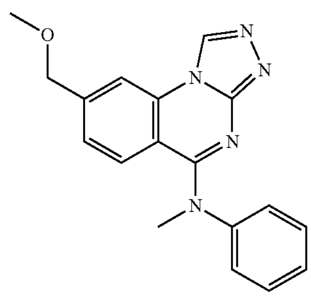 [SMILES: COCc1ccc2c(N(C)c3ccccc3)nc3nncn3c2c1] |
| 145 | 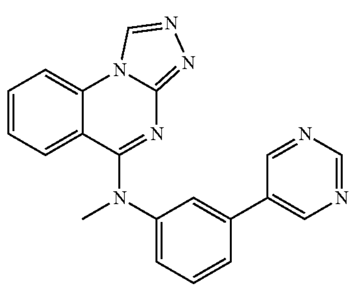 [SMILES: CN(c1cccc(-c2cncnc2)c1)c1nc2nncn2c2ccccc12] |
| 146 | 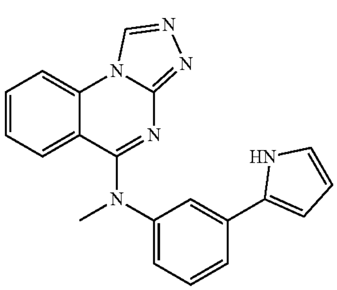 [SMILES: CN(c1cccc(-c2ccc[nH]2)c1)c1nc2nncn2c2ccccc12] |
| 147 | 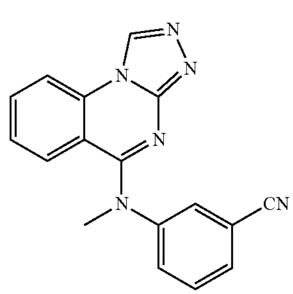 [SMILES: CN(c1cccc(C#N)c1)c1nc2nncn2c2ccccc12] |
| 148 | |
| 149 | |
| 150 | |
| 151 | |
| 152 | |

TABLE 1G-continued
Compounds
| Ex. | Chemical Structure |
|---|---|
| 153 | 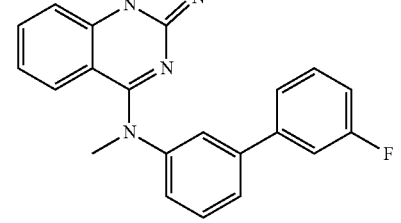 |
| 154 | 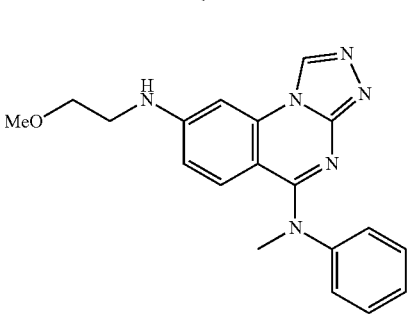 |
| 155 | 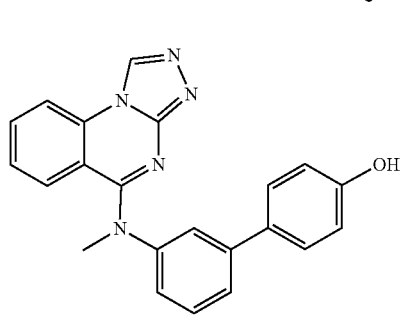 |
| 156 | 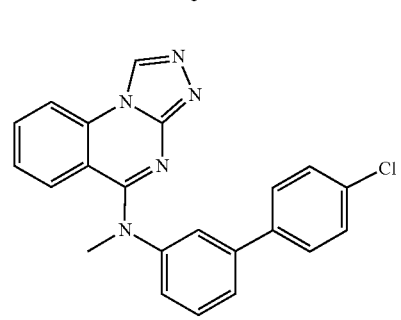 |
| 157 | 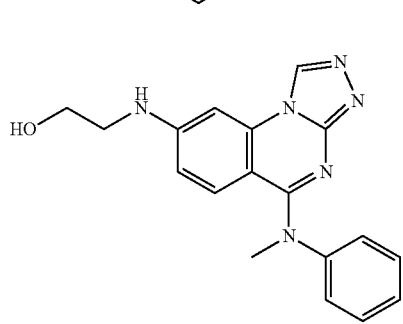 |
TABLE 1G-continued
Compounds
| Ex. | Chemical Structure |
|---|---|
| 158 | 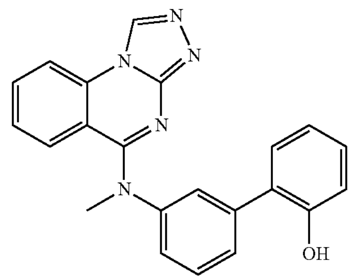 |
| 159 | 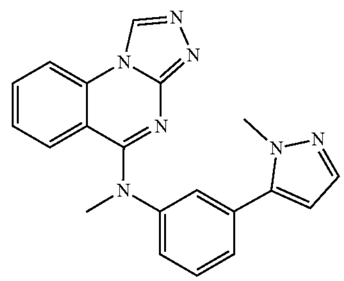 |
| 160 | 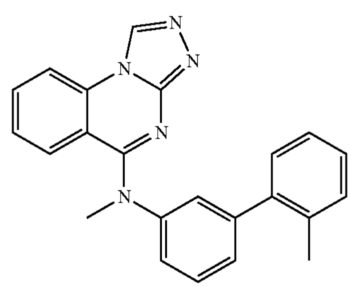 |
| 161 | 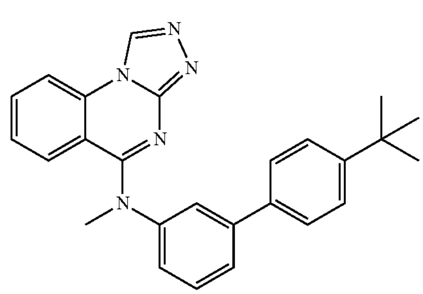 [SMILES: CN(c1cccc(-c2ccc(C(C)(C)C)cc2)c1)c1nc2nncn2c2ccccc12] |

TABLE 1H

| Ex. | Chemical Structure |
|---|---|
| 162 | 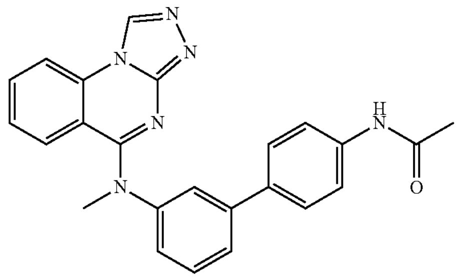 |
| 163 | 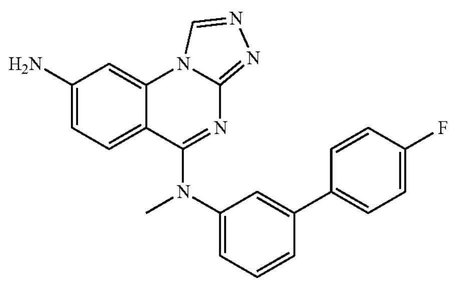 |
| 164 | 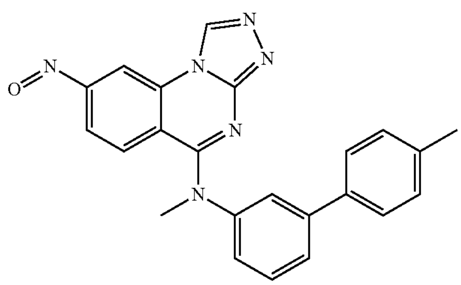 |
| 165 | 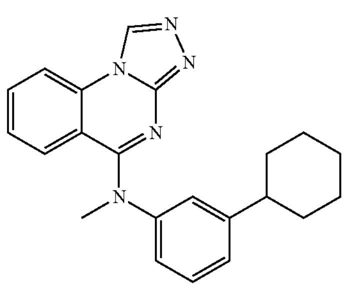 |
| 166 | 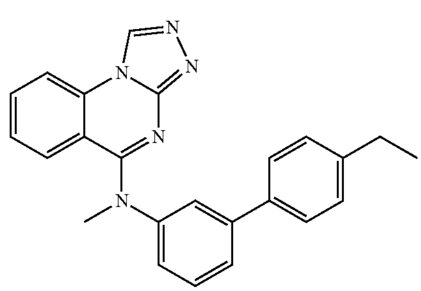 |

TABLE 1H-continued

| Ex. | Chemical Structure |
|---|---|
| 167 | 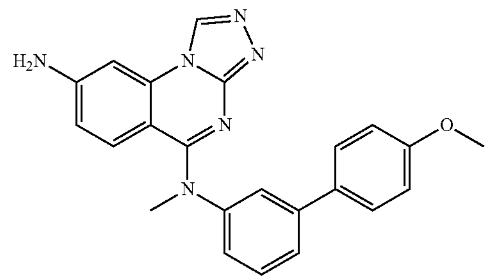 |
| 168 | 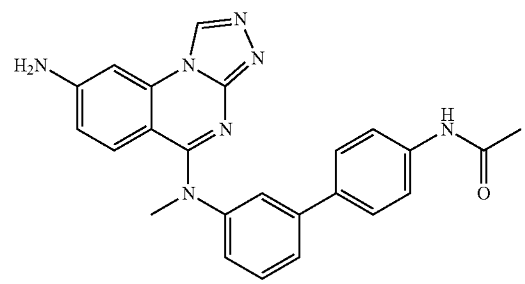 |
| 169 | 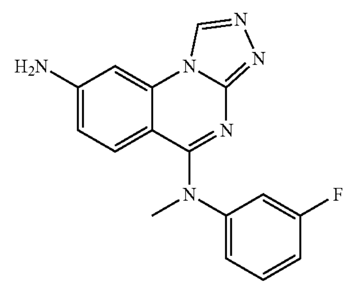 |
| 170 | 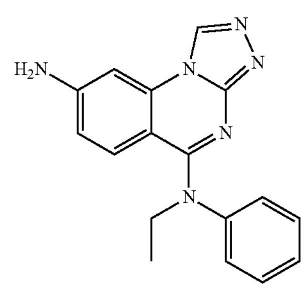 |
| 171 | 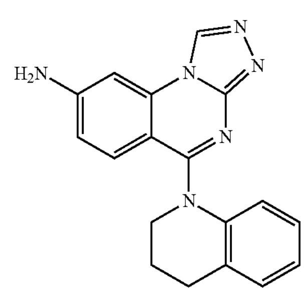 |

TABLE 1H-continued

Compounds

| Ex. | Chemical Structure |
|---|---|
| 172 | 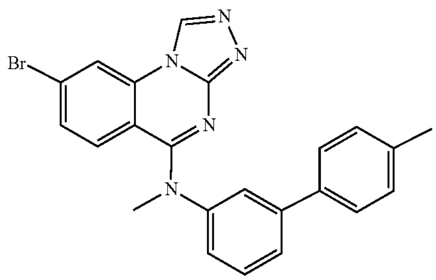 |
| 173 | 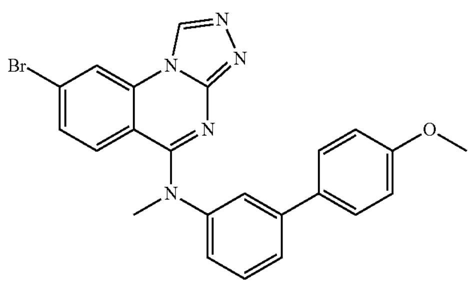 |
| 174 | 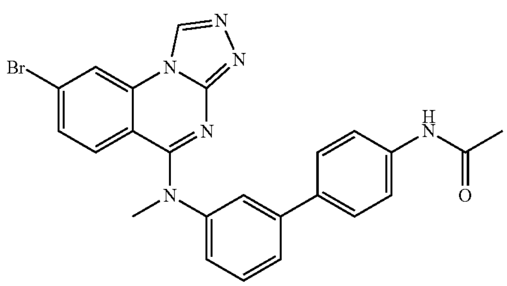 |
| 175 | 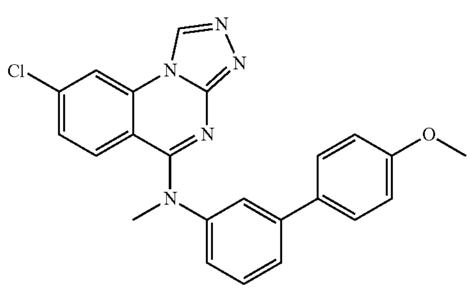 [SMILES: COc1ccc(-c2cccc(N(C)c3nc4nncn4c4cc(Cl)ccc34)c2)cc1] |
| 176 | 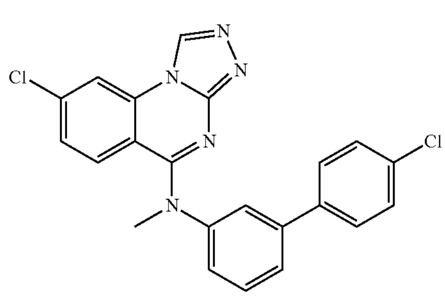 |
| 177 | 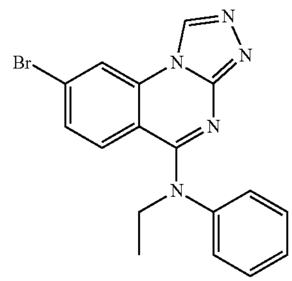 [SMILES: CCN(c1ccccc1)c1nc2nncn2c2cc(Br)ccc12] |
| 178 | 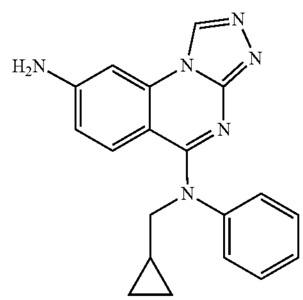 |
| 179 | 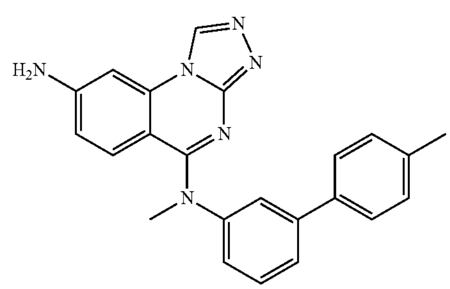 |
| 180 | 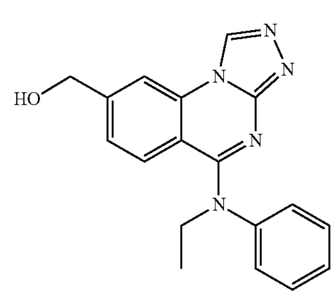 [SMILES: CCN(c1ccccc1)c1nc2nncn2c2cc(CO)ccc12] |

TABLE 1I
| Ex. | Chemical Structure |
|---|---|
| 181 | 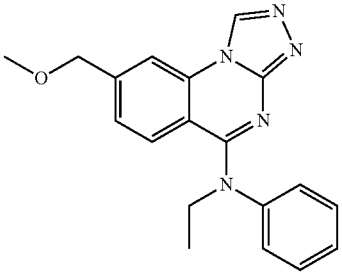 |
| 182 | 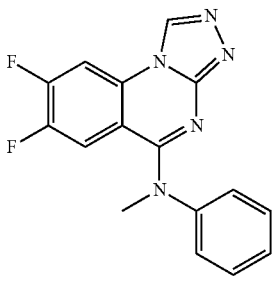 |
| 183 | 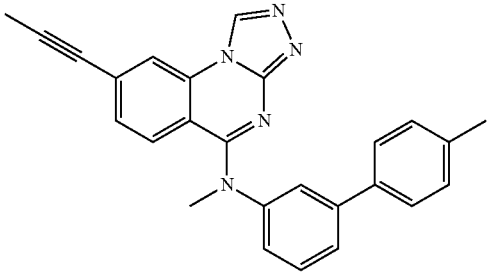 [SMILES: CC#Cc1ccc2c(N(C)c3cccc(-c4ccc(C)cc4)c3)nc3nncn3c2c1] |
| 184 | 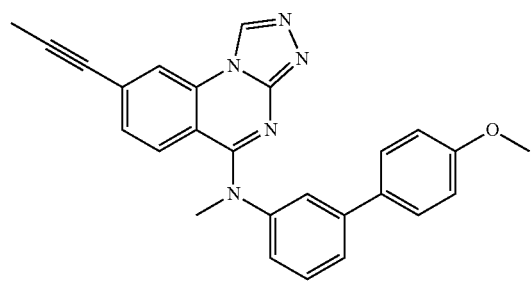 [SMILES: CC#Cc1ccc2c(N(C)c3cccc(-c4ccc(OC)cc4)c3)nc3nncn3c2c1] |
| 185 | 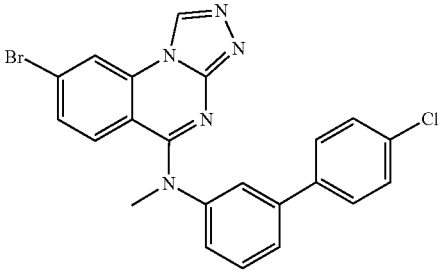 |
TABLE 1I-continued
| Ex. | Chemical Structure |
|---|---|
| 186 | 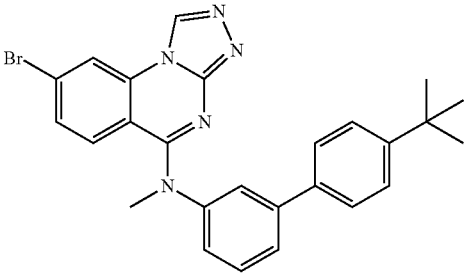 |
| 187 | 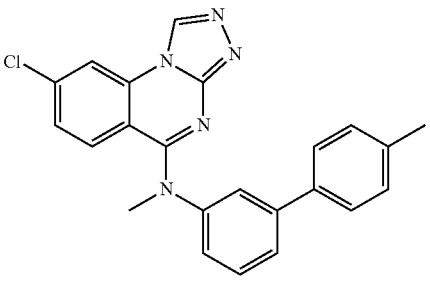 [SMILES: Cc1ccc(-c2cccc(N(C)c3nc4nncn4c4cc(Cl)ccc34)c2)cc1] |
| 188 | 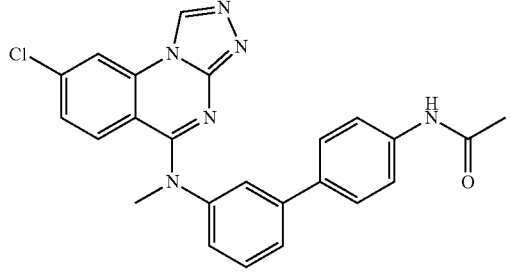 |
| 189 | 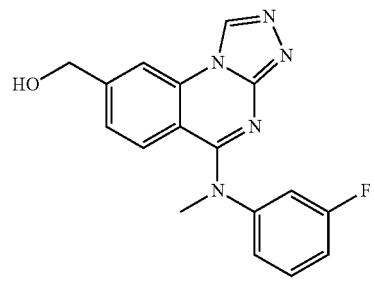 [SMILES: CN(c1cccc(F)c1)c1nc2nncn2c2cc(CO)ccc12] |
| 190 | 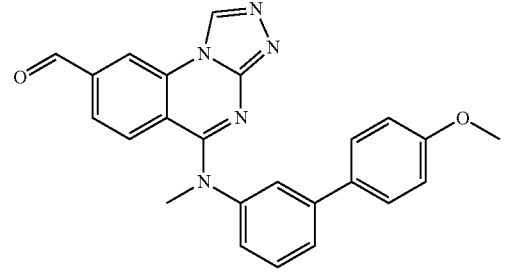 |

TABLE 1I-continued
Compounds
| Ex. | Chemical Structure |
|---|---|
| 191 | 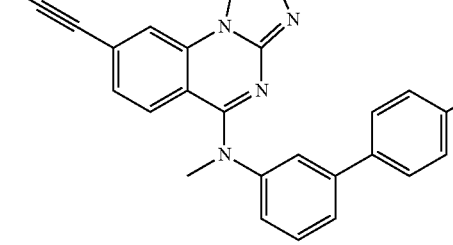 |
| 192 | 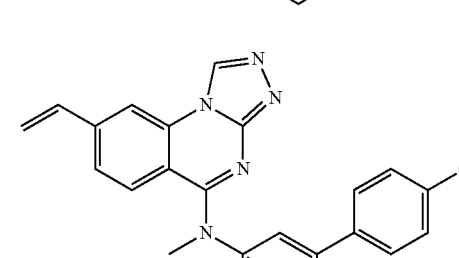 |
| 193 | 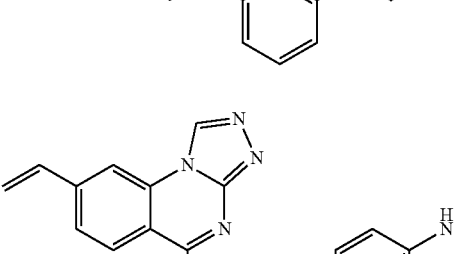 |
| 194 | 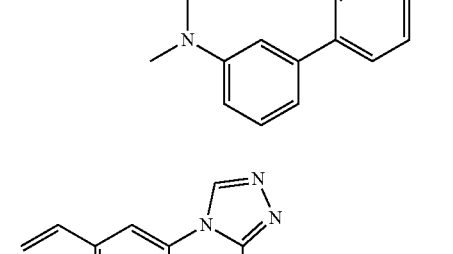 |
| 195 | 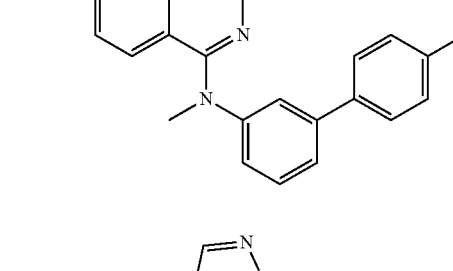 |**
TABLE 1I-continued
Compounds
| Ex. | Chemical Structure |
|---|---|
| 196 | 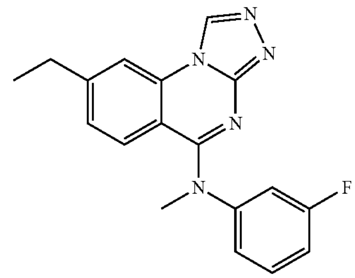 |
| 197 | 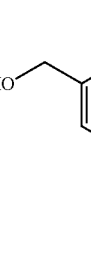 |
| 198 | 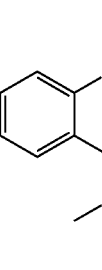 |
| 199 | 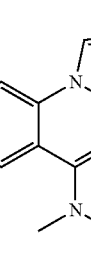 |
TABLE 1J
Compounds
| Ex. | Chemical Structure |
|---|---|
| 200 | 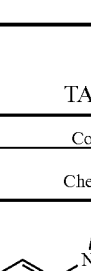 |

TABLE 1J-continued
Compounds
| Ex. | Chemical Structure |
|---|---|
| 201 | 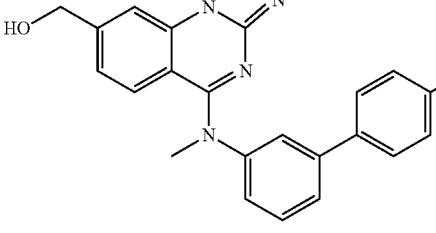 |
| 202 | 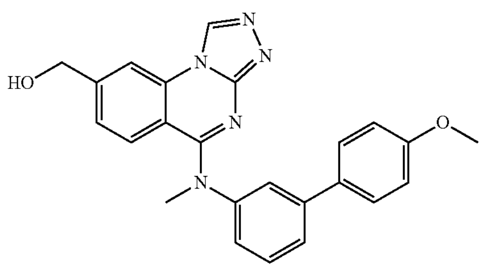 [SMILES: COc1ccc(-c2cccc(N(C)c3nc4nncn4c4cc(CO)ccc34)c2)cc1] |
| 203 | 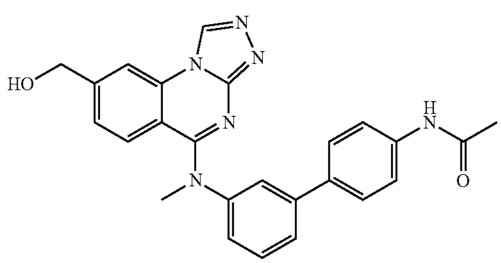 |
| 204 | 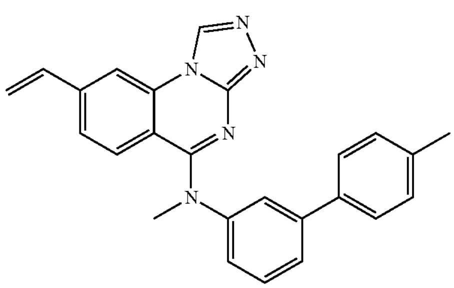 |
| 205 | 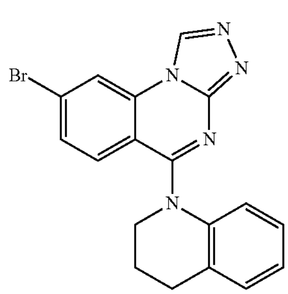 [SMILES: Brc1ccc2c(N3CCCc4ccccc43)nc3nncn3c2c1] |
| 206 | 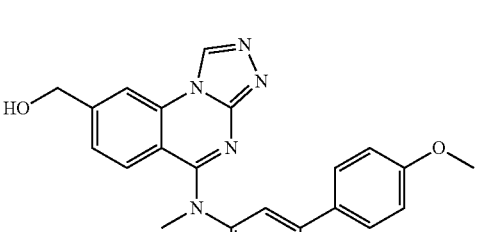 |
| 207 | |
| 208 | |
| 209 | |
| 210 | |

TABLE 1J-continued

Compounds

| Ex. | Chemical Structure |
|---|---|
| 211 | 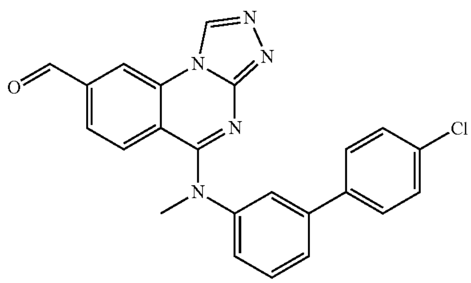 [SMILES: CN(c1cccc(-c2ccc(Cl)cc2)c1)c1nc2nncn2c2cc(C=O)ccc12] |
| 212 | 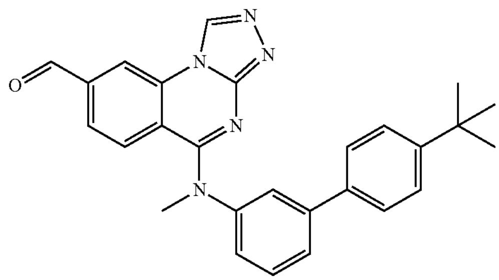 |
| 213 | 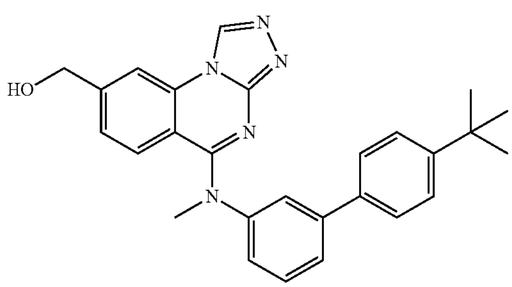 |
| 214 | 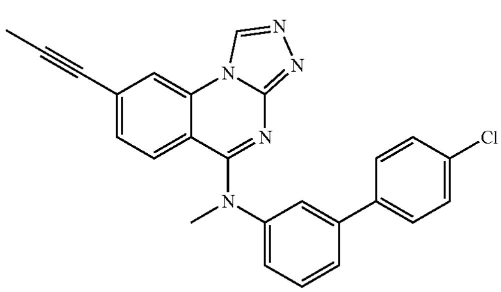 [SMILES: CC#Cc1ccc2c(N(C)c3cccc(-c4ccc(Cl)cc4)c3)nc3nncn3c2c1] |
| 215 | 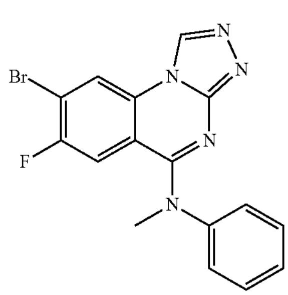 |
| 216 | |
| 217 | |
| 218 | |
| 219 | |
| 220 | |

TABLE 2A

| Ex. | Chemical Structure |
|---|---|
| 221 | 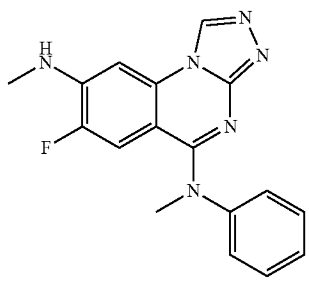 |
| 222 | 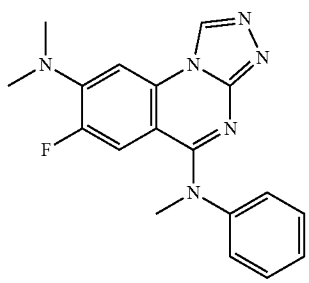 |
| 223 | 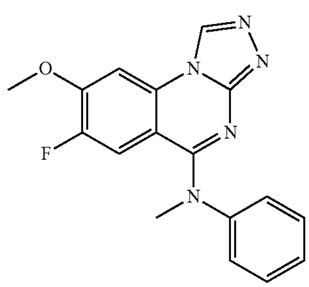 [SMILES: COc1cc2c(cc1F)c(N(C)c1ccccc1)nc1nncn12] |
| 224 | 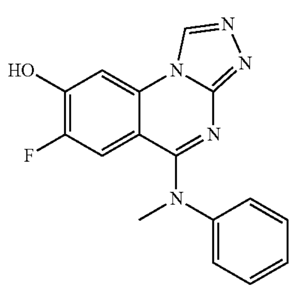 [SMILES: CN(c1ccccc1)c1nc2nncn2c2cc(O)c(F)cc12] |
| 225 | 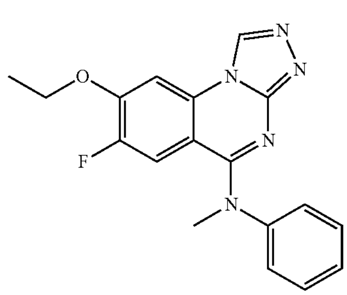 [SMILES: CCOc1cc2c(cc1F)c(N(C)c1ccccc1)nc1nncn12] |

TABLE 2A-continued

| Ex. | Chemical Structure |
|---|---|
| 226 | 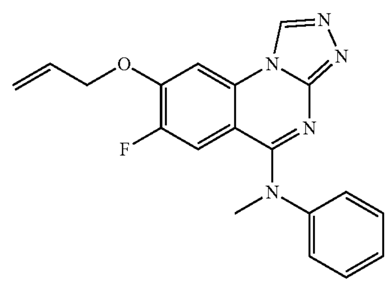 |
| 227 | 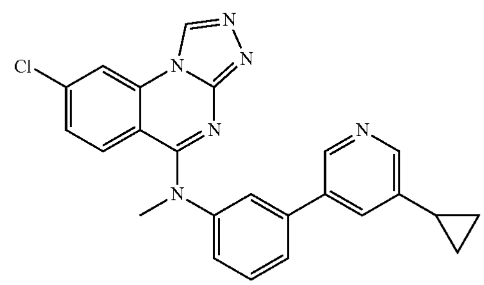 [SMILES: CN(c1cccc(-c2cncc(C3CC3)c2)c1)c1nc2nncn2c2cc(Cl)ccc12] |
| 228 | 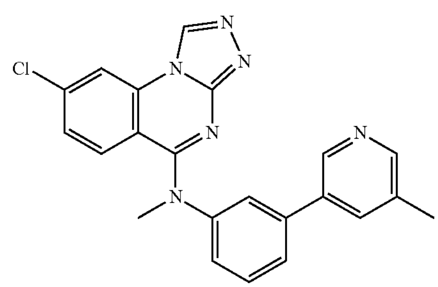 [SMILES: Cc1cncc(-c2cccc(N(C)c3nc4nncn4c4cc(Cl)ccc34)c2)c1] |
| 229 | 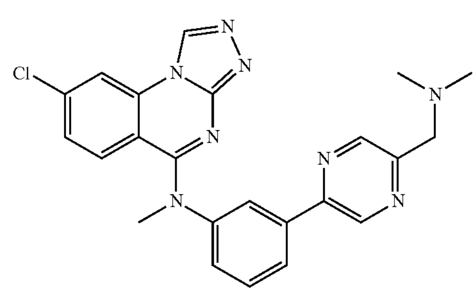 [SMILES: CN(C)Cc1cnc(-c2cccc(N(C)c3nc4nncn4c4cc(Cl)ccc34)c2)cn1] |
| 230 | 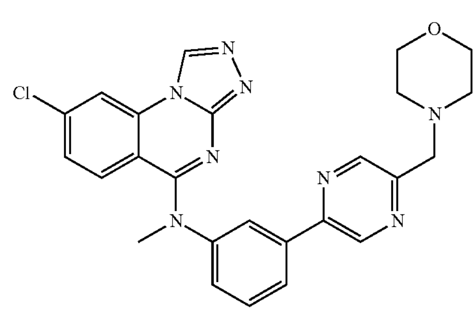 |

TABLE 2A-continued

| Ex. | Chemical Structure |
|---|---|
| 231 | (structure) |
| 232 | (structure) |
| 233 | (structure) |
| 234 | (structure) |
| 235 | (structure) |
| 236 | (structure) |
| 237 | (structure) |
| 238 | (structure) |
| 239 | (structure) |
| 240 | (structure) |

TABLE 2A-continued

| Ex. | Chemical Structure |
|-----|-------------------|
| 241 | (structure) |
| 242 | (structure) |
| 243 | (structure) |
| 244 | (structure) |
| 245 | (structure) |
| 246 | (structure) |
| 247 | (structure) |
| 248 | (structure) |
| 249 | (structure) |

TABLE 2B

| Ex. | Chemical Structure |
|---|---|
| 250 | 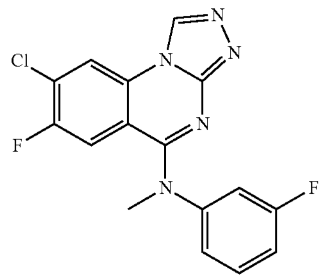 [SMILES: CN(c1cccc(F)c1)c1nc2nncn2c2cc(Cl)c(F)cc12] |
| 251 | 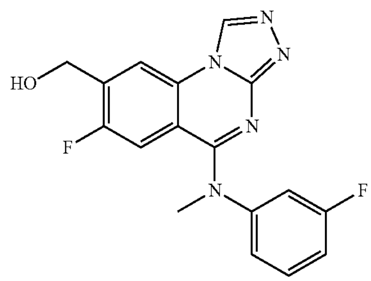 |
| 252 | 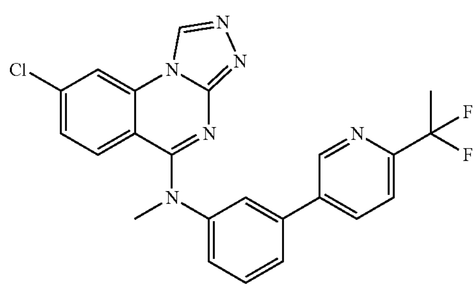 |
| 253 | 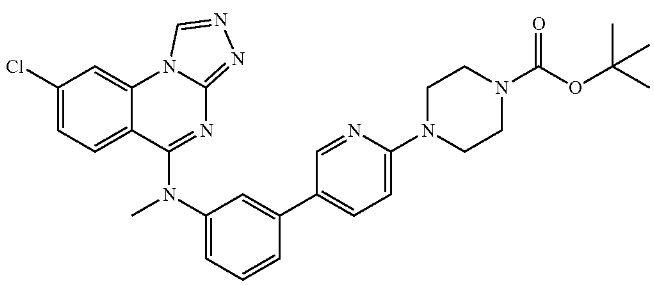 [SMILES: CN(c1cccc(-c2ccc(N3CCN(C(=O)OC(C)(C)C)CC3)nc2)c1)c1nc2nncn2c2cc(Cl)ccc12] |
| 254 | 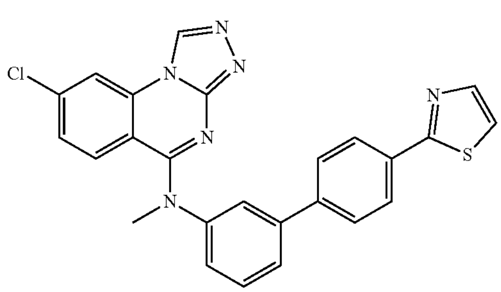 [SMILES: CN(c1cccc(-c2ccc(-c3nccs3)cc2)c1)c1nc2nncn2c2cc(Cl)ccc12] |

TABLE 2B-continued
| Compounds | |
|---|---|
| Ex. | Chemical Structure |
| 255 | 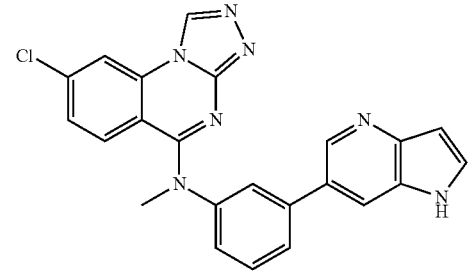 |
| 256 | 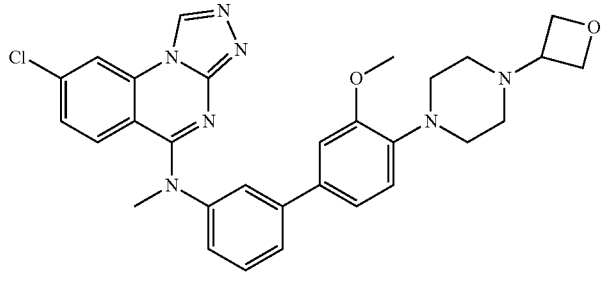 [SMILES: COc1cc(-c2cccc(N(C)c3nc4nncn4c4cc(Cl)ccc34)c2)ccc1N1CCN(C2COC2)CC1] |
| 257 | 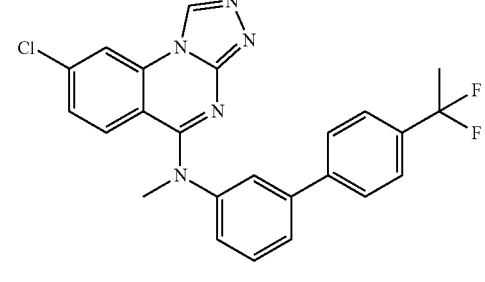 |
| 258 | 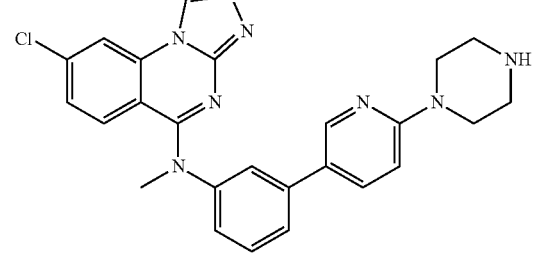 |
| 259 | 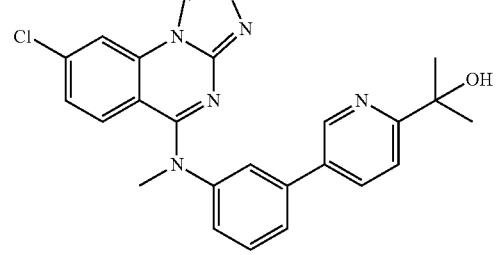 |

TABLE 2B-continued

| Ex. | Chemical Structure |
|---|---|
| 260 | 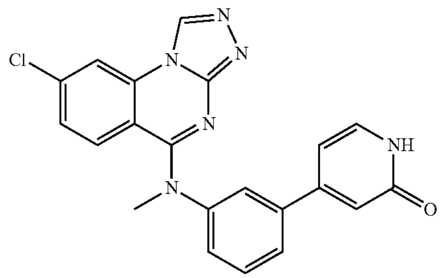 |
| 261 | 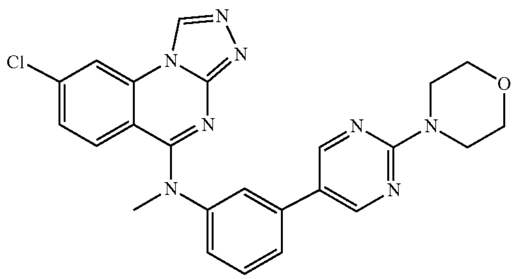 |
| 262 | 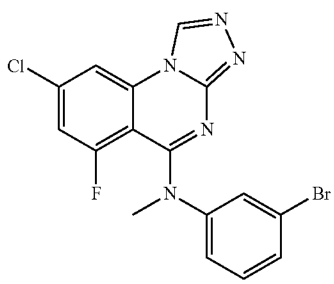 [SMILES: CN(c1cccc(Br)c1)c1nc2nncn2c2cc(Cl)cc(F)c12] |
| 263 | 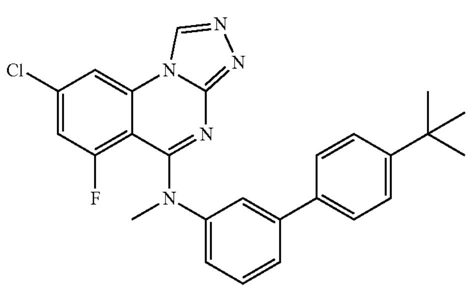 |
| 264 | 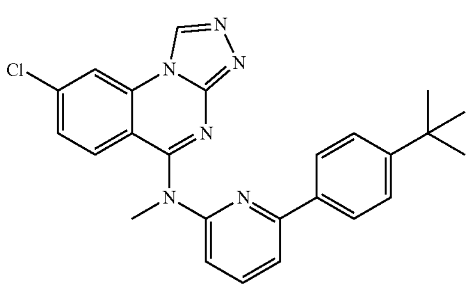 |

TABLE 2B-continued

| Ex. | Chemical Structure |
|---|---|
| 265 | 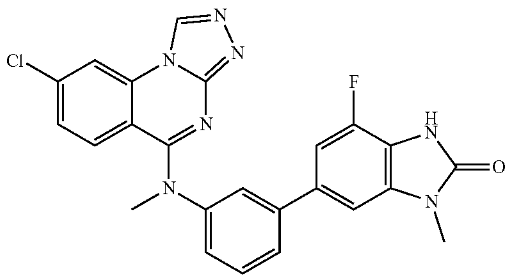 |
| 266 | 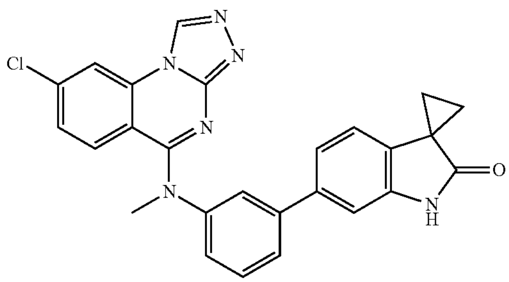 [SMILES: CN(c1cccc(-c2ccc3c(c2)NC(=O)C32CC2)c1)c1nc2nncn2c2cc(Cl)ccc12] |
| 267 | 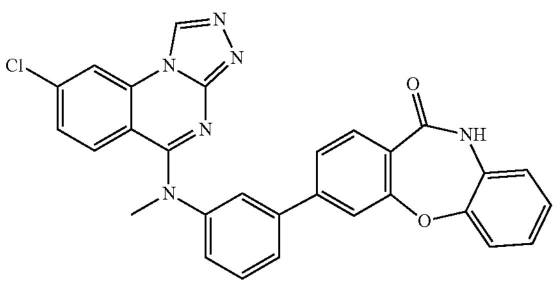 |
| 268 | 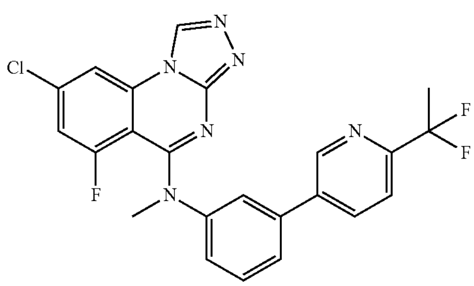 |
| 269 | 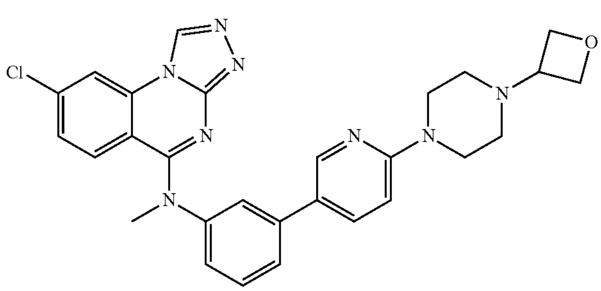 [SMILES: CN(c1cccc(-c2ccc(N3CCN(C4COC4)CC3)nc2)c1)c1nc2nncn2c2cc(Cl)ccc12] |

TABLE 2B-continued

| Ex. | Chemical Structure |
|---|---|
| 270 | 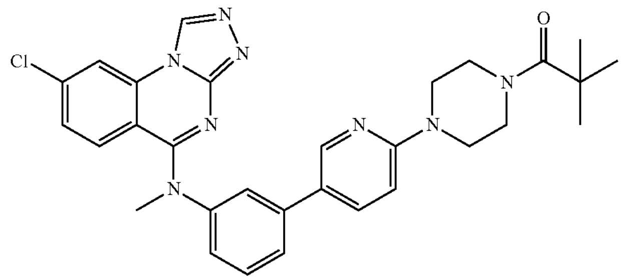 [SMILES: CN(c1cccc(-c2ccc(N3CCN(C(=O)C(C)(C)C)CC3)nc2)c1)c1nc2nncn2c2cc(Cl)ccc12] |
| 271 | 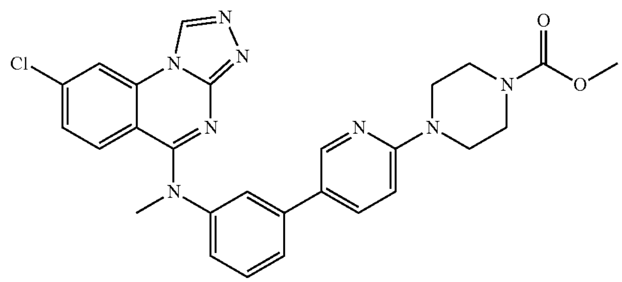 [SMILES: COC(=O)N1CCN(c2ccc(-c3cccc(N(C)c4nc5nncn5c5cc(Cl)ccc45)c3)cn2)CC1] |
| 272 | 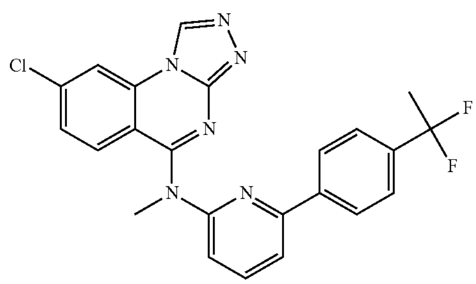 |
| 273 | 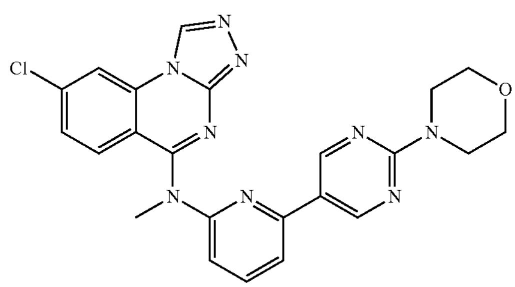 [SMILES: CN(c1cccc(-c2cnc(N3CCOCC3)nc2)n1)c1nc2nncn2c2cc(Cl)ccc12] |
| 274 | 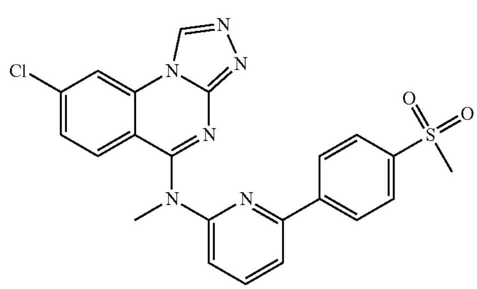 [SMILES: CN(c1cccc(-c2ccc(S(C)(=O)=O)cc2)n1)c1nc2nncn2c2cc(Cl)ccc12] |

TABLE 2B-continued

| Ex. | Chemical Structure |
|---|---|
| 275 | 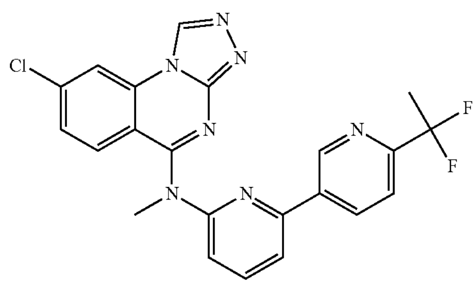 |
| 276 | 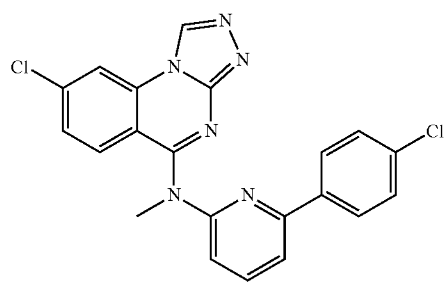 |
| 277 | 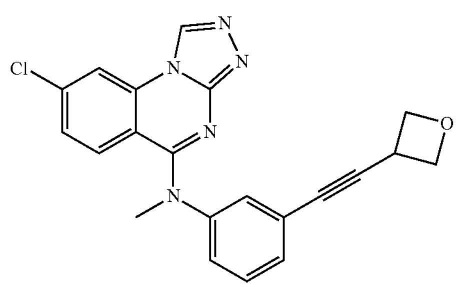 |
| 278 | 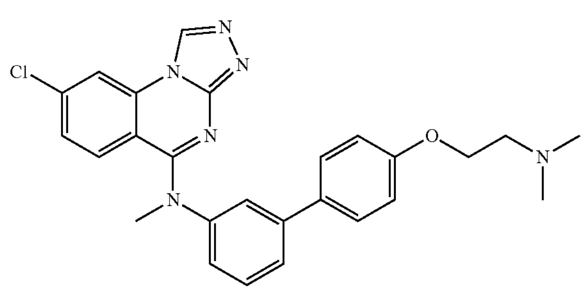 |
| 279 | 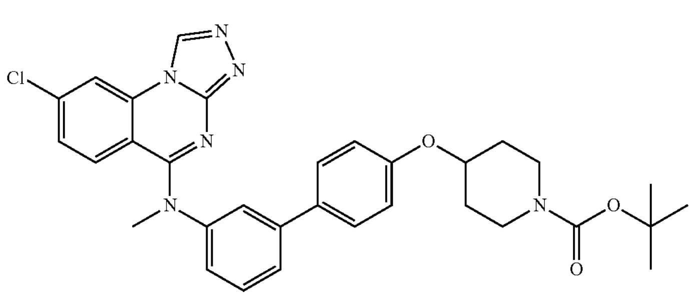 [SMILES: CN(c1cccc(-c2ccc(OC3CCN(C(=O)OC(C)(C)C)CC3)cc2)c1)c1nc2nncn2c2cc(Cl)ccc12] |

TABLE 2C

| Ex. | Chemical Structure |
|---|---|
| 280 | 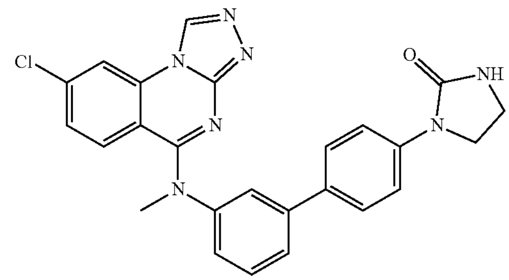 [SMILES: CN(c1cccc(-c2ccc(N3CCNC3=O)cc2)c1)c1nc2nncn2c2cc(Cl)ccc12] |
| 281 | 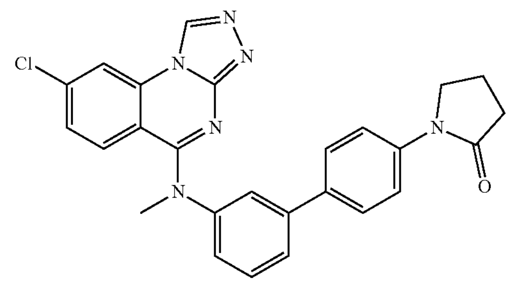 [SMILES: CN(c1cccc(-c2ccc(N3CCCC3=O)cc2)c1)c1nc2nncn2c2cc(Cl)ccc12] |
| 282 | 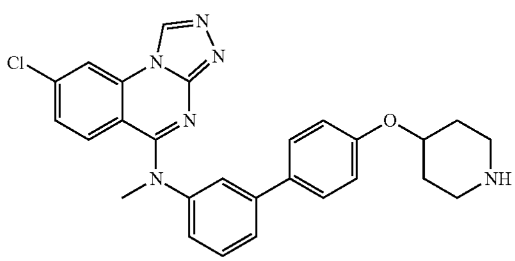 |
| 283 | 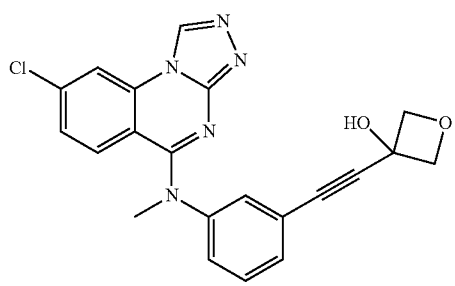 [SMILES: CN(c1cccc(C#CC2(O)COC2)c1)c1nc2nncn2c2cc(Cl)ccc12] |
| 284 | 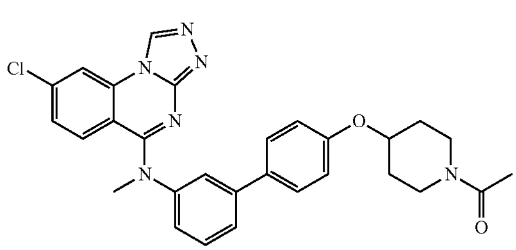 [SMILES: CC(=O)N1CCC(Oc2ccc(-c3cccc(N(C)c4nc5nncn5c5cc(Cl)ccc45)c3)cc2)CC1] |

TABLE 2C-continued

| Ex. | Chemical Structure |
|---|---|
| 285 | 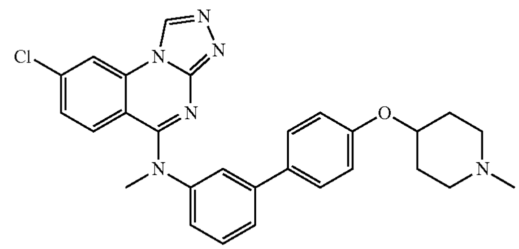 [SMILES: CN1CCC(Oc2ccc(-c3cccc(N(C)c4nc5nncn5c5cc(Cl)ccc45)c3)cc2)CC1] |
| 286 | 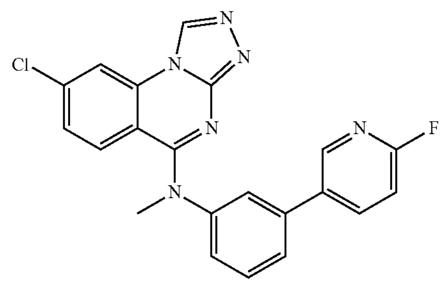 [SMILES: CN(c1cccc(-c2ccc(F)nc2)c1)c1nc2nncn2c2cc(Cl)ccc12] |
| 287 | 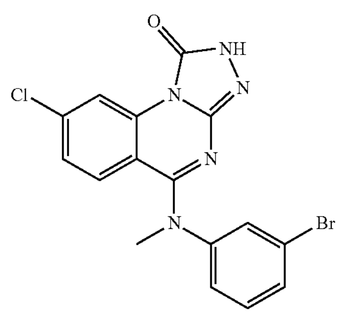 [SMILES: CN(c1cccc(Br)c1)c1nc2n[nH]c(=O)n2c2cc(Cl)ccc12] |
| 288 | 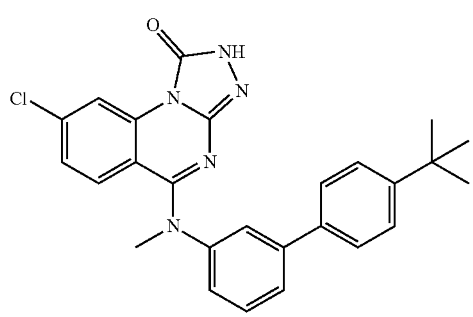 [SMILES: CN(c1cccc(-c2ccc(C(C)(C)C)cc2)c1)c1nc2n[nH]c(=O)n2c2cc(Cl)ccc12] |
| 289 | 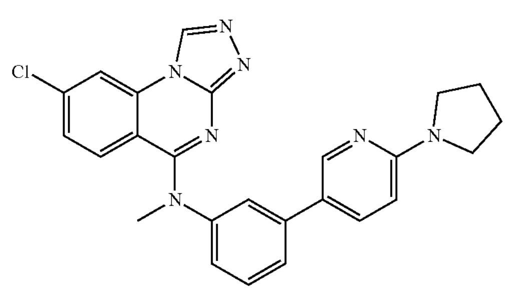 |

TABLE 2C-continued

Compounds

| Ex. | Chemical Structure |
|---|---|
| 290 | 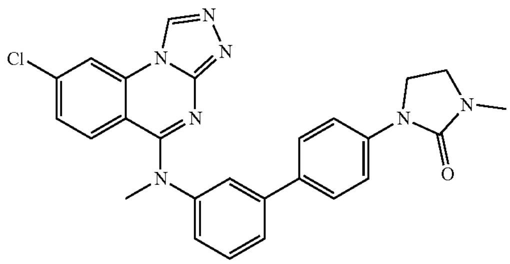 [SMILES: CN1CCN(c2ccc(-c3cccc(N(C)c4nc5nncn5c5cc(Cl)ccc45)c3)cc2)C1=O] |
| 291 | 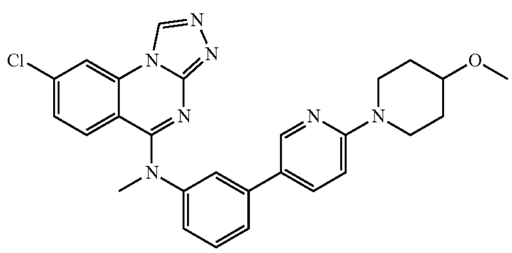 |
| 292 | 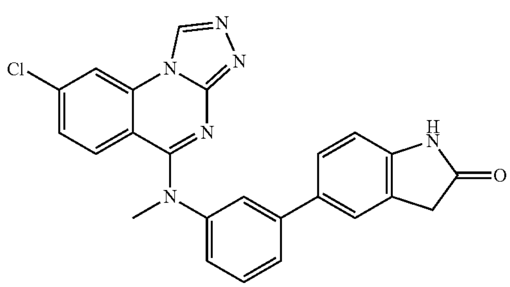 |
| 293 | 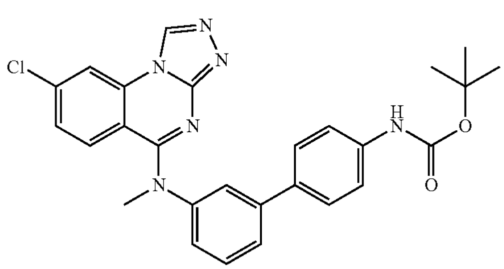 |
| 294 | 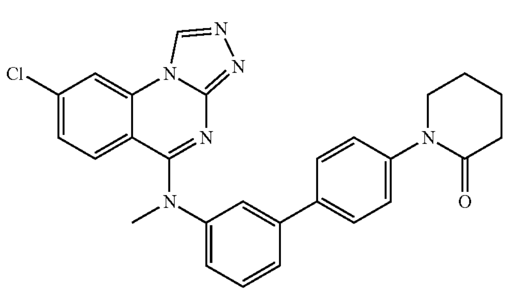 |
| 295 | |
| 296 | |
| 297 | |
| 298 | |
| 299 | |

TABLE 2C-continued
Compounds
| Ex. | Chemical Structure |
|---|---|
| 300 | 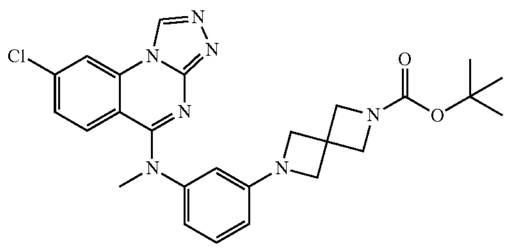 |
| 301 | 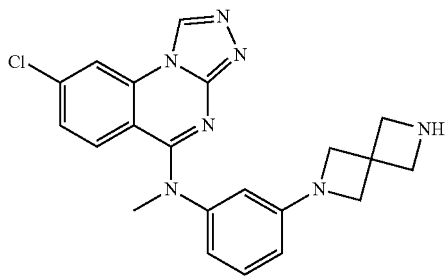 |
| 302 | 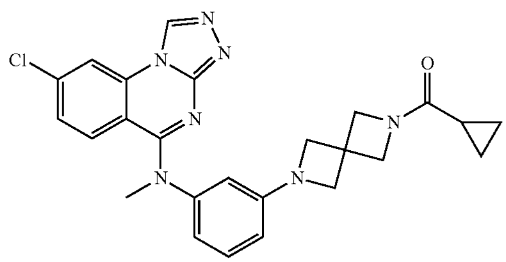 |
| 303 | 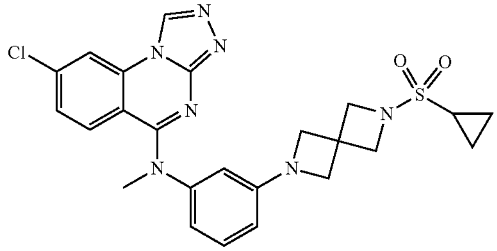 |
| 304 | 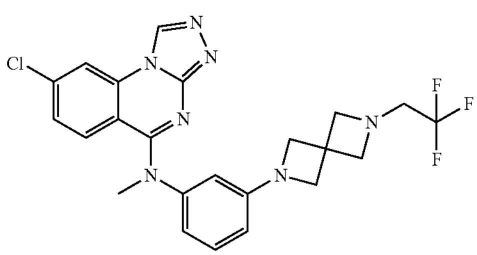 [SMILES: CN(c1cccc(N2CC3(CN(CC(F)(F)F)C3)C2)c1)c1nc2nncn2c2cc(Cl)ccc12] |
| 305 | 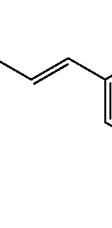 |
| 306 | |
| 307 | |
| 308 | |
| 309 | |

TABLE 2C-continued
Compounds
| Ex. | Chemical Structure |
|---|---|
| 310 | 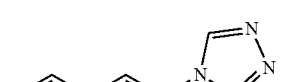 |
TABLE 2D
Compounds
| Ex. | Chemical Structure |
|---|---|
| 311 | |
| 312 | |
| 313 | |
| 314 | 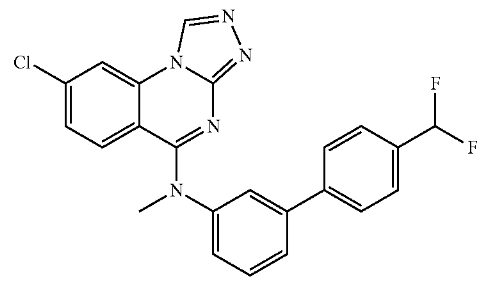 [SMILES: CN(c1cccc(-c2ccc(C(F)F)cc2)c1)c1nc2nncn2c2cc(Cl)ccc12] |
| 315 | 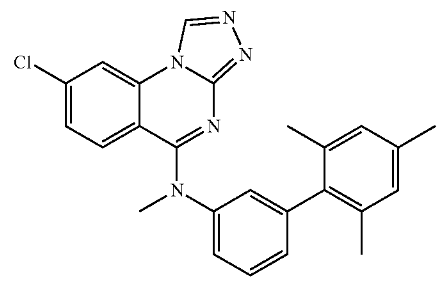 |
| 316 | 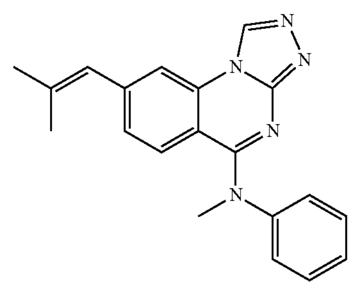 |
| 317 | 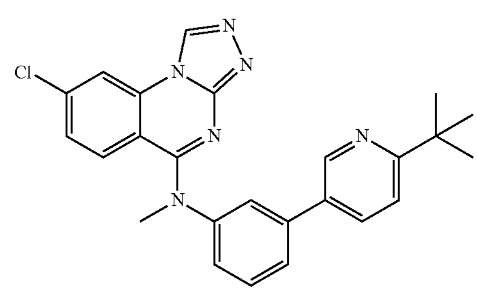 [SMILES: CN(c1cccc(-c2ccc(C(C)(C)C)nc2)c1)c1nc2nncn2c2cc(Cl)ccc12] |
| 318 | 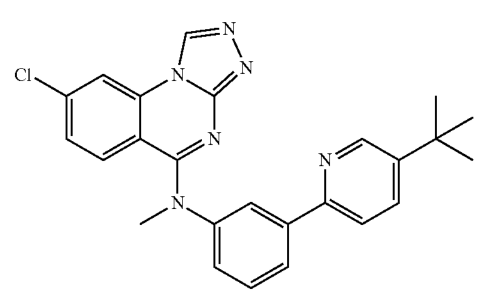 [SMILES: CN(c1cccc(-c2ccc(C(C)(C)C)cn2)c1)c1nc2nncn2c2cc(Cl)ccc12] |

TABLE 2D-continued
Compounds
| Ex. | Chemical Structure |
|---|---|
| 319 | 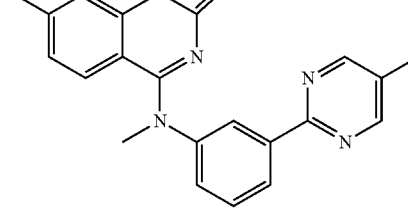 |
| 320 | 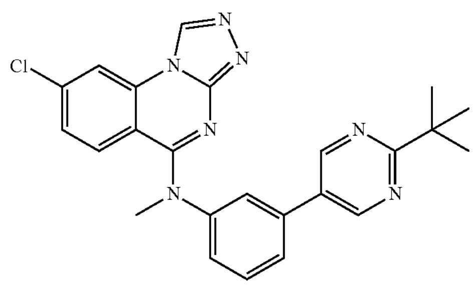 [SMILES: CN(c1cccc(-c2cnc(C(C)(C)C)nc2)c1)c1nc2nncn2c2cc(Cl)ccc12] |
| 321 | 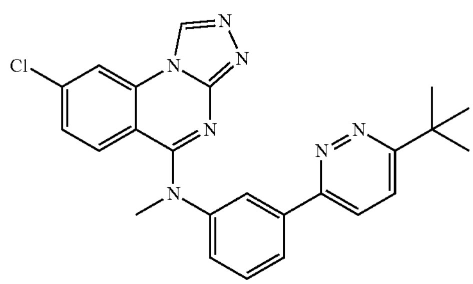 |
| 322 | 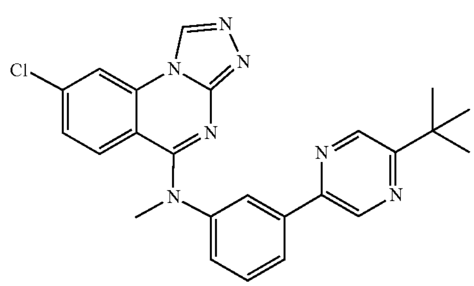 |
| 323 | 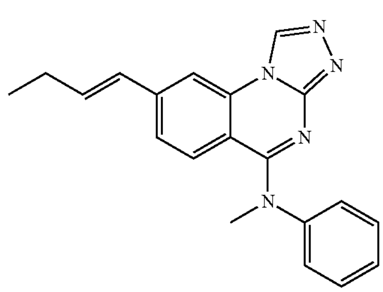 [SMILES: CC/C=C/c1ccc2c(N(C)c3ccccc3)nc3nncn3c2c1] |
| 324 | 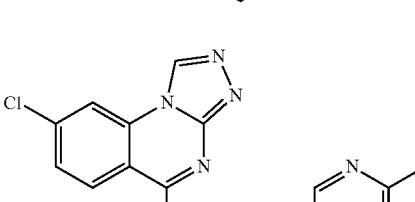 |
| 325 | |
| 326 | |
| 327 | |
| 328 | |

TABLE 2D-continued

Compounds

| Ex. | Chemical Structure |
|---|---|
| 329 | 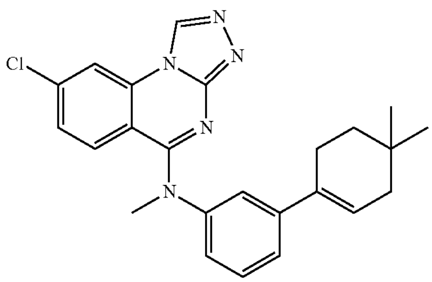 |
| 330 | 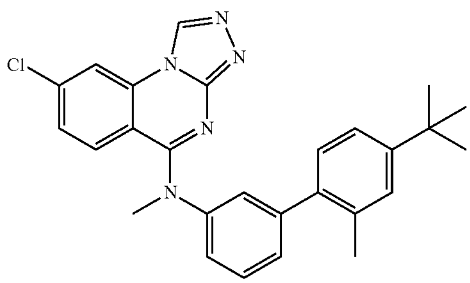 [SMILES: Cc1cc(C(C)(C)C)ccc1-c1cccc(N(C)c2nc3nncn3c3cc(Cl)ccc23)c1] |
| 331 | 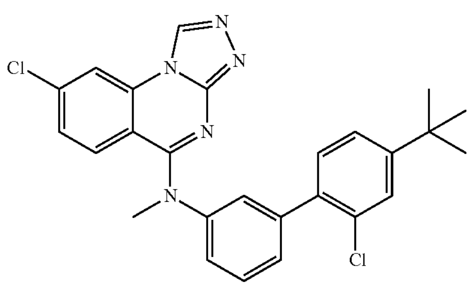 [SMILES: CN(c1cccc(-c2ccc(C(C)(C)C)cc2Cl)c1)c1nc2nncn2c2cc(Cl)ccc12] |
| 332 | 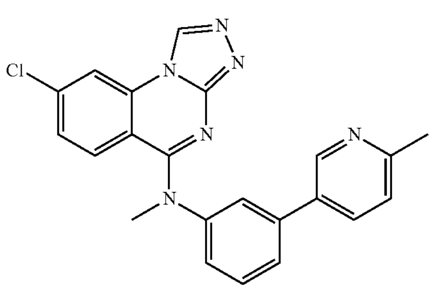 |
| 333 | 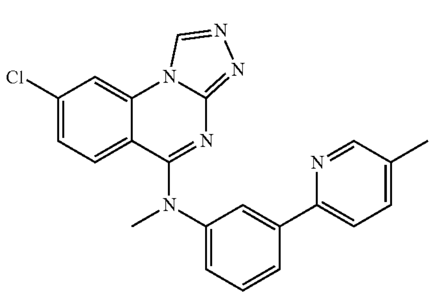 [SMILES: Cc1ccc(-c2cccc(N(C)c3nc4nncn4c4cc(Cl)ccc34)c2)nc1] |
| 334 | |
| 335 | |
| 336 | |
| 337 | |
| 338 | |

TABLE 2D-continued

| Ex. | Chemical Structure |
|---|---|
| 339 | 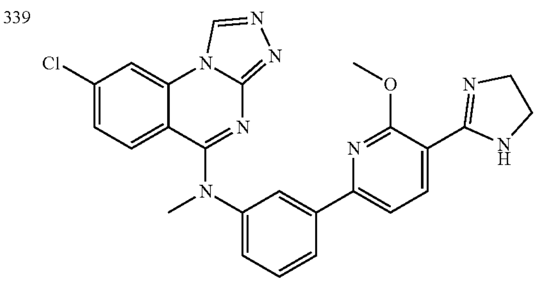 |
| 340 | 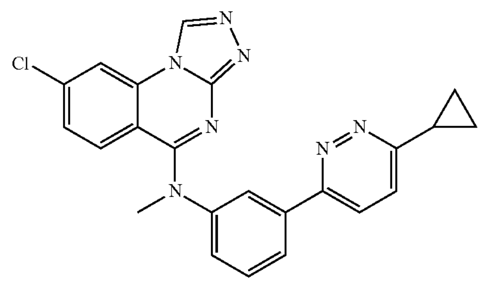 |

TABLE 2E

| Ex. | Chemical Structure |
|---|---|
| 341 | 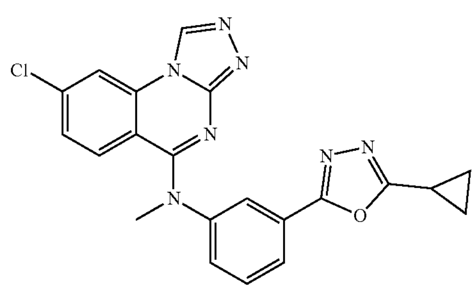 [SMILES: CN(c1cccc(-c2nnc(C3CC3)o2)c1)c1nc2nncn2c2cc(Cl)ccc12] |
| 342 | 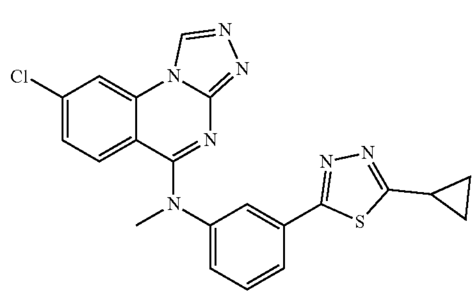 [SMILES: CN(c1cccc(-c2nnc(C3CC3)s2)c1)c1nc2nncn2c2cc(Cl)ccc12] |

TABLE 2E-continued

| Ex. | Chemical Structure |
|---|---|
| 343 | 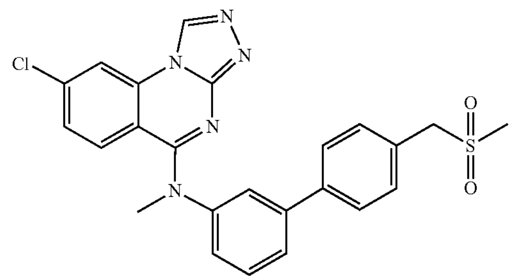 [SMILES: CN(c1cccc(-c2ccc(CS(C)(=O)=O)cc2)c1)c1nc2nncn2c2cc(Cl)ccc12] |
| 344 | 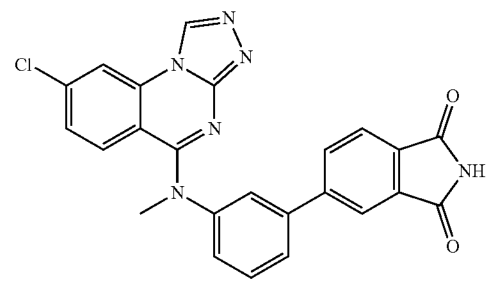 [SMILES: CN(c1cccc(-c2ccc3c(c2)C(=O)NC3=O)c1)c1nc2nncn2c2cc(Cl)ccc12] |
| 345 | 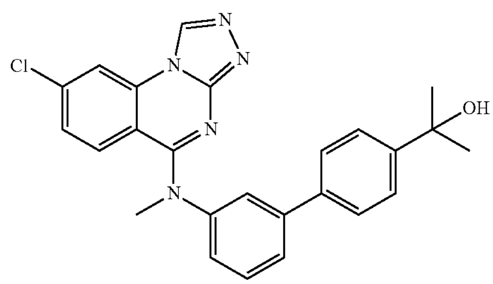 |
| 346 | 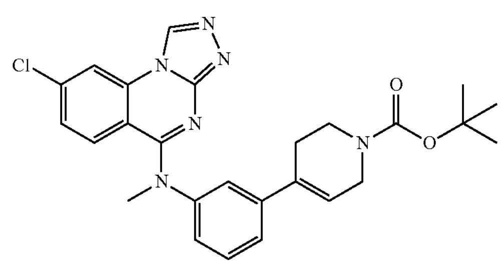 [SMILES: CN(c1cccc(C2=CCN(C(=O)OC(C)(C)C)CC2)c1)c1nc2nncn2c2cc(Cl)ccc12] |
| 347 | 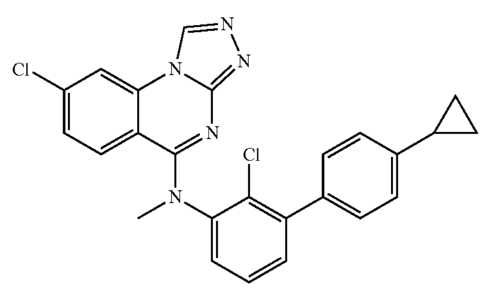 |

TABLE 2E-continued

Compounds

| Ex. | Chemical Structure |
|---|---|
| 348 | 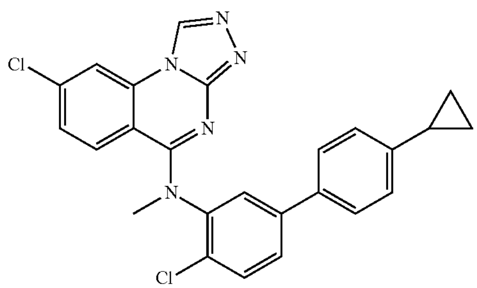 |
| 349 | 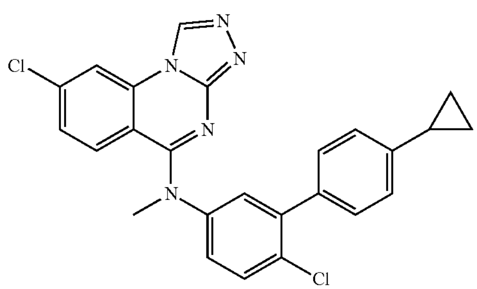 |
| 350 | 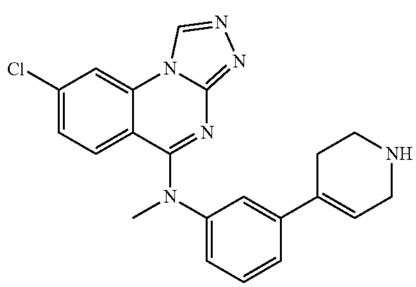 |
| 351 | 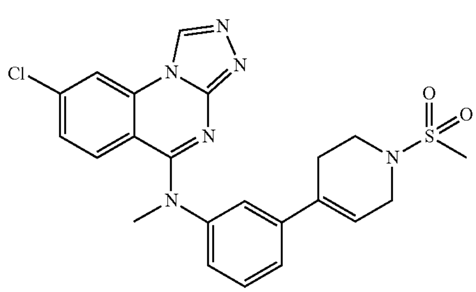 [SMILES: CN(c1cccc(C2=CCN(S(C)(=O)=O)CC2)c1)c1nc2nncn2c2cc(Cl)ccc12] |
| 352 | 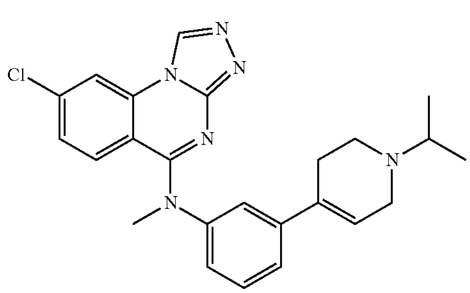 [SMILES: CC(C)N1CC=C(c2cccc(N(C)c3nc4nncn4c4cc(Cl)ccc34)c2)CC1] |
| 353 | |
| 354 | |
| 355 | |
| 356 | |
| 357 | |

TABLE 2E-continued

Compounds

| Ex. | Chemical Structure |
|---|---|
| 358 | 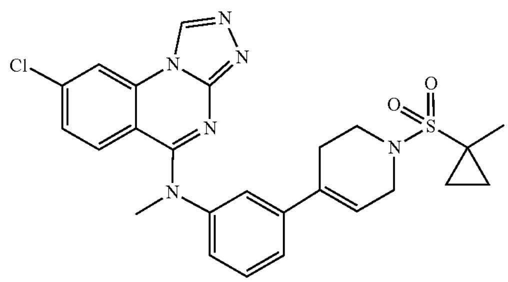 [SMILES: CN(c1cccc(C2=CCN(S(=O)(=O)C3(C)CC3)CC2)c1)c1nc2nncn2c2cc(Cl)ccc12] |
| 359 | 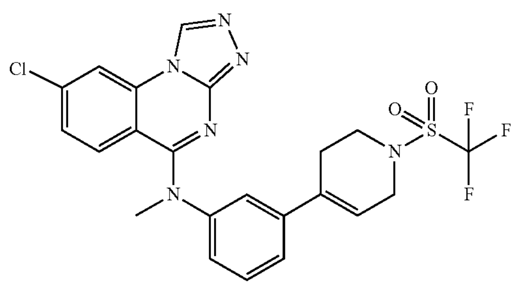 [SMILES: CN(c1cccc(C2=CCN(S(=O)(=O)C(F)(F)F)CC2)c1)c1nc2nncn2c2cc(Cl)ccc12] |
| 360 | 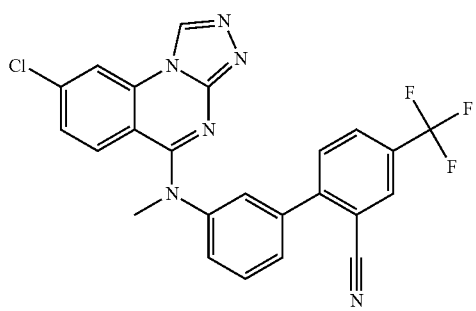 |
| 361 | 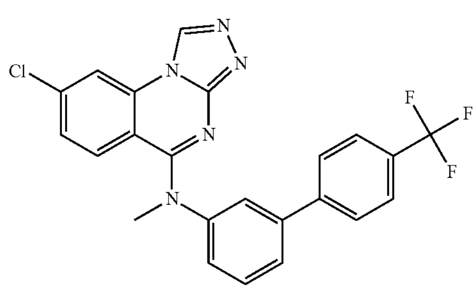 |
| 362 | 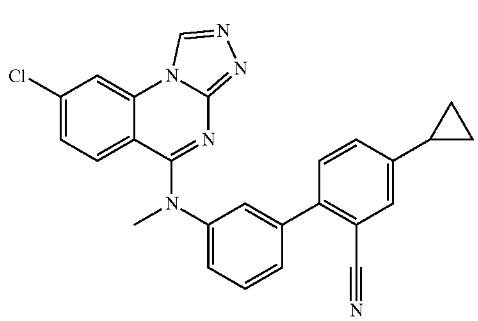 |
| 363 | |
| 364 | |
| 365 | |
| 366 | |
| 367 | |

TABLE 2E-continued

| Ex. | Chemical Structure |
|---|---|
| 368 | (8-chloro-[1,2,4]triazolo[4,3-a]quinazolin-5-yl)(methyl)(3-(4-hydroxy-4-(trifluoromethyl)but-1-yn-1-yl)phenyl)amine |
| 369 | (8-chloro-[1,2,4]triazolo[4,3-a]quinazolin-5-yl)(methyl)(3-((1-hydroxycyclobutyl)ethynyl)phenyl)amine |
| 370 | 1-(4'-((8-chloro-[1,2,4]triazolo[4,3-a]quinazolin-5-yl)(methyl)amino)-[1,1'-biphenyl]-4-yl)-2,2,2-trifluoroethan-1-ol |
| 371 | (8-chloro-[1,2,4]triazolo[4,3-a]quinazolin-5-yl)(3-(4-methoxy-4-methylpent-1-yn-1-yl)phenyl)(methyl)amine |

TABLE 2F

| Ex. | Chemical Structure |
|---|---|
| 372 | (8-chloro-[1,2,4]triazolo[4,3-a]quinazolin-5-yl)(3-(4-fluoro-4-methyl-3-hydroxybut-1-yn-1-yl)phenyl)(methyl)amine |

TABLE 2F-continued

| Ex. | Chemical Structure |
|---|---|
| 373 | (S)-4-(3-((8-chloro-[1,2,4]triazolo[4,3-a]quinazolin-5-yl)(methyl)amino)phenyl)-1-fluoro-2-methylbut-3-yn-2-ol |
| 374 | (R)-4-(3-((8-chloro-[1,2,4]triazolo[4,3-a]quinazolin-5-yl)(methyl)amino)phenyl)-1-fluoro-2-methylbut-3-yn-2-ol |
| 375 | 3-((3-((8-chloro-[1,2,4]triazolo[4,3-a]quinazolin-5-yl)(methyl)amino)phenyl)ethynyl)tetrahydrofuran-3-ol |
| 376 | 4-(3-((1,8-dichloro-[1,2,4]triazolo[4,3-a]quinazolin-5-yl)(methyl)amino)phenyl)-2-methylbut-3-yn-2-ol |
| 377 | (1,8-dichloro-[1,2,4]triazolo[4,3-a]quinazolin-5-yl)(3-(5-cyclopropylpyrazin-2-yl)phenyl)(methyl)amine |

TABLE 2F-continued

Compounds

| Ex. | Chemical Structure |
|---|---|
| 378 | 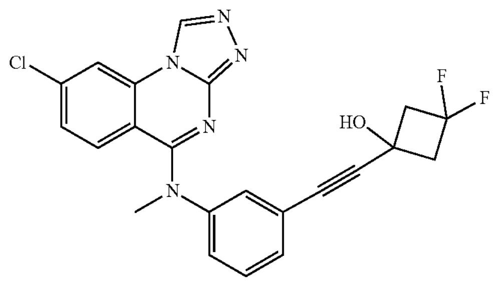 [SMILES: CN(c1cccc(C#CC2(O)CC(F)(F)C2)c1)c1nc2nncn2c2cc(Cl)ccc12] |
| 379 | 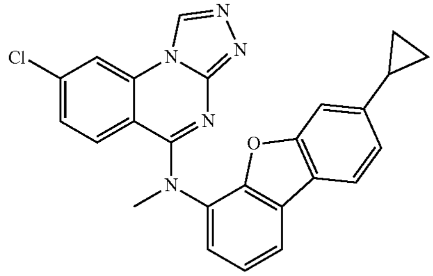 [SMILES: CN(c1nc2nncn2c2cc(Cl)ccc12)c1cccc2c1oc1cc(C3CC3)ccc12] |
| 380 | 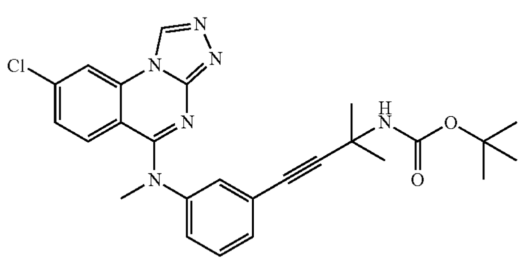 [SMILES: CN(c1cccc(C#CC(C)(C)NC(=O)OC(C)(C)C)c1)c1nc2nncn2c2cc(Cl)ccc12] |
| 381 | 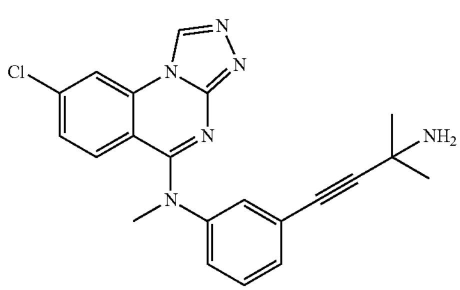 [SMILES: CN(c1cccc(C#CC(C)(C)N)c1)c1nc2nncn2c2cc(Cl)ccc12] |
| 382 | 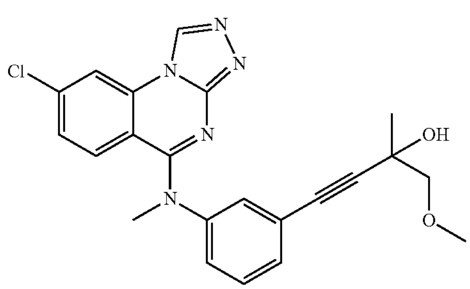 |
| 383 | |
| 384 | |
| 385 | |
| 386 | |
| 387 | |

TABLE 2F-continued

| Ex. | Chemical Structure |
|---|---|
| 388 | [chemical structure] |
| 389 | [chemical structure] |
| 390 | [chemical structure] |
| 391 | [chemical structure] |
| 392 | [chemical structure] |
| 393 | [chemical structure] |
| 394 | [chemical structure] |
| 395 | [chemical structure] |
| 396 | [chemical structure] |
| 397 | [chemical structure] |

TABLE 2F-continued
| Ex. | Chemical Structure |
|---|---|
| 398 | 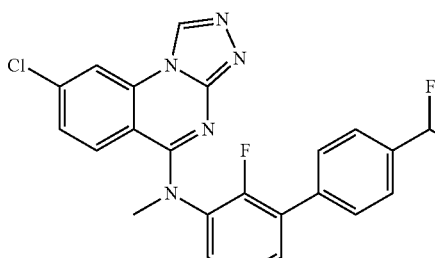 |
| 399 | 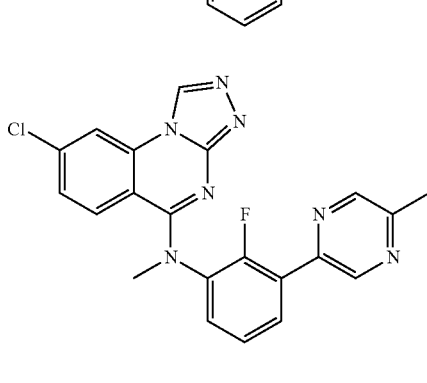 |
| 400 | 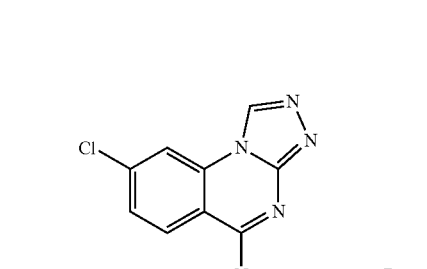 |
TABLE 2G
| Ex. | Chemical Structure |
|---|---|
| 401 | 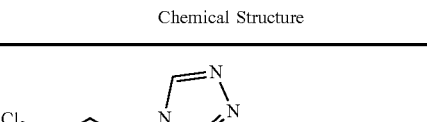 |
TABLE 2G-continued
| Ex. | Chemical Structure |
|---|---|
| 402 | 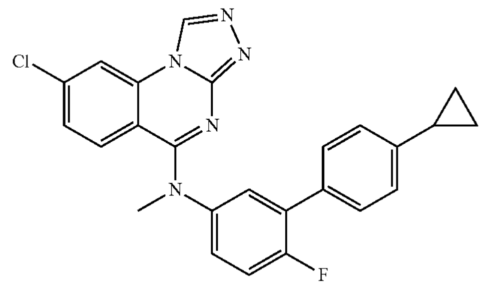 [SMILES: CN(c1ccc(F)c(-c2ccc(C3CC3)cc2)c1)c1nc2nncn2c2cc(Cl)ccc12] |
| 403 | 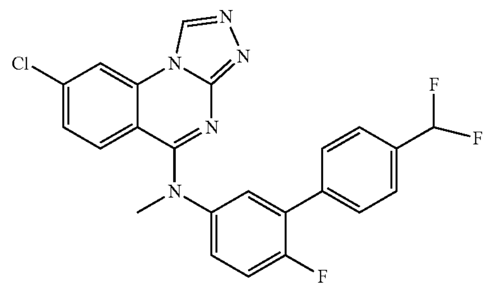 [SMILES: CN(c1ccc(F)c(-c2ccc(C(F)F)cc2)c1)c1nc2nncn2c2cc(Cl)ccc12] |
| 404 | 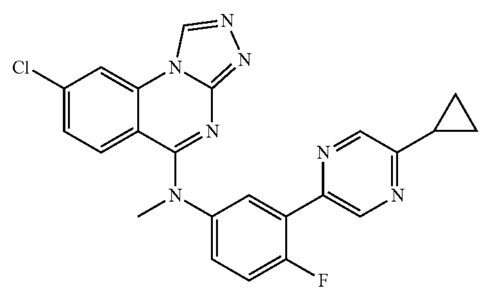 [SMILES: CN(c1ccc(F)c(-c2cnc(C3CC3)cn2)c1)c1nc2nncn2c2cc(Cl)ccc12] |
| 405 | 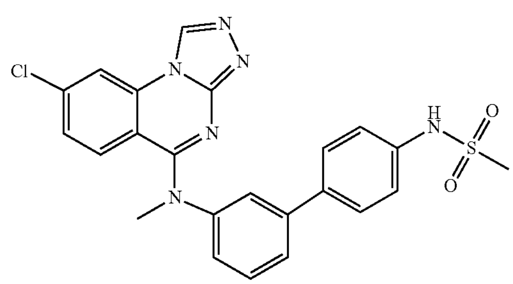 |
| 406 | 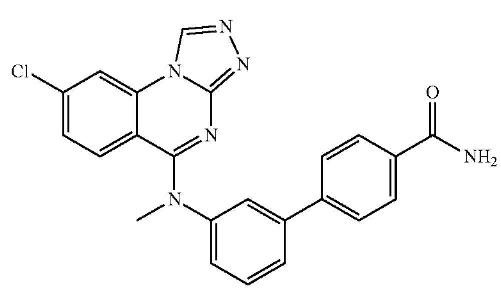 |

TABLE 2G-continued

Compounds

| Ex. | Chemical Structure |
|---|---|
| 407 | |
| 408 | |
| 409 | |
| 410 | |
| 411 | 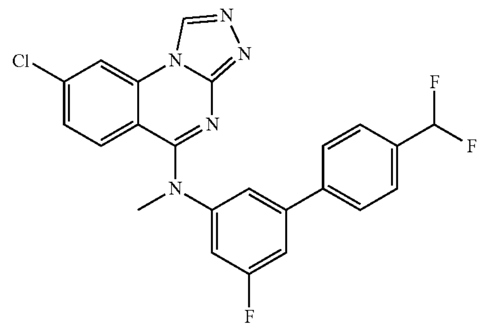 |
| 412 | 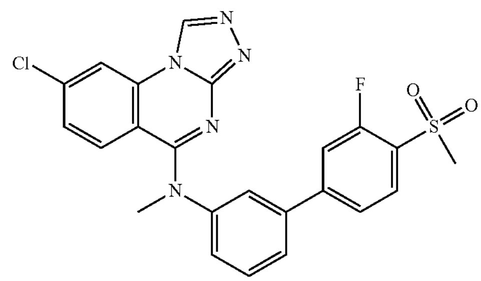 |
| 413 | 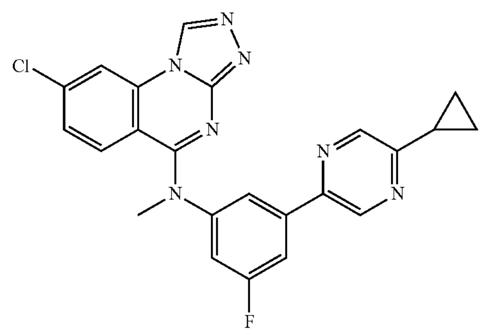 [SMILES: CN(c1cc(F)cc(-c2cnc(C3CC3)cn2)c1)c1nc2nncn2c2cc(Cl)ccc12] |
| 414 | 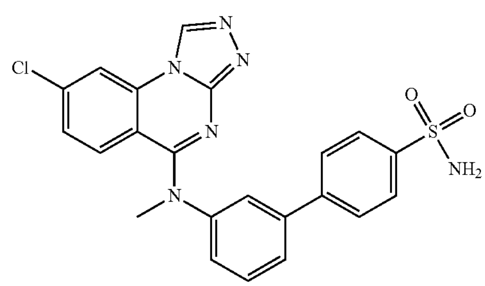 |
| 415 | 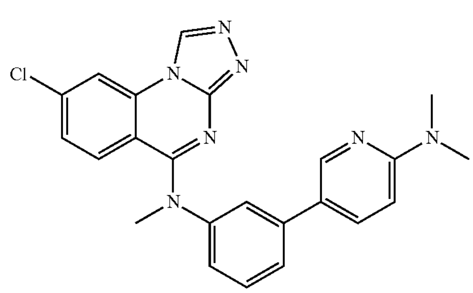 [SMILES: CN(C)c1ccc(-c2cccc(N(C)c3nc4nncn4c4cc(Cl)ccc34)c2)cn1] |

TABLE 2G-continued
Compounds
| Ex. | Chemical Structure |
|---|---|
| 416 | 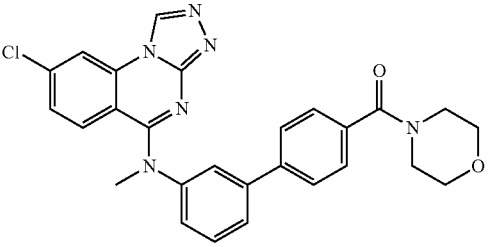 |
| 417 | 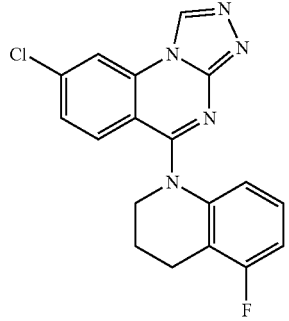 |
| 418 | 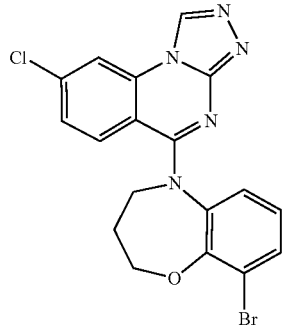 |
| 419 | 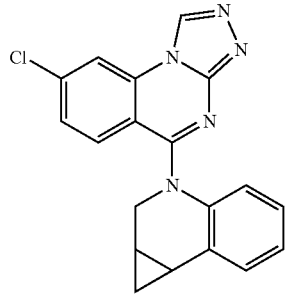 [SMILES: Clc1ccc2c(N3CC4CC4c4ccccc43)nc3nncn3c2c1] |
| 420 | 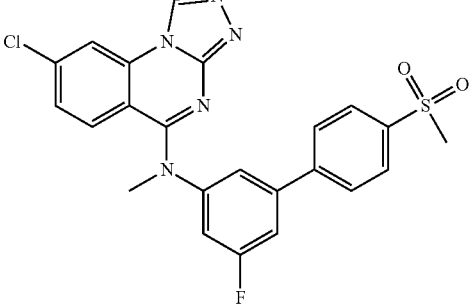 |
| 421 | 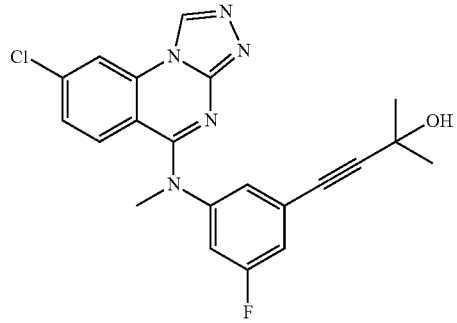 |
| 422 | 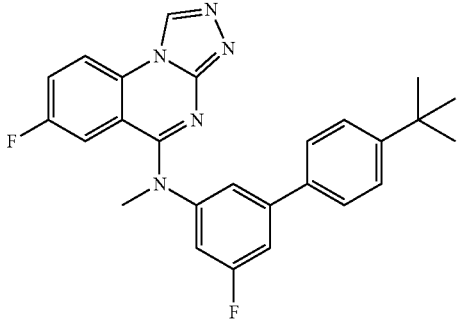 [SMILES: CN(c1cc(F)cc(-c2ccc(C(C)(C)C)cc2)c1)c1nc2nncn2c2ccc(F)cc12] |
| 423 | 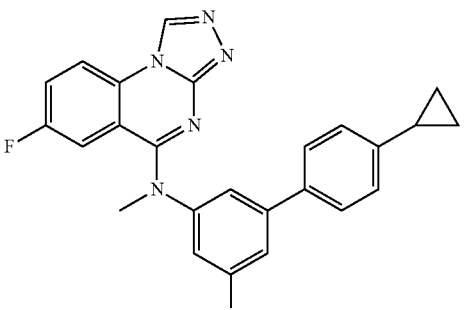 |
| 424 | 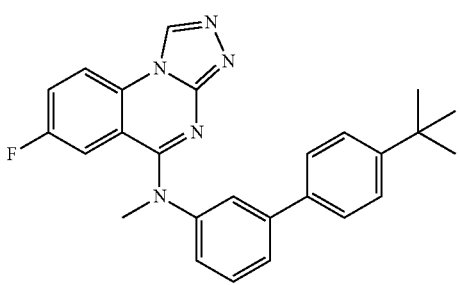 [SMILES: CN(c1cccc(-c2ccc(C(C)(C)C)cc2)c1)c1nc2nncn2c2ccc(F)cc12] |
| 425 | 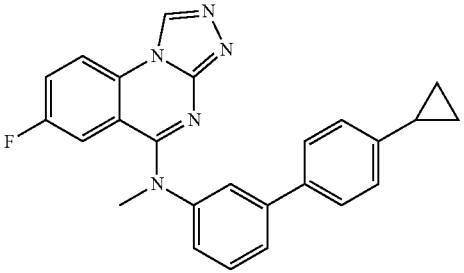 |

TABLE 2G-continued

Compounds

| Ex. | Chemical Structure |
|---|---|
| 426 | 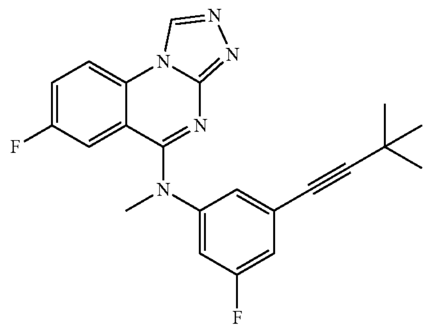 |
| 427 | 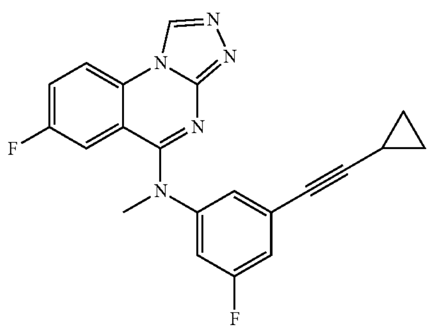 |
| 428 | 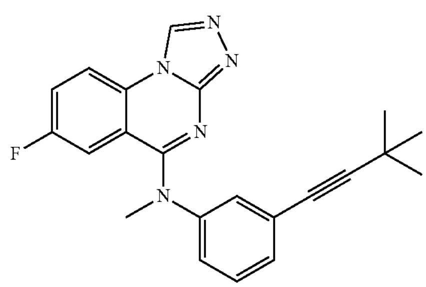 |
| 429 | 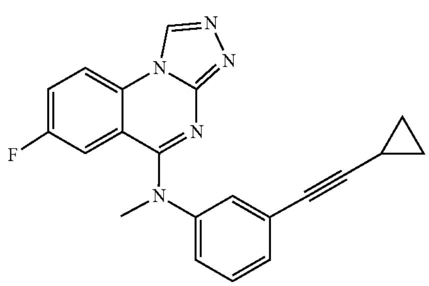 |
| 430 | 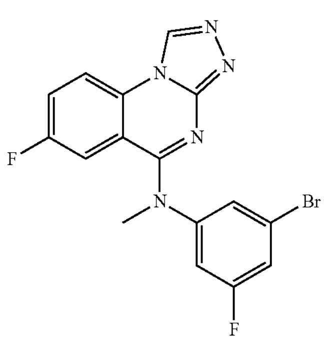 [SMILES: CN(c1cc(F)cc(Br)c1)c1nc2nncn2c2ccc(F)cc12] |

TABLE 2H

Compounds

| Ex. | Chemical Structure |
|---|---|
| 431 | 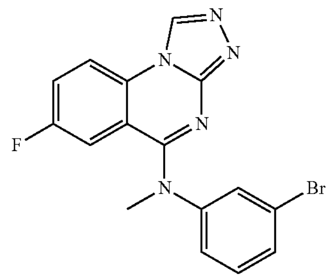 |
| 432 | 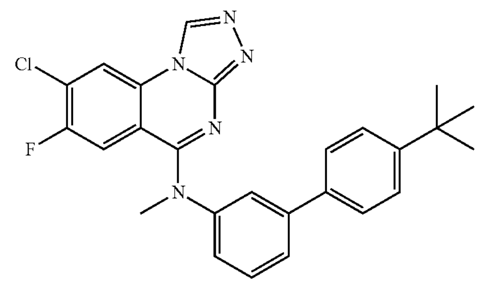 [SMILES: CN(c1cccc(-c2ccc(C(C)(C)C)cc2)c1)c1nc2nncn2c2cc(Cl)c(F)cc12] |
| 433 | 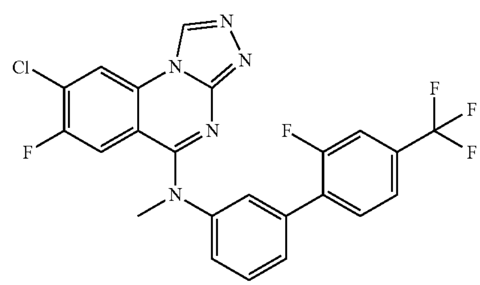 |
| 434 | 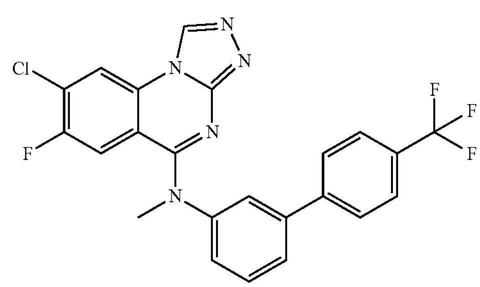 |
| 435 | 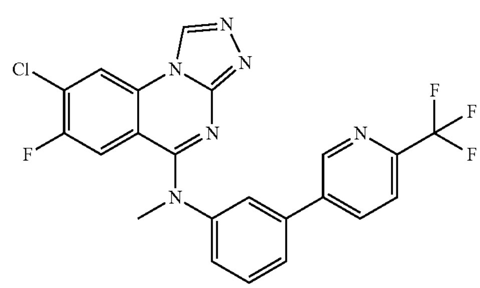 |

TABLE 2H-continued

Compounds

| Ex. | Chemical Structure |
|---|---|
| 436 | 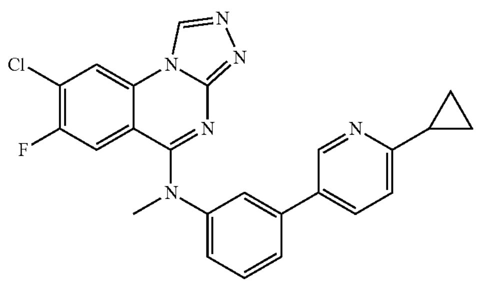 [SMILES: CN(c1cccc(-c2ccc(C3CC3)nc2)c1)c1nc2nncn2c2cc(Cl)c(F)cc12] |
| 437 | 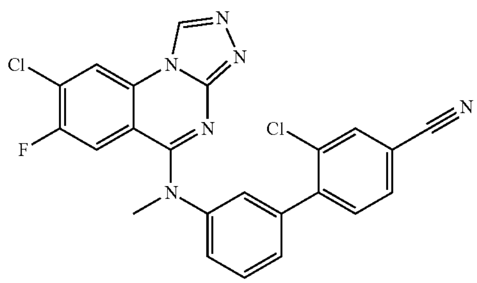 |
| 438 | 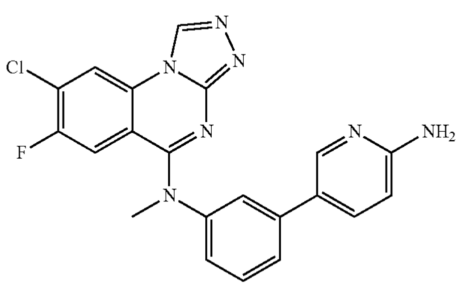 |
| 439 | 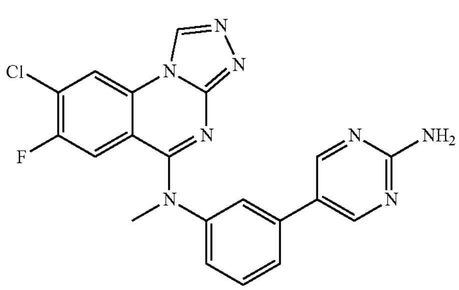 |
| 440 | 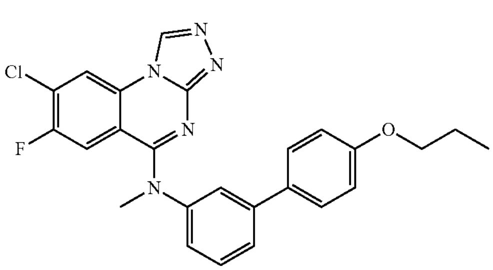 [SMILES: CCCOc1ccc(-c2cccc(N(C)c3nc4nncn4c4cc(Cl)c(F)cc34)c2)cc1] |
| 441 | |
| 442 | |
| 443 | |
| 444 | |
| 445 | |

TABLE 2H-continued
| Ex. | Chemical Structure |
|---|---|
| 446 | 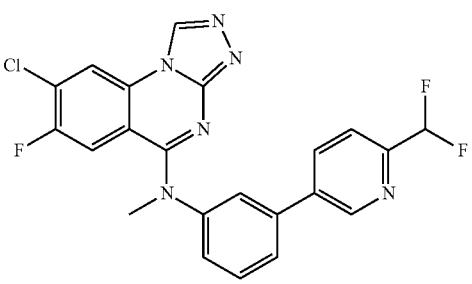 |
| 447 | 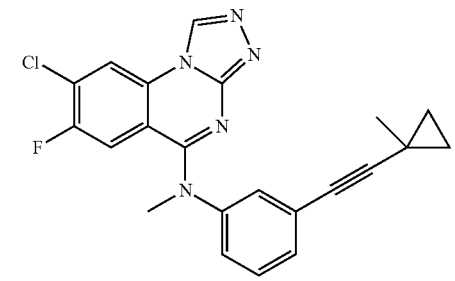 [SMILES: CN(c1cccc(C#CC2(C)CC2)c1)c1nc2nncn2c2cc(Cl)c(F)cc12] |
| 448 | 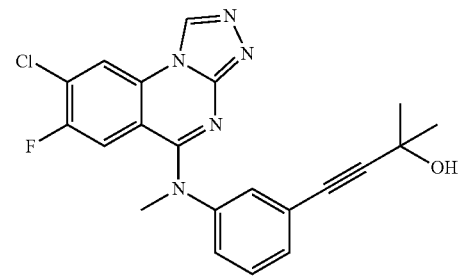 |
| 449 | 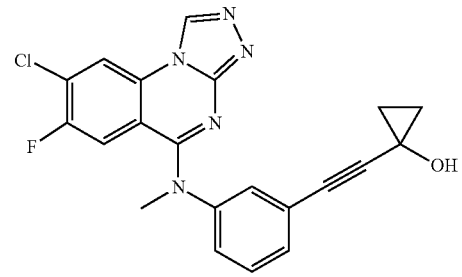 |
| 450 | 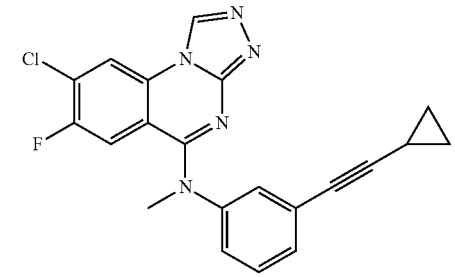 [SMILES: CN(c1cccc(C#CC2CC2)c1)c1nc2nncn2c2cc(Cl)c(F)cc12] |
| 451 | 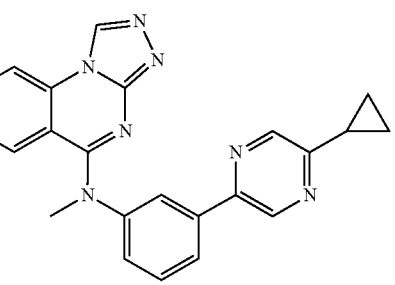 |
| 452 | 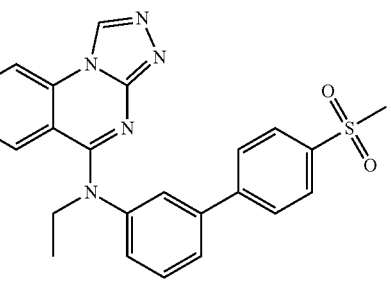 |
| 453 | 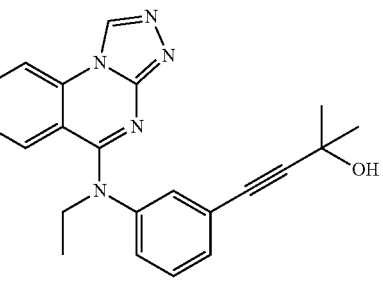 |
| 454 | 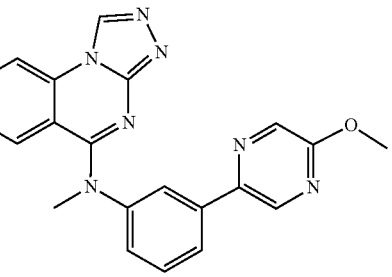 |
| 455 | 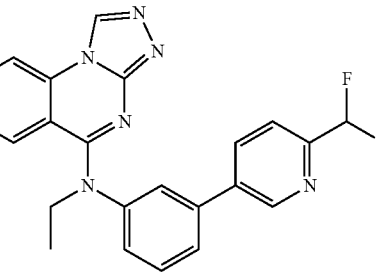 |

TABLE 2H-continued
| Compounds | |
|---|---|
| Ex. | Chemical Structure |
| 456 | 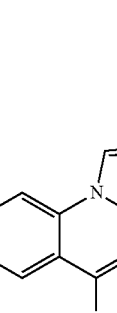 |
| 457 | 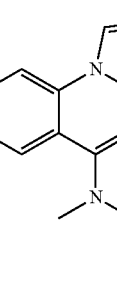 |
| 458 | 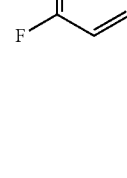 |
| 459 | 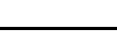 |
TABLE 2I
| Compounds | |
|---|---|
| Ex. | Chemical Structure |
| 460 | 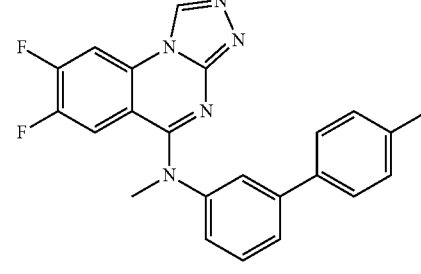 |
TABLE 2I-continued
| Compounds | |
|---|---|
| Ex. | Chemical Structure |
| 461 | 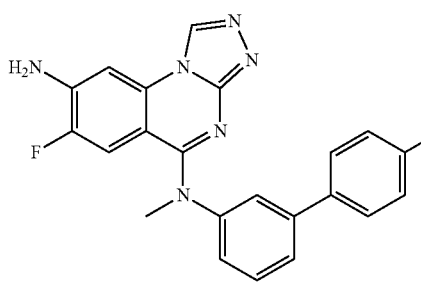 |
| 462 | 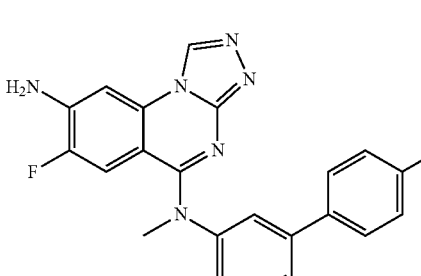 |
| 463 | 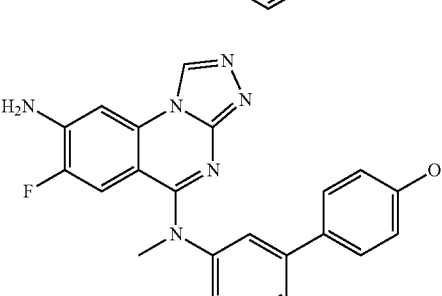 |
| 464 | 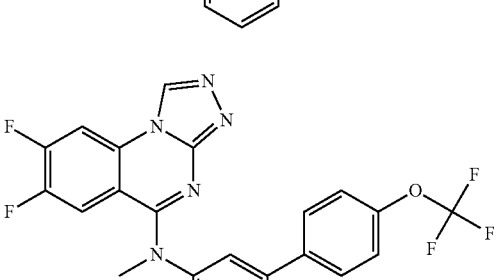 |
| 465 | |

TABLE 2I-continued
Compounds
| Ex. | Chemical Structure |
|---|---|
| 466 | 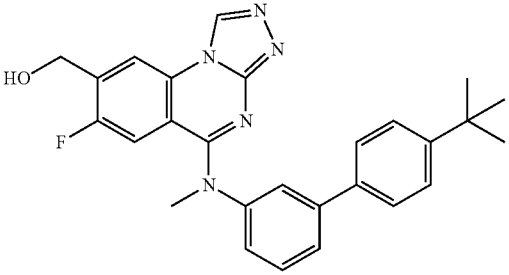 [SMILES: CN(c1cccc(-c2ccc(C(C)(C)C)cc2)c1)c1nc2nncn2c2cc(CO)c(F)cc12] |
| 467 | 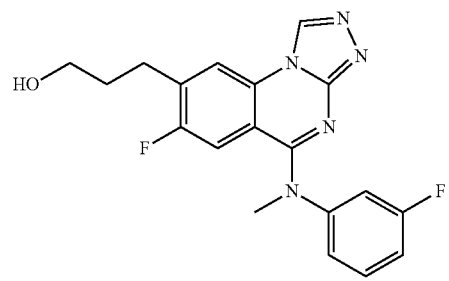 |
| 468 | 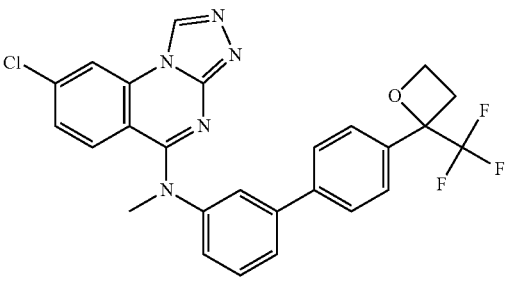 [SMILES: CN(c1cccc(-c2ccc(C3(C(F)(F)F)CCO3)cc2)c1)c1nc2nncn2c2cc(Cl)ccc12] |
| 469 | 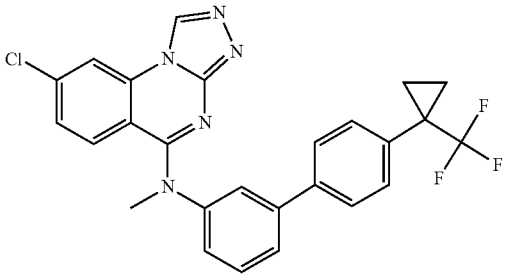 [SMILES: CN(c1cccc(-c2ccc(C3(C(F)(F)F)CC3)cc2)c1)c1nc2nncn2c2cc(Cl)ccc12] |
| 470 | 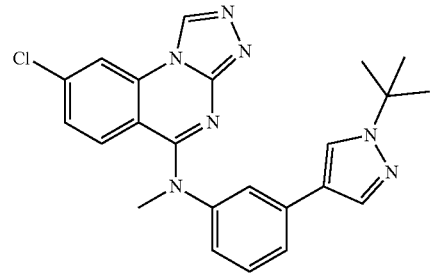 |
| 471 | 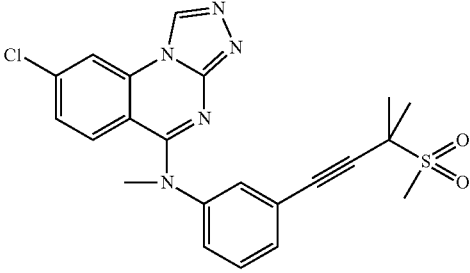 [SMILES: CN(c1cccc(C#CC(C)(C)S(C)(=O)=O)c1)c1nc2nncn2c2cc(Cl)ccc12] |
| 472 | 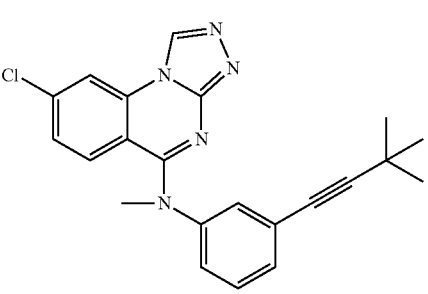 [SMILES: CN(c1cccc(C#CC(C)(C)C)c1)c1nc2nncn2c2cc(Cl)ccc12] |
| 473 | 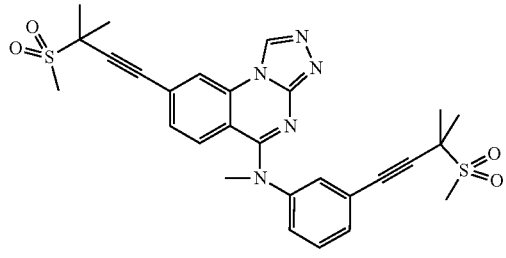 [SMILES: CN(c1cccc(C#CC(C)(C)S(C)(=O)=O)c1)c1nc2nncn2c2cc(C#CC(C)(C)S(C)(=O)=O)ccc12] |
| 474 | 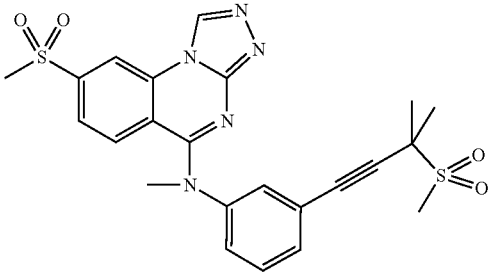 [SMILES: CN(c1cccc(C#CC(C)(C)S(C)(=O)=O)c1)c1nc2nncn2c2cc(S(C)(=O)=O)ccc12] |
| 475 | 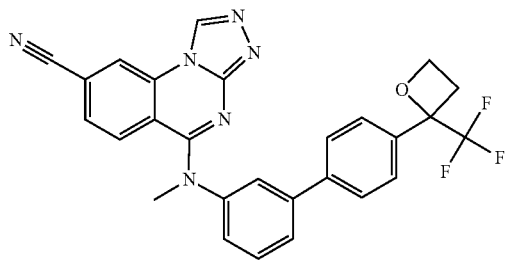 [SMILES: CN(c1cccc(-c2ccc(C3(C(F)(F)F)CCO3)cc2)c1)c1nc2nncn2c2cc(C#N)ccc12] |

TABLE 2I-continued

Compounds

| Ex. | Chemical Structure |
|---|---|
| 476 | 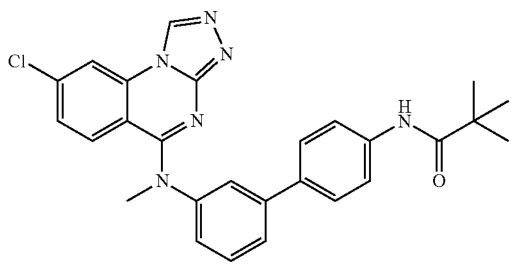 [SMILES: CN(c1cccc(-c2ccc(NC(=O)C(C)(C)C)cc2)c1)c1nc2nncn2c2cc(Cl)ccc12] |
| 477 | 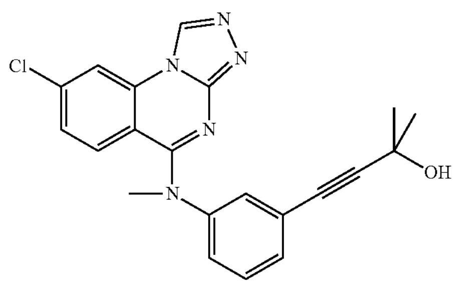 [SMILES: CN(c1cccc(C#CC(C)(C)O)c1)c1nc2nncn2c2cc(Cl)ccc12] |
| 478 | 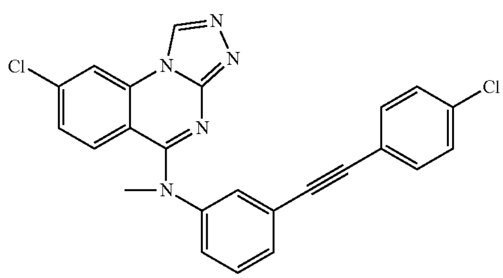 [SMILES: CN(c1cccc(C#Cc2ccc(Cl)cc2)c1)c1nc2nncn2c2cc(Cl)ccc12] |
| 479 | 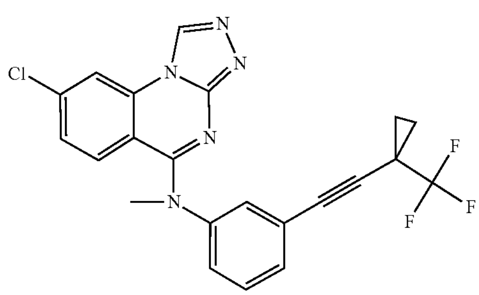 [SMILES: CN(c1cccc(C#CC2(C(F)(F)F)CC2)c1)c1nc2nncn2c2cc(Cl)ccc12] |
| 480 | 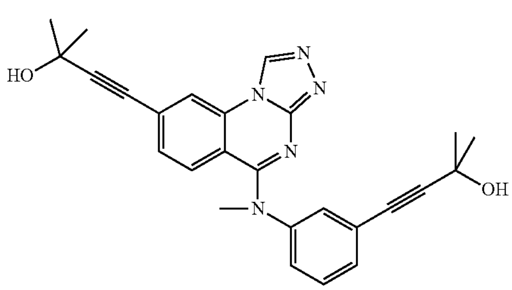 [SMILES: CN(c1cccc(C#CC(C)(C)O)c1)c1nc2nncn2c2cc(C#CC(C)(C)O)ccc12] |
| 481 | |
| 482 | |
| 483 | |
| 484 | |
| 485 | |

TABLE 2I-continued

| Ex. | Chemical Structure |
|---|---|
| 486 | (structure) |
| 487 | (structure) |
| 488 | (structure) |
| 489 | (structure) |
| 490 | (structure) |

TABLE 2J

| Ex. | Chemical Structure |
|---|---|
| 491 | (structure) |
| 492 | (structure) |
| 493 | (structure) |
| 494 | (structure) |
| 495 | (structure) |

TABLE 2J-continued

| Ex. | Chemical Structure |
|---|---|
| 496 | 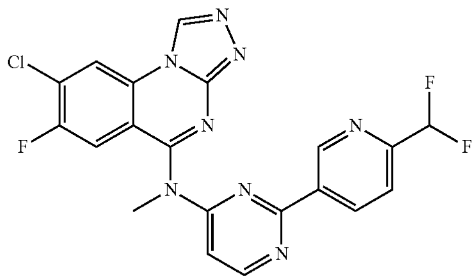 [SMILES: CN(c1ccnc(-c2ccc(C(F)F)nc2)n1)c1nc2nncn2c2cc(Cl)c(F)cc12] |
| 497 | 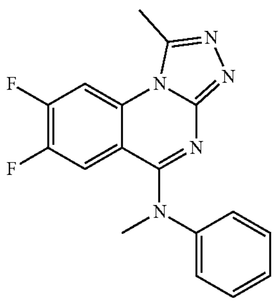 [SMILES: Cc1nnc2nc(N(C)c3ccccc3)c3cc(F)c(F)cc3n12] |
| 498 | 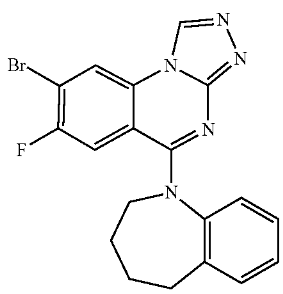 |
| 499 | 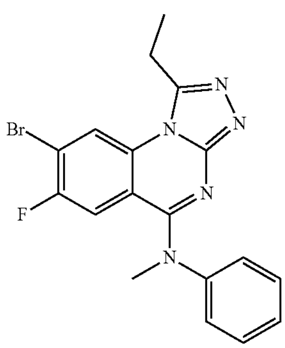 |
| 500 | 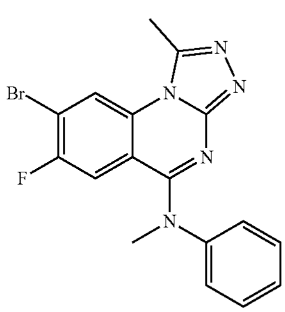 |
| 501 | |
| 502 | |
| 503 | |
| 504 | |
| 505 | |

TABLE 2J-continued

Compounds

| Ex. | Chemical Structure |
|---|---|
| 506 | 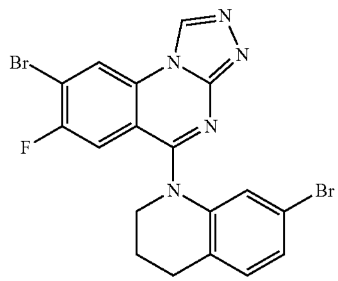 [SMILES: Fc1cc2c(N3CCCc4ccc(Br)cc43)nc3nncn3c2cc1Br] |
| 507 | 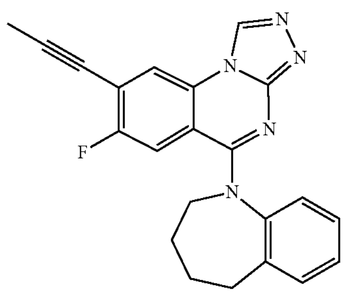 |
| 508 | 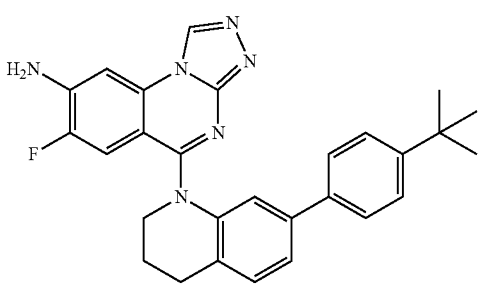 [SMILES: CC(C)(C)c1ccc(-c2ccc3c(c2)N(c2nc4nncn4c4cc(N)c(F)cc24)CCC3)cc1] |
| 509 | 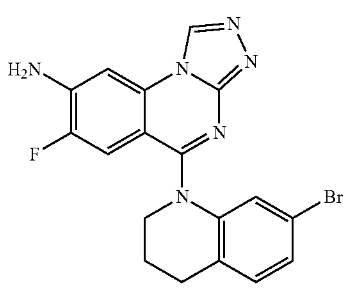 |
| 510 | 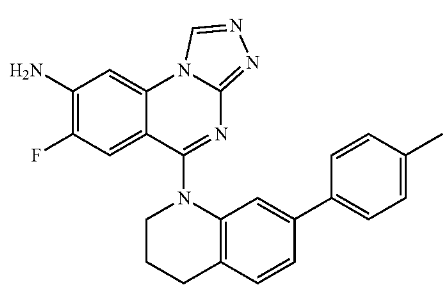 |
| 511 | |
| 512 | |
| 513 | |
| 514 | |

TABLE 2J-continued
Compounds
| Ex. | Chemical Structure |
|---|---|
| 515 | 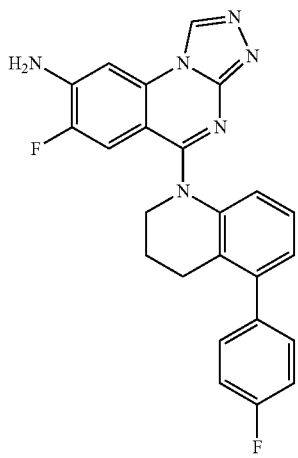 |
| 516 | 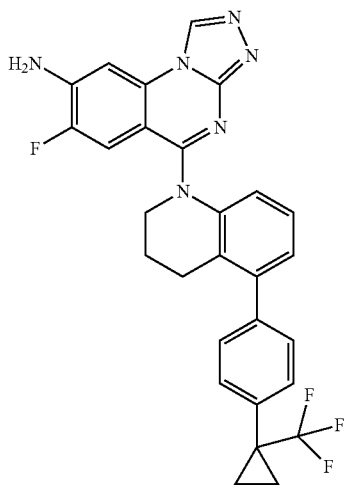 [SMILES: Nc1cc2c(cc1F)c(N1CCCc3c(-c4ccc(C5(C(F)(F)F)CC5)cc4)cccc31)nc1nncn12] |
| 517 | 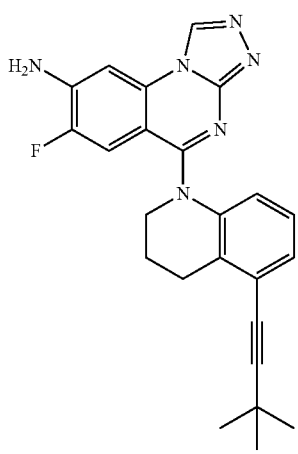 |
TABLE 2J-continued
Compounds
| Ex. | Chemical Structure |
|---|---|
| 518 | 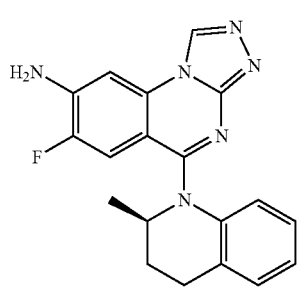 |
| 519 | 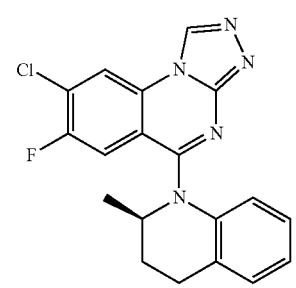 |
TABLE 2K
Compounds
| Ex. | Chemical Structure |
|---|---|
| 520 | 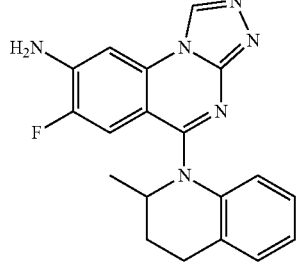 |
| 521 | 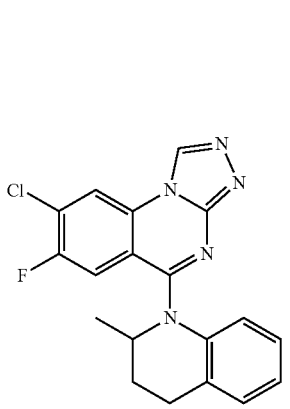 [SMILES: CC1CCc2ccccc2N1c1nc2nncn2c2cc(Cl)c(F)cc12] |

TABLE 2K-continued
Compounds
| Ex. | Chemical Structure |
|---|---|
| 522 | 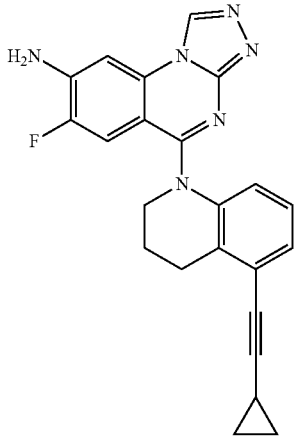 |
| 523 | 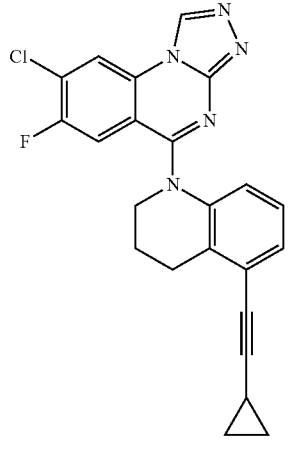 [SMILES: Fc1cc2c(N3CCCc4c(C#CC5CC5)cccc43)nc3nncn3c2cc1Cl] |
| 524 | 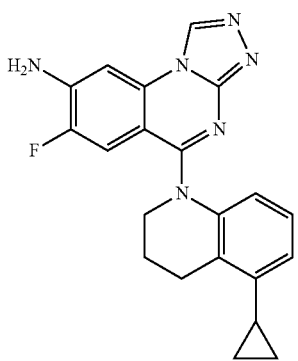 |
| 525 | 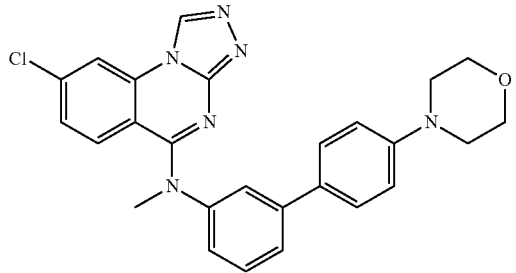 [SMILES: CN(c1cccc(-c2ccc(N3CCOCC3)cc2)c1)c1nc2nncn2c2cc(Cl)ccc12] |
| 526 | 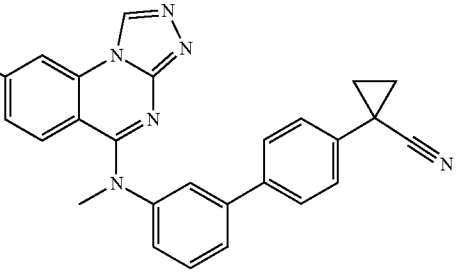 |
| 527 | 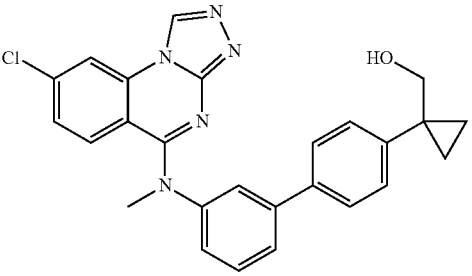 |
| 528 | 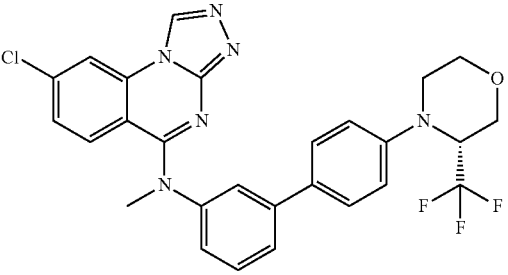 [SMILES: CN(c1cccc(-c2ccc(N3CCOC[C@@H]3C(F)(F)F)cc2)c1)c1nc2nncn2c2cc(Cl)ccc12] |
| 529 | 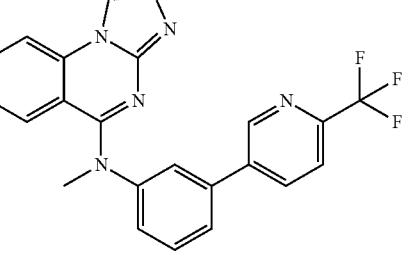 |
| 530 | 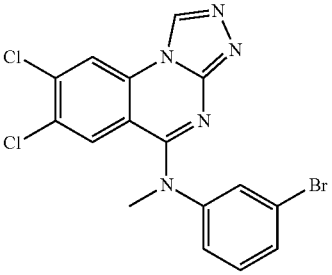 [SMILES: CN(c1cccc(Br)c1)c1nc2nncn2c2cc(Cl)c(Cl)cc12] |

TABLE 2K-continued

Compounds

| Ex. | Chemical Structure |
|---|---|
| 531 | 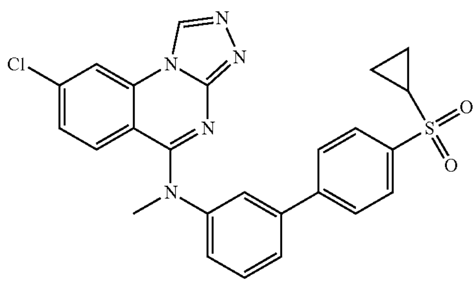 [SMILES: CN(c1cccc(-c2ccc(S(=O)(=O)C3CC3)cc2)c1)c1nc2nncn2c2cc(Cl)ccc12] |
| 532 | 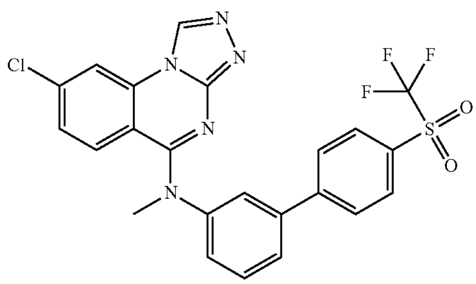 [SMILES: CN(c1cccc(-c2ccc(S(=O)(=O)C(F)(F)F)cc2)c1)c1nc2nncn2c2cc(Cl)ccc12] |
| 533 | 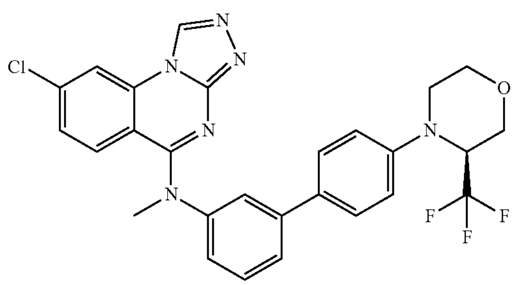 [SMILES: CN(c1cccc(-c2ccc(N3CCOC[C@H]3C(F)(F)F)cc2)c1)c1nc2nncn2c2cc(Cl)ccc12] |
| 534 | 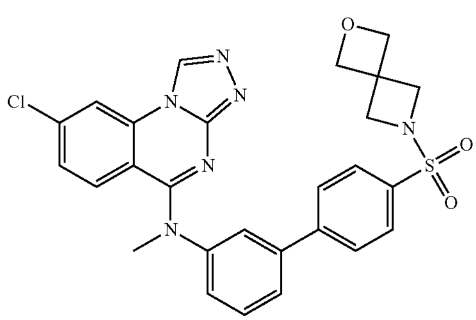 |
| 535 | 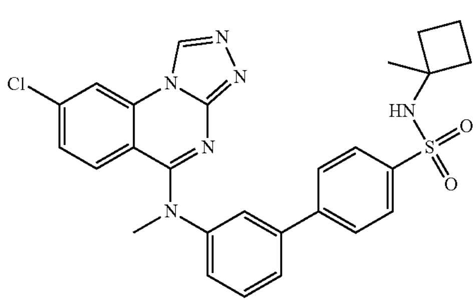 |
| 536 | 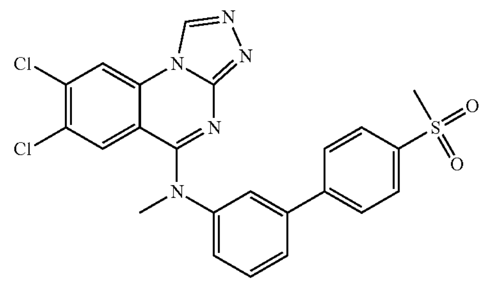 [SMILES: CN(c1cccc(-c2ccc(S(C)(=O)=O)cc2)c1)c1nc2nncn2c2cc(Cl)c(Cl)cc12] |
| 537 | 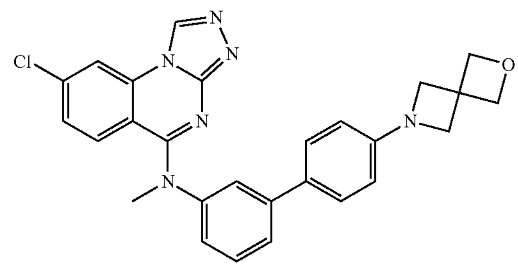 |
| 538 | 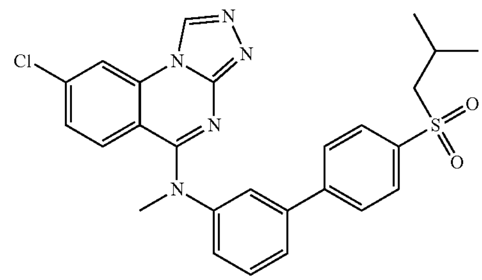 |
| 539 | 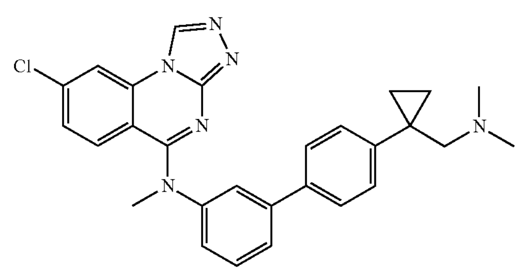 |
| 540 | 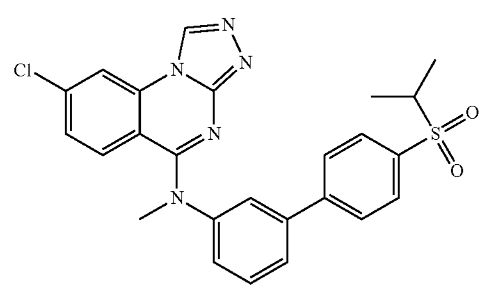 |

TABLE 2K-continued
Compounds
| Ex. | Chemical Structure |
|---|---|
| 541 | 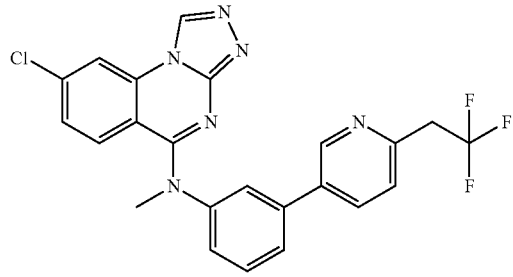 |
| 542 | 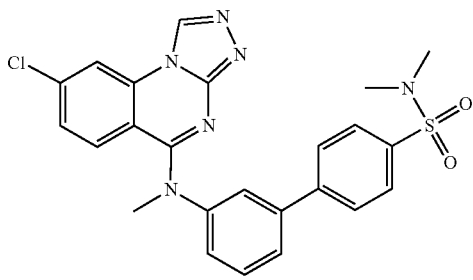 |
| 543 | 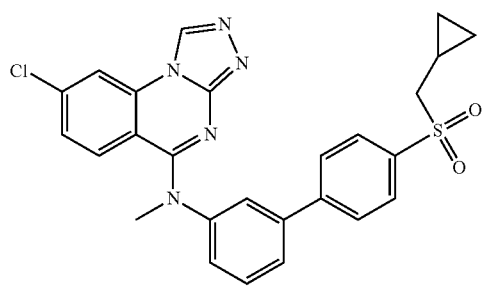 [SMILES: CN(c1cccc(-c2ccc(S(=O)(=O)CC3CC3)cc2)c1)c1nc2nncn2c2cc(Cl)ccc12] |
| 544 | 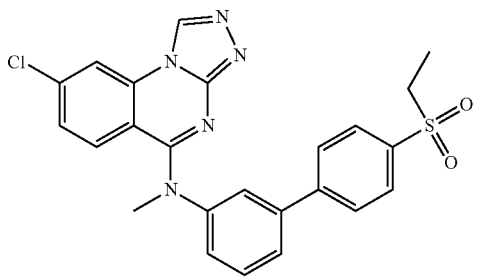 |
| 545 | 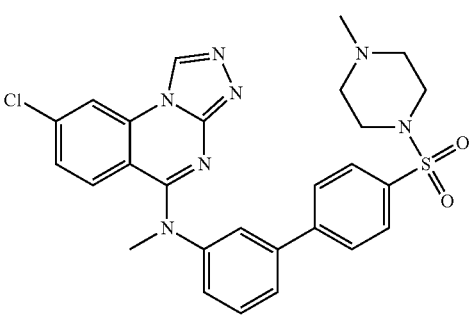 [SMILES: CN1CCN(S(=O)(=O)c2ccc(-c3cccc(N(C)c4nc5nncn5c5cc(Cl)ccc45)c3)cc2)CC1] |
| 546 | 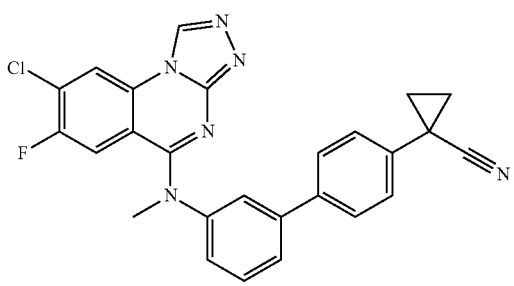 |
| 547 | 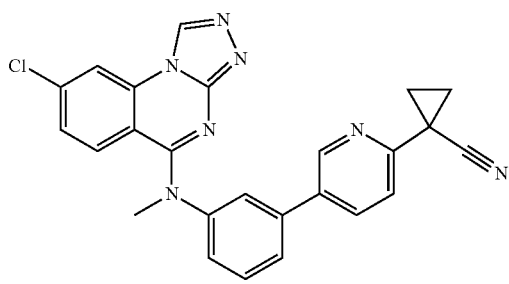 [SMILES: CN(c1cccc(-c2ccc(C3(C#N)CC3)nc2)c1)c1nc2nncn2c2cc(Cl)ccc12] |
| 548 | 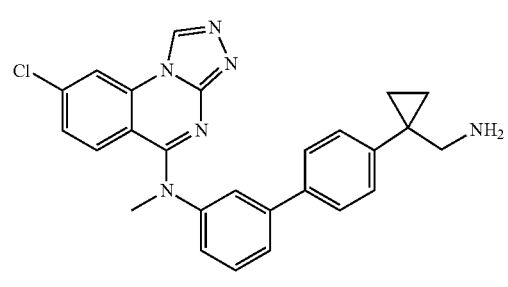 [SMILES: CN(c1cccc(-c2ccc(C3(CN)CC3)cc2)c1)c1nc2nncn2c2cc(Cl)ccc12] |

TABLE 2L

| Compounds | |
|---|---|
| Ex. | Chemical Structure |
| 549 | |
| 550 | |
| 551 | |
| 552 | |
| 553 | |

TABLE 2L-continued
| Ex. | Chemical Structure |
|---|---|
| 554 | 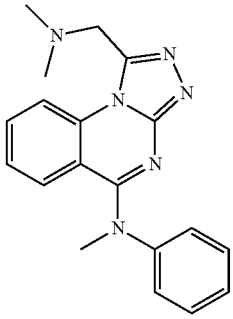 [SMILES: CN(C)Cc1nnc2nc(N(C)c3ccccc3)c3ccccc3n12] |
| 555 | 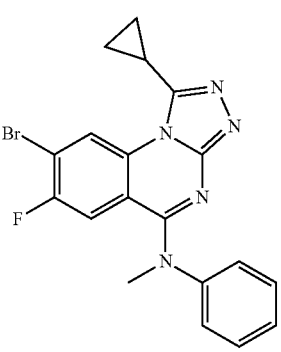 |
| 556 | 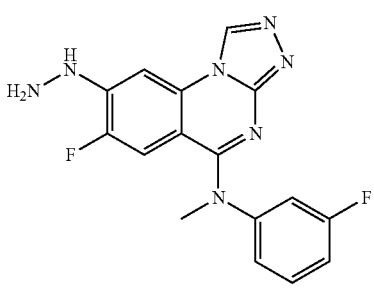 |
| 557 | 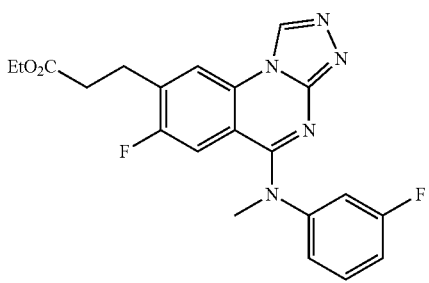 |
| 558 | 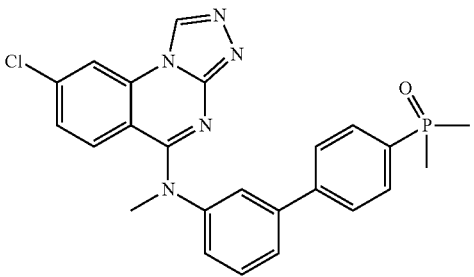 [SMILES: CN(c1cccc(-c2ccc(P(C)(C)=O)cc2)c1)c1nc2nncn2c2cc(Cl)ccc12] |

TABLE 2L-continued
| | Compounds |
|---|---|
| Ex. | Chemical Structure |
| 559 | 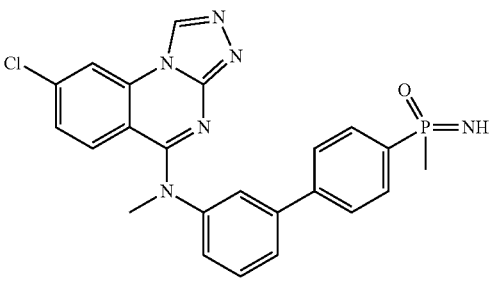 |
| 560 | 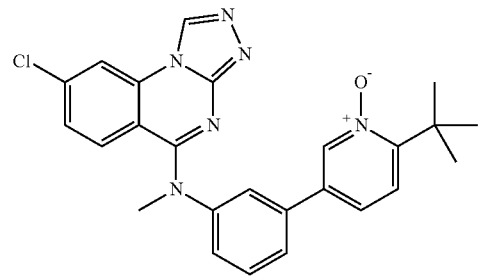 |
| 561 | 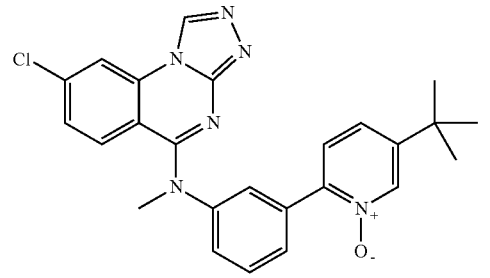 |
| 563 | 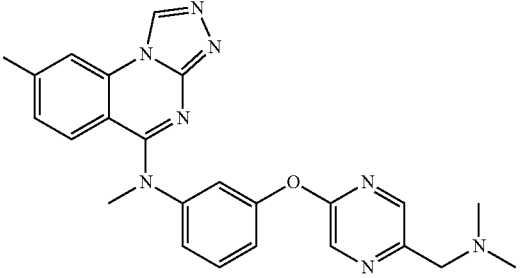 |
| 564 | 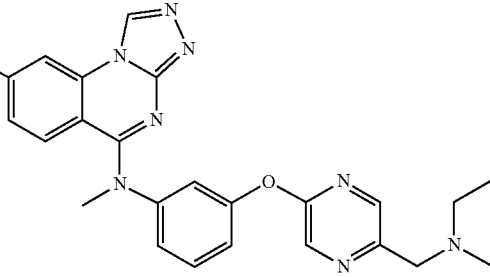 |

TABLE 2L-continued

| Ex. | Chemical Structure |
|---|---|
| 565 | 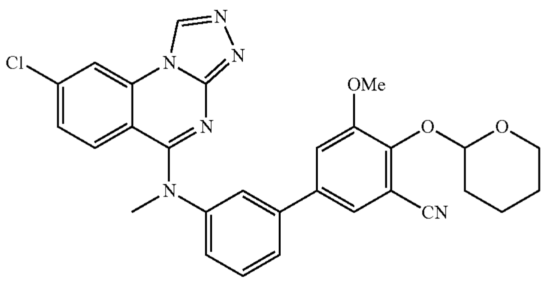 [SMILES: COc1cc(-c2cccc(N(C)c3nc4nncn4c4cc(Cl)ccc34)c2)cc(C#N)c1OC1CCCCO1] |
| 566 | 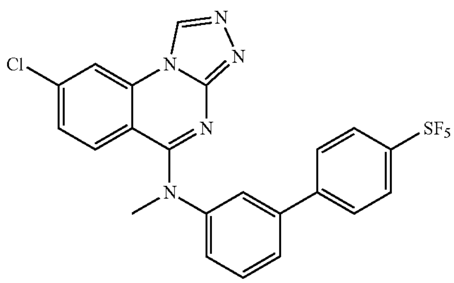 |
| 567 | 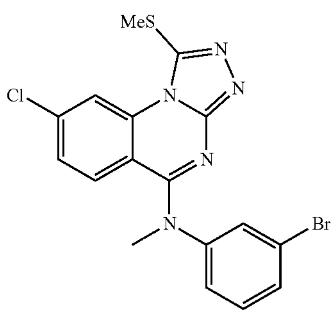 [SMILES: CSc1nnc2nc(N(C)c3cccc(Br)c3)c3ccc(Cl)cc3n12] |
| 569 | 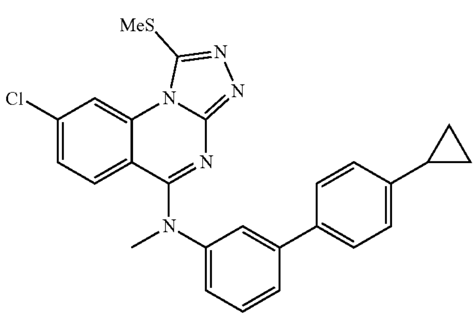 [SMILES: CSc1nnc2nc(N(C)c3cccc(-c4ccc(C5CC5)cc4)c3)c3ccc(Cl)cc3n12] |
| 570 | 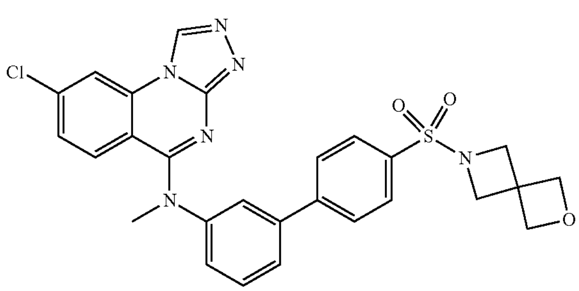 [SMILES: CN(c1cccc(-c2ccc(S(=O)(=O)N3CC4(COC4)C3)cc2)c1)c1nc2nncn2c2cc(Cl)ccc12] |

TABLE 2L-continued

| Ex. | Chemical Structure |
|---|---|
| 571 | 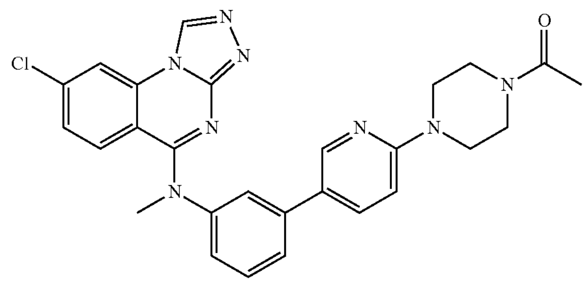 [SMILES: CC(=O)N1CCN(c2ccc(-c3cccc(N(C)c4nc5nncn5c5cc(Cl)ccc45)c3)cn2)CC1] |
| 572 | 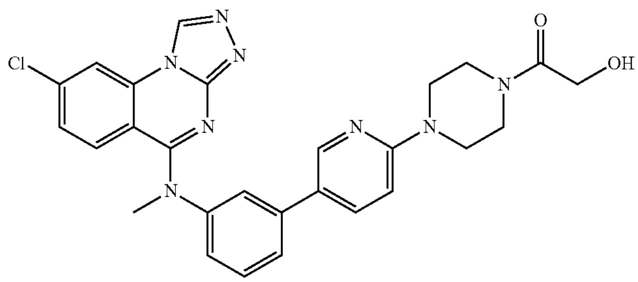 [SMILES: CN(c1cccc(-c2ccc(N3CCN(C(=O)CO)CC3)nc2)c1)c1nc2nncn2c2cc(Cl)ccc12] |
| 573 | 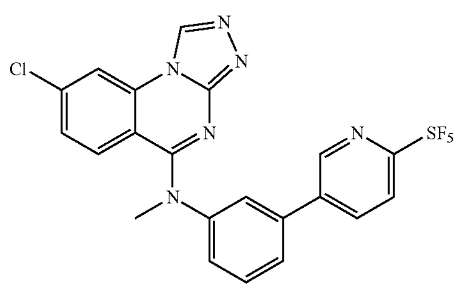 |
| 574 | 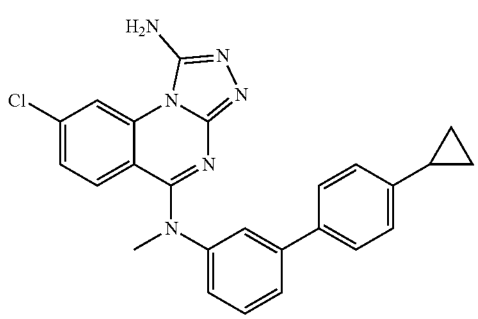 |
| 575 | 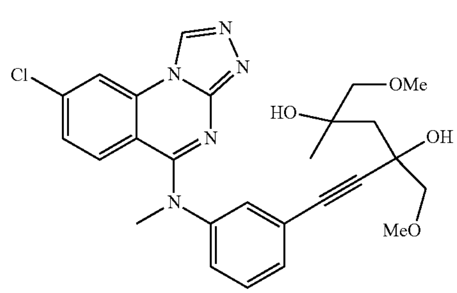 [SMILES: COCC(C)(O)CC(O)(C#Cc1cccc(N(C)c2nc3nncn3c3cc(Cl)ccc23)c1)COC] |

TABLE 2L-continued
Compounds
| Ex. | Chemical Structure |
|---|---|
| 576 | 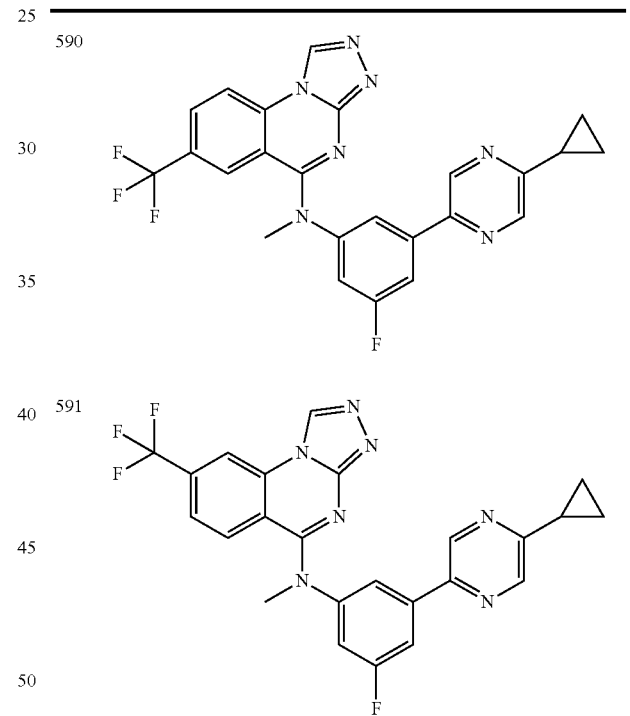 |
TABLE 3A
Compounds
| Ex. | Chemical Structure |
|---|---|
| 587 | 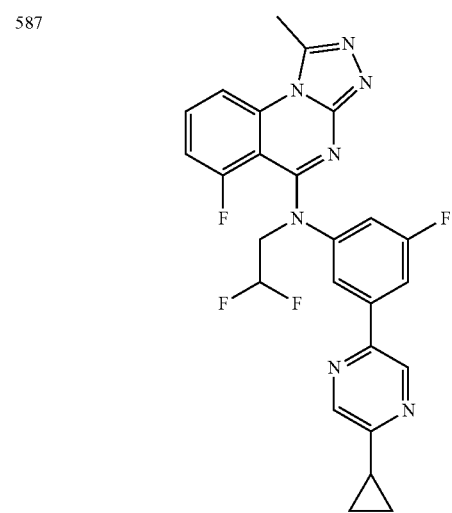 |
| 589 | 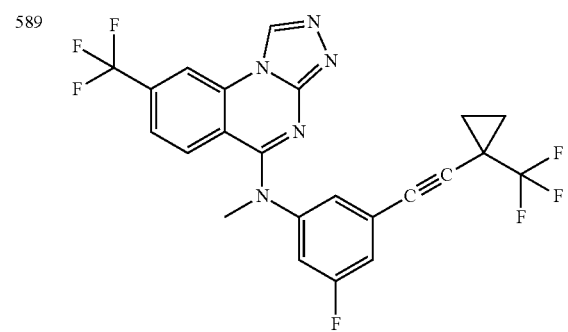 |
TABLE 3A-continued
Compounds
| Ex. | Chemical Structure |
|---|---|
| 590 | 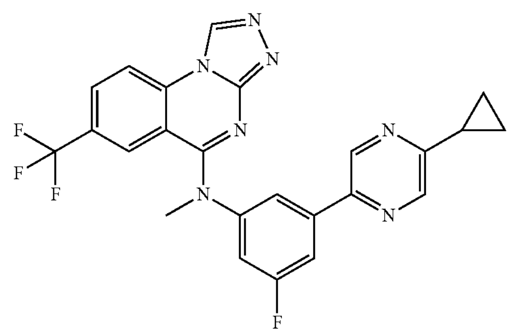 [SMILES: CN(c1cc(F)cc(-c2cnc(C3CC3)cn2)c1)c1nc2nncn2c2ccc(C(F)(F)F)cc12] |
| 591 | 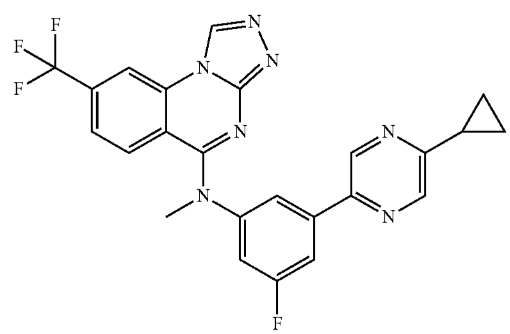 [SMILES: CN(c1cc(F)cc(-c2cnc(C3CC3)cn2)c1)c1nc2nncn2c2cc(C(F)(F)F)ccc12] |
| 592 | 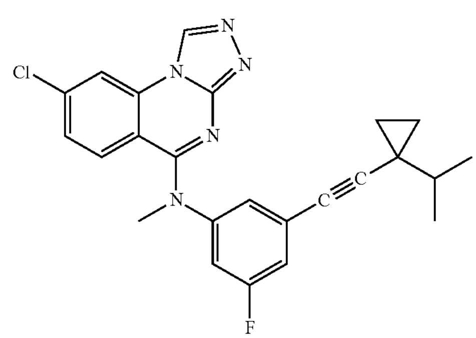 [SMILES: CC(C)C1(C#Cc2cc(F)cc(N(C)c3nc4nncn4c4cc(Cl)ccc34)c2)CC1] |

TABLE 3A-continued

| Ex. | Chemical Structure |
|---|---|
| 593 | 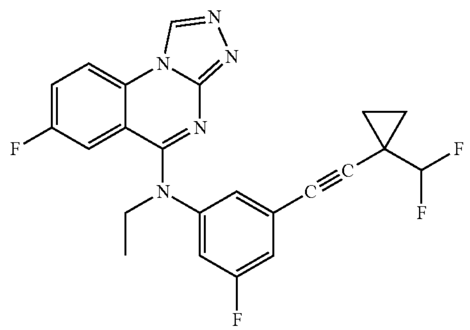 [SMILES: CCN(c1cc(F)cc(C#CC2(C(F)F)CC2)c1)c1nc2nncn2c2ccc(F)cc12] |
| 594 | 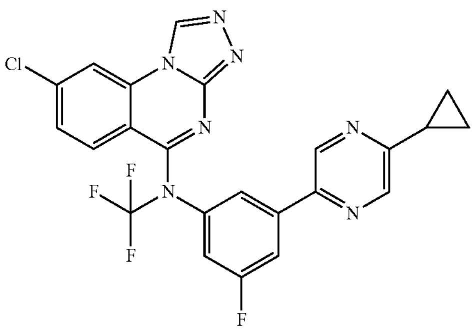 [SMILES: Fc1cc(-c2cnc(C3CC3)cn2)cc(N(c2nc3nncn3c3cc(Cl)ccc23)C(F)(F)F)c1] |
| 595 | 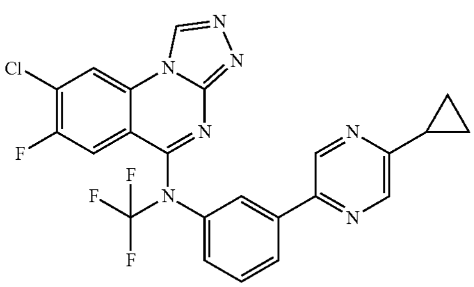 [SMILES: Fc1cc2c(N(c3cccc(-c4cnc(C5CC5)cn4)c3)C(F)(F)F)nc3nncn3c2cc1Cl] |
| 596 | 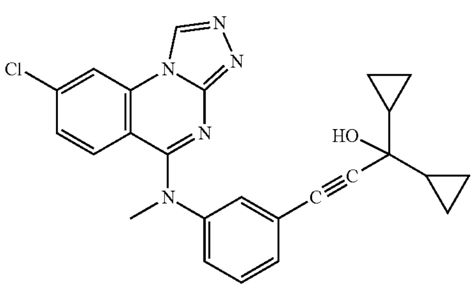 [SMILES: CN(c1cccc(C#CC(O)(C2CC2)C2CC2)c1)c1nc2nncn2c2cc(Cl)ccc12] |
| 597 | 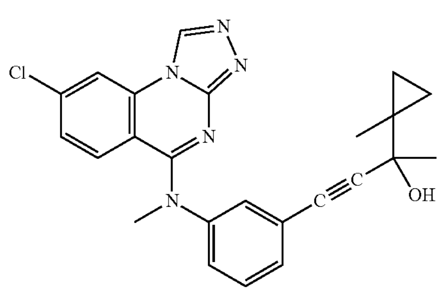 [SMILES: CN(c1cccc(C#CC(C)(O)C2(C)CC2)c1)c1nc2nncn2c2cc(Cl)ccc12] |
| 598 | |
| 599 | |
| 600 | |
| 601 | |
| 602 | |

TABLE 3A-continued
Compounds
| Ex. | Chemical Structure |
|---|---|
| 603 | 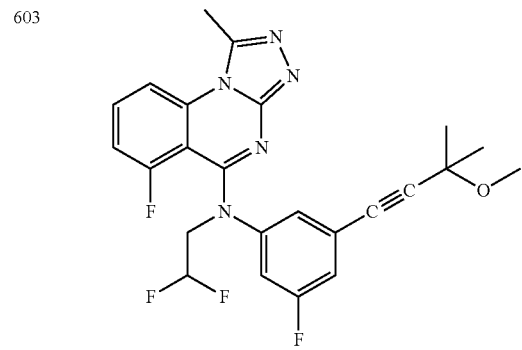 |
| 604 | 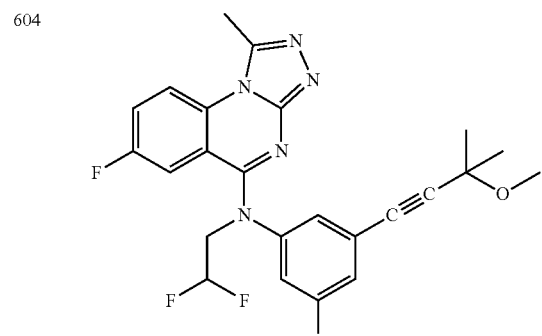 |
| 606 | 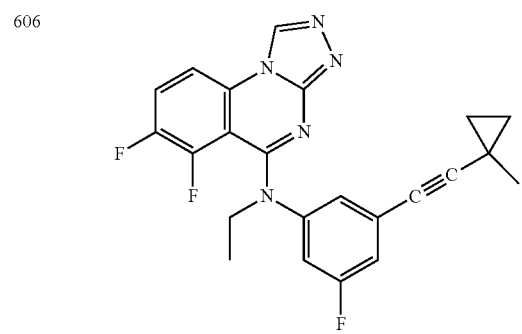 |
| 607 | 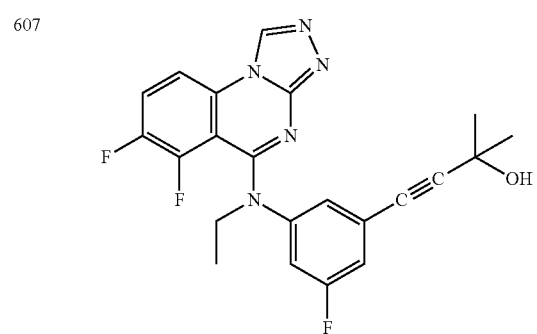 |
TABLE 3A-continued
Compounds
| Ex. | Chemical Structure |
|---|---|
| 608 | 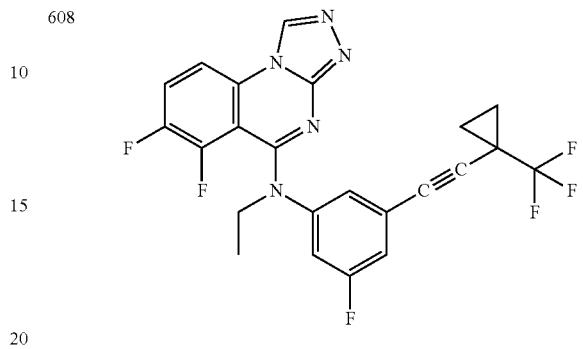 |
| 609 | 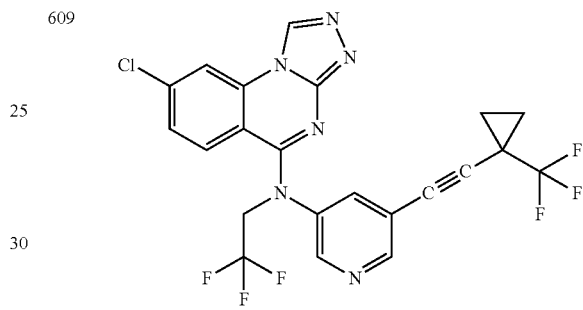 |
| 610 | 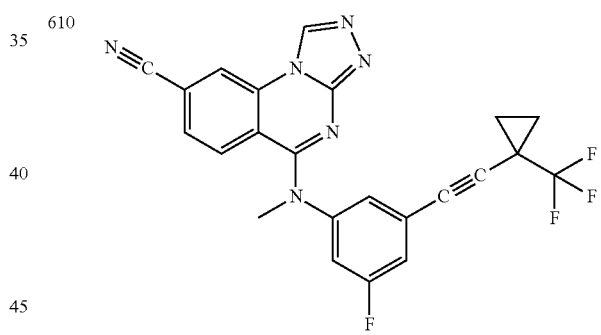 |
| 611 | 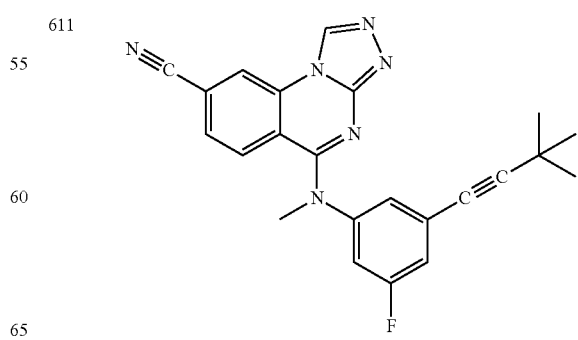 |

323
TABLE 3A-continued
Compounds
| Ex. | Chemical Structure |
|---|---|
| 612 | 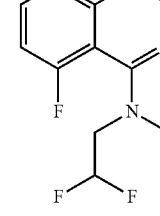 |
| 613 | 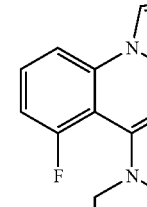 |
TABLE 3B
Compounds
| Ex. | Chemical Structure |
|---|---|
| 614 | 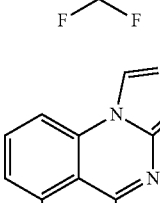 |
| 615 | 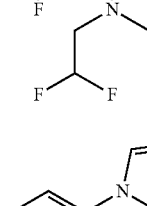 |
324
TABLE 3B-continued
Compounds
| Ex. | Chemical Structure |
|---|---|
| 616 | 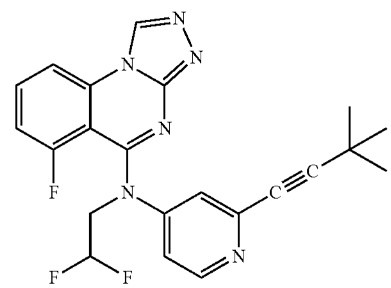 [SMILES: CC(C)(C)C#Cc1cc(N(CC(F)F)c2nc3nncn3c3cccc(F)c23)ccn1] |
| 617 | 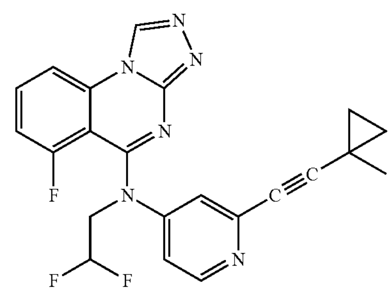 [SMILES: CC1(C#Cc2cc(N(CC(F)F)c3nc4nncn4c4cccc(F)c34)ccn2)CC1] |
| 618 | 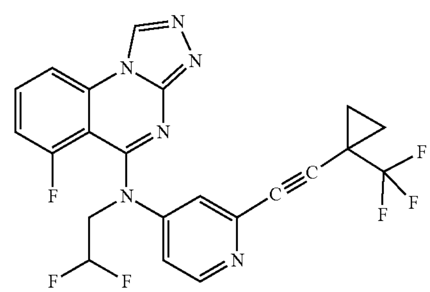 [SMILES: Fc1cccc2c1c(N(CC(F)F)c1ccnc(C#CC3(C(F)(F)F)CC3)c1)nc1nncn12] |
| 619 | 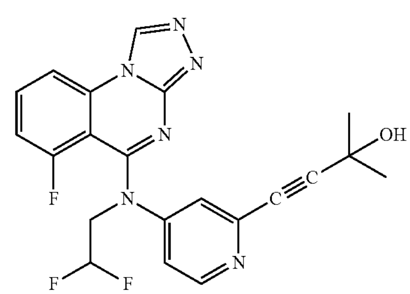 [SMILES: CC(C)(O)C#Cc1cc(N(CC(F)F)c2nc3nncn3c3cccc(F)c23)ccn1] |
| 620 | 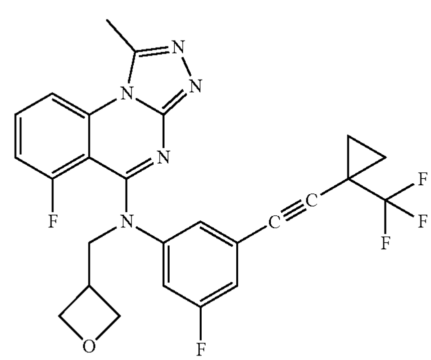 [SMILES: Cc1nnc2nc(N(CC3COC3)c3cc(F)cc(C#CC4(C(F)(F)F)CC4)c3)c3c(F)cccc3n12] |
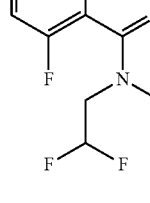

TABLE 3B-continued

| Ex. | Chemical Structure |
|---|---|
| 621 | |
| 622 | |
| 623 | |
| 624 | |
| 625 | |
| 626 | |
| 627 | |
| 628 | |
| 785 | |
| 793 | |

US 11,845,723 B2

TABLE 3B-continued

Compounds

| Ex. | Chemical Structure |
|---|---|
| 811 | (structure) |

TABLE 3C

Compounds

| Ex. | Chemical Structure |
|---|---|
| 629 | (structure) |
| 630 | (structure) |
| 631 | (structure) |

TABLE 3C-continued

Compounds

| Ex. | Chemical Structure |
|---|---|
| 632 | (structure) |
| 633 | (structure) |
| 634 | (structure) |
| 635 | (structure) |
| 814 | (structure) |

TABLE 3C-continued

| Ex. | Chemical Structure |
|---|---|
| 815 | |
| 816 | |
| 817 | |
| 818 | |
| 819 | 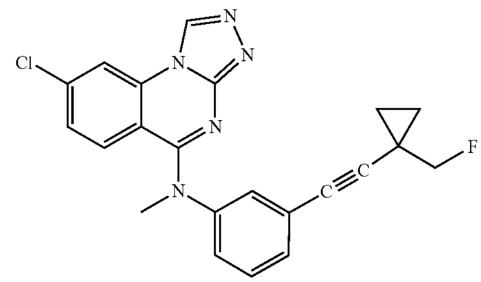 [SMILES: CN(c1cccc(C#CC2(CF)CC2)c1)c1nc2nncn2c2cc(Cl)ccc12] |
| 820 | 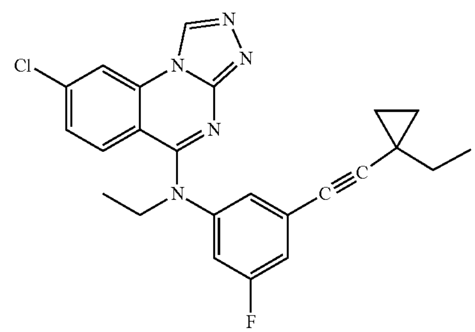 [SMILES: CCN(c1cc(F)cc(C#CC2(CC)CC2)c1)c1nc2nncn2c2cc(Cl)ccc12] |
| 821 | 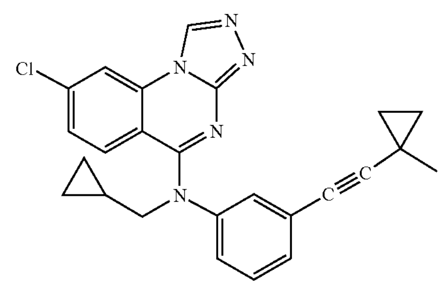 [SMILES: CC1(C#Cc2cccc(N(CC3CC3)c3nc4nncn4c4cc(Cl)ccc34)c2)CC1] |
| 822 | 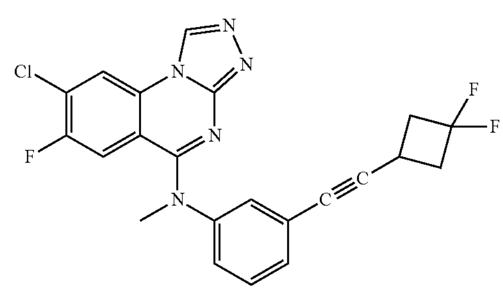 [SMILES: CN(c1cccc(C#CC2CC(F)(F)C2)c1)c1nc2nncn2c2cc(Cl)c(F)cc12] |
| 823 | 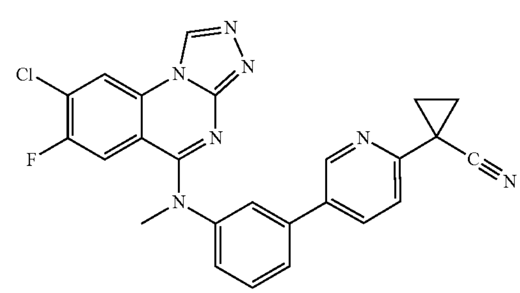 [SMILES: CN(c1cccc(-c2ccc(C3(C#N)CC3)nc2)c1)c1nc2nncn2c2cc(Cl)c(F)cc12] |

TABLE 3C-continued
| Ex. | Chemical Structure |
|---|---|
| 824 | 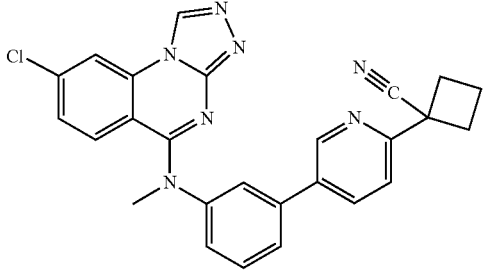 [SMILES: CN(c1cccc(-c2ccc(C3(C#N)CCC3)nc2)c1)c1nc2nncn2c2cc(Cl)ccc12] |
TABLE 3D
| Ex. | Chemical Structure |
|---|---|
| 656 | 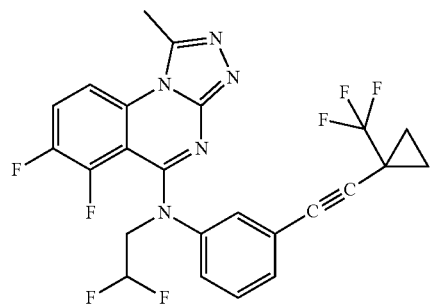 [SMILES: Cc1nnc2nc(N(CC(F)F)c3cccc(C#CC4(C(F)(F)F)CC4)c3)c3c(F)c(F)ccc3n12] |
| 657 | 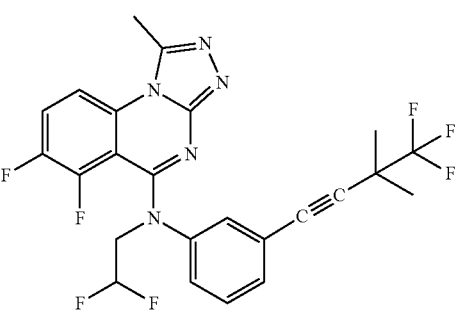 [SMILES: Cc1nnc2nc(N(CC(F)F)c3cccc(C#CC(C)(C)C(F)(F)F)c3)c3c(F)c(F)ccc3n12] |
| 658 | 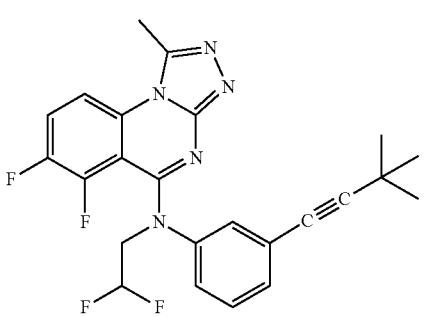 [SMILES: Cc1nnc2nc(N(CC(F)F)c3cccc(C#CC(C)(C)C)c3)c3c(F)c(F)ccc3n12] |
TABLE 3D-continued
| Ex. | Chemical Structure |
|---|---|
| 659 | 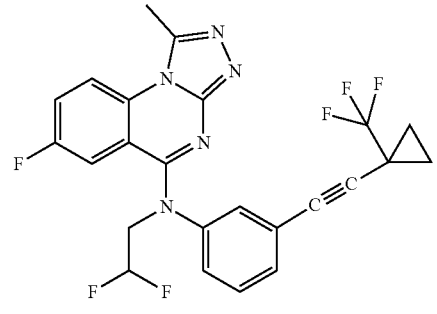 [SMILES: Cc1nnc2nc(N(CC(F)F)c3cccc(C#CC4(C(F)(F)F)CC4)c3)c3cc(F)ccc3n12] |
| 660 | 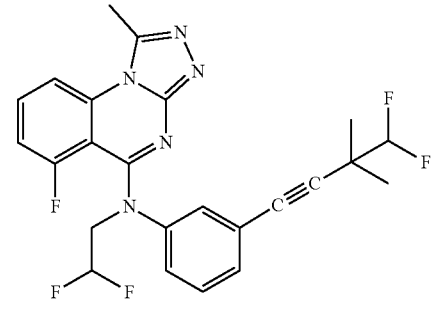 [SMILES: Cc1nnc2nc(N(CC(F)F)c3cccc(C#CC(C)(C)C(F)F)c3)c3c(F)cccc3n12] |
| 661 | 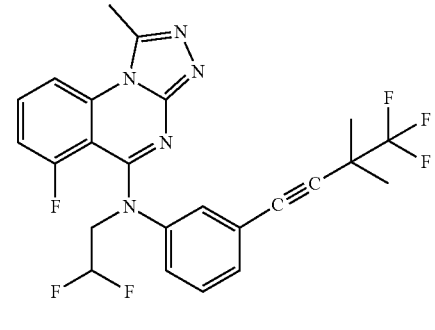 [SMILES: Cc1nnc2nc(N(CC(F)F)c3cccc(C#CC(C)(C)C(F)(F)F)c3)c3c(F)cccc3n12] |
| 662 | 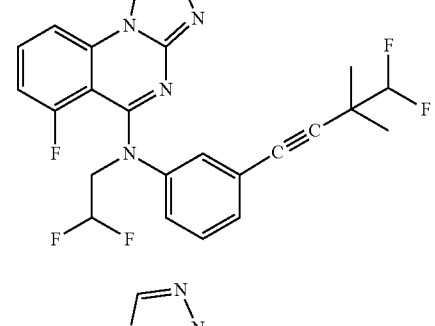 |
| 663 | 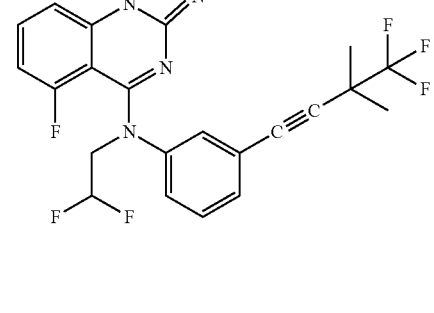 |

TABLE 3D-continued
Compounds
| Ex. | Chemical Structure |
|---|---|
| 664 | 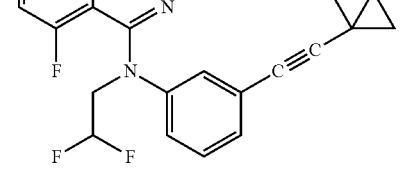 |
| 665 | 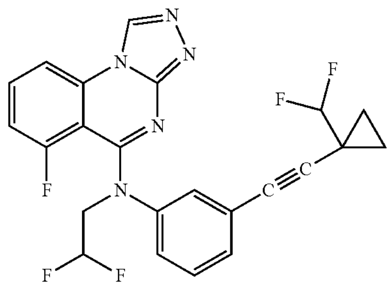 [SMILES: Fc1cccc2c1c(N(CC(F)F)c1cccc(C#CC3(C(F)F)CC3)c1)nc1nncn12] |
| 667 | 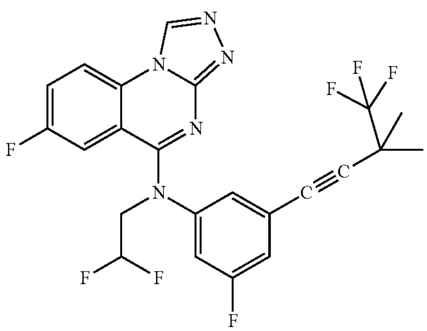 [SMILES: CC(C)(C#Cc1cc(F)cc(N(CC(F)F)c2nc3nncn3c3ccc(F)cc23)c1)C(F)(F)F] |
| 668 | 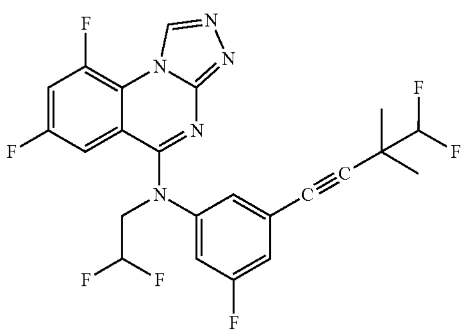 [SMILES: CC(C)(C#Cc1cc(F)cc(N(CC(F)F)c2nc3nncn3c3c(F)cc(F)cc23)c1)C(F)F] |
| 669 | 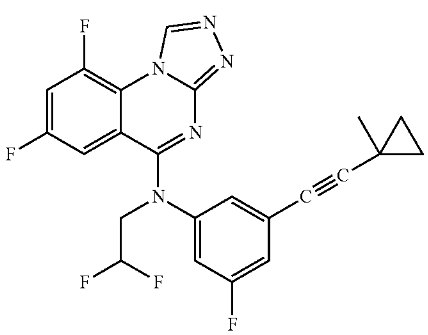 [SMILES: CC1(C#Cc2cc(F)cc(N(CC(F)F)c3nc4nncn4c4c(F)cc(F)cc34)c2)CC1] |
| 670 | 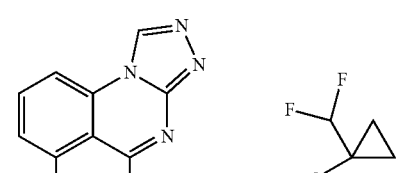 |
| 671 | 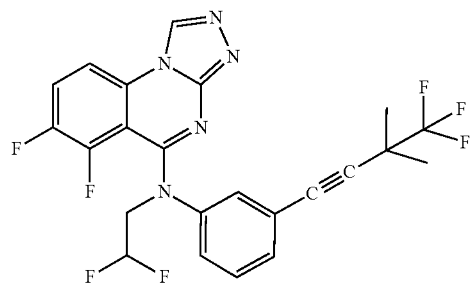 [SMILES: CC(C)(C#Cc1cccc(N(CC(F)F)c2nc3nncn3c3ccc(F)c(F)c23)c1)C(F)(F)F] |
| 672 | 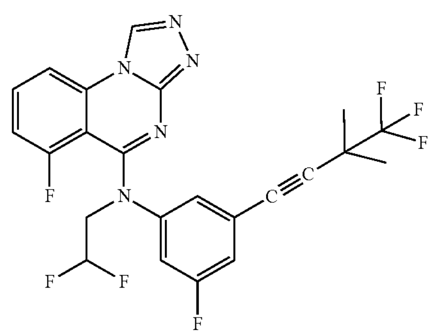 [SMILES: CC(C)(C#Cc1cc(F)cc(N(CC(F)F)c2nc3nncn3c3cccc(F)c23)c1)C(F)(F)F] |
| 673 | 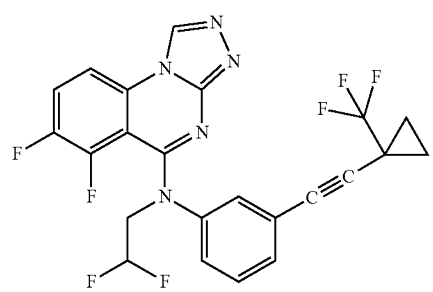 [SMILES: Fc1ccc2c(c(N(CC(F)F)c3cccc(C#CC4(C(F)(F)F)CC4)c3)nc3nncn32)c1F] |

TABLE 3D-continued
Compounds
| Ex. | Chemical Structure |
|---|---|
| 674 | 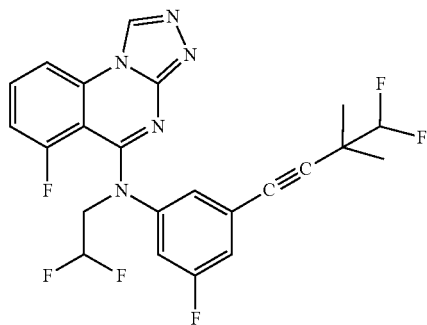 [SMILES: CC(C)(C#Cc1cc(F)cc(N(CC(F)F)c2nc3nncn3c3cccc(F)c23)c1)C(F)F] |
| 675 | 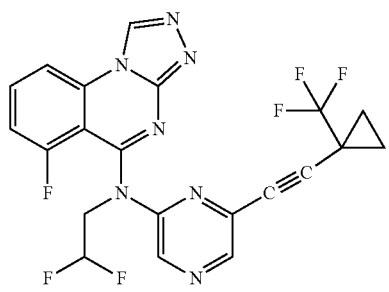 [SMILES: Fc1cccc2c1c(N(CC(F)F)c1cncc(C#CC3(C(F)(F)F)CC3)n1)nc1nncn12] |
| 676 | 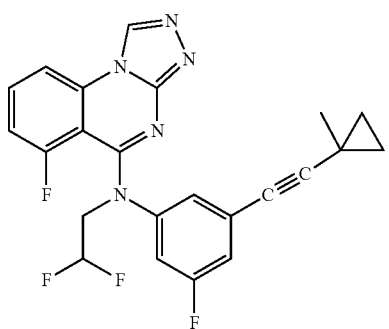 [SMILES: CC1(C#Cc2cc(F)cc(N(CC(F)F)c3nc4nncn4c4cccc(F)c34)c2)CC1] |
| 677 | 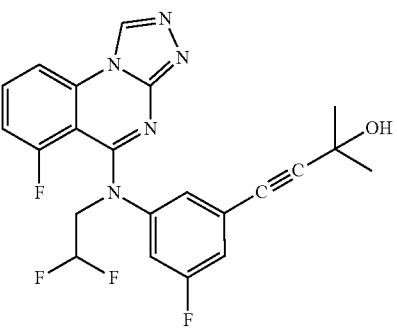 [SMILES: CC(C)(O)C#Cc1cc(F)cc(N(CC(F)F)c2nc3nncn3c3cccc(F)c23)c1] |
| 678 | 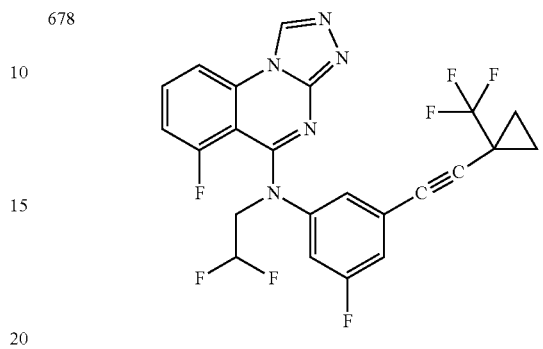 |
| 679 | 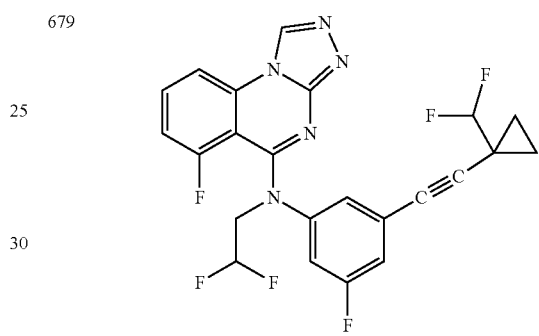 |
| 680 | 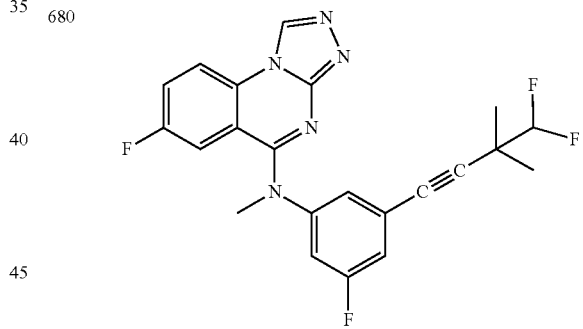 |
| 681 | 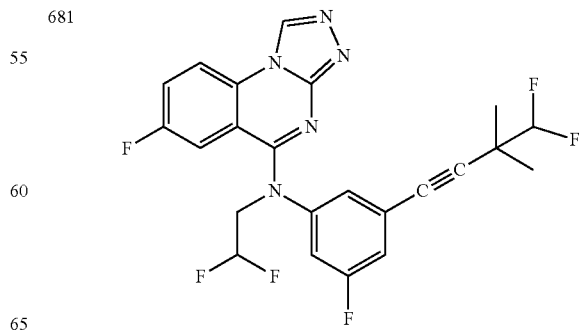 |

TABLE 3D-continued

Compounds

| Ex. | Chemical Structure |
|-----|--------------------|
| 682 | 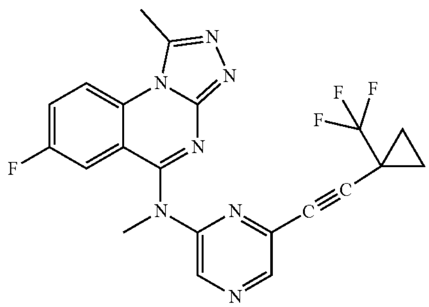 [SMILES: Cc1nnc2nc(N(C)c3cncc(C#CC4(C(F)(F)F)CC4)n3)c3cc(F)ccc3n12] |
| 683 | 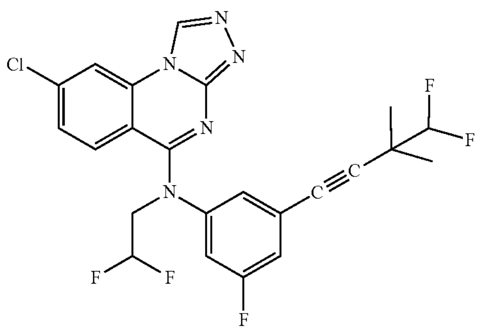 [SMILES: CC(C)(C#Cc1cc(F)cc(N(CC(F)F)c2nc3nncn3c3cc(Cl)ccc23)c1)C(F)F] |
| 684 | 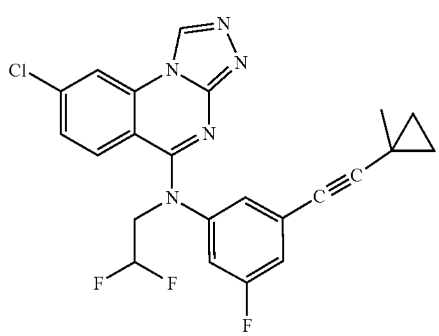 [SMILES: CC1(C#Cc2cc(F)cc(N(CC(F)F)c3nc4nncn4c4cc(Cl)ccc34)c2)CC1] |
| 685 | 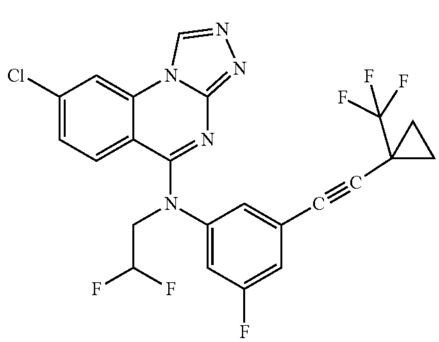 [SMILES: Fc1cc(C#CC2(C(F)(F)F)CC2)cc(N(CC(F)F)c2nc3nncn3c3cc(Cl)ccc23)c1] |

TABLE 3D-continued

Compounds

| Ex. | Chemical Structure |
|-----|--------------------|
| 676 | 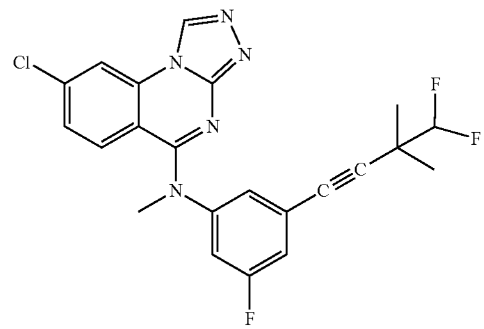 [SMILES: CN(c1cc(F)cc(C#CC(C)(C)C(F)F)c1)c1nc2nncn2c2cc(Cl)ccc12] |
| 687 | 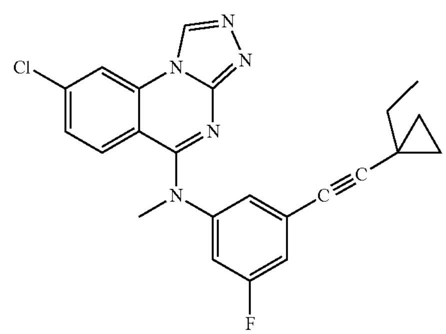 [SMILES: CCC1(C#Cc2cc(F)cc(N(C)c3nc4nncn4c4cc(Cl)ccc34)c2)CC1] |
| 688 | 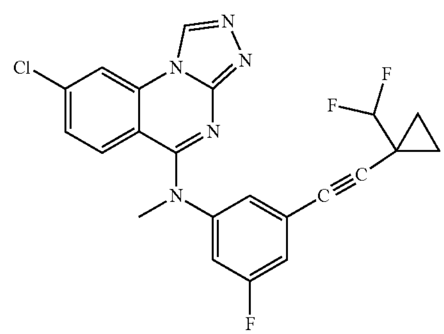 [SMILES: CN(c1cc(F)cc(C#CC2(C(F)F)CC2)c1)c1nc2nncn2c2cc(Cl)ccc12] |
| 689 | 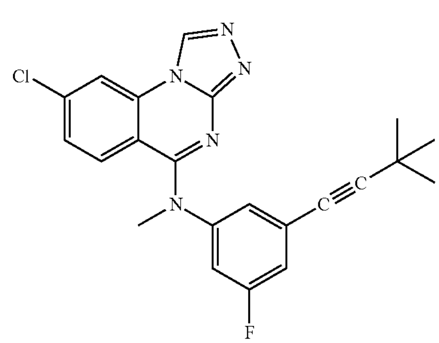 [SMILES: CN(c1cc(F)cc(C#CC(C)(C)C)c1)c1nc2nncn2c2cc(Cl)ccc12] |

TABLE 3D-continued

Compounds

| Ex. | Chemical Structure |
|---|---|
| 690 | 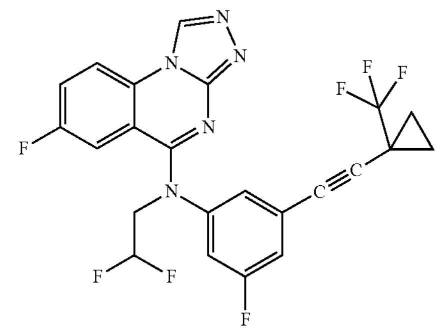 [SMILES: Fc1cc(C#CC2(C(F)(F)F)CC2)cc(N(CC(F)F)c2nc3nncn3c3ccc(F)cc23)c1] |
| 691 | 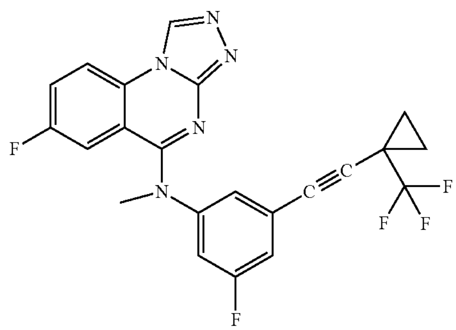 [SMILES: CN(c1cc(F)cc(C#CC2(C(F)(F)F)CC2)c1)c1nc2nncn2c2ccc(F)cc12] |
| 692 | 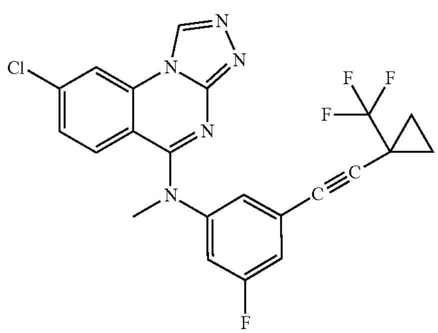 [SMILES: CN(c1cc(F)cc(C#CC2(C(F)(F)F)CC2)c1)c1nc2nncn2c2cc(Cl)ccc12] |
| 693 | 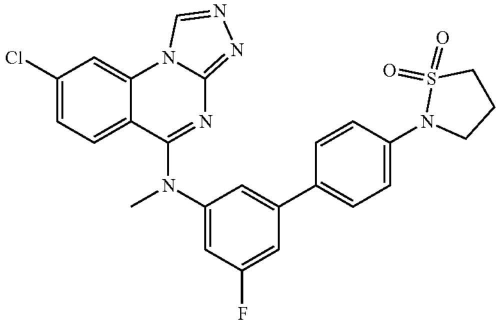 [SMILES: CN(c1cc(F)cc(-c2ccc(N3CCCS3(=O)=O)cc2)c1)c1nc2nncn2c2cc(Cl)ccc12] |

TABLE 3D-continued

Compounds

| Ex. | Chemical Structure |
|---|---|
| 694 | 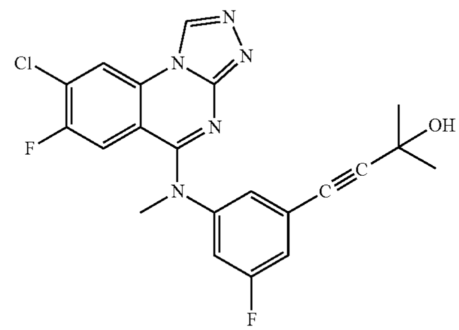 [SMILES: CN(c1cc(F)cc(C#CC(C)(C)O)c1)c1nc2nncn2c2cc(Cl)c(F)cc12] |
| 695 | 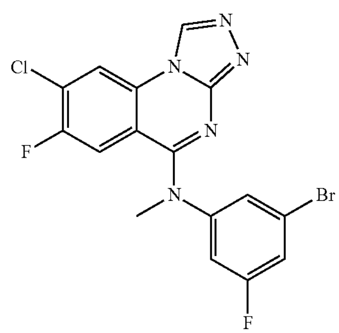 [SMILES: CN(c1cc(F)cc(Br)c1)c1nc2nncn2c2cc(Cl)c(F)cc12] |
| 698 | 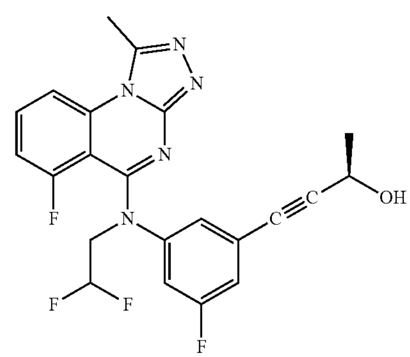 [SMILES: Cc1nnc2nc(N(CC(F)F)c3cc(F)cc(C#C[C@@H](C)O)c3)c3c(F)cccc3n12] |
| 699 | 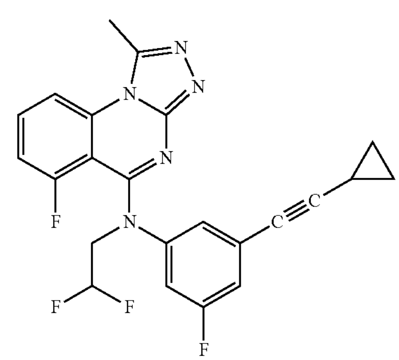 [SMILES: Cc1nnc2nc(N(CC(F)F)c3cc(F)cc(C#CC4CC4)c3)c3c(F)cccc3n12] |

TABLE 3D-continued

| Compounds | |
|---|---|
| Ex. | Chemical Structure |
| 705 | |
| 706 | |
| 707 | |
| 708 | |

TABLE 3D-continued

| Compounds | |
|---|---|
| Ex. | Chemical Structure |
| 709 | |
| 731 | |
| 732 | |
| 733 | |

TABLE 3D-continued

Compounds

| Ex. | Chemical Structure |
|---|---|
| 734 | 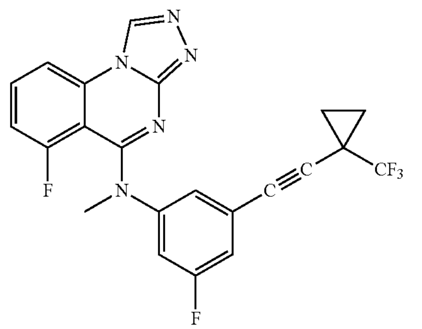 [SMILES: CN(c1cc(F)cc(C#CC2(C(F)(F)F)CC2)c1)c1nc2nncn2c2cccc(F)c12] |
| 735 | 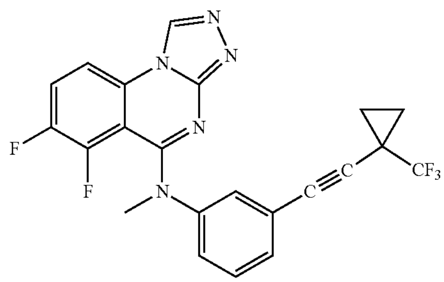 [SMILES: CN(c1cccc(C#CC2(C(F)(F)F)CC2)c1)c1nc2nncn2c2ccc(F)c(F)c12] |
| 736 | 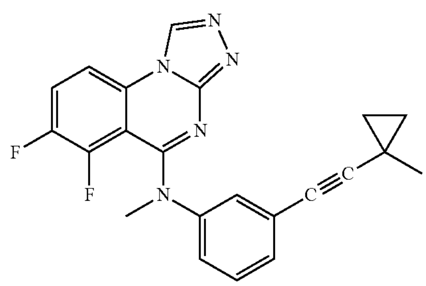 [SMILES: CN(c1cccc(C#CC2(C)CC2)c1)c1nc2nncn2c2ccc(F)c(F)c12] |
| 737 | 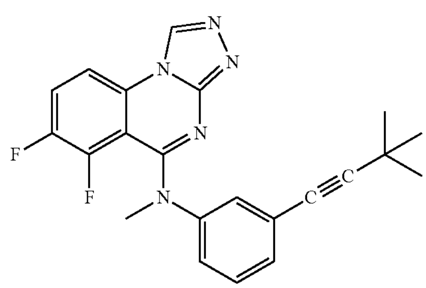 [SMILES: CN(c1cccc(C#CC(C)(C)C)c1)c1nc2nncn2c2ccc(F)c(F)c12] |
| 738 | 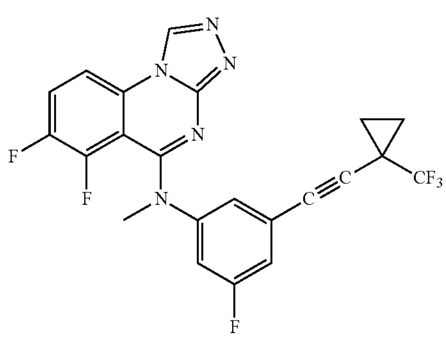 [SMILES: CN(c1cc(F)cc(C#CC2(C(F)(F)F)CC2)c1)c1nc2nncn2c2ccc(F)c(F)c12] |

TABLE 3E

Compounds

| Ex. | Chemical Structure |
|---|---|
| 681 | 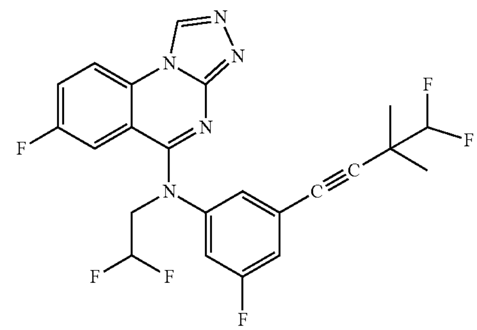 [SMILES: CC(C)(C#Cc1cc(F)cc(N(CC(F)F)c2nc3nncn3c3ccc(F)cc23)c1)C(F)F] |
| 682 | 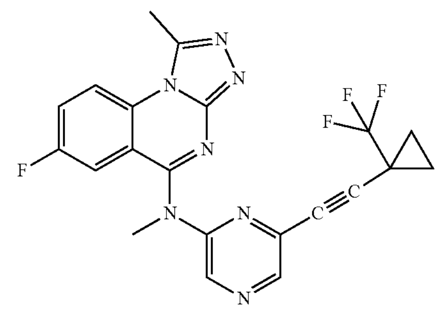 [SMILES: Cc1nnc2nc(N(C)c3cncc(C#CC4(C(F)(F)F)CC4)n3)c3cc(F)ccc3n12] |
| 683 | 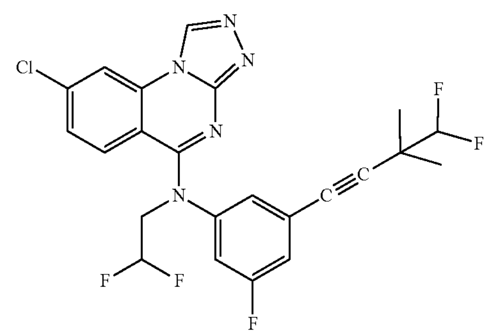 [SMILES: CC(C)(C#Cc1cc(F)cc(N(CC(F)F)c2nc3nncn3c3cc(Cl)ccc23)c1)C(F)F] |
| 684 | 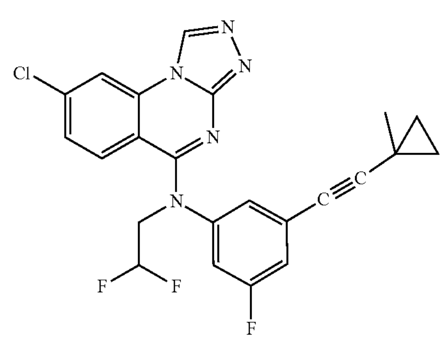 [SMILES: CC1(C#Cc2cc(F)cc(N(CC(F)F)c3nc4nncn4c4cc(Cl)ccc34)c2)CC1] |

TABLE 3E-continued

Compounds

| Ex. | Chemical Structure |
|---|---|
| 685 | 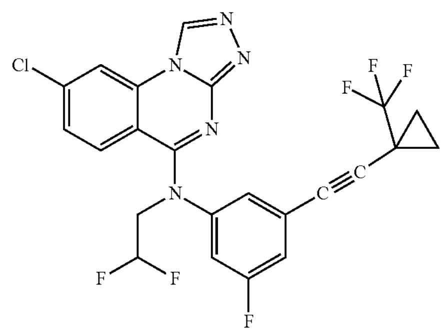 [SMILES: Fc1cc(C#CC2(C(F)(F)F)CC2)cc(N(CC(F)F)c2nc3nncn3c3cc(Cl)ccc23)c1] |
| 686 | 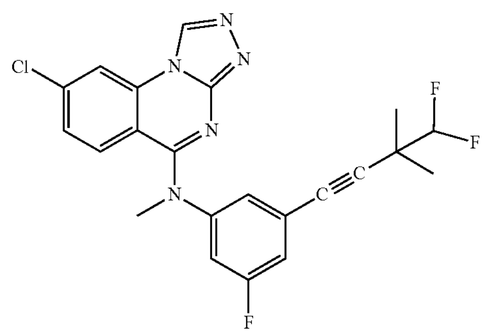 [SMILES: CN(c1cc(F)cc(C#CC(C)(C)C(F)F)c1)c1nc2nncn2c2cc(Cl)ccc12] |
| 687 | 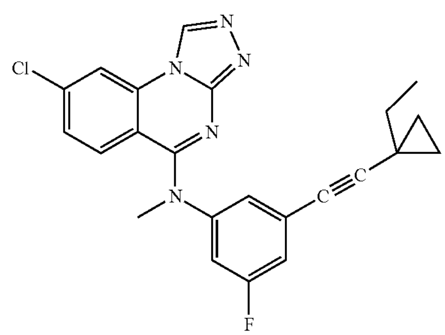 [SMILES: CCC1(C#Cc2cc(F)cc(N(C)c3nc4nncn4c4cc(Cl)ccc34)c2)CC1] |
| 688 | 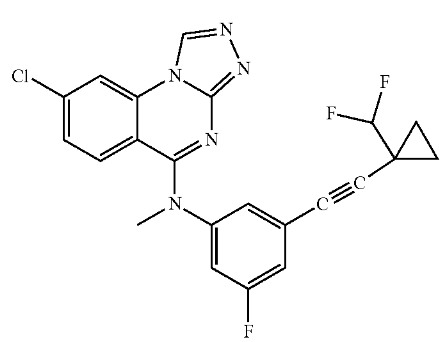 [SMILES: CN(c1cc(F)cc(C#CC2(C(F)F)CC2)c1)c1nc2nncn2c2cc(Cl)ccc12] |
| 689 | 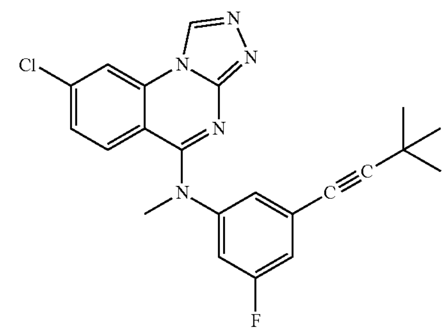 [SMILES: CN(c1cc(F)cc(C#CC(C)(C)C)c1)c1nc2nncn2c2cc(Cl)ccc12] |
| 690 | 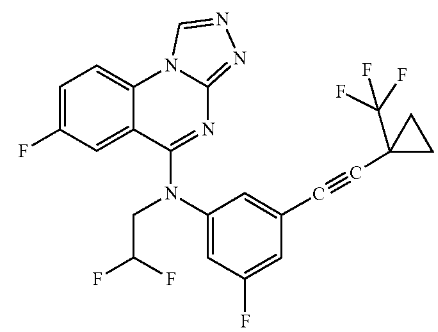 |
| 691 | 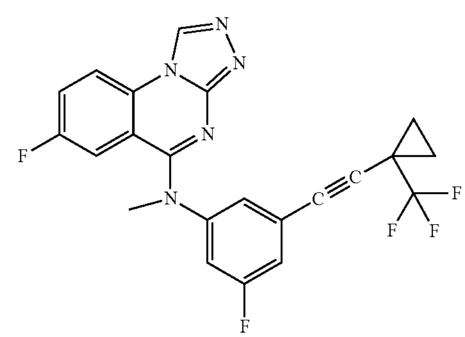 [SMILES: CN(c1cc(F)cc(C#CC2(C(F)(F)F)CC2)c1)c1nc2nncn2c2ccc(F)cc12] |
| 692 | 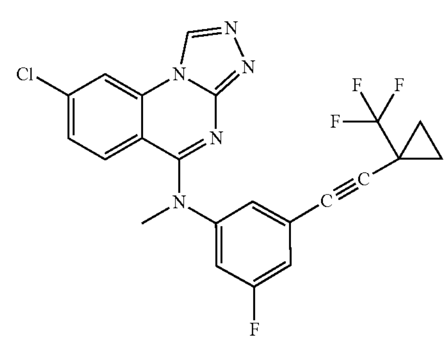 [SMILES: CN(c1cc(F)cc(C#CC2(C(F)(F)F)CC2)c1)c1nc2nncn2c2cc(Cl)ccc12] |

TABLE 3E-continued

| Ex. | Chemical Structure |
|---|---|
| 693 | 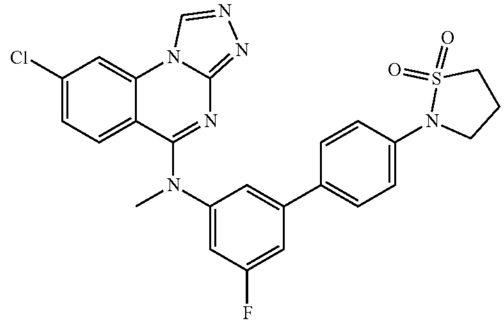 [SMILES: CN(c1cc(F)cc(-c2ccc(N3CCCS3(=O)=O)cc2)c1)c1nc2nncn2c2cc(Cl)ccc12] |
| 694 | 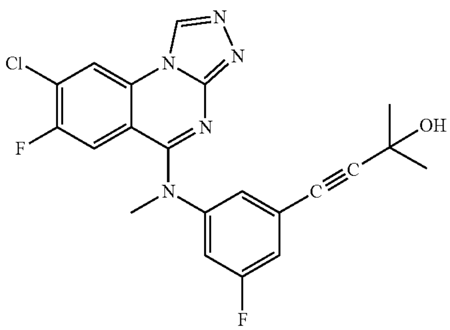 [SMILES: CN(c1cc(F)cc(C#CC(C)(C)O)c1)c1nc2nncn2c2cc(Cl)c(F)cc12] |
| 695 | 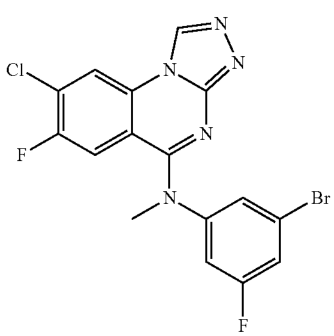 [SMILES: CN(c1cc(F)cc(Br)c1)c1nc2nncn2c2cc(Cl)c(F)cc12] |
| 698 | 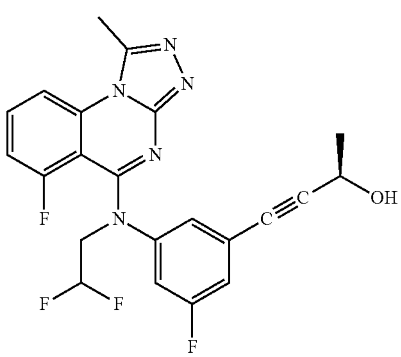 [SMILES: Cc1nnc2nc(N(CC(F)F)c3cc(F)cc(C#C[C@@H](C)O)c3)c3c(F)cccc3n12] |

TABLE 3E-continued

| Ex. | Chemical Structure |
|---|---|
| 699 | 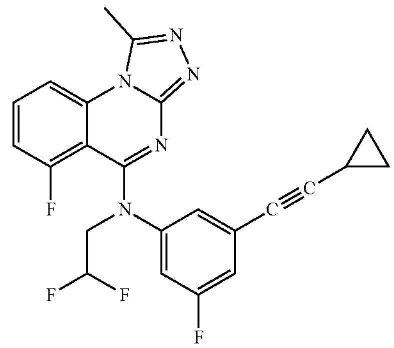 [SMILES: Cc1nnc2nc(N(CC(F)F)c3cc(F)cc(C#CC4CC4)c3)c3c(F)cccc3n12] |
| 705 | 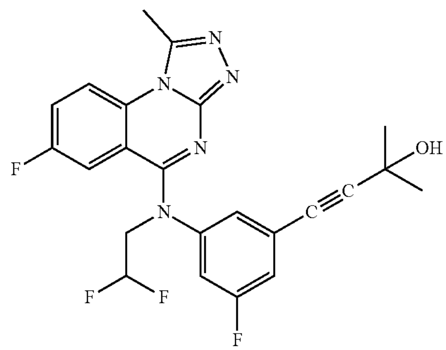 [SMILES: Cc1nnc2nc(N(CC(F)F)c3cc(F)cc(C#CC(C)(C)O)c3)c3cc(F)ccc3n12] |
| 706 | 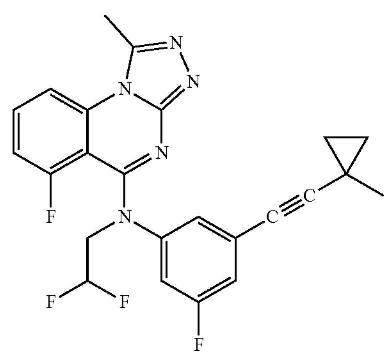 [SMILES: Cc1nnc2nc(N(CC(F)F)c3cc(F)cc(C#CC4(C)CC4)c3)c3c(F)cccc3n12] |
| 707 | 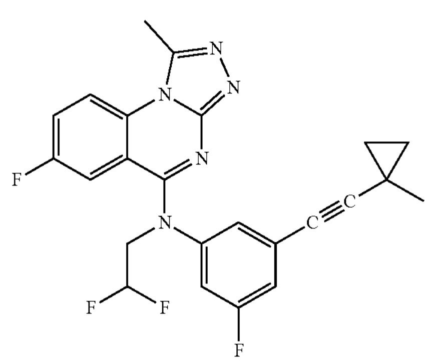 [SMILES: Cc1nnc2nc(N(CC(F)F)c3cc(F)cc(C#CC4(C)CC4)c3)c3cc(F)ccc3n12] |

TABLE 3E-continued
Compounds
| Ex. | Chemical Structure |
|---|---|
| 708 | 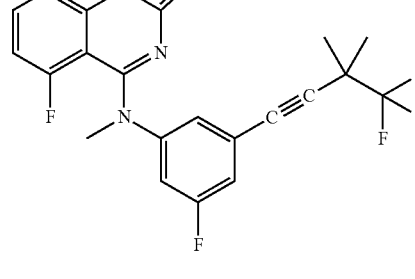 |
| 709 | 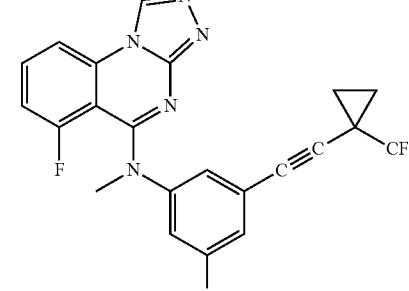 |
| 731 | 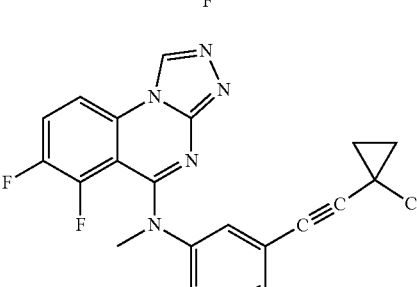 |
| 732 | 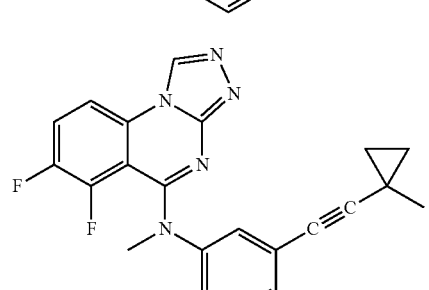 |
| 733 | 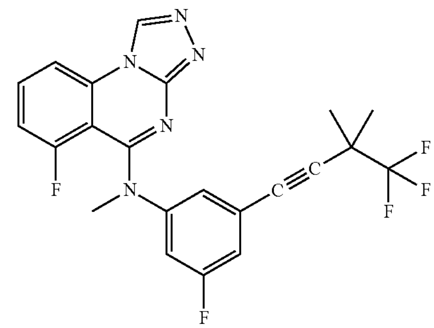 [SMILES: CN(c1cc(F)cc(C#CC(C)(C)C(F)(F)F)c1)c1nc2nncn2c2cccc(F)c12] |
| 734 | 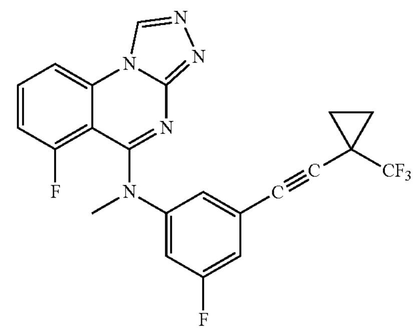 [SMILES: CN(c1cc(F)cc(C#CC2(C(F)(F)F)CC2)c1)c1nc2nncn2c2cccc(F)c12] |
| 735 | 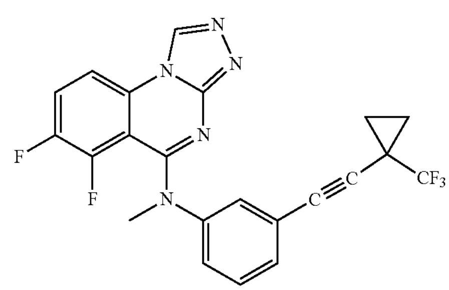 [SMILES: CN(c1cccc(C#CC2(C(F)(F)F)CC2)c1)c1nc2nncn2c2ccc(F)c(F)c12] |
| 736 | 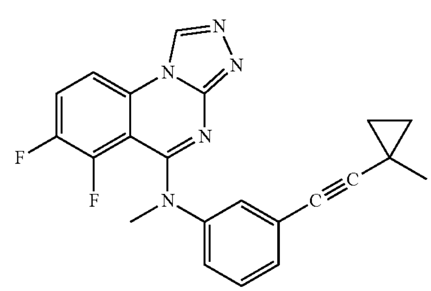 [SMILES: CN(c1cccc(C#CC2(C)CC2)c1)c1nc2nncn2c2ccc(F)c(F)c12] |
| 737 | 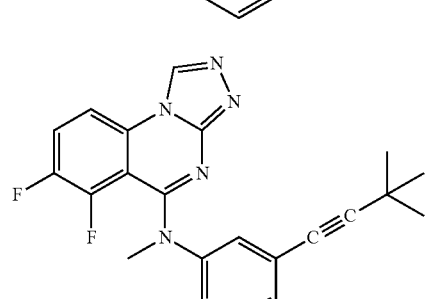 |

TABLE 3E-continued
| Compounds | |
|---|---|
| Ex. | Chemical Structure |
| 738 | 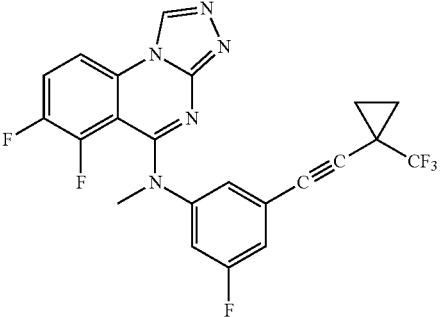 |
TABLE 3F
| Compounds | |
|---|---|
| Ex. | Chemical Structure |
| 655 | 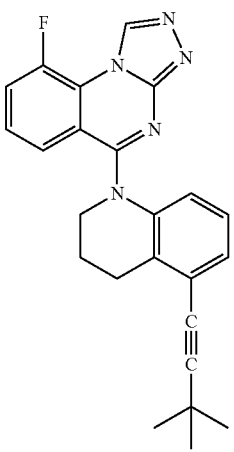 [SMILES: CC(C)(C)C#Cc1cccc2c1CCCN2c1nc2nncn2c2c(F)cccc12] |
| 700 | 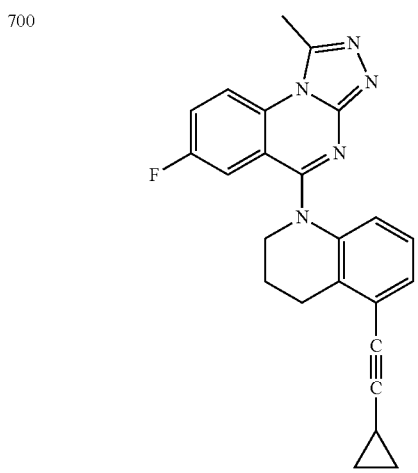 |
TABLE 3F-continued
| Compounds | |
|---|---|
| Ex. | Chemical Structure |
| 701 | 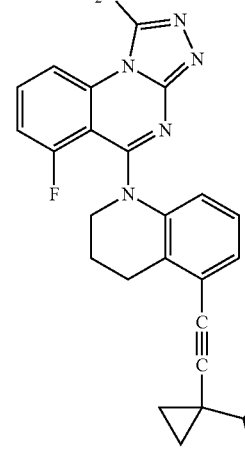 |
| 702 | 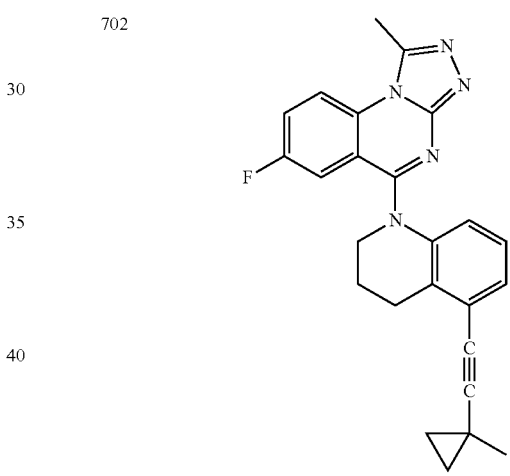 |
| 703 | 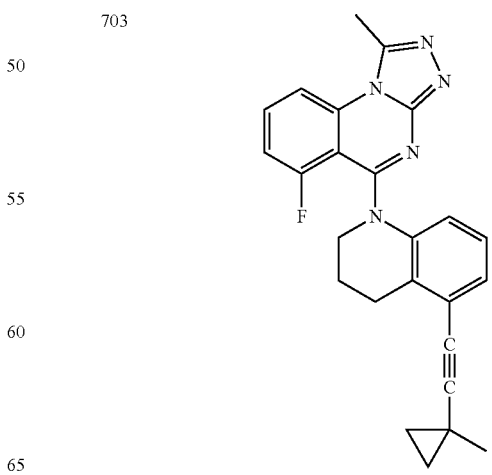 |

TABLE 3F-continued
Compounds
| Ex. | Chemical Structure |
|---|---|
| 710 | 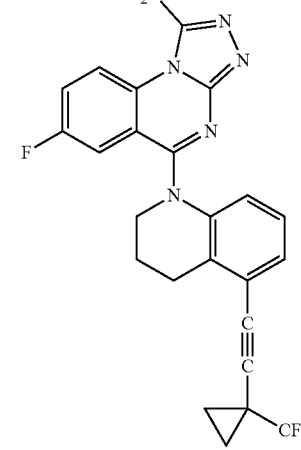 |
| 711 | 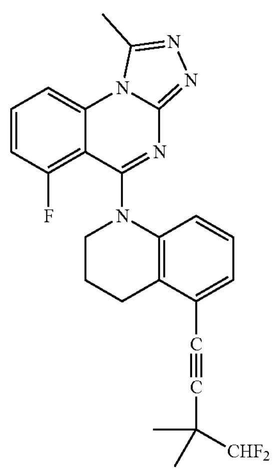 [SMILES: Cc1nnc2nc(N3CCCc4c(C#CC(C)(C)C(F)F)cccc43)c3c(F)cccc3n12] |
| 712 | 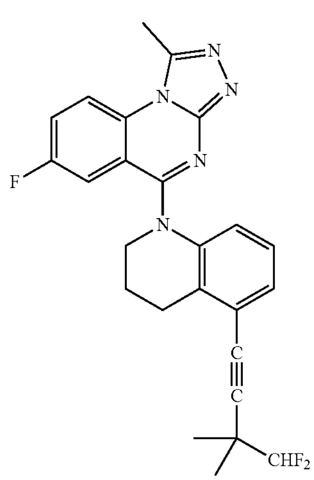 [SMILES: Cc1nnc2nc(N3CCCc4c(C#CC(C)(C)C(F)F)cccc43)c3cc(F)ccc3n12] |
TABLE 3F-continued
Compounds
| Ex. | Chemical Structure |
|---|---|
| 713 | 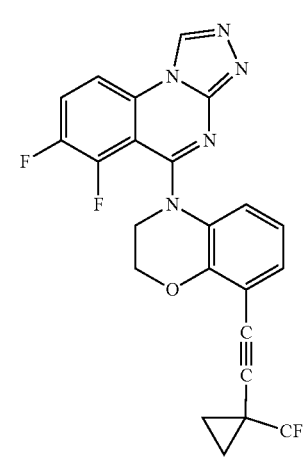 |
| 714 | 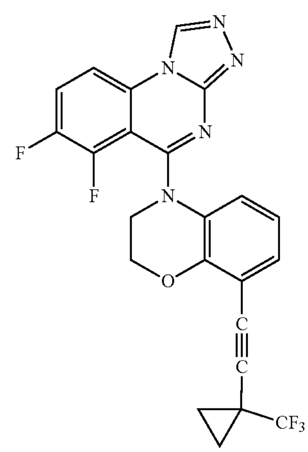 [SMILES: Fc1ccc2c(c(N3CCOc4c(C#CC5(C(F)(F)F)CC5)cccc43)nc3nncn32)c1F] |
| 715 | 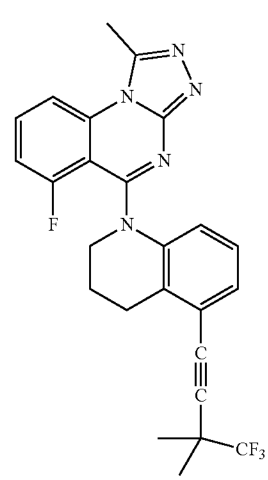 [SMILES: Cc1nnc2nc(N3CCCc4c(C#CC(C)(C)C(F)(F)F)cccc43)c3c(F)cccc3n12] |

TABLE 3F-continued

| Compounds | |
|---|---|
| Ex. | Chemical Structure |
| 716 | |
| 717 | |
| 718 | |
| 723 | |
| 724 | |
| 725 | |

TABLE 3F-continued
| Ex. | Chemical Structure |
|---|---|
| 726 | 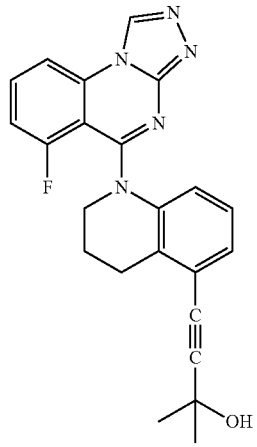 [SMILES: CC(C)(O)C#Cc1cccc2c1CCCN2c1nc2nncn2c2cccc(F)c12] |
| 727 | 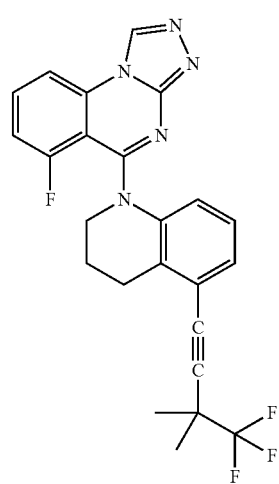 [SMILES: CC(C)(C#Cc1cccc2c1CCCN2c1nc2nncn2c2cccc(F)c12)C(F)(F)F] |
| 728 | 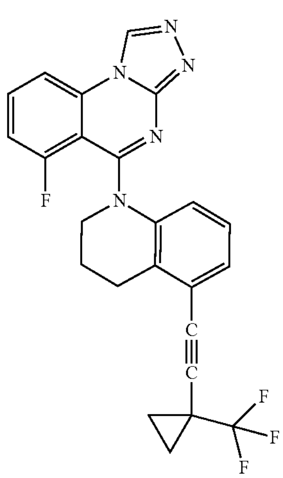 [SMILES: Fc1cccc2c1c(N1CCCc3c(C#CC4(C(F)(F)F)CC4)cccc31)nc1nncn12] |
TABLE 3F-continued
| Ex. | Chemical Structure |
|---|---|
| 729 | 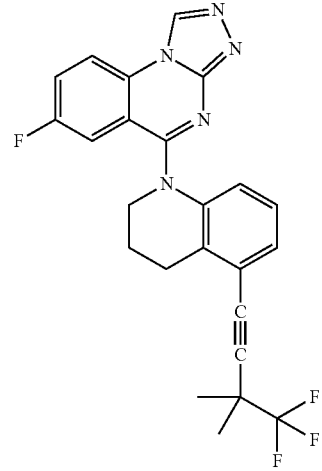 [SMILES: CC(C)(C#Cc1cccc2c1CCCN2c1nc2nncn2c2ccc(F)cc12)C(F)(F)F] |
| 730 | 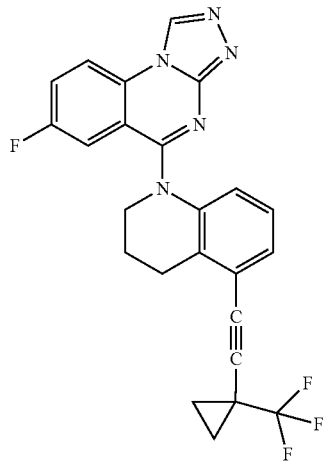 [SMILES: Fc1ccc2c(c1)c(N1CCCc3c(C#CC4(C(F)(F)F)CC4)cccc31)nc1nncn12] |
TABLE 3G
| Ex. | Chemical Structure |
|---|---|
| 704 | 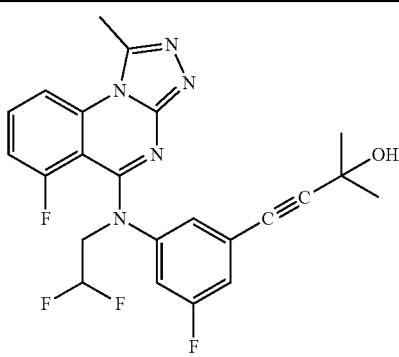 |

TABLE 3G-continued

Compounds

| Ex. | Chemical Structure |
|---|---|
| 739 | |
| 740 | |
| 741 | |
| 742 | |
| 743 | |
| 744 | |
| 745 | |
| 746 | |
| 752 | |

TABLE 3G-continued

Compounds

| Ex. | Chemical Structure |
|---|---|
| 753 | 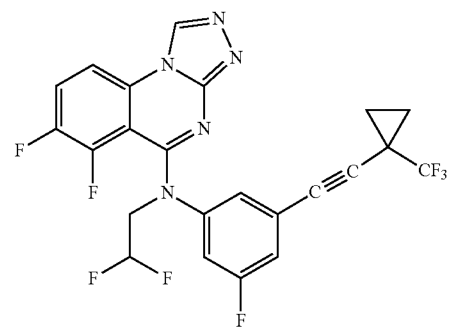 [SMILES: Fc1cc(C#CC2(C(F)(F)F)CC2)cc(N(CC(F)F)c2nc3nncn3c3ccc(F)c(F)c23)c1] |
| 754 | 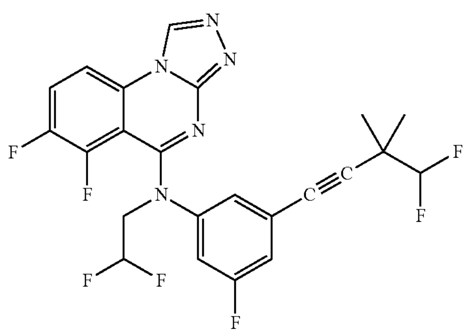 [SMILES: CC(C)(C#Cc1cc(F)cc(N(CC(F)F)c2nc3nncn3c3ccc(F)c(F)c23)c1)C(F)F] |
| 755 | 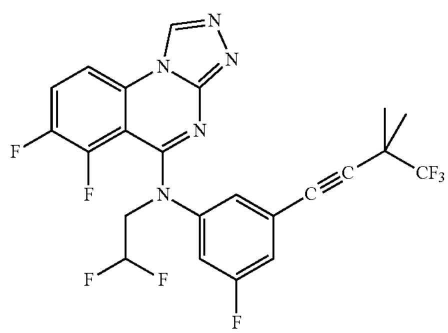 [SMILES: CC(C)(C#Cc1cc(F)cc(N(CC(F)F)c2nc3nncn3c3ccc(F)c(F)c23)c1)C(F)(F)F] |
| 756 | 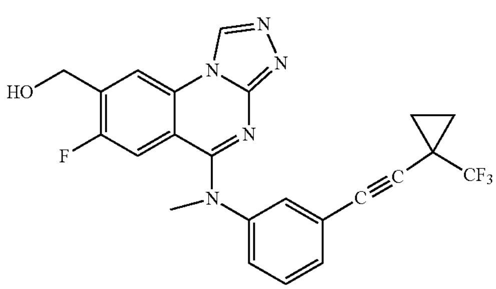 [SMILES: CN(c1cccc(C#CC2(C(F)(F)F)CC2)c1)c1nc2nncn2c2cc(CO)c(F)cc12] |
| 757 | 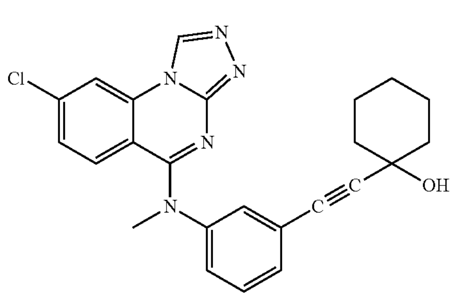 [SMILES: CN(c1cccc(C#CC2(O)CCCCC2)c1)c1nc2nncn2c2cc(Cl)ccc12] |
| 758 | |
| 759 | |
| 760 | |
| 761 | |

TABLE 3G-continued

Compounds

| Ex. | Chemical Structure |
|---|---|
| 762 | 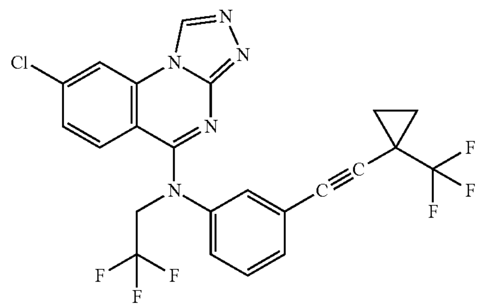 [SMILES: FC(F)(F)CN(c1cccc(C#CC2(C(F)(F)F)CC2)c1)c1nc2nncn2c2cc(Cl)ccc12] |
| 763 | 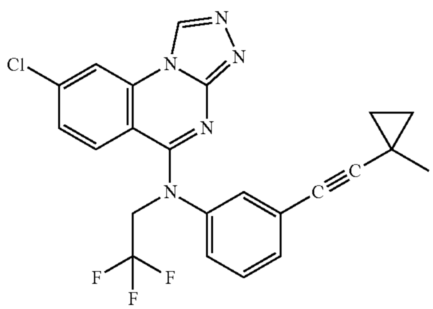 [SMILES: CC1(C#Cc2cccc(N(CC(F)(F)F)c3nc4nncn4c4cc(Cl)ccc34)c2)CC1] |
| 764 | 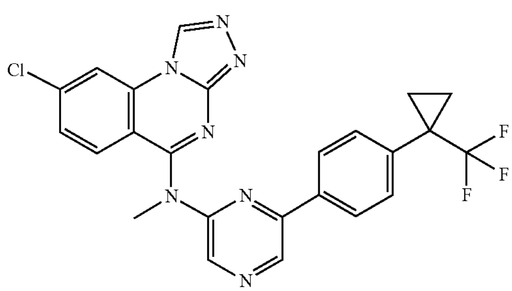 [SMILES: CN(c1cncc(-c2ccc(C3(C(F)(F)F)CC3)cc2)n1)c1nc2nncn2c2cc(Cl)ccc12] |
| 765 | 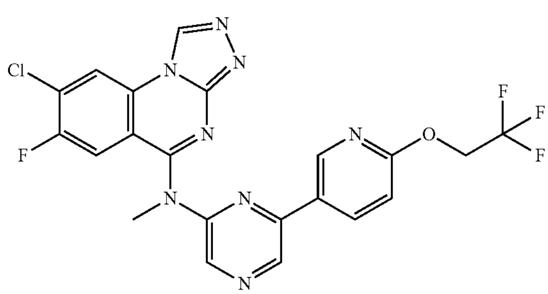 [SMILES: CN(c1cncc(-c2ccc(OCC(F)(F)F)nc2)n1)c1nc2nncn2c2cc(Cl)c(F)cc12] |
| 766 | 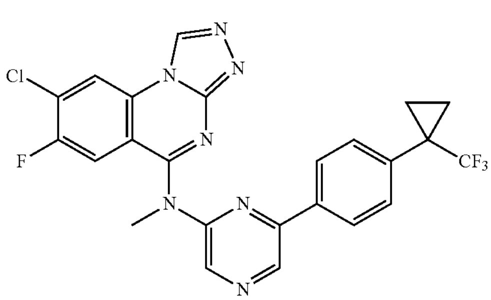 [SMILES: CN(c1cncc(-c2ccc(C3(C(F)(F)F)CC3)cc2)n1)c1nc2nncn2c2cc(Cl)c(F)cc12] |

TABLE 3G-continued

Compounds

| Ex. | Chemical Structure |
|---|---|
| 788 | 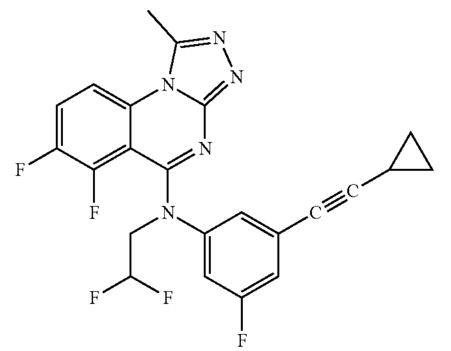 [SMILES: Cc1nnc2nc(N(CC(F)F)c3cc(F)cc(C#CC4CC4)c3)c3c(F)c(F)ccc3n12] |
| 796 | 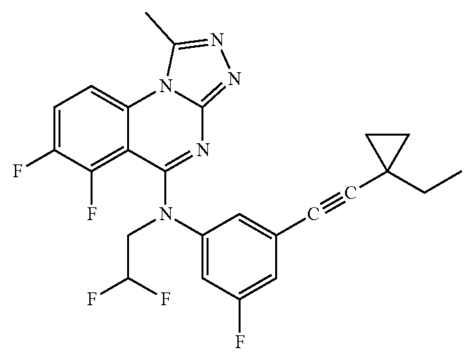 [SMILES: CCC1(C#Cc2cc(F)cc(N(CC(F)F)c3nc4nnc(C)n4c4ccc(F)c(F)c34)c2)CC1] |
| 801 | 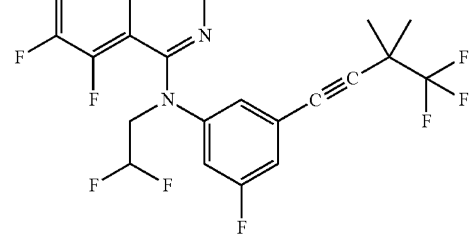 |
| 802 | 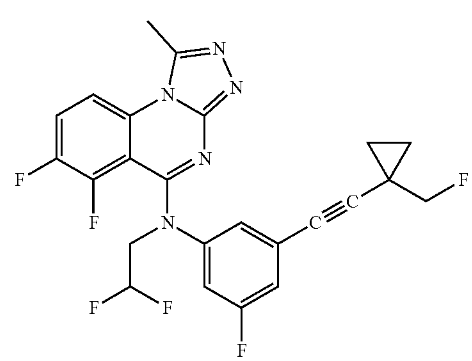 [SMILES: Cc1nnc2nc(N(CC(F)F)c3cc(F)cc(C#CC4(CF)CC4)c3)c3c(F)c(F)ccc3n12] |

TABLE 3G-continued

| Ex. | Chemical Structure |
|---|---|
| 803 | 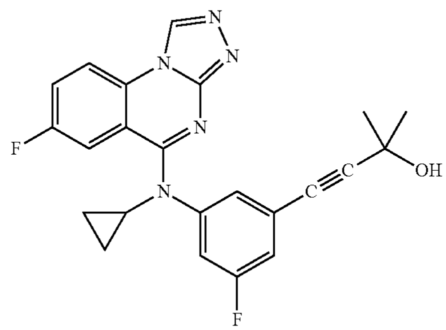 [SMILES: CC(C)(O)C#Cc1cc(F)cc(N(c2nc3nncn3c3ccc(F)cc23)C2CC2)c1] |
| 804 | 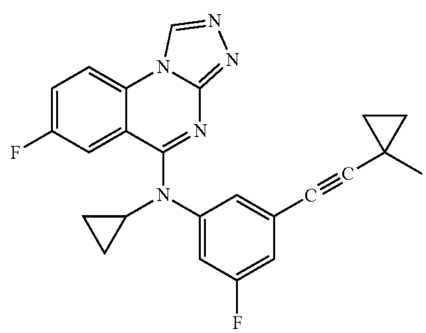 [SMILES: CC1(C#Cc2cc(F)cc(N(c3nc4nncn4c4ccc(F)cc34)C3CC3)c2)CC1] |
| 805 | 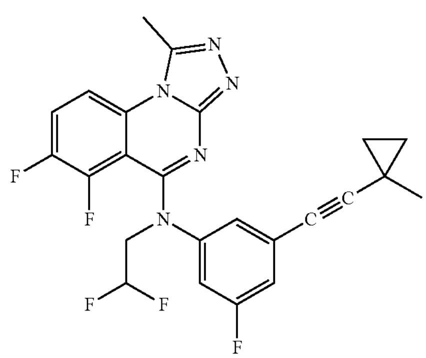 [SMILES: Cc1nnc2nc(N(CC(F)F)c3cc(F)cc(C#CC4(C)CC4)c3)c3c(F)c(F)ccc3n12] |
| 806 | 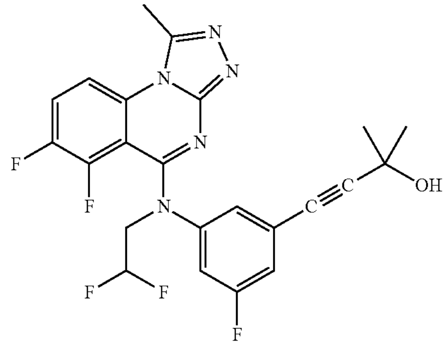 [SMILES: Cc1nnc2nc(N(CC(F)F)c3cc(F)cc(C#CC(C)(C)O)c3)c3c(F)c(F)ccc3n12] |

TABLE 3G-continued

| Ex. | Chemical Structure |
|---|---|
| 807 | |

TABLE 3H

| Ex. | Chemical Structure |
|---|---|
| 577 | 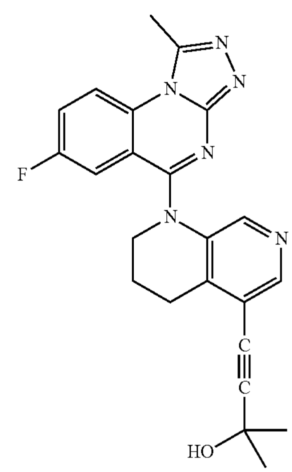 [SMILES: Cc1nnc2nc(N3CCCc4c(C#CC(C)(C)O)cncc43)c3cc(F)ccc3n12] |
| 578 | 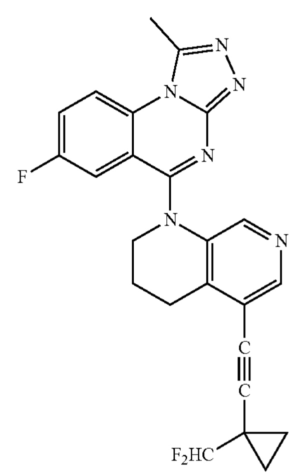 [SMILES: Cc1nnc2nc(N3CCCc4c(C#CC5(C(F)F)CC5)cncc43)c3cc(F)ccc3n12] |

TABLE 3H-continued
| Compounds | |
|---|---|
| Ex. | Chemical Structure |
| 579 | 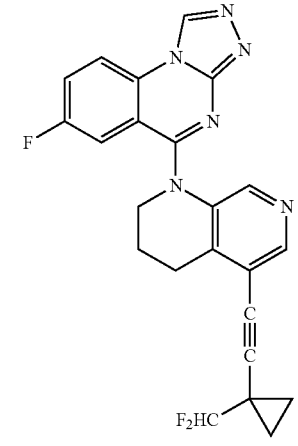 |
| 580 | |
| 581 | |
TABLE 3H-continued
| Compounds | |
|---|---|
| Ex. | Chemical Structure |
| 582 | 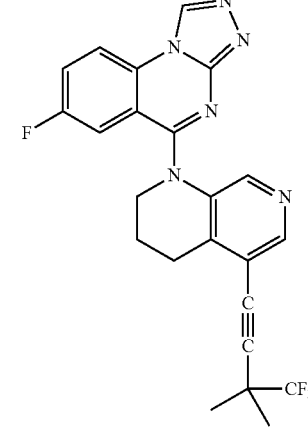 |
| 583 | |
| 584 | 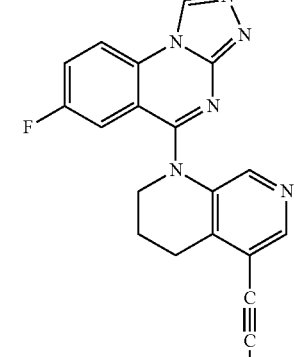 |

TABLE 3H-continued
| Ex. | Chemical Structure |
|---|---|
| 747 | 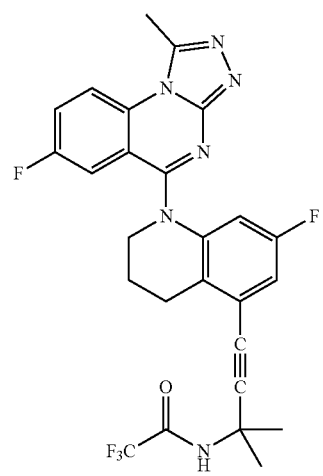 [SMILES: Cc1nnc2nc(N3CCCc4c(C#CC(C)(C)NC(=O)C(F)(F)F)cc(F)cc43)c3cc(F)ccc3n12] |
| 748 | 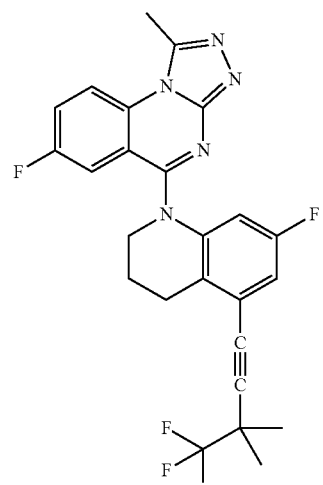 |
| 749 | 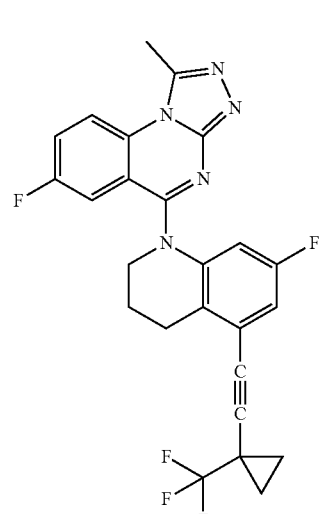 |
| 750 | 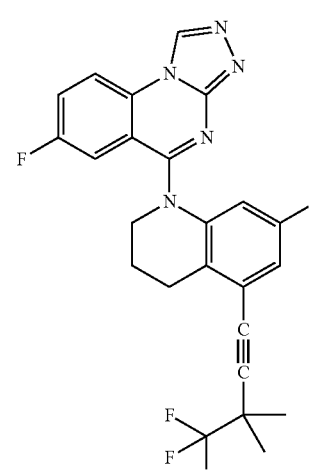 |
| 751 | 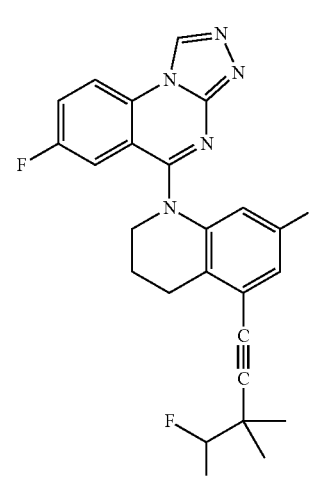 |
| 767 | 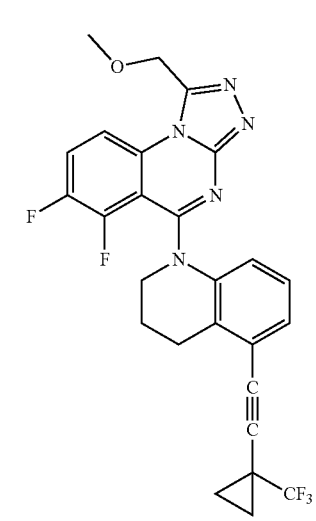 [SMILES: COCc1nnc2nc(N3CCCc4c(C#CC5(C(F)(F)F)CC5)cccc43)c3c(F)c(F)ccc3n12] |

TABLE 3H-continued

| Compounds | |
|---|---|
| Ex. | Chemical Structure |
| 768 | |
| 769 | |
| 770 | |
| 771 | |
| 772 | |
| 773 | |

TABLE 3H-continued

| Ex. | Chemical Structure |
|---|---|
| 774 | (structure) |
| 775 | (structure) |
| 776 | (structure) |
| 777 | (structure) |

TABLE 3I

| Ex. | Chemical Structure |
|---|---|
| 585 | (structure) |

TABLE 3I-continued
| Compounds | |
|---|---|
| Ex. | Chemical Structure |
| 586 | 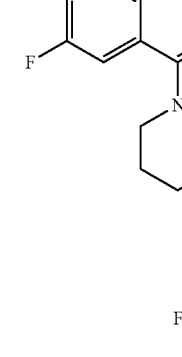 |
| 605 | 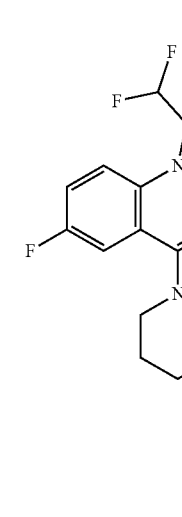 |
| 645 | 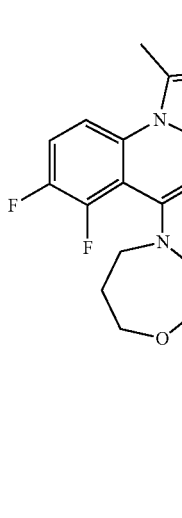 |
| 646 | 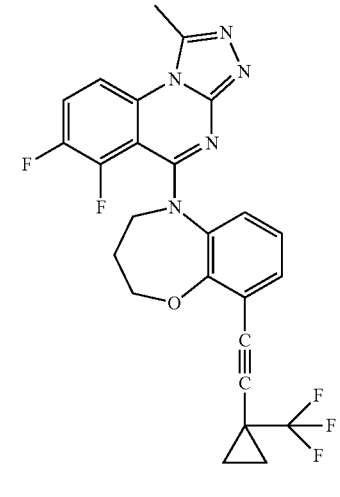 [SMILES: Cc1nnc2nc(N3CCCOc4c(C#CC5(C(F)(F)F)CC5)cccc43)c3c(F)c(F)ccc3n12] |
| 666 | 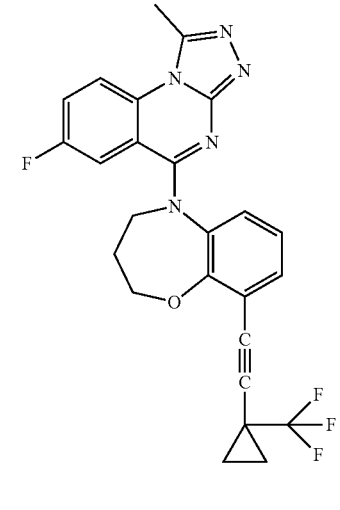 [SMILES: Cc1nnc2nc(N3CCCOc4c(C#CC5(C(F)(F)F)CC5)cccc43)c3cc(F)ccc3n12] |
| 719 | 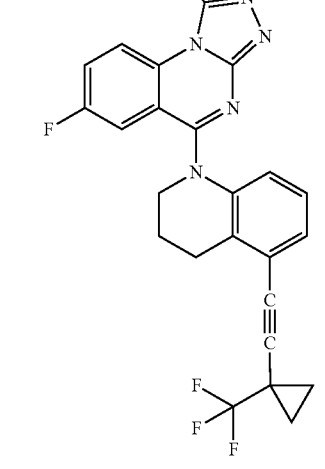 |

TABLE 3I-continued

| Ex. | Chemical Structure |
|---|---|
| 720 | 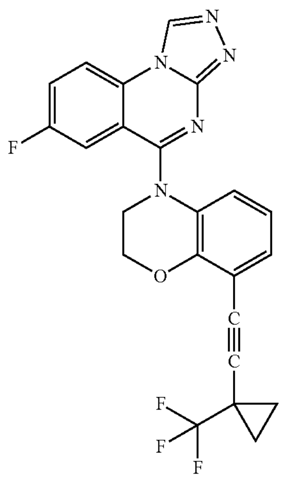 [SMILES: Fc1ccc2c(c1)c(N1CCOc3c(C#CC4(C(F)(F)F)CC4)cccc31)nc1nncn12] |
| 721 | 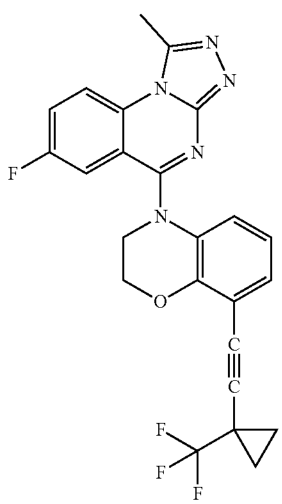 [SMILES: Cc1nnc2nc(N3CCOc4c(C#CC5(C(F)(F)F)CC5)cccc43)c3cc(F)ccc3n12] |
| 722 | 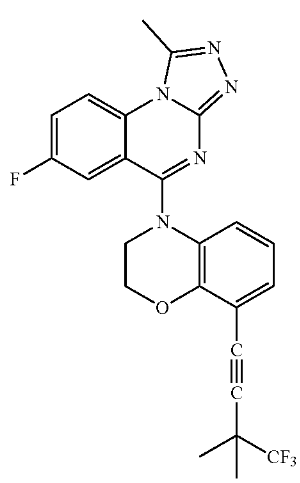 [SMILES: Cc1nnc2nc(N3CCOc4c(C#CC(C)(C)C(F)(F)F)cccc43)c3cc(F)ccc3n12] |
| 778 | |
| 779 | |
| 780 | |

TABLE 3I-continued

| Compounds | |
|---|---|
| Ex. | Chemical Structure |
| 781 | |
| 782 | |
| 783 | |
| 784 | |
| 786 | |
| 789 | |

TABLE 3J
| Ex. | Chemical Structure |
|---|---|
| 588 | 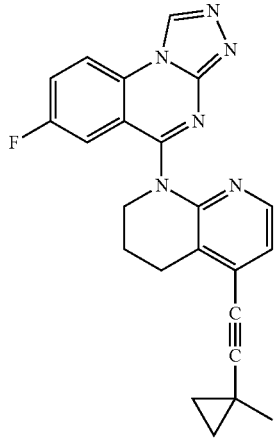 [SMILES: CC1(C#Cc2ccnc3c2CCCN3c2nc3nncn3c3ccc(F)cc23)CC1] |
| 636 | 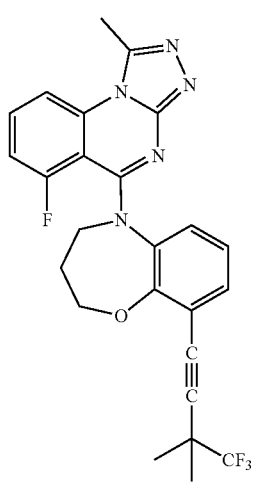 [SMILES: Cc1nnc2nc(N3CCCOc4c(C#CC(C)(C)C(F)(F)F)cccc43)c3c(F)cccc3n12] |
| 637 | 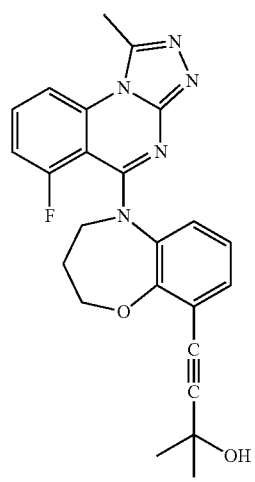 [SMILES: Cc1nnc2nc(N3CCCOc4c(C#CC(C)(C)O)cccc43)c3c(F)cccc3n12] |
TABLE 3J-continued
| Ex. | Chemical Structure |
|---|---|
| 638 | 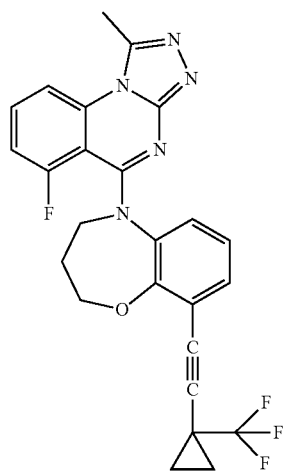 [SMILES: Cc1nnc2nc(N3CCCOc4c(C#CC5(C(F)(F)F)CC5)cccc43)c3c(F)cccc3n12] |
| 639 | 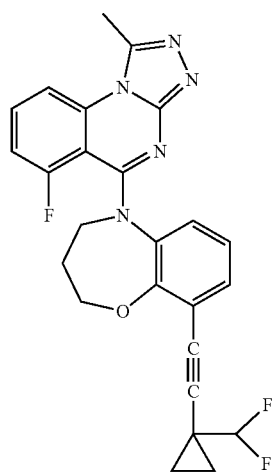 [SMILES: Cc1nnc2nc(N3CCCOc4c(C#CC5(C(F)F)CC5)cccc43)c3c(F)cccc3n12] |
| 640 | 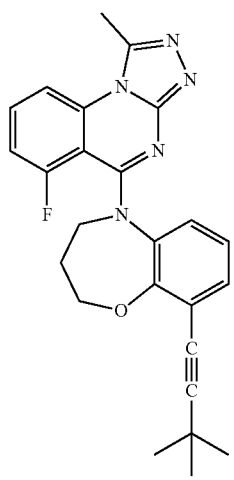 [SMILES: Cc1nnc2nc(N3CCCOc4c(C#CC(C)(C)C)cccc43)c3c(F)cccc3n12] |

TABLE 3J-continued

| Ex. | Chemical Structure |
|---|---|
| 641 | 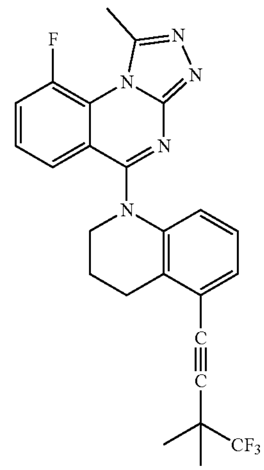 [SMILES: Cc1nnc2nc(N3CCCc4c(C#CC(C)(C)C(F)(F)F)cccc43)c3cccc(F)c3n12] |
| 642 | 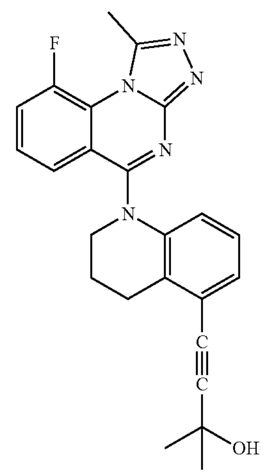 [SMILES: Cc1nnc2nc(N3CCCc4c(C#CC(C)(C)O)cccc43)c3cccc(F)c3n12] |
| 643 | 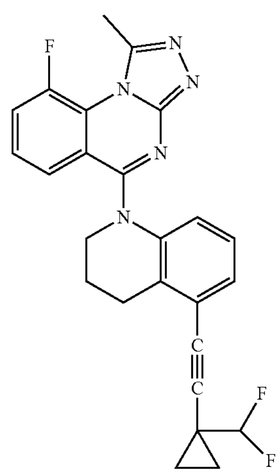 [SMILES: Cc1nnc2nc(N3CCCc4c(C#CC5(C(F)F)CC5)cccc43)c3cccc(F)c3n12] |
| 787 | |
| 790 | |
| 791 | |

TABLE 3J-continued
Compounds
| Ex. | Chemical Structure |
|---|---|
| 792 | 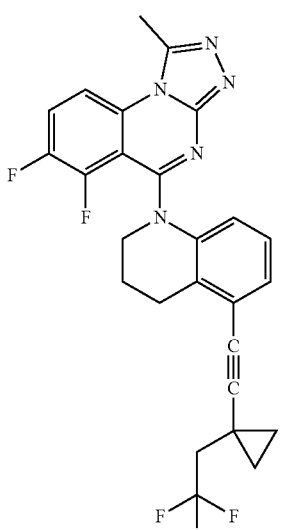 |
| 794 | 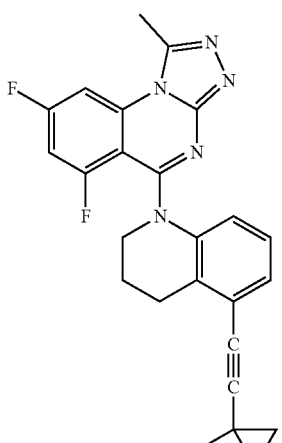 |
| 795 | 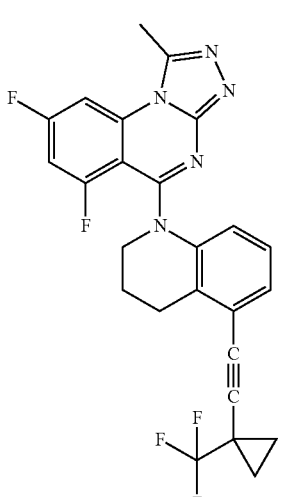 |
| 797 | 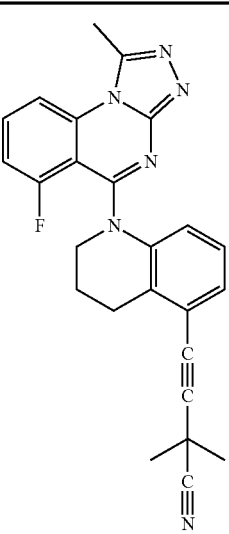 |
| 798 | 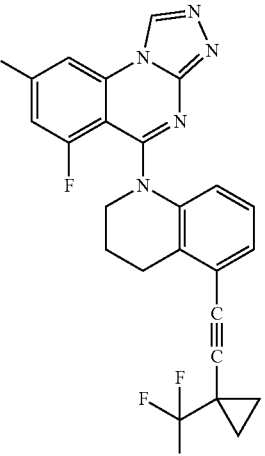 |
| 799 | 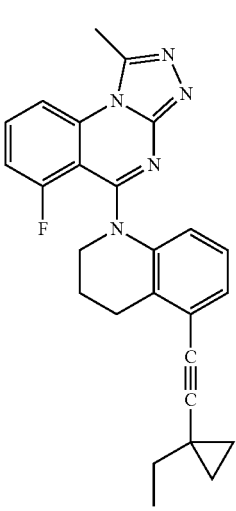 [SMILES: CCC1(C#Cc2cccc3c2CCCN3c2nc3nnc(C)n3c3cccc(F)c23)CC1] |

TABLE 3J-continued
| Compounds | |
|---|---|
| Ex. | Chemical Structure |
| 800 | 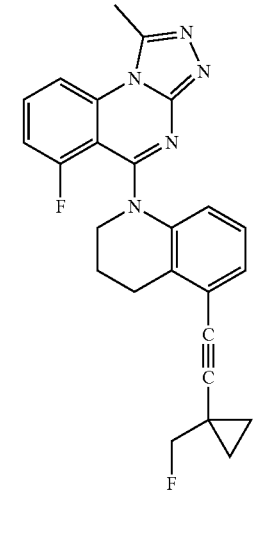 |
| 808 | |
TABLE 3K
| Compounds | |
|---|---|
| Ex. | Chemical Structure |
| 644 | 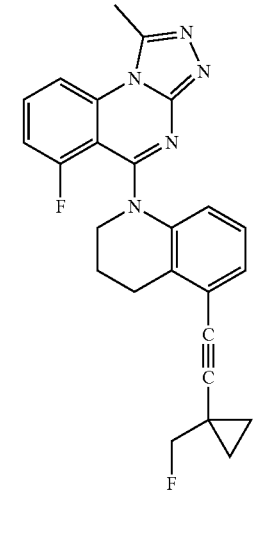 |
| 647 | |
| 648 | |

TABLE 3K-continued
Compounds
| Ex. | Chemical Structure |
|---|---|
| 649 | 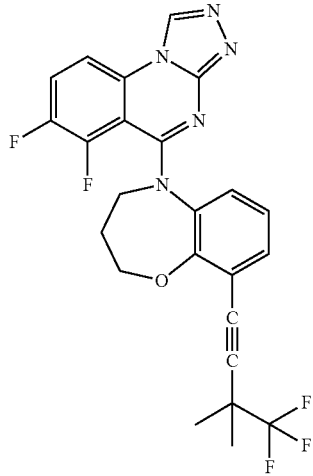 [SMILES: CC(C)(C#Cc1cccc2c1OCCCN2c1nc2nncn2c2ccc(F)c(F)c12)C(F)(F)F] |
| 650 | 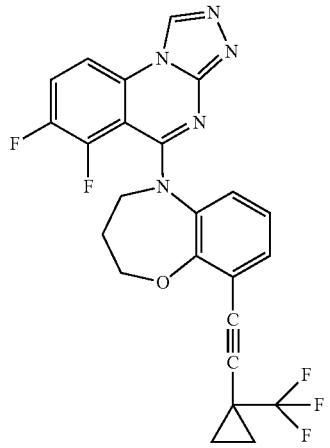 [SMILES: Fc1ccc2c(c(N3CCCOc4c(C#CC5(C(F)(F)F)CC5)cccc43)nc3nncn32)c1F] |
| 651 | 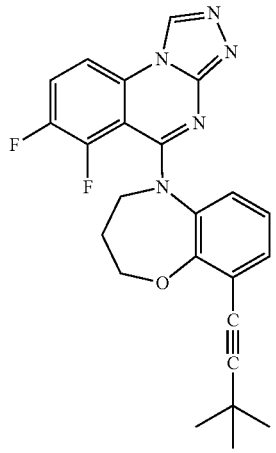 [SMILES: CC(C)(C)C#Cc1cccc2c1OCCCN2c1nc2nncn2c2ccc(F)c(F)c12] |
TABLE 3K-continued
Compounds
| Ex. | Chemical Structure |
|---|---|
| 652 | 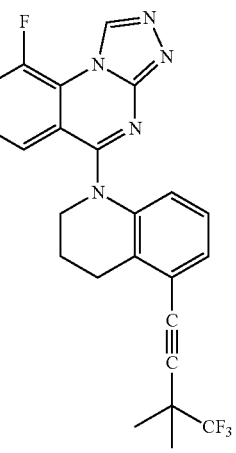 |
| 653 | 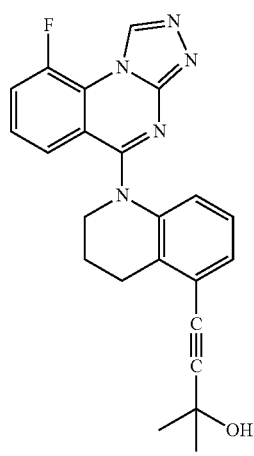 [SMILES: CC(C)(O)C#Cc1cccc2c1CCCN2c1nc2nncn2c2c(F)cccc12] |
| 654 | 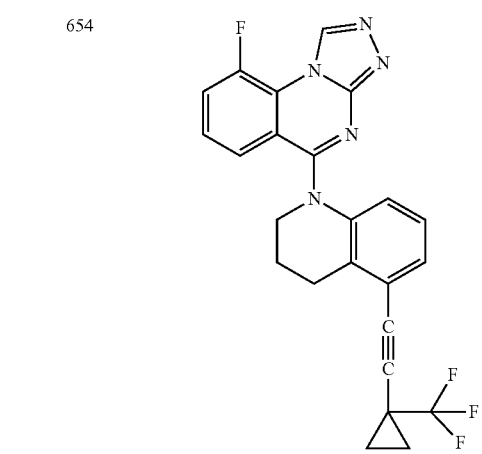 |

TABLE 3K-continued

| Ex. | Chemical Structure |
|---|---|
| 696 | 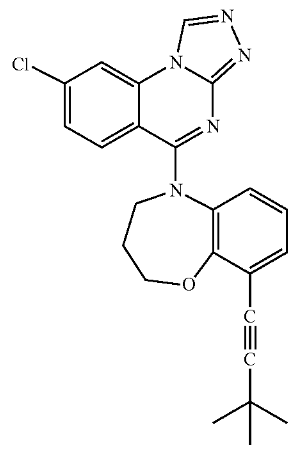 [SMILES: CC(C)(C)C#Cc1cccc2c1OCCCN2c1nc2nncn2c2cc(Cl)ccc12] |
| 697 | 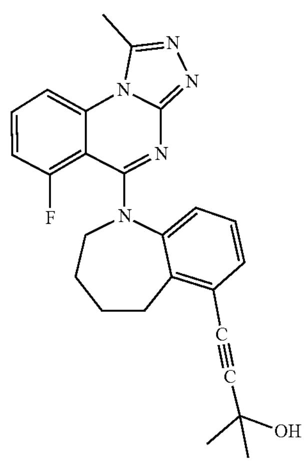 [SMILES: Cc1nnc2nc(N3CCCCc4c(C#CC(C)(C)O)cccc43)c3c(F)cccc3n12] |
| 809 | 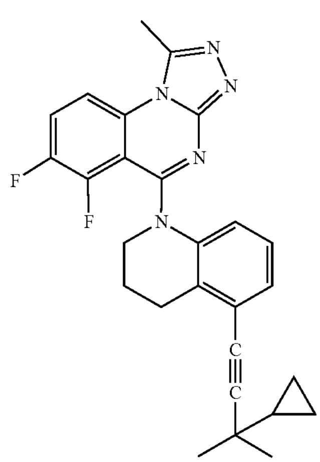 [SMILES: Cc1nnc2nc(N3CCCc4c(C#CC(C)(C)C5CC5)cccc43)c3c(F)c(F)ccc3n12] |
| 810 | |
| 812 | |
| 813 | |

TABLE 3K-continued

| Ex. | Chemical Structure |
|---|---|
| 825 | 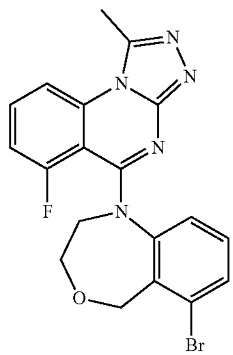 [SMILES: Cc1nnc2nc(N3CCOCc4c(Br)cccc43)c3c(F)cccc3n12] |
| 826 | 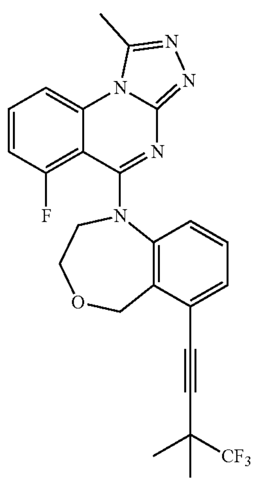 |
| 827 | 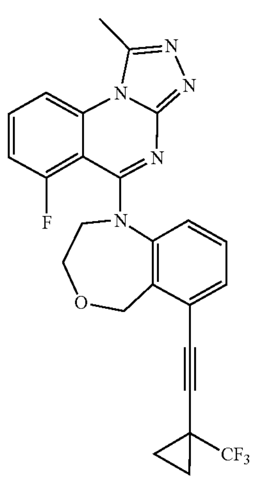 [SMILES: Cc1nnc2nc(N3CCOCc4c(C#CC5(C(F)(F)F)CC5)cccc43)c3c(F)cccc3n12] |
| 828 | 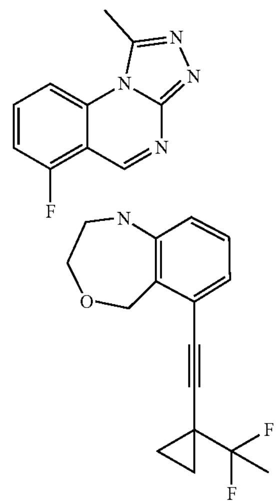 |
| 829 | 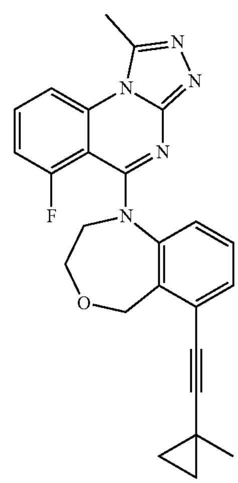 |

TABLE 1A-1

| Ex. | Chemical Structure |
|---|---|
| 3 | 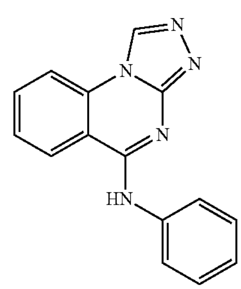 [SMILES: c1ccc(Nc2nc3nncn3c3ccccc23)cc1] |

TABLE 1A-1-continued

Compounds

| Ex. | Chemical Structure |
|---|---|
| 7 | 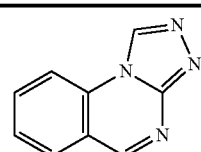 |

Also falling within the scope herein are the in vivo metabolic products of the compounds described herein, to the extent such products are novel and unobvious over the prior art. Such products may result for example from the oxidation, reduction, hydrolysis, amidation, esterification and the like of the administered compound, primarily due to enzymatic processes. Accordingly, included are novel and unobvious compounds produced by a process comprising contacting a compound with a mammal for a period of time sufficient to yield a metabolic product thereof. Such products typically are identified by preparing a radiolabelled (e.g. $^{14}$C or $^3$H) compound, administering it parenterally in a detectable dose (e.g. greater than about 0.5 mg/kg) to an animal such as rat, mouse, guinea pig, monkey, or to man, allowing sufficient time for metabolism to occur (typically from about 30 seconds to about 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS or NMR analysis. In general, analysis of metabolites is done in the same way as conventional drug metabolism studies well-known to those skilled in the art.

In some embodiments, a compound of the present disclosure has selectivity for DGKα over one or more of the other DGK isoforms, e.g., β, γ, δ, ε, ζ, η, θ, ι, and/or κ. Selectivity can be measured by relative values in corresponding biochemical assays, e.g., activity to inhibit a DGK isoform. In some embodiments, the compound comprises an activity against DGKβ, DGKγ, DGKδ, DGKε, DGKζ, DGKη, DGKθ, DGKι, and/or DGKκ, wherein the IC$_{50}$ is greater than about 30 μM in a biochemical assay.

In some embodiments, a compound of the present disclosure has selectivity for DGKα of at least about 1.2, about 1.5, about 2, about 3, about 4, about 5, about 6, about 7, about 8, about 9, about 10, about 15, about 20, about 30, about 40, about 50, about 60, about 70, about 80, about 90, about 100, about 200, about 300, about 400, about 500, about 1000, about 2000, about 3000, about 4000, about 5000, or about 10000-fold or more over one or more, e.g., 2, 3, 4, 5, 6, 7, 8, or 9 or more, other DGK isoforms including DGKθ, DGKγ, DGKδ, DGKε, DGKζ, DGKη, DGKθ, DGKι, and/or DGKκ. In some embodiments, the compound has selectivity for DGKα of at least about 1.2, about 1.5, about 2, about 3, about 4, about 5, about 6, about 7, about 8, about 9, about 10, about 15, about 20, about 30, about 40, about 50, about 60, about 70, about 80, about 90, about 100, about 200, about 300, about 400, about 500, about 1000, about 2000, about 3000, about 4000, about 5000, or about 10000-fold or more over DGKβ and/or DGKγ. In some embodiments, the compound has selectivity for DGKα of at least about 1.2, about 1.5, about 2, about 3, about 4, about 5, about 6, about 7, about 8, about 9, about 10, about 15, about 20, about 30, about 40, about 50, about 60, about 70, about 80, about 90, about 100, about 200, about 300, about 400, about 500, about 1000, about 2000, about 3000, about 4000, about 5000, or about 10000-fold or more over DGKθ. In some embodiments, the compound has selectivity for DGKα of at least about 1.2, about 1.5, about 2, about 3, about 4, about 5, about 6, about 7, about 8, about 9, about 10, about 15, about 20, about 30, about 40, about 50, about 60, about 70, about 80, about 90, about 100, about 200, about 300, about 400, about 500, about 1000, about 2000, about 3000, about 4000, about 5000, or about 10000-fold or more over DGKγ. In some embodiments, the compound has selectivity for DGKα of at least about 1.2, about 1.5, about 2, about 3, about 4, about 5, about 6, about 7, about 8, about 9, about 10, about 15, about 20, about 30, about 40, about 50, about 60, about 70, about 80, about 90, about 100, about 200, about 300, about 400, about 500, about 1000, about 2000, about 3000, about 4000, about 5000, or about 10000-fold or more over DGKδ. In some embodiments, the compound has selectivity for DGKα of at least about 1.2, about 1.5, about 2, about 3, about 4, about 5, about 6, about 7, about 8, about 9, about 10, about 15, about 20, about 30, about 40, about 50, about 60, about 70, about 80, about 90, about 100, about 200, about 300, about 400, about 500, about 1000, about 2000, about 3000, about 4000, about 5000, or about 10000-fold or more over DGKε. In some embodiments, the compound has selectivity for DGKα of at least about 1.2, about 1.5, about 2, about 3, about 4, about 5, about 6, about 7, about 8, about 9, about 10, about 15, about 20, about 30, about 40, about 50, about 60, about 70, about 80, about 90, about 100, about 200, about 300, about 400, about 500, about 1000, about 2000, about 3000, about 4000, about 5000, or about 10000-fold or more over DGKζ. In some embodiments, the compound has selectivity for DGKα of at least about 1.2, about 1.5, about 2, about 3, about 4, about 5, about 6, about 7, about 8, about 9, about 10, about 15, about 20, about 30, about 40, about 50, about 60, about 70, about 80, about 90, about 100, about 200, about 300, about 400, about 500, about 1000, about 2000, about 3000, about 4000, about 5000, or about 10000-fold or more over DGKη. In some embodiments, the compound has selectivity for DGKα of at least about 1.2, about 1.5, about 2, about 3, about 4, about 5, about 6, about 7, about 8, about 9, about 10, about 15, about 20, about 30, about 40, about 50, about 60, about 70, about 80, about 90, about 100, about 200, about 300, about 400, about 500, about 1000, about 2000, about 3000, about 4000, about 5000, or about 10000-fold or more over DGKθ. In some embodiments, the compound has selectivity for DGKα of at least about 1.2, about 1.5, about 2, about 3, about 4, about 5, about 6, about 7, about 8, about 9, about 10, about 15, about 20, about 30, about 40, about 50, about 60, about 70, about 80, about 90, about 100, about 200, about 300, about 400, about 500, about 1000, about 2000, about 3000, about 4000, about 5000, or about 10000-fold or more over DGKι. In some embodiments, the compound has selectivity for DGKα of at least about 1.2, about 1.5, about 2, about 3, about 4, about 5, about 6, about 7, about 8, about 9, about 10, about 15, about 20, about 30, about 40, about 50, about 60, about 70, about 80, about 90, about 100, about 200, about 300, about 400, about 500, about 1000, about 2000, about 3000, about 4000, about 5000, or about 10000-fold or more over DGKκ.

III. Pharmaceutical Formulations

In some embodiments, the present disclosure provides a pharmaceutical formulation comprising a pharmaceutically effective amount of a compound of the present disclosure, or a pharmaceutically acceptable salt thereof, and a pharmaceutically acceptable carrier or excipient. Also provided herein is a pharmaceutical formulation comprising a pharmaceutically effective amount of a compound of Formula (I), (I-1), (Ia), (Ia-1), (Ib), (Ic), (IIa), (IIa-1), (IIc), (IIc-1), (IIc-2), (IIc-2), (IIc-3), (IIc-4), (IIc-5), (IIc-6), (IIc-7), or (IIc-8), or a pharmaceutically acceptable salt, solvate, and/or ester thereof, and a pharmaceutically acceptable carrier or excipient.

In some embodiments, the pharmaceutical composition further comprises one or more additional therapeutic agents. Any suitable additional therapeutic agent or combination therapy can be used with the compounds of Formula (I), (I-1), (Ia), (Ia-1), (Ib), (Ic), (IIa), (IIa-1), (IIc), (IIc-1), (IIc-2), (IIc-2), (IIc-3), (IIc-4), (IIc-5), (IIc-6), (IIc-7), or (IIc-8), or a pharmaceutically acceptable salt thereof, such as the agents and therapies described within.

In some embodiments, the pharmaceutical composition comprises a compound of Formula (I), (I-1), (Ia), (Ia-1), (Ib), (Ic), (IIa), (IIa-1), (IIc), (IIc-1), (IIc-2), (IIc-2), (IIc-3), (IIc-4), (IIc-5), (IIc-6), (IIc-7), or (IIc-8), and an additional therapeutic agent, wherein the additional therapeutic agent is an anticancer agent. In some embodiments, the pharmaceutical composition is the pharmaceutical composition wherein the additional therapeutic agent is independently an anti-neoplastic agent, nivolumab, pembrolizumab, atezolizumab, ipilimumab, chemotherapy, radiation therapy, or resection therapy. In some embodiments, the pharmaceutical composition is the pharmaceutical composition wherein the additional therapeutic agent is independently rituxan, doxorubicin, gemcitabine, nivolumab, pembrolizumab, artezolizumab, nivolumab, pembrolizumab, atezolizumab, or ipilimumab. In some embodiments, the pharmaceutical composition is the pharmaceutical composition wherein the additional therapeutic agent is a PD-1/PD-L1 inhibitor. In some embodiments, the pharmaceutical composition is the pharmaceutical composition wherein the additional therapeutic agent is a vaccine.

In some embodiments, the pharmaceutical composition is the pharmaceutical composition wherein the additional therapeutic agent comprises one or more populations of immune cells, such as natural killer (NK) cells, NK-T cells, T cells, cytokine-induced killer (CIK) cells, macrophage (MAC) cells, tumor infiltrating lymphocytes (TILs) and dendritic cell (DCs).

In some embodiments, the pharmaceutical composition is the pharmaceutical composition wherein the additional therapeutic agent comprises one or more chimeric antigen receptors (CARs).

In some embodiments, the pharmaceutical composition is the pharmaceutical composition wherein the additional therapeutic agent comprises an immunotherapy, an immunostimulatory therapy, a cytokine therapy, a chemokine therapy, a cellular therapy, a gene therapy, or combinations thereof.

In some embodiments, the pharmaceutical composition comprises a compound of Formula (I), (I-1), (Ia), (Ia-1), (Ib), (Ic), (IIa), (IIa-1), (IIc), (IIc-1), (IIc-2), (IIc-2), (IIc-3), (IIc-4), (IIc-5), (IIc-6), (IIc-7), or (IIc-8), and an additional therapeutic agent, wherein the additional therapeutic agent is an agent effective against a viral infection. In some embodiments, the viral infection is HIV. In some embodiments, the viral infection is hepatitis B virus. In some embodiments, the pharmaceutical composition comprises a compound of Formula (I), (I-1), (Ia), (Ia-1), (Ib), (Ic), (IIa), (IIa-1), (IIc), (IIc-1), (IIc-2), (IIc-2), (IIc-3), (IIc-4), (IIc-5), (IIc-6), (IIc-7), or (IIc-8), and an additional therapeutic agent, wherein additional therapeutic agent comprises a vaccine.

In some embodiments, the pharmaceutical composition is for use in treating a cancer.

In some embodiments, the pharmaceutical composition is for use in treating an HIV or hepatitis B infection.

In some embodiments, compounds disclosed herein are formulated with conventional carriers and excipients, which can be selected in accord with ordinary practice. Tablets can contain excipients, glidants, fillers, binders and the like. Aqueous formulations can be prepared in sterile form, and can be isotonic, for instance when intended for delivery by other than oral administration. In some embodiments, formulations can optionally contain excipients such as those set forth in the "Handbook of Pharmaceutical Excipients" (1986). Excipients can include, for example, ascorbic acid and other antioxidants, chelating agents such as EDTA, carbohydrates such as dextran, hydroxyalkylcellulose, hydroxyalkylmethylcellulose, stearic acid and the like. The pH of the formulations ranges from about 3 to about 11, for example from about 7 to about 10.

In some embodiments, the compounds disclosed herein are administered alone. In some embodiments, compounds disclosed herein are administered in pharmaceutical formulations. In some embodiments a formulation, for veterinary and/or for human use, comprises at least one compound of Formula (I), (I-1), (Ia), (Ia-1), (Ib), (Ic), (IIa), (IIa-1), (IIc), (IIc-1), (IIc-2), (IIc-2), (IIc-3), (IIc-4), (IIc-5), (IIc-6), (IIc-7), or (IIc-8), or a pharmaceutically acceptable salt, solvate, and/or ester thereof, together with one or more acceptable carriers and optionally other therapeutic ingredients, such as those additional therapeutic ingredients discussed herein. In some embodiments, carrier(s) are "acceptable" in the sense of being compatible with the other ingredients of the formulation and physiologically innocuous to the recipient thereof.

In some embodiments, formulations of the disclosure include those suitable for the foregoing administration routes. In some embodiments, formulations are presented in unit dosage form. Formulations may be prepared by methods known in the art of pharmacy. Techniques and formulations can be found, for example, in Remington's Pharmaceutical Sciences (Mack Publishing Co., Easton, PA). Such methods include, for instance, a step of bringing into association the active ingredient with a carrier comprising one or more accessory ingredients. In some embodiments, formulations are prepared by bringing into association the active ingredient with liquid carriers or finely divided solid carriers or both, and then, in some embodiments, shaping the product.

Formulations suitable for oral administration may be presented as discrete units such as capsules, cachets or tablets each containing a predetermined amount of active ingredient, such as a compound of Formula (I), (I-1), (Ia), (Ia-1), (Ib), (Ic), (IIa), (IIa-1), (IIc), (IIc-1), (IIc-2), (IIc-2), (IIc-3), (IIc-4), (IIc-5), (IIc-6), (IIc-7), or (IIc-8), or a pharmaceutically acceptable salt, solvate, and/or ester thereof; as a powder or granules; as a solution or a suspension in an aqueous or non-aqueous liquid; or as an oil-in-water liquid emulsion or a water-in-oil liquid emulsion. In some embodiments, an active ingredient is administered as a bolus, electuary or paste.

A tablet can be made, for example, by compression or molding, optionally with one or more accessory ingredients. Compressed tablets may be prepared, for example, by compressing in a suitable machine the active ingredient in a free-flowing form such as a powder or granules, optionally mixed with a binder, lubricant, inert diluent, preservative, surface active or dispersing agent. Molded tablets may be made, for instance, by molding in a suitable machine a mixture of the powdered active ingredient moistened with an inert liquid diluent. The tablets may optionally be coated or scored. In some embodiments, tablets are formulated so as to provide slow or controlled release of the active ingredient therefrom.

For infections of the eye or other external tissues e.g. mouth and skin, the formulations can be applied as a topical ointment or cream containing a compound of Formula (I), (I-1), (Ia), (Ia-1), (Ib), (Ic), (IIa), (IIa-1), (Ic), (IIc-1), (IIc-2), (IIc-2), (IIc-3), (IIc-4), (IIc-5), (IIc-6), (IIc-7), or (IIc-8) in an amount of, for example, about 0.075 to about 20% w/w (including active ingredient(s) in a range between about 0.1% and about 20% in increments of about 0.1% w/w such as about 0.6% w/w, about 0.7% w/w, etc.), such as about 0.2 to about 15% w/w and such as about 0.5 to about 10% w/w. When formulated in an ointment, a compound of Formula (I), (I-1), (Ia), (Ia-1), (Ib), (Ic), (IIa), (IIa-1), (Ic), (IIc-1), (IIc-2), (IIc-2), (IIc-3), (IIc-4), (IIc-5), (IIc-6), (IIc-7), or (IIc-8) may be employed with either a paraffinic or a water-miscible ointment base. Alternatively, a compound of Formula (I), (I-1), (Ia), (Ia-1), (Ib), (Ic), (IIa), (IIa-1), (IIc), (IIc-1), (IIc-2), (IIc-2), (IIc-3), (IIc-4), (IIc-5), (IIc-6), (IIc-7), or (IIc-8) may be formulated in a cream with an oil-in-water cream base.

If desired, the aqueous phase of the cream base may include, for example, at least about 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may in some embodiments include a compound which enhances absorption or penetration of the active ingredient through the skin or other affected areas. Examples of such dermal penetration enhancers include dimethyl sulfoxide and related analogs.

The oily phase of the emulsions may be constituted from known ingredients in a known manner. While the phase may comprise merely an emulsifier (otherwise known as an emulgent), it can comprise, for example, a mixture of at least one emulsifier with a fat or an oil or with both a fat and an oil. In some embodiments, a hydrophilic emulsifier is included together with a lipophilic emulsifier which acts as a stabilizer. In some embodiments, an emulsion includes both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation include, for instance, Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired properties. The cream can be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used. These may be used alone or in combination depending on the properties required. Alternatively, high melting point lipids such as white soft paraffin and/or liquid paraffin or other mineral oils can be used.

In some embodiments, pharmaceutical formulations herein comprise a combination together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, solutions, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally-occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally-occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions may be in the form of a sterile injectable or intravenous preparations, such as a sterile injectable aqueous or oleaginous suspension. Such suspensions may be formulated according to the known art using those suitable dispersing or wetting agents and suspending agents which have been mentioned above. Sterile injectable or intravenous preparations may also include a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form can vary depending upon the host treated and the particular mode of administration. For example, a time-release formulation intended for oral administration to humans may contain about 1 to about 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to about 500 g of the active ingredient per milliliter of solution in order that infusion of a suitable volume at a rate of about 30 mL/hr can occur.

Formulations suitable for topical administration to the eye also include eye drops wherein the active ingredient is dissolved or suspended in a suitable carrier, especially an aqueous solvent for the active ingredient. The active ingredient can be present in such formulations in a concentration of about 0.5 to about 20%, such as about 0.5 to about 10%, for example about 1.5% w/w.

Formulations suitable for topical administration in the mouth include, for example, lozenges comprising the active ingredient in a flavored basis, such as sucrose and acacia or tragacanth; pastilles comprising the active ingredient in an inert basis, such as gelatin and glycerin, or sucrose and acacia; and mouthwashes comprising the active ingredient in a suitable liquid carrier.

Formulations for rectal administration may be presented as a suppository with a suitable base comprising, for example, cocoa butter or a salicylate.

Formulations suitable for intrapulmonary or nasal administration have a particle size, for example, in the range of about 0.1 to about 500 microns, such as about 0.5, about 1, about 30, or about 35, etc., which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment of cancer as described below.

In some embodiments, an inhalable composition comprises a compound of Formula (I), (I-1), (Ia), (Ia-1), (Ib), (Ic), (IIa), (IIa-1), (IIc), (IIc-1), (IIc-2), (IIc-2), (IIc-3), (IIc-4), (IIc-5), (IIc-6), (IIc-7), or (IIc-8), or a pharmaceutically acceptable salt thereof. In some embodiments, the inhalable composition is suitable for treating cancer. In some embodiments, pharmaceutically acceptable salts are inorganic acid salts including hydrochloride, hydrobromide, sulfate or phosphate salts. For example, such salts may cause less pulmonary irritation relative to other salts. In some embodiments, an inhalable composition is delivered to the endobronchial space in an aerosol comprising particles with a mass median aerodynamic diameter (MMAD) between about 1 and about 5 µm. In some embodiments, the compound of Formula (I), (I-1), (Ia), (Ia-1), (Ib), (Ic), (IIa), (IIa-1), (IIc), (IIc-1), (IIc-2), (IIc-2), (IIc-3), (IIc-4), (IIc-5), (IIc-6), (IIc-7), or (IIc-8) is formulated for aerosol delivery using a nebulizer, pressurized metered dose inhaler (pMDI), or dry powder inhaler (DPI).

Non-limiting examples of nebulizers include atomizing, jet, ultrasonic, pressurized, vibrating porous plate, or equivalent nebulizers including those nebulizers utilizing adaptive aerosol delivery technology (Denyer, *J Aerosol medicine Pulmonary Drug Delivery* 2010, 23 Supp 1, S1-S10). A jet nebulizer utilizes air pressure to break a liquid solution into aerosol droplets. An ultrasonic nebulizer works by a piezoelectric crystal that shears a liquid into small aerosol droplets. A pressurized nebulization system forces solution under pressure through small pores to generate aerosol droplets. A vibrating porous plate device utilizes rapid vibration to shear a stream of liquid into appropriate droplet sizes.

In some embodiments, a formulation for nebulization is delivered to the endobronchial space in an aerosol comprising particles with a MMAD predominantly between about 1 µm and about 5 µm using a nebulizer able to aerosolize the formulation of the compound of Formula (I), (I-1), (Ia), (Ia-1), (Ib), (Ic), (IIa), (IIa-1), (IIc), (IIc-1), (IIc-2), (IIc-2), (IIc-3), (IIc-4), (IIc-5), (IIc-6), (IIc-7), or (IIc-8) into particles of the required MMAD. To be optimally therapeutically effective and to avoid upper respiratory and systemic side effects, the majority of aerosolized particles should not have a MMAD greater than about 5 µm. If an aerosol contains a large number of particles with a MMAD larger than about 5 µm, the particles are deposited in the upper airways decreasing the amount of drug delivered to the site of inflammation and bronchoconstriction in the lower respiratory tract. If the MMAD of the aerosol is smaller than about 1 µm, then the particles can in some cases remain suspended in the inhaled air and may be subsequently exhaled during expiration.

When formulated and delivered according to methods herein, the aerosol formulation for nebulization delivers a therapeutically efficacious dose of the compound of Formula (I), (I-1), (Ia), (Ia-1), (Ib), (Ic), (IIa), (IIa-1), (IIc), (IIc-1), (IIc-2), (IIc-2), (IIc-3), (IIc-4), (IIc-5), (IIc-6), (IIc-7), or (IIc-8) to a therapeutic target, such as the site of a cancer. The amount of drug administered can be adjusted to reflect the efficiency of the delivery of a therapeutically efficacious dose of the compound of Formula (I), (I-1), (Ia), (Ia-1), (Ib), (Ic), (IIa), (IIa-1), (IIc), (IIc-1), (IIc-2), (IIc-2), (IIc-3), (IIc-4), (IIc-5), (IIc-6), (IIc-7), or (IIc-8). In some embodiments, a combination of the aqueous aerosol formulation with the atomizing, jet, pressurized, vibrating porous plate, or ultrasonic nebulizer permits, depending on the nebulizer, from about 20 to about 90%, such as about 70% delivery of the administered dose of the compound of Formula (I), (I-1), (Ia), (Ia-1), (Ib), (Ic), (IIa), (IIa-1), (IIc), (IIc-1), (IIc-2), (IIc-2), (IIc-3), (IIc-4), (IIc-5), (IIc-6), (IIc-7), or (IIc-8) into the airways. In some embodiments, from about 30 to about 50% of the active compound is delivered. For example, from about 70 to about 90% of the active compound can be delivered.

In some embodiments, a compound of Formula (I), (I-1), (Ia), (Ia-1), (Ib), (Ic), (IIa), (IIa-1), (IIc), (IIc-1), (IIc-2), (IIc-2), (IIc-3), (IIc-4), (IIc-5), (IIc-6), (IIc-7), or (IIc-8) or a pharmaceutically acceptable salt thereof, is delivered as a dry inhalable powder. The compounds are administered endobronchially as a dry powder formulation to efficacious deliver fine particles of compound into the endobronchial space using dry powder or metered dose inhalers. For delivery by DPI, the compound of Formula (I), (I-1), (Ia), (Ia-1), (Ib), (Ic), (IIa), (IIa-1), (IIc), (IIc-1), (IIc-2), (IIc-2), (IIc-3), (IIc-4), (IIc-5), (IIc-6), (IIc-7), or (IIc-8) is processed into particles with, predominantly, MMAD between about 1 µm and about 5 µm by milling spray drying, critical fluid processing, or precipitation from solution. Media milling, jet milling and spray-drying devices and procedures capable of producing the particle sizes with a MMAD between about 1 µm and about 5 µm are well known in the art. In some embodiments, excipients are added to the compound of Formula (I), (I-1), (Ia), (Ia-1), (Ib), (Ic), (IIa), (IIa-1), (IIc), (IIc-1), (IIc-2), (IIc-2), (IIc-3), (IIc-4), (IIc-5), (IIc-6), (IIc-7), or (IIc-8) before processing into particles of the required sizes. In some embodiments, excipients are blended with the particles of the required size to aid in dispersion of the drug particles, for example by using lactose as an excipient.

Particle size determinations are made using devices well known in the art. For example a multi-stage Anderson cascade impactor or other suitable method such as those specifically cited within the US Pharmacopoeia Chapter 601 as characterizing devices for aerosols within metered-dose and dry powder inhalers.

In some embodiments, a compound of Formula (I), (I-1), (Ia), (Ia-1), (Ib), (Ic), (IIa), (IIa-1), (IIc), (IIc-1), (IIc-2), (IIc-2), (IIc-3), (IIc-4), (IIc-5), (IIc-6), (IIc-7), or (IIc-8) can be delivered as a dry powder using a device such as a dry powder inhaler or other dry powder dispersion devices. Non-limiting examples of dry powder inhalers and devices include those disclosed in U.S. Pat. Nos. 5,458,135; 5,740, 794; 5,775,320; 5,785,049; 3,906,950; 4,013,075; 4,069, 819; 4,995,385; 5,522,385; 4,668,218; 4,667,668; 4,805,811 and 5,388,572. There are two major designs of dry powder inhalers. One design is a metering device in which a reservoir for the drug is place within the device and the patient adds a dose of the drug into the inhalation chamber. The second design is a factory-metered device in which each individual dose has been manufactured in a separate container. Both systems depend on the formulation of the drug into small particles of MMAD from about 1 µm to about 5 µm and often involve co-formulation with larger excipient particles such as, but not limited to, lactose. Drug powder is placed in the inhalation chamber (either by device metering or by breakage of a factory-metered dosage) and the inspiratory flow of the patient accelerates the powder out of the device and into the oral cavity. Non-laminar flow characteristics of the powder path cause the excipient-drug aggregates to decompose, and the mass of the large excipient particles causes their impaction at the back of the throat, while the smaller drug particles are deposited deep in the lungs. In some embodiments, a compound of Formula (I), (I-1), (Ia), (Ia-1), (Ib), (Ic), (IIa), (IIa-1), (IIc), (IIc-1), (IIc-2), (IIc-2), (IIc-3), (IIc-4), (IIc-5), (IIc-6), (IIc-7), or (IIc-8), or a pharmaceutically acceptable salt thereof, is delivered as a dry powder using either type of dry powder inhaler as described herein, wherein the MMAD of the dry powder, exclusive of any excipients, is predominantly in the range of about 1 µm to about 5 µm.

In some embodiments, a compound of Formula (I), (I-1), (Ia), (Ia-1), (Ib), (Ic), (IIa), (IIa-1), (IIc), (IIc-1), (IIc-2), (IIc-2), (IIc-3), (IIc-4), (IIc-5), (IIc-6), (IIc-7), or (IIc-8) is delivered as a dry powder using a metered dose inhaler. Non-limiting examples of metered dose inhalers and devices include those disclosed in U.S. Pat. Nos. 5,261,538; 5,544, 647; 5,622,163; 4,955,371; 3,565,070; 3,361,306 and 6,116, 234. In some embodiments, a compound of Formula (I), (I-1), (Ia), (Ia-1), (Ib), (Ic), (IIa), (IIa-1), (IIc), (IIc-1), (IIc-2), (IIc-2), (IIc-3), (IIc-4), (IIc-5), (IIc-6), (IIc-7), or (IIc-8), or a pharmaceutically acceptable salt thereof, is delivered as a dry powder using a metered dose inhaler wherein the MMAD of the dry powder, exclusive of any excipients, is predominantly in the range of about 1 to about 5 µm.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Unit dosage formulations include those containing a daily dose or unit daily sub-dose, as herein above recited, or an appropriate fraction thereof, of the active ingredient.

It should be understood that in addition to the ingredients particularly mentioned above the formulations may include other agents conventional in the art having regard to the type of formulation in question, for example those suitable for oral administration may include flavoring agents.

Further provided are veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds herein are used to provide controlled release pharmaceutical formulations containing as active ingredient one or more of the compounds ("controlled release formulations") in which the release of the active ingredient is controlled and regulated to allow less frequency dosing or to improve the pharmacokinetic or toxicity profile of a given active ingredient.

Effective dose of active ingredient depends at least on the nature of the condition being treated, toxicity, the method of delivery, and the pharmaceutical formulation, and can be determined by the clinician using conventional dose escalation studies. It can be expected to be from about 0.0001 to about 100 mg/kg body weight per day; typically, from about 0.01 to about 10 mg/kg body weight per day; more typically, from about 0.01 to about 5 mg/kg body weight per day; most typically, from about 0.05 to about 0.5 mg/kg body weight per day. For example, the daily candidate dose for an adult human of about 70 kg body weight can range from about 1 mg to about 1000 mg, such as between about 5 mg and about 500 mg, and may take the form of single or multiple doses.

IV. Routes of Administration

One or more of the compounds of Formula (I), (I-1), (Ia), (Ia-1), (Ib), (Ic), (IIa), (IIa-1), (IIc), (IIc-1), (IIc-2), (IIc-2), (IIc-3), (IIc-4), (IIc-5), (IIc-6), (IIc-7), or (IIc-8) (herein referred to as the active ingredients) are administered by any route appropriate to the condition to be treated. Suitable routes include oral, rectal, nasal, pulmonary, topical (including buccal and sublingual), vaginal and parenteral (including subcutaneous, intramuscular, intravenous, intradermal, intrathecal and epidural), and the like. It will be appreciated that the route may vary with for example the condition of the recipient. An advantage of the compounds herein is that they are orally bioavailable and can be dosed orally.

The compounds of the present disclosure (also referred to herein as the active ingredients), can be administered by any route appropriate to the condition to be treated. Suitable routes include oral, rectal, nasal, topical (including buccal and sublingual), transdermal, vaginal and parenteral (including subcutaneous, intramuscular, intravenous, intradermal, intrathecal and epidural), and the like. It will be appreciated that the route may vary with for example the condition of the recipient. An advantage of certain compounds disclosed herein is that they are orally bioavailable and can be dosed orally.

A compound of the present disclosure may be administered to an individual in accordance with an effective dosing regimen for a desired period of time or duration, such as at least about one month, at least about 2 months, at least about 3 months, at least about 6 months, or at least about 12 months or longer. In some embodiments, the compound is administered on a daily or intermittent schedule for the duration of the individual's life.

The dosage or dosing frequency of a compound of the present disclosure may be adjusted over the course of the treatment, based on the judgment of the administering physician.

The compound may be administered to an individual (e.g., a human) in an effective amount. In some embodiments, the compound is administered once daily.

The compound can be administered by any useful route and means, such as by oral or parenteral (e.g., intravenous) administration. Therapeutically effective amounts of the compound may include from about 0.00001 mg/kg body weight per day to about 10 mg/kg body weight per day, such as from about 0.0001 mg/kg body weight per day to about 10 mg/kg body weight per day, or such as from about 0.001 mg/kg body weight per day to about 1 mg/kg body weight per day, or such as from about 0.01 mg/kg body weight per day to about 1 mg/kg body weight per day, or such as from about 0.05 mg/kg body weight per day to about 0.5 mg/kg body weight per day, or such as from about 0.3 mg to about 30 mg per day, or such as from about 30 mg to about 300 mg per day.

A compound of the present disclosure may be combined with one or more additional therapeutic agents in any dosage amount of the compound of the present disclosure (e.g., from about 1 mg to about 1000 mg of compound). Therapeutically effective amounts may include from about 1 mg per dose to about 1000 mg per dose, such as from about 50 mg per dose to about 500 mg per dose, or such as from about 100 mg per dose to about 400 mg per dose, or such as from about 150 mg per dose to about 350 mg per dose, or such as from about 200 mg per dose to about 300 mg per dose. Other therapeutically effective amounts of the compound of the present disclosure are about 100, about 125, about 150, about 175, about 200, about 225, about 250, about 275, about 300, about 325, about 350, about 375, about 400, about 425, about 450, about 475, or about 500 mg per dose. Other therapeutically effective amounts of the compound of the present disclosure are about 100 mg per dose, or about 125, about 150, about 175, about 200, about 225, about 250, about 275, about 300, about 325, about 350, about 375, about 400, about 425, about 450, or about 500 mg per dose. A single dose can be administered hourly, daily, or weekly. For example, a single dose can be administered once about every 1 hour, about 2, about 3, about 4, about 6, about 8, about 12, about 16 or once about every 24 hours. A single dose can also be administered once about every 1 day, about 2, about 3, about 4, about 5, about 6, or once about every 7 days. A single dose can also be administered once about every 1 week, about 2, about 3, or once about every 4 weeks. In some embodiments, a single dose can be administered once about every week. A single dose can also be administered once about every month.

Other therapeutically effective amounts of the compound of the present disclosure are about 20, about 25, about 30, about 35, about 40, about 45, about 50, about 55, about 60, about 65, about 70, about 75, about 80, about 85, about 90, about 95, or about 100 mg per dose.

The frequency of dosage of the compound of the present disclosure can be determined by the needs of the individual patient and can be, for example, once per day or twice, or more times, per day. Administration of the compound continues for as long as necessary to treat the disease or condition. For example, a compound can be administered to a human having cancer for a period of from about 20 days to about 180 days or, for example, for a period of from about 20 days to about 90 days or, for example, for a period of from about 30 days to about 60 days.

Administration can be intermittent, with a period of several or more days during which a patient receives a daily dose of the compound of the present disclosure followed by a period of several or more days during which a patient does not receive a daily dose of the compound. For example, a patient can receive a dose of the compound every other day, or three times per week. Again by way of example, a patient can receive a dose of the compound each day for a period of from about 1 to about 14 days, followed by a period of about 7 to about 21 days during which the patient does not receive a dose of the compound, followed by a subsequent period (e.g., from about 1 to about 14 days) during which the patient again receives a daily dose of the compound. Alternating periods of administration of the compound, followed by non-administration of the compound, can be repeated as clinically required to treat the patient.

In some embodiments, pharmaceutical compositions comprising a compound of the present disclosure, or a pharmaceutically acceptable salt thereof, in combination with one or more (e.g., one, two, three, four, one or two, one to three, or one to four) additional therapeutic agents, and a pharmaceutically acceptable excipient are provided.

In some embodiments, kits comprising a compound of the present disclosure, or a pharmaceutically acceptable salt thereof, in combination with one or more (e.g., one, two, three, four, one or two, one to three, or one to four) additional therapeutic agents are provided.

In some embodiments, a compound of the present disclosure, or a pharmaceutically acceptable salt thereof, is combined with one, two, three, four or more additional therapeutic agents. In some embodiments, a compound of the present disclosure, or a pharmaceutically acceptable salt thereof, is combined with two additional therapeutic agents. In some embodiments, a compound of the present disclosure, or a pharmaceutically acceptable salt thereof, is combined with three additional therapeutic agents. In some embodiments, a compound of the present disclosure, or a pharmaceutically acceptable salt thereof, is combined with four additional therapeutic agents. The one, two, three, four or more additional therapeutic agents can be different therapeutic agents selected from the same class of therapeutic agents, and/or they can be selected from different classes of therapeutic agents.

In some embodiments, when a compound of the present disclosure is combined with one or more additional therapeutic agents as described herein, the components of the composition are administered as a simultaneous or sequential regimen. When administered sequentially, the combination may be administered in two or more administrations.

In some embodiments, a compound of the present disclosure is combined with one or more additional therapeutic agents in a unitary dosage form for simultaneous administration to a patient, for example as a solid dosage form for oral administration.

In some embodiments, a compound of the present disclosure is co-administered with one or more additional therapeutic agents.

In order to prolong the effect of a compound of the present disclosure, it is often desirable to slow the absorption of a compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending a compound in an oil vehicle. Injectable depot forms are made by forming microencapsule matrices of a compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping a compound in liposomes or microemulsions that are compatible with body tissues.

V. Combination Therapy

The compounds of the present disclosure and compositions provided herein are also used in combination with other active therapeutic agents. The other active therapeutic agents may be anti-cancer or antiviral, e.g., anti-HIV or anti-hepatitis B virus, agents as appropriate.

A. Combination Therapies

1. Cancer

In some embodiments, a compound as described herein, is combined with one or more additional therapeutic agents, e.g., an inhibitory immune checkpoint blocker or inhibitor, a stimulatory immune checkpoint stimulator, agonist or activator, a chemotherapeutic agent, an anti-cancer agent, a radiotherapeutic agent, an anti-neoplastic agent, an anti-proliferation agent, an anti-angiogenic agent, an anti-inflammatory agent, an immunotherapeutic agent, a therapeutic antigen-binding molecule (mono- and multi-specific antibodies and fragments thereof in any format (e.g., including without limitation DARTs®, Duobodies®, BiTEs®, BiKEs, TriKEs, XmAbs®, TandAbs®, scFvs, Fabs, Fab derivatives), bi-specific antibodies, non-immunoglobulin antibody mimetics (e.g., including without limitation adnectins, affilins, affimers, affitins, alphabodies, anticalins, peptide aptamers, armadillo repeat proteins (ARMs), atrimers, avimers, designed ankyrin repeat proteins (DARPins®), fynomers, knottins, Kunitz domain peptides, monobodies, and nanoCLAMPs), antibody-drug conjugates (ADC), antibody-peptide conjugate), an oncolytic virus, a gene modifier or editor, a cell comprising a chimeric antigen receptor (CAR), e.g., including a T-cell immunotherapeutic agent, an NK-cell immunotherapeutic agent, or a macrophage immunotherapeutic agent, a cell comprising an engineered T-cell receptor (TCR-T), or any combination thereof.

Illustrative Targets

In some embodiments, the one or more additional therapeutic agents include, without limitation, an inhibitor, agonist, antagonist, ligand, modulator, stimulator, blocker, activator or suppressor of a target (e.g., polypeptide or polynucleotide) including without limitation: Abelson murine leukemia viral oncogene homolog 1 gene (ABL, such as ABL1), Acetyl-CoA carboxylase (such as ACC1/2), activated CDC kinase (ACK, such as ACK1), Adenosine deaminase, adenosine receptor (such as A2BR, A2aR, A3aR), Adenylate cyclase, ADP ribosyl cyclase-1, adrenocorticotropic hormone receptor (ACTH), Aerolysin, AKT1 gene, Alk-5 protein kinase, Alkaline phosphatase, Alpha 1 adrenoceptor, Alpha 2 adrenoceptor, Alpha-ketoglutarate dehydrogenase (KGDH), Aminopeptidase N, AMP activated protein kinase, anaplastic lymphoma kinase (ALK, such as ALK1), Androgen receptor, Angiopoietin (such as ligand-1, ligand-2), Angiotensinogen (AGT) gene, murine thymoma viral oncogene homolog 1 (AKT) protein kinase (such as AKT1, AKT2, AKT3), apolipoprotein A-I (APOA1) gene, Apoptosis inducing factor, apoptosis protein (such as 1, 2), apoptosis signal-regulating kinase (ASK, such as ASK1), Arginase (I), Arginine deiminase, Aromatase, Asteroid homolog 1 (ASTE1) gene, ataxia telangiectasia and Rad 3 related (ATR) serine/threonine protein kinase, Aurora protein kinase (such as 1, 2), Axl tyrosine kinase receptor, 4-1BB ligand (CD137L), Baculoviral IAP repeat containing 5 (BIRC5) gene, Basigin, B-cell lymphoma 2 (BCL2) gene, Bcl2 binding component 3, Bcl2 protein, BCL2L11 gene, BCR (breakpoint cluster region) protein and gene, Beta adrenoceptor, Beta-catenin, B-lymphocyte antigen CD19, B-lymphocyte antigen CD20, B-lymphocyte cell adhesion molecule, B-lymphocyte stimulator ligand, Bone morphogenetic protein-10 ligand, Bone morphogenetic protein-9 ligand modulator, Brachyury protein, Bradykinin receptor, B-Raf proto-oncogene (BRAF), Brc-Abl tyrosine kinase, Bromodomain and external domain (BET) bromodomain containing protein (such as BRD2, BRD3, BRD4), Bruton's tyrosine kinase (BTK), Calmodulin, calmodulin-dependent protein kinase (CaMK, such as CAMKII), Cancer testis antigen 2, Cancer testis antigen NY-ESO-1, cancer/testis antigen 1B (CTAG1) gene, Cannabinoid receptor (such as CB1, CB2), Carbonic anhydrase, casein kinase (CK, such as CKI, CKII), Caspase (such as caspase-3, caspase-7, Caspase-9), caspase 8 apoptosis-related cysteine peptidase CASP8-FADD-like regulator, Caspase recruitment domain protein-15, Cathepsin G, CCR5 gene, CDK-activating kinase (CAK), Checkpoint kinase (such as CHK1, CHK2), chemokine (C-C motif) receptor (such as CCR2, CCR4, CCR5, CCR8), chemokine (C-X-C motif) receptor (such as CXCR1, CXCR2, CXCR3 and CXCR4), Chemokine CC21 ligand, Cholecystokinin CCK2 receptor, Chorionic gonadotropin, c-Kit (tyrosine-protein kinase Kit or CD117), CISH (Cytokine-inducible SH2-containing protein), Claudin (such as 6, 18), cluster of differentiation (CD) such as CD4, CD27, CD29, CD30, CD33, CD37, CD40, CD40 ligand receptor, CD40 ligand, CD40LG gene, CD44, CD45, CD47, CD49b, CD51, CD52, CD55, CD58, CD66e (CEACAM6), CD70 gene, CD74, CD79, CD79b, CD79B gene, CD80, CD95, CD99, CD117, CD122, CDw123, CD134, CDw137, CD158a, CD158b1, CD158b2, CD223, CD276 antigen; clusterin (CLU) gene, Clusterin, c-Met (hepatocyte growth factor receptor (HGFR)), Complement C3, Connective tissue growth factor, COP9 signalosome subunit 5, CSF-1 (colony-stimulating factor 1 receptor), CSF2 gene, CTLA-4 (cytotoxic T-lymphocyte protein 4) receptor, C-type lectin domain protein 9A (CLEC9A), Cyclin D1, Cyclin GI, cyclin-dependent kinases (CDK, such as CDK1, CDK12, CDK1B, CDK2-9), cyclooxygenase (such as COX1, COX2), CYP2B1 gene, Cysteine palmitoyltransferase porcupine, Cytochrome P450 11B2, Cytochrome P450 17, cytochrome P450 17A1, Cytochrome P450 2D6, cytochrome P450 3A4, Cytochrome P450 reductase, cytokine signalling-1, cytokine signalling-3, Cytoplasmic isocitrate dehydrogenase, Cytosine deaminase, cytosine DNA methyltransferase, cytotoxic T-lymphocyte protein-4, DDR2 gene, DEAD-box helicase 6 (DDX6), Death receptor 5 (DR5, TRAILR2), Death receptor 4 (DR4, TRAILR1), Delta-like protein ligand (such as 3, 4), Deoxyribonuclease, Deubiquitinating enzymes (DUBs), Dickkopf-1 ligand, dihydrofolate reductase (DHFR), Dihydropyrimidine dehydrogenase, Dipeptidyl peptidase IV, discoidin domain receptor (DDR, such as DDR1), Diacylglycerol kinase zeta (DGKZ), DNA binding protein (such as HU-beta), DNA dependent protein kinase, DNA gyrase, DNA methyltransferase, DNA polymerase (such as alpha), DNA primase, dUTP pyrophosphatase, L-dopachrome tautomerase, E3 ubiquitin-protein ligase (such as RNF128, CBL-B), echinoderm microtubule like protein 4, EGFR tyrosine kinase receptor, Elastase, Elongation factor 1 alpha 2, Elongation factor 2, Endoglin, Endonuclease, endoplasmic reticulum aminopeptidase (ERAP, such as ERAP 1, ERAP2), Endoplasmin, Endosialin, Endostatin, endothelin (such as ET-A, ET-B), Enhancer of zeste homolog 2 (EZH2), Ephrin (EPH) tyrosine kinase (such as Epha3, Ephb4), Ephrin B2 ligand, epidermal growth factor, epidermal growth factor receptors (EGFR), epidermal growth factor receptor (EGFR) gene, Epigen, Epithelial cell adhesion molecule (EpCAM), Erb-b2 (v-erb-b2 avian erythroblastic leukemia viral oncogene homolog 2) tyrosine kinase receptor, Erb-b3 tyrosine kinase receptor, Erb-b4 tyrosine kinase receptor, E-selectin, Estradiol 17 beta dehydrogenase, Estrogen receptor (such as alpha, beta), Estrogen related receptor, Eukaryotic translation initiation factor 5A (EIF5A) gene, Exportin 1, Extracellular signal related kinase (such as 1, 2), Extracellular signal-regulated kinases (ERK), Hypoxia-inducible factor prolyl hydroxylase (HIF-PH or EGLN), Factor (such as Xa, VIIa), farnesoid x receptor (FXR), Fas ligand, Fatty acid synthase (FASN), Ferritin, FGF-2 ligand, FGF-5 ligand, fibroblast growth factor (FGF, such as FGF1, FGF2, FGF4), Fibronectin, focal adhesion kinase (FAK, such as FAK2), folate hydrolase prostate-specific membrane antigen 1 (FOLH1), Folate receptor (such as alpha), Folate, Folate transporter 1, FYN tyrosine kinase, paired basic amino acid cleaving enzyme (FURIN), Beta-glucuronidase, Galactosyltransferase, Galectin-3, Ganglioside GD2, Glucocorticoid, glucocorticoid-induced TNFR-related protein GITR receptor, Glutamate carboxypeptidase II, glutaminase, Glutathione S-transferase P, glycogen synthase kinase (GSK, such as 3-beta), Glypican 3 (GPC3), gonadotropin-releasing hormone (GNRH), Granulocyte macrophage colony stimulating factor (GM-CSF) receptor, Granulocyte-colony stimulating factor (GCSF) ligand, growth factor receptor-bound protein 2 (GRB2), Grp78 (78 kDa glucose-regulated protein) calcium binding protein, molecular chaperone groEL2 gene, Heme oxygenase 1 (HO1), Heme oxygenase 2 (HO2), Heat shock protein (such as 27, 70, 90 alpha, beta), Heat shock protein gene, Heat stable enterotoxin receptor, Hedgehog protein, Heparanase, Hepatocyte growth factor, HERV-H LTR associating protein 2, Hexose kinase, Histamine H2 receptor, Histone methyltransferase (DOT1L), histone deacetylase (HDAC, such as 1, 2, 3, 6, 10, 11), Histone H1, Histone H3, HLA class I antigen (A-2 alpha), HLA class II antigen, HLA class I antigen alpha G (HLA-G), Non-classical HLA, Homeobox protein NANOG, HSPB1 gene, Human leukocyte antigen (HLA), Human papillomavirus (such as E6, E7) protein, Hyaluronic acid, Hyaluronidase, Hypoxia inducible factor-1 alpha (HIF1α), Imprinted Maternally Expressed Transcript (H19) gene, mitogen-activated protein kinase 1 (MAP4K1), tyrosine-protein kinase HCK, I-Kappa-B kinase (IKK, such as IKKbe), IL-1 alpha, IL-1 beta, IL-12, IL-12 gene, IL-15, IL-17, IL-2 gene, IL-2 receptor alpha subunit, IL-2, IL-3 receptor, IL-4, IL-6, IL-7, IL-8, immunoglobulin (such as G, G1, G2, K, M), Immunoglobulin Fc receptor, Immunoglobulin gamma Fc receptor (such as I, III, IIIA), indoleamine 2,3-dioxygenase (IDO, such as IDO1 and IDO2), indoleamine pyrrole 2,3-dioxygenase 1 inhibitor, insulin receptor, Insulin-like growth factor (such as 1, 2), Integrin alpha-4/beta-1, integrin alpha-4/beta-7, Integrin alpha-5/beta-1, Integrin alpha-V/beta-3, Integrin alpha-V/beta-5, Integrin alpha-V/beta-6, Intercellular adhesion molecule 1 (ICAM-1), interferon (such as alpha, alpha 2, beta, gamma), Interferon inducible protein absent in melanoma 2 (AIM2), interferon type I receptor, Interleukin 1 ligand, Interleukin 13 receptor alpha 2, interleukin 2 ligand, interleukin-1 receptor-associated kinase 4 (IRAK4), Interleukin-2, Interleukin-29 ligand, Interleukin 35 (IL-35), isocitrate dehydrogenase (such as IDH1, IDH2), Janus kinase (JAK, such as JAK1, JAK2), Jun N terminal kinase, kallikrein-related peptidase 3 (KLK3) gene, Killer cell Ig like receptor, Kinase insert domain receptor (KDR), Kinesin-like protein KIF11, Kirsten rat sarcoma viral oncogene homolog (KRAS) gene, Kisspeptin (KiSS-1) receptor, KIT gene, v-kit Hardy-Zuckerman 4 feline sarcoma viral oncogene homolog (KIT) tyrosine kinase, lactoferrin, Lanosterol-14 demethylase, LDL receptor related protein-1, Leukocyte immunoglobulin-like receptor subfamily B member 1 (ILT2), Leukocyte immunoglobulin-like receptor subfamily B member 2 (ILT4), Leukotriene A4 hydrolase, Listeriolysin, L-Selectin, Luteinizing hormone receptor, Lyase, lymphocyte activation gene 3 protein (LAG-3), Lymphocyte antigen 75, Lymphocyte function antigen-3 receptor, lymphocyte-specific protein tyrosine kinase (LCK), Lymphotactin, Lyn (Lck/Yes novel) tyrosine kinase, lysine demethylases (such as KDM1, KDM2, KDM4, KDM5, KDM6, A/B/C/D), Lysophosphatidate-1 receptor, lysosomal-associated membrane protein family (LAMP) gene, Lysyl oxidase homolog 2, lysyl oxidase protein (LOX), 5-Lipoxygenase (5-LOX), Hematopoietic Progenitor Kinase 1 (HPK1), Hepatocyte growth factor receptor (MET) gene, macrophage colony-stimulating factor (MCSF) ligand, Macrophage migration inhibitory fact, MAGEC1 gene, MAGEC2 gene, Major vault protein, MAPK-activated protein kinase (such as MK2), Mas-related G-protein coupled receptor, matrix metalloprotease (MMP, such as MMP2, MMP9), Mcl-1 differentiation protein, Mdm2 p53-binding protein, Mdm4 protein, Melan-A (MART-1) melanoma antigen, Melanocyte protein Pmel 17, melanocyte stimulating hormone ligand, melanoma antigen family A3 (MAGEA3) gene, Melanoma associated antigen (such as 1, 2, 3, 6), Membrane copper amine oxidase, Mesothelin, MET tyrosine kinase, Metabotropic glutamate receptor 1, Metalloreductase STEAP1 (six transmembrane epithelial antigen of the prostate 1), Metastin, methionine aminopeptidase-2, Methyltransferase, Mitochondrial 3 ketoacyl CoA thiolase, mitogen-activate protein kinase (MAPK), mitogen-activated protein kinase (MEK, such as MEK1, MEK2), mTOR (mechanistic target of rapamycin (serine/threonine kinase), mTOR complex (such as 1,2), mucin (such as 1, 5A, 16), mut T homolog (MTH, such as MTH1), Myc proto-oncogene protein, myeloid cell leukemia 1 (MCL1) gene, myristoylated alanine-rich protein kinase C substrate (MARCKS) protein, NAD ADP ribosyltransferase, natriuretic peptide receptor C, Neural cell adhesion molecule 1, Neurokinin 1 (NK1) receptor, Neurokinin receptor, Neuropilin 2, NF kappa B activating protein, NIMA-related kinase 9 (NEK9), Nitric oxide synthase, NK cell receptor, NK3 receptor, NKG2 A B activating NK receptor, NLRP3 (NACHT LRR PYD domain protein 3) modulators, Noradrenaline transporter, Notch (such as Notch-2 receptor, Notch-3 receptor, Notch-4 receptor), Nuclear erythroid 2-related factor 2, Nuclear Factor (NF) kappa B, Nucleolin, Nucleophosmin, nucleophosmin-anaplastic lymphoma kinase (NPM-ALK), 2 oxoglutarate dehydrogenase, 2,5-oligoadenylate synthetase, O-methylguanine DNA methyltransferase, Opioid receptor (such as delta), Omithine decarboxylase, Orotate phosphoribosyltransferase, orphan nuclear hormone receptor NR4A1, Osteocalcin, Osteoclast differentiation factor, Osteopontin, OX-40 (tumor necrosis factor receptor superfamily member 4 TNFRSF4, or CD134) receptor, P3 protein, p38 kinase, p38 MAP kinase, p53 tumor suppressor protein, Parathyroid hormone ligand, peroxisome proliferator-activated receptors (PPAR, such as alpha, delta, gamma), P-Glycoprotein (such as 1), phosphatase and tensin homolog (PTEN), phosphatidylinositol 3-kinase (PI3K), phosphoinositide-3 kinase (PI3K such as alpha, delta, gamma), phosphorylase kinase (PK), PKN3 gene, placenta growth factor, platelet-derived growth factor (PDGF, such as alpha, beta), Platelet-derived growth factor (PDGF, such as alpha, beta), Pleiotropic drug resistance transporter, Plexin B1, PLKI gene, polo-like kinase (PLK), Polo-like kinase 1, Poly (ADP-ribose) polymerase (PARP, such as PARP1, PARP2 and PARP3, PARP7, and mono-PARPs), Preferentially expressed antigen in melanoma (PRAME) gene, Prenyl-binding protein (PrPB), Probable transcription factor PML, Progesterone receptor, Programmed cell death 1 (PD-1), Programmed cell death ligand 1 inhibitor (PD-L1), Prosaposin (PSAP) gene, Prostanoid receptor (EP4), Prostaglandin E2 synthase, prostate specific antigen, Prostatic acid phosphatase, proteasome, Protein E7, Protein famesyltransferase, protein kinase (PK, such as A, B, C), protein tyrosine kinase, Protein tyrosine phosphatase beta, Proto-oncogene serine/threonine-protein kinase (PIM, such as PIM-1, PIM-2, PIM-3), P-Selectin, Purine nucleoside phosphorylase, purinergic receptor P2X ligand gated ion channel 7 (P2X7), Pyruvate dehydrogenase (PDH), Pyruvate dehydrogenase kinase, Pyruvate kinase (PYK), 5-Alpha-reductase, Raf protein kinase (such as 1, B), RAF1 gene, Ras gene, Ras GTPase, RET gene, Ret tyrosine kinase receptor, retinoblastoma associated protein, retinoic acid receptor (such as gamma), Retinoid X receptor, Rheb (Ras homolog enriched in brain) GTPase, Rho (Ras homolog) associated protein kinase 2, ribonuclease, Ribonucleotide reductase (such as M2 subunit), Ribosomal protein S6 kinase, RNA polymerase (such as I, II), Ron (Recepteur d'Origine Nantais) tyrosine kinase, ROS1 (ROS proto-oncogene 1, receptor tyrosine kinase) gene, Ros1 tyrosine kinase, Runt-related transcription factor 3, Gamma-secretase, S100 calcium binding protein A9, Sarco endoplasmic calcium ATPase, Second mitochondria-derived activator of caspases (SMAC) protein, Secreted frizzled related protein-2, Secreted phospholipase A2, Semaphorin-4D, Serine protease, serine/threonine kinase (STK), serine/threonine-protein kinase (TBK, such as TBK1), signal transduction and transcription (STAT, such as STAT-1, STAT-3, STAT-5), Signaling lymphocytic activation molecule (SLAM) family member 7, six-transmembrane epithelial antigen of the prostate (STEAP) gene, SL cytokine ligand, smoothened (SMO) receptor, Sodium iodide cotransporter, Sodium phosphate cotransporter 2B, Somatostatin receptor (such as 1, 2, 3, 4, 5), Sonic hedgehog protein, Son of sevenless (SOS), Specific protein 1 (Sp1) transcription factor, Sphingomyelin synthase, Sphingosine kinase (such as 1, 2), Sphingosine-1-phosphate receptor-1, spleen tyrosine kinase (SYK), SRC gene, Src tyrosine kinase, Stabilin-1 (STAB1), STAT3 gene, Steroid sulfatase, Stimulator of interferon genes (STING) receptor, stimulator of interferon genes protein, Stromal cell-derived factor 1 ligand, SUMO (small ubiquitin-like modifier), Superoxide dismutase, Suppressor of cytokine signaling modulators (SOCS), Survivin protein, Synapsin 3, Syndecan-1, Synuclein alpha, T cell surface glycoprotein CD28, tank-binding kinase (TBK), TATA box-binding protein-associated factor RNA polymerase I subunit B (TAF1B) gene, T-cell CD3 glycoprotein zeta chain, T-cell differentiation antigen CD6, T-cell immunoglobulin and mucin-domain containing-3 (TIM-3), T-cell surface glycoprotein CD8, Tec protein tyrosine kinase, Tek tyrosine kinase receptor, telomerase, Telomerase reverse transcriptase (TERT) gene, Tenascin, Three prime repair exonuclease 1 (TREX1), Three prime repair exonuclease 2 (TREX2), Thrombopoietin receptor, Thymidine kinase, Thymidine phosphorylase, Thymidylate synthase, Thymosin (such as alpha 1), Thyroid hormone receptor, Thyroid stimulating hormone receptor, Tissue factor, TNF related apoptosis inducing ligand, TNFR1 associated death domain protein, TNF-related apoptosis-inducing ligand (TRAIL) receptor, TNFSF11 gene, TNFSF9 gene, Toll-like receptor (TLR such as 1-13), topoisomerase (such as I, II, III), Transcription factor, Transferase, transferrin (TF), transforming growth factor alpha (TGFα), transforming growth factor beta (TGFB) and isoforms thereof, TGF beta 2 ligand, Transforming growth factor TGF-β receptor kinase, Transglutaminase, Translocation associated protein, Transmembrane glycoprotein NMB, Trop-2 calcium signal transducer, trophoblast glycoprotein (TPBG) gene, Trophoblast glycoprotein, Tropomyosin receptor kinase (Trk) receptor (such as TrkA, TrkB, TrkC), tryptophan 2,3-dioxygenase (TDO), Tryptophan 5-hydroxylase, Tubulin, Tumor necrosis factor (TNF, such as alpha, beta), Tumor necrosis factor 13C receptor, tumor progression locus 2 (TPL2), Tumor protein 53 (TP53) gene, Tumor suppressor candidate 2 (TUSC2) gene, Tumor specific neoantigens, Tyrosinase, Tyrosine hydroxylase, tyrosine kinase (TK), Tyrosine kinase receptor, Tyrosine kinase with immunoglobulin-like and EGF-like domains (TIE) receptor, Tyrosine protein kinase ABL1 inhibitor, Ubiquitin, Ubiquitin carboxyl hydrolase isozyme L5, Ubiquitin thioesterase-14, Ubiquitin-conjugating enzyme E21 (UBE2I, UBC9), Ubiquitin-specific-processing protease 7 (USP7), Urease, Urokinase plasminogen activator, Uteroglobin, Vanilloid VR1, Vascular cell adhesion protein 1, vascular endothelial growth factor receptor (VEGFR), V-domain Ig suppressor of T-cell activation (VISTA), VEGF-1 receptor, VEGF-2 receptor, VEGF-3 receptor, VEGF-A, VEGF-B, Vimentin, Vitamin D3 receptor, Proto-oncogene tyrosine-protein kinase, Mer (Mer tyrosine kinase receptor modulators), YAP (Yes-associated protein modulators)es, Wee-1 protein kinase, Werner Syndrome RecQ Like Helicase (WRN), Wilms' tumor antigen 1, Wilms' tumor protein, WW domain containing transcription regulator protein 1 (TAZ), X-linked inhibitor of apoptosis protein, Zinc finger protein transcription factor or any combination thereof.

Illustrative Mechanisms of Action

In some embodiments, the one or more additional therapeutic agents may be categorized by their mechanism of action into, for example, the following groups:

anti-metabolites/anti-cancer agents, such as pyrimidine analogs floxuridine, capecitabine, cytarabine, CPX-351 (liposomal cytarabine, daunorubicin), and TAS-118;

Alpha 1 adrenoceptor/Alpha 2 adrenoceptor antagonists, such as phenoxybenzamine hydrochloride (injectable, pheochromocytoma);

Androgen receptor antagonists, such as nilutamide;

anti-cadherin antibodies, such as HKT-288;

anti-leucine-rich repeat containing 15 (LRRC15) antibodies, such as ABBV-085. ARGX-110;

angiotensin receptor blockers, nitric oxide donors;

antisense oligonucleotides, such as AEG35156, IONIS-KRAS-2.5Rx, EZN-3042, RX-0201, IONIS-AR-2.5Rx, BP-100 (prexigebersen), IONIS-STAT3-2.5Rx;

anti-angiopoietin (ANG)-2 antibodies, such as MED13617, and LY3127804;

anti-ANG-1/ANG-2 antibodies, such as AMG-780;

anti-CSF1R antibodies, such as emactuzumab, LY3022855, AMG-820, FPA-008 (cabiralizumab);

anti-endoglin antibodies, such as TRC105 (carotuximab);

anti-ERBB antibodies, such as CDX-3379, HLX-02, seribantumab;

anti-HER2 antibodies, such as HERCEPTIN® (trastuzumab), trastuzumab biosimimar, margetuximab, MED14276, BAT-8001, Pertuzumab (Perjeta), RG6264, ZW25 (a bispecific HER2-directed antibody targeting the extracellular domains 2 and 4; Cancer Discov. 2019 January; 9(1):8; PMID: 30504239);

anti-HLA-DR antibodies, such as IMMU-114;

anti-IL-3 antibodies, such as JNJ-56022473;

anti-TNF receptor superfamily member 18 (TNFRSF18, GITR; NCBI Gene ID: 8784) antibodies, such as MK-4166, MEDI1873, FPA-154, INCAGN-1876, TRX-518, BMS-986156, MK-1248, GWN-323; and those described, e.g. in Intl. Patent Publ. Nos. WO 2017/096179, WO 2017/096276, WO 2017/096189; and WO 2018/089628;

anti-EphA3 antibodies, such as KB-004;

anti-CD37 antibodies, such as otlertuzumab (TRU-016);

anti-FGFR-3 antibodies, such as LY3076226, B-701;

anti-FGFR-2 antibodies, such as GAL-F2;

anti-C5 antibodies, such as ALXN-1210;

anti-EpCAM antibodies, such as VB4-845;

anti-CEA antibodies, such as RG-7813;

CD66C) antibodies, such as BAY-1834942, NEO-201 (CEACAM 5/6);

anti-GD2 antibodies, such as APN-301;

anti-interleukin-17 (IL-17) antibodies, such as CJM-112;

anti-interleukin-1 beta antibodies, such as canakinumab (ACZ885), VPM087;

anti-carbonic anhydrase 9 (CA9, CAIX) antibodies, such as TX-250;

anti-CD38 antibodies, such as isatuximab, MOR-202, TAK-079;

anti-CD38-attenukine, such as TAK573;

anti-Mucin 1 (MUC1) antibodies, such as gatipotuzumab, Mab-AR-20.5;

anti-CD33 antibodies, such as IMGN-779;

anti-KMA antibodies, such as MDX-1097;

anti-CD55 antibodies, such as PAT-SC1;

anti-c-Met antibodies, such as ABBV-399;

anti-PSMA antibodies, such as ATL-101;

anti-CD100 antibodies, such as VX-15;

anti-EPHA3 antibodies, such as fibatuzumab;

anti-APRIL antibodies, such as BION-1301;

anti-fibroblast activation protein (FAP)/IL-2R antibodies, such as RG7461;

anti-fibroblast activation protein (FAP)/TRAIL-R2 antibodies, such as RG7386;

anti-fucosyl-GM1 antibodies, such as BMS-986012;

anti-IL-8 (Interleukin-8) antibodies, such as HuMax-Inflam;

anti-myostatin inhibitors, such as landogrozumab;

anti-delta-like protein ligand 3 (DDL3) antibodies, such as rovalpituzumab tesirine;

anti-DLL4 (delta like ligand 4) antibodies, such as demcizumab;

anti-clusterin antibodies, such as AB-16B5;

anti-Ephrin-A4 (EFNA4) antibodies, such as PF-06647263;

anti-RANKL antibodies, such as denosumab;

anti-mesothelin antibodies, such as BMS-986148, Anti-MSLN-MMAE;

anti-sodium phosphate cotransporter 2B (NaP2B) antibodies, such as lifastuzumab anti-TGFb antibodies, such as SAR439459;

anti-transforming growth factor-beta (TGF-beta) antibodies, such as ABBV-151, LY3022859, NIS793, XOMA 089;

purine analogs, folate antagonists (such as pralatrexate), cladribine, pentostatin, fludarabine and related inhibitors;

antiproliferative/antimitotic agents including natural products, such as *vinca* alkaloids (vinblastine, vincristine) and microtubule disruptors such as taxane (paclitaxel, docetaxel), vinblastin, nocodazole, epothilones, vinorelbine (NAVELBINE®), and epipodophyllotoxins (etoposide, teniposide);

DNA damaging agents, such as actinomycin, amsacrine, busulfan, carboplatin, chlorambucil, cisplatin, cyclophosphamide (CYTOXAN®), dactinomycin, daunorubicin, doxorubicin, DEBDOX, epirubicin, iphosphamide, melphalan, merchlorethamine, mitomycin C, mitoxantrone, nitrosourea, procarbazine, taxol, Taxotere, teniposide, etoposide, and triethylenethiophosphoramide;

DNA-hypomethylating agents, such as guadecitabine (SGI-110), ASTX727;

antibiotics such as dactinomycin, daunorubicin, doxorubicin, idarubicin, anthracyclines, mitoxantrone, bleomycins, plicamycin (mithramycin);

enzymes such as L-asparaginase which systemically metabolizes L-asparagine and deprives cells which do not have the capacity to synthesize their own asparagine;

DNAi oligonucleotides targeting Bcl-2, such as PNT2258; agents that activate or reactivate latent human immunodeficiency virus (HIV), such as panobinostat and romidepsin;

asparaginase stimulators, such as crisantaspase (Erwinase®) and GRASPA (ERY-001, ERY-ASP), calaspargase pegol, pegaspargase;

pan-Trk, ROS1 and ALK inhibitors, such as entrectinib, TPX-0005;

anaplastic lymphoma kinase (ALK) inhibitors, such as alectinib, ceritinib, alecensa (RG7853), ALUNBRIG® (brigatinib);

antiproliferative/antimitotic alkylating agents, such as nitrogen mustard cyclophosphamide and analogs (e.g., melphalan, chlorambucil, hexamethylmelamine, thiotepa), alkyl nitrosoureas (e.g., carmustine) and analogs, streptozocin, and triazenes (e.g., dacarbazine);

antiproliferative/antimitotic antimetabolites, such as folic acid analogs (methotrexate);

platinum coordination complexes (e.g., cisplatin, oxiloplatinim, and carboplatin), procarbazine, hydroxyurea, mitotane, and aminoglutethimide;

hormones, hormone analogs (e.g., estrogen, tamoxifen, goserelin, bicalutamide, and nilutamide), and aromatase inhibitors (e.g., letrozole and anastrozole);

antiplatelet agents; anticoagulants such as heparin, synthetic heparin salts, and other inhibitors of thrombin;

fibrinolytic agents such as tissue plasminogen activator, streptokinase, urokinase, aspirin, dipyridamole, ticlopidine, and clopidogrel;

antimigratory agents; antisecretory agents (e.g., breveldin);

immunosuppressives, such as tacrolimus, sirolimus, azathioprine, and mycophenolate;

growth factor inhibitors, and vascular endothelial growth factor inhibitors;

fibroblast growth factor inhibitors, such as FPA14;

AMP activated protein kinase stimulators, such as metformin hydrochloride;

ADP ribosyl cyclase-1 inhibitors, such as daratumumab (DARZALEX®);

Caspase recruitment domain protein-15 stimulators, such as mifamurtide (liposomal);

CCR5 chemokine antagonists, such as MK-7690 (vicriviroc);

CDC17 protein kinase inhibitors, such as TAK-931;

Cholesterol side-chain cleavage enzyme inhibitors, such as ODM-209;

Dihydropyrimidine dehydrogenase/Orotate phosphoribosyltransferase inhibitors, such as Cefesone (tegafur+gimeracil+oteracil potassium);

DNA polymerase/Ribonucleotide reductase inhibitors, such as clofarabine;

DNA interference oligonucleotides, such as PNT2258, AZD-9150;

Estrogen receptor modulators, such as bazedoxifene;

Estrogen receptor agonists/Progesterone receptor antagonists, such as TRI-CYCLEN LO (norethindrone+ethinyl estradiol);

HLA class I antigen A-2 alpha modulators, such as FH-MCVA2TCR;

HLA class I antigen A-2 alpha/MART-1 melanoma antigen modulators, such as MART-1 F5 TCR engineered PBMC;

Human Granulocyte Colony Stimulating Factors, such as PF-06881894;

GNRH receptor agonists, such as leuprorelin acetate, leuprorelin acetate sustained release depot (ATRIGEL), triptorelin pamoate, goserelin acetate;

GNRH receptor antagonists, such as elagolix, relugolix, degarelix;

Endoplasmin modulators, such as anlotinib;

H+K+ATPase inhibitors, such as omeprazole, esomeprazole;

ICAM-1/CD55 modulators, such as cavatak (V-937);

IL-15/IL-12 modulators, such as SAR441000;

Interleukin 23A inhibitors, such as guselkumab;

Lysine specific histone demethylase 1 inhibitors, such as CC-90011;

IL-12 Mma, such as MEDI1191;

RIG-I modulators, such as RGT-100;

NOD2 modulators, such as SB-9200, and IR-103.

Progesterone receptor agonists, such as levonorgestrel;

Protein cereblon modulators, such as CC-92480, CC-90009;

Protein cereblon modulators/DNA binding protein Ikaros inhibitors/Zinc finger binding protein Aiolos inhibitors, such as iberdomide;

Retinoid X receptor modulators, such as alitretinoin, bexarotene (oral formulation);

RIP-1 kinase inhibitors, such as GSK-3145095;

selective oestrogen receptor degraders, such as AZD9833;

SUMO inhibitors, such as TAK-981;

Thrombopoietin receptor agonists, such as eltrombopag;

Thyroid hormone receptor agonists, such as levothyroxine sodium;

TNF agonists, such as tasonermin;

Tyrosine phosphatase substrate 1 inhibitors, such as CC-95251;

HER2 inhibitors, such as neratinib, tucatinib (ONT-380);

EGFR/ErbB2/Ephb4 inhibitors, such as tesevatinib;

EGFR/HER2 inhibitors, such as TAK-788;

EGFR family tyrosine kinase receptor inhibitors, such as DZD-9008

EGFR/ErbB-2 inhibitors, such as varlitinib;

Mutant selective EGFR inhibitors, such as PF-06747775, EGF816 (nazartinib), ASP8273, ACEA-0010, BI-1482694;

epha2 inhibitors, such as MM-310;
polycomb protein (EED) inhibitors, such as MAK683;
DHFR inhibitor/Folate transporter 1 modulator/Folate receptor antagonist, such as pralatrexate;
DHFR/GAR transformylase/Thymidylate synthase/Transferase inhibitors, such as pemetrexed disodium;
p38 MAP kinase inhibitors, such as ralimetinib;
PRMT inhibitors, such as MS203, PF-06939999, GSK3368715, GSK3326595;
Sphingosine kinase 2 (SK2) inhibitors, such as opaganib;
Nuclear erythroid 2-related factor 2 stimulators, such as omaveloxolone (RTA-408);
Tropomyosin receptor kinase (TRK) inhibitors, such as LOXO-195, ONO-7579;
Mucin 1 inhibitors, such as GO-203-2C;
MARCKS protein inhibitors, such as BIO-11006;
Folate antagonists, such as arfolitixorin;
Galectin-3 inhibitors, such as GR-MD-02;
Phosphorylated P68 inhibitors, such as RX-5902;
CD95/TNF modulators, such as ofranergene obadenovec;
pan-PIM kinase inhibitors, such as INCB-053914;
IL-12 gene stimulators, such as EGEN-001, tavokinogene telseplasmid;
Heat shock protein HSP90 inhibitors, such as TAS-116, PEN-866;
VEGF/HGF antagonists, such as MP-0250;
VEGF ligand inhibitors, such as bevacizumab biosimilar;
VEGF receptor antagonists/VEGF ligand inhibitors, such as ramucirumab;
VEGF-1/VEGF-2/VEGF-3 receptor antagonists; such as fruquintinib;
VEGF-1/VEGF-2 receptor modulators, such as HLA-A2402/HLA-A0201 restricted epitope peptide vaccine;
Placenta growth factor ligand inhibitor/VEGF-A ligand inhibitor, such as aflibercept;
SYK tyrosine kinase/JAK tyrosine kinase inhibitors, such as ASN-002;
Trk tyrosine kinase receptor inhibitors, such as larotrectinib sulfate;
JAK3/JAK/TBK1 kinase inhibitors, such as CS-12912;
IL-24 antagonist, such as AD-IL24;
NLRP3 (NACHT LRR PYD domain protein 3) modulators, such as BMS-986299;
RIG-I agonists, such as RGT-100;
Aerolysin stimulators, such as topsalysin;
P-Glycoprotein 1 inhibitors, such as HM-30181A;
CSF-1 antagonists, such as ARRY-382, BLZ-945;
CCR8 inhibitors, such as I-309, SB-649701, HG-1013, RAP-310;
anti-Mesothelin antibodies, such as SEL-403;
Thymidine kinase stimulators, such as aglatimagene besadenovec;
Polo-like kinase 1 inhibitors, such as PCM-075, onvansertib;
NAE inhibitors, such as pevonedistat (MLN-4924), TAS-4464;
Pleiotropic pathway modulators, such as avadomide (CC-122);
Amyloid protein binding protein-1 inhibitorS/Ubiquitin ligase modulators, such as pevonedistat;
FoxM1 inhibitors, such as thiostrepton;
UBA1 inhibitors, such as TAK-243;
Src tyrosine kinase inhibitors, such as VAL-201;
VDAC/HK inhibitors, such as VDA-1102;
Elf4a inhibitors, such as rohinitib, eFT226;
TP53 gene stimulators, such as ad-p53;
Retinoic acid receptor agonists, such as tretinoin;
Retinoic acid receptor alpha (RARα) inhibitors, such as SY-1425;
SIRT3 inhibitors, such as YC8-02;
Stromal cell-derived factor 1 ligand inhibitors, such as olaptesed pegol (NOX-A12);
IL-4 receptor modulators, such as MDNA-55;
Arginase-I stimulators, such as pegzilarginase;
Topoisomerase I inhibitors, such as irinotecan hydrochloride, Onivyde;
Topoisomerase I inhibitor/hypoxia inducible factor-1 alpha inhibitors, such as PEG-SN38 (firtecan pegol);
Hypoxia inducible factor-1 alpha inhibitors, such as PT-2977, PT-2385;
CD122 (IL-2 receptor) agonists, such as proleukin (aldesleukin, IL-2); pegylated IL-2 (eg NKTR-214); modified variants of IL-2 (eg THOR-707);
TLR7/TLR8 agonist, such as NKTR-262;
TLR7 agonists, such as DS-0509, GS-9620, LHC-165, TMX-101 (imiquimod);
p53 tumor suppressor protein stimulators such as kevetrin;
Mdm4/Mdm2 p53-binding protein inhibitors, such as ALRN-6924;
kinesin spindle protein (KSP) inhibitors, such as filanesib (ARRY-520);
CD80-fc fusion protein inhibitors, such as FPT-155;
Menin and mixed lineage leukemia (MLL) inhibitors such as KO-539;
Liver x receptor agonists, such as RGX-104;
IL-10 agonists, such as Pegilodecakin (AM-0010);
VEGFR/PDGFR inhibitors, such as vorolanib;
IRAK4 inhibitors, such as CA-4948;
anti-TLR-2 antibodies, such as OPN-305;
Calmodulin modulators, such as CBP-501;
Glucocorticoid receptor antagonists, such as relacorilant (CORT-125134);
Second mitochondria-derived activator of caspases (SMAC) protein inhibitors, such as BI-891065;
Lactoferrin modulators, such as LTX-315;
KIT proto-oncogene, receptor tyrosine kinase (KIT) inhibitors, such as PLX-9486;
platelet derived growth factor receptor alpha (PDGFRA)/KIT proto-oncogene, receptor tyrosine kinase (KIT) mutant-specific antagonists/inhibitors such as BLU-285, DCC-2618;
Exportin 1 inhibitors, such as eltanexor;
CHST15 gene inhibitors, such as STNM-01;
Somatostatin receptor antagonist, such as OPS-201;
CEBPA gene stimulators, such as MTL-501;
DKK3 gene modulators, such as MTG-201;
Chemokine (CXCR1/CXCR2) inhibitors, such as SX-682;
p70s6k inhibitors, such as MSC2363318A;
methionine aminopeptidase 2 (MetAP2) inhibitors, such as M8891, APL-1202;
arginine N-methyltransferase 5 inhibitors, such as GSK-3326595;
CD71 modulators, such as CX-2029 (ABBV-2029);
ATM (ataxia telangiectasia) inhibitors, such as AZD0156, AZD1390;
CHK1 inhibitors, such as GDC-0575, LY2606368 (prexasertib), SRA737, RG7741 (CHK1/2);
CXCR4 antagonists, such as BL-8040, LY2510924, burixafor (TG-0054), X4P-002, X4P-001-IO, Plerixafor;
EXH2 inhibitors, such as GSK2816126;

KDM1 inhibitors, such as ORY-1001, IMG-7289, INCB-59872, GSK-2879552;
CXCR2 antagonists, such as AZD-5069;
GM-CSF antibodies, such as lenzilumab;
DNA dependent protein kinase inhibitors, such as MSC2490484A (nedisertib), VX-984, AsiDNA (DT-01); protein kinase C (PKC) inhibitors, such as LXS-196, sotrastaurin;
Selective estrogen receptor downregulators (SERD), such as fulvestrant (Faslodex®), RG6046, RG6047, RG6171, elacestrant (RAD-1901), SAR439859 and AZD9496;
Selective estrogen receptor covalent antagonists (SERCAs), such as H3B-6545;
selective androgen receptor modulator (SARM), such as GTX-024, darolutamide;
transforming growth factor-beta (TGF-beta) kinase antagonists, such as galunisertib, LY3200882; TGF-beta inhibitors described in WO 2019/103203;
TGF beta receptor 1 inhibitors, such as PF-06952229;
bispecific antibodies, such as ABT-165 (DLL4/VEGF), MM-141 (IGF-1/ErbB3), MM-111 (Erb2/Erb3), JNJ-64052781 (CD19/CD3), PRS-343 (CD-137/HER2), AFM26 (BCMA/CD16A), JNJ-61186372 (EGFR/cMET), AMG-211 (CEA/CD3), RG7802 (CEA/CD3), ERY-974 (CD3/GPC3) vancizumab (angiopoietins/VEGF), PF-06671008 (Cadherins/CD3), AFM-13 (CD16/CD30), APV0436 (CD123/CD3), flotetuzumab (CD123/CD3), REGN-1979 (CD20/CD3), MCLA-117 (CD3/CLEC12A), MCLA-128 (HER2/HER3), JNJ-0819, JNJ-7564 (CD3/heme), AMG-757 (DLL3-CD3), MGD-013 (PD-1/LAG-3), FS-118 (LAG-3/PD-L1) MGD-019 (PD-1/CTLA-4), KN-046 (PD-1/CTLA-4), MEDI-5752 (CTLA-4/PD-1), RO-7121661 (PD-1/TIM-3), XmAb-20717 (PD-1/CTLA-4), AK-104 (CTLA-4/PD-1), AMG-330 (CD33/CD3), AMG-420 (BCMA/CD3), BI-836880 (VEFG/ANG2), JNJ-63709178 (CD123/CD3), MGD-007 (CD3/gpA33), MGD-009 (CD3/B7H3), AGEN1223, IMCgp100 (CD3/gp100), AGEN-1423, ATOR-1015 (CTLA-4/OX40), LY-3415244 (TIM-3/PDL1), INHIBRX-105 (4-1BB/PDL1), faricimab (VEGF-A/ANG-2), FAP-4-IBBL (4-1BB/FAP), XmAb-13676 (CD3/CD20), TAK-252 (PD-1/OX40L), TG-1801 (CD19/CD47), XmAb-18087 (SSTR2/CD3), catumaxomab (CD3/EpCAM), SAR-156597 (IL4/IL13), EMB-01 (EGFR/cMET), REGN-4018 (MUC16/CD3), REGN-1979 (CD20/CD3), RG-7828 (CD20/CD3), CC-93269 (CD3/BCMA), REGN-5458 (CD3/BCMA), navicixizumab (DLL4/VEGF), GRB-1302 (CD3/Erbb2), vanucizumab (VEGF-A/ANG-2), GRB-1342 (CD38/CD3), GEM-333 (CD3/CD33), IMM-0306 (CD47/CD20), RG6076, MEDI5752 (PD-1/CTLA-4), LY3164530 (MET/EGFR);
Alpha-ketoglutarate dehydrogenase (KGDH) inhibitors, such as CPI-613;
XPO1 inhibitors, such as selinexor (KPT-330);
Isocitrate dehydrogenase 2 (IDH2) inhibitors, such as enasidenib (AG-221);
IDH1 inhibitors such as AG-120, and AG-881 (IDH1 and IDH2), IDH-305, BAY-1436032;
IDH1 gene inhibitors, such as ivosidenib;
interleukin-3 receptor (IL-3R) modulators, such as SL-401;
Arginine deiminase stimulators, such as pegargiminase (ADI-PEG-20);
claudin-18 inhibitors, such as claudiximab;

β-catenin inhibitors, such as CWP-291;
chemokine receptor 2 (CCR) inhibitors, such as PF-04136309, CCX-872, BMS-813160 (CCR2/CCR5)
thymidylate synthase inhibitors, such as ONX-0801;
ALK/ROS1 inhibtors, such as lorlatinib;
tankyrase inhibitors, such as G007-LK;
Mdm2 p53-binding protein inhibitors, such as CMG-097, HDM-201; c-PIM inhibitors, such as PIM447;
sphingosine kinase-2 (SK2) inhibitors, such as Yeliva® (ABC294640);
DNA polymerase inhibitors, such as sapacitabine;
Cell cycle/Microtubule inhibitors, such as eribulin mesylate;
c-MET inhibitors, such as AMG-337, savolitinib, tivantinib (ARQ-197), capmatinib, and tepotinib, ABT-700, AG213, AMG-208, JNJ-38877618 (OMO-1), merestinib, HQP-8361;
c-Met/VEGFR inhibitors, such as BMS-817378, TAS-115;
c-Met/RON inhibitors, such as BMS-777607;
BCR/ABL inhibitors, such as rebastinib, asciminib, ponatinib (ICLUSIG®);
MNK1/MNK2 inhibitors, such as eFT-508;
Cytochrome P450 11B2/Cytochrome P450 17/AKT protein kinase inhibitors, such as LAE-201;
Cytochrome P450 3A4 stimulators, such as mitotane;
lysine-specific demethylase-1 (LSD1) inhibitors, such as CC-90011;
CSF1R/KIT and FLT3 inhibitors, such as pexidartinib (PLX3397);
Flt3 tyrosine kinase/Kit tyrosine kinase inhibitor and PDGF receptor antagonists, such as quizartinib dihydrochloride;
kinase inhibitors, such as vandetanib;
E selectin antagonists, such as GMI-1271;
differentiation inducers, such as tretinoin;
epidermal growth factor receptor (EGFR) inhibitors, such as osimertinib (AZD-9291), cetuximab;
topoisomerase inhibitors, such as Adriamycin, doxorubicin, daunorubicin, dactinomycin, DaunoXome, Caelyx, eniposide, epirubicin, etoposide, idarubicin, irinotecan, mitoxantrone, pixantrone, sobuzoxane, topotecan, irinotecan, MM-398 (liposomal irinotecan), vosaroxin and GPX-150, aldoxorubicin, AR-67, mavelertinib, AST-2818, avitinib (ACEA-0010), irofulven (MGI-114);
corticosteroids, such as cortisone, dexamethasone, hydrocortisone, methylprednisolone, prednisone, prednisolone;
growth factor signal transduction kinase inhibitors;
nucleoside analogs, such as DFP-10917;
Axl inhibitors, such as BGB-324 (bemcentinib), SLC-0211;
Axl/Flt3 inhibitors, such as gilteritinib;
Inhibitors of bromodomain and extraterminal motif (BET) proteins, including ABBV-744, BRD2 (NCBI Gene ID: 6046), BRD3 (NCBI Gene ID: 8019), BRD4 (NCBI Gene ID: 23476), and bromodomain testis-specific protein (BRDT; NCBI Gene ID: 676), such as INCB-054329, INCB057643, TEN-010, AZD-5153, ABT-767, BMS-986158, CC-90010, GSK525762 (molibresib), NHWD-870, ODM-207, GSK-2820151, GSK-1210151A, ZBC246, ZBC260, ZEN3694, FT-1101, RG-6146, CC-90010, CC-95775, mivebresib, BI-894999, PLX-2853, PLX-51107, CPI-0610, GS-5829;

PARP inhibitors, such as olaparib (MK7339), rucaparib, veliparib, talazoparib, ABT-767, BGB-290, fluzolepali (SHR-3162), niraparib (JNJ-64091742), bendamustine hydrochloride, PARP/Tankyrase inhibitors such as 2X-121 (e-7499); IMP-4297, SC-10914, IDX-1197, HWH-340, CK-102, simmiparib;

Proteasome inhibitors, such as ixazomib (NINLARO®), carfilzomib (Kyprolis®), marizomib, bortezomib;

Glutaminase inhibitors, such as CB-839 (telaglenastat), bis-2-(5-phenylacetamido-1,3,4-thiadiazol-2-yl)ethyl sulfide (BPTES);

mitochondrial complex I inhibitors, such as metformin, phenformin;

Vaccines, such as peptide vaccine TG-01 (RAS), GALE-301, GALE-302, nelipepimut-s, SurVaxM, DSP-7888, TPIV-200, PVX-410, VXL-100, DPX-E7, ISA-101, 6MHP, OSE-2101, galinpepimut-S, SVN53-67/M57-KLH, IMU-131, peptide subunit vaccine (acute lymphoblastic leukemia, University Children's Hospital Tuebingen); bacterial vector vaccines such as CRS-207/GVAX, axalimogene filolisbac (ADXS11-001); adenovirus vector vaccines such as nadofaragene firadenovec; autologous Gp96 vaccine; dendritic cells vaccines, such as CVactm, tapuldencel-T, eltrapuldencel-T, SL-701, BSK01TM, rocapuldencel-T (AGS-003), DCVAC, CVactm, stapuldencel-T, eltrapuldencel-T, SL-701, BSKO1TM, ADXS31-142, autologous dendritic cell vaccine (metastatic malignant melanoma, intradermal/intravenous, Universitatsklinikum Erlangen); oncolytic vaccines such as, talimogene laherparepvec, pexastimogene devacirepvec, GL-ONC1, MG1-MA3, parvovirus H-1, ProstAtak, enadenotucirev, MG1MA3, ASN-002 (TG-1042); therapeutic vaccines, such as CVAC-301, CMP-001, CreaVax-BC, PF-06753512, VBI-1901, TG-4010, ProscaVax™; tumor cell vaccines, such as Vigil® (IND-14205), Oncoquest-L vaccine; live attenuated, recombinant, serotype 1 poliovirus vaccine, such as PVS-RIPO; Adagloxad simolenin; MEDI-0457; DPV-001 a tumor-derived, autophagosome enriched cancer vaccine; RNA vaccines such as, CV-9209, LV-305; DNA vaccines, such as MEDI-0457, MVI-816, INO-5401; modified vaccinia virus Ankara vaccine expressing p53, such as MVA-p53; DPX-Survivac; BriaVax™; GI-6301; GI-6207; GI-4000; 10-103; Neoantigen peptide vaccines, such as AGEN-2017, GEN-010, NeoVax, RG-6180, GEN-009, PGV-001 (TLR-3 agonist), GRANITE-001, NEO-PV-01; Peptide vaccines that target heat shock proteins, such as PhosphoSynVax™; Vitespen (HSPPC-96-C), NANT Colorectal Cancer Vaccine containing aldoxorubicin, autologous tumor cell vaccine+systemic CpG-B+IFN-alpha (cancer), I0-120+I0-103 (PD-L1/PD-L2 vaccines), HB-201, HB-202, HB-301, TheraT®*-based vaccines;

TLR-3 agonist/interferon inducers, such as Poly-ICLC (NSC-301463);

STAT-3 inhibitors, such as napabucasin (BBI-608);

ATPase p97 inhibitors, such as CB-5083;

smoothened (SMO) receptor inhibitors, such as Odomzo® (sonidegib, formerly LDE-225), LEQ506, vismodegib (GDC-0449), BMS-833923, glasdegib (PF-04449913), LY2940680, and itraconazole;

interferon alpha ligand modulators, such as interferon alpha-2b, interferon alpha-2a biosimilar (Biogenomics), ropeginterferon alfa-2b (AOP-2014, P-1101, PEG IFN alpha-2b), Multiferon (Alfanative, Viragen), interferon alpha 1b, Roferon-A (Canferon, Ro-25-3036), interferon alfa-2a follow-on biologic (Biosidus)(Inmutag, Inter 2A), interferon alfa-2b follow-on biologic (Biosidus—Bioferon, Citopheron, Ganapar, Beijing Kawin Technology—Kaferon), Alfaferone, pegylated interferon alpha-1b, peginterferon alfa-2b follow-on biologic (Amega), recombinant human interferon alpha-1b, recombinant human interferon alpha-2a, recombinant human interferon alpha-2b, veltuzumab-IFN alpha 2b conjugate, Dynavax (SD-101), and interferon alfa-n1 (Humoferon, SM-10500, Sumiferon);

interferon gamma ligand modulators, such as interferon gamma (OH-6000, Ogamma 100);

IL-6 receptor modulators, such as tocilizumab, AS-101 (CB-06-02, IVX-Q-101);

Heat shock protein inhibitors/IL-6 receptor antagonists, such as siltuximab;

Telomerase modulators, such as, tertomotide (GV-1001, HR-2802, Riavax) and imetelstat (GRN-163, JNJ-63935937);

DNA methyltransferases inhibitors, such as temozolomide (CCRG-81045), decitabine, guadecitabine (S-110, SGI-110), KRX-0402, RX-3117, RRx-001, and azacytidine (CC-486);

DNA gyrase inhibitors, such as pixantrone and sobuzoxane;

DNA gyrase inhibitors/Topoisimerase II inhibitors, such as amrubicin;

Bcl-2 family protein inhibitors, such as ABT-263, venetoclax (ABT-199), ABT-737, RG7601, and AT-101;

Bcl-2/Bcl-XL inhibitors, such as novitoclax;

Notch inhibitors, such as LY3039478 (crenigacestat), tarextumab (anti-Notch2/3), BMS-906024;

hyaluronidase stimulators, such as PEGPH-20;

Erbb2 tyrosine kinase receptor inhibitors/Hyaluronidase stimulators, such as Herceptin Hylecta;

Wnt pathway inhibitors, such as SM-04755, PRI-724, WNT-974;

gamma-secretase inhibitors, such as PF-03084014, MK-0752, RO-4929097;

Grb-2 (growth factor receptor bound protein-2) inhibitors, such as BP1001;

TRAIL pathway-inducing compounds, such as ONC201, ABBV-621;

TRAIL modulators, such as SCB-313;

Focal adhesion kinase inhibitors, such as VS-4718, defactinib, GSK2256098;

hedgehog inhibitors, such as saridegib, sonidegib (LDE225), glasdegib;

Aurora kinase inhibitors, such as alisertib (MLN-8237), and AZD-2811, AMG-900, barasertib, ENMD-2076;

HSPB1 modulators (heat shock protein 27, HSP27), such as brivudine, apatorsen;

ATR inhibitors, such as BAY-937, AZD6738, AZD6783, VX-803, VX-970 (berzosertib) and VX-970;

Hsp90 inhibitors, such as AUY922, onalespib (AT13387), SNX-2112, SNX5422;

Murine double minute (mdm2) oncogene inhibitors, such as DS-3032b, RG7775, AMG-232, HDM201, and idasanutlin (RG7388);

CD137 agonists, such as urelumab, utomilumab (PF-05082566), AGEN2373, ADG-106, BT-7480;

STING agonists, such as ADU-5100 (MIW-815), SB-11285, MK-1454, SR-8291, AdVCA0848, GSK-532, SYN-STING, MSA-1, SR-8291, GSK3745417;

FGFR inhibitors, such as FGF-401, INCB-054828, BAY-1163877, AZD4547, JNJ-42756493, LY2874455, Debio-1347;

fatty acid synthase (FASN) inhibitors, such as TVB-2640;

Antigen CD19 inhibitors, such as MOR208, MEDI-551, AFM-11, inebilizumab;

CD44 binders, such as A6;

protein phosphatease 2A (PP2A) inhibitors, such as LB-100;

CYP17 inhibitors, such as seviteronel (VT-464), ASN-001, ODM-204, CFG920, abiraterone acetate;

RXR agonists, such as IRX4204;

hedgehog/smoothened (hh/Smo) antagonists, such as taladegib, patidegib, vismodegib;

complement C3 modulators, such as Imprime PGG;

IL-15 agonists, such as ALT-803, NKTR-255, interleukin-15/Fc fusion protein, AM-0015, NIZ-985, and hetIL-15;

EZH2 (enhancer of zeste homolog 2) inhibitors, such as tazemetostat, CPI-1205, GSK-2816126, PF-06821497;

Oncolytic viruses, such as pelareorep, CG-0070, MV-NIS therapy, HSV-1716, DS-1647, VCN-01, ONCOS-102, TBI-1401, tasadenoturev (DNX-2401), vocimagene amiretrorepvec, RP-1, CVA21, Celyvir, LOAd-703, OBP-301, IMLYGIC®;

DOT1L (histone methyltransferase) inhibitors, such as pinometostat (EPZ-5676);

toxins such as Cholera toxin, ricin, *Pseudomonas* exotoxin, *Bordetella pertussis* adenylate cyclase toxin, diphtheria toxin, and caspase activators;

DNA plasmids, such as BC-819

PLK inhibitors of PLK 1, 2, and 3, such as volasertib (PLKI);

WEE1 inhibitors, such as AZD-1775 (adavosertib); Rho kinase (ROCK) inhibitors, such as AT13148, KD025;

Inhibition of Apoptosis Protein (IAP) inhibitors, such as ASTX660, debio-1143, birinapant, APG-1387, LCL-161;

RNA polymerase inhibitors, such has lurbinectedin (PM-1183), CX-5461;

Tubulin inhibitors, such as PM-184, BAL-101553 (lisavanbulin), and OXI-4503, fluorapacin (AC-0001), plinabulin, vinflunine;

Toll-like receptor 4 (TLR-4) agonists, such as G100, GSK1795091, and PEPA-10;

Elongation factor 1 alpha 2 inhibitors, such as plitidepsin;

Elongation factor 2 inhibitors/Interleukin-2 ligands/NAD ADP ribosyltransferase stimulators, such as denileukin diftitox;

CD95 inhibitors, such as APG-101, APO-010, asunercept;

WT1 inhibitors, such as DSP-7888;

splicing factor 3B subunit1 (SF3B1) inhibitors, such as H3B-8800 retinoid Z receptor gamma (RORγ) agonists, such as LYC-55716; and

Microbiome modulators, such as SER-401, EDP-1503, MRx-0518.

In some embodiments, a compound as described herein, is co-administered with one or more additional therapeutic agents comprising an inhibitor or antagonist of: myeloid cell leukemia sequence 1 (MCL1) apoptosis regulator (NCBI Gene ID: 4170); mitogen-activated protein kinase 1 (MAP4K1) (also called Hematopoietic Progenitor Kinase 1 (HPK1), NCBI Gene ID: 11184); diacylglycerol kinase alpha (DGKA, DAGK, DAGK1 or DGK-alpha; NCBI Gene ID: 1606); 5'-nucleotidase ecto (NT5E or CD73; NCBI Gene ID: 4907); ectonucleoside triphosphate diphosphohydrolase 1 (ENTPD1 or CD39; NCBI Gene ID: 593); transforming growth factor beta 1 (TGFB1 or TGFβ; NCBI Gene ID: 7040); heme oxygenase 1 (HMOX1, HO-1 or HO1; NCBI Gene ID: 3162); heme oxygenase 2 (HMOX2, HO-2 or HO2; NCBI Gene ID: 3163); vascular endothelial growth factor A (VEGFA or VEGF; NCBI Gene ID: 7422); erb-b2 receptor tyrosine kinase 2 (ERBB2, HER2, HER2/neu or CD340; NCBI Gene ID: 2064), epidermal growth factor receptor (EGFR, ERBB, ERBB1 or HER1; NCBI Gene ID: 1956); ALK receptor tyrosine kinase (ALK, CD246; NCBI Gene ID: 238); poly(ADP-ribose) polymerase 1 (PARP1; NCBI Gene ID: 142); poly(ADP-ribose) polymerase 2 (PARP2; NCBI Gene ID: 10038); TCDD inducible poly (ADP-ribose) polymerase (TIPARP, PARP7; NCBI Gene ID: 25976); cyclin dependent kinase 4 (CDK4; NCBI Gene ID: 1019); cyclin dependent kinase 6 (CDK6; NCBI Gene ID: 1021); TNF receptor superfamily member 14 (TNFRSF14, HVEM, CD270; NCBI Gene ID: 8764); T cell immunoreceptor with Ig and ITIM domains (TIGIT; NCBI Gene ID: 201633); X-linked inhibitor of apoptosis (XIAP, BIRC4, IAP-3; NCBI Gene ID: 331); baculoviral IAP repeat containing 2 (BIRC2, cIAP1; NCBI Gene ID: 329); baculoviral IAP repeat containing 3 (BIRC3, cIAP2; NCBI Gene ID: 330); baculoviral IAP repeat containing 5 (BIRC5, surviving; NCBI Gene ID: 332); C-C motif chemokine receptor 2 (CCR2, CD192; NCBI Gene ID: 729230); C-C motif chemokine receptor 5 (CCR5, CD195; NCBI Gene ID: 1234); C-C motif chemokine receptor 8 (CCR8, CDw198; NCBI Gene ID: 1237); C-X-C motif chemokine receptor 2 (CXCR2, CD182; NCBI Gene ID: 3579); C-X-C motif chemokine receptor 3 (CXCR3, CD182, CD183; NCBI Gene ID: 2833); C-X-C motif chemokine receptor 4 (CXCR4, CD184; NCBI Gene ID: 7852); arginase (ARG1 (NCBI Gene ID: 383), ARG2 (NCBI Gene ID: 384)), carbonic anhydrase (CA1 (NCBI Gene ID: 759), CA2 (NCBI Gene ID: 760), CA3 (NCBI Gene ID: 761), CA4 (NCBI Gene ID: 762), CASA (NCBI Gene ID: 763), CASB (NCBI Gene ID: 11238), CA6 (NCBI Gene ID: 765), CA7 (NCBI Gene ID: 766), CA8 (NCBI Gene ID: 767), CA9 (NCBI Gene ID: 768), CA10 (NCBI Gene ID: 56934), CA11 (NCBI Gene ID: 770), CA12 (NCBI Gene ID: 771), CA13 (NCBI Gene ID: 377677), CA14 (NCBI Gene ID: 23632)), prostaglandin-endoperoxide synthase 1 (PTGS1, COX-1; NCBI Gene ID: 5742), prostaglandin-endoperoxide synthase 2 (PTGS2, COX-2; NCBI Gene ID: 5743), secreted phospholipase A2, prostaglandin E synthase (PTGES, PGES; Gene ID: 9536), arachidonate 5-lipoxygenase (ALOX5, 5-LOX; NCBI Gene ID: 240) and/or soluble epoxide hydrolase 2 (EPHX2, SEH; NCBI Gene ID: 2053); a secreted phospholipase A2 (e.g., PLA2G1B (NCBI Gene ID: 5319); PLA2G7 (NCBI Gene ID: 7941), PLA2G3 (NCBI Gene ID: 50487), PLA2G2A (NCBI Gene ID: 5320); PLA2G4A (NCBI Gene ID: 5321); PLA2G12A (NCBI Gene ID: 81579); PLA2G12B (NCBI Gene ID: 84647); PLA2G10 (NCBI Gene ID: 8399); PLA2G5 (NCBI Gene ID: 5322); PLA2G2D (NCBI Gene ID: 26279); PLA2G15 (NCBI Gene ID: 23659)); indoleamine 2,3-dioxygenase 1 (IDO1; NCBI Gene ID: 3620); indoleamine 2,3-dioxygenase 2 (IDO2; NCBI Gene ID: 169355); hypoxia inducible factor 1 subunit alpha (HIF1A; NCBI Gene ID: 3091); angiopoietin 1 (ANGPT1; NCBI Gene ID: 284); Endothelial TEK tyrosine kinase (TIE-2, TEK, CD202B; NCBI Gene ID: 7010); Janus kinase 1 (JAK1; NCBI Gene ID: 3716); catenin beta 1 (CTNNB1; NCBI Gene ID: 1499); histone deacetylase 9 (HDAC9; NCBI Gene ID: 9734) and/or 5'-3' exoribonuclease 1 (XRN1; NCBI Gene ID: 54464).

TCR Signaling Modulators

In some embodiments, a compound as described herein, is combined with one or more agonist or antagonist of T-Cell Receptor (TCR) signaling modulators. Activation of T cells through the TCR and is essential for thymocyte development and effector T cell function. TCR activation promotes signaling cascades that ultimately determine cell fate through regulating cytokine production, cell survival, proliferation, and differentiation. Examples of TCR signaling modulators include without limitation CD2 (cluster of differentiation 2, LFA-2, T11, LFA-3 receptor), CD3 (cluster of differentiation 3), CD4 (cluster of differentiation 4), CD8 (cluster of differentiation 8), CD28 (cluster of differentiation 28), CD45 (PTPRC, B220, GP180), LAT (Linker for activation of T cells, LAT1), Lck, LFA-1 (ITGB2, CD18, LAD, LCAMB), Src, Zap-70, SLP-76, DGKalpha, CBL-b, CISH, HPK.

Examples of agonist of cluster of differentiation 3 (CD3) that can be co-administered include without limitation MGD015.

In some embodiments, a compound as described herein, is combined with one or more blockers or inhibitors of inhibitory immune checkpoint proteins or receptors and/or with one or more stimulators, activators or agonists of one or more stimulatory immune checkpoint proteins or receptors. Blockade or inhibition of inhibitory immune checkpoints can positively regulate T-cell or NK cell activation and prevent immune escape of cancer cells within the tumor microenvironment. Activation or stimulation of stimulatory immune check points can augment the effect of immune checkpoint inhibitors in cancer therapeutics. In some embodiments, the immune checkpoint proteins or receptors regulate T cell responses (e.g., reviewed in Xu, et al., *J Exp Cin Cancer Res*. (2018) 37:110). In some embodiments, the immune checkpoint proteins or receptors regulate NK cell responses (e.g., reviewed in Davis, et al., *Semin Immunol*. (2017) 31:64-75 and Chiossone, et al., *Nat Rev Immunol*. (2018) 18(11):671-688).

Examples of immune checkpoint proteins or receptors include without limitation CD27, CD70; CD40, CD40LG; CD47, CD48 (SLAMF2), transmembrane and immunoglobulin domain containing 2 (TMIGD2, CD28H), CD84 (LY9B, SLAMF5), CD96, CD160, MS4A1 (CD20), CD244 (SLAMF4); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); natural killer cell cytotoxicity receptor 3 ligand 1 (NCR3LG1, B7H6); HERV-H LTR-associating 2 (HHLA2, B7H7); inducible T cell co-stimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF8 (CD30), TNFSF8 (CD30L); TNFRSF10A (CD261, DR4, TRAILR1), TNFRSF9 (CD137), TNFSF9 (CD137L); TNFRSF10B (CD262, DR5, TRAILR2), TNFRSF10 (TRAIL); TNFRSF14 (HVEM, CD270), TNFSF14 (HVEML); CD272 (B and T lymphocyte associated (BTLA)); TNFRSF17 (BCMA, CD269), TNFSF13B (BAFF); TNFRSF18 (GITR), TNFSF18 (GITRL); MHC class I polypeptide-related sequence A (MICA); MHC class I polypeptide-related sequence B (MICB); CD274 (PDL1, PD-L1); programmed cell death 1 (PDCD1, PD-1, PD-1); cytotoxic T-lymphocyte associated protein 4 (CTLA4, CD152); CD80 (B7-1), CD28; nectin cell adhesion molecule 2 (NECTIN2, CD112); CD226 (DNAM-1); Poliovirus receptor (PVR) cell adhesion molecule (PVR, CD155); PVR related immunoglobulin domain containing (PVRIG, CDI12R); T cell immunoreceptor with Ig and ITIM domains (TIGIT); T cell immunoglobulin and mucin domain containing 4 (TIMD4; TIM4); hepatitis A virus cellular receptor 2 (HAVCR2, TIMD3, TIM-3); galectin 9 (LGALS9); lymphocyte activating 3 (LAG-3, CD223); signaling lymphocytic activation molecule family member 1 (SLAMF1, SLAM, CD150); lymphocyte antigen 9 (LY9, CD229, SLAMF3); SLAM family member 6 (SLAMF6, CD352); SLAM family member 7 (SLAMF7, CD319); UL16 binding protein 1 (ULBP1); UL16 binding protein 2 (ULBP2); UL16 binding protein 3 (ULBP3); retinoic acid early transcript 1E (RAET1E; ULBP4); retinoic acid early transcript 1G (RAET1G; ULBP5); retinoic acid early transcript 1L (RAET1L; ULBP6); lymphocyte activating 3 (CD223); killer cell immunoglobulin like receptor (KIR); killer cell lectin like receptor C1 (KLRC1, NKG2A, CD159A); killer cell lectin like receptor K1 (KLRK1, NKG2D, CD314); killer cell lectin like receptor C2 (KLRC2, CD159c, NKG2C); killer cell lectin like receptor C3 (KLRC3, NKG2E); killer cell lectin like receptor C4 (KLRC4, NKG2F); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor D1 (KLRD1).

In some embodiments, a compound as described herein, is combined with one or more blockers or inhibitors of one or more T-cell inhibitory immune checkpoint proteins or receptors. Illustrative T-cell inhibitory immune checkpoint proteins or receptors include without limitation CD274 (PDL1, PD-L1); programmed cell death 1 ligand 2 (PDCD1LG2, PD-L2, CD273); programmed cell death 1 (PDCD1, PD1, PD-1); cytotoxic T-lymphocyte associated protein 4 (CTLA4, CD152); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); TNFRSF14 (HVEM, CD270), TNFSF14 (HVEML); CD272 (B and T lymphocyte associated (BTLA)); PVR related immunoglobulin domain containing (PVRIG, CDI12R); T cell immunoreceptor with Ig and ITIM domains (TIGIT); lymphocyte activating 3 (LAG-3, CD223); hepatitis A virus cellular receptor 2 (HAVCR2, TIMD3, TIM-3); galectin 9 (LGALS9); killer cell immunoglobulin like receptor (KIR); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); and killer cell immunoglobulin like receptor, three Ig domains and long cytoplasmic tail 1 (KIR3DL1). In some embodiments, a compound as described herein, is combined with one or more agonist or activators of one or more T-cell stimulatory immune checkpoint proteins or receptors. Illustrative T-cell stimulatory immune checkpoint proteins or receptors include without limitation CD27, CD70; CD40, CD40LG; inducible T cell costimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF9 (CD137), TNFSF9 (CD137L); TNFRSF18 (GITR), TNFSF18 (GITRL); CD80 (B7-1), CD28; nectin cell adhesion molecule 2 (NECTIN2, CD112); CD226 (DNAM-1); CD244 (2B4, SLAMF4), Poliovirus receptor (PVR) cell adhesion molecule (PVR, CD155). See, e.g., Xu, et al., *J Exp Cin Cancer Res.* (2018) 37:110.

In some embodiments, a compound as described herein, is combined with one or more blockers or inhibitors of one or more NK-cell inhibitory immune checkpoint proteins or receptors. Illustrative NK-cell inhibitory immune checkpoint proteins or receptors include without limitation killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor C1 (KLRC1, NKG2A, CD159A); and killer cell lectin like receptor D1 (KLRD1, CD94). In some embodiments, a compound as described herein, is combined with one or more agonist or activators of one or more NK-cell stimulatory immune checkpoint proteins or receptors. Illustrative NK-cell stimulatory immune checkpoint proteins or receptors include without limitation CD16, CD226 (DNAM-1); CD244 (2B4, SLAMF4); killer cell lectin like receptor K1 (KLRK1, NKG2D, CD314); SLAM family member 7 (SLAMF7). See, e.g., Davis, et al., *Semin Immunol.* (2017) 31:64-75; Fang, et al., *Semin Immunol.* (2017) 31:37-54; and Chiossone, et al., *Nat Rev Immunol.* (2018) 18(11):671-688.

In some embodiments, a compound as described herein, is combined with an inhibitor of CD47 (IAP, MER6, OA3; NCBI Gene ID: 961; UniProt Q08722). Examples of CD47 inhibitors include without limitation to anti-CD47 mAbs (Vx-1004), anti-human CD47 mAbs (CNTO-7108), CC-90002, CC-90002-ST-001, humanized anti-CD47 antibody (Hu5F9-G4), NI-1701, NI-1801, RCT-1938, ALX-148, TTI-621, RRx-001, DSP-107, VT-1021, TTI-621, TTI-622, and IMM-02 SGN-CD47M. Examples of anti-CD47 antibodies include IBI-188, TJC-4, SHR-1603, HLX-24, LQ-001, IMC-002, ZL-1201, IMM-01, B6H12, GenSci-059, TAY-018, PT-240, 1F8-GMCSF, SY-102, KD-015.

In some embodiments, the inhibitor of CD47 is a bi-specific antibody targeting CD47. Examples of bi-specific antibodies targeting CD47 include IBI-322 (CD47/PD-L1), IMM-0306 (CD47/CD20), TJ-L1C4 (CD47/PD-L1), HX-009 (CD47/PD-1), PMC-122 (CD47/PD-L1), PT-217, (CD47/DLL3), IMM-26011 (CD47/FLT3), IMM-0207 (CD47/VEGF), IMM-2902 (CD47/HER2), BH29xx (CD47/PD-L1), IMM-03 (CD47/CD20), IMM-2502 (CD47/PD-L1), HMBD-004B (CD47/BCMA), and HMBD-004A (CD47/CD33).

In some embodiments, the anti-CD47 targeting agent is one described in patent publication numbers WO199727873, WO199940940, WO2002092784, WO2005044857, WO2009046541, WO2010070047, WO2011143624, WO2012170250, WO2013109752, WO2013119714, WO2014087248, WO2015191861, WO2016022971, WO2016023040, WO2016024021, WO2016081423, WO2016109415, WO2016141328, WO2016188449, WO2017027422, WO2017049251, WO2017053423, WO2017121771, WO2017194634, WO2017196793, WO2017215585, WO2018075857, WO2018075960, WO2018089508, WO2018095428, WO2018137705, WO2018233575, WO2019027903, WO2019034895, WO2019042119, WO2019042285, WO2019042470, WO2019086573, WO2019108733, WO2019138367, WO2019144895, WO2019157843, WO2019179366, WO2019184912, WO2019185717, WO2019201236, WO2019238012, WO2019241732, WO2020019135, WO2020036977, WO2020043188, or WO2020009725.

In some embodiments, the one or more immune checkpoint inhibitors comprises a proteinaceous (e.g., antibody or fragment thereof, or antibody mimetic) inhibitor of PD-L1 (CD274), PD-1 (PDCD1) or CTLA4. In some embodiments, the one or more immune checkpoint inhibitors comprises a small organic molecule inhibitor of PD-L1 (CD274), PD-1 (PDCD1) or CTLA4.

Examples of inhibitors of CTLA4 that can be co-administered include without limitation ipilimumab, tremelimumab, BMS-986218, AGEN1181, AGEN1884, BMS-986249, MK-1308, REGN-4659, ADU-1604, CS-1002, BCD-145, APL-509, JS-007, BA-3071, ONC-392, AGEN-2041, JHL-1155, KN-044, CG-0161, ATOR-1144, PBI-5D3H5, BPI-002, HBM-4003, as well as multi-specific inhibitors FPT-155 (CTLA4/PD-L1/CD28), PF-06936308 (PD-1/CTLA4), MGD-019 (PD-1/CTLA4), KN-046 (PD-1/CTLA4), MEDI-5752 (CTLA4/PD-1), XmAb-20717 (PD-1/CTLA4), and AK-104 (CTLA4/PD-1).

Examples of inhibitors/antibodies of PD-L1 (CD274) or PD-1 (PDCD1) that can be co-administered include without limitation pembrolizumab, nivolumab, cemiplimab, pidilizumab, AMG-404, AMP-224, MEDI0680 (AMP-514), spartalizumab, atezolizumab, avelumab, durvalumab, BMS-936559, CK-301, PF-06801591, BGB-A317 (tislelizumab), GEN-1046 (PD-L1/4-1BB), GLS-010 (WBP-3055), AK-103 (HX-008), AK-105, CS-1003, HLX-10, MGA-012, BI-754091, AGEN-2034, JS-001 (toripalimab), JNJ-63723283, genolimzumab (CBT-501), LZM-009, BCD-100, LY-3300054, SHR-1201, SHR-1210 (camrelizumab), Sym-021, ABBV-181, PD1-PIK, BAT-1306, (MSB0010718C), CX-072, CBT-502, TSR-042 (dostarlimab), MSB-2311, JTX-4014, BGB-A333, SHR-1316, CS-1001 (WBP-3155, KN-035, IBI-308 (sintilimab), HLX-20, KL-A167, STI-A1014, STI-A1015 (IMC-001), BCD-135, FAZ-053, TQB-2450, MDX1105-01, GS-4224, GS-4416, INCB086550, MAX10181, as well as multi-specific inhibitors FPT-155 (CTLA4/PD-L1/CD28), PF-06936308 (PD-1/CTLA4), MGD-013 (PD-1/LAG-3), RO-7247669 (PD-1/LAG-3), FS-118 (LAG-3/PD-L1) MGD-019 (PD-1/CTLA4), KN-046 (PD-1/CTLA4), MEDI-5752 (CTLA4/PD-1), RO-7121661 (PD-1/TIM-3), XmAb-20717 (PD-1/CTLA4), AK-104 (CTLA4/PD-1), M7824 (PD-L1/TGFβ-EC domain), CA-170 (PD-L1/VISTA), CDX-527 (CD27/PD-L1), LY-3415244 (TIM-3/PDL1), RG7769 (PD-1/TIM-3) and INBRX-105 (4-1BB/PDL1), GNS-1480 (PD-L1/EGFR), RG-7446 (Tecentriq, atezolizumab), ABBV-181, nivolumab (OPDIVO®, BMS-936558, MDX-1106), pembrolizumab (KEYTRUDA®, MK-3477, SCH-900475, lambrolizumab, CAS Reg. No. 1374853-91-4), pidilizumab, PF-06801591, BGB-A317 (tislelizumab), GLS-010 (WBP-3055), AK-103 (HX-008), CS-1003, HLX-10, MGA-012, BI-754091, REGN-2810 (cemiplimab), AGEN-2034, JS-001 (toripalimab), JNJ-63723283, genolimzumab (CBT-501), LZM-009, BCD-100, LY-3300054, SHR-1201, SHR-1210 (camrelizumab), Sym-021, ABBV-181, AK-105, PD1-PIK, BAT-1306, BMS-936559, atezolizumab (MPDL3280A), durvalumab (MEDI-4736), avelumab, CK-301, (MSB0010718C), MEDI-0680, CX-072, CBT-502, PDR-001 (spartalizumab), PDR001+Tafinlar®+Mekinist®, MSB-2311, JTX-4014, BGB-A333, SHR-1316, CS-1001 (WBP-3155, KN-035, IBI-308 (sintilimab), HLX-20, KL-A167, STI-A1014, STI-A1015 (IMC-001), BCD-135, FAZ-053, TQB-2450, and MDX1105-01; and those described, e.g. in Intl. Patent Publ. Nos. WO2018195321, WO2020014643, WO2019160882, and WO2018195321.

Examples of inhibitors of PVRIG that can be co-administered include without limitation: COM-701.

Examples of inhibitors of TIGIT that can be co-administered include without limitation: BMS-986207, RG-6058, AGEN-1307, COM-902.

Examples of inhibitors of TIM-3 that can be co-administered include without limitation: TSR-022, LY-3321367, MBG-453, INCAGN-2390, RO-7121661 (PD-1/TIM-3), LY-3415244 (TIM-3/PDL1), RG7769 (PD-1/TIM-3).

Examples of inhibitors of LAG-3 that can be co-administered include without limitation: relatlimab (ONO-4482), LAG-525, MK-4280, REGN-3767, INCAGN2385, TSR-033, MGD-013 (PD-1/LAG-3), FS-118 (LAG-3/PD-L1).

Examples of anti-killer cell immunoglobulin like receptor, three Ig domains and long cytoplasmic tail 1 (KIR3DL1; KIR; NCBI Gene ID: 3811) monoclonal antibodies, such as lirilumab (IPH-2102), IPH-4102.

Examples of anti-NKG2a antibodies that can be co-administered include without limitation: monalizumab.

Examples of anti-VISTA antibodies that can be co-administered include without limitation: HMBD-002, CA-170 (PD-L1/VISTA).

Examples of anti-CD70 antibodies that can be co-administered include without limitation: AMG-172.

Examples of anti-CD20 antibodies that can be co-administered include without limitation: obinutuzumab, IGN-002, PF-05280586.

Examples of anti-ICOS antibodies that can be co-administered include without limitation: JTX-2011, GSK3359609.

Examples of ICOS agonists that can be co-administered include without limitation: ICOS-L.COMP (Gariepy, J. et al. 106th Annu Meet Am Assoc Immunologists (AAI) (May 9-13, San Diego) 2019, Abst 71.5).

TNF Receptor Superfamily (TNFRSF) Member Agonists or Activators

In some embodiments, a compound as described herein, is combined with an agonist of one or more TNF receptor superfamily (TNFRSF) members, e.g., an agonist of one or more of TNFRSF1A (NCBI Gene ID: 7132), TNFRSF1B (NCBI Gene ID: 7133), TNFRSF4 (OX40, CD134; NCBI Gene ID: 7293), TNFRSF5 (CD40; NCBI Gene ID: 958), TNFRSF6 (FAS, NCBI Gene ID: 355), TNFRSF7 (CD27, NCBI Gene ID: 939), TNFRSF8 (CD30, NCBI Gene ID: 943), TNFRSF9 (4-1BB, CD137, NCBI Gene ID: 3604), TNFRSF10A (CD261, DR4, TRAILR1, NCBI Gene ID: 8797), TNFRSF10B (CD262, DR5, TRAILR2, NCBI Gene ID: 8795), TNFRSF10C (CD263, TRAILR3, NCBI Gene ID: 8794), TNFRSF10D (CD264, TRAILR4, NCBI Gene ID: 8793), TNFRSF11A (CD265, RANK, NCBI Gene ID: 8792), TNFRSF11B (NCBI Gene ID: 4982), TNFRSF12A (CD266, NCBI Gene ID: 51330), TNFRSF13B (CD267, NCBI Gene ID: 23495), TNFRSF13C (CD268, NCBI Gene ID: 115650), TNFRSF16 (NGFR, CD271, NCBI Gene ID: 4804), TNFRSF17 (BCMA, CD269, NCBI Gene ID: 608), TNFRSF18 (GITR, CD357, NCBI Gene ID: 8784), TNFRSF19 (NCBI Gene ID: 55504), TNFRSF21 (CD358, DR6, NCBI Gene ID: 27242), and TNFRSF25 (DR3, NCBI Gene ID: 8718).

Example anti-TNFRSF4 (OX40) antibodies that can be co-administered include without limitation, MEDI6469, MEDI6383, MEDI0562 (tavolixizumab), MOXR0916, PF-04518600, RG-7888, GSK-3174998, INCAGN1949, BMS-986178, GBR-8383, ABBV-368, and those described in WO2016179517, WO2017096179, WO2017096182, WO2017096281, and WO2018089628.

Examples anti-TNF receptor superfamily member 10b (TNFRSF10B, DR5, TRAILR2) antibodies that can be co-administered include without limitation, such as DS-8273, CTB-006, INBRX-109, GEN-1029.

Example anti-TNFRSF5 (CD40) antibodies that can be co-administered include without limitation RG7876, SEA-CD40, APX-005M and ABBV-428, ABBV-927, JNJ-64457107.

In some embodiments, the anti-TNFRSF7 (CD27) antibody varlilumab (CDX-1127) is co-administered.

Example anti-TNFRSF9 (4-1BB, CD137) antibodies that can be co-administered include without limitation urelumab, utomilumab (PF-05082566), AGEN2373 and ADG-106.

In some embodiments, the anti-TNFRSF17 (BCMA) antibody GSK-2857916 is co-administered.

Example anti-TNFRSF18 (GITR) antibodies that can be co-administered include without limitation, MED11873, FPA-154, INCAGN-1876, TRX-518, BMS-986156, MK-1248, GWN-323, and those described in WO2017096179, WO2017096276, WO2017096189, and WO2018089628. In some embodiments, an antibody, or fragment thereof, co-targeting TNFRSF4 (OX40) and TNFRSF18 (GITR) is co-administered. Such antibodies are described, e.g., in WO2017096179 and WO2018089628.

Example anti-TRAILR1, anti-TRAILR2, anti-TRAILR3, anti-TRAILR4 antibodies that can be co-administered include without limitation ABBV-621.

Bi-specific antibodies targeting TNFRSF family members that can be co-administered include without limitation PRS-343 (CD-137/HER2), AFM26 (BCMA/CD16A), AFM-13 (CD16/CD30), REGN-1979 (CD20/CD3), AMG-420 (BCMA/CD3), INHIBRX-105 (4-1BB/PDL1), FAP-4-IBBL (4-1BB/FAP), XmAb-13676 (CD3/CD20), RG-7828 (CD20/CD3), CC-93269 (CD3/BCMA), REGN-5458 (CD3/BCMA), and IMM-0306 (CD47/CD20), AMG-424 (CD38.CD3).

Adenosine Generation and Signaling

In some embodiments, a compound as described herein, is combined with an agonist or antagonist of A1R, A2AR, A2BR, A3R, CD73, CD39, CD26.

Examples of Adenosine A3 receptor (A3R) agonists, such as namodenoson (CF102).

Examples of A2aR/A2bR antagonists, such as AB928.

Examples of anti-CD73 antibodies, such as MEDI-9447 (oleclumab), CPX-006, IPH-53, BMS-986179, NZV-930, CPI-006.

Examples of CD73 inhibitors, such as AB-680, PSB-12379, PSB-12441, PSB-12425, CB-708; and those described in Int Patent Publication No. WO19173692.

Examples of CD39/CD73 inhibitors, such as PBF-1662.

Examples of anti-CD39 antibodies, such as TTX-030.

Examples of Adenosine A2A receptor antagonists, such as CPI-444, AZD-4635, preladenant, PBF-509.

Examples of Adenosine deaminase inhibitors, such as pentostatin, cladribine.

c-kit Targeting Agents

In various embodiments, a compound as described herein, is combined with an inhibitor of c-kit (PBT, SCFR, CD117, MASTC; NCBI Gene ID:3815; Uniprot—P10721).

Examples of c-kit inhibitors include imatinib mesylate, JSP-191, BLU-263, CD117-ADC, AZD3229 (c-kit/PDGFR inhibitor), telatinib (c-kit/PDGF/VEGF2 inhibitor), quizartinib dihydrochloride (FLT3/c-kit), pexidartinib hydrochloride (CSF1R/FLT3/c-kit), avapritinib (PDGFR/c-Kit inhibitor), vorolanib (multikinase VEGF/PDGFR/c-kit inhibitor), and ripretinib (c-kit/PDGFRα inhibitor).

Examples of c-kit multi-kinase inhibitors include dasatinib, imatinib, nilotinib, sorafenib, lenvatinib mesylate, cabozantinib malate, AL-8326, ZLJ-33, KBP-7018, sunitinib malate, pazopanib derivatives, AGX-73, rebastinib, NMS-088, lucitanib hydrochloride, midostaurin, cediranib, dovitinib, sitravatinib, tivozanib, masitinib, regorafenib, HQP-1351, cabozantinib, ponatinib, and famitinib L-malate. Examples of anti-c-kit antibodies include CDX-0158, CDX-0159 and FSI-174.

In some embodiments, the anti-c-kit targeting agent is one described in patent publication numbers WO199203459, WO199221766, WO2004080462, WO2005020921, WO2006009755, WO2007078034, WO2007092403, WO2007127317, WO2008005877, WO2012154480, WO2014100620, WO2014039714, WO2015134536, WO2017167182, WO2018112136, WO2018112140, WO2019155067, WO2020076105, and patent application no. PCT/US2019/063091.

SIRPα Targeting Agents

In various embodiments, a compound as described herein, is combined with an inhibitor of SIRPα (NCBI Gene ID: 140885; UniProt P78324).

Examples of SIRPα inhibitors, such as AL-008, RRx-001, and CTX-5861.

Examples of anti-SIRPα-antibodies, such as FSI-189, ES-004, BI765063, ADU1805, and CC-95251.

In some embodiments, the SIRPα-targeting agent is one described in WO0200140307, WO2002092784, WO2007133811, WO2009046541, WO2010083253, WO2011076781, WO2013056352, WO2015138600, WO2016179399, WO2016205042, WO2017178653, WO2018026600, WO2018057669, WO2018107058, WO2018190719, WO2018210793, WO2019023347, WO2019042470, WO2019175218, WO2019183266, WO2020013170, or WO2020068752.

Bi-Specific T-Cell Engagers

In some embodiments, a compound as described herein, is combined with a bi-specific T-cell engager (e.g., not having an Fc) or an anti-CD3 bi-specific antibody (e.g., having an Fc). Illustrative anti-CD3 bi-specific antibodies or BiTEs that can be co-administered include AMG-160 (PSMA/CD3), AMG-212 (PSMA/CD3), AMG-330 (CD33/CD3), AMG-420 (BCMA/CD3), AMG-427 (FLT3/CD3), AMG-562 (CD19/CD3), AMG-596 (EGFRvIII/CD3), AMG-673 (CD33/CD3), AMG-701 (BCMA/CD3), AMG-757 (DLL3/CD3), JNJ-64052781 (CD19/CD3), AMG-211 (CEA/CD3), BLINCYTO® (CD19/CD3), RG7802 (CEA/CD3), ERY-974 (CD3/GPC3), huGD2-BsAb (CD3/GD2), PF-06671008 (Cadherins/CD3), APV0436 (CD123/CD3), ERY974, flotetuzumab (CD123/CD3), GEM333 (CD3/CD33), GEMoab (CD3/PSCA), REGN-1979 (CD20/CD3), REGN-5678 (PSMA/CD28), MCLA-117 (CD3/CLEC12A), JNJ-0819, JNJ-7564 (CD3/heme), JNJ-63709178 (CD123/CD3), MGD-007 (CD3/gpA33), MGD-009 (CD3/B7H3), IMCgp100 (CD3/gp100), XmAb-14045 (CD123/CD3), XmAb-13676 (CD3/CD20), XmAb-18087 (SSTR2/CD3), catumaxomab (CD3/EpCAM), REGN-4018 (MUC16/CD3), RG6026, RG6076, RG6194, RG-7828 (CD20/CD3), CC-93269 (CD3/BCMA), REGN-5458 (CD3/BCMA), GRB-1302 (CD3/Erbb2), GRB-1342 (CD38/CD3), GEM-333 (CD3/CD33), PF-06863135 (BCMA/CD3), SAR440234 (CD3/CDw123). As appropriate, the anti-CD3 binding bi-specific molecules may or may not have an Fc. Illustrative bi-specific T-cell engagers that can be co-administered target CD3 and a tumor-associated antigen as described herein, including, e.g., CD19 (e.g., blinatumomab); CD33 (e.g., AMG330); CEA (e.g., MEDI-565); receptor tyrosine kinase-like orphan receptor 1 (ROR1) (Gohil, et al., *Oncoimmunology.* (2017) May 17; 6(7):e1326437); PD-L1 (Horn, et al., *Oncotarget.* 2017 Aug. 3; 8(35):57964-57980); and EGFRvIII (Yang, et al., *Cancer Lett.* 2017 Sep. 10; 403:224-230).

Bi- and Tri-Specific Natural Killer (NK)-Cell Engagers

In some embodiments, a compound as described herein, is combined with a bi-specific NK-cell engager (BiKE) or a tri-specific NK-cell engager (TriKE) (e.g., not having an Fc) or bi-specific antibody (e.g., having an Fc) against an NK cell activating receptor, e.g., CD16A, C-type lectin receptors (CD94/NKG2C, NKG2D, NKG2E/H and NKG2F), natural cytotoxicity receptors (NKp30, NKp44 and NKp46), killer cell C-type lectin-like receptor (NKp65, NKp80), Fc receptor FcγR (which mediates antibody-dependent cell cytotoxicity), SLAM family receptors (e.g., 2B4, SLAM6 and SLAM7), killer cell immunoglobulin-like receptors (KIR) (KIR-2DS and KIR-3DS), DNAM-1 and CD137 (41BB). Illustrative anti-CD16 bi-specific antibodies, BiKEs or TriKEs that can be co-administered include AFM26 (BCMA/CD16A) and AFM-13 (CD16/CD30). As appropriate, the anti-CD16 binding bi-specific molecules may or may not have an Fc. Illustrative bi-specific NK-cell engagers that can be co-administered target CD16 and one or more tumor-associated antigens as described herein, including, e.g., CD19, CD20, CD22, CD30, CD33, CD123, EGFR, EpCAM, ganglioside GD2, HER2/neu, HLA Class II and FOLR1. BiKEs and TriKEs are described, e.g., in Felices, et al., *Methods Mol Biol.* (2016) 1441:333-346; Fang, et al., *Semin Immunol.* (2017) 31:37-54.

MCL1 Apoptosis Regulator, BCL2 Family Member (MCL1) Inhibitors

In some embodiments, a compound as described herein, is combined with an inhibitor of MCL1 apoptosis regulator, BCL2 family member (MCL1, TM; EAT; MCL1L; MCL1S; Mcl-1; BCL2L3; MCL1-ES; bcl2-L-3; mcl1/EAT; NCBI Gene ID: 4170). Examples of MCL1 inhibitors include AMG-176, AMG-397, S-64315, and AZD-5991, 483-LM, A-1210477, UMI-77, JKY-5-037, and those described in WO2018183418, WO2016033486, and WO2017147410.

Hematopoietic Progenitor Kinase 1 (HPK1) Inhibitors

In some embodiments, a compound as described herein, is combined with an inhibitor of mitogen-activated protein kinase kinase kinase kinase 1 (MAP4K1, HPK1; NCBI Gene ID: 11184). Examples of Hematopoietic Progenitor Kinase 1 (HPK1) inhibitors include without limitation, those described in WO-2018183956, WO-2018183964, WO-2018167147, WO-2018183964, WO-2016205942, WO-2018049214, WO-2018049200, WO-2018049191, WO-2018102366, WO-2018049152, WO2020092528, WO2020092621, and WO-2016090300.

Apoptosis Signal-Regulating Kinase (ASK) Inhibitors

In some embodiments, a compound as described herein, is combined with an inhibitor of an ASK inhibitor, e.g., mitogen-activated protein kinase kinase kinase 5 (MAP3K5; ASK1, MAPKKK5, MEKK5; NCBI Gene ID: 4217). Examples of ASK1 inhibitors include without limitation, those described in WO 2011/008709 (Gilead Sciences) and WO 2013/112741 (Gilead Sciences).

Bruton Tyrosine Kinase (BTK) Inhibitors

In some embodiments, a compound as described herein, is combined with an inhibitor of Bruton tyrosine kinase (BTK, AGMX1, AT, ATK, BPK, IGHD3, IMD1, PSCTK1, XLA; NCBI Gene ID: 695). Examples of BTK inhibitors include without limitation, (S)-6-amino-9-(1-(but-2-ynoyl)pyrrolidin-3-yl)-7-(4-phenoxyphenyl)-7H-purin-8(9H)-one, acalabrutinib (ACP-196), BGB-3111, CB988, HM71224, ibrutinib (Imbruvica), M-2951 (evobrutinib), M7583, tirabrutinib (ONO-4059), PRN-1008, spebrutinib (CC-292), TAK-020, vecabrutinib, ARQ-531, SHR-1459, DTRMWXHS-12, TAS-5315, Calquence+AZD6738, Calquence+danvatirsen.

Cyclin-Dependent Kinase (CDK) Inhibitors

In some embodiments, a compound as described herein, is combined with an inhibitor of cyclin dependent kinase 1 (CDK1, CDC2; CDC28A; P34CDCl$_2$; NCBI Gene ID: 983); cyclin dependent kinase 2 (CDK2, CDKN2; p33(CDK2); NCBI Gene ID: 1017); cyclin dependent kinase 3 (CDK3, NCBI Gene ID: 1018); cyclin dependent kinase 4 (CDK4, CMM3; PSK-J3; NCBI Gene ID: 1019); cyclin dependent kinase 6 (CDK6, MCPH12; PLSTIRE; NCBI Gene ID: 1021); cyclin dependent kinase 7 (CDK7, CAK; CAK1; HCAK; M015; STK1; CDKN7; p39MO15; NCBI Gene ID: 1022); cyclin dependent kinase 9 (CDK9, TAK; C-2k; CTK1; CDCl$_2$L4; PITALRE; NCBI Gene ID: 1025). Inhibitors of CDK 1, 2, 3, 4, 6, 7 and/or 9, include without limitation abemaciclib, alvocidib (HMR-1275, flavopiridol), AT-7519, dinaciclib, ibrance, FLX-925, LEE001, palbociclib, ribociclib, rigosertib, selinexor, UCN-01, SY1365, CT-7001, SY-1365, G1T38, milciclib, trilaciclib, PF-06873600, AZD4573, and TG-02.

Discoidin Domain Receptor (DDR) Inhibitors

In some embodiments, a compound as described herein, is combined with an inhibitor of discoidin domain receptor tyrosine kinase 1 (DDRT, CAK, CD167, DDR, EDDR1, HGK2, MCK10, NEP, NTRK4, PTK3, PTK3A, RTK6, TRKE; NCBI Gene ID: 780); and/or discoidin domain receptor tyrosine kinase 2 (DDR2, MIG20a, NTRKR3, TKT, TYRO10, WRCN; NCBI Gene ID: 4921). Examples of DDR inhibitors include without limitation, dasatinib and those disclosed in WO2014/047624 (Gilead Sciences), US 2009-0142345 (Takeda Pharmaceutical), US 2011-0287011 (Oncomed Pharmaceuticals), WO 2013/027802 (Chugai Pharmaceutical), and WO2013/034933 (Imperial Innovations).

Histone Deacetylase (HDAC) Inhibitors

In some embodiments, a compound as described herein, is combined with an inhibitor of a histone deacetylase, e.g., histone deacetylase 9 (HDAC9, HD7, HD7b, HD9, HDAC, HDAC7, HDAC7B, HDAC9B, HDAC9FL, HDRP, MITR; Gene ID: 9734). Examples of HDAC inhibitors include without limitation, abexinostat, ACY-241, AR-42, BEBT-908, belinostat, CKD-581, CS-055 (HBI-8000), CUDC-907 (fimepinostat), entinostat, givinostat, mocetinostat, panobinostat, pracinostat, quisinostat (JNJ-26481585), resminostat, ricolinostat, SHP-141, valproic acid (VAL-001), vorinostat, tinostamustine, remetinostat, entinostat, romidepsin, tucidinostat.

Indoleamine-Pyrrole-2,3-Dioxygenase (IDO1) Inhibitors

In some embodiments, a compound as described herein, is combined with an inhibitor of indoleamine 2,3-dioxygenase 1 (IDO1; NCBI Gene ID: 3620). Examples of IDO1 inhibitors include without limitation, BLV-0801, epacadostat, F-001287, GBV-1012, GBV-1028, GDC-0919, indoximod, NKTR-218, NLG-919-based vaccine, PF-06840003, pyranonaphthoquinone derivatives (SN-35837), resminostat, SBLK-200802, BMS-986205, and shIDO-ST, EOS-200271, KHK-2455, LY-3381916.

Janus Kinase (JAK) Inhibitors

In some embodiments, a compound as described herein, is combined with an inhibitor of Janus kinase 1 (JAK1, JAK1A, JAK1B, JTK3; NCBI Gene ID: 3716); Janus kinase 2 (JAK2, JTK10, THCYT3; NCBI Gene ID: 3717); and/or Janus kinase 3 (JAK3, JAK-3, JAK3_HUMAN, JAKL, L-JAK, LJAK; NCBI Gene ID: 3718). Examples of JAK inhibitors include without limitation, AT9283, AZD1480, baricitinib, BMS-911543, fedratinib, filgotinib (GLPG0634), gandotinib (LY2784544), INCB039110 (itacitinib), lestaurtinib, momelotinib (CYT0387), NS-018, pacritinib (SB1518), peficitinib (ASP015K), ruxolitinib, tofacitinib (formerly tasocitinib), INCB052793, and XL019.

Matrix Metalloprotease (MMP) Inhibitors

In some embodiments, a compound as described herein, is combined with an inhibitor of a matrix metallopeptidase (MMP), e.g., an inhibitor of MMP1 (NCBI Gene ID: 4312), MMP2 (NCBI Gene ID: 4313), MMP3 (NCBI Gene ID: 4314), MMP7 (NCBI Gene ID: 4316), MMP8 (NCBI Gene ID: 4317), MMP9 (NCBI Gene ID: 4318); MMP10 (NCBI Gene ID: 4319); MMP11 (NCBI Gene ID: 4320); MMP12 (NCBI Gene ID: 4321), MMP13 (NCBI Gene ID: 4322), MMP14 (NCBI Gene ID: 4323), MMP15 (NCBI Gene ID: 4324), MMP16 (NCBI Gene ID: 4325), MMP17 (NCBI Gene ID: 4326), MMP19 (NCBI Gene ID: 4327), MMP20 (NCBI Gene ID: 9313), MMP21 (NCBI Gene ID: 118856), MMP24 (NCBI Gene ID: 10893), MMP25 (NCBI Gene ID: 64386), MMP26 (NCBI Gene ID: 56547), MMP27 (NCBI Gene ID: 64066) and/or MMP28 (NCBI Gene ID: 79148). Examples of MMP9 inhibitors include without limitation, marimastat (BB-2516), cipemastat (Ro 32-3555), GS-5745 (andecaliximab) and those described in WO 2012/027721 (Gilead Biologics).

RAS and RAS Pathway Inhibitors

In some embodiments, a compound as described herein, is combined with an inhibitor of KRAS proto-oncogene, GTPase (KRAS; a.k.a., NS; NS3; CFC2; RALD; K-Ras; KRAS1; KRAS2; RASK2; KI-RAS; C-K-RAS; K-RAS2A; K-RAS2B; K-RAS4A; K-RAS4B; c-Ki-ras2; NCBI Gene ID: 3845); NRAS proto-oncogene, GTPase (NRAS; a.k.a., NS6; CMNS; NCMS; ALPS4; N-ras; NRAS1; NCBI Gene ID: 4893); HRas proto-oncogene, GTPase (HRAS; a.k.a., CTLO; KRAS; HAMSV; HRAS1; KRAS2; RASH1; RASK2; Ki-Ras; p21ras; C-H-RAS; c-K-ras; H-RASIDX; c-Ki-ras; C-BAS/HAS; C-HA-RAS1; NCBI Gene ID: 3265). The Ras inhibitors can inhibit Ras at either the polynucleotide (e.g., transcriptional inhibitor) or polypeptide (e.g., GTPase enzyme inhibitor) level. In some embodiments, the inhibitors target one or more proteins in the Ras pathway, e.g., inhibit one or more of EGFR, Ras, Raf (A-Raf, B-Raf, C-Raf), MEK (MEK1, MEK2), ERK, PI3K, AKT and mTOR.

In some embodiments, a compound as described herein, is combined with an inhibitor of KRAS. Examples of KRAS inhibitors include AMG-510, COTI-219, MRTX-1257, ARS-3248, ARS-853, WDB-178, BI-3406, BI-1701963, ARS-1620 (G12C), SML-8-73-1 (G12C), Compound 3144 (G12D), Kobe0065/2602 (Ras GTP), RT11, MRTX-849 (G12C) and K-Ras(G12D)-selective inhibitory peptides, including KRpep-2 (Ac-RRCPLYISYDPVCRR-NH$_2$) (SEQ ID NO:108) and KRpep-2d (Ac-RRRRCPLYI-SYDPVCRRRR-NH$_2$) (SEQ ID NO:109).

In some embodiments, a compound as described herein, is combined with an inhibitor of KRAS mRNA. Illustrative KRAS mRNA inhibitors include anti-KRAS U1 adaptor, AZD-4785, siG12D-LODER™, and siG12D exosomes.

In some embodiments, a compound as described herein, is combined with an inhibitor of MEK. Illustrative MEK inhibitors that can be co-administered include binimetinib, cobimetinib, PD-0325901, pimasertib, RG-7304, selumetinib, trametinib, selumetinib.

In some embodiments, a compound as described herein, is combined with an inhibitor of AKT. Illustrative AKT inhibitors that can be co-administered include RG7440, MK-2206, ipatasertib, afuresertib, AZD5363, and ARQ-092, capivasertib, triciribine, ABTL-0812 (PI3K/Akt/mTOR).

In some embodiments, a compound as described herein, is combined with an inhibitor of Raf. Illustrative Raf inhibitors that can be co-administered BGB-283 (Raf/EGFR), HM-95573, LXH-254, LY-3009120, RG7304, TAK-580, dabrafenib, vemurafenib, encorafenib (LGX818), PLX8394, RAF-265 (Raf/VEGFR), ASN-003 (Raf/PI3K).

In some embodiments, a compound as described herein, is combined with an inhibitor of ERK. Illustrative ERK inhibitors that can be co-administered include LTT-462, LY-3214996, MK-8353, ravoxertinib, GDC-0994, and ulixertinib.

In some embodiments, a compound as described herein, is combined with an inhibitor of PI3K. Illustrative PI3K inhibitors that can be co-administered include idelalisib (Zydelig®), alpelisib, buparlisib, pictilisib. Illustrative PI3K/mTOR inhibitors that can be co-administered include dactolisib, omipalisib, voxtalisib, gedatolisib, GSK2141795, RG6114.

In some embodiments, a compound as described herein, is combined with an inhibitor of mTOR. Illustrative mTOR inhibitors that can be co-administered include as sapanisertib, vistusertib (AZD2014), ME-344, sirolimus (oral nano-amorphous formulation, cancer), TYME-88 (mTOR/cytochrome P450 3A4).

In some embodiments, Ras-driven cancers (e.g., NSCLC) having CDKN2A mutations can be inhibited by co-administration of the MEK inhibitor selumetinib and the CDK4/6 inhibitor palbociclib. See, e.g., Zhou, et al., *Cancer Lett.* 2017 Nov. 1; 408:130-137. Also, K-RAS and mutant N-RAS can be reduced by the irreversible ERBB1/2/4 inhibitor neratinib. See, e.g., Booth, et al., *Cancer Biol Ther.* 2018 Feb. 1; 19(2):132-137.

In some embodiments, a compound as described herein, is combined with an inhibitor of RAS. Examples of RAS inhibitors include NEO-100, rigosertib.

In some embodiments, a compound as described herein, is combined with an antagonist of EGFR, such as AMG-595, necitumumab, ABBV-221, depatuxizumab mafodotin (ABT-414), tomuzotuximab, ABT-806, vectibix, modotuximab, RM-1929.

In some embodiments, a compound as described herein, is combined with an inhibitor of protein tyrosine phosphatase non-receptor type 11 (PTPN11; BPTP3, CFC, JMML, METCDS, NS1, PTP-1D, PTP2C, SH-PTP2, SH-PTP3, SHP2; NCBI Gene ID: 5781). Examples of SHP2 inhibitors include TNO155 (SHP-099), RMC-4550, JAB-3068, RMC-4630, SAR442720 and those described in WO2018172984 and WO2017211303.

In some embodiments, a compound as described herein, is combined with an inhibitor of mitogen-activated protein kinase 7 (MAP2K7, JNKK2, MAPKK7, MEK, MEK 7, MKK7, PRKMK7, SAPKK-4, SAPKK4; NCBI Gene ID: 5609). Examples of MEK inhibitors include antroquinonol, binimetinib, CK-127, cobimetinib (GDC-0973, XL-518), MT-144, selumetinib (AZD6244), sorafenib, trametinib (GSK1120212), uprosertib+trametinib, PD-0325901, pimasertib, LTT462, AS703988, CC-90003, refametinib, TAK-733, CI-1040, RG7421.

Phosphatidylinositol 3-kinase (PI3K) Inhibitors

In some embodiments, a compound as described herein, is combined with an inhibitor of a phosphatidylinositol-4,5-bisphosphate 3-kinase catalytic subunit, e.g., phosphatidylinositol-4,5-bisphosphate 3-kinase catalytic subunit alpha (PIK3CA, CLAPO, CLOVE, CWS5, MCAP, MCM, MCMTC, PI3K, PI3K-alpha, p110-alpha; NCBI Gene ID: 5290); phosphatidylinositol-4,5-bisphosphate 3-kinase catalytic subunit beta (PIK3CB, P110BETA, PI3K, PI3KBETA, PIK3C1; NCBI Gene ID: 5291); phosphatidylinositol-4,5-bisphosphate 3-kinase catalytic subunit gamma (PIK3CG, PI3CG, PI3K, PI3Kgamma, PIK3, p110gamma, p120-PI3K; Gene ID: 5494); and/or phosphatidylinositol-4,5-bisphosphate 3-kinase catalytic subunit delta (PIK3CD, APDS, IMD14, P110DELTA, PI3K, p110D, NCBI Gene ID: 5293).

In some embodiments, the PI3K inhibitor is a pan-PI3K inhibitor. Examples of PI3K inhibitors include without limitation, ACP-319, AEZA-129, AMG-319, AS252424, AZD8186, BAY 10824391, BEZ235, buparlisib (BKM120), BYL719 (alpelisib), CH5132799, copanlisib (BAY 80-6946), duvelisib, GDC-0032, GDC-0077, GDC-0941, GDC-0980, GSK2636771, GSK2269557, idelalisib (Zydelig®), INCB50465, IPI-145, IPI-443, IPI-549, KAR4141, LY294002, LY3023414, MLN1117, OXY111A, PA799, PX-866, RG7604, rigosertib, RP5090, RP6530, SRX3177, taselisib, TG100115, TGR-1202 (umbralisib), TGX221, WX-037, X-339, X-414, XL147 (SAR245408), XL499, XL756, wortmannin, ZSTK474, and the compounds described in WO 2005/113556 (ICOS), WO 2013/052699 (Gilead Calistoga), WO 2013/116562 (Gilead Calistoga), WO 2014/100765 (Gilead Calistoga), WO 2014/100767 (Gilead Calistoga), and WO 2014/201409 (Gilead Sciences).

Mitogen-activated Protein Kinase (MEK) Inhibitors

In some embodiments, a compound as described herein, is combined with an inhibitor of mitogen-activated protein kinase kinase 7 (MAP2K7, JNKK2, MAPKK7, MEK, MEK 7, MKK7, PRKMK7, SAPKK-4, SAPKK4; NCBI Gene ID: 5609). Examples of MEK inhibitors include antroquinonol, binimetinib, cobimetinib (GDC-0973, XL-518), MT-144, selumetinib (AZD6244), sorafenib, trametinib (GSK1120212), uprosertib+trametinib, PD-0325901, pimasertib, LTT462, AS703988, CC-90003, refametinib.

Spleen Tyrosine Kinase (SYK) Inhibitors

In some embodiments, a compound as described herein, is combined with an inhibitor of spleen associated tyrosine kinase (SYK, p72-Syk, Gene ID: 6850). Examples of SYK inhibitors include without limitation, 6-(1H-indazol-6-yl)-N-(4-morpholinophenyl)imidazo[1,2-a]pyrazin-8-amine, BAY-61-3606, cerdulatinib (PRT-062607), entospletinib, fostamatinib (R788), HMPL-523, NVP-QAB 205 AA, R112, R343, tamatinib (R406), and those described in U.S. Pat. No. 8,450,321 (Gilead Connecticut) and those described in U.S. 2015/0175616.

Toll-Like Receptor (TLR) Agonists

In some embodiments, a compound as described herein, is combined with an agonist of a toll-like receptor (TLR), e.g., an agonist of TLR1 (NCBI Gene ID: 7096), TLR2 (NCBI Gene ID: 7097), TLR3 (NCBI Gene ID: 7098), TLR4 (NCBI Gene ID: 7099), TLR5 (NCBI Gene ID: 7100), TLR6 (NCBI Gene ID: 10333), TLR7 (NCBI Gene ID: 51284), TLR8 (NCBI Gene ID: 51311), TLR9 (NCBI Gene ID: 54106), and/or TLR10 (NCBI Gene ID: 81793). Example TLR7 agonists that can be co-administered include without limitation DS-0509, GS-9620, LHC-165, TMX-101 (imiquimod), GSK-2245035, resiquimod, DSR-6434, DSP-3025, IMO-4200, MCT-465, MEDI-9197, 3M-051, SB-9922, 3M-052, Limtop, TMX-30X, TMX-202, RG-7863, RG-7795, and the compounds disclosed in US20100143301 (Gilead Sciences), US20110098248 (Gilead Sciences), and US20090047249 (Gilead Sciences), US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics). An TLR7/TLR8 agonist that can be co-administered is NKTR-262. Example TLR8 agonists that can be co-administered include without limitation E-6887, IMO-4200, IMO-8400, IMO-9200, MCT-465, MEDI-9197, motolimod, resiquimod, GS-9688, VTX-1463, VTX-763, 3M-051, 3M-052, and the compounds disclosed in US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics). Example TLR9 agonists that can be co-administered include without limitation AST-008, CMP-001, IMO-2055, IMO-2125, litenimod, MGN-1601, BB-001, BB-006, IMO-3100, IMO-8400, IR-103, IMO-9200, agatolimod, DIMS-9054, DV-1079, DV-1179, AZD-1419, leftolimod (MGN-1703), CYT-003, CYT-003-QbG10 and PUL-042. Examples of TLR3 agonist include rintatolimod, poly-ICLC, RIBOXXON®, Apoxxim, RIBOXXIM®, IPH-33, MCT-465, MCT-475, and ND-1.1.

Examples of TLR8 inhibitors include, but are not limited to, E-6887, IMO-8400, IMO-9200 and VTX-763.

Examples of TLR8 agonists include, but are not limited to, MCT-465, motolimod, GS-9688, and VTX-1463.

Examples of TLR9 inhibitors include but are not limited to, AST-008, IMO-2055, IMO-2125, lefitolimod, litenimod, MGN-1601, and PUL-042.

Examples of TLR7/TLR8 agonist, such as NKTR-262, IMO-4200, MEDI-9197 (telratolimod), resiquimod.

Examples of TLR agonists include without limitation: lefitolimod, tilsotolimod, rintatolimod, DSP-0509, AL-034, G-100, cobitolimod, AST-008, motolimod, GSK-1795091, GSK-2245035, VTX-1463, GS-9688, LHC-165, BDB-001, RG-7854, telratolimod.

In some embodiments, the therapeutic agent is a stimulator of interferon genes (STING) In some embodiments, the STING receptor agonist or activator is selected from the group consisting of ADU-S100 (MIW-815), SB-11285, MK-1454, SR-8291, AdVCA0848, GSK-532, SYN-STING, MSA-1, SR-8291, 5,6-dimethylxanthenone-4-acetic acid (DMXAA), cyclic-GAMP (cGAMP) and cyclic-di-AMP.

Indoleamine-Pyrrole-2,3-Dioxygenase (IDO1) Inhibitors

In some embodiments, a compound as described herein, is combined with an inhibitor of indoleamine 2,3-dioxygenase 1 (IDO1; NCBI Gene ID: 3620). Examples of IDO1 inhibitors include without limitation, BLV-0801, epacadostat, F-001287, GBV-1012, GBV-1028, GDC-0919, indoximod, NKTR-218, NLG-919-based vaccine, PF-06840003, pyranonaphthoquinone derivatives (SN-35837), resminostat, SBLK-200802, BMS-986205, and shIDO-ST, EOS-200271, KHK-2455, LY-3381916.

In some embodiments, the therapeutic agent is a small organic compound. In some embodiments, the therapeutic agent is an agonist or activator of a toll-like receptor (TLR) or a stimulator of interferon genes (STING) In some embodiments, the STING receptor agonist or activator is selected from the group consisting of ADU-100 (MIW-815), SB-11285, MK-1454, SR-8291, AdVCA0848, GSK-532, SYN-STING, MSA-1, SR-8291, 5,6-dimethylxanthenone-4-acetic acid (DMXAA), cyclic-GAMP (cGAMP) and cyclic-di-AMP.

Tyrosine-Kinase Inhibitors (TKIs)

In some embodiments, a compound as described herein, is combined with a tyrosine kinase inhibitor (TKI). TKIs may target epidermal growth factor receptors (EGFRs) and receptors for fibroblast growth factor (FGF), platelet-derived growth factor (PDGF), and vascular endothelial growth factor (VEGF). Examples of TKIs include without limitation, axitinib, afatinib, ARQ-087 (derazantinib), asp5878, AZD3759, AZD4547, bosutinib, brigatinib, cabozantinib, cediranib, crenolanib, dacomitinib, dasatinib, dovitinib, E-6201, erdafitinib, erlotinib, gefitinib, gilteritinib (ASP-2215), FP-1039, HM61713, icotinib, imatinib, KX2-391 (Src), lapatinib, lestaurtinib, lenvatinib, midostaurin, nintedanib, ODM-203, olmutinib, osimertinib (AZD-9291), pazopanib, ponatinib, poziotinib, quizartinib, radotinib, rociletinib, sulfatinib (HMPL-012), sunitinib, famitinib L-malate, (MAC-4), tivoanib, TH-4000, tivoanib, and MEDI-575 (anti-PDGFR antibody), TAK-659, Cabozantinib.

Chemotherapeutic Agents (Standard of Care)

In some embodiments, a compound as described herein, is combined with a chemotherapeutic agent or anti-neoplastic agent.

As used herein, the term "chemotherapeutic agent" or "chemotherapeutic" (or "chemotherapy" in the case of treatment with a chemotherapeutic agent) is meant to encompass any non-proteinaceous (e.g., non-peptidic) chemical compound useful in the treatment of cancer. Examples of chemotherapeutic agents include but not limited to: alkylating agents such as thiotepa and cyclophosphamide (CYTOXAN®); alkyl sulfonates such as busulfan, improsulfan, and piposulfan; aziridines such as benzodepa, carboquone, meturedepa, and uredepa; ethylenimines and methylamelamines including altretamine, triethylenemelamine, triethylenephosphoramide, triethylenethiophosphoramide, and trimemylolomelamine; acetogenins, e.g., bullatacin and bullatacinone; a camptothecin, including synthetic analog topotecan; bryostatin, callystatin; CC-1065, including its adozelesin, carzelesin, and bizelesin synthetic analogs; cryptophycins, particularly cryptophycin 1 and cryptophycin 8; dolastatin; duocarmycin, including the synthetic analogs KW-2189 and CBI-TMI; eleutherobin; 5-azacytidine; pancratistatin; a sarcodictyin; spongistatin; nitrogen mustards such as chlorambucil, chlornaphazine, cyclophosphamide, glufosfamide, evofosfamide, bendamustine, estramustine, ifosfamide, mechlorethamine, mechlorethamine oxide hydrochloride, melphalan, novembichin, phenesterine, prednimustine, trofosfamide, and uracil mustard; nitrosoureas such as carmustine, chlorozotocin, foremustine, lomustine, nimustine, and ranimustine; antibiotics such as the enediyne antibiotics (e.g., calicheamicin, especially calicheamicin gammaII and calicheamicin phiI1), dynemicin including dynemicin A, bisphosphonates such as clodronate, an esperamicin, neocarzinostatin chromophore and related chromoprotein enediyne antibiotic chromomophores, aclacinomycins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin, and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, and zorubicin; anti-metabolites such as methotrexate and 5-fluorouracil (5-FU); folic acid analogs such as demopterin, methotrexate, pteropterin, and trimetrexate; purine analogs such as cladribine, pentostatin, fludarabine, 6-mercaptopurine, thiamiprine, and thioguanine; pyrimidine analogs such as ancitabine, azacitidine, 6-azauridine, carmofur, cytarabine, dideoxyuridine, doxifluridine, enocitabine, and floxuridine; androgens such as calusterone, dromostanolone propionate, epitiostanol, mepitiostane, and testolactone; anti-adrenals such as aminoglutethimide, mitotane, and trilostane; folic acid replinishers such as frolinic acid; radiotherapeutic agents such as Radium-223; trichothecenes, especially T-2 toxin, verracurin A, roridin A, and anguidine; taxoids such as paclitaxel (TAXOL®), abraxane, docetaxel (TAXOTERE®), cabazitaxel, BIND-014, tesetaxel; platinum analogs such as cisplatin and carboplatin, NC-6004 nanoplatin; aceglatone; aldophosphamide glycoside; aminolevulinic acid; eniluracil; amsacrine; hestrabucil; bisantrene; edatraxate; defofamine; demecolcine; diaziquone; elformthine; elliptinium acetate; an epothilone; etoglucid; gallium nitrate; hydroxyurea; lentinan; leucovorin; lonidamine; maytansinoids such as maytansine and ansamitocins; mitoguazone; mitoxantrone; mopidamol; nitracrine; pentostatin; phenamet; pirarubicin; losoxantrone; fluoropyrimidine; folinic acid; podophyllinic acid; 2-ethylhydrazide; procarbazine; polysaccharide-K (PSK); razoxane; rhizoxin; sizofiran; spirogermanium; tenuazonic acid; trabectedin, triaziquone; 2,2',2"-trichlorotriemylamine; urethane; vindesine; dacarbazine; mannomustine; mitobronitol; mitolactol; pipobroman; gacytosine; arabinoside ("Ara-C"); cyclophosphamide; thiopeta; chlorambucil; gemcitabine (GEMZAR®); 6-thioguanine; mercaptopurine; methotrexate; vinblastine; platinum; etoposide (VP-16); ifosfamide; mitroxantrone; vancristine; vinorelbine (NAVELBINE®); novantrone; teniposide; edatrexate; daunomycin; aminopterin; xeoloda; ibandronate; CPT-11; topoisomerase inhibitor RFS 2000; difluoromethylomithine (DFMO); retinoids such as retinoic acid; capecitabine; NUC-1031; FOLFOX (folinic acid, 5-fluorouracil, oxaliplatin); FOLFIRI (folinic acid, 5-fluorouracil, irinotecan); FOLFOXIRI (folinic acid, 5-fluorouracil, oxaliplatin, irinotecan), FOLFIRINOX (folinic acid, 5-fluorouracil, irinotecan, oxaliplatin), and pharmaceutically acceptable salts, acids, or derivatives of any of the above. Such agents can be conjugated onto an antibody or any targeting agent described herein to create an antibody-drug conjugate (ADC) or targeted drug conjugate.

Anti-Hormonal Agents

Also included in the definition of "chemotherapeutic agent" are anti-hormonal agents such as anti-estrogens and selective estrogen receptor modulators (SERMs), inhibitors of the enzyme aromatase, anti-androgens, and pharmaceutically acceptable salts, acids or derivatives of any of the above that act to regulate or inhibit hormone action on tumors.

Examples of anti-estrogens and SERMs include, for example, tamoxifen (including NOLVADEX™), raloxifene, droloxifene, 4-hydroxytamoxifen, trioxifene, keoxifene, LY117018, onapristone, and toremifene (FARESTON®).

Inhibitors of the enzyme aromatase regulate estrogen production in the adrenal glands. Examples include 4(5)-imidazoles, aminoglutethimide, megestrol acetate (MEGACE®), exemestane, formestane, fadrozole, vorozole (RIVISOR®), letrozole (FEMARA®), and anastrozole (ARIMIDEX®).

Examples of anti-androgens include apalutamide, abiraterone, enzalutamide, flutamide, galeterone, nilutamide, bicalutamide, leuprolide, goserelin, ODM-201, APC-100, ODM-204.

An example progesterone receptor antagonist includes onapristone.

Anti-Angiogenic Agents

In some embodiments, a compound as described herein, is combined with an anti-angiogenic agent. Anti-angiogenic agents that can be co-administered include, but are not limited to, retinoid acid and derivatives thereof, 2-methoxyestradiol, ANGIOSTATIN®, ENDOSTATIN®, regorafenib, necuparanib, suramin, squalamine, tissue inhibitor of metalloproteinase-1, tissue inhibitor of metalloproteinase-2, plasminogen activator inhibitor-1, plasminogen activator inhibitor-2, cartilage-derived inhibitor, paclitaxel (nab-paclitaxel), platelet factor 4, protamine sulphate (clupeine), sulphated chitin derivatives (prepared from queen crab shells), sulphated polysaccharide peptidoglycan complex (sp-pg), staurosporine, modulators of matrix metabolism including proline analogs such as 1-azetidine-2-carboxylic acid (LACA), cishydroxyproline, d,I-3,4-dehydroproline, thiaproline, α,α'-dipyridyl, beta-aminopropionitrile fumarate, 4-propyl-5-(4-pyridinyl)-2(3h)-oxazolone, methotrexate, mitoxantrone, heparin, interferons, 2 macroglobulin-serum, chicken inhibitor of metalloproteinase-3 (ChIMP-3), chymostatin, beta-cyclodextrin tetradecasulfate, eponemycin, fumagillin, gold sodium thiomalate, d-penicillamine, beta-1-anticollagenase-serum, alpha-2-antiplasmin, bisantrene, lobenzarit disodium, n-2-carboxyphenyl-4-chloroanthronilic acid disodium or "CCA", thalidomide, angiostatic steroid, carboxy aminoimidazole, metalloproteinase inhibitors such as BB-94, inhibitors of S100A9 such as tasquinimod. Other anti-angiogenesis agents include antibodies, e.g., monoclonal antibodies against these angiogenic growth factors: beta-FGF, alpha-FGF, FGF-5, VEGF isoforms, VEGF-C, HGF/SF, and Ang-1/Ang-2.

Anti-Fibrotic Agents

In some embodiments, a compound as described herein, is combined with an anti-fibrotic agent. Anti-fibrotic agents that can be co-administered include, but are not limited to, the compounds such as beta-aminoproprionitrile (BAPN), as well as the compounds disclosed in U.S. Pat. No. 4,965,288 relating to inhibitors of lysyl oxidase and their use in the treatment of diseases and conditions associated with the abnormal deposition of collagen and U.S. Pat. No. 4,997,854 relating to compounds which inhibit LOX for the treatment of various pathological fibrotic states, which are herein incorporated by reference. Further exemplary inhibitors are described in U.S. Pat. No. 4,943,593 relating to compounds such as 2-isobutyl-3-fluoro-, chloro-, or bromo-allylamine, U.S. Pat. Nos. 5,021,456, 5,059,714, 5,120,764, 5,182,297, 5,252,608 relating to 2-(1-naphthyloxymemyl)-3-fluoroallylamine, and US 2004-0248871, which are herein incorporated by reference.

Exemplary anti-fibrotic agents also include the primary amines reacting with the carbonyl group of the active site of the lysyl oxidases, and more particularly those which produce, after binding with the carbonyl, a product stabilized by resonance, such as the following primary amines: emylenemamine, hydrazine, phenylhydrazine, and their derivatives; semicarbazide and urea derivatives; aminonitriles such as BAPN or 2-nitroethylamine; unsaturated or saturated haloamines such as 2-bromo-ethylamine, 2-chloroethylamine, 2-trifluoroethylamine, 3-bromopropylamine, and p-halobenzylamines; and selenohomocysteine lactone.

Other anti-fibrotic agents are copper chelating agents penetrating or not penetrating the cells. Exemplary compounds include indirect inhibitors which block the aldehyde derivatives originating from the oxidative deamination of the lysyl and hydroxylysyl residues by the lysyl oxidases. Examples include the thiolamines, particularly D-penicillamine, and its analogs such as 2-amino-5-mercapto-5-methylhexanoic acid, D-2-amino-3-methyl-3-((2-acetamidoethyl)dithio)butanoic acid, p-2-amino-3-methyl-3-((2-aminoethyl)dithio)butanoic acid, sodium-4-((p-1-dimethyl-2-amino-2-carboxyethyl)dithio)butane sulphurate, 2-acetamidoethyl-2-acetamidoethanethiol sulphanate, and sodium-4-mercaptobutanesulphinate trihydrate.

Anti-Inflammatory Agents

In some embodiments, a compound as described herein, is combined with an anti-inflammatory agent. Example anti-inflammatory agents include without limitation inhibitors of one or more of arginase (ARG1 NCBI Gene ID: 383), ARG2 (NCBI Gene ID: 384)), carbonic anhydrase (CA (NCBI Gene ID: 759), CA2 (NCBI Gene ID: 760), CA3 (NCBI Gene ID: 761), CA4 (NCBI Gene ID: 762), CA5A (NCBI Gene ID: 763), CA5B (NCBI Gene ID: 11238), CA6 (NCBI Gene ID: 765), CA7 (NCBI Gene ID: 766), CA8 (NCBI Gene ID: 767), CA9 (NCBI Gene ID: 768), CA10 (NCBI Gene ID: 56934), CA11 (NCBI Gene ID: 770), CA12 (NCBI Gene ID: 771), CA13 (NCBI Gene ID: 377677), CA14 (NCBI Gene ID: 23632)), prostaglandin-endoperoxide synthase 1 (PTGS1, COX-1; NCBI Gene ID: 5742), prostaglandin-endoperoxide synthase 2 (PTGS2, COX-2; NCBI Gene ID: 5743), secreted phospholipase A2, prostaglandin E synthase (PTGES, PGES; Gene ID: 9536), arachidonate 5-lipoxygenase (ALOX5, 5-LOX; NCBI Gene ID: 240), soluble epoxide hydrolase 2 (EPHX2, SEH; NCBI Gene ID: 2053) and/or mitogen-activated protein kinase kinase kinase 8 (MAP3K8, TPL2; NCBI Gene ID: 1326). In some embodiments, the inhibitor is a dual inhibitor, e.g., a dual inhibitor of COX-2/COX-1, COX-2/SEH, COX-2/CA, COX-2/5-LOX.

Examples of inhibitors of prostaglandin-endoperoxide synthase 1 (PTGS1, COX-1; NCBI Gene ID: 5742) that can be co-administered include without limitation mofezolac, GLY-230, and TRK-700.

Examples of inhibitors of prostaglandin-endoperoxide synthase 2 (PTGS2, COX-2; NCBI Gene ID: 5743) that can be co-administered include without limitation diclofenac, meloxicam, parecoxib, etoricoxib, AP-101, celecoxib, AXS-06, diclofenac potassium, DRGT-46, AAT-076, meisuoshuli, lumiracoxib, meloxicam, valdecoxib, zaltoprofen, nimesulide, Anitrazafen, Apricoxib, Cimicoxib, Deracoxib, Flumizole, Firocoxib, Mavacoxib, NS-398, Pamicogrel, Parecoxib, Robenacoxib, Rofecoxib, Rutecarpine, Tilmacoxib, and Zaltoprofen. Examples of dual COX1/COX2 inhibitors that can be co-administered include without limitation, HP-5000, lomoxicam, ketorolac tromethamine, bromfenac sodium, ATB-346, HP-5000. Examples of dual COX-2/carbonic anhydrase (CA) inhibitors that can be co-administered include without limitation polmacoxib and imrecoxib.

Examples of inhibitors of secreted phospholipase A2, prostaglandin E synthase (PTGES, PGES; Gene ID: 9536) that can be co-administered include without limitation LY3023703, GRC 27864, and compounds described in WO2015158204, WO2013024898, WO2006063466, WO2007059610, WO2007124589, WO2010100249, WO2010034796, WO2010034797, WO2012022793, WO2012076673, WO2012076672, WO2010034798, WO2010034799, WO2012022792, WO2009103778, WO2011048004, WO2012087771, WO2012161965, WO2013118071, WO2013072825, WO2014167444, WO2009138376, WO2011023812, WO2012110860, WO2013153535, WO2009130242, WO2009146696, WO2013186692, WO2015059618, WO2016069376, WO2016069374, WO2009117985, WO2009064250, WO2009064251, WO2009082347, WO2009117987, and WO2008071173. Metformin has further been found to repress the COX2/PGE2/STAT3 axis, and can be co-administered. See, e.g., Tong, et al., *Cancer Lett.* (2017) 389:23-32; and Liu, et al., *Oncotarget.* (2016) 7(19):28235-46.

Examples of inhibitors of carbonic anhydrase (e.g., one or more of CA1 (NCBI Gene ID: 759), CA2 (NCBI Gene ID: 760), CA3 (NCBI Gene ID: 761), CA4 (NCBI Gene ID: 762), CA5A (NCBI Gene ID: 763), CA5B (NCBI Gene ID: 11238), CA6 (NCBI Gene ID: 765), CA7 (NCBI Gene ID: 766), CA8 (NCBI Gene ID: 767), CA9 (NCBI Gene ID: 768), CA10 (NCBI Gene ID: 56934), CA11 (NCBI Gene ID: 770), CA12 (NCBI Gene ID: 771), CA13 (NCBI Gene ID: 377677), CA14 (NCBI Gene ID: 23632)) that can be co-administered include without limitation acetazolamide, methazolamide, dorzolamide, zonisamide, brinzolamide and dichlorphenamide. A dual COX-2/CA1/CA2 inhibitor that can be co-administered includes CG100649.

Examples of inhibitors of arachidonate 5-lipoxygenase (ALOX5, 5-LOX; NCBI Gene ID: 240) that can be co-administered include without limitation meclofenamate sodium, zileuton.

Examples of inhibitors of soluble epoxide hydrolase 2 (EPHX2, SEH; NCBI Gene ID: 2053) that can be co-administered include without limitation compounds described in WO2015148954. Dual inhibitors of COX-2/SEH that can be co-administered include compounds described in WO2012082647. Dual inhibitors of SEH and fatty acid amide hydrolase (FAAH; NCBI Gene ID: 2166) that can be co-administered include compounds described in WO2017160861.

Examples of inhibitors of mitogen-activated protein kinase kinase kinase 8 (MAP3K8, tumor progression loci-2, TPL2; NCBI Gene ID: 1326) that can be co-administered include without limitation GS-4875, GS-5290, BHM-078 and those described, e.g., in WO2006124944, WO2006124692, WO2014064215, WO2018005435, Teli, et al., *J Enzyme Inhib Med Chem.* (2012) 27(4):558-70; Gangwall, et al., *Curr Top Med Chem.* (2013) 13(9):1015-35; Wu, et al., *Bioorg Med Chem Lett.* (2009) 19(13):3485-8; Kaila, et al., *Bioorg Med Chem.* (2007) 15(19):6425-42; and Hu, et al., *Bioorg Med Chem Lett.* (2011) 21(16):4758-61.

Tumor Oxygenation Agents

In some embodiments, a compound as described herein, is combined with an agent that promotes or increases tumor oxygenation or reoxygenation, or prevents or reduces tumor hypoxia. Illustrative agents that can be co-administered include, e.g., Hypoxia inducible factor-1 alpha (HIF-1α) inhibitors, such as PT-2977, PT-2385; VEGF inhibitors, such as bevasizumab, IMC-3C5, GNR-011, tanibirumab, LYN-00101, ABT-165; and/or an oxygen carrier protein (e.g., a heme nitric oxide and/or oxygen binding protein (HNOX)), such as OMX-302 and HNOX proteins described in WO 2007/137767, WO 2007/139791, WO 2014/107171, and WO 2016/149562.

Immunotherapeutic Agents

In some embodiments, a compound as described herein, is combined with an immunotherapeutic agent. Example immunotherapeutic agents that can be co-administered include without limitation abagovomab, ABP-980, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, CC49, cetuximab, citatuzumab, cixutumumab, clivatuzumab, conatumumab, dacetuzumab, dalotuzumab, daratumumab, detumomab, dinutuximab, drozitumab, duligotumab, dusigitumab, ecromeximab, elotuzumab, emibetuzumab, ensituximab, ertumaxomab, etaracizumab, farletuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab (YERVOY®, MDX-010, BMS-734016, and MDX-101), iratumumab, labetuzumab, lexatumumab, lintuzumab, lorvotuzumab, lucatumumab, mapatumumab, matuzumab, milatuzumab, minretumomab, mitumomab, mogamulizumab, moxetumomab, naptumomab, narnatumab, necitumumab, nimotuzumab, nofetumomab, OBI-833, obinutuzumab, ocaratuzumab, ofatumumab, olaratumab, onartuzumab, oportuzumab, oregovomab, panitumumab, parsatuzumab, pasudotox, patritumab, pemtumomab, pertuzumab, pintumomab, pritumumab, racotumomab, radretumab, ramucirumab (Cyramza®), rilotumumab, rituximab, robatumumab, samalizumab, satumomab, sibrotuzumab, siltuximab, solitomab, simtuzumab, tacatuzumab, taplitumomab, tenatumomab, teprotumumab, tigatuzumab, tositumomab, trastuzumab, tucotuzumab, ubilituximab, veltuzumab, vorsetuzumab, votumumab, zalutumumab, and 3F8. Rituximab can be used for treating indolent B-cell cancers, including marginal-zone lymphoma, WM, CLL and small lymphocytic lymphoma. A combination of Rituximab and chemotherapy agents is especially effective.

The exemplified therapeutic antibodies may be further labeled or combined with a radioisotope particle such as indium-111, yttrium-90 (90Y-clivatuzumab), or iodine-131.

In some embodiments, the immunotherapeutic agent is an antibody-drug conjugate (ADC). Illustrative ADCs that can be co-administered include without limitation drug-conjugated antibodies, fragments thereof, or antibody mimetics targeting the proteins or antigens listed above and herein. Example ADCs that can be co-administered include without limitation gemtuzumab, brentuximab, trastuzumab, inotuzumab, glembatumumab, anetumab, mirvetuximab, depatuxizumab, rovalpituzumab, vadastuximab, labetuzumab, sacituzumab, lifastuzumab, indusatumab, polatzumab, pinatuzumab, coltuximab, indatuximab, milatuzumab, rovalpituzumab, ABBV-399, AGS-16C3F, ASG-22ME, AGS67E, AMG172, AMG575, BAY1129980, BAY1187982, BAY94-9343, GSK2857916, Humax-TF-ADC, IMGN289, IMGN529, IMGN853, LOP628, PCA062, MDX-1203 (BMS936561), MEDI-547, PF-06263507, PF-06647020, PF-06647263, PF-06664178, RG7450, RG7458, RG7598, SAR566658, SGN-CD19A, SGN-CD33A, SGN-CD70A, SGN-LIV1A and SYD985. ADCs that can be co-administered are described, e.g., in Lambert, et al., *Adv Ther* (2017) 34:1015-1035 and in de Goeij, *Current Opinion in Immunology* (2016) 40:14-23.

Illustrative therapeutic agents (e.g., anticancer or antineoplastic agents) that can be conjugated to the drug-conjugated antibodies, fragments thereof, or antibody mimetics include without limitation monomethyl auristatin E (MMAE), monomethyl auristatin F (MMAF), a calicheamicin, ansamitocin, maytansine or an analog thereof (e.g., mertansine/emtansine (DM1), ravtansine/soravtansine (DM4)), an anthracyline (e.g., doxorubicin, daunorubicin, epirubicin, idarubicin), pyrrolobenzodiazepine (PBD) DNA cross-linking agent SC-DR002 (D6.5), duocarmycin, a microtubule inhibitors (MTI) (e.g., a taxane, a vinca alkaloid, an epothilone), a pyrrolobenzodiazepine (PBD) or dimer thereof, a duocarmycin (A, B1, B2, C1, C2, D, SA, CC-1065), and other anticancer or anti-neoplastic agents described herein.

Cancer Gene Therapy and Cell Therapy

In some embodiments, a compound as described herein, is combined with a cancer gene therapy and cell therapy. Cancer gene therapies and cell therapies include the insertion of a normal gene into cancer cells to replace a mutated or altered gene; genetic modification to silence a mutated gene; genetic approaches to directly kill the cancer cells; including the infusion of immune cells designed to replace most of the patient's own immune system to enhance the immune response to cancer cells, or activate the patient's own immune system (T cells or Natural Killer cells) to kill cancer cells, or find and kill the cancer cells; genetic approaches to modify cellular activity to further alter endogenous immune responsiveness against cancer.

Cellular Therapies

In some embodiments, a compound as described herein, is combined with one or more cellular therapies. Illustrative cellular therapies include without limitation co-administration of one or more of a population of immune cells. In some embodiments, the immune cells are natural killer (NK) cells, NK-T cells, T cells, gamma delta T cells, B-cells, cytokine-induced killer (CIK) cells, macrophage (MAC) cells, tumor infiltrating lymphocytes (TILs) a granulocyte, an innate lymphoid cell, a megakaryocyte, a monocyte, a macrophage, a platelet, a thymocyte, a myeloid cell, and/or dendritic cells (DCs). In some embodiments, the cellular therapy entails a T cell therapy, e.g., co-administering a population of alpha/beta TCR T cells, gamma/delta TCR T cells, regulatory T (Treg) cells and/or TRuC™ T cells. In some embodiments, the cellular therapy entails a NK cell therapy, e.g., co-administering NK-92 cells. As appropriate, a cellular therapy can entail the co-administration of cells that are autologous, syngeneic or allogeneic to the subject.

In some embodiments, the cellular therapy entails co-administering immune cells engineered to express chimeric antigen receptors (CARs) or T cell receptors (TCRs) TCRs. In particular embodiments, a population of immune cells is engineered to express a CAR, wherein the CAR comprises a tumor antigen-binding domain. In other embodiments, a population of immune cells is engineered to express T cell receptors (TCRs) engineered to target tumor derived peptides presented on the surface of tumor cells. In one embodiment, the immune cell engineered to express chimeric antigen receptors (CARs) or T cell receptors (TCRs) TCRs is a T cell. In another embodiment, the immune cell engineered to express chimeric antigen receptors (CARs) or T cell receptors (TCRs) TCRs is an NK cell.

With respect to the structure of a CAR, in some embodiments, the CAR comprises an antigen binding domain, a transmembrane domain, and an intracellular signaling domain. In some embodiments, the intracellular domain comprises a primary signaling domain, a costimulatory domain, or both of a primary signaling domain and a costimulatory domain. In some embodiments, the primary signaling domain comprises a functional signaling domain of one or more proteins selected from the group consisting of CD3 zeta, CD3 gamma, CD3 delta, CD3 epsilon, common FcR gamma (FCERIG), FcR beta (Fc Epsilon R1b), CD79a, CD79b, Fcgamma RIIa, DAP10, and DAP12

4-1BB/CD137, activating NK cell receptors, an Immunoglobulin protein, B7-H3, BAFFR, BLAME (SLAMF8), BTLA, CD100 (SEMA4D), CD103, CD160 (BY55), CD18, CD19, CD19a, CD2, CD247, CD27, CD276 (B7-H3), CD28, CD29, CD3 delta, CD3 epsilon, CD3 gamma, CD30, CD4, CD40, CD49a, CD49D, CD49f, CD69, CD7, CD84, CD8alpha, CD8beta, CD96 (Tactile), CD11a, CD11b, CD11c, CD11d, CDS, CEACAM1, CRT AM, cytokine receptor, DAP-10, DNAM1 (CD226), Fc gamma receptor, GADS, GITR, HVEM (LIGHTR), IA4, ICAM-1, ICAM-1, Ig alpha (CD79a), IL-2R beta, IL-2R gamma, IL-7R alpha, inducible T cell costimulator (ICOS), integrins, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, ligand that binds with CD83, LIGHT, LIGHT, LTBR, Ly9 (CD229), Ly108), lymphocyte function-associated antigen-1 (LFA-1; CD1-1a/CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A, SLAMF7, SLP-76, TNF receptor proteins, TNFR2, TNFSF14, a Toll ligand receptor, TRANCE/RANKL, VLA1, or VLA-6, or a fragment, truncation, or a combination thereof.

In some embodiments, the costimulatory domain comprises a functional domain of one or more proteins selected from the group consisting of CD27, CD28, 4-1BB(CD137), OX40, CD30, CD40, PD-1, ICOS, CD2, CD7, LIGHT, NKG2C, lymphocyte function-associated antigen-1 (LFA-1), MYD88, B7-H3, a ligand that specifically binds with CD83, CDS, ICAM-1, GITR, BAFFR, HVEM (LIGHTR), SLAMF7, NKp80 (KLRFI), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, ITGAE, CD103, ITGAL, CD1A (NCBI Gene ID: 909), CDIB (NCBI Gene ID: 910), CDIC (NCBI Gene ID: 911), CDID (NCBI Gene ID: 912), CD1E (NCBI Gene ID: 913), ITGAM, ITGAX, ITGB1, CD29, ITGB2 (CD18, LFA-1), ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D.

In some embodiments, the transmembrane domain comprises a transmembrane domain derived from a protein selected from the group consisting of the alpha, beta or zeta chain of the T-cell receptor, CD28, CD3 epsilon, CD3 delta, CD3 gamma, CD45, CD4, CD5, CD7, CD8 alpha, CD8 beta, CD9, CD11a, CD11b, CD11c, CD11d, CD16, CD18, CD22, CD33, CD37, CD64, CD80, CD86, CD134, CD137, CD154, KIRDS2, OX40, CD2, CD27, ICOS (CD278), 4-1BB(CD137), GITR, CD40, BAFFR, HVEM (LIGHTR), SLAMF7, NKp80 (KLRF1), CD19, CD19a, IL2R beta, IL2R gamma, IL7R alpha, ITGA1, VLA1, CD49a, ITGA4, IA4, CD49D, ITGA6, VLA-6, CD49f, ITGAD, CD1A, CD1B, CD1C, CD1D, CD1E, ITGAE, CD103, ITGAL, ITGAM, ITGAX, ITGB1, ITGB2, ITGB7, CD29, ITGB2 (LFA-1, CD18), ITGB7, TNFR2, DNAM1 (CD226), SLAMF4 (CD244, 2B4), CD84, CD96 (TACTILE), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D, and NKG2C activating NK cell receptors, an Immunoglobulin protein, BTLA, CD247, CD276 (B7-H3), CD30, CD84, CDS, cytokine receptor, Fc gamma receptor, GADS, ICAM-1, Ig alpha (CD79a), integrins, LAT, a ligand that binds with CD83, LIGHT, MHC class 1 molecule, PAG/Cbp, TNFSF14, a Toll ligand receptor, TRANCE/RANKL, or a fragment, truncation, or a combination thereof.

In some embodiments, the CAR comprises a hinge domain. A hinge domain may be derived from a protein selected from the group consisting of the CD2, CD3 delta, CD3 epsilon, CD3 gamma, CD4, CD7, CD8.alpha., CD8.beta., CD11a (ITGAL), CD11b (ITGAM), CD11c (ITGAX), CD11d (ITGAD), CD18 (ITGB2), CD19 (B4), CD27 (TNFRSF7), CD28, CD28T, CD29 (ITGB1), CD30 (TNFRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (OX40), CD137 (4-1BB), CD150 (SLAMF1), CD158A (KIR2DL1), CD158B1 (KIR2DL2), CD158B2 (KIR2DL3), CD158C (KIR3DP1), CD158D (KIRDL4), CD158F1 (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355 (CRTAM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA-1, SLAMF9, LAT, GADS (GrpL), SLP-76 (LCP2), PAG1/CBP, a CD83 ligand, Fc gamma receptor, MHC class 1 molecule, MHC class 2 molecule, a TNF receptor protein, an immunoglobulin protein, a cytokine receptor, an integrin, activating NK cell receptors, or Toll ligand receptor, IgG1, IgG2, IgG3, IgG4, IgA, IgD, IgE, IgM or fragment or combination thereof.

In some embodiments, the one or more additional therapeutic agents comprises an immunotherapy, an immunostimulatory therapy, a cytokine therapy, a chemokine therapy, a cellular therapy, a gene therapy, and combinations thereof. In some embodiments, the immunotherapy comprises co-administering one or more antibodies or antigen-binding antibody fragments thereof, or antibody-drug conjugates thereof, CD3-targeting multi-specific molecules, CD16-targeting multi-specific molecules, or non-immunoglobulin antigen-binding domains or antibody mimetic proteins directed against one or more targets or tumor associated antigens (TAAs).

In some embodiments, the TCR or CAR antigen binding domain or the immunotherapeutic agent described herein (e.g., monospecific or multi-specific antibody or antigen-binding fragment thereof or antibody mimetic) binds a tumor-associated antigen (TAA). In some embodiments, the tumor-associated antigen is selected from the group consisting of: CD19; CD123; CD22; CD30; CD171; CS-1 (also referred to as CD2 subset 1, CRACC, SLAMF7, CD319, and 19A24); C-type lectin-like molecule-1 (CLL-1 or CLECLI); CD33; epidermal growth factor receptor variant III (EGFRvlll); ganglioside G2 (GD2); ganglioside GD3

(αNeuSAc(2-8)αNeuSAc(2-3)βDGaip(1-4)bDGlcp(1-1) Cer); ganglioside GM3 (αNeuSAc(2-3)βDGalp(1-4) βDGlcp(1-1)Cer); GM-CSF receptor; TNF receptor superfamily member 17 (TNFRSF17, BCMA); B-lymphocyte cell adhesion molecule; Tn antigen ((Tn Ag) or (GaINAcu-Ser/Thr)); prostate-specific membrane antigen (PSMA); Receptor tyrosine kinase-like orphan receptor 1 (RORI); Tumor-associated glycoprotein 72 (TAG72); CD38; CD44v6; Carcinoembryonic antigen (CEA); Epithelial cell adhesion molecule (EPCAM); B7H3 (CD276); KIT (CD117); Interleukin-13 receptor subunit alpha-2 (IL-13Ra2 or CD213A2); Mesothelin; Interleukin 11 receptor alpha (IL-11Ra); prostate stem cell antigen (PSCA); Protease Serine 21 (Testisin or PRSS21); vascular endothelial growth factor receptor 2 (VEGFR2); HLA class I antigen A-2 alpha; HLA antigen; Lewis(Y) antigen; CD24; Platelet-derived growth factor receptor beta (PDGFR-beta); Stage-specific embryonic antigen-4 (SSEA-4); CD20; delta like 3 (DLL3); Folate receptor alpha; Folate receptor beta, GDNF alpha 4 receptor, Receptor tyrosine-protein kinase, ERBB2 (Her2/ neu); Mucin 1, cell surface associated (MUC1); APRIL receptor; ADP ribosyl cyclase-1; Ephb4 tyrosine kinase receptor, DCAMKL1 serine threonine kinase, Aspartate beta-hydroxylase, epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); ephrin type-A receptor 3 (EphA3), Fucosyl GM1; sialyl Lewis adhesion molecule (sLe); transglutaminase 5 (TGS5); high molecular weight-melanomaassociatedantigen (HMWMAA); o-acetyl-GD2 ganglioside (OAcGD2); Folate receptor beta; tumor endothelial marker 1 (TEM1/CD248); tumor endothelial marker 7-related (TEM7R); six transmembrane epithelial antigen of the prostate I (STEAP1); claudin 6 (CLDN6); thyroid stimulating hormone receptor (TSHR); G protein-coupled receptor class C group 5, member D (GPRCSD); IL-15 receptor (IL-15); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GoboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (ORS IE2); TCR Gamma Alternate Reading Frame Protein (TARP); Wilms tumor protein (WT1); Cancer/testis antigen 1 (NY-ESO-1); Cancer/testis antigen 2 (LAGE-la); Melanoma associated antigen 1 (MAGE-A1); Melanoma associated antigen 3 (MAGE-A3); Melanoma associated antigen 4 (MAGE-A4); T cell receptor beta 2 chain C; ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MADCT-1); melanoma cancer testis antigen-2 (MAD-CT-2); Fos-related antigen 1; tumor protein p53, (p53); p53 mutant; prostein; survivin; telomerase; prostate carcinoma tumor antigen-1 (PCTA-1 or Galectin 8), melanoma antigen recognized by T cells 1 (MelanA or MARTI); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin-A1; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B1(CYP IBI); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAX5); proacrosin binding protein sp32 (OY-TES I); lymphocyte-specific protein tyrosine kinase (LCK); A kinase anchor protein 4 (AKAP-4); Peptidoglycan recognition protein, synovial sarcoma, X breakpoint 2 (SSX2); Receptor for Advanced Glycation Endproducts (RAGE-I); renal ubiquitous 1 (RUI); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIRI); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module containing mucin-like hormone receptor-like 2 (EMR2); lymphocyte antigen 75 (LY75); Glypican-2 (GPC2); Glypican-3 (GPC3); Fc receptor-like 5 (FCRL5); and immunoglobulin lambda-like polypeptide 1 (IGLL1). In some embodiments, the target is an epitope of the tumor associated antigen presented in an MHC.

In some embodiments, the tumor antigen is selected from CD150, 5T4, ActRIIA, B7, TNF receptor superfamily member 17 (TNFRSF17, BCMA), CA-125, CCNA1, CD123, CD126, CD138, CD14, CD148, CD15, CD19, CD20, CD200, CD21, CD22, CD23, CD24, CD25, CD26, CD261, CD262, CD30, CD33, CD362, CD37, CD38, CD4, CD40, CD40L, CD44, CD46, CD5, CD52, CD53, CD54, CD56, CD66a-d, CD74, CD8, CD80, CD92, CE7, CS-1, CSPG4, ED-B fibronectin, EGFR, EGFRvIII, EGP-2, EGP-4, EPHa2, ErbB2, ErbB3, ErbB4, FBP, HER1-HER2 in combination, HER2-HER3 in combination, HERV-K, HIV-1 envelope glycoprotein gp120, HIV-1 envelope glycoprotein gp41, HLA-DR, HLA class I antigen alpha G, HM1.24, K-Ras GTPase, HMW-MAA, Her2, Her2/neu, IGF-1R, IL-11Ralpha, IL-13R-alpha2, IL-2, IL-22R-alpha, IL-6, IL-6R, Ia, Ii, L1-CAM, L1-cell adhesion molecule, Lewis Y, L1-CAM, MAGE A3, MAGE-A1, MART-1, MUC1, NKG2C ligands, NKG2D Ligands, NYESO-1, OEPHa2, PIGF, PSCA, PSMA, RORI, T101, TAC, TAG72, TIM-3, TRAIL-R1, TRAIL-R1 (DR4), TRAIL-R$^2$ (DR5), VEGF, VEGFR2, WT-I, a G-protein coupled receptor, alphafetoprotein (AFP), an angiogenesis factor, an exogenous cognate binding molecule (ExoCBM), oncogene product, anti-folate receptor, c-Met, carcinoembryonic antigen (CEA), cyclin (D 1), ephrinB2, epithelial tumor antigen, estrogen receptor, fetal acetylcholine e receptor, folate binding protein, gp100, hepatitis B surface antigen, Epstein-Barr nuclear antigen 1, Latent membrane protein 1, Secreted protein BARF1, P2X7 purinoceptor, Syndecan-1, kappa chain, kappa light chain, kdr, lambda chain, livin, melanoma-associated antigen, mesothelin, mouse double minute 2 homolog (MDM2), mucin 16 (MUC16), mutated p53, mutated ras, necrosis antigens, oncofetal antigen, ROR2, progesterone receptor, prostate specific antigen, tEGFR, tenascin, P2-Microgiobuiin, Fc Receptor-like 5 (FcRL5).

Examples of cell therapies include without limitation: AMG-119, Algenpantucel-L, ALOFISEL®, Sipuleucel-T, (BPX-501) rivogenlecleucel U.S. Pat. No. 9,089,520, WO2016100236, AU-105, ACTR-087, activated allogeneic natural killer cells CNDO-109-AANK, MG-4101, AU-101, BPX-601, FATE-NK100, LFU-835 hematopoietic stem cells, Imilecleucel-T, baltaleucel-T, PNK-007, UCARTCS1, ET-1504, ET-1501, ET-1502, ET-190, CD19-ARTEMIS, ProHema, FT-1050-treated bone marrow stem cell therapy, CD4CARNK-92 cells, SNK-01, NEXI-001, CryoStim, AlloStim, lentiviral transduced huCART-meso cells, CART-22 cells, EGFRt/19-28z/4-1BBL CAR T cells, autologous 4H11-28z/fIL-12/EFGRt T cell, CCR5-SBC-728-HSPC, CAR4-1BBZ, CH-296, dnTGFbRII-NY-ESOc259T, Ad-RTS-IL-12, IMA-101, IMA-201, CARMA-0508, TT-18, CMD-501, CMD-503, CMD-504, CMD-502, CMD-601, CMD-602, CSG-005, LAAP T-cell therapy, PD-1 knockout T cell therapy (esophageal cancer/NSCLC), anti-MUC1 CAR T-cell therapy (esophageal cancer/NSCLC), anti-MUC1 CAR T-cell therapy+PD-1 knockout T cell therapy (esophageal cancer/NSCLC), anti-KRAS G12D mTCR PBL, anti-CD123 CAR T-cell therapy, anti-mutated neoantigen TCR T-cell therapy, tumor lysate/MUC1/survivin PepTivator-loaded dendritic cell vaccine, autologous dendritic cell vaccine (metastatic malignant melanoma, intradermal/intravenous), anti-LeY-scFv-CD28-zeta CAR T-cells, PRGN-3005, iC9-GD2-CAR-IL-15 T-cells, HSC-100, ATL-DC-101, MIDRIX4-LUNG, MIDRIXNEO, FCR-001, PLX stem cell therapy, MDR-101, GeniusVac-Mel4, ilixadencel, allogeneic mesenchymal stem cell therapy, romyelocel L, CYNK-001, ProTrans, ECT-100, MSCTRAIL, dilanubicel, FT-516, ASTVAC-2, E-CEL UVEC, CK-0801, allogenic alpha/beta CD3+ T cell and CD19+ B cell depleted stem cells (hematologic diseases, TBX-1400, HLCN-061, umbilical cord derived Hu-PHEC cells (hematological malignancies/aplastic anemia), AP-011, apceth-201, apceth-301, SENTI-101, stem cell therapy (pancreatic cancer), ICO-VIR15-cBiTE, CD33HSC/CD33 CAR-T, PLX-Immune, SUBCUVAX, CRISPR allogeneic gamma-delta T-cell based gene therapy (cancer), ex vivo CRISPR allogeneic healthy donor NK-cell based gene therapy (cancer), ex-vivo allogeneic induced pluripotent stem cell-derived NK-cell based gene therapy (solid tumor), and anti-CD20 CAR T-cell therapy (non-Hodgkin's lymphoma).

Additional Agents for Targeting Tumors Include without Limitation:

Alpha-fetoprotein, such as ET-1402, and AFP-TCR;

Anthrax toxin receptor 1, such as anti-TEM8 CAR T-cell therapy;

TNF receptor superfamily member 17 (TNFRSF17, BCMA), such as bb-2121 (ide-cel), bb-21217, JCARH125, UCART-BCMA, ET-140, KITE-585, MCM-998, LCAR-B38M, CART-BCMA, SEA-BCMA, BB212, ET-140, P-BCMA-101, AUTO-2 (APRIL-CAR), JNJ-68284528;

Anti-CLL-1 antibodies, such as KITE-796. See, for example, PCT/US2017/025573;

Anti-PD-L-CAR tank cell therapy, such as KD-045;

Anti-PD-L1 t-haNK, such as PD-L1 t-haNK;

anti-CD45 antibodies, such as 131I-BC8 (lomab-B);

anti-HER3 antibodies, such as LJM716, GSK2849330;

anti-CD52 antibodies, such as alemtuzumab;

APRIL receptor modulator, such as anti-BCMA CAR T-cell therapy, Descartes-011;

ADP ribosyl cyclase-1/APRIL receptor modulator, such as dual anti-BCMA/anti-CD38 CAR T-cell therapy; CART-ddBCMA;

B7 homolog 6, such as CAR-NKp30 and CAR-B7H6;

B-lymphocyte antigen CD19, such as TBI-1501, CTL-119 huCART-19 T cells, iso-cel, JCAR-015 U.S. Pat. No. 7,446,190, JCAR-014, JCAR-017, (WO2016196388, WO2016033570, WO2015157386), axicabtagene ciloleucel (KTE-C19, Yescarta®), KTE-X19, U.S. Pat. Nos. 7,741,465, 6,319,494, UCART-19, EBV-CTL, T tisagenlecleucel-T (CTL019), WO2012079000, WO2017049166, CD19CAR-CD28-CD3zeta-EGFRt-expressing T cells, CD19/4-1BBL armored CAR T cell therapy, C-CAR-011, CIK-CAR.CD19, CD19CAR-28-zeta T cells, PCAR-019, MatchCART, DSCAR-01, IM19 CAR-T, TC-110; anti-CD19 CAR T-cell therapy (B-cell acute lymphoblastic leukemia, Universiti Kebangsaan Malaysia); anti-CD19 CAR T-cell therapy (acute lymphoblastic leukemia/Non-Hodgkin's lymphoma, University Hospital Heidelberg), anti-CD19 CAR T-cell therapy (silenced IL-6 expression, cancer, Shanghai Unicar-Therapy Biomedicine Technology), MB-CART2019.1 (CD19/CD20), GC-197 (CD19/CD7), CLIC-1901, ET-019003, anti-CD19-STAR-T cells, AVA-001, BCMA-CD19 cCAR (CD19/APRIL), ICG-134, ICG-132 (CD19/CD20), CTA-101, WZTL-002, dual anti-CD19/anti-CD20 CAR T-cells (chronic lymphocytic leukemia/B-cell lymphomas), HY-001, ET-019002, YTB-323, GC-012 (CD19/APRIL), GC-022 (CD19/CD22), CD19CAR-CD28-CD3zeta-EGFRt-expressing Tn/mem; UCAR-011, ICTCAR-014, GC-007F, PTG-01, CC-97540;

Allogeneic anti-CD19 CART cells, such as GC-007G;

Allogenic T cells expressing CD20 CAR, such as LB-1905;

APRIL receptor modulator; SLAM family member 7 modulator, BCMA-CS1 cCAR;

Autologous dendritic cell tumor antigen (ADCTA), such as ADCTA-SSI-G;

B-lymphocyte antigen CD20, such as ACTR707 ATTCK-20, PBCAR-20A;

B-lymphocyte antigen CD19/B-lymphocyte antigen 22, such as TC-310;

B-lymphocyte antigen 22 cell adhesion, such as UCART-22, JCAR-018 WO2016090190;

NY-ESO-1 modulators, such as GSK-3377794, TBI-1301, GSK3537142;

Carbonic anhydrase, such as DC-Ad-GMCAIX;

Caspase 9 suicide gene, such as CaspaCIDe DLI, BPX-501;

CCR5, such as SB-728;

CCR5 gene inhibitor/TAT gene/TRIM5 gene stimulator, such as lentivirus vector CCR5 shRNA/TRIM5alpha/TAR decoy-transduced autologous CD34-positive hematopoietic progenitor cells;

CDw123, such as MB-102, IM-23, JEZ-567, UCART-123;

CD4, such as ICG-122;

CD5 modulators, such as CD5.28z CART cells;

Anti-CD22, such as anti-CD22 CART;

Anti-CD30, such as TT-11;

CD33, such as CIK-CAR.CD33, CD33CART;

Dual anti-CD33/anti-CLL1, such as LB-1910;

CD38, such as T-007, UCART-38;

CD40 ligand, such as BPX-201, MEDI5083;

CD56, such as allogeneic CD56-positive CD3-negative natural killer cells (myeloid malignancies);
CD19/CD7 modulator, such as GC-197;
T-cell antigen CD7 modulator, such as anti-CD7 CAR T-cell therapy (CD7-positive hematological malignancies);
CD123 modulator, such as UniCAR02-T-CD123;
Anti-CD276, such as anti-CD276 CART;
CEACAM protein 5 modulators, such as MG7-CART;
Claudin 6, such as CSG-002;
Claudin 18.2, such as LB-1904;
Chlorotoxin, such as CLTX-CART;
EBV targeted, such as CMD-003;
MUC16EGFR, such as autologous 4H11-28z/fIL-12/EFGRt T cell;
Endonuclease, such as PGN-514, PGN-201;
Epstein-Barr virus specific T-lymphocytes, such as TT-10;
Epstein-Barr nuclear antigen 1/Latent membrane protein 1/Secreted protein BARF1 modulator, such as TT-10X;
Erbb2, such as CST-102, CIDeCAR;
Ganglioside (GD2), such as 4SCAR-GD2;
Gamma delta T cells, such as ICS-200;
folate hydrolase 1 (FOLH1, Glutamate carboxypeptidase II, PSMA; NCBI Gene ID: 2346), such as CIK-CAR.PSMA, CART-PSMA-TGFβRDN, P-PSMA-101;
Glypican-3(GPC3), such as TT-16, GLYCAR;
Hemoglobin, such as PGN-236;
Hepatocyte growth factor receptor, such as anti-cMet RNA CAR T;
HLA class I antigen A-2 alpha modulator, such as FH-MCVA2TCR;
HLA class I antigen A-2 alpha/Melanoma associated antigen 4 modulator, such as ADP-A2M4CD8;
HLA antigen modulator, such as FIT-001, NeoTCR-P1;
Human papillomavirus E7 protein, such as KITE-439. See, for example, PCT/US2015/033129;
ICAM-1 modulator, such as AIC-100;
Immunoglobulin gamma Fc receptor III, such as ACTR087;
IL-12, such as DC-RTS-IL-12;
IL-12 agonist/mucin 16, such as JCAR-020;
IL-13 alpha 2, such as MB-101;
IL-15 receptor agonist, such as PRGN-3006, ALT-803; interleukin-15/Fc fusion protein (e.g., XmAb24306); recombinant interleukin-15 (e.g., AM0015, NIZ-985); pegylated IL-15 (e.g., NKTR-255);
IL-2, such as CST-101;
Interferon alpha ligand, such as autologous tumor cell vaccine+systemic CpG-B+IFN-alpha (cancer);
K-Ras GTPase, such as anti-KRAS G12V mTCR cell therapy;
Neural cell adhesion molecule L1 L1CAM (CD171), such as JCAR-023;
Latent membrane protein 1/Latent membrane protein 2, such as Ad5f35-LMPd1-2-transduced autologous dendritic cells;
MART-1 melanoma antigen modulator, such as MART-1 F5 TCR engineered PBMC;
Melanoma associated antigen 10, such as MAGE-A10C796T MAGE-A10 TCR;
Melanoma associated antigen 3/Melanoma associated antigen 6 (MAGE A3/A6) such as KITE-718 (see, for example, PCT/US2013/059608);
Mesothelin, such as CSG-MESO, TC-210;
Mucin 1 modulator, such as ICTCAR-052, Tn MUC-1 CAR-T, ICTCAR-053;
Anti-MICA/MICB, such as CYAD-02;
NKG2D, such as NKR-2;
Ntrkr1 tyrosine kinase receptor, such as JCAR-024;
PRAMET cell receptor, such as BPX-701;
Prostate stem cell antigen modulator, such as MB-105;
Roundabout homolog 1 modulator, such as ATCG-427;
Peptidoglycan recognition protein modulator, such as Tag-7 gene modified autologous tumor cell vaccine;
PSMA, such as PSMA-CAR T-cell therapy (lentiviral vector, castrate-resistant prostate cancer);
SLAM family member 7 modulator, such as IC9-Luc90-CD828Z;
TGF beta receptor modulator, such as DNR.NPC T-cells;
T-lymphocyte, such as TT-12;
T-lymphocyte stimulator, such as ATL-001;
TSH receptor modulator, such as ICTCAR-051;
Tumor infiltrating lymphocytes, such as LN-144, LN-145; and/or
Wilms tumor protein, such as JTCR-016, WT1-CTL.

Agonists of Fins Related Receptor Tyrosine Kinase 3 (FLT3)

In some embodiments, a compound as described herein, is combined with an agonist of fins related receptor tyrosine kinase 3 (FLT3); FLK2; STK1; CD135; FLK-2; NCBI Gene ID: 2322). Examples of FLT3 agonists include CDX-301 and GS-3583.

MCL1 Apoptosis Regulator, BCL2 Family Member (MCL1) Inhibitors

In some embodiments, a compound as described herein, is combined with an inhibitor of MCL1 apoptosis regulator, BCL2 family member (MCL1, TM; EAT; MCL1L; MCL1S; Mcl-1; BCL2L3; MCL1-ES; bcl2-L-3; mcl1/EAT; NCBI Gene ID: 4170). Examples of MCL1 inhibitors include AMG-176, AMG-397, S-64315, and AZD-5991, 483-LM, A-1210477, UMI-77, JKY-5-037, and those described in WO2018183418, WO2016033486, WO2019222112 and WO2017147410.

Cytokine Inducible SH2 Containing Protein (CISH) Inhibitors

In some embodiments, a compound as described herein, is combined with an inhibitor of cytokine inducible SH2 containing protein (CISH; CIS; G18; SOCS; CIS-1; BACTS2; NCBI Gene ID: 1154). Examples of CISH inhibitors include those described in WO2017100861, WO2018075664 and WO2019213610.

Gene Editors

In some embodiments, a compound as described herein, is combined with gene editor. Illustrative gene editing system that can be co-administered include without limitation a CRISPR/Cas9 system, a zinc finger nuclease system, a TALEN system, a homing endonucleases system (e.g., an ARCUS), and a homing meganuclease system.

Others Drugs with Unspecified Targets

In some embodiments, a compound as described herein, is combined with human immunoglobulin (10% liquid formulation), Cuvitru (human immunoglobulin (20% solution), levofolinate disodium, IMSA-101, BMS-986288, IMUNO BGC Moreau RJ, R-OKY-034F, GP-2250, AR-23, calcium levofolinate, porfimer sodium, RG6160, ABBV-155, CC-99282, polifeprosan 20 with carmustine, Veregen, gadoxetate disodium, gadobutrol, gadoterate meglumine, gadoteridol, 99mTc-sestamibi, pomalidomide, pacibanil, or valrubicin.

2. Human Immunodeficiency Virus (HIV)

In some embodiments, the additional therapeutic agent may be an anti-HIV agent. In some instances, the additional therapeutic agent can be HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, HIV capsid inhibitors, HIV Tat or Rev inhibitors, immunomodulators, immunotherapeutic agents, antibody-drug conjugates, gene modifiers, gene editors (such as CRISPR/Cas9, zinc finger nucleases, homing nucleases, synthetic nucleases, TALENs), cell therapies (such as chimeric antigen receptor T-cell, CAR-T, and engineered T-cell receptors, TCR-T, autologous T-cell therapies, engineered B cells), latency reversing agents, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, HIV-1 Nef modulators, Hck tyrosine kinase modulators, mixed lineage kinase-3 (MLK-3) inhibitors, HIV-1 splicing inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, HIV vaccines, and combinations thereof.

In some embodiments, the additional therapeutic agent is selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and combinations thereof.

3. Hepatitis B Virus

In some embodiments, a compound of the present disclosure, or pharmaceutically acceptable salt thereof, is combined with one, two, three, four or more additional therapeutic agents selected from HBV combination drugs, HBV vaccines, HBV DNA polymerase inhibitors, immunomodulators, toll-like receptor (TLR) modulators, interferon alpha receptor ligands, hyaluronidase inhibitors, hepatitis b core antigen (HBcAg) inhibitors, hepatitis b surface antigen (HBsAg) inhibitors, cytotoxic T-lymphocyte-associated protein 4 (ipi4) inhibitors, cyclophilin inhibitors, HBV viral entry inhibitors, antisense oligonucleotide targeting viral mRNA, short interfering RNAs (siRNA) and ddRNAi, endonuclease modulators, ribonucelotide reductase inhibitors, HBV E antigen inhibitors, covalently closed circular DNA (cccDNA) inhibitors, farnesoid X receptor agonists, STING agonists, anti-HBV antibodies, CCR2 chemokine antagonists, thymosin agonists, cytokines, nucleoprotein modulators, retinoic acid-inducible gene 1 stimulators, NOD2 stimulators, phosphatidylinositol 3-kinase (PI3K) inhibitors, indoleamine-2, 3-dioxygenase (IDO) pathway inhibitors, PD-1 inhibitors, PD-L1 inhibitors, recombinant thymosin alpha-1, bruton's tyrosine kinase (BTK) inhibitors, KDM inhibitors, HBV replication inhibitors, arginase inhibitors, gene therapy and cell therapy, gene editors, CAR-T cell therapy, TCR-T cell therapy, and other HBV drugs.

In some embodiments, a compound of the present disclosure, or pharmaceutically acceptable salt thereof, may be used or combined with one or more of a chemotherapeutic agent, an immunomodulator, an immunotherapeutic agent, a therapeutic antibody, a therapeutic vaccine, a bispecific antibody and "antibody-like" therapeutic protein (such as DARPins®, anti-pMHC TCR-like antibodies, DARTs®, Duobodies®, Bites®, XmAbs®, TandAbs®, Fab derivatives), an antibody-drug conjugate (ADC), gene modifiers or gene editors (such as CRISPR Cas9, zinc finger nucleases, homing endonucleases, homing meganucleases (e.g., ARCUS), synthetic nucleases, TALENs), cell therapies such as CAR-T (chimeric antigen receptor T-cell), and TCR-T (an engineered T cell receptor) agent or any combination thereof.

In some embodiments, an agent as described herein, is combined with one, two, three, four or more additional therapeutic agents, e.g., as 3-dioxygenase (IDO) inhibitors, apolipoprotein A1 modulator, arginase inhibitors, B- and T-lymphocyte attenuator inhibitors, Bruton's tyrosine kinase (BTK) inhibitors, CCR2 chemokine antagonist, CD137 inhibitors, CD160 inhibitors, CD305 inhibitors, CD4 agonist and modulator, compounds targeting hepatitis B core antigen (HBcAg), core protein allosteric modulators, covalently closed circular DNA (cccDNA) inhibitors, cyclophilin inhibitors, cytotoxic T-lymphocyte-associated protein 4 (ipi4) inhibitors, DNA polymerase inhibitor, endonuclease modulators, epigenetic modifiers, Farnesoid X receptor agonists, HBV DNA polymerase inhibitors, HBV replication inhibitors, HBV RNAse inhibitors, HBV viral entry inhibitors, HBx inhibitors, Hepatitis B large envelope protein modulator, Hepatitis B large envelope protein stimulator, Hepatitis B structural protein modulator, hepatitis B surface antigen (HBsAg) inhibitors, hepatitis B surface antigen (HBsAg) secretion or assembly inhibitors, hepatitis B virus E antigen inhibitors, hepatitis B virus replication inhibitors, Hepatitis virus structural protein inhibitor, HIV-1 reverse transcriptase inhibitor, Hyaluronidase inhibitor, inhibitor of apoptosis proteins family proteins (IAPs) inhibitors, IL-2 agonist, IL-7 agonist, immunomodulators, indoleamine-2 inhibitors, inhibitors of ribonucleotide reductase, Interleukin-2 ligand, ipi4 inhibitors, lysine demethylase inhibitors, histone demethylase inhibitors, KDM1 inhibitors, KDM5 inhibitors, killer cell lectin-like receptor subfamily G member 1 inhibitors, lymphocyte-activation gene 3 inhibitors, lymphotoxin beta receptor activators, modulators of Axl, modulators of B7-H3, modulators of B7-H4, modulators of CD160, modulators of CD161, modulators of CD27, modulators of CD47, modulators of CD70, modulators of GITR, modulators of HEVEM, modulators of ICOS, modulators of Mer, modulators of NKG2A, modulators of NKG2D, modulators of OX40, modulators of SIRPalpha, modulators of TIGIT, modulators of Tim-4, modulators of Tyro, Na+-taurocholate cotransporting polypeptide (NTCP) inhibitors, natural killer cell receptor 2B4 inhibitors, NOD2 gene stimulator, Nucleoprotein inhibitor, nucleoprotein modulators, OX-40 receptor agonist, PD-1 inhibitors, PD-L1 inhibitors, peptidylprolyl isomerase inhibitor, phosphatidylinositol-3 kinase (PI3K) inhibitors, Retinoic acid-inducible gene 1 stimulator, Reverse transcriptase inhibitor, Ribonuclease inhibitor, RNA DNA polymerase inhibitor, SLC10A1 gene inhibitor, SMAC mimetics, Src tyrosine kinase inhibitor, stimulator of interferon gene (STING)

agonists, stimulators of NOD1, T cell surface glycoprotein CD28 inhibitor, T-cell surface glycoprotein CD8 modulator, Thymosin agonist, Thymosin alpha 1 ligand, Tim-3 inhibitors, TLR-3 agonists, TLR-7 agonists, TLR-9 agonists, TLR9 agonists or gene stimulator, toll-like receptor (TLR) modulators, viral ribonucleotide reductase inhibitors, and combinations thereof.

B. Exemplified Combination Therapies

1. Cancer

Lymphoma or Leukemia Combination Therapy

Some chemotherapy agents are suitable for treating lymphoma or leukemia. These agents include aldesleukin, alvocidib, amifostine trihydrate, aminocamptothecin, antineoplaston A10, antineoplaston AS2-1, anti-thymocyte globulin, arsenic trioxide, Bcl-2 family protein inhibitor ABT-263, beta alethine, BMS-345541bortezomib (VELCADE®, PS-341), bryostatin 1, bulsulfan, campath-1H, carboplatin, carfilzomib (Kyprolis®), carmustine, caspofungin acetate, CC-5103, chlorambucil, CHOP (cyclophosphamide, doxorubicin, vincristine, and prednisone), cisplatin, cladribine, clofarabine, curcumin, CVP (cyclophosphamide, vincristine, and prednisone), cyclophosphamide, cyclosporine, cytarabine, denileukin diftitox, dexamethasone, docetaxel, dolastatin 10, doxorubicin, doxorubicin hydrochloride, DT-PACE (dexamethasone, thalidomide, cisplatin, doxorubicin, cyclophosphamide, and etoposide), enzastaurin, epoetin alfa, etoposide, everolimus (RAD001), FCM (fludarabine, cyclophosphamide, and mitoxantrone), FCR (fludarabine, cyclophosphamide, and rituximab), fenretinide, filgrastim, flavopiridol, fludarabine, FR (fludarabine and rituximab), geldanamycin (17 AAG), hyperCVAD (hyperfractionated cyclophosphamide, vincristine, doxorubicin, dexamethasone, methotrexate, and cytarabine), ICE (iphosphamide, carboplatin, and etoposide), ifosfamide, irinotecan hydrochloride, interferon alpha-2b, ixabepilone, lenalidomide (REVLIMID®, CC-5013), pomalidomide (POMALYST®/IMNOVID®)lymphokine-activated killer cells, MCP (mitoxantrone, chlorambucil, and prednisolone), melphalan, mesna, methotrexate, mitoxantrone hydrochloride, motexafin gadolinium, mycophenolate mofetil, nelarabine, obatoclax (GX15-070), oblimersen, octreotide acetate, omega-3 fatty acids, Omr-IgG-am (WNIG, Omrix), oxaliplatin, paclitaxel, palbociclib (PD0332991), pegfilgrastim, PEGylated liposomal doxorubicin hydrochloride, perifosin, prednisolone, prednisone, recombinant flt3 ligand, recombinant human thrombopoietin, recombinant interferon alfa, recombinant interleukin-11, recombinant interleukin-12, rituximab, R-CHOP (rituximab and CHOP), R-CVP (rituximab and CVP), R-FCM (rituximab and FCM), R-ICE (rituximab and ICE), and R MCP (rituximab and MCP), R-roscovitine (seliciclib, CYC202), sargramostim, sildenafil citrate, simvastatin, sirolimus, styryl sulphones, tacrolimus, tanespimycin, temsirolimus (CC-779), thalidomide, therapeutic allogeneic lymphocytes, thiotepa, tipifarnib, vincristine, vincristine sulfate, vinorelbine ditartrate, SAHA (suberanilohydroxamic acid, or suberoyl, anilide, and hydroxamic acid), vemurafenib (Zelboraf®), venetoclax (ABT-199).

One modified approach is radioimmunotherapy, wherein a monoclonal antibody is combined with a radioisotope particle, such as indium-111, yttrium-90, and iodine-131. Examples of combination therapies include, but are not limited to, iodine-131 tositumomab (BEXXAR®), yttrium-90 ibritumomab tiuxetan (ZEVALIN®), and BEXXAR® with CHOP.

The abovementioned therapies can be supplemented or combined with stem cell transplantation or treatment. Therapeutic procedures include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme technique, low-LET cobalt-60 gamma ray therapy, bleomycin, conventional surgery, radiation therapy, and nonmyeloablative allogeneic hematopoietic stem cell transplantation.

Non-Hodgkin's Lymphomas Combination Therapy

Treatment of non-Hodgkin's lymphomas (NHL), especially those of B cell origin, includes using monoclonal antibodies, standard chemotherapy approaches (e.g., CHOP (cyclophosphamide, doxorubicin, vincristine, and prednisone), CVP (cyclophosphamide, vincristine, and prednisone), FCM (fludarabine, cyclophosphamide, and mitoxantrone), MCP (Mitoxantrone, Chlorambucil, Prednisolone), all optionally including rituximab (R) and the like), radio-immunotherapy, and combinations thereof, especially integration of an antibody therapy with chemotherapy.

Examples of unconjugated monoclonal antibodies for the treatment of NHL/B-cell cancers include rituximab, alemtuzumab, human or humanized anti-CD20 antibodies, lumiliximab, anti-TNF-related apoptosis-inducing ligand (anti-TRAIL), bevacizumab, galiximab, epratuzumab, SGN-40, and anti-CD74.

Examples of experimental antibody agents used in treatment of NHL/B-cell cancers include ofatumumab, ha20, PRO131921, alemtuzumab, galiximab, SGN-40, CHIR-12.12, epratuzumab, lumiliximab, apolizumab, milatuzumab, and bevacizumab.

Examples of standard regimens of chemotherapy for NHL/B-cell cancers include CHOP, FCM, CVP, MCP, R-CHOP (rituximab, cyclophosphamide, doxorubicin, vincristine, and prednisone), R-FCM, R-CVP, and R MCP.

Examples of radioimmunotherapy for NHL/B-cell cancers include yttrium-90 ibritumomab tiuxetan (ZEVALIN®) and iodine-131 tositumomab (BEXXAR®).

Mantle Cell Lymphoma Combination Therapy

Therapeutic treatments for mantle cell lymphoma (MCL) include combination chemotherapies such as CHOP, hyperCVAD, and FCM. These regimens can also be supplemented with the monoclonal antibody rituximab to form combination therapies R-CHOP, hyperCVAD-R, and R-FCM. Any of the abovementioned therapies may be combined with stem cell transplantation or ICE in order to treat MCL.

An alternative approach to treating MCL is immunotherapy. One immunotherapy uses monoclonal antibodies like rituximab. Another uses cancer vaccines, such as GTOP-99, which are based on the genetic makeup of an individual patient's tumor.

A modified approach to treat MCL is radioimmunotherapy, wherein a monoclonal antibody is combined with a radioisotope particle, such as iodine-131 tositumomab (BEXXAR®) and yttrium-90 ibritumomab tiuxetan (ZEVALIN®). In another example, BEXXAR® is used in sequential treatment with CHOP.

Other approaches to treating MCL include autologous stem cell transplantation coupled with high-dose chemotherapy, administering proteasome inhibitors such as bortezomib (VELCADE® or PS-341), or administering antiangiogenesis agents such as thalidomide, especially in combination with rituximab.

Another treatment approach is administering drugs that lead to the degradation of Bcl-2 protein and increase cancer cell sensitivity to chemotherapy, such as oblimersen, in combination with other chemotherapeutic agents.

A further treatment approach includes administering mTOR inhibitors, which can lead to inhibition of cell growth and even cell death. Non-limiting examples are sirolimus, temsirolimus (TORISEL®, CCI-779), CC-115, CC-223, SF-1126, PQR-309 (bimiralisib), voxtalisib, GSK-2126458, and temsirolimus in combination with RITUXAN®, VELCADE®, or other chemotherapeutic agents.

Other recent therapies for MCL have been disclosed. Such examples include flavopiridol, palbociclib (PD0332991), R-roscovitine (selicicilib, CYC202), styryl sulphones, obatoclax (GX15-070), TRAIL, Anti-TRAIL death receptors DR4 and DR5 antibodies, temsirolimus (TORISEL®, CCl-779), everolimus (RAD001), BMS-345541, curcumin, SAHA, thalidomide, lenalidomide (REVLIMID®, CC-5013), and geldanamycin (17 AAG).

Waldenstrom's Macroglobulinemia Combination Therapy

Therapeutic agents used to treat Waldenstrom's Macroglobulinemia (WM) include aldesleukin, alemtuzumab, alvocidib, amifostine trihydrate, aminocamptothecin, antineoplaston A10, antineoplaston AS2-1, anti-thymocyte globulin, arsenic trioxide, autologous human tumor-derived HSPPC-96, Bcl-2 family protein inhibitor ABT-263, beta alethine, bortezomib (VELCADE®), bryostatin 1, busulfan, campath-1H, carboplatin, carmustine, caspofungin acetate, CC-5103, cisplatin, clofarabine, cyclophosphamide, cyclosporine, cytarabine, denileukin diftitox, dexamethasone, docetaxel, dolastatin 10, doxorubicin hydrochloride, DT-PACE, enzastaurin, epoetin alfa, epratuzumab (hLL2-anti-CD22 humanized antibody), etoposide, everolimus, fenretinide, filgrastim, fludarabine, ibrutinib, ifosfamide, indium-111 monoclonal antibody MN-14, iodine-131 tositumomab, irinotecan hydrochloride, ixabepilone, lymphokine-activated killer cells, melphalan, mesna, methotrexate, mitoxantrone hydrochloride, monoclonal antibody CD19 (such as tisagenlecleucel-T, CART-19, CTL-019), monoclonal antibody CD20, motexafin gadolinium, mycophenolate mofetil, nelarabine, oblimersen, octreotide acetate, omega-3 fatty acids, oxaliplatin, paclitaxel, pegfilgrastim, PEGylated liposomal doxorubicin hydrochloride, pentostatin, perifosine, prednisone, recombinant flt3 ligand, recombinant human thrombopoietin, recombinant interferon alfa, recombinant interleukin-11, recombinant interleukin-12, rituximab, sargramostim, sildenafil citrate (VIAGRA®), simvastatin, sirolimus, tacrolimus, tanespimycin, thalidomide, therapeutic allogeneic lymphocytes, thiotepa, tipifarnib, tositumomab, ulocuplumab, veltuzumab, vincristine sulfate, vinorelbine ditartrate, vorinostat, WTT 126-134 peptide vaccine, WT-1 analog peptide vaccine, yttrium-90 ibritumomab tiuxetan, yttrium-90 humanized epratuzumab, and any combination thereof.

Examples of therapeutic procedures used to treat WM include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme techniques, low-LET cobalt-60 gamma ray therapy, bleomycin, conventional surgery, radiation therapy, and nonmyeloablative allogeneic hematopoietic stem cell transplantation.

Diffuse Large B-Cell Lymphoma Combination Therapy

Therapeutic agents used to treat diffuse large B-cell lymphoma (DLBCL) include cyclophosphamide, doxorubicin, vincristine, prednisone, anti-CD20 monoclonal antibodies, etoposide, bleomycin, many of the agents listed for WM, and any combination thereof, such as ICE and R ICE.

Chronic Lymphocytic Leukemia Combination Therapy

Examples of therapeutic agents used to treat chronic lymphocytic leukemia (CLL) include chlorambucil, cyclophosphamide, fludarabine, pentostatin, cladribine, doxorubicin, vincristine, prednisone, prednisolone, alemtuzumab, many of the agents listed for WM, and combination chemotherapy and chemoimmunotherapy, including the following common combination regimens: CVP, R-CVP, ICE, R-ICE, FCR, and FR.

Myelofibrosis Combination Therapy

Myelofibrosis inhibiting agents include, but are not limited to, hedgehog inhibitors, histone deacetylase (HDAC) inhibitors, and tyrosine kinase inhibitors. Non-limiting examples of hedgehog inhibitors are saridegib and vismodegib. Examples of HDAC inhibitors include, but are not limited to, pracinostat and panobinostat. Non-limiting examples of tyrosine kinase inhibitors are lestaurtinib, bosutinib, imatinib, radotinib, and cabozantinib.

Hyperproliferative Disorder Combination Therapy

Gemcitabine, nab-paclitaxel, and gemcitabine/nab-paclitaxel may be used with a JAK inhibitor and/or PI3Kδ inhibitor to treat hyperproliferative disorders.

Bladder Cancer Combination Therapy

Therapeutic agents used to treat bladder cancer include atezolizumab, carboplatin, cisplatin, docetaxel, doxorubicin, fluorouracil (5-FU), gemcitabine, idosfamide, Interferon alfa-2b, methotrexate, mitomycin, nab-paclitaxel, paclitaxel, pemetrexed, thiotepa, vinblastine, and any combination thereof.

Breast Cancer Combination Therapy

Therapeutic agents used to treat breast cancer include albumin-bound paclitaxel, anastrozole, capecitabine, carboplatin, cisplatin, cyclophosphamide, docetaxel, doxorubicin, epirubicin, everolimus, exemestane, fluorouracil, fulvestrant, gemcitabine, Ixabepilone, lapatinib, Letrozole, methotrexate, mitoxantrone, paclitaxel, pegylated liposomal doxorubicin, pertuzumab, tamoxifen, toremifene, trastuzumab, vinorelbine, and any combinations thereof.

Triple Negative Breast Cancer Combination Therapy

Therapeutic agents used to treat triple negative breast cancer include cyclophosphamide, docetaxel, doxorubicin, epirubicin, fluorouracil, paclitaxel, and combinations thereof.

Colorectal Cancer Combination Therapy

Therapeutic agents used to treat colorectal cancer include bevacizumab, capecitabine, cetuximab, fluorouracil, irinotecan, leucovorin, oxaliplatin, panitumumab, ziv-aflibercept, and any combinations thereof.

Castration-Resistant Prostate Cancer Combination Therapy

Therapeutic agents used to treat castration-resistant prostate cancer include abiraterone, cabazitaxel, docetaxel, enzalutamide, prednisone, sipuleucel-T, and any combinations thereof.

Esophageal and Esophagogastric Junction Cancer Combination Therapy

Therapeutic agents used to treat esophageal and esophagogastric junction cancer include capecitabine, carboplatin, cisplatin, docetaxel, epirubicin, fluoropyrimidine, fluorouracil, irinotecan, leucovorin, oxaliplatin, paclitaxel, ramucirumab, trastuzumab, and any combinations thereof.

Gastric Cancer Combination Therapy

Therapeutic agents used to treat gastric cancer include capecitabine, carboplatin, cisplatin, docetaxel, epirubicin, fluoropyrimidine, fluorouracil, Irinotecan, leucovorin, mitomycin, oxaliplatin, paclitaxel, ramucirumab, trastuzumab, and any combinations thereof.

Head and Neck Cancer Combination Therapy

Therapeutic agents used to treat head & neck cancer include afatinib, bleomycin, capecitabine, carboplatin, cetuximab, cisplatin, docetaxel, fluorouracil, gemcitabine, hydroxyurea, methotrexate, nivolumab, paclitaxel, pembrolizumab, vinorelbine, and any combinations thereof.

Hepatobiliary Cancer Combination Therapy

Therapeutic agents used to treat hepatobiliary cancer include capecitabine, cisplatin, fluoropyrimidine, 5-fluorourcil, gemecitabine, oxaliplatin, sorafenib, and any combinations thereof.

Hepatocellular Carcinoma Combination Therapy

Therapeutic agents used to treat hepatocellular carcinoma include capecitabine, doxorubicin, gemcitabine, sorafenib, and any combinations thereof.

Non-Small Cell Lung Cancer Combination Therapy

Therapeutic agents used to treat non-small cell lung cancer (NSCLC) include afatinib, albumin-bound paclitaxel, alectinib, bevacizumab, bevacizumab, cabozantinib, carboplatin, cisplatin, crizotinib, dabrafenib, docetaxel, erlotinib, etoposide, gemcitabine, nivolumab, paclitaxel, pembrolizumab, pemetrexed, ramucirumab, trametinib, trastuzumab, vandetanib, vemurafenib, vinblastine, vinorelbine, and any combinations thereof.

Small Cell Lung Cancer Combination Therapy

Therapeutic agents used to treat small cell lung cancer (SCLC) include bendamustine, carboplatin, cisplatin, cyclophosphamide, docetaxel, doxorubicin, etoposide, gemcitabine, ipilimumab, irinotecan, nivolumab, paclitaxel, temozolomide, topotecan, vincristine, vinorelbine, and any combinations thereof.

Melanoma Combination Therapy

Therapeutic agents used to treat melanoma cancer include albumin bound paclitaxel, carboplatin, cisplatin, cobiemtinib, dabrafenib, dacrabazine, IL-2, imatinib, interferon alfa-2b, ipilimumab, nitrosourea, nivolumab, paclitaxel, pembrolizumab, pilimumab, temozolomide, trametinib, vemurafenib, vinblastine, and any combinations thereof.

Ovarian Cancer Combination Therapy

Therapeutic agents used to treat ovarian cancer include 5-flourouracil, albumin bound paclitaxel, altretamine, anastrozole, bevacizumab, capecitabine, carboplatin, cisplatin, cyclophosphamide, docetaxel, doxorubicin, etoposide, exemestane, gemcitabine, ifosfamide, irinotecan, letrozole, leuprolide acetate, liposomal doxorubicin, megestrol acetate, melphalan, olaparib, oxaliplatin, paclitaxel, Pazopanib, pemetrexed, tamoxifen, topotecan, vinorelbine, and any combinations thereof.

Pancreatic Cancer Combination Therapy

Therapeutic agents used to treat pancreatic cancer include 5-fluorourcil, albumin-bound paclitaxel, capecitabine, cisplatin, docetaxel, erlotinib, fluoropyrimidine, gemcitabine, irinotecan, leucovorin, oxaliplatin, paclitaxel, and any combinations thereof.

Renal Cell Carcinoma Combination Therapy

Therapeutic agents used to treat renal cell carcinoma include axitinib, bevacizumab, cabozantinib, erlotinib, everolimus, levantinib, nivolumab, pazopanib, sorafenib, sunitinib, temsirolimus, and any combinations thereof.

Serum Half-Life-Extending Fc Mutations

In some embodiments, the Fc region or Fc domain of the directed antibody comprise amino acid modifications that promote an increased serum half-life of the anti-binding molecule. Mutations that increase the half-life of an antibody have been described. In one embodiment, the Fc region or Fc domain of one or both of the CD3-targeting heavy chain and the HIV antigen-targeting heavy chain comprise a methionine to tyrosine substitution at position 252 (EU numbering), a serine to threonine substitution at position 254 (EU numbering), and a threonine to glutamic acid substitution at position 256 (EU numbering). See, e.g., U.S. Pat. No. 7,658,921. This type of mutant, designated as a "YTE mutant" exhibits a four-fold increased half-life relative to wild-type versions of the same antibody (Dall'Acqua, et al., J Biol Chem, 281: 23514-24 (2006); Robbie, et al., Antimicrob Agents Chemotherap., 57(12):6147-6153 (2013)). In certain embodiments, the Fc region or Fc domain of one or both of the CD3-targeting heavy chain and the HIV antigen-targeting heavy chain comprise an IgG constant domain comprising one, two, three or more amino acid substitutions of amino acid residues at positions 251-257, 285-290, 308-314, 385-389, and 428-436 (EU numbering). Alternatively, M428L and N434S ("LS") substitutions can increase the pharmacokinetic half-life of the multi-specific antigen binding molecule. In other embodiments, the Fc region or Fc domain of one or both of the CD3-targeting heavy chain and the HIV antigen-targeting heavy chain comprise a M428L and N434S substitution (EU numbering). In other embodiments, the Fc region or Fc domain of one or both of the CD3-targeting heavy chain and the HIV antigen-targeting heavy chain comprise T250Q and M428L (EU numbering) mutations. In other embodiments, the Fc region or Fc domain of one or both of the CD3-targeting heavy chain and the HIV antigen-targeting heavy chain comprise H433K and N434F (EU numbering) mutations.

Effector Enhancing Fc Mutations

In some embodiments, the Fc region or Fe domain of the antibody comprise post-translational and/or amino acid modifications that increase effector activity, e.g., have improved FcγIIIa binding and increased antibody-dependent cellular cytotoxicity (ADCC). In some embodiments, the Fc region or Fe domain of the antibody comprises DE modifications (i.e., S239D and 1332E by EU numbering) in the Fc region. In some embodiments, the Fc region or Fe domain of the antibody comprises DEL modifications (i.e., S239D, 1332E and A330L by EU numbering) in the Fc region. In some embodiments, the Fc region or Fe domain of the antibody comprises DEA modifications (i.e., S239D, 1332E and G236A by EU numbering) in the Fc region. In some embodiments, the Fc region or Fe domain of the antibody comprises DEAL modifications (i.e., S239D, 1332E, G236A and A330L by EU numbering) in the Fc region. See, e.g., U.S. Pat. Nos. 7,317,091; 7,662,925; 8,039,592; 8,093,357; 8,093,359; 8,383,109; 8,388,955; 8,735,545; 8,858,937; 8,937,158; 9,040,041; 9,353,187; 10,184,000; and 10,584,176. Additional amino acid modifications that increase effector activity, e.g., have improved FcγIIIa binding and increased antibody-dependent cellular cytotoxicity (ADCC) include without limitation (EU numbering) F243L/R292P/Y300L/V305I/P396L; S298A/E333A/K334A; or L234Y/L235Q/G236W/S239M/H268D/D270E/S298A on a first Fe domain and D270E/K326D/A330M/K334E on a second Fe domain. Amino acid mutations that increase C1q binding and complement-dependent cytotoxicity (CDC) include without limitation (EU numbering) S267E/H268F/S324T or K326W/E333S. Fc region mutations that enhance effector activity are reviewed in, e.g., Wang, et al., *Protein Cell* (2018) 9(1): 63-73; and Saunders, *Front Immunol*. (2019) 10:1296.

In other embodiments, the antibody or antigen-binding fragment thereof has modified glycosylation, which, e.g., may be introduced post-translationally or through genetic engineering. In some embodiments, the antibody or antigen-binding fragment thereof is afucosylated, e.g., at a glycosylation site present in the antibody or antigen-binding fragment thereof. Most approved monoclonal antibodies are of the IgG1 isotype, where two N-linked biantennary complex-type oligosaccharides are bound to the Fc region. The Fc region exercises the effector function of ADCC through its interaction with leukocyte receptors of the FcγR family. Afucosylated monoclonal antibodies are monoclonal antibodies engineered so that the oligosaccharides in the Fc region of the antibody do not have any fucose sugar units.

2. Human Immunodeficiency Virus (HIV)

In some embodiments, the agents described herein are combined with an HIV combination drug. Examples of combination drugs that can be employed with an agent of this disclosure include ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); darunavir, tenofovir alafenamide hemifumarate, emtricitabine, and cobicistat; efavirenz, lamivudine, and tenofovir disoproxil fumarate; lamivudine and tenofovir disoproxil fumarate; tenofovir and lamivudine; tenofovir alafenamide and emtricitabine; tenofovir alafenamide hemifumarate and emtricitabine; tenofovir alafenamide hemifumarate, emtricitabine, and rilpivirine; tenofovir alafenamide hemifumarate, emtricitabine, cobicistat, and elvitegravir; COMBIVIR® (zidovudine and lamivudine; AZT+3TC); EPZICOM® (LIVEXA®; abacavir sulfate and lamivudine; ABC+3TC); KALETRA® (ALUVIA®; lopinavir and ritonavir); TRIUMEQ® (dolutegravir, abacavir, and lamivudine); BIKTARVY (bictegravir+emtricitabine+tenofovir alafenamide), DOVATO, TRIZIVIR® (abacavir sulfate, zidovudine, and lamivudine; ABC+AZT+3TC); atazanavir and cobicistat; atazanavir sulfate and cobicistat; atazanavir sulfate and ritonavir; darunavir and cobicistat; dolutegravir and rilpivirine; dolutegravir and rilpivirine hydrochloride; dolutegravir, abacavir sulfate, and lamivudine; lamivudine, nevirapine, and zidovudine; raltegravir and lamivudine; doravirine, lamivudine, and tenofovir disoproxil fumarate; doravirine, lamivudine, and tenofovir disoproxil; dolutegravir+lamivudine, lamivudine+abacavir+zidovudine, lamivudine+abacavir, lamivudine+tenofovir disoproxil fumarate, lamivudine+zidovudine+nevirapine, lopinavir+ritonavir, lopinavir+ritonavir+abacavir+lamivudine, lopinavir+ritonavir+zidovudine+lamivudine, tenofovir+lamivudine, and tenofovir disoproxil fumarate+emtricitabine+rilpivirine hydrochloride, lopinavir, ritonavir, zidovudine and lamivudine; cabotegravir+rilpivirine; elpida (elsulfavirine; VM-1500; VM-1500A).

Examples of other drugs for treating HIV that can be combined with an agent of this disclosure include acemannan, alisporivir, BanLec, deferiprone, Gamimune, metenkefalin, naltrexone, Prolastin, REP 9, RPI-MN, VSSP, Hlviral, SB-728-T, 1,5-dicaffeoylquinic acid, rHIV7-shl-TAR-CCR5RZ, AAV-eCD4-Ig gene therapy, MazF gene therapy, BlockAide, ABX-464, AG-1105, APH-0812, BIT-225, CYT-107, HGTV-43, HPH-116, HS-10234, IMO-3100, IND-02, MK-1376, MK-2048, MK-4250, MK-8507, MK-8591, NOV-205, PA-1050040 (PA-040), PGN-007, SCY-635, SB-9200, SCB-719, TR-452, TEV-90110, TEV-90112, TEV-90111, TEV-90113, RN-18, Immuglo, and VIR-576.

HIV Protease Inhibitors

In some embodiments, the agents described herein are combined with an HIV protease inhibitor. Examples of HIV protease inhibitors that can be combined with an agent of this disclosure include amprenavir, atazanavir, brecanavir, darunavir, fosamprenavir, fosamprenavir calcium, indinavir, indinavir sulfate, lopinavir, nelfinavir, nelfinavir mesylate, ritonavir, saquinavir, saquinavir mesylate, tipranavir, DG-17, TMB-657 (PPL-100), T-169, BL-008, MK-8122, TMB-607, and TMC-310911.

HIV Reverse Transcriptase Inhibitors

In some embodiments, the agents described herein are combined with a non-nucleoside or non-nucleotide inhibitor. Examples of HIV non-nucleoside or non-nucleotide inhibitors of reverse transcriptase that can be combined with an agent of this disclosure include dapivirine, delavirdine, delavirdine mesylate, doravirine, efavirenz, etravirine, lentinan, nevirapine, rilpivirine, ACC-007, AIC-292, KM-023, PC-1005, and elsulfavirine (VM-1500.).

In some embodiments, the agents described herein are combined with an HIV nucleoside or nucleotide inhibitor. Examples of HIV nucleoside or nucleotide inhibitors of reverse transcriptase that can be combined with an agent of this disclosure include adefovir, adefovir dipivoxil, azvudine, emtricitabine, tenofovir, tenofovir alafenamide, tenofovir alafenamide fumarate, tenofovir alafenamide hemifumarate, tenofovir disoproxil, tenofovir disoproxil fumarate, tenofovir disoproxil hemifumarate, VIDEX® and VIDEX EC® (didanosine, ddI), abacavir, abacavir sulfate, alovudine, apricitabine, censavudine, didanosine, elvucitabine, festinavir, fosalvudine tidoxil, CMX-157, dapivirine, doravirine, etravirine, OCR-5753, tenofovir disoproxil orotate, fozivudine tidoxil, lamivudine, phosphazid, stavudine, zalcitabine, zidovudine, rovafovir etalafenamide (GS-9131), GS-9148, MK-8504, MK-8591, MK-8583, VM-2500 and KP-1461.

HIV Integrase Inhibitors

In some embodiments, the agents described herein are combined with an HIV integrase inhibitor. Examples of HIV integrase inhibitors that can be combined with an agent of this disclosure include elvitegravir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, dolutegravir, JTK-351, bictegravir, AVX-15567, cabotegravir (long-acting injectable), diketo quinolin-4-1 derivatives, integrase-LEDGF inhibitor, ledgins, M-522, M-532, NSC-310217, NSC-371056, NSC-48240, NSC-642710, NSC-699171, NSC-699172, NSC-699173, NSC-699174, stilbenedisulfonic acid, T-169, VM-3500 and cabotegravir.

In some embodiments, the agents described herein are combined with a HIV non-catalytic site, or allosteric, integrase inhibitor (NCINI). Examples of HIV non-catalytic site, or allosteric, integrase inhibitors (NCINI) that can be combined with an agent of this disclosure include CX-05045, CX-05168, and CX-14442.

HIV Entry Inhibitors

In some embodiments, the agents described herein are combined with an HIV entry inhibitor. Examples of HIV entry (fusion) inhibitors that can be combined with an agent of this disclosure include cenicriviroc, CCR5 inhibitors, gp41 inhibitors, CD4 attachment inhibitors, gp120 inhibitors, and CXCR4 inhibitors.

In some embodiments, the agents described herein are combined with a CCR5 inhibitor. Examples of CCR5 inhibitors that can be combined with an agent of this disclosure include aplaviroc, vicriviroc, maraviroc, cenicriviroc, leronlimab (PRO-140), adaptavir (RAP-101), nifeviroc (TD-0232), anti-GP120/CD4 or CCR5 bispecific antibodies, B-07, MB-66, polypeptide C25P, TD-0680, and vMIP (Haimipu).

In some embodiments, the agents described herein are combined with a gp41 inhibitor. Examples of gp41 inhibitors that can be combined with an agent of this disclosure include albuvirtide, enfuvirtide, BMS-986197, enfuvirtide biobetter, enfuvirtide biosimilar, HIV-1 fusion inhibitors (P26-Bapc), ITV-1, ITV-2, ITV-3, ITV-4, PIE-12 trimer and sifuvirtide.

In some embodiments, the agents are combined with a CD4 attachment inhibitor. Examples of CD4 attachment inhibitors that can be combined with an agent of this disclosure include ibalizumab and CADA analogs.

In some embodiments, the agents described herein are combined with a gp120 inhibitor. Examples of gp120 inhibitors that can be combined with an agent of this disclosure include Radha-108 (receptol) 3B3-PE38, BanLec, bentonite-based nanomedicine, fostemsavir tromethamine, IQP-0831, and BMS-663068.

In some embodiments, the agent described herein are combined with a CXCR4 inhibitor. Examples of CXCR4 inhibitors that can be combined with an agent of this disclosure include plerixafor, ALT-1188, N15 peptide, and vMIP (Haimipu).

In some embodiments, the agents described herein are combined with a HIV maturation inhibitor. Examples of HIV maturation inhibitors that can be combined with an agent of this disclosure include BMS-955176, GSK-3640254 and GSK-2838232.

Latency Reversing Agents

In some embodiments, the agents described herein are combined with a latency reversing agent (LRA). Examples of latency reversing agents that can be combined with an agent of this disclosure include toll-like receptor (TLR) agonists (including TLR7 agonists, e.g., GS-9620), histone deacetylase (HDAC) inhibitors, proteasome inhibitors such as velcade, protein kinase C (PKC) activators, Smyd2 inhibitors, BET-bromodomain 4 (BRD4) inhibitors, ionomycin, IAP antagonists (inhibitor of apoptosis proteins, such as APG-1387, LBW-242), SMAC mimetics (including TL32711, LCL161, GDC-0917, HGS1029, AT-406), PMA, SAHA (suberanilohydroxamic acid, or suberoyl, anilide, and hydroxamic acid), NIZ-985, IL-15 modulating antibodies (including IL-15, IL-15 fusion proteins and IL-15 receptor agonists), JQ1, disulfiram, amphotericin B, and ubiquitin inhibitors such as largazole analogs, APH-0812, and GSK-343. Examples of PKC activators include indolactam, prostratin, ingenol B, and DAG-lactones.

Histone Deacetylase (HDAC) Inhibitors

In some embodiments, the agents as described herein are combined with an inhibitor of a histone deacetylase, e.g., histone deacetylase 9 (HDAC9, HD7, HD7b, HD9, HDAC, HDAC7, HDAC7B, HDAC9B, HDAC9FL, HDRP, MITR; Gene ID: 9734). Examples of HDAC inhibitors include without limitation, abexinostat, ACY-241, AR-42, BEBT-908, belinostat, CKD-581, CS-055 (HBI-8000), CUDC-907 (fimepinostat), entinostat, givinostat, mocetinostat, panobinostat, pracinostat, quisinostat (JNJ-26481585), resminostat, ricolinostat, romidepsin, SHP-141, valproic acid (VAL-001), vorinostat, tinostamustine, remetinostat, entinostat.

Capsid Inhibitor

In some embodiments, the agents described herein are combined with a capsid inhibitor. Examples of capsid inhibitors that can be combined with an agent of this disclosure include capsid polymerization inhibitors or capsid disrupting compounds, HIV nucleocapsid p7 (NCp7) inhibitors such as azodicarbonamide, HIV p24 capsid protein inhibitors, GS-6207, GS-CA1, AVI-621, AVI-101, AVI-201, AVI-301, and AVI-CAN1-15 series, and compounds described in this patent (GSK WO2019/087016)

Immune Checkpoint Modulators

In some embodiments, the agents as described herein, are combined with one or more blockers or inhibitors of inhibitory immune checkpoint proteins or receptors and/or with one or more stimulators, activators or agonists of one or more stimulatory immune checkpoint proteins or receptors. Blockade or inhibition of inhibitory immune checkpoints can positively regulate T-cell or NK cell activation and prevent immune escape of infected cells. Activation or stimulation of stimulatory immune check points can augment the effect of immune checkpoint inhibitors in infective therapeutics. In some embodiments, the immune checkpoint proteins or receptors regulate T cell responses (e.g., reviewed in Xu, et al., *J Exp Cin Cancer Res*. (2018) 37:110). In some embodiments, the immune checkpoint proteins or receptors regulate NK cell responses (e.g., reviewed in Davis, et al., *Semin Immunol*. (2017) 31:64-75 and Chiossone, et al., *Nat Rev Immunol*. (2018) 18(11):671-688).

Examples of immune checkpoint proteins or receptors include without limitation CD27, CD70; CD40, CD40LG; CD47, CD48 (SLAMF2), transmembrane and immunoglobulin domain containing 2 (TMIGD2, CD28H), CD84 (LY9B, SLAMF5), CD96, CD160, MS4A1 (CD20), CD244 (SLAMF4); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); natural killer cell cytotoxicity receptor 3 ligand 1 (NCR3LG1, B7H6); HERV-H LTR-associating 2 (HHLA2, B7H7); inducible T cell co-stimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF8 (CD30), TNFSF8 (CD30L); TNFRSF10A (CD261, DR4, TRAILR1), TNFRSF9 (CD137), TNFSF9 (CD137L); TNFRSF10B (CD262, DR5, TRAILR2), TNFRSF10 (TRAIL); TNFRSF14 (HVEM, CD270), TNFSF14 (HVEML); CD272 (B and T lymphocyte associated (BTLA)); TNFRSF17 (BCMA, CD269), TNFSF13B (BAFF); TNFRSF18 (GITR), TNFSF18 (GITRL); MHC class I polypeptide-related sequence A (MICA); MHC class I polypeptide-related sequence B (MICB); CD274 (CD274, PDL1, PD-L1); programmed cell death 1 (PDCD1, PD1, PD-1); cytotoxic T-lymphocyte associated protein 4 (CTLA4, CD152); CD80 (B7-1), CD28; nectin cell adhesion molecule 2 (NECTIN2, CD112); CD226 (DNAM-1); Poliovirus receptor (PVR) cell adhesion molecule (PVR, CD155); PVR related immunoglobulin domain containing (PVRIG, CDI12R); T cell immunoreceptor with Ig and ITIM domains (TIGIT); T cell immunoglobulin and mucin domain containing 4 (TIMD4; TIM4);

hepatitis A virus cellular receptor 2 (HAVCR2, TIMD3, TIM3); galectin 9 (LGALS9); lymphocyte activating 3 (LAG3, CD223); signaling lymphocytic activation molecule family member 1 (SLAMF1, SLAM, CD150); lymphocyte antigen 9 (LY9, CD229, SLAMF3); SLAM family member 6 (SLAMF6, CD352); SLAM family member 7 (SLAMF7, CD319); UL16 binding protein 1 (ULBP1); UL16 binding protein 2 (ULBP2); UL16 binding protein 3 (ULBP3); retinoic acid early transcript 1E (RAET1E; ULBP4); retinoic acid early transcript 1G (RAET1G; ULBP5); retinoic acid early transcript 1L (RAET1L; ULBP6); lymphocyte activating 3 (CD223); killer cell immunoglobulin like receptor, three Ig domains and long cytoplasmic tail 1 (KIR, CD158E1); killer cell lectin like receptor C1 (KLRC1, NKG2A, CD159A); killer cell lectin like receptor K1 (KLRK1, NKG2D, CD314); killer cell lectin like receptor C2 (KLRC2, CD159c, NKG2C); killer cell lectin like receptor C3 (KLRC3, NKG2E); killer cell lectin like receptor C4 (KLRC4, NKG2F); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor D1 (KLRD1); and SLAM family member 7 (SLAMF7).

In some embodiments, the agents described herein, are combined with one or more blockers or inhibitors of one or more T-cell inhibitory immune checkpoint proteins or receptors. Illustrative T-cell inhibitory immune checkpoint proteins or receptors include without limitation CD274 (CD274, PDL1, PD-L1); programmed cell death 1 ligand 2 (PDCD1LG2, PD-L2, CD273); programmed cell death 1 (PDCD1, PD1, PD-1); cytotoxic T-lymphocyte associated protein 4 (CTLA4, CD152); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); TNFRSF14 (HVEM, CD270), TNFSF14 (HVEML); CD272 (B and T lymphocyte associated (BTLA)); PVR related immunoglobulin domain containing (PVRIG, CDI12R); T cell immunoreceptor with Ig and ITIM domains (TIGIT); lymphocyte activating 3 (LAG3, CD223); hepatitis A virus cellular receptor 2 (HAVCR2, TIMD3, TIM3); galectin 9 (LGALS9); killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); and killer cell immunoglobulin like receptor, three Ig domains and long cytoplasmic tail 1 (KIR3DL1). In some embodiments, the agents, as described herein, are combined with one or more agonist or activators of one or more T-cell stimulatory immune checkpoint proteins or receptors. Illustrative T-cell stimulatory immune checkpoint proteins or receptors include without limitation CD27, CD70; CD40, CD40LG; inducible T cell costimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF9 (CD137), TNFSF9 (CD137L); TNFRSF18 (GITR), TNFSF18 (GITRL); CD80 (B7-1), CD28; nectin cell adhesion molecule 2 (NECTIN2, CD112); CD226 (DNAM-1); CD244 (2B4, SLAMF4), Poliovirus receptor (PVR) cell adhesion molecule (PVR, CD155). See, e.g., Xu, et al., *J Exp Clin Cancer Res*. (2018) 37:110.

In some embodiments, the agents as described herein, are combined with one or more blockers or inhibitors of one or more NK-cell inhibitory immune checkpoint proteins or receptors. Illustrative NK-cell inhibitory immune checkpoint proteins or receptors include without limitation killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor C1 (KLRC1, NKG2A, CD159A); and killer cell lectin like receptor D1 (KLRD1, CD94). In some embodiments, the agents as described herein, are combined with one or more agonist or activators of one or more NK-cell stimulatory immune checkpoint proteins or receptors. Illustrative NK-cell stimulatory immune checkpoint proteins or receptors include without limitation CD16, CD226 (DNAM-1); CD244 (2B4, SLAMF4); killer cell lectin like receptor K1 (KLRK1, NKG2D, CD314); SLAM family member 7 (SLAMF7). See, e.g., Davis, et al., *Semin Immunol*. (2017) 31:64-75; Fang, et al., *Semin Immunol*. (2017) 31:37-54; and Chiossone, et al., *Nat Rev Immunol*. (2018) 18(11):671-688.

In some embodiments, the one or more immune checkpoint inhibitors comprises a proteinaceous (e.g., antibody or fragment thereof, or antibody mimetic) inhibitor of PD-L1 (CD274), PD-1 (PDCD1) or CTLA4. In some embodiments, the one or more immune checkpoint inhibitors comprises a small organic molecule inhibitor of PD-L1 (CD274), PD-1 (PDCD1) or CTLA4. In some embodiments, the small molecule inhibitor of CD274 or PDCD1 is selected from the group consisting of GS-4224, GS-4416, INCB086550 and MAX10181. In some embodiments, the small molecule inhibitor of CTLA4 comprises BPI-002.

Examples of inhibitors of CTLA4 that can be co-administered include without limitation ipilimumab, tremelimumab, BMS-986218, AGEN1181, AGEN1884, BMS-986249, MK-1308, REGN-4659, ADU-1604, CS-1002, BCD-145, APL-509, JS-007, BA-3071, ONC-392, AGEN-2041, JHL-1155, KN-044, CG-0161, ATOR-1144, PBI-5D3H5, BPI-002, as well as multi-specific inhibitors FPT-155 (CTLA4/PD-L1/CD28), PF-06936308 (PD-1/CTLA4), MGD-019 (PD-1/CTLA4), KN-046 (PD-1/CTLA4), MEDI-5752 (CTLA4/PD-1), XmAb-20717 (PD-1/CTLA4), and AK-104 (CTLA4/PD-1).

Examples of inhibitors of PD-L1 (CD274) or PD-1 (PDCD1) that can be co-administered include without limitation pembrolizumab, nivolumab, cemiplimab, pidilizumab, AMP-224, MEDI0680 (AMP-514), spartalizumab, atezolizumab, avelumab, durvalumab, BMS-936559, CK-301, PF-06801591, BGB-A317 (tislelizumab), GLS-010 (WBP-3055), AK-103 (HX-008), AK-105, CS-1003, HLX-10, MGA-012, BI-754091, AGEN-2034, JS-001 (toripalimab), JNJ-63723283, genolimzumab (CBT-501), LZM-009, BCD-100, LY-3300054, SHR-1201, SHR-1210 (camrelizumab), Sym-021, ABBV-181, PD1-PIK, BAT-1306, (MSB0010718C), CX-072, CBT-502, TSR-042 (dostarlimab), MSB-2311, JTX-4014, BGB-A333, SHR-1316, CS-1001 (WBP-3155, KN-035, IBI-308 (sintilimab), HLX-20, KL-A167, STI-A1014, STI-A1015 (IMC-001), BCD-135, FAZ-053, TQB-2450, MDX1105-01, GS-4224, GS-4416, INCB086550, MAX10181, as well as multi-specific inhibitors FPT-155 (CTLA4/PD-L1/CD28), PF-06936308 (PD-1/CTLA4), MGD-013 (PD-1/LAG-3), FS-118 (LAG-3/PD-L1) MGD-019 (PD-1/CTLA4), KN-046 (PD-1/CTLA4), MEDI-5752 (CTLA4/PD-1), RO-7121661 (PD-1/TIM-3), XmAb-20717 (PD-1/CTLA4), AK-104 (CTLA4/PD-1), M7824 (PD-L1/TGFβ-EC domain), CA-170 (PD-L1/VISTA), CDX-527 (CD27/PD-L1), LY-3415244 (TIM3/PDL1), and INBRX-105 (4-1BB/PDL1).

In some embodiments, the agents as described herein are combined with anti-TIGIT antibodies, such as BMS-986207, RG-6058, AGEN-1307

TNF Receptor Superfamily (TNFRSF) Member Agonists or Activators

In some embodiments, the agents as described herein are combined with an agonist of one or more TNF receptor superfamily (TNFRSF) members, e.g., an agonist of one or more of TNFRSF1A (NCBI Gene ID: 7132), TNFRSF1B (NCBI Gene ID: 7133), TNFRSF4 (OX40, CD134; NCBI Gene ID: 7293), TNFRSF5 (CD40; NCBI Gene ID: 958), TNFRSF6 (FAS, NCBI Gene ID: 355), TNFRSF7 (CD27, NCBI Gene ID: 939), TNFRSF8 (CD30, NCBI Gene ID: 943), TNFRSF9 (4-1BB, CD137, NCBI Gene ID: 3604), TNFRSF10A (CD261, DR4, TRAILR1, NCBI Gene ID: 8797), TNFRSF10B (CD262, DR5, TRAILR2, NCBI Gene ID: 8795), TNFRSF10C (CD263, TRAILR3, NCBI Gene ID: 8794), TNFRSF10D (CD264, TRAILR4, NCBI Gene ID: 8793), TNFRSF11A (CD265, RANK, NCBI Gene ID: 8792), TNFRSF11B (NCBI Gene ID: 4982), TNFRSF12A (CD266, NCBI Gene ID: 51330), TNFRSF13B (CD267, NCBI Gene ID: 23495), TNFRSF13C (CD268, NCBI Gene ID: 115650), TNFRSF16 (NGFR, CD271, NCBI Gene ID: 4804), TNFRSF17 (BCMA, CD269, NCBI Gene ID: 608), TNFRSF18 (GITR, CD357, NCBI Gene ID: 8784), TNFRSF19 (NCBI Gene ID: 55504), TNFRSF21 (CD358, DR6, NCBI Gene ID: 27242), and TNFRSF25 (DR3, NCBI Gene ID: 8718).

Example anti-TNFRSF4 (OX40) antibodies that can be co-administered include without limitation, MEDI6469, MEDI6383, MEDI0562 (tavolixizumab), MOXR0916, PF-04518600, RG-7888, GSK-3174998, INCAGN1949, BMS-986178, GBR-8383, ABBV-368, and those described in WO2016179517, WO2017096179, WO2017096182, WO2017096281, and WO2018089628.

Example anti-TNFRSF5 (CD40) antibodies that can be co-administered include without limitation RG7876, SEA-CD40, APX-005M and ABBV-428.

In some embodiments, the anti-TNFRSF7 (CD27) antibody varlilumab (CDX-1127) is co-administered.

Example anti-TNFRSF9 (4-1BB, CD137) antibodies that can be co-administered include without limitation urelumab, utomilumab (PF-05082566), AGEN2373 and ADG-106.

Example anti-TNFRSF18 (GITR) antibodies that can be co-administered include without limitation, MEDI1873, FPA-154, INCAGN-1876, TRX-518, BMS-986156, MK-1248, GWN-323, and those described in WO2017096179, WO2017096276, WO2017096189, and WO2018089628. In some embodiments, an antibody, or fragment thereof, co-targeting TNFRSF4 (OX40) and TNFRSF18 (GITR) is co-administered. Such antibodies are described, e.g., in WO2017096179 and WO2018089628.

Bi- and Tri-Specific Natural Killer (NK)-Cell Engagers

In some embodiments, the agents as described herein, are combined with a bi-specific NK-cell engager (BiKE) or a tri-specific NK-cell engager (TriKE) (e.g., not having an Fc) or bi-specific antibody (e.g., having an Fc) against an NK cell activating receptor, e.g., CD16A, C-type lectin receptors (CD94/NKG2C, NKG2D, NKG2E/H and NKG2F), natural cytotoxicity receptors (NKp30, NKp44 and NKp46), killer cell C-type lectin-like receptor (NKp65, NKp8O), Fc receptor FcγR (which mediates antibody-dependent cell cytotoxicity), SLAM family receptors (e.g., 2B4, SLAM6 and SLAM7), killer cell immunoglobulin-like receptors (KIR) (KIR-2DS and KIR-3DS), DNAM-1 and CD137 (41BB). As appropriate, the anti-CD16 binding bi-specific molecules may or may not have an Fc. Illustrative bi-specific NK-cell engagers that can be co-administered target CD16 and one or more HIV-associated antigens as described herein. BiKEs and TriKEs are described, e.g., in Felices, et al., *Methods Mol Biol.* (2016) 1441:333-346; Fang, et al., *Semin Immunol.* (2017) 31:37-54. Examples of a trispecific NK cell engager (TRiKE) include OXS-3550, and CD16-IL-15-B7H3 TriKe.

Indoleamine-Pyrrole-2,3-Dioxygenase (IDO1) Inhibitors

In some embodiments, the agents as described herein, are combined with an inhibitor of indoleamine 2,3-dioxygenase 1 (IDO1; NCBI Gene ID: 3620). Examples of IDO1 inhibitors include without limitation, BLV-0801, epacadostat, F-001287, GBV-1012, GBV-1028, GDC-0919, indoximod, NKTR-218, NLG-919-based vaccine, PF-06840003, pyranonaphthoquinone derivatives (SN-35837), resminostat, SBLK-200802, BMS-986205, and shIDO-ST, EOS-200271, KHK-2455, LY-3381916.

Toll-Like Receptor (TLR) Agonists

In some embodiments, the agents as described herein, are combined with an agonist of a toll-like receptor (TLR), e.g., an agonist of TLR1 (NCBI Gene ID: 7096), TLR2 (NCBI Gene ID: 7097), TLR3 (NCBI Gene ID: 7098), TLR4 (NCBI Gene ID: 7099), TLR5 (NCBI Gene ID: 7100), TLR6 (NCBI Gene ID: 10333), TLR7 (NCBI Gene ID: 51284), TLR8 (NCBI Gene ID: 51311), TLR9 (NCBI Gene ID: 54106), and/or TLR10 (NCBI Gene ID: 81793). Example TLR7 agonists that can be co-administered include without limitation AL-034, DSP-0509, GS-9620 (vesatolimod), LHC-165, TMX-101 (imiquimod), GSK-2245035, resiquimod, DSR-6434, DSP-3025, IMO-4200, MCT-465, MEDI-9197, 3M-051, SB-9922, 3M-052, Limtop, TMX-30X, TMX-202, RG-7863, RG-7854, RG-7795, and the compounds disclosed in US20100143301 (Gilead Sciences), US20110098248 (Gilead Sciences), and US20090047249 (Gilead Sciences), US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics). An TLR7/TLR8 agonist that can be co-administered is NKTR-262, telratolimod and BDB-001. Example TLR8 agonists that can be co-administered include without limitation E-6887, IMO-4200, IMO-8400, IMO-9200, MCT-465, MEDI-9197, motolimod, resiquimod, GS-9688, VTX-1463, VTX-763, 3M-051, 3M-052, and the compounds disclosed in US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics). Example TLR9 agonists that can be co-administered include without limitation AST-008, cobitolimod, CMP-001, IMO-2055, IMO-2125, litenimod, MGN-1601, BB-001, BB-006, IMO-3100, IMO-8400, IR-103, IMO-9200, agatolimod, DIMS-9054, DV-1079, DV-1179, AZD-1419, lefitolimod (MGN-1703), CYT-003, CYT-003-QbG10, tilsotolimod and PUL-042. Examples of TLR3 agonist include rintatolimod, poly-ICLC, RIBOXXON®, Apoxxim, RIBOXXIM®, IPH-33, MCT-465, MCT-475, and ND-1.1. Examples of TLR4 agonist include G-100, and GSK-1795091.

STING Agonists, RIG-I and NOD2 Modulators

In some embodiments, the agents described herein are combined with a stimulator of interferon genes (STING). In some embodiments, the STING receptor agonist or activator is selected from the group consisting of ADU-S100 (MIW-815), SB-11285, MK-1454, SR-8291, AdVCA0848, GSK-532, SYN-STING, MSA-1, SR-8291, 5,6-dimethylxanthenone-4-acetic acid (DMXAA), cyclic-GAMP (cGAMP) and cyclic-di-AMP. In some embodiments, the agents described herein are combined with a RIG-I modulator such as RGT-100, or NOD2 modulator, such as SB-9200, and IR-103.

LAG-3 and TIM-3 Inhibitors

In some embodiments, the agents as described herein are combined with an anti-TIM-3 antibody, such as TSR-022, LY-3321367, MBG-453, INCAGN-2390.

In some embodiments, the antibodies or antigen-binding fragments described herein are combined with an anti LAG-3 (Lymphocyte-activation) antibody, such as relatlimab (ONO-4482), LAG-525, MK-4280, REGN-3767, INCAGN2385.

Interleukin Agonists

In some embodiments, the agents described herein are combined with an interleukin agonist, such as IL-2, IL-7, IL-15, IL-10, IL-12 agonists; examples of IL-2 agonists such as proleukin (aldesleukin, IL-2); pegylated IL-2 (eg NKTR-214); modified variants of IL-2 (eg THOR-707), bempegaldesleukin, AIC-284, ALKS-4230, CUI-101, Neo-2/15; examples of IL-15 agonists, such as ALT-803, NKTR-255, and hetIL-15, interleukin-15/Fc fusion protein, AM-0015, NIZ-985, SO-C101, IL-15 Synthorin (pegylated 11-15), P-22339, and a IL-15-PD-1 fusion protein N-809; examples of IL-7 include CYT-107.

Examples of additional immune-based therapies that can be combined with an agent of this disclosure include interferon alfa; interferon alfa-2b; interferon alfa-n3; pegylated interferon alfa; interferon gamma; Flt3 agonists; gepon; normferon, peginterferon alfa-2a, peginterferon alfa-2b, RPI-MN.

Phosphatidylinositol 3-Kinase (PI3K) Inhibitors

In some embodiments, the agents described herein are combined with a PI3K inhibitor. Examples of PI3K inhibitors that can be combined with an agent of this disclosure include idelalisib, alpelisib, buparlisib, CAI orotate, copanlisib, duvelisib, gedatolisib, neratinib, panulisib, perifosine, pictilisib, pilaralisib, puquitinib mesylate, rigosertib, rigosertib sodium, sonolisib, taselisib, AMG-319, AZD-8186, BAY-1082439, CLR-1401, CLR-457, CUDC-907, DS-7423, EN-3342, GSK-2126458, GSK-2269577, GSK-2636771, INCB-040093, LY-3023414, MLN-1117, PQR-309, RG-7666, RP-6530, RV-1729, SAR-245409, SAR-260301, SF-1126, TGR-1202, UCB-5857, VS-5584, XL-765, and ZSTK-474.

alpha-4/beta-7 Antagonists

In some embodiments, the agents described herein are combined with an alpha-4/beta-7 antagonist. Examples of Integrin alpha-4/beta-7 antagonists that can be combined with an agent of this disclosure include PTG-100, TRK-170, abrilumab, etrolizumab, carotegrast methyl, and vedolizumab.

HIV Targeting Antibodies

Examples of HIV antibodies, bispecific antibodies, and "antibody-like" therapeutic proteins that can be combined with an agent of this disclosure include DARTs®, DUOBODIES®, BITES®, XmAbs®, TandAbs®, Fab derivatives, bNAbs (broadly neutralizing HIV-1 antibodies), TMB-360, and those targeting HIV gp120 or gp41, antibody-Recruiting Molecules targeting HIV, anti-CD63 monoclonal antibodies, anti-GB virus C antibodies, anti-GP120/CD4, CCR5 bispecific antibodies, anti-Nef single domain antibodies, anti-Rev antibody, camelid derived anti-CD18 antibodies, camelid-derived anti-ICAM-1 antibodies, DCVax-001, gp140 targeted antibodies, gp41-based HIV therapeutic antibodies, human recombinant mAbs (PGT-121), ibalizumab, Immuglo, MB-66.

Various bNAbs are known in the art and may be used in this invention. Examples include, but are not limited to, those described in U.S. Pat. Nos. 8,673,307, 9,493,549, 9,783,594, WO2014/063059, WO2012/158948, WO2015/117008, and PCT/US2015/41272, and WO2017/096221, including antibodies 12A12, 12A21, NIH45-46, bANC131, 8ANC134, 1B2530, INC9, 8ANC195. 8ANC196, 10-259, 10-303, 10-410, 10-847, 10-996, 10-1074, 10-1121, 10-1130, 10-1146, 10-1341, 10-1369, and 10-1074GM. Additional examples include those described in Klein et al., Nature, 492(7427): 118-22 (2012), Horwitz et al., Proc Natl Acad Sci USA, 110(41): 16538-43 (2013), Scheid, et al., Science, 333: 1633-1637 (2011), Scheid, et al., Nature, 458:636-640 (2009), Eroshkin et al, Nucleic Acids Res., 42 (Database issue):Dl 133-9 (2014), Mascola et al., Immunol Rev., 254(1):225-44 (2013), such as 2F5, 4E10, M66.6, CAP206-CH12, 10E81 (all of which bind the MPER of gp41); PG9, PG16, CH01-04 (all of which bind V1V2-glycan), 2G12 (which binds to outer domain glycan); b12, HJ16, CH103-106, VRC01-03, VRC-PG04, 04b, VRC-CH30-34, 3BNC62, 3BNC89, 3BNC91, 3BNC95, 3BNC104, 3BNC176, and 8ANC131 (all of which bind to the CD4 binding site).

Additional broadly neutralizing antibodies which can be used as a second therapeutic agent in a combination therapy are described, e.g., in U.S. Pat. Nos. 8,673,307; 9,493,549; 9,783,594; and WO 2012/154312; WO2012/158948; WO 2013/086533; WO 2013/142324; WO2014/063059; WO 2014/089152, WO 2015/048462; WO 2015/103549; WO 2015/117008; WO2016/014484; WO 2016/154003; WO 2016/196975; WO 2016/149710; WO2017/096221; WO 2017/133639; WO 2017/133640, which are hereby incorporated herein by reference in their entireties for all purposes. Additional examples include those described in Sajadi, et al., Cell. (2018) 173(7):1783-1795; Sajadi, et al., J Infect Dis. (2016) 213(1):156-64; Klein et al., Nature, 492(7427): 118-22 (2012), Horwitz et al., Proc Natl Acad Sci USA, 110(41): 16538-43 (2013), Scheid, et al., Science, 333: 1633-1637 (2011), Scheid, et al., Nature, 458:636-640 (2009), Eroshkin et al, Nucleic Acids Res., 42 (Database issue):Dl 133-9 (2014), Mascola et al., Immunol Rev., 254(1):225-44 (2013), such as 2F5, 4E10, M66.6, CAP206-

CH12, 10E8, 10E8v4, 10E8-5R-100cF, DH511.11P, 7b2, and LN01 (all of which bind the MPER of gp41).

Examples of additional antibodies include bavituximab, UB-421, BF520.1, CH01, CH$_{59}$, C2F5, C4E10, C2F5+C2G12+C4E10, 3BNC117, 3BNC117-LS, 3BNC60, DH270.1, DH270.6, D1D2, 10-1074-LS, GS-9722, DH411-2, BG18, PGT145, PGT121, PGT-121.60, PGT-121.66, PGT122, PGT-123, PGT-124, PGT-125, PGT-126, PGT-151, PGT-130, PGT-133, PGT-134, PGT-135, PGT-128, PGT-136, PGT-137, PGT-138, PGT-139, MDX010 (ipilimumab), DH511, DH511-2, N6, N6LS, N49P6, N49P7, N49P7.1, N49P9, N49P11, N60P1.1, N60P25.1, N60P2.1, N60P31.1, N60P22, NIH 45-46, PGC14, PGG14, PGT-142, PGT-143, PGT-144, PGDM1400, PGDM12, PGDM21, PCDN-33A, 2Dm2m, 4Dm2m, 6Dm2m, PGDM1400, MDX010 (ipilimumab), VRC01, VRC-01-LS, A32, 7B2, 10E8, VRC-07-523, VRC07-523LS, VRC24, VRC41.01, 10E8VLS, 3810109, 10E8v4, IMC-HIV, iMabm36, eCD4-Ig, IOMA, CAP256-VRC26.25, DRVIA7, VRC-HIVMAB080-00-AB, VRC-HIVMAB060-00-AB, P2G12, VRC07, 354BG8, 354BG18, 354BG42, 354BG33, 354BG129, 354BG188, 354BG411, 354BG426, VRC29.03, CAP256, CAP256-VRC26.08, CAP256-VRC26.09, CAP256-VRC26.25, PCT64-24E and CAP256-VRC26.25, PCT64-24E and CAP248-2B, 35022, ACS202, VRC34 and VRC34.01, 10E8, 10E8v4, 10E8-5R-100cF, 4E10, DH511.11P, 2F5, 7b2, and LN01.

Example of HIV bispecific and trispecific antibodies include MGD014, B12BiTe, TMB-bispecific, SAR-441236, VRC-01/PGDM-1400/10E8v4, 10E8.4/iMab, 10E8v4/PGT121-VRC01.

Example of in vivo delivered bnabs such as AAV8-VRC07; mRNA encoding anti-HIV antibody VRC01; and engineered B-cells encoding 3BNC117 (Hartweger et al, J. Exp. Med. 2019, 1301).

Pharmacokinetic Enhancers

In some embodiments, the agents described herein are combined with a pharmacokinetic enhancer. Examples of pharmacokinetic enhancers that can be combined with an agent of this disclosure include cobicistat and ritonavir.

Additional Therapeutic Agents

Examples of additional therapeutic agents that can be combined with an agent of this disclosure include the compounds disclosed in WO 2004/096286 (Gilead Sciences), WO 2006/015261 (Gilead Sciences), WO 2006/110157 (Gilead Sciences), WO 2012/003497 (Gilead Sciences), WO 2012/003498 (Gilead Sciences), WO 2012/145728 (Gilead Sciences), WO 2013/006738 (Gilead Sciences), WO 2013/159064 (Gilead Sciences), WO 2014/100323 (Gilead Sciences), US 2013/0165489 (University of Pennsylvania), US 2014/0221378 (Japan Tobacco), US 2014/0221380 (Japan Tobacco), WO 2009/062285 (Boehringer Ingelheim), WO 2010/130034 (Boehringer Ingelheim), WO 2013/006792 (Pharma Resources), US 20140221356 (Gilead Sciences), US 20100143301 (Gilead Sciences) and WO 2013/091096 (Boehringer Ingelheim).

HIV Vaccines

In some embodiments, the agents described herein are combined with an HIV vaccine. Examples of HIV vaccines that can be combined with an agent of this disclosure include peptide vaccines, recombinant subunit protein vaccines, live vector vaccines, DNA vaccines, CD4-derived peptide vaccines, vaccine combinations, adenoviral vector vaccines (an adenoviral vector such as Ad5, Ad26 or Ad35), simian adenovirus (chimpanzee, gorilla, rhesus i.e. rhAd), adeno-associated virus vector vaccines, Chimpanzee adenoviral vaccines (e.g., ChAdOX1, ChAd68, ChAd3, ChAd63, ChAd83, ChAd155, ChAd157, Pan5, Pan6, Pan7, Pan9), Coxsackieviruses based vaccines, enteric virus based vaccines, Gorilla adenovirus vaccines, lentiviral vector based vaccine, arenavirus vaccines (such as LCMV, Pichinde), bi-segmented or tri-segmented arenavirus based vaccine, measles virus based vaccine, flavivirus vector based vaccines, tobacco mosaic virus vector based vaccine, Varicella-zoster virus based vaccine, Human parainfluenza virus 3 (PIV3) based vaccines, poxvirus based vaccine (modified vaccinia virus Ankara (MVA), orthopoxvirus-derived NYVAC, and avipoxvirus-derived ALVAC (canarypox virus) strains); fowlpox virus based vaccine, rhabdovirus-based vaccines, such as VSV and marabavirus; recombinant human CMV (rhCMV) based vaccine, alphavirus-based vaccines, such as semliki forest virus, venezuelan equine encephalitis virus and sindbis virus; (see Lauer, *Clinical and Vaccine Immunology,* 2017, DOI: 10.1128/CVI.00298-16); LNP formulated mRNA based therapeutic vaccines; LNP-formulated self-replicating RNA/self-amplifying RNA vaccines.

Examples of vaccines include: rgp120 (AIDSVAX), ALVAC HIV (vCP1521)/AIDSVAX B/E (gp120) (RV144), monomeric gp120 HIV-1 subtype C vaccine, Remune, ITV-1, Contre Vir, Ad5-ENVA-48, DCVax-001 (CDX-2401), Vacc-4x, Vacc-C5, VAC-3S, multiclade DNA recombinant adenovirus-5 (rAd5), rAd5 gag-pol env A/B/C vaccine, Pennvax-G, Pennvax-GP, Pennvax-G/MVA-CMDR, HIV-TriMix-mRNA vaccine, HIV-LAMP-vax, Ad35, Ad35-GRIN, NAcGM3/VSSP ISA-51, poly-ICLC adjuvanted vaccines, TatImmune, GTU-multiHIV (FIT-06), gp140 [delta]V2.TV1+MF-59, rVSVIN HIV-1 gag vaccine, SeV-Gag vaccine, AT-20, DNK-4, ad35-Grin/ENV, TBC-M4, HIVAX, HIVAX-2, NYVAC-HIV-PT1, NYVAC-HIV-PT4, DNA-HIV-PT123, rAAV1-PG9DP, GOVX-B11, GOVX-B21, TVI-HIV-1, Ad-4 (Ad4-env Clade C+Ad4-mGag), Paxvax, EN41-UGR7C, EN41-FPA2, PreVaxTat, AE-H, MYM-V101, CombiHIVvac, ADVAX, MYM-V201, MVA-CMDR, DNA-Ad5 gag/pol/nef/nev (HVTN505), MVATG-17401, ETV-01, CDX-1401, rcAD26.MOS1.HIV-Env, Ad26.Mod.HIV vaccine, Ad26.Mod.HIV+MVA mosaic vaccine+gp140, AGS-004, AVX-101, AVX-201, PEP-6409, SAV-001, ThV-01, TL-01, TUTI-16, VGX-3300, IHV-001, and virus-like particle vaccines such as pseudovirion vaccine, CombiVICHvac, LFn-p24 B/C fusion vaccine, GTU-based DNA vaccine, HIV gag/pol/nef/env DNA vaccine, anti-TAT HIV vaccine, conjugate polypeptides vaccine, dendritic-cell vaccines (such as DermaVir), gag-based DNA vaccine, GI-2010, gp41 HIV-1 vaccine, HIV vaccine (PIKA adjuvant), i-key/MHC class II epitope hybrid peptide vaccines, ITV-2, ITV-3, ITV-4, LIPO-5, multiclade Env vaccine, MVA vaccine, Pennvax-GP, pp71-deficient HCMV vector HIV gag vaccine, rgp160 HIV vaccine, RNActive HIV vaccine, SCB-703, Tat Oyi vaccine, TBC-M4, UBI HIV gp120, Vacc-4x+romidepsin, variant gp120 polypeptide vaccine, rAd5 gag-pol env A/B/C vaccine, DNA.HTI and MVA.HTI, VRC-HIVDNA016-00-VP+VRC-HIVADV014-00-VP, INO-6145, JNJ-9220, gp145 C.6980; eOD-GT8 60mer based vaccine, PD-201401, env (A, B, C, A/E)/gag (C) DNA Vaccine, gp120 (A,B,C,A/E) protein vaccine, PDPHV-201401, Ad4-EnvCN54, EnvSeq-1 Envs HIV-1 vaccine (GLA-SE adjuvanted), HIV p24gag prime-boost plasmid DNA vaccine, arenavirus vector-based vaccines (Vaxwave, TheraT), MVA-BN HIV-1 vaccine regimen, UBI HIV gp120, mRNA based prophylactic vaccines, and TBL-1203HI.

Birth Control (Contraceptive) Combination Therapy

In some embodiments, the agents described herein are combined with a birth control or contraceptive regimen. Therapeutic agents used for birth control (contraceptive) that can be combined with an agent of this disclosure include cyproterone acetate, desogestrel, dienogest, drospirenone, estradiol valerate, ethinyl Estradiol, ethynodiol, etonogestrel, levomefolate, levonorgestrel, lynestrenol, medroxyprogesterone acetate, mestranol, mifepristone, misoprostol, nomegestrol acetate, norelgestromin, norethindrone, noretynodrel, norgestimate, ormeloxifene, segestersone acetate, ulipristal acetate, and any combinations thereof.

In some embodiments, an agent disclosed herein, or a pharmaceutically acceptable salt thereof, is combined with one, two, three, four or more additional therapeutic agents selected from ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); BIKTARVY (bictegravir+emtricitabine+tenofovir alafenamide), adefovir; adefovir dipivoxil; cobicistat; emtricitabine; tenofovir; tenofovir disoproxil; tenofovir disoproxil fumarate; tenofovir alafenamide; tenofovir alafenamide hemifumarate; TRIUMEQ® (dolutegravir, abacavir, and lamivudine); dolutegravir, abacavir sulfate, and lamivudine; raltegravir; raltegravir and lamivudine; maraviroc; enfuvirtide; ALUVIA® (KALETRA®; lopinavir and ritonavir); COMBIVIR® (zidovudine and lamivudine; AZT+3TC); EPZICOM® (LIVEXA®; abacavir sulfate and lamivudine; ABC+3TC); TRIZIVIR® (abacavir sulfate, zidovudine, and lamivudine; ABC+AZT+3TC); rilpivirine; rilpivirine hydrochloride; atazanavir sulfate and cobicistat; atazanavir and cobicistat; darunavir and cobicistat; atazanavir; atazanavir sulfate; dolutegravir; elvitegravir; ritonavir; atazanavir sulfate and ritonavir; darunavir; lamivudine; prolastin; fosamprenavir; fosamprenavir calcium efavirenz; etravirine; nelfinavir; nelfinavir mesylate; interferon; didanosine; stavudine; indinavir; indinavir sulfate; tenofovir and lamivudine; zidovudine; nevirapine; saquinavir; saquinavir mesylate; aldesleukin; zalcitabine; tipranavir; amprenavir; delavirdine; delavirdine mesylate; Radha-108 (receptol); lamivudine and tenofovir disoproxil fumarate; efavirenz, lamivudine, and tenofovir disoproxil fumarate; phosphazid; lamivudine, nevirapine, and zidovudine; abacavir; and abacavir sulfate.

In some embodiments, an agent disclosed herein, or a pharmaceutical composition thereof, is combined with an HIV nucleoside or nucleotide inhibitor of reverse transcriptase and an HIV non-nucleoside inhibitor of reverse transcriptase. In another specific embodiment, an agent disclosed herein, or a pharmaceutical composition thereof, is combined with an HIV nucleoside or nucleotide inhibitor of reverse transcriptase, and an HIV protease inhibiting compound. In an additional embodiment, an agent disclosed herein, or a pharmaceutical composition thereof, is combined with an HIV nucleoside or nucleotide inhibitor of reverse transcriptase, an HIV non-nucleoside inhibitor of reverse transcriptase, and a pharmacokinetic enhancer. In some embodiments, an agent disclosed herein, or a pharmaceutical composition thereof, is combined with at least one HIV nucleoside inhibitor of reverse transcriptase, an integrase inhibitor, and a pharmacokinetic enhancer. In some embodiments, an agent disclosed herein, or a pharmaceutical composition thereof, is combined with two HIV nucleoside or nucleotide inhibitors of reverse transcriptase.

In some embodiments, an agent disclosed herein, or a pharmaceutical composition thereof, is combined with abacavir sulfate, tenofovir, tenofovir disoproxil, tenofovir disoproxil fumarate, tenofovir disoproxil hemifumarate, tenofovir alafenamide, or tenofovir alafenamide hemifumarate.

In some embodiments, an agent disclosed herein, or a pharmaceutical composition thereof, is combined with tenofovir, tenofovir disoproxil, tenofovir disoproxil fumarate, tenofovir alafenamide, or tenofovir alafenamide hemifumarate.

In some embodiments, an agent disclosed herein, or a pharmaceutical composition thereof, is combined with a first additional therapeutic agent selected from the group consisting of abacavir sulfate, tenofovir, tenofovir disoproxil, tenofovir disoproxil fumarate, tenofovir alafenamide, and tenofovir alafenamide hemifumarate, and a second additional therapeutic agent selected from the group consisting of emtricitabine and lamivudine.

In some embodiments, an agent disclosed herein, or a pharmaceutical composition thereof, is combined with a first additional therapeutic agent selected from the group consisting of tenofovir, tenofovir disoproxil, tenofovir disoproxil fumarate, tenofovir alafenamide, and tenofovir alafenamide hemifumarate, and a second additional therapeutic agent, wherein the second additional therapeutic agent is emtricitabine.

In some embodiments, an agent disclosed herein, or a pharmaceutical composition thereof, is combined with a first additional therapeutic agent (a contraceptive) selected from the group consisting of cyproterone acetate, desogestrel, dienogest, drospirenone, estradiol valerate, ethinyl Estradiol, ethynodiol, etonogestrel, levomefolate, levonorgestrel, lynestrenol, medroxyprogesterone acetate, mestranol, mifepristone, misoprostol, nomegestrol acetate, norelgestromin, norethindrone, noretynodrel, norgestimate, ormeloxifene, segestersone acetate, ulipristal acetate, and any combinations thereof.

Gene Therapy and Cell Therapy

In some embodiments, the agents described herein are combined with a gene or cell therapy regimen. Gene therapy and cell therapy include without limitation the genetic modification to silence a gene; genetic approaches to directly kill the infected cells; the infusion of immune cells designed to replace most of the patient's own immune system to enhance the immune response to infected cells, or activate the patient's own immune system to kill infected cells, or find and kill the infected cells; genetic approaches to modify cellular activity to further alter endogenous immune responsiveness against the infection. Examples of dendritic cell therapy include AGS-004. CCR5 gene editing agents include SB-728T. CCR5 gene inhibitors include Cal-1. In some embodiments, C34-CCR5/C34-CXCR4 expressing CD4-positive T-cells are co-administered with one or more multi-specific antigen binding molecules. In some embodiments, the agents described herein are co-administered with AGT-103-transduced autologous T-cell therapy or AAV-eCD4-Ig gene therapy.

Gene Editors

In some embodiments, the agents described herein are combined with a gene editor, e.g., an HIV targeted gene editor. In some embodiments, the genome editing system can be selected from the group consisting of: a CRISPR/

Cas9 complex, a zinc finger nuclease complex, a TALEN complex, a homing endonucleases complex, and a meganuclease complex. An illustrative HIV targeting CRISPR/Cas9 system includes without limitation EBT-101.

CAR-T-Cell Therapy

In some embodiments, the agents described herein can be co-administered with a population of immune effector cells engineered to express a chimeric antigen receptor (CAR), wherein the CAR comprises an HIV antigen binding domain. The HIV antigen include an HIV envelope protein or a portion thereof, gp120 or a portion thereof, a CD4 binding site on gp120, the CD4-induced binding site on gp120, N glycan on gp120, the V2 of gp120, the membrane proximal region on gp41. The immune effector cell is a T-cell or an NK cell. In some embodiments, the T-cell is a CD4+ T-cell, a CD8+ T-cell, or a combination thereof. Cells can be autologous or allogeneic. Examples of HIV CAR-T include VC-CAR-T, CMV-N6-CART, anti-CD4 CART-cell therapy, CD4 CAR+C34-CXCR4+CCR5 ZFN T-cells, autologous hematopoietic stem cells genetically engineered to express a CD4 CAR and the C46 peptide.

TCR-T-Cell Therapy

In some embodiments, the agents described herein are combined with a population of TCR-T-cells. TCR-T-cells are engineered to target HIV derived peptides present on the surface of virus-infected cells, for example ImmTAV B-Cell Therapy In some embodiments, the antibodies or antigen-binding fragments described herein are combined with a population of B cells genetically modified to express broadly neutralizing antibodies, such as 3BNC117 (Hartweger et al, *J. Exp. Med.* 2019, 1301, Moffett et al., *Sci. Immunol.* 4, eaax0644 (2019) 17 May 2019).

3. Hepatitis B Virus

Examples of other drugs for the treatment of HBV include alpha-hydroxytropolones, amdoxovir, antroquinonol, beta-hydroxycytosine nucleosides, ARB-199, CCC-0975, ccc-R08, elvucitabine, ezetimibe, cyclosporin A, gentiopicrin (gentiopicroside), HH-003, hepalatide, JNJ-56136379, nitazoxanide, birinapant, NJK14047, NOV-205 (molixan, BAM-205), oligotide, mivotilate, feron, GST-HG-131, levamisole, Ka Shu Ning, alloferon, WS-007, Y-101 (Ti Fen Tai), rSIFN-co, PEG-IIFNm, KW-3, BP-Inter-014, oleanolic acid, HepB-nRNA, cTP-5 (rTP-5), HSK-II-2, HEISCO-106-1, HEISCO-106, Hepbama, IBPB-0061A, Hepuyinfen, DasKloster 0014-01, ISA-204, Jiangantai (Ganxikang), MIV-210, OB-AI-004, PF-06, picroside, DasKloster-0039, hepulantai, IMB-2613, TCM-800B, reduced glutathione, RO-6864018, RG-7834, QL-007sofosbuvir, ledipasvir, UB-551, and ZH-2N, and the compounds disclosed in US20150210682, (Roche), US 2016/0122344 (Roche), WO2015173164, WO2016023877, US2015252057A (Roche), WO016128335A1 (Roche), WO16120186A1 (Roche), US2016237090A (Roche), WO016107833A1 (Roche), WO16107832A1 (Roche), US2016176899A (Roche), WO016102438A1 (Roche), WO016012470A1 (Roche), US2016220586A (Roche), and US2015031687A (Roche).

HBV Vaccines

HBV vaccines include both prophylactic and therapeutic vaccines. Examples of HBV prophylactic vaccines include Vaxelis, Hexaxim, Heplisav, Mosquirix, DTwP-HBV vaccine, Bio-Hep-B, D/T/P/HBV/M (LBVP-0101; LBVW-0101), DTwP-Hepb-Hib-IPV vaccine, Heberpenta L, DTwP-HepB-Hib, V-419, CVI-HBV-001, Tetrabhay, hepatitis B prophylactic vaccine (Advax Super D), Hepatrol-07, GSK-223192A, ENGERIX B®, recombinant hepatitis B vaccine (intramuscular, Kangtai Biological Products), recombinant hepatitis B vaccine (Hansenual polymorpha yeast, intramuscular, Hualan Biological Engineering), recombinant hepatitis B surface antigen vaccine, Bimmugen, CARG-101, Euforavac, Eutravac, anrix-DTaP-IPV-Hep B, HBAI-20, Infanrix-DTaP-IPV-Hep B-Hib, Pentabio Vaksin DTP-HB-Hib, Comvac 4, Twinrix, Euvax-B, Tritanrix HB, Infanrix Hep B, Comvax, DTP-Hib-HBV vaccine, DTP-HBV vaccine, Yi Tai, Heberbiovac HB, Trivac HB, GerVax, DTwP-Hep B-Hib vaccine, Bilive, Hepavax-Gene, SUPERVAX, Comvac5, Shanvac-B, Hebsulin, Recombivax HB, Revac B mcf, Revac B+, Fendrix, DTwP-HepB-Hib, DNA-001, Shan5, Shan6, rhHBsAG vaccine, HBI pentavalent vaccine, LBVD, Infanrix HeXa, YS-HBV-001 and DTaP-rHB-Hib vaccine.

Examples of HBV therapeutic vaccines include HBsAG-HBIG complex, ARB-1598, Bio-Hep-B, NASVAC, abi-HB (intravenous), ABX-203, Tetrabhay, GX-110E, GS-4774, peptide vaccine (epsilonPA-44), Hepatrol-07, NASVAC (NASTERAP), IMP-321, BEVAC, Revac B mcf, Revac B+, MGN-1333, KW-2, CVI-HBV-002, AltraHepB, VGX-6200, FP-02, FP-02.2 (HepTcell), NU-500, HBVax, im/TriGrid/antigen vaccine, Mega-CD40L-adjuvanted vaccine, HepB-v, RG7944 (INO-1800), recombinant VLP-based therapeutic vaccine (HBV infection, VLP Biotech), AdTG-17909, AdTG-17910 AdTG-18202, ChronVac-B, TG-1050, VVX-001, GSK-3528869A (ChAd155-hli-HBV+MVA-HBV+Hbc-HBs/AS01B-4), VBI-2601, VTP-300 (ChAdOx1-SIi-HBV-CPmut-TPA-Ssh prime and MVA-SIi-HBV-CPmut-TPA-Ssh boost), MVA-BN, and Lm HBV. HBV Arenavirus vaccines are described, e.g., in WO2017076988 and WO2017198726.

HBV DNA Polymerase Inhibitors

Examples of HBV DNA polymerase inhibitors include adefovir (HEPSERA®), emtricitabine (EMTRIVA®), tenofovir disoproxil fumarate (VIREAD®), tenofovir alafenamide, tenofovir, tenofovir disoproxil, tenofovir alafenamide fumarate, tenofovir alafenamide hemifumarate, tenofovir dipivoxil, tenofovir dipivoxil fumarate, tenofovir octadecyloxyethyl ester, CMX-157, tenofovir exalidex, besifovir, entecavir (BARACLUDE®), entecavir maleate, telbivudine (TYZEKA®), filocilovir, pradefovir, clevudine, ribavirin, lamivudine (EPIVIR-HBV®), phosphazide, famciclovir, fusolin, metacavir, SNC-019754, FMCA, AGX-1009, AR-II-04-26, HIP-1302, tenofovir disoproxil aspartate, tenofovir disoproxil orotate, and HS-10234.

Immunomodulators

Examples of immunomodulators include rintatolimod, imidol hydrochloride, ingaron, dermaVir, plaquenil (hydroxychloroquine), proleukin, hydroxyurea, mycophenolate mofetil (MPA) and its ester derivative mycophenolate mofetil (MMF), JNJ-440, WF-10, AB-452, ribavirin, IL-12, INO-9112, polymer polyethyleneimine (PEI), Gepon, VGV-1, MOR-22, CRV-431, JNJ-0535, TG-1050, ABI-H2158, BMS-936559, GS-9688, RO-7011785, RG-7854, RO-6871765, AIC-649, and IR-103.

Toll-Like Receptor (TLR) Agonists

In some embodiments, the agents as described herein, are combined with an agonist of a toll-like receptor (TLR), e.g., an agonist of TLR1 (NCBI Gene ID: 7096), TLR2 (NCBI Gene ID: 7097), TLR3 (NCBI Gene ID: 7098), TLR4 (NCBI Gene ID: 7099), TLR5 (NCBI Gene ID: 7100), TLR6 (NCBI Gene ID: 10333), TLR7 (NCBI Gene ID: 51284), TLR8 (NCBI Gene ID: 51311), TLR9 (NCBI Gene ID: 54106), and/or TLR10 (NCBI Gene ID: 81793), TLR11, TLR12 and TLR13.

Examples of TLR3 modulators include rintatolimod, poly-ICLC, RIBOXXON®, Apoxxim, RIBOXXIM®, IPH-33, MCT-465, MCT-475 and ND-1.1.

Examples of TLR4 agonist include G-100, and GSK-1795091.

Example TLR7 agonists that can be co-administered include without limitation AL-034, DSP-0509, GS-9620 (vesatolimod), LHC-165, TMX-101 (imiquimod), GSK-2245035, resiquimod, DSR-6434, DSP-3025, IMO-4200, MCT-465, MEDI-9197, 3M-051, SB-9922, 3M-052, Limtop, TMX-30X, TMX-202, RG-7863, RG-7854, RG-7795, and the compounds disclosed in US20100143301 (Gilead Sciences), US20110098248 (Gilead Sciences), and US20090047249 (Gilead Sciences), US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics).

An TLR7/TLR8 agonist that can be co-administered is NKTR-262, telratolimod and BDB-001.

Example TLR8 agonists that can be co-administered include without limitation E-6887, IMO-4200, IMO-8400, IMO-9200, MCT-465, MEDI-9197, motolimod, resiquimod, selgantolimod (GS-9688), VTX-1463, VTX-763, 3M-051, 3M-052, ZG-170607, and the compounds disclosed in US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics), U.S. Pat. No. 9,670,205 (Gilead Sciences, Inc.), US20160289229 (Gilead Sciences, Inc.), WO2017/048727 (Gilead Sciences, Inc.), US20180065938 (Gilead Sciences, Inc.), and US20180086755 (Gilead Sciences, Inc.).

Example TLR9 agonists that can be co-administered include without limitation AST-008, cobitolimod, CMP-001, IMO-2055, IMO-2125, litenimod, MGN-1601, BB-001, BB-006, IMO-3100, IMO-8400, IR-103, IMO-9200, agatolimod, DIMS-9054, DV-1079, DV-1179, AZD-1419, lefitolimod (MGN-1703), CYT-003, CYT-003-QbG10, tilsotolimod and PUL-042.

Examples of TLR7, TLR8 and TLR9 modulators include the compounds disclosed in WO2017047769 (Teika Seiyaku), WO2015014815 (Janssen), WO2018045150 (Gilead Sciences Inc), WO2018045144 (Gilead Sciences Inc), WO2015162075 (Roche), WO2017034986 (University of Kansas), WO2018095426 (Jiangsu Hengrui Medicine Co Ltd), WO2016091698(Roche), WO2016075661 (GaxoSmithKline Biologicals), WO2016180743 (Roche), WO2018089695 (Dynavax Technologies), WO2016055553 (Roche), WO2015168279 (Novartis), WO2016107536 (Medshine Discovery), WO2018086593 (Livo (Shanghai) Pharmaceutical), WO2017106607 (Merck), WO2017061532 (Sumitomo Dainippon Pharma), WO2016023511 (Chia Tai Tianqing Pharmaceutical), WO2017076346 (Chia Tai Tianqing Pharmaceutical), WO2017046112 (Roche), WO2018078149 (Roche), WO2017040233 (3M Co), WO2016141092 (Gilead Sciences), WO2018049089 (BristolMyers Squibb), WO2015057655 (Eisai Co Ltd), WO2017001307 (Roche), WO2018005586 (BristolMyers Squibb), WO0201704023 (3M Co), WO2017163264 (Council of Scientific and Industrial Research (India)), WO2018046460 (GlaxoSmithKline Biologicals), WO2018047081 (Novartis), WO2016142250 (Roche), WO2015168269 (Novartis), WO0201804163 (Roche), WO2018038877 (3M Co), WO2015057659 (Eisai Co Ltd), WO2017202704 (Roche), WO2018026620 (BristolMyers Squibb), WO2016029077 (Janus Biotherapeutics), WO0201803143 (Merck), WO2016096778 (Roche), WO2017190669 (Shanghai De Novo Pharmatech), U.S. Ser. No. 09/884,866 (University of Minnesota), WO2017219931 (Sichuan KelunBiotech Biopharmaceutical), WO2018002319 (Janssen Sciences), WO2017216054 (Roche), WO2017202703 (Roche), WO2017184735 (IFM Therapeutics), WO2017184746 (IFM Therapeutics), WO2015088045 (Takeda Pharmaceutical), WO2017038909 (Takeda Pharmaceutical), WO2015095780 (University of Kansas), WO2015023958 (University of Kansas).

In some embodiments, an agent as described herein is co-administered with a TLR7, TLR8 or TLR9 agonist.

Interferon Alpha Receptor Ligands

Examples of interferon alpha receptor ligands include interferon alpha-2b (INTRON A®), pegylated interferon alpha-2a (PEGASYS®), PEGylated interferon alpha-1b, interferon alpha 1b (HAPGEN®), Veldona, Infradure, Roferon-A, YPEG-interferon alfa-2a (YPEG-rhIFNalpha-2a), P-1101, Algeron, Alfarona, Ingaron (interferon gamma), rSIFN-co (recombinant super compound interferon), Ypeginterferon alfa-2b (YPEG-rhIFNalpha-2b), MOR-22, peginterferon alfa-2b (PEG-INTRON®), Bioferon, Novaferon, Inmutag (Inferon), MULTIFERON®, interferon alfa-n1(HUMOFERON®), interferon beta-1a (AVONEX®), Shaferon, interferon alfa-2b (Axxo), Alfaferone, interferon alfa-2b (BioGeneric Pharma), interferon-alpha 2 (CJ), Laferonum, VIPEG, BLAUFERON-A, BLAUFERON-B, Intermax Alpha, Realdiron, Lanstion, Pegaferon, PDferon-B PDferon-B, interferon alfa-2b (IFN, Laboratorios Bioprofarma), alfainterferona 2b, Kalferon, Pegnano, Feronsure, PegiHep, interferon alfa 2b (Zydus-Cadila), interferon alfa 2a, Optipeg A, Realfa 2B, Reliferon, interferon alfa-2b (Amega), interferon alfa-2b (Virchow), ropeginterferon alfa-2b, rHSA-IFN alpha-2a (recombinant human serum albumin intereferon alpha 2a fusion protein), PEG-IFN-alpha, rHSA-IFN alpha 2b, recombinant human interferon alpha-(1b, 2a, 2b), peginterferon alfa-2b (Amega), peginterferon alfa-2a, Reaferon-EC, Proquiferon, Uniferon, Urifron, interferon alfa-2b (Changchun Institute of Biological Products), Anterferon, Shanferon, Layfferon, Shang Sheng Lei Tai, INTEFEN, SINOGEN, Fukangtai, Pegstat, rHSA-IFN alpha-2b, SFR-9216, and Interapo (Interapa).

Hyaluronidase Inhibitors

Examples of hyaluronidase inhibitors include astodrimer.

Hepatitis B Surface Antigen (HBsAg) Inhibitors

Examples of HBsAg inhibitors include AK-074, HBF-0259, PBHBV-001, PBHBV-2-15, PBHBV-2-1, REP-9AC, REP-9C, REP-9, REP-2139, REP-2139-Ca, REP-2055, REP-2163, REP-2165, REP-2053, REP-2031, REP-006, and REP-9AC'.

Examples of HBsAg secretion inhibitors include BM601, GST-HG-131, AB-452

Cytotoxic T-Lymphocyte-Associated Protein 4 (Ipi4) Inhibitors

Examples of Cytotoxic T-lymphocyte-associated protein 4 (ipi4) inhibitors include AGEN-2041, AGEN-1884, ipilumimab, belatacept, PSI-001, PRS-010, Probody mAbs, tremelimumab, and JHL-1155.

Cyclophilin Inhibitors

Examples of cyclophilin inhibitors include CPI-431-32, EDP-494, OCB-030, SCY-635, NVP-015, NVP-018, NVP-019, STG-175, and the compounds disclosed in U.S. Pat. No. 8,513,184 (Gilead Sciences), US20140030221 (Gilead Sciences), US20130344030 (Gilead Sciences), and US20130344029 (Gilead Sciences).

HBV Viral Entry Inhibitors

Examples of HBV viral entry inhibitors include Myrcludex B.

Antisense Oligonucleotide Targeting Viral mRNA

Examples of antisense oligonucleotide targeting viral mRNA include ISIS-HBVRx, IONIS-HBVRx, IONIS-HBV-LRx, IONIS-GSK6-LRx, GSK-3389404, and RG-6004.

Short Interfering RNAs (siRNA) and ddRNAi

Examples of siRNA include TKM-HBV (TKM-HepB), ALN-HBV, SR-008, HepB-nRNA, ARC-520, ARC-521, ARB-1740, ARB-1467, AB-729, DCR-HBVS, RG-6084 (PD-L1), RG-6217, ALN-HBV-02, JNJ-3989 (ARO-HBV), STSG-0002, ALG-010133, ALG-ASO, LUNAR-HBV and DCR-HBVS (DCR-S219).

Examples of DNA-directed RNA interference (ddRNAi) include BB-HB-331.

Endonuclease Modulators

Examples of endonuclease modulators include PGN-514.

Ribonucleotide Reductase Inhibitors

Examples of inhibitors of ribonucleotide reductase include Trimidox.

Nonnucleoside Reverse Transcriptase Inhibitors

Examples of Nonnucleoside Reverse Transcriptase Inhibitors (NNRTIs) include the compounds disclosed in WO2018118826 (Merck), WO2018080903(Merck), WO2018119013 (Merck), WO2017100108 (Idenix), WO2017027434 (Merck), WO2017007701 (Merck), WO2008005555 (Gilead).

HBV Replication Inhibitors

Examples of hepatitis B virus replication inhibitors include GP-31502, isothiafludine, IQP-HBV, RM-5038, and Xingantie.

Covalently Closed Circular DNA (cccDNA) Inhibitors

Examples of cccDNA inhibitors include BSBI-25, ccc-R08, and CHR-101.

Farnesoid X Receptor Agonist

Examples of farnesoid x receptor agonists include, e.g., EYP-001, GS-9674, EDP-305, MET-409, Tropifexor, AKN-083, RDX-023, BWD-100, LMB-763, INV-3, NTX-023-1, EP-024297 and GS-8670.

Additional HBV Antibodies

Examples of HBV antibodies targeting the surface antigens of the hepatitis B virus include lenvervimab (GC-1102), XTL-17, XTL-19, KN-003, IV Hepabulin SN, VIR-3434, and fully human monoclonal antibody therapy (hepatitis B virus infection, Humabs BioMed).

Examples of HBV antibodies, including monoclonal antibodies and polyclonal antibodies, include Zutectra, Shang Sheng Gan Di, Uman Big (Hepatitis B Hyperimmune), Omri-Hep-B, Nabi-HB, Hepatect CP, HepaGam B, igantibe, Niuliva, CT-P24, hepatitis B immunoglobulin (intravenous, pH4, HBV infection, Shanghai RAAS Blood Products), and Fovepta (BT-088).

Examples of fully human monoclonal antibodies include HBC-34.

Antibodies against HBV viral peptide/major histocompatibility complex (MHC) class I (pMHC) complexes are described, e.g., in Sastry, et al., J Virol. 2011 March; 85(5):1935-42 and in WO2011062562.

CCR2 Chemokine Antagonists

Examples of CCR2 chemokine antagonists include propagermanium.

Thymosin Agonists

Examples of thymosin agonists include Thymalfasin, and recombinant thymosin alpha 1 (GeneScience).

Cytokines

Examples of cytokines include recombinant IL-7, CYT-107, interleukin-2 (IL-2, Immunex), recombinant human interleukin-2 (Shenzhen Neptunus), IL-15, IL-21, IL-24, and celmoleukin.

Interleukin Agonists

In some embodiments, the agents described herein are combined with an interleukin agonist, such as IL-2, IL-7, IL-15, IL-10, IL-12 agonists; examples of IL-2 agonists such as proleukin (aldesleukin, IL-2); pegylated IL-2 (eg NKTR-214); modified variants of IL-2 (eg THOR-707), bempegaldesleukin, AIC-284, ALKS-4230, CUI-101, Neo-2/15; examples of IL-15 agonists, such as ALT-803, NKTR-255, and hetIL-15, interleukin-15/Fc fusion protein, AM-0015, NIZ-985, SO-C101, IL-15 Synthorin (pegylated 11-15), P-22339, and a IL-15-PD-1 fusion protein N-809; examples of IL-7 include CYT-107.

Nucleoprotein Modulators

Nucleoprotein modulators may be either HBV core or capsid protein inhibitors. Examples of nucleoprotein modulators include GS-4882, AB-423, AT-130, ALG-001075, ALG-001024, ALG-000184, EDP-514, GLS4, NVR-1221, NVR-3778, AL-3778, BAY 41-4109, morphothiadine mesilate, ARB-168786, ARB-880, ARB-1820, GST-HG-141, JNJ-379, JNJ-632, RG-7907, GST-HG-141, HEC-72702, KL-060332, AB-506, ABI-H0731, ABI-H3733, JNJ-440, ABI-H2158, CB-HBV-001 and DVR-23.

Examples of capsid inhibitors include the compounds disclosed in US20140275167 (Novira Therapeutics), US20130251673 (Novira Therapeutics), US20140343032 (Roche), WO2014037480 (Roche), US20130267517 (Roche), WO2014131847 (Janssen), WO2014033176 (Janssen), WO2014033170 (Janssen), WO2014033167 (Janssen), WO2015/059212 (Janssen), WO2015118057(Janssen), WO2015011281 (Janssen), WO2014184365 (Janssen), WO2014184350 (Janssen), WO2014161888 (Janssen), WO2013096744 (Novira), US20150225355 (Novira), US20140178337 (Novira), US20150315159 (Novira), US20150197533 (Novira), US20150274652 (Novira), US20150259324, (Novira), US20150132258 (Novira), U.S. Pat. No. 9,181,288 (Novira), WO2014184350 (Janssen), WO2013144129 (Roche), WO2017198744 (Roche), US 20170334882 (Novira), US 20170334898 (Roche), WO2017202798(Roche), WO2017214395 (Enanta), WO2018001944 (Roche), WO2018001952(Roche), WO2018005881 (Novira), WO2018005883 (Novira), WO2018011100(Roche), WO2018011160 (Roche), WO2018011162 (Roche), WO2018011163(Roche), WO2018036941 (Roche), WO2018043747 (Kyoto Univ), US20180065929 (Janssen), WO2016168619 (Indiana University), WO2016195982 (The Penn State Foundation), WO2017001655 (Janssen), WO2017048950 (Assembly Biosciences), WO2017048954 (Assembly Biosciences), WO2017048962 (Assembly Biosciences), US20170121328 (Novira), US20170121329 (Novira).

Examples of transcript inhibitors include the compounds disclosed in WO2017013046 (Roche), WO2017016960 (Roche), WO2017017042 (Roche), WO2017017043 (Roche), WO2017061466 (Toyoma chemicals), WO2016177655 (Roche), WO2016161268 (Enanta). WO2017001853 (Redex Pharma), WO2017211791 (Roche), WO2017216685 (Novartis), WO2017216686 (Novartis), WO2018019297 (Ginkgo Pharma), WO2018022282 (Newave Pharma), US20180030053 (Novartis), WO2018045911 (Zhejiang Pharma).

STING Agonists, RIG-I and NOD2 Modulators

In some embodiments, the agents described herein are combined with a stimulator of interferon genes (STING). In some embodiments, the STING receptor agonist or activator is selected from the group consisting of ADU-S100 (MIW-815), SB-11285, MK-1454, SR-8291, AdVCA0848, STINGVAX, GSK-532, SYN-STING, MSA-1, SR-8291, 5,6-dimethylxanthenone-4-acetic acid (DMXAA), cyclic-GAMP (cGAMP) and cyclic-di-AMP. In some embodiments, the agents described herein are combined with a RIG-I modulator such as RGT-100, or NOD2 modulator, such as SB-9200, and IR-103.

Examples of STING agonists include the compounds disclosed in WO 2018065360 ("Biolog Life Science Institute Forschungslabor und Biochemica-Vertrieb GmbH, Germany), WO 2018009466 (Aduro Biotech), WO 2017186711 (InvivoGen), WO 2017161349 (Immune Sensor), WO 2017106740 (Aduro Biotech), US 20170158724 (Glaxo Smithkline), WO 2017075477 (Aduro Biotech), US 20170044206 (Merck), WO 2014179760 (University of California), WO2018098203 (Janssn), WO2018118665 (Merck), WO2018118664 (Merck), WO2018100558 (Takeda), WO2018067423 (Merck), WO2018060323 (Boehringer).

Retinoic Acid-Inducible Gene 1 Stimulators

Examples of stimulators of retinoic acid-inducible gene 1 include inarigivir soproxil (SB-9200), SB-40, SB-44, ORI-7246, ORI-9350, ORI-7537, ORI-9020, ORI-9198, ORI-7170, and RGT-100.

NOD2 Stimulators

Examples of stimulators of NOD2 include inarigivir soproxil (SB-9200).

Phosphatidylinositol 3-kinase (PI3K) Inhibitors

Examples of PI3K inhibitors include idelalisib, ACP-319, AZD-8186, AZD-8835, buparlisib, CDZ-173, CLR-457, pictilisib, neratinib, rigosertib, rigosertib sodium, EN-3342, TGR-1202, alpelisib, duvelisib, IPI-549, UCB-5857, taselisib, XL-765, gedatolisib, ME-401, VS-5584, copanlisib, CAI orotate, perifosine, RG-7666, GSK-2636771, DS-7423, panulisib, GSK-2269557, GSK-2126458, CUDC-907, PQR-309, INCB-40093, pilaralisib, BAY-1082439, puquitinib mesylate, SAR-245409, AMG-319, RP-6530, ZSTK-474, MLN-1117, SF-1126, RV-1729, sonolisib, LY-3023414, SAR-260301, TAK-117, HMPL-689, tenalisib, voxtalisib, and CLR-1401.

Immune Checkpoint Modulators

In some embodiments, the agents as described herein, are combined with one or more blockers or inhibitors of inhibitory immune checkpoint proteins or receptors and/or with one or more stimulators, activators or agonists of one or more stimulatory immune checkpoint proteins or receptors. Blockade or inhibition of inhibitory immune checkpoints can positively regulate T-cell or NK cell activation and prevent immune escape of infected cells. Activation or stimulation of stimulatory immune check points can augment the effect of immune checkpoint inhibitors in infective therapeutics. In some embodiments, the immune checkpoint proteins or receptors regulate T cell responses (e.g., reviewed in Xu, et al., *J Exp Cin Cancer Res*. (2018) 37:110). In some embodiments, the immune checkpoint proteins or receptors regulate NK cell responses (e.g., reviewed in Davis, et al., *Semin Immunol*. (2017) 31:64-75 and Chiossone, et al., *Nat Rev Immunol*. (2018) 18(11):671-688).

Examples of immune checkpoint proteins or receptors include without limitation CD27, CD70; CD40, CD40LG; CD47, CD48 (SLAMF2), transmembrane and immunoglobulin domain containing 2 (TMIGD2, CD28H), CD84 (LY9B, SLAMF5), CD96, CD160, MS4A1 (CD20), CD244 (SLAMF4); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); natural killer cell cytotoxicity receptor 3 ligand 1 (NCR3LG1, B7H6); HERV-H LTR-associating 2 (HHLA2, B7H7); inducible T cell co-stimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF8 (CD30), TNFSF8 (CD30L); TNFRSF10A (CD261, DR4, TRAILR1), TNFRSF9 (CD137), TNFSF9 (CD137L); TNFRSF10B (CD262, DR5, TRAILR2), TNFRSF10 (TRAIL); TNFRSF14 (HVEM, CD270), TNFSF14 (HVEML); CD272 (B and T lymphocyte associated (BTLA)); TNFRSF17 (BCMA, CD269), TNFSF13B (BAFF); TNFRSF18 (GITR), TNFSF18 (GITRL); MHC class I polypeptide-related sequence A (MICA); MHC class I polypeptide-related sequence B (MICB); CD274 (CD274, PDL1, PD-L1); programmed cell death 1 (PDCD1, PD1, PD-1); cytotoxic T-lymphocyte associated protein 4 (CTLA4, CD152); CD80 (B7-1), CD28; nectin cell adhesion molecule 2 (NECTIN2, CD112); CD226 (DNAM-1); Poliovirus receptor (PVR) cell adhesion molecule (PVR, CD155); PVR related immunoglobulin domain containing (PVRIG, CDI12R); T cell immunoreceptor with Ig and ITIM domains (TIGIT); T cell immunoglobulin and mucin domain containing 4 (TIMD4; TIM4); hepatitis A virus cellular receptor 2 (HAVCR2, TIMD3, TIM3); galectin 9 (LGALS9); lymphocyte activating 3 (LAG3, CD223); signaling lymphocytic activation molecule family member 1 (SLAMF1, SLAM, CD150); lymphocyte antigen 9 (LY9, CD229, SLAMF3); SLAM family member 6 (SLAMF6, CD352); SLAM family member 7 (SLAMF7, CD319); UL16 binding protein 1 (ULBP1); UL16 binding protein 2 (ULBP2); UL16 binding protein 3 (ULBP3); retinoic acid early transcript 1E (RAET1E; ULBP4); retinoic acid early transcript 1G (RAET1G; ULBP5); retinoic acid early transcript 1L (RAET1L; ULBP6); lymphocyte activating 3 (CD223); killer cell immunoglobulin like receptor, three Ig domains and long cytoplasmic tail 1 (KIR, CD158E1); killer cell lectin like receptor C1 (KLRC1, NKG2A, CD159A); killer cell lectin like receptor K1 (KLRK1, NKG2D, CD314); killer cell lectin like receptor C2 (KLRC2, CD159c, NKG2C); killer cell lectin like receptor C3 (KLRC3, NKG2E); killer cell lectin like receptor C4 (KLRC4, NKG2F); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor D1 (KLRD1); and SLAM family member 7 (SLAMF7).

In some embodiments, the agents described herein, are combined with one or more blockers or inhibitors of one or more T-cell inhibitory immune checkpoint proteins or receptors. Illustrative T-cell inhibitory immune checkpoint proteins or receptors include without limitation CD274 (CD274, PDL1, PD-L1); programmed cell death 1 ligand 2 (PDCD1LG2, PD-L2, CD273); programmed cell death 1 (PDCD1, PD1, PD-1); cytotoxic T-lymphocyte associated protein 4 (CTLA4, CD152); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); TNFRSF14 (HVEM, CD270), TNFSF14 (HVEML); CD272 (B and T lymphocyte associated (BTLA)); PVR related immunoglobulin domain containing (PVRIG, CDI12R); T cell immunoreceptor with Ig and ITIM domains (TIGIT); lymphocyte activating 3 (LAG3, CD223); hepatitis A virus cellular receptor 2 (HAVCR2, TIMD3, TIM3); galectin 9 (LGALS9); killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); and killer cell immunoglobulin like receptor, three Ig domains and long cytoplasmic tail 1 (KIR3DL1). In some embodiments, the agents, as described herein, are combined with one or more agonist or activators of one or more T-cell stimulatory immune checkpoint proteins or receptors. Illustrative T-cell stimulatory immune checkpoint proteins or receptors include without limitation CD27, CD70; CD40, CD40LG; inducible T cell costimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF9 (CD137), TNFSF9 (CD137L); TNFRSF18 (GITR), TNFSF18 (GITRL); CD80 (B7-1), CD28; nectin cell adhesion molecule 2 (NECTIN2, CD112); CD226 (DNAM-1); CD244 (2B4, SLAMF4), Poliovirus receptor (PVR) cell adhesion molecule (PVR, CD155). See, e.g., Xu, et al., *J Exp Cin Cancer Res*. (2018) 37:110.

In some embodiments, the agents as described herein, are combined with one or more blockers or inhibitors of one or more NK-cell inhibitory immune checkpoint proteins or receptors. Illustrative NK-cell inhibitory immune checkpoint proteins or receptors include without limitation killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor C1 (KLRC1, NKG2A, CD159A); and killer cell lectin like receptor D1 (KLRD1, CD94). In some embodiments, the agents as described herein, are combined with one or more agonist or activators of one or more NK-cell stimulatory immune checkpoint proteins or receptors.

Illustrative NK-cell stimulatory immune checkpoint proteins or receptors include without limitation CD16, CD226 (DNAM-1); CD244 (2B4, SLAMF4); killer cell lectin like receptor K1 (KLRK1, NKG2D, CD314); SLAM family member 7 (SLAMF7). See, e.g., Davis, et al., *Semin Immu-*

*nol*. (2017) 31:64-75; Fang, et al., *Semin Immunol*. (2017) 31:37-54; and Chiossone, et al., *Nat Rev Immunol*. (2018) 18(11):671-688.

In some embodiments, the one or more immune checkpoint inhibitors comprises a proteinaceous (e.g., antibody or fragment thereof, or antibody mimetic) inhibitor of PD-L1 (CD274), PD-1 (PDCD1) or CTLA4. In some embodiments, the one or more immune checkpoint inhibitors comprises a small organic molecule inhibitor of PD-L1 (CD274), PD-1 (PDCD1) or CTLA4. In some embodiments, the small molecule inhibitor of CD274 or PDCD1 is selected from the group consisting of GS-4224, GS-4416, INCB086550 and MAX10181. In some embodiments, the small molecule inhibitor of CTLA4 comprises BPI-002.

Examples of inhibitors of CTLA4 that can be co-administered include without limitation ipilimumab, tremelimumab, BMS-986218, AGEN1181, AGEN1884, BMS-986249, MK-1308, REGN-4659, ADU-1604, CS-1002, BCD-145, APL-509, JS-007, BA-3071, ONC-392, AGEN-2041, JHL-I155, KN-044, CG-0161, ATOR-1144, PBI-5D3H5, BPI-002, as well as multi-specific inhibitors FPT-155 (CTLA4/PD-L1/CD28), PF-06936308 (PD-1/CTLA4), MGD-019 (PD-1/CTLA4), KN-046 (PD-1/CTLA4), MEDI-5752 (CTLA4/PD-1), XmAb-20717 (PD-1/CTLA4), and AK-104 (CTLA4/PD-1).

Examples of inhibitors of PD-L1 (CD274) or PD-1 (PDCD1) that can be co-administered include without limitation pembrolizumab, nivolumab, cemiplimab, pidilizumab, AMP-224, MED10680 (AMP-514), spartalizumab, atezolizumab, avelumab, durvalumab, ALN-PDL, BMS-936559, CK-301, PF-06801591, BGB-108, BGB-A317 (tislelizumab), GLS-010 (WBP-3055), AK-103 (HX-008), GB-226, AK-105, CS-1003, HLX-10, MGA-012, BI-754091, PDR-001, AGEN-2034, JS-001 (toripalimab), JNJ-63723283, genolimzumab (CBT-501), LZM-009, BCD-100, LY-3300054, SHR-1201, SHR-1210 (camrelizumab), Sym-021, ABBV-181, PD1-PIK, BAT-1306, RO-6084 (PD-L1 antisense oligonucleotide), STI-1110, GX-P2, RG-7446, mDX-400, (MSB0010718C), CX-072, CBT-502, TSR-042 (dostarlimab), MSB-2311, JTX-4014, BGB-A333, SHR-1316, CS-1001 (WBP-3155), MEDI-0680, envafolimab (KN-035), KD-033, KY-1003, IBI-308 (sintilimab), HLX-20, KL-A167, STI-A1014, STI-A1015 (IMC-001), BCD-135, FAZ-053, TQB-2450, MDX1105-01, MSB-0010718C, GS-4224, GS-4416, INCB086550, MAX10181, as well as multi-specific inhibitors FPT-155 (CTLA4/PD-L1/CD28), PF-06936308 (PD-1/CTLA4), MGD-013 (PD-1/LAG-3), FS-118 (LAG-3/PD-L1) MGD-019 (PD-1/CTLA4), KN-046 (PD-1/CTLA4), MEDI-5752 (CTLA4/PD-1), RO-7121661 (PD-1/TIM-3), XmAb-20717 (PD-1/CTLA4), AK-104 (CTLA4/PD-1), M7824 (PD-L1/TGFβ-EC domain), CA-170 (PD-L1/VISTA), CDX-527 (CD27/PD-L1), LY-3415244 (TIM3/PDL1), GNS-1480 (Epidermal growth factor receptor antagonist; Programmed cell death ligand 1 inhibitor), M-7824 (PD-L1/TGF-β bifunctional fusion protein), and INBRX-105 (4-1BB/PDL1).

Examples of PD-1 inhibitors include the compounds disclosed in WO2017112730 (Incyte Corp), WO2017087777(Incyte Corp), WO2017017624, WO2014151634 (BristolMyers Squibb Co), WO0201317322 (BristolMyers Squibb Co), WO2018119286 (Incyte Corp), WO2018119266 (Incyte Corp), WO2018119263(Incyte Corp), WO2018119236 (Incyte Corp), WO2018119221(Incyte Corp), WO2018118848 (BristolMyers Squibb Co), WO20161266460(BristolMyers Squibb Co), WO2017087678 (BristolMyers Squibb Co), WO2016149351 (BristolMyers Squibb Co), WO2015033299 (Aurigene Discovery Technologies Ltd), WO2015179615(Eisai Co Ltd; Eisai Research Institute), WO2017066227(BristolMyers Squibb Co), WO2016142886 (Aurigene Discovery Technologies Ltd), WO2016142852(Aurigene Discovery Technologies Ltd), WO2016142835 (Aurigene Discovery Technologies Ltd; Individual), WO2016142833 (Aurigene Discovery Technologies Ltd), WO2018085750 (BristolMyers Squibb Co), WO2015033303 (Aurigene Discovery Technologies Ltd), WO2017205464 (Incyte Corp), WO2016019232 (3M Co; Individual; Texas A&M University System), WO2015160641 (BristolMyers Squibb Co), WO2017079669 (Incyte Corp), WO2015033301 (Aurigene Discovery Technologies Ltd), WO2015034820 (BristolMyers Squibb Co), WO2018073754 (Aurigene Discovery Technologies Ltd), WO2016077518 (BristolMyers Squibb Co), WO2016057624 (BristolMyers Squibb Co), WO2018044783 (Incyte Corp), WO2016100608 (BristolMyers Squibb Co), WO2016100285 (BristolMyers Squibb Co), WO2016039749 (BristolMyers Squibb Co), WO2015019284 (Cambridge Enterprise Ltd), WO2016142894 (Aurigene Discovery Technologies Ltd), WO2015134605 (BristolMyers Squibb Co), WO2018051255 (Aurigene Discovery Technologies Ltd), WO2018051254 (Aurigene Discovery Technologies Ltd), WO2017222976 (Incyte Corp), WO2017070089 (Incyte Corp), WO2018044963 (BristolMyers Squibb Co), WO2013144704 (Aurigene Discovery Technologies Ltd), WO2018013789 (Incyte Corp), WO2017176608 (BristolMyers Squibb Co), WO2018009505 (BristolMyers Squibb Co), WO2011161699 (Aurigene Discovery Technologies Ltd), WO2015119944 (Incyte Corp; Merck Sharp & Dohme Corp), WO2017192961 (Incyte Corp), WO2017106634 (Incyte Corp), WO2013132317 (Aurigene Discovery Technologies Ltd), WO2012168944 (Aurigene Discovery Technologies Ltd), WO2015036927 (Aurigene Discovery Technologies Ltd), WO2015044900 (Aurigene Discovery Technologies Ltd), WO2018026971 (Arising International).

In some embodiments, the agents as described herein are combined with anti-TIGIT antibodies, such as BMS-986207, RG-6058, AGEN-1307.

TNF Receptor Superfamily (TNFRSF) Member Agonists or Activators

In some embodiments, the agents as described herein are combined with an agonist of one or more TNF receptor superfamily (TNFRSF) members, e.g., an agonist of one or more of TNFRSF1A (NCBI Gene ID: 7132), TNFRSF1B (NCBI Gene ID: 7133), TNFRSF4 (OX40, CD134; NCBI Gene ID: 7293), TNFRSF5 (CD40; NCBI Gene ID: 958), TNFRSF6 (FAS, NCBI Gene ID: 355), TNFRSF7 (CD27, NCBI Gene ID: 939), TNFRSF8 (CD30, NCBI Gene ID: 943), TNFRSF9 (4-1BB, CD137, NCBI Gene ID: 3604), TNFRSF10A (CD261, DR4, TRAILR1, NCBI Gene ID: 8797), TNFRSF10B (CD262, DR5, TRAILR2, NCBI Gene ID: 8795), TNFRSF10C (CD263, TRAILR3, NCBI Gene ID: 8794), TNFRSF10D (CD264, TRAILR4, NCBI Gene ID: 8793), TNFRSF11A (CD265, RANK, NCBI Gene ID: 8792), TNFRSF11B (NCBI Gene ID: 4982), TNFRSF12A (CD266, NCBI Gene ID: 51330), TNFRSF13B (CD267, NCBI Gene ID: 23495), TNFRSF13C (CD268, NCBI Gene ID: 115650), TNFRSF16 (NGFR, CD271, NCBI Gene ID: 4804), TNFRSF17 (BCMA, CD269, NCBI Gene ID: 608), TNFRSF18 (GITR, CD357, NCBI Gene ID: 8784), TNFRSF19 (NCBI Gene ID: 55504), TNFRSF21 (CD358, DR6, NCBI Gene ID: 27242), and TNFRSF25 (DR3, NCBI Gene ID: 8718).

Example anti-TNFRSF4 (OX40) antibodies that can be co-administered include without limitation, MEDI6469, MEDI6383, MEDI0562 (tavolixizumab), MOXR0916, PF-04518600, RG-7888, GSK-3174998, INCAGN1949, BMS-986178, GBR-8383, ABBV-368, IBI-101 and those described in WO2016179517, WO2017096179, WO2017096182, WO2017096281, and WO2018089628.

Example anti-TNFRSF5 (CD40) antibodies that can be co-administered include without limitation RG7876, SEA-CD40, APX-005M and ABBV-428.

In some embodiments, the anti-TNFRSF7 (CD27) antibody varlilumab (CDX-1127) is co-administered.

Example anti-TNFRSF9 (4-1BB, CD137) antibodies that can be co-administered include without limitation urelumab, utomilumab (PF-05082566), AGEN2373 and ADG-106.

Example anti-TNFRSF18 (GITR) antibodies that can be co-administered include without limitation, MEDI1873, FPA-154, INCAGN-1876, TRX-518, BMS-986156, MK-1248, GWN-323, and those described in WO2017096179, WO2017096276, WO2017096189, and WO2018089628. In some embodiments, an antibody, or fragment thereof, co-targeting TNFRSF4 (OX40) and TNFRSF18 (GITR) is co-administered. Such antibodies are described, e.g., in WO2017096179 and WO2018089628.

Indoleamine-Pyrrole-2,3-Dioxygenase (IDO1) Inhibitors

In some embodiments, the agents as described herein, are combined with an inhibitor of indoleamine 2,3-dioxygenase 1 (IDO1; NCBI Gene ID: 3620). Examples of IDO1 inhibitors include without limitation, BLV-0801, epacadostat, resminostat, F-001287, GBV-1012, GBV-1028, GDC-0919, indoximod, NKTR-218, NLG-919-based vaccine, PF-06840003, pyranonaphthoquinone derivatives (SN-35837), SBLK-200802, BMS-986205, and shIDO-ST, EOS-200271, KHK-2455, LY-3381916, and the compounds disclosed in US20100015178 (Incyte), US2016137652 (Flexus Biosciences, Inc.), WO2014073738 (Flexus Biosciences, Inc.), and WO2015188085(Flexus Biosciences, Inc.).

LAG-3 and TIM-3 Inhibitors

In some embodiments, the agents as described herein are combined with an anti-TIM-3 antibody, such as TSR-022, LY-3321367, MBG-453, INCAGN-2390.

In some embodiments, the antibodies or antigen-binding fragments described herein are combined with an anti LAG-3 (Lymphocyte-activation) antibody, such as relatlimab (ONO-4482), LAG-525, MK-4280, REGN-3767, INCAGN2385.

Examples of additional immune-based therapies that can be combined with an agent of this disclosure include interferon alfa; interferon alfa-2b; interferon alfa-n3; pegylated interferon alfa; interferon gamma; Flt3 agonists; gepon; normferon, peginterferon alfa-2a, peginterferon alfa-2b, RPI-MN.

Inhibitor of Apoptosis Proteins Family Proteins (IAPs)

Examples of IAP inhibitors include APG-1387.

Recombinant Thymosin Alpha-1

Examples of recombinant thymosin alpha-1 include NL-004 and PEGylated thymosin alpha-1.

Bruton's Tyrosine Kinase (BTK) Inhibitors

Examples of BTK inhibitors include ABBV-105, acalabrutinib (ACP-196), ARQ-531, BMS-986142, dasatinib, ibrutinib, GDC-0853, PRN-1008, SNS-062, ONO-4059, BGB-3111, ML-319, MSC-2364447, RDX-022, X-022, AC-058, RG-7845, spebrutinib, TAS-5315, TP-0158, TP-4207, HM-71224, KBP-7536, M-2951, TAK-020, AC-0025, and the compounds disclosed in US20140330015 (Ono Pharmaceutical), US20130079327 (Ono Pharmaceutical), and US20130217880 (Ono Pharmaceutical).

KDM Inhibitors

Examples of KDM5 inhibitors include the compounds disclosed in WO2016057924 (Genentech/Constellation Pharmaceuticals), US20140275092 (Genentech/Constellation Pharmaceuticals), US20140371195 (Epitherapeutics), US20140371214 (Epitherapeutics), US20160102096 (Epitherapeutics), US20140194469 (Quanticel), US20140171432, US20140213591 (Quanticel), US20160039808 (Quanticel), US20140275084 (Quanticel), and WO2014164708 (Quanticel).

Examples of KDM1 inhibitors include the compounds disclosed in U.S. Pat. No. 9,186,337B2 (Oryzon Genomics), GSK-2879552, RG-6016, and ORY-2001.

Arginase Inhibitors

Examples of Arginase inhibitors include CB-1158, C-201, and resminostat.

Bi- and Tri-Specific Natural Killer (NK)-Cell Engagers

In some embodiments, the agents as described herein, are combined with a bi-specific NK-cell engager (BiKE) or a tri-specific NK-cell engager (TriKE) (e.g., not having an Fc) or bi-specific antibody (e.g., having an Fc) against an NK cell activating receptor, e.g., CD16A, C-type lectin receptors (CD94/NKG2C, NKG2D, NKG2E/H and NKG2F), natural cytotoxicity receptors (NKp30, NKp44 and NKp46), killer cell C-type lectin-like receptor (NKp65, NKp80), Fc receptor FcγR (which mediates antibody-dependent cell cytotoxicity), SLAM family receptors (e.g., 2B4, SLAM6 and SLAM7), killer cell immunoglobulin-like receptors (KIR) (KIR-2DS and KIR-3DS), DNAM-1 and CD137 (41BB). As appropriate, the anti-CD16 binding bi-specific molecules may or may not have an Fc. Illustrative bi-specific NK-cell engagers that can be co-administered target CD16 and one or more HBV-associated antigens as described herein. BiKEs and TriKEs are described, e.g., in Felices, et al., *Methods Mol Biol*. (2016) 1441:333-346; Fang, et al., *Semin Immunol*. (2017) 31:37-54.

Long Acting Treatments

Long acting entecavir (subcutaneous depot), long acting tenofovir (TFD and TAF) implants (devices) or subcutaneous depot. An example of long acting entecavir is described in Exploration of long-acting implant formulations of hepatitis B drug entecavir., Eur J Pharm Sci. 2019 Aug. 1; 136:104958;

Gene Therapy and Cell Therapy

In some embodiments, the agents described herein are combined with a gene or cell therapy regimen. Gene therapy and cell therapy include without limitation the genetic modification to silence a gene; genetic approaches to directly kill the infected cells; the infusion of immune cells designed to replace most of the patient's own immune system to enhance the immune response to infected cells, or activate the patient's own immune system to kill infected cells, or find and kill the infected cells; genetic approaches to modify cellular activity to further alter endogenous immune responsiveness against the infection.

Gene Editors

The genome editing system is selected from the group consisting of: a CRISPR/Cas9 system, a zinc finger nuclease system, a TALEN system, a homing endonucleases system, and a meganuclease system (e.g., an ARCUS system); e.g., cccDNA elimination via targeted cleavage, and altering one or more of the hepatitis B virus (HBV) viral genes. Altering (e.g., knocking out and/or knocking down) the PreC, C, X PreSI, PreS2, S, P or SP gene refers to (1) reducing or eliminating PreC, C, X PreSI, PreS2, S, P or SP gene expression, (2) interfering with Precore, Core, X protein, Long surface protein, middle surface protein, S protein (also known as HBs antigen and HBsAg), polymerase protein, and/or Hepatitis B spliced protein function (HBe, HBc, HBx, PreS1, PreS2, S, Pol, and/or HBSP or (3) reducing or eliminating the intracellular, serum and/or intraparenchymal levels of HBe, HBc, HBx, LHBs, MHBs, SHBs, Pol, and/or HBSP proteins. Knockdown of one or more of the PreC, C, X PreSI, PreS2, S, P and/or SP gene(s) is performed by targeting the gene(s) within HBV cccDNA and/or integrated HBV DNA.

Example of gene therapy, such as liver targeted anti-HBV gene therapy (using ARCUS technology), or using CRISPR/Cas9 gene editing technology, or EBT-106 (LNP-delivered CRISPR/CasX nuclease.

CAR-T Cell Therapy

CAR-T cell therapy includes a population of immune effector cells engineered to express a chimeric antigen receptor (CAR), wherein the CAR includes an HBV antigen-binding domain. In some embodiments, the antigen-binding domain is a domain disclosed herein. In some embodiments, the antigen-binding domain is other than a domain disclosed herein. In some embodiments, the antigen is HBsAg (i.e. HbsAg-CART). The immune effector cell is a T-cell or an NK cell. In some embodiments, the T-cell is a CD4+ T-cell, a CD8+ T-cell, a NK cell or a combination thereof. Cells can be autologous or allogeneic. An example of a CART directed to HBV is described in Cytotherapy. 2018 May; 20(5):697-705. doi: 10.1016/j.jcyt.2018.02.

TCR-T Cell Therapy

TCR-T cell therapy includes T cells expressing HBV-specific T cell receptors. TCR-T cells are engineered to target HBV derived peptides presented on the surface of virus-infected cells. An example of a TCR directed to HBV is described in Wisskirchen, K. et al. T cell receptor grafting allows virological control of hepatitis B virus infection. J Clin Invest. 2019; 129(7):2932-2945.

TCR-T cell therapy includes T-Cells expressing HBV surface antigen (HBsAg)-specific TCR.

TCR-T cell therapy includes TCR-T therapy directed to treatment of HBV, such as LTCR-H2-1.

In another specific embodiment, an agent disclosed herein, or a pharmaceutically acceptable salt thereof, is combined with an HBV DNA polymerase inhibitor, one or two additional therapeutic agents selected from the group consisting of immunomodulators, TLR modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, P13K inhibitors, IDO inhibitors, and stimulators of NOD2, and one or two additional therapeutic agents selected from the group consisting of HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators).

In another specific embodiment, an agent disclosed herein, or a pharmaceutically acceptable salt thereof, is combined with at least a second additional therapeutic agent selected from the group consisting of: HBV DNA polymerase inhibitors, immunomodulator, TLR modulators, HBsAg inhibitors, HBV therapeutic vaccines, HBV antibodies including HBV antibodies targeting the surface antigens of the hepatitis B virus and bispecific antibodies and "antibody-like" therapeutic proteins (such as DARPins®, anti-pMHC TCR-like antibodies, DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2.

In another specific embodiment, an agent disclosed herein, or a pharmaceutically acceptable salt thereof, is combined with at least a second additional therapeutic agent selected from the group consisting of: HBV DNA polymerase inhibitors, HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein inhibitors).

In a particular embodiment, an agent disclosed herein, or a pharmaceutically acceptable salt thereof, is combined with compounds such as those disclosed in U.S. Publication No. 2010/0143301 (Gilead Sciences), U.S. Publication No. 2011/0098248 (Gilead Sciences), U.S. Publication No. 2009/0047249 (Gilead Sciences), U.S. Pat. No. 8,722,054 (Gilead Sciences), U.S. Publication No. 2014/0045849 (Janssen), U.S. Publication No. 2014/0073642 (Janssen), WO2014/056953 (Janssen), WO2014/076221 (Janssen), WO2014/128189 (Janssen), U.S. Publication No. 2014/0350031 (Janssen), WO2014/023813 (Janssen), U.S. Publication No. 2008/0234251 (Array Biopharma), U.S. Publication No. 2008/0306050 (Array Biopharma), U.S. Publication No. 2010/0029585 (Ventirx Pharma), U.S. Publication No. 2011/0092485 (Ventirx Pharma), US2011/0118235 (Ventirx Pharma), U.S. Publication No. 2012/0082658 (Ventirx Pharma), U.S. Publication No. 2012/0219615 (Ventirx Pharma), U.S. Publication No. 2014/0066432 (Ventirx Pharma), U.S. Publication No. 2014/0088085 (Ventirx Pharma), U.S. Publication No. 2014/0275167 (Novira Therapeutics), U.S. Publication No. 2013/0251673 (Novira Therapeutics), U.S. Pat. No. 8,513,184 (Gilead Sciences), U.S. Publication No. 2014/0030221 (Gilead Sciences), U.S. Publication No. 2013/0344030 (Gilead Sciences), U.S. Publication No. 2013/0344029 (Gilead Sciences), US20140275167 (Novira Therapeutics), US20130251673 (Novira Therapeutics), U.S. Publication No. 2014/0343032 (Roche), WO2014037480 (Roche), U.S. Publication No. 2013/0267517 (Roche), WO2014131847 (Janssen), WO2014033176 (Janssen), WO2014033170 (Janssen), WO2014033167 (Janssen), WO2015/059212 (Janssen), WO2015118057(Janssen), WO2015011281 (Janssen), WO2014184365 (Janssen), WO2014184350 (Janssen), WO2014161888 (Janssen), WO2013096744 (Novira), US20150225355 (Novira), US20140178337 (Novira), US20150315159 (Novira), US20150197533 (Novira), US20150274652 (Novira), US20150259324, (Novira), US20150132258 (Novira), U.S. Pat. No. 9,181,288 (Novira), WO2014184350 (Janssen), WO2013144129 (Roche), US20100015178 (Incyte), US2016137652 (Flexus Biosciences, Inc.), WO2014073738 (Flexus Biosciences, Inc.), WO2015188085(Flexus Biosciences, Inc.), U.S. Publication No. 2014/0330015 (Ono Pharmaceutical), U.S. Publication No. 2013/0079327 (Ono Pharmaceutical), U.S. Publication No. 2013/0217880 (Ono pharmaceutical), WO2016057924 (Genentech/Constellation Pharmaceuticals), US20140275092 (Genentech/Constellation Pharmaceuticals), US20140371195 (Epitherapeutics) and US20140371214 (Epitherapeutics). US20160102096 (Epitherapeutics), US20140194469 (Quanticel), US20140171432, US20140213591 (Quanticel), US20160039808 (Quanticel), US20140275084 (Quanticel), WO2014164708 (Quanticel), U.S. Pat. No. 9,186,337B2 (Oryzon Genomics), and other drugs for treating HBV, and combinations thereof.

In some embodiments, an agent disclosed herein, or a pharmaceutically acceptable salt thereof, is combined with 5-30 mg tenofovir alafenamide fumarate, tenofovir alafenamide hemifumarate, or tenofovir alafenamide. In some embodiments, an agent disclosed herein, or a pharmaceutically acceptable salt thereof, is combined with 5-10; 5-15; 5-20; 5-25; 25-30; 20-30; 15-30; or 10-30 mg tenofovir alafenamide fumarate, tenofovir alafenamide hemifumarate, or tenofovir alafenamide. In some embodiments, an agent disclosed herein, or a pharmaceutically acceptable salt thereof, is combined with 10 mg tenofovir alafenamide fumarate, tenofovir alafenamide hemifumarate, or tenofovir alafenamide. In some embodiments, an agent disclosed herein, or a pharmaceutically acceptable salt thereof, is combined with 25 mg tenofovir alafenamide fumarate, tenofovir alafenamide hemifumarate, or tenofovir alafenamide. An agent as disclosed herein may be combined with the agents provided herein in any dosage amount of the compound (e.g., from 50 mg to 500 mg of compound) the same as if each combination of dosages were specifically and individually listed.

In some embodiments, an agent disclosed herein, or a pharmaceutically acceptable salt thereof, is combined with 100-400 mg tenofovir disoproxil fumarate, tenofovir disoproxil hemifumarate, or tenofovir disoproxil. In some embodiments, an agent disclosed herein, or a pharmaceutically acceptable salt thereof, is combined with 100-150; 100-200, 100-250; 100-300; 100-350; 150-200; 150-250; 150-300; 150-350; 150-400; 200-250; 200-300; 200-350; 200-400; 250-350; 250-400; 350-400 or 300-400 mg tenofovir disoproxil fumarate, tenofovir disoproxil hemifumarate, or tenofovir disoproxil. In some embodiments, an agent disclosed herein, or a pharmaceutically acceptable salt thereof, is combined with 300 mg tenofovir disoproxil fumarate, tenofovir disoproxil hemifumarate, or tenofovir disoproxil. In some embodiments, an agent disclosed herein, or a pharmaceutically acceptable salt thereof, is combined with 250 mg tenofovir disoproxil fumarate, tenofovir disoproxil hemifumarate, or tenofovir disoproxil. In some embodiments, an agent herein, or a pharmaceutically acceptable salt thereof, is combined with 150 mg tenofovir disoproxil fumarate, tenofovir disoproxil hemifumarate, or tenofovir disoproxil. An agent as disclosed herein may be combined with the agents provided herein in any dosage amount of the compound (e.g., from 50 mg to 500 mg of compound) the same as if each combination of dosages were specifically and individually listed.

VI. Methods of Treatment

In some embodiments, the present disclosure provides method of inhibiting DGKα in a subject in need thereof, the method comprising administering to the subject a therapeutically effective amount of a compound of the present disclosure, or a pharmaceutically acceptable salt thereof, or a pharmaceutical composition of the present disclosure. In some embodiments, the present disclosure provides method of inhibiting DGKα in a subject in need thereof, the method comprising administering to the subject a therapeutically effective amount of a compound of the present disclosure, e.g., a compound of Formula (I), (I-1), (Ia), (Ia-1), (Ib), (Ic), (IIa), (IIa-1), (IIc), (IIc-1), (IIc-2), (IIc-2), (IIc-3), (IIc-4), (IIc-5), (IIc-6), (IIc-7), or (IIc-8), or a pharmaceutically acceptable salt thereof, or a pharmaceutical composition of the present disclosure.

In some embodiments, the present disclosure provides a method of inhibiting DGKα in a subject in need thereof that comprises administering to the subject a therapeutically effective amount of a compound of Formula (I):

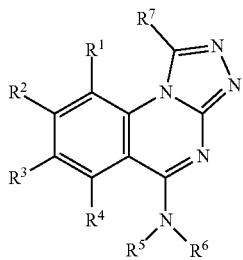

(I)

or a pharmaceutically acceptable salt thereof, wherein
$R^1$ is hydrogen, $C_{1-6}$ alkyl, $C_{2-6}$ alkenyl, $C_{2-6}$ alkynyl, $C_{1-6}$ alkoxy, halogen, $C_{1-6}$ haloalkyl, $C_{1-6}$ haloalkoxy, or —CN;

$R^2$ is hydrogen, $C_{1-6}$ alkyl, $C_{2-6}$ alkenyl, $C_{2-6}$ alkynyl, $C_{1-6}$ hydroxyalkyl, $C_{1-6}$ aminoalkyl, $C_{1-6}$ alkoxy, $C_{2-6}$ alkoxyalkyl, halogen, $C_{1-6}$ haloalkyl, $C_{1-6}$ haloalkoxy, —CN, —NO, —NO$_2$, —C(O)R$^{2a}$, —C(O)OR$^{2a}$, —OC(O)R$^{2a}$, —C(O)N(R$^{2a}$)(R$^{2b}$), —N(R$^{2a}$)C(O)R$^{2b}$, —OC(O)N(R$^{2a}$)(R$^{2b}$), —N(R$^{2a}$)C(O)OR$^{2b}$, —C(=NR$^{2a}$)N(R$^{2b}$)(R$^{2c}$), —N(R$^{2a}$)(R$^{2b}$), —N(R$^{2a}$)N(R$^{2b}$)(R$^{2c}$), —N(R$^{2a}$)N=C(R$^{2b}$)(OR$^{2c}$), —OR$^{2a}$, —SR$^{2a}$, —S(O)R$^{2a}$, —S(O)(NR$^{2a}$)(R$^{2b}$), —S(NR$^{2a}$)(NR$^{2b}$)(R$^{2c}$), —S(O)$_2$R$^{2a}$, —S(O)$_2$N(R$^{2a}$)(R$^{2b}$), —N(R$^{2a}$)S(O)$_2$(R$^{2b}$), —P(R$^{2a}$)(R$^{2b}$), —P(O)(R$^{2a}$)(R$^{2b}$), —P(O)(OR$^{2a}$)(R$^{2b}$), —P(O)(OR$^{2a}$)(OR$^{2b}$), $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, $C_{1-6}$ alkyl-(heterocycloalkyl), heteroaryl, or $C_{1-6}$ alkyl-(heteroaryl), wherein each alkyl, alkenyl or alkynyl is independently optionally substituted with 1 to 3 R$^{2d}$ groups, each cycloalkyl is optionally substituted with 1 to 3 R$^{2e}$ groups, each aryl is optionally substituted with 1 to 3 R$^{2f}$ groups, each heterocycloalkyl is optionally substituted with 1 to 3 R$^{2g}$ groups, and each heteroaryl is optionally substituted with 1 to 3 R$^{2h}$ groups;

each R$^{2a}$, R$^{2b}$, and R$^{2c}$ is independently hydrogen, $C_{1-6}$ alkyl, $C_{2-6}$ alkenyl, $C_{2-6}$ alkynyl, $C_{1-6}$ hydroxyalkyl, $C_{1-6}$ aminoalkyl, $C_{2-6}$ alkoxyalkyl, $C_{1-6}$ haloalkyl, $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, $C_{1-6}$ alkyl-(heterocycloalkyl), heteroaryl, or $C_{1-6}$ alkyl-(heteroaryl), wherein the aryl or heteroaryl is optionally substituted with 1 to 3 R$^{2j}$;

alternatively, R$^{2a}$, R$^{2b}$, and R$^{2c}$ when attached to the same atom can be combined with the atom to which they are attached to form a heterocycloalkyl;

each R$^{2d}$ is independently —CN, —C(O)R$^{2d1}$, —C(O)OR$^{2d1}$, —OC(O)R$^{2d1}$, —C(O)N(R$^{2d1}$)(R$^{2d2}$), —N(R$^{2d1}$)C(O)R$^{2d2}$, —OC(O)N(R$^{2d1}$)(R$^{2d2}$), —N(R$^{2d1}$)C(O)OR$^{2d2}$, —N(R$^{2d1}$)(R$^{2d2}$), =O, —OR$^{2d1}$, —SR$^{2d1}$, —S(O)R$^{2d1}$, —S(O)(NR$^{2d1}$)(R$^{2d2}$), —S(O)$_2$R$^{2d1}$, —S(O)N(R$^{2d1}$)(R$^{2d2}$), —N(R$^{2d1}$)S(O)$_2$R$^{2d2}$, $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, $C_{1-6}$ alkyl-(heterocycloalkyl), heteroaryl, or $C_{1-6}$ alkyl-(heteroaryl);

each R$^{2d1}$ and R$^{2d2}$ is independently hydrogen, $C_{1-6}$ alkyl, $C_{1-6}$ hydroxyalkyl, $C_{1-6}$ aminoalkyl, $C_{2-6}$ alkoxyalkyl, or $C_{1-6}$ haloalkyl;

each R$^{2e}$, R$^{2f}$, R$^{2g}$, and R$^{2h}$ is independently hydrogen, $C_{1-6}$ alkyl, $C_{1-6}$ hydroxyalkyl, $C_{1-6}$ aminoalkyl, $C_{1-6}$ alkoxy, $C_{2-6}$ alkoxyalkyl, halogen, $C_{1-6}$ haloalkyl, $C_{1-6}$ haloalkoxy, —CN, or —OH;

each R$^{2j}$ is independently $C_{1-6}$ alkyl, $C_{1-6}$ hydroxyalkyl, $C_{1-6}$ aminoalkyl, $C_{1-6}$ alkoxy, $C_{2-6}$ alkoxyalkyl, halogen, $C_{1-6}$ haloalkyl, or $C_{1-6}$ haloalkoxy;

R$^3$ is hydrogen, $C_{1-6}$ alkyl, $C_{2-6}$ alkenyl, $C_{2-6}$ alkynyl, $C_{1-6}$ hydroxyalkyl, $C_{1-6}$ aminoalkyl, $C_{1-6}$ alkoxy, $C_{2-6}$ alkoxyalkyl, halogen, $C_{1-6}$ haloalkyl, $C_{1-6}$ haloalkoxy, —CN, —NO, —NO$_2$, —C(O)R$^{3a}$, —C(O)OR$^{3a}$, —OC(O)R$^{3a}$, —C(O)N(R$^{3a}$)(R$^{3b}$), —N(R$^{3a}$)C(O)R$^{3b}$, —OC(O)N(R$^{3a}$)(R$^{3b}$), —N(R$^{3a}$)C(O)OR$^{3b}$, —C(=NR$^{3a}$)N(R$^{3b}$)(R$^{3c}$), —N(R$^{3a}$)(R$^{3b}$), —N(R$^{3a}$)N(R$^{3b}$)(R$^{3c}$), —N(R$^{3a}$)N=C(R$^{3b}$)(OR$^{3c}$), —OR$^{3a}$, —SR$^{3a}$, —S(O)R$^{3a}$, —S(O)(NR$^{3a}$)(R$^{3b}$), —S(NR$^{3a}$)(NR$^{3b}$)(R$^{3c}$), —S(O)$_2$R$^{3a}$, —S(O)$_2$N(R$^{3a}$)(R$^{3b}$), —N(R$^{3a}$)S(O)$_2$(R$^{3b}$), —P(R$^{3a}$)(R$^{3b}$), —P(O)(R$^{3a}$)(R$^{3b}$), —P(O)(OR$^{3a}$)(R$^{3b}$), —P(O)(OR$^{3a}$)(OR$^{3b}$), $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, $C_{1-6}$ alkyl-(heterocycloalkyl), heteroaryl, or $C_{1-6}$ alkyl-(heteroaryl), wherein each alkenyl or alkynyl is independently optionally substituted with 1 to 3 R$^{3d}$ groups, each cycloalkyl is optionally substituted with 1 to 3 R$^{3e}$ groups, each aryl is optionally substituted with 1 to 3 R$^{3f}$ groups, each heterocycloalkyl is optionally substituted with 1 to 3 R$^{3g}$ groups, and each heteroaryl is optionally substituted with 1 to 3 R$^{3h}$ groups;

each R$^{3a}$, R$^{3b}$, and R$^{3c}$ is independently hydrogen, $C_{1-6}$ alkyl, $C_{1-6}$ hydroxyalkyl, $C_{2-6}$ alkoxyalkyl, $C_{1-6}$ haloalkyl, $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, or heteroaryl;

alternatively, R$^{3a}$, R$^{3b}$, and R$^{3c}$ when attached to the same atom can be combined with the atom to which they are attached to form a heterocycloalkyl;

each R$^{3d}$ is independently —N(R$^{3d1}$)(R$^{3d2}$), —OR$^{3d1}$, $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, or heteroaryl;

each R$^{3d1}$ and R$^{3d2}$ is independently hydrogen, $C_{1-6}$ alkyl, or —C(O)O—($C_{1-6}$ alkyl);

each R$^{3e}$, R$^{3f}$, R$^{3g}$, and R$^{3h}$ is independently hydrogen, $C_{1-6}$ alkyl, $C_{1-6}$ alkoxy, halogen, $C_{1-6}$ haloalkyl or $C_{1-6}$ haloalkoxy;

R$^4$ is hydrogen, $C_{1-6}$ alkyl, $C_{2-6}$ alkenyl, $C_{2-6}$ alkynyl, $C_{1-6}$ alkoxy, halogen, $C_{1-6}$ haloalkyl, $C_{1-6}$ haloalkoxy, or —CN;

R$^5$ is hydrogen, $C_{1-6}$ alkyl, $C_{2-6}$ alkenyl, $C_{2-6}$ alkynyl, $C_{1-6}$ hydroxyalkyl, $C_{2-6}$ alkoxyalkyl, $C_{1-6}$ haloalkyl, $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, $C_{1-6}$ alkyl-(heterocycloalkyl), heteroaryl, or $C_{1-6}$ alkyl-(heteroaryl), wherein the alkyl is optionally substituted with R$^{5a}$;

R$^{5a}$ is —OSi(R$^{5a1}$)(R$^{5a2}$)(R$^{5a3}$);

R$^{5a1}$, R$^{5a2}$, and R$^{5a3}$ are each independently $C_{1-6}$ alkyl; and

R$^6$ is C$_{1-6}$ alkyl, C$_{2-6}$ alkenyl, C$_{2-6}$ alkynyl, C$_{1-6}$ haloalkyl, C$_{6-12}$ aryl, or heteroaryl, wherein the aryl or heteroaryl are each optionally substituted with 1 to 3 R$^{6a}$;

each R$^{6a}$ is independently C$_{1-6}$ alkyl, C$_{2-6}$ alkenyl, C$_{2-6}$ alkynyl, C$_{1-6}$ hydroxyalkyl, C$_{1-6}$ aminoalkyl, C$_{1-6}$ alkoxy, C$_{2-6}$ alkoxyalkyl, halogen, C$_{1-6}$ haloalkyl, C$_{1-6}$ haloalkoxy, —CN, —NO$_2$, —C(O)R$^{6b}$, —C(O)OR$^{6b}$, —OC(O)R$^{6b}$, —C(O)N(R$^{6b}$)(R$^{6c}$), —N(R$^{6b}$)C(O)R$^{6c}$, —C(=NR$^{6b}$)N(R$^{6c}$)(R$^{6d}$), —N(R$^{6b}$)(R$^{6c}$), —OR$^{6b}$, —SR$^{6b}$, —S(O)R$^{6b}$, —S(O)$_2$R$^{6b}$, —S(NR$^{6b}$)(NR$^{6c}$)R$^{6d}$, —S(O)(NR$^{6b}$)(R$^{6c}$), —S(O)$_2$N(R$^{6b}$)(R$^{6c}$), —N(R$^{6b}$)S(O)$_2$(R$^{6c}$), —P(R$^{6b}$)(R$^{6c}$), —P(O)(R$^{6b}$)(R$^{6c}$), —P(O)(OR$^{6b}$)(R$^{6c}$), —P(O)(OR$^{6b}$)(OR$^{6c}$), C$_{3-10}$ cycloalkyl, C$_{1-6}$ alkyl-C$_{3-10}$ cycloalkyl, C$_{6-12}$ aryl, C$_{1-6}$ alkyl-C$_{6-12}$ aryl, heterocycloalkyl, C$_{1-6}$ alkyl-(heterocycloalkyl), heteroaryl, or C$_{1-6}$ alkyl-(heteroaryl), wherein the cycloalkyl, aryl, heterocycloalkyl, or heteroaryl is each optionally substituted with 1 to 3 R$^6$, the alkyl is optionally substituted with R$^{6f}$, and the alkynyl is optionally substituted with 1 to 4 R$^{6j}$;

each R$^{6b}$, R$^{6c}$ and R$^{6d}$ is independently hydrogen, C$_{1-6}$ alkyl, C$_{1-6}$ hydroxyalkyl, C$_{1-6}$ aminoalkyl, C$_{2-6}$ alkoxyalkyl, C$_{1-6}$ haloalkyl, C$_{3-10}$ cycloalkyl, C$_{1-6}$ alkyl-C$_{3-10}$ cycloalkyl, C$_{6-12}$ aryl, C$_{1-6}$ alkyl-C$_{6-12}$ aryl, heterocycloalkyl, C$_{1-6}$ alkyl-(heterocycloalkyl), heteroaryl, or C$_{1-6}$ alkyl-(heteroaryl), wherein the cycloalkyl, aryl, heterocycloalkyl, or heteroaryl is optionally substituted by 1 to 3 R$^{6k}$;

each R$^{6k}$ is independently C$_{1-6}$ alkyl, C$_{1-6}$ hydroxyalkyl, C$_{1-6}$ aminoalkyl, C$_{1-6}$ alkoxy, C$_{2-6}$ alkoxyalkyl, C$_{1-6}$ haloalkyl, C$_{1-6}$ haloalkoxy, C$_{3-10}$ cycloalkyl, C$_{1-6}$ alkyl-C$_{3-10}$ cycloalkyl, heterocycloalkyl, or C$_{1-6}$ alkyl-(heterocycloalkyl);

each R$^{6e}$ is independently C$_{1-6}$ alkyl, C$_{2-6}$ alkenyl, C$_{2-6}$ alkynyl, C$_{1-6}$ hydroxyalkyl, C$_{1-6}$ aminoalkyl, C$_{1-6}$ alkoxy, C$_{2-6}$ alkoxyalkyl, halogen, C$_{1-6}$ haloalkyl, C$_{1-6}$ haloalkoxy, —CN, —NO$_2$, —C(O)R$^{6e1}$, —C(O)OR$^{6e1}$, —OC(O)R$^{6e1}$, —C(O)N(R$^{6e1}$)(R$^{6e2}$), —N(R$^{6e1}$)C(O)R$^{6e2}$, —OC(O)N(R$^{6e1}$)(R$^{6e2}$), —N(R$^{6e1}$)C(O)OR$^{6e2}$, —C(=NR$^{6e1}$)N(R$^{6e2}$)(R$^{6e3}$), —N(R$^{6e1}$)(R$^{6e2}$), =O, —OR$^{6e1}$, —SR$^{6e1}$, —S(O)R$^{6e1}$, —S(NR$^{6e1}$)(NR$^{6e2}$), —S(O)(NR$^{6e1}$)(R$^{6e2}$), —S(O)$_2$R$^{6e1}$, —S(O)$_2$N(R$^{6e1}$)(R$^{6e2}$), —SF$_5$, —N(R$^{6e1}$)S(O)$_2$(R$^{6e2}$), —P(R$^{6e1}$)(R$^{6e2}$), —P(O)(R$^{6e1}$)(R$^{6e2}$), —P(O)(OR$^{6e1}$)(R$^{6e2}$), —P(O)(OR$^{6e1}$)(OR$^{6e2}$), —Si(R$^{6e1}$)(R$^{6e2}$)(R$^{6e3}$), C$_{3-10}$ cycloalkyl, C$_{1-6}$ alkyl-C$_{3-10}$ cycloalkyl, C$_{6-12}$ aryl, C$_{1-6}$ alkyl-C$_{6-12}$ aryl, heterocycloalkyl, C$_{1-6}$ alkyl-heterocycloalkyl, heteroaryl, or C$_{1-6}$ alkyl-heteroaryl, wherein the cycloalkyl, aryl, heterocycloalkyl, or heteroaryl is each optionally substituted with 1 to 3 R$^{6h}$, and the alkyl is optionally substituted with 1 to 3 R$^{6m}$;

each R$^{6e1}$, R$^{6e2}$, and R$^{6e3}$ is independently hydrogen, C$_{1-6}$ alkyl, C$_{1-6}$ hydroxyalkyl, C$_{1-6}$ aminoalkyl, C$_{1-6}$ alkoxyalkyl, C$_{1-6}$ haloalkyl, C$_{3-10}$ cycloalkyl, C$_{1-6}$ alkyl-C$_{3-10}$ cycloalkyl, C$_{6-10}$ aryl, C$_{1-6}$ alkyl-C$_{6-10}$ aryl, heterocycloalkyl, C$_{1-6}$ alkyl-(heterocycloalkyl), heteroaryl, or C$_{1-6}$ alkyl-(heteroaryl), wherein the cycloalkyl, aryl, heterocycloalkyl, or heteroaryl is optionally substituted with 1 to 3 R$^{6n}$;

each R$^{6n}$ is C$_{1-6}$ alkyl, C$_{2-6}$ alkenyl, C$_{2-6}$ alkynyl, C$_{1-6}$ hydroxyalkyl, C$_{1-6}$ aminoalkyl, C$_{1-6}$ alkoxy, C$_{2-6}$ alkoxyalkyl, halogen, C$_{1-6}$ haloalkyl, C$_{1-6}$ haloalkoxy, —CN, —C(O)R$^{6n1}$, —C(O)OR$^{6n1}$, —OC(O)R$^{6n1}$, —C(O)N(R$^{6n1}$)(R$^{6n2}$), —N(R$^{6n1}$)C(O)R$^{6n2}$, —OC(O)N(R$^{6n1}$)(R$^{6n2}$), —N(R$^{6n1}$)C(O)OR$^{6n2}$, —C(=NR$^{6n1}$)N(R$^{6n2}$)(R$^{6n3}$), —N(R$^{6n1}$)(R$^{6n2}$), =O, —OH, —SR$^{6n1}$, —S(O)R$^{6n1}$, —S(NR$^{6n1}$)(NR$^{6n2}$)R$^{6n3}$, —S(O)(NR$^{6n1}$)(R$^{6n2}$), —S(O)$_2$R$^{6n1}$, —S(O)$_2$N(R$^{6n1}$)(R$^{6n2}$), or —N(R$^{6n1}$)S(O)$_2$(R$^{6n2}$);

each R$^{6n1}$, R$^{6n2}$ and R$^{6n3}$ is independently hydrogen, C$_{1-6}$ alkyl, C$_{1-6}$ hydroxyalkyl, C$_{1-6}$ aminoalkyl, C$_{2-6}$ alkoxyalkyl, C$_{1-6}$ haloalkyl, C$_{3-10}$ cycloalkyl, C$_{1-6}$ alkyl-C$_{3-10}$ cycloalkyl, C$_{6-10}$ aryl, C$_{1-6}$ alkyl-C$_{6-10}$ aryl, heterocycloalkyl, C$_{1-6}$ alkyl-(heterocycloalkyl), heteroaryl, or C$_{1-6}$ alkyl-(heteroaryl);

each R$^{6h}$ is independently C$_{1-6}$ alkyl, C$_{2-6}$ alkenyl, C$_{2-6}$ alkynyl, C$_{1-6}$ hydroxyalkyl, C$_{1-6}$ aminoalkyl, C$_{1-6}$ alkoxy, C$_{2-6}$ alkoxyalkyl, halogen, C$_{1-6}$ haloalkyl, C$_{1-6}$ haloalkoxy, —CN, —C(O)R$^{6h1}$, —C(O)OR$^{6h1}$, —OC(O)R$^{6h1}$, —C(O)N(R$^{6h1}$)(R$^{6h2}$), —N(R$^{6h1}$)C(O)R$^{6h2}$, —OC(O)N(R$^{6h1}$)(R$^{6h2}$), —N(R$^{6h1}$)C(O)OR$^{6h2}$, —C(=NR$^{6h1}$)N(R$^{6h2}$)(R$^{6h3}$), —N(R$^{6h1}$)(R$^{6h2}$), =O, —OH, —SR$^{6h1}$, —S(O)R$^{6h1}$, —S(NR$^{6h1}$)(NR$^{6h2}$)R$^{6h3}$, —S(O)(NR$^{6h1}$)(R$^{6h2}$), —S(O)$_2$R$^{6h1}$, —S(O)$_2$N(R$^{6h1}$)(R$^{6h2}$), —N(R$^{6h1}$)S(O)$_2$(R$^{6h2}$), C$_{3-10}$ cycloalkyl, C$_{1-6}$ alkyl-C$_{3-10}$ cycloalkyl, heterocycloalkyl, or C$_{1-6}$ alkyl-(heterocycloalkyl);

each R$^{6h1}$, R$^{6h2}$, and R$^{6h3}$ is independently hydrogen, C$_{1-6}$ alkyl, C$_{1-6}$ hydroxyalkyl, C$_{1-6}$ aminoalkyl, C$_{2-6}$ alkoxyalkyl, C$_{1-6}$ haloalkyl, C$_{3-10}$ cycloalkyl, C$_{1-6}$ alkyl-C$_{3-10}$ cycloalkyl, C$_{6-10}$ aryl, C$_{1-6}$ alkyl-C$_{6-10}$ aryl, heterocycloalkyl, C$_{1-6}$ alkyl-(heterocycloalkyl), heteroaryl, or C$_{1-6}$ alkyl-(heteroaryl);

each R$^{6m}$ is independently halogen, C$_{1-6}$ haloalkyl, C$_{1-6}$ haloalkoxy, —CN, —C(O)R$^{6m1}$, —C(O)OR$^{6m1}$, —OC(O)R$^{6m1}$, —C(O)N(R$^{6m1}$)(R$^{6m2}$), —N(R$^{6m3}$)C(O)R$^{6m2}$, —OC(O)N(R$^{6m1}$)(R$^{6m2}$), —N(R$^{6m1}$)C(O)OR$^{6m2}$, —C(=NR$^{6m3}$)N(R$^{6m1}$)(R$^{6m2}$), —N(R$^{6m1}$)(R$^{6m2}$), =O, —OH, —SR$^{6m1}$, —S(O)R$^{6m1}$, —S(NR$^{6m1}$)(NR$^{6m2}$)R$^{6m3}$, —S(O)(NR$^{6m1}$)(R$^{6m2}$), —S(O)$_2$R$^{6m1}$, —S(O)$_2$N(R$^{6m1}$)(R$^{6m2}$), or —N(R$^{6m3}$)S(O)$_2$(R$^{6m2}$);

each R$^{6m1}$, R$^{6m2}$, and R$^{6m3}$ is independently hydrogen, C$_{1-6}$ alkyl, C$_{1-6}$ hydroxyalkyl, C$_{1-6}$ aminoalkyl, C$_{2-6}$ alkoxyalkyl, C$_{1-6}$ haloalkyl, C$_{3-10}$ cycloalkyl, C$_{1-6}$ alkyl-C$_{3-10}$ cycloalkyl, C$_{6-10}$ aryl, C$_{1-6}$ alkyl-C$_{6-10}$ aryl, heterocycloalkyl, C$_{1-6}$ alkyl-(heterocycloalkyl), heteroaryl, or C$_{1-6}$ alkyl-(heteroaryl);

R$^{6f}$ is —OSi(R$^{6f1}$)(R$^{6f2}$)(R$^{6f3}$);

R$^{6f1}$, R$^{6f2}$, and R$^{6f3}$ are each independently C$_{1-6}$ alkyl;

each R$^{6j}$ is independently C$_{2-6}$ alkoxyalkyl, halogen, C$_{1-6}$ haloalkyl, C$_{1-6}$ haloalkoxy, —CN, —C(O)R$^{6j1}$, —C(O)OR$^{6j1}$, —OC(O)R$^{6j1}$, —C(O)N(R$^{6j1}$)(R$^{6j2}$), —N(R$^{6j3}$)C(O)R$^{6j2}$, —OC(O)N(R$^{6j1}$)(R$^{6j2}$), —N(R$^{6j1}$)C(O)OR$^{6j2}$, —C(=NR$^{6j3}$)N(R$^{6j1}$)(R$^{6j2}$), —N(R$^{6j1}$)(R$^{6j2}$), =O, —OR$^{6j}$, —SR$^{61}$, —S(O)R$^{6j1}$, —S(NR$^{6j1}$)(NR$^{6j2}$), —S(NR$^{6j1}$)(NR$^{6j2}$)R$^{6j3}$, —S(O)(NR$^{6j1}$)(R$^{6j2}$), —S(O)$_2$R$^{6j1}$, —S(O)$_2$N(R$^{6j1}$)(R$^{6j2}$), —N(R$^{6j1}$)S(O)$_2$(R$^{6j2}$), —Si(R$^{6j1}$)(R$^{6j2}$)(R$^{6j3}$), C$_{3-10}$ cycloalkyl, C$_{6-12}$ aryl, heterocycloalkyl, or heteroaryl, wherein the cycloalkyl, aryl, heterocycloalkyl, or heteroaryl is optionally substituted with 1 to 3 R$^{6p}$;

each R$^{6j1}$, R$^{6j2}$, and R$^{6j3}$ is independently hydrogen, C$_{1-6}$ alkyl, C$_{1-6}$ hydroxyalkyl, C$_{1-6}$ aminoalkyl, C$_{2-6}$ alkoxyalkyl, C$_{1-6}$ haloalkyl, C$_{3-10}$ cycloalkyl, C$_{1-6}$ alkyl-C$_{3-10}$ cycloalkyl, C$_{6-10}$ aryl, C$_{1-6}$ alkyl-C$_{6-10}$ aryl, heterocycloalkyl, C$_{1-6}$ alkyl-(heterocycloalkyl), heteroaryl, or C$_{1-6}$ alkyl-(heteroaryl);

each R$^{6p}$ is independently C$_{1-6}$ alkyl, C$_{1-6}$ hydroxyalkyl, C$_{1-6}$ aminoalkyl, C$_{1-6}$ alkoxy, C$_{2-6}$ alkoxyalkyl, halogen, C$_{1-6}$ haloalkyl, C$_{1-6}$ haloalkoxy, —CN, —C(O)R$^{6p1}$, —C(O)OR$^{6p1}$, —OC(O)R$^{6p1}$, —C(O)N(R$^{6p1}$)(R$^{6p2}$), —N(R$^{6p1}$)C(O)R$^{6p2}$, —OC(O)N(R$^{6p1}$)(R$^{6p2}$), —N($R^{6p1}$)C(O)O$R^{6p2}$,  —C(=N$R^{6p3}$)N($R^{6p1}$)($R^{6p2}$), —N($R^{6p1}$)($R^{6p2}$), =O, —OH, —S$R^{6p1}$, —S(O)$R^{6p1}$, —S(N$R^{6p1}$)(N$R^{6p2}$)$R^{6p3}$, —S(O)(N$R^{6p1}$)($R^{6p2}$), —S(O)$_2R^{6p1}$, —S(O)$_2$N($R^{6p1}$)($R^{6p2}$), or —N($R^{6p1}$)S(O)$_2$($R^{6p2}$);

each $R^{6p1}$, $R^{6p2}$, and $R^{6p3}$ is independently hydrogen, $C_{1-6}$ alkyl, $C_{1-6}$ hydroxyalkyl, $C_{1-6}$ aminoalkyl, $C_{2-6}$ alkoxyalkyl, $C_{1-6}$ haloalkyl, $C_{3-10}$ cycloalkyl, $C_{1-6}$ alkyl-$C_{3-10}$ cycloalkyl, $C_{6-10}$ aryl, $C_{1-6}$ alkyl-$C_{6-10}$ aryl, heterocycloalkyl, $C_{1-6}$ alkyl-(heterocycloalkyl), heteroaryl, or $C_{1-6}$ alkyl-(heteroaryl);

or $R^5$ and one $R^{6a}$ together with the atoms to which they are attached form a heterocycloalkyl, optionally substituted with 1 to 3 $R^{6g}$;

each $R^{6g}$ is independently $C_{1-6}$ alkyl, $C_{2-6}$ alkenyl, $C_{2-6}$ alkynyl, $C_{1-6}$ hydroxyalkyl, $C_{1-6}$ aminoalkyl, $C_{2-6}$ alkoxyalkyl, halogen, $C_{1-6}$ haloalkyl, $C_{1-6}$ haloalkoxy, or —CN;

$R^7$ is hydrogen, $C_{1-6}$ alkyl, $C_{1-6}$ hydroxyalkyl, $C_{1-6}$ aminoalkyl, $C_{1-6}$ alkoxy, $C_{2-6}$ alkoxyalkyl, $C_{1-6}$ alkylthio, halogen, $C_{1-6}$ haloalkyl, —CN, —OH, —NH$_2$, $C_{3-10}$ cycloalkyl, $C_{1-6}$ alkyl-$C_{3-10}$ cycloalkyl, heterocycloalkyl, or $C_{1-6}$ alkyl-(heterocycloalkyl);

each heterocycloalkyl is a 3 to 20 membered ring having 1 to 4 heteroatoms each independently N, O or S; and each heteroaryl is a 5 to 18 membered ring having 1 to 4 heteroatoms each independently N, O or S.

In some embodiments, the present disclosure provides a method of inhibiting DGKα in a subject in need thereof comprises administering to the subject a therapeutically effective amount of a compound of Formula (I):

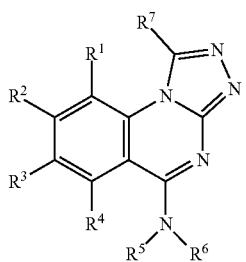

(I)

or a pharmaceutically acceptable salt thereof, wherein $R^1$ is hydrogen, $C_{1-6}$ alkyl, $C_{2-6}$ alkenyl, $C_{2-6}$ alkynyl, $C_{1-6}$ alkoxy, halogen, $C_{1-6}$ haloalkyl, $C_{1-6}$ haloalkoxy, or —CN;

$R^2$ is hydrogen, $C_{1-6}$ alkyl, $C_{2-6}$ alkenyl, $C_{2-6}$ alkynyl, $C_{1-6}$ hydroxyalkyl, $C_{1-6}$ alkoxy, $C_{2-6}$ alkoxyalkyl, halogen, $C_{1-6}$ haloalkyl, $C_{1-6}$ haloalkoxy, —CN, —NO, —NO$_2$, —C(O)$R^{2a}$, —C(O)O$R^{2a}$, —OC(O)$R^{2a}$, —C(O)N($R^{2a}$)($R^{2b}$), —N($R^{2a}$)C(O)$R^{2b}$, —OC(O)N($R^{2a}$)($R^{2b}$), —N($R^{2a}$)C(O)O$R^{2b}$, —C(=N$R^{2a}$)N($R^{2b}$)($R^{2c}$), —N($R^{2a}$)($R^{2b}$), —O$R^{2a}$, —S$R^{2a}$, —S(O)$R^{2a}$, —S(O)$_2R^{2a}$, —S(O)$_2$N($R^{2a}$)($R^{2b}$), —N($R^{2a}$)S(O)$_2$($R^{2b}$), —P(O)($R^{2a}$)($R^{2b}$), —P(O)(O$R^{2a}$)($R^{2b}$), —P(O)(O$R^{2a}$)(O$R^{2b}$), $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, or heteroaryl, wherein each alkenyl or alkynyl is independently optionally substituted with 1 to 3 $R^{2d}$ groups, each cycloalkyl is optionally substituted with 1 to 3 $R^{2e}$ groups, each aryl is optionally substituted with 1 to 3 $R^{2f}$ groups, each heterocycloalkyl is optionally substituted with 1 to 3 $R^{2g}$ groups, and each heteroaryl is optionally substituted with 1 to 3 $R^{2h}$ groups;

each $R^{2a}$, $R^{2b}$, and $R^{2c}$ is independently hydrogen, $C_{1-6}$ alkyl, $C_{1-6}$ hydroxyalkyl, $C_{2-6}$ alkoxyalkyl, $C_{1-6}$ haloalkyl, $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, or heteroaryl;

alternatively, $R^{2a}$, $R^{2b}$, and $R^{2c}$ when attached to the same atom can be combined with the atom to which they are attached to form a heterocycloalkyl;

each $R^{2d}$ is independently —N($R^{2d1}$)($R^{2d2}$), —O$R^{2d1}$, $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, or heteroaryl;

each $R^{2d1}$ and $R^{2d2}$ is independently hydrogen, $C_{1-6}$ alkyl, or —C(O)O—($C_{1-6}$ alkyl);

each $R^{2e}$, $R^{2f}$, $R^{2g}$, and $R^{2h}$ is independently hydrogen, $C_{1-6}$ alkyl, $C_{1-6}$ alkoxy, halogen, $C_{1-6}$ haloalkyl or $C_{1-6}$ haloalkoxy;

$R^3$ is hydrogen, $C_{1-6}$ alkyl, $C_{2-6}$ alkenyl, $C_{2-6}$ alkynyl, $C_{1-6}$ hydroxyalkyl, $C_{1-6}$ alkoxy, $C_{2-6}$ alkoxyalkyl, halogen, $C_{1-6}$ haloalkyl, $C_{1-6}$ haloalkoxy, —CN, —NO, —NO$_2$, —C(O)$R^{3a}$, —C(O)O$R^{3a}$, —OC(O)$R^{3a}$, —C(O)N($R^{3a}$)($R^{3b}$), —N($R^{3a}$)C(O)$R^{3b}$, —OC(O)N($R^{3a}$)($R^{3b}$), —N($R^{3a}$)C(O)O$R^{3b}$, —C(=N$R^{3a}$)N($R^{3b}$)($R^{3c}$), —N($R^{3a}$)($R^{3b}$), —O$R^{3a}$, —S$R^{3a}$, —S(O)$R^{3a}$, —S(O)$_2R^{3a}$, —S(O)$_2$N($R^{3a}$)($R^{3b}$), —N($R^{3a}$)S(O)$_2$($R^{3b}$), —P(O)($R^{3a}$)($R^{3b}$), —P(O)(O$R^{3a}$)($R^{3b}$), —P(O)(O$R^{3a}$)(O$R^{3b}$), $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, or heteroaryl, wherein each alkenyl or alkynyl is independently optionally substituted with 1 to 3 $R^{3d}$ groups, each cycloalkyl is optionally substituted with 1 to 3 $R^{3e}$ groups, each aryl is optionally substituted with 1 to 3 $R^{3f}$ groups, each heterocycloalkyl is optionally substituted with 1 to 3 $R^{3g}$ groups, and each heteroaryl is optionally substituted with 1 to 3 $R^{3h}$ groups;

each $R^{3a}$, $R^{3b}$, and $R^{3c}$ is independently hydrogen, $C_{1-6}$ alkyl, $C_{1-6}$ hydroxyalkyl, $C_{2-6}$ alkoxyalkyl, $C_{1-6}$ haloalkyl, $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, or heteroaryl;

alternatively, $R^{3a}$, $R^{3b}$, and $R^{3c}$ when attached to the same atom can be combined with the atom to which they are attached to form a heterocycloalkyl;

each $R^{3d}$ is independently —N($R^{3d1}$)($R^{3d2}$), —O$R^{3d1}$, $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, or heteroaryl;

each $R^{3d1}$ and $R^{3d2}$ is independently hydrogen, $C_{1-6}$ alkyl, or —C(O)O—($C_{1-6}$ alkyl);

each $R^{3e}$, $R^{3f}$, $R^{3g}$, and $R^{3h}$ is independently hydrogen, $C_{1-6}$ alkyl, $C_{1-6}$ alkoxy, halogen, $C_{1-6}$ haloalkyl or $C_{1-6}$ haloalkoxy;

$R^4$ is hydrogen, $C_{1-6}$ alkyl, $C_{2-6}$ alkenyl, $C_{2-6}$ alkynyl, $C_{1-6}$ alkoxy, halogen, $C_{1-6}$ haloalkyl, $C_{1-6}$ haloalkoxy, or —CN;

$R^5$ is hydrogen, $C_{1-6}$ alkyl, $C_{2-6}$ alkenyl, $C_{2-6}$ alkynyl, $C_{1-6}$ hydroxyalkyl, $C_{2-6}$ alkoxyalkyl, $C_{1-6}$ haloalkyl, $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, $C_{1-6}$ alkyl-(heterocycloalkyl), heteroaryl, or $C_{1-6}$ alkyl-(heteroaryl), wherein the alkyl is optionally substituted with $R^{5a}$;

$R^{5a}$ is —OSi($R^{5a1}$)($R^{5a2}$)($R^{5a3}$);

$R^{5a1}$, $R^{5a2}$, and $R^{5a3}$ are each independently $C_{1-6}$ alkyl; and $R^6$ is $C_{1-6}$ alkyl, $C_{2-6}$ alkenyl, $C_{2-6}$ alkynyl, $C_{1-6}$ haloalkyl, $C_{6-12}$ aryl, or heteroaryl, wherein the aryl or heteroaryl are each optionally substituted with 1 to 3 $R^{6a}$;

each $R^{6a}$ is independently $C_{1-6}$ alkyl, $C_{2-6}$ alkenyl, $C_{2-6}$ alkynyl, $C_{1-6}$ hydroxyalkyl, $C_{1-6}$ alkoxy, $C_{2-6}$ alkoxyalkyl, halogen, $C_{1-6}$ haloalkyl, $C_{1-6}$ haloalkoxy, —CN, —$NO_2$, —C(O)$R^{6b}$, —C(O)O$R^{6b}$, —OC(O)$R^{6b}$, —C(O)N($R^{6b}$)($R^{6c}$), —N($R^{6b}$)C(O)$R^{6c}$, —C(=N$R^{6b}$)N($R^6$)($R^{6d}$), —N($R^{6b}$)($R^{6c}$), —O$R^{6b}$, —S$R^{6b}$, —S(O)$R^{6b}$, —S(O)$_2R^{6b}$, —S(O)$_2$N($R^{6b}$)($R^{6c}$), —N($R^{6b}$)S(O)$_2$($R^{6c}$), $C_{3-10}$ cycloalkyl, $C_{6-12}$ aryl, heterocycloalkyl, or heteroaryl, wherein the cycloalkyl, aryl, heterocycloalkyl, or heteroaryl is each optionally substituted with 1 to 3 $R^{6e}$, and the alkyl is optionally substituted with $R^{6f}$;

or $R^5$ and one $R^{6a}$ together with the atoms to which they are attached form a heterocycloalkyl, optionally substituted with 1 to 3 $R^{6g}$;

each $R^{6b}$, $R^{6c}$ and $R^{6d}$ is independently hydrogen, $C_{1-6}$ alkyl, $C_{1-6}$ hydroxyalkyl, $C_{2-6}$ alkoxyalkyl, $C_{1-6}$ haloalkyl, $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, or heteroaryl;

each $R^{6e}$ is independently $C_{1-6}$ alkyl, $C_{2-6}$ alkenyl, $C_{2-6}$ alkynyl, $C_{1-6}$ hydroxyalkyl, $C_{1-6}$ alkoxy, $C_{2-6}$ alkoxyalkyl, halogen, $C_{1-6}$ haloalkyl, $C_{1-6}$ haloalkoxy, —CN, —$NO_2$, —C(O)$R^{6e1}$, —C(O)O$R^{6e1}$, —OC(O)$R^{6e1}$, —C(O)N($R^{6e1}$)($R^{6e2}$), —N($R^{6e1}$)C(O)$R^{6e2}$, —C(=N$R^{6e1}$)N($R^{6e2}$)($R^{6e3}$), —N($R^{6e1}$)($R^{6e2}$), —O$R^{6e1}$, —S$R^{6e1}$, —S(O)$R^{6e1}$, —S(O)$_2R^{6e1}$, —S(O)$_2$N($R^{6e1}$)($R^{6e2}$), —N($R^{6e1}$)S(O)$_2$($R^{6e2}$), $C_{3-10}$ cycloalkyl, $C_{6-12}$ aryl, heterocycloalkyl, or heteroaryl, wherein the cycloalkyl, aryl, heterocycloalkyl, or heteroaryl is each optionally substituted with 1 to 3 $R^{6h}$;

each $R^{6e1}$, $R^{6e2}$, and $R^{6e3}$ is independently hydrogen or $C_{1-6}$ alkyl;

$R^{6f}$ is —OSi($R^{6f1}$)($R^{6f2}$)($R^{6f3}$);

$R^{6f1}$, $R^{6f2}$, and $R^{6f3}$ are each independently $C_{1-6}$ alkyl;

each $R^{6g}$ is independently $C_{1-6}$ alkyl, $C_{2-6}$ alkenyl, $C_{2-6}$ alkynyl, halogen, $C_{1-6}$ haloalkyl, $C_{1-6}$ haloalkoxy, or —CN;

each $R^{6h}$ is independently $C_{1-6}$ alkyl, $C_{2-6}$ alkenyl, $C_{2-6}$ alkynyl, $C_{1-6}$ alkoxy, halogen, $C_{1-6}$ haloalkyl, $C_{1-6}$ haloalkoxy, —C(O)$R^{6h1}$, —C(O)O$R^{6h1}$, —OC(O)$R^{6h1}$, —C(O)N($R^{6h1}$)($R^{6h2}$), —N($R^{6h1}$)C(O)$R^{6h2}$, —C(=N$R^{6h1}$)N($R^{6h2}$)($R^{6h3}$), —N($R^{6h1}$)($R^{6h2}$), —OH, —S$R^{6h1}$, —S(O)$R^{6h1}$, —S(O)$_2R^{6h1}$, —S(O)$_2$N($R^{6h1}$)($R^{6h2}$), or —N($R^{6h1}$)S(O)$_2$($R^{6h2}$);

each $R^{6h1}$, $R^{6h2}$, and $R^{6h3}$ is independently hydrogen or $C_{1-6}$ alkyl;

$R^7$ is hydrogen, $C_{1-6}$ alkyl, halogen, $C_{1-6}$ haloalkyl, —CN, or —OH;

each heterocycloalkyl is a 3 to 10 membered ring having 1 to 4 heteroatoms each independently N, O or S; and each heteroaryl is a 5 to 10 membered ring having 1 to 4 heteroatoms each independently N, O or S.

In some embodiments, a method of inhibiting DGKα in a subject in need thereof comprises administering to the subject a therapeutically effective amount of the compound having the structure of a compound in Table 1A, Table 1B, Table 1C, Table 1D, Table 1E, Table 1F, Table 1G, Table 1H, Table 11, Table 1J, Table 2A, Table 2B, Table 2C, Table 2D, Table 2E, Table 2F, Table 2G, Table 2H, Table 21, Table 2J, Table 2K, Table 2L, Table 3A, Table 3B, Table 3C, Table 3D, Table 3E, Table 3F, Table 3G, Table 3H, Table 3I, Table 3J, or Table 3K, or a pharmaceutically acceptable salt thereof, or a pharmaceutical composition thereof. In some embodiments, a method of inhibiting DGKα in a subject in need thereof comprises administering to the subject a therapeutically effective amount of the compound having the structure of a compound in Table 3F, Table 3H, Table 3I, Table 3J, or Table 3K, or a pharmaceutically acceptable salt thereof, or a pharmaceutical composition thereof.

In some embodiments, the present disclosure provides a method of treating cancer in a subject in need thereof, the method comprising administering to the subject a therapeutically effective amount of a compound of the present disclosure, or a pharmaceutically acceptable salt thereof, or a pharmaceutical composition thereof.

In some embodiments, the cancer is pancreatic cancer, bladder cancer, colorectal cancer, breast cancer, prostate cancer, renal cancer, hepatocellular cancer, lung cancer, ovarian cancer, cervical cancer, gastric cancer, esophageal cancer, head and neck cancer, melanoma, neuroendocrine cancer, CNS cancer, brain cancer, bone cancer, soft tissue sarcoma, non-small cell lung cancer, small-cell lung cancer or colon cancer. In some embodiments, the cancer is acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CML), multiple myeloma (MM), non-Hodgkin's lymphoma (NHL), mantle cell lymphoma (MCL), follicular lymphoma, Waldestrom's macroglobulinemia (WM), T-cell lymphoma, B-cell lymphoma or diffuse large B-cell lymphoma (DLBCL). In some embodiments, the cancer is brain (gliomas), glioblastomas, astrocytomas, glioblastoma multiforme, Bannayan-Zonana syndrome, Cowden disease, Lhermitte-Duclos disease, breast, colon, head and neck, kidney, lung, liver, melanoma, ovarian, pancreatic, adenocarcinoma, ductal adenocarcinoma, adenosquamous carcinoma, acinar cell carcinoma, glucagonoma, insulinoma, prostate, sarcoma or thyroid.

In some embodiments, the cancer is a solid tumor, a hematological cancer, or a metastatic lesion. In some embodiments, the solid tumor is a sarcoma, a fibroblastic sarcoma, a carcinoma, or an adenocarcinoma. In some embodiments, the hematological cancer is a leukemia, a lymphoma, or a myeloma.

In some embodiments, the cancer is a lung cancer, a melanoma, a renal cancer, a liver cancer, a myeloma, a prostate cancer, a breast cancer, an ovarian cancer, a colorectal cancer, a pancreatic cancer, a head and neck cancer, an anal cancer, a gastro-esophageal cancer, a mesothelioma, a nasopharyngeal cancer, a thyroid cancer, a cervical cancer, an epithelial cancer, a peritoneal cancer, a lymphoproliferative disease, an acute lymphoblastic leukemia (ALL), an acute myelogenous leukemia (AML), a chronic lymphocytic leukemia (CLL), a chronic myelogenous leukemia (CML), a chronic myelomonocytic leukemia (CMML), a hairy cell leukemia, a B cell lymphoma, a diffuse large B-cell lymphoma (DLBCL), an activated B-cell like (ABC) diffuse large B cell lymphoma, a germinal center B cell (GCB) diffuse large B cell lymphoma, a mantle cell lymphoma, a Hodgkin lymphoma, a non-Hodgkin lymphoma, a relapsed non-Hodgkin lymphoma, a refractory non-Hodgkin lymphoma, a recurrent follicular non-Hodgkin lymphoma, a Burkitt lymphoma, a small lymphocytic lymphoma, a follicular lymphoma, a lymphoplasmacytic lymphoma, or an extranodal marginal zone lymphoma.

In some embodiments, the cancer is an epithelial tumor (e.g., a carcinoma, a squamous cell carcinoma, a basal cell carcinoma, a squamous intraepithelial neoplasia), a glandular tumor (e.g., an adenocarcinoma, an adenoma, an adenomyoma), a mesenchymal or soft tissue tumor (e.g., a sarcoma, a rhabdomyosarcoma, a leiomyosarcoma, a liposarcoma, a fibrosarcoma, a dermatofibrosarcoma, a neurofibrosarcoma, a fibrous histiocytoma, an angiosarcoma, an angiomyxoma, a leiomyoma, a chondroma, a chondrosarcoma, an alveolar soft-part sarcoma, an epithelioid hemangioendothelioma, a Spitz tumor, a synovial sarcoma), or a lymphoma.

In some embodiments, the cancer is a solid tumor in or arising from a tissue or organ selected from the group consisting of: bone (e.g., adamantinoma, aneurysmal bone cysts, angiosarcoma, chondroblastoma, chondroma, chondromyxoid fibroma, chondrosarcoma, chordoma, dedifferentiated chondrosarcoma, enchondroma, epithelioid hemangioendothelioma, fibrous dysplasia of the bone, giant cell tumour of bone, haemangiomas and related lesions, osteoblastoma, osteochondroma, osteosarcoma, osteoid osteoma, osteoma, periosteal chondroma, Desmoid tumor, Ewing sarcoma); lips and oral cavity (e.g., odontogenic ameloblastoma, oral leukoplakia, oral squamous cell carcinoma, primary oral mucosal melanoma); salivary glands (e.g., pleomorphic salivary gland adenoma, salivary gland adenoid cystic carcinoma, salivary gland mucoepidermoid carcinoma, salivary gland Warthin's tumors); esophagus (e.g., Barrett's esophagus, dysplasia and adenocarcinoma); gastrointestinal tract, including stomach (e.g., gastric adenocarcinoma, primary gastric lymphoma, gastrointestinal stromal tumors (GISTs), metastatic deposits, gastric carcinoids, gastric sarcomas, neuroendocrine carcinoma, gastric primary squamous cell carcinoma, gastric adenoacanthomas), intestines and smooth muscle (e.g., intravenous leiomyomatosis), colon (e.g., colorectal adenocarcinoma), rectum, anus; pancreas (e.g., serous neoplasms, including microcystic or macrocystic serous cystadenoma, solid serous cystadenoma, Von Hippel-Landau (VHL)-associated serous cystic neoplasm, serous cystadenocarcinoma, mucinous cystic neoplasms (MCN), intraductal papillary mucinous neoplasms (IPMN), intraductal oncocytic papillary neoplasms (IOPN), intraductal tubular neoplasms, cystic acinar neoplasms, including acinar cell cystadenoma, acinar cell cystadenocarcinoma, pancreatic adenocarcinoma, invasive pancreatic ductal adenocarcinomas, including tubular adenocarcinoma, adenosquamous carcinoma, colloid carcinoma, medullary carcinoma, hepatoid carcinoma, signet ring cell carcinoma, undifferentiated carcinoma, undifferentiated carcinoma with osteoclast-like giant cells, acinar cell carcinoma, neuroendocrine neoplasms, neuroendocrine microadenoma, neuroendocrine tumors (NET), neuroendocrine carcinoma (NEC), including small cell or large cell NEC, insulinoma, gastrinoma, glucagonoma, serotonin-producing NET, somatostatinoma, VIPoma, solid-pseudopapillary neoplasms (SPN), pancreatoblastoma); gall bladder (e.g. carcinoma of the gallbladder and extrahepatic bile ducts, intrahepatic cholangiocarcinoma); neuro-endocrine (e.g., adrenal cortical carcinoma, carcinoid tumors, phaeochromocytoma, pituitary adenomas); thyroid (e.g., anaplastic (undifferentiated) carcinoma, medullary carcinoma, oncocytic tumors, papillary carcinoma, adenocarcinoma); liver (e.g., adenoma, combined hepatocellular and cholangiocarcinoma, fibrolamellar carcinoma, hepatoblastoma, hepatocellular carcinoma, mesenchymal, nested stromal epithelial tumor, undifferentiated carcinoma, hepatocellular carcinoma, intrahepatic cholangiocarcinoma, bile duct cystadenocarcinoma, epithelioid hemangioendothelioma, angiosarcoma, embryonal sarcoma, rhabdomyosarcoma, solitary fibrous tumor, teratoma, York sac tumor, carcinosarcoma, rhabdoid tumor); kidney (e.g., ALK-rearranged renal cell carcinoma, chromophobe renal cell carcinoma, clear cell renal cell carcinoma, clear cell sarcoma, metanephric adenoma, metanephric adenofibroma, mucinous tubular and spindle cell carcinoma, nephroma, nephroblastoma (Wilms tumor), papillary adenoma, papillary renal cell carcinoma, renal oncocytoma, renal cell carcinoma, succinate dehydrogenase-deficient renal cell carcinoma, collecting duct carcinoma); breast (e.g., invasive ductal carcinoma, including without limitation, acinic cell carcinoma, adenoid cystic carcinoma, apocrine carcinoma, cribriform carcinoma, glycogen-rich/clear cell, inflammatory carcinoma, lipid-rich carcinoma, medullary carcinoma, metaplastic carcinoma, micropapillary carcinoma, mucinous carcinoma, neuroendocrine carcinoma, oncocytic carcinoma, papillary carcinoma, sebaceous carcinoma, secretory breast carcinoma, tubular carcinoma, lobular carcinoma, including without limitation, pleomorphic carcinoma, signet ring cell carcinoma, peritoneum (e.g., mesothelioma, primary peritoneal cancer)); female sex organ tissues, including ovary (e.g., choriocarcinoma, epithelial tumors, germ cell tumors, sex cord-stromal tumors), Fallopian tubes (e.g., serous adenocarcinoma, mucinous adenocarcinoma, endometrioid adenocarcinoma, clear cell adenocarcinoma, transitional cell carcinoma, squamous cell carcinoma, undifferentiated carcinoma, mullerian tumors, adenosarcoma, leiomyosarcoma, teratoma, germ cell tumors, choriocarcinoma, trophoblastic tumors), uterus (e.g., carcinoma of the cervix, endometrial polyps, endometrial hyperplasia, intraepithelial carcinoma (EIC), endometrial carcinoma (e.g., endometrioid carcinoma, serous carcinoma, clear cell carcinoma, mucinous carcinoma, squamous cell carcinoma, transitional carcinoma, small cell carcinoma, undifferentiated carcinoma, mesenchymal neoplasia), leiomyoma (e.g., endometrial stromal nodule, leiomyosarcoma, endometrial stromal sarcoma (ESS), mesenchymal tumors), mixed epithelial and mesenchymal tumors (e.g., adenofibroma, carcinofibroma, adenosarcoma, carcinosarcoma (malignant mixed mesodermal sarcoma—MMMT)), endometrial stromal tumors, endometrial malignant mullerian mixed tumours, gestational trophoblastic tumors (partial hydatiform mole, complete hydatiform mole, invasive hydatiform mole, placental site tumour)), vulva, vagina; male sex organ tissues, including prostate, testis (e.g., germ cell tumors, spermatocytic seminoma), penis; bladder (e.g., squamous cell carcinoma, urothelial carcinoma, bladder urothelial carcinoma); brain, (e.g., gliomas (e.g., astrocytomas, including non-infiltrating, low-grade, anaplastic, glioblastomas; oligodendrogliomas, ependymomas), meningiomas, gangliogliomas, schwannomas (neurilemmomas), craniopharyngiomas, chordomas, Non-Hodgkin lymphomas, pituitary tumors; eye (e.g., retinoma, retinoblastoma, ocular melanoma, posterior uveal melanoma, iris hamartoma); head and neck (e.g., nasopharyngeal carcinoma, Endolymphatic Sac Tumor (ELST), epidermoid carcinoma, laryngeal cancers including squamous cell carcinoma (SCC) (e.g., glottic carcinoma, supraglottic carcinoma, subglottic carcinoma, transglottic carcinoma), carcinoma in situ, verrucous, spindle cell and basaloid SCC, undifferentiated carcinoma, laryngeal adenocarcinoma, adenoid cystic carcinoma, neuroendocrine carcinomas, laryngeal sarcoma), head and neck paragangliomas (e.g., carotid body, jugulotympanic, vagal); thymus (e.g., thymoma); heart (e.g., cardiac myxoma); lung (e.g., small cell carcinoma (SCLC), non-small cell lung carcinoma (NSCLC), including squamous cell carcinoma (SCC), adenocarcinoma and large cell carcinoma, carcinoids (typical or atypical), carcinosarcomas, pulmonary blastomas, giant cell carcinomas, spindle cell carcinomas, pleuropulmonary blastoma); lymph (e.g., lymphomas, including Hodgkin's lymphoma, non-Hodgkin's lymphoma, Epstein-Barr virus (EBV)-associated lymphoproliferative diseases, including B cell lymphomas and T cell lymphomas (e.g., Burkitt lymphoma, large B cell lymphoma, diffuse large B-cell lymphoma (DLBCL), mantle cell lymphoma, indolent B-cell lymphoma, low grade B cell lymphoma, fibrin-associated diffuse large cell lymphoma; primary effusion lymphoma; plasmablastic lymphoma; extranodal NK/T cell lymphoma, nasal type; peripheral T cell lymphoma, cutaneous T cell lymphoma, angioimmunoblastic T cell lymphoma; follicular T cell lymphoma; systemic T cell lymphoma), lymphangioleiomyomatosis); central nervous system (CNS) (e.g., gliomas including astrocytic tumors (e.g., pilocytic astrocytoma, pilomyxoid astrocytoma, subependymal giant cell astrocytoma, pleomorphic xanthoastrocytoma, diffuse astrocytoma, fibrillary astrocytoma, gemistocytic astrocytoma, protoplasmic astrocytoma, anaplastic astrocytoma, glioblastoma (e.g., giant cell glioblastoma, gliosarcoma, glioblastoma multiforme) and gliomatosis cerebri), oligodendroglial tumors (e.g., oligodendroglioma, anaplastic oligodendroglioma), oligoastrocytic tumors (e.g., oligoastrocytoma, anaplastic oligoastrocytoma), ependymal tumors (e.g., subependymom, myxopapillary ependymoma, ependymomas (e.g., cellular, papillary, clear cell, tanycytic), anaplastic ependymoma), optic nerve glioma, and non-gliomas (e.g., choroid plexus tumors, neuronal and mixed neuronal-glial tumors, pineal region tumors, embryonal tumors, medulloblastoma, meningeal tumors, primary CNS lymphomas, germ cell tumors, pituitary adenomas, cranial and paraspinal nerve tumors, stellar region tumors), neurofibroma, meningioma, peripheral nerve sheath tumors, peripheral neuroblastic tumours (including without limitation neuroblastoma, ganglioneuroblastoma, ganglioneuroma), trisomy 19 ependymoma); neuroendocrine tissues (e.g., paraganglionic system including adrenal medulla (pheochromocytomas) and extra-adrenal paraganglia ((extra-adrenal) paragangliomas); skin (e.g., clear cell hidradenoma, cutaneous benign fibrous histiocytomas, cylindroma, hidradenoma, melanoma (including cutaneous melanoma, mucosal melanoma), pilomatricoma, Spitz tumors); and soft tissues (e.g., aggressive angiomyxoma, alveolar rhabdomyosarcoma, alveolar soft part sarcoma, angiofibroma, angiomatoid fibrous histiocytoma, synovial sarcoma, biphasic synovial sarcoma, clear cell sarcoma, dermatofibrosarcoma protuberans, desmoid-type fibromatosis, small round cell tumor, desmoplastic small round cell tumor, elastofibroma, embryonal rhabdomyosarcoma, Ewing's tumors/primitive neurectodermal tumors (PNET), extraskeletal myxoid chondrosarcoma, extraskeletal osteosarcoma, paraspinal sarcoma, inflammatory myofibroblastic tumor, bpoblastoma, lipoma, chondroid lipoma, bposarcoma/malignant lipomatous tumors, bposarcoma, myxoid bposarcoma, fibromyxoid sarcoma, lymphangioleiomyoma, malignant myoepithelioma, malignant melanoma of soft parts, myoepithelial carcinoma, myoepithelioma, myxoinflammatory fibroblastic sarcoma, undifferentiated sarcoma, pericytoma, rhabdomyosarcoma, non rhabdomyosarcoma soft tissue sarcoma (NRSTS), soft tissue leiomyosarcoma, undifferentiated sarcoma, well-differentiated bposarcoma.

In some embodiments, the cancer is a melanoma, a gastric cancer, a triple-negative breast cancer (TNBC), a non-small cell lung cancer (NSCLC), a rectal adenocarcinoma, a colorectal cancer, a renal cell carcinoma, an ovarian cancer, a prostate cancer, an oral squamous cell carcinoma (SCC), a head and neck squamous cell carcinoma (HNSCC), a urothelial bladder cancer, a glioblastoma (GBM), a meningioma, adrenal cancer, or an endometrial cancer.

In some embodiments, the method further comprises administering one or more additional therapeutic agents to the subject. The additional therapeutic agent can include any therapeutic agent described above for combination therapy. In some embodiments, the additional therapeutic agent is independently an anti-neoplastic agent, nivolumab, pembrolizumab, atezolizumab, ipilimumab, chemotherapy, radiation therapy, or resection therapy. In some embodiments, the additional therapeutic agent is independently rituxan, doxorubicin, gemcitabine, nivolumab, pembrolizumab, artezolizumab, nivolumab, pembrolizumab, atezolizumab, or ipilimumab.

In some embodiments, the method comprises one or more additional therapeutic agents, wherein the additional therapeutic agent is a PD-1/PD-L1 inhibitor.

In some embodiments, the anti-neoplastic agent is an anti-microtubule agent, a platinum coordination complex, an alkylating agent, an antibiotic agent, a topoisomerase II inhibitor, an antimetabolite, a topoisomerase I inhibitor, a hormone or hormonal analogue, a signal transduction pathway inhibitor, a non-receptor tyrosine kinase angiogenesi, an inhibitor, an immunotherapeutic agent, a proapoptotic agent, a cell cycle signaling inhibitor, a proteasome inhibitor, a inhibitor of cancer metabolism, an anti-PD-L1 agent, a PD-1 antagonist, an immuno-modulator, a STING modulating compound, a CD39 inhibitor, an A2a and A2a adenosine antagonist, a TLR4 antagonist, an antibody to ICOS, or OX40.

In some embodiments, the compound or pharmaceutical composition is co-administered with one or more additional therapeutic agents comprising an activator or agonist of a fins related tyrosine kinase 3 (FLT3; CD 135) receptor, a toll-like receptor (TLR) or a stimulator of interferon genes (STING) receptor.

In some embodiments, the TLR agonist or activator is a TLR2 agonist, a TLR3 agonist, a TLR7 agonist, a TLR8 agonist and a TLR9 agonist.

In some embodiments, the STING receptor agonist or activator is ADU-S100 (MIW-815), SB-11285, MK-1454, SR-8291, AdVCA0848, GSK-532, SYN-STING, MSA-1, SR-8291, 5,6-dimethylxanthenone-4-acetic acid (DMXAA), cyclic-GAMP (cGAMP) and cyclic-di-AMP.

In some embodiments, the compound or pharmaceutical composition is co-administered with one or more additional therapeutic agents comprising an inhibitor or antagonist of: protein tyrosine phosphatase, non-receptor type 11 (PTPN11 or SHP2), myeloid cell leukemia sequence 1 (MCL1) apoptosis regulator; mitogen-activated protein kinase kinase kinase kinase 1 (MAP4K1) (also called Hematopoietic Progenitor Kinase 1 (HPK1)); diacylglycerol kinase alpha (DGKA, DAGK, DAGK1 or DGK-alpha); 5'-nucleotidase ecto (NT5E or CD73); transforming growth factor beta 1 (TGFB1 or TGF); heme oxygenase 1 (HMOX1, HO-1 or HO1); vascular endothelial growth factor A (VEGFA or VEGF); erb-b2 receptor tyrosine kinase 2 (ERBB2 HER2, HER2/neu or CD340); epidermal growth factor receptor (EGFR, ERBB, ERBB1 or HER1); ALK receptor tyrosine kinase (ALK, CD246); poly(ADP-ribose) polymerase 1 (PARP1 or PARP); cyclin dependent kinase 4 (CDK4); cyclin dependent kinase 6 (CDK6); C-C motif chemokine receptor 8 (CCR8, CDw198); CD274 molecule (CD274, PDL1 or PD-L1); programmed cell death 1 (PDCD1, PD1 or PD-1); and/or cytotoxic T-lymphocyte associated protein 4 (CTLA4, CTLA-4, CD 152).

In some embodiments, the inhibitor comprises an antigen binding molecule, an antibody or an antigen-binding fragment thereof.

In some embodiments, the inhibitor of MCL1 is AMG-176, AMG-397, 5-64315, AZD-5991, 483-LM, A1210477, UMI-77, or JKY-5-037.

In some embodiments, the inhibitor of PTPN11 or SHP2 is TN0155 (SHP-099), RMC-4550, JAB-3068 and RMC-4630.

In some embodiments, the additional therapeutic agent is a chemotherapeutic, an anti-neoplastic, a radiotherapeutic, or a checkpoint targeting agent. In some embodiments, the one or more anti-neoplastic or chemotherapeutic agents are a nucleoside analog (e.g., 5-fluorouracil, gemcitabine, cytarabine), a taxane (e.g., paclitaxel, nab-paclitaxel, docetaxel, cabazitaxel), a platinum coordination complex (cisplatin, carboplatin, oxaliplatin, nedaplatin, triplatin tetranitrate, phenanthriplatin, picoplatin, satraplatin, dicycloplatin, eptaplatin, lobaplatin, miriplatin), a dihydrofolate reductase (DHFR) inhibitor (e.g., methotrexate, trimetrexate, pemetrexed), a topoisomerase inhibitor (e.g., doxorubicin, daunorubicin, dactinomycin, eniposide, epirubicin, etoposide, idarubicin, irinotecan, mitoxantrone, pixantrone, sobuzoxane, topotecan, irinotecan, MM-398 (liposomal irinotecan), vosaroxin and GPX-150, a1 doxorubicin, AR-67, mavelertinib, AST-2818, avitinib (ACEA-0010), irofulven (MGI-114)), an alkylating agent (e.g., a nitrogen mustard (e.g., cyclophosphamide, chlormethine, uramustine or uracil mustard, melphalan, chlorambucil, ifosfamide, bendamustine, temozolomide, carmustine), a nitrosourea (e.g., carmustine, lomustine, streptozocin), an alkyl sulfonate (e.g., busulfan)), or mixtures thereof.

In some embodiments, the checkpoint targeting agent is an antagonist anti-PD-antibody, an antagonist anti-PD-L1 antibody, an antagonist anti-PD-L2 antibody, an antagonist anti-CTLA-4 antibody, an antagonist anti-TIM-3 antibody, an antagonist anti-LAG-3 antibody, an antagonist anti-CEACAM1 antibody, an agonist anti-GITR antibody, an antagonist anti-TIGIT antibody, an antagonist anti-VISTA antibody, an agonist anti-CD 137 antibody, or an agonist anti-OX40 antibody.

In some embodiments, the additional therapeutic agent comprises one or more cellular therapies. In some embodiments, the cellular therapy comprises one or more of a population of natural killer (NK) cells, NK-T cells, T cells, cytokine-induced killer (CIK) cells, macrophage (MAC) cells, tumor infiltrating lymphocytes (TILs) and/or dendritic cells (DCs). In some embodiments, the cellular therapy entails a T cell therapy, e.g., co-administering a population of alpha/beta TCR T cells, gamma/delta TCR T cells, regulatory T (Treg) cells and/or TRuC™ T cells. In some embodiments, the cellular therapy entails a NK cell therapy, e.g., co-administering NK-92 cells. A cellular therapy can entail the co-administration of cells that are autologous, syngeneic or allogeneic to the subject. In some embodiments, the one or more of a population of immune cells comprise one or more chimeric antigen receptors (CARs).

In some embodiments, the additional therapeutic agent comprises an antibody or an antigen-binding fragment thereof, or antibody-drug conjugate thereof, CD3-targeting multi-specific molecule, CD16-targeting multi-specific molecule, non-immunoglobulin antigen binding molecule or antibody mimetic protein.

In some embodiments, the one or more additional therapeutic agents comprises an immunotherapy, an immunostimulatory therapy, a cytokine therapy, a chemokine therapy, a cellular therapy, a gene therapy, and combinations thereof. In some embodiments, the immunotherapy comprises co-administering one or more antibodies or antigen-binding antibody fragments thereof, or antibody-drug conjugates thereof, CD3-targeting multi-specific molecules, CD16-targeting multi-specific molecules, or non-immunoglobulin antigen-binding domains or antibody mimetic proteins directed against one or more targets or tumor associated antigens (TAAs).

In some embodiments, the present disclosure provides method of treating an HIV or hepatitis B virus infection in a subject in need thereof, the method comprising administering to the subject a therapeutically effective amount of a compound of the present disclosure, or a pharmaceutically acceptable salt thereof, or a pharmaceutical composition thereof. In some embodiments, the compound or pharmaceutical composition is co-administered with one or more additional therapeutic agents. In some embodiments, the one or more additional therapeutic agents comprises a vaccine.

In some embodiments, a method for manufacturing a medicament for treating cancer in a subject in need thereof is characterized in that a compound of the present disclosure, or a pharmaceutically acceptable salt thereof, is used.

In some embodiments, a method for manufacturing a medicament for inhibiting cancer metastasis in a subject in need thereof is characterized in that a compound of the present disclosure, or a pharmaceutically acceptable salt thereof, is used.

In some embodiments, a method for manufacturing a medicament for treating an HIV or hepatitis B virus infection in a subject in need thereof is characterized in that a compound of the present disclosure, or a pharmaceutically acceptable salt thereof, is used.

In some embodiments, a use of the compound of the present disclosure, or a pharmaceutically acceptable salt thereof, is for the manufacture of a medicament for the treatment of cancer in a subject.

In some embodiments, a use of the compound of the present disclosure, or a pharmaceutically acceptable salt thereof, is for the manufacture of a medicament for inhibiting cancer metastasis in a subject.

In some embodiments, a use of the compound of the present disclosure, or a pharmaceutically acceptable salt thereof, is for the manufacture of a medicament for the treatment of an HIV or hepatitis B infection in a subject.

In some embodiments, a compound of the present disclosure is for use in therapy. In some embodiments, the compound is for use in the treatment of a cancer in a subject in need thereof. In some embodiments, the compound is for use in inhibiting cancer metastasis in a subject in need thereof. In some embodiments, the compound is for use in the treatment of an HIV or hepatitis B virus infection in a subject in need thereof.

VII. Methods of Synthesis

Abbreviations. Certain abbreviations and acronyms are used in describing the experimental details. Although most of these would be understood by one skilled in the art, Table 4 contains a list of many of these abbreviations and acronyms.

TABLE 4

List of abbreviations and acronyms.

| Abbreviation | Meaning |
| --- | --- |
| Ac | acetyl |
| AcOEt | ethyl acetate (also EtOAc) |
| ACN | acetonitrile |
| Bn | benzyl |
| Boc | tert-butoxycarbonyl |

TABLE 4-continued

List of abbreviations and acronyms.

| Abbreviation | Meaning |
|---|---|
| BOP | benzotriazol-1-yloxytris(dimethylamino)phosphonium hexafluorophosphate |
| BroP | bromotris(dimethylamino)phosphonium hexafluorophosphate |
| Bu | butyl |
| nBuLi | n-butyllithium |
| CDCl$_3$ | Chloroform-d |
| dba | dibenzylideneacetone |
| DBU | 1,8-Diazabicyclo[5.4.0]undec-7-ene |
| DCM | dichloromethane |
| DMSO | dimethylsulfoxide |
| DMF | dimethylformamide |
| dppf | 1,1'-Bis(diphenylphosphino)ferrocene |
| EA | Ethyl acetate |
| Et | ethyl |
| iBu | isobutyl |
| IPA | isopropanol |
| iPr | isopropyl |
| LC | liquid chromatography |
| LDA | lithium diisopropylamide |
| Me | methyl |
| m/z | mass to charge ratio |
| MS or ms | mass spectrum |
| NMP | N-methyl-2-pyrrolidone |
| Ph | phenyl |
| Ph$_3$P | triphenylphosphine |
| prep. HPLC | preparative high performance liquid chromatography (also prep-HPLC) |
| RT | room temperature |
| SEM | 2-(Trimethylsilyl)ethoxymethyl |
| SEM-Cl | 2-(Trimethylsilyl)ethoxymethyl Chloride |
| Si-column | Silica column |
| tBu | tert-butyl |
| TFA | trifluoroacetic acid |
| THF | tetrahydrofuran |
| TLC | thin layer chromatography |
| δ | parts per million referenced to residual non-deuterated solvent peak |

General Synthetic Schemes

Compounds of Formula (I), (I-1), (Ia), (Ia-1), (Ib), (Ic), (IIa), (IIa-1), (Ic), (Ic-1), (IIc-2), (IIc-2), (IIc-3), (IIc-4), (IIc-5), (Ic-6), (Ic-7), or (Ic-8) of the present disclosure can be prepared, for example, according to the following schemes. During any of the processes for preparation of the subject compounds, it may be necessary and/or desirable to protect sensitive or reactive groups on any of the molecules concerned. This may be achieved by means of conventional protecting groups as described in standard works, such as T. W. Greene and P. G. M. Wuts, "Protective Groups in Organic Synthesis," 4th ed., Wiley, New York 2006. For example, in some embodiments, a protecting includes a benzyloxycarbonyl group or a tert-butyloxycarbonyl group as an amino-protecting group, and/or a tert-butylmethylsilyl group etc. as a hydroxy-protecting group. The protecting groups may be removed at a convenient subsequent stage using methods known from the art.

Exemplary chemical entities useful in methods of the embodiments will now be described by reference to illustrative synthetic schemes for their general preparation herein and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups. Each of the reactions depicted in the general schemes, unless otherwise specified, can be run at a temperature from about 0° C. to the reflux temperature of the organic solvent used. Each of variable sites disclosed in the following schemes is applicable to every functional group in the compounds of Formula (I), (I-1), (Ia), (Ia-1), (Ib), (Ic), (IIa), (IIa-1), (IIc), (IIc-1), (IIc-2), (IIc-2), (IIc-3), (IIc-4), (IIc-5), (IIc-6), (IIc-7), or (IIc-8) provided by the present disclosure.

The embodiments are also directed to processes and intermediates useful for preparing the subject compounds or pharmaceutically acceptable salts thereof.

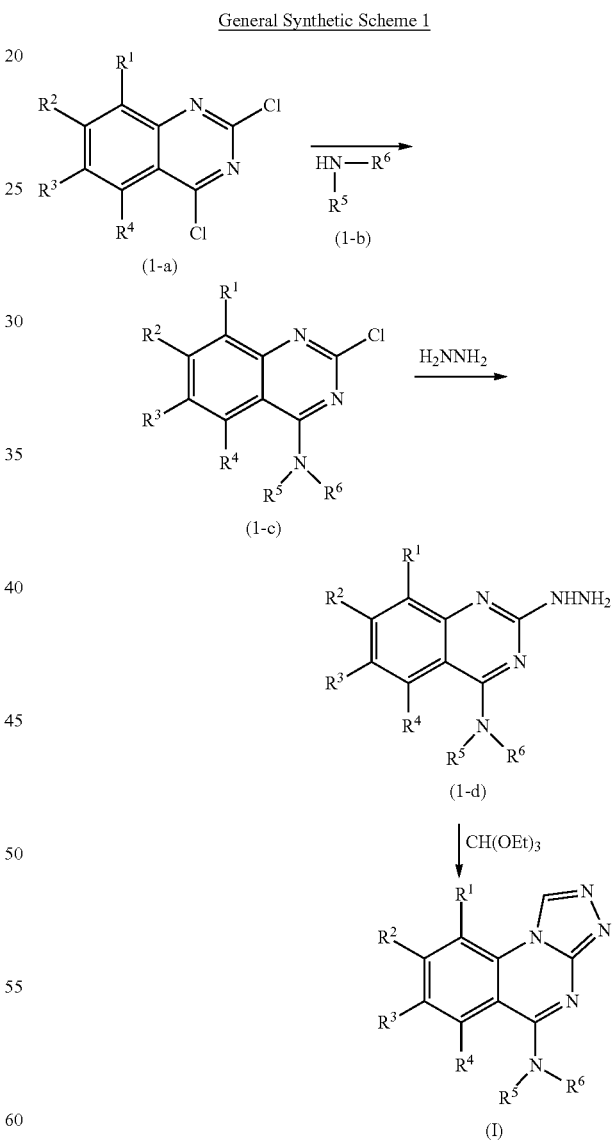

General Synthetic Scheme 1

Compounds of Formula (I), (I-1), (Ia), (Ia-1), (Ib), (Ic), (IIa), (IIa-1), (IIc), (IIc-1), (IIc-2), (IIc-2), (IIc-3), (IIc-4), (IIc-5), (IIc-6), (IIc-7), or (IIc-8) can be prepared according to General Synthetic Scheme 1, wherein $R^1$, $R^2$, $R^3$, $R^4$, $R^5$ and $R^6$ are as described above.

In accordance with General Synthetic Scheme 1, a compound of Formula (1-a) can react with a compound of Formula (1-b) in a solvent to generate a compound of Formula (1-c). It is contemplated that any suitable non-reactive solvent can be used for this reaction, such as DMF. This reaction can be carried out at a time and temperature suitable to generate a desired quantity of a compound of Formula (1-c), for example at a temperature ranging from room temperature to 100° C. and at a time ranging for several minutes to several hours, for instance at room temperature for an hour.

A compound of Formula (1-a), can be purchased or readily synthesized through methods known to those skilled in the art, such as methods described at J. Med. Chem. 2014, 57, 5141-5156 or similar methods. Compounds of Formula (1-b) are commercially available, or can be readily prepared by persons skilled in the art according to known methods.

A compound of Formula (1-c) can be combined with hydrazine in a suitable solvent, such as an alcohol, to generate a compound of Formula (1-d). Suitable solvents can include non-reactive solvents, and the reaction can be carried out at a time and temperature suitable to generate a desired quantity of a compound of Formula (1-d), such as a temperature ranging from room temperature to 100° C. and a time ranging from several minutes to several hours. For example, the reaction can be conducted in ethanol solvent at a temperature below 50° C. for an hour.

A compound of Formula (1-d) can be converted to a compound of Formula (I), (I-1), (Ia), (Ia-1), (Ib), (Ic), (IIa), (IIa-1), (IIc), (IIc-1), (IIc-2), (IIc-2), (IIc-3), (IIc-4), (IIc-5), (IIc-6), (IIc-7), or (IIc-8) by reacting 1 to 5 mole equivalents of triethyl orthoformate with a compound of Formula (1-d) at a time and temperature suitable to generate a desired quantity of a compound of Formula (I), (I-1), (Ia), (Ia-1), (Ib), (Ic), (IIa), (IIa-1), (Ic), (IIc-1), (IIc-2), (IIc-2), (IIc-3), (IIc-4), (IIc-5), (IIc-6), (IIc-7), or (IIc-8). For example, a compound of Formula (1-d) can undergo reaction with triethyl orthoformate at a temperature ranging from room temperature to 120° C., for instance at a temperature of 100° C., for several minutes to several days, such as from one minute to an hour.

A compound of Formula (I), (I-1), (Ia), (Ia-1), (Ib), (Ic), (IIa), (IIa-1), (IIc), (IIc-1), (IIc-2), (IIc-2), (IIc-3), (IIc-4), (IIc-5), (IIc-6), (IIc-7), or (IIc-8) can also be prepared according to the following General Synthetic Scheme 2:

General Synthetic Scheme 2

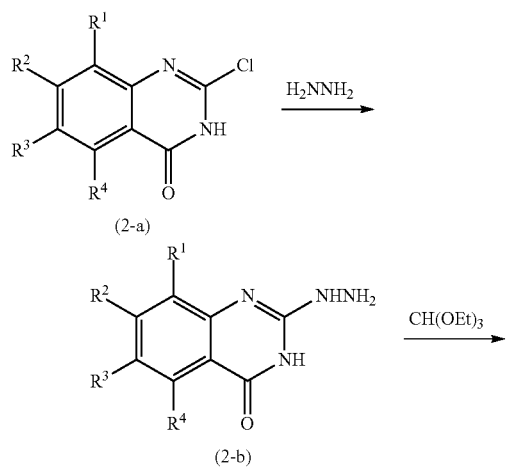

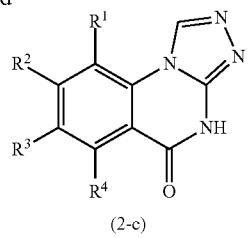

(2-c)

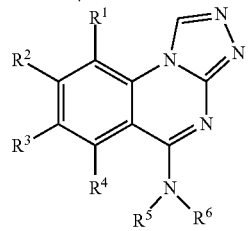

(1-b)

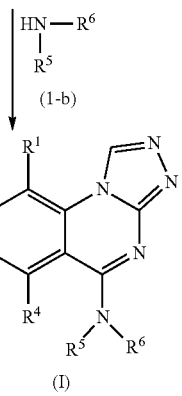

(I)

wherein $R^1$, $R^2$, $R^3$, $R^4$, $R^5$ and $R^6$ are as described herein.

In accordance with General Synthetic Scheme 2, a compound of Formula (2-a) can be combined with hydrazine in a suitable non-reactive solvent, such as an alcohol. The reaction can be carried out at a temperature ranging from room temperature to 100° C., at a time sufficient to produce a desired quantity of a compound of Formula (2-b), for example ranging from several minutes to several hours. For example, a compound of Formula (2-b) can be suitably generated at a temperature between room temperature and 50° C. for an hour. A compound of Formula (2-a) can be obtained commercially or can be readily prepared by a person of ordinary skill in the art through known methods, such as through a reaction of a compound of Formula (1-a) with a base in a suitable solvent.

A compound of Formula (2-b) can be combined with 1 to 5 mole equivalents of triethyl orthoformate under suitable reaction conditions to produce a compound according to Formula (2-c). For example, a reaction to generate a compound of Formula (2-c) can be carried out at a temperature ranging from room temperature to 120° C. at a time ranging from several minutes to several days. For example, a desired quantity of the compound of Formula (2-c) can be generated at a reaction temperature of 100° C. for 1 minute to an hour.

A compound of Formula (I), (I-1), (Ia), (Ia-1), (Ib), (Ic), (IIa), (IIa-1), (IIc), (IIc-1), (IIc-2), (IIc-2), (IIc-3), (IIc-4), (IIc-5), (IIc-6), (IIc-7), or (IIc-8) can be obtained, in accordance with General Synthetic Scheme 2, by reacting a compound of Formula (2-c) with 1 to 5 mole equivalents of a compound of Formula (1-b) using 1 to 5 mole equivalents of a dehydrating condensing agent in a solvent in the presence of a base. Any suitable solvent may be used, including solvents that are not reactive in the reaction. Non-limiting examples of suitable solvents for this reaction include acetonitrile, NMP, DMF, and the like. Suitable dehydrating condensing agents are known to those skilled in the art, including for instance, but not by way of limitation, a phosphonium-based dehydrating condensing agent such as BOP reagent. Exemplary bases suitable for this reaction include, for example, an inorganic base such as cesium carbonate, or an organic amine such as triethylamine.

The reaction can be carried out, for instance, using an acetonitrile solvent, using 1 to 5 mole equivalents of BroP (bromotris(dimethylamino)phosphonium hexafluorophosphate) reagent as the dehydrating condensing agent and 1 to 5 mole equivalents of DBU as the base at a temperature between room temperature and 120° C. for several minutes to several days, such as at 50° C. for 1 minute to an hour.

Alternatively, the conversion of a compound of Formula (2-c) to a compound of Formula (I), (I-1), (Ia), (Ia-1), (Ib), (Ic), (IIa), (IIa-1), (IIc), (IIc-1), (IIc-2), (IIc-2), (IIc-3), (IIc-4), (IIc-5), (IIc-6), (IIc-7), or (IIc-8) can be carried out without using a dehydrating condensing agent. For example, a compound of Formula (2-c) can be reacted with 1 to 5 mole equivalents of the compound of Formula (1-b) in a solvent in the presence of a strong base. Any non-reactive solvent is contemplated as suitable for the reaction, such as an ether-based solvent, or for example THF. Non-limiting examples of suitable strong base include an organic base such as n-BuLi. In some embodiments, 1 to 5 mole equivalents of LDA can be used. The reaction can be carried out at a temperature ranging from −100° C. to 0° C. for several minutes to several days. For example, a desired quantity of the compound of Formula (I), (I-1), (Ia), (Ia-1), (Ib), (Ic), (IIa), (IIa-1), (IIc), (IIc-1), (IIc-2), (IIc-2), (IIc-3), (IIc-4), (IIc-5), (IIc-6), (IIc-7), or (IIc-8) can be generated by carrying out this reaction at a temperature of −78° C. for 1 to 20 hours.

Further a compound of the present disclosure having a desired functional group at a desired position can be prepared by a suitable combination of the methods above, or a procedure usually carried out in an organic synthesis (for example, alkylation reaction of an amino group, oxidation reaction of an alkylthio group into a sulfoxide group or a sulfone group, converting reaction of an alkoxy group into a hydroxy group, or opposite converting reaction thereof).

VIII. Examples

Many general references providing commonly known chemical synthetic schemes and conditions useful for synthesizing the disclosed compounds are available (see, e.g., Smith, March's Advanced Organic Chemistry: Reactions, Mechanisms, and Structure, 7$^{th}$ edition, Wiley-Interscience, 2013.)

Compounds as described herein can be purified by any of the means known in the art, including chromatographic means, such as high performance liquid chromatography (HPLC), preparative thin layer chromatography, flash column chromatography and ion exchange chromatography. Any suitable stationary phase can be used, including normal and reversed phases as well as ionic resins. For example, disclosed compounds can be purified via silica gel chromatography. See, e.g., Introduction to Modern Liquid Chromatography, 2nd ed., ed. L. R. Snyder and J. J. Kirkland, John Wiley and Sons, 1979; and Thin Layer Chromatography, E. Stahl (ed.), Springer-Verlag, New York, 1969.

Compounds were characterized using standard instrumentation methods. Identification of the compound was carried out by hydrogen nuclear magnetic resonance spectrum ($^1$H-NMR) and mass spectrum (MS). $^1$H-NMR was measured at 400 MHz, unless otherwise specified. In some cases, exchangeable hydrogen could not be clearly observed depending on the compound and measurement conditions. The designation br. or broad, used herein, refers to a broad signal. HPLC preparative chromatography was carried out by a commercially available ODS column in a gradient mode using water/methanol (containing formic acid) as eluents, unless otherwise specified.

The Examples provided herein describe the synthesis of compounds disclosed herein as well as intermediates used to prepare the compounds. It is to be understood that individual steps described herein may be combined. It is also to be understood that separate batches of a compound may be combined and then carried forth in the next synthetic step.

In the following description of the Examples, specific embodiments are described. These embodiments are described in sufficient detail to enable those skilled in the art to practice certain embodiments of the present disclosure. Other embodiments may be utilized and logical and other changes may be made without departing from the scope of the disclosure. The following description is, therefore, not intended to limit the scope of the present disclosure.

Representative syntheses of compounds of the present disclosure are described in schemes below, and the particular examples that follow.

A. Intermediates

Intermediate 1. 5-Chloro-[1,2,4]triazolo[4,3-a]quinazoline

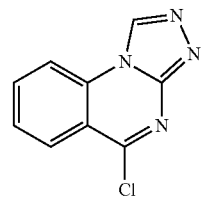 [SMILES: Clc1nc2nncn2c2ccccc12]

(Step 1) Synthesis of 2-Chloroquinazolin-4(1H)-one

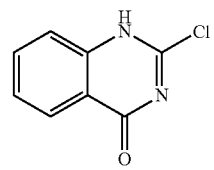 [SMILES: O=c1nc(Cl)[nH]c2ccccc12]

To a stirred solution of 2,4-dichloroquinazoline (5.0 g, 25.12 mmol) in THF (50 mL) was added 1M NaOH solution (50 mL) at 0° C. and the mixture was stirred for 16 h at RT. The reaction mixture was acidified with acetic acid to pH~6. The resulting solids were filtered and dried under vacuum to give the desired product. LCMS(m/z) 181.08 [M+H]+.

(Step 2) Synthesis of 2-Hydrazinylquinazolin-4(1H)-one

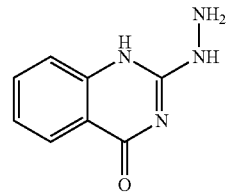 [SMILES: NNc1nc(=O)c2ccccc2[nH]1]

To a stirred solution of 2-chloroquinazolin-4(1H)-one (4.0 g, 22.22 mmol) in EtOH (80 mL) was added hydrazine hydrate (3.33 g, 66.66 mmol) at RT and the mixture was heated to 50° C. for 4 h. The reaction mixture was diluted with petroleum ether. The resulting solids were filtered and dried under vacuum to give the desired product. LCMS(m/z) 177.13 [M+H]+. (Step 3) Synthesis of [1,2,4]Triazolo[4,3-a]quinazolin-5(4H)-one (Intermediate 2)

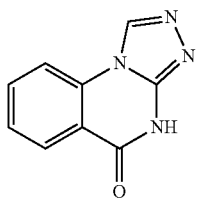 [SMILES: O=c1[nH]c2nncn2c2ccccc12]

The mixture of 2-hydrazinylquinazolin-4(1H)-one (4.0 g, 22.22 mmol) and formic acid (80 mL) was heated to 100° C. for 16 h. The reaction mixture was evaporated under reduced pressure, and the residue was washed with ethanol and n-hexane. The resulting solids were purified by column chromatography (Si-column, hexane:AcOEt=10:0-4:6) to give the desired product. LCMS(m/z) 187.05 [M+H]+.

(Step 4) Synthesis of 5-Chloro-[1,2,4]triazolo[4,3-a]quinazoline

The mixture of [1,2,4]triazolo[4,3-a]quinazolin-5(4H)-one (1.0 g, 5.37 mmol) and phosphorus oxychloride (20 mL) was heated to 110° C. for 6 h. The reaction mixture was evaporated under reduced pressure, and the residue was neutralized with sat. sodium bicarbonate solution at 0° C. The resulting solids were filtered and dried under vacuum to give the desired product. LCMS(m/z) 204.93 [M+H]+.

Intermediate 2. [1,2,4]triazolo[4,3-a]quinazolin-5(4H)-one

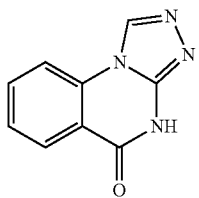 [SMILES: O=c1[nH]c2nncn2c2ccccc12]

[1,2,4]triazolo[4,3-a]quinazolin-5(4H)-one (Intermediate 2) can be alternatively synthesized according to the following route.

(Step 1) Synthesis of 2-chloro-4(3H)-quinazolinone

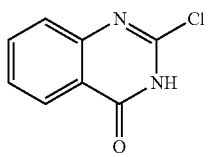 [SMILES: O=c1[nH]c(Cl)nc2ccccc12]

A mixture of 2,4-dichloroquinazoline (5 g, 25.1 mmol) in 2M NaOH solution (60 mL, 60 mmol) and THF (60 mL) was stirred for 1.5h at RT. The reaction mixture was cooled and adjusted to pH 5 with AcOH. The precipitated solids were collected and washed with water, EtOH to give the desired product. LCMS(m/z) 181.06 [M+H]+.

(Step 2) Synthesis of 2-Chloro-3-((2-(trimethylsilyl)ethoxy)methyl)quinazolin-4(3H)-one

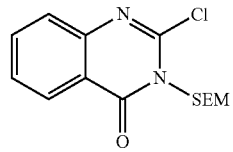 [SMILES: C[Si](C)(C)CCOCn1c(Cl)nc2ccccc2c1=O]

A solution of 2-chloro-4(3H)-quinazolinone (3.9 g, 21.60 mmol), SEM-Cl (4.21 ml, 23.76 mmol) and $K_2CO_3$ (3.58 g, 25.9 mmol) in DMF (50 mL) was stirred overnight at RT. The reaction mixture was diluted with EtOAc, washed successively with water and brine, dried over $Na_2SO_4$, and concentrated in vacuo. The crude was used for the next step without purification.

(Step 3) Synthesis of 2-Hydrazinyl-3-((2-(trimethylsilyl)ethoxy)methyl)quinazolin-4(3H)-one

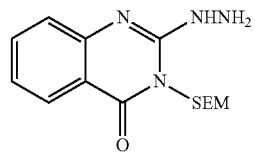 [SMILES: C[Si](C)(C)CCOCn1c(NN)nc2ccccc2c1=O]

A solution of 2-Chloro-3-((2-(trimethylsilyl)ethoxy)methyl)quinazolin-4(3H)-one (170 mg, 0.547 mmol) in a mixture of hydrazine hydrate (0.5 mL, 15.93 mmol) and EtOH (2 mL) was stirred for 1.5h at RT. The reaction mixture was diluted with EtOAc, washed successively with water and brine, dried over $Na_2SO_4$, and concentrated in vacuo. The crude material was used for the next step without purification. LCMS(m/z) 307.18 [M+H]+.

(Step 4) Synthesis of 4-((2-(trimethylsilyl)ethoxy)methyl)-[1,2,4]triazolo[4,3-a]quinazolin-5(4H)-one

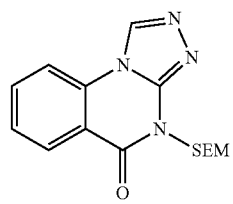 [SMILES: C[Si](C)(C)CCOCn1c(=O)c2ccccc2n2cnnc12]

A solution of the resulting 2-hydrazinyl-3-((2-(trimethylsilyl)ethoxy)methyl)quinazolin-4(3H)-one in triethoxymethane (3 mL) was stirred for overnight at 100° C.

The reaction mixture was purified by column chromatography (Si-column, hexane:AcOEt=100:0-0:100) to give the desired product.

(Step 5) Synthesis of [1,2,4]triazolo[4,3-a]quinazolin-5(4H)-one

A mixture of 4-((2-(trimethylsilyl)ethoxy)methyl)-[1,2,4]triazolo[4,3-a]quinazolin-5(4H)-one (187 mg, 0.591 mmol) and 2,2,2-trifluoroacetic acid (2 mL, 0.591 mmol) was stirred for 1 h at RT. The reaction mixture was concentrated in vacuo. The resulting solids were collected to give the desired product. LCMS(m/z) 187.11 [M+H]+; $^1$H NMR (400 MHz, DMSO-$d_6$) δ 12.80 (s, 1H), 9.40 (s, 1H), 8.21-8.12 (m, 2H), 7.96-7.85 (m, 1H), 7.57 (ddd, J=8.1, 7.4, 1.0 Hz, 1H).

Intermediate 3. 8-bromo-5-chloro-[1,2,4]triazolo[4,3-a]quinazoline

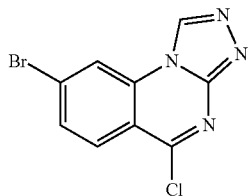

(Step 1) Synthesis of 7-Bromoquinazoline-2,4(1H,3H)-dione

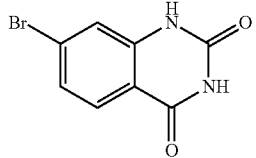

A mixture of 2-amino-4-bromobenzoic acid (20 g, 92.59 mmol) and urea (55.55 g, 925.92 mmol) was heated to 150° C. for 16 h. The progress of the reaction was monitored by TLC. After completion of the reaction, the reaction mixture was diluted with ice-water and stirred for 30 min. The resulting solids were collected, and triturated with glacial acetic acid and washed with petroleum ether to give the desired product. LCMS(m/z) 241.06 [M+H]+.

(Step 2) Synthesis of 7-Bromo-2,4-dichloroquinazoline

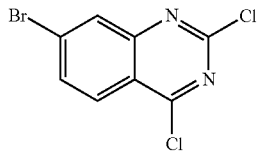 [SMILES: Clc1nc(Cl)c2ccc(Br)cc2n1]

To a stirred solution of 7-bromoquinazoline-2,4(1H,3H)-dione (19 g, 79.17 mmol) in phosphorus oxychloride (74 mL, 791.67 mmol) was added N,N-diisopropylethylamine (19.6 mL, 118.75 mmol) at 0° C., and the mixture was heated to 110° C. for 16 h. The progress of the reaction was monitored by TLC. After completion of the reaction, the reaction mixture was diluted with ice-water and stirred for 30 min. The resulting solids were collected, and washed with cold water and dried under vacuum to afford the desired product. LCMS(m/z) 277.08 [M+H]+.

(Step 3) Synthesis of 7-Bromo-2-chloroquinazolin-4(3H)-one

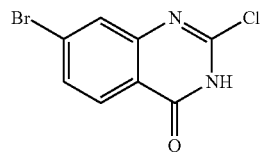 [SMILES: O=c1[nH]c(Cl)nc2cc(Br)ccc12]

To a stirred solution of 7-bromo-2,4-dichloroquinazoline (22.0 g, 79.71 mmol) in THF (200 mL) was added 1M NaOH (191 mL, 191.30 mmol) at 0° C., and the mixture was stirred for 2 h at RT. The progress of the reaction was monitored by TLC. After completion of the reaction, the reaction mixture was acidified with glacial acetic acid to pH~5. The resulting solids were filtered and dried under vacuum to give the desired product. LCMS(m/z) 259.17 [M+H]+.

(Step 4) Synthesis of 7-Bromo-2-chloro-3-((2-(trimethylsilyl)ethoxy)methyl)quinazolin-4(3H)-one

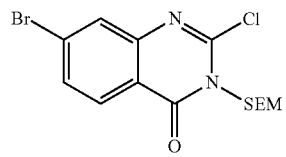

To a stirred solution of 7-bromo-2-chloroquinazolin-4(3H)-one (14.5 g, 56.20 mmol) in DMF (150 mL) were added potassium carbonate (8.53 g, 61.82 mmol) and 2-(trimethylsilyl)ethoxymethyl chloride (10.96 mL g, 61.82 mmol) at 0° C., and the mixture was stirred for 4 h a RT. The progress of the reaction was monitored by TLC. After completion of the reaction, the reaction mixture was diluted with water and extracted with ethyl acetate. The organic layer was washed successively with water and brine, dried over $Na_2SO_4$, filtered and evaporated under reduced pressure to give the desired product.

(Step 5) Synthesis of 7-Bromo-2-hydrazinyl-3-((2-(trimethylsilyl)ethoxy)methyl)-quinazolin-4(3H)-one

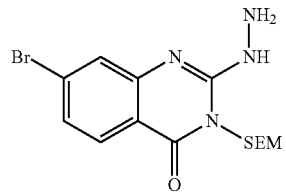

To a stirred solution of 7-bromo-2-chloro-3-((2-(trimethylsilyl)ethoxy)methyl)quinazolin-4(3H)-one (15 g, 38.66 mmol) in EtOH (150 mL) was added hydrazine (386 mL, 386.60 mmol, 1.0 M in THF) at 0° C., and the mixture was stirred for 2 h at RT. The progress of the reaction was monitored by TLC. After completion of the reaction, the reaction mixture was diluted with water and extracted with 10% methanol/dichloromethane. The organic layer was washed successively with water and brine, dried over Na₂SO₄, filtered and evaporated under reduced pressure to give the desired product. LCMS(m/z) 385.40 [M+H]+.

(Step 6) Synthesis of 8-Bromo-4-((2-(trimethylsilyl)ethoxy)methyl)-[1,2,4]triazolo[4,3-a]quinazolin-5(4H)-one

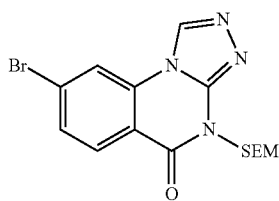 [SMILES: C[Si](C)(C)CCOCn1c(=O)c2ccc(Br)cc2n2cnnc12]

A mixture of 7-bromo-2-hydrazinyl-3-((2-(trimethylsilyl)ethoxy)methyl)quinazolin-4(3H)-one (17 g, 44.27 mmol) and triethylorthoformate (43.74 mL, 265.62 mmol) was heated to 100° C. for 16 h. The progress of the reaction was monitored by TLC. After completion of the reaction, the reaction mixture was evaporated under reduced pressure. The resulting residue was triturated with diethyl ether to give the desired product. LCMS(m/z) 397.35 [M+H+2, isotopic mass]+.

(Step 7) Synthesis of 8-Bromo-[1,2,4]triazolo[4,3-a]quinazolin-5(4H)-one

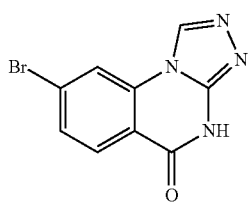

To a stirred solution of 8-bromo-4-((2-(trimethylsilyl)ethoxy)methyl)-[1,2,4]triazolo[4,3-a]quinazolin-5(4H)-one (1.5 g, 5.1 mmol) in methanol (15 mL) was added trifluoroacetic acid (1.5 mL) at RT, and the mixture was stirred at RT for 16 h. The progress of the reaction was monitored by TLC. After completion of the reaction, the reaction mixture evaporated under reduced pressure. The resulting residue was triturated with diethyl ether to afford the desired product. LCMS(m/z) 265.27 [M+H]+; ¹H NMR (400 MHz, DMSO-d₆) δ=12.88 (br. s, 1H), 9.41 (s, 1H), 8.55 (d, J=1.5 Hz, 1H), 8.05 (d, J=8.6 Hz, 1H), 7.75 (dd, J=1.6, 8.4 Hz, 1H).

Synthesis of 8-Bromo-5-chloro-[1,2,4]triazolo[4,3-a]quinazoline

A mixture of 8-bromo-[1,2,4]triazolo[4,3-a]quinazolin-5(4H)-one (2.0 g, 7.57 mmol) in phosphorus oxychloride (15 mL) was refluxed for 6 h. The progress of the reaction was monitored by TLC. After completion of the reaction, the reaction mixture was evaporated under reduced pressure. The residue was dissolved in toluene and evaporated twice to afford the desired product: LCMS(m/z) 283.20 [M+H]+.

Intermediate 4. 8-Nitro-[1,2,4]triazolo[4,3-a]quinazolin-5(4H)-one

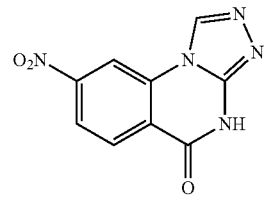 [SMILES: O=c1[nH]c2nncn2c2cc([N+](=O)[O-])ccc12]

(Step 1) Synthesis of 7-Nitroquinazoline-2,4(1H,3H)-dione

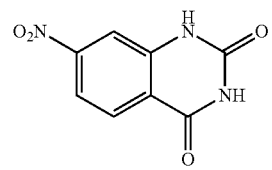 [SMILES: O=c1[nH]c(=O)c2ccc([N+](=O)[O-])cc2[nH]1]

A mixture of 2-amino-4-nitrobenzoic acid (10 g, 54.94 mmol) and urea (32.96 g, 549.45 mmol) was heated to 150° C. for 16 h. The progress of the reaction was monitored by TLC. After completion of the reaction, the reaction mixture was diluted with ice-water and stirred for 10 min. The resulting solids were collected and triturated with glacial acetic acid to give the desired product. LCMS(m/z) 208.14 [M+H]+.

(Step 2) Synthesis of 2,4-Dichloro-7-nitroquinazoline

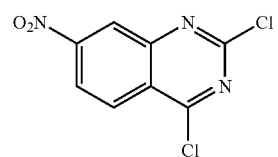 [SMILES: O=[N+]([O-])c1ccc2c(Cl)nc(Cl)nc2c1]

To a stirred solution of 7-nitroquinazoline-2,4(1H,3H)-dione (10.3 g, 49.76 mmol) in phosphorus oxychloride (48 mL, 497.58 mmol) and N,N-diisopropylethylamine (13 mL, 74.64 mmol) at 0° C. and the mixture was heated to 110° C. for 16 h. The progress of the reaction was monitored by TLC. After completion of the reaction, the reaction mixture was quenched with crushed ice and stirred for 10 min. The resulting solids were filtered and dried under vacuum to give the desired product. LCMS(m/z) 244.11 [M+H]+.

(Step 3) Synthesis of
2-Chloro-7-nitroquinazolin-4(3H)-one

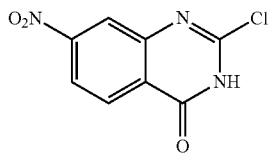 [SMILES: O=c1[nH]c(Cl)nc2cc([N+](=O)[O-])ccc12]

To a stirred solution of 2,4-dichloro-7-nitroquinazoline (20 g, 82.3 mmol) in THF (5 mL) was added 1M NaOH solution (197 mL, 197.53 mmol) at 0° C. and the mixture was stirred for 2 h at RT. The progress of the reaction was monitored by TLC. After completion of the reaction, the reaction mixture was acidified with acetic acid to pH~5 at 0° C. The resulting solids were filtered and dried under vacuum to give the desired product. LCMS(m/z) 226.21 [M+H]+.

(Step 4) Synthesis of 2-Chloro-7-nitro-3-((2-(trimethylsilyl)ethoxy)methyl)quinazolin-4(3H)-one

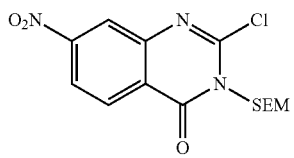 [SMILES: C[Si](C)(C)CCOCn1c(Cl)nc2cc([N+](=O)[O-])ccc2c1=O]

To a stirred solution of 2-chloro-7-nitroquinazolin-4(3H)-one (15.6 g, 69.33 mmol) in DMF (160 mL) were added potassium carbonate (10.54 g, 76.27 mmol) and 2-(trimethylsilyl)ethoxymethyl chloride (13.52 mL, 76.27 mmol) at 0° C. and the mixture was stirred for 4 h at RT. The progress of the reaction was monitored by TLC. After completion of the reaction, the reaction mixture was diluted with water and extracted with ethyl acetate. The organic layer was washed successively with water and brine, dried over $Na_2SO_4$, filtered and evaporated under reduced pressure to give the desired product. LCMS(m/z) 356.42 [M+H]+.

(Step 5) Synthesis of 2-Hydrazinyl-7-nitro-3-((2-(trimethylsilyl)ethoxy)methyl)-quinazolin-4(3H)-one

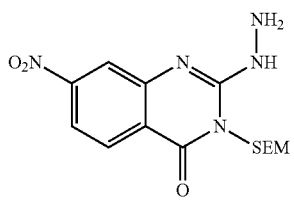 [SMILES: C[Si](C)(C)CCOCn1c(NN)nc2cc([N+](=O)[O-])ccc2c1=O]

To a stirred solution of 2-chloro-7-nitro-3-((2-(trimethylsilyl)ethoxy)methyl)quinazolin-4(3H)-one 5 (crude, 10 g, 28.17 mmol) in EtOH (100 mL) was added hydrazine (281 mL, 281.69 mmol, 1.0M in THF) at 0° C. and the mixture was stirred for 2 h at RT. The progress of the reaction was monitored by TLC. After completion of the reaction, the reaction mixture was diluted with water and extracted with 10% methanol/dichloromethane. The organic layer was dried over $Na_2SO_4$, filtered and evaporated under reduced pressure to give the desired product. LCMS(m/z) 352.53 [M+H]+.

(Step 6) Synthesis of 8-Nitro-4-((2-(trimethylsilyl)ethoxy)methyl)-[1,2,4]triazolo[4,3-a]quinazolin-5(4H)-one

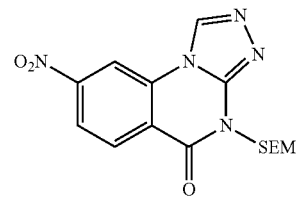 [SMILES: C[Si](C)(C)CCOCn1c(=O)c2ccc([N+](=O)[O-])cc2n2cnnc12]

The mixture of 2-hydrazinyl-7-nitro-3-((2-(trimethylsilyl)ethoxy)methyl)quinazolin-4(3H)-one (crude, 12.0 g, 34.19 mmol) and triethylorthoformate (34.15 mL, 205.13 mmol, 6.0 eq.) was heated to 100° C. for 16 h. The progress of the reaction was monitored by TLC. After completion of the reaction, the reaction mixture was evaporated under reduced pressure, and the residue was washed with diethyl ether and dried under vacuum to give the desired product. LCMS(m/z) 362.40 [M+H]+.

(Step 7) Synthesis of 8-Nitro-[1,2,4]triazolo[4,3-a]quinazolin-5(4H)-one

To a stirred solution of 8-nitro-4-((2-(trimethylsilyl)ethoxy)methyl)-[1,2,4]triazolo[4,3-a]quinazolin-5(4H)-one (6.3 g, 24.14 mmol) in MeOH (60 mL) was added triethylamine (6.09 mL, 43.45 mmol) at RT and the mixture was stirred for 16 h at the same temperature. The progress of the reaction was monitored by TLC. After completion of the reaction, the reaction mixture was evaporated under reduced pressure, and the residue was washed successively with diethyl ether, n-pentane, and dried under vacuum to afford the desired product: LCMS(m/z) 231.9 [M+H]+; $^1$H NMR (500 MHz, DMSO-$d_6$) δ=13.10 (brs, 1H), 9.65 (s, 1H), 9.10 (d, J=2.1 Hz, 1H), 8.40-8.36 (m, 1H), 8.31 (dd, J=2.0, 9.0 Hz, 1H).

Intermediate 5. 5,8-Dichloro-[1,2,4]triazolo[4,3-a]quinazoline

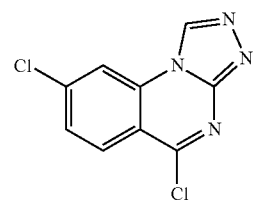 [SMILES: Clc1ccc2c(Cl)nc3nncn3c2c1]

(Step 1) synthesis of 7-Chloroquinazoline-2,4(1H,3H)-dione

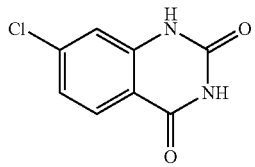

A mixture of 2-amino-4-chlorobenzoic acid (10 g, 58.48 mmol) and urea (35.09 g, 584.79 mmol) was stirred at 150° C. for 16 h. The reaction mixture was diluted with ice-cold water at 100° C. The resulting solids were filtered, washed with water and dried under vacuum to give the desired product: LCMS(m/z) 197.13 [M+H]+.

(Step 2) synthesis of 2,4,7-Trichloroquinazoline

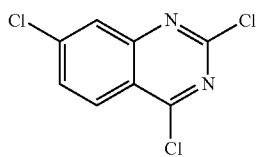 [SMILES: Clc1ccc2c(Cl)nc(Cl)nc2c1]

To a solution of 7-chloroquinazoline-2,4(1H,3H)-dione (9.1 g, 46.43 mmol) in phosphorus oxychloride (43.39 mL, 464.28 mmol) was added N, N-diisopropylethylamine (12.14 mL, 69.64 mmol) at 0° C. and the mixture was stirred at 110° C. for 16 h. The reaction mixture was diluted with ice-cold water, and the resulting solids were filtered, washed with water and dried under vacuum to give the desired product.

(Step 3) synthesis of 2,7-Dichloroquinazolin-4(3H)-one

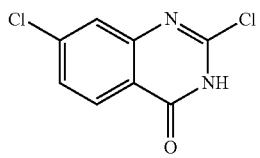 [SMILES: O=c1[nH]c(Cl)nc2cc(Cl)ccc12]

To a solution of 2,4,7-trichloroquinazoline (10 g, 43.10 mmol) in THF (100 mL) was added 1M NaOH solution (103.45 mL, 103.45 mmol) at 0° C. and the mixture was stirred for 2 h at RT. The reaction mixture was acidified with acetic acid to pH~5 at 0° C. The resulting solids were filtered, washed with water, petroleum ether and dried under vacuum to give the desired product. LCMS(m/z) 215.09 [M+H]+.

(Step 4) synthesis of 2,7-Dichloro-3-((2-(trimethyl-silyl)ethoxy)methyl)quinazolin-4(3H)-one

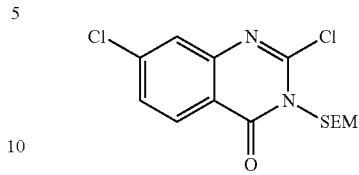

To a solution of 2,7-dichloroquinazolin-4(3H)-one (8.6 g, 40 mmol) in DMF (90 mL) were added potassium carbonate (6.07 g, 44 mmol) and 2-(trimethylsilyl)ethoxymethyl chloride (7.80 mL, 44 mmol) at 0° C. and the mixture was stirred for 4 h at RT. The reaction mixture was diluted with ice-water and extracted with ethyl acetate. The organic layer was washed with ice-water, brine, dried over Na$_2$SO$_4$, and evaporated under reduced pressure to give the desired product. LCMS(m/z) 345.33 [M+H]+.

(Step 5) synthesis of 7-Chloro-2-hydrazinyl-3-((2-(trimethylsilyl)ethoxy)methyl)-quinazolin-4(3H)-one

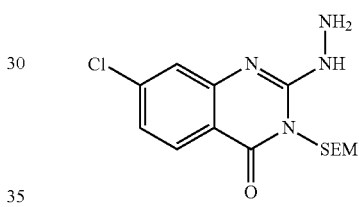

To a solution of 2,7-dichloro-3-((2-(trimethylsilyl)ethoxy)methyl)quinazolin-4(3H)-one (5 g, 14.53 mmol) in EtOH (50 mL) was added hydrazine (145 mL, 145.35 mmol, 1.0 M in THF) at 0° C. and the mixture was stirred for 2 h at RT. The reaction mixture was diluted with water and extracted with 10% methanol/dichloromethane. The organic layer was washed with brine, dried over Na$_2$SO$_4$, filtered and evaporated under reduced pressure. The residue was washed with diethyl ether to give the desired product. LCMS(m/z) 341.37 [M+H]+.

(Step 6) synthesis of 8-Chloro-4-((2-(trimethylsilyl)ethoxy)methyl)-[1,2,4]triazolo[4,3-a]quinazolin-5(4H)-one

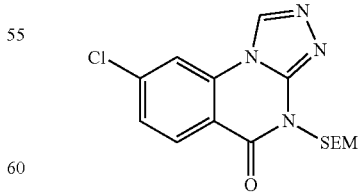

A mixture of 7-chloro-2-hydrazinyl-3-((2-(trimethylsilyl)ethoxy)methyl)quinazolin-4(3H)-one (4.9 g, 14.41 mmol) and triethyl orthoformate (14.39 mL, 86.47 mmol) was stirred at 100° C. for 16 h. The reaction mixture was diluted with diethyl ether and evaporated under reduced pressure.

The residue was dissolved in diethyl ether and evaporated to give the desired product. LCMS(m/z) 351.42 [M+H]+.

(Step 7) synthesis of 8-Chloro-4-(hydroxymethyl)-[1,2,4]triazolo[4,3-a]quinazolin-5(4H)-one

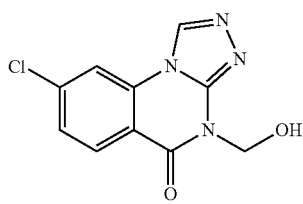 [SMILES: O=c1c2ccc(Cl)cc2n2cnnc2n1CO]

To a solution of 8-chloro-4-((2-(trimethylsilyl)ethoxy)methyl)-[1,2,4]triazolo[4,3-a]quinazolin-5(4H)-one 7 (2.18 g, 6.23 mmol) in dichloromethane (20 mL) was added trifluoroacetic acid (5.72 mL, 74.74 mmol) at 0° C. and the mixture was stirred for 16 h at RT. The reaction mixture was evaporated under reduced pressure, and the residue was dissolved in dichloromethane and evaporated. The resulting solids were washed with diethyl ether to give the desired product.

(Step 8) synthesis of 8-Chloro-[1,2,4]triazolo[4,3-a]quinazolin-5(4H)-one

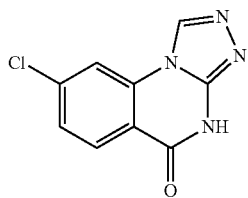 [SMILES: O=c1[nH]c2nncn2c2cc(Cl)ccc12]

To a solution of 8-chloro-4-(hydroxymethyl)-[1,2,4]triazolo[4,3-a]quinazolin-5(4H)-one (1.8 g, 7.2 mmol) in MeOH (20 mL) was added triethylamine (2.02 mL, 14.4 mmol) at 0° C. and the mixture was stirred for 16 h at RT. The reaction mixture was evaporated under reduced pressure, and the residue was dissolved in diethyl ether and evaporated. The resulting solids were washed with diethyl ether to give the desired product. LCMS(m/z) 221.21 [M+H]+.

(Step 9) synthesis of 5,8-Dichloro-[1,2,4]triazolo[4,3-a]quinazoline

A solution of 8-chloro-[1,2,4]triazolo[4,3-a]quinazolin-5(4H)-one (1.2 g, 5.45 mmol) in phosphorus oxychloride (15 mL) was stirred at 100° C. for 6 h. The reaction mixture was evaporated under reduced pressure. The residue was dissolved in toluene and evaporated to give the desired product. LCMS(m/z) 239.17 [M+H]+.

B. Examples

Example 1. N-methyl-N-phenyl-[1,2,4]triazolo[4,3-a]quinazolin-5-amine

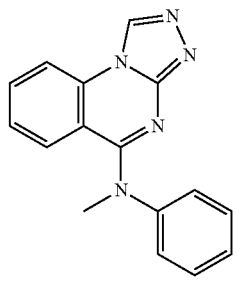 [SMILES: CN(c1ccccc1)c1nc2nncn2c2ccccc12]

(Step 1) Synthesis of 2-chloro-N-methyl-N-phenylquinazolin-4-amine

N-methyl aniline (59.2 mg, 0.553 mmol) and sodium hydroxide (20 mg, 0.500 mmol) were added to a DMF solution (5 ml) of 2,4-dichloroquinazoline (100 mg, 0.502 mmol), and stirred at room temperature for 2 hours. Ethyl acetate and water were added to the reaction solution and an organic layer was separated. The organic layer was washed with a saturated aqueous ammonium chloride solution, and dried over anhydrous magnesium sulfate. The solvent was evaporated under reduced pressure, and the residue was purified with a silica gel column chromatography (hexane:ethyl acetate=1:0 to 4:1) to give 2-chloro-N-methyl-N-phenylquinazolin-4-amine: $^1$H-NMR (400 MHz, DMSO-$d_6$) δ 7.70-7.65 (m, 2H), 7.53-7.46 (m, 2H), 7.44-7.36 (m, 3H), 7.11 (ddd, J=8.4, 4.8, 3.5 Hz, 1H), 6.83 (dt, J=8.6, 1.0 Hz, 1H), 3.56); LCMS(m/z) 270.13 [M+H]$^+$.

(Step 2) Synthesis of 2-hydrazyl-N-methyl-7-phenylquinazolin-4-amine

An ethanol solution (3 ml) of 2-chloro-N-methyl-N-phenylquinazolin-4-amine (135 mmol, 0.500 mmol) and hydrazine monohydrate (75 mg, 1.50 mmol) was stirred at 50° C. for an hour. The reaction mixture was cooled to room temperature, ethyl acetate and water were added, and the organic layer was separated. The organic layer was washed with brine, and dried over anhydrous magnesium sulfate. The solvent was evaporated under reduced pressure to give 2-hydrazyl-N-methyl-7-phenylquinazolin-4-amine: $^1$H NMR (400 MHz, Methanol-$d_4$) δ 8.36 (d, J=8.3 Hz, 1H), 7.88-7.76 (m, 3H), 7.67 (d, J=8.4 Hz, 1H), 7.59 (t, J=7.7 Hz, 1H), 7.41 (t, J=7.8 Hz, 2H), 7.21 (t, J=7.4 Hz, 1H), 3.55 (s, 3H); LCMS(m/z) 266.13 [M+H]$^+$.

(Step 3) Synthesis of N-methyl-N-phenyl-[1,2,4]triazolo[4,3-a]quinazolin-5-amine A mixture of 2-hydrazyl-N-methyl-7-phenylquinazolin-4-amine (78 mg, 0.294 mmol) and triethyl orthoformate (1 ml) was stirred at 50° C. for an hour. The reaction mixture was cooled to room temperature and purified with a silica gel column chromatography (chloroform:methanol=1:0 to 10:1) to give the titled compound: $^1$H-NMR 400 MHz, DMSO-$d_6$)

δ 9.62 (s, 1H), 8.29 (d, J=8.3 Hz, 1H), 7.77 (ddd, J=8.4, 6.7, 1.7 Hz, 1H), 7.44-7.21 (m, 7H), 3.32 (s, 3H).; LCMS(m/z) 276.1 [M+H]+.

Example 2. N-(3-chlorophenyl)-N-methyl-[1,2,4]triazolo[4,3-a]quinazolin-5-amine

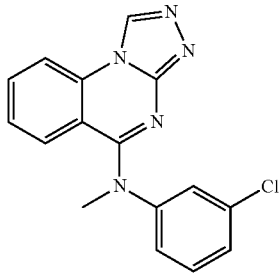 [SMILES: CN(c1cccc(Cl)c1)c1nc2nncn2c2ccccc12]

(Step 1) Synthesis of 2-hydrazyl-quinazolin-4(3H)-one

An ethanol solution (2 ml) of 2-chloroquinazolin-4(3H)-one (50 mg, 0.277 mmol) and hydrazine monohydrate (41.6 mg, 0.831 mmol) was heated to 50° C. and stirred for 1.5 hours. The reaction mixture was cooled to room temperature, ethyl acetate and water were added and the organic layer was separated. The organic layer was washed with brine, and dried over anhydrous magnesium sulfate. The solvent was evaporated and 2-hydrazyl-quinazolin-4(3H)-one was obtained: $^1$H-NMR (DMSO-$d_6$) δ (ppm): 8.08-6.85 (m, 4H); LCMS(m/z) 177.11 [M+H]+.

(Step 2) Synthesis of [1,2,4]-triazolo-[4,3-a]quinazolin-5(4H)-one

A mixture of 2-hydrazyl-quinazolin-4(3H)-one (1.26 g, 7.15 mmol) and triethyl orthoformate (10 ml) was heated to 80° C. and stirred for 2 hours. The reaction mixture was cooled to room temperature, and the solvent was evaporated under reduced pressure. The residue was purified with a silica gel chromatography (chloroform:methanol=1:0 to 20:1) to give [1,2,4]-triazolo-[4,3-a]quinazolin-5(4H)-one: $^1$H-NMR (DMSO-$d_6$) δ (ppm): 12.80 (s, 1H), 9.40 (s, 1H), 8.20-8.12 (m, 2H), 7.96-7.85 (m, 1H), 7.57 (ddd, J=8.1, 7.4, 1.0 Hz, 1H); LCMS(m/z) 187.16 [M+H]+.

(Step 3) Synthesis of N-(3-chlorophenyl)-N-methyl-[1,2,4]triazolo[4,3-a]quinazolin-5-amine LDA (0.147 ml, 0.293 mmol) was added at 0° C. to a THF solution (2 ml) of [1,2,4]-triazolo-[4,3-a]quinazolin-5(4H)-one (30 mg, 0.147 mmol) and stirred for 30 minutes. A THF solution (31 ml) of 3-chloro-N-methylalinin (31.1 mg, 0.22 mmol) was added to this solution and stirred at room temperature for an hour. Ethyl acetate and water were added to the reaction solution and the organic layer was separated. The organic layer was washed with brine, and dried over anhydrous magnesium sulfate. The solvent was evaporated under reduced pressure and the residue was purified with a preparative HPLC chromatography to give the titled compound: $^1$H-NMR (DMSO-$d_6$) δ (ppm): 9.66 (s, 1H), 8.36-8.28 (m, 1H), 7.82 (ddd, J=8.5, 6.4, 2.2 Hz, 1H), 7.48 (t, J=2.1 Hz, 1H), 7.42-7.21 (m, 5H), 3.55 (s, 3H); LCMS(m/z) 310.13 [M+H]+.

Example 3. N-phenyl-[1,2,4]triazolo[4,3-a]quinazolin-5-amine

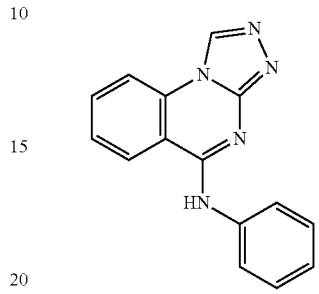

(Step 1) Synthesis of 2-chloro-N-phenylquinazolin-4-amine

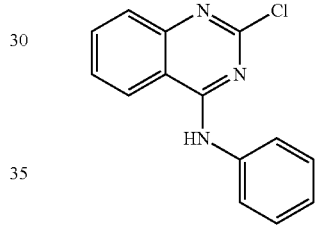

To a solution of 2,4-dichloroquinazoline (100 mg, 0.502 mmol) in DMF (2.5 mL) were added aniline (46.8 mg, 0.502 mmol) and sodium hydroxide (20.1 mg, 0.502 mmol), and the mixture was stirred for 30 min at RT. The reaction mixture was diluted with water, and extracted with AcOEt. The organic layer was concentrated in vacuo. The crude product was used for next step without further purification. LCMS(m/z) 256.09 [M+H]+.

(Step 2) Synthesis of N-phenyl-[1,2,4]triazolo[4,3-a]quinazolin-5-amine

A mixture of the resulting 2-chloro-N-phenylquinazolin-4-amine (70 mg, 0.274 mmol) and formohydrazide (32.9 mg, 0.548 mmol) in toluene (1.37 mL) was refluxed for 2.5 days. The reaction mixture was diluted with MeOH/AcOEt, concentrated in vacuo. The residue was dissolved in MeOH and evaporated to remove the residual solvent. The residue was suspended with MeOH, and the resulting solids were collected and washed to give the desired product: $^1$H-NMR (DMSO-$d_6$) δ 9.80 (s, 1H), 9.53 (s, 1H), 8.67 (dd, J=8.3, 1.2 Hz, 1H), 8.33 (dd, J=8.3, 1.1 Hz, 1H), 7.99 (ddd, J=8.4, 7.2, 1.2 Hz, 1H), 7.94-7.83 (m, 2H), 7.71 (ddd, J=8.3, 7.2, 1.1 Hz, 1H), 7.49-7.38 (m, 2H), 7.23-7.14 (m, 1H); LCMS(m/z) 262.2 [M+H]+.

Example 4. 5-(3,4-dihydroquinolin-1(2H)-yl)-[1,2,4]triazolo[4,3-a]quinazoline

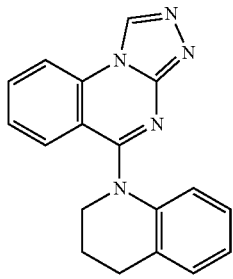 [SMILES: c1ccc2c(c1)CCCN2c1nc2nncn2c2ccccc12]

(Step 1) Synthesis of 2-chloro-4-(3,4-dihydroquinolin-1(2H)-yl)quinazoline

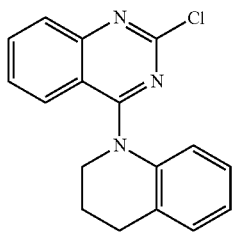 [SMILES: Clc1nc(N2CCCc3ccccc32)c2ccccc2n1]

To a solution of 2,4-dichloroquinazoline (150 mg, 0.615 mmol) in DMF (2.5 mL) were added 1,2,3,4-tetrahydroquinoline (66.9 mg, 0.502 mmol) and sodium hydride (22.1 mg, 0.553 mmol), and the mixture was stirred for 2 h at RT. The reaction mixture was diluted with AcOEt, and washed successively with water and brine, and dried over $Na_2SO_4$. The organic layer was concentrated in vacuo. The resultant residue was used for the next step without further purification. LCMS(m/z) 296.08 $[M+H]^+$.

(Step 2) Synthesis of 5-(3,4-dihydroquinolin-1(2H)-yl)-[1,2,4]triazolo[4,3-a]quinazoline A mixture of the resulting 2-chloro-4-(3,4-dihydroquinolin-1(2H)-yl)quinazoline (50 mg, 0.172 mmol) and formohydrazide (20.3 mg, 0.338 mmol) in toluene (0.84 mL) was refluxed for 2.5 days. The reaction mixture was diluted with MeOH/AcOEt and concentrated in vacuo. The residue was purified by prep. HPLC to afford the desired product: $^1$H-NMR (DMSO-$d_6$) δ 9.70 (s, 1H), 8.40-8.29 (m, 1H), 7.87 (ddd, J=8.5, 7.3, 1.4 Hz, 1H), 7.57 (dd, J=8.3, 1.3 Hz, 1H), 7.37 (ddd, J=8.3, 7.2, 1.2 Hz, 1H), 7.27 (dd, J=7.4, 1.6 Hz, 1H), 7.04-6.88 (m, 2H), 6.72 (dd, J=8.0, 1.2 Hz, 1H), 3.92 (t, J=6.5 Hz, 2H), 2.89 (t, J=6.6 Hz, 2H), 2.12-1.96 (m, 2H). LCMS(m/z) 302.2 $[M+H]^+$.

Example 5. N-(4-methoxyphenyl)-N-methyl-[1,2,4]triazolo[4,3-a]quinazolin-5-amine

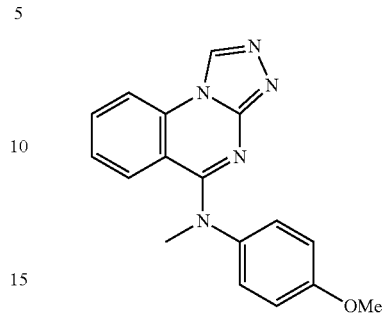

(Step 1) Synthesis of 2-chloro-N-(4-methoxyphenyl)-N-methylquinazolin-4-amine

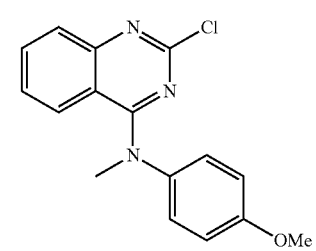 [SMILES: COc1ccc(N(C)c2nc(Cl)nc3ccccc23)cc1]

To a solution of 2,4-dichloroquinazoline (100 mg, 0.502 mmol) in DMF (2.5 mL) were added 4-methoxy-N-methylaniline (68.9 mg, 0.502 mmol) and sodium hydroxide (20.1 mg, 0.502 mmol), and the mixture was stirred for 0.5 h at RT. The reaction mixture was diluted with AcOEt, washed successively with water and brine, and dried over $Na_2SO_4$. The organic layer was concentrated in vacuo. The resultant residue was used for the next step without further purification. LCMS(m/z) 300.08 $[M+H]^+$.

(Step 2) Synthesis of N-(4-methoxyphenyl)-N-methyl-[1,2,4]triazolo[4,3-a]quinazolin-5-amine A mixture of the resulting 2-chloro-N-(4-methoxyphenyl)-N-methylquinazolin-4-amine (71 mg, 0.237 mmol) and formohydrazide (21.3 mg, 0.355 mmol) in toluene (1.18 mL) was stirred reflux for 2 days. The reaction mixture was diluted with MeOH/AcOEt, concentrated in vacuo. The residue was purified by prep. HPLC to afford the desired product: $^1$H-NMR (Methanol-$d_4$) δ 9.38 (d, J=2.5 Hz, 1H), 8.10 (t, J=6.6 Hz, 1H), 7.71 (t, J=7.6 Hz, 1H), 7.21-7.16 (m, 4H), 6.97 (s, 1H), 6.85-6.72 (m, 1H), 3.82 (s, 3H), 3.60 (d, J=2.6 Hz, 3H); LCMS(m/z) 306.2 $[M+H]^+$.

Example 6. N-(2-fluorophenyl)-N-methyl-[1,2,4]triazolo[4,3-a]quinazolin-5-amine

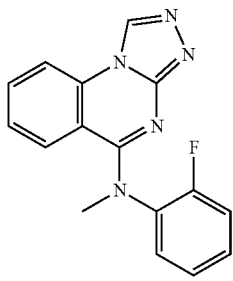

(Step 1) Synthesis of 2-chloro-N-(2-fluorophenyl)-N-methylquinazolin-4-amine

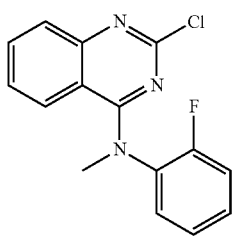 [SMILES: CN(c1ccccc1F)c1nc(Cl)nc2ccccc12]

To a suspension of 2,4-dichloroquinazoline (100 mg, 0.502 mmol) in DMF (2.5 mL) were added 2-fluoro-N-methylaniline (62.9 mg, 0.502 mmol) and sodium hydroxide (20.1 mg, 0.502 mmol), and the mixture was stirred for 30 min at RT. The reaction mixture was diluted with AcOEt, washed successively with water and brine, and dried over Na$_2$SO$_4$. The organic layer was concentrated in vacuo. The residue was purified by column chromatography (Si-column, hexane:AcOEt=10:0-6:4) to give the desired product. LCMS(m/z) 288.13 [M+H]+.

(Step 2) Synthesis of N-(2-fluorophenyl)-N-methyl-[1,2,4]triazolo[4,3-a]quinazolin-5-amine A mixture of 2-chloro-N-(2-fluorophenyl)-N-methylquinazolin-4-amine (47 mg, 0.163 mmol) and formohydrazide (19.62 mg, 0.327 mmol) in toluene (0.82 mL) was refluxed for 2 days. The reaction mixture was diluted with MeOH/AcOEt, concentrated in vacuo. The residue was dissolved in MeOH and evaporated. The residue was purified by prep-HPLC to afford the desired product: $^1$H-NMR (Methanol-d$_4$) δ 9.46 (s, 1H), 8.21 (d, J=8.3 Hz, 1H), 7.80 (t, J=7.8 Hz, 1H), 7.45-7.24 (m, 6H), 3.63 (s, 3H). LCMS(m/z) 294.2 [M+H]+.

Example 7. N,N-dimethyl-[1,2,4]triazolo[4,3-a]quinazolin-5-amine

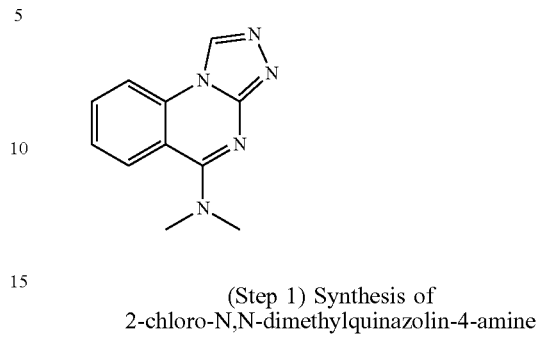

(Step 1) Synthesis of 2-chloro-N,N-dimethylquinazolin-4-amine

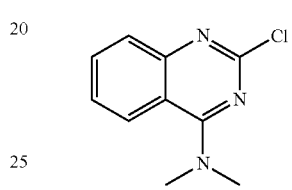

To a suspension of 2,4-dichloroquinazoline (80 mg, 0.402 mmol) in DMF (2.01 ml) were added dimethylamine (18.12 mg, 0.402 mmol) and sodium hydroxide (16.08 mg, 0.402 mmol), and the mixture was stirred for 30 min at RT. The reaction mixture was diluted with AcOEt, and washed successively with water and brine. The organic layer was concentrated in vacuo to give the desired product, which was used for next step without further purification. LCMS(m/z) 208.10 [M+H]+.

(Step 2) Synthesis of N,N-dimethyl-[1,2,4]triazolo[4,3-a]quinazolin-5-amine

A mixture of 2-chloro-N,N-dimethylquinazolin-4-amine (83 mg, 0.4 mmol) and formohydrazide (48 mg, 0.8 mmol) in toluene (2 mL) was refluxed for 2 days. The reaction mixture was dissolved in MeOH/AcOEt, and concentrated in vacuo. The residue was dissolved in MeOH, and evaporated. The residue was purified by prep-HPLC to afford the desired product: $^1$H-NMR (Methanol-d$_4$) δ 9.34 (s, 1H), 8.31 (dd, J=8.4, 1.2 Hz, 1H), 8.19 (dd, J=8.4, 1.1 Hz, 1H), 7.92 (ddd, J=8.4, 7.3, 1.3 Hz, 1H), 7.65 (ddd, J=8.4, 7.2, 1.2 Hz, 1H), 3.40 (s, 6H). LCMS(m/z) 214.1 [M+H]+.

Example 8. 7-methoxy-N-methyl-N-phenyl-[1,2,4]triazolo[4,3-a]quinazolin-5-amine

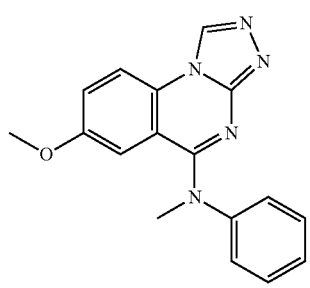 [SMILES: COc1ccc2c(c1)c(N(C)c1ccccc1)nc1nncn12]

(Step 1) Synthesis of 2-chloro-6-methoxy-N-methyl-N-phenylquinazolin-4-amine

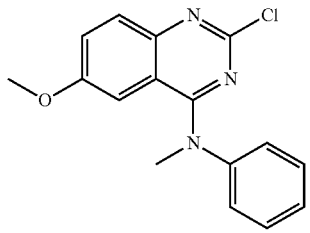 [SMILES: COc1ccc2nc(Cl)nc(N(C)c3ccccc3)c2c1]

To a suspension of 2,4-dichloro-6-methoxyquinazoline (100 mg, 0.437 mmol) in 2-Propanol (2.1 mL) were added N-methylaniline (46.8 mg, 0.437 mmol) and NaOH (15.62 mg, 0.428 mmol), and the mixture was stirred for 3 days at RT. The reaction mixture was filtered and washed with 2-propanol to give the desired product. The product was used for next step without further purification: LCMS(m/z) 309.09 [M+H]+.

(Step 2) Synthesis of 7-methoxy-N-methyl-N-phenyl-[1,2,4]triazolo[4,3-a]quinazolin-5-amine A mixture of 2-chloro-6-methoxy-N-methyl-N-phenylquinazolin-4-amine (70 mg, 0.234 mmol) and formohydrazide (28.0 mg, 0.467 mmol) in Toluene (0.5 mL) was refluxed for 2 days. The reaction mixture was diluted with MeOH/AcOEt, concentrated in vacuo. The residue was dissolved in MeOH and evaporated, and the residue was purified by prep. HPLC to afford the desired product: $^1$H-NMR (Methanol-d4) δ 9.36 (s, 1H), 8.06 (d, J=9.1 Hz, 1H), 7.53-7.40 (m, 2H), 7.38-7.27 (m, 4H), 6.74 (d, J=2.7 Hz, 1H), 3.66 (s, 3H), 3.33 (s, 3H). LCMS(m/z) 306.2 [M+H]+.

Example 9. N-(3-methoxyphenyl)-N-methyl-[1,2,4]triazolo[4,3-a]quinazolin-5-amine

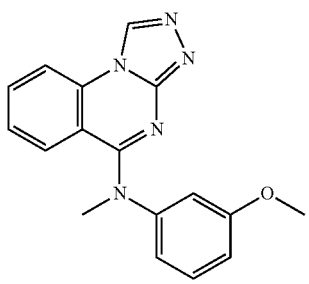 [SMILES: COc1cccc(N(C)c2nc3nncn3c3ccccc23)c1]

To a mixture of [1,2,4]triazolo[4,3-a]quinazolin-5(4H)-one (50 mg, 0.269 mmol) and DBU (0.061 mL, 0.403 mmol) in NMP (1 mL) was added BOP (143 mg, 0.322 mmol) at RT. The mixture was stirred for 10 min at RT. Then, 3-methoxy-N-methylaniline (47.9 mg, 0.349 mmol) was added to the mixture at RT, and the stirring was continued for 3h at RT and then overnight at 55° C. The reaction mixture was purified by prep-LCMS (acidic condition) to afford crude product, which was purified by column chromatography (Si-column, hexane:AcOEt=100:0-0:100, then MeOH) to afford the desired product: $^1$H-NMR (DMSO-d$_6$) δ 9.62 (s, 1H), 8.32-8.25 (m, 1H), 7.78 (ddd, J=8.4, 7.2, 1.4 Hz, 1H), 7.37-7.20 (m, 3H), 6.93 (t, J=2.3 Hz, 1H), 6.82 (m, 2H), 3.71 (s, 3H), 3.54 (s, 3H). LCMS(m/z) 306.1 [M+H]+.

Example 10. 9-fluoro-N-methyl-N-phenyl-[1,2,4]triazolo[4,3-a]quinazolin-5-amine

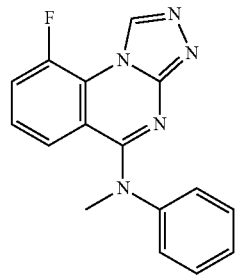

(Step 1)Synthesis of 2-chloro-8-fluoro-N-methyl-N-phenylquinazolin-4-amine

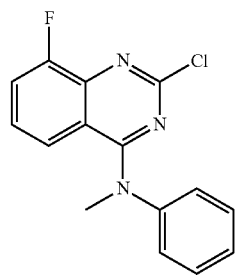 [SMILES: CN(c1ccccc1)c1nc(Cl)nc2c(F)cccc12]

To a suspension of 2,4-dichloro-8-fluoroquinazoline (120 mg, 0.553 mmol) in 2-propanol (2.7 mL) were added N-methylaniline (59.3 mg, 0.553 mmol) and sodium hydroxide (23 mg, 0.55 mmol), and the mixture was stirred for 30 min at RT. The reaction mixture was filtered and washed with 2-propanol to give the desired product, which was used for next step without further purification. LCMS (m/z) 288.08 [M+H]$^+$.

(Step 2) Synthesis of 8-fluoro-2-hydrazinyl-N-methyl-N-phenylquinazolin-4-amine

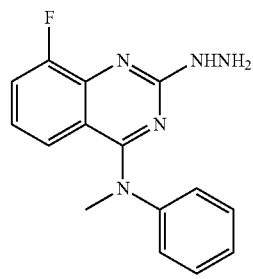 [SMILES: CN(c1ccccc1)c1nc(NN)nc2c(F)cccc12]

A mixture of 2-chloro-8-fluoro-N-methyl-N-phenylquinazolin-4-amine (63 mg, 0.219 mmol) and hydrazine hydrate (54.8 mg, 1.095 mmol) in EtOH (1.1 mL) was stirred for 4 h at 55° C. The reaction mixture was concentrated in vacuo. The resultant residue was used for the next step without further purification. LCMS(m/z) 284.18 [M+H]⁺.

(Step 3) Synthesis of 9-fluoro-N-methyl-N-phenyl-[1,2,4]triazolo[4,3-a]quinazolin-5-amine A mixture of 8-fluoro-2-hydrazinyl-N-methyl-N-phenylquinazolin-4-amine (61 mg, crude) and triethoxymethane (17.26 mg, 0.116 mmol) was stirred at 70° C. for 3 h. A small amount of AcOH was added the reaction mixture, the reaction mixture was concentrated in vacuo. The residue was purified by column chromatography (Si-column, CHCl₃: MeOH=10:0-95:5) to afford the desired product: ¹H-NMR (Methanol-d₄) δ 9.25 (t, J=3.6 Hz, 1H), 7.67-7.56 (m, 1H), 7.42 (t, J=7.7 Hz, 2H), 7.34-7.28 (m, 3H), 7.16 (dd, J=7.9, 4.5 Hz, 2H), 3.66 (d, J=1.9 Hz, 3H). LCMS(m/z) 294.1 [M+H]+.

Example 11. 8-chloro-N-methyl-N-phenyl-[1,2,4]triazolo[4,3-a]quinazolin-5-amine

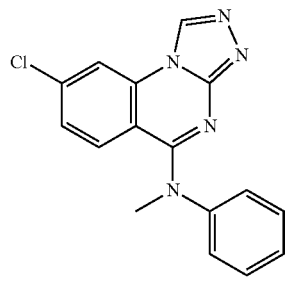 [SMILES: CN(c1ccccc1)c1nc2nncn2c2cc(Cl)ccc12]

(Step 1) Synthesis of 2,7-dichloro-N-methyl-N-phenylquinazolin-4-amine

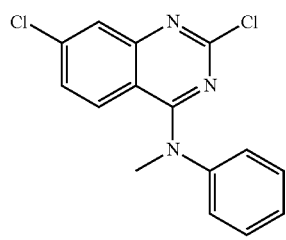 [SMILES: CN(c1ccccc1)c1nc(Cl)nc2cc(Cl)ccc12]

To a suspension of 2,4,7-trichloroquinazoline (513 mg, 2.197 mmol) in DMF (1.1 mL) were added N-methylaniline (235 mg, 2.197 mmol) and sodium hydroxide (111 mg, 2.78 mmol), and the mixture was stirred for 1 h at RT. The reaction mixture was diluted with AcOEt, washed successively with water and brine, and dried over Na₂SO₄. The organic layer was concentrated in vacuo to give the desired product. LCMS(m/z) 305.1 [M+H]⁺.

(Step 2) Synthesis of 7-chloro-2-hydrazinyl-N-methyl-N-phenylquinazolin-4-amine

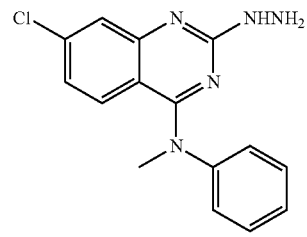 [SMILES: CN(c1ccccc1)c1nc(NN)nc2cc(Cl)ccc12]

To a solution of 2,7-dichloro-N-methyl-N-phenylquinazolin-4-amine (572 mg, 2.2 mmol) in EtOH (11 mL) was added hydrazine hydrate (0.11 g, 2.2 mmol), and the mixture was stirred for 2 h at 50° C. The reaction mixture was diluted with AcOEt, washed successively with water and brine, and dried over Na₂SO₄. The organic layer was concentrated in vacuo to give the desired product. LCMS(m/z) 300.13 [M+H]⁺.

(Step 3) Synthesis of 8-chloro-N-methyl-N-phenyl-[1,2,4]triazolo[4,3-a]quinazolin-5-amine A mixture of 7-chloro-2-hydrazinyl-N-methyl-N-phenylquinazolin-4-amine (659 mg, 2.2 mmol) and triethoxymethane (324 mg, 2.2 mmol) was stirred for 1 h at 100° C. The reaction mixture was concentrated in vacuo, and the residue was purified by column chromatography (Si-column, CHCl₃:MeOH=10:0-9:1) to afford the desired product: ¹H-NMR (Methanol-d₄) δ 9.45-9.40 (m, 1H), 8.33 (d, J=2.0 Hz, 1H), 7.49-7.39 (m, 2H), 7.34-7.13 (m, 5H), 3.65 (s, 3H). LCMS(m/z) 310.0 [M+H]+.

Example 12. 9-methoxy-N-methyl-N-phenyl-[1,2,4]triazolo[4,3-a]quinazolin-5-amine

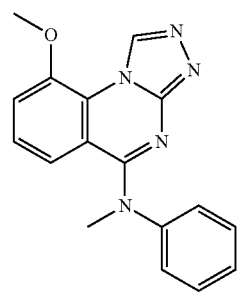

(Step 1) Synthesis of 2-chloro-8-methoxy-N-methyl-N-phenylquinazolin-4-amine

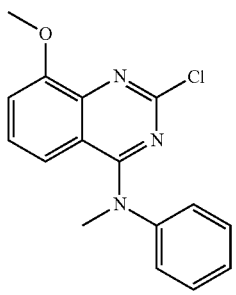 [SMILES: COc1cccc2c(N(C)c3ccccc3)nc(Cl)nc12]

To a suspension of 2,4-dichloro-8-methoxyquinazoline (100 mg, 0.437 mmol) in DMF (2.2 mL) were added N-methylaniline (46.8 mg, 0.437 mmol) and sodium hydroxide (17.46 mg, 0.437 mmol), and the mixture was stirred for 1 h at RT. The reaction mixture was diluted with AcOEt, washed successively with water and brine, and dried over $Na_2SO_4$. The organic layer was concentrated in vacuo to give the desired product, which was used for next step without further purification. LCMS(m/z) 300.18 $[M+H]^+$.

(Step 2) Synthesis of 2-hydrazinyl-8-methoxy-N-methyl-N-phenylquinazolin-4-amine

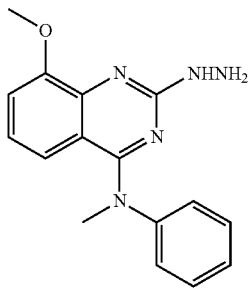 [SMILES: COc1cccc2c(N(C)c3ccccc3)nc(NN)nc12]

To a solution of 2-chloro-8-methoxy-N-methyl-N-phenylquinazolin-4-amine (131 mg, crude) in EtOH (2.2 mL) was added hydrazine hydrate (43.8 mg, 0.874 mmol), and the mixture was stirred for 2 h at 50° C. The reaction mixture was diluted with AcOEt, washed successively with water and brine, and dried over $Na_2SO_4$. The organic layer was concentrated in vacuo to give the desired product, which was used for next step without further purification. LCMS(m/z) 296.18 $[M+H]^+$.

(Step 3) Synthesis of 9-methoxy-N-methyl-N-phenyl-[1,2,4]triazolo[4,3-a]quinazolin-5-amine A mixture of 2-hydrazinyl-8-methoxy-N-methyl-N-phenylquinazolin-4-amine (119 mg, crude) and triethoxymethane (259 mg, 1.748 mmol) and a drop of acetic acid (12.04 mg, 0.201 mmol) was stirred at 90° C. for 1 h. The reaction mixture was concentrated in vacuo, and the residue was purified by column chromatography (Si-column, $CHCl_3$:MeOH=10:0-9:1 gradient) to afford the desired product: $^1$H-NMR (Methanol-$d_4$) δ 9.51 (s, 1H), 7.44-7.16 (m, 6H), 7.08 (t, J=8.3 Hz, 1H), 6.87 (d, J=8.4 Hz, 1H), 4.12 (s, 3H), 3.62 (s, 3H). LCMS(m/z) 306.1 [M+H]+.

Example 13. N-(4-fluorophenyl)-N-methyl-[1,2,4]triazolo[4,3-a]quinazolin-5-amine

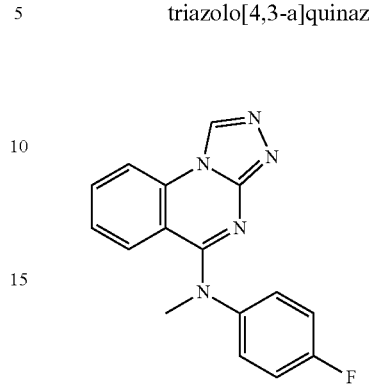

(Step 1) Synthesis of 2-chloro-N-(4-fluorophenyl)-N-methylquinazolin-4-amine

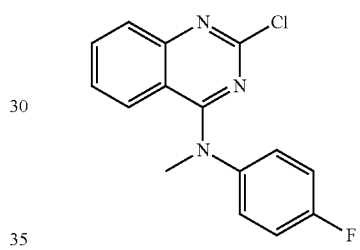

To a suspension of 2,4-dichloroquinazoline (100 mg, 0.502 mmol) in DMF (0.25 mL) were added N-methyl-4-fluoroaniline (62.9 mg, 0.502 mmol) and sodium hydroxide (20.1 mg, 0.502 mmol), and the mixture was stirred for 1 h at RT. The reaction mixture was diluted with AcOEt, washed successively with water and brine, and dried over $Na_2SO_4$. The resultant residue was used for the next step without further purification. LCMS(m/z) 288.03 $[M+H]^+$.

(Step 2) Synthesis of N-(4-fluorophenyl)-2-hydrazinyl-N-methylquinazolin-4-amine

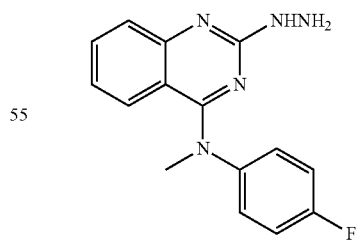

To a solution of 2-chloro-N-(4-fluorophenyl)-N-methylquinazolin-4-amine (68 mg, crude) in EtOH (1.2 mL) was added hydrazine hydrate (23.66 mg, 0.473 mmol), and the mixture was stirred for 2 h at 50° C. The reaction mixture was diluted with AcOEt, washed successively with water and brine, and dried over $Na_2SO_4$. The organic layer was (Step 3) Synthesis of N-(4-fluorophenyl)-N-methyl-[1,2,4]triazolo[4,3-a]quinazolin-5-amine A mixture of N-(4-fluorophenyl)-2-hydrazinyl-N-methylquinazolin-4-amine (51 mg, crude) and triethoxymethane (175 mg, 1.182 mmol) and acetic acid (12.04 mg, 0.201 mmol) at 90° C. The reaction mixture was concentrated in vacuo, and the residue was purified by column chromatography (Si-column, CHC$_3$:MeOH=10:0-9:1) to afford the desired product: $^1$H-NMR (Methanol-d$_4$) δ 9.44 (s, 1H), 8.19 (d, J=7.9 Hz, 1H), 7.81-7.72 (m, 1H), 7.38-7.31 (m, 3H), 7.27-7.20 (m, 1H), 7.19-7.15 (m, 2H), 3.63 (s, 3H). LCMS(m/z) 294.1 [M+H]+.

Example 14. 6-chloro-N-methyl-N-phenyl-[1,2,4]triazolo[4,3-a]quinazolin-5-amine

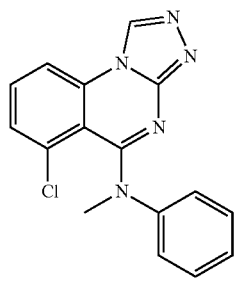

(Step 1) Synthesis of 2,5-dichloro-N-methyl-N-phenylquinazolin-4-amine

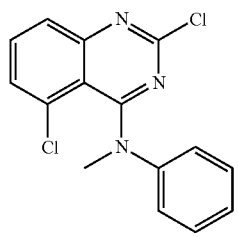

To a suspension of 2,4,5-trichloroquinazoline (100 mg, 0.428 mmol) in 2-propanol (2.1 mL) were added N-methylaniline (45.9 mg, 0.428 mmol) and conc. HCl (37%, 15.62 mg, 0.428 mmol), and the mixture was stirred for 1 h at RT. The precipitates were collected and washed with 2-propanol to give the desired product. LCMS(m/z) 304.08 [M+H]+.

concentrated in vacuo. The resultant residue was used for the next step without further purification. LCMS(m/z) 284.13 [M+H]$^+$.

(Step 2) Synthesis of 5-chloro-2-hydrazinyl-N-methyl-N-phenylquinazolin-4-amine

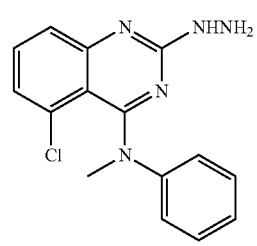

To a solution of 2,5-dichloro-N-methyl-N-phenylquinazolin-4-amine (61 mg, 0.201 mmol) in EtOH (1 mL) was added hydrazine hydrate (20.08 mg, 0.401 mmol), and the mixture was stirred for 2 h at 50° C. The reaction mixture was diluted with AcOEt, washed successively with water and brine, and dried over Na$_2$SO$_4$. The organic layer was concentrated in vacuo to give the desired product. LCMS (m/z) 300.08 [M+H]+.

(Step 3) Synthesis of 6-chloro-N-methyl-N-phenyl-[1,2,4]triazolo[4,3-a]quinazolin-5-amine A mixture of 5-chloro-2-hydrazinyl-N-methyl-N-phenylquinazolin-4-amine (54 mg, crude) and triethoxymethane (29.7 mg, 0.201 mmol) and a drop of acetic acid (12.04 mg, 0.201 mmol) was heated to 90° C. for 2 h. The reaction mixture was concentrated in vacuo, and the residue was purified by column chromatography (Si-column, CHC$_3$:MeOH=10:0-9:1) to afford the desired product: $^1$H-NMR (Methanol-d$_4$) δ 9.46 (s, 1H), 8.17 (dd, J=8.4, 0.9 Hz, 1H), 7.76 (t, J=8.1 Hz, 1H), 7.40-7.33 (m, 1H), 7.25-7.15 (m, 2H), 7.08 (t, J=7.4 Hz, 1H), 7.02-6.93 (m, 2H), 3.68 (s, 3H). LCMS(m/z) 310.1 [M+H]+.

Example 15. N-ethyl-N-phenyl-[1,2,4]triazolo[4,3-a]quinazolin-5-amine

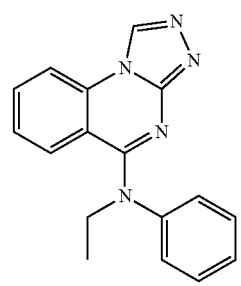 [SMILES: CCN(c1ccccc1)c1nc2nncn2c2ccccc12]

(Step 1) Synthesis of
2-chloro-N-ethyl-N-phenylquinazolin-4-amine

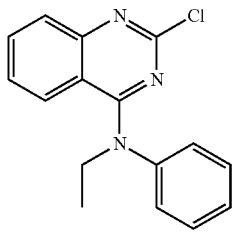 [SMILES: CCN(c1ccccc1)c1nc(Cl)nc2ccccc12]

To a solution of 2,4-dichloroquinazoline (200 mg, 1.005 mmol) in DMF (5 mL) were added N-methylaniline (121 mg, 1.005 mmol) and sodium hydroxide (40.2 mg, 1.005 mmol), and the mixture was stirred for 3 h at RT. The mixture was diluted with AcOEt, washed successively with water and brine, dried over $Na_2SO_4$. The resultant residue was used for the next step without further purification. LCMS(m/z) 284.13 $[M+H]^+$.

(Step 2) Synthesis of
2-hydrazinyl-N-ethyl-N-phenylquinazolin-4-amine

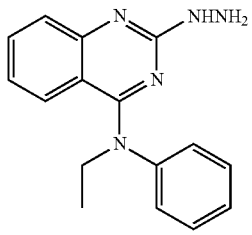 [SMILES: CCN(c1ccccc1)c1nc(NN)nc2ccccc12]

To a solution of 2-chloro-N-ethyl-N-phenylquinazolin-4-amine (210 mg, crude) in EtOH (3.7 mL) was added hydrazine hydrate (37 mg, 0.74 mmol), and the mixture was stirred for 2 h at 50° C. The reaction mixture was diluted with AcOEt, washed successively with water and brine, and dried over $Na_2SO_4$. The organic layer was concentrated in vacuo. The resultant residue was used for the next step without further purification. LCMS(m/z) 280.18 $[M+H]^+$.

(Step 3) Synthesis of N-ethyl-N-phenyl-[1,2,4]triazolo[4,3-a]quinazolin-5-amine

A mixture of 2-hydrazinyl-N-ethyl-N-phenylquinazolin-4-amine (185 mg, crude) and triethoxymethane (110 mg, 0.740 mmol) and acetic acid (12.04 mg, 0.201 mmol) at 90° C. The reaction mixture was concentrated in vacuo, and the residue was purified by column chromatography (Si-column, $CHCl_3$:MeOH=10:0-9:1) to afford the desired product: $^1$H-NMR ($CDCl_3$) δ 8.92 (s, 1H), 7.78 (dd, J=8.3, 1.1 Hz, 1H), 7.62 (ddd, J=8.4, 7.2, 1.3 Hz, 1H), 7.43-7.32 (m, 2H), 7.32-7.22 (m, 2H), 7.19-7.04 (m, 3H), 4.25 (q, J=7.0 Hz, 2H), 1.35 (t, J=7.0 Hz, 3H). LCMS(m/z) 290.2 [M+H]+.

Example 16. N,9-dimethyl-N-phenyl-[1,2,4]triazolo[4,3-a]quinazolin-5-amine

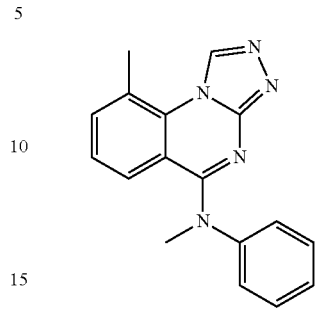

(Step 1) Synthesis of
8-methylquinazoline-2,4(1H,3H)-dione

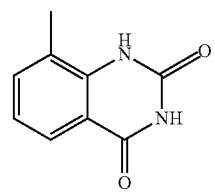

To a suspension of 2-amino-3-methylbenzoic acid (500 mg, 3.31 mmol) in water (5 mL) was added acetic acid (0.5 mL), and the suspension was heated to 35° C. A freshly prepared solution of potassium cyanate (268 mg, 3.31 mmol) in water (0.5 mL) was added dropwise to the suspension over the period of 1 h. The mixture was stirred for 1 h at 40° C. NaOH (8 g) was added portion-wise to the reaction mixture by maintaining the internal temperature below 50° C., and the mixture was further stirred for 2 h. The precipitate was collected by filtration to give the desired product. LCMS(m/z) 177.11 $[M+H]^+$.

(Step 2) Synthesis of
2,4-dichloro-8-methylquinazoline

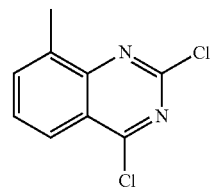

A mixture of 8-methylquinazoline-2,4(1H,3H)-dione (120 mg, 0.68 mmol) and phosphoryl trichloride (1521 mg, 9.92 mmol) was stirred for 3 h at 100° C. The reaction mixture was concentrated in vacuo, and the resultant residue was used for the next step without further purification. LCMS(m/z) 213.10 $[M+H]^+$.

(Step 3) Synthesis of 2-chloro-N,8-dimethyl-N-phenylquinazolin-4-amine

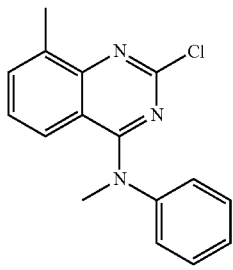 [SMILES: Cc1cccc2c(N(C)c3ccccc3)nc(Cl)nc12]

To a suspension of 2,4-dichloro-8-methylquinazoline (100 mg, 0.469 mmol) in DMF (2.35 mL) were added N-methylaniline (50.3 mg, 0.469 mmol) and sodium hydroxide (18.77 mg, 0.469 mmol), and the mixture was stirred for 1 h at RT. The reaction mixture was diluted with AcOEt, washed successively with water and brine, and dried over $Na_2SO_4$. The organic layer was concentrated in vacuo to give the desired product, which was used for the next step without further purification. LCMS(m/z) 284.8 $[M+H]^+$.

(Step 4) Synthesis of 2-hydrazinyl-N,8-dimethyl-N-phenylquinazolin-4-amine

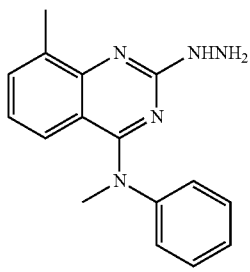 [SMILES: Cc1cccc2c(N(C)c3ccccc3)nc(NN)nc12]

To a solution of 2-chloro-N,8-dimethyl-N-phenylquinazolin-4-amine (69 mg, 0.243 mmol) in EtOH (1.2 mL) was added hydrazine hydrate (24.35 mg, 0.486 mmol), and the mixture was stirred for 2 h at 50° C. The reaction mixture was diluted with AcOEt, washed successively with water and brine, and dried over $Na_2SO_4$. The organic layer was concentrated in vacuo to give the desired product. LCMS (m/z) 280.18 $[M+H]^+$.

(Step 5) Synthesis of N,9-dimethyl-N-phenyl-[1,2,4]triazolo[4,3-a]quinazolin-5-amine A mixture of 2-hydrazinyl-N,8-dimethyl-N-phenylquinazolin-4-amine (54 mg, 0.192 mmol) and triethoxymethane (108 mg, 0.729 mmol) was stirred at 90° C. overnight. The reaction mixture was concentrated in vacuo, and the residue was purified by column chromatography (Si-column, $CHCl_3$:MeOH=10:0-9:1) to afford the desired product: $^1$H-NMR (Methanol-$d_4$) δ 9.41 (s, 1H), 7.53 (d, J=7.3 Hz, 1H), 7.39-7.31 (m, 2H), 7.25 (q, J=8.3, 7.4 Hz, 2H), 7.17 (dd, J=7.6, 2.0 Hz, 2H), 7.02 (t, J=7.9 Hz, 1H), 3.62 (d, J=1.9 Hz, 3H), 2.82 (s, 3H); LCMS(m/z) 290.1 [M+H]+.

Example 17. N-(3-fluorophenyl)-N-methyl-[1,2,4]triazolo[4,3-a]quinazolin-5-amine

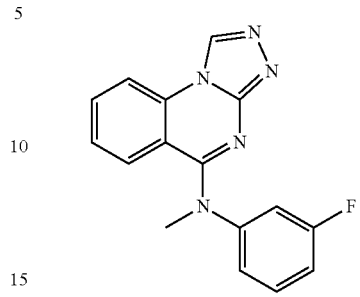

To a solution of 5-chloro-[1,2,4]triazolo[4,3-a]quinazoline (70 mg, 0.376 mmol), BOP (183 mg, 0.414 mmol) and DBU (0.068 ml, 0.451 mmol) in NMP (2 mL) was added 3-fluoro-N-methylaniline (51.8 mg, 0.414 mmol) at RT. The mixture was stirred for 4.5 h at 55° C. The reaction mixture was purified by prep-LCMS to afford the desired product: $^1$H-NMR (DMSO-$d_6$) δ 9.66 (s, 1H), 8.32 (d, J=8.2 Hz, 1H), 7.81 (ddd, J=8.5, 7.0, 1.7 Hz, 1H), 7.44-7.23 (m, 4H), 7.14-7.02 (m, 2H), 3.56 (s, 3H). LCMS(m/z) 294.1 [M+H]+.

Example 18. 6-fluoro-N-methyl-N-phenyl-[1,2,4]triazolo[4,3-a]quinazolin-5-amine

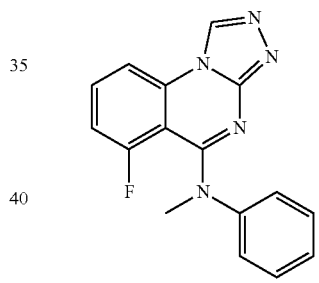

(Step 1) Synthesis of 2-chloro-5-fluoro-N-methyl-N-phenylquinazolin-4-amine

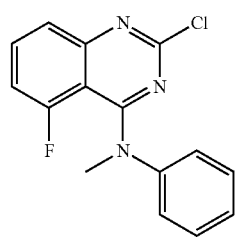

To a suspension of 2,4-dichloro-5-fluoroquinazoline (100 mg, 0.461 mmol) in 2-propanol (2.3 mL) were added N-methylaniline (49.4 mg, 0.461 mmol) and a drop of conc. HCl (37%), and the mixture was stirred for 30 min at RT. The reaction mixture was filtered and washed with 2-propanol to give the desired product. LCMS(m/z) 288.08 $[M+H]^+$.

(Step 2) Synthesis of 5-fluoro-2-hydrazinyl-N-methyl-N-phenylquinazolin-4-amine

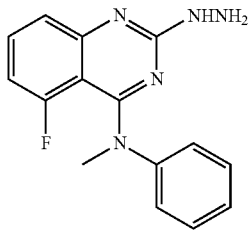

To a solution of 2-chloro-5-fluoro-N-methyl-N-phenylquinazolin-4-amine (43 mg, 0.149 mmol) in ethanol (0.75 mL) was added hydrazine hydrate (11.22 mg, 0.224 mmol), and the mixture was stirred for 2 h at 50° C. The reaction mixture was diluted with AcOEt, washed successively with water and brine, and dried over $Na_2SO_4$. The organic layer was concentrated in vacuo to give the desired product, which was used for the next step without further purification. LCMS(m/z) 284.13 [M+H]$^+$.

(Step 3) Synthesis of 6-fluoro-N-methyl-N-phenyl-[1,2,4]triazolo[4,3-a]quinazolin-5-amine A mixture of 5-fluoro-2-hydrazinyl-N-methyl-N-phenylquinazolin-4-amine (39 mg, crude) and triethoxymethane (111 mg, 0.747 mmol) and acetic acid (12.04 mg, 0.201 mmol) for 2 h at 90° C. The reaction mixture was concentrated in vacuo, and the residue was purified by column chromatography (Si-column, $CHCl_3$:MeOH=10:0-9:1) to afford the desired product: $^1$H-NMR (Methanol-d4) δ 9.44 (s, 1H), 8.02 (d, J=8.3 Hz, 1H), 7.83 (td, J=8.3, 5.1 Hz, 1H), 7.32-7.23 (m, 2H), 7.21-7.06 (m, 3H), 6.99 (dd, J=11.6, 8.3 Hz, 1H), 3.64 (s, 3H); LCMS(m/z) 295.1 [M+H]+.

Example 19. N-methyl-N,8-diphenyl-[1,2,4]triazolo[4,3-a]quinazolin-5-amine

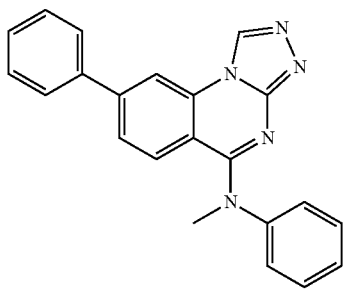 [SMILES: CN(c1ccccc1)c1nc2nncn2c2cc(-c3ccccc3)ccc12]

A mixture of 8-bromo-N-methyl-N-phenyl-[1,2,4]triazolo[4,3-a]quinazolin-5-amine (Example 28) (50 mg, 0.161 mmol), phenylboronic acid (49.2 mg, 0.404 mmol), cesium fluoride (73.6 mg, 0.484 mmol) and Bis[di-tert-butyl(4-dimethylaminophenyl)phosphine]palladium(0) (11 mg, 0.016 mmol) in dioxane (0.8 mL) was treated in a microwave reactor for 2 h at 100° C., then at 120° C. for 2 h. The reaction mixture was concentrated in vacuo, and purified by column chromatography (Si-column, $CHCl_3$:MeOH=10:0-9:1 to afford the desired product: $^1$H-NMR (Methanol-d4) δ 9.46 (s, 1H), 8.22 (d, J=1.8 Hz, 1H), 7.67-7.57 (m, 2H), 7.43-7.36 (m, 5H), 7.33-7.26 (m, 2H), 7.21 (dd, J=7.5, 1.5 Hz, 2H), 7.12 (d, J=8.8 Hz, 1H), 3.58 (s, 3H). LCMS(m/z) 352.1 [M+H]+.

Example 20. 8-methoxy-N-methyl-N-phenyl-[1,2,4]triazolo[4,3-a]quinazolin-5-amine

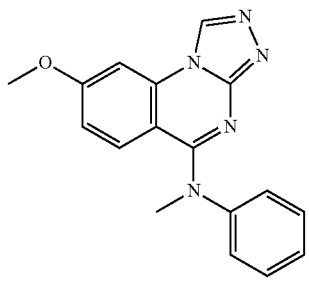 [SMILES: COc1ccc2c(N(C)c3ccccc3)nc3nncn3c2c1]

(Step 1) Synthesis of 2-chloro-7-methoxy-N-methyl-N-phenylquinazolin-4-amine

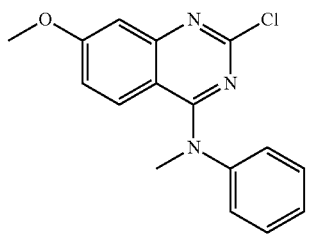 [SMILES: COc1ccc2c(N(C)c3ccccc3)nc(Cl)nc2c1]

To a solution of 2,4-dichloro-7-methoxyquinazoline (100 mg, 0.44 mmol) in DMF (7 mL) were added N-methylaniline (46.7 mg, 0.44 mmol) and sodium hydroxide (18.4 mmol, 0.46 mmol). The mixture was stirred for 1 h at RT and for 2 h at 60° C. The mixture was diluted with AcOEt, washed successively with water and brine, and dried over $Na_2SO_4$. The organic layer was concentrated in vacuo to give the desired product. LCMS(m/z) 300.08 [M+H]$^+$.

(Step 2) Synthesis of 2-hydrazinyl-7-methoxy-N-methyl-N-phenylquinazolin-4-amine

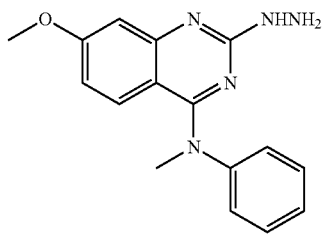 [SMILES: COc1ccc2c(N(C)c3ccccc3)nc(NN)nc2c1]

To a solution of 2-chloro-7-methoxy-N-methyl-N-phenylquinazolin-4-amine (92 mg, 0.340 mmol) in EtOH (1.7 mL) was added hydrazine hydrate (17.01 mg, 0.340 mmol), and the mixture was stirred for 2 h at 50° C. The reaction mixture was diluted with AcOEt, washed successively with water and brine, and dried over Na₂SO₄. The organic layer was concentrated in vacuo to give the desired product. LCMS(m/z) 296.18 [M+H]⁺.

(Step 3) Synthesis of 8-methoxy-N-methyl-N-phenyl-[1,2,4]triazolo[4,3-a]quinazolin-5-amine A mixture of 2-hydrazinyl-7-methoxy-N-methyl-N-phenylquinazolin-4-amine (67 mg, crude) and triethoxymethane (201 mg, 1.359 mmol) and acetic acid (12.04 mg, 0.201 mmol) for 2 h at 90° C. The reaction mixture was concentrated in vacuo, and the residue was purified by column chromatography (Si-column, CHCl₃:MeOH=10:0-9:1) to afford the desired product: ¹H-NMR (DMSO-d₆) δ 9.62 (s, 1H), 7.80 (d, J=2.5 Hz, 1H), 7.43-7.33 (m, 2H), 7.31-7.20 (m, 3H), 7.15 (d, J=9.3 Hz, 1H), 6.81 (dd, J=9.3, 2.5 Hz, 1H), 3.91 (s, 3H), 3.51 (s, 3H). LCMS(m/z) 306.1 [M+H]+.

Example 21. 7-fluoro-N-methyl-N-phenyl-[1,2,4]triazolo[4,3-a]quinazolin-5-amine

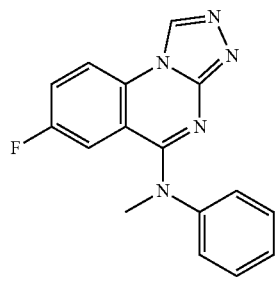

(Step 1) Synthesis of 2-chloro-6-fluoro-N-methyl-N-phenylquinazolin-4-amine

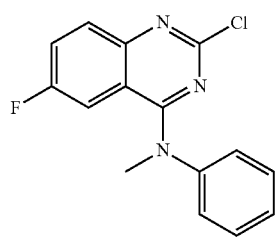

To a solution of N-methylaniline (148 mg, 1.382 mmol) and NaH (60.8 mg, 1.521 mmol) in DMF (10 mL) was added 2,4-dichloro-6-fluoroquinazoline (300 mg, 1.382 mmol) at RT, and the mixture was stirred for 3.5 h at RT. The reaction mixture was diluted with EtOAc, washed successively with water and brine, dried over Na₂SO₄, and concentrated in vacuo to give the desired product, which was used for the next step without purification. LCMS(m/z) 288.08 [M+H]⁺.

(Step 2) Synthesis of 6-fluoro-2-hydrazinyl-N-methyl-N-phenylquinazolin-4-amine

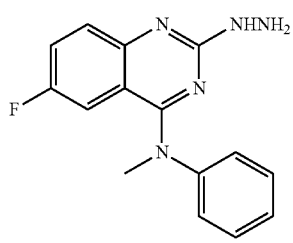

To a solution of 2-chloro-6-fluoro-N-methyl-N-phenylquinazolin-4-amine (398 mg, crude) in EtOH (5 mL) was added hydrazine hydrate (1 mL, 20.61 mmol) at RT, and the mixture was stirred overnight at 50° C. The reaction mixture was cooled to RT, and filtered to give the desired product, which was used for the next step without purification. LCMS(m/z) 284.13 [M+H]⁺.

(Step 3) Synthesis of 7-fluoro-N-methyl-N-phenyl-[1,2,4]triazolo[4,3-a]quinazolin-5-amine A mixture of 6-fluoro-2-hydrazinyl-N-methyl-N-phenylquinazolin-4-amine (42 mg, crude) and triethoxymethane (3 mL) was stirred for 2 h at 100° C. The reaction mixture was cooled to RT and filtered to afford the crude product. The crude compound was purified by prep-LCMS to afford the desired product: ¹H-NMR (DMSO-d₆) δ 9.63 (s, 1H), 8.38 (dd, J=9.2, 4.9 Hz, 1H), 7.75 (ddd, J=9.2, 8.0, 2.8 Hz, 1H), 7.48-7.38 (m, 2H), 7.38-7.27 (m, 3H), 6.81 (dd, J=10.5, 2.8 Hz, 1H), 3.54 (s, 3H). LCMS(m/z) 294.2 [M+H]+.

Example 22. N-methyl-N-(pyridin-2-yl)-[1,2,4]triazolo[4,3-a]quinazolin-5-amine

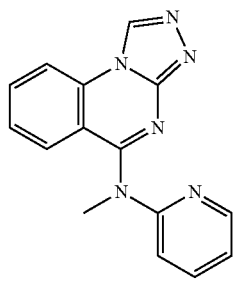 [SMILES: CN(c1ccccn1)c1nc2nncn2c2ccccc12]

(Step 1) Synthesis of 2-chloro-N-methyl-N-(pyridin-2-yl)quinazolin-4-amine

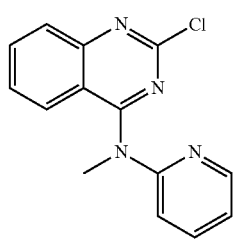 [SMILES: CN(c1ccccn1)c1nc(Cl)nc2ccccc12]

To a stirred solution of 2,4-dichloroquinazoline (0.5 g, 2.51 mmol) in DMF (10 mL) was added 60% sodium hydride (0.150 g, 3.77 mmol) at 0° C. and the mixture was stirred for 1 h at RT, followed by the addition of N-methylpyridin-2-amine (0.407 g, 3.77 mmol) at 0° C., and the mixture was stirred for 1 h at RT. The progress of the reaction was monitored by TLC. After completion of the reaction, the reaction mixture was diluted with ice-water and extracted with ethyl acetate twice. The combined organic layers were washed with brine, dried over $Na_2SO_4$, filtered and evaporated under reduced pressure. The residue was purified by column chromatography (Si-column, AcOEt: petroleum ether=3:7-1:1) to give the desired product.

(Step 2) Synthesis of N-methyl-N-(pyridin-2-yl)-[1, 2,4]triazolo[4,3-a]quinazolin-5-amine To a stirred solution of 2-chloro-N-methyl-N-(pyridin-2-yl)quinazolin-4-amine (0.1 g, 0.37 mmol) in toluene (2 mL) was added formohydrazide (0.044 g, 0.74 mmol) at RT, and the mixture was heated to 110° C. for 48 h. The progress of the reaction was monitored by TLC. After completion of the reaction, the reaction mixture was evaporated under reduced pressure. The residue was purified by prep. HPLC to afford the desired product: $^1$H-NMR (DMSO-$d_6$) δ 9.73 (s, 1H), 8.35 (d, J=8.3 Hz, 1H), 8.22 (ddd, J=5.0, 1.9, 0.9 Hz, 1H), 7.86 (ddd, J=8.4, 6.9, 1.7 Hz, 1H), 7.78 (ddd, J=8.2, 7.2, 2.0 Hz, 1H), 7.41-7.23 (m, 3H), 7.12 (ddd, J=7.4, 4.9, 0.9 Hz, 1H), 3.64 (s, 3H); LCMS(m/z) 277.2 [M+H]+.

Example 23. N-methyl-N-(pyridin-3-yl)-[1,2,4]triazolo[4,3-a]quinazolin-5-amine

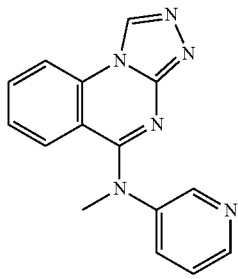 [SMILES: CN(c1cccnc1)c1nc2nncn2c2ccccc12]

(Step 1) Synthesis of 2-chloro-N-methyl-N-(pyridin-3-yl)quinazolin-4-amine

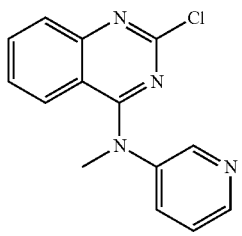 [SMILES: CN(c1cccnc1)c1nc(Cl)nc2ccccc12]

To a stirred solution of 2,4-dichloroquinazoline (0.5 g, 2.51 mmol) in DMF (10 mL) was added 60% sodium hydride (0.150 g, 3.77 mmol) at 0° C. and the mixture was stirred at room temperature for 1 h, followed by the addition of N-methylpyridin-3-amine (0.407 g, 3.77 mmol) at 0° C., and the mixture was stirred for 1 h at RT. The progress of the reaction was monitored by TLC. After completion of the reaction, the reaction mixture was diluted with ice-water and extracted with ethyl acetate twice. The combined organic layers were washed with brine, dried over $Na_2SO_4$, filtered and evaporated under reduced pressure. The residue was purified by column chromatography (Si-column, AcOEt: petroleum ether=3:7-1:1) to give the desired product.

(Step 2) Synthesis of N-methyl-N-(pyridin-3-yl)-[1, 2,4]triazolo[4,3-a]quinazolin-5-amine To a stirred solution of 2-chloro-N-methyl-N-(pyridin-3-yl)quinazolin-4-amine (0.120 g, 0.44 mmol) in toluene (4 mL) was added formohydrazide (0.053 g, 0.88 mmol) at RT and the mixture was heated to 120° C. for 48 h. The progress of the reaction was monitored by TLC. After completion of the reaction, the reaction mixture was evaporated under reduced pressure. The residue was purified by prep. HPLC to afford the desired product: $^1$H-NMR (DMSO-$d_6$) δ 9.66 (s, 1H), 8.51 (d, J=2.7 Hz, 1H), 8.42 (dd, J=4.8, 1.4 Hz, 1H), 8.37-8.27 (m, 1H), 7.87-7.71 (m, 2H), 7.42 (ddd, J=8.2, 4.7, 0.8 Hz, 1H), 7.33-7.23 (m, 2H), 3.58 (s, 3H); LCMS(m/z) 277.2 [M+H]+.

Example 24. N-methyl-N-(pyridin-4-yl)-[1,2,4]triazolo[4,3-a]quinazolin-5-amine

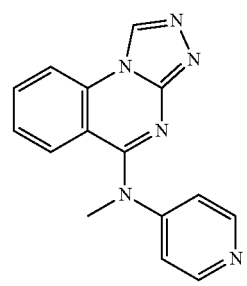 [SMILES: CN(c1ccncc1)c1nc2nncn2c2ccccc12]

(Step 1) Synthesis of 2-chloro-N-methyl-N-(pyridin-4-yl)quinazolin-4-amine

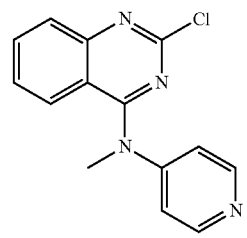 [SMILES: CN(c1ccncc1)c1nc(Cl)nc2ccccc12]

To a stirred solution of 2,4-dichloroquinazoline (0.5 g, 2.51 mmol) in DMF (10 mL) were added sodium hydroxide (0.1 g, 2.51 mmol) and N-methylpyridin-4-amine (0.271 g, 2.51 mmol) at RT, and the mixture was stirred for 4 h at RT. The progress of the reaction was monitored by TLC. After completion of the reaction, the reaction mixture was diluted with ice-water and extracted with ethyl acetate. The organic layer was washed with brine, dried over $Na_2SO_4$, filtered and evaporated under reduced pressure to give the desired product.

(Step 2) Synthesis of N-methyl-N-(pyridin-4-yl)-[1,2,4]triazolo[4,3-a]quinazolin-5-amine To a stirred solution of 2-chloro-N-methyl-N-(pyridin-4-yl)quinazolin-4-amine (0.250 g, 0.92 mmol) in toluene (5 mL) was added formohydrazide (0.111 g, 1.85 mmol) at RT, and the mixture was heated to 120° C. for 48 h. The progress of the reaction was monitored by TLC. After completion of the reaction, the reaction mixture was evaporated under reduced pressure. The residue was purified by prep. HPLC to afford the desired product: $^1$H-NMR (DMSO-$d_6$) δ 9.80 (s, 1H), 8.57-8.29 (m, 3H), 7.92 (ddd, J=8.5, 7.2, 1.4 Hz, 1H), 7.55 (dd, J=8.3, 1.4 Hz, 1H), 7.43 (ddd, J=8.2, 7.2, 1.1 Hz, 1H), 7.19-6.98 (m, 2H), 3.60 (s, 3H); LCMS(m/z) 277.2 [M+H]+.

Example 25. N-(2-chlorophenyl)-N-methyl-[1,2,4]triazolo[4,3-a]quinazolin-5-amine

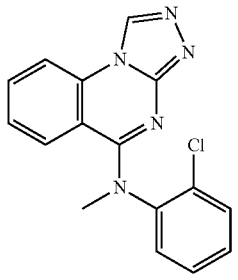 [SMILES: CN(c1ccccc1Cl)c1nc2nncn2c2ccccc12]

To a solution of 5-chloro-[1,2,4]triazolo[4,3-a]quinazoline (50 mg, 0.269 mmol), Bromotris(dimethylamino)phosphonium hexafluorophosphate (BrOP) (125 mg, 0.322 mmol) and DBU (49.1 mg, 0.322 mmol) in acetonitrile (1 mL) was added to 2-chloro-N-methylaniline (41.8 mg, 0.295 mmol) at RT. The mixture was stirred overnight at 80° C. The reaction mixture was concentrated in vacuo, and the residue was purified by column chromatography (Si-column, $CHCl_3$:MeOH=100:0-95:5) to afford a crude product. The crude compound was further purified by prep-LCMS to afford the desired product: $^1$H-NMR (CDCl$_3$) δ 8.94 (s, 1H), 7.82 (ddd, J=8.3, 1.2, 0.6 Hz, 1H), 7.66 (ddd, J=8.4, 6.7, 1.8 Hz, 1H), 7.60-7.52 (m, 1H), 7.34-7.29 (m, 1H), 7.26 (td, J=7.6, 1.7 Hz, 1H), 7.20-7.10 (m, 3H), 3.59 (s, 3H); LCMS (m/z) 310.2 [M+H]+.

Example 26. N-(2-cyanophenyl)-N-methyl-[1,2,4]triazolo[4,3-a]quinazolin-5-amine

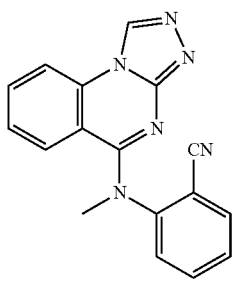

To a solution of 5-chloro-[1,2,4]triazolo[4,3-a]quinazoline (80 mg, 0.430 mmol), BrOP (200 mg, 0.516 mmol) and DBU (79 mg, 0.516 mmol) in acetonitrile (2 mL) was added to 2-cyano-N-methylaniline (56.8 mg, 0.430 mmol) at RT. The mixture was stirred overnight at 80° C. The reaction mixture was subjected to solid phase extraction (washed with MeOH, then eluted with $NH_3$ in MeOH) using Bond Elut SCX cartridge (Agilent), and the collected fractions were concentrated in vacuo. Then, the residue was purified by preparative LCMS to afford the desired product: $^1$H-NMR (CDCl$_3$) δ 9.05 (s, 1H), 7.92 (d, J=8.2 Hz, 1H), 7.81 (dd, J=7.8, 1.6 Hz, 1H), 7.72 (ddd, J=8.4, 5.2, 3.4 Hz, 1H), 7.54 (td, J=7.9, 1.7 Hz, 1H), 7.41 (td, J=7.7, 1.1 Hz, 1H), 7.24-7.14 (m, 2H), 7.10 (dd, J=8.2, 1.1 Hz, 1H), 3.73 (s, 3H); LCMS(m/z) 301.2 [M+H]+.

Example 27. N-(2-bromophenyl)-N-methyl-[1,2,4]triazolo[4,3-a]quinazolin-5-amine

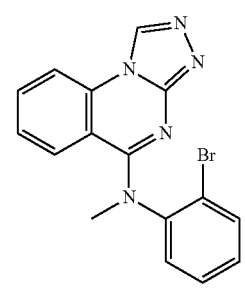 [SMILES: CN(c1ccccc1Br)c1nc2nncn2c2ccccc12]

To a solution of 5-chloro-[1,2,4]triazolo[4,3-a]quinazoline (50 mg, 0.269 mmol), BrOP (125 mg, 0.322 mmol) and DBU (49.1 mg, 0.322 mmol) in acetonitrile (1 mL) was added to 2-bromo-N-methylaniline (50 mg, 0.269 mmol) at RT. The mixture was stirred overnight at 80° C. The reaction mixture was subjected to solid phase extraction (washed with MeOH, then eluted with $NH_3$ in MeOH) using Bond Elut SCX cartridge (Agilent), and the collected fractions were concentrated in vacuo. Then, the residue was purified by prep-LCMS to afford the desired product: $^1$H-NMR (CDCl$_3$) δ 9.13 (s, 1H), 7.97 (d, J=8.3 Hz, 1H), 7.79-7.65 (m, 2H), 7.29 (dt, J=7.6, 1.6 Hz, 2H), 7.23-7.09 (m, 3H), 3.60 (s, 3H); LCMS(m/z) 355.6 [M+H]+.

Example 28. 8-bromo-N-methyl-N-phenyl-[1,2,4]triazolo[4,3-a]quinazolin-5-amine

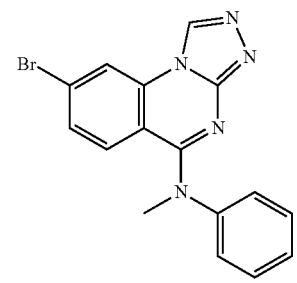

(Step 1) Synthesis of 7-bromo-2-chloro-N-methyl-N-phenylquinazolin-4-amine

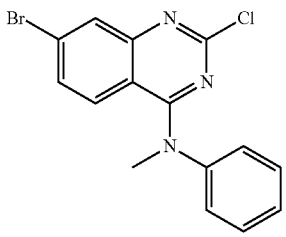

To a solution of N-methylaniline (0.327 mL, 3.02 mmol) and NaH (121 mg, 3.02 mmol) in DMF (30 mL) was added 7-bromo-2,4-dichloroquinazoline (800 mg, 2.88 mmol) at RT. The reaction mixture was stirred for 5 h at RT. The mixture was diluted with AcOEt, washed successively with water and brine, and dried over $Na_2SO_4$. The organic layer was concentrated in vacuo. The resulting residue was used in the next step without further purification. LCMS(m/z) 347.98 [M+H]+.

(Step 2) Synthesis of 7-bromo-2-hydrazinyl-N-methyl-N-phenylquinazolin-4-amine

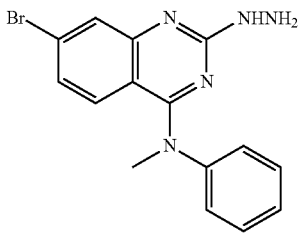 [SMILES: CN(c1ccccc1)c1nc(NN)nc2cc(Br)ccc12]

The resulting 7-bromo-2-chloro-N-methyl-N-phenylquinazolin-4-amine and hydrazine hydrate (2 mL) in EtOH (5 mL) was stirred for 1 h at 50° C. The reaction mixture was cooled to room temperature, and then diluted with EtOAc. The solution was washed successively with water and brine, and dried over $Na_2SO_4$, and concentrated in vacuo. The crude was used in the next step without purification. LCMS (m/z) 344.08 [M+H]+.

(Step 3) Synthesis of 8-bromo-N-methyl-N-phenyl-[1,2,4]triazolo[4,3-a]quinazolin-5-amine The resulting 7-bromo-2-hydrazinyl-N-methyl-N-phenylquinazolin-4-amine and triethoxymethane (5 mL) in EtOH (20 mL) was stirred overnight at 100° C. The reaction mixture was concentrated in vacuo. The residue was purified by column chromatography (Si-column, $CHCl_3$:MeOH=100:0-95:5) to afford the desired product: $^1$H-NMR (Methanol-$d_4$) δ 9.29 (d, J=2.3 Hz, 1H), 8.29 (d, J=4.8 Hz, 1H), 7.32 (t, J=7.6 Hz, 2H), 7.24-7.14 (m, 4H), 6.95 (t, J=8.1 Hz, 1H), 3.51 (d, J=2.2 Hz, 3H); LCMS(m/z) 355.0 [M+H]+.

Example 29. N,8-dimethyl-N-phenyl-[1,2,4]triazolo[4,3-a]quinazolin-5-amine

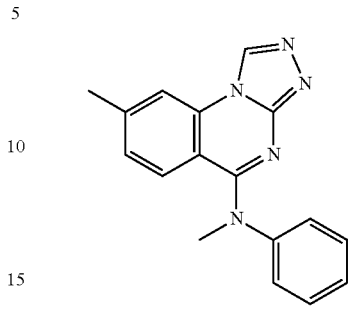

(Step 1) Synthesis of 7-methylquinazoline-2,4(1H,3H)-dione

To a suspension of 2-amino-4-methylbenzoic acid (500 mg, 3.31 mmol) in water (5 mL) was added acetic acid (0.5 mL), and the suspension was heated to 35° C. A freshly prepared solution of potassium cyanate (268 mg, 3.31 mmol) in water (0.5 mL) was added dropwise to the suspension over the period of 1 h. The mixture was stirred for 1 h at 40° C. NaOH (8 g) was added portion-wise to the reaction mixture by maintaining the internal temperature below 50° C., and the mixture was further stirred for 2 h. The precipitate was collected by filtration to give the desired product. LCMS(m/z) 177.11 [M+H]+.

(Step 2) Synthesis of 2,4-dichloro-7-methylquinazoline

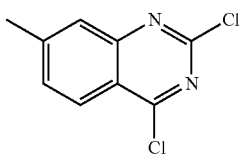

A mixture of 7-methylquinazoline-2,4(1H,3H)-dione (100 mg, 0.568 mmol) and phosphoryl trichloride (435 mg, 2.84 mmol) was heated to 100° C. for 3 h. The reaction mixture was concentrated in vacuo to give the desired product. LCMS(m/z) 213.05 [M+H]+.

(Step 3) Synthesis of
2-chloro-N,7-dimethyl-N-phenylquinazolin-4-amine

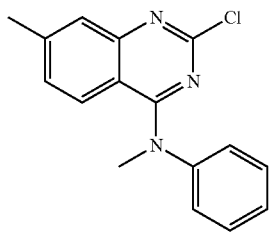 [SMILES: Cc1ccc2c(N(C)c3ccccc3)nc(Cl)nc2c1]

To a solution of 2,4-dichloro-7-methylquinazoline (100 mg, 0.47 mmol) in DMF (2.3 mL) were added N-methylaniline (55.3 mg, 0.516 mmol) and sodium hydroxide (18.77 mg, 0.469 mmol), and the mixture was stirred for 1 h at RT. The reaction mixture was diluted with AcOEt, washed successively with H$_2$O and brine, and dried over Na$_2$SO$_4$. The organic layer was concentrated in vacuo to give the desired product. LCMS(m/z) 284.8 [M+H]$^+$.

(Step 4) Synthesis of 2-hydrazinyl-N,7-dimethyl-N-phenylquinazolin-4-amine

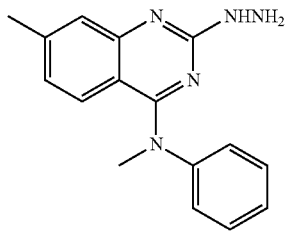 [SMILES: Cc1ccc2c(N(C)c3ccccc3)nc(NN)nc2c1]

To a solution of 2-chloro-N,7-dimethyl-N-phenylquinazolin-4-amine (71 mg, 0.25 mmol) in EtOH (1.25 mL) was added hydrazine hydrate (25.05 mg, 0.5 mmol), and the mixture was stirred for 2 h at 50° C. The reaction mixture was diluted with AcOEt, washed successively with water and brine, and dried over Na$_2$SO$_4$. The organic layer was concentrated in vacuo to give the desired product. LCMS (m/z) 280.18 [M+H]$^+$.

(Step 5) Synthesis of N,8-dimethyl-N-phenyl-[1,2,4]triazolo[4,3-a]quinazolin-5-amine A mixture of 2-hydrazinyl-N,7-dimethyl-N-phenylquinazolin-4-amine (68 mg, crude) and triethoxymethane (111 mg, 0.751 mmol) and a drop of acetic acid (12.04 mg, 0.201 mmol) was heated to 90° C. for 2 h. The reaction mixture was concentrated in vacuo, and purified by prep-HPLC to afford the desired product: $^1$H-NMR (Methanol-d$_4$) δ 9.39 (s, 1H), 7.99 (d, J=1.5 Hz, 1H), 7.47-7.39 (m, 2H), 7.34-7.22 (m, 3H), 7.16 (d, J=8.6 Hz, 1H), 6.99 (dd, J=8.5, 1.6 Hz, 1H), 3.64 (s, 3H), 2.47 (s, 3H); LCMS(m/z) 290.2 [M+H]+.

Example 30. 8-cyclopropyl-N-methyl-N-phenyl-[1,2,4]triazolo[4,3-a]quinazolin-5-amine

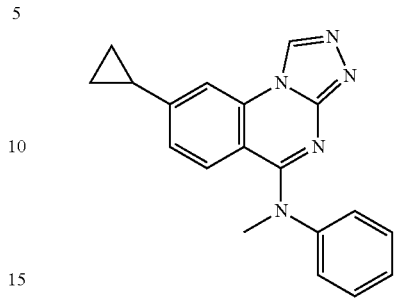

A mixture of 8-bromo-N-methyl-N-phenyl-[1,2,4]triazolo[4,3-a]quinazolin-5-amine (Example 28) (20 mg, 0.056 mmol), K$_3$PO$_4$ (30.0 mg, 0.141 mmol), Pd(OAc)$_2$ (2.54 mg, 0.011 mmol), tricyclohexylphosphine (1.583 mg, 5.65 μmol) and cyclopropylboronic acid (12.13 mg, 0.141 mmol) in dioxane/water (0.28 mL) was treated in a microwave reactor at 120° C. for 2 h. The reaction mixture was purified by column chromatography (Si-column, CHCl$_3$:MeOH=10:0-9:1) to afford the desired product: $^1$H-NMR (Methanol-d4) δ 9.44 (s, 1H), 7.81 (d, J=1.9 Hz, 1H), 7.47-7.37 (m, 2H), 7.36-7.20 (m, 3H), 7.10 (dd, J=8.9, 4.4 Hz, 1H), 6.84 (dt, J=8.8, 2.1 Hz, 1H), 3.63 (s, 3H), 2.10-1.98 (m, 1H), 1.20-1.06 (m, 2H), 0.87 (dt, J=7.0, 4.7 Hz, 2H); LCMS(m/z) 316.0 [M+H]+.

Example 31. N-methyl-N-phenyl-8-(pyridin-4-yl)-[1,2,4]triazolo[4,3-a]quinazolin-5-amine

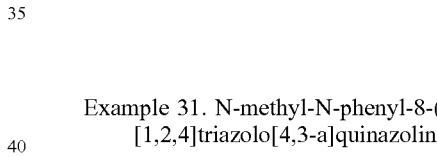

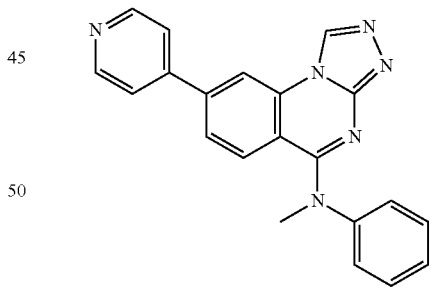

A mixture of 8-bromo-N-methyl-N-phenyl-[1,2,4]triazolo[4,3-a]quinazolin-5-amine (Example 28) (20 mg, 0.056 mmol), K$_3$PO$_4$ (30.0 mg, 0.141 mmol), Pd(OAc)$_2$ (2.54 mg, 0.011 mmol), tricyclohexylphosphine (1.583 mg, 5.65 μmol) and pyridin-4-ylboronic acid (17.35 mg, 0.141 mmol) in dioxane/water (0.28 mL) was treated in a microwave reactor at 120° C. for 2 h. The reaction mixture was concentrated in vacuo. The residue was purified by preparative-HPLC to afford the desired product: $^1$H-NMR (Methanol-d$_4$) δ 9.61 (s, 1H), 8.71-8.61 (m, 4H), 7.89-7.83 (m, 2H), 7.60 (dd, J=8.8, 1.8 Hz, 1H), 7.46 (d, J=8.2 Hz, 3H), 7.37-7.31 (m, 2H), 3.70 (s, 3H); LCMS(m/z) 353.2 [M+H]+.

Example 32. N-(2-iodophenyl)-N-methyl-[1,2,4]triazolo[4,3-a]quinazolin-5-amine

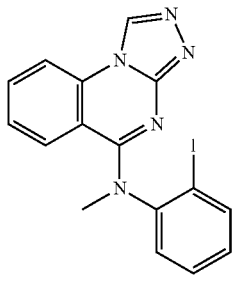

To a solution of 5-chloro-[1,2,4]triazolo[4,3-a]quinazoline (32 mg, 0.172 mmol), BrOP (73.3 mg, 0.189 mmol) and DBU (28.7 mg, 0.189 mmol) in acetonitrile (1 mL) was added to 2-iodo-N-methylaniline (40 mg, 0.172 mmol) at RT. The mixture was stirred overnight at 80° C. The reaction mixture was concentrated in vacuo, and the residue was purified by column chromatography (Si-column, CHCl$_3$:MeOH=100:0-95:5) to afford the crude product. The crude compound was further purified by prep-LCMS to afford the desired product: $^1$H-NMR (Methanol-d$_4$) δ 9.44 (s, 1H), 8.20 (dd, J=8.4, 1.0 Hz, 1H), 8.07 (dd, J=8.0, 1.4 Hz, 1H), 7.78 (ddd, J=8.5, 7.2, 1.4 Hz, 1H), 7.46 (td, J=7.6, 1.4 Hz, 1H), 7.33 (dd, J=7.9, 1.6 Hz, 1H), 7.25-7.09 (m, 3H), 3.56 (s, 3H); LCMS(m/z) 402.1 [M+H]+.

Example 33. N-methyl-N-(o-tolyl)-[1,2,4]triazolo[4,3-a]quinazolin-5-amine

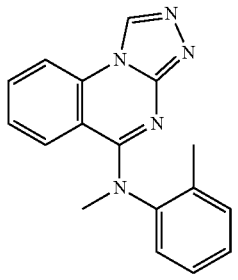 [SMILES: Cc1ccccc1N(C)c1nc2nncn2c2ccccc12]

To a solution of 5-chloro-[1,2,4]triazolo[4,3-a]quinazoline (50 mg, 0.269 mmol), BrOP (115 mg, 0.295 mmol) and DBU (45 mg, 0.295 mmol) in acetonitrile (2 mL) was added to N,2-dimethylaniline (32.5 mg, 0.269 mmol) at RT. The mixture was stirred overnight at 80° C. The reaction mixture was concentrated in vacuo, and the residue was purified by column chromatography (Si-column, CHCl$_3$:MeOH=100:0-95:5) to give the crude product. The crude compound was further purified by prep-LCMS to afford the desired product: $^1$H-NMR (Methanol-d4) δ 9.40 (s, 1H), 8.17 (dt, J=8.3, 0.8 Hz, 1H), 7.74 (ddd, J=8.4, 6.8, 1.8 Hz, 1H), 7.46-7.39 (m, 1H), 7.39-7.21 (m, 2H), 7.19-7.07 (m, 3H), 3.56 (s, 3H), 2.31 (s, 3H); LCMS(m/z) 290.2 [M+H]+.

Example 34. N-methyl-N-(m-tolyl)-[1,2,4]triazolo[4,3-a]quinazolin-5-amine

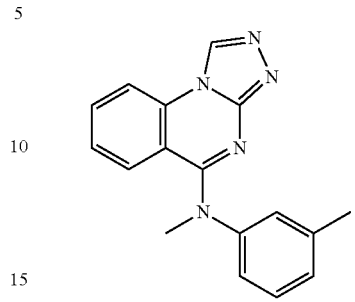

To a solution of 5-chloro-[1,2,4]triazolo[4,3-a]quinazoline (50 mg, 0.269 mmol), BrOP (115 mg, 0.295 mmol) and DBU (45.0 mg, 0.295 mmol) in acetonitrile (2 mL) was added to N,3-dimethylaniline (32.5 mg, 0.269 mmol) at RT. The mixture was stirred overnight at 50° C. The reaction mixture was concentrated in vacuo, and the residue was purified by column chromatography (Si-column, CHCl$_3$:MeOH=100:0-95:5) to give the crude product. The crude compound was further purified by prep-LCMS to afford the desired product: $^1$H-NMR (Methanol-d4) δ 9.43 (s, 1H), 8.21-8.07 (m, 1H), 7.75 (ddd, J=8.5, 7.2, 1.3 Hz, 1H), 7.37-7.24 (m, 2H), 7.23-7.11 (m, 3H), 7.11-7.03 (m, 1H), 3.65 (s, 3H), 2.33 (d, J=0.8 Hz, 3H); LCMS(m/z) 290.2 [M+H]+.

Example 35. 7-chloro-N-methyl-N-phenyl-[1,2,4]triazolo[4,3-a]quinazolin-5-amine

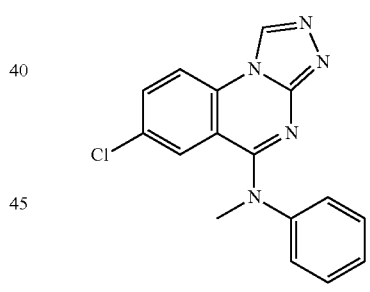

(Step 1) Synthesis of 2,6-dichloro-N-methyl-N-phenylquinazolin-4-amine

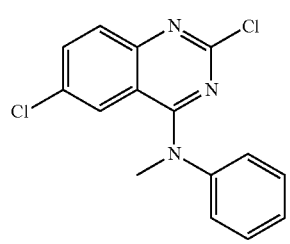 [SMILES: CN(c1ccccc1)c1nc(Cl)nc2ccc(Cl)cc12]

To a solution of N-methylaniline (138 mg, 1.285 mmol) and NaH (56.5 mg, 1.413 mmol) in DMF (10 mL) was added 2,4,6-trichloroquinazoline (300 mg, 1.285 mmol) at RT. The mixture was stirred for 1 h at RT. The reaction mixture was diluted with EtOAc, washed successively with water and brine, dried over Na₂SO₄, and concentrated in vacuo to give the desired product, which was used for the next step without purification. LCMS(m/z) 304.03 [M+H]+.

(Step 2) Synthesis of 6-chloro-2-hydrazinyl-N-methyl-N-phenylquinazolin-4-amine

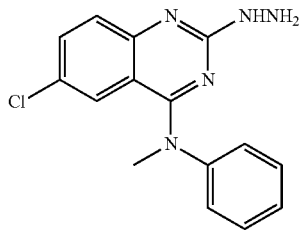 [SMILES: CN(c1ccccc1)c1nc(NN)nc2ccc(Cl)cc12]

To a solution of 2,6-dichloro-N-methyl-N-phenylquinazolin-4-amine (117 mg, crude) in EtOH (5 mL) was added hydrazine hydrate (2 mL) at RT. The mixture was stirred for 2 h at 50° C. The reaction mixture was cooled to RT, diluted with EtOAc, washed successively with water and brine, dried over Na₂SO₄, and concentrated in vacuo. The crude product was used for the next step without purification. LCMS(m/z) 300.08 [M+H]+.

(Step 3) Synthesis of 7-chloro-N-methyl-N-phenyl-[1,2,4]triazolo[4,3-a]quinazolin-5-amine A solution of crude 6-chloro-2-hydrazinyl-N-methyl-N-phenylquinazolin-4-amine in triethoxymethane (5 mL) was stirred overnight at 100° C. The reaction mixture was concentrated in vacuo, and the residue was purified by column chromatography (Si-column, hexane:AcOEt=100:0-0:100, then MeOH) to give the crude product. The crude compound was further purified by prep-LCMS to afford the desired product: ¹H-NMR (DMSO-d₆) δ 9.62 (s, 1H), 8.33 (d, J=8.8 Hz, 1H), 7.87 (dd, J=8.9, 2.3 Hz, 1H), 7.49-7.28 (m, 5H), 7.10 (d, J=2.3 Hz, 1H), 3.55 (s, 3H). LCMS(m/z) 310.1 [M+H]+.

Example 36. N,7-dimethyl-N-phenyl-[1,2,4]triazolo[4,3-a]quinazolin-5-amine

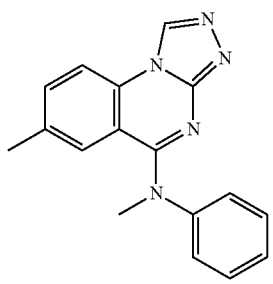 [SMILES: Cc1ccc2c(c1)c(N(C)c1ccccc1)nc1nncn12]

(Step 1) Synthesis of 2-chloro-N,6-dimethyl-N-phenylquinazolin-4-amine

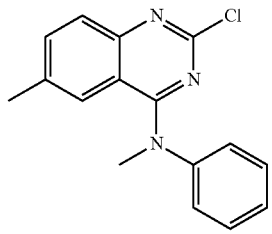 [SMILES: Cc1ccc2nc(Cl)nc(N(C)c3ccccc3)c2c1]

To a solution of N-methylaniline (151 mg, 1.408 mmol) and NaH (61.9 mg, 1.549 mmol) in DMF (10 mL) was added 2,4-dichloro-6-methylquinazoline (300 mg, 1.408 mmol) at RT. The mixture was stirred for 5h at RT. The reaction mixture was quenched with water, and diluted with AcOEt. The organic layer was washed with brine, dried over Na₂SO₄, and concentrated in vacuo to give the desired product. LCMS(m/z) 284.13 [M+H]+.

(Step 2) Synthesis of 2-hydrazinyl-N,6-dimethyl-N-phenylquinazolin-4-amine

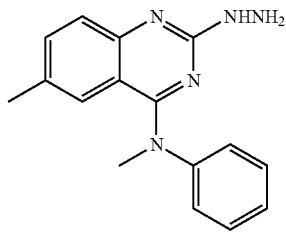 [SMILES: Cc1ccc2nc(NN)nc(N(C)c3ccccc3)c2c1]

A mixture of 2-chloro-N,6-dimethyl-N-phenylquinazolin-4-amine (123 mg, 0.43 mmol) and hydrazine hydrate (2 mL) in EtOH (5 mL) was stirred overnight at 50° C. The reaction mixture was cooled to RT, diluted with EtOAc, washed successively with water and brine, dried over Na₂SO₄, and concentrated in vacuo to give the desired product, which was used for the next step without purification. LCMS(m/z) 280.18 [M+H]+.

(Step 3) Synthesis of N,7-dimethyl-N-phenyl-[1,2,4]triazolo[4,3-a]quinazolin-5-amine A solution of 2-hydrazinyl-N,6-dimethyl-N-phenylquinazolin-4-amine (89 mg, crude) and triethoxymethane (5 mL) in EtOH (5 mL) was stirred for 4 h at 100° C. The reaction mixture was concentrated in vacuo. The residue was purified by column chromatography (Si-column, CHCl₃:MeOH=100:0-95:5) to give the crude product. The crude compound was further purified by prep-LCMS to afford the desired product: ¹H-NMR (DMSO-d₆) δ 9.57 (s, 1H), 8.18 (d, J=8.4 Hz, 1H), 7.61 (ddd, J=8.4, 1.9, 0.7 Hz, 1H), 7.45-7.35 (m, 2H), 7.33-7.24 (m, 3H), 7.00-6.94 (m, 1H), 3.54 (s, 3H), 2.05 (s, 3H); LCMS(m/z) 290.2 [M+H]+.

Example 37. N-methyl-N-phenyl-8-(prop-1-yn-1-yl)-[1,2,4]triazolo[4,3-a]quinazolin-5-amine

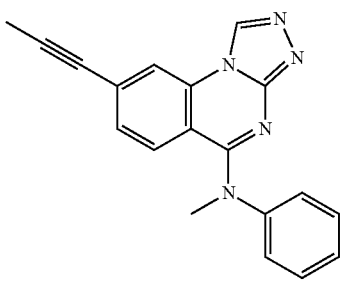 [SMILES: CC#Cc1ccc2c(N(C)c3ccccc3)nc3nncn3c2c1]

A mixture of 8-bromo-N-methyl-N-phenyl-[1,2,4]triazolo[4,3-a]quinazolin-5-amine (Example 28) (30 mg, 0.085 mmol), prop-1-yne (8.48 mg, 0.212 mmol), triethylamine (8.57 mg, 0.085 mmol), Pd(OAc)₂ (3.80 mg, 0.017 mmol), triphenylphosphine (19.99 mg, 0.076 mmol) and copper(I) iodide (3.23 mg, 0.017 mmol) in dioxane (0.4 mL) was treated in a microwave reactor at 120° C. for 2 h. The reaction mixture was purified by column chromatography (Si-column, CHCl₃:MeOH=10:0-9:1) to afford the desired product: ¹H-NMR (CDCl₃) δ 8.90 (s, 1H), 7.77 (d, J=1.5 Hz, 1H), 7.44-7.32 (m, 2H), 7.31-7.22 (m, 1H), 7.23-7.11 (m, 3H), 7.05 (dd, J=8.7, 1.6 Hz, 1H), 3.67 (s, 3H), 2.08 (s, 3H); LCMS(m/z) 314.2 [M+H]+.

Example 38. 5-(methyl(phenyl)amino)-[1,2,4]triazolo[4,3-a]quinazolin-8-ol

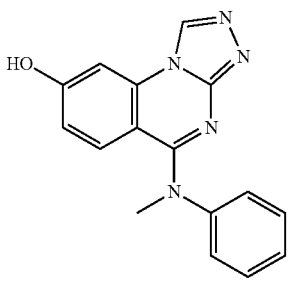 [SMILES: CN(c1ccccc1)c1nc2nncn2c2cc(O)ccc12]

To a solution 8-methoxy-N-methyl-N-phenyl-[1,2,4]triazolo[4,3-a]quinazolin-5-amine (Example 20) (20 mg, 0.066 mmol) in 1,2-dichloroethane (1 mL) was added tribromoborane (0.197 mL, 0.197 mmol) at RT, and the mixture was stirred for 1 h at 50° C. The reaction mixture was concentrated in vacuo, and the residue was purified by column chromatography (Si-column, CHCl₃:MeOH=100:0-90:10) to afford the desired product: ¹H-NMR (DMSO-d₆) δ 9.48 (s, 1H), 7.50 (d, J=2.4 Hz, 1H), 7.38 (dd, J=8.5, 7.1 Hz, 2H), 7.28-7.19 (m, 3H), 7.09 (d, J=9.1 Hz, 1H), 6.62 (dd, J=9.2, 2.4 Hz, 1H), 3.50 (s, 3H); LCMS(m/z) 292.2 [M+H]+.

Example 39. N-phenyl-N-propyl-[1,2,4]triazolo[4,3-a]quinazolin-5-amine

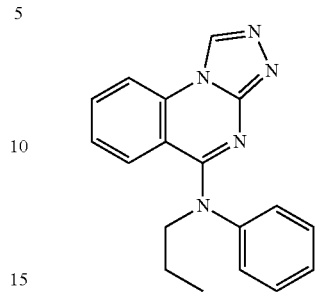

(Step 1) Synthesis of 2-chloro-N-phenyl-N-propylquinazolin-4-amine

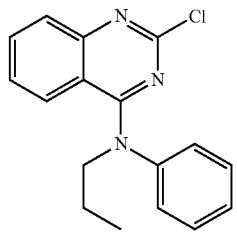 [SMILES: CCCN(c1ccccc1)c1nc(Cl)nc2ccccc12]

To a solution of 60% sodium hydride (0.12 g, 3.01 mmol) in DMF (10 mL) was added N-propylaniline (0.339 g, 2.51 mmol) at 0° C. and the mixture was stirred for 1 h at RT, followed by the addition of 2,4-dichloroquinazoline (0.5 g, 2.51 mmol) at 0° C., and the mixture was stirred for 16 h at RT. The reaction mixture was diluted with ice-water. The resulting solids were filtered and dried under vacuum to give the desired product. LCMS: 298.14 (M+H).

(Step 2) Synthesis of 2-hydrazinyl-N-phenyl-N-propylquinazolin-4-amine

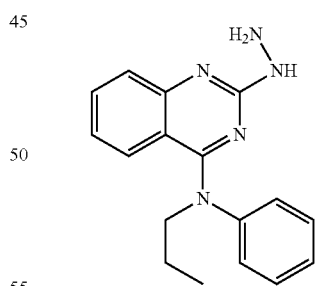

To a stirred solution of 2-chloro-N-phenyl-N-propylquinazolin-4-amine (crude, 0.2 g, 0.67 mmol) in EtOH (5 mL) was added hydrazine hydrate (0.067 g, 1.34 mmol) at RT and the mixture was stirred at 50° C. for 16 h. The reaction mixture was evaporated under reduced pressure to give the desired product. LCMS: 294.09 (M+H).

(Step 3) Synthesis of N-phenyl-N-propyl-[1,2,4]triazolo[4,3-a]quinazolin-5-amine A mixture of 2-hydrazinyl-N-phenyl-N-propylquinazolin-4-amine (crude, 0.15 g, 0.51 mmol) and triethyl orthoformate (3 mL) was stirred at 80° C. for 3 h. The reaction mixture was evaporated under reduced pressure, and the residue was purified by prep. HPLC to afford the desired product: $^1$H-NMR (DMSO-$d_6$) δ 9.60 (s, 1H), 8.27 (dd, J=8.3, 1.1 Hz, 1H), 7.75 (ddd, J=8.4, 7.0, 1.6 Hz, 1H), 7.43-7.33 (m, 2H), 7.30-7.14 (m, 5H), 4.13-3.94 (m, 2H), 1.74 (d, J=7.5 Hz, 2H), 0.95 (t, J=7.4 Hz, 3H); LCMS(m/z) 304.18 [M+H]+.

Example 40. N-benzyl-N-phenyl-[1,2,4]triazolo[4,3-a]quinazolin-5-amine

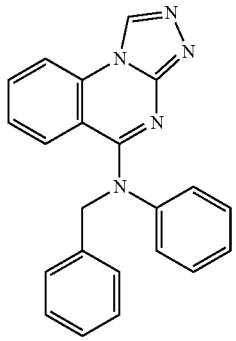

To a solution of N-benzylaniline (0.018 g, 0.098 mmol) in THF (1 mL) was added LDA (0.1 mL, 0.2 mmol, 2.0 M in THF) at 0° C. and the mixture was stirred at RT for 1 h, followed by the addition of 5-chloro-[1,2,4]triazolo[4,3-a]quinazoline (0.02 g, 0.098 mmol) at 0° C., and the mixture was stirred for 2 h at RT. The reaction mixture was diluted with water and extracted with ethyl acetate. The organic layer was dried over Na$_2$SO$_4$, filtered and evaporated under reduced pressure. The residue was purified by silica gel column chromatography, eluted with 5% methanol/dichloromethane to afford the desired product: $^1$H-NMR (DMSO-$d_6$) δ 9.64 (s, 1H), 8.30 (d, J=8.3 Hz, 1H), 7.55-7.05 (m, 13H), 5.40 (s, 2H); LCMS(m/z) 352.2 [M+H]+.

Example 41. N-(cyclopropylmethyl)-N-phenyl-[1,2,4]triazolo[4,3-a]quinazolin-5-amine

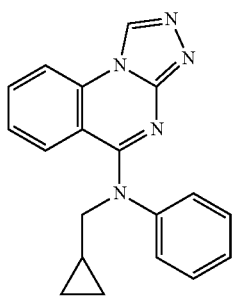 [SMILES: c1ccc(N(CC2CC2)c2nc3nncn3c3ccccc23)cc1]

(Step 1) Synthesis of N-(cyclopropylmethyl)aniline

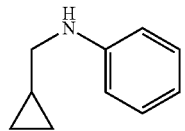 [SMILES: c1ccc(NCC2CC2)cc1]

To a solution of aniline (2.0 g, 21.47 mmol) in EtOH (20 mL) were added cyclopropanecarbaldehyde (3.01 g, 42.95 mmol) and a catalytic amount of acetic acid at RT and the mixture was stirred at RT for 1 h, followed by the addition of sodium triacetoxyborohydride (9.10 g, 42.95 mmol) at RT, and the mixture was stirred at RT for 2 h. The reaction mixture was evaporated under reduced pressure, the residue was purified by silica gel column chromatography and eluted with 10% ethyl acetate/petroleum ether to give the desired product. LCMS: 148.31 (M+H).

(Step 2) Synthesis of N-(cyclopropylmethyl)-N-phenyl-[1,2,4]triazolo[4,3-a]quinazolin-5-amine To a solution of N-(cyclopropylmethyl)aniline (crude, 0.014 g, 0.098 mmol) in THF (1 mL) was added LDA (0.15 mL, 0.20 mmol, 1.0 M in THF) at 0° C. and the mixture was stirred at RT for 0.5 h, followed by the addition of 5-chloro-[1,2,4]triazolo[4,3-a]quinazoline (0.02 g, 0.098 mmol) at 0° C. The mixture was stirred at the RT for 1 h. The reaction mixture was diluted with water and extracted with ethyl acetate. The organic layer was dried over Na$_2$SO$_4$, filtered and evaporated under reduced pressure. The residue was purified by silica gel column chromatography and eluted with 100% ethyl acetate to afford the desired product: $^1$H-NMR (DMSO-$d_6$) δ 9.60 (s, 1H), 8.28 (dd, J=8.3, 1.1 Hz, 1H), 7.76 (ddd, J=8.4, 7.1, 1.4 Hz, 1H), 7.40-7.36 (m, 2H), 7.30-7.17 (m, 5H), 3.96 (d, J=6.8 Hz, 2H), 1.45-1.31 (m, 1H), 0.44-0.33 (m, 2H), 0.20-0.09 (m, 2H); LCMS(m/z) 316.4 [M+H]+.

Example 42. 4-([1,2,4]triazolo[4,3-a]quinazolin-5-yl)-3,4-dihydro-2H-benzo[b][1,4]oxazine

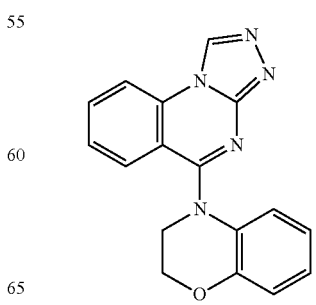

(Step 1) Synthesis of 4-(2-chloroquinazolin-4-yl)-3,4-dihydro-2H-benzo[b][1,4]oxazine

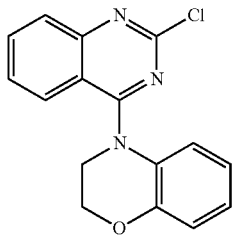 [SMILES: Clc1nc(N2CCOc3ccccc32)c2ccccc2n1]

To a stirred solution of 60% sodium hydride (0.120 g, 3.01 mmol) in DMF (10 mL) was added 3,4-dihydro-2H-benzo[b][1,4]oxazine (0.339 g, 2.51 mmol) at 0° C. and the mixture was stirred for 2 h at RT, followed by the addition of 2,4-dichloroquinazoline (0.5 g, 2.51 mmol) at 0° C., and the mixture was stirred for 8 h at RT. The reaction mixture was quenched with ice-water. The resulting solids were filtered and dried under vacuum to give the desired product. LCMS: 298.11 (M+H).

(Step 2) Synthesis of 4-(2-hydrazinylquinazolin-4-yl)-3,4-dihydro-2H-benzo[b][1,4]oxazine

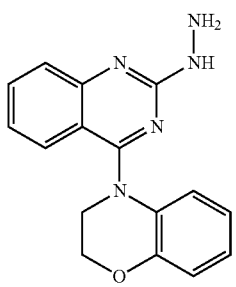 [SMILES: NNc1nc(N2CCOc3ccccc32)c2ccccc2n1]

To a solution of 4-(2-chloroquinazolin-4-yl)-3,4-dihydro-2H-benzo[b][1,4]oxazine (0.3 g, 1.01 mmol) in EtOH (10 mL) was added hydrazine hydrate (0.101 mL, 2.02 mmol) at RT and the mixture was stirred at 50° C. for 5 h. The reaction mixture was evaporated under reduced pressure. The residue was washed with n-pentane and diethyl ether to give the desired product. LCMS: 294.18 (M+H).

(Step 3) Synthesis of 4-([1,2,4]triazolo[4,3-a]quinazolin-5-yl)-3,4-dihydro-2H-benzo[b][1,4]oxazine A mixture of 4-(2-hydrazinylquinazolin-4-yl)-3,4-dihydro-2H-benzo[b][1,4]oxazine (crude, 0.2 g, 0.68 mmol) and triethyl orthoformate (0.3 g, 2.05 mmol) was stirred at 90° C. for 2 h. The reaction mixture was diluted with ethanol and the resulting solids were collected by filtration to give a crude product. The crude product was purified by prep. HPLC to afford the desired product: $^1$H-NMR (500 MHz, DMSO-$d_6$) δ 9.74 (s, 1H), 8.41 (dd, J=8.4, 1.1 Hz, 1H), 8.08 (dd, J=8.3, 1.3 Hz, 1H), 7.97 (ddd, J=8.5, 7.3, 1.4 Hz, 1H), 7.56 (ddd, J=8.3, 7.3, 1.1 Hz, 1H), 7.00-6.92 (m, 2H), 6.92-6.84 (m, 1H), 6.71 (ddd, J=8.4, 5.5, 3.3 Hz, 1H), 4.41 (dd, J=5.2, 3.7 Hz, 2H), 4.03 (t, J=4.5 Hz, 2H); LCMS(m/z) 304.2.

Example 43. N,N-diphenyl-[1,2,4]triazolo[4,3-a]quinazolin-5-amine

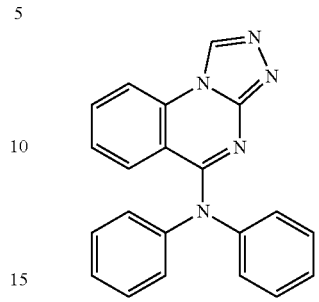

(Step 1) Synthesis of 2-chloro-N,N-diphenylquinazolin-4-amine

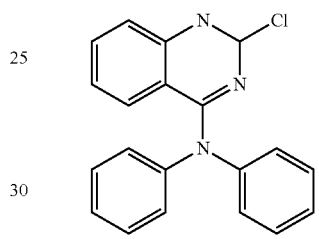

To a solution of 2,4-dichloroquinazoline (1.0 g, 5.02 mmol) in DMF (20 mL) was added 60% sodium hydride (0.241 g, 6.03 mmol) at 0° C. and the mixture was stirred for 1 h at RT, followed by the addition of diphenylamine (0.849 g, 5.02 mmol) at 0° C., and the mixture was stirred for 2 h at RT. The reaction mixture was diluted with ice-water and extracted with ethyl acetate twice. The combined organic layer was washed with brine, dried over anhydrous $Na_2SO_4$, filtered and evaporated under reduced pressure to give the desired product. LCMS: 332.15 (M+H).

(Step 2) Synthesis of 2-hydrazinyl-N,N-diphenylquinazolin-4-amine

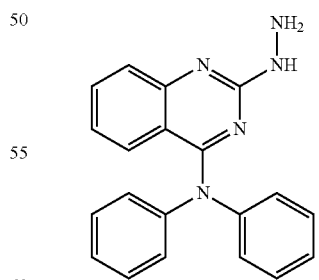

To a solution of 2-chloro-N,N-diphenylquinazolin-4-amine (0.3 g, 0.90 mmol) in EtOH (10 mL) was added hydrazine hydrate (0.090 g, 1.8 mmol) at RT and the mixture was stirred at 50° C. for 16 h. The reaction mixture was evaporated under reduced pressure to give the desired product. LCMS: 328.23 (M+H).

(Step 3) Synthesis of N,N-diphenyl-[1,2,4]triazolo[4,3-a]quinazolin-5-amine

A mixture of 2-hydrazinyl-N,N-diphenylquinazolin-4-amine (0.3 g, 0.91 mmol) and triethyl orthoformate (0.407 g, 2.75 mmol) was stirred to 80° C. for 3 h. The reaction mixture was evaporated under reduced pressure. The residue was purified by prep. HPLC to afford the desired product: $^1$H-NMR (DMSO-$d_6$) δ 9.72 (s, 1H), 8.37 (dd, J=8.3, 1.1 Hz, 1H), 7.87 (ddd, J=8.5, 7.3, 1.3 Hz, 1H), 7.59 (dd, J=8.5, 1.3 Hz, 1H), 7.48-7.29 (m, 5H), 7.29-7.10 (m, 6H); LCMS(m/z) 338.3 [M+H]+.

Example 44. N-methyl-N-(thiophen-3-yl)-[1,2,4]triazolo[4,3-a]quinazolin-5-amine

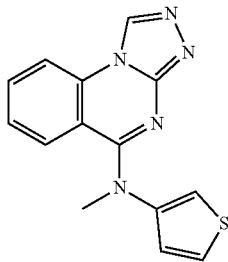

(Step 1) Synthesis of 2-chloro-N-methyl-N-(thiophen-3-yl)quinazolin-4-amine

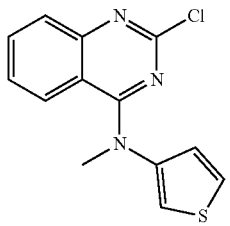 [SMILES: CN(c1ccsc1)c1nc(Cl)nc2ccccc12]

To a stirred solution of N-methylthiophen-3-amine (0.051 g, 0.45 mmol) in DMF (3 mL) was added 60% sodium hydride (0.018 g, 0.45 mmol) at 0° C. and the mixture was stirred for 1 h at RT, followed by the addition of 2,4-dichloroquinazoline (0.09 g, 0.45 mmol) at 0° C., and the mixture was stirred for 12 h at RT. The progress of the reaction was monitored by TLC. After completion of the reaction, the reaction mixture was diluted with ice-water and extracted with ethyl acetate twice. The combined organic layers were washed successively with water, brine, dried over Na$_2$SO$_4$, filtered and evaporated under reduced pressure. The residue was purified by silica gel column chromatography and eluted with 4% methanol/dichloromethane to give the desired product: LCMS(m/z) 276.07 [M+H]$^+$.

(Step 2) Synthesis of N-methyl-N-(thiophen-3-yl)-[1,2,4]triazolo[4,3-a]quinazolin-5-amine To a stirred solution of 2-chloro-N-methyl-N-(thiophen-3-yl)quinazolin-4-amine (0.030 g, 0.11 mmol) in toluene (3 mL) was added formohydrazide (0.013 g, 0.22 mmol) at RT and the mixture was heated to 120° C. for 72 h. The progress of the reaction was monitored by TLC. After completion of the reaction, the reaction mixture was evaporated under reduced pressure. The residue was purified by prep. HPLC to afford the desired product: $^1$H-NMR (CDCl$_3$) δ 8.93 (s, 1H), 7.80 (dd, J=8.4, 1.2 Hz, 1H), 7.68 (ddd, J=8.5, 7.3, 1.3 Hz, 1H), 7.47-7.34 (m, 2H), 7.20 (ddd, J=8.5, 7.3, 1.2 Hz, 1H), 7.04-6.95 (m, 1H), 6.85 (dd, J=3.2, 1.5 Hz, 1H), 3.64 (s, 3H); LCMS(m/z) 282.1 [M+H]+.

Example 45. 8-(furan-2-yl)-N-methyl-N-phenyl-[1,2,4]triazolo[4,3-a]quinazolin-5-amine

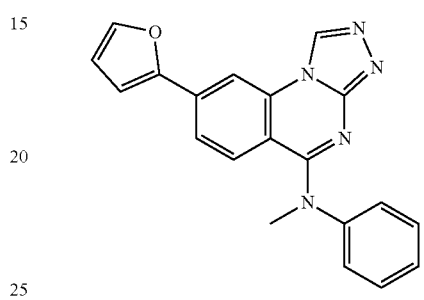

A mixture of 8-bromo-N-methyl-N-phenyl-[1,2,4]triazolo[4,3-a]quinazolin-5-amine (Example 28) (30 mg, 0.085 mmol), K$_3$PO$_4$ (17.98 mg, 0.085 mmol), Pd(OAc)$_2$ (3.80 mg, 0.017 mmol), tricyclohexylphosphine (4.75 mg, 0.017 mmol) and furan-2-ylboronic acid (23.69 mg, 0.212 mmol) in dioxane/water (0.42 mL) was heated at 100° C. for 3 h. The reaction mixture was concentrated in vacuo. The residue was purified by column chromatography (Si-column, CHCl$_3$:MeOH=10:0-9:1) to afford the desired product: $^1$H-NMR (Methanol-$d_4$) δ 9.32 (s, 1H), 8.06 (s, 1H), 7.97 (s, 1H), 7.49 (s, 1H), 7.30 (t, J=7.7 Hz, 2H), 7.19 (t, J=7.5 Hz, 1H), 7.13 (t, J=7.5 Hz, 3H), 6.94 (d, J=8.8 Hz, 1H), 6.81 (s, 1H), 3.49 (s, 3H); LCMS(m/z) 342.0.

Example 46. N-methyl-N-phenyl-8-(1H-pyrazol-4-yl)-[1,2,4]triazolo[4,3-a]quinazolin-5-amine

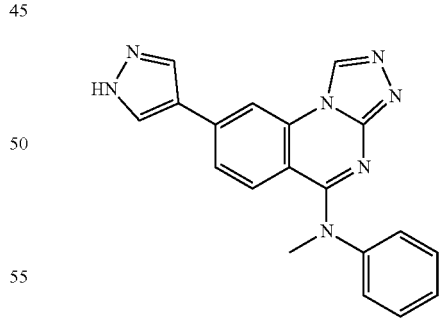

A mixture of 8-bromo-N-methyl-N-phenyl-[1,2,4]triazolo[4,3-a]quinazolin-5-amine (Example 28) (20 mg, 0.056 mmol), K$_3$PO$_4$ (30.0 mg, 0.141 mmol), Pd(OAc)$_2$ (2.54 mg, 0.011 mmol), tricyclohexylphosphine (3.17 mg, 0.011 mmol) and (1H-pyrazol-4-yl)boronic acid (15.79 mg, 0.141 mmol) in dioxane/water (0.28 mL) was treated in a microwave reactor at 100° C. for 3 h. The reaction mixture was purified by column chromatography (Si-column, CHCl$_3$:MeOH=10:0-9:1) to afford the desired product: $^1$H-NMR (Methanol-d$_4$) δ 9.50 (s, 1H), 8.37 (s, 1H), 8.18 (s, 2H), 7.48-7.25 (m, 7H), 7.20 (d, J=8.8 Hz, 1H), 3.64 (s, 3H); LCMS(m/z) 342.2 [M+H]+.

Example 47. N-methyl-N-phenyl-8-(thiophen-2-yl)-[1,2,4]triazolo[4,3-a]quinazolin-5-amine

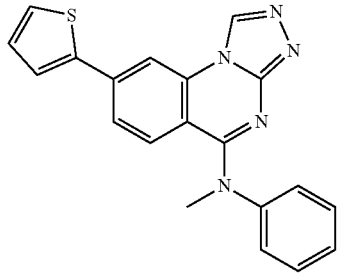 [SMILES: CN(c1ccccc1)c1nc2nncn2c2cc(-c3ccco3)ccc12]

A mixture of 8-bromo-N-methyl-N-phenyl-[1,2,4]triazolo[4,3-a]quinazolin-5-amine (Example 28) (20 mg, 0.056 mmol), K$_3$PO$_4$ (23.97 mg, 0.113 mmol), Pd(OAc)$_2$ (2.54 mg, 0.011 mmol), tricyclohexylphosphine (3.17 mg, 0.011 mmol) and thiophen-2-ylboronic acid (18.06 mg, 0.141 mmol) in dioxane/water (0.28 ml) was heated at 120° C. for 2 h. The reaction mixture was concentrated in vacuo. The residue was column chromatography (Si-column, CHCl$_3$: MeOH=10:0-9:1) to afford the desired product: $^1$H-NMR (CDCl$_3$) δ 9.00 (s, 1H), 7.92 (d, J=1.7 Hz, 1H), 7.46 (dd, J=3.7, 1.1 Hz, 1H), 7.43-7.33 (m, 3H), 7.31-7.27 (m, 1H), 7.24 (s, 1H), 7.21-7.14 (m, 2H), 7.11 (dd, J=5.1, 3.7 Hz, 1H), 3.65 (s, 3H); LCMS(m/z) 358.2 [M+H]+.

Example 48. 4-([1,2,4]triazolo[4,3-a]quinazolin-5-yl(methyl)amino)phenol

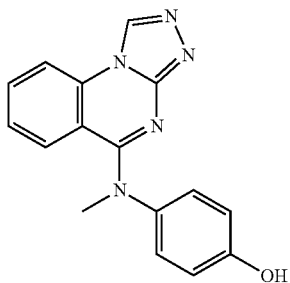 [SMILES: CN(c1ccc(O)cc1)c1nc2nncn2c2ccccc12]

To a solution of N-(4-methoxyphenyl)-N-methyl-[1,2,4]triazolo[4,3-a]quinazolin-5-amine (Example 5) (15 mg, 0.049 mmol) in 1,2-dichloroethane (1 mL) was added BBr$_3$ (0.147 mL, 0.147 mmol) at RT. The mixture was stirred for 1.5 h at 50° C. The reaction mixture was concentrated in vacuo, and the residue was purified by prep-LCMS to afford the desired product: $^1$H-NMR (DMSO-d$_6$) δ 9.64 (s, 1H), 9.56 (s, 1H), 8.29-8.21 (m, 1H), 7.75 (ddd, J=8.4, 7.1, 1.5 Hz, 1H), 7.28 (dd, J=8.4, 1.4 Hz, 1H), 7.22 (ddd, J=8.4, 7.1, 1.2 Hz, 1H), 7.16-7.02 (m, 2H), 6.84-6.71 (m, 2H), 3.46 (s, 3H); LCMS(m/z) 292.2 [M+H]+.

Example 49. 2-([1,2,4]triazolo[4,3-a]quinazolin-5-yl(methyl)amino)phenol

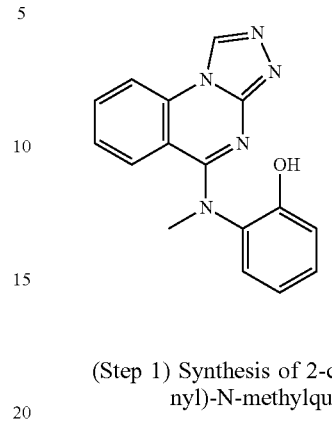

(Step 1) Synthesis of 2-chloro-N-(2-methoxyphenyl)-N-methylquinazolin-4-amine

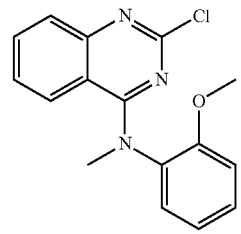 [SMILES: COc1ccccc1N(C)c1nc(Cl)nc2ccccc12]

To a suspension of 2,4-dichloroquinazoline (100 mg, 0.502 mmol) in DMF (2.5 mL) were added 2-methoxy-N-methylaniline (68.9 mg, 0.502 mmol) and sodium hydroxide (20.1 mg, 0.502 mmol), and the mixture was stirred for 2 h at RT. The reaction mixture was diluted with AcOEt, washed successively with water and brine, and dried over Na$_2$SO$_4$. The organic layer was concentrated in vacuo to give the desired product, which was used for the next step without further purification. LCMS: 300.18 (M+H).

(Step 2) Synthesis of N-(2-methoxyphenyl)-N-methyl-[1,2,4]triazolo[4,3-a]quinazolin-5-amine

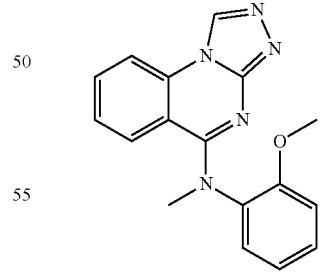

A mixture of 2-chloro-N-(2-methoxyphenyl)-N-methylquinazolin-4-amine (59 mg, crude) and formohydrazide (23.64 mg, 0.394 mmol) in toluene (1 mL) was stirred reflux for 3 days. The reaction mixture was dissolved in MeOH/AcOEt, concentrated in vacuo. The residue was dissolved in MeOH and evaporated, and the residue was purified by prep-HPLC to give the desired product. LCMS: 306.13 (M+H).

(Step 3) Synthesis of 2-([1,2,4]triazolo[4,3-a]quinazolin-5-yl(methyl)amino)phenol To a solution of N-(2-methoxyphenyl)-N-methyl-[1,2,4]triazolo[4,3-a]quinazolin-5-amine (15 mg, 0.049 mmol) in 1,2-dichloroethane (1 mL) was added BBr$_3$ (0.147 mL, 0.147 mmol) at RT. The mixture was stirred for 1.5 h at 50° C. The reaction mixture was concentrated in vacuo, and the residue was purified by prep-LCMS to afford the desired product: $^1$H-NMR (DMSO-d$_6$) δ 9.91 (s, 1H), 9.55 (s, 1H), 8.26 (dd, J=8.5, 1.1 Hz, 1H), 7.75 (ddd, J=8.4, 7.2, 1.4 Hz, 1H), 7.30 (dd, J=8.4, 1.3 Hz, 1H), 7.23-7.11 (m, 3H), 6.96 (dd, J=8.1, 1.4 Hz, 1H), 6.82 (td, J=7.6, 1.4 Hz, 1H), 3.41 (s, 3H); LCMS(m/z) 292.2 [M+H]+.

Example 50. 3-([1,2,4]triazolo[4,3-a]quinazolin-5-yl(methyl)amino)phenol

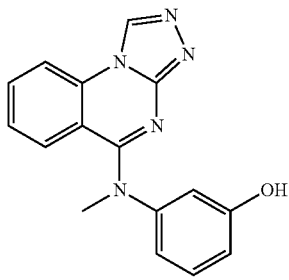

To a solution of N-(3-methoxyphenyl)-N-methyl-[1,2,4]triazolo[4,3-a]quinazolin-5-amine (Example 9) (10 mg, 0.033 mmol) in 1,2-dichloroethane (1 mL) was added BBr$_3$ (0.098 mL, 0.098 mmol) at RT. The mixture was stirred for 1.5 h at 50° C. The reaction mixture was concentrated in vacuo, and the residue was purified by prep-LCMS to afford the desired product: $^1$H-NMR (Methanol-d$_4$) δ 9.42 (s, 1H), 8.16 (dd, J=8.3, 1.0 Hz, 1H), 7.75 (ddd, J=8.5, 7.3, 1.3 Hz, 1H), 7.46 (dd, J=8.4, 1.2 Hz, 1H), 7.27-7.18 (m, 2H), 6.79-6.72 (m, 3H), 6.67 (t, J=2.2 Hz, 1H), 3.63 (s, 3H); LCMS(m/z) 292.2 [M+H]+.

Example 51. N-butyl-N-phenyl-[1,2,4]triazolo[4,3-a]quinazolin-5-amine

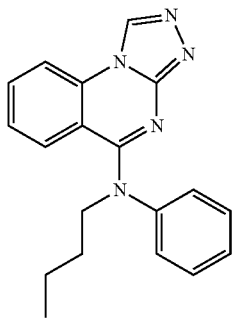 [SMILES: CCCCN(c1ccccc1)c1nc2nncn2c2ccccc12]

To a solution of N-butylaniline (0.036 g, 0.24 mmol) in THF (10 mL) was added LDA (0.24 mL, 0.49 mmol, 2.0 M in THF) at 0° C. and the mixture was stirred at RT for 1 h, followed by the addition of 5-chloro-[1,2,4]triazolo[4,3-a]quinazoline (0.05 g, 0.24 mmol) at 0° C., and the mixture was stirred at RT for 2 h. The reaction mixture was diluted with water and extracted with ethyl acetate. The organic layer was dried over Na$_2$SO$_4$, filtered and evaporated under reduced pressure. The residue was purified by prep. HPLC to afford the desired product: $^1$H-NMR (500 MHz, DMSO-d$_6$) δ 9.61 (s, 1H), 8.27 (dd, J=8.3, 1.1 Hz, 1H), 7.75 (ddd, J=8.4, 6.9, 1.6 Hz, 1H), 7.45-7.34 (m, 2H), 7.30-7.14 (m, 5H), 4.11-4.03 (m, 2H), 1.70 (ddt, J=9.4, 7.5, 3.6 Hz, 2H), 1.38 (h, J=7.4 Hz, 2H), 0.90 (t, J=7.4 Hz, 3H); LCMS(m/z) 318.2 [M+H]+.

Example 52. N-(2-methoxyethyl)-N-phenyl-[1,2,4]triazolo[4,3-a]quinazolin-5-amine

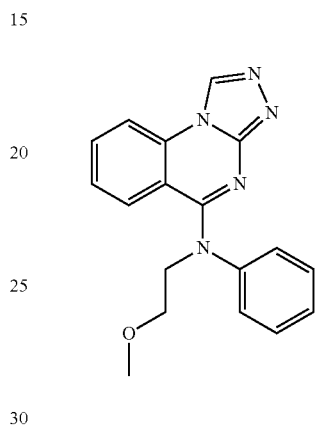

(Step 1) Synthesis of N-(2-methoxyethyl)aniline

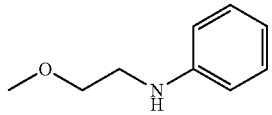

To a solution of aniline (1.0 g, 10.74 mmol) in N-methyl 2 pyrrolidone (10 mL) were added potassium carbonate (1.48 g, 10.74 mmol) and 1-bromo-2-methoxyethane (1.18 g, 8.59 mmol) at RT and the mixture was stirred at 80° C. for 5 h. The reaction mixture was diluted with water and extracted with ethyl acetate. The organic layer was dried over Na$_2$SO$_4$, filtered and evaporated under reduced pressure. The residue was purified by silica gel column chromatography, eluted with 20% ethyl acetate/petroleum ether to give the desired product. LCMS: 152.13 (M+H).

(Step 2) Synthesis of N-(2-methoxyethyl)-N-phenyl-[1,2,4]triazolo[4,3-a]quinazolin-5-amine To a solution of N-(2-methoxyethyl)aniline (0.014 g, 0.098 mmol) in THF (1 mL) was added LDA (0.1 mL, 0.20 mmol, 2.0 M in THF) at RT and the mixture was stirred at RT for 10 mins, followed by the addition of 5-chloro-[1,2,4]triazolo[4,3-a]quinazoline (0.02 g, 0.098 mmol) at RT, and the mixture was stirred at RT for 2 h. The reaction mixture was diluted with water and extracted with ethyl acetate. The organic layer was dried over Na$_2$SO$_4$, filtered and evaporated under reduced pressure. The residue was purified by silica gel column chromatography, eluted with 5% methanol/dichloromethane to afford the desired product: $^1$H-NMR (500 MHz, DMSO-d$_6$) δ 9.62 (s, 1H), 8.28 (dt, J=8.3, 0.9 Hz, 1H), 7.76 (ddd, J=8.4, 5.5, 3.0 Hz, 1H), 7.42-7.34 (m, 2H), 7.34-7.15 (m, 5H), 4.24 (t, J=5.9 Hz, 2H), 3.69 (t, J=5.9 Hz, 2H), 3.26 (s, 3H); LCMS(m/z) 320.1 [M+H]+.

Example 53. N-(cyclohexylmethyl)-N-phenyl-[1,2,4]triazolo[4,3-a]quinazolin-5-amine

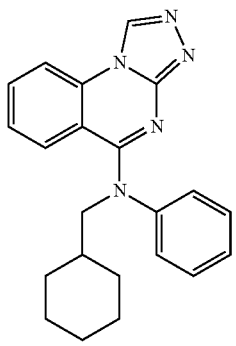 [SMILES: c1ccc(N(CC2CCCCC2)c2nc3nncn3c3ccccc23)cc1]

(Step 1) Synthesis of N-(cyclohexylmethyl)aniline

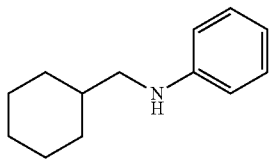 [SMILES: c1ccc(NCC2CCCCC2)cc1]

To a mixture of aniline (2.0 g, 21.47 mmol) and cyclohexanecarbaldehyde (2.59 mL, 21.47 mmol) in acetonitrile (20 mL) were added acetic acid (5 mL, 85.9 mmol) at 0° C. and the mixture was stirred for 1 h at RT, followed by the addition of sodium triacetoxyborohydride (13.66 g, 64.42 mmol) at 0° C. and the mixture was then stirred for 3 h at RT. The reaction mixture was diluted with ice-water and extracted with ethyl acetate. The organic layer was washed with brine, dried over Na$_2$SO$_4$, filtered and evaporated under reduced pressure. The residue was purified by silica gel chromatography, eluted with 2% ethyl acetate/petroleum ether to give the desired product. LCMS: 190.12 (M+H).

(Step 2) Synthesis of 2-chloro-N-(cyclohexylmethyl)-N-phenylquinazolin-4-amine

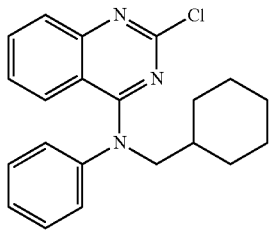 [SMILES: Clc1nc(N(CC2CCCCC2)c2ccccc2)c2ccccc2n1]

To a mixture of 2,4-dichloroquinazoline (0.525 g, 2.64 mmol) and N-(cyclohexylmethyl)aniline (0.501 g, 2.64 mmol) in DMF (5 mL) was added sodium hydroxide (0.211 g, 5.28 mmol) at 0° C. and the mixture was stirred for 72 h at RT. The reaction mixture was diluted with ice-water and extracted with ethyl acetate. The organic layer was washed with brine, dried over Na$_2$SO$_4$, filtered and evaporated under reduced pressure. The residue was purified by silica gel chromatography, eluted with 5% ethyl acetate/petroleum ether to give the desired product. LCMS: 352.32 (M+H).

(Step 3) Synthesis of N-(cyclohexylmethyl)-2-hydrazinyl-N-phenylquinazolin-4-amine

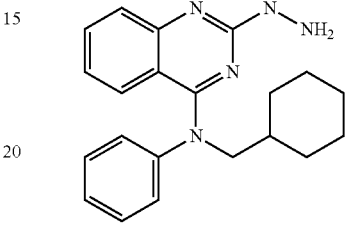

To a stirred solution of 2-chloro-N-(cyclohexylmethyl)-N-phenylquinazolin-4-amine (0.24 g, 0.68 mmol) in EtOH (5 mL) was added hydrazine hydrate (0.068 g, 1.36 mmol) at RT and the mixture was stirred at 50° C. for 16 h. The reaction mixture was evaporated under reduced pressure to give the desired product. LCMS: 348.22 (M+H).

(Step 4) Synthesis of N-(cyclohexylmethyl)-N-phenyl-[1,2,4]triazolo[4,3-a]quinazolin-5-amine A mixture of N-(cyclohexylmethyl)-2-hydrazinyl-N-phenylquinazolin-4-amine (0.215 g, 0.62 mmol) and triethyl orthoformate (2 mL) was stirred at 100° C. for 16 h. The reaction mixture was evaporated under reduced pressure, and the residue was purified by prep. HPLC to afford the desired product: $^1$H-NMR (DMSO-d$_6$) δ 9.62 (s, 1H), 8.28 (dd, J=8.4, 1.2 Hz, 1H), 7.76 (ddd, J=8.5, 7.2, 1.4 Hz, 1H), 7.39-7.16 (m, 7H), 3.94 (d, J=7.2 Hz, 2H), 1.91 (d, J=12.0 Hz, 1H), 1.80 (d, J=8.5 Hz, 2H), 1.70-1.57 (m, 3H), 1.13 (q, J=10.8 Hz, 5H); LCMS(m/z) 358.3 [M+H]+.

Example 54. N-neopentyl-N-phenyl-[1,2,4]triazolo[4,3-a]quinazolin-5-amine

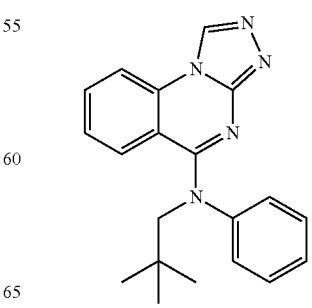

(Step 1) Synthesis of N-neopentylaniline

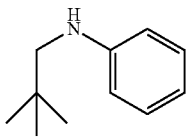

To a solution of aniline (0.5 g, 5.37 mmol) in acetonitrile (10 mL) were added pivalaldehyde (0.508 g, 5.91 mmol) and acetic acid (1.288 g, 21.48 mmol) at 0° C. and the mixture was stirred for 2 h at RT, followed by the addition of sodium triacetoxyborohydride (2.27 g, 10.74 mmol) at 0° C., and the mixture was stirred for 2 h at RT. The reaction mixture was diluted with ice-water and extracted with ethyl acetate. The organic layer was washed with brine, dried over $Na_2SO_4$, filtered and evaporated under reduced pressure. The residue was purified by silica gel column chromatography, eluted with 5% ethyl acetate/petroleum ether to give the desired product. LCMS: 164.09 (M+H).

(Step 2) Synthesis of N-Neopentyl-N-phenyl-[1,2,4]triazolo[4,3-a]quinazolin-5-amine To a solution of N-neopentylaniline (0.024 g, 0.15 mmol) in THF (2 mL) was added LDA (0.09 mL, 0.18 mmol, 2.0M in THF) at 0° C. and the mixture was stirred at RT for 1 h, followed by the addition of 5-chloro-[1,2,4]triazolo[4,3-a]quinazoline (0.025 g, 0.12 mmol) at 0° C., and the mixture was stirred at RT for 1 h. The reaction mixture was quenched with ice-water and extracted with ethyl acetate twice. The combined organic layer was washed successively with water and brine, dried over $Na_2SO_4$, filtered and evaporated under reduced pressure. The residue was purified by silica gel column chromatography, eluted with 4% methanol/dichloromethane to afford the desired product: $^1$H-NMR (DMSO-$d_6$) δ 9.70 (s, 1H), 8.33 (dd, J=8.3, 1.1 Hz, 1H), 7.81 (ddd, J=8.4, 7.2, 1.4 Hz, 1H), 7.51 (dd, J=8.4, 1.3 Hz, 1H), 7.35-7.24 (m, 3H), 7.19-7.07 (m, 3H), 4.09 (s, 2H), 0.98 (s, 9H); LCMS(m/z) 332.2 [M+H]+.

Example 55. N-(But-2-yn-1-yl)-N-phenyl-[1,2,4]triazolo[4,3-a]quinazolin-5-amine

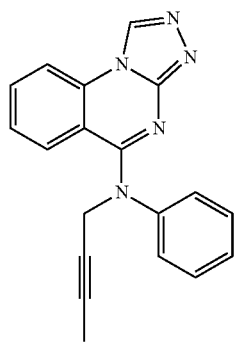 [SMILES: CC#CCN(c1ccccc1)c1nc2nncn2c2ccccc12]

(Step 1) Synthesis of N-(but-2-yn-1-yl)aniline

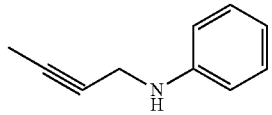

To a solution of aniline (0.3 g, 3.22 mmol) in acetonitrile (10 mL) was added potassium carbonate (0.445 g, 3.22 mmol) at RT and the mixture was stirred at RT for 10 min, followed by the addition of 1-bromobut-2-yne (0.385 g, 2.90 mmol) at RT and the mixture was stirred at RT for 16 h. The reaction mixture was diluted with cold-water and extracted with ethyl acetate. The combined organic layers were washed successively with water and brine, dried over $Na_2SO_4$, filtered and evaporated under reduced pressure. The residue was purified by silica gel chromatography and eluted with 30% ethyl acetate/petroleum ether to give the desired product. LCMS(m/z) 146.09 [M+H]+.

(Step 2) Synthesis of N-(but-2-yn-1-yl)-2-chloro-N-phenylquinazolin-4-amine

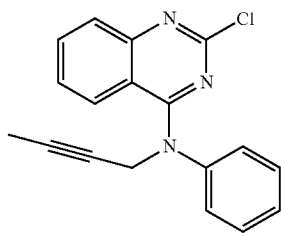 [SMILES: CC#CCN(c1ccccc1)c1nc(Cl)nc2ccccc12]

To a solution of N-(but-2-yn-1-yl)aniline (0.131 g, 0.9 mmol) in DMF (5 mL) was added 60% sodium hydride (0.036 g, 0.90 mmol) at 0° C. and the mixture was stirred at RT for 1 h, followed by the addition of 2,4-dichloroquinazoline (0.180 g, 0.90 mmol) at RT and the mixture was then stirred at 80° C. for 16 h. The reaction mixture was diluted with water and extracted with ethyl acetate. The organic layer was washed successively with water and brine solution, dried over $Na_2SO_4$, filtered and evaporated under reduced pressure. The residue was purified by silica gel column chromatography and eluted with 25% ethyl acetate/petroleum ether to give the desired product. LCMS(m/z) 308.23 [M+H]+.

(Step 3) Synthesis of N-(But-2-yn-1-yl)-N-phenyl-[1,2,4]triazolo[4,3-a]quinazolin-5-amine To a stirred solution of N-(but-2-yn-1-yl)-2-chloro-N-phenylquinazolin-4-amine (0.07 g, 0.23 mmol) in toluene (4 mL) was added formohydrazide (0.027 g, 0.46 mmol) at RT and the mixture was stirred under reflux for 16 h. The reaction mixture was evaporated under reduced pressure, and the residue was purified by silica gel column chromatography, followed by prep. HPLC to afford the desired product: $^1$H-NMR (500 MHz, DMSO-$d_6$) δ 9.64 (s, 1H), 8.29 (dd, J=8.2, 1.1 Hz, 1H), 7.78 (ddd, J=8.5, 6.9, 1.7 Hz, 1H), 7.44-7.36 (m, 2H), 7.33-7.17 (m, 5H), 4.80 (q, J=2.3 Hz, 2H), 1.71 (t, J=2.3 Hz, 3H). LCMS(m/z) 314.1 [M+H]+.

Example 56. N-(but-3-yn-1-yl)-N-phenyl-[1,2,4]triazolo[4,3-a]quinazolin-5-amine

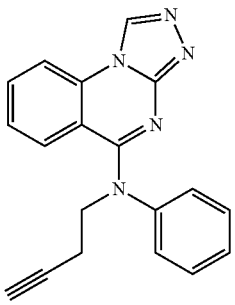

(Step 1) Synthesis of N-(but-3-yn-1-yl)aniline

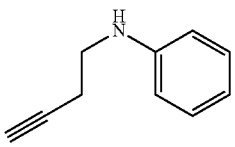

To a stirred solution of aniline (0.5 g, 5.38 mmol) in acetonitrile (5 mL) were added 4-bromobut-1-yne (0.643 g, 4.84 mmol) and potassium carbonate (0.742 g, 5.38 mmol) at RT and the mixture was stirred at RT for 16 h. The reaction mixture was diluted with water and extracted with ethyl acetate. The organic layer was washed with brine, dried over $Na_2SO_4$, filtered and evaporated under reduced pressure. The residue was purified by silica gel column chromatography and eluted with 10% ethyl acetate/petroleum ether to give the desired product. LCMS(m/z) 146.09 [M+H]$^+$.

(Step 2) Synthesis of N-(but-3-yn-1-yl)-N-phenyl-[1,2,4]triazolo[4,3-a]quinazolin-5-amine To a solution of N-(but-3-yn-1-yl)aniline (0.021 g, 0.15 mmol) in THF (2 mL) was added LDA (0.09 mL, 0.18 mmol, 2.0M in THF) at 0° C. and the mixture was stirred at RT for 1 h, followed by the addition of 5-chloro-[1,2,4]triazolo[4,3-a]quinazoline (0.025 g, 0.12 mmol) at 0° C., and the mixture then was stirred at RT for 1 h. The reaction mixture was quenched with ice-water and extracted with ethyl acetate twice. The combined organic layer was washed successively with water and brine, dried over $Na_2SO_4$, filtered and evaporated under reduced pressure. The residue was purified by prep. HPLC to afford the desired product: $^1$H-NMR (DMSO-$d_6$) δ 9.63 (s, 1H), 8.29 (d, J=8.3 Hz, 1H), 7.77 (ddd, J=8.5, 6.3, 2.3 Hz, 1H), 7.44-7.15 (m, 7H), 4.20 (t, J=7.3 Hz, 2H), 2.91 (t, J=2.6 Hz, 1H), 2.66 (td, J=7.5, 2.7 Hz, 2H); LCMS(m/z) 314.2 [M+H]+.

Example 57. N-methyl-N-(thiophen-2-yl)-[1,2,4]triazolo[4,3-a]quinazolin-5-amine

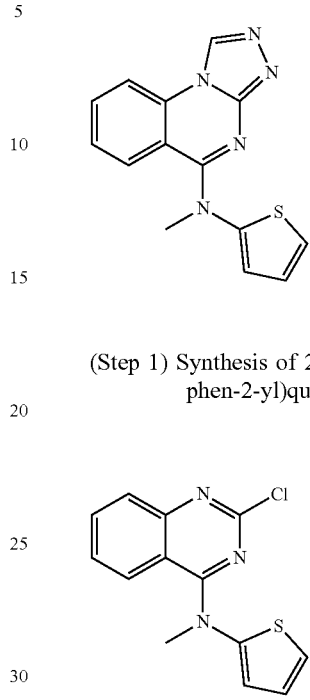

(Step 1) Synthesis of 2-chloro-N-methyl-N-(thiophen-2-yl)quinazolin-4-amine

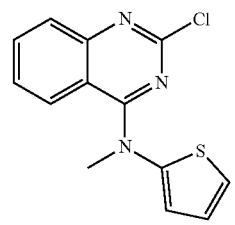 [SMILES: CN(c1cccs1)c1nc(Cl)nc2ccccc12]

To a stirred solution of 2,4-dichloroquinazoline (0.280 g, 1.40 mmol) in DMF (4 mL) was added 60% sodium hydride (0.056 g, 1.40 mmol) at 0° C., and the mixture was stirred for 1 h at RT, followed by the addition of N-methylthiophen-2-amine hydrochloride (0.209 g, 1.40 mmol) at 0° C. and the mixture was stirred for 16 h at RT. The progress of the reaction was monitored by TLC. After completion of the reaction, the reaction mixture was diluted with ice-water and extracted with ethyl acetate twice. The combined organic layers were washed successively with water and brine, dried over $Na_2SO_4$, filtered and evaporated under reduced pressure. The residue was purified by silica gel column chromatography, eluted with 15% ethyl acetate/petroleum ether to give the desired product. LCMS(m/z) 276.04 [M+H]$^+$.

(Step 2) Synthesis of N-methyl-N-(thiophen-2-yl)-[1,2,4]triazolo[4,3-a]quinazolin-5-amine To a stirred solution of 2-chloro-N-methyl-N-(thiophen-2-yl)quinazolin-4-amine (0.06 g, 0.22 mmol) in toluene (4 mL) was added formohydrazide (0.026 g, 0.44 mmol) at RT and the mixture was stirred under reflux condition for 16 h. The progress of the reaction was monitored by TLC. After completion of the reaction, the reaction mixture was diluted with MeOH/THF and evaporated under reduced pressure. The residue was diluted with AcOEt, and washed with brine, dried over $Na_2SO_4$, filtered and evaporated under reduced pressure. The residue was purified by silica gel column chromatography and eluted with 4% methanol/dichloromethane to afford the desired product: $^1$H-NMR (500 MHz, DMSO-$d_6$) δ 9.65 (s, 1H), 8.32 (dd, J=8.5, 1.2 Hz, 1H), 7.83 (ddd, J=8.5, 7.3, 1.3 Hz, 1H), 7.59 (dd, J=8.4, 1.3 Hz, 1H), 7.44-7.27 (m, 2H), 7.03-6.89 (m, 2H), 3.57 (s, 3H); LCMS(m/z) 282.1 [M+H]+.

Example 58. 2-([1,2,4]triazolo[4,3-a]quinazolin-5-yl(methyl)amino)benzoic Acid

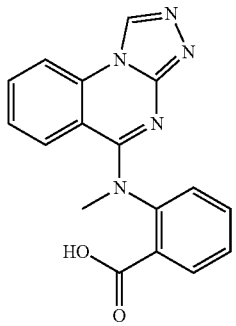

To a solution of 5-chloro-[1,2,4]triazolo[4,3-a]quinazoline (600 mg, 3.22 mmol), BrOP (1376 mg, 3.55 mmol) and DBU (589 mg, 3.87 mmol) in Acetonitrile (10.0 ml) was added to methyl 2-(methylamino)benzoate (0.518 mL, 3.55 mmol) at RT. The mixture was stirred overnight at 80° C. The reaction mixture was concentrated in vacuo, and the residue was purified by column chromatography (Si-column, CHCl$_3$:MeOH=100:0-95:5) to give a crude product. The crude compound was further purified by prep-LCMS to afford the desired product: $^1$H-NMR (DMSO-d$_6$) δ 11.50 (s, 1H), 9.62 (s, 1H), 8.88 (d, J=8.3 Hz, 1H), 8.40 (d, J=8.2 Hz, 1H), 8.35 (d, J=8.2 Hz, 1H), 8.08 (dd, J=8.0, 1.6 Hz, 1H), 8.04 (t, J=7.9 Hz, 1H), 7.81 (q, J=8.3, 7.9 Hz, 2H), 7.30 (t, J=7.5 Hz, 1H), 3.90 (s, 3H); LCMS(m/z) 320.2 [M+H]+.

Example 59. N-methyl-8-nitro-N-phenyl-[1,2,4]triazolo[4,3-a]quinazolin-5-amine

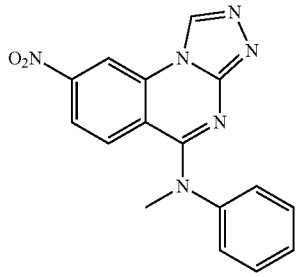

(Step 1) Synthesis of 7-nitroquinazoline-2,4(1H,3H)-dione

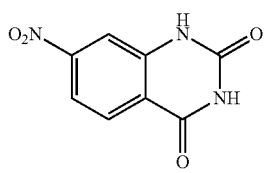 [SMILES: O=c1[nH]c(=O)c2ccc([N+](=O)[O-])cc2[nH]1]

A mixture of 2-amino-4-nitrobenzoic acid (3.34 g, 18.3 mmol) and urea (3.30 g, 55 mmol) in NMP (10 mL) was stirred for 5.5h at 160° C. The reaction mixture was cooled to RT and diluted with water. The resulting precipitates were collected and washed with water, EtOH to give the desired product. LCMS(m/z) 206.01 [M−H]+.

(Step 2) Synthesis of 2,4-dichloro-7-nitroquinazoline

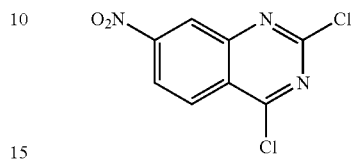

A mixture of 7-nitroquinazoline-2,4(1H,3H)-dione (500 mg, 2.414 mmol) and phosphoryl trichloride (10 mL, 2.414 mmol) was stirred at 100° C. for 6 h. The reaction was monitored by LCMS (quenched by MeOH). The reaction mixture was cooled to RT, and poured slowly over ice. The resulting solids were collected and dried. The obtained solids were used in the next step without further purification.

(Step 3) Synthesis of 2-chloro-N-methyl-7-nitro-N-phenylquinazolin-4-amine

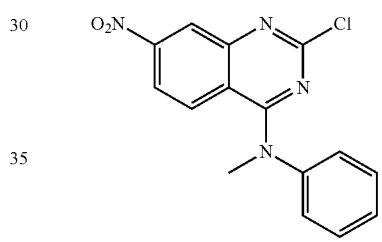

To a solution of 2,4-dichloro-7-nitroquinazoline (1.5 g, 6.15 mmol) in DMF (30.7 mL) were added N-methylaniline (0.659 g, 6.15 mmol) and sodium hydride (0.148 g, 6.15 mmol), and the mixture was stirred at RT for 1 h. The mixture was diluted with AcOEt, washed successively with water and brine, and dried over Na$_2$SO$_4$. The organic layer was concentrated in vacuo. The resulting residue was used in the next step without further purification. LCMS(m/z) 315.03 [M+H]+.

(Step 4) Synthesis of 2-hydrazinyl-N-methyl-7-nitro-N-phenylquinazolin-4-amine

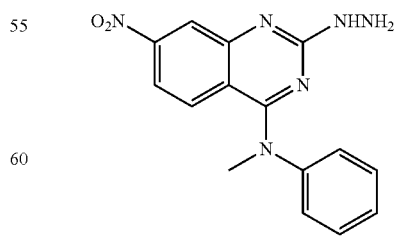

The resulting 2-chloro-N-methyl-7-nitro-N-phenylquinazolin-4-amine (1.2 g, 3.81 mmol) and hydrazine hydrate (0.191 g, 3.81 mmol) in ethanol (19.06 mL) was stirred at RT for 1 h. The mixture was diluted with AcOEt, washed successively with water and brine, and dried over Na₂SO₄. The organic layer was concentrated in vacuo. The resulting residue was used in the next step without further purification. LCMS(m/z) 311.08 [M+H]⁺.

(Step 5) Synthesis of N-methyl-8-nitro-N-phenyl-[1,2,4]triazolo[4,3-a]quinazolin-5-amine A mixture of 2-hydrazinyl-N-methyl-7-nitro-N-phenylquinazolin-4-amine (800 mg, 2.58 mmol) and triethoxymethane (10 mL, 2.58 mmol) was stirred at 100° C. overnight. The reaction mixture was concentrated in vacuo. The residue was purified by column chromatography (Si-column, CHCl₃:MeOH=10:0-9:1) to afford the desired product: ¹H-NMR (DMSO-d₆) δ 9.89 (s, 1H), 9.22 (d, J=2.3 Hz, 1H), 7.99 (dd, J=9.1, 2.3 Hz, 1H), 7.46 (d, J=9.1 Hz, 1H), 7.43-7.38 (m, 2H), 7.37-7.32 (m, 2H), 7.32-7.25 (m, 1H), 3.56 (s, 3H); LCMS(m/z) 321.2.

Example 60. N-(2,6-difluorophenyl)-N-methyl-[1,2,4]triazolo[4,3-a]quinazolin-5-amine

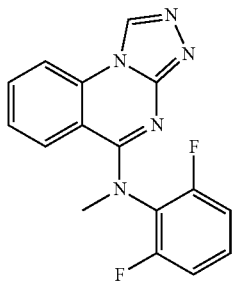 [SMILES: CN(c1c(F)cccc1F)c1nc2nncn2c2ccccc12]

To a solution of 5-chloro-[1,2,4]triazolo[4,3-a]quinazoline (50 mg, 0.269 mmol), BrOP (115 mg, 0.295 mmol) and DBU (82 mg, 0.537 mmol) in acetonitrile (2 mL) was added 2,6-difluoro-N-methylaniline hydrochloride (48.2 mg, 0.269 mmol) at RT. The mixture was stirred for 2h at 80° C. The reaction mixture was subjected to solid phase extraction (washed with MeOH, then eluted with NH₃ in MeOH) using Bond Elut SCX cartridge (Agilent), and the collected fractions were concentrated in vacuo. Then, the residue was purified by prep-LCMS to afford the desired product: ¹H-NMR (DMSO-d₆) δ 9.66 (s, 1H), 8.36 (dt, J=8.4, 0.8 Hz, 1H), 7.87 (ddd, J=8.4, 7.0, 1.6 Hz, 1H), 7.49 (tt, J=8.0, 6.4 Hz, 1H), 7.38-7.24 (m, 4H), 3.49 (s, 3H); LCMS(m/z) 312.1 [M+H]+.

Example 61. 5-(2,3,4,5-tetrahydrobenzo[b]azepin-1-yl)-[1,2,4]triazolo[4,3-a]quinazoline

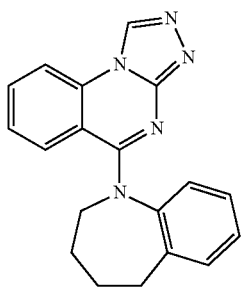 [SMILES: c1ccc2c(c1)CCCCN2c1nc2nncn2c2ccccc12]

(Step 1) Synthesis of 1-(2-chloroquinazolin-4-yl)-2,3,4,5-tetrahydro-1H-benzo[b]azepine

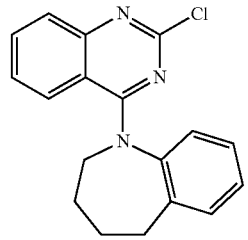 [SMILES: Clc1nc(N2CCCCc3ccccc32)c2ccccc2n1]

To a stirred mixture of 2,4-dichloroquinazoline (0.15 g, 0.75 mmol) and 2,3,4,5-tetrahydro-1H-benzo[b]azepine (0.11 g, 0.75 mmol) in DMF (10 mL) was added sodium hydroxide (0.060 g, 1.5 mmol) at RT and the mixture was then stirred at the same temperature for 16 h. The reaction mixture was diluted with ice-water and extracted with ethyl acetate. The organic layer was washed with brine, dried over Na₂SO₄, filtered and evaporated under reduced pressure to give the desired product. LCMS: 310.13 (M+H).

(Step 2) Synthesis of 1-(2-Hydrazinylquinazolin-4-yl)-2,3,4,5-tetrahydro-1H-benzo[b]azepine

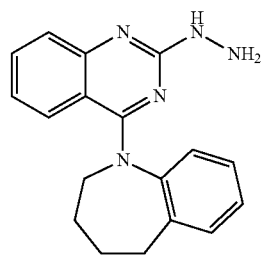 [SMILES: NNc1nc(N2CCCCc3ccccc32)c2ccccc2n1]

To a stirred solution of 1-(2-chloroquinazolin-4-yl)-2,3,4,5-tetrahydro-1H-benzo[b]azepine (crude, 0.1 g, 0.32 mmol) in EtOH (10 mL) was added hydrazine hydrate (0.032 g, 0.65 mmol) at RT and the mixture was stirred at 70° C. for 16 h. The reaction mixture was diluted with water and extracted with ethyl acetate. The organic layer was washed successively with water and brine, dried over Na₂SO₄, filtered and evaporated under reduced pressure to give the desired product. LCMS: 306.21 (M+H).

(Step 3) Synthesis of 5-(2,3,4,5-tetrahydrobenzo[b]azepin-1-yl)-[1,2,4]triazolo[4,3-a]quinazoline The mixture of 1-(2-hydrazinylquinazolin-4-yl)-2,3,4,5-tetrahydro-1H-benzo[b]azepine (0.1 g, 0.33 mmol) and triethyl orthoformate (0.145 g, 0.99 mmol) was stirred at 80° C. for 16 h. The reaction mixture was evaporated under reduced pressure, and the residue was purified by prep. HPLC to afford the desired product: ¹H-NMR (DMSO-d₆) δ 9.57 (s, 1H), 8.26 (dd, J=8.4, 1.1 Hz, 1H), 7.74 (ddd, J=8.4, 7.2, 1.3 Hz, 1H), 7.46 (dd, J=7.5, 1.5 Hz, 1H), 7.29-7.03 (m, 3H), 6.89 (ddd, J=29.0, 8.1, 1.3 Hz, 2H), 4.44-3.57 (m, 2H), 3.01 (t, J=5.8 Hz, 2H), 1.91-1.59 (m, 4H); LCMS(m/z) 316.2 [M+H]+.

Example 62. 7-bromo-N-methyl-N-phenyl-[1,2,4]triazolo[4,3-a]quinazolin-5-amine

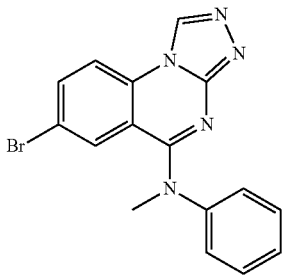 [SMILES: CN(c1ccccc1)c1nc2nncn2c2ccc(Br)cc12]

(Step 1) Synthesis of 6-bromo-2-chloro-N-methyl-N-phenylquinazolin-4-amine

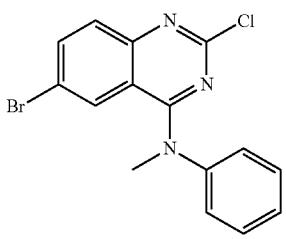

To a solution of N-methylaniline (38.6 mg, 0.360 mmol) and NaH (14.39 mg, 0.360 mmol) in DMF (1.8 mL) was added 6-bromo-2,4-dichloroquinazoline (100 mg, 0.360 mmol) at RT. The mixture was stirred for 1h at RT. The reaction mixture was diluted with AcOEt, washed successively with water and brine, and dried over Na$_2$SO$_4$. The organic layer was concentrated in vacuo. The resulting residue was used in the next step without further purification. LCMS(m/z) 348.27 [M+H]$^+$.

(Step 2) Synthesis of 6-bromo-2-hydrazinyl-N-methyl-N-phenylquinazolin-4-amine

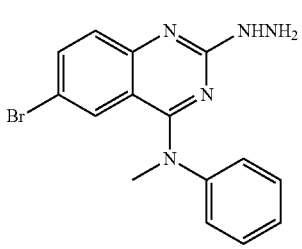 [SMILES: CN(c1ccccc1)c1nc(NN)nc2ccc(Br)cc12]

The resulting 6-bromo-2-chloro-N-methyl-N-phenylquinazolin-4-amine (134 mg, 0.384 mmol) and hydrazine hydrate (38.5 mg, 0.769 mmol) in EtOH (3 mL) was stirred for 2h at 50° C. The reaction mixture was cooled to RT, and then diluted with EtOAc. The solution was washed successively with water and brine, and dried over Na$_2$SO$_4$, and concentrated in vacuo. The resulting crude material was used in the next step without purification. LCMS(m/z) 346.10 [M+H]$^+$.

(Step 3) Synthesis of 7-bromo-N-methyl-N-phenyl-[1,2,4]triazolo[4,3-a]quinazolin-5-amine The resulting 6-bromo-2-hydrazinyl-N-methyl-N-phenylquinazolin-4-amine (136 mg, 0.158 mmol) and triethoxymethane (3 mL) was stirred overnight at 100° C. The reaction mixture was concentrated in vacuo. The residue was purified by column chromatography (Si-column, CHCl$_3$:MeOH=100:0-95:5) to afford the desired product: $^1$H-NMR (Methanol-d$_4$) δ 9.42 (s, 1H), 8.11 (d, J=8.8 Hz, 1H), 7.88 (dd, J=8.8, 2.1 Hz, 1H), 7.53-7.28 (m, 6H), 4.99-4.77 (m, 3H); LCMS(m/z) 354.1 [M+H]+.

Example 63. N-methyl-N-phenyl-8-(pyridin-3-yl)-[1,2,4]triazolo[4,3-a]quinazolin-5-amine

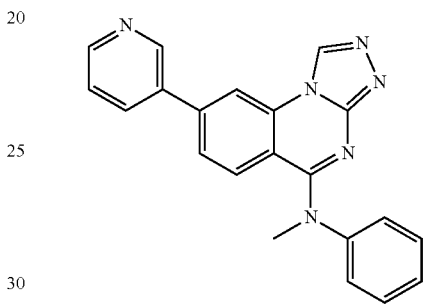

A mixture of 8-bromo-N-methyl-N-phenyl-[1,2,4]triazolo[4,3-a]quinazolin-5-amine (Example 28) (20 mg, 0.056 mmol), K$_3$PO$_4$ (23.97 mg, 0.113 mmol), Pd(OAc)$_2$ (2.54 mg, 0.011 mmol), tricyclohexylphosphine (3.17 mg, 0.011 mmol) and pyridin-3-ylboronic acid (17.35 mg, 0.141 mmol) in dioxane/water (0.28 ml) was heated at 120° C. for 2 h. The reaction mixture was concentrated in vacuo. The residue was purified by column chromatography (Si-column, CHCl$_3$:MeOH=10:0-9:1) to afford the desired product: $^1$H-NMR (Methanol-d4) δ 9.54 (d, J=3.5 Hz, 1H), 8.90 (d, J=2.4 Hz, 1H), 8.61-8.54 (m, 1H), 8.47-8.40 (m, 1H), 8.23-8.14 (m, 1H), 7.58-7.37 (m, 4H), 7.36-7.21 (m, 4H), 3.64 (d, J=3.3 Hz, 3H); LCMS(m/z) 353.2 [M+H]+.

Example 64. 8-iodo-N-methyl-N-phenyl-[1,2,4]triazolo[4,3-a]quinazolin-5-amine

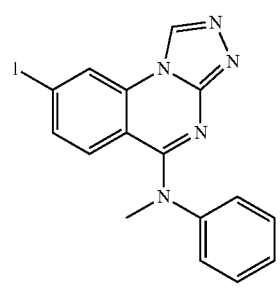

(Step 1) Synthesis of 8-(hydroxyamino)-N-methyl-N-phenyl-[1,2,4]triazolo[4,3-a]quinazolin-5-amine

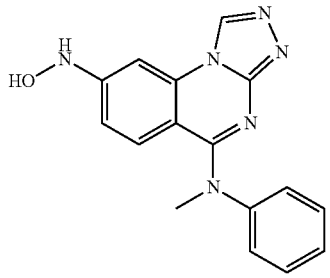

A mixture of N-methyl-8-nitro-N-phenyl-[1,2,4]triazolo[4,3-a]quinazolin-5-amine (Example 59) (30 mg, 0.094 mmol) and Pd/C (30 mg, 0.282 mmol) in EtOH (3 mL) was stirred for 3h at RT under H2 atmosphere. The reaction mixture was filtered through a bed of Celite and concentrated in vacuo to give the desired product.

(Step 2) Synthesis of 8-iodo-N-methyl-N-phenyl-[1,2,4]triazolo[4,3-a]quinazolin-5-amine To a solution of 8-(hydroxyamino)-N-methyl-N-phenyl-[1,2,4]triazolo[4,3-a]quinazolin-5-amine (25 mg, 0.082 mmol) and diiodomethane (0.033 ml, 0.408 mmol) in THF (1 mL) was added tert-butyl nitrite (0.041 ml, 0.343 mmol) at RT. The mixture was stirred for 2 h at 60° C. The reaction mixture was concentrated in vacuo, and the residue was purified by column chromatography (Si-column, CHCl$_3$:MeOH=100:0-95:5) to give the crude product.

The crude compound was further purified by prep-LCMS to afford the desired product: $^1$H-NMR (Methanol-d4) δ 9.43 (s, 1H), 8.64 (d, J=1.6 Hz, 1H), 7.49 (dd, J=8.8, 1.6 Hz, 1H), 7.46-7.38 (m, 2H), 7.36-7.30 (m, 1H), 7.30-7.23 (m, 2H), 6.97 (d, J=8.8 Hz, 1H), 3.63 (s, 3H); LCMS(m/z) 401.7 [M+H]+.

Example 65. N-(4-bromophenyl)-N-methyl-[1,2,4]triazolo[4,3-a]quinazolin-5-amine

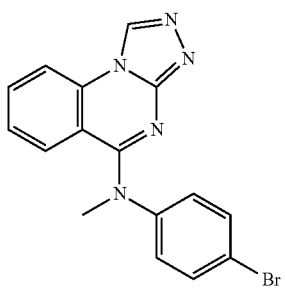 [SMILES: CN(c1ccc(Br)cc1)c1nc2nncn2c2ccccc12]

To a solution of N-methyl-N-phenyl-[1,2,4]triazolo[4,3-a]quinazolin-5-amine (Example 1) (30 mg, 0.109 mmol) in DMF (0.55 mL) was added NBS (5.82 mg, 0.033 mmol), and the mixture was stirred for 30 min at 0° C. Then the mixture was added another NBS (5.82 mg, 0.033 mmol), and stirred for 1 h at 0° C. The reaction mixture was subjected to solid phase extraction (washed with MeOH, then eluted with NH$_3$ in MeOH) using Bond Elut SCX cartridge (Agilent), and the collected fractions were concentrated in vacuo. The residue was purified by prep-LCMS to afford the desired product: $^1$H-NMR (Methanol-d$_4$) δ 9.45 (s, 1H), 8.17 (dd, J=8.4, 1.0 Hz, 1H), 7.77 (ddd, J=8.5, 7.2, 1.4 Hz, 1H), 7.61-7.50 (m, 2H), 7.37 (dd, J=8.4, 1.2 Hz, 1H), 7.31-7.16 (m, 3H), 3.63 (s, 3H); LCMS(m/z) 354.3.

Example 66. N-5-methyl-N5-phenyl-[1,2,4]triazolo[4,3-a]quinazoline-5,8-diamine

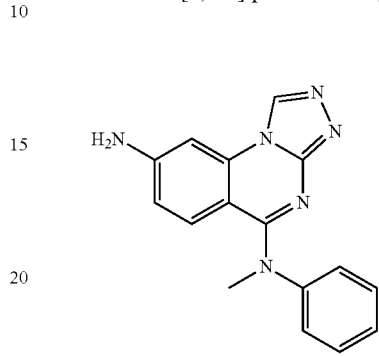

A mixture of N-methyl-8-nitro-N-phenyl-[1,2,4]triazolo[4,3-a]quinazolin-5-amine (Example 59) (429 mg, 1.339 mmol) and Pd/C (20 mg) in ethanol (6.7 mL) was stirred at 60° C. under H2 atmosphere overnight. Pd/C was removed by filtration and, the filtrate was purified by column chromatography (Si-column, CHCl$_3$:MeOH=10:0-9:1) to afford the desired product: $^1$H-NMR (DMSO-d$_6$) δ 9.28 (s, 1H), 7.41-7.31 (m, 2H), 7.24-7.15 (m, 3H), 7.02 (d, J=2.2 Hz, 1H), 6.92 (d, J=9.1 Hz, 1H), 6.41 (s, 2H), 6.35 (dd, J=9.1, 2.2 Hz, 1H), 3.47 (s, 3H); LCMS(m/z) 291.2 [M+H]+.

Example 67. N,6-dimethyl-N-phenyl-[1,2,4]triazolo[4,3-a]quinazolin-5-amine

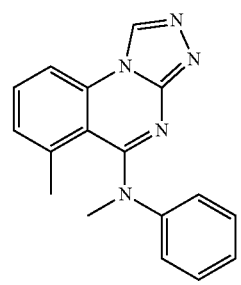

(Step 1) Synthesis of 5-methylquinazoline-2,4(1H,3H)-dione

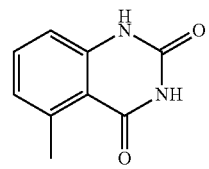

To a suspension of 2-amino-6-methylbenzoic acid (1.5 g, 9.92 mmol) in water (10 mL) was added acetic acid (1 mL), and the suspension was heated to 35° C. To this suspension, a freshly prepared solution of potassium cyanate (2.012 g, 24.81 mmol) in water (2 mL) was added dropwise over the period of 1 h. The mixture was stirred for 1 h at 40° C. NaOH (20 g) was added portion-wise to the reaction mixture by maintaining the internal temperature below 50° C., and the mixture was further stirred for 2 h. The precipitates were collected by filtration to give the desired product. LCMS (m/z) 177.16 [M+H]+.

(Step 2) Synthesis of 2,4-dichloro-5-methylquinazoline

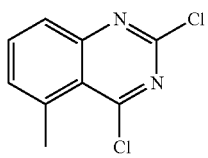

A solution of 5-methylquinazoline-2,4(1H,3H)-dione (300 mg, 1.703 mmol) in N,N-dimethylaniline (0.5 mL, 1.703 mmol) and POCl$_3$ (3 mL) was stirred for 3 h at 110° C. The reaction mixture was cooled to RT, diluted with EtOAc, washed successively with water and brine, dried over Na$_2$SO$_4$, and concentrated in vacuo. The residue was purified by column chromatography (Si-column, hexane:AcOEt=100:0-80:20) to give the desired product.

(Step 3) Synthesis of 2-chloro-N,5-dimethyl-N-phenylquinazolin-4-amine

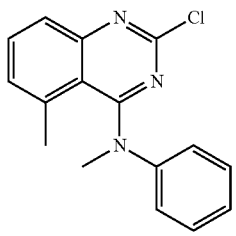 [SMILES: Cc1cccc2nc(Cl)nc(N(C)c3ccccc3)c12]

To a mixture of N-methylaniline (58.1 mg, 0.542 mmol) and sodium hydride (21.68 mg, 0.542 mmol) in DMF (5 mL) was added 2,4-dichloro-5-methylquinazoline (105 mg, 0.493 mmol) at RT. The mixture was stirred overnight at RT. The reaction mixture was diluted with EtOAc, washed successively with NH$_4$Cl(aq) and brine, dried over Na$_2$SO$_4$, and concentrated in vacuo. The residue was purified by column chromatography (Si-column, hexane:AcOEt=100:0-90:10) to give the desired product. LCMS(m/z) 284.8 [M+H]+.

(Step 4) Synthesis of 2-hydrazinyl-N,5-dimethyl-N-phenylquinazolin-4-amine

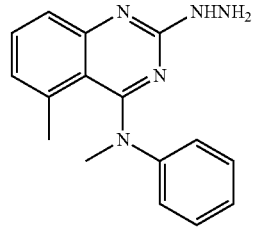 [SMILES: Cc1cccc2nc(NN)nc(N(C)c3ccccc3)c12]

A solution of 2-chloro-N,5-dimethyl-N-phenylquinazolin-4-amine (80 mg, 0.282 mmol) in hydrazine hydrate (1 mL) and EtOH (2 mL) was stirred for 1.5h at 50° C. The reaction mixture was diluted with EtOAc, washed successively with water and brine, dried over Na$_2$SO$_4$, and concentrated in vacuo. The residue was used for the next step without purification. LCMS(m/z) 280.23 [M+H]+.

(Step 5) Synthesis of N,6-dimethyl-N-phenyl-[1,2,4]triazolo[4,3-a]quinazolin-5-amine A solution of crude 2-hydrazinyl-N,5-dimethyl-N-phenylquinazolin-4-amine in triethoxymethane (1 mL) was stirred for 3 h at 100° C. The reaction mixture was concentrated in vacuo, and the residue was purified by column chromatography (Si-column, CHCl$_3$:MeOH=100:0-95:5) to afford the crude product. The crude compound was further purified by prep LCMS to afford the desired product: $^1$H-NMR (Methanol-d$_4$) δ 9.45 (s, 1H), 8.04 (ddd, J=8.2, 1.3, 0.7 Hz, 1H), 7.70 (t, J=7.9 Hz, 1H), 7.25-7.13 (m, 3H), 7.13-7.03 (m, 1H), 6.97-6.88 (m, 2H), 3.67 (s, 3H), 2.30 (s, 3H); LCMS(m/z) 290.2 [M+H]+.

Example 68. N-(5-(methyl(phenyl)amino)-[1,2,4]triazolo[4,3-a]quinazolin-8-yl)acetamide

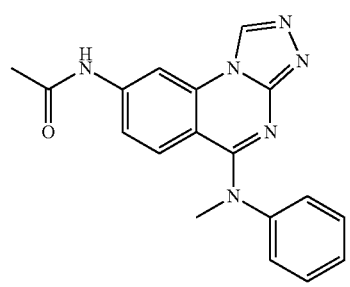 [SMILES: CC(=O)Nc1ccc2c(N(C)c3ccccc3)nc3nncn3c2c1]

A solution of N5-methyl-N5-phenyl-[1,2,4]triazolo[4,3-a]quinazoline-5,8-diamine (Example 66) (50 mg, 0.172 mmol) and acetyl chloride (0.037 mL, 0.517 mmol) in DMA (1 mL) was stirred for 4h at 80° C. The reaction mixture was purified by column chromatography (Si-column, CHCl$_3$:MeOH=10:0-95:5) and further purified by prep-LCMS to afford the desired product: $^1$H NMR (DMSO-d$_6$) δ 10.61 (s, 1H), 9.53 (s, 1H), 8.50 (d, J=1.9 Hz, 1H), 7.42 (tt, J=7.6, 2.1 Hz, 2H), 7.36-7.26 (m, 3H), 7.19-7.05 (m, 2H), 3.56 (s, 3H), 2.11 (s, 3H); LCMS(m/z) 333.2 [M+H]+.

Example 69. N5,N8-dimethyl-N5-phenyl-[1,2,4]triazolo[4,3-a]quinazoline-5,8-diamine

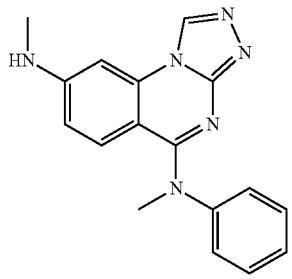 [SMILES: CNc1ccc2c(N(C)c3ccccc3)nc3nncn3c2c1]

To a solution of N5-methyl-N5-phenyl-[1,2,4]triazolo[4,3-a]quinazoline-5,8-diamine (Example 66) (50 mg, 0.172 mmol) and AcOH (0.039 mL, 0.689 mmol) in CH$_3$CN (2 mL) was added formaldehyde (0.021 mL, 0.775 mmol) at RT. The mixture was stirred for 30 min at RT. Then, NaCNBH$_4$ (64.9 mg, 1.033 mmol) was added to the mixture at RT, and the mixture was stirred overnight at 60° C. The reaction mixture was subjected to solid phase extraction (washed with MeOH, then eluted with NH$_3$ in MeOH) using Bond Elut SCX cartridge (Agilent), and the collected fractions were concentrated in vacuo. The residue was purified by prep-LCMS to afford the desired product: $^1$H-NMR (DMSO-d$_6$) δ 9.50 (s, 1H), 7.40-7.30 (m, 2H), 7.23-7.14 (m, 3H), 7.03 (d, J=2.3 Hz, 1H), 6.98 (q, J=4.8 Hz, 1H), 6.91 (d, J=9.2 Hz, 1H), 6.38 (dd, J=9.3, 2.3 Hz, 1H), 3.47 (s, 3H), 2.81 (d, J=4.9 Hz, 3H); LCMS(m/z) 305.0 [M+H]+.

Example 70. N-methyl-N-(p-tolyl)-[1,2,4]triazolo[4,3-a]quinazolin-5-amine

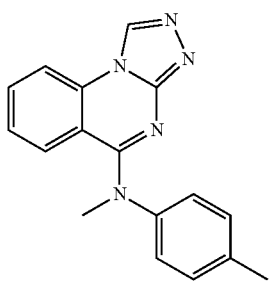 [SMILES: Cc1ccc(N(C)c2nc3nncn3c3ccccc23)cc1]

To a solution of 5-chloro-[1,2,4]triazolo[4,3-a]quinazoline (50 mg, 0.269 mmol), BrOP (115 mg, 0.295 mmol) and DBU (49.1 mg, 0.322 mmol) in acetonitrile (1 mL) was added to N,4-dimethylaniline (35.8 mg, 0.295 mmol) at RT. The mixture was stirred for 2 h at 50° C. The reaction mixture was subjected to solid phase extraction (washed with MeOH, then eluted with NH$_3$ in MeOH) using Bond Elut SCX cartridge (Agilent), and the collected fractions were concentrated in vacuo. Then, the residue was purified by prep-LCMS to afford the desired product: $^1$H NMR (DMSO-d$_6$) δ 9.61 (s, 1H), 8.34-8.24 (m, 1H), 7.76 (ddd, J=8.4, 7.1, 1.5 Hz, 1H), 7.35-7.14 (m, 6H), 3.50 (s, 3H), 2.30 (s, 3H); LCMS(m/z) 290.2 [M+H]+.

Example 71. N-(4-chlorophenyl)-N-methyl-[1,2,4]triazolo[4,3-a]quinazolin-5-amine

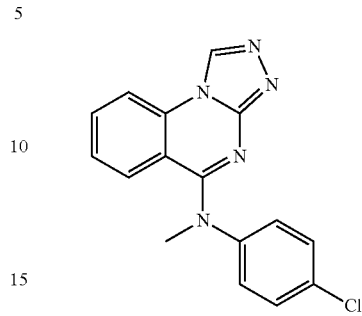

To a solution of 5-chloro-[1,2,4]triazolo[4,3-a]quinazoline (50 mg, 0.269 mmol), BrOP (115 mg, 0.295 mmol) and DBU (49.1 mg, 0.322 mmol) in acetonitrile (2 mL) was added to 4-chloro-N-methylaniline (41.8 mg, 0.295 mmol) at RT. The mixture was stirred for 2h at 50° C. The reaction mixture was subjected to solid phase extraction (washed with MeOH, then eluted with NH$_3$ in MeOH) using Bond Elut SCX cartridge (Agilent), and the collected fractions were concentrated in vacuo. Then, the mixture was purified by prep-LCMS to afford the desired product: $^1$H NMR (Methanol-d$_4$) δ 9.44 (s, 1H), 8.16 (ddd, J=8.4, 1.2, 0.5 Hz, 1H), 7.76 (ddd, J=8.5, 7.2, 1.4 Hz, 1H), 7.45-7.38 (m, 2H), 7.36 (ddd, J=8.5, 1.4, 0.5 Hz, 1H), 7.31-7.17 (m, 3H), 3.63 (s, 3H); LCMS(m/z) 310.0 [M+H]+.

Example 72. 8-(furan-3-yl)-N-methyl-N-phenyl-[1,2,4]triazolo[4,3-a]quinazolin-5-amine

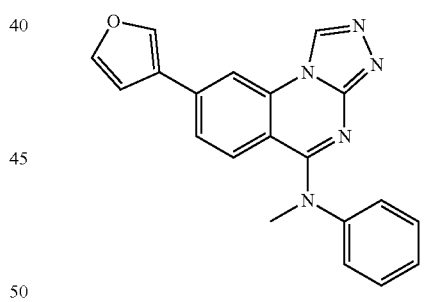

A mixture of 8-bromo-N-methyl-N-phenyl-[1,2,4]triazolo[4,3-a]quinazolin-5-amine (Example 28) (15 mg, 0.042 mmol), K$_3$PO$_4$ (27.0 mg, 0.127 mmol), Pd(OAc)$_2$ (1.901 mg, 8.47 µmol), tricyclohexylphosphine (2.375 mg, 8.47 µmol) and 3-furylboronic Acid (13.68 mg, 0.040 mmol) in dioxane/water (0.21 mL) was heated at 120° C. for 2 h. The reaction mixture was subjected to solid phase extraction (washed with MeOH, then eluted with NH$_3$ in MeOH) using Bond Elut SCX cartridge (Agilent), and the collected fractions were concentrated in vacuo. The residue was purified by column chromatography (Si-column, CHC$_3$:MeOH=10:0-9:1) to afford the desired product: $^1$H-NMR (CDCl$_3$) δ 9.02 (s, 1H), 7.91-7.83 (m, 2H), 7.54 (t, J=1.7 Hz, 1H), 7.44-7.32 (m, 2H), 7.35-7.14 (m, 5H), 6.79-6.73 (m, 1H), 3.68 (s, 3H); LCMS(m/z) 342.0 [M+H]+.

Example 73. N-methyl-N-phenyl-8-(thiophen-3-yl)-[1,2,4]triazolo[4,3-a]quinazolin-5-amine

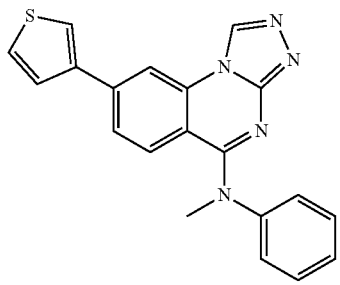 [SMILES: CN(c1ccccc1)c1nc2nncn2c2cc(-c3ccsc3)ccc12]

A mixture of 8-bromo-N-methyl-N-phenyl-[1,2,4]triazolo[4,3-a]quinazolin-5-amine (Example 28) (15 mg, 0.042 mmol), $K_3PO_4$ (27.0 mg, 0.127 mmol), $Pd(OAc)_2$ (1.901 mg, 8.47 μmol), tricyclohexylphosphine (2.375 mg, 8.47 μmol) and thiophen-3-ylboronic acid (13.55 mg, 0.106 mmol) in dioxane/water (0.21 mL) was heated at 120° C. for 2 h. The reaction mixture was subjected to solid phase extraction (washed with MeOH, then eluted with $NH_3$ in MeOH) using Bond Elut SCX cartridge (Agilent), and the collected fractions were concentrated in vacuo. The residue was purified by column chromatography (Si-column, $CHCl_3$:MeOH=10:0-9:1) to afford the desired product: $^1$H-NMR ($CDCl_3$) δ 9.00 (s, 1H), 7.94 (d, J=1.6 Hz, 1H), 7.64 (dd, J=2.9, 1.4 Hz, 1H), 7.48-7.36 (m, 4H), 7.32-7.23 (m, 3H), 7.21-7.16 (m, 2H), 3.67 (s, 3H); LCMS(m/z) 358.1 [M+H]+.

Example 74. N-methyl-N-phenyl-8-(1H-pyrazol-3-yl)-[1,2,4]triazolo[4,3-a]quinazolin-5-amine

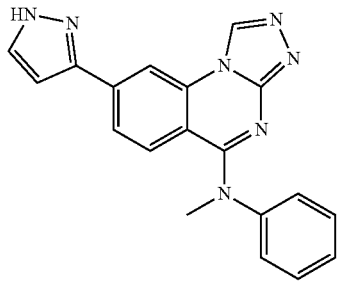 [SMILES: CN(c1ccccc1)c1nc2nncn2c2cc(-c3cc[nH]n3)ccc12]

A mixture of 8-bromo-N-methyl-N-phenyl-[1,2,4]triazolo[4,3-a]quinazolin-5-amine (Example 28) (15 mg, 0.042 mmol), $K_3PO_4$ (27.0 mg, 0.127 mmol), $Pd(OAc)_2$ (1.901 mg, 8.47 μmol), tricyclohexylphosphine (2.375 mg, 8.47 μmol) and (1H-pyrazol-3-yl)boronic acid (11.85 mg, 0.106 mmol) in dioxane/water (0.21 mL) was heated at 120° C. for 1 h. The reaction mixture was subjected to solid phase extraction (washed with MeOH, then eluted with $NH_3$ in MeOH) using Bond Elut SCX cartridge (Agilent), and the collected fractions were concentrated in vacuo. The residue was purified by column chromatography (Si-column, $CHCl_3$:MeOH=10:0-9:1) to afford the desired product: $^1$H NMR (DMSO-$d_6$) δ 13.21 (s, 1H), 9.74 (s, 1H), 8.63 (d, J=1.6 Hz, 1H), 7.91-7.85 (m, 1H), 7.66 (dd, J=8.8, 1.6 Hz, 1H), 7.44-7.35 (m, 2H), 7.37-7.21 (m, 4H), 6.97 (t, J=2.1 Hz, 1H), 3.55 (s, 3H); LCMS(m/z) 342.0 [M+H]+.

Example 75. N-methyl-N-phenyl-7-(pyridin-4-yl)-[1,2,4]triazolo[4,3-a]quinazolin-5-amine

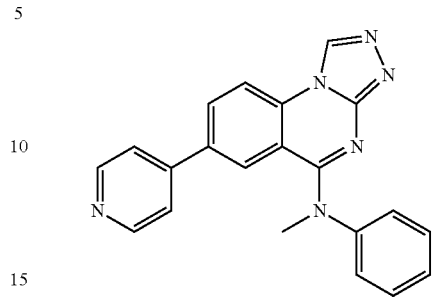

A mixture of 7-bromo-N-methyl-N-phenyl-[1,2,4]triazolo[4,3-a]quinazolin-5-amine (Example 62) (15 mg, 0.042 mmol), $K_3PO_4$ (27.0 mg, 0.127 mmol), $Pd(OAc)_2$ (1.901 mg, 8.47 μmol), tricyclohexylphosphine (2.375 mg, 8.47 μmol) and pyridin-4-ylboronic acid (13.01 mg, 0.106 mmol) in dioxane/water (0.21 mL) was heated at 120° C. for 1 h. The reaction mixture was subjected to solid phase extraction (washed with MeOH, then eluted with $NH_3$ in MeOH) using Bond Elut SCX cartridge (Agilent), and the collected fractions were concentrated in vacuo. The residue was purified by column chromatography (Si-column, $CHCl_3$:MeOH=10:0-9:1) to afford the desired product: $^1$H NMR (Methanol-$d_4$) δ 9.49 (s, 1H), 8.53-8.47 (m, 2H), 8.32 (d, J=8.6 Hz, 1H), 8.16 (dd, J=8.6, 2.0 Hz, 1H), 7.68 (d, J=1.9 Hz, 1H), 7.60-7.50 (m, 2H), 7.50-7.37 (m, 3H), 7.21-7.13 (m, 2H), 3.72 (s, 3H); LCMS(m/z) 353.2 [M+H]+.

Example 76. N5,N8,N8-trimethyl-N5-phenyl-[1,2,4]triazolo[4,3-a]quinazoline-5,8-diamine

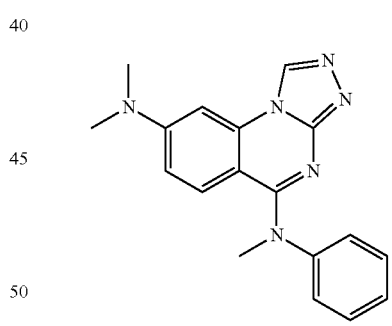

To a mixture of N5-methyl-N5-phenyl-[1,2,4]triazolo[4,3-a]quinazoline-5,8-diamine (Example 66) (30 mg, 0.103 mmol) and NaH (12.4 mg, 0.310 mmol) in DMF (2 mL) was added MeI (0.039 mL, 0.620 mmol) at RT. The mixture was stirred for 1.5 h at RT. The reaction mixture was quenched with water. The reaction mixture was subjected to solid phase extraction (washed with MeOH, then eluted with $NH_3$ in MeOH) using Bond Elut SCX cartridge (Agilent), and the collected fractions were concentrated in vacuo. The residue was purified by prep-LCMS to afford the desired product: $^1$H NMR (Methanol-d4) δ 9.41 (s, 1H), 7.45-7.36 (m, 2H), 7.31-7.19 (m, 3H), 7.10 (d, J=2.6 Hz, 1H), 7.07 (d, J=9.5 Hz, 1H), 6.52 (dd, J=9.5, 2.6 Hz, 1H), 3.60 (s, 3H), 3.10 (s, 6H); LCMS(m/z) 319.0 [M+H]+.

Example 77. N-(cyclobutylmethyl)-N-phenyl-[1,2,4]triazolo[4,3-a]quinazolin-5-amine

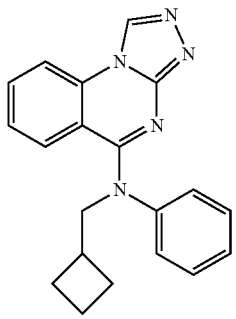 [SMILES: c1ccc(N(CC2CCC2)c2nc3nncn3c3ccccc23)cc1]

(Step 1) Synthesis of N-(cyclobutylmethyl)aniline

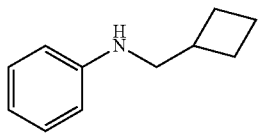 [SMILES: c1ccc(NCC2CCC2)cc1]

To a mixture of aniline (0.2 g, 2.15 mmol) and cyclobutanecarbaldehyde (0.180 g, 2.15 mmol) in MeOH (10 mL) was added N, N-diisopropylethylamine (2.25 mL, 12.90 mmol) at 0° C. and the mixture was stirred at RT for 1 h, followed by the addition of sodium triacetoxyborohydride (0.338 g, 5.38 mmol) at 0° C., and the mixture was stirred at RT for 3 h. The reaction mixture was diluted with ice-water and extracted with ethyl acetate. The organic layer was washed with brine, dried over $Na_2SO_4$, filtered and evaporated under reduced pressure. The residue was purified by silica gel chromatography, eluted with 10% ethyl acetate/petroleum ether to give the desired product. LCMS: 162.08 (M+H).

(Step 2) Synthesis of 2-chloro-N-(cyclobutylmethyl)-N-phenylquinazolin-4-amine

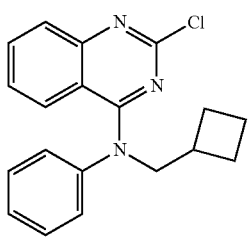 [SMILES: Clc1nc(N(CC2CCC2)c2ccccc2)c2ccccc2n1]

To a mixture of 2,4-dichloroquinazoline (0.09 g, 0.45 mmol) and N-(cyclobutylmethyl)aniline (0.073 g, 0.45 mmol) in DMF (2 mL) was added sodium hydroxide (0.036 g, 0.90 mmol) at 0° C. and the mixture was stirred for 72 h at RT. The reaction mixture was diluted with ice-water and extracted with ethyl acetate. The organic layer was washed with brine, dried over $Na_2SO_4$, filtered and evaporated under reduced pressure. The residue was purified by silica gel chromatography and eluted with 5% ethyl acetate/petroleum ether to give the desired product. LCMS: 324.13 (M+H).

(Step 3) Synthesis of N-(cyclobutylmethyl)-2-hydrazinyl-N-phenylquinazolin-4-amine

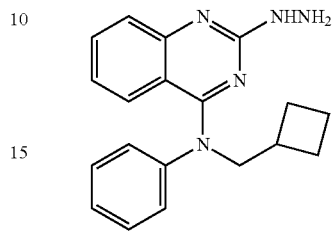

To a solution of 2-chloro-N-(cyclobutylmethyl)-N-phenylquinazolin-4-amine (0.045 g, 0.14 mmol) in EtOH (2 mL) was added hydrazine hydrate (0.014 g, 0.28 mmol) at RT and the mixture was stirred at 50° C. for 16 h. The reaction mixture was evaporated under reduced pressure to give the desired product. LCMS: 320.21 (M+H).

(Step 4) Synthesis of N-(Cyclobutylmethyl)-N-phenyl-[1,2,4]triazolo[4,3-a]quinazolin-5-amine A mixture of N-(cyclobutylmethyl)-2-hydrazinyl-N-phenylquinazolin-4-amine (0.045 g, 0.14 mmol) and triethyl orthoformate (1 mL) was stirred at 100° C. for 16 h. The reaction mixture was evaporated under reduced pressure, and the residue was purified by prep. HPLC to afford the desired product: $^1$H NMR (DMSO-$d_6$) δ 9.60 (s, 1H), 8.35-8.23 (m, 1H), 7.75 (ddd, J=8.5, 7.1, 1.5 Hz, 1H), 7.37-7.12 (m, 7H), 4.13 (d, J=7.2 Hz, 2H), 2.93-2.84 (m, 1H), 1.96-1.82 (m, 2H), 1.82-1.71 (m, 4H); LCMS(m/z) 330.2 [M+H]+.

Example 78. N-phenyl-N-((tetrahydro-2H-pyran-4-yl)methyl)-[1,2,4]triazolo[4,3-a]quinazolin-5-amine

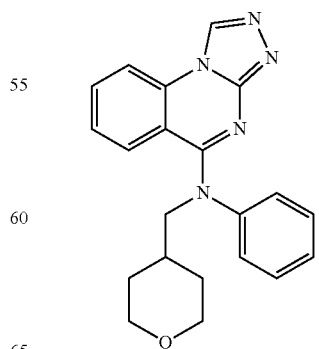

(Step 1) Synthesis of N-((Tetrahydro-2H-pyran-4-yl)methyl)aniline

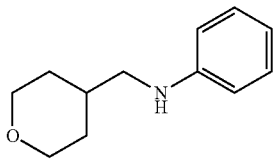 [SMILES: c1ccc(NCC2CCOCC2)cc1]

To a mixture of (tetrahydro-2H-pyran-4-yl)methanamine (0.4 g, 3.28 mmol) and phenylboronic acid (0.754 g, 6.56 mmol) in acetonitrile (10 mL) were added copper acetate (0.595 g, 3.28 mmol) and triethylamine (0.92 mL, 6.55 mmol) at RT and the mixture was stirred at 80° C. for 3 h. The reaction mixture was filtered through a bed of celite, and the filtrate was diluted with water and extracted with ethyl acetate. The organic layer was washed successively with water and brine, dried over $Na_2SO_4$, filtered and evaporated under reduced pressure. The residue was purified by silica gel column chromatography, eluted with 25% ethyl acetate/petroleum ether to give the desired product. LCMS(m/z) 192.18 $[M+H]^+$.

(Step 2) Synthesis of 2-chloro-N-phenyl-N-((tetrahydro-2H-pyran-4-yl)methyl)quinazolin-4-amine

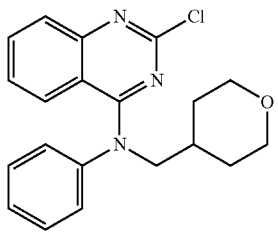 [SMILES: Clc1nc(N(CC2CCOCC2)c2ccccc2)c2ccccc2n1]

To a solution of N-((tetrahydro-2H-pyran-4-yl)methyl)aniline (0.240 g, 1.26 mmol) in DMF (6 mL) was added sodium hydroxide (0.050 g, 1.26 mmol) at 0° C. and the mixture was stirred for 1 h at RT, followed by the addition of 2,4-dichloroquinazoline (0.250 g, 1.26 mmol) at RT, and the mixture was stirred at RT for 24 h then heated to 80° C. for 2 h. The reaction mixture was diluted with water and extracted with ethyl acetate. The organic layer was washed successively with water and brine, dried over $Na_2SO_4$, filtered and evaporated under reduced pressure. The residue was purified by silica gel column chromatography, eluted with 25% ethyl acetate/petroleum ether to give the desired product. LCMS(m/z) 354.18 $[M+H]^+$.

(Step 3) Synthesis of N-Phenyl-N-((tetrahydro-2H-pyran-4-yl)methyl)-[1,2,4]triazolo[4,3-a]quinazolin-5-amine To a stirred solution of 2-chloro-N-phenyl-N-((tetrahydro-2H-pyran-4-yl)methyl)quinazolin-4-amine (0.1 g, 0.28 mmol) in toluene (5 mL) was added formohydrazide (0.034 g, 0.56 mmol) at room temperature and the mixture was refluxed for 72 h. The reaction mixture was evaporated under reduced pressure, and the residue was purified by silica gel column chromatography, followed by preparative HPLC to afford the desired product: $^1$H NMR (DMSO-$d_6$) δ 9.64 (s, 1H), 8.29 (dd, J=8.3, 1.2 Hz, 1H), 7.76 (ddd, J=8.4, 7.2, 1.4 Hz, 1H), 7.39-7.17 (m, 7H), 3.99 (d, J=7.2 Hz, 2H), 3.87-3.80 (m, 2H), 3.42-3.32 (m, 1H), 3.32-3.15 (m, 3H), 2.16 (ddd, J=12.0, 9.2, 5.5 Hz, 1H), 1.46-1.34 (m, 2H); LCMS(m/z) 360.2 $[M+H]+$.

Example 79. 5-(3,4,5,6-tetrahydrobenzo[b]azocin-1(2H)-yl)-[1,2,4]triazolo[4,3-a]quinazoline

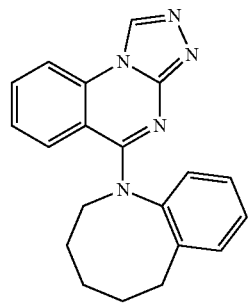 [SMILES: c1ccc2c(c1)CCCCCN2c1nc2nncn2c2ccccc12]

(Step 1) Synthesis of 3,4,5,6-Tetrahydrobenzo[b]azocin-2(1H)-one

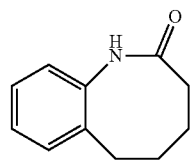 [SMILES: O=C1CCCCc2ccccc2N1]

To a solution of 6,7,8,9-tetrahydro-5H-benzo[7]annulen-5-one (4 g, 25 mmol) in concentrated HCl (40 mL) was added sodium azide (6.5 g, 100 mmol) at RT and the mixture was stirred at RT for 24 h. The reaction mixture was diluted with water, neutralized with saturated sodium bicarbonate aqueous solution and extracted with ethyl acetate. The organic layer was dried over $Na_2SO_4$, filtered and evaporated under reduced pressure. The residue was purified by silica gel column chromatography, eluted with 50% ethyl acetate/petroleum ether to give the desired product. LCMS (m/z) 176.13 $[M+H]^+$.

(Step 2) Synthesis of 1,2,3,4,5,6-hexahydrobenzo[b]azocine

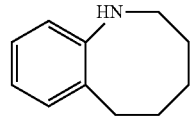 [SMILES: c1ccc2c(c1)CCCCCN2]

To a stirred solution of 3,4,5,6-tetrahydrobenzo[b]azocin-2(1H)-one (1.2 g, 6.85 mmol) in tetrahydrofuran (20 mL) was added LDA (13.7 mL, 13.71 mmol, 1.0 M in THF) at 0° C. and the mixture was stirred at 70° C. for 16 h. The reaction mixture was diluted with water and extracted with ethyl acetate. The organic layer was dried over $Na_2SO_4$, filtered and evaporated under reduced pressure to give the desired product. LCMS(m/z) 162.06 [M+H]+.

(Step 3) Synthesis of 5-(3,4,5,6-tetrahydrobenzo[b]azocin-1(2H)-yl)-[1,2,4]triazolo[4,3-a]quinazoline To a solution of 1,2,3,4,5,6-hexahydrobenzo[b]azocine (0.024 g, 0.15 mmol) in THF (10 mL) was added LDA (0.17 mL, 0.17 mmol, 1.0 M in THF) at 0° C. and the mixture was stirred at RT for 1 h, followed by the addition of 5-chloro-[1,2,4]triazolo[4,3-a]quinazoline (0.03 g, 0.15 mmol) at 0° C., and the mixture was stirred for 2 h at RT. The reaction mixture was diluted with water and extracted with ethyl acetate. The organic layer was dried over Na$_2$SO$_4$, filtered and evaporated under reduced pressure. The residue was purified by silica gel column chromatography, followed by prep. HPLC to afford the desired product: $^1$H NMR (DMSO-d$_6$) δ 9.55 (s, 1H), 8.26 (dd, J=8.2, 1.3 Hz, 1H), 7.74 (ddd, J=8.4, 7.0, 1.5 Hz, 1H), 7.46 (dd, J=7.6, 1.7 Hz, 1H), 7.40 (td, J=7.5, 1.3 Hz, 1H), 7.28 (td, J=7.6, 1.7 Hz, 1H), 7.15 (ddd, J=8.4, 7.0, 1.2 Hz, 1H), 7.09 (ddd, J=8.6, 3.3, 1.4 Hz, 2H), 4.06-3.93 (m, 2H), 2.77 (t, J=5.9 Hz, 2H), 1.73 (s, 2H), 1.61 (d, J=7.0 Hz, 4H); LCMS(m/z) 330.2 [M+H]+.

Example 80. N-(2-((tert-butyldimethylsilyl)oxy)ethyl)-N-phenyl-[1,2,4]triazolo[4,3-a]quinazolin-5-amine

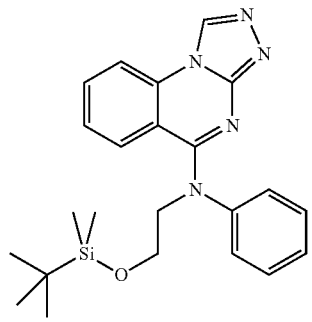 [SMILES: CC(C)(C)[Si](C)(C)OCCN(c1ccccc1)c1nc2nncn2c2ccccc12]

(Step 1) Synthesis of N-(2-((tert-butyldimethylsilyl)oxy)ethyl)aniline

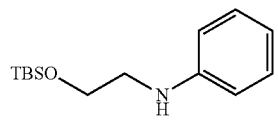 [SMILES: CC(C)(C)[Si](C)(C)OCCNc1ccccc1]

To a solution of 2-(phenylamino)ethan-1-ol (0.2 g, 1.46 mmol) in dichloromethane (10 mL) were added tert-butyldimethylsilyl chloride (0.219 g, 1.46 mmol) and imidazole (0.099 g, 1.46 mmol) at RT and the mixture was stirred at RT for 16 h. The reaction mixture was diluted with water and extracted with dichloromethane. The organic layer was dried over Na$_2$SO$_4$, filtered and evaporated under reduced pressure. The residue was purified by silica gel column chromatography and eluted with 20% ethyl acetate/petroleum ether to give the desired product. LCMS: 252.50 (M+H).

(Step 2) Synthesis of N-(2-((tert-butyldimethylsilyl)oxy)ethyl)-N-phenyl-[1,2,4]triazolo[4,3-a]quinazolin-5-amine To a solution of N-(2-((tert-butyldimethylsilyl)oxy)ethyl)aniline (0.024 g, 0.098 mmol) in THF (2 mL) was added LDA (0.1 mL, 0.2 mmol, 2.0 M in THF) at 0° C. and the mixture was stirred for 1 h at RT, followed by the addition of 5-chloro-[1,2,4]triazolo[4,3-a]quinazoline (0.02 g, 0.098 mmol) at 0° C., and the mixture was then stirred for 2 h at RT. The reaction mixture was diluted with water and extracted with ethyl acetate. The organic layer was dried over Na$_2$SO$_4$, filtered and evaporated under reduced pressure. The residue was purified by silica gel column chromatography, eluted with 3% methanol/dichloromethane to afford the desired product: $^1$H NMR (DMSO-d$_6$) δ 9.63 (s, 1H), 8.37-8.23 (m, 1H), 7.76 (ddd, J=8.5, 6.6, 2.1 Hz, 1H), 7.39-7.31 (m, 4H), 7.24-7.14 (m, 3H), 4.21 (t, J=5.8 Hz, 2H), 3.95 (t, J=5.8 Hz, 2H), 0.79 (s, 9H), −0.06 (s, 6H); LCMS(m/z) 420.2 [M+H]+.

Example 81. N-methyl-N-(3-(trifluoromethyl)phenyl)-[1,2,4]triazolo[4,3-a]quinazolin-5-amine

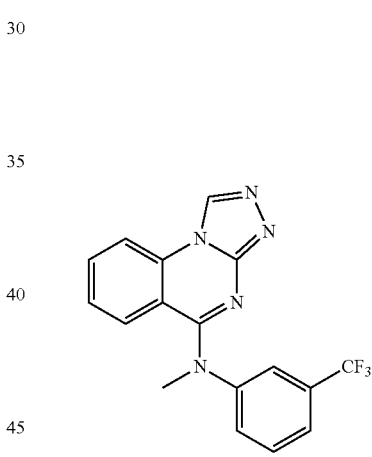

To a stirred solution of N-methyl-3-(trifluoromethyl)aniline (0.052 g, 0.29 mmol) in THF (5 mL) was added LDA (0.22 mL, 0.44 mmol, 1.5 eq., 2.0 M in THF) at 0° C. and the mixture was stirred for 1 h at RT, followed by the addition of 5-chloro-[1,2,4]triazolo[4,3-a]quinazoline (0.067 g, 0.29 mmol) at 0° C., and the mixture was stirred for 1 h at RT. The progress of the reaction was monitored by TLC. After completion of the reaction, the reaction mixture was quenched with sat. NH$_4$Cl solution and extracted with ethyl acetate. The organic layer was dried over Na$_2$SO$_4$, filtered and evaporated under reduced pressure. The residue was purified by prep. HPLC to afford the desired product: $^1$H NMR (DMSO-d$_6$) δ 9.68 (s, 1H), 8.33 (dd, J=8.3, 1.0 Hz, 1H), 7.81 (ddd, J=8.4, 6.3, 2.3 Hz, 1H), 7.75-7.66 (m, 1H), 7.65-7.52 (m, 3H), 7.32-7.19 (m, 2H), 3.60 (s, 3H); LCMS(m/z) 344.1 [M+H]+.

Example 82. N-methyl-N-(3-(trifluoromethoxy)phenyl)-[1,2,4]triazolo[4,3-a]quinazolin-5-amine

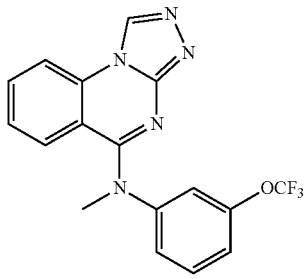 [SMILES: CN(c1cccc(OC(F)(F)F)c1)c1nc2nncn2c2ccccc12]

(Step 1) Synthesis of N-methyl-3-(trifluoromethoxy)aniline

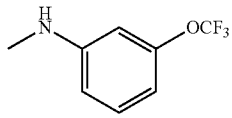

To a stirred solution of 3-(trifluoromethoxy)aniline (1.0 g, 5.64 mmol) in MeOH (10 mL) were added 37% formaldehyde (0.254 g, 8.47 mmol) and sodium methoxide (1.52 g, 28.22 mmol) at 0° C. and the mixture was stirred for 3 h at RT, followed by the addition of sodium borohydride (0.214 g, 5.64 mmol) at 0° C., and the mixture was heated to 60° C. for 3 h. The progress of the reaction was monitored by TLC. After completion of the reaction, the reaction mixture was evaporated under reduced pressure. The residue was diluted with water and extracted with ethyl acetate. The organic layer was washed successively with water and brine, and dried over $Na_2SO_4$, filtered and evaporated under reduced pressure. The residue was purified by silica gel column chromatography and eluted with 10% ethyl acetate/petroleum ether to give the desired product. LCMS: 192.11 (M+H).

(Step 2) Synthesis of N-methyl-N-(3-(trifluoromethoxy)phenyl)-[1,2,4]triazolo[4,3-a]quinazolin-5-amine To a stirred solution of N-methyl-3-(trifluoromethoxy)aniline (0.188 g, 0.98 mmol) in THF (10 mL) was added LDA (0.27 mL, 0.54 mmol, 2.0 M in THF) at 0° C. and the mixture was stirred at RT for 1 h, followed by the addition of 5-chloro-[1,2,4]triazolo[4,3-a]quinazoline (0.1 g, 0.49 mmol) at 0° C., and the mixture was stirred at RT for 1 h. The progress of the reaction was monitored by TLC. After completion of the reaction, the reaction mixture was quenched with saturated $NH_4Cl$ solution and extracted with ethyl acetate. The organic layer was dried over $Na_2SO_4$, filtered and evaporated under reduced pressure. The residue was purified by silica gel column chromatography, eluted with 1% methanol/dichloromethane and then prep. HPLC to afford the desired product: $^1$H NMR (DMSO-$d_6$) δ 9.67 (s, 1H), 8.32 (d, J=8.3 Hz, 1H), 7.81 (ddd, J=8.4, 5.5, 3.0 Hz, 1H), 7.50 (t, J=8.1 Hz, 1H), 7.40-7.33 (m, 2H), 7.31-7.24 (m, 2H), 7.20 (ddt, J=8.3, 2.3, 1.1 Hz, 1H), 3.58 (s, 3H); LCMS(m/z) 360.1 [M+H]+.

Example 83. (3-([1,2,4]triazolo[4,3-a]quinazolin-5-yl(methyl)amino)phenyl)methanol

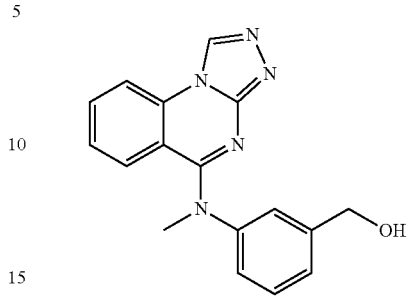

To a solution of N-(3-(((tert-butyldimethylsilyl)oxy)methyl)phenyl)-N-methyl-[1,2,4]triazolo[4,3-a]quinazolin-5-amine (Example 104) (0.06 g, 0.14 mmol) in THF (4 mL) was added tetra-n-butylammonium fluoride (0.041 g, 0.16 mmol) at 0° C. and the mixture was stirred for 2 h at RT. The progress of the reaction was monitored by TLC. After completion of the reaction, the reaction mixture was diluted with water and extracted with ethyl acetate. The organic layer was washed successively with water and brine, dried over $Na_2SO_4$, filtered and evaporated under reduced pressure. The crude compound was purified by silica gel column chromatography, eluted with 4% methanol/dichloromethane, followed by prep. HPLC to afford the desired product: $^1$H NMR (DMSO-$d_6$) δ 9.62 (s, 1H), 8.29 (dd, J=8.5, 1.2 Hz, 1H), 7.77 (ddd, J=8.5, 7.1, 1.4 Hz, 1H), 7.33-7.18 (m, 5H), 7.14-7.08 (m, 1H), 5.23 (t, J=5.7 Hz, 1H), 4.46 (d, J=5.7 Hz, 2H), 3.53 (s, 3H); LCMS(m/z) 306.2 [M+H]+.

Example 84. N-methyl-N-phenyl-8-(1H-pyrrol-2-yl)-[1,2,4]triazolo[4,3-a]quinazolin-5-amine

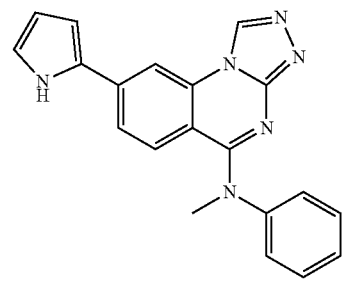 [SMILES: CN(c1ccccc1)c1nc2nncn2c2cc(-c3ccc[nH]3)ccc12]

A mixture of 8-bromo-N-methyl-N-phenyl-[1,2,4]triazolo[4,3-a]quinazolin-5-amine (Example 28) (15 mg, 0.042 mmol), $K_3PO_4$ (27.0 mg, 0.127 mmol), Pd(OAc)$_2$ (1.901 mg, 8.47 µmol), tricyclohexylphosphine (2.375 mg, 8.47 µmol) and tert-butyl 2-(5-(methyl(phenyl)amino)-[1,2,4]triazolo[4,3-a]quinazolin-8-yl)-1H-pyrrole-1-carboxylate (22.34 mg, 0.106 mmol) in dioxane/water (0.21 mL) was heated at 120° C. for 1 h. The reaction mixture was subjected to solid phase extraction (washed with MeOH, then eluted with $NH_3$ in MeOH) using Bond Elut SCX cartridge (Agilent), and the collected fractions were concentrated in vacuo. The residue was purified by column chromatography (Si-column, CHC$_3$:MeOH=10:0-9:1) to afford the desired product: $^1$H-NMR (Methanol-d4) δ 9.36 (s, 1H), 8.28 (d, J=1.8 Hz, 1H), 7.48-7.39 (m, 2H), 7.38-7.26 (m, 5H), 7.21 (d, J=8.9 Hz, 1H), 6.98-6.92 (m, 1H), 6.82 (dd, J=3.6, 1.4 Hz, 1H), 6.27-6.20 (m, 1H), 3.65 (s, 3H); LCMS(m/z) 341.0 [M+H]+.

Example 85. N-(5-(methyl(phenyl)amino)-[1,2,4]triazolo[4,3-a]quinazolin-8-yl)methanesulfonamide

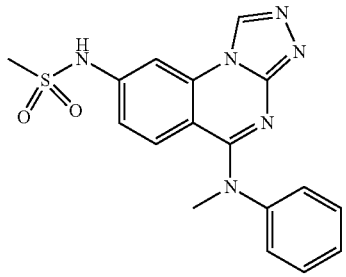 [SMILES: CN(c1ccccc1)c1nc2nncn2c2cc(NS(C)(=O)=O)ccc12]

A mixture of N5-methyl-N5-phenyl-[1,2,4]triazolo[4,3-a]quinazoline-5,8-diamine (Example 66) (40 mg, 0.138 mmol), triethylamine (0.192 mL, 1.378 mmol) and methanesulfonyl chloride (6M in 1,2-dichloroethane, 2 mL) was stirred for 4.5 h at 70° C. The reaction mixture was evaporated in vacuo. The residue was dissolved in DMA (2 mL), and methanesulfonyl chloride (6M in 1,2-dichloroethane, 2 mL) was added to the solution at RT. The mixture was stirred overnight at 110° C. The reaction mixture was subjected to solid phase extraction (washed with MeOH, then eluted with NH$_3$ in MeOH) using Bond Elut SCX cartridge (Agilent), and the collected fractions were concentrated in vacuo. The residue was purified by prep-LCMS to afford the desired product: $^1$H NMR (DMSO-d$_6$) δ 10.67 (s, 1H), 9.48 (s, 1H), 7.72 (s, 1H), 7.47-7.33 (m, 2H), 7.27 (dt, J=8.2, 1.8 Hz, 3H), 7.13 (d, J=9.1 Hz, 1H), 6.85 (dd, J=9.1, 2.2 Hz, 1H), 3.51 (s, 3H), 3.19 (s, 3H); LCMS(m/z) 369.3 [M+H]+.

Example 86. N-methyl-N-phenyl-8-(piperidin-1-yl)-[1,2,4]triazolo[4,3-a]quinazolin-5-amine

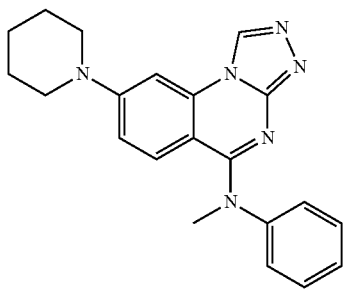 [SMILES: CN(c1ccccc1)c1nc2nncn2c2cc(N3CCCCC3)ccc12]

A mixture of 8-bromo-N-methyl-N-phenyl-[1,2,4]triazolo[4,3-a]quinazolin-5-amine (Example 28) (20 mg, 0.056 mmol), K$_2$CO$_3$ (15.61 mg, 0.113 mmol), Pd(dba)$_3$ (0.011 mmol) and piperidine (5.77 mg, 0.068 mmol) in DMF (282 μL) was stirred for overnight at 100° C. The reaction mixture was concentrated in vacuo, and the residue was purified by column chromatography (Si-column, CHCl$_3$:MeOH=0-20%) to afford the desired product: $^1$H NMR (Methanol-d4) δ 9.36 (s, 1H), 7.46-7.32 (m, 2H), 7.33-7.15 (m, 4H), 6.93 (d, J=9.5 Hz, 1H), 6.58 (dd, J=9.6, 2.6 Hz, 1H), 3.56 (s, 3H), 3.43 (dd, J=6.2, 4.0 Hz, 4H), 1.72-1.61 (m, 6H); LCMS(m/z) 359.2 [M+H]+.

Example 87. Methyl 5-(methyl(phenyl)amino)-[1,2,4]triazolo[4,3-a]quinazoline-8-carboxylate

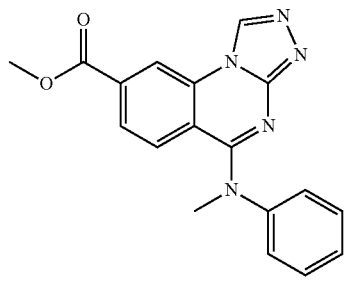 [SMILES: COC(=O)c1ccc2c(N(C)c3ccccc3)nc3nncn3c2c1]

A mixture of 8-bromo-N-methyl-N-phenyl-[1,2,4]triazolo[4,3-a]quinazolin-5-amine (Example 28) (10 mg, 0.028 mmol), Mo(CO)$_6$ (7.45 mg, 0.028 mmol), Pd(OAc)$_2$ 1.268 mg, 0.0056 mmol) and Pd(dppf)$_2$ (0.0056 mmol) in DMA/MeOH (1:1, 0.14 mL) was stirred for 2 h at 100° C. The reaction mixture was filtered through a bed of celite with MeOH. The filtrate was concentrated in vacuo, and the residue was purified by prep-HPLC to afford the desired product: $^1$H NMR (Methanol-d$_4$) δ 9.74 (s, 1H), 8.90 (d, J=1.6 Hz, 1H), 7.81 (dd, J=8.9, 1.6 Hz, 1H), 7.61-7.50 (m, 3H), 7.47-7.40 (m, 2H), 7.30 (d, J=8.8 Hz, 1H), 3.98 (s, 3H), 3.81 (s, 3H); LCMS(m/z) 334.2 [M+H]+.

Example 88. N-methyl-N-(3-nitrophenyl)-[1,2,4]triazolo[4,3-a]quinazolin-5-amine

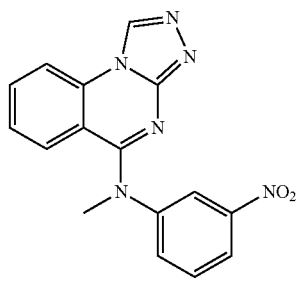 [SMILES: CN(c1cccc([N+](=O)[O-])c1)c1nc2nncn2c2ccccc12]

(Step 1) Synthesis of 2-chloro-N-methyl-N-(3-nitrophenyl)quinazolin-4-amine

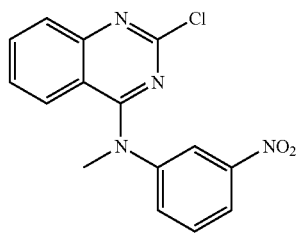 [SMILES: CN(c1cccc([N+](=O)[O-])c1)c1nc(Cl)nc2ccccc12]

To a stirred solution of N-methyl-3-nitrobenzenamine (0.382 g, 2.51 mmol) in DMF (10 mL) was added 60% sodium hydride (0.120 g, 3.01 mmol) at 0° C. and the mixture was stirred for 1 h at RT, followed by the addition of 2,4-dichloroquinazoline (0.5 g, 2.51 mmol) at 0° C. The mixture was stirred for 3 h at RT. The progress of the reaction was monitored by TLC. After completion of the reaction, the reaction mixture was diluted with ice-water. The resulting solids were filtered and dried under vacuum to give the desired product. LCMS: 315.10 (M+H).

(Step 2) Synthesis of N-methyl-N-(3-nitrophenyl)-[1,2,4]triazolo[4,3-a]quinazolin-5-amine To a stirred solution of 2-chloro-N-methyl-N-(3-nitrophenyl)quinazolin-4-amine (0.1 g, 0.32 mmol) in toluene (4 mL) was added formic hydrazide (0.038 g, 0.63 mmol) at RT and the mixture was heated to 120° C. for 72 h. The progress of the reaction was monitored by TLC. After completion of the reaction, the reaction mixture was evaporated under reduced pressure. The residue was washed with diethyl ether and purified by prep. HPLC to give the desired product: $^1$H NMR (DMSO-$d_6$) δ 9.70 (s, 1H), 8.42-8.33 (m, 1H), 8.19 (t, J=2.2 Hz, 1H), 8.03 (ddd, J=8.2, 2.3, 1.0 Hz, 1H), 7.83 (ddd, J=8.4, 7.1, 1.4 Hz, 1H), 7.67 (ddd, J=8.2, 2.2, 1.0 Hz, 1H), 7.58 (t, J=8.1 Hz, 1H), 7.37 (dd, J=8.3, 1.4 Hz, 1H), 7.32 (m, 1H), 3.63 (s, 3H); LCMS(m/z) 321.1 [M+H]+.

Example 89. N-(3-(methoxymethyl)phenyl)-N-methyl-[1,2,4]triazolo[4,3-a]quinazolin-5-amine

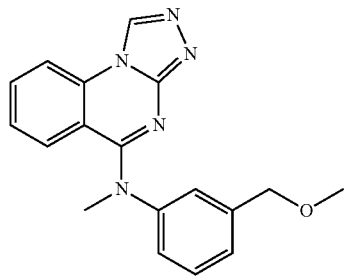 [SMILES: COCc1cccc(N(C)c2nc3nncn3c3ccccc23)c1]

To a solution of (3-([1,2,4]triazolo[4,3-a]quinazolin-5-yl(methyl)amino)phenyl)methanol (Example 83) (0.03 g, 0.098 mmol) in DMF (2 mL) was added 60% sodium hydride (0.005 g, 0.12 mmol) at 0° C. and the mixture was stirred for 15 min at RT, followed by the addition of methyl iodide (0.007 mL, 0.12 mmol) at 0° C. The mixture was stirred for 16 h at RT. The reaction mixture was diluted with cold water and extracted with ethyl acetate. The organic layer was washed successively with water and brine, dried over Na$_2$SO$_4$, filtered and evaporated under reduced pressure. The residue was purified by prep. HPLC to afford the desired product: $^1$H-NMR (DMSO-$d_6$) δ 9.62 (s, 1H), 8.29 (dd, J=8.3, 1.2 Hz, 1H), 7.77 (ddd, J=8.5, 7.1, 1.5 Hz, 1H), 7.37 (td, J=7.2, 1.9 Hz, 1H), 7.31-7.17 (m, 5H), 4.36 (s, 2H), 3.54 (s, 3H), 3.20 (s, 3H); LCMS(m/z) 320.2 [M+H]+.

Example 90. N-(3-(fluoromethyl)phenyl)-N-methyl-[1,2,4]triazolo[4,3-a]quinazolin-5-amine

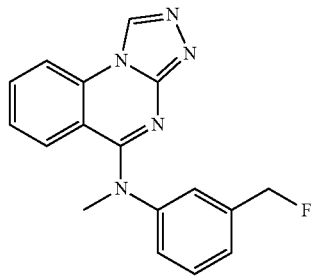

To a solution of (3-([1,2,4]triazolo[4,3-a]quinazolin-5-yl(methyl)amino)phenyl)methanol (Example 83) (0.05 g, 0.16 mmol) in dichloromethane (4 mL) was added diethylaminosulfur trifluoride (0.04 mL, 0.33 mmol) at −78° C. and the mixture was stirred for 2 h at RT. The reaction mixture was quenched with saturated sodium bicarbonate aqueous solution and extracted with dichloromethane. The organic layer was washed successively with water and brine, dried over Na$_2$SO$_4$, filtered and evaporated under reduced pressure. The residue was purified by prep. HPLC to afford the desired product: $^1$H-NMR (500 MHz, DMSO-$d_6$) δ 9.64 (s, 1H), 8.30 (dd, J=8.3, 1.3 Hz, 1H), 7.78 (ddd, J=8.4, 7.1, 1.5 Hz, 1H), 7.43-7.37 (m, 2H), 7.29 (ddd, J=8.1, 4.4, 1.7 Hz, 3H), 7.25-7.22 (m, 1H), 5.37 (d, J=47.5 Hz, 2H), 3.55 (s, 3H); LCMS(m/z) 308.1 [M+H]+.

Example 91. N-(3-ethylphenyl)-N-methyl-[1,2,4]triazolo[4,3-a]quinazolin-5-amine

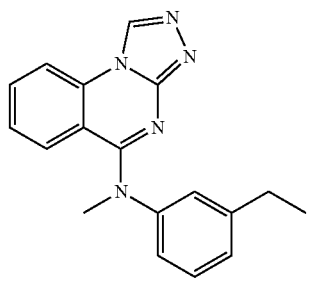

To a stirred solution of 3-ethyl-N-methylaniline (0.066 g, 0.49 mmol) in THF (3 mL) was added LDA (0.18 mL, 0.37 mmol, 2.0 M in THF) at 0° C., and the mixture was stirred for 1 h at RT. Then, 5-chloro-[1,2,4]triazolo[4,3-a]quinazoline (0.05 g, 0.24 mmol) was added to the solution at 0° C., and the mixture was stirred for 1 h at RT. The progress of the reaction was monitored by TLC. After completion of the reaction, the reaction mixture was diluted with ice-water and extracted with ethyl acetate. The organic layer was dried over Na$_2$SO$_4$, filtered and evaporated under reduced pressure. The residue was purified by prep. HPLC to afford the desired product: $^1$H-NMR (DMSO-$d_6$) δ 9.61 (s, 1H), 8.43-8.23 (m, 1H), 7.76 (ddd, J=8.4, 7.0, 1.6 Hz, 1H), 7.34-7.16 (m, 3H), 7.15-7.08 (m, 3H), 3.53 (s, 3H), 2.65-2.51 (m, 2H), 1.08 (t, J=7.6 Hz, 3H); LCMS(m/z) 304.2 [M+H]+.

Example 92. 8-(cyclopropylethynyl)-N-methyl-N-phenyl-[1,2,4]triazolo[4,3-a]quinazolin-5-amine

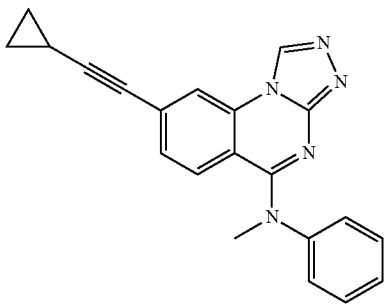

A mixture of 8-bromo-N-methyl-N-phenyl-[1,2,4]triazolo[4,3-a]quinazolin-5-amine (Example 28) (20 mg, 0.056 mmol), prop-1-yne (0.02 mL, 2 mmol, 0.1 M THF solution), triethylamine (22.85 mg, 0.226 mmol), Pd(OAc)$_2$ (3.80 mg, 0.017 mmol), triphenylphosphine (19.99 mg, 0.076 mmol) and copper(I) iodide (3.23 mg, 0.017 mmol) in dioxane (0.4 mL) was treated in a microwave reactor at 120° C. for 2 h. The reaction mixture was purified by column chromatography (Si-column, CHC$_3$:MeOH=10:0-9:1) to afford the desired product: $^1$H-NMR (CDCl$_3$) δ 8.91 (s, 1H), 7.73 (d, J=1.5 Hz, 1H), 7.46-7.30 (m, 2H), 7.31-7.22 (m, 1H), 7.22-7.09 (m, 3H), 7.03 (dd, J=8.7, 1.6 Hz, 1H), 3.67 (s, 3H), 1.44-1.30 (m, 1H), 0.48-0.35 (m, 2H), 0.20-0.10 (m, 2H); LCMS(m/z) 340.3 [M+H]+.

Example 93. 9-chloro-N-methyl-N-phenyl-[1,2,4]triazolo[4,3-a]quinazolin-5-amine

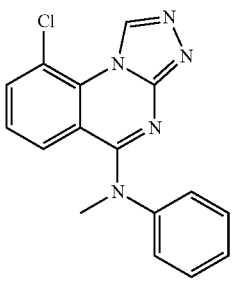

(Step 1) Synthesis of 2,8-dichloro-N-methyl-N-phenylquinazolin-4-amine

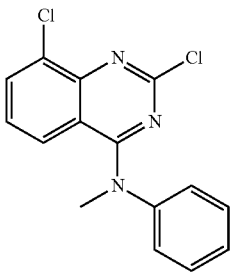

To a solution of 2,4,8-trichloroquinazoline (100 mg, 0.428 mmol) in DMF (2.1 mL) were added N-methylaniline (45.9 mg, 0.428 mmol) and sodium hydroxide (17.13 mg, 0.428 mmol), and the mixture was stirred for 1 h at RT. The reaction mixture was diluted with AcOEt, washed successively with water and brine, and dried over Na$_2$SO$_4$. The organic layer was concentrated in vacuo to give the desired product. LCMS(m/z) 303.98 [M–H]+.

(Step 2) Synthesis of 8-chloro-2-hydrazinyl-N-methyl-N-phenylquinazolin-4-amine

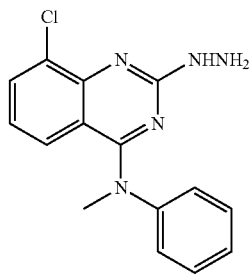

To a solution of 2,8-dichloro-N-methyl-N-phenylquinazolin-4-amine (61 mg, 0.201 mmol) in EtOH (1 mL) was added hydrazine hydrate (20.08 mg, 0.401 mmol), and the mixture was stirred for 2 h at 50° C. The reaction mixture was diluted with AcOEt, washed successively with water and brine, and dried over Na$_2$SO$_4$. The organic layer was concentrated in vacuo to give the desired product. LCMS (m/z) 300.13 [M+H]+.

(Step 3) Synthesis of 9-chloro-N-methyl-N-phenyl-[1,2,4]triazolo[4,3-a]quinazolin-5-amine A mixture of 8-chloro-2-hydrazinyl-N-methyl-N-phenylquinazolin-4-amine (53 mg, 0.177 mmol) and triethoxymethane (52 mg, 0.354 mmol) was stirred for 1 h at 100° C. The reaction mixture was concentrated in vacuo, and the residue was purified by column chromatography (Si-column, CHC$_3$:MeOH=10:0-9:1), followed by prep-HPLC to afford the desired product: $^1$H NMR (Methanol-d$_4$) δ 10.02 (s, 1H), 7.89 (d, J=7.9 Hz, 1H), 7.45 (t, J=7.6 Hz, 2H), 7.40-7.13 (m, 5H), 3.71 (s, 3H); LCMS(m/z) 310.1 [M+H]+.

Example 94. 5-(methyl(phenyl)amino)-[1,2,4]triazolo[4,3-a]quinazoline-8-carbonitrile

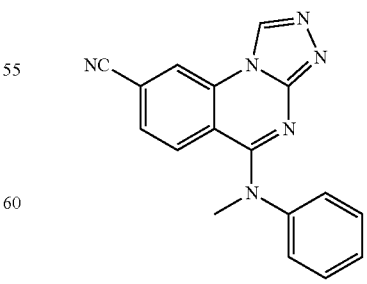

To a solution of 8-bromo-N-methyl-N-phenyl-[1,2,4]triazolo[4,3-a]quinazolin-5-amine (Example 28) (30 mg, 0.085 mmol) in DMF (423 μL) were added zinc cyanide (19.89 mg, 0.169 mmol) and Pd(PPh$_3$)$_4$ (19.57 mg, 0.017 mmol), and the mixture was treated in a microwave reactor for 2 h at 100° C. The reaction mixture was subjected to solid phase extraction (washed with MeOH, then eluted with NH$_3$ in MeOH) using Bond Elut SCX cartridge (Agilent), and the collected fractions were concentrated in vacuo. The residue was purified by column chromatography (Si-column, CHCl$_3$:MeOH=10:0-9:1) to afford the desired product: $^1$H NMR (Methanol-d$_4$) δ 9.45 (s, 1H), 8.65 (d, J=1.5 Hz, 1H), 7.46-7.29 (m, 7H), 3.65 (s, 3H); LCMS(m/z) 301.2 [M+H]+.

Example 95. N-methyl-N-phenyl-8-(trifluoromethyl)-[1,2,4]triazolo[4,3-a]quinazolin-5-amine

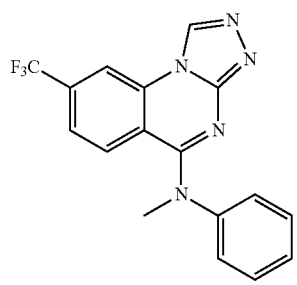

(Step 1) Synthesis of 7-(trifluoromethyl)quinazoline-2,4(1H,3H)-dione

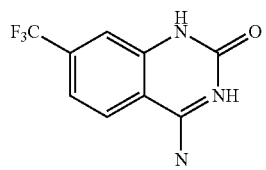 [SMILES: Nc1nc(=O)[nH]c2cc(C(F)(F)F)ccc12]

A mixture of 2-amino-4-chlorobenzoic acid (5 g, 29.1 mmol) and urea (6.13 g, 102 mmol) was stirred overnight at 200° C. The reaction mixture was cooled to RT, and diluted with water. The resulting solids were collected and washed with water to give the desired product.

(Step 2) Synthesis of 2,4-dichloro-7-(trifluoromethyl)quinazoline

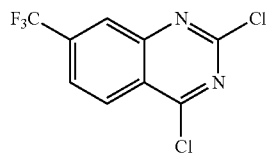 [SMILES: FC(F)(F)c1ccc2c(Cl)nc(Cl)nc2c1]

A mixture of 7-(trifluoromethyl)quinazoline-2,4(1H,3H)-dione (500 mg, 2.17 mmol) and phosphoryl trichloride (833 mg, 5.43 mmol) was stirred for 6 h at 100° C. The reaction mixture was concentrated in vacuo. Ice-water was added to the residue, and the resulting solids were collected and washed with water to give the desired product. The residue was used for the next step without further purification.

(Step 3) Synthesis of 2-chloro-N-methyl-N-phenyl-7-(trifluoromethyl)quinazolin-4-amine

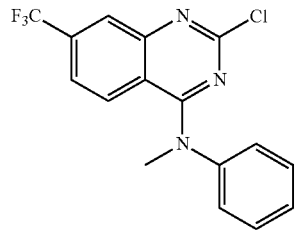 [SMILES: CN(c1ccccc1)c1nc(Cl)nc2cc(C(F)(F)F)ccc12]

To a solution of 2,4-dichloro-7-(trifluoromethyl)quinazoline (130 mg, crude) in DMF (2.4 mL) were added sodium hydride (11.68 mg, 0.487 mmol) and N-methylaniline (52.2 mg, 0.487 mmol), and the mixture was stirred for 30 min at RT. The mixture was diluted with AcOEt, washed successively with water and brine, and dried over Na$_2$SO$_4$. The organic layer was concentrated in vacuo. The residue was used for the next step without further purification. LCMS (m/z) 338.03 [M+H]$^+$.

(Step 4) Synthesis of 2-hydrazinyl-N-methyl-N-phenyl-7-(trifluoromethyl)quinazolin-4-amine

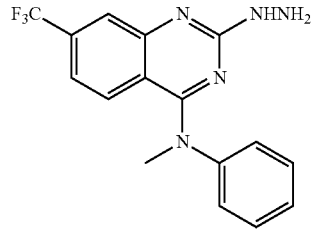 [SMILES: CN(c1ccccc1)c1nc(NN)nc2cc(C(F)(F)F)ccc12]

To a solution of 2-chloro-N-methyl-N-phenyl-7-(trifluoromethyl)quinazolin-4-amine (171 mg, crude) in EtOH (2.5 mL) was added hydrazine hydrate (50.7 mg, 1.013 mmol), and the mixture was stirred for 2 h at 50° C. The reaction mixture was diluted with AcOEt, washed successively with water and brine, and dried over Na$_2$SO$_4$. The organic layer was concentrated in vacuo. The residue was used for the next step. LCMS(m/z) 334.13 [M+H]$^+$.

(Step 5) Synthesis of N-methyl-N-phenyl-8-(trifluoromethyl)-[1,2,4]triazolo[4,3-a]quinazolin-5-amine A mixture of 2-hydrazinyl-N-methyl-N-phenyl-7-(trifluoromethyl)quinazolin-4-amine (162 mg, crude) and triethoxymethane (224 mg, 1.519 mmol) was stirred for 2 h at 90° C. The mixture was concentrated in vacuo. The residue was purified by column chromatography (Si-column, CHCl$_3$:MeOH=10:0-9:1) and prep-HPLC to afford the desired product: $^1$H-NMR (Methanol-d$_4$) δ 9.70 (s, 1H), 8.75 (dt, J=1.7, 0.8 Hz, 1H), 7.60-7.47 (m, 4H), 7.46-7.38 (m, 3H), 3.79 (s, 3H); LCMS(m/z) 344.2 [M+H]+.

Example 96. N-methyl-N-phenyl-8-(prop-1-en-2-yl)-[1,2,4]triazolo[4,3-a]quinazolin-5-amine

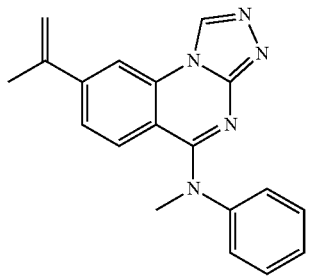

A mixture of 8-bromo-N-methyl-N-phenyl-[1,2,4]triazolo[4,3-a]quinazolin-5-amine (Example 28) (25 mg, 0.071 mmol), $K_3PO_4$ (17.98 mg, 0.085 mmol), $Pd(OAc)_2$ (7.92 mg, 0.035 mmol), tricyclohexylphosphine (19.79 mg, 0.071 mmol) and 4,4,5,5-tetramethyl-2-(prop-1-en-2-yl)-1,3,2-dioxaborolane (11.86 mg, 0.071 mmol) in dioxane/water (0.35 mL) was heated at 67° C. for 1 h. The reaction mixture was subjected to solid phase extraction (washed with MeOH, then eluted with $NH_3$ in MeOH) using Bond Elut SCX cartridge (Agilent), and the collected fractions were concentrated in vacuo. The residue was purified by column chromatography (Si-column, $CHCl_3$:MeOH=10:0-9:1) to afford the desired product: $^1$H-NMR (Methanol-$d_4$) δ 9.54 (s, 1H), 8.21 (d, J=1.7 Hz, 1H), 7.50-7.16 (m, 7H), 5.65-5.64 (m, 1H), 5.33-5.32 (m, 1H), 3.65 (s, 3H), 2.20 (dd, J=1.5, 0.8 Hz, 3H); LCMS(m/z) 316.2 [M+H]+.

Example 97. 8-(2-fluorophenyl)-N-methyl-N-phenyl-[1,2,4]triazolo[4,3-a]quinazolin-5-amine

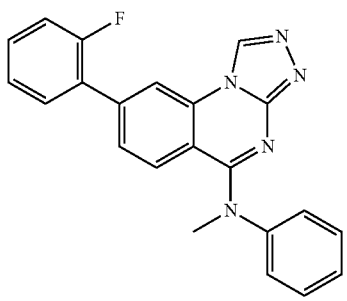

A mixture of 8-bromo-N-methyl-N-phenyl-[1,2,4]triazolo[4,3-a]quinazolin-5-amine (Example 28) (20 mg, 0.056 mmol), $K_3PO_4$ (23.97 mg, 0.113 mmol), $Pd(OAc)_2$ (2.54 mg, 0.011 mmol), tricyclohexylphosphine (3.17 mg, 0.011 mmol) and (2-fluorophenyl)boronic acid (15.80 mg, 0.113 mmol) in dioxane/water (0.28 ml) was heated at 100° C. for 1 h. The reaction mixture was subjected to solid phase extraction (washed with MeOH, then eluted with $NH_3$ in MeOH) using Bond Elut SCX cartridge (Agilent), and the collected fractions were purified by column chromatography, $CHCl_3$:MeOH=10:0-9:1) to afford the desired product: $^1$H NMR (Methanol-$d_4$) δ 9.49 (s, 1H), 8.31 (q, J=1.0 Hz, 1H), 7.56 (td, J=7.8, 1.8 Hz, 1H), 7.49-7.40 (m, 3H), 7.36-7.17 (m, 7H), 3.66 (s, 3H); LCMS(m/z) 370.3 [M+H]+.

Example 98. 8-(4-fluorophenyl)-N-methyl-N-phenyl-[1,2,4]triazolo[4,3-a]quinazolin-5-amine

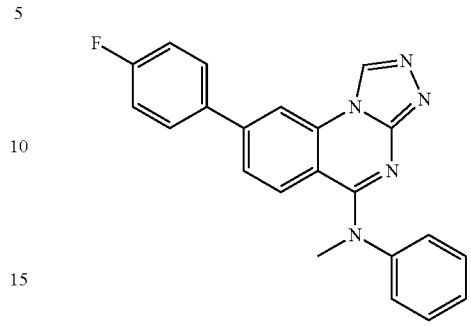

A mixture of 8-bromo-N-methyl-N-phenyl-[1,2,4]triazolo[4,3-a]quinazolin-5-amine (Example 28) (20 mg, 0.056 mmol), $K_3PO_4$ (23.97 mg, 0.113 mmol), $Pd(OAc)_2$ (2.54 mg, 0.011 mmol), tricyclohexylphosphine (3.17 mg, 0.011 mmol) and (4-fluorophenyl)boronic acid (19.75 mg, 0.141 mmol) in dioxane/water (0.28 ml) was heated at 100° C. for 1 h. The reaction mixture was subjected to solid phase extraction (washed with MeOH, then eluted with $NH_3$ in MeOH) using Bond Elut SCX cartridge (Agilent), and the collected fractions were concentrated in vacuo. The residue was purified by column chromatography (Si-column, $CHC_3$:MeOH=10:0-9:1) to afford the desired product: $^1$H NMR (Methanol-$d_4$) δ 9.54 (s, 1H), 8.38 (d, J=1.8 Hz, 1H), 7.83-7.73 (m, 2H), 7.49-7.38 (m, 3H), 7.36-7.27 (m, 4H), 7.25-7.17 (m, 2H), 3.66 (s, 3H); LCMS(m/z) 370.3 [M+H]+.

Example 99. 5-(methyl(phenyl)amino)-[1,2,4]triazolo[4,3-a]quinazoline-8-carbonitrile

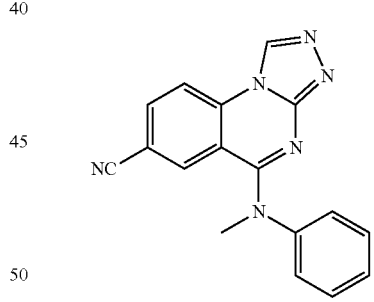

A mixture of 7-bromo-N-methyl-N-phenyl-[1,2,4]triazolo[4,3-a]quinazolin-5-amine (Example 62) (20 mg, 0.056 mmol), zinc cyanide (13.26 mg, 0.113 mmol), and $Pd(PPh_3)_4$ (13.05 mg, 0.011 mmol) in dioxane/water (0.35 mL) was heated at 80° C. for 1 h. The reaction mixture was subjected to solid phase extraction (washed with MeOH, then eluted with $NH_3$ in MeOH) using Bond Elut SCX cartridge (Agilent), and the collected fractions were concentrated in vacuo. The residue was purified by column chromatography (Si-column, $CHCl_3$:MeOH=10:0-9:1) to afford the desired product: $^1$H NMR (Methanol-$d_4$) δ 9.47 (s, 1H), 8.32 (d, J=8.6 Hz, 1H), 8.03 (dd, J=8.6, 1.7 Hz, 1H), 7.55-7.46 (m, 3H), 7.46-7.39 (m, 1H), 7.38-7.32 (m, 2H), 3.68 (s, 3H); LCMS(m/z) 301.2.

Example 100. N-(3-bromophenyl)-N-methyl-[1,2,4]triazolo[4,3-a]quinazolin-5-amine

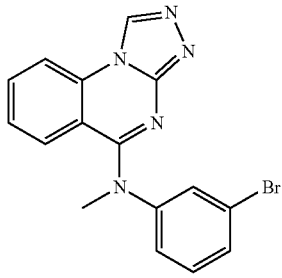 [SMILES: CN(c1cccc(Br)c1)c1nc2nncn2c2ccccc12]

(Step 1) Synthesis of N-(3-bromophenyl)-2-chloro-N-methylquinazolin-4-amine

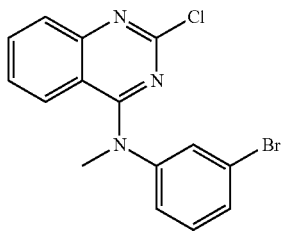 [SMILES: CN(c1cccc(Br)c1)c1nc(Cl)nc2ccccc12]

To a stirred mixture of 2,4-dichloroquinazoline (1.0 g, 5.02 mmol) and 3-bromo-N-methylaniline (0.96 mL, 7.54 mmol) in DMF (15 mL) was added sodium hydroxide (0.402 g, 10.05 mmol) at 0° C. and the mixture was stirred for 5 h at RT. The progress of the reaction was monitored by TLC. After completion of the reaction, the reaction mixture was diluted with ice-water. The resulting solids were filtered and dried under vacuum. The residue was purified by silica gel column chromatography, eluted with 19% ethyl acetate/petroleum ether to give the desired product. LCMS: 348.34 (M+H).

(Step 2) Synthesis of N-(3-bromophenyl)-N-methyl-[1,2,4]triazolo[4,3-a]quinazolin-5-amine To a stirred solution of N-(3-bromophenyl)-2-chloro-N-methylquinazolin-4-amine (0.1 g, 0.29 mmol) in toluene (3 mL) was added formic hydrazide (0.034 g, 0.57 mmol) at RT and the mixture was heated to 120° C. for 78 h. The progress of the reaction was monitored by TLC. After completion of the reaction, the reaction mixture was evaporated under reduced pressure. The residue was washed with diethyl ether and purified by prep. HPLC to afford the desired product: $^1$H-NMR (DMSO-$d_6$) δ 9.65 (s, 1H), 8.32 (dd, J=8.3, 1.0 Hz, 1H), 7.81 (ddd, J=8.5, 6.3, 2.3 Hz, 1H), 7.59 (t, J=1.9 Hz, 1H), 7.42 (dt, J=7.1, 2.0 Hz, 1H), 7.31 (ddt, J=8.8, 4.0, 2.4 Hz, 4H), 3.55 (s, 3H); LCMS(m/z) 354.1 [M+H]+.

Example 101. N-(3-iodophenyl)-N-methyl-[1,2,4]triazolo[4,3-a]quinazolin-5-amine

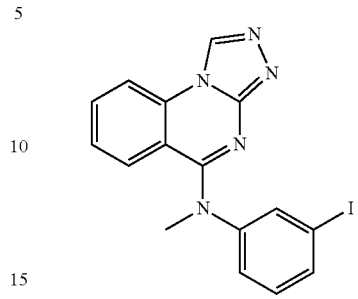

To a stirred solution of 3-iodo-N-methylaniline (0.228 g, 0.98 mmol) in THF (5 mL) was added LDA (0.36 mL, 0.73 mmol, 2.0 M in THF) at 0° C. and the mixture was stirred for 1 h at RT. 5-chloro-[1,2,4]triazolo[4,3-a]quinazoline (0.1 g, 0.49 mmol) at 0° C. was added, and the mixture was stirred for 1 h at RT. The progress of the reaction was monitored by TLC. After completion of the reaction, the reaction mixture was diluted with water and extracted with ethyl acetate. The organic layer was washed successively with water and brine, and dried over $Na_2SO_4$, filtered and evaporated under reduced pressure. The residue was purified by silica gel column chromatography, eluted with 4% methanol/dichloromethane, and followed by prep. HPLC to afford the desired product: $^1$H NMR (DMSO-$d_6$) δ 9.64 (s, 1H), 8.31 (d, J=8.4 Hz, 1H), 7.81 (ddd, J=8.5, 5.5, 3.1 Hz, 1H), 7.72 (t, J=1.9 Hz, 1H), 7.59 (dt, J=7.8, 1.2 Hz, 1H), 7.30 (dq, J=4.8, 1.6, 1.1 Hz, 3H), 7.14 (t, J=8.0 Hz, 1H), 3.53 (s, 3H); LCMS(m/z) 402.0 [M+H]+.

Example 102. N1-([1,2,4]triazolo[4,3-a]quinazolin-5-yl)-N1-methylbenzene-1,3-diamine

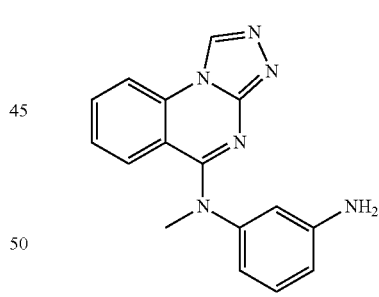

To a stirred solution of N-methyl-N-(3-nitrophenyl)-[1,2,4]triazolo[4,3-a]quinazolin-5-amine (Example 88) (0.350 g, 1.09 mmol) in EtOH/water (20 mL, 1:1) were added zinc (0.715 g, 10.94 mmol) and $NH_4Cl$ (0.585 g, 10.94 mmol) at RT and the mixture was stirred for 16 h at the same temperature. The progress of the reaction was monitored by TLC. After completion of the reaction, the reaction mixture was filtered through a bed of celite and washed with ethyl acetate. The organic layer was dried over $Na_2SO_4$, filtered and evaporated under reduced pressure. The residue was purified by silica-gel column chromatography and eluted with 5% methanol/dichloromethane to afford the desired product: $^1$H NMR (DMSO-$d_6$) δ 9.58 (s, 1H), 8.26 (dd, J=8.3, 1.2 Hz, 1H), 7.77 (ddd, J=8.4, 7.3, 1.3 Hz, 1H), 7.46

(dd, J=8.5, 1.3 Hz, 1H), 7.26 (ddd, J=8.4, 7.2, 1.2 Hz, 1H), 7.11-6.93 (m, 1H), 6.51-6.35 (m, 3H), 5.20 (s, 2H), 3.47 (s, 3H); LCMS(m/z) 291.2 [M+H]+.

Example 103. Methyl 3-(([1,2,4]triazolo[4,3-a]quinazolin-5-yl(methyl)amino)benzoate

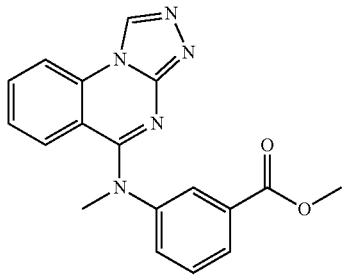 [SMILES: COC(=O)c1cccc(N(C)c2nc3nncn3c3ccccc23)c1]

(Step 1) Synthesis of methyl-3-((tert-butoxycarbonyl)amino)benzoate (2)

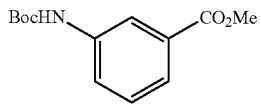

To a stirred solution of methyl-3-aminobenzoate (10 g, 66.14 mmol) in THF/water (60 mL, 5:1) were added sodium bicarbonate (11.11 g, 132.27 mmol) and di-tert-butyl dicarbonate (14.42 g, 66.14 mmol) at RT and the mixture was stirred at RT for 16 h. The progress of the reaction was monitored by TLC. After completion of the reaction, the reaction mixture was diluted with water and extracted with ethyl acetate. The organic layer was washed with brine, dried over Na₂SO₄, filtered and evaporated under reduced pressure. The crude compound was purified by silica gel column chromatography, eluted with 18% ethyl acetate/petroleum ether to give the desired product. LCMS(m/z) 252.11 [M+H]+.

(Step 2) Synthesis of Methyl 3-((tert-butoxycarbonyl)(methyl)amino)benzoate

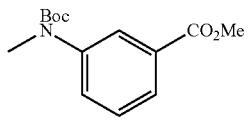 [SMILES: COC(=O)c1cccc(N(C)C(=O)OC(C)(C)C)c1]

To a stirred solution of methyl-3-((tert-butoxycarbonyl)amino)benzoate (12.3 g, 48.96 mmol) in DMF (120 mL) was added 60% sodium hydride (1.95 g, 48.96 mmol) and methyl iodide (3.65 mL, 58.76 mmol) at 0° C. and the mixture was stirred for 2 h at RT. The progress of the reaction was monitored by TLC. After completion of the reaction, the reaction mixture was diluted with ice-water and extracted with ethyl acetate. The organic layer was washed with brine, dried over Na₂SO₄, filtered and evaporated under reduced pressure to give the desired product. LCMS(m/z) 266.21 [M+H]+.

(Step 3) Synthesis of Methyl 3-(methylamino)benzoate

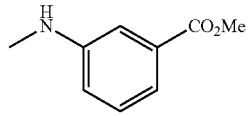

To a stirred solution of methyl 3-((tert-butoxycarbonyl)(methyl)amino)benzoate (2.0 g, 7.55 mmol) in dichloromethane (20 mL) was added 4N HCl in 1,4-dioxane (15 mL) at 0° C. and the mixture was stirred for 2 h at RT. The progress of the reaction was monitored by TLC. After completion of the reaction, the reaction mixture was poured into ice-water, neutralized with sat. NaHCO₃ solution and extracted with dichloromethane. The organic layer was washed successively with water and brine, dried over Na₂SO₄, filtered and evaporated under reduced pressure to give the desired product. LCMS(m/z) 166.46 [M+H]+.

(Step 4) Synthesis of Methyl 3-((2-chloroquinazolin-4-yl)(methyl)amino)benzoate

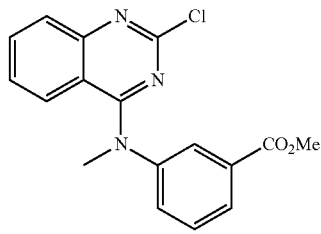 [SMILES: COC(=O)c1cccc(N(C)c2nc(Cl)nc3ccccc23)c1]

To a stirred solution of methyl 3-(methylamino)benzoate (crude, 0.249 g, 1.50 mmol) in DMF (6 mL) was added 60% sodium hydride (0.048 g, 1.21 mmol) at 0° C. and the mixture was stirred for 1 h at RT, followed by the addition of 2,4-dichloroquinazoline (0.2 g, 1.0 mmol) at 0° C., and the mixture was stirred for 5 h at RT. The progress of the reaction was monitored by TLC. After completion of the reaction, the reaction mixture was diluted with ice-water and extracted with ethyl acetate. The organic layer was washed with brine, dried over Na₂SO₄, filtered and evaporated under reduced pressure. The residue was purified by silica gel column chromatography, eluted with 10% ethyl acetate/petroleum ether to afford the desired product. LCMS(m/z) 328.18 [M+H]+.

(Step 5) Synthesis of Methyl 3-((2-hydrazinylquinazolin-4-yl)(methyl)amino)benzoate

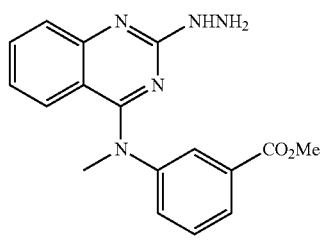 [SMILES: COC(=O)c1cccc(N(C)c2nc(NN)nc3ccccc23)c1]

To a stirred solution of methyl 3-((2-chloroquinazolin-4-yl)(methyl)amino)benzoate (0.04 g, 0.12 mmol) in ethanol (2 mL) was added hydrazine hydrate (0.006 mL, 0.12 mmol) at RT and the mixture was heated to 50° C. for 4 h. The progress of the reaction was monitored by TLC. After completion of the reaction, the reaction mixture was diluted with petroleum ether. The obtained solids were filtered and dried under vacuum to give the desired product. LC-MS: 324.19 (M+H).

(Step 6) Synthesis of Methyl 3-([1,2,4]triazolo[4,3-a]quinazolin-5-yl(methyl)amino)benzoate The mixture of methyl 3-((2-hydrazinylquinazolin-4-yl)(methyl)amino)benzoate (0.035 g, 0.11 mmol) and triethyl orthoformate (2 mL) was heated to 80° C. for 4 h. The progress of the reaction was monitored by TLC. After completion of the reaction, the reaction mixture was purified by prep. HPLC to afford the desired product: $^1$H NMR (DMSO-d$_6$) δ 9.65 (s, 1H), 8.31 (dd, J=8.2, 1.1 Hz, 1H), 7.94-7.66 (m, 3H), 7.70-7.40 (m, 2H), 7.38-7.13 (m, 2H), 3.83 (s, 3H), 3.57 (s, 3H); LCMS(m/z) 334.2 [M+H]+.

Example 104. N-(3-(((tert-butyldimethylsilyl)oxy)methyl)phenyl)-N-methyl-triazolo[4,3-a]quinazolin-5-amine

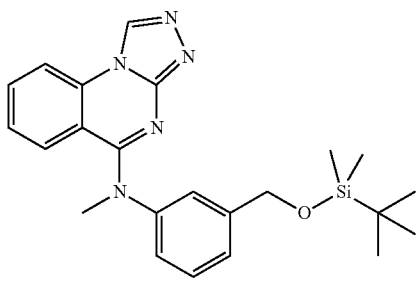 [SMILES: CN(c1cccc(CO[Si](C)(C)C(C)(C)C)c1)c1nc2nncn2c2ccccc12]

(Step 1) Synthesis of 3-(((tert-butyldimethylsilyl)oxy)methyl)aniline

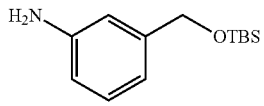 [SMILES: CC(C)(C)[Si](C)(C)OCc1cccc(N)c1]

To a solution of (3-aminophenyl)methanol (1.0 g, 8.12 mmol) in DMF (10 mL) were added imidazole (0.828 g, 12.18 mmol) at 0° C. and the mixture was stirred at RT for 10 min, followed by the addition of tert-butyldimethylsilyl chloride (1.34 g, 8.93 mmol) at 0° C., and the mixture was stirred for 16 h at RT. The reaction mixture was diluted with water and extracted with ethyl acetate. The organic layer was washed successively with water and brine, and dried over Na$_2$SO$_4$, filtered and evaporated under reduced pressure. The residue was purified by silica gel column chromatography and eluted with 15% ethyl acetate/petroleum ether to give the desired product. LCMS: 238.57 (M+H).

(Step 2) Synthesis of 3-(((tert-butyldimethylsilyl)oxy)methyl)-N-methylaniline

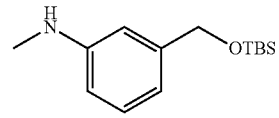 [SMILES: CNc1cccc(CO[Si](C)(C)C(C)(C)C)c1]

To a stirred solution of 3-(((tert-butyldimethylsilyl)oxy)methyl)aniline (0.5 g, 2.11 mmol) in MeOH (10 mL) were added 37% formaldehyde (0.28 mL, 3.16 mmol) and sodium methoxide (0.228 g, 4.22 mmol) at 0° C. and the mixture was heated to 50° C. for 4 h, followed by the addition of sodium borohydride (0.159 g, 4.22 mmol) at RT. The mixture was stirred at RT for 16 h. The progress of the reaction was monitored by TLC. After completion of the reaction, the reaction mixture was quenched with water and extracted with dichloromethane. The organic layer was washed successively with water and brine, dried over Na$_2$SO$_4$, filtered and evaporated under reduced pressure. The residue was purified by silica gel column chromatography, eluted with 30% ethyl acetate/petroleum ether to give the desired product. LC-MS: 252.72 (M+H).

(Step 3) Synthesis of N-(3-(((tert-butyldimethylsilyl)oxy)methyl)phenyl)-N-methyl-[1,2,4]triazolo[4,3-a]quinazolin-5-amine To a stirred solution of 3-(((tert-butyldimethylsilyl)oxy)methyl)-N-methylaniline (0.22 g, 0.88 mmol) in THF (6 mL) was added LDA (0.65 mL, 1.31 mmol, 2.0M in THF) at 0° C. and the mixture was stirred for 1 h at RT, followed by the addition of 5-chloro-[1,2,4]triazolo[4,3-a]quinazoline (0.214 g, 1.05 mmol) at 0° C., and the mixture was stirred for 1 h at RT. The reaction mixture was quenched with sat. NH$_4$Cl solution and extracted with ethyl acetate. The organic layer was washed successively with water and brine, dried over Na$_2$SO$_4$, filtered and evaporated under reduced pressure. The residue was purified by silica gel column chromatography and eluted with 30% ethyl acetate/petroleum ether to give the desired product: $^1$H NMR (500 MHz, DMSO-d$_6$) δ 9.66 (d, J=4.6 Hz, 1H), 8.35-8.23 (m, 1H), 7.79 (ddt, J=8.4, 7.2, 1.3 Hz, 1H), 7.36 (dt, J=24.6, 7.8 Hz, 1H), 7.30-7.11 (m, 5H), 4.55 (d, J=87.9 Hz, 2H), 3.54 (d, J=4.4 Hz, 3H), 3.35-3.25 (m, 9H), −0.05 (d, J=5.8 Hz, 6H); LCMS(m/z) 420.2 [M+H]+.

Example 105. N-(3-Cyclopropylphenyl)-N-methyl-[1,2,4]triazolo[4,3-a]quinazolin-5-amine

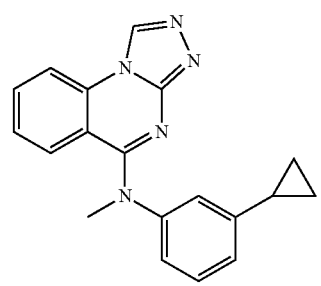 [SMILES: CN(c1cccc(C2CC2)c1)c1nc2nncn2c2ccccc12]

To a stirred solution of N-(3-iodophenyl)-N-methyl-[1,2,4]triazolo[4,3-a]quinazolin-5-amine (Example 101) (0.140 g, 0.35 mmol) in a mixture of toluene and water (7.5 mL, 4:1) were added cyclopropylboronic acid (0.060 g, 0.70 mmol) and potassium phosphate (0.222 g, 1.05 mmol) at RT and the mixture was deoxygenated with argon for 10 min, followed by the addition of tricyclohexylphosphine (0.019 g, 0.07 mmol) and palladium(II) acetate (0.004 g, 0.02 mmol) at RT, and the mixture was heated to 100° C. for 16 h. The progress of the reaction was monitored by TLC. After completion of the reaction, the reaction mixture was filtered through celite bed and washed with ethyl acetate. The organic layer was washed successively with water and brine, dried over Na$_2$SO$_4$, filtered and evaporated under reduced pressure. The residue was purified by prep. HPLC to afford the desired product: $^1$H NMR (DMSO-d$_6$) δ 9.60 (s, 1H), 8.27 (dd, J=8.2, 1.1 Hz, 1H), 7.76 (ddd, J=8.4, 6.8, 1.9 Hz, 1H), 7.32-7.15 (m, 3H), 7.08-6.84 (m, 3H), 3.52 (s, 3H), 1.96-1.74 (m, 1H), 1.00-0.79 (m, 2H), 0.71-0.54 (m, 2H); LCMS(m/z) 316.2 [M+H]+.

Example 106. N-([1,1'-biphenyl]-3-yl)-N-methyl-[1,2,4]triazolo[4,3-a]quinazolin-5-amine

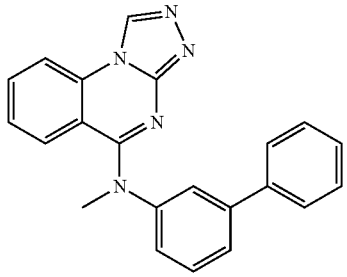 [SMILES: CN(c1cccc(-c2ccccc2)c1)c1nc2nncn2c2ccccc12]

The stirred mixture of N-(3-iodophenyl)-N-methyl-[1,2,4]triazolo[4,3-a]quinazolin-5-amine (Example 101) (0.02 g, 0.05 mmol), sodium carbonate (0.011 g, 0.11 mmol) and phenylboronic acid (0.008 g, 0.07 mmol) in 1,4-dioxane/water (4 mL, 1:1) was deoxygenated with argon for 10 min, followed by the addition of triphenylphosphine (0.0026 g, 0.009 mmol) and palladium(II) acetate (0.0005 g, 0.002 mmol) at RT, and the mixture was heated to 100° C. for 3 h. The progress of the reaction was monitored by TLC. After completion of the reaction, the reaction mixture was diluted with water and extracted with ethyl acetate. The organic layer was washed with brine, dried over Na$_2$SO$_4$, filtered and evaporated under reduced pressure. The residue was purified by silica gel column chromatography, eluted with 10% ethyl acetate/petroleum ether to afford the desired product: $^1$H NMR (DMSO-d$_6$) δ 9.62 (s, 1H), 8.29 (dd, J=8.4, 1.2 Hz, 1H), 7.76 (ddd, J=8.4, 7.2, 1.4 Hz, 1H), 7.67-7.59 (m, 3H), 7.57 (dt, J=7.8, 1.3 Hz, 1H), 7.51-7.13 (m, 7H), 3.62 (s, 3H); LCMS(m/z) 352.2 [M+H]+.

Example 107. N-methyl-N-(3-(pyrrolidin-1-yl)phenyl)-[1,2,4]triazolo[4,3-a]quinazolin-5-amine

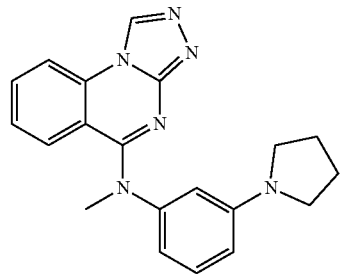 [SMILES: CN(c1cccc(N2CCCC2)c1)c1nc2nncn2c2ccccc12]

To a stirred solution of N-(3-iodophenyl)-N-methyl-[1,2,4]triazolo[4,3-a]quinazolin-5-amine (Example 101) (0.1 g, 0.25 mmol) in 1,4-dioxane (6 mL) were added pyrrolidine (0.03 mL, 0.37 mmol) and NatOBu (0.048 g, 0.49 mmol) at RT, and the mixture was deoxygenated with argon for 10 min. Chloro[2-(dicyclohexylphosphino)-3,6-dimethoxy-2',4',6'-triisopropyl-1,1'-biphenyl][2-(2-aminoethyl)phenyl]palladium(II) (BrettphosPd-G1, 0.04 g, 0.05 mmol) and 2-dicyclohexylphosphino-2',6'-diisopropoxybiphenyl (RuPhos, 0.035 g, 0.07 mmol) were added at RT and the mixture was heated to 100° C. for 4 h. The progress of the reaction was monitored by TLC. After completion of the reaction, the reaction mixture was filtered through a bed of celite and washed with ethyl acetate. The organic layer was evaporated under reduced pressure and the residue was purified by silica gel column chromatography and eluted with 4% methanol/dichloromethane, followed by prep. HPLC to afford the desired product: $^1$H NMR (DMSO-d$_6$) δ 9.57 (s, 1H), 8.45-8.12 (m, 1H), 7.75 (ddd, J=8.3, 7.2, 1.3 Hz, 1H), 7.44 (dd, J=8.4, 1.4 Hz, 1H), 7.23 (ddd, J=8.5, 7.1, 1.2 Hz, 1H), 7.12 (t, J=7.9 Hz, 1H), 6.59-6.10 (m, 3H), 3.53 (s, 3H), 3.21-3.00 (m, 4H), 2.11-1.78 (m, 4H); LCMS(m/z) 345.3 [M+H]+.

Example 108. N-methyl-N-(3-morpholinophenyl)-[1,2,4]triazolo[4,3-a]quinazolin-5-amine

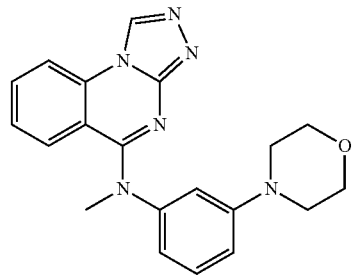

To a stirred solution of N-(3-iodophenyl)-N-methyl-[1,2,4]triazolo[4,3-a]quinazolin-5-amine (Example 101) (0.1 g, 0.25 mmol) in 1,4-dioxane (6 mL) were added morpholine (0.032 g, 0.37 mmol) and sodium tert-butoxide (0.048 g, 0.49 mmol) at RT and the mixture was deoxygenated with argon for 10 min, followed by the addition of Chloro[2-(dicyclohexylphosphino)-3,6-dimethoxy-2',4',6'-triisopropyl-1,1'-biphenyl][2-(2-aminoethyl)phenyl]palladium(II) (BrettphosPd-G1, 0.04 g, 0.05 mmol) and 2-dicyclohexylphosphino-2',6'-diisopropoxybiphenyl (RuPhos, 0.035 g, 0.07 mmol) at RT. The mixture was heated to 100° C. for 4 h. The progress of the reaction was monitored by TLC. After completion of the reaction, the reaction mixture was filtered through a bed of celite and washed with ethyl acetate. The organic layer was evaporated under reduced pressure and the residue was purified by silica gel column chromatography, eluted with 4% methanol/dichloromethane, followed by prep. HPLC to afford the desired product: $^1$H NMR (DMSO-d$_6$) δ 9.59 (s, 1H), 8.26 (dd, J=8.4, 1.3 Hz, 1H), 7.76 (ddd, J=8.5, 7.3, 1.4 Hz, 1H), 7.34 (dd, J=8.5, 1.3 Hz, 1H), 7.27-7.17 (m, 2H), 6.92-6.80 (m, 2H), 6.75-6.61 (m, 1H), 3.73-3.64 (m, 4H), 3.53 (s, 3H), 3.11-2.98 (m, 4H); LCMS (m/z) 361.2 [M+H]+.

Example 109. N-methyl-N-(3-(prop-1-yn-1-yl)phenyl)-[1,2,4]triazolo[4,3-a]quinazolin-5-amine

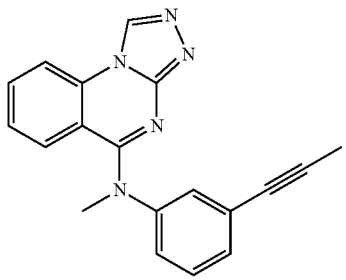

To a stirred solution of N-(3-iodophenyl)-N-methyl-[1,2,4]triazolo[4,3-a]quinazolin-5-amine (Example 101) (0.03 g, 0.07 mmol) in 1,4-dioxane (3 mL) was added triethylamine (0.01 mL, 0.07 mmol) at RT and the mixture was deoxygenated with argon for 10 min, followed by the addition of palladium(II) acetate (0.003 g, 0.01 mmol), triphenylphosphine (0.018 g, 0.07 mmol) and copper iodide (0.003 g, 0.014 mmol) at RT. The mixture was purged with prop-1-yne gas for 10 min, then treated in a microwave reactor at 120° C. for 1 h. The progress of the reaction was monitored by TLC. After completion of the reaction, the reaction mixture was filtered through a bed of celite and washed with ethyl acetate. The organic layer was evaporated under reduced pressure. The residue was purified by prep. HPLC to afford the desired product: $^1$H NMR (DMSO-d$_6$) δ 9.63 (s, 1H), 8.42-8.25 (m, 1H), 7.79 (ddd, J=8.5, 6.6, 2.0 Hz, 1H), 7.33-7.23 (m, 6H), 3.53 (s, 3H), 1.99 (s, 3H); LCMS(m/z) 314.2 [M+H]+.

Example 110. N-methyl-N-phenyl-8-vinyl-[1,2,4]triazolo[4,3-a]quinazolin-5-amine

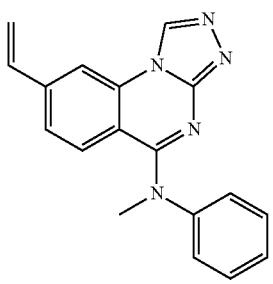 [SMILES: C=Cc1ccc2c(N(C)c3ccccc3)nc3nncn3c2c1]

To a solution of N-methyl-N-phenyl-8-vinyl-[1,2,4]triazolo[4,3-a]quinazolin-5-amine (Example 110) (20 mg, 0.066 mmol) in EtOH (0.33 mL) was added Pd/C (7 mg), and the mixture was stirred for 3 h at RT under H$_2$ atmo- A mixture of 8-bromo-N-methyl-N-phenyl-[1,2,4]triazolo[4,3-a]quinazolin-5-amine (Example 28) (50 mg, 0.141 mmol), K$_3$PO$_4$ (47.5 mg, 0.423 mmol), Pd(PPh$_3$)$_4$ (32.6 mg, 0.028 mmol) and 4,4,5,5-tetramethyl-2-vinyl-1,3,2-dioxaborolane (43.5 mg, 0.282 mmol) in BuOH (0.71 ml) was heated to 80° C. for 1 h. The reaction mixture was subjected to solid phase extraction (washed with MeOH, then eluted with NH$_3$ in MeOH) using Bond Elut SCX cartridge (Agilent), and the collected fractions were concentrated in vacuo. The residue was purified by column chromatography (Si-column, CHCl$_3$:MeOH=10:0-9:1) to afford the desired product: $^1$H NMR (Methanol-d4) δ 9.43 (s, 1H), 8.13 (d, J=1.6 Hz, 1H), 7.47-7.37 (m, 2H), 7.37-7.07 (m, 5H), 6.80 (dd, J=17.6, 10.9 Hz, 1H), 6.06 (d, J=17.5 Hz, 1H), 5.51 (d, J=10.9 Hz, 1H), 3.62 (s, 3H); LCMS(m/z) 302.2 [M+H]+.

Example 111. 8-Isopropyl-N-methyl-N-phenyl-[1,2,4]triazolo[4,3-a]quinazolin-5-amine

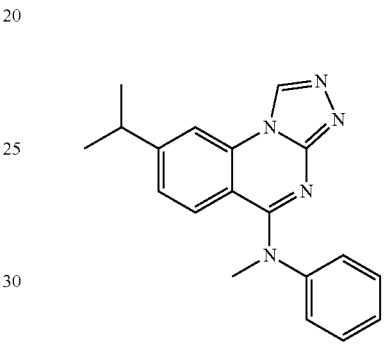

To a solution of N-methyl-N-phenyl-8-(prop-1-en-2-yl)-[1,2,4]triazolo[4,3-a]quinazolin-5-amine (Example 96) (20 mg, 0.063 mmol) in EtOH (0.32 mL) was added Pd/C (7 mg, 0.066 mmol), and the mixture was stirred for 3 h at RT under H$_2$ atmosphere. After removal of Pd/C by filtration, the filtrate was concentrated in vacuo. The residue was purified by column chromatography (Si-column, CHCl$_3$:MeOH=10:0-9:1) to the desired product: $^1$H NMR (CDCl$_3$) δ 8.94 (s, 1H), 7.58 (d, J=1.7 Hz, 1H), 7.42-7.32 (m, 2H), 7.33-7.12 (m, 4H), 6.97 (dd, J=8.9, 1.7 Hz, 1H), 3.66 (s, 3H), 3.01 (m, J=6.9 Hz, 1H), 1.28 (d, J=6.9 Hz, 6H); LCMS(m/z) 318.2 [M+H]+.

Example 112. 8-Ethyl-N-methyl-N-phenyl-[1,2,4]triazolo[4,3-a]quinazolin-5-amine

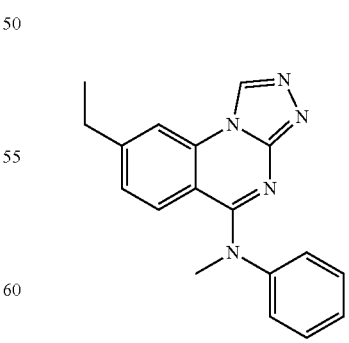

sphere. After removal of Pd/C by filtration, the filtrate was concentrated in vacuo. The residue was purified by column chromatography (Si-column, CHCl$_3$:MeOH=10:0-9:1) to afford the desired product: $^1$H NMR (Methanol-d$_4$) δ 9.42 (d, J=1.9 Hz, 1H), 8.02-7.95 (m, 1H), 7.45-7.36 (m, 2H), 7.35-7.11 (m, 4H), 7.00 (dq, J=8.6, 1.6 Hz, 1H), 3.66-3.54 (m, 3H), 2.82-2.71 (m, 2H), 1.26 (td, J=7.7, 0.8 Hz, 3H); LCMS(m/z) 304.2 [M+H]+.

Example 113. N-methyl-N-phenyl-8-(phenylethynyl)-[1,2,4]triazolo[4,3-a]quinazolin-5-amine

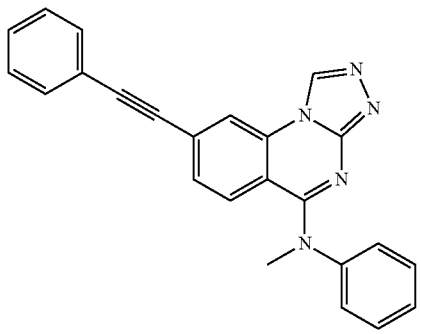

A mixture of 8-bromo-N-methyl-N-phenyl-[1,2,4]triazolo[4,3-a]quinazolin-5-amine (Example 28) (15 mg, 0.042 mmol), ethynylbenzene (6.49 mg, 0.064 mmol) and copper (I) iodide (8.07 mg, 0.042 mmol) in acetonitrile (0.21 mL) was heated at 80° C. for 1 h. The reaction mixture was subjected to solid phase extraction (washed with MeOH, then eluted with NH$_3$ in MeOH) using Bond Elut SCX cartridge (Agilent), and the collected fractions were concentrated in vacuo. The residue was purified by column chromatography (Si-column, CHC$_3$:MeOH=0-20%), and prep-HPLC (general condition) to afford the desired product: $^1$H NMR (CDCl$_3$) δ 8.94 (s, 1H), 7.91 (dd, J=1.6, 0.6 Hz, 1H), 7.58-7.49 (m, 2H), 7.45-7.33 (m, 5H), 7.33-7.13 (m, 5H), 3.68 (s, 3H); LCMS(m/z) 376.3 [M+H]+.

Example 114. 8-(2-Methoxyphenyl)-N-methyl-N-phenyl-[1,2,4]triazolo[4,3-a]quinazolin-5-amine

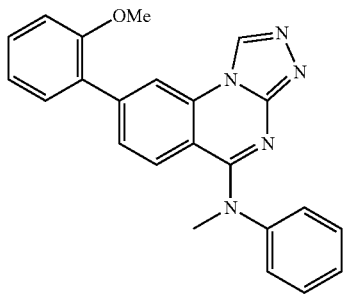 [SMILES: COc1ccccc1-c1ccc2c(N(C)c3ccccc3)nc3nncn3c2c1]

A mixture of 8-bromo-N-methyl-N-phenyl-[1,2,4]triazolo[4,3-a]quinazolin-5-amine (Example 28) (20 mg, 0.056 mmol), K$_3$PO$_4$ (36.0 mg, 0.169 mmol), Pd(OAc)$_2$ (2.54 mg, 0.011 mmol), tricyclohexylphosphine (3.17 mg, 0.011 mmol) and (2-methoxyphenyl)boronic acid (21.45 mg, 0.141 mmol) in dioxane/water (0.28 mL) was heated at 100° C. for 1 h. The reaction mixture was subjected to solid phase extraction (washed with MeOH, then eluted with NH$_3$ in MeOH) using Bond Elut SCX cartridge (Agilent), and the collected fractions were concentrated in vacuo. The residue was purified by column chromatography (Si-column, CHCl$_3$:MeOH=10:0-9:1) to afford the desired product: $^1$H NMR (CDCl$_3$) δ 8.97 (s, 1H), 8.01 (t, J=1.0 Hz, 1H), 7.44-7.36 (m, 3H), 7.34-7.20 (m, 6H), 7.09-6.99 (m, 2H), 3.82 (s, 3H), 3.70 (s, 3H); LCMS(m/z) 382.3 [M+H]+.

Example 115. 3-(5-(Methyl(phenyl)amino)-[1,2,4]triazolo[4,3-a]quinazolin-8-yl)prop-2-yn-1-ol

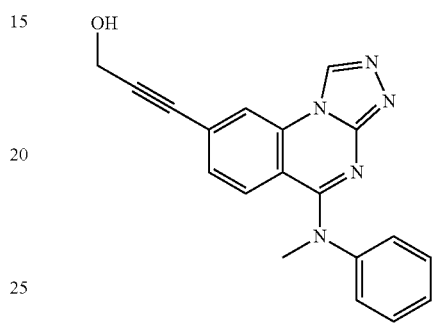

(Step 1)Synthesis of N-methyl-N-phenyl-8-((((tetrahydro-2H-pyran-2-yl)oxy)ethynyl)-[1,2,4]triazolo[4,3-a]quinazolin-5-amine

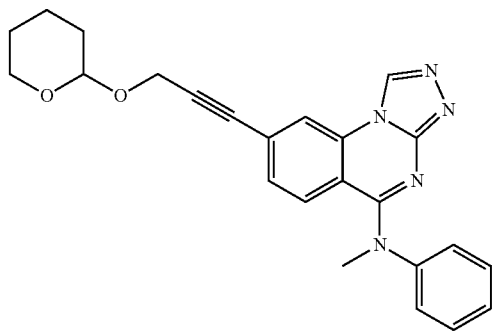 [SMILES: CN(c1ccccc1)c1nc2nncn2c2cc(C#CCOC3CCCCO3)ccc12]

A mixture of 8-bromo-N-methyl-N-phenyl-[1,2,4]triazolo[4,3-a]quinazolin-5-amine (Example 28) (15 mg, 0.042 mmol), PdCl$_2$(dppf) (6.20 mg, 8.47 μmol), triethylamine (17.14 mg, 0.169 mmol), 2-(prop-2-yn-1-yloxy)tetrahydro-2H-pyran (17.81 mg, 0.127 mmol) and copper(I) iodide (1.613 mg, 8.47 μmol) in DMF (0.21 mL) was treated in a microwave reactor for 2 h at 80° C. The reaction mixture was purified by column chromatography (Si-column, CHCl$_3$: MeOH=10:0-9:1) to give the desired product. LCMS(m/z) 414.28 [M+H]$^+$.

(Step 2) Synthesis of 3-(5-(methyl(phenyl)amino)-[1,2,4]triazolo[4,3-a]quinazolin-8-yl)prop-2-yn-1-ol A mixture of N-methyl-N-phenyl-8-((((tetrahydro-2H-pyran-2-yl)oxy)ethynyl)-[1,2,4]triazolo[4,3-a]quinazolin-5-amine (12 mg, 0.029 mmol) and 2N HCl aq. (1 mL) was stirred for 1 h at RT. The reaction mixture was neutralized with 2N NaOH aq. and the mixture was concentrated in vacuo. The residue was purified by column chromatography (Si-column, CHCl₃:MeOH=10:0-8:2) to afford the desired product: ¹H NMR (CDCl₃) δ 10.13 (s, 1H), 8.79 (s, 1H), 7.51 (td, J=10.8, 9.5, 4.3 Hz, 3H), 7.34 (d, J=7.2 Hz, 2H), 7.12 (d, J=8.7 Hz, 1H), 6.94 (d, J=8.7 Hz, 1H), 4.47 (s, 2H), 3.79 (s, 3H); LCMS(m/z) 330.2 [M+H]+.

Example 116. 8-(3-Fluorophenyl)-N-methyl-N-phenyl-[1,2,4]triazolo[4,3-a]quinazolin-5-amine

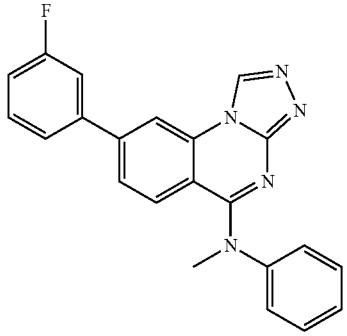 [SMILES: CN(c1ccccc1)c1nc2nncn2c2cc(-c3cccc(F)c3)ccc12]

A mixture of 8-bromo-N-methyl-N-phenyl-[1,2,4]triazolo[4,3-a]quinazolin-5-amine (Example 28) (20 mg, 0.056 mmol), K₃PO₄ (23.97 mg, 0.113 mmol), Pd(OAc)₂ (2.54 mg, 0.011 mmol), tricyclohexylphosphine (3.17 mg, 0.011 mmol) and (4-fluorophenyl)boronic acid (19.75 mg, 0.141 mmol) in dioxane/water (0.28 m 1) was heated at 100° C. for 1 h. The reaction mixture was subjected to solid phase extraction (washed with MeOH, then eluted with NH₃ in MeOH) using Bond Elut SCX cartridge (Agilent), and the collected fractions were concentrated in vacuo. The residue was purified by column chromatography (Si-column, CHC₃:MeOH=10:0-9:1) to afford the desired product: ¹H NMR (CDCl₃) δ 9.06 (s, 1H), 7.95 (d, J=1.7 Hz, 1H), 7.48-7.27 (m, 8H), 7.23-7.17 (m, 2H), 7.13 (tdd, J=8.3, 2.6, 1.1 Hz, 1H), 3.69 (s, 3H); LCMS(m/z) 370.3 [M+H]+.

Example 117. 5-(Methyl(phenyl)amino)-[1,2,4]triazolo[4,3-a]quinazoline-8-carbaldehyde

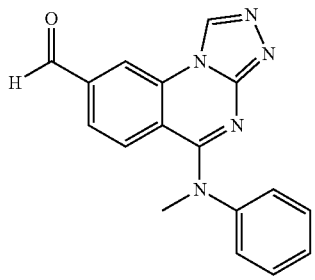 [SMILES: CN(c1ccccc1)c1nc2nncn2c2cc(C=O)ccc12]

To a solution of N-methyl-N-phenyl-8-vinyl-[1,2,4]triazolo[4,3-a]quinazolin-5-amine (Example 110) (50 mg, 0.166 mmol) in acetone/water (1:1, 0.83 mL) were added osmium(VIII) oxide (8.44 mg, 0.033 mmol) and sodium periodate (42.6 mg, 0.199 mmol), and the mixture was stirred overnight at RT. The reaction mixture was subjected to solid phase extraction (washed with MeOH, then eluted with NH₃ in MeOH) using Bond Elut SCX cartridge (Agilent), and the collected fractions were concentrated in vacuo. The residue was purified with prep-HPLC to afford the desired product: ¹H NMR (Methanol-d₄) δ 9.49 (s, 1H), 7.44 (td, J=6.9, 6.5, 1.6 Hz, 2H), 7.37-7.26 (m, 6H), 5.61 (s, 1H), 3.68 (s, 3H); LCMS(m/z) 304.2 [M+H]+.

Example 118. 5-(Methyl(phenyl)amino)-[1,2,4]triazolo[4,3-a]quinazoline-8-carboxylic Acid

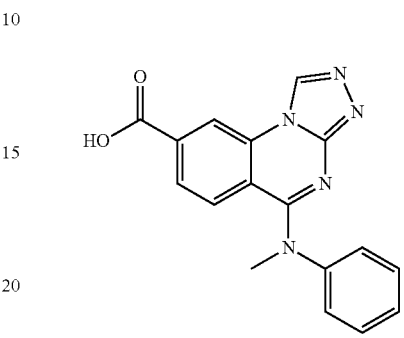

A mixture of 5-(methyl(phenyl)amino)-[1,2,4]triazolo[4,3-a]quinazoline-8-carbonitrile (Example 94) (50 mg, 0.166 mmol) and sulfuric acid (2 mL, 0.166 mmol) was heated to 80° C. for 5 h. The reaction mixture was cooled to 0° C., and neutralized with 4N NaOH aq. The mixture was concentrated in vacuo. DMSO was added to the mixture, and the resulting solids were filtered off. The filtrate was purified by prep-HPLC to afford the desired product: ¹H NMR (Methanol-d4) δ 9.52 (s, 1H), 8.65 (s, 1H), 7.68 (d, J=8.6 Hz, 1H), 7.50-7.27 (m, 6H), 3.69 (s, 3H); LCMS(m/z) 320.2 [M+H]+.

Example 119. N-([1,1'-Biphenyl]-3-yl)-N-methyl-8-nitro-[1,2,4]triazolo[4,3-a]quinazolin-5-amine

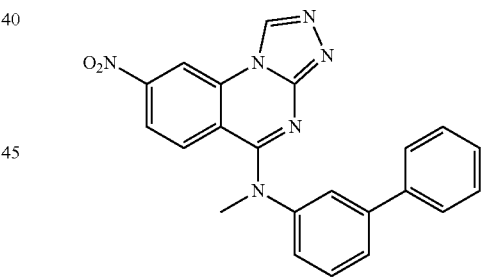

(Step 1) Synthesis of N-(biphenyl-3-yl)-2-chloro-N-methyl-7-nitroquinazolin-4-amine

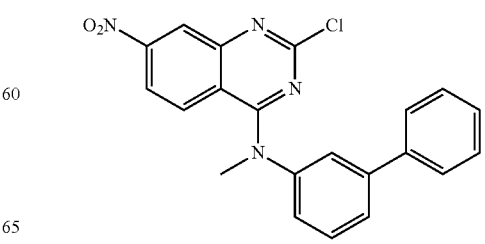

To a solution of N-methylbiphenyl-4-amine (22.9 mg, 0.125 mmol) in DMF (0.62 mL) were added 2,4-dichloro-7-nitroquinazoline (30.5 mg, 0.125 mmol) and sodium hydride (3 mg, 0.125 mmol), and the mixture was stirred for 1 h at RT. The reaction mixture was diluted with AcOEt, and washed successively with water and brine, and dried with Na₂SO₄. The organic layer was concentrated in vacuo. The residue was used for the next step without further purification. LCMS(m/z) 391.18 [M+H]⁺.

(Step 2) Synthesis of N-(biphenyl-3-yl)-2-hydrazinyl-N-methyl-7-nitroquinazolin-4-amine

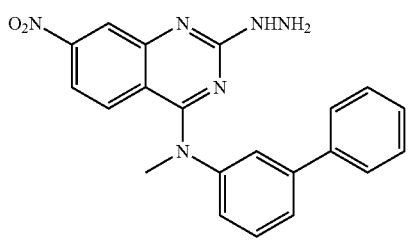 [SMILES: CN(c1cccc(-c2ccccc2)c1)c1nc(NN)nc2cc([N+](=O)[O-])ccc12]

A mixture of N-(biphenyl-3-yl)-2-chloro-N-methyl-7-nitroquinazolin-4-amine (crude, 61 mg, 0.156 mmol) and hydrazine hydrate (15.63 mg, 0.312 mmol) in EtOH (0.78 mL) was stirred at RT to 50° C. to for 2 h. The reaction mixture was diluted with AcOEt, and washed successively with water and brine. The organic layer was concentrated in vacuo. The residue was used for the next step without further purification. LCMS(m/z) 387.23 [M+H]⁺.

(Step 3) Synthesis of N-([1,1'-biphenyl]-3-yl)-N-methyl-8-nitro-[1,2,4]triazolo[4,3-a]quinazolin-5-amine A mixture of N-(biphenyl-3-yl)-2-hydrazinyl-N-methyl-7-nitroquinazolin-4-amine (crude, 62 mg, 0.160 mmol) and triethoxymethane (71.3 mg, 0.481 mmol) was heated at 95° C. for 1 h. The reaction mixture was concentrated in vacuo, and the residue was purified by column chromatography (Si-column, CHC₃:MeOH=10:0-9:1) to afford the desired product: ¹H NMR (CDCl₃) δ 9.08 (s, 1H), 8.66 (d, J=2.2 Hz, 1H), 7.93 (dd, J=9.1, 2.2 Hz, 1H), 7.66-7.33 (m, 9H), 7.17 (ddd, J=7.8, 2.2, 1.1 Hz, 1H), 3.76 (s, 3H); LCMS(m/z) 397.3 [M+H]+.

Example 120. N-(4'-Fluoro-[1,1'-biphenyl]-3-yl)-N-methyl-[1,2,4]triazolo[4,3-a]quinazolin-5-amine

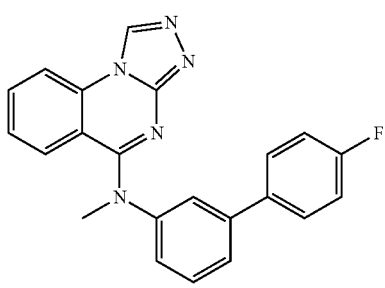 [SMILES: CN(c1cccc(-c2ccc(F)cc2)c1)c1nc2nncn2c2ccccc12]

A mixture of N-(3-iodophenyl)-N-methyl-[1,2,4]triazolo[4,3-a]quinazolin-5-amine (Example 101) (15 mg, 0.037 mmol), (4-fluorophenyl)boronic acid (13.08 mg, 0.093 mmol), K₃PO₄ (23.81 mg, 0.112 mmol), Pd(OAc)₂ (1.679 mg, 7.48 μmol) and tricyclohexylphosphine (2.097 mg, 7.48 μmol) in dioxane/water (0.2 mL) was heated at 100° C. for 1 h. The reaction mixture was subjected to solid phase extraction (washed with MeOH, then eluted with NH₃ in MeOH) using Bond Elut SCX cartridge (Agilent), and the collected fractions were concentrated in vacuo. The residue was purified by column chromatography (Si-column, CHCl₃:MeOH=10:0-9:1) to afford the desired product: ¹H NMR (CDCl₃) δ 8.99 (s, 1H), 7.89-7.80 (m, 1H), 7.67 (ddd, J=8.4, 7.2, 1.3 Hz, 1H), 7.46-7.40 (m, 5H), 7.32 (dq, J=1.5, 0.9 Hz, 1H), 7.17-7.08 (m, 4H), 3.73 (s, 3H); LCMS(m/z) 370.3 [M+H]+.

Example 121. N-(3-(Furan-2-yl)phenyl)-N-methyl-[1,2,4]triazolo[4,3-a]quinazolin-5-amine

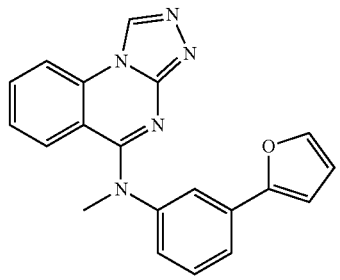 [SMILES: CN(c1cccc(-c2ccco2)c1)c1nc2nncn2c2ccccc12]

A mixture of N-(3-iodophenyl)-N-methyl-[1,2,4]triazolo[4,3-a]quinazolin-5-amine (Example 101) (15 mg, 0.037 mmol), K₃PO₄ (15.87 mg, 0.075 mmol), Pd(OAc)₂ (1.679 mg, 0.0075 mmol), tricyclohexylphosphine (2.10 mg, 0.0075 mmol), and furan-2-ylboronic acid (6.27 mg, 0.056 mmol) in dioxane/water (0.2 mL) was heated at 100° C. for 1 h. The reaction mixture was subjected to solid phase extraction (washed with MeOH, then eluted with NH₃ in MeOH) using Bond Elut SCX cartridge (Agilent), and the collected fractions were concentrated in vacuo. The residue was purified by column chromatography (Si-column, CHCl₃:MeOH=10:0-9:1) to afford the desired product: ¹H NMR (CDCl₃) δ 8.96 (s, 1H), 7.89-7.76 (m, 1H), 7.65 (ddd, J=8.4, 7.3, 1.3 Hz, 1H), 7.60-7.41 (m, 4H), 7.36 (t, J=7.9 Hz, 1H), 7.13 (ddd, J=8.5, 7.3, 1.2 Hz, 1H), 7.01 (ddd, J=7.9, 2.2, 1.0 Hz, 1H), 6.66 (dd, J=3.4, 0.8 Hz, 1H), 6.47 (dd, J=3.4, 1.8 Hz, 1H), 3.70 (s, 3H); LCMS(m/z) 342.2 [M+H]+.

Example 122. 3-([1,2,4]Triazolo[4,3-a]quinazolin-5-yl(methyl)amino)benzaldehyde

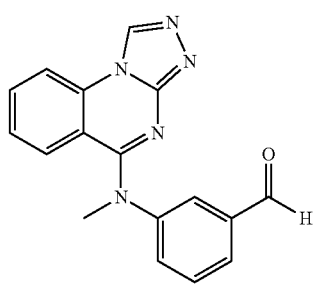 [SMILES: CN(c1cccc(C=O)c1)c1nc2nncn2c2ccccc12]

To a stirred solution of (3-([1,2,4]triazolo[4,3-a]quinazolin-5-yl(methyl)amino)phenyl)methanol (Example 83) (0.06 g, 0.19 mmol) in dichloromethane (6 mL) was added manganese(IV) oxide (0.173 g, 1.97 mmol) at RT and the mixture was stirred at RT for 24 h. The progress of the reaction was monitored by TLC. After completion of the reaction, the reaction mixture was filtered through a bed of celite. The filtrate was evaporated under reduced pressure, and the residue was purified by silica gel column chromatography, eluted with 4% methanol/dichloromethane to afford the desired product: $^1$H NMR (DMSO-$d_6$) δ 9.95 (s, 1H), 9.68 (s, 1H), 8.41-8.17 (m, 1H), 7.91-7.71 (m, 3H), 7.69-7.54 (m, 2H), 7.38-7.21 (m, 2H), 3.60 (s, 3H); LCMS (m/z) 304.1 [M+H]+.

Example 123. 7-Ethyl-N-methyl-N-phenyl-[1,2,4]triazolo[4,3-a]quinazolin-5-amine

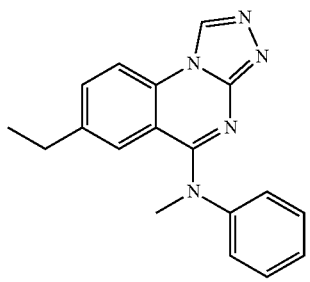 [SMILES: CCc1ccc2c(c1)c(N(C)c1ccccc1)nc1nncn12]

(Step 1) Synthesis of 6-bromoquinazoline-2,4(1H,3H)-dione

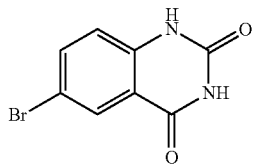

A stirred mixture of 2-amino-5-bromobenzoic acid (2.0 g, 9.26 mmol) and urea (5.5 g, 92.59 mmol) was heated to 150° C. for 16 h. After cooling to RT, the reaction mixture was diluted with ice-water and stirred for 5 min. The resulting solids were filtered and dried under vacuum to give crude product. The crude compound was triturated with glacial acetic acid to give the desired product. LCMS(m/z) 241.07 [M+H]+.

(Step 2) Synthesis of 6-bromo-2,4-dichloroquinazoline

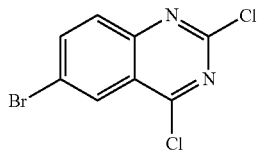 [SMILES: Clc1nc(Cl)c2cc(Br)ccc2n1]

To a solution of 6-bromoquinazoline-2,4(1H,3H)-dione (1.7 g, 7.08 mmol) in phosphorus oxychloride (6.62 mL, 70.83 mmol) was added N, N-diisopropylethylamine (1.85 mL, 10.62 mmol) at 0° C. and the mixture was stirred at 120° C. for 3 h. The reaction mixture was diluted with ice-water, and the resulting solids were collected. The solids were dissolved in dichloromethane, and washed with water and brine, dried over $Na_2SO_4$, filtered and evaporated under reduced pressure to give the desired product. LCMS(m/z) 277.15 [M+H]+.

(Step 3) Synthesis of 6-bromo-2-chloro-N-methyl-N-phenylquinazolin-4-amine

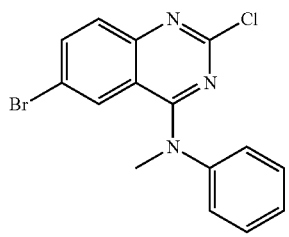

To a solution of N-methylaniline (0.2 mL, 1.81 mmol) in DMF (10 mL) was added sodium hydroxide (0.072 g, 1.81 mmol) at 0° C. and the mixture was stirred for 1 h at RT, followed by the addition of 6-bromo-2,4-dichloroquinazoline (0.5 g, 1.81 mmol) at 0° C. The mixture was then stirred at RT for 2 h. The reaction mixture was diluted with water and extracted with ethyl acetate. The organic layer was washed successively with water and brine, dried over $Na_2SO_4$, filtered and evaporated under reduced pressure. The residue was purified by silica gel column chromatography, eluted with 15% ethyl acetate/petroleum ether to give the desired product. LCMS(m/z) 348.27 [M+H]+.

(Step 4) Synthesis of 6-bromo-2-hydrazinyl-N-methyl-N-phenylquinazolin-4-amine

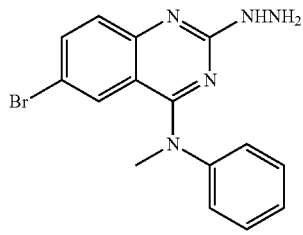

To a solution of 6-bromo-2-chloro-N-methyl-N-phenylquinazolin-4-amine (1 g, 2.87 mmol) in EtOH (15 mL) was added hydrazine hydrate (0.28 mL, 5.74 mmol) at RT and the mixture was stirred at 50° C. for 16 h. The reaction mixture was diluted with water and extracted with ethyl acetate. The organic layer was washed successively with water and brine, dried over $Na_2SO_4$, filtered and evaporated under reduced pressure to give the desired product. LCMS (m/z) 346.10 [M+H]+.

(Step 5) Synthesis of 7-bromo-N-methyl-N-phenyl-[1,2,4]triazolo[4,3-a]quinazolin-5-amine

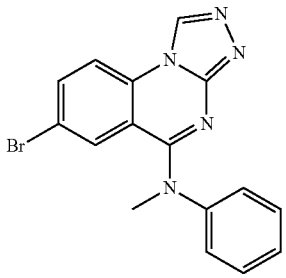 [SMILES: CN(c1ccccc1)c1nc2nncn2c2ccc(Br)cc12]

A mixture of 6-bromo-2-hydrazinyl-N-methyl-N-phenylquinazolin-4-amine (0.9 g, 2.62 mmol) and triethyl orthoformate (1.3 mL, 7.87 mmol) was heated to 100° C. for 16 h. The reaction mixture was diluted with diethyl ether and stirred for few minutes. The resulting solids were filtered and dried under vacuum to give crude product. The crude compound was washed with diethyl ether to give the desired product. LCMS(m/z) 354.13 [M+H]+.

(Step 6) Synthesis of 7-ethyl-N-methyl-N-phenyl-[1,2,4]triazolo[4,3-a]quinazolin-5-amine To a solution of 7-bromo-N-methyl-N-phenyl-[1,2,4]triazolo[4,3-a]quinazolin-5-amine (0.05 g, 0.14 mmol) in 1,4-dioxane/water (5 mL, 4:1) was added ethylboronic acid (0.026 g, 0.35 mmol) and potassium phosphate (0.090 g, 0.42 mmol) at RT and the mixture was deoxygenated with argon for 10 mins, followed by the addition of tricyclohexylphosphine (0.04 g, 0.14 mmol) and Pd(OAc)$_2$ (0.006 g, 0.03 mmol) at RT, and the mixture was treated in a microwave reactor at 110° C. for 2 h. The reaction mixture was diluted with water and extracted with ethyl acetate. The organic layer was washed with water and brine, dried over Na$_2$SO$_4$, filtered and evaporated under reduced pressure to give crude product. The crude compound was purified by prep. HPLC to afford the desired product: $^1$H NMR (DMSO-d$_6$) δ 9.57 (s, 1H), 8.19 (d, J=8.4 Hz, 1H), 7.62 (dd, J=8.5, 1.9 Hz, 1H), 7.41 (dd, J=8.4, 7.2 Hz, 2H), 7.36-7.22 (m, 3H), 7.05 (d, J=1.8 Hz, 1H), 3.55 (s, 3H), 2.38 (q, J=7.6 Hz, 2H), 0.79 (t, J=7.6 Hz, 3H); LCMS(m/z) 304.3 [M+H]+.

Example 124. N-Methyl-7-nitro-N-phenyl-[1,2,4]triazolo[4,3-a]quinazolin-5-amine

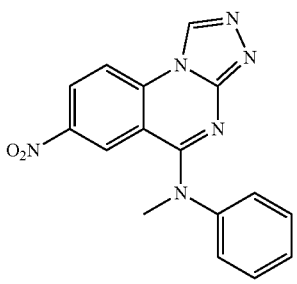 [SMILES: CN(c1ccccc1)c1nc2nncn2c2ccc([N+](=O)[O-])cc12]

(Step 1) Synthesis of 6-Nitroquinazoline-2,4(1H,3H)-dione

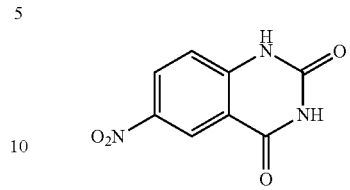

A mixture of 2-amino-5-nitrobenzoic acid (4.0 g, 21.98 mmol) and urea (13.18 g, 219.78 mmol) was heated to 150° C. for 16 h. After cooling to RT, the reaction mixture was diluted with ice-water, and stirred for 5 min. The resulting solids were filtered and dried under vacuum to give crude product. The crude compound was triturated with glacial acetic acid to afford the desired product. LCMS(m/z) 208.06 [M+H]+.

(Step 2) Synthesis of 2,4-Dichloro-6-nitroquinazoline

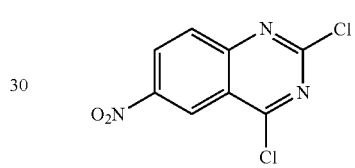

To a solution of 6-nitroquinazoline-2,4(1H,3H)-dione (1.5 g, 7.24 mmol) in phosphorus oxychloride (6.94 mL, 72.46 mmol) was added N,N-diisopropylethylamine (1.89 mL, 10.87 mmol) at 0° C. and the mixture was stirred at 120° C. for 16 h. The reaction mixture was diluted with ice-water and extracted with ethyl acetate. The organic layer was washed successively with water and brine, dried over Na$_2$SO$_4$, filtered and evaporated under reduced pressure. The residue was purified by silica gel column chromatography and eluted with 10% ethyl acetate/petroleum ether to give the desired product.

(Step 3) Synthesis of 2-chloro-N-methyl-6-nitro-N-phenylquinazolin-4-amine

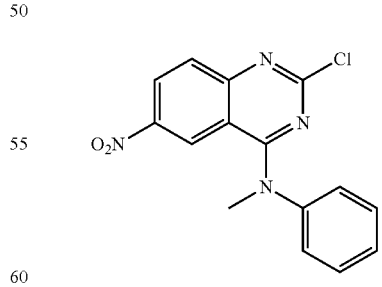

To a solution of N-methylaniline (0.132 g, 1.23 mmol) in DMF (8 mL) was added sodium hydroxide (0.050 g, 1.23 mmol) at 0° C. and the mixture was stirred for 1 h at RT, followed by the addition of 2,4-dichloro-6-nitroquinazoline (0.3 g, 1.23 mmol) at 0° C. The mixture was then stirred for 16 h at RT. The reaction mixture was diluted with water and extracted with ethyl acetate. The organic layer was washed with ice-water, brine, dried over Na$_2$SO$_4$, filtered and evaporated under reduced pressure. The residue was purified by silica gel column chromatography, eluted with 20% ethyl acetate/petroleum ether to give the desired product. LCMS (m/z) 315.15 [M+H]+.

(Step 4) Synthesis of 2-Hydrazinyl-N-methyl-6-nitro-N-phenylquinazolin-4-amine

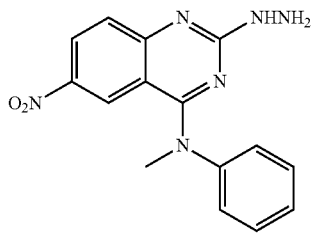 [SMILES: CN(c1ccccc1)c1nc(NN)nc2ccc([N+](=O)[O-])cc12]

To a solution of 2-chloro-N-methyl-6-nitro-N-phenylquinazolin-4-amine 4 (0.38 g, 1.21 mmol) in EtOH (10 mL) was added hydrazine hydrate (0.12 mL, 2.42 mmol) at RT and the mixture was stirred at 50° C. for 16 h. The reaction mixture was evaporated under reduced pressure to give the desired product. LCMS(m/z) 311.01 [M+H]$^+$.

(Step 5) Synthesis of N-methyl-7-nitro-N-phenyl-[1,2,4]triazolo[4,3-a]quinazolin-5-amine A mixture of 2-hydrazinyl-N-methyl-6-nitro-N-phenylquinazolin-4-amine (0.3 g, 0.97 mmol) and triethyl orthoformate (1 mL, 5.80 mmol) was stirred at 100° C. for 16 h. The reaction mixture was diluted with diethyl ether and stirred for few minutes. The resulting solids were filtered and dried under vacuum to give crude product. The crude compound was washed with diethyl ether to afford the desired product: $^1$H NMR (DMSO-d$_6$) δ 9.71 (s, 1H), 8.58 (dd, J=9.1, 2.4 Hz, 1H), 8.50 (d, J=9.1 Hz, 1H), 8.02 (d, J=2.4 Hz, 1H), 7.53-7.39 (m, 4H), 7.38-7.29 (m, 1H), 3.59 (s, 3H); LCMS(m/z) 321.1 [M+H]+.

Example 125. 5-(Methyl(phenyl)amino)-[1,2,4]triazolo[4,3-a]quinazoline-7-carboxamide

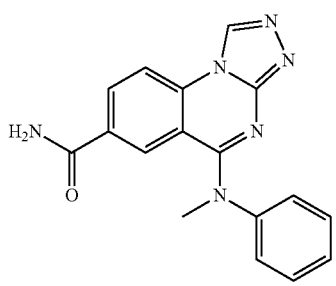

(Step 1) Synthesis of 5-(methyl(phenyl)amino)-[1,2,4]triazolo[4,3-a]quinazoline-7-carbonitrile

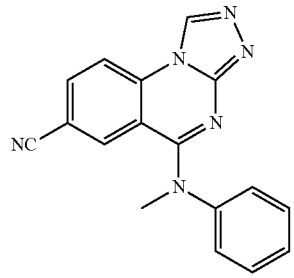 [SMILES: CN(c1ccccc1)c1nc2nncn2c2ccc(C#N)cc12]

To a solution of 7-bromo-N-methyl-N-phenyl-[1,2,4]triazolo[4,3-a]quinazolin-5-amine (0.1 g, 0.28 mmol) in DMF (4 mL) were added zinc cyanide (0.166 g, 1.42 mmol) and zinc dust (0.055 g, 0.84 mmol) at RT and the mixture was deoxygenated with argon for 10 mins, followed by the addition of tetrakis(triphenylphosphine)palladium(0) (0.065 g, 0.06 mmol) at RT. The mixture was then treated in a microwave reactor at 110° C. for 2 h. The reaction mixture was filtered through a bed of celite and washed with ethyl acetate. The filtrate was washed successively with water and brine, dried over Na$_2$SO$_4$, filtered and evaporated under reduced pressure. The residue was purified by silica gel column chromatography, eluted with 4% methanol/dichloromethane to give the desired product. LCMS(m/z) 301.31 [M+H]$^+$.

(Step 2) Synthesis of 5-(methyl(phenyl)amino)-[1,2,4]triazolo[4,3-a]quinazoline-7-carboxamide To a solution of 5-(methyl(phenyl)amino)-[1,2,4]triazolo[4,3-a]quinazoline-7-carbonitrile (0.1 g, 0.33 mmol) in MeOH (5 mL) were added nickel(ii) chloride hexahydrate (0.031 g, 0.13 mmol) and sodium borohydride (0.177 g, 4.66 mmol) at 0° C. and the mixture was stirred for 48 h at RT. The reaction mixture was quenched with saturated NH$_4$Cl solution and extracted with 10% methanol/dichloromethane. The organic layer was washed successively with water and brine, dried over Na$_2$SO$_4$, filtered and evaporated under reduced pressure. The residue was purified by silica gel column chromatography, eluted with 4% methanol/dichloromethane, followed by prep. HPLC to afford the desired product: $^1$H NMR (DMSO-d$_6$) δ 9.63 (s, 1H), 8.34 (d, J=8.6 Hz, 1H), 8.18 (dd, J=8.6, 1.8 Hz, 1H), 7.87 (d, J=1.9 Hz, 2H), 7.41-7.27 (m, 5H), 7.27-7.18 (m, 1H), 3.55 (s, 3H); LCMS(m/z) 319.3 [M+H]+.

Example 126. N5-([1,1'-Biphenyl]-3-yl)-N5-methyl-[1,2,4]triazolo[4,3-a]quinazoline-5,8-diamine

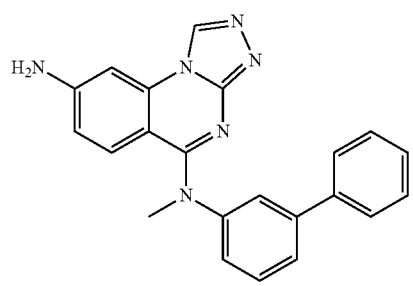

To a solution of N-([1,1'-biphenyl]-3-yl)-N-methyl-8-nitro-[1,2,4]triazolo[4,3-a]quinazolin-5-amine (Example 119) (23 mg, 0.058 mmol) in EtOH (0.29 ml) was added Pd/C (6.17 mg), and the mixture was stirred overnight at 70° C. under H$_2$ atmosphere. After removal of Pd/C by filtration, the filtrate was concentrated in vacuo. The residue was purified by prep-HPLC to afford the desired product: $^1$H NMR (Methanol-d$_4$) δ 9.19 (s, 1H), 7.57-7.47 (m, 5H), 7.43 (ddd, J=7.7, 6.9, 1.3 Hz, 2H), 7.39-7.31 (m, 1H), 7.22 (ddd, J=7.8, 2.3, 1.2 Hz, 1H), 7.16-7.05 (m, 2H), 6.44 (dd, J=9.2, 2.2 Hz, 1H), 3.68 (s, 3H); LCMS(m/z) 367.3 [M+H]+.

Example 127. N-Methyl-N-(3-(pyridin-4-yl)phenyl)-[1,2,4]triazolo[4,3-a]quinazolin-5-amine

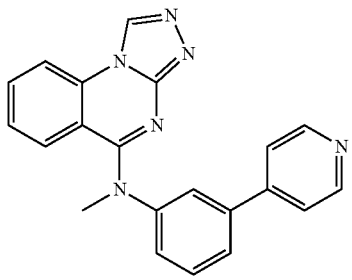 [SMILES: CN(c1cccc(-c2ccncc2)c1)c1nc2nncn2c2ccccc12]

A mixture of N-(3-iodophenyl)-N-methyl-[1,2,4]triazolo[4,3-a]quinazolin-5-amine (Example 101) (15 mg, 0.037 mmol), pyridin-4-ylboronic acid (4.60 mg, 0.037 mmol), K$_3$PO$_4$ (7.94 mg, 0.037 mmol), Pd(OAc)$_2$ (8.39 mg, 0.037 mmol) and tricyclohexylphosphine (10.48 mg, 0.037 mmol) in dioxane/water (0.2 mL) was heated at 100° C. for 1 h. The reaction mixture was subjected to solid phase extraction (washed with MeOH, then eluted with NH$_3$ in MeOH) using Bond Elut SCX cartridge (Agilent), and the collected fractions were concentrated in vacuo. The residue was purified by column chromatography (Si-column, CHC$_3$:MeOH=10:0-9:1) to afford the desired product: $^1$H NMR (CDCl$_3$) δ 8.99 (s, 1H), 8.80-8.73 (m, 1H), 8.68-8.58 (m, 2H), 7.91-7.81 (m, 1H), 7.68 (ddd, J=8.4, 7.3, 1.3 Hz, 1H), 7.57-7.52 (m, 2H), 7.46-7.34 (m, 3H), 7.26 (d, J=7.7 Hz, 1H), 7.16 (ddd, J=8.5, 7.3, 1.2 Hz, 1H), 3.74 (s, 3H); LCMS(m/z) 353.3 [M+H]+.

Example 128. N-([1,1'-Biphenyl]-3-yl)-8-bromo-N-methyl-[1,2,4]triazolo[4,3-a]quinazolin-5-amine

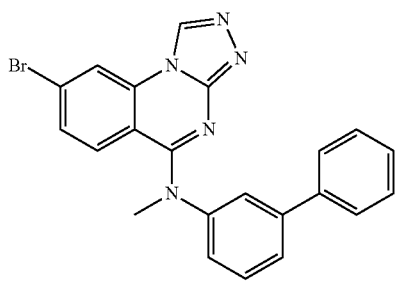 [SMILES: CN(c1cccc(-c2ccccc2)c1)c1nc2nncn2c2cc(Br)ccc12]

(Step 1) Synthesis of N-(biphenyl-3-yl)-7-bromo-2-chloro-N-methylquinazolin-4-amine

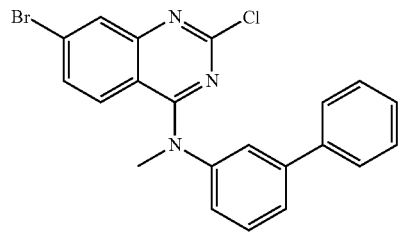 [SMILES: CN(c1cccc(-c2ccccc2)c1)c1nc(Cl)nc2cc(Br)ccc12]

To a solution of 7-bromo-2,4-dichloroquinazoline (291 mg, 1.049 mmol) in DMF (5 mL) were added N-methylbiphenyl-4-amine (183 mg, 0.999 mmol) and sodium hydride (23.96 mg, 0.999 mmol). The mixture was stirred for 1 h at RT. The reaction mixture was diluted with AcOEt, and washed successively with water and brine, and dried over Na$_2$SO$_4$. The organic layer was concentrated in vacuo. The residue was used for the next step without further purification. LCMS(m/z) 424.13 [M+H]$^+$.

(Step 2) Synthesis of N-(biphenyl-3-yl)-7-bromo-2-hydrazinyl-N-methylquinazolin-4-amine

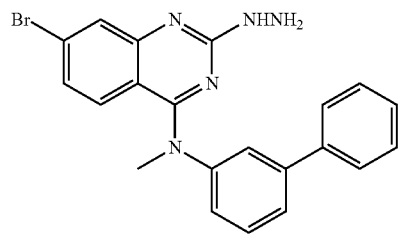 [SMILES: CN(c1cccc(-c2ccccc2)c1)c1nc(NN)nc2cc(Br)ccc12]

A mixture of N-(biphenyl-3-yl)-7-bromo-2-chloro-N-methylquinazolin-4-amine (310 mg, crude) and hydrazine hydrate (73.1 mg, 1.460 mmol) in EtOH (3.6 mL) was stirred for 3 h at 50° C. The reaction mixture was diluted with AcOEt, and washed successively with water and brine. The organic layer was concentrated in vacuo. The residue was used for the next step without further purification. LCMS(m/z) 420.18 [M+H]$^+$.

(Step 3) Synthesis of N-([1,1'-biphenyl]-3-yl)-8-bromo-N-methyl-[1,2,4]triazolo[4,3-a]quinazolin-5-amine A mixture of N-(biphenyl-3-yl)-7-bromo-2-hydrazinyl-N-methylquinazolin-4-amine (256 mg, crude) and triethoxymethane (89 mg, 0.603 mmol) was heated to 100° C. for 2 h. The reaction mixture was concentrated in vacuo. The residue was purified by column chromatography (Si-column, CHCl$_3$:MeOH=10:0-9:1) to afford the desired product: $^1$H NMR (CDCl$_3$) δ 8.91 (s, 1H), 7.98 (dd, J=1.6, 0.7 Hz, 1H), 7.54-7.36 (m, 8H), 7.28-7.24 (m, 2H), 7.14 (ddd, J=7.8, 2.2, 1.1 Hz, 1H), 3.71 (s, 3H); LCMS(m/z) 432.2/433.2 [M+H]$^+$.

Example 129. 3-([1,2,4]Triazolo[4,3-a]quinazolin-5-yl(methyl)amino)benzamide

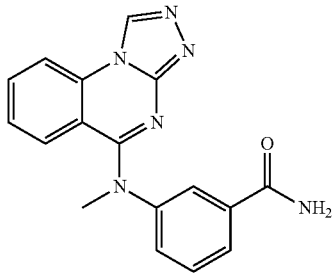 [SMILES: CN(c1cccc(C(N)=O)c1)c1nc2nncn2c2ccccc12]

(Step 1) Synthesis of 3-([1,2,4]triazolo[4,3-a]quinazolin-5-yl(methyl)amino)benzoic Acid

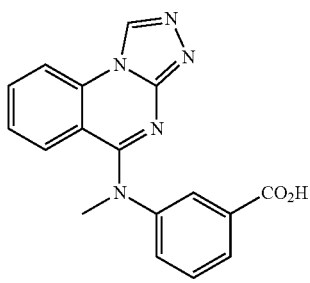 [SMILES: CN(c1cccc(C(=O)O)c1)c1nc2nncn2c2ccccc12]

To a stirred solution of methyl 3-([1,2,4]triazolo[4,3-a]quinazolin-5-yl(methyl)amino)benzoate (Example 103) (0.065 g, 0.19 mmol) in THF/water (4 mL, 1:1) was added lithium hydroxide monohydrate (0.025 g, 0.58 mmol) at RT and the mixture was stirred at RT for 16 h. The progress of the reaction was monitored by TLC. After completion of the reaction, the reaction mixture was evaporated under reduced pressure, and the residue was acidified with dilute HCl and evaporated under reduced pressure. The residue was purified by prep. HPLC to give the desired product. LCMS: 320.19 (M+H).

(Step 2) Synthesis of 3-([1,2,4]triazolo[4,3-a]quinazolin-5-yl(methyl)amino)benzamide To a stirred solution of 3-([1,2,4]Triazolo[4,3-a]quinazolin-5-yl(methyl)amino)benzoic acid (0.040 g, 0.12 mmol) in DMF (1 mL) were added 1-[Bis(dimethylamino)methylene]-1H-1,2,3-triazolo[4,5-b]pyridinium 3-oxidehexafluorophosphate (0.095 g, 0.25 mmol) and N, N-diisopropylethylamine (0.043 mL, 0.25 mmol) at RT, followed by the addition of 7N ammonia in methanol (12 mL) at 0° C. and the mixture was stirred for 16 h at RT. The progress of the reaction was monitored by TLC. After completion of the reaction, the reaction mixture was evaporated under reduced pressure. The residue was purified by prep. HPLC to afford the desired product: $^1$H NMR (DMSO-$d_6$) δ 9.65 (s, 1H), 8.47-8.23 (m, 1H), 7.92 (brs, 1H), 7.83-7.70 (m, 3H), 7.47-7.44 (m, 2H), 7.38 (brs, 1H), 7.29-7.19 (m, 2H), 3.57 (s, 3H); LCMS(m/z) 319.3 [M+H]+.

Example 130. (5-(Methyl(phenyl)amino)-[1,2,4]triazolo[4,3-a]quinazolin-7-yl)methanol

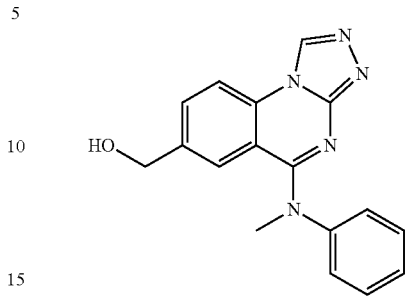

(Step 1) Synthesis of N-methyl-N-phenyl-7-vinyl-[1,2,4]triazolo[4,3-a]quinazolin-5-amine

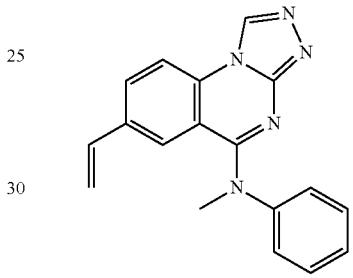

To a stirred solution of 7-bromo-N-methyl-N-phenyl-[1,2,4]triazolo[4,3-a]quinazolin-5-amine (0.5 g, 1.41 mmol) in n-butanol (10 mL) was added 4,4,5,5-tetramethyl-2-vinyl-1,3,2-dioxaborolane (0.48 mL, 2.82 mmol) at RT and the mixture was deoxygenated with argon for 10 mins, followed by the addition of potassium tert-butoxide (0.475 g, 4.23 mmol) and tetrakis(triphenylphosphine)palladium(0) (0.325 g, 0.28 mmol) at RT. The mixture was then stirred at 80° C. for 2 h. The reaction mixture was evaporated under reduced pressure, and the residue was purified by silica gel column chromatography, eluted with 5% methanol/dichloromethane to give the desired product. LCMS(m/z) 302.21 [M+H]$^+$.

(Step 2) Synthesis of 5-(methyl(phenyl)amino)-[1,2,4]triazolo[4,3-a]quinazoline-7-carbaldehyde

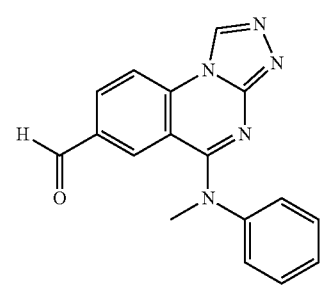 [SMILES: CN(c1ccccc1)c1nc2nncn2c2ccc(C=O)cc12]

To a solution of N-methyl-N-phenyl-7-vinyl-[1,2,4]triazolo[4,3-a]quinazolin-5-amine (0.5 g, 1.66 mmol) in acetonitrile/water (15 mL, 2:1) were added sodium periodate (0.426 g, 1.99 mmol) and potassium osmate(VI) dihydrate (0.122 g, 0.33 mmol) at 0° C. and the mixture was stirred at the RT for 16 h. The reaction mixture was evaporated under reduced pressure, and the residue was diluted with water and extracted with ethyl acetate. The organic layer was washed successively with water and brine, dried over $Na_2SO_4$, filtered and evaporated under reduced pressure to give the desired product. LCMS(m/z) 304.12 $[M+H]^+$.

(Step 3) Synthesis of (5-(methyl(phenyl)amino)-[1,2,4]triazolo[4,3-a]quinazolin-7-yl)methanol To a stirred solution of 5-(methyl(phenyl)amino)-[1,2,4]triazolo[4,3-a]quinazoline-7-carbaldehyde (crude, 0.480 g, 1.58 mmol) in MeOH (10 mL) was added sodium borohydride (0.120 g, 3.17 mmol) at 0° C. and the mixture was stirred for 3 h at RT. The reaction mixture was quenched with cold-water and extracted with dichloromethane. The organic layer was washed successively with water and brine, dried over $Na_2SO_4$, filtered and evaporated under reduced pressure. The residue was purified by silica gel column chromatography, eluted with 5% methanol/dichloromethane to afford the desired product: $^1$H NMR (DMSO-$d_6$) δ 9.58 (s, 1H), 8.24 (d, J=8.5 Hz, 1H), 7.70 (dd, J=8.5, 1.8 Hz, 1H), 7.44-7.34 (m, 2H), 7.32-7.17 (m, 4H), 5.13 (t, J=5.5 Hz, 1H), 4.22 (d, J=5.5 Hz, 2H), 3.55 (s, 3H); LCMS(m/z) 306.1 [M+H]+.

Example 131. N5-Methyl-N5-phenyl-[1,2,4]triazolo[4,3-a]quinazoline-5,7-diamine

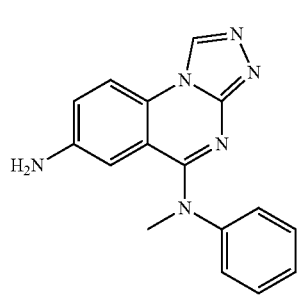

To a solution of N-methyl-7-nitro-N-phenyl-[1,2,4]triazolo[4,3-a]quinazolin-5-amine (Example 124) (0.2 g, 0.62 mmol) in MeOH (10 mL) was added Pd/C (0.04 g) at RT and the mixture was stirred under $H_2$ atmosphere for 3 h. The reaction mixture was filtered through a bed of celite and washed with methanol. The filtrate was evaporated under reduced pressure, and the residue was purified by prep. HPLC to afford the desired product: $^1$H NMR (DMSO-$d_6$) δ 9.44 (s, 1H), 7.98 (d, J=8.8 Hz, 1H), 7.46-7.27 (m, 2H), 7.28-7.11 (m, 3H), 7.01 (dd, J=8.8, 2.4 Hz, 1H), 6.42 (d, J=2.4 Hz, 1H), 5.29 (s, 2H), 3.49 (s, 3H); LCMS(m/z) 291.1 [M+H]+.

Example 132. N-(5-(methyl(phenyl)amino)-[1,2,4]triazolo[4,3-a]quinazolin-7-yl)methanesulfonamide

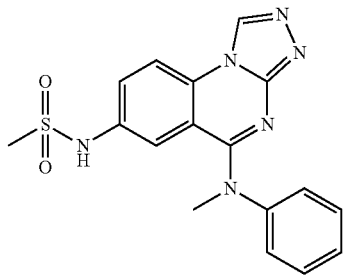 [SMILES: CN(c1ccccc1)c1nc2nncn2c2ccc(NS(C)(=O)=O)cc12]

To a stirred solution of N5-methyl-N5-phenyl-[1,2,4]triazolo[4,3-a]quinazoline-5,7-diamine (Example 131) (0.08 g, 0.27 mmol) in THF (5 mL) were added triethylamine (0.058 mL, 0.41 mmol) and methanesulfonyl chloride (0.032 mL, 0.41 mmol) at 0° C. and the mixture was stirred for 24 h at RT. The reaction was quenched with water and extracted with ethyl acetate. The organic layer was washed successively with water and brine, dried over $Na_2SO_4$, filtered and evaporated under reduced pressure. The residue was purified by prep. HPLC to afford the desired product: $^1$H NMR (DMSO-$d_6$) δ 9.94 (brs, 1H), 9.57 (s, 1H), 8.26 (d, J=8.9 Hz, 1H), 7.49 (dd, J=8.9, 2.4 Hz, 1H), 7.40-7.34 (m, 2H), 7.30 (d, J=2.4 Hz, 1H), 7.28-7.23 (m, 2H), 7.24-7.19 (m, 1H), 3.52 (s, 3H), 2.50 (s, 3H); LCMS(m/z) 369.1 [M+H]+.

Example 133. N-(2'-Fluoro-[1,1'-biphenyl]-3-yl)-N-methyl-[1,2,4]triazolo[4,3-a]quinazolin-5-amine

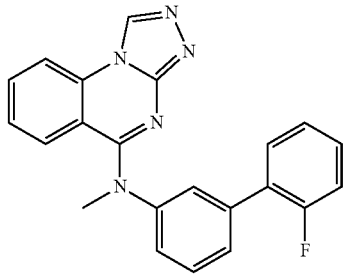 [SMILES: CN(c1cccc(-c2ccccc2F)c1)c1nc2nncn2c2ccccc12]

A mixture of N-(3-iodophenyl)-N-methyl-[1,2,4]triazolo[4,3-a]quinazolin-5-amine (Example 101) (15 mg, 0.037 mmol), K3P04 (15.87 mg, 0.075 mmol), Pd(OAc)$_2$ (1.679 mg, 7.48 μmol), tricyclohexylphosphine (2.097 mg, 7.48 μmol), and (1H-pyrazol-4-yl)boronic acid (6.28 mg, 0.056 mmol) in dioxane/water (0.20 mL) was heated at 100° C. for 1 h. The reaction mixture was subjected to solid phase extraction (washed with MeOH, then eluted with $NH_3$ in MeOH) using Bond Elut SCX cartridge (Agilent), and the collected fractions were concentrated in vacuo. The residue was purified by column chromatography (Si-column, CHCl$_3$:MeOH=10:0-9:1) to afford the desired product: $^1$H NMR (CDCl$_3$) δ 8.96 (s, 1H), 7.82 (dd, J=8.3, 1.1 Hz, 1H), 7.66 (ddd, J=8.3, 7.3, 1.1 Hz, 1H), 7.46-7.40 (m, 3H), 7.35-7.28 (m, 3H), 7.20-7.08 (m, 4H), 3.72 (s, 3H); LCMS (m/z) 370.3 [M+H]+.

Example 134. N-(4'-Methoxy-[1,1'-biphenyl]-3-yl)-N-methyl-[1,2,4]triazolo[4,3-a]quinazolin-5-amine

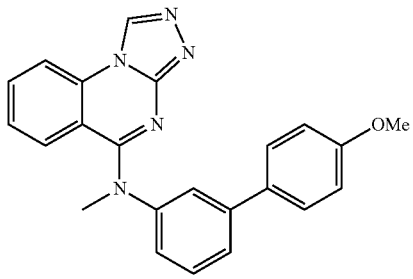 [SMILES: COc1ccc(-c2cccc(N(C)c3nc4nncn4c4ccccc34)c2)cc1]

A mixture of N-(3-iodophenyl)-N-methyl-[1,2,4]triazolo[4,3-a]quinazolin-5-amine (Example 101) (15 mg, 0.037 mmol), $K_3PO_4$ (15.87 mg, 0.075 mmol), Pd(OAc)$_2$ (1.679 mg, 0.0075 mmol), tricyclohexylphosphine (2.097 mg, 0.0075 mmol), and (4-methoxyphenyl)boronic acid (8.52 mg, 0.056 mmol) in dioxane/water (0.2 mL) was heated at 100° C. for 1 h. The reaction mixture was subjected to solid phase extraction (washed with MeOH, then eluted with $NH_3$ in MeOH) using Bond Elut SCX cartridge (Agilent), and the collected fractions were concentrated in vacuo. The residue was purified by column chromatography (Si-column, $CHCl_3$:MeOH=10:0-9:1) to afford the desired product: $^1$H NMR (CDCl$_3$) δ 8.95 (s, 1H), 7.88-7.77 (m, 1H), 7.64 (ddd, J=8.4, 7.3, 1.3 Hz, 1H), 7.47-7.39 (m, 5H), 7.33 (t, J=1.9 Hz, 1H), 7.19-7.08 (m, 2H), 7.01-6.85 (m, 2H), 3.83 (s, 3H), 3.72 (s, 3H); LCMS(m/z) 382.3 [M+H]+.

Example 135. N-(3'-Methoxy-[1,1'-biphenyl]-3-yl)-N-methyl-[1,2,4]triazolo[4,3-a]quinazolin-5-amine

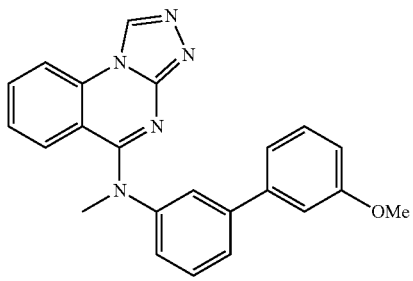 [SMILES: COc1cccc(-c2cccc(N(C)c3nc4nncn4c4ccccc34)c2)c1]

A mixture of N-(3-iodophenyl)-N-methyl-[1,2,4]triazolo[4,3-a]quinazolin-5-amine (Example 101) (15 mg, 0.037 mmol), $K_3PO_4$ (15.87 mg, 0.075 mmol), Pd(OAc)$_2$ (1.679 mg, 0.0075 mmol), tricyclohexylphosphine (2.097 mg, 0.0075 mmol), and pyrimidin-5-ylboronic acid (6.95 mg, 0.056 mmol) in dioxane/water (0.20 ml) was heated at 100° C. for 1 h. The reaction mixture was subjected to solid phase extraction (washed with MeOH, then eluted with $NH_3$ in MeOH) using Bond Elut SCX cartridge (Agilent), and the collected fractions were concentrated in vacuo. The residue was purified by column chromatography (Si-column, $CHCl_3$:MeOH=10:0-9:1) to afford the desired product: $^1$H NMR (Methanol-d4) δ 9.40 (s, 1H), 8.13 (dd, J=8.3, 1.2 Hz, 1H), 7.72 (ddd, J=8.3, 7.2, 1.2 Hz, 1H), 7.58-7.46 (m, 3H), 7.37 (dd, J=8.5, 1.4 Hz, 1H), 7.33-7.20 (m, 2H), 7.17 (ddd, J=8.5, 7.2, 1.2 Hz, 1H), 7.07 (dt, J=7.7, 1.3 Hz, 1H), 7.01 (t, J=2.1 Hz, 1H), 6.87 (ddd, J=8.2, 2.8, 1.0 Hz, 1H), 3.78 (s, 3H), 3.70 (s, 3H); LCMS(m/z) 382.3 [M+H]+.

Example 136. 7-(Methoxymethyl)-N-methyl-N-phenyl-[1,2,4]triazolo[4,3-a]quinazolin-5-amine

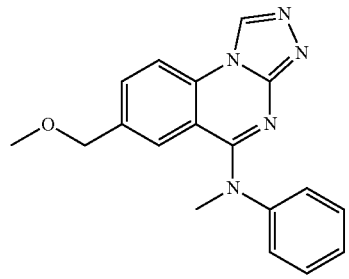 [SMILES: COCc1ccc2c(c1)c(N(C)c1ccccc1)nc1nncn12]

To a stirred solution of (5-(methyl(phenyl)amino)-[1,2,4]triazolo[4,3-a]quinazolin-7-yl)methanol (Example 130) (0.150 g, 0.49 mmol) in DMF (5 mL) was added 60% sodium hydride (0.023 g, 0.59 mmol) at 0° C. and the mixture was stirred for 10 mins at RT, followed by the addition of methyl iodide (0.036 mL, 0.59 mmol) at 0° C., and the mixture was stirred for 16 h at RT. The reaction mixture was quenched with cold-water and extracted with ethyl acetate. The organic layer was washed successively with water and brine, dried over $Na_2SO_4$, filtered and evaporated under reduced pressure. The residue was purified by prep. HPLC to afford the desired product: $^1$H NMR (DMSO-d$_6$) δ 9.60 (s, 1H), 8.27 (d, J=8.5 Hz, 1H), 7.69 (dd, J=8.5, 1.8 Hz, 1H), 7.42-7.37 (m, 2H), 7.33-7.29 (m, 2H), 7.28-7.24 (m, 1H), 7.20 (d, J=1.8 Hz, 1H), 4.17 (s, 2H), 3.55 (s, 3H), 2.95 (s, 3H); LCMS(m/z) 320.4 [M+H]+.

Example 137. N-methyl-N-(3-(pyridin-3-yl)phenyl)-[1,2,4]triazolo[4,3-a]quinazolin-5-amine

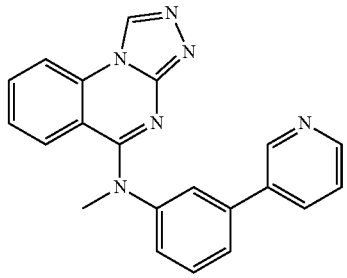

A mixture of N-(3-iodophenyl)-N-methyl-[1,2,4]triazolo[4,3-a]quinazolin-5-amine (Example 101) (15 mg, 0.037 mmol), $K_3PO_4$ (15.87 mg, 0.075 mmol), Pd(OAc)$_2$ (1.679 mg, 0.0075 mmol), tricyclohexylphosphine (2.097 mg, 0.0075 mmol), and pyrimidin-5-ylboronic acid (6.95 mg, 0.056 mmol) in dioxane/water (0.2 mL) was heated at 100° C. for 1 h. The reaction mixture was subjected to solid phase extraction (washed with MeOH, then eluted with $NH_3$ in MeOH) using Bond Elut SCX cartridge (Agilent), and the collected fractions were concentrated in vacuo. The residue was purified by column chromatography (Si-column, $CHCl_3$:MeOH=10:0-9:1) to afford the desired product: $^1$H NMR (CDCl$_3$) δ 8.97 (s, 1H), 8.70 (dd, J=2.4, 0.9 Hz, 1H), 8.58 (dd, J=4.8, 1.6 Hz, 1H), 7.84 (dd, J=8.4, 1.1 Hz, 1H), 7.77 (ddd, J=7.9, 2.4, 1.6 Hz, 1H), 7.67 (ddd, J=8.4, 7.3, 1.3 Hz, 1H), 7.53-7.45 (m, 2H), 7.41 (dd, J=8.4, 1.3 Hz, 1H), 7.36-7.31 (m, 2H), 7.22 (dt, J=7.0, 2.2 Hz, 1H), 7.15 (ddd, J=8.5, 7.2, 1.2 Hz, 1H), 3.73 (s, 3H); LCMS(m/z) 353.3 [M+H]+.

Example 138. N-(3-(1H-pyrazol-4-yl)phenyl)-N-methyl-[1,2,4]triazolo[4,3-a]quinazolin-5-amine

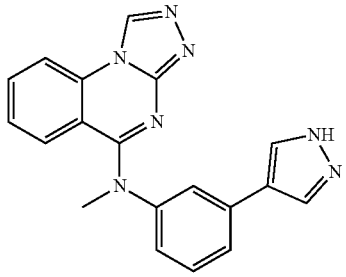

A mixture of N-(3-iodophenyl)-N-methyl-[1,2,4]triazolo[4,3-a]quinazolin-5-amine (Example 101) (15 mg, 0.037 mmol), K3P04 (15.87 mg, 0.075 mmol), Pd(OAc)$_2$ (1.679 mg, 0.0075 mmol), tricyclohexylphosphine (2.097 mg, 0.0075 mmol), and (1H-pyrazol-4-yl)boronic acid (6.28 mg, 0.056 mmol) in dioxane/water (0.2 mL) was heated at 100° C. for 1 h. The reaction mixture was subjected to solid phase extraction (washed with MeOH, then eluted with NH$_3$ in MeOH) using Bond Elut SCX cartridge (Agilent), and the collected fractions were concentrated in vacuo. The residue was purified by column chromatography (Si-column, CHCl$_3$:MeOH=10:0-9:1) to afford the desired product: $^1$H NMR (CDCl$_3$) δ 8.96 (s, 1H), 7.90-7.74 (m, 3H), 7.65 (ddd, J=8.4, 7.3, 1.3 Hz, 1H), 7.47-7.41 (m, 2H), 7.39 (dd, J=7.7, 0.5 Hz, 1H), 7.31 (dd, J=2.2, 1.5 Hz, 1H), 7.14 (ddd, J=8.5, 7.3, 1.2 Hz, 1H), 7.03 (ddd, J=7.7, 2.2, 1.2 Hz, 1H), 3.70 (s, 3H); LCMS(m/z) 342.3 [M+H]+.

Example 139. (5-(Methyl(phenyl)amino)-[1,2,4]triazolo[4,3-a]quinazolin-8-yl)methanol

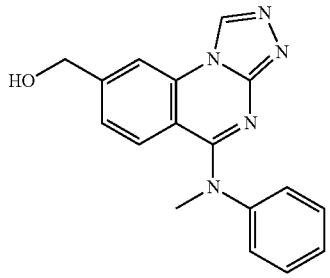 [SMILES: CN(c1ccccc1)c1nc2nncn2c2cc(CO)ccc12]

To a solution of 5-(methyl(phenyl)amino)-[1,2,4]triazolo[4,3-a]quinazoline-8-carbaldehyde (Example 117) (89 mg, 0.293 mmol) in MeOH (1.48 mL) was added NaBH$_4$ (22.20 mg, 0.587 mmol), and the mixture was stirred for 1 h at RT. The reaction mixture was subjected to solid phase extraction (washed with MeOH, then eluted with NH$_3$ in MeOH) using Bond Elut SCX cartridge (Agilent), and the collected fractions were concentrated in vacuo. The residue was purified by column chromatography (Si-column, CHCl$_3$:MeOH=10:0-9:1) to afford the desired product: $^1$H NMR (Methanol-d$_4$) δ 9.44 (s, 1H), 8.14 (d, J=1.5 Hz, 1H), 7.48-7.36 (m, 2H), 7.36-7.25 (m, 4H), 7.19-7.07 (m, 1H), 4.73 (s, 2H), 3.65 (s, 3H); LCMS(m/z) 306.2 [M+H]+.

Example 140. N-methyl-N-(3-(1-methyl-1H-pyrazol-4-yl)phenyl)-[1,2,4]triazolo[4,3-a]quinazolin-5-amine

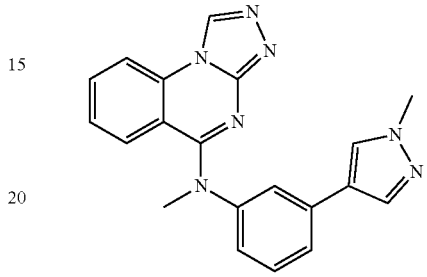

A mixture of N-(3-iodophenyl)-N-methyl-[1,2,4]triazolo[4,3-a]quinazolin-5-amine (Example 101) (15 mg, 0.037 mmol), K$_3$PO$_4$ (15.87 mg, 0.075 mmol), Pd(OAc)$_2$ (1.679 mg, 0.0075 mmol), tricyclohexylphosphine (2.097 mg, 0.0075 mmol), and 1-methyl-4-(4,4,5,5-tetramethyl-1,3,2-dioxaborolan-2-yl)-1H-pyrazole (11.67 mg, 0.056 mmol) in dioxane/water (0.20 ml) was heated at 100° C. for 1 h. The reaction mixture was subjected to solid phase extraction (washed with MeOH, then eluted with NH$_3$ in MeOH) using Bond Elut SCX cartridge (Agilent), and the collected fractions were concentrated in vacuo. The residue was purified by column chromatography (Si-column, CHCl$_3$:MeOH=10:0-9:1) to afford the desired product: $^1$H NMR (CDCl$_3$) δ 8.95 (s, 1H), 7.81 (dd, J=8.3, 1.2 Hz, 1H), 7.69 (d, J=0.8 Hz, 1H), 7.64 (ddd, J=8.4, 7.3, 1.3 Hz, 1H), 7.56 (dd, J=13.9, 0.8 Hz, 2H), 7.43-7.40 (m, 2H), 7.37-7.36 (m, 1H), 7.25 (m, 1H), 7.01 (dt, J=6.8, 2.1 Hz, 1H), 3.91 (s, 3H), 3.68 (s, 3H); LCMS(m/z) 356.3 [M+H]+.

Example 141. N-Methyl-N-(3-(thiophen-3-yl)phenyl)-[1,2,4]triazolo[4,3-a]quinazolin-5-amine

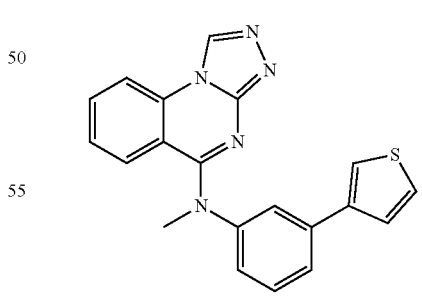

A mixture of N-(3-iodophenyl)-N-methyl-[1,2,4]triazolo[4,3-a]quinazolin-5-amine (Example 101) (15 mg, 0.037 mmol), K$_3$P04 (15.87 mg, 0.075 mmol), tricyclohexylphosphine (2.097 mg, 0.0075 mmol), Pd(OAc)$_2$ (1.679 mg, 0.0075 mmol), and thiophen-3-ylboronic acid (7.18 mg, 0.056 mmol) in dioxane/water (0.2 mL) was heated at 100° C. for 1 h. The reaction mixture was subjected to solid phase extraction (washed with MeOH, then eluted with NH$_3$ in MeOH) using Bond Elut SCX cartridge (Agilent), and the collected fractions were concentrated in vacuo. The residue was purified by column chromatography (Si-column, CHC$_3$: MeOH=10:0-9:1) to afford the desired product: $^1$H NMR (CDCl$_3$) δ 8.96 (s, 1H), 7.85-7.79 (m, 1H), 7.64 (ddd, J=8.4, 7.3, 1.3 Hz, 1H), 7.50 (ddd, J=7.7, 1.7, 1.0 Hz, 1H), 7.45-7.35 (m, 5H), 7.30 (dd, J=5.0, 1.3 Hz, 1H), 7.12 (ddd, J=8.4, 7.3, 1.3 Hz, 1H), 7.07 (ddd, J=7.9, 2.2, 1.0 Hz, 1H), 3.70 (s, 3H); LCMS(m/z) 358.2 [M+H]+.

Example 142. Methyl 5-(methyl(phenyl)amino)-[1,2,4]triazolo[4,3-a]quinazoline-7-carboxylate

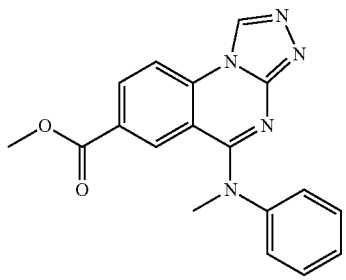 [SMILES: COC(=O)c1ccc2c(c1)c(N(C)c1ccccc1)nc1nncn12]

(Step 1) Synthesis of 5-(methyl(phenyl)amino)-[1,2,4]triazolo[4,3-a]quinazoline-7-carboxylic Acid

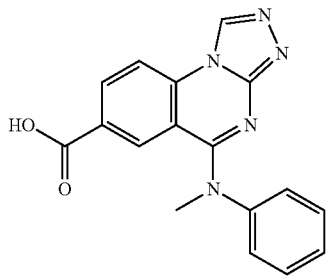 [SMILES: CN(c1ccccc1)c1nc2nncn2c2ccc(C(=O)O)cc12]

To a stirred solution of 5-(methyl(phenyl)amino)-[1,2,4]triazolo[4,3-a]quinazoline-7-carbaldehyde (0.2 g, 0.66 mmol) in DMF (6 mL) was added oxone (0.405 g, 1.32 mmol) at RT and the mixture was stirred at RT for 16 h. The reaction mixture was quenched with cold-water and extracted with ethyl acetate. The organic layer was washed successively with water and brine, dried over Na$_2$SO$_4$, filtered and evaporated under reduced pressure. The residue was purified by prep. HPLC to give the desired product. LC-MS: 320.23 (M+H).

(Step 2) Synthesis of Methyl 5-(methyl(phenyl)amino)-[1,2,4]triazolo[4,3-a]quinazoline-7-carboxylate To a solution of 5-(methyl(phenyl)amino)-[1,2,4]triazolo[4,3-a]quinazoline-7-carboxylic acid (0.15 g, 0.47 mmol) in MeOH (6 mL) was added 4N HCl in MeOH (1 mL) at RT and the mixture was stirred at 80° C. for 3 h. The reaction mixture was evaporated under reduced pressure, and the residue was purified by prep. HPLC to afford the desired product: $^1$H-NMR (DMSO-d$_6$) δ 9.65 (s, 1H), 8.37 (d, J=8.7 Hz, 1H), 8.23 (dd, J=8.7, 1.8 Hz, 1H), 7.89 (d, J=1.8 Hz, 1H), 7.47-7.39 (m, 2H), 7.38-7.28 (m, 3H), 3.71 (s, 3H), 3.57 (s, 3H); LCMS(m/z) 334.3 [M+H]+.

Example 143. 6-Bromo-N-methyl-N-phenyl-[1,2,4]triazolo[4,3-a]quinazolin-5-amine

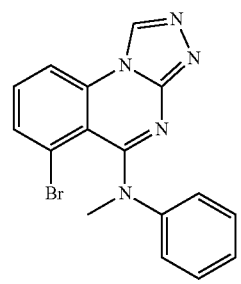

(Step 1) Synthesis of 5-bromoquinazoline-2,4(1H,3H)-dione

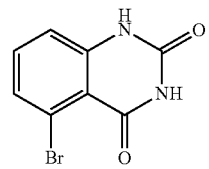 [SMILES: O=c1[nH]c(=O)c2c(Br)cccc2[nH]1]

A mixture of 2-amino-6-bromobenzoic acid (5 g, 23.14 mmol) and urea (13.88 g, 231.37 mmol) was heated to 150° C. for 16 h. The reaction mixture was diluted with ice-water and stirred for 30 min. The resulting solids were collected, and the solids were triturated with glacial acetic acid and washed with water and dried under vacuum to give the desired product. LCMS(m/z) 241.02 [M+H]$^+$.

(Step 2) Synthesis of 5-bromo-2,4-dichloroquinazoline

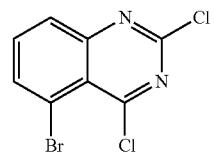 [SMILES: Clc1nc(Cl)c2c(Br)cccc2n1]

To a stirred solution of 5-bromoquinazoline-2,4(1H,3H)-dione (crude, 3.2 g, 13.33 mmol) in phosphorus oxychloride (13 mL, 133.33 mmol) was added N, N-diisopropylethylamine (3.48 mL, 19.99 mmol) at 0° C. and the mixture was stirred at 110° C. for 3 h. The reaction mixture was diluted with ice-water and stirred for 30 min. The resulting solids were filtered, washed with water and dried under vacuum to give the desired product. LCMS(m/z) 277.11 [M+H]$^+$.

(Step 3) Synthesis of 5-bromo-2-chloro-N-methyl-N-phenylquinazolin-4-amine

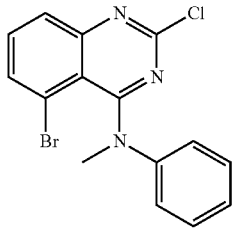 [SMILES: CN(c1ccccc1)c1nc(Cl)nc2cccc(Br)c12]

To a stirred mixture of N-methylaniline (0.892 g, 8.33 mmol) in DMF (25 mL) was added sodium hydroxide (0.333 g, 8.33 mmol) at 0° C. and the mixture was stirred at the RT for 1 h, followed by the addition of 5-bromo-2,4-dichloro-quinazoline (crude, 2.3 g, 8.33 mmol) at 0° C. The mixture was then stirred for 2 h at RT. The reaction mixture was diluted with water and extracted with ethyl acetate. The organic layer was washed successively with water and brine, dried over $Na_2SO_4$, filtered and evaporated under reduced pressure to give the desired product. LCMS(m/z) 348.15 $[M+H]^+$.

(Step 4) Synthesis of 5-bromo-2-hydrazinyl-N-methyl-N-phenylquinazolin-4-amine

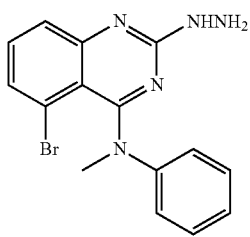 [SMILES: CN(c1ccccc1)c1nc(NN)nc2cccc(Br)c12]

To a stirred solution of 5-bromo-2-chloro-N-methyl-N-phenylquinazolin-4-amine (0.5 g, 1.44 mmol) in EtOH (6 mL) was added hydrazine hydrate (0.14 mL g, 2.87 mmol) at RT and the mixture was stirred at RT for 6 h. The reaction mixture was evaporated under reduced pressure to give the desired product. LCMS(m/z) 344.36 $[M+H]^+$.

(Step 5) Synthesis of 6-bromo-N-methyl-N-phenyl-[1,2,4]triazolo[4,3-a]quinazolin-5-amine The mixture of 5-bromo-2-hydrazinyl-N-methyl-N-phenylquinazolin-4-amine (0.5 g, 1.45 mmol) and triethyl orthoformate (1.45 mL, 8.72 mmol) was stirred at 100° C. for 16 h. The reaction mixture was diluted with diethyl ether and filtered. The filtrate was evaporated under reduced pressure, and the residue was purified by silica gel column chromatography, eluted with 5% methanol/dichloromethane and further purified by prep. HPLC to afford the desired product: $^1$H-NMR (DMSO-$d_6$) δ 9.70 (s, 1H), 8.38 (dd, J=8.3, 1.2 Hz, 1H), 7.75 (t, J=8.0 Hz, 1H), 7.67 (dd, J=8.0, 1.2 Hz, 1H), 7.24-7.12 (m, 2H), 7.07-6.91 (m, 3H), 3.51 (s, 3H); LCMS(m/z) 354.27/356.25 [M+H]+.

Example 144. 8-(Methoxymethyl)-N-methyl-N-phenyl-[1,2,4]triazolo[4,3-a]quinazolin-5-amine

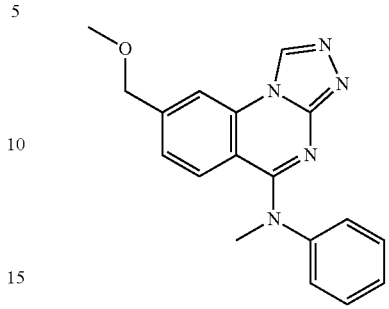

To a solution of (5-(methyl(phenyl)amino)-[1,2,4]triazolo[4,3-a]quinazolin-8-yl)methanol (Example 139) (15 mg, 0.049 mmol) in DMF (0.25 mL) were added iodomethane (8.37 mg, 0.059 mmol) and sodium hydride (1.415 mg, 0.059 mmol), and the mixture was stirred for 3 h at RT. The reaction mixture was diluted with AcOEt, washed successively with water and brine. The organic layer was concentrated in vacuo, and purified by prep-HPLC to afford the desired product: $^1$H NMR (Methanol-$d_4$) δ 9.46 (s, 1H), 8.16-8.14 (m, 1H), 7.46-7.40 (m, 2H), 7.35-7.31 (m, 1H), 7.30-7.26 (m, 3H), 7.17-7.06 (m, 1H), 4.57 (m, 2H), 3.66 (s, 3H), 3.43 (s, 3H); LCMS(m/z) 320.2 [M+H]+.

Example 145. N-Methyl-N-(3-(pyrimidin-5-yl)phenyl)-[1,2,4]triazolo[4,3-a]quinazolin-5-amine

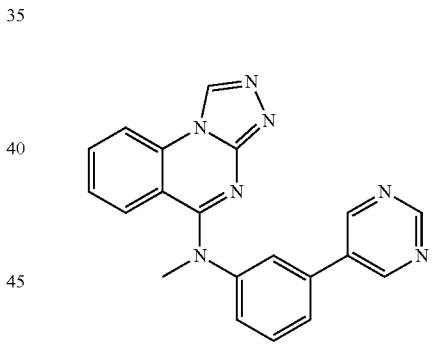

A mixture of N-(3-iodophenyl)-N-methyl-[1,2,4]triazolo[4,3-a]quinazolin-5-amine (Example 101) (15 mg, 0.037 mmol), $K_3PO_4$ (15.87 mg, 0.075 mmol), Pd(OAc)$_2$ (1.679 mg, 0.0075 mmol), tricyclohexylphosphine (2.097 mg, 0.0075 mmol), and pyrimidin-5-ylboronic acid (6.95 mg, 0.056 mmol) in dioxane/water (0.2 mL) was heated at 100° C. for 1 h. The reaction mixture was subjected to solid phase extraction (washed with MeOH, then eluted with $NH_3$ in MeOH) using Bond Elut SCX cartridge (Agilent), and the collected fractions were concentrated in vacuo. The residue was purified by column chromatography (Si-column, CHCl$_3$:MeOH=10:0-9:1) to afford the desired product: $^1$H NMR (CDCl$_3$) δ 8.81 (s, 1H), 7.76-7.68 (m, 1H), 7.66 (t, J=1.9 Hz, 1H), 7.60 (ddd, J=8.4, 7.3, 1.3 Hz, 1H), 7.49 (ddd, J=7.9, 1.9, 1.0 Hz, 1H), 7.45-7.34 (m, 2H), 7.12-7.02 (m, 2H), 6.80 (td, J=2.7, 1.5 Hz, 1H), 6.55 (ddd, J=3.9, 2.6, 1.5 Hz, 1H), 6.30-6.19 (m, 1H), 3.61 (s, 3H); LCMS(m/z) 354.3 [M+H]+.

Example 146. N-(3-(1H-Pyrrol-2-yl)phenyl)-N-methyl-[1,2,4]triazolo[4,3-a]quinazolin-5-amine

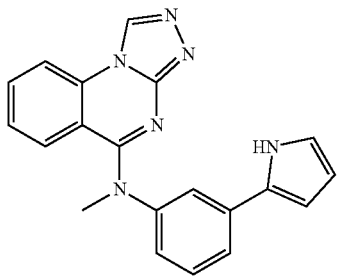 [SMILES: CN(c1cccc(-c2ccc[nH]2)c1)c1nc2nncn2c2ccccc12]

A mixture of N-(3-iodophenyl)-N-methyl-[1,2,4]triazolo[4,3-a]quinazolin-5-amine (Example 101) (15 mg, 0.037 mmol), K3PO4 (15.87 mg, 0.075 mmol), Pd(OAc)$_2$ (1.679 mg, 0.0075 mmol), tricyclohexylphosphine (2.097 mg, 0.0075 mmol) and (1-(tert-butoxycarbonyl)-1H-pyrrol-2-yl)boronic acid (11.83 mg, 0.056 mmol) in dioxane/water (0.2 mL) was treated in a microwave reactor at 100° C. for 1 h. The reaction mixture was subjected to solid phase extraction (washed with MeOH, then eluted with NH$_3$ in MeOH) using Bond Elut SCX cartridge (Agilent), and the collected fractions were concentrated in vacuo. The residue was purified by column chromatography (Si-column, CHCl$_3$:MeOH=10:0-9:1) to afford the desired product: $^1$H NMR (CDCl$_3$) δ 10.56 (s, 1H), 8.77 (s, 1H), 7.77 (t, J=1.9 Hz, 1H), 7.69 (dd, J=8.3, 1.2 Hz, 1H), 7.59 (ddd, J=8.4, 7.2, 1.3 Hz, 1H), 7.51 (ddd, J=7.9, 1.8, 1.1 Hz, 1H), 7.41 (t, J=7.9 Hz, 1H), 7.36 (dd, J=8.5, 1.2 Hz, 1H), 7.13-7.04 (m, 2H), 6.78 (td, J=2.7, 1.5 Hz, 1H), 6.56 (ddd, J=3.9, 2.7, 1.4 Hz, 1H), 6.21 (dt, J=3.5, 2.5 Hz, 1H), 3.59 (s, 3H); LCMS(m/z) 341.3 [M+H]+.

Example 147. 3-([1,2,4]Triazolo[4,3-a]quinazolin-5-yl(methyl)amino)benzonitrile

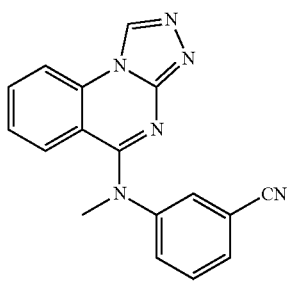 [SMILES: CN(c1cccc(C#N)c1)c1nc2nncn2c2ccccc12]

A mixture of N-(3-iodophenyl)-N-methyl-[1,2,4]triazolo[4,3-a]quinazolin-5-amine (Example 101) (20 mg, 0.050 mmol), zinc(II) cyanide (11.71 mg, 0.100 mmol) and Pd(PPh$_3$)$_4$ (11.52 mg, 0.010 mmol) in DMF (0.25 mL) was treated in a microwave reactor at 80° C. for 1 h. Then added zinc(II) cyanide (11.71 mg, 0.100 mmol) and Pd(PPh$_3$)$_4$ (11.52 mg, 0.010 mmol), and treated in a microwave reactor at 80° C. for 1 h. The reaction mixture was subjected to solid phase extraction (washed with MeOH, then eluted with NH$_3$ in MeOH) using Bond Elut SCX cartridge (Agilent), and the collected fractions were concentrated in vacuo. The residue was concentrated in vacuo. The residue was purified by column chromatography (Si-column, CHCl$_3$:MeOH=10:0-9:1) to afford the desired product: $^1$H NMR (Methanol-d$_4$) δ 9.50 (s, 1H), 8.23 (dd, J=8.5, 1.1 Hz, 1H), 7.85-7.75 (m, 1H), 7.77-7.69 (m, 1H), 7.63 (ddd, J=6.2, 2.5, 1.4 Hz, 1H), 7.60-7.53 (m, 2H), 7.36 (dd, J=8.5, 1.4 Hz, 1H), 7.28 (ddd, J=8.4, 7.2, 1.2 Hz, 1H), 3.68 (s, 3H); LCMS(m/z) 301.2/302.2 [M+H]+.

Example 148. N-(2'-Methoxy-[1,1'-biphenyl]-3-yl)-N-methyl-[1,2,4]triazolo[4,3-a]quinazolin-5-amine

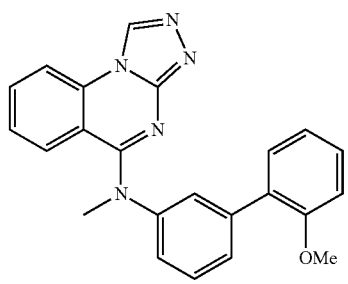 [SMILES: COc1ccccc1-c1cccc(N(C)c2nc3nncn3c3ccccc23)c1]

A mixture of N-(3-iodophenyl)-N-methyl-[1,2,4]triazolo[4,3-a]quinazolin-5-amine (Example 101) (15 mg, 0.037 mmol), K$_3$PO$_4$ (15.87 mg, 0.075 mmol), Pd(OAc)$_2$ (1.679 mg, 0.0075 mmol), tricyclohexylphosphine (2.097 mg, 0.0075 mmol), and (2-methoxyphenyl)boronic acid (8.52 mg, 0.056 mmol) in dioxane/water (0.2 mL) was heated at 100° C. for 1 h. The reaction mixture was subjected to solid phase extraction (washed with MeOH, then eluted with NH$_3$ in MeOH) using Bond Elut SCX cartridge (Agilent), and the collected fractions were concentrated in vacuo. The residue was purified by column chromatography (Si-column, CHCl$_3$:MeOH=10:0-9:1) to afford the desired product: $^1$H NMR (CDCl$_3$) δ 8.95 (d, J=0.8 Hz, 1H), 7.82 (dt, J=8.0, 0.8 Hz, 1H), 7.66 (ddd, J=8.4, 7.3, 1.3 Hz, 1H), 7.48-7.39 (m, 3H), 7.34-7.27 (m, 2H), 7.21 (dd, J=7.5, 1.8 Hz, 1H), 7.19-7.12 (m, 2H), 6.98 (td, J=7.5, 1.1 Hz, 1H), 6.92 (dd, J=8.3, 1.1 Hz, 1H), 3.71 (s, 3H), 3.64 (s, 3H); LCMS(m/z) 382.3 [M+H]+.

Example 149. tert-Butyl (3-(5-(methyl(phenyl)amino)-[1,2,4]triazolo[4,3-a]quinazolin-8-yl)prop-2-yn-1-yl)carbamate

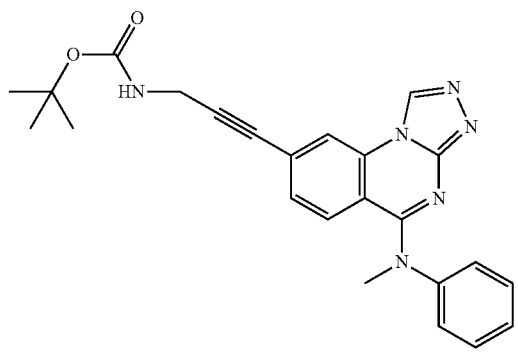 [SMILES: CN(c1ccccc1)c1nc2nncn2c2cc(C#CCNC(=O)OC(C)(C)C)ccc12]

A mixture of 8-bromo-N-methyl-N-phenyl-[1,2,4]triazolo[4,3-a]quinazolin-5-amine (Example 28) (30 mg, 0.085 mmol), Pd(dppf)$_2$Cl (12.39 mg, 0.017 mmol), triethylamine (25.7 mg, 0.254 mmol), tert-butyl prop-2-yn-1-ylcarbamate (26.3 mg, 0.169 mmol) and copper(I) iodide (3.23 mg, 0.017 mmol) in acetonitrile (0.42 mL) was treated in a microwave reactor at 80° C. for 2 h. The reaction mixture was subjected to solid phase extraction (washed with MeOH, then eluted with $NH_3$ in MeOH) using Bond Elut SCX cartridge (Agilent), and the collected fractions were concentrated in vacuo. The filtrate was purified by prep-HPLC to afford the desired product: $^1$H NMR (Methanol-$d_4$) δ 9.40 (s, 1H), 8.24 (d, J=1.5 Hz, 1H), 7.50-7.37 (m, 2H), 7.37-7.30 (m, 1H), 7.30-7.19 (m, 3H), 7.13 (dd, J=8.7, 1.5 Hz, 1H), 4.08 (s, 2H), 3.64 (s, 3H), 1.45 (s, 9H); LCMS(m/z) 429.4 [M+H]+.

Example 150. 8-(3-Aminoprop-1-yn-1-yl)-N-methyl-N-phenyl-[1,2,4]triazolo[4,3-a]quinazolin-5-amine

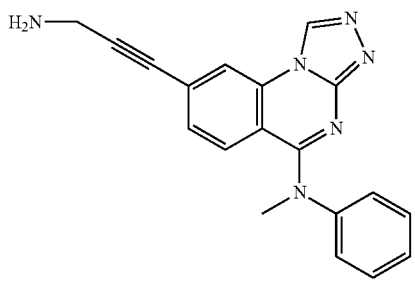 [SMILES: CN(c1ccccc1)c1nc2nncn2c2cc(C#CCN)ccc12]

A mixture of tert-butyl (3-(5-(methyl(phenyl)amino)-[1,2,4]triazolo[4,3-a]quinazolin-8-yl)prop-2-yn-1-yl)carbamate (Example 149) (25 mg, 0.058 mmol) and TFA (5 mL) was stirred for 3 h at RT, then stirred overnight at 50° C. The reaction mixture was concentrated in vacuo. 4N HCl (5 mL) was added to the residue and the solution was stirred for 3 h at RT, then stirred for overnight at 50° C. The reaction mixture was concentrated in vacuo. The residue was purified by column chromatography (Si-column, $CHCl_3$:MeOH=10:0-9:1) to afford the desired product: $^1$H NMR (Methanol-$d_4$) δ 9.64 (s, 1H), 8.54 (d, J=1.5 Hz, 1H), 7.58-7.52 (m, 3H), 7.49-7.42 (m, 2H), 7.35 (dd, J=8.8, 1.5 Hz, 1H), 7.17 (d, J=8.8 Hz, 1H), 4.12 (s, 2H), 3.80 (s, 3H); LCMS(m/z) 329.2 [M+H]+.

Example 151. N-Methyl-N-(4'-(trifluoromethyl)-[1,1'-biphenyl]-3-yl)-[1,2,4]triazolo[4,3-a]quinazolin-5-amine

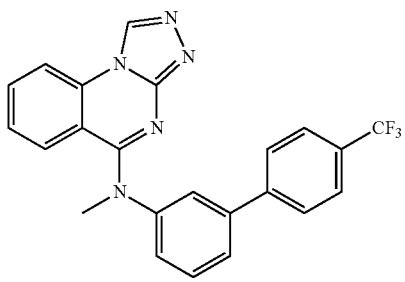 [SMILES: CN(c1cccc(-c2ccc(C(F)(F)F)cc2)c1)c1nc2nncn2c2ccccc12]

A mixture of N-(3-iodophenyl)-N-methyl-[1,2,4]triazolo[4,3-a]quinazolin-5-amine (Example 101) (15 mg, 0.037 mmol), $K_3PO_4$ (15.87 mg, 0.075 mmol), Pd(OAc)$_2$ (1.679 mg, 0.0075 mmol), tricyclohexylphosphine (2.097 mg, 0.0075 mmol), and (4-(trifluoromethyl)phenyl)boronic acid (10.65 mg, 0.056 mmol) in dioxane/water (0.2 mL) was heated at 100° C. for 1 h. The reaction mixture was subjected to solid phase extraction (washed with MeOH, then eluted with $NH_3$ in MeOH) using Bond Elut SCX cartridge (Agilent), and the collected fractions were concentrated in vacuo. The residue was purified by column chromatography (Si-column, $CHCl_3$:MeOH=10:0-9:1) to afford the desired product: $^1$H NMR (Methanol-d4) δ 9.42 (s, 1H), 8.13 (dd, J=8.5, 1.2 Hz, 1H), 7.76-7.66 (m, 5H), 7.66-7.58 (m, 2H), 7.53 (t, J=7.8 Hz, 1H), 7.37 (dd, J=8.5, 1.3 Hz, 1H), 7.30 (ddd, J=7.9, 2.2, 1.0 Hz, 1H), 7.17 (ddd, J=8.5, 7.3, 1.2 Hz, 1H), 3.71 (s, 3H); LCMS(m/z) 420.3 [M+H]+.

Example 152. N-Methyl-N-(4'-methyl-[1,1'-biphenyl]-3-yl)-[1,2,4]triazolo[4,3-a]quinazolin-5-amine

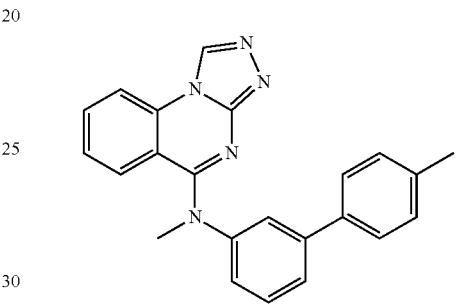

A mixture of N-(3-iodophenyl)-N-methyl-[1,2,4]triazolo[4,3-a]quinazolin-5-amine (Example 101) (15 mg, 0.037 mmol), $K_3PO_4$ (15.87 mg, 0.075 mmol), Pd(OAc)$_2$ (1.679 mg, 0.0075 mmol), tricyclohexylphosphine (2.097 mg, 0.0075 mmol), and p-tolylboronic acid (7.62 mg, 0.056 mmol) in dioxane/water (0.2 mL) was heated to 100° C. for 1 h. The reaction mixture was subjected to solid phase extraction (washed with MeOH, then eluted with $NH_3$ in MeOH) using Bond Elut SCX cartridge (Agilent), and the collected fractions were concentrated in vacuo. The residue was purified by column chromatography (Si-column, $CHCl_3$:MeOH=10:0-9:1) to afford the desired product: $^1$H NMR (Methanol-$d_4$) δ 9.40 (s, 1H), 8.19-8.08 (m, 1H), 7.70 (ddd, J=8.5, 7.3, 1.3 Hz, 1H), 7.53 (ddd, J=7.8, 1.8, 1.1 Hz, 1H), 7.50-7.42 (m, 2H), 7.42-7.31 (m, 3H), 7.19-7.16 (m, 3H), 7.15-7.12 (m, 1H), 3.68 (s, 3H), 2.32 (s, 3H); LCMS (m/z) 366.3 [M+H]+.

Example 153. N-(3'-Fluoro-[1,1'-biphenyl]-3-yl)-N-methyl-[1,2,4]triazolo[4,3-a]quinazolin-5-amine

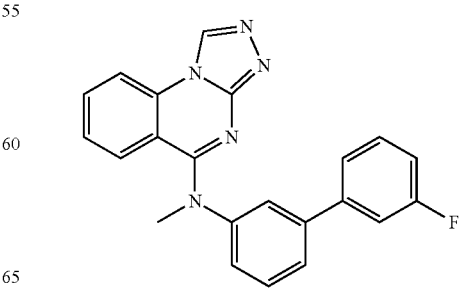

A mixture of N-(3-iodophenyl)-N-methyl-[1,2,4]triazolo[4,3-a]quinazolin-5-amine (Example 101) (15 mg, 0.037 mmol), K₃PO₄ (15.87 mg, 0.075 mmol), Pd(OAc)₂ (1.679 mg, 0.0075 mmol), tricyclohexylphosphine (2.097 mg, 0.0075 mmol), and (4-(trifluoromethyl)phenyl)boronic acid (10.65 mg, 0.056 mmol) in dioxane/water (0.2 mL) was heated at 100° C. for 1 h. The reaction mixture was subjected to solid phase extraction (washed with MeOH, then eluted with NH₃ in MeOH) using Bond Elut SCX cartridge (Agilent), and the collected fractions were concentrated in vacuo. The residue was purified by column chromatography (Si-column, CHCl₃:MeOH=10:0-9:1) to afford the desired product: ¹H-NMR (Methanol-d4) δ 9.45 (s, 1H), 8.24 (d, J=8.6 Hz, 1H), 8.02 (dd, J=8.6, 2.0 Hz, 1H), 7.58-7.51 (m, 3H), 7.48-7.41 (m, 1H), 7.40-7.31 (m, 3H), 7.06 (tdd, J=8.5, 2.6, 0.9 Hz, 1H), 6.93 (dt, J=7.8, 1.2 Hz, 1H), 6.76 (dt, J=10.3, 2.1 Hz, 1H), 3.71 (s, 3H); LCMS(m/z) 370.3 [M+H]+.

Example 154. N8-(2-Methoxyethyl)-N5-methyl-N5-phenyl-[1,2,4]triazolo[4,3-a]quinazoline-5,8-diamine

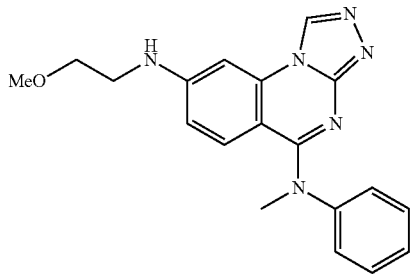 [SMILES: COCCNc1ccc2c(N(C)c3ccccc3)nc3nncn3c2c1]

To a solution of 8-bromo-N-methyl-N-phenyl-[1,2,4]triazolo[4,3-a]quinazolin-5-amine (Example 28) (20 mg, 0.056 mmol) in acetonitrile (0.28 mL) were added 2-methoxyethan-1-amine (4.24 mg, 0.056 mmol), K₂CO₃ (7.80 mg, 0.056 mmol), Pd(dba)₃ (0.056 mmol) and (9,9-dimethyl-9H-xanthene-4,5-diyl)bis(diphenylphosphine) (32.7 mg, 0.056 mmol). The mixture was stirred for 2 h at 80° C. The reaction mixture was concentrated in vacuo. The residue was purified by column chromatography (Si-column, CHCl₃:MeOH=10:0-85:15), and further purified by prep-HPLC to afford the desired product: ¹H NMR (Methanol-d₄) δ 9.32 (s, 1H), 7.49-7.37 (m, 2H), 7.32-7.25 (m, 1H), 7.25-7.19 (m, 2H), 7.04 (t, J=1.8 Hz, 1H), 7.01-6.89 (m, 1H), 6.40 (ddd, J=9.3, 2.4, 0.7 Hz, 1H), 3.62-3.57 (m, 5H), 3.41 (t, J=5.3 Hz, 2H), 3.37 (s, 3H); LCMS(m/z) 349.3 [M+H]+.

Example 155. 3'-([1,2,4]Triazolo[4,3-a]quinazolin-5-yl(methyl)amino)-[1,1'-biphenyl]-4-ol

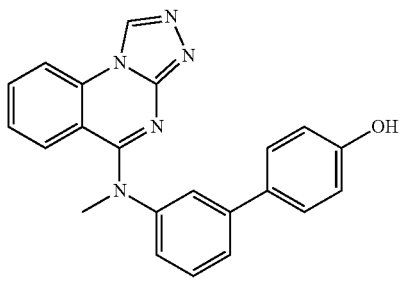 [SMILES: CN(c1cccc(-c2ccc(O)cc2)c1)c1nc2nncn2c2ccccc12]

A mixture of N-(3-iodophenyl)-N-methyl-[1,2,4]triazolo[4,3-a]quinazolin-5-amine (Example 101) (15 mg, 0.037 mmol), K₃PO₄ (15.87 mg, 0.075 mmol), Pd(OAc)₂ (1.679 mg, 0.0075 mmol), tricyclohexylphosphine (2.097 mg, 0.0075 mmol), and (4-hydroxyphenyl)boronic acid (7.74 mg, 0.056 mmol) in dioxane/water (0.2 mL) was heated at 100° C. for 1 h. The reaction mixture was subjected to solid phase extraction (washed with MeOH, then eluted with NH₃ in MeOH) using Bond Elut SCX cartridge (Agilent), and the collected fractions were concentrated in vacuo. The residue was purified by column chromatography (Si-column, CHCl₃:MeOH=10:0-9:1) to afford the desired product: ¹H NMR (Methanol-d₄) δ 9.44 (s, 1H), 8.18 (dd, J=8.3, 1.1 Hz, 1H), 7.75 (ddd, J=8.5, 7.3, 1.3 Hz, 1H), 7.52 (ddd, J=7.8, 1.8, 1.1 Hz, 1H), 7.48-7.43 (m, 3H), 7.41-7.35 (m, 2H), 7.24-7.14 (m, 2H), 6.83-6.80 (m, 2H), 3.71 (s, 3H); LCMS (m/z) 368.3 [M+H]+.

Example 156. N-(4'-Chloro-[1,1'-biphenyl]-3-yl)-N-methyl-[1,2,4]triazolo[4,3-a]quinazolin-5-amine

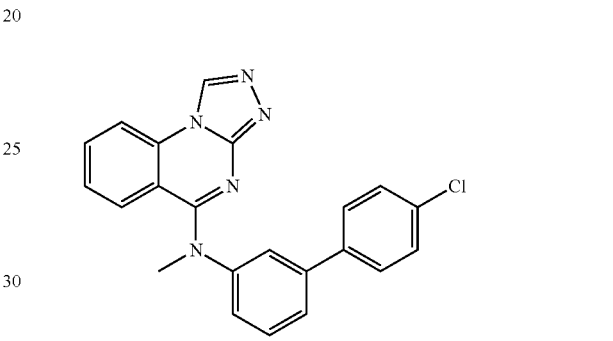

A mixture of N-(3-iodophenyl)-N-methyl-[1,2,4]triazolo[4,3-a]quinazolin-5-amine (Example 101) (15 mg, 0.037 mmol), K₃PO₄ (15.87 mg, 0.075 mmol), Pd(OAc)₂ (1.679 mg, 0.0075 mmol), tricyclohexylphosphine (2.097 mg, 0.0075 mmol), and (4-chlorophenyl)boronic acid (8.77 mg, 0.056 mmol) in dioxane/water (0.2 mL) was heated at 100° C. for 1 h. The reaction mixture was subjected to solid phase extraction (washed with MeOH, then eluted with NH₃ in MeOH) using Bond Elut SCX cartridge (Agilent), and the collected fractions were concentrated in vacuo. The residue was purified by column chromatography (Si-column, CHCl₃:MeOH=10:0-9:1) to afford the desired product: ¹H NMR (Methanol-d₄) δ 9.44 (s, 1H), 8.26-8.08 (m, 1H), 7.75 (ddd, J=8.5, 7.3, 1.3 Hz, 1H), 7.58 (ddd, J=7.8, 1.8, 1.1 Hz, 1H), 7.56-7.48 (m, 4H), 7.44-7.34 (m, 3H), 7.28 (ddd, J=7.9, 2.3, 1.1 Hz, 1H), 7.20 (ddd, J=8.5, 7.3, 1.1 Hz, 1H), 3.71 (s, 3H); LCMS(m/z) 386.3 [M+H]+.

Example 157. 2-((5-(Methyl(phenyl)amino)-[1,2,4]triazolo[4,3-a]quinazolin-8-yl)amino)ethanol

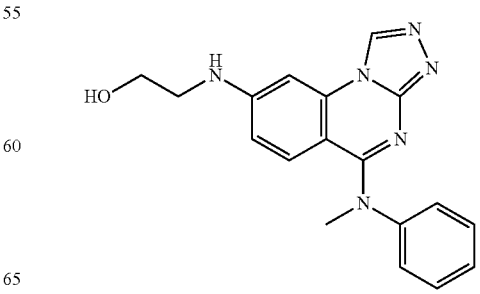

To a solution of 8-bromo-N-methyl-N-phenyl-[1,2,4]triazolo[4,3-a]quinazolin-5-amine (Example 28) (20 mg, 0.056 mmol) in acetonitrile (0.42 mL) were added 2-aminoethan-1-ol (6.21 mg, 0.102 mmol), K₂CO₃ (17.56 mg, 0.127 mmol) and Pd(dba)₃ (0.085 mmol). The mixture was stirred for 2 h at 80° C. The reaction mixture was concentrated in vacuo. The residue was purified by column chromatography (Si-column, CHCl₃:MeOH=10:0-85:15), and further purified by prep-HPLC to afford the desired product: ¹H NMR (Methanol-d4) δ 9.31 (s, 1H), 7.43-7.37 (m, 2H), 7.30-7.25 (m, 1H), 7.25-7.20 (m, 2H), 7.02 (d, J=2.3 Hz, 1H), 6.90 (d, J=9.3 Hz, 1H), 6.39 (dd, J=9.3, 2.3 Hz, 1H), 3.75 (t, J=5.6 Hz, 2H), 3.59 (s, 3H), 3.37 (d, J=5.6 Hz, 2H); LCMS(m/z) 335.3 [M+H]+.

Example 158. 3'-([1,2,4]Triazolo[4,3-a]quinazolin-5-yl(methyl)amino)-[1,1'-biphenyl]-2-ol

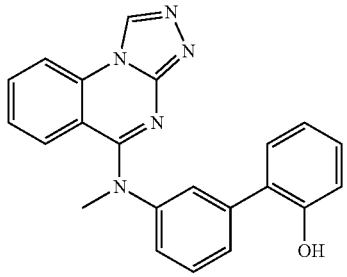 [SMILES: CN(c1cccc(-c2ccccc2O)c1)c1nc2nncn2c2ccccc12]

A mixture of N-(3-iodophenyl)-N-methyl-[1,2,4]triazolo[4,3-a]quinazolin-5-amine (Example 101) (15 mg, 0.037 mmol), K₃PO₄ (15.87 mg, 0.075 mmol), Pd(OAc)₂ (1.679 mg, 0.0075 mmol), tricyclohexylphosphine (2.097 mg, 0.0075 mmol), and (2-hydroxyphenyl)boronic acid (7.74 mg, 0.056 mmol) in dioxane/water (0.2 mL) was heated at 100° C. for 1 h. The reaction mixture was subjected to solid phase extraction (washed with MeOH, then eluted with NH₃ in MeOH) using Bond Elut SCX cartridge (Agilent), and the collected fractions were concentrated in vacuo. The residue was purified by column chromatography (Si-column, CHCl₃:MeOH=10:0-9:1) to afford the desired product: ¹H NMR (Methanol-d₄) δ 9.39 (s, 1H), 8.12 (dd, J=8.4, 1.1 Hz, 1H), 7.72 (ddd, J=8.4, 7.3, 1.3 Hz, 1H), 7.53-7.47 (m, 2H), 7.46-7.38 (m, 2H), 7.25-7.05 (m, 4H), 6.87-6.82 (m, 2H), 3.68 (s, 3H); LCMS(m/z) 368.3 [M+H]+.

Example 159. N-Methyl-N-(3-(1-methyl-1H-pyrazol-5-yl)phenyl)-[1,2,4]triazolo[4,3-a]quinazolin-5-amine

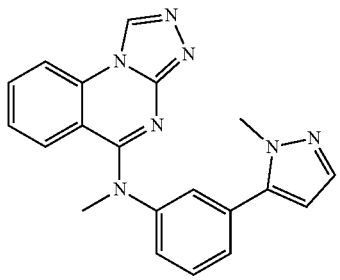 [SMILES: CN(c1cccc(-c2ccnn2C)c1)c1nc2nncn2c2ccccc12]

A mixture of N-(3-iodophenyl)-N-methyl-[1,2,4]triazolo[4,3-a]quinazolin-5-amine (Example 101) (15 mg, 0.037 mmol), K₃PO₄ (15.87 mg, 0.075 mmol), Pd(OAc)₂ (1.679 mg, 0.0075 mmol), tricyclohexylphosphine (2.097 mg, 0.0075 mmol), and 1-methyl-5-(4,4,5,5-tetramethyl-1,3,2-dioxaborolan-2-yl)-1H-pyrazole (11.67 mg, 0.056 mmol) in dioxane/water (0.2 mL) was heated at 100° C. for 1 h. The reaction mixture was subjected to solid phase extraction (washed with MeOH, then eluted with NH₃ in MeOH) using Bond Elut SCX cartridge (Agilent), and the collected fractions were concentrated in vacuo. The residue was purified by column chromatography (Si-column, CHCl₃:MeOH=10:0-9:1) to afford the desired product: ¹H NMR (Methanol-d₄) δ 9.44 (s, 1H), 8.24-8.10 (m, 1H), 7.76 (ddd, J=8.5, 7.3, 1.3 Hz, 1H), 7.59-7.55 (m, 1H), 7.45-7.39 (m, 4H), 7.33 (t, J=1.9 Hz, 1H), 7.24 (ddd, J=8.6, 7.3, 1.3 Hz, 1H), 6.32 (d, J=2.0 Hz, 1H), 3.71 (s, 3H), 3.62 (s, 3H); LCMS(m/z) 356.3 [M+H]+.

Example 160. N-Methyl-N-(2'-methyl-[1,1'-biphenyl]-3-yl)-[1,2,4]triazolo[4,3-a]quinazolin-5-amine

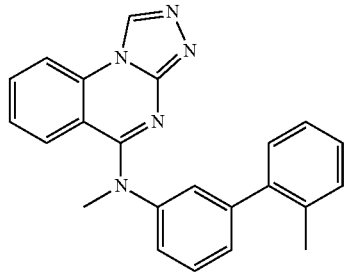

A mixture of N-(3-iodophenyl)-N-methyl-[1,2,4]triazolo[4,3-a]quinazolin-5-amine (Example 101) (15 mg, 0.037 mmol), K₃PO₄ (15.87 mg, 0.075 mmol), Pd(OAc)₂ (1.679 mg, 0.0075 mmol), tricyclohexylphosphine (2.097 mg, 0.0075 mmol), and o-tolylboronic acid (7.62 mg, 0.056 mmol) in dioxane/water (0.2 mL) was heated at 100° C. for 1 h. The reaction mixture was subjected to solid phase extraction (washed with MeOH, then eluted with NH₃ in MeOH) using Bond Elut SCX cartridge (Agilent), and the collected fractions were concentrated in vacuo. The residue was purified by column chromatography (Si-column, CHCl₃:MeOH=10:0-9:1) to afford the desired product: ¹H NMR (Methanol-d₄) δ 9.40 (s, 1H), 8.23-8.08 (m, 1H), 7.74 (ddd, J=8.5, 7.2, 1.3 Hz, 1H), 7.51 (t, J=7.8 Hz, 1H), 7.41 (dd, J=8.5, 1.1 Hz, 1H), 7.34 (ddd, J=8.1, 2.3, 1.1 Hz, 1H), 7.27-7.20 (m, 2H), 7.17-7.13 (m, 3H), 7.07 (t, J=1.9 Hz, 2H), 3.68 (s, 3H), 2.02 (s, 3H); LCMS(m/z) 366.3 [M+H]+.

Example 161. N-(4'-(tert-Butyl)-[1,1'-biphenyl]-3-yl)-N-methyl-[1,2,4]triazolo[4,3-a]quinazolin-5-amine

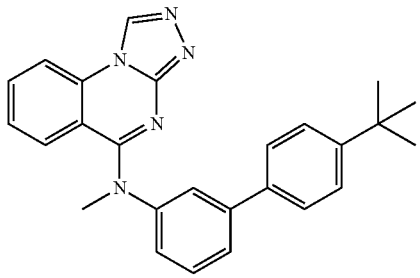 [SMILES: CN(c1cccc(-c2ccc(C(C)(C)C)cc2)c1)c1nc2nncn2c2ccccc12]

NA mixture of N-(3-iodophenyl)-N-methyl-[1,2,4]triazolo[4,3-a]quinazolin-5-amine (Example 101) (15 mg, 0.037 mmol), K$_3$PO$_4$ (15.87 mg, 0.075 mmol), Pd(OAc)$_2$ (1.679 mg, 0.0075 mmol), tricyclohexylphosphine (2.097 mg, 0.0075 mmol), and (4-(tert-butyl)phenyl)boronic acid (9.98 mg, 0.056 mmol) in dioxane/water (0.2 mL) was heated at 100° C. for 1 h. The reaction mixture was subjected to solid phase extraction (washed with MeOH, then eluted with NH$_3$ in MeOH) using Bond Elut SCX cartridge (Agilent), and the collected fractions were concentrated in vacuo. The residue was purified by column chromatography (Si-column, CHCl$_3$:MeOH=100:0-85:15) to afford the desired product: $^1$H NMR (Methanol-d$_4$) δ 9.43 (s, 1H), 8.23-8.09 (m, 1H), 7.74 (ddd, J=8.5, 7.3, 1.3 Hz, 1H), 7.58 (ddd, J=7.8, 1.7, 1.0 Hz, 1H), 7.51 (dd, J=4.1, 2.1 Hz, 1H), 7.48-7.41 (m, 6H), 7.29-7.11 (m, 2H), 3.71 (s, 3H), 1.32 (s, 9H); LCMS (m/z) 408.3.

Example 162. N-(3'-([1,2,4]Triazolo[4,3-a]quinazolin-5-yl(methyl)amino)-[1,1'-biphenyl]-4-yl)acetamide

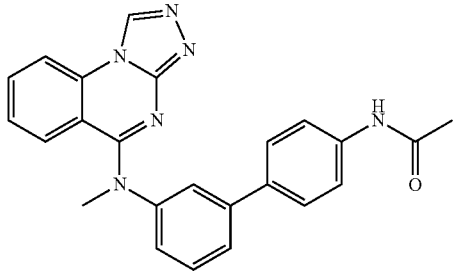

A mixture of N-(3-iodophenyl)-N-methyl-[1,2,4]triazolo[4,3-a]quinazolin-5-amine (Example 101) (15 mg, 0.037 mmol), K$_3$PO$_4$ (15.87 mg, 0.075 mmol), Pd(OAc)$_2$ (1.679 mg, 0.0075 mmol), tricyclohexylphosphine (2.097 mg, 0.0075 mmol), and (4-acetamidophenyl)boronic acid (9.98 mg, 0.056 mmol) in dioxane/water (0.2 mL) was heated at 100° C. for 1 h. The reaction mixture was subjected to solid phase extraction (washed with MeOH, then eluted with NH$_3$ in MeOH) using Bond Elut SCX cartridge (Agilent), and the collected fractions were concentrated in vacuo. The residue was purified by column chromatography (Si-column, CHCl$_3$:MeOH=100:0-85:15) to afford the desired product: $^1$H NMR (Methanol-d4) δ 9.42 (s, 1H), 8.16 (d, J=8.3 Hz, 1H), 7.77-7.69 (m, 1H), 7.60-7.55 (m, 3H), 7.50 (ddd, J=10.8, 5.8, 3.2 Hz, 4H), 7.42 (m, 1H), 7.24-7.13 (m, 2H), 3.71 (s, 3H), 2.12 (s, 3H); LCMS(m/z) 409.3.

Example 163. N5-(4'-Fluoro-[1,1'-biphenyl]-3-yl)-N5-methyl-[1,2,4]triazolo[4,3-a]quinazoline-5,8-diamine

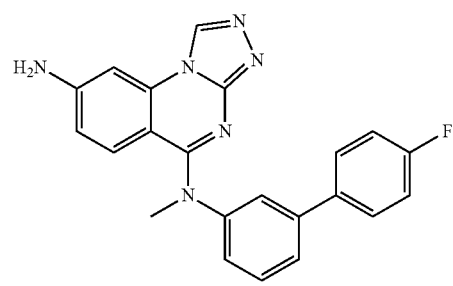

(Step 1) Synthesis of 2-chloro-N-(3-iodophenyl)-N-methyl-7-nitroquinazolin-4-amine

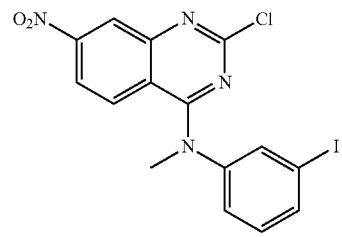 [SMILES: CN(c1cccc(I)c1)c1nc(Cl)nc2cc([N+](=O)[O-])ccc12]

To a solution of 2-chloro-7-nitroquinazolin-4(3H)-one (400 mg, 1.639 mmol) in DMF (8.2 mL) were added 3-iodo-N-methylaniline (382 mg, 1.639 mmol) and sodium hydride (39.3 mg, 1.639 mmol), and the mixture was stirred for 0.5 h at RT. The reaction mixture was diluted with AcOEt, washed successively with water and brine. The organic layer was concentrated in vacuo. The residue was used for the next step without further purification. LCMS (m/z) 440.99 [M+H]$^+$.

(Step 2) Synthesis of 2-hydrazinyl-N-(3-iodophenyl)-N-methyl-7-nitroquinazolin-4-amine

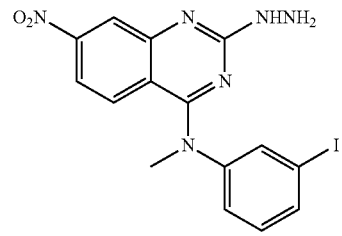 [SMILES: CN(c1cccc(I)c1)c1nc(NN)nc2cc([N+](=O)[O-])ccc12]

A mixture of 2-chloro-N-(3-iodophenyl)-N-methyl-7-nitroquinazolin-4-amine (crude, 256 mg, 0.581 mmol) and hydrazine hydrate (58.2 mg, 1.162 mmol) in EtOH (2.9 mL) was stirred for 2 h at 50° C. The reaction mixture was diluted with AcOEt, washed successively with water and brine, and dried over Na$_2$SO$_4$. The organic layer was concentrated in vacuo. The residue was used for the next step without further purification. LCMS(m/z) 437.03 [M+H]$^+$.

(Step 3) Synthesis of N-(3-iodophenyl)-N-methyl-8-nitro-[1,2,4]triazolo[4,3-a]quinazolin-5-amine

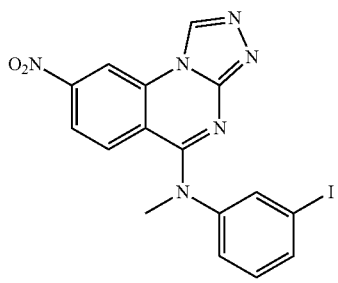 [SMILES: CN(c1cccc(I)c1)c1nc2nncn2c2cc([N+](=O)[O-])ccc12]

A mixture of 2-hydrazinyl-N-(3-iodophenyl)-N-methyl-7-nitroquinazolin-4-amine (208 mg, 0.477 mmol) and triethoxymethane (5 mL, 0.477 mmol) was heated to 100° C. for overnight. The reaction mixture was concentrated in vacuo. The residue was purified by column chromatography (Si-column, CHCl$_3$:MeOH=10:0-9:1) to give the desired product. LCMS(m/z) 447.04 [M+H]$^+$.

(Step 4) Synthesis of N-(4'-fluoro-[1,1'-biphenyl]-3-yl)-N-methyl-8-nitro-[1,2,4]triazolo[4,3-a]quinazolin-5-amine

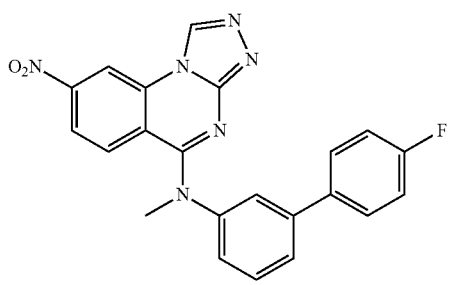 [SMILES: CN(c1cccc(-c2ccc(F)cc2)c1)c1nc2nncn2c2cc([N+](=O)[O-])ccc12]

A mixture of N-(3-iodophenyl)-N-methyl-8-nitro-[1,2,4]triazolo[4,3-a]quinazolin-5-amine (50 mg, 0.112 mmol), tricyclohexylphosphine (6.28 mg, 0.022 mmol), K$_3$PO$_4$ (47.6 mg, 0.224 mmol), Pd(OAc)$_2$ (5.03 mg, 0.022 mmol) and (4-fluorophenyl)boronic acid (23.52 mg, 0.168 mmol) in dioxane/water (0.56 mL) was stirred for 1 h at 100° C. The reaction mixture was subjected to solid phase extraction (washed with MeOH, then eluted with NH$_3$ in MeOH) using Bond Elut SCX cartridge (Agilent), and the collected fractions were concentrated in vacuo. The filtrate was concentrated in vacuo. The residue was used for the next step without further purification. LCMS(m/z) 415.18 [M+H]$^+$.

(Step 5) Synthesis of N5-(4'-fluoro-[1,1'-biphenyl]-3-yl)-N5-methyl-[1,2,4]triazolo[4,3-a]quinazoline-5,8-diamine A mixture of N-(4'-fluoro-[1,1'-biphenyl]-3-yl)-N-methyl-8-nitro-[1,2,4]triazolo[4,3-a]quinazolin-5-amine (crude, 36 mg) and Pd/C (10 mg) in EtOH (0.43 mL) was stirred for overnight at 60° C. under H$_2$ atmosphere. After removal of Pd/C by filtration, the filtrate was concentrated in vacuo. The residue was purified by column chromatography (Si-column, CHCl$_3$ MeOH=10:0-85:15) to afford the desired product: $^1$H NMR (CDCl$_3$) δ 8.81 (s, 1H), 7.52-7.39 (m, 4H), 7.30 (dd, J=2.5, 1.4 Hz, 1H), 7.17-7.07 (m, 4H), 6.92 (d, J=2.2 Hz, 1H), 6.36 (dd, J=9.1, 2.3 Hz, 1H), 4.44 (s, 2H), 3.67 (s, 3H); LCMS(m/z) 385.3.

Example 164. N-Methyl-N-(4'-methyl-[1,1'-biphenyl]-3-yl)-8-nitroso-[1,2,4]triazolo[4,3-a]quinazolin-5-amine

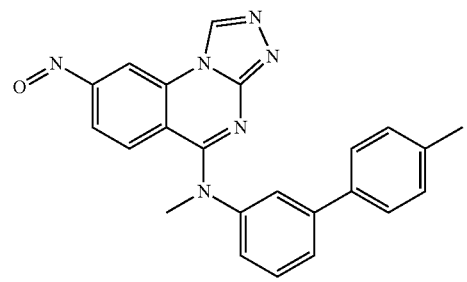 [SMILES: Cc1ccc(-c2cccc(N(C)c3nc4nncn4c4cc(N=O)ccc34)c2)cc1]

To a solution of N-methyl-N-(4'-methyl-[1,1'-biphenyl]-3-yl)-8-nitro-[1,2,4]triazolo[4,3-a]quinazolin-5-amine (Example 179, Step 1, 41.0 mg, crude) in EtOH (0.5 mL) was added Pd/C (6 mg), and the suspension was stirred overnight at 60° C. under H$_2$ atmosphere. After removal of Pd/C by filtration, the filtrate was concentrated in vacuo. The residue was purified by column chromatography (Si-column, CHCl$_3$:MeOH=10:0-85:15) to afford the desired product: $^1$H NMR (Methanol-d4) δ 8.05 (s, 1H), 6.21 (dt, J=7.8, 1.4 Hz, 1H), 6.14 (m, 3H), 5.96-5.90 (m, 3H), 5.86 (ddd, J=7.7, 2.2, 1.2 Hz, 1H), 5.79 (d, J=9.3 Hz, 1H), 5.68 (d, J=2.3 Hz, 1H), 5.09 (dd, J=9.3, 2.3 Hz, 1H), 2.35 (s, 3H), 1.59 (s, 3H); LCMS(m/z) 395.3.

Example 165. N-(3-Cyclohexylphenyl)-N-methyl-[1,2,4]triazolo[4,3-a]quinazolin-5-amine

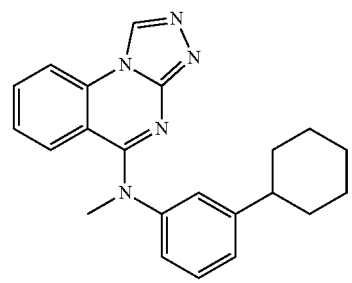

(Step 1) Synthesis of N-(3-cyclohexenylphenyl)-N-methyl-[1,2,4]triazolo[4,3-a]quinazolin-5-amine

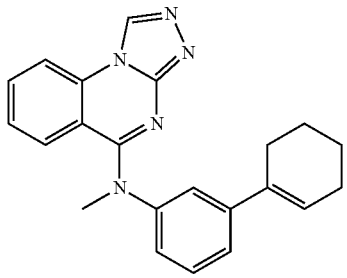

A mixture of N-(3-iodophenyl)-N-methyl-[1,2,4]triazolo[4,3-a]quinazolin-5-amine (Example 101) (20 mg, 0.050 mmol), tricyclohexylphosphine (2.80 mg, 0.010 mmol), $K_3PO_4$ (21.16 mg, 0.100 mmol), Pd(OAc)$_2$ (2.238 mg, 0.010 mmol) and cyclohex-1-en-1-ylboronic acid (9.42 mg, 0.075 mmol) in dioxane/water (0.25 mL) was treated in a microwave reactor for 1 h at 100° C. The reaction mixture was subjected to solid phase extraction (washed with MeOH, then eluted with NH$_3$ in MeOH) using Bond Elut SCX cartridge (Agilent), and the collected fractions were concentrated in vacuo. The residue was used for the next step without further purification. LCMS: 356.18 (M+H).

(Step 2) Synthesis of N-(3-cyclohexylphenyl)-N-methyl-[1,2,4]triazolo[4,3-a]quinazolin-5-amine To a solution of N-(3-cyclohexenylphenyl)-N-methyl-[1,2,4]triazolo[4,3-a]quinazolin-5-amine (crude, 31 mg, 0.087 mmol) in EtOH (0.436 mL) was added Pd/C (5 mg), and the mixture was stirred overnight at 50° C. under H$_2$ atmosphere. After removal of Pd/C by filtration, the filtrate was concentrated in vacuo. The residue was purified by column chromatography (Si-column, CHCl$_3$:MeOH=10:0-9:1) to afford the desired product: $^1$H NMR (Methanol-d$_4$) δ 9.39 (s, 1H), 8.09 (ddd, J=8.4, 1.2, 0.6 Hz, 1H), 7.69 (ddd, J=8.4, 7.2, 1.4 Hz, 1H), 7.34 (t, J=7.8 Hz, 1H), 7.21-7.14 (m, 2H), 7.13-7.07 (m, 2H), 7.04 (t, J=1.9 Hz, 1H), 3.62 (s, 3H), 2.45 (tt, J=8.2, 3.6 Hz, 1H), 1.86-1.65 (m, 6H), 1.37-1.28 (m, 4H); LCMS(m/z) 358.3.

Example 166. N-(4'-Ethyl-[1,1'-biphenyl]-3-yl)-N-methyl-[1,2,4]triazolo[4,3-a]quinazolin-5-amine

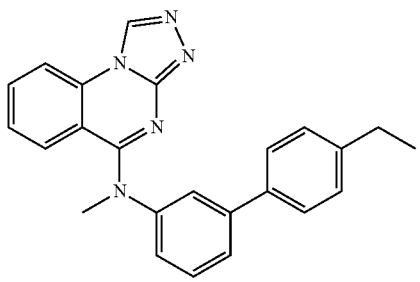 [SMILES: CCc1ccc(-c2cccc(N(C)c3nc4nncn4c4ccccc34)c2)cc1]

A mixture of N-(3-iodophenyl)-N-methyl-[1,2,4]triazolo[4,3-a]quinazolin-5-amine (Example 101) (20 mg, 0.050 mmol), tricyclohexylphosphine (2.80 mg, 0.010 mmol), $K_3PO_4$ (21.16 mg, 0.100 mmol), Pd(OAc)$_2$ (2.238 mg, 0.010 mmol) and (4-ethylphenyl)boronic acid (11.21 mg, 0.075 mmol) in dioxane/water (0.25 mL) was treated in a microwave reactor at 100° C. for 1 h. The reaction mixture was subjected to solid phase extraction (washed with MeOH, then eluted with NH$_3$ in MeOH) using Bond Elut SCX cartridge (Agilent), and the collected fractions were concentrated in vacuo. The residue was purified by column chromatography (Si-column, CHCl$_3$:MeOH=10:0-9:1) to afford the desired product: $^1$H NMR (Methanol-d4) δ 9.40 (s, 1H), 8.18-8.05 (m, 1H), 7.70 (ddd, J=8.4, 7.3, 1.3 Hz, 1H), 7.54 (ddd, J=7.8, 1.8, 1.1 Hz, 1H), 7.49-7.39 (m, 4H), 7.35 (dd, J=8.5, 1.3 Hz, 1H), 7.22-7.11 (m, 4H), 3.68 (s, 3H), 2.63 (q, J=7.6 Hz, 2H), 1.21 (t, J=7.6 Hz, 3H); LCMS (m/z) 380.3.

Example 167. N5-(4'-Methoxy-[1,1'-biphenyl]-3-yl)-N5-methyl-[1,2,4]triazolo[4,3-a]quinazoline-5,8-diamine

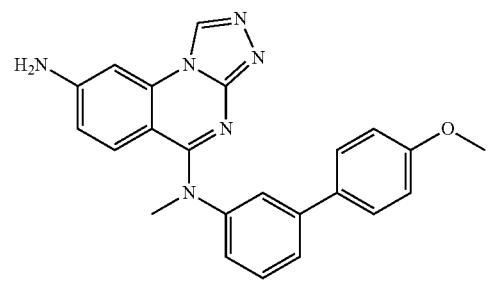

(Step 1) Synthesis of N-(4'-methoxy-[1,1'-biphenyl]-3-yl)-N-methyl-8-nitro-[1,2,4]triazolo[4,3-a]quinazolin-5-amine

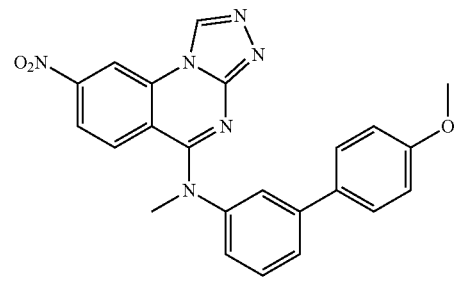 [SMILES: COc1ccc(-c2cccc(N(C)c3nc4nncn4c4cc([N+](=O)[O-])ccc34)c2)cc1]

A mixture of N-(3-iodophenyl)-N-methyl-8-nitro-[1,2,4]triazolo[4,3-a]quinazolin-5-amine 6 (40 mg, 0.090 mmol), tricyclohexylphosphine (5.03 mg, 0.018 mmol), $K_3PO_4$ (38.1 mg, 0.179 mmol), Pd(OAc)$_2$ (4.03 mg, 0.018 mmol) and (4-methoxyphenyl)boronic acid (20.43 mg, 0.134 mmol) in dioxane/water (0.45 mL) was treated in a microwave reactor for 1 h at 100° C.

The reaction mixture was subjected to solid phase extraction (washed with MeOH, then eluted with NH$_3$ in MeOH) using Bond Elut SCX cartridge (Agilent), and the collected fractions were concentrated in vacuo. The residue was used for the next step without further purification. LCMS(m/z) 427.18 [M+H]$^+$.

(Step 2) Synthesis of N5-(4'-methoxy-[1,1'-biphenyl]-3-yl)-N5-methyl-[1,2,4]triazolo[4,3-a]quinazoline-5,8-diamine To a solution of N-(4'-methoxy-[1,1'-biphenyl]-3-yl)-N-methyl-8-nitro-[1,2,4]triazolo[4,3-a]quinazolin-5-amine (crude, 24 mg) in EtOH (0.28 mL) was added Pd/C (5 mg), and the mixture was stirred overnight at 60° C. under $H_2$ atmosphere. After removal of Pd/C by filtration, the filtrate was concentrated in vacuo. The residue was purified by column chromatography (Si-column, $CHCl_3$:MeOH=10:0-9:1) to afford the desired product: $^1$H NMR (Methanol-d4) δ 9.16 (s, 1H), 8.22 (s, 1H), 7.53-7.38 (m, 4H), 7.13 (ddd, J=7.8, 2.2, 1.1 Hz, 1H), 7.09-6.97 (m, 2H), 6.97-6.90 (m, 2H), 6.39 (dd, J=9.2, 2.2 Hz, 1H), 3.80 (s, 3H), 3.63 (s, 3H). LCMS(m/z) 397.3.

Example 168. N-(3'-((8-Amino-[1,2,4]triazolo[4,3-a]quinazolin-5-yl)(methyl)amino)-[1,1'-biphenyl]-4-yl)acetamide

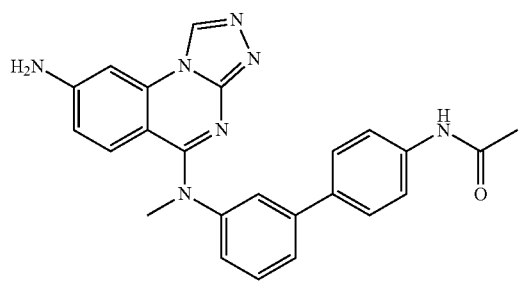

(Step 1) Synthesis of N-(3'-(methyl(8-nitro-[1,2,4]triazolo[4,3-a]quinazolin-5-yl)amino)-[1,1'-biphenyl]-4-yl)acetamide

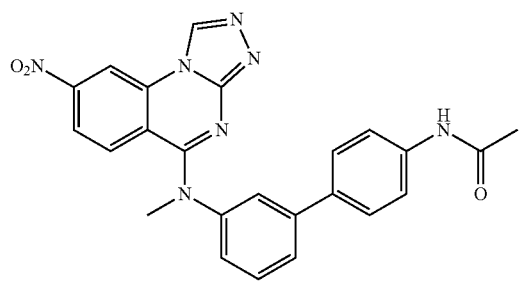 [SMILES: CC(=O)Nc1ccc(-c2cccc(N(C)c3nc4nncn4c4cc([N+](=O)[O-])ccc34)c2)cc1]

A mixture of N-(3-iodophenyl)-N-methyl-8-nitro-[1,2,4]triazolo[4,3-a]quinazolin-5-amine (40 mg, 0.090 mmol), tricyclohexylphosphine (5.03 mg, 0.018 mmol), $K_3PO_4$ (38.1 mg, 0.179 mmol), Pd(OAc)$_2$ (4.03 mg, 0.018 mmol) and (4-acetamidophenyl)boronic acid (24.07 mg, 0.134 mmol) in dioxane/water (0.45 mL) was heated to 100° C. for 1 h. The reaction mixture was subjected to solid phase extraction (washed with MeOH, then eluted with $NH_3$ in MeOH) using Bond Elut SCX cartridge (Agilent), and the collected fractions were concentrated in vacuo. The residue was used for the next step without further purification. LCMS(m/z) 454.19 [M+H]$^+$.

(Step 2) Synthesis of N-(3'-((8-amino-[1,2,4]triazolo[4,3-a]quinazolin-5-yl)(methyl)amino)-[1,1'-biphenyl]-4-yl)acetamide To a solution of N-(3'-(methyl(8-nitro-[1,2,4]triazolo[4,3-a]quinazolin-5-yl)amino)-[1,1'-biphenyl]-4-yl)acetamide (30 mg, crude) in EtOH (0.33 mL) was added Pd/C (5 mg), and the mixture was stirred under $H_2$ atmosphere for overnight at 50° C. After removal of Pd/C by filtration, the filtrate was concentrated in vacuo. The residue was purified by column chromatography (Si-column, $CHCl_3$:MeOH=10:0-9:1) to afford the desired product: $^1$H NMR (Methanol-d4) δ 9.16 (s, 1H), 7.67-7.37 (m, 7H), 7.19-7.13 (m, 1H), 7.07-7.00 (m, 2H), 6.39 (dd, J=9.2, 2.2 Hz, 1H), 3.64 (s, 3H), 2.13 (s, 3H); LCMS(m/z) 424.3.

Example 169. N5-(3-Fluorophenyl)-N5-methyl-[1,2,4]triazolo[4,3-a]quinazoline-5,8-diamine

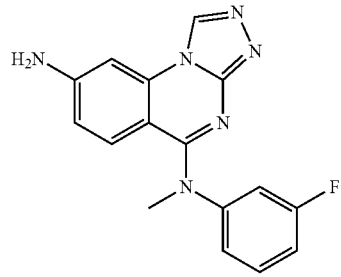

(Step 1) Synthesis of 2-chloro-N-(3-fluorophenyl)-N-methyl-7-nitroquinazolin-4-amine

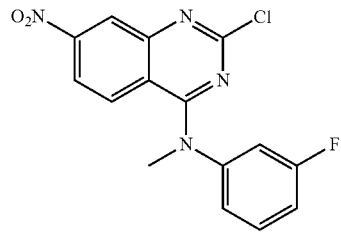 [SMILES: CN(c1cccc(F)c1)c1nc(Cl)nc2cc([N+](=O)[O-])ccc12]

To a solution of 2,4-dichloro-7-nitroquinazoline (100 mg, 0.41 mmol) in DMF (2.1 mL) were added 3-fluoro-N-methylaniline (51.3 mg, 0.41 mmol) and sodium hydride (9.83 mg, 0.41 mmol), and the mixture was stirred for 1 h at RT. The reaction mixture was diluted with AcOEt, washed successively with water and brine. The organic layer was concentrated in vacuo. The residue was used for the next step without further purification. LCMS(m/z) 332.8 [M+H]$^+$.

(Step 2) Synthesis of N-(3-fluorophenyl)-2-hydrazinyl-N-methyl-7-nitroquinazolin-4-amine

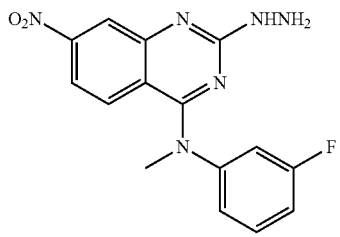 [SMILES: CN(c1cccc(F)c1)c1nc(NN)nc2cc([N+](=O)[O-])ccc12]

To a solution of 2-chloro-N-(3-fluorophenyl)-N-methyl-7-nitroquinazolin-4-amine (crude, 114 mg, 0.343 mmol) in EtOH (1.7 mL) was added hydrazine hydrate (17.15 mg, 0.343 mmol), and the mixture was stirred for 1 h at 50° C. The reaction mixture was diluted with AcOEt, washed successively with water and brine. The organic layer was concentrated in vacuo. The residue was used for the next step without further purification. LCMS(m/z) 328.9 [M+H]+.

(Step 3) Synthesis of N-(3-fluorophenyl)-N-methyl-8-nitro-[1,2,4]triazolo[4,3-a]quinazolin-5-amine

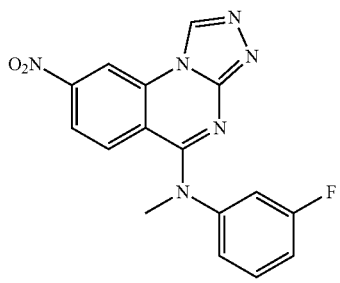

A mixture of N-(3-fluorophenyl)-2-hydrazinyl-N-methyl-7-nitroquinazolin-4-amine (crude, 101 mg, 0.308 mmol) and triethoxymethane (3 mL, 0.308 mmol) was stirred at 100° C. overnight. The reaction mixture was concentrated in vacuo, and the residue was purified by column chromatography (Si-column, CHCl$_3$:MeOH=10:0-85:15) to give the desired product. LCMS(m/z) 339.08 [M+H]+.

(Step 4) Synthesis of N5-(3-fluorophenyl)-N5-methyl-[1,2,4]triazolo[4,3-a]quinazoline-5,8-diamine To a solution of N-(3-fluorophenyl)-N-methyl-8-nitro-[1,2,4]triazolo[4,3-a]quinazolin-5-amine (66 mg, 0.195 mmol) in EtOH (0.98 mL) was added Pd/C (10 mg), and the suspension was stirred under H2 atmosphere overnight at 60° C. After removal of Pd/C by filtration, the filtrate was concentrated in vacuo. The residue was purified by column chromatography (Si-column, CHCl$_3$:MeOH=10:0-85:15) to afford the desired product: $^1$H NMR (Methanol-d4) δ 9.15 (d, J=1.8 Hz, 1H), 7.35 (td, J=8.2, 6.5 Hz, 1H), 7.08-6.96 (m, 5H), 6.42 (dt, J=9.4, 2.0 Hz, 1H), 3.56 (d, J=1.3 Hz, 3H); LCMS(m/z) 309.1.

Example 170. N5-Ethyl-N5-phenyl-[1,2,4]triazolo[4,3-a]quinazoline-5,8-diamine

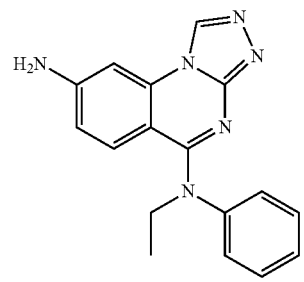

(Step 1) Synthesis of 2-chloro-N-ethyl-7-nitro-N-phenylquinazolin-4-amine

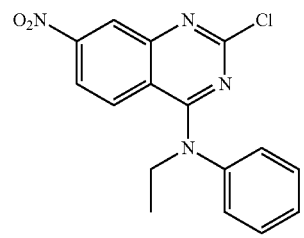 [SMILES: CCN(c1ccccc1)c1nc(Cl)nc2cc([N+](=O)[O-])ccc12]

To a solution of 2,4-dichloro-7-nitroquinazoline (200 mg, 0.820 mmol) in DMF (4.1 mL) were added N-ethylaniline (99 mg, 0.820 mmol) and sodium hydride (19.67 mg, 0.820 mmol), and the mixture was stirred for 1 h at RT. The reaction mixture was diluted with AcOEt, washed successively with water and brine. The organic layer was concentrated in vacuo. The residue was used for the next step without further purification. LCMS(m/z) 329.08 [M+H]+.

(Step 2) Synthesis of N-ethyl-2-hydrazinyl-7-nitro-N-phenylquinazolin-4-amine

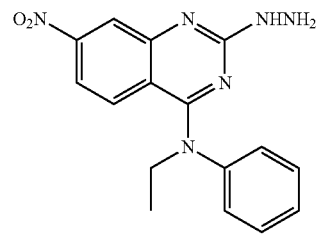 [SMILES: CCN(c1ccccc1)c1nc(NN)nc2cc([N+](=O)[O-])ccc12]

To a solution of 2-chloro-N-ethyl-7-nitro-N-phenylquinazolin-4-amine (crude, 171 mg, 0.52 mmol) in EtOH (2.6 mL) was added hydrazine hydrate (65.1 mg, 1.3 mmol), and the mixture was stirred for 3 h at RT. The reaction mixture was diluted with AcOEt, washed successively with water and brine, and dried over Na$_2$SO$_4$. The organic layer was concentrated vacuo. The residue was used for the next step without further purification. LCMS(m/z) 325.08 [M+H]+.

(Step 3) Synthesis of N-ethyl-8-nitro-N-phenyl-[1,2,4]triazolo[4,3-a]quinazolin-5-amine

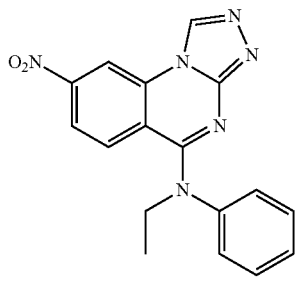 [SMILES: CCN(c1ccccc1)c1nc2nncn2c2cc([N+](=O)[O-])ccc12]

A mixture of N-ethyl-2-hydrazinyl-7-nitro-N-phenylquinazolin-4-amine (147 mg, 0.453 mmol) and triethoxymethane (5 mL, 0.453 mmol) was stirred at 100° C. overnight. The reaction mixture was concentrated in vacuo. The residue was purified by column chromatography (Si-column, CHCl$_3$:MeOH=10:0-9:1) to give the desired product. LCMS (m/z) 335.03 [M+H]$^+$.

(Step 4) Synthesis of N5-ethyl-N5-phenyl-[1,2,4]triazolo[4,3-a]quinazoline-5,8-diamine To a solution of N-ethyl-8-nitro-N-phenyl-[1,2,4]triazolo[4,3-a]quinazolin-5-amine (102 mg, 0.305 mmol) in EtOH (1.5 mL) was added Pd/C (15 mg), and the suspension was stirred overnight at 60° C. under H$_2$ atmosphere. After removal of Pd/C by filtration, the filtrate was concentrated in vacuo. The residue was purified by column chromatography (Si-column, CHCl$_3$:MeOH=10:0-9:1) to afford the desired product: $^1$H NMR (CDCl$_3$) δ 8.78 (s, 1H), 7.35 (t, J=7.6 Hz, 2H), 7.22 (s, 1H), 7.13 (d, J=7.6 Hz, 2H), 7.00 (d, J=9.3 Hz, 1H), 6.89 (s, 1H), 6.36-6.25 (m, 1H), 3.72 (q, J=7.0 Hz, 2H), 1.31 (t, J=7.0 Hz, 3H); LCMS(m/z) 305.2.

Example 171. 5-(3,4-Dihydroquinolin-1(2H)-yl)-[1,2,4]triazolo[4,3-a]quinazolin-8-amine

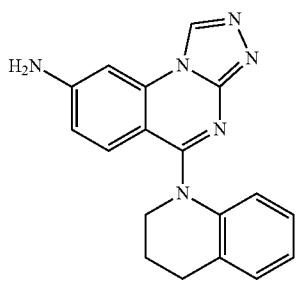

(Step 1) Synthesis of 2-chloro-4-(3,4-dihydroquinolin-1(2H)-yl)-7-nitroquinazoline

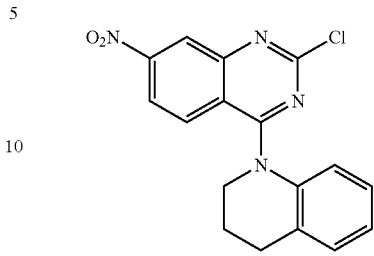

To a solution of 2,4-dichloro-7-nitroquinazoline (500 mg, 2.049 mmol) in DMF (3.1 mL) were added 1,2,3,4-tetrahydroquinoline (273 mg, 2.049 mmol) and sodium hydride (49.2 mg, 2.049 mmol), and the mixture was stirred for 1 h at RT. The reaction mixture was diluted with AcOEt, washed successively with water and brine, and dried over Na$_2$SO$_4$. The organic layer was concentrated in vacuo. The residue was used for the next step without further purification. LCMS(m/z) 341.03 [M+H]$^+$.

(Step 2) Synthesis of 4-(3,4-dihydroquinolin-1(2H)-yl)-2-hydrazinyl-7-nitroquinazoline

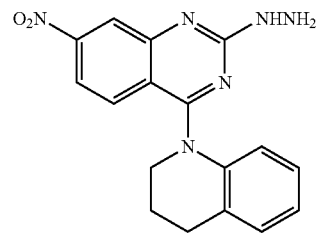 [SMILES: NNc1nc(N2CCCc3ccccc32)c2ccc([N+](=O)[O-])cc2n1]

To a solution of 2-chloro-4-(3,4-dihydroquinolin-1(2H)-yl)-7-nitroquinazoline (462 mg, crude) in EtOH (6.8 mL) was added hydrazine hydrate (136 mg, 2.71 mmol), and the mixture was stirred for 1 h at RT. The reaction mixture was diluted with AcOEt and washed successively with water and brine. The organic layer was concentrated in vacuo. The residue was used for the next step without further purification. LCMS(m/z) 337.08 [M+H]$^+$.

(Step 3) Synthesis of 5-(3,4-dihydroquinolin-1(2H)-yl)-8-nitro-[1,2,4]triazolo[4,3-a]quinazoline

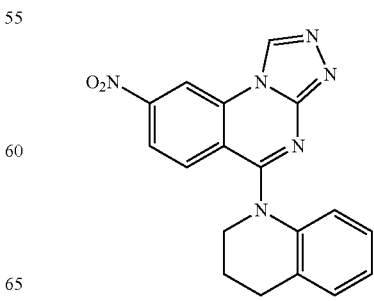

A mixture of 4-(3,4-dihydroquinolin-1(2H)-yl)-2-hydrazinyl-7-nitroquinazoline (387 mg, 1.151 mmol) and triethoxymethane (171 mg, 1.151 mmol) was stirred at 100° C. overnight.

The reaction mixture was concentrated in vacuo. The residue was purified by column chromatography (Si-column, CHC₃:MeOH=10:0-9:1). LCMS(m/z) 347.13 [M+H]⁺.

(Step 4) Synthesis of 5-(3,4-dihydroquinolin-1(2H)-yl)-[1,2,4]triazolo[4,3-a]quinazolin-8-amine A mixture of 5-(3,4-dihydroquinolin-1(2H)-yl)-8-nitro-[1,2,4]triazolo[4,3-a]quinazoline (60 mg, 0.173 mmol) and Pd/C (5 mg) in EtOH (0.87 mL) was stirred overnight at 60° C. under H₂ atmosphere. After removal of Pd/C by filtration, the filtrate was concentrated in vacuo. The residue was purified by column chromatography (Si-column, CHCl₃:MeOH=10:0-9:1) to afford the desired product: $^1$H NMR (Methanol-d4) δ 9.14 (s, 1H), 7.17 (d, J=9.1 Hz, 1H), 7.15-7.11 (m, 1H), 7.01 (d, J=2.2 Hz, 1H), 6.91-6.82 (m, 2H), 6.55 (dd, J=7.7, 1.6 Hz, 1H), 6.45 (dd, J=9.1, 2.2 Hz, 1H), 3.86 (t, J=6.6 Hz, 2H), 2.81 (t, J=6.6 Hz, 2H), 2.02 (q, J=6.6 Hz, 2H); LCMS(m/z) 317.2.

Example 172. 8-Bromo-N-methyl-N-(4'-methyl-[1,1'-biphenyl]-3-yl)-[1,2,4]triazolo[4,3-a]quinazolin-5-amine

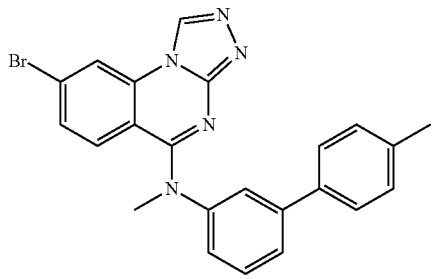

(Step 1) Synthesis of N,4'-Dimethyl-[1,1'-biphenyl]-3-amine

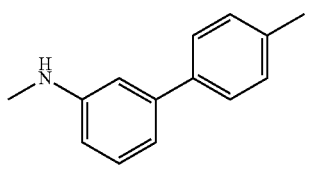

To a stirred solution of 3-iodo-N-methylaniline (2.0 g, 8.58 mmol) and p-tolylboronic acid (2.33 g, 17.16 mmol) in 1,4-dioxane/water (30 mL, 5:1) were added sodium carbonate (1.82 g, 171.7 mmol) and [1,1'-bis(diphenylphosphino)ferrocene]palladium(II) dichloride (0.630 g, 0.86 mmol) at RT, and the mixture was heated to 80° C. for 3 h. The progress of the reaction was monitored by TLC. After completion of the reaction, the reaction mixture was filtered through a bed of celite and washed with ethyl acetate. The organic layer was washed with brine, dried over Na₂SO₄, filtered and evaporated under reduced pressure. The residue was purified by silica gel column chromatography, eluted with 10% ethyl acetate/petroleum ether to give the desired product.

(Step 2) Synthesis of 8-bromo-N-methyl-N-(4'-methyl-[1,1'-biphenyl]-3-yl)-[1,2,4]triazolo[4,3-a]quinazolin-5-amine To a stirred solution of 8-bromo-5-chloro-[1,2,4]triazolo[4,3-a]quinazoline (0.06 g, 0.21 mmol) and N,4'-dimethyl-[1,1'-biphenyl]-3-amine (0.063 g, 0.32 mmol) in MeOH (4 mL) was added triethylamine (0.06 mL, 0.42 mmol) at RT, and the mixture was stirred at RT for 16 h. The progress of the reaction was monitored by TLC. After completion of the reaction, the reaction mixture was quenched with water and extracted with 10% methanol/dichloromethane. The organic layer was washed with brine, dried over Na₂SO₄, filtered and evaporated under reduced pressure. The residue was purified by silica gel column chromatography, eluted with 4% methanol/dichloromethane and further purified by prep. HPLC to afford the desired product: $^1$H NMR (DMSO-d₆) δ 9.63 (s, 1H), 8.66 (d, J=2.0 Hz, 1H), 7.62 (t, J=1.9 Hz, 1H), 7.59-7.51 (m, 3H), 7.48-7.40 (m, 2H), 7.32-7.19 (m, 4H), 3.59 (s, 3H), 2.32 (s, 3H); LCMS(m/z) 444.28/446.26.

Example 173. 8-Bromo-N-(4'-methoxy-[1,1'-biphenyl]-3-yl)-N-methyl-[1,2,4]triazolo[4,3-a]quinazolin-5-amine

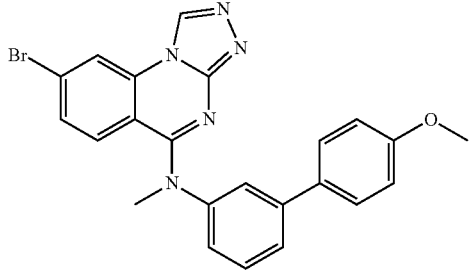

(Step 1) Synthesis of 3-iodo-N-methylaniline

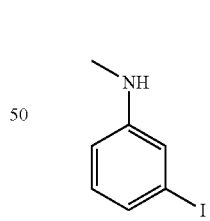

To a stirred solution of 3-iodoaniline (10 g, 45.66 mmol) in methanol (150 mL) was added 37% formaldehyde solution (5.55 mL, 68.49 mmol), followed by the addition of sodium methoxide (4.93 g, 91.32 mmol) at RT and the mixture was heated to 60° C. for 3 h. Then sodium borohydride (3.45 g, 91.32 mmol) was added to the solution at RT and the mixture was stirred at RT for 16 h. The progress of the reaction was monitored by TLC. After completion of the reaction, the reaction mixture was diluted with water and extracted with dichloromethane.

The organic layer was washed with brine, dried over Na₂SO₄, filtered and evaporated under reduced pressure.

(Step 2) Synthesis of 4'-Methoxy-N-methyl-[1,1'-biphenyl]-3-amine

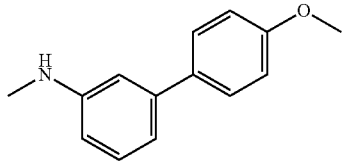

To a stirred solution of 3-iodo-N-methylaniline (2 g, 8.58 mmol) in 1,4-dioxane/water (30 mL, 5:1) were added (4-methoxyphenyl)boronic acid (2.61 g, 17.17 mmol), sodium carbonate (1.82 g, 171.7 mmol) and [1,1'-bis(diphenylphosphino)ferrocene]palladium(II) dichloride (0.630 g, 0.86 mmol) at RT, and the mixture was heated to 80° C. for 3 h. The progress of the reaction was monitored by TLC. After completion of the reaction, the reaction mixture was diluted with water and extracted with ethyl acetate. The organic layer was washed with brine, dried over $Na_2SO_4$, filtered and evaporated under reduced pressure. The residue was purified by silica gel column chromatography, eluted with 15% ethyl acetate/petroleum ether to give the desired product. LCMS(m/z) 214.36 [M+H]+.

(Step 3) Synthesis of 8-bromo-N-(4'-methoxy-[1,1'-biphenyl]-3-yl)-N-methyl-[1,2,4]triazolo[4,3-a]quinazolin-5-amine To a stirred solution of 8-bromo-5-chloro-[1,2,4]triazolo[4,3-a]quinazoline (0.04 g, 0.14 mmol) in MeOH (2 mL) were added 4'-methoxy-N-methyl-[1,1'-biphenyl]-3-amine (0.039 g, 0.18 mmol) and triethylamine (0.03 mL, 0.21 mmol) at RT, and the mixture was stirred at RT for 16 h. The progress of the reaction was monitored by TLC. After completion of the reaction, the reaction mixture was diluted with water and extracted with dichloromethane. The organic layer was washed with brine, dried over $Na_2SO_4$, filtered and evaporated under reduced pressure. The residue was purified by prep. HPLC to afford the desired product: $^1$H NMR (DMSO-$d_6$) δ 9.64 (s, 1H), 8.67 (d, J=2.0 Hz, 1H), 7.61-7.56 (m, 3H), 7.56-7.51 (m, 1H), 7.49-7.38 (m, 2H), 7.23 (dd, J=8.4, 2.7 Hz, 2H), 7.03-6.91 (m, 2H), 3.77 (s, 3H), 3.59 (d, J=2.1 Hz, 3H); LCMS(m/z) 460.19/462.20.

Example 174. N-(3'-((8-Bromo-[1,2,4]triazolo[4,3-a]quinazolin-5-yl)(methyl)amino)-[1,1'-biphenyl]-4-yl)acetamide (Step 1) Synthesis of N-(3'-(methylamino)-[1,1'-biphenyl]-4-yl)acetamide

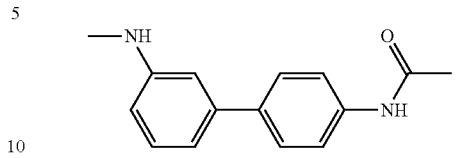

To a stirred solution of 3-iodo-N-methylaniline (2.0 g, 8.58 mmol) and (4-acetamidophenyl)boronic acid (3.07 g, 17.16 mmol) in 1,4-dioxane/water (30 mL, 5:1) was added sodium carbonate (1.82 g, 171.7 mmol) at RT and the mixture was degassed with argon for 10 min, followed by the addition of [1,1'-bis(diphenylphosphino)ferrocene]palladium(II) dichloride (0.630 g, 0.86 mmol) at RT and the mixture was heated to 80° C. for 3 h. The progress of the reaction was monitored by TLC. After completion of the reaction, the reaction mixture was filtered through a bed of celite and washed with ethyl acetate. The organic layer was washed with brine, dried over $Na_2SO_4$, filtered and evaporated under reduced pressure. The residue was purified by silica gel column chromatography and eluted with 20% ethyl acetate/petroleum ether to give the desired product. LCMS (m/z) 241.17 [M+H]$^+$.

(Step 2) Synthesis of N-(3'-((8-bromo-[1,2,4]triazolo[4,3-a]quinazolin-5-yl)(methyl)amino)-[1,1'-biphenyl]-4-yl)acetamide To a stirred solution of 8-bromo-5-chloro-[1,2,4]triazolo[4,3-a]quinazoline (0.110 g, 0.39 mmol) in MeOH (6 mL) were added N-(3'-(methylamino)-[1,1'-biphenyl]-4-y)acetamide (0.140 g, 0.58 mmol) and triethylamine (0.109 mL, 0.78 mmol) at RT and the mixture was stirred at RT for 16 h. The progress of the reaction was monitored by TLC. After completion of the reaction, the reaction mixture was diluted with water and extracted with 10% methanol/dichloromethane. The organic layer was washed with water, brine, dried over $Na_2SO_4$, filtered and evaporated under reduced pressure. The residue was purified by prep. HPLC to afford the desired product: $^1$H NMR (DMSO-$d_6$) δ 10.02 (s, 1H), 9.64 (s, 1H), 8.67 (d, J=2.0 Hz, 1H), 7.70-7.50 (m, 6H), 7.47-7.39 (m, 2H), 7.24 (dd, J=8.3, 4.8 Hz, 2H), 3.59 (s, 3H), 2.05 (s, 3H); LCMS(m/z) 486.8/488.8.

Example 175. 8-Chloro-N-(4'-methoxy-[1,1'-biphenyl]-3-yl)-N-methyl-[1,2,4]triazolo[4,3-a]quinazolin-5-amine

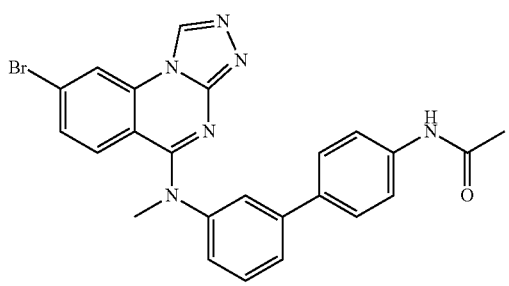

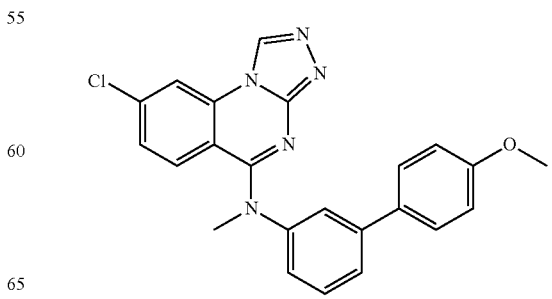

To a stirred solution of 5,8-dichloro-[1,2,4]triazolo[4,3-a]quinazoline (0.1 g, 0.42 mmol) in DMF (5 mL) were added 4'-methoxy-N-methyl-[1,1'-biphenyl]-3-amine (0.134 g, 0.63 mmol) and sodium hydroxide (0.34 g, 0.84 mmol) at RT and the mixture was stirred at RT for 3 h. The reaction mixture was diluted with water and extracted with ethyl acetate. The organic layer was washed with brine, dried over $Na_2SO_4$, filtered and evaporated under reduced pressure. The residue was purified by silica gel column chromatography, eluted with 6% methanol/dichloromethane to afford the desired product: $^1$H NMR (DMSO-$d_6$) δ 9.63 (s, 1H), 8.53 (t, J=1.2 Hz, 1H), 7.61-7.57 (m, 3H), 7.54 (dt, J=8.0, 1.3 Hz, 1H), 7.44 (t, J=7.8 Hz, 1H), 7.31 (m, 2H), 7.23 (ddd, J=8.0, 2.2, 1.1 Hz, 1H), 7.01-6.94 (m, 2H), 3.77 (s, 3H), 3.59 (s, 3H); LCMS(m/z) 416.3.

Example 176. 8-Chloro-N-(4'-chloro-[1,1'-biphenyl]-3-yl)-N-methyl-[1,2,4]triazolo[4,3-a]quinazolin-5-amine

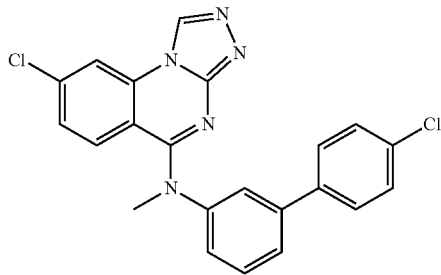

To a stirred solution of 5,8-dichloro-[1,2,4]triazolo[4,3-a]quinazoline (0.150 g, 0.63 mmol) in DMF (10 mL) were added 4'-chloro-N-methyl-[1,1'-biphenyl]-3-amine (0.178 g, 0.82 mmol) and triethylamine (0.18 mL, 1.26 mmol) at RT and the mixture was stirred at RT for 16 h. The reaction mixture was diluted with water and extracted with dichloromethane. The organic layer was washed with brine, dried over $Na_2SO_4$, filtered and evaporated under reduced pressure. The residue was purified by silica gel column chromatography, eluted with 6% methanol/dichloromethane, followed by prep. HPLC purification to afford the desired product: $^1$H NMR (DMSO-$d_6$) δ 9.64 (s, 1H), 8.54 (t, J=1.3 Hz, 1H), 7.74-7.65 (m, 3H), 7.59 (dt, J=8.0, 1.2 Hz, 1H), 7.54-7.43 (m, 3H), 7.36-7.24 (m, 3H), 3.59 (s, 3H); LCMS (m/z) 420.2.

Example 177. 8-Bromo-N-ethyl-N-phenyl-[1,2,4]triazolo[4,3-a]quinazolin-5-amine

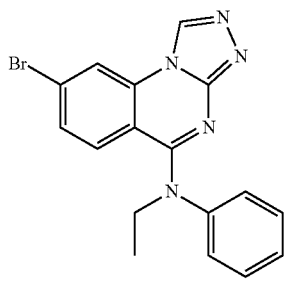

(Step 1) Synthesis of 7-bromo-2-chloro-N-ethyl-N-phenylquinazolin-4-amine

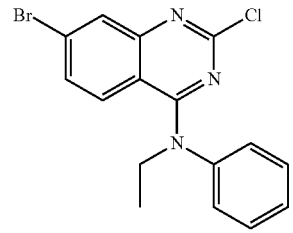

To a solution of 7-bromo-2,4-dichloroquinazoline (300 mg, 1.079 mmol) in DMF (5.4 mL) were added sodium hydride (25.9 mg, 1.079 mmol) and N-ethylaniline (131 mg, 1.079 mmol), and the mixture was stirred for 1 h at RT. The mixture was diluted with AcOEt and washed successively with water and brine. The organic layer was concentrated in vacuo. The residue was used for the next step without further purification. LCMS(m/z) 363.7 [M+H]$^+$.

(Step 2) Synthesis of 7-bromo-N-ethyl-2-hydrazinyl-N-phenylquinazolin-4-amine

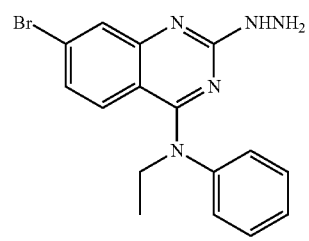

To a solution of 7-bromo-2-chloro-N-ethyl-N-phenylquinazolin-4-amine (234 mg, crude) in EtOH (3.2 ml) was added hydrazine hydrate (64.6 mg, 1.290 mmol), and the mixture was stirred at RT for 1 h. The reaction mixture was diluted with AcOEt, washed successively with water and brine, and dried over $Na_2SO_4$. The organic layer was concentrated in vacuo. The residue was used for the next step without further purification. LCMS(m/z) 359.8 [M+H]$^+$.

(Step 3) Synthesis of 8-bromo-N-ethyl-N-phenyl-[1,2,4]triazolo[4,3-a]quinazolin-5-amine A mixture of 7-bromo-N-ethyl-2-hydrazinyl-N-phenylquinazolin-4-amine (198 mg, crude) and triethoxymethane (7 mL, 0.553 mmol) was stirred overnight at 100° C. The reaction mixture was concentrated in vacuo. The residue was purified by column chromatography (Si-column, $CHCl_3$: MeOH=10:0-85:15) to afford the desired product: $^1$H NMR (Methanol-$d_4$) δ 9.38 (s, 1H), 8.37 (d, J=1.9 Hz, 1H), 7.46-7.40 (m, 2H), 7.37-7.30 (m, 1H), 7.26 (d, J=1.5 Hz, 3H), 7.02 (d, J=9.0 Hz, 1H), 4.21 (q, J=6.9 Hz, 2H), 1.29 (t, J=6.9 Hz, 3H); LCMS(m/z) 368.0/380.1.

Example 178. N5-(Cyclopropylmethyl)-N5-phenyl-[1,2,4]triazolo[4,3-a]quinazoline-5,8-diamine

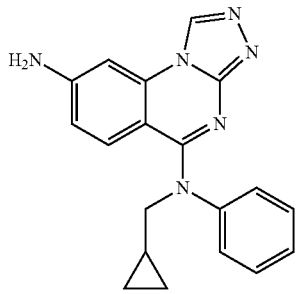

(Step 1) Synthesis of 2-chloro-N-(cyclopropylmethyl)-7-nitro-N-phenylquinazolin-4-amine

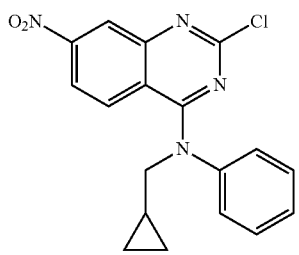 [SMILES: O=[N+]([O-])c1ccc2c(N(CC3CC3)c3ccccc3)nc(Cl)nc2c1]

To a solution of 2,4-dichloro-7-nitroquinazoline (250 mg, 1.024 mmol) in DMF (5.1 mL) were added N-(cyclopropylmethyl)aniline (151 mg, 1.024 mmol) and sodium hydride (24.58 mg, 1.024 mmol), and the mixture was stirred for 1 h at RT. The reaction mixture was diluted with AcOEt and washed successively with water and brine. The organic layer was concentrated in vacuo. The residue was used for the next step without further purification. LCMS(m/z) 355.18 [M+H]+.

(Step 2) Synthesis of N-(cyclopropylmethyl)-2-hydrazinyl-7-nitro-N-phenylquinazolin-4-amine

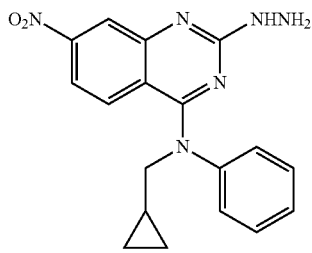 [SMILES: NNc1nc(N(CC2CC2)c2ccccc2)c2ccc([N+](=O)[O-])cc2n1]

To a solution of 2-chloro-N-(cyclopropylmethyl)-7-nitro-N-phenylquinazolin-4-amine (302 mg, crude) in EtOH (4.3 mL) was added hydrazine hydrate (42.6 mg, 0.851 mmol) and the mixture was stirred for 30 min at 50° C. The reaction mixture was diluted with AcOEt and washed successively with water and brine. The organic layer was concentrated in vacuo. The residue was used for the next step without further purification. LCMS(m/z) 351.18 [M+H]+.

(Step 3) Synthesis of N-(cyclopropylmethyl)-8-nitro-N-phenyl-[1,2,4]triazolo[4,3-a]quinazolin-5-amine

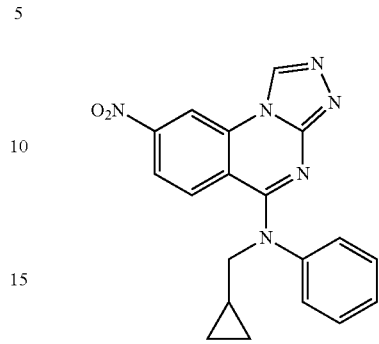

A mixture of N-(cyclopropylmethyl)-2-hydrazinyl-7-nitro-N-phenylquinazolin-4-amine (238 mg, crude) and triethoxymethane (7 mL, 0.679 mmol) was stirred at 100° C. for 4 h. The reaction mixture was concentrated in vacuo, and purified by column chromatography (Si-column, CHCl$_3$:MeOH=10:0-9:1) to give the desired product. LCMS(m/z) 361.13 [M+H]+.

(Step 4) N5-(cyclopropylmethyl)-N5-phenyl-[1,2,4]triazolo[4,3-a]quinazoline-5,8-diamine To a solution of N-(cyclopropylmethyl)-8-nitro-N-phenyl-[1,2,4]triazolo[4,3-a]quinazolin-5-amine (212 mg, 0.588 mmol) in EtOH (3.1 mL) was added Pd/C (10 mg) and the suspension was stirred overnight at 60° C. under H$_2$ atmosphere. After removal of Pd/C by filtration, the filtrate was concentrated in vacuo. The residue was purified by column chromatography (Si-column, CHCl$_3$:MeOH=10:0-85:15) to afford the desired product: $^1$H NMR (Methanol-d$_4$) δ 9.23 (m, 1H), 7.45-7.36 (m, 2H), 7.30-7.21 (m, 3H), 7.04-6.91 (m, 2H), 6.42-6.22 (m, 1H), 4.00 (d, J=6.8 Hz, 2H), 1.29-1.02 (m, 1H), 0.43-0.37 (m, 2H), 0.19-0.10 (m, 2H); LCMS(m/z) 331.1.

Example 179. N5-Methyl-N5-(4'-methyl-[1,1'-biphenyl]-3-yl)-[1,2,4]triazolo[4,3-a]quinazoline-5,8-diamine

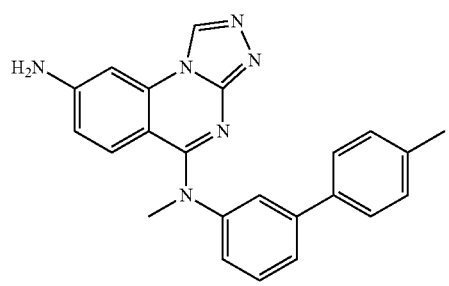 [SMILES: Cc1ccc(-c2cccc(N(C)c3nc4nncn4c4cc([N+](=O)[O-])ccc34)c2)cc1]

(Step 1) Synthesis of N-methyl-N-(4'-methyl-[1,1'-biphenyl]-3-yl)-8-nitro-[1,2,4]triazolo[4,3-a]quinazolin-5-amine

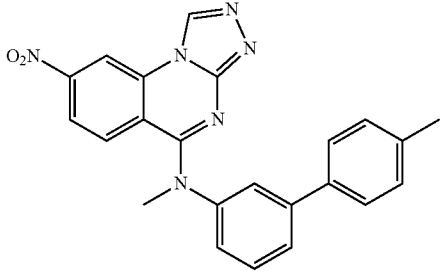

A mixture of N-(3-iodophenyl)-N-methyl-8-nitro-[1,2,4]triazolo[4,3-a]quinazolin-5-amine (50 mg, 0.112 mmol), Pd(OAc)$_2$ (5.03 mg, 0.022 mmol), K$_3$PO4 (47.6 mg, 0.224 mmol), tricyclohexylphosphine (6.28 mg, 0.022 mmol) and p-tolylboronic acid (18.28 mg, 0.134 mmol) in dioxane/water (0.56 mL) was heated for 1 h at 100° C. The reaction mixture was subjected to solid phase extraction (washed with MeOH, then eluted with NH$_3$ in MeOH) using Bond Elut SCX cartridge (Agilent), and the collected fractions were concentrated in vacuo. The residue was used for the next step without further purification. LCMS(m/z) 411.1 [M+H]$^+$.

(Step 2) Synthesis of N5-methyl-N5-(4'-methyl-[1,1'-biphenyl]-3-yl)-[1,2,4]triazolo[4,3-a]quinazoline-5,8-diamine To a solution of N-methyl-N-(4'-methyl-[1,1'-biphenyl]-3-yl)-8-nitro-[1,2,4]triazolo[4,3-a]quinazolin-5-amine (45 mg, 0.110 mmol) in EtOH (0.55 mL) was added Pd/C (5 mg), and the suspension was heated to 60° C. under H$_2$ atmosphere overnight. After removal of Pd/C by filtration, the filtrate was concentrated in vacuo. The residue was purified by column chromatography (Si-column, CHC$_3$:MeOH=10:0-80:20) to afford the desired product: $^1$H NMR (Methanol-d$_4$) δ 9.17 (s, 1H), 7.53-7.47 (m, 1H), 7.44-7.41 (m, 3H), 7.24-7.21 (m, 3H), 7.20-7.14 (m, 1H), 7.09 (d, J=9.2 Hz, 1H), 7.07 (d, J=2.2 Hz, 1H), 6.41 (dd, J=9.2, 2.2 Hz, 1H), 3.65 (s, 3H), 2.35 (s, 3H); LCMS(m/z) 381.2.

Example 180. (5-(Ethyl(phenyl)amino)-[1,2,4]triazolo[4,3-a]quinazolin-8-yl)methanol

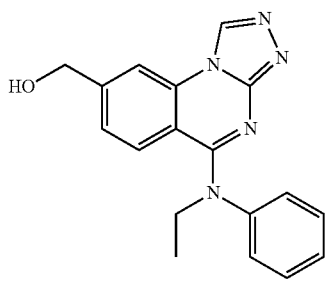 [SMILES: CCN(c1ccccc1)c1nc2nncn2c2cc(CO)ccc12]

(Step 1) Synthesis of N-ethyl-N-phenyl-8-vinyl-[1,2,4]triazolo[4,3-a]quinazolin-5-amine

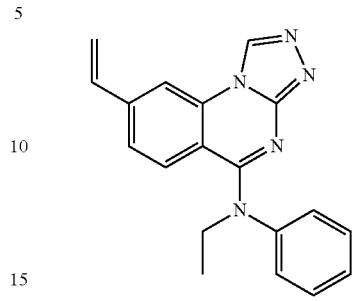

A mixture of 8-bromo-N-ethyl-N-phenyl-[1,2,4]triazolo[4,3-a]quinazolin-5-amine (Example 177) (300 mg, 0.815 mmol), K$_3$PO$_4$ (346 mg, 1.629 mmol), Pd(OAc)$_2$ (36.6 mg, 0.163 mmol), 4,4,5,5-tetramethyl-2-vinyl-1,3,2-dioxaborolane (188 mg, 1.222 mmol) and tricyclohexylphosphine (45.7 mg, 0.163 mmol) in dioxane/water (4.1 mL) was heated to 100° C. for 1 h. The reaction mixture was concentrated in vacuo. The residue was purified by column chromatography (Si-column, CHCl$_3$:MeOH=10:0-9:1) to give the desired product. LCMS(m/z) 316.08 [M+H]$^+$.

(Step 2) Synthesis of 5-(ethyl(phenyl)amino)-[1,2,4]triazolo[4,3-a]quinazoline-8-carbaldehyde

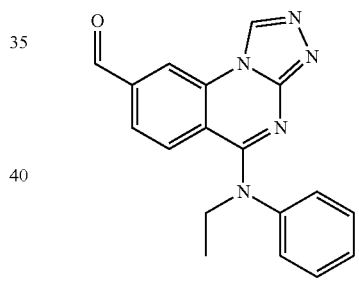

To a solution of N-ethyl-N-phenyl-8-vinyl-[1,2,4]triazolo[4,3-a]quinazolin-5-amine (100 mg, 0.317 mmol) in acetone/water (1:1, 1.6 mL) were added osmium(VIII) oxide (8.1 mg, 0.032 mmol) and sodium periodate (81 mg, 0.317 mmol), and the mixture was stirred overnight at RT. The reaction mixture was subjected to solid phase extraction (washed with MeOH, then eluted with NH$_3$ in MeOH) using Bond Elut SCX cartridge (Agilent), and the collected fractions were concentrated in vacuo. The residue was used for the next step without further purification. LCMS(m/z) 318.03 [M+H]$^+$.

(Step 3) Synthesis of (5-(ethyl(phenyl)amino)-[1,2,4]triazolo[4,3-a]quinazolin-8-yl)methanol To a solution of 5-(ethyl(phenyl)amino)-[1,2,4]triazolo[4,3-a]quinazoline-8-carbaldehyde (98 mg, 0.31 mmol) in MeOH (1.5 mL) was added NaBH$_4$ (12.90 mg, 0.341 mmol), and the mixture was stirred for 2 h at RT. The reaction mixture was concentrated in vacuo. The residue was purified by column chromatography (Si-column, CHC$_3$:MeOH=10:0-85:15) to afford the desired product: $^1$H NMR (Methanol-d4) δ 9.42 (d, J=0.9 Hz, 1H), 8.13 (s, 1H), 7.48-7.21 (m, 6H), 7.12 (d, J=8.7 Hz, 1H), 4.72 (s, 2H), 4.26 (q, J=7.0 Hz, 2H), 3.35 (s, 1H), 1.36-1.32 (t, J=7.0 Hz, 3H); LCMS(m/z) 320.1.

Example 181. N-Ethyl-8-(methoxymethyl)-N-phenyl-[1,2,4]triazolo[4,3-a]quinazolin-5-amine

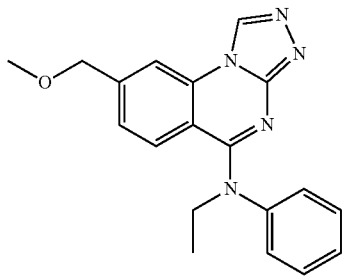 [SMILES: CCN(c1ccccc1)c1nc2nncn2c2cc(COC)ccc12]

To a solution of (5-(ethyl(phenyl)amino)-[1,2,4]triazolo[4,3-a]quinazolin-8-yl)methanol (Example 180) (50 mg, 0.157 mmol) in DMF (0.78 mL) were added iodomethane (24.44 mg, 0.172 mmol) and sodium hydride (4.51 mg, 0.188 mmol), and the mixture was stirred for 4 h at RT. The reaction mixture was concentrated in vacuo. The residue was purified by column chromatography (Si-column, CHC₃: MeOH=10:0-9:1) to afford the desired product: ¹H NMR (Methanol-d4) δ 9.37 (s, 1H), 8.05-7.89 (m, 1H), 7.45-7.38 (m, 2H), 7.35-7.28 (m, 1H), 7.26-7.19 (m, 2H), 7.09 (d, J=8.7 Hz, 1H), 7.00 (dd, J=8.7, 1.7 Hz, 1H), 4.52 (s, 2H), 4.21 (q, J=7.0 Hz, 2H), 3.42 (s, 3H), 1.29 (t, J=7.0 Hz, 3H); LCMS(m/z) 334.1.

Example 182. 7,8-Difluoro-N-methyl-N-phenyl-[1,2,4]triazolo[4,3-a]quinazolin-5-amine

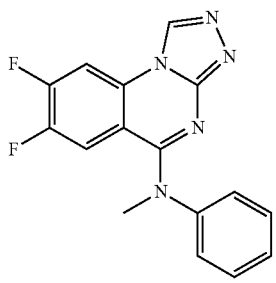 [SMILES: CN(c1ccccc1)c1nc2nncn2c2cc(F)c(F)cc12]

(Step 1) Synthesis of 6,7-difluoroquinazoline-2,4(1H,3H)-dione

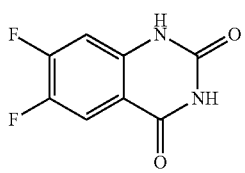

A mixture of 2-amino-4,5-difluorobenzoic acid (1 g, 5.78 mmol) and urea (0.520 g, 8.66 mmol) in NMP (5 mL) was stirred for 15 h at 150° C. The reaction mixture was poured onto ice, and the resulting solids were collected. The crude solids were used in the next step without further purification. LCMS(m/z) 199.19 [M+H]⁺.

(Step 2) Synthesis of 2,4-dichloro-6,7-difluoroquinazoline

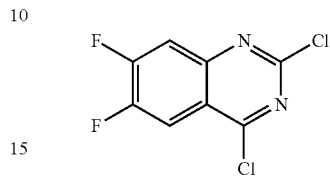

A mixture of 6,7-difluoroquinazoline-2,4(1H,3H)-dione (1.26 g, 6.36 mmol) and phosphoryl trichloride (10 mL, 6.36 mmol) was stirred for 2 days at 110° C. The reaction mixture was poured slowly into ice-water. The resulting solids were collected to give the desired product. The crude solids were used in the next step without further purification. LCMS(m/z) 235.09 [M+H]⁺.

(Step 3) Synthesis of 2-chloro-6,7-difluoro-N-methyl-N-phenylquinazolin-4-amine

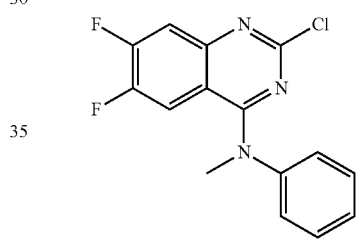

To a solution of the resulting 2,4-dichloro-6, 7-difluoroquinazoline (450 mg, 1.915 mmol) in DMF (9.57 mL) were added sodium hydride (46.0 mg, 1.915 mmol) and N-methylaniline (215 mg, 2.011 mmol), and the mixture was stirred for 0.5 h at RT. The reaction mixture was diluted with AcOEt, washed successively with water and brine, and dried over Na₂SO₄. The organic layer was concentrated in vacuo. The resulting residue was used in the next step without further purification. LCMS(m/z) 306.03 [M+H]⁺.

(Step 4) Synthesis of 6,7-difluoro-2-hydrazinyl-N-methyl-N-phenylquinazolin-4-amine

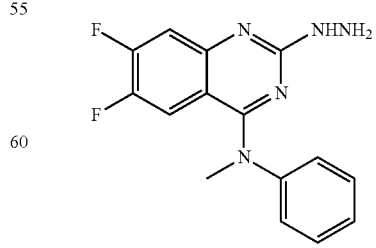

Hydrazine hydrate (0.035 g, 0.697 mmol) was added slowly to a stirred solution of the resulting 2-chloro-6,7- difluoro-N-methyl-N-phenylquinazolin-4-amine (0.71 g, 2.32 mmol) in ethanol (11.6 mL) at RT. After 1 h and 2h, additional portions of hydrazine hydrate (0.035 g×2, 1.394 mmol) were added slowly to the solution, and the stirring was continued for 1 h. The mixture was diluted with AcOEt, and then washed successively with water and brine and dried over Na$_2$SO$_4$. The organic layer was concentrated in vacuo. The resulting residue was used in the next step without further purification. LCMS(m/z) 302.10 [M+H]$^+$.

(Step 5) Synthesis of 7,8-difluoro-N-methyl-N-phenyl-[1,2,4]triazolo[4,3-a]quinazolin-5-amine A mixture of the resulting 6,7-difluoro-2-hydrazinyl-N-methyl-N-phenylquinazolin-4-amine (0.65 g, 2.16 mmol) and triethylorthoformate (7 mL, 2.18 mmol) was heated to 100° C. for 16 h. The progress of the reaction was monitored by TLC. After completion of the reaction, the mixture was concentrated in vacuo. The residue was purified by column chromatography (Si-column, CHCl$_3$:MeOH=10:0-9:1) to afford the desired product: $^1$H NMR (Methanol-d$_4$) δ 9.37 (s, 1H), 8.27 (dd, J=10.5, 7.0 Hz, 1H), 7.52-7.45 (m, 2H), 7.43-7.36 (m, 1H), 7.35-7.29 (m, 2H), 7.06 (dd, J=12.1, 8.2 Hz, 1H), 3.65 (s, 3H); LCMS(m/z) 312.1.

Example 183. N-Methyl-N-(4'-methyl-[1,1'-biphenyl]-3-yl)-8-(prop-1-yn-1-yl)-[1,2,4]triazolo[4,3-a]quinazolin-5-amine

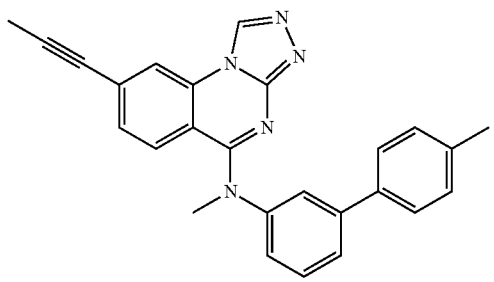 [SMILES: CC#Cc1ccc2c(N(C)c3cccc(-c4ccc(C)cc4)c3)nc3nncn3c2c1]

To a stirred and degassed solution of 8-bromo-5-chloro-[1,2,4]triazolo[4,3-a]quinazoline (0.150 g, 0.34 mmol) in 1,4-dioxane (6 mL) was added triethylamine (0.047 mL, 0.34 mmol) at RT and the mixture was degassed with argon for 10 min, followed by the addition of triphenylphosphine (0.080 g, 0.30 mmol), copper iodide (0.013 g, 0.07 mmol), Pd(OAc)$_2$ (0.015 g, 0.07 mmol) and 1-propyne (0.13 mL, 1.69 mmol) at RT, and the mixture was heated to 100° C. for 4 h in a sealed tube. The progress of the reaction was monitored by TLC. After completion of the reaction, the reaction mixture was filtered through a bed of celite and washed with ethyl acetate. The filtrate was evaporated under reduced pressure and the residue was purified by silica gel column chromatography, eluted with 4% methanol/dichloromethane and further purified by prep. HPLC to afford the desired product: $^1$H NMR (DMSO-d$_6$) δ 9.63 (s, 1H), 8.40 (d, J=1.6 Hz, 1H), 7.62-7.49 (m, 4H), 7.45 (t, J=7.8 Hz, 1H), 7.30-7.20 (m, 4H), 7.17 (dd, J=8.7, 1.6 Hz, 1H), 3.59 (s, 3H), 2.31 (s, 3H), 2.09 (s, 3H); LCMS(m/z) 404.2.

Example 184. N-(4'-Methoxy-[1,1'-biphenyl]-3-yl)-N-methyl-8-(prop-1-yn-1-yl)-[1,2,4]triazolo[4,3-a]quinazolin-5-amine

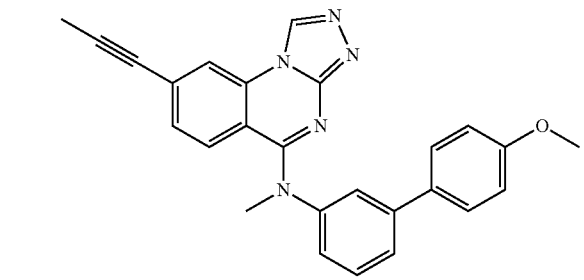 [SMILES: CC#Cc1ccc2c(N(C)c3cccc(-c4ccc(OC)cc4)c3)nc3nncn3c2c1]

To a stirred and degassed solution of 8-bromo-N-(4'-methoxy-[1,1'-biphenyl]-3-yl)-N-methyl-[1,2,4]triazolo[4,3-a]quinazolin-5-amine (Example 173) (0.1 g, 0.22 mmol) in 1,4-dioxane (10 mL) were added triphenylphosphine (0.051 g, 0.19 mmol), triethylamine (0.03 mL, 0.22 mmol), copper iodide (0.008 g, 0.04 mmol), palladium acetate (0.010 g, 0.04 mmol) and 1-propyne (0.13 mL, 2.18 mmol) at RT, and the mixture was heated to 100° C. for 6 h. The progress of the reaction was monitored by TLC. After completion of the reaction, the reaction mixture was diluted with water and extracted with ethyl acetate. The organic layer was washed with brine, dried over Na$_2$SO$_4$, filtered and evaporated under reduced pressure. The residue was purified by prep. HPLC to afford the desired product: $^1$H NMR (DMSO-d$_6$) δ 9.63 (s, 1H), 8.40 (d, J=1.6 Hz, 1H), 7.62-7.54 (m, 3H), 7.54-7.49 (m, 1H), 7.43 (t, J=7.8 Hz, 1H), 7.27 (d, J=8.7 Hz, 1H), 7.22 (ddd, J=7.8, 2.2, 1.0 Hz, 1H), 7.17 (dd, J=8.7, 1.6 Hz, 1H), 7.01-6.90 (m, 2H), 3.77 (s, 3H), 3.59 (s, 3H), 2.09 (s, 3H); LCMS(m/z) 420.2.

Example 185. 8-Bromo-N-(4'-chloro-[1,1'-biphenyl]-3-yl)-N-methyl-[1,2,4]triazolo[4,3-a]quinazolin-5-amine

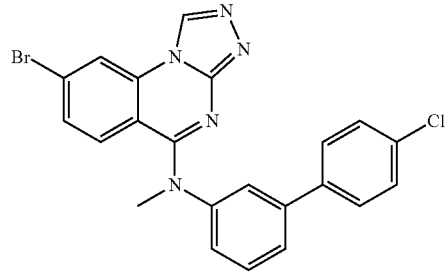

(Step 1) Synthesis of 7-bromoquinazoline-2,4(1H,3H)-dione

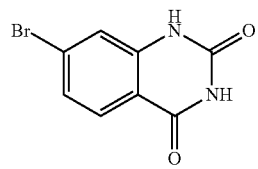

A mixture of 2-amino-4-bromobenzoic acid (20.0 g, 92.59 mmol) and urea (55.55 g, 925.92 mmol) was heated to 150° C. for 16 h. The progress of the reaction was monitored by TLC. After completion of the reaction, the reaction mixture was diluted with ice-water and stirred for 30 min. The resulting solids were filtered off and triturated with glacial acetic acid. The resulting solids were collected and washed with petroleum ether to give the desired product. LCMS(m/z) 241.06 [M+H]$^+$.

(Step 2) Synthesis of
7-bromo-2,4-dichloroquinazoline

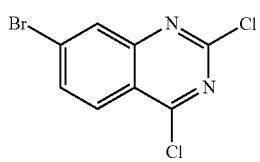

To a stirred solution of 7-bromoquinazoline-2,4(1H,3H)-dione (19.0 g, 79.17 mmol) in phosphorus oxychloride (74 mL, 791.67 mmol) was added N, N-diisopropylethylamine (19.6 mL, 118.75 mmol) at 0° C., and the mixture was heated to 110° C. for 16 h. The progress of the reaction was monitored by TLC. After completion of the reaction, the reaction mixture was diluted with ice-water and stirred for 30 min. The resulting solid was filtered off, washed with cold water, and dried under vacuum to give the desired product as crude. LCMS(m/z) 279.06 [M+H]$^+$.

(Step 3) Synthesis of
7-bromo-2-chloroquinazolin-4(3H)-one

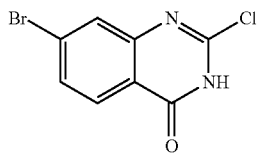 [SMILES: O=c1[nH]c(Cl)nc2cc(Br)ccc12]

To a stirred solution of 7-bromo-2,4-dichloroquinazoline (crude, 22.0 g, 79.71 mmol, crude) in tetrahydrofuran (200 mL) was added 1M sodium hydroxide (191 mL, 191.30 mmol) at 0° C., and the mixture was stirred for 2 h at RT. The progress of the reaction was monitored by TLC. After completion of the reaction, the reaction mixture was acidified with glacial acetic acid to pH~5. The resulting solid was filtered and dried under vacuum to give the desired product. LCMS(m/z) 259.17 [M+H]$^+$.

(Step 4) Synthesis of 7-bromo-2-chloro-3-((2-(trimethylsilyl)ethoxy)methyl)quinazolin-4(3H)-one

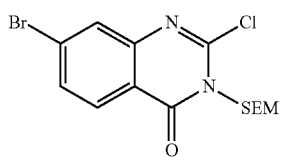

To a stirred solution of 7-bromo-2-chloroquinazolin-4(3H)-one (14.5 g, 56.20 mmol) in N, N-dimethylformamide (150 mL) were added potassium carbonate (8.53 g, 61.82 mmol) and 2-(trimethylsilyl)ethoxymethyl chloride (10.96 mL, 61.82 mmol) at 0° C., and the mixture was stirred for 4 h at RT. The progress of the reaction was monitored by TLC. After completion of the reaction, the reaction mixture was diluted with water and extracted with ethyl acetate. The organic layer was washed with water, brine, dried over anhydrous Na$_2$SO$_4$, filtered and evaporated under reduced pressure to give the desired product.

(Step 5) Synthesis of 7-bromo-2-hydrazinyl-3-((2-(trimethylsilyl)ethoxy)methyl)quinazolin-4(3H)-one

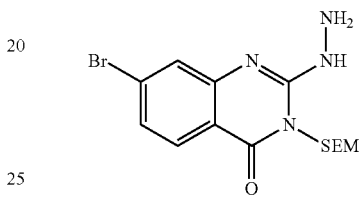

To a stirred solution of 7-bromo-2-chloro-3-((2-(trimethylsilyl)ethoxy)methyl)quinazolin-4(3H)-one (15.0 g, 38.66 mmol) in ethanol (150 mL) was added hydrazine (386 mL, 386.60 mmol, 1.0 M in tetrahydrofuran) at 0° C., and the mixture was stirred for 2 h at RT. The progress of the reaction was monitored by TLC. After completion of the reaction, the reaction mixture was diluted with water and extracted with 10% methanol/dichloromethane. The organic layer was washed with water, brine, dried over anhydrous Na$_2$SO$_4$, filtered and evaporated under reduced pressure to give the desired product. LCMS(m/z) 385.44 [M+H]$^+$.

(Step 6) Synthesis of 8-bromo-4-((2-(trimethylsilyl)ethoxy)methyl)-[1,2,4]triazolo[4,3-a]quinazolin-5(4H)-one (26)

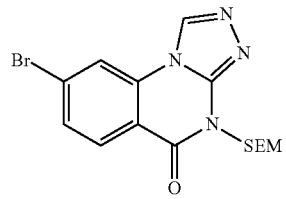

A mixture of 7-bromo-2-hydrazinyl-3-((2-(trimethylsilyl)ethoxy)methyl)quinazolin-4(3H)-one (crude, 17 g, 44.27 mmol) and triethylorthoformate (43.74 mL, 265.62 mmol) was heated to 100° C. for 16 h. The progress of the reaction was monitored by TLC. After completion of the reaction, the reaction mixture was evaporated under reduced pressure to give crude compound. The crude compound was triturated with diethyl ether and collected to afford the desired product. LCMS(m/z) 397.35 [M+H]$^+$.

(Step 7) Synthesis of 8-bromo-[1,2,4]triazolo[4,3-a]quinazolin-5(4H)-one

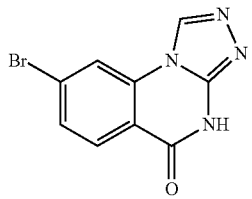

To a stirred solution of 8-bromo-4-((2-(trimethylsilyl)ethoxy)methyl)-[1,2,4]triazolo[4,3-a]quinazolin-5(4H)-one (1.5 g, 5.10 mmol) in methanol (15 mL) was added trifluoroacetic acid (1.5 mL) at RT, and the mixture was stirred for 16 h at RT. The progress of the reaction was monitored by TLC. After completion of the reaction, the reaction mixture evaporated under reduced pressure to give crude compound. The crude compound was triturated with diethyl ether and collected to afford the desired product. LCMS(m/z) 265.27 [M+H]$^+$.

(Step 8) Synthesis of 8-bromo-5-chloro-[1,2,4]triazolo[4,3-a]quinazoline

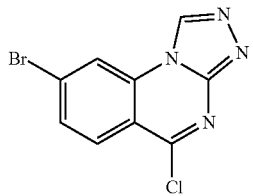

The mixture of 8-bromo-[1,2,4]triazolo[4,3-a]quinazolin-5(4H)-one (2.0 g, 7.57 mmol) in phosphorus oxychloride (15 mL) was stirred for 6 h under reflux condition. The progress of the reaction was monitored by TLC. After completion of the reaction, the reaction mixture was evaporated under reduced pressure to give crude product. The crude product was dissolved in toluene and evaporated twice to afford the desired product. LCMS(m/z) 283.20 [M+H]$^+$.

(Step 9) Synthesis of 8-bromo-N-(4'-chloro-[1,1'-biphenyl]-3-yl)-N-methyl-[1,2,4]triazolo[4,3-a]quinazolin-5-amine To a stirred solution of 8-bromo-5-chloro-[1,2,4]triazolo[4,3-a]quinazoline (0.1 g, 0.35 mmol) in N, N-dimethylformamide (5 mL) were added 4'-chloro-N-methylbiphenyl-3-amine (0.115 g, 0.53 mmol) and potassium carbonate (0.028 g, 0.71 mmol) at RT, and the mixture was stirred for 3 h at RT. The progress of the reaction was monitored by TLC. After completion of the reaction, the reaction mixture was diluted with water and extracted with ethyl acetate. The organic layer was washed with brine, dried over anhydrous Na$_2$SO$_4$, filtered and evaporated under reduced pressure to give crude residue. The residue was purified by prep. HPLC to afford the desired product: $^1$H NMR (DMSO-d$_6$) δ 9.64 (s, 1H), 8.67 (d, J=1.9 Hz, 1H), 7.71-7.65 (m, 3H), 7.59 (dt, J=7.9, 1.2 Hz, 1H), 7.51-7.45 (m, 3H), 7.43 (dd, J=8.9, 1.9 Hz, 1H), 7.31 (ddd, J=7.9, 2.3, 1.0 Hz, 1H), 7.23 (d, J=8.9 Hz, 1H), 3.59 (s, 3H); LCMS(m/z) 464.32/466.34.

Example 186. 8-Bromo-N-(4'-(tert-butyl)-[1,1'-biphenyl]-3-yl)-N-methyl-[1,2,4]triazolo[4,3-a]quinazolin-5-amine

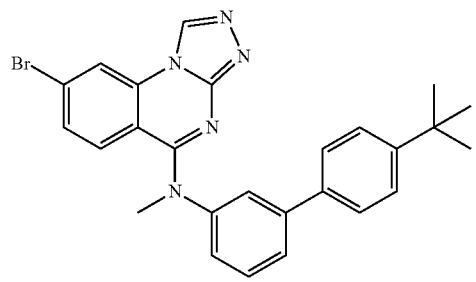

(Step 1) Synthesis of 4'-(tert-butyl)-N-methyl-[1,1'-biphenyl]-3-amine

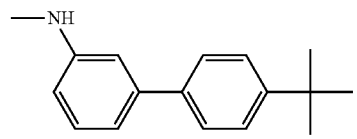 [SMILES: CNc1cccc(-c2ccc(C(C)(C)C)cc2)c1]

To a stirred solution of 3-iodo-N-methylbenzenamine (0.8 g, 3.43 mmol) in 1,4-dioxane/water (20 mL, 3:1) were added (4-(tert-butyl)phenyl)boronic acid (1.22 g, 6.87 mmol), sodium carbonate (0.728 g, 6.87 mmol) and [1,1'-bis(diphenylphosphino)ferrocene]palladium(II) dichloride (0.250 g, 0.34 mmol) at RT, and the mixture was heated to 80° C. for 3 h. The progress of the reaction was monitored by TLC. After completion of the reaction, the reaction mixture was diluted with water and extracted with ethyl acetate. The organic layer was washed with brine, dried over Na$_2$SO$_4$, filtered and evaporated under reduced pressure. The residue was purified by silica gel column chromatography, eluted with 15% ethyl acetate/petroleum ether to give the desired product. LCMS(m/z) 240.23 [M+H]$^+$.

(Step 2) Synthesis of 8-bromo-N-(4'-(tert-butyl)-[1,1'-biphenyl]-3-yl)-N-methyl-[1,2,4]triazolo[4,3-a]quinazolin-5-amine To a stirred solution of 8-bromo-5-chloro-[1,2,4]triazolo[4,3-a]quinazoline (0.5 g, 1.77 mmol) in DMF (10 mL) were added 4'-(tert-Butyl)-N-methyl-[1,1'-biphenyl]-3-amine (0.635 g, 2.66 mmol) and potassium carbonate (0.489 g, 3.54 mmol) at 0° C., and the mixture was stirred for 3 h at RT. The progress of the reaction was monitored by TLC. After completion of the reaction, the reaction mixture was diluted with water and extracted with ethyl acetate. The organic layer was washed with brine, dried over Na$_2$SO$_4$, filtered and evaporated under reduced pressure. The residue was purified by silica gel column chromatography, eluted with 10% methanol/dichloromethane, followed by prep. HPLC to afford the desired product: $^1$H NMR (DMSO-d$_6$) δ 9.64 (s, 1H), 8.67 (d, J=2.0 Hz, 1H), 7.61-7.50 (m, 4H), 7.48 (d, J=7.8 Hz, 1H), 7.44-7.39 (m, 3H), 7.29 (ddd, J=8.0, 2.2, 1.1 Hz, 1H), 7.22 (d, J=8.9 Hz, 1H), 3.59 (s, 3H), 1.28 (s, 9H); LCMS(m/z) 486.14/488.14.

Example 187. 8-Chloro-N-methyl-N-(4'-methyl-[1,1'-biphenyl]-3-yl)-[1,2,4]triazolo[4,3-a]quinazolin-5-amine

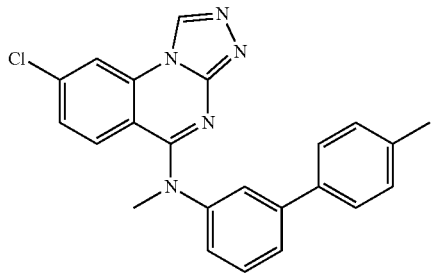

To a stirred solution of N,4'-dimethyl-[1,1'-biphenyl]-3-amine (0.124 g, 0.63 mmol) in DMF (6 mL) was added potassium carbonate (0.116 g, 0.84 mmol) at 0° C. and the mixture was stirred for 10 min at RT, followed by the addition of 5,8-dichloro-[1,2,4]triazolo[4,3-a]quinazoline (0.1 g, 0.42 mmol) at RT, and the mixture was stirred at RT for 3 h. The reaction mixture was diluted with ice-water and extracted with ethyl acetate. The organic layer was washed successively with water and brine, dried over $Na_2SO_4$, filtered and evaporated under reduced pressure. The residue was purified by prep. HPLC to afford the desired product: $^1$H NMR (DMSO-$d_6$) δ 9.62 (s, 1H), 8.53 (t, J=1.2 Hz, 1H), 7.62 (t, J=1.9 Hz, 1H), 7.58-7.51 (m, 3H), 7.45 (t, J=7.8 Hz, 1H), 7.31 (d, J=1.2 Hz, 2H), 7.26 (ddd, J=8.0, 2.3, 1.0 Hz, 1H), 7.24-7.18 (m, 2H), 3.59 (s, 3H), 2.32 (s, 3H); LCMS (m/z) 400.2.

Example 188. N-(3'-((8-Chloro-[1,2,4]triazolo[4,3-a]quinazolin-5-yl)(methyl)amino)-[1,1'-biphenyl]-4-yl)acetamide

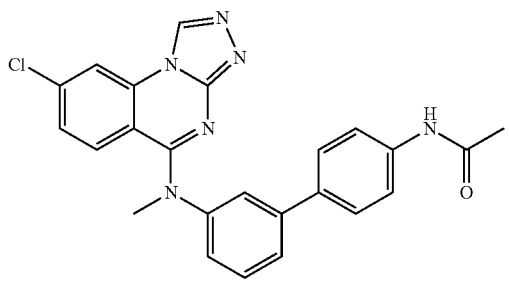

To a stirred solution of N-(3'-(methylamino)-[1,1'-biphenyl]-4-yl)acetamide (0.151 g, 0.63 mmol) in DMF (5 mL) was added sodium hydroxide (0.033 g, 0.84 mmol) at 0° C. and the mixture was stirred for 10 min at RT, followed by the addition of 5,8-dichloro-[1,2,4]triazolo[4,3-a]quinazoline (0.1 g, 0.42 mmol) at RT, and the mixture was stirred at RT for 3 h. The reaction mixture was diluted with ice-water and extracted with ethyl acetate. The organic layer was washed successively with water and brine, dried over $Na_2SO_4$, filtered and evaporated under reduced pressure. The residue was purified by prep. HPLC to afford the desired product: $^1$H NMR (DMSO-$d_6$) δ 10.02 (s, 1H), 9.63 (s, 1H), 8.54 (t, J=1.2 Hz, 1H), 7.66-7.54 (m, 6H), 7.45 (t, J=7.9 Hz, 1H), 7.31 (d, J=1.2 Hz, 2H), 7.25 (ddd, J=7.9, 2.2, 1.0 Hz, 1H), 3.59 (s, 3H), 2.04 (s, 3H); LCMS(m/z) 443.4.

Example 189. (5-((3-Fluorophenyl)(methyl)amino)-[1,2,4]triazolo[4,3-a]quinazolin-8-yl)methanol

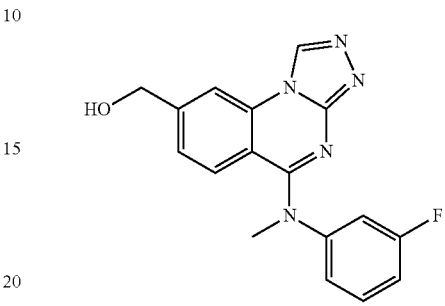

(Step 1) Synthesis of 7-bromo-2-chloro-N-(3-fluorophenyl)-N-methylquinazolin-4-amine

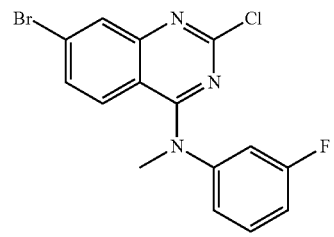 [SMILES: CN(c1cccc(F)c1)c1nc(Cl)nc2cc(Br)ccc12]

To a solution of 7-bromo-2,4-dichloroquinazoline (450 mg, 1.619 mmol) in DMF (8.1 mL) were added 3-fluoro-N-methylaniline (203 mg, 1.619 mmol) and sodium hydride (38.9 mg, 1.619 mmol), and the mixture was stirred for 1 h at RT. The reaction mixture was diluted with AcOEt, washed successively with water and brine. The organic layer was concentrated in vacuo to give the desired product, which was used for the next step without further purification. LCMS (m/z) 367.98 [M+H]$^+$.

(Step 2) Synthesis of 7-bromo-N-(3-fluorophenyl)-2-hydrazinyl-N-methylquinazolin-4-amine

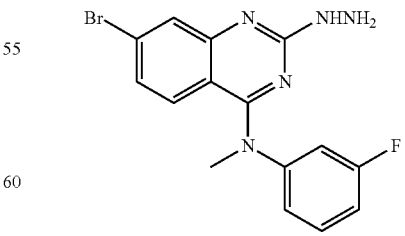

To a solution of 7-bromo-2-chloro-N-(3-fluorophenyl)-N-methylquinazolin-4-amine (387 mg, crude) in EtOH (5.3 mL) was added hydrazine hydrate (52.8 mg, 1.056 mmol), and the mixture was stirred for 1 h at RT. The reaction mixture was diluted with AcOEt, washed successively with water and brine. The organic layer was concentrated in vacuo to give the desired product, which was used for the next step without further purification. LCMS(m/z) 363.18 [M+H]⁺.

(Step 3) Synthesis of 8-bromo-N-(3-fluorophenyl)-N-methyl-[1,2,4]triazolo[4,3-a]quinazolin-5-amine

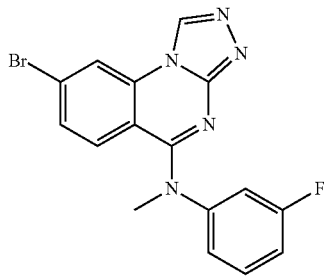 [SMILES: CN(c1cccc(F)c1)c1nc2nncn2c2cc(Br)ccc12]

A mixture of 7-bromo-N-(3-fluorophenyl)-2-hydrazinyl-N-methylquinazolin-4-amine (300 mg, crude) and triethoxymethane (10 mL, 0.828 mmol) was stirred at 100° C. overnight. The reaction mixture was concentrated in vacuo. The residue was purified by column chromatography (Si-column, CHCl₃:MeOH=10:0-9:1) to the desired product. LCMS(m/z) 373.13 [M+H]⁺.

(Step 4) Synthesis of N-(3-fluorophenyl)-N-methyl-8-vinyl-[1,2,4]triazolo[4,3-a]quinazolin-5-amine

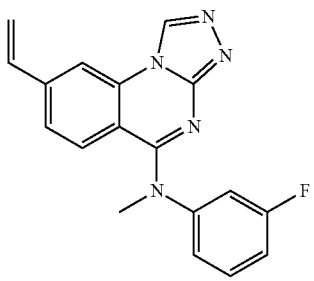 [SMILES: C=Cc1ccc2c(N(C)c3cccc(F)c3)nc3nncn3c2c1]

A mixture of 8-bromo-N-(3-fluorophenyl)-N-methyl-[1,2,4]triazolo[4,3-a]quinazolin-5-amine (232 mg, 0.623 mmol), K₃PO4 (265 mg, 1.247 mmol), Pd(OAc)₂ (28.0 mg, 0.125 mmol), 4,4,5,5-tetramethyl-2-vinyl-1,3,2-dioxaborolane (144 mg, 0.935 mmol) and tricyclohexylphosphine (35.0 mg, 0.125 mmol) was stirred at 100° C. overnight. The reaction mixture was concentrated in vacuo. The residue was purified by column chromatography (Si-column, CHCl₃:MeOH=10:0-9:1) to give the desired product. LCMS(m/z) 319.9 [M+H]⁺.

(Step 5) Synthesis of 5-((3-fluorophenyl)(methyl)amino)-[1,2,4]triazolo[4,3-a]quinazoline-8-carbaldehyde

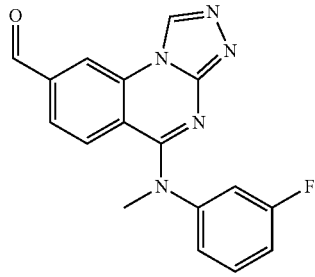 [SMILES: CN(c1cccc(F)c1)c1nc2nncn2c2cc(C=O)ccc12]

To a solution of N-(3-fluorophenyl)-N-methyl-8-vinyl-[1,2,4]triazolo[4,3-a]quinazolin-5-amine (128 mg, 0.401 mmol) in acetone/water (1:1, 2 mL) were added osmium (VIII) oxide (0.2 N in BuOH, 0.4 mL, 0.080 mmol) and sodium periodate (103 mg, 0.481 mmol), and the mixture was stirred for overnight at RT. The reaction mixture was subjected to solid phase extraction (washed with MeOH, then eluted with NH₃ in MeOH) using Bond Elut SCX cartridge (Agilent), and the collected fractions were concentrated in vacuo. The residue was concentrated in vacuo to give the desired product. LCMS(m/z) 322.08 [M+H]⁺.

(Step 6) Synthesis of (5-((3-fluorophenyl)(methyl)amino)-[1,2,4]triazolo[4,3-a]quinazolin-8-yl)methanol To a solution of 5-((3-fluorophenyl)(methyl)amino)-[1,2,4]triazolo[4,3-a]quinazoline-8-carbaldehyde (crude, 129 mg, 0.4 mmol) in MeOH (2 mL) was added NaBH₄ (16.65 mg, 0.440 mmol), and the mixture was stirred overnight at RT. The reaction mixture was concentrated in vacuo. The residue was purified by column chromatography (Si-column, CHCl₃:MeOH=10:0-9:1) to afford the desired product: ¹H NMR (Methanol-d₄) δ 9.48 (s, 1H), 8.18 (s, 1H), 7.48-7.33 (m, 2H), 7.23 (d, J=8.8 Hz, 1H), 7.19-7.00 (m, 3H), 4.76 (s, 2H), 3.66 (s, 3H); LCMS(m/z) 324.1.

Example 190. 5-((4'-Methoxy-[1,1'-biphenyl]-3-yl)(methyl)amino)-[1,2,4]triazolo[4,3-a]quinazoline-8-carbaldehyde

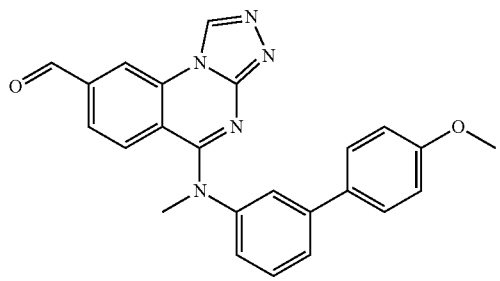 [SMILES: COc1ccc(-c2cccc(N(C)c3nc4nncn4c4cc(C=O)ccc34)c2)cc1]

To a stirred solution of N-(4'-methoxy-[1,1'-biphenyl]-3-yl)-N-methyl-8-vinyl-[1,2,4]triazolo[4,3-a]quinazolin-5-amine (Example 192) (0.150 g, 0.37 mmol) in THF/water (9 mL, 2:1) were added sodium periodate (0.235 g, 1.10 mmol)

and potassium osmate (VI) dihydrate (0.007 g, 0.02 mmol) at 0° C., and the mixture was stirred at RT for 2 h. The progress of the reaction was monitored by TLC. After completion of the reaction, the reaction mixture was diluted with water and extracted with ethyl acetate. The organic layer was washed with brine, dried over Na$_2$SO$_4$, filtered and evaporated under reduced pressure. The residue was purified by silica gel column chromatography, eluted with 8% methanol/dichloromethane to afford the desired product: $^1$H NMR (DMSO-d$_6$) δ 10.05 (s, 1H), 9.78 (s, 1H), 8.81 (d, J=1.5 Hz, 1H), 7.69 (dd, J=8.5, 1.5 Hz, 1H), 7.64-7.50 (m, 5H), 7.44 (t, J=7.9 Hz, 1H), 7.27 (ddd, J=7.9, 2.3, 1.0 Hz, 1H), 7.01-6.92 (m, 2H), 3.76 (s, 3H), 3.62 (s, 3H); LCMS(m/z) 410.2.

Example 191. N-(4'-(tert-Butyl)-[1,1'-biphenyl]-3-yl)-N-methyl-8-(prop-1-yn-1-yl)-[1,2,4]triazolo[4,3-a]quinazolin-5-amine

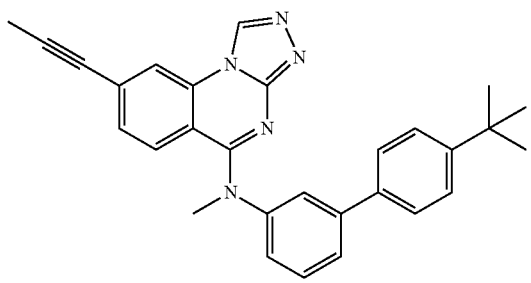 [SMILES: CC#Cc1ccc2c(N(C)c3cccc(-c4ccc(C(C)(C)C)cc4)c3)nc3nncn3c2c1]

To a degassed solution of 8-bromo-N-(4'-(tert-butyl)-[1,1'-biphenyl]-3-yl)-N-methyl-[1,2,4]triazolo[4,3-a]quinazolin-5-amine (Example 186) (0.1 g, 0.21 mmol) in 1,4-dioxane (5 mL) were added triphenylphosphine (0.048 g, 0.18 mmol), triethylamine (0.029 mL, 0.21 mmol), copper iodide (0.0078 g, 0.04 mmol), palladium acetate (0.009 g, 0.04 mmol) and 1-propyne (0.06 mL, 1.03 mmol) at RT, and the mixture was heated to 100° C. for 6 h. The progress of the reaction was monitored by TLC. After completion of the reaction, the reaction mixture was diluted with water and extracted with ethyl acetate. The organic layer was washed with brine, dried over anhydrous Na$_2$SO$_4$, filtered and evaporated under reduced pressure. The residue was purified by prep. HPLC to afford the desired product: $^1$H NMR (DMSO-d$_6$) δ 9.63 (s, 1H), 8.40 (d, J=1.6 Hz, 1H), 7.58-7.50 (m, 4H), 7.50-7.37 (m, 3H), 7.33-7.24 (m, 2H), 7.17 (dd, J=8.7, 1.6 Hz, 1H), 3.59 (s, 3H), 2.09 (s, 3H), 1.28 (s, 9H); LCMS(m/z) 446.3.

Example 192. N-(4'-Methoxy-[1,1'-biphenyl]-3-yl)-N-methyl-8-vinyl-[1,2,4]triazolo[4,3-a]quinazolin-5-amine

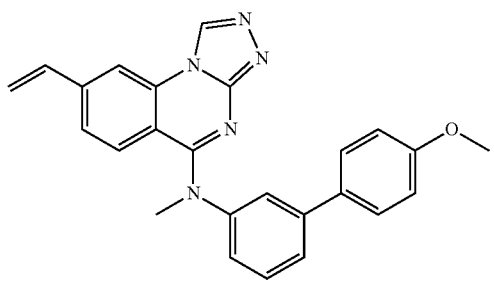 [SMILES: C=Cc1ccc2c(N(C)c3cccc(-c4ccc(OC)cc4)c3)nc3nncn3c2c1]

To a stirred solution of 8-bromo-N-(4'-methoxy-[1,1'-biphenyl]-3-yl)-N-methyl-[1,2,4]triazolo[4,3-a]quinazolin-5-amine (Example 173) (0.1 g, 0.22 mmol) in t-butanol (5 mL) were added potassium tert-butoxide (0.048 g, 0.43 mmol), tetrakis(triphenylphosphine)palladium (0) (0.025 g, 0.02 mmol) and 4,4,5,5-tetramethyl-2-vinyl-1,3,2-dioxaborolane (0.05 g, 0.33 mmol) at RT, and the mixture was heated to 100° C. for 6 h. The progress of the reaction was monitored by TLC. After completion of the reaction, the reaction mixture was diluted with water and extracted with ethyl acetate. The organic layer was washed with brine, dried over Na$_2$SO$_4$, filtered and evaporated under reduced pressure. The residue was purified by prep. HPLC to afford the desired product: $^1$H NMR (DMSO-d$_6$) δ 9.62 (s, 1H), 8.39 (d, J=1.7 Hz, 1H), 7.64-7.55 (m, 3H), 7.53 (dt, J=7.9, 1.3 Hz, 1H), 7.43 (t, J=7.8 Hz, 1H), 7.35 (dd, J=8.9, 1.7 Hz, 1H), 7.28 (d, J=8.7 Hz, 1H), 7.25-7.16 (m, 1H), 7.01-6.92 (m, 2H), 6.78 (dd, J=17.6, 10.9 Hz, 1H), 6.16 (d, J=17.6 Hz, 1H), 5.54 (d, J=11.0 Hz, 1H), 3.77 (s, 3H), 3.60 (s, 3H); LCMS(m/z) 408.2.

Example 193. N-(3'-(Methyl(8-vinyl-[1,2,4]triazolo[4,3-a]quinazolin-5-yl)amino)-[1,1'-biphenyl]-4-yl)acetamide

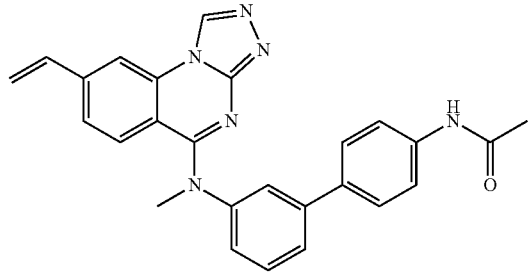 [SMILES: C=Cc1ccc2c(N(C)c3cccc(-c4ccc(NC(C)=O)cc4)c3)nc3nncn3c2c1]

To a stirred solution of N-(3'-((8-bromo-[1,2,4]triazolo[4,3-a]quinazolin-5-yl)(methyl)amino)-[1,1'-biphenyl]-4-yl)acetamide (Example 174) (0.2 g, 0.41 mmol) in DMF (6 mL) was added cesium carbonate (0.267 g, 0.82 mmol) at RT and the mixture was degassed with argon for 10 min, followed by the addition of bis(triphenylphosphine)palladium(II) dichloride (0.029 g, 0.04 mmol) and 4,4,5,5-tetramethyl-2-vinyl-1,3,2-dioxaborolane (0.127 g, 0.82 mmol) at RT. The mixture was heated to 100° C. for 3 h in a sealed tube. The progress of the reaction was monitored by TLC. After completion of the reaction, the reaction mixture was diluted with water and stirred for a few minutes. The resulting solids were filtered and dried under vacuum. The residue was purified by prep. HPLC to afford the desired product: $^1$H NMR (DMSO-d$_6$) δ 10.02 (s, 1H), 9.62 (s, 1H), 8.39 (d, J=1.7 Hz, 1H), 7.66-7.59 (m, 5H), 7.55 (dt, J=8.0, 1.2 Hz, 1H), 7.44 (t, J=7.9 Hz, 1H), 7.35 (dd, J=8.8, 1.6 Hz, 1H), 7.28 (d, J=8.7 Hz, 1H), 7.23 (ddd, J=8.0, 2.2, 1.0 Hz, 1H), 6.78 (dd, J=17.6, 11.0 Hz, 1H), 6.16 (d, J=17.6 Hz, 1H), 5.54 (d, J=10.9 Hz, 1H), 3.60 (s, 3H), 2.04 (s, 3H); LCMS (m/z) 435.1.

Example 194. N-(4'-(tert-Butyl)-[1,1'-biphenyl]-3-yl)-N-methyl-8-vinyl-[1,2,4]triazolo[4,3-a]quinazolin-5-amine

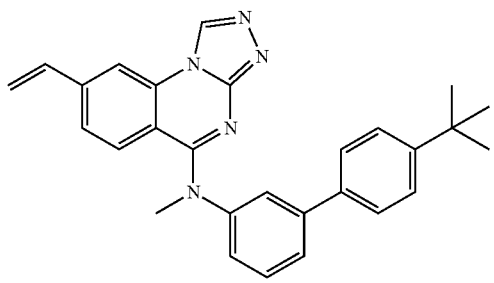

To a stirred solution of 8-bromo-N-(4'-(tert-butyl)-[1,1'-biphenyl]-3-yl)-N-methyl-[1,2,4]triazolo[4,3-a]quinazolin-5-amine (Example 186) (0.1 g, 0.21 mmol) in t-butanol (5 mL) were added potassium tert-butoxide (0.046 g, 0.41 mmol), tetrakis(triphenylphosphine)palladium (0) (0.024 g, 0.02 mmol) and 4,4,5,5-tetramethyl-2-vinyl-1,3,2-dioxaborolane (0.048 g, 0.31 mmol) at RT, and the mixture was heated to 100° C. for 6 h. The progress of the reaction was monitored by TLC. After completion of the reaction, the reaction mixture was diluted with water and extracted with ethyl acetate. The organic layer was washed with brine, dried over Na$_2$SO$_4$, filtered and evaporated under reduced pressure. The residue was purified by prep. HPLC to afford the desired product: $^1$H NMR (DMSO-d$_6$) δ 9.62 (s, 1H), 8.39 (d, J=1.6 Hz, 1H), 7.60-7.50 (m, 4H), 7.49-7.39 (m, 3H), 7.34 (dd, J=8.7, 1.6 Hz, 1H), 7.31-7.24 (m, 2H), 6.78 (dd, J=17.6, 11.0 Hz, 1H), 6.16 (d, J=17.6 Hz, 1H), 5.54 (d, J=11.0 Hz, 1H), 3.60 (s, 3H), 1.28 (s, 9H); LCMS(m/z) 434.3.

Example 195. N-(4'-(tert-Butyl)-[1,1'-biphenyl]-3-yl)-8-chloro-N-methyl-[1,2,4]triazolo[4,3-a]quinazolin-5-amine

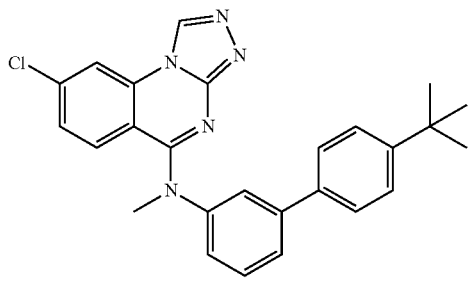

To a stirred solution of 5,8-dichloro-[1,2,4]triazolo[4,3-a]quinazoline (0.1 g, 0.42 mmol) in DMF (5 mL) were added 4'-(tert-butyl)-N-methyl-[1,1'-biphenyl]-3-amine (0.150 g, 0.63 mmol) and potassium carbonate (0.115 g, 0.84 mmol) at RT and the mixture was stirred at RT for 4 h. The reaction mixture was diluted with water and extracted with ethyl acetate. The organic layer was washed with brine, dried over Na$_2$SO$_4$, filtered and evaporated under reduced pressure. The residue was purified by silica gel column chromatography, eluted with 8% methanol/dichloromethane, followed by prep. HPLC to afford the desired product: $^1$H NMR (DMSO-d$_6$) δ 9.63 (s, 1H), 8.65-8.42 (m, 1H), 7.60-7.52 (m, 4H), 7.48 (d, J=8.0 Hz, 1H), 7.43 (dd, J=8.4, 6.3 Hz, 2H), 7.33-7.25 (m, 3H), 3.59 (s, 3H), 1.28 (s, 9H); LCMS(m/z) 442.2.

Example 196. 8-Ethyl-N-(3-fluorophenyl)-N-methyl-[1,2,4]triazolo[4,3-a]quinazolin-5-amine

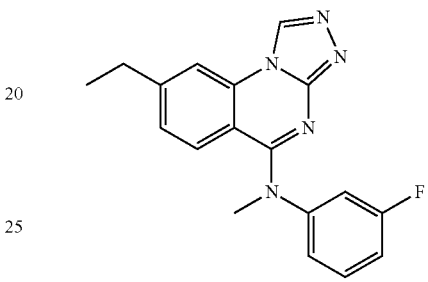

To a solution of N-(3-fluorophenyl)-N-methyl-8-vinyl-[1,2,4]triazolo[4,3-a]quinazolin-5-amine (128 mg, 0.401 mmol) in acetone/water (1:1, 2 mL) were added osmium (VIII) oxide (0.2 N in BuOH, 0.4 mL, 0.080 mmol) and sodium periodate (103 mg, 0.481 mmol), and the mixture was stirred for overnight at RT. The reaction mixture was subjected to solid phase extraction (washed with MeOH, then eluted with NH$_3$ in MeOH) using Bond Elut SCX cartridge (Agilent), and the collected fractions were concentrated in vacuo. The residue was concentrated in vacuo, and the residue was purified by column chromatography (Si-column, CHCl$_3$:MeOH=10:0-9:1) to give the desired product: $^1$H NMR (Methanol-d4) δ 9.46 (s, 1H), 8.09-7.99 (m, 1H), 7.44-7.37 (m, 1H), 7.28-7.22 (m, 1H), 7.12-7.03 (m, 4H), 3.64 (s, 3H), 2.80 (q, J=7.6 Hz, 2H), 1.30-1.26 (m, 3H); LCMS(m/z) 322.1.

Example 197. (5-(3,4-Dihydroquinolin-1(2H)-yl)-[1,2,4]triazolo[4,3-a]quinazolin-8-yl)methanol

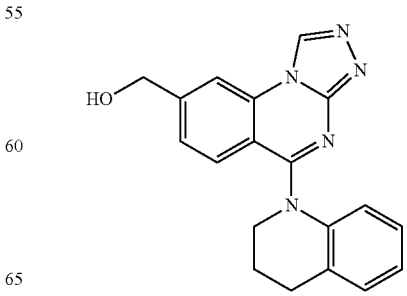

(Step 1) Synthesis of 5-(3,4-dihydroquinolin-1(2H)-yl)-8-vinyl-[1,2,4]triazolo[4,3-a]quinazoline

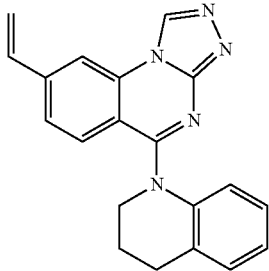 [SMILES: C=Cc1ccc2c(N3CCCc4ccccc43)nc3nncn3c2c1]

A mixture of 8-bromo-5-(3,4-dihydroquinolin-1(2H)-yl)-[1,2,4]triazolo[4,3-a]quinazoline (Example 205) (600 mg, 1.578 mmol), $K_3PO_4$ (670 mg, 3.16 mmol), Pd(OAc)$_2$ (70.9 mg, 0.316 mmol), 4,4,5,5-tetramethyl-2-vinyl-1,3,2-dioxaborolane (365 mg, 2.367 mmol) and tricyclohexylphosphine (89 mg, 0.316 mmol) in dioxane/water (7.9 mL) was heated for 1 h at 100° C. The reaction mixture was concentrated in vacuo. The residue was purified by column chromatography (Si-column, CHCl$_3$:MeOH=10:0-9:1) to give the desired product. LCMS(m/z) 328.13 [M+H]$^+$.

(Step 2) Synthesis of 5-(3,4-dihydroquinolin-1(2H)-yl)-[1,2,4]triazolo[4,3-a]quinazoline-8-carbaldehyde

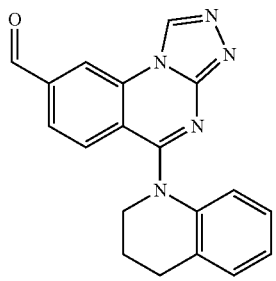 [SMILES: O=Cc1ccc2c(N3CCCc4ccccc43)nc3nncn3c2c1]

To a solution of 5-(3,4-dihydroquinolin-1(2H)-yl)-8-vinyl-[1,2,4]triazolo[4,3-a]quinazoline (630 mg) in acetone/water (1:1, 9.6 mL) were added osmium(VIII) oxide (98 mg, 0.385 mmol) and sodium periodate (823 mg, 3.85 mmol), and the mixture was stirred for overnight at RT. The reaction mixture was concentrated in vacuo to give the desired product as crude. The residue was used for the next step without further purification. LCMS(m/z) 330.08 [M+H]$^+$.

(Step 3) Synthesis of (5-(3,4-dihydroquinolin-1 (2H)-yl)-[1,2,4]triazolo[4,3-a]quinazolin-8-yl) methanol To a solution of 5-(3,4-dihydroquinolin-1(2H)-yl)-[1,2,4]triazolo[4,3-a]quinazoline-8-carbaldehyde (crude, 680 mg, 2.065 mmol) in DMF (10 mL) was added NaBH$_4$ (86 mg, 2.271 mmol) and the mixture was stirred for overnight at RT. The mixture was concentrated in vacuo. The residue was purified by column chromatography (Si-column, CHCl$_3$:MeOH=10:0-85:15) to afford the desired product: $^1$H NMR (Methanol-d4) δ 9.50 (s, 1H), 8.19 (s, 1H), 7.59-7.47 (m, 1H), 7.36-7.25 (m, 2H), 7.05 (tt, J=7.5, 1.0 Hz, 1H), 6.93 (t, J=7.7 Hz, 1H), 6.68 (d, J=8.0 Hz, 1H), 4.78 (s, 2H), 4.09-3.95 (m, 2H), 3.61 (q, J=7.0 Hz, 1H), 2.93 (t, J=6.6 Hz, 2H), 2.15 (p, J=6.7 Hz, 2H); LCMS(m/z) 332.1.

Example 198. 5-(Methyl(4'-methyl-[1,1'-biphenyl]-3-yl)amino)-[1,2,4]triazolo[4,3-a]quinazoline-8-carbaldehyde

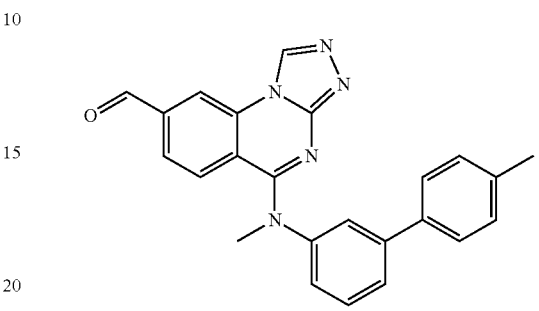

To a stirred solution of N-methyl-N-(4'-methyl-[1,1'-biphenyl]-3-yl)-8-vinyl-[1,2,4]triazolo[4,3-a]quinazolin-5-amine (Example 204) (0.550 g, 1.40 mmol) in THF/water (15 mL, 2:1) were added sodium periodate (0.903 g, 4.22 mmol) and potassium osmate (VI) dihydrate (0.026 g, 0.07 mmol) at 0° C., and the mixture was stirred for 16 h at RT. The progress of the reaction was monitored by TLC. After completion of the reaction, the reaction mixture was quenched with ice-water and stirred for few minutes. The resulting solids were filtered and dried under vacuum to afford the desired product: $^1$H NMR (DMSO-d$_6$) δ 10.04 (s, 1H), 9.77 (s, 1H), 8.81 (d, J=1.5 Hz, 1H), 7.68 (dd, J=8.5, 1.5 Hz, 1H), 7.64 (t, J=2.0 Hz, 1H), 7.56 (dt, J=8.3, 1.4 Hz, 1H), 7.53 (d, J=8.3 Hz, 3H), 7.46 (t, J=7.8 Hz, 1H), 7.32-7.27 (m, 1H), 7.21 (d, J=7.8 Hz, 2H), 3.62 (s, 3H), 2.31 (s, 3H); LCMS(m/z) 394.4.

Example 199. N-(3'-((8-Formyl-[1,2,4]triazolo[4,3-a]quinazolin-5-yl)(methyl)amino)-[1,1'-biphenyl]-4-yl)acetamide

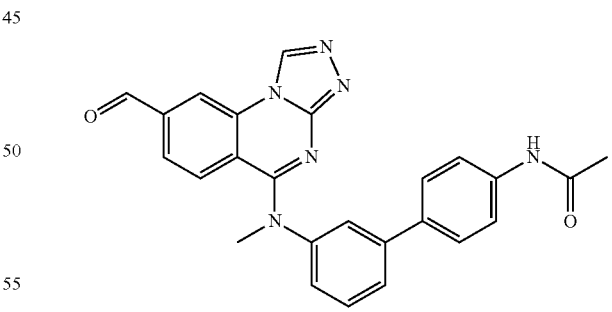

To a stirred solution of N-(3'-(methyl(8-vinyl-[1,2,4]triazolo[4,3-a]quinazolin-5-yl)amino)-[1,1'-biphenyl]-4-yl)acetamide (Example 193) (0.080 g, 0.18 mmol) in THF/water (6 mL, 2:1) were added sodium periodate (0.118 g, 0.55 mmol) and potassium osmate (VI) dihydrate (0.003 g, 0.009 mmol) at 0° C., and the mixture was stirred at RT for 16 h. The progress of the reaction was monitored by TLC. After completion of the reaction, the reaction mixture was diluted with water and stirred for few min. The resulting solids were filtered and dried under vacuum. The residue was purified by silica gel column chromatography, eluted with 8% methanol/dichloromethane to afford the desired product: ¹H NMR (500 MHz, DMSO-d₆) δ 10.05 (s, 1H), 10.01 (s, 1H), 9.78 (s, 1H), 8.81 (d, J=1.5 Hz, 1H), 7.69 (dd, J=8.5, 1.5 Hz, 1H), 7.61-7.52 (m, 7H), 7.45 (t, J=7.9 Hz, 1H), 7.28 (ddd, J=8.0, 2.2, 1.0 Hz, 1H), 3.62 (s, 3H), 2.04 (s, 3H); LCMS(m/z) 437.2.

Example 200. N-(3'-(Methyl(8-(prop-1-yn-1-yl)-[1,2,4]triazolo[4,3-a]quinazolin-5-yl)amino)-[1,1'-biphenyl]-4-yl)acetamide

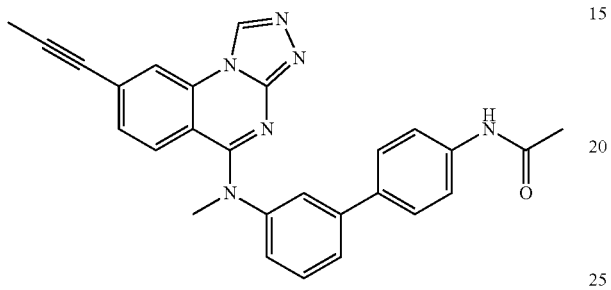

To a stirred and degassed solution of N-(3'-((8-bromo-[1,2,4]triazolo[4,3-a]quinazolin-5-yl)(methyl)amino)-[1,1'-biphenyl]-4-yl)acetamide (Example 174) (0.2 g, 0.41 mmol) in 1,4-dioxane (8 mL) was added triethylamine (0.057 mL, 0.41 mmol) at RT and the mixture was degassed with argon for 10 min, followed by the addition of triphenylphosphine (0.097 g, 0.37 mmol), copper iodide (0.015 g, 0.08 mmol), palladium acetate (0.018 g, 0.07 mmol) and 1-propyne (0.15 mL, 2.06 mmol) at RT, and the mixture was heated to 100° C. for 3 h in a sealed tube. The progress of the reaction was monitored by TLC. After completion of the reaction, the reaction mixture was filtered through a bed of celite and washed with ethyl acetate. The filtrate was evaporated under reduced pressure, and the residue was purified by silica gel column chromatography, eluted with 4% methanol/dichloromethane and further purified by prep. HPLC to afford the desired product: ¹H NMR (DMSO-d₆) δ 10.01 (brs, 1H), 9.63 (s, 1H), 8.40 (d, J=1.6 Hz, 1H), 7.66-7.52 (m, 6H), 7.44 (t, J=7.8 Hz, 1H), 7.27 (d, J=8.7 Hz, 1H), 7.23 (ddd, J=8.1, 2.3, 1.0 Hz, 1H), 7.18 (dd, J=8.7, 1.6 Hz, 1H), 3.58 (s, 3H), 2.09 (s, 3H), 2.04 (s, 3H); LCMS(m/z) 447.2.

Example 201. (5-(Methyl(4'-methyl-[1,1'-biphenyl]-3-yl)amino)-[1,2,4]triazolo[4,3-a]quinazolin-8-yl)methanol

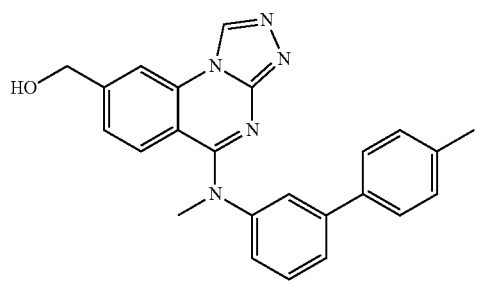 [SMILES: Cc1ccc(-c2cccc(N(C)c3nc4nncn4c4cc(CO)ccc34)c2)cc1]

To a stirred solution of 5-(methyl(4'-methyl-[1,1'-biphenyl]-3-yl)amino)-[1,2,4]triazolo[4,3-a]quinazoline-8-carbaldehyde (Example 198) (0.370 g, 0.94 mmol) in THF (10 mL) was added sodium borohydride (0.071 g, 1.88 mmol) at 0° C., and the mixture was stirred for 4 h at RT. The progress of the reaction was monitored by TLC. After completion of the reaction, the reaction mixture was quenched with ice-water and stirred for few minutes. The resulting solid was filtered and dried under vacuum. The residue was purified by prep. HPLC to afford the desired product: ¹H NMR (DMSO-d₆) δ 9.63 (s, 1H), 8.21 (d, J=1.6 Hz, 1H), 7.60 (t, J=1.9 Hz, 1H), 7.58-7.51 (m, 3H), 7.44 (t, J=7.8 Hz, 1H), 7.30 (d, J=8.6 Hz, 1H), 7.25-7.20 (m, 3H), 7.14 (dd, J=8.8, 1.5 Hz, 1H), 5.50 (s, 1H), 4.60 (s, 2H), 3.60 (s, 3H), 2.31 (s, 3H); LCMS(m/z) 396.4.

Example 202. (5-((4'-Methoxy-[1,1'-biphenyl]-3-yl)(methyl)amino)-[1,2,4]triazolo[4,3-a]quinazolin-8-yl)methanol

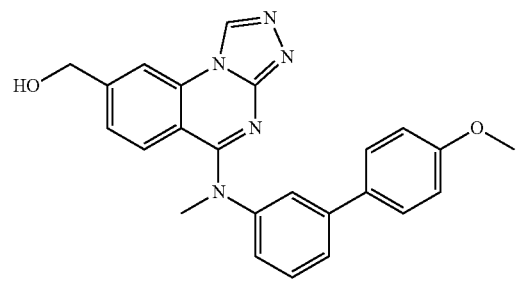

To a stirred solution of 5-((4'-Methoxy-[1,1'-biphenyl]-3-yl)(methyl)amino)-[1,2,4]triazolo[4,3-a]quinazoline-8-carbaldehyde (Example 190) (0.1 g, 0.24 mmol) in THF/water (5 mL, 1:1) was added sodium borohydride (0.018 g, 0.49 mmol) at 0° C., and the mixture was stirred at RT for 2 h. The progress of the reaction was monitored by TLC. After completion of the reaction, the reaction mixture was diluted with water and extracted with ethyl acetate. The organic layer was washed with brine, dried over Na₂SO₄, filtered and evaporated under reduced pressure. The residue was purified by silica gel column chromatography, eluted with 8% methanol/dichloromethane to afford the desired product: ¹H NMR (DMSO-d₆) δ 9.64 (s, 1H), 8.21 (d, J=1.6 Hz, 1H), 7.64-7.54 (m, 3H), 7.55-7.48 (m, 1H), 7.42 (t, J=7.8 Hz, 1H), 7.30 (d, J=8.6 Hz, 1H), 7.25-7.08 (m, 2H), 7.03-6.90 (m, 2H), 5.50 (t, J=5.6 Hz, 1H), 4.60 (d, J=5.6 Hz, 2H), 3.77 (s, 3H), 3.59 (s, 3H); LCMS(m/z) 412.5.

Example 203. N-(3'-((8-(Hydroxymethyl)-[1,2,4]triazolo[4,3-a]quinazolin-5-yl)(methyl)amino)-[1,1'-biphenyl]-4-yl)acetamide

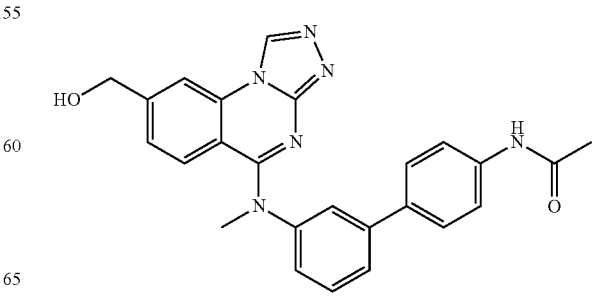

To a stirred solution of N-(3'-((8-formyl-[1,2,4]triazolo[4,3-a]quinazolin-5-yl)(methyl)amino)-[1,1'-biphenyl]-4-yl)acetamide (Example 199) (0.220 g, 0.50 mmol) in THF (6 mL) was added sodium borohydride (0.038 g, 1.01 mmol) at 0° C. and the mixture was stirred at RT for 4 h. The progress of the reaction was monitored by TLC. After completion of the reaction, the reaction mixture was diluted with water and stirred for a few minutes. The resulting solids were filtered and dried under vacuum. The residue was purified by prep. HPLC to afford the desired product: $^1$H NMR (DMSO-$d_6$) δ 10.01 (s, 1H), 9.64 (s, 1H), 8.21 (d, J=1.6 Hz, 1H), 7.65-7.50 (m, 6H), 7.43 (t, J=7.9 Hz, 1H), 7.30 (d, J=8.6 Hz, 1H), 7.21 (ddd, J=7.9, 2.1, 1.0 Hz, 1H), 7.14 (dd, J=8.7, 1.6 Hz, 1H), 5.49 (t, J=5.6 Hz, 1H), 4.60 (d, J=5.6 Hz, 2H), 3.59 (s, 3H), 2.04 (s, 3H); LCMS(m/z) 439.2.

Example 204. N-Methyl-N-(4'-methyl-[1,1'-biphenyl]-3-yl)-8-vinyl-[1,2,4]triazolo[4,3-a]quinazolin-5-amine

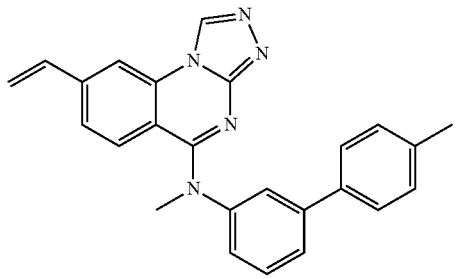 [SMILES: C=Cc1ccc2c(N(C)c3cccc(-c4ccc(C)cc4)c3)nc3nncn3c2c1]

To a stirred solution of 8-bromo-N-methyl-N-(4'-methyl-[1,1'-biphenyl]-3-yl)-[1,2,4]triazolo[4,3-a]quinazolin-5-amine (Example 172) (0.3 g, 0.68 mmol) in t-butanol (10 mL) were added potassium tert-butoxide (0.228 g, 2.03 mmol) at RT and the mixture was degassed with argon for 10 min, followed by the addition of tetrakis(triphenylphosphine)palladium (0) (0.156 g, 0.13 mmol) and 4,4,5,5-tetramethyl-2-vinyl-1,3,2-dioxaborolane (0.208 g, 1.35 mmol) at RT, and the mixture was heated to 80° C. for 4 h in a sealed tube. The progress of the reaction was monitored by TLC. After completion of the reaction, the reaction mixture was diluted with water and extracted with ethyl acetate. The organic layer was washed with brine, dried over Na$_2$SO$_4$, filtered and evaporated under reduced pressure. The residue was purified by prep. HPLC to afford the desired product: $^1$H NMR (500 MHz, DMSO-$d_6$) δ 9.62 (s, 1H), 8.39 (d, J=1.6 Hz, 1H), 7.62 (t, J=1.9 Hz, 1H), 7.57-7.51 (m, 3H), 7.45 (t, J=7.8 Hz, 1H), 7.35 (dd, J=8.7, 1.7 Hz, 1H), 7.28 (d, J=8.7 Hz, 1H), 7.26-7.20 (m, 3H), 6.78 (dd, J=17.6, 11.0 Hz, 1H), 6.15 (d, J=17.6 Hz, 1H), 5.54 (d, J=11.0 Hz, 1H), 3.60 (s, 3H), 2.31 (s, 3H); LCMS(m/z) 392.3.

Example 205. 8-Bromo-5-(3,4-dihydroquinolin-1(2H)-yl)-[1,2,4]triazolo[4,3-a]quinazoline

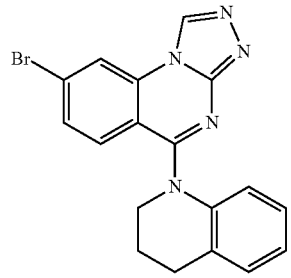 [SMILES: Brc1ccc2c(N3CCCc4ccccc43)nc3nncn3c2c1]

(Step 1) Synthesis of 7-bromo-2-chloro-4-(3,4-dihydroquinolin-1(2H)-yl)quinazoline

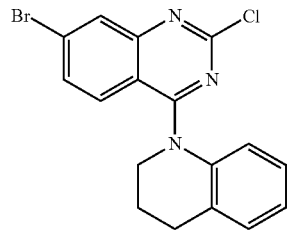 [SMILES: Clc1nc(N2CCCc3ccccc32)c2ccc(Br)cc2n1]

To a solution of 6-bromo-2,4-dichloroquinazoline (2 g, 7.20 mmol) in DMF (36 mL) were added 1,2,3,4-tetrahydroquinoline (0.958 g, 7.20 mmol) and sodium hydride (0.173 g, 7.20 mmol), and the mixture was stirred for 1 h at RT. The reaction mixture was diluted with AcOEt, and washed successively with water and brine, and dried over Na$_2$SO$_4$. The organic layer was concentrated in vacuo. The residue was used for the next step without further purification. LCMS(m/z) 376.03 [M+H]$^+$.

(Step 2) Synthesis of 7-bromo-4-(3,4-dihydroquinolin-1(2H)-yl)-2-hydrazinylquinazoline

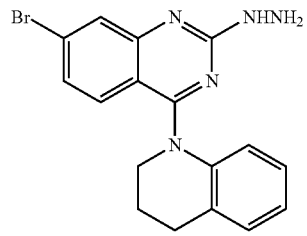 [SMILES: NNc1nc(N2CCCc3ccccc32)c2ccc(Br)cc2n1]

To a solution of 7-bromo-2-chloro-4-(3,4-dihydroquinolin-1(2H)-yl)quinazoline (1.22 g, 3.26 mmol) in EtOH (16.28 mL) was added hydrazine hydrate (0.326 g, 6.51 mmol), and the mixture was stirred for 2 h at RT. The reaction mixture was diluted with AcOEt, and washed successively with water and brine. The organic layer was concentrated in vacuo. The residue was used for the next step without further purification. LCMS(m/z) 370.08 [M+H]+.

(Step 3) Synthesis of 8-bromo-5-(3,4-dihydroquino-lin-1(2H)-yl)-[1,2,4]triazolo[4,3-a]quinazoline A mixture of 7-bromo-4-(3,4-dihydroquinolin-1(2H)-yl)-2-hydrazinylquinazoline (crude, 1.1 g, 2.97 mmol) and triethoxymethane (15 mL, 2.97 mmol) was stirred overnight at 100° C. The reaction mixture was concentrated in vacuo. The residue was purified by column chromatography (Si-column, CHCl$_3$:MeOH=10:0-9:1) to afford the desired product: $^1$H NMR (DMSO-d$_6$) δ 9.71 (s, 1H), 8.74 (d, J=1.9 Hz, 1H), 7.57 (dd, J=8.8, 1.9 Hz, 1H), 7.45 (d, J=8.8 Hz, 1H), 7.27 (d, J=7.1 Hz, 1H), 7.01 (td, J=7.4, 1.3 Hz, 1H), 6.95 (td, J=7.6, 1.7 Hz, 1H), 6.78-6.74 (m, 1H), 3.90 (t, J=6.5 Hz, 2H), 2.89 (t, J=6.6 Hz, 2H), 2.08 (q, J=6.6 Hz, 2H); LCMS(m/z) 380.1/382.1.

Example 206. 7-Fluoro-N5-methyl-N5-phenyl-[1,2,4]triazolo[4,3-a]quinazoline-5,8-diamine

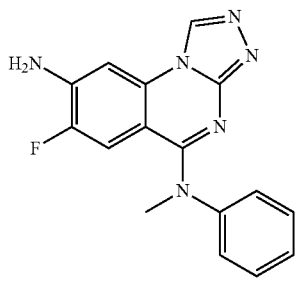

(Step 1) Synthesis of 8-azido-7-fluoro-N-methyl-N-phenyl-[1,2,4]triazolo[4,3-a]quinazolin-5-amine

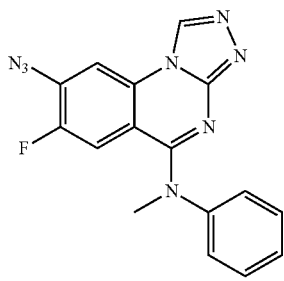

To a solution of 7,8-difluoro-N-methyl-N-phenyl-[1,2,4]triazolo[4,3-a]quinazolin-5-amine (Example 182) (20 mg, 0.064 mmol) in DMSO (321 μL) was added sodium azide (20.68 mg, 0.318 mmol), and the mixture was heated to 90° C. for 2 h. The reaction mixture was diluted with AcOEt, washed successively with water and brine, and dried over Na$_2$SO$_4$. The organic layer was concentrated in vacuo. The resulting residue was used in the next step without further purification. LCMS(m/z) 336.14 [M+H]$^+$.

(Step 2) Synthesis of 7-fluoro-N-methyl-N-phenyl-[1,2,4]triazolo[4,3-a]quinazoline-5,8-diamine A mixture of the resulting 8-azido-7-fluoro-N-methyl-N-phenyl-[1,2,4]triazolo[4,3-a]quinazolin-5-amine (80 mg, 0.239 mmol) and Pd/C (10 mg) in ethanol (1.2 mL) was heated to 60° C. for 2 days under H$_2$ atmosphere. Pd/C was removed by filtration, and the filtrate was concentrated in vacuo. The residue was purified by column chromatography (Si-column, CHCl$_3$:MeOH=0-15%) to afford the desired product: $^1$H NMR (DMSO-d$_6$) δ 9.31 (s, 1H), 7.47-7.36 (m, 2H), 7.31-7.21 (m, 4H), 6.65 (d, J=13.3 Hz, 1H), 6.58 (s, 2H), 3.48 (s, 3H); LCMS(m/z) 309.1.

Example 207. N5-Ethyl-7-fluoro-N5-phenyl-[1,2,4]triazolo[4,3-a]quinazoline-5,8-diamine

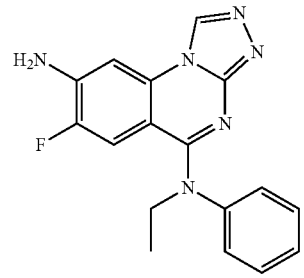 [SMILES: CCN(c1ccccc1)c1nc2nncn2c2cc(N)c(F)cc12]

(Step 1) Synthesis of 2-chloro-N-ethyl-6,7-difluoro-N-phenylquinazolin-4-amine

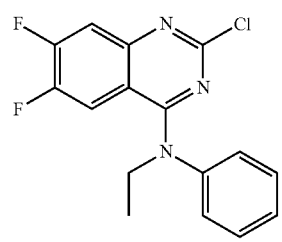

To a solution of 2,4-dichloro-6,7-difluoroquinazoline (1.1 g, 4.68 mmol) in DMF (23.4 mL) were added sodium hydride (0.112 g, 4.68 mmol) and N-methylaniline (0.567 g, 4.68 mmol), and the mixture was stirred for 0.5 h at RT. The reaction mixture was diluted with AcOEt, washed successively with water and brine, and dried over Na$_2$SO$_4$. The organic layer was concentrated in vacuo. The resulting residue was used in the next step without further purification. LCMS(m/z) 320.14 [M+H]$^+$.

(Step 2) Synthesis of N-ethyl-6,7-difluoro-2-hydrazinyl-N-phenylquinazolin-4-amine

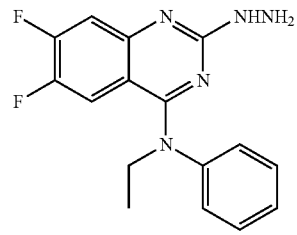

Hydrazine hydrate (0.038 g, 0.760 mmol) was added slowly to a stirred solution of 2-chloro-N-ethyl-6,7-difluoro- N-phenylquinazolin-4-amine (crude, 0.81 g, 2.53 mmol) in ethanol (12.67 mL) at RT. After 1 h and 2 h, additional portions of hydrazine hydrate (0.038 g×2, 1.520 mmol) were added slowly to the solution, and stirring was continued for 1 h. The mixture was diluted with AcOEt, washed successively with water and brine, and dried over Na$_2$SO$_4$. The organic layer was concentrated in vacuo. The resulting residue was used in the next step without further purification. LCMS(m/z) 316.14 [M+H]$^+$.

(Step 3) Synthesis of N-ethyl-7,8-difluoro-N-phenyl-[1,2,4]triazolo[4,3-a]quinazolin-5-amine

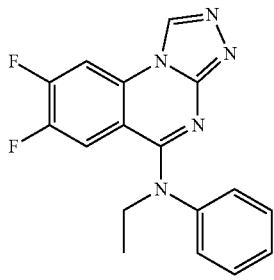

A mixture of N-ethyl-6,7-difluoro-2-hydrazinyl-N-phenylquinazolin-4-amine (crude, 0.69 g, 2.188 mmol)) and triethylorthoformate (10 mL, 2.188 mmol) was heated to 100° C. for 3 h. After completion of the reaction, the mixture was concentrated in vacuo. The residue was purified by column chromatography (Si-column, CHC$_3$:MeOH=10:0-9:1) to give the desired product. LCMS(m/z) 326.14 [M+H]$^+$.

(Step 4) Synthesis of 8-azido-N-ethyl-7-fluoro-N-phenyl-[1,2,4]triazolo[4,3-a]quinazolin-5-amine

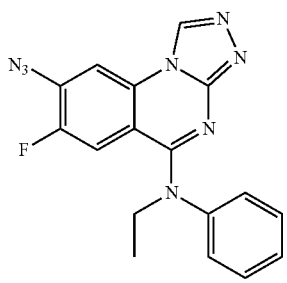 [SMILES: CCN(c1ccccc1)c1nc2nncn2c2cc(N=[N+]=[N-])c(F)cc12]

To a solution of N-ethyl-7,8-difluoro-N-phenyl-[1,2,4]triazolo[4,3-a]quinazolin-5-amine (crude, 400 mg, 1.23 mmol) in DMSO (6148 µL) was added sodium azide (84 mg, 1.291 mmol), and the mixture was heated to 60° C. for 2 h. The reaction mixture was diluted with AcOEt, and washed successively with water and brine, and dried over Na$_2$SO$_4$. The organic layer was concentrated in vacuo. The resulting residue was used in the next step without further purification. LCMS(m/z) 349.14 [M+H]$^+$.

(Step 5) Synthesis of N5-ethyl-7-fluoro-N-phenyl-[1,2,4]triazolo[4,3-a]quinazoline-5,8-diamine A mixture of 8-azido-N-ethyl-7-fluoro-N-phenyl-[1,2,4]triazolo[4,3-a]quinazolin-5-amine (crude, 0.46 g, 1.321 mmol) and Pd/C (30 mg) in ethanol (6.6 mL) was heated to 60° C. for overnight. Pd/C was removed by filtration, and the filtrate was concentrated in vacuo. The residue was purified by column chromatography (Si-column, CHC$_3$:MeOH=10:0-9:1) to afford the desired product: $^1$H NMR (Methanol-d$_4$) δ 9.17 (s, 1H), 7.55-7.43 (m, 2H), 7.41-7.32 (m, 1H), 7.31-7.17 (m, 3H), 6.68 (dd, J=13.5, 1.3 Hz, 1H), 4.22 (q, J=6.9 Hz, 2H), 1.33 (t, J=7.0 Hz, 3H); LCMS(m/z) 323.1.

Example 208. 7-Fluoro-N5-(3-fluorophenyl)-N5-methyl-[1,2,4]triazolo[4,3-a]quinazoline-5,8-diamine

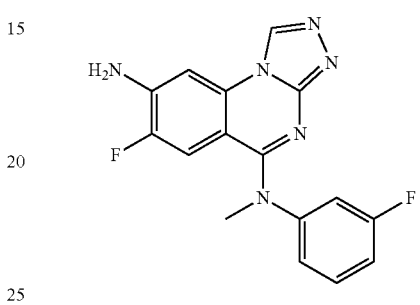

(Step 1) Synthesis of 2-chloro-6,7-difluoro-N-(3-fluorophenyl)-N-methylquinazolin-4-amine

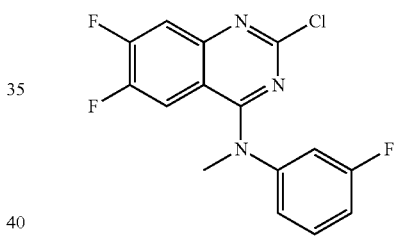

To a solution of 2,4-dichloro-6, 7-difluoroquinazoline (1.05 g, 4.47 mmol) in DMF (22.3 mL) were added 3-fluoro-N-methylaniline (0.559 g, 4.47 mmol) and sodium hydride (0.107 g, 4.47 mmol), and the mixture was stirred for 1 h at RT. The reaction mixture was diluted with AcOEt, then washed successively with water and brine and dried over Na$_2$SO$_4$. The organic layer was concentrated in vacuo. The resulting residue was used in the next step without further purification. LCMS(m/z) 324.04 [M+H]$^+$.

(Step 2) Synthesis of 6,7-difluoro-N-(3-fluorophenyl)-2-hydrazinyl-N-methylquinazolin-4-amine

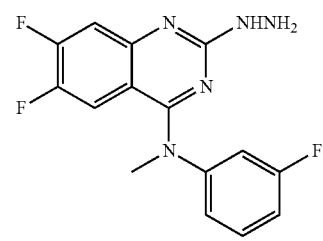 [SMILES: CN(c1cccc(F)c1)c1nc(NN)nc2cc(F)c(F)cc12]

Hydrazine hydrate (0.118 g, 2.354 mmol) was added slowly to a stirred solution of 2-chloro-6,7-difluoro-N-(3-fluorophenyl)-N-methylquinazolin-4-amine (crude, 2.54 g, 7.85 mmol) in ethanol (39.2 mL) at RT. After 1 h and 2 h, additional portions of hydrazine hydrate (0.118 g×4.708 mmol) were added slowly to the solution, and the stirring continued for 1 h. The mixture was diluted with AcOEt, washed successively with water and brine, and dried over Na$_2$SO$_4$. The organic layer was concentrated in vacuo. The resulting residue was used in the next step without further purification. LCMS(m/z) 320.14 [M+H]$^+$.

(Step 3) Synthesis of 7,8-difluoro-N-(3-fluorophenyl)-N-methyl-[1,2,4]triazolo[4,3-a]quinazolin-5-amine

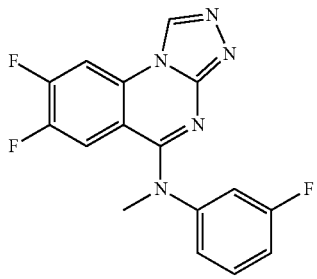 [SMILES: CN(c1cccc(F)c1)c1nc2nncn2c2cc(F)c(F)cc12]

A mixture of 6,7-difluoro-N-(3-fluorophenyl)-2-hydrazinyl-N-methylquinazolin-4-amine (crude, 0.51 g, 1.597 mmol) and triethoxymethane (5 mL, 1.597 mmol) was stirred at 100° C. for 4 h. The reaction mixture was concentrated in vacuo. The residue was purified by column chromatography (Si-column, CHC$_3$. MeOH=0-15%) to give the desired product. LCMS(m/z) 330.09 [M+H]$^+$.

(Step 4) Synthesis of 8-azido-7-fluoro-N-(3-fluorophenyl)-N-methyl-[1,2,4]triazolo[4,3-a]quinazolin-5-amine

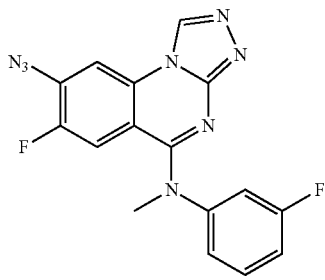 [SMILES: CN(c1cccc(F)c1)c1nc2nncn2c2cc(N=[N+]=[N-])c(F)cc12]

To a solution of 7,8-difluoro-N-(3-fluorophenyl)-N-methyl-[1,2,4]triazolo[4,3-a]quinazolin-5-amine (0.29 g, 0.881 mmol) in DMSO (2.94 mL) was added sodium azide (0.057 g, 0.881 mmol), and the mixture was stirred for 2 h at 60° C. The reaction mixture was diluted with AcOEt, and then washed successively with water and brine, and dried over Na$_2$SO$_4$. The organic layer was concentrated in vacuo. The resulting residue was used in the next step without further purification.

(Step 5) Synthesis of 7-fluoro-N5-(3-fluorophenyl)-N5-methyl-[1,2,4]triazolo[4,3-a]quinazoline-5,8-diamine To a solution of 8-azido-7-fluoro-N-(3-fluorophenyl)-N-methyl-[1,2,4]triazolo[4,3-a]quinazolin-5-amine (crude, 0.32 g, 0.908 mmol) in ethanol (4.54 mL) was added Pd/C (30 mg), and the suspension was stirred for 5 h at 60° C. under H$_2$ gas atmosphere. Pd/C was removed by filtration, and the filtrate was concentrated in vacuo. The residue was purified by column chromatography (Si-column, CHC$_3$: MeOH=10:0-9:1) to afford the desired product: $^1$H NMR (DMSO-d$_6$) δ 9.37 (s, 1H), 7.38 (td, J=8.2, 6.8 Hz, 1H), 7.28 (d, J=7.9 Hz, 1H), 7.19 (dt, J=10.8, 2.3 Hz, 1H), 7.10-6.97 (m, 2H), 6.77 (d, J=12.9 Hz, 1H), 6.67 (s, 2H), 3.49 (s, 3H); LCMS(m/z) 327.1.

Example 209. (5-((4'-Chloro-[1,1'-biphenyl]-3-yl)(methyl)amino)-[1,2,4]triazolo[4,3-a]quinazolin-8-yl)methanol

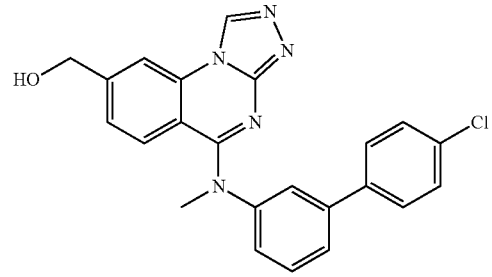 [SMILES: CN(c1cccc(-c2ccc(Cl)cc2)c1)c1nc2nncn2c2cc(CO)ccc12]

To a stirred solution of 5-((4'-chloro-[1,1'-biphenyl]-3-yl)(methyl)amino)-[1,2,4]triazolo[4,3-a]quinazoline-8-carbaldehyde (Example 211) (0.1 g, 0.24 mmol) in tetrahydrofuran (5 mL) was added sodium borohydride (0.018 g, 0.48 mmol) at 0° C., and the mixture was stirred for 3 h at RT. The progress of the reaction was monitored by TLC. After completion of the reaction, the reaction mixture was diluted with water and extracted with 10% methanol/dichloromethane. The organic layer was washed with brine, dried over anhydrous Na$_2$SO$_4$, filtered and evaporated under reduced pressure to give crude compound. The crude was purified by prep. HPLC to afford the desired compound: $^1$H NMR (DMSO-d$_6$) δ 9.64 (s, 1H), 8.21 (d, J=1.6 Hz, 1H), 7.72-7.64 (m, 3H), 7.57 (dt, J=8.1, 1.3 Hz, 1H), 7.50-7.43 (m, 3H), 7.32-7.24 (m, 2H), 7.14 (dd, J=8.6, 1.6 Hz, 1H), 5.50 (t, J=5.6 Hz, 1H), 4.61 (d, J=5.4 Hz, 2H), 3.60 (s, 3H); LCMS(m/z) 416.4.

Example 210. N-(4'-Chloro-[1,1'-biphenyl]-3-yl)-N-methyl-8-vinyl-[1,2,4]triazolo[4,3-a]quinazolin-5-amine

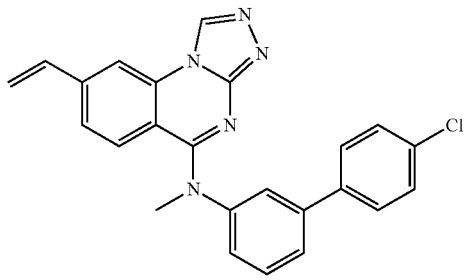 [SMILES: C=Cc1ccc2c(N(C)c3cccc(-c4ccc(Cl)cc4)c3)nc3nncn3c2c1]

To a stirred solution of 8-bromo-N-(4'-chloro-[1,1'-biphenyl]-3-yl)-N-methyl-[1,2,4]triazolo[4,3-a]quinazolin-5-amine (Example 185) (0.2 g, 0.43 mmol) in t-butanol (5 mL) were added potassium tert-butoxide (0.096 g, 0.86 mmol), tetrakis(triphenylphosphine)palladium (0) (0.049 g, 0.04 mmol) and 4,4,5,5-tetramethyl-2-vinyl-1,3,2-dioxaborolane (0.099 g, 0.65 mmol) at RT, and the mixture was heated to 100° C. for 6 h. The progress of the reaction was monitored by TLC. After completion of the reaction, the reaction mixture was diluted with water and extracted with ethyl acetate. The organic layer was washed with brine, dried over anhydrous $Na_2SO_4$, filtered and evaporated under reduced pressure to give crude residue. The residue was purified by prep. HPLC to afford the desired product: $^1$H NMR (DMSO-$d_6$) δ 9.63 (s, 1H), 8.39 (d, J=1.6 Hz, 1H), 7.71-7.64 (m, 3H), 7.58 (dt, J=8.1, 1.3 Hz, 1H), 7.51-7.44 (m, 3H), 7.35 (dd, J=8.7, 1.6 Hz, 1H), 7.32-7.25 (m, 2H), 6.78 (dd, J=17.6, 10.9 Hz, 1H), 6.16 (d, J=17.6 Hz, 1H), 5.54 (d, J=10.9 Hz, 1H), 3.60 (s, 3H); LCMS(m/z) 412.4.

Example 211. 5-((4'-Chloro-[1,1'-biphenyl]-3-yl)(methyl)amino)-[1,2,4]triazolo[4,3-a]quinazoline-8-carbaldehyde

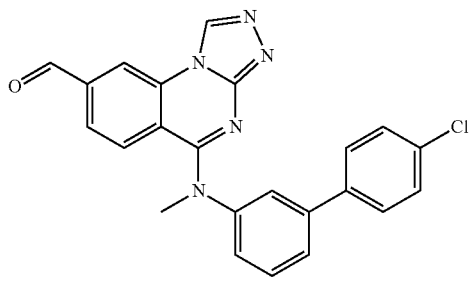 [SMILES: CN(c1cccc(-c2ccc(Cl)cc2)c1)c1nc2nncn2c2cc(C=O)ccc12]

To a stirred solution of N-(4'-chloro-[1,1'-biphenyl]-3-yl)-N-methyl-8-vinyl-[1,2,4]triazolo[4,3-a]quinazolin-5-amine (Example 210) (0.140 g, 0.34 mmol) in a mixture of tetrahydrofuran/water (13 mL, 10:3) were added sodium periodate (0.218 g, 1.02 mmol) and potassium osmate (VI) dihydrate (0.006 g, 0.02 mmol) at 0° C., and the mixture was stirred for 2 h at RT. The progress of the reaction was monitored by TLC. After completion of the reaction, the reaction mixture was diluted with ice-water. The resulting solid was filtered and dried under vacuum to give crude residue. The residue was purified by silica gel column chromatography, eluted with 6% methanol/dichloromethane to afford the desired product: $^1$H NMR (DMSO-$d_6$) δ 10.05 (s, 1H), 9.79 (s, 1H), 8.81 (d, J=1.5 Hz, 1H), 7.72-7.64 (m, 4H), 7.62-7.57 (m, 1H), 7.53 (d, J=8.5 Hz, 1H), 7.49-7.43 (m, 3H), 7.35 (ddd, J=7.8, 2.1, 1.0 Hz, 1H), 3.62 (s, 3H); LCMS(m/z) 414.4.

Example 212. 5-((4'-(tert-Butyl)-[1,1'-biphenyl]-3-yl)(methyl)amino)-[1,2,4]triazolo[4,3-a]quinazoline-8-carbaldehyde

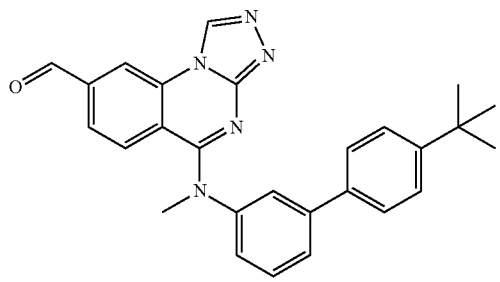 [SMILES: CN(c1cccc(-c2ccc(C(C)(C)C)cc2)c1)c1nc2nncn2c2cc(C=O)ccc12]

To a stirred solution of N-(4'-(tert-butyl)-[1,1'-biphenyl]-3-yl)-N-methyl-8-vinyl-[1,2,4]triazolo[4,3-a]quinazolin-5-amine (Example 194) (0.360 g, 0.83 mmol) in THF/water (20 mL, 2:1) were added sodium periodate (0.533 g, 2.49 mmol) and potassium osmate (VI) dihydrate (0.015 g, 0.04 mmol) at 0° C., and the mixture was stirred at RT for 16 h. The progress of the reaction was monitored by TLC. After completion of the reaction, the reaction mixture was diluted with ice-water. The resulting solids were filtered and dried under vacuum. The crude solids were purified by prep. HPLC to afford the desired product: $^1$H NMR (DMSO-$d_6$) δ 10.05 (s, 1H), 9.78 (s, 1H), 8.81 (d, J=1.5 Hz, 1H), 7.68 (dd, J=8.5, 1.5 Hz, 1H), 7.60 (m, 1H), 7.58-7.51 (m, 4H), 7.49 (m, 1H), 7.43-7.39 (m, 2H), 7.33 (ddd, J=7.8, 2.2, 1.1 Hz, 1H), 3.63 (s, 3H), 1.27 (s, 9H); LCMS(m/z) 436.3.

Example 213. (5-((4'-(tert-Butyl)-[1,1'-biphenyl]-3-yl)(methyl)amino)-[1,2,4]triazolo[4,3-a]quinazolin-8-yl)methanol

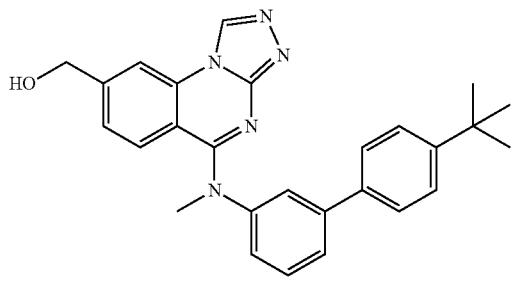 [SMILES: CN(c1cccc(-c2ccc(C(C)(C)C)cc2)c1)c1nc2nncn2c2cc(CO)ccc12]

To a stirred solution of 5-((4'-(tert-butyl)-[1,1'-biphenyl]-3-yl)(methyl)amino)-[1,2,4]triazolo[4,3-a]quinazoline-8-carbaldehyde (Example 212) (0.09 g, 0.21 mmol) in THF/water (5 mL, 1:1) was added sodium borohydride (0.015 g, 0.41 mmol) at 0° C., and the mixture was stirred at RT for 4 h. The progress of the reaction was monitored by TLC. After completion of the reaction, the reaction mixture was diluted with ice-water and extracted with ethyl acetate. The organic layer was washed with brine, dried over Na₂SO₄, filtered and evaporated under reduced pressure. The residue was purified by silica gel column chromatography, eluted with 4% methanol/dichloromethane to afford the desired product: ¹H NMR (DMSO-d₆) δ 9.63 (s, 1H), 8.21 (d, J=1.6 Hz, 1H), 7.61-7.51 (m, 4H), 7.49-7.39 (m, 3H), 7.29 (d, J=8.6 Hz, 1H), 7.25 (ddd, J=8.0, 2.3, 1.1 Hz, 1H), 7.14 (d, J=1.6 Hz, 1H), 5.49 (t, J=5.6 Hz, 1H), 4.60 (d, J=5.4 Hz, 2H), 3.60 (s, 3H), 1.28 (s, 9H); LCMS(m/z) 438.5.

Example 214. N-(4'-Chloro-[1,1'-biphenyl]-3-yl)-N-methyl-8-(prop-1-yn-1-yl)-[1,2,4]triazolo[4,3-a]quinazolin-5-amine

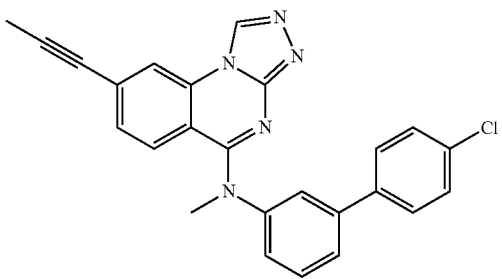 [SMILES: CC#Cc1ccc2c(N(C)c3cccc(-c4ccc(Cl)cc4)c3)nc3nncn3c2c1]

To a stirred and degassed solution of 8-bromo-N-(4'-chloro-[1,1'-biphenyl]-3-yl)-N-methyl-[1,2,4]triazolo[4,3-a]quinazolin-5-amine (Example 185) (0.1 g, 0.21 mmol) in 1,4-dioxane (3 mL) were added triphenylphosphine (0.051 g, 0.19 mmol), triethylamine (0.03 mL, 0.21 mmol), copper iodide (0.008 g, 0.04 mmol), palladium acetate (0.010 g, 0.04 mmol) and 1-propyne (0.13 mL, 2.16 mmol) at RT and the mixture was heated to 100° C. for 6 h. The progress of the reaction was monitored by TLC. After completion of the reaction, the reaction mixture was diluted with water and extracted with ethyl acetate. The organic layer was washed with brine, dried over Na₂SO₄, filtered and evaporated under reduced pressure. The residue was purified by prep. HPLC to afford the desired product: ¹H NMR (500 MHz, DMSO-d₆) δ 9.64 (s, 1H), 8.40 (d, J=1.6 Hz, 1H), 7.69-7.63 (m, 3H), 7.57 (ddd, J=7.9, 1.9, 1.1 Hz, 1H), 7.50-7.44 (m, 3H), 7.31 (ddd, J=8.0, 2.2, 1.0 Hz, 1H), 7.27 (d, J=8.7 Hz, 1H), 7.18 (dd, J=8.6, 1.6 Hz, 1H), 3.59 (s, 3H), 2.09 (s, 3H); LCMS (m/z) 424.4.

Example 215. 8-Bromo-7-fluoro-N-methyl-N-phenyl-[1,2,4]triazolo[4,3-a]quinazolin-5-amine

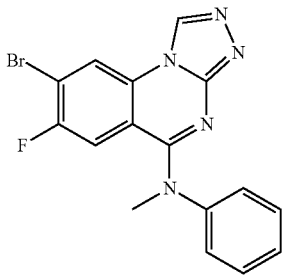

To a solution of 7-fluoro-N5-methyl-N5-phenyl-[1,2,4]triazolo[4,3-a]quinazoline-5,8-diamine (Example 206) (25 mg, 0.081 mmol) in acetonitrile (1 mL) were added copper (II) bromide (49.1 mg, 0.220 mmol) and tert-butyl nitrite (24.75 mg, 0.240 mmol), and the mixture was stirred for 2 h at RT. The reaction mixture was diluted with AcOEt, washed successively with water and brine, and dried over Na₂SO₄. The organic layer was concentrated in vacuo. The resulting residue was purified by column chromatography (Si-column, CHCl₃:MeOH=0-15%) to give the crude product. The reaction mixture was purified by solid phase extraction (washed with MeOH, then eluted with NH₃ in MeOH) using Bond Elut SCX cartridge (Agilent), and the collected fractions were concentrated to afford the desired product: ¹H NMR (Methanol-d₄) δ 9.33 (s, 1H), 8.54 (d, J=6.0 Hz, 1H), 7.41-7.36 (m, 2H), 7.33-7.27 (m, 1H), 7.25-7.21 (m, 2H), 6.82 (d, J=10.3 Hz, 1H), 3.55 (s, 3H); LCMS(m/z) 374.1/375.2.

Example 216. 7-Fluoro-5-(7-fluoro-3,4-dihydroquinolin-1(2H)-yl)-[1,2,4]triazolo[4,3-a]quinazolin-8-amine

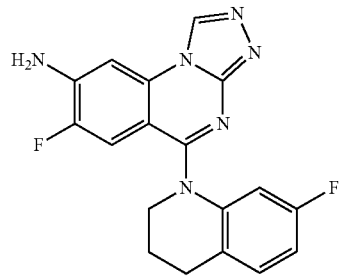 [SMILES: Nc1cc2c(cc1F)c(N1CCCc3ccc(F)cc31)nc1nncn12]

(Step 1) Synthesis of Methyl 3-(4-fluoro-2-nitrophenyl)acrylate

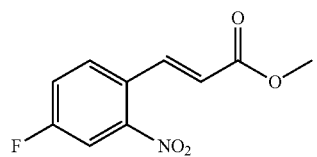 [SMILES: COC(=O)/C=C/c1ccc(F)cc1[N+](=O)[O-]]

A mixture of 4-fluoro-2-nitroaniline (200 mg, 1.281 mmol), methyl acrylate (132 mg, 1.537 mmol), tertbutyl nitrite (145 mg, 1.409 mmol) and Pd(OAc)₂ (57.5 mg, 0.256 mmol) in MeOH (6.4 mL) was stirred for 4 h at 60° C. The reaction mixture was diluted with AcOEt and washed successively with water and brine. The organic layer was concentrated in vacuo to give the desired product.

(Step 2) Synthesis of 7-fluoro-3,4-dihydroquinolin-2(1H)-one

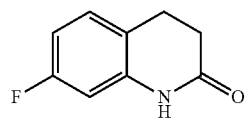

A mixture of methyl 3-(4-fluoro-2-nitrophenyl)acrylate (163 mg, 0.724 mmol) and Pd(OAc)$_2$ (163 mg, 0.724 mmol) in MeOH (3.6 mL) was stirred for overnight at 60° C. The mixture was concentrated in vacuo. The residue was purified by column chromatography (Si-column, hexane:AcOEt=10: 0-9:1) to give the desired product. LCMS(m/z) 166.14 [M+H]$^+$.

(Step 3) Synthesis of 7-fluoro-1,2,3,4-tetrahydroquinoline

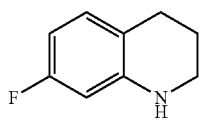

A mixture of 7-fluoro-3,4-dihydroquinolin-2(1H)-one (97 mg, 0.587 mmol) and BH$_3$ in THF (0.2 M solution) (12.19 mg, 0.881 mmol) in THF (2.9 mL) was stirred overnight at 50° C.

The reaction mixture was concentrated in vacuo. The residue was purified by column chromatography (Si-column, hexane:AcOEt=10:0-9:1) to give the desired product: $^1$H NMR (400 MHz, CDCl$_3$) δ 6.85 (ddt, J=8.4, 6.6, 1.0 Hz, 1H), 6.27 (td, J=8.5, 2.6 Hz, 1H), 6.15 (dd, J=10.8, 2.6 Hz, 1H), 3.39-3.20 (m, 2H), 2.70 (t, J=6.4 Hz, 2H), 2.05-1.83 (m, 2H).

(Step 4) Synthesis of 2-chloro-6,7-difluoro-4-(7-fluoro-3,4-dihydroquinolin-1(2H)-yl)quinazoline

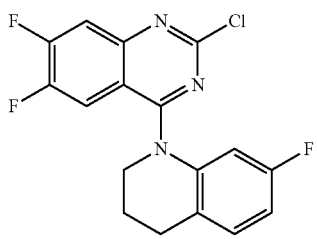 [SMILES: Fc1ccc2c(c1)N(c1nc(Cl)nc3cc(F)c(F)cc13)CCC2]

To a solution of 2,4-dichloro-6,7-difluoroquinazoline (0.89 g, 3.79 mmol) in DMF (18.93 ml) were added 7-fluoro-1,2,3,4-tetrahydroquinoline (0.573 g, 3.79 mmol) and sodium hydride (0.091 g, 3.79 mmol), and the mixture was stirred for 2 h at RT. The reaction mixture was diluted with AcOEt and washed successively with water and brine. The organic layer was concentrated in vacuo. The residue was used for the next step without further purification. LCMS(m/z) 350.14 [M+H]$^+$.

(Step 5) Synthesis of 6,7-difluoro-4-(7-fluoro-3,4-dihydroquinolin-1(2H)-yl)-2-hydrazinylquinazoline

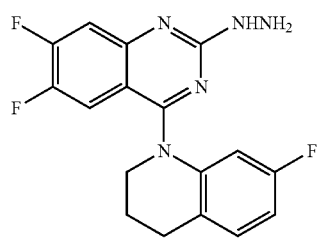 [SMILES: NNc1nc(N2CCCc3ccc(F)cc32)c2cc(F)c(F)cc2n1]

To a solution of 2-chloro-6,7-difluoro-4-(7-fluoro-3,4-dihydroquinolin-1(2H)-yl)quinazoline (0.35 g, crude) in EtOH (5 mL) was added hydrazine hydrate (0.015 g, 0.3 mmol) slowly, and the mixture was stirred for 30 min at RT. After 0.5 h and 1 h, additional portions of hydrazine hydrate (0.015 g×2, 0.6 mmol) were added slowly to the solution, and the stirring was continued for 1 h. The reaction mixture was diluted with AcOEt and washed successively with water and brine. The organic layer was concentrated in vacuo. The residue was used for the next step without further purification. LCMS(m/z) 346.14 [M+H]$^+$.

(Step 6) Synthesis of 7,8-difluoro-5-(7-fluoro-3,4-dihydroquinolin-1(2H)-yl)-[1,2,4]triazolo[4,3-a]quinazoline

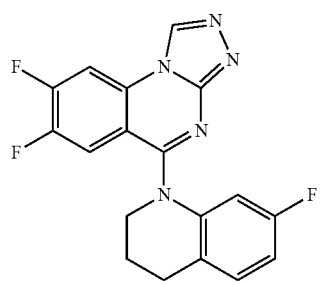 [SMILES: Fc1ccc2c(c1)N(c1nc3nncn3c3cc(F)c(F)cc13)CCC2]

A mixture of 6,7-difluoro-4-(7-fluoro-3,4-dihydroquinolin-1(2H)-yl)-2-hydrazinylquinazoline (0.21 g, crude) and triethoxymethane (10 mL, 0.608 mmol) was stirred at 100° C. overnight. The reaction mixture was concentrated in vacuo. The residue was purified by column chromatography (Si-column, CHCl$_3$:MeOH=10:0-85:15) to give the desired product. LCMS(m/z) 356.0 [M+H]+.

(Step 7) Synthesis of 8-azido-7-fluoro-5-(7-fluoro-3,4-dihydroquinolin-1(2H)-yl)-[1,2,4]triazolo[4,3-a]quinazoline

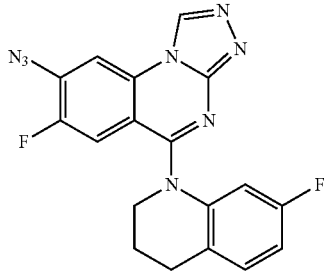 [SMILES: [N-]=[N+]=Nc1cc2c(cc1F)c(N1CCCc3ccc(F)cc31)nc1nncn12]

A mixture of 7,8-difluoro-5-(7-fluoro-3,4-dihydroquinolin-1(2H)-yl)-[1,2,4]triazolo[4,3-a]quinazoline (50 mg, 0.141 mmol) and sodium azide (4.57 mg, 0.07 mmol) in DMSO (0.35 mL) was stirred at 60° C. for 30 min. The mixture was diluted with AcOEt, washed successively with water and brine. The organic layer was concentrated in vacuo to give the desired product, which was used for the next step without further purification. LCMS(m/z) 379.19 [M+H]+.

(Step 8) Synthesis of 7-fluoro-5-(7-fluoro-3,4-dihydroquinolin-1(2H)-yl)-[1,2,4]triazolo[4,3-a]quinazolin-8-amine A mixture of 8-azido-7-fluoro-5-(7-fluoro-3,4-dihydroquinolin-1(2H)-yl)-[1,2,4]triazolo[4,3-a]quinazoline (12 mg, 0.032 mmol) and Pd/C (3 mg) in EtOH (0.16 mL) was stirred overnight at 60° C. under H$_2$ atmosphere. After removal of Pd/C by filtration, the filtrate was concentrated in vacuo. The residue was purified by column chromatography (Si-column, CHCl$_3$:MeOH=10:0-85:15) to afford the desired product: $^1$H NMR (Methanol-d$_4$) δ 9.28 (s, 1H), 7.35 (d, J=7.5 Hz, 1H), 7.23 (ddt, J=8.4, 6.4, 0.9 Hz, 1H), 7.13 (d, J=12.3 Hz, 1H), 6.72 (td, J=8.4, 2.5 Hz, 1H), 6.47-6.37 (m, 1H), 3.95 (t, J=6.4 Hz, 2H), 2.90 (t, J=6.6 Hz, 2H), 2.12 (p, J=6.5 Hz, 2H); LCMS(m/z) 353.3.

Example 217. 5-(3,4-Dihydroquinolin-1(2H)-yl)-7-fluoro-[1,2,4]triazolo[4,3-a]quinazolin-8-amine

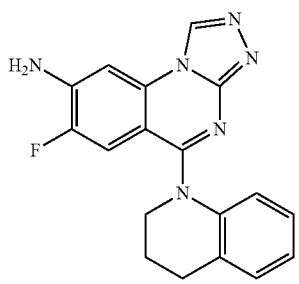

(Step 1) Synthesis of 2-chloro-4-(3,4-dihydroquinolin-1(2H)-yl)-6,7-difluoroquinazoline

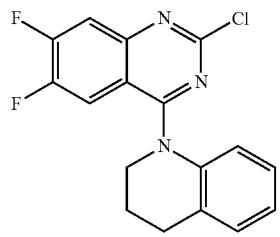 [SMILES: Fc1cc2nc(Cl)nc(N3CCCc4ccccc43)c2cc1F]

To a solution of 2,4-dichloro-6,7-difluoroquinazoline (1.1 g, 4.68 mmol) in DMF (23.4 mL) were added 1,2,3,4-tetrahydroquinoline (0.623 g, 4.68 mmol) and sodium hydride (0.112 g, 4.68 mmol), and the mixture was stirred for 1 h at RT. The mixture was diluted with AcOEt, washed successively with water and brine. The organic layer was concentrated in vacuo to give the desired product. LCMS (m/z) 332.19 [M+H]+.

(Step 2) Synthesis of 4-(3,4-dihydroquinolin-1(2H)-yl)-6,7-difluoro-2-hydrazinylquinazoline

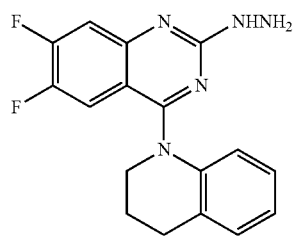 [SMILES: NNc1nc(N2CCCc3ccccc32)c2cc(F)c(F)cc2n1]

To a solution of 2-chloro-4-(3,4-dihydroquinolin-1(2H)-yl)-6,7-difluoroquinazoline (0.35 g, 1.055 mmol) in EtOH (5.28 mL) was added hydrazine hydrate (0.017 g, 0.351 mmol), and the mixture was stirred for 0.5 h. After 0.5 h and 1 h, additional portions of hydrazine hydrate (0.017 g×2, 0.7 mmol) were added slowly to the solution, and the stirring was continued for 1 h. The reaction mixture was diluted with AcOEt and washed successively with water and brine. The organic layer was concentrated in vacuo. The residue was used for the next step without further purification. LCMS (m/z) 328.14 [M+H]+.

(Step 3) Synthesis of 5-(3,4-dihydroquinolin-1(2H)-yl)-7,8-difluoro-[1,2,4]triazolo[4,3-a]quinazoline

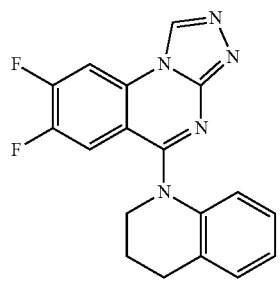 [SMILES: Fc1cc2c(N3CCCc4ccccc43)nc3nncn3c2cc1F]

A mixture of 4-(3,4-dihydroquinolin-1(2H)-yl)-6,7-difluoro-2-hydrazinylquinazoline (0.21 g, crude) and triethoxymethane (3 mL, 0.642 mmol) was stirred at 100° C. overnight. The reaction mixture was concentrated in vacuo. The residue was purified by column chromatography (Si-column, CHCl$_3$:MeOH=10:0-85:15) to give the desired product. LCMS(m/z) 338.18 [M+H]$^+$.

(Step 4) Synthesis of 8-azido-5-(3,4-dihydroquinolin-1(2H)-yl)-7-fluoro-[1,2,4]triazolo[4,3-a]quinazoline

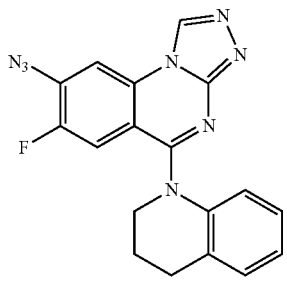 [SMILES: [N-]=[N+]=Nc1cc2c(cc1F)c(N1CCCc3ccccc31)nc1nncn12]

A mixture of 5-(3,4-dihydroquinolin-1(2H)-yl)-7,8-difluoro-[1,2,4]triazolo[4,3-a]quinazoline (62 mg, 0.184 mmol) and sodium azide (12.55 mg, 0.193 mmol) in DMSO (0.92 mL) was stirred at 60° C. for 1 h. The reaction mixture was diluted with AcOEt and washed successively with water and brine. The organic layer was concentrated in vacuo to give the desired product, which was used for the next step without further purification. LCMS(m/z) 361.19 [M+H]$^+$.

(Step 5) Synthesis of 5-(3,4-dihydroquinolin-1(2H)-yl)-7-fluoro-[1,2,4]triazolo[4,3-a]quinazolin-8-amine A mixture of 8-azido-5-(3,4-dihydroquinolin-1(2H)-yl)-7-fluoro-[1,2,4]triazolo[4,3-a]quinazoline (51 mg, crude) and Pd/C (5 mg) in EtOH (0.71 mL) was stirred overnight at 60° C. under H$_2$ atmosphere. After removal of Pd/C by filtration, the filtrate was concentrated in vacuo. The residue was purified by column chromatography (Si-column, CHCl$_3$:MeOH=10:0-85 15) to afford the desired product: $^1$H NMR (Methanol-d$_4$) δ 9.23 (s, 1H), 7.34-7.23 (m, 2H), 7.06-6.97 (m, 3H), 6.72-6.65 (m, 1H), 3.98 (t, J=6.6 Hz, 2H), 2.91 (t, J=6.6 Hz, 2H), 2.13 (t, J=6.6 Hz, 2H); LCMS (m/z) 335.2.

Example 218. 8-Fluoro-N-methyl-N-phenyl-[1,2,4]triazolo[4,3-a]quinazolin-5-amine

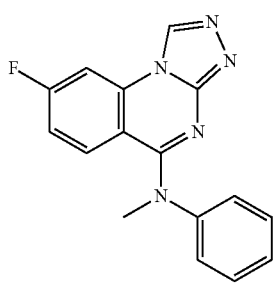 [SMILES: CN(c1ccccc1)c1nc2nncn2c2cc(F)ccc12]

(Step 1) Synthesis of 2-chloro-7-fluoro-N-methyl-N-phenylquinazolin-4-amine

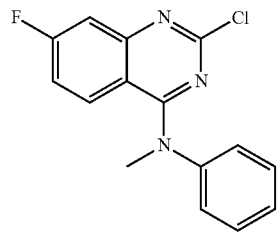 [SMILES: CN(c1ccccc1)c1nc(Cl)nc2cc(F)ccc12]

To a suspension of 2,4-dichloro-7-fluoroquinazoline (100 mg, 0.461 mmol) in 2-propanol (2.3 mL) were added N-methylaniline (49.4 mg, 0.461 mmol) and concentrated HCl (37%, 15.62 mg, 0.428 mmol), and the mixture was stirred for 30 min at RT. The reaction mixture was concentrated in vacuo. The residue was purified by column chromatography (Si-column, hexane:AcOEt=10:0-6:4) to give the desired product: LCMS(m/z) 288.08 [M+H]+.

(Step 2) Synthesis of 7-fluoro-2-hydrazinyl-N-methyl-N-phenylquinazolin-4-amine

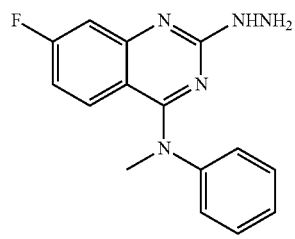

To 2-chloro-7-fluoro-N-methyl-N-phenylquinazolin-4-amine (25 mg, 0.087 mmol) was added hydrazine hydrate (21.75 mg, 0.434 mmol), and the reaction mixture was stirred for 3 h at RT. The reaction mixture was diluted with AcOEt and washed successively with water and brine. The organic layer was concentrated in vacuo. The residue was purified by column chromatography (Si-column, CHCl$_3$:MeOH=10:0-9:1) to give the desired product: LCMS(m/z) 284.13 [M+H]$^+$.

(Step 3) Synthesis of 8-fluoro-N-methyl-N-phenyl-[1,2,4]triazolo[4,3-a]quinazolin-5-amine A mixture of 7-fluoro-2-hydrazinyl-N-methyl-N-phenylquinazolin-4-amine (12 mg, 0.042 mmol) and triethoxymethane (18.83 mg, 0.127 mmol) was heated to 70° C. for 20 min. The reaction mixture was directly purified by column chromatography (Si-column, CHCl$_3$. MeOH=10:0-9:1) to afford the desired product: $^1$H NMR (Methanol-d$_4$) δ 9.42 (s, 1H), 8.05 (dd, J=9.1, 2.6 Hz, 1H), 7.44-7.32 (m, 6H), 7.04-6.94 (m, 1H), 3.67 (s, 3H); LCMS(m/z) 294.1.

Example 219. 8-(3,3-Dimethylbut-1-yn-1-yl)-N-methyl-N-phenyl-[1,2,4]triazolo[4,3-a]quinazolin-5-amine

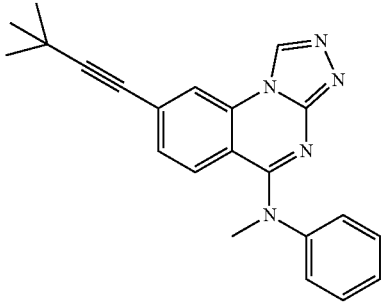 [SMILES: CN(c1ccccc1)c1nc2nncn2c2cc(C#CC(C)(C)C)ccc12]

A mixture of 8-bromo-N-methyl-N-phenyl-[1,2,4]triazolo[4,3-a]quinazolin-5-amine (Example 28) (20 mg, 0.056 mmol), Pd(dppf)Cl2 (8.26 mg, 0.011 mmol), triethylamine (17.14 mg, 0.169 mmol), 3,3-dimethylbut-1-yne (11.60 mg, 0.141 mmol) and copper(I) iodide (2.151 mg, 0.011 mmol) in acetonitrile (0.28 mL) was treated in a microwave reactor for 2 h at 80° C. The reaction mixture was subjected to solid phase extraction (washed with MeOH, then eluted with NH3 in MeOH) using Bond Elut SCX cartridge (Agilent), and the collected fractions were concentrated in vacuo. The residue was purified by prep-HPLC to afford the desired product: $^1$H NMR (Methanol-$d_4$) δ 9.57 (s, 1H), 7.55 (m, 7H), 7.14 (m, 1H), 3.79 (s, 3H), 3.67 (m, 9H); LCMS(m/z) 356.2.

Example 220. 7-Fluoro-5-((3-fluorophenyl)(methyl)amino)-[1,2,4]triazolo[4,3-a]quinazoline-8-carboxylic Acid

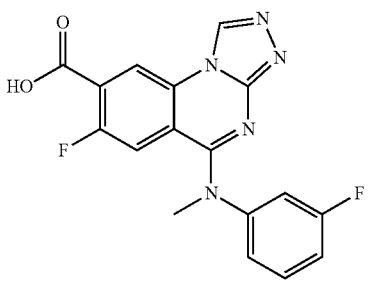 [SMILES: CN(c1cccc(F)c1)c1nc2nncn2c2cc(C(=O)O)c(F)cc12]

(Step 1) Synthesis of 8-bromo-7-fluoro-N-(3-fluorophenyl)-N-methyl-[1,2,4]triazolo[4,3-a]quinazolin-5-amine

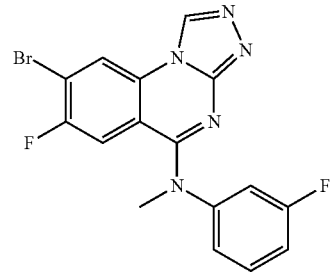

To a solution of 7-fluoro-N5-(3-fluorophenyl)-N5-methyl-[1,2,4]triazolo[4,3-a]quinazoline-5,8-diamine (Example 208) (315 mg, 0.965 mmol) in acetonitrile (4.8 mL) were added tert-butyl nitrite (149 mg, 1.448 mmol) and copper(II) bromide (237 mg, 1.062 mmol), and the mixture was stirred for 2 h at RT. The reaction mixture was filtered, and washed successively with AcOEt and MeOH, and the filtrate was concentrated in vacuo. The residue was diluted with AcOEt and washed successively with water and brine. The organic layer was concentrated in vacuo. The residue was used for the next step without further purification. LCMS(m/z) 390.09/392.09 [M+H]$^+$.

(Step 2) Synthesis of 7-fluoro-N-(3-fluorophenyl)-N-methyl-8-vinyl-[1,2,4]triazolo[4,3-a]quinazolin-5-amine

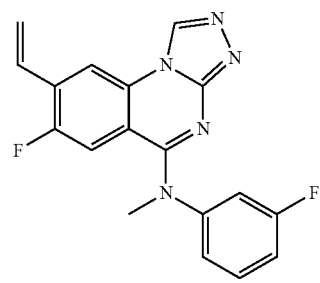

A mixture of 8-bromo-7-fluoro-N-(3-fluorophenyl)-N-methyl-[1,2,4]triazolo[4,3-a]quinazolin-5-amine (200 mg, crude), K3PO4 (109 mg, 0.513 mmol), Pd(OAc)2 (115 mg, 0.513 mmol), 4,4,5,5-tetramethyl-2-vinyl-1,3,2-dioxaborolane (118 mg, 0.769 mmol) and tricyclohexylphosphine (28.7 mg, 0.103 mmol) in dioxane/water (1:1, 2.3 mL) was stirred at 100° C. for 1.5 h. The mixture was concentrated in vacuo. The residue was purified by column chromatography (Si-column, CHC3:MeOH=10:0-8:2) to give the desired product.

(Step 3) Synthesis of 7-fluoro-5-((3-fluorophenyl)(methyl)amino)-[1,2,4]triazolo[4,3-a]quinazoline-8-carboxylic Acid

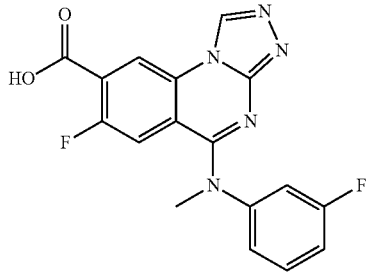 [SMILES: CN(c1cccc(F)c1)c1nc2nncn2c2cc(C(=O)O)c(F)cc12]

A mixture of 7-fluoro-N-(3-fluorophenyl)-N-methyl-8-vinyl-[1,2,4]triazolo[4,3-a]quinazolin-5-amine (50 mg, 0.148 mmol), osmium(VIII) oxide (0.2 M in BuOH, 0.15 mL, 0.030 mmol) and sodium periodate (79 mg, 0.371 mmol) in acetone/water (1:1, 0.74 mL, ratio=1:1) was stirred overnight at RT. The reaction mixture was concentrated in vacuo, and the residue was purified by column chromatography (Si-column, $CHCl_3$:MeOH=10:0-8:2) to afford the desired product: $^1$H NMR (DMSO-$d_6$) δ 9.86 (s, 1H), 8.82 (d, J=6.2 Hz, 1H), 7.45 (dd, J=8.3, 6.8 Hz, 1H), 7.40-7.33 (m, 1H), 7.25-7.14 (m, 2H), 6.96 (d, J=11.7 Hz, 1H), 3.58 (s, 3H); LCMS(m/z) 356.2.

Example 221. 7-fluoro-N5,N8-dimethyl-N5-phenyl-[1,2,4]triazolo[4,3-a]quinazoline-5,8-diamine

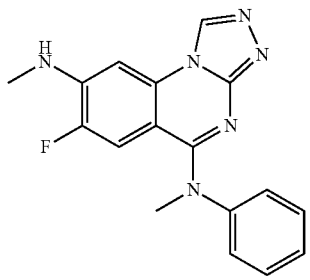 [SMILES: CNc1cc2c(cc1F)c(N(C)c1ccccc1)nc1nncn12]

A vigorously stirred mixture of Example 182 (7.1 mg, 23 μmol) and methylamine solution (9.8 M in methanol, 1.5 mL, 15 mmol) was heated to 110° C. in a microwave reactor. After 30 min, the reaction mixture was cooled to room temperature and the solvent was removed under reduced pressure. The residue was purified by reverse-phase preparative HPLC (0.1% trifluoroacetic acid in acetonitrile/water) to give the title compound: $^1$H NMR (400 MHz, DMSO-$d_6$) δ 9.83 (s, 1H), 7.53 (dd, J=8.3, 6.9 Hz, 2H), 7.48-7.32 (m, 4H), 6.46 (d, J=14.0 Hz, 1H), 3.61 (s, 3H), 2.91 (d, J=4.7 Hz, 3H); LCMS(m/z) 323.3.

Example 222. 7-fluoro-N5,N8,N8-trimethyl-N5-phenyl-[1,2,4]triazolo[4,3-a]quinazoline-5,8-diamine

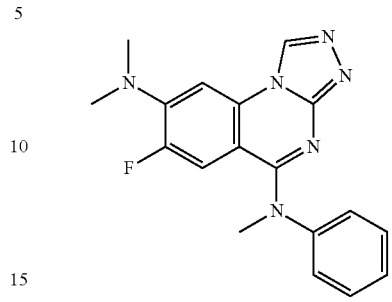

Example 222 was synthesized in a manner similar to Example 221, except using dimethylamine instead of methylamine. $^1$H NMR (400 MHz, DMSO-$d_6$) δ 9.88 (s, 1H), 7.55 (dd, J=8.3, 6.9 Hz, 2H), 7.51-7.35 (m, 4H), 6.46 (d, J=17.0 Hz, 1H), 3.62 (s, 3H), 3.11 (d, J=2.4 Hz, 6H); LCMS(m/z) 337.3.

Example 223. 7-fluoro-8-methoxy-N-methyl-N-phenyl-[1,2,4]triazolo[4,3-a]quinazolin-5-amine

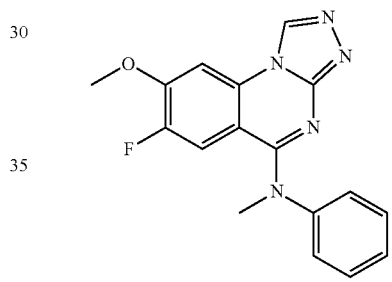

Example 223 was synthesized in a manner similar to Example 221 using ammonia solution (7.0 M in methanol) instead of methylamine solution (9.8 M in methanol). $^1$H NMR (400 MHz, DMSO-$d_6$) δ 9.89 (s, 1H), 8.15 (d, J=7.7 Hz, 1H), 7.56-7.48 (m, 2H), 7.49-7.34 (m, 3H), 6.70 (d, J=13.1 Hz, 1H), 4.07 (s, 3H), 3.62 (s, 3H); LCMS(m/z) 324.3.

Example 224. 7-fluoro-8-methoxy-N-methyl-N-phenyl-[1,2,4]triazolo[4,3-a]quinazolin-5-amine

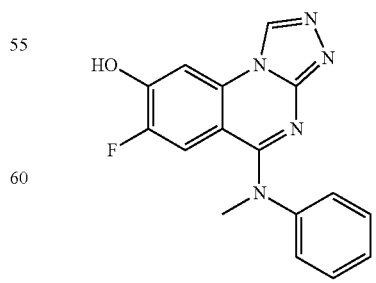

Aqueous sodium hydroxide solution (2.0 M, 3.0 mL, 6.0 mmol) was added via syringe to a vigorously stirred mixture of Example 182 (64.5 mg, 0.207 mmol) in dimethyl sulfoxide (3.0 mL), and the resulting mixture heated to 90° C. After 1 h, the resulting mixture was cooled to room temperature and was purified by reverse-phase preparative HPLC (0.1% trifluoroacetic acid in acetonitrile/water) to give the title compound: $^1$H NMR (400 MHz, DMSO-$d_6$) δ 11.64 (s, 1H), 9.50 (s, 1H), 7.70 (d, J=7.6 Hz, 1H), 7.44 (t, J=7.7 Hz, 2H), 7.38-7.20 (m, 4H), 6.79 (d, J=12.7 Hz, 1H), 6.52 (s, 1H), 3.52 (s, 3H); LCMS(m/z) 310.3.

Example 225. 8-ethoxy-7-fluoro-N-methyl-N-phenyl-[1,2,4]triazolo[4,3-a]quinazolin-5-amine

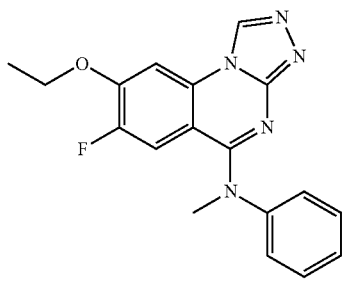 [SMILES: CCOc1cc2c(cc1F)c(N(C)c1ccccc1)nc1nncn12]

Iodoethane (9.1 µL, 110 µmol) was added via syringe to a vigorously stirred mixture of potassium carbonate (15.6 mg, 0.113 mmol) and Example 224 (7.00 mg, 22.6 µmol) in acetone (0.5 mL), and the resulting mixture was heated to 50° C. After 90 min, the reaction mixture was cooled to room temperature, and ethyl acetate (5 mL) and water (5 mL) were added sequentially. The organic layer was washed with brine, was dried over anhydrous magnesium sulfate, was filtered, and was concentrated under reduced pressure. The residue was purified by reverse-phase preparative HPLC (0.1% trifluoroacetic acid in acetonitrile/water) to give the title compound: $^1$H NMR (400 MHz, DMSO-$d_6$) δ 9.72 (s, 1H), 8.04 (d, J=7.6 Hz, 1H), 7.46 (t, J=7.7 Hz, 2H), 7.35 (d, J=7.9 Hz, 3H), 6.76 (d, J=13.0 Hz, 1H), 4.33 (q, J=7.0 Hz, 2H), 3.56 (s, 3H), 1.42 (t, J=7.0 Hz, 3H); LCMS (m/z) 338.3.

Example 226. 8-(allyloxy)-7-fluoro-N-methyl-N-phenyl-[1,2,4]triazolo[4,3-a]quinazolin-5-amine

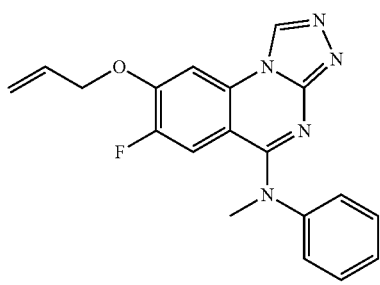 [SMILES: C=CCOc1cc2c(cc1F)c(N(C)c1ccccc1)nc1nncn12]

Example 226 was synthesized in a manner similar to Example 225, except using 3-bromoprop-1-ene instead of ethyl iodide. $^1$H NMR (400 MHz, DMSO-$d_6$) δ 9.80 (s, 1H), 8.12 (d, J=7.6 Hz, 1H), 7.58-7.34 (m, 5H), 6.72 (d, J=13.0 Hz, 1H), 6.12 (ddt, J=17.4, 10.8, 5.6 Hz, 1H), 5.52 (dt, J=17.3, 1.6 Hz, 1H), 5.38 (dt, J=10.5, 1.4 Hz, 1H), 4.87 (dt, J=5.7, 1.4 Hz, 2H), 3.61 (d, J=9.7 Hz, 3H); LCMS(m/z) 350.3.

Example 227. 8-chloro-N-(3-(5-cyclopropylpyridin-3-yl)phenyl)-N-methyl-[1,2,4]triazolo[4,3-a]quinazolin-5-amine

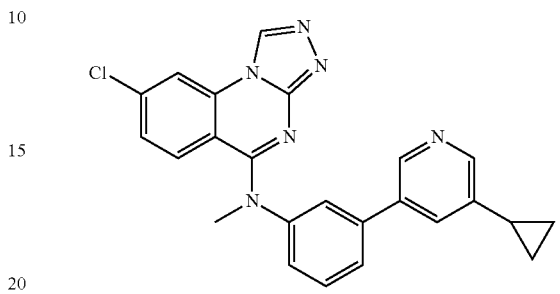

A vigorously stirred mixture of Example 308 (9.5 mg, 24.4 µmol), (5-cyclopropyl-3-pyridyl)boronic acid (6.05 mg, 37.1 µmol), [1,1'-bis(diphenylphosphino)ferrocene]dichloropalladium(II) (1.73 mg, 2.4 µmol), and aqueous sodium carbonate solution (2.0 M, 122 µL, 244 µmol) in 1,4-dioxane (0.5 mL) was heated to 100° C. After 5 min, the resulting mixture was cooled to room temperature and was concentrated under reduced pressure. The residue was purified by reverse-phase preparative HPLC (0.1% trifluoroacetic acid in acetonitrile/water) to give the title compound: $^1$H NMR (400 MHz, Acetone-$d_6$) δ 9.48 (s, 1H), 8.63 (s, 1H), 8.53-8.24 (m, 2H), 7.80 (t, J=2.1 Hz, 1H), 7.68 (q, J=4.0, 2.2 Hz, 2H), 7.59 (t, J=7.8 Hz, 1H), 7.48 (dd, J=22.1, 8.2 Hz, 2H), 7.36-7.23 (m, 1H), 3.72 (s, 3H), 1.17-1.00 (m, 2H), 0.83 (dt, J=6.6, 4.3 Hz, 2H); LCMS(m/z) 427.3.

Example 228. 8-chloro-N-methyl-N-(3-(5-methylpyridin-3-yl)phenyl)-[1,2,4]triazolo[4,3-a]quinazolin-5-amine

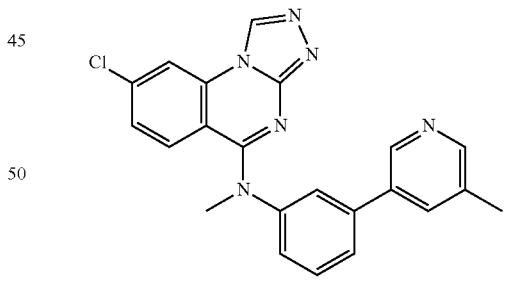

Example 228 was synthesized in a manner similar to Example 227 using 3-methyl-5-(4,4,5,5-tetramethyl-1,3,2-dioxaborolan-2-yl)pyridine instead of (5-cyclopropyl-3-pyridyl)boronic acid and chloro(2-dicyclohexylphosphino-2',4',6'-triisopropyl-1,1'-biphenyl)[2-(2'-amino-1,1'-biphenyl)]palladium(II) instead of [1,1'-bis(diphenylphosphino)ferrocene]dichloropalladium(II). $^1$H NMR (400 MHz, Acetone-$d_6$) δ 9.46 (s, 1H), 8.66 (s, 1H), 8.48-8.33 (m, 2H), 7.92 (s, 1H), 7.78 (t, J=2.1 Hz, 1H), 7.68 (d, J=7.6 Hz, 2H), 7.56 (dd, J=29.8, 8.4 Hz, 2H), 7.44 (d, J=7.3 Hz, 1H), 7.28 (dd, J=8.9, 2.2 Hz, 1H), 3.71 (s, 3H), 0.89 (s, 3H); LCMS(m/z) 401.3.

Compound 229-1 was prepared from the corresponding bromide Example 308 according to the procedure described in the first step of Example 413.

Example 229. 8-chloro-N-(3-(5-((dimethylamino)methyl)pyrazin-2-yl)phenyl)-N-methyl-[1,2,4]triazolo[4,3-a]quinazolin-5-amine

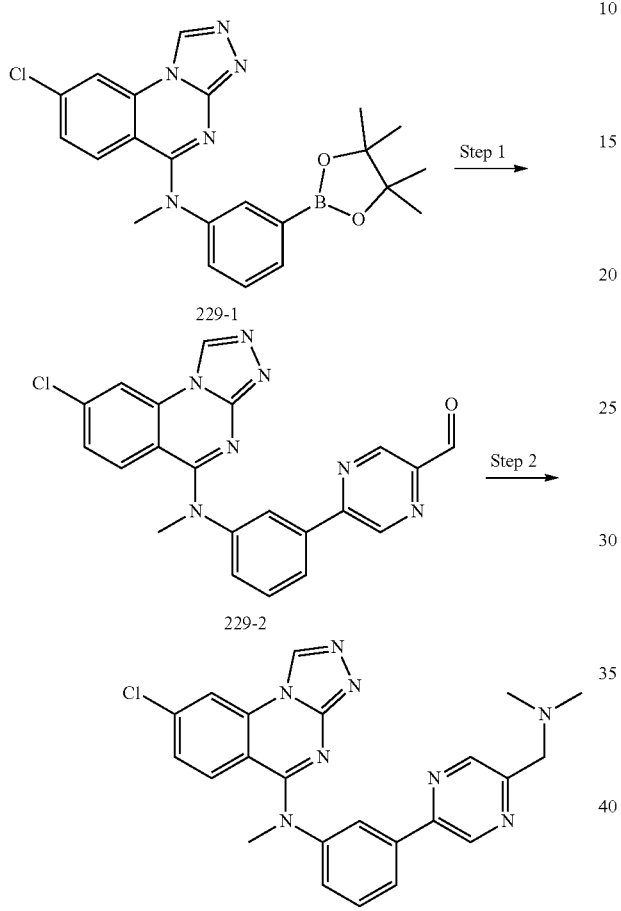

Step 1: A vigorously stirred mixture of Compound 229-1 (50.0 mg, 11.5 µmol), 5-bromopyrazine-2-carbaldehyde (258 mg, 1.38 mmol), [2-(2-aminophenyl)phenyl]-chloropalladium; dicyclohexyl-[2-(2,4,6-triisopropylphenyl)phenyl]phosphane; dicyclohexyl-[3-(2,4,6-triisopropylphenyl)phenyl]phosphane (43.0 mg, 27.3 µmol), and aqueous sodium carbonate solution (2.0 M, 1.1 mL, 2.3 mmol) in 1,4-dioxane (3.0 mL) was heated to 60° C. After 90 min, the resulting mixture was diluted with ethyl acetate (15 mL) and water (15 mL) sequentially. The organic layer was separated, was washed with brine (15 mL), was dried over anhydrous magnesium sulfate, was filtered, and was concentrated under reduced pressure. The residue was purified by flash column chromatography on silica gel (0% to 100% methanol in dichloromethane) to give Compound 229-2.

Step 2: Dimethylamine solution (2.0 M in tetrahydrofuran, 140 µL, 290 µmol) was added to a vigorously stirring mixture of glacial acetic acid (16.3 µL, 289 µmol), sodium triacetoxyborohydride (61.2 mg, 289 µmol), and Compound 229-2 (15.0 mg, 36.1 µmol) in dichloromethane (1.5 mL). The reaction mixture was heated to 40° C. After 10 min, solvent was removed under reduced pressure. The residue was purified by reverse-phase preparative HPLC (0.1% trifluoroacetic acid in acetonitrile/water) to give the title compound: $^1$H NMR (400 MHz, Methanol-$d_4$) δ 9.55 (s, 1H), 9.37-9.19 (m, 1H), 8.89-8.69 (m, 1H), 8.46 (d, J=2.0 Hz, 1H), 8.32-8.14 (m, 2H), 7.71 (t, J=7.9 Hz, 1H), 7.66-7.50 (m, 1H), 7.38 (d, J=9.1 Hz, 1H), 7.29 (dd, J=8.9, 2.1 Hz, 1H), 4.61 (s, 2H), 3.81 (s, 3H), 3.01 (s, 6H); LCMS(m/z) 445.2.

Example 230. 8-chloro-N-methyl-N-(3-(5-(morpholinomethyl)pyrazin-2-yl)phenyl)-[1,2,4]triazolo[4,3-a]quinazolin-5-amine

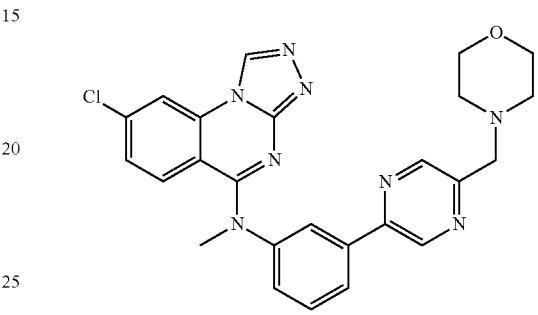

Example 230 was synthesized in a manner similar to Example 229, except using neat morpholine instead of dimethylamine solution. $^1$H NMR (400 MHz, Methanol-d4) δ 9.57 (s, 1H), 9.37-9.15 (m, 1H), 8.78 (s, 1H), 8.48 (d, J=2.1 Hz, 1H), 8.35-8.13 (m, 2H), 7.73 (t, J=7.9 Hz, 1H), 7.59 (d, J=7.9 Hz, 1H), 7.47-7.22 (m, 2H), 4.60 (s, 2H), 3.95 (s, 2H), 3.83 (s, 3H), 3.41 (s, 2H); LCMS(m/z) 487.3.

Example 231. 2-(5-(3-((8-chloro-[1,2,4]triazolo[4,3-a]quinazolin-5-yl)(methyl)amino)phenyl)pyrazin-2-yl)propan-2-ol

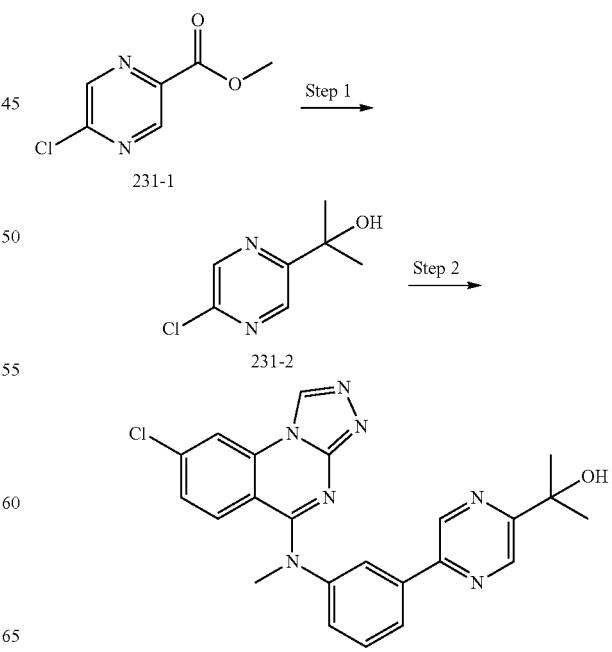

Step 1: Bromo(methyl)magnesium (3.0 M in diethyl ether, 2.9 mL, 8.7 mmol) was added by syringe to a vigorously stirred mixture of methyl 5-chloropyrazine-2-carboxylate (Compound 231-1, 500 mg, 2.90 mmol) in tetrahydrofuran (12.1 mL) at 0° C. After 1 h, the reaction was quenched with aqueous hydrochloric acid (2.0 M, 18 mL, 36 mmol), then extracted with ethyl acetate (2×30 mL). The organic layers were combined, were rinsed with brine (30 mL), were dried over anhydrous magnesium sulfate, were filtered, and were concentrated under reduced pressure. The residue was purified by flash column chromatography on silica gel (0% to 30% ethyl acetate in hexanes) to give Compound 231-2.

Step 2: 2-(5-Chloropyrazin-2-yl)propan-2-ol (24.2 mg, 140 µmol) was added to a vigorously stirred mixture containing Compound 229-1 (12.2 mg, 28.9 mmol), [2-(2-aminophenyl)phenyl]-chloro-palladium; dicyclohexyl-[2-(2,4,6-triisopropylphenyl)phenyl]phosphane; dicyclohexyl-[3-(2,4,6-triisopropylphenyl)phenyl]phosphane (4.4 mg, 2.8 µmol), and aqueous sodium carbonate solution (2.0 M, 70.0 µL, 140 µmol) in 1,4-dioxane (1.0 mL). The reaction was sealed and heated to 60° C. After 90 min, the reaction mixture was heated to 100° C. After 20 min, the reaction was cooled to room temperature and was diluted with ethyl acetate (15 mL) and water (15 mL) sequentially. The organic layer was separated, was dried over anhydrous magnesium sulfate, was filtered, and was concentrated under reduced pressure. The residue was purified by reverse-phase preparative HPLC (0.1% trifluoroacetic acid in acetonitrile/water) to give the title compound: $^1$H NMR (400 MHz, Methanol-$d_4$) δ 9.53 (s, 1H), 8.99 (d, J=34.1 Hz, 1H), 8.45 (s, 1H), 8.15 (s, 1H), 7.74-7.12 (m, 6H), 3.82 (s, 3H), 1.60 (s, 6H); LCMS(m/z) 446.3.

Example 232. 3'-((8-chloro-[1,2,4]triazolo[4,3-a]quinazolin-5-yl)(methyl)amino)-[1,1'-biphenyl]-4-carboxylic Acid

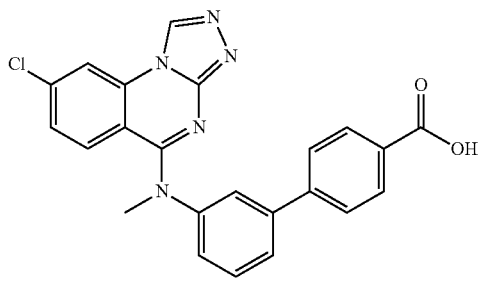 [SMILES: CN(c1cccc(-c2ccc(C(=O)O)cc2)c1)c1nc2nncn2c2cc(Cl)ccc12]

Example 232 was synthesized in a manner similar to Example 227, except using 4-(4,4,5,5-tetramethyl-1,3,2-dioxaborolan-2-yl)benzoic acid instead of (5-cyclopropyl-3-pyridyl)boronic acid. $^1$H NMR (400 MHz, Methanol-$d_4$) δ 9.59 (s, 1H), 8.51 (d, J=2.3 Hz, 1H), 8.23-8.05 (m, 2H), 7.92-7.79 (m, 2H), 7.79-7.65 (m, 3H), 7.50 (d, J=7.9 Hz, 1H), 7.39 (dd, J=9.1, 2.1 Hz, 1H), 7.36-7.28 (m, 1H), 3.87 (s, 3H); LCMS(m/z) 430.3.

Example 233. 2-(3'-((8-chloro-[1,2,4]triazolo[4,3-a]quinazolin-5-yl)(methyl)amino)-[1,1'-biphenyl]-4-yl)-2-methylpropanoic Acid

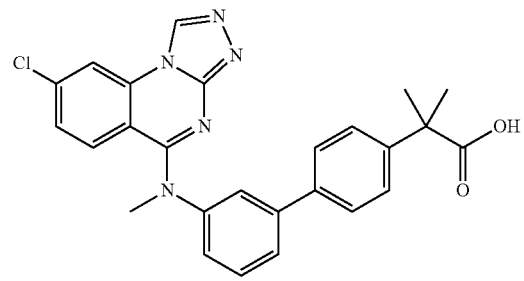 [SMILES: CN(c1cccc(-c2ccc(C(C)(C)C(=O)O)cc2)c1)c1nc2nncn2c2cc(Cl)ccc12]

Example 233 was synthesized in a manner similar to Example 227, except using 2-(4-boronophenyl)-2-methylpropanoic acid instead of (5-cyclopropyl-3-pyridyl)boronic acid. $^1$H NMR (400 MHz, Methanol-d4) δ 9.55 (s, 1H), 8.46 (s, 1H), 7.76 (d, J=7.6 Hz, 1H), 7.70 (s, 1H), 7.66-7.54 (m, 3H), 7.48 (d, J=8.2 Hz, 2H), 7.36 (dd, J=19.1, 5.0 Hz, 3H), 3.83 (s, 3H), 1.59 (s, 6H); LCMS(m/z) 472.4.

Example 234. 2-(3'-((8-chloro-[1,2,4]triazolo[4,3-a]quinazolin-5-yl)(methyl)amino)-[1,1'-biphenyl]-4-yl)-2-methylpropanamide

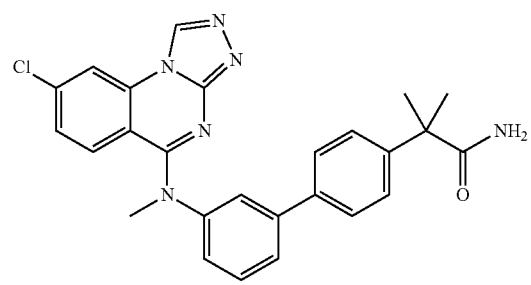 [SMILES: CN(c1cccc(-c2ccc(C(C)(C)C(N)=O)cc2)c1)c1nc2nncn2c2cc(Cl)ccc12]

Ammonia solution (0.4 M in tetrahydrofuran, 700 µL, 300 µmol) was added to a vigorously stirred mixture of 3-(ethyliminomethyleneamino)-N,N-dimethyl-propan-1-amine hydrochloride (26.4 mg, 138 µmol), N,N-dimethylpyridin-4-amine (33.7 mg, 275 µmol), and Example 233 (13.0 mg, 27.5 µmol) in dichloromethane (1.3 mL), and the resulting mixture was heated to 40° C. After 2 h, solvent was removed under reduced pressure. The residue was purified by reverse-phase preparative HPLC (0.1% trifluoroacetic acid in acetonitrile/water) to give the title compound: $^1$H NMR (400 MHz, Methanol-$d_4$) δ 9.59 (s, 1H), 8.51 (d, J=1.8 Hz, 1H), 7.87-7.78 (m, 1H), 7.73 (t, J=2.0 Hz, 1H), 7.72-7.56 (m, 2H), 7.53-7.42 (m, 3H), 7.38 (dd, J=9.1, 2.2 Hz, 1H), 7.28 (d, J=9.2 Hz, 1H), 3.87 (s, 3H), 1.58 (s, 6H); LCMS(m/z) 471.3.

Example 235. 2-(3'-((8-chloro-[1,2,4]triazolo[4,3-a]quinazolin-5-yl)(methyl)amino)-[1,1'-biphenyl]-4-yl)-2-methylpropanenitrile

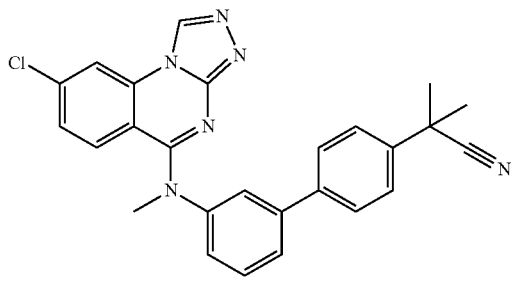

Example 235 was synthesized in a manner similar to Example 227, except using [4-(1-cyano-1-methyl-ethyl)phenyl]boronic acid instead of (5-cyclopropyl-3-pyridyl)boronic acid. $^1$H NMR (400 MHz, Methanol-$d_4$) δ 9.60 (s, 1H), 8.52 (d, J=2.0 Hz, 1H), 7.88-7.80 (m, 1H), 7.80-7.74 (m, 1H), 7.74-7.59 (m, 5H), 7.53-7.44 (m, 1H), 7.44-7.34 (m, 1H), 7.30 (d, J=9.2 Hz, 1H), 3.88 (s, 3H), 1.76 (s, 6H); LCMS(m/z) 453.3.

Example 237. 8-chloro-N-(3'-fluoro-4'-(trifluoromethyl)-[1,1'-biphenyl]-3-yl)-N-methyl-[1,2,4]triazolo[4,3-a]quinazolin-5-amine

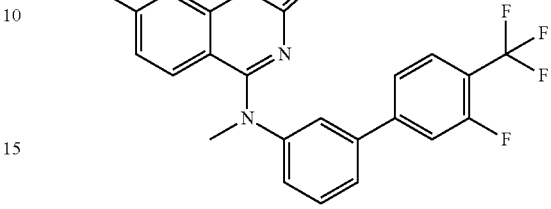

Example 237 was synthesized in a manner similar to Example 227, except using [3-fluoro-4-(trifluoromethyl)phenyl]boronic acid instead of (5-cyclopropyl-3-pyridyl)boronic acid. $^1$H NMR (400 MHz, Methanol-$d_4$) δ 9.61 (s, 1H), 8.52 (d, J=2.1 Hz, 1H), 7.93-7.83 (m, 2H), 7.79 (t, J=7.9 Hz, 1H), 7.76-7.49 (m, 4H), 7.39 (dd, J=8.0, 3.2 Hz, 1H), 7.31 (d, J=9.1 Hz, 1H), 3.87 (d, J=4.5 Hz, 3H); LCMS(m/z) 472.3.

Example 236. 8-chloro-N-(3'-methoxy-4'-(trifluoromethyl)-[1,1'-biphenyl]-3-yl)-N-methyl-[1,2,4]triazolo[4,3-a]quinazolin-5-amine

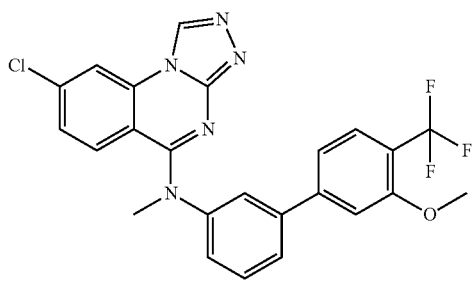

Example 236 was synthesized in a manner similar to Example 227, except using [3-methoxy-4-(trifluoromethyl)phenyl]boronic acid instead of (5-cyclopropyl-3-pyridyl) boronic acid. $^1$H NMR (400 MHz, Methanol-$d_4$) δ 9.58 (s, 1H), 8.49 (s, 1H), 7.81 (d, J=18.6 Hz, 2H), 7.65 (s, 2H), 7.49 (s, 1H), 7.41-7.24 (m, 4H), 3.97 (s, 3H), 3.86 (s, 3H); LCMS(m/z) 484.3.

Example 238. 8-chloro-N-(3'-chloro-4'-(trifluoromethyl)-[1,1'-biphenyl]-3-yl)-N-methyl-[1,2,4]triazolo[4,3-a]quinazolin-5-amine

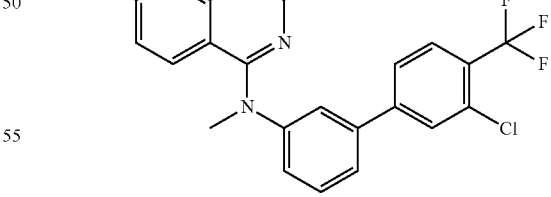

Example 238 was synthesized in a manner similar to Example 227, except using [3-chloro-4-(trifluoromethyl)phenyl]boronic acid instead of (5-cyclopropyl-3-pyridyl) boronic acid. $^1$H NMR (400 MHz, Methanol-d4) δ 9.61 (s, 1H), 8.52 (d, J=2.3 Hz, 1H), 7.97-7.81 (m, 4H), 7.73 (dd, J=20.9, 8.3 Hz, 2H), 7.55 (d, J=8.2 Hz, 1H), 7.40 (dd, J=9.2, 2.2 Hz, 1H), 7.36-7.28 (m, 1H), 3.87 (s, 3H); LCMS(m/z) 488.3.

Example 239. N-(3',4'-bis(trifluoromethyl)-[1,1'-biphenyl]-3-yl)-8-chloro-N-methyl-[1,2,4]triazolo[4,3-a]quinazolin-5-amine

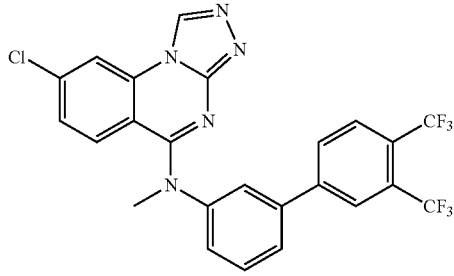

Example 239 was synthesized in a manner similar to Example 227, except using [3,4-bis(trifluoromethyl)phenyl]boronic acid instead of (5-cyclopropyl-3-pyridyl)boronic acid. $^1$H NMR (400 MHz, Methanol-$d_4$) δ 9.50 (s, 1H), 8.41 (d, J=2.1 Hz, 1H), 8.18 (s, 3H), 7.99 (s, 2H), 7.79 (d, J=2.1 Hz, 1H), 7.74 (d, J=7.8 Hz, 1H), 7.63 (t, J=7.9 Hz, 1H), 7.46-7.37 (m, 1H), 7.29 (dd, J=9.0, 2.1 Hz, 1H), 3.78 (s, 3H); LCMS(m/z) 522.3.

Example 241. 8-chloro-N-methyl-N-(3-(6-((1,1,1-trifluoropropan-2-yl)oxy)pyridin-3-yl)phenyl)-[1,2,4]triazolo[4,3-a]quinazolin-5-amine

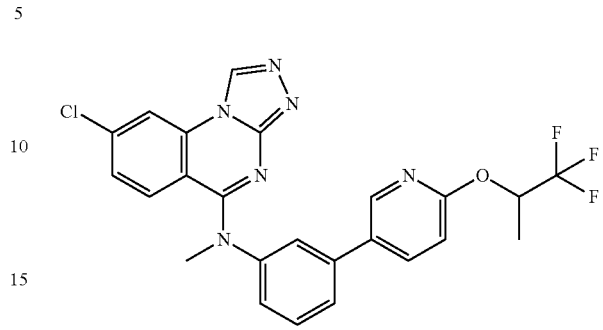

Example 241 was synthesized in a manner similar to Example 240, except using 1,1,1-trifluoropropan-2-ol instead of 2,2,2-trifluoroethanol. $^1$H NMR (400 MHz, Methanol-d4) δ 9.48 (s, 1H), 8.39 (d, J=2.2 Hz, 2H), 7.98 (dd, J=8.6, 2.6 Hz, 1H), 7.66-7.59 (m, 2H), 7.56 (t, J=8.1 Hz, 1H), 7.41 (d, J=9.0 Hz, 1H), 7.32 (d, J=8.2 Hz, 1H), 7.26 (dd, J=9.0, 2.1 Hz, 1H), 6.95-6.90 (m, 1H), 5.88 (p, J=6.7 Hz, 1H), 3.75 (s, 3H), 1.50 (d, J=6.5 Hz, 3H); LCMS(m/z) 499.3.

Example 240. 8-chloro-N-methyl-N-(3-(6-(2,2,2-trifluoroethoxy)pyridin-3-yl)phenyl)-[1,2,4]triazolo[4,3-a]quinazolin-5-amine

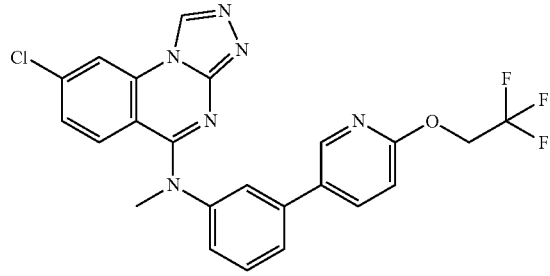 [SMILES: CN(c1cccc(-c2ccc(OCC(F)(F)F)nc2)c1)c1nc2nncn2c2cc(Cl)ccc12]

Sodium hydride (4.3 mg, 190 µmol) was added to a vigorously stirred mixture of Example 286 (5.00 mg, 12.4 µmol) and 2,2,2-trifluoroethanol (13.3 µL, 185 µmol) in N,N-dimethylformamide (0.5 mL) at 0° C. The reaction mixture was heated to 45° C. After 50 min, the reaction mixture was cooled to room temperature. The mixture was purified by reverse-phase preparative HPLC (0.1% trifluoroacetic acid in acetonitrile/water) to give the title compound: $^1$H NMR (400 MHz, Methanol-$d_4$) δ 9.56 (s, 1H), 8.48 (s, 1H), 8.42 (d, J=2.5 Hz, 1H), 8.01 (dd, J=8.6, 2.5 Hz, 1H), 7.77-7.69 (m, 2H), 7.64 (t, J=7.9 Hz, 1H), 7.43 (d, J=8.1 Hz, 1H), 7.36-7.30 (m, 2H), 7.00 (d, J=8.6 Hz, 1H), 3.83 (s, 3H), 1.96 (s, 2H); LCMS(m/z) 485.3.

Example 242. 4-(3-((8-chloro-[1,2,4]triazolo[4,3-a]quinazolin-5-yl)(methyl)amino)phenyl)-2-cyclopropylbut-3-yn-2-ol

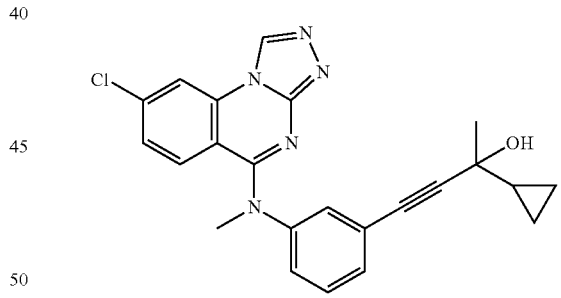

2-Cyclopropylbut-3-yn-2-ol (75% purity by wt, 44 µL, 240 µmol) was added to a vigorously stirred mixture of Example 308 (18.5 mg, 47.6 µmol), [1,1'-bis(diphenylphosphino)ferrocene]dichloropalladium(II) (12.2 mg, 16.7 µmol), triethylamine (166 µL, 1.19 mmol), and zinc bromide (53.6 mg, 238 mmol) in 1-methylpyrrolidin-2-one (0.5 mL). The reaction mixture was sealed and heated to 110° C. After 10 min, the reaction mixture was cooled to room temperature. The mixture was purified by reverse-phase preparative HPLC (0.1% trifluoroacetic acid in acetonitrile/water) to give the title compound: $^1$H NMR (400 MHz, Methanol-d4) δ 9.49 (s, 1H), 8.40 (s, 1H), 8.09 (s, 1H), 7.50-7.22 (m, 5H), 3.68 (d, J=6.0 Hz, 3H), 1.98-1.87 (m, 1H), 1.58 (s, 3H), 1.25-1.07 (m, 2H), 0.49 (q, J=5.5, 4.6 Hz, 2H); LCMS(m/z) 418.1.

Example 243. N-methyl-N-(naphthalen-1-yl)-8-nitro-[1,2,4]triazolo[4,3-a]quinazolin-5-amine

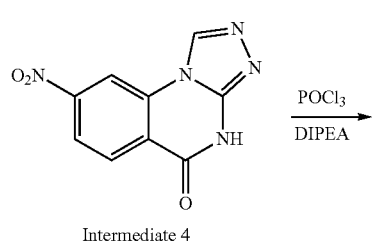

Intermediate 4

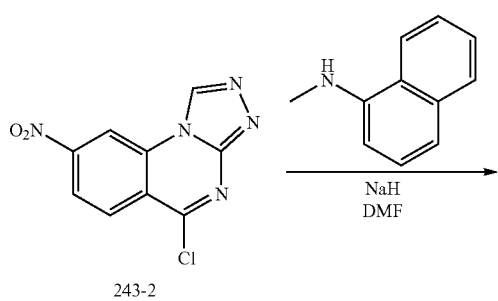

Synthesis of 5-chloro-8-nitro-[1,2,4]triazolo[4,3-a]quinazoline (Compound 243-2): A mixture of 8-nitro-[1,2,4]triazolo[4,3-a]quinazolin-5(4H)-one (Intermediate 4, 1.0 g, 4.33 mmol) and phosphoryl trichloride (13.3 g, 86 mmol) was stirred at 100° C. for 6 h. The reaction was monitored by LCMS. The reaction mixture was cooled to room temperature then evaporated under reduced pressure. The crude product was used in the next step without further purification.

Synthesis of N-methyl-N-(naphthalen-1-yl)-8-nitro-[1,2,4]triazolo[4,3-a]quinazolin-5-amine: To a solution of crude 5-chloro-8-nitro-[1,2,4]triazolo[4,3-a]quinazoline (50 mg, 0.20 mmol) in DMF (5 ml) was added N-methylnaphthalen-1-amine (22 mg, 0.14 mmol) and sodium hydride (5.6 mg, 0.14 mmol) at room temperature. The mixture was stirred for 1 h. The mixture was diluted with AcOEt, washed successively with water and brine, and dried over MgSO$_4$. The organic layer was concentrated in vacuo. The resulting residue was purified under reverse phase chromatography ACN/Water 15-95% 0.1% TFA 15 min to obtain the title compound: $^1$H NMR (400 MHz, Methanol-d4) δ 9.83 (s, 1H), 9.24 (d, J=2.3 Hz, 1H), 8.24-8.03 (m, 3H), 7.88 (dd, J=9.3, 2.3 Hz, 1H), 7.77-7.67 (m, 2H), 7.65-7.45 (m, 2H), 7.15 (d, J=9.3 Hz, 1H), 3.91 (s, 3H); LCMS(m/z) 371.3.

Example 244. N-methyl-N-(naphthalen-2-yl)-8-nitro-[1,2,4]triazolo[4,3-a]quinazolin-5-amine

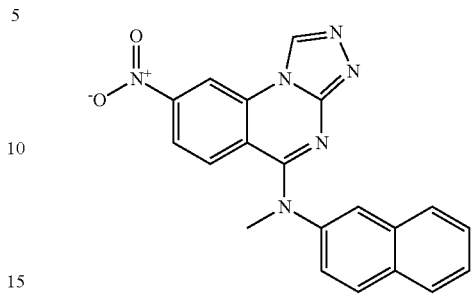

Example 244 was synthesized in a manner similar to Example 243, except using N-methylnaphthalen-2-amine instead of N-methylnaphthalen-1-amine. $^1$H NMR (400 MHz, Chloroform-d) δ 9.34 (s, 1H), 8.94 (d, J=2.2 Hz, 1H), 8.06 (d, J=8.7 Hz, 1H), 8.00-7.92 (m, 1H), 7.88 (dd, J=9.3, 2.1 Hz, 1H), 7.85-7.75 (m, 2H), 7.69-7.57 (m, 2H), 7.47-7.34 (m, 2H), 3.91 (s, 3H); LCMS(m/z) 371.3.

Example 245. N-(2,2-difluoroethyl)-8-nitro-N-phenyl-[1,2,4]triazolo[4,3-a]quinazolin-5-amine

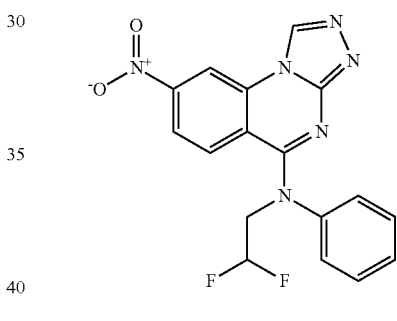

Example 245 was synthesized in a manner similar to Example 243, except using N-(2,2-difluoroethyl)aniline instead of N-methylnaphthalen-1-amine. $^1$H NMR (400 MHz, Chloroform-d) δ 9.42 (s, 1H), 8.99 (d, J=2.2 Hz, 1H), 8.06 (d, J=8.7 Hz, 1H), 8.00-7.93 (m, 1H), 7.88-7.76 (m, 2H), 7.67-7.56 (m, 2H), 7.44 (dd, J=8.7, 2.2 Hz, 1H), 7.37 (d, J=9.3 Hz, 1H), 4.0-3.8 (m, 3H); LCMS(m/z) 371.3.

Example 246. N-methyl-N-(8-nitro-[1,2,4]triazolo[4,3-a]quinazolin-5-yl)benzo[d]thiazol-2-amine

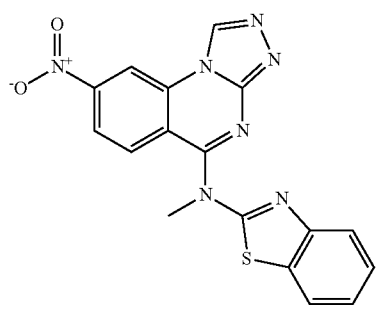

Example 246 was synthesized in a manner similar to Example 243, except using N-methylbenzo[d]thiazol-2-amine instead of N-methylnaphthalen-1-amine. $^1$H NMR (400 MHz, Chloroform-d) δ 9.42 (s, 1H), 8.99 (d, J=2.2 Hz, 1H), 8.06 (d, J=8.7 Hz, 1H), 8.00-7.93 (m, 1H), 7.89-7.75 (m, 1H), 7.69-7.57 (m, 1H), 7.48-7.33 (m, 2H), 3.90 (s, 3H); LCMS(m/z) 378.2.

Example 247. N-methyl-N-(8-nitro-[1,2,4]triazolo[4,3-a]quinazolin-5-yl)benzo[d]thiazol-2-amine

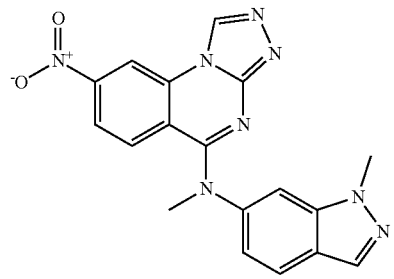

Example 247 was synthesized in a manner similar to Example 243, except using N,1-dimethyl-1H-indazol-6-amine instead of N-methylnaphthalen-1-amine. $^1$H NMR (400 MHz, Chloroform-d) δ 7.49 (s, 1H), 7.36 (t, J=7.9 Hz, 2H), 7.24 (d, J=7.7 Hz, 1H), 7.20-7.10 (m, 2H), 6.90 (d, J=8.5 Hz, 1H), 6.64 (t, J=7.7 Hz, 1H), 3.59 (s, 3H), 2.09-1.97 (m, 3H); LCMS(m/z) 375.2.

Example 248. 1-(5-(methyl(phenyl)amino)-[1,2,4]triazolo[4,3-a]quinazolin-8-yl)propan-1-ol

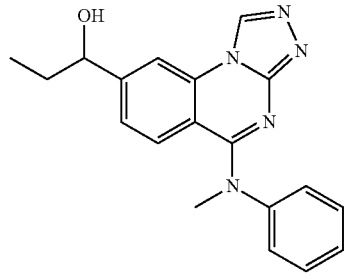

A flask was evacuated and fed with nitrogen After THF (6 mL) and 5-(methylphenyl)amino)-[1,2,4]triazolo[4,3-a]quinazolin-8-carbaldehyde (Example 117.25 mg, 0.082 mmol) were added as a solution, the mixture was kept at 0° C. in ice water bath. Then EtMgBr vas added (1.0 M, 0.082 mmol), the mixture vas further stirred at room temperature for 24 h, and then water and DCM were added. The organic layer was washed successively with water and brine. The organic layer was dried over MgSO$_4$ aid evaporated under reduced pressure. The crude products were subjected to reverse phase chromatography ACN/Water 15-95% with 0.1% TFA for 15 min to obtain the title compound as a mixture of isomers: $^1$H NMR (400 MHz, Methanol-d$_4$) δ 9.63 (s, 1H), 8.29 (d, J=1.6 Hz, 1H), 7.63-7.50 (m, 3H), 7.48-7.41 (m, 2H), 7.29 (dd, J=8.9, 1.7 Hz, 1H), 7.16 (d, J=8.8 Hz, 1H), 4.74 (dd, J=7.3, 5.4 Hz, 1H), 3.81 (s, 3H), 1.88-1.66 (m, 2H), 0.94 (t, J=7.4 Hz, 3H); LCMS(m/z) 334.3.

Example 249. 7,8-difluoro-N-(3-fluorophenyl)-N-methyl-[1,2,4]triazolo[4,3-a]quinazolin-5-amine

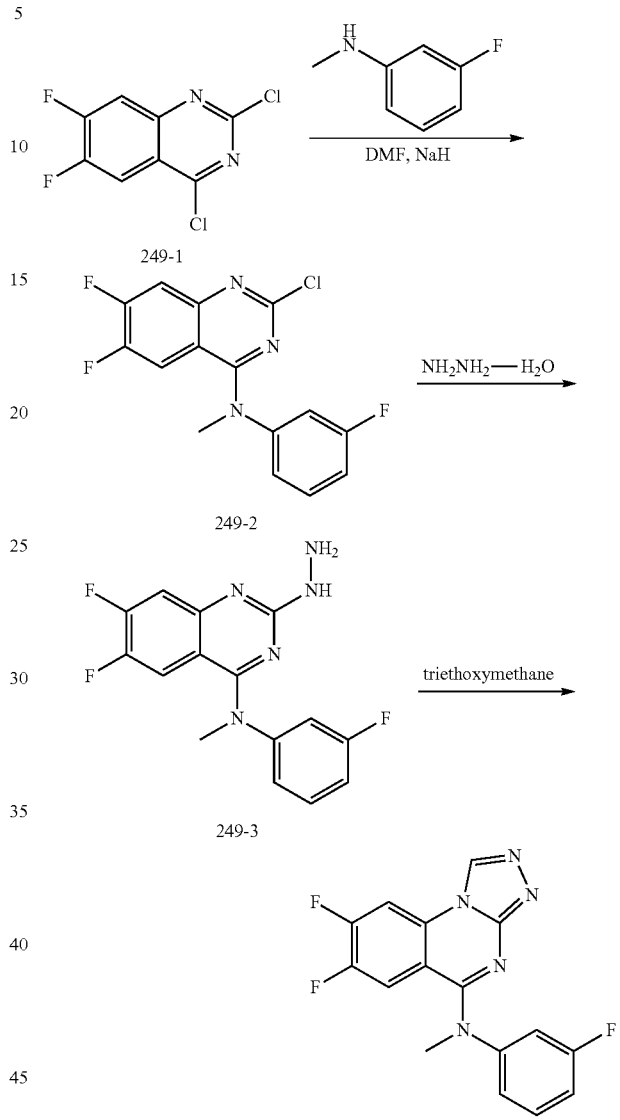

Synthesis of 2-chloro-6,7-difluoro-N-(3-fluorophenyl)-N-methylquinazolin-4-amine (Compound 249-2): To a solution of 2,4-dichloro-6,7-difluoroquinazoline (Compound 249-1, 3 g, 12.8 mmol) in DMF (20 ml) were added 3-fluoro-N-methylaniline (1.76 g, 14 mmol) and sodium hydride (587 mg, 14.7 mmol) then the mixture was stirred for 1 h at RT. Water was added to the reaction mixture and the mixture filtered. The resulting residue was used in the next step without further purification.

Synthesis of 6,7-difluoro-N-(3-fluorophenyl)-2-hydrazineyl-N-methylquinazolin-4-amine (Compound 249-3): Hydrazine hydrate (0.018 g, 0.23 mmol) was added slowly to a stirred solution of crude 2-chloro-6,7-difluoro-N-(3-fluorophenyl)-N-methylquinazolin-4-amine (Compound 249-2, 254 mg, 0.78 mmol) in ethanol (4 ml) at room temperature. The mixture was diluted with DCM, and then washed successively with water and brine, and dried over MgSO$_4$. The organic layer was concentrated in vacuo. The resulting residue was used in the next step without further purification.

Synthesis of 7,8-difluoro-N-(3-fluorophenyl)-N-methyl-[1,2,4]triazolo[4,3-a]quinazolin-5-amine: A mixture of crude 6,7-difluoro-N-(3-fluorophenyl)-2-hydrazinyl-N-methylquinazolin-4-amine (Compound 249-3) (340 mg, 1.06 mmol) and triethoxymethane (789 mg, 5.32 mmol) was stirred at 100° C. for 4 h. The reaction mixture was concentrated in vacuo. The residue was purified reverse phase chromatography ACN/Water 15-95% with 0.1% TFA for 15 min to yield the title compound: $^1$H NMR (400 MHz, Chloroform-d) δ 8.90 (s, 1H), 7.67 (dd, J=9.3, 6.6 Hz, 1H), 7.40 (td, J=8.2, 6.3 Hz, 1H), 7.18 (dd, J=11.2, 8.0 Hz, 1H), 7.06 (td, J=8.4, 2.2 Hz, 1H), 6.99-6.87 (m, 2H), 3.68 (s, 3H); LCMS(m/z) 330.3.

Example 250. 8-chloro-7-fluoro-N-(3-fluorophenyl)-N-methyl-[1,2,4]triazolo[4,3-a]quinazolin-5-amine

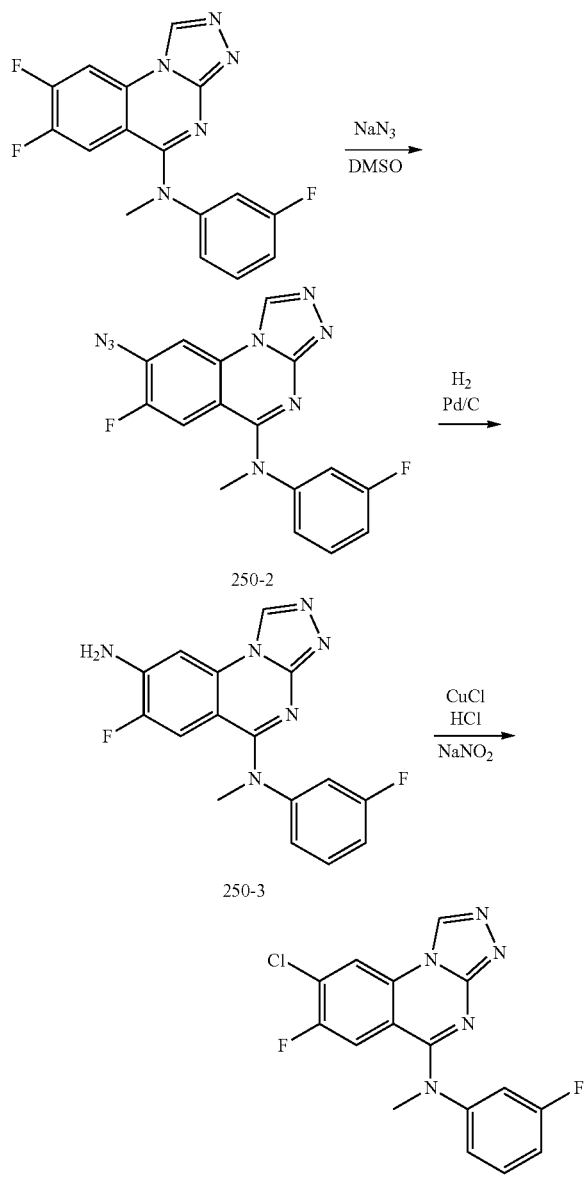

Synthesis of 8-azido-7-fluoro-N-(3-fluorophenyl)-N-methyl-[1,2,4]triazolo[4,3-a]quinazolin-5-amine (Compound 250-2): To a solution of 7,8-difluoro-N-(3-fluorophenyl)-N-methyl-[1,2,4]triazolo[4,3-a]quinazolin-5-amine (Example 249, 2.4 g, 7.71 mmol) in DMSO (10 ml) was added sodium azide (2.5 g, 38.8 mmol), and the mixture was stirred for 2 h at 100° C. The reaction mixture was diluted with DCM, and then washed successively with water and brine, and dried over MgSO$_4$. The organic layer was concentrated in vacuo. The resulting residue was used in the next step without further purification.

Synthesis of 7-fluoro-N5-(3-fluorophenyl)-N5-methyl-[1,2,4]triazolo[4,3-a]quinazoline-5,8-diamine (Compound 250-3): To a solution of crude 8-azido-7-fluoro-N-(3-fluorophenyl)-N-methyl-[1,2,4]triazolo[4,3-a]quinazolin-5-amine (2) (0.6 g, 1.7 mmol) in ethanol (5 ml) was added Pd/C and the suspension was stirred for 5 h at room temperature under hydrogen gas atmosphere. Pd/C was removed by filtration, and the filtrate was concentrated in vacuo. The crude product was used in the next step.

Synthesis of 8-chloro-7-fluoro-N-(3-fluorophenyl)-N-methyl-[1,2,4]triazolo[4,3-a]quinazolin-5-amine: A solution of sodium nitrite (23.3 mg, 0.33 mmol) in water (2 ml) was added dropwise to a stirred, suspension of 7-fluoro-N5-(3-fluorophenyl)-N5-methyl-[1,2,4]triazolo[4,3-a]quinazoline-5,8-diamine (100 mg, 0.306 mmol) in hydrochloric acid (37% w/v, 4 ml) at 0° C. The solution was stirred at 0° C. for 30 min and then added in portions to a stirred, boiling solution of copper (I) chloride (48 mg, 0.33 mmol) in hydrochloric acid (37% w/v, 2 ml). The stirred mixture was boiled for a further 15 min and left cool overnight. Water was added, and the product extracted into DCM. The etherate extract was washed with water, 10% w/v sodium hydroxide solution and then dried over MgSO$_4$. The solvent removed in vacuo. The residue was purified by reverse phase chromatography ACN/Water 15-95% with 0.1% TFA for 15 min to yield the title compound: $^1$H NMR (400 MHz, Chloroform-d) δ 9.22 (s, 1H), 8.31 (d, J=7.7 Hz, 1H), 7.54 (q, J=7.8 Hz, 1H), 7.24 (t, J=8.1 Hz, 1H), 7.09 (dd, J=11.8, 8.7 Hz, 2H), 6.89 (d, J=10.2 Hz, 1H), 3.77 (d, J=2.0 Hz, 3H); LCMS(m/z) 346.

Example 251. (7-fluoro-5-((3-fluorophenyl)(methyl)amino)-[1,2,4]triazolo[4,3-a]quinazolin-8-yl)methanol

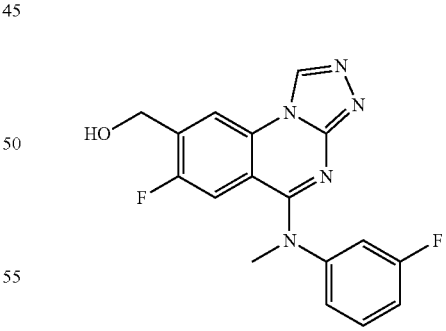

To a solution of methylthiomethyl p-tolyl sulfone (131 mg, 0.6 mmol) in DMF (5 mL) was added 60% sodium hydride (24 mg, 0.6 mmol). The resulting mixture was stirred at 0° C. for 1 h followed by addition of 7,8-difluoro-N-(3-fluorophenyl)-N-methyl-[1,2,4]triazolo[4,3-a]quinazolin-5-amine (Example 249, 00 mg, 0.30 mmol). The reaction was then carried out at room temperature for 24 h and was quenched by addition of 5 ml 10% HCl. To the mixture was added DCM and water. The organic phase was then washed with water and brine, dried over MgSO$_4$. and concentrated to dryness. The residue was purified reverse phase chromatography ACN/Water 15-95% with 0.1% TFA for 15 min to yield the title compound: $^1$H NMR (400 MHz, Methanol-d$_4$) δ 9.71 (s, 1H), 8.50 (d, J=6.2 Hz, 1H), 7.72-7.53 (m, 1H), 7.43-7.18 (m, 3H), 6.80 (d, J=11.5 Hz, 1H), 4.83 (s, 2H), 3.81 (s, 3H); LCMS(m/z) 342.2.

Example 252. 8-chloro-N-(3-(6-(1,1-difluoroethyl) pyridin-3-yl)phenyl)-N-methyl-[1,2,4]triazolo[4,3-a] quinazolin-5-amine

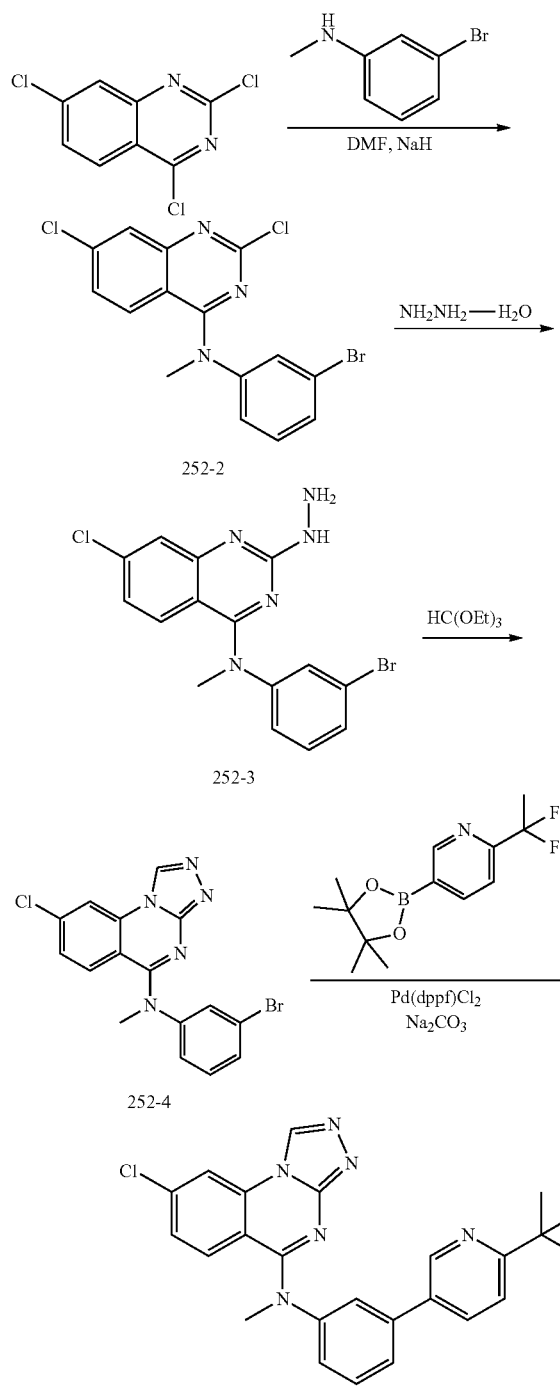

Synthesis of N-(3-bromophenyl)-2,7-dichloro-N-methylquinazolin-4-amine (Compound 252-2): To a solution of 2,4,7-trichloroquinazoline (1 g, 4.28 mmol) in DMF (20 ml) were added 3-fluoro-N-methylaniline (837 mg, 4.5 mmol) and sodium hydride (965 mg, 24.1 mmol). The mixture was stirred for 24 h at room temperature. Water was added to the reaction mixture and the mixture filtered. The resulting residue was used in the next step without further purification.

Synthesis of N-(3-bromophenyl)-7-chloro-2-hydrazinyl-N-methylquinazolin-4-amine (Compound 252-3): Hydrazine hydrate (2.8 g, 56.4 mmol) was added slowly to a stirred solution of crude N-(3-bromophenyl)-2,7-dichloro-N-methylquinazolin-4-amine (252-2) (800 mg, 2.1 mmol) in ethanol (6 ml) and THF (1 ml). The mixture was stirred at room temperature for 4 hrs. The mixture was evaporated and then dissolved in DCM and then washed successively with water and brine, and dried over MgSO$_4$. The organic layer was concentrated in vacuo. The resulting residue was used in the next step without further purification.

Synthesis of N-(3-bromophenyl)-8-chloro-N-methyl-[1,2,4]triazolo[4,3-a]quinazolin-5-amine (Compound 252-4): A mixture of crude N-(3-bromophenyl)-7-chloro-2-hydrazineyl-N-methylquinazolin-4-amine (252-3) (550 mg, 1.45 mmol) and triethoxymethane (3.2 g, 21 mmol) was stirred at 100° C. for 4 h. Hexanes were added to reaction mixture to precipitate a crude product, which was used in the next step.

Synthesis of 8-chloro-N-(3-(6-(1,1-difluoroethyl)pyridin-3-yl)phenyl)-N-methyl-[1,2,4]triazolo[4,3-a]quinazolin-5-amine: To a solution of N-(3-bromophenyl)-8-chloro-N-methyl-[1,2,4]triazolo[4,3-a]quinazolin-5-amine (252-4, 20 mg, 0.05 mmol) and 2-(1,1-difluoroethyl)-5-(4,4,5,5-tetramethyl-1,3,2-dioxaborolan-2-yl)pyridine (15 mg, 0.056 mmol) in 1,4-dioxane (5 ml) were added Pd(dppf)Cl2 (8 mg, 0.01 mmol) and 2 ml of a saturated aqueous solution of Na$_2$CO$_3$. The mixture was stirred at 90° C. for 10 min. The residue was purified reverse phase chromatography ACN/Water 15-95% with 0.1% TFA for 15 min to yield the title compound: $^1$H NMR (400 MHz, Chloroform-d) δ 9.12 (s, 1H), 8.85 (s, 1H), 8.03 (s, 2H), 7.74 (d, J=24.2 Hz, 3H), 7.64-7.34 (m, 2H), 7.26-7.3 (m, 2H), 3.86 (s, 3H), 2.06 (t, J=18.1 Hz, 3H); LCMS(m/z) 451.4.

Example 253. tert-butyl 4-(5-(3-((8-chloro-[1,2,4] triazolo[4,3-a]quinazolin-5-yl)(methyl)amino)phenyl)pyridin-2-yl)piperazine-1-carboxylate

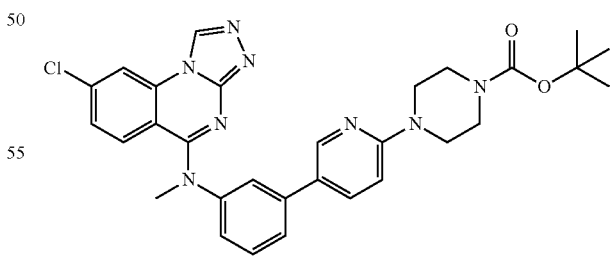

Example 253 was prepared in a similar manner as Example 252. $^1$H NMR (400 MHz, Chloroform-d) δ 9.14 (s, 1H), 8.51 (s, 1H), 8.08 (s, 1H), 8.00 (d, J=9.3 Hz, 1H), 7.61 (d, J=6.5 Hz, 2H), 7.43 (s, 1H), 7.36 (dt, J=6.9, 2.2 Hz, 1H), 7.20 (s, 2H), 7.01 (d, J=9.3 Hz, 1H), 3.75 (d, J=12.5 Hz, 7H), 3.65 (dd, J=6.8, 3.6 Hz, 4H), 1.49 (d, J=20.5 Hz, 9H); LCMS(m/z) 571.3.

Example 254. 8-chloro-N-methyl-N-(4'-(thiazol-2-yl)-[1,1'-biphenyl]-3-yl)-[1,2,4]triazolo[4,3-a]quinazolin-5-amine

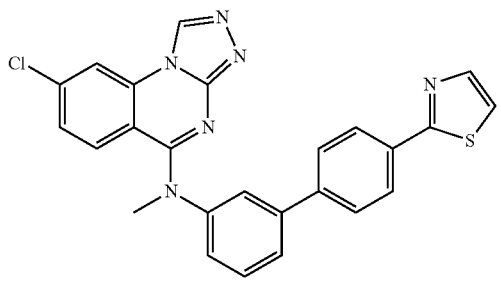 [SMILES: CN(c1cccc(-c2ccc(-c3nccs3)cc2)c1)c1nc2nncn2c2cc(Cl)ccc12]

Example 254 was prepared in a similar manner as Example 252. ¹H NMR (400 MHz, Chloroform-d) δ 9.10 (s, 1H), 8.15-7.92 (m, 4H), 7.78 (d, J=7.7 Hz, 1H), 7.72-7.60 (m, 3H), 7.57 (s, 1H), 7.44 (d, J=3.3 Hz, 1H), 7.32 (d, J=7.7 Hz, 1H), 7.22 (q, J=9.5 Hz, 3H), 3.86 (s, 3H); LCMS(m/z) 469.3.

Example 255. N-(3-(1H-pyrrolo[3,2-b]pyridin-6-yl)phenyl)-8-chloro-N-methyl-[1,2,4]triazolo[4,3-a]quinazolin-5-amine

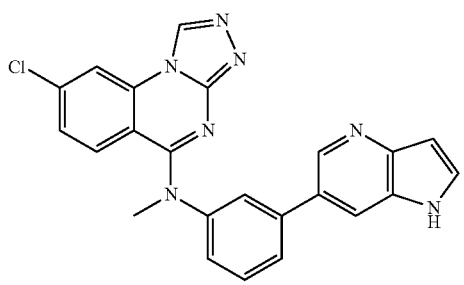 [SMILES: CN(c1cccc(-c2cnc3cc[nH]c3c2)c1)c1nc2nncn2c2cc(Cl)ccc12]

Example 255 was prepared in a similar manner as Example 252. ¹H NMR (400 MHz, Methanol-d4) δ 9.56 (s, 1H), 8.87 (d, J=1.6 Hz, 1H), 8.75 (d, J=1.3 Hz, 1H), 8.47 (d, J=2.1 Hz, 1H), 8.17 (d, J=3.2 Hz, 1H), 7.88 (d, J=8.2 Hz, 2H), 7.71 (t, J=7.8 Hz, 1H), 7.52 (d, J=8.6 Hz, 1H), 7.42 (d, J=9.0 Hz, 1H), 7.33 (dd, J=9.0, 2.1 Hz, 1H), 6.90 (d, J=3.4 Hz, 1H), 3.84 (s, 3H); LCMS(m/z) 426.2.

Example 256. 8-chloro-N-(3'-methoxy-4'-(4-(oxetan-3-yl)piperazin-1-yl)-[1,1'-biphenyl]-3-yl)-N-methyl-[1,2,4]triazolo[4,3-a]quinazolin-5-amine

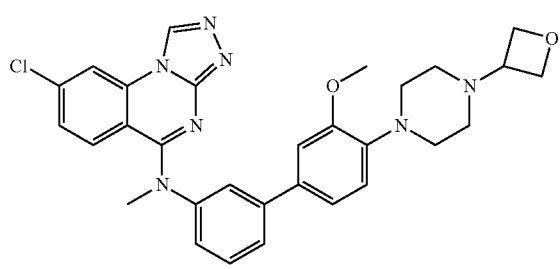 [SMILES: COc1cc(-c2cccc(N(C)c3nc4nncn4c4cc(Cl)ccc34)c2)ccc1N1CCN(C2COC2)CC1]

Example 256 was prepared in a similar manner as Example 252. ¹H NMR (400 MHz, Methanol-d₄) δ 9.57 (s, 1H), 8.49 (d, J=2.0 Hz, 1H), 7.78 (dt, J=8.0, 1.2 Hz, 1H), 7.71 (t, J=2.0 Hz, 1H), 7.63 (t, J=7.9 Hz, 1H), 7.44-7.28 (m, 3H), 7.22 (d, J=7.4 Hz, 2H), 7.11-7.02 (m, 1H), 4.93 (t, J=7.7 Hz, 4H), 4.50 (tt, J=7.2, 5.6 Hz, 1H), 3.93 (s, 4H), 3.86 (s, 4H), 3.31 (d, J=1.5 Hz, 3H); LCMS(m/z) 556.4.

Example 257. 8-chloro-N-(4'-(1,1-difluoroethyl)-[1,1'-biphenyl]-3-yl)-N-methyl-[1,2,4]triazolo[4,3-a]quinazolin-5-amine

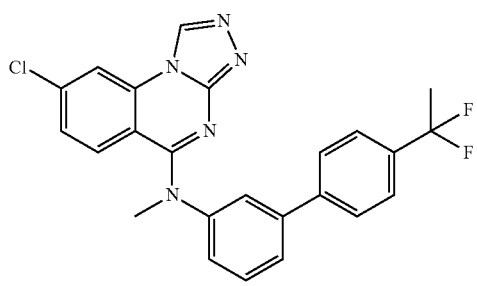 [SMILES: CN(c1cccc(-c2ccc(C(C)(F)F)cc2)c1)c1nc2nncn2c2cc(Cl)ccc12]

Example 257 was prepared in a similar manner as Example 252. ¹H NMR (400 MHz, Chloroform-d) δ 9.04 (s, 1H), 8.03 (s, 1H), 7.70 (d, J=7.8 Hz, 1H), 7.66-7.57 (m, 4H), 7.48 (d, J=1.9 Hz, 1H), 7.30 (d, J=1.7 Hz, 2H), 7.21 (s, 2H), 3.83 (s, 3H), 1.97 (d, J=36.2 Hz, 3H); LCMS(m/z) 450.3.

Example 258. 8-chloro-N-methyl-N-(3-(6-(piperazin-1-yl)pyridin-3-yl)phenyl)-[1,2,4]triazolo[4,3-a]quinazolin-5-amine

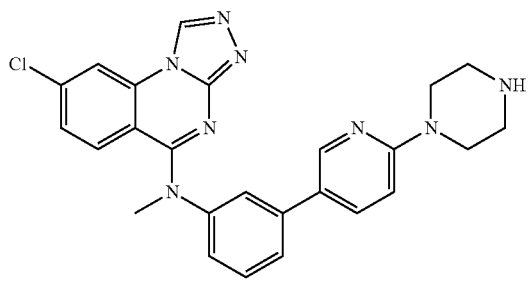 [SMILES: CN(c1cccc(-c2ccc(N3CCNCC3)nc2)c1)c1nc2nncn2c2cc(Cl)ccc12]

To a solution of tert-butyl 4-(5-(3-((8-chloro-[1,2,4]triazolo[4,3-a]quinazolin-5-yl)(methyl)amino)phenyl)pyridin-2-yl)piperazine-1-carboxylate (Example 253, 20 mg, 0.05 mmol) in DCM (5 ml) was added TFA (2 ml) and then stirred at room temperature for 2 hr. The residue was evaporated under reduced pressure and then purified by reverse phase chromatography ACN/Water 15-95% with 0.1% TFA for 15 min to yield the title compound: ¹H NMR (400 MHz, Chloroform-d) δ 9.04 (s, 1H), 8.03 (s, 1H), 7.70 (d, J=7.8 Hz, 1H), 7.64-7.57 (m, 4H), 7.48 (d, J=1.9 Hz, 1H), 7.30 (d, J=1.7 Hz, 1H), 7.21 (s, 2H), 3.83 (s, 3H), 3.13 (s, 8H); LCMS(m/z) 471.3.

Example 259. 2-(5-(3-((8-chloro-[1,2,4]triazolo[4,3-a]quinazolin-5-yl)(methyl)amino)phenyl)pyridin-2-yl)propan-2-ol

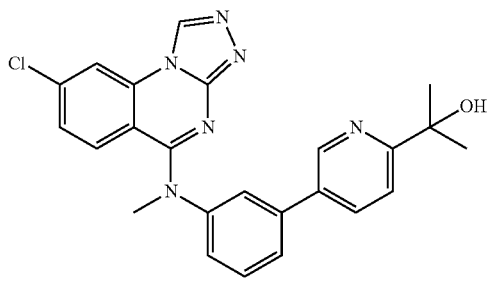

Example 259 was prepared in a similar manner as Example 252. ¹H NMR (400 MHz, Methanol-d₄) δ 9.62 (s, 1H), 8.87 (dd, J=2.3, 0.7 Hz, 1H), 8.59 (dd, J=8.5, 2.3 Hz, 1H), 8.53 (d, J=2.0 Hz, 1H), 8.07 (dd, J=8.5, 0.7 Hz, 1H), 7.96-7.87 (m, 2H), 7.75 (t, J=8.2 Hz, 1H), 7.64-7.53 (m, 1H), 7.41-7.25 (m, 2H), 3.88 (s, 3H), 1.67 (s, 5H); LCMS (m/z) 445.3.

Example 260. 2-(5-(3-((8-chloro-[1,2,4]triazolo[4,3-a]quinazolin-5-yl)(methyl)amino)phenyl)pyridin-2-yl)propan-2-ol

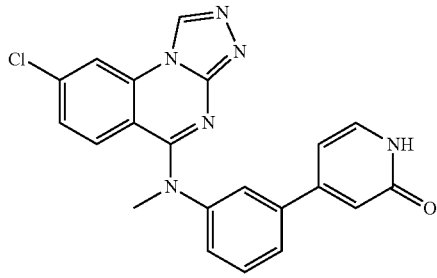 [SMILES: CN(c1cccc(-c2cc[nH]c(=O)c2)c1)c1nc2nncn2c2cc(Cl)ccc12]

Example 260 was prepared in a similar manner as Example 252. ¹H NMR (400 MHz, Methanol-d₄) δ 9.57 (s, 1H), 8.49 (d, J=2.0 Hz, 1H), 7.78 (dt, J=8.0, 1.2 Hz, 1H), 7.71 (t, J=2.0 Hz, 1H), 7.63 (t, J=7.9 Hz, 1H), 7.44-7.27 (m, 2H), 7.10-7.03 (m, 1H), 4.93 (t, J=7.7 Hz, 2H), 4.50 (tt, J=7.2, 5.6 Hz, 1H), 3.93 (s, 3H); LCMS(m/z) 403.3.

Example 261. 8-chloro-N-methyl-N-(3-(2-morpholinopyrimidin-5-yl)phenyl)-[1,2,4]triazolo[4,3-a]quinazolin-5-amine

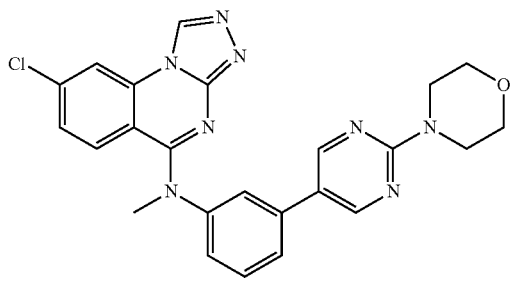

Example 261 was prepared in a similar manner as Example 252. ¹H NMR (400 MHz, Chloroform-d) δ 9.14 (s, 1H), 8.51 (s, 1H), 8.08 (s, 1H), 8.00 (d, J=9.3 Hz, 1H), 7.61 (d, J=6.5 Hz, 2H), 7.43 (s, 1H), 7.36 (dt, J=6.9, 2.2 Hz, 1H), 7.20 (s, 1H), 7.01 (d, J=9.3 Hz, 1H), 3.75 (d, J=12.5 Hz, 7H), 3.65 (dd, J=6.8, 3.6 Hz, 4H); LCMS(m/z) 473.2.

Example 262. N-(3-bromophenyl)-8-chloro-6-fluoro-N-methyl-[1,2,4]triazolo[4,3-a]quinazolin-5-amine

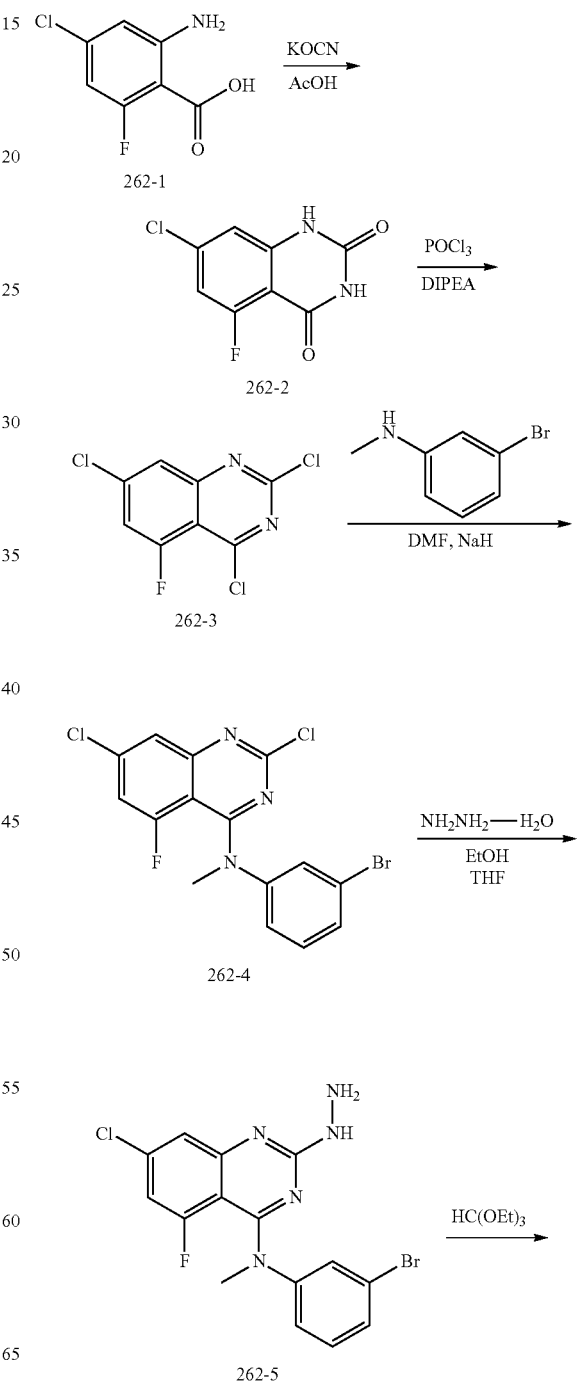

-continued

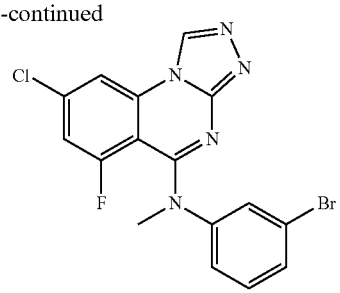

Synthesis of 7-chloro-5-fluoroquinazoline-2,4(1H,3H)-dione (Compound 262-2): To a solution of 2-amino-4-chloro-6-fluorobenzoic acid (5.0 g, 26.4 mmol) dissolved in acetic acid (20 ml) was added KOCN (3.2 g, 39.6 mmol) dissolved in 10 ml of water and then stirred at room temperature for 5 hrs. Another portion of KOCN (640 mg, 7.9 mmol) was added and the mixture was stirred for 5 more hours. A saturated aqueous solution of NaHCO$_3$ was added slowly to the mixture, and solids filtered out.

Synthesis of 2,4,7-trichloro-5-fluoroquinazoline (Compound 262-3): A mixture of 7-chloro-5-fluoroquinazoline-2,4(1H,3H)-dione (Compound 262-2, 1.3 g, 6.06 mmol), phosphoryl trichloride (2.3 g, 15.1 mmol) and DIPEA (2.2 ml, 12.12 mmol) was stirred at 100° C. for 1 h. The reaction was monitored by LCMS. The reaction mixture was cooled to room temperature, evaporated under reduced pressure. The residue was purified in normal phase chromatography Hex:EtOAc 1:2. Appropriate fractions were evaporated and used in the next step.

Synthesis of N-(3-bromophenyl)-2,7-dichloro-N-methylquinazolin-4-amine (Compound 262-4): A solution of 3-bromo-N-methylaniline (160 mg, 0.86 mmol) and sodium hydride (109 mg, 2.7 mmol) in DMF was stirred at room temperature for 30 min. To this mixture 2,4,7-trichloro-5-fluoroquinazoline (Compound 262-3, 173 mg, 0.68 mmol) was added and mixture was stirred for 24h at room temperature. Water and DCM were added to the mixture and the organic phase was dried over MgSO$_4$ and evaporated under reduced pressure. The crude product was used in the next step.

Synthesis of N-(3-bromophenyl)-7-chloro-2-hydrazineyl-N-methylquinazolin-4-amine (Compound 262-5): Hydrazine hydrate (1 g, 20.2 mmol) was added slowly to a stirred solution of crude N-(3-bromophenyl)-2,7-dichloro-N-methylquinazolin-4-amine (Compound 262-4) (300 mg, 0.74 mmol) in ethanol 6 ml and THF 1 ml at room temperature. The mixture was evaporated under reduced pressure and dissolved with DCM and then washed successively with water and brine and dried over MgSO$_4$. The organic layer was concentrated in vacuo. The resulting residue was used in the next step without further purification.

Synthesis of N-(3-bromophenyl)-8-chloro-N-methyl-[1,2,4]triazolo[4,3-a]quinazolin-5-amine: A mixture of crude N-(3-bromophenyl)-7-chloro-2-hydrazinyl-N-methylquinazolin-4-amine (Compound 262-5) (200 mg, 0.5 mmol) and triethoxymethane (1.4 g, 10 mmol) was stirred at 95° C. for 4 h. The residue was evaporated under reduced pressure and then purified reverse phase chromatography ACN/Water 15-95% with 0.1% TFA for 15 min to give the title compound: $^1$H NMR (400 MHz, Chloroform-d) δ 8.95 (s, 1H), 7.72 (s, 1H), 7.39-7.32 (m, 1H), 7.24 (d, J=2.1 Hz, 1H), 7.16 (t, J=8.0 Hz, 1H), 7.00 (dd, J=11.0, 1.9 Hz, 1H), 6.96-6.89 (m, 1H), 3.68 (s, 3H); LCMS(m/z) 408.2.

Example 263. N-(4'-(tert-butyl)-[1,1'-biphenyl]-3-yl)-8-chloro-6-fluoro-N-methyl-[1,2,4]triazolo[4,3-a]quinazolin-5-amine

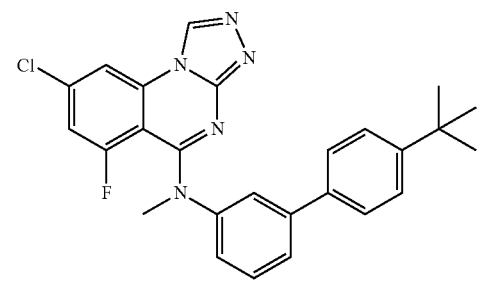

Example 263 was prepared in a similar manner as Example 252, except using Example 262 instead of Compound 252-4 and (4-(tert-butyl)phenyl)boronic acid instead of 2-(1,1-difluoroethyl)-5-(4,4,5,5-tetramethyl-1,3,2-dioxaborolan-2-yl)pyridine. $^1$H NMR (400 MHz, Chloroform-d) δ 9.25 (s, 1H), 8.06 (s, 1H), 7.60-7.52 (m, 1H), 7.48 (d, J=8.6 Hz, 2H), 7.46-7.38 (m, 3H), 7.35 (t, J=1.9 Hz, 1H), 7.08-6.97 (m, 2H), 3.84 (s, 3H), 1.37 (s, 9H); LCMS(m/z) 460.4.

Example 264. N-(6-(4-(tert-butyl)phenyl)pyridin-2-yl)-8-chloro-N-methyl-[1,2,4]triazolo[4,3-a]quinazolin-5-amine

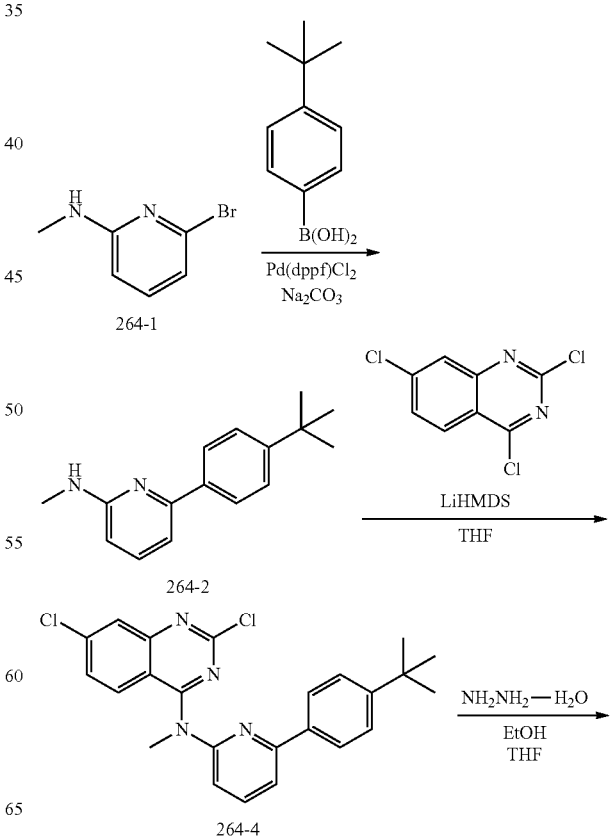

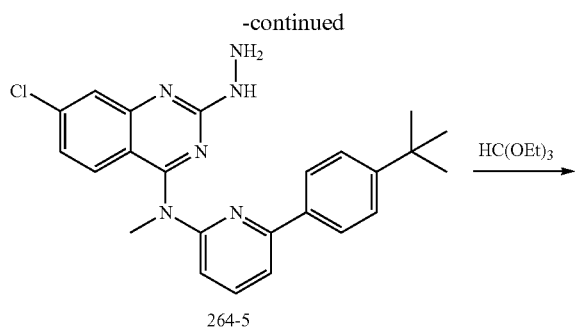

264-5

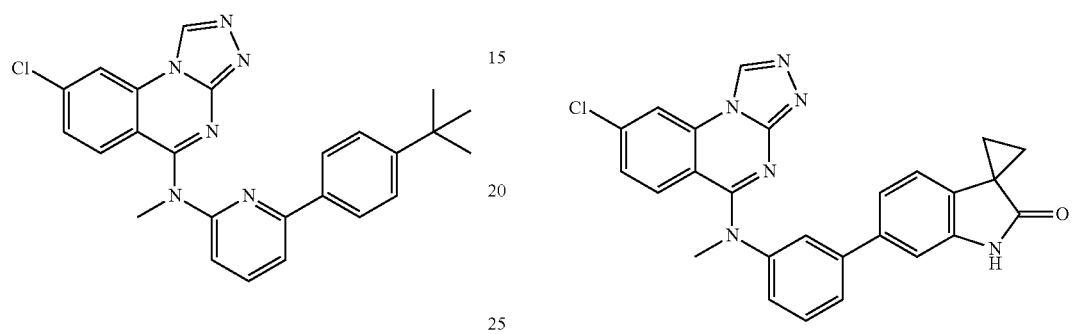

Synthetic route to prepare 6-(4-(tert-butyl)phenyl)-N-methylpyridin-2-amine. (Compound 264-2) was analogous to that used in the preparation of Example 252.

Synthesis of N-(6-(4-(tert-butyl)phenyl)pyridin-2-yl)-8-chloro-N-methyl-[1,2,4]triazolo[4,3-a]quinazolin-5-amine (Compound 264-4): A solution of 2,4,7-trichloroquinazoline (173 mg, 0.68 mmol) in THF (5 ml) at −20° C. were added 6-(4-(tert-butyl)phenyl)-N-methylpyridin-2-amine (160 mg, 0.86 mmol) and LiHMDS in THF (1M, 0.3 ml, 0.32 mmol). The mixture was stirred for 2 hours at −20° C. Water and DCM were added to the mixture and the organic phase was dried over MgSO₄ and evaporated under reduced pressure. Solids were used in the next step.

Synthetic routes to prepare Compound 264-5 and the title compound were analogous to those described in the preparation of Example 252. ¹H NMR (400 MHz, Chloroform-d) δ 9.30 (s, 1H), 8.18 (d, J=1.7 Hz, 1H), 7.82 (t, J=7.8 Hz, 1H), 7.68 (dd, J=15.3, 8.0 Hz, 3H), 7.44 (d, J=8.2 Hz, 2H), 7.24-7.16 (m, 2H), 7.06 (d, J=7.9 Hz, 1H), 3.88 (s, 3H), 1.35 (s, 9H); LCMS(m/z) 443.4.

Example 265. 6-(3-((8-chloro-[1,2,4]triazolo[4,3-a]quinazolin-5-yl)(methyl)amino)phenyl)-4-fluoro-1-methyl-1,3-dihydro-2H-benzo[d]imidazol-2-one

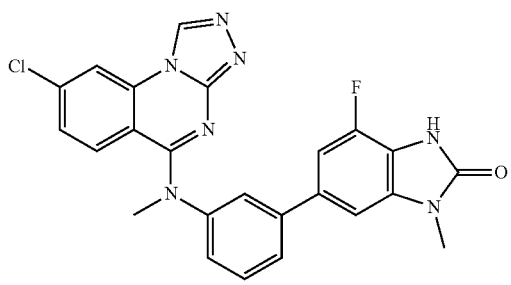 [SMILES: CN(c1cccc(-c2cc(F)c3[nH]c(=O)n(C)c3c2)c1)c1nc2nncn2c2cc(Cl)ccc12]

Example 265 was prepared in a similar manner as Example 252. ¹H NMR (400 MHz, Methanol-d₄) δ 9.58 (s, 1H), 8.50 (d, J=2.0 Hz, 1H), 7.76 (ddd, J=7.9, 1.9, 1.0 Hz, 1H), 7.71 (t, J=2.0 Hz, 1H), 7.64 (t, J=7.9 Hz, 1H), 7.46-7.28 (m, 3H), 7.21-7.08 (m, 2H), 3.85 (s, 3H), 3.61-3.54 (m, 3H); LCMS(m/z) 474.4.

Example 266. 6'-(3-((8-chloro-[1,2,4]triazolo[4,3-a]quinazolin-5-yl)(methyl)amino)phenyl)spiro[cyclopropane-1,3'-indolin]-2'-one

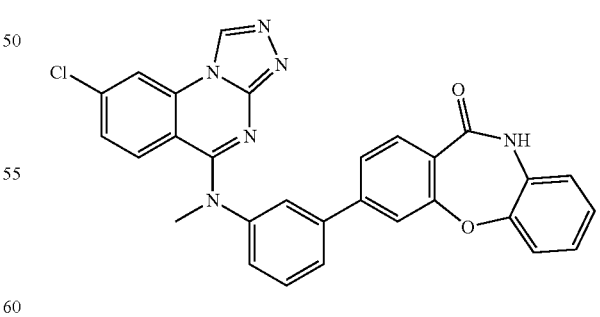

Example 266 was prepared in a similar manner as Example 252. ¹H NMR (400 MHz, Methanol-d₄) δ 9.59 (s, 1H), 8.50 (d, J=2.0 Hz, 1H), 7.78 (dt, J=7.8, 1.3 Hz, 1H), 7.71 (t, J=2.0 Hz, 1H), 7.65 (t, J=7.9 Hz, 1H), 7.44 (ddd, J=7.9, 2.3, 1.0 Hz, 1H), 7.38 (dd, J=9.1, 2.0 Hz, 1H), 7.30 (d, J=9.2 Hz, 1H), 7.27-7.18 (m, 2H), 7.01 (d, J=7.8 Hz, 1H), 3.86 (s, 3H), 1.78-1.53 (m, 4H); LCMS(m/z) 467.2.

Example 267. 3-(3-((8-chloro-[1,2,4]triazolo[4,3-a]quinazolin-5-yl)(methyl)amino)phenyl)dibenzo[b,f][1,4]oxazepin-11(10H)-one Example 267 was prepared in a similar manner as Example 252. ¹H NMR (400 MHz, Methanol-d₄) δ 9.60 (s, 1H), 8.52 (d, J=2.0 Hz, 1H), 7.98-7.81 (m, 3H), 7.70 (t, J=7.9 Hz, 1H), 7.62-7.47 (m, 3H), 7.39 (dd, J=9.2, 2.0 Hz, 1H), 7.34-7.27 (m, 2H), 7.24-7.09 (m, 3H), 3.87 (s, 3H); LCMS(m/z) 519.4.

Example 268. 8-chloro-N-(3-(6-(1,1-difluoroethyl)pyridin-3-yl)phenyl)-6-fluoro-N-methyl-[1,2,4]triazolo[4,3-a]quinazolin-5-amine

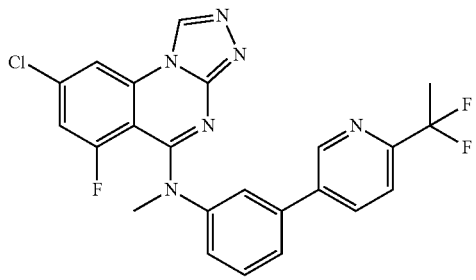

Example 268 was prepared in a similar manner as Example 252. $^1$H NMR (400 MHz, Methanol-$d_4$) δ 9.60 (s, 1H), 8.74 (s, 1H), 8.38 (s, 1H), 8.12 (dd, J=8.3, 2.3 Hz, 1H), 7.77 (d, J=8.3 Hz, 1H), 7.72-7.51 (m, 3H), 7.38 (dd, J=23.4, 9.8 Hz, 2H), 3.86 (s, 3H), 2.17-1.78 (m, 3H); LCMS(m/z) 469.4.

Example 269. 8-chloro-N-methyl-N-(3-(6-(4-(oxetan-3-yl)piperazin-1-yl)pyridin-3-yl)phenyl)-[1,2,4]triazolo[4,3-a]quinazolin-5-amine

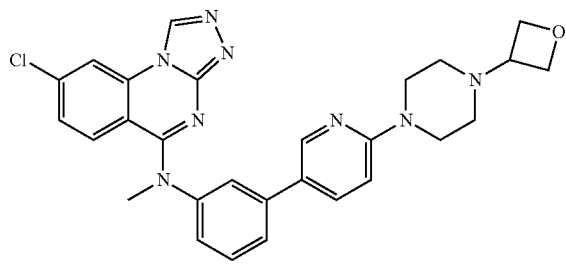 [SMILES: CN(c1cccc(-c2ccc(N3CCN(C4COC4)CC3)nc2)c1)c1nc2nncn2c2cc(Cl)ccc12]

A solution of 8-chloro-N-methyl-N-(3-(6-(piperazin-1-yl)pyridin-3-yl)phenyl)-[1,2,4]triazolo[4,3-a]quinazolin-5-amine (Example 258, 20 mg, 0.04 mmol) and oxetan-3-one (10 mg, 0.15 mmol) in THF (5 ml) at room temperature was added sodium triacetoxyborohydride (40 mg, 0.19 mmol). The mixture was stirred at room temperature for 1 hr. Water and DCM were added to the mixture and the organic phase was dried over MgSO$_4$ and evaporated under reduced pressure. The crude product was purified by reverse phase chromatography ACN/Water 15-95% with 0.1% TFA for 15 min to afford the title compound: $^1$H NMR (400 MHz, Methanol-$d_4$) δ 9.59 (s, 1H), 8.58-8.36 (m, 2H), 8.02-7.88 (m, 1H), 7.82-7.56 (m, 3H), 7.48-7.33 (m, 2H), 7.30 (d, J=9.1 Hz, 1H), 7.07 (d, J=8.9 Hz, 1H), 4.93 (d, J=7.7 Hz, 4H), 4.40 (q, J=6.3 Hz, 1H), 3.86 (s, 3H), 3.30 (s, 8H); LCMS(m/z) 527.3.

Example 270. 1-(4-(5-(3-((8-chloro-[1,2,4]triazolo[4,3-a]quinazolin-5-yl)(methyl)amino)phenyl)pyridin-2-yl)piperazin-1-yl)-2,2-dimethylpropan-1-one

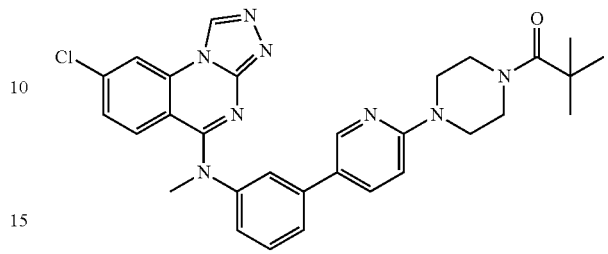

A solution of 8-chloro-N-methyl-N-(3-(6-(piperazin-1-yl)pyridin-3-yl)phenyl)-[1,2,4]triazolo[4,3-a]quinazolin-5-amine (Example 258, 20 mgs, 0.04 mmol) and pivalic anhydride (10 mgs, 0.15 mmol) in pyridine (5 ml) was stirred at room temperature for 24 hrs. reaction mixture was evaporated and then purified in reverse phase chromatography ACN/Water 15-95% with 0.1% TFA for 15 min to afford the title compound: $^1$H NMR (400 MHz, Methanol-$d_4$) δ 9.61 (s, 1H), 8.52 (d, J=2.1 Hz, 1H), 8.33 (d, J=2.5 Hz, 1H), 8.16 (dd, J=9.3, 2.5 Hz, 1H), 7.85-7.73 (m, 2H), 7.68 (t, J=7.8 Hz, 1H), 7.53-7.44 (m, 1H), 7.37 (dd, J=9.1, 2.1 Hz, 1H), 7.30 (d, J=9.1 Hz, 1H), 7.24 (d, J=9.3 Hz, 1H), 3.88 (d, J=10.9 Hz, 7H), 3.74 (dd, J=6.7, 3.9 Hz, 4H), 1.34 (s, 9H); LCMS(m/z) 555.4.

Example 271. 1-(4-(5-(3-((8-chloro-[1,2,4]triazolo[4,3-a]quinazolin-5-yl)(methyl)amino)phenyl)pyridin-2-yl)piperazin-1-yl)-2,2-dimethylpropan-1-one

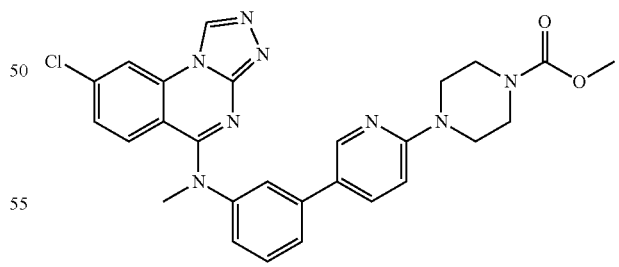

Example 271 was prepared in an analogous procedure to the preparation of Example 270. $^1$H NMR (400 MHz, Methanol-$d_4$) δ 9.60 (s, 1H), 8.51 (d, J=2.0 Hz, 1H), 8.32 (d, J=2.3 Hz, 1H), 8.07 (dd, J=9.2, 2.5 Hz, 1H), 7.84-7.71 (m, 2H), 7.66 (t, J=7.9 Hz, 1H), 7.45 (ddd, J=8.0, 2.2, 1.0 Hz, 1H), 7.37 (dd, J=9.1, 2.0 Hz, 1H), 7.30 (d, J=9.1 Hz, 1H), 7.16 (d, J=9.2 Hz, 1H), 3.86 (s, 3H), 3.76 (s, 3H), 3.74-3.62 (m, 8H); LCMS(m/z) 529.4.

Example 272. 8-chloro-N-(6-(4-(1,1-difluoroethyl)phenyl)pyridin-2-yl)-N-methyl-[1,2,4]triazolo[4,3-a]quinazolin-5-amine

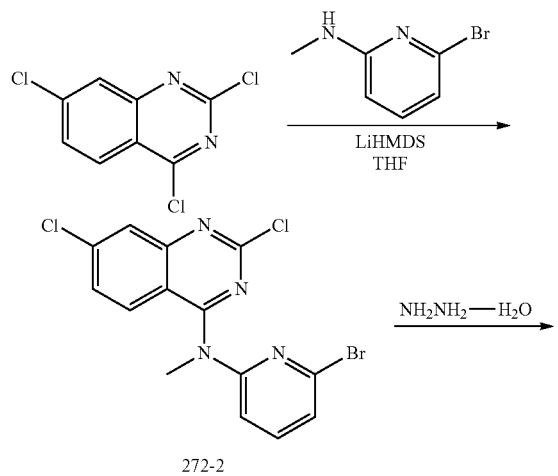

272-2

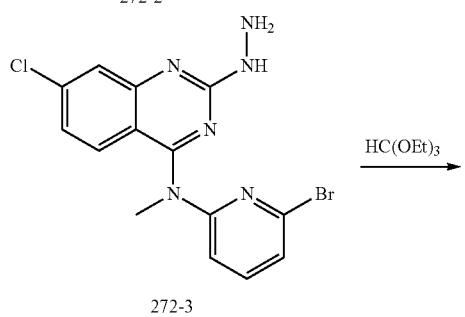

272-3

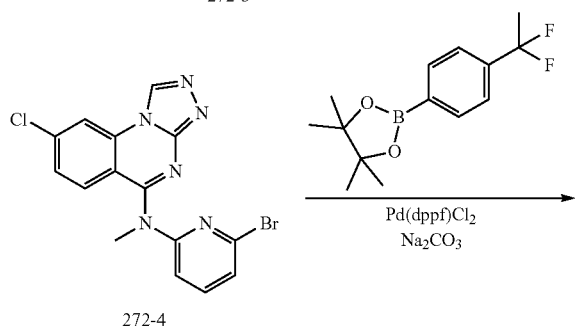

272-4

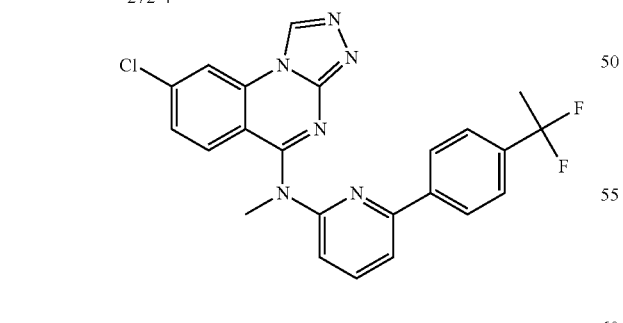

Synthesis of N-(6-bromopyridin-2-yl)-2,7-dichloro-N-methylquinazolin-4-amine (Compound 272-2): A solution of 2,4,7-trichloroquinazoline (280 mg, 1.2 mmol) in THF (5 ml) at −20 C were added 6-bromo-N-methylpyridin-2-amine (234 mg, 1.25 mmol) and LiHMDS in THF (1.0 M, 1.6 ml, 1.2 mmol). The mixture was stirred for 2 hours at −20° C. Water and DCM were added to the mixture and the organic phase was dried over MgSO$_4$ and evaporated under reduced pressure. The crude product was used in the next step without further purification.

Synthesis of Compounds 272-3 and 272-4 were achieved through a similar procedure as described to synthesize Example 249.

The final step of the synthesis of 8-chloro-N-(6-(4-(1,1-difluoroethyl)phenyl)-pyridin-2-yl)-N-methyl-[1,2,4]triazolo[4,3-a]quinazolin-5-amine was achieved through a similar procedure described in Example 252. $^1$H NMR (400 MHz, Methanol-d$_4$) δ 9.67 (s, 1H), 8.55 (s, 1H), 8.03 (t, J=7.8 Hz, 1H), 7.90 (d, J=8.8 Hz, 2H), 7.62-7.51 (m, 2H), 7.41 (d, J=8.7 Hz, 2H), 7.29 (d, J=9.0 Hz, 1H), 6.87 (t, J=8.3 Hz, 1H), 3.92 (s, 3H), 2.04-1.76 (m, 3H); LCMS(m/z) 451.4.

Example 273. 8-chloro-N-methyl-N-(6-(2-morpholinopyrimidin-5-yl)pyridin-2-yl)-[1,2,4]triazolo[4,3-a]quinazolin-5-amine

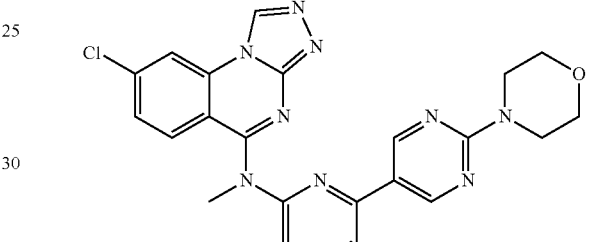

Example 273 was synthesized in a similar manner as that described for Example 272. $^1$H NMR (400 MHz, Methanol-d$_4$) δ 9.68 (s, 1H), 8.77 (s, 2H), 8.57 (d, J=2.1 Hz, 1H), 7.99 (t, J=7.9 Hz, 1H), 7.84 (d, J=7.8 Hz, 1H), 7.50-7.34 (m, 2H), 7.34-7.13 (m, 1H), 3.99-3.68 (m, 11H); LCMS(m/z) 474.4.

Example 274. 8-chloro-N-methyl-N-(6-(4-(methylsulfonyl)phenyl)pyridin-2-yl)-[1,2,4]triazolo[4,3-a]quinazolin-5-amine

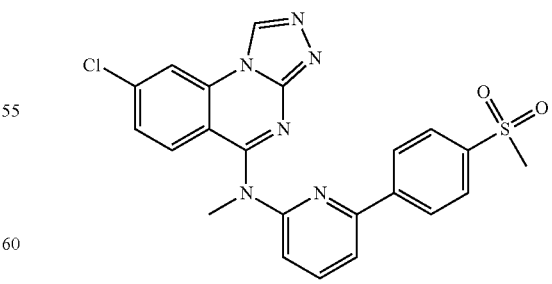

Example 274 was synthesized in a similar manner as that described for Example 272. $^1$H NMR (400 MHz, Methanol-d$_4$) δ 9.4 (s, 1H), 8.5 (s, 1H), 8.17-6.95 (m, 9H), 3.14 (s, 6H); LCMS(m/z) 465.3.

Example 275. 8-chloro-N-(6'-(1,1-difluoroethyl)-[2,3'-b]pyridin-6-yl)-N-methyl-[1,2,4]triazolo[4,3-a]quinazolin-5-amine

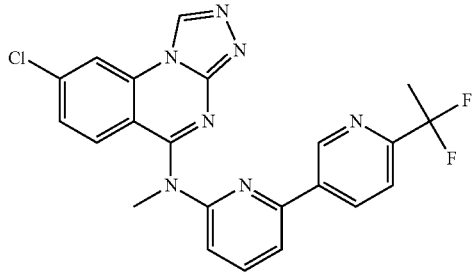

Example 275 was synthesized in a similar manner as that described for Example 272. ¹H NMR (400 MHz, Methanol-d₄) δ 9.63 (s, 1H), 8.26 (s, 1H), 8.08 (s, 1H), 7.96-7.30 (m, 4H), 7.25-6.74 (m, 3H), 3.31 (s, 3H), 2.24-1.73 (m, 3H); LCMS(m/z) 452.3.

Example 276. 8-chloro-N-(6-(4-chlorophenyl)pyridin-2-yl)-N-methyl-[1,2,4]triazolo[4,3-a]quinazolin-5-amine

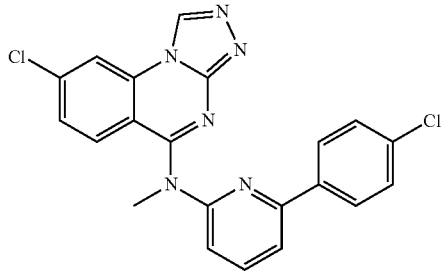

Example 276 was synthesized in a similar manner as that described for Example 272. ¹H NMR (400 MHz, Methanol-d₄) δ 9.59 (s, 1H), 8.27 (s, 2H), 8.02 (s, 1H), 7.83 (s, 1H), 7.67-7.01 (m, 6H), 3.90 (s, 3H); LCMS(m/z) 421.3.

Example 277. 8-chloro-N-methyl-N-(3-(oxetan-3-ylethynyl)phenyl)-[1,2,4]triazolo[4,3-a]quinazolin-5-amine

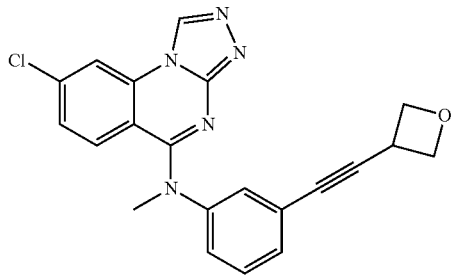 [SMILES: CN(c1cccc(C#CC2COC2)c1)c1nc2nncn2c2cc(Cl)ccc12]

A vial with stir bar was charged with N-(3-bromophenyl)-8-chloro-N-methyl-[1,2,4]triazolo[4,3-a]quinazolin-5-amine (Example 308, 50 mg, 0.13 mmol), 3-ethynyloxetane (21 mg, 0.26 mmol), Pd(PPh₃)Cl₂ (0.9 mg, 0.0013 mmol), and CuI (1.2 mg, 0.0064 mmol). The vial was then charged with DMF (2.0 mL) and DIPEA (0.045 mL, 0.26 mmol) and the suspension bubbled with nitrogen for 5 minutes. The reaction was heated to 100° C. for 24 hours at which point LC/MS indicated incomplete conversion. An additional portion of alkyne, Pd, CuI, and DIPEA were added and the reaction heated for a further 24 hours. LC/MS indicated near complete conversion and the reaction was filtered through a plug of Celite and eluted with EtOAc. The filtrate was evaporated to a residue which was purified by normal phase flash chromatography using 3:1 EtOAc:EtOH in heptanes. The crude product was further purified via prep-HPLC to give the title compound: ¹H NMR (400 MHz, DMSO-d₆) δ 9.74 (s, 1H), 8.61 (d, J=2.1 Hz, 1H), 7.51-7.47 (m, 1H), 7.46-7.35 (m, 4H), 7.23 (d, J=9.0 Hz, 1H), 4.77 (dd, J=8.5, 5.4 Hz, 2H), 4.58 (dd, J=7.1, 5.4 Hz, 2H), 4.12 (ddd, J=15.6, 8.5, 7.1 Hz, 1H), 3.57 (s, 3H); LCMS(m/z) 390.1.

Example 278. 8-chloro-N-(4'-(2-(dimethylamino)ethoxy)-[1,1'-biphenyl]-3-yl)-N-methyl-[1,2,4]triazolo[4,3-a]quinazolin-5-amine

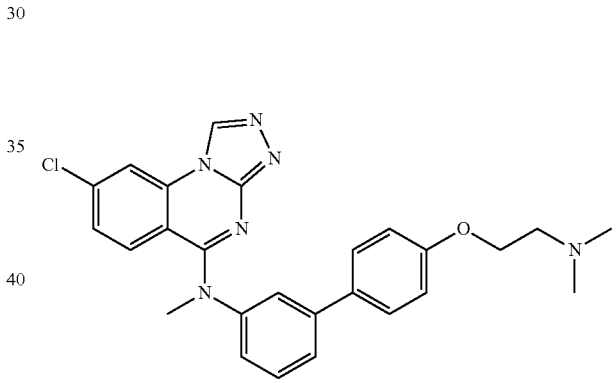

A vial with stir bar was charged with N-(3-bromophenyl)-8-chloro-N-methyl-[1,2,4]triazolo[4,3-a]quinazolin-5-amine (Example 308, 30 mg, 0.077 mmol), N,N-dimethyl-2-[4-(4,4,5,5-tetramethyl-1,3,2-dioxaborolan-2-yl)phenoxy]ethanamine (45 mg, 0.15 mmol), and (dtbpf)PdCl₂ (2.7 mg, 0.004 mmol). The vial was then flushed with nitrogen and charged with dioxane (1.0 mL) and nitrogen sparged 2M aqueous Na₂CO₃ (0.2 mL). The reaction was warmed to 50° C. and monitored via LC/MS. Once complete (about 18 hours), the reaction was filtered through a plug of Celite and eluted with EtOAc. The filtrate was then evaporated, and the residue purified via prep-HPLC to give the title compound: ¹H NMR (400 MHz, DMSO-d₆) δ 9.72 (s, 1H), 9.57 (s, 1H), 8.59 (d, J=2.1 Hz, 1H), 7.67-7.58 (m, 4H), 7.51 (t, J=7.8 Hz, 1H), 7.40-7.29 (m, 2H), 7.28 (d, J=9.0 Hz, 1H), 7.09-7.01 (m, 2H), 4.34 (t, J=5.0 Hz, 2H), 3.64 (s, 3H), 3.52 (q, J=5.0 Hz, 2H), 2.87 (s, 3H), 2.86 (s, 3H); LCMS(m/z) 473.2.

Example 279. tert-butyl 4-((3'-((8-chloro-[1,2,4]triazolo[4,3-a]quinazolin-5-yl)(methyl)amino)-[1,1'-biphenyl]-4-yl)oxy)piperidine-1-carboxylate

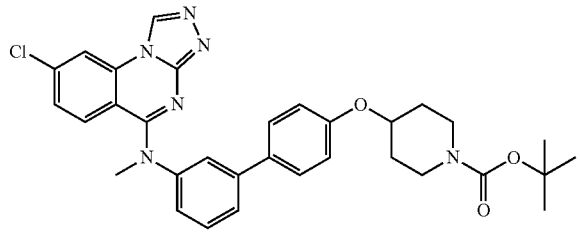 [SMILES: CN(c1cccc(-c2ccc(OC3CCN(C(=O)OC(C)(C)C)CC3)cc2)c1)c1nc2nncn2c2cc(Cl)ccc12]

Example 279 was synthesized according to a similar procedure as that described for Example 278. $^1$H NMR (400 MHz, DMSO-$d_6$) δ 9.76 (s, 1H), 8.61 (d, J=2.1 Hz, 1H), 7.66 (s, 1H), 7.63 (d, J=7.9 Hz, 1H), 7.57 (d, J=8.8 Hz, 2H), 7.51 (t, J=7.9 Hz, 1H), 7.39 (dd, J=9.0, 2.0 Hz, 1H), 7.36-7.30 (m, 1H), 7.27 (d, J=9.0 Hz, 1H), 7.03 (d, J=8.8 Hz, 2H), 4.64-4.55 (m, 1H), 3.69-3.60 (m, 5H), 3.27-3.12 (m, 2H), 1.98-1.83 (m, 2H), 1.59-1.45 (m, 2H), 1.40 (s, 9H); LCMS (m/z) 585.2.

Example 280. 1-(3'-((8-chloro-[1,2,4]triazolo[4,3-a]quinazolin-5-yl)(methyl)amino)-[1,1'-biphenyl]-4-yl)imidazolidin-2-one

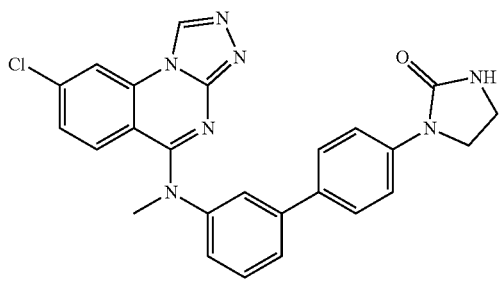 [SMILES: CN(c1cccc(-c2ccc(N3CCNC3=O)cc2)c1)c1nc2nncn2c2cc(Cl)ccc12]

Example 280 was synthesized according to a similar procedure as that described for Example 278. $^1$H NMR (400 MHz, DMSO-$d_6$) δ 9.75 (s, 1H), 8.61 (d, J=2.1 Hz, 1H), 7.70 (s, 1H), 7.66 (d, J=8.0 Hz, 1H), 7.61 (s, 4H), 7.51 (t, J=7.9 Hz, 1H), 7.40 (dd, J=9.0, 2.1 Hz, 1H), 7.35-7.30 (m, 1H), 7.28 (d, J=9.0 Hz, 1H), 7.01 (s, 1H), 3.86 (dd, J=9.3, 6.6 Hz, 2H), 3.66 (s, 3H), 3.46-3.36 (m, 2H); LCMS(m/z) 470.1.

Example 281. 1-(3'-((8-chloro-[1,2,4]triazolo[4,3-a]quinazolin-5-yl)(methyl)amino)-[1,1'-biphenyl]-4-yl)pyrrolidin-2-one

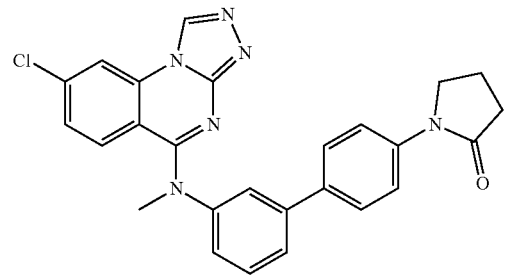 [SMILES: CN(c1cccc(-c2ccc(N3CCCC3=O)cc2)c1)c1nc2nncn2c2cc(Cl)ccc12]

A microwave reaction vial (0.5-2 mL) with stirring vane was charged with 1-(4-bromophenyl)pyrrolidin-2-one (15 mg, 0.064 mmol), bis(pinacolato)diboron (20 mg, 0.077 mmol), Pd(PPh$_3$)Cl$_2$ (4.5 mg, 0.0064 mmol), and KOAc (19 mg, 0.19 mmol). The vial was then flushed with nitrogen and charged with dioxane (1.0 mL). The reaction was irradiated (Biotage Initiator) at 120° C. until complete conversion to the intermediate boronate was observed via LC/MS (typically 45-90 minutes). N-(3-bromophenyl)-8-chloro-N-methyl-[1,2,4]triazolo[4,3-a]quinazolin-5-amine (25 mg, 0.064 mmol) and nitrogen sparged 2M aqueous Na$_2$CO$_3$ (0.16 mL) were then added and the reaction heated to 100° C. until complete conversion was observed via LC/MS (typically 15-60 minutes). The reaction was then filtered through a plug of Celite and eluted with EtOAc. The filtrate was evaporated, and the residue purified via prep-HPLC to afford the title compound. $^1$H NMR (400 MHz, Methanol-$d_4$) δ 9.56 (s, 1H), 8.48 (d, J=2.1 Hz, 1H), 7.81-7.77 (m, 1H), 7.73-7.69 (m, 3H), 7.66-7.61 (m, 3H), 7.43-7.39 (m, 1H), 7.36 (dd, J=9.2, 2.0 Hz, 1H), 7.28 (d, J=9.2 Hz, 1H), 3.95 (t, J=7.1 Hz, 2H), 3.84 (s, 3H), 2.61 (t, J=8.1 Hz, 2H), 2.25-2.14 (m, 2H); LCMS(m/z) 469.1.

Example 282. 8-chloro-N-methyl-N-(4'-(piperidin-4-yloxy)-[1,1'-biphenyl]-3-yl)-[1,2,4]triazolo[4,3-a]quinazolin-5-amine

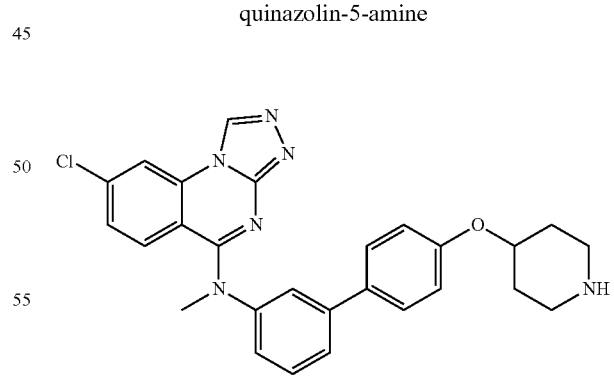

To a solution of tert-butyl 4-[4-[3-[(8-chloro-[1,2,4]triazolo[4,3-a]quinazolin-5-yl)-methyl-amino]phenyl]phenoxy]piperidine-1-carboxylate (Example 279, 98 mg, 0.15 mL) in DCM (5 mL) was added TFA (0.23 mL, 3.0 mmol). After 3 hours, the reaction was evaporated. The resulting residue was purified via prep-HPLC to give the title compound: $^1$H NMR (400 MHz, DMSO-$d_6$) δ 9.71 (s, 1H), 8.59 (d, J=2.1 Hz, 1H), 8.43 (s, 1H), 7.64-7.57 (m, 4H), 7.50 (t, J=7.8 Hz, 1H), 7.36 (dd, J=9.0, 2.1 Hz, 1H), 7.34-7.30 (m, 1H), 7.28 (d, J=9.0 Hz, 1H), 7.10-7.01 (m, 2H), 4.73-4.64 (m, 1H), 3.64 (s, 3H), 3.32-3.18 (m, 2H), 3.15-3.01 (m, 2H), 2.08 (dd, J=15.3, 6.3 Hz, 2H), 1.87-1.73 (m, 2H); LCMS (m/z) 485.2.

Example 283. 3-((3-((8-chloro-[1,2,4]triazolo[4,3-a]quinazolin-5-yl)(methyl)amino)phenyl)ethynyl)oxetan-3-ol

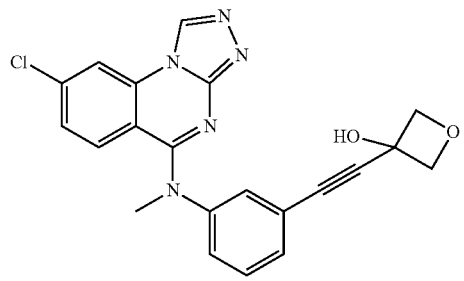 [SMILES: CN(c1cccc(C#CC2(O)COC2)c1)c1nc2nncn2c2cc(Cl)ccc12]

Example 283 was synthesized in a similar manner to the procedure described for Example 277. $^1$H NMR (400 MHz, DMSO-d$_6$) δ 9.75 (s, 1H), 8.62 (d, J=2.1 Hz, 1H), 7.57-7.50 (m, 1H), 7.50-7.38 (m, 4H), 7.23 (d, J=9.0 Hz, 1H), 6.61 (s, 1H), 4.72 (d, J=6.4 Hz, 2H), 4.57 (d, J=6.4 Hz, 2H), 3.58 (s, 3H); LCMS(m/z) 406.1.

Example 284. 1-(4-((3'-((8-chloro-[1,2,4]triazolo[4,3-a]quinazolin-5-yl)(methyl)amino)-[1,1'-biphenyl]-4-yl)oxy)piperidin-1-yl)ethan-1-one

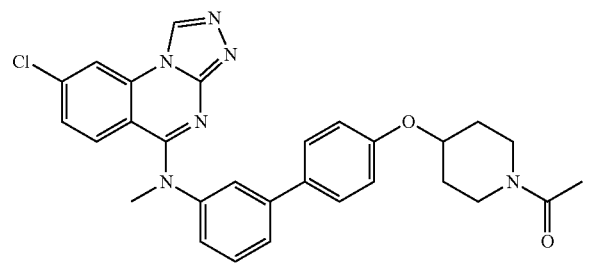 [SMILES: CC(=O)N1CCC(Oc2ccc(-c3cccc(N(C)c4nc5nncn5c5cc(Cl)ccc45)c3)cc2)CC1]

A suspension of 8-chloro-N-methyl-N-[3-[4-(4-piperidyloxy)phenyl]phenyl]-[1,2,4]triazolo[4,3-a]quinazolin-5-amine (Example 282, 10 mg, 0.017 mmol) in DCM (0.75 mL) was treated with acetic anhydride (0.017 mmol) and stirred at ambient temperature. After 2 hours, triethylamine (0.002 mL, 0.017 mmol) was added and the solution stirred a further hour at which point LC/MS indicated complete conversion. The reaction was evaporated, and the residue purified via prep-HPLC to give the title compound: $^1$H NMR (400 MHz, DMSO-d$_6$) δ 9.63 (s, 1H), 8.54 (d, J=1.3 Hz, 1H), 7.61-7.51 (m, 4H), 7.44 (t, J=7.8 Hz, 1H), 7.31 (s, 2H), 7.27-7.22 (m, 1H), 7.05-6.99 (m, 2H), 4.68-4.61 (m, 1H), 3.87-3.78 (m, 1H), 3.71-3.62 (m, 1H), 3.59 (s, 3H), 3.38-3.33 (m, 1H), 3.28-3.17 (m, 1H), 2.01 (s, 3H), 2.00-1.91 (m, 1H), 1.93-1.81 (m, 1H), 1.67-1.54 (m, 1H), 1.56-1.42 (m, 1H); LCMS(m/z) 527.2.

Example 285. 8-chloro-N-methyl-N-(4'-((1-methylpiperidin-4-yl)oxy)-[1,1'-biphenyl]-3-yl)-[1,2,4]triazolo[4,3-a]quinazolin-5-amine

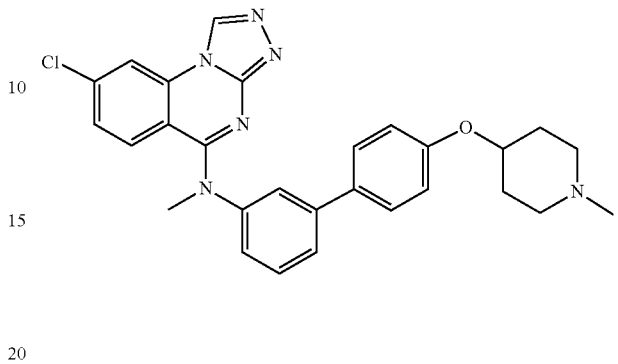

A suspension of 8-chloro-N-methyl-N-[3-[4-(4-piperidyloxy)phenyl]phenyl]-[1,2,4]triazolo[4,3-a]quinazolin-5-amine (Example 282. 15 mg, 0.025 mmol) in DCM (1.0 mL) was treated with formaldehyde (0.005 mL, 0.063 mmol) and stirred at ambient temperature for 5 minutes. Na(OAc)$_3$BH (5.8 mg, 0.028 mmol) was then added and the solution stirred at ambient for 3 hours. A second portion of borohydride was added, and the reaction stirred a further 45 minutes to affect complete conversion. The reaction was evaporated, and the residue purified via prep-HPLC to provide the title compound: $^1$H NMR (400 MHz, DMSO-d$_6$) δ 9.70 (s, 1H), 8.58 (d, J=2.0 Hz, 1H), 7.66-7.55 (m, 4H), 7.49 (t, J=7.8 Hz, 1H), 7.39-7.25 (m, 3H), 7.12-7.00 (m, 2H), 4.81-4.51 (m, 1H), 3.63 (s, 3H), 3.51 (d, J=12.4 Hz, 1H), 3.32 (d, J=12.2 Hz, 1H), 3.23-3.02 (m, 2H), 2.82 (dd, J=10.1, 4.8 Hz, 3H), 2.26 (d, J=13.5 Hz, 1H), 2.07 (d, J=14.8 Hz, 1H), 1.95 (t, J=13.4 Hz, 1H), 1.79-1.64 (m, 1H); LCMS(m/z) 499.2.

Example 286. 8-chloro-N-(3-(6-fluoropyridin-3-yl)phenyl)-N-methyl-[1,2,4]triazolo[4,3-a]quinazolin-5-amine

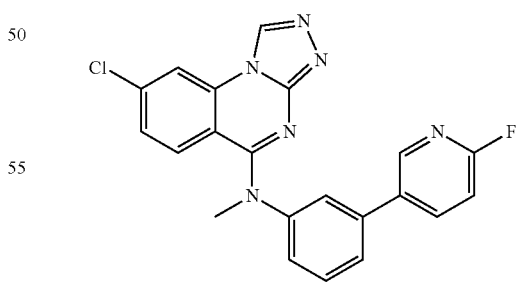

Example 286 was synthesized in a similar manner to the procedure described for Example 278. $^1$H NMR (400 MHz, DMSO-d$_6$) δ 9.78 (s, 1H), 8.63 (d, J=2.1 Hz, 1H), 8.54 (d, J=2.6 Hz, 1H), 8.28 (td, J=8.2, 2.7 Hz, 1H), 7.86-7.81 (m, 1H), 7.76-7.70 (m, 1H), 7.57 (t, J=7.9 Hz, 1H), 7.46-7.36 (m, 2H), 7.32-7.25 (m, 2H), 3.67 (s, 3H); LCMS(m/z) 405.1.

Example 287. 5-((3-bromophenyl)(methyl)amino)-8-chloro-[1,2,4]triazolo[4,3-a]quinazolin-1(2H)-one

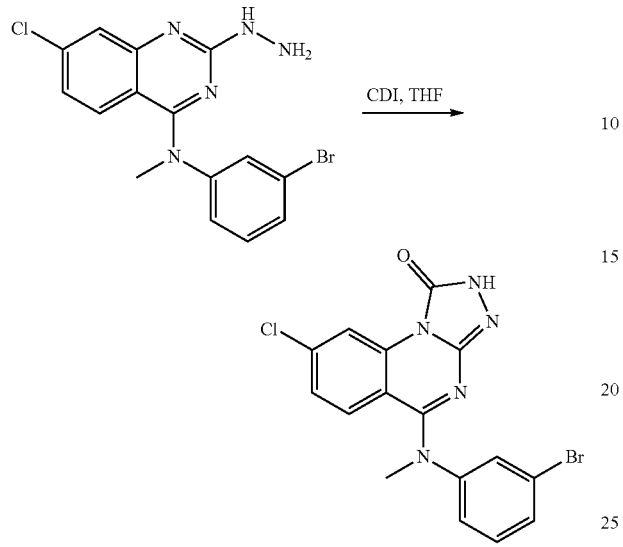

A solution of N-(3-bromophenyl)-7-chloro-2-hydrazino-N-methyl-quinazolin-4-amine (216 mg, 0.46 mmol) and carbonyldiimidazole (CDI, 89 mg, 0.55 mmol) in THF (4 mL) was stirred at ambient temperature for 90 minutes. The solution was then evaporated, and the resultant residue purified by flash chromatography using 10% MeOH/DCM. A portion was further purified via prep-HPLC to afford the title compound: $^1$H NMR (400 MHz, DMSO-$d_6$) δ 12.17 (s, 1H), 8.75 (d, J=2.3 Hz, 1H), 7.63 (s, 1H), 7.46-7.41 (m, 1H), 7.36-7.28 (m, 2H), 7.24 (dd, J=8.9, 2.2 Hz, 1H), 7.10 (d, J=8.8 Hz, 1H), 3.45 (s, 3H); LCMS(m/z) 406.0/404.0.

Example 288. 5-((4'-(tert-butyl)-[1,1'-biphenyl]-3-yl)(methyl)amino)-8-chloro-[1,2,4]triazolo[4,3-a]quinazolin-1(2H)-one

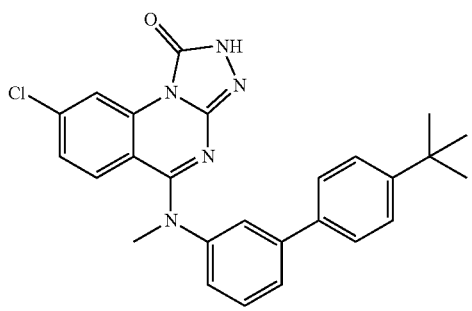 [SMILES: CN(c1cccc(-c2ccc(C(C)(C)C)cc2)c1)c1nc2n[nH]c(=O)n2c2cc(Cl)ccc12]

A vial with stir bar was charged with 5-(3-bromo-N-methyl-anilino)-8-chloro-2H-[1,2,4]triazolo[4,3-a]quinazolin-1-one (Example 287, 36 mg, 0.079 mmol), 4-tert-Butylphenylboronic acid (15 mg, 0.083 mmol), and Pd(PPh$_3$)Cl$_2$ (5.5 mg, 0.008 mmol). The vial was then flushed with nitrogen and charged with dioxane (1.0 mL) and nitrogen sparged 2M aqueous Na$_2$CO$_3$ (0.08 mL). The reaction was heated to 100° C. for 18 hours at which point LC/MS indicated partial conversion. An additional portion of boronic acid, catalyst, and base were added and the reaction heated for a further 4.5 hours at which point LC/MS indicated near complete conversion. The reaction was filtered through a plug of Celite and eluted with EtOAc. The filtrate was evaporated, and the residue purified via prep-HPLC to give the title compound: $^1$H NMR (400 MHz, DMSO-$d_6$) δ 12.11 (s, 1H), 8.75 (d, J=2.0 Hz, 1H), 7.60-7.54 (m, 4H), 7.50-7.42 (m, 3H), 7.29 (dd, J=7.4, 2.1 Hz, 1H), 7.19-7.10 (m, 2H), 3.52 (s, 3H), 1.29 (s, 9H); LCMS (m/z) 458.2.

Example 289. 8-chloro-N-methyl-N-(3-(6-(pyrrolidin-1-yl)pyridin-3-yl)phenyl)-[1,2,4]triazolo[4,3-a]quinazolin-5-amine

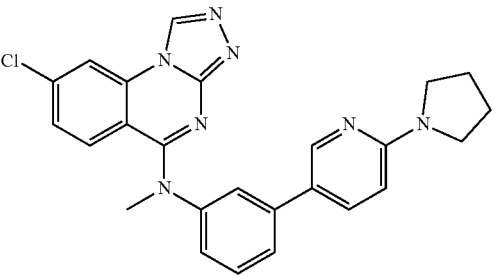 [SMILES: CN(c1cccc(-c2ccc(N3CCCC3)nc2)c1)c1nc2nncn2c2cc(Cl)ccc12]

A solution of 8-chloro-N-[3-(6-fluoro-3-pyridyl)phenyl]-N-methyl-[1,2,4]triazolo[4,3-a]quinazolin-5-amine (Example 286, 16.5 mg, 0.037 mmol) in DMF (0.5 mL) was treated with pyrrolidine (0.005 mL, 0.055 mmol) and the reaction warmed to 80° C. After 18 hours LC/MS indicated partial conversion. Pyrrolidine (0.002 mL, 0.028 mmol) was added and the reaction heated a further 5 hours. The reaction was then diluted with EtOAc and washed once with saturated brine. The organic phase was then filtered through a plug of Celite, evaporated, and the residue purified via prep-HPLC to give the title compound: $^1$H NMR (400 MHz, DMSO-$d_6$) δ 9.74 (s, 1H), 8.60 (d, J=2.1 Hz, 1H), 8.20 (s, 1H), 8.11 (s, 1H), 7.72 (t, J=2.0 Hz, 1H), 7.65 (d, J=7.9 Hz, 1H), 7.52 (t, J=7.9 Hz, 1H), 7.41-7.32 (m, 2H), 7.28 (d, J=9.0 Hz, 1H), 6.92 (s, 1H), 3.65 (s, 3H), 3.54-3.44 (m, 4H), 2.06-1.95 (m, 4H); LCMS(m/z) 456.1.

Example 290. 1-(3'-((8-chloro-[1,2,4]triazolo[4,3-a]quinazolin-5-yl)(methyl)amino)-[1,1'-biphenyl]-4-yl)-3-methylimidazolidin-2-one

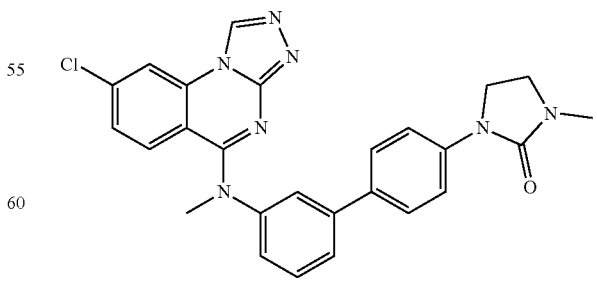

Example 290 was synthesized according to the general route described for Example 281. $^1$H NMR (400 MHz, DMSO-$d_6$) δ 9.76 (s, 1H), 8.61 (d, J=2.1 Hz, 1H), 7.70 (t, J=1.8 Hz, 1H), 7.69-7.64 (m, 1H), 7.62 (s, 4H), 7.52 (t, J=7.9 Hz, 1H), 7.40 (dd, J=9.1, 2.1 Hz, 1H), 7.35-7.31 (m, 1H), 7.28 (d, J=9.0 Hz, 1H), 3.85-3.76 (m, 2H), 3.67 (s, 3H), 3.50-3.41 (m, 2H), 2.77 (s, 3H); LCMS(m/z) 484.2.

Example 291. 8-chloro-N-(3-(6-(4-methoxypiperidin-1-yl)pyridin-3-yl)phenyl)-N-methyl-[1,2,4]triazolo[4,3-a]quinazolin-5-amine

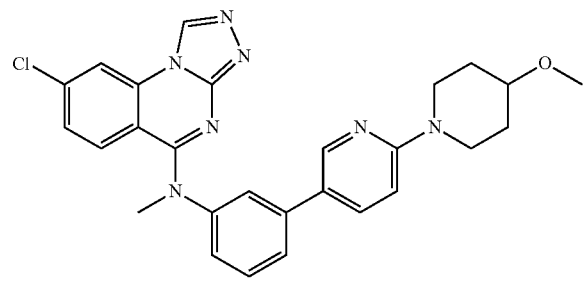 [SMILES: COC1CCN(c2ccc(-c3cccc(N(C)c4nc5nncn5c5cc(Cl)ccc45)c3)cn2)CC1]

A solution of 8-chloro-N-[3-(6-fluoro-3-pyridyl)phenyl]-N-methyl-[1,2,4]triazolo[4,3-a]quinazolin-5-amine (Example 286.20 mg, 0.045 mmol) in DMSO (0.75 mL) was treated with NaHCO₃ (19 mg, 0.22 mmol) and 4-Methoxypiperidine (0.009 mL, 0.078 mmol). The reaction was heated at 100° C. for 3.5 hours and 130° C. for a further 18 hours. The reaction was then filtered and purified via prep-HPLC to give the title compound: ¹H NMR (400 MHz, DMSO-d₆) δ 9.76 (s, 1H), 8.61 (d, J=2.1 Hz, 1H), 8.36 (d, J=2.6 Hz, 1H), 7.87 (d, J=9.1 Hz, 1H), 7.70-7.66 (m, 1H), 7.64 (d, J=8.0 Hz, 1H), 7.51 (t, J=7.8 Hz, 1H), 7.39 (dd, J=9.0, 2.1 Hz, 1H), 7.32 (d, J=8.9 Hz, 1H), 7.27 (d, J=9.0 Hz, 1H), 6.97 (d, J=9.0 Hz, 1H), 3.95 (dt, J=13.4, 4.8 Hz, 2H), 3.66 (s, 3H), 3.48-3.38 (m, 1H), 3.27 (s, 3H), 3.25-3.19 (m, 2H), 1.94-1.83 (m, 2H), 1.48-1.36 (m, 2H); LCMS(m/z) 500.2.

Example 292. 5-(3-((8-chloro-[1,2,4]triazolo[4,3-a]quinazolin-5-yl)(methyl)amino)phenyl)indolin-2-one

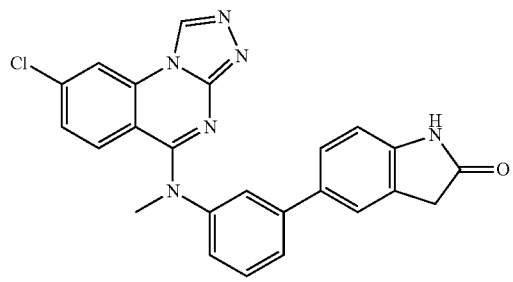 [SMILES: CN(c1cccc(-c2ccc3c(c2)CC(=O)N3)c1)c1nc2nncn2c2cc(Cl)ccc12]

Example 292 was synthesized according to the general route described for Example 278. ¹H NMR (400 MHz, DMSO-d₆) δ 10.49 (s, 1H), 9.82 (s, 1H), 8.64 (d, J=2.1 Hz, 1H), 7.69 (t, J=2.0 Hz, 1H), 7.69-7.63 (m, 1H), 7.57-7.51 (m, 2H), 7.48 (dd, J=8.1, 1.9 Hz, 1H), 7.44 (dd, J=9.1, 2.1 Hz, 1H), 7.39-7.34 (m, 1H), 7.25 (d, J=9.1 Hz, 1H), 6.87 (d, J=8.1 Hz, 1H), 3.69 (s, 3H), 3.51 (s, 2H); LCMS(m/z) 441.1.

Example 293. tert-butyl (3'-((8-chloro-[1,2,4]triazolo[4,3-a]quinazolin-5-yl)(methyl)amino)-[1,1'-biphenyl]-4-yl)carbamate

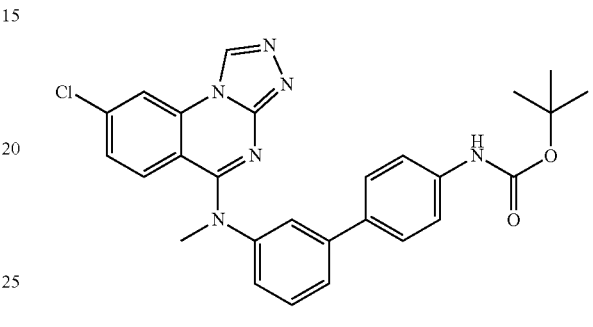

Example 293 was synthesized according to the general route described for Example 278. ¹H NMR (400 MHz, DMSO-d₆) δ 9.78 (s, 1H), 9.46 (s, 1H), 8.62 (d, J=2.1 Hz, 1H), 7.69 (t, J=2.0 Hz, 1H), 7.66 (d, J=8.0 Hz, 1H), 7.59-7.49 (m, 5H), 7.41 (dd, J=9.0, 2.1 Hz, 1H), 7.35-7.30 (m, 1H), 7.27 (d, J=9.1 Hz, 1H), 3.67 (s, 3H), 1.48 (s, 9H); LCMS(m/z) 501.2.

Example 294. 1-(3'-((8-chloro-[1,2,4]triazolo[4,3-a]quinazolin-5-yl)(methyl)amino)-[1,1'-biphenyl]-4-yl)piperidin-2-one

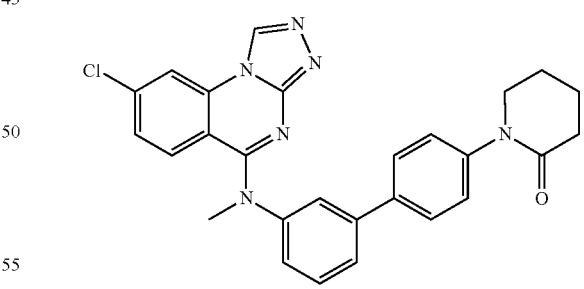

Example 294 was synthesized according to the general route described for Example 281. ¹H NMR (400 MHz, DMSO-d₆) δ 9.77 (s, 1H), 8.62 (d, J=2.1 Hz, 1H), 7.74 (t, J=2.0 Hz, 1H), 7.72-7.68 (m, 1H), 7.68-7.63 (m, 2H), 7.56 (t, J=7.9 Hz, 1H), 7.42-7.37 (m, 2H), 7.37-7.32 (m, 2H), 7.27 (d, J=9.1 Hz, 1H), 3.68 (s, 3H), 3.65-3.59 (m, 2H), 2.43-2.37 (m, 2H), 1.91-1.80 (m, 4H); LCMS(m/z) 483.2.

Example 295. 1-(3'-((8-chloro-[1,2,4]triazolo[4,3-a]quinazolin-5-yl)(methyl)amino)-[1,1'-biphenyl]-4-yl)pinerid2-(3'-((8-chloro-[1,2,4]triazolo[4,3-a]quinazolin-5-yl)(methyl)amino)-[1,1'-biphenyl]-4-yl)isothiazolidine 1,1-dioxide

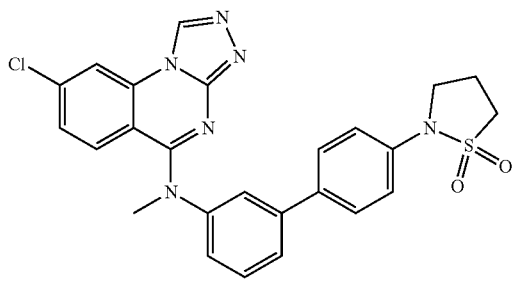 [SMILES: CN(c1cccc(-c2ccc(N3CCCS3(=O)=O)cc2)c1)c1nc2nncn2c2cc(Cl)ccc12]

Example 295 was synthesized according to the general route described for Example 278. $^1$H NMR (400 MHz, DMSO-$d_6$) δ 9.79 (s, 1H), 8.63 (d, J=2.1 Hz, 1H), 7.73 (t, J=2.0 Hz, 1H), 7.71-7.65 (m, 3H), 7.55 (t, J=7.9 Hz, 1H), 7.42 (dd, J=9.1, 2.1 Hz, 1H), 7.37 (dd, J=7.6, 2.1 Hz, 1H), 7.29-7.23 (m, 3H), 3.77 (t, J=6.5 Hz, 2H), 3.68 (s, 3H), 3.53 (t, J=7.4 Hz, 2H), 2.42 (p, J=6.9 Hz, 2H); LCMS(m/z) 505.1.

Example 297. 8-chloro-N-(3-(6-((2-methoxyethyl)(methyl)amino)pyridin-3-yl)phenyl)-N-methyl-[1,2,4]triazolo[4,3-a]quinazolin-5-amine

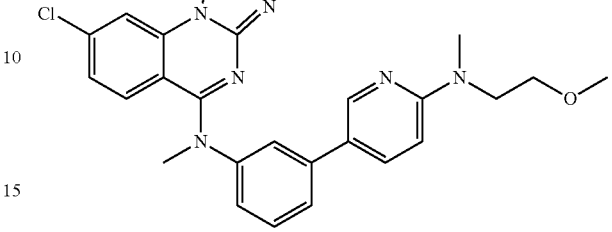

Example 297 was synthesized according to the general route described for Example 291. $^1$H NMR (400 MHz, DMSO-$d_6$) δ 9.77 (s, 1H), 8.62 (d, J=2.1 Hz, 1H), 8.30 (s, 1H), 7.91 (s, 1H), 7.68 (s, 1H), 7.64 (d, J=7.9 Hz, 1H), 7.52 (t, J=7.9 Hz, 1H), 7.39 (dd, J=9.0, 2.1 Hz, 1H), 7.33 (d, J=7.9 Hz, 1H), 7.27 (d, J=9.0 Hz, 1H), 6.84 (s, 1H), 3.74 (t, J=5.7 Hz, 2H), 3.66 (s, 3H), 3.51 (t, J=5.6 Hz, 2H), 3.24 (s, 3H), 3.08 (s, 3H); LCMS(m/z) 474.2.

Example 296. 3-((3-((8-chloro-[1,2,4]triazolo[4,3-a]quinazolin-5-yl)(methyl)amino)phenyl)ethynyl)-3-hydroxy-1-methylpyrrolidin-2-one

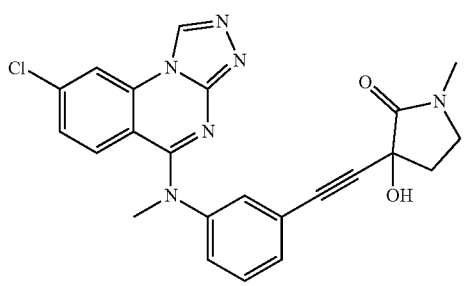 [SMILES: CN1CCC(O)(C#Cc2cccc(N(C)c3nc4nncn4c4cc(Cl)ccc34)c2)C1=O]

Example 296 was synthesized according to the general route described for Example 277. $^1$H NMR (400 MHz, DMSO-$d_6$) δ 9.74 (s, 1H), 8.62 (d, J=2.1 Hz, 1H), 7.49-7.35 (m, 5H), 7.21 (d, J=9.0 Hz, 1H), 3.58 (s, 3H), 3.37-3.26 (m, 2H), 2.77 (s, 3H), 2.43-2.35 (m, 1H), 2.20-2.10 (m, 1H); LCMS(m/z) 447.1.

Example 298. 1-(3'-((8-chloro-[1,2,4]triazolo[4,3-a]quinazolin-5-yl)(methyl)amino)-[1,1'-biphenyl]-4-yl)azetidin-2-one

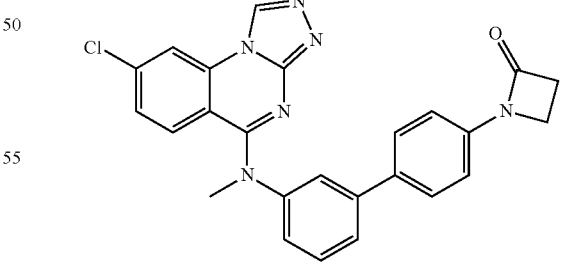

Example 298 was synthesized according to the general route described for Example 281. $^1$H NMR (400 MHz, DMSO-$d_6$) δ 9.78 (s, 1H), 8.62 (d, J=2.1 Hz, 1H), 7.73 (t, J=2.0 Hz, 1H), 7.71-7.64 (m, 3H), 7.53 (t, J=7.9 Hz, 1H), 7.44-7.37 (m, 3H), 7.37-7.33 (m, 1H), 7.27 (d, J=9.1 Hz, 1H), 3.67 (s, 3H), 3.65 (t, J=4.6 Hz, 2H), 3.10 (t, J=4.5 Hz, 2H); LCMS(m/z) 455.1.

Example 299. 5-(3-((8-chloro-[1,2,4]triazolo[4,3-a]quinazolin-5-yl)(methyl)amino)phenyl)-1-methylindolin-2-one

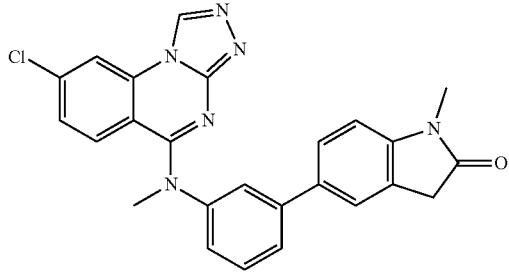 [SMILES: CN1C(=O)Cc2cc(-c3cccc(N(C)c4nc5nncn5c5cc(Cl)ccc45)c3)ccc21]

Example 299 was synthesized according to the general route described for Example 278. ¹H NMR (400 MHz, DMSO-d₆) δ 9.78 (s, 1H), 8.62 (d, J=2.1 Hz, 1H), 7.73 (t, J=2.0 Hz, 1H), 7.71-7.64 (m, 3H), 7.53 (t, J=7.9 Hz, 1H), 7.44-7.37 (m, 3H), 7.37-7.33 (m, 1H), 7.27 (d, J=9.1 Hz, 1H), 3.67 (s, 3H), 3.65 (t, J=4.6 Hz, 2H), 3.10 (t, J=4.5 Hz, 2H); LCMS(m/z) 455.1.

Example 300. tert-butyl 6-(3-((8-chloro-[1,2,4]triazolo[4,3-a]quinazolin-5-yl)(methyl)amino)phenyl)-2,6-diazaspiro[3.3]heptane-2-carboxylate

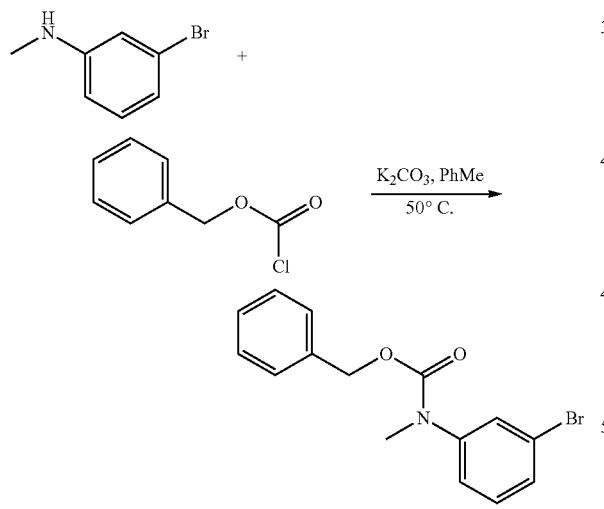

Synthesis of benzyl N-(3-bromophenyl)-N-methyl-carbamate: A solution of 3-Bromo-N-methylaniline (500 mg, 2.7 mmol) in toluene (13 mL) was treated with potassium carbonate (743 mg, 5.4 mmol) and benzyl chloroformate (0.66 mL, 4.7 mmol). The reaction was warmed to 50° C. and stirred for 16 hours. The reaction was then partitioned between EtOAc and water. The aqueous was extracted once with EtOAc and the combined organics were washed with brine and dried over MgSO₄. The organics were filtered, evaporated, and the resultant residue purified via normal phase flash chromatography using 30% EtOAc/Hexanes. ES/MS m/z: 322.0/320.1.

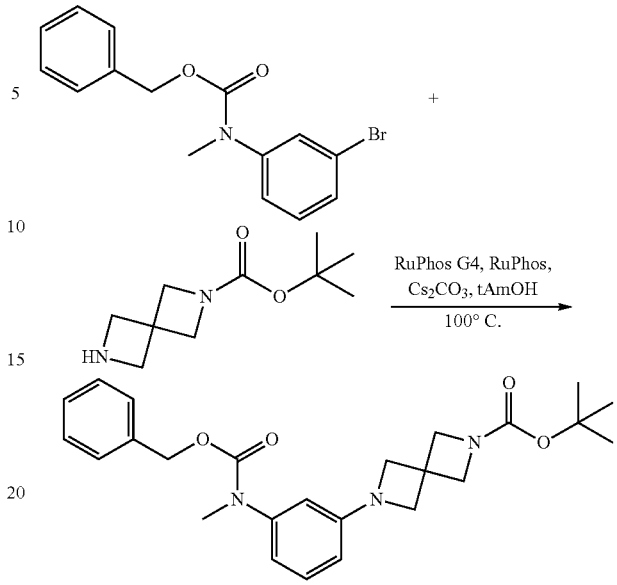

Synthesis of tert-butyl 6-[3-[benzyloxycarbonyl(methyl)amino]phenyl]-2,6-diazaspiro[3.3]heptane-2-carboxylate: A vial with stir bar was charged with tert-butyl 2,6-diazaspiro[3.3]heptane-2-carboxylate (650 mg, 3.3 mmol), RuPhos Pd Gen 4 (93 mg, 0.11 mmol), RuPhos (98 mg, 0.22 mmol), and Cs₂CO₃ (1780 mg, 5.5 mmol). The vial was then flushed with nitrogen and charged with benzyl N-(3-bromophenyl)-N-methyl-carbamate (700 mg, 2.2 mmol) as a solution in tert-amyl alcohol (8 mL). The reaction was warmed to 100° C. for 2.5 hours and then filtered through a plug of Celite. Product was eluted with EtOAc and the filtrate was then evaporated. The crude material was purified via normal phase flash chromatography using 50% EtOAc/Hexanes to give purified product: ¹H NMR (400 MHz, Chloroform-d) δ 7.31 (d, J=3.7 Hz, 5H), 7.17 (t, J=8.0 Hz, 1H), 6.63 (dt, J=8.0, 1.3 Hz, 1H), 6.35-6.27 (m, 2H), 5.16 (s, 2H), 4.07 (s, 4H), 3.92 (s, 4H), 3.29 (s, 3H), 1.45 (s, 9H); ES/MS m/z: 438.4.

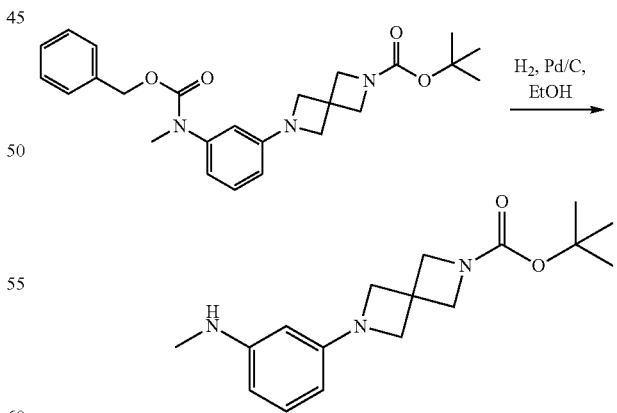

Synthesis of tert-butyl 6-[3-(methylamino)phenyl]-2,6-diazaspiro[3.3]heptane-2-carboxylate: 10% Pd/C (100 mg) was added to a nitrogen flushed vial and wet with EtOH (5 mL). tert-butyl 6-[3-[benzyloxycarbonyl(methyl)amino]phenyl]-2,6-diazaspiro[3.3]heptane-2-carboxylate (809 mg, 1.66 mmol) and EtOH (37 mL) were then added. The headspace was purged with nitrogen and then hydrogen gas was added via balloon. The mixture was stirred rapidly at ambient temperature for 2 hours before the catalyst was filtered off. The filtrate was evaporated to give product: $^1$H NMR (400 MHz, DMSO-d$_6$) δ 6.85 (t, J=7.9 Hz, 1H), 5.91 (ddd, J=8.0, 2.2, 0.9 Hz, 1H), 5.64 (ddd, J=7.9, 2.2, 0.9 Hz, 1H), 5.56 (t, J=2.1 Hz, 1H), 5.42 (q, J=5.0 Hz, 1H), 4.00 (s, 4H), 3.83 (s, 4H), 1.38 (s, 9H); ES/MS m/z: 304.3.

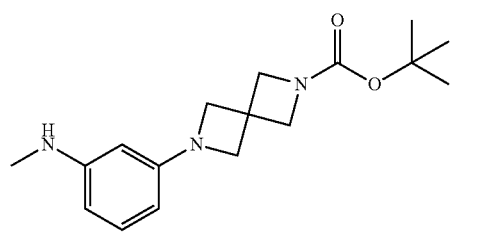

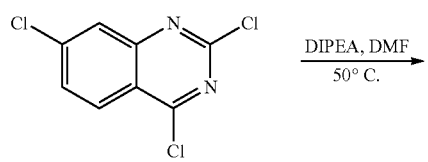

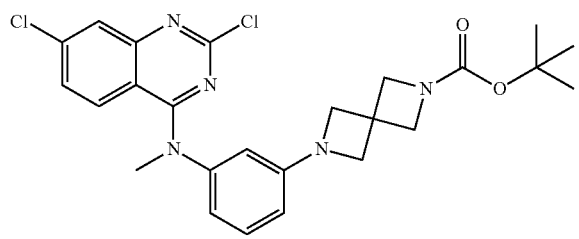

Synthesis of tert-butyl 6-[3-[(2,7-dichloroquinazolin-4-yl)-methyl-amino]phenyl]-2,6-diazaspiro[3.3]heptane-2-carboxylate: A solution of tert-butyl 6-[3-(methylamino)phenyl]-2,6-diazaspiro[3.3]heptane-2-carboxylate (239 mg, 0.79 mmol) and 2,4,7-trichloroquinazoline (184 mg, 0.79 mmol) in DMF (2.0 m) was treated with DIPEA (0.34 mL, 2.0 mmol) and warmed to 50° C. After 45 minutes, the reaction was cooled and diluted with water. The mixture was extracted three times with EtOAc and the combined organics were dried over Na$_2$SO$_4$, filtered and evaporated. The residue was purified via normal phase flash chromatography using 40% EtOAc/Hexanes to provide product: $^1$H NMR (400 MHz, DMSO-d$_6$) δ 7.72 (d, J=2.2 Hz, 1H), 7.26 (dd, J=8.8, 7.8 Hz, 1H), 7.19 (dd, J=9.2, 2.3 Hz, 1H), 6.90 (d, J=9.2 Hz, 1H), 6.66-6.61 (m, 1H), 6.49-6.43 (m, 2H), 4.00 (s, 4H), 3.91 (s, 4H), 3.51 (s, 3H), 1.37 (s, 9H); ES/MS m/z: 502.2/500.3.

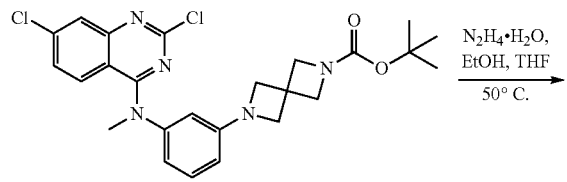

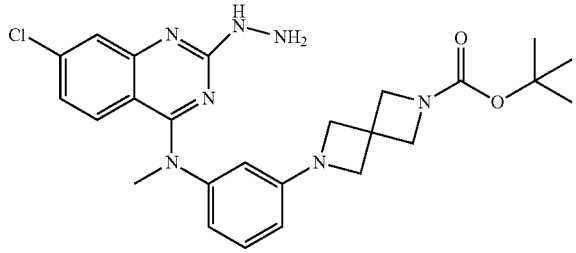

Synthesis of tert-butyl 6-[3-[(7-chloro-2-hydrazino-quinazolin-4-yl)-methyl-amino]phenyl]-2,6-diazaspiro[3.3]heptane-2-carboxylate: A solution of tert-butyl 6-[3-[(2,7-dichloroquinazolin-4-yl)-methyl-amino]phenyl]-2,6-diazaspiro[3.3]heptane-2-carboxylate (331 mg, 0.63 mmol) in EtOH (14 ml) and THF (6.9 ml) was treated with hydrazine hydrate (0.31 mL, 6.3 mmol). This was stirred at ambient temperature for 90 minutes and then warmed to 50° C. for 21 hours. The volatiles were evaporated, and the residue triturated with heptanes to give product: ES/MS m/z: 496.4.

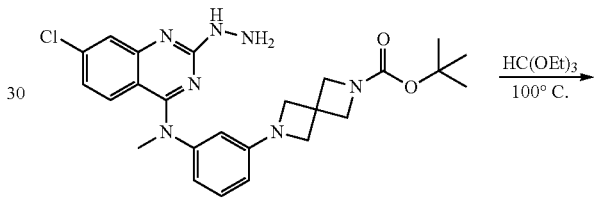

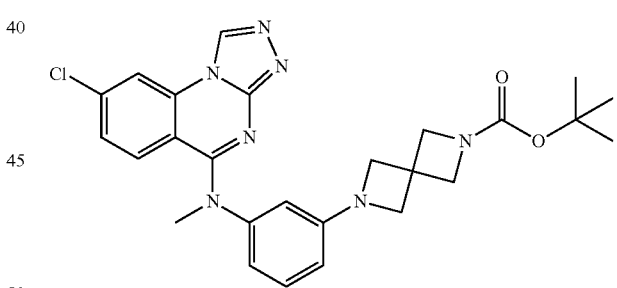

Synthesis of tert-butyl 6-[3-[(8-chloro-[1,2,4]triazolo[4,3-a]quinazolin-5-yl)-methyl-amino]phenyl]-2,6-diazaspiro[3.3]heptane-2-carboxylate: tert-butyl 6-[3-[(7-chloro-2-hydrazino-quinazolin-4-yl)-methyl-amino]phenyl]-2,6-diazaspiro[3.3]heptane-2-carboxylate (312 mg, 0.63 mmol) was suspended in triethyl orthoformate (5.0 mL, 30 mmol) and heated to 100° C. for 1 hour. The volatiles were evaporated. The residue was purified via normal phase flash chromatography using 80% (3:1 EtOAc:EtOH)/Heptanes to provide product. A small portion was purified via prep-HPLC to give the title compound: $^1$H NMR (400 MHz, DMSO-d$_6$) δ 9.75 (s, 1H), 8.60 (d, J=2.1 Hz, 1H), 7.42 (dd, J=9.1, 2.1 Hz, 1H), 7.28-7.20 (m, 2H), 6.63 (dd, J=7.8, 2.0 Hz, 1H), 6.49-6.38 (m, 2H), 4.00 (s, 4H), 3.90 (s, 4H), 3.58 (s, 3H), 1.37 (s, 9H); LCMS(m/z) 506.2.

Example 301. N-(3-(2,6-diazaspiro[3.3]heptan-2-yl)phenyl)-8-chloro-N-methyl-[1,2,4]triazolo[4,3-a]quinazolin-5-amine

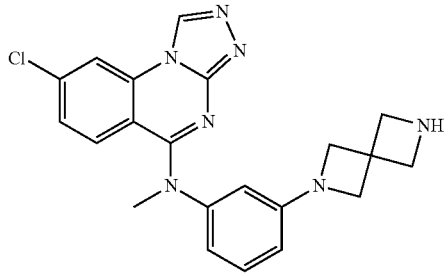 [SMILES: CN(c1cccc(N2CC3(CNC3)C2)c1)c1nc2nncn2c2cc(Cl)ccc12]

A solution of tert-butyl 6-[3-[(8-chloro-[1,2,4]triazolo[4,3-a]quinazolin-5-yl)-methyl-amino]phenyl]-2,6-diazaspiro[3.3]heptane-2-carboxylate (Example 300, 80 mg, 0.14 mmol) in DCM (3.0 mL) was treated with 85% aqueous phosphoric acid (0.029 mL, 0.43 mmol) and stirred at ambient temperature. After 30 minutes the reaction was evaporated, and the residue purified via prep-HPLC to afford the title compound: $^1$H NMR (400 MHz, DMSO-$d_6$) δ 9.66 (s, 1H), 8.56 (d, J=2.1 Hz, 1H), 7.34 (dd, J=9.0, 2.1 Hz, 1H), 7.27 (d, J=9.0 Hz, 1H), 7.20 (t, J=8.0 Hz, 1H), 6.65-6.57 (m, 1H), 6.43 (t, J=2.2 Hz, 1H), 6.41-6.37 (m, 1H), 4.13 (t, J=6.1 Hz, 4H), 3.93 (s, 4H), 3.53 (s, 3H); LCMS(m/z) 406.1.

Example 302. (6-(3-((8-chloro-[1,2,4]triazolo[4,3-a]quinazolin-5-yl)(methyl)amino)phenyl)-2,6-diazaspiro[3.3]heptan-2-yl)(cyclopropyl)methanone

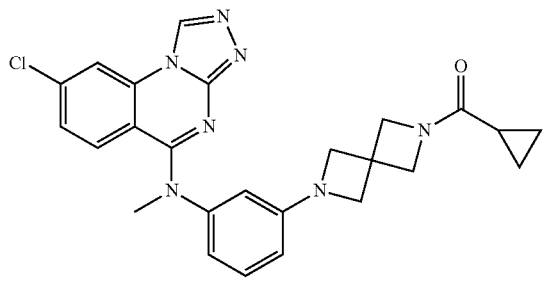 [SMILES: CN(c1cccc(N2CC3(CN(C(=O)C4CC4)C3)C2)c1)c1nc2nncn2c2cc(Cl)ccc12]

A suspension of 8-chloro-N-[3-(2,6-diazaspiro[3.3]heptan-2-yl)phenyl]-N-methyl-[1,2,4]triazolo[4,3-a]quinazolin-5-amine (Example 301, 13 mg, 0.023 mmol) in DCM (1.0 mL) was treated with cyclopropanecarboxylic acid chloride (0.003 mL, 0.028 mmol) and TEA (0.010 mL, 0.068 mmol). The mixture was stirred at ambient temperature for 80 minutes and then evaporated. The residue was purified via prep-HPLC to give the title compound: $^1$H NMR (400 MHz, DMSO-$d_6$) δ 9.74 (s, 1H), 8.60 (d, J=2.1 Hz, 1H), 7.42 (dd, J=9.0, 2.1 Hz, 1H), 7.29-7.20 (m, 2H), 6.63 (d, J=7.9 Hz, 1H), 6.48-6.46 (m, 1H), 6.46-6.42 (m, 1H), 4.41 (s, 2H), 4.01 (s, 2H), 3.98-3.90 (m, 4H), 3.58 (s, 3H), 1.54-1.46 (m, 1H), 0.74-0.63 (m, 4H); LCMS(m/z) 474.2.

Example 303. 8-chloro-N-(3-(6-(cyclopropylsulfonyl)-2,6-diazaspiro[3.3]heptan-2-yl)phenyl)-N-methyl-[1,2,4]triazolo[4,3-a]quinazolin-5-amine

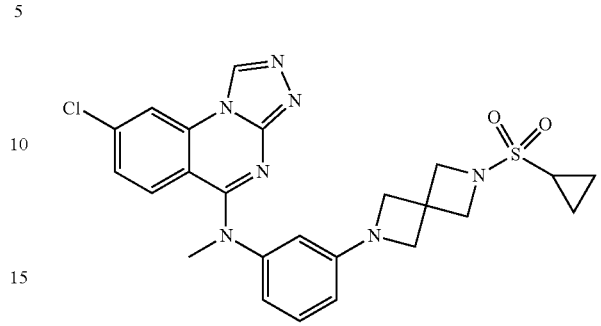

A suspension of 8-chloro-N-[3-(2,6-diazaspiro[3.3]heptan-2-yl)phenyl]-N-methyl-[1,2,4]triazolo[4,3-a]quinazolin-5-amine (Example 301, 15 mg, 0.026 mmol) in DCM (1.2 mL) was treated with cyclopropanesulfonyl chloride (0.003 mL, 0.031 mmol) and TEA (0.011 mL, 0.078 mmol). The mixture was stirred at ambient temperature for 90 minutes and then evaporated. The residue was purified via prep-HPLC to give the title compound: $^1$H NMR (400 MHz, DMSO-$d_6$) δ 9.76 (s, 1H), 8.61 (d, J=2.1 Hz, 1H), 7.42 (dd, J=9.0, 2.1 Hz, 1H), 7.28-7.21 (m, 2H), 6.68-6.61 (m, 1H), 6.49-6.46 (m, 1H), 6.46-6.43 (m, 1H), 4.08 (s, 4H), 3.95 (s, 4H), 3.58 (s, 3H), 2.79-2.69 (m, 1H), 1.05-0.98 (m, 2H), 0.96-0.89 (m, 2H); LCMS(m/z) 510.2.

Example 304. 8-chloro-N-methyl-N-(3-(6-(2,2,2-trifluoroethyl)-2,6-diazaspiro[3.3]heptan-2-yl)phenyl)-[1,2,4]triazolo[4,3-a]quinazolin-5-amine

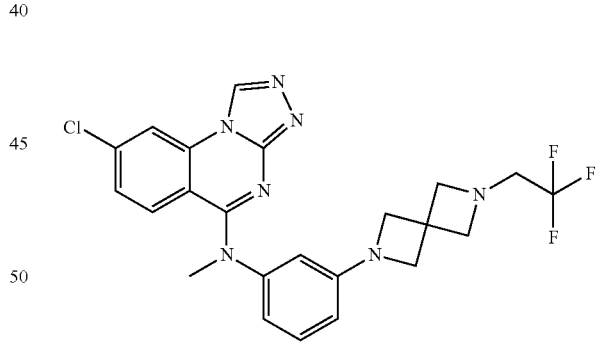

A solution of 8-chloro-N-[3-(2,6-diazaspiro[3.3]heptan-2-yl)phenyl]-N-methyl-[1,2,4]triazolo[4,3-a]quinazolin-5-amine (13 mg, 0.022 mmol) in ACN (1.0 mL) was treated with 2,2,2-Trifluoroethyl trifluoromethanesulfonate (0.004 mL, 0.026 mmol) and DIPEA (0.011 mL, 0.066 mmol). The mixture was stirred at ambient temperature for 2 hours and then evaporated. The residue was purified via prep-HPLC to give product: $^1$H NMR (400 MHz, Acetone-$d_6$) δ 9.49 (s, 1H), 8.43 (d, J=2.0 Hz, 1H), 7.45 (d, J=9.0 Hz, 1H), 7.31 (dd, J=9.0, 2.1 Hz, 1H), 7.24 (t, J=8.0 Hz, 1H), 6.68-6.61 (m, 1H), 6.49 (t, J=2.1 Hz, 1H), 6.47-6.42 (m, 1H), 3.93 (s, 4H), 3.66 (s, 4H), 3.63 (s, 3H), 3.23 (q, J=9.8 Hz, 2H); LCMS (m/z) 488.1.

Example 305. 8-(but-1-yn-1-yl)-N-methyl-N-phenyl-[1,2,4]triazolo[4,3-a]quinazolin-5-amine

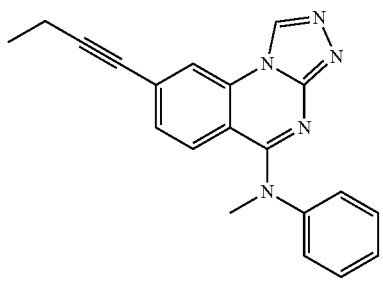

A vigorously stirred mixture of 8-bromo-N-methyl-N-phenyl-[1,2,4]triazolo[4,3-a]quinazolin-5-amine (Example 28, 10.0 mg, 28.2 μmol), but-1-yne (36.7 mg, 678 μmol), triethylamine (100 μL, 717 μmol), copper(I) iodide (5.4 mg, 28 μmol), 2-dicyclohexylphosphino-2',4',6'-triisopropylbiphenyl (9.1 mg, 19 μmol), tris(dibenzylideneacetone)palladium(0) (5.2 mg, 5.7 μmol), and 1-methylpyrrolidin-2-one (0.5 mL) was heated to 75° C. After 4 h, the resulting mixture was cooled to room temperature and was purified by reverse phase preparative HPLC (0.1% trifluoroacetic acid in acetonitrile/water) to give the title compound: $^1$H NMR (400 MHz, Acetone-$d_6$) δ 8.30 (s, 1H), 7.51-7.27 (m, 7H), 7.19 (d, J=8.5 Hz, 1H), 2.49 (q, J=7.5 Hz, 2H), 1.22 (t, J=7.5 Hz, 3H); LCMS(m/z) 328.3.

Example 306. (E)-N-methyl-N-phenyl-8-(prop-1-en-1-yl)-[1,2,4]triazolo[4,3-a]quinazolin-5-amine

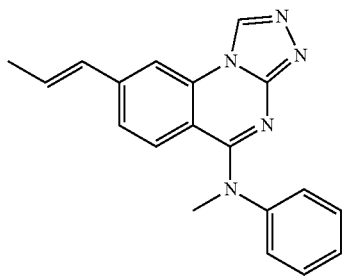

A vigorously stirred mixture of 8-bromo-N-methyl-N-phenyl-[1,2,4]triazolo[4,3-a]quinazolin-5-amine (Example 28, 10.0 mg, 28.2 μmol), potassium trans-1-propenyltrifluoroborate (16.7 mg, 113 μmol), chloro(2-dicyclohexylphosphino-2',4',6'-triisopropyl-1,1'-biphenyl)[2-(2'-amino-1,1'-biphenyl)]palladium(II) (4.4 mg, 5.7 μmol), and 1,4-dioxane (0.5 mL) was heated to 100° C. After 10 min, the resulting mixture was cooled to room temperature and was concentrated under reduced pressure. The residue was purified by reverse phase preparative HPLC (0.1% trifluoroacetic acid in acetonitrile/water) to give the title compound: $^1$H NMR (400 MHz, Acetone-$d_6$) δ 9.58 (s, 1H), 8.36 (d, J=1.7 Hz, 1H), 7.56-7.48 (m, 2H), 7.48-7.38 (m, 3H), 7.32 (dd, J=8.8, 1.6 Hz, 1H), 7.21 (d, J=8.8 Hz, 1H), 6.73 (dq, J=15.6, 6.6 Hz, 1H), 6.57 (dd, J=15.9, 1.9 Hz, 1H), 3.72 (s, 3H), 1.94 (dd, J=6.6, 1.6 Hz, 3H); LCMS(m/z) 316.3.

Example 307. 8-ethynyl-N-methyl-N-phenyl-[1,2,4]triazolo[4,3-a]quinazolin-5-amine

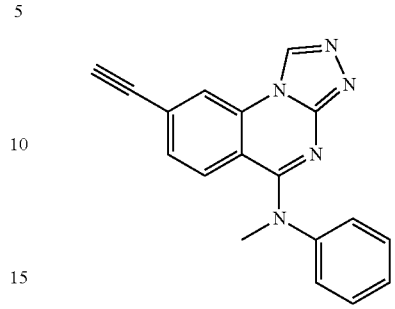

Example 307 was synthesized in a manner similar to Example 306 except using potassium ethynyltrifluoroborate instead of potassium trans-1-propenyltrifluoroborate. $^1$H NMR (400 MHz, Acetone-$d_6$) δ 9.51 (s, 1H), 8.42 (s, 1H), 7.51-7.24 (m, 8H), 4.07 (s, 1H), 3.65 (s, 3H); LCMS(m/z) 300.3.

Example 308. N-(3-bromophenyl)-8-chloro-N-methyl-[1,2,4]triazolo[4,3-a]quinazolin-5-amine

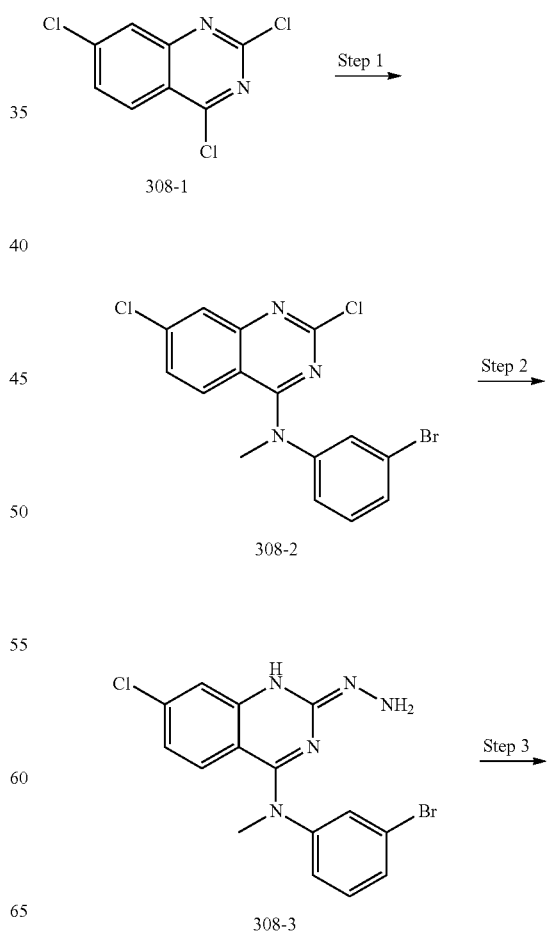

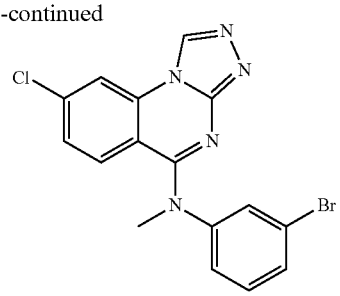

Step 1: Sodium hydride (60% wt dispersion in mineral oil, 382 mg, 9.97 mmol) was added to a vigorously stirred mixture of 2,4,7-trichloroquinazoline (Compound 308-1, 1.94 g, 8.31 mmol) and 3-bromo-N-methylaniline (1.11 mL, 8.72 mmol) in N,N-dimethylformamide (30 mL) at 0° C. After 60 min, sodium hydride (60% wt dispersion in mineral oil, 260 mg, 6.79 mmol) was added. After 2 h, the resulting mixture was poured into a mixture of saturated aqueous ammonium chloride solution (50 mL), brine (5100 mL), and ice (75 g), and the resulting suspension was swirled vigorously until all of the ice melted. The resulting suspension was filtered, and the filter cake was washed sequentially with ice-cold water (2×25 mL) and hexanes (25 mL) to give Compound 308-2.

Step 2: Hydrazine monohydrate (3.22 mL, 66.5 mmol) was added via syringe to a vigorously stirred solution of 308-2 (3.18 g, 8.31 mmol) in ethanol (60 mL) and tetrahydrofuran (40 mL) at room temperature. After 35 min, hydrazine monohydrate (6.00 mL, 123 mmol) was added via syringe. After 19 h, water (100 mL), brine (100 mL), ethyl acetate (150 mL), and tetrahydrofuran (75 mL) were added sequentially. The biphasic mixture was agitated, and the layers were separated. The aqueous layer was extracted with a mixture of ethyl acetate (200 mL) and tetrahydrofuran (100 mL). The combined organic layers were washed with a mixture of water (235 mL) and brine (115 mL), were dried over anhydrous sodium sulfate, were filtered, and were concentrated under reduced pressure to give Compound 308-3.

Step 3: A vigorously stirred mixture of Compound 308-3 (3.15 g, 8.31 mmol) and triethyl orthoformate (60 mL) was heated to 120° C. After 212 min, the resulting mixture was heated to 150° C. After 90 min, the resulting mixture was cooled to room temperature and was concentrated under reduced pressure until the volume of the resulting suspensions was approximately 10 mL. Hexanes (70 mL) were added, and the resulting crude material was triturated. The resulting suspension was cooled to 0° C. After 20 min, the resulting suspension was filtered, and the filter cake was washed sequentially with a mixture of hexanes and diethyl ether (4:1 v:v, 60 mL) and hexanes (75 mL) and was dried under reduced pressure to give the title compound: $^1$H NMR (400 MHz, DMSO-d$_6$) δ 9.67 (s, 1H), 8.58 (d, J=2.1 Hz, 1H), 7.63 (q, J=1.5 Hz, 1H), 7.48-7.37 (m, 2H), 7.35-7.26 (m, 3H), 3.54 (s, 3H); LCMS(m/z) 388.1.

Example 309. (E)-7-fluoro-N-(3-fluorophenyl)-N-methyl-8-(prop-1-en-1-yl)-[1,2,4]triazolo[4,3-a]quinazolin-5-amine

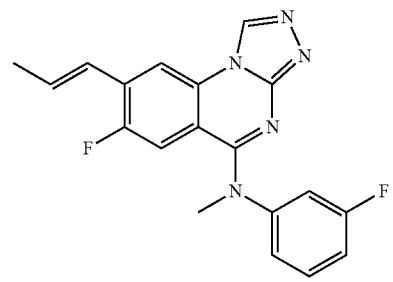 [SMILES: C/C=C/c1cc2c(cc1F)c(N(C)c1cccc(F)c1)nc1nncn12]

Example 309 was synthesized in a manner similar to Example 306, except using 8-bromo-7-fluoro-N-(3-fluorophenyl)-N-methyl-[1,2,4]triazolo[4,3-a]quinazolin-5-amine (Example 215) instead of 8-bromo-N-methyl-N-phenyl-[1,2,4]triazolo[4,3-a]quinazolin-5-amine (Example 28) and using potassium ethynyltrifluoroborate instead of potassium trans-1-propenyltrifluoroborate. $^1$H NMR (400 MHz, Acetone-d$_6$) δ 9.58 (s, 1H), 8.58 (d, J=6.6 Hz, 1H), 7.55 (td, J=8.2, 6.5 Hz, 1H), 7.34-7.25 (m, 2H), 7.18 (tdd, J=8.4, 2.5, 0.9 Hz, 1H), 6.98 (d, J=12.1 Hz, 1H), 6.86 (dq, J=15.9, 6.7 Hz, 1H), 6.70-6.56 (m, 1H), 3.70 (s, 3H), 1.99 (dd, J=6.7, 1.7 Hz, 3H); LCMS(m/z) 352.3.

Example 310. (Z)—N-methyl-N-phenyl-8-(prop-1-en-1-yl)-[1,2,4]triazolo[4,3-a]quinazolin-5-amine

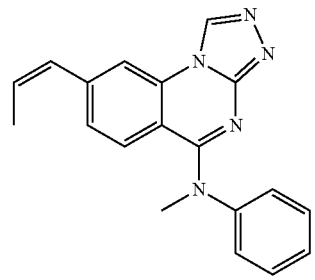 [SMILES: C/C=C\c1ccc2c(N(C)c3ccccc3)nc3nncn3c2c1]

Example 310 was synthesized in a manner similar to Example 306, except using cis-1-propen-1-ylboronic acid instead of potassium trans-1-propenyltrifluoroborate. $^1$H NMR (400 MHz, Acetone-d$_6$) δ 9.56 (s, 1H), 8.24 (d, J=1.5 Hz, 1H), 7.55-7.46 (m, 2H), 7.46-7.36 (m, 3H), 7.30 (d, J=8.7 Hz, 1H), 7.24 (dd, J=8.8, 1.6 Hz, 1H), 6.56 (dd, J=11.7, 2.0 Hz, 1H), 6.09 (dq, J=11.7, 7.3 Hz, 1H), 3.71 (s, 3H), 1.96 (dd, J=7.3, 1.9 Hz, 3H); LCMS(m/z) 316.3.

Example 311. (E)-8-(but-2-en-2-yl)-N-methyl-N-phenyl-[1,2,4]triazolo[4,3-a]quinazolin-5-amine

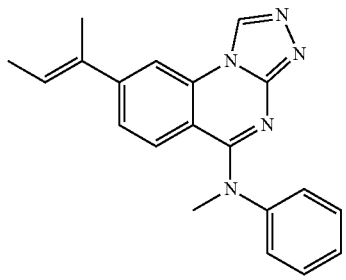

Example 311 was synthesized in a manner similar to Example 306, except using potassium (2Z)-2-buten-2-yltrifluoroborate instead of potassium trans-1-propenyltrifluoroborate. $^1$H NMR (400 MHz, Acetone-$d_6$) δ 9.67 (s, 1H), 8.35 (d, J=1.9 Hz, 1H), 7.59-7.49 (m, 2H), 7.48-7.41 (m, 3H), 7.38 (dd, J=8.9, 1.9 Hz, 1H), 7.22 (d, J=8.9 Hz, 1H), 6.29 (q, J=6.9 Hz, 1H), 3.72 (s, 3H), 2.11 (t, J=1.3 Hz, 3H), 1.86 (dq, J=6.9, 1.1 Hz, 3H); LCMS(m/z) 330.3.

Example 312. 8-chloro-N-(4'-isopropyl-[1,1'-biphenyl]-3-yl)-N-methyl-[1,2,4]triazolo[4,3-a]quinazolin-5-amine

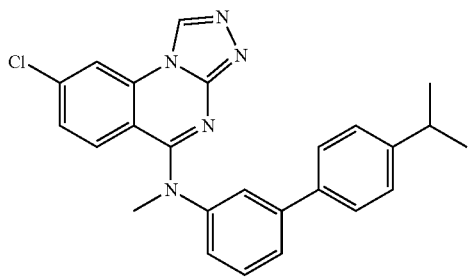

A vigorously stirred mixture of Example 308 (5.0 mg, 13 μmol), (4-isopropylphenyl)boronic acid (8.4 mg, 52 μmol), [1,1'-bis(diphenylphosphino)ferrocene]dichloropalladium(II) (1.9 mg, 2.6 μmol), aqueous sodium carbonate solution (2.0 M, 97 μL, 190 μmol), and 1,4-dioxane (0.5 mL) was heated to 100° C. After 5 min, the resulting mixture was cooled to room temperature and was concentrated under reduced pressure. The residue was purified by reverse phase preparative HPLC (0.1% trifluoroacetic acid in acetonitrile/water) to give the title compound: $^1$H NMR (400 MHz, Acetone-$d_6$) δ 9.44 (s, 1H), 8.39 (d, J=2.1 Hz, 1H), 7.66 (t, J=2.0 Hz, 1H), 7.61 (dt, J=7.9, 1.4 Hz, 1H), 7.59-7.47 (m, 4H), 7.39-7.29 (m, 3H), 7.26 (dd, J=9.0, 2.1 Hz, 1H), 3.70 (s, 3H), 3.08-2.75 (m, 1H), 1.26 (d, J=6.9 Hz, 6H); LCMS (m/z) 428.3.

Example 313. 8-chloro-N-(4'-cyclopropyl-[1,1'-biphenyl]-3-yl)-N-methyl-[1,2,4]triazolo[4,3-a]quinazolin-5-amine

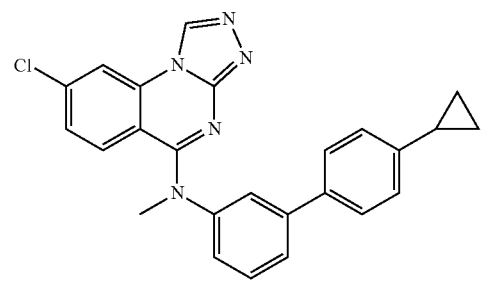

Example 313 was synthesized in a manner similar to Example 312, except using (4-cyclopropylphenyl)boronic acid instead of (4-isopropylphenyl)boronic acid. $^1$H NMR (400 MHz, Acetone-$d_6$) δ 9.49 (s, 1H), 8.43 (d, J=2.1 Hz, 1H), 7.67 (t, J=2.0 Hz, 1H), 7.63 (ddd, J=7.8, 1.8, 1.1 Hz, 1H), 7.57-7.45 (m, 4H), 7.36 (ddd, J=7.9, 2.2, 1.1 Hz, 1H), 7.29 (dd, J=9.0, 2.1 Hz, 1H), 7.18-7.06 (m, 2H), 3.72 (s, 3H), 2.03-1.85 (m, 1H), 1.03-0.93 (m, 2H), 0.77-0.64 (m, 2H); LCMS(m/z) 426.3.

Example 314. 8-chloro-N-(4'-(difluoromethyl)-[1,1'-biphenyl]-3-yl)-N-methyl-[1,2,4]triazolo[4,3-a]quinazolin-5-amine

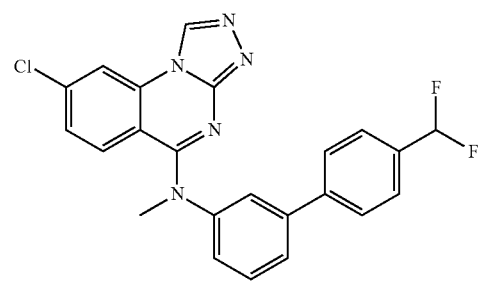

Example 314 was synthesized in a manner similar to Example 312, except using [4-(difluoromethyl)phenyl]boronic acid instead of (4-isopropylphenyl)boronic acid. $^1$H NMR (400 MHz, Acetone-$d_6$) δ 9.47 (s, 1H), 8.42 (d, J=2.1 Hz, 1H), 7.83-7.74 (m, 3H), 7.67 (dd, J=13.3, 7.8 Hz, 3H), 7.58 (t, J=7.9 Hz, 1H), 7.52 (d, J=9.0 Hz, 1H), 7.43 (d, J=8.0 Hz, 1H), 7.29 (dd, J=9.0, 2.1 Hz, 1H), 6.95 (t, J=56.1 Hz, 1H), 3.72 (s, 3H); LCMS(m/z) 436.3.

Example 315. 8-chloro-N-methyl-N-(2',4',6'-trimethyl-[1,1'-biphenyl]-3-yl)-[1,2,4]triazolo[4,3-a]quinazolin-5-amine

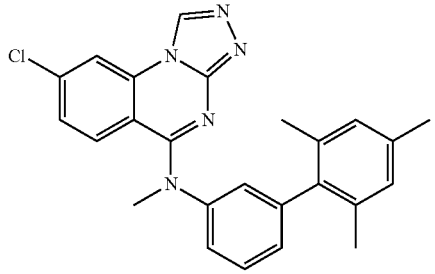

Example 315 was synthesized in a manner similar to Example 312, except using (2,4,6-trimethylphenyl)boronic acid instead of (4-isopropylphenyl)boronic acid. $^1$H NMR (400 MHz, Acetone-d$_6$) δ 9.51 (s, 1H), 8.46 (d, J=2.1 Hz, 1H), 7.64 (t, J=7.8 Hz, 1H), 7.58-7.47 (m, 2H), 7.39 (dd, J=9.0, 2.1 Hz, 1H), 7.16 (dt, J=7.6, 1.3 Hz, 1H), 7.04 (t, J=1.9 Hz, 1H), 6.88 (s, 2H), 3.73 (s, 3H), 2.25 (s, 3H), 1.89 (s, 6H); LCMS(m/z) 428.3.

Example 316. N-methyl-8-(2-methylprop-1-en-1-yl)-N-phenyl-[1,2,4]triazolo[4,3-a]quinazolin-5-amine

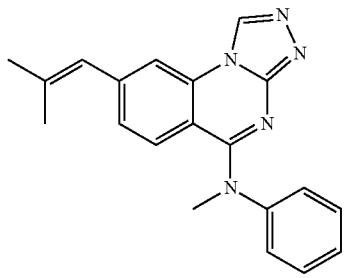

Example 316 was synthesized in a manner similar to Example 306 except using 4,4,5,5-tetramethyl-2-(2-methylprop-1-en-1-yl)-1,3,2-dioxaborolane instead of potassium trans-1-propenyltrifluoroborate. H NMR (400 MHz, Acetone-d$_6$) δ 9.56 (s, 1H), 8.17 (d, J=1.6 Hz, 1H), 7.56-7.47 (m, 2H), 7.47-7.37 (m, 3H), 7.26 (d, J=8.7 Hz, 1H), 7.17 (dd, J=8.8, 1.6 Hz, 1H), 6.41 (s, 1H), 3.71 (s, 3H), 1.97 (d, J=1.5 Hz, 3H), 1.96 (d, J=1.4 Hz, 3H); LCMS(m/z) 330.3.

Example 317. N-(3-(6-(tert-butyl)pyridin-3-yl)phenyl)-8-chloro-N-methyl-[1,2,4]triazolo[4,3-a]quinazolin-5-amine

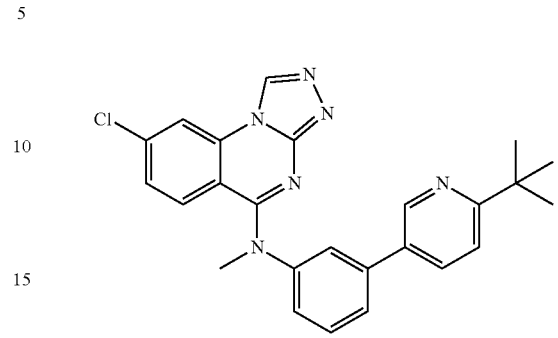

Example 317 was synthesized in a manner similar to Example 337, except using 5-bromo-2-tert-butyl-pyridine instead of 2-bromo-5-cyclopropylpyrazine and using chloro (2-dicyclohexylphosphino-2',4',6'-triisopropyl-1,1'-biphenyl)[2-(2'-amino-1,1'-biphenyl)]palladium(II) instead of [1,1'-bis(diphenylphosphino)ferrocene]dichloropalladium (II). $^1$H NMR (400 MHz, Acetone-d$_6$) δ 9.47 (s, 1H), 8.75 (d, J=2.6 Hz, 1H), 8.42 (d, J=2.2 Hz, 1H), 7.96 (dd, J=8.3, 2.6 Hz, 1H), 7.77-7.72 (m, 1H), 7.68-7.63 (m, 1H), 7.59 (t, J=8.0 Hz, 1H), 7.55-7.47 (m, 2H), 7.47-7.41 (m, 1H), 7.29 (dd, J=8.9, 2.2 Hz, 1H), 3.72 (s, 3H), 1.37 (s, 9H); LCMS (m/z) 443.3.

Example 318. N-(3-(5-(tert-butyl)pyridin-2-yl)phenyl)-8-chloro-N-methyl-[1,2,4]triazolo[4,3-a]quinazolin-5-amine

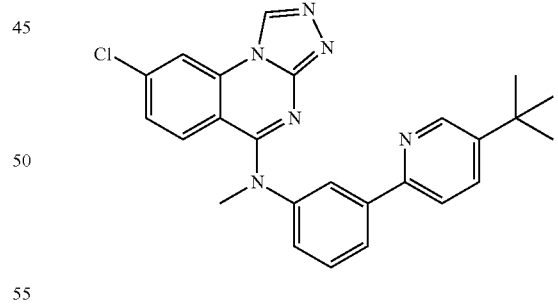

Example 318 was synthesized in a manner similar to Example 337, except using 5-tert-butyl-2-chloro-pyridine instead of 2-bromo-5-cyclopropylpyrazine and using chloro (2-dicyclohexylphosphino-2',4',6'-triisopropyl-1,1'-biphenyl)[2-(2'-amino-1,1'-biphenyl)]palladium(II) instead of [1,1'-bis(diphenylphosphino)ferrocene]dichloropalladium (II). $^1$H NMR (400 MHz, Acetone-d$_6$) δ 9.51 (s, 1H), 8.75 (s, 1H), 8.44 (d, J=2.3 Hz, 1H), 8.15 (t, J=2.1 Hz, 1H), 8.12 (d, J=8.1 Hz, 1H), 7.94-7.83 (m, 2H), 7.58 (t, J=7.8 Hz, 1H), 7.50 (d, J=9.1 Hz, 1H), 7.47-7.33 (m, 1H), 7.30 (dd, J=8.9, 2.2 Hz, 1H), 3.74 (s, 3H), 1.39 (s, 9H); LCMS(m/z) 443.3.

Example 319. N-(3-(5-(tert-butyl)pyrimidin-2-yl)phenyl)-8-chloro-N-methyl-[1,2,4]triazolo[4,3-a]quinazolin-5-amine

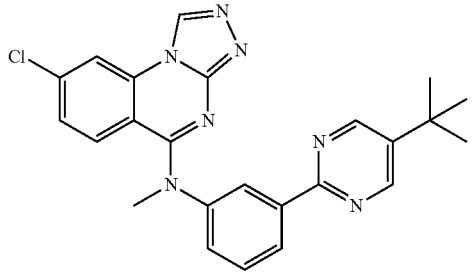

Example 319 was synthesized in a manner similar to Example 337, except using 2-bromo-5-tert-butyl-pyrimidine instead of 2-bromo-5-cyclopropylpyrazine and using chloro (2-dicyclohexylphosphino-2',4',6'-triisopropyl-1,1'-biphenyl)[2-(2'-amino-1,1'-biphenyl)]palladium(II) instead of [1,1'-bis(diphenylphosphino)ferrocene]dichloropalladium (II). $^1$H NMR (400 MHz, Acetone-$d_6$) δ 9.46 (s, 1H), 8.76 (d, J=5.3 Hz, 1H), 8.48-8.40 (m, 3H), 7.64-7.41 (m, 4H), 7.28 (dd, J=9.0, 2.1 Hz, 1H), 3.71 (s, 3H), 1.40 (s, 9H); LCMS(m/z) 444.3.

Example 321. N-(3-(6-(tert-butyl)pyridazin-3-yl)phenyl)-8-chloro-N-methyl-[1,2,4]triazolo[4,3-a]quinazolin-5-amine

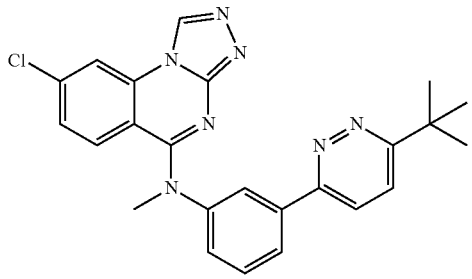

Example 321 was synthesized in a manner similar to Example 337, except using 3-bromo-6-tert-butyl-pyridazine instead of 2-bromo-5-cyclopropylpyrazine and using chloro (2-dicyclohexylphosphino-2',4',6'-triisopropyl-1,1'-biphenyl)[2-(2'-amino-1,1'-biphenyl)]palladium(II) instead of [1,1'-bis(diphenylphosphino)ferrocene]dichloropalladium (II). $^1$H NMR (400 MHz, Acetone-$d_6$) δ 9.53 (s, 1H), 8.46 (d, J=2.1 Hz, 1H), 8.23 (t, J=2.0 Hz, 1H), 8.22-8.15 (m, 1H), 8.08 (d, J=9.0 Hz, 1H), 7.80 (d, J=9.0 Hz, 1H), 7.65 (t, J=7.9 Hz, 1H), 7.58-7.51 (m, 2H), 7.31 (dd, J=9.0, 2.1 Hz, 1H), 3.76 (s, 3H), 1.47 (s, 9H); LCMS(m/z) 444.3.

Example 320. N-(3-(2-(tert-butyl)pyrimidin-5-yl)phenyl)-8-chloro-N-methyl-[1,2,4]triazolo[4,3-a]quinazolin-5-amine

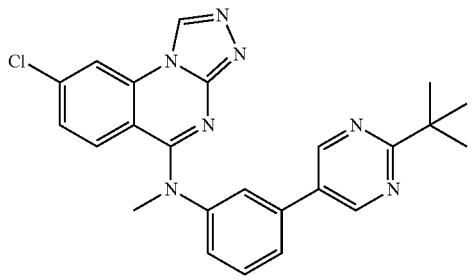

Example 320 was synthesized in a manner similar to Example 337, except using 5-bromo-2-tert-butyl-pyrimidine instead of 2-bromo-5-cyclopropylpyrazine and using chloro (2-dicyclohexylphosphino-2',4',6'-triisopropyl-1,1'-biphenyl)[2-(2'-amino-1,1'-biphenyl)]palladium(II) instead of [1,1'-bis(diphenylphosphino)ferrocene]dichloropalladium (II). $^1$H NMR (400 MHz, Acetone-$d_6$) δ 9.54 (s, 1H), 8.94 (s, 2H), 8.47 (d, J=2.2 Hz, 1H), 7.84 (t, J=2.0 Hz, 1H), 7.79-7.72 (m, 1H), 7.66 (t, J=7.8 Hz, 1H), 7.58-7.46 (m, 2H), 7.32 (dd, J=9.0, 2.1 Hz, 1H), 3.76 (s, 3H), 1.40 (s, 9H); LCMS(m/z) 444.3.

Example 322. N-(3-(5-(tert-butyl)pyrazin-2-yl)phenyl)-8-chloro-N-methyl-[1,2,4]triazolo[4,3-a]quinazolin-5-amine

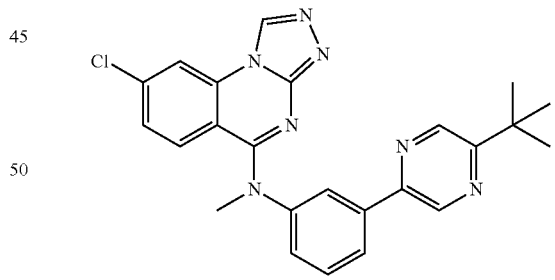

Example 322 was synthesized in a manner similar to Example 337, except using 2-tert-butyl-5-chloro-pyrazine instead of 2-bromo-5-cyclopropylpyrazine and using chloro (2-dicyclohexylphosphino-2',4',6'-triisopropyl-1,1'-biphenyl)[2-(2'-amino-1,1'-biphenyl)]palladium(II) instead of [1,1'-bis(diphenylphosphino)ferrocene]dichloropalladium (II). $^1$H NMR (400 MHz, Acetone-$d_6$) δ 9.50 (s, 1H), 9.06 (d, J=1.6 Hz, 1H), 8.75 (d, J=1.6 Hz, 1H), 8.43 (d, J=2.1 Hz, 1H), 8.15 (t, J=2.0 Hz, 1H), 8.12 (dt, J=7.7, 1.3 Hz, 1H), 7.62 (t, J=7.9 Hz, 1H), 7.55-7.46 (m, 2H), 7.29 (dd, J=9.0, 2.1 Hz, 1H), 3.73 (s, 3H), 1.42 (s, 9H); LCMS(m/z) 444.3.

Example 323. (E)-8-(but-1-en-1-yl)-N-methyl-N-phenyl-[1,2,4]triazolo[4,3-a]quinazolin-5-amine

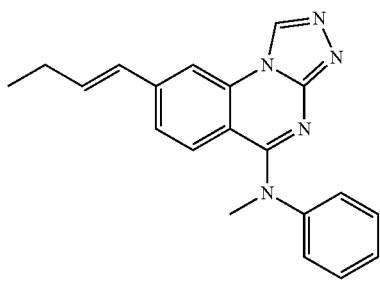 [SMILES: CC/C=C/c1ccc2c(N(C)c3ccccc3)nc3nncn3c2c1]

Example 323 was synthesized in a manner similar to Example 306, except using [(E)-but-1-enyl]boronic acid instead of potassium trans-1-propenyltrifluoroborate. $^1$H NMR (400 MHz, Acetone-d$_6$) δ 9.56 (s, 1H), 8.38 (d, J=1.7 Hz, 1H), 7.58-7.47 (m, 2H), 7.47-7.38 (m, 3H), 7.34 (dd, J=8.8, 1.7 Hz, 1H), 7.22 (d, J=8.8 Hz, 1H), 6.77 (dt, J=16.0, 6.6 Hz, 1H), 6.55 (d, J=15.9 Hz, 1H), 3.71 (s, 3H), 2.31 (pd, J=7.5, 1.6 Hz, 2H), 1.10 (t, J=7.4 Hz, 3H); LCMS(m/z) 330.3.

Example 324. 8-(but-1-yn-1-yl)-7-fluoro-N-(3-fluorophenyl)-N-methyl-[1,2,4]triazolo[4,3-a]quinazolin-5-amine

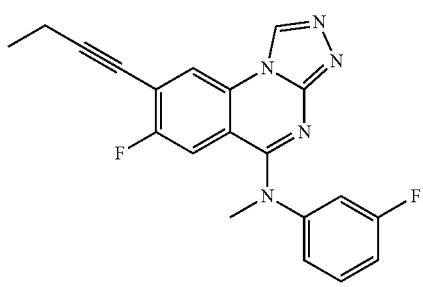 [SMILES: CCC#Cc1cc2c(cc1F)c(N(C)c1cccc(F)c1)nc1nncn12]

Example 324 was synthesized in a manner similar to Example 305, except using 8-bromo-7-fluoro-N-(3-fluorophenyl)-N-methyl-[1,2,4]triazolo[4,3-a]quinazolin-5-amine (Example 215) instead of 8-bromo-N-methyl-N-phenyl-[1,2,4]triazolo[4,3-a]quinazolin-5-amine. $^1$H NMR (400 MHz, Acetone-d$_6$) δ 9.61 (s, 1H), 8.49 (d, J=6.2 Hz, 1H), 7.55 (td, J=8.1, 6.5 Hz, 1H), 7.37-7.26 (m, 2H), 7.22-7.17 (m, 1H), 7.05 (d, J=10.7 Hz, 1H), 3.71 (s, 3H), 2.56 (q, J=7.5 Hz, 2H), 1.25 (t, J=7.5 Hz, 3H); LCMS(m/z) 364.3.

Example 325. 8-(cyclopent-1-en-1-yl)-N-methyl-N-phenyl-[1,2,4]triazolo[4,3-a]quinazolin-5-amine

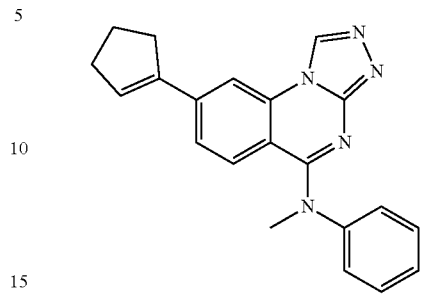

Example 325 was synthesized in a manner similar to Example 306, except using cyclopenten-1-ylboronic acid instead of potassium trans-1-propenyltrifluoroborate. $^1$H NMR (400 MHz, Acetone-d$_6$) δ 9.59 (s, 1H), 8.37-8.19 (m, 1H), 7.55-7.45 (m, 2H), 7.45-7.32 (m, 4H), 7.26 (d, J=8.9 Hz, 1H), 6.75-6.60 (m, 1H), 3.68 (s, 3H), 2.86-2.71 (m, 2H), 2.65-2.48 (m, 2H), 2.15-1.98 (m, 2H); LCMS(m/z) 342.3.

Example 326. 8-(cyclohex-1-en-1-yl)-N-methyl-N-phenyl-[1,2,4]triazolo[4,3-a]quinazolin-5-amine

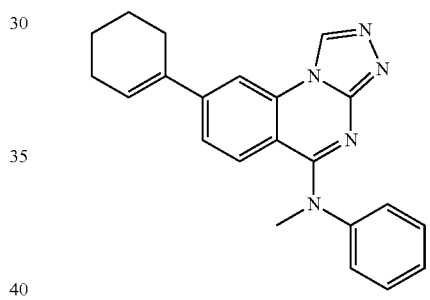

Example 326 was synthesized in a manner similar to Example 306, except using cyclohexen-1-ylboronic acid instead of potassium trans-1-propenyltrifluoroborate. $^1$H NMR (400 MHz, Acetone-d$_6$) δ 9.65 (s, 1H), 8.32 (d, J=1.9 Hz, 1H), 7.57-7.47 (m, 2H), 7.47-7.40 (m, 3H), 7.40-7.35 (m, 1H), 7.24 (d, J=9.0 Hz, 1H), 6.54 (td, J=4.1, 2.1 Hz, 1H), 3.70 (s, 3H), 2.55-2.44 (m, 2H), 2.35-2.23 (m, 2H), 1.88-1.74 (m, 2H), 1.74-1.62 (m, 2H); LCMS(m/z) 356.3.

Example 327. N-methyl-8-(methylsulfonyl)-N-phenyl-[1,2,4]triazolo[4,3-a]quinazolin-5-amine

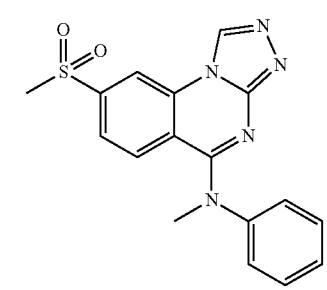 [SMILES: CN(c1ccccc1)c1nc2nncn2c2cc(S(C)(=O)=O)ccc12]

A vigorously stirred mixture of 8-bromo-N-methyl-N-phenyl-[1,2,4]triazolo[4,3-a]quinazolin-5-amine (Example 28, 10.0 mg, 28.2 µmol), sodium methanesulfinate (28.8 mg, 282 µmol), copper(I) iodide (53.8 mg, 282 µmol), and 1-methylpyrrolidin-2-one (0.5 mL) was heated to 140° C. After 60 min, the resulting mixture was cooled to room temperature and was purified by reverse phase preparative HPLC (0.1% trifluoroacetic acid in acetonitrile/water) to give the title compound: $^1$H NMR (400 MHz, Acetone-$d_6$) δ 9.67 (s, 1H), 8.77 (d, J=1.7 Hz, 1H), 7.73 (dd, J=8.7, 1.8 Hz, 1H), 7.62 (d, J=8.7 Hz, 1H), 7.53-7.43 (m, 2H), 7.43-7.39 (m, 2H), 7.39-7.31 (m, 1H), 3.67 (s, 3H), 3.25 (s, 3H); LCMS(m/z) 354.3.

Example 328. N-(3-bromophenyl)-8-(4-(tert-butyl)-1H-imidazol-1-yl)-N-methyl-[1,2,4]triazolo[4,3-a]quinazolin-5-amine

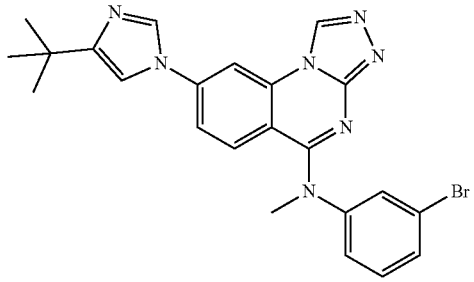 [SMILES: CN(c1cccc(Br)c1)c1nc2nncn2c2cc(-n3cnc(C(C)(C)C)c3)ccc12]

A vigorously stirred mixture of Example 308 (10.0 mg, 25.7 µmol), 4-(tert-butyl)-1H-imidazole (9.6 mg, 77 µmol), copper(I) iodide (2.5 mg, 13 µmol), potassium carbonate (17.9 mg, 129 µmol), L-proline (3.0 mg, 26 µmol), and dimethylsulfoxide (0.7 mL) was heated to 90° C. After 30 min, the resulting mixture was heated to 120° C. After 13.5 h, the resulting mixture was cooled to room temperature and was purified by reverse phase preparative HPLC (0.1% trifluoroacetic acid in acetonitrile/water) to give the title compound: $^1$H NMR (400 MHz, Acetone-$d_6$) δ 9.49 (s, 1H), 8.74 (d, J=2.3 Hz, 1H), 8.64 (d, J=1.5 Hz, 1H), 7.76-7.65 (m, 3H), 7.58 (d, J=9.1 Hz, 1H), 7.53 (dt, J=6.8, 1.9 Hz, 1H), 7.48-7.38 (m, 2H), 3.69 (s, 3H), 1.36 (s, 9H); LCMS(m/z) 476.3.

Example 329. 8-chloro-N-(4',4'-dimethyl-2',3',4',5'-tetrahydro-[1,1'-biphenyl]-3-yl)-N-methyl-[1,2,4]triazolo[4,3-a]quinazolin-5-amine

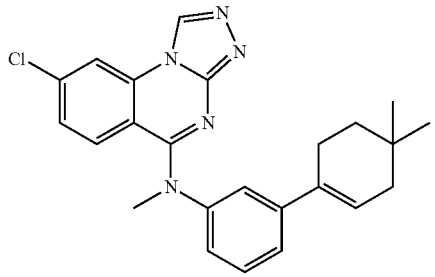

Example 329 was synthesized in a manner similar to Example 312, except using (4,4-dimethylcyclohex-1-en-1-yl)boronic acid instead of (4-isopropylphenyl)boronic acid. $^1$H NMR (400 MHz, Acetone-$d_6$) δ 9.53 (s, 1H), 8.46 (d, J=2.1 Hz, 1H), 7.52-7.36 (m, 4H), 7.33 (dd, J=9.0, 2.1 Hz, 1H), 7.27 (dt, J=7.3, 1.9 Hz, 1H), 6.13 (tt, J=3.9, 1.7 Hz, 1H), 3.70 (s, 3H), 2.45-2.33 (m, 2H), 2.01-1.95 (m, 2H), 1.51 (t, J=6.4 Hz, 2H), 0.95 (s, 6H); LCMS(m/z) 476.3.

Example 330. N-(4'-(tert-butyl)-2'-methyl-[1,1'-biphenyl]-3-yl)-8-chloro-N-methyl-[1,2,4]triazolo[4,3-a]quinazolin-5-amine

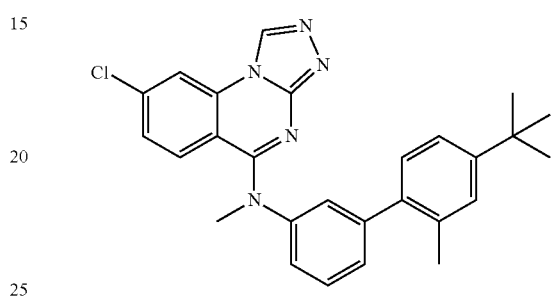

Example 330 was synthesized in a manner similar to Example 337, except using 4-(tert-butyl)-2-methylphenyl trifluoromethanesulfonate instead of 2-bromo-5-cyclopropylpyrazine and using chloro(2-dicyclohexylphosphino-2',4',6'-triisopropyl-1,1'-biphenyl)[2-(2'-amino-1,1'-biphenyl)]palladium(II) instead of [1,1'-bis(diphenylphosphino)ferrocene]dichloropalladium(II). $^1$H NMR (400 MHz, Acetone-$d_6$) δ 9.41 (s, 1H), 8.38 (s, 1H), 7.61-7.14 (m, 8H), 7.08 (d, J=7.9 Hz, 1H), 3.67 (s, 3H), 2.81 (s, 3H), 1.31 (s, 9H); LCMS(m/z) 456.4.

Example 331. N-(4'-(tert-butyl)-2'-chloro-[1,1'-biphenyl]-3-yl)-8-chloro-N-methyl-[1,2,4]triazolo[4,3-a]quinazolin-5-amine

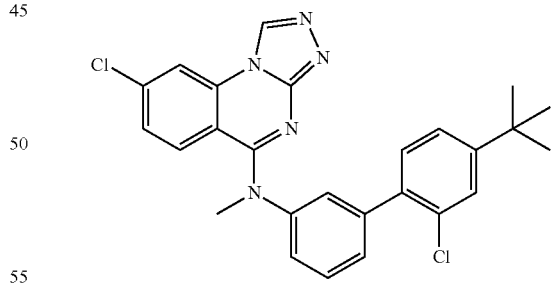

Example 331 was synthesized in a manner similar to Example 337, except using 4-(tert-butyl)-2-chlorophenyl trifluoromethanesulfonate instead of 2-bromo-5-cyclopropylpyrazine and using chloro(2-dicyclohexylphosphino-2',4',6'-triisopropyl-1,1'-biphenyl)[2-(2'-amino-1,1'-biphenyl)]palladium(II) instead of [1,1'-bis(diphenylphosphino)ferrocene]dichloropalladium(II). $^1$H NMR (400 MHz, Acetone-$d_6$) δ 9.43 (s, 1H), 8.39 (d, J=2.1 Hz, 1H), 7.65-7.40 (m, 6H), 7.40-7.25 (m, 3H), 3.68 (s, 3H), 1.34 (s, 9H); LCMS(m/z) 476.3.

Example 332. 8-chloro-N-methyl-N-(3-(6-methylpyridin-3-yl)phenyl)-[1,2,4]triazolo[4,3-a]quinazolin-5-amine

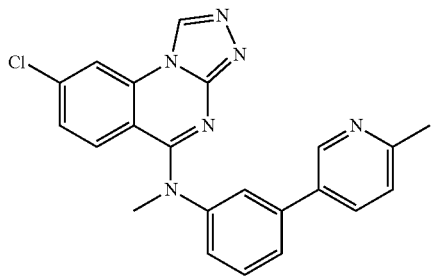

Example 332 was synthesized in a manner similar to Example 337, except using 5-bromo-2-methylpyridine instead of 2-bromo-5-cyclopropylpyrazine and using chloro(2-dicyclohexylphosphino-2',4',6'-triisopropyl-1,1'-biphenyl)[2-(2'-amino-1,1'-biphenyl)]palladium(II) instead of [1,1'-bis(diphenylphosphino)ferrocene]dichloropalladium (II). $^1$H NMR (400 MHz, Acetone-d$_6$) δ 9.44 (s, 1H), 8.69 (s, 1H), 8.39 (d, J=2.0 Hz, 1H), 7.92-7.86 (m, 1H), 7.72 (s, 1H), 7.63 (d, J=7.9 Hz, 1H), 7.57 (d, J=7.8 Hz, 1H), 7.52 (d, J=9.1 Hz, 1H), 7.44-7.36 (m, 1H), 7.35-7.22 (m, 2H), 3.70 (s, 3H), 2.52 (s, 3H); LCMS(m/z) 401.2.

Example 333. 8-chloro-N-methyl-N-(3-(5-methylpyridin-2-yl)phenyl)-[1,2,4]triazolo[4,3-a]quinazolin-5-amine

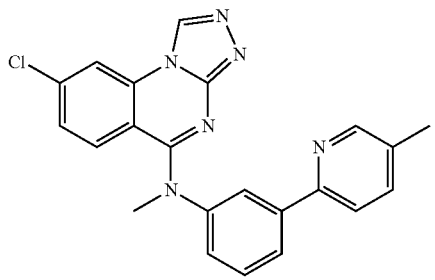

Example 333 was synthesized in a manner similar to Example 337, except using 2-bromo-5-methylpyridine instead of 2-bromo-5-cyclopropylpyrazine and using chloro(2-dicyclohexylphosphino-2',4',6'-triisopropyl-1,1'-biphenyl)[2-(2'-amino-1,1'-biphenyl)]palladium(II) instead of [1,1'-bis(diphenylphosphino)ferrocene]dichloropalladium (II). $^1$H NMR (400 MHz, Acetone-d$_6$) δ 9.48 (s, 1H), 8.51 (d, J=2.3 Hz, 1H), 8.42 (d, J=2.1 Hz, 1H), 8.13 (d, J=2.1 Hz, 1H), 8.09 (d, J=8.0 Hz, 1H), 7.84 (d, J=8.1 Hz, 1H), 7.68 (d, J=8.0 Hz, 1H), 7.57-7.47 (m, 2H), 7.41 (d, J=7.8 Hz, 1H), 7.28 (dd, J=9.1, 2.1 Hz, 1H), 3.72 (s, 3H), 2.37 (s, 3H); LCMS(m/z) 401.2.

Example 334. 8-chloro-N-methyl-N-(3-(5-methylpyrazin-2-yl)phenyl)-[1,2,4]triazolo[4,3-a]quinazolin-5-amine

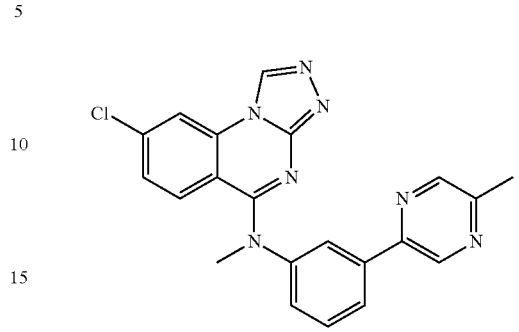

Example 334 was synthesized in a manner similar to Example 337, except using 2-bromo-5-methylpyrazine instead of 2-bromo-5-cyclopropylpyrazine and using chloro(2-dicyclohexylphosphino-2',4',6'-triisopropyl-1,1'-biphenyl)[2-(2'-amino-1,1'-biphenyl)]palladium(II) instead of [1,1'-bis(diphenylphosphino)ferrocene]dichloropalladium (II). $^1$H NMR (400 MHz, Acetone-d$_6$) δ 9.48 (s, 1H), 9.02 (s, 1H), 8.56 (s, 1H), 8.42 (d, J=2.0 Hz, 1H), 8.24-8.07 (m, 2H), 7.70-7.41 (m, 3H), 7.32-7.25 (m, 1H), 3.72 (s, 3H), 2.56 (s, 3H); LCMS(m/z) 402.2.

Example 335. 8-chloro-N-(3-(6-cyclopropylpyridin-3-yl)phenyl)-N-methyl-[1,2,4]triazolo[4,3-a]quinazolin-5-amine

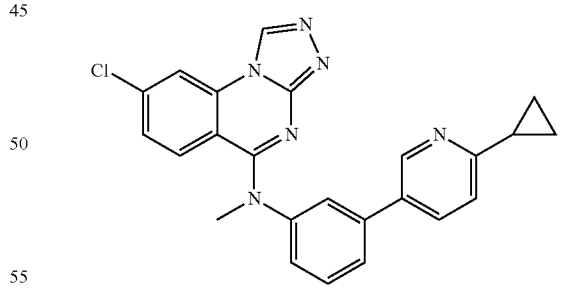

Example 335 was synthesized in a manner similar to Example 312, except using 2-cyclopropyl-5-(4,4,5,5-tetramethyl-1,3,2-dioxaborolan-2-yl)pyridine instead of (4-isopropylphenyl)boronic acid. $^1$H NMR (400 MHz, Acetone-d$_6$) δ 9.59 (s, 1H), 8.69 (d, J=2.5 Hz, 1H), 8.50 (d, J=2.3 Hz, 1H), 7.97 (dd, J=8.1, 2.5 Hz, 1H), 7.84-7.77 (m, 1H), 7.77-7.70 (m, 1H), 7.64 (dd, J=9.0, 6.6 Hz, 1H), 7.56-7.44 (m, 2H), 7.44-7.33 (m, 2H), 3.79 (d, J=2.8 Hz, 3H), 2.27-2.14 (m, 1H), 1.08-0.99 (m, 4H); LCMS(m/z) 427.3.

Example 336. 8-chloro-N-(3-(5-cyclopropylpyridin-2-yl)phenyl)-N-methyl-[1,2,4]triazolo[4,3-a]quinazolin-5-amine

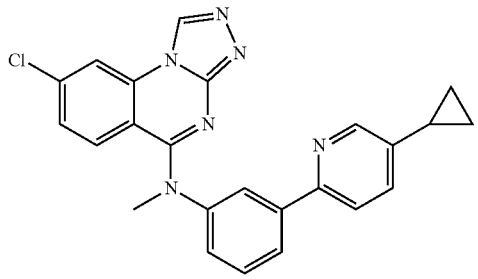

Example 336 was synthesized in a manner similar to Example 337, except using 2-bromo-5-cyclopropylpyridine instead of 2-bromo-5-cyclopropylpyrazine and using chloro(2-dicyclohexylphosphino-2',4',6'-triisopropyl-1,1'-biphenyl)[2-(2'-amino-1,1'-biphenyl)]palladium(II) instead of [1,1'-bis(diphenylphosphino)ferrocene]dichloropalladium(II). ¹H NMR (400 MHz, Acetone-$d_6$) δ 9.45 (s, 1H), 8.49 (d, J=2.3 Hz, 1H), 8.39 (d, J=2.3 Hz, 1H), 8.14-8.02 (m, 2H), 7.81 (d, J=8.3 Hz, 1H), 7.59-7.41 (m, 3H), 7.42-7.33 (m, 1H), 7.25 (d, J=8.9 Hz, 1H), 3.69 (s, 3H), 2.03-1.52 (m, 1H), 1.12-1.00 (m, 2H), 0.84-0.73 (m, 2H); LCMS(m/z) 427.3.

Example 337. 8-chloro-N-(3-(5-cyclopropylpyrazin-2-yl)phenyl)-N-methyl-[1,2,4]triazolo[4,3-a]quinazolin-5-amine

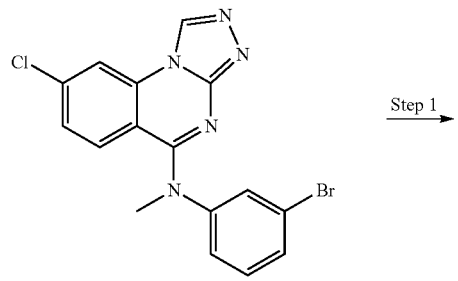

Step 1 →

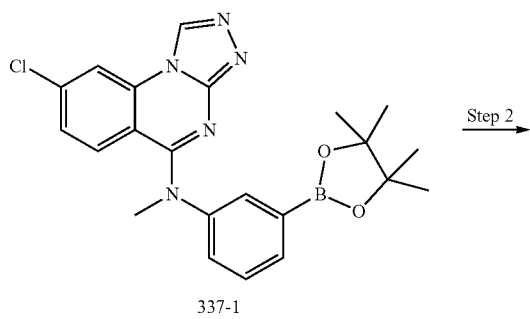

337-1

Step 2 →

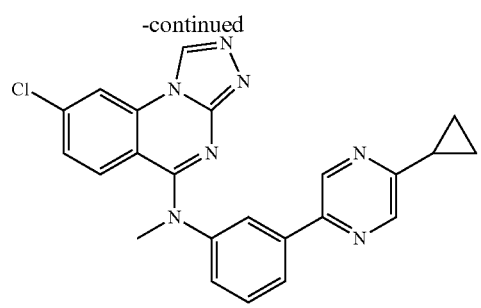

Step 1: A vigorously stirred mixture of Example 308 (300 mg, 772 μmol), 4,4,4',4',5,5,5',5'-octamethyl-2,2'-bi(1,3,2-dioxaborolane) (216 mg, 849 μmol), [1,1'-bis(diphenylphosphino)ferrocene]dichloropalladium(II) (28.2 mg, 38.6 μmol), potassium acetate (379 mg, 3.86 mmol), and 1,4-dioxane (10 mL) was heated to 110° C. After 20 min, the resulting mixture was cooled to room temperature. Silica gel (12 g) and ethyl acetate (75 mL) were added sequentially, and the resulting mixture was concentrated under reduced pressure. The residue was purified by flash column chromatography on silica gel (0 to 15% methanol in dichloromethane) to give Compound 337-1.

Step 2: A vigorously stirred mixture of Compound 313-1 (60.0 mg, 138 μmol), 2-bromo-5-cyclopropylpyrazine (41.1 mg, 207 μmol), [1,1'-bis(diphenylphosphino)ferrocene]dichloropalladium(II) (10.1 mg, 13.8 μmol), aqueous sodium carbonate solution (2.0 M, 689 μL, 1.38 mmol), and 1,4-dioxane (0.5 mL) was heated to 120° C. After 35 min, the resulting mixture was cooled to room temperature and was concentrated under reduced pressure. The residue was purified by reverse phase preparative HPLC (0.1% trifluoroacetic acid in acetonitrile/water) to give the title compound: ¹H NMR (400 MHz, Acetone-$d_6$) δ 9.48 (s, 1H), 8.95 (d, J=1.5 Hz, 1H), 8.62 (d, J=1.5 Hz, 1H), 8.42 (d, J=2.1 Hz, 1H), 8.12 (t, J=2.0 Hz, 1H), 8.10-8.03 (m, 1H), 7.59 (t, J=7.8 Hz, 1H), 7.51 (d, J=9.0 Hz, 1H), 7.48-7.43 (m, 1H), 7.28 (dd, J=9.0, 2.1 Hz, 1H), 3.72 (s, 3H), 2.29-2.20 (m, 1H), 1.12-1.00 (m, 4H); LCMS(m/z) 428.3.

Example 338. N-(3'-(tert-butyl)-[1,1'-biphenyl]-3-yl)-8-chloro-N-methyl-[1,2,4]triazolo[4,3-a]quinazolin-5-amine

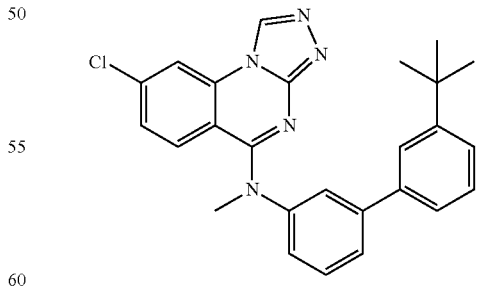

Example 338 was synthesized in a manner similar to Example 312, except using (3-tert-butylphenyl)boronic acid instead of (4-isopropylphenyl)boronic acid. ¹H NMR (400 MHz, Acetone-$d_6$) δ 9.50 (s, 1H), 8.45 (d, J=2.1 Hz, 1H), 7.71 (t, J=2.1 Hz, 1H), 7.65 (dt, J=8.0, 1.3 Hz, 1H), 7.60 (t, J=1.9 Hz, 1H), 7.56 (t, J=7.9 Hz, 1H), 7.50 (d, J=9.0 Hz, 1H), 7.47-7.34 (m, 4H), 7.32 (dd, J=9.0, 2.1 Hz, 1H), 3.74 (s, 3H), 1.33 (s, 9H); LCMS(m/z) 442.3.

Example 339. 8-chloro-N-(3-(5-(4,5-dihydro-1H-imidazol-2-yl)-6-methoxypyridin-2-yl)phenyl)-N-methyl-[1,2,4]triazolo[4,3-a]quinazolin-5-amine

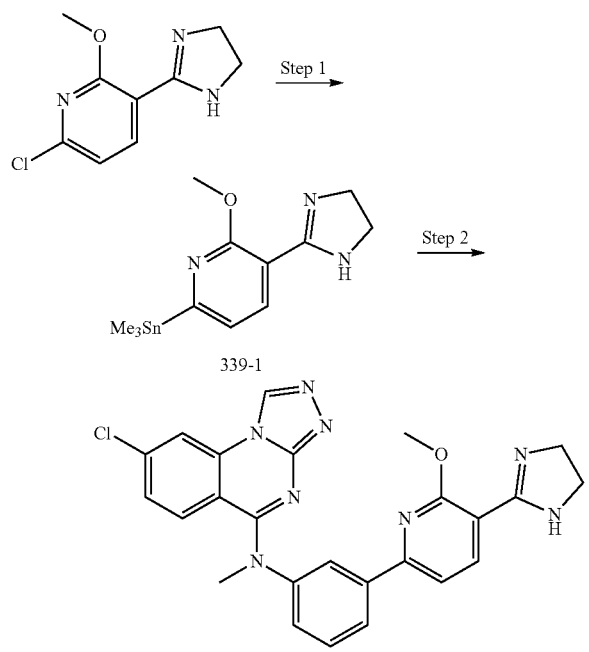

Step 1: A stirred mixture of 6-chloro-3-(4,5-dihydro-1H-imidazol-2-yl)-2-methoxypyridine (500 mg, 2.36 mmol), hexamethyl ditin (967 mg, 2.95 mmol), [1,1'-bis(diphenylphosphino)ferrocene]dichloropalladium(II) (86.4 mg, 118 μmol), and toluene (10 mL) was heated to 115° C. After 17 h, the resulting mixture was cooled to room temperature and was purified via flash column chromatography on silica gel (0 to 100% ethyl acetate in hexanes) to give Compound 339-1.

Step 2: A vigorously stirred mixture of Example 308 (10.0 mg, 25.7 μmol), 339-1 (13.1 mg, 38.6 μmol), [1,1'-bis(diphenylphosphino)ferrocene]dichloropalladium(II) (3.8 mg, 5.2 μmol), cesium fluoride (39.1 mg, 257 μmol), and 1,4-dioxane (1.0 mL) was heated to 105° C. After 7 min, the resulting mixture was heated to 120° C. After 3 h, the resulting mixture was cooled to 80° C. After 13 h, the resulting mixture was cooled to room temperature and was filtered through Celite®. The filter cake was extracted with dichloromethane, and the combined filtrates were concentrated under reduced pressure. The residue was purified by reverse phase preparative HPLC (0.1% trifluoroacetic acid in acetonitrile/water) to give the title compound: $^1$H NMR (400 MHz, Methanol-$d_4$) δ 9.61 (s, 1H), 8.52 (d, J=2.0 Hz, 1H), 8.40-8.27 (m, 1H), 7.99 (d, J=11.4 Hz, 1H), 7.82 (d, J=8.1 Hz, 1H), 7.75 (d, J=7.9 Hz, 1H), 7.70 (d, J=9.7 Hz, 1H), 7.60 (ddd, J=7.9, 2.2, 1.0 Hz, 1H), 7.38-7.33 (m, 1H), 7.33-7.28 (m, 1H), 4.21 (s, 3H), 4.11 (s, 4H), 3.88 (s, 3H); LCMS(m/z) 485.3.

Example 340. 8-chloro-N-(3-(6-cyclopropylpyridazin-3-yl)phenyl)-N-methyl-[1,2,4]triazolo[4,3-a]quinazolin-5-amine

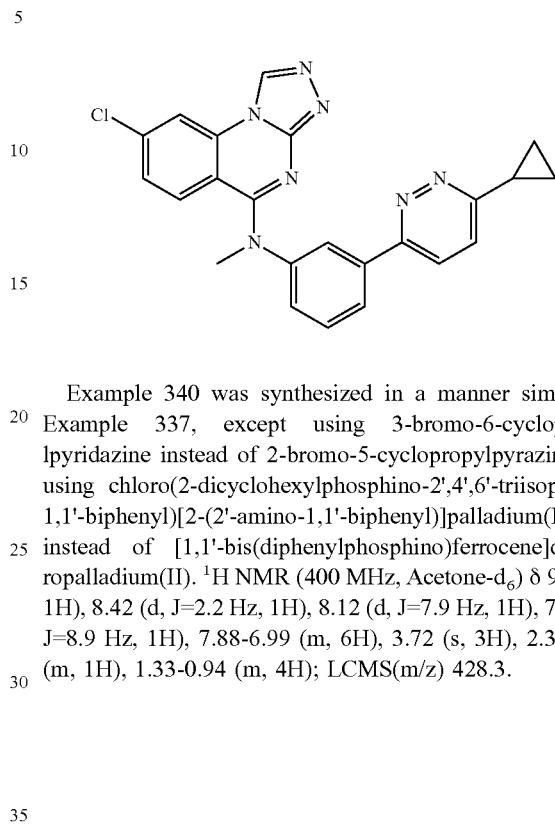

Example 340 was synthesized in a manner similar to Example 337, except using 3-bromo-6-cyclopropylpyridazine instead of 2-bromo-5-cyclopropylpyrazine and using chloro(2-dicyclohexylphosphino-2',4',6'-triisopropyl-1,1'-biphenyl)[2-(2'-amino-1,1'-biphenyl)]palladium(II) instead of [1,1'-bis(diphenylphosphino)ferrocene]dichloropalladium(II). $^1$H NMR (400 MHz, Acetone-$d_6$) δ 9.48 (s, 1H), 8.42 (d, J=2.2 Hz, 1H), 8.12 (d, J=7.9 Hz, 1H), 7.99 (d, J=8.9 Hz, 1H), 7.88-6.99 (m, 6H), 3.72 (s, 3H), 2.34-2.17 (m, 1H), 1.33-0.94 (m, 4H); LCMS(m/z) 428.3.

Example 341. 8-chloro-N-(3-(5-cyclopropyl-1,3,4-oxadiazol-2-yl)phenyl)-N-methyl-[1,2,4]triazolo[4,3-a]quinazolin-5-amine

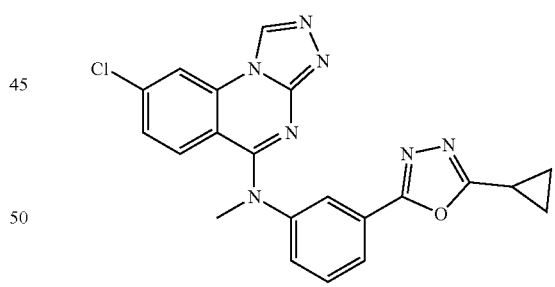

Example 341 was synthesized in a manner similar to Example 337, except using 2-bromo-5-cyclopropyl-1,3,4-oxadiazole instead of 2-bromo-5-cyclopropylpyrazine and using chloro(2-dicyclohexylphosphino-2',4',6'-triisopropyl-1,1'-biphenyl)[2-(2'-amino-1,1'-biphenyl)]palladium(II) instead of [1,1'-bis(diphenylphosphino)ferrocene]dichloropalladium(II). $^1$H NMR (400 MHz, Acetone-$d_6$) δ 9.49 (s, 1H), 8.43 (d, J=2.0 Hz, 1H), 8.01 (d, J=2.5 Hz, 1H), 7.91 (d, J=7.5 Hz, 1H), 7.60 (d, J=7.8 Hz, 1H), 7.56-7.52 (m, 1H), 7.51 (d, J=9.0 Hz, 1H), 7.29 (dd, J=9.0, 2.1 Hz, 1H), 3.70 (s, 3H), 2.50-2.19 (m, 1H), 1.41-0.79 (m, 4H); LCMS(m/z) 418.2.

Example 342. 8-chloro-N-(3-(5-cyclopropyl-1,3,4-thiadiazol-2-yl)phenyl)-N-methyl-[1,2,4]triazolo[4,3-a]quinazolin-5-amine

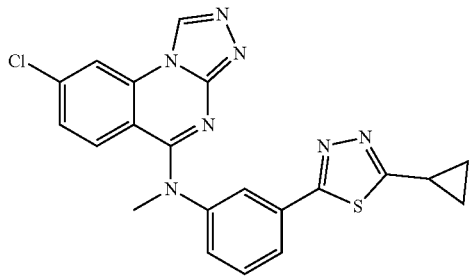

Example 342 was synthesized in a manner similar to Example 337, except using 2-bromo-5-cyclopropyl-1,3,4-thiadiazole instead of 2-bromo-5-cyclopropylpyrazine and using chloro(2-dicyclohexylphosphino-2',4',6'-triisopropyl-1,1'-biphenyl)[2-(2'-amino-1,1'-biphenyl)]palladium(II) instead of [1,1'-bis(diphenylphosphino)ferrocene]dichloropalladium(II). $^1$H NMR (400 MHz, Acetone-$d_6$) δ 9.60 (s, 1H), 8.52 (d, J=2.1 Hz, 1H), 8.02 (t, J=2.0 Hz, 1H), 7.92 (dt, J=7.6, 1.4 Hz, 1H), 7.64 (t, J=7.8 Hz, 1H), 7.58 (ddd, J=8.1, 2.3, 1.2 Hz, 1H), 7.51 (d, J=9.0 Hz, 1H), 7.38 (dd, J=9.0, 2.1 Hz, 1H), 3.78 (s, 3H), 2.54 (tt, J=8.3, 4.9 Hz, 1H), 1.33-1.24 (m, 2H), 1.16-1.07 (m, 2H); LCMS(m/z) 434.2.

Example 343. 8-chloro-N-methyl-N-(4'-((methylsulfonyl)methyl)-[1,1'-biphenyl]-3-yl)-[1,2,4]triazolo[4,3-a]quinazolin-5-amine

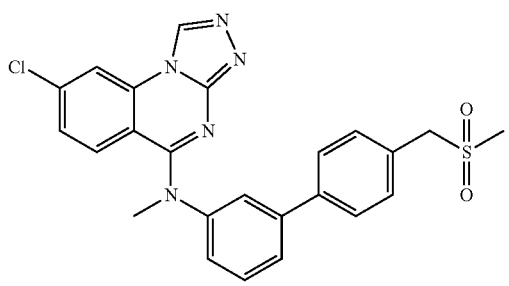 [SMILES: CN(c1cccc(-c2ccc(CS(C)(=O)=O)cc2)c1)c1nc2nncn2c2cc(Cl)ccc12]

Example 343 was synthesized in a manner similar to Example 337, except using 1-bromo-4-((methylsulfonyl)methyl)benzene instead of 2-bromo-5-cyclopropylpyrazine and using chloro(2-dicyclohexylphosphino-2',4',6'-triisopropyl-1,1'-biphenyl)[2-(2'-amino-1,1'-biphenyl)]palladium(II) instead of [1,1'-bis(diphenylphosphino)ferrocene]dichloropalladium(II). $^1$H NMR (400 MHz, Acetone-$d_6$) δ 9.44 (s, 1H), 8.39 (d, J=2.2 Hz, 1H), 7.77-7.42 (m, 8H), 7.42-7.35 (m, 1H), 7.26 (dd, J=8.9, 2.1 Hz, 1H), 4.43 (s, 2H), 3.70 (s, 3H), 2.88 (s, 3H); LCMS(m/z) 478.2.

Example 344. 5-(3-((8-chloro-[1,2,4]triazolo[4,3-a]quinazolin-5-yl)(methyl)amino)phenyl)isoindoline-1,3-dione

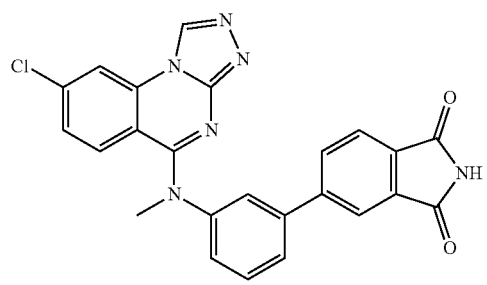 [SMILES: CN(c1cccc(-c2ccc3c(c2)C(=O)NC3=O)c1)c1nc2nncn2c2cc(Cl)ccc12]

Example 344 was synthesized in a manner similar to Example 312, except using 5-(4,4,5,5-tetramethyl-1,3,2-dioxaborolan-2-yl)isoindoline-1,3-dione instead of (4-isopropylphenyl)boronic acid. $^1$H NMR (400 MHz, Acetone-$d_6$) δ 10.14 (s, 1H), 9.52 (s, 1H), 8.45 (d, J=2.2 Hz, 1H), 8.17-8.10 (m, 1H), 8.10-8.03 (m, 1H), 7.95 (t, J=2.1 Hz, 1H), 7.89 (d, J=7.9 Hz, 1H), 7.82 (d, J=7.7 Hz, 1H), 7.71-7.59 (m, 1H), 7.59-7.45 (m, 2H), 7.42-7.25 (m, 1H), 3.76 (s, 3H); LCMS (m/z) 455.3.

Example 345. 2-(3'-((8-chloro-[1,2,4]triazolo[4,3-a]quinazolin-5-yl)(methyl)amino)-[1,1'-biphenyl]-4-yl)propan-2-ol

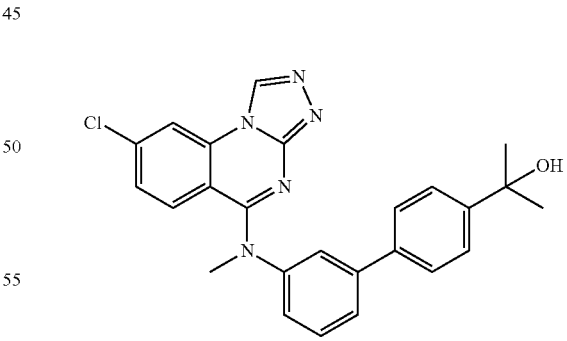

Example 345 was synthesized in a manner similar to Example 312, except using (4-(2-hydroxypropan-2-yl)phenyl)boronic acid instead of (4-isopropylphenyl)boronic acid. $^1$H NMR (400 MHz, Methanol-$d_4$) δ 9.55 (s, 1H), 8.47 (dd, J=1.8, 0.7 Hz, 1H), 7.77 (ddd, J=7.9, 1.8, 1.0 Hz, 1H), 7.70 (t, J=2.0 Hz, 1H), 7.62 (t, J=7.9 Hz, 1H), 7.58 (s, 4H), 7.39 (ddd, J=7.9, 2.3, 1.0 Hz, 1H), 7.37-7.30 (m, 2H), 3.83 (s, 3H), 1.56 (s, 6H); LCMS(m/z) 444.3.

Example 346. tert-butyl 4-(3-((8-chloro-[1,2,4]tri-azolo[4,3-a]quinazolin-5-yl)(methyl)amino)phenyl)-3,6-dihydropyridine-1(2H)-carboxylate

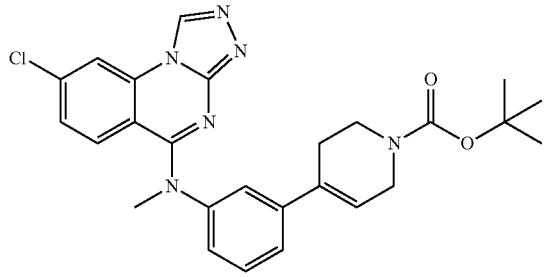 [SMILES: CN(c1cccc(C2=CCN(C(=O)OC(C)(C)C)CC2)c1)c1nc2nncn2c2cc(Cl)ccc12]

Example 346 was synthesized in a manner similar to Example 312, except using tert-butyl 4-(4,4,5,5-tetramethyl-1,3,2-dioxaborolan-2-yl)-3,6-dihydropyridine-1(2H)-carboxylate instead of (4-isopropylphenyl)boronic acid. $^1$H NMR (400 MHz, Acetone-d$_6$) δ 9.54 (s, 1H), 8.47 (s, 1H), 7.56-7.43 (m, 3H), 7.43-7.36 (m, 1H), 7.36-7.26 (m, 2H), 6.19 (s, 1H), 4.08-3.93 (m, 2H), 3.70 (s, 3H), 3.63-3.54 (m, 2H), 2.58-2.37 (m, 2H), 1.46 (d, J=3.1 Hz, 9H); LCMS(m/z) 491.2.

Example 347. 8-chloro-N-(2-chloro-4'-cyclopropyl-[1,1'-biphenyl]-3-yl)-N-methyl-[1,2,4]triazolo[4,3-a]quinazolin-5-amine

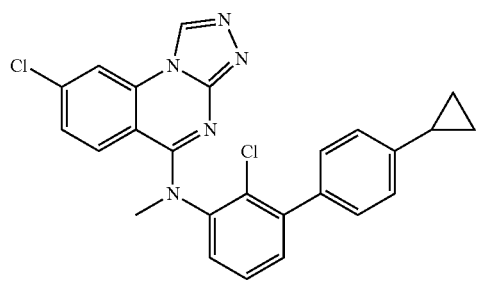

Example 347 was synthesized in a manner similar to Example 312, except using Compound 349-3 in place of Example 308 and using (4-cyclopropylphenyl)boronic acid in place of (4-isopropylphenyl)boronic acid. $^1$H NMR (400 MHz, Acetone-d$_6$) δ 9.55 (s, 1H), 8.51 (d, J=2.1 Hz, 1H), 7.60-7.48 (m, 3H), 7.48-7.36 (m, 3H), 7.30 (d, J=9.0 Hz, 1H), 7.22 (d, J=8.3 Hz, 2H), 3.65 (s, 3H), 2.30-1.80 (m, 1H), 1.18-0.58 (m, 4H); LCMS(m/z) 460.3.

Example 348. 8-chloro-N-(4-chloro-4'-cyclopropyl-[1,1'-biphenyl]-3-yl)-N-methyl-[1,2,4]triazolo[4,3-a]quinazolin-5-amine

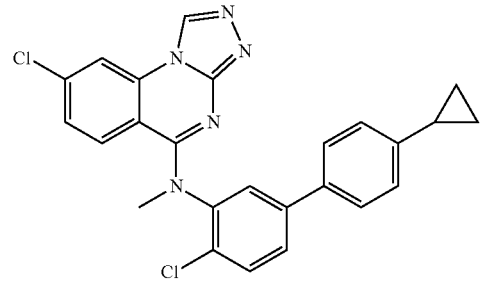

Example 348 was synthesized in a manner similar to Example 312, except using Compound 349-2 in place of Example 308 and using (4-cyclopropylphenyl)boronic acid in place of (4-isopropylphenyl)boronic acid. $^1$H NMR (400 MHz, Acetone-d$_6$) δ 9.66 (s, 1H), 8.58 (d, J=2.1 Hz, 1H), 7.89 (d, J=2.1 Hz, 1H), 7.84 (dd, J=8.4, 2.2 Hz, 1H), 7.78 (d, J=8.4 Hz, 1H), 7.73-7.50 (m, 2H), 7.46 (dd, J=9.1, 2.0 Hz, 1H), 7.36 (d, J=9.0 Hz, 1H), 7.19-7.11 (m, 2H), 3.73 (s, 3H), 2.28-1.79 (m, 1H), 1.09-0.95 (m, 2H), 0.80-0.61 (m, 2H); LCMS(m/z) 460.3.

Example 349. 8-chloro-N-(6-chloro-4'-cyclopropyl-[1,1'-biphenyl]-3-yl)-N-methyl-[1,2,4]triazolo[4,3-a]quinazolin-5-amine

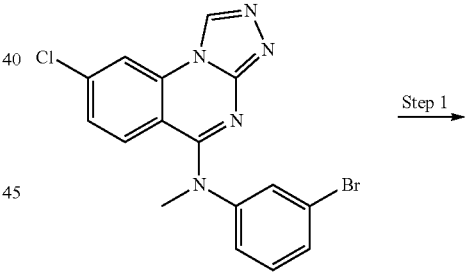

Step 1

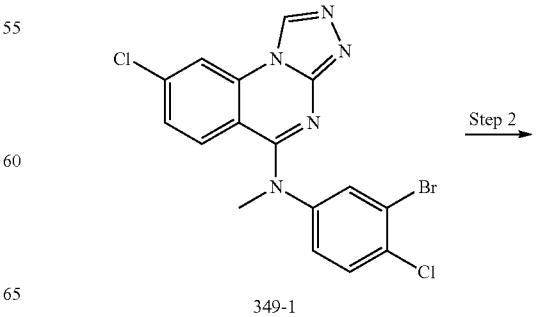

349-1

Step 2

-continued

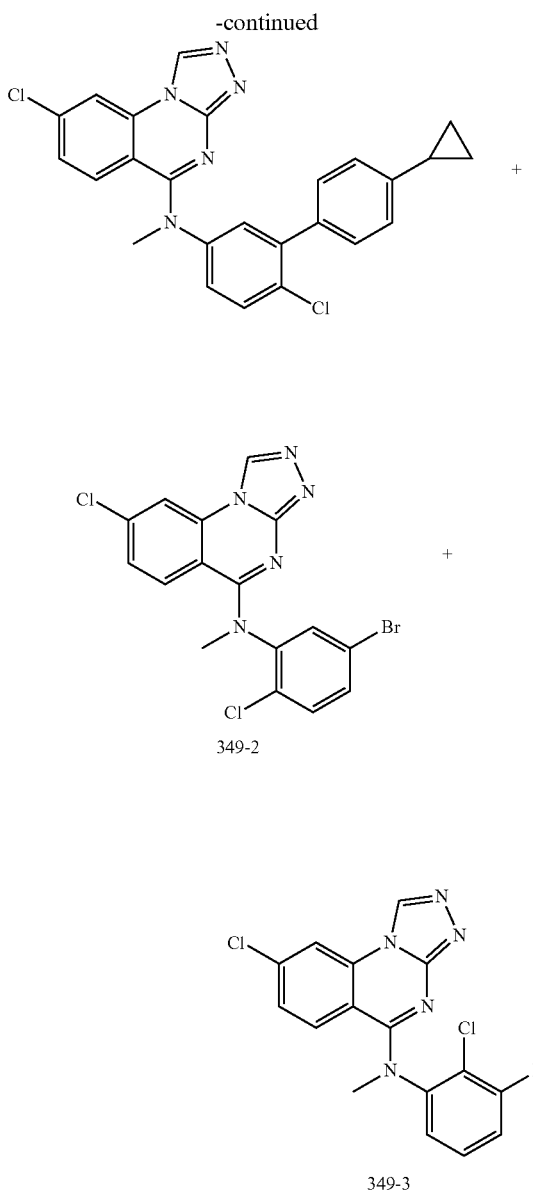

349-2

349-3

Step 1: 2-Chloro-1,3-bis(methoxycarbonyl)guanidine (10.8 mg, 51.5 µmol) was added to a stirred solution of Example 308 (20.0 mg, 51.5 µmol) in acetonitrile (0.8 mL) and chloroform (0.5 mL) at 0° C. After 5 min, the resulting mixture was warmed to room temperature. After 25 min, hydrogen chloride solution (4.0 M in 1,4-dioxane, 12.9 µL, 52 µmol) was added via syringe. After 95 min, the resulting mixture was concentrated under reduced pressure. The residue was purified by reverse phase preparative HPLC (0.1% trifluoroacetic acid in acetonitrile/water) to give Compounds 349-1, 349-2, and 349-3.

Step 2: Example 349 was synthesized in a manner similar to Example 312, except using Compound 349-1 in place of Example 308 and using (4-cyclopropylphenyl)boronic acid in place of (4-isopropylphenyl)boronic acid. $^1$H NMR (400 MHz, Acetone-$d_6$) δ 9.50 (s, 1H), 8.45 (d, J=2.1 Hz, 1H), 7.59 (dd, J=8.7, 1.5 Hz, 2H), 7.46-7.35 (m, 3H), 7.31-7.23 (m, 2H), 7.18-7.10 (m, 2H), 3.71 (s, 3H), 2.05-1.87 (m, 1H), 1.08-0.94 (m, 2H), 0.76-0.60 (m, 2H); LCMS(m/z) 460.3.

Example 350. 8-chloro-N-methyl-N-(3-(1,2,3,6-tetrahydropyridin-4-yl)phenyl)-[1,2,4]triazolo[4,3-a]quinazolin-5-amine

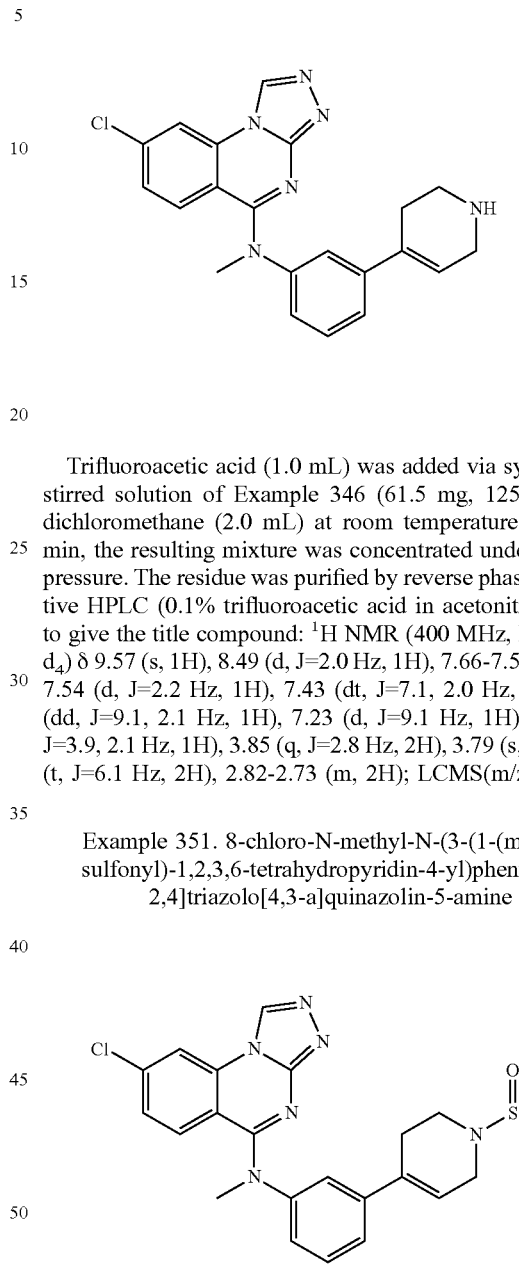

Trifluoroacetic acid (1.0 mL) was added via syringe to a stirred solution of Example 346 (61.5 mg, 125 µmol) in dichloromethane (2.0 mL) at room temperature. After 20 min, the resulting mixture was concentrated under reduced pressure. The residue was purified by reverse phase preparative HPLC (0.1% trifluoroacetic acid in acetonitrile/water) to give the title compound: $^1$H NMR (400 MHz, Methanol-$d_4$) δ 9.57 (s, 1H), 8.49 (d, J=2.0 Hz, 1H), 7.66-7.56 (m, 2H), 7.54 (d, J=2.2 Hz, 1H), 7.43 (dt, J=7.1, 2.0 Hz, 1H), 7.32 (dd, J=9.1, 2.1 Hz, 1H), 7.23 (d, J=9.1 Hz, 1H), 6.23 (dt, J=3.9, 2.1 Hz, 1H), 3.85 (q, J=2.8 Hz, 2H), 3.79 (s, 3H), 3.47 (t, J=6.1 Hz, 2H), 2.82-2.73 (m, 2H); LCMS(m/z) 391.2.

Example 351. 8-chloro-N-methyl-N-(3-(1-(methylsulfonyl)-1,2,3,6-tetrahydropyridin-4-yl)phenyl)-[1,2,4]triazolo[4,3-a]quinazolin-5-amine Methanesulfonyl chloride (5.0 µL, 64 µmol) was added via syringe to a stirred mixture of Example 350 (5.0 mg, 13 µmol) and triethylamine (35.7 µL, 256 µmol) in dichloromethane (0.5 mL) at room temperature. After 20 min, the resulting mixture was concentrated under reduced pressure. The residue was purified by reverse phase preparative HPLC (0.1% trifluoroacetic acid in acetonitrile/water) to give the title compound: $^1$H NMR (400 MHz, Acetone-$d_6$) δ 9.53 (s, 1H), 8.46 (d, J=2.1 Hz, 1H), 7.57-7.54 (m, 1H), 7.54-7.45 (m, 2H), 7.41 (d, J=9.0 Hz, 1H), 7.38-7.28 (m, 2H), 6.29-6.20 (m, 1H), 3.91 (q, J=2.9 Hz, 2H), 3.70 (s, 3H), 3.46 (t, J=5.7 Hz, 2H), 2.87 (s, 3H), 2.70-2.56 (m, 2H); LCMS(m/z) 469.3.

Example 352. 8-chloro-N-(3-(1-isopropyl-1,2,3,6-tetrahydropyridin-4-yl)phenyl)-N-methyl-[1,2,4]triazolo[4,3-a]quinazolin-5-amine

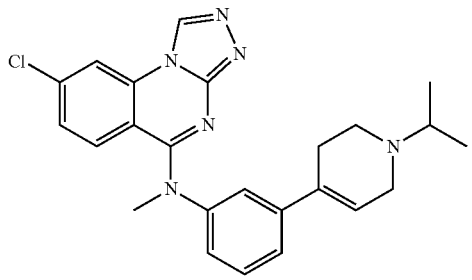

Sodium triacetoxyborohydride (54.0 mg, 256 μmol) was added to a stirred mixture of Example 350 (5.0 mg, 13 μmol), acetone (18.9 μL, 256 μmol), triethylamine (17.8 μL, 128 μmol), and acetic acid (7.3 μL, 128 μmol) in dichloromethane (0.5 mL) at room temperature, and the resulting mixture was heated to 45° C. After 150 min, the resulting mixture was cooled to room temperature and was concentrated under reduced pressure. The residue was purified by reverse phase preparative HPLC (0.1% trifluoroacetic acid in acetonitrile/water) to give the title compound: $^1$H NMR (400 MHz, Methanol-$d_4$) δ 9.58 (s, 1H), 8.50 (d, J=2.1 Hz, 1H), 7.68-7.57 (m, 2H), 7.54 (s, 1H), 7.46 (d, J=7.3 Hz, 1H), 7.31 (dd, J=9.1, 2.1 Hz, 1H), 7.22 (d, J=9.1 Hz, 1H), 6.28-6.20 (m, 1H), 3.98-3.89 (m, 2H), 3.80 (s, 3H), 3.77-3.70 (m, 2H), 3.66 (hept, J=6.9 Hz, 1H), 2.95-2.78 (m, 2H), 1.43 (d, J=6.6 Hz, 6H); LCMS(m/z) 433.2.

Example 353. 8-chloro-N-methyl-N-(3-(6-(trifluoromethyl)pyridin-3-yl)phenyl)-[1,2,4]triazolo[4,3-a]quinazolin-5-amine

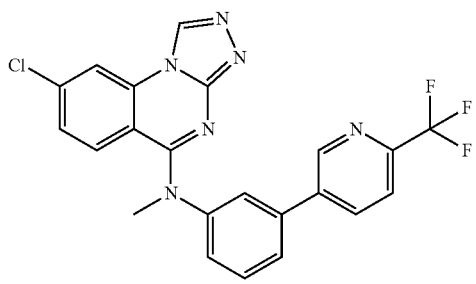 [SMILES: CN(c1cccc(-c2ccc(C(F)(F)F)nc2)c1)c1nc2nncn2c2cc(Cl)ccc12]

Example 353 was synthesized in a manner similar to Example 312, except using 5-(4,4,5,5-tetramethyl-1,3,2-dioxaborolan-2-yl)-2-(trifluoromethyl)pyridine instead of (4-isopropylphenyl)boronic acid. $^1$H NMR (400 MHz, Acetone-$d_6$) δ 9.50 (s, 1H), 9.00 (d, J=2.3 Hz, 1H), 8.44 (d, J=2.2 Hz, 1H), 8.32 (dd, J=8.2, 2.3 Hz, 1H), 7.95-7.85 (m, 2H), 7.85-7.73 (m, 1H), 7.66 (t, J=7.9 Hz, 1H), 7.58-7.45 (m, 2H), 7.30 (dd, J=9.0, 2.1 Hz, 1H), 3.74 (s, 3H); LCMS (m/z) 455.3.

Example 354. 8-chloro-N-(3-(6-(difluoromethyl)pyridin-3-yl)phenyl)-N-methyl-[1,2,4]triazolo[4,3-a]quinazolin-5-amine

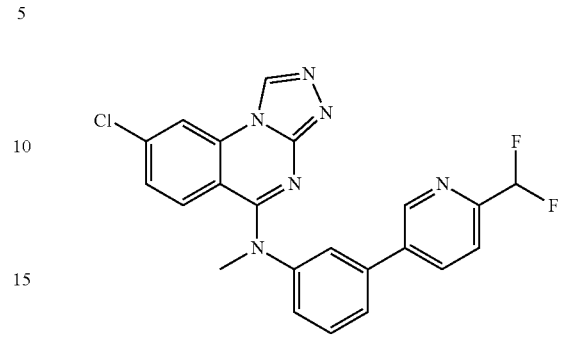

Example 354 was synthesized in a manner similar to Example 312, except using 5-(4,4,5,5-tetramethyl-1,3,2-dioxaborolan-2-yl)-2-(difluoromethyl)pyridine instead of (4-isopropylphenyl)boronic acid. $^1$H NMR (400 MHz, Acetone-$d_6$) δ 9.63 (s, 1H), 8.92 (d, J=2.2 Hz, 1H), 8.54 (d, J=2.1 Hz, 1H), 8.26 (dd, J=8.1, 2.3 Hz, 1H), 7.94 (t, J=2.0 Hz, 1H), 7.85 (dt, J=8.0, 1.3 Hz, 1H), 7.78 (d, J=8.1 Hz, 1H), 7.71 (t, J=7.9 Hz, 1H), 7.59 (ddd, J=8.0, 2.2, 1.0 Hz, 1H), 7.50 (d, J=9.1 Hz, 1H), 7.39 (dd, J=9.1, 2.1 Hz, 1H), 6.84 (t, J=55.3 Hz, 1H), 3.82 (s, 3H); LCMS(m/z) 437.3.

Example 355. 3'-((8-chloro-[1,2,4]triazolo[4,3-a]quinazolin-5-yl)(methyl)amino)-4-(trifluoromethyl)-[1,1'-biphenyl]-2-carboxamide

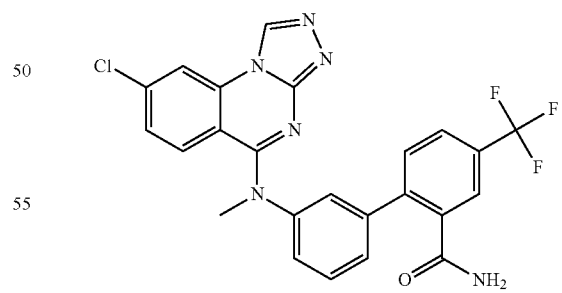

Example 355 was synthesized in a manner similar to Example 312, except using 2-(4,4,5,5-tetramethyl-1,3,2-dioxaborolan-2-yl)-5-(trifluoromethyl)benzonitrile instead of (4-isopropylphenyl)boronic acid. $^1$H NMR (400 MHz, Acetonitrile-$d_3$) δ 9.11 (d, J=3.7 Hz, 1H), 8.23 (s, 1H), 7.95-7.80 (m, 2H), 7.70-7.41 (m, 4H), 7.43-7.18 (m, 3H), 6.58 (s, 1H), 6.13 (s, 1H), 3.76 (s, 3H); LCMS(m/z) 497.3.

Example 356. 1-(4-(3-((8-chloro-[1,2,4]triazolo[4,3-a]quinazolin-5-yl)(methyl)amino)phenyl)-3,6-dihydropyridin-1(2H)-yl)ethan-1-one

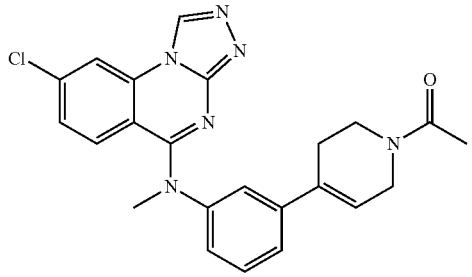 [SMILES: CC(=O)N1CC=C(c2cccc(N(C)c3nc4nncn4c4cc(Cl)ccc34)c2)CC1]

Acetic anhydride (9.6 μL, 100 μmol) was added via syringe to a stirred mixture of Example 350 (4.0 mg, 10 μmol) and N,N-diisopropylethylamine (28.5 μL, 164 μmol) in dichloromethane (0.5 mL) at room temperature. After 10 min, the resulting mixture was concentrated under reduced pressure. The residue was purified by reverse phase preparative HPLC (0.1% trifluoroacetic acid in acetonitrile/water) to give the title compound: $^1$H NMR (400 MHz, Acetone-$d_6$) δ 9.57 (s, 1H), 8.49 (d, J=2.0 Hz, 1H), 7.61-7.43 (m, 3H), 7.43-7.28 (m, 3H), 6.28-6.14 (m, 1H), 4.21-4.08 (m, 2H), 3.72 (s, 3H), 3.72-3.64 (m, 2H), 2.65-2.52 (m, 1H), 2.52-2.38 (m, 1H), 2.16-1.94 (m, 3H); LCMS(m/z) 433.3.

Example 357. 1-(4-(3-((8-chloro-[1,2,4]triazolo[4,3-a]quinazolin-5-yl)(methyl)amino)phenyl)-3,6-dihydropyridin-1(2H)-yl)-2,2-dimethylpropan-1-one

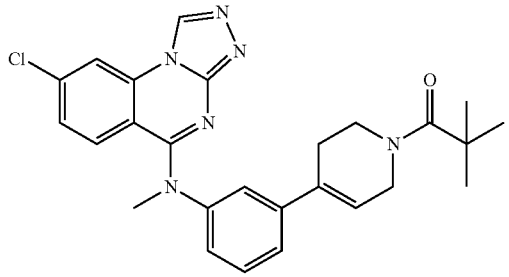

Pivalic anhydride (12.6 μL, 62.1 μmol) was added via syringe to a stirred mixture of Example 350 (4.0 mg, 10 μmol) and N,N-diisopropylethylamine (28.5 μL, 164 μmol) in dichloromethane (0.5 mL) at room temperature. After 20 min, the resulting mixture was concentrated under reduced pressure. The residue was purified by reverse phase preparative HPLC (0.1% trifluoroacetic acid in acetonitrile/water) to give the title compound: $^1$H NMR (400 MHz, Acetone-$d_6$) δ 9.54 (s, 1H), 8.47 (d, J=2.1 Hz, 1H), 7.57-7.44 (m, 3H), 7.41 (d, J=9.0 Hz, 1H), 7.38-7.29 (m, 2H), 6.25 (tt, J=3.5, 1.6 Hz, 1H), 4.21 (q, J=3.0 Hz, 2H), 3.82 (t, J=5.7 Hz, 2H), 3.71 (s, 3H), 2.54 (dt, J=7.9, 3.9 Hz, 2H), 1.26 (s, 9H); LCMS(m/z) 475.3.

Example 358. 8-chloro-N-methyl-N-(3-(1-((1-methylcyclopropyl)sulfonyl)-1,2,3,6-tetrahydropyridin-4-yl)phenyl)-[1,2,4]triazolo[4,3-a]quinazolin-5-amine

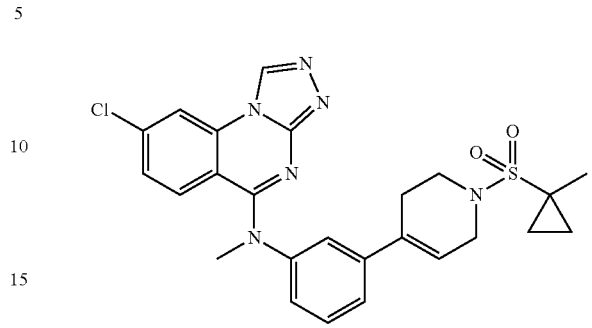

1-Methylcyclopropane-1-sulfonyl chloride (16.0 mg, 104 μmol) was added to a stirred mixture of Example 350 (4.0 mg, 10 μmol) and N,N-diisopropylethylamine (28.5 μL, 164 μmol) in dichloromethane (0.5 mL) at room temperature. After 23 min, the resulting mixture was heated to 60° C. After 30 min, the resulting mixture was cooled to room temperature and was concentrated under reduced pressure. The residue was purified by reverse phase preparative HPLC (0.1% trifluoroacetic acid in acetonitrile/water) to give the title compound: $^1$H NMR (400 MHz, Acetone-$d_6$) δ 9.50 (s, 1H), 8.44 (d, J=2.0 Hz, 1H), 7.57-7.49 (m, 1H), 7.49-7.44 (m, 2H), 7.42 (d, J=9.0 Hz, 1H), 7.39-7.25 (m, 2H), 6.28-6.16 (m, 1H), 4.04 (q, J=3.0 Hz, 2H), 3.68 (s, 3H), 3.59 (t, J=5.7 Hz, 2H), 2.66-2.50 (m, 2H), 1.45 (s, 3H), 1.31-1.21 (m, 2H), 0.91-0.75 (m, 2H); LCMS(m/z) 509.3.

Example 359. 8-chloro-N-methyl-N-(3-(1-((trifluoromethyl)sulfonyl)-1,2,3,6-tetrahydropyridin-4-yl)phenyl)-[1,2,4]triazolo[4,3-a]quinazolin-5-amine

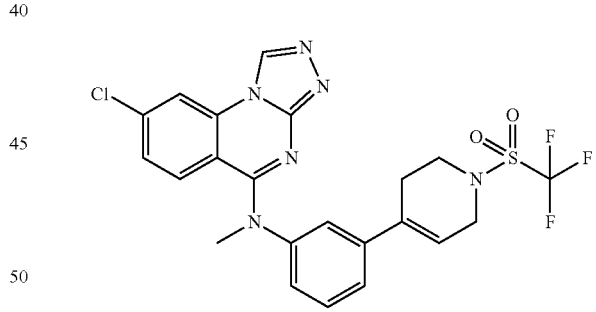

Trifluoromethanesulfonic anhydride (2.6 μL, 15 μmol) was added via syringe to a stirred mixture of Example 350 (4.0 mg, 10 μmol) and N,N-diisopropylethylamine (28.5 μL, 164 μmol) in dichloromethane (0.5 mL) at −78° C. After 10 min, water (0.1 mL) was added, and the resulting mixture was warmed to room temperature and was concentrated under reduced pressure. The residue was purified by reverse phase preparative HPLC (0.1% trifluoroacetic acid in acetonitrile/water) to give the title compound: $^1$H NMR (400 MHz, Acetone-$d_6$) δ 9.46 (s, 1H), 8.41 (d, J=2.1 Hz, 1H), 7.53 (t, J=1.6 Hz, 1H), 7.50-7.39 (m, 3H), 7.39-7.30 (m, 1H), 7.27 (dd, J=9.0, 2.1 Hz, 1H), 6.32-6.16 (m, 1H), 4.28-4.13 (m, 2H), 3.91-3.69 (m, 2H), 3.65 (s, 3H), 2.79-2.61 (m, 2H); LCMS(m/z) 523.2.

Example 360. N-methyl-8-(methylsulfonyl)-N-phenyl-[1,2,4]triazolo[4,3-a]quinazolin-5-amine

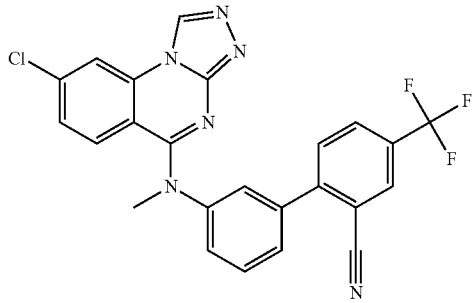 [SMILES: CN(c1cccc(-c2ccc(C(F)(F)F)cc2C#N)c1)c1nc2nncn2c2cc(Cl)ccc12]

A vigorously stirred mixture of Example 308 (5.0 mg, 13 µmol), (2-cyano-4-(trifluoromethyl)phenyl)boronic acid (4.2 mg, 19 µmol), cesium fluoride (19.5 mg, 129 µmol), [1,1'-bis(diphenylphosphino)ferrocene]dichloropalladium (II) (1.0 mg, 1.4 µmol), and 1,4-dioxane was heated to 100° C. After 14 min, the resulting mixture was heated to 120° C. After 50 min, the resulting mixture was cooled to room temperature and was concentrated under reduced pressure. The residue was purified by reverse phase preparative HPLC (0.1% trifluoroacetic acid in acetonitrile/water) to give the title compound: $^1$H NMR (400 MHz, Acetonitrile-$d_3$) δ 9.13 (s, 1H), 8.36-8.17 (m, 2H), 8.17-7.99 (m, 1H), 7.84-7.60 (m, 4H), 7.52 (s, 1H), 7.33 (s, 2H), 3.79 (s, 3H); LCMS(m/z) 479.3.

Example 361. 8-chloro-N-methyl-N-(4'-(trifluoromethyl)-[1,1'-biphenyl]-3-yl)-[1,2,4]triazolo[4,3-a]quinazolin-5-amine

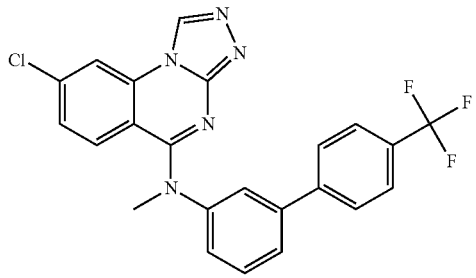 [SMILES: CN(c1cccc(-c2ccc(C(F)(F)F)cc2)c1)c1nc2nncn2c2cc(Cl)ccc12]

Example 361 was synthesized in a manner similar to Example 312, except using [4-(trifluoromethyl)phenyl]boronic acid instead of (4-isopropylphenyl)boronic acid. $^1$H NMR (400 MHz, Acetone-$d_6$) δ 9.46 (s, 1H), 8.41 (d, J=2.3 Hz, 1H), 7.88 (d, J=8.0 Hz, 2H), 7.84-7.73 (m, 3H), 7.70 (d, J=7.5 Hz, 1H), 7.59 (t, J=7.9 Hz, 1H), 7.53 (d, J=8.9 Hz, 1H), 7.50-7.41 (m, 1H), 7.28 (dd, J=9.0, 2.2 Hz, 1H), 3.71 (s, 3H); LCMS(m/z) 454.3.

Example 362. 3'-((8-chloro-[1,2,4]triazolo[4,3-a]quinazolin-5-yl)(methyl)amino)-4-cyclopropyl-[1,1'-biphenyl]-2-carbonitrile

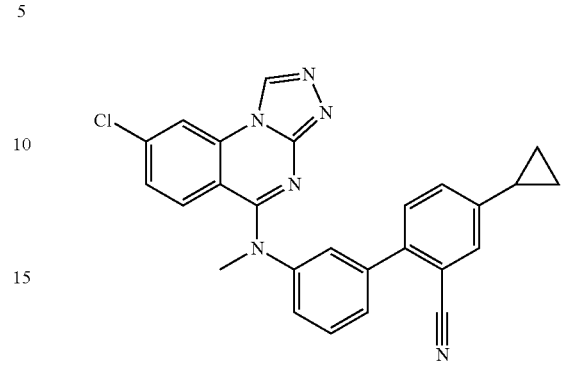

Example 362 was synthesized in a manner similar to Example 312, except using 5-cyclopropyl-2-(4,4,5,5-tetramethyl-1,3,2-dioxaborolan-2-yl)benzonitrile instead of (4-isopropylphenyl)boronic acid. $^1$H NMR (400 MHz, Acetonitrile-$d_3$) δ 9.11 (s, 1H), 8.19 (d, J=2.1 Hz, 1H), 7.70-7.50 (m, 4H), 7.49-7.43 (m, 2H), 7.40 (dt, J=7.2, 2.1 Hz, 1H), 7.35 (d, J=9.1 Hz, 1H), 7.27 (dd, J=9.1, 2.1 Hz, 1H), 3.73 (s, 3H), 2.07-1.92 (m, 1H), 1.25-0.94 (m, 2H), 0.80 (dt, J=6.8, 4.6 Hz, 2H); LCMS(m/z) 451.3.

Example 363. (E)-8-chloro-N-(3-(3,3-dimethylbut-1-en-1-yl)phenyl)-N-methyl-[1,2,4]triazolo[4,3-a]quinazolin-5-amine

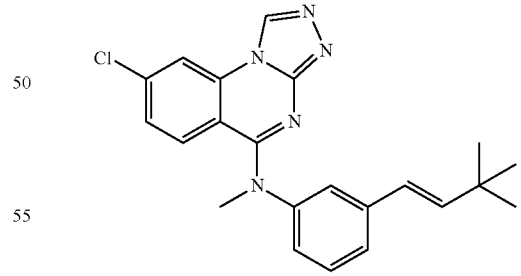

Example 363 was synthesized in a manner similar to Example 312, except using [(E)-3,3-dimethylbut-1-enyl]boronic acid instead of (4-isopropylphenyl)boronic acid. $^1$H NMR (400 MHz, Acetone-$d_6$) δ 9.43 (s, 1H), 8.39 (d, J=2.1 Hz, 1H), 7.50-7.43 (m, 2H), 7.44-7.32 (m, 2H), 7.28 (dd, J=9.0, 2.1 Hz, 1H), 7.16 (dt, J=7.4, 1.8 Hz, 1H), 6.42 (d, J=16.3 Hz, 1H), 6.35 (d, J=16.3 Hz, 1H), 3.62 (s, 3H), 1.10 (s, 9H); LCMS(m/z) 392.3.

Example 364. 1,8-dichloro-N-(4'-cyclopropyl-[1,1'-biphenyl]-3-y)-N-methyl-[1,2,4]triazolo[4,3-a]quinazolin-5-amine

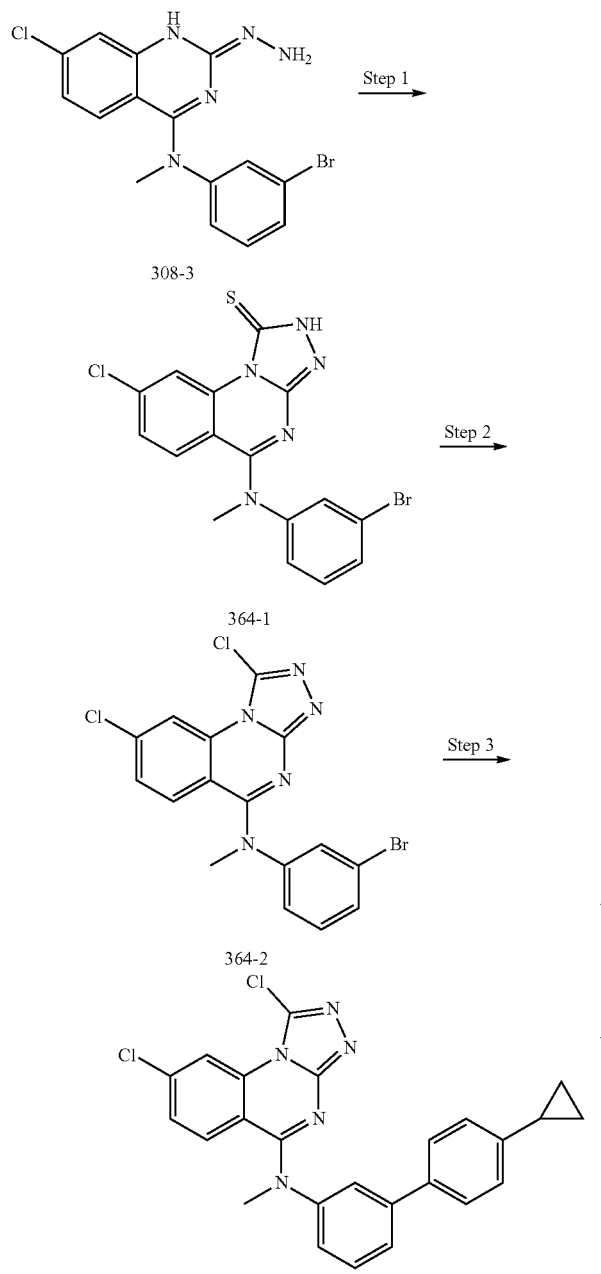

Step 1: A vigorously stirred mixture of Compound 308-3 (1.00 g, 2.64 mmol), carbon disulfide (1.36 mL, 22.7 mmol), and pyridine (13.6 mL, 169 mmol) was heated to 110° C. After 17 h, the resulting mixture was poured into a mixture of ice (75 g), water (25 mL), and saturated aqueous ammonium chloride solution (40 mL), and the resulting suspension was swirled until all of the ice melted. The resulting suspension was filtered, and the filter cake was washed sequentially with water (50 mL) and hexanes (30 mL) and was dried under reduced pressure to give Compound 364-1.

Step 2: A stirred mixture of Compound 364-1 (98.0 mg, 233 µmol) and phosphoryl trichloride (2.3 mL) was heated to 110° C. After 19 min, the resulting mixture was heated to 120° C. After 17 h, the resulting mixture was concentrated under reduced pressure. The residue was purified by reverse phase preparative HPLC (0.1% trifluoroacetic acid in acetonitrile/water) to give Compound 364-2.

Step 3: A vigorously stirred mixture of Compound 364-2 (21.2 mg, 50.1 µmol), (4-cyclopropylphenyl)boronic acid (16.2 mg, 100 µmol), [1,1'-bis(diphenylphosphino)ferrocene]dichloropalladium(II) (3.7 mg, 5.0 µmol), aqueous sodium carbonate solution (2.0 M, 250 µL, 500 µmol), and 1,4-dioxane (0.5 mL) was heated to 90° C. After 25 min, the resulting mixture was cooled to room temperature. Acetic acid (0.4 mL) was added via syringe, and the resulting mixture was concentrated under reduced pressure. The residue was purified by reverse phase preparative HPLC (0.1% trifluoroacetic acid in acetonitrile/water) to give the title compound: $^1$H NMR (400 MHz, Acetone-$d_6$) δ 8.78 (d, J=2.1 Hz, 1H), 7.68-7.61 (m, 2H), 7.59 (dt, J=7.8, 1.3 Hz, 1H), 7.54-7.47 (m, 3H), 7.37-7.31 (m, 2H), 7.18-7.12 (m, 2H), 3.69 (s, 3H), 2.03-1.91 (m, 1H), 1.05-0.93 (m, 2H), 0.78-0.68 (m, 2H); LCMS(m/z) 460.3.

Example 365. 8-chloro-N-methyl-N-(4'-(1,1,1-trifluoro-2-methylpropan-2-yl)-[1,1'-biphenyl]-3-yl)-[1,2,4]triazolo[4,3-a]quinazolin-5-amine

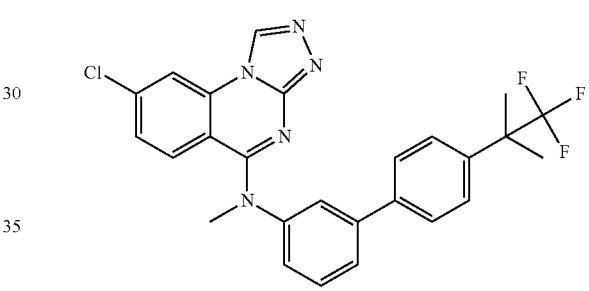

Example 365 was synthesized in a manner similar to Example 312, except using 4,4,5,5-tetramethyl-2-(4-(1,1,1-trifluoro-2-methylpropan-2-yl)phenyl)-1,3,2-dioxaborolane instead of (4-isopropylphenyl)boronic acid. $^1$H NMR (400 MHz, Acetone-$d_6$) δ 9.44 (s, 1H), 8.39 (d, J=2.1 Hz, 1H), 7.70 (t, J=2.0 Hz, 1H), 7.68-7.48 (m, 5H), 7.38 (ddd, J=7.9, 2.3, 1.1 Hz, 2H), 7.26 (dd, J=8.9, 2.1 Hz, 1H), 6.88-6.80 (m, 1H), 3.69 (s, 3H), 1.62 (s, 6H); LCMS(m/z) 496.3.

Example 366. 8-chloro-N-(4'-cyclopropyl-[1,1'-biphenyl]-3-yl)-1-methoxy-N-methyl-[1,2,4]triazolo[4,3-a]quinazolin-5-amine

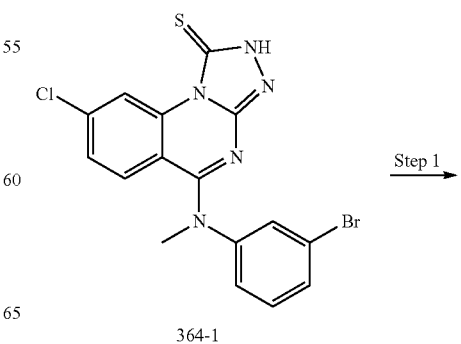

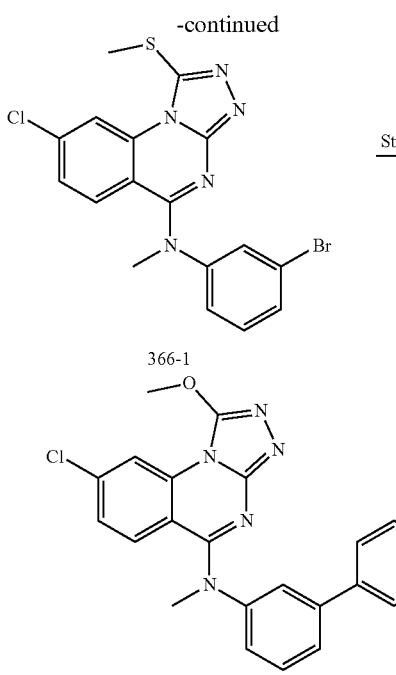

Step 1: Aqueous sodium hydroxide solution (2.0 M, 360 µL, 720 µmol) was added via syringe to a stirred solution of Compound 364-1 (316 mg, 631 µmol) in ethanol (9.0 mL) and tetrahydrofuran (3.0 mL) at room temperature. After 5 min, the resulting mixture was cooled to 0° C., and iodomethane (78.8 µL, 1.26 mmol) was added via syringe. After 90 min, citric acid (200 mg), water (60 mL), ethyl acetate (120 mL), and brine (40 mL) were added sequentially. The resulting biphasic mixture was agitated, and the layers were separated. The organic layer was dried over anhydrous magnesium sulfate, was filtered, and was concentrated under reduced pressure. The residue was purified by flash column chromatography on silica gel (0 to 100% ethyl acetate in hexanes) to give Compound 366-1.

Step 2: 3-Chlorobenzoperoxoic acid (77% wt, 6.0 mg, 27 µmol) was added to a stirred solution of Compound 366-1 (5.0 mg, 12 µmol) in methanol (1.0 mL) at room temperature. After 25 min, 3-chlorobenzoperoxoic acid (77% wt, 8.0 mg, 36 µmol) was added. After 29 min, the resulting mixture was heated to 60° C. After 30 min, the resulting mixture was heated to 70° C. After 80 min, the resulting mixture was cooled to room temperature, and triethylamine (16.0 µL, 115 µmol) was added via syringe. After 2 min, sodium methoxide solution (25% wt in methanol, 78.9 µL, 350 µmol) was added via syringe. After 35 min, saturated aqueous ammonium chloride solution (1.0 mL) and ethyl acetate (50 mL) were added sequentially. The organic layer was washed sequentially with water (25 mL) and a mixture of water and brine (1:1 v:v, 25 mL), was dried over anhydrous magnesium sulfate, was filtered, and was concentrated under reduced pressure. The residue was dissolved in 1,4-dioxane (0.5 mL), and the resulting mixture was stirred at room temperature. (4-Cyclopropylphenyl)boronic acid (2.8 mg, 17 µmol), [1,1'-bis(diphenylphosphino)ferrocene]dichloropalladium(II) (0.8 mg, 1 µmol), and aqueous sodium carbonate solution (2.0 M, 58 µL, 120 µmol) were added sequentially, and the resulting mixture was heated to 100° C. After 5 min, the resulting mixture was cooled to room temperature. Acetic acid (0.1 mL) was added via syringe, and the resulting mixture was concentrated under reduced pressure. The residue was purified by reverse phase preparative HPLC (0.1% trifluoroacetic acid in acetonitrile/water) to give the title compound: $^1$H NMR (400 MHz, Acetone-$d_6$) δ 8.33 (d, J=2.2 Hz, 1H), 7.65-7.42 (m, 6H), 7.31-7.25 (m, 1H), 7.21 (dd, J=8.9, 2.2 Hz, 1H), 7.19-7.10 (m, 2H), 4.37 (s, 3H), 3.63 (s, 3H), 2.03-1.89 (m, 1H), 1.07-0.89 (m, 2H), 0.74-0.66 (m, 2H); LCMS(m/z) 456.3.

Example 367. 1-chloro-N5-(4'-cyclopropyl-[1,1'-biphenyl]-3-yl)-N5-methyl-[1,2,4]triazolo[4,3-a]quinazoline-5,8-diamine

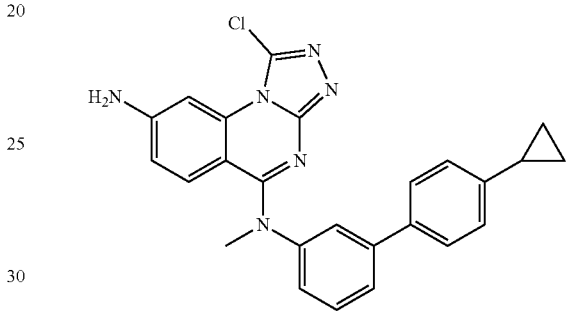

A stirred mixture of Compound 364-2 (20.0 mg, 47.3 µmol), sodium azide (38.3 mg, 589 µmol), and dimethylsulfoxide (0.7 mL) was heated to 80° C. After 44 min, the resulting mixture was heated to 95° C. After 30 min, the resulting mixture was cooled to room temperature, and acetic acid (33.8 µL, 591 µmol), trimethylphosphine solution (1.0 M in tetrahydrofuran, 615 µL, 620 µmol), and water (0.5 mL) were added sequentially. After 75 min ethyl acetate (30 mL) and saturated aqueous sodium bicarbonate solution (5 mL) were added sequentially. The organic layer was washed sequentially with water (50 mL) and a mixture of water and brine (6:1 v:v, 50 mL), was dried over anhydrous magnesium sulfate, was filtered, and was concentrated under reduced pressure. The residue was dissolved in 1,4-dioxane (1.3 mL), and the resulting mixture was stirred at room temperature. (4-Cyclopropylphenyl)boronic acid (15.3 mg, 94.5 µmol), [1,1'-bis(diphenylphosphino)ferrocene]dichloropalladium(II) (2.1 mg, 2.8 µmol), and aqueous sodium carbonate solution (2.0 M, 180 µL, 360 µmol) were added sequentially, and the resulting mixture was heated to 100° C. After 35 min, the resulting mixture was cooled to room temperature. Acetic acid (0.1 mL) was added via syringe, and the resulting mixture was concentrated under reduced pressure. The residue was purified by reverse phase preparative HPLC (0.1% trifluoroacetic acid in acetonitrile/water) to give the title compound: $^1$H NMR (400 MHz, Methanol-$d_4$) δ 7.92 (d, J=2.2 Hz, 1H), 7.67 (d, J=8.1 Hz, 1H), 7.60-7.53 (m, 2H), 7.53-7.25 (m, 3H), 7.15 (d, J=8.3 Hz, 2H), 7.11 (d, J=9.4 Hz, 1H), 6.50 (dd, J=9.3, 2.2 Hz, 1H), 3.76 (s, 3H), 2.00-1.89 (m, 1H), 1.04-0.96 (m, 3H), 0.72 (dt, J=6.6, 4.5 Hz, 3H); LCMS(m/z) 441.3.

Example 368. 4-(3-((8-chloro-[1,2,4]triazolo[4,3-a]quinazolin-5-yl)(methyl)amino)phenyl)-1,1,1-trifluoro-2-methylbut-3-yn-2-ol

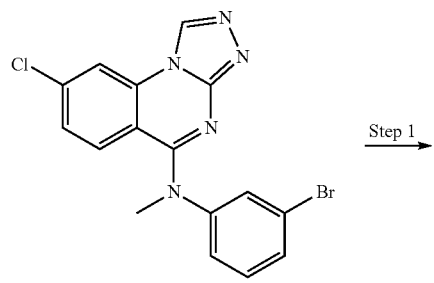

Step 1

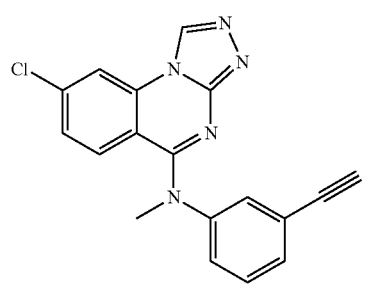

368-1

Step 2

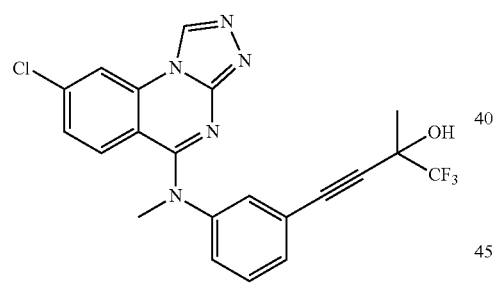

Step 1: A stirred mixture of Example 308 (38.6 mg, 99.3 μmol), trimethyl((tributylstannyl)ethynyl)silane (55.5 μL, 149 μmol), and [1,1'-bis(diphenylphosphino)ferrocene]dichloropalladium(II) (7.3 mg, 9.9 μmol) in 1-methylpyrrolidin-2-one (2.0 mL) was heated to 110° C. After 20 min, the resulting mixture was cooled to room temperature, and methanol (2.0 mL) and potassium carbonate (207 mg, 1.49 mmol) were added sequentially. After 20 min, the resulting mixture was purified by reverse phase preparative HPLC (0.1% trifluoroacetic acid in acetonitrile/water) to give Compound 368-1.

Step 2: Lithium bis(trimethylsilyl)amide solution (1.0 M in tetrahydrofuran, 150 μL, 150 μmol) was added via syringe to a stirred solution of Compound 368-1 (5.0 mg, 15 μmol) in tetrahydrofuran (1.0 mL) at −20° C. After 10 min, 1,1,1-trifluoroacetone (26.8 μL, 300 μmol) was added via syringe. After 10 min, trifluoroacetic acid (0.1 mL) was added via syringe, and the resulting mixture was warmed to room temperature and was concentrated under reduced pressure. The residue was purified by reverse phase preparative HPLC (0.1% trifluoroacetic acid in acetonitrile/water) to give the title compound: $^1$H NMR (400 MHz, Acetone-$d_6$) δ 9.46 (s, 1H), 8.42 (d, J=2.1 Hz, 1H), 7.53-7.43 (m, 3H), 7.43-7.37 (m, 2H), 7.33 (dd, J=9.0, 2.1 Hz, 1H), 5.96 (br-s, 1H), 3.63 (s, 3H), 1.68 (d, J=1.0 Hz, 3H); LCMS(m/z) 446.3.

Example 369. 1-((3-((8-chloro-[1,2,4]triazolo[4,3-a]quinazolin-5-yl)(methyl)amino)phenyl)ethynyl)cyclobutan-1-ol

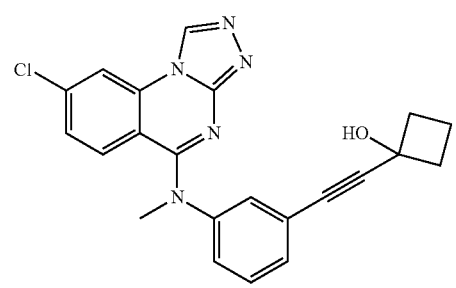 [SMILES: CN(c1cccc(C#CC2(O)CCC2)c1)c1nc2nncn2c2cc(Cl)ccc12]

Example 369 was synthesized in a manner similar to Example 368, except using cyclobutanone instead of 1,1,1-trifluoroacetone. $^1$H NMR (400 MHz, Acetone-$d_6$) δ 9.45 (d, J=1.8 Hz, 1H), 8.41 (d, J=2.1 Hz, 1H), 7.52-7.37 (m, 3H), 7.36-7.30 (m, 3H), 3.62 (s, 2H), 2.50-1.69 (m, 8H); LCMS (m/z) 446.3.

Example 370. 1-(3'-((8-chloro-[1,2,4]triazolo[4,3-a]quinazolin-5-yl)(methyl)amino)-[1,1'-biphenyl]-4-yl)-2,2,2-trifluoroethan-1-ol

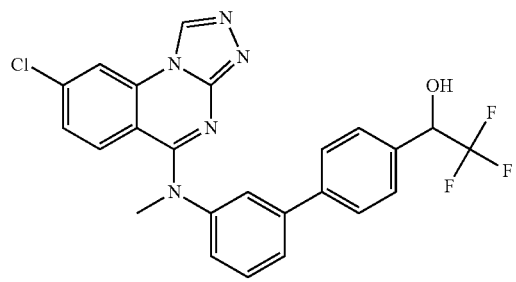

Example 370 was synthesized in a manner similar to Example 312, except using 2,2,2-trifluoro-1-(4-(4,4,5,5-tetramethyl-1,3,2-dioxaborolan-2-yl)phenyl)ethan-1-ol instead of (4-isopropylphenyl)boronic acid. $^1$H NMR (400 MHz, Acetone-$d_6$) δ 9.44 (s, 1H), 8.39 (d, J=2.0 Hz, 1H), 7.75-7.59 (m, 6H), 7.58-7.50 (m, 2H), 7.38 (ddd, J=7.9, 2.2, 1.1 Hz, 1H), 7.26 (dd, J=9.0, 2.1 Hz, 1H), 5.92 (br-s, 1H), 5.27 (q, J=7.2 Hz, 1H), 3.70 (s, 3H); LCMS(m/z) 484.3.

Example 371. 8-chloro-N-(3-(3-methoxy-3-methyl-but-1-yn-1-yl)phenyl)-N-methyl-[1,2,4]triazolo[4,3-a]quinazolin-5-amine Example 372. 4-(3-((8-chloro-[1,2,4]triazolo[4,3-a]quinazolin-5-yl)(methyl)amino)phenyl)-1,1-difluoro-2-methylbut-3-yn-2-ol

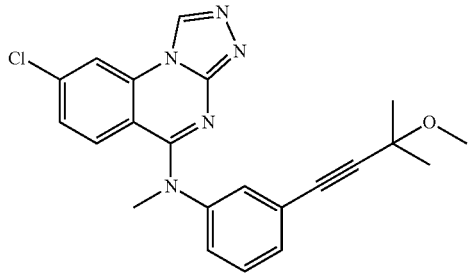 [SMILES: COC(C)(C)C#Cc1cccc(N(C)c2nc3nncn3c3cc(Cl)ccc23)c1]

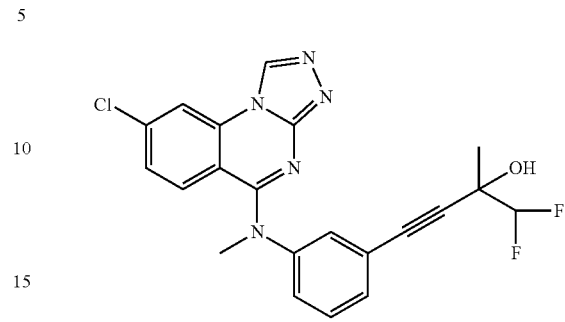

Example 372 was synthesized in a manner similar to Example 376, except using Example 308 instead of Compound 364-2 and using 1,1-difluoro-2-methylbut-3-yn-2-ol instead of 2-methylbut-3-yn-2-ol. $^1$H NMR (400 MHz, Acetone-$d_6$) δ 9.46 (s, 1H), 8.41 (d, J=2.1 Hz, 1H), 7.50-7.30 (m, 6H), 5.84 (t, J=56.3 Hz, 1H), 3.62 (s, 3H), 1.54 (t, J=1.6 Hz, 3H); LCMS(m/z) 428.3.

Example 371 was synthesized in a manner similar to Example 376, except using Example 308 instead of Compound 364-2 and using 3-methoxy-3-methylbut-1-yne instead of 2-methylbut-3-yn-2-ol. $^1$H NMR (400 MHz, Acetone-$d_6$) δ 9.45 (s, 1H), 8.41 (d, J=2.1 Hz, 1H), 7.51-7.44 (m, 2H), 7.44-7.29 (m, 4H), 3.62 (s, 3H), 3.34 (s, 3H), 1.47 (s, 6H); LCMS(m/z) 406.2.

Example 373. (R)-4-(3-((8-chloro-[1,2,4]triazolo[4,3-a]quinazolin-5-yl)(methyl)amino)phenyl)-1-fluoro-2-methylbut-3-yn-2-ol

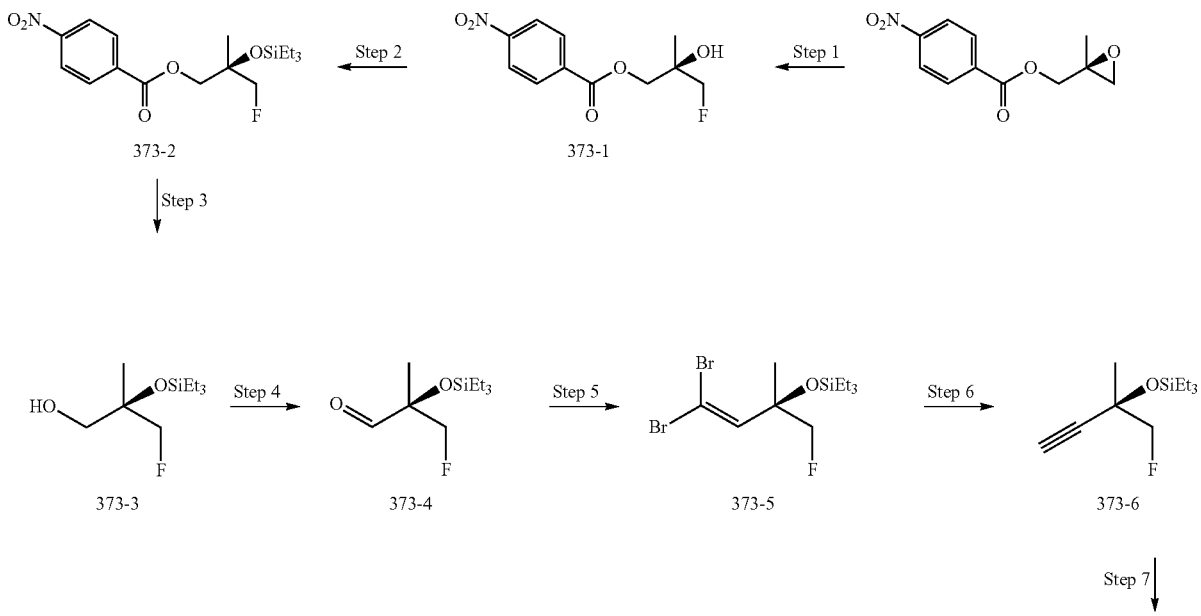

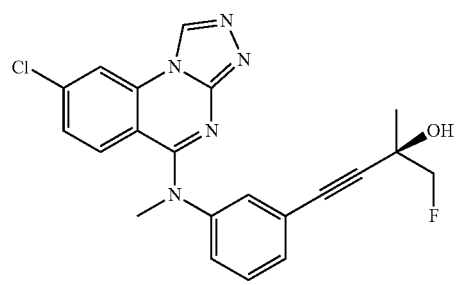

Step 1: A stirred heterogeneous mixture of (S)-(2-methyloxiran-2-yl)methyl 4-nitrobenzoate (4.00 g, 16.9 mmol) and triethylamine trihydrofluoride (6.87 mL, 42.2 mmol) was heated to 80° C. After the mixture became homogeneous, the mixture was heated to 120° C. After 90 min, the resulting mixture was cooled to room temperature and water was added. The aqueous layer was extracted twice with ethyl acetate. Aqueous sodium bicarbonate solution (1.0 M) was added to the combined organic layers, and the resulting mixture was stirred vigorously. After 15 minutes, the resulting mixture was dried over anhydrous sodium sulfate, was filtered, and was concentrated under reduced pressure. The residue was purified by flash column chromatography on silica gel (0 to 20% ethyl acetate in hexanes) to give Compound 373-1.

Step 2: Triethylsilyl trifluoromethanesulfonate (3.82 mL, 16.9 mmol) was added via syringe to a stirred mixture of Compound 373-1 (2.90 g, 11.3 mmol) and 2,6-lutidine (3.94 mL, 33.8 mmol) in dichloromethane (30 mL) at −78° C., and the resulting mixture was warmed to 0° C. After 60 min, the resulting mixture was warmed to room temperature, and the organic layer was washed with aqueous sodium bicarbonate solution (1.0 M, 50 mL). The aqueous layer was extracted with dichloromethane (20 mL), and the combined organic layers were washed with aqueous acetic acid solution (20% v, 50 mL), and the aqueous layer was extracted with dichloromethane (10 mL). The combined organic layers were washed with water (50 mL), were dried over anhydrous sodium sulfate, were filtered, and were concentrated under reduced pressure. The residue was purified by flash column chromatography on silica gel (10% ethyl acetate in hexanes) to give Compound 373-2.

Step 3: Diisobutylaluminum hydride solution (1.0 M in hexanes, 23.6 mL, 24 mmol) was added dropwise via syringe to a stirred solution of Compound 373-2 (3.48 g, 9.37 mmol) in dichloromethane (30 mL) and hexanes (10 mL) at −78° C. After 60 min, saturated aqueous sodium potassium tartrate solution (50 mL) was added slowly, and the resulting mixture was warmed to 0° C. After 45 min, Celite® was added, and the resulting suspension was filtered. The filter cake was extracted with dichloromethane, and the aqueous layer of the combined filtrates was extracted with dichloromethane. The combined organic layers were dried over anhydrous sodium sulfate, were filtered, and were concentrated under reduced pressure. The residue was purified by flash column chromatography on silica gel (0 to 10% ethyl acetate in hexanes) to give Compound 373-3.

Step 4: 1,1,1-Tris(acetyloxy)-1,1-dihydro-1,2-benziodoxol-3-(1H)-one (1.76 g, 4.16 mmol) was added to a stirred solution of Compound 373-3 (840 mg, 3.78 mmol) in dichloromethane (15 mL) at room temperature. After 90 min, the resulting mixture was concentrated under reduced pressure, and the residue was triturated with hexanes (10 mL). The resulting suspension was filtered, and the filter cake was extracted with hexanes. The combined filtrates were washed sequentially with water (10 mL) and aqueous sodium bicarbonate solution (1.0 M). The organic layer was dried over anhydrous sodium sulfate, was filtered, and was concentrated under reduced pressure to give Compound 373-4.

Step 5: A solution of carbon tetrabromide (3.76 g, 11.3 mmol) in toluene (6 mL) was added to a stirred mixture of Compound 373-4 (832 mg, 3.78 mmol) and triphenylphosphine (5.94 g, 22.7 mmol) in toluene (30 mL) at room temperature. After 90 min, the resulting inhomogeneous mixture was filtered, and the filter cake was extracted with hexanes. The combined filtrates were concentrated under reduced pressure. The residue was dissolved in hexanes, and the resulting mixture was filtered through a plug of silica. The filter cake was extracted with hexanes (100 mL), and the combined filtrates were concentrated under reduced pressure. The residue was purified by flash column chromatography on silica gel (hexanes) to give Compound 373-5.

Step 6: Ethylmagnesium bromide solution (3.0 M in diethyl ether, 3.80 mL, 11 mmol) was added dropwise via syringe to a stirred solution of Compound 373-5 (1.10 g, 2.92 mmol) in 2-methyltetrahydrofuran (12 mL) at 0° C. After 2 h, aqueous ammonium chloride solution (4.0 M, 20 mL) and 2-methyltetrahydrofuran (10 mL) were added sequentially. The resulting biphasic mixture was agitated, and the layers were separated. The aqueous layer was extracted with 2-methyltetrahydrofuran, and the combined organic layers were dried over anhydrous sodium sulfate, were filtered, and was concentrated under reduced pressure. The residue was purified by flash column chromatography on silica gel (pentane) to give Compound 373-6.

Step 7: A vigorously stirred mixture of Example 308 (5.0 mg, 13 µmol), Compound 373-6 (8.4 mg, 39 µmol), zinc(II) bromide (14.5 mg, 64.3 µmol), triethylamine (35.9 µL, 257 µmol), and [1,1'-bis(diphenylphosphino)ferrocene]dichloropalladium(II) (2.8 mg, 3.9 µmol) in 1-methylpyrrolidin-2-one (0.9 mL) was heated to 110° C. After 5 min, the resulting mixture was cooled to room temperature, and triethylamine trihydrofluoride (69.2 µL, 425 µmol) was added via syringe. After 20 min, boric acid (40.0 mg, 647 µmol) was added. After 5 min, the resulting mixture was purified by reverse phase preparative HPLC (0.1% trifluoroacetic acid in acetonitrile/water) to give the title compound: $^1$H NMR (400 MHz, Acetone-d$_6$) δ 9.45 (s, 1H), 8.41 (d, J=2.1 Hz, 1H), 7.50-7.39 (m, 3H), 7.34 (tdd, J=8.9, 4.3, 1.8 Hz, 3H), 4.36 (d, J=47.6 Hz, 1H), 3.62 (s, 3H), 1.52 (d, J=2.1 Hz, 3H); LCMS(m/z) 410.3.

Example 374. (S)-4-(3-((8-chloro-[1,2,4]triazolo[4,3-a]quinazolin-5-yl)(methyl)amino)phenyl)-1-fluoro-2-methylbut-3-yn-2-ol

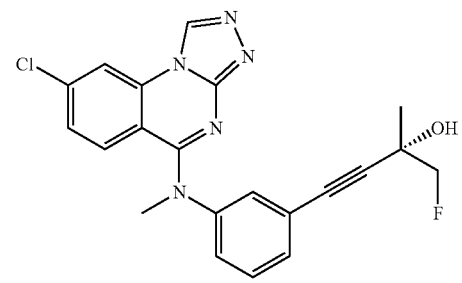 [SMILES: CN(c1cccc(C#C[C@](C)(O)CF)c1)c1nc2nncn2c2cc(Cl)ccc12]

Example 374 was synthesized in a manner similar to Example 373, except using (R)-(2-methyloxiran-2-yl)methyl 4-nitrobenzoate instead of (S)-(2-methyloxiran-2-yl)methyl 4-nitrobenzoate. $^1$H NMR (400 MHz, Acetone-d$_6$) δ 9.45 (s, 1H), 8.41 (d, J=2.0 Hz, 1H), 7.51-7.39 (m, 3H), 7.39-7.29 (m, 3H), 4.36 (d, J=47.6 Hz, 2H), 3.62 (s, 3H), 1.52 (d, J=2.1 Hz, 3H); LCMS(m/z) 410.3.

Example 375. 3-((3-((8-chloro-[1,2,4]triazolo[4,3-a]quinazolin-5-yl)(methyl)amino)phenyl)ethynyl)tetrahydrofuran-3-ol

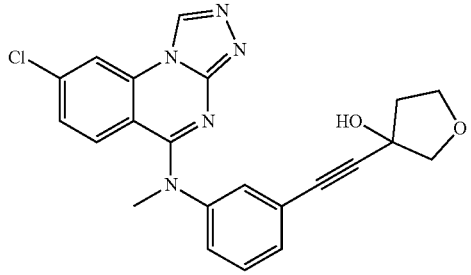 [SMILES: CN(c1cccc(C#CC2(O)CCOC2)c1)c1nc2nncn2c2cc(Cl)ccc12]

A vigorously stirred mixture of Example 308 (5.0 mg, 13 μmol), 3-((trimethylsilyl)ethynyl)tetrahydrofuran-3-ol (10 mg, 54.3 μmol), zinc(II) bromide (14.5 mg, 64.3 μmol), triethylamine (35.9 μL, 257 μmol), cesium fluoride (19.7 mg, 130 μmol), and [1,1'-bis(diphenylphosphino)ferrocene]dichloropalladium(II) (2.8 mg, 3.9 μmol) in 1-methylpyrrolidin-2-one (0.9 mL) was heated to 110° C. After 5 min, the resulting mixture was cooled to room temperature, and the resulting mixture was purified by reverse phase preparative HPLC (0.1% trifluoroacetic acid in acetonitrile/water) to give the title compound: $^1$H NMR (400 MHz, Acetone-d$_6$) δ 9.47 (s, 1H), 8.42 (d, J=2.0 Hz, 1H), 7.49-7.30 (m, 6H), 4.10-3.64 (m, 4H), 3.63 (s, 3H), 2.36-2.16 (m, 2H); LCMS (m/z) 420.3.

Example 376. 4-(3-((1,8-dichloro-[1,2,4]triazolo[4,3-a]quinazolin-5-yl)(methyl)amino)phenyl)-2-methylbut-3-yn-2-ol

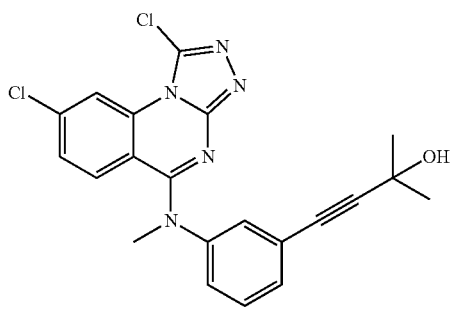 [SMILES: CN(c1cccc(C#CC(C)(C)O)c1)c1nc2nnc(Cl)n2c2cc(Cl)ccc12]

A vigorously stirred mixture of Compound 364-2 (10.0 mg, 23.6 μmol), 2-methylbut-3-yn-2-ol (6.9 μL, 71 μmol), zinc(II) bromide (26.6 mg, 118 μmol), triethylamine (65.9 μL, 473 μmol), [1,1'-bis(diphenylphosphino)ferrocene]dichloropalladium(II) (5.2 mg, 7.1 μmol), and 1-methylpyrrolidin-2-one (0.9 mL) was heated to 110° C. After 5 min, the resulting mixture was cooled to room temperature and was purified by reverse phase preparative HPLC (0.1% trifluoroacetic acid in acetonitrile/water) to give the title compound: $^1$H NMR (400 MHz, Acetone-d$_6$) δ 8.80 (d, J=2.1 Hz, 1H), 7.57 (d, J=8.9 Hz, 1H), 7.46-7.36 (m, 3H), 7.36-7.28 (m, 2H), 3.62 (s, 3H), 1.51 (s, 6H); LCMS(m/z) 426.2.

Example 377. 1,8-dichloro-N-(3-(5-cyclopropylpyrazin-2-yl)phenyl)-N-methyl-[1,2,4]triazolo[4,3-a]quinazolin-5-amine

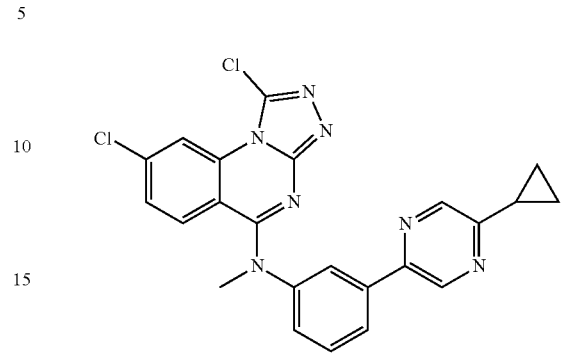

A vigorously stirred mixture of Compound 364-2 (14.0 mg, 33.1 μmol), 4,4,4',4',5,5,5',5'-octamethyl-2,2'-bi(1,3,2-dioxaborolane) (10.1 mg, 39.7 μmol), [1,1'-bis(diphenylphosphino)ferrocene]dichloropalladium(II) (3.6 mg, 5.0 μmol), potassium acetate (32.5 mg, 331 mmol), and 1,4-dioxane (1.0 mL) was heated to 115° C. After 10 min, the resulting mixture was cooled to room temperature, and, 4,4',4',5,5,5',5'-octamethyl-2,2'-bi(1,3,2-dioxaborolane) (4.2 mg, 17 μmol) and [1,1'-bis(diphenylphosphino)ferrocene]dichloropalladium(II) (1.8 mg, 2.5 μmol) were added sequentially. The resulting mixture was heated to 125° C. After 47 min, the resulting mixture was cooled to room temperature, and 2-bromo-5-cyclopropylpyrazine (32.9 mg, 165 μmol), [1,1'-bis(diphenylphosphino)ferrocene]dichloropalladium(II) (2.4 mg, 3.3 μmol), and aqueous sodium carbonate solution (2.0 M, 165 μL, 330 μmol) were added sequentially. The resulting mixture was heated to 110° C. After 40 min, the resulting mixture was cooled to room temperature and was concentrated under reduced pressure. The residue was purified by reverse phase preparative HPLC (0.1% trifluoroacetic acid in acetonitrile/water) to give the title compound: $^1$H NMR (400 MHz, Acetone-d$_6$) δ 8.91 (d, J=1.5 Hz, 1H), 8.79 (d, J=2.0 Hz, 1H), 8.62 (d, J=1.5 Hz, 1H), 8.09 (t, J=2.0 Hz, 1H), 8.07 (s, 1H), 7.63 (d, J=9.0 Hz, 1H), 7.57 (t, J=7.9 Hz, 1H), 7.45 (ddd, J=8.0, 2.3, 1.0 Hz, 1H), 7.35 (dd, J=9.0, 2.1 Hz, 1H), 3.71 (s, 3H), 2.35-1.88 (m, 1H), 1.18-0.99 (m, 4H); LCMS(m/z) 462.3.

Example 378. 1-((3-((8-chloro-[1,2,4]triazolo[4,3-a]quinazolin-5-yl)(methyl)amino)phenyl)ethynyl)-3,3-difluorocyclobutan-1-ol

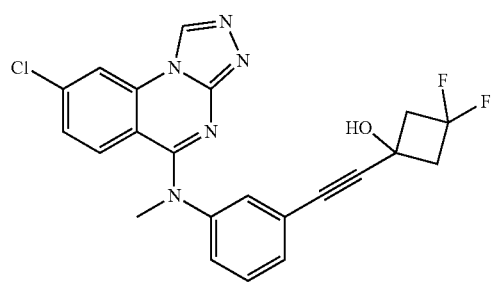 [SMILES: CN(c1cccc(C#CC2(O)CC(F)(F)C2)c1)c1nc2nncn2c2cc(Cl)ccc12]

Lithium bis(trimethylsilyl)amide solution (1.0 M in tetrahydrofuran, 193 μL, 190 μmol) was added via syringe to a stirred solution of 1-ethynyl-3,3-difluorocyclobutan-1-ol (8.5 mg, 64 µmol) in tetrahydrofuran (0.5 mL) at 0° C. After 10 min, tributyltin chloride (41.9 µL, 154 µmol) was added via syringe. After 1 min, the resulting mixture was warmed to room temperature. After 25 min, diethyl ether (30 mL) and saturated aqueous ammonium chloride solution (5 mL) were added sequentially, and the organic layer was washed with water (20 mL), was dried over anhydrous magnesium sulfate, was filtered, and was concentrated under reduced pressure. The residue was dissolved in 1-methylpyrrolidin-2-one (0.9 mL), and the resulting mixture was stirred at room temperature. Example 308 (5.0 mg, 13 µmol) and [1,1'-bis(diphenylphosphino)ferrocene]dichloropalladium (II) (2.8 mg, 3.9 µmol) were added sequentially, and the resulting mixture was heated to 120° C. After 25 min, the resulting mixture was cooled to room temperature and was purified by reverse phase preparative HPLC (0.1% trifluoroacetic acid in acetonitrile/water) to give the title compound: $^1$H NMR (400 MHz, Acetone-$d_6$) δ 9.46 (s, 1H), 8.42 (s, 1H), 7.52-7.29 (m, 6H), 3.62 (s, 3H), 3.17-3.03 (m, 2H), 3.02-2.69 (m, 2H); LCMS(m/z) 440.1.

Example 379. 8-chloro-N-(7-cyclopropyldibenzo[b,d]furan-4-yl)-N-methyl-[1,2,4]triazolo[4,3-a]quinazolin-5-amine Step 2: A vigorously stirred mixture of Compound 379-1 (240 mg, 914 µml) and potassium carbonate (158 mg, 1.13 mmol) in N,N-dimethylformamide (5.0 mL) was heated to 100° C. After 69 min, the resulting mixture was heated to 140° C. After 125 min, the resulting mixture was cooled to room temperature, and ethyl acetate (20 mL), diethyl ether (100 mL), and saturated aqueous ammonium chloride solution (5 mL) were added sequentially. The organic layer was washed with water (2×100 mL), was dried over anhydrous magnesium sulfate, was filtered, and was concentrated under reduced pressure. The residue was purified by flash column chromatography on silica gel (0 to 5% ethyl acetate in hexanes) to give Compound 379-2.

Step 3: A vigorously stirred mixture of Compound 379-2 (100 mg, 412 µmol), methylamine solution (2.0 M in tetrahydrofuran, 412 µL, 820 µmol), sodium tert-butoxide solution (2.0 M in tetrahydrofuran, 278 µL, 560 µmol), and [(2-di-cyclohexylphosphino-3,6-dimethoxy-2',4',6'-triisopropyl-1,1'-biphenyl)-2-(2'-(methylamino)-1,1'-biphenyl)]palladium(II) methanesulfonate (19.0 mg, 20.6 µmol) in tert-butyl alcohol (1.0 mL) was heated to 65° C. After 15 min, the resulting mixture was cooled to room temperature, and saturated aqueous ammonium chloride solution (5 mL) and ethyl acetate (60 mL) were added sequentially. The organic layer was washed with a mixture of water and brine

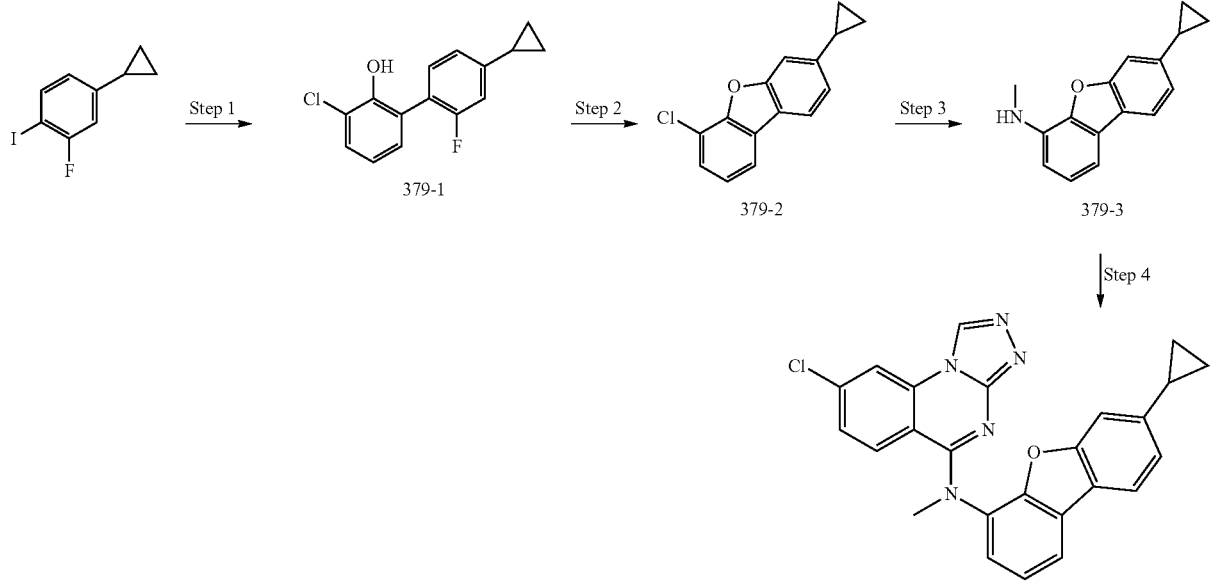

Step 1: A vigorously stirred mixture of 4-cyclopropyl-2-fluoro-1-iodobenzene (250 mg, 954 µmol), (3-chloro-2-hydroxyphenyl)boronic acid (164 mg, 954 µmol), tetrakis(triphenylphosphine)palladium(0) (33.1 mg, 28.6 µmol), aqueous sodium carbonate solution (2.0 M, 1.43 mL, 2.9 mmol), and tetrahydrofuran (2.4 mL) was heated to 75° C. After 16 h, the resulting mixture was cooled to room temperature, and ethyl acetate (60 mL) and aqueous citric acid solution (10% wt, 5 mL) were added sequentially. The organic layer was washed with a mixture of water and brine (2:1 v:v, 50 mL), was dried over anhydrous magnesium sulfate, and was concentrated under reduced pressure. The residue was purified by flash column chromatography on silica gel (0 to 20% ethyl acetate in hexanes) to give Compound 379-1.

(1:1 v:v, 50 mL), was dried over anhydrous magnesium sulfate, was filtered, and was concentrated under reduced pressure. The residue was purified by flash column chromatography on silica gel (0 to 20% ethyl acetate in hexanes) to give Compound 379-3.

Step 4: Sodium bis(trimethylsilyl)amide solution (1.0 M in tetrahydrofuran, 62.1 µL, 120 µmol) was added via syringe to a stirred solution of Compound 379-3 (27.0 mg, 113 µmol) in N,N-dimethylformamide (0.3 mL) at 0° C. After 5 sec, a solution of Intermediate 5 (13.4 mg, 56.5 µmol) in N,N-dimethylformamide (0.7 mL) and tetrahydrofuran (0.3 mL) was added via syringe. After 1 min, the resulting mixture was warmed to room temperature. After 15 min, acetic acid (0.1 mL) was added, and the resulting mixture was concentrated under reduced pressure. The residue was purified by reverse phase preparative HPLC (0.1% trifluoroacetic acid in acetonitrile/water) to give the title compound: ¹H NMR (400 MHz, Acetone-d₆) δ 9.56 (s, 1H), 8.46 (d, J=2.1 Hz, 1H), 8.09-8.05 (m, 1H), 8.03 (d, J=8.1 Hz, 1H), 7.45-7.36 (m, 3H), 7.32 (d, J=1.4 Hz, 1H), 7.24 (dd, J=8.1, 1.5 Hz, 1H), 7.20 (dd, J=9.0, 2.1 Hz, 1H), 3.80 (s, 3H), 2.18-1.95 (m, 1H), 1.13-1.01 (m, 2H), 0.89-0.76 (m, 2H); LCMS(m/z) 440.2.

Example 380. N-methyl-8-(methylsulfonyl)-N-phenyl-[1,2,4]triazolo[4,3-a]quinazolin-5-amine

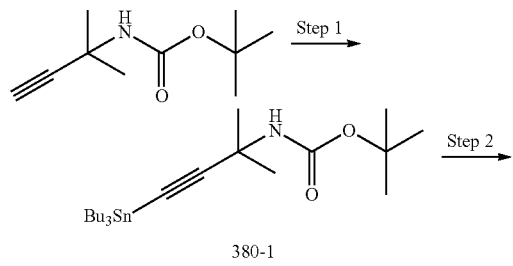

380-1

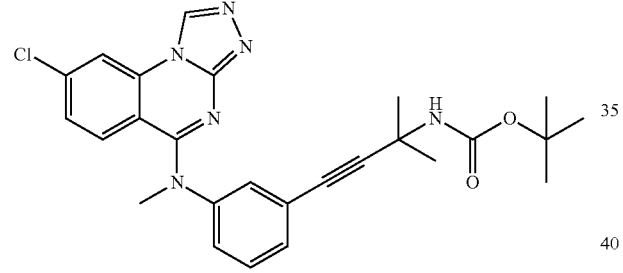

Step 1: n-Butyl lithium solution (2.2 M in heptane, 1.27 mL, 2.8 mmol) was added over 1 min via syringe to a stirred solution of tert-butyl (2-methylbut-3-yn-2-yl)carbamate (252 mg, 1.38 mmol) in tetrahydrofuran (6.0 mL) at −78° C., and the resulting mixture was warmed to 0° C. After 15 min, tributyltin chloride (747 μL, 2.75 μmol) was added via syringe. After 20 min, the resulting mixture was warmed to room temperature. After 90 min, diethyl ether (50 mL) and saturated aqueous ammonium chloride solution (10 mL) were added sequentially. The organic layer was washed sequentially with water (30 mL) and a mixture of water and brine (1:1 v:v, 30 mL), was dried over anhydrous magnesium sulfate, and was concentrated under reduced pressure to give Compound 380-1.

Step 2: Example 380 was synthesized in a manner similar to Example 385, except using Compound 380-1 instead of Compound 385-3. ¹H NMR (400 MHz, Acetone-d₆) δ 9.45 (s, 1H), 8.40 (d, J=2.1 Hz, 1H), 7.46 (d, J=8.9 Hz, 1H), 7.44-7.26 (m, 5H), 3.61 (s, 3H), 1.62 (s, 6H), 1.39 (s, 9H); LCMS(m/z) 491.3.

Example 381. N-methyl-8-(methylsulfonyl)-N-phenyl-[1,2,4]triazolo[4,3-a]quinazolin-5-amine

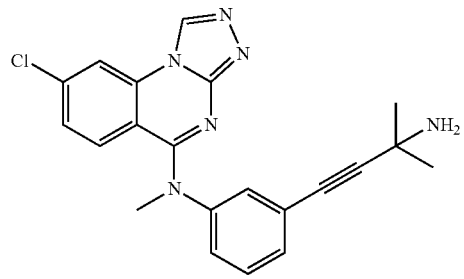 [SMILES: CN(c1cccc(C#CC(C)(C)N)c1)c1nc2nncn2c2cc(Cl)ccc12]

Example 381 was synthesized in a manner similar to Example 350, except starting from Example 380. ¹H NMR (400 MHz, Methanol-d₄) δ 9.57 (s, 1H), 8.49 (d, J=2.0 Hz, 1H), 7.61-7.46 (m, 4H), 7.35 (dd, J=9.1, 2.0 Hz, 1H), 7.27 (d, J=9.0 Hz, 1H), 3.74 (s, 3H), 1.71 (s, 6H); LCMS(m/z) 391.2.

Example 382. N-methyl-8-(methylsulfonyl)-N-phenyl-[1,2,4]triazolo[4,3-a]quinazolin-5-amine

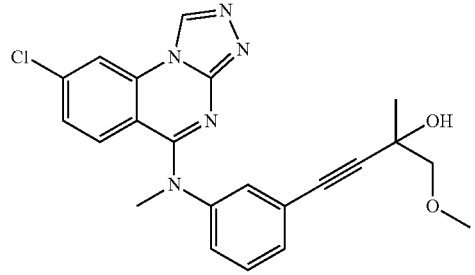 [SMILES: COCC(C)(O)C#Cc1cccc(N(C)c2nc3nncn3c3cc(Cl)ccc23)c1]

Example 382 was synthesized in a manner similar to Example 376, except using Example 308 instead of Compound 364-2 and using 1-methoxy-2-methylbut-3-yn-2-ol instead of 2-methylbut-3-yn-2-ol. ¹H NMR (400 MHz, Acetone-d₆) δ 9.45 (s, 1H), 8.41 (d, J=2.1 Hz, 1H), 7.45 (d, J=8.9 Hz, 1H), 7.43-7.36 (m, 2H), 7.36-7.27 (m, 3H), 3.62 (s, 3H), 3.44 (s, 2H), 3.40 (s, 3H), 1.46 (s, 3H); LCMS(m/z) 422.2.

Example 383. N-methyl-8-(methylsulfonyl)-N-phenyl-[1,2,4]triazolo[4,3-a]quinazolin-5-amine

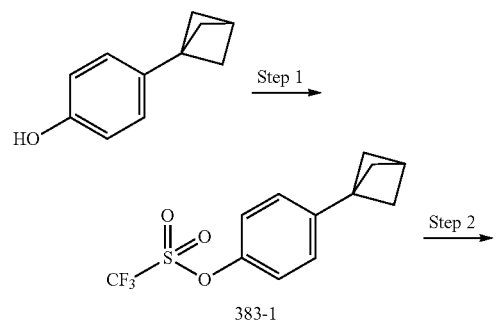

383-1

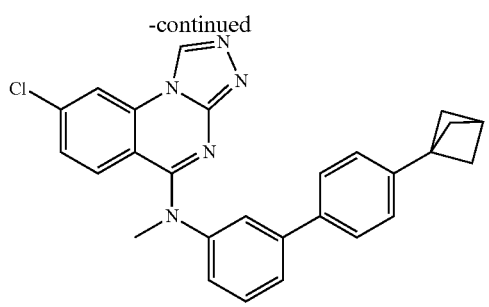

Step 1: Trifluoromethanesulfonic anhydride (257 μL, 1.53 mmol) was added over 3 min via syringe to a stirred mixture of 4-(bicyclo[0.1.1]pentan-1-yl)phenol (122 mg, 763 μmol) and N,N-diisopropylethylamine (532 μL, 3.05 mmol) in dichloromethane (3.0 mL) at 0° C. After 20 min, the resulting mixture was purified by flash column chromatography on silica gel (hexanes) to give Compound 383-1.

Step 2: Example 383 was synthesized in a manner similar to Example 337 using Compound 383-1 instead of 2-bromo-5-cyclopropylpyrazine. $^1$H NMR (400 MHz, Acetone-$d_6$) δ 9.43 (s, 1H), 8.38 (d, J=2.1 Hz, 1H), 7.64 (t, J=2.0 Hz, 1H), 7.61-7.47 (m, 5H), 7.40-7.31 (m, 1H), 7.31-7.22 (m, 3H), 3.68 (s, 3H), 2.55 (s, 1H), 2.10 (s, 6H); LCMS(m/z) 452.3.

Example 384. N-methyl-8-(methylsulfonyl)-N-phenyl-[1,2,4]triazolo[4,3-a]quinazolin-5-amine

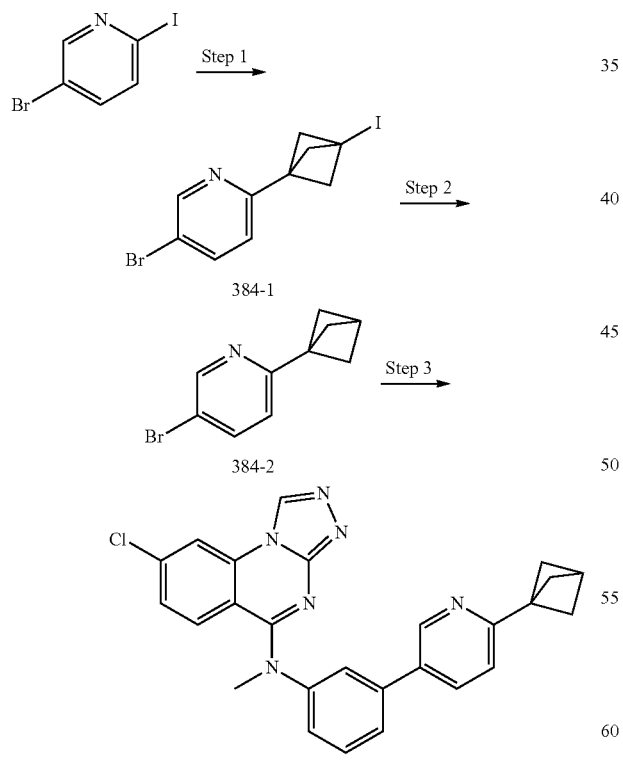

Step 1: A mixture of 5-bromo-2-iodopyridine (500 mg, 1.76 mmol), tricyclo[1.1.1.0$^{1,3}$]pentane solution (0.77 M in diethyl ether, 4.55 mL, 3.5 mmol), [4,4'-bis(1,1-dimethylethyl)-2,2'-bipyridine-N1,N1']bis[3,5-difluoro-2-[5-(trifluoromethyl)-2-pyridinyl-N]phenyl-C]Iridium(III) hexafluorophosphate (49.4 mg, 44.0 μmol), and trimethylacetonitrile (11.7 mL) was degassed via three freeze-thaw-pump cycles (with reduced pressure only applied at −78° C.), was placed under an argon atmosphere, and was stirred at room temperature. The resulting mixture was irradiate with blue light for 16 h and was concentrated under reduced pressure. The residue was purified by flash column chromatography on silica gel (dichloromethane) to give Compound 384-1.

Step 2: Triethylborane solution (1.0 M in hexane, 80.4 μL, 80 μmol) was added via syringe to a stirred mixture of Compound 384-1 (281 mg, 804 μmol) and tributylstannane (237 μL, 884 μmol) in tetrahydrofuran at −78° C. After 15 min, the resulting mixture was warmed to room temperature, was stirred vigorously, and was opened to air. After 120 min aqueous sodium thiosulfate solution (1.0 M, 5 mL), saturated aqueous sodium bicarbonate solution (5 mL), and water (30 mL) were added sequentially. The aqueous layer was extracted with diethyl ether (60 mL), and the organic layer was dried over anhydrous magnesium sulfate, was filtered, and was purified by flash column chromatography on silica gel (0 to 90% dichloromethane in hexanes) to give Compound 384-2.

Step 3: Example 384 was synthesized in a manner similar to Example 337 using Compound 384-2 instead of 2-bromo-5-cyclopropylpyrazine. $^1$H NMR (400 MHz, Acetone-$d_6$) δ 9.46 (s, 1H), 8.71 (dd, J=2.4, 0.9 Hz, 1H), 8.40 (d, J=2.1 Hz, 1H), 7.95 (dd, J=8.1, 2.4 Hz, 1H), 7.71 (t, J=2.0 Hz, 1H), 7.64 (dt, J=7.8, 1.4 Hz, 1H), 7.58 (t, J=7.8 Hz, 1H), 7.51 (d, J=9.0 Hz, 1H), 7.44 (ddd, J=7.8, 2.2, 1.2 Hz, 1H), 7.31 (dd, J=8.1, 0.9 Hz, 1H), 7.27 (dd, J=9.0, 2.1 Hz, 1H), 3.71 (s, 3H), 2.55 (s, 1H), 2.16 (s, 6H); LCMS(m/z) 453.3.

Example 385. N-methyl-8-(methylsulfonyl)-N-phenyl-[1,2,4]triazolo[4,3-a]quinazolin-5-amine

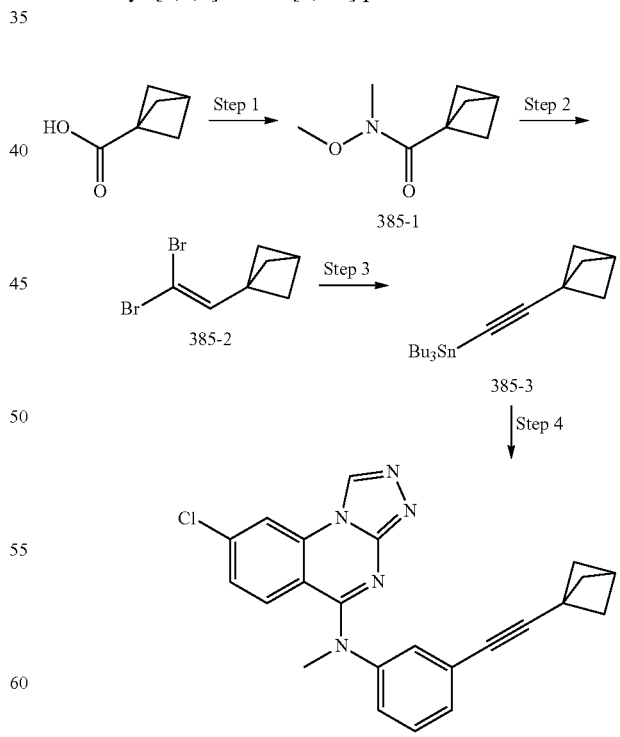

Step 1: 3-(((Ethylimino)methylene)amino)-N,N-dimethylpropan-1-amine hydrochloride (573 mg, 2.99 mmol) was added to a stirred solution of bicyclo[1.1.1]pentane-1-carboxylic acid (223 mg, 1.99 mmol) in dichloromethane (2.5 mL) at room temperature. After 5 min, 1-hydroxybenzotriazole (53.8 mg, 398 µmol), N,O-dimethylhydroxylamine hydrochloride (389 mg, 3.98 mmol), and N,N-diisopropylethylamine (1.21 mL, 6.97 mmol) were added sequentially. After 63 h, the resulting mixture was purified by flash column chromatography on silica gel (0 to 65% diethyl ether in hexanes) to give Compound 385-1.

Step 2: Diisobutylaluminum hydride solution (1.0 M in dichloromethane, 2.32 mL, 2.3 mmol) was added over 2 min via syringe to a stirred solution of Compound 385-1 (266 mg, 1.72 mmol) in dichloromethane (3.0 mL) at −78° C. After 85 min, the resulting mixture was warmed to 0° C. After 17 min, the resulting mixture was warmed to room temperature, and diisobutylaluminum hydride solution (1.0 M in dichloromethane, 1.80 mL, 1.8 mmol) was added via syringe. After 273 min, the resulting mixture was cooled to 0° C., and water (2.0 mL) and aqueous hydrogen chloride solution (2.0 M, 3.0 mL) were added sequentially. The resulting mixture was warmed to room temperature, and water (15 mL) was added. The resulting mixture was filtered through Celite®, and the filter cake was extracted with dichloromethane (25 mL). The combined filtrates were agitated, and the layers were separated. The aqueous layer was extracted with dichloromethane (25 mL), and the combined organic layers were dried over anhydrous magnesium sulfate and were filtered through Celite®. Triphenylphosphine (3.69 g, 14.1 mmol) was added to the filtrate, and the resulting mixture was stirred and was cooled to 0° C. Carbon tetrabromide (2.28 g, 6.87 mmol) was added, and the resulting mixture was warmed to room temperature. After 12 h, the resulting mixture was concentrated under reduced pressure to a volume of approximately 60 mL. The mixture was triturated thoroughly with a mixture of hexanes and diethyl ether (10:1 v:v, 60 mL), and filtered. The filter cake was extracted with hexanes (60 mL), and the combined filtrates were concentrated under reduced pressure. The residue was purified by flash column chromatography on silica gel (hexanes) to give Compound 385-2.

Step 3: n-Butyl lithium solution (2.7 M in heptanes, 83.5 µL, 230 µmol) was added over 1 min via syringe to a stirred solution of Compound 385-2 (7.1 mg, 28.2 µmol) in tetrahydrofuran (3.0 mL) at −78° C. After 60 min, the resulting mixture was warmed to 0° C. After 45 min, tributyltin chloride (61.2 µL, 225 µmol) was added via syringe, and the resulting mixture was warmed to room temperature. After 45 min, diethyl ether (40 mL), hexanes (20 mL), and saturated aqueous sodium bicarbonate solution (10 mL) were added sequentially. The organic layer was washed with anhydrous magnesium sulfate, was filtered, and was concentrated under reduced pressure to give Compound 385-3.

Step 4: A vigorously stirred mixture of Example 308 (5.0 mg, 13 µmol), Compound 385-3 (16.0 mg, 41.9 µmol), [1,1'-bis(diphenylphosphino)ferrocene]dichloropalladium (II) (2.8 mg, 3.9 µmol), and 1-methylpyrrolidin-2-one (0.9 mL) was heated to 110° C. After 12 min, the resulting mixture was cooled to room temperature and was purified by reverse phase preparative HPLC (0.1% trifluoroacetic acid in acetonitrile/water) to give partially purified product, which was further purified by flash column chromatography on silica gel (0 to 100% ethyl acetate in hexanes to 0 to 10% methanol in dichloromethane), and additionally purified by reverse phase preparative HPLC (0.1% trifluoroacetic acid in acetonitrile/water) to give the title compound: $^{1}$H NMR (400 MHz, Acetone-d$_{6}$) δ 9.47 (s, 1H), 8.41 (d, J=2.1 Hz, 1H), 7.46-7.36 (m, 3H), 7.36-7.29 (m, 3H), 3.63 (s, 3H), 2.32 (s, 1H), 2.13 (s, 6H); LCMS(m/z) 400.2.

Example 386. N-(4'-(tert-butyl)-4-fluoro-[1,1'-biphenyl]-3-yl)-8-chloro-N-methyl-[1,2,4]triazolo[4,3-a]quinazolin-5-amine

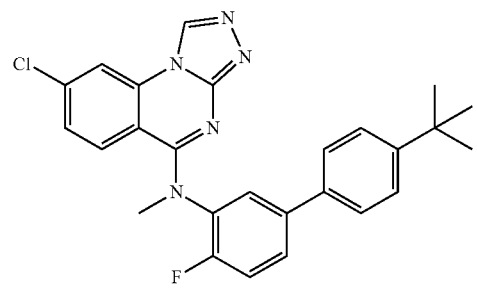 [SMILES: CN(c1cc(-c2ccc(C(C)(C)C)cc2)ccc1F)c1nc2nncn2c2cc(Cl)ccc12]

The title compound was synthesized according to the general procedure described for Example 409: $^{1}$H NMR (400 MHz, Methanol-d$_{4}$) δ 9.60 (s, 1H), 8.53 (d, J=1.9 Hz, 1H), 7.81 (ddd, J=6.9, 3.3, 1.2 Hz, 2H), 7.68-7.28 (m, 7H), 3.81 (s, 3H), 1.35 (s, 9H); LCMS(m/z) 460.4.

Example 387. 8-chloro-N-(4'-cyclopropyl-4-fluoro-[1,1'-biphenyl]-3-yl)-N-methyl-[1,2,4]triazolo[4,3-a]quinazolin-5-amine

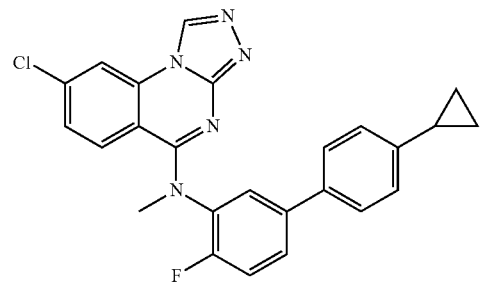 [SMILES: CN(c1cc(-c2ccc(C3CC3)cc2)ccc1F)c1nc2nncn2c2cc(Cl)ccc12]

The title compound was synthesized according to the general procedure described for Example 409: $^{1}$H NMR (400 MHz, Methanol-d$_{4}$) δ 9.60 (s, 1H), 8.53 (d, J=1.8 Hz, 1H), 7.86-7.34 (m, 7H), 7.16 (d, J=8.3 Hz, 2H), 3.81 (s, 3H), 1.94 (tt, J=8.7, 4.2 Hz, 1H), 1.06-0.91 (m, 2H), 0.72 (dt, J=6.6, 4.5 Hz, 2H); LCMS(m/z) 444.4.

Example 388. 8-chloro-N-(4'-(difluoromethyl)-4-fluoro-[1,1'-biphenyl]-3-yl)-N-methyl-[1,2,4]triazolo[4,3-a]quinazolin-5-amine

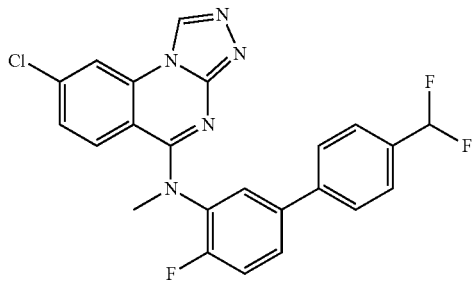 [SMILES: CN(c1cc(-c2ccc(C(F)F)cc2)ccc1F)c1nc2nncn2c2cc(Cl)ccc12]

The title compound was synthesized according to the general procedure described for Example 409: $^1$H NMR (400 MHz, Methanol-d$_4$) δ 9.61 (s, 1H), 8.62-8.49 (m, 1H), 7.88 (ddd, J=10.5, 7.3, 3.1 Hz, 2H), 7.74 (d, J=7.9 Hz, 2H), 7.63 (d, J=8.0 Hz, 2H), 7.59-7.38 (m, 3H), 6.82 (t, J=56.2 Hz, 1H), 3.82 (s, 3H); LCMS(m/z) 454.3.

Example 389. 8-chloro-N-(3-(6-methoxypyridin-3-yl)phenyl)-N-methyl-[1,2,4]triazolo[4,3-a]quinazolin-5-amine

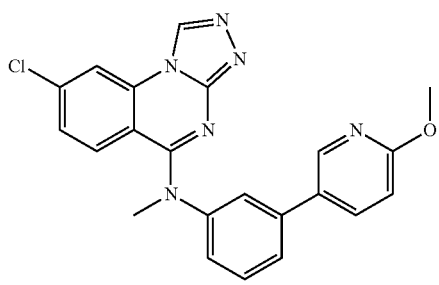 [SMILES: COc1ccc(-c2cccc(N(C)c3nc4nncn4c4cc(Cl)ccc34)c2)cn1]

The title compound was synthesized according to the general procedure described for Example 409: $^1$H NMR (400 MHz, Methanol-d$_4$) δ 9.60 (s, 1H), 8.51 (d, J=2.2 Hz, 1H), 8.38 (d, J=2.7 Hz, 1H), 8.03-7.92 (m, 1H), 7.88-7.59 (m, 3H), 7.54-7.23 (m, 3H), 6.90 (d, J=8.8 Hz, 1H), 3.96 (s, 3H), 3.87 (s, 3H); LCMS(m/z) 417.3.

Example 390. 8-chloro-N-methyl-N-(3-(1-(methylsulfonyl)-1H-pyrazol-4-yl)phenyl)-[1,2,4]triazolo[4,3-a]quinazolin-5-amine

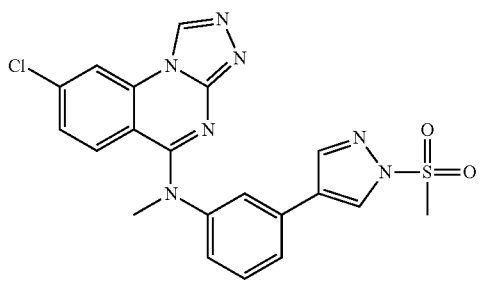 [SMILES: CN(c1cccc(-c2cnn(S(C)(=O)=O)c2)c1)c1nc2nncn2c2cc(Cl)ccc12]

The title compound was synthesized according to the general procedure described for Example 409: $^1$H NMR (400 MHz, Methanol-d$_4$) δ 9.60 (s, 1H), 8.62 (d, J=0.8 Hz, 1H), 8.50 (d, J=2.0 Hz, 1H), 8.29 (d, J=0.8 Hz, 1H), 7.88-7.77 (m, 2H), 7.61 (t, J=7.9 Hz, 1H), 7.46-7.25 (m, 3H), 3.83 (s, 3H), 3.45 (s, 3H); LCMS(m/z) 454.1.

Example 391. 5-(3-((8-chloro-[1,2,4]triazolo[4,3-a]quinazolin-5-yl)(methyl)amino)phenyl)pyrimidine-2-carbonitrile

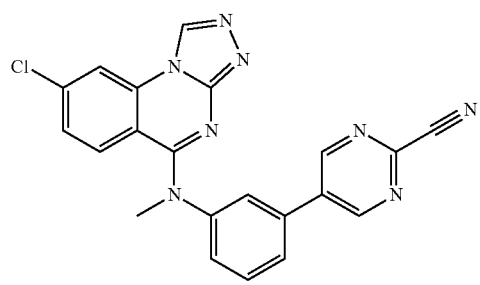 [SMILES: CN(c1cccc(-c2cnc(C#N)nc2)c1)c1nc2nncn2c2cc(Cl)ccc12]

The title compound was synthesized according to the general procedure described for Example 409: $^1$H NMR (400 MHz, Methanol-d$_4$) δ 9.60 (s, 1H), 9.22 (s, 2H), 8.58-8.46 (m, 1H), 7.93 (dt, J=6.8, 1.6 Hz, 2H), 7.75 (t, J=8.2 Hz, 1H), 7.67-7.51 (m, 1H), 7.44-7.26 (m, 2H), 3.85 (s, 3H); LCMS(m/z) 413.3.

Example 392. 8-chloro-N-methyl-N-(4'-(methylsulfonyl)-[1,1'-biphenyl]-3-yl)-[1,2,4]triazolo[4,3-a]quinazolin-5-amine

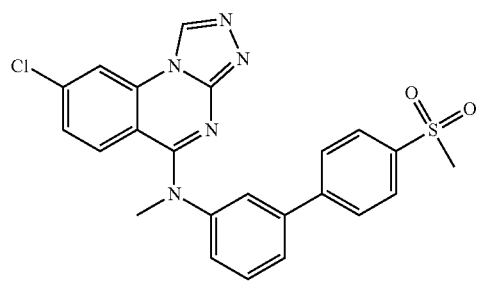

The title compound was synthesized according to the general procedure described for Example 409: $^1$H NMR (400 MHz, Methanol-d$_4$) δ 9.60 (s, 1H), 8.51 (d, J=2.2 Hz, 1H), 8.38 (d, J=2.7 Hz, 1H), 8.02-7.88 (m, 1H), 7.85-7.60 (m, 3H), 7.55-7.20 (m, 3H), 6.90 (d, J=8.7 Hz, 1H), 3.96 (d, J=3.1 Hz, 3H), 3.87 (s, 3H); LCMS(m/z) 464.3.

Example 393. 8-chloro-N-(5-(5-cyclopropylpyrazin-2-yl)-2-fluorophenyl)-N-methyl-[1,2,4]triazolo[4,3-a]quinazolin-5-amine

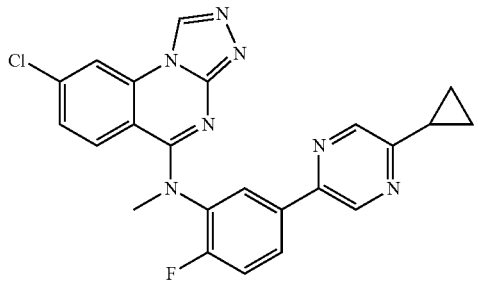

The title compound was synthesized according to the general procedure described for Example 413: $^1$H NMR (400 MHz, Methanol-d$_4$) δ 9.63 (s, 1H), 8.91 (d, J=1.4 Hz, 1H), 8.66-8.49 (m, 2H), 8.43-8.18 (m, 2H), 7.70-7.31 (m, 3H), 3.83 (s, 3H), 2.22 (ddd, J=8.0, 5.3, 3.1 Hz, 1H), 1.23-0.99 (m, 4H); LCMS(m/z) 446.3.

Example 394. N-(5-bromo-2-fluorophenyl)-8-chloro-N-methyl-[1,2,4]triazolo[4,3-a]quinazolin-5-amine

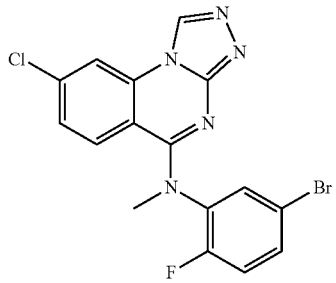 [SMILES: CN(c1cc(Br)ccc1F)c1nc2nncn2c2cc(Cl)ccc12]

The title compound was synthesized according to the general procedure described for Example 409: $^1$H NMR (400 MHz, DMSO-d$_6$) δ 9.67 (s, 1H), 8.60 (d, J=2.1 Hz, 1H), 7.76 (dd, J=7.4, 2.5 Hz, 1H), 7.56 (ddd, J=8.8, 4.3, 2.5 Hz, 1H), 7.48-7.23 (m, 3H), 3.33 (s, 3H); LCMS(m/z) 406.3.

Example 395. N-(3-bromo-2-fluorophenyl)-8-chloro-N-methyl-[1,2,4]triazolo[4,3-a]quinazolin-5-amine

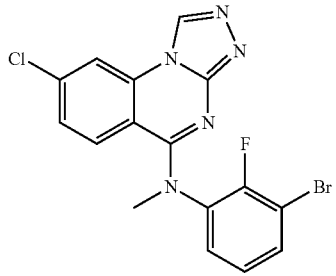

The title compound was synthesized according to the general procedure described for Example 409: $^1$H NMR (400 MHz, DMSO-d$_6$) δ 9.67 (s, 1H), 8.60 (d, J=2.1 Hz, 1H), 7.68 (ddd, J=8.0, 6.4, 1.6 Hz, 1H), 7.49-7.36 (m, 2H), 7.27 (d, J=8.9 Hz, 1H), 7.18 (td, J=8.0, 1.3 Hz, 1H), 3.49 (s, 3H); LCMS(m/z) 406.2.

Example 396. N-(4'-(tert-butyl)-2-fluoro-[1,1'-biphenyl]-3-yl)-8-chloro-N-methyl-[1,2,4]triazolo[4,3-a]quinazolin-5-amine

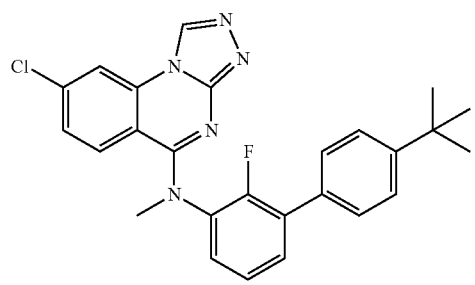

The title compound was synthesized according to the general procedure described for Example 409: $^1$H NMR (400 MHz, Methanol-d$_4$) δ 9.55 (s, 1H), 8.49 (s, 1H), 7.87-7.37 (m, 9H), 3.77 (s, 3H), 1.38 (s, 9H); LCMS(m/z) 460.4.

Example 397. 8-chloro-N-(4'-cyclopropyl-2-fluoro-[1,1'-biphenyl]-3-yl)-N-methyl-[1,2,4]triazolo[4,3-a]quinazolin-5-amine

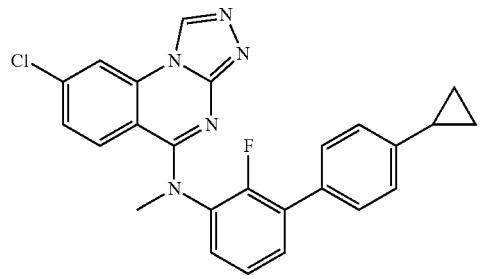

The title compound was synthesized according to the general procedure described for Example 409: $^1$H NMR (400 MHz, Methanol-d$_4$) δ 9.60 (s, 1H), 8.53 (d, J=1.8 Hz, 1H), 7.86-7.34 (m, 7H), 7.16 (d, J=8.3 Hz, 2H), 3.81 (s, 3H), 1.94 (tt, J=8.7, 4.2 Hz, 1H), 1.06-0.91 (m, 2H), 0.72 (dt, J=6.6, 4.5 Hz, 2H); LCMS(m/z) 444.4.

Example 398. 8-chloro-N-(4'-(difluoromethyl)-2-fluoro-[1,1'-biphenyl]-3-yl)-N-methyl-[1,2,4]triazolo[4,3-a]quinazolin-5-amine

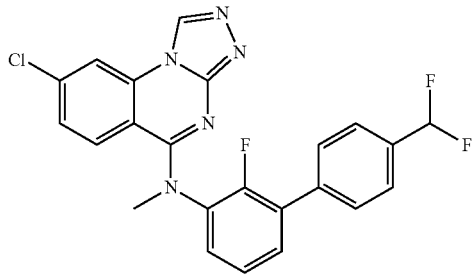

The title compound was synthesized according to the general procedure described for Example 409: $^1$H NMR (400 MHz, Methanol-$d_4$) δ 9.61 (s, 1H), 8.56 (d, J=2.1 Hz, 1H), 7.84-7.38 (m, 9H), 6.84 (t, J=56.1 Hz, 1H), 3.83 (s, 3H); LCMS(m/z) 454.3.

Example 399. 8-chloro-N-(3-(5-cyclopropylpyrazin-2-yl)-2-fluorophenyl)-N-methyl-[1,2,4]triazolo[4,3-a]quinazolin-5-amine

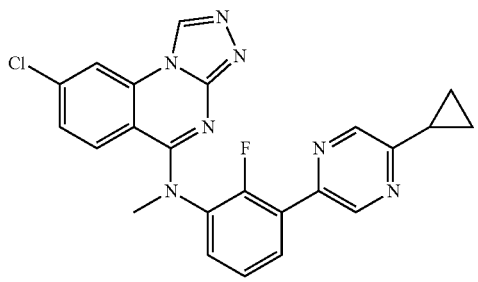

The title compound was synthesized according to the general procedure described for Example 413: $^1$H NMR (400 MHz, Methanol-$d_4$) δ 9.63 (s, 1H), 8.79 (dd, J=2.7, 1.5 Hz, 1H), 8.69 (d, J=1.5 Hz, 1H), 8.57 (d, J=2.0 Hz, 1H), 8.21-8.03 (m, 1H), 7.64 (td, J=7.6, 1.8 Hz, 1H), 7.57-7.34 (m, 3H), 3.84 (s, 3H), 2.26 (tt, J=8.0, 4.9 Hz, 1H), 1.14 (ddt, J=15.1, 5.0, 2.7 Hz, 4H); LCMS(m/z) 446.3.

Example 400. N-(3-bromo-4-fluorophenyl)-8-chloro-N-methyl-[1,2,4]triazolo[4,3-a]quinazolin-5-amine

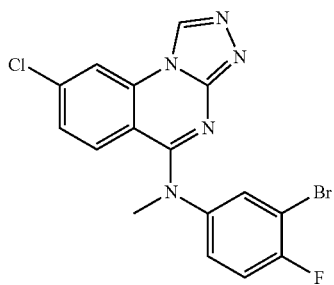 [SMILES: CN(c1ccc(F)c(Br)c1)c1nc2nncn2c2cc(Cl)ccc12]

The title compound was synthesized according to the general procedure described for Example 409: $^1$H NMR (400 MHz, Methanol-$d_4$) δ 9.62 (s, 1H), 8.54 (d, J=2.1 Hz, 1H), 7.84 (dd, J=6.0, 2.6 Hz, 1H), 7.59-7.37 (m, 3H), 7.30 (d, J=9.1 Hz, 1H), 3.78 (s, 3H); LCMS(m/z) 406.2.

Example 401. N-(4'-(tert-butyl)-6-fluoro-[1,1'-biphenyl]-3-yl)-8-chloro-N-methyl-[1,2,4]triazolo[4,3-a]quinazolin-5-amine

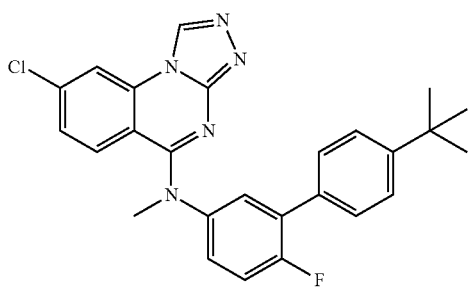 [SMILES: CN(c1ccc(F)c(-c2ccc(C(C)(C)C)cc2)c1)c1nc2nncn2c2cc(Cl)ccc12]

The title compound was synthesized according to the general procedure described for Example 409: $^1$H NMR (400 MHz, Methanol-$d_4$) δ 9.59 (s, 1H), 8.52 (d, J=2.1 Hz, 1H), 7.70-7.08 (m, 9H), 3.84 (s, 3H), 1.35 (s, 9H); LCMS (m/z) 460.4.

Example 402. 8-chloro-N-(4'-cyclopropyl-6-fluoro-[1,1'-biphenyl]-3-yl)-N-methyl-[1,2,4]triazolo[4,3-a]quinazolin-5-amine

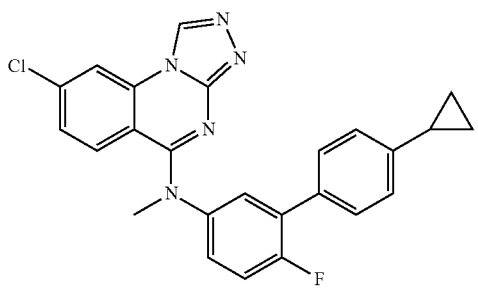

The title compound was synthesized according to the general procedure described for Example 409: $^1$H NMR (400 MHz, Methanol-$d_4$) δ 9.45 (s, 1H), 8.37 (d, J=2.3 Hz, 1H), 7.84-7.05 (m, 9H), 3.70 (d, J=3.5 Hz, 3H), 2.04-1.86 (m, 1H), 1.10-0.66 (m, 4H); LCMS(m/z) 444.4.

Example 403. 8-chloro-N-(4'-(difluoromethyl)-6-fluoro-[1,1'-biphenyl]-3-yl)-N-methyl-[1,2,4]triazolo[4,3-a]quinazolin-5-amine

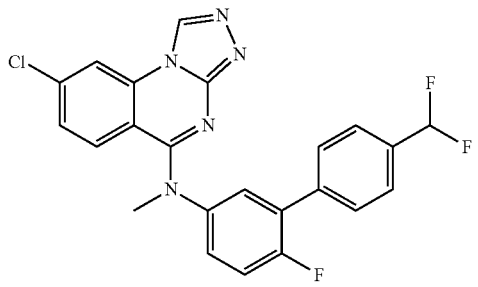 [SMILES: CN(c1ccc(F)c(-c2ccc(C(F)F)cc2)c1)c1nc2nncn2c2cc(Cl)ccc12]

The title compound was synthesized according to the general procedure described for Example 409: ¹H NMR (400 MHz, Methanol-d₄) δ 9.60 (s, 1H), 8.53 (d, J=2.0 Hz, 1H), 7.75-7.30 (m, 9H), 6.83 (t, J=56.1 Hz, 1H), 3.84 (s, 3H); LCMS(m/z) 454.3.

Example 404. 8-chloro-N-(3-(5-cyclopropylpyrazin-2-yl)-4-fluorophenyl)-N-methyl-[1,2,4]triazolo[4,3-a]quinazolin-5-amine

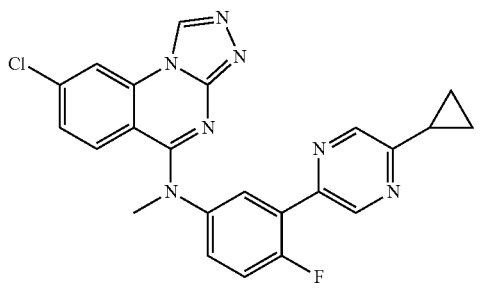

The title compound was synthesized according to the general procedure described for Example 413: ¹H NMR (400 MHz, Methanol-d₄) δ 9.60 (s, 1H), 8.92 (dd, J=2.6, 1.5 Hz, 1H), 8.63 (d, J=1.5 Hz, 1H), 8.52 (d, J=2.1 Hz, 1H), 8.18-8.02 (m, 1H), 7.61-7.26 (m, 4H), 3.84 (s, 3H), 2.24 (tt, J=7.9, 5.0 Hz, 1H), 1.14 (tt, J=7.8, 2.8 Hz, 4H); LCMS(m/z) 446.3.

Example 405. N-(3'-((8-chloro-[1,2,4]triazolo[4,3-a]quinazolin-5-yl)(methyl)amino)-[1,1'-biphenyl]-4-yl)methanesulfonamide

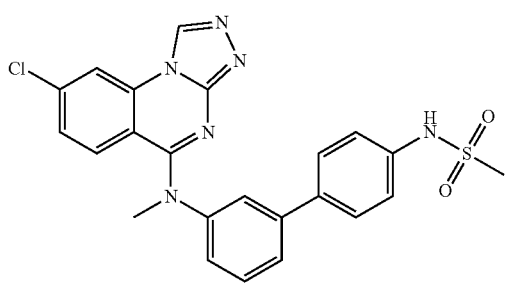

The title compound was synthesized according to the general procedure described for Example 409: ¹H NMR (400 MHz, Methanol-d₄) δ 9.58 (s, 1H), 8.50 (d, J=2.0 Hz, 1H), 7.79 (dt, J=8.1, 1.2 Hz, 1H), 7.72 (t, J=1.9 Hz, 1H), 7.71-7.54 (m, 3H), 7.51-7.23 (m, 5H), 3.86 (s, 3H), 3.00 (s, 3H); LCMS(m/z) 479.3.

Example 406. 3'-((8-chloro-[1,2,4]triazolo[4,3-a]quinazolin-5-yl)(methyl)amino)-[1,1'-biphenyl]-4-carboxamide

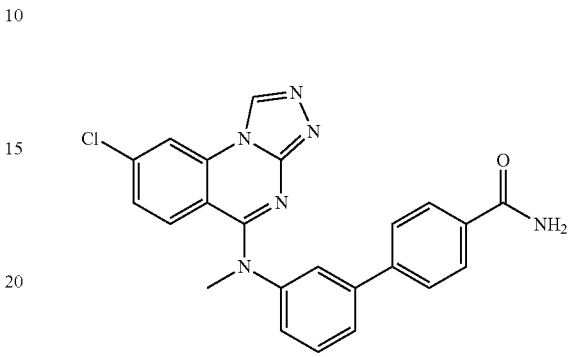

The title compound was synthesized according to the general procedure described for Example 409: ¹H NMR (400 MHz, Methanol-d₄) δ 9.60 (s, 1H), 8.52 (d, J=2.0 Hz, 1H), 8.03-7.92 (m, 2H), 7.87 (d, J=8.0 Hz, 1H), 7.81 (t, J=1.9 Hz, 1H), 7.71 (dd, J=17.1, 8.3 Hz, 3H), 7.56-7.48 (m, 1H), 7.39 (dd, J=9.1, 2.0 Hz, 1H), 7.30 (d, J=9.1 Hz, 1H), 3.88 (s, 3H); LCMS(m/z) 429.3.

Example 407. 8-chloro-N-(3-(3,3-dimethylbut-1-yn-1-yl)-2-fluorophenyl)-N-methyl-[1,2,4]triazolo[4,3-a]quinazolin-5-amine

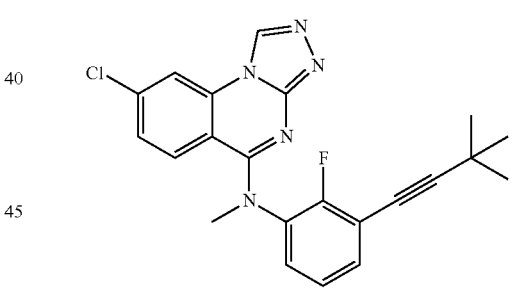

The title compound was synthesized according to the general procedure described for Example 421: ¹H NMR (400 MHz, Methanol-d₄) δ 9.61 (s, 1H), 8.55 (d, J=2.0 Hz, 1H), 7.64-7.39 (m, 3H), 7.38-7.24 (m, 2H), 3.74 (s, 3H), 1.33 (s, 9H); LCMS(m/z) 408.3.

Example 408. N-(3-bromo-5-fluorophenyl)-8-chloro-N-methyl-[1,2,4]triazolo[4,3-a]quinazolin-5-amine

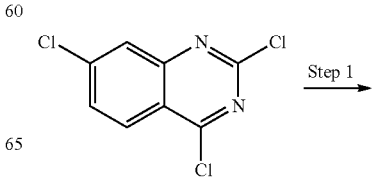

Step 1

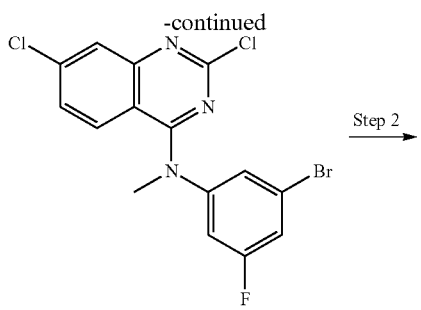

-continued

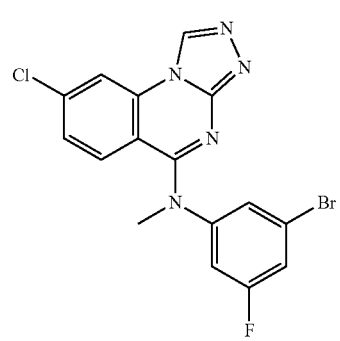

Step 1: To a solution of 2,4,7-trichloroquinazoline (400 mg, 1.71 mmol) and 3-bromo-5-fluoro-N-methylaniline (447 mg, 2.19 mmol, 1.28 equiv.) in DMF (5 mL) at 0° C. was added sodium hydride (60% dispersion in mineral oil, 51 mg, 2.19 mmol, 1.28 equiv.) in one portion. The ice bath was removed, and the mixture was stirred at room temperature for 2h. Upon completion, the reaction mixture was cooled to 0° C. and quenched by slowly addition of saturated aqueous ammonium chloride solution. The material was collected by filtration, washed with water, hexanes, and hexanes/ether (2:1) to remove all impurities. The residue was then further dried under high vacuum to afford N-(3-bromo-5-fluorophenyl)-2,7-dichloro-N-methylquinazolin-4-amine.

Step 2: To a solution of N-(3-bromo-5-fluorophenyl)-2,7-dichloro-N-methylquinazolin-4-amine (1.71 mmol) in THF (15 mL)/ethanol (10 mL) was added hydrazine monohydrate (1.7 ml, 34.3 mmol, 20 equiv.) and the mixture was left stirring at room temperature overnight. Upon completion, ethyl acetate and water were added to the mixture. The aqueous layer was extracted with ethyl acetate (×2). The combined organic layer was washed with brine, dried (MgSO$_4$) and concentrated in vacuo. To the crude (1.71 mmol) was added triethyl orthoformate (12 ml, 74.3 mmol, 43.4 equiv.) and the mixture was heated to 100° C. and stirred for 30 min. Upon completion, the reaction mixture was cooled to room temperature and concentrated under reduced pressure to a minimum volume (<1 ml). The residue was triturated with hexanes and sonicated for a few minutes. The residue was collected by filtration, washed with hexanes: ether (5:1) and dried under high vacuum to afford the title compound: $^1$H NMR (400 MHz, Methanol-d$_4$) δ 9.64 (s, 1H), 8.55 (d, J=2.0 Hz, 1H), 7.58-7.46 (m, 3H), 7.37 (t, J=9.1 Hz, 2H), 3.78 (s, 3H); LCMS(m/z) 406.2.

Example 409. N-(4'-(tert-butyl)-5-fluoro-[1,1'-biphenyl]-3-yl)-8-chloro-N-methyl-[1,2,4]triazolo[4,3-a]quinazolin-5-amine

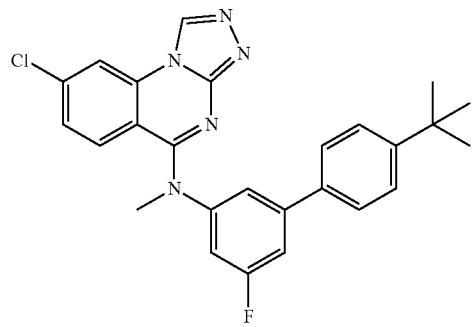

N-(3-bromo-5-fluorophenyl)-8-chloro-N-methyl-[1,2,4]triazolo[4,3-a] quinazolin-5-amine (Example 408, 25 mg, 61.5 μmol), (4-tert-butylphenyl) boronic acid (11 mg, 61.5 μmol, 1.0 equiv.) were dissolved in dimethylformamide (1 ml) and water (0.1 ml). Potassium carbonate (21 mg, 154 μmol, 2.5 equiv.) and tetrakis(triphenylphosphine)palladium (0) (14 mg, 12.3 μmol, 20 mol %) were added. The mixture was purged with argon and then heated to 84° C. Upon completing, ethyl acetate and water were added to the mixture. The organic layer was concentrated in vacuo. The residue was purified by reverse phase HPLC (0.1% trifluoroacetic acid in acetonitrile/water) providing the title compound as the mono-TFA salt: $^1$H NMR (400 MHz, Methanol-d$_4$) δ 9.50 (s, 1H), 8.41 (d, J=2.0 Hz, 1H), 7.54-7.43 (m, 5H), 7.45-7.28 (m, 3H), 7.13 (dt, J=9.5, 2.1 Hz, 1H), 3.75 (s, 3H), 1.35 (s, 9H); LCMS(m/z) 460.4.

Example 410. 8-chloro-N-(4'-cyclopropyl-5-fluoro-[1,1'-biphenyl]-3-yl)-N-methyl-[1,2,4]triazolo[4,3-a]quinazolin-5-amine

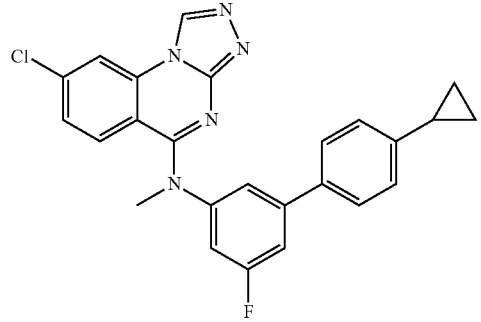 [SMILES: CN(c1cc(F)cc(-c2ccc(C3CC3)cc2)c1)c1nc2nncn2c2cc(Cl)ccc12]

The title compound was synthesized according to the general procedure described for Example 409: $^1$H NMR (400 MHz, Methanol-d$_4$) δ 9.48 (s, 1H), 8.39 (d, J=2.0 Hz, 1H), 7.47 (dd, J=14.6, 8.7 Hz, 3H), 7.40-7.25 (m, 3H), 7.19-7.00 (m, 3H), 3.73 (s, 3H), 1.99-1.85 (m, 1H), 1.00 (dd, J=8.5, 2.1 Hz, 2H), 0.78-0.62 (m, 2H); LCMS(m/z) 444.4.

Example 411. 8-chloro-N-(4'-(difluoromethyl)-5-fluoro-[1,1'-biphenyl]-3-yl)-N-methyl-[1,2,4]triazolo[4,3-a]quinazolin-5-amine

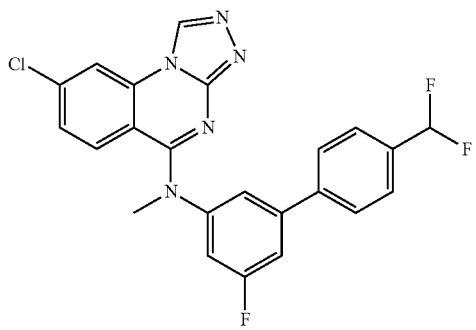 [SMILES: CN(c1cc(F)cc(-c2ccc(C(F)F)cc2)c1)c1nc2nncn2c2cc(Cl)ccc12]

The title compound was synthesized according to the general procedure described for Example 409: $^1$H NMR (400 MHz, Methanol-$d_4$) δ 9.61 (s, 1H), 8.52 (t, J=1.2 Hz, 1H), 7.74 (d, J=8.1 Hz, 2H), 7.68-7.55 (m, 4H), 7.50-7.39 (m, 2H), 7.34 (dt, J=9.1, 2.2 Hz, 1H), 6.82 (t, J=56.1 Hz, 1H), 3.84 (s, 3H); LCMS(m/z) 454.3.

Example 412. 8-chloro-N-(3'-fluoro-4'-(methylsulfonyl)-[1,1'-biphenyl]-3-yl)-N-methyl-[1,2,4]triazolo[4,3-a]quinazolin-5-amine

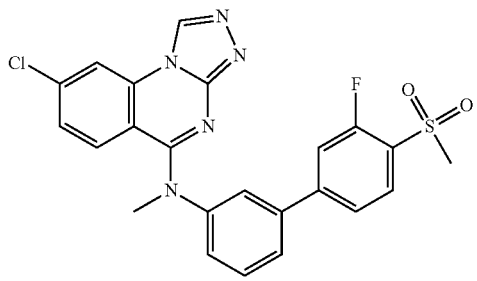 [SMILES: CN(c1cccc(-c2ccc(S(C)(=O)=O)c(F)c2)c1)c1nc2nncn2c2cc(Cl)ccc12]

The title compound was synthesized according to the general procedure described for Example 409: $^1$H NMR (400 MHz, Methanol-$d_4$) δ 9.60 (s, 1H), 8.51 (d, J=2.0 Hz, 1H), 8.01 (t, J=7.7 Hz, 1H), 7.92-7.81 (m, 2H), 7.79-7.65 (m, 3H), 7.56 (ddd, J=8.0, 2.2, 1.0 Hz, 1H), 7.38 (dd, J=9.1, 2.0 Hz, 1H), 7.31 (d, J=9.1 Hz, 1H), 3.86 (s, 3H), 3.29 (s, 3H); LCMS(m/z) 482.2.

Example 413. 8-chloro-N-(3-(5-cyclopropylpyrazin-2-yl)-5-fluorophenyl)-N-methyl-[1,2,4]triazolo[4,3-a]quinazolin-5-amine

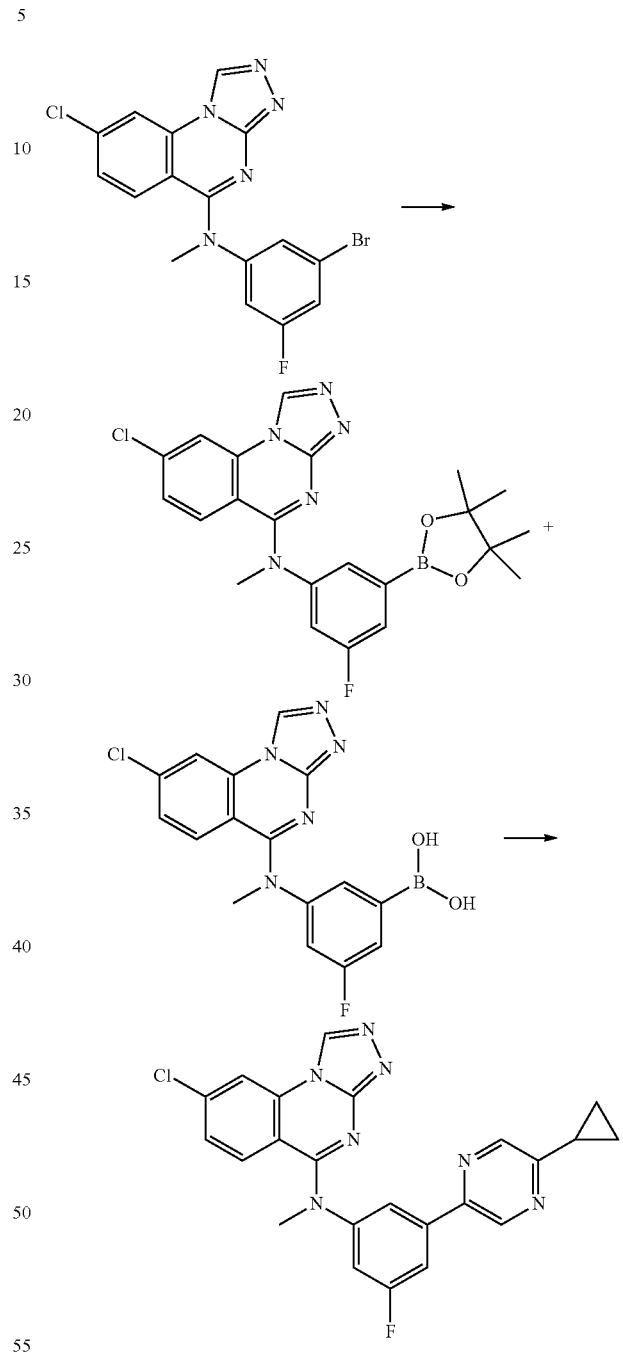

To the mixture of N-(3-bromo-5-fluorophenyl)-8-chloro-N-methyl-[1,2,4]triazolo[4,3-a]quinazolin-5-amine (Example 408, 60 mg, 148 μmol) and bis(pinacolato)diboron (41 mg, 162 μmol, 1.1 equiv.) in 1,4-dioxane (2 ml) was added potassium acetate (72 mg, 738 μmol, 5.0 equiv.), bis(diphenylphosphino)ferrocene)palladium(II) dichloride (5.4 mg, 7.38 μmol, 5 mol %). The mixture was purged with argon and then heated to 110° C. Upon completion, the mixture was cooled to room temperature, silica gel (250 mg) and ethyl acetate were added, and the mixture was concentrated to dryness. The crude was dry-loaded to a silica gel column and eluted with 0-20% methanol/dichloromethane to afford a mixture of 8-chloro-N-(3-fluoro-5-(4,4,5,5-tetramethyl-1,3,2-dioxaborolan-2-yl) phenyl)-N-methyl-[1,2,4] triazolo[4,3-a]quinazolin-5-amine and its corresponding boronic acid.

To the above mixture (148 µmol) in 1,4-dioxane (1 ml) and water (0.1 ml) was added 2-bromo-5-cyclopropylpyrazine (44 mg, 221 µmol, 1.5 equiv.), potassium carbonate (72 mg, 516 µmol, 3.5 equiv.) and bis(diphenylphosphino)ferrocene) palladium (II) dichloride (12 mg, 14.8 µmol, 10 mol %). The mixture was purged with argon and then heated to 120° C. Upon completing, the mixture was filtered through a short bed of Celite®, rinsed the Celite® with ethyl acetate, the filtrate was concentrated in vacuo. The residue was dissolved in methanol (3 ml) and trifluoroacetic acid (0.2 ml), and purified by reverse phase HPLC (0.1% trifluoroacetic acid in acetonitrile/water) providing the title compound as the mono-TFA salt: $^1$H NMR (400 MHz, Methanol-$d_4$) δ 9.64 (s, 1H), 8.92 (d, J=1.5 Hz, 1H), 8.60 (d, J=1.5 Hz, 1H), 8.54 (dd, J=1.7, 0.7 Hz, 1H), 8.04-7.92 (m, 2H), 7.49-7.24 (m, 3H), 3.86 (s, 3H), 2.23 (tt, J=8.0, 4.9 Hz, 1H), 1.12 (ddt, J=14.5, 5.0, 2.7 Hz, 4H); LCMS(m/z) 446.3.

Example 414. 3'-((8-chloro-[1,2,4]triazolo[4,3-a]quinazolin-5-yl)(methyl)amino)-[1,1'-biphenyl]-4-sulfonamide

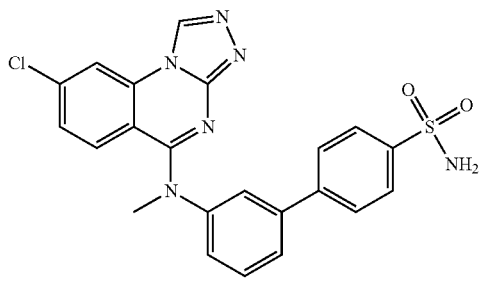 [SMILES: CN(c1cccc(-c2ccc(S(N)(=O)=O)cc2)c1)c1nc2nncn2c2cc(Cl)ccc12]

The title compound was synthesized according to the general procedure described for Example 409: $^1$H NMR (400 MHz, Methanol-$d_4$) δ 9.59 (s, 1H), 8.50 (d, J=2.0 Hz, 1H), 7.98 (d, J=8.5 Hz, 2H), 7.93-7.77 (m, 4H), 7.69 (t, J=7.9 Hz, 1H), 7.50 (ddd, J=7.9, 2.3, 1.0 Hz, 1H), 7.43-7.27 (m, 2H), 3.86 (s, 3H); LCMS(m/z) 465.3.

Example 415. 8-chloro-N-(3-(6-(dimethylamino)pyridin-3-yl)phenyl)-N-methyl-[1,2,4]triazolo[4,3-a]quinazolin-5-amine

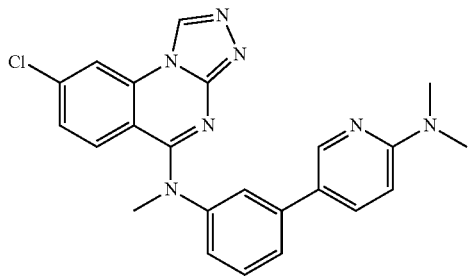 [SMILES: CN(C)c1ccc(-c2cccc(N(C)c3nc4nncn4c4cc(Cl)ccc34)c2)cn1]

The title compound was synthesized according to the general procedure described for Example 409: $^1$H NMR (400 MHz, Methanol-$d_4$) δ 9.59 (s, 1H), 8.50 (dd, J=1.9, 0.6 Hz, 1H), 8.27 (dd, J=9.6, 2.4 Hz, 1H), 8.17 (dd, J=2.4, 0.7 Hz, 1H), 7.77 (dt, J=3.2, 1.9 Hz, 2H), 7.67 (t, J=8.1 Hz, 1H), 7.48 (ddd, J=7.9, 2.1, 1.1 Hz, 1H), 7.36-7.26 (m, 3H), 3.84 (s, 3H), 3.33 (s, 6H); LCMS(m/z) 430.3.

Example 416. (3'-((8-chloro-[1,2,4]triazolo[4,3-a]quinazolin-5-yl)(methyl)amino)-[1,1'-biphenyl]-4-yl)(morpholino)methanone

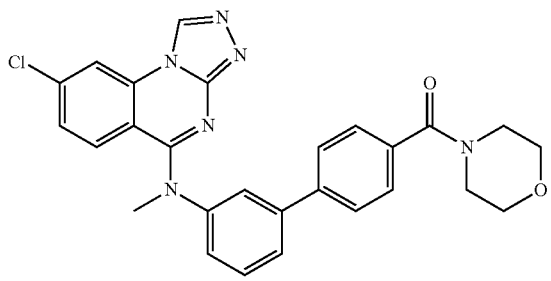

The title compound was synthesized according to the general procedure described for Example 409: $^1$H NMR (400 MHz, Methanol-$d_4$) δ 9.59 (s, 1H), 8.51 (d, J=2.0 Hz, 1H), 7.85 (ddd, J=7.8, 1.8, 1.0 Hz, 1H), 7.80-7.64 (m, 4H), 7.61-7.45 (m, 3H), 7.38 (dd, J=9.2, 2.1 Hz, 1H), 7.30 (d, J=9.1 Hz, 1H), 3.87 (s, 3H), 3.84-3.38 (m, 8H); LCMS(m/z) 499.3.

Example 417. 8-chloro-5-(5-fluoro-3,4-dihydroquinolin-1(2H)-yl)-[1,2,4]triazolo[4,3-a]quinazoline

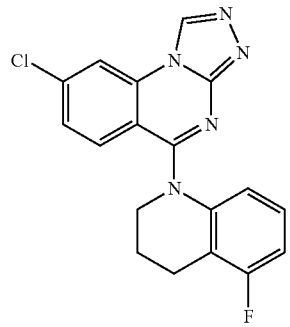

The title compound was synthesized according to the general procedure described for Example 498: $^1$H NMR (400 MHz, Methanol-$d_4$) δ 9.66 (s, 1H), 8.56 (d, J=2.0 Hz, 1H), 7.74 (d, J=9.0 Hz, 1H), 7.52 (dd, J=9.0, 2.0 Hz, 1H), 7.17-6.93 (m, 2H), 6.79 (d, J=8.1 Hz, 1H), 4.22 (t, J=6.3 Hz, 2H), 3.01 (t, J=6.8 Hz, 2H), 2.25 (q, J=6.5 Hz, 2H); LCMS(m/z) 354.3.

Example 418. 9-bromo-5-(8-chloro-[1,2,4]triazolo[4,3-a]quinazolin-5-yl)-2,3,4,5-tetrahydrobenzo[b][1,4]oxazepine

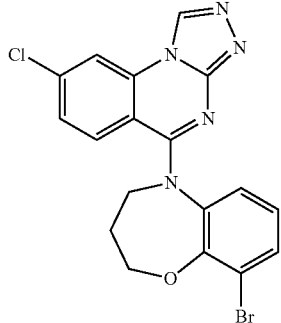

The title compound was synthesized according to the general procedure described for Example 498: $^1$H NMR (400 MHz, Methanol-$d_4$) δ 9.61 (s, 1H), 8.52 (d, J=2.1 Hz, 1H), 7.75 (dd, J=8.0, 1.7 Hz, 1H), 7.44 (dd, J=9.1, 2.1 Hz, 1H), 7.18-6.95 (m, 3H), 4.50-4.29 (m, 2H), 3.37-3.28 (m, 2H), 2.37-2.16 (m, 2H); LCMS(m/z) 430.4.

Example 419. 8-chloro-5-(1,1a,2,7b-tetrahydro-3H-cyclopropa[c]quinolin-3-yl)-[1,2,4]triazolo[4,3-a]quinazoline

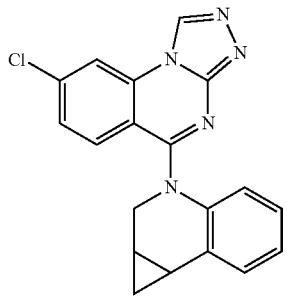

The title compound was synthesized according to the general procedure described for Example 498: $^1$H NMR (400 MHz, Methanol-$d_4$) δ 9.62 (s, 1H), 8.53 (d, J=2.0 Hz, 1H), 7.57 (dd, J=7.6, 1.5 Hz, 1H), 7.51 (d, J=9.0 Hz, 1H), 7.45 (dd, J=9.0, 2.0 Hz, 1H), 7.26 (td, J=7.5, 1.2 Hz, 1H), 7.04 (td, J=7.8, 1.5 Hz, 1H), 6.84 (dd, J=8.0, 1.2 Hz, 1H), 5.12 (dd, J=12.6, 1.7 Hz, 1H), 3.40 (dd, J=12.7, 2.0 Hz, 1H), 2.32 (q, J=7.2 Hz, 1H), 2.16 (dp, J=8.1, 1.9 Hz, 1H), 1.31-1.13 (m, 2H); LCMS(m/z) 348.3.

Example 420. 8-chloro-N-(5-fluoro-4'-(methylsulfonyl)-[1,1'-biphenyl]-3-yl)-N-methyl-[1,2,4]triazolo[4,3-a]quinazolin-5-amine

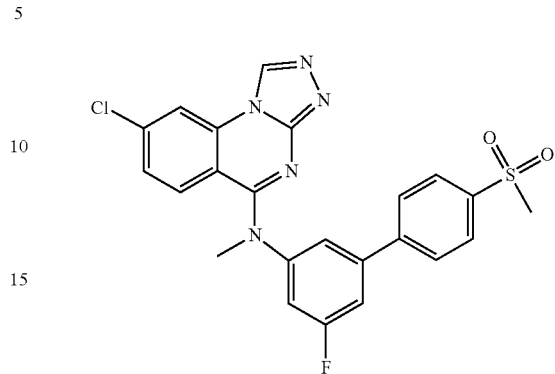

The title compound was synthesized according to the general procedure described for Example 409: $^1$H NMR (400 MHz, Methanol-$d_4$) δ 9.64 (s, 1H), 8.55 (d, J=1.9 Hz, 1H), 8.05 (d, J=8.5 Hz, 2H), 7.89 (d, J=8.6 Hz, 2H), 7.73-7.61 (m, 2H), 7.50-7.36 (m, 3H), 3.87 (s, 3H), 3.16 (s, 3H); LCMS(m/z) 482.3.

Example 421. 4-(3-((8-chloro-[1,2,4]triazolo[4,3-a]quinazolin-5-yl)(methyl)amino)-5-fluorophenyl)-2-methylbut-3-yn-2-ol

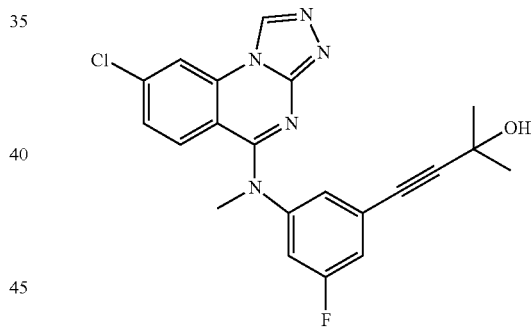

N-(3-bromo-5-fluorophenyl)-8-chloro-N-methyl-[1,2,4]triazolo[4,3-a] quinazolin-5-amine (20 mg, 49.2 μmol), 2-methylbut-3-yn-2-ol (12 mg, 148 μmol, 3.0 equiv.) were dissolved in N-methyl-2-pyrrolidone (1 ml). Zinc bromide (55 mg, 246 μmol, 5.0 equiv.), (1,1'-bis(diphenylphosphino)ferrocene) palladium (II) dichloride (11 mg, 14.8 μmol, 30 mol %) and triethylamine (0.14 ml, 984 μmol, 20.0 equiv.) were added. The mixture was heated at 110° C. for 10 minutes. Upon completion, the mixture was cooled to room temperature, and ethyl acetate and water were added to the mixture. The organic layer was concentrated in vacuo. The residue was purified by reverse phase HPLC (0.1% trifluoroacetic acid in acetonitrile/water) providing the title compound as the mono-TFA salt: $^1$H NMR (400 MHz, Methanol-$d_4$) δ 9.63 (s, 1H), 8.55 (d, J=2.1 Hz, 1H), 7.49 (dd, J=9.1, 2.1 Hz, 1H), 7.43-7.19 (m, 4H), 3.78 (s, 3H), 1.53 (s, 6H); LCMS(m/z) 410.2.

Example 422. N-(4'-(tert-butyl)-5-fluoro-[1,1'-biphenyl]-3-yl)-7-fluoro-N-methyl-[1,2,4]triazolo[4,3-a]quinazolin-5-amine

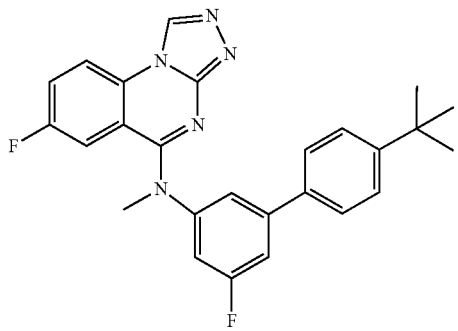

The title compound was synthesized according to the general procedure described for Example 409: ¹H NMR (400 MHz, Methanol-d₄) δ 9.62 (s, 1H), 8.41 (dd, J=9.2, 4.7 Hz, 1H), 7.79 (ddd, J=9.2, 7.5, 2.7 Hz, 1H), 7.64-7.45 (m, 6H), 7.35-7.23 (m, 1H), 7.03 (dd, J=10.3, 2.7 Hz, 1H), 3.86 (s, 3H), 1.35 (s, 9H); LCMS(m/z) 444.4.

Example 423. N-(4'-cyclopropyl-5-fluoro-[1,1'-biphenyl]-3-yl)-7-fluoro-N-methyl-[1,2,4]triazolo[4,3-a]quinazolin-5-amine

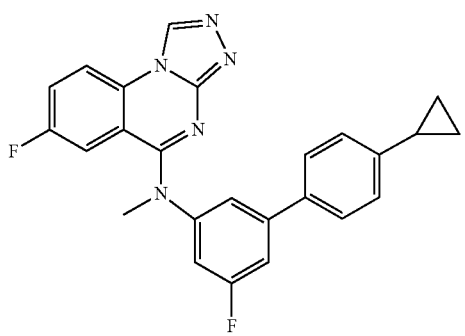

The title compound was synthesized according to the general procedure described for Example 409: ¹H NMR (400 MHz, Methanol-d₄) δ 9.62 (s, 1H), 8.42 (dd, J=9.2, 4.7 Hz, 1H), 7.80 (ddd, J=9.2, 7.5, 2.7 Hz, 1H), 7.69-7.52 (m, 6H), 7.30 (dd, J=9.0, 2.1 Hz, 1H), 7.02 (dd, J=10.3, 2.7 Hz, 1H), 3.85 (s, 3H), 2.02-1.91 (m, 1H), 1.06-0.96 (m, 2H), 0.79-0.68 (m, 2H); LCMS(m/z) 428.3.

Example 424. N-(4'-(tert-butyl)-[1,1'-biphenyl]-3-yl)-7-fluoro-N-methyl-[1,2,4]triazolo[4,3-a]quinazolin-5-amine

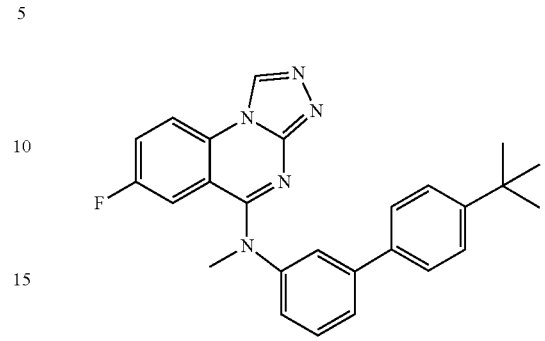

The title compound was synthesized according to the general procedure described for Example 409: ¹H NMR (400 MHz, Methanol-d₄) δ 9.60 (s, 1H), 8.40 (dd, J=9.2, 4.8 Hz, 1H), 7.89-7.82 (m, 1H), 7.80-7.33 (m, 8H), 6.88 (dd, J=10.6, 2.7 Hz, 1H), 3.88 (s, 3H), 1.35 (s, 9H); LCMS(m/z) 426.3.

Example 425. N-(4'-cyclopropyl-[1,1'-biphenyl]-3-yl)-7-fluoro-N-methyl-[1,2,4]triazolo[4,3-a]quinazolin-5-amine

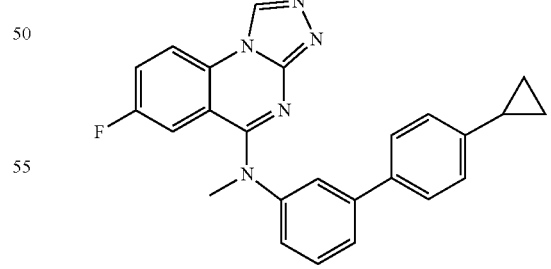

The title compound was synthesized according to the general procedure described for Example 409: ¹H NMR (400 MHz, Methanol-d₄) δ 9.59 (s, 1H), 8.39 (dd, J=9.2, 4.7 Hz, 1H), 7.94-7.38 (m, 9H), 6.95-6.83 (m, 1H), 3.87 (s, 3H), 1.99-1.90 (m, 1H), 1.06-0.97 (m, 2H), 0.82-0.67 (m, 2H); LCMS(m/z) 410.4.

Example 426. N-(3-(3,3-dimethylbut-1-yn-1-yl)-5-fluorophenyl)-7-fluoro-N-methyl-[1,2,4]triazolo[4,3-a]quinazolin-5-amine

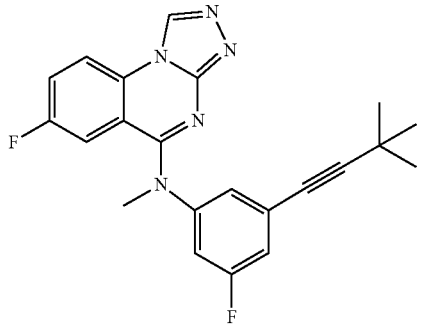

The title compound was synthesized according to the general procedure described for Example 421: $^1$H NMR (400 MHz, Methanol-d$_4$) δ 9.63 (s, 1H), 8.43 (dd, J=9.3, 4.7 Hz, 1H), 7.83 (ddd, J=9.2, 7.6, 2.7 Hz, 1H), 7.40-7.15 (m, 3H), 6.96 (dd, J=10.2, 2.7 Hz, 1H), 3.78 (s, 3H), 1.31 (s, 9H); LCMS(m/z) 392.4.

Example 427. N-(3-(cyclopropylethynyl)-5-fluorophenyl)-7-fluoro-N-methyl-[1,2,4]triazolo[4,3-a]quinazolin-5-amine

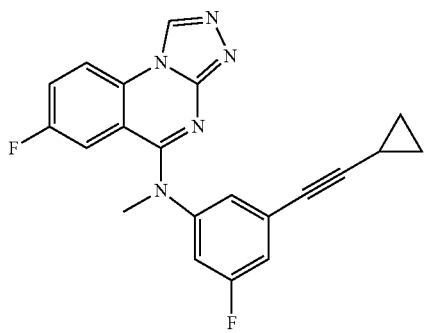

The title compound was synthesized according to the general procedure described for Example 421: $^1$H NMR (400 MHz, Methanol-d$_4$) δ 9.62 (s, 1H), 8.42 (dd, J=9.2, 4.7 Hz, 1H), 7.82 (ddd, J=10.0, 7.6, 2.7 Hz, 1H), 7.34-7.12 (m, 3H), 6.96 (dd, J=10.2, 2.7 Hz, 1H), 3.76 (s, 3H), 1.58-1.43 (m, 1H), 0.91 (dt, J=8.2, 3.3 Hz, 2H), 0.85-0.66 (m, 2H); LCMS(m/z) 376.3.

Example 428. N-(3-(3,3-dimethylbut-1-yn-1-yl)phenyl)-7-fluoro-N-methyl-[1,2,4]triazolo[4,3-a]quinazolin-5-amine

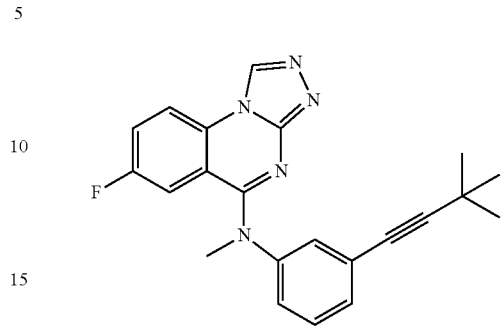

The title compound was synthesized according to the general procedure described for Example 421: $^1$H NMR (400 MHz, Methanol-d$_4$) δ 9.60 (s, 1H), 8.41 (dd, J=9.2, 4.8 Hz, 1H), 7.81 (ddd, J=9.2, 7.5, 2.7 Hz, 1H), 7.61-7.37 (m, 4H), 6.83 (dd, J=10.5, 2.7 Hz, 1H), 3.80 (s, 3H), 1.32 (s, 9H); LCMS(m/z) 374.3.

Example 429. N-(3-(cyclopropylethynyl)phenyl)-7-fluoro-N-methyl-[1,2,4]triazolo[4,3-a]quinazolin-5-amine

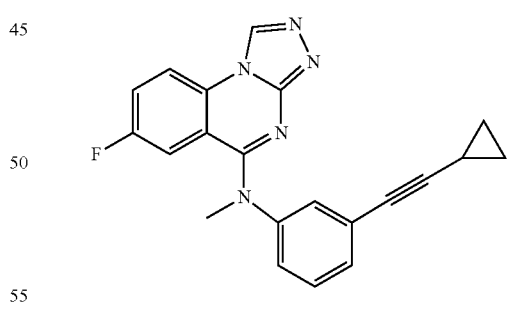

The title compound was synthesized according to the general procedure described for Example 421: $^1$H NMR (400 MHz, Methanol-d$_4$) δ 9.60 (s, 1H), 8.41 (dd, J=9.2, 4.7 Hz, 1H), 7.86-7.73 (m, 1H), 7.64-7.32 (m, 4H), 6.81 (dd, J=10.5, 2.7 Hz, 1H), 3.79 (s, 3H), 1.48 (ddd, J=8.2, 5.0, 3.3 Hz, 1H), 0.97-0.85 (m, 2H), 0.76 (dt, J=4.9, 3.1 Hz, 2H); LCMS(m/z) 358.3.

Example 430. N-(3-bromo-5-fluorophenyl)-7-fluoro-N-methyl-[1,2,4]triazolo[4,3-a]quinazolin-5-amine

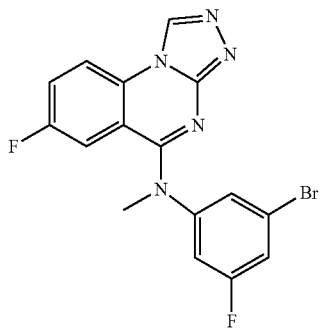

The title compound was synthesized according to the general procedure described for Example 409: ¹H NMR (400 MHz, Methanol-$d_4$) δ 9.65 (s, 1H), 8.45 (dd, J=9.2, 4.7 Hz, 1H), 7.84 (ddd, J=9.2, 7.6, 2.7 Hz, 1H), 7.56 (dd, J=7.1, 2.2 Hz, 2H), 7.38 (dt, J=9.3, 2.2 Hz, 1H), 7.00 (dd, J=10.0, 2.7 Hz, 1H), 3.78 (s, 3H); LCMS(m/z) 390.2.

Example 431. N-(3-bromophenyl)-7-fluoro-N-methyl-[1,2,4]triazolo[4,3-a]quinazolin-5-amine

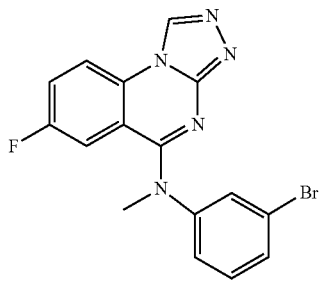

The title compound was synthesized according to the general procedure described for Example 409: ¹H NMR (400 MHz, Methanol-$d_4$) δ 9.63 (s, 1H), 8.43 (dd, J=9.2, 4.8 Hz, 1H), 7.82 (ddd, J=9.2, 7.5, 2.7 Hz, 1H), 7.74 (tq, J=3.1, 1.8 Hz, 2H), 7.60-7.47 (m, 2H), 6.86 (dd, J=10.3, 2.7 Hz, 1H), 3.80 (s, 3H); LCMS(m/z) 372.2.

Example 432. N-(4'-(tert-butyl)-[1,1'-biphenyl]-3-yl)-8-chloro-7-fluoro-N-methyl-[1,2,4]triazolo[4,3-a]quinazolin-5-amine

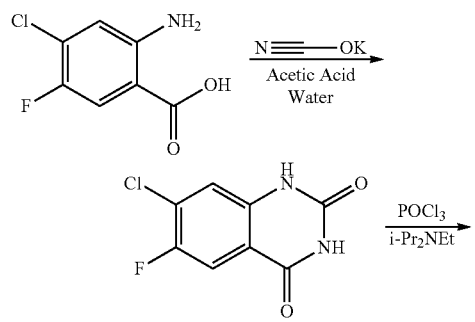

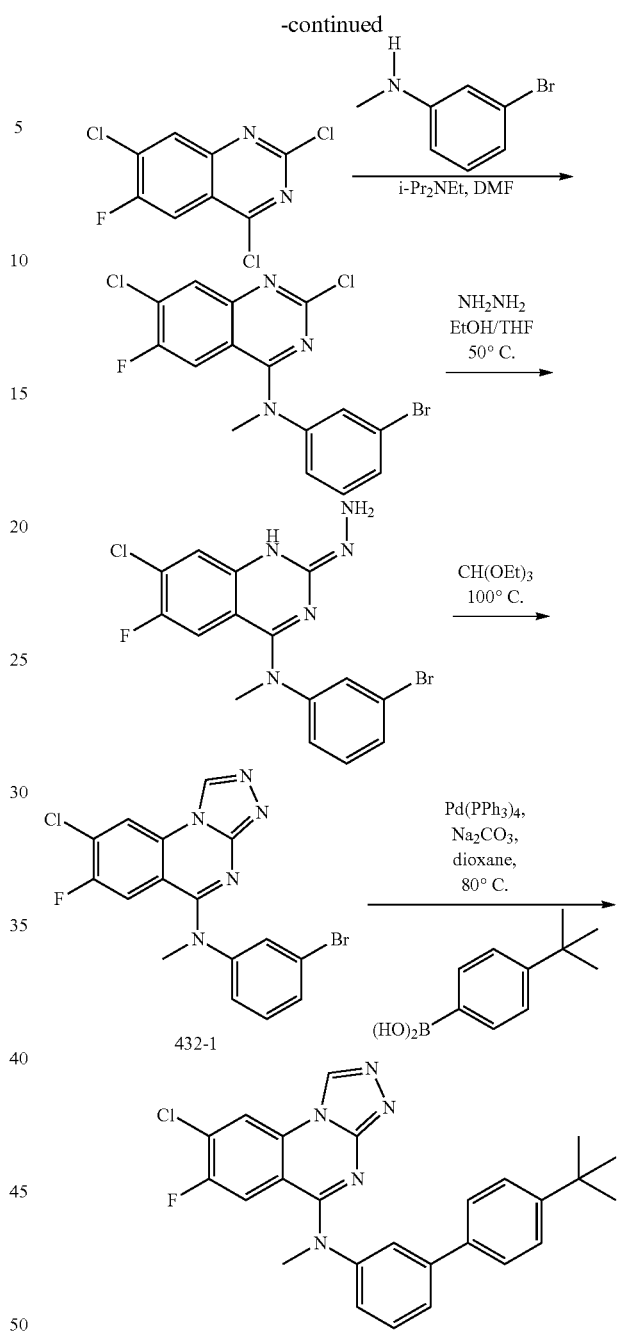

Synthesis of 7-chloro-6-fluoroquinazoline-2,4(1H,3H)-dione: 2-amino-4-chloro-5-fluorobenzoic acid (10 g, 51.7 mmol) was dissolved in AcOH (100 ml) and treated slowly with a solution of potassium cyanate (8.7 g, 103 mmol) in water (100 ml). After stirring at rt for 24 h, water (500 ml) was added. The resulting precipitate was collected by filtration and washed with water. The resultant material was suspended in MeOH (500 ml) and 3 N NaOH (110 mL) was added. The suspension was stirred at rt for 12 h, after which time, the reaction mixture was adjusted to pH to −3 with 6N HCl. The resultant material was collected by filtration, washed with water (100 ml), and dried under high vacuum to afford desired product: MS (m/z) 215.0 [M+H]⁺.

Synthesis of 2,4,7-trichloro-6-fluoroquinazoline: To a mixture of 7-chloro-6-fluoroquinazoline-2,4(1H,3H)-dione (1 g, 4.66 mmol) and DIPEA (1.51 mL, 8.68 mmol) was added phosphoryl chloride (3.25 mL, 34.9 mmol) dropwise at rt and the mixture was stirred for 5 min and then heated at 100° C. for 3 hr. The mixture was then carefully poured over crushed ice and stirred vigorously until a suspension was formed. To this mixture was added DCM and transferred to a separatory funnel. The aqueous layer was extracted with DCM (×2), and the combined organic layers were washed with a 10% solution of citric acid (aq), washed with brine, dried over $Na_2SO_4$. The solvent was removed under reduced pressure and dried under reduced pressure to provide the 2,4,7-trichloro-6-fluoroquinazoline: MS (m/z) 252.4 [M+H]$^+$.

Synthesis of N-(3-bromophenyl)-2,7-dichloro-6-fluoro-N-methylquinazolin-4-amine: To a solution of 2,4,7-trichloro-6-fluoroquinazoline (860 mg, 3.42 mmol) and 3-bromo-N-methylaniline (636 mg, 3.42 mmol) in DMF (5.0 mL) at RT was added DIPEA (1.52 mL, 8.55 mmol). The resulting mixture was stirred at rt for 2 hr. Upon completion, the reaction was poured into water and transferred to a separatory funnel and extracted with EA (×3). The combined organic layers were washed with brine, dried over $Na_2SO_4$, and concentrated under reduced pressure to afford the crude product. The residue was suspended in heptane, filtered and further dried in vacuo to afford the desired product: MS (m/z) 402.0 [M+H]$^+$.

Synthesis of (E)-N-(3-bromophenyl)-7-chloro-6-fluoro-2-hydrazono-N-methyl-1,2-dihydroquinazolin-4-amine: To a solution of N-(3-bromophenyl)-2,7-dichloro-6-fluoro-N-methylquinazolin-4-amine (1470 mg, 3.67 mmol) in THF (20 mL) and ethanol (20 mL) was added hydrazine (1470 mg, 39.5 mmol) at 0° C. The resultant mixture was stirred at RT for 30 mins. Upon completion, the reaction was concentrated under reduced pressure and dried in vacuo to afford the product: MS (m/z) 398.0 [M+H]$^+$.

Synthesis of N-(3-bromophenyl)-8-chloro-7-fluoro-N-methyl-[1,2,4]triazolo[4,3-a]quinazolin-5-amine: A solution of (E)-N-(3-bromophenyl)-7-chloro-6-fluoro-2-hydrazono-N-methyl-1,2-dihydroquinazolin-4-amine (1400 mg, 3.53 mmol) and triethyl orthoformate (6.27 g, 42.4 mmol) was heated to 100° C. for 1 h. Upon completion, the reaction was cooled to RT, and concentrated under reduced pressure to afford the crude product. The crude product was triturated with heptane. The resulting material was collected by filtration, washed with heptane: ether (1:1) and dried in vacuo to afford Compound 432-1.

Synthesis of N-(4'-(tert-butyl)-[1,1'-biphenyl]-3-yl)-8-chloro-7-fluoro-N-methyl-[1,2,4]triazolo[4,3-a]quinazolin-5-amine: To a solution of N-(3-bromophenyl)-8-chloro-7-fluoro-N-methyl-[1,2,4]triazolo[4,3-a]quinazolin-5-amine (Compound 432-1, 25.0 mg, 0.062 mmol) in dioxane (1.0 mL) was added (4-(tert-butyl)phenyl)boronic acid (24.2 mg, 0.14 mmol) Tetrakis(triphenylphosphine)palladium(0) (2.16 mg, 1.9 μmmol), and a 2 M solution of $Na_2CO_3$(aq) (0.154 mL, 0.307 mmol) and the mixture was purged with nitrogen gas and heated at 80° C. for 20 min. Upon completion, the mixture was diluted with EA, filtered through Celite®, and concentrated under reduced pressure. The crude product was dissolved in DMSO and purified via reverse phase HPLC to afford the title compound: $^1$H NMR (400 MHz, DMSO-d$_6$) δ 9.74 (s, 1H), 8.83 (d, J=6.6 Hz, 1H), 7.71 (dd, J=4.3, 2.3 Hz, 2H), 7.59 (dd, J=8.2, 4.6 Hz, 3H), 7.49-7.36 (m, 3H), 6.99 (d, J=10.9 Hz, 1H), 3.67 (s, 3H), 1.29 (s, 9H); LCMS (m/z) 460.2.

Example 433. 8-chloro-7-fluoro-N-[3-[2-fluoro-4-(trifluoromethyl)phenyl]phenyl]-N-methyl-[1,2,4]triazolo[4,3-a]quinazolin-5-amine

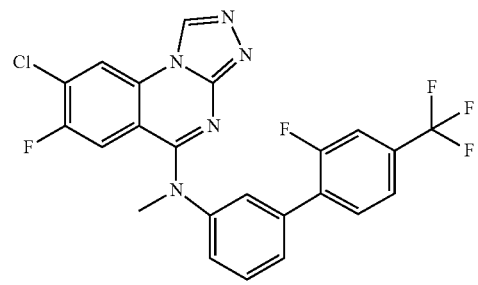

The title compound was prepared according to the method presented for the synthesis of Example 432 starting with N-(3-bromophenyl)-8-chloro-7-fluoro-N-methyl-[1,2,4]triazolo[4,3-a]quinazolin-5-amine and 2-[2-fluoro-4-(trifluoromethyl)phenyl]-4,4,5,5-tetramethyl-1,3,2-dioxaborolane. $^1$H NMR (400 MHz, DMSO-d$_6$) δ 9.72 (s, 1H), 8.83 (d, J=6.6 Hz, 1H), 7.82-7.71 (m, 2H), 7.69-7.59 (m, 4H), 7.55 (dt, J=7.7, 1.9 Hz, 1H), 7.03 (d, J=10.8 Hz, 1H), 3.65 (s, 3H); LCMS(m/z) 490.1.

Example 434. 8-chloro-7-fluoro-N-methyl-N-[3-[4-(trifluoromethyl)phenyl]phenyl]-[1,2,4]triazolo[4,3-a]quinazolin-5-amine

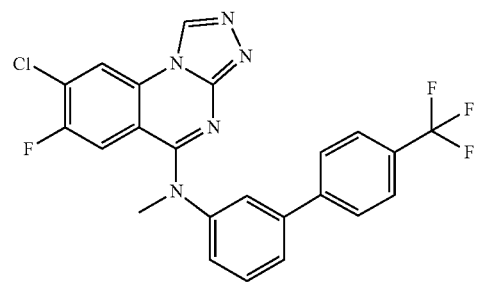

The title compound was prepared according to the method presented for the synthesis of Example 432 starting with N-(3-bromophenyl)-8-chloro-7-fluoro-N-methyl-[1,2,4]triazolo[4,3-a]quinazolin-5-amine and (trifluoromethyl)phenyl]boronic acid. $^1$H NMR (400 MHz, DMSO-d$_6$) δ 9.73 (s, 1H), 8.83 (d, J=6.6 Hz, 1H), 7.97-7.76 (m, 7H), 7.62 (t, J=7.9 Hz, 1H), 7.53-7.42 (m, 1H), 7.04 (d, J=10.7 Hz, 1H), 3.67 (s, 3H); LCMS(m/z) 472.1.

Example 435. 8-chloro-7-fluoro-N-methyl-N-[3-[6-(trifluoromethyl)-3-pyridyl]phenyl]-[1,2,4]triazolo[4,3-a]quinazolin-5-amine

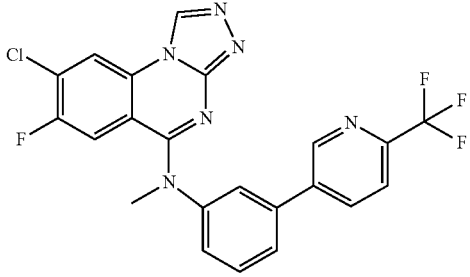

To a solution of N-(3-bromophenyl)-8-chloro-7-fluoro-N-methyl-[1,2,4]triazolo[4,3-a]quinazolin-5-amine (Compound 432-1, 25 mg, 0.062 mmol) in dioxane (2 mL) was added [6-(trifluoromethyl)-3-pyridyl]boronic acid (24.6 mg, 0.13 mmol), Pd(dppf)Cl2 (2.54 mg, 3.07 µmol), and 2 M solution of Na$_2$CO$_3$(aq) (0.154 mL, 0.307 mmol) and the mixture was purged with nitrogen and heated at 80° C. for 20 min. Upon completion, the mixture was diluted with EA, filtered through Celite®, and concentrated under reduced pressure. The crude product was dissolved in DMSO and purified via reverse phase HPLC to afford the title compound: $^1$H NMR (400 MHz, DMSO-d$_6$) δ 9.74 (s, 1H), 9.08 (d, J=2.2 Hz, 1H), 8.84 (d, J=6.6 Hz, 1H), 8.39 (dd, J=8.2, 2.2 Hz, 1H), 7.98 (d, J=8.2 Hz, 1H), 7.93 (d, J=1.9 Hz, 1H), 7.85 (d, J=7.7 Hz, 1H), 7.65 (t, J=7.9 Hz, 1H), 7.53 (dd, J=8.1, 2.1 Hz, 1H), 7.07 (d, J=10.7 Hz, 1H), 3.67 (s, 3H); LCMS(m/z) 473.1.

Example 436. 8-chloro-N-[3-(6-cyclopropyl-3-pyridyl)phenyl]-7-fluoro-N-methyl-[1,2,4]triazolo[4,3-a]quinazolin-5-amine

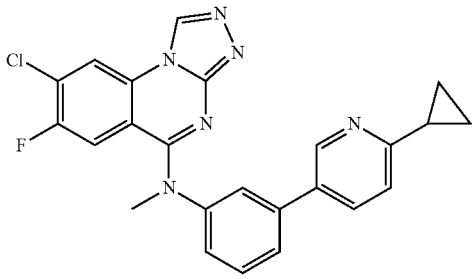 [SMILES: CN(c1cccc(-c2ccc(C3CC3)nc2)c1)c1nc2nncn2c2cc(Cl)c(F)cc12]

The title compound was prepared according to the method presented for the synthesis of Example 435 starting with N-(3-bromophenyl)-8-chloro-7-fluoro-N-methyl-[1,2,4]triazolo[4,3-a]quinazolin-5-amine and (6-cyclopropyl-3-pyridyl)boronic acid. $^1$H NMR (400 MHz, DMSO-d$_6$) δ 9.70 (s, 1H), 8.81 (d, J=6.6 Hz, 1H), 8.70 (d, J=2.3 Hz, 1H), 8.00 (d, J=8.1 Hz, 1H), 7.76 (s, 1H), 7.72 (d, J=7.9 Hz, 1H), 7.58 (t, J=7.8 Hz, 1H), 7.41 (dd, J=17.8, 7.9 Hz, 2H), 7.04 (d, J=10.7 Hz, 1H), 2.14 (dd, J=8.6, 4.1 Hz, 1H), 1.00 (d, J=8.0 Hz, 2H), 0.95 (dd, J=5.0, 2.5 Hz, 2H); LCMS(m/z) 445.1.

Example 437. 3-chloro-4-[3-[(8-chloro-7-fluoro-[1,2,4]triazolo[4,3-a]quinazolin-5-yl)-methyl-amino]phenyl]benzonitrile

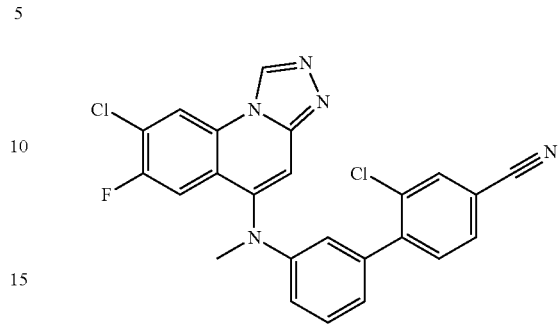

The title compound was prepared according to the method presented for the synthesis of Example 435 starting with N-(3-bromophenyl)-8-chloro-7-fluoro-N-methyl-[1,2,4]triazolo[4,3-a]quinazolin-5-amine and (2-chloro-4-cyano-phenyl)boronic acid. $^1$H NMR (400 MHz, DMSO-d$_6$) δ 9.72 (s, 1H), 8.83 (d, J=6.6 Hz, 1H), 8.15 (d, J=1.6 Hz, 1H), 7.91 (dd, J=7.9, 1.7 Hz, 1H), 7.76-7.53 (m, 3H), 7.54-7.41 (m, 2H), 7.05 (d, J=10.7 Hz, 1H), 3.64 (s, 3H); LCMS(m/z) 463.0.

Example 438. N-[3-(6-amino-3-pyridyl)phenyl]-8-chloro-7-fluoro-N-methyl-[1,2,4]triazolo[4,3-a]quinazolin-5-amine

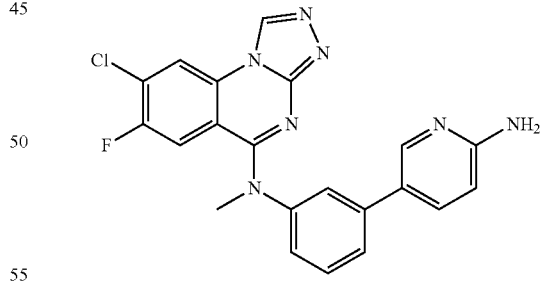

The title compound was prepared according to the method presented for the synthesis of Example 435 starting with N-(3-bromophenyl)-8-chloro-7-fluoro-N-methyl-[1,2,4]triazolo[4,3-a]quinazolin-5-amine and 5-(4,4,5,5-tetramethyl-1,3,2-dioxaborolan-2-yl)pyridin-2-amine. $^1$H NMR (400 MHz, DMSO-d$_6$) δ 9.68 (s, 1H), 8.80 (d, J=6.6 Hz, 1H), 8.27 (d, J=8.9 Hz, 2H), 7.98 (s, 2H), 7.73 (d, J=2.0 Hz, 1H), 7.65 (d, J=7.8 Hz, 1H), 7.55 (t, J=7.9 Hz, 1H), 7.40 (dd, J=7.9, 2.1 Hz, 1H), 7.03 (dd, J=16.9, 9.9 Hz, 2H), 3.62 (s, 3H); LCMS(m/z) 420.1.

Example 439. N-[3-(2-aminopyrimidin-5-yl)phenyl]-8-chloro-7-fluoro-N-methyl-[1,2,4]triazolo[4,3-a]quinazolin-5-amine

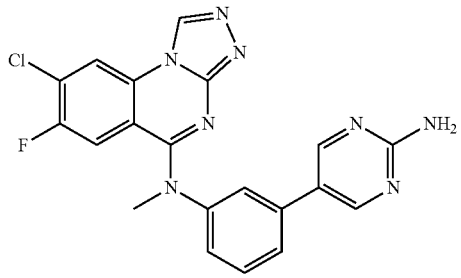 [SMILES: CN(c1cccc(-c2cnc(N)nc2)c1)c1nc2nncn2c2cc(Cl)c(F)cc12]

The title compound was prepared according to the method presented for the synthesis of Example 435 starting with N-(3-bromophenyl)-8-chloro-7-fluoro-N-methyl-[1,2,4]triazolo[4,3-a]quinazolin-5-amine and 5-(4,4,5,5-tetramethyl-1,3,2-dioxaborolan-2-yl)pyrimidin-2-amine. $^1$H NMR (400 MHz, DMSO-d$_6$) δ 9.74 (s, 1H), 8.83 (d, J=6.6 Hz, 1H), 8.61 (s, 2H), 7.79-7.63 (m, 2H), 7.53 (t, J=7.9 Hz, 1H), 7.44-7.29 (m, 1H), 7.02 (d, J=10.8 Hz, 1H), 6.96 (s, 2H), 3.65 (s, 3H); LCMS(m/z) 421.1.

Example 440. 8-chloro-7-fluoro-N-methyl-N-[3-(4-propoxyphenyl)phenyl]-[1,2,4]triazolo[4,3-a]quinazolin-5-amine

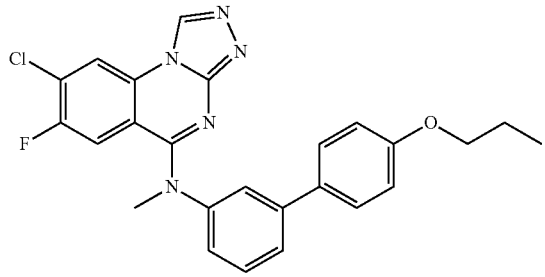 [SMILES: CCCOc1ccc(-c2cccc(N(C)c3nc4nncn4c4cc(Cl)c(F)cc34)c2)cc1]

The title compound was prepared according to the method presented for the synthesis of Example 435 starting with N-(3-bromophenyl)-8-chloro-7-fluoro-N-methyl-[1,2,4]triazolo[4,3-a]quinazolin-5-amine and (4-propoxyphenyl)boronic acid. $^1$H NMR (400 MHz, DMSO-d$_6$) δ 9.71 (s, 1H), 8.81 (d, J=6.6 Hz, 1H), 7.77-7.69 (m, 2H), 7.68-7.63 (m, 2H), 7.57 (t, J=7.8 Hz, 1H), 7.43-7.34 (m, 3H), 7.02 (d, J=10.8 Hz, 1H), 4.48 (s, 2H), 3.65 (d, J=6.5 Hz, 3H), 3.48 (q, J=7.0 Hz, 2H), 1.15 (t, J=7.0 Hz, 3H); LCMS(m/z) 462.1.

Example 441. 8-chloro-7-fluoro-N-methyl-N-[3-[4-(trifluoromethoxy)phenyl]phenyl]-[1,2,4]triazolo[4,3-a]quinazolin-5-amine

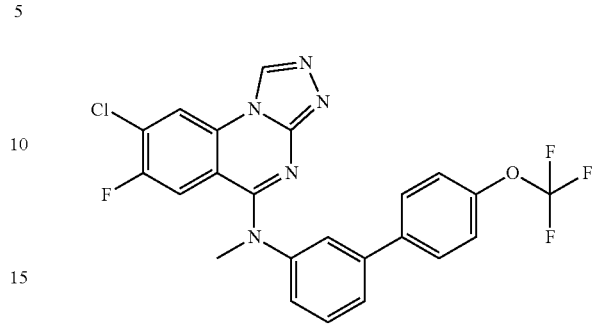

The title compound was prepared according to the method presented for the synthesis of Example 435 starting with N-(3-bromophenyl)-8-chloro-7-fluoro-N-methyl-[1,2,4]triazolo[4,3-a]quinazolin-5-amine and [4-(trifluoromethoxy)phenyl]boronic acid. $^1$H NMR (400 MHz, DMSO-d$_6$) δ 9.72 (s, 1H), 8.82 (d, J=6.6 Hz, 1H), 7.86-7.76 (m, 3H), 7.76-7.70 (m, 1H), 7.58 (q, J=7.2, 6.5 Hz, 2H), 7.48-7.42 (m, 3H), 7.03 (d, J=10.7 Hz, 1H), 3.66 (s, 3H); LCMS(m/z) 488.1.

Example 442. 8-chloro-7-fluoro-N-methyl-N-[3-[6-(2,2,2-trifluoroethoxy)-3-pyridyl]phenyl]-[1,2,4]triazolo[4,3-a]quinazolin-5-amine

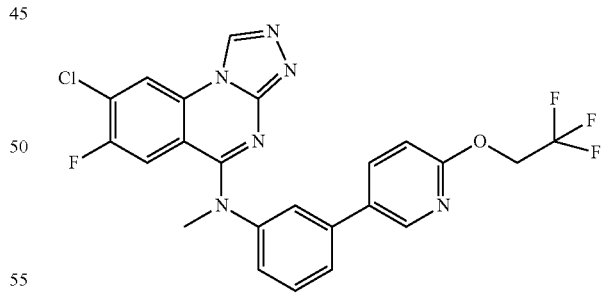

The title compound was prepared according to the method presented for the synthesis of Example 435 starting with N-(3-bromophenyl)-8-chloro-7-fluoro-N-methyl-[1,2,4]triazolo[4,3-a]quinazolin-5-amine and [6-(2,2,2-trifluoroethoxy)-3-pyridyl]boronic acid. $^1$H NMR (400 MHz, DMSO-d$_6$) δ 9.72 (s, 1H), 8.82 (d, J=6.6 Hz, 1H), 8.51 (d, J=2.6 Hz, 1H), 8.13 (dd, J=8.6, 2.6 Hz, 1H), 7.78 (d, J=2.1 Hz, 1H), 7.73 (d, J=7.9 Hz, 1H), 7.57 (d, J=7.9 Hz, 1H), 7.48-7.37 (m, 1H), 7.05 (dd, J=12.0, 9.7 Hz, 2H), 5.03 (q, J=9.1 Hz, 2H), 3.65 (s, 3H); LCMS(m/z) 503.1.

Example 443. 8-chloro-7-fluoro-N-[3-(5-fluoro-6-methoxy-3-pyridyl)phenyl]-N-methyl-[1,2,4]triazolo[4,3-a]quinazolin-5-amine

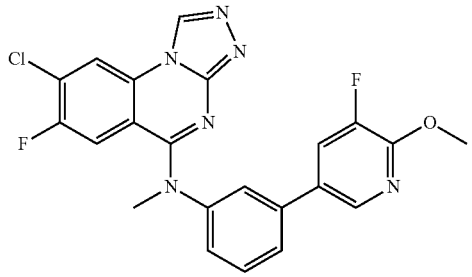 [SMILES: COc1ncc(-c2cccc(N(C)c3nc4nncn4c4cc(Cl)c(F)cc34)c2)cc1F]

The title compound was prepared according to the method presented for the synthesis of Example 435 starting with N-(3-bromophenyl)-8-chloro-7-fluoro-N-methyl-[1,2,4]triazolo[4,3-a]quinazolin-5-amine and (5-fluoro-6-methoxy-3-pyridyl)boronic acid. $^1$H NMR (400 MHz, DMSO-d$_6$) δ 9.75 (s, 1H), 8.84 (d, J=6.6 Hz, 1H), 8.34 (d, J=2.1 Hz, 1H), 8.09 (dd, J=11.9, 2.1 Hz, 1H), 7.86-7.76 (m, 2H), 7.58 (t, J=7.9 Hz, 1H), 7.43 (dd, J=8.0, 2.1 Hz, 1H), 7.03 (d, J=10.7 Hz, 1H), 3.97 (s, 3H), 3.66 (s, 3H); LCMS(m/z) 453.1.

Example 444. 8-chloro-N-[3-(6-ethoxy-3-pyridyl)phenyl]-7-fluoro-N-methyl-[1,2,4]triazolo[4,3-a]quinazolin-5-amine

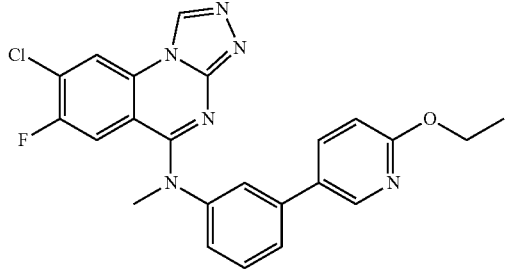 [SMILES: CCOc1ccc(-c2cccc(N(C)c3nc4nncn4c4cc(Cl)c(F)cc34)c2)cn1]

The title compound was prepared according to the method presented for the synthesis of Example 435 starting with N-(3-bromophenyl)-8-chloro-7-fluoro-N-methyl-[1,2,4]triazolo[4,3-a]quinazolin-5-amine and 2-ethoxy-5-(4,4,5,5-tetramethyl-1,3,2-dioxaborolan-2-yl)pyridine. $^1$H NMR (400 MHz, DMSO-d$_6$) δ 9.74 (s, 1H), 8.83 (d, J=6.6 Hz, 1H), 8.46 (d, J=2.6 Hz, 1H), 8.01 (dd, J=8.7, 2.7 Hz, 1H), 7.79-7.68 (m, 2H), 7.58 (t, J=7.9 Hz, 1H), 7.42 (dd, J=8.0, 2.2 Hz, 1H), 7.02 (d, J=10.8 Hz, 1H), 6.86 (d, J=8.6 Hz, 1H), 4.32 (q, J=7.0 Hz, 2H), 3.66 (s, 3H), 1.32 (t, J=7.1 Hz, 3H); LCMS (m/z) 449.1.

Example 445. 8-chloro-7-fluoro-N-methyl-N-[3-(4-methylsulfonylphenyl)phenyl]-[1,2,4]triazolo[4,3-a]quinazolin-5-amine

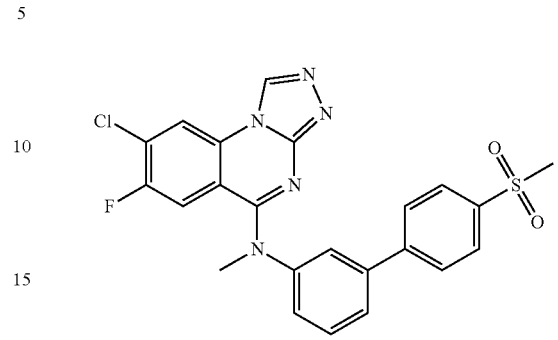

The title compound was prepared according to the method presented for the synthesis of Example 435 starting with N-(3-bromophenyl)-8-chloro-7-fluoro-N-methyl-[1,2,4]triazolo[4,3-a]quinazolin-5-amine and (4-methylsulfonylphenyl)boronic acid. $^1$H NMR (400 MHz, DMSO-d$_6$) δ 9.74 (s, 1H), 8.83 (d, J=6.6 Hz, 1H), 8.05-7.92 (m, 4H), 7.86 (t, J=2.0 Hz, 1H), 7.81 (dt, J=8.0, 1.2 Hz, 1H), 7.63 (t, J=7.9 Hz, 1H), 7.50 (ddd, J=8.0, 2.2, 1.0 Hz, 1H), 7.03 (d, J=10.8 Hz, 1H), 3.68 (s, 3H), 3.24 (s, 3H); LCMS(m/z) 482.2.

Example 446. 8-chloro-N-[3-[6-(difluoromethyl)-3-pyridyl]phenyl]-7-fluoro-N-methyl-[1,2,4]triazolo[4,3-a]quinazolin-5-amine

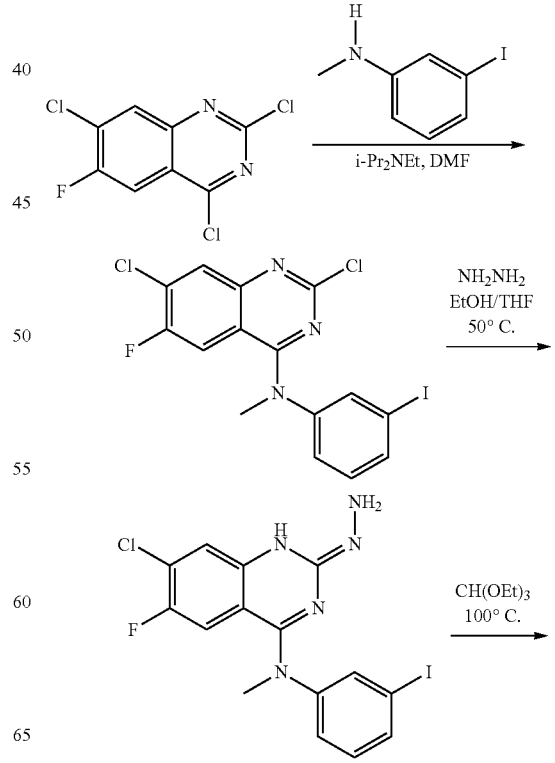

-continued

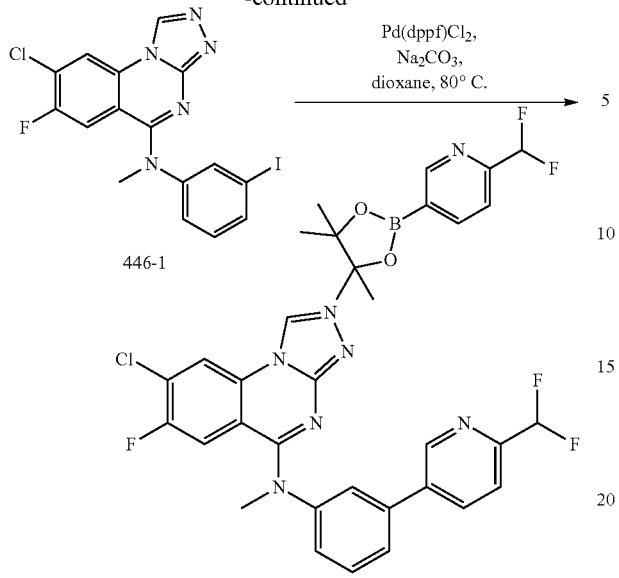

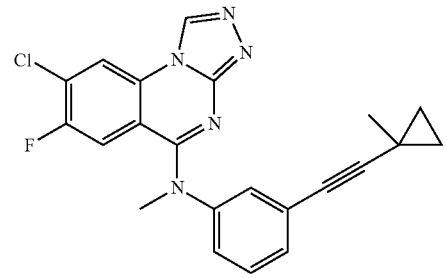 [SMILES: CN(c1cccc(C#CC2(C)CC2)c1)c1nc2nncn2c2cc(Cl)c(F)cc12]

Synthesis of 2,7-dichloro-6-fluoro-N-(3-iodophenyl)-N-methylquinazolin-4-amine: To a solution of 2,4,7-trichloro-6-fluoroquinazoline 760 mg, 3.02 mmol) and 3-iodo-N-methylaniline (704 mg, 3.02 mmol) in DMF (5.0 mL) at RT was added DIPEA (1.35 mL, 7.56 mmol). The resulting mixture was stirred at rt for 2 hr. Upon completion, the reaction was poured into water and transferred to a separatory funnel and extracted with EA (×3). The combined organic layers were washed with brine, dried over Na$_2$SO$_4$, and concentrated under reduced pressure to afford the crude product. The residue was suspended in heptane, filtered and further dried in vacuo to afford the desired compound: MS (m/z) 449.0 [M+H]$^+$.

Synthesis of (E)-N-(3-iodophenyl)-7-chloro-6-fluoro-2-hydrazono-N-methyl-1,2-dihydroquinazolin-4-amine: To a solution of 2,7-dichloro-6-fluoro-N-(3-iodophenyl)-N-methylquinazolin-4-amine (653 mg, 1.46 mmol) in THF (10 mL) and ethanol (10 mL) was added hydrazine (503 mg, 15.7 mmol) at 0° C. The resultant mixture was stirred at RT for 30 mins. Upon completion, the reaction was concentrated under reduced pressure and dried in vacuo to afford the product: MS (m/z) 444.0 [M+H]$^+$.

Synthesis of N-(3-iodophenyl)-8-chloro-7-fluoro-N-methyl-[1,2,4]triazolo[4,3-a]quinazolin-5-amine (Compound 446-1): A solution of (E)-N-(3-iodophenyl)-7-chloro-6-fluoro-2-hydrazono-N-methyl-1,2-dihydroquinazolin-4-amine (647 mg, 1.46 mmol) and triethyl orthoformate (2.59 g, 17.5 mmol) was heated to 100° C. for 1 h. Upon completion, the reaction was cooled to RT, and concentrated under reduced pressure to afford the crude product. The crude product was triturated with heptane. The resulting material was collected by filtration, washed with heptane: ether (1:1) and dried in vacuo to afford the desired compound: MS (m/z) 454.0 [M+H]$^+$.

The title compound was prepared according to the method presented for the synthesis of Example 435 starting with N-(3-Iodophenyl)-8-chloro-7-fluoro-N-methyl-[1,2,4]triazolo[4,3-a]quinazolin-5-amine and 2-(difluoromethyl)-5-(4,4,5,5-tetramethyl-1,3,2-dioxaborolan-2-yl)pyridine. $^1$H NMR (400 MHz, DMSO-d$_6$) δ 9.74 (s, 1H), 8.99 (d, J=2.2 Hz, 1H), 8.83 (d, J=6.6 Hz, 1H), 8.30 (dd, J=8.2, 2.3 Hz, 1H), 7.93-7.86 (m, 1H), 7.83 (d, J=7.7 Hz, 1H), 7.77 (d, J=8.2 Hz, 1H), 7.63 (t, J=7.9 Hz, 1H), 7.56-7.43 (m, 1H), 7.17-6.80 (m, 2H), 3.67 (s, 3H); LCMS(m/z) 455.1.

Example 447. 8-chloro-7-fluoro-N-methyl-N-[3-[2-(1-methylcyclopropyl)ethynyl]phenyl]-[1,2,4]triazolo[4,3-a]quinazolin-5-amine

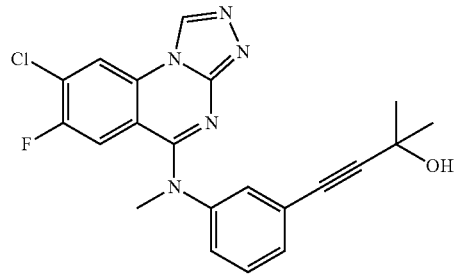 [SMILES: CN(c1cccc(C#CC(C)(C)O)c1)c1nc2nncn2c2cc(Cl)c(F)cc12]

To a solution of N-(3-iodophenyl)-8-chloro-7-fluoro-N-methyl-[1,2,4]triazolo[4,3-a]quinazolin-5-amine (Compound 446-1, 25 mg, 0.055 mmol) in DMF (2 mL) was added 1-ethynyl-1-methyl-cyclopropane (5.3 mg, 0.07 mmol), Pd(PPh$_3$)$_2$Cl$_2$ (1.55 mg, 2.2 µmol), CuI (0.3 mg, 0.03 mmol) and triethylamine (0.7 mL, 5.51 mmol) and the mixture was purged with nitrogen and heated at 84° C. for 10 min. Upon completion, the mixture was partitioned between EA (20 mL) and water (20 mL), organics separated and dried over Na$_2$SO$_4$. The resultant was and concentrated under reduced pressure. The crude product was dissolved in DMSO and purified via reverse phase HPLC to afford the title compound: $^1$H NMR (400 MHz, DMSO-d$_6$) δ 9.72 (s, 1H), 8.83 (d, J=6.6 Hz, 1H), 7.46-7.38 (m, 2H), 7.35 (dd, J=6.9, 1.8 Hz, 2H), 6.97 (d, J=10.7 Hz, 1H), 3.56 (s, 3H), 1.29 (s, 3H), 0.92 (q, J=3.9 Hz, 2H), 0.77-0.57 (m, 2H); LCMS(m/z) 406.1.

Example 448. 4-[3-[(8-chloro-7-fluoro-[1,2,4]triazolo[4,3-a]quinazolin-5-yl)-methyl-amino]phenyl]-2-methyl-but-3-yn-2-ol

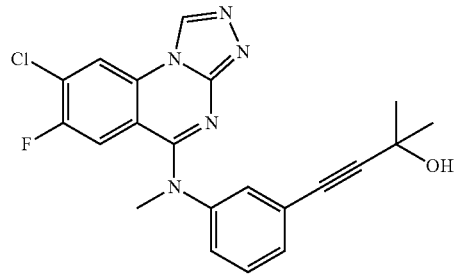 [SMILES: CN(c1cccc(C#CC(C)(C)O)c1)c1nc2nncn2c2cc(Cl)c(F)cc12]

The title compound was prepared according to the method presented for the synthesis of Example 447 starting with N-(3-Iodophenyl)-8-chloro-7-fluoro-N-methyl-[1,2,4]triazolo[4,3-a]quinazolin-5-amine (Compound 446-1) and 2-methylbut-3-yn-2-ol. $^1$H NMR (400 MHz, DMSO-d$_6$) δ 9.73 (s, 1H), 8.84 (d, J=6.7 Hz, 1H), 7.51-7.43 (m, 2H), 7.40 (d, J=7.9 Hz, 2H), 6.97 (dd, J=10.8, 1.6 Hz, 1H), 3.58 (s, 3H), 1.44 (s, 6H); LCMS(m/z) 410.1.

Example 449. 1-[2-[3-[(8-chloro-7-fluoro-[1,2,4]triazolo[4,3-a]quinazolin-5-yl)-methyl-amino]phenyl]ethynyl]cyclopropanol

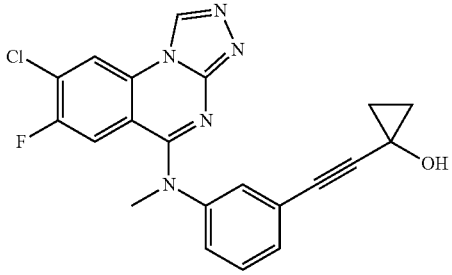 [SMILES: CN(c1cccc(C#CC2(O)CC2)c1)c1nc2nncn2c2cc(Cl)c(F)cc12]

The title compound was prepared according to the method presented for the synthesis of Example 447 starting with N-(3-Iodophenyl)-8-chloro-7-fluoro-N-methyl-[1,2,4]triazolo[4,3-a]quinazolin-5-amine (Compound 446-1) and 1-ethynylcyclopropanol. $^1$H NMR (400 MHz, DMSO-$d_6$) δ 9.70 (s, 1H), 8.82 (d, J=6.6 Hz, 1H), 7.50-7.41 (m, 2H), 7.40-7.33 (m, 2H), 6.98 (d, J=10.7 Hz, 1H), 3.61-3.52 (m, 3H), 0.97 (dd, J=3.3, 2.1 Hz, 2H), 0.94 (dd, J=3.2, 2.2 Hz, 2H); LCMS(m/z) 408.1.

Example 451. 8-chloro-N-[3-(5-cyclopropylpyrazin-2-yl)phenyl]-7-fluoro-N-methyl-[1,2,4]triazolo[4,3-a]quinazolin-5-amine

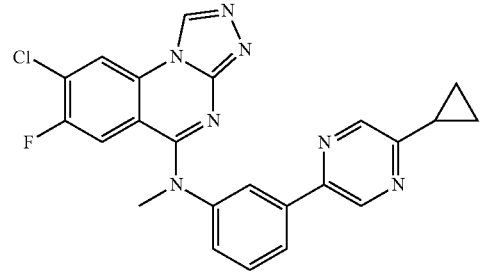

The title compound was prepared according to the method presented for the synthesis of Example 435 starting with N-(3-Iodophenyl)-8-chloro-7-fluoro-N-methyl-[1,2,4]triazolo[4,3-a]quinazolin-5-amine (Compound 446-1) and 2-cyclopropyl-5-(4,4,5,5-tetramethyl-1,3,2-dioxaborolan-2-yl)pyrazine. $^1$H NMR (400 MHz, DMSO-$d_6$) δ 9.70 (s, 1H), 9.03 (d, J=1.5 Hz, 1H), 8.81 (d, J=6.6 Hz, 1H), 8.66 (d, J=1.5 Hz, 1H), 8.13-8.05 (m, 2H), 7.60 (t, J=8.1 Hz, 1H), 7.52-7.42 (m, 1H), 7.04 (d, J=10.8 Hz, 1H), 3.64 (s, 3H), 2.24 (td, J=8.2, 4.2 Hz, 1H), 1.07 (dt, J=8.0, 3.1 Hz, 2H), 1.01-0.93 (m, 2H); LCMS(m/z) 446.1.

Example 450. 8-chloro-N-[3-(2-cyclopropylethynyl)phenyl]-7-fluoro-N-methyl-[1,2,4]triazolo[4,3-a]quinazolin-5-amine

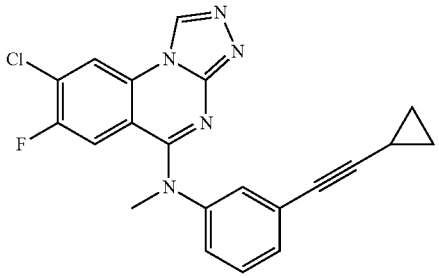 [SMILES: CN(c1cccc(C#CC2CC2)c1)c1nc2nncn2c2cc(Cl)c(F)cc12]

The title compound was prepared according to the method presented for the synthesis of Example 447 starting with N-(3-Iodophenyl)-8-chloro-7-fluoro-N-methyl-[1,2,4]triazolo[4,3-a]quinazolin-5-amine (Compound 446-1) and ethynylcyclopropane. $^1$H NMR (400 MHz, DMSO-$d_6$) δ 9.71 (s, 1H), 8.83 (d, J=6.6 Hz, 1H), 7.48-7.39 (m, 2H), 7.39-7.33 (m, 2H), 6.97 (d, J=10.7 Hz, 1H), 3.56 (s, 3H), 1.52 (tt, J=8.3, 5.0 Hz, 1H), 0.96-0.84 (m, 2H), 0.72 (dq, J=5.0, 3.9 Hz, 2H); LCMS(m/z) 392.1.

Example 452. 8-chloro-N-ethyl-N-[3-(4-methylsulfonylphenyl)phenyl]-[1,2,4]triazolo[4,3-a]quinazolin-5-amine

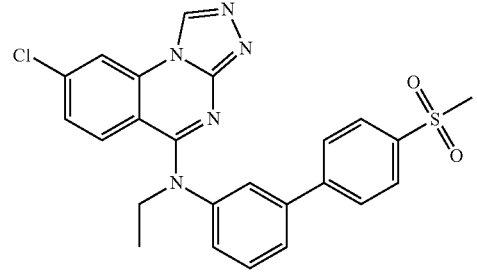

The title compound was prepared according to the method presented for the synthesis of Example 455 starting with N-(3-bromophenyl)-8-chloro-N-ethyl-[1,2,4]triazolo[4,3-a]quinazolin-5-amine and (4-methylsulfonylphenyl)boronic acid. $^1$H NMR (400 MHz, DMSO-$d_6$) δ 9.77 (s, 1H), 8.61 (d, J=2.1 Hz, 1H), 8.01-7.90 (m, 4H), 7.83 (t, J=2.0 Hz, 1H), 7.79 (dd, J=7.7, 1.3 Hz, 1H), 7.61 (t, J=7.9 Hz, 1H), 7.47 (ddd, J=8.0, 2.2, 1.0 Hz, 1H), 7.38 (dd, J=9.0, 2.1 Hz, 1H), 7.23 (d, J=9.0 Hz, 1H), 4.26 (q, J=6.9 Hz, 2H), 3.24 (s, 3H), 1.29 (t, J=7.0 Hz, 3H); LCMS(m/z) 478.1.

Example 453. 4-[3-[(8-chloro-[1,2,4]triazolo[4,3-a]quinazolin-5-yl)-ethyl-amino]phenyl]-2-methyl-but-3-yn-2-ol

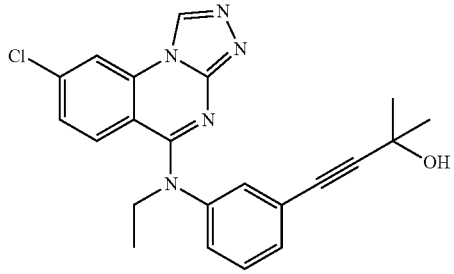

To a solution of N-(3-bromophenyl)-8-chloro-N-ethyl-[1,2,4]triazolo[4,3-a]quinazolin-5-amine (Compound 455-1, 25 mg, 0.62 mmol) in DMF (2 mL) was added 2-methylbut-3-yn-2-ol (52 mg, 0.06 mmol), Pd(dppf)Cl2 (5.13 mg, 6.2 μmol), dibromozinc (70 mg, 0.31 mmol) and Et₃N (0.173 mL, 1.24 mmol) and the mixture was purged with nitrogen and heated at 100° C. for 10 min. Upon completion, the reaction was poured into water and transferred to a separatory funnel and extracted with EA (×3). The combined organic layers were washed with brine, dried over Na₂SO₄, and concentrated under reduced pressure to afford the crude product. The crude product was dissolved in DMSO and purified via reverse phase HPLC to afford the title compound: $^1$H NMR (400 MHz, DMSO-$d_6$) δ 9.74 (s, 1H), 8.61 (d, J=2.1 Hz, 1H), 7.51-7.41 (m, 3H), 7.37 (t, J=5.0 Hz, 2H), 7.18 (d, J=9.0 Hz, 1H), 4.16 (q, J=6.9 Hz, 2H), 1.43 (s, 6H), 1.23 (t, J=6.9 Hz, 3H); LCMS(m/z) 406.1.

Example 454. 8-chloro-7-fluoro-N-[3-(5-methoxypyrazin-2-yl)phenyl]-N-methyl-[1,2,4]triazolo[4,3-a]quinazolin-5-amine

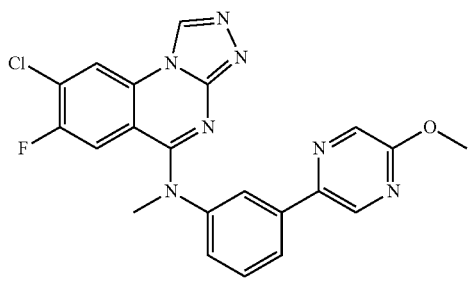

The title compound was prepared according to the method presented for the synthesis of Example 435 starting with N-(3-Iodophenyl)-8-chloro-7-fluoro-N-methyl-[1,2,4]triazolo[4,3-a]quinazolin-5-amine and 2-methoxy-5-(4,4,5,5-tetramethyl-1,3,2-dioxaborolan-2-yl)pyrazine. $^1$H NMR (400 MHz, DMSO-$d_6$) δ 9.72 (d, J=4.7 Hz, 1H), 8.95-8.73 (m, 2H), 8.37 (d, J=1.4 Hz, 1H), 8.13-7.98 (m, 2H), 7.61 (t, J=8.0 Hz, 1H), 7.53-7.42 (m, 1H), 7.13-6.91 (m, 1H), 3.95 (s, 3H), 3.66 (s, 3H); LCMS(m/z) 436.1.

Example 455. 8-chloro-N-[3-[6-(difluoromethyl)-3-pyridyl]phenyl]-N-ethyl-[1,2,4]triazolo[4,3-a]quinazolin-5-amine

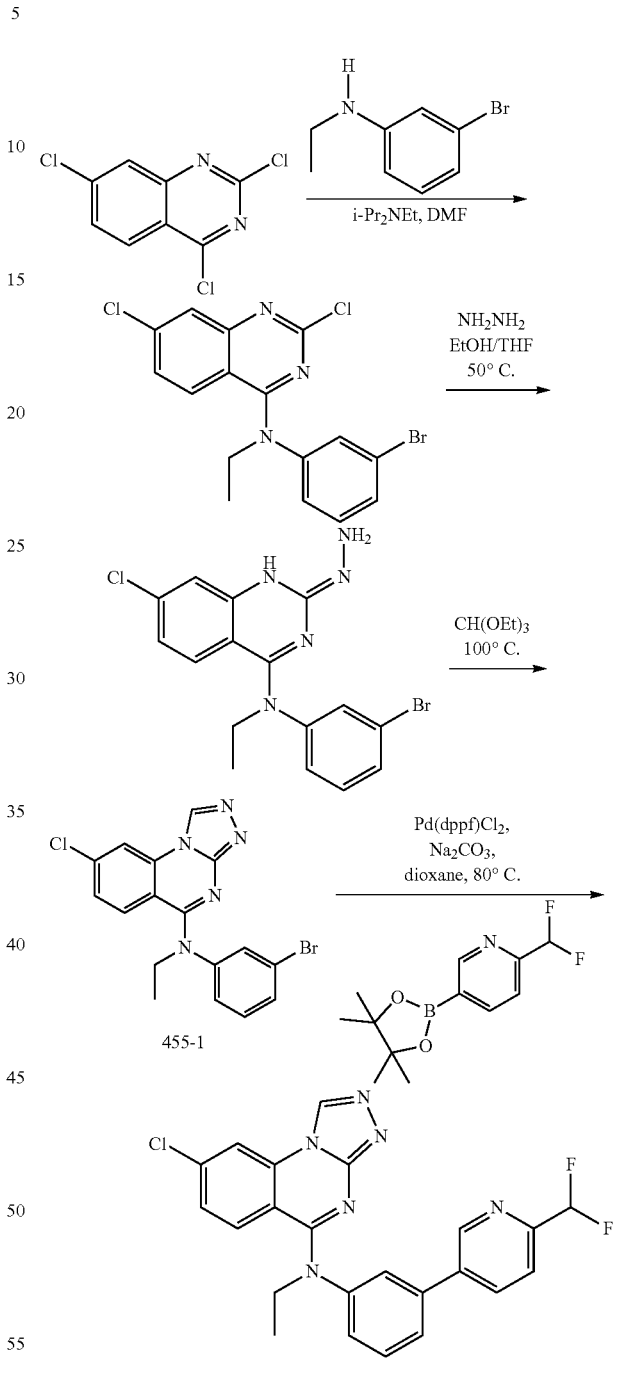

Synthesis of N-(3-bromophenyl)-2,6,7-trichloro-N-ethylquinazolin-4-amine: To a solution of 2,4,7-trichloroquinazoline (1000 mg, 4.28 mmol) and 3-bromo-N-ethylaniline (998 mg, 4.99 mmol) in DMF (5.0 mL) at RT was added DIPEA (1.91 mL, 10.7 mmol). The resulting mixture was stirred at 40° C. for 2 hr. Upon completion, the reaction was poured into water and transferred to a separatory funnel and extracted with EA (×3). The combined organic layers were washed with brine, dried over Na₂SO₄, and concentrated under reduced pressure to afford the crude product. The crude residue was purified by column chromatography on silica gel using 0-30% EA in hexanes as the eluant to afford desired product: MS (m/z) 398.0 [M+H]⁺.

Synthesis of N-(3-bromophenyl)-7-chloro-N-ethyl-2-hydrazino-quinazolin-4-amine: To a solution of N-(3-bromophenyl)-2,7-dichloro-N-ethyl-quinazolin-4-amine (511 mg, 1.29 mmol) in THF (10 mL) and ethanol (10 mL) was added hydrazine (412 mg, 12.9 mmol) at 0° C. The resultant mixture was stirred at RT for 30 mins. Upon completion, the reaction was poured into water and transferred to a separatory funnel and extracted with DCM (×3). The combined organic layers were washed with brine, dried over $Na_2SO_4$, and concentrated under reduced pressure to afford the crude product: MS (m/z) 393.0 [M+H]⁺.

Synthesis of N-(3-bromophenyl)-8-chloro-N-ethyl-[1,2,4]triazolo[4,3-a]quinazolin-5-amine (Compound 455-1): A solution of N-(3-bromophenyl)-7-chloro-N-ethyl-2-hydrazino-quinazolin-4-amine (450 mg, 1.15 mmol) and triethyl orthoformate (2.04 g, 13.8 mmol) was heated to 100° C. for 1 h. Upon completion, the reaction was cooled to RT, and concentrated under reduced pressure to afford the crude product. The crude product was triturated with heptane and the material was collected by filtration, washed with heptane:ether (1:1) and dried in vacuo to afford the desired product: MS (m/z) 403.0 [M+H]⁺.

To a solution of N-(3-bromophenyl)-8-chloro-N-ethyl-[1,2,4]triazolo[4,3-a]quinazolin-5-amine (25 mg, 0.062 mmol) in dioxane (2 mL) was added 2-(difluoromethyl)-5-(4,4,5,5-tetramethyl-1,3,2-dioxaborolan-2-yl)pyridine (15.8 mg, 0.06 mmol), Pd(dppf)C12 (2.57 mg, 3.1 µmol), and 2 M solution of $Na_2CO_3$(aq) (0.154 mL, 0.307 mmol) and the mixture was purged with nitrogen and heated at 80° C. for 20 min. Upon completion, the mixture was diluted with EA, filtered through Celite®, and concentrated under reduced pressure. The crude product was dissolved in DMSO and purified via reverse phase HPLC to afford the title compound: ¹H NMR (400 MHz, DMSO-$d_6$) δ 9.77 (s, 1H), 8.97 (d, J=2.2 Hz, 1H), 8.61 (d, J=2.1 Hz, 1H), 8.28 (dd, J=8.2, 2.3 Hz, 1H), 7.89 (d, J=2.0 Hz, 1H), 7.80 (dd, J=16.7, 8.0 Hz, 2H), 7.61 (t, J=7.9 Hz, 1H), 7.50-7.41 (m, 1H), 7.38 (dd, J=9.0, 2.1 Hz, 1H), 7.25 (d, J=9.0 Hz, 1H), 7.00 (t, J=54.9 Hz, 1H), 4.27 (q, J=7.0 Hz, 2H), 1.29 (t, J=6.9 Hz, 3H); LCMS(m/z) 451.1.

Example 456. 8-chloro-7-fluoro-N-methyl-N-phenyl-[1,2,4]triazolo[4,3-a]quinazolin-5-amine

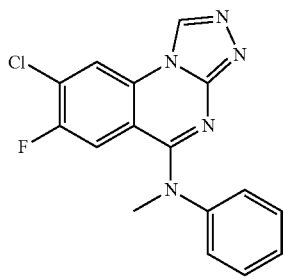

The title compound was synthesized according to the general procedure described for Example 11: ¹H NMR (400 MHz, DMSO-$d_6$) δ 9.60 (s, 1H), 8.75 (d, J=6.7 Hz, 1H), 7.47-7.41 (m, 2H), 7.38-7.30 (m, 3H), 6.90 (d, J=10.8 Hz, 1H), 3.54 (s, 3H); LCMS(m/z) 328.1.

Example 457. 5-(4-(tert-butyl)phenyl)-N-(8-chloro-[1,2,4]triazolo[4,3-a]quinazolin-5-yl)-N-methylthiazol-2-amine

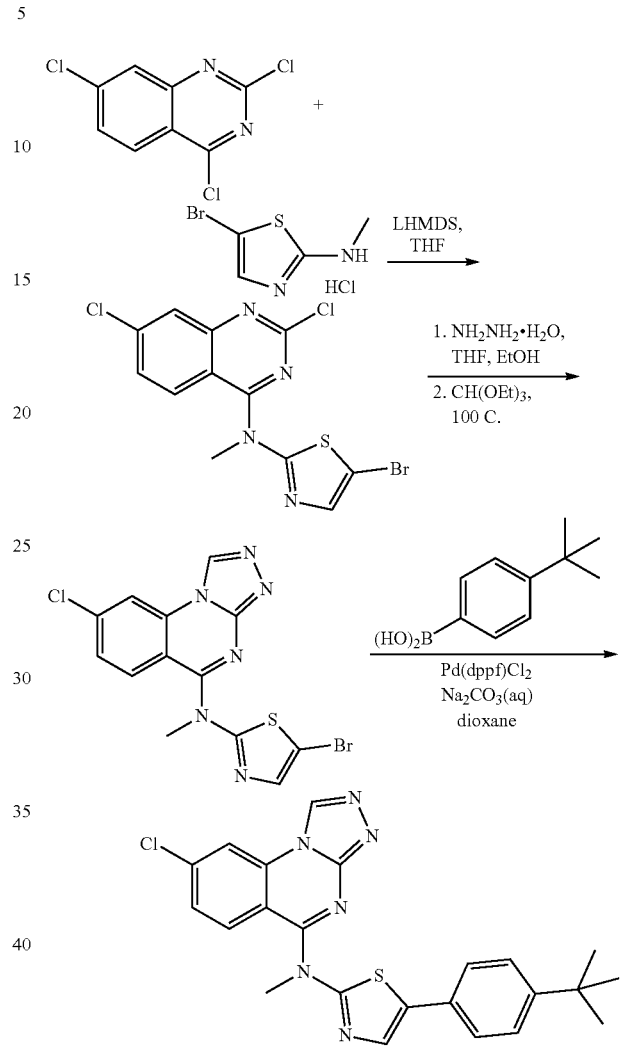

To a solution of 2,4,7-trichloroquinazoline (124 mg, 0.526 mmol) and 5-bromo-N-methylthiazol-2-amine hydrochloride (130.0 mg, 0.565 mmol) in tetrahydrofuran (5 mL) cooled to −20° C. was added a 1 molar solution of lithium hexamethyldisilazide in tetrahydrofuran (1.55 mL, 1.55 mmol). The reaction was stirred at −20° C. for one hour then partitioned between dichloromethane and water. The aqueous phase was extracted to dichloromethane, combined organics dried over sodium sulfate, filtered, and concentrated under reduced pressure to afford 186 mg 5-bromo-N-(2,7-dichloroquinazolin-4-yl)-N-methylthiazol-2-amine which was carried forward without further purification. ¹H NMR (400 MHz, Chloroform-d) δ 8.02 (d, J=9.1 Hz, 1H), 7.95 (d, J=2.2 Hz, 1H), 7.55-7.48 (m, 2H), 4.08 (s, 3H).

To a solution of 5-bromo-N-(2,7-dichloroquinazolin-4-yl)-N-methylthiazol-2-amine (186 mg, 0.477 mmol) in tetrahydrofuran (1.5 mL) and ethanol (0.8 mL) was added hydrazine hydrate (0.25 mL, 5.14 mmol) and the mixture stirred for 30 minutes. The reaction mixture was diluted with water then extracted to dichloromethane. The organic phase was washed with brine, dried over sodium sulfate, and concentrated under reduced pressured to afford crude 5-bromo-N-(7-chloro-2-hydrazineylquinazolin-4-yl)-N-methylthiazol-2-amine which was carried forward without further purification.

A suspension of crude 5-bromo-N-(7-chloro-2-hydrazineylquinazolin-4-yl)-N-methylthiazol-2-amine (0.477 mmol maximum) and triethyl orthoformate (2.00 mL, 12.0 mmol) was stirred at 100° C. for 90 minutes at which point the reaction mixture was cooled to room temperature and hexanes added to precipitate solids, which was collected by filtration with hexanes trituration. The collected solids were purified by silica gel chromatography (0-100% ethyl acetate:hexanes) to afford 5-bromo-N-(8-chloro-[1,2,4]triazolo[4,3-a]quinazolin-5-yl)-N-methylthiazol-2-amine.

A solution of 5-bromo-N-(8-chloro-[1,2,4]triazolo[4,3-a]quinazolin-5-yl)-N-methylthiazol-2-amine (24.0 mg, 0.0607 mmol), (4-tert-butylphenyl)boronic acid (22.0 mg, 0.124 mmol), 1,1'-bis(diphenylphosphino)ferrocene (11.0 mg, 0.0153 mmol) in dioxane (1 mL) and saturated aqueous sodium carbonate (0.1 mL) was stirred at 90° C. for 18 hours, and then at 120° C. for an additional 3.5 hours. The reaction mixture was concentrated under reduced pressure, dissolved in N,N-dimethylfomamide, passed through a syringe filter, and purified by preparative HPLC (10-100% acetonitrile in water, 0.1% TFA buffer) to afford the title compound: $^1$H NMR (400 MHz, DMSO-$d_6$) δ 9.83 (s, 1H), 8.71 (d, J=2.0 Hz, 1H), 7.97 (d, J=8.9 Hz, 1H), 7.80 (s, 1H), 7.66 (dd, J=8.9, 2.1 Hz, 1H), 7.53 (d, J=8.4 Hz, 2H), 7.49-7.41 (m, 2H), 3.80 (s, 3H), 1.30 (s, 9H); LCMS(m/z) 449.3.

Example 458. 2-(4-(tert-butyl)phenyl)-N-(8-chloro-[1,2,4]triazolo[4,3-a]quinazolin-5-yl)-N-methylthiazol-5-amine

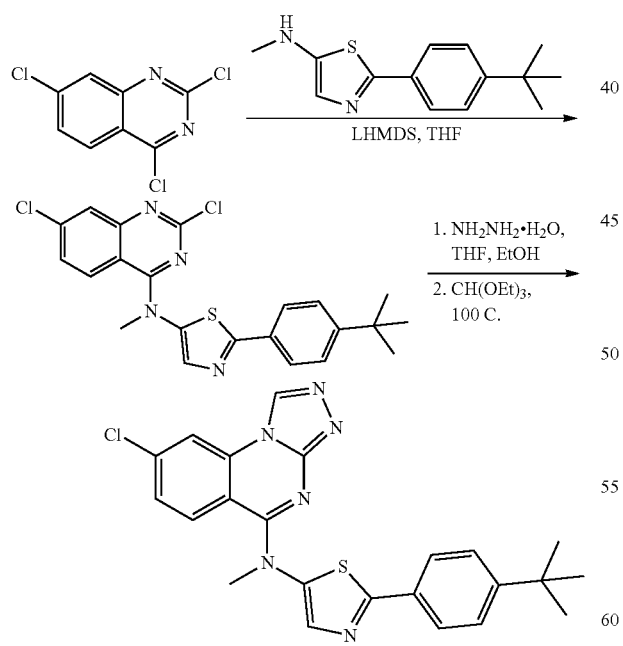

To a solution of 2,4,7-trichloroquinazoline (34 mg, 0.114 mmol) and 2-(4-(tert-butyl)phenyl)-N-methylthiazol-5-amine (35.7 mg, 0.145 mmol) in tetrahydrofuran (1 mL) cooled to −20° C. was added a 1 molar solution of lithium hexamethyldisilazide in tetrahydrofuran (0.3 mL, 0.3 mmol). The reaction was stirred at −20° C. for 30 minutes then partitioned between dichloromethane and water. The aqueous phase was extracted to dichloromethane, combined organics dried over sodium sulfate, filtered, concentrated under reduced pressure, and purified by silica gel chromatography (0-20% ethyl acetate:hexanes) to afford 2-(4-(tert-butyl)phenyl)-N-(2,7-dichloroquinazolin-4-yl)-N-methylthiazol-5-amine. $^1$H NMR (400 MHz, Chloroform-d) δ 9.96 (d, J=9.2 Hz, 1H), 8.06-7.98 (m, 2H), 7.85 (d, J=8.4 Hz, 2H), 7.59 (dd, J=9.2, 2.2 Hz, 1H), 7.55 (d, J=8.5 Hz, 2H), 3.37 (s, 3H), 1.41 (s, 9H).

To a solution of 2-(4-(tert-butyl)phenyl)-N-(2,7-dichloroquinazolin-4-yl)-N-methylthiazol-5-amine (28 mg, 0.063 mmol) in tetrahydrofuran (1.6 mL) and ethanol (0.8 mL) was added hydrazine hydrate (0.05 mL, 1.03 mmol) and the mixture stirred for 2 hours, at which point additional hydrazine hydrate (0.05 mL, 1.03 mmol) was added and stirring continued for 18 hours. The reaction mixture was diluted with water then extracted to dichloromethane. The organic phase was washed with brine, dried over sodium sulfate, and concentrated under reduced pressured to afford crude 2-(4-(tert-butyl)phenyl)-N-(7-chloro-2-hydrazineylquinazolin-4-yl)-N-methylthiazol-5-amine which was carried forward without further purification.

A suspension of crude 2-(4-(tert-butyl)phenyl)-N-(7-chloro-2-hydrazineylquinazolin-4-yl)-N-methylthiazol-5-amine (0.063 mmol maximum) and triethyl orthoformate (1.00 mL, 6.0 mmol) was stirred at 100° C. for 90 minutes at which point the reaction mixture was cooled to room temperature and hexanes added to precipitate material which was collected by filtration with hexanes trituration. The crude material was purified by preparative HPLC (10-100% acetonitrile in water, 0.1% TFA buffer) to afford the title compound: $^1$H NMR (400 MHz, DMSO-$d_6$) δ 10.10 (dd, J=12.2, 7.2 Hz, 2H), 9.78 (s, 1H), 8.61 (d, J=2.1 Hz, 1H), 7.90-7.79 (m, 3H), 7.56 (d, J=8.3 Hz, 2H), 3.30 (d, J=4.9 Hz, 3H), 1.35 (s, 9H); LCMS(m/z) 449.3.

Example 459. N-(3-bromophenyl)-7,8-difluoro-N-methyl-[1,2,4]triazolo[4,3-a]quinazolin-5-amine

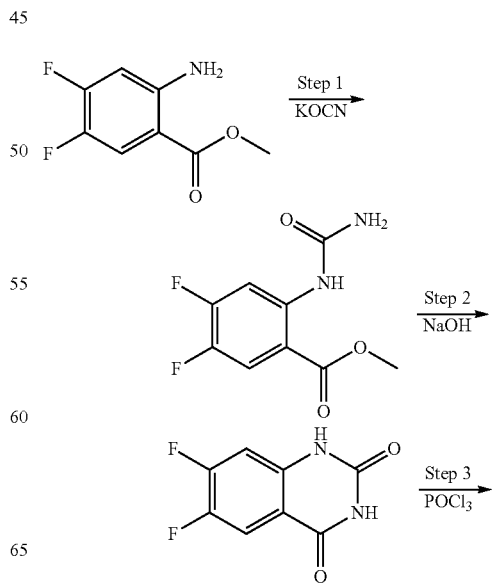

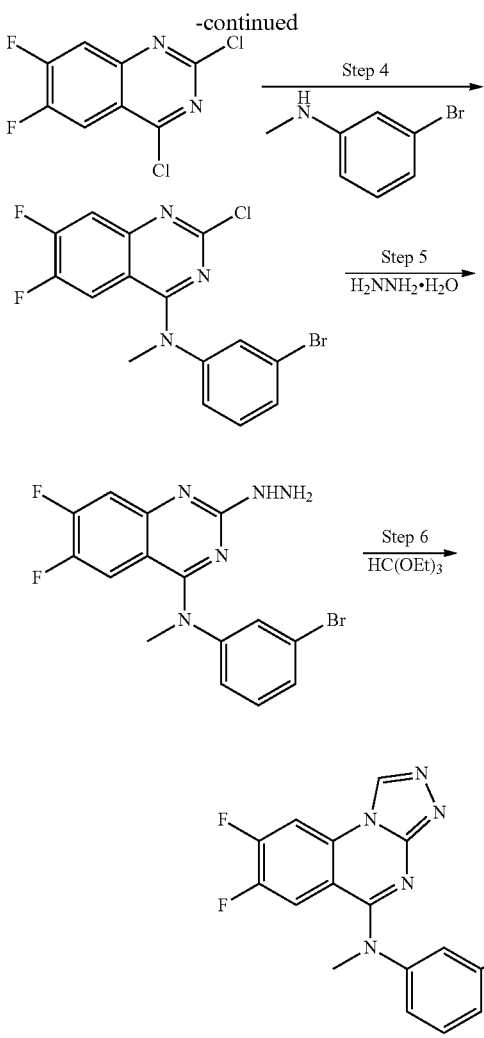

Step 1: Synthesis of Methyl 4, 5-difluoro-2-ureido-benzoate: Methyl 2-amino-4, 5-difluoro-benzoate (52.2 g, 273 mmol) was dissolved in acetic acid (350 mL) and treated slowly with a solution of potassium cyanate (46.2 g, 547 mmol) in water (150 mL). After stirring at room temperature for 20 hours and then 60° C. for 2 hours, 350 mL of water was added into the reaction mixture. The resulting precipitate was collected by filtration and washed with water. The precipitate was used directly in next step.

Step 2: Synthesis of 6, 7-difluoro-1H-quinazoline-2,4-dione: To a suspension of the material obtained above in methanol (500 mL) was added 109 mL of 3N sodium hydroxide aqueous solution. The suspension was stirred vigorously at room temperature for 20 hours. 165 mL of 2N HCl aqueous solution was added slowly with vigorous stirring to adjust pH to ~3. The solid was collected by filtration followed by a wash with water (50 mL). The filtrate was concentrated to remove most of the organic solvent. The precipitate was collected by filtration. The two batches were combined and dried on lyophlizer for 24 h to afford the desired product: $^1$H NMR (400 MHz, DMSO-$d_6$) δ 11.48 (s, 1H), 11.27 (s, 1H), 7.84 (dd, J=10.3, 8.5 Hz, 1H), 7.10 (dd, J=11.1, 6.6 Hz, 1H).

Step 3: Synthesis of 2,4-dichloro-6,7-difluoro-quinazoline: 6,7-difluoro-1H-quinazoline-2,4-dione (9.4 g, 47.4 mmol) was added into toluene (150 mL) in a 1.0 liter two neck round bottom flask. The mixture was treated with $POCl_3$ (10.2 mL, 109 mmol). The mixture was stirred at room temperature for 10 min and then warmed to 55° C. Tripropylamine (19 mL, 99.6 mmol) was added. After stirring at 55° C. for 10 min, the mixture was heated at 105° C. for 4 hours. Upon cooling down to room temperature, the solution was poured slowly to 300 mL of water (with 2 mL of 1N aqueous HCl) while stirring followed by dilution with toluene (200 ml). After stirring for 30 min, the aqueous layer was removed. The organic layer (with rag layer) was filtered and the filter cake was washed with toluene (50 mL) and water (40 mL). The two layers of the filtrate were separated, the organic layer was washed with water (200 mL×2) and brine (200 mL) until pH>3. It was dried over $MgSO_4$ and concentrated to dryness to afford the desired product: $^1$H NMR (400 MHz, Chloroform-d) δ 8.05 (dd, J=9.4, 8.0 Hz, 1H), 7.80 (dd, J=9.9, 7.2 Hz, 1H).

Step 4: Synthesis of N-(3-bromophenyl)-2-chloro-6,7-difluoro-N-methyl-quinazolin-4-amine: To a solution of 3-bromo-N-methylaniline (1.6 mL, 12.5 mmol) and 2,4-dichloro-6,7-difluoro-quinazoline (2.68 g, 11.4 mmol) in DMF (50 mL) at 0° C. was added NaH (60% purity) (547 mg, 13.7 mmol). The reaction mixture was warmed to RT and stirred for 4 hrs. The mixture was quenched with ice-cold saturated $NH_4Cl$ aqueous solution (40 mL), diluted with EtOAc (150 mL) and washed with water (100 mL). The precipitate formed between the aqueous and organic layers was collected by filtration, which was the desired product. The organic layer was further washed with brine (50 ml), dried over $Na_2SO_4$ and concentrated in vacuo. The resulting residue was purified by column chromatography using 0-35% EtOAc in hexanes to afford the desired product. The two batches of product were combined: $[M+H]^+$=384.2.

Step 5: Synthesis of N-(3-bromophenyl)-6,7-difluoro-2-hydrazino-N-methyl-quinazolin-4-amine: The resulting product (1.94 g, 5.0 mmol) from Step 4 was added into EtOH (21 mL) and THF (5 mL). hydrazine monohydrate (7.5 ml, 150 mmol) was added slowly in several portions and the reaction mixture was stirred at RT overnight until reaction went to completion. The reaction mixture diluted with EtOAc. The solution was washed successively with water and brine, dried over $Na_2SO_4$, and concentrated in vacuo. The crude was used in the next step without purification. $[M+H]^+$=380.2.

Step 6: To the resulting crude from above was added triethyl orthoformate (4 ml). The mixture was stirred at 100° C. for 16 h. The mixture was concentrated in vacuo and EtOAc (100 mL) was added to the resulting residue. The solution was washed successively with water and brine, dried over $Na_2SO_4$, and concentrated in vacuo. The crude was purified by column chromatography using 0-10% MeOH in DCM to afford the title compound: $^1$H NMR (400 MHz, Methanol-$d_4$) δ 9.43 (s, 1H), 8.33 (dd, J=10.5, 7.0 Hz, 1H), 7.59 (t, J=2.0 Hz, 1H), 7.55 (m, 1H), 7.39 (t, J=8.0 Hz, 1H), 7.32 (m, 1H), 7.16 (dd, J=11.8, 8.1 Hz, 1H), 3.66 (s, 3H); LCMS(m/z) 390.2.

Example 460. N-(4'-(tert-butyl)-[1,1'-biphenyl]-3-yl)-7,8-difluoro-N-methyl-[1,2,4]triazolo[4,3-a]quinazolin-5-amine

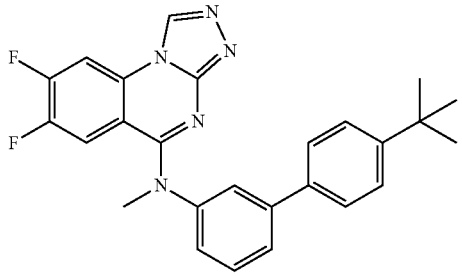

To a mixture of N-(3-bromophenyl)-7,8-difluoro-N-methyl-[1,2,4]triazolo[4,3-a]quinazolin-5-amine (Example 459, 100 mg, 0.256 mmol), (4-tert-butylphenyl)boronic acid (91 mg, 0.51 mmol), Pd(PPh$_3$)$_4$ (30 mg, 26 µmol) were added DME (3 mL) and 2M aqueous sodium carbonate (0.26 mL). After degassing and refilling with nitrogen several times, the reaction mixture was heated at 80° C. for 6 h. After cooling to RT, water and EtOAc were added. The two layers were separated and the organic layer was dried and concentrated. The crude was purified by column chromatography using 60-100% EtOAc in hexanes to afford the desired product: $^1$H NMR (400 MHz, Methanol-d$_4$) δ 9.36 (s, 1H), 8.32-8.20 (m, 1H), 7.64 (dt, J=7.9, 1.3 Hz, 1H), 7.59-7.42 (m, 6H), 7.26 (m, 1H), 7.19-7.06 (m, 1H), 3.71 (s, 3H), 1.33 (s, 9H); LCMS(m/z) 444.4.

Example 461. 7,8-difluoro-N-methyl-N-(4'-(trifluoromethyl)-[1,1'-biphenyl]-3-yl)-[1,2,4]triazolo[4,3-a]quinazolin-5-amine

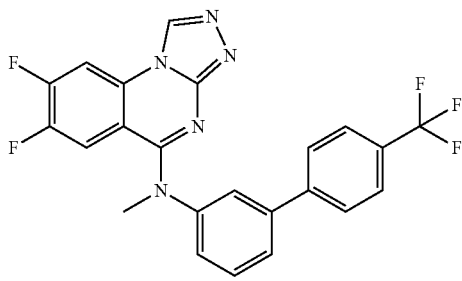

Example 461 was prepared according to the procedure described in Example 460. $^1$H NMR (400 MHz, Methanol-d$_4$) δ 9.37 (s, 1H), 8.27 (dd, J=10.2, 7.0 Hz, 1H), 7.79-7.65 (m, 5H), 7.64-7.55 (m, 2H), 7.35 (m, 1H), 7.15 (dd, J=11.8, 8.1 Hz, 1H), 3.73 (s, 3H); LCMS(m/z) 456.3.

Example 462. N5-(4'-(tert-butyl)-[1,1'-biphenyl]-3-yl)-7-fluoro-N5-methyl-[1,2,4]triazolo[4,3-a]quinazoline-5,8-diamine

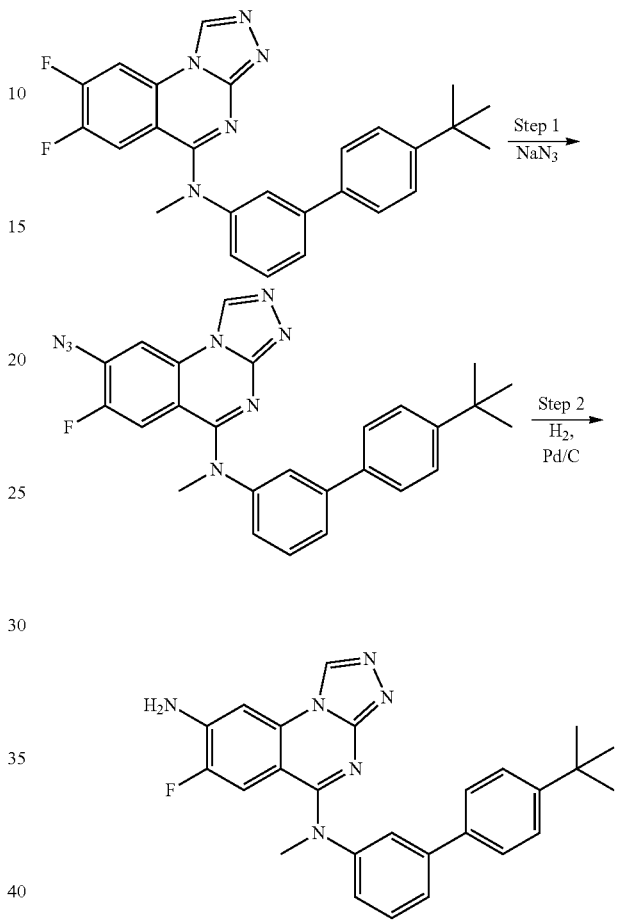

Step 1: Synthesis of 8-azido-N-[3-(4-tert-butylphenyl)phenyl]-7-fluoro-N-methyl-[1,2,4]triazolo[4,3-a]quinazolin-5-amine: A mixture of N-[3-(4-tert-butylphenyl)phenyl]-7,8-difluoro-N-methyl-[1,2,4]triazolo[4,3-a]quinazolin-5-amine (Example 460, 175 g, 0.40 mmol), sodium azide (129 mg, 1.98 mmol) in DMSO (3 mL) was heated at 90° C. for 4 h. To the mixture was added EtOAc (100 mL) and the solution was washed with water and brine. The organic layer was dried and concentrated to afford the crude product, which was used directly in next step. [M+H]$^+$=467.1.

Step 2: Synthesis of N5-[3-(4-tert-butylphenyl)phenyl]-7-fluoro-N5-methyl-[1,2,4]triazolo[4,3-a]quinazoline-5,8-diamine: To the product of Step 1 was added EtOH/EtOAc (3/3 mL) and 10% Pd/C (20 mg). The reaction mixture was degassed and recharged with hydrogen (gas bag) for several times. Then it was stirred under hydrogen overnight. Pd/C was filtered off. The filtrate was concentrated and purified by column chromatography using 5-10% MeOH in DCM to afford the title compound: $^1$H NMR (400 MHz, Methanol-d$_4$) δ 9.09 (s, 1H), 7.59 (dt, J=7.8, 1.3 Hz, 1H), 7.53-7.47 (m, 3H), 7.46 (d, J=3.3 Hz, 2H), 7.39 (d, J=2.0 Hz, 1H), 7.23 (d, J=7.6 Hz, 1H), 7.19 (m, 1H), 6.74 (dd, J=13.1, 1.3 Hz, 1H), 3.67 (s, 3H), 1.33 (s, 9H); LCMS(m/z) 441.4.

Example 463. 7-fluoro-N5-methyl-N5-(4'-(trifluoromethyl)-[1,1'-biphenyl]-3-yl)-[1,2,4]triazolo[4,3-a]quinazoline-5,8-diamine

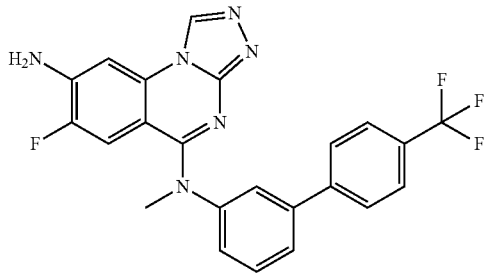

Example 463 was prepared according to the procedure described in Example 462 starting from Example 461. ¹H NMR (400 MHz, Methanol-d₄) δ 9.14 (s, 1H), 7.68 (s, 3H), 7.62 (d, J=3.7 Hz, 2H), 7.57 (t, J=7.8 Hz, 1H), 7.47 (t, J=1.9 Hz, 1H), 7.30 (m, 1H), 7.24 (d, J=7.7 Hz, 1H), 6.74 (d, J=13.1 Hz, 1H), 3.69 (s, 3H); LCMS(m/z) 453.3.

Example 464. 7-fluoro-N5-methyl-N5-(4'-(trifluoromethoxy)-[1,1'-biphenyl]-3-yl)-[1,2,4]triazolo[4,3-a]quinazoline-5,8-diamine

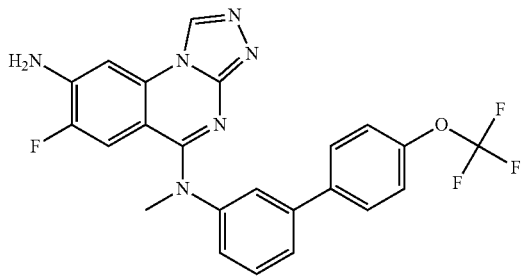

Example 464 was prepared according to the procedure described in Example 462 starting from Example 465. ¹H NMR (400 MHz, DMSO-d₆) δ 9.33 (s, 1H), 7.85-7.72 (m, 2H), 7.63 (t, J=2.0 Hz, 1H), 7.60-7.56 (m, 1H), 7.50 (t, J=7.8 Hz, 1H), 7.45-7.39 (m, 2H), 7.31-7.22 (m, 2H), 6.78 (d, J=13.1 Hz, 1H), 6.58 (s, 2H), 3.55 (s, 3H); LCMS(m/z) 469.3.

Example 465. 7,8-difluoro-N-methyl-N-(4'-(trifluoromethoxy)-[1,1'-biphenyl]-3-yl)-[1,2,4]triazolo[4,3-a]quinazolin-5-amine

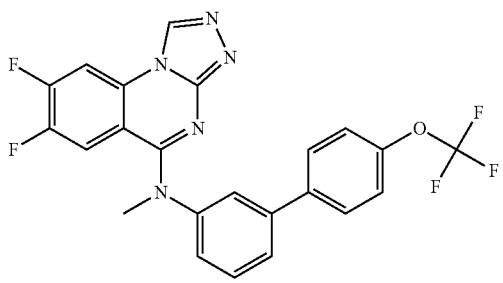

Example 465 was prepared according to the procedure described in Example 460. ¹H NMR (400 MHz, Chloroform-d) δ 9.99 (s, 1H), 8.65 (m, 1H), 7.76-7.68 (m, 2H), 7.68-7.59 (m, 3H), 7.48 (dd, J=9.7, 7.7 Hz, 1H), 7.30 (d, J=8.1 Hz, 2H), 6.97 (dd, J=11.7, 7.7 Hz, 1H), 3.86 (s, 3H); LCMS(m/z) 472.3.

Example 466. (5-((4'-(tert-butyl)-[1,1'-biphenyl]-3-yl)(methyl)amino)-7-fluoro-[1,2,4]triazolo[4,3-a]quinazolin-8-yl)methanol

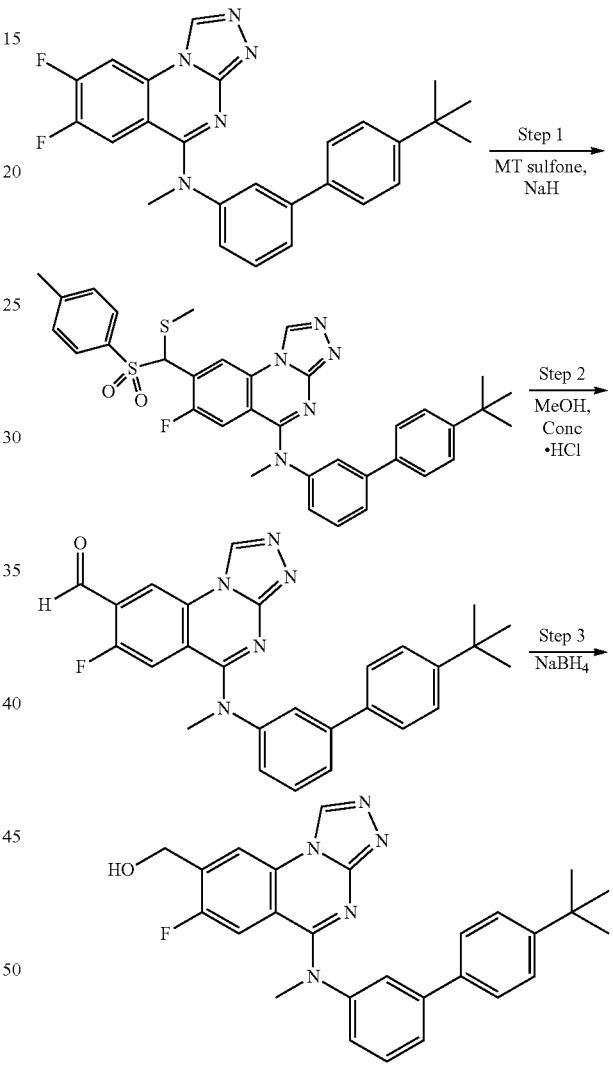

Step 1: Synthesis of N-(4'-(tert-butyl)-[1,1'-biphenyl]-3-yl)-7-fluoro-N-methyl-8-((methylthio)(tosyl)methyl)-[1,2,4]triazolo[4,3-a]quinazolin-5-amine: N-[3-(4-tert-butylphenyl)phenyl]-7,8-difluoro-N-methyl-[1,2,4]triazolo[4,3-a]quinazolin-5-amine (Example 460, 167 mg, 0.38 mmol) and 1-methyl-4-methylsulfanylmethylsulfonyl)benzene (163 mg, 0.75 mmol) were dissolved in DMF (6 mL). Sodium hydride (60%, 45 mg, 1.13 mmol) was added. The mixture was stirred at RT for 4 h until completion. The mixture was poured into ice cold sat. NH₄Cl solution and diluted with EtOAc (100 ml). The organic layer was washed with brine, dried and concentrated. The crude residue was purified by column chromatography using 80-100% EtOAc in hexanes to give desired product: [M+H]⁺=640.1.

Step 2: Synthesis of 5-((4'-(tert-butyl)-[1,1'-biphenyl]-3-yl)(methyl)amino)-7-fluoro-[1,2,4]triazolo[4,3-a]quinazoline-8-carbaldehyde: The product from Step 1 above was dissolved in MeOH (4 mL) in 20 ml of reaction tube, concentrated HCl(12 N)(1 mL) was added. The reaction tube was sealed and heated at 90° C. for 18 h. THF (5 mL) was added and the mixture was concentrated. The addition of THF and evaporation was repeated four times to afford the desired aldehyde: [M+H]⁺=454.4.

Step 3: Synthesis of N-[3-(4-tert-butylphenyl)phenyl]-7,8-difluoro-N-methyl-[1,2,4]triazolo[4,3-a]quinazolin-5-amine: The product of Step 2 obtained above was dissolved in THF (6 mL) and water (0.2 mL). 5 eq of NaBH₄ was added and reaction mixture was stirred at rt for 4 h. 5 mL of NaHCO₃ saturated aqueous solution was added. The reaction mixture was extracted with EtOAc (30 mL), and DCM/EtOH (5/1, 30 mL×2). The organic layers were combined, dried and concentrated. The residue was purified by RP-HPLC to afford the desired product: ¹H NMR (400 MHz, Methanol-d₄) δ 9.60 (s, 1H), 8.42 (d, J=6.2 Hz, 1H), 7.85-7.79 (m, 1H), 7.71-7.60 (m, 2H), 7.56-7.52 (m, 2H), 7.50-7.46 (m, 2H), 7.39 (m, 1H), 6.81 (d, J=11.7 Hz, 1H), 4.79 (s, 2H), 3.85 (s, 3H), 1.35 (s, 9H); LCMS(m/z) 456.4.

Example 467. 3-[7-fluoro-5-(3-fluoro-N-methyl-anilino)-[1,2,4]triazolo[4,3-a]quinazolin-8-yl]propan-1-ol

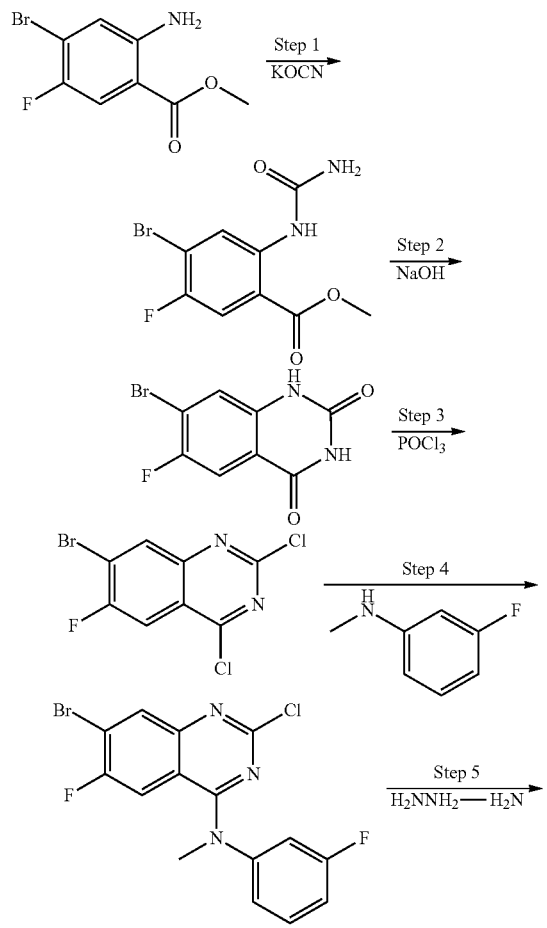

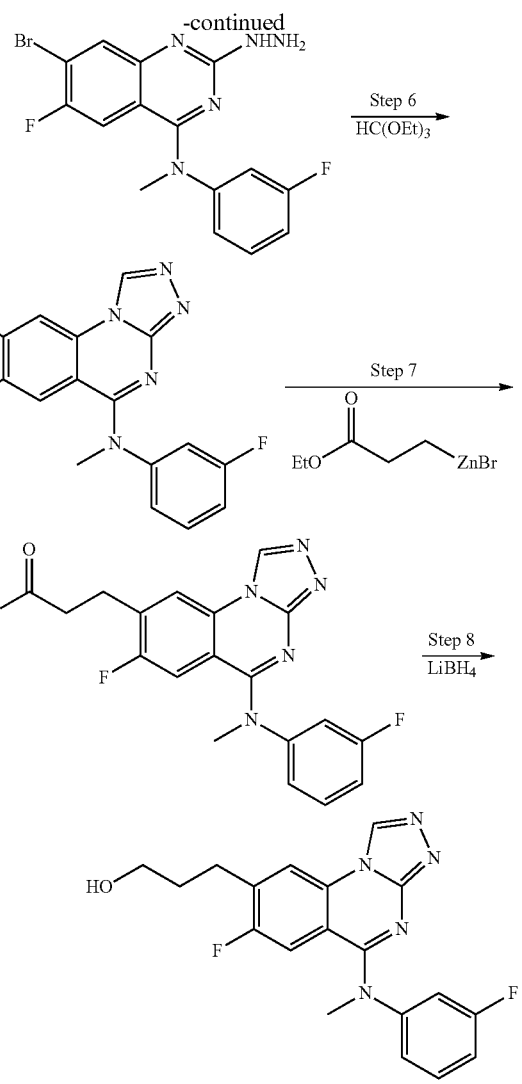

Step 1: Synthesis of Methyl 4-bromo-5-fluoro-2-ureido-benzoate: Methyl 2-amino-4-bromo-5-fluoro-benzoate (20.0 g, 79.0 mmol) was dissolved in acetic acid (200 mL) and treated slowly with a solution of potassium cyanate (13.4 g, 158 mmol) in water (40 mL). After stirring at room temperature for 20 h and then 60° C. for 2 h, 250 mL of water was added into the reaction mixture. The resulting material was collected by filtration and wash with water. It was used directly in next step. [M+H]⁺=290.77.

Step 2: Synthesis of 7-Bromo-6-fluoro-1H-quinazoline-2,4-dione: To a suspension of the product of Step 1 obtained above in methanol (300 mL) was added 95 mL of 1N sodium hydroxide aqueous solution. The suspension was stirred vigorously at room temperature for 16 h. 49 mL of 2N HCl aqueous solution was added slowly with vigorous stirring to adjust pH to ~3. The material was collected by filtration followed by wash with water (50 mL). The filtrate was concentrated to remove most of the organic solvent. The precipitate was collected by filtration. The two batches were combined and dried in vacuum oven to afford the desired product: ¹H NMR (400 MHz, DMSO-d₆) δ 11.51 (s, 1H), 11.25 (s, 1H), 7.77 (d, J=34.5, 1H), 7.44 (d, J=5.6 Hz, 1H).

Step 3: Synthesis of 7-Bromo-2,4-dichloro-6-fluoro-quinazoline: 7-Bromo-6-fluoro-1H-quinazoline-2,4-dione (6.4 g, 24.7 mmol) was added into toluene (100 mL) in a 1 liter two neck round bottom flask. The mixture was treated with POCl$_3$ (5.3 mL, 56.8 mmol). The mixture was stirred at room temperature for 10 min and then warmed to 55° C. Tripropylamine (9.9 mL, 51.9 mmol) was added. After stirring at 55° C. for 10 min, reaction mixture was heated at 105° C. for 5 hours. Upon cooling down to room temperature, the solution was poured slowly to 200 mL of water (with 2 mL of 1N aqueous HCl) while stirring followed by dilution with toluene (200 ml).

After stirring for 30 min, the aqueous layer was removed. The organic layer (with rag layer) was filtered and the filter cake was washed with toluene (50 mL) and water (40 mL). The two layers of the filtrate were separated, the organic layer was washed with water (200 mL×2) and brine (200 mL) until pH>3. It was dried over MgSO$_4$ and concentrated to dryness to afford the desired product: $^1$H NMR (400 MHz, Chloroform-d) δ 8.33 (d, J=6.3 Hz, 1H), 7.95 (d, J=7.8 Hz, 1H).

Step 4: Synthesis of 7-bromo-2-chloro-6-fluoro-N-(3-fluorophenyl)-N-methyl-quinazolin-4-amine: To a solution of 3-fluoro-N-methylaniline (1.76 mL, 15.6 mmol) and 7-bromo-2,4-dichloro-6-fluoro-quinazoline (4.2 g, 14.2 mmol) in DMF (78 mL) at 0° C. was added NaH (60% purity) (738 mg, 18.5 mmol). The reaction mixture was warmed to RT and stirred overnight. The mixture was quenched with ice-cold saturated NH$_4$Cl aqueous solution (40 mL), diluted with AcOEt (200 mL) and washed with water (100 mL). The organic layer was further washed with brine (50 ml), dried over Na$_2$SO$_4$ and concentrated in vacuo. The resulting residue was recharged with EtOAc (30 mL) and the resulting precipitate was collected by filtration, which was the desired product. The filtrate was purified by column chromatography using 0-40% EtOAc in hexanes to afford the desired product. The two batches of product were combined: [M+H]$^+$=384.3.

Step 5: Synthesis of 7-bromo-N-(3-fluorophenyl)-6-fluoro-2-hydrazino-N-methyl-quinazolin-4-amine: The product (3.8 g, 5.0 mmol) from Step 4 was added into EtOH (44 mL) and THF (11 mL). Hydrazine monohydrate (7.5 ml) was added slowly in several portions and the reaction mixture was stirred at RT overnight until reaction went to completion. The resulting precipitate was collected by filtration, which was the desired product based on LC/MS. The filtrate was diluted with EtOAc, washed successively with water and brine, dried over Na$_2$SO$_4$, and concentrated in vacuo. The crude was combined with the precipitate batch and used in the next step without purification. [M+H]$^+$=380.2.

Step 6: Synthesis of 8-bromo-7-fluoro-N-(3-fluorophenyl)-N-methyl-[1,2,4]triazolo[4,3-a]quinazolin-5-amine: To the resulting product from Step 5 obtained from above was added triethyl orthoformate (33 ml). The reaction mixture was stirred at 100° C. for 16 h. The reaction mixture was concentrated in vacuo and EtOAc (100 mL) was added to the resulting residue. The solution was washed successively with water and brine, dried over Na$_2$SO$_4$, and concentrated in vacuo. The crude was purified by column chromatography using 5-10% MeOH in DCM to afford the desired product. [M+H]$^+$=390.2.

Step 7: Synthesis of ethyl 3-[7-fluoro-5-(3-fluoro-N-methyl-anilino)-[1,2,4]triazolo[4,3-a]quinazolin-8-yl]propanoate: 8-bromo-7-fluoro-N-(3-fluorophenyl)-N-methyl-[1,2,4]triazolo[4,3-a]quinazolin-5-amine (90 mg, 0.23 mmol), Pd(dba)$_2$ (13 mg, 0.023 mmol), 1,2,3,4,5-pentaphenyl-1'-(di-tert-butylphosphino)ferrocene (16 mg, 0.023 mmol) were added into a 100 mL flask. The mixture was degassed and refilled with nitrogen several times and then THF (4 mL) was added followed by addition of bromo-(3-ethoxy-3-oxo-propyl)zinc reagent (0.5 M in THF, 0.92 mL). The mixture was stirred at RT for 15 min and the reaction went to completion. 10 mL of saturated NH$_4$Cl aqueous solution was added to quench the reaction. 60 mL of EtOAc and 20 mL of water were added. The two layers were separated. The organic layer was washed with brine, dried, concentrated and the crude was purified by column chromatography using EtOAc to afford the desired ester: [M+H]$^+$=412.3.

Step 8: To the ester obtained above (36 mg, 0.088 mmol) in THF (4 mL) were added LiBH$_4$ (4 mg, 0.18 mmol) and 0.2 mL of MeOH. The reaction mixture was stirred at RT for 18 h until completion. 10 mL of saturated NH$_4$Cl aqueous solution was added to quench the reaction. The mixture was diluted with 60 mL of EtOAc and washed with water (20 mL). The organic layer was washed with brine, dried, concentrated and the crude was purified by RP-HPLC to afford the title compound: $^1$H NMR (400 MHz, Methanol-d$_4$) δ 9.63 (s, 1H), 8.40-8.28 (m, 1H), 7.68-7.56 (m, 1H), 7.40-7.26 (m, 3H), 6.79 (dd, J=11.4, 8.6 Hz, 1H), 3.80 (s, 3H), 3.63 (t, J=6.2 Hz, 2H), 2.98-2.90 (m, 2H), 1.99-1.84 (m, 2H); LCMS(m/z) 370.3.

Example 468. 8-chloro-N-methyl-N-[3-[4-[2-(trifluoromethyl)oxetan-2-yl]phenyl]phenyl]-[1,2,4]triazolo[4,3-a]quinazolin-5-amine

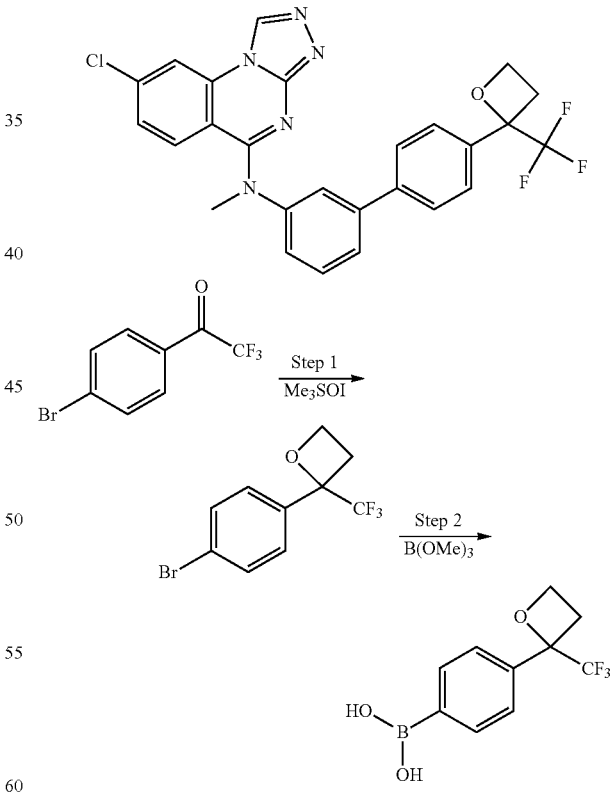

Step 1: Synthesis of 2-(4-bromophenyl)-2-(trifluoromethyl)oxetane: To a round bottom flask containing potassium tert-butoxide (3.30 g, 29.3 mmol) in DMSO (40 mL) was added trimethylsulfoxonium iodide (6.45 g, 29.3 mmol), and the reaction was stirred at room temperature for 20 min. A solution of the 4-bromo-trifluoroacetophenone (2.6 g, 9.76 mmol) in DMSO (10 mL) was added dropwise to the reaction, and the resulting solution was stirred at room temperature overnight. The crude reaction mixture was partitioned between diethyl ether and brine. The organic layer was separated, washed once more with brine, dried over anhydrous sodium sulfate, and concentrated under reduced pressure. The crude product was purified by column chromatography using 0-50% EtOAc in hexane to afford the corresponding trifluoromethyl oxetane: $^1$H NMR (400 MHz, Chloroform-d) δ 7.60-7.55 (m, 2H), 7.34 (s, 2H), 4.85 (m, 1H), 4.61 (dt, J=9.2, 6.0 Hz, 1H), 3.28 (m, 1H), 2.89 (m, 1H).

Step 2: Synthesis of (4-(2-(trifluoromethyl)oxetan-2-yl) phenyl)boronic acid: To the trifluoromethyl oxetane of Step 1 above (1.5 g, 5.07 mmol) in THF (15 mL) at −78° C. was added 1.6M butyllithium in hexane (3.5 mL, 5.58 mmol). After stirring one hour, trimethylborate (0.87 mL, 7.6 mmol) was added. After warming to room temp, the THF was removed in vacuo. The residue was taken up in water and extracted with ether to remove non-polar impurities. The aqueous layer was acidified and extracted with ethyl acetate. The organic layer was washed with saturated sodium chloride, dried over sodium sulfate, filtered and concentrated to dryness. The crude was further purified by column using 20-80% EtOAc in hexane to afford the desired phenylboronic acid: $^1$H NMR (400 MHz, Chloroform-d) δ 8.31 (d, J=7.7 Hz, 1H), 7.60 (d, J=7.7 Hz, 1H), 7.48 (d, J=7.7 Hz, 1H), 4.89 (m, 1H), 4.74-4.56 (m, 1H), 3.35 (m, 1H), 2.99 (dt, J=19.5, 10.0 Hz, 1H).

N-(3-bromophenyl)-8-chloro-N-methyl-[1,2,4]triazolo[4,3-a]quinazolin-5-amine (Example 308, 80 mg, 0.20 mmol), [4-[2-(trifluoromethyl)oxetan-2-yl]phenyl]boronic acid (76 mg, 0.31 mmol), and Pd(PPh$_3$)$_4$ (24 mg, 0.02 mmol) were added into dioxane (3 mL) and 2M aqueous sodium carbonate solution (0.2 mL) was added. The mixture was degassed and refilled with N$_2$ several times. The mixture was heated at 80° C. for 90 min. After cooling to RT, water and EtOAc were added. The two layers were separated, and the organic layer was washed with brine, dried and concentrated. The crude material was purified by column chromatography using 80-100% EtOAc in hexanes to obtain the title compound: $^1$H NMR (400 MHz, Methanol-d$_4$) δ 9.44 (s, 1H), 8.32 (d, J=2.1 Hz, 1H), 7.69-7.59 (m, 4H), 7.58-7.45 (m, 3H), 7.36 (d, J=9.0 Hz, 1H), 7.32-7.26 (m, 1H), 7.21 (dd, J=9.0, 2.0 Hz, 1H), 4.81 (m, 1H), 4.61 (dt, J=9.2, 6.0 Hz, 1H), 3.72 (s, 3H), 3.32-3.24 (m, 1H), 3.05-2.92 (m, 1H); LCMS(m/z) 510.3.

Example 469. 8-chloro-N-methyl-N-(4'-(1-(trifluoromethyl)cyclopropyl)-[1,1'-biphenyl]-3-yl)-[1,2,4]triazolo[4,3-a]quinazolin-5-amine

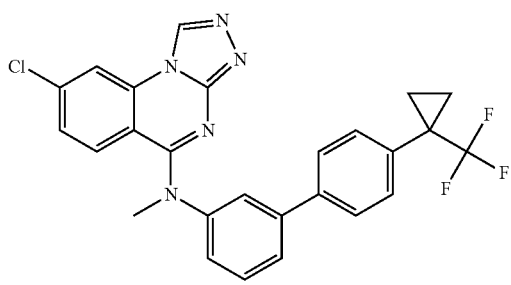

Example 469 was synthesized using the method described for Example 468 with the corresponding boronic acid or ester. $^1$H NMR (400 MHz, Methanol-d$_4$) δ 9.55 (s, 1H), 8.55-8.43 (m, 1H), 7.77 (dt, J=8.0, 1.2 Hz, 1H), 7.71 (t, J=2.0 Hz, 1H), 7.67-7.59 (m, 3H), 7.56 (d, J=8.2 Hz, 2H), 7.41 (m, 1H), 7.33 (t, J=1.5 Hz, 2H), 3.83 (s, 3H), 1.39 (d, J=1.9 Hz, 1H), 1.31 (s, 2H), 1.12-1.10 (m, 1H); LCMS(m/z) 494.3.

Example 470. N-(3-(1-(tert-butyl)-1H-pyrazol-4-yl) phenyl)-8-chloro-N-methyl-[1,2,4]triazolo[4,3-a]quinazolin-5-amine

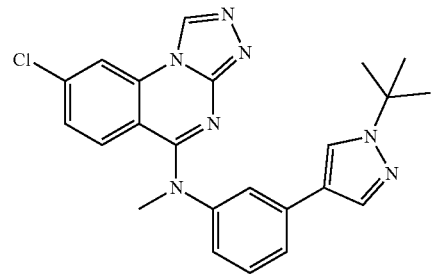

Example 470 was synthesized using the method described for Example 468 with the corresponding boronic acid or ester. $^1$H NMR (400 MHz, Methanol-d$_4$) δ 9.44 (s, 1H), 8.32 (d, J=2.1 Hz, 1H), 8.16 (s, 1H), 7.85 (s, 1H), 7.61-7.53 (m, 2H), 7.47-7.33 (m, 2H), 7.20 (dd, J=9.0, 2.1 Hz, 1H), 7.14-7.08 (m, 1H), 3.69 (s, 3H), 1.61 (s, 9H); LCMS(m/z) 432.3.

Example 471. 8-chloro-N-methyl-N-[3-(3-methyl-3-methylsulfonyl-but-1-ynyl)phenyl]-[1,2,4]triazolo[4,3-a]quinazolin-5-amine Synthesis of 3-methyl-3-(methylsulfonyl)but-1-yne

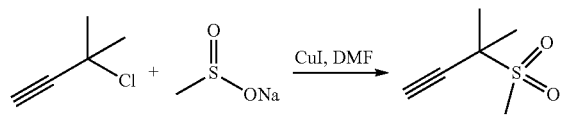

To a stirred suspension of sodium methanesulfinate (8.96 g, 83.4 mmol), copper(I) iodide (1.39 g, 7.3 mmol) in DMF (25 mL) was added 3-chloro-3-methylbut-1-yne (8.2 mL, 73.1 mmol) dropwise. The resulting reaction mixture was heated at 40° C. for 20 h. Upon cooling to RT, reaction mixture was diluted with EtOAc (300 ml), washed with water (100 ml) and brine (100 ml), dried and concentrated. The crude was purified by column chromatography using 10-60% EtOAc in hexane to afford the desired product: $^1$H NMR (400 MHz, Chloroform-d) δ 3.06 (s, 3H), 2.60 (s, 1H), 1.69 (s, 6H).

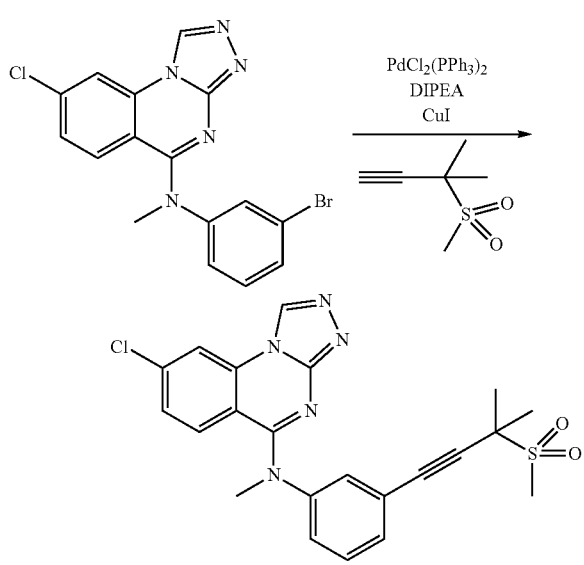

A mixture of N-(3-bromophenyl)-8-chloro-N-methyl-[1,2,4]triazolo[4,3-a]quinazolin-5-amine (Example 308, 30 mg, 0.077 mmol), 3-methyl-3-(methylsulfonyl)but-1-yne (23 mg, 0.154 mmol), DIPEA (27 uL, 0.154 mmol), CuI (3 mg, 0.015 mmol), PdCl$_2$(PPh$_3$)$_2$ (5.4 mg, 8 umol) in DMF (2 mL) was degassed and refilled with nitrogen for several times and then it was heated at 100° C. overnight. The reaction mixture was diluted with EtOAc, washed with water and brine, dried, and concentrated. The crude was purified by column chromatography using 20-100% of (EtOAc/EtOH 3/1) in hexanes to afford the desired product: $^1$H NMR (400 MHz, Methanol-d$_4$) δ 9.46 (s, 1H), 8.36 (d, J=2.0 Hz, 1H), 7.47 (dt, J=2.3, 1.0 Hz, 1H), 7.45-7.42 (m, 2H), 7.36-7.30 (m, 2H), 7.26 (dd, J=9.0, 2.0 Hz, 1H), 3.64 (s, 3H), 3.11 (s, 3H), 1.71 (s, 6H); LCMS(m/z) 454.1.

Example 472. 8-chloro-N-(3-(3,3-dimethylbut-1-yn-1-yl)phenyl)-N-methyl-[1,2,4]triazolo[4,3-a]quinazolin-5-amine

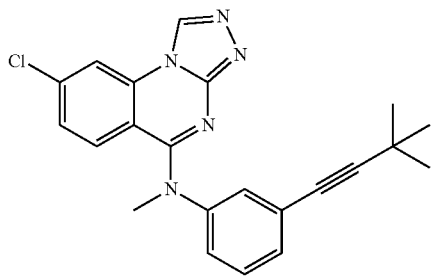

Example 472 was prepared according to the method described for Example 471 with Example 308 and the corresponding alkyne. $^1$H NMR (400 MHz, Methanol-d$_4$) δ 9.46 (s, 1H), 8.36 (d, J=2.0 Hz, 1H), 7.37 (d, J=7.8 Hz, 1H), 7.33 (dt, J=5.7, 2.1 Hz, 3H), 7.27 (dd, J=9.0, 2.0 Hz, 1H), 7.19 (m, 1H), 3.64 (s, 3H), 1.31 (s, 9H); LCMS(m/z) 390.3.

Example 473. N-methyl-8-(3-methyl-3-(methyl-sulfonyl)but-1-yn-1-yl)-N-(3-(3-methyl-3-(methyl-sulfonyl)but-1-yn-1-yl)phenyl)-[1,2,4]triazolo[4,3-a]quinazolin-5-amine

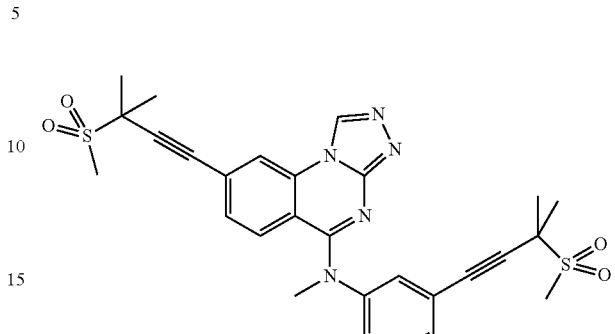

Example 473 was isolated as an additional product from the Sonogashira reaction described in Example 471. $^1$H NMR (400 MHz, Methanol-d$_4$) δ 9.69 (s, 1H), 8.50 (d, J=1.3 Hz, 1H), 7.59-7.53 (m, 3H), 7.46 (m, 1H), 7.40 (m, 1H), 7.27 (dd, J=8.9, 2.1 Hz, 1H), 3.77 (s, 3H), 3.18 (s, 3H), 3.10 (s, 6H), 1.80 (s, 6H), 1.67 (s, 6H); LCMS(m/z) 564.1.

Example 474. N-methyl-N-(3-(3-methyl-3-(methyl-sulfonyl)but-1-yn-1-yl)phenyl)-8-(methylsulfonyl)-[1,2,4]triazolo[4,3-a]quinazolin-5-amine

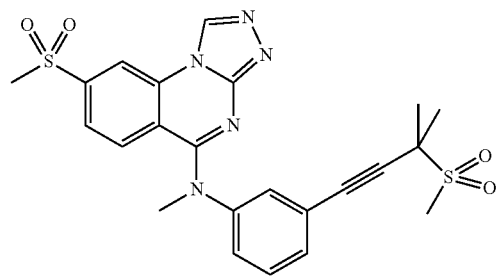

Example 474 was isolated as an additional product from the Sonogashira reaction described in Example 471. $^1$H NMR (400 MHz, Methanol-d$_4$) δ 9.84 (s, 1H), 8.91 (d, J=1.8 Hz, 1H), 7.85 (dd, J=8.8, 1.7 Hz, 1H), 7.64-7.50 (m, 4H), 7.48 (dt, J=7.7, 2.0 Hz, 1H), 3.79 (s, 3H), 3.26 (s, 3H), 3.11 (s, 3H), 1.71 (s, 6H); LCMS(m/z) 498.1.

Example 475. 5-(methyl(4'-(2-(trifluoromethyl)oxetan-2-yl)-[1,1'-biphenyl]-3-yl)amino)-[1,2,4]triazolo[4,3-a]quinazoline-8-carbonitrile

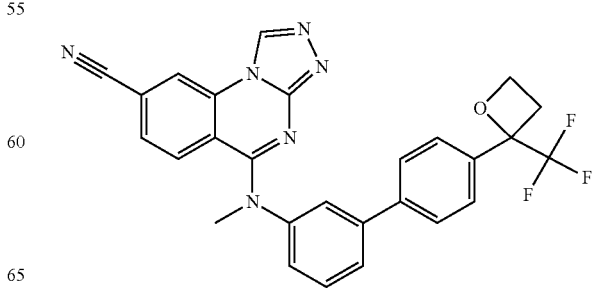

8-Chloro-N-methyl-N-[3-[4-[2-(trifluoromethyl)oxetan-2-yl]phenyl]phenyl]-[1,2,4]triazolo[4,3-a]quinazolin-5-amine (Example 468.18 mg, 0.035 mmol), K₄Fe(CN)₆·3H₂O (4 mg, 9 umol), Pd(OAc)₂ (1 mg, 4 umol), XPhos (3 mg, 7 umol), K₂CO₃ (1 mg, 9 umol) were added in THF/water (1 mL/1 mL). The reaction mixture was degassed and refilled with nitrogen for several times. It was heated at 120° C. for 10 h. After cooling to RT, water and EtOAc were added. The two layers were separated, the organic layer was washed with brine, dried and concentrated. The crude residue was purified by column chromatography using 50-100% EtOH/EtOAc (1/3) in hexanes to afford the desired product: ¹H NMR (400 MHz, Methanol-d₄) δ 9.44 (s, 1H), 8.32 (d, J=2.1 Hz, 1H), 7.69-7.59 (m, 4H), 7.58-7.45 (m, 3H), 7.36 (d, J=9.0 Hz, 1H), 7.32-7.26 (m, 1H), 7.21 (dd, J=9.0, 2.0 Hz, 1H), 4.81 (m, 1H), 4.61 (dt, J=9.2, 6.0 Hz, 1H), 3.72 (s, 3H), 3.32-3.24 (m, 1H), 3.05-2.92 (m, 1H); LCMS(m/z) 510.3.

Example 476. N-(3'-((8-chloro-[1,2,4]triazolo[4,3-a]quinazolin-5-yl)(methyl)amino)-[1,1'-biphenyl]-4-yl)pivalamide

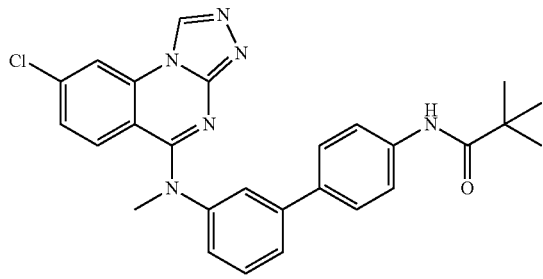

Example 476 was prepared according to the method described for Example 468 using Example 308 and the corresponding boronic acid or ester. ¹H NMR (400 MHz, Methanol-d₄) δ 9.58 (s, 1H), 8.50 (d, J=2.0 Hz, 1H), 7.80 (m, 1H), 7.73 (t, J=2.0 Hz, 1H), 7.69-7.63 (m, 3H), 7.61-7.57 (m, 2H), 7.44-7.34 (m, 2H), 7.30 (d, J=9.1 Hz, 1H), 3.86 (s, 3H), 1.32 (s, 9H); LCMS(m/z) 485.4.

Example 477. 4-(3-((8-chloro-[1,2,4]triazolo[4,3-a]quinazolin-5-yl)(methyl)amino)phenyl)-2-methyl-but-3-yn-2-ol

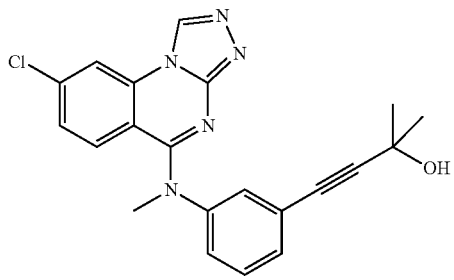

Example 477 was prepared according to the method described for Example 471 with Example 308 and the corresponding alkyne. ¹H NMR (400 MHz, Methanol-d₄) δ 9.61 (s, 1H), 8.51 (d, J=2.0 Hz, 1H), 7.57-7.51 (m, 2H), 7.51-7.48 (m, 1H), 7.44 (m, 1H), 7.39 (dd, J=9.1, 2.0 Hz, 1H), 7.23 (dd, J=9.1, 1.2 Hz, 1H), 3.78 (s, 3H), 1.54 (s, 6H); LCMS(m/z) 392.2.

Example 478. 8-chloro-N-(3-((4-chlorophenyl)ethynyl)phenyl)-N-methyl-[1,2,4]triazolo[4,3-a]quinazolin-5-amine

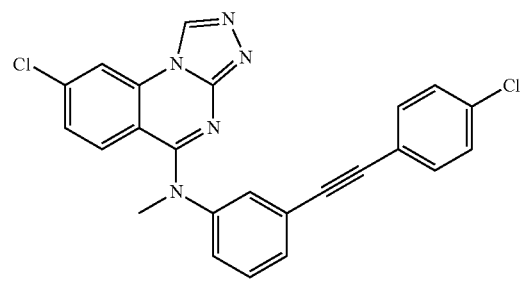

Example 478 was prepared according to the method described for Example 471 with Example 308 and the corresponding alkyne. ¹H NMR (400 MHz, Methanol-d₄) δ 9.62 (s, 1H), 8.50 (d, J=2.0 Hz, 1H), 7.65 (d, J=7.7 Hz, 2H), 7.62-7.55 (m, 2H), 7.47 (d, J=8.6 Hz, 2H), 7.40-7.35 (m, 2H), 7.24 (d, J=9.1 Hz, 2H), 3.81 (s, 3H); LCMS(m/z) 444.3.

Example 479. 8-chloro-N-methyl-N-(3-((1-(trifluoromethyl)cyclopropyl)ethynyl)phenyl)-[1,2,4]triazolo[4,3-a]quinazolin-5-amine

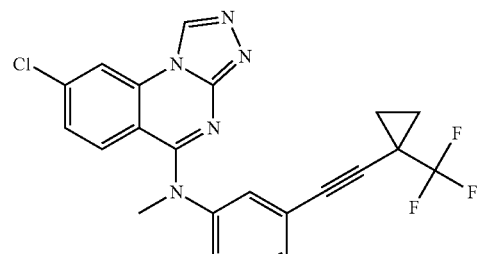

Example 479 was prepared according to the method described for Example 471 with Example 308 and the corresponding alkyne. ¹H NMR (400 MHz, Methanol-d₄) δ 9.43 (s, 1H), 8.34 (d, J=1.9 Hz, 1H), 7.42-7.36 (m, 3H), 7.29 (d, J=9.0 Hz, 1H), 7.23 (m, 2H), 3.65 (s, 3H), 1.43-1.35 (m, 2H), 1.28 (d, J=3.2 Hz, 2H); LCMS(m/z) 442.3.

Example 480. 4-(3-((8-(3-hydroxy-3-methylbut-1-yn-1-yl)-[1,2,4]triazolo[4,3-a]quinazolin-5-yl)(methyl)amino)phenyl)-2-methylbut-3-yn-2-ol

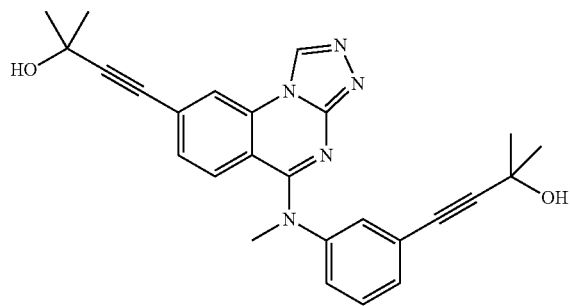

Example 480 was prepared according to the method described for Example 471 with Example 308 and the corresponding alkyne. $^1$H NMR (400 MHz, Methanol-$d_4$) δ 9.62 (s, 1H), 8.42 (d, J=1.5 Hz, 1H), 7.54 (m, 2H), 7.50 (m, 1H), 7.48-7.40 (m, 1H), 7.33 (dd, J=8.8, 1.5 Hz, 1H), 7.20 (d, J=8.8 Hz, 1H), 3.79 (s, 3H), 1.59 (s, 6H), 1.54 (s, 6H); LCMS(m/z) 440.3.

Example 481. 1-((3-((8-chloro-[1,2,4]triazolo[4,3-a]quinazolin-5-yl)(methyl)amino)phenyl)ethynyl)cyclopentan-1-ol

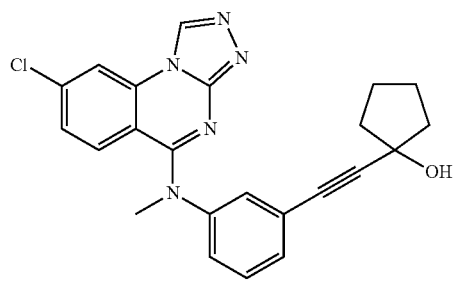

Example 481 was prepared according to the method described for Example 471 with Example 308 and the corresponding alkyne. $^1$H NMR (400 MHz, Methanol-$d_4$) δ 9.48 (s, 1H), 8.38 (m, 1H), 7.51-7.32 (m, 4H), 7.32-7.22 (m, 2H), 3.66 (s, 3H), 1.89-1.72 (m, 5H), 1.65 (s, 2H), 1.21 (m, 1H); LCMS(m/z) 418.2.

Example 482. N-(3-((8-chloro-[1,2,4]triazolo[4,3-a]quinazolin-5-yl)(methyl)amino)phenyl)benzamide

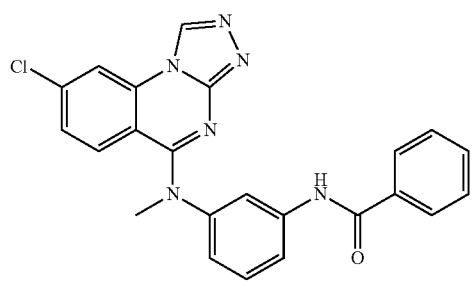

Example 482 was prepared according to the method described for Example 483, except starting from tert-butyl (3-aminophenyl)(methyl)carbamate and benzoic acid instead of aniline and 3-((tert-butoxycarbonyl)(methyl)amino)benzoic acid. $^1$H NMR (400 MHz, DMSO-$d_6$) δ 10.39 (s, 1H), 9.77 (s, 1H), 8.63 (d, J=2.1 Hz, 1H), 7.99-7.88 (m, 3H), 7.76 (d, J=8.1 Hz, 1H), 7.65-7.57 (m, 1H), 7.53 (t, J=7.4 Hz, 2H), 7.50-7.39 (m, 2H), 7.30 (d, J=9.0 Hz, 1H), 7.09 (dd, J=7.8, 2.1 Hz, 1H), 3.62 (s, 3H); LCMS(m/z) 429.1.

Example 483. 3-((8-chloro-[1,2,4]triazolo[4,3-a]quinazolin-5-yl)(methyl)amino)-N-phenylbenzamide

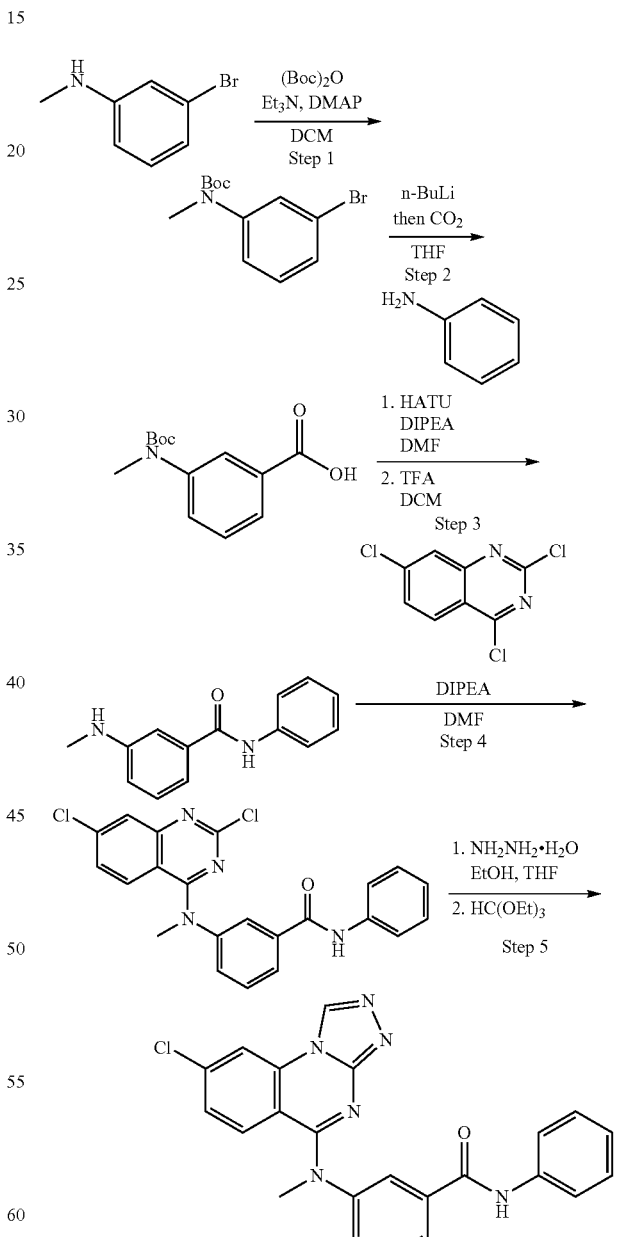

Step 1: tert-butyl N-(3-bromophenyl)-N-methyl-carbamate: To a solution of 3-bromo-N-methyl-aniline (4.00 g, 21.5 mmol) and Di-tert-butyl decarbonate (5.16 g, 23.6 mmol) in DCM was added triethylamine (12 mL, 86.0 mmol) and 4-dimethylaminopyridine (5.25 g, 4.3 mmol). The reaction mixture was stirred at room temperature for 24 h, then poured into water and extracted twice with ethyl acetate (ca. 150 mL each). The organic layers were combined and washed with 0.5 N HCl, then brine, dried with anhydrous magnesium sulfate, and concentrated under reduced pressure. Purification by flash chromatography (elution with 0-10% v/v ethyl acetate in hexanes) afforded tert-butyl N-(3-bromophenyl)-N-methyl-carbamate.

Step 2: 3-[tert-butoxycarbonyl(methyl)amino]benzoic acid: A solution of tert-butyl N-(3-bromophenyl)-N-methyl-carbamate (1.25 g, 4.37 mmol) in THF (50 mL) was sparged with nitrogen for 15 min and cooled to −78° C. followed by the addition of n-BuLi (3.49 mL, 2.50 M, 8.74 mmol). The reaction mixture was stirred at this temperature for 1 h, at which time carbon dioxide was bubbled through the reaction mixture and the solution was allowed to warm to room temperature. Once the reaction mixture reached room temperature the addition of carbon dioxide was ceased and the solution was poured into water. The resulting aqueous mixture was made basic with the addition of 1 N NaOH and washed with dichloromethane. The aqueous layer was then acidified with 1 N HCl to a pH of 3 and extracted twice with ethyl acetate (ca. 75 mL each). The organic layers were combined, washed with brine, dried with anhydrous magnesium sulfate, and concentrated under reduced pressure. Purification by flash chromatography (elution with 10-100% v/v ethyl acetate in hexanes) afforded 3-[tert-butoxycarbonyl(methyl)amino]benzoic acid.

Step 3: 3-(methylamino)-N-phenyl-benzamide: To a solution of 3-[tert-butoxycarbonyl(methyl)amino]benzoic acid (62.8 mg, 0.250 mmol) and aniline (34.2 µL, 0.375 mmol) in DMF (1 mL) was added HATU (190 mg, 0.500 mmol) and N,N-diisopropylethylamine (131 µL, 0.750 mmol). The resulting solution was stirred at room temperature for 3.5 h then poured into water and extracted with ethyl acetate, washed with 1 N HCl, then washed twice with water, then brine, dried with anhydrous magnesium sulfate, and concentrated under reduced pressure. The crude residue was taken up in dichloromethane (4 mL) followed by the addition of trifluoroacetic acid (0.5 mL). The resulting solution was stirred for 16 h, then poured into water, extracted with ethyl acetate, washed with saturated aqueous sodium bicarbonate, then brine, dried with anhydrous magnesium sulfate, and concentrated under reduced pressure. Purification by flash chromatography (elution with 0-100% v/v ethyl acetate in hexanes) afforded 3-(methylamino)-N-phenyl-benzamide.

Step 4: N-[3-[(2,7-dichloroquinazolin-4-yl)-methyl-amino]phenyl]benzamide: To a solution of N-[3-(methylamino)phenyl]benzamide (15 mg, 66.3 µmol) and 2,4,7-trichloroquinazoline (23.2 mg, 99.4 µmol) in DMF (0.5 mL) was added N,N-diisopropylethylamine (29 µL, 0.166 mmol). The resulting solution was heated to 40° C. for 1 h, then poured into water, extracted with ethyl acetate, washed twice with water, then brine, dried with anhydrous magnesium sulfate, and concentrated under reduced pressure. Purification by flash chromatography (elution with 0-100% v/v ethyl acetate in hexanes) afforded N-[3-[(2,7-dichloro-quinazolin-4-yl)-methyl-amino]phenyl]benzamide.

Step 5: N-[3-[(8-chloro-[1,2,4]triazolo[4,3-a]quinazolin-5-yl)-methyl-amino]phenyl]benzamide: To a solution of N-[3-[(2,7-dichloroquinazolin-4-yl)-methyl-amino]phenyl] benzamide (17.6 mg, 39.5 µmol) in ethanol (2.2 mL) and THF (1.2 mL) was added hydrazine hydrate (19.2 µL, 0.395 mmol). The resulting solution was stirred at 40° C. for 16 h, then concentrated under reduced pressure. The crude material was then taken up in triethyl orthoformate (0.66 mL) and heated to 100° C. for 1 h, then cooled to room temperature and concentrated under reduced pressure. Purification by reverse-phase HPLC afforded the title compound: ¹H NMR (400 MHz, DMSO-d₆) δ 10.29 (s, 1H), 9.79 (s, 1H), 8.65 (d, J=2.1 Hz, 1H), 8.02 (s, 1H), 7.95 (d, J=7.3 Hz, 1H), 7.74 (d, J=7.4 Hz, 2H), 7.64-7.50 (m, 2H), 7.42 (dd, J=9.0, 2.1 Hz, 1H), 7.36 (t, J=7.9 Hz, 2H), 7.24 (d, J=9.0 Hz, 1H), 7.12 (t, J=7.3 Hz, 1H), 3.68 (s, 3H); LCMS(m/z) 429.1.

Example 484. 8-chloro-N-(3-(5-(difluoromethyl) furan-2-yl)phenyl)-N-methyl-[1,2,4]triazolo[4,3-a] quinazolin-5-amine

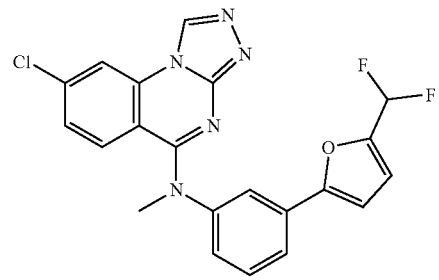

tert-Butyl N-[3-(5-formyl-2-furyl)phenyl]-N-methyl-carbamate: To a solution of tert-butyl N-(3-bromophenyl)-N-methyl-carbamate (560 mg, 1.96 mmol) and (5-formyl-2-furyl)boronic acid (411 mg, 2.94 mmol) in 1,4-dioxane (19 mL) was added aqueous sodium carbonate (9.8 mL, 2 N, 19.6 mmol) and XPhos Pd G3 (73.6 mg, 97.8 µmol). The mixture was heated to 100° C. for 1.5 h, then cooled to room temperature, filtered through Celite®, diluted with ethyl acetate, washed with water, then brine, dried with anhydrous magnesium sulfate, and concentrated under reduced pressure. Purification by flash chromatography (elution with 0-100% v/v ethyl acetate in hexanes) afforded tert-butyl N-[3-(5-formyl-2-furyl)phenyl]-N-methyl-carbamate.

3-[5-(difluoromethyl)-2-furyl]-N-methyl-aniline: To a solution of tert-butyl N-[3-(5-formyl-2-furyl)phenyl]-N-methyl-carbamate (150 mg, 0.498 mmol) in DCM (4 mL) was added trifluoroacetic acid (0.5 mL). The resulting solution was stirred at room temperature for 1.5 h, then poured into saturated aqueous sodium bicarbonate, extracted with ethyl acetate, washed with brine, dried with anhydrous magnesium sulfate, and concentrate under reduced pressure. The resulting crude was taken up in DCM (4 mL) followed by the addition of diethylaminosulfur trifluoride (0.257 mL, 1.95 mmol) and the resulting solution was stirred at room temperature for 24 h, then poured into saturated aqueous sodium bicarbonate, extracted with ethyl acetate, washed with water, then brine, dried with anhydrous magnesium sulfate, and concentrated under reduced pressure. Purification by flash chromatography (elution with 0-100% v/v ethyl acetate in hexanes) afforded 3-[5-(difluoromethyl)-2-furyl]-N-methyl-aniline.

Example 484 was prepared by the method described for Example 483, except using 3-[5-(difluoromethyl)-2-furyl]-N-methyl-aniline instead of 3-(methylamino)-N-phenyl-benzamide. ¹H NMR (400 MHz, DMSO-d₆) δ 9.78 (s, 1H), 8.63 (d, J=2.0 Hz, 1H), 7.88-7.81 (m, 1H), 7.76 (d, J=7.8 Hz, 1H), 7.54 (t, J=7.9 Hz, 1H), 7.42 (dd, J=9.0, 2.1 Hz, 1H), 7.35 (dd, J=7.9, 2.1 Hz, 1H), 7.29-6.98 (m, 4H), 3.66 (s, 3H); LCMS(m/z) 426.1.

Example 485. 3-((8-chloro-[1,2,4]triazolo[4,3-a]quinazolin-5-yl)(methyl)amino)-N-methyl-N-phenylbenzamide

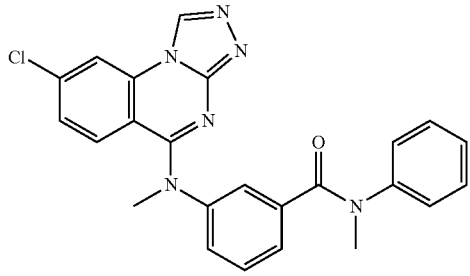

Example 485 was prepared according to the method described for Example 483, except using N-methylaniline instead of aniline. ¹H NMR (400 MHz, DMSO-d₆) δ 9.76 (s, 1H), 8.62 (d, J=2.0 Hz, 1H), 7.33-7.25 (m, 6H), 7.22-7.13 (m, 4H), 6.85 (d, J=9.0 Hz, 1H), 3.40 (s, 3H), 3.34 (s, 3H); LCMS(m/z) 443.1.

Example 486. N-(3-((8-chloro-[1,2,4]triazolo[4,3-a]quinazolin-5-yl)(methyl)amino)phenyl)-N-methylbenzamide

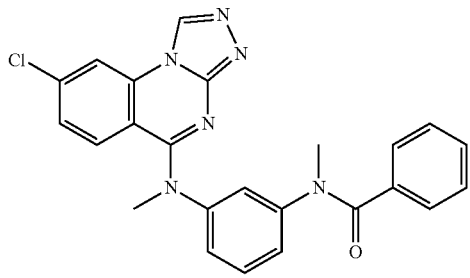

N-methyl-N-[3-(methylamino)phenyl]benzamide: To a solution of benzoic acid (100 mg, 0.819 mmol) and N,N'-dimethylbenzene-1,3-diamine (0.210 mL, 1.64 mmol) in DMF (2 mL) was added HATU (544 mg, 1.43 mmol) and N,N-diisopropylethylamine (0.374 mL, 2.15 mmol). The reaction mixture was stirred at room temperature for 4 h, then poured into water and extracted with ethyl acetate, washed with 1 N HCl, then washed twice with water, then brine, dried with anhydrous magnesium sulfate, and concentrated under reduced pressure. Purification by flash chromatography (elution with 0-100% v/v ethyl acetate in hexanes) afforded N-methyl-N-[3-(methylamino)phenyl]benzamide.

Example 486 was prepared according to the method described for Example 483, except using N-methyl-N-[3-(methylamino)phenyl]benzamide instead of 3-(methylamino)-N-phenylbenzamide. ¹H NMR (400 MHz, DMSO-d₆) δ 9.75 (s, 1H), 8.61 (d, J=2.1 Hz, 1H), 7.37-7.22 (m, 9H), 7.15 (d, J=8.6 Hz, 1H), 7.07 (dd, J=7.9, 2.1 Hz, 1H), 6.94 (d, J=9.0 Hz, 1H), 3.44 (s, 3H), 3.34 (s, 3H); LCMS(m/z) 443.1.

Example 487. 8-chloro-N-methyl-N-(3-(5-(morpholinomethyl)furan-2-yl)phenyl)-[1,2,4]triazolo[4,3-a]quinazolin-5-amine

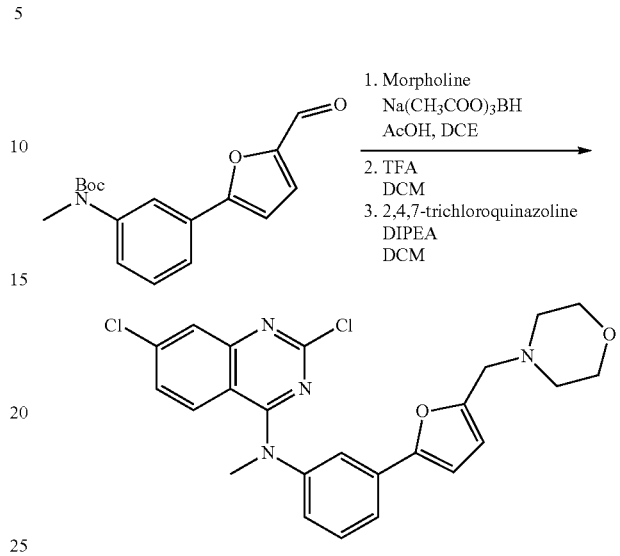

2,7-dichloro-N-methyl-N-[3-[5-(morpholinomethyl)-2-furyl]phenyl]quinazolin-4-amine: To a solution of tert-butyl N-[3-(5-formyl-2-furyl)phenyl]-N-methyl-carbamate (40 mg, 0.133 mmol), morpholine (23 μL, 0.265 mmol) and acetic acid (38 μL) in 1,2-dichloroethane (1.5 mL) was added sodium triacetoxyborohydride (56.3 mg, 0.265 mmol). The reaction mixture was stirred at room temperature for 16 h, then poured into water, extracted with ethyl acetate, washed with brine, dried with anhydrous magnesium sulfate, then concentrated under reduced pressure. The resulting crude material was taken up in DCM (4 mL) followed by the addition of trifluoroacetic acid (0.5 mL). The resulting solution was stirred at room temperature for 30 min, then poured into water, extracted with ethyl acetate, washed with brine, dried with anhydrous magnesium sulfate, and concentrated under reduced pressure. The resulting crude material was combined with 2,4,7-trichloroquinazoline (46.6 mg, 0.200 mmol) in DMF (1.5 mL) followed by the addition of N,N-diisopropylethylamine (58 μL, 0.333 mmol). The reaction mixture was heated to 40° C. for 2 h, then poured into water, extracted with ethyl acetate, washed with water, then brine, dried with anhydrous magnesium sulfate, and concentrated under reduced pressure. Purification by flash chromatography (elution with 0-100% v/v ethyl acetate in hexanes) afforded 2,7-dichloro-N-methyl-N-[3-[5-(morpholinomethyl)-2-furyl]phenyl]quinazolin-4-amine.

Example 487 was prepared according to the method described for Example 483, except using 2,7-dichloro-N-methyl-N-[3-[5-(morpholinomethyl)-2-furyl]phenyl]quinazolin-4-amine instead of N-[3-[(2,7-dichloroquinazolin-4-yl)-methyl-amino]phenyl]benzamide. ¹H NMR (400 MHz, DMSO-d₆) δ 9.74 (s, 1H), 8.61 (d, J=2.1 Hz, 1H), 7.78-7.73 (m, 1H), 7.70 (d, J=7.9 Hz, 1H), 7.51 (t, J=7.9 Hz, 1H), 7.38 (dd, J=9.0, 2.1 Hz, 1H), 7.33-7.25 (m, 2H), 7.09 (d, J=3.4 Hz, 1H), 6.79 (d, J=3.4 Hz, 1H), 4.47 (s, 2H), 3.96 (s, 4H), 3.62 (s, 3H), 3.37-3.03 (m, 4H); LCMS(m/z) 475.1.

Example 488. [5-[3-[(8-chloro-[1,2,4]triazolo[4,3-a]quinazolin-5-yl)-methyl-amino]phenyl]-2-furyl]methanol

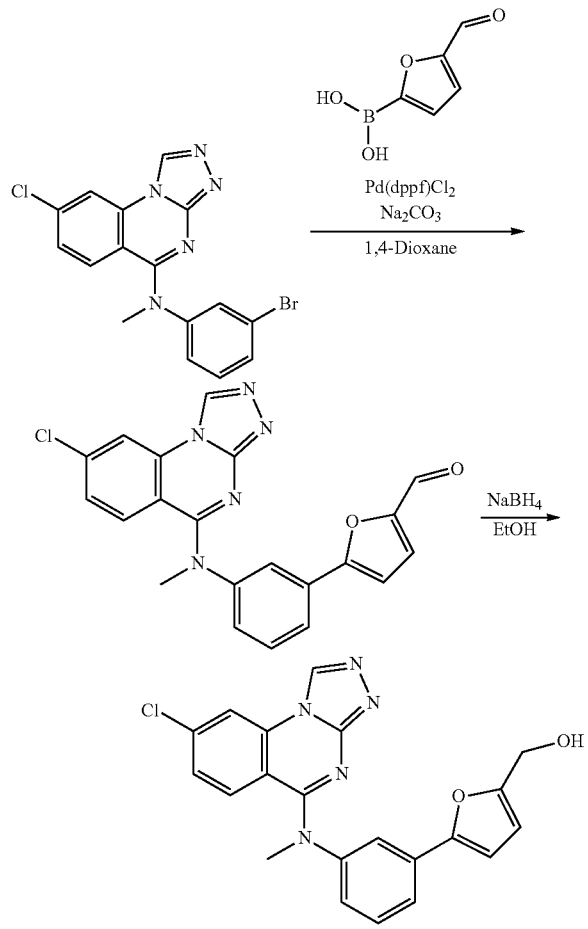

5-[3-[(8-chloro-[1,2,4]triazolo[4,3-a]quinazolin-5-yl)-methyl-amino]phenyl]furan-2-carbaldehyde: To a solution of N-(3-bromophenyl)-8-chloro-N-methyl-[1,2,4]triazolo[4,3-a]quinazolin-5-amine (Example 308, 100 mg, 0.257 mmol) and (5-formyl-2-furyl)boronic acid (39.6 mg, 0.283 mmol) in 1,4-dioxane (1 mL) was added Pd(dppf)Cl2 (21.3 mg, 25.7 µmol) and aqueous sodium carbonate (0.643 mL, 2 M, 1.29 mmol). The resulting solution was heated to 100° C. for 1 h, then filtered through Celite®, diluted with ethyl acetate, washed with water, then brine, dried with anhydrous magnesium sulfate, and concentrated under reduced pressure. Purification by flash chromatography (elution with 0-100% v/v ethyl acetate in hexanes) afforded 5-[3-[(8-chloro-[1,2,4]triazolo[4,3-a]quinazolin-5-yl)-methyl-amino]phenyl]furan-2-carbaldehyde.

[5-[3-[(8-chloro-[1,2,4]triazolo[4,3-a]quinazolin-5-yl)-methyl-amino]phenyl]-2-furyl]methanol: To a solution of 5-[3-[(8-chloro-[1,2,4]triazolo[4,3-a]quinazolin-5-yl)-methyl-amino]phenyl]furan-2-carbaldehyde (45 mg, 0.111 mmol) in ethanol (5 mL) at 0° C. was added sodium borohydride (5 mg, 0.134 mmol). After 20 min at this temperature the reaction mixture was quenched with water and concentrated under reduced pressure. The resulting crude material was taken up in ethyl acetate, washed with water, then brine, dried with anhydrous magnesium sulfate, and concentrated under reduced pressure. Purification by reverse-phase HPLC afforded the title compound: $^1$H NMR (400 MHz, DMSO-$d_6$) δ 9.76 (s, 1H), 8.62 (d, J=2.1 Hz, 1H), 7.72 (t, J=1.8 Hz, 1H), 7.70-7.65 (m, 1H), 7.49 (t, J=7.9 Hz, 1H), 7.42 (dd, J=9.0, 2.1 Hz, 1H), 7.30-7.22 (m, 2H), 6.94 (d, J=3.3 Hz, 1H), 6.40 (d, J=3.3 Hz, 1H), 4.43 (s, 2H), 3.64 (s, 3H); LCMS(m/z) 406.1.

Example 489. 8-chloro-N-[3-[5-(methoxymethyl)-2-furyl]phenyl]-N-methyl-[1,2,4]triazolo[4,3-a]quinazolin-5-amine

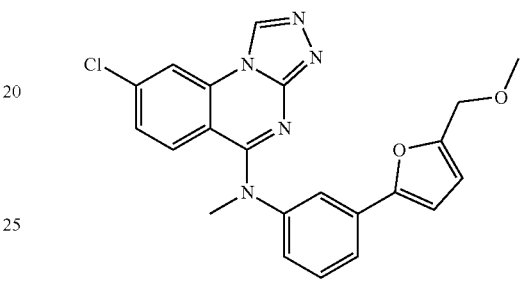

8-chloro-N-[3-[5-(methoxymethyl)-2-furyl]phenyl]-N-methyl-[1,2,4]triazolo[4,3-a]quinazolin-5-amine: To a solution of [5-[3-[(8-chloro-[1,2,4]triazolo[4,3-a]quinazolin-5-yl)-methyl-amino]phenyl]-2-furyl]methanol (25 mg, 61.6 µmol) and iodomethane (37.5 µL, 0.616 mmol) in DMSO (2 mL) at 0° C. was added NaH (3.4 mg, 60 wt % in mineral oil, 92.4 µmol). The reaction mixture was then warmed to room temperature and stirred at this temperature for 3 h. The reaction mixture was then quenched with water, diluted with ethyl acetate, washed with water, then brine, dried with anhydrous magnesium sulfate, and concentrated under reduced pressure. Purification by reverse-phase HPLC gave the title compound: $^1$H NMR (400 MHz, DMSO-$d_6$) δ 9.76 (s, 1H), 8.62 (d, J=2.1 Hz, 1H), 7.74 (t, J=1.9 Hz, 1H), 7.71-7.66 (m, 1H), 7.49 (t, J=7.9 Hz, 1H), 7.42 (dd, J=9.0, 2.1 Hz, 1H), 7.29-7.23 (m, 2H), 6.98 (d, J=3.4 Hz, 1H), 6.56 (d, J=3.4 Hz, 1H), 4.38 (s, 2H), 3.64 (s, 3H), 3.26 (s, 3H); LCMS(m/z) 420.1.

Example 490. 8-chloro-N-(6-(6-cyclopropylpyridin-3-yl)pyrazin-2-yl)-N-methyl-[1,2,4]triazolo[4,3-a]quinazolin-5-amine

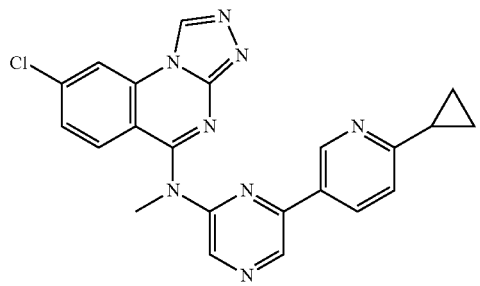

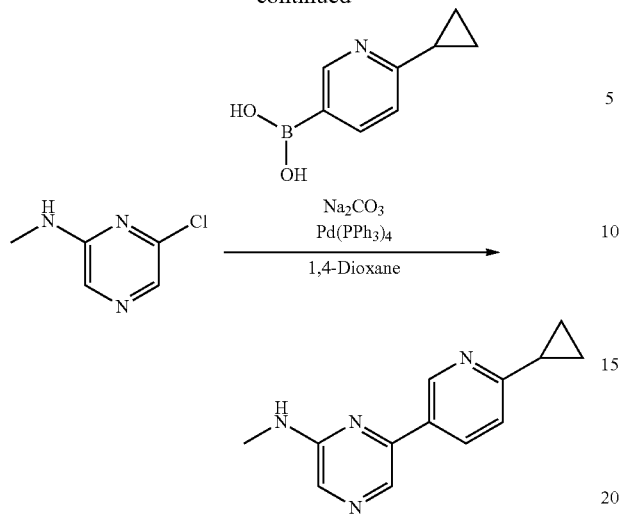

6-(6-cyclopropyl-3-pyridyl)-N-methyl-pyrazin-2-amine:
To a solution of 6-chloro-N-methyl-pyrazin-2-amine (57.3 mg, 0.399 mmol) and (6-cyclopropyl-3-pyridyl)boronic acid (50 mg, 0.307 mmol) in 1,4-dioxane (2 mL) was added Pd(PPh$_3$)$_4$ (35.5 mg, 30.7 μmol) and aqueous sodium carbonate (0.46 mL, 2 N, 0.920 mmol). The resulting solution was heated to 90° C. for 2 h, then cooled to room temperature, diluted with ethyl acetate, filtered through Celite®, and concentrated under reduced pressure. Purification by flash chromatography (elution with 0-100% v/v ethyl acetate in hexanes) afforded 6-(6-cyclopropyl-3-pyridyl)-N-methyl-pyrazin-2-amine.

Example 490 was prepared according to the method described for Example 483, except using 6-(6-cyclopropyl-3-pyridyl)-N-methyl-pyrazin-2-amine instead of 3-(methylamino)-N-phenyl-benzamide. $^1$H NMR (400 MHz, DMSO-d$_6$) δ 9.86 (s, 1H), 8.96-8.89 (m, 2H), 8.73 (d, J=2.0 Hz, 1H), 8.53 (s, 1H), 8.18 (dd, J=8.3, 2.3 Hz, 1H), 7.65 (d, J=8.8 Hz, 1H), 7.52 (dd, J=8.8, 2.0 Hz, 1H), 7.41 (d, J=8.3 Hz, 1H), 3.77 (s, 3H), 2.22-2.12 (m, 1H), 1.06-0.95 (m, 4H); LCMS (m/z) 429.1.

Example 491. 8-chloro-N-(6-(6-methoxypyridin-3-yl)pyrazin-2-yl)-N-methyl-[1,2,4]triazolo[4,3-a]quinazolin-5-amine

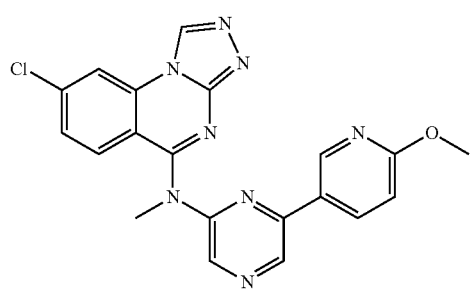

6-(6-Methoxypyridin-3-yl)-N-methylpyrazin-2-amine was prepared according to the Suzuki coupling procedure described for Example 490, except using 6-chloro-N-methylpyrazin-2-amine and (6-methoxypyridin-3-yl)boronic acid. Example 491 was prepared according to the method described for Example 483, except using 6-(6-methoxypyridin-3-yl)-N-methylpyrazin-2-amine instead of 3-(methylamino)-N-phenyl-benzamide. $^1$H NMR (400 MHz, DMSO-d6) δ 9.87 (s, 1H), 8.93 (s, 1H), 8.74 (dd, J=6.1, 1.9 Hz, 2H), 8.50 (s, 1H), 8.21 (dd, J=8.7, 2.5 Hz, 1H), 7.62 (d, J=8.8 Hz, 1H), 7.52 (dd, J=8.9, 2.1 Hz, 1H), 6.91 (dd, J=8.7, 0.7 Hz, 1H), 3.90 (s, 3H), 3.77 (s, 3H); LCMS(m/z) 419.1.

Example 492. 8-chloro-N-(2-(6-methoxypyridin-3-yl)pyrimidin-4-yl)-N-methyl-[1,2,4]triazolo[4,3-a]quinazolin-5-amine

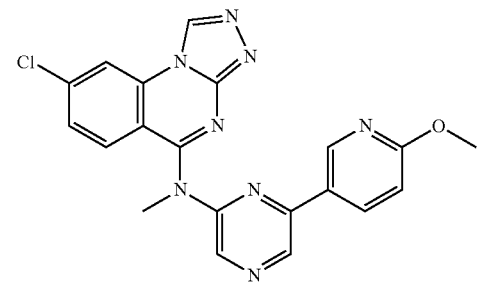

2-(6-Methoxypyridin-3-yl)-N-methylpyrimidin-4-amine was prepared according to the Suzuki coupling procedure described for Example 490, except using 2-chloro-N-methylpyrimidin-4-amine and (6-methoxypyridin-3-yl)boronic acid. Example 492 was prepared according to the method described for Example 483, except using 2-(6-methoxypyridin-3-yl)-N-methylpyrimidin-4-amine instead of 3-(methylamino)-N-phenyl-benzamide. $^1$H NMR (400 MHz, DMSO-d$_6$) δ 9.95 (s, 1H), 8.80 (d, J=2.3 Hz, 1H), 8.78 (d, J=2.0 Hz, 1H), 8.52 (d, J=6.0 Hz, 1H), 8.29 (dd, J=8.7, 2.4 Hz, 1H), 7.83 (d, J=8.8 Hz, 1H), 7.60 (dd, J=8.8, 2.0 Hz, 1H), 6.99 (d, J=6.0 Hz, 1H), 6.85 (dd, J=8.7, 0.7 Hz, 1H), 3.89 (s, 3H), 3.72 (s, 3H); LCMS(m/z) 419.1.

Example 493. 8-chloro-N-(6-(6-(difluoromethyl)pyridin-3-yl)pyrazin-2-yl)-N-methyl-[1,2,4]triazolo[4,3-a]quinazolin-5-amine

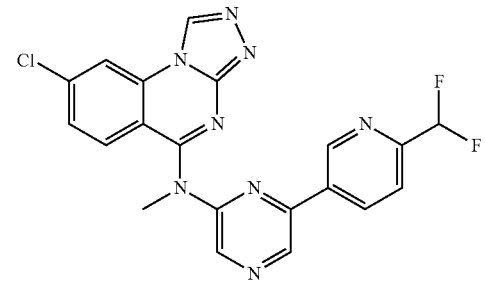

6-(6-(Difluoromethyl)pyridin-3-yl)-N-methylpyrazin-2-amine was prepared according to the method of Example 490, except using 2-(difluoromethyl)-5-(4,4,5,5-tetramethyl-1,3,2-dioxaborolan-2-yl)pyridine instead of (6-cyclopropyl-3-pyridyl)boronic acid. Example 493 was prepared according to the method described in Example 483, except using 6-(6-(difluoromethyl)pyridin-3-yl)-N-methylpyrazin- 2-amine instead of 3-(methylamino)-N-phenyl-benzamide. $^1$H NMR (400 MHz, DMSO-d$_6$) δ 9.87 (s, 1H), 9.18 (d, J=2.1 Hz, 1H), 9.03 (s, 1H), 8.74 (d, J=2.0 Hz, 1H), 8.61 (s, 1H), 8.51 (dd, J=8.2, 2.2 Hz, 1H), 7.80 (d, J=8.2 Hz, 1H), 7.72 (d, J=8.9 Hz, 1H), 7.53 (dd, J=8.9, 2.0 Hz, 1H), 7.02 (t, J=54.8 Hz, 1H), 3.79 (s, 3H); LCMS(m/z) 439.1.

Example 494. 8-chloro-N-(2-(6-(difluoromethyl)pyridin-3-yl)pyrimidin-4-yl)-N-methyl-[1,2,4]triazolo[4,3-a]quinazolin-5-amine

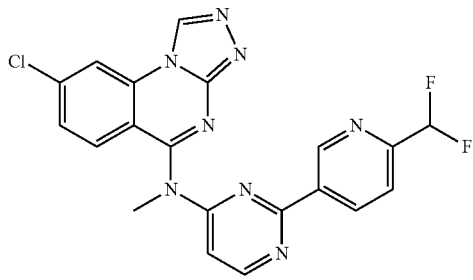

2-(6-(Difluoromethyl)pyridin-3-yl)-N-methylpyrimidin-4-amine was prepared according to the method of Example 490, except using 2-(difluoromethyl)-5-(4,4,5,5-tetramethyl-1,3,2-dioxaborolan-2-yl)pyridine and 2-chloro-N-methylpyrimidin-4-amine instead of (6-cyclopropyl-3-pyridyl)boronic acid and 6-chloro-N-methyl-pyrazin-2-amine. Example 494 was prepared according to the method described in Example 483, except using 2-(6-(difluoromethyl)pyridin-3-yl)-N-methylpyrimidin-4-amine instead of 3-(methylamino)-N-phenyl-benzamide. $^1$H NMR (400 MHz, DMSO-d$_6$) δ 9.95 (s, 1H), 9.22 (s, 1H), 8.79 (d, J=2.0 Hz, 1H), 8.63-8.55 (m, 2H), 7.86 (d, J=8.8 Hz, 1H), 7.76 (d, J=8.2 Hz, 1H), 7.61 (dd, J=8.8, 2.0 Hz, 1H), 7.16-6.84 (m, 2H), 3.74 (s, 3H); LCMS(m/z) 439.1.

Example 495. 8-chloro-N-(6-(6-(difluoromethyl)pyridin-3-yl)pyrazin-2-yl)-7-fluoro-N-methyl-[1,2,4]triazolo[4,3-a]quinazolin-5-amine

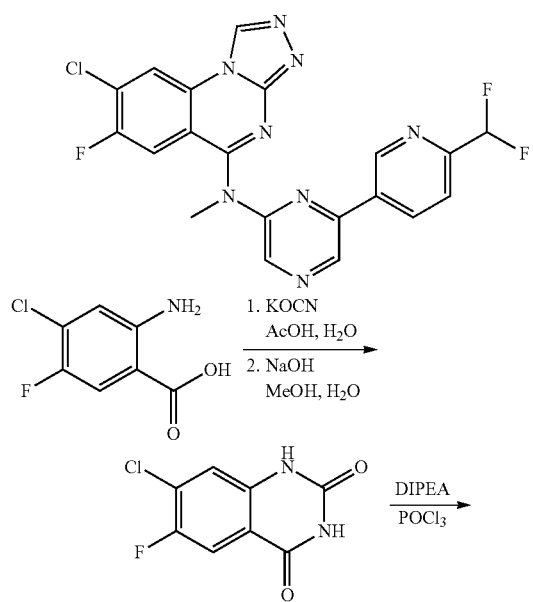

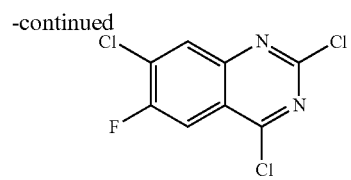

7-chloro-6-fluoro-1H-quinazoline-2,4-dione: A solution of potassium cyanate (8.74 g, 103 mmol) in water (40 mL) was added slowly to a solution of 2-amino-4-chloro-5-fluoro-benzoic acid (10 g, 51.7 mmol) in acetic acid (200 mL). The reaction mixture was stirred at room temperature for 24 h, then poured into water (500 mL). The precipitate was then collected by filtration and added to MeOH (300 mL) followed by the addition of aqueous sodium hydroxide (25.8 mL, 4 M, 103 mmol). The resulting mixture was then stirred at room temperature for 16 h, then acidified with 1N HCl to pH 3, and the precipitate was collected by filtration and dried in vacuo to afford 7-chloro-6-fluoro-1H-quinazoline-2,4-dione.

2,4,7-trichloro-6-fluoro-quinazoline: 7-chloro-6-fluoro-1H-quinazoline-2,4-dione (1 g, 4.66 mmol) was dissolved in POCl$_3$ (3.25 mL, 35 mmol) followed by the addition N,N-diisopropylethylamine (1.51 mL, 8.68 mmol). The resulting solution was heated to 100° C. for 1 h, then carefully poured into water (500 mL). The precipitate was collected by filtration, then dissolved in dichloromethane and washed with water, dried with anhydrous magnesium sulfate, and concentrated under reduced pressure. The resulting crude material was then further dried in vacuo to afford 2,4,7-trichloro-6-fluoro-quinazoline.

Example 495 was prepared according to the method of Example 483, except using 2,4,7-trichloro-6-fluoro-quinazoline and 6-(6-(difluoromethyl)pyridin-3-yl)-N-methylpyrazin-2-amine instead of 2,4,7-trichloroquinazoline and N-[3-(methylamino)phenyl]benzamide. $^1$H NMR (400 MHz, DMSO-d$_6$) δ 9.86 (s, 1H), 9.19 (d, J=2.1 Hz, 1H), 9.01 (s, 1H), 8.96 (d, J=6.4 Hz, 1H), 8.63 (s, 1H), 8.50 (dd, J=8.2, 2.2 Hz, 1H), 7.86 (d, J=9.7 Hz, 1H), 7.80 (d, J=8.2 Hz, 1H), 7.02 (t, J=54.8 Hz, 1H), 3.76 (s, 3H); LCMS(m/z) 457.1.

Example 496. 8-chloro-N-(2-(6-(difluoromethyl)pyridin-3-yl)pyrimidin-4-yl)-7-fluoro-N-methyl-[1,2,4]triazolo[4,3-a]quinazolin-5-amine

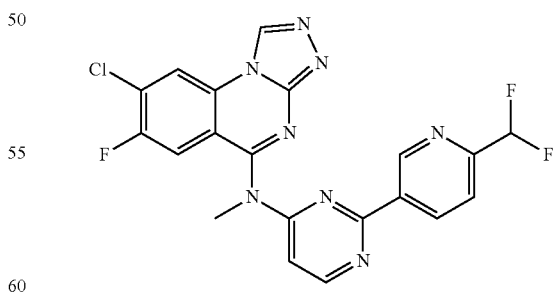

Example 496 was prepared according to the method of Example 483, except using 2,4,7-trichloro-6-fluoro-quinazoline and 2-(6-(difluoromethyl)pyridin-3-yl)-N-methylpyrimidin-4-amine instead of 2,4,7-trichloroquinazoline and N-[3-(methylamino)phenyl]benzamide. $^1$H NMR (400 MHz, DMSO-d$_6$) δ 9.94 (s, 1H), 9.24 (s, 1H), 9.01 (d, J=6.3

Hz, 1H), 8.63-8.56 (m, 2H), 8.00 (d, J=9.5 Hz, 1H), 7.76 (d, J=8.2 Hz, 1H), 7.17-6.85 (m, 2H), 3.71 (s, 3H); LCMS(m/z) 457.1.

Example 497. 7,8-difluoro-N,1-dimethyl-N-phenyl-[1,2,4]triazolo[4,3-a]quinazolin-5-amine

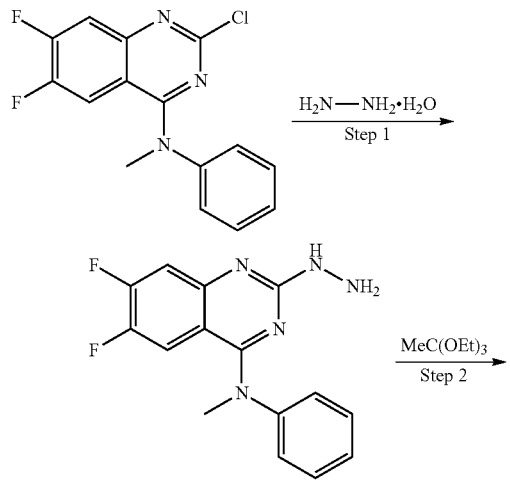

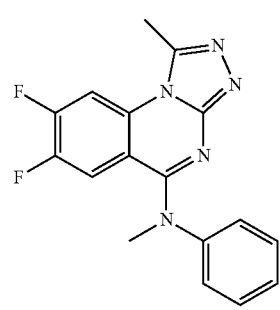

Step 1: Preparation of 6,7-difluoro-2-hydrazineyl-N-methyl-N-phenylquinazolin-4-amine: A solution of 2-chloro-6,7-difluoro-N-methyl-N-phenylquinazolin-4-amine (174.7 mg, 0.571 mmol) in ethanol (4 mL) and THF (1 mL) was treated with hydrazine hydrate (1092 mg, 38.1 eq) at rt for 20 h. The resulting suspension was filtered. The filtrate was collected to give 6,7-difluoro-2-hydrazineyl-N-methyl-N-phenylquinazolin-4-amine. LCMS-ESI+ (m/z): [M+H]+calcd for C$_{15}$H$_{13}$F$_2$N: 302.11 (M+1), found: 302.20 (M+1).

Step 2: Preparation of 7,8-difluoro-N,1-dimethyl-N-phenyl-[1,2,4]triazolo[4,3-a]quinazolin-5-amine: A solution of 6,7-difluoro-2-hydrazineyl-N-methyl-N-phenylquinazolin-4-amine (30.0 mg, 0.0996 mmol) in triethyl orthoformate (80.0 mg, 0.498 mmol, 5 equiv.) was stirred and heated at 100° C. for 19 h. The resulting suspension was filtered. The filtrate was collected to give the title compound: $^1$H NMR (400 MHz, DMSO-d$_6$) δ 8.19 (dd, J=11.5, 7.1 Hz, 1H), 7.42 (t, J=7.7 Hz, 2H), 7.29 (dd, J=7.7, 5.3 Hz, 3H), 7.15 (dd, J=12.0, 8.5 Hz, 1H), 3.52 (s, 3H), 2.93 (s, 3H); LCMS(m/z) 326.2.

Example 498. 1-(7-bromo-2-chloro-6-fluoroquinazolin-4-yl)-2,3,4,5-tetrahydro-1H-benzo[b]azepine

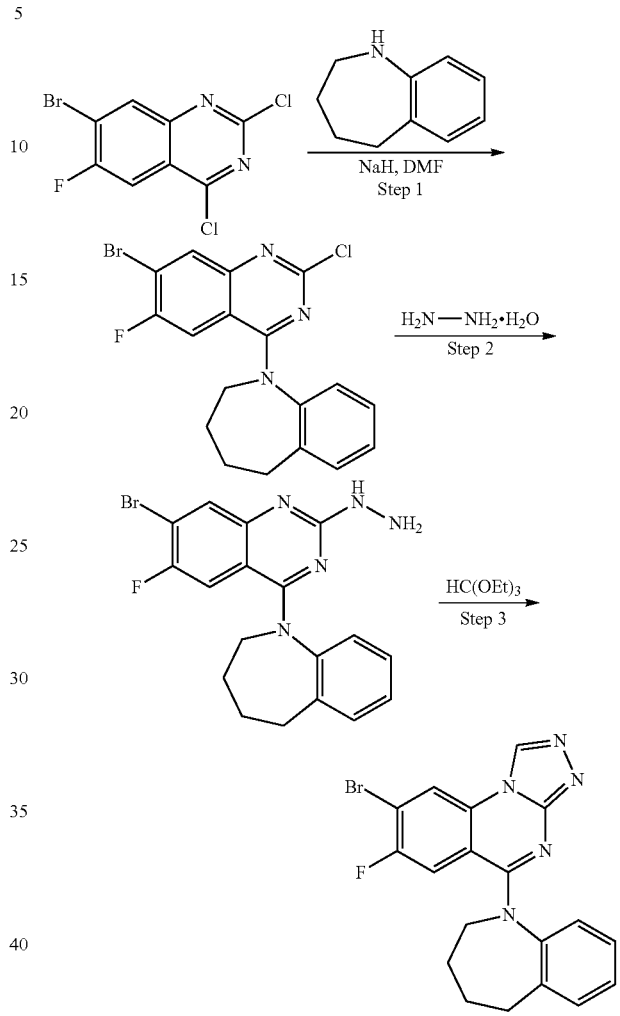

Step 1: Preparation of 1-(7-bromo-2-chloro-6-fluoroquinazolin-4-yl)-2,3,4,5-tetrahydro-1H-benzo[b]azepine:
7-Bromo-2,4-dichloro-6-fluoroquinazoline (500 mg, 1.69 mmol), 2,3,4,5-tetrahydro-1H-1-benzazepine (249 mg, 1.69 mmol, 1 equiv.) was treated with sodium hydride (155.4 mg, 4.1 mmol, 2.4 equiv.) in DMF (5 mL) at rt for 3 h. To the mixture was added water (30 mL), followed by extraction with EtOAc (30 mL, x3). Organic layer was washed with brine (30 mL) and dried over Na$_2$SO$_4$. Organic solvent was removed under reduced pressure to give the crude product, This was used for the subsequent step without further purification. LCMS-ESI+ (m/z): [M+H]+ calcd for C$_{19}$H$_{17}$BrFN$_5$: 406.00 (M–1+1), 408.00 (M+1+1), found: 406.19 (M–1+1), 408.14 (M+1+1).

Step 2: Preparation of 1-(7-bromo-6-fluoro-2-hydraziney-lquinazolin-4-yl)-2,3,4,5-tetrahydro-1H-benzo[b]azepine:
1-(7-bromo-2-chloro-6-fluoroquinazolin-4-yl)-2,3,4,5-tetrahydro-1H-benzo[b]azepine (506 mg, from step 1) in ethanol (15 mL) and THF (4 mL) was treated with hydrazine hydrate (1675 mg, 27 eq.) at 55° C. for 16 h. To the mixture was added water (30 mL) and the whole was extracted with EtOAc (30 mL, x3). Organic layer was washed with brine (30 mL) and dried over Na$_2$SO$_4$. Organic solvent was removed under a reduced pressure to give crude product. The crude product was purified by preparative reverse phase high performance liquid chromatography to give 1-(7-bromo-6-fluoro-2-hydrazineylquinazolin-4-yl)-2,3,4,5-tetrahydro-1H-benzo[b]azepine: LCMS-ESI+(m/z): [M+H]+ calcd for $C_{18}H_{17}BrFN_5$: 402.07 (M−1+1), 404.06 (M+1+1), found: 402.23 (M−1+1), 404.19 (M+1+1).

Step 3: Preparation of 8-bromo-7-fluoro-5-(2,3,4,5-tetrahydro-1H-benzo[b]azepin-1-yl)-[1,2,4]triazolo[4,3-a]quinazoline: A solution of 1-(7-bromo-6-fluoro-2-hydrazineylquinazolin-4-yl)-2,3,4,5-tetrahydro-1H-benzo[b]azepine (from step 1) in triethyl orthoformate (427 mg, 2.88 mmol, 5 eq) was heated at 100° C. for 3 h. The reaction mixture was purified by preparative reverse phase high performance liquid chromatography to give the title compound: $^1$H NMR (400 MHz, Acetone-d$_6$) δ 9.71 (s, 1H), 8.92 (d, J=6.1 Hz, 1H), 7.63 (dd, J=7.6, 1.6 Hz, 1H), 7.54 (td, J=7.5, 1.3 Hz, 1H), 7.37 (td, J=7.6, 1.6 Hz, 1H), 7.23 (dd, J=7.8, 1.3 Hz, 1H), 6.60 (d, J=10.8 Hz, 1H), 5.37 (s, 1H), 3.03 (d, J=5.9 Hz, 3H), 2.44-1.25 (m, 4H); LCMS(m/z) 412.2/414.2.

Example 499. 8-bromo-1-ethyl-7-fluoro-N-methyl-N-phenyl-[1,2,4]triazolo[4,3-a]quinazolin-5-amine

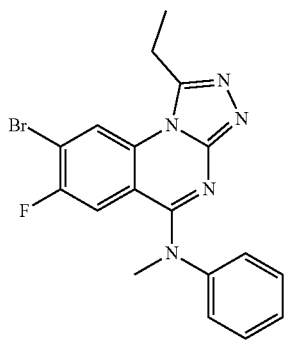

Example 499 was synthesized in a similar fashion as Example 500, except using 1,1,1-trimethoxypropane instead of 1,1,1-triethoxyethane. $^1$H NMR (400 MHz, DMSO-d$_6$) δ 8.30 (d, J=6.0 Hz, 1H), 7.41 (dd, J=8.6, 7.0 Hz, 2H), 7.30 (d, J=7.8 Hz, 3H), 7.04 (d, J=10.1 Hz, 1H), 3.52 (s, 3H), 3.34 (t, J=7.3 Hz, 2H), 1.46 (t, J=7.3 Hz, 3H); LCMS(m/z) 400.3/402.2.

Example 500. 8-bromo-7-fluoro-N,1-dimethyl-N-phenyl-[1,2,4]triazolo[4,3-a]quinazolin-5-amine

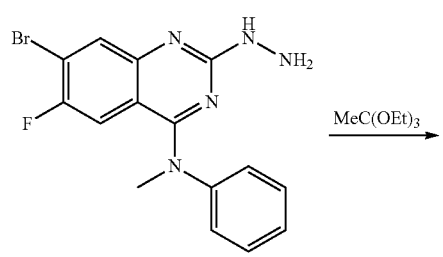

-continued

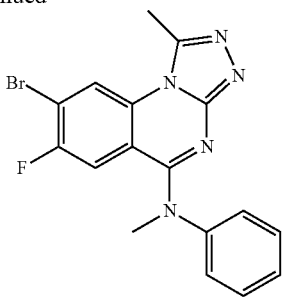

A solution of 7-bromo-6-fluoro-2-hydrazineyl-N-methyl-N-phenylquinazolin-4-amine (20.0 mg, 0.0552 mmol) in 1,1,1-triethoxyethane (74.1 mg, 0.457 mmol, 8.3 equiv.) was stirred and heated at 100° C. for 1 h. The resulting suspension was filtered. The filtrate was collected to give the title compound: $^1$H NMR (400 MHz, DMSO-d$_6$) δ 8.90 (d, J=6.0 Hz, 1H), 7.94-7.83 (m, 2H), 7.82-7.70 (m, 3H), 7.63 (d, J=10.1 Hz, 1H), 4.04 (s, 3H), 3.47 (s, 3H); LCMS(m/z) 386.2/388.1.

Example 501. 8-bromo-7-fluoro-1-isopropyl-N-methyl-N-phenyl-[1,2,4]triazolo[4,3-a]quinazolin-5-amine

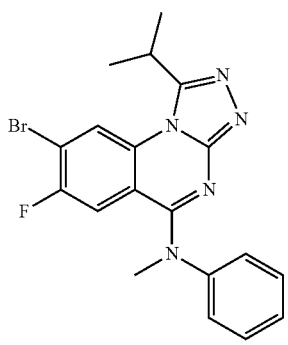

Example 501 was synthesized in a similar fashion as Example 500, except using 1,1,1-trimethoxy-2-methylpropane instead of 1,1,1-triethoxyethane. $^1$H NMR (400 MHz, DMSO-d$_6$) δ 8.29 (d, J=6.0 Hz, 1H), 7.41 (dd, J=8.4, 7.1 Hz, 2H), 7.36-7.23 (m, 3H), 7.06 (d, J=10.1 Hz, 1H), 3.82 (p, J=6.7 Hz, 1H), 3.52 (s, 3H), 1.45 (d, J=6.6 Hz, 6H); LCMS(m/z) 414.2/416.2.

Example 502. (7-fluoro-1-methyl-5-(methyl(phenyl)amino)-[1,2,4]triazolo[4,3-a]quinazolin-8-yl)methanol

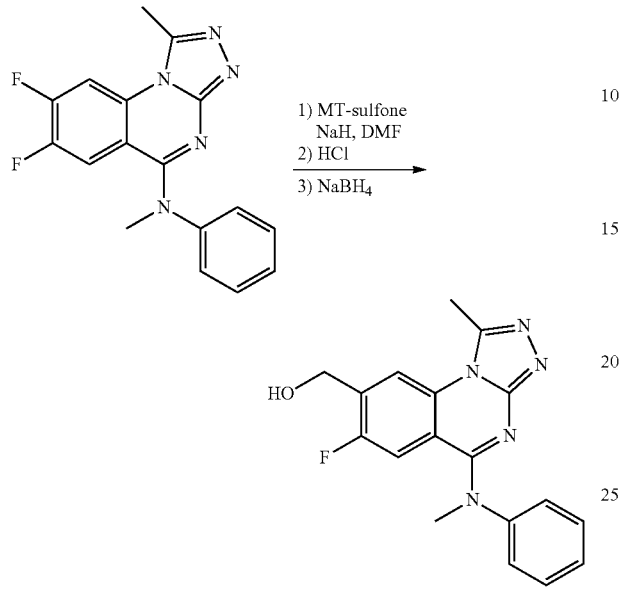

A solution of 7,8-difluoro-N,1-dimethyl-N-phenyl-[1,2,4]triazolo[4,3-a]quinazolin-5-amine (Example 497, 15.0 mg, 0.0461 mmol) and 1-methyl-4-(methylsulfanylmethylsulfonyl)benzene (MT sulfone, 20 mg, 0.092 mmol, 2 equiv.) in DMF (2 mL) was treated with sodium hydride (60% in mineral oil, 10 mg) at rt for 1 h. To the reaction mixture was added TFA (0.3 mL). The reaction mixture directly injected into preparative reverse phase high performance liquid chromatography (Phenomenex Luna C18 column, 5% to 100% gradient acetonitrile in water with 0.1% TFA) to give 7-fluoro-N,1-dimethyl-8-((methylthio)(tosyl)methyl)-N-phenyl-[1,2,4]triazolo[4,3-a]quinazolin-5-amine. LCMS-ESI+(m/z): [M+H]$^+$ calcd for $C_{26}H_{24}FN_5O_2S_2$: 522.14 (M+1), found: 522.02 (M+1).

7-Fluoro-N,1-dimethyl-8-((methylthio)(tosyl)methyl)-N-phenyl-[1,2,4]triazolo[4,3-a]quinazolin-5-amine was dissolved in MeOH (3 mL) and 12N HCl (1 mL) was stirred and heated at 80° C. for 16.5 h. To the mixture was added THF (20 mL) and the solvent was removed under reduced pressure. This was repeated three times to remove MeOH from the system (the aldehyde and its hydrate were observed by LCMS). The residue was dissolved into THF (2 mL) and water (1 mL). To the mixture was added sodium borohydride (excess amount) and the mixture was stirred at rt for 10 min. To the mixture was added water (30 mL) and the whole was extracted with EtOAc (30 mL, x3). Organic layer was washed with brine (30 mL) and dried over $Na_2SO_4$. The water layer was concentrated down to ~2 mL. The water layer was purified by preparative reverse phase high performance liquid chromatography to give the title compound: $^1$H NMR (400 MHz, Methanol-$d_4$) δ 8.46 (d, J=6.2 Hz, 1H), 7.65-7.49 (m, 3H), 7.48-7.38 (m, 2H), 6.80 (d, J=11.8 Hz, 1H), 4.80 (s, 2H), 3.79 (s, 3H), 3.09 (s, 3H); LCMS(m/z) 338.3.

Example 503. 7-fluoro-N-methyl-N-phenyl-8-(prop-1-yn-1-yl)-[1,2,4]triazolo[4,3-a]quinazolin-5-amine

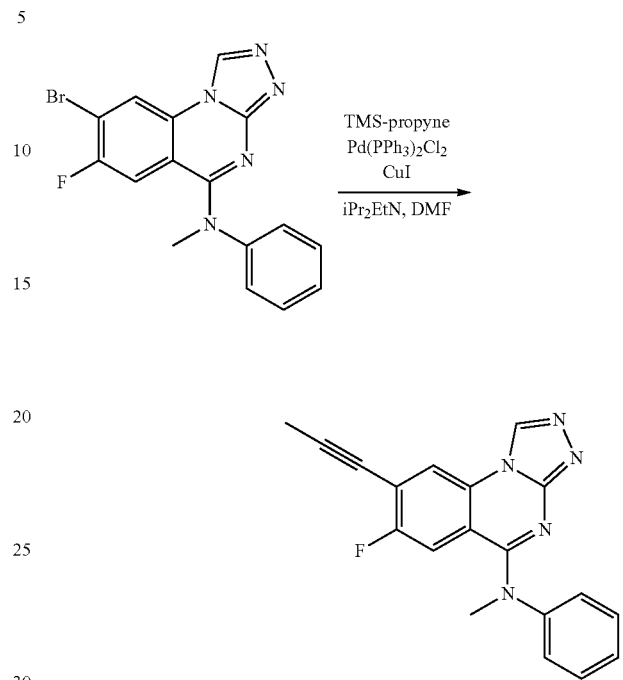

8-Bromo-7-fluoro-N-methyl-N-phenyl-[1,2,4]triazolo[4,3-a]quinazolin-5-amine (20 mg, 0.539 mmol), trimethyl(prop-2-ynyl)silane (12.1 mg, 0.108 mmol, 2 equiv.), DIPEA (13.9 mg, 0.108 mmol, 2 equiv.), CuI (2.1 mg, 0.108 mmol, 0.2 equiv.) and bis(triphenylphosphine)palladium chloride (3.8 mg, 0.0539 mmol, 0.1 equiv.) was heated at 80° C. for 1 h, 100° C. for 1 h and then 150° C. for 1 h in DMF (2 mL) under a nitrogen atmosphere. After a filtration, the mixture was purified by preparative reverse phase high performance liquid chromatography to give the title compound: $^1$H NMR (400 MHz, Methanol-$d_4$) δ 9.53 (s, 1H), 8.44 (d, J=6.2 Hz, 1H), 7.67-7.54 (m, 3H), 7.52-7.38 (m, 2H), 6.68 (d, J=11.2 Hz, 1H), 3.79 (s, 3H), 2.15 (s, 3H); LCMS(m/z) 332.2.

Example 504. 7-fluoro-5-(2,3,4,5-tetrahydro-1H-benzo[b]azepin-1-yl)-[1,2,4]triazolo[4,3-a]quinazolin-8-amine

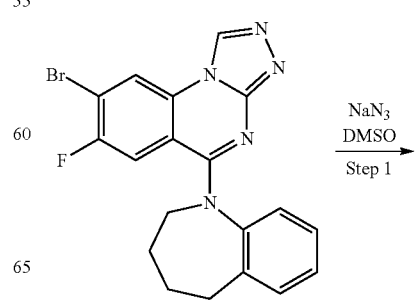

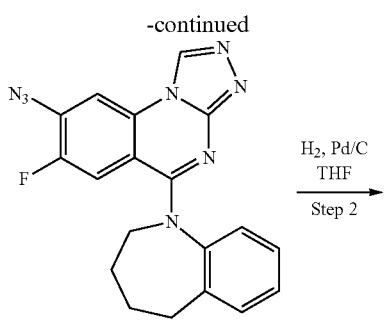

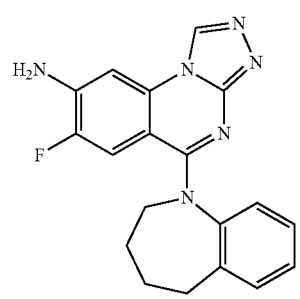

Step 1: Preparation of 8-azido-7-fluoro-5-(2,3,4,5-tetrahydro-1H-benzo[b]azepin-1-yl)-[1,2,4]triazolo[4,3-a]quinazoline: 8-Bromo-7-fluoro-5-(2,3,4,5-tetrahydro-1H-benzo[b]azepin-1-yl)-[1,2,4]triazolo[4,3-a]quinazoline (Example 498, 30.0 mg, 0.728 mmol) was treated with sodium azide (23.8 mg, 0.366 mmol, 5 equiv.) in DMSO (1 mL) at 100° C. for 60 min. To the mixture was added water (30 mL), followed by extraction with EtOAc (30 mL×3). Organic layer was washed with brine (30 mL) and dried over Na$_2$SO$_4$. Organic solvent was removed under reduced pressure to give the crude product. This was used for the subsequent step without further purification. 8-azido-7-fluoro-5-(2,3,4,5-tetrahydro-1H-benzo[b]azepin-1-yl)-[1,2,4]triazolo[4,3-a]quinazoline: LCMS-ESI+(m/z): [M+H]+ calcd for C$_{19}$H$_{15}$FN$_8$: 375.14 (M+1), found: 375.02 (M+1).

Step 2: Preparation of 7-fluoro-5-(2,3,4,5-tetrahydro-1H-benzo[b]azepin-1-yl)-[1,2,4]triazolo[4,3-a]quinazolin-8-amine: 8-Azido-7-fluoro-5-(2,3,4,5-tetrahydro-1H-benzo[b]azepin-1-yl)-[1,2,4]triazolo[4,3-a]quinazoline (35.5 mg, 0.0948 mmol) was treated with 10% palladium carbon (15.2 mg) in THF (2 mL) under hydrogen atmosphere at rt for 30 min. After a filtration, the reaction mixture was purified by preparative reverse phase high performance liquid chromatography to give the title compound: $^1$H NMR (400 MHz, Methanol-d$_4$) δ 9.25 (s, 1H), 7.62-7.42 (m, 2H), 7.39-7.26 (m, 2H), 7.12 (d, J=7.9 Hz, 1H), 6.27 (d, J=14.1 Hz, 1H), 5.44 (s, 1H), 3.13 (s, OH), 2.95 (s, 2H), 1.97 (d, J=29.4 Hz, 4H), 1.63 (s, 2H); LCMS(m/z) 349.2.

Example 505. 8-chloro-7-fluoro-5-(2,3,4,5-tetrahydro-1H-benzo[b]azepin-1-yl)-[1,2,4]triazolo[4,3-a]quinazoline

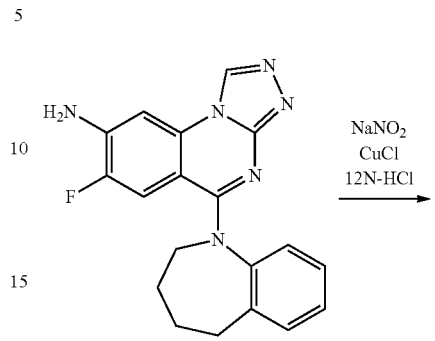

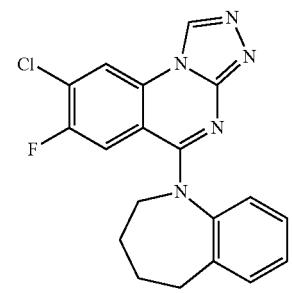

7-Fluoro-5-(2,3,4,5-tetrahydro-1H-benzo[b]azepin-1-yl)-[1,2,4]triazolo[4,3-a]quinazolin-8-amine (Example 504, 15.7 mg, 0.0451 mmol) was dissolved into 12N HCl (1 mL). To the solution was added sodium nitrite (4.7 mg, 0.0676 mmol, 1.5 equiv) in water (1 mL) at 0° C. and the mixture was stirred at the same temperature for 1 h. To the reaction mixture was added a solution of Cu(I)Cl (6.6 mg, 0.0676 mmol, 1.5 equiv.) in 12N HCl (1 mL). And then the reaction temperature was increased to 100° C. and the mixture was stirred at the same temperature for 10 min. After a filtration, the reaction mixture was purified by preparative reverse phase high performance liquid chromatography to give the title compound: $^1$H NMR (400 MHz, Methanol-d$_4$) δ 9.52 (s, 1H), 8.65 (d, J=6.6 Hz, 1H), 7.64-7.48 (m, 2H), 7.36 (td, J=7.6, 1.6 Hz, 1H), 7.15 (dd, J=7.7, 1.3 Hz, 1H), 6.55 (d, J=11.3 Hz, 1H), 5.43 (s, 1H), 3.00 (s, 2H), 2.06 (d, J=19.6 Hz, 4H), 1.68 (s, 1H); LCMS(m/z) 350.4.

Example 506. 8-bromo-5-(7-bromo-3,4-dihydroquinolin-1(2H)-yl)-7-fluoro-[1,2,4]triazolo[4,3-a]quinazoline

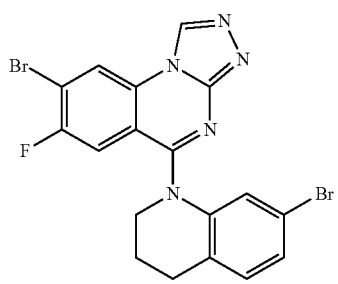

The title compound was prepared according to the procedure described for Example 498. $^1$H NMR (400 MHz, Methanol-$d_4$) δ 9.63 (s, 1H), 8.87 (d, J=5.9 Hz, 1H), 7.39 (dd, J=8.1, 1.9 Hz, 1H), 7.33 (dd, J=8.8, 5.9 Hz, 2H), 7.23 (d, J=1.9 Hz, 1H), 4.15 (t, J=6.7 Hz, 2H), 2.93 (t, J=6.6 Hz, 2H), 2.16 (p, J=6.7 Hz, 2H); LCMS(m/z) 478.1.

Example 507. 7-fluoro-8-(prop-1-yn-1-yl)-5-(2,3,4,5-tetrahydro-1H-benzo[b]azepin-1-yl)-[1,2,4]triazolo[4,3-a]quinazoline

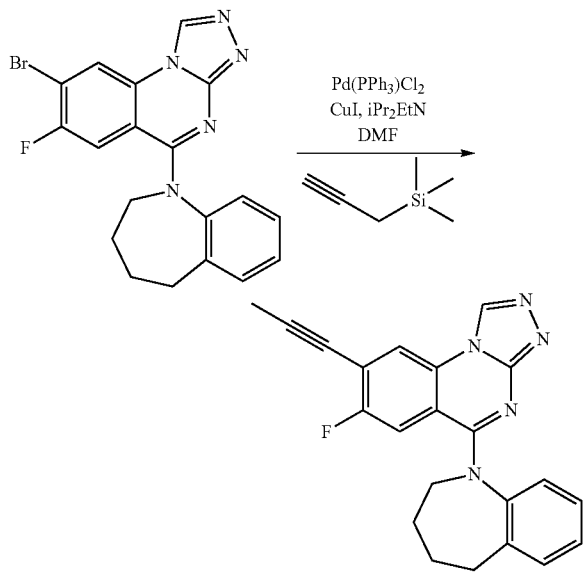

8-Bromo-7-fluoro-5-(2,3,4,5-tetrahydro-1H-benzo[b]azepin-1-yl)-[1,2,4]triazolo[4,3-a]quinazoline (Example 498, 38.2 mg, 0.0929 mmol), trimethyl(prop-2-ynyl)silane (20.9 mg, 0.186 mmol, 2 equiv.), DIPEA (24.0 mg, 0.186 mmol, 2 equiv.), CuI (3.5 mg, 0.186 mmol, 0.2 equiv.) and bis(triphenylphosphine)palladium chloride (6.5 mg, 0.0539 mmol, 0.1 equiv.) was heated at 100° C. for 15.5 h in DMF (2 mL) under a nitrogen atmosphere. After a filtration, the reaction mixture was purified by preparative reverse phase high performance liquid chromatography to give the title compound: $^1$H NMR (400 MHz, Methanol-$d_4$) δ 9.50 (s, 1H), 8.44 (d, J=6.3 Hz, 1H), 7.63-7.46 (m, 2H), 7.35 (td, J=7.6, 1.6 Hz, 1H), 7.14 (dd, J=7.9, 1.2 Hz, 1H), 6.43 (d, J=11.5 Hz, 1H), 5.43 (br s, 1H), 3.20 (br s, 1H), 2.98 (br s, 2H), 2.15 (s, 3H), 2.07 (br s, 2H), 1.67 (br s, 1H), 1.30 (br d, J=5.1 Hz, 1H); LCMS(m/z) 372.3.

Example 508. 5-(7-(4-(tert-butyl)phenyl)-3,4-dihydroquinolin-1(2H)-yl)-7-fluoro-[1,2,4]triazolo[4,3-a]quinazolin-8-amine

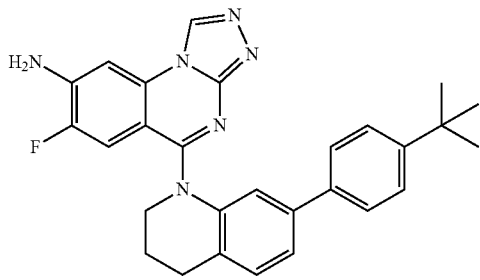 [SMILES: CC(C)(C)c1ccc(-c2ccc3c(c2)N(c2nc4nncn4c4cc(N)c(F)cc24)CCC3)cc1]

Example 508 was synthesized in the similar fashion as Example 510, except using (4-(tert-butyl)phenyl)boronic acid instead of p-tolylboronic acid. $^1$H NMR (400 MHz, Methanol-$d_4$) δ 9.27 (s, 1H), 7.42-7.27 (m, 5H), 7.24 (d, J=8.4 Hz, 2H), 7.15 (d, J=12.6 Hz, 1H), 6.92 (s, 1H), 4.06 (t, J=6.5 Hz, 2H), 2.98 (t, J=6.5 Hz, 2H), 2.19 (t, J=6.5 Hz, 2H), 1.30 (s, 9H); LCMS(m/z) 467.4.

Example 509. 5-(7-bromo-3,4-dihydroquinolin-1(2H)-yl)-7-fluoro-[1,2,4]triazolo[4,3-a]quinazolin-8-amine

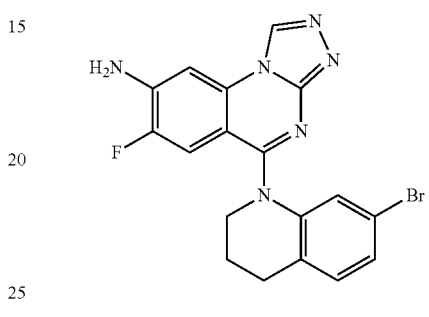

The title compound was prepared according to the procedure described in Example 504. $^1$H NMR (400 MHz, Methanol-$d_4$) δ 9.41 (s, 1H), 7.42 (d, J=7.5 Hz, 1H), 7.34 (dd, J=8.2, 1.9 Hz, 1H), 7.28 (d, J=8.2 Hz, 1H), 7.20 (d, J=1.9 Hz, 1H), 7.10 (d, J=12.6 Hz, 1H), 4.12 (t, J=6.6 Hz, 2H), 2.90 (t, J=6.6 Hz, 2H), 2.13 (p, J=6.6 Hz, 2H); LCMS(m/z) 413.2/415.2.

Example 510. 7-fluoro-5-(7-(p-tolyl)-3,4-dihydroquinolin-1(2H)-yl)-[1,2,4]triazolo[4,3-a]quinazolin-8-amine

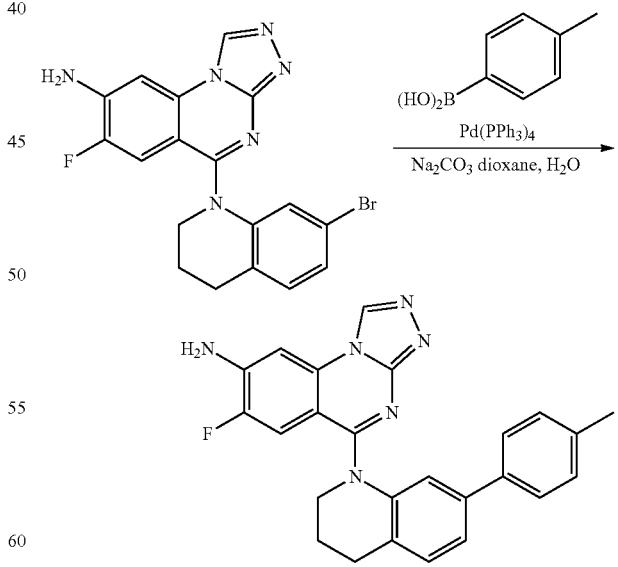

5-(7-Bromo-3,4-dihydroquinolin-1(2H)-yl)-7-fluoro-[1,2,4]triazolo[4,3-a]quinazolin-8-amine (Example 509, 7.2 mg, 0.0174 mmol), p-tolylboronic acid (4.7 mg, 0.0348 mmol, 2 equiv.), tetrakis(triphenylphosphine)palladium(0) (4.0 mg, 0.00348 mmol, 0.2 equiv.) and 2M-Na2CO3 (0.5 mL) was heated in 1,4-dioxane (2 mL) at 100° C. for 30 min under a nitrogen atmosphere. After a filtration, the reaction mixture was purified by preparative reverse phase high performance liquid chromatography. Then, the product was re-purified by silica gel column chromatography (gradient 0% to 20% MeOH/CH$_2$Cl$_2$) to give the title compound: $^1$H NMR (400 MHz, Methanol-d$_4$) δ 9.27 (s, 1H), 7.35 (dd, J=7.8, 4.7 Hz, 2H), 7.28 (dd, J=7.8, 1.8 Hz, 1H), 7.19 (d, J=8.1 Hz, 2H), 7.15 (d, J=12.7 Hz, 1H), 7.11 (d, J=8.1 Hz, 2H), 6.90 (d, J=1.7 Hz, 1H), 4.06 (t, J=6.5 Hz, 2H), 2.98 (t, J=6.6 Hz, 2H), 2.30 (s, 3H), 2.18 (p, J=6.6 Hz, 2H); LCMS(m/z) 425.3.

Example 511. 5-(7-(4-(tert-butyl)phenyl)-3,4-dihydroquinolin-1(2H)-yl)-8-chloro-7-fluoro-[1,2,4]triazolo[4,3-a]quinazoline

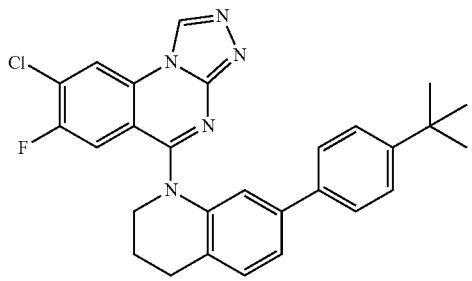 [SMILES: CC(C)(C)c1ccc(-c2ccc3c(c2)N(c2nc4nncn4c4cc(Cl)c(F)cc24)CCC3)cc1]

5-(7-(4-(tert-butyl)phenyl)-3,4-dihydroquinolin-1(2H)-yl)-7-fluoro-[1,2,4]triazolo[4,3-a]quinazolin-8-amine (Example 508, 5.0 mg, 0.0107 mmol) was dissolved into 12N HCl (1 mL). To the solution was added sodium nitrite (1.1 mg, 0.0161 mmol, 1.5 equiv) in water (1 mL) at 0° C. and the reaction mixture was stirred at the same temperature for 30 min. To the reaction mixture was added a solution of Cu(I)Cl (1.6 mg, 0.0161 mmol, 1.5 equiv.) in 12N HCl (1 mL). And then the reaction temperature was increased to 100° C. and the mixture was stirred at the same temperature for 10 min. To the mixture was added water (30 mL) and the whole was extracted with EtOAc (30 mL, ×3). Organic layer was washed with brine (30 mL) and dried over Na$_2$SO$_4$. Organic solvent was removed under a reduced pressure to give a crude mixture. The crude mixture was purified by preparative reverse phase high performance liquid chromatography to give the title compound: $^1$H NMR (400 MHz, Methanol-d$_4$) δ 9.60 (s, 1H), 8.70 (d, J=6.3 Hz, 1H), 7.64-7.46 (m, 2H), 7.42-7.20 (m, 6H), 4.25 (t, J=6.8 Hz, 2H), 3.00 (dd, J=8.1, 4.9 Hz, 2H), 2.20 (q, J=6.6 Hz, 2H), 1.29 (s, 9H); LCMS(m/z) 486.4.

Example 512. 7-fluoro-8-(methylthio)-5-(2,3,4,5-tetrahydro-1H-benzo[b]azepin-1-yl)-[1,2,4]triazolo[4,3-a]quinazoline

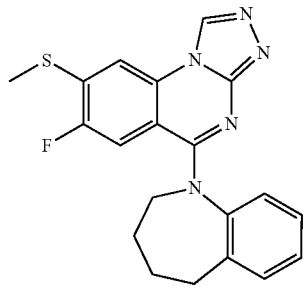

8-Bromo-7-fluoro-5-(2,3,4,5-tetrahydro-1H-benzo[b]azepin-1-yl)-[1,2,4]triazolo[4,3-a]quinazoline (Example 498) and 1-methyl-4-(methylsulfanylmethylsulfonyl)benzene (MT sulfone, 15.7 mg, 0.0728 mmol, 2 equiv.) in DMF (2 mL) was treated with sodium hydride (60% in mineral oil, 10 mg) at rt for 1.5 h. The reaction mixture directly injected into preparative reverse phase high performance liquid chromatography to give the title compound: $^1$H NMR (400 MHz, Methanol-d$_4$) δ 9.55 (s, 1H), 7.94 (d, J=6.8 Hz, 1H), 7.50 (dd, J=7.6, 1.5 Hz, 1H), 7.37 (td, J=7.5, 1.3 Hz, 1H), 7.21 (td, J=7.6, 1.6 Hz, 1H), 6.94 (dd, J=7.8, 1.2 Hz, 1H), 6.46 (d, J=12.4 Hz, 1H), 3.04 (t, J=5.9 Hz, 2H), 2.68 (s, 3H), 2.02-1.71 (m, 4H), 1.28 (d, J=19.1 Hz, 2H); LCMS(m/z) 380.3.

Example 513. 5-(5-bromo-3,4-dihydroquinolin-1(2H)-yl)-7-fluoro-[1,2,4]triazolo[4,3-a]quinazolin-8-amine

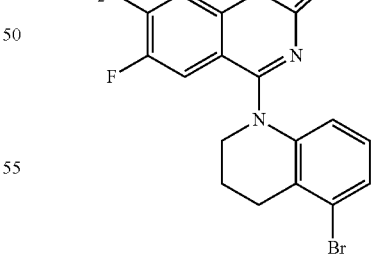

The title compound was prepared according to the procedure described in Example 504. $^1$H NMR (400 MHz, Methanol-d$_4$) δ 9.38 (s, 1H), 7.44 (dd, J=7.9, 1.2 Hz, 1H), 7.38 (d, J=7.5 Hz, 1H), 7.13 (d, J=12.4 Hz, 1H), 6.97 (t, J=8.0 Hz, 1H), 6.91 (dd, J=8.1, 1.2 Hz, 1H), 4.10 (t, J=6.3 Hz, 2H), 3.02 (t, J=6.7 Hz, 2H), 2.17 (p, J=6.6 Hz, 2H); LCMS(m/z) 413.2/415.2.

Example 514. 7-fluoro-5-(5-(p-tolyl)-3,4-dihydroquinolin-1(2H)-yl)-[1,2,4]triazolo[4,3-a]quinazolin-8-amine

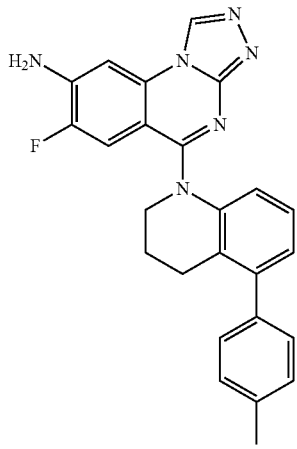

Example 514 was synthesized according to the method of Example 510, except using Example 513 instead of Example 509. $^1$H NMR (400 MHz, DMSO-d$_6$) δ 9.41 (s, 1H), 7.38-7.23 (m, 5H), 7.12-6.98 (m, 2H), 6.91 (dd, J=7.6, 1.2 Hz, 1H), 6.72 (s, 2H), 6.68 (d, J=8.1 Hz, 1H), 3.83 (t, J=6.7 Hz, 2H), 2.74 (t, J=6.5 Hz, 2H), 2.38 (s, 3H), 2.02-1.88 (m, 2H); LCMS(m/z) 425.4.

Example 515. 7-fluoro-5-(5-(4-fluorophenyl)-3,4-dihydroquinolin-1(2H)-yl)-[1,2,4]triazolo[4,3-a]quinazolin-8-amine

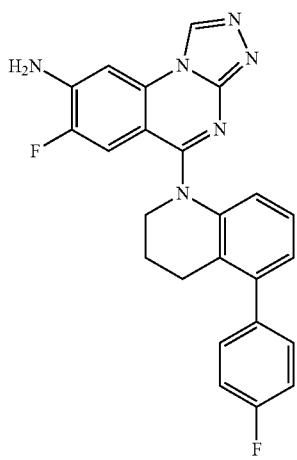

Example 515 was synthesized according to the method of Example 510, except using Example 513 and (4-fluorophenyl)boronic acid instead of Example 509 and p-tolylboronic acid. $^1$H NMR (400 MHz, Methanol-d$_4$) δ 9.25 (s, 1H), 7.43 (dd, J=8.7, 5.4 Hz, 2H), 7.33 (d, J=7.6 Hz, 1H), 7.21 (t, J=8.8 Hz, 2H), 7.12-6.96 (m, 3H), 6.75 (d, J=8.6 Hz, 1H), 3.98 (t, J=6.9 Hz, 3H), 2.80 (t, J=6.4 Hz, 3H), 2.11-1.97 (m, 4H); LCMS(m/z) 429.3.

Example 516. 7-fluoro-5-(5-(4-(1-(trifluoromethyl)cyclopropyl)phenyl)-3,4-dihydroquinolin-1(2H)-yl)-[1,2,4]triazolo[4,3-a]quinazolin-8-amine

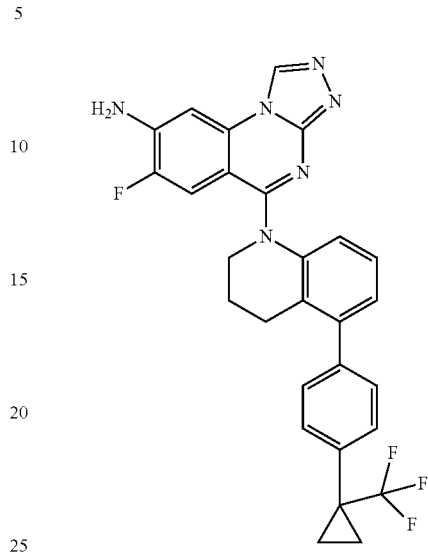

Example 516 was synthesized according to the method of Example 510, except using Example 513 and 4,4,5,5-tetramethyl-2-(4-(1-(trifluoromethyl)cyclopropyl)phenyl)-1,3,2-dioxaborolane instead of Example 509 and p-tolylboronic acid. $^1$H NMR (400 MHz, Methanol-d$_4$) δ 9.38 (s, 1H), 7.62 (d, J=8.1 Hz, 2H), 7.45 (d, J=8.2 Hz, 2H), 7.38 (d, J=7.5 Hz, 2H), 7.26 (dd, J=7.6, 1.4 Hz, 1H), 7.20 (t, J=7.8 Hz, 1H), 7.03 (dd, J=7.9, 1.3 Hz, 1H), 6.96 (d, J=12.8 Hz, 1H), 4.12 (t, J=7.1 Hz, 2H), 2.84 (t, J=6.4 Hz, 2H), 2.11-1.97 (m, 2H), 1.47-1.37 (m, 2H), 1.22-1.10 (m, 2H); LCMS(m/z) 519.4.

Example 517. 5-(5-(3,3-dimethylbut-1-yn-1-yl)-3,4-dihydroquinolin-1(2H)-yl)-7-fluoro-[1,2,4]triazolo[4,3-a]quinazolin-8-amine

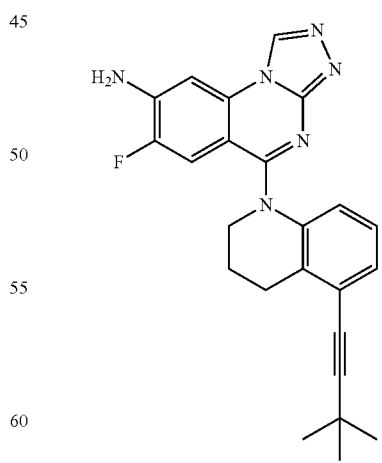

Example 517 was prepared according to the method of Example 522, except using 3,3-dimethylbut-1-yne instead of ethynylcyclopropane. $^1$H NMR (400 MHz, Methanol-d$_4$) δ 9.24 (s, 1H), 7.27 (d, J=7.5 Hz, 1H), 7.15-7.00 (m, 2H), 6.87

(t, J=7.9 Hz, 1H), 6.57 (d, J=8.1 Hz, 1H), 3.97 (s, 2H), 3.02 (t, J=6.7 Hz, 2H), 2.14 (t, J=6.5 Hz, 2H), 1.36 (s, 9H); LCMS(m/z) 415.4.

Example 518. (R)-7-fluoro-5-(2-methyl-3,4-dihydroquinolin-1(2H)-yl)-[1,2,4]triazolo[4,3-a]quinazolin-8-amine

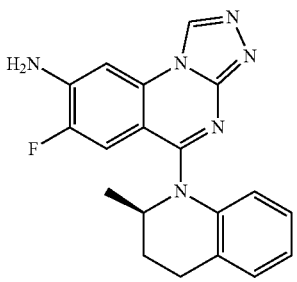 [SMILES: C[C@@H]1CCc2ccccc2N1c1nc2nncn2c2cc(N)c(F)cc12]

The title compound was prepared according to the procedure described in Example 504. $^1$H NMR (400 MHz, Methanol-$d_4$) δ 9.33 (s, 1H), 7.40 (dd, J=7.6, 1.4 Hz, 1H), 7.34 (d, J=7.6 Hz, 1H), 7.26 (td, J=7.5, 1.2 Hz, 1H), 7.13 (td, J=7.7, 1.5 Hz, 1H), 6.96-6.88 (m, 1H), 6.77 (d, J=13.0 Hz, 1H), 5.00 (q, J=6.5 Hz, 1H), 3.00-2.75 (m, 2H), 2.53 (dq, J=13.3, 6.5 Hz, 1H), 1.64 (ddt, J=13.7, 8.5, 5.8 Hz, 1H), 1.31 (d, J=6.5 Hz, 3H); LCMS(m/z) 349.2.

Example 519. (R)-8-chloro-7-fluoro-5-(2-methyl-3,4-dihydroquinolin-1(2H)-yl)-[1,2,4]triazolo[4,3-a]quinazoline

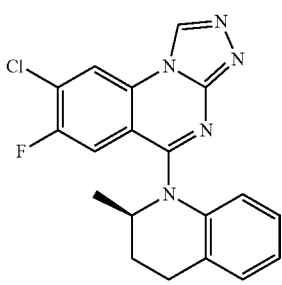

The title compound was prepared according to the procedure described in Example 505. $^1$H NMR (400 MHz, Methanol-$d_4$) δ 9.55 (s, 1H), 8.62 (d, J=6.3 Hz, 1H), 7.44 (d, J=7.5 Hz, 1H), 7.30 (t, J=7.5 Hz, 1H), 7.13 (t, J=7.9 Hz, 1H), 7.04 (d, J=10.3 Hz, 1H), 6.91 (d, J=7.8 Hz, 1H), 5.08 (s, 1H), 2.99-2.86 (m, 3H), 2.60 (d, J=6.3 Hz, 1H), 1.70-1.80 (m, 1H), 1.38 (d, J=6.4 Hz, 4H); LCMS(m/z) 368.2.

Example 520. 7-fluoro-5-(2-methyl-3,4-dihydroquinolin-1(2H)-yl)-[1,2,4]triazolo[4,3-a]quinazolin-8-amine

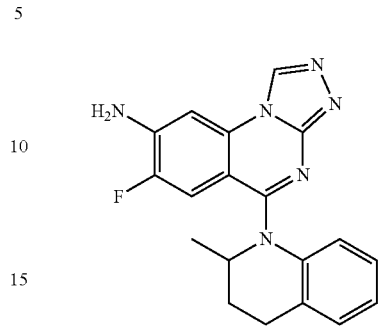

The title compound was prepared according to the procedure described in Example 504. LCMS(m/z) 349.3.

Example 521. 8-chloro-7-fluoro-5-(2-methyl-3,4-dihydroquinolin-1(2H)-yl)-[1,2,4]triazolo[4,3-a]quinazoline

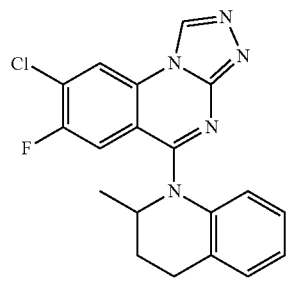 [SMILES: CC1CCc2ccccc2N1c1nc2nncn2c2cc(Cl)c(F)cc12]

The title compound was prepared according to the procedure described in Example 505. $^1$H NMR (400 MHz, Methanol-$d_4$) δ 9.57 (s, 1H), 8.67 (d, J=6.4 Hz, 1H), 7.50 (d, J=7.5 Hz, 1H), 7.40 (td, J=7.5, 1.1 Hz, 1H), 7.19 (td, J=7.7, 1.4 Hz, 1H), 7.03 (d, J=7.9 Hz, 1H), 6.98 (d, J=10.5 Hz, 1H), 5.17 (dt, J=7.8, 6.2 Hz, 1H), 3.01-2.79 (m, 2H), 2.67 (ddt, J=13.3, 8.0, 5.4 Hz, 1H), 1.62 (ddt, J=12.7, 9.6, 6.1 Hz, 1H), 1.37 (d, J=6.4 Hz, 3H); LCMS(m/z) 368.2.

Example 522. 5-(5-(cyclopropylethynyl)-3,4-dihydroquinolin-1(2H)-yl)-7-fluoro-[1,2,4]triazolo[4,3-a]quinazolin-8-amine

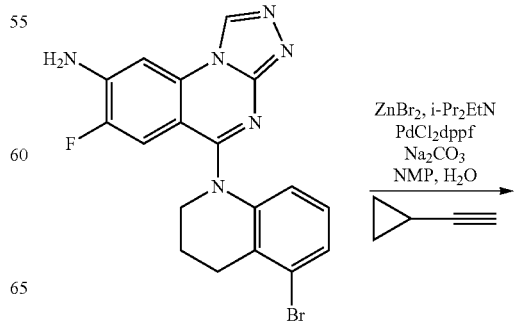

-continued

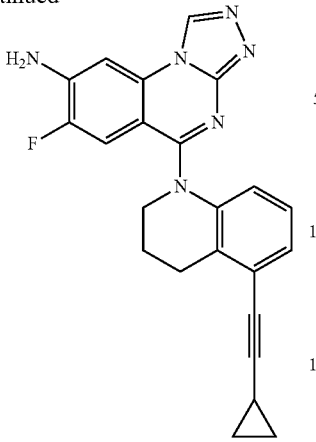

5-(5-Bromo-3,4-dihydroquinolin-1(2H)-yl)-7-fluoro-[1,2,4]triazolo[4,3-a]quinazolin-8-amine (Example 513, 35.0 mg, 0.0847 mmol), ethynylcyclopropane (56.0 mg, 0.847 mmol, 10 equiv.), DIPEA (219.0 mg, 1.69 mmol, 20 equiv.), zinc bromide (191.0 mg, 0.847 mmol, 10 equiv.) and [1,1'-bis(diphenylphosphino)ferrocene] dichloropalladium(II) (6.3 mg, 0.00847 mmol, 0.1 equiv.) were heated in NMP (2 mL) at 100° C. for 30 min, 120° C. for 1 h and 120° C. for 1 h under a nitrogen atmosphere. After a filtration, the reaction mixture was purified by preparative reverse phase high performance liquid chromatography to give the title compound: $^1$H NMR (400 MHz, Methanol-$d_4$) δ 9.37 (s, 1H), 7.37 (d, J=7.5 Hz, 1H), 7.25 (dd, J=7.7, 1.1 Hz, 1H), 7.08-6.95 (m, 2H), 6.90 (dd, J=8.1, 1.1 Hz, 1H), 4.13 (t, J=6.5 Hz, 2H), 3.03 (t, J=6.7 Hz, 2H), 2.15 (p, J=6.6 Hz, 2H), 1.56 (tt, J=8.3, 5.0 Hz, 1H), 0.95 (dt, J=8.2, 3.2 Hz, 2H), 0.86-0.75 (m, 2H); LCMS(m/z) 399.3.

Example 523. 5-(5-(cyclopropylethynyl)-3,4-dihydroquinolin-1(2H)-yl)-7-fluoro-[1,2,4]triazolo[4,3-a]quinazolin-8-amine

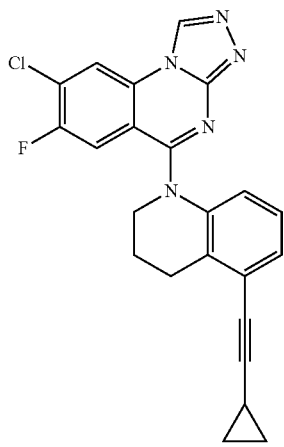 [SMILES: Fc1cc2c(N3CCCc4c(C#CC5CC5)cccc43)nc3nncn3c2cc1Cl]

5-(5-(Cyclopropylethynyl)-3,4-dihydroquinolin-1(2H)-yl)-7-fluoro-[1,2,4]triazolo[4,3-a]quinazolin-8-amine (Example 522, 6.5 mg, 0.0163 mmol), copper(I) chloride (2.4 mg, 0.0245 mmol, 1.5 equiv.) was dissolved in acetonitrile (0.5 mL). To the mixture was added a solution of tert-butyl nitrite (2.5 mg, 0.0245 mmol, 1.5 equiv.) in acetonitrile (0.5 mL). Since the reaction did not go to completion after 40 min at rt, additional reagents were added [copper(I) chloride (4.8 mg, 3.0 equiv.) and tert-butyl nitrite (5.0 mg, 3.0 equiv.)]. The reaction mixture was stirred at rt for 1 h 20 min. After a filtration, the reaction mixture was purified by preparative reverse phase high performance liquid chromatography to give the title compound: $^1$H NMR (400 MHz, Methanol-$d_4$) δ 9.61 (s, 1H), 8.70 (d, J=6.4 Hz, 1H), 7.40-7.18 (m, 2H), 7.04 (t, J=7.9 Hz, 1H), 6.93 (dd, J=8.2, 1.2 Hz, 1H), 4.19 (t, J=6.7 Hz, 2H), 3.07 (t, J=6.6 Hz, 2H), 2.18 (quin, J=6.6 Hz, 2H), 1.57 (tt, J=8.3, 5.0 Hz, 1H), 1.09-0.90 (m, 2H), 0.89-0.73 (m, 2H); LCMS(m/z) 418.3.

Example 524. 5-(5-cyclopropyl-3,4-dihydroquinolin-1(2H)-yl)-7-fluoro-[1,2,4]triazolo[4,3-a]quinazolin-8-amine

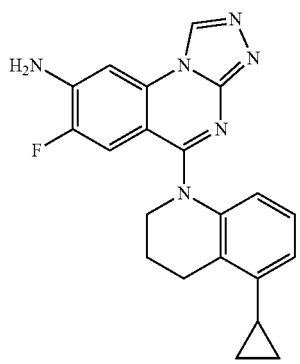 [SMILES: Nc1cc2c(cc1F)c(N1CCCc3c(C4CC4)cccc31)nc1nncn12]

5-(5-Bromo-3,4-dihydroquinolin-1(2H)-yl)-7-fluoro-[1,2,4]triazolo[4,3-a]quinazolin-8-amine (Example 513, 35.0 mg, 0.0847 mmol), cyclopropylboronic acid (43.6 mg, 0.508 mmol, 6 equiv.), diacetoxypalladium (3.8 mg, 0.0169 mmol, 0.2 equiv.), tricyclohexylphosphane (19 mg, 0.0678 mmol, 0.8 equiv.) and dipotassiooxyphosphoryloxypotassium (162 mg, 0.762 mmol, 9 equiv.) were heated in 1,4-dioxane (2 mL) and water (0.2 mL) at 100° C. for 21 h under a nitrogen atmosphere. After a filtration, the reaction mixture was purified by preparative reverse phase high performance liquid chromatography to give the title compound: $^1$H NMR (400 MHz, Methanol-$d_4$) δ 9.34 (s, 1H), 7.35 (d, J=7.6 Hz, 1H), 7.05-6.94 (m, 2H), 6.91 (d, J=12.9 Hz, 1H), 6.80 (dd, J=7.5, 1.6 Hz, 1H), 4.15 (t, J=6.4 Hz, 2H), 3.11 (t, J=6.7 Hz, 2H), 2.18 (p, J=6.6 Hz, 2H), 2.06 (ddd, J=13.9, 8.6, 5.4 Hz, 1H), 1.11-0.97 (m, 2H), 0.80-0.63 (m, 2H); LCMS(m/z) 375.2.

Example 525. 8-chloro-N-methyl-N-(4'-morpholino-[1,1'-biphenyl]-3-yl)-[1,2,4]triazolo[4,3-a]quinazolin-5-amine

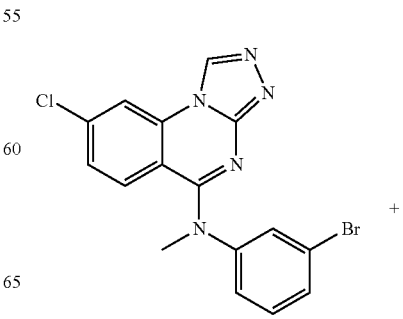

-continued

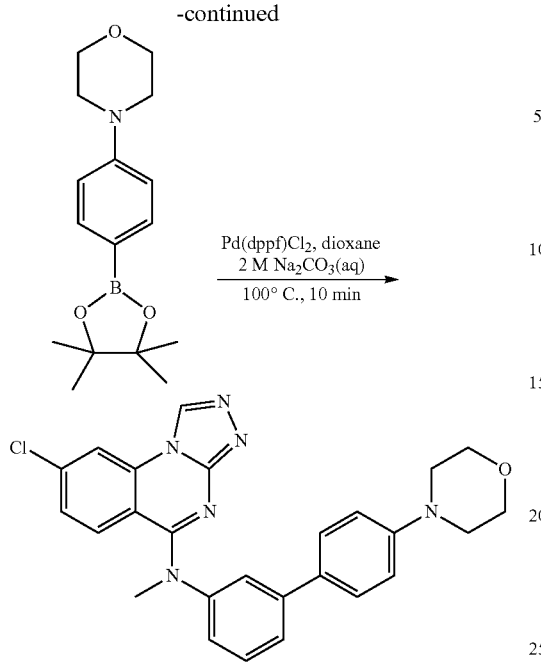

To a solution of N-(3-bromophenyl)-8-chloro-N-methyl-[1,2,4]triazolo[4,3-a]quinazolin-5-amine (Example 308, 35.0 mg, 0.090 mmol) in dioxane (1.0 mL) was added 4-(4-(4,4,5,5-tetramethyl-1,3,2-dioxaborolan-2-yl)phenyl)morpholine (26.0 mg, 0.09 mmol), Pd(dppf)Cl₂ (3.72 mg, 4.5 μmmol), and a 2 M solution of Na₂CO₃(aq) (47.7 mg, 0.450 mmol) and the mixture was purged with nitrogen gas and heated at 100° C. for 15 min. Upon completion, the mixture was diluted with EA, filtered through Celite®, and concentrated under reduced pressure. The crude product was dissolved in DMSO and purified via reverse phase HPLC to afford the title compound: ¹H NMR (400 MHz, DMSO-d₆) δ 9.80 (s, 1H), 8.63 (d, J=1.9 Hz, 1H), 7.66 (d, J=8.2 Hz, 2H), 7.55-7.50 (m, 3H), 7.44-7.40 (m, 1H), 7.32 (d, J=8.4 Hz, 1H), 7.26 (d, J=9.1 Hz, 1H), 6.99 (d, J=8.8 Hz, 2H), 3.77-3.70 (m, 4H), 3.68 (s, 3H), 3.18-3.10 (m, 4H); LCMS (m/z) 471.1.

Example 526. 1-(3'-((8-chloro-[1,2,4]triazolo[4,3-a]quinazolin-5-yl)(methyl)amino)-[1,1'-biphenyl]-4-yl)cyclopropane-1-carbonitrile

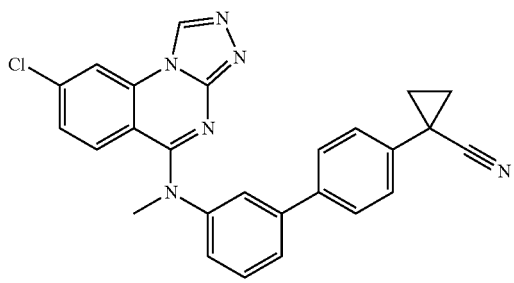

Example 526 was prepared according to the method of Example 525. ¹H NMR (400 MHz, DMSO-d₆) δ 9.78 (s, 1H), 8.63 (d, J=1.9 Hz, 1H), 7.76-7.66 (m, 4H), 7.67 (d, J=8.5 Hz, 3H), 7.56 (t, J=7.9 Hz, 1H), 7.44-7.35 (m, 5H), 7.26 (d, J=9.0 Hz, 1H), 3.68 (s, 3H), 1.79 (m, 2H), 1.55-1.50 (m, 2H); LCMS(m/z) 451.1.

Example 527. (1-(3'-((8-chloro-[1,2,4]triazolo[4,3-a]quinazolin-5-yl)(methyl)amino)-[1,1'-biphenyl]-4-yl)cyclopropyl)methanol

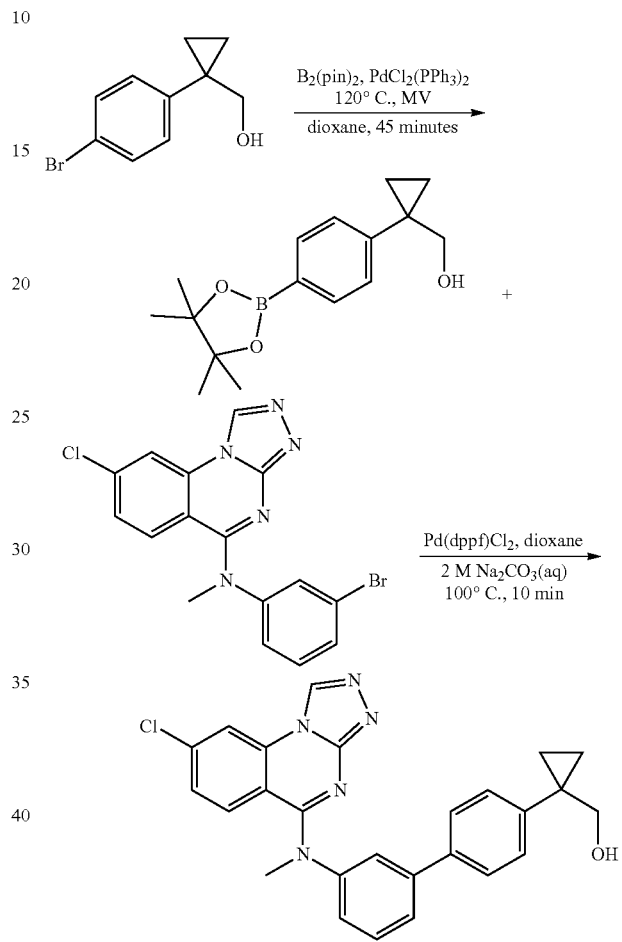

Synthesis of (1-(4-(4,4,5,5-tetramethyl-1,3,2-dioxaborolan-2-yl)phenyl)cyclopropyl)methanol: A microwave vial equipped with a stir bar was charged with (1-(4-bromophenyl)cyclopropyl)methanol (60.0 mg, 0.264 mmol), bis(pinacolato)diboron (80.5 mg, 0.317 mmol), PdCl₂(PPh₃)₂ (9.27 mg, 0.013 mmol), KOAc (77.8 mg, 0.793 mmol) and dioxane (1 mL). The vial was purged with nitrogen, sealed and the mixture was irradiated at 120° C. for 45 min. The mixture was then diluted with EA, filtered through Celite®, concentrated under reduced pressure and used in the next step with no further purification. MS (m/z) 297.1 [M+Na]⁺.

Synthesis of (1-(3'-((8-chloro-[1,2,4]triazolo[4,3-a]quinazolin-5-yl)(methyl)amino)-[1,1'-biphenyl]-4-yl)cyclopropyl)methanol: To a solution of N-(3-bromophenyl)-8-chloro-N-methyl-[1,2,4]triazolo[4,3-a]quinazolin-5-amine (Example 308, 103 mg, 0.264 mmol) in dioxane (2.6 mL) was added (1-(4-(4,4,5,5-tetramethyl-1,3,2-dioxaborolan-2-yl)phenyl)cyclopropyl)methanol (72.4 mg, 0.264 mmol), Pd(dppf)C12 (10.9 mg, 0.013 mmol), and a 2 M solution of Na₂CO₃(aq) (140 mg, 1.32 mmol) and the mixture was purged with nitrogen and then heated at 100° C. for 10 min.

Upon completion, the mixture was diluted with EA, filtered through Celite®, and concentrated under reduced pressure. The crude product was dissolved in DMSO and purified via reverse phase HPLC to afford the title compound: $^1$H NMR (400 MHz, DMSO-$d_6$) δ 9.80 (s, 1H), 8.63 (d, J=1.9 Hz, 1H), 7.68 (m, 2H), 7.61-7.50 (m, 4H), 7.45-7.37 (m, 2H), 7.35 (d, J=8.3 Hz, 2H), 7.24 (d, J=9.1 Hz, 1H), 3.68 (s, 2H), 3.54 (s, 2H), 0.86 (m, 2H), 0.73 (m, 2H); LCMS(m/z) 456.2.

Example 528. (R)-8-chloro-N-methyl-N-(4'-(3-(trifluoromethyl)morpholino)-[1,1'-biphenyl]-3-yl)-[1,2,4]triazolo[4,3-a]quinazolin-5-amine

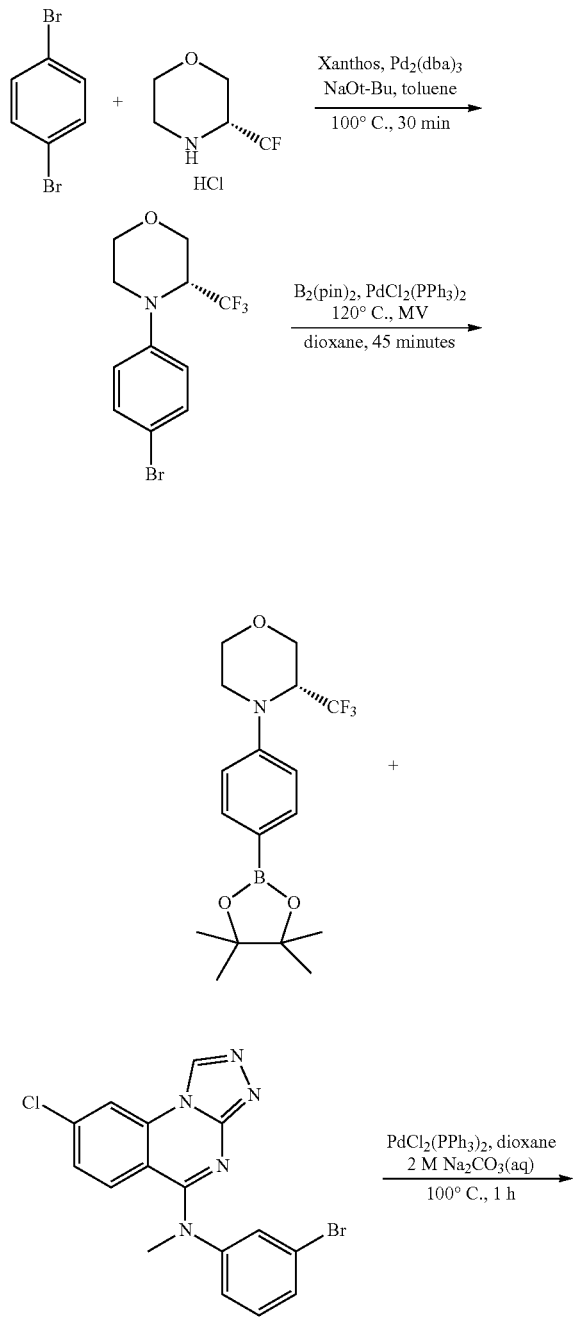

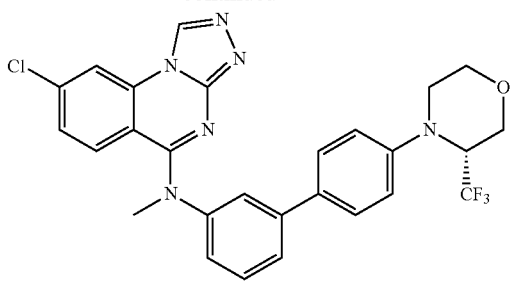

Synthesis of (R)-4-(4-bromophenyl)-3-(trifluoromethyl)morpholine: A solution of 1,4-diboromobenzene (200 mg, 0.848 mmol), (R)-3-(trifluoromethyl)morpholine hydrochloride (171 mg, 0.890 mmol), sodium tert-butoxide (204 mg, 2.12 mmol), and Pd$_2$(dba)$_3$ (38.8 mg, 0.042 mmol) in toluene (1.00 mL) was purged with nitrogen gas and heated at 90° C. for 30 min. Upon completion, the reaction was diluted with EA, filtered through Celite and concentrated under reduced pressure. The crude product was purified with silica gel chromatography eluting with EA in hexanes 0-100%. MS (m/z) 310.1 [M+H]$^+$.

Synthesis of (R)-4-(4-(4,4,5,5-tetramethyl-1,3,2-dioxaborolan-2-yl)phenyl)-3-(trifluoromethyl)morpholine: A microwave vial equipped with a stir bar was charged with (R)-4-(4-bromophenyl)-3-(trifluoromethyl)morpholine (30.0 mg, 0.097 mmol), bis(pinacolato)diboron (29.5 mg, 0.116 mmol), PdCl$_2$(PPh$_3$)$_2$ (3.40 mg, 0.0048 mmol), KOAc (28.5 mg, 0.290 mmol) and dioxane (1 mL). The vial was purged with nitrogen gas, sealed and the reaction mixture was irradiated at 120° C. for 45 min. The mixture was then diluted with EA, filtered through Celite®, concentrated under reduced pressure and used in the next step with no further purification. MS (m/z) 358.2 [M+H]$^+$.

Synthesis of (R)-8-chloro-N-methyl-N-(4'-(3-(trifluoromethyl)morpholino)-[1,1'-biphenyl]-3-yl)-[1,2,4]triazolo[4,3-a]quinazolin-5-amine: A microwave vial charged with N-(3-bromophenyl)-8-chloro-N-methyl-[1,2,4]triazolo[4,3-a]quinazolin-5-amine (37.6 mg, 0.097 mmol), (R)-4-(4-(4,4,5,5-tetramethyl-1,3,2-dioxaborolan-2-yl)phenyl)-3-(trifluoromethyl)morpholine (34.6 mg, 0.097 mmol), PdCl$_2$(PPh$_3$)$_2$ (3.40 mg, 0.0048 mmol), a 2 M solution of Na$_2$CO$_3$ (aq) (51.3 mg, 0.484 mmol) and dioxane (1.0 mL). The mixture was purged with nitrogen, sealed and irradiated at 100° C. for 1 hr. Upon completion, the mixture was diluted with EA, filtered through Celite®, concentrated under reduced pressure. The crude product was dissolved in DMSO and purified via reverse phase HPLC to afford the title compound: $^1$H NMR (400 MHz, DMSO-$d_6$) δ 9.73 (s, 1H), 8.60 (d, J=1.9 Hz, 1H), 7.67 (s, 1H), 7.62 (d, J=8.6 Hz, 1H), 7.55 (d, J=8.7 Hz, 2H), 7.48 (t, J=7.9 Hz, 1H), 7.38 (d, J=9.3 Hz, 1H), 7.29 (d, J=9.0 Hz, 2H), 7.05 (d, J=8.9 Hz, 2H), 4.85 (m, 1H), 4.16 (d, J=12.5 Hz, 1H), 3.99 (s, 1H), 3.79 (s, 1H), 3.65 (s, 3H), 3.60-3.52 (m, 1H), 3.33 (m, 2H); LCMS(m/z) 539.2.

Example 529. 7,8-dichloro-N-methyl-N-(3-(6-(trifluoromethyl)pyridin-3-yl)phenyl)-[1,2,4]triazolo[4,3-a]quinazolin-5-amine

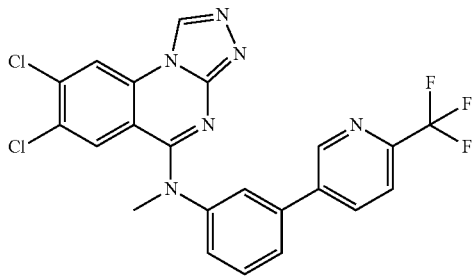 [SMILES: CN(c1cccc(-c2ccc(C(F)(F)F)nc2)c1)c1nc2nncn2c2cc(Cl)c(Cl)cc12]

Synthesis of 7,8-dichloro-N-methyl-N-(3-(6-(trifluoromethyl)pyridin-3-yl)phenyl)-[1,2,4]triazolo[4,3-a]quinazolin-5-amine: The title compound was prepared according to the method presented for the synthesis of Example 528 starting with Example 530 and [6-(trifluoromethyl)-3-pyridyl]boronic acid. $^1$H NMR (400 MHz, DMSO-$d_6$) δ 9.72 (s, 1H), 9.06 (d, J=2.2 Hz, 1H), 8.82 (s, 1H), 8.37 (dd, J=8.2, 2.2 Hz, 1H), 7.98 (d, J=8.2 Hz, 1H), 7.92 (d, J=2.0 Hz, 1H), 7.85 (d, J=7.5 Hz, 1H), 7.66 (t, J=7.9 Hz, 1H), 7.55 (dd, J=7.7, 2.2 Hz, 1H), 7.32 (s, 1H), 3.66 (s, 3H); LCMS(m/z) 489.

Example 530. N-(3-bromophenyl)-7,8-dichloro-N-methyl-[1,2,4]triazolo[4,3-a]quinazolin-5-amine

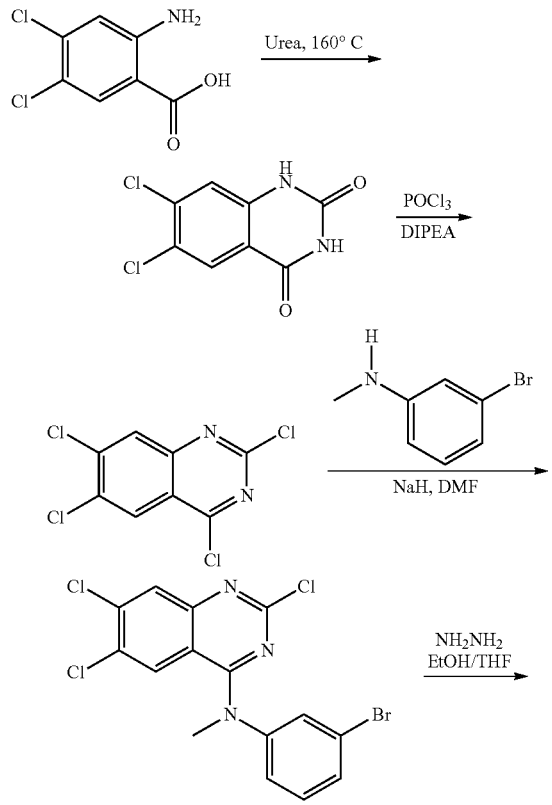

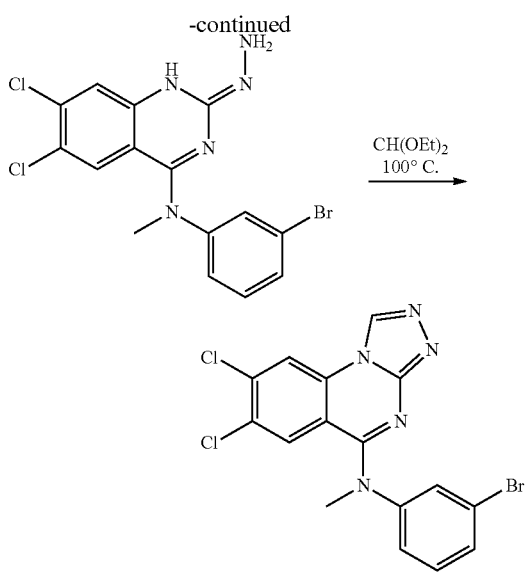

Synthesis of 6,7-dichloroquinazoline-2,4(1H,3H)-dione: A mixture of urea (2.86 g, 47.6 mmol) and 2-amino-4,5-dichlorobenzoic acid (1.00 g, 4.76 mmol) was heated at 160° C. for 18 hr. The mixture was cooled to 100° C. and water was added to suspend the material and heating was continued for an additional 10 min. The resultant mixture was filtered and transferred to a flask. A solution of 0.5 N NaOH (aq) was added until a suspension was formed, and the mixture was heated at 100° C. for 10 min. The reaction was then cooled to rt, and the pH was adjusted to pH of 2 with HCl (conc) and the mixture filtered. The resulting residue was washed with water:MeOH (1:1) (60 mL) and dried in vacuo to provide the product: MS (m/z) 230.9 [M+H]$^+$.

Synthesis of 2,4,6,7-tetrachloroquinazoline: To a mixture of 6,7-dichloroquinazoline-2,4(1H,3H)-dione (467 mg, 1.98 mmol) and DIPEA (538 mg, 4.16 mmol) was added phosphoryl chloride (3.84 g, 25.1 mmol) dropwise at rt and the mixture was stirred at rt for 5 min and then heated at 107° C. for 3 hr. The mixture was then carefully poured over crushed ice and stirred vigorously until a suspension was formed. To this mixture was added DCM and transferred to a separatory funnel. The aqueous layer was extracted with DCM (×2), and the combined organic layers were washed with a 10% solution of citric acid (aq), washed with brine, dried over Na$_2$SO$_4$. The solvent was removed under reduced pressure to give the desired intermediate.

Synthesis of N-(3-bromophenyl)-2,6,7-trichloro-N-methylquinazolin-4-amine: To a solution of 2,4,6,7-tetrachloroquinazoline (451 mg, 1.68 mmol) and 3-bromo-N-methylaniline (329 mg, 1.77 mmol) in DMF (4.0 mL) at 0° C. was added NaH (60% dispersion in mineral oil) (148 mg, 3.87 mmol) in one portion. The cold bath was removed, and the mixture was stirred at rt for 2 hr. Upon completion, the reaction was cooled to 0° C. and a solution of sat. NH$_4$C(aq) was added slowly. The reaction was transferred to a separatory funnel and extracted with EA (×3). The combined organic layers were washed with brine, dried over Na$_2$SO$_4$, and concentrated under reduced pressure to afford the crude product, which was suspended in heptane, filtered and further dried in vacuo to afford the indicated intermediate: MS (m/z) 416.1 [M+H]$^+$.

Synthesis of (E)-N-(3-bromophenyl)-6,7-dichloro-2-hydrazono-N-methyl-1,2-dihydroquinazolin-4-amine: To a solution of N-(3-bromophenyl)-2,6,7-trichloro-N-methylquinazolin-4-amine (236 mg, 0.565 mmol) in THF (5.60 mL) and ethanol (9.40 mL) was added hydrazine monohydrate (141 mg, 2.81 mmol) and the mixture was stirred at 50° C. for 1 hr. Upon completion, the reaction was cooled to rt, and concentrated under reduced pressure and dried in vacuo to afford the intermediate. MS (m/z) 414.1 [M+H]+.

Synthesis of N-(3-bromophenyl)-7,8-dichloro-N-methyl-[1,2,4]triazolo[4,3-a]quinazolin-5-amine: A solution of (E)-N-(3-bromophenyl)-6,7-dichloro-2-hydrazono-N-methyl-1,2-dihydroquinazolin-4-amine (234 mg, 0.566 mmol) and triethyl orthoformate (1.65 g, 11.1 mmol) was heated to 100° C. for 30 min. Upon completion, the reaction was cooled to RT, and concentrated under reduced pressure to afford the crude product. The crude product was triturated with heptane and the materials were collected by filtration, washed with heptane:ether (3:1) and dried in vacuo to afford a partially purified product. The crude material was dissolved in DMSO and purified via reverse phase HPLC to afford the title compound: 1H NMR (400 MHz, DMSO-$d_6$) δ 9.74 (s, 1H), 8.85 (s, 1H), 7.73 (s, 1H), 7.58 (m, 1H), 7.43 (m, 2H), 7.27 (s, 1H), 3.59 (s, 3H); LCMS(m/z) 422.1.

Example 531. 8-chloro-N-(4'-(cyclopropylsulfonyl)-[1,1'-biphenyl]-3-yl)-N-methyl-[1,2,4]triazolo[4,3-a]quinazolin-5-amine

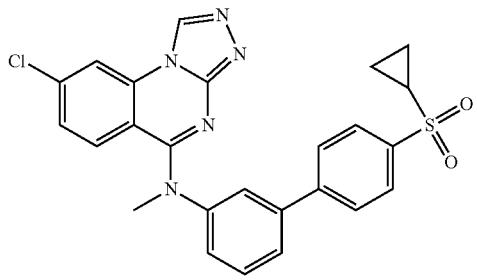 [SMILES: CN(c1cccc(-c2ccc(S(=O)(=O)C3CC3)cc2)c1)c1nc2nncn2c2cc(Cl)ccc12]

Example 531 was prepared according to the method of Example 525. 1H NMR (400 MHz, DMSO-$d_6$) δ 9.81 (s, 1H), 8.64 (d, J=1.9 Hz, 1H), 7.94 (m, 4H), 7.87 (s, 1H), 7.80 (d, J=7.8 Hz, 1H), 7.62 (t, J=7.9 Hz, 1H), 7.50 (d, J=7.7 Hz, 1H), 7.42 (dd, J=9.1, 2.0 Hz, 1H), 7.27 (d, J=9.1 Hz, 1H), 3.70 (s, 3H), 2.93-2.85 (m, 1H), 1.13 (d, J=6.9 Hz, 2H), 1.05 (d, J=10.0 Hz, 2H); LCMS(m/z) 490.1.

Example 532. 8-chloro-N-methyl-N-(4'-((trifluoromethyl)sulfonyl)-[1,1'-biphenyl]-3-yl)-[1,2,4]triazolo[4,3-a]quinazolin-5-amine

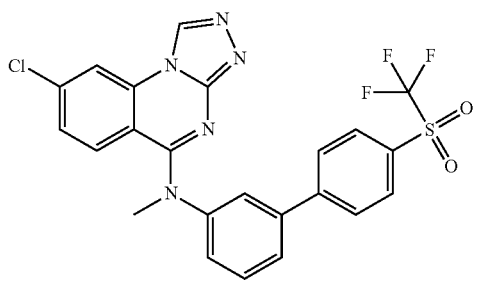

Example 532 was prepared according to the method of Example 525. 1H NMR (400 MHz, DMSO-$d_6$) δ 9.80 (d, J=1.9 Hz, 1H), 8.64 (s, 1H), 8.20 (d, J=8.3 Hz, 2H), 8.13 (d, J=8.4 Hz, 2H), 7.95 (s, 1H), 7.84 (d, J=7.9 Hz, 1H), 7.64 (t, J=7.8 Hz, 1H), 7.53 (d, J=7.8 Hz, 1H), 7.41 (d, J=9.0 Hz, 1H), 7.29 (d, J=9.0 Hz, 1H), 3.69 (s, 3H); LCMS(m/z) 518.1.

Example 533. (S)-8-chloro-N-methyl-N-(4'-(3-(trifluoromethyl)morpholino)-[1,1'-biphenyl]-3-yl)-[1,2,4]triazolo[4,3-a]quinazolin-5-amine

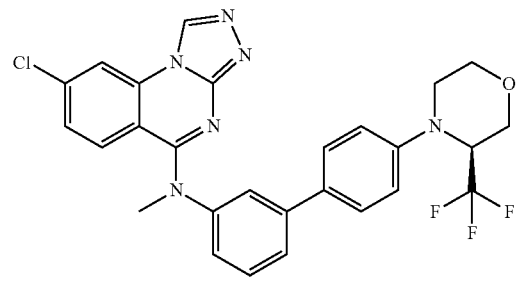 [SMILES: CN(c1cccc(-c2ccc(N3CCOC[C@H]3C(F)(F)F)cc2)c1)c1nc2nncn2c2cc(Cl)ccc12]

Synthesis of (S)-8-chloro-N-methyl-N-(4'-(3-(trifluoromethyl)morpholino)-[1,1'-biphenyl]-3-yl)-[1,2,4]triazolo[4,3-a]quinazolin-5-amine: The title compound was prepared according to the method presented for the synthesis of Example 528, except starting with (S)-3-(trifluoromethyl)morpholine. H NMR (400 MHz, DMSO-$d_6$) δ 9.76 (s, 1H), 8.61 (d, J=1.6 Hz, 1H), 7.68 (s, 1H), 7.64 (d, J=8.1 Hz, 1H), 7.54 (d, J=8.7 Hz, 2H), 7.49 (t, J=7.9 Hz, 1H), 7.40 (dd, J=9.2, 1.7 Hz, 1H), 7.31-7.24 (m, 2H), 7.06 (d, J=8.8 Hz, 2H), 4.91-4.79 (m, 1H), 4.17 (d, J=12.6 Hz, 1H), 3.98 (d, J=10.3 Hz, 1H), 3.78 (d, J=14.7 Hz, 1H), 3.66 (s, 3H), 3.58 (td, J=12.9, 12.5, 6.6 Hz, 1H), 3.31 (d, J=16.0 Hz, 2H); LCMS(m/z) 540.2.

Example 534. N-(4'-((2-oxa-6-azaspiro[3.3]heptan-6-yl)sulfonyl)-[1,1'-biphenyl]-3-yl)-8-chloro-N-methyl-[1,2,4]triazolo[4,3-a]quinazolin-5-amine

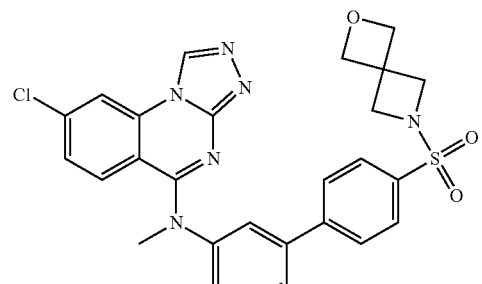

Example 534 was prepared according to the method of Example 525. 1H NMR (400 MHz, DMSO-$d_6$) δ 9.65 (s, 1H), 8.56 (d, J=2.0 Hz, 1H), 7.95 (d, J=8.4 Hz, 2H), 7.82 (d, J=8.4 Hz, 2H), 7.79 (s, 1H), 7.69 (d, J=7.7 Hz, 1H), 7.53 (t, J=7.9 Hz, 1H), 7.39 (d, J=8.9 Hz, 1H), 7.33 (s, 2H), 4.44 (s, 4H), 3.90 (s, 4H), 3.61 (s, 3H); LCMS(m/z) 547.1.

Example 535. 3'-((8-chloro-[1,2,4]triazolo[4,3-a]quinazolin-5-yl)(methyl)amino)-N-(1-methylcyclobutyl)-[1,1'-biphenyl]-4-sulfonamide

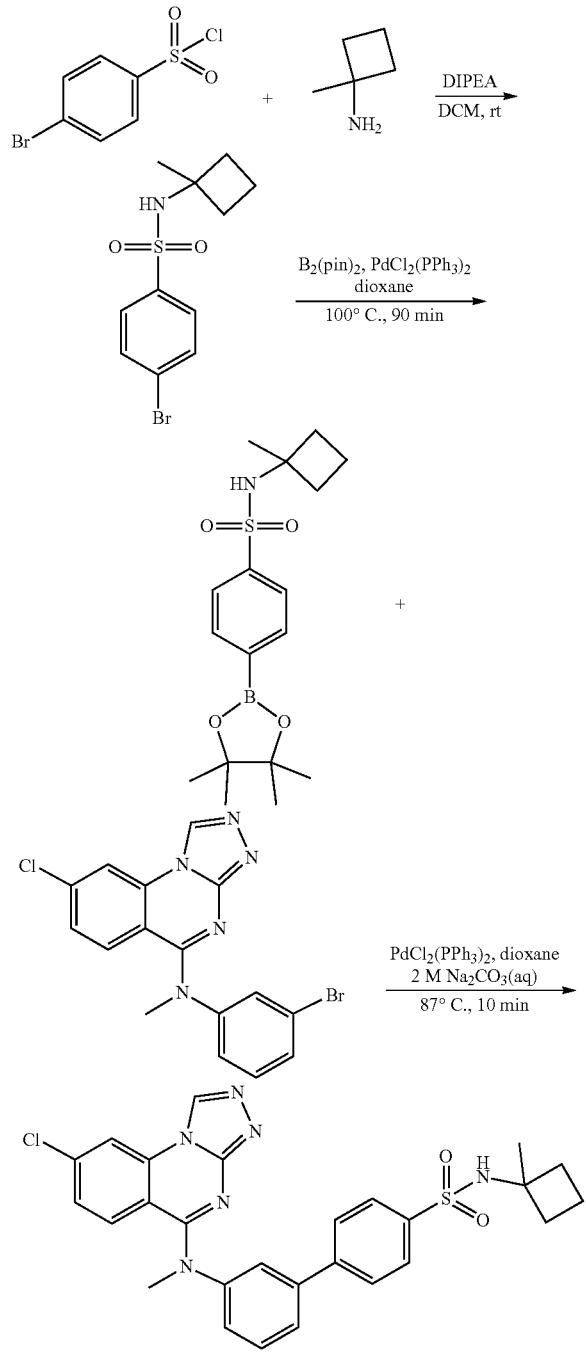

Synthesis of 4-bromo-N-(1-methylcyclobutyl)benzenesulfonamide: To a suspension of 4-bromobenzenesulfonyl chloride (200 mg, 0.783 mmol), 1-methylcyclobutanamine (80.0 mg, 0.939 mmol) in DCM (3.10 mL) was added DIPEA (202 mg, 1.57 mmol) at rt under an inert atmosphere. The reaction was stirred for 18 hr and then concentrated under reduced pressure. The crude residue was purified with silica gel chromatography eluting with EA in hexanes 0-25% to afford the desired sulfonamide. MS (m/z) 303.5 [M+H]$^+$. $^1$H NMR (400 MHz, Chloroform-d) δ 7.75 (d, J=8.7 Hz, 2H), 7.63 (d, J=8.7 Hz, 2H), 2.16 (d, J=9.4 Hz, 2H), 1.92-1.82 (m, 2H), 1.79-1.67 (m, 2H), 1.38 (s, 3H).

Synthesis of N-(1-methylcyclobutyl)-4-(4,4,5,5-tetramethyl-1,3,2-dioxaborolan-2-yl)benzenesulfonamide: A solution of 4-bromo-N-(1-methylcyclobutyl)benzenesulfonamide (52.0 mg, 0.171 mmol), bis(pinacolato)diboron (52.1 mg, 0.205 mmol), Pd(dppf)Cl2 (2.79 mg, 0.0034 mmol), KOAc (50.3 mg, 0.513 mmol) and dioxane (1.10 mL) was purged with nitrogen and heated at 100° C. for 90 min. Upon completion, the mixture was diluted with EA, filtered through Celite®, concentrated under reduced pressure and used in the next step with no further purification. MS (m/z) 352.2 [M+H]$^+$.

Synthesis of 3'-((8-chloro-[1,2,4]triazolo[4,3-a]quinazolin-5-yl)(methyl)amino)-N-(1-methylcyclobutyl)-[1,1'-biphenyl]-4-sulfonamide: To a solution of N-(3-bromophenyl)-8-chloro-N-methyl-[1,2,4]triazolo[4,3-a]quinazolin-5-amine (Example 308, 30.0 mg, 0.077 mmol) in dioxane (0.7 mL) was added N-(1-methylcyclobutyl)-4-(4,4,5,5-tetramethyl-1,3,2-dioxaborolan-2-yl)benzenesulfonamide (29.8 mg, 0.085 mmol), Pd(dppf)Cl2 (3.19 mg, 3.90 μmol), and 2 M solution of Na$_2$CO$_3$(aq) (40.9 mg, 0.386 mmol) and the mixture was purged with nitrogen and heated at 87° C. for 10 min. Upon completion, EA was added, and the mixture was filtered through Celite®, and concentrated under reduced pressure. The crude product was dissolved in DMSO and purified via reverse phase HPLC to afford the title compound: $^1$H NMR (400 MHz, DMSO-d$_6$) δ 9.79 (s, 1H), 8.63 (d, J=2.0 Hz, 1H), 7.91 (s, 1H), 7.86 (s, 5H), 7.77 (d, J=7.9 Hz, 1H), 7.58 (t, J=7.9 Hz, 1H), 7.45-7.39 (m, 2H), 7.29 (d, J=9.0 Hz, 1H), 3.68 (s, 3H), 2.18-2.05 (m, 2H), 1.69-1.55 (m, 4H), 1.27 (s, 3H); LCMS(m/z) 533.1.

Example 536. 7,8-dichloro-N-methyl-N-(4'-(methylsulfonyl)-[1,1'-biphenyl]-3-yl)-[1,2,4]triazolo[4,3-a]quinazolin-5-amine

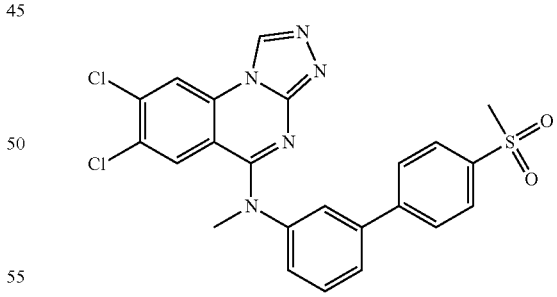

Synthesis of 7,8-dichloro-N-methyl-N-(4'-(methylsulfonyl)-[1,1'-biphenyl]-3-yl)-[1,2,4]triazolo[4,3-a]quinazolin-5-amine: The title compound was prepared according to the method presented for the synthesis of Example 528 starting with Example 530 and 4,4,5,5-tetramethyl-2-(4-methylsulfonylphenyl)-1,3,2-dioxaborolane. $^1$H NMR (400 MHz, DMSO-d$_6$) δ 9.73 (s, 1H), 8.82 (s, 1H), 7.99 (d, J=8.6 Hz, 2H), 7.94 (d, J=8.6 Hz, 2H), 7.87 (s, 1H), 7.82 (d, J=8.0 Hz, 1H), 7.65 (t, J=7.9 Hz, 1H), 7.52 (d, J=6.7 Hz, 1H), 7.27 (s, 1H), 3.68 (s, 3H), 3.24 (s, 3H); LCMS(m/z) 498.

Example 537. N-(4'-(2-oxa-6-azaspiro[3.3]heptan-6-yl)-[1,1'-biphenyl]-3-yl)-8-chloro-N-methyl-[1,2,4]triazolo[4,3-a]quinazolin-5-amine Example 539. 8-chloro-N-(4'-(1-((dimethylamino)methyl)cyclopropyl)-[1,1'-biphenyl]-3-yl)-N-methyl-[1,2,4]triazolo[4,3-a]quinazolin-5-amine

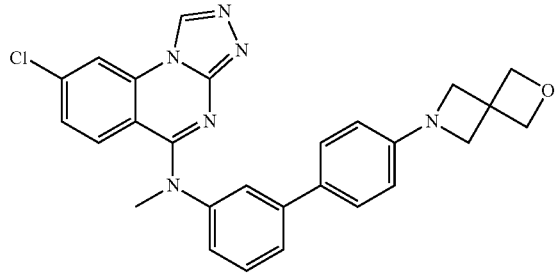 [SMILES: CN(c1cccc(-c2ccc(N3CC4(COC4)C3)cc2)c1)c1nc2nncn2c2cc(Cl)ccc12]

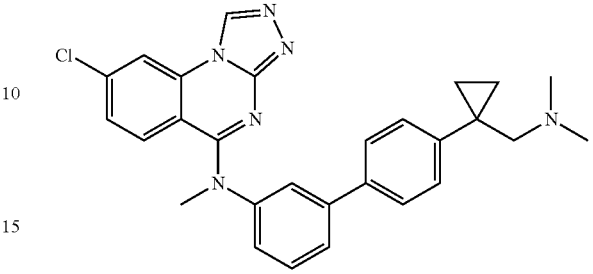

Synthesis of N-(4'-(2-oxa-6-azaspiro[3.3]heptan-6-yl)-[1,1'-biphenyl]-3-yl)-8-chloro-N-methyl-[1,2,4]triazolo[4,3-a]quinazolin-5-amine: The title compound was prepared according to the method presented for the synthesis of Example 528, except starting with 2-oxa-6-azaspiro[3.3]heptane. $^1$H NMR (400 MHz, DMSO-$d_6$) δ 9.62 (s, 1H), 8.53 (d, J=1.9 Hz, 1H), 7.53-7.44 (m, 4H), 7.39 (d, J=7.8 Hz, 1H), 7.30 (d, J=1.2 Hz, 2H), 7.19-7.13 (m, 1H), 6.45 (dd, J=9.0, 2.3 Hz, 2H), 4.71 (s, 4H), 3.98 (s, 4H), 3.58 (s, 3H); LCMS(m/z) 483.2.

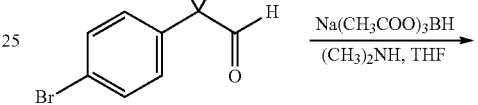

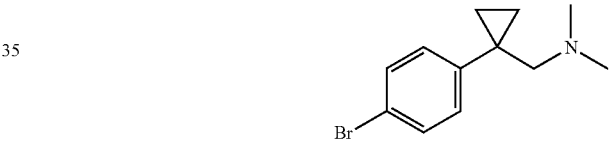

Example 538. 8-chloro-N-(4'-(isobutylsulfonyl)-[1,1'-biphenyl]-3-yl)-N-methyl-[1,2,4]triazolo[4,3-a]quinazolin-5-amine

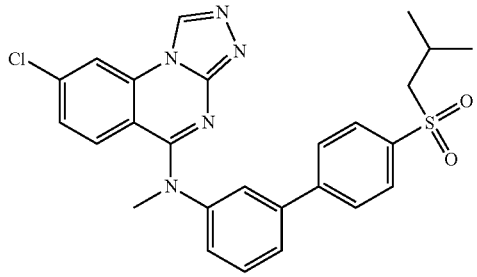 [SMILES: CC(C)CS(=O)(=O)c1ccc(-c2cccc(N(C)c3nc4nncn4c4cc(Cl)ccc34)c2)cc1]

Synthesis of 1-(1-(4-bromophenyl)cyclopropyl)-N,N-dimethylmethanamine: To a solution of 1-(4-bromo-phenyl)-cyclopropanecarbaldehyde (176 mg, 0.782 mmol) in THF (6.0 mL) was added a solution of dimethylamine in THF (2M, 0.938 mmol), glacial acetic acid (56.3 mg, 0.938 mmol) and sodium triacetoxyborohydride (199 mg, 0.938 mmol). The mixture was stirred for 48 hr at RT, quenched with aqueous sodium bicarbonate solution and extracted twice with EA. The combined organic layers were dried over MgSO$_4$ and concentrated under reduced pressure. The crude product was dissolved in DMSO and purified via reverse phase HPLC to afford the desired amine. $^1$H NMR (400 MHz, DMSO-$d_6$) δ 7.55 (d, J=8.4 Hz, 2H), 7.43 (d, J=8.5 Hz, 2H), 3.44 (d, J=5.8 Hz, 2H), 2.68 (d, J=4.8 Hz, 6H), 1.02 (m, 4H); MS (m/z) 254.1 [M+H]$^+$.

Synthesis of 8-chloro-N-(4'-(isobutylsulfonyl)-[1,1'-biphenyl]-3-yl)-N-methyl-[1,2,4]triazolo[4,3-a]quinazolin-5-amine: The title compound was prepared according to the method presented for the synthesis of Example 525. $^1$H NMR (400 MHz, DMSO-$d_6$) δ 9.75 (s, 1H), 8.61 (s, 1H), 7.94 (s, 4H), 7.84 (s, 1H), 7.77 (d, J=4.3 Hz, 1H), 7.61-7.55 (m, 1H), 7.45 (d, J=9.1 Hz, 1H), 7.39 (s, 1H), 7.29 (d, J=9.0 Hz, 1H), 3.66 (s, 3H), 3.24 (d, J=6.5 Hz, 2H), 2.04-1.94 (m, 1H), 0.97 (d, J=6.7 Hz, 6H); LCMS(m/z) 506.1.

Synthesis of 8-chloro-N-(4'-(1-((dimethylamino)methyl)cyclopropyl)-[1,1'-biphenyl]-3-yl)-N-methyl-[1,2,4]triazolo[4,3-a]quinazolin-5-amine: The title compound was prepared according to the method presented for the synthesis of Example 535 starting with 1-(1-(4-bromophenyl)cyclopropyl)-N,N-dimethylmethanamine. $^1$H NMR (400 MHz, DMSO-$d_6$) δ 9.71 (s, 1H), 8.87 (brs, 1H), 8.59 (d, J=2.1 Hz, 1H), 7.67-7.60 (m, 4H), 7.55 (d, J=7.7 Hz, 1H), 7.50 (d, J=8.4 Hz, 2H), 7.39 (d, J=8.9 Hz, 1H), 7.33 (dd, J=9.0, 1.9 Hz, 1H), 7.26 (d, J=9.0 Hz, 1H), 3.63 (s, 3H), 3.47 (d, J=5.5 Hz, 2H), 2.70 (s, 3H), 2.69 (s, 3H), 1.03 (m, 4H); LCMS (m/z) 483.1.

Example 540. 8-chloro-N-(4'-(isopropylsulfonyl)-[1,1'-biphenyl]-3-yl)-N-methyl-[1,2,4]triazolo[4,3-a]quinazolin-5-amine

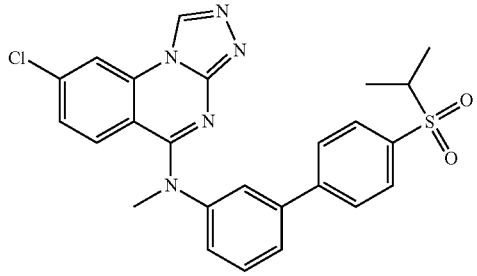

Synthesis of 8-chloro-N-(4'-(isopropylsulfonyl)-[1,1'-biphenyl]-3-yl)-N-methyl-[1,2,4]triazolo[4,3-a]quinazolin-5-amine: The title compound was prepared according to the method presented for the synthesis of Example 525. $^1$H NMR (400 MHz, DMSO-$d_6$) δ 9.80 (s, 1H), 8.64 (d, J=2.1 Hz, 1H), 7.95 (d, J=8.5 Hz, 2H), 7.92-7.86 (m, 3H), 7.79 (d, J=7.8 Hz, 1H), 7.61 (t, J=7.9 Hz, 1H), 7.48 (dd, J=7.6, 2.1 Hz, 1H), 7.41 (dd, J=9.0, 2.1 Hz, 1H), 7.29 (d, J=9.0 Hz, 1H), 3.69 (s, 3H), 3.44 (q, J=6.8 Hz, 1H), 1.17 (d, J=6.8 Hz, 6H); LCMS(m/z) 492.1.

Example 541. 8-chloro-N-methyl-N-(3-(6-(2,2,2-trifluoroethyl)pyridin-3-yl)phenyl)-[1,2,4]triazolo[4,3-a]quinazolin-5-amine

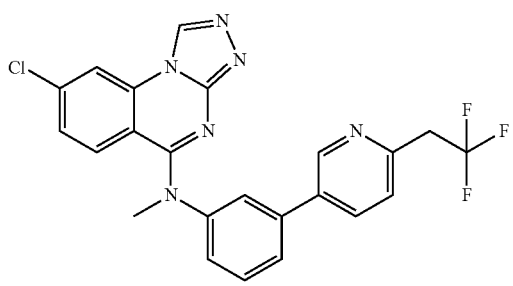

Example 541 was prepared according to the method of Example 525. $^1$H NMR (400 MHz, DMSO-$d_6$) δ 9.77 (s, 1H), 8.84 (d, J=2.4 Hz, 1H), 8.62 (s, 1H), 8.11 (dd, J=8.1, 2.4 Hz, 1H), 7.86-7.82 (m, 1H), 7.78-7.70 (m, 1H), 7.59 (d, J=9.1 Hz, 1H), 7.54 (d, J=8.1 Hz, 1H), 7.46-7.35 (m, 2H), 7.29 (d, J=9.2 Hz, 1H), 3.85 (q, J=11.4 Hz, 2H), 3.67 (s, 3H); LCMS(m/z) 469.1.

Example 542. 3'-((8-chloro-[1,2,4]triazolo[4,3-a]quinazolin-5-yl)(methyl)amino)-N,N-dimethyl-[1,1'-biphenyl]-4-sulfonamide

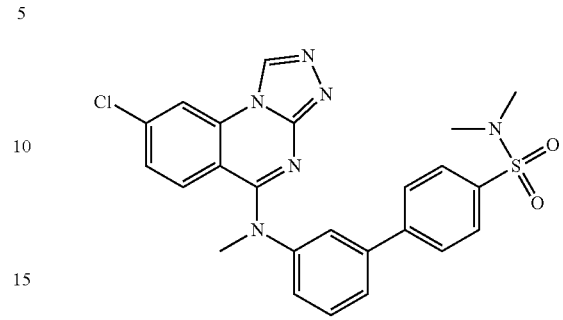

Example 542 was prepared according to the method of Example 525. $^1$H NMR (400 MHz, DMSO-$d_6$) δ 9.78 (s, 1H), 8.63 (d, J=2.0 Hz, 1H), 7.93 (d, J=8.5 Hz, 2H), 7.86 (s, 1H), 7.82-7.75 (m, 3H), 7.60 (t, J=7.9 Hz, 1H), 7.47 (d, J=9.1 Hz, 1H), 7.41 (dd, J=9.0, 2.0 Hz, 1H), 7.29 (d, J=9.0 Hz, 1H), 3.68 (s, 3H), 2.63 (s, 6H); LCMS(m/z) 493.1.

Example 543. 8-chloro-N-(4'-((cyclopropylmethyl)sulfonyl)-[1,1'-biphenyl]-3-yl)-N-methyl-[1,2,4]triazolo[4,3-a]quinazolin-5-amine

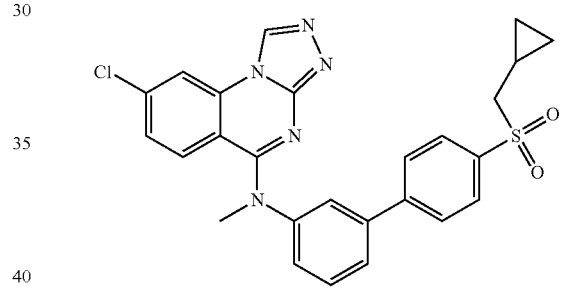

Example 543 was prepared according to the method of Example 525. $^1$H NMR (400 MHz, DMSO-$d_6$) δ 9.76 (s, 1H), 8.62 (s, 1H), 7.94 (s, 4H), 7.86 (s, 1H), 7.77 (d, J=8.1 Hz, 1H), 7.59 (t, J=7.9 Hz, 1H), 7.45 (d, J=8.1 Hz, 1H), 7.39 (d, J=9.0 Hz, 1H), 7.30 (d, J=9.1 Hz, 1H), 3.67 (s, 3H), 3.29 (d, J=7.1 Hz, 2H), 0.87-0.80 (m, 1H), 0.45 (q, J=6.0, 5.3 Hz, 2H), 0.13 (d, J=6.1 Hz, 2H); LCMS(m/z) 504.1.

Example 544. 8-chloro-N-(4'-(ethylsulfonyl)-[1,1'-biphenyl]-3-yl)-N-methyl-[1,2,4]triazolo[4,3-a]quinazolin-5-amine

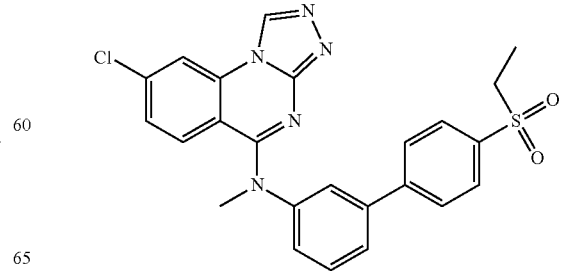

Example 544 was prepared according to the method of Example 525. ¹H NMR (400 MHz, DMSO-d₆) δ 9.73 (s, 1H), 8.83 (d, J=6.6 Hz, 1H), 7.77-7.71 (m, 2H), 7.69 (d, J=8.5 Hz, 2H), 7.59 (t, J=7.8 Hz, 1H), 7.43 (dd, J=7.2, 2.0 Hz, 1H), 7.39 (d, J=8.5 Hz, 2H), 7.00 (d, J=10.9 Hz, 1H), 3.67 (s, 3H), 1.80-1.75 (m, 2H), 1.56-1.50 (m, 2H); LCMS (m/z) 478.1.

Example 545. 8-chloro-N-methyl-N-(4'-((4-methylpiperazin-1-yl)sulfonyl)-[1,1'-biphenyl]-3-yl)-[1,2,4]triazolo[4,3-a]quinazolin-5-amine

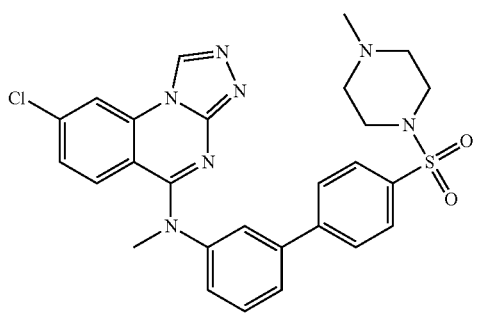 [SMILES: CN1CCN(S(=O)(=O)c2ccc(-c3cccc(N(C)c4nc5nncn5c5cc(Cl)ccc45)c3)cc2)CC1]

Example 545 was prepared according to the method of Example 525. ¹H NMR (400 MHz, DMSO-d₆) δ 9.76 (s, 1H), 8.62-8.61 (m, 1H), 7.98 (d, J=8.5 Hz, 2H), 7.83 (d, J=8.3 Hz, 4H), 7.75 (d, J=7.9 Hz, 1H), 7.61 (t, J=7.9 Hz, 1H), 7.49 (d, J=9.0 Hz, 1H), 7.37 (dd, J=9.0, 2.0 Hz, 1H), 7.29 (d, J=9.0 Hz, 1H), 3.88-3.73 (m, 2H), 3.66 (s, 3H), 3.54-3.38 (m, 2H), 3.24-3.08 (m, 2H), 2.79 (s, 3H), 2.50 (m, 2H); LCMS(m/z) 548.1.

Example 546. 1-(3'-((8-chloro-7-fluoro-[1,2,4]triazolo[4,3-a]quinazolin-5-yl)(methyl)amino)-[1,1'-biphenyl]-4-yl)cyclopropane-1-carbonitrile

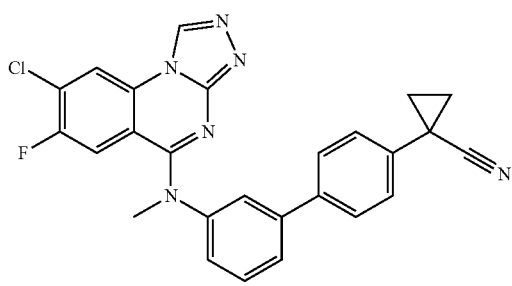

The title compound was prepared according to the procedure described in Example 525. ¹H NMR (400 MHz, DMSO-d₆) δ 9.73 (s, 1H), 8.83 (d, J=6.6 Hz, 1H), 7.77-7.71 (m, 2H), 7.69 (d, J=8.5 Hz, 2H), 7.59 (t, J=7.8 Hz, 1H), 7.43 (dd, J=7.2, 2.0 Hz, 1H), 7.39 (d, J=8.5 Hz, 2H), 7.00 (d, J=10.9 Hz, 1H), 3.67 (s, 3H), 1.80-1.75 (m, 2H), 1.56-1.50 (m, 2H); LCMS(m/z) 469.1.

Example 547. 1-(5-(3-((8-chloro-[1,2,4]triazolo[4,3-a]quinazolin-5-yl)(methyl)amino)phenyl)pyridin-2-yl)cyclopropane-1-carbonitrile

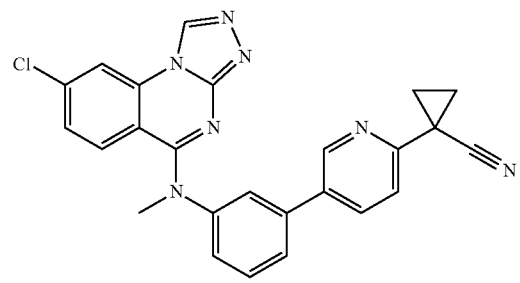

Synthesis of 1-(5-(3-((8-chloro-[1,2,4]triazolo[4,3-a]quinazolin-5-yl)(methyl)amino)phenyl)pyridin-2-yl)cyclopropane-1-carbonitrile: The title compound was prepared according to the method presented for the synthesis of Example 527, except starting with 1-(5-bromopyridin-2-yl)cyclopropane-1-carbonitrile. ¹H NMR (400 MHz, DMSO-d₆) δ 9.80 (s, 1H), 8.79-8.76 (m, 1H), 8.64 (d, J=1.9 Hz, 1H), 8.12 (dd, J=8.3, 2.3 Hz, 1H), 7.82 (s, 1H), 7.75 (d, J=7.9 Hz, 1H), 7.59 (dd, J=8.0, 5.7 Hz, 2H), 7.46 (d, J=6.3 Hz, 1H), 7.41 (dd, J=9.0, 2.0 Hz, 1H), 7.27 (d, J=9.0 Hz, 1H), 3.68 (s, 3H), 1.86-1.82 (m, 2H), 1.70 (q, J=4.9, 4.5 Hz, 2H); LCMS (m/z) 452.1.

Example 548. N-(4'-(1-(aminomethyl)cyclopropyl)-[1,1'-biphenyl]-3-yl)-8-chloro-N-methyl-[1,2,4]triazolo[4,3-a]quinazolin-5-amine

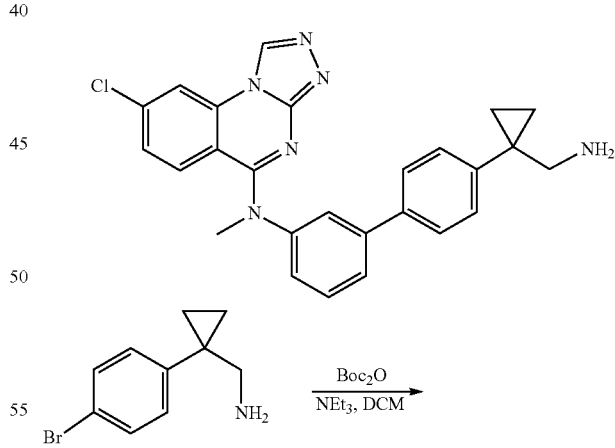

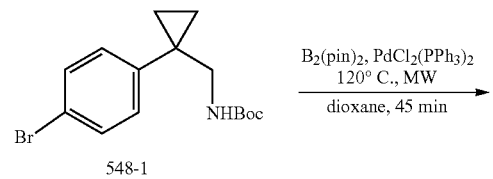

548-1

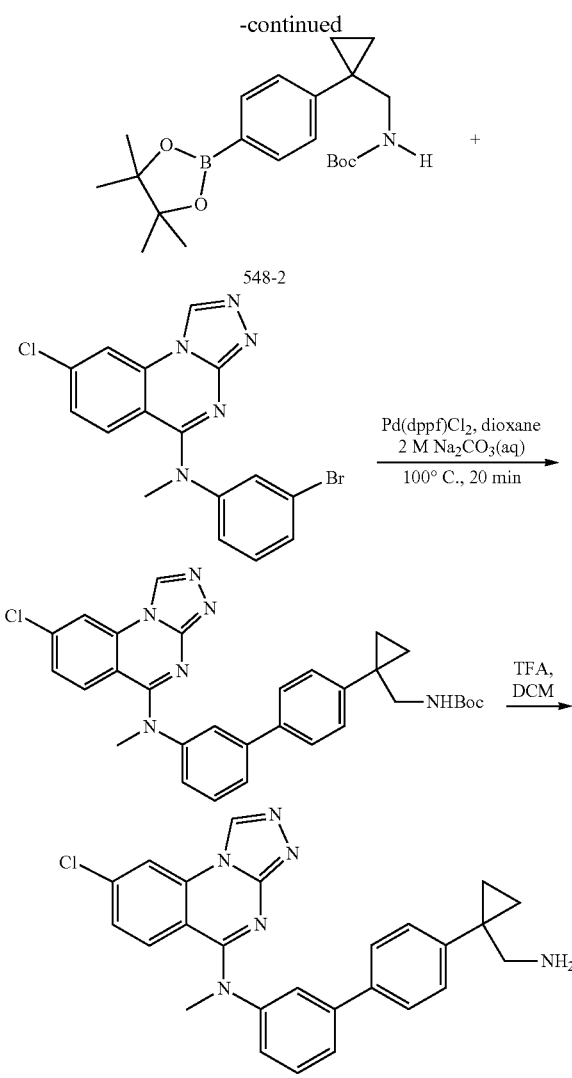

Synthesis of tert-butyl ((1-(3'-((8-chloro-[1,2,4]triazolo[4,3-a]quinazolin-5-yl)(methyl)amino)-[1,1'-biphenyl]-4-yl)cyclopropyl)methyl)carbamate (Intermediate 548-3): To a solution of N-(3-bromophenyl)-8-chloro-N-methyl-[1,2,4]triazolo[4,3-a]quinazolin-5-amine (Example 308, 59.0 mg, 0.152 mmol) in dioxane (1.7 mL) was added tert-butyl ((1-(4-(4,4,5,5-tetramethyl-1,3,2-dioxaborolan-2 yl)phenyl)cyclopropyl)methyl)carbamate (57.8 mg, 0.155 mmol), Pd(dppf)C12 (6.28 mg, 7.59 µmol), and 2 M solution of Na$_2$CO$_3$(aq) (80.4 mg, 0.759 mmol) and the mixture was purged with nitrogen and heated at 100° C. for 20 min. Upon completion, the mixture was diluted with EA, filtered through Celite®, and concentrated under reduced pressure. The crude product was purified using silica chromatography eluting with EA in hexanes 0-100%, followed by MeOH in EA 0-35% to afford the desired intermediate. MS (m/z) 554.2 [M+H]$^+$.

To a solution of tert-butyl ((1-(3'-((8-chloro-[1,2,4]triazolo[4,3-a]quinazolin-5-yl)(methyl)amino)-[1,1'-biphenyl]-4-yl)cyclopropyl)methyl)carbamate (77.0 mg, 0.139 mmol) in DCM (1.4 mL) at rt was added TFA (347 mg, 6.94 mmol) and the mixture was stirred for 20 min. Upon completion, the reaction mixture was concentrated under reduced pressure and the crude residue was dissolved in DMSO and purified via reverse phase HPLC to afford the title compound: $^1$H NMR (400 MHz, DMSO-d$_6$) δ 9.73 (s, 1H), 8.60 (d, J=1.9 Hz, 1H), 7.73 (brs, 2H), 7.69-7.62 (m, 3H), 7.62 (d, J=8.3 Hz, 2H), 7.55 (t, J=8.1 Hz, 1H), 7.42 (d, J=8.2 Hz, 3H), 7.35 (dd, J=9.0, 1.9 Hz, 1H), 7.25 (d, J=9.0 Hz, 1H), 3.65 (s, 3H), 3.13-3.04 (m, 2H), 1.01 (m, 2H), 0.94-0.88 (m, 2H); LCMS(m/z) 455.2.

Example 549. N-methyl-8-((methylamino)methyl)-N-phenyl-[1,2,4]triazolo[4,3-a]quinazolin-5-amine

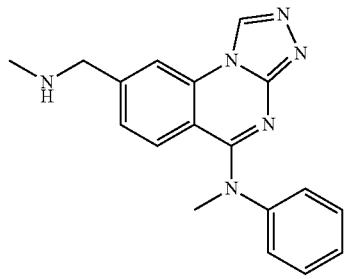

Titanium (IV) Isopropoxide (0.39 ml, 1.45 mmol) was added dropwise to a commercially available solution of 2M dimethylamine in methanol (0.14 ml, 1.9 mmol) followed by the addition of aldehyde Example 117 (200 mg, 0.6 mmol). The reaction mixture was stirred at ambient temperature for 4.5 h, after which sodium borohydride (48 mg, 1.3 mmol) was added and the resulting mixture was further stirred for another period of 1.5 h. The reaction was then quenched by the addition of water, the resulting inorganic precipitate was filtered, washed with diethyl ether and the aqueous filtrate was extracted with diethyl ether. The combined ether extracts were dried MgSO$_4$ and concentrated in vacuo to give N-methyl-8-((methylamino)methyl)-N-phenyl-[1,2,4]triazolo[4,3-a]quinazolin-5-amine: $^1$H NMR (400 MHz, Methanol-d+) δ 9.52 (s, 1H), 8.46 (d, J=1.7 Hz, 1H), 7.62-7.47 (m, 3H), 7.47-7.41 (m, 2H), 7.37 (dd, J=8.8, 1.7

Synthesis of tert-Butyl-4-Bromophenethylcarbamate (Intermediate 548-1): To a solution of 2-(4-bromophenyl)ethanamine (300 mg, 1.33 mmol) in DCM (7.0 mL) was added triethylamine (161 mg, 1.59 mmol) and di-tert-butyl dicarbonate (347 mg, 1.59 mmol) at 0° C. The mixture was gradually warmed to rt and stirred for 18 hr. The reaction mixture was concentrated under reduced pressure and the crude product was purified using silica gel chromatography eluting with EA in hexanes 0-100% to afford the intermediate carbamate. MS (m/z) 350.1 [M+Na]$^+$. $^1$H NMR (400 MHz, DMSO-d$_6$) δ 7.48-7.40 (m, 2H), 7.26-7.18 (m, 2H), 6.87 (t, J=5.9 Hz, 1H), 3.16 (d, J=6.1 Hz, 2H), 1.32 (s, 6H), 0.83 (t, J=3.1 Hz, 2H), 0.69 (q, J=4.4 Hz, 2H).

Synthesis of tert-butyl ((1-(4-(4,4,5,5-tetramethyl-1,3,2-dioxaborolan-2 yl)phenyl)cyclopropyl)methyl)carbamate (Intermediate 548-2): A microwave vial equipped with a stir bar was charged with tert-Butyl-4-Bromophenethylcarbamate (50.0 mg, 0.153 mmol), bis(pinacolato)diboron (46.7 mg, 0.184 mmol), PdCl$_2$(PPh$_3$)$_2$ (11.9 mg, 0.017 mmol), KOAc (45.1 mg, 0.460 mmol) and dioxane (2.0 mL). The vial was purged with nitrogen gas, sealed and the reaction mixture was irradiated at 120° C. for 45 min. The mixture was then diluted with EA, filtered through Celite®, concentrated under reduced pressure and used in the next step with no further purification. MS (m/z) 396.3 [M+Na]$^+$.

Hz, 1H), 7.29 (d, J=8.8 Hz, 1H), 4.38 (s, 2H), 3.80 (s, 3H), 2.79 (s, 3H); LCMS(m/z) 319.2.

Example 550. N-methyl-8-(morpholinomethyl)-N-phenyl-[1,2,4]triazolo[4,3-a]quinazolin-5-amine

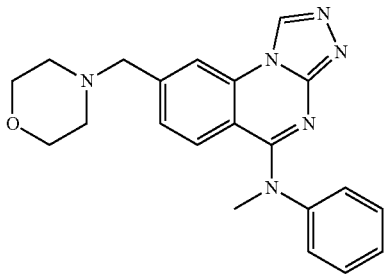 [SMILES: CN(c1ccccc1)c1nc2nncn2c2cc(CN3CCOCC3)ccc12]

The title compound was synthesized according to the general procedure described for Example 549: ¹H NMR (400 MHz, Methanol-d₄) δ 9.52 (d, J=3.1 Hz, 1H), 8.48 (d, J=1.7 Hz, 1H), 7.63-7.49 (m, 3H), 7.49-7.37 (m, 3H), 7.29-7.19 (m, 1H), 4.40 (s, 2H), 3.95-3.85 (m, 3H), 3.81 (d, J=7.2 Hz, 4H), 3.27-3.13 (m, 4H); LCMS(m/z) 375.1.

Example 551. 8-((dimethylamino)methyl)-N-methyl-N-phenyl-[1,2,4]triazolo[4,3-a]quinazolin-5-amine

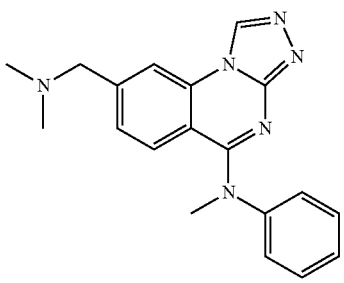

The title compound was synthesized according to the general procedure described for Example 549: ¹H NMR (400 MHz, Methanol-d₄) δ 9.51 (d, J=1.9 Hz, 1H), 8.46 (dd, J=24.2, 1.7 Hz, 1H), 7.62-7.50 (m, 3H), 7.49-7.35 (m, 3H), 7.28 (dd, J=8.8, 5.2 Hz, 1H), 4.43 (d, J=43.9 Hz, 2H), 3.82 (d, J=1.8 Hz, 3H), 2.92 (s, 3H); LCMS(m/z) 333.2.

Example 552. 7-fluoro-N-methyl-N-(4'-(trifluoromethyl)-[1,1'-biphenyl]-3-yl)-8-(4-(trifluoromethyl)phenoxy)-[1,2,4]triazolo[4,3-a]quinazolin-5-amine

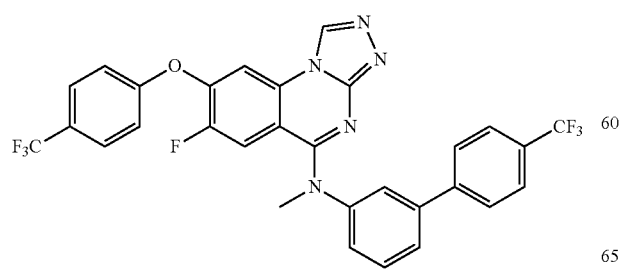

The title compound was isolated from the crude product mixture during the synthesis of Example 465. ¹H NMR (400 MHz, Chloroform-d) δ 9.09 (s, 1H), 7.76-7.59 (m, 9H), 7.53 (t, J=2.0 Hz, 1H), 7.36 (m, 1H), 7.20 (d, J=8.5 Hz, 2H), 7.09 (d, J=11.9 Hz, 1H), 3.78 (s, 3H); LCMS(m/z) 598.4.

Example 553. ethyl (E)-N-(5-((3-bromophenyl)(methyl)amino)-7-fluoro-[1,2,4]triazolo[4,3-a]quinazolin-8-yl)formohydrazonate

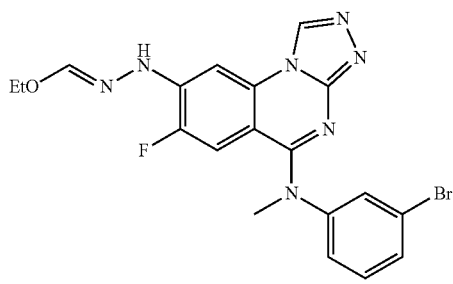 [SMILES: CCO/C=N/Nc1cc2c(cc1F)c(N(C)c1cccc(Br)c1)nc1nncn12]

The title compound was isolated from the crude product mixture during the synthesis of Example 459. ¹H NMR (400 MHz, DMSO-d₆) δ 9.59 (s, 1H), 8.76-8.61 (m, 1H), 7.89 (d, J=7.3 Hz, 1H), 7.51 (t, J=2.0 Hz, 1H), 7.41 (m, 1H), 7.32 (t, J=8.0 Hz, 1H), 7.29-7.22 (m, 1H), 7.14 (s, 1H), 6.88 (d, J=13.2 Hz, 1H), 4.25 (q, J=7.1 Hz, 2H), 3.52 (s, 3H), 1.34 (t, J=7.1 Hz, 3H); LCMS(m/z) 458.2.

Example 554. 1-((Dimethylamino)methyl)-N-methyl-N-phenyl-[1,2,4]triazolo[4,3-a]quinazolin-5-amine

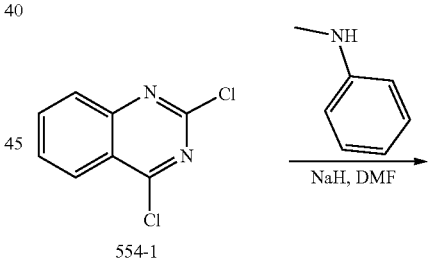

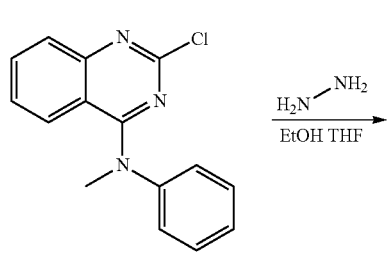

-continued

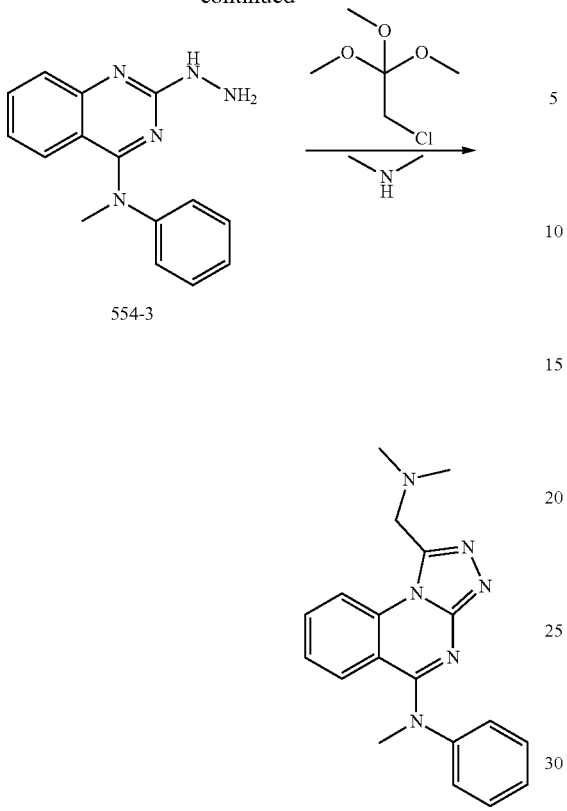

554-3

Synthesis of 2-chloro-N-methyl-N-phenylquinazolin-4-amine (554-2): To a solution of 2,4-dichloroquinazoline (Intermediate 554-1, 4 g, 20.1 mmol) in DMF (20 ml) were added N-methylaniline (2.58 g, 24.1 mmol) and sodium hydride (965 mg, 24.1 mmol) then the mixture was stirred for 1 h at RT. Water was added to the reaction mixture and the resultant mixture was filtered. The resulting residue was used in the next step without further purification.

Synthesis of 2-hydrazineyl-N-methyl-N-phenylquinazolin-4-amine (554-3): Hydrazine hydrate (817 mg, 16.3 mmol) was added slowly to a stirred solution of crude 2-chloro-N-methyl-N-phenylquinazolin-4-amine (Intermediate 554-2, 2.2 g, 8.16 mmol) in a solution of ethanol and THF 2:1 (10 ml). The mixture was heated at 60° C. for 18 hrs. The mixture was diluted with DCM, and then washed successively with water and brine, and dried over $MgSO_4$. The organic layer was concentrated in vacuo. The resulting residue was used in the next step without further purification.

A solution of 2-chloro-1,1,1-trimethoxyethane (1.7 g, 10.9 mmol) and the crude 2-hydrazineyl-N-methyl-N-phenylquinazolin-4-amine (Intermediate 554-3, 20 mg, 0.08 mmol) was stirred at 100° C. for 24 h. The mixture was concentrated in vacuo, and then dissolved in a solution of 2N dimethyl amine in THF (2 ml) and stirred at room temperature for another 24 hrs. The mixture was concentrated in vacuo and then the residue purified by reverse phase chromatography ACN/Water 15-95% with 0.1% TFA for 15 min to yield the title compound: $^1$H NMR (400 MHz, Methanol-$d_4$) δ 8.08 (d, J=8.7 Hz, 1H), 7.91 (ddd, J=8.7, 7.2, 1.5 Hz, 1H), 7.56-7.49 (m, 2H), 7.48-7.40 (m, 2H), 7.40-7.25 (m, 3H), 5.16 (s, 2H), 3.78 (s, 3H), 3.16 (s, 6H); LCMS(m/z) 333.2.

Example 555. 8-bromo-1-cyclopropyl-7-fluoro-N-methyl-N-phenyl-[1,2,4]triazolo[4,3-a]quinazolin-5-amine

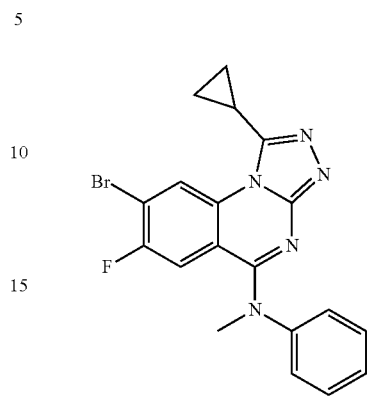

Example 555 was synthesized in a similar fashion as Example 500, except using trimethoxymethylcyclopropane instead of 1,1,1-triethoxyethane. LCMS-ESI+(m/z): [M+H]+ calcd for $C_{19}H_{17}BrFN_5$: 412.05 (M−1+1), 414.05 (M+1+1), found: 412.22 (M−1+1), 414.17 (M+1+1).

Example 556. 7-fluoro-N-(3-fluorophenyl)-8-hydrazineyl-N-methyl-[1,2,4]triazolo[4,3-a]quinazolin-5-amine

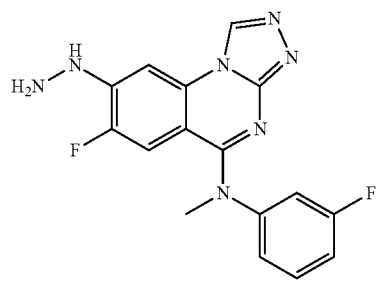

Hydrazine hydrate (304 mg, 6 mmol) was added slowly to a stirred solution of crude 7,8-difluoro-N-(3-fluorophenyl)-N-methyl-[1,2,4]triazolo[4,3-a]quinazolin-5-amine (Example 249, 20 mg, 0.06 mmol) in a solution of ethanol and THF 2:1 (5 ml). The mixture was heated at 100° C. for 24 hrs. The mixture was diluted with DCM, and then washed successively with water and brine, and dried over $MgSO_4$. The mixture was concentrated in vacuo and then the residue was purified by reverse phase chromatography ACN/Water 15-95% with 0.1% TFA for 15 min to yield the title compound: $^1$H NMR (400 MHz, Methanol-$d_4$) δ 9.33 (s, 1H), 7.69 (d, J=7.5 Hz, 1H), 7.43 (q, J=7.8 Hz, 1H), 7.06 (tt, J=8.9, 4.0 Hz, 3H), 6.78 (d, J=13.6 Hz, 1H), 3.62 (s, 3H); LCMS(m/z) 342.1.

Example 557. Ethyl 3-(7-fluoro-5-((3-fluorophenyl)(methyl)amino)-[1,2,4]triazolo[4,3-a]quinazolin-8-yl)propanoate

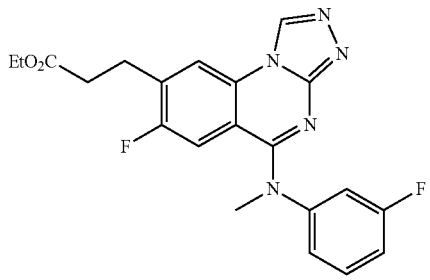

The title compound was isolated in Step 7 of the synthesis of Example 467. ¹H NMR (400 MHz, Chloroform-d) δ 9.11 (s, 1H), 7.94 (d, J=6.3 Hz, 1H), 7.39 (m, 1H), 7.04 (m, 1H), 6.98 (m, 1H), 6.94-6.86 (m, 2H), 4.12 (q, J=7.1 Hz, 2H), 3.66 (s, 3H), 3.11 (t, J=7.3 Hz, 2H), 2.72 (t, J=7.3 Hz, 2H), 1.22 (t, J=7.1 Hz, 3H); LCMS(m/z) 412.3.

Example 558. (3'-((8-chloro-[1,2,4]triazolo[4,3-a]quinazolin-5-yl)(methyl)amino)-[1,1'-biphenyl]-4-yl)dimethylphosphine oxide

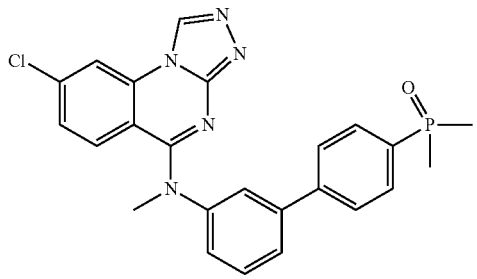

The title compound was synthesized in a similar manner as described for Example 337, except using (4-bromophenyl)dimethylphosphine oxide instead of 2-bromo-5-cyclopropylpyrazine and using chloro(2-dicyclohexylphosphino-2',4',6'-triisopropyl-1,1'-biphenyl)[2-(2'-amino-1,1'-biphenyl)]palladium(II) instead of [1,1'-bis(diphenylphosphino)ferrocene]dichloropalladium(II). ¹H NMR (400 MHz, Acetone-$d_6$) δ 9.47 (s, 1H), 8.42 (d, J=2.1 Hz, 1H), 7.95-7.73 (m, 5H), 7.70 (d, J=7.8 Hz, 1H), 7.59 (t, J=7.8 Hz, 1H), 7.51 (d, J=9.0 Hz, 1H), 7.49-7.41 (m, 1H), 7.28 (dd, J=9.0, 2.1 Hz, 1H), 3.72 (s, 3H), 1.71 (d, J=13.3 Hz, 6H); LCMS(m/z) 462.2.

Example 559. (3'-((8-chloro-[1,2,4]triazolo[4,3-a]quinazolin-5-yl)(methyl)amino)-[1,1'-biphenyl]-4-yl)(imino)(methyl)-l6-sulfanone

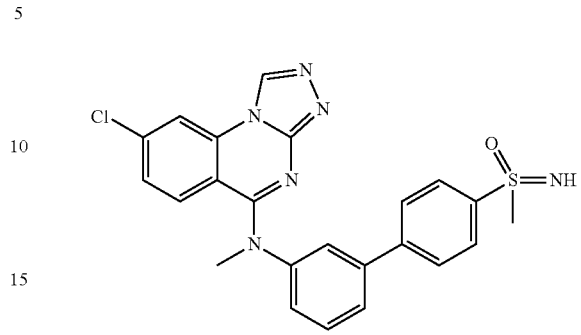

The title compound was synthesized in a similar manner as described for Example 337, except using (4-bromophenyl)(imino)(methyl)-$\lambda^6$-sulfanone instead of 2-bromo-5-cyclopropylpyrazine and using chloro(2-dicyclohexylphosphino-2',4',6'-triisopropyl-1,1'-biphenyl)[2-(2'-amino-1,1'-biphenyl)]palladium(II) instead of [1,1'-bis(diphenylphosphino)ferrocene]dichloropalladium(II). ¹H NMR (400 MHz, Acetone-$d_6$) δ 9.46 (s, 1H), 8.41 (d, J=2.1 Hz, 1H), 8.05-7.97 (m, 3H), 7.86 (d, J=8.4 Hz, 2H), 7.79 (t, J=2.1 Hz, 1H), 7.71 (d, J=7.7 Hz, 1H), 7.64-7.44 (m, 3H), 7.28 (dd, J=8.9, 2.1 Hz, 1H), 3.71 (s, 3H), 3.09 (s, 3H); LCMS(m/z) 463.2.

Example 560. 2-(tert-butyl)-5-(3-((8-chloro-[1,2,4]triazolo[4,3-a]quinazolin-5-yl)(methyl)amino)phenyl)pyridine 1-oxide

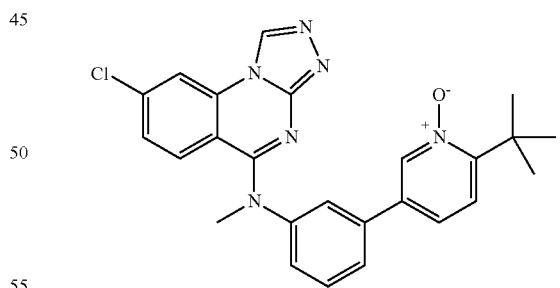

The title compound was synthesized in a similar manner as described for Example 337, except using 5-bromo-2-(tert-butyl)pyridine 1-oxide instead of 2-bromo-5-cyclopropylpyrazine and using chloro(2-dicyclohexylphosphino-2',4',6'-triisopropyl-1,1'-biphenyl)[2-(2'-amino-1,1'-biphenyl)]palladium(II) instead of [1,1'-bis(diphenylphosphino)ferrocene]dichloropalladium(II). ¹H NMR (400 MHz, Acetone-$d_6$) δ 9.45 (s, 1H), 8.40 (d, J=2.0 Hz, 1H), 8.35 (d, J=1.9 Hz, 1H), 7.82-7.43 (m, 7H), 7.27 (dd, J=8.8, 2.0 Hz, 1H), 3.71 (s, 3H), 1.50 (s, 9H); LCMS(m/z) 459.3.

Example 561. 5-(tert-butyl)-2-(3-((8-chloro-[1,2,4]triazolo[4,3-a]quinazolin-5-yl)(methyl)amino)phenyl)pyridine 1-oxide

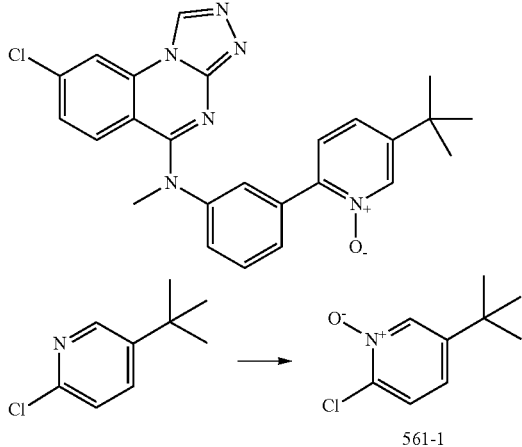

561-1

3-Chlorobenzoperoxoic acid (77% wt, 109 mg, 485 μmol) was added to a stirred solution of 5-(tert-butyl)-2-chloropyridine (30.0 mg, 177 μmol) in dichloromethane (0.5 mL) at room temperature. After 19 h, the resulting mixture was purified by flash column chromatography on silica gel (hexanes) to give Intermediate 561-1.

The title compound was synthesized in a similar manner as described for Example 337, except using Intermediate 561-1 instead of 2-bromo-5-cyclopropylpyrazine and using chloro(2-dicyclohexylphosphino-2',4',6'-triisopropyl-1,1'-biphenyl)[2-(2'-amino-1,1'-biphenyl)]palladium(II) instead of [1,1'-bis(diphenylphosphino)ferrocene]dichloropalladium(II). $^1$H NMR (400 MHz, Acetone-d$_6$) δ 9.45 (s, 1H), 8.40 (d, J=2.0 Hz, 1H), 8.22 (d, J=1.9 Hz, 1H), 7.95 (d, J=2.1 Hz, 1H), 7.87 (d, J=7.7 Hz, 1H), 7.59-7.49 (m, 3H), 7.49-7.41 (m, 2H), 7.27 (dd, J=9.0, 2.1 Hz, 1H), 3.68 (s, 3H), 1.37 (s, 9H); LCMS(m/z) 459.3.

Example 563. 8-chloro-N-(3-((5-((dimethylamino)methyl)pyrazin-2-yl)oxy)phenyl)-N-methyl-[1,2,4]triazolo[4,3-a]quinazolin-5-amine

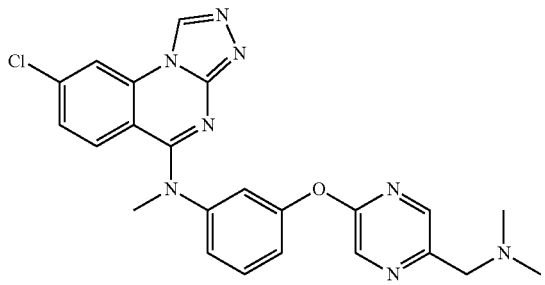 [SMILES: CN(C)Cc1cnc(Oc2cccc(N(C)c3nc4nncn4c4cc(Cl)ccc34)c2)cn1]

The title compound was isolated from the crude product mixture in the synthesis of Example 229. $^1$H NMR (400 MHz, Methanol-d$_4$) δ 9.53 (s, 1H), 8.58 (d, J=1.4 Hz, 1H), 8.45 (d, J=2.0 Hz, 1H), 8.20 (s, 1H), 7.60 (t, J=8.4 Hz, 1H), 7.46-7.37 (m, 2H), 7.34 (d, J=7.8 Hz, 1H), 7.32-7.25 (m, 2H), 4.48 (s, 2H), 3.76 (s, 3H), 2.95 (s, 6H); LCMS(m/z) 461.3.

Example 564. 8-chloro-N-methyl-N-(3-((5-(morpholinomethyl)pyrazin-2-yl)oxy)phenyl)-[1,2,4]triazolo[4,3-a]quinazolin-5-amine

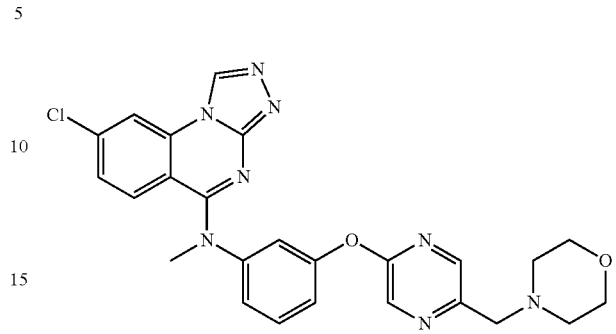

The title compound was isolated from the crude product mixture in the synthesis of Example 230. $^1$H NMR (400 MHz, Methanol-d$_4$) δ 9.56 (s, 1H), 8.60 (d, J=1.6 Hz, 1H), 8.49 (d, J=2.1 Hz, 1H), 8.23 (d, J=1.6 Hz, 1H), 7.63 (t, J=7.7 Hz, 1H), 7.46-7.31 (m, 5H), 4.51 (s, 2H), 3.94 (s, 4H), 3.79 (s, 3H), 3.38 (m, 4H); LCMS(m/z) 503.3.

Example 565. 3'-((8-chloro-[1,2,4]triazolo[4,3-a]quinazolin-5-yl)(methyl)amino)-5-methoxy-4-((tetrahydro-2H-pyran-2-yl)oxy)-[1,1'-biphenyl]-3-carbonitrile

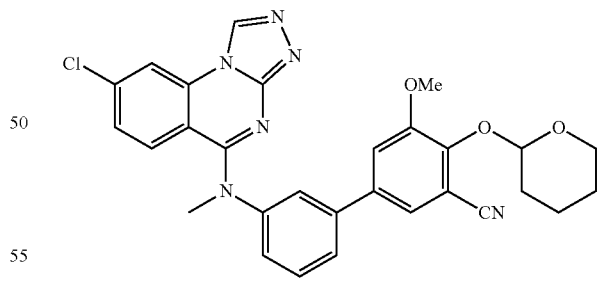

The title compound was synthesized in a similar manner as described for Example 252: $^1$H NMR (400 MHz, Methanol-d$_4$) δ 9.57 (s, 1H), 8.49 (d, J=2.0 Hz, 1H), 7.78 (dt, J=8.0, 1.2 Hz, 1H), 7.71 (t, J=2.0 Hz, 1H), 7.63 (t, J=7.9 Hz, 1H), 7.44-7.25 (m, 2H), 7.22 (d, J=7.4 Hz, 2H), 7.12-7.01 (m, 1H), 4.93 (t, J=7.7 Hz, 2H), 3.93 (s, 3H), 3.86 (s, 3H), 3.35-3.29 (m, 6H); LCMS(m/z) 541.3.

Example 566. 8-chloro-N-methyl-N-(4'-(pentafluoro-16-sulfanyl)-[1,1'-biphenyl]-3-yl)-[1,2,4]triazolo[4,3-a]quinazolin-5-amine

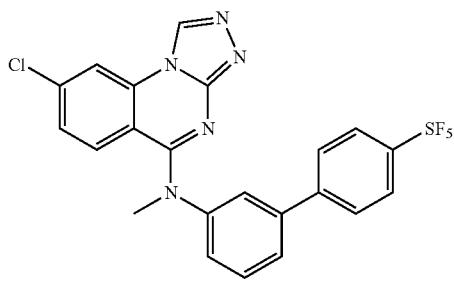

The title compound was synthesized in a similar manner as Example 312, except using using (4-(pentafluoro-$\lambda^6$-sulfanyl)phenyl)boronic acid instead of (4-isopropylphenyl) boronic acid. $^1$H NMR (400 MHz, Acetone-$d_6$) δ 9.52 (s, 1H), 8.45 (d, J=2.3 Hz, 1H), 8.01-7.92 (m, 2H), 7.92-7.81 (m, 3H), 7.75 (d, J=7.4 Hz, 1H), 7.63 (t, J=7.8 Hz, 1H), 7.51 (dd, J=8.5, 3.2 Hz, 2H), 7.38-7.26 (m, 1H), 3.75 (s, 3H); LCMS(m/z) 512.3.

Example 567. N-(3-bromophenyl)-8-chloro-N-methyl-1-(methylthio)-[1,2,4]triazolo[4,3-a]quinazolin-5-amine

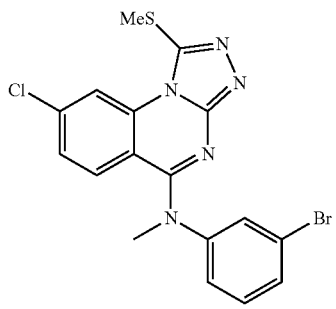

The title compound was prepared as described for Intermediate 366-1: $^1$H NMR (400 MHz, Acetone-$d_6$) δ 8.64 (d, J=2.0 Hz, 1H), 7.59 (td, J=1.8, 0.9 Hz, 1H), 7.56 (d, J=8.9 Hz, 1H), 7.48-7.41 (m, 1H), 7.39 (dd, J=8.9, 2.0 Hz, 1H), 7.37-7.33 (m, 2H), 3.63 (s, 3H), 2.91 (s, 3H); LCMS(m/z) 434.3.

Example 569. 8-chloro-N-(4'-cyclopropyl-[1,1'-biphenyl]-3-yl)-N-methyl-1-(methylthio)-[1,2,4]triazolo[4,3-a]quinazolin-5-amine

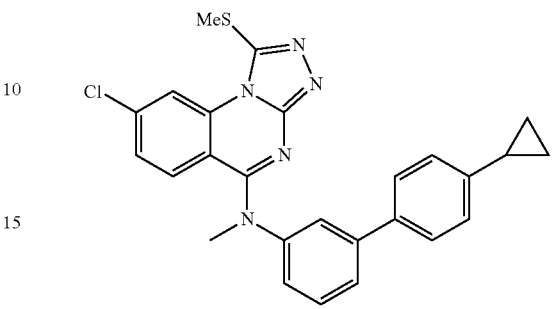

The title compound was synthesized in a manner similar to Example 312, except using (4-cyclopropylphenyl)boronic acid instead of (4-isopropylphenyl)boronic acid and using Intermediate 366-1 instead of Example 308. $^1$H NMR (400 MHz, Acetone-$d_6$) δ 8.62 (d, J=2.0 Hz, 1H), 7.64-7.54 (m, 3H), 7.54-7.46 (m, 3H), 7.34-7.26 (m, 2H), 7.18-7.11 (m, 2H), 3.68 (s, 3H), 2.90 (s, 3H), 2.02-1.90 (m, 1H), 1.04-0.94 (m, 2H), 0.76-0.65 (m, 2H); LCMS(m/z) 472.3.

Example 570. N-(4'-((2-oxa-6-azaspiro[3.3]heptan-6-yl)sulfonyl)-[1,1'-biphenyl]-3-yl)-8-chloro-N-methyl-[1,2,4]triazolo[4,3-a]quinazolin-5-amine

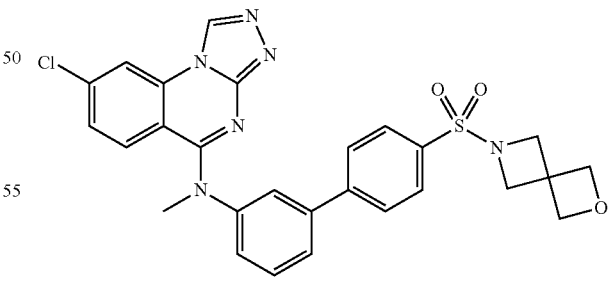

The title compound was synthesized according to the general procedure described for Example 535. $^1$H NMR (400 MHz, DMSO-$d_6$) δ 9.65 (s, 1H), 8.56 (d, J=2.0 Hz, 1H), 7.95 (d, J=8.4 Hz, 2H), 7.82 (d, J=8.4 Hz, 2H), 7.79 (s, 1H), 7.69 (d, J=7.7 Hz, 1H), 7.53 (t, J=7.9 Hz, 1H), 7.39 (d, J=8.9 Hz, 1H), 7.33 (s, 2H), 4.44 (s, 4H), 3.90 (s, 4H), 3.61 (s, 3H); LCMS(m/z) 547.1.

Example 571. 1-(4-(5-(3-((8-chloro-[1,2,4]triazolo[4,3-a]quinazolin-5-yl)(methyl)amino)phenyl)pyridin-2-yl)piperazin-1-yl)ethan-1-one

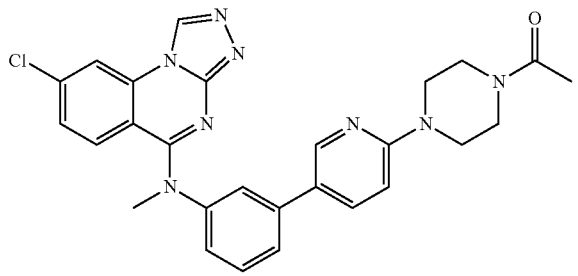 [SMILES: CC(=O)N1CCN(c2ccc(-c3cccc(N(C)c4nc5nncn5c5cc(Cl)ccc45)c3)cn2)CC1]

A solution of 8-chloro-N-methyl-N-(3-(6-(piperazin-1-yl)pyridin-3-yl)phenyl)-[1,2,4]triazolo[4,3-a]quinazolin-5-amine (Example 258.20 mg, 0.04 mmol), DIPEA (52.2 mg, 0.4 mmol), acetic acid (7 mg, 0.12 mmol) and HATU (32 mg, 0.08 mmol) in DMF (5 ml) was stirred at room temperature for 1 hr. Product was extracted with DCM. Organic layer was evaporated and then the residue was purified by reverse phase chromatography ACN/Water 15-95% with 0.1% TFA for 15 min to yield the title compound: $^1$H NMR (400 MHz, Methanol-$d_4$) δ 9.60 (s, 1H), 8.52 (d, J=2.1 Hz, 1H), 8.32-8.19 (m, 2H), 7.85-7.63 (m, 3H), 7.59-7.49 (m, 1H), 7.37 (dt, J=9.1, 1.9 Hz, 2H), 7.29 (d, J=9.1 Hz, 1H), 3.87 (s, 3H), 3.86-3.73 (m, 8H), 2.18 (s, 3H); LCMS(m/z) 513.4.

Example 572. 1-(4-(5-(3-((8-chloro-[1,2,4]triazolo[4,3-a]quinazolin-5-yl)(methyl)amino)phenyl)pyridin-2-yl)piperazin-1-yl)-2-hydroxyethan-1-one

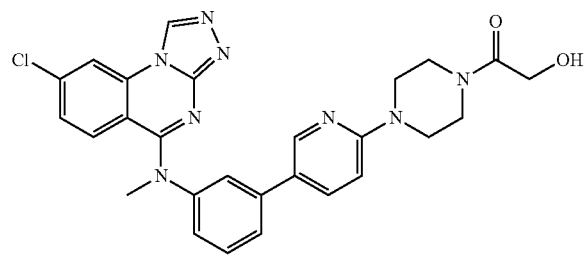 [SMILES: CN(c1cccc(-c2ccc(N3CCN(C(=O)CO)CC3)nc2)c1)c1nc2nncn2c2cc(Cl)ccc12]

The title compound was obtained by a procedure similar to that used to prepare Example 571. $^1$H NMR (400 MHz, Methanol-$d_4$) δ 9.60 (s, 1H), 8.52 (d, J=2.0 Hz, 1H), 8.32-8.15 (m, 2H), 7.86-7.61 (m, 3H), 7.52 (ddd, J=8.0, 2.2, 1.0 Hz, 1H), 7.41-7.21 (m, 3H), 4.31 (s, 3H), 3.99-3.56 (m, 11H); LCMS(m/z) 529.5.

Example 573. 8-chloro-N-methyl-N-(3-(6-(pentafluoro-16-sulfanyl)pyridin-3-yl)phenyl)-[1,2,4]triazolo[4,3-a]quinazolin-5-amine

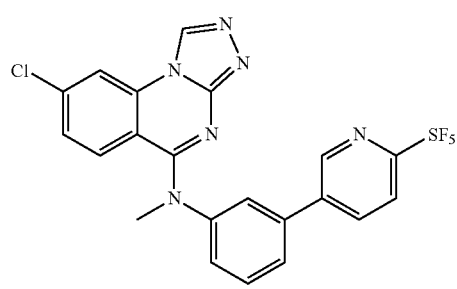

The title compound was synthesized in a manner similar to Example 337, except using 5-bromo-2-(pentafluoro-$\lambda^6$-sulfanyl)pyridine instead of 2-bromo-5-cyclopropylpyrazine. $^1$H NMR (400 MHz, Acetone-$d_6$) δ 9.46 (s, 1H), 8.85 (d, J=2.4 Hz, 1H), 8.43-8.36 (m, 2H), 8.00 (d, J=8.6 Hz, 1H), 7.88 (t, J=2.0 Hz, 1H), 7.83-7.72 (m, 1H), 7.64 (t, J=7.8 Hz, 1H), 7.58-7.50 (m, 2H), 7.27 (dd, J=9.0, 2.1 Hz, 1H), 3.72 (s, 3H); LCMS(m/z) 513.3.

Example 574. 8-chloro-N5-(4'-cyclopropyl-[1,1'-biphenyl]-3-yl)-N5-methyl-[1,2,4]triazolo[4,3-a]quinazoline-1,5-diamine

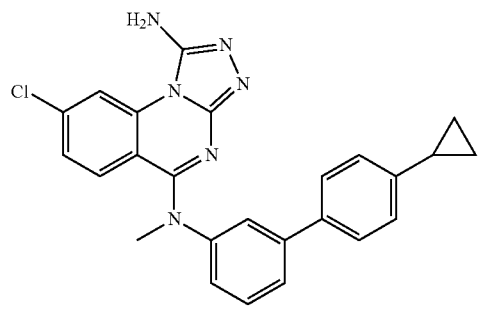 [SMILES: CN(c1cccc(-c2ccc(C3CC3)cc2)c1)c1nc2nnc(N)n2c2cc(Cl)ccc12]

The title compound was prepared according to the general procedure described for Example 367. $^1$H NMR (400 MHz, Methanol-$d_4$) δ 8.60 (d, J=2.0 Hz, 1H), 7.72 (d, J=8.0 Hz, 1H), 7.65 (d, J=2.3 Hz, 1H), 7.59 (t, J=7.9 Hz, 1H), 7.48 (d, J=8.3 Hz, 2H), 7.41-7.31 (m, 3H), 7.15 (d, J=8.2 Hz, 2H), 3.81 (s, 3H), 2.01-1.89 (m, 1H), 1.07-0.98 (m, 2H), 0.76-0.65 (m, 2H); LCMS(m/z) 441.3.

Example 575. 6-(3-((8-chloro-[1,2,4]triazolo[4,3-a]quinazolin-5-yl)(methyl)amino)phenyl)-1-methoxy-4-(methoxymethyl)-2-methylhex-5-yne-2,4-diol

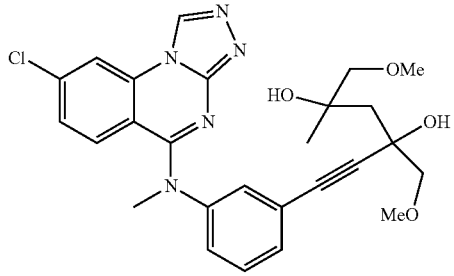 [SMILES: COCC(C)(O)CC(O)(C#Cc1cccc(N(C)c2nc3nncn3c3cc(Cl)ccc23)c1)COC]

The title compound was synthesized in a manner similar to Example 376 using Example 308 instead of Intermediate 364-2 and using 1-methoxy-4-(methoxymethyl)-2-methyl-hex-5-yne-2,4-diol instead of 2-methylbut-3-yn-2-ol. $^1$H NMR (400 MHz, Acetone-$d_6$) δ 9.45 (s, 1H), 8.40 (d, J=2.0 Hz, 1H), 7.62-7.19 (m, 6H), 4.10-3.21 (m, 6H), 3.63 (s, 3H), 3.40 (s, 3H), 3.35 (s, 3H), 1.86 (s, 3H); LCMS(m/z) 510.2.

Example 576. 3'-((8-chloro-[1,2,4]triazolo[4,3-a]quinazolin-5-yl)(methyl)amino)-N-(2-hydroxyethyl)-[1,1'-biphenyl]-4-sulfonamide

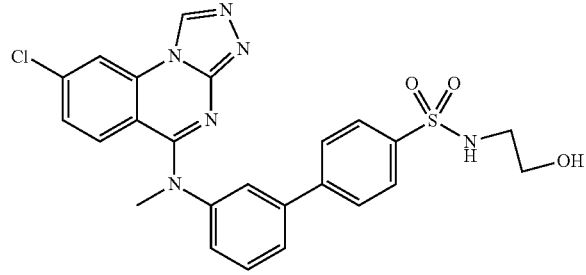 [SMILES: CN(c1cccc(-c2ccc(S(=O)(=O)NCCO)cc2)c1)c1nc2nncn2c2cc(Cl)ccc12]

The title compound was prepared according to the general procedure described for Example 525. $^1$H NMR (400 MHz, DMSO-$d_6$) δ 9.78 (s, 1H), 8.62 (d, J=2.0 Hz, 1H), 7.88 (d, J=8.6 Hz, 2H), 7.85 (s, 3H), 7.76 (d, J=7.9 Hz, 1H), 7.66 (t, J=5.9 Hz, 1H), 7.59 (t, J=7.8 Hz, 1H), 7.44 (d, J=7.9 Hz, 1H), 7.40 (dd, J=9.0, 2.0 Hz, 1H), 7.28 (d, J=9.0 Hz, 1H), 3.68 (s, 3H), 3.37 (t, J=6.3 Hz, 2H), 2.81-2.75 (m, 2H); LCMS(m/z) 509.1.

Example 577. 4-(1-(7-fluoro-1-methyl-[1,2,4]triazolo[4,3-a]quinazolin-5-yl)-1,2,3,4-tetrahydro-1,7-naphthyridin-5-yl)-2-methylbut-3-yn-2-ol

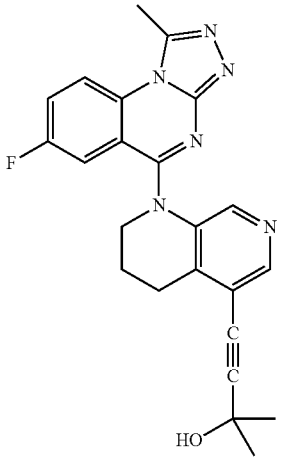 [SMILES: Cc1nnc2nc(N3CCCc4c(C#CC(C)(C)O)cncc43)c3cc(F)ccc3n12]

The title compound was synthesized in a manner similar to Example 421, except using 5-(5-bromo-3,4-dihydro-1,7-naphthyridin-1(2H)-yl)-7-fluoro-1-methyl-[1,2,4]triazolo[4,3-a]quinazoline instead of N-(3-bromo-5-fluorophenyl)-8-chloro-N-methyl-[1,2,4]triazolo[4,3-a]quinazolin-5-amine. $^1$H NMR (400 MHz, DMSO-$d_6$) δ 8.44 (dd, J=9.4, 4.5 Hz, 1H), 8.24 (s, 1H), 8.12 (s, 1H), 7.94 (ddd, J=9.3, 7.9, 2.9 Hz, 1H), 7.78 (dd, J=9.3, 2.9 Hz, 1H), 4.04-3.95 (m, 2H), 3.03 (s, 3H), 2.99 (t, J=6.7 Hz, 2H), 2.18-2.00 (m, 2H), 1.53 (s, 6H); LCMS(m/z) 417.7[M+H]$^+$.

Example 578. 5-(5-((1-(difluoromethyl)cyclopropyl)ethynyl)-3,4-dihydro-1,7-naphthyridin-1(2H)-yl)-7-fluoro-1-methyl-[1,2,4]triazolo[4,3-a]quinazoline

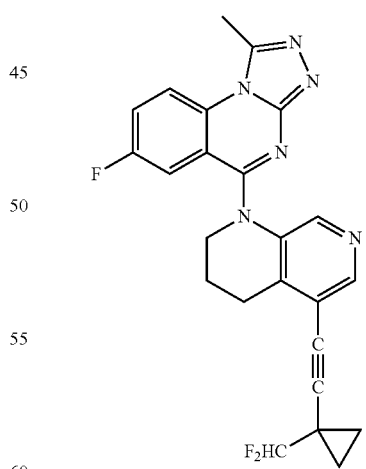

The title compound was synthesized in a manner similar to Example 421, except using 5-(5-bromo-3,4-dihydro-1,7-naphthyridin-1(2H)-yl)-7-fluoro-1-methyl-[1,2,4]triazolo[4,3-a]quinazoline instead of N-(3-bromo-5-fluorophenyl)-8-chloro-N-methyl-[1,2,4]triazolo[4,3-a]quinazolin-5-amine, and using 1-(difluoromethyl)-1-ethynylcyclopropane instead of 2-methylbut-3-yn-2-ol. $^1$H NMR (400 MHz, DMSO-d$_6$) δ 8.44 (dd, J=9.4, 4.5 Hz, 1H), 8.26 (s, 1H), 8.12 (s, 1H), 7.94 (ddd, J=9.3, 7.9, 2.9 Hz, 1H), 7.79 (dd, J=9.3, 2.9 Hz, 1H), 5.83 (t, J=55.4 Hz, 1H), 4.00 (t, J=5.8 Hz, 4H), 3.03 (s, 3H), 2.98 (t, J=6.6 Hz, 2H), 2.17-2.01 (m, 2H), 1.29 (dq, J=7.8, 2.7 Hz, 4H); LCMS(m/z) 469.6[M+H]$^+$.

Example 579. 7-fluoro-1-methyl-5-(5-(4,4,4-trifluoro-3,3-dimethylbut-1-yn-1-yl)-3,4-dihydro-1,7-naphthyridin-1(2H)-yl)-[1,2,4]triazolo[4,3-a]quinazoline

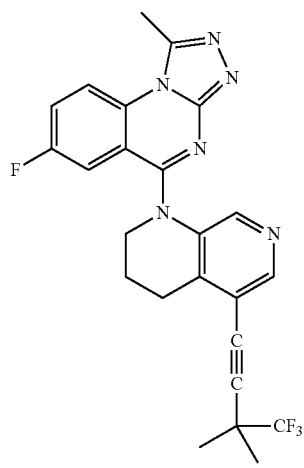 [SMILES: Cc1nnc2nc(N3CCCc4c(C#CC(C)(C)C(F)(F)F)cncc43)c3cc(F)ccc3n12]

The title compound was synthesized in a manner similar to Example 421, except using 5-(5-bromo-3,4-dihydro-1,7-naphthyridin-1(2H)-yl)-7-fluoro-1-methyl-[1,2,4]triazolo[4,3-a]quinazoline instead of N-(3-bromo-5-fluorophenyl)-8-chloro-N-methyl-[1,2,4] triazolo[4,3-a] quinazolin-5-amine, and using 4,4,4-trifluoro-3,3-dimethylbut-1-yne instead of 2-methylbut-3-yn-2-ol. $^1$H NMR (400 MHz, DMSO-d$_6$) δ 8.45 (dd, J=9.4, 4.5 Hz, 1H), 8.29 (s, 1H), 8.16 (s, 1H), 7.96 (ddd, J=9.3, 7.9, 2.9 Hz, 1H), 7.82 (dd, J=9.3, 2.9 Hz, 1H), 4.05-3.97 (m, 2H), 3.04 (s, 3H), 2.98 (t, J=6.7 Hz, 2H), 2.11 (p, J=6.7 Hz, 2H), 1.57 (s, 6H). LCMS(m/z) 469.6[M+H]$^+$.

Example 580. 7-fluoro-1-methyl-5-(5-((1-(trifluoromethyl)cyclopropyl)ethynyl)-3,4-dihydro-1,7-naphthyridin-1(2H)-yl)-[1,2,4]triazolo[4,3-a]quinazoline

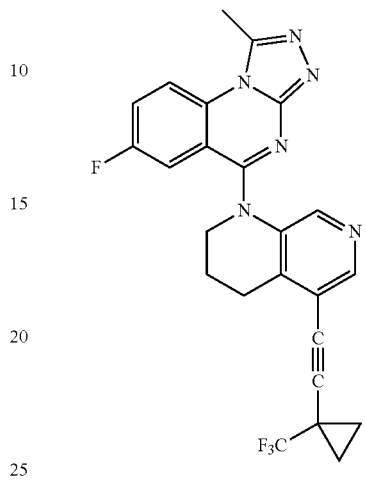

The title compound was synthesized in a manner similar to Example 421, except using 5-(5-bromo-3,4-dihydro-1,7-naphthyridin-1(2H)-yl)-7-fluoro-1-methyl-[1,2,4]triazolo[4,3-a]quinazoline instead of N-(3-bromo-5-fluorophenyl)-8-chloro-N-methyl-[1,2,4] triazolo[4,3-a]quinazolin-5-amine, and using 1-ethynyl-1-(trifluoromethyl)cyclopropane instead of 2-methylbut-3-yn-2-ol. $^1$H NMR (400 MHz, DMSO-d$_6$) δ 8.45 (dd, J=9.4, 4.5 Hz, 1H), 8.30 (s, 1H), 8.16 (s, 1H), 7.96 (ddd, J=9.4, 7.9, 2.9 Hz, 1H), 7.81 (dd, J=9.3, 2.9 Hz, 1H), 4.02 (t, J=5.7 Hz, 2H), 3.04 (s, 3H), 2.98 (t, J=6.7 Hz, 2H), 2.10 (p, J=6.4 Hz, 2H), 1.59-1.51 (m, 2H), 1.51-1.41 (m, 2H). LCMS(m/z) 467.7[M+H]$^+$.

Example 581. 4-(1-(7-fluoro-[1,2,4]triazolo[4,3-a]quinazolin-5-yl)-1,2,3,4-tetrahydro-1,7-naphthyridin-5-yl)-2-methylbut-3-yn-2-ol

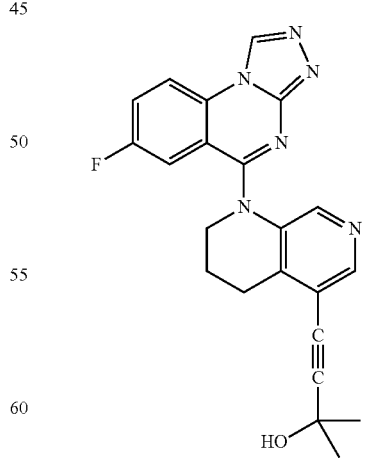

The title compound was synthesized in a manner similar to Example 421, except using 5-(5-bromo-3,4-dihydro-1,7-naphthyridin-1(2H)-yl)-7-fluoro-[1,2,4]triazolo[4,3-a]quinazoline instead of N-(3-bromo-5-fluorophenyl)-8-chloro- N-methyl-[1,2,4] triazolo[4,3-a] quinazolin-5-amine. $^1$H NMR (400 MHz, DMSO-d$_6$) δ 9.91 (s, 1H), 8.57 (dd, J=9.2, 4.7 Hz, 1H), 8.28 (s, 1H), 8.22 (s, 1H), 8.04 (ddd, J=9.2, 8.2, 2.8 Hz, 1H), 7.74 (dd, J=9.4, 2.8 Hz, 1H), 4.17-3.88 (m, 2H), 3.00 (t, J=6.6 Hz, 2H), 2.09 (dd, J=11.3, 5.4 Hz, 2H), 1.54 (s, 6H). LCMS(m/z) 403.6[M+H]$^+$.

Example 582. 5-(5-((1-(difluoromethyl)cyclopropyl)ethynyl)-3,4-dihydro-1,7-naphthyridin-1(2H)-yl)-7-fluoro-[1,2,4]triazolo[4,3-a]quinazoline

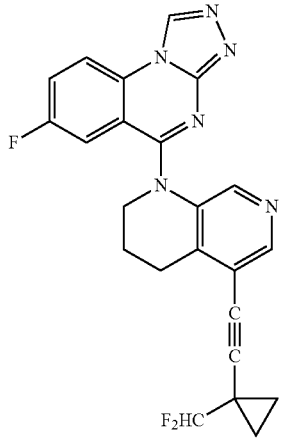 [SMILES: Fc1ccc2c(c1)c(N1CCCc3c(C#CC4(C(F)F)CC4)cncc31)nc1nncn12]

The title compound was synthesized in a manner similar to Example 421, except using 5-(5-bromo-3,4-dihydro-1,7-naphthyridin-1(2H)-yl)-7-fluoro-[1,2,4]triazolo[4,3-a]quinazoline instead of N-(3-bromo-5-fluorophenyl)-8-chloro-N-methyl-[1,2,4] triazolo[4,3-a] quinazolin-5-amine, and using 1-(difluoromethyl)-1-ethynylcyclopropane instead of 2-methylbut-3-yn-2-ol $^1$H NMR (400 MHz, DMSO-d$_6$) δ 9.87 (s, 1H), 8.55 (dd, J=9.2, 4.7 Hz, 1H), 8.26 (s, 1H), 8.17 (s, 1H), 8.01 (td, J=8.7, 2.8 Hz, 1H), 7.72 (dd, J=9.4, 2.8 Hz, 1H), 5.83 (t, J=55.5 Hz, 1H), 4.00 (dd, J=6.7, 4.8 Hz, 2H), 2.97 (t, J=6.6 Hz, 2H), 2.18-2.01 (m, 2H), 1.40-1.19 (m, 4H); LCMS(m/z) 435.7[M+H]$^+$.

Example 583. 7-fluoro-5-(5-(4,4,4-trifluoro-3,3-dimethylbut-1-yn-1-yl)-3,4-dihydro-1,7-naphthyridin-1(2H)-yl)-[1,2,4]triazolo[4,3-a]quinazoline

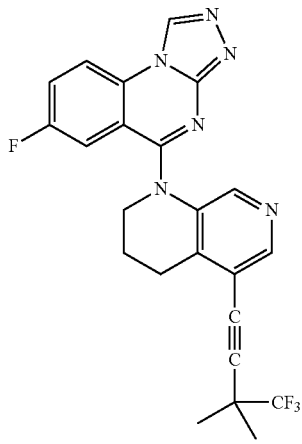 [SMILES: CC(C)(C#Cc1cncc2c1CCCN2c1nc2nncn2c2ccc(F)cc12)C(F)(F)F]

The title compound was synthesized in a manner similar to Example 584, except using 5-(5-bromo-3,4-dihydro-1,7-naphthyridin-1(2H)-yl)-7-fluoro-[1,2,4]triazolo[4,3-a]quinazoline instead of N-(3-bromo-5-fluorophenyl)-8-chloro-N-methyl-[1,2,4] triazolo[4,3-a]quinazolin-5-amine, and using 4,4,4-trifluoro-3,3-dimethylbut-1-yne instead of 2-methylbut-3-yn-2-ol. $^1$H NMR (400 MHz, DMSO-d$_6$) δ 9.90 (s, 1H), 8.57 (dd, J=9.2, 4.6 Hz, 1H), 8.29 (s, 1H), 8.22 (s, 1H), 8.03 (td, J=8.7, 2.8 Hz, 1H), 7.76 (dd, J=9.4, 2.8 Hz, 1H), 4.02 (dd, J=6.8, 4.6 Hz, 2H), 2.98 (t, J=6.7 Hz, 2H), 2.23-2.01 (m, 2H), 1.57 (s, 6H); LCMS(m/z) 455.6[M+H]$^+$.

Example 584. 7-fluoro-5-(5-((1-(trifluoromethyl)cyclopropyl)ethynyl)-3,4-dihydro-1,7-naphthyridin-1(2H)-yl)-[1,2,4]triazolo[4,3-a]quinazoline

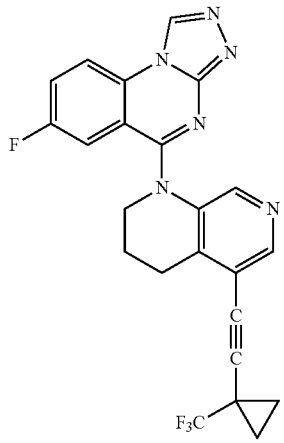 [SMILES: Fc1ccc2c(c1)c(N1CCCc3c(C#CC4(C(F)(F)F)CC4)cncc31)nc1nncn12]

The title compound was synthesized in a manner similar to Example 585, except using 5-(5-bromo-3,4-dihydro-1,7-naphthyridin-1(2H)-yl)-7-fluoro-[1,2,4]triazolo[4,3-a]quinazoline instead of N-(3-bromo-5-fluorophenyl)-8-chloro-N-methyl-[1,2,4] triazolo[4,3-a] quinazolin-5-amine, and using 1-ethynyl-1-(trifluoromethyl)cyclopropane instead of 2-methylbut-3-yn-2-ol. $^1$H NMR (400 MHz, DMSO-d$_6$) δ 9.89 (s, 1H), 8.56 (dd, J=9.2, 4.6 Hz, 1H), 8.29 (s, 1H), 8.21 (s, 1H), 8.02 (ddd, J=9.1, 8.2, 2.8 Hz, 1H), 7.74 (dd, J=9.4, 2.8 Hz, 1H), 4.09-3.89 (m, 2H), 2.98 (t, J=6.6 Hz, 2H), 2.16-2.01 (m, 2H), 1.63-1.36 (m, 4H); LCMS(m/z) 453.6 [M+H]$^+$.

Example 585. 5-(5-((1-(difluoromethyl)cyclopropyl)ethynyl)-3,4-dihydroquinolin-1(2H)-yl)-6-fluoro-1-methyl-[1,2,4]triazolo[4,3-a]quinazoline

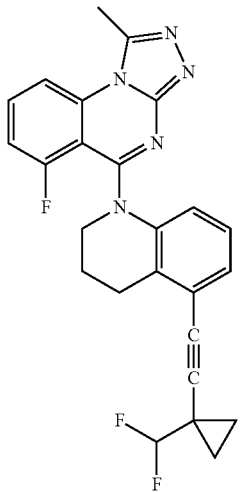 [SMILES: Cc1nnc2nc(N3CCCc4c(C#CC5(C(F)F)CC5)cccc43)c3c(F)cccc3n12]

The title compound was synthesized in a manner similar to Example 421, except using 5-(5-bromo-3,4-dihydroquinolin-1(2H)-yl)-6-fluoro-1-methyl-[1,2,4]triazolo[4,3-a]quinazoline instead of N-(3-bromo-5-fluorophenyl)-8-chloro-N-methyl-[1,2,4] triazolo[4,3-a] quinazolin-5-amine, and using 1-(difluoromethyl)-1-ethynylcyclopropane instead of 2-methylbut-3-yn-2-ol. $^1$H NMR (400 MHz, DMSO-$d_6$) δ 8.18 (d, J=8.6 Hz, 1H), 8.00 (td, J=8.4, 5.4 Hz, 1H), 7.37 (dd, J=11.8, 8.2 Hz, 1H), 7.14 (d, J=7.5 Hz, 1H), 6.93 (t, J=7.9 Hz, 1H), 6.83 (d, J=8.2 Hz, 1H), 5.81 (t, J=55.6 Hz, 1H), 4.26-3.96 (m, 2H), 3.0-2.7 (m, 5H), 2.29-1.80 (m, 2H), 1.38-1.14 (m, 4H); LCMS(m/z) 448.3[M+H]$^+$.

Example 586. 5-(5-((1-(difluoromethyl)cyclopropyl)ethynyl)-3,4-dihydroquinolin-1(2H)-yl)-7-fluoro-1-methyl-[1,2,4]triazolo[4,3-a]quinazoline

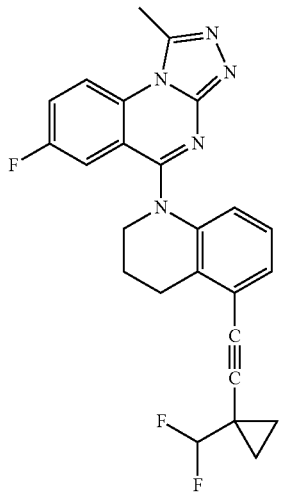 [SMILES: Cc1nnc2nc(N3CCCc4c(C#CC5(C(F)F)CC5)cccc43)c3cc(F)ccc3n12]

The title compound was synthesized in a manner similar to Example 421, except using 5-(5-bromo-3,4-dihydroquinolin-1(2H)-yl)-7-fluoro-1-methyl-[1,2,4]triazolo[4,3-a]quinazoline instead of N-(3-bromo-5-fluorophenyl)-8-chloro-N-methyl-[1,2,4] triazolo[4,3-a] quinazolin-5-amine, and using 1-(difluoromethyl)-1-ethynylcyclopropane instead of 2-methylbut-3-yn-2-ol. $^1$H NMR (400 MHz, DMSO-$d_6$) δ 8.37 (dd, J=9.4, 4.6 Hz, 1H), 7.86 (td, J=8.6, 2.9 Hz, 1H), 7.42 (dd, J=9.6, 2.9 Hz, 1H), 7.16 (d, J=7.5 Hz, 1H), 6.98 (t, J=7.9 Hz, 1H), 6.79 (d, J=8.2 Hz, 1H), 5.81 (t, J=55.6 Hz, 1H), 3.96 (t, J=6.2 Hz, 2H), 2.99 (d, J=5.7 Hz, 5H), 2.21-2.00 (m, 2H), 1.26 (dt, J=10.1, 2.8 Hz, 4H). LCMS(m/z) 448.3[M+H]$^+$.

Example 587. N-(3-(5-cyclopropylpyrazin-2-yl)-5-fluorophenyl)-N-(2,2-difluoroethyl)-6-fluoro-1-methyl-[1,2,4]triazolo[4,3-a]quinazolin-5-amine

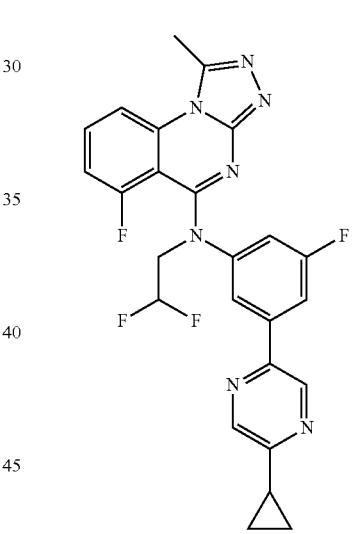

The title compound was synthesized in a manner similar to Example 591, except using N-(3-bromo-5-fluorophenyl)-N-(2,2-difluoroethyl)-6-fluoro-1-methyl-[1,2,4]triazolo[4,3-a]quinazolin-5-amine instead of N-(3-bromo-5-fluorophenyl)-N-methyl-8-(trifluoromethyl)-[1,2,4]triazolo[4,3-a]quinazolin-5-amine. $^1$H NMR (400 MHz, DMSO-$d_6$) δ 8.88 (d, J=1.5 Hz, 1H), 8.65 (d, J=1.5 Hz, 1H), 8.18 (d, J=8.6 Hz, 1H), 7.95 (td, J=8.4, 5.4 Hz, 1H), 7.76-7.48 (m, 2H), 7.35-6.91 (m, 2H), 6.80-6.36 (m, 1H), 4.89-4.62 (m, 2H), 3.03 (s, 3H), 2.23 (tt, J=8.1, 4.7 Hz, 1H), 1.18-1.00 (m, 2H), 0.96 (dt, J=4.6, 3.0 Hz, 2H); LCMS(m/z) 491.1[M+H]$^+$.

Example 588. 7-fluoro-5-(5-((1-methylcyclopropyl)ethynyl)-3,4-dihydro-1,8-naphthyridin-1(2H)-yl)-[1,2,4]triazolo[4,3-a]quinazoline

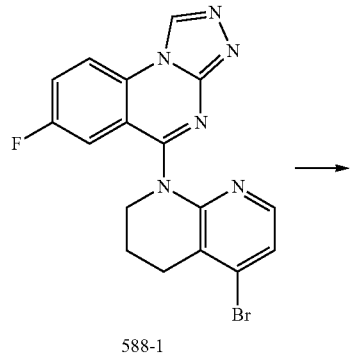

588-1

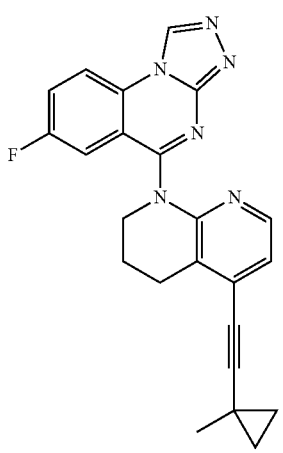

Compound 588-1 (5-(5-bromo-3,4-dihydro-1,8-naphthyridin-1(2H)-yl)-7-fluoro-[1,2,4]triazolo[4,3-a]quinazoline) was synthesized in a manner similar to Example 498, except using 2,4-dichloro-6-fluoroquinazoline instead of 7-bromo-2,4-dichloro-6-fluoroquinazoline, and using 5-bromo-1,2,3,4-tetrahydro-1,8-naphthyridine instead of 2,3,4,5-tetrahydro-1H-benzo[b]azepine.

The title compound was synthesized in a manner similar to Example 421, except using 5-(5-bromo-3,4-dihydro-1,8-naphthyridin-1(2H)-yl)-7-fluoro-[1,2,4]triazolo[4,3-a]quinazoline instead of N-(3-bromo-5-fluorophenyl)-8-chloro-N-methyl-[1,2,4] triazolo[4,3-a] quinazolin-5-amine, and using 1-ethynyl-1-methylcyclopropane instead of 2-methyl-but-3-yn-2-ol. ¹H NMR (400 MHz, DMSO-d₆) δ 9.85 (s, 1H), 8.49 (dd, J=9.2, 4.6 Hz, 1H), 7.92 (ddd, J=9.2, 8.3, 2.8 Hz, 1H), 7.69 (d, J=5.1 Hz, 1H), 7.41 (dd, J=9.5, 2.8 Hz, 1H), 6.90 (d, J=5.1 Hz, 1H), 3.97 (dd, J=6.7, 4.6 Hz, 2H), 2.95 (d, J=6.7 Hz, 2H), 2.24-2.11 (m, 2H), 1.37 (s, 3H), 1.04 (q, J=4.0 Hz, 2H), 0.89-0.78 (m, 2H); LCMS(m/z) 399.1 [M+H]⁺.

Example 589. N-(3-fluoro-5-((1-(trifluoromethyl)cyclopropyl)ethynyl)phenyl)-N-methyl-8-(trifluoromethyl)-[1,2,4]triazolo[4,3-a]quinazolin-5-amine

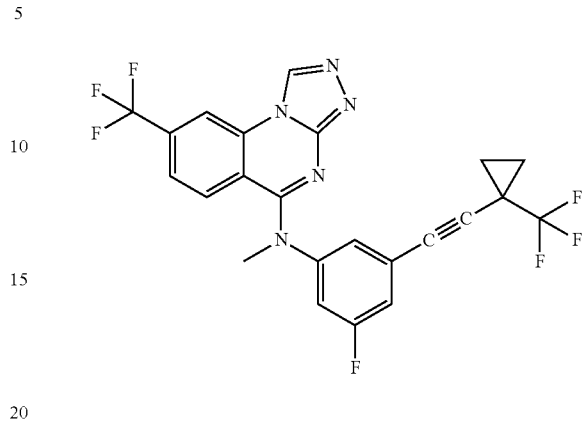

The title compound was synthesized in a manner similar to Example 421, except using N-(3-bromo-5-fluorophenyl)-N-methyl-8-(trifluoromethyl)-[1,2,4]triazolo[4,3-a]quinazolin-5-amine instead of N-(3-bromo-5-fluorophenyl)-8-chloro-N-methyl-[1,2,4] triazolo[4,3-a]quinazolin-5-amine, and using 1-ethynyl-1-(trifluoromethyl)cyclopropane instead of 2-methylbut-3-yn-2-ol. ¹H NMR (400 MHz, DMSO-d₆) δ 9.92 (s, 1H), 8.98-8.80 (m, 1H), 7.75 (dd, J=8.8, 1.7 Hz, 1H), 7.56 (d, J=8.7 Hz, 1H), 7.49-7.32 (m, 2H), 7.32-7.18 (m, 1H), 3.60 (s, 3H), 1.45 (dt, J=6.8, 3.8 Hz, 2H), 1.42-1.28 (m, 2H). LCMS(m/z) 494.1[M+H]⁺.

Example 590. N-(3-(5-cyclopropylpyrazin-2-yl)-5-fluorophenyl)-N-methyl-7-(trifluoromethyl)-[1,2,4]triazolo[4,3-a]quinazolin-5-amine

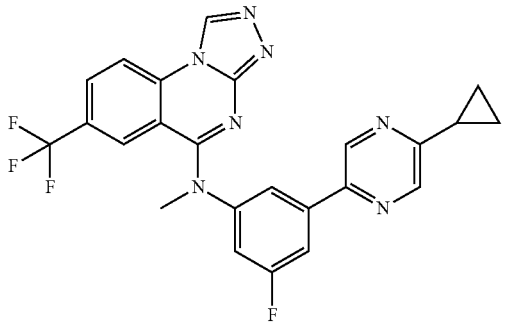 [SMILES: CN(c1cc(F)cc(-c2cnc(C3CC3)cn2)c1)c1nc2nncn2c2ccc(C(F)(F)F)cc12]

The title compound was synthesized in a manner similar to Example 591, except using 2,4-dichloro-6-(trifluoromethyl)quinazoline instead of 2,4-dichloro-7-(trifluoromethyl)quinazoline. ¹H NMR (400 MHz, DMSO-d₆) δ 9.88 (s, 1H), 8.99 (d, J=1.5 Hz, 1H), 8.67 (d, J=1.5 Hz, 1H), 8.59 (d, J=8.7 Hz, 1H), 8.27 (dd, J=8.8, 1.9 Hz, 1H), 7.98 (t, J=1.7 Hz, 1H), 7.91 (ddd, J=9.8, 2.4, 1.4 Hz, 1H), 7.64-7.47 (m, 2H), 3.71 (s, 3H), 2.25 (td, J=8.1, 4.1 Hz, 1H), 1.14-1.03 (m, 2H), 1.03-0.90 (m, 2H); LCMS(m/z) 480.1[M+H]⁺.

Example 591. N-(3-(5-cyclopropylpyrazin-2-yl)-5-fluorophenyl)-N-methyl-8-(trifluoromethyl)-[1,2,4]triazolo[4,3-a]quinazolin-5-amine

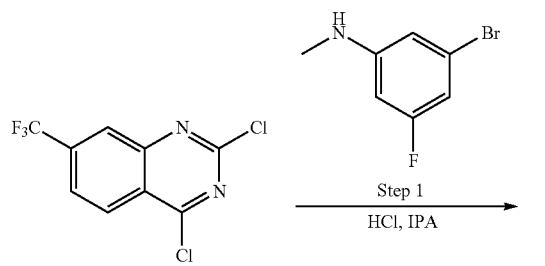

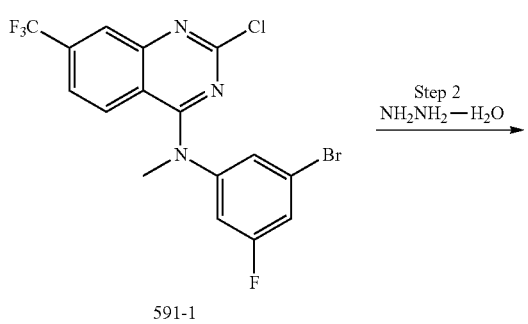

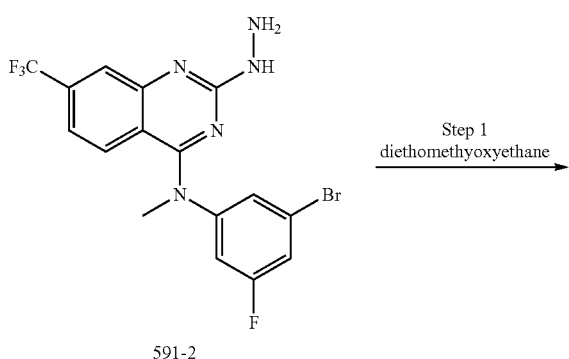

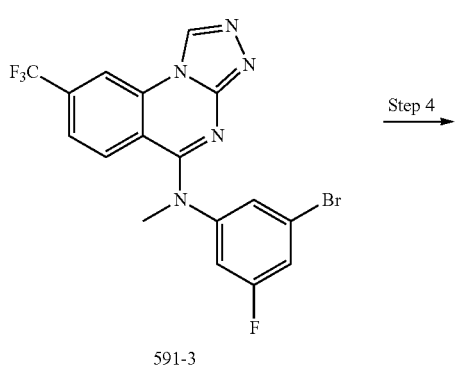

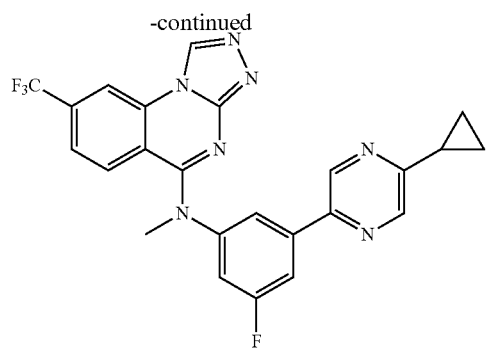

(Step 1) Synthesis of N-(3-bromo-5-fluorophenyl)-2-chloro-N-methyl-7 (trifluoromethyl)quinazolin-4-amine (Compound 591-1)

To a mixture of 3-bromo-5-fluoro-N-methyl-aniline (0 mL, 4.90 mmol) and 2,4-dichloro-7-(trifluoromethyl)quinazoline (1309 mg, 4.90 mmol) in IPA (7.00 mL) was added hydrochloric acid (37.0%, 483 mg, 4.90 mmol). The mixture was stirred at rt for 16 hr, whereupon the solid was filtered, and washed with 2 mL cold IPA. The filtrate was used in the next reaction without further purification. LCMS(m/z) 434.28 [M+H]$^+$.

(Step 2) Synthesis of N-(3-bromo-5-fluorophenyl)-2-hydrazinyl-N-methyl-7-(trifluoromethyl)quinazolin-4-amine (Compound 591-2)

N-(3-bromo-5-fluorophenyl)-2-hydrazinyl-N-methyl-7-(trifluoromethyl)quinazolin-4-amine was synthesized in a manner similar to Compound 308-3, except using N-(3-bromo-5-fluorophenyl)-2-chloro-N-methyl-7 (trifluoromethyl)quinazolin-4-amine instead of N-(3-bromophenyl)-2,7-dichloro-N-methylquinazolin-4-amine (Compound 308-2). LCMS(m/z) 430.32.1[M+H]$^+$.

(Step 3) Synthesis of N-(3-bromo-5-fluorophenyl)-N-methyl-8-(trifluoromethyl)-[1,2,4]triazolo[4,3-a]quinazolin-5-amine (Compound 591-3)

Compound 591-3 was synthesized in a manner similar to Compound 308-3, except using N-(3-bromo-5-fluorophenyl)-2-hydrazinyl-N-methyl-7-(trifluoromethyl)quinazolin-4-amine instead of N-(3-bromophenyl)-7-chloro-2-hydrazinyl-N-methylquinazolin-4-amine. LCMS(m/z) 440.31[M+H]$^+$.

(Step 4) Synthesis of N-(3-(5-cyclopropylpyrazin-2-yl)-5-fluorophenyl)-N-methyl-8-(trifluoromethyl)-[1,2,4]triazolo[4,3-a]quinazolin-5-amine (Compound 591-4)

Compound 591-4 was synthesized in a manner similar to 8-chloro-N-(3-(5-cyclopropylpyrazin-2-yl)phenyl)-7-fluoro-N-(trifluoromethyl)-[1,2,4]triazolo[4,3-a]quinazolin-5-amine (Example 595), except using N-(3-bromo-5-fluorophenyl)-N-methyl-8-(trifluoromethyl)-[1,2,4]triazolo[4,3-a]quinazolin-5-amine instead of 8-chloro-7-fluoro-N-(3-iodophenyl)-N-(trifluoromethyl)-[1,2,4]triazolo[4,3-a]quinazolin-5-amine. LCMS(m/z) 480.1[M+H]$^+$.

Example 592. 8-chloro-N-(3-fluoro-5-((1-isopropyl-cyclopropyl)ethynyl)phenyl)-N-methyl-[1,2,4]triazolo[4,3-a]quinazolin-5-amine

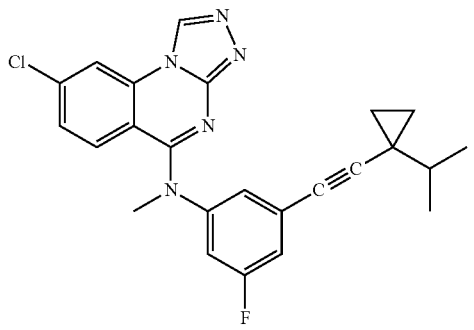 [SMILES: CC(C)C1(C#Cc2cc(F)cc(N(C)c3nc4nncn4c4cc(Cl)ccc34)c2)CC1]

The title compound was synthesized according to the procedures described for Example 421.
$^1$H NMR (400 MHz, DMSO-$d_6$) δ 9.84 (s, 1H), 8.50 (dd, J=9.2, 4.8 Hz, 1H), 8.06-7.83 (m, 1H), 7.44 (dt, J=10.0, 2.2 Hz, 1H), 7.35 (t, J=1.6 Hz, 1H), 7.30 (dt, J=8.8, 1.9 Hz, 1H), 6.93 (dd, J=10.2, 2.7 Hz, 1H), 5.75 (t, J=55.5 Hz, 1H), 4.18 (q, J=6.9 Hz, 2H), 1.35-1.03 (m, 8H); LCMS(m/z) 434.1.

Example 593. N-(3-((1-(difluoromethyl)cyclopropyl)ethynyl)-5-fluorophenyl)-N-ethyl-7-fluoro-[1,2,4]triazolo[4,3-a]quinazolin-5-amine

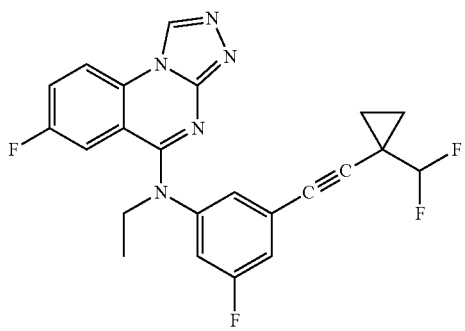

The title compound was synthesized according to the procedures described for Example 421.
$^1$H NMR (400 MHz, DMSO-$d_6$) δ 9.81 (s, 1H), 8.48 (dd, J=9.2, 4.8 Hz, 1H), 7.91 (ddd, J=9.2, 8.1, 2.8 Hz, 1H), 7.70-7.50 (m, 1H), 7.42 (dt, J=10.0, 2.3 Hz, 1H), 7.33 (d, J=1.7 Hz, 1H), 7.28 (dd, J=9.0, 2.0 Hz, 1H), 6.93 (dd, J=10.2, 2.7 Hz, 1H), 5.75 (t, J=55.5 Hz, 1H), 4.17 (d, J=7.0 Hz, 2H), 1.41-0.88 (m, 7H); LCMS(m/z) 440.1.

Example 594. 8-chloro-N-(3-(5-cyclopropylpyrazin-2-yl)-5-fluorophenyl)-N-(trifluoromethyl)-[1,2,4]triazolo[4,3-a]quinazolin-5-amine

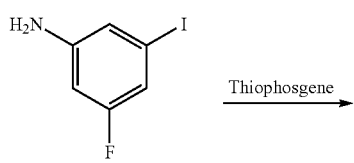

Thiophosgene

-continued

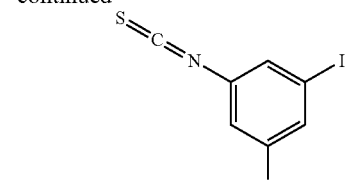

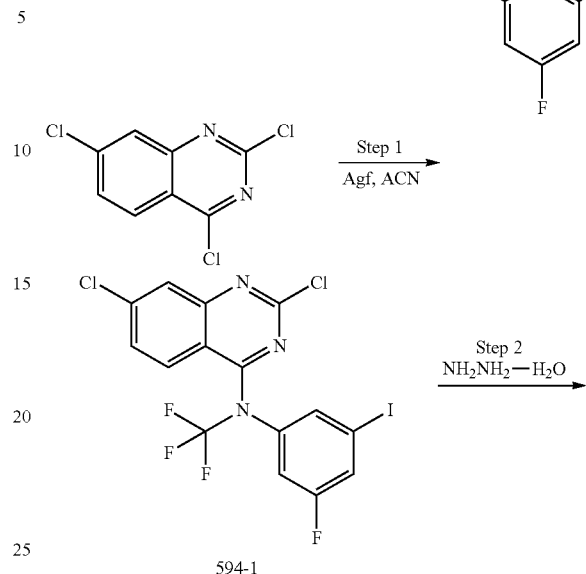

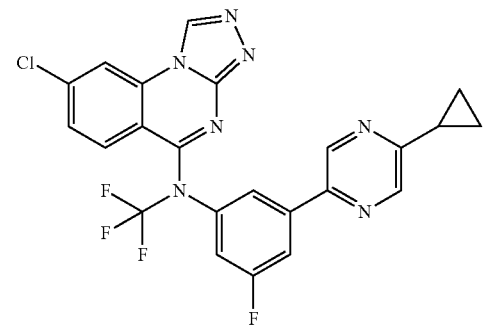

Synthesis of 1-fluoro-3-iodo-5-isothiocyanatobenzene

A solution of 3-fluoro-5-iodo-aniline (4.0 g, 16.9 mmol) and sodium carbonate (2.68 g, 25.3 mmol) in acetone (100 mL) was stirred in an ice bath under an atmosphere of nitrogen. Thiophosgene (1.94 mL, 25.3 mmol) was added drop wise over 30 minutes. The reaction was stirred for another 30 minutes in the ice bath before being removed and allowed to warm to RT. The reaction was stirred at RT for 1.5 h before the reaction solution was concentrated under reduced pressure. The residue was azeotroped with toluene to removed residual thiophosgene and to give the desired product.

Example 594 was synthesized in a manner similar to Example 595, except using 1-fluoro-3-iodo-5-isothiocyanatobenzene instead of 1-iodo-3-isothiocyanato-benzene, and using 2,4,7-trichloroquinazoline instead 2,4,7-trichloro-6-fluoro-quinazoline. $^1$H NMR (400 MHz, DMSO-$d_6$) δ 9.94 (s, 1H), 9.09 (d, J=1.4 Hz, 1H), 8.79-8.71 (m, 1H), 8.69 (d, J=1.4 Hz, 1H), 8.18-7.94 (m, 3H), 7.76-7.54 (m, 2H), 2.32-2.18 (m, 1H), 1.11-1.04 (m, 2H), 1.02-0.92 (m, 2H); LCMS(m/z) 500.1[M+H]$^+$.

Example 595. 8-chloro-N-(3-(5-cyclopropylpyrazin-2-yl)phenyl)-7-fluoro-N-(trifluoromethyl)-[1,2,4]triazolo[4,3-a]quinazolin-5-amine

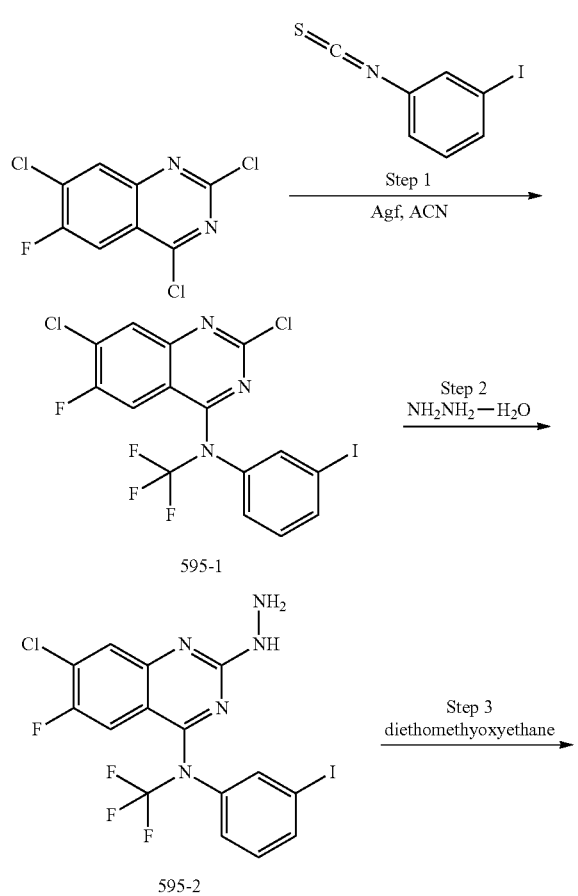

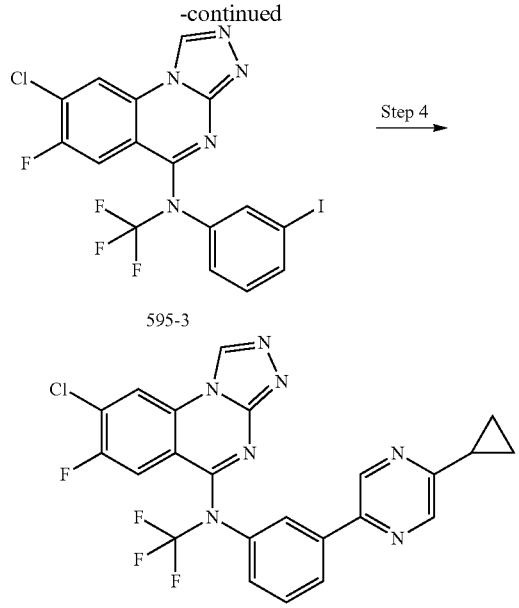

(Step 1) Synthesis of 2,7-dichloro-6-fluoro-N-(3-iodophenyl)-N-(trifluoromethyl)quinazolin-4-amine (Compound 595-1)

A mixture of 2,4,7-trichloro-6-fluoro-quinazoline (393 mg, 1.56 mmol), 1-iodo-3-isothiocyanato-benzene (400 mg, 1.53 mmol) and silver(I) fluoride (972 mg, 7.66 mmol) in MeCN (12.0 mL) was stirred vigorously at 70° C. for 30 min. Poured into 100 mL DCM, filtered through celite, and was concentrated under reduced pressure. The residue was purified by flash column chromatography on silica gel (0% to 75% dichloromethane in Hexanes) to give Compound 595-1. LCMS(m/z) 502.17 [M+H]$^+$.

(Step 2) Synthesis of 7-chloro-6-fluoro-2-hydrazinyl-N-(3-iodophenyl)-N-(trifluoromethyl)quinazolin-4-amine (Compound 595-2)

To a mixture of 2,7-dichloro-6-fluoro-N-(3-iodophenyl)-N-(trifluoromethyl)quinazolin-4-amine (388 mg, 0.773 mmol) in EtOH (2.61 mL) and THF (1.74 mL) was added hydrazine (50.0%, 0.241 mL, 3.86 mmol). The resulting mixture was stirred vigorously at r.t. for 30 min. Water (5 mL), THF (40 mL), and EtOAc (80 mL) were added in succession. The mixture was washed with 4:1 water:brine (2×75 mL), dried over magnesium sulfate, filtered, concentrated under reduced pressure. The residue was azeotroped from THF:toluene, and used in the next step without further purification. LCMS(m/z) 498.15 [M+H]$^+$.

(Step 3) Synthesis of 8-chloro-7-fluoro-N-(3-iodophenyl)-N-(trifluoromethyl)-[1,2,4]triazolo[4,3-a]quinazolin-5-amine (Compound 595-3)

A mixture of N-(3-bromophenyl)-7-chloro-6-fluoro-2-hydrazino-N-(trifluoromethyl)quinazolin-4-amine (385 mg, 0.854 mmol) in diethoxymethoxyethane (6.17 mL, 37.1 mmol), stirred vigorously at 160° C. for 60 min, cooled to rt and concentrated under reduced pressure. The residue was (Step 4) Synthesis of 8-chloro-N-(3-(5-cyclopropylpyrazin-2-yl)phenyl)-7-fluoro-N-(trifluoromethyl)-[1,2,4]triazolo[4,3-a]quinazolin-5-amine To a solution of 8-chloro-7-fluoro-N-(3-iodophenyl)-N-(trifluoromethyl)-[1,2,4]triazolo[4,3-a]quinazolin-5-amine (30.0 mg, 0.0591 mmol) was added tributyl-(5-cyclopropylpyrazin-2-yl)stannane (27.3 mg, 0.0668 mmol) and tetrakis(triphenylphosphine)palladium(0) (6.83 mg, 0.00591 mmol). The reaction mixture was heated to 100° C. for 12h. The reaction was cooled to room temperature and was diluted with ethyl acetate (5 mL) and water (5 mL) sequentially. The organic layer was separated and concentrated under reduced pressure. The residue was purified by reverse-phase preparative HPLC (0.1% trifluoroacetic acid in acetonitrile/water) to give the title compound. $^1$H NMR (400 MHz, DMSO-$d_6$) δ 9.90 (s, 1H), 9.06 (d, J=1.4 Hz, 1H), 8.92 (d, J=6.3 Hz, 1H), 8.67 (d, J=1.4 Hz, 1H), 8.27 (d, J=1.9 Hz, 1H), 8.15 (dt, J=7.9, 1.3 Hz, 1H), 7.98 (d, J=9.5 Hz, 1H), 7.79 (dd, J=7.9, 2.1 Hz, 1H), 7.64 (t, J=7.9 Hz, 1H), 2.24 (tt, J=8.1, 4.7 Hz, 1H), 1.11-1.04 (m, 2H), 1.04-0.90 (m, 2H). LCMS(m/z) 500.10 [M+H]$^+$.

Example 596. 3-[3-[(8-chloro-[1,2,4]triazolo[4,3-a]quinazolin-5-yl)-methyl-amino]phenyl]-1,1-dicyclopropyl-prop-2-yn-1-ol

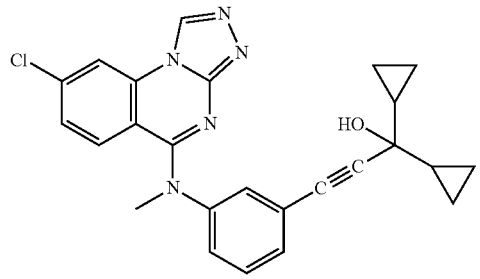 [SMILES: CN(c1cccc(C#CC(O)(C2CC2)C2CC2)c1)c1nc2nncn2c2cc(Cl)ccc12]

1,1-Dicyclopropylprop-2-yn-1-ol (52% purity by wt, 20 μL, 61 μmol) was added to a vigorously stirred mixture of Example 308 (7.0 mg, 18 μmol), [1,1'-bis(diphenylphosphino)ferrocene]dichloropalladium(II) (4.6 mg, 6.3 μmol), triethylamine (63 μL, 450 μmol), and zinc bromide (20.3 mg, 90.1 μmol) in 1-methylpyrrolidin-2-one (0.5 mL). The reaction mixture was sealed and heated to 110° C. After 20 min, the reaction mixture was cooled to room temperature. The mixture was purified by reverse-phase preparative HPLC (0.1% trifluoroacetic acid in acetonitrile/water). Ethyl acetate (10 mL), water (5 mL), and saturated aqueous sodium bicarbonate solution (5 mL) were added sequentially. The organic layer was separated, was dried over anhydrous sodium sulfate, was filtered, and was concentrated under reduced pressure to provide the title compound: $^1$H NMR (400 MHz, Methanol-$d_4$) δ 9.47 (d, J=1.8 Hz, 1H), 8.38 (d, J=2.0 Hz, 1H), 7.43-7.37 (m, 1H), 7.37-7.30 (m, 3H), 7.30-7.20 (m, 2H), 3.66 (s, 3H), 1.29-1.21 (m, 2H), 0.71-0.59 (m, 2H), 0.59-0.40 (m, 6H); LCMS(m/z) 444.1.

Example 597. 4-[3-[(8-chloro-[1,2,4]triazolo[4,3-a]quinazolin-5-yl)-methyl-amino]phenyl]-2-(1-methylcyclopropyl)but-3-yn-2-ol

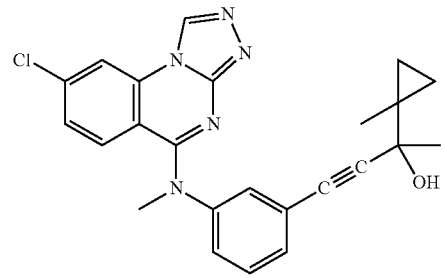 [SMILES: CN(c1cccc(C#CC(C)(O)C2(C)CC2)c1)c1nc2nncn2c2cc(Cl)ccc12]

Example 597 was prepared in a manner similar to Example 596, using 2-(1-methylcyclopropyl)but-3-yn-2-ol instead of 1,1-dicyclopropylprop-2-yn-1-ol. $^1$H NMR (400 MHz, Methanol-$d_4$) δ 9.47 (s, 1H), 8.38 (d, J=2.0 Hz, 1H), 7.41 (t, J=7.9 Hz, 1H), 7.35 (dt, J=3.9, 2.0 Hz, 2H), 7.33 (s, 1H), 7.29-7.23 (m, 2H), 3.66 (s, 3H), 1.54 (s, 3H), 1.20 (s, 3H), 0.95-0.76 (m, 2H), 0.29 (q, J=2.6 Hz, 2H); LCMS(m/z) 432.2.

Example 598. 4-[3-[(8-chloro-[1,2,4]triazolo[4,3-a]quinazolin-5-yl)-methyl-amino]phenyl]-2-cyclobutyl-but-3-yn-2-ol

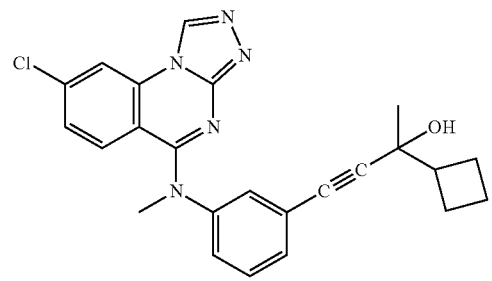 [SMILES: CN(c1cccc(C#CC(C)(O)C2CCC2)c1)c1nc2nncn2c2cc(Cl)ccc12]

Example 598 was prepared in a manner similar to Example 596, using 2-cyclobutylbut-3-yn-2-ol instead of 1,1-dicyclopropylprop-2-yn-1-ol. $^1$H NMR (400 MHz, Chloroform-d) δ 8.98 (s, 1H), 8.02 (m, 1H), 7.72-7.65 (m, 1H), 7.53 (d, J=8.8 Hz, 1H), 7.49-7.32 (m, 2H), 7.20 (d, J=11.0 Hz, 2H), 3.77 (s, 3H), 2.30 (s, 1H), 2.17-2.08 (m, 1H), 1.83 (s, 1H), 1.66 (q, J=8.2 Hz, 1H), 1.47 (s, 3H), 1.42-1.29 (m, 1H), 1.01-0.88 (m, 2H); LCMS(m/z) 432.2.

Example 599. N-(2,2-difluoroethyl)-7-fluoro-N-(2-fluoro-3-(4,4,4-trifluoro-3,3-dimethylbut-1-yn-1-yl)phenyl)-[1,2,4]triazolo[4,3-a]quinazolin-5-amine

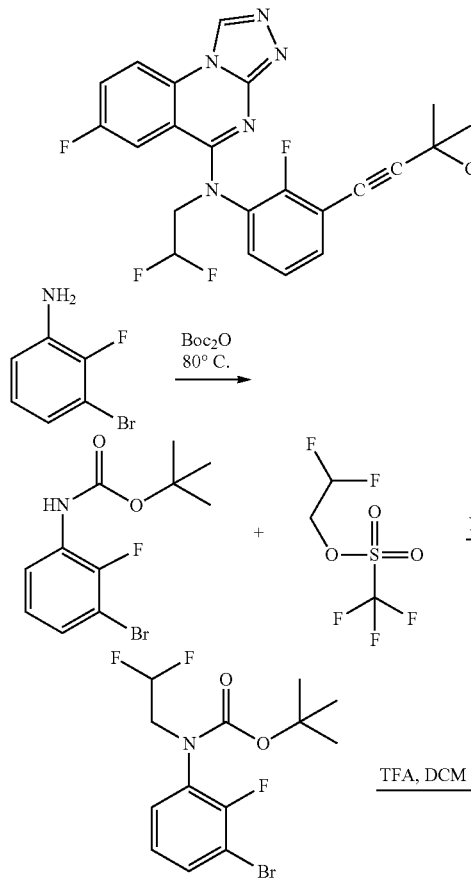

Synthesis of tert-butyl (3-bromo-2-fluorophenyl)carbamate: 3-bromo-2-fluoro-aniline (0.0105 mol) is added to a vial followed by di-tert-butyl dicarbonate (0.0210 mol) and heated to 80° C. while stirring for 7 hours. Reaction cool to room temperature, concentrated, and purified via column chromatography (hexanes to 15% EtOAc in hexanes): MS (m/z) 290.129 [M+H]+.

Synthesis of tert-butyl (3-bromo-2-fluorophenyl)(2,2-difluoroethyl)carbamate: tert-butyl (3-bromo-2-fluorophenyl) carbamate (0.00276 mol) added to a vial and dissolved in DMF (9.5 mL) and cooled to 0° C. Sodium hydride (60%, 0.00551 mol) added to solution and allowed to stir for 30 minutes. 2,2-difluoroethyl trifluoromethanesulfonate (0.00331 mol) is added and the solution allowed to warm to room temperature and stir for 1 hour. Reaction quenched with ammonium chloride solution, poured into water, extracted with EtOAc, washed with water, washed with brine, concentrated and carried forward to deprotection. MS (m/z) 354.163 [M+H]+.

Synthesis of 3-bromo-N-(2,2-difluoroethyl)-2-fluoroaniline: tert-butyl (3-bromo-2-fluorophenyl)(2,2-difluoroethyl) carbamate (0.00270 mol) is dissolved in DCM (12 mL) and trifluoroacetic acid (99%, 5 mL) is added. Reaction stirred at room temperature for 30 minutes, concentrated, and dissolved in EtOAc. This solution is then washed with saturated sodium bicarbonate solution, washed with brine, dried over Na₂SO₄, and concentrated to afford title aniline. MS (m/z) 254.242 [M+H]+.

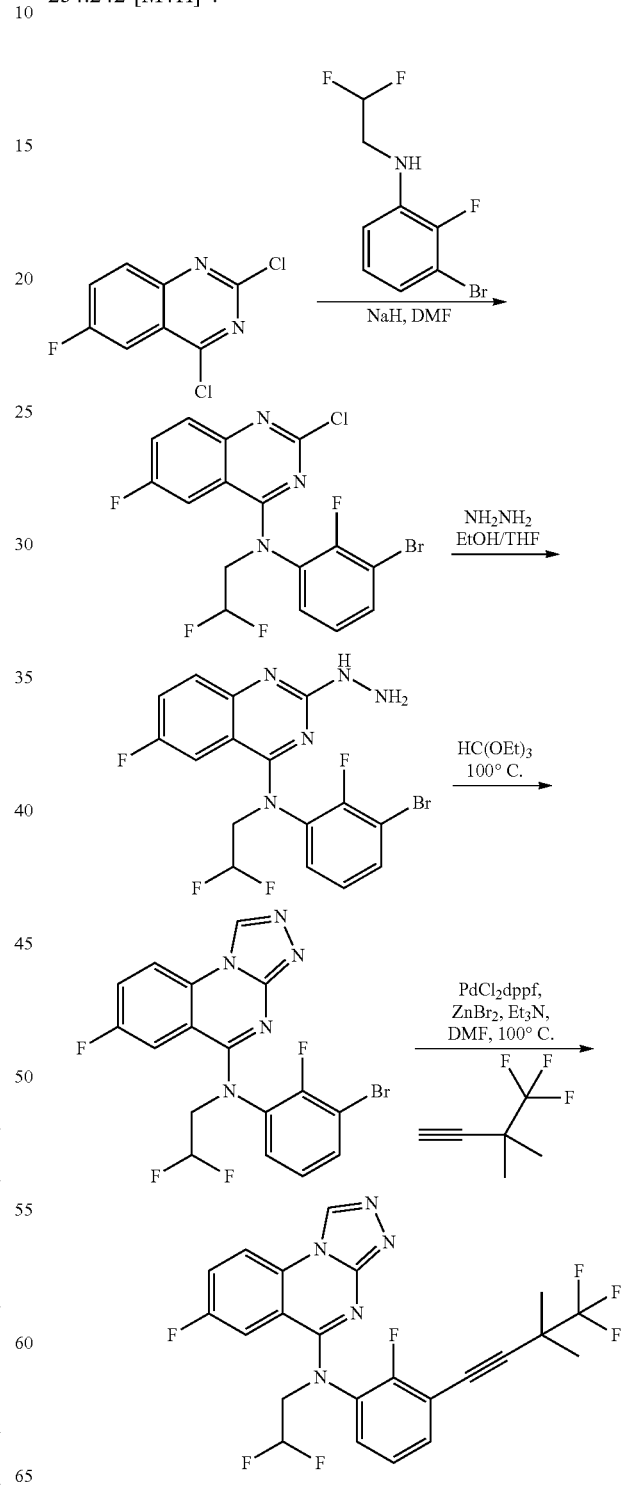

Synthesis of N-(3-bromo-2-fluorophenyl)-2-chloro-N-(2,2-difluoroethyl)-6-fluoroquinazolin-4-amine: To a solution of 3-bromo-N-(2,2-difluoroethyl)-2-fluoro-aniline (0.92 mmol) in DMF (3.0 mL) at 0° C. was added NaH (60% dispersion in mineral oil) (1.01 mmol) in one portion. The mixture was stirred at 0° C. for 30 min, followed by the 2,4-dichloro-6-fluoro-quinazoline (1.01 mmol) in one portion and the mixture was warmed to room temperature over 16 h. Upon completion, the mixture was cooled to 0° C. and quenched with a few drops of a solution of sat. NH$_4$Cl(aq) and stirred until solid crashed out. The solid was filtered off and washed with a mixture of hexanes:diethyl ether 4:1 and dried in vacuo and was used with no further purification: MS (m/z) 434.391 [M+H]$^+$.

Synthesis of N-(3-bromo-2-fluorophenyl)-N-(2,2-difluoroethyl)-6-fluoro-2-hydrazinylquinazolin-4-amine: To a solution of N-(3-bromo-2-fluoro-phenyl)-2-chloro-N-(2,2-difluoroethyl)-6-fluoro-quinazolin-4-amine (0.658 mmol) in THF (3.5 mL) and ethanol (3.5 mL) was added hydrazine monohydrate (7.9 mmol) and the mixture was stirred at room temperature for 12 h. Upon completion, the reaction was diluted with EA and washed with water, dried over Na$_2$SO$_4$ and concentrated under reduced pressure to afford the product. MS (m/z) 430.198 [M+H]$^+$.

Synthesis of N-(3-bromo-2-fluorophenyl)-N-(2,2-difluoroethyl)-7-fluoro-[1,2,4]triazolo[4,3-a]quinazolin-5-amine: A solution of N-(3-bromo-2-fluoro-phenyl)-N-(2,2-difluoroethyl)-6-fluoro-2-hydrazino-quinazolin-4-amine (0.604 mmol) and triethyl orthoformate (22.5 mmol) was heated to 110° C. for 16 h. Upon completion, the reaction was cooled to room temperature, and concentrated under reduced pressure to afford the crude product. The crude product was triturated with heptane and the solids were collected by filtration, washed with hexanes:diethyl ether (4:1) and dried in vacuo to afford product. MS (m/z) 443.307 [M+H]$^+$.

Synthesis of N-(2,2-difluoroethyl)-7-fluoro-N-(2-fluoro-3-(4,4,4-trifluoro-3,3-dimethylbut-1-yn-1-yl)phenyl)-[1,2,4]triazolo[4,3-a]quinazolin-5-amine: A solution of N-(3-bromo-2-fluoro-phenyl)-N-(2,2-difluoroethyl)-7-fluoro-[1,2,4]triazolo[4,3-a]quinazolin-5-amine (0.0606 mmol), zinc bromide (0.303 mmol), (1,1'-)bis(diphenylphosphino)ferrocene) palladium (II) dichloride (0.00303 mmol), and triethylamine (0.303 mmol) in DMF (0.70 mL) was purged with nitrogen gas for 5 minutes. 4,4,4-trifluoro-3,3-dimethyl-but-1-yne (0.00728 mol) was then added and the mixture was heated at 100° C. for 30 minutes. Upon completion, the mixture was cooled to room temperature, and ethyl acetate and sat. NH$_4$Cl (aq) were added to the mixture. The aqueous layer was extracted with EA and the combined organic layers were dried over Na$_2$SO$_4$ and concentrated in vacuo. The residue was purified by reverse phase HPLC (0.1% trifluoroacetic acid in acetonitrile/water) providing the title compound as the mono-TFA salt. $^1$H NMR (400 MHz, DMSO-d$_6$) δ 9.79 (s, 1H), 8.52 (dd, J=9.2, 4.9 Hz, 1H), 7.94 (ddd, J=9.2, 8.0, 2.8 Hz, 1H), 7.69 (td, J=8.0, 1.7 Hz, 1H), 7.57 (ddd, J=8.0, 6.4, 1.6 Hz, 1H), 7.34 (t, J=7.9 Hz, 1H), 6.86 (dd, J=10.1, 2.7 Hz, 1H), 6.60 (tt, J=55.9, 4.2 Hz, 1H), 4.48 (td, J=13.8, 4.2 Hz, 2H), 1.48 (s, 6H); MS (m/z) 497.969 [M+H]$^+$.

Example 600. N-(2,2-difluoroethyl)-7-fluoro-N-(2-fluoro-3-(4,4,4-trifluoro-3,3-dimethylbut-1-yn-1-yl)phenyl)-[1,2,4]triazolo[4,3-a]quinazolin-5-amine

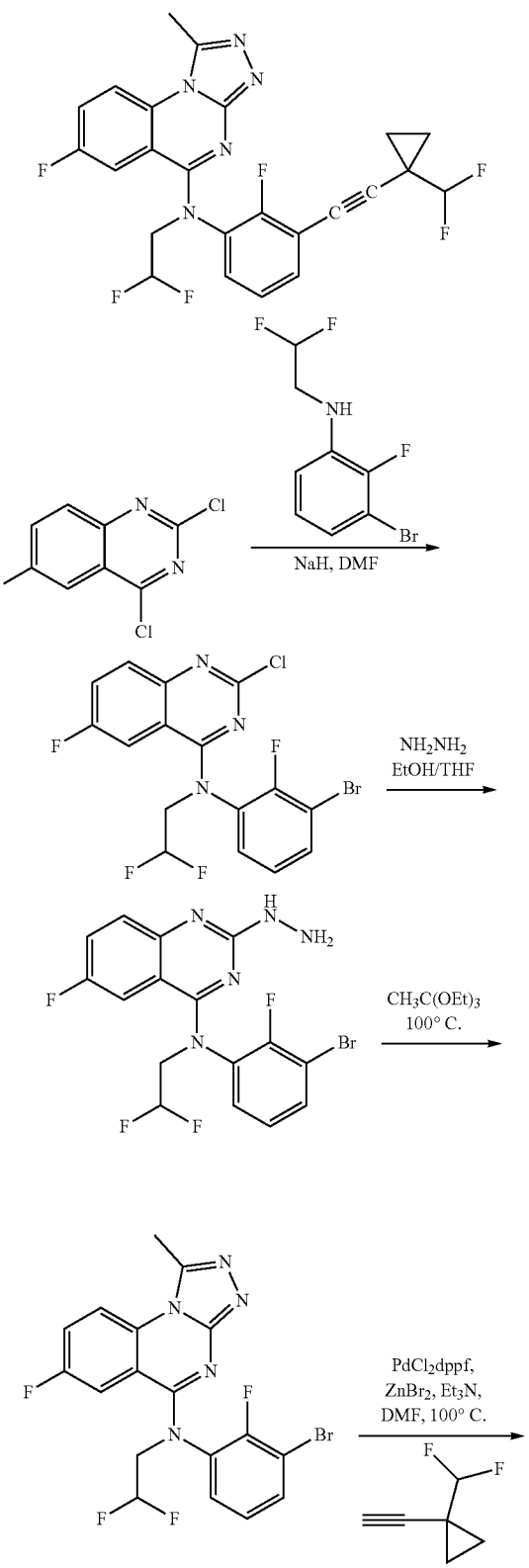

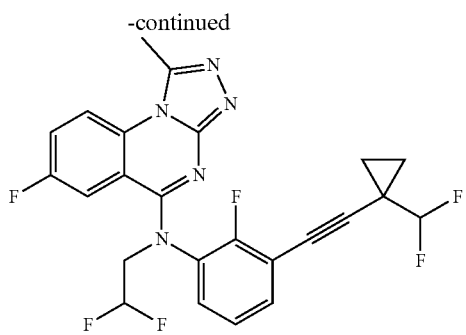

Synthesis of N-(3-bromo-2-fluorophenyl)-2-chloro-N-(2,2-difluoroethyl)-6-fluoroquinazolin-4-amine: To a solution of 3-bromo-N-(2,2-difluoroethyl)-2-fluoro-aniline (0.92 mmol) in DMF (3.0 mL) at 0° C. was added NaH (60% dispersion in mineral oil) (1.01 mmol) in one portion. The mixture was stirred at 0° C. for 30 min, followed by the 2,4-dichloro-6-fluoro-quinazoline (1.01 mmol) in one portion and the mixture was warmed to room temperature over 16 h. Upon completion, the mixture was cooled to 0° C. and quenched with a few drops of a solution of sat. NH₄Cl(aq) and stirred until solid crashed out. The solid was filtered off and washed with a mixture of hexanes:diethyl ether 4:1 and dried in vacuo and was used with no further purification. MS (m/z) 434.391 [M+H]⁺.

Synthesis of N-(3-bromo-2-fluorophenyl)-N-(2,2-difluoroethyl)-6-fluoro-2-hydrazinylquinazolin-4-amine: To a solution of N-(3-bromo-2-fluoro-phenyl)-2-chloro-N-(2,2-difluoroethyl)-6-fluoro-quinazolin-4-amine (0.658 mmol) in THF (3.5 mL) and ethanol (3.5 mL) was added hydrazine monohydrate (7.9 mmol) and the mixture was stirred at room temperature for 12 h. Upon completion, the reaction was diluted with EA and washed with water, dried over Na₂SO₄ and concentrated under reduced pressure to afford the product. MS (m/z) 430.198 [M+H]⁺.

Synthesis of N-(3-bromo-2-fluorophenyl)-N-(2,2-difluoroethyl)-7-fluoro-1-methyl-[1,2,4]triazolo[4,3-a]quinazolin-5-amine: A solution of N-(3-bromo-2-fluoro-phenyl)-N-(2,2-difluoroethyl)-6-fluoro-2-hydrazino-quinazolin-4-amine (0.818 mmol) and triethyl orthoacetate (27.5 mmol) was heated to 110° C. for 16 h. Upon completion, the reaction was cooled to room temperature, and concentrated under reduced pressure to afford the crude product. The crude product was triturated with heptane and the solids were collected by filtration, washed with hexanes:diethyl ether (4:1) and dried in vacuo to afford product. MS (m/z) 457.52 [M+H]⁺.

Synthesis of N-(2,2-difluoroethyl)-N-[3-[2-[1-(difluoromethyl)cyclopropyl]ethynyl]-2-fluoro-phenyl]-7-fluoro-1-methyl-[1,2,4]triazolo[4,3-a]quinazolin-5-amine: A solution of N-(3-bromo-2-fluoro-phenyl)-N-(2,2-difluoroethyl)-7-fluoro-[1,2,4]triazolo[4,3-a]quinazolin-5-amine (0.0550 mmol), zinc bromide (0.275 mmol), (1,1'-)bis(diphenylphosphino)ferrocene) palladium (II) dichloride (0.00275 mmol), and triethylamine (0.275 mmol) in DMF (0.70 mL) was purged with nitrogen gas for 5 minutes. 1-(Difluoromethyl)-1-ethynyl-cyclopropane (0.00660 mol) was then added and the mixture was heated at 100° C. for 30 minutes. Upon completion, the mixture was cooled to room temperature, and ethyl acetate and sat. NH₄Cl (aq) were added to the mixture. The aqueous layer was extracted with EA and the combined organic layers were dried over Na₂SO₄ and concentrated in vacuo. The residue was purified by reverse phase HPLC (0.1% trifluoroacetic acid in acetonitrile/water) providing the title compound as the mono-TFA salt. ¹H NMR (400 MHz, DMSO-d₆) δ 8.40 (dd, J=9.4, 4.7 Hz, 1H), 7.87 (ddd, J=9.4, 7.7, 2.9 Hz, 1H), 7.68 (td, J=8.0, 1.7 Hz, 1H), 7.53 (ddd, J=8.0, 6.5, 1.6 Hz, 1H), 7.35 (t, J=7.9 Hz, 1H), 6.98 (dd, J=10.0, 2.9 Hz, 1H), 6.76-6.44 (m, 1H), 5.74 (t, J=55.4 Hz, 1H), 4.50 (td, J=13.9, 4.1 Hz, 2H), 3.00 (s, 3H), 1.26-1.15 (m, 4H); MS (m/z) 491.866 [M+H]⁺.

Example 601. N-(2,2-difluoroethyl)-7-fluoro-N-(3-fluoro-5-(3-methoxy-3-methylbut-1-yn-1-yl)phenyl)-[1,2,4]triazolo[4,3-a]quinazolin-5-amine

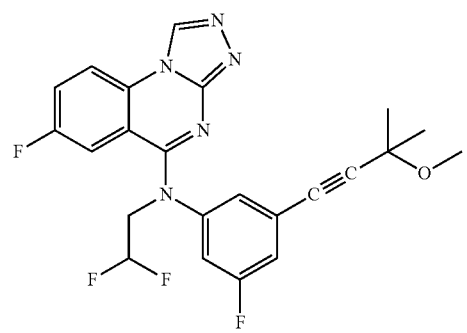 [SMILES: COC(C)(C)C#Cc1cc(F)cc(N(CC(F)F)c2nc3nncn3c3ccc(F)cc23)c1]

The title compound was synthesized according to the procedures described in Example 599.

¹H NMR (400 MHz, DMSO-d₆) δ 9.80 (s, 1H), 8.50 (dd, J=9.2, 4.8 Hz, 1H), 7.91 (ddd, J=9.2, 8.1, 2.8 Hz, 1H), 7.37-7.31 (m, 2H), 7.25-7.20 (m, 1H), 6.97 (dd, J=9.9, 2.8 Hz, 1H), 6.73-6.39 (m, 1H), 4.58 (td, J=14.3, 4.0 Hz, 2H), 3.28 (s, 3H), 1.44 (s, 6H); MS (m/z) 458.175 [M+H]⁺.

Example 602. N-(2,2-difluoroethyl)-6-fluoro-N-(3-fluoro-5-(3-methoxy-3-methylbut-1-yn-1-yl)phenyl)-[1,2,4]triazolo[4,3-a]quinazolin-5-amine

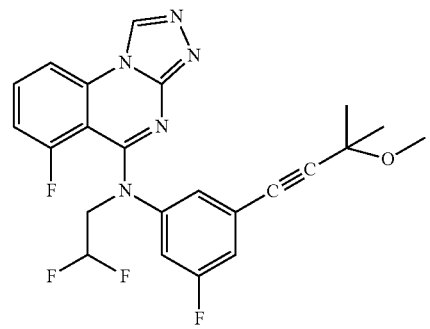 [SMILES: COC(C)(C)C#Cc1cc(F)cc(N(CC(F)F)c2nc3nncn3c3cccc(F)c23)c1]

The title compound was synthesized according to the procedures described in Example 603 using triethylorthoformate instead of triethylorthoacetate. ¹H NMR (400 MHz, DMSO-d₆) δ 9.82 (d, J=0.8 Hz, 1H), 8.26 (d, J=8.3 Hz, 1H), 8.01 (dd, J=8.6, 5.2 Hz, 1H), 7.26 (dd, J=11.9, 8.3 Hz, 1H), 7.23-7.14 (m, 2H), 7.05 (d, J=9.0 Hz, 1H), 6.72-6.36 (m, 1H), 4.73-4.55 (m, 2H), 3.26 (s, 3H), 1.43 (s, 6H); MS (m/z) 458.2 [M+H]⁺.

955

Example 603. N-(2,2-difluoroethyl)-6-fluoro-N-[3-fluoro-5-(3-methoxy-3-methyl-but-1-ynyl)phenyl]-1-methyl-[1,2,4]triazolo[4,3-a]quinazolin-5-amine

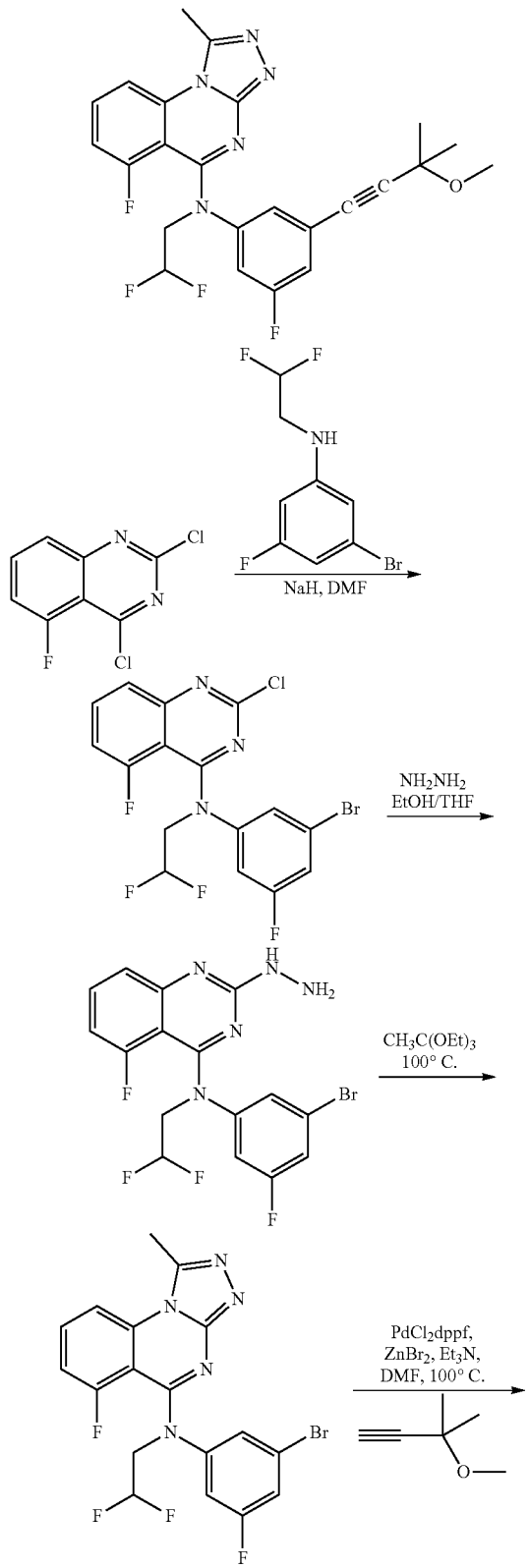

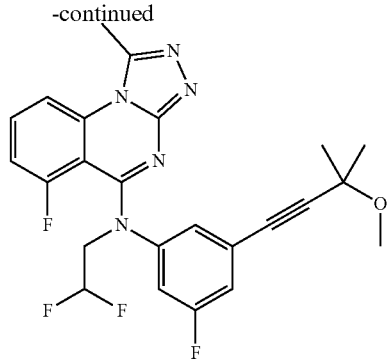

Synthesis of N-(3-bromo-5-fluorophenyl)-2-chloro-N-(2,2-difluoroethyl)-5-fluoroquinazolin-4-amine: To a solution of 3-bromo-N-(2,2-difluoroethyl)-5-fluoroaniline (1.97 mmol) in DMF (3.0 mL) at 0° C. was added NaH (60% dispersion in mineral oil) (2.36 mmol) in one portion. The mixture was stirred at 0° C. for 30 min, followed by the 2,4-dichloro-5-fluoro-quinazoline (1.97 mmol) in one portion and the mixture was warmed to room temperature over 16 h. Upon completion, the mixture was cooled to 0° C. and quenched with a few drops of a solution of sat. NH₄Cl(aq) and stirred until solid crashed out. The solid was filtered off and washed with a mixture of hexanes:diethyl ether 4:1 and dried in vacuo and was used with no further purification. MS (m/z) 436.340 [M+H]⁺.

Synthesis of N-(3-bromo-5-fluorophenyl)-N-(2,2-difluoroethyl)-5-fluoro-2-hydrazinylquinazolin-4-amine: To a solution of N-(3-bromo-2-fluoro-phenyl)-2-chloro-N-(2,2-difluoroethyl)-5-fluoro-quinazolin-4-amine (1.27 mmol) in THF (3.5 mL) and ethanol (3.5 mL) was added hydrazine monohydrate (15.2 mmol) and the mixture was stirred at room temperature for 12 h. Upon completion, the reaction was diluted with EA and washed with water, dried over Na₂SO₄ and concentrated under reduced pressure to afford the product. MS (m/z) 433.134 [M+H]⁺.

Synthesis of N-(3-bromo-5-fluorophenyl)-N-(2,2-difluoroethyl)-6-fluoro-1-methyl-[1,2,4]triazolo[4,3-a]quinazolin-5-amine: A solution of N-(3-bromo-5-fluorophenyl)-N-(2,2-difluoroethyl)-5-fluoro-2-hydrazinylquinazolin-4-amine (0.604 mmol) and triethyl orthoacetate (22.5 mmol) was heated to 110° C. for 16 h. Upon completion, the reaction was cooled to room temperature, and concentrated under reduced pressure to afford the crude product. The crude product was triturated with heptane and the solids were collected. MS (m/z) 457.360 [M+H]⁺.

Synthesis of N-(2,2-difluoroethyl)-6-fluoro-N-[3-fluoro-5-(3-methoxy-3-methyl-but-1-ynyl)phenyl]-1-methyl-[1,2,4]triazolo[4,3-a]quinazolin-5-amine: N-(3-bromo-5-fluorophenyl)-N-(2,2-difluoroethyl)-6-fluoro-1-methyl-[1,2,4]triazolo[4,3-a]quinazolin-5-amine (0.00568 mmol), zinc bromide (0.284 mmol), (1,1'-)bis(diphenylphosphino)ferrocene) palladium (II) dichloride (0.00284 mmol), and triethylamine (0.284 mmol) in DMF (0.70 mL) was purged with nitrogen gas for 5 minutes. 3-methoxy-3-methyl-but-1-yne (0.170 mol) was then added and the mixture was heated at 100° C. for 30 minutes. Upon completion, the mixture was cooled to room temperature, and ethyl acetate and sat. NH₄Cl (aq) were added to the mixture. The aqueous layer was extracted with EA and the combined organic layers were dried over Na₂SO₄ and concentrated in vacuo. The residue was purified by reverse phase HPLC (0.1% trifluoroacetic acid in acetonitrile/water) providing the title compound as the mono-TFA salt. $^1$H NMR (400 MHz, DMSO-d$_6$) δ 8.17 (d, J=8.6 Hz, 1H), 7.98 (q, J=8.3 Hz, 1H), 7.36-7.24 (m, 1H), 7.17 (s, 1H), 7.15-7.09 (m, 1H), 7.05 (d, J=9.0 Hz, 1H), 6.70-6.35 (m, 1H), 4.65 (t, J=14.1 Hz, 2H), 3.26 (s, 3H), 3.02 (s, 3H), 1.43 (s, 6H); MS (m/z) 472.2 [M+H]$^+$.

Example 604. N-(2,2-difluoroethyl)-7-fluoro-N-(3-fluoro-5-(3-methoxy-3-methylbut-1-yn-1-yl)phenyl)-1-methyl-[1,2,4]triazolo[4,3-a]quinazolin-5-amine

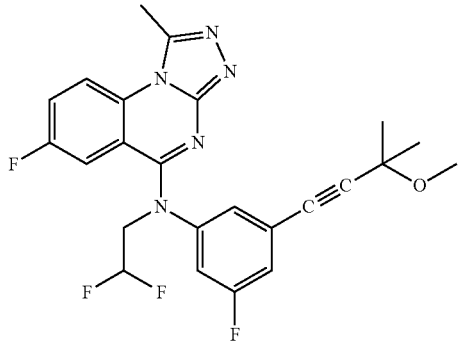 [SMILES: COC(C)(C)C#Cc1cc(F)cc(N(CC(F)F)c2nc3nnc(C)n3c3ccc(F)cc23)c1]

The title compound was synthesized according to the procedures described for Example 600.

$^1$H NMR (400 MHz, DMSO-d$_6$) δ 8.39 (dd, J=9.5, 4.6 Hz, 1H), 7.90-7.80 (m, 1H), 7.31 (d, J=7.3 Hz, 2H), 7.25 (d, J=8.8 Hz, 1H), 7.09 (dd, J=9.8, 2.9 Hz, 1H), 6.75-6.37 (m, 1H), 4.60 (td, J=14.5, 14.0, 3.6 Hz, 2H), 3.28 (s, 3H), 3.02 (s, 3H), 1.44 (s, 6H); MS (m/z) 472.2 [M+H]$^+$.

Example 605. 1-(difluoromethyl)-7-fluoro-5-(5-((1-methylcyclopropyl)ethynyl)-3,4-dihydroquinolin-1(2H)-yl)-[1,2,4]triazolo[4,3-a]quinazoline

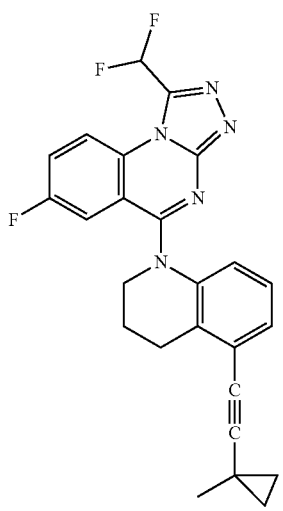 [SMILES: CC1(C#Cc2cccc3c2CCCN3c2nc3nnc(C(F)F)n3c3ccc(F)cc23)CC1]

The title compound was synthesized according to the procedures described for Example 713.

$^1$H NMR (400 MHz, DMSO-d$_6$) 8.21 (dd, J=9.3, 4.5 Hz, 1H), 7.98-7.89 (m, 1H), 7.77 (d, J=51.4 Hz, 1H), 7.42 (dd, J=9.5, 2.9 Hz, 1H), 7.09 (d, J=7.5 Hz, 1H), 6.92 (t, J=7.9 Hz, 1H), 6.83 (d, J=8.1 Hz, 1H), 3.94 (d, J=12.4 Hz, 2H), 2.95 (t, J=6.7 Hz, 2H), 2.08 (p, J=6.7 Hz, 2H), 1.37 (s, 3H), 1.00 (q, J=4.0 Hz, 2H), 0.80 (q, J=4.1 Hz, 2H); MS (m/z) 448.2 [M+H]$^+$.

Example 606. N-ethyl-6,7-difluoro-N-[3-fluoro-5-[2-(1-methylcyclopropyl)ethynyl]phenyl]-[1,2,4]triazolo[4,3-a]quinazolin-5-amine

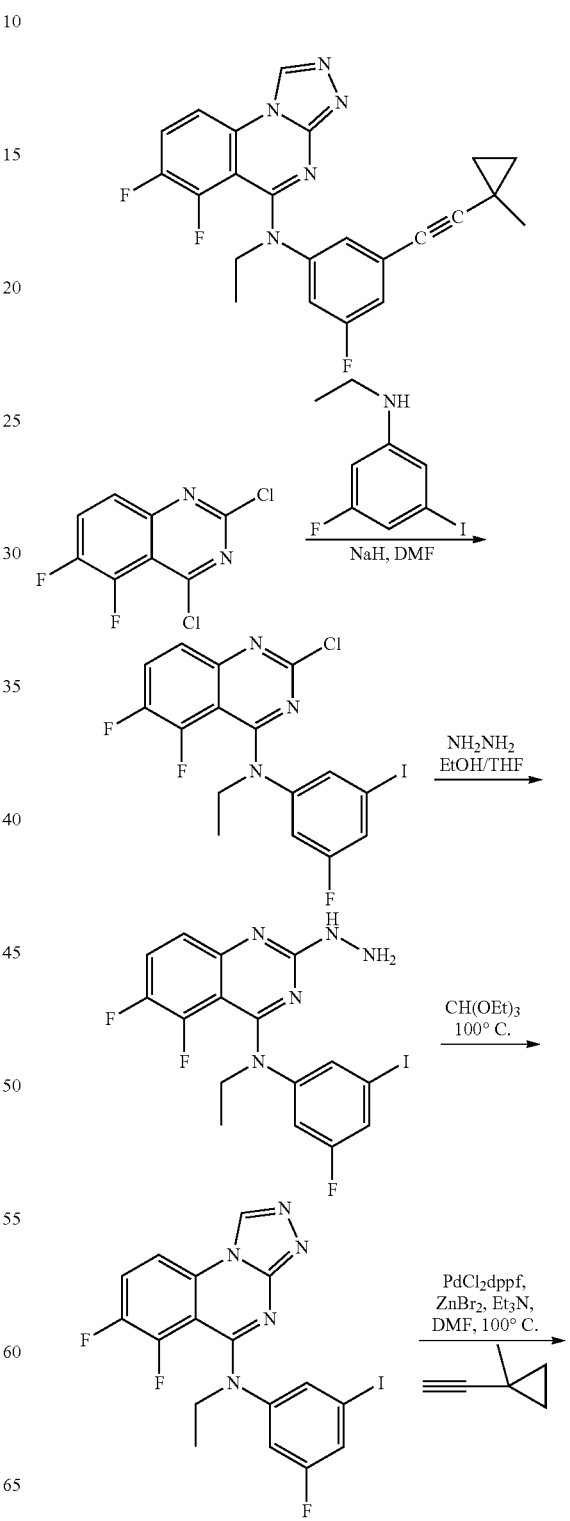

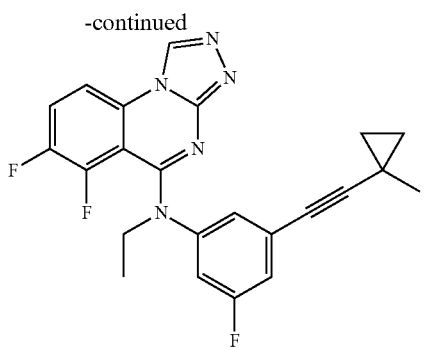

Synthesis of 2-chloro-N-ethyl-5,6-difluoro-N-(3-fluoro-5-iodophenyl)quinazolin-4-amine: To a solution of N-ethyl-3-fluoro-5-iodoaniline (1.40 mmol) in DMF (3.0 mL) at 0° C. was added NaH (60% dispersion in mineral oil) (1.53 mmol) in one portion. The mixture was stirred at 0° C. for 30 min, followed by the 2,4-dichloro-5,6-difluoroquinazoline (1.28 mmol) in one portion and the mixture was warmed to room temperature over 16 h. Upon completion, the mixture was cooled to 0° C. and quenched with a few drops of a solution of sat. NH$_4$Cl(aq) and stirred until solid crashed out. The solid was filtered off and washed with a mixture of hexanes:diethyl ether 4:1 and dried in vacuo and was used with no further purification. MS (m/z) 466.285 [M+H]$^+$.

Synthesis of N-ethyl-5,6-difluoro-N-(3-fluoro-5-iodophenyl)-2-hydrazinylquinazolin-4-amine: To a solution of N-(3-iodo-5-fluorophenyl)-2-chloro-N-ethyl-5,6-difluoroquinazolin-4-amine (0.597 mmol) in THF (3.5 mL) and ethanol (3.5 mL) was added hydrazine monohydrate (5.97 mmol) and the mixture was stirred at room temperature for 12 h. Upon completion, the reaction was diluted with EA and washed with water, dried over Na$_2$SO$_4$ and concentrated under reduced pressure to afford the product. MS (m/z) 461.688 [M+H]$^+$.

Synthesis of N-ethyl-6,7-difluoro-N-(3-fluoro-5-iodophenyl)-[1,2,4]triazolo[4,3-a]quinazolin-5-amine: A solution of N-(3-iodo-5-fluorophenyl)-N-ethyl-5,6-difluoro-2-hydrazinylquinazolin-4-amine (0.603 mmol) and triethyl orthoformate (7.24 mmol) was heated to 110° C. for 16 h. Upon completion, the reaction was cooled to room temperature, and concentrated under reduced pressure to afford the crude product. The crude product was triturated with heptane and the solids were collected. MS (m/z) 471.728 [M+H]$^+$.

Synthesis of N-ethyl-6,7-difluoro-N-[3-fluoro-5-[2-(1-methylcyclopropyl)ethynyl]phenyl]-[1,2,4]triazolo[4,3-a]quinazolin-5-amine: N-(3-iodo-5-fluorophenyl)-N-ethyl-6,7-difluoro-[1,2,4]triazolo[4,3-a]quinazolin-5-amine (0.107 mmol), zinc bromide (0.533 mmol), (1,1'-)bis(diphenylphosphino)ferrocene) palladium (II) dichloride (0.0107 mmol), and triethylamine (2.13 mmol) in DMF (0.70 mL) was purged with nitrogen gas for 5 minutes. 1-ethynyl-1-methyl-cyclopropane (0.6398 mol) was then added and the mixture was heated at 100° C. for 30 minutes. Upon completion, the mixture was cooled to room temperature, and ethyl acetate and sat. NH$_4$Cl (aq) were added to the mixture. The aqueous layer was extracted with EA and the combined organic layers were dried over Na$_2$SO$_4$ and concentrated in vacuo. The residue was purified by reverse phase HPLC (0.1% trifluoroacetic acid in acetonitrile/water) providing the title compound as the mono-TFA salt. $^1$H NMR (400 MHz, DMSO-d$_6$) δ 9.78 (s, 1H), 8.33-8.24 (m, 1H), 8.21-8.08 (m, 1H), 7.19 (dt, J=10.6, 2.3 Hz, 1H), 7.14 (t, J=1.6 Hz, 1H), 7.03-6.97 (m, 1H), 4.19 (q, J=6.9 Hz, 2H), 1.27 (s, 3H), 1.22 (t, J=6.9 Hz, 3H), 0.92 (q, J=4.0 Hz, 2H), 0.72 (q, J=4.1 Hz, 2H); MS (m/z) 422.1 [M+H]$^+$.

Example 607. 4-(3-((6,7-difluoro-[1,2,4]triazolo[4,3-a]quinazolin-5-yl)(ethyl)amino)-5-fluorophenyl)-2-methylbut-3-yn-2-ol

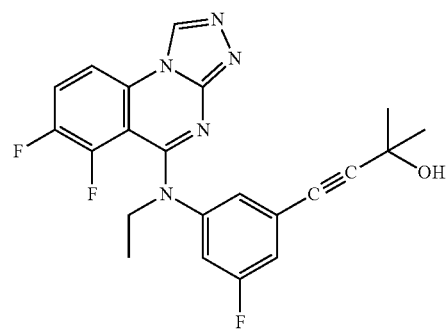 [SMILES: CCN(c1cc(F)cc(C#CC(C)(C)O)c1)c1nc2nncn2c2ccc(F)c(F)c12]

The title compound was synthesized according to the procedures described for Example 606.

$^1$H NMR (400 MHz, DMSO-d$_6$) δ 9.79 (s, 1H), 8.34-8.24 (m, 1H), 8.16 (q, J=9.2 Hz, 1H), 7.26-7.19 (m, 1H), 7.18 (t, J=1.6 Hz, 1H), 7.04-6.98 (m, 1H), 4.20 (q, J=6.9 Hz, 2H), 1.42 (s, 6H), 1.23 (t, J=6.9 Hz, 3H); MS (m/z) 426.1 [M+H]$^+$.

Example 608. N-ethyl-6,7-difluoro-N-(3-fluoro-5-((1-(trifluoromethyl)cyclopropyl)ethynyl)phenyl)-[1,2,4]triazolo[4,3-a]quinazolin-5-amine

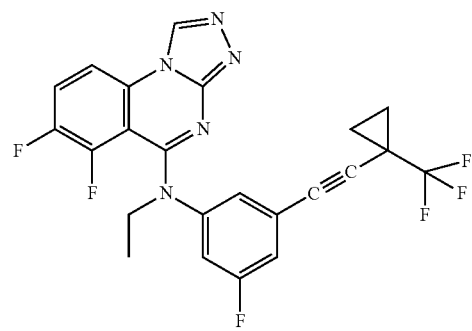 [SMILES: CCN(c1cc(F)cc(C#CC2(C(F)(F)F)CC2)c1)c1nc2nncn2c2ccc(F)c(F)c12]

The title compound was synthesized according to the procedures described for Example 606.

$^1$H NMR (400 MHz, DMSO-d$_6$) δ 9.79 (s, 1H), 8.32-8.26 (m, 1H), 8.21-8.12 (m, 1H), 7.30-7.25 (m, 2H), 7.15-7.09 (m, 1H), 4.20 (q, J=6.9 Hz, 2H), 1.45-1.41 (m, 2H), 1.39-1.34 (m, 2H), 1.23 (t, J=6.9 Hz, 3H); MS (m/z) 476.1 [M+H]$^+$.

Example 609. 8-chloro-N-(2,2,2-trifluoroethyl)-N-(5-((1-(trifluoromethyl)cyclopropyl)ethynyl)pyridin-3-yl)-[1,2,4]triazolo[4,3-a]quinazolin-5-amine

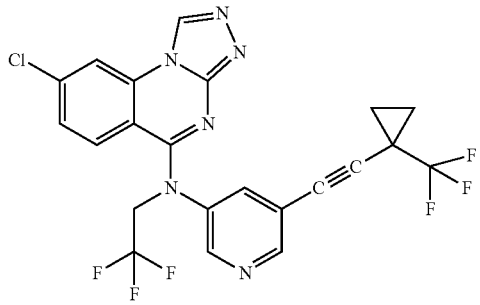 [SMILES: FC(F)(F)CN(c1cncc(C#CC2(C(F)(F)F)CC2)c1)c1nc2nncn2c2cc(Cl)ccc12]

(Step 1) Synthesis of N-(5-bromopyridin-3-yl)-2,2,2-trifluoroacetamide

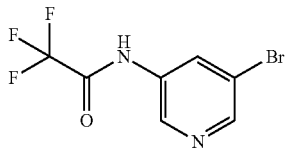 [SMILES: O=C(Nc1cncc(Br)c1)C(F)(F)F]

A solution of 5-bromopyridin-3-amine (5.00 g, 28.9 mmol) and HOBt hydrate (4.87 g, 31.8 mmol) in DCM (150 mL) was treated with TFA (2.21 mL, 28.9 mmol) followed by DIPEA (5.54 mL, 31.8 mmol) and EDC hydrochloride (6.09 g, 31.8 mmol). The resulting mixture was stirred overnight at RT. An aqueous solution of HCl (1 M) was added with stirring, and the resulting suspension was filtered. The filtrate layers were separated, and the organic layer was washed with sat. aqueous NaHCO3. The organic layer was dried over Na2SO4, filtered, and concentrated in vacuo to afford the desired product, which was used in the next step without further purification. LCMS(m/z) 268.9 [M+H]+.

(Step 2) Synthesis of 5-bromo-N-(2,2,2-trifluoroethyl)pyridin-3-amine

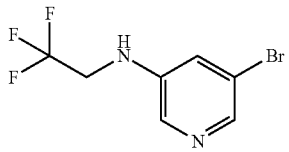 [SMILES: FC(F)(F)CNc1cncc(Br)c1]

A solution of N-(5-bromopyridin-3-yl)-2,2,2-trifluoroacetamide (2.17 g, 8.07 mmol) in THF (21 mL) under N2 was treated with BH3·THF (20.2 mL, 1.0 M solution in THF, 20.2 mmol). The resulting mixture was stirred at reflux for 3 h. The mixture was then cooled to RT, and quenched carefully by dropwise addition of MeOH (20 mL). The mixture was then refluxed for an additional 1 h, then cooled to RT and concentrated in vacuo. The resulting residue was purified by silica gel chromatography (0 to 55% EtOAc in hexanes) to afford the desired product. LCMS(m/z) 255.3 [M+H]+.

(Step 3) Synthesis of N-(5-bromopyridin-3-yl)-2,7-dichloro-N-(2,2,2-trifluoroethyl)quinazolin-4-amine

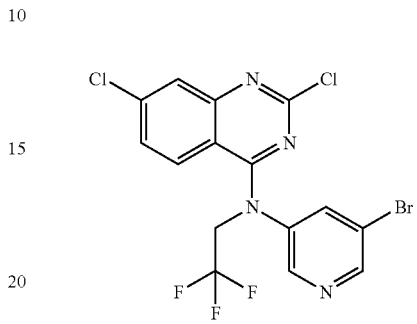

A solution of 5-bromo-N-(2,2,2-trifluoroethyl)pyridin-3-amine (353 mg, 1.38 mmol) in DMF (2.0 mL) was treated with NaH (60% dispersion in mineral oil, 63.6 mg, 1.66 mmol) at 0° C. After stirring for 30 min, 2,4,7-trichloroquinazoline (323 mg, 1.38 mmol) was added in a single portion, and the reaction mixture was warmed to RT with stirring. After 2 h, the reaction mixture was carefully diluted with water and extracted with EtOAc. The organic layer was washed twice more with water, then concentrated in vacuo. The residue was purified by silica gel chromatography (0 to 20% EtOAc in hexanes) to afford the desired product. LCMS(m/z) 251.3 [M+H]+.

(Step 4) Synthesis of N-(5-bromopyridin-3-yl)-7-chloro-2-hydrazineyl-N-(2,2,2-trifluoroethyl)quinazolin-4-amine

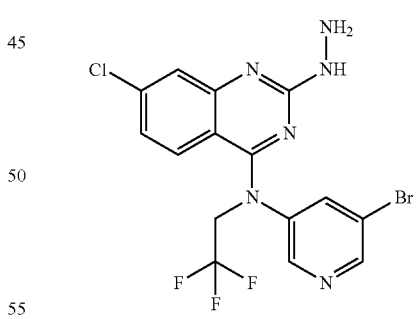

A solution of N-(5-bromopyridin-3-yl)-2,7-dichloro-N-(2,2,2-trifluoroethyl)quinazolin-4-amine (279 mg, 617 umol) in THF (2.0 mL) and EtOH (2.0 mL) was treated with hydrazine (192 uL, 3.09 mmol). The reaction mixture was stirred for 1 h at RT, then diluted with EtOAc and washed with 4:1 water/brine. The organic layer was dried over MgSO4, filtered, and concentrated in vacuo. The residue was co-evaporated with PhMe to afford the desired product, which was used in the next step without further purification. LCMS(m/z) 447.4 [M+H]+.

(Step 5) Synthesis of N-(5-bromopyridin-3-yl)-8-chloro-N-(2,2,2-trifluoroethyl)-[1,2,4]triazolo[4,3-a]quinazolin-5-amine

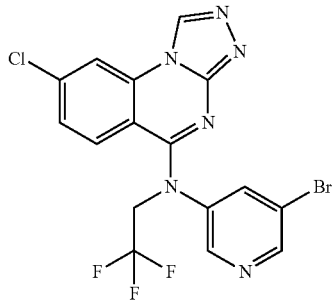 [SMILES: FC(F)(F)CN(c1cncc(Br)c1)c1nc2nncn2c2cc(Cl)ccc12]

A suspension of N-(5-bromopyridin-3-yl)-7-chloro-2-hydrazineyl-N-(2,2,2-trifluoroethyl)quinazolin-4-amine (200 mg, 447 umol) in triethyl orthoformate (3.23 mL, 19.4 mmol) was stirred at 130° C. for 3 h. The reaction mixture was cooled to RT and concentrated in vacuo. The residue was purified by silica gel chromatography (0 to 100% EtOAc in hexanes) to afford the desired product. LCMS(m/z) 457.4 [M+H]+.

(Step 6) Synthesis of 8-chloro-N-(2,2,2-trifluoroethyl)-N-(5-((1-(trifluoromethyl)cyclopropyl)ethynyl)pyridin-3-yl)-[1,2,4]triazolo[4,3-a]quinazolin-5-amine

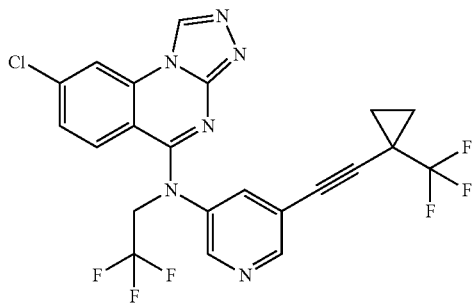 [SMILES: FC(F)(F)CN(c1cncc(C#CC2(C(F)(F)F)CC2)c1)c1nc2nncn2c2cc(Cl)ccc12]

A suspension of N-(5-bromopyridin-3-yl)-8-chloro-N-(2,2,2-trifluoroethyl)-[1,2,4]triazolo[4,3-a]quinazolin-5-amine (30 mg, 66 umol), zinc bromide (74 mg, 328 umol), Pd(dppf)Cl2 (9.3 mg, 13 umol), and triethylamine (183 uL, 1.31 mmol) in DMF (2.0 mL) was sparged with N2 for 1 minute, then 1-ethynyl-1-(trifluoromethyl)cyclopropane (13 mg, 98 umol) was added. The vial was quickly sealed and the mixture was stirred vigorously at 100° C. for 5 min, then cooled immediately in an ice bath. The reaction mixture was diluted with EtOAc and 4:1 water/brine, then filtered through Celite. The filtrate layers were separated, and the organic layer washed twice more with 4:1 water/brine, followed by brine. The organic layer was then and concentrated in vacuo and the resulting residue was purified by reverse phase preparative HPLC to afford the desired product: $^1$H NMR (400 MHz, DMSO-d$_6$) δ 9.82 (s, 1H), 8.68 (d, J=2.0 Hz, 1H), 8.51-8.47 (m, 2H), 7.94 (dd, J=2.2 Hz, 1H), 7.45 (dd, J=8.9, 2.0 Hz, 1H), 7.36 (d, J=8.9 Hz, 1H), 5.14 (q, J=9.2 Hz, 2H), 1.50-1.38 (m, 4H); LCMS(m/z) 511.1 [M+H]+.

Example 610. 5-((3-fluoro-5-((1-(trifluoromethyl)cyclopropyl)ethynyl)phenyl)(methyl)amino)-[1,2,4]triazolo[4,3-a]quinazoline-8-carbonitrile (Step 1) Synthesis of 4-((3-bromo-5-fluorophenyl)(methyl)amino)-2-chloroquinazoline-7-carbonitrile

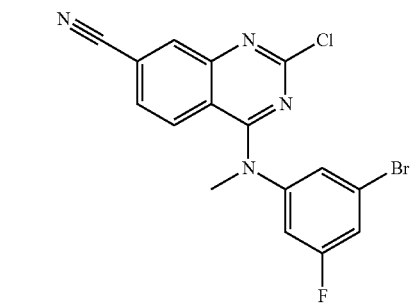 [SMILES: CN(c1cc(F)cc(Br)c1)c1nc(Cl)nc2cc(C#N)ccc12]

To a suspension of 2,4-dichloroquinazoline-7-carbonitrile (483 mg, 2.17 mmol) and 3-bromo-5-fluoro-N-methylaniline (400 mg, 1.96 mmol) in 2-propanol (3.0 mL) was added conc. HCl (37%, 164 uL, 1.96 mmol), and the mixture was stirred for 1 h at RT. The precipitates were collected and washed with 2-propanol to give the desired product, which was used for the next step without further purification. LCMS(m/z) 391.3 [M+H]+.

(Step 2) Synthesis of 4-((3-bromo-5-fluorophenyl)(methyl)amino)-2-hydrazineylquinazoline-7-carbonitrile

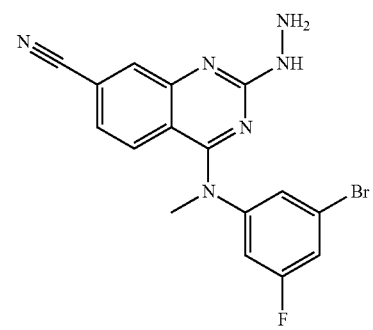 [SMILES: CN(c1cc(F)cc(Br)c1)c1nc(NN)nc2cc(C#N)ccc12]

To a solution of 4-((3-bromo-5-fluorophenyl)(methyl)amino)-2-chloroquinazoline-7-carbonitrile (181 mg, 0.462 mmol) in THF (3 mL) and EtOH (5 mL) was added hydrazine hydrate (0.294 mL, 9.24 mmol), and the mixture was stirred for 3 h at RT. The reaction mixture was diluted with EtOAc, washed successively with water and brine, and dried over Na2SO4. The organic layer was concentrated in vacuo to give the desired product, which was used for the next step without further purification. LCMS(m/z) 387.3 [M+H]+.

(Step 3) Synthesis of 5-((3-bromo-5-fluorophenyl)(methyl)amino)-[1,2,4]triazolo[4,3-a]quinazoline-8-carbonitrile

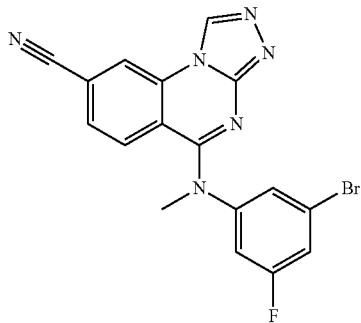 [SMILES: CN(c1cc(F)cc(Br)c1)c1nc2nncn2c2cc(C#N)ccc12]

A mixture of 4-((3-bromo-5-fluorophenyl)(methyl)amino)-2-hydrazineylquinazoline-7-carbonitrile (179 mg, 0.462 mmol) and triethyl orthoformate (4.0 mL, 24 mmol) was stirred at 120° C. for 1 h. The reaction mixture was concentrated in vacuo, and the residue was purified by column chromatography (DCM/EtOAc; 0 to 40%), followed by reverse phase preparative HPLC to afford the desired product. LCMS(m/z) 397.2 [M+H]$^+$.

(Step 4) Synthesis of 5-((3-fluoro-5-((1-(trifluoromethyl)cyclopropyl)ethynyl)phenyl)(methyl)amino)-[1,2,4]triazolo[4,3-a]quinazoline-8-carbonitrile

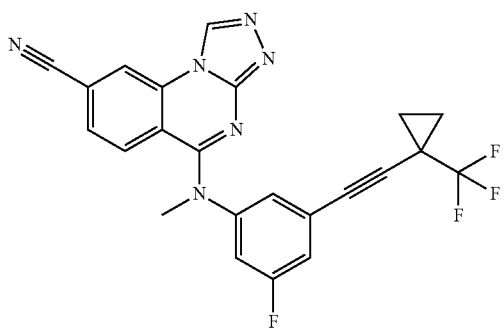 [SMILES: CN(c1cc(F)cc(C#CC2(C(F)(F)F)CC2)c1)c1nc2nncn2c2cc(C#N)ccc12]

A suspension of 5-((3-bromo-5-fluorophenyl)(methyl)amino)-[1,2,4]triazolo[4,3-a]quinazoline-8-carbonitrile (30 mg, 60 umol), zinc bromide (68 mg, 302 umol), Pd(dppf)Cl$_2$ (8.6 mg, 12 umol), and triethylamine (169 uL, 1.21 mmol) in NMP (2.0 mL) was sparged with N2 for 1 minute, then 1-ethynyl-1-(trifluoromethyl)cyclopropane (32 mg, 24 umol) was added. The vial was quickly sealed and the mixture was stirred vigorously at 100° C. for 20 min, then cooled immediately in an ice bath. The reaction mixture was diluted with water and extracted 3× with EtOAc. The combined organic layers were concentrated in vacuo, and the resulting residue purified by silica gel chromatography (0 to 20% of a pre-mixed solution of 4:1 EtOAc/MeOH as the polar solvent, with DCM as the non-polar solvent). Product-containing fractions were combined and concentrated in vacuo, and the resulting residue was further purified by reverse phase preparative HPLC to afford the desired product: $^1$H NMR (400 MHz, DMSO-d$_6$) δ 9.77 (s, 1H), 9.03 (d, J=1.5 Hz, 1H), 7.80 (dd, J=8.6, 1.6 Hz, 1H), 7.48 (d, J=8.6 Hz, 1H), 7.44 (dt, J=10.2, 2.3 Hz, 1H), 7.39 (t, J=1.6 Hz, 1H), 7.30-7.25 (m, 1H), 3.58 (s, 3H), 1.47-1.33 (m, 4H); LCMS(m/z) 451.1 [M+H]$^+$.

Example 611. 5-((3-(3,3-dimethylbut-1-yn-1-yl)-5-fluorophenyl)(methyl)amino)-[1,2,4]triazolo[4,3-a]quinazoline-8-carbonitrile

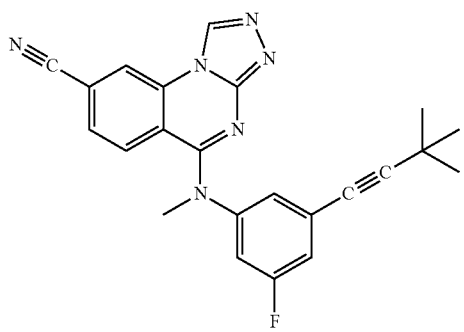 [SMILES: CN(c1cc(F)cc(C#CC(C)(C)C)c1)c1nc2nncn2c2cc(C#N)ccc12]

The title compound was synthesized according to the procedures described for Example 610.

$^1$H NMR (400 MHz, DMSO-d$_6$) δ 9.77 (s, 1H), 9.03 (d, J=1.6 Hz, 1H), 7.81 (dd, J=8.6, 1.6 Hz, 1H), 7.48 (d, J=8.6 Hz, 1H), 7.35 (dt, J=10.1, 2.3 Hz, 1H), 7.28 (t, J=1.7 Hz, 1H), 7.18-7.14 (m, 3H), 3.58 (s, 3H), 1.25 (s, 9H); LCMS (m/z) 451.1 [M+H]$^+$.

Example 612. N-(2,2-difluoroethyl)-N-(2-(3,3-dimethylbut-1-yn-1-yl)pyridin-4-yl)-6-fluoro-1-methyl-[1,2,4]triazolo[4,3-a]quinazolin-5-amine

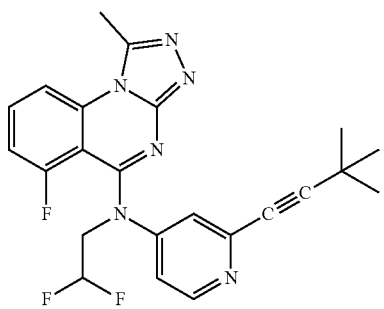

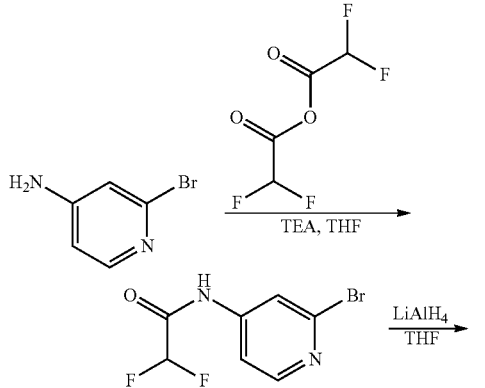

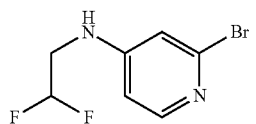

Synthesis of N-(2-bromopyridin-4-yl)-2,2-difluoroacetamide: To a solution of 2-bromopyridin-4-amine (9.1 g, 52.6 mmol) in dry THF (20 mL) under argon was added TEA (8.36 mL, 57.9 mmol) and dropwise 2,2-difluoroacetic anhydride (10.1 g, 57.9 mmol). The solution was stirred at room temperature for 3 h. The reaction was poured into ice water, basified by saturated aqueous NaHCO$_3$, and then extracted with ethyl acetate. The combined organic phases were dried over MgSO$_4$, concentrated and dried under vacuum to afford the desired compound.

Synthesis of 2-bromo-N-(2,2-difluoroethyl)pyridin-4-amine: A solution of LiAlH$_4$ in THF (1M, 52.6 mmol) was added portion-wise to a solution of 2,2-difluoroacetic anhydride (12 g, 47.8 mmol) in THF (40 ml) at 0° C. under nitrogen-atmosphere. After 10 min at 0° C. the reaction mixture was allowed to reach room temperature and stirring was continued for 6 h. The mixture was quenched with water at 0° C. and extracted with ethyl acetate. The aqueous phase was washed with saturated sodium chloride solution, dried with MgSO$_4$ and concentrated under reduced pressure. The crude product was purified by column-chromatography on silica (Hexanes:Ethyl acetate 3:1) to give 2-bromo-N-(2,2-difluoroethyl)pyridin-4-amine.

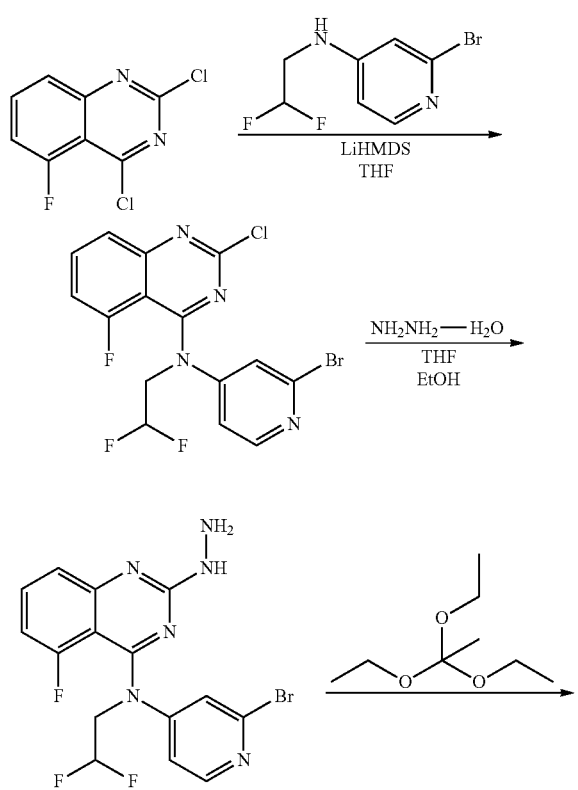

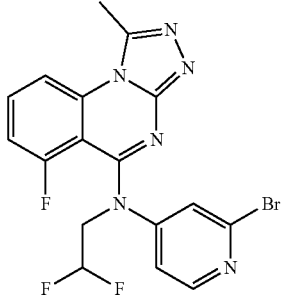

Synthesis of N-(2-bromopyridin-4-yl)-2-chloro-N-(2,2-difluoroethyl)-5-fluoroquinazolin-4-amine: A solution of 2,4-dichloro-5-fluoroquinazoline (500 mg, 2.3 mmol) in THF (5 ml) at −20 C were added 2-bromo-N-(2,2-difluoroethyl)pyridin-4-amine (573 mg, 2.42 mmol) and LiHMDS in THF (1.0 M, 2.53 ml, 1.1 eq). The mixture was stirred for 2 hours at −20° C. Water and ethyl acetate were added to the mixture and the organic phase was dried over MgSO$_4$ and evaporated under reduced pressure. The crude product was used in the next step without further purification.

Synthesis of N-(2-bromopyridin-4-yl)-N-(2,2-difluoroethyl)-5-fluoro-2-hydrazineylquinazolin-4-amine and N-(2-bromopyridin-4-yl)-N-(2,2-difluoroethyl)-6-fluoro-1-methyl-[1,2,4]triazolo[4,3-a]quinazolin-5-amine: Syntheses of these compounds were achieved through a similar procedure as described to synthesize Example 249 using 1,1,1-triethoxyethane instead of triethoxymethane.

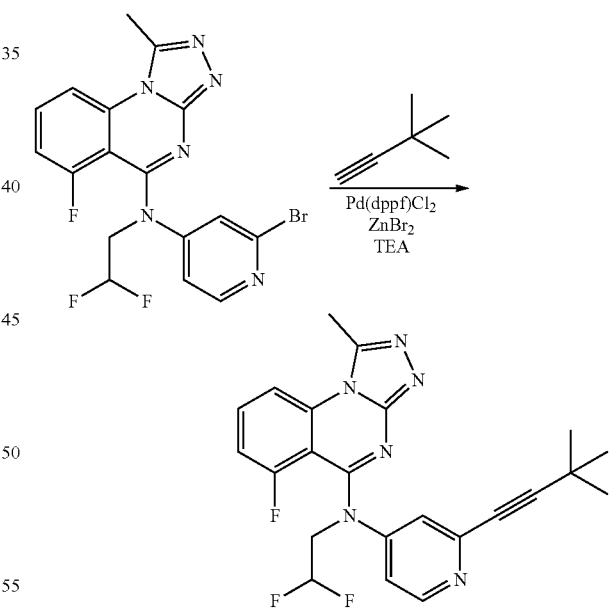

Synthesis of N-(2,2-difluoroethyl)-N-(2-(3,3-dimethylbut-1-yn-1-yl)pyridin-4-yl)-6-fluoro-1-methyl-[1,2,4]triazolo[4,3-a]quinazolin-5-amine: N-(2-bromopyridin-4-yl)-N-(2,2-difluoroethyl)-6-fluoro-1-methyl-[1,2,4]triazolo[4,3-a]quinazolin-5-amine (19.0 mg, 0.044 mmol), 3,3-dimethylbut-1-yne (3.9 mg, 0.048 mmol, 1.1 equiv.), TEA (0.1 ml, 0.86 mmol, 20 equiv.), zinc bromide (41.3 mg, 0.2 mmol, 5 equiv.) and [1,1'-bis(diphenylphosphino)ferrocene]dichloropalladium(II) (9.15 mg, 0.013 mmol, 0.3 equiv.) were heated in DMF (2 mL) at 100° C. for 10 min. After a filtration, the reaction mixture was purified by preparative reverse phase high performance liquid chromatography to give N-(2,2-difluoroethyl)-N-(2-(3,3-dimethylbut-1-yn-1-yl)pyridin-4-yl)-6-fluoro-1-methyl-[1,2,4]triazolo[4,3-a]quinazolin-5-amine. $^1$H NMR (400 MHz, Methanol-$d_4$) δ 8.30 (d, J=8.6 Hz, 1H), 8.18 (d, J=7.1 Hz, 1H), 8.13-8.00 (m, 1H), 7.37 (d, J=17.8 Hz, 2H), 7.24 (s, 1H), 6.33 (t, J=55.1 Hz, 1H), 4.65 (d, J=14.4 Hz, 1H), 3.16-3.05 (m, 2H), 1.38-1.13 (m, 9H). LCMS(m/z) 439.18.

Example 613. N-(2,2-difluoroethyl)-6-fluoro-1-methyl-N-(2-((1-methylcyclopropyl)ethynyl)pyridin-4-yl)-[1,2,4]triazolo[4,3-a]quinazolin-5-amine

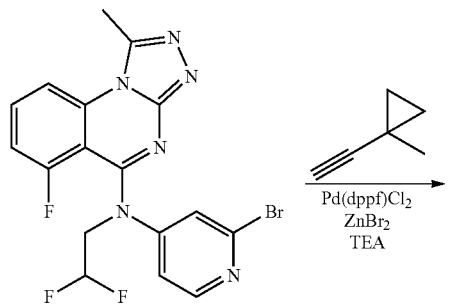

The title compound was prepared according to the method of Example 612, except using 1-ethynyl-1-methylcyclopropane instead of 3,3-dimethylbut-1-yne in the coupling step with N-(2-bromopyridin-4-yl)-N-(2,2-difluoroethyl)-6-fluoro-1-methyl-[1,2,4]triazolo[4,3-a]quinazolin-5-amine. $^1$H NMR (400 MHz, Methanol-$d_4$) δ 8.40 (d, J=8.6 Hz, 1H), 8.26 (d, J=7.0 Hz, 1H), 8.16 (td, J=8.5, 5.6 Hz, 1H), 7.53-7.41 (m, 2H), 7.32 (d, J=6.9 Hz, 1H), 6.42 (tt, J=54.8, 3.5 Hz, 1H), 4.73 (d, J=14.8 Hz, 2H), 3.19 (s, 3H), 1.36 (s, 3H), 1.11 (q, J=4.3 Hz, 2H), 0.91-0.83 (m, 2H). LCMS(m/z) 437.16.

Example 614. 4-(4-((2,2-difluoroethyl)(6-fluoro-1-methyl-[1,2,4]triazolo[4,3-a]quinazolin-5-yl)amino)pyridin-2-yl)-2-methylbut-3-yn-2-ol

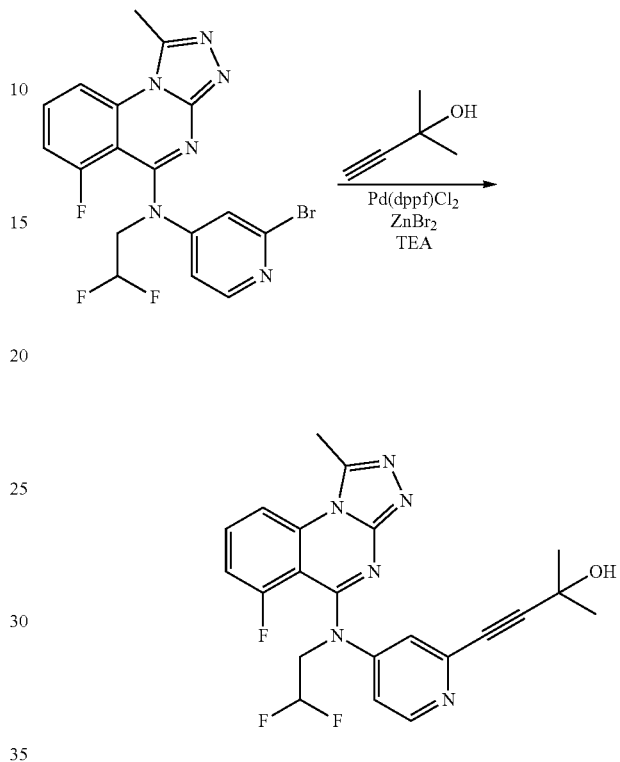

The title compound was prepared according to the method of Example 612, except using 2-methylbut-3-yn-2-ol instead of 3,3-dimethylbut-1-yne in the coupling step with N-(2-bromopyridin-4-yl)-N-(2,2-difluoroethyl)-6-fluoro-1-methyl-[1,2,4]triazolo[4,3-a]quinazolin-5-amine. $^1$H NMR (400 MHz, Methanol-$d_4$) δ 8.41 (d, J=8.6 Hz, 1H), 8.33 (d, J=7.0 Hz, 1H), 8.17 (td, J=8.5, 5.6 Hz, 1H), 7.54 (d, J=2.6 Hz, 1H), 7.52-7.42 (m, 1H), 7.37 (d, J=6.7 Hz, 1H), 6.43 (tt, J=54.9, 3.5 Hz, 1H), 4.84-4.65 (m, 2H), 3.20 (s, 3H), 1.56 (s, 6H). LCMS(m/z) 441.16.

Example 615. N-(2,2-difluoroethyl)-6-fluoro-1-methyl-N-(2-((1-(trifluoromethyl)cyclopropyl)ethynyl)pyridin-4-yl)-[1,2,4]triazolo[4,3-a]quinazolin-5-amine

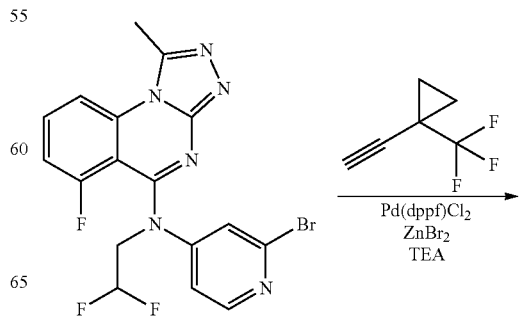

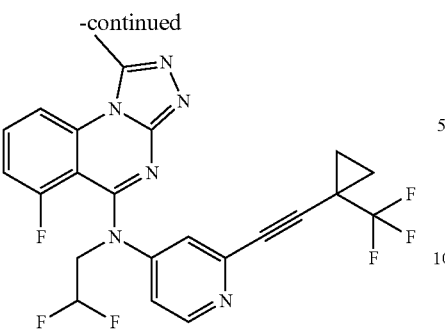

The title compound was prepared according to the method of Example 612, except using 1-ethynyl-1-(trifluoromethyl)cyclopropane instead of 3,3-dimethylbut-1-yne in the coupling step with N-(2-bromopyridin-4-yl)-N-(2,2-difluoroethyl)-6-fluoro-1-methyl-[1,2,4]triazolo[4,3-a]quinazolin-5-amine. $^1$H NMR (400 MHz, Methanol-$d_4$) δ 8.39 (d, J=8.6 Hz, 1H), 8.33 (d, J=6.8 Hz, 1H), 8.15 (td, J=8.5, 5.5 Hz, 1H), 7.55 (d, J=2.7 Hz, 1H), 7.45 (ddd, J=12.0, 8.4, 0.8 Hz, 1H), 7.35 (dd, J=6.9, 2.7 Hz, 1H), 6.42 (tt, J=54.9, 3.6 Hz, 1H), 4.82-4.65 (m, 2H), 3.19 (s, 3H), 1.60-1.37 (m, 4H). LCMS (m/z) 491.22.

Example 616. N-(2,2-difluoroethyl)-N-(2-(3,3-dimethylbut-1-yn-1-yl)pyridin-4-yl)-6-fluoro-[1,2,4]triazolo[4,3-a]quinazolin-5-amine

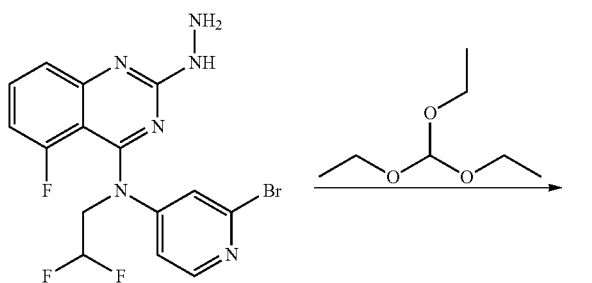

Synthesis of N-(2-bromopyridin-4-yl)-N-(2,2-difluoroethyl)-6-fluoro-[1,2,4]triazolo[4,3-a]quinazolin-5-amine: Synthesis of the above compound was achieved through a similar procedure as described to synthesize Example 249.

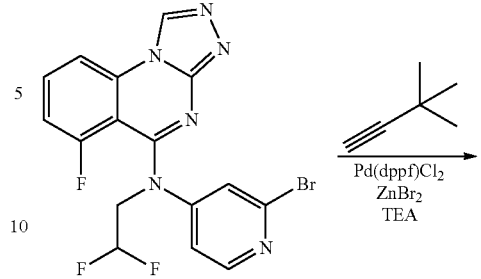

The title compound was prepared according to the method of Example 612, except using N-(2-bromopyridin-4-yl)-N-(2,2-difluoroethyl)-6-fluoro-[1,2,4]triazolo[4,3-a]quinazolin-5-amine instead of N-(2-bromopyridin-4-yl)-N-(2,2-difluoroethyl)-6-fluoro-1-methyl-[1,2,4]triazolo[4,3-a]quinazolin-5-amine in the final coupling step. $^1$H NMR (400 MHz, Methanol-$d_4$) δ 9.90 (s, 1H), 8.38 (dd, J=8.4, 0.9 Hz, 1H), 8.30 (d, J=7.0 Hz, 1H), 8.18 (td, J=8.4, 5.3 Hz, 1H), 7.58-7.42 (m, 2H), 7.37 (d, J=6.7 Hz, 1H), 6.44 (tt, J=54.9, 3.5 Hz, 1H), 4.78 (d, J=14.9 Hz, 2H), 1.37 (s, 9H); LCMS (m/z) 425.17.

Example 617. N-(2,2-difluoroethyl)-6-fluoro-N-(2-((1-methylcyclopropyl)ethynyl)pyridin-4-yl)-[1,2,4]triazolo[4,3-a]quinazolin-5-amine

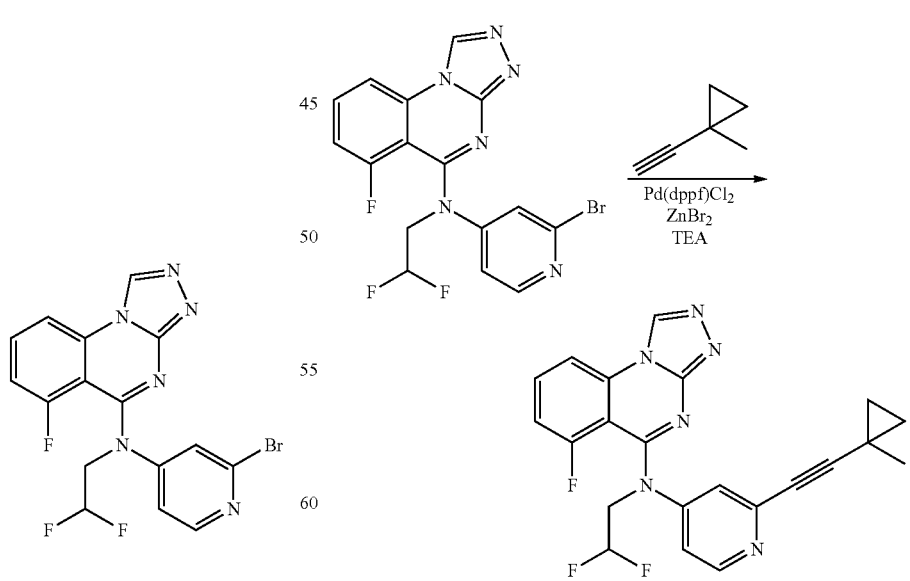

The title compound was prepared according to the method of Example 616, except using N-(2-bromopyridin-4-yl)-N-(2,2-difluoroethyl)-6-fluoro-[1,2,4]triazolo[4,3-a]quinazolin-5-amine instead of N-(2-bromopyridin-4-yl)-N-(2,2-difluoroethyl)-6-fluoro-1-methyl-[1,2,4]triazolo[4,3-a]quinazolin-5-amine in the final coupling step. $^1$H NMR (400 MHz, Methanol-$d_4$) δ 9.88 (s, 1H), 8.37 (d, J=8.4 Hz, 1H), 8.27 (d, J=7.0 Hz, 1H), 8.16 (td, J=8.4, 5.3 Hz, 1H), 7.46 (ddd, J=12.1, 8.8, 1.3 Hz, 2H), 7.34 (s, 1H), 6.42 (tt, J=54.7, 3.4 Hz, 1H), 1.36 (s, 3H), 1.11 (q, J=4.3 Hz, 2H), 0.88 (q, J=4.3 Hz, 2H); LCMS(m/z) 423.17.

Example 618. N-(2,2-difluoroethyl)-6-fluoro-N-(2-((1-(trifluoromethyl)cyclopropyl)ethynyl)pyridin-4-yl)-[1,2,4]triazolo[4,3-a]quinazolin-5-amine

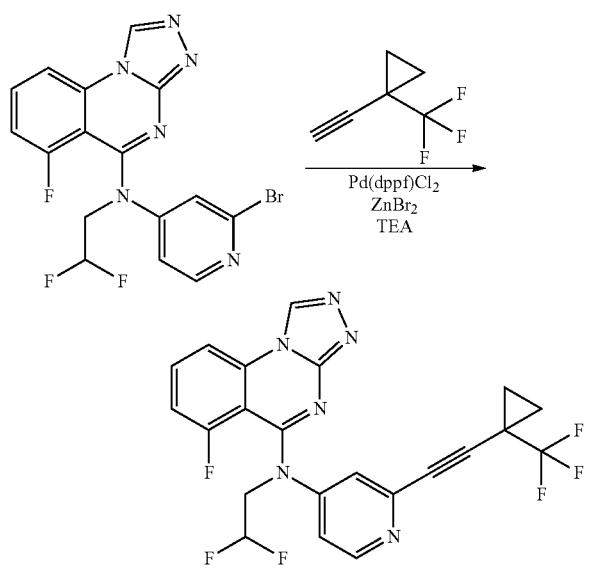

The title compound was prepared according to the method of Example 616, except using N-(2-bromopyridin-4-yl)-N-(2,2-difluoroethyl)-6-fluoro-[1,2,4]triazolo[4,3-a]quinazolin-5-amine instead of N-(2-bromopyridin-4-yl)-N-(2,2-difluoroethyl)-6-fluoro-1-methyl-[1,2,4]triazolo[4,3-a]quinazolin-5-amine in the final coupling step. $^1$H NMR (400 MHz, Methanol-$d_4$) δ 9.86 (s, 1H), 8.34 (t, J=7.2 Hz, 2H), 8.15 (td, J=8.4, 5.2 Hz, 1H), 7.57 (d, J=2.7 Hz, 1H), 7.48-7.26 (m, 2H), 6.43 (tt, J=55.0, 3.6 Hz, 1H), 4.83-4.67 (m, 2H), 1.60-1.38 (m, 4H); LCMS(m/z) 477.15.

Example 619. 4-(4-((2,2-difluoroethyl)(6-fluoro-[1,2,4]triazolo[4,3-a]quinazolin-5-yl)amino)pyridin-2-yl)-2-methylbut-3-yn-2-ol

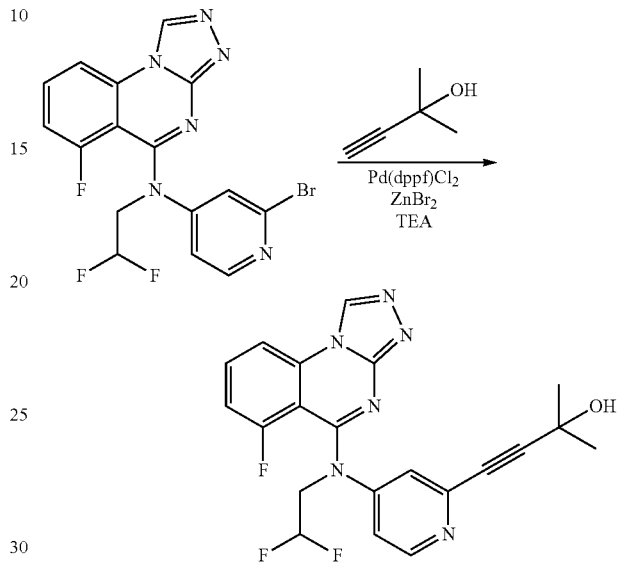

The title compound was prepared according to the method of Example 616, except using N-(2-bromopyridin-4-yl)-N-(2,2-difluoroethyl)-6-fluoro-[1,2,4]triazolo[4,3-a]quinazolin-5-amine instead of N-(2-bromopyridin-4-yl)-N-(2,2-difluoroethyl)-6-fluoro-1-methyl-[1,2,4]triazolo[4,3-a] quinazolin-5-amine in the final coupling step. $^1$H NMR (400 MHz, Methanol-$d_4$) δ 9.87 (s, 1H), 8.34 (dd, J=14.3, 7.7 Hz, 2H), 8.15 (td, J=8.4, 5.3 Hz, 1H), 7.54 (d, J=2.7 Hz, 1H), 7.50-7.41 (m, 1H), 7.36 (d, J=5.6 Hz, 1H), 6.63-6.23 (m, 1H), 4.78 (s, 2H), 1.56 (s, 6H); LCMS(m/z) 427.18.

Example 620. 6-fluoro-N-(3-fluoro-5-((1-(trifluoromethyl)cyclopropyl)ethynyl)phenyl)-1-methyl-N-(oxetan-3-ylmethyl)-[1,2,4]triazolo[4,3-a]quinazolin-5-amine

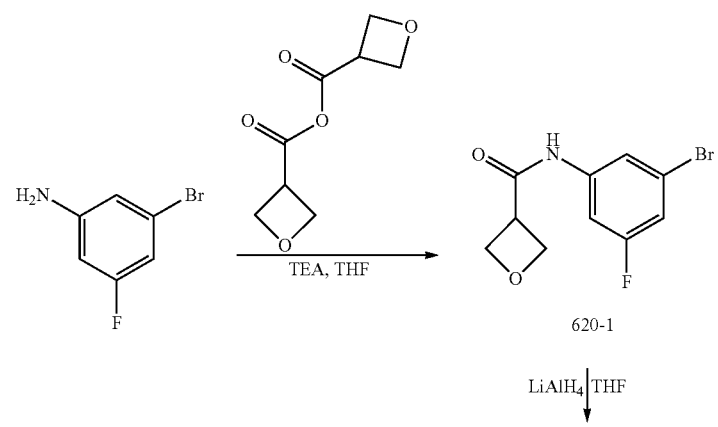

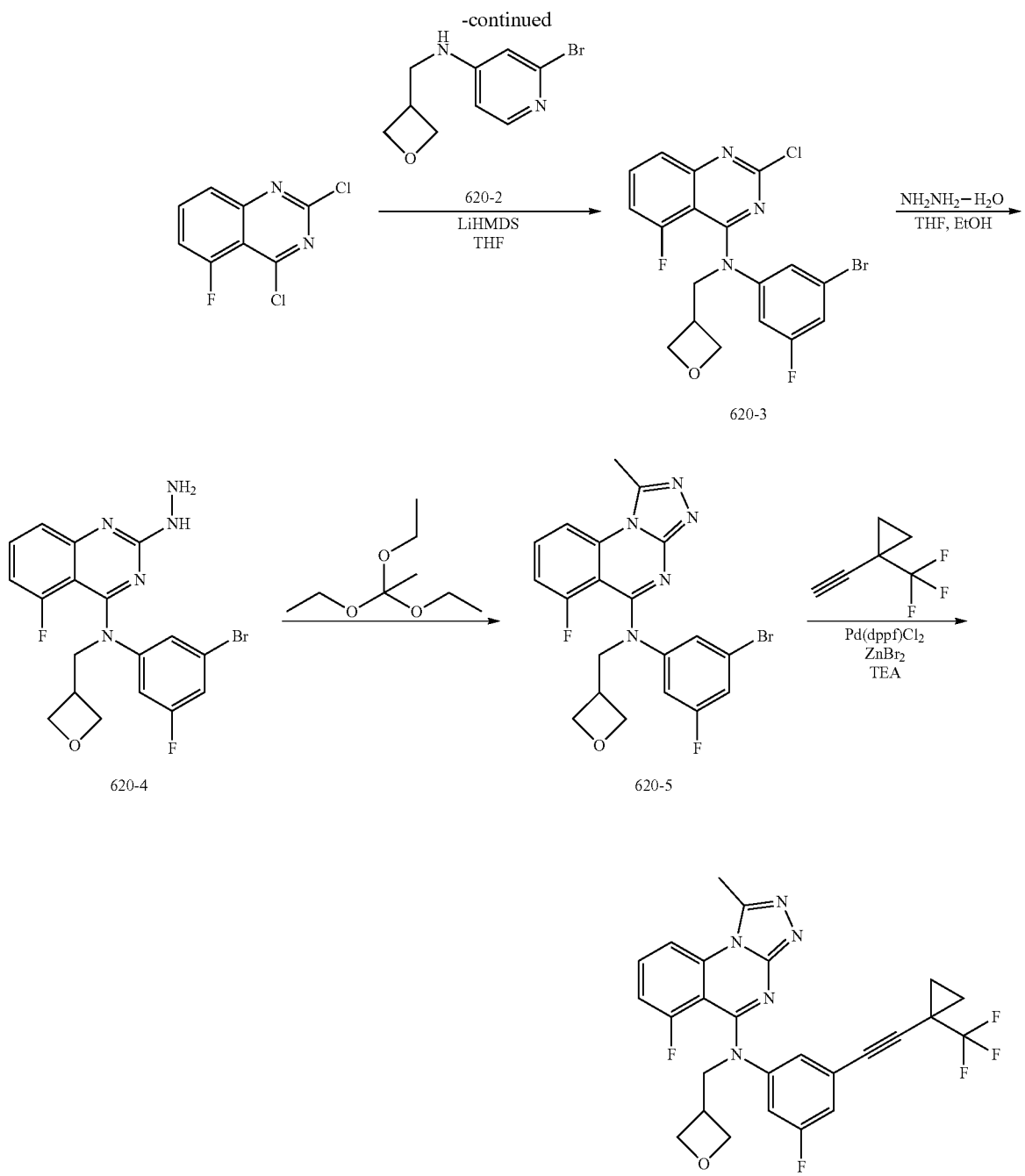

Synthesis of N-(3-bromo-5-fluorophenyl)oxetane-3-carboxamide (Compound 620-1): Synthesis of Compound 620-1 was achieved through a similar procedure as described in Example 612 using oxetane-3-carboxylic anhydride instead of 2,2-difluoroacetic anhydride.

Synthesis of the title compound was achieved through a similar procedure as described to synthesize Example 612. $^1$H NMR (400 MHz, Methanol-$d_4$) δ 8.16 (d, J=8.5 Hz, 1H), 7.92 (td, J=8.4, 5.5 Hz, 1H), 7.60 (t, J=6.1 Hz, 1H), 7.53 (dd, J=7.3, 3.4 Hz, 1H), 7.14 (dd, J=11.8, 8.3 Hz, 1H), 7.00 (d, J=10.1 Hz, 1H), 4.79-4.68 (m, 2H), 4.62 (t, J=6.5 Hz, 2H), 4.50 (d, J=6.8 Hz, 21H), 3.68 (dt, J=13.2, 5.3 Hz, 1H), 3.07 (s, 3H), 1.46-1.22 (m, 4H); LCMS(m/z) 514.22.

Example 621. N-(2,2-difluoroethyl)-6-fluoro-N-(5-((1-(trifluoromethyl)cyclopropyl)ethynyl)pyridin-3-yl)-[1,2,4]triazolo[4,3-a]quinazolin-5-amine

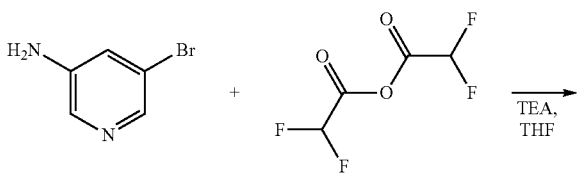

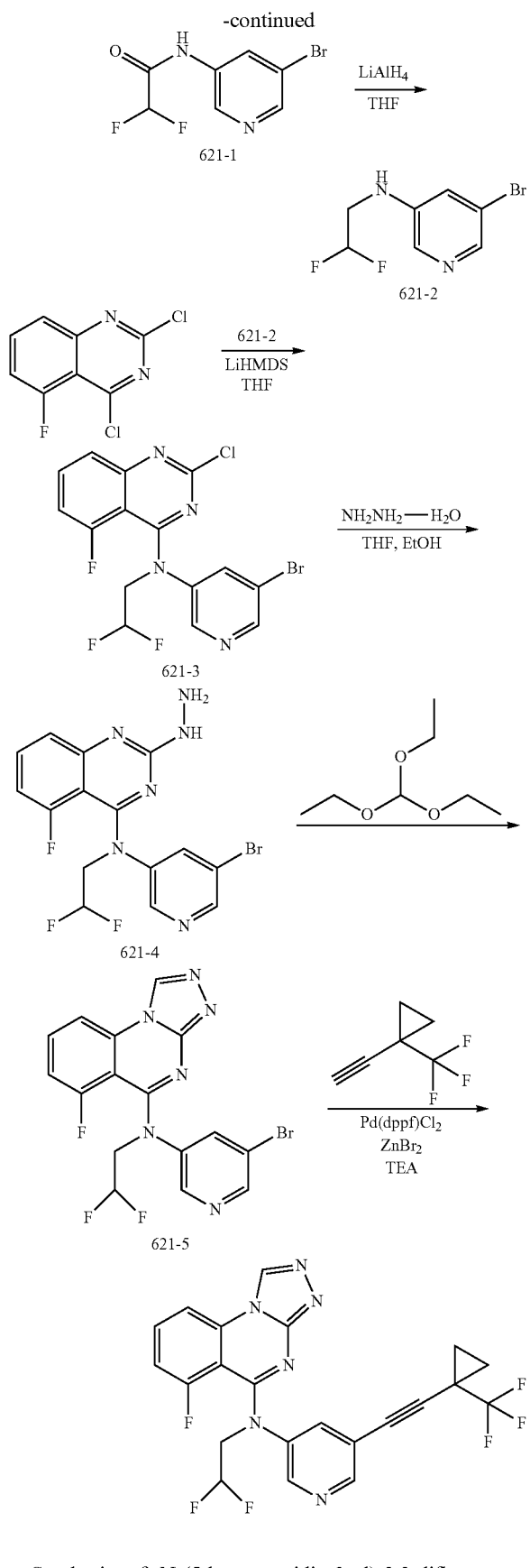

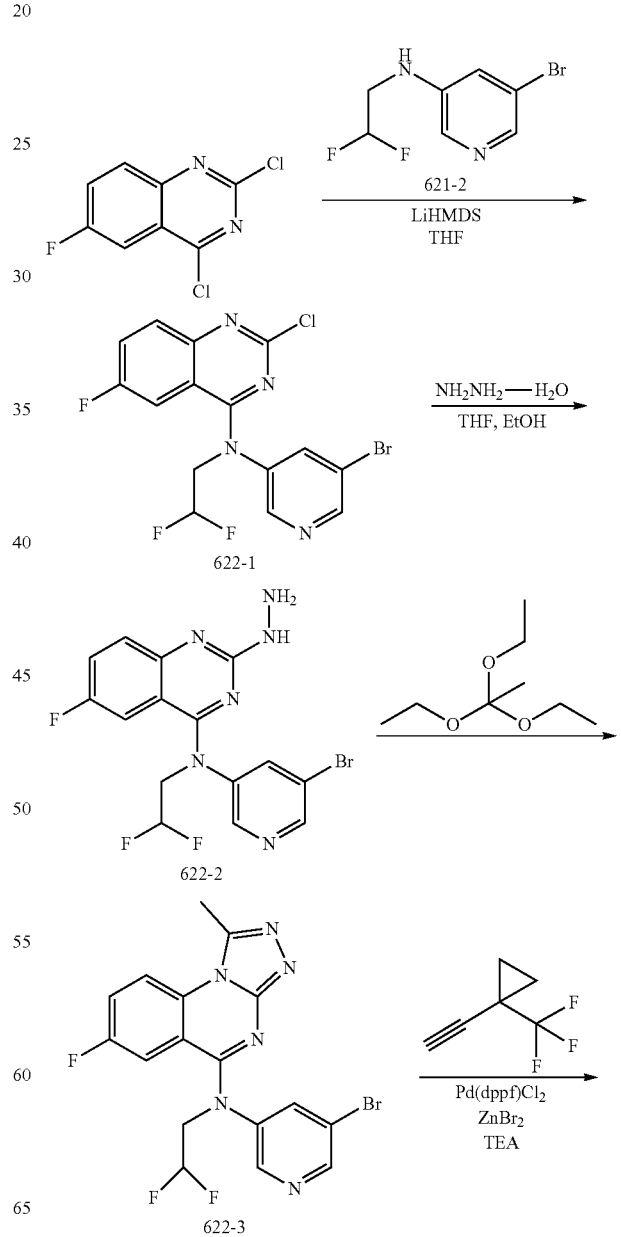

Synthesis of N-(5-bromopyridin-3-yl)-2,2-difluoroacetamide (compound 621-1): Synthesis of Compound 621-1 was achieved through a similar procedure as described to synthesize Example 42-1 using 5-bromopyridin-3-amine instead of 2-bromopyridin-4-amine.

Syntheses of Compounds 621-2, 621-3, 621-4, 621-5, and Example 621 were achieved through a similar procedure as described to synthesize Example 616. $^1$H NMR (400 MHz, Methanol-$d_4$) δ 9.73 (s, 1H), 8.47 (dd, J=7.9, 2.1 Hz, 2H), 8.26 (d, J=8.3 Hz, 1H), 8.09 (td, J=8.4, 5.1 Hz, 1H), 7.92 (t, J=2.1 Hz, 1H), 7.28 (dd, J=12.0, 8.2 Hz, 1H), 6.72-6.31 (m, 1H), 4.72 (td, J=13.6, 4.0 Hz, 2H), 1.52-1.42 (m, 2H), 1.38 (d, J=19.4 Hz, 2H). LCMS(m/z) 477.25.

Example 622. N-(2,2-difluoroethyl)-7-fluoro-1-methyl-N-(5-((1-(trifluoromethyl)cyclopropyl)ethynyl)pyridin-3-yl)-[1,2,4]triazolo[4,3-a]quinazolin-5-amine

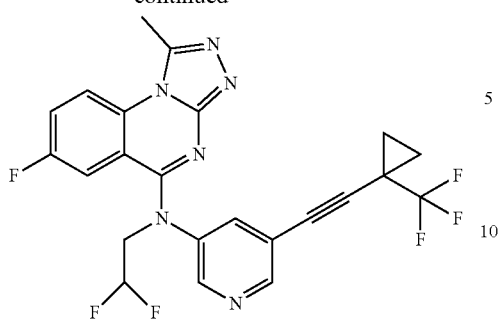

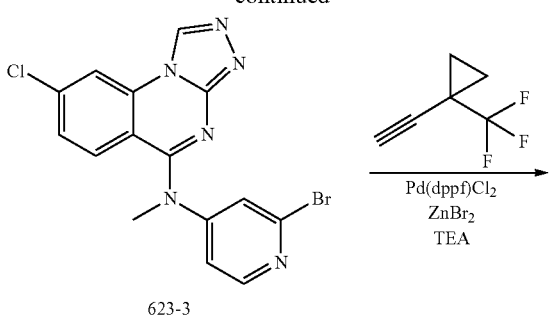

Synthesis of N-(5-bromopyridin-3-yl)-2-chloro-N-(2,2-difluoroethyl)-6-fluoroquinazolin-4-amine (Compound 622-1): Synthesis of Compound 622-1 was achieved through a similar procedure as described to synthesize Example 612-4 using 2,4-dichloro-6-fluoroquinazoline instead of 2,4-dichloro-5-fluoroquinazoline.

Syntheses of Compounds 622-2, 622-3 and Example 622 were achieved through a similar procedure as described to synthesize Example 612. $^1$H NMR (400 MHz, Methanol-$d_4$) δ 8.55-8.31 (m, 2H), 7.91 (t, J=2.1 Hz, 1H), 7.71 (ddd, J=9.6, 7.7, 2.9 Hz, 1H), 7.62-7.43 (m, 1H), 7.08 (dd, J=9.5, 2.9 Hz, 1H), 6.68-6.31 (m, 1H), 4.60 (td, J=14.2, 4.1 Hz, 2H), 3.08 (s, 3H), 1.56-1.31 (m, 4H); LCMS(m/z) 491.23.

Example 623. 8-chloro-N-methyl-N-(2-((1-(trifluoromethyl)cyclopropyl)ethynyl)pyridin-4-yl)-[1,2,4]triazolo[4,3-a]quinazolin-5-amine

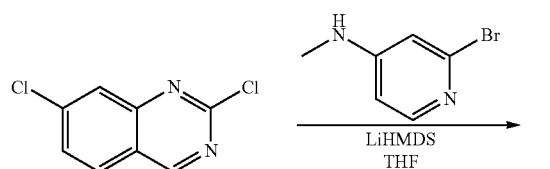

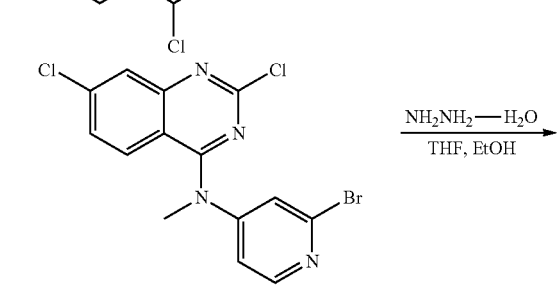

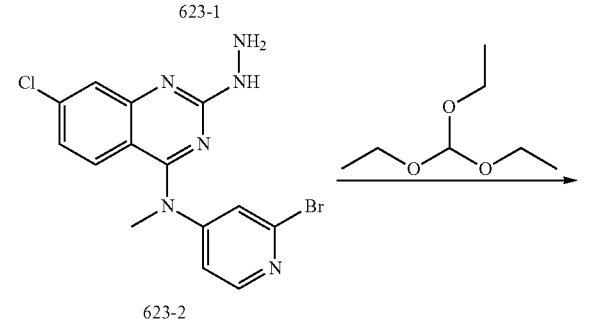

Syntheses of Compounds 623-1, 623-2, 623-3 and Example 623 were achieved through a similar procedure as described to synthesize Example 616. $^1$H NMR (400 MHz, Methanol-$d_4$) δ 9.86 (s, 1H), 8.70 (d, J=1.9 Hz, 1H), 8.34 (d, J=7.0 Hz, 1H), 7.98 (d, J=8.8 Hz, 1H), 7.74 (dd, J=8.8, 1.9 Hz, 1H), 7.56 (d, J=2.7 Hz, 1H), 7.38-7.28 (m, 1H), 3.78 (d, J=9.5 Hz, 3H), 1.63-1.51 (m, 2H), 1.46 (dtt, J=5.7, 2.8, 1.5 Hz, 2H); LCMS(m/z) 443.15.

Example 624. 8-chloro-N-(2,2-difluoroethyl)-6-fluoro-N-(3-fluoro-5-((1-(trifluoromethyl)cyclopropyl)ethynyl)phenyl)-[1,2,4]triazolo[4,3-a]quinazolin-5-amine

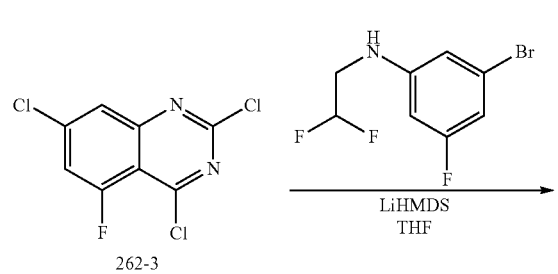

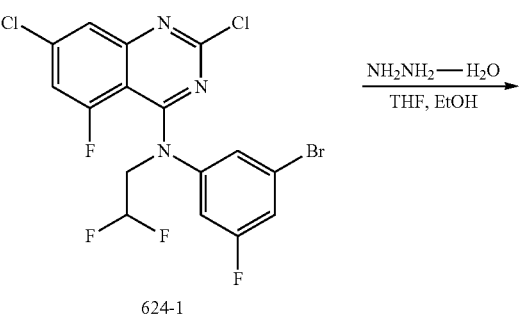

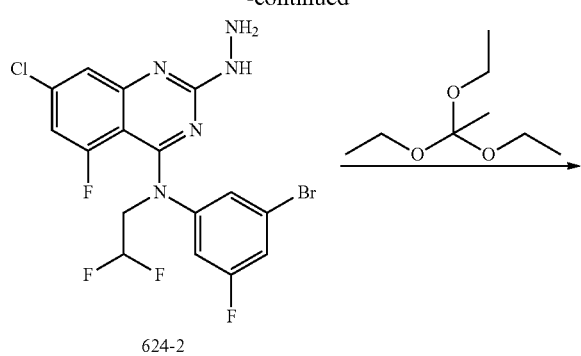

624-2

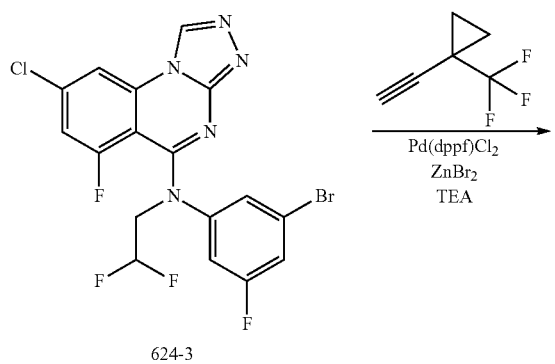

624-3

Syntheses of compounds 624-1, 624-2, and 624-3 were achieved through a similar procedure as described to synthesize Example 261.

Synthesis of the title compound was achieved through a similar procedure as described to synthesize Example 612. $^1$H NMR (400 MHz, Methanol-$d_4$) δ 9.77 (s, 1H), 8.52 (t, J=1.4 Hz, 1H), 7.54 (dd, J=11.5, 1.9 Hz, 1H), 7.50-7.12 (m, 3H), 6.47 (tt, J=55.7, 4.0 Hz, 1H), 4.73 (td, J=13.4, 4.0 Hz, 2H), 1.48-1.37 (m, 2H), 1.34-1.22 (m, 2H). LCMS(m/z) 528.2.

Example 625. 8-chloro-N-methyl-N-(5-((1-(trifluoromethyl)cyclopropyl)ethynyl)pyridin-3-yl)-[1,2,4]triazolo[4,3-a]quinazolin-5-amine

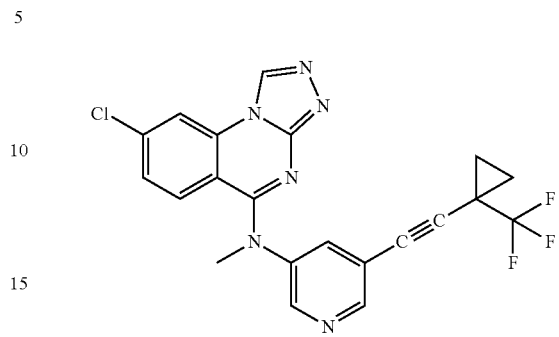

Synthesis of the title compound was achieved through a similar procedure as described to synthesize Example 612 using 5-bromo-N-methylpyridin-3-amine instead of 2-bromo-N-methylpyridin-4-amine. $^1$H NMR (400 MHz, Methanol-$d_4$) δ 9.65 (s, 1H), 8.66 (s, 1H), 8.56 (q, J=4.4, 3.9 Hz, 2H), 8.09 (d, J=2.1 Hz, 1H), 7.49 (dd, J=9.0, 2.1 Hz, 1H), 7.33 (d, J=9.1 Hz, 1H), 3.80 (s, 3H), 1.53-1.44 (m, 2H), 1.41-1.33 (m, 2H); LCMS(m/z) 443.00.

Example 626. 8-chloro-6-fluoro-N-(3-fluoro-5-((1-(trifluoromethyl)cyclopropyl)ethynyl)phenyl)-N-methyl-[1,2,4]triazolo[4,3-a]quinazolin-5-amine

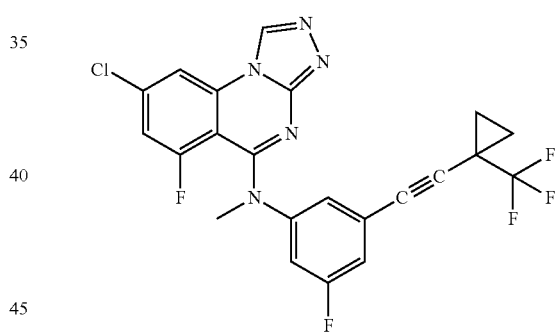

Synthesis of the title compound was achieved through a similar procedure as described to synthesize Example 624 using 3-bromo-5-fluoro-N-methylaniline instead of 3-bromo-N-(2,2-difluoroethyl)-5-fluoroaniline. $^1$H NMR (400 MHz, Chloroform-d) δ 8.95 (s, 1H), 7.71 (t, J=1.6 Hz, 1H), 7.03 (dd, J=11.0, 1.9 Hz, 1H), 6.99-6.94 (m, 1H), 6.85 (d, J=1.7 Hz, 1H), 6.70 (dt, J=9.6, 2.3 Hz, 1H), 3.65 (s, 3H), 1.43-1.33 (m, 2H), 1.31-1.22 (m, 2H); LCMS(m/z) 478.00.

Example 627. 1-[4-[3-[(8-chloro-[1,2,4]triazolo[4,3-a]quinazolin-5-yl)-methyl-amino]phenyl]phenyl]-4,4-dimethyl-pyrrolidin-2-one

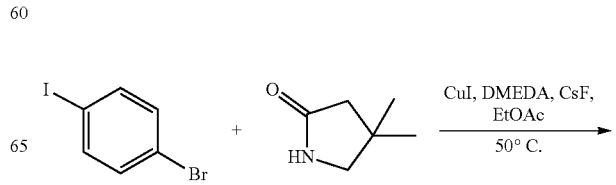

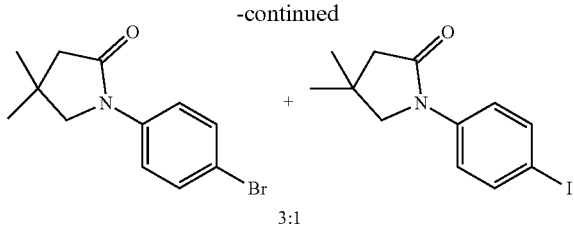

3:1

Synthesis of 1-(4-bromophenyl)-4,4-dimethylpyrrolidin-2-one: A vial with stir bar was charged with 4,4-dimethylpyrroldin-2-one (150 mg, 1.3 mmol), 1-Bromo-4-iodobenzene (450 mg, 1.6 mmol), CuI (76 mg, 0.4 mmol), and CsF (503 mg, 3.3 mmol). The vial was then flushed with nitrogen and charged with anhydrous EtOAc (5.0 mL) and DMEDA (70 mg, 0.8 mmol). The reaction was stirred at 50° C. for 16 hours at which point LC/MS indicated complete conversion to a ~3:1 mixture of bromo and iodo products. The reaction was cooled and filtered through Celite, eluting with EtOAc. The filtrate was evaporated, and the residue purified via normal phase flash chromatography using 35% EtOAc/Hexanes to give material that was a 3:1 mixture of bromo and iodo products.

Synthesis of 4,4-dimethyl-1-(4-(4,4,5,5-tetramethyl-1,3,2-dioxaborolan-2-yl)phenyl)pyrrolidin-2-one: A solution containing a 3:1 mixture of 1-(4-bromophenyl)-4,4-dimethylpyrrolidin-2-one and 1-(4-iodophenyl)-4,4-dimethylpyrrolidin-2-one (155 mg) in dioxane (7.3 mL) was degassed via nitrogen stream. To this was added Bis(pinacolato) diboron (221 mg, 0.87 mmol), (dppf)PdCl$_2$ (41 mg, 0.06 mmol), and KOAc (171 mg, 1.7 mmol). The reaction was stirred at 100° C. for 16 hours at which point LC/MS indicated partial conversion of the bromide. (dppf)PdCl$_2$ (41 mg, 0.06 mmol), B$_2$pin$_2$ (221 mg, 0.87 mmol), and KOAc (171 mg, 1.7 mmol) were added and the reaction stirred at 80° C. for 24 hours. LC/MS indicated incomplete conversion so additional (dppf)PdCl$_2$ (41 mg, 0.06 mmol), B$_2$pin$_2$ (221 mg, 0.87 mmol), and KOAc (171 mg, 1.7 mmol) were added. The reaction was stirred at 80° C. an additional 60 hours. LC/MS indicated complete conversion and the reaction was filtered through Celite and eluted with EtOAc. The filtrate was evaporated and purified via normal phase flash chromatography using 60% EtOAc/Hex to provide product: ES/MS m/z: 316.2.

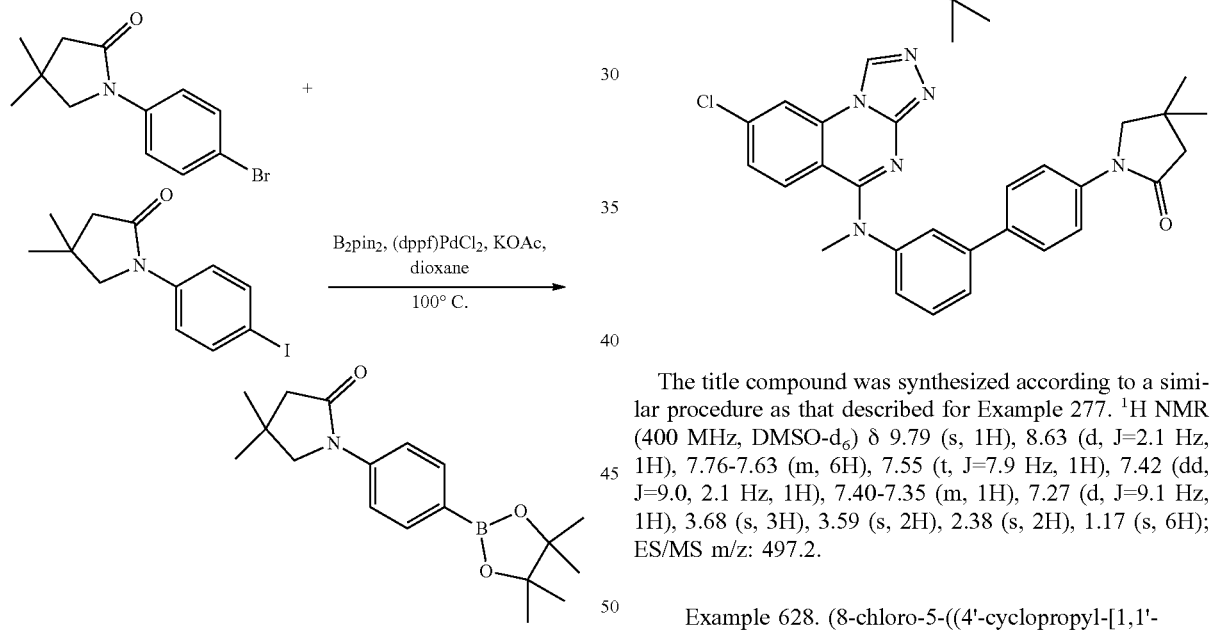

The title compound was synthesized according to a similar procedure as that described for Example 277. $^1$H NMR (400 MHz, DMSO-d$_6$) δ 9.79 (s, 1H), 8.63 (d, J=2.1 Hz, 1H), 7.76-7.63 (m, 6H), 7.55 (t, J=7.9 Hz, 1H), 7.42 (dd, J=9.0, 2.1 Hz, 1H), 7.40-7.35 (m, 1H), 7.27 (d, J=9.1 Hz, 1H), 3.68 (s, 3H), 3.59 (s, 2H), 2.38 (s, 2H), 1.17 (s, 6H); ES/MS m/z: 497.2.

Example 628. (8-chloro-5-((4'-cyclopropyl-[1,1'-biphenyl]-3-yl)(methyl)amino)-[1,2,4]triazolo[4,3-a]quinazolin-1-yl)methanol

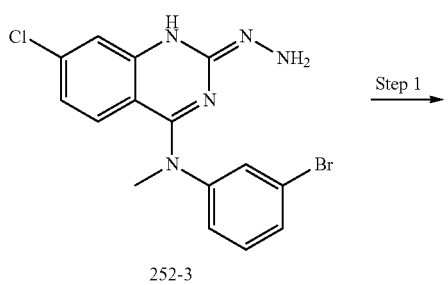

252-3

Step 1

985

-continued

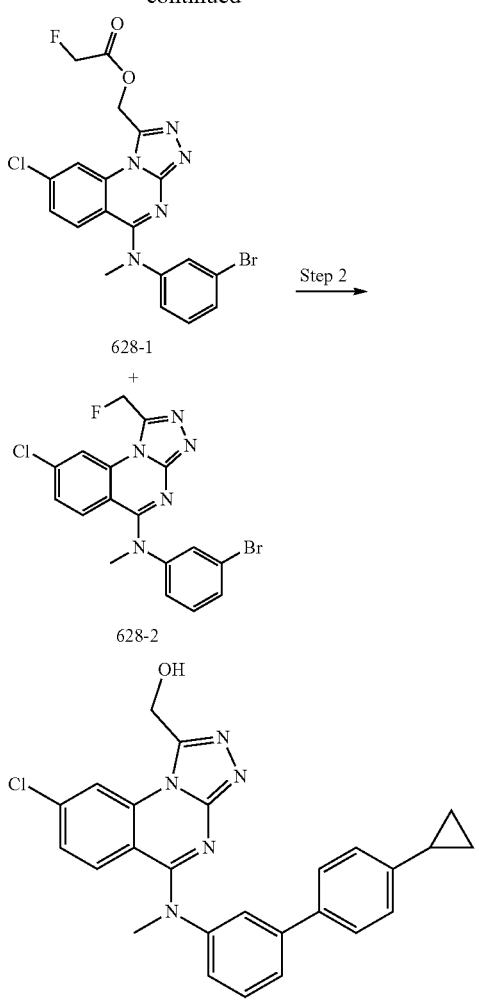

628-1

+

628-2

Step 1: A stirred mixture of Compound 252-3 (210 mg, 555 µmol) and ethyl fluoroacetate (6.00 mL, 62.1 mmol) was heated to 220° C. in a microwave reactor. After 11 h, the resulting mixture was cooled to room temperature and was concentrated under reduced pressure. The residue was purified by flash column chromatography on silica gel (0 to 100% ethyl acetate in hexanes) to give a mixture of Compound 628-1 and 628-2.

Step 2: A vigorously stirred mixture of 628-1 and 628-2 (30 mg), (4-cyclopropylphenyl)boronic acid (13.3 mg, 82.0 µmol), [1,1'-bis(diphenylphosphino)ferrocene]dichloropalladium(II) (5.6 mg, 7.7 µmol), aqueous sodium carbonate solution (2.0 M, 360 µL, 720 µmol), and 1,4-dioxane (1.0 mL) was heated to 100° C. After 5 min, the resulting mixture was cooled to room temperature. Acetic acid (0.1 mL) was added via syringe, and the resulting mixture was concentrated under reduced pressure. The residue was purified by reverse phase preparative HPLC (0.1% trifluoroacetic acid in acetonitrile/water) to give the title compound: $^1$H NMR (400 MHz, Acetone-d6) δ 8.63 (d, J=2.1 Hz, 1H), 7.63 (t, J=2.0 Hz, 1H), 7.60-7.46 (m, 5H), 7.36-7.26 (m, 2H), 7.15 (d, J=8.3 Hz, 2H), 5.23 (s, 2H), 3.70 (s, 3H), 2.13-1.88 (m, 1H), 1.09-0.95 (m, 2H), 0.78-0.63 (m, 2H); LCMS(m/z) 456.3.

986

Example 629. 8-chloro-N-(3-(5-cyclopropylpyrazin-2-yl)phenyl)-1-(difluoromethyl)-N-methyl-[1,2,4]triazolo[4,3-a]quinazolin-5-amine

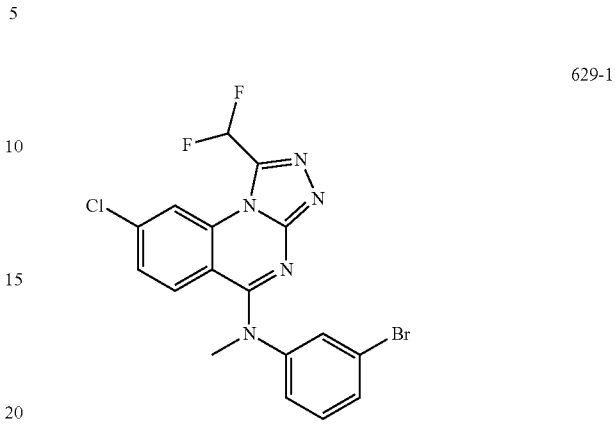

629-1

A stirred mixture of Compound 252-3 (500 mg, 1.32 mmol) and ethyl difluoroacetate (5.00 mL, 47.5 mmol) was heated to 150° C. in a microwave reactor. After 15 min, the resulting mixture was cooled to room temperature. Acetic acid (10 mL) was added, and the resulting mixture was heated to 180° C. in a microwave reactor. After 17.5 min, the resulting mixture was cooled to room temperature and was poured into a solution of sodium carbonate (10 g) in water (50 mL). The aqueous layer was extracted with ethyl acetate (100 mL), and the organic layer was washed with water (50 mL), was dried over anhydrous magnesium sulfate, was filtered, and was concentrated under reduced pressure. The residue was purified by flash column chromatography on silica gel (0 to 80% ethyl acetate in hexanes) to give Compound 629-1.

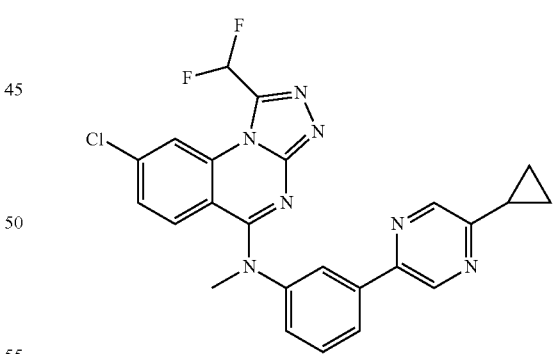

The title compound was synthesized according to the methods of Example 376, except using Compound 629-1 instead of Compound 364-2. $^1$H NMR (400 MHz, Acetone-d6) δ 8.92 (d, J=1.5 Hz, 1H), 8.62 (d, J=1.5 Hz, 1H), 8.25 (d, J=2.0 Hz, 1H), 8.14 (t, J=2.0 Hz, 1H), 8.09 (dt, J=7.8, 1.3 Hz, 1H), 7.66 (d, J=9.0 Hz, 1H), 7.60 (t, J=52.0 Hz, 1H), 7.59 (t, J=7.9 Hz, 1H), 7.49 (ddd, J=8.3, 2.4, 1.2 Hz, 1H), 7.38 (dd, J=9.0, 2.0 Hz, 1H), 3.75 (s, 3H), 2.30-2.01 (m, 1H), 1.15-0.99 (m, 4H); LCMS(m/z) 478.3.

Example 630. 8-chloro-N-(4'-cyclopropyl-[1,1'-biphenyl]-3-yl)-1-(difluoromethyl)-N-methyl-[1,2,4]triazolo[4,3-a]quinazolin-5-amine

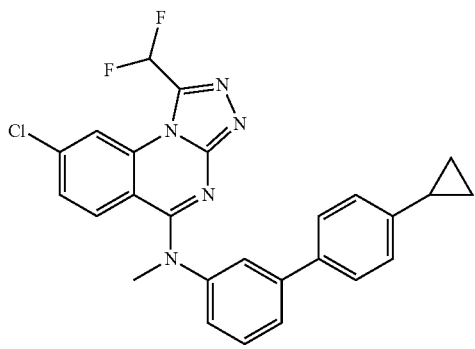 [SMILES: CN(c1cccc(-c2ccc(C3CC3)cc2)c1)c1nc2nnc(C(F)F)n2c2cc(Cl)ccc12]

The title compound was synthesized according to the methods of Example 312, except using Compound 629-1 and (4-cyclopropylphenyl)boronic acid instead of Example 308 and (4-isopropylphenyl)boronic acid. $^1$H NMR (400 MHz, Acetone-d6) δ 8.24 (d, J=2.0 Hz, 1H), 7.76-7.45 (m, 6H), 7.61 (t, J=51.8 Hz, 1H), 7.38 (dd, J=8.9, 2.0 Hz, 2H), 7.17-7.09 (m, 2H), 3.73 (s, 3H), 2.02-1.88 (m, 1H), 1.06-0.94 (m, 2H), 0.75-0.67 (m, 2H); LCMS(m/z) 476.3.

Example 631. 8-chloro-N-(4'-cyclopropyl-[1,1'-biphenyl]-3-yl)-1-(difluoromethyl)-N-methyl-[1,2,4]triazolo[4,3-a]quinazolin-5-amine

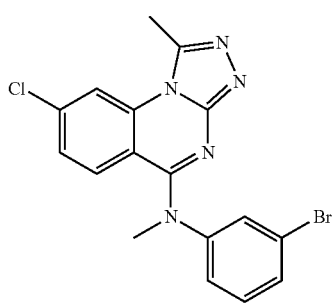

631-1

Compound 631-1 was synthesized in a manner similar to Example 252 using triethyl orthoacetate instead of triethyl orthoformate.

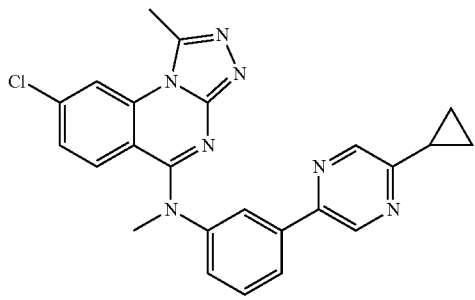 [SMILES: Cc1nnc2nc(N(C)c3cccc(-c4cnc(C5CC5)cn4)c3)c3ccc(Cl)cc3n12]

The title compound was synthesized according to the methods of Example 376, except using Compound 631-1 instead of Compound 364-2. $^1$H NMR (400 MHz, Acetone-d6) δ 8.92 (d, J=1.5 Hz, 1H), 8.61 (d, J=1.6 Hz, 1H), 8.21 (d, J=2.0 Hz, 1H), 8.04-8.00 (m, 2H), 7.62 (d, J=8.9 Hz, 1H), 7.55 (t, J=7.8 Hz, 1H), 7.39 (ddd, J=8.0, 2.3, 1.0 Hz, 1H), 7.28 (dd, J=8.9, 2.0 Hz, 1H), 3.68 (s, 3H), 3.05 (s, 3H), 2.29-1.98 (m, 1H), 1.14-1.00 (m, 4H); LCMS(m/z) 442.3.

Example 632. 8-chloro-N-(4'-cyclopropyl-[1,1'-biphenyl]-3-yl)-N,1-dimethyl-[1,2,4]triazolo[4,3-a]quinazolin-5-amine

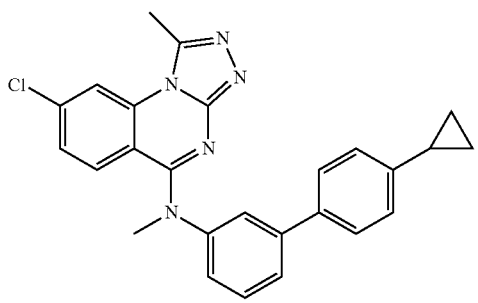 [SMILES: Cc1nnc2nc(N(C)c3cccc(-c4ccc(C5CC5)cc4)c3)c3ccc(Cl)cc3n12]

The title compound was synthesized according to the methods of Example 312, using (4-cyclopropylphenyl)boronic acid instead of (4-isopropylphenyl)boronic acid and using Compound 631-1 instead of Example 308. $^1$H NMR (400 MHz, Acetone-d$_6$) δ 8.28 (d, J=2.1 Hz, 1H), 7.66-7.57 (m, 3H), 7.57-7.47 (m, 3H), 7.39-7.31 (m, 2H), 7.19-7.11 (m, 2H), 3.73 (s, 3H), 3.10 (s, 3H), 2.02-1.91 (m, 1H), 1.05-0.95 (m, 2H), 0.77-0.66 (m, 2H); LCMS(m/z) 440.3.

Example 633. (R)-8-chloro-N-methyl-N-(3-(6-((1,1,1-trifluoropropan-2-yl)oxy)pyridin-3-yl)phenyl)-[1,2,4]triazolo[4,3-a]quinazolin-5-amine

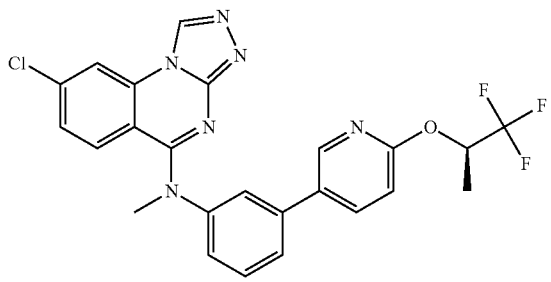 [SMILES: C[C@@H](Oc1ccc(-c2cccc(N(C)c3nc4nncn4c4cc(Cl)ccc34)c2)cn1)C(F)(F)F]

The title compound was synthesized according to the methods of Example 240, except using (R)-1,1,1-trifluoropropan-2-ol instead of (±)-1,1,1-trifluoropropan-2-ol. $^1$H NMR (400 MHz, Acetone-d6) δ 9.46 (s, 1H), 8.42 (dd, J=2.6, 0.7 Hz, 1H), 8.41 (d, J=2.1 Hz, 1H), 8.05 (dd, J=8.6, 2.6 Hz, 1H), 7.72 (t, J=2.0 Hz, 1H), 7.69-7.61 (m, 1H), 7.61-7.48 (m, 2H), 7.47-7.35 (m, 1H), 7.28 (dd, J=9.0, 2.1 Hz, 1H), 6.94 (dd, J=8.6, 0.7 Hz, 1H), 6.00-5.87 (m, 1H), 3.70 (s, 3H), 1.51 (d, J=6.5 Hz, 3H); LCMS(m/z) 499.3.

Example 634. N-(3-(5-(bicyclo[1.1.1]pentan-1-yl)pyridin-2-yl)phenyl)-8-chloro-N-methyl-[1,2,4]triazolo[4,3-a]quinazolin-5-amine

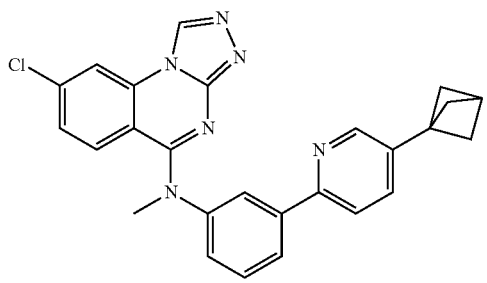

The title compound was synthesized according to the methods of Example 384, except using 2-chloro-5-iodopyridine instead of 5-bromo-2-iodopyridine. $^1$H NMR (400 MHz, Acetone-d6) δ 9.44 (s, 1H), 8.52 (dd, J=2.3, 0.9 Hz, 1H), 8.39 (d, J=2.1 Hz, 1H), 8.09 (d, J=2.0 Hz, 1H), 8.08-8.04 (m, 1H), 7.86 (dd, J=8.2, 0.9 Hz, 1H), 7.67 (dd, J=8.2, 2.3 Hz, 1H), 7.59-7.47 (m, 2H), 7.40 (d, J=9.0 Hz, 1H), 7.24 (dd, J=8.9, 2.1 Hz, 1H), 3.69 (s, 3H), 2.59 (s, 1H), 2.17 (s, 6H); LCMS(m/z) 453.3.

Example 635. 8-chloro-N-methyl-N-(3-(4,4,4-trifluoro-3,3-dimethylbut-1-yn-1-yl)phenyl)-[1,2,4]triazolo[4,3-a]quinazolin-5-amine

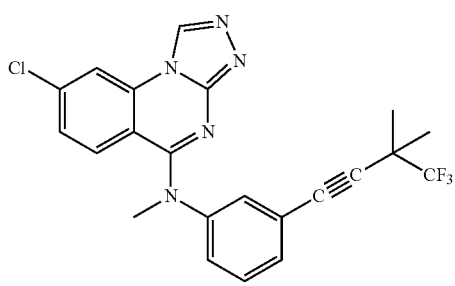

The title compound was synthesized according to the methods of Example 385, except using 3,3,3-trifluoro-2,2-dimethylpropanal instead of bicyclo[1.1.1]pentane-1-carbaldehyde. $^1$H NMR (400 MHz, Acetone-d6) δ 9.47 (s, 1H), 8.42 (d, J=2.1 Hz, 1H), 7.52 (s, 1H), 7.46 (d, J=8.9 Hz, 1H), 7.41 (d, J=7.6 Hz, 1H), 7.40-7.31 (m, 3H), 3.63 (s, 3H), 1.51 (s, 6H); LCMS(m/z) 444.3.

Example 636. 5-(6-fluoro-1-methyl-[1,2,4]triazolo[4,3-a]quinazolin-5-yl)-9-(4,4,4-trifluoro-3,3-dimethylbut-1-yn-1-yl)-2,3,4,5-tetrahydrobenzo[b][1,4]oxazepine

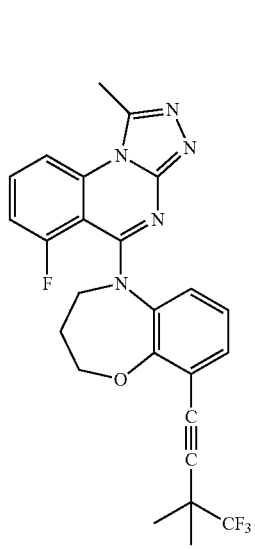 [SMILES: Cc1nnc2nc(N3CCCOc4c(C#CC(C)(C)C(F)(F)F)cccc43)c3c(F)cccc3n12]

The title compound was synthesized according to the preparation of the core structures as described in Example 261, with the final coupling reaction as described in Example 421. $^1$H NMR (400 MHz, Methanol-d$_4$) δ 8.21 (d, J=8.6 Hz, 1H), 8.02 (td, J=8.5, 5.3 Hz, 1H), 7.33 (q, J=4.3 Hz, 1H), 7.29-7.10 (m, 1H), 6.86-6.71 (m, 2H), 4.44 (b, 2H), 3.39-3.25 (m, 2H), 3.09 (s, 3H), 2.38-2.09 (m, 2H), 1.58 (s, 6H); LCMS(m/z) 484.4.

Example 637. 4-(5-(6-fluoro-1-methyl-[1,2,4]triazolo[4,3-a]quinazolin-5-yl)-2,3,4,5-tetrahydrobenzo[b][1,4]oxazepin-9-yl)-2-methylbut-3-yn-2-ol

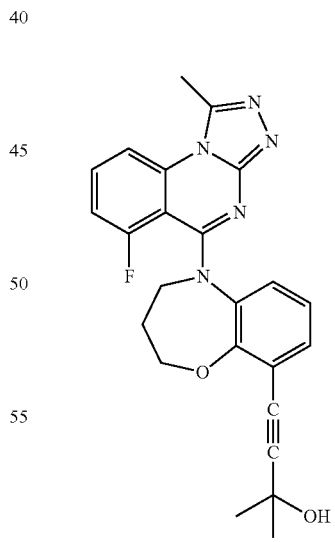

The title compound was synthesized according to the preparation of the core structures as described in Example 261, with the final coupling reaction as described in Example 421. $^1$H NMR (400 MHz, Methanol-d$_4$) δ 8.22 (d, J=8.6 Hz, 1H), 8.02 (q, J=8.4 Hz, 1H), 7.34 (dd, J=6.7, 2.7 Hz, 1H), 7.23 (dd, J=11.5, 8.3 Hz, 1H), 6.85-6.71 (m, 2H), 4.46 (b, 2H), 3.39-3.25 (m, 2H), 3.09 (s, 3H), 2.28 (b, 2H), 1.63 (s, 6H); LCMS(m/z) 432.3.

Example 638. 5-(6-fluoro-1-methyl-[1,2,4]triazolo[4,3-a]quinazolin-5-yl)-9-((1-(trifluoromethyl)cyclopropyl)ethynyl)-2,3,4,5-tetrahydrobenzo[b][1,4]oxazepine

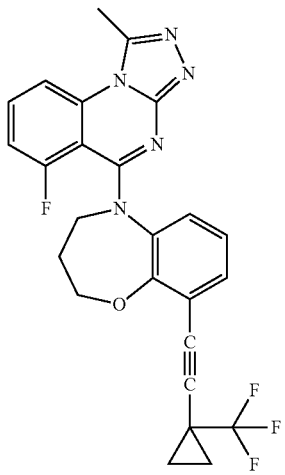 [SMILES: Cc1nnc2nc(N3CCCOc4c(C#CC5(C(F)(F)F)CC5)cccc43)c3c(F)cccc3n12]

The title compound was synthesized according to the preparation of the core structures as described in Example 261, with the final coupling reaction as described in Example 421. ¹H NMR (400 MHz, Methanol-d₄) δ 8.22 (d, J=8.6 Hz, 1H), 8.02 (td, J=8.5, 5.3 Hz, 1H), 7.35 (dd, J=5.5, 3.8 Hz, 1H), 7.24 (dd, J=11.5, 8.3 Hz, 1H), 6.87-6.70 (m, 2H), 4.46 (b, 2H), 3.39-3.25 (m, 2H), 3.09 (s, 3H), 2.28 (d, J=5.7 Hz, 2H), 1.58-1.26 (m, 4H); LCMS(m/z) 482.3.

Example 639. 9-(1-(difluoromethyl)cyclopropyl)ethynyl)-5-(6-fluoro-1-methyl-[1,2,4]triazolo[4,3-a]quinazolin-5-yl)-2,3,4,5-tetrahydrobenzo[b][1,4]oxazepine

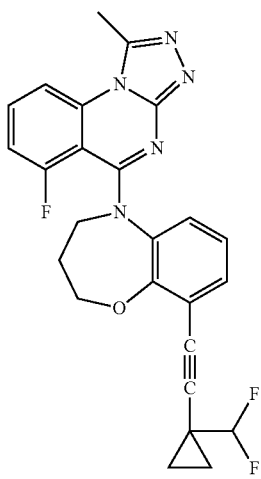 [SMILES: Cc1nnc2nc(N3CCCOc4c(C#CC5(C(F)F)CC5)cccc43)c3c(F)cccc3n12]

The title compound was synthesized according to the preparation of the core structures as described in Example 261, with the final coupling reaction as described in Example 421. ¹H NMR (400 MHz, Methanol-d₄) δ 8.20 (d, J=8.6 Hz, 1H), 8.00 (td, J=8.4, 5.3 Hz, 1H), 7.33 (dd, J=6.8, 2.5 Hz, 1H), 7.22 (dd, J=11.5, 8.3 Hz, 1H), 6.82-6.65 (m, 2H), 5.75 (t, J=56.7 Hz, 1H), 4.44 (b, 2H), 3.39-3.25 (m, 2H), 3.08 (s, 3H), 2.36-2.16 (m, 2H), 1.39-1.16 (m, 4H); LCMS(m/z) 464.4.

Example 640. 9-(3,3-dimethylbut-1-yn-1-yl)-5-(6-fluoro-1-methyl-[1,2,4]triazolo[4,3-a]quinazolin-5-yl)-2,3,4,5-tetrahydrobenzo[b][1,4]oxazepine

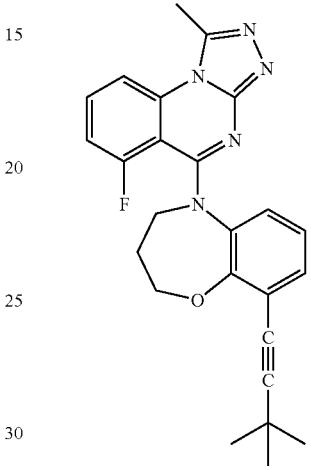

The title compound was synthesized according to the preparation of the core structures as described in Example 261, with the final coupling reaction as described in Example 421. ¹H NMR (400 MHz, Methanol-d₄) δ 8.20 (d, J=8.6 Hz, 1H), 8.01 (td, J=8.5, 5.3 Hz, 1H), 7.36-7.16 (m, 2H), 6.83-6.66 (m, 2H), 4.42 (b, 2H), 3.39-3.25 (m, 2H), 3.08 (s, 3H), 2.33-2.19 (m, 2H), 1.38 (s, 9H); LCMS(m/z) 430.3.

Example 641. 9-fluoro-1-methyl-5-(5-(4,4,4-trifluoro-3,3-dimethylbut-1-yn-1-yl)-3,4-dihydroquinolin-1(2H)-yl)-[1,2,4]triazolo[4,3-a]quinazoline

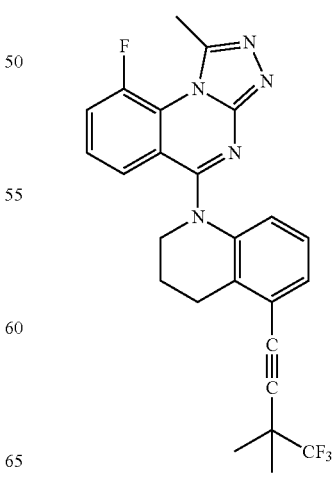

The title compound was synthesized according to the preparation of the core structures as described in Example 261, with the final coupling reaction as described in Example 421. ¹H NMR (400 MHz, Methanol-d₄) δ 7.85 (ddd, J=13.1, 7.4, 2.2 Hz, 1H), 7.60-7.45 (m, 2H), 7.35 (dd, J=7.6, 1.3 Hz, 1H), 7.04 (t, J=7.9 Hz, 1H), 6.97 (dd, J=8.2, 1.2 Hz, 1H), 4.22 (t, J=6.6 Hz, 2H), 3.12 (t, J=6.7 Hz, 2H), 2.99 (d, J=14.2 Hz, 3H), 2.24 (p, J=6.6 Hz, 2H), 1.59 (s, 6H); LCMS(m/z) 468.4.

Example 642. 4-(1-(9-fluoro-1-methyl-[1,2,4]triazolo[4,3-a]quinazolin-5-yl)-1,2,3,4-tetrahydroquinolin-5-yl)-2-methylbut-3-yn-2-ol

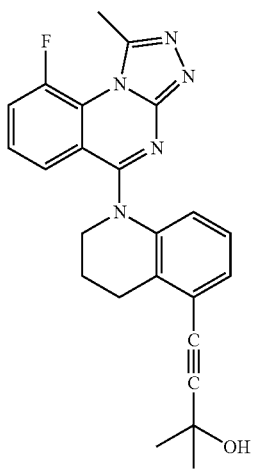 [SMILES: Cc1nnc2nc(N3CCCc4c(C#CC(C)(C)O)cccc43)c3cccc(F)c3n12]

The title compound was synthesized according to the preparation of the core structures as described in Example 261, with the final coupling reaction as described in Example 421. ¹H NMR (400 MHz, Methanol-d₄) δ 7.88-7.79 (m, 1H), 7.62-7.45 (m, 2H), 7.33 (d, J=7.5 Hz, 1H), 7.02 (t, J=7.9 Hz, 1H), 6.93 (d, J=8.1 Hz, 1H), 4.22 (t, J=6.6 Hz, 2H), 3.14 (t, J=6.6 Hz, 2H), 2.99 (d, J=14.1 Hz, 3H), 2.23 (p, J=6.6 Hz, 2H), 1.64 (s, 6H); LCMS(m/z) 416.3.

Example 643. 5-(5-((1-(difluoromethyl)cyclopropyl)ethynyl)-3,4-dihydroquinolin-1(2H)-yl)-9-fluoro-1-methyl-[1,2,4]triazolo[4,3-a]quinazoline

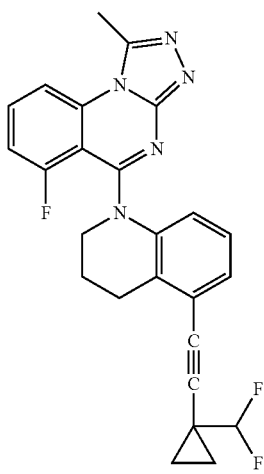 [SMILES: Cc1nnc2nc(N3CCCc4c(C#CC5(C(F)F)CC5)cccc43)c3c(F)cccc3n12]

The title compound was synthesized according to the preparation of the core structures as described in Example 261, with the final coupling reaction as described in Example 421. ¹H NMR (400 MHz, Methanol-d₄) δ 7.85 (ddd, J=13.1, 7.1, 2.4 Hz, 1H), 7.59-7.43 (m, 2H), 7.33 (dd, J=7.6, 1.2 Hz, 1H), 7.02 (t, J=7.9 Hz, 1H), 6.93 (dd, J=8.1, 1.2 Hz, 1H), 5.71 (t, J=56.5 Hz, 1H), 4.22 (t, J=6.6 Hz, 2H), 3.13 (t, J=6.7 Hz, 2H), 2.99 (d, J=14.2 Hz, 3H), 2.23 (p, J=6.6 Hz, 2H), 1.39-1.09 (m, 4H); LCMS(m/z) 448.4.

Example 644. 5-(5-((1-(difluoromethyl)cyclopropyl)ethynyl)-3,4-dihydroquinolin-1(2H)-yl)-9-fluoro-1-methyl-[1,2,4]triazolo[4,3-a]quinazoline

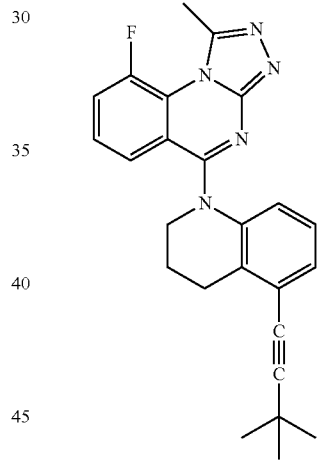

The title compound was synthesized according to the preparation of the core structures as described in Example 261, with the final coupling reaction as described in Example 421. ¹H NMR (400 MHz, Methanol-d₄) δ 7.84 (ddd, J=13.1, 6.8, 2.7 Hz, 1H), 7.54-7.44 (m, 2H), 7.28 (dd, J=7.6, 1.2 Hz, 1H), 7.00 (t, J=7.9 Hz, 1H), 6.89 (dd, J=8.2, 1.2 Hz, 1H), 4.22 (t, J=6.6 Hz, 2H), 3.11 (t, J=6.7 Hz, 2H), 2.99 (d, J=14.2 Hz, 3H), 2.24 (q, J=6.6 Hz, 2H), 1.40 (s, 9H); LCMS(m/z) 414.4.

Example 645. 5-(6,7-difluoro-1-methyl-[1,2,4]triazolo[4,3-a]quinazolin-5-yl)-9-(4,4,4-trifluoro-3,3-dimethylbut-1-yn-1-yl)-2,3,4,5-tetrahydrobenzo[b][1,4]oxazepine

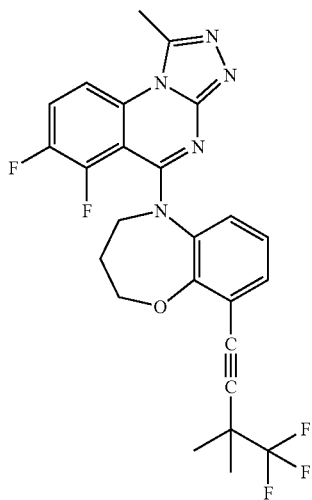 [SMILES: Cc1nnc2nc(N3CCCOc4c(C#CC(C)(C)C(F)(F)F)cccc43)c3c(F)c(F)ccc3n12]

The title compound was synthesized according to the preparation of the core structures as described in Example 261, with the final coupling reaction as described in Example 421. $^1$H NMR (400 MHz, Methanol-d$_4$) δ 8.22 (ddd, J=9.6, 3.9, 1.9 Hz, 1H), 7.98 (td, J=9.4, 7.9 Hz, 1H), 7.36 (dd, J=7.0, 2.3 Hz, 1H), 6.90-6.72 (m, 2H), 4.44 (s, 2H), 3.39-3.25 (m, 2H), 3.08 (s, 3H), 2.36-2.21 (m, 2H), 1.63-1.51 (m, 6H); LCMS(m/z) 502.4.

Example 646. 5-(6,7-difluoro-1-methyl-[1,2,4]triazolo[4,3-a]quinazolin-5-yl)-9-((1-(trifluoromethyl)cyclopropyl)ethynyl)-2,3,4,5-tetrahydrobenzo[b][1,4]oxazepine

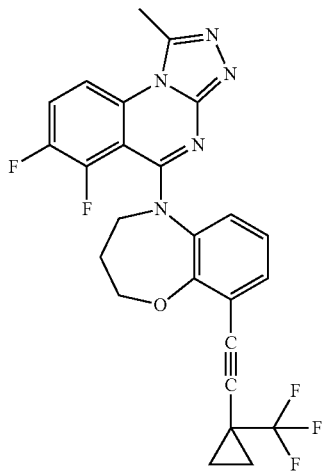 [SMILES: Cc1nnc2nc(N3CCCOc4c(C#CC5(C(F)(F)F)CC5)cccc43)c3c(F)c(F)ccc3n12]

The title compound was synthesized according to the preparation of the core structures as described in Example 261, with the final coupling reaction as described in Example 421. $^1$H NMR (400 MHz, Methanol-d$_4$) δ 8.22 (ddd, J=9.5, 3.8, 1.8 Hz, 1H), 8.07-7.86 (m, 1H), 7.38 (dd, J=6.9, 2.5 Hz, 1H), 6.89-6.72 (m, 2H), 4.45 (s, 2H), 3.39-3.25 (m, 2H), 3.08 (s, 3H), 2.28 (t, J=5.7 Hz, 2H), 1.55-1.28 (m, 4H); LCMS(m/z) 500.4.

Example 647. 5-(6,7-difluoro-1-methyl-[1,2,4]triazolo[4,3-a]quinazolin-5-yl)-9-((1-(difluoromethyl)cyclopropyl)ethynyl)-2,3,4,5-tetrahydrobenzo[b][1,4]oxazepine

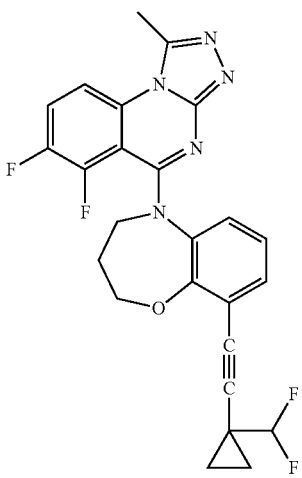 [SMILES: Cc1nnc2nc(N3CCCOc4c(C#CC5(C(F)F)CC5)cccc43)c3c(F)c(F)ccc3n12]

The title compound was synthesized according to the preparation of the core structures as described in Example 261, with the final coupling reaction as described in Example 421. $^1$H NMR (400 MHz, Methanol-d4) δ 8.22 (ddd, J=9.5, 3.9, 1.8 Hz, 1H), 7.98 (td, J=9.4, 7.9 Hz, 1H), 7.37 (dd, J=7.4, 2.0 Hz, 1H), 6.88-6.72 (m, 2H), 5.77 (t, J=56.7 Hz, 1H), 4.45 (s, 2H), 3.39-3.25 (m, 2H), 3.08 (s, 3H), 2.28 (t, J=5.8 Hz, 2H), 1.39-1.14 (m, 4H); LCMS(m/z) 482.4.

Example 648. 5-(6,7-difluoro-1-methyl-[1,2,4]triazolo[4,3-a]quinazolin-5-yl)-9-(3,3-dimethylbut-1-yn-1-yl)-2,3,4,5-tetrahydrobenzo[b][1,4]oxazepine

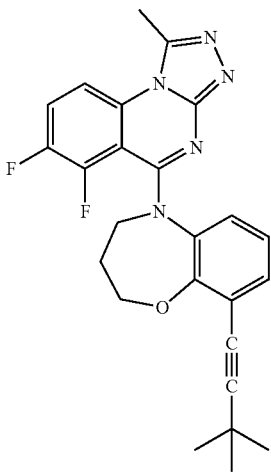 [SMILES: Cc1nnc2nc(N3CCCOc4c(C#CC(C)(C)C)cccc43)c3c(F)c(F)ccc3n12]

The title compound was synthesized according to the preparation of the core structures as described in Example 261, with the final coupling reaction as described in Example 421. ¹H NMR (400 MHz, Methanol-d₄) δ 8.21 (ddd, J=9.5, 3.9, 1.8 Hz, 1H), 7.98 (dd, J=9.4, 7.9 Hz, 1H), 7.31 (dd, J=7.7, 1.7 Hz, 1H), 6.78 (t, J=7.8 Hz, 1H), 6.71 (dd, J=7.9, 1.7 Hz, 1H), 4.41 (s, 2H), 3.39-3.25 (m, 2H), 3.07 (s, 3H), 2.36-2.15 (m, 2H), 1.38 (s, 9H); LCMS(m/z) 448.4.

Example 649. 5-(6,7-difluoro-[1,2,4]triazolo[4,3-a]quinazolin-5-yl)-9-(4,4,4-trifluoro-3,3-dimethylbut-1-yn-1-yl)-2,3,4,5-tetrahydrobenzo[b][1,4]oxazepine

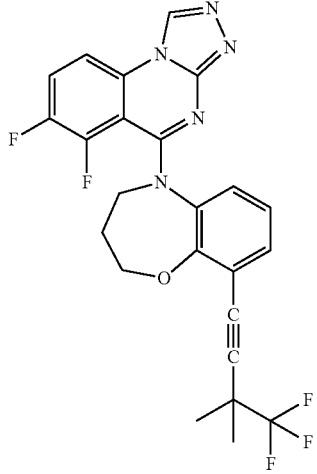 [SMILES: CC(C)(C#Cc1cccc2c1OCCCN2c1nc2nncn2c2ccc(F)c(F)c12)C(F)(F)F]

The title compound was synthesized according to the preparation of the core structures as described in Example 261, with the final coupling reaction as described in Example 421. ¹H NMR (400 MHz, Methanol-d₄) δ 9.62 (s, 1H), 8.20 (ddd, J=9.4, 4.0, 1.8 Hz, 1H), 8.02 (td, J=9.4, 7.6 Hz, 1H), 7.46-7.30 (m, 1H), 6.90-6.74 (m, 2H), 4.44 (s, 2H), 3.39-3.24 (m, 2H), 2.28 (t, J=5.6 Hz, 2H), 1.59 (s, 6H); LCMS(m/z) 488.3.

Example 650. 5-(6,7-difluoro-[1,2,4]triazolo[4,3-a]quinazolin-5-yl)-9-((1-(trifluoromethyl)cyclopropyl)ethynyl)-2,3,4,5-tetrahydrobenzo[b][1,4]oxazepine

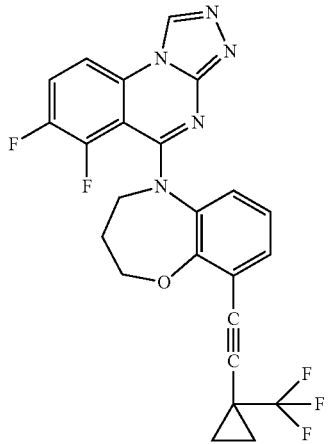 [SMILES: Fc1ccc2c(c(N3CCCOc4c(C#CC5(C(F)(F)F)CC5)cccc43)nc3nncn32)c1F]

The title compound was synthesized according to the preparation of the core structures as described in Example 261, with the final coupling reaction as described in Example 421. ¹H NMR (400 MHz, Methanol-d₄) δ 9.59 (s, 1H), 8.18 (d, J=8.9 Hz, 1H), 8.00 (q, J=8.9 Hz, 1H), 7.36 (t, J=4.7 Hz, 1H), 6.81 (d, J=4.7 Hz, 2H), 4.43 (s, 2H), 3.39-3.24 (m, 2H), 2.38-2.14 (m, 2H), 1.54-1.26 (m, 4H); LCMS(m/z) 486.3.

Example 651. 5-(6,7-difluoro-[1,2,4]triazolo[4,3-a]quinazolin-5-yl)-9-(3,3-dimethylbut-1-yn-1-yl)-2,3,4,5-tetrahydrobenzo[b][1,4]oxazepine

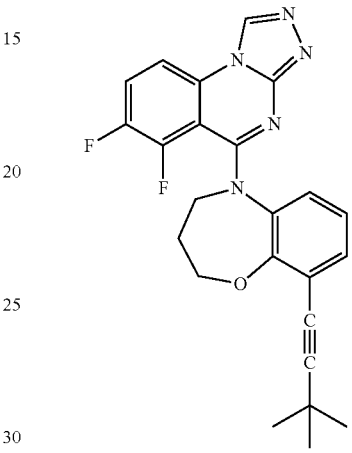

The title compound was synthesized according to the preparation of the core structures as described in Example 261, with the final coupling reaction as described in Example 421. ¹H NMR (400 MHz, Methanol-d₄) δ 9.60 (s, 1H), 8.18 (ddd, J=9.2, 4.0, 1.8 Hz, 1H), 8.00 (td, J=9.4, 7.6 Hz, 1H), 7.31 (dd, J=7.6, 1.8 Hz, 1H), 6.87-6.64 (m, 2H), 4.41 (s, 2H), 3.39-3.24 (m, 2H), 2.34-2.13 (m, 2H), 1.39 (s, 9H); LCMS(m/z) 434.3.

Example 652. 9-fluoro-5-(5-(4,4,4-trifluoro-3,3-dimethylbut-1-yn-1-yl)-3,4-dihydroquinolin-1(2H)-yl)-[1,2,4]triazolo[4,3-a]quinazoline

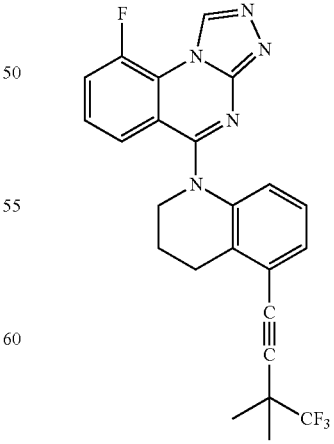

The title compound was synthesized according to the preparation of the core structures as described in Example 261, with the final coupling reaction as described in Example 421. ¹H NMR (400 MHz, Methanol-d₄) δ 9.47 (d, J=2.5 Hz, 1H), 7.88 (ddd, J=11.5, 7.4, 2.0 Hz, 1H), 7.54-7.40 (m, 2H), 7.35 (dd, J=7.6, 1.2 Hz, 1H), 7.06 (t, J=7.9 Hz, 1H), 6.98 (dd, J=8.1, 1.2 Hz, 1H), 4.23 (t, J=6.6 Hz, 2H), 3.11 (t, J=6.7 Hz, 2H), 2.24 (p, J=6.7 Hz, 2H), 1.65-1.53 (m, 6H); LCMS(m/z) 454.4.

Example 653. 4-(1-(9-fluoro-[1,2,4]triazolo[4,3-a]quinazolin-5-yl)-1,2,3,4-tetrahydroquinolin-5-yl)-2-methylbut-3-yn-2-ol

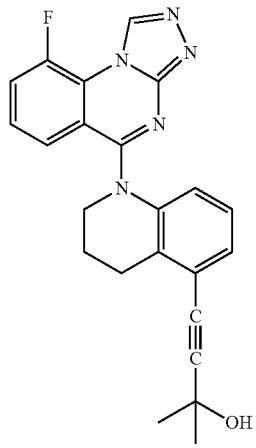 [SMILES: CC(C)(O)C#Cc1cccc2c1CCCN2c1nc2nncn2c2c(F)cccc12]

The title compound was synthesized according to the preparation of the core structures as described in Example 261, with the final coupling reaction as described in Example 421. ¹H NMR (400 MHz, Methanol-d₄) δ 9.47 (d, J=2.5 Hz, 1H), 7.94-7.76 (m, 1H), 7.58-7.40 (m, 2H), 7.34 (d, J=7.6 Hz, 1H), 7.04 (t, J=7.9 Hz, 1H), 6.95 (d, J=8.1 Hz, 1H), 4.23 (t, J=6.7 Hz, 2H), 3.17-3.09 (m, 2H), 2.23 (t, J=6.6 Hz, 2H), 1.64 (s, 6H); LCMS(m/z) 402.3.

Example 654. 9-fluoro-5-(5-((1-(trifluoromethyl)cyclopropyl)ethynyl)-3,4-dihydroquinolin-1(2H)-yl)-[1,2,4]triazolo[4,3-a]quinazoline

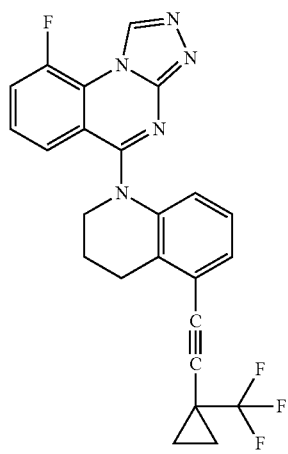 [SMILES: Fc1cccc2c(N3CCCc4c(C#CC5(C(F)(F)F)CC5)cccc43)nc3nncn3c12]

The title compound was synthesized according to the preparation of the core structures as described in Example 261, with the final coupling reaction as described in Example 421. ¹H NMR (400 MHz, Methanol-d₄) δ 9.37 (d, J=3.2 Hz, 1H), 7.83-7.69 (m, 1H), 7.51 (d, J=8.3 Hz, 1H), 7.41 (td, J=8.2, 5.0 Hz, 1H), 7.19 (dd, J=7.7, 1.1 Hz, 1H), 6.95 (t, J=7.9 Hz, 1H), 6.84-6.67 (m, 1H), 4.14-4.02 (m, 2H), 3.08 (t, J=6.7 Hz, 2H), 2.21 (p, J=6.6 Hz, 2H), 1.53-1.30 (m, 4H); LCMS(m/z) 452.3.

Example 655. 5-(5-(3,3-dimethylbut-1-yn-1-yl)-3,4-dihydroquinolin-1(2H)-yl)-9-fluoro-[1,2,4]triazolo[4,3-a]quinazoline

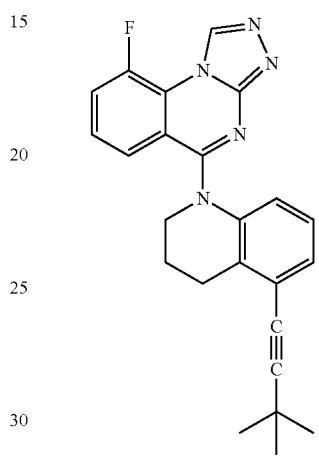

The title compound was synthesized according to the preparation of the core structures as described in Example 261, with the final coupling reaction as described in Example 421. ¹H NMR (400 MHz, Methanol-d₄) δ 9.46 (d, J=2.5 Hz, 1H), 7.87 (ddd, J=11.5, 7.9, 1.4 Hz, 1H), 7.55-7.38 (m, 2H), 7.29 (dd, J=7.6, 1.2 Hz, 1H), 7.01 (t, J=7.9 Hz, 1H), 6.91 (d, J=8.1 Hz, 1H), 4.23 (t, J=6.6 Hz, 2H), 3.11 (t, J=6.7 Hz, 2H), 2.22 (t, J=6.7 Hz, 2H), 1.40 (s, 9H); LCMS(m/z) 400.5.

Example 656. N-(2,2-difluoroethyl)-6,7-difluoro-1-methyl-N-(3-((1-(trifluoromethyl)cyclopropyl)ethynyl)phenyl)-[1,2,4]triazolo[4,3-a]quinazolin-5-amine

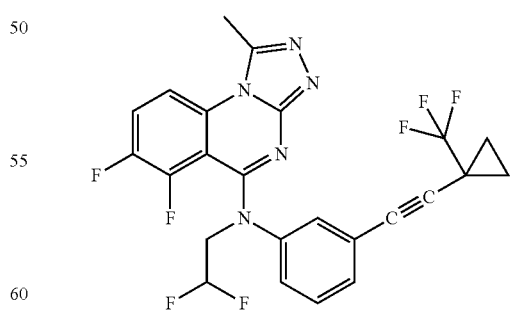

The title compound was synthesized according to the preparation of the core structures as described in Example 261, with the final coupling reaction as described in Example 421. ¹H NMR (400 MHz, Methanol-d₄) δ 8.26 (ddd, J=9.4, 3.9, 1.8 Hz, 1H), 8.01 (q, J=9.1 Hz, 1H), 7.44-7.22 (m, 4H), 6.48 (tt, J=55.9, 4.1 Hz, 1H), 4.67 (td, J=13.6, 4.1 Hz, 2H), 3.11 (s, 3H), 1.47-1.20 (m, 4H); LCMS(m/z) 508.3.

Example 657. N-(2,2-difluoroethyl)-6,7-difluoro-1-methyl-N-(3-(4,4,4-trifluoro-3,3-dimethylbut-1-yn-1-yl)phenyl)-[1,2,4]triazolo[4,3-a]quinazolin-5-amine

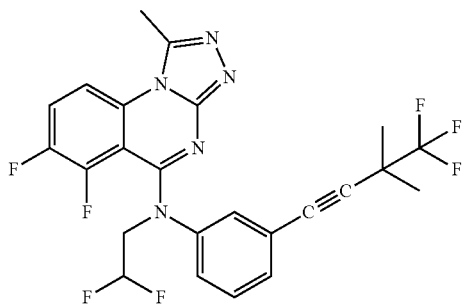 [SMILES: Cc1nnc2nc(N(CC(F)F)c3cccc(C#CC(C)(C)C(F)(F)F)c3)c3c(F)c(F)ccc3n12]

The title compound was synthesized according to the preparation of the core structures as described in Example 261, with the final coupling reaction as described in Example 421. $^1$H NMR (400 MHz, Methanol-d$_4$) δ 8.16 (ddd, J=9.5, 3.9, 1.8 Hz, 1H), 7.88 (td, J=9.4, 7.8 Hz, 1H), 7.33-7.22 (m, 3H), 7.14 (dt, J=7.5, 2.2 Hz, 1H), 6.49 (tt, J=56.1, 4.1 Hz, 1H), 4.59 (td, J=13.6, 4.1 Hz, 2H), 3.06 (s, 3H), 1.49 (s, 6H); LCMS(m/z) 510.3.

Example 658. N-(2,2-difluoroethyl)-N-(3-(3,3-dimethylbut-1-yn-1-yl)phenyl)-6,7-difluoro-1-methyl-[1,2,4]triazolo[4,3-a]quinazolin-5-amine

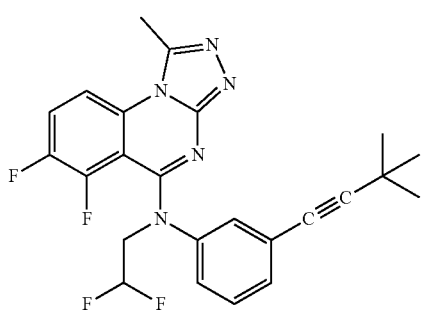 [SMILES: Cc1nnc2nc(N(CC(F)F)c3cccc(C#CC(C)(C)C)c3)c3c(F)c(F)ccc3n12]

The title compound was synthesized according to the preparation of the core structures as described in Example 261, with the final coupling reaction as described in Example 421. $^1$H NMR (400 MHz, Methanol-d$_4$) δ 8.16 (d, J=8.7 Hz, 1H), 7.88 (q, J=9.1 Hz, 1H), 7.29-7.10 (m, 3H), 7.10-6.98 (m, 1H), 6.74-6.26 (m, 1H), 4.76-4.49 (m, 2H), 3.06 (s, 3H), 1.30 (s, 9H); LCMS(m/z) 456.3.

Example 659. N-(2,2-difluoroethyl)-7-fluoro-1-methyl-N-(3-((1-(trifluoromethyl)cyclopropyl)ethynyl)phenyl)-[1,2,4]triazolo[4,3-a]quinazolin-5-amine

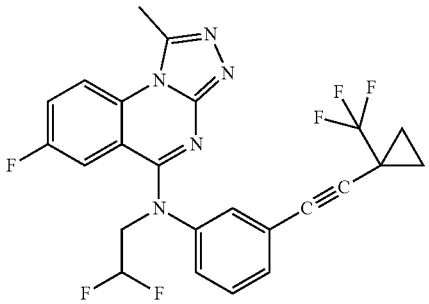 [SMILES: Cc1nnc2nc(N(CC(F)F)c3cccc(C#CC4(C(F)(F)F)CC4)c3)c3cc(F)ccc3n12]

The title compound was synthesized according to the preparation of the core structures as described in Example 261, with the final coupling reaction as described in Example 421. $^1$H NMR (400 MHz, Methanol-d$_4$) δ 8.26 (ddd, J=9.4, 3.9, 1.8 Hz, 1H), 8.01 (q, J=9.1 Hz, 1H), 7.44-7.22 (m, 4H), 6.48 (tt, J=55.9, 4.1 Hz, 1H), 4.67 (td, J=13.6, 4.1 Hz, 2H), 3.11 (s, 3H), 1.47-1.20 (m, 4H); LCMS(m/z) 508.3.

Example 660. N-(3-(4,4-difluoro-3,3-dimethylbut-1-yn-1-yl)phenyl)-N-(2,2-difluoroethyl)-6-fluoro-1-methyl-[1,2,4]triazolo[4,3-a]quinazolin-5-amine

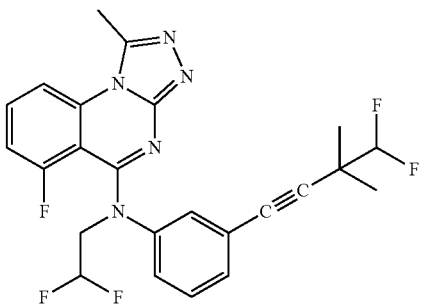 [SMILES: Cc1nnc2nc(N(CC(F)F)c3cccc(C#CC(C)(C)C(F)F)c3)c3c(F)cccc3n12]

The title compound was synthesized according to the preparation of the core structures as described in Example 261, with the final coupling reaction as described in Example 421. $^1$H NMR (400 MHz, Methanol-d$_4$) δ 8.27 (d, J=8.6 Hz, 1H), 8.06 (td, J=8.5, 5.3 Hz, 1H), 7.38-7.14 (m, 5H), 6.66-6.23 (m, 1H), 5.74 (t, J=56.7 Hz, 1H), 4.67 (td, J=13.5, 4.1 Hz, 2H), 3.12 (s, 3H), 1.33 (t, J=1.1 Hz, 6H); LCMS(m/z) 474.3.

Example 661. N-(2,2-difluoroethyl)-6-fluoro-1-methyl-N-(3-(4,4,4-trifluoro-3,3-dimethylbut-1-yn-1-yl)phenyl)-[1,2,4]triazolo[4,3-a]quinazolin-5-amine

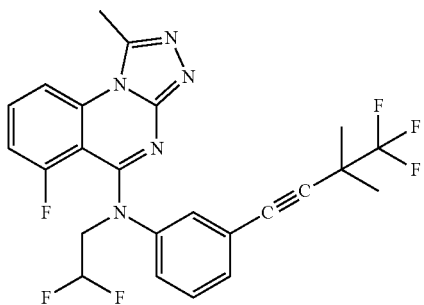 [SMILES: Cc1nnc2nc(N(CC(F)F)c3cccc(C#CC(C)(C)C(F)(F)F)c3)c3c(F)cccc3n12]

The title compound was synthesized according to the preparation of the core structures as described in Example 261, with the final coupling reaction as described in Example 421. $^1$H NMR (400 MHz, Methanol-d$_4$) δ 8.27 (d, J=8.5 Hz, 1H), 8.07 (td, J=8.4, 5.3 Hz, 1H), 7.44-7.17 (m, 5H), 6.47 (tt, J=55.9, 4.1 Hz, 1H), 4.68 (td, J=13.5, 4.1 Hz, 2H), 3.12 (s, 3H), 1.59-1.42 (m, 6H); LCMS(m/z) 492.3.

Example 662. N-(3-(4,4-difluoro-3,3-dimethylbut-1-n-1-yl)phenyl)-N-(2,2-difluoroethyl)-6-fluoro-[1,2,4]triazolo[4,3-a]quinazolin-5-amine

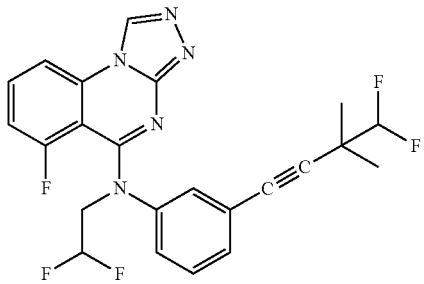 [SMILES: CC(C)(C#Cc1cccc(N(CC(F)F)c2nc3nncn3c3cccc(F)c23)c1)C(F)F]

The title compound was synthesized according to the preparation of the core structures as described in Example 261, with the final coupling reaction as described in Example 421. $^1$H NMR (400 MHz, Methanol-d$_4$) δ 9.68 (s, 1H), 8.21 (d, J=8.4 Hz, 1H), 8.06 (td, J=8.3, 5.0 Hz, 1H), 7.44-7.13 (m, 5H), 6.75-6.24 (m, 1H), 5.75 (t, J=56.7 Hz, 1H), 4.68 (td, J=13.5, 4.1 Hz, 2H), 1.33 (t, J=1.1 Hz, 6H); LCMS(m/z) 460.3.

Example 663. N-(2,2-difluoroethyl)-6-fluoro-N-(3-(4,4,4-trifluoro-3,3-dimethylbut-1-yn-1-yl)phenyl)-[1,2,4]triazolo[4,3-a]quinazolin-5-amine

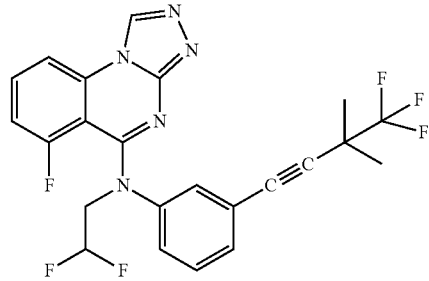 [SMILES: CC(C)(C#Cc1cccc(N(CC(F)F)c2nc3nncn3c3cccc(F)c23)c1)C(F)(F)F]

The title compound was synthesized according to the preparation of the core structures as described in Example 261, with the final coupling reaction as described in Example 421. $^1$H NMR (400 MHz, Methanol-d$_4$) δ 9.69 (s, 1H), 8.22 (d, J=8.3 Hz, 1H), 8.06 (td, J=8.3, 5.0 Hz, 1H), 7.47-7.15 (m, 5H), 6.49 (tt, J=55.9, 4.1 Hz, 1H), 4.68 (td, J=13.5, 4.1 Hz, 2H), 1.54-1.42 (m, 6H); LCMS(m/z) 478.3.

Example 664. N-(2,2-difluoroethyl)-6-fluoro-N-(3-((1-(trifluoromethyl)cyclopropyl)ethynyl)phenyl)-[1,2,4]triazolo[4,3-a]quinazolin-5-amine

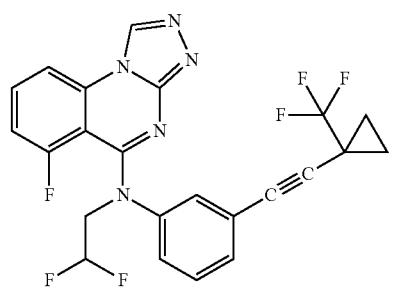 [SMILES: Fc1cccc2c1c(N(CC(F)F)c1cccc(C#CC3(C(F)(F)F)CC3)c1)nc1nncn12]

The title compound was synthesized according to the preparation of the core structures as described in Example 261, with the final coupling reaction as described in Example 421. $^1$H NMR (400 MHz, Methanol-d$_4$) δ 9.68 (s, 1H), 8.21 (d, J=8.3 Hz, 1H), 8.05 (td, J=8.3, 5.0 Hz, 1H), 7.47-7.12 (m, 5H), 6.48 (tt, J=55.9, 4.1 Hz, 1H), 4.67 (td, J=13.5, 4.1 Hz, 2H), 1.50-1.23 (m, 4H); LCMS(m/z) 476.3.

Example 665. N-(2,2-difluoroethyl)-6-fluoro-N-(3-((1-(difluoromethyl)cyclopropyl)ethynyl)phenyl)-[1,2,4]triazolo[4,3-a]quinazolin-5-amine

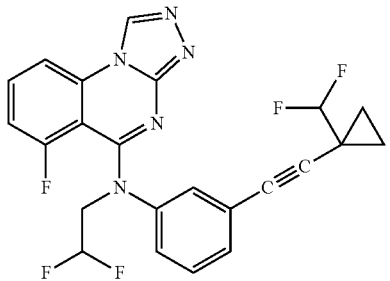 [SMILES: Fc1cccc2c1c(N(CC(F)F)c1cccc(C#CC3(C(F)F)CC3)c1)nc1nncn12]

The title compound was synthesized according to the preparation of the core structures as described in Example 261, with the final coupling reaction as described in Example 421. ¹H NMR (400 MHz, Methanol-d$_4$) δ 9.67 (s, 1H), 8.20 (d, J=8.4 Hz, 1H), 8.05 (td, J=8.4, 5.0 Hz, 1H), 7.41-7.10 (m, 5H), 6.48 (tt, J=55.9, 4.1 Hz, 1H), 5.63 (t, J=56.5 Hz, 1H), 4.66 (td, J=13.5, 4.1 Hz, 2H), 1.23-1.03 (m, 4H); LCMS(m/z) 458.3.

Example 666. 5-(7-fluoro-1-methyl-[1,2,4]triazolo[4,3-a]quinazolin-5-yl)-9-((1-(trifluoromethyl)cyclopropyl)ethynyl)-2,3,4,5-tetrahydrobenzo[b][1,4]oxazepine

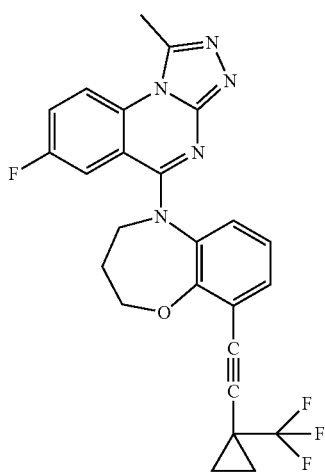 [SMILES: Cc1nnc2nc(N3CCCOc4c(C#CC5(C(F)(F)F)CC5)cccc43)c3cc(F)ccc3n12]

The title compound was synthesized according to the preparation of the core structures as described in Example 261, with the final coupling reaction as described in Example 421. ¹H NMR (400 MHz, Methanol-d$_4$) δ 8.44 (dd, J=9.4, 4.6 Hz, 1H), 7.78 (ddd, J=9.9, 7.4, 2.9 Hz, 1H), 7.56 (dd, J=5.5, 3.9 Hz, 1H), 7.09-6.97 (m, 2H), 6.82 (dd, J=10.2, 2.8 Hz, 1H), 4.40 (b, 2H), 3.08 (s, 3H), 3.37-3.28 (m, 2H), 2.26 (b, 2H), 1.56-1.25 (m, 4H); LCMS(m/z) 482.4.

Example 667. N-(2,2-difluoroethyl)-7-fluoro-N-(3-fluoro-5-(4,4,4-trifluoro-3,3-dimethylbut-1-yn-1-yl)phenyl)-[1,2,4]triazolo[4,3-a]quinazolin-5-amine

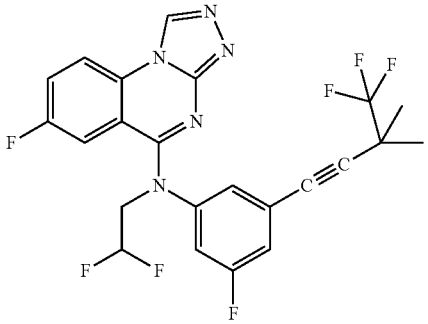 [SMILES: CC(C)(C#Cc1cc(F)cc(N(CC(F)F)c2nc3nncn3c3ccc(F)cc23)c1)C(F)(F)F]

The title compound was synthesized according to the preparation of the core structures as described in Example 261, with the final coupling reaction as described in Example 421. ¹H NMR (400 MHz, Methanol-d$_4$) δ 9.56 (s, 1H), 8.36 (dd, J=9.2, 4.7 Hz, 1H), 7.72 (ddd, J=9.1, 7.7, 2.7 Hz, 1H), 7.30 (t, J=1.6 Hz, 1H), 7.25 (dt, J=9.7, 2.2 Hz, 1H), 7.21-7.12 (m, 1H), 7.03 (dd, J=9.9, 2.7 Hz, 1H), 6.75-6.39 (m, 1H), 4.63-4.52 (m, 2H), 1.52 (s, 6H); LCMS(m/z) 496.3.

Example 668. N-(3-(4,4-difluoro-3,3-dimethylbut-1-yn-1-yl)-5-fluorophenyl)-N-(2,2-difluoroethyl)-7,9-difluoro-[1,2,4]triazolo[4,3-a]quinazolin-5-amine

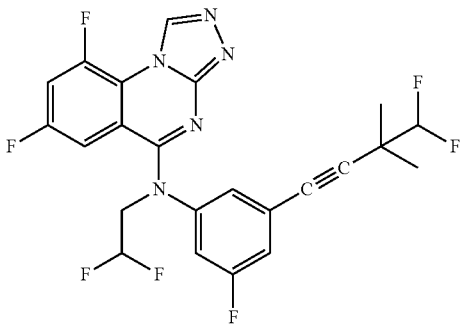

The title compound was synthesized according to the preparation of the core structures as described in Example 261, with the final coupling reaction as described in Example 421. ¹H NMR (400 MHz, Methanol-d$_4$) δ 9.47 (d, J=2.8 Hz, 1H), 7.98-7.82 (m, 1H), 7.40-7.17 (m, 3H), 6.88 (dt, J=9.7, 2.0 Hz, 1H), 6.55 (t, J=56.0 Hz, 1H), 5.78 (t, J=56.6 Hz, 1H), 4.62 (td, J=13.5, 4.2 Hz, 2H), 1.36 (d, J=1.1 Hz, 6H); LCMS(m/z) 496.3.

Example 669. N-(2,2-difluoroethyl)-7,9-difluoro-N-(3-fluoro-5-((1-methylcyclopropyl)ethynyl)phenyl)-[1,2,4]triazolo[4,3-a]quinazolin-5-amine

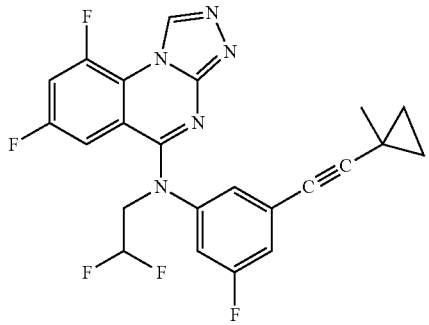 [SMILES: CC1(C#Cc2cc(F)cc(N(CC(F)F)c3nc4nncn4c4c(F)cc(F)cc34)c2)CC1]

The title compound was synthesized according to the preparation of the core structures as described in Example 261, with the final coupling reaction as described in Example 421. ¹H NMR (400 MHz, Methanol-$d_4$) δ 9.36 (d, J=3.3 Hz, 1H), 7.76 (ddd, J=11.2, 8.2, 2.6 Hz, 1H), 7.21-7.10 (m, 3H), 6.92 (ddd, J=9.6, 2.6, 1.6 Hz, 1H), 6.75-6.30 (m, 1H), 4.55 (td, J=13.7, 4.2 Hz, 2H), 1.32 (s, 3H), 0.97 (q, J=4.1 Hz, 2H), 0.79-0.65 (m, 2H); LCMS(m/z) 458.3.

Example 671. N-(2,2-difluoroethyl)-6,7-difluoro-N-(3-(4,4,4-trifluoro-3,3-dimethylbut-1-yn-1-yl)phenyl)-[1,2,4]triazolo[4,3-a]quinazolin-5-amine

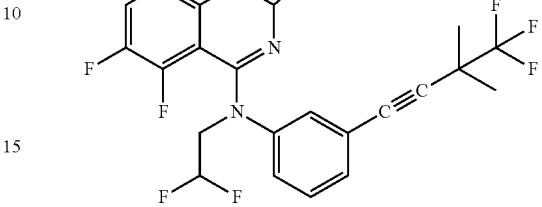

The title compound was synthesized according to the preparation of the core structures as described in Example 261, with the final coupling reaction as described in Example 421. ¹H NMR (400 MHz, Methanol-$d_4$) δ 9.65 (s, 1H), 8.22 (ddd, J=9.3, 4.0, 1.8 Hz, 1H), 8.02 (td, J=9.4, 7.6 Hz, 1H), 7.44-7.32 (m, 3H), 7.27 (td, J=4.6, 2.3 Hz, 1H), 6.48 (tt, J=55.9, 4.1 Hz, 1H), 4.66 (td, J=13.6, 4.1 Hz, 2H), 1.56-1.46 (m, 6H); LCMS(m/z) 496.3.

Example 670. N-(2,2-difluoroethyl)-7,9-difluoro-N-(3-fluoro-5-((1-(trifluoromethyl)cyclopropyl)ethynyl)phenyl)-[1,2,4]triazolo[4,3-a]quinazolin-5-amine

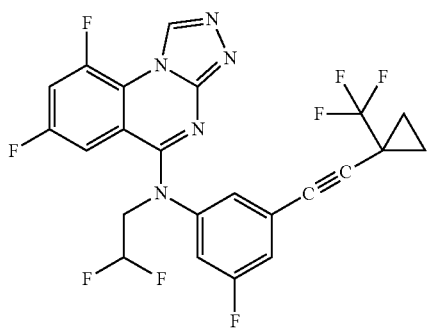 [SMILES: Fc1cc(C#CC2(C(F)(F)F)CC2)cc(N(CC(F)F)c2nc3nncn3c3c(F)cc(F)cc23)c1]

The title compound was synthesized according to the preparation of the core structures as described in Example 261, with the final coupling reaction as described in Example 421. ¹H NMR (400 MHz, Methanol-$d_4$) δ 9.37 (d, J=3.3 Hz, 1H), 7.77 (ddd, J=11.2, 8.2, 2.6 Hz, 1H), 7.35-7.21 (m, 2H), 7.19 (ddd, J=8.8, 2.4, 1.3 Hz, 1H), 6.92 (dt, J=9.6, 2.0 Hz, 1H), 6.56 (tt, J=56.3, 4.2 Hz, 1H), 4.62-4.52 (m, 2H), 1.49-1.23 (m, 4H); LCMS(m/z) 512.3.

Example 672. N-(2,2-difluoroethyl)-6-fluoro-N-(3-fluoro-5-(4,4,4-trifluoro-3,3-dimethylbut-1-yn-1-yl)phenyl)-[1,2,4]triazolo[4,3-a]quinazolin-5-amine

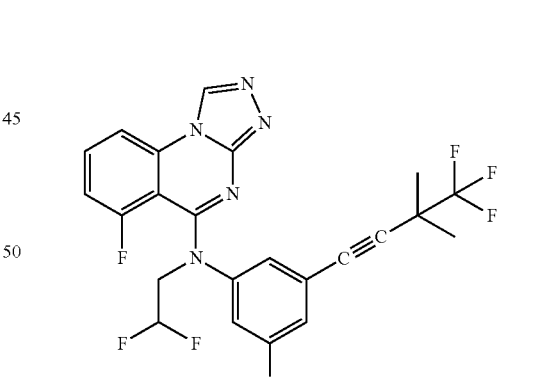

The title compound was synthesized according to the preparation of the core structures as described in Example 261, with the final coupling reaction as described in Example 421. ¹H NMR (400 MHz, Methanol-$d_4$) δ 9.70 (s, 1H), 8.23 (d, J=8.4 Hz, 1H), 8.08 (td, J=8.4, 5.0 Hz, 1H), 7.28 (ddd, J=11.9, 8.3, 1.0 Hz, 1H), 7.23-7.14 (m, 2H), 7.09 (ddd, J=8.8, 2.4, 1.2 Hz, 1H), 6.50 (tt, J=55.9, 4.0 Hz, 1H), 4.69 (td, J=13.7, 4.1 Hz, 2H), 1.56-1.45 (m, 6H); LCMS(m/z) 496.3.

Example 673. N-(2,2-difluoroethyl)-6,7-difluoro-N-(3-((1-(trifluoromethyl)cyclopropyl)ethynyl)phenyl)-[1,2,4]triazolo[4,3-a]quinazolin-5-amine

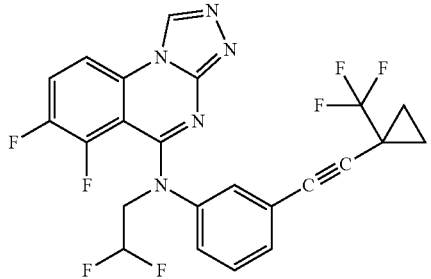 [SMILES: Fc1ccc2c(c(N(CC(F)F)c3cccc(C#CC4(C(F)(F)F)CC4)c3)nc3nncn32)c1F]

The title compound was synthesized according to the preparation of the core structures as described in Example 261, with the final coupling reaction as described in Example 421. ¹H NMR (400 MHz, Methanol-d₄) δ 9.68 (s, 1H), 8.25 (ddd, J=9.4, 4.0, 1.8 Hz, 1H), 8.05 (td, J=9.3, 7.6 Hz, 1H), 7.49-7.20 (m, 4H), 6.49 (tt, J=55.9, 4.1 Hz, 1H), 4.68 (td, J=13.6, 4.1 Hz, 2H), 1.46-1.31 (m, 2H), 1.29 (dq, J=3.3, 1.7 Hz, 2H); LCMS(m/z) 494.2.

Example 675. N-(2,2-difluoroethyl)-6-fluoro-N-(6-((1-(trifluoromethyl)cyclopropyl)ethynyl)pyrazin-2-yl)-[1,2,4]triazolo[4,3-a]quinazolin-5-amine

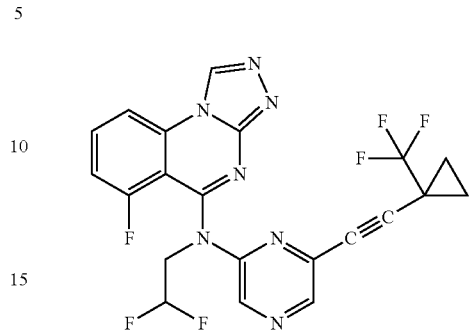

The title compound was synthesized according to the preparation of the core structures as described in Example 261, with the final coupling reaction as described in Example 421. ¹H NMR (400 MHz, Methanol-d₄) δ 9.77 (s, 1H), 8.49 (s, 1H), 8.40 (s, 1H), 8.29 (d, J=8.4 Hz, 1H), 8.09 (td, J=8.3, 5.2 Hz, 1H), 7.32 (ddd, J=12.3, 8.3, 1.0 Hz, 1H), 6.56 (tt, J=56.2, 4.1 Hz, 1H), 4.92-4.79 (m, 2H), 1.56-1.27 (m, 4H); LCMS(m/z) 478.2.

Example 674. N-(3-(4,4-difluoro-3,3-dimethylbut-1-yn-1-yl)-5-fluorophenyl)-N-(2,2-difluoroethyl)-6-fluoro-[1,2,4]triazolo[4,3-a]quinazolin-5-amine

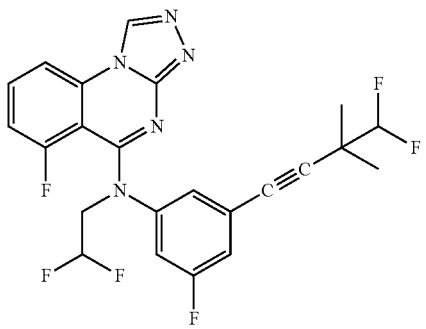 [SMILES: CC(C)(C#Cc1cc(F)cc(N(CC(F)F)c2nc3nncn3c3cccc(F)c23)c1)C(F)F]

The title compound was synthesized according to the preparation of the core structures as described in Example 261, with the final coupling reaction as described in Example 421. ¹H NMR (400 MHz, Methanol-d₄) δ 9.70 (s, 1H), 8.23 (d, J=8.4 Hz, 1H), 8.07 (td, J=8.3, 5.0 Hz, 1H), 7.28 (dd, J=11.7, 8.3 Hz, 1H), 7.21-7.09 (m, 2H), 7.07 (ddd, J=8.9, 2.4, 1.3 Hz, 1H), 6.48 (tt, J=55.9, 4.1 Hz, 1H), 5.74 (t, J=56.6 Hz, 1H), 4.68 (td, J=13.6, 4.0 Hz, 2H), 1.32 (t, J=1.1 Hz, 6H); LCMS(m/z) 478.3.

Example 676. N-(2,2-difluoroethyl)-6-fluoro-N-(3-fluoro-5-((1-methylcyclopropyl)ethynyl)phenyl)-[1,2,4]triazolo[4,3-a]quinazolin-5-amine

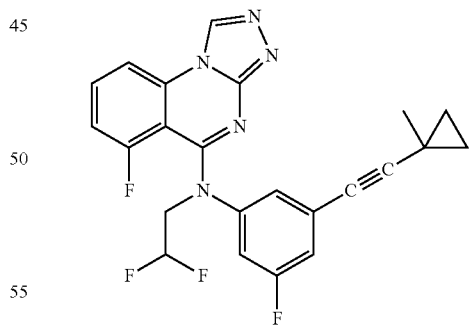

The title compound was synthesized according to the preparation of the core structures as described in Example 261, with the final coupling reaction as described in Example 421. ¹H NMR (400 MHz, Methanol-d₄) δ 9.69 (s, 1H), 8.22 (d, J=8.3 Hz, 1H), 8.07 (td, J=8.3, 4.9 Hz, 1H), 7.27 (dd, J=11.8, 8.3 Hz, 1H), 7.08 (d, J=9.2 Hz, 2H), 6.99 (dd, J=9.0, 1.8 Hz, 1H), 6.74-6.24 (m, 1H), 4.67 (td, J=13.5, 4.0 Hz, 2H), 1.29 (s, 3H), 0.93 (q, J=4.1 Hz, 2H), 0.76-0.59 (m, 2H); LCMS(m/z) 440.3.

Example 677. 4-(3-((2,2-difluoroethyl)(6-fluoro-[1,2,4]triazolo[4,3-a]quinazolin-5-yl)amino)-5-fluorophenyl)-2-methylbut-3-yn-2-ol

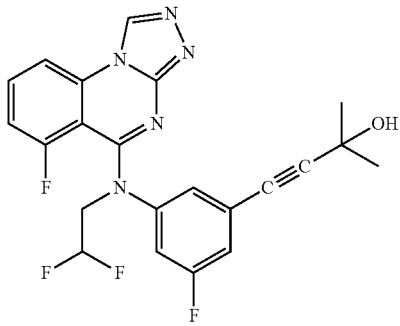 [SMILES: CC(C)(O)C#Cc1cc(F)cc(N(CC(F)F)c2nc3nncn3c3cccc(F)c23)c1]

The title compound was synthesized according to the preparation of the core structures as described in Example 261, with the final coupling reaction as described in Example 421. $^1$H NMR (400 MHz, Methanol-$d_4$) δ 9.67 (s, 1H), 8.21 (d, J=8.4 Hz, 1H), 8.05 (td, J=8.3, 5.0 Hz, 1H), 7.25 (dd, J=11.8, 8.2 Hz, 1H), 7.11 (d, J=11.1 Hz, 2H), 7.04 (dd, J=8.9, 1.8 Hz, 1H), 6.49 (t, J=55.9 Hz, 1H), 4.67 (td, J=13.6, 4.0 Hz, 2H), 1.51 (s, 6H); LCMS(m/z) 444.2.

Example 679. N-(2,2-difluoroethyl)-N-(3-((1-(difluoromethyl)cyclopropyl)ethynyl)-5-fluorophenyl)-6-fluoro-[1,2,4]triazolo[4,3-a]quinazolin-5-amine

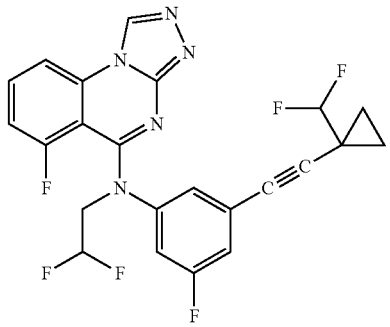

The title compound was synthesized according to the preparation of the core structures as described in Example 261, with the final coupling reaction as described in Example 421. $^1$H NMR (400 MHz, Methanol-$d_4$) δ 9.70 (s, 1H), 8.23 (d, J=8.4 Hz, 1H), 8.07 (td, J=8.3, 5.0 Hz, 1H), 7.27 (dd, J=11.8, 8.2 Hz, 1H), 7.15 (dd, J=8.9, 2.0 Hz, 2H), 7.07 (dt, J=8.6, 1.9 Hz, 1H), 6.48 (tt, J=55.9, 4.0 Hz, 1H), 5.63 (t, J=56.5 Hz, 1H), 4.68 (td, J=13.6, 4.1 Hz, 2H), 1.28-1.01 (m, 4H); LCMS(m/z) 476.3.

Example 678. N-(2,2-difluoroethyl)-6-fluoro-N-(3-fluoro-5-((1-(trifluoromethyl)cyclopropyl)ethynyl)phenyl)-[1,2,4]triazolo[4,3-a]quinazolin-5-amine

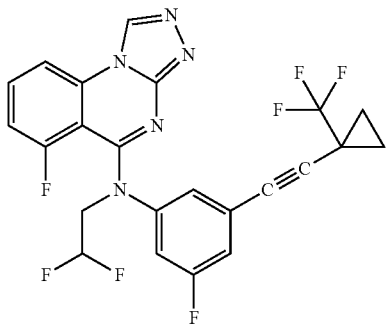 [SMILES: Fc1cc(C#CC2(C(F)(F)F)CC2)cc(N(CC(F)F)c2nc3nncn3c3cccc(F)c23)c1]

The title compound was synthesized according to the preparation of the core structures as described in Example 261, with the final coupling reaction as described in Example 421. $^1$H NMR (400 MHz, Methanol-$d_4$) δ 9.69 (s, 1H), 8.22 (d, J=8.4 Hz, 1H), 8.07 (td, J=8.3, 5.0 Hz, 1H), 7.27 (dd, J=11.8, 8.3 Hz, 1H), 7.21-7.14 (m, 2H), 7.15-7.02 (m, 1H), 6.64-6.22 (m, 1H), 4.68 (td, J=13.6, 4.0 Hz, 2H), 1.47-1.35 (m, 2H), 1.35-1.14 (m, 2H); LCMS(m/z) 494.3.

Example 680. N-(3-(4,4-difluoro-3,3-dimethylbut-1-yn-1-yl)-5-fluorophenyl)-7-fluoro-N-methyl-[1,2,4]triazolo[4,3-a]quinazolin-5-amine

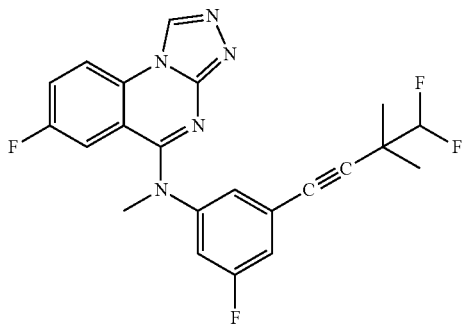 [SMILES: CN(c1cc(F)cc(C#CC(C)(C)C(F)F)c1)c1nc2nncn2c2ccc(F)cc12]

The title compound was synthesized according to the preparation of the core structures as described in Example 261, with the final coupling reaction as described in Example 421. $^1$H NMR (400 MHz, Methanol-$d_4$) δ 9.64 (s, 1H), 8.44 (dd, J=9.2, 4.7 Hz, 1H), 7.84 (ddd, J=9.2, 7.6, 2.7 Hz, 1H), 7.43-7.22 (m, 3H), 6.97 (dd, J=10.2, 2.7 Hz, 1H), 5.78 (t, J=56.6 Hz, 1H), 3.78 (s, 3H), 1.36 (d, J=1.2 Hz, 6H); LCMS(m/z) 428.3.

Example 681. N-(3-(4,4-difluoro-3,3-dimethylbut-1-yn-1-yl)-5-fluorophenyl)-7-fluoro-N-methyl-[1,2,4]triazolo[4,3-a]quinazolin-5-amine

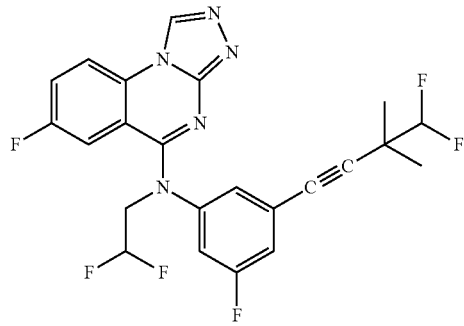 [SMILES: CC(C)(C#Cc1cc(F)cc(N(CC(F)F)c2nc3nncn3c3ccc(F)cc23)c1)C(F)F]

The title compound was synthesized according to the preparation of the core structures as described in Example 261, with the final coupling reaction as described in Example 421. $^1$H NMR (400 MHz, Methanol-$d_4$) δ 9.71 (s, 1H), 8.47 (dd, J=9.2, 4.7 Hz, 1H), 7.86 (ddd, J=9.3, 7.6, 2.7 Hz, 1H), 7.46-7.23 (m, 3H), 6.95 (dd, J=10.0, 2.7 Hz, 1H), 6.79-6.35 (m, 1H), 5.78 (t, J=56.6 Hz, 1H), 4.63 (td, J=13.4, 4.2 Hz, 2H), 1.36 (d, J=1.2 Hz, 6H); LCMS(m/z) 478.3.

Example 683. 8-chloro-N-(3-(4,4-difluoro-3,3-dimethylbut-1-yn-1-yl)-5-fluorophenyl)-N-(2,2-difluoroethyl)-[1,2,4]triazolo[4,3-a]quinazolin-5-amine

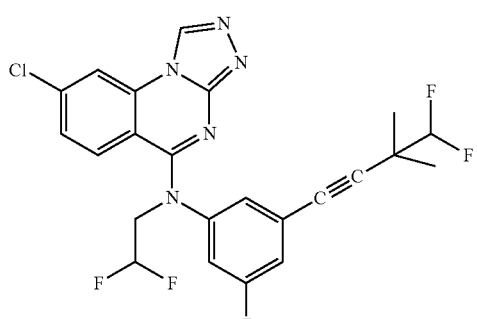

The title compound was synthesized according to the preparation of the core structures as described in Example 261, with the final coupling reaction as described in Example 421. $^1$H NMR (400 MHz, Methanol-$d_4$) δ 9.69 (s, 1H), 8.58 (d, J=2.1 Hz, 1H), 7.51 (dd, J=9.1, 2.1 Hz, 1H), 7.47-7.19 (m, 4H), 6.52 (tt, J=56.0, 4.2 Hz, 1H), 5.77 (t, J=56.6 Hz, 1H), 4.62 (d, J=4.2 Hz, 2H), 1.35 (t, J=1.1 Hz, 6H); LCMS(m/z) 494.3.

Example 682. 7-fluoro-N,1-dimethyl-N-(6-((1-(trifluoromethyl)cyclopropyl)ethynyl)pyrazin-2-yl)-[1,2,4]triazolo[4,3-a]quinazolin-5-amine

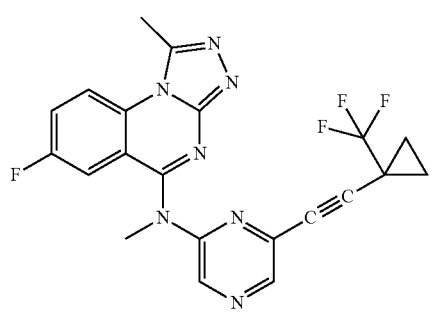 [SMILES: Cc1nnc2nc(N(C)c3cncc(C#CC4(C(F)(F)F)CC4)n3)c3cc(F)ccc3n12]

The title compound was synthesized according to the preparation of the core structures as described in Example 261, with the final coupling reaction as described in Example 421. $^1$H NMR (400 MHz, Methanol-$d_4$) δ 8.60-8.47 (m, 2H), 8.46 (s, 1H), 7.88 (ddd, J=9.4, 7.7, 2.9 Hz, 1H), 7.37 (dd, J=9.1, 2.9 Hz, 1H), 3.84 (s, 3H), 3.14 (s, 3H), 1.57-1.30 (m, 4H); LCMS(m/z) 442.3.

Example 684. 8-chloro-N-(2,2-difluoroethyl)-N-(3-fluoro-5-((1-methylcyclopropyl)ethynyl)phenyl)-[1,2,4]triazolo[4,3-a]quinazolin-5-amine

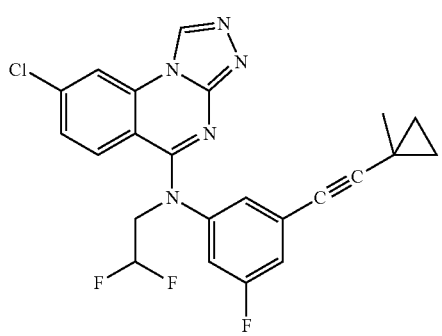 [SMILES: CC1(C#Cc2cc(F)cc(N(CC(F)F)c3nc4nncn4c4cc(Cl)ccc34)c2)CC1]

The title compound was synthesized according to the preparation of the core structures as described in Example 261, with the final coupling reaction as described in Example 421. $^1$H NMR (400 MHz, Methanol-$d_4$) δ 9.68 (s, 1H), 8.57 (d, J=2.0 Hz, 1H), 7.50 (dd, J=9.1, 2.0 Hz, 1H), 7.43-7.08 (m, 4H), 6.76-6.23 (m, 1H), 4.60 (td, J=13.4, 4.2 Hz, 2H), 1.32 (s, 3H), 0.97 (q, J=4.1 Hz, 2H), 0.84-0.61 (m, 2H); LCMS(m/z) 456.3.

Example 685. 8-chloro-N-(2,2-difluoroethyl)-N-(3-fluoro-5-((1-(trifluoromethyl)cyclopropyl)ethynyl)phenyl)-[1,2,4]triazolo[4,3-a]quinazolin-5-amine

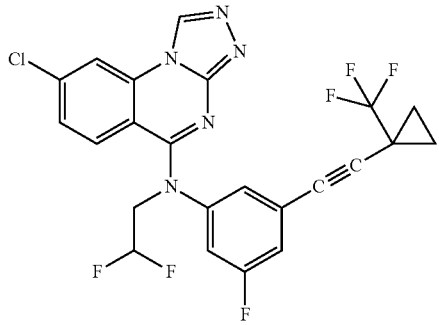 [SMILES: Fc1cc(C#CC2(C(F)(F)F)CC2)cc(N(CC(F)F)c2nc3nncn3c3cc(Cl)ccc23)c1]

The title compound was synthesized according to the preparation of the core structures as described in Example 261, with the final coupling reaction as described in Example 421. $^1$H NMR (400 MHz, Methanol-$d_4$) δ 9.69 (s, 1H), 8.57 (d, J=2.0 Hz, 1H), 7.51 (dd, J=9.1, 2.1 Hz, 1H), 7.43-7.22 (m, 4H), 6.74-6.27 (m, 1H), 4.62 (td, J=13.4, 4.2 Hz, 2H), 1.52-1.22 (m, 4H); LCMS(m/z) 510.3.

Example 686. 8-chloro-N-(3-(4,4-difluoro-3,3-dimethylbut-1-yn-1-yl)-5-fluorophenyl)-N-methyl-[1,2,4]triazolo[4,3-a]quinazolin-5-amine

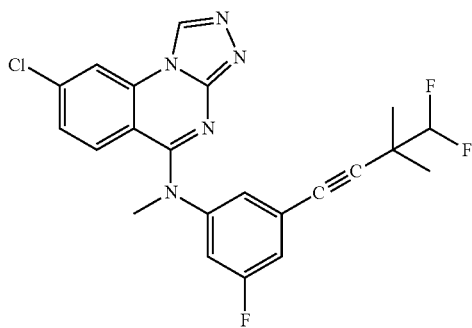 [SMILES: CN(c1cc(F)cc(C#CC(C)(C)C(F)F)c1)c1nc2nncn2c2cc(Cl)ccc12]

The title compound was synthesized according to the preparation of the core structures as described in Example 261, with the final coupling reaction as described in Example 421. $^1$H NMR (400 MHz, Methanol-$d_4$) δ 9.62 (s, 1H), 8.63-8.38 (m, 1H), 7.49 (dd, J=9.2, 2.0 Hz, 1H), 7.39-7.11 (m, 4H), 5.77 (t, J=56.6 Hz, 1H), 3.77 (s, 3H), 1.35 (d, J=1.2 Hz, 6H); LCMS(m/z) 444.3.

Example 687. 8-chloro-N-(3-((1-ethylcyclopropyl)ethynyl)-5-fluorophenyl)-N-methyl-[1,2,4]triazolo[4,3-a]quinazolin-5-amine

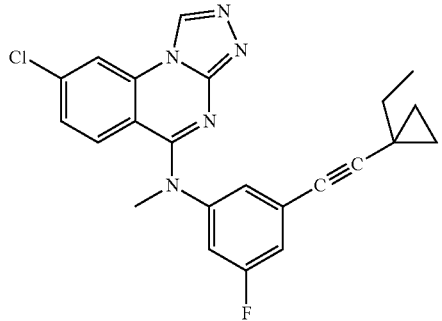 [SMILES: CCC1(C#Cc2cc(F)cc(N(C)c3nc4nncn4c4cc(Cl)ccc34)c2)CC1]

The title compound was synthesized according to the preparation of the core structures as described in Example 261, with the final coupling reaction as described in Example 421. $^1$H NMR (400 MHz, Methanol-$d_4$) δ 9.61 (s, 1H), 8.53 (d, J=2.0 Hz, 1H), 7.49 (dd, J=9.1, 2.1 Hz, 1H), 7.38-7.11 (m, 4H), 3.76 (s, 3H), 1.45 (q, J=7.4 Hz, 2H), 1.11 (t, J=7.3 Hz, 3H), 0.94 (q, J=4.1 Hz, 2H), 0.79-0.61 (m, 2H); LCMS(m/z) 420.3.

Example 688. 8-chloro-N-(3-((1-(difluoromethyl)cyclopropyl)ethynyl)-5-fluorophenyl)-N-methyl-[1,2,4]triazolo[4,3-a]quinazolin-5-amine

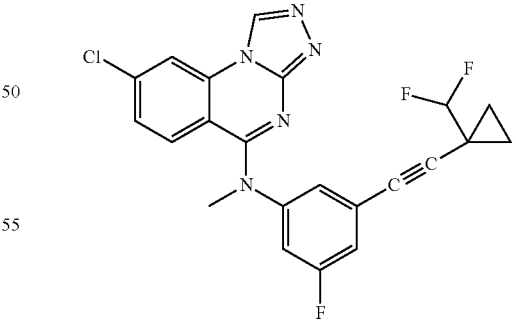

The title compound was synthesized according to the preparation of the core structures as described in Example 261, with the final coupling reaction as described in Example 421. $^1$H NMR (400 MHz, Methanol-$d_4$) δ 9.62 (s, 1H), 8.53 (d, J=2.1 Hz, 1H), 7.49 (dd, J=9.1, 2.1 Hz, 1H), 7.43-7.16 (m, 4H), 5.64 (t, J=56.4 Hz, 1H), 3.77 (s, 3H), 1.32-1.06 (m, 4H); LCMS(m/z) 442.3.

Example 689. 8-chloro-N-(3-(3,3-dimethylbut-1-yn-1-yl)-5-fluorophenyl)-N-methyl-[1,2,4]triazolo[4,3-a]quinazolin-5-amine

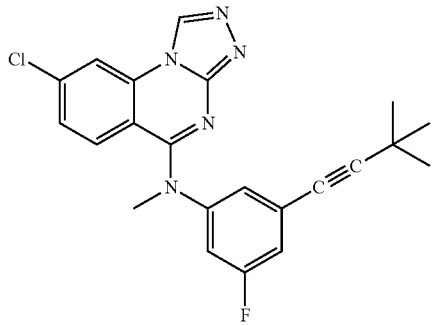 [SMILES: CN(c1cc(F)cc(C#CC(C)(C)C)c1)c1nc2nncn2c2cc(Cl)ccc12]

The title compound was synthesized according to the preparation of the core structures as described in Example 261, with the final coupling reaction as described in Example 421. $^1$H NMR (400 MHz, Methanol-$d_4$) δ 9.62 (s, 1H), 8.54 (d, J=2.1 Hz, 1H), 7.49 (dd, J=9.1, 2.1 Hz, 1H), 7.44-7.14 (m, 4H), 3.77 (s, 3H), 1.30 (s, 9H); LCMS(m/z) 408.4.

Example 690. N-(2,2-difluoroethyl)-7-fluoro-N-(3-fluoro-5-((1-(trifluoromethyl)cyclopropyl)ethynyl)phenyl)-[1,2,4]triazolo[4,3-a]quinazolin-5-amine

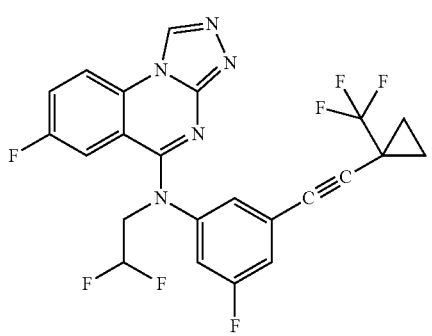 [SMILES: Fc1cc(C#CC2(C(F)(F)F)CC2)cc(N(CC(F)F)c2nc3nncn3c3ccc(F)cc23)c1]

The title compound was synthesized according to the preparation of the core structures as described in Example 261, with the final coupling reaction as described in Example 421. $^1$H NMR (400 MHz, Methanol-$d_4$) δ 9.71 (s, 1H), 8.47 (dd, J=9.2, 4.7 Hz, 1H), 7.86 (ddd, J=9.2, 7.6, 2.7 Hz, 1H), 7.50-7.22 (m, 3H), 6.95 (dd, J=10.0, 2.7 Hz, 1H), 6.54 (tt, J=56.0, 4.2 Hz, 1H), 4.63 (td, J=13.4, 4.2 Hz, 2H), 1.51-1.25 (m, 4H); LCMS(m/z) 494.3.

Example 691. 7-fluoro-N-(3-fluoro-5-((1-(trifluoromethyl)cyclopropyl)ethynyl)phenyl)-N-methyl-[1,2,4]triazolo[4,3-a]quinazolin-5-amine

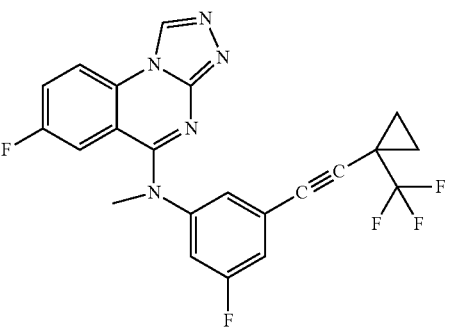

The title compound was synthesized according to the preparation of the core structures as described in Example 261, with the final coupling reaction as described in Example 421. $^1$H NMR (400 MHz, Methanol-$d_4$) δ 9.65 (s, 1H), 8.44 (dd, J=9.2, 4.7 Hz, 1H), 7.84 (ddd, J=9.3, 7.6, 2.7 Hz, 1H), 7.46-7.28 (m, 3H), 6.96 (dd, J=10.1, 2.7 Hz, 1H), 3.79 (s, 3H), 1.50-1.24 (m, 4H); LCMS(m/z) 444.3.

Example 692. 8-chloro-N-(3-fluoro-5-((1-(trifluoromethyl)cyclopropyl)ethynyl)phenyl)-N-methyl-[1,2,4]triazolo[4,3-a]quinazolin-5-amine

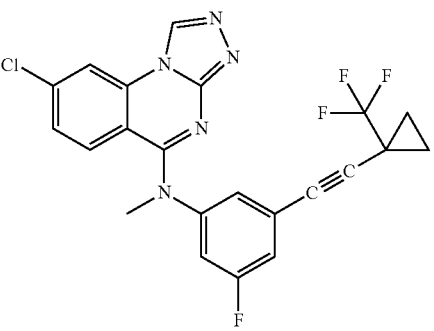 [SMILES: CN(c1cc(F)cc(C#CC2(C(F)(F)F)CC2)c1)c1nc2nncn2c2cc(Cl)ccc12]

The title compound was synthesized according to the preparation of the core structures as described in Example 261, with the final coupling reaction as described in Example 421. $^1$H NMR (400 MHz, Methanol-$d_4$) δ 9.63 (s, 1H), 8.54 (d, J=2.1 Hz, 1H), 7.49 (dd, J=9.1, 2.1 Hz, 1H), 7.47-7.21 (m, 4H), 3.77 (s, 3H), 1.49-1.40 (m, 2H), 1.32 (dtd, J=6.0, 3.9, 1.4 Hz, 2H); LCMS(m/z) 460.3.

Example 693. 2-(3'-((8-chloro-[1,2,4]triazolo[4,3-a]quinazolin-5-yl)(methyl)amino)-5'-fluoro-[1,1'-biphenyl]-4-yl)isothiazolidine 1,1-dioxide

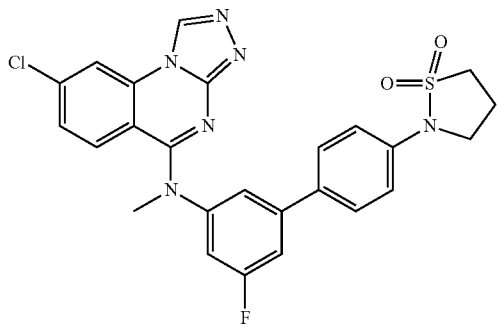 [SMILES: CN(c1cc(F)cc(-c2ccc(N3CCCS3(=O)=O)cc2)c1)c1nc2nncn2c2cc(Cl)ccc12]

The title compound was synthesized according to the preparation of the core structures as described in Example 261, with the final coupling reaction as described in Example 421. $^1$H NMR (400 MHz, Methanol-d$_4$) δ 9.60 (s, 1H), 8.51 (t, J=1.3 Hz, 1H), 7.70-7.29 (m, 8H), 7.26 (dt, J=9.1, 2.2 Hz, 1H), 3.98-3.72 (m, 5H), 3.48 (t, J=7.4 Hz, 2H), 2.65-2.45 (m, 2H); LCMS(m/z) 523.2.

Example 695. N-(3-bromo-5-fluorophenyl)-8-chloro-7-fluoro-N-methyl-[1,2,4]triazolo[4,3-a]quinazolin-5-amine

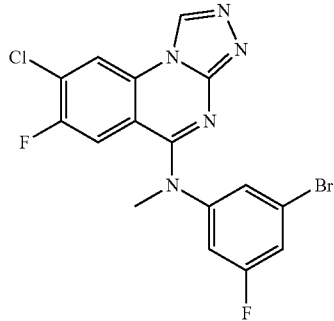

The title compound was synthesized according to the preparation of the core structures as described in Example 261, with the final coupling reaction as described in Example 421. $^1$H NMR (400 MHz, Methanol-d$_4$) δ 9.60 (s, 1H), 8.70 (d, J=6.4 Hz, 1H), 7.64-7.30 (m, 3H), 7.12 (d, J=10.4 Hz, 1H), 3.76 (s, 3H); LCMS(m/z) 424.2.

Example 696. 5-(8-chloro-[1,2,4]triazolo[4,3-a]quinazolin-5-yl)-9-(3,3-dimethylbut-1-yn-1-yl)-2,3,4,5-tetrahydrobenzo[b][1,4]oxazepine

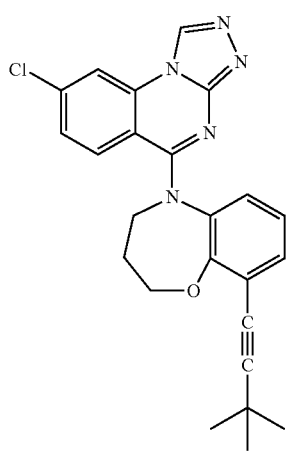 [SMILES: CC(C)(C)C#Cc1cccc2c1OCCCN2c1nc2nncn2c2cc(Cl)ccc12]

Example 694. 4-(3-((8-chloro-7-fluoro-[1,2,4]triazolo[4,3-a]quinazolin-5-yl)(methyl)amino)-5-fluorophenyl)-2-methylbut-3-yn-2-ol

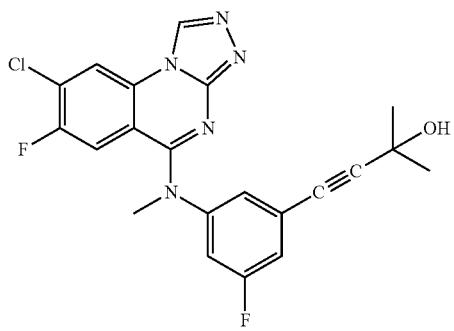

The title compound was synthesized according to the preparation of the core structures as described in Example 261, with the final coupling reaction as described in Example 421. $^1$H NMR (400 MHz, Methanol-d$_4$) δ 9.57 (s, 1H), 8.68 (d, J=6.4 Hz, 1H), 7.37-7.22 (m, 3H), 7.09 (d, J=10.5 Hz, 1H), 3.74 (s, 3H), 1.54 (s, 6H); LCMS(m/z) 428.2.

The title compound was synthesized according to the preparation of the core structures as described in Example 261, with the final coupling reaction as described in Example 421. $^1$H NMR (400 MHz, Methanol-d$_4$) δ 9.57 (s, 1H), 8.48 (d, J=2.1 Hz, 1H), 7.42 (ddd, J=21.0, 8.2, 2.0 Hz, 2H), 7.14 (d, J=9.1 Hz, 1H), 7.05-6.89 (m, 2H), 4.36 (b, 2H), 3.37-3.28 (m, 2H), 2.23 (b, 2H), 1.38 (s, 9H); LCMS(m/z) 432.4.

Example 697. 4-(1-(6-fluoro-1-methyl-[1,2,4]triazolo[4,3-a]quinazolin-5-yl)-2,3,4,5-tetrahydro-1H-benzo[b]azepin-6-yl)-2-methylbut-3-yn-2-ol

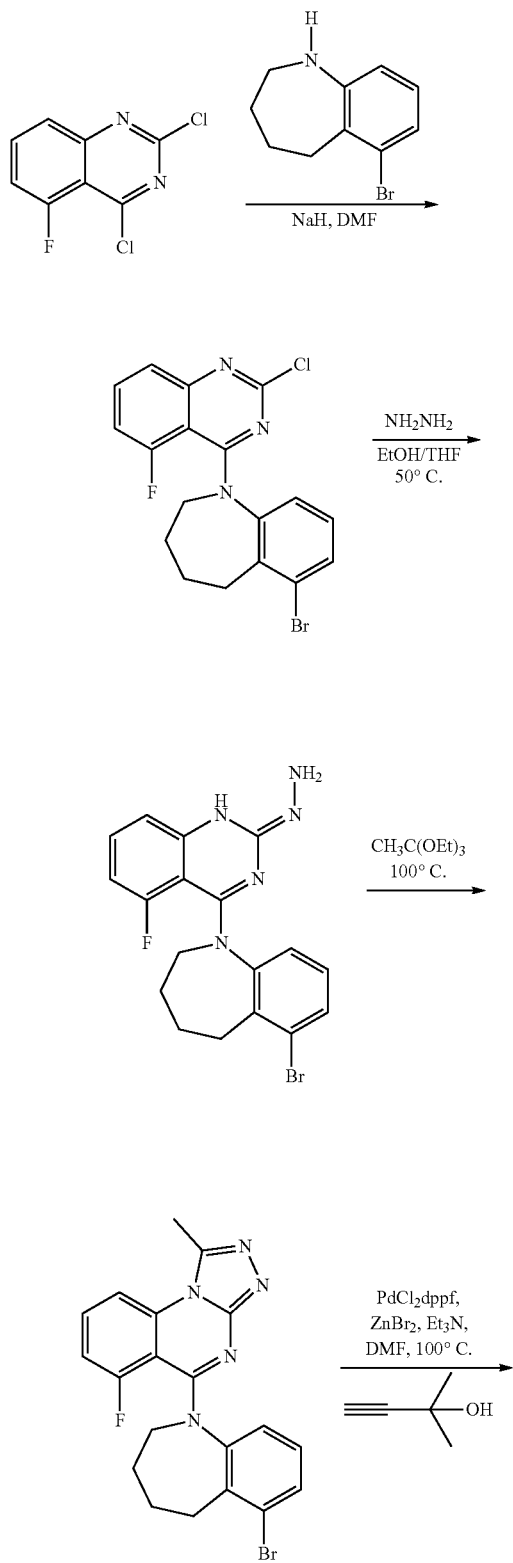

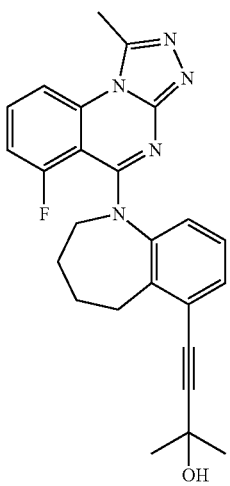

Synthesis of 6-bromo-1-(2-chloro-5-fluoro-quinazolin-4-yl)-2,3,4,5-tetrahydro-1-benzazepine: To a solution of 6-bromo-2,3,4,5-tetrahydro-1H-1-benzazepine (521 mg, 2.3 mmol) in DMA (5.0 mL) at 0° C. was added NaH (60% dispersion in mineral oil) (177 mg, 4.61 mmol) in one portion. The mixture was stirred at 0° C. for 30 min, followed by the 2,4-dichloro-5-fluoroquinazoline (500 mg, 2.3 mmol) in one portion and the mixture was warmed to room temperature over 16 h. Upon completion, the mixture was poured into water (50 mL) and extracted with ethyl acetate (2×50 ml each). The organics were separated and dried over sodium sulfate, filtered and concentrated under vacuum. The crude was purified by column chromatography on silica gel using ethyl acetate in hexanes 0-40% as the eluent. Appropriate fractions were combined and concentrated in vacuo to afford the desired compound. (MS (m/z) 407.2 [M+H]+.

Synthesis of [4-(6-bromo-2,3,4,5-tetrahydro-1-benzazepin-1-yl)-5-fluoro-quinazolin-2-yl]hydrazine: To a solution of 6-bromo-1-(2-chloro-5-fluoro-quinazolin-4-yl)-2,3,4,5-tetrahydro-1-benzazepine (200 mg, 0.492 mmol) in THF (10 mL) and ethanol (10 mL) was added anhydrous hydrazine (158 mg, 4.92 mmol) and the mixture was stirred at room temperature for 5 hrs. Upon completion, the reaction was diluted with dichloromethane and washed with water followed by brine. The resulting organics were dried over Na$_2$SO$_4$, filtered and concentrated under reduced pressure to afford the desired compound. MS (m/z) 403.2 [M+H]+.

Synthesis of 5-(6-bromo-2,3,4,5-tetrahydro-1-benzazepin-1-yl)-6-fluoro-1-methyl-[1,2,4]triazolo[4,3-a]quinazoline: A solution of [4-(6-bromo-2,3,4,5-tetrahydro-1-benzazepin-1-yl)-5-fluoro-quinazolin-2-yl]hydrazine (75 mg, 0.186 mmol) and triethyl orthoacetate (0.9 g, 5.62 mmol) was heated to 100° C. for 16 hrs. Upon completion, the reaction was cooled to room temperature, and concentrated under reduced pressure to afford the crude product. The crude product was triturated with heptane and the solids were collected by filtration, washed with heptanes and dried in vacuo to afford the desired compound. MS (m/z) 427.2 [M+H]+.

Synthesis of 4-[1-(6-fluoro-1-methyl-[1,2,4]triazolo[4,3-a]quinazolin-5-yl)-2,3,4,5-tetrahydro-1-benzazepin-6-yl]-2-methyl-but-3-yn-2-ol: A solution of 5-(6-bromo-2,3,4,5-tetrahydro-1-benzazepin-1-yl)-6-fluoro-1-methyl-[1,2,4]triazolo[4,3-a]quinazoline (25.9 mg, 0.0606 mmol), zinc bromide (68.3 mg, 0.303 mmol), (1,1'-)bis(diphenylphosphino)ferrocene) palladium (II) dichloride (2.5 mg, 0.00303 mmol), and triethylamine (61 mg, 0.6 mmol) in DMF (2 mL) was purged with nitrogen gas for 2 minutes. 2-methylbut-3-yn-2-ol (10 mg, 0.121 mmol) was then added and the mixture was heated at 100° C. for 2 hrs. Upon completion, the mixture was cooled to room temperature, and ethyl acetate and sat. NH$_4$Cl (aq) were added to the mixture. The aqueous layer was extracted with EA and the combined organic layers were dried over Na$_2$SO$_4$ and concentrated in vacuo. The residue was purified by reverse phase HPLC (0.1% trifluoroacetic acid in acetonitrile/water), providing the title compound as the mono-TFA salt. 1H NMR (400 MHz, DMSO-d$_6$) δ 8.12 (d, J=8.6 Hz, 1H), 7.93 (td, J=8.4, 5.3 Hz, 1H), 7.37-7.15 (m, 2H), 6.94 (t, J=7.8 Hz, 1H), 6.74 (d, J=7.9 Hz, 1H), 3.44 (d, J=164.0 Hz, 6H), 2.99 (s, 3H), 1.85 (s, 2H), 1.52 (s, 6H); MS (m/z) 430.2 [M+H]$^+$.

Example 698. (R)-4-(3-((2,2-difluoroethyl)(6-fluoro-1-methyl-[1,2,4]triazolo[4,3-a]quinazolin-5-yl)amino)-5-fluorophenyl)but-3-yn-2-ol

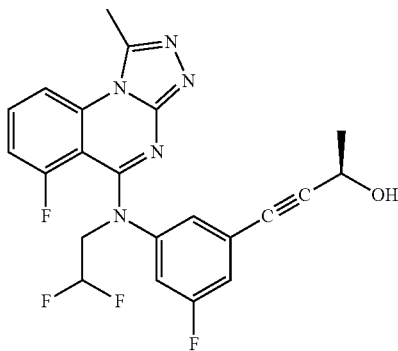 [SMILES: Cc1nnc2nc(N(CC(F)F)c3cc(F)cc(C#C[C@@H](C)O)c3)c3c(F)cccc3n12]

The title compound was prepared according to the general procedures described for Example 704. 1H NMR (400 MHz, DMSO-d$_6$) δ 8.16 (d, J=8.6 Hz, 1H), 8.06-7.79 (m, 1H), 7.29 (dd, J=12.0, 8.1 Hz, 1H), 7.18-7.04 (m, 2H), 6.99 (d, J=8.7 Hz, 1H), 6.74-6.32 (m, 1H), 4.70-4.55 (m, 2H), 4.53 (q, J=6.5 Hz, 1H), 3.01 (s, 3H), 1.33 (d, J=6.6 Hz, 3H); LCMS(m/z) 444.1.

Example 699. N-(3-(cyclopropylethynyl)-5-fluoro-phenyl)-N-(2,2-difluoroethyl)-6-fluoro-1-methyl-[1,2,4]triazolo[4,3-a]quinazolin-5-amine

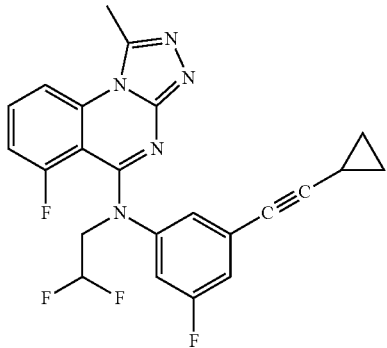 [SMILES: Cc1nnc2nc(N(CC(F)F)c3cc(F)cc(C#CC4CC4)c3)c3c(F)cccc3n12]

The title compound was prepared according to the general procedures described for Example 704. 1H NMR (400 MHz, DMSO-d$_6$) δ 8.16 (d, J=8.6 Hz, 1H), 7.97 (td, J=8.4, 5.3 Hz, 1H), 7.29 (dd, J=12.0, 8.2 Hz, 1H), 7.13-7.06 (m, 1H), 7.03 (s, 1H), 6.95 (dd, J=9.1, 1.9 Hz, 1H), 6.77-6.11 (m, 1H), 4.74-4.49 (m, 2H), 3.01 (s, 3H), 1.49 (ddd, J=13.3, 8.6, 5.0 Hz, 1H), 0.86 (dt, J=8.2, 3.3 Hz, 2H), 0.79-0.58 (m, 2H); LCMS(m/z) 440.1.

Example 700. 5-(5-(cyclopropylethynyl)-3,4-dihyd-roquinolin-1(2H)-yl)-7-fluoro-1-methyl-[1,2,4]tri-azolo[4,3-a]quinazoline

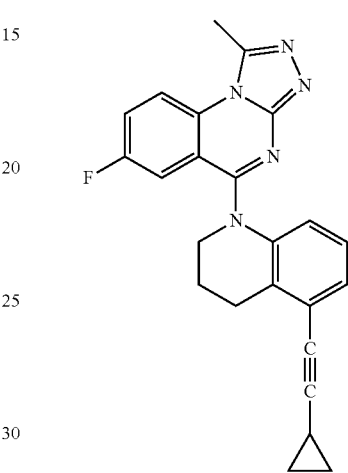

The title compound was prepared according to the general procedures described for Example 719. 1H NMR (400 MHz, DMSO-d$_6$) δ 8.39 (dd, J=9.4, 4.6 Hz, 1H), 8.00-7.79 (m, 1H), 7.39 (dd, J=9.6, 2.9 Hz, 1H), 7.16 (d, J=7.6 Hz, 1H), 6.97 (t, J=7.9 Hz, 1H), 6.79 (d, J=8.1 Hz, 1H), 3.98 (t, J=6.3 Hz, 2H), 3.01 (s, 3H), 2.96 (t, J=6.7 Hz, 2H), 2.10 (q, J=6.6 Hz, 2H), 1.62 (td, J=8.4, 4.3 Hz, 1H), 1.00-0.89 (m, 2H), 0.84-0.73 (m, 2H); LCMS(m/z) 398.1.

Example 701. 6-fluoro-5-(5-((1-(trifluoromethyl)cyclopropyl)ethynyl)-3,4-dihydroquinolin-1(2H)-yl)-[1,2,4]triazolo[4,3-a]quinazolin-1-amine

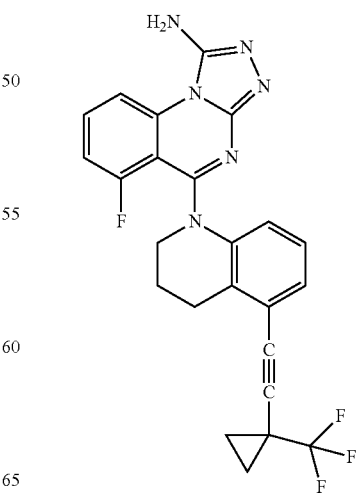

The title compound was prepared according to the general procedures described for Example 704. 1H NMR (400 MHz, DMSO-$d_6$) δ 8.30 (d, J=8.5 Hz, 1H), 8.09-7.84 (m, 1H), 7.35 (dd, J=11.9, 8.4 Hz, 2H), 7.20 (dd, J=7.2, 1.6 Hz, 1H), 7.08-6.82 (m, 2H), 3.87 (s, 2H), 2.92 (s, 2H), 2.08 (s, 2H), 1.66-1.24 (m, 4H); LCMS(m/z) 467.2.

Example 702. 7-fluoro-1-methyl-5-(5-((1-methylcyclopropyl)ethynyl)-3,4-dihydroquinolin-1(2H)-yl)-[1,2,4]triazolo[4,3-a]quinazoline

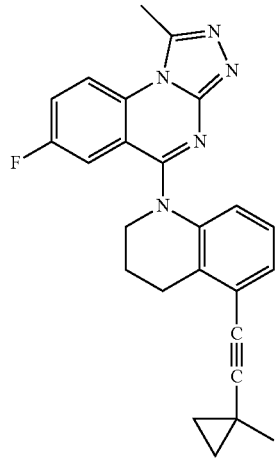 [SMILES: Cc1nnc2nc(N3CCCc4c(C#CC5(C)CC5)cccc43)c3cc(F)ccc3n12]

The title compound was prepared according to the general procedures described for Example 719. 1H NMR (400 MHz, DMSO-$d_6$) δ 8.38 (dd, J=9.4, 4.6 Hz, 1H), 7.87 (td, J=8.7, 2.9 Hz, 1H), 7.39 (dd, J=9.6, 2.9 Hz, 1H), 7.14 (d, J=7.5 Hz, 1H), 6.96 (t, J=7.9 Hz, 1H), 6.77 (d, J=8.1 Hz, 1H), 3.97 (t, J=6.2 Hz, 2H), 3.01 (s, 3H), 2.96 (t, J=6.7 Hz, 2H), 2.10 (p, J=6.5 Hz, 2H), 1.37 (s, 3H), 1.11-0.94 (m, 2H), 0.91-0.71 (m, 2H); LCMS(m/z) 412.2.

Example 703. 6-fluoro-1-methyl-5-(5-((1-methylcyclopropyl)ethynyl)-3,4-dihydroquinolin-1(2H)-yl)-[1,2,4]triazolo[4,3-a]quinazoline

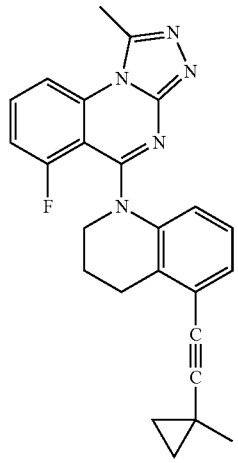 [SMILES: Cc1nnc2nc(N3CCCc4c(C#CC5(C)CC5)cccc43)c3c(F)cccc3n12]

The title compound was prepared according to the general procedures described for Example 719. 1H NMR (400 MHz, DMSO-$d_6$) δ 8.16 (d, J=8.6 Hz, 1H), 7.99 (td, J=8.4, 5.3 Hz, 1H), 7.35 (dd, J=11.8, 8.2 Hz, 1H), 7.07 (d, J=7.5 Hz, 1H), 6.89 (t, J=7.9 Hz, 1H), 6.76 (d, J=8.1 Hz, 1H), 3.87 (bs, 2H), 2.99 (s, 3H), 2.89 (bs, 2H), 2.07 (m, 2H), 1.39-1.31 (m, 3H), 1.05-0.95 (m, 2H), 0.80 (d, J=5.2 Hz, 2H); LCMS(m/z) 412.2.

Example 704. 4-(3-((2,2-difluoroethyl)(6-fluoro-1-methyl-[1,2,4]triazolo[4,3-a]quinazolin-5-yl)amino)-5-fluorophenyl)-2-methylbut-3-yn-2-ol

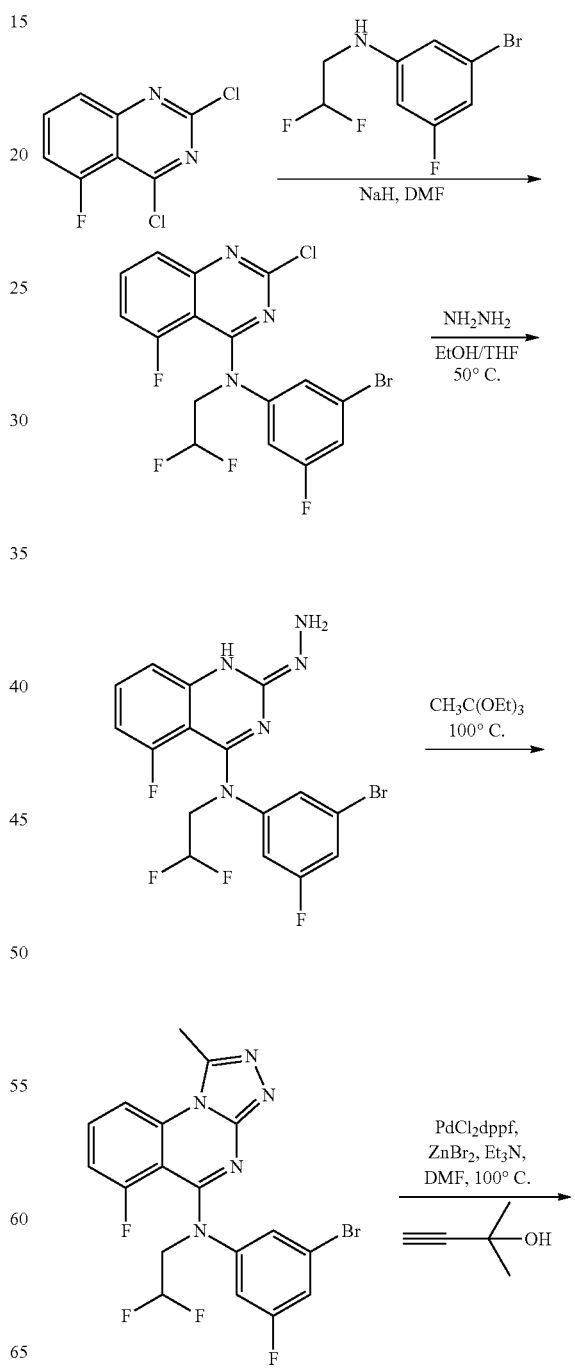

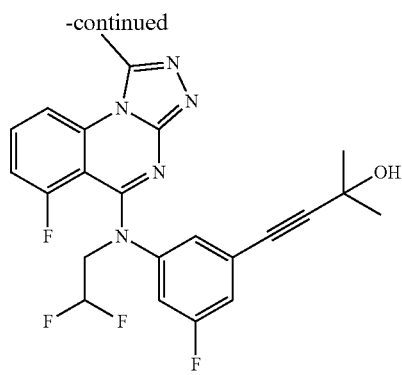

Synthesis of N-(3-bromo-5-fluoro-phenyl)-2-chloro-N-(2,2-difluoroethyl)-5-fluoro-quinazolin-4-amine: To a solution of 3-bromo-N-(2,2-difluoroethyl)-5-fluoro-aniline (300 mg, 1.38 mmol) in DMF (2.0 mL) at 0° C. was added NaH (60% dispersion in mineral oil) (63 mg, 1.66 mmol) in one portion. The mixture was stirred at 0° C. for 30 min, followed by the 2,4-dichloro-5-fluoro-quinazoline (300 mg, 1.38 mmol) in one portion and the mixture was warmed to room temperature over 2 h. Upon completion, the mixture was poured into water (20 mL) and extracted with ethyl acetate (2×20 ml each). The organics were separated and dried over sodium sulfate, filtered and concentrated under vacuum. The crude was purified by column chromatography on silica gel using ethyl acetate in hexanes 0-40% as the eluent. Appropriate fractions were combined and concentrated in vacuo to afford the desired compound. (MS (m/z) 435.6 [M+H]+.

Synthesis of N-(3-bromo-5-fluoro-phenyl)-N-(2,2-difluoroethyl)-5-fluoro-2-hydrazino-quinazolin-4-amine: To a solution of N-(3-bromo-5-fluoro-phenyl)-2-chloro-N-(2,2-difluoroethyl)-5-fluoro-quinazolin-4-amine (300 mg, 0.69 mmol) in THF (5 mL) and ethanol (5 mL) was added anhydrous hydrazine (221 mg, 6.90 mmol) and the mixture was stirred at room temperature for 5 hrs. Upon completion, the reaction was diluted with dichloromethane and washed with water followed by brine. The resulting organics were dried over Na$_2$SO$_4$, filtered and concentrated under reduced pressure to afford the desired compound. MS (m/z) 431.2 [M+H]+.

Synthesis of N-(3-bromo-5-fluoro-phenyl)-N-(2,2-difluoroethyl)-6-fluoro-1-methyl-[1,2,4]triazolo[4,3-a]quinazolin-5-amine: A solution of N-(3-bromo-5-fluoro-phenyl)-N-(2,2-difluoroethyl)-5-fluoro-2-hydrazino-quinazolin-4-amine (106 mg, 0.246 mmol) and triethyl orthoacetate (0.9 g, 5.62 mmol) was heated to 100° C. for 16 hrs. Upon completion, the reaction was cooled to room temperature, and concentrated under reduced pressure to afford the crude product. The crude product was triturated with heptane and the solids were collected by filtration, washed with heptanes and dried in vacuo to afford the desired compound. MS (m/z) 455.2 [M+H]+.

Synthesis of 4-[3-[2,2-difluoroethyl-(6-fluoro-1-methyl-[1,2,4]triazolo[4,3-a]quinazolin-5-yl)amino]-5-fluoro-phenyl]-2-methyl-but-3-yn-2-ol: A solution of N-(3-bromo-5-fluoro-phenyl)-N-(2,2-difluoroethyl)-6-fluoro-1-methyl-[1,2,4]triazolo[4,3-a]quinazolin-5-amine (30 mg, 0.066 mmol), zinc bromide (74.4 mg, 0.33 mmol), (1,1'-)bis(diphenylphosphino)ferrocene) palladium (II) dichloride (2.73 mg, 0.00330 mmol), and triethylamine (134 mg, 1.32 mmol) in DMF (2 mL) was purged with nitrogen gas for 2 minutes. 2-methylbut-3-yn-2-ol (16.7 mg, 0.198 mmol) was then added and the mixture was heated at 100° C. for 2 hrs. Upon completion, the mixture was cooled to room temperature, and ethyl acetate and sat. NH$_4$Cl (aq) were added to the mixture. The aqueous layer was extracted with EA and the combined organic layers were dried over Na$_2$SO$_4$ and concentrated in vacuo. The residue was purified by reverse phase HPLC (0.1% trifluoroacetic acid in acetonitrile/water) providing the title compound as the mono-TFA salt. 1H NMR (400 MHz, DMSO-d$_6$) δ 8.17 (d, J=8.5 Hz, 1H), 7.97 (td, J=8.5, 5.4 Hz, 1H), 7.29 (dd, J=11.9, 8.3 Hz, 1H), 7.10 (d, J=7.6 Hz, 2H), 6.97 (d, J=9.0 Hz, 1H), 6.53 (tt, J=55.8, 3.9 Hz, 1H), 4.63 (td, J=14.6, 3.9 Hz, 2H), 3.01 (s, 3H), 1.42 (s, 6H); MS (m/z) 458.1 [M+H]+.

Example 705. 4-(3-((2,2-difluoroethyl)(7-fluoro-1-methyl-[1,2,4]triazolo[4,3-a]quinazolin-5-yl)amino)-5-fluorophenyl)-2-methylbut-3-yn-2-ol

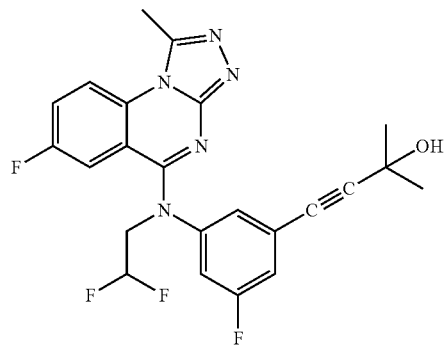 [SMILES: Cc1nnc2nc(N(CC(F)F)c3cc(F)cc(C#CC(C)(C)O)c3)c3cc(F)ccc3n12]

The title compound was prepared according to the general procedures described for Example 704. 1H NMR (400 MHz, DMSO-d$_6$) δ 8.38 (dd, J=9.4, 4.6 Hz, 1H), 7.84 (td, J=8.8, 2.9 Hz, 1H), 7.31 (d, J=10.3 Hz, 1H), 7.23 (s, 1H), 7.15 (d, J=8.9 Hz, 1H), 7.07 (dd, J=9.8, 2.9 Hz, 1H), 6.56 (tt, J=55.7, 4.1 Hz, 1H), 4.58 (td, J=14.4, 4.0 Hz, 2H), 3.01 (s, 3H), 1.43 (s, 6H); LCMS(m/z) 458.1.

Example 706. N-(2,2-difluoroethyl)-6-fluoro-N-(3-fluoro-5-((1-methylcyclopropyl)ethynyl)phenyl)-1-methyl-[1,2,4]triazolo[4,3-a]quinazolin-5-amine

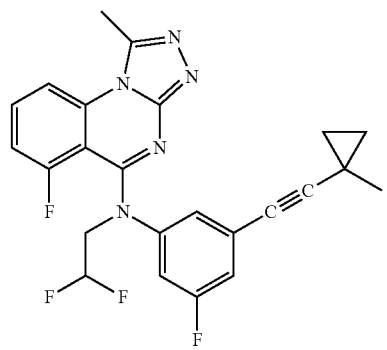 [SMILES: Cc1nnc2nc(N(CC(F)F)c3cc(F)cc(C#CC4(C)CC4)c3)c3c(F)cccc3n12]

The title compound was prepared according to the general procedures described for Example 704. 1H NMR (400 MHz, DMSO-d$_6$) δ 8.16 (d, J=8.6 Hz, 1H), 7.97 (q, J=8.0 Hz, 1H), 7.29 (dd, J=12.0, 8.3 Hz, 1H), 7.06 (d, J=7.1 Hz, 2H), 6.95

(d, J=9.1 Hz, 1H), 6.74-6.28 (m, 1H), 4.61 (td, J=14.7, 3.8 Hz, 2H), 3.01 (s, 3H), 1.26 (s, 3H), 0.90 (d, J=4.6 Hz, 2H), 0.77-0.67 (m, 2H); LCMS(m/z) 454.2.

Example 707. N-(2,2-difluoroethyl)-7-fluoro-N-(3-fluoro-5-((1-methylcyclopropyl)ethynyl)phenyl)-1-methyl-[1,2,4]triazolo[4,3-a]quinazolin-5-amine

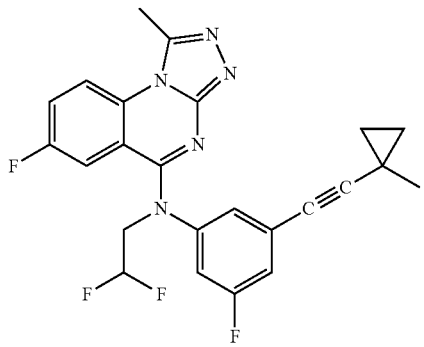 [SMILES: Cc1nnc2nc(N(CC(F)F)c3cc(F)cc(C#CC4(C)CC4)c3)c3cc(F)ccc3n12]

The title compound was prepared according to the general procedures described for Example 704. 1H NMR (400 MHz, DMSO-d$_6$) δ 8.37 (dd, J=9.4, 4.6 Hz, 1H), 7.84 (td, J=8.7, 2.8 Hz, 1H), 7.25 (d, J=10.3 Hz, 1H), 7.20 (s, 1H), 7.13 (d, J=9.1 Hz, 1H), 7.07 (dd, J=9.8, 2.9 Hz, 1H), 6.74-6.27 (m, 1H), 4.57 (td, J=14.4, 4.0 Hz, 2H), 3.01 (s, 3H), 1.27 (s, 3H), 1.02-0.90 (m, 2H), 0.73 (q, J=4.1 Hz, 2H); LCMS(m/z) 454.2.

Example 708. N-(2,2-difluoroethyl)-7-fluoro-N-(3-fluoro-5-((1-methylcyclopropyl)ethynyl)phenyl)-1-methyl-[1,2,4]triazolo[4,3-a]quinazolin-5-amine

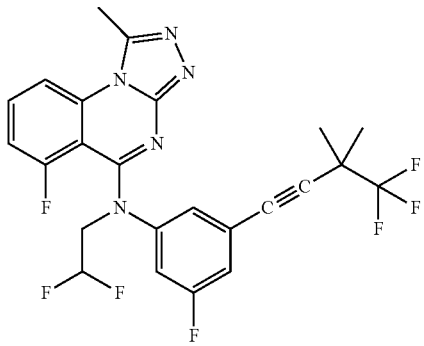 [SMILES: Cc1nnc2nc(N(CC(F)F)c3cc(F)cc(C#CC(C)(C)C(F)(F)F)c3)c3c(F)cccc3n12]

The title compound was prepared according to the general procedures described for Example 704. 1H NMR (400 MHz, DMSO-d$_6$) δ 8.17 (d, J=8.6 Hz, 1H), 7.98 (td, J=8.3, 5.2 Hz, 1H), 7.30 (dd, J=12.0, 8.3 Hz, 1H), 7.21 (s, 1H), 7.13 (d, J=10.7 Hz, 1H), 7.06 (d, J=8.9 Hz, 1H), 6.80-6.26 (m, 1H), 4.65 (td, J=14.7, 3.8 Hz, 2H), 3.02 (s, 3H), 1.47 (s, 6H); LCMS(m/z) 510.1.

Example 709. N-(2,2-difluoroethyl)-6-fluoro-N-(3-fluoro-5-((1-(trifluoromethyl)cyclopropyl)ethynyl)phenyl)-1-methyl-[1,2,4]triazolo[4,3-a]quinazolin-5-amine

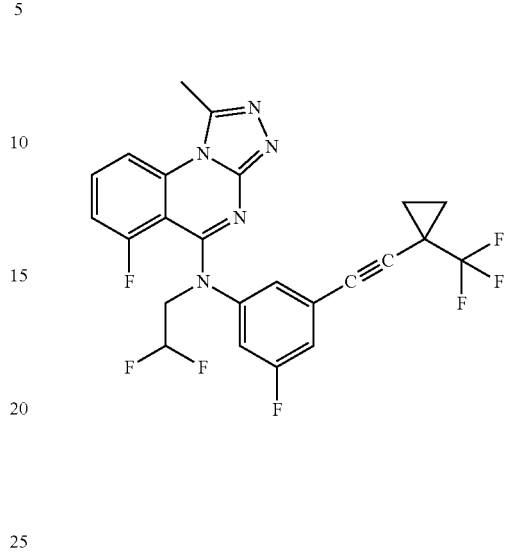

The title compound was prepared according to the general procedures described for Example 704. 1H NMR (400 MHz, DMSO-d$_6$) δ 8.17 (d, J=8.5 Hz, 1H), 7.97 (q, J=7.6 Hz, 1H), 7.28 (dd, J=11.9, 8.3 Hz, 1H), 7.19 (s, 1H), 7.14 (d, J=10.9 Hz, 1H), 7.07 (d, J=9.0 Hz, 1H), 6.53 (tt, J=55.6, 4.0 Hz, 1H), 4.75-4.36 (m, 2H), 3.01 (s, 3H), 1.53-1.15 (m, 4H); LCMS(m/z) 508.1.

Example 710. 4-(1-(6-fluoro-1-methyl-[1,2,4]triazolo[4,3-a]quinazolin-5-yl)-1,2,3,4-tetrahydroquinolin-5-yl)-2-methylbut-3-yn-2-ol

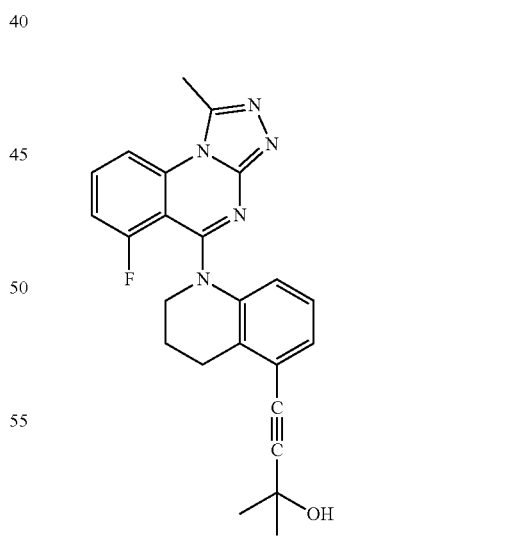

The title compound was prepared according to the general procedures described for Example 719. 1H NMR (400 MHz, DMSO-d$_6$) δ 8.17 (d, J=8.6 Hz, 1H), 7.99 (td, J=8.4, 5.4 Hz, 1H), 7.35 (dd, J=11.8, 8.2 Hz, 1H), 7.10 (d, J=7.5 Hz, 1H), 6.92 (t, J=7.9 Hz, 1H), 6.79 (d, J=8.1 Hz, 1H), 3.95 (s, 2H), 3.00 (s, 5H), 2.07 (s, 2H), 1.51 (s, 6H); LCMS(m/z) 416.2.

Example 711. 5-(5-(4,4-difluoro-3,3-dimethylbut-1-yn-1-yl)-3,4-dihydroquinolin-1(2H)-yl)-6-fluoro-1-methyl-[1,2,4]triazolo[4,3-a]quinazoline

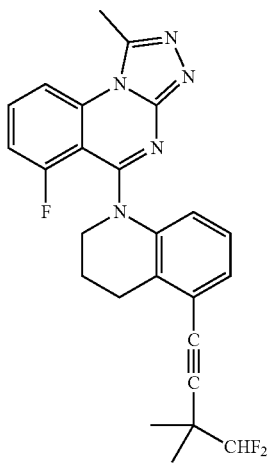 [SMILES: Cc1nnc2nc(N3CCCc4c(C#CC(C)(C)C(F)F)cccc43)c3c(F)cccc3n12]

The title compound was prepared according to the general procedures described for Example 719. 1H NMR (400 MHz, DMSO-d$_6$) δ 8.18 (d, J=8.6 Hz, 1H), 8.01 (td, J=8.4, 5.3 Hz, 1H), 7.37 (dd, J=11.8, 8.2 Hz, 1H), 7.14 (d, J=7.5 Hz, 1H), 6.94 (t, J=7.9 Hz, 1H), 6.84 (d, J=8.1 Hz, 1H), 6.09 (t, J=56.4 Hz, 1H), 4.07 (m, 2H), 3.01 (s, 3H), 2.93 (s, 3H), 2.67 (s, 1H), 1.37 (s, 6H); LCMS(m/z) 450.2.

Example 712. 5-(5-(4,4-difluoro-3,3-dimethylbut-1-yn-1-yl)-3,4-dihydroquinolin-1(2H)-yl)-7-fluoro-1-methyl-[1,2,4]triazolo[4,3-a]quinazoline

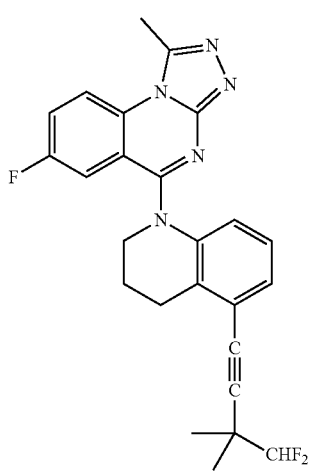 [SMILES: Cc1nnc2nc(N3CCCc4c(C#CC(C)(C)C(F)F)cccc43)c3cc(F)ccc3n12]

The title compound was prepared according to the general procedures described for Example 719. 1H NMR (400 MHz, DMSO-d$_6$) δ 8.38 (dd, J=9.4, 4.6 Hz, 1H), 7.87 (ddd, J=10.5, 7.9, 2.9 Hz, 1H), 7.44 (dd, J=9.6, 2.9 Hz, 1H), 7.29-7.09 (m, 1H), 6.99 (t, J=7.9 Hz, 1H), 6.81 (d, J=8.1 Hz, 1H), 6.09 (t, J=56.4 Hz, 1H), 3.97 (t, J=6.2 Hz, 2H), 3.00 (d, J=6.5 Hz, 5H), 2.16-1.93 (m, 2H), 1.38 (s, 6H); LCMS(m/z) 450.2.

Example 713. 1-(difluoromethyl)-7-fluoro-5-(5-((1-(trifluoromethyl)cyclopropyl)ethynyl)-3,4-dihydroquinolin-1(2H)-yl)-[1,2,4]triazolo[4,3-a]quinazoline

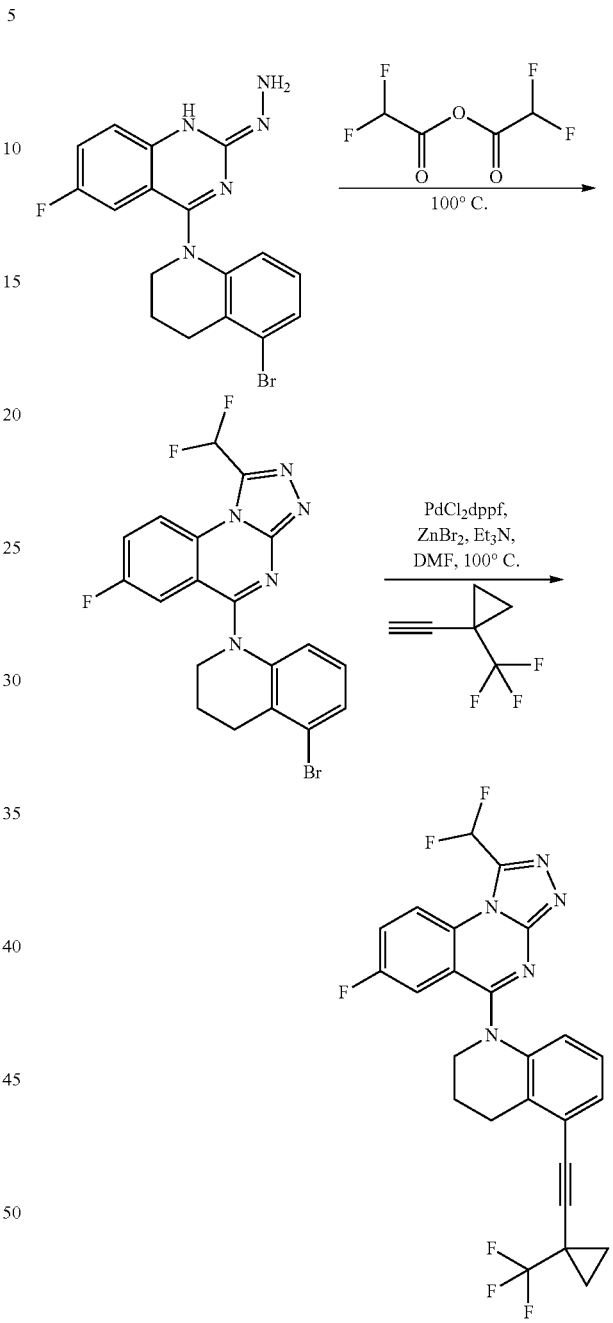

Synthesis of 5-(5-bromo-3,4-dihydro-2H-quinolin-1-yl)-1-(difluoromethyl)-7-fluoro-[1,2,4]triazolo[4,3-a]quinazoline: 2,2-Difluoroacetate (978 mg, 5.62 mmol) was added to [4-(5-bromo-3,4-dihydro-2H-quinolin-1-yl)-6-fluoro-quinazolin-2-yl]hydrazine (170 mg, 0.438 mmol) and the resultant mixture was heated to 50° C. for 10 mins. Thereafter, THF (2 mL) was added and the mixture was heated to 150° C. for 15 mins in a microwave. The crude mixture was then allowed to cool to room temperature, and the mixture was concentrated in vacuo. The crude product was purified by column chromatography on silica gel using ethyl acetate in hexanes (0-70%) as the eluant. The appropriate fractions were combined and concentrated in vacuo to afford the desired compound.

Synthesis of 1-(difluoromethyl)-7-fluoro-5-[5-[2-[1-(trifluoromethyl)cyclopropyl]ethynyl]-3,4-dihydro-2H-quinolin-1-yl]-[1,2,4]triazolo[4,3-a]quinazoline: 5-(5-Bromo-3,4-dihydro-2H-quinolin-1-yl)-1-(difluoromethyl)-7-fluoro-[1,2,4]triazolo[4,3-a]quinazoline (30 mg, 0.0669 mmol), zinc bromide (76.4 mg, 0.34 mmol), (1,1'-)bis(diphenylphosphino)ferrocene) palladium (II) dichloride (5.53 mg, 0.00669 mmol), and triethylamine (135 mg, 1.34 mmol) in DMF (2 mL) was purged with nitrogen gas for 2 minutes. 1-Ethynyl-1-(trifluoromethyl)cyclopropane (72 mg, 0.535 mmol) was then added and the mixture was heated at 100° C. for 2 hrs. The mixture was then allowed to cool to room temperature. Ethyl acetate and sat. NH$_4$Cl (aq) were added to the mixture. The aqueous layer was extracted with ethyl acetate. The combined organic layers were dried over Na$_2$SO$_4$ and concentrated in vacuo. The residue was purified by reverse phase HPLC (0.1% trifluoroacetic acid in acetonitrile/water), providing the title compound as the mono-TFA salt. 1H NMR (400 MHz, DMSO-d$_6$) δ 8.22 (dd, J=9.4, 4.5 Hz, 1H), 8.05-7.62 (m, 2H), 7.48 (dd, J=9.5, 2.9 Hz, 1H), 7.17 (d, J=7.3 Hz, 1H), 7.02-6.89 (m, 2H), 3.95 (t, J=6.1 Hz, 2H), 2.98 (t, J=6.7 Hz, 2H), 2.10 (p, J=6.5 Hz, 2H), 1.49 (t, J=3.3 Hz, 2H), 1.43 (d, J=5.1 Hz, 3H); MS (m/z) 502.1 [M+H]$^+$.

Example 714. 4-(6,7-difluoro-[1,2,4]triazolo[4,3-a]quinazolin-5-yl)-8-((1-(trifluoromethyl)cyclopropyl)ethynyl)-3,4-dihydro-2H-benzo[b][1,4]oxazine

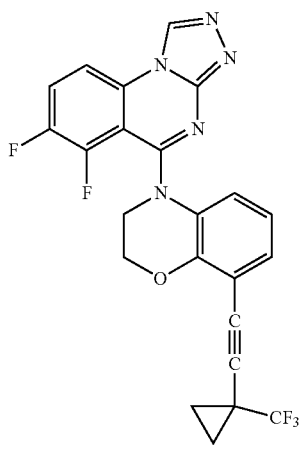

The title compound was prepared according to the general procedures described for Example 724. 1H NMR (400 MHz, DMSO-d$_6$) δ 9.79 (s, 1H), 8.33 (dd, J=9.5, 4.1 Hz, 1H), 8.24 (q, J=9.2 Hz, 1H), 7.09 (dd, J=17.8, 7.9 Hz, 2H), 6.73 (t, J=7.9 Hz, 1H), 4.78-3.82 (m, 4H), 1.50-1.42 (m, 2H), 1.37 (s, 2H); LCMS(m/z) 472.1.

Example 715. 6-fluoro-1-methyl-5-(5-(4,4,4-trifluoro-3,3-dimethylbut-1-yn-1-yl)-3,4-dihydroquinolin-1(2H)-yl)-[1,2,4]triazolo[4,3-a]quinazoline

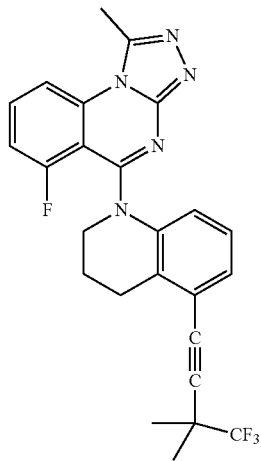 [SMILES: Cc1nnc2nc(N3CCCc4c(C#CC(C)(C)C(F)(F)F)cccc43)c3c(F)cccc3n12]

The title compound was prepared according to the general procedures described for Example 719. 1H NMR (400 MHz, DMSO-d$_6$) δ 8.17 (d, J=8.6 Hz, 1H), 7.99 (td, J=8.4, 5.3 Hz, 1H), 7.36 (dd, J=12.0, 8.2 Hz, 1H), 7.14 (d, J=7.5 Hz, 1H), 6.95 (t, J=7.9 Hz, 1H), 6.85 (d, J=8.2 Hz, 1H), 4.01 (m, 2H), 3.00 (s, 3H), 2.90 (m, 2H), 2.08 (m, 2H), 1.55 (s, 6H); LCMS(m/z) 468.2.

Example 716. 6-fluoro-1-methyl-5-(5-((1-(trifluoromethyl)cyclopropyl)ethynyl)-3,4-dihydroquinolin-1(2H)-yl)-[1,2,4]triazolo[4,3-a]quinazoline

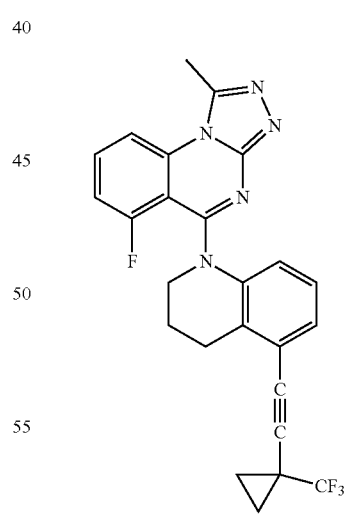

The title compound was prepared according to the general procedures described for Example 719. 1H NMR (400 MHz, DMSO-d$_6$) δ 8.18 (d, J=8.6 Hz, 1H), 8.01 (td, J=8.4, 5.4 Hz, 1H), 7.38 (dd, J=11.8, 8.2 Hz, 1H), 7.17 (dd, J=7.6, 1.2 Hz, 1H), 6.96 (t, J=7.9 Hz, 1H), 6.87 (d, J=8.1 Hz, 1H), 4.47-3.52 (m, 2H), 3.01 (s, 3H), 2.93 (s, 2H), 2.29-1.68 (m, 2H), 1.53-1.39 (m, 4H); LCMS(m/z) 466.2.

Example 717. 6-fluoro-1-methyl-5-(5-((1-(trifluoromethyl)cyclopropyl)ethynyl)-3,4-dihydroquinolin-1(2H)-yl)-[1,2,4]triazolo[4,3-a]quinazoline

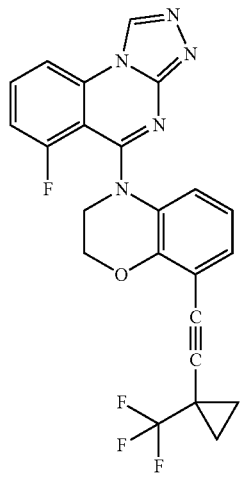 [SMILES: Fc1cccc2c1c(N1CCOc3c(C#CC4(C(F)(F)F)CC4)cccc31)nc1nncn12]

The title compound was prepared according to the general procedures described for Example 722. 1H NMR (400 MHz, DMSO-d$_6$) δ 9.79 (s, 1H), 8.27 (d, J=8.4 Hz, 1H), 8.06 (td, J=8.3, 5.1 Hz, 1H), 7.45 (dd, J=12.0, 8.2 Hz, 1H), 7.10 (dd, J=7.6, 1.5 Hz, 1H), 7.03 (dd, J=8.2, 1.5 Hz, 1H), 6.71 (t, J=7.9 Hz, 1H), 4.44 (s, 2H), 1.50-1.42 (m, 2H), 1.37 (s, 2H); LCMS(m/z) 454.1.

Example 718. 7-fluoro-1-methyl-5-(5-(4,4,4-trifluoro-3,3-dimethylbut-1-yn-1-yl)-3,4-dihydroquinolin-1(2H)-yl)-[1,2,4]triazolo[4,3-a]quinazoline

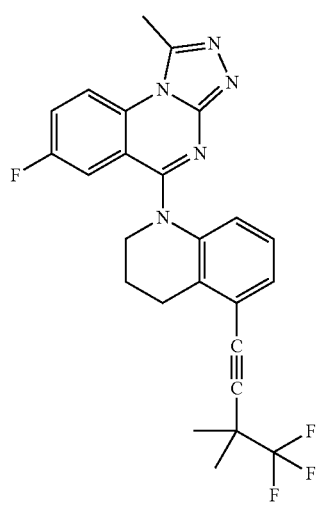 [SMILES: Cc1nnc2nc(N3CCCc4c(C#CC(C)(C)C(F)(F)F)cccc43)c3cc(F)ccc3n12]

The title compound was prepared according to the general procedures described for Example 719. 1H NMR (400 MHz, DMSO-d$_6$) δ 8.40 (dd, J=9.4, 4.6 Hz, 1H), 7.89 (ddd, J=9.3, 7.9, 2.9 Hz, 1H), 7.47 (dd, J=9.6, 2.9 Hz, 1H), 7.22 (dd, J=7.6, 1.1 Hz, 1H), 7.02 (t, J=7.9 Hz, 1H), 6.87 (d, J=8.2 Hz, 1H), 4.00 (t, J=6.1 Hz, 2H), 3.01 (d, J=11.0 Hz, 5H), 2.12 (p, J=6.5 Hz, 2H), 1.56 (s, 6H); LCMS(m/z) 468.2.

Example 719. 7-fluoro-1-methyl-5-(5-(4,4,4-trifluoro-3,3-dimethylbut-1-yn-1-yl)-3,4-dihydroquinolin-1(2H)-yl)-[1,2,4]triazolo[4,3-a]quinazoline

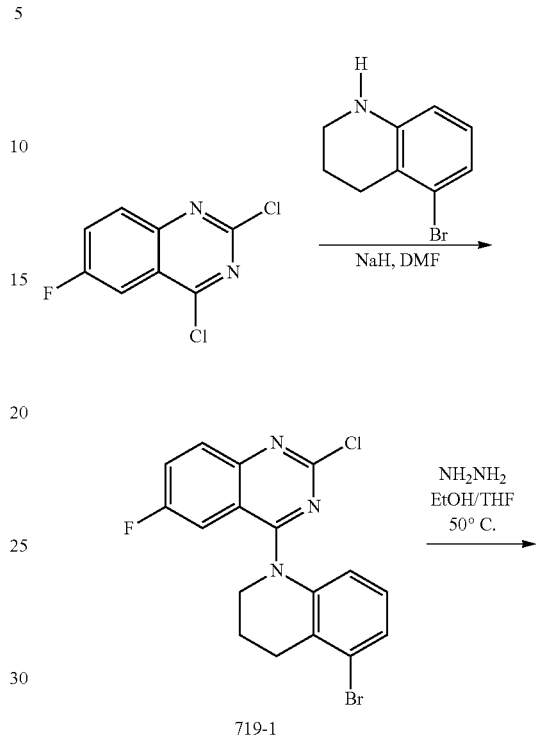

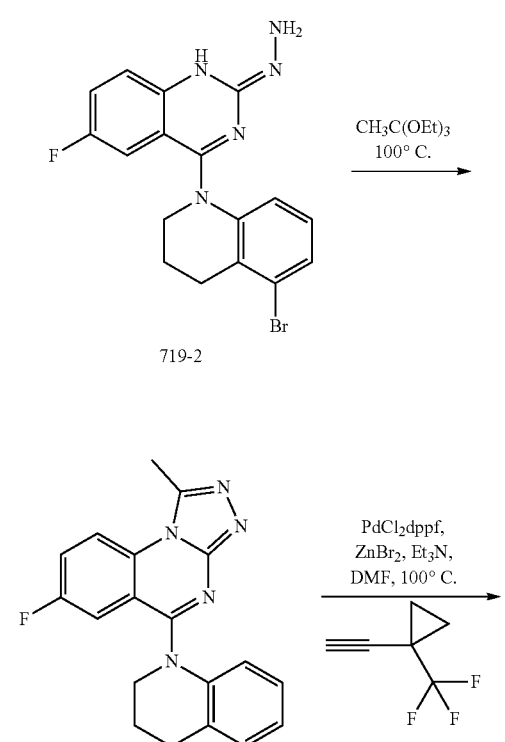

-continued

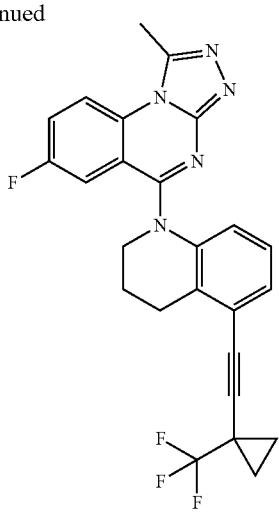

Synthesis of 4-(5-bromo-3,4-dihydroquinolin-1(2H)-yl)-2-chloro-6-fluoroquinazoline (Compound 719-1): To a solution of 5-bromo-1,2,3,4-tetrahydroquinoline (195 mg, 0.92 mmol) in DMA (2.0 mL) at 0° C. was added NaH (60% dispersion in mineral oil) (70 mg, 1.84 mmol) in one portion. The mixture was stirred at 0° C. for 30 min, followed by addition of the 2,4-dichloro-6-fluoroquinazoline (200 mg, 0.92 mmol) in one portion. The resultant mixture was warmed to room temperature over 16 h. Upon completion, the mixture was poured into water (20 mL) and extracted with ethyl acetate (2×20 ml each). The organics were separated and dried over sodium sulfate, filtered, and concentrated under vacuum. The crude residue was purified by column chromatography on silica gel using ethyl acetate in hexanes 0-40% as the eluent. Appropriate fractions were combined and concentrated in vacuo to afford the desired compound. (MS (m/z) 393.2 [M+H]$^+$.

Synthesis of [4-(5-bromo-3,4-dihydro-2H-quinolin-1-yl)-6-fluoro-quinazolin-2-yl]hydrazine (Compound 719-2): To a solution of 4-(5-bromo-3,4-dihydroquinolin-1(2H)-yl)-2-chloro-6-fluoroquinazoline (185 mg, 0.47 mmol) in THF (5 mL) and ethanol (5 mL) was added anhydrous hydrazine (151 mg, 4.71 mmol) and the mixture was stirred at room temperature for 5 hrs. Upon completion, the reaction was diluted with dichloromethane and washed with water followed by brine. The resulting organics were dried over Na$_2$SO$_4$, filtered, and concentrated under reduced pressure to afford the desired compound. MS (m/z) 390.4 [M+H]$^+$.

Synthesis of 5-(4-bromo-3,4-dihydroquinolin-1(2H)-yl)-7-fluoro-1-methyl-[1,2,4]triazolo[4,3-a]quinazoline (Compound 719-3): A solution of [4-(5-bromo-3,4-dihydro-2H-quinolin-1-yl)-6-fluoro-quinazolin-2-yl]hydrazine (400 mg, 1.03 mmol) and triethyl orthoacetate (0.9 g, 5.62 mmol) was heated to 100° C. for 16 hrs. The reaction was then allowed to cool to room temperature, whereupon the mixture was concentrated under reduced pressure to afford the crude residue. This residue was triturated with heptane and the solids were collected by filtration, washed with heptanes and dried in vacuo to afford the desired compound. MS (m/z) 412.4, 414.3 [M+H]$^+$.

Synthesis of 7-fluoro-1-methyl-5-[5-[2-[1-(trifluoromethyl)cyclopropyl]ethynyl]-3,4-dihydro-2H-quinolin-1-yl]-[1,2,4]triazolo[4,3-a]quinazoline: A solution of 5-(5-bromo-3,4-dihydro-2H-quinolin-1-yl)-7-fluoro-1-methyl-[1,2,4]triazolo[4,3-a]quinazoline (26.4 mg, 0.0641 mmol), zinc bromide (72.2 mg, 0.32 mmol), (1,1'-)bis(diphenylphosphino)ferrocene) palladium (II) dichloride (5.3 mg, 0.00641 mmol), and triethylamine (130 mg, 1.28 mmol) in DMF (2 mL) was purged with nitrogen gas for 2 minutes. 1-Ethynyl-1-(trifluoromethyl)cyclopropane (53 mg, 0.396 mmol) was then added and the mixture was heated at 100° C. for 2 hrs. The mixture was then allowed to cool to room temperature, and ethyl acetate and sat. NH$_4$Cl(aq) were added. The aqueous layer was extracted with ethyl acetate. The combined organic layers were dried over Na$_2$SO$_4$ and concentrated in vacuo. The resulting crude residue was purified by reverse phase HPLC (0.1% trifluoroacetic acid in acetonitrile/water) to give the title compound as the mono-TFA salt. 1H NMR (400 MHz, DMSO-d$_6$) δ 8.40 (dd, J=9.4, 4.6 Hz, 1H), 7.89 (ddd, J=9.3, 7.8, 2.9 Hz, 1H), 7.45 (dd, J=9.5, 2.9 Hz, 1H), 7.22 (dd, J=7.6, 1.1 Hz, 1H), 7.02 (t, J=7.9 Hz, 1H), 6.87 (d, J=8.1 Hz, 1H), 3.99 (t, J=6.2 Hz, 2H), 3.00 (d, J=10.3 Hz, 5H), 2.11 (p, J=6.5 Hz, 2H), 1.55-1.40 (m, 4H); MS (m/z) 466.2 [M+H]$^+$.

Example 720. 4-(7-fluoro-[1,2,4]triazolo[4,3-a]quinazolin-5-yl)-8-((1-(trifluoromethyl)cyclopropyl)ethynyl)-3,4-dihydro-2H-benzo[b][1,4]oxazine

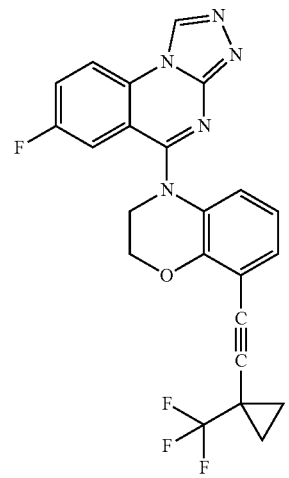 [SMILES: Fc1ccc2c(c1)c(N1CCOc3c(C#CC4(C(F)(F)F)CC4)cccc31)nc1nncn12]

The title compound was synthesized according to the general procedures described for Example 724. 1H NMR (400 MHz, DMSO-d$_6$) δ 9.85 (t, J=2.0 Hz, 1H), 8.54 (dd, J=9.2, 4.6 Hz, 1H), 8.01 (t, J=8.8 Hz, 1H), 7.90 (dt, J=9.5, 2.2 Hz, 1H), 7.13 (dt, J=7.6, 1.3 Hz, 1H), 7.01 (dt, J=8.2, 1.6 Hz, 1H), 6.74 (t, J=7.9 Hz, 1H), 4.51 (t, J=4.4 Hz, 2H), 4.10 (s, 2H), 1.61-1.42 (m, 2H), 1.42-1.28 (m, 2H); LCMS(m/z) 454.1.

Example 721. 4-(7-fluoro-1-methyl-[1,2,4]triazolo [4,3-a]quinazolin-5-yl)-8-((1-(trifluoromethyl)cyclopropyl)ethynyl)-3,4-dihydro-2H-benzo[b][1,4] oxazine

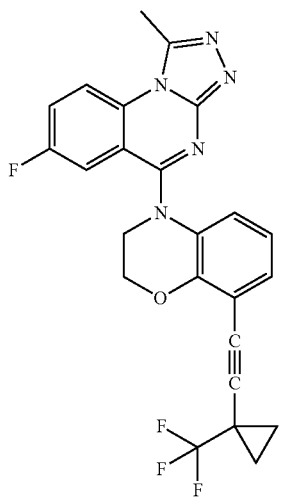

The title compound was synthesized according to the general procedures described for Example 722. 1H NMR (400 MHz, DMSO-$d_6$) δ 8.41 (dd, J=9.2, 4.6 Hz, 1H), 7.99-7.87 (m, 2H), 7.12 (dd, J=7.6, 1.5 Hz, 1H), 6.92 (dd, J=8.2, 1.5 Hz, 1H), 6.73 (t, J=7.9 Hz, 1H), 4.51 (t, J=4.4 Hz, 2H), 4.08 (d, J=4.5 Hz, 2H), 3.01 (s, 3H), 1.51-1.39 (m, 2H), 1.38 (d, J=6.1 Hz, 2H); LCMS(m/z) 468.1.

Example 722. 4-(7-fluoro-1-methyl-[1,2,4]triazolo [4,3-a]quinazolin-5-yl)-8-(4,4,4-trifluoro-3,3-dimethylbut-1-yn-1-yl)-3,4-dihydro-2H-benzo[b][1,4] oxazine

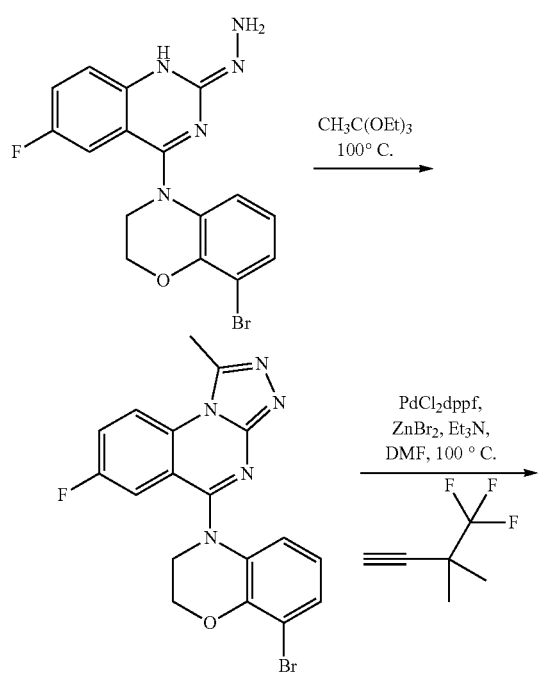

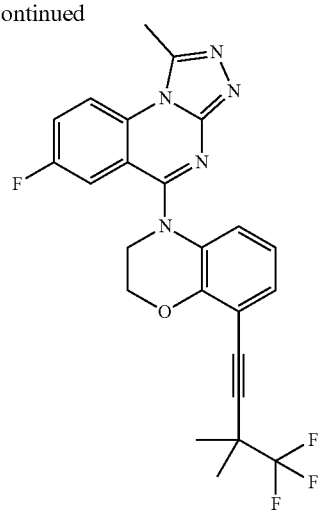

Synthesis of 8-bromo-4-(7-fluoro-1-methyl-[1,2,4]triazolo[4,3-a]quinazolin-5-yl)-2,3-dihydro-1,4-benzoxazine: A solution of [4-(8-bromo-2,3-dihydro-1,4-benzoxazin-4-yl)-6-fluoro-quinazolin-2-yl]hydrazine (350 mg, 0.897 mmol) and triethyl orthoacetate (0.9 g, 5.62 mmol) was heated to 100° C. for 16 hrs. The reaction was then cooled to room temperature, and concentrated under reduced pressure to afford the crude product. The crude product was triturated with heptanes and the solids were collected by filtration, washed with heptanes and dried in vacuo to afford the desired compound. MS (m/z) 414.4, 416.3 [M+H]⁺.

Synthesis of 4-(7-fluoro-1-methyl-[1,2,4]triazolo[4,3-a] quinazolin-5-yl)-8-(4,4,4-trifluoro-3,3-dimethyl-but-1-ynyl)-2,3-dihydro-1,4-benzoxazine: A solution of 8-bromo-4-(7-fluoro-1-methyl-[1,2,4]triazolo[4,3-a]quinazolin-5-yl)-2,3-dihydro-1,4-benzoxazine (31.1 mg, 0.0751 mmol), zinc bromide (84.6 mg, 0.376 mmol), (1,1'-)bis(diphenylphosphino)ferrocene) palladium (II) dichloride (6.2 mg, 0.00751 mmol), and triethylamine (152 mg, 1.50 mmol) in DMF (2 mL) was purged with nitrogen gas for 2 minutes. 4,4,4-Trifluoro-3,3-dimethyl-but-1-yne (63 mg, 0.464 mmol) was then added and the mixture was heated at 100° C. for 2 hrs. The mixture was then cooled to room temperature, and ethyl acetate and sat. NH₄Cl (aq) were added to the mixture. The aqueous layer was extracted with EA and the combined organic layers were dried over Na₂SO₄ and concentrated in vacuo. The residue was purified by reverse phase HPLC (0.1% trifluoroacetic acid in acetonitrile/water) providing the title compound as the mono-TFA salt. TH NMR (400 MHz, DMSO-$d_6$) δ 8.41 (dd, J=9.3, 4.5 Hz, 1H), 7.93 (ddd, J=16.8, 8.8, 2.9 Hz, 2H), 7.10 (dd, J=7.6, 1.5 Hz, 1H), 6.92 (dd, J=8.2, 1.4 Hz, 1H), 6.73 (t, J=7.9 Hz, 1H), 4.52 (t, J=4.4 Hz, 2H), 4.09 (s, 2H), 3.01 (s, 3H), 1.52 (s, 6H); MS (m/z) 470.2 [M+H]⁺.

Example 723. 4-(4-(7-fluoro-[1,2,4]triazolo[4,3-a]quinazolin-5-yl)-3,4-dihydro-2H-benzo[b][1,4]oxazin-8-yl)-2-methylbut-3-yn-2-ol

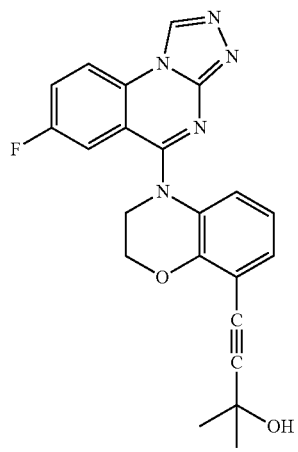

The title compound was synthesized according to the general procedures described for Example 724. TH NMR (400 MHz, DMSO-d$_6$) δ 9.80 (s, 1H), 8.52 (dd, J=9.1, 4.7 Hz, 1H), 7.98 (td, J=8.7, 2.8 Hz, 1H), 7.86 (dd, J=9.4, 2.8 Hz, 1H), 7.04 (dd, J=7.6, 1.5 Hz, 1H), 6.97-6.90 (m, 1H), 6.71 (t, J=7.9 Hz, 1H), 4.48 (t, J=4.5 Hz, 2H), 4.06 (s, 2H), 1.48 (s, 6H); LCMS(m/z) 404.1.

Example 724. 4-(7-fluoro-[1,2,4]triazolo[4,3-a]quinazolin-5-yl)-8-(4,4,4-trifluoro-3,3-dimethylbut-1-yn-1-yl)-3,4-dihydro-2H-benzo[b][1,4]oxazine

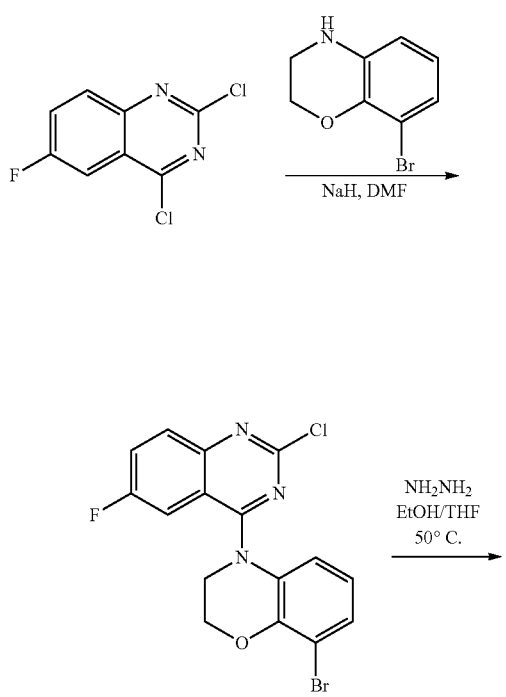

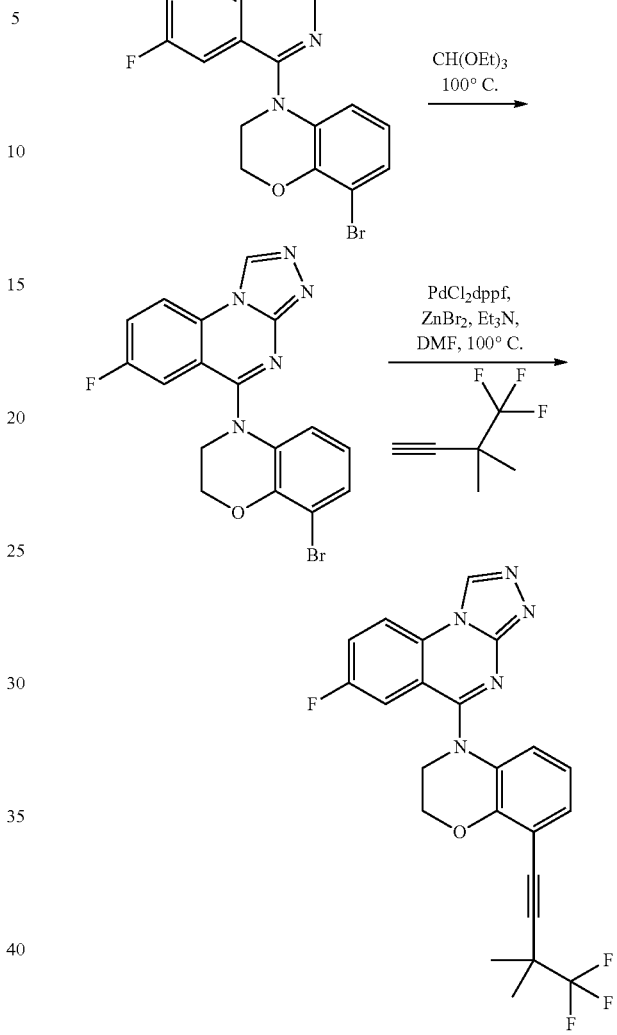

Synthesis of 8-bromo-4-(2-chloro-6-fluoroquinazolin-4-yl)-3,4-dihydro-2H-benzo[b][1,4]oxazine: To a solution of 8-bromo-3,4-dihydro-2H-1,4-benzoxazine (569 mg, 0.27 mmol) in DMA (2.0 mL) at 0° C. was added NaH (60% dispersion in mineral oil) (212 mg, 0.55 mmol) in one portion. The mixture was stirred at 0° C. for 30 min, followed by the 2,4-dichloro-6-fluoroquinazoline (600 mg, 0.27 mmol) in one portion and the mixture was warmed to room temperature over 16 h. Upon completion, the mixture was poured into water (20 mL) and extracted with ethyl acetate (2×20 ml each). The organics were separated and dried over sodium sulfate, filtered and concentrated under vacuum. The crude was purified by column chromatography on silica gel using ethyl acetate in hexanes 0-40% as the eluent. Appropriate fractions were combined and concentrated in vacuo to afford the desired compound. MS (m/z) 395.2[M+H]$^+$.

Synthesis of [4-(8-bromo-2,3-dihydro-1,4-benzoxazin-4-yl)-6-fluoro-quinazolin-2-yl]hydrazine: To a solution of 8-bromo-4-(2-chloro-6-fluoroquinazolin-4-yl)-3,4-dihydro-2H-benzo[b][1,4]oxazine (790 mg, 2.0 mmol) in THF (10 mL) and ethanol (10 mL) was added anhydrous hydrazine (642 mg, 20.0 mmol) and the mixture was stirred at room temperature for 30 mins. Upon completion, the reaction was diluted with dichloromethane and washed with water followed by brine. The resulting organics were dried over Na$_2$SO$_4$, filtered and concentrated under reduced pressure to afford the desired compound. MS (m/z) 391.5, 393.5 [M+H]$^+$.

Synthesis of 8-bromo-4-(7-fluoro-[1,2,4]triazolo[4,3-a]quinazolin-5-yl)-3,4-dihydro-2H-benzo[b][1,4]oxazine: A solution of [4-(8-bromo-2,3-dihydro-1,4-benzoxazin-4-yl)-6-fluoro-quinazolin-2-yl]hydrazine (350 mg, 0.897 mmol) and triethyl orthoformate (0.8 g, 5.62 mmol) was heated to 100° C. for 16 hrs. Upon completion, the reaction was cooled to room temperature, and concentrated under reduced pressure to afford the crude product. The crude product was triturated with heptanes and the solids were collected by filtration, washed with heptanes and dried in vacuo to afford the desired compound. MS (m/z) 399.7, 401.2 [M+H]$^+$.

Synthesis of 4-(7-fluoro-[1,2,4]triazolo[4,3-a]quinazolin-5-yl)-8-(4,4,4-trifluoro-3,3-dimethylbut-1-yn-1-yl)-3,4-dihydro-2H-benzo[b][1,4]oxazine: A solution of 8-bromo-4-(7-fluoro-[1,2,4]triazolo[4,3-a]quinazolin-5-yl)-3,4-dihydro-2H-benzo[b][1,4]oxazine (30.1 mg, 0.0751 mmol), zinc bromide (84.6 mg, 0.376 mmol), (1,1'-)bis(diphenylphosphino)ferrocene) palladium (II) dichloride (6.2 mg, 0.00751 mmol), and triethylamine (152 mg, 1.50 mmol) in DMF (2 mL) was purged with nitrogen gas for 2 minutes. 4,4,4-trifluoro-3,3-dimethyl-but-1-yne (63 mg, 0.464 mmol) was then added and the mixture was heated at 100° C. for 2 hrs. Upon completion, the mixture was cooled to room temperature, and ethyl acetate and sat. NH$_4$Cl (aq) were added to the mixture. The aqueous layer was extracted with EA and the combined organic layers were dried over Na$_2$SO$_4$ and concentrated in vacuo. The residue was purified by reverse phase HPLC (0.1% trifluoroacetic acid in acetonitrile/water) providing the title compound. 1H NMR (400 MHz, DMSO-d$_6$) δ 9.82 (s, 1H), 8.53 (dd, J=9.2, 4.7 Hz, 1H), 7.99 (td, J=8.6, 2.7 Hz, 1H), 7.89 (dd, J=9.5, 2.8 Hz, 1H), 7.09 (dd, J=7.6, 1.5 Hz, 1H), 6.98 (dd, J=8.3, 1.5 Hz, 1H), 6.73 (t, J=7.9 Hz, 1H), 4.54-4.47 (m, 2H), 4.08 (t, J=4.3 Hz, 2H), 1.52 (s, 6H); MS (m/z) 456.1 [M+H]$^+$.

Example 725. 6-fluoro-5-(5-((1-methylcyclopropyl)ethynyl)-3,4-dihydroquinolin-1(2H)-yl)-[1,2,4]triazolo[4,3-a]quinazoline

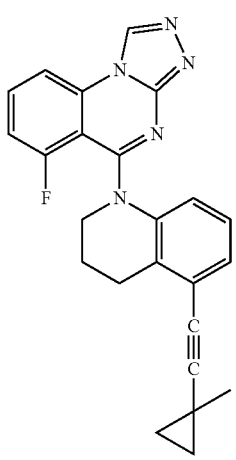 [SMILES: CC1(C#Cc2cccc3c2CCCN3c2nc3nncn3c3cccc(F)c23)CC1]

The title compound was synthesized according to the general procedures described for Example 730. 1H NMR (400 MHz, DMSO-d$_6$) δ 9.79 (s, 1H), 8.24 (d, J=8.3 Hz, 1H), 8.01 (td, J=8.3, 5.1 Hz, 1H), 7.31 (dd, J=11.9, 8.2 Hz, 1H), 7.06 (dd, J=7.5, 1.2 Hz, 1H), 6.89 (t, J=7.8 Hz, 1H), 6.85-6.77 (m, 1H), 4.13-3.66 (m, 2H), 3.04-2.76 (m, 2H), 2.06 (m, 2H), 1.36 (s, 3H), 0.98 (q, J=4.0 Hz, 2H), 0.79 (q, J=4.1 Hz, 2H); LCMS(m/z) 398.1.

Example 726. 4-(1-(6-fluoro-[1,2,4]triazolo[4,3-a]quinazolin-5-yl)-1,2,3,4-tetrahydroquinolin-5-yl)-2-methylbut-3-yn-2-ol

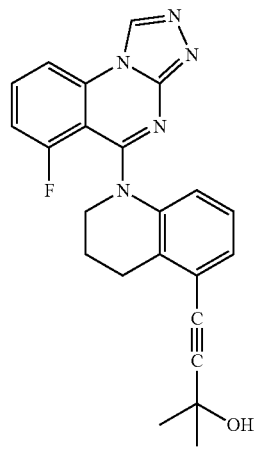 [SMILES: CC(C)(O)C#Cc1cccc2c1CCCN2c1nc2nncn2c2cccc(F)c12]

The title compound was synthesized according to the general procedures described for Example 730. 1H NMR (400 MHz, DMSO-d$_6$) δ 9.79 (s, 1H), 8.24 (d, J=8.3 Hz, 1H), 8.01 (td, J=8.3, 5.1 Hz, 1H), 7.31 (dd, J=12.0, 8.2 Hz, 1H), 7.17-7.04 (m, 1H), 6.98-6.77 (m, 2H), 3.89 (s, 2H), 3.05-2.78 (m, 2H), 2.24-1.95 (m, 2H), 1.51 (s, 6H); LCMS (m/z) 402.1.

Example 727. 6-fluoro-5-(5-(4,4,4-trifluoro-3,3-dimethylbut-1-yn-1-yl)-3,4-dihydroquinolin-1(2H)-yl)-[1,2,4]triazolo[4,3-a]quinazoline

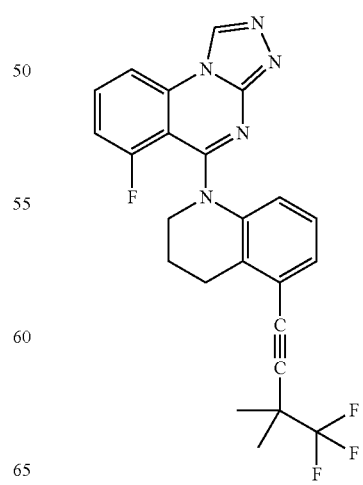

The title compound was synthesized according to the general procedures described for Example 730. 1H NMR (400 MHz, DMSO-d$_6$) δ 9.81 (s, 1H), 8.25 (d, J=8.3 Hz, 1H), 8.03 (td, J=8.3, 5.1 Hz, 1H), 7.33 (dd, J=12.0, 8.2 Hz, 1H), 7.14 (dd, J=7.2, 1.5 Hz, 1H), 7.06-6.82 (m, 2H), 3.9 (m, 2H), 2.92 (tt, J=15.2, 7.7 Hz, 2H), 2.22-1.79 (m, 2H), 1.55 (s, 6H); LCMS(m/z) 454.2.

Example 728. 6-fluoro-5-(5-((1-(trifluoromethyl)cyclopropyl)ethynyl)-3,4-dihydroquinolin-1(2H)-yl)-[1,2,4]triazolo[4,3-a]quinazoline

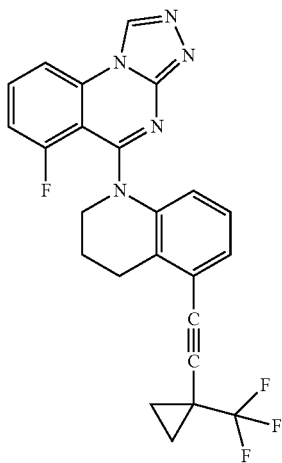 [SMILES: Fc1cccc2c1c(N1CCCc3c(C#CC4(C(F)(F)F)CC4)cccc31)nc1nncn12]

The title compound was synthesized according to the general procedures described for Example 730. 1H NMR (400 MHz, DMSO-d$_6$) δ 9.80 (s, 1H), 8.25 (d, J=8.3 Hz, 1H), 8.02 (td, J=8.3, 5.1 Hz, 1H), 7.32 (dd, J=12.0, 8.2 Hz, 1H), 7.14 (dd, J=7.2, 1.5 Hz, 1H), 7.01-6.74 (m, 2H), 3.9 (m, 2H), 2.92 (m, 2H), 2.08 (m, 2H), 1.67-1.26 (m, 4H); LCMS(m/z) 452.1.

Example 729. 7-fluoro-5-(5-(4,4,4-trifluoro-3,3-dimethylbut-1-yn-1-yl)-3,4-dihydroquinolin-1(2H)-yl)-[1,2,4]triazolo[4,3-a]quinazoline

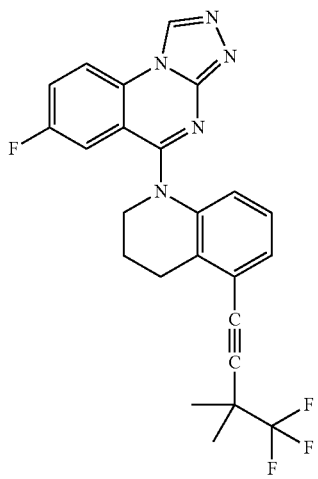 [SMILES: CC(C)(C#Cc1cccc2c1CCCN2c1nc2nncn2c2ccc(F)cc12)C(F)(F)F]

The title compound was synthesized according to the general procedures described for Example 730. H NMR (400 MHz, DMSO-d$_6$) δ 9.84 (s, 1H), 8.51 (dd, J=9.2, 4.7 Hz, 1H), 7.95 (td, J=8.6, 2.8 Hz, 1H), 7.39 (dd, J=9.7, 2.8 Hz, 1H), 7.20 (dd, J=7.6, 1.2 Hz, 1H), 7.01 (t, J=7.9 Hz, 1H), 6.92 (dd, J=8.3, 1.1 Hz, 1H), 3.98 (t, J=6.2 Hz, 2H), 2.98 (t, J=6.7 Hz, 2H), 2.11 (p, J=6.4 Hz, 2H), 1.55 (s, 6H); LCMS(m/z) 454.2.

Example 730. 7-fluoro-5-(5-((1-(trifluoromethyl)cyclopropyl)ethynyl)-3,4-dihydroquinolin-1(2H)-yl)-[1,2,4]triazolo[4,3-a]quinazoline

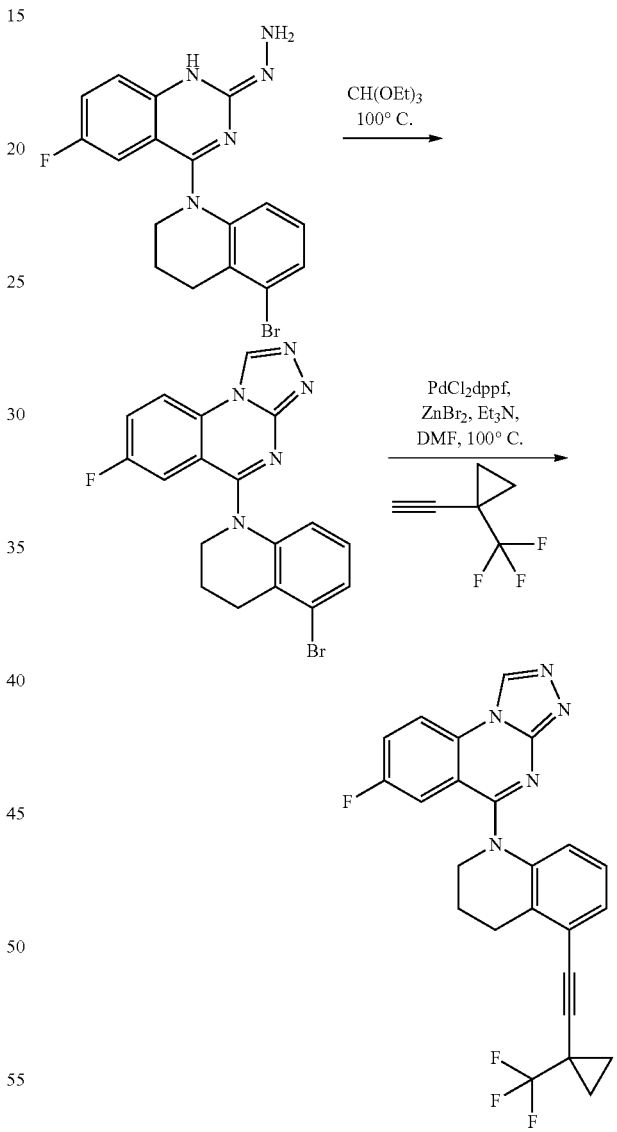

Synthesis of 5-(5-bromo-3,4-dihydroquinolin-1(2H)-yl)-7-fluoro-[1,2,4]triazolo[4,3-a]quinazoline: A solution of [4-(5-bromo-3,4-dihydro-2H-quinolin-1-yl)-6-fluoro-quinazolin-2-yl]hydrazine (300 mg, 0.77 mmol) and triethyl orthoformate (1.4 g, 9.3 mmol) was heated to 100° C. for 12 h. Upon completion, the reaction was cooled to room temperature, and concentrated under reduced pressure to afford the crude product. The crude product was triturated with heptanes and the solids were collected by filtration, washed with heptanes and dried in vacuo to afford the title compound. MS (m/z) 400.8 [M+H]⁺.

Synthesis of 7-fluoro-5-(5-((1-(trifluoromethyl)cyclopropyl)ethynyl)-3,4-dihydroquinolin-1(2H)-yl)-[1,2,4]triazolo[4,3-a]quinazoline: A solution of 5-(3,4-dihydroquinolin-1(2H)-yl)-7-fluoro-1-methyl-[1,2,4]triazolo[4,3-a]quinazoline (30 mg, 0.0753 mmol), zinc bromide (84.8 mg, 0.377 mmol), (1,1'-)bis(diphenylphosphino)ferrocene) palladium (II) dichloride (6.23 mg, 0.00753 mmol), and triethylamine (152 mg, 1.51 mmol) in DMF (2 mL) was purged with nitrogen gas for 2 minutes. 1-ethynyl-1-(trifluoromethyl)cyclopropane (80.8 mg, 0.603 mol) was then added and the mixture was heated at 100° C. for 10 minutes. Upon completion, the mixture was cooled to room temperature, and ethyl acetate and sat. NH₄C (aq) were added to the mixture. The aqueous layer was extracted with EA and the combined organic layers were dried over Na₂SO₄ and concentrated in vacuo. The residue was purified by reverse phase HPLC (0.1% trifluoroacetic acid in acetonitrile/water) providing the title compound as the mono-TFA salt: ¹H NMR (400 MHz, DMSO-d₆) δ 9.84 (s, 1H), 8.51 (dd, J=9.2, 4.7 Hz, 1H), 8.08-7.79 (m, 1H), 7.37 (dd, J=9.7, 2.8 Hz, 1H), 7.20 (dd, J=7.5, 1.2 Hz, 1H), 7.01 (t, J=7.9 Hz, 1H), 6.92 (dd, J=8.2, 1.2 Hz, 1H), 3.98 (t, J=6.2 Hz, 2H), 2.98 (t, J=6.7 Hz, 2H), 2.10 (p, J=6.5 Hz, 2H), 1.50 (td, J=6.2, 2.0 Hz, 2H), 1.47-1.33 (m, 2H); LCMS(m/z) 452.1.

Example 731. 7-fluoro-5-(5-((1-(trifluoromethyl)cyclopropyl)ethynyl)-3,4-dihydroquinolin-1(2H)-yl)-[1,2,4]triazolo[4,3-a]quinazoline

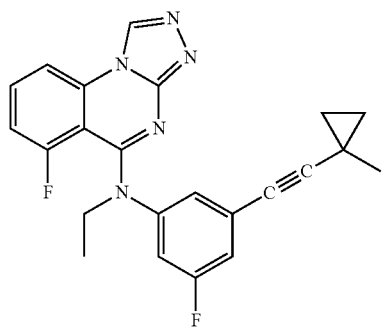 [SMILES: CCN(c1cc(F)cc(C#CC2(C)CC2)c1)c1nc2nncn2c2cccc(F)c12]

The title compound was synthesized according to the general procedures described for Example 453. 1H NMR (400 MHz, DMSO-d₆) δ 9.82 (s, 1H), 8.24 (d, J=8.3 Hz, 1H), 8.01 (td, J=8.3, 5.1 Hz, 1H), 7.32-7.16 (m, 2H), 7.13 (t, J=1.7 Hz, 1H), 7.01 (dt, J=9.1, 1.7 Hz, 1H), 4.21 (q, J=6.9 Hz, 2H), 1.42-1.06 (m, 6H), 0.90 (q, J=4.0 Hz, 2H), 0.85-0.63 (m, 2H); LCMS(m/z) 404.1.

Example 732. N-ethyl-6-fluoro-N-(3-fluoro-5-((1-(trifluoromethyl)cyclopropyl)ethynyl)phenyl)-[1,2,4]triazolo[4,3-a]quinazolin-5-amine

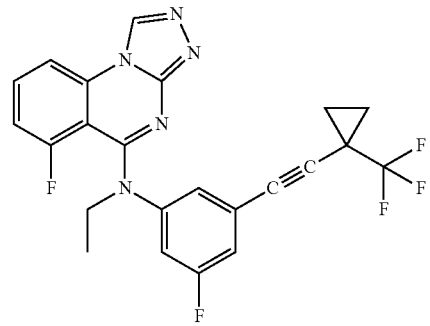 [SMILES: CCN(c1cc(F)cc(C#CC2(C(F)(F)F)CC2)c1)c1nc2nncn2c2cccc(F)c12]

The title compound was synthesized according to the general procedures described for Example 453. 1H NMR (400 MHz, DMSO-d₆) δ 9.83 (s, 1H), 8.24 (d, J=8.3 Hz, 1H), 8.01 (td, J=8.3, 5.1 Hz, 1H), 7.40-7.20 (m, 3H), 7.14 (dt, J=9.2, 1.7 Hz, 1H), 4.22 (q, J=6.9 Hz, 2H), 1.43 (dt, J=6.5, 3.3 Hz, 2H), 1.38-1.31 (m, 2H), 1.23 (t, J=6.9 Hz, 3H); LCMS(m/z) 458.1.

Example 733. 6-fluoro-N-(3-fluoro-5-(4,4,4-trifluoro-3,3-dimethylbut-1-yn-1-yl)phenyl)-N-methyl-[1,2,4]triazolo[4,3-a]quinazolin-5-amine

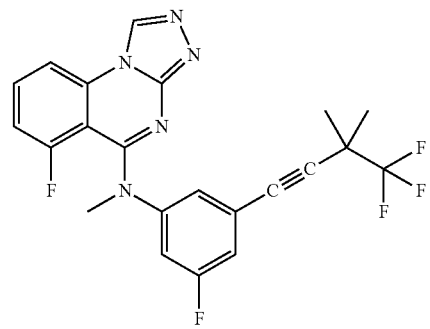 [SMILES: CN(c1cc(F)cc(C#CC(C)(C)C(F)(F)F)c1)c1nc2nncn2c2cccc(F)c12]

The title compound was synthesized according to the general procedures described for Example 453. 1H NMR (400 MHz, DMSO-d₆) δ 9.81 (s, 1H), 8.25 (d, J=8.3 Hz, 1H), 8.01 (td, J=8.3, 5.1 Hz, 1H), 7.42-7.18 (m, 3H), 7.09 (dt, J=8.6, 1.9 Hz, 1H), 3.58 (s, 3H), 1.46 (s, 6H); LCMS (m/z) 446.1.

Example 734. 6-fluoro-N-(3-fluoro-5-((1-(trifluoromethyl)cyclopropyl)ethynyl)phenyl)-N-methyl-[1,2,4]triazolo[4,3-a]quinazolin-5-amine

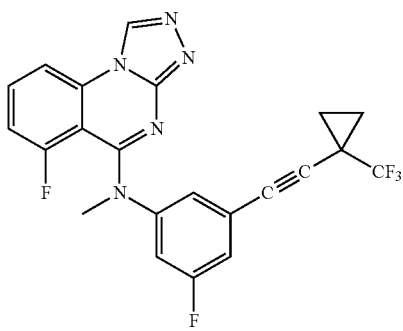 [SMILES: CN(c1cc(F)cc(C#CC2(C(F)(F)F)CC2)c1)c1nc2nncn2c2cccc(F)c12]

The title compound was synthesized according to the general procedures described for Example 453. 1H NMR (400 MHz, DMSO-d$_6$) δ 9.83 (s, 1H), 8.25 (d, J=8.3 Hz, 1H), 8.01 (td, J=8.3, 5.1 Hz, 1H), 7.36-7.20 (m, 3H), 7.12 (dt, J=9.0, 1.7 Hz, 1H), 3.58 (s, 3H), 1.43 (dt, J=6.6, 3.5 Hz, 2H), 1.36 (dt, J=8.5, 5.7 Hz, 2H); LCMS(m/z) 444.1.

Example 736. 6,7-difluoro-N-methyl-N-(3-((1-methylcyclopropyl)ethynyl)phenyl)-[1,2,4]triazolo[4,3-a]quinazolin-5-amine

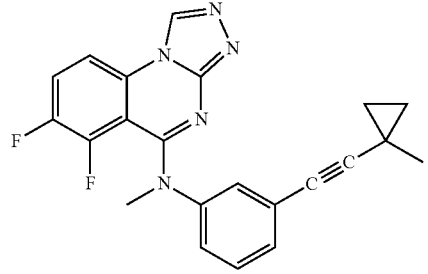

The title compound was synthesized according to the general procedures described for Example 453. 1H NMR (400 MHz, DMSO-d$_6$) δ 9.78 (s, 1H), 8.37-8.22 (m, 1H), 8.15 (q, J=9.2 Hz, 1H), 7.33 (t, J=1.9 Hz, 1H), 7.24 (dd, J=9.0, 6.6 Hz, 1H), 7.17 (dd, J=6.8, 1.8 Hz, 2H), 3.56 (s, 3H), 1.27 (s, 3H), 0.90 (q, J=3.9 Hz, 2H), 0.76-0.58 (m, 2H); LCMS(m/z) 390.1.

Example 735. 6,7-difluoro-N-methyl-N-(3-((1-(trifluoromethyl)cyclopropyl)ethynyl)phenyl)-[1,2,4]triazolo[4,3-a]quinazolin-5-amine

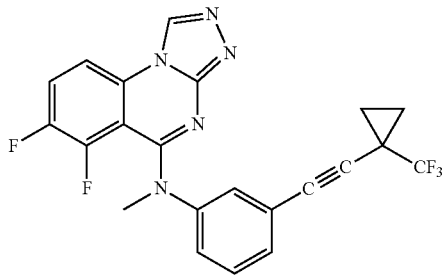 [SMILES: CN(c1cccc(C#CC2(C(F)(F)F)CC2)c1)c1nc2nncn2c2ccc(F)c(F)c12]

The title compound was synthesized according to the general procedures described for Example 453. 1H NMR (400 MHz, DMSO-d$_6$) δ 9.78 (s, 1H), 8.28 (ddd, J=9.3, 4.3, 1.4 Hz, 1H), 8.15 (td, J=9.6, 7.7 Hz, 1H), 7.46 (d, J=1.9 Hz, 1H), 7.34-7.16 (m, 3H), 3.57 (s, 3H), 1.42 (h, J=3.3, 2.8 Hz, 2H), 1.41-1.30 (m, 2H); LCMS(m/z) 444.1.

Example 737. N-(3-(3,3-dimethylbut-1-yn-1-yl)phenyl)-6,7-difluoro-N-methyl-[1,2,4]triazolo[4,3-a]quinazolin-5-amine

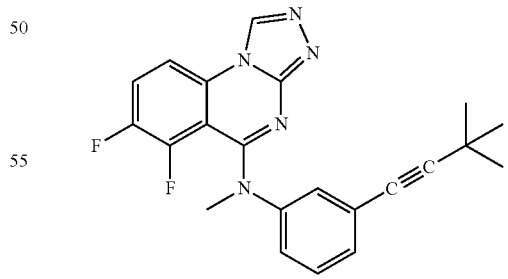

The title compound was synthesized according to the general procedures described for Example 453. 1H NMR (400 MHz, DMSO-d$_6$) δ 9.77 (s, 1H), 8.33-8.22 (m, 1H), 8.15 (q, J=9.0 Hz, 1H), 7.34 (t, J=1.9 Hz, 1H), 7.23 (t, J=7.8 Hz, 1H), 7.16 (ddt, J=9.3, 8.0, 1.5 Hz, 2H), 3.51 (s, 3H), 1.26 (s, 9H); LCMS(m/z) 392.1.

Example 738. 6,7-difluoro-N-(3-fluoro-5-((1-(trifluoromethyl)cyclopropyl)ethynyl)phenyl)-N-methyl-[1,2,4]triazolo[4,3-a]quinazolin-5-amine

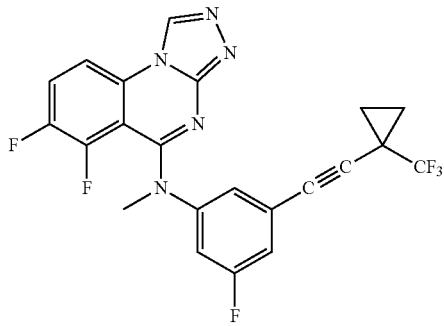 [SMILES: CN(c1cc(F)cc(C#CC2(C(F)(F)F)CC2)c1)c1nc2nncn2c2ccc(F)c(F)c12]

The title compound was synthesized according to the general procedures described for Example 453. 1H NMR (400 MHz, DMSO-$d_6$) δ 9.80 (s, 1H), 8.30 (ddd, J=9.3, 4.4, 1.4 Hz, 1H), 8.20-8.10 (m, 1H), 7.34-7.24 (m, 2H), 7.11 (dt, J=8.8, 1.8 Hz, 1H), 3.56 (s, 3H), 1.56-1.21 (m, 4H); LCMS (m/z) 462.1.

Example 739. 6,7-difluoro-N-(3-fluoro-5-((1-methylcyclopropyl)ethynyl)phenyl)-N-methyl-[1,2,4]triazolo[4,3-a]quinazolin-5-amine

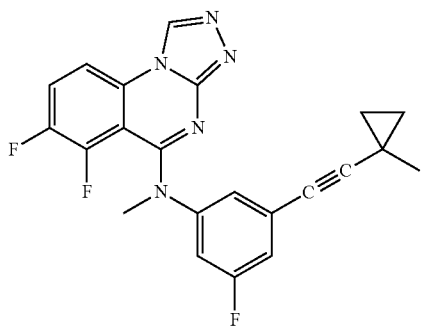 [SMILES: CN(c1cc(F)cc(C#CC2(C)CC2)c1)c1nc2nncn2c2ccc(F)c(F)c12]

The title compound was synthesized according to the general procedures described for Example 421. 1H NMR (400 MHz, DMSO-$d_6$) δ 9.80 (s, 1H), 8.30 (ddd, J=9.2, 4.4, 1.5 Hz, 1H), 8.18 (td, J=9.6, 7.7 Hz, 1H), 7.30-7.12 (m, 2H), 7.10-6.94 (m, 1H), 3.55 (s, 3H), 1.27 (s, 3H), 0.91 (q, J=4.0 Hz, 2H), 0.72 (q, J=4.1 Hz, 2H); LCMS(m/z) 408.1.

Example 740. N-ethyl-7-fluoro-N-(3-fluoro-5-(4,4,4-trifluoro-3,3-dimethylbut-1-yn-1-yl)phenyl)-[1,2,4]triazolo[4,3-a]quinazolin-5-amine

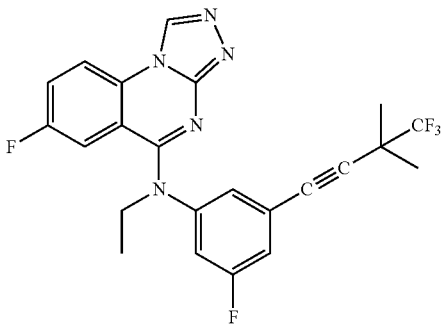 [SMILES: CCN(c1cc(F)cc(C#CC(C)(C)C(F)(F)F)c1)c1nc2nncn2c2ccc(F)cc12]

The title compound was synthesized according to the general procedures described for Example 421. 1H NMR (400 MHz, DMSO-$d_6$) δ 9.82 (s, 1H), 8.49 (dd, J=9.2, 4.8 Hz, 1H), 8.06-7.72 (m, 1H), 7.45 (dt, J=10.1, 2.3 Hz, 1H), 7.39 (d, J=1.6 Hz, 1H), 7.35-7.29 (m, 1H), 6.94 (dd, J=10.1, 2.8 Hz, 1H), 4.18 (q, J=6.9 Hz, 2H), 1.48 (s, 6H), 1.25 (t, J=6.9 Hz, 3H); LCMS(m/z) 460.2.

Example 741. N-methyl-7-fluoro-N-(3-fluoro-5-(4,4,4-trifluoro-3,3-dimethylbut-1-yn-1-yl)phenyl)-[1,2,4]triazolo[4,3-a]quinazolin-5-amine

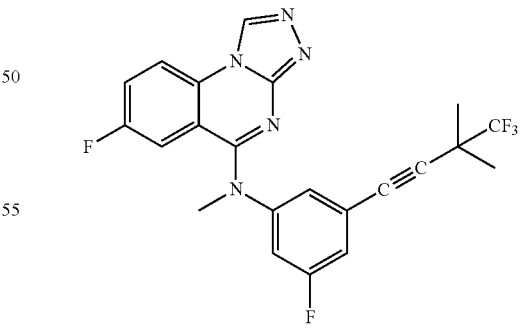

The title compound was synthesized according to the general procedures described for Example 421. 1H NMR (400 MHz, DMSO-$d_6$) δ 9.81 (s, 1H), 8.49 (dd, J=9.2, 4.8 Hz, 1H), 7.92 (ddd, J=9.1, 8.1, 2.8 Hz, 1H), 7.65-7.33 (m, 2H), 7.34-7.16 (m, 1H), 7.01 (dd, J=10.0, 2.8 Hz, 1H), 3.59 (s, 3H), 1.47 (s, 6H); LCMS(m/z) 446.1.

Example 742. N-ethyl-7-fluoro-N-(3-fluoro-5-((1-(trifluoromethyl)cyclopropyl)ethynyl)phenyl)-[1,2,4]triazolo[4,3-a]quinazolin-5-amine

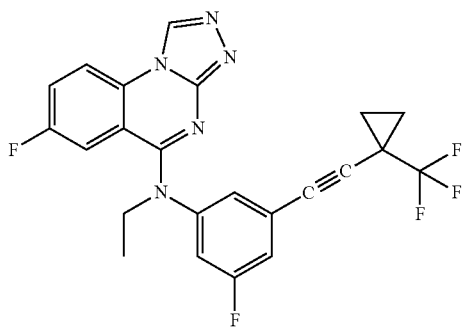 [SMILES: CCN(c1cc(F)cc(C#CC2(C(F)(F)F)CC2)c1)c1nc2nncn2c2ccc(F)cc12]

The title compound was synthesized according to the general procedures described for Example 447. 1H NMR (400 MHz, DMSO-d$_6$) δ 9.88-9.78 (m, 1H), 8.49 (dd, J=9.2, 4.8 Hz, 1H), 7.93 (td, J=8.6, 2.8 Hz, 1H), 7.46 (dt, J=9.9, 2.0 Hz, 1H), 7.39 (d, J=1.7 Hz, 1H), 7.34 (dd, J=8.9, 2.0 Hz, 1H), 6.93 (dd, J=10.1, 2.8 Hz, 1H), 4.18 (q, J=6.9 Hz, 2H), 1.50-1.42 (m, 2H), 1.39 (d, J=6.0 Hz, 2H), 1.25 (t, J=6.9 Hz, 3H); LCMS(m/z) 458.1.

Example 743. N-ethyl-7-fluoro-N-(3-fluoro-5-((1-methylcyclopropyl)ethynyl)phenyl)-[1,2,4]triazolo[4,3-a]quinazolin-5-amine

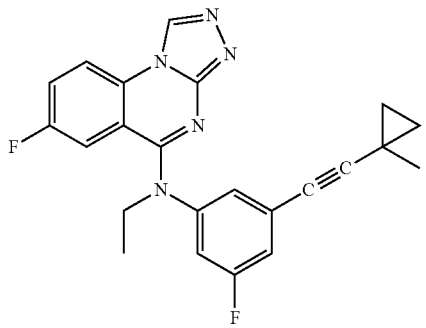 [SMILES: CCN(c1cc(F)cc(C#CC2(C)CC2)c1)c1nc2nncn2c2ccc(F)cc12]

The title compound was synthesized according to the general procedures described for Example 447. 1H NMR (400 MHz, DMSO-d$_6$) δ 9.78 (s, 1H), 8.47 (dd, J=9.1, 4.8 Hz, 1H), 7.97-7.81 (m, 1H), 7.36-7.31 (m, 1H), 7.24 (d, J=2.1 Hz, 1H), 7.18 (d, J=9.0 Hz, 1H), 6.92 (dd, J=10.1, 2.8 Hz, 1H), 4.15 (q, J=6.9 Hz, 2H), 1.28 (s, 3H), 1.24 (t, J=7.0 Hz, 3H), 0.93 (q, J=4.0 Hz, 2H), 0.74 (q, J=4.1 Hz, 2H); LCMS(m/z) 404.2.

Example 744. N-ethyl-7-fluoro-1-methyl-N-[3-[2-(1-methylcyclopropyl)ethynyl]phenyl]-[1,2,4]triazolo[4,3-a]quinazolin-5-amine

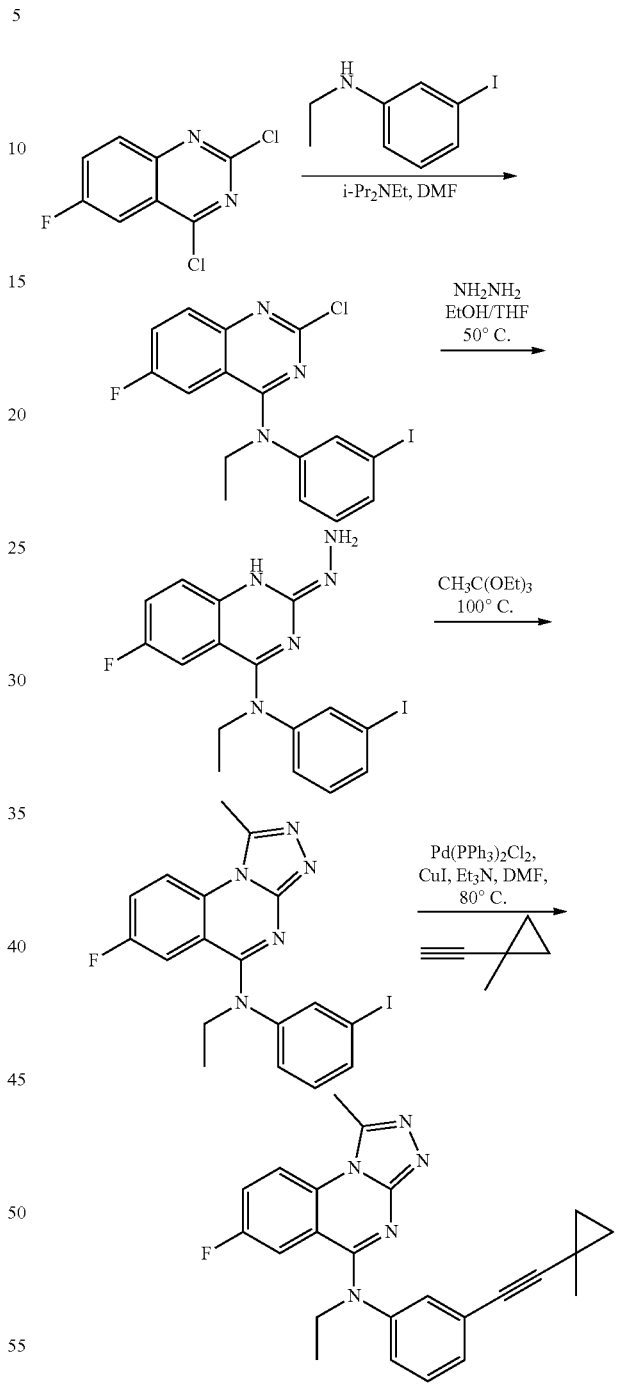

Synthesis of 2-chloro-N-ethyl-6-fluoro-N-(3-iodophenyl)quinazolin-4-amine: To a solution of N-ethyl-3-iodoaniline (752 mg, 3.04 mmol) in DMF (5.0 mL) at 0° C. was added 2,4-dichloro-6-fluoro-quinazoline (700 mg, 3.23 mmol) and N,N-Diisopropylamine (1042 mg, 8.06 mmol). The mixture was stirred at 40° C. for 2 hrs. Upon completion, the mixture was poured into water (100 mL) and extracted with ethyl acetate (2×50 ml each). The organics were separated and dried over sodium sulfate, filtered and concentrated under vacuum. The crude was triturated with heptanes and the solid was filtered to afford the desired compound. MS (m/z) 428.6 [M+H]⁺.

Synthesis of N-ethyl-6-fluoro-2-hydrazino-N-(3-iodophenyl)quinazolin-4-amine: To a solution of 2-chloro-N-ethyl-6-fluoro-N-(3-iodophenyl)quinazolin-4-amine (1132 mg, 2.65 mmol) in THF (10 mL) and ethanol (10 mL) was added anhydrous hydrazine (914 mg, 28.5 mmol) and the mixture was stirred at room temperature for 30 minutes. Upon completion, the reaction was diluted with ethyl acetate and washed with water, dried over Na₂SO₄ and concentrated under reduced pressure to afford the desired compound. MS (m/z) 425.5 [M+H]⁺.

Synthesis of N-ethyl-7-fluoro-N-(3-iodophenyl)-1-methyl-[1,2,4]triazolo[4,3-a]quinazolin-5-amine: A solution of N-ethyl-6-fluoro-2-hydrazino-N-(3-iodophenyl)quinazolin-4-amine (450 mg, 1.06 mmol) and triethyl orthoacetate (1.9 g, 11.7 mmol) was heated to 100° C. for 1 h. Upon completion, the reaction was cooled to room temperature, and concentrated under reduced pressure to afford the crude product. The crude product was triturated with heptanes and the solids were collected by filtration, washed with heptanes and dried in vacuo to afford the desired compound. MS (m/z) 448.2 [M+H]⁺.

Synthesis of N-ethyl-7-fluoro-1-methyl-N-[3-[2-(1-methylcyclopropyl)ethynyl]phenyl]-[1,2,4]triazolo[4,3-a]quinazolin-5-amine: A solution of N-ethyl-7-fluoro-N-(3-iodophenyl)-1-methyl-[1,2,4]triazolo[4,3-a]quinazolin-5-amine (25 mg, 0.0559 mmol) in DMF (2 mL) was added 1-ethynyl-1-methyl-cyclopropane (5.6 mg, 0.07 mmol), Pd(PPh₃)₂Cl₂ (1.57 mg, 2.2 μmol), CuI (0.3 mg, 0.002 mmol) and triethylamine (0.2 mL, 1.12 mmol) and the mixture was purged with nitrogen and heated at 84° C. for 10 min. Upon completion, the mixture was partitioned between EA (20 mL) and water (20 mL), organics separated and dried over Na₂SO₄ and concentrated in vacuo. The residue was purified by reverse phase HPLC (0.1% trifluoroacetic acid in acetonitrile/water) providing the title compound as the mono-TFA salt. 1H NMR (400 MHz, DMSO-d₆) δ 8.37 (dd, J=9.4, 4.7 Hz, 1H), 7.83 (ddd, J=10.1, 7.7, 2.9 Hz, 1H), 7.47-7.33 (m, 4H), 6.90 (dd, J=10.3, 2.9 Hz, 1H), 4.18 (q, J=6.9 Hz, 2H), 3.00 (s, 3H), 1.28 (s, 3H), 1.24 (t, J=7.0 Hz, 3H), 0.92 (q, J=4.0 Hz, 2H), 0.73 (q, J=4.1 Hz, 2H); MS (m/z) 400.1 [M+H]⁺.

Example 745. N-ethyl-7-fluoro-N-(3-((1-methylcyclopropyl)ethynyl)phenyl)-[1,2,4]triazolo[4,3-a]quinazolin-5-amine

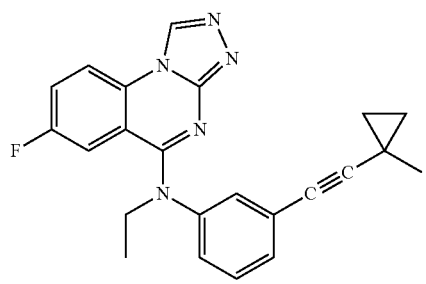 [SMILES: CCN(c1cccc(C#CC2(C)CC2)c1)c1nc2nncn2c2ccc(F)cc12]

The title compound was synthesized according to the general procedures described for Example 447. 1H NMR (400 MHz, DMSO-d₆) δ 9.82 (s, 1H), 8.48 (dd, J=9.2, 4.9 Hz, 1H), 7.98-7.85 (m, 1H), 7.51-7.30 (m, 4H), 6.76 (dd, J=10.5, 2.8 Hz, 1H), 4.17 (q, J=7.0 Hz, 2H), 1.29 (s, 3H), 1.24 (t, J=6.9 Hz, 3H), 0.93 (q, J=4.0 Hz, 2H), 0.73 (q, J=4.0 Hz, 2H); LCMS(m/z) 386.2.

Example 746. N-ethyl-7-fluoro-N-(3-((1-methylcyclopropyl)ethynyl)phenyl)-[1,2,4]triazolo[4,3-a]quinazolin-5-amine

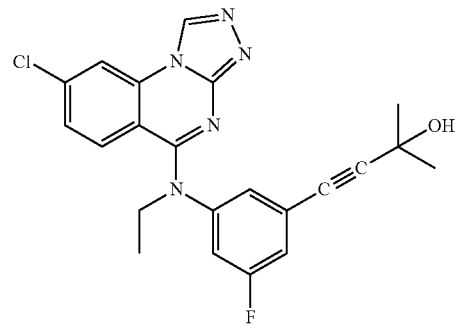 [SMILES: CCN(c1cc(F)cc(C#CC(C)(C)O)c1)c1nc2nncn2c2cc(Cl)ccc12]

The title compound was synthesized according to the general procedures described for Example 447. 1H NMR (400 MHz, DMSO-d₆) δ 9.76 (s, 1H), 8.63 (d, J=2.1 Hz, 1H), 7.47 (dd, J=9.0, 2.1 Hz, 1H), 7.43-7.36 (m, 1H), 7.33-7.23 (m, 2H), 7.18 (d, J=9.1 Hz, 1H), 4.17 (q, J=7.0 Hz, 2H), 1.42 (s, 6H), 1.23 (t, J=6.9 Hz, 3H); LCMS(m/z) 424.1.

Example 747. 2,2,2-trifluoro-N-[3-[7-fluoro-1-(7-fluoro-1-methyl-[1,2,4]triazolo[4,3-a]quinazolin-5-yl]-3,4-dihydro-2H-quinolin-5-yl]-1,1-dimethyl-prop-2-ynyl]acetamide

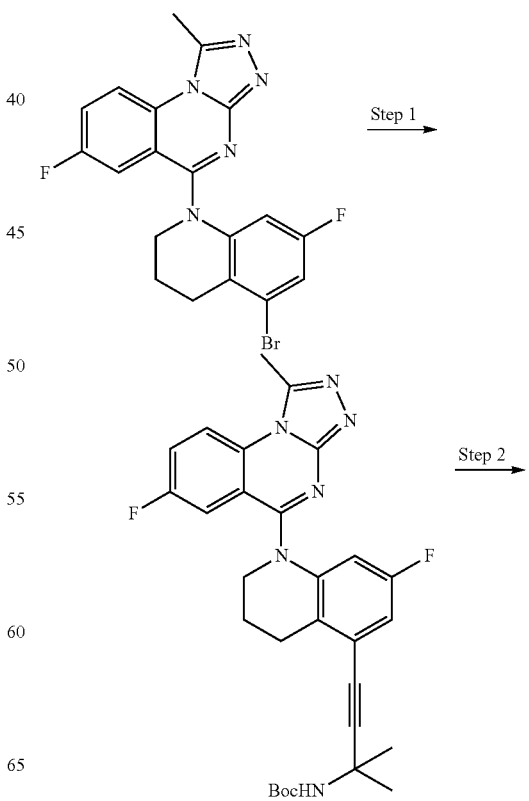

-continued

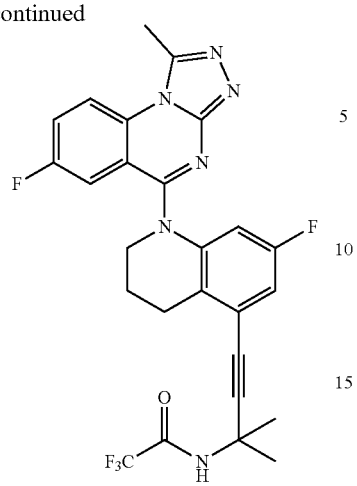

Step 1: synthesis of tert-butyl N-[3-[7-fluoro-1-(7-fluoro-1-methyl-[1,2,4]triazolo[4,3-a]quinazolin-5-yl]-3,4-dihydro-2H-quinolin-5-yl]-1,1-dimethyl-prop-2-ynyl]carbamate. 5-(5-Bromo-7-fluoro-3,4-dihydro-2H-quinolin-1-yl)-7-fluoro-1-methyl-[1,2,4]triazolo[4,3-a]quinazoline (90 mg, 209 µmol), tert-butyl N-(1,1-dimethylprop-2-ynyl)carbamate (153 mg, 837 µmol) were dissolved in N-methyl-2-pyrrolidone (2 ml). Zinc bromide (236 mg, 1050 µmol), (1,1'-bis(diphenylphosphino)ferrocene) palladium (II) dichloride (17 mg, 21 µmol) and triethylamine (0.44 ml, 3140 µmol) were added. The mixture was bubbled through with N₂ for 1 min and then heated at 105° C. for 14 h minutes. The mixture was cooled to room temperature, and ethyl acetate and water were added to the mixture. The organic layer was concentrated in vacuo. The residue was used directly in next step.

Step 2: synthesis of 2,2,2-trifluoro-N-[3-[7-fluoro-1-(7-fluoro-1-methyl-[1,2,4]triazolo[4,3-a]quinazolin-5-yl)-3,4-dihydro-2H-quinolin-5-yl]-1,1-dimethyl-prop-2-ynyl]acetamide. To the crude residue obtained from above was added DCM (4 ml) and it was cooled to 0° C. TFA (2 ml) was added slowly. After stirring at rt for 1 h, reaction mixture was concentrated to dryness by co-evaporation with DCM for several times. To the crude residue was added DCM (4 ml) followed by the addition of triethyl amine (0.23 ml, 1.67 mmol) and acetic chloride (0.06 ml, 0.84 mmol) at 0° C. After stirring at room temperature for 1 h, The reaction was quenched with water (1 ml). The reaction mixture was diluted with EtOAc, washed with water and brine, dried and concentrated. The resulting crude was purified by column chromatography using 0-15% MeOH in DCM. The fractions containing the desired product was collected and concentrated. It was further purified by reverse phase HPLC to afford the desired product. ¹H NMR (400 MHz, Methanol-d₄) δ 8.48 (m, 1H), 7.85 (m, 1H), 7.47 (m, 1H), 7.03 (m, 1H), 6.73 (m, 1H), 4.14 (m, 2H), 3.11 (s, 3H), 3.07 (m, 2H), 2.21 (m, 2H), 1.79 (s, 6H); LCMS(m/z) 529.4.

Example 748. 7-fluoro-5-(7-fluoro-5-(4,4,4-trifluoro-3,3-dimethylbut-1-yn-1-yl)-3,4-dihydroquinolin-1(2H)-yl)-1-methyl-[1,2,4]triazolo[4,3-a]quinazoline

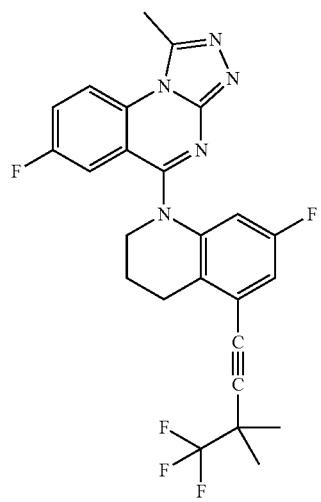 [SMILES: Cc1nnc2nc(N3CCCc4c(C#CC(C)(C)C(F)(F)F)cc(F)cc43)c3cc(F)ccc3n12]

The title compound was synthesized according to the general procedures described for Example 421. ¹H NMR (400 MHz, Methanol-d₄) δ 8.52 (dd, J=9.4, 4.4 Hz, 1H), 7.90 (ddd, J=9.4, 7.5, 2.8 Hz, 1H), 7.49 (dd, J=9.3, 2.9 Hz, 1H), 7.11 (dd, J=8.7, 2.6 Hz, 1H), 6.85 (dd, J=10.0, 2.5 Hz, 1H), 4.20 (t, J=6.4 Hz, 2H), 3.13 (s, 3H), 3.12-3.04 (m, 2H), 2.22 (m, 2H), 1.60 (s, 6H); LCMS(m/z) 486.4.

Example 749. 7-fluoro-5-(7-fluoro-5-((1-(trifluoromethyl)cyclopropyl)ethynyl)-3,4-dihydroquinolin-1(2H)-yl)-1-methyl-[1,2,4]triazolo[4,3-a]quinazoline

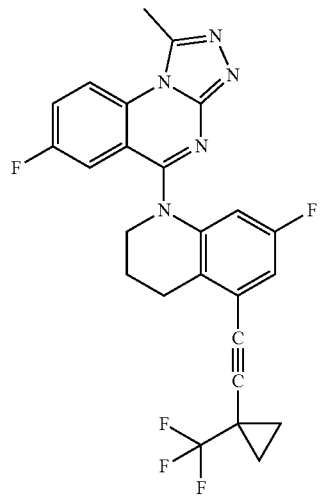 [SMILES: Cc1nnc2nc(N3CCCc4c(C#CC5(C(F)(F)F)CC5)cc(F)cc43)c3cc(F)ccc3n12]

The title compound was synthesized according to the general procedures described for Example 421. ¹H NMR (400 MHz, Methanol-d₄) δ 8.52 (dd, J=9.4, 4.4 Hz, 1H), 7.90 (ddd, J=9.4, 7.5, 2.9 Hz, 1H), 7.48 (dd, J=9.3, 2.8 Hz, 1H), 7.11 (dd, J=8.8, 2.6 Hz, 1H), 6.84 (dd, J=9.9, 2.5 Hz, 1H), 4.20 (t, J=6.4 Hz, 2H), 3.13 (s, 3H), 3.11-3.05 (m, 2H), 2.22 (p, J=6.5 Hz, 2H), 1.54-1.48 (m, 2H), 1.46-1.35 (m, 2H); LCMS(m/z) 484.4.

Example 750. 7-fluoro-5-(7-fluoro-5-(4,4,4-trifluoro-3,3-dimethylbut-1-yn-1-yl)-3,4-dihydroquinolin-1(2H)-yl)-[1,2,4]triazolo[4,3-a]quinazoline

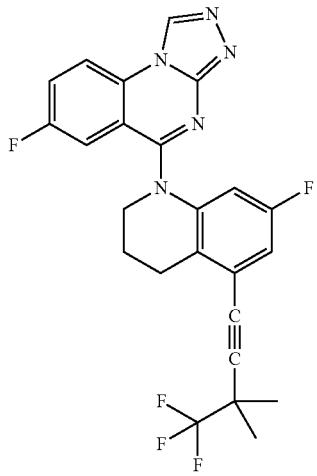 [SMILES: CC(C)(C#Cc1cc(F)cc2c1CCCN2c1nc2nncn2c2ccc(F)cc12)C(F)(F)F]

The title compound was synthesized according to the general procedures described for Example 421. ¹H NMR (400 MHz, Methanol-d₄) δ 9.72 (s, 1H), 8.49 (dd, J=9.2, 4.6 Hz, 1H), 7.91 (m, 1H), 7.42 (dd, J=9.4, 2.7 Hz, 1H), 7.11 (dd, J=8.8, 2.5 Hz, 1H), 6.89 (dd, J=9.9, 2.5 Hz, 1H), 4.21 (t, J=6.4 Hz, 2H), 3.08 (t, J=6.6 Hz, 2H), 2.22 (p, J=6.5 Hz, 2H), 1.60 (s, 6H); LCMS(m/z) 472.4.

Example 751. 5-(5-(4,4-difluoro-3,3-dimethylbut-1-yn-1-yl)-7-fluoro-3,4-dihydroquinolin-1(2H)-yl)-7-fluoro-[1,2,4]triazolo[4,3-a]quinazoline

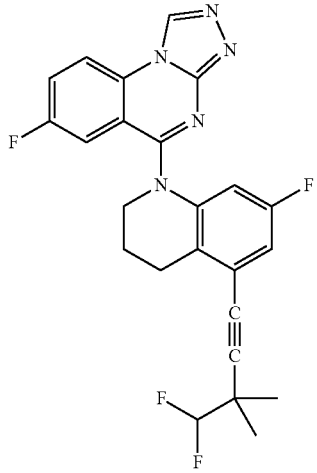 [SMILES: CC(C)(C#Cc1cc(F)cc2c1CCCN2c1nc2nncn2c2ccc(F)cc12)C(F)F]

The title compound was synthesized according to the general procedures described for Example 421. 1H NMR (400 MHz, Acetonitrile-d3) δ 9.30 (s, 1H), 8.26 (dt, J=8.7, 4.4 Hz, 1H), 7.82 (m, 1H), 7.44 (dd, J=9.5, 2.8 Hz, 1H), 7.04 (dd, J=9.0, 2.6 Hz, 1H), 6.70-6.60 (m, 1H), 5.87 (t, J=56.6 Hz, 1H), 4.10 (t, J=6.2 Hz, 2H), 3.04 (m, 2H), 2.18 (p, J=6.5 Hz, 2H), 1.44 (s, 6H); LCMS(m/z) 454.4.

Example 752. N-(2,2-difluoroethyl)-6,7-difluoro-N-(3-fluoro-5-((1-methylcyclopropyl)ethynyl)phenyl)-[1,2,4]triazolo[4,3-a]quinazolin-5-amine

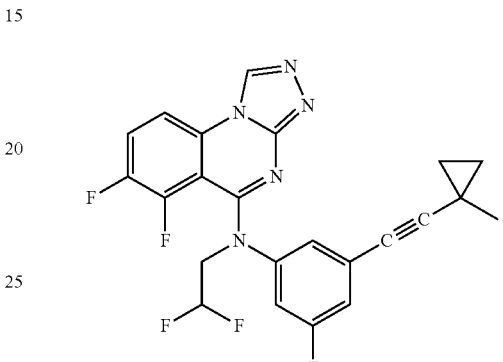

The title compound was synthesized according to the general procedures described for Example 421. ¹H NMR (400 MHz, Methanol-d₄) δ 9.64 (s, 1H), 8.22 (m, 1H), 8.01 (td, J=9.4, 7.6 Hz, 1H), 7.08-6.95 (m, 3H), 6.46 (tt, J=55.9, 4.0 Hz, 1H), 4.64 (td, J=13.7, 4.0 Hz, 2H), 1.30 (s, 3H), 0.95 (q, J=4.1 Hz, 2H), 0.74-0.64 (m, 2H); LCMS(m/z) 458.3.

Example 753. N-(2,2-difluoroethyl)-6,7-difluoro-N-(3-fluoro-5-((1-(trifluoromethyl)cyclopropyl)ethynyl)phenyl)-[1,2,4]triazolo[4,3-a]quinazolin-5-amine

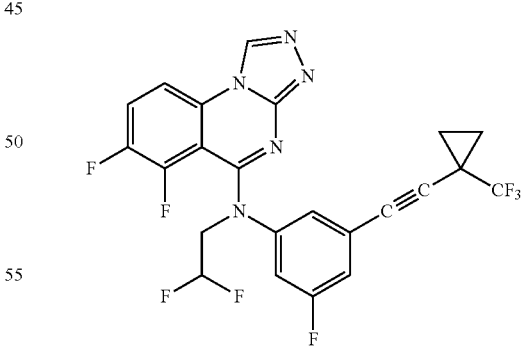

The title compound was synthesized according to the general procedures described for Example 276. ¹H NMR (400 MHz, Methanol-d₄) δ 9.69 (s, 1H), 8.26 (m, 1H), 8.06 (td, J=9.4, 7.6 Hz, 1H), 7.19 (dd, J=8.2, 2.0 Hz, 2H), 7.15-7.08 (m, 1H), 6.49 (tt, J=55.9, 4.0 Hz, 1H), 4.68 (td, J=13.7, 4.0 Hz, 2H), 1.44-1.38 (m, 2H), 1.30 (m, 2H); LCMS(m/z) 512.3.

Example 754. N-(3-(4,4-difluoro-3,3-dimethylbut-1-yn-1-yl)-5-fluorophenyl)-N-(2,2-difluoroethyl)-6,7-difluoro-[1,2,4]triazolo[4,3-a]quinazolin-5-amine

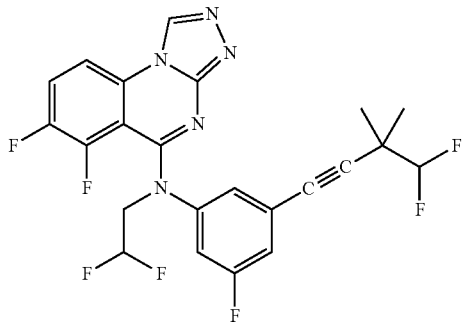 [SMILES: CC(C)(C#Cc1cc(F)cc(N(CC(F)F)c2nc3nncn3c3ccc(F)c(F)c23)c1)C(F)F]

The title compound was synthesized according to the general procedures described for Example 421. $^1$H NMR (400 MHz, Methanol-d$_4$) δ 9.70 (s, 1H), 8.33-8.21 (m, 1H), 8.07 (q, J=8.9 Hz, 1H), 7.23-7.13 (m, 2H), 7.09 (dt, J=9.0, 1.8 Hz, 1H), 6.49 (tt, J=56.0, 4.0 Hz, 1H), 5.76 (t, J=56.6 Hz, 1H), 4.68 (td, J=13.7, 4.0 Hz, 2H), 1.34 (s, 6H); LCMS(m/z) 496.3.

Example 755. N-(2,2-difluoroethyl)-6,7-difluoro-N-(3-fluoro-5-(4,4,4-trifluoro-3,3-dimethylbut-1-yn-1-yl)phenyl)-[1,2,4]triazolo[4,3-a]quinazolin-5-amine

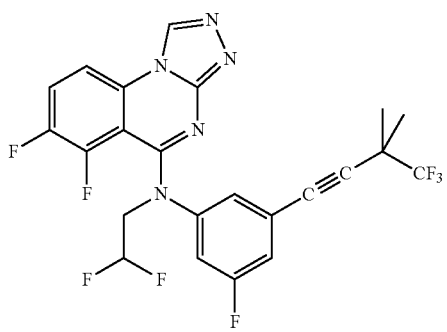

The title compound was synthesized according to the general procedures described for Example 421. $^1$H NMR (400 MHz, Methanol-d$_4$) δ 9.70 (s, 1H), 8.27 (m, 1H), 8.07 (td, J=9.4, 7.6 Hz, 1H), 7.26-7.16 (m, 2H), 7.12 (m, 1H), 6.49 (tt, J=55.8, 4.0 Hz, 1H), 4.69 (td, J=13.7, 4.0 Hz, 2H), 1.49 (s, 6H); LCMS(m/z) 514.3.

Example 756. (7-fluoro-5-(methyl(3-((1-(trifluoromethyl)cyclopropyl)ethynyl)phenyl)amino)-[1,2,4]triazolo[4,3-a]quinazolin-8-yl)methanol

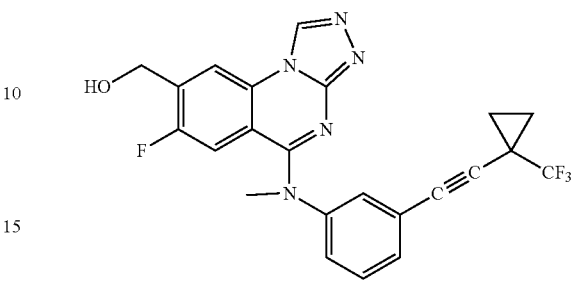

The title compound was synthesized according to the general procedures described for Example 276. $^1$H NMR (400 MHz, Methanol-d$_4$) δ 9.69 (s, 1H), 8.48 (d, J=6.3 Hz, 1H), 7.65-7.53 (m, 3H), 7.49 (dt, J=6.5, 2.4 Hz, 1H), 6.77 (d, J=11.6 Hz, 1H), 4.83 (d, J=1.0 Hz, 2H), 3.78 (s, 3H), 1.42 (m, 2H), 1.32 (m, 2H); LCMS(m/z) 456.4.

Example 757. 1-((3-((8-chloro-[1,2,4]triazolo[4,3-a]quinazolin-5-yl)(methyl)amino)phenyl)ethynyl)cyclohexan-1-ol

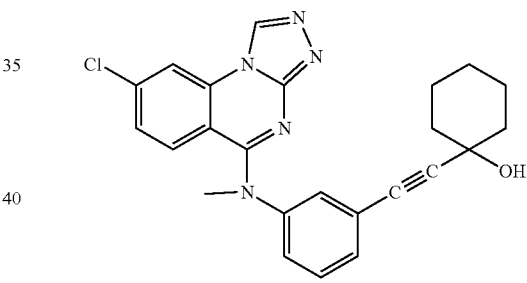

The title compound was synthesized according to the general procedures described for Example 276. $^1$H NMR (400 MHz, Methanol-d$_4$) δ 9.59 (s, 1H), 8.51 (d, J=2.1 Hz, 1H), 7.60-7.48 (m, 3H), 7.48-7.36 (m, 2H), 7.24 (d, J=9.1 Hz, 1H), 3.79 (s, 3H), 2.02-1.90 (m, 2H), 1.74 (m, 2H), 1.67-1.55 (m, 5H), 1.37-1.26 (m, 1H); LCMS(m/z) 432.2.

Example 758. 8-chloro-N-(3-fluoro-5-((1-(trifluoromethyl)cyclopropyl)ethynyl)phenyl)-1-methyl-N-(2,2,2-trifluoroethyl)-[1,2,4]triazolo[4,3-a]quinazolin-5-amine Step 1

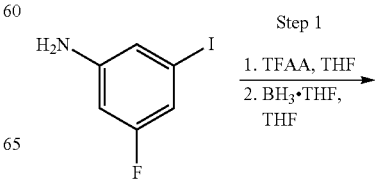

1. TFAA, THF
2. BH$_3$·THF, THF

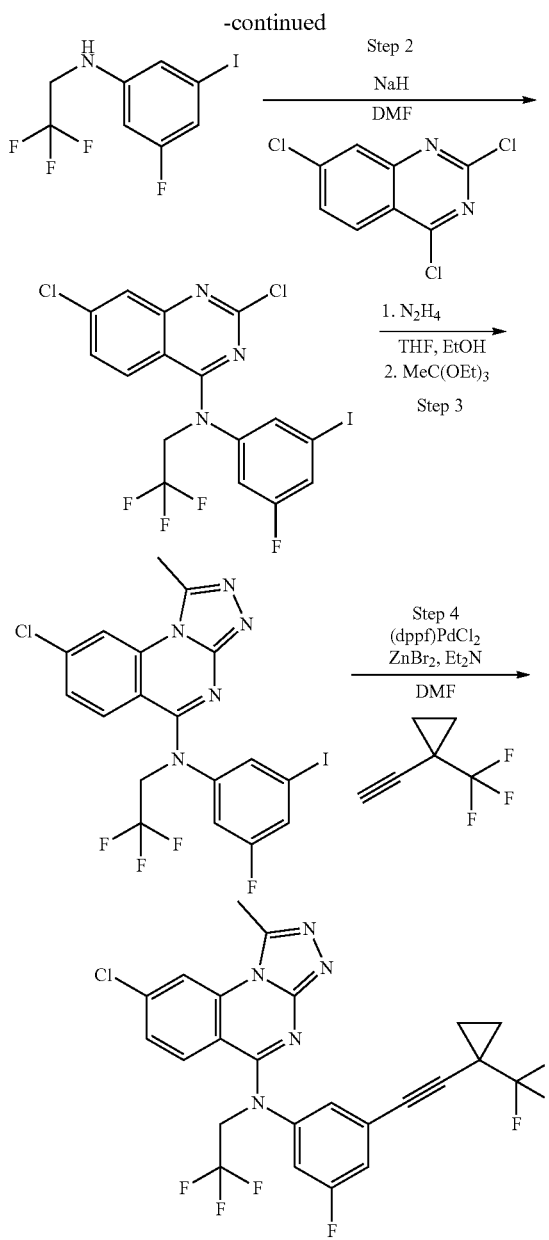

DMF (2.5 mL). The resulting suspension was stirred at RT for 30 min followed by the addition of 2,4,7-trichloroquinazoline (487 mg, 2.09 mmol) as a solution in DMF (5 mL). The reaction mixture was then warmed to RT and stirred for an additional 1.5 h. The reaction mixture was cooled to 0° C., quenched with water, and extracted with EtOAc. The organic layer was washed with water (2×), and brine then dried with anhydrous magnesium sulfate, and concentrated under reduced pressure. Purification by flash chromatography (elution with 0-100% v/v ethyl acetate in hexanes) afforded 2,7-dichloro-N-(3-fluoro-5-iodo-phenyl)-N-(2,2,2-trifluoroethyl)quinazolin-4-amine.

Step 3: Hydrazine (0.255 mL, 8.14 mmol) was added to a solution of 2,7-dichloro-N-(3-fluoro-5-iodo-phenyl)-N-(2,2,2-trifluoroethyl)quinazolin-4-amine (420 mg, 0.814 mmol) in THF (3 mL) and EtOH (6 mL). The resulting solution was heated to 40° C. for 3 h, then concentrated under reduced pressure to give desired product which was used without further purification.

A suspension of 7-chloro-N-(3-fluoro-5-iodo-phenyl)-2-hydrazino-N-(2,2,2-trifluoroethyl)quinazolin-4-amine (200 mg, 0.391 mmol) in triethyl orthoacetate (5 mL) was heated to 120° C. for 2 h, then cooled to RT and concentrated under reduced pressure. Purification by flash chromatography (elution with 0-100% v/v ethyl acetate in hexanes) afforded 8-chloro-N-(3-fluoro-5-iodo-phenyl)-1-methyl-N-(2,2,2-trifluoroethyl)-[1,2,4]triazolo[4,3-a]quinazolin-5-amine.

Step 4: To a suspension of 8-chloro-N-(3-fluoro-5-iodo-phenyl)-1-methyl-N-(2,2,2-trifluoroethyl)-[1,2,4]triazolo[4,3-a]quinazolin-5-amine (31.8 mg, 0.059 mmol), 1,1'-Bis(diphenylphosphino)ferrocene-palladium(II)dichloride dichloromethane complex (4.9 mg, 0.006 mmol), and dibromozinc (67 mg, 0.297 mmol) in DMF (1 mL) was added triethylamine (0.166 mL, 1.19 mmol). The resulting mixture was sparged with nitrogen for 5 min, followed by the addition of 1-ethynyl-1-(trifluoromethyl)cyclopropane (0.01 mL, 0.073 mmol). The reaction mixture was then heated to 80° C. for 10 min then cooled to RT and diluted with water and ethyl acetate. The organic layer was then washed twice with water then brine, dried with anhydrous magnesium sulfate, and concentrated under reduced pressure. Isolation via HPLC and lyophilization gave the title compound: 1H NMR (400 MHz, DMSO-$d_6$) δ 8.23 (d, J=1.8 Hz, 1H), 7.55 (dd, J=8.9, 1.9 Hz, 1H), 7.49 (d, J=8.9 Hz, 1H), 7.31-7.17 (m, 3H), 5.11 (q, J=9.2 Hz, 2H), 3.04 (s, 3H), 1.49-1.41 (m, 2H), 1.40-1.33 (m, 2H); LCMS(m/z) 542.

Example 759. 8-chloro-N-(3-fluoro-5-((1-(trifluoromethyl)cyclopropyl)ethynyl)phenyl)-N-(2,2,2-trifluoroethyl)-[1,2,4]triazolo[4,3-a]quinazolin-5-amine

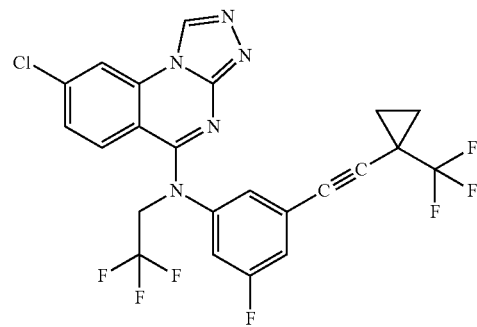 [SMILES: Fc1cc(C#CC2(C(F)(F)F)CC2)cc(N(CC(F)(F)F)c2nc3nncn3c3cc(Cl)ccc23)c1]

Step 1: Trifluoroacetic anhydride was added to a solution of 3-fluoro-5-iodo-aniline (2 g, 8.44 mmol) in THF (40 mL) at 0° C. The reaction mixture was warmed to RT and stirred for 45 min. The reaction mixture was then quenched with sat. aq. NaHCO$_3$ and extracted with Et$_2$O. The organic layer was washed with NaHCO$_3$, water, and brine then dried with anhydrous magnesium sulfate, and concentrated under reduced pressure. The crude material was then dissolved in THF (40 mL) followed by the addition of BH$_3$ THF (16.9 mL, 1M in THF, 16.9 mmol). The resulting solution was then heated to 65° C. for 16 h then cooled to RT. Excess Borane was quenched by the addition of MeOH (8 mL) and the reaction mixture was concentrated under reduced pressure. Purification by flash chromatography (elution with 0-100% v/v ethyl acetate in hexanes) afforded 3-fluoro-5-iodo-N-(2,2,2-trifluoroethyl)aniline.

Step 2: To a suspension of NaH (71 mg, 1.86 mmol) in DMF (5 mL) at 0° C. was added a solution of 3-fluoro-5-iodo-N-(2,2,2-trifluoroethyl)aniline (370 mg, 1.16 mmol) in The title compound was synthesized according to the procedures described for Example 758, except using triethyl orthoformate instead of triethyl orthoacetate in Step 3. 1H NMR (400 MHz, DMSO-d$_6$) δ 9.82 (s, 1H), 8.67 (d, J=2.0 Hz, 1H), 7.49 (dd, J=8.9, 2.0 Hz, 1H), 7.40 (d, J=8.9 Hz, 1H), 7.33-7.27 (m, 2H), 7.23 (d, J=7.9 Hz, 1H), 5.11 (q, J=9.2 Hz, 2H), 1.47-1.41 (m, 2H), 1.41-1.35 (m, 2H); LCMS(m/z) 528.1.

Example 760. 7-fluoro-N-(3-fluoro-5-((1-(trifluoromethyl)cyclopropyl)ethynyl)phenyl)-N-(2,2,2-trifluoroethyl)-[1,2,4]triazolo[4,3-a]quinazolin-5-amine

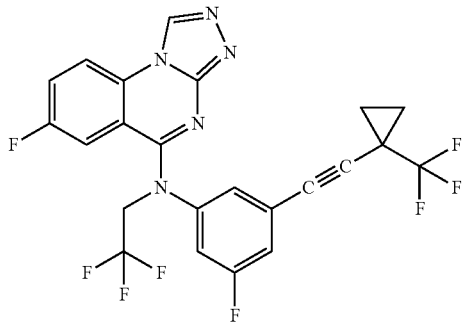 [SMILES: Fc1cc(C#CC2(C(F)(F)F)CC2)cc(N(CC(F)(F)F)c2nc3nncn3c3ccc(F)cc23)c1]

The title compound was synthesized according to the procedures described for Example 759, except using 2,4-dichloro-6-fluoroquinazoline instead of 2,4,7-trichloroquinazoline in Step 2. 1H NMR (400 MHz, DMSO-d$_6$) δ 9.86 (s, 1H), 8.53 (dd, J=9.2, 4.7 Hz, 1H), 7.94 (td, J=8.7, 2.8 Hz, 1H), 7.39-7.32 (m, 2H), 7.27 (d, J=8.9 Hz, 1H), 7.04 (dd, J=9.7, 2.8 Hz, 1H), 5.11 (q, J=9.2 Hz, 2H), 1.48-1.34 (m, 4H); LCMS(m/z) 512.1.

Example 761. 7-fluoro-N-(3-fluoro-5-((3-methyloxetan-3-yl)ethynyl)phenyl)-N-methyl-[1,2,4]triazolo[4,3-a]quinazolin-5-amine

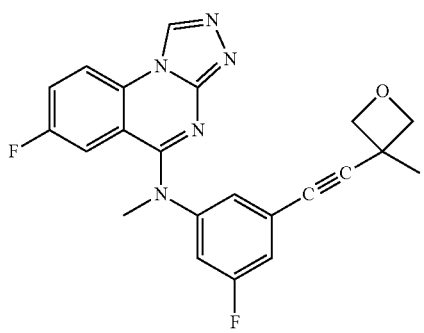 [SMILES: CN(c1cc(F)cc(C#CC2(C)COC2)c1)c1nc2nncn2c2ccc(F)cc12]

The title compound was synthesized according to the procedures described for Example 426. 1H NMR (400 MHz, DMSO-d$_6$) δ 9.88 (s, 1H), 8.52 (dd, J=9.2, 4.8 Hz, 1H), 7.96 (ddd, J=9.1, 8.0, 2.8 Hz, 1H), 7.46 (dt, J=10.0, 2.2 Hz, 1H), 7.39 (s, 1H), 7.37-7.29 (m, 1H), 6.99 (dd, J=10.1, 2.8 Hz, 1H), 4.71 (d, J=5.5 Hz, 2H), 4.41 (d, J=5.5 Hz, 2H), 3.61 (s, 3H), 1.60 (s, 3H); LCMS(m/z) 406.1.

Example 762. 8-chloro-N-(2,2,2-trifluoroethyl)-N-(3-((1-(trifluoromethyl)cyclopropyl)ethynyl)phenyl)-[1,2,4]triazolo[4,3-a]quinazolin-5-amine

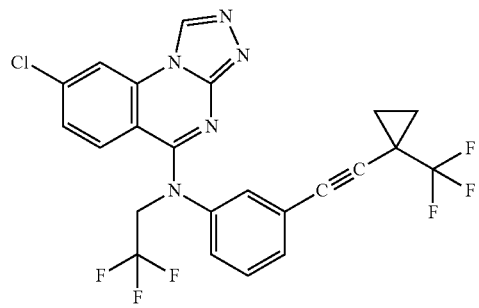 [SMILES: FC(F)(F)CN(c1cccc(C#CC2(C(F)(F)F)CC2)c1)c1nc2nncn2c2cc(Cl)ccc12]

The title compound was synthesized according to the procedures described for Example 759, except using 3-iodo-N-(2,2,2-trifluoroethyl)aniline instead of 3-fluoro-5-iodo-N-(2,2,2-trifluoroethyl)aniline in Step 2. 1H NMR (400 MHz, DMSO-d$_6$) δ 9.79 (s, 1H), 8.65 (d, J=2.1 Hz, 1H), 7.49-7.47 (m, 1H), 7.44 (dd, J=9.0, 2.1 Hz, 1H), 7.41-7.28 (m, 4H), 5.08 (q, J=9.2 Hz, 2H), 1.46-1.40 (m, 2H), 1.39-1.33 (m, 2H); LCMS(m/z) 510.1.

Example 763. 8-chloro-N-(2,2,2-trifluoroethyl)-N-(3-((1-methylcyclopropyl)ethynyl)phenyl)-[1,2,4]triazolo[4,3-a]quinazolin-5-amine

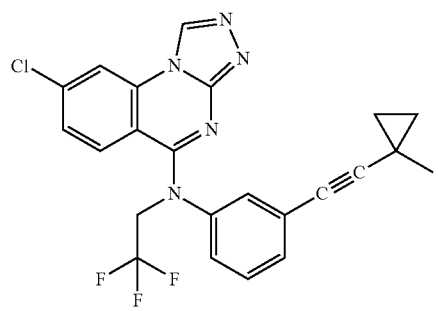 [SMILES: CC1(C#Cc2cccc(N(CC(F)(F)F)c3nc4nncn4c4cc(Cl)ccc34)c2)CC1]

The title compound was synthesized according to the procedures described for Example 759, except using 1-ethynyl-1-methylcyclopropane instead of 1-ethynyl-1-(trifluoromethyl)cyclopropane in Step 4. 1H NMR (400 MHz, DMSO-d$_6$) δ 9.78 (s, 1H), 8.64 (d, J=2.1 Hz, 1H), 7.44 (dd, J=9.0, 2.1 Hz, 1H), 7.37-7.34 (m, 1H), 7.34-7.28 (m, 2H), 7.27-7.22 (m, 2H), 5.06 (q, J=9.2 Hz, 2H), 1.28 (s, 3H), 0.91 (dd, J=3.9 Hz, 2H), 0.73 (dd, 2H); LCMS(m/z) 456.1.

Example 764. 8-chloro-N-methyl-N-(6-(4-(1-(trifluoromethyl)cyclopropyl)phenyl)pyrazin-2-yl)-[1,2,4]triazolo[4,3-a]quinazolin-5-amine

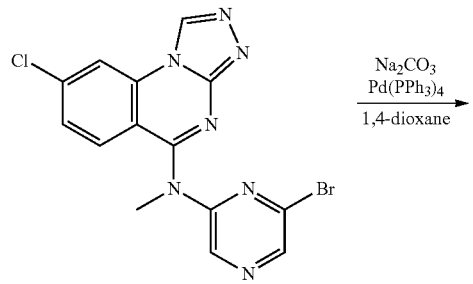

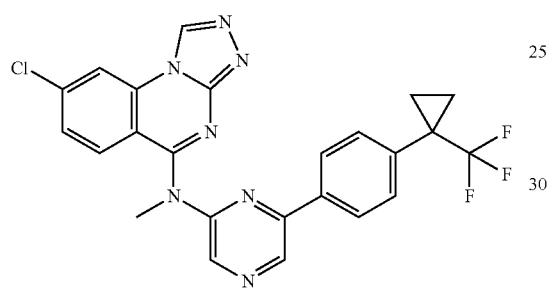

N-(6-Bromopyrazin-2-yl)-8-chloro-N-methyl-[1,2,4]triazolo[4,3-a]quinazolin-5-amine was prepared according to the method of preparing 8-chloro-N-(3-fluoro-5-iodophenyl)-N-(2,2,2-trifluoroethyl)-[1,2,4]triazolo[4,3-a]quinazolin-5-amine as described for Example 759, except using 6-bromo-N-methylpyrazin-2-amine instead of 3-iodo-N-(2,2,2-trifluoroethyl)aniline.

To a solution of N-(6-bromopyrazin-2-yl)-8-chloro-N-methyl-[1,2,4]triazolo[4,3-a]quinazolin-5-amine (30 mg, 77 μmol) and 4,4,5,5-tetramethyl-2-[4-[1-(trifluoromethyl)cyclopropyl]phenyl]-1,3,2-dioxaborolanein (18.7 mg, 60 μmol) 1,4-dioxane (0.75 mL) was added Pd(PPh$_3$)$_4$ (4.5 mg, 3.8 μmol) and aqueous sodium carbonate (0.115 mL, 2 N, 230 mmol). The resulting solution was heated to 90° C. for 3 h, then cooled to room temperature, diluted with ethyl acetate, filtered through Celite®, and concentrated under reduced pressure. The resultant residue was purified via prep HPLC and appropriate fractions were lyophilized to afford the title compound: 1H NMR (400 MHz, DMSO-d$_6$) δ 9.86 (s, 1H), 8.91 (s, 1H), 8.73 (d, J=2.1 Hz, 1H), 8.55 (s, 1H), 7.91 (d, J=8.4 Hz, 2H), 7.63 (d, J=8.8 Hz, 1H), 7.57-7.48 (m, 3H), 3.77 (s, 3H), 1.39-1.32 (m, 2H), 1.20-1.11 (m, 2H); LCMS(m/z) 496.1.

Example 765. 8-chloro-7-fluoro-N-methyl-N-(6-(6-(2,2,2-trifluoroethoxy)pyridin-3-yl)pyrazin-2-yl)-[1,2,4]triazolo[4,3-a]quinazolin-5-amine

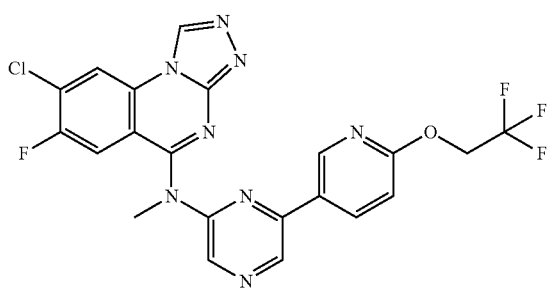 [SMILES: CN(c1cncc(-c2ccc(OCC(F)(F)F)nc2)n1)c1nc2nncn2c2cc(Cl)c(F)cc12]

The title compound was synthesized according to procedures described for Example 495. 1H NMR (400 MHz, DMSO-d$_6$) δ 9.86 (s, 1H), 8.95 (d, J=6.4 Hz, 1H), 8.93 (s, 1H), 8.79 (d, J=2.1 Hz, 1H), 8.54 (s, 1H), 8.33 (dd, J=8.7, 2.5 Hz, 1H), 7.77 (d, J=9.7 Hz, 1H), 7.09 (d, J=8.7 Hz, 1H), 5.05 (q, J=9.1 Hz, 2H), 3.74 (s, 3H); LCMS(m/z) 505.1.

Example 766. 8-chloro-7-fluoro-N-methyl-N-(6-(4-(1-(trifluoromethyl)cyclopropyl)phenyl)pyrazin-2-yl)-[1,2,4]triazolo[4,3-a]quinazolin-5-amine

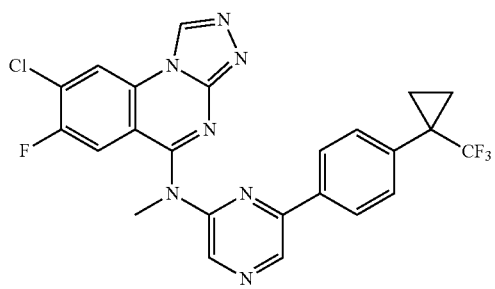 [SMILES: CN(c1cncc(-c2ccc(C3(C(F)(F)F)CC3)cc2)n1)c1nc2nncn2c2cc(Cl)c(F)cc12]

The title compound was synthesized according to procedures described for Example 495. 1H NMR (400 MHz, DMSO-d$_6$) δ 9.85 (s, 1H), 8.95 (d, J=6.4 Hz, 1H), 8.90 (s, 1H), 8.57 (s, 1H), 7.91 (d, J=8.4 Hz, 2H), 7.74 (d, J=9.7 Hz, 1H), 7.53 (d, J=8.1 Hz, 2H), 3.74 (s, 3H), 1.40-1.32 (m, 2H), 1.19-1.12 (m, 2H); LCMS(m/z) 514.1.

Example 767. 6,7-difluoro-1-(methoxymethyl)-5-(5-((1-(trifluoromethyl)cyclopropyl)ethynyl)-3,4-dihydroquinolin-1(2H)-yl)-[1,2,4]triazolo[4,3-a]quinazoline

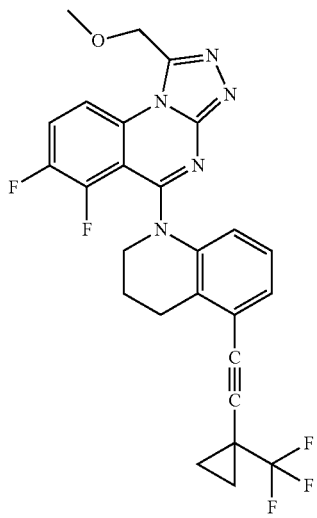 [SMILES: COCc1nnc2nc(N3CCCc4c(C#CC5(C(F)(F)F)CC5)cccc43)c3c(F)c(F)ccc3n12]

The title compound was synthesized according to procedures described for Example 522. $^1$H NMR (400 MHz, Methanol-$d_4$) δ 8.29 (dd, J=9.3, 3.7 Hz, 1H), 8.06 (q, J=9.0 Hz, 1H), 7.31 (dd, J=7.6, 1.2 Hz, 1H), 7.00 (t, J=7.8 Hz, 1H), 6.96-6.87 (m, 1H), 5.11 (s, 2H), 4.20 (br s, 2H), 3.54 (s, 3H), 3.10 (br s, 2H), 2.21 (br s, 2H), 1.53-1.43 (m, 2H), 1.38 (d, J=5.8 Hz, 2H); LCMS(m/z) 514.4.

Example 768. 7-fluoro-5-(6-((1-(trifluoromethyl)cyclopropyl)ethynyl)-2,3,4,5-tetrahydro-1H-benzo[b]azepin-1-yl)-[1,2,4]triazolo[4,3-a]quinazoline

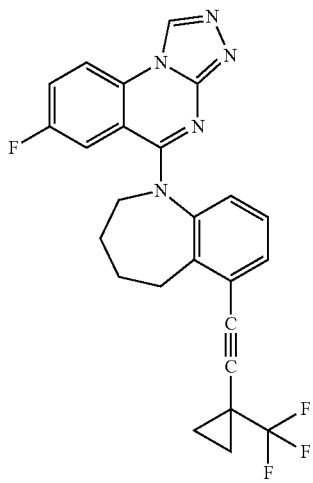 [SMILES: Fc1ccc2c(c1)c(N1CCCCc3c(C#CC4(C(F)(F)F)CC4)cccc31)nc1nncn12]

The title compound was synthesized according to procedures described for Example 522. $^1$H NMR (400 MHz, Methanol-$d_4$) δ 9.57 (s, 1H), 8.40 (dd, J=9.2, 4.8 Hz, 1H), 7.78 (ddd, J=9.3, 7.4, 2.7 Hz, 1H), 7.63 (dd, J=7.8, 1.2 Hz, 1H), 7.30 (t, J=7.9 Hz, 1H), 7.15 (dd, J=7.9, 1.2 Hz, 1H), 6.56 (dd, J=10.7, 2.7 Hz, 1H), 5.31 (br s, 1H), 3.53 (br s, 1H), 2.95 (br s, 1H), 2.15 (br s, 3H), 1.94 (br s, 1H), 1.66 (br s, 1H), 1.48 (q, J=4.2, 3.2 Hz, 2H), 1.45-1.33 (m, 2H); LCMS(m/z) 466.4.

Example 769. 6,7-difluoro-1-methyl-5-(6-((1-(trifluoromethyl)cyclopropyl)ethynyl)-2,3,4,5-tetrahydro-1H-benzo[b]azepin-1-yl)-[1,2,4]triazolo[4,3-a]quinazoline

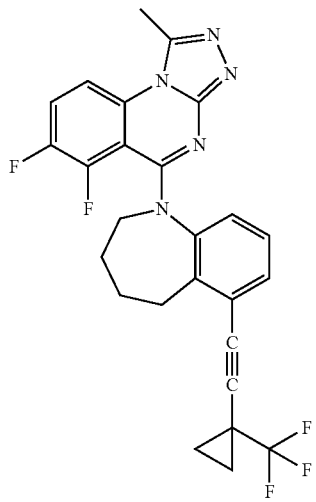 [SMILES: Cc1nnc2nc(N3CCCCc4c(C#CC5(C(F)(F)F)CC5)cccc43)c3c(F)c(F)ccc3n12]

The title compound was synthesized according to procedures described for Example 522. $^1$H NMR (400 MHz, Methanol-$d_4$) δ 8.20 (ddd, J=9.5, 4.0, 1.8 Hz, 1H), 7.96 (td, J=9.4, 7.9 Hz, 1H), 7.42 (dd, J=7.8, 1.2 Hz, 1H), 7.01 (t, J=7.9 Hz, 1H), 6.79 (dd, J=7.9, 1.2 Hz, 1H), 5.06 (br s, 1H), 3.48 (br s, 2H), 3.10 (br s, 1H), 3.06 (s, 3H), 2.37-1.59 (m, 4H), 1.53-1.45 (m, 2H), 1.41-1.33 (m, 2H); LCMS(m/z) 498.4.

Example 770. 6,7-difluoro-1-methyl-5-(6-(4,4,4-trifluoro-3,3-dimethylbut-1-yn-1-yl)-2,3,4,5-tetrahydro-1H-benzo[b]azepin-1-yl)-[1,2,4]triazolo[4,3-a]quinazoline

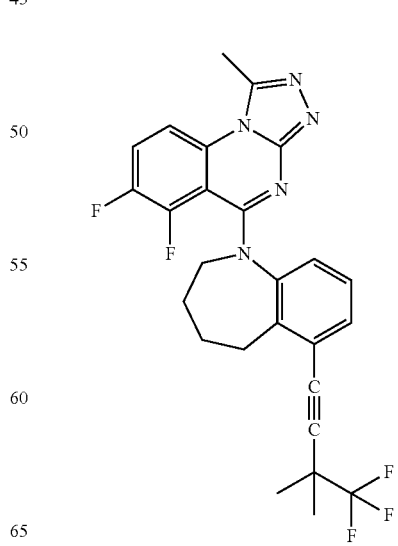

The title compound was synthesized according to procedures described for Example 522. ¹H NMR (400 MHz, Methanol-d₄) δ 8.21 (ddd, J=9.5, 4.0, 1.8 Hz, 1H), 7.96 (td, J=9.4, 7.9 Hz, 1H), 7.42 (dd, J=7.8, 1.2 Hz, 1H), 7.02 (t, J=7.8 Hz, 1H), 6.80 (dd, J=8.0, 1.1 Hz, 1H), 5.08 (br s, 1H), 3.45 (br s, 2H), 3.10 (br s, 1H), 3.06 (s, 3H), 2.25-1.55 (br s, 4H), 1.58 (s, 6H); LCMS(m/z) 500.4.

Example 771. 5-(5-(4,4-difluoro-3,3-dimethylbut-1-yn-1-yl)-3,4-dihydroquinolin-1(2H)-yl)-6,7-difluoro-1-methyl-[1,2,4]triazolo[4,3-a]quinazoline

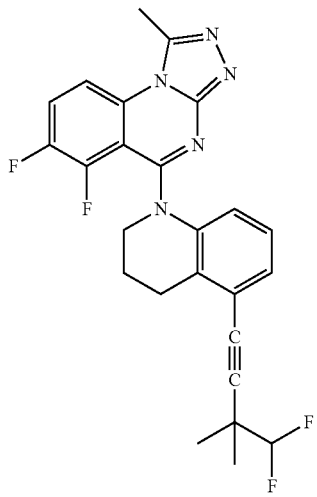 [SMILES: Cc1nnc2nc(N3CCCc4c(C#CC(C)(C)C(F)F)cccc43)c3c(F)c(F)ccc3n12]

The title compound was synthesized according to procedures described for Example 522. ¹H NMR (400 MHz, Methanol-d₄) δ 8.26 (ddd, J=9.7, 3.9, 1.8 Hz, 1H), 8.11-7.97 (m, 1H), 7.30 (dd, J=7.7, 1.2 Hz, 1H), 6.98 (t, J=7.9 Hz, 1H), 6.89 (d, J=8.1 Hz, 1H), 5.84 (t, J=56.7 Hz, 1H), 4.08 (br s, 2H), 3.25-2.85 (br s, 2H), 3.08 (s, 3H), 2.20 (br s, 2H), 1.42 (d, J=1.2 Hz, 6H); LCMS(m/z) 468.3.

Example 772. 5-(5-((1-(1,1-difluoroethyl)cyclopropyl)ethynyl)-3,4-dihydroquinolin-1(2H)-yl)-6,7-difluoro-1-methyl-[1,2,4]triazolo[4,3-a]quinazoline

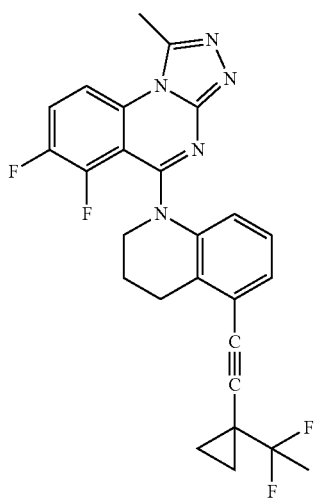 [SMILES: Cc1nnc2nc(N3CCCc4c(C#CC5(C(C)(F)F)CC5)cccc43)c3c(F)c(F)ccc3n12]

The title compound was synthesized according to procedures described for Example 522. ¹H NMR (400 MHz, Methanol-d₄) δ 8.32-8.20 (m, 1H), 8.04 (q, J=9.2 Hz, 1H), 7.29 (dd, J=7.7, 1.2 Hz, 1H), 6.98 (t, J=7.9 Hz, 1H), 6.89 (d, J=8.0 Hz, 1H), 4.19 (br s, 2H), 315-3.00 (br s, 2H), 3.08 (br s, 3H), 2.20 (br s, 2H), 1.97-1.79 (m, 3H), 1.36-1.25 (m, 2H), 1.15 (dq, J=4.9, 3.3, 2.6 Hz, 2H); LCMS(m/z) 480.3.

Example 773. 6,7-difluoro-5-(6-((1-(trifluoromethyl)cyclopropyl)ethynyl)-2,3,4,5-tetrahydro-1H-benzo[b]azepin-1-yl)-[1,2,4]triazolo[4,3-a]quinazoline

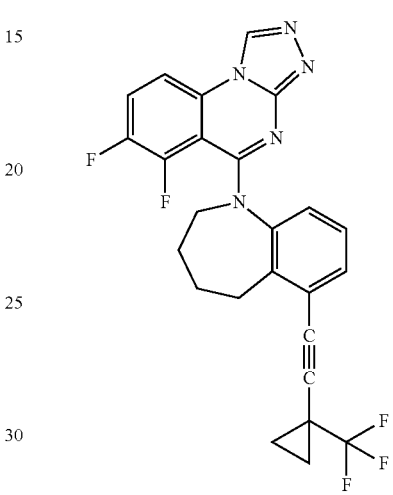

The title compound was synthesized according to procedures described for Example 522. ¹H NMR (400 MHz, Methanol-d₄) δ 9.59 (s, 1H), 8.18 (ddd, J=9.3, 4.1, 1.9 Hz, 1H), 8.07-7.94 (m, 1H), 7.43 (dd, J=7.8, 1.2 Hz, 1H), 7.03 (t, J=7.8 Hz, 1H), 6.83 (dd, J=8.0, 1.2 Hz, 1H), 5.10-4.90 (m, 1H), 3.71-3.35 (m, 2H), 1.94 (d, J=6.8 Hz, 5H), 1.52-1.45 (m, 2H), 1.38 (s, 2H); LCMS(m/z) 484.3.

Example 774. 6,7-difluoro-1-methyl-5-(5-((1-(trifluoromethyl)cyclopropyl)ethynyl)-3,4-dihydroquinolin-1(2H)-yl)-[1,2,4]triazolo[4,3-a]quinazoline

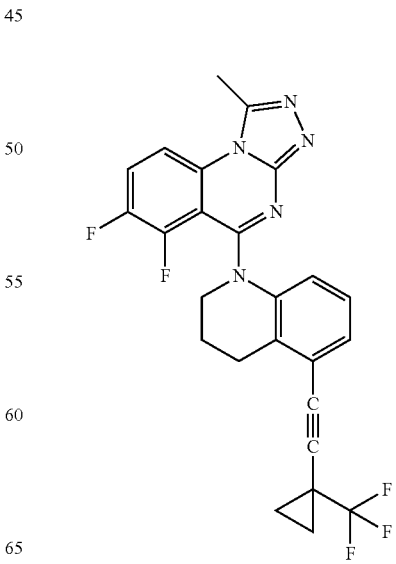

The title compound was synthesized according to procedures described for Example 522. ¹H NMR (400 MHz, Methanol-d₄) δ 8.11 (ddd, J=9.4, 3.9, 1.8 Hz, 1H), 7.84 (td, J=9.4, 7.8 Hz, 1H), 7.13 (dd, J=7.7, 1.1 Hz, 1H), 6.88 (t, J=7.9 Hz, 1H), 6.62 (d, J=8.1 Hz, 1H), 4.05 (br s, 2H), 3.03 (m, 5H), 2.31-2.02 (br s, 2H), 1.48-1.29 (m, 4H); LCMS (m/z) 484.3.

Example 775. 6,7-difluoro-5-(6-(4,4,4-trifluoro-3,3-dimethylbut-1-yn-1-yl)-2,3,4,5-tetrahydro-1H-benzo[b]azepin-1-yl)-[1,2,4]triazolo[4,3-a]quinazoline

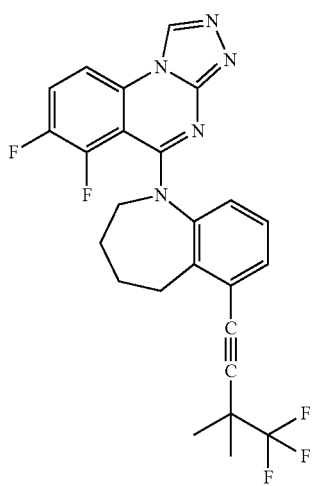

The title compound was synthesized according to procedures described for Example 522. ¹H NMR (400 MHz, Methanol-d₄) δ 9.56-9.29 (m, 1H), 8.06 (s, 1H), 7.96-7.69 (m, 1H), 7.33 (d, J=9.0 Hz, 1H), 6.97 (q, J=9.9, 8.7 Hz, 1H), 6.76-6.59 (m, 1H), 5.59-5.44 (m, 1H), 4.36 (d, J=189.5 Hz, 1H), 3.18 (s, 1H), 1.98 (d, J=72.6 Hz, 5H), 1.65-1.51 (m, 6H); LCMS(m/z) 486.3.

Example 776. 8-chloro-7-fluoro-1-(methoxymethyl)-5-(5-(4,4,4-trifluoro-3,3-dimethylbut-1-yn-1-yl)-3,4-dihydroquinolin-1(2H)-yl)-[1,2,4]triazolo[4,3-a]quinazoline

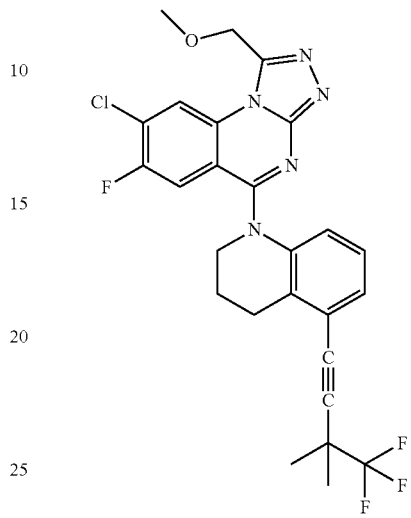

The title compound was synthesized in a similar fashion as Example 500, except using 1,1,1,2-tetramethoxyethane and [7-chloro-6-fluoro-4-[5-(4,4,4-trifluoro-3,3-dimethyl-but-1-ynyl)-3,4-dihydro-2H-quinolin-1-yl]quinazolin-2-yl]hydrazine instead of 1,1,1-triethoxyethane and 7-bromo-6-fluoro-2-hydrazineyl-N-methyl-N-phenylquinazolin-4-amine. ¹H NMR (400 MHz, Methanol-d₄) δ 8.58 (d, J=6.3 Hz, 1H), 7.45-7.33 (m, 2H), 7.09 (t, J=7.9 Hz, 1H), 6.99 (dd, J=8.2, 1.1 Hz, 1H), 5.13 (s, 2H), 4.21 (t, J=6.5 Hz, 2H), 3.55 (s, 3H), 3.11 (t, J=6.6 Hz, 2H), 2.22 (p, J=6.6 Hz, 2H), 1.58 (s, 6H); LCMS(m/z) 532.4.

Example 777. 5-(5-((1-(1,1-difluoroethyl)cyclopropyl)ethynyl)-3,4-dihydroquinolin-1(2H)-yl)-6,7-difluoro-[1,2,4]triazolo[4,3-a]quinazoline

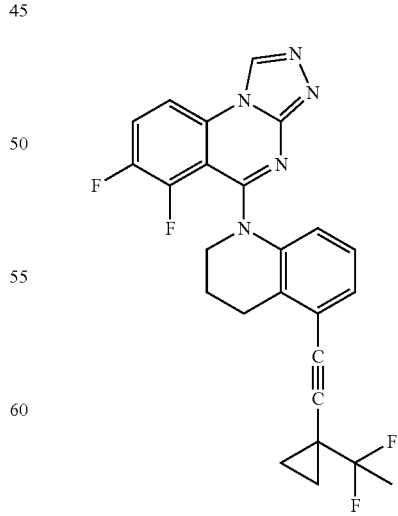

The title compound was synthesized according to procedures described for Example 522. ¹H NMR (400 MHz, Methanol-d$_4$) δ 9.46 (s, 1H), 8.10 (ddd, J=9.2, 4.0, 1.8 Hz, 1H), 7.86 (td, J=9.4, 7.6 Hz, 1H), 7.13 (dd, J=7.7, 1.1 Hz, 1H), 6.89 (t, J=7.9 Hz, 1H), 6.68-6.61 (m, 1H), 4.02 (br s, 2H), 3.01 (br s, 2H), 2.16 (br s, 2H), 1.89 (t, J=17.9 Hz, 3H), 1.34-1.21 (m, 2H), 1.12 (ddq, J=4.8, 3.1, 2.0 Hz, 2H); LCMS(m/z) 466.3.

Example 778. 6,7-difluoro-1-methyl-5-(5-(4,4,4-trifluoro-3,3-dimethylbut-1-yn-1-yl)-3,4-dihydroquinolin-1(2H)-yl)-[1,2,4]triazolo[4,3-a]quinazoline

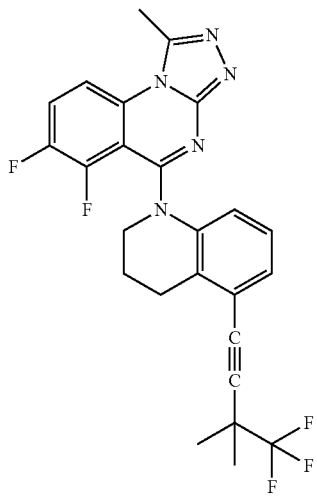 [SMILES: Cc1nnc2nc(N3CCCc4c(C#CC(C)(C)C(F)(F)F)cccc43)c3c(F)c(F)ccc3n12]

The title compound was synthesized according to procedures described for Example 522. $^1$H NMR (400 MHz, Methanol-d$_4$) δ 8.15 (ddd, J=9.6, 3.9, 1.9 Hz, 1H), 7.88 (td, J=9.5, 8.0 Hz, 1H), 7.13 (dd, J=7.7, 1.1 Hz, 1H), 6.92 (t, J=7.9 Hz, 1H), 6.71 (d, J=8.0 Hz, 1H), 4.01 (br s, 2H), 3.03 (br s, 2H), 2.48-1.88 (br s, 2H), 1.57 (s, 6H); LCMS(m/z) 486.3.

Example 779. 6,7-difluoro-5-(5-(4,4,4-trifluoro-3,3-dimethylbut-1-yn-1-yl)-3,4-dihydroquinolin-1(2H)-yl)-[1,2,4]triazolo[4,3-a]quinazoline

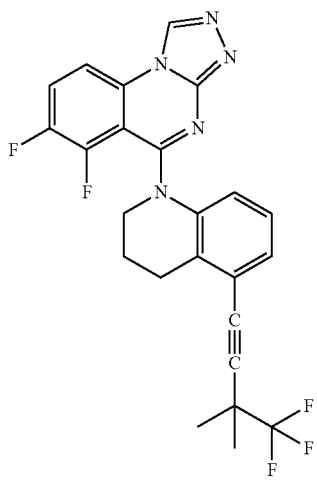 [SMILES: CC(C)(C#Cc1cccc2c1CCCN2c1nc2nncn2c2ccc(F)c(F)c12)C(F)(F)F]

The title compound was synthesized according to procedures described for Example 522. $^1$H NMR (400 MHz, Methanol-d$_4$) δ 9.64 (s, 1H), 8.24 (ddd, J=9.3, 4.1, 1.8 Hz, 1H), 8.08 (td, J=9.4, 7.6 Hz, 1H), 7.31 (dd, J=7.5, 1.3 Hz, 1H), 7.07-6.89 (m, 2H), 4.18 (br s, 2H), 3.06 (br s, 2H), 2.18 (br s, J=20.9 Hz, 2H), 1.58 (s, 6H); LCMS(m/z) 472.3.

Example 780. 8-chloro-7-fluoro-1-methyl-5-(6-(4,4,4-trifluoro-3,3-dimethylbut-1-yn-1-yl)-2,3,4,5-tetrahydro-1H-benzo[b]azepin-1-yl)-[1,2,4]triazolo[4,3-a]quinazoline

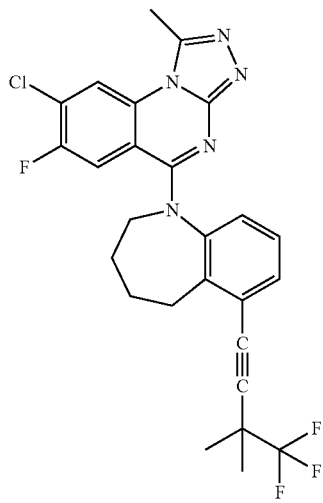 [SMILES: Cc1nnc2nc(N3CCCCc4c(C#CC(C)(C)C(F)(F)F)cccc43)c3cc(F)c(Cl)cc3n12]

The title compound was synthesized in a similar fashion as Example 500, except using [7-chloro-6-fluoro-4-[6-(4,4,4-trifluoro-3,3-dimethyl-but-1-ynyl)-2,3,4,5-tetrahydro-1-benzazepin-1-yl]quinazolin-2-yl]hydrazine instead of 7-bromo-6-fluoro-2-hydrazineyl-N-methyl-N-phenylquinazolin-4-amine. $^1$H NMR (400 MHz, Methanol-d$_4$) δ 8.42 (d, J=6.4 Hz, 1H), 7.63 (dd, J=7.9, 1.3 Hz, 1H), 7.30 (t, J=7.9 Hz, 1H), 7.10 (dd, J=8.0, 1.3 Hz, 1H), 6.77 (d, J=10.8 Hz, 1H), 5.25 (br s, 1H), 3.48 (br s, 3H), 3.07 (s, 3H), 1.94 (s, 4H), 1.58 (s, 6H); LCMS(m/z) 516.4.

Example 781. 8-chloro-5-(5-(4,4,4-trifluoro-3,3-dimethylbut-1-yn-1-yl)-3,4-dihydroquinolin-1(2H)-yl)-[1,2,4]triazolo[4,3-a]quinazoline

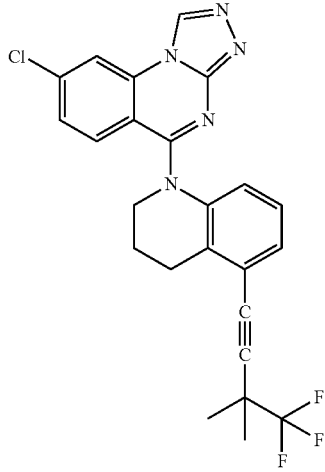

The title compound was synthesized according to procedures described for Example 522. $^1$H NMR (400 MHz, Methanol-d$_4$) δ 9.64 (s, 1H), 8.54 (d, J=2.0 Hz, 1H), 7.57 (d, J=9.0 Hz, 1H), 7.48 (dd, J=9.0, 2.0 Hz, 1H), 7.36 (dd, J=7.5, 1.3 Hz, 1H), 7.07 (t, J=7.8 Hz, 1H), 7.01 (dd, J=8.2, 1.2 Hz, 1H), 4.22 (t, J=6.6 Hz, 2H), 3.09 (t, J=6.7 Hz, 2H), 2.22 (p, J=6.7 Hz, 2H), 1.58 (s, 6H); LCMS(m/z) 470.4.

Example 782. 8-chloro-5-(5-(4,4-difluoro-3,3-dimethylbut-1-yn-1-yl)-3,4-dihydroquinolin-1(2H)-yl)-[1,2,4]triazolo[4,3-a]quinazoline

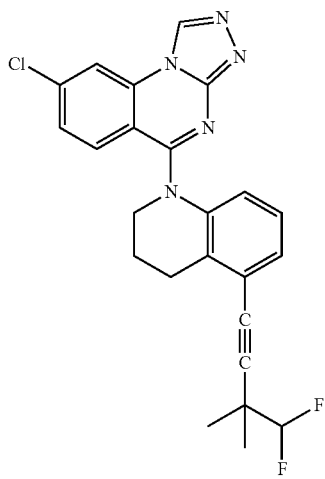 [SMILES: CC(C)(C#Cc1cccc2c1CCCN2c1nc2nncn2c2cc(Cl)ccc12)C(F)F]

The title compound was synthesized according to procedures described for Example 522. $^1$H NMR (400 MHz, Methanol-d$_4$) δ 9.55 (s, 1H), 8.45 (d, J=2.0 Hz, 1H), 7.58 (d, J=9.0 Hz, 1H), 7.41 (dd, J=9.0, 2.0 Hz, 1H), 7.22 (dd, J=7.6, 1.1 Hz, 1H), 6.98 (t, J=7.9 Hz, 1H), 6.81 (dd, J=8.2, 1.1 Hz, 1H), 5.83 (t, J=56.7 Hz, 1H), 4.10 (t, J=6.5 Hz, 2H), 3.07 (t, J=6.7 Hz, 2H), 2.19 (p, J=6.3 Hz, 2H), 1.42 (d, J=1.1 Hz, 6H); LCMS(m/z) 452.4.

Example 783. 8-chloro-7-fluoro-5-(5-(4,4,4-trifluoro-3,3-dimethylbut-1-yn-1-yl)-3,4-dihydroquinolin-1(2H)-yl)-[1,2,4]triazolo[4,3-a]quinazoline

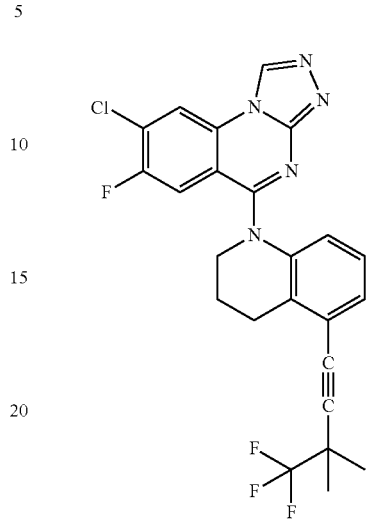

The title compound was synthesized in a similar fashion as Example 523, except using 7-fluoro-5-[5-(4,4,4-trifluoro-3,3-dimethyl-but-1-ynyl)-3,4-dihydro-2H-quinolin-1-yl]-[1,2,4]triazolo[4,3-a]quinazolin-8-amine instead of 5-(5-(cyclopropylethynyl)-3,4-dihydroquinolin-1(2H)-yl)-7-fluoro-[1,2,4]triazolo[4,3-a]quinazolin-8-amine. $^1$H NMR (400 MHz, Methanol-d$_4$) δ 9.40 (s, 1H), 8.48 (d, J=6.2 Hz, 1H), 7.28 (d, J=9.7 Hz, 1H), 7.24-7.16 (m, 1H), 6.95 (t, J=7.9 Hz, 1H), 6.65 (d, J=8.1 Hz, 1H), 4.05 (t, J=6.5 Hz, 2H), 3.04 (t, J=6.7 Hz, 2H), 2.18 (t, J=6.5 Hz, 2H), 1.55 (s, 6H); LCMS (m/z) 488.4.

Example 784. 8-chloro-5-(5-(4,4-difluoro-3,3-dimethylbut-1-yn-1-yl)-3,4-dihydroquinolin-1(2H)-yl)-7-fluoro-[1,2,4]triazolo[4,3-a]quinazoline

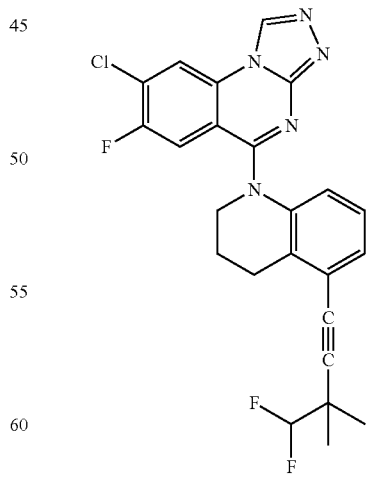

The title compound was synthesized according to procedures described for Example 522. $^1$H NMR (400 MHz, Methanol-d$_4$) δ 9.45 (s, 1H), 8.53 (d, J=6.3 Hz, 1H), 7.28 (d, J=9.8 Hz, 1H), 7.21 (dd, J=7.8, 1.1 Hz, 1H), 6.96 (t, J=7.9

Hz, 1H), 6.68 (d, J=8.1 Hz, 1H), 5.75 (t, J=56.8 Hz, 1H), 4.06 (t, J=6.5 Hz, 2H), 3.06 (t, J=6.7 Hz, 2H), 2.18 (p, J=6.6 Hz, 2H), 1.41 (d, J=1.2 Hz, 6H); LCMS(m/z) 470.3.

Example 785. 8-chloro-N-(3-(4,4-difluoro-3,3-dimethylbut-1-yn-1-yl)phenyl)-N-methyl-[1,2,4]triazolo[4,3-a]quinazolin-5-amine

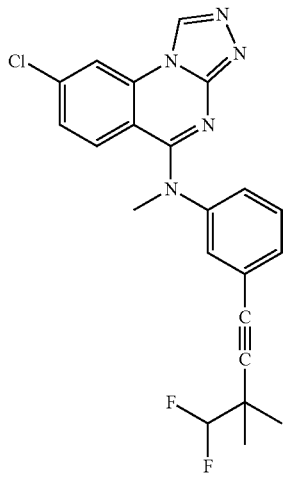 [SMILES: CN(c1cccc(C#CC(C)(C)C(F)F)c1)c1nc2nncn2c2cc(Cl)ccc12]

The title compound was synthesized according to procedures described for Example 522. ¹H NMR (400 MHz, Methanol-d₄) δ 9.60 (s, 1H), 8.53 (d, J=2.1 Hz, 1H), 7.64-7.48 (m, 3H), 7.43 (ddd, J=9.1, 5.6, 2.5 Hz, 2H), 7.22 (d, J=9.2 Hz, 1H), 5.77 (t, J=56.7 Hz, 1H), 3.79 (s, 3H), 1.36 (d, J=1.2 Hz, 6H); LCMS(m/z) 426.3.

Example 786. 8-chloro-7-fluoro-5-(5-((1-(trifluoromethyl)cyclopropyl)ethynyl)-3,4-dihydroquinolin-1(2H)-yl)-[1,2,4]triazolo[4,3-a]quinazoline

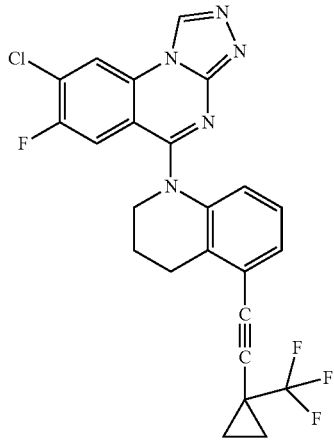 [SMILES: Fc1cc2c(N3CCCc4c(C#CC5(C(F)(F)F)CC5)cccc43)nc3nncn3c2cc1Cl]

The title compound was synthesized in a similar fashion as Example 523, except using 5-[5-[2-[1-(trifluoromethyl)cyclopropyl]ethynyl]-3,4-dihydro-2H-quinolin-1-yl]-[1,2,4]triazolo[4,3-a]quinazolin-8-amine instead of 5-(5-(cyclopropylethynyl)-3,4-dihydroquinolin-1(2H)-yl)-7-fluoro-[1,2,4]triazolo[4,3-a]quinazolin-8-amine. ¹H NMR (400 MHz, Methanol-d₄) δ 9.67 (s, 1H), 8.73 (d, J=6.3 Hz, 1H), 7.40 (d, J=7.5 Hz, 1H), 7.32 (d, J=10.0 Hz, 1H), 7.10 (t, J=7.9 Hz, 1H), 7.03 (d, J=8.1 Hz, 1H), 4.22 (t, J=6.6 Hz, 2H), 3.10 (t, J=6.6 Hz, 2H), 2.21 (p, J=6.6 Hz, 2H), 1.48 (q, J=5.0, 4.3 Hz, 2H), 1.38 (s, 2H); LCMS(m/z) 486.2.

Example 787. 8-chloro-7-fluoro-5-(5-((1-methylcyclopropyl)ethynyl)-3,4-dihydroquinolin-1(2H)-yl)-[1,2,4]triazolo[4,3-a]quinazoline

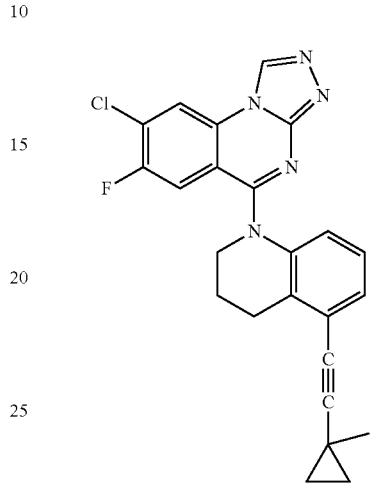

The title compound was synthesized in a similar fashion as Example 523, except using 7-fluoro-5-[5-[2-(1-methylcyclopropyl)ethynyl]-3,4-dihydro-2H-quinolin-1-yl]-[1,2,4]triazolo[4,3-a]quinazolin-8-amine instead of 5-(5-(cyclopropylethynyl)-3,4-dihydroquinolin-1(2H)-yl)-7-fluoro-[1,2,4]triazolo[4,3-a]quinazolin-8-amine. ¹H NMR (400 MHz, Methanol-d₄) δ 9.61 (s, 1H), 8.70 (d, J=6.3 Hz, 1H), 7.33 (dd, J=7.7, 1.1 Hz, 1H), 7.27 (d, J=10.1 Hz, 1H), 7.05 (t, J=7.9 Hz, 1H), 6.93 (dd, J=8.1, 1.1 Hz, 1H), 4.20 (t, J=6.7 Hz, 2H), 3.07 (t, J=6.6 Hz, 2H), 2.19 (p, J=6.7 Hz, 2H), 1.40 (s, 3H), 1.04 (q, J=4.1 Hz, 2H), 0.84-0.75 (m, 2H); LCMS (m/z) 432.3.

Example 788. N-(3-(cyclopropylethynyl)-5-fluorophenyl)-N-(2,2-difluoroethyl)-6,7-difluoro-1-methyl-[1,2,4]triazolo[4,3-a]quinazolin-5-amine

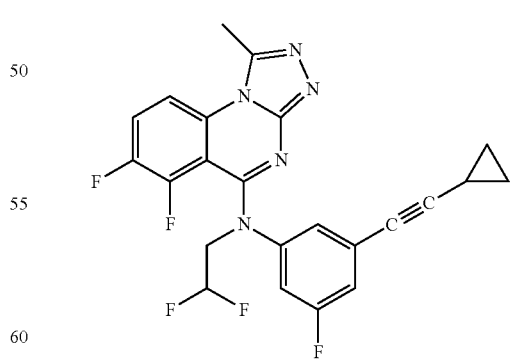

The title compound was synthesized in an analogous manner according to the procedures described for Example 690. 1H NMR (400 MHz, DMSO-d₆) δ 8.16 (dd, J=10.0, 4.3 Hz, 1H), 8.10-8.02 (m, 1H), 7.08 (d, J=16.7 Hz, 2H), 6.95 (d, J=9.7 Hz, 1H), 6.68-6.35 (m, 1H), 4.61 (td, J=15.6, 15.0, 3.7 Hz, 2H), 2.99 (d, J=3.6 Hz, 3H), 1.50 (ddd, J=13.5, 8.6, 5.3 Hz, 1H), 0.90-0.83 (m, 2H), 0.70 (dt, J=6.9, 3.4 Hz, 2H); LCMS(m/z) 458.2.

Example 789. 1-(1-(6-fluoro-1-methyl-[1,2,4]triazolo[4,3-a]quinazolin-5-yl)-1,2,3,4-tetrahydroquinolin-5-yl)-3-methylpent-1-yn-3-ol

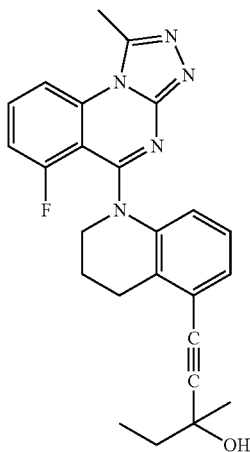 [SMILES: CCC(C)(O)C#Cc1cccc2c1CCCN2c1nc2nnc(C)n2c2cccc(F)c12]

The title compound was synthesized in an analogous manner according to the procedures described for Example 719. 1H NMR (400 MHz, DMSO-$d_6$) δ 8.18 (d, J=8.6 Hz, 1H), 8.01 (td, J=8.4, 5.5 Hz, 1H), 7.37 (dd, J=11.8, 8.3 Hz, 1H), 7.12 (d, J=7.5 Hz, 1H), 6.93 (d, J=7.8 Hz, 1H), 6.82 (d, J=8.1 Hz, 1H), 4.09-3.95 (m, 2H), 3.00 (s, 3H), 2.90-2.73 (m, 2H), 2.17-2.00 (m, 2H), 1.69 (tt, J=13.3, 6.2 Hz, 3H), 1.47 (s, 3H), 1.04 (t, J=7.4 Hz, 3H); LCMS(m/z) 430.2.

Example 790. 1-(1-(6-fluoro-1-methyl-[1,2,4]triazolo[4,3-a]quinazolin-5-yl)-1,2,3,4-tetrahydroquinolin-5-yl)-4-methylpent-1-yn-3-ol

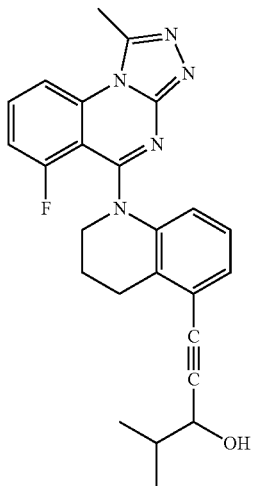 [SMILES: Cc1nnc2nc(N3CCCc4c(C#CC(O)C(C)C)cccc43)c3c(F)cccc3n12]

The title compound was synthesized in an analogous manner according to the procedures described for Example 719. 1H NMR (400 MHz, DMSO-$d_6$) δ 8.18 (d, J=8.6 Hz, 1H), 8.01 (td, J=8.3, 5.5 Hz, 1H), 7.38 (dd, J=11.7, 8.4 Hz, 1H), 7.15 (d, J=7.5 Hz, 1H), 6.95 (t, J=7.9 Hz, 1H), 6.84 (d, J=8.2 Hz, 1H), 4.31 (d, J=5.6 Hz, 1H), 3.99-3.75 (m, 2H), 3.01 (s, 3H), 2.93-2.75 (m, 2H), 2.21-1.98 (m, 2H), 1.86 (dq, J=13.1, 6.7 Hz, 1H), 1.01 (dd, J=10.8, 6.7 Hz, 6H); LCMS (m/z) 430.2.

Example 791. 1-(1-(6-fluoro-1-methyl-[1,2,4]triazolo[4,3-a]quinazolin-5-yl)-1,2,3,4-tetrahydroquinolin-5-yl)pent-1-yn-3-ol

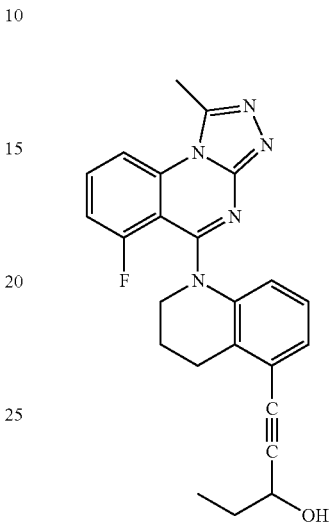

The title compound was synthesized in an analogous manner according to the procedures described for Example 719. 1H NMR (400 MHz, DMSO-$d_6$) δ 8.18 (d, J=8.6 Hz, 1H), 8.01 (td, J=8.4, 5.5 Hz, 1H), 7.37 (dd, J=11.8, 8.3 Hz, 1H), 7.14 (d, J=7.5 Hz, 1H), 6.94 (d, J=15.8 Hz, 1H), 6.83 (d, J=7.8 Hz, 1H), 4.46 (t, J=6.4 Hz, 1H), 4.02-3.85 (m, 2H), 3.00 (s, 3H), 2.89-2.69 (m, 2H), 2.19-2.02 (m, 2H), 1.75-1.67 (m, 2H), 1.01 (t, J=7.4 Hz, 3H); LCMS(m/z) 416.2.

Example 792. 6,7-difluoro-1-methyl-5-(5-((1-(2,2,2-trifluoroethyl)cyclopropyl)ethynyl)-3,4-dihydroquinolin-1(2H)-yl)-[1,2,4]triazolo[4,3-a]quinazoline

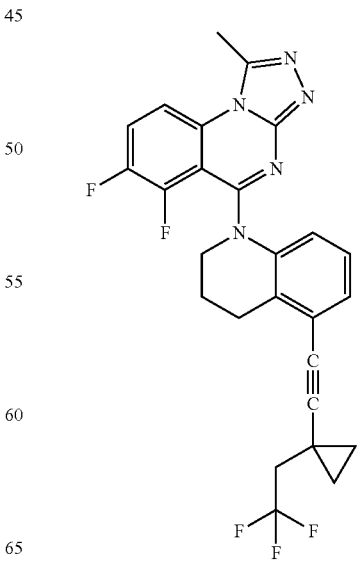

The title compound was synthesized in an analogous manner according to the procedures described for Example 719. 1H NMR (400 MHz, DMSO-d$_6$) δ 8.17 (dd, J=9.5, 3.8 Hz, 1H), 8.09 (q, J=9.4 Hz, 1H), 7.06 (d, J=7.5 Hz, 1H), 6.92 (t, J=7.9 Hz, 1H), 6.80 (d, J=8.1 Hz, 1H), 4.00-3.75 (m, 2H), 2.99 (s, 3H), 2.82 (d, J=19.2 Hz, 2H), 2.62-2.53 (m, 2H), 2.09-1.85 (m, 2H), 1.15-1.04 (m, 4H); LCMS(m/z) 498.2.

Example 793. N-(2,2-difluoroethyl)-N-(3-((1-(1,1-difluoroethyl)cyclopropyl)ethynyl)-5-fluorophenyl)-6,7-difluoro-1-methyl-[1,2,4]triazolo[4,3-a]quinazolin-5-amine

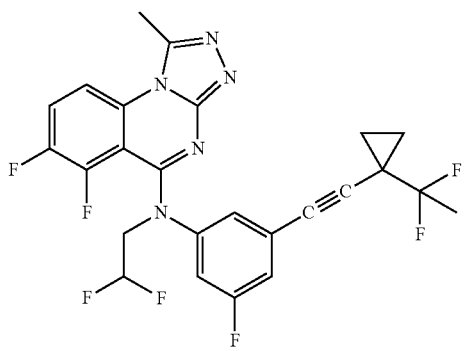 [SMILES: Cc1nnc2nc(N(CC(F)F)c3cc(F)cc(C#CC4(C(C)(F)F)CC4)c3)c3c(F)c(F)ccc3n12]

The title compound was synthesized in an analogous manner according to the procedures described for Example 690. 1H NMR (400 MHz, DMSO-d$_6$) δ 8.17 (dd, J=9.5, 3.5 Hz, 1H), 8.07 (q, J=9.4 Hz, 1H), 7.17 (s, 1H), 7.12 (d, J=10.8 Hz, 1H), 7.06 (d, J=8.8 Hz, 1H), 6.53 (tt, J=55.9, 3.8 Hz, 1H), 4.63 (t, J=16.0 Hz, 2H), 3.00 (s, 3H), 1.79 (t, J=18.5 Hz, 3H), 1.25-1.08 (m, 4H); LCMS(m/z) 522.1.

Example 794. 6,8-difluoro-1-methyl-5-(5-((1-methylcyclopropyl)ethynyl)-3,4-dihydroquinolin-1(2H)-yl)-[1,2,4]triazolo[4,3-a]quinazoline

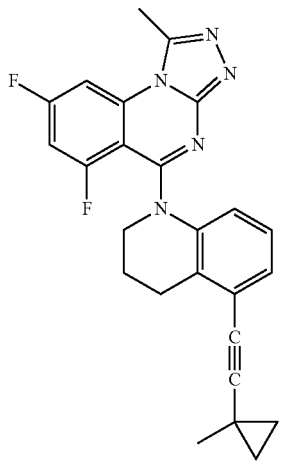 [SMILES: Cc1nnc2nc(N3CCCc4c(C#CC5(C)CC5)cccc43)c3c(F)cc(F)cc3n12]

The title compound was synthesized according to the general procedure described for Example 795 using 1-ethynyl-1-methylcyclopropane in place of 1-ethynyl-1-(trifluoromethyl)cyclopropane. 1H NMR (400 MHz, DMSO-d$_6$) δ 7.94 (d, J=10.1 Hz, 1H), 7.50 (dd, J=11.8, 9.3 Hz, 1H), 7.06 (d, J=7.5 Hz, 1H), 6.89 (d, J=7.8 Hz, 1H), 6.76 (d, J=8.1 Hz, 1H), 4.03-3.72 (m, 2H), 2.98 (s, 3H), 2.87-2.71 (m, 2H), 2.38-1.96 (m, 2H), 1.36 (s, 3H), 0.98 (q, J=4.0 Hz, 2H), 0.79 (q, J=4.1 Hz, 2H); LCMS(m/z) 430.2.

Example 795. 6,8-difluoro-1-methyl-5-(5-((1-(trifluoromethyl)cyclopropyl)ethynyl)-3,4-dihydroquinolin-1(2H)-yl)-[1,2,4]triazolo[4,3-a]quinazoline

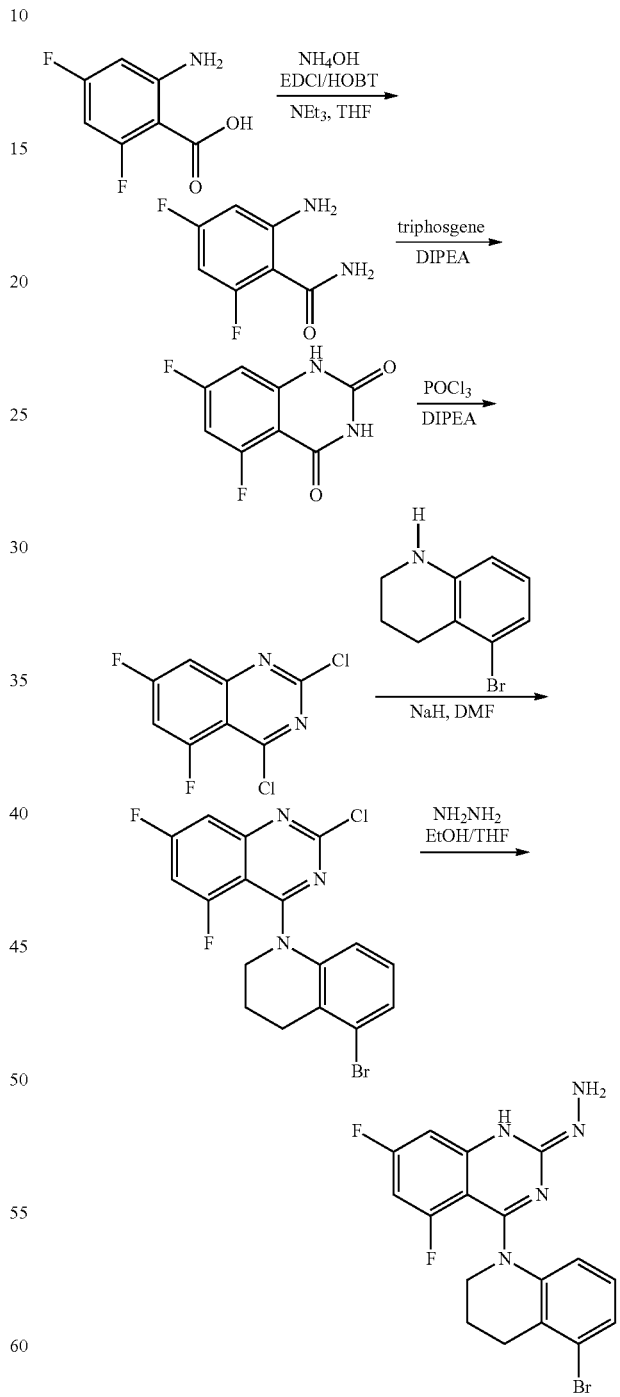

Synthesis of 2-amino-4,6-difluorobenzamide: A solution of 2-amino-4,6-difluorobenzoic acid (1.5 g, 8.66 mmol), triethyl amine (3.5 g, 34.7 mmol), EDCl·HCl (3.3 g, 17.3 mmol), and HOBt (2.9 g, 21.7 mmol) in THF (86.0 mL) was stirred at room temperature for 1 h, followed by the addition of a solution of NH₄OH (5.6 g, 477 mmol, 61.0 mL) and the mixture was stirred for 16 h. The reaction was quenched with water, extracted with DCM, washed with brine and concentrated under reduced pressure. The crude product was purified using flash chromatography eluting with EA in hexanes 0-100% to afford the product. MS (m/z) 172.8 [M+H]⁺.

Synthesis of 5,7-difluoroquinazoline-2,4(1H,3H)-dione: To a solution of 2-amino-4,6-difluorobenzamide (492 mg, 2.86 mmol) in dioxane (1.1 mL) was added DIPEA (924 mg, 7.14 mmol) at 0° C. and the mixture was stirred for 5 minutes, followed by the addition of triphosgene (1.2 g, 4.08 mmol). The cold bath was removed, and the mixture was heated at 100° C. for 12 h. The mixture was concentrated under reduced pressure and the product was triturated with DCM, filtered, and dried in vacuo before use. MS (m/z) 199.2 [M+H]⁺.

Synthesis of 2,4-dichloro-5,7-difluoroquinazoline: To a mixture of 5,7-difluoroquinazoline-2,4(1H,3H)-dione (236 mg, 1.17 mmol) and DIPEA (317 mg, 2.45 mmol) was added phosphoryl chloride (2.1 g, 14.0 mmol) dropwise at rt and the mixture was continued stirring at room temperature for 5 minutes and then heated at 107° C. for 1 hr. The reaction mixture was then carefully poured over crushed ice and stirred vigorously until solid crashed out. The solid was filtered off, washed with water and then dissolved in DCM and dried over Na₂SO₄. The mixture was filtered and concentrated under reduced pressure and used without further purification.

Synthesis of 4-(5-bromo-3,4-dihydroquinolin-1(2H)-yl)-2-chloro-5,7-difluoroquinazoline: To a solution of 5-bromo-1,2,3,4-tetrahydroquinoline (247 mg, 1.17 mmol) in DMF (1.0 mL) at 0° C. was added NaH (60% dispersion in mineral oil) (58.1 mg, 1.52 mmol) in one portion. The mixture was stirred at 0° C. for 30 min, followed by the 2,4-dichloro-5,7-difluoroquinazoline (274 mg, 1.17 mmol) in one portion and the mixture was warmed to room temperature over 16 h. Upon completion, the mixture was cooled to 0° C. and quenched with a few drops of a solution of sat. NH₄Cl(aq) and stirred until solid crashed out. The solid was filtered off and washed with a mixture of hexanes:diethyl ether 4:1 and dried in vacuo and was used with no further purification. MS (m/z) 410.4 [M+H]⁺.

Synthesis of (E)-4-(5-bromo-3,4-dihydroquinolin-1(2H)-yl)-5,7-difluoro-2-hydrazono-1,2-dihydroquinazoline: To a solution of 4-(5-bromo-3,4-dihydroquinolin-1(2H)-yl)-2-chloro-5,7-difluoroquinazoline (330 mg, 0.804 mmol) in THF (10.0 mL) and ethanol (5.00 mL) was added hydrazine monohydrate (644 mg, 20.1 mmol) and the mixture was stirred at room temperature for 12 h. Upon completion, the reaction was diluted with EA and washed with water, dried over Na₂SO₄ and concentrated under reduced pressure to afford the product. MS (m/z) 406.3 [M+H]⁺.

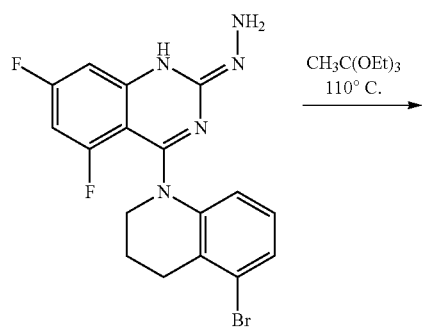

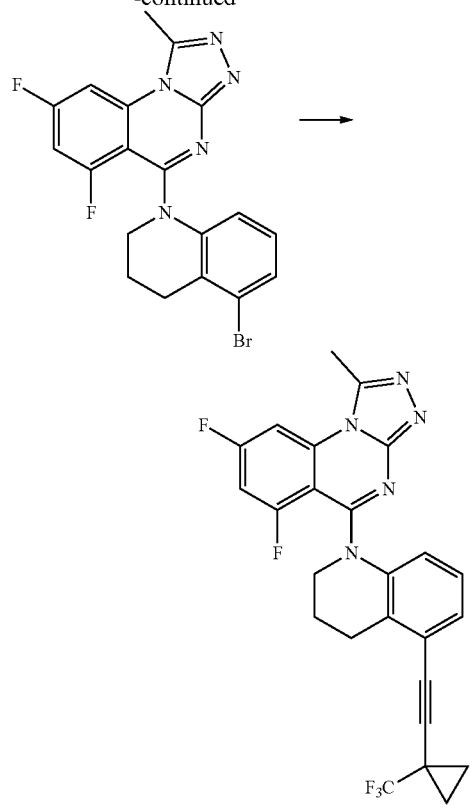

Synthesis of 5-(5-bromo-3,4-dihydroquinolin-1(2H)-yl)-6,8-difluoro-1-methyl-[1,2,4]triazolo[4,3-a]quinazoline: A solution of (E)-N-(3-bromophenyl)-6,7-dichloro-2-hydrazono-N-methyl-1,2-dihydroquinazolin-4-amine (124 mg, 0.305 mmol) and triethyl orthoacetate (1.98 g, 12.2 mmol) was heated to 110° C. for 16 h. Upon completion, the reaction was cooled to room temperature, and concentrated under reduced pressure to afford the crude product. The crude product was triturated with heptane and the solids were collected by filtration, washed with hexanes:ether (4:1) and dried in vacuo to afford the desired product. MS (m/z) 430.3 [M+H]⁺.

Synthesis of 6,8-difluoro-1-methyl-5-(5-((1-(trifluoromethyl)cyclopropyl)ethynyl)-3,4-dihydroquinolin-1(2H)-yl)-[1,2,4]triazolo[4,3-a]quinazoline: a solution of 5-(5-bromo-3,4-dihydroquinolin-1(2H)-yl)-6,8-difluoro-1-methyl-[1,2,4]triazolo[4,3-a]quinazoline (20.9 mg, 0.0486 mmol), zinc bromide (54.7 mg, 0.243 mmol), (1,1'-)bis(diphenylphosphino)ferrocene) palladium (II) dichloride (1.79 mg, 0.00243 mmol), and triethylamine (98.3 mg, 0.972 mmol) in DMF (0.6 mL) was purged with nitrogen gas for 5 minutes. 1-ethynyl-1-(trifluoromethyl)cyclopropane (16.3 mg, 0.121 mol) was then added and the mixture was heated at 100° C. for 30 minutes. Upon completion, the mixture was cooled to room temperature, and ethyl acetate and sat. NH₄Cl (aq) were added to the mixture. The aqueous layer was extracted with EA and the combined organic layers were dried over Na₂SO₄ and concentrated in vacuo. The residue was purified by reverse phase HPLC (0.1% trifluoroacetic acid in acetonitrile/water) providing the title compound as the mono-TFA salt: 1H NMR (400 MHz, DMSO-d₆) δ 7.95 (d, J=10.7 Hz, 1H), 7.55-7.48 (m, 1H), 7.14 (d, J=7.5 Hz, 1H), 6.95 (t, J=7.9 Hz, 1H), 6.86 (d, J=8.2 Hz, 1H), 4.09 (m, 2H), 2.99

(s, 3H), 2.88-2.77 (m, 2H), 2.15-1.96 (m, 2H), 1.52-1.38 (m, 4H); MS (m/z) 484.1 [M+H]+.

Example 796. N-(2,2-difluoroethyl)-N-(3-((1-ethyl-cyclopropyl)ethynyl)-5-fluorophenyl)-6,7-difluoro-1-methyl-[1,2,4]triazolo[4,3-a]quinazolin-5-amine

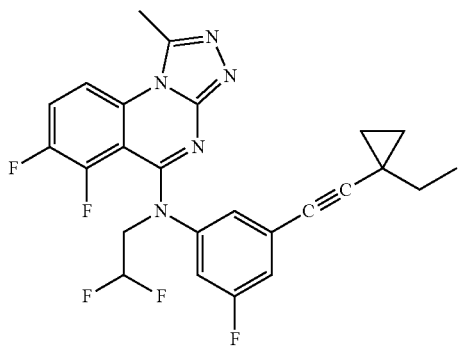 [SMILES: CCC1(C#Cc2cc(F)cc(N(CC(F)F)c3nc4nnc(C)n4c4ccc(F)c(F)c34)c2)CC1]

The title compound was synthesized in an analogous manner according to the procedures described for Example 690. 1H NMR (400 MHz, DMSO-d6) δ 8.17 (dd, J=9.5, 3.6 Hz, 1H), 8.11-8.03 (m, 1H), 7.11-7.03 (m, 2H), 6.97 (d, J=10.9 Hz, 1H), 6.52 (tt, J=56.0, 3.7 Hz, 1H), 4.68-4.57 (m, 2H), 3.00 (s, 3H), 1.40 (q, J=7.3 Hz, 2H), 1.02 (t, J=7.3 Hz, 3H), 0.91-0.87 (m, 2H), 0.74-0.69 (m, 2H); LCMS(m/z) 486.2.

Example 797. 4-(1-(6-fluoro-1-methyl-[1,2,4]triazolo[4,3-a]quinazolin-5-yl)-1,2,3,4-tetrahydroquinolin-5-yl)-2,2-dimethylbut-3-ynenitrile

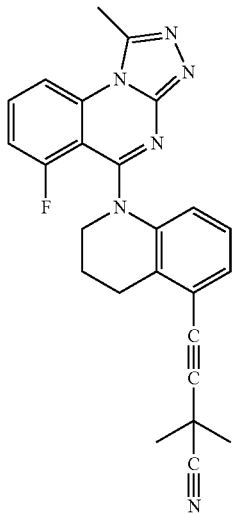 [SMILES: Cc1nnc2nc(N3CCCc4c(C#CC(C)(C)C#N)cccc43)c3c(F)cccc3n12]

The title compound was synthesized in an analogous manner according to the procedures described for Example 719. 1H NMR (400 MHz, DMSO-d6) δ 8.18 (d, J=8.6 Hz, 1H), 8.01 (td, J=8.4, 5.5 Hz, 1H), 7.37 (dd, J=11.6, 8.4 Hz, 1H), 7.19 (d, J=7.5 Hz, 1H), 6.97 (t, J=7.9 Hz, 1H), 6.89 (d, J=8.2 Hz, 1H), 3.90 (m, 2H), 3.00 (s, 3H), 2.98-2.82 (m, 2H), 2.18-2.01 (m, 2H), 1.77 (s, 6H); LCMS(m/z) 425.2.

Example 798. 6,8-difluoro-5-(5-((1-(trifluoromethyl)cyclopropyl)ethynyl)-3,4-dihydroquinolin-1(2H)-yl)-[1,2,4]triazolo[4,3-a]quinazoline

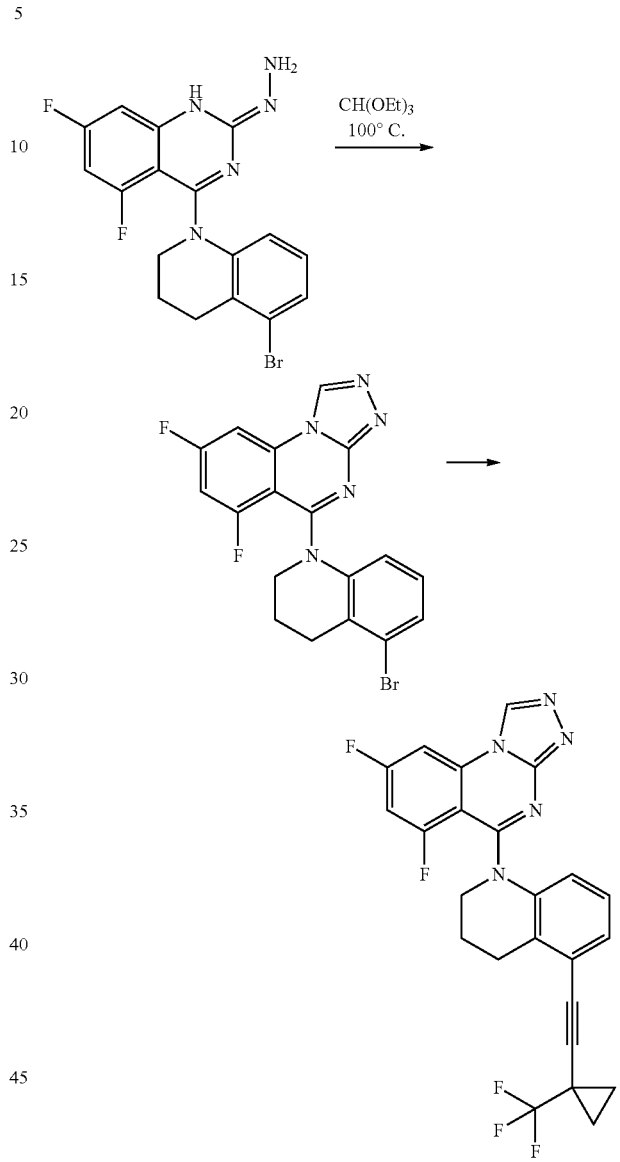

(E)-4-(5-Bromo-3,4-dihydroquinolin-1(2H)-yl)-5,7-difluoro-2-hydrazono-1,2-dihydroquinazoline was prepared as described in Example 795.

Synthesis of 5-(5-bromo-3,4-dihydroquinolin-1(2H)-yl)-6,8-difluoro-[1,2,4]triazolo[4,3-a]quinazoline: A solution of (E)-4-(5-bromo-3,4-dihydroquinolin-1(2H)-yl)-5,7-difluoro-2-hydrazineylidene-1,2-dihydroquinazoline (75.8 mg, 0.197 mmol) and triethyl orthoformate (1.1 g, 7.46 mmol) was heated to 110° C. for 16 h. Upon completion, the reaction was cooled to room temperature, and concentrated under reduced pressure to afford the crude product. The crude product was triturated with heptane and the solids were collected by filtration, washed with hexanes:diethyl ether (4:1) and dried in vacuo to afford. MS (m/z) 416.3 [M+H]+.

Synthesis of 6,8-difluoro-5-(5-((1-(trifluoromethyl)cyclopropyl)ethynyl)-3,4-dihydroquinolin-1(2H)-yl)-[1,2,4]triazolo[4,3-a]quinazoline: a solution of 5-(5-bromo-3,4-dihydroquinolin-1(2H)-yl)-6,8-difluoro-[1,2,4]triazolo[4,3-a]quinazoline (21.6 mg, 0.0519 mmol), zinc bromide (58.4 mg, 0.259 mmol), (1,1'-)bis(diphenylphosphino)ferrocene) palladium (II) dichloride (3.83 mg, 0.00519 mmol), and triethylamine (105 mg, 1.04 mmol) in DMF (0.60 mL) was purged with nitrogen gas for 5 minutes. 1-ethynyl-1-(trifluoromethyl)cyclopropane (23.4 mg, 0.156 mol) was then added and the mixture was heated at 100° C. for 30 minutes. Upon completion, the mixture was cooled to room temperature, and ethyl acetate and sat. NH$_4$Cl (aq) were added to the mixture. The aqueous layer was extracted with EA and the combined organic layers were dried over Na$_2$SO$_4$ and concentrated in vacuo. The residue was purified by reverse phase HPLC (0.1% trifluoroacetic acid in acetonitrile/water) providing the title compound as the mono-TFA salt. 1H NMR (400 MHz, DMSO-d$_6$) δ 9.69 (s, 1H), 8.29 (d, J=10.0 Hz, 1H), 7.48-7.40 (m, 1H), 7.12 (dd, J=7.3, 1.2 Hz, 1H), 6.92 (dd, J=14.2, 8.3 Hz, 2H), 3.90 (m, 2H), 2.98-2.82 (m, 2H), 2.13-1.97 (m, 2H), 1.51-1.39 (m, 4H); LCMS(m/z) 470.1.

Example 799. 5-(5-((1-ethylcyclopropyl)ethynyl)-3,4-dihydroquinolin-1(2H)-yl)-6-fluoro-1-methyl-[1,2,4]triazolo[4,3-a]quinazoline

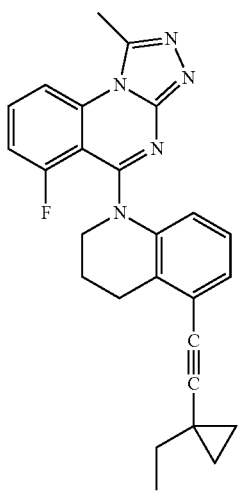 [SMILES: CCC1(C#Cc2cccc3c2CCCN3c2nc3nnc(C)n3c3cccc(F)c23)CC1]

The title compound was synthesized in an analogous manner according to the procedures described for Example 719. 1H NMR (400 MHz, DMSO-d$_6$) δ 8.17 (d, J=8.6 Hz, 1H), 8.01 (dt, J=8.5, 4.3 Hz, 1H), 7.37 (dd, J=11.8, 8.3 Hz, 1H), 7.09 (d, J=7.5 Hz, 1H), 6.90 (t, J=7.9 Hz, 1H), 6.77 (d, J=7.9 Hz, 1H), 3.00 (s, 3H), 1.47 (q, J=7.3 Hz, 2H), 1.11 (t, J=7.3 Hz, 3H), 0.98-0.93 (m, 2H), 0.80-0.75 (m, 2H); LCMS(m/z) 426.2.

Example 800. 6-fluoro-5-(5-((1-(fluoromethyl)cyclopropyl)ethynyl)-3,4-dihydroquinolin-1(2H)-yl)-1-methyl-[1,2,4]triazolo[4,3-a]quinazoline

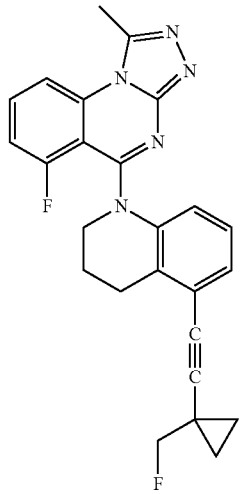 [SMILES: Cc1nnc2nc(N3CCCc4c(C#CC5(CF)CC5)cccc43)c3c(F)cccc3n12]

The title compound was synthesized in an analogous manner according to the procedures described for Example 719. 1H NMR (400 MHz, DMSO-d$_6$) δ 8.18 (d, J=8.6 Hz, 1H), 8.04-7.95 (m, 1H), 7.36 (t, J=11.9 Hz, 1H), 7.12 (d, J=7.3 Hz, 1H), 6.91 (d, J=7.7 Hz, 1H), 6.81 (d, J=7.8 Hz, 1H), 4.41 (d, J=48.5 Hz, 2H), 3.00 (s, 3H), 1.17-1.05 (m, 4H); LCMS(m/z) 430.2.

Example 801. N-(2,2-difluoroethyl)-6,7-difluoro-N-(3-fluoro-5-(4,4,4-trifluoro-3,3-dimethylbut-1-yn-1-yl)phenyl)-1-methyl-[1,2,4]triazolo[4,3-a]quinazolin-5-amine

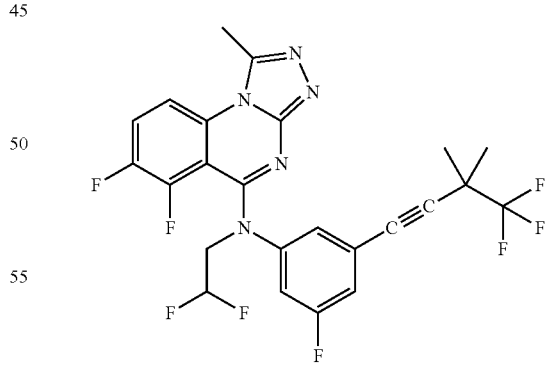

The title compound was synthesized in an analogous manner according to the procedures described for Example 690. 1H NMR (400 MHz, DMSO-d$_6$) δ 8.20-8.16 (m, 1H), 8.08 (q, J=9.5 Hz, 1H), 7.23 (s, 1H), 7.14 (dt, J=10.7, 2.2 Hz, 1H), 7.08-7.03 (m, 1H), 6.53 (tt, J=55.7, 3.8 Hz, 1H), 4.64 (td, J=15.3, 14.9, 3.5 Hz, 2H), 3.00 (s, 3H), 1.48 (s, 6H); LCMS(m/z) 528.1.

1091

Example 802. N-(2,2-difluoroethyl)-6,7-difluoro-N-(3-fluoro-5-((1-(fluoromethyl)cyclopropyl)ethynyl)phenyl)-1-methyl-[1,2,4]triazolo[4,3-a]quinazolin-5-amine

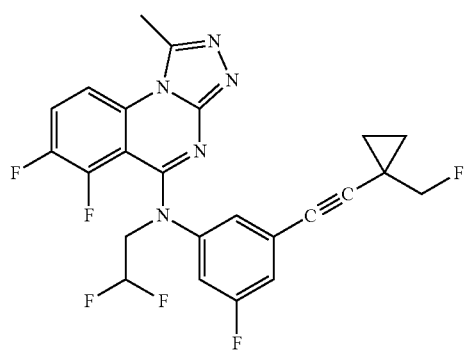 [SMILES: Cc1nnc2nc(N(CC(F)F)c3cc(F)cc(C#CC4(CF)CC4)c3)c3c(F)c(F)ccc3n12]

The title compound was synthesized in an analogous manner according to the procedures described for Example 690. 1H NMR (400 MHz, DMSO-d$_6$) δ 8.17 (dd, J=9.2, 3.7 Hz, 1H), 8.08 (q, J=9.0 Hz, 1H), 7.11 (d, J=14.6 Hz, 2H), 6.52 (tt, J=56.1, 4.2 Hz, 1H), 4.62 (t, J=15.3 Hz, 2H), 4.33 (d, J=48.5 Hz, 2H), 3.00 (s, 3H), 1.13-0.99 (m, 4H); LCMS (m/z) 490.1.

Example 803. 4-(3-(cyclopropyl(7-fluoro-[1,2,4]triazolo[4,3-a]quinazolin-5-yl)amino)-5-fluorophenyl)-2-methylbut-3-yn-2-ol

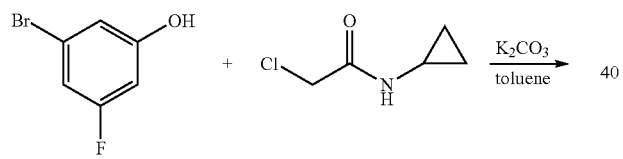

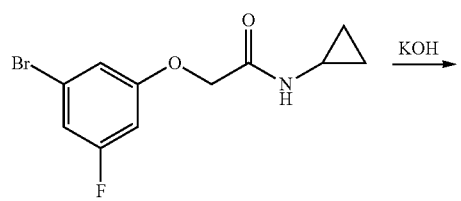

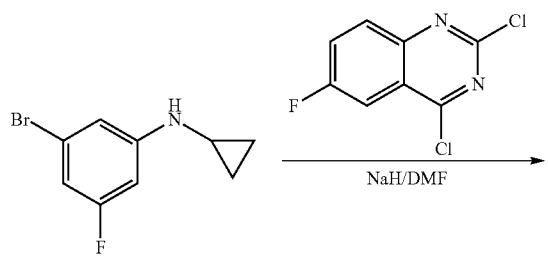

1092

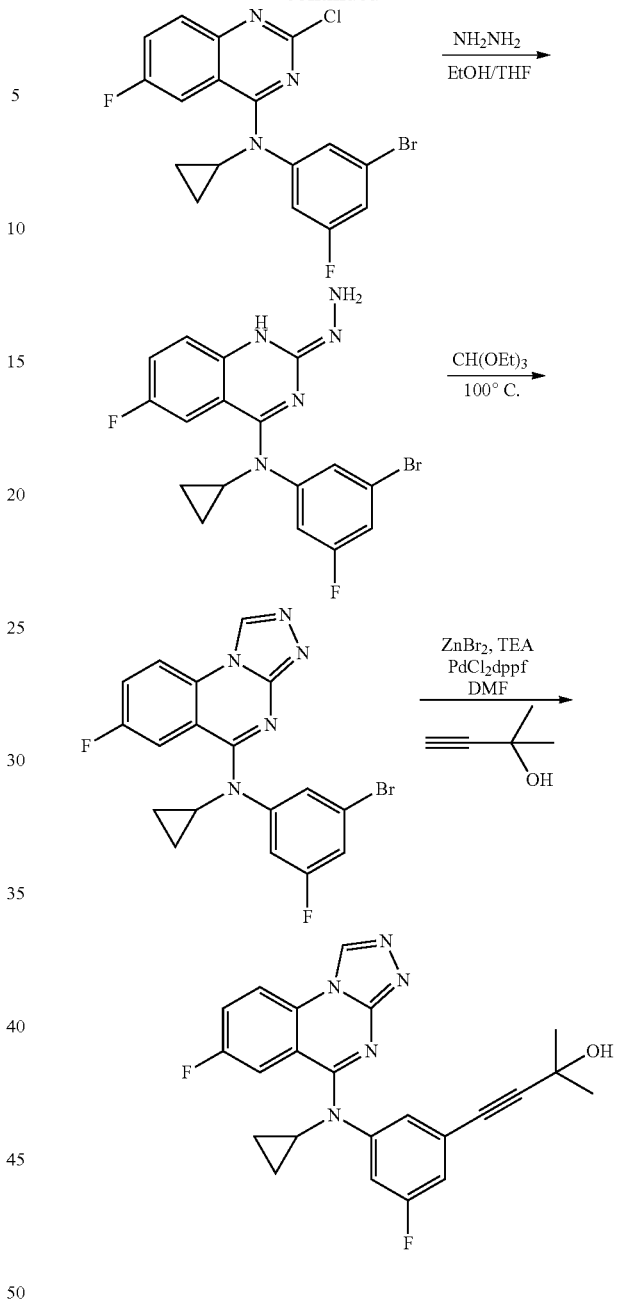

Synthesis of 2-(3-bromo-5-fluorophenoxy)-N-cyclopropylacetamide: To a stirred solution of K$_2$CO$_3$ (2.59 g, 18.7 moles) in toluene (7.0 mL) at room temperature was added 3-bromo-4-fluorophenol (3.58 g, 18.7 moles) and 2-chloro-N-cyclopropylacetamide (1.00 g, 7.49 mmol) and the mixture was heated at 105° C. for 18 h. Upon completion, the solvent was removed under reduced pressure and the mixture was dissolved in DCM, filtered and concentrated under reduced pressure to afford the crude product which was used without further purification. MS (m/z) 288.3 [M+H]$^+$.

Synthesis of 3-bromo-N-cyclopropyl-5-fluoroaniline: To a solution of KOH (841 mg, 15.0 mmol) in NMP (9.30 mL) and toluene (37.0 mL) was added 2-(3-bromo-5-fluorophenoxy)-N-cyclopropylacetamide (2.16 g, 7.50 mmol) and the mixture was heated at 120° C. for 16 hr. The solvent was removed under reduced pressure and the crude product was purified using flash chromatography eluting with EA in hexanes 0-50% to afford the final product. MS (m/z) 230.4 [M+H]⁺.

Synthesis of N-(3-bromo-5-fluorophenyl)-2-chloro-N-cyclopropyl-6-fluoroquinazolin-4-amine: To a solution of 3-bromo-N-cyclopropyl-5-fluoroaniline (318 mg, 1.38 mmol) in DMF (2.0 mL) at 0° C. was added NaH (60% dispersion in mineral oil) (68.9 mg, 1.80 mmol) in one portion. The mixture was stirred at 0° C. for 30 minutes, followed by the addition of 2,4-dichloro-6-fluoro-quinazoline (300 mg, 1.38 mmol). The cold bath was removed, and the mixture was stirred at room temperature for 2 h. Upon completion, the reaction was cooled to 0° C. and quenched with a few drops of a solution of sat. NH₄Cl(aq) and stirred until solid crashed out. The solid was filtered off and washed with a mixture of hexanes:diethyl ether 4:1 and dried in vacuo and was used with no further purification. MS (m/z) 410.4 [M+H]⁺.

Synthesis of (E)-N-(3-bromo-5-fluorophenyl)-N-cyclopropyl-6-fluoro-2-hydrazono-1,2-dihydroquinazolin-4-amine: To a solution of N-(3-bromo-5-fluorophenyl)-2-chloro-N-cyclopropyl-6-fluoroquinazolin-4-amine (427 mg, 1.04 mmol) in THF (10.0 mL) and ethanol (5.00 mL) was added hydrazine monohydrate (833 mg, 26.0 mmol) and the mixture was stirred at room temperature for 12 h. Upon completion, the reaction was diluted with EA and washed with water, dried over Na₂SO₄ and concentrated under reduced pressure to afford the product. MS (m/z) 406.5 [M+H]⁺.

Synthesis of N-(3-bromo-5-fluorophenyl)-N-cyclopropyl-7-fluoro-[1,2,4]triazolo[4,3-a]quinazolin-5-amine: A solution of (E)-N-(3-bromo-5-fluorophenyl)-N-cyclopropyl-6-fluoro-2-hydrazono-1,2-dihydroquinazolin-4-amine (232 mg, 0.571 mmol) and triethyl orthoformate (3.39 g, 22.8 mmol) was heated to 110° C. for 16 h. Upon completion, the reaction was cooled to room temperature, and concentrated under reduced pressure to afford the crude product. The crude product was triturated with heptane and the solids were collected by filtration, washed with hexanes: diethyl ether (4:1) and dried in vacuo to afford desired product. MS (m/z) 416.3 [M+H]⁺.

Synthesis of 4-(3-(cyclopropyl(7-fluoro-[1,2,4]triazolo[4, 3-a]quinazolin-5-yl)amino)-5-fluorophenyl)-2-methylbut-3-yn-2-ol: A solution of N-(3-bromo-5-fluorophenyl)-N-cyclopropyl-7-fluoro-[1,2,4]triazolo[4,3-a]quinazolin-5-amine (24.5 mg, 0.0589 mmol), zinc bromide (66.3 mg, 0.294 mmol), (1,1'-)bis(diphenylphosphino)ferrocene) palladium (II) dichloride (2.17 mg, 0.00294 mmol), and triethylamine (119 mg, 1.18 mmol) in DMF (0.60 mL) was purged with nitrogen gas for 5 minutes. 2-Methylbut-3-yn-2-ol (14.9 mg, 0.177 mol) was then added and the mixture was heated at 100° C. for 30 minutes. Upon completion, the mixture was cooled to room temperature, and ethyl acetate and sat. NH₄Cl (aq) were added to the mixture. The organic layer was dried over Na₂SO₄ and concentrated in vacuo. The residue was purified by reverse phase HPLC (0.1% trifluoroacetic acid in acetonitrile/water) providing the title compound as the mono-TFA salt. 1H NMR (400 MHz, DMSO-d₆) δ 9.87 (s, 1H), 8.53 (dd, J=9.2, 4.7 Hz, 1H), 7.97 (td, J=8.6, 2.6 Hz, 1H), 7.55 (dd, J=9.7, 2.6 Hz, 1H), 7.28 (d, J=12.4 Hz, 1H), 7.22 (s, 1H), 7.10-7.04 (m, 1H), 3.25 (m, 1H), 1.43 (s, 6H), 1.01 (q, J=6.7 Hz, 2H), 0.86 (q, J=8.4, 6.4 Hz, 2H); MS (m/z) 420.1 [M+H]⁺.

Example 804. 4-(3-(cyclopropyl(7-fluoro-[1,2,4] triazolo[4,3-a]quinazolin-5-yl)amino)-5-fluorophenyl)-2-methylbut-3-yn-2-ol

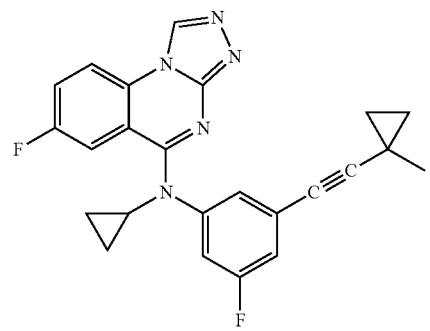 [SMILES: CC1(C#Cc2cc(F)cc(N(c3nc4nncn4c4ccc(F)cc34)C3CC3)c2)CC1]

The title compound was synthesized in an analogous fashion as the preparation for Example 803. 1H NMR (400 MHz, DMSO-d₆) δ 9.88 (s, 1H), 8.56-8.50 (m, 1H), 7.97 (t, J=9.9 Hz, 1H), 7.52 (dd, J=9.7, 2.3 Hz, 1H), 7.27 (d, J=10.7 Hz, 1H), 7.18 (s, 1H), 7.09-7.03 (m, 1H), 3.23 (m, 1H), 1.27 (s, 3H), 1.00 (q, J=6.4, 5.8 Hz, 2H), 0.92 (d, J=2.5 Hz, 2H), 0.87 (m, 2H), 0.73 (q, J=4.0 Hz, 2H); LCMS(m/z) 416.1.

Example 805. N-(2,2-difluoroethyl)-6,7-difluoro-N-(3-fluoro-5-((1-methylcyclopropyl)ethynyl)phenyl)-1-methyl-[1,2,4]triazolo[4,3-a]quinazolin-5-amine

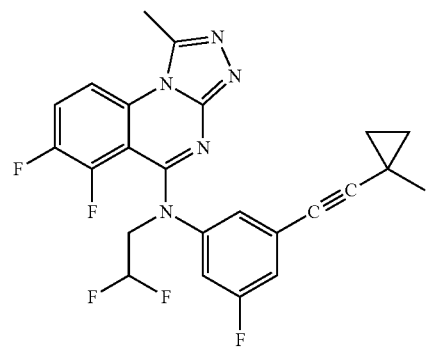 [SMILES: Cc1nnc2nc(N(CC(F)F)c3cc(F)cc(C#CC4(C)CC4)c3)c3c(F)c(F)ccc3n12]

The title compound was synthesized in an analogous fashion as the preparation for Example 690. 1H NMR (400 MHz, DMSO-d₆) δ 8.17 (dd, J=9.6, 3.5 Hz, 1H), 8.08 (q, J=9.3 Hz, 1H), 7.08 (m, 2H), 7.00-6.93 (m, 1H), 6.52 (tt, J=55.9, 3.7 Hz, 1H), 4.67-4.56 (m, 2H), 3.00 (s, 3H), 1.27 (s, 3H), 0.92 (q, J=4.0 Hz, 2H), 0.73 (q, J=4.1 Hz, 2H); LCMS(m/z) 472.1.

Example 806. 4-(3-((6,7-difluoro-1-methyl-[1,2,4]triazolo[4,3-a]quinazolin-5-yl)(2,2-difluoroethyl)amino)-5-fluorophenyl)-2-methylbut-3-yn-2-ol

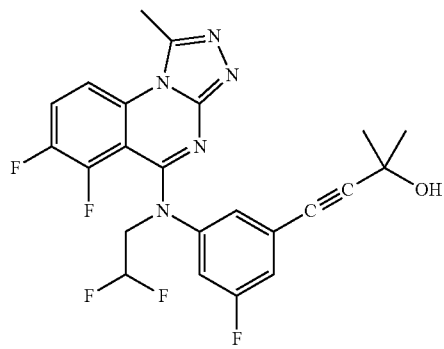

The title compound was synthesized in an analogous fashion as the preparation for Example 690. 1H NMR (400 MHz, DMSO-$d_6$) δ 8.18 (dd, J=9.3, 3.8 Hz, 1H), 8.08 (q, J=9.2 Hz, 1H), 7.12 (m, 2H), 6.99 (d, J=8.8 Hz, 1H), 6.53 (tt, J=56.0, 3.8 Hz, 1H), 4.64 (t, J=15.3 Hz, 2H), 3.00 (s, 3H), 1.43 (s, 6H); LCMS(m/z) 476.1.

Example 807. N-(2,2-difluoroethyl)-6,7-difluoro-N-(3-fluoro-5-((1-(trifluoromethyl)cyclopropyl)ethynyl)phenyl)-1-methyl-[1,2,4]triazolo[4,3-a]quinazolin-5-amine

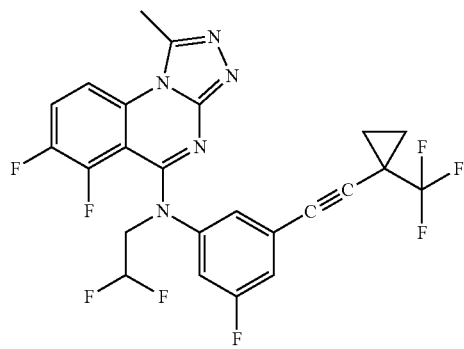 [SMILES: Cc1nnc2nc(N(CC(F)F)c3cc(F)cc(C#CC4(C(F)(F)F)CC4)c3)c3c(F)c(F)ccc3n12]

The title compound was synthesized in an analogous fashion as the preparation for Example 690. 1H NMR (400 MHz, DMSO-$d_6$) δ 8.18 (dd, J=9.4, 3.6 Hz, 1H), 8.11 (d, J=9.2 Hz, 1H), 7.23 (s, 1H), 7.17 (d, J=10.7 Hz, 1H), 7.12-7.08 (m, 1H), 6.53 (tt, J=55.9, 3.6 Hz, 1H), 4.69-4.59 (m, 2H), 3.01 (s, 3H), 1.46-1.34 (m, 4H); LCMS(m/z) 526.1.

Example 808. 5-(5-((1-ethylcyclopropyl)ethynyl)-3,4-dihydroquinolin-1(2H)-y)-7-fluoro-1-methyl-[1,2,4]triazolo[4,3-a]quinazoline

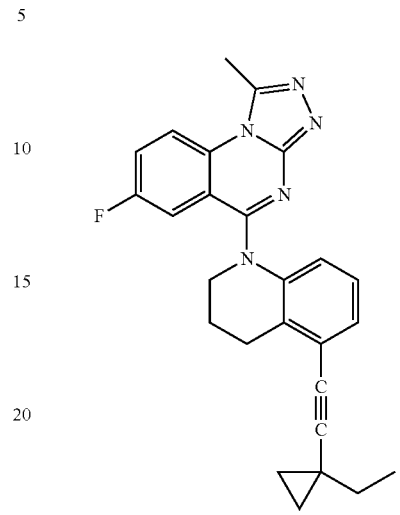

The title compound was synthesized in an analogous fashion as the preparation for Example 719. 1H NMR (400 MHz, DMSO-$d_6$) δ 8.40 (dd, J=9.4, 4.5 Hz, 1H), 7.89 (ddd, J=10.1, 7.9, 2.9 Hz, 1H), 7.41 (dd, J=9.6, 2.7 Hz, 1H), 7.16 (d, J=7.5 Hz, 1H), 6.96 (d, J=7.8 Hz, 1H), 6.79 (d, J=8.1 Hz, 1H), 4.00 (t, J=6.1 Hz, 2H), 3.02 (s, 3H), 2.98 (t, J=6.7 Hz, 2H), 2.11 (p, J=6.0 Hz, 2H), 1.48 (q, J=7.3 Hz, 2H), 1.13 (t, J=7.3 Hz, 3H), 0.97 (q, J=4.0 Hz, 2H), 0.80 (q, J=4.1 Hz, 2H); LCMS(m/z) 426.2.

Example 809. 5-(5-(3-cyclopropyl-3-methylbut-1-yn-1-yl)-3,4-dihydroquinolin-1(2H)-yl)-6,7-difluoro-1-methyl-[1,2,4]triazolo[4,3-a]quinazoline

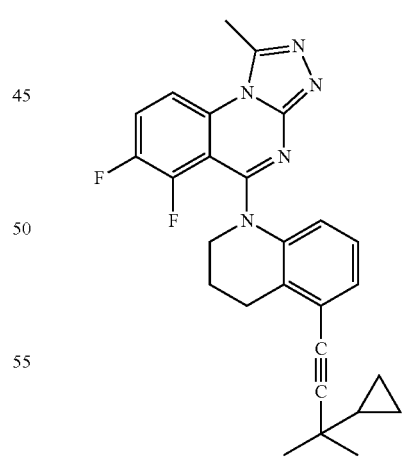

The title compound was synthesized in an analogous fashion as the preparation for Example 719. 1H NMR (400 MHz, DMSO-$d_6$) δ 8.19-8.14 (m, 1H), 8.12-8.03 (m, 1H), 7.04 (d, J=7.5 Hz, 1H), 6.90 (d, J=7.8 Hz, 1H), 6.78 (d, J=8.4 Hz, 1H), 4.08-3.90 (m, 2H), 2.98 (s, 3H), 2.89-2.80 (m, 2H), 2.19-1.93 (m, 2H), 1.37 (s, 6H), 0.96-0.90 (m, 1H), 0.44 (d, J=5.1 Hz, 4H); LCMS(m/z) 458.2.

Example 810. 5-(5-((1-ethylcyclopropyl)ethynyl)-3,4-dihydroquinolin-1(2H)-yl)-6,7-difluoro-1-methyl-[1,2,4]triazolo[4,3-a]quinazoline

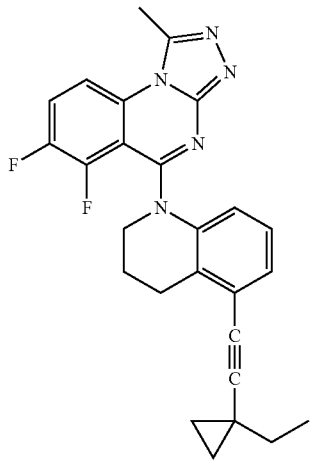 [SMILES: CCC1(C#Cc2cccc3c2CCCN3c2nc3nnc(C)n3c3ccc(F)c(F)c23)CC1]

The title compound was synthesized in an analogous fashion as the preparation for Example 719. 1H NMR (400 MHz, DMSO-d$_6$) δ 8.18-8.07 (m, 2H), 7.08 (d, J=7.7 Hz, 1H), 6.92 (t, J=7.8 Hz, 1H), 6.79 (d, J=8.0 Hz, 1H), 4.27-3.82 (m, 2H), 2.99 (s, 3H), 2.90-2.71 (m, 2H), 2.16-1.89 (m, 2H), 1.51-1.44 (m, 2H), 1.12 (t, J=7.3 Hz, 3H), 0.96 (q, J=4.1 Hz, 2H), 0.78 (q, J=4.1 Hz, 2H); LCMS(m/z) 444.2.

Example 811. 8-chloro-N-(3-(3-cyclopropyl-3-methylbut-1-yn-1-yl)-5-fluorophenyl)-N-(2,2-difluoroethyl)-[1,2,4]triazolo[4,3-a]quinazolin-5-amine

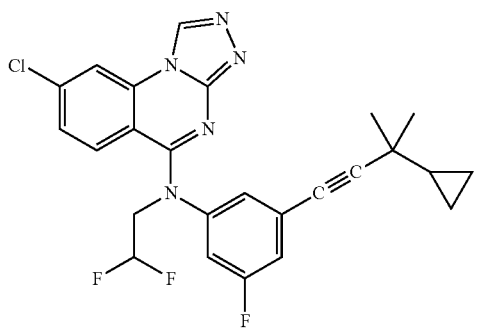 [SMILES: CC(C)(C#Cc1cc(F)cc(N(CC(F)F)c2nc3nncn3c3cc(Cl)ccc23)c1)C1CC1]

The title compound was synthesized in an analogous fashion as the preparation for Example 421. 1H NMR (400 MHz, DMSO-d$_6$) δ 9.77 (s, 1H), 8.65 (s, 1H), 7.48 (d, J=9.0 Hz, 1H), 7.34-7.29 (m, 1H), 7.24 (m, 2H), 7.08 (d, J=7.5 Hz, 1H), 6.70-6.38 (m, 1H), 4.62-4.50 (m, 2H), 1.27 (s, 6H), 0.90 (s, 1H), 0.37 (m, 4H); LCMS(m/z) 484.1.

Example 812. 5-(5-((1-ethylcyclopropyl)ethynyl)-3,4-dihydroquinolin-1(2H)-yl)-6-fluoro-[1,2,4]triazolo[4,3-a]quinazoline

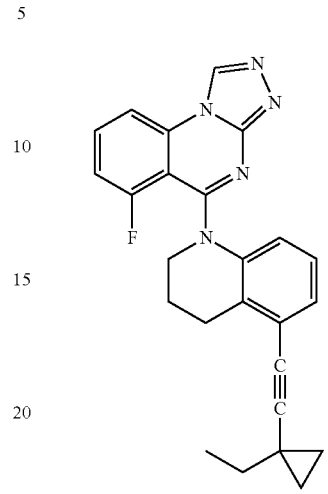

The title compound was synthesized in an analogous fashion as the preparation for Example 719. 1H NMR (400 MHz, DMSO-d$_6$) δ 9.77 (s, 1H), 8.23 (d, J=8.3 Hz, 1H), 8.04-7.97 (m, 1H), 7.30 (dd, J=11.8, 8.3 Hz, 1H), 7.05 (d, J=7.3 Hz, 1H), 6.88 (t, J=7.9 Hz, 1H), 6.79 (d, J=8.1 Hz, 1H), 3.78 (m, 2H), 3.04-2.76 (m, 2H), 2.15-1.91 (m, 2H), 1.47 (q, J=7.3 Hz, 2H), 1.12 (t, J=7.3 Hz, 3H), 0.96 (q, J=4.0 Hz, 2H), 0.80-0.75 (m, 2H); LCMS(m/z) 412.2.

Example 813. 5-(5-((1-fluoromethylcyclopropyl)ethynyl)-3,4-dihydroquinolin-1(2H)-yl)-6-fluoro-[1,2,4]triazolo[4,3-a]quinazoline The title compound was synthesized in an analogous fashion as the preparation for Example 719. 1H NMR (400 MHz, DMSO-d$_6$) δ 9.80 (s, 1H), 8.24 (d, J=8.4 Hz, 1H), 8.05-7.97 (m, 1H), 7.31 (dd, J=11.9, 8.3 Hz, 1H), 7.09 (d, J=7.4 Hz, 1H), 6.91 (t, J=7.9 Hz, 1H), 6.84 (d, J=8.0 Hz, 1H), 4.47 (s, 1H), 4.35 (s, 1H), 3.78 (m, 2H), 2.99-2.81 (m, 2H), 2.16-1.95 (m, 2H), 1.16-1.07 (m, 4H); LCMS(m/z) 416.1.

Example 814. N-(3-(3-cyclopropyl-3-methylbut-1-yn-1-yl)-5-fluorophenyl)-N-(2,2-difluoroethyl)-7-fluoro-[1,2,4]triazolo[4,3-a]quinazolin-5-amine

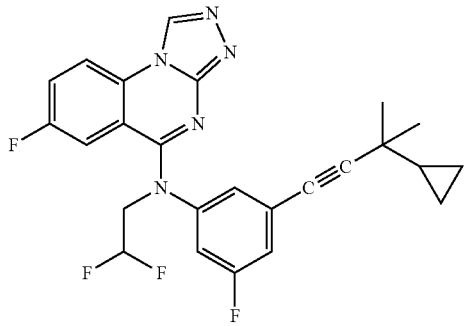 [SMILES: CC(C)(C#Cc1cc(F)cc(N(CC(F)F)c2nc3nncn3c3ccc(F)cc23)c1)C1CC1]

The title compound was synthesized in an analogous fashion as the preparation for Example 690. 1H NMR (400 MHz, DMSO-$d_6$) δ 9.82 (s, 1H), 8.50 (dd, J=9.2, 4.8 Hz, 1H), 7.92 (dd, J=17.2, 2.7 Hz, 1H), 7.32-7.25 (m, 2H), 7.13 (d, J=9.1 Hz, 1H), 6.95 (dd, J=9.9, 2.7 Hz, 1H), 6.72-6.40 (m, 1H), 4.63-4.47 (m, 2H), 1.28 (s, 6H), 0.92-0.85 (m, 1H), 0.43-0.31 (m, 4H); LCMS(m/z) 468.2.

Example 815. 4-(3-((2,2-difluoroethyl)(7-fluoro-[1,2,4]triazolo[4,3-a]quinazolin-5-yl)amino)-5-fluorophenyl)-2,2-dimethylbut-3-ynenitrile

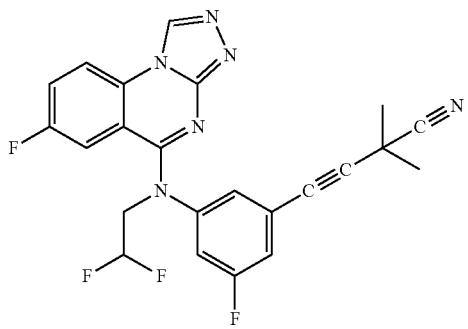 [SMILES: CC(C)(C#N)C#Cc1cc(F)cc(N(CC(F)F)c2nc3nncn3c3ccc(F)cc23)c1]

The title compound was synthesized in an analogous fashion as the preparation for Example 690. 1H NMR (400 MHz, DMSO-$d_6$) δ 9.85-9.75 (s, 1H), 8.53-8.46 (m, 1H), 7.91 (t, J=8.6 Hz, 1H), 7.40 (d, J=9.9 Hz, 2H), 7.29 (d, J=9.4 Hz, 1H), 6.97 (d, J=9.8 Hz, 1H), 6.57 (t, J=56.1 Hz, 1H), 4.58 (t, J=15.0 Hz, 2H), 1.69 (s, 6H); LCMS(m/z) 453.1.

Example 816. 4-(3-((2,2-difluoroethyl)(7-fluoro-[1,2,4]triazolo[4,3-a]quinazolin-5-yl)amino)-5-fluorophenyl)-2,2-dimethylbut-3-ynenitrile

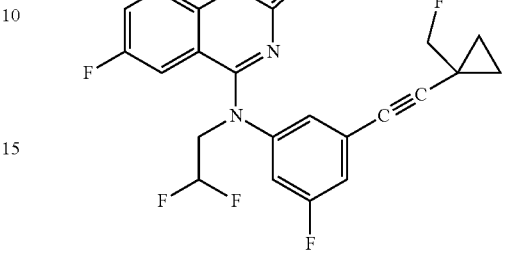

The title compound was synthesized in an analogous fashion as the preparation for Example 690. 1H NMR (400 MHz, DMSO-$d_6$) δ 9.82 (s, 1H), 8.50 (dd, J=9.2, 4.8 Hz, 1H), 7.92 (td, J=8.8, 2.7 Hz, 1H), 7.36-7.28 (m, 2H), 7.19 (d, J=8.9 Hz, 1H), 6.96 (dd, J=9.9, 2.7 Hz, 1H), 6.55 (tt, J=56.0, 3.9 Hz, 1H), 4.56 (td, J=14.4, 3.7 Hz, 2H), 4.40 (s, 1H), 4.27 (s, 1H), 1.12-1.01 (m, 4H); LCMS(m/z) 458.1.

Example 817. N-(3-((1-ethylcyclopropyl)ethynyl)-5-fluorophenyl)-7-fluoro-N-methyl-[1,2,4]triazolo[4,3-a]quinazolin-5-amine

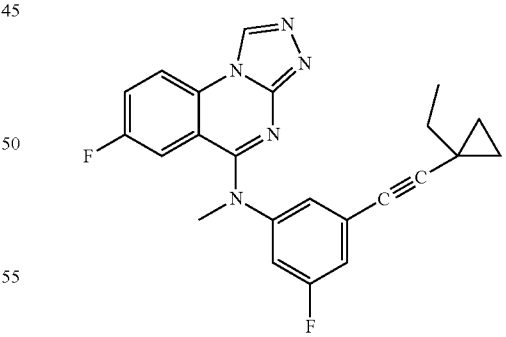

The title compound was synthesized in an analogous fashion as the preparation for Example 690. 1H NMR (400 MHz, DMSO-$d_6$) δ 9.85 (s, 1H), 8.51 (dd, J=9.2, 4.8 Hz, 1H), 7.99-7.90 (m, 1H), 7.38 (d, J=10.0 Hz, 1H), 7.29 (s, 1H), 7.23 (d, J=8.3 Hz, 1H), 6.97 (dd, J=10.1, 2.7 Hz, 1H), 3.59 (s, 3H), 1.40 (q, J=7.3 Hz, 2H), 1.03 (t, J=7.3 Hz, 3H), 0.90 (q, J=4.0 Hz, 2H), 0.75-0.71 (m, 2H); LCMS(m/z) 404.1.

Example 818. 8-chloro-N-(3-(3-cyclopropyl-3-methylbut-1-yn-1-yl)-5-fluorophenyl)-N-methyl-[1,2,4]triazolo[4,3-a]quinazolin-5-amine

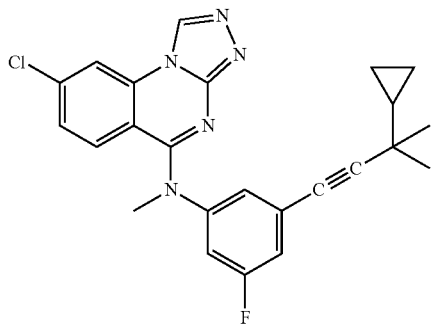 [SMILES: CN(c1cc(F)cc(C#CC(C)(C)C2CC2)c1)c1nc2nncn2c2cc(Cl)ccc12]

The title compound was synthesized in an analogous fashion as the preparation for Example 447. 1H NMR (400 MHz, DMSO-d$_6$) δ 9.76 (s, 1H), 8.64 (d, J=2.0 Hz, 1H), 7.51-7.46 (m, 1H), 7.37-7.27 (m, 2H), 7.23 (s, 1H), 7.12 (d, J=8.5 Hz, 1H), 3.57 (s, 3H), 1.27 (s, 6H), 0.88 (tt, J=7.8, 5.6 Hz, 1H), 0.39-0.33 (m, 4H); LCMS(m/z) 434.1.

Example 819. 8-chloro-N-(3-((1-(fluoromethyl)cyclopropyl)ethynyl)phenyl)-N-methyl-[1,2,4]triazolo[4,3-a]quinazolin-5-amine

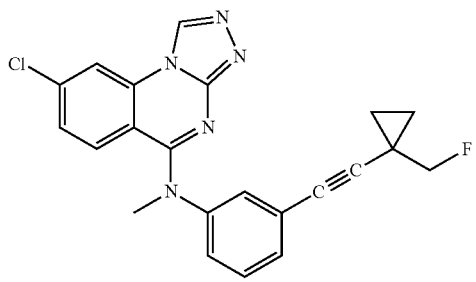 [SMILES: CN(c1cccc(C#CC2(CF)CC2)c1)c1nc2nncn2c2cc(Cl)ccc12]

The title compound was synthesized in an analogous fashion as the preparation for Example 447. 1H NMR (400 MHz, DMSO-d$_6$) δ 9.77 (s, 1H), 8.63 (d, J=2.0 Hz, 1H), 7.48-7.33 (m, 5H), 7.21 (d, J=9.0 Hz, 1H), 4.33 (d, J=48.5 Hz, 2H), 3.58 (s, 3H), 1.10-1.00 (m, 4H); LCMS(m/z) 406.1.

Example 820. 8-chloro-N-ethyl-N-(3-((1-ethylcyclopropyl)ethynyl)-5-fluorophenyl)-[1,2,4]triazolo[4,3-a]quinazolin-5-amine

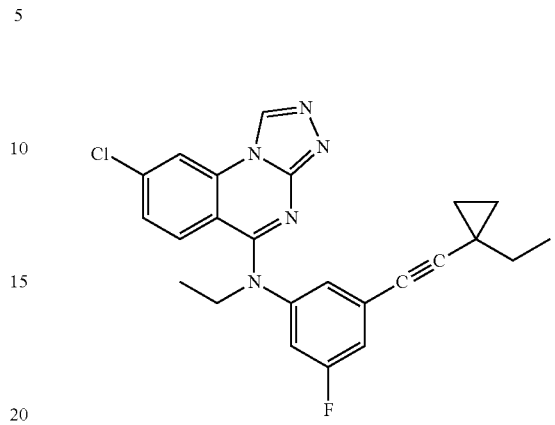

The title compound was synthesized in an analogous fashion as the preparation for Example 447. 1H NMR (400 MHz, DMSO-d$_6$) δ 9.79 (s, 1H), 8.64 (d, J=2.0 Hz, 1H), 7.49 (dd, J=9.0, 2.1 Hz, 1H), 7.34 (dt, J=10.1, 2.1 Hz, 1H), 7.29 (d, J=9.0 Hz, 1H), 7.24 (d, J=1.5 Hz, 1H), 7.22-7.17 (m, 1H), 4.16 (q, J=6.9 Hz, 2H), 1.40 (q, J=7.3 Hz, 2H), 1.23 (t, J=7.0 Hz, 3H), 1.02 (t, J=7.3 Hz, 3H), 0.91-0.86 (m, 2H), 0.75-0.70 (m, 2H); LCMS(m/z) 434.1.

Example 821. 8-chloro-N-(cyclopropylmethyl)-N-(3-((1-methylcyclopropyl)ethynyl)phenyl)-[1,2,4]triazolo[4,3-a]quinazolin-5-amine

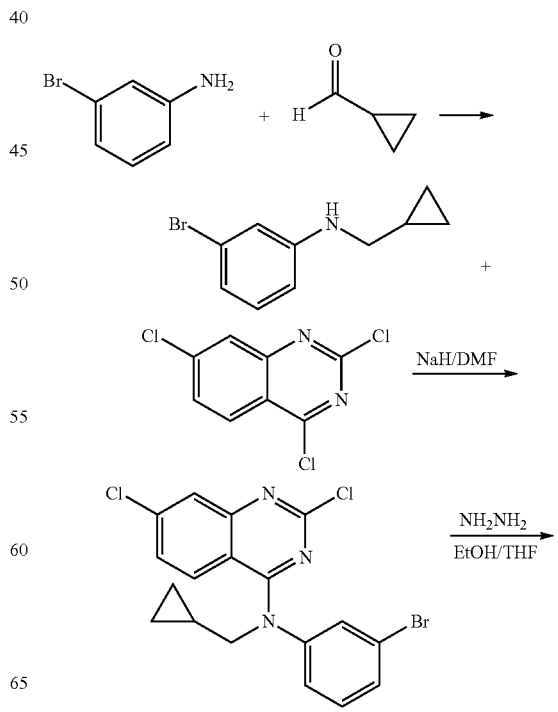

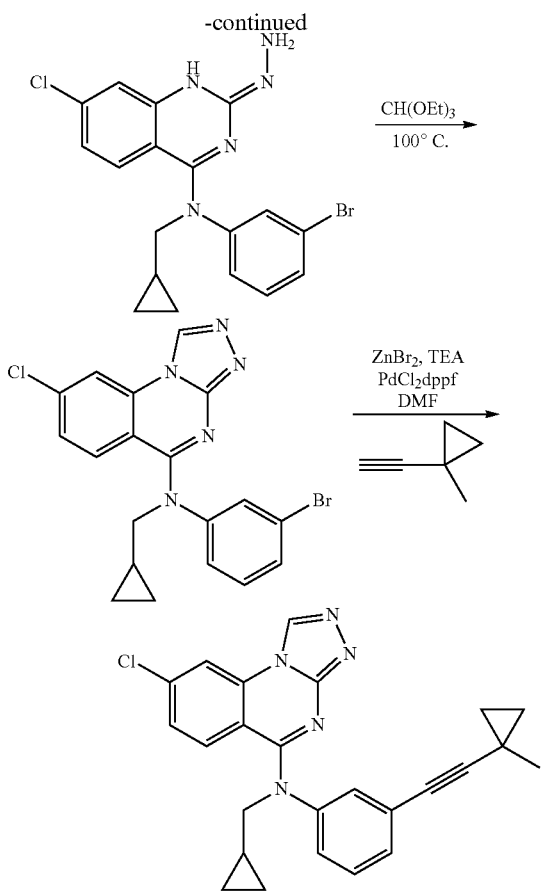

Synthesis of 3-bromo-N-(cyclopropylmethyl) aniline: To a solution of cyloropanealdehyde (204 mg, 2.91 mmol) and 3-bromoaniline (500 mg, 2.91 mmol) in DCM (4.20 mL) was added sodium triacetoxyborohydride (1.30 g, 6.13 mmol) at room temperature and the mixture was stirred for 48 h. Upon completion, the reaction was quenched with sat. sodium bicarbonate solution (bubbling observed), and the mixture was transferred to a separatory funnel and the aqueous phase was extracted with DCM. The combined organic layers were washed with brine, dried over Na$_2$SO$_4$, concentrated under reduced pressure. The crude product was purified using flash chromatography eluting with EA in hexanes 0-30% to afford the product. MS (m/z) 227.9 [M+H]$^+$.

Synthesis of N-(3-bromophenyl)-2,7-dichloro-N-(cyclopropylmethyl)quinazolin-4-amine: This intermediate was prepared in a similar fashion as described in Example 803 using 3-bromo-N-(cyclopropylmethyl)aniline and 2,4,7-trichloroquinazoline.

Synthesis of (E)-N-(3-bromophenyl)-7-chloro-N-(cyclopropylmethyl)-2-hydrazono-1,2-dihydroquinazolin-4-amine: This intermediate was prepared in a similar fashion as described in Example 803 using N-(3-bromophenyl)-2,7-dichloro-N-(cyclopropylmethyl)quinazolin-4-amine.

Synthesis of N-(3-bromophenyl)-8-chloro-N-(cyclopropylmethyl)-[1,2,4]triazolo[4,3-a]quinazolin-5-amine: This intermediate was prepared in a similar fashion as described in Example 803 using (E)-N-(3-bromophenyl)-7-chloro-N-(cyclopropylmethyl)-2-hydrazono-1,2-dihydroquinazolin-4-amine.

Synthesis of 8-chloro-N-(cyclopropylmethyl)-N-(3-((1-methylcyclopropyl)ethynyl)phenyl)-[1,2,4]triazolo[4,3-a]quinazolin-5-amine: The title compound was synthesized using the method as described in Example 803 using N-(3-bromophenyl)-8-chloro-N-(cyclopropylmethyl)-[1,2,4]triazolo[4,3-a]quinazolin-5-amine and 1-ethynyl-1-methylcyclopropane. 1H NMR (400 MHz, DMSO-d$_6$) δ 9.70 (s, 1H), 8.59 (d, J=1.9 Hz, 1H), 7.42-7.33 (m, 3H), 7.32-7.27 (m, 2H), 7.22 (d, J=9.0 Hz, 1H), 3.97 (d, J=6.8 Hz, 2H), 1.36-1.30 (m, 1H), 1.28 (s, 3H), 0.91 (q, J=3.9 Hz, 2H), 0.72 (q, J=4.1 Hz, 2H), 0.42-0.36 (m, 2H), 0.12 (m, 2H); MS (m/z) 428.1 [M+H]$^+$.

Example 822. 8-chloro-N-(3-((3,3-difluorocyclobutyl)ethynyl)phenyl)-7-fluoro-N-methyl-[1,2,4]triazolo[4,3-a]quinazolin-5-amine

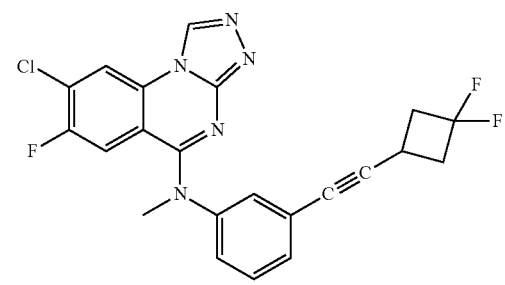 [SMILES: CN(c1cccc(C#CC2CC(F)(F)C2)c1)c1nc2nncn2c2cc(Cl)c(F)cc12]

The title compound was synthesized in an analogous fashion as the preparation for Example 447. 1H NMR (400 MHz, DMSO-d$_6$) δ 9.71 (s, 1H), 8.83 (d, J=6.2 Hz, 1H), 7.50 (s, 1H), 7.49-7.37 (m, 3H), 6.98 (d, J=11.1 Hz, 1H), 3.57 (s, 3H), 3.28-3.20 (m, 1H), 3.00 (q, J=9.1 Hz, 1H), 2.77-2.64 (m, 2H); LCMS(m/z) 442.2.

Example 823. 1-(5-(3-((8-chloro-7-fluoro-[1,2,4]triazolo[4,3-a]quinazolin-5-yl)(methyl)amino)phenyl)pyridin-2-yl)cyclopropane-1-carbonitrile

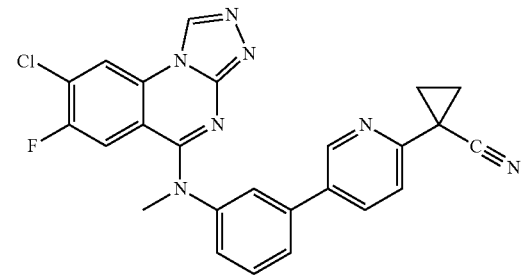 [SMILES: CN(c1cccc(-c2ccc(C3(C#N)CC3)nc2)c1)c1nc2nncn2c2cc(Cl)c(F)cc12]

The title compound was synthesized in an analogous fashion as the preparation for Example 527. 1H NMR (400 MHz, DMSO-d$_6$) δ 9.76 (s, 1H), 8.85 (d, J=6.6 Hz, 1H), 8.81 (dd, J=2.4, 0.9 Hz, 1H), 8.14 (dd, J=8.3, 2.4 Hz, 1H), 7.87-7.75 (m, 2H), 7.67-7.56 (m, 2H), 7.53-7.45 (m, 1H), 7.02 (d, J=10.8 Hz, 1H), 3.67 (s, 3H), 1.86-1.82 (m, 2H), 1.73-1.68 (m, 2H); LCMS(m/z) 470.1.

Example 824. 1-(5-(3-((8-chloro-[1,2,4]triazolo[4,3-a]quinazolin-5-yl)(methyl)amino)phenyl)pyridin-2-yl)cyclobutane-1-carbonitrile

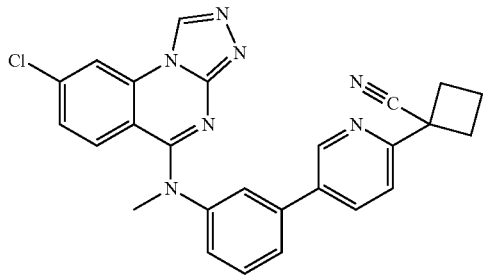 [SMILES: CN(c1cccc(-c2ccc(C3(C#N)CCC3)nc2)c1)c1nc2nncn2c2cc(Cl)ccc12]

The title compound was synthesized in an analogous fashion as the preparation for Example 527. 1H NMR (400 MHz, DMSO-$d_6$) δ 9.79 (s, 1H), 8.90 (d, J=2.1 Hz, 1H), 8.63 (s, 1H), 8.18-8.14 (m, 1H), 7.84 (s, 1H), 7.77 (d, J=8.0 Hz, 1H), 7.66 (d, J=8.2 Hz, 1H), 7.61 (t, J=7.9 Hz, 1H), 7.47 (d, J=7.8 Hz, 1H), 7.40 (d, J=10.7 Hz, 1H), 7.29 (d, J=9.0 Hz, 1H), 3.68 (s, 3H), 2.81-2.68 (m, 4H), 2.35-2.21 (m, 1H), 2.12-2.00 (m, 1H); LCMS(m/z) 466.1.

Example 825. 6-bromo-1-(6-fluoro-1-methyl-[1,2,4]triazolo[4,3-a]quinazolin-5-yl)-3,5-dihydro-2H-4,1-benzoxazepine

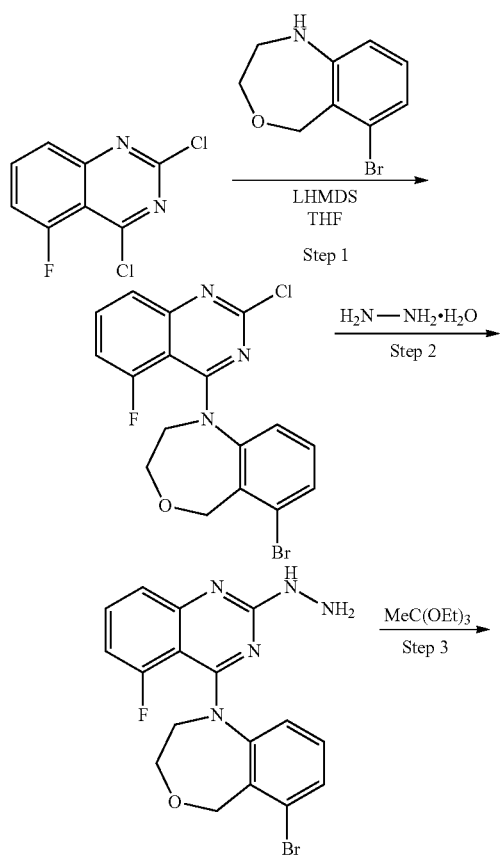

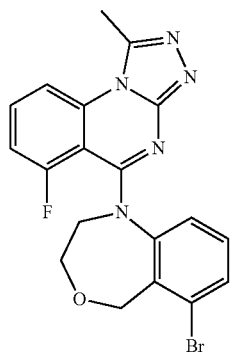

Step 1: Preparation of 6-bromo-1-(2-chloro-5-fluoro-quinazolin-4-yl)-3,5-dihydro-2H-4,1-benzoxazepine:

6-Bromo-1,2,3,5-tetrahydro-4,1-benzoxazepine (300 mg, 1.32 mmol) was treated with LHMDS (1.0 M THF solution Aldrich, 1.45 mL, 1.45 mmol, 1.1 equiv) in THF (10 mL) at rt for 20 min. To the reaction mixture was added 2,4-dichloro-5-fluoro-quinazoline (285 mg, 1.32 mmol, 1 equiv.) to stir at the same temperature for 1 h. The mixture was subjected to the next step without a work-up procedure.

Step 2: Preparation of [4-(6-bromo-3,5-dihydro-2H-4,1-benzoxazepin-1-yl)-5-fluoro-quinazolin-2-yl]hydrazine:

The reaction mixture containing 6-bromo-1-(2-chloro-5-fluoro-quinazolin-4-yl)-3,5-dihydro-2H-4,1-benzoxazepine (from the step 1) in ethanol (2 mL) and THF (4 mL) was treated with hydrazine hydrate (1912 mg, 38.2 mmol, 27 eq) at 60° C. for 1 h. To the mixture was added water (30 mL) and the whole was extracted with EtOAc (30 mL, ×3). Organic layer was washed with brine (30 mL) and dried over $Na_2SO_4$. Organic solvent was removed under a reduced pressure to give crude product. The crude product was purified by preparative reverse phase high performance liquid chromatography to give [4-(6-bromo-3,5-dihydro-2H-4,1-benzoxazepin-1-yl)-5-fluoro-quinazolin-2-yl]hydrazine: LCMS-ESI+(m/z): [M+H]+ calcd for $C_{17}H_{15}BrFN_5O$: 404.04 (M−1+1), 406.04 (M+1+1), found: 404.29 (M−1+1), 406.20 (M+1+1).

Step 3: Preparation of 6-bromo-1-(6-fluoro-1-methyl-[1,2,4]triazolo[4,3-a]quinazolin-5-yl)-3,5-dihydro-2H-4,1-benzoxazepine: A solution of [4-(6-bromo-3,5-dihydro-2H-4,1-benzoxazepin-1-yl)-5-fluoro-quinazolin-2-yl]hydrazine (275 mg, 0.68 mol, from step 2) in triethyl orthoacetate (552 mg, 3.40 mmol, 5 eq) was heated at 120° C. for 16 h. To the reaction mixture was added hexane (5 mL) to form precipitate. The precipitate was collected by a filtration through a glass filter to give the title compound: ¹H NMR (400 MHz, Methanol-$d_4$) δ 8.18-8.09 (m, 1H), 7.94-7.81 (m, 1H), 7.43 (d, J=8.0 Hz, 1H), 7.09 (dd, J=12.3, 8.4 Hz, 1H), 6.91 (t, J=8.1 Hz, 1H), 6.65 (d, J=7.9 Hz, 1H), 5.20 (br s, 4H), 4.06 (br s, 2H), 3.05 (s, 3H); LCMS-ESI+(m/z): [M+H]+ calcd for $C_{19}H_{15}BrFN_5O$: 428.04 (M−1+1), 430.04 (M+1+1), found: 428.25 (M−1+1), 430.20 (M+1+1).

1107

Example 826. 1-(6-fluoro-1-methyl-[1,2,4]triazolo[4,3-a]quinazolin-5-yl)-6-(4,4,4-trifluoro-3,3-dimethyl-but-1-ynyl)-3,5-dihydro-2H-4,1-benzoxazepine

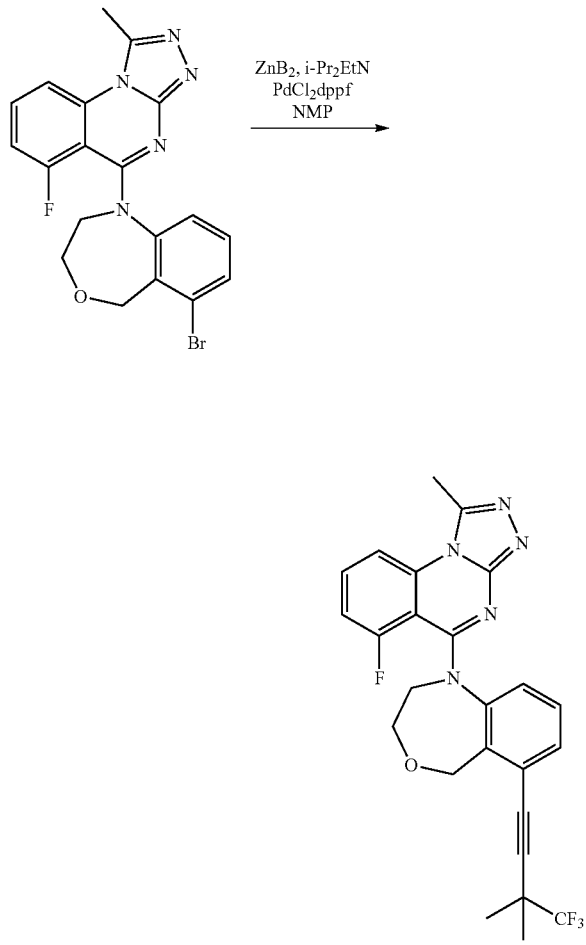 [SMILES: Cc1nnc2nc(N3CCOCc4c(Br)cccc43)c3c(F)cccc3n12 ; Cc1nnc2nc(N3CCOCc4c(C#CC(C)(C)C(F)(F)F)cccc43)c3c(F)cccc3n12]

6-bromo-1-(6-fluoro-1-methyl-[1,2,4]triazolo[4,3-a]quinazolin-5-yl)-3,5-dihydro-2H-4,1-benzoxazepine (Example 825, 11.1 mg, 0.0258 mmol), 4,4,4-trifluoro-3,3-dimethyl-but-1-yne (21.1 mg, 0.155 mmol, 6 equiv.), DIPEA (33.4 mg, 0.258 mmol, 10 equiv.), zinc bromide (58.1 mg, 0.258 mmol, 10 equiv.) and [1,1'-bis(diphenylphosphino)ferrocene]dichloropalladium(II) (1.91 mg, 0.00258 mmol, 0.1 equiv.) were heated in NMP (0.3 mL) at 120° C. for 40 min under a nitrogen atmosphere. After a filtration, the reaction mixture was purified by preparative reverse phase high performance liquid chromatography to give the title compound. $^1$H NMR (400 MHz, Methanol-$d_4$) δ 8.24 (d, J=8.6 Hz, 1H), 8.04 (td, J=8.4, 5.4 Hz, 1H), 7.40 (dd, J=7.8, 1.1 Hz, 1H), 7.23 (ddd, J=11.9, 8.3, 0.9 Hz, 1H), 7.07 (t, J=7.9 Hz, 1H), 6.86 (dd, J=8.0, 1.1 Hz, 1H), 5.90-5.10 (br s, 4H), 4.15 (s, 2H), 3.09 (s, 3H), 1.58 (s, 6H); LCMS-ESI+(m/z): [M+H]$^+$ calcd for $C_{23}H_{19}FN_6$: 484.17 (M+1), found: 484.31 (M+1).

1108

Example 827. 1-(6-fluoro-1-methyl-[1,2,4]triazolo[4,3-a]quinazolin-5-yl)-6-[2-[1-(trifluoromethyl)cyclopropyl]ethynyl]-3,5-dihydro-2H-4,1-benzoxazepine

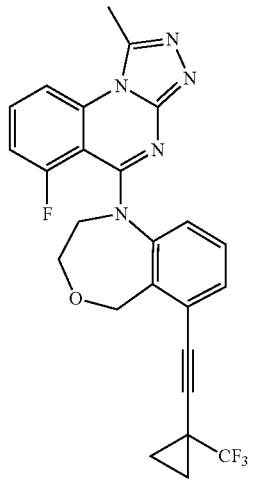 [SMILES: Cc1nnc2nc(N3CCOCc4c(C#CC5(C(F)(F)F)CC5)cccc43)c3c(F)cccc3n12]

The title compound was synthesized in a similar fashion as Example 826, except using 1-ethynyl-1-(trifluoromethyl)cyclopropane instead of 4,4,4-trifluoro-3,3-dimethyl-but-1-yne. $^1$H NMR (400 MHz, Methanol-$d_4$) δ 8.24 (d, J=8.6 Hz, 1H), 8.04 (td, J=8.5, 5.4 Hz, 1H), 7.40 (dd, J=7.8, 1.2 Hz, 1H), 7.28-7.17 (m, 1H), 7.06 (t, J=7.9 Hz, 1H), 6.86 (dd, J=8.1, 1.1 Hz, 1H), 5.40 (br s, 4H), 4.15 (br s, 2H), 3.09 (s, 3H), 1.55-1.43 (m, 2H), 1.42-1.29 (m, 2H); LCMS-ESI+(m/z): [M+H]+ calcd for $C_{25}H_{19}F_4N_5O$: 482.15 (M+1), found: 482.36 (M+1).

Example 828. 6-[2-[1-(1,1-difluoroethyl)cyclopropyl]ethynyl]-1-(6-fluoro-1-methyl-[1,2,4]triazolo[4,3-a]quinazolin-5-yl)-3,5-dihydro-2H-4,1-benzoxazepine

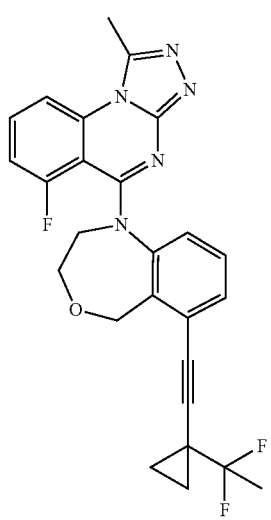 [SMILES: Cc1nnc2nc(N3CCOCc4c(C#CC5(C(C)(F)F)CC5)cccc43)c3c(F)cccc3n12]

The title compound was synthesized in a similar fashion as Example 826, except using 1-(1,1-difluoroethyl)-1-ethynyl-cyclopropane instead of 4,4,4-trifluoro-3,3-dimethyl-but-1-yne. $^1$H NMR (400 MHz, Methanol-$d_4$) δ 8.24 (d, J=8.6 Hz, 1H), 8.03 (td, J=8.4, 5.4 Hz, 1H), 7.37 (dd, J=7.8, 1.2 Hz, 1H), 7.22 (ddd, J=11.9, 8.4, 0.9 Hz, 1H), 7.04 (t, J=7.9 Hz, 1H), 6.82 (dd, J=8.0, 1.1 Hz, 1H), 5.44 (br s, 4H), 4.14 (br s, 2H), 3.09 (s, 3H), 1.89 (t, J=18.0 Hz, 3H), 1.37-1.28 (m, 2H), 1.17 (tq, J=5.0, 3.3, 2.4 Hz, 2H); LCMS-ESI+(m/z): [M+H]+ calcd for $C_{26}H_{22}F_3N_5O$: 478.18 (M+1), found: 478.38 (M+1).

Example 829. 1-(6-fluoro-1-methyl-[1,2,4]triazolo[4,3-a]quinazolin-5-yl)-6-[2-(1-methylcyclopropyl)ethynyl]-3,5-dihydro-2H-4,1-benzoxazepine

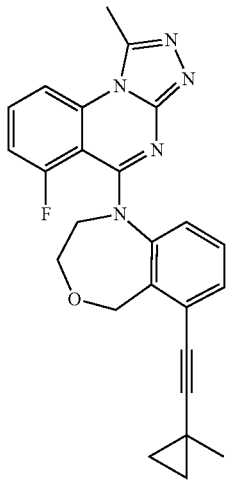 [SMILES: Cc1nnc2nc(N3CCOCc4c(C#CC5(C)CC5)cccc43)c3c(F)cccc3n12]

The title compound was synthesized in a similar fashion as Example 826, except using 1-ethynyl-1-methyl-cyclopropane instead of 4,4,4-trifluoro-3,3-dimethyl-but-1-yne. $^1$H NMR (400 MHz, Methanol-$d_4$) δ 8.23 (d, J=8.6 Hz, 1H), 8.03 (td, J=8.5, 5.4 Hz, 1H), 7.31 (dd, J=7.8, 1.1 Hz, 1H), 7.21 (dd, J=11.7, 8.3 Hz, 1H), 7.00 (t, J=7.9 Hz, 1H), 6.75 (d, J=7.9 Hz, 1H), 5.46 (br s, 4H), 4.13 (br s, 2H), 3.09 (s, 3H), 1.40 (s, 3H), 1.04 (q, J=4.1 Hz, 2H), 0.87-0.70 (m, 2H); LCMS-ESI+(m/z): [M+H]+ calcd for $C_{25}H_{22}FN_5O$: 428.18 (M+1), found: 428.29 (M+1).

Example 830. Biological Activity

Measuring DGKα Activity

A 10 mM solution of the test compound in DMSO was further diluted with DMSO to ten levels of the concentration (0.0001 mM, 0.0003 mM, 0.001 mM, 0.003 mM, 0.01 mM, 0.03 mM, 0.1 mM, 0.3 mM, 1 mM, 3 mM), each of which was subjected to a 25-fold dilution with the assay buffer to obtain the drug solutions (4% DMSO solutions).

A drug solution of each concentration was added to each well to give a final volume of 20 µL. The kinase-inhibitory activity was evaluated using QSS Assist ADP-Glo™ Assay Kit (BTN-DGKα; Carna Biosciences, Inc., No. 12-403-20N).

The kinase activity was measured using ADP-Glo™ Kinase Assay (Promega Corporation). 10 µL of ADP-Glo™ Reagent (10 mM Mg added) provided by the kit was added to each well and incubated at 25° C. for 40 minutes. Then, 20 µL of Kinase Detection Reagent was added and incubated at 25° C. for 40 minutes. Luciferase activity of each well was measured using a microplate reader (EnVision, PerkinElmer, Inc.)

Evaluation of Inhibitory Activity

The $IC_{50}$ value was calculated via a regression analysis of the inhibition rate (%) measured from the intensity of the luminescence at each concentration and the test compound concentration (logarithmic value), wherein the intensity of the group with an enzyme added without a compound was set as 100%, and the intensity without an enzyme nor a compound was set as 0%.

Inhibitory effect of exemplary compounds on DGKα activity is shown below in Table 5.

TABLE 5

| Activity Data | |
|---|---|
| Example No. | DGKα $IC_{50}$ (nM) |
| 1 | 292.0 |
| 2 | 599.8 |
| 3 | 4004.0 |
| 4 | 857.0 |
| 5 | 12972.8 |
| 6 | 342.8 |
| 7 | 10296.2 |
| 8 | 2878.4 |
| 9 | 2186.2 |
| 10 | 1586.9 |
| 11 | 84.8 |
| 12 | 6307.5 |
| 13 | 2070.8 |
| 14 | 832.9 |
| 15 | 497.8 |
| 16 | 3723.8 |
| 17 | 697.2 |
| 18 | 279.4 |
| 19 | 1832.2 |
| 20 | 580.1 |
| 21 | 99.2 |
| 22 | 18125.3 |
| 23 | 9049.5 |
| 24 | 9366.6 |
| 25 | 2923.7 |
| 26 | 17317.5 |
| 27 | 5311.6 |
| 28 | 63.2 |
| 29 | 117.5 |
| 30 | 1262.8 |
| 31 | 806.4 |
| 32 | 17781.4 |
| 33 | 1383.5 |
| 34 | 3176.8 |
| 35 | 316.8 |
| 36 | 574.0 |
| 37 | 49.0 |
| 38 | 145.7 |
| 39 | 302.2 |
| 40 | 14455.4 |
| 41 | 370.1 |
| 42 | 3626.9 |
| 43 | 1139.7 |
| 44 | 348.9 |
| 45 | 316.0 |
| 46 | 6260.0 |
| 47 | 498.2 |
| 48 | 1661.4 |
| 49 | 28277.5 |
| 50 | 2343.1 |
| 51 | 626.5 |
| 52 | 1789.1 |
| 53 | 10381.4 |
| 54 | 6222.1 |
| 55 | 2766.9 |
| 56 | 280.8 |
| 57 | 282.2 |
| 58 | 15321.0 |

TABLE 5-continued

Activity Data

| Example No. | DGKα IC$_{50}$ (nM) |
|---|---|
| 59 | 365.3 |
| 60 | 3512.1 |
| 61 | 349.7 |
| 62 | 278.9 |
| 63 | 2561.4 |
| 64 | 38.3 |
| 65 | 7229.7 |
| 66 | 22.5 |
| 67 | 5539.1 |
| 68 | 419.1 |
| 69 | 413.7 |
| 70 | 8316.0 |
| 71 | 9268.6 |
| 72 | 406.9 |
| 73 | 187.6 |
| 74 | 4506.7 |
| 75 | 22678.4 |
| 76 | 1056.3 |
| 77 | 439.5 |
| 78 | 10163.0 |
| 79 | 4596.0 |
| 80 | 2177.8 |
| 81 | 849.3 |
| 82 | 3717.2 |
| 83 | 15642.8 |
| 84 | 291.2 |
| 85 | 3575.6 |
| 86 | 3922.5 |
| 87 | 751.7 |
| 88 | 2098.7 |
| 89 | 2763.5 |
| 90 | 4448.2 |
| 91 | 7013.5 |
| 92 | 23942.4 |
| 93 | 7008.8 |
| 94 | 278.7 |
| 95 | 1012.1 |
| 96 | 2393.3 |
| 97 | 3680.1 |
| 98 | 9320.5 |
| 99 | 594.6 |
| 100 | 647.3 |
| 101 | 1037.3 |
| 102 | 9593.6 |
| 103 | 271.8 |
| 104 | 20879.5 |
| 105 | 7386.6 |
| 106 | 18.3 |
| 107 | 3897.9 |
| 108 | 6254.1 |
| 109 | 145.3 |
| 110 | 468.3 |
| 111 | 3586.5 |
| 112 | 754.3 |
| 113 | 18391.4 |
| 114 | 26657.0 |
| 115 | 128.5 |
| 116 | 2419.6 |
| 117 | 286.0 |
| 118 | 14555.0 |
| 119 | 21.0 |
| 120 | 48.0 |
| 121 | 12.0 |
| 122 | 5100.0 |
| 123 | 10919.0 |
| 124 | 98.0 |
| 125 | 1444.0 |
| 126 | 6.0 |
| 127 | 725.0 |
| 128 | 5.0 |
| 129 | 12435.0 |
| 130 | 4090.0 |
| 131 | 6117.0 |
| 132 | 3203.0 |
| 133 | 66.0 |
| 134 | 26.0 |
| 135 | 349.0 |
| 136 | 4289.0 |
| 137 | 556.0 |
| 138 | 1444.0 |
| 139 | 43.0 |
| 140 | 363.0 |
| 141 | 26.0 |
| 142 | 13717.0 |
| 143 | 4289.6 |
| 144 | 49.0 |
| 145 | 6727.6 |
| 146 | 256.4 |
| 147 | 2764.9 |
| 148 | 585.1 |
| 149 | 26812.3 |
| 150 | 1136.2 |
| 151 | 84.9 |
| 152 | 16.5 |
| 153 | 1482.7 |
| 154 | 1769.0 |
| 155 | 55.8 |
| 156 | 54.5 |
| 157 | 325.2 |
| 158 | 25.1 |
| 159 | 3395.0 |
| 160 | 663.8 |
| 161 | 51.5 |
| 162 | 24.7 |
| 163 | 6.7 |
| 164 | 6970.0 |
| 165 | 4207.8 |
| 166 | 17.2 |
| 167 | 6.7 |
| 168 | 18.2 |
| 169 | 30.1 |
| 170 | 20.4 |
| 171 | 69.2 |
| 172 | 4.0 |
| 173 | 14.0 |
| 174 | 12.0 |
| 175 | 8.0 |
| 176 | 13.0 |
| 177 | 66.0 |
| 178 | 50.0 |
| 179 | 9.0 |
| 180 | 81.2 |
| 181 | 39.7 |
| 182 | 213.1 |
| 183 | 6.0 |
| 184 | 11.2 |
| 185 | 9.2 |
| 186 | 14.2 |
| 187 | 3.8 |
| 188 | 6.9 |
| 189 | 49.0 |
| 190 | 14.9 |
| 191 | 7.0 |
| 192 | 14.8 |
| 193 | 11.1 |
| 194 | 25.9 |
| 195 | 6.8 |
| 196 | 82.6 |
| 197 | 62.1 |
| 198 | 10.3 |
| 199 | 22.4 |
| 200 | 15.0 |
| 201 | 3.3 |
| 202 | 4.0 |
| 203 | 6.4 |
| 204 | 4.1 |
| 205 | 43.0 |
| 206 | 4.7 |
| 207 | 8.6 |
| 208 | 6.6 |
| 209 | 6.1 |
| 210 | 11.2 |

TABLE 5-continued

Activity Data

| Example No. | DGKα IC$_{50}$ (nM) |
|---|---|
| 211 | 18.9 |
| 212 | 17.4 |
| 213 | 7.8 |
| 214 | 7.0 |
| 215 | 38.8 |
| 216 | 21.8 |
| 217 | 54.4 |
| 218 | 2119 |
| 219 | 1512 |
| 220 | 11548.2 |

DGKα Biochemical Activity Assay

Alternatively, the enzymatic activity of human DGKα was monitored in a biochemical assay in the presence or absence of compounds and using micelles containing 18:1 Diacylglycerol (DAG), 16:0-18:1 PS (POPS) and Octylglucoside as substrate. DGKα activity led to conversion of DAG and ATP to Phosphatidic Acid (PA) and ADP. Levels of ADP were monitored by bioluminescence using the ADP-Glo Kinase Assay (Promega) and were indicative of DGKα activity.

Ten nanoliters of test compound dissolved in DMSO at various concentrations were dispensed into a 384-well low volume nonbinding service white plates (Corning #3824) using a Labcyte Echo instrument. Recombinant DGKα (Carna Biosciences) in assay buffer (5 μL in 50 mM MOPS [3-(N-morpholino) propanesulfonic acid], pH 7.2; 0.0025% Triton X-100; 1 mM dithiothreitol; 5 mM MgCl$_2$, 200 μM ATP) was added to the compound-containing plate and was incubated for 15 minutes at 25° C. A substrate solution (5 μL in 1.7 mM 1,2-dioleoyl-sn-glycerol [18:1 DAG], 13.5 mM 1-palmitoyl-2-oleoyl-sn-glycero-3-phospho-L-serine [16:0-18:1 PS](POPS), 2 μM CaCl$_2$, 100 mM Octylglucoside (OG), 1 mM DTT) (obtained from Carna Biosciences) diluted in DGK ALPHA assay buffer was then added to start the reaction. Final concentrations were 1 nM DGKα, 100 μM ATP, 1 μM calcium chloride, 0.85 mM 1,2-dioleoyl-sn-glycerol (18:1 DAG), 6.75 mM 1-palmitoyl-2-oleoyl-sn-glycero-3-phospho-L-serine (16:0-18:1 PS) (POPS), 1 μM CaCl$_2$, 50 mM Octylglucoside (OG) and 5 mM MgCl$_2$. The reaction mixture was incubated at 25° C. for 1 hour. ADP-Glo Reagent (10 μL, 10 mM Mg added) provided by the kit was added to each well and incubated at 25° C. for 40 minutes. Then, 20 μL of Kinase Detection Reagent was added and incubated at 25° C. for 40 minutes. Luciferase activity of each well was measured via luminescence on an Envision plate reader (PerkinElmer).

Data were normalized based on maximum inhibition (50 μM of kinase inhibitor CU3) and no inhibition (DMSO) controls. Least squares curve fittings were performed using a four-parameter variable slope nonlinear regression model. IC$_{50}$ was defined as the concentration of compound required to inhibit 50% of maximum activity. IC$_{50}$ values from multiple experiments were averaged by geometric mean and the standard deviation was calculated.

Exemplary biochemical data are shown in Table 6 below.

TABLE 6

DGKα Biochemical Activity

| Example | DGKα IC$_{50}$ (nM) |
|---|---|
| 1 | 932.6 |
| 2 | 840.5 |
| 3 | >10000 |
| 4 | 1535.5 |
| 5 | >10000 |
| 6 | 731.4 |
| 8 | 4669.7 |
| 9 | 2734.8 |
| 10 | 1961.5 |
| 12 | 4818 |
| 13 | 2510.2 |
| 14 | 1245 |
| 15 | 551.1 |
| 16 | 1319.2 |
| 18 | 568.8 |
| 19 | 1730.5 |
| 20 | 929.1 |
| 21 | 228.1 |
| 23 | 9343.8 |
| 24 | >10000 |
| 26 | >10000 |
| 28 | 74.1 |
| 34 | 3464.9 |
| 35 | 485.4 |
| 36 | 1474.1 |
| 37 | 57.6 |
| 38 | 252.8 |
| 39 | 515 |
| 40 | >10000 |
| 41 | 608.5 |
| 42 | 8141.7 |
| 43 | 2273.5 |
| 45 | 554.8 |
| 46 | 9395.8 |
| 47 | 543.1 |
| 51 | 831.7 |
| 52 | 2956.4 |
| 53 | >10000 |
| 54 | 7807.8 |
| 55 | 4643.4 |
| 56 | 500.3 |
| 58 | >10000 |
| 59 | 776.1 |
| 60 | 5988.3 |
| 61 | 929.9 |
| 63 | 4433.4 |
| 65 | >10000 |
| 66 | 54.8 |
| 67 | >10000 |
| 68 | 633.7 |
| 70 | >10000 |
| 71 | >10000 |
| 72 | 585 |
| 73 | 221.2 |
| 74 | 4262.1 |
| 75 | >10000 |
| 77 | 799.9 |
| 78 | >10000 |
| 79 | 6977.7 |
| 80 | 5658 |
| 81 | 1510.2 |
| 82 | 5406.7 |
| 83 | >10000 |
| 84 | 428.7 |
| 86 | 3730.8 |
| 88 | 1838.1 |
| 89 | 4761.4 |
| 91 | 8371.2 |
| 92 | >10000 |
| 93 | 8808.7 |
| 94 | 778.2 |
| 96 | 2243 |
| 97 | 3603.4 |
| 98 | >10000 |
| 99 | 989.8 |
| 100 | 878.9 |
| 101 | 1529.6 |

TABLE 6-continued

DGKα Biochemical Activity

| Example | DGKα IC$_{50}$ (nM) |
|---|---|
| 102 | >10000 |
| 104 | >10000 |
| 105 | 8441.8 |
| 106 | 46.1 |
| 107 | 4829.5 |
| 108 | 9579.7 |
| 110 | 993.7 |
| 111 | 7276.9 |
| 112 | 1376.8 |
| 113 | >10000 |
| 114 | >10000 |
| 115 | 419.9 |
| 116 | 3841.5 |
| 121 | 21.4 |
| 122 | 7243.8 |
| 123 | 9001.9 |
| 124 | 193.1 |
| 125 | 3243.7 |
| 126 | 6.98 |
| 127 | 984.5 |
| 128 | 14.2 |
| 129 | >10000 |
| 130 | 9439.2 |
| 131 | >10000 |
| 132 | 6170.1 |
| 134 | 724.4 |
| 137 | 1349.1 |
| 138 | 1864.2 |
| 139 | 141.8 |
| 141 | 36.1 |
| 142 | >10000 |
| 143 | 7728.3 |
| 144 | 641.1 |
| 145 | >10000 |
| 146 | 1426.4 |
| 148 | 1212.3 |
| 151 | 92.6 |
| 152 | 14.8 |
| 153 | 2585.3 |
| 154 | 2247.5 |
| 155 | 40.7 |
| 156 | 125.0 |
| 157 | 528.2 |
| 158 | 38.2 |
| 159 | 6777.2 |
| 160 | 1436.7 |
| 161 | 69.9 |
| 162 | 51.5 |
| 163 | 26.5 |
| 165 | 4923.2 |
| 166 | 37.2 |
| 167 | 1.87 |
| 168 | 10.3 |
| 169 | 62.9 |
| 170 | 56.1 |
| 171 | 143.3 |
| 172 | 18.3 |
| 173 | 8.1 |
| 174 | 12.3 |
| 175 | 14.3 |
| 176 | 45.7 |
| 177 | 92.0 |
| 178 | 54.7 |
| 179 | 6.9 |
| 180 | 91.9 |
| 181 | 63.6 |
| 182 | 385.8 |
| 183 | 12.8 |
| 184 | 11.8 |
| 185 | 28.7 |
| 186 | 58.1 |
| 187 | 8.0 |
| 188 | 12.1 |
| 190 | 12.9 |
| 191 | 32.8 |
| 192 | 28.0 |
| 193 | 19.7 |
| 194 | 331.1 |
| 195 | 32.6 |
| 197 | 159.7 |
| 198 | 13.8 |
| 199 | 19.1 |
| 200 | 14.7 |
| 201 | 5.8 |
| 202 | 5.9 |
| 203 | 5.1 |
| 204 | 37.9 |
| 205 | 91.4 |
| 206 | 12.3 |
| 207 | 10.3 |
| 208 | 8.1 |
| 209 | 8.6 |
| 210 | 69.4 |
| 211 | 18.9 |
| 212 | 86.1 |
| 213 | 11.4 |
| 214 | 25.9 |
| 215 | 36.1 |
| 216 | 15.1 |
| 217 | 15.4 |
| 218 | 1560 |
| 220 | 9042.1 |
| 221 | 105.2 |
| 222 | 381.2 |
| 223 | 212.6 |
| 224 | 387.8 |
| 225 | 178.6 |
| 226 | 265.4 |
| 227 | 588.4 |
| 228 | 2817.4 |
| 229 | 417.0 |
| 230 | 188.1 |
| 231 | 180.9 |
| 232 | 717.8 |
| 233 | 45.0 |
| 234 | 61.0 |
| 235 | 13.3 |
| 236 | 4679.3 |
| 237 | 177.9 |
| 238 | 328.4 |
| 239 | >10000 |
| 240 | 27.4 |
| 241 | 57.9 |
| 242 | 19.8 |
| 243 | >10000 |
| 244 | >10000 |
| 245 | >10000 |
| 246 | >10000 |
| 247 | >10000 |
| 248 | 1530.7 |
| 249 | 336.7 |
| 250 | 54.2 |
| 251 | 44.7 |
| 252 | 22.8 |
| 253 | 11.1 |
| 254 | 15.8 |
| 255 | 113.6 |
| 256 | 201.7 |
| 257 | 16 |
| 258 | 962.6 |
| 259 | 66.5 |
| 260 | 3359.7 |
| 261 | 96.7 |
| 262 | 135 |
| 263 | 21.9 |
| 264 | 15.5 |
| 265 | 190.5 |
| 266 | 49.5 |
| 267 | 525.4 |
| 268 | 31.5 |
| 269 | 80.7 |
| 270 | 12.3 |

TABLE 6-continued

DGKα Biochemical Activity

| Example | DGKα IC$_{50}$ (nM) |
|---|---|
| 271 | 19.4 |
| 272 | 12.1 |
| 273 | 131.3 |
| 274 | 91.6 |
| 275 | 99.6 |
| 276 | 38.3 |
| 277 | 10.0 |
| 278 | 177.7 |
| 279 | 15.1 |
| 280 | 24.9 |
| 281 | 8.8 |
| 282 | 207.0 |
| 283 | 70.7 |
| 284 | 28.9 |
| 285 | 215.0 |
| 286 | 110.0 |
| 287 | >10000 |
| 288 | 2071 |
| 289 | 20.3 |
| 290 | 6.86 |
| 291 | 44.0 |
| 292 | 38.3 |
| 293 | 22.3 |
| 294 | 7.1 |
| 295 | 11.1 |
| 296 | 17.6 |
| 297 | 59.9 |
| 298 | 12.9 |
| 299 | 16.4 |
| 300 | 88.0 |
| 301 | >10000 |
| 302 | 789.9 |
| 303 | 458.5 |
| 304 | 135.9 |
| 305 | 600.4 |
| 306 | 29.6 |
| 307 | 658.3 |
| 308 | 153.9 |
| 309 | 9.8 |
| 310 | 486.1 |
| 311 | 653.5 |
| 312 | 5.5 |
| 313 | 3.3 |
| 314 | 4.6 |
| 315 | 73.7 |
| 316 | 92.9 |
| 317 | 65.6 |
| 318 | 10.6 |
| 319 | 572.2 |
| 320 | 186.9 |
| 321 | 19.9 |
| 322 | 21.3 |
| 323 | 570.3 |
| 324 | 365.4 |
| 325 | 286.6 |
| 326 | 4273.7 |
| 327 | 4237.6 |
| 328 | 2138.1 |
| 329 | 76.1 |
| 330 | 24.3 |
| 331 | 63.3 |
| 332 | 95.6 |
| 333 | 9.5 |
| 334 | 50.3 |
| 335 | 34.6 |
| 336 | 8.8 |
| 337 | 7.8 |
| 338 | 2391 |
| 339 | 3009.7 |
| 340 | 76.2 |
| 341 | 93.2 |
| 342 | 15.1 |
| 343 | 36.4 |
| 344 | 330.1 |
| 345 | 9.8 |
| 346 | 23.1 |
| 347 | 7.2 |
| 348 | 413.6 |
| 349 | 2588.4 |
| 350 | 3939.7 |
| 351 | 12.3 |
| 352 | 256.8 |
| 353 | 54.5 |
| 354 | 15.8 |
| 355 | 385.8 |
| 356 | 46.7 |
| 357 | 28.1 |
| 358 | 8.4 |
| 359 | 9.0 |
| 360 | 73.7 |
| 361 | 22.7 |
| 362 | 24.6 |
| 363 | 62.7 |
| 364 | 7.8 |
| 365 | 10.0 |
| 366 | 290.0 |
| 367 | 17.2 |
| 368 | 26.4 |
| 369 | 12.6 |
| 370 | 7.5 |
| 371 | 12.0 |
| 372 | 13.5 |
| 373 | 5.7 |
| 374 | 6.8 |
| 375 | 24.6 |
| 376 | 12.3 |
| 377 | 13.4 |
| 378 | 38.1 |
| 379 | 615.1 |
| 380 | 3.1 |
| 381 | 245.9 |
| 382 | 56.9 |
| 383 | 45.6 |
| 384 | 92.0 |
| 385 | 26.2 |
| 386 | 741.4 |
| 387 | 151.9 |
| 388 | 122.5 |
| 389 | 35.7 |
| 390 | 311.0 |
| 391 | 6038.6 |
| 392 | 29.2 |
| 393 | 176.8 |
| 394 | 2097.6 |
| 395 | 38.0 |
| 396 | 35.3 |
| 397 | 4.3 |
| 398 | 2.7 |
| 399 | 3.7 |
| 400 | 614.8 |
| 401 | 140.4 |
| 402 | 29.5 |
| 403 | 35.7 |
| 404 | 19.2 |
| 405 | 19.5 |
| 406 | 30.1 |
| 407 | 24.5 |
| 408 | 205.1 |
| 409 | 15.8 |
| 410 | 9.0 |
| 411 | 8.6 |
| 412 | 117.1 |
| 413 | 7.7 |
| 414 | 19.3 |
| 415 | 21.1 |
| 416 | 27.6 |
| 417 | 160.4 |
| 418 | 22.8 |
| 419 | >10000 |
| 420 | 21.9 |
| 421 | 7.1 |
| 422 | |

TABLE 6-continued

DGKα Biochemical Activity

| Example | DGKα IC$_{50}$ (nM) |
|---|---|
| 423 | 8.1 |
| 424 | 86.7 |
| 425 | 35.4 |
| 426 | |
| 427 | 8.5 |
| 428 | 56.5 |
| 429 | 8.7 |
| 430 | 381.6 |
| 431 | 170.4 |
| 432 | 17.1 |
| 433 | 33.9 |
| 434 | 18.3 |
| 435 | 46.7 |
| 436 | 14.8 |
| 437 | 66.1 |
| 438 | 17.2 |
| 439 | 236.9 |
| 440 | 3.6 |
| 441 | 5.1 |
| 442 | 3.0 |
| 443 | 123.9 |
| 444 | 15.7 |
| 445 | 11.5 |
| 446 | 9.1 |
| 447 | 3.4 |
| 448 | 5.4 |
| 449 | 3.5 |
| 450 | 2.6 |
| 451 | 4.5 |
| 452 | 17.6 |
| 453 | 7.0 |
| 454 | 8.8 |
| 455 | 17.8 |
| 456 | 45.0 |
| 457 | 3497.5 |
| 458 | >10000 |
| 459 | 295.9 |
| 460 | 45.5 |
| 461 | 153.0 |
| 462 | 2.1 |
| 463 | 8.6 |
| 464 | 5.4 |
| 465 | 15.0 |
| 466 | 4.3 |
| 467 | 171.5 |
| 468 | 31.5 |
| 469 | 20.0 |
| 470 | 273.6 |
| 471 | 61.6 |
| 472 | 11.1 |
| 473 | 201.2 |
| 474 | 5727.6 |
| 475 | 130.6 |
| 476 | 5.6 |
| 477 | 7.3 |
| 478 | 27.2 |
| 479 | 6.9 |
| 480 | 110.3 |
| 481 | 10.6 |
| 482 | 146.4 |
| 483 | 254.3 |
| 484 | 21.3 |
| 485 | 8039.3 |
| 486 | 6312.8 |
| 487 | 150.1 |
| 488 | 61.3 |
| 489 | 30.2 |
| 490 | 40.3 |
| 491 | 175.6 |
| 492 | 311.9 |
| 493 | 53.7 |
| 494 | 26.9 |
| 495 | 14.9 |
| 496 | 20.0 |
| 497 | 554.4 |
| 498 | 6.6 |
| 499 | 1742.5 |
| 500 | 160.2 |
| 501 | 6752.7 |
| 502 | 54.4 |
| 503 | 5.8 |
| 504 | 16.8 |
| 505 | 22.6 |
| 506 | >10000 |
| 507 | 167.6 |
| 508 | >10000 |
| 509 | 1939.1 |
| 510 | >10000 |
| 511 | >10000 |
| 512 | 76.2 |
| 513 | 9.9 |
| 514 | 24.7 |
| 515 | 10.1 |
| 516 | 53.9 |
| 517 | 36.6 |
| 518 | 14.7 |
| 519 | 39.2 |
| 520 | 24.6 |
| 521 | 75.0 |
| 522 | |
| 523 | 1.0 |
| 524 | |
| 525 | 7.4 |
| 526 | 13.9 |
| 527 | 39.8 |
| 528 | 4.3 |
| 529 | 463.5 |
| 530 | 8507.3 |
| 531 | 46.9 |
| 532 | 94.9 |
| 533 | 19.6 |
| 534 | 411.1 |
| 535 | 36.8 |
| 536 | 344.1 |
| 537 | 3.3 |
| 538 | 45.5 |
| 539 | 185.0 |
| 540 | 52.7 |
| 541 | 13.2 |
| 542 | 64.0 |
| 543 | 54.3 |
| 544 | 25.0 |
| 545 | 431.7 |
| 546 | 15.0 |
| 547 | 29.0 |
| 548 | 1218.3 |
| 549 | 2319.9 |
| 550 | 4386.3 |
| 551 | 2109.4 |
| 552 | >10000 |
| 553 | 1927.8 |
| 554 | >10000 |
| 555 | >10000 |
| 556 | 74.8 |
| 557 | >10000 |
| 558 | 227.1 |
| 559 | 187.5 |
| 560 | 1391.6 |
| 561 | 52.5 |
| 563 | 5138.8 |
| 564 | 472.7 |
| 565 | 901.1 |
| 566 | 48.5 |
| 567 | >10000 |
| 569 | 180.7 |
| 570 | 411.1 |
| 571 | |
| 572 | |
| 573 | 107.3 |
| 574 | 54.4 |
| 575 | 654.8 |
| 576 | 243.3 |

TABLE 6-continued

DGKα Biochemical Activity

| Example | DGKα IC$_{50}$ (nM) |
|---|---|
| 577 | 77.4 |
| 578 | 28.6 |
| 579 | 60.4 |
| 580 | 27.3 |
| 581 | 47.6 |
| 582 | 3.7 |
| 583 | 28.1 |
| 584 | 8.4 |
| 585 | 24.0 |
| 586 | 10.7 |
| 587 | 19.4 |
| 588 | 390.7 |
| 589 | 41.9 |
| 590 | 112.6 |
| 591 | 22.5 |
| 592 | 50.3 |
| 593 | 10.1 |
| 594 | 71.6 |
| 595 | 22.6 |
| 596 | 19.4 |
| 597 | 17.3 |
| 598 | 48.9 |
| 599 | 87.0 |
| 600 | 6.4 |
| 601 | 23.3 |
| 602 | 45.9 |
| 603 | 79.9 |
| 604 | 29.2 |
| 605 | 88.8 |
| 606 | 9.1 |
| 607 | 8.5 |
| 608 | 21.1 |
| 609 | 48.7 |
| 610 | 60.9 |
| 611 | 78.9 |
| 612 | 24.9 |
| 613 | 3.3 |
| 614 | 176.9 |
| 615 | 16.4 |
| 616 | 24.8 |
| 617 | 6.6 |
| 618 | 3.7 |
| 619 | 67.6 |
| 620 | 30.2 |
| 621 | 88.4 |
| 622 | 11.8 |
| 623 | 3.3 |
| 624 | 237.8 |
| 625 | 5.0 |
| 626 | 7.9 |
| 627 | 7.2 |
| 628 | 52.6 |
| 629 | 276.2 |
| 630 | 184.9 |
| 631 | 9.1 |
| 632 | 22.1 |
| 633 | 934.2 |
| 634 | 36.6 |
| 635 | 34.7 |
| 636 | 69.2 |
| 637 | 38.5 |
| 638 | 45.3 |
| 639 | 20.6 |
| 640 | 82.9 |
| 641 | 530.9 |
| 642 | 277.9 |
| 643 | 200.4 |
| 644 | 198.4 |
| 645 | 13.3 |
| 646 | 9.1 |
| 647 | 8.6 |
| 648 | 11.7 |
| 649 | 6.1 |
| 650 | 7.5 |
| 651 | 8.4 |
| 652 | 43.5 |
| 653 | 25.0 |
| 654 | 38.1 |
| 655 | 40.6 |
| 656 | 28.5 |
| 657 | 35.7 |
| 658 | 23.6 |
| 659 | 44.3 |
| 660 | 40.9 |
| 661 | 46.5 |
| 662 | 26.5 |
| 663 | 39.9 |
| 664 | 36.7 |
| 665 | 15.4 |
| 666 | 25.5 |
| 667 | 64.6 |
| 668 | 13.3 |
| 669 | 9.6 |
| 670 | 14.8 |
| 671 | 36.7 |
| 672 | 62.1 |
| 673 | 33.9 |
| 674 | 34.0 |
| 675 | 82.1 |
| 676 | 23.1 |
| 677 | 17.3 |
| 678 | 37.9 |
| 679 | 13.1 |
| 680 | 21.5 |
| 681 | 24.0 |
| 682 | 28.5 |
| 683 | 27.3 |
| 684 | 12.5 |
| 685 | 48.8 |
| 686 | 12.7 |
| 687 | 71.3 |
| 688 | 7.6 |
| 689 | 12.9 |
| 690 | 32.9 |
| 691 | 18.5 |
| 692 | 5.7 |
| 693 | 29.9 |
| 694 | 4.1 |
| 695 | 71.3 |
| 696 | 35.0 |
| 697 | 5.7 |
| 698 | 30.0 |
| 699 | 25.5 |
| 700 | 7.3 |
| 701 | 44.4 |
| 702 | 13.2 |
| 703 | 23.4 |
| 704 | 29.4 |
| 705 | 18.4 |
| 706 | 54.9 |
| 707 | 30.5 |
| 708 | 56.3 |
| 709 | 62.4 |
| 710 | 24.0 |
| 711 | 53.8 |
| 712 | 30.7 |
| 713 | 61.7 |
| 714 | 40.2 |
| 715 | 123.6 |
| 716 | 41.8 |
| 717 | 59.7 |
| 718 | 45.8 |
| 719 | 22.3 |
| 720 | 44.5 |
| 721 | 61.3 |
| 722 | 126.0 |
| 723 | 63.2 |
| 724 | 100.4 |
| 725 | 12.1 |
| 726 | 7.4 |
| 727 | 41.7 |
| 728 | 24.8 |

TABLE 6-continued

DGKα Biochemical Activity

| Example | DGKα IC$_{50}$ (nM) |
|---|---|
| 729 | 54.2 |
| 730 | 31.5 |
| 731 | 20.8 |
| 732 | 32.4 |
| 733 | 35.2 |
| 734 | 13.8 |
| 735 | 6.0 |
| 736 | 5.0 |
| 737 | 9.3 |
| 738 | 9.7 |
| 739 | 5.5 |
| 740 | 72.4 |
| 741 | 17.9 |
| 742 | 22.3 |
| 743 | 18.6 |
| 744 | 39.9 |
| 745 | 17.0 |
| 746 | 6.4 |
| 747 | 16.0 |
| 748 | 23.4 |
| 749 | 26.3 |
| 750 | 19.8 |
| 751 | 14.1 |
| 752 | 34.1 |
| 753 | 34.4 |
| 754 | 35.9 |
| 755 | 37.4 |
| 756 | 14.8 |
| 757 | 6.1 |
| 758 | 38.0 |
| 759 | 160.6 |
| 760 | 131.0 |
| 761 | 24.7 |
| 762 | 12.1 |
| 763 | 58.3 |
| 764 | 16.6 |
| 765 | 13.3 |
| 766 | 22.4 |
| 767 | 391.4 |
| 768 | 31.4 |
| 769 | 24.3 |
| 770 | 33.3 |
| 771 | 22.7 |
| 772 | 31.7 |
| 773 | 8.4 |
| 774 | 27.3 |
| 775 | 37.7 |
| 776 | 394.5 |
| 777 | 30.9 |
| 778 | 25.0 |
| 779 | 31.0 |
| 780 | 121.1 |
| 781 | 10.3 |
| 782 | 14.9 |
| 783 | 35.7 |
| 784 | 8.6 |
| 785 | 11.3 |
| 786 | 18.2 |
| 787 | 31.6 |
| 788 | 24.5 |
| 789 | 19.1 |
| 790 | 27.1 |
| 791 | 3.0 |
| 792 | 67.9 |
| 793 | 30.3 |
| 794 | 16.6 |
| 795 | 27.2 |
| 796 | 48.9 |
| 797 | 14.7 |
| 798 | 24.6 |
| 799 | 132.8 |
| 800 | 11.2 |
| 801 | 62.0 |
| 802 | 6.1 |
| 803 | 68.5 |
| 804 | 148.5 |
| 805 | 10.8 |
| 806 | 15.5 |
| 807 | 25.1 |
| 808 | 78.6 |
| 809 | 336.6 |
| 810 | 91.6 |
| 811 | 104.4 |
| 812 | 70.1 |
| 813 | 7.1 |
| 814 | 7.0 |
| 815 | 27.6 |
| 816 | 5.4 |
| 817 | 39.1 |
| 818 | 3.9 |
| 819 | 19.0 |
| 820 | 124.1 |
| 821 | 37.3 |
| 822 | 9.4 |
| 823 | 27.9 |
| 824 | 43.4 |
| 825 | 290.1 |
| 826 | 9.5 |
| 827 | 11.5 |
| 828 | 8.6 |
| 829 | 2.7 |

Jurkat NFκB-Luciferase Assay

The activity of compounds was tested in a cell based NFκB reporter assay. Jurkat cells that are stably expressing a luciferase reporter construct under the transcriptional control of a NFκB reporter element were activated with an anti-CD3 antibody and luciferase levels were measured with a bioluminescence readout. An increase in the levels of bioluminescence was indicative of enhanced T-cell activation following DGKα inhibition by the compound.

Flat-bottom polystyrene plates (384-well, tissue culture treated) were coated overnight at 4° C. with 20 ul/well of a solution of phosphate-buffered saline supplemented with S5 ug/ml anti-CD3 antibody (clone OKT3, Biolegend). The day after, the excess antibody was washed out five times with 100 ul/well of assay medium (RPMI supplemented with 1000 fetal bovine serum) using a Biotek EL406 instrument and leaving 20 ul of residual volume in each well. Jurkat NFκB-luciferase cells (Promega #) were harvested and diluted to 1 million cells/ml in assay medium. Sixty nanoliters of test compound dissolved in DMSO at various concentrations were dispensed into 384-well v-bottom polypropylene plates (Greiner) using a Labcyte Echo instrument. Thirty microliters of medium containing the Jurkat NFκB-luciferase cells were then dispensed using a Biotek MicroFlo instrument in each well of the compound-containing plate. The medium/cell/compound mixture was mixed with a Bravo instrument and 20 ul/well of the mixture was transferred to the anti-CD3-coated plate. The assay mixture was then incubated for 2.5 hrs at 37° C. followed by equilibration at 25° C. for 30 min. Forty microliters of One-Glo Ex (Promega) was then added to the assay mixture and luciferase activity was read on a Envision plate reader 7 minutes later.

Bioluminescence data were normalized based on maximum enhancement (1 micromolar of compound) and on basal activation (DMSO) controls. Least squares curve fittings were performed using a four-parameter variable slope nonlinear regression model. EC$_{50}$ is defined as the concentration of compound required to produce 50% of maximum NFκB luciferase signal. $EC_{50}$ values from multiple experiments were averaged by geometric mean and the standard deviation was calculated.

Exemplary cell data are shown in Table 7 below.

TABLE 7

DGKα inhibition in Jurkat cells

| Example | DGKα $EC_{50}$ (nM) |
|---|---|
| 1 | 265.9 |
| 2 | 98.6 |
| 3 | >10000 |
| 4 | 246.9 |
| 5 | >10000 |
| 6 | 239.4 |
| 8 | 1383 |
| 9 | 1684.7 |
| 10 | 3619.8 |
| 12 | 898.9 |
| 13 | 942.2 |
| 14 | 448.5 |
| 15 | 343.1 |
| 16 | 1197.4 |
| 18 | 69.3 |
| 19 | 77.7 |
| 20 | 238.0 |
| 21 | 41.3 |
| 23 | 5234.2 |
| 24 | 6903.5 |
| 26 | 6682.9 |
| 28 | 4.5 |
| 34 | 981.4 |
| 35 | 74.9 |
| 36 | 301.8 |
| 37 | 11.0 |
| 38 | 3826.4 |
| 39 | 89.1 |
| 40 | 3779.1 |
| 41 | 141.7 |
| 42 | 4971.1 |
| 43 | 400.8 |
| 45 | 32.6 |
| 46 | 3211.6 |
| 47 | 29.9 |
| 51 | 295.2 |
| 52 | 1585.7 |
| 53 | 1583.1 |
| 54 | 614.3 |
| 55 | 1162.8 |
| 56 | 355.0 |
| 58 | >10000 |
| 59 | 302.7 |
| 60 | 4489.3 |
| 61 | 77.4 |
| 63 | 1392.9 |
| 65 | 753.1 |
| 66 | 10.5 |
| 67 | 1683.8 |
| 68 | 229.2 |
| 70 | 3461.6 |
| 71 | 1295.2 |
| 72 | 15.4 |
| 73 | 6.7 |
| 74 | 836.9 |
| 75 | >10000 |
| 77 | 129.4 |
| 78 | 4963.4 |
| 79 | 771.0 |
| 80 | 286.8 |
| 81 | 213.8 |
| 82 | 353.2 |
| 83 | >10000 |
| 84 | 17.8 |
| 86 | 462.0 |
| 88 | 959.5 |
| 89 | 1837.6 |
| 91 | 3625.3 |
| 92 | 3843.3 |
| 93 | 1736.2 |
| 94 | 211.1 |
| 96 | 311.0 |
| 97 | 183.3 |
| 98 | 787.8 |
| 99 | 554.3 |
| 100 | 243.5 |
| 101 | 333.5 |
| 102 | 3873.3 |
| 104 | 7268.7 |
| 105 | 920.7 |
| 106 | 2.1 |
| 107 | 192.4 |
| 108 | 1135.9 |
| 110 | 23.9 |
| 111 | 439.2 |
| 112 | 309.4 |
| 113 | 6060.8 |
| 114 | 1847.8 |
| 115 | 253.1 |
| 116 | 50.9 |
| 121 | 3.1 |
| 122 | 3189.4 |
| 123 | 665.9 |
| 124 | 57.9 |
| 125 | >10000 |
| 126 | 2.4 |
| 127 | 18.4 |
| 128 | 0.59 |
| 129 | 7251.8 |
| 130 | 4993.3 |
| 131 | 2818.4 |
| 132 | >10000 |
| 134 | 5.8 |
| 137 | 91.1 |
| 138 | 727.6 |
| 139 | 94.8 |
| 141 | 2.6 |
| 142 | 2101.4 |
| 143 | 343.1 |
| 144 | 48.8 |
| 145 | 1986.2 |
| 146 | 33.1 |
| 148 | 6.5 |
| 151 | 0.63 |
| 152 | 0.41 |
| 153 | 6361.2 |
| 154 | 315.9 |
| 155 | 1.7 |
| 156 | 2.0 |
| 157 | 1104.2 |
| 158 | 1.7 |
| 159 | 379 |
| 160 | 36.8 |
| 161 | 0.56 |
| 162 | 110.9 |
| 163 | 2.9 |
| 165 | 88.7 |
| 166 | 0.60 |
| 167 | 4.4 |
| 168 | 9875.8 |
| 169 | 21.2 |
| 170 | 14.7 |
| 171 | 10.5 |
| 172 | 0.99 |
| 173 | 0.73 |
| 174 | 25.1 |
| 175 | 1.1 |
| 176 | 0.51 |
| 177 | 14.4 |
| 178 | 7.4 |
| 179 | 1.5 |
| 180 | 49.7 |
| 181 | 15.6 |
| 182 | 237.3 |
| 183 | 0.46 |
| 184 | 0.42 |

TABLE 7-continued

DGKα inhibition in Jurkat cells

| Example | DGKα EC$_{50}$ (nM) |
|---|---|
| 185 | 0.56 |
| 186 | 0.51 |
| 187 | 0.52 |
| 188 | 19.4 |
| 190 | 4.3 |
| 191 | 71.3 |
| 192 | 0.89 |
| 193 | 31.9 |
| 194 | 0.58 |
| 195 | 0.51 |
| 197 | 30.9 |
| 198 | 1.8 |
| 199 | 487.6 |
| 200 | 8.5 |
| 201 | 1.3 |
| 202 | 2.9 |
| 203 | 2376.8 |
| 204 | 0.97 |
| 205 | 2.3 |
| 206 | 3.7 |
| 207 | 1.7 |
| 208 | 4.9 |
| 209 | 1.4 |
| 210 | 0.66 |
| 211 | 2.3 |
| 212 | 2.1 |
| 213 | 1.2 |
| 214 | 0.64 |
| 215 | 3.2 |
| 216 | 3.1 |
| 217 | 1.9 |
| 218 | 317.9 |
| 220 | 2805.4 |
| 221 | 55.9 |
| 222 | 192.2 |
| 223 | 45.5 |
| 224 | 2701.7 |
| 225 | 31.0 |
| 226 | 13.3 |
| 227 | 23.2 |
| 228 | 81.0 |
| 229 | 44.3 |
| 230 | 43.6 |
| 231 | 78.6 |
| 232 | 5023.1 |
| 233 | 303.6 |
| 234 | 51.8 |
| 235 | 0.62 |
| 236 | 17.8 |
| 237 | 2.2 |
| 238 | 2.1 |
| 239 | 69.0 |
| 240 | 0.38 |
| 241 | 0.67 |
| 242 | 2.4 |
| 243 | 397.2 |
| 244 | >10000 |
| 245 | >10000 |
| 246 | 3628.4 |
| 247 | >10000 |
| 248 | 1233.4 |
| 249 | 288.0 |
| 250 | 5.6 |
| 251 | 14.7 |
| 252 | 1.1 |
| 253 | 0.16 |
| 254 | 0.73 |
| 255 | 56.8 |
| 256 | 5.9 |
| 257 | 0.48 |
| 258 | 180.0 |
| 259 | 12.8 |
| 260 | 1398.4 |
| 261 | 3.4 |
| 262 | 6.9 |
| 263 | 0.37 |
| 264 | 0.57 |
| 265 | 20.4 |
| 266 | 9.0 |
| 267 | 48.4 |
| 268 | 1.6 |
| 269 | 5.2 |
| 270 | 1.3 |
| 271 | 1.6 |
| 272 | 1.3 |
| 273 | 11.1 |
| 274 | 81.4 |
| 275 | 11.3 |
| 276 | 1.8 |
| 277 | 2.4 |
| 278 | 3.6 |
| 279 | 0.35 |
| 280 | 17.1 |
| 281 | 3.9 |
| 282 | 1217.8 |
| 283 | 99.1 |
| 284 | 9.4 |
| 285 | 5.8 |
| 286 | 4.6 |
| 287 | 1832.8 |
| 288 | 6.9 |
| 289 | 0.51 |
| 290 | 1.6 |
| 291 | 1.2 |
| 292 | 12.5 |
| 293 | 0.49 |
| 294 | 4.8 |
| 295 | 3.4 |
| 296 | 1109.3 |
| 297 | 3.3 |
| 298 | 1.9 |
| 299 | 2.3 |
| 300 | 9.0 |
| 301 | >10000 |
| 302 | 741.1 |
| 303 | 443.0 |
| 304 | |
| 305 | 58.2 |
| 306 | 2.9 |
| 307 | 118.4 |
| 308 | 13.1 |
| 309 | 1.5 |
| 310 | 19.5 |
| 311 | 22.4 |
| 312 | 0.54 |
| 313 | 0.51 |
| 314 | 0.51 |
| 315 | 5.4 |
| 316 | 5.5 |
| 317 | 1.0 |
| 318 | 0.96 |
| 319 | 41.7 |
| 320 | 4.1 |
| 321 | 4.1 |
| 322 | 0.72 |
| 323 | 18.5 |
| 324 | 12.2 |
| 325 | 8.3 |
| 326 | 105.1 |
| 327 | 7247.8 |
| 328 | 467.4 |
| 329 | 1.6 |
| 330 | 0.81 |
| 331 | 0.88 |
| 332 | 4.4 |
| 333 | 3.6 |
| 334 | 7.4 |
| 335 | 2.0 |
| 336 | 1.3 |
| 337 | 1.1 |
| 338 | 11.0 |
| 339 | 49.6 |

TABLE 7-continued

DGKα inhibition in Jurkat cells

| Example | DGKα EC$_{50}$ (nM) |
|---|---|
| 340 | 11.1 |
| 341 | 37.1 |
| 342 | 3.3 |
| 343 | 41.1 |
| 344 | 121.8 |
| 345 | 1.6 |
| 346 | 0.73 |
| 347 | 0.82 |
| 348 | 11.1 |
| 349 | 66.6 |
| 350 | 4042.1 |
| 351 | 24.6 |
| 352 | 25.4 |
| 353 | 2.6 |
| 354 | 1.7 |
| 355 | 193.4 |
| 356 | 41.5 |
| 357 | 4.0 |
| 358 | 2.0 |
| 359 | 0.72 |
| 360 | 1.5 |
| 361 | 0.45 |
| 362 | 1.6 |
| 363 | 0.81 |
| 364 | 0.59 |
| 365 | 0.34 |
| 366 | 3.7 |
| 367 | 1.1 |
| 368 | 3.7 |
| 369 | 9.5 |
| 370 | 3.2 |
| 371 | 0.69 |
| 372 | 10.1 |
| 373 | 8.4 |
| 374 | 6.5 |
| 375 | 93.2 |
| 376 | 7.1 |
| 377 | 1.1 |
| 378 | 6.1 |
| 379 | 5.6 |
| 380 | 0.92 |
| 381 | 14.7 |
| 382 | 82.7 |
| 383 | 0.32 |
| 384 | 5.0 |
| 385 | 2.1 |
| 386 | 6.6 |
| 387 | 2.7 |
| 388 | 3.2 |
| 389 | 2.8 |
| 390 | 44.7 |
| 391 | 1212.1 |
| 392 | 8.9 |
| 393 | 2.6 |
| 394 | 449.8 |
| 395 | 2.9 |
| 396 | 0.35 |
| 397 | 0.43 |
| 398 | 0.64 |
| 399 | 0.97 |
| 400 | 59.1 |
| 401 | 0.70 |
| 402 | 0.50 |
| 403 | 0.86 |
| 404 | 0.89 |
| 405 | 51.1 |
| 406 | 126.1 |
| 407 | 0.50 |
| 408 | 8.1 |
| 409 | 0.24 |
| 410 | 0.26 |
| 411 | 0.42 |
| 412 | 13.0 |
| 413 | 0.64 |
| 414 | 85.3 |
| 415 | 0.78 |
| 416 | 34 |
| 417 | 18.3 |
| 418 | 0.62 |
| 419 | 2160.7 |
| 420 | 12.0 |
| 421 | 4.2 |
| 422 | 0.50 |
| 423 | 0.50 |
| 424 | 0.62 |
| 425 | 0.37 |
| 426 | 0.88 |
| 427 | 0.68 |
| 428 | 0.74 |
| 429 | 1.2 |
| 430 | 34.0 |
| 431 | 37.3 |
| 432 | 0.22 |
| 433 | 0.47 |
| 434 | 0.34 |
| 435 | 1.1 |
| 436 | 1.1 |
| 437 | 2.4 |
| 438 | 11.8 |
| 439 | 390.7 |
| 440 | 0.53 |
| 441 | 0.30 |
| 442 | 0.26 |
| 443 | 11.1 |
| 444 | 0.68 |
| 445 | 24.3 |
| 446 | 1.8 |
| 447 | 0.34 |
| 448 | 12.9 |
| 449 | 5.0 |
| 450 | 0.50 |
| 451 | 1.2 |
| 452 | 3.9 |
| 453 | 4.1 |
| 454 | 2.9 |
| 455 | 1.2 |
| 456 | 9.2 |
| 457 | 61.2 |
| 458 | >10000 |
| 459 | >10000 |
| 460 | 1.7 |
| 461 | 33.3 |
| 462 | 0.36 |
| 463 | 1.2 |
| 464 | 3.3 |
| 465 | 9.7 |
| 466 | 0.61 |
| 467 | 65.9 |
| 468 | 0.38 |
| 469 | 0.62 |
| 470 | 4.9 |
| 471 | 22.6 |
| 472 | 0.11 |
| 473 | 90.2 |
| 474 | >10000 |
| 475 | 2.2 |
| 476 | 1.3 |
| 477 | 5.3 |
| 478 | 1.4 |
| 479 | 0.59 |
| 480 | 73.4 |
| 481 | 5.9 |
| 482 | 12.8 |
| 483 | 57.4 |
| 484 | 1.6 |
| 485 | 1181.2 |
| 486 | 2679 |
| 487 | 9.3 |
| 488 | 10.6 |
| 489 | 1.5 |
| 490 | 9.1 |
| 491 | 27.2 |

TABLE 7-continued

DGKα inhibition in Jurkat cells

| Example | DGKα EC$_{50}$ (nM) |
|---|---|
| 492 | 31.1 |
| 493 | 15.5 |
| 494 | 7.2 |
| 495 | 12.0 |
| 496 | 8.6 |
| 497 | 348.1 |
| 498 | 0.30 |
| 499 | 339.3 |
| 500 | 25.5 |
| 501 | 270.7 |
| 502 | 46.2 |
| 503 | 0.57 |
| 504 | 1.7 |
| 505 | 3.2 |
| 506 | 9.9 |
| 507 | 2.0 |
| 508 | 3394.6 |
| 509 | 14.6 |
| 510 | 53.9 |
| 511 | 2739.7 |
| 512 | 1.5 |
| 513 | 0.60 |
| 514 | 0.67 |
| 515 | 0.86 |
| 516 | 0.52 |
| 517 | 3.5 |
| 518 | 1.2 |
| 519 | |
| 520 | 3.0 |
| 521 | 5.3 |
| 522 | 0.48 |
| 523 | 0.24 |
| 524 | 1.8 |
| 525 | 0.39 |
| 526 | 0.45 |
| 527 | 2.4 |
| 528 | 0.70 |
| 529 | 21.4 |
| 530 | 356.4 |
| 531 | 6.4 |
| 532 | 0.55 |
| 533 | 0.51 |
| 534 | 137.2 |
| 535 | 4.1 |
| 536 | >10000 |
| 537 | 0.76 |
| 538 | 1.7 |
| 539 | 2.4 |
| 540 | 6.6 |
| 541 | 1.9 |
| 542 | 3.3 |
| 543 | 5.2 |
| 544 | 4.6 |
| 545 | 36.3 |
| 546 | 1.5 |
| 547 | 4.7 |
| 548 | 186.8 |
| 549 | 279.5 |
| 550 | 4922.3 |
| 551 | 415.2 |
| 552 | 3911 |
| 553 | 3.4 |
| 554 | 6461.7 |
| 555 | 3794.9 |
| 556 | 26.6 |
| 557 | 478.1 |
| 558 | 766.3 |
| 559 | 327.1 |
| 560 | 303.8 |
| 561 | 31.5 |
| 563 | 379.0 |
| 564 | 206.1 |
| 565 | 26.7 |
| 566 | 0.26 |
| 567 | 760.4 |
| 569 | 6.1 |
| 570 | 137.2 |
| 571 | |
| 572 | |
| 573 | 1.9 |
| 574 | 0.74 |
| 575 | 300.5 |
| 576 | 1418.4 |
| 577 | 245.0 |
| 578 | 5.3 |
| 579 | 10.4 |
| 580 | 0.53 |
| 581 | 535.8 |
| 582 | 1.3 |
| 583 | 7.8 |
| 584 | 1.7 |
| 585 | 0.88 |
| 586 | 2.6 |
| 587 | 5.8 |
| 588 | 13.6 |
| 589 | 0.75 |
| 590 | 3.2 |
| 591 | 1.8 |
| 592 | 0.57 |
| 593 | 1.8 |
| 594 | 1.4 |
| 595 | 1.3 |
| 596 | 2.6 |
| 597 | 2.3 |
| 598 | 3.1 |
| 599 | 0.93 |
| 600 | 0.71 |
| 601 | 2.0 |
| 602 | 2.4 |
| 603 | 4.2 |
| 604 | 5.2 |
| 605 | 2.8 |
| 606 | 0.83 |
| 607 | 4.9 |
| 608 | 0.69 |
| 609 | 1.7 |
| 610 | 1.7 |
| 611 | 1.1 |
| 612 | 6.5 |
| 613 | 9.1 |
| 614 | >1000 |
| 615 | 4.8 |
| 616 | 7.1 |
| 617 | 4.0 |
| 618 | 6.4 |
| 619 | >1000 |
| 620 | 6.8 |
| 621 | 7.3 |
| 622 | 0.81 |
| 623 | 2.2 |
| 624 | 1.1 |
| 625 | 0.60 |
| 626 | 0.41 |
| 627 | 0.86 |
| 628 | 0.64 |
| 629 | 1.52 |
| 630 | 0.78 |
| 631 | 1.5 |
| 632 | 0.53 |
| 633 | 0.97 |
| 634 | 0.67 |
| 635 | 0.65 |
| 636 | 2.0 |
| 637 | 98.6 |
| 638 | 4.2 |
| 639 | 2.0 |
| 640 | 4.1 |
| 641 | 7.7 |
| 642 | 36.8 |
| 643 | 13.4 |
| 644 | 4.4 |
| 645 | 1.3 |

TABLE 7-continued

DGKα inhibition in Jurkat cells

| Example | DGKα EC$_{50}$ (nM) |
|---|---|
| 646 | 2.2 |
| 647 | 3.9 |
| 648 | 2.0 |
| 649 | 0.40 |
| 650 | 0.91 |
| 651 | 1.2 |
| 652 | 2.1 |
| 653 | 16.1 |
| 654 | 2.9 |
| 655 | 1.8 |
| 656 | 4.3 |
| 657 | 0.79 |
| 658 | 1.4 |
| 659 | 1.9 |
| 660 | 6.3 |
| 661 | 3.1 |
| 662 | 1.2 |
| 663 | 0.87 |
| 664 | 2.1 |
| 665 | 2.5 |
| 666 | 2.2 |
| 667 | 0.59 |
| 668 | 4.8 |
| 669 | 1.3 |
| 670 | 1.9 |
| 671 | 2.1 |
| 672 | 2.3 |
| 673 | 0.85 |
| 674 | 1.4 |
| 675 | 12.2 |
| 676 | 1.4 |
| 677 | 14.1 |
| 678 | 1.4 |
| 679 | 1.8 |
| 680 | 0.57 |
| 681 | 1.7 |
| 682 | 8.2 |
| 683 | 0.79 |
| 684 | 0.89 |
| 685 | 0.75 |
| 686 | 0.92 |
| 687 | 0.43 |
| 688 | 0.49 |
| 689 | 0.34 |
| 690 | 0.7 |
| 691 | 1.0 |
| 692 | 0.5 |
| 693 | 3.4 |
| 694 | 3.2 |
| 695 | 3.8 |
| 696 | 0.58 |
| 697 | 11.8 |
| 698 | 12.8 |
| 699 | 2.0 |
| 700 | 1.1 |
| 701 | 0.91 |
| 702 | 1.5 |
| 703 | 0.98 |
| 704 | 14.4 |
| 705 | 32.7 |
| 706 | 1.85 |
| 707 | 1.2 |
| 708 | 1.7 |
| 709 | 1.1 |
| 710 | 9.0 |
| 711 | 4.1 |
| 712 | 1.5 |
| 713 | 1.9 |
| 714 | 2.0 |
| 715 | 1.6 |
| 716 | 2.8 |
| 717 | 4.6 |
| 718 | 1.4 |
| 719 | 1.9 |
| 720 | 1.6 |
| 721 | 4.6 |
| 722 | 4.2 |
| 723 | 114.9 |
| 724 | 1.5 |
| 725 | 0.57 |
| 726 | 6.0 |
| 727 | 0.46 |
| 728 | 0.60 |
| 729 | 0.69 |
| 730 | 0.65 |
| 731 | 0.44 |
| 732 | 0.71 |
| 733 | 0.49 |
| 734 | 0.59 |
| 735 | 0.59 |
| 736 | 0.55 |
| 737 | 0.74 |
| 738 | 0.44 |
| 739 | 0.66 |
| 740 | 0.58 |
| 741 | 0.68 |
| 742 | 0.70 |
| 743 | 0.57 |
| 744 | 1.3 |
| 745 | 0.47 |
| 746 | 2.9 |
| 747 | 9.0 |
| 748 | 0.40 |
| 749 | 0.88 |
| 750 | 0.43 |
| 751 | 0.41 |
| 752 | 1.1 |
| 753 | 1.1 |
| 754 | 1.4 |
| 755 | 1.2 |
| 756 | 1.5 |
| 757 | 1.1 |
| 758 | 1.5 |
| 759 | 0.73 |
| 760 | 2.8 |
| 761 | 2.7 |
| 762 | 0.72 |
| 763 | 0.47 |
| 764 | 0.49 |
| 765 | 0.46 |
| 766 | 0.30 |
| 767 | 3.8 |
| 768 | 0.35 |
| 769 | 0.16 |
| 770 | 0.59 |
| 771 | 0.93 |
| 772 | 1.1 |
| 773 | 0.23 |
| 774 | 1.1 |
| 775 | 0.95 |
| 776 | 1.0 |
| 777 | 0.43 |
| 778 | 1.3 |
| 779 | 1.0 |
| 780 | 0.60 |
| 781 | 0.39 |
| 782 | 0.53 |
| 783 | 0.97 |
| 784 | 0.64 |
| 785 | 0.52 |
| 786 | 0.35 |
| 787 | 0.31 |
| 788 | 4.2 |
| 789 | 13.2 |
| 790 | 8.4 |
| 791 | 5.2 |
| 792 | 2.2 |
| 793 | 1.7 |
| 794 | 1.5 |
| 795 | 2.2 |
| 796 | 1.9 |
| 797 | 2.3 |

TABLE 7-continued

DGKα inhibition in Jurkat cells

| Example | DGKα EC$_{50}$ (nM) |
|---|---|
| 798 | 2.2 |
| 799 | 1.4 |
| 800 | 1.4 |
| 801 | 1.5 |
| 802 | 3.5 |
| 803 | 12.6 |
| 804 | 2.8 |
| 805 | 1.4 |
| 806 | 17.0 |
| 807 | 2.4 |
| 808 | 2.5 |
| 809 | 2.1 |
| 810 | 2.2 |
| 811 | 0.85 |
| 812 | 1.6 |
| 813 | 0.74 |
| 814 | 2.4 |
| 815 | 7.9 |
| 816 | 3.2 |
| 817 | 1.3 |
| 818 | 0.41 |
| 819 | 0.62 |
| 820 | 0.33 |
| 821 | 0.68 |
| 822 | 0.75 |
| 823 | 1.4 |
| 824 | 1.5 |
| 825 | 13.1 |
| 826 | 1.8 |
| 827 | 1.2 |
| 828 | 0.84 |
| 829 | 0.47 |

Although the foregoing invention has been described in some detail by way of illustration and Example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A compound of Formula (I):

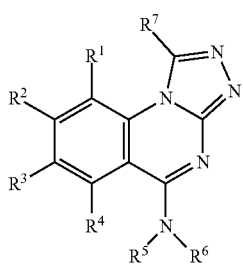

(I)

or a pharmaceutically acceptable salt thereof, wherein
R$^1$ is hydrogen, C$_{1-6}$ alkyl, C$_{2-6}$ alkenyl, C$_{2-6}$ alkynyl, C$_{1-6}$ alkoxy, halogen, C$_{1-6}$ haloalkyl, C$_{1-6}$ haloalkoxy, or —CN;
R$^2$ is hydrogen, C$_{1-6}$ alkyl, C$_{2-6}$ alkenyl, C$_{2-6}$ alkynyl, C$_{1-6}$ hydroxyalkyl, C$_{1-6}$ aminoalkyl, C$_{1-6}$ alkoxy, C$_{2-6}$ alkoxyalkyl, halogen, C$_{1-6}$ haloalkyl, C$_{1-6}$ haloalkoxy, —CN, —NO, —NO$_2$, —C(O)R$^{2a}$, —C(O)OR$^{2a}$, —OC(O)R$^{2a}$, —C(O)N(R$^{2a}$)(R$^{2b}$), —N(R$^{2a}$)C(O)R$^{2b}$, —OC(O)N(R$^{2a}$)(R$^{2b}$), —N(R$^{2a}$)C(O)OR$^{2b}$, —C(=NR$^{2a}$)N(R$^{2b}$)(R$^{2c}$), —N(R$^{2a}$)(R$^{2b}$), —N(R$^{2a}$)N(R$^{2b}$)(R$^{2c}$), —N(R$^{2a}$)N=C(R$^{2b}$)(OR$^{2c}$), —OR$^{2a}$, —SR$^{2a}$, —S(O)R$^{2a}$, —S(O)(NR$^{2a}$)(R$^{2b}$), S(NR$^{2a}$)(NR$^{2b}$)(R$^{2c}$), —S(O)$_2$R$^{2a}$, —S(O)$_2$N(R$^{2a}$)(R$^{2b}$), —N(R$^{2a}$)S(O)$_2$(R$^{2b}$), —P(R$^{2a}$)(R$^{2b}$), —P(O)(R$^{2a}$)(R$^{2b}$), —P(O)(OR$^{2a}$)(R$^{2b}$), —P(O)(OR$^{2a}$)(OR$^{2b}$), C$_{3-10}$ cycloalkyl, C$_{1-6}$ alkyl-C$_{3-10}$ cycloalkyl, C$_{6-12}$ aryl, C$_{1-6}$ alkyl-C$_{6-12}$ aryl, heterocycloalkyl, C$_{1-6}$ alkyl-(heterocycloalkyl), heteroaryl, or C$_{1-6}$ alkyl-(heteroaryl), wherein each alkyl, alkenyl or alkynyl is independently optionally substituted with 1 to 3 R$^{2d}$ groups, each cycloalkyl is optionally substituted with 1 to 3 R$^{2e}$ groups, each aryl is optionally substituted with 1 to 3 R$^{2f}$ groups, each heterocycloalkyl is optionally substituted with 1 to 3 R$^g$ groups, and each heteroaryl is optionally substituted with 1 to 3 R$^{2h}$ groups;
each R$^{2a}$, R$^{2b}$, and R$^{2c}$ is independently hydrogen, C$_{1-6}$ alkyl, C$_{2-6}$ alkenyl, C$_{2-6}$ alkynyl, C$_{1-6}$ hydroxyalkyl, C$_{1-6}$ aminoalkyl, C$_{2-6}$ alkoxyalkyl, C$_{1-6}$ haloalkyl, C$_{3-10}$ cycloalkyl, C$_{1-6}$ alkyl-C$_{3-10}$ cycloalkyl, C$_{6-12}$ aryl, C$_{1-6}$ alkyl-C$_{6-12}$ aryl, heterocycloalkyl, C$_{1-6}$ alkyl-(heterocycloalkyl), heteroaryl, or C$_{1-6}$ alkyl-(heteroaryl), wherein the aryl or heteroaryl is optionally substituted with 1 to 3 R$^{2j}$;
alternatively, R$^{2a}$, R$^{2b}$, and R$^{2c}$ when attached to the same atom can be combined with the atom to which they are attached to form a heterocycloalkyl;
each R$^{2d}$ is independently —CN, —C(O)R$^{2d1}$, —C(O)OR$^{2d1}$, —OC(O)R$^{2d1}$, —C(O)N(R$^{2d1}$)(R$^{2d2}$), —N(R$^{2d1}$)C(O)R$^{2d2}$, —OC(O)N(R$^{2d1}$)(R$^{2d2}$), —N(R$^{2d1}$)C(O)OR$^{2d2}$, —N(R$^{2d1}$)(R$^{2d2}$), =O, —OR$^{2d1}$, —SR$^{2d1}$, —S(O)R$^{2d1}$, —S(O)(NR$^{2d1}$)(R$^{2d2}$), —S(O)$_2$R$^{2d1}$, —S(O)N(R$^{2d1}$)(R$^{2d2}$), —N(R$^{2d1}$)S(O)$_2$R$^{2d2}$, C$_{3-10}$ cycloalkyl, C$_{1-6}$ alkyl-C$_{3-10}$ cycloalkyl, C$_{6-12}$ aryl, C$_{1-6}$ alkyl-C$_{6-12}$ aryl, heterocycloalkyl, C$_{1-6}$ alkyl-(heterocycloalkyl), heteroaryl, or C$_{1-6}$ alkyl-(heteroaryl);
each R$^{2d1}$ and R$^{2d2}$ is independently hydrogen, C$_{1-6}$ alkyl, C$_{1-6}$ hydroxyalkyl, C$_{1-6}$ aminoalkyl, C$_{2-6}$ alkoxyalkyl, or C$_{1-6}$ haloalkyl;
each R$^{2e}$, R$^{2f}$, R$^{2g}$, and R$^{2h}$ is independently hydrogen, C$_{1-6}$ alkyl, C$_{1-6}$ hydroxyalkyl, C$_{1-6}$ aminoalkyl, C$_{1-6}$ alkoxy, C$_{2-6}$ alkoxyalkyl, halogen, C$_{1-6}$ haloalkyl, C$_{1-6}$ haloalkoxy, —CN, or —OH;
each R$^{2j}$ is independently C$_{1-6}$ alkyl, C$_{1-6}$ hydroxyalkyl, C$_{1-6}$ aminoalkyl, C$_{1-6}$ alkoxy, C$_{2-6}$ alkoxyalkyl, halogen, C$_{1-6}$ haloalkyl, or C$_{1-6}$ haloalkoxy;
R$^3$ is hydrogen, C$_{1-6}$ alkyl, C$_{2-6}$ alkenyl, C$_{2-6}$ alkynyl, C$_{1-6}$ hydroxyalkyl, C$_{1-6}$ aminoalkyl, C$_{1-6}$ alkoxy, C$_{2-6}$ alkoxyalkyl, halogen, C$_{1-6}$ haloalkyl, C$_{1-6}$ haloalkoxy, —CN, —NO, —NO$_2$, —C(O)R$^{3a}$, —C(O)OR$^{3a}$, —OC(O)R$^{3a}$, —C(O)N(R$^{3a}$)(R$^{3b}$), —N(R$^{3a}$)C(O)R$^{3b}$, —OC(O)N(R$^{3a}$)(R$^{3b}$), —N(R$^{3a}$)C(O)OR$^{3b}$, —C(=NR$^{3a}$)N(R$^{3b}$)(R$^{3c}$), —N(R$^{3a}$)(R$^{3b}$), —N(R$^{3a}$)N(R$^{3b}$)(R$^{3c}$), —N(R$^{3a}$)N=C(R$^{3b}$)(OR$^{3c}$), —OR$^{3a}$, —SR$^{3a}$, —S(O)R$^{3a}$, —S(O)(NR$^{3a}$)(R$^{3b}$), —S(NR$^{3a}$)(NR$^{3b}$)(R$^{3c}$), —S(O)$_2$R$^{3a}$, —S(O)$_2$N(R$^{3a}$)(R$^{3b}$), —N(R$^{3a}$)S(O)$_2$(R$^{3b}$), —P(R$^{3a}$)(R$^{3b}$), —P(O)(R$^{3a}$)(R$^{3b}$), —P(O)(OR$^{3a}$)(R$^{3b}$), —P(O)(OR$^{3a}$)(OR$^{3b}$), C$_{3-10}$ cycloalkyl, C$_{1-6}$ alkyl-C$_{3-10}$ cycloalkyl, C$_{6-12}$ aryl, C$_{1-6}$ alkyl-C$_{6-12}$ aryl, heterocycloalkyl, C$_{1-6}$ alkyl-(heterocycloalkyl), heteroaryl, or C$_{1-6}$ alkyl-(heteroaryl), wherein each alkenyl or alkynyl is independently optionally substituted with 1 to 3 R$^{3d}$ groups, each cycloalkyl is optionally substituted with 1 to 3 R$^{3e}$ groups, each aryl is optionally substituted with 1 to 3 R$^{3f}$ groups, each heterocycloalkyl is optionally substituted with 1 to 3 R$^{3g}$ groups, and each heteroaryl is optionally substituted with 1 to 3 R$^{3h}$ groups;

each R$^{3a}$, R$^{3b}$, and R$^{3c}$ is independently hydrogen, C$_{1-6}$ alkyl, C$_{1-6}$ hydroxyalkyl, C$_{2-6}$ alkoxyalkyl, C$_{1-6}$ haloalkyl, C$_{3-10}$ cycloalkyl, C$_{1-6}$ alkyl-C$_{3-10}$ cycloalkyl, C$_{6-12}$ aryl, C$_{1-6}$ alkyl-C$_{6-12}$ aryl, heterocycloalkyl, or heteroaryl;

alternatively, R$^{3a}$, R$^{3b}$, and R$^{3c}$ when attached to the same atom can be combined with the atom to which they are attached to form a heterocycloalkyl;

each R$^{3d}$ is independently —N(R$^{3d1}$)(R$^{3d2}$), —OR$^{3d1}$, C$_{3-10}$ cycloalkyl, C$_{1-6}$ alkyl-C$_{3-10}$ cycloalkyl, C$_{6-12}$ aryl, C$_{1-6}$ alkyl-C$_{6-12}$ aryl, heterocycloalkyl, or heteroaryl;

each R$^{3d1}$ and R$^{3d2}$ is independently hydrogen, C$_{1-6}$ alkyl, or —C(O)O—(C$_{1-6}$ alkyl);

each R$^{3e}$, R$^{3f}$, R$^{3g}$, and R$^{3h}$ is independently hydrogen, C$_{1-6}$ alkyl, C$_{1-6}$ alkoxy, halogen, C$_{1-6}$ haloalkyl or C$_{1-6}$ haloalkoxy;

R$^4$ is hydrogen, C$_{1-6}$ alkyl, C$_{2-6}$ alkenyl, C$_{2-6}$ alkynyl, C$_{1-6}$ alkoxy, halogen, C$_{1-6}$ haloalkyl, C$_{1-6}$ haloalkoxy, or —CN;

R$^5$ is hydrogen, C$_{1-6}$ alkyl, C$_{2-6}$ alkenyl, C$_{2-6}$ alkynyl, C$_{1-6}$ hydroxyalkyl, C$_{2-6}$ alkoxyalkyl, C$_{1-6}$ haloalkyl, C$_{3-10}$ cycloalkyl, C$_{1-6}$ alkyl-C$_{3-10}$ cycloalkyl, C$_{6-12}$ aryl, C$_{1-6}$ alkyl-C$_{6-12}$ aryl, heterocycloalkyl, C$_{1-6}$ alkyl-(heterocycloalkyl), heteroaryl, or C$_{1-6}$ alkyl-(heteroaryl), wherein the alkyl is optionally substituted with R$^{5a}$;

R$^{5a}$ is —OSi(R$^{5a1}$)(R$^{5a2}$)(R$^{5a3}$);

R$^{5a1}$, R$^{5a2}$, and R$^{5a3}$ are each independently C$_{1-6}$ alkyl; and

R$^6$ is

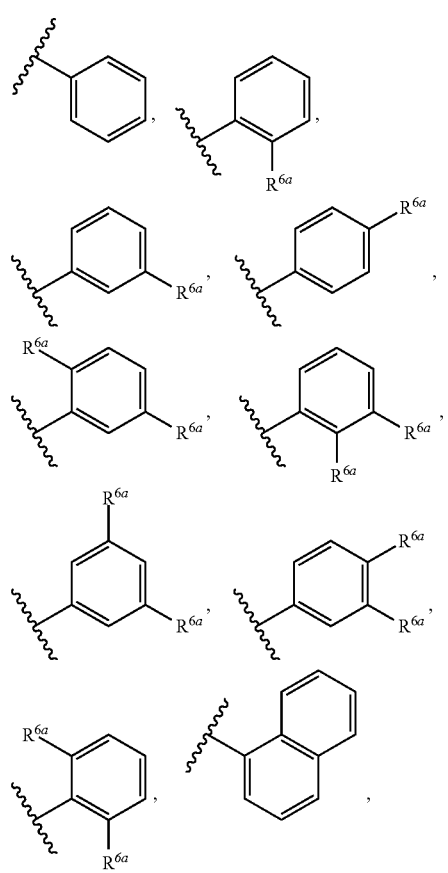

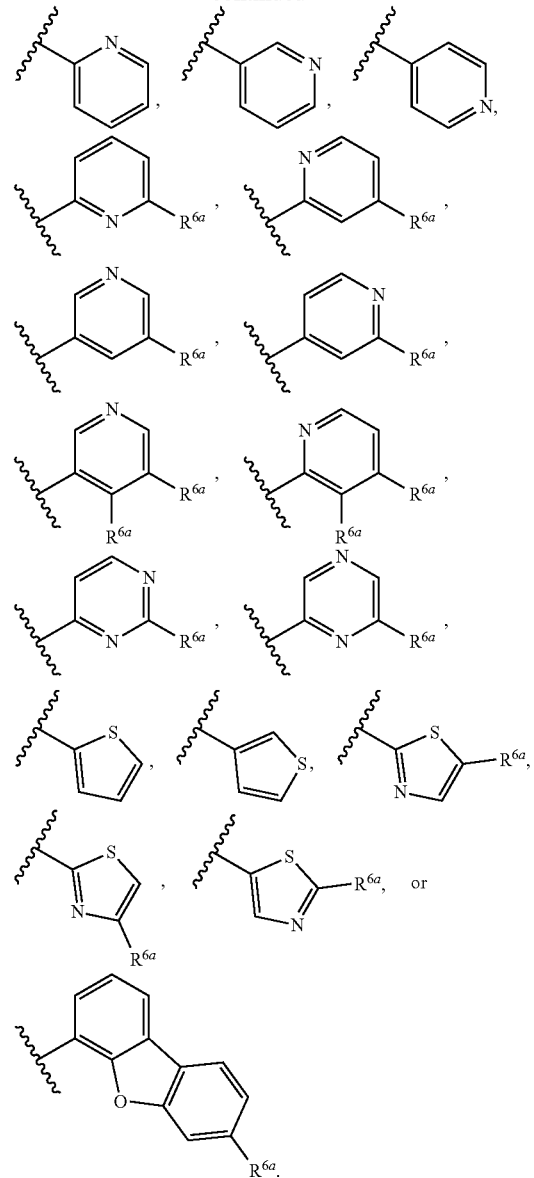

each R$^{6a}$ is independently C$_{1-6}$ alkyl, C$_{2-6}$ alkenyl, C$_{2-6}$ alkynyl, C$_{1-6}$ hydroxyalkyl, C$_{1-6}$ aminoalkyl, C$_{1-6}$ alkoxy, C$_{2-6}$ alkoxyalkyl, halogen, C$_{1-6}$ haloalkyl, C$_{1-6}$ haloalkoxy, —CN, —NO$_2$, —C(O)R$^{6b}$, —C(O)OR$^{6b}$, —OC(O)R$^{6b}$, —C(O)N(R$^{6b}$)(R$^{6c}$), —N(R$^{6b}$)C(O)R$^{6c}$, —C(=NR$^{6b}$)N(R$^{6c}$)(R$^{6d}$), —N(R$^{6b}$)(R$^{6c}$), —OR$^{6b}$, —SR$^{6b}$, —S(O)R$^{6b}$, —S(O)$_2$R$^{6b}$, —S(NR$^{6b}$)(NR$^{6c}$)R$^{6d}$, —S(O)(NR$^{6b}$)(R$^{6c}$), —S(O)$_2$N(R$^{6b}$)(R$^{6c}$), —N(R$^{6b}$)S(O)$_2$(R$^{6c}$), —P(R$^{6b}$)(R$^{6c}$), —P(O)(R$^{6b}$)(R$^{6c}$), —P(O)(OR$^{6b}$)(R$^{6c}$), —P(O)(OR$^{6b}$)(OR$^{6c}$), C$_{3-10}$ cycloalkyl, C$_{1-6}$ alkyl-C$_{3-10}$ cycloalkyl, C$_{6-12}$ aryl, C$_{1-6}$ alkyl-C$_{6-12}$ aryl, heterocycloalkyl, C$_{1-6}$ alkyl-(heterocycloalkyl), heteroaryl, or C$_{1-6}$ alkyl-(heteroaryl), wherein the cycloalkyl, aryl, heterocycloalkyl, or heteroaryl is each optionally substituted with 1 to 3 R$^{6e}$, the alkyl is optionally substituted with R$^{6f}$, and the alkynyl is optionally substituted with 1 to 4 R$^{6j}$;

each R$^{6b}$, R$^{6c}$ and R$^{6d}$ is independently hydrogen, C$_{1-6}$ alkyl, C$_{1-6}$ hydroxyalkyl, C$_{1-6}$ aminoalkyl, C$_{2-6}$ alkoxyalkyl, C$_{1-6}$ haloalkyl, C$_{3-10}$ cycloalkyl, C$_{1-6}$ alkyl-C$_{3-10}$ cycloalkyl, $C_{6-12}$ aryl, $C_{1-6}$ alkyl-$C_{6-12}$ aryl, heterocycloalkyl, $C_{1-6}$ alkyl-(heterocycloalkyl), heteroaryl, or $C_{1-6}$ alkyl-(heteroaryl), wherein the cycloalkyl, aryl, heterocycloalkyl, or heteroaryl is optionally substituted by 1 to 3 $R^{6k}$;

each $R^{6k}$ is independently $C_{1-6}$ alkyl, $C_{1-6}$ hydroxyalkyl, $C_{1-6}$ aminoalkyl, $C_{1-6}$ alkoxy, $C_{2-6}$ alkoxyalkyl, $C_{1-6}$ haloalkyl, $C_{1-6}$ haloalkoxy, $C_{3-10}$ cycloalkyl, $C_{1-6}$ alkyl-$C_{3-10}$ cycloalkyl, heterocycloalkyl, or $C_{1-6}$ alkyl-(heterocycloalkyl));

each $R^{6e}$ is independently $C_{1-6}$ alkyl, $C_{2-6}$ alkenyl, $C_{2-6}$ alkynyl, $C_{1-6}$ hydroxyalkyl, $C_{1-6}$ aminoalkyl, $C_{1-6}$ alkoxy, $C_{2-6}$ alkoxyalkyl, halogen, $C_{1-6}$ haloalkyl, $C_{1-6}$ haloalkoxy, —CN, —NO$_2$, —C(O)R$^{6e1}$, —C(O)OR$^{6e1}$, —OC(O)R$^{6e1}$, —C(O)N(R$^{6e1}$)(R$^{6e2}$), —N(R$^{6e1}$)C(O)R$^{6e2}$, —OC(O)N(R$^{6e1}$)(R$^{6e2}$), —N(R$^{6e1}$)C(O)OR$^{6e2}$, —C(=NR$^{6e1}$)N(R$^{6e2}$)(R$^{6e3}$), —N(R$^{6e1}$)(R$^{6e2}$), =O, —OR$^{6e1}$, —SR$^{6e1}$, —S(O)R$^{6e1}$, —S(NR$^{6e1}$)(NR$^{6e2}$), —S(O)(NR$^{6e1}$)(R$^{6e2}$), —S(O)$_2$R$^{6e1}$, —S(O)$_2$N(R$^{6e1}$)(R$^{6e2}$), —SF5, —N(R$^{6e1}$)S(O)$_2$(R$^{6e2}$), —P(R$^{6e1}$)(R$^{6e2}$), —P(O)(R$^{6e1}$)(R$^{6e2}$), —P(O)(OR$^{6e1}$)(R$^{6e2}$), —P(O)(OR$^{6e1}$)(OR$^{6e2}$), —Si(R$^{6e1}$)(R$^{6e2}$)(R$^{6e3}$), $C_{3-10}$ cycloalkyl, $C_{1-6}$ alkyl-$C_{3-10}$ cycloalkyl, $C_{6-12}$ aryl, $C_{1-6}$ alkyl-$C_{6-12}$ aryl, heterocycloalkyl, $C_{1-6}$ alkyl-heterocycloalkyl, heteroaryl, or $C_{1-6}$ alkyl-heteroaryl, wherein the cycloalkyl, aryl, heterocycloalkyl, or heteroaryl is each optionally substituted with 1 to 3 $R^{6h}$, and the alkyl is optionally substituted with 1 to 3 $R^{6m}$;

each $R^{6e1}$, $R^{6e2}$, and $R^{6e3}$ is independently hydrogen, $C_{1-6}$ alkyl, $C_{1-6}$ hydroxyalkyl, $C_{1-6}$ aminoalkyl, $C_{1-6}$ alkoxyalkyl, $C_{1-6}$ haloalkyl, $C_{3-10}$ cycloalkyl, $C_{1-6}$ alkyl-$C_{3-10}$ cycloalkyl, $C_{6-10}$ aryl, $C_{1-6}$ alkyl-$C_{6-10}$ aryl, heterocycloalkyl, $C_{1-6}$ alkyl-(heterocycloalkyl), heteroaryl, or $C_{1-6}$ alkyl-(heteroaryl), wherein the cycloalkyl, aryl, heterocycloalkyl, or heteroaryl is optionally substituted with 1 to 3 $R^{6n}$;

each $R^{6n}$ is $C_{1-6}$ alkyl, $C_{2-6}$ alkenyl, $C_{2-6}$ alkynyl, $C_{1-6}$ hydroxyalkyl, $C_{1-6}$ aminoalkyl, $C_{1-6}$ alkoxy, $C_{2-6}$ alkoxyalkyl, halogen, $C_{1-6}$ haloalkyl, $C_{1-6}$ haloalkoxy, —CN, —C(O)R$^{6n1}$, —C(O)OR$^{6n1}$, —OC(O)R$^{6n1}$, —C(O)N(R$^{6n1}$)(R$^{6n2}$), —N(R$^{6n1}$)C(O)R$^{6n2}$, —OC(O)N(R$^{6n1}$)(R$^{6n2}$), —N(R$^{6n1}$)C(O)OR$^{6n2}$, —C(=NR$^{6n1}$)N(R$^{6n2}$)(R$^{6n3}$), —N(R$^{6n1}$)(R$^{6n2}$), =O, —OH, —SR$^{6n1}$, —S(O)R$^{6n1}$, —S(NR$^{6n1}$)(NR$^{6n2}$)R$^{6n3}$, —S(O)(NR$^{6n1}$)(R$^{6n2}$), —S(O)$_2$R$^{6n1}$, —S(O)$_2$N(R$^{6n1}$)(R$^{6n2}$), or —N(R$^{6n1}$)S(O)$_2$(R$^{6n2}$);

each $R^{6n1}$, $R^{6n2}$ and $R^{6n3}$ is independently hydrogen, $C_{1-6}$ alkyl, $C_{1-6}$ hydroxyalkyl, $C_{1-6}$ aminoalkyl, $C_{2-6}$ alkoxyalkyl, $C_{1-6}$ haloalkyl, $C_{3-10}$ cycloalkyl, $C_{1-6}$ alkyl-$C_{3-10}$ cycloalkyl, $C_{6-10}$ aryl, $C_{1-6}$ alkyl-$C_{6-10}$ aryl, heterocycloalkyl, $C_{1-6}$ alkyl-(heterocycloalkyl), heteroaryl, or $C_{1-6}$ alkyl-(heteroaryl);

each $R^{6h}$ is independently $C_{1-6}$ alkyl, $C_{2-6}$ alkenyl, $C_{2-6}$ alkynyl, $C_{1-6}$ hydroxyalkyl, $C_{1-6}$ aminoalkyl, $C_{1-6}$ alkoxy, $C_{2-6}$ alkoxyalkyl, halogen, $C_{1-6}$ haloalkyl, $C_{1-6}$ haloalkoxy, —CN, —C(O)R$^{6h1}$, —C(O)OR$^{6h1}$, —OC(O)R$^{6h1}$, —C(O)N(R$^{6h1}$)(R$^{6h2}$), —N(R$^{6h1}$)C(O)R$^{6h2}$, —OC(O)N(R$^{6h1}$)(R$^{6h2}$), —N(R$^{6h1}$)C(O)OR$^{6h2}$, —C(=NR$^{6h1}$)N(R$^{6h2}$)(R$^{6h3}$), —N(R$^{6h1}$)(R$^{6h2}$), =O, —OH, —SR$^{6h1}$, —S(O)R$^{6h1}$, —S(NR$^{6h1}$)(NR$^{6h2}$)R$^{6h3}$, —S(O)(NR$^{6h1}$)(R$^{6h2}$), —S(O)$_2$R$^{6h1}$, —S(O)$_2$N(R$^{6h1}$)(R$^{6h2}$), —N(R$^{6h1}$)S(O)$_2$(R$^{6h2}$), $C_{3-10}$ cycloalkyl, $C_{1-6}$ alkyl-$C_{3-10}$ cycloalkyl, heterocycloalkyl, or $C_{1-6}$ alkyl-(heterocycloalkyl);

each $R^{6h1}$, $R^{6h2}$, and $R^{6h3}$ is independently hydrogen, $C_{1-6}$ alkyl, $C_{1-6}$ hydroxyalkyl, $C_{1-6}$ aminoalkyl, $C_{2-6}$ alkoxyalkyl, $C_{1-6}$ haloalkyl, $C_{3-10}$ cycloalkyl, $C_{1-6}$ alkyl-$C_{3-10}$ cycloalkyl, $C_{6-10}$ aryl, $C_{1-6}$ alkyl-$C_{6-10}$ aryl, heterocycloalkyl, $C_{1-6}$ alkyl-(heterocycloalkyl), heteroaryl, or $C_{1-6}$ alkyl-(heteroaryl);

each $R^{6m}$ is independently halogen, $C_{1-6}$ haloalkyl, $C_{1-6}$ haloalkoxy, —CN, —C(O)R$^{6m1}$, —C(O)OR$^{6m1}$, —OC(O)R$^{6m1}$, —C(O)N(R$^{6m1}$)(R$^{6m2}$), —N(R$^{6m3}$)C(O)R$^{6m2}$, —OC(O)N(R$^{6m1}$)(R$^{6m2}$), —N(R$^{6m1}$)C(O)OR$^{6m2}$, —C(=NR$^{6m3}$)N(R$^{6m1}$)(R$^{6m2}$), —N(R$^{6m1}$)(R$^{6m2}$), =O, —OH, —SR$^{6m1}$, —S(O)R$^{6m1}$, —S(NR$^{6m1}$)(NR$^{6m2}$)R$^{6m3}$, —S(O)(NR$^{6m1}$)(R$^{6m2}$), —S(O)$_2$R$^{6m1}$, —S(O)$_2$N(R$^{6m1}$)(R$^{6m2}$), or —N(R$^{6m3}$)S(O)$_2$(R$^{6m2}$);

each $R^{6m1}$, $R^{6m2}$, and $R^{6m3}$ is independently hydrogen, $C_{1-6}$ alkyl, $C_{1-6}$ hydroxyalkyl, $C_{1-6}$ aminoalkyl, $C_{2-6}$ alkoxyalkyl, $C_{1-6}$ haloalkyl, $C_{3-10}$ cycloalkyl, $C_{1-6}$ alkyl-$C_{3-10}$ cycloalkyl, $C_{6-10}$ aryl, $C_{1-6}$ alkyl-$C_{6-10}$ aryl, heterocycloalkyl, $C_{1-6}$ alkyl-(heterocycloalkyl), heteroaryl, or $C_{1-6}$ alkyl-(heteroaryl);

$R^{6f}$ is —OSi(R$^{6f1}$)(R$^{6f2}$)(R$^{6f3}$);

$R^{6f1}$, $R^{6f2}$, and $R^{6f3}$ are each independently $C_{1-6}$ alkyl;

each $R^{6j}$ is independently $C_{2-6}$ alkoxyalkyl, halogen, $C_{1-6}$ haloalkyl, $C_{1-6}$ haloalkoxy, —CN, —C(O)R$^{6j1}$, —C(O)OR$^{6j1}$, —OC(O)R$^{6j1}$, —C(O)N(R$^{6j1}$)(R$^{6j2}$), —N(R$^{6j3}$)C(O)R$^{6j2}$, —OC(O)N(R$^{6j1}$)(R$^{6j2}$), —N(R$^{6j1}$)C(O)OR$^{6j2}$, —C(=NR$^{6j3}$)N(R$^{6j1}$)(R$^{6j2}$), —N(R$^{6j1}$)(R$^{6j2}$), =O, —OR$^{6j1}$, —SR$^{6j1}$, —S(O)R$^{6j1}$, —S(NR$^{6j1}$)(NR$^{6j2}$), —S(NR$^{6j1}$)NR$^{6j2}$)R$^{6j3}$, —S(O)(NR$^{6j1}$)(R$^{6j2}$), —S(O)$_2$R$^{6j1}$, —S(O)$_2$N(R$^{6j1}$)(R$^{6j2}$), —N(R$^{6j1}$)S(O)$_2$(R$^{6j2}$), —Si(R$^{6j1}$)(R$^{6j2}$)(R$^{6j3}$), $C_{3-10}$ cycloalkyl, $C_{6-12}$ aryl, heterocycloalkyl, or heteroaryl, wherein the cycloalkyl, aryl, heterocycloalkyl, or heteroaryl is optionally substituted with 1 to 3 $R^{6p}$;

each $R^{6j1}$, $R^{6j2}$, and $R^{6j3}$ is independently hydrogen, $C_{1-6}$ alkyl, $C_{1-6}$ hydroxyalkyl, $C_{1-6}$ aminoalkyl, $C_{2-6}$ alkoxyalkyl, $C_{1-6}$ haloalkyl, $C_{3-10}$ cycloalkyl, $C_{1-6}$ alkyl-$C_{3-10}$ cycloalkyl, $C_{6-10}$ aryl, $C_{1-6}$ alkyl-$C_{6-10}$ aryl, heterocycloalkyl, $C_{1-6}$ alkyl-(heterocycloalkyl), heteroaryl, or $C_{1-6}$ alkyl-(heteroaryl);

each $R^{6p}$ is independently $C_{1-6}$ alkyl, $C_{1-6}$ hydroxyalkyl, $C_{1-6}$ aminoalkyl, $C_{1-6}$ alkoxy, $C_{2-6}$ alkoxyalkyl, halogen, $C_{1-6}$ haloalkyl, $C_{1-6}$ haloalkoxy, —CN, —C(O)R$^{6p1}$, —C(O)OR$^{6p1}$, —OC(O)R$^{6p1}$, —C(O)N(R$^{6p1}$)(R$^{6p2}$), —N(R$^{6p1}$)C(O)R$^{6p2}$, —OC(O)N(R$^{6p1}$)(R$^{6p2}$), —N(R$^{6p1}$)C(O)OR$^{6p2}$, —C(=NR$^{6p3}$)N(R$^{6p1}$)(R$^{6p2}$), —N(R$^{6p1}$)(R$^{6p2}$), =O, —OH, —SR$^{6p1}$, —S(O)R$^{6p1}$, —S(NR$^{6p1}$)(NR$^{6p2}$)R$^{6p3}$, —S(O)(NR$^{6p1}$)(R$^{6p2}$), —S(O)$_2$R$^{6p1}$, —S(O)$_2$N(R$^{6p1}$)(R$^{6p2}$), or —N(R$^{6p1}$)S(O)$_2$(R$^{6p2}$);

each $R^{6p1}$, $R^{6p2}$, and $R^{6p3}$ is independently hydrogen, $C_{1-6}$ alkyl, $C_{1-6}$ hydroxyalkyl, $C_{1-6}$ aminoalkyl, $C_{2-6}$ alkoxyalkyl, $C_{1-6}$ haloalkyl, $C_{3-10}$ cycloalkyl, $C_{1-6}$ alkyl-$C_{3-10}$ cycloalkyl, $C_{6-10}$ aryl, $C_{1-6}$ alkyl-$C_{6-10}$ aryl, heterocycloalkyl, $C_{1-6}$ alkyl-(heterocycloalkyl), heteroaryl, or $C_{1-6}$ alkyl-(heteroaryl);

or $R^5$ and one $R^{6a}$ together with the atoms to which they are attached form a heterocycloalkyl, optionally substituted with 1 to 3 $R^{6g}$;

each $R^{6g}$ is independently $C_{1-6}$ alkyl, $C_{2-6}$ alkenyl, $C_{2-6}$ alkynyl, $C_{1-6}$ hydroxyalkyl, $C_{1-6}$ aminoalkyl, $C_{2-6}$ alkoxyalkyl, halogen, $C_{1-6}$ haloalkyl, $C_{1-6}$ haloalkoxy, or —CN;

$R^7$ is hydrogen, $C_{1-6}$ alkyl, $C_{1-6}$ hydroxyalkyl, $C_{1-6}$ aminoalkyl, $C_{1-6}$ alkoxy, $C_{2-6}$ alkoxyalkyl, $C_{1-6}$ alkylthio, halogen, $C_{1-6}$ haloalkyl, —CN, —OH, —NH$_2$, $C_{3-10}$ cycloalkyl, $C_{1-6}$ alkyl-$C_{3-10}$ cycloalkyl, heterocycloalkyl, or $C_{1-6}$ alkyl-(heterocycloalkyl);

each heterocycloalkyl is a 3 to 20 membered ring having 1 to 4 heteroatoms each independently N, O or S; and each heteroaryl is a 5 to 18 membered ring having 1 to 4 heteroatoms each independently N, O or S;

provided that $R^5$ and $R^6$ are not both $C_{1-4}$ alkyl; and when $R^5$ is hydrogen, $R^6$ is not isopropyl or phenyl substituted with 2-Me.

2. The compound of claim 1, or a pharmaceutically acceptable salt thereof, wherein $R^1$ is hydrogen, Me, —OMe, F, or Cl.

3. The compound of claim 1, or a pharmaceutically acceptable salt thereof, wherein $R^1$ is hydrogen.

4. The compound of claim 1, or a pharmaceutically acceptable salt thereof, wherein $R^2$ is hydrogen, Me, Et, iPr, —CH=CH2, —CH=CHMe, —C(Me)=CH2, —CMe=CHMe, —CH=C(Me)$_2$, —CH=CHEt, —C≡CH, —C≡C-Me, —C≡C-Et, —C≡C-tBu, —C≡C—CH$_2$OH, —C≡C—CMe$_2$(OH), —C≡C—CH$_2$NH$_2$, —C≡C—CH$_2$NHC(O)OtBu, —C≡C—CMe$_2$(SO2Me), —CH$_2$OH, —CH$_2$CH$_2$CH$_2$OH, —CH(OH)CH$_2$CH$_3$, —OMe, —OEt, —OCH$_2$CH=CH$_2$, —CH$_2$OMe, —CH$_2$NHMe, —CH$_2$NMe$_2$, —CH$_2$CH$_2$COOEt, F, Cl, Br, I, —CF$_3$, —CN, —NO, —NO$_2$, —C(O)H, —COOH, —COOMe, —NHCOMe, —NH$_2$, —NHMe, —NMe$_2$, —NHCH$_2$CH$_2$OH, —NHCH$_2$CH$_2$OMe, —NHSO$_2$Me, —OH, —NH—N=CH—OEt, —NH—NH$_2$, SMe, SO$_2$Me, cyclopropyl,

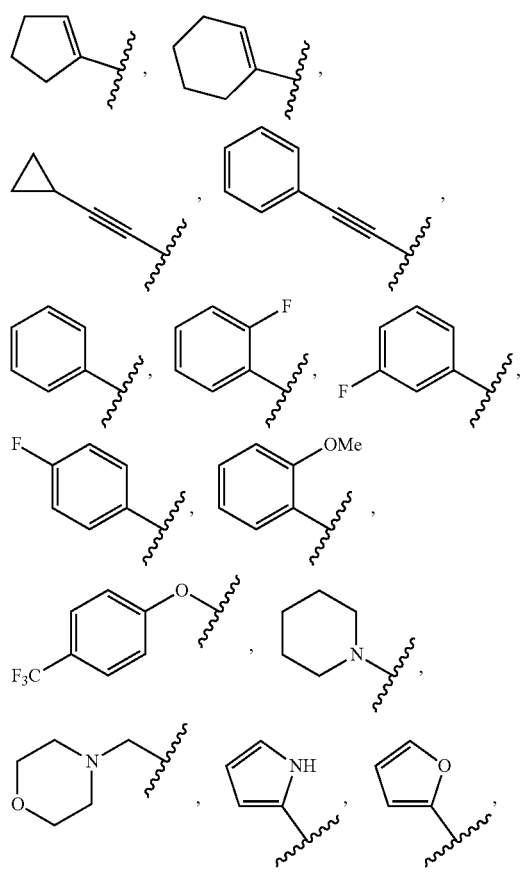

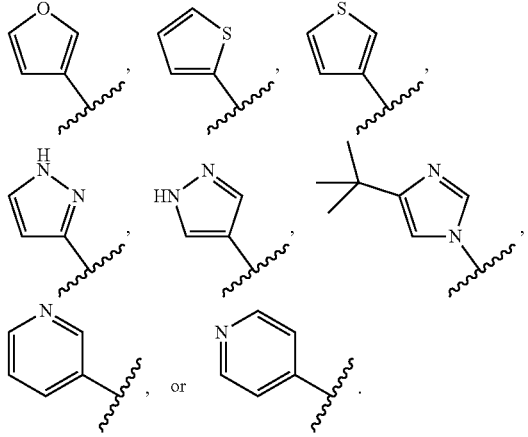

5. The compound of claim 1, or a pharmaceutically acceptable salt thereof, wherein $R^3$ is hydrogen, Me, Et, —CH$_2$OH, —OMe, —CH$_2$OMe, F, Cl, Br, —CF$_3$, —CN, —NO$_2$, —COOMe, —CONH$_2$, —NH$_2$, —NHSO$_2$Me, or

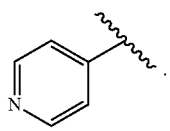 [SMILES: *c1ccncc1]

6. The compound of claim 1, or a pharmaceutically acceptable salt thereof, wherein $R^4$ is hydrogen, Me, F, Cl, or Br.

7. The compound of claim 1, or a pharmaceutically acceptable salt thereof, wherein $R^4$ is hydrogen.

8. The compound of claim 1, or a pharmaceutically acceptable salt thereof, wherein $R^1$ is hydrogen;

$R^2$ is hydrogen, $C_{1-3}$ alkyl, $C_{2-3}$ alkenyl, $C_{2-6}$ alkynyl, $C_{1-3}$ hydroxyalkyl, $C_{2-3}$ alkoxyalkyl, halogen, —CN, —NO, —NO$_2$, —C(O)R$^{2a}$, —N(R$^{2a}$)C(O)R$^{2b}$, —N(R$^{2a}$)(R$^{2b}$), —OR$^{2a}$, or a 5 to 6 membered heteroaryl ring having 1 to 2 heteroatoms each independently N, O, or S;

$R^{2a}$ and $R^{2b}$ are each independently hydrogen or $C_{1-3}$ alkyl;

$R^3$ is hydrogen, $C_{1-3}$ alkyl, halogen, —CN or —NO$_2$; and $R^4$ is hydrogen.

9. The compound of claim 1, or a pharmaceutically acceptable salt thereof, wherein $R^5$ is Me, Et, nPr, nBu, —CH$_2$CMe$_3$, —CH$_2$C—CMe, —CH$_2$CH$_2$C—CH, —CH$_2$CH$_2$OMe, —CH$_2$CH$_2$OSi(Me)$_2$(tBu), CF$_3$, —CH$_2$CF$_2$H, —CH$_2$CF$_3$, -continued

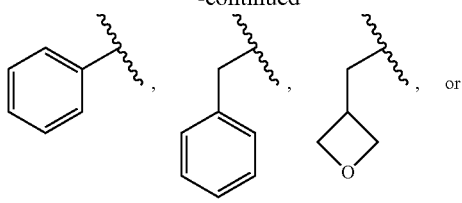

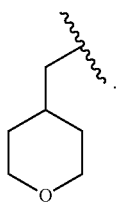

10. The compound of claim 1, or a pharmaceutically acceptable salt thereof, wherein $R^7$ is hydrogen, Me, Et, OMe, —$CH_2NMe_2$, Cl, OH, $NH_2$, SMe, or

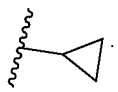

11. The compound of claim 1, or a pharmaceutically acceptable salt thereof, having the Formula (IIa):

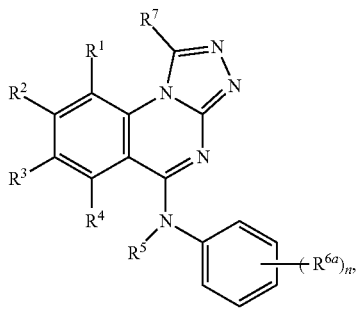

(IIa)

wherein n is 0, 1, or 2.

12. The compound of claim 1, or a pharmaceutically acceptable salt thereof, having the Formula (IIa-1):

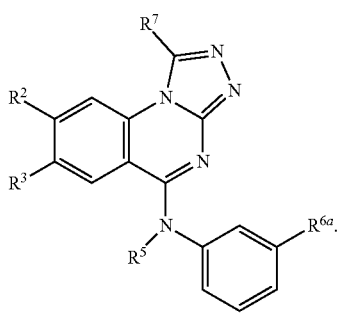

(IIa-1)

13. The compound of claim 1, or a pharmaceutically acceptable salt thereof, wherein each $R^{6a}$ is independently $C_{1-6}$ alkyl, $C_{2-6}$ alkynyl, $C_{1-6}$ hydroxyalkyl, $C_{1-6}$ alkoxy, $C_{2-6}$ alkoxyalkyl, halogen, $C_{1-6}$ haloalkyl, $C_{1-6}$ haloalkoxy, —CN, —$NO_2$, —C(O)$R^{6b}$, —C(O)O$R^{6b}$, —C(O)N($R^{6b}$)($R^{6c}$), —N($R^{6b}$)($R^{6c}$), —O$R^{6b}$, $C_{3-10}$ cycloalkyl, $C_{6-12}$ aryl, heterocycloalkyl, or heteroaryl, wherein the cycloalkyl, aryl, heterocycloalkyl, or heteroaryl is each optionally substituted with 1 to 3 $R^{6e}$, and the alkyl is optionally substituted with $R^{6f}$;

each $R^{6b}$ and $R^{6c}$ is independently hydrogen or $C_{1-6}$ alkyl;

each $R^{6e}$ is independently $C_{1-6}$ alkyl, $C_{2-6}$ alkenyl, $C_{2-6}$ alkynyl, $C_{1-6}$ hydroxyalkyl, $C_{1-6}$ alkoxy, $C_{2-6}$ alkoxyalkyl, halogen, $C_{1-6}$ haloalkyl, —C(O)O$R^{6e1}$, —OC(O)$R^{6e1}$, —C(O)N($R^{6e1}$)($R^{6e2}$), —N($R^{6e1}$)C(O)$R^{6e2}$, —O$R^{6e1}$, —S(O)$_2$N($R^{6e1}$)($R^{6e2}$), —N($R^{6e1}$)S(O)$_2$($R^{6e2}$);

each $R^{6e1}$ and $R^{6e2}$ is independently hydrogen or $C_{1-6}$ alkyl;

$R^{6f}$ is —OSi($R^{6f1}$)($R^{6f2}$)($R^{6f3}$); and $R^{6f1}$, $R^{6f2}$, and $R^{6f3}$ are each independently $C_{1-6}$ alkyl.

14. The compound of claim 1, or a pharmaceutically acceptable salt thereof, wherein each $R^{6h}$ is independently Me, —$CH_2OH$, —$CH_2NHMe$, OMe, $NH_2$, $CF_3$, CN, —(CO)Me, —(CO)tBu, —(CO)—$CH_2OH$, $CO_2Me$, $CO_2tBu$, =O, or

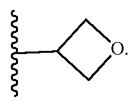

15. The compound of claim 1, or a pharmaceutically acceptable salt thereof, wherein each $R^{6m}$ is independently OH, $CF_3$, CN, $CO_2H$, $CONH_2$, $NMe_2$, $SO_2Me$, or

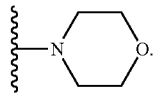

16. The compound of claim 1, or a pharmaceutically acceptable salt thereof, wherein each $R^{6e}$ is independently Me, Et, iPr, tBu, —$CH_2OH$, —C(OH)Me$_2$, —OMe, —OEt, —OCH$_2$CH$_2$CH$_3$, —CH$_2$OMe, —OCH$_2$CH$_2$NMe$_2$, F, Cl, Br, CHF$_2$, —CF$_3$, —CH$_2$CHF$_2$, —CH$_2$CF$_3$, —CF$_2$CH$_3$, —C(CH$_3$)$_2$CF$_3$, OCF$_3$, —OCH$_2$CF$_3$, —OCH(CH$_3$)CF$_3$, CN, —C(O)Me, —C(O)tBu, CO$_2$H, CO$_2$Me, CO$_2$tBu, C(O)NH$_2$, =O, OH, NH$_2$, NMe$_2$, —NMeCH$_2$CH$_2$OMe, —NHC(O)Me, —NHC(O)tBu, —NHCO$_2$tBu, SO$_2$Me, SO$_2$Et, SO$_2$(iPr), SO$_2$(iBu), SO$_2$CF$_3$, —CH$_2$SO$_2$Me, SO(N=H)Me, SO$_2$NH$_2$, SO$_2$NHMe, SO$_2$NMe$_2$, —SO$_2$NHCH$_2$CH$_2$OH, —NHSO$_2$Me, SF$_5$, —POMe$_2$,

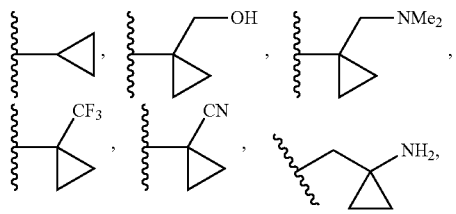

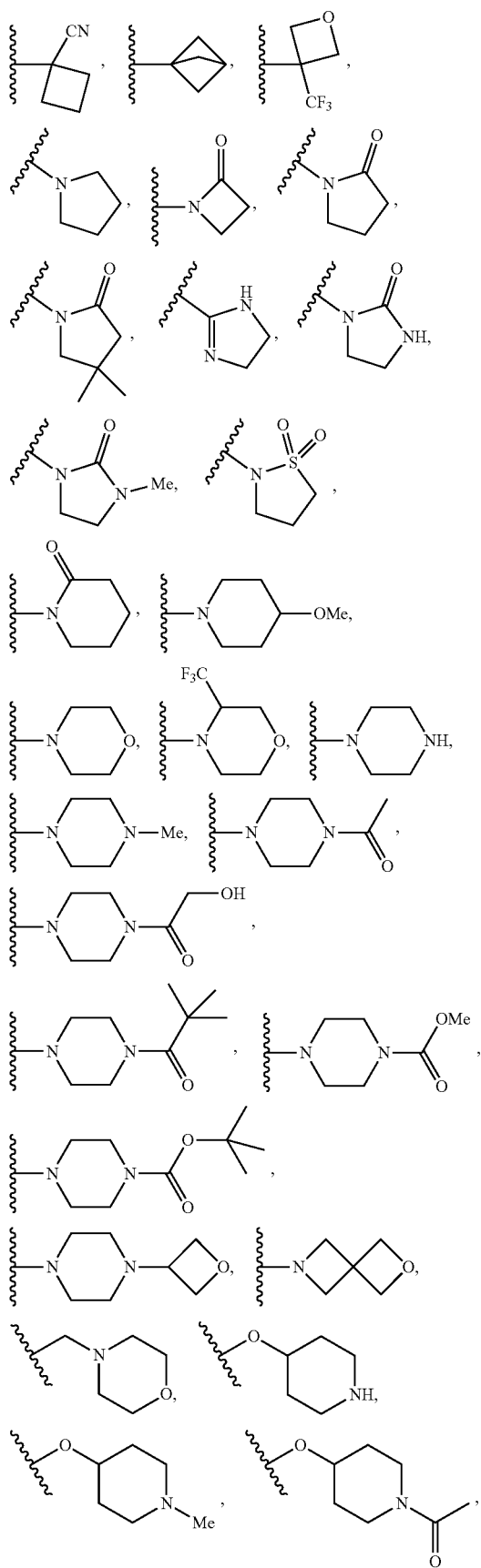
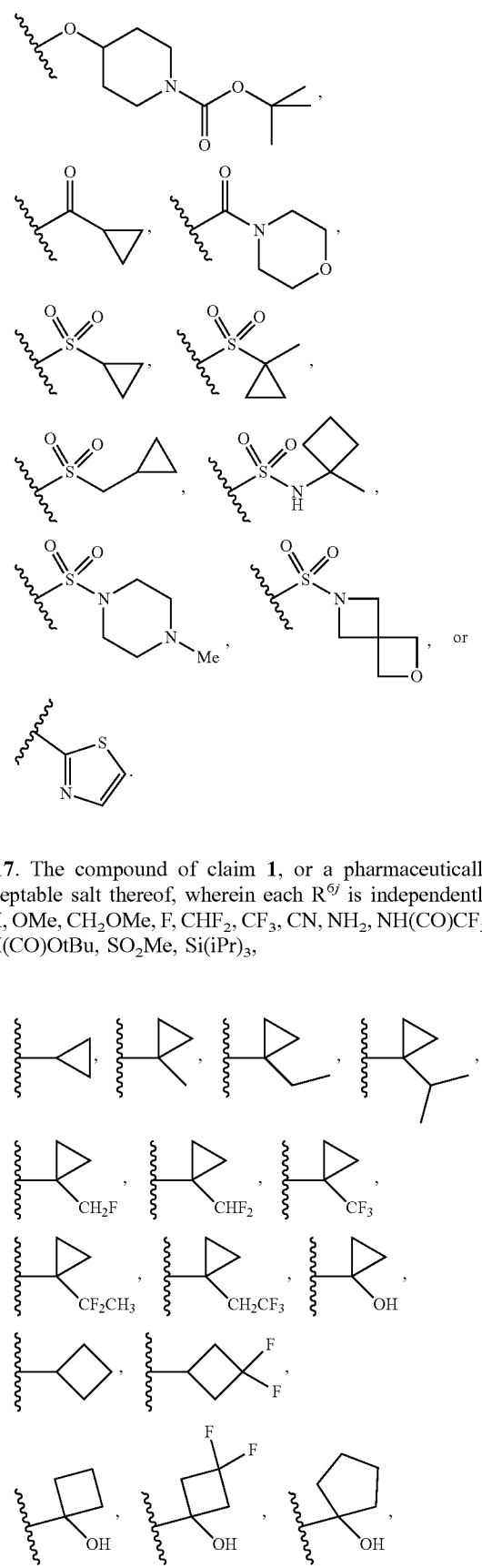
17. The compound of claim 1, or a pharmaceutically acceptable salt thereof, wherein each $R^{6j}$ is independently OH, OMe, $CH_2OMe$, F, $CHF_2$, $CF_3$, CN, $NH_2$, $NH(CO)CF_3$, $NH(CO)OtBu$, $SO_2Me$, $Si(iPr)_3$, -continued

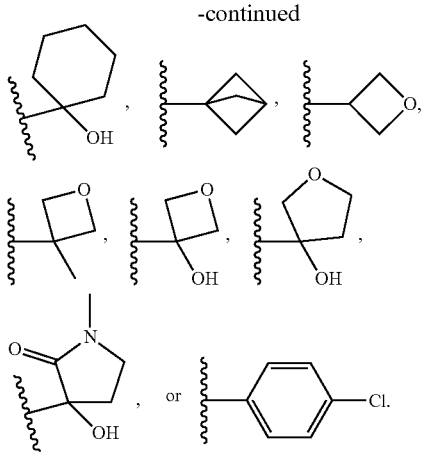

18. The compound of claim 1, or a pharmaceutically acceptable salt thereof, wherein each $R^{6p}$ is independently Me, Et, iPr, F, Cl, $CH_2F$, $CHF_2$, $CF_3$, $CF_2CH_3$, $CH_2CF_3$, =O, or OH.

19. The compound of claim 1, or a pharmaceutically acceptable salt thereof, wherein each $R^{6g}$ is methyl.

20. The compound of claim 1, or a pharmaceutically acceptable salt thereof, having the structure of Formula (IIc):

(IIc)

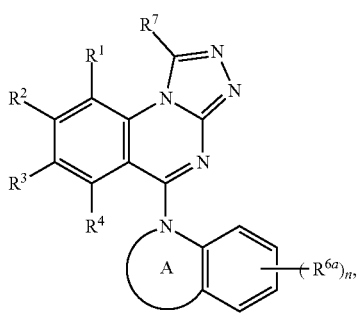

wherein

Ring A is a 5 to 8 membered heterocycloalkyl optionally having 1 to 2 additional heteroatoms each independently N, O, or S, and optionally wherein Ring A is substituted with 1 or 2 $R^{6g}$; and n is 0, 1, or 2.

21. The compound of claim 20, wherein
$R^1$ is hydrogen, $C_{1-3}$ alkyl, or halogen;
$R^2$ is hydrogen, $C_{1-3}$ alkyl, $C_{1-3}$ hydroxyalkyl, $C_{2-3}$ alkoxyalkyl, halogen, or —CN;
$R^3$ is hydrogen, $C_{1-3}$ alkyl, or halogen;
$R^4$ is hydrogen, $C_{1-3}$ alkyl, or halogen;
each $R^{6a}$ is independently $C_{1-3}$ alkyl, $C_{2-3}$ alkenyl, or $C_{2-3}$ alkynyl, wherein the alkynyl is optionally substituted with 1 to 3 $R^{6j}$;
each $R^{6j}$ is independently $C_{2-3}$ alkoxyalkyl, halogen, $C_{1-3}$ haloalkyl, $C_{1-3}$ haloalkoxy, —CN, $C_{3-8}$ cycloalkyl, or heterocycloalkyl, wherein the cycloalkyl or heterocycloalkyl is optionally substituted with 1 to 3 $R^{6p}$;
each $R^{6p}$ is independently $C_{1-3}$ alkyl, $C_{1-3}$ hydroxyalkyl, $C_{2-3}$ alkoxyalkyl, halogen, $C_{1-3}$ haloalkyl, $C_{1-3}$ haloalkoxy, or —CN; and
$R^7$ is hydrogen, $C_{1-3}$ alkyl, $C_{2-3}$ alkoxyalkyl, $C_{1-3}$ haloalkyl, or —$NH_2$.

22. The compound of claim 20, wherein
$R^1$ is hydrogen or halogen.

23. The compound of claim 20, wherein
$R^1$ is hydrogen or F.

24. The compound of claim 20, wherein
$R^4$ is hydrogen, $C_{1-3}$ alkyl, or halogen.

25. The compound of claim 20, wherein
$R^4$ is hydrogen, Me, or F.

26. The compound of claim 1, or a pharmaceutically acceptable salt thereof, having the structure of Formula (IIc-1):

(IIc-1)

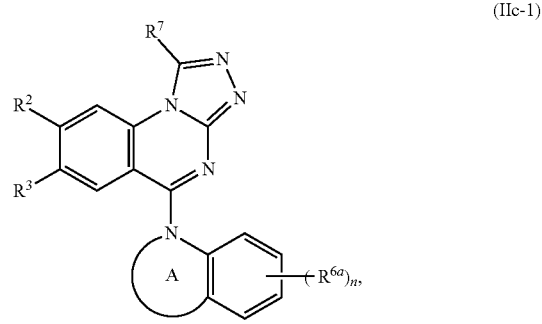

wherein

Ring A is a 5 to 8 membered heterocycloalkyl optionally having 1 to 2 additional heteroatoms each independently N, O, or S, and optionally wherein Ring A is substituted with 1 or 2 $R^{6g}$; and n is 0, 1, or 2.

27. The compound of claim 20, or a pharmaceutically acceptable salt thereof, wherein

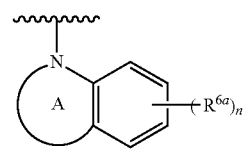

has the structure

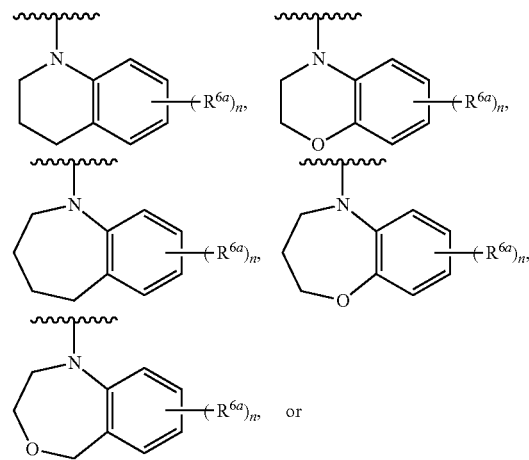

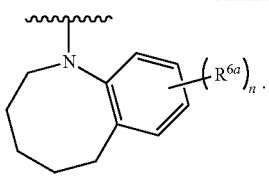
28. The compound of claim 20, or a pharmaceutically acceptable salt thereof, wherein
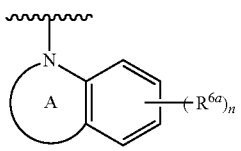
has the structure
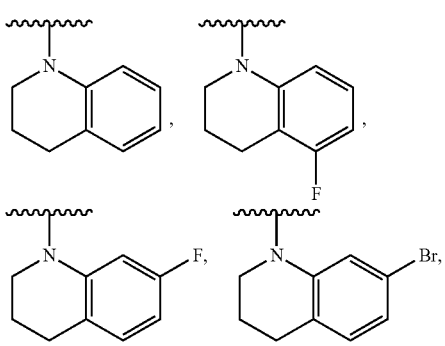
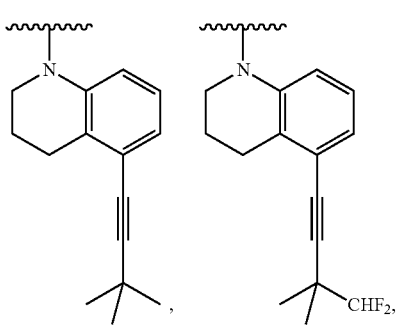
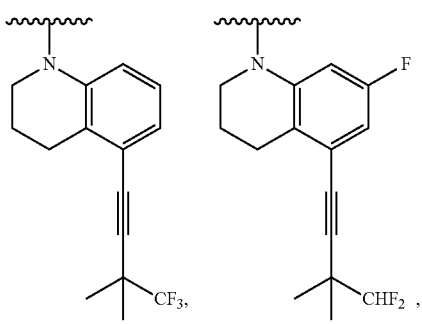
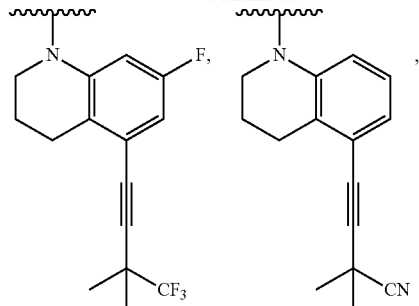
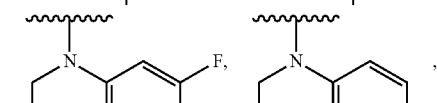
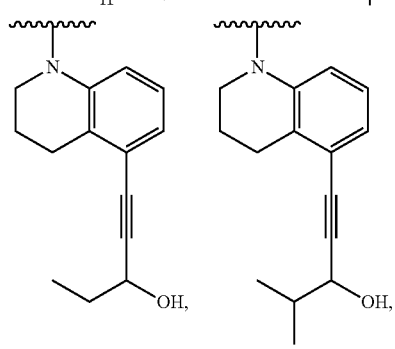
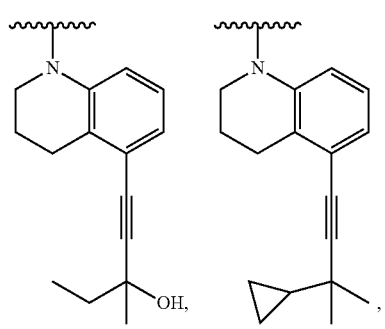
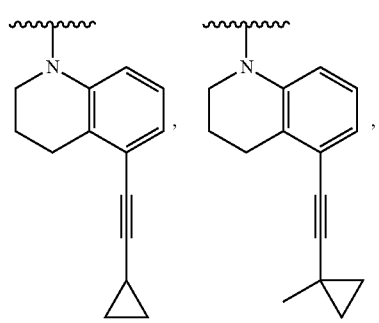

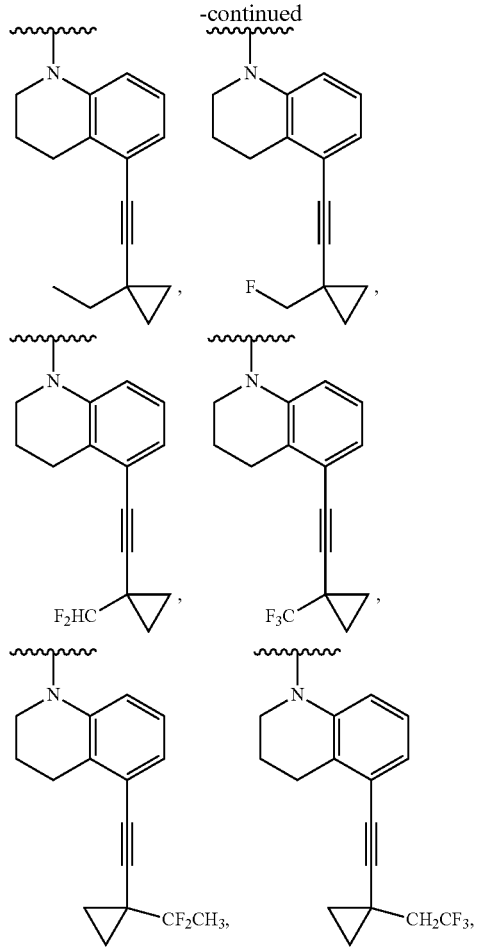
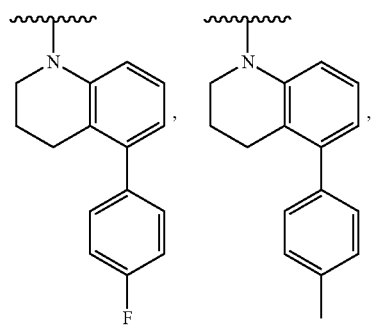
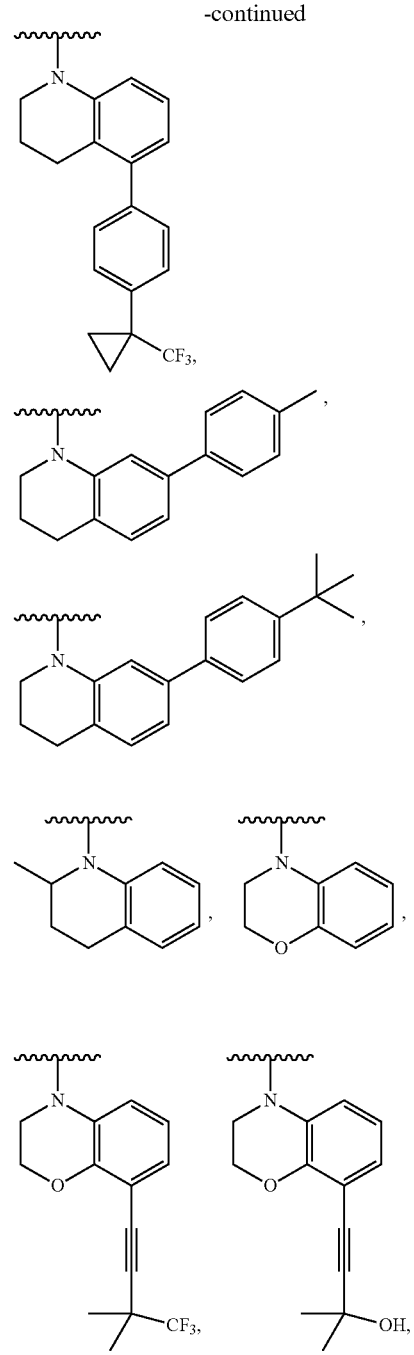

-continued

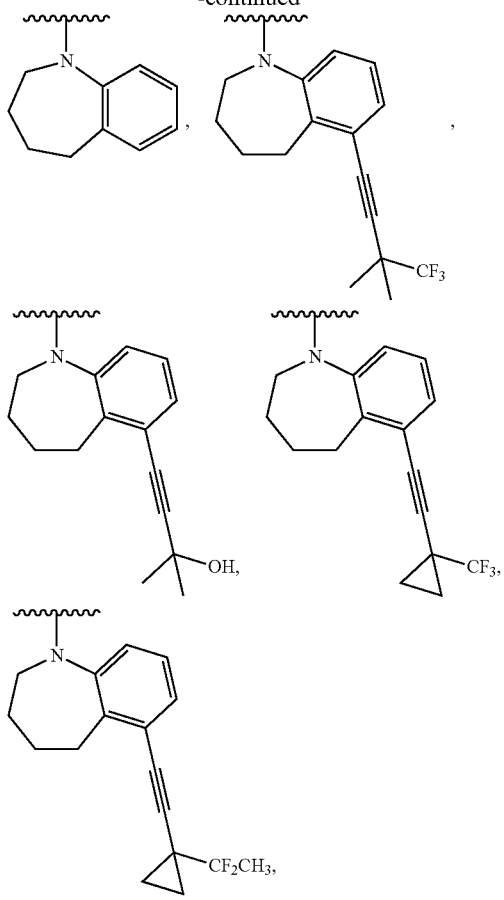

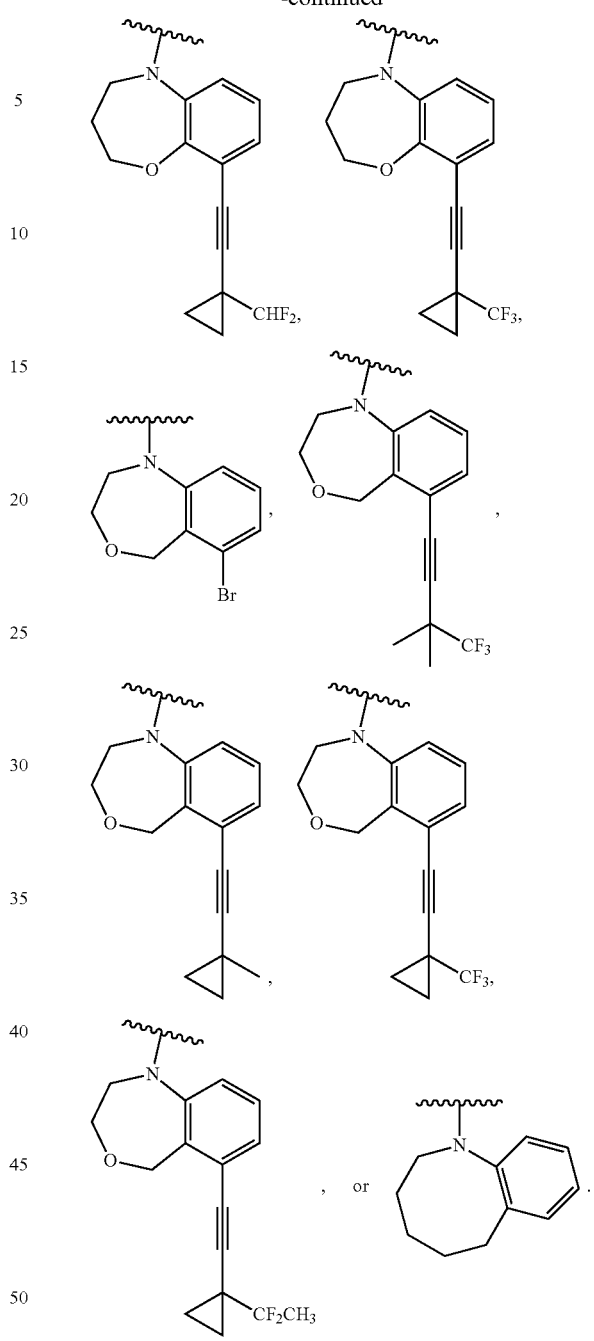

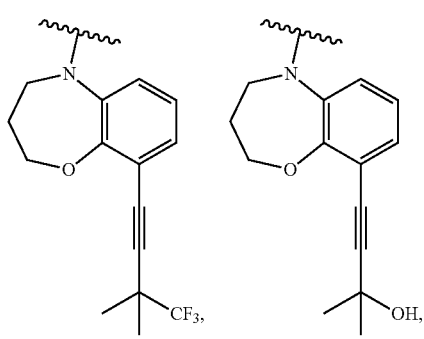

29. The compound of claim 20, or a pharmaceutically acceptable salt thereof, wherein
R$^2$ is hydrogen, C$_{1-3}$ alkyl, C$_{1-3}$ hydroxyalkyl, C$_{2-3}$ alkoxyalkyl, halogen, or —CN;
R$^3$ is hydrogen, C$_{1-3}$ alkyl, or halogen;
each R$^{6a}$ is independently C$_{1-3}$ alkyl, C$_{2-3}$ alkenyl, or C$_{2-3}$ alkynyl, wherein the alkynyl is optionally substituted with 1 to 3 R$^{6j}$;
each R$^{6j}$ is independently C$_{2-3}$ alkoxyalkyl, halogen, C$_{1-3}$ haloalkyl, C$_{1-3}$ haloalkoxy, —CN, C$_{3-8}$ cycloalkyl, or heterocycloalkyl, wherein the cycloalkyl or heterocycloalkyl is optionally substituted with 1 to 3 R$^{6p}$;

each $R^{6p}$ is independently $C_{1-3}$ alkyl, $C_{1-3}$ hydroxyalkyl, $C_{2-3}$ alkoxyalkyl, halogen, $C_{1-3}$ haloalkyl, $C_{1-3}$ haloalkoxy, or —CN;
$R^7$ is hydrogen or $C_{1-3}$ alkyl; and

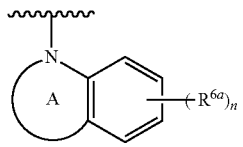

has the structure

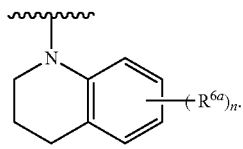

30. The compound of claim 20, or a pharmaceutically acceptable salt thereof, wherein $R^2$ is hydrogen, F, or Cl.

31. The compound of claim 20, or a pharmaceutically acceptable salt thereof, wherein $R^3$ is hydrogen, F, or Cl.

32. The compound of claim 20, or a pharmaceutically acceptable salt thereof, wherein each $R^{6a}$ is independently $C_{2-3}$ alkynyl or halogen, wherein the alkynyl is optionally substituted with 1 to 3 $R^{6j}$.

33. The compound of claim 20, or a pharmaceutically acceptable salt thereof, wherein each $R^{6j}$ is independently $C_{2-3}$ alkoxyalkyl, halogen, $C_{1-3}$ haloalkyl, —CN, $C_{3-6}$ cycloalkyl, or heterocycloalkyl, wherein the cycloalkyl or heterocycloalkyl is optionally substituted with 1 to 3 $R^{6p}$, and each heterocycloalkyl is a 3 to 6 membered ring having 1 to 2 heteroatoms each independently N, O or S.

34. The compound of claim 20, or a pharmaceutically acceptable salt thereof, wherein each $R^{6p}$ is independently Me, Et, $CH_2OH$, F, $CH_2F$, $CHF_2$, $CF_3$, $CH_2CF_3$, $CF_2CH_3$, or —CN.

35. The compound of claim 20, or a pharmaceutically acceptable salt thereof, wherein

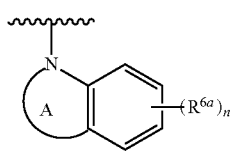

has the structure

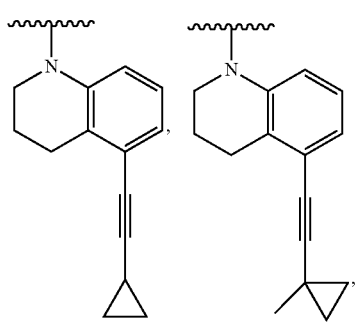

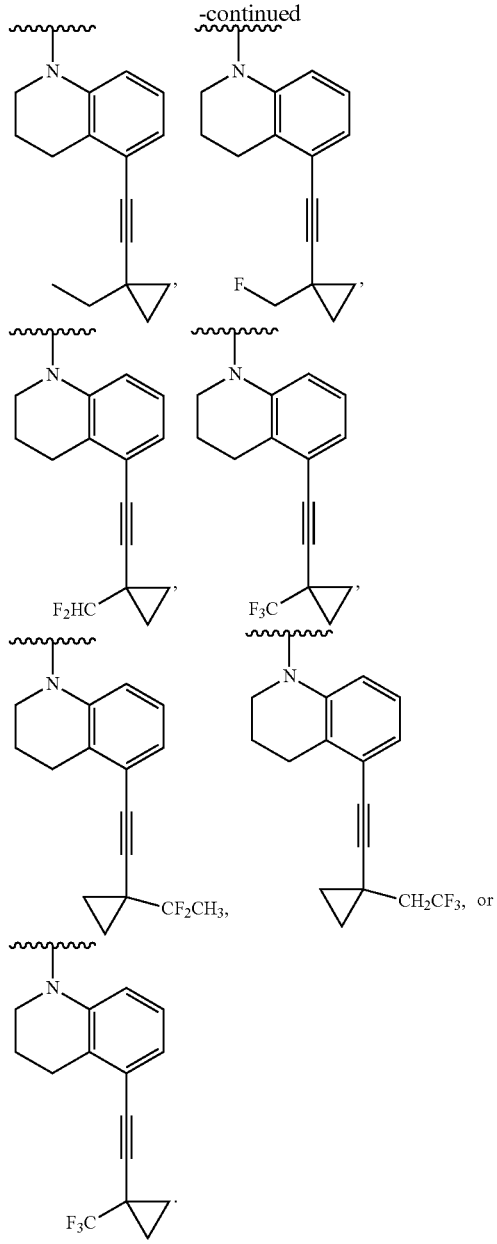

36. A pharmaceutical composition comprising a pharmaceutically effective amount of a compound of claim 1 or a pharmaceutically acceptable salt thereof, and a pharmaceutically acceptable carrier or excipient.

37. The pharmaceutical composition of claim 36, further comprising one or more additional therapeutic agents.

38. The pharmaceutical composition of claim 37, wherein the one or more additional therapeutic agents is independently an anti-neoplastic agent, nivolumab, pembrolizumab, atezolizumab, ipilimumab, chemotherapy, radiation therapy, or resection therapy.

39. The pharmaceutical composition of claim 37, wherein the one or more additional therapeutic agents is independently rituxan, doxorubicin, gemcitabine, nivolumab, pembrolizumab, artezolizumab, nivolumab, pembrolizumab, atezolizumab, or ipilimumab.

40. The pharmaceutical composition of claim 37, wherein the one or more additional therapeutic agents is a PD-1/PD-L1 inhibitor.

41. The pharmaceutical composition of claim 37, wherein the one or more additional therapeutic agents is a vaccine.

\* \* \* \* \*